US010329260B2

United States Patent
Kotian et al.

(10) Patent No.: US 10,329,260 B2
(45) Date of Patent: *Jun. 25, 2019

(54) HUMAN PLASMA KALLIKREIN INHIBITORS

(71) Applicant: BioCryst Pharmaceuticals, Inc., Durham, NC (US)

(72) Inventors: Pravin L. Kotian, Hoover, AL (US); Yarlagadda S. Babu, Birmingham, AL (US); Minwan Wu, Vestavia Hills, AL (US); Venkat R. Chintareddy, Vestavia Hills, AL (US); V. Satish Kumar, Birmingham, AL (US); Weihe Zhang, Vestavia, AL (US)

(73) Assignee: BioCryst Pharmaceuticals, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/977,129

(22) Filed: May 11, 2018

(65) Prior Publication Data

US 2018/0258049 A1  Sep. 13, 2018

Related U.S. Application Data

(63) Continuation of application No. 15/123,059, filed as application No. PCT/US2015/019535 on Mar. 9, 2015, now Pat. No. 10,125,102.

(60) Provisional application No. 61/981,515, filed on Apr. 18, 2014, provisional application No. 61/949,808, filed on Mar. 7, 2014.

(51) Int. Cl.

| C07D 231/14 | (2006.01) |
|---|---|
| C07D 417/12 | (2006.01) |
| C07D 413/12 | (2006.01) |
| C07D 413/04 | (2006.01) |
| C07D 405/12 | (2006.01) |
| C07D 403/12 | (2006.01) |
| C07D 401/12 | (2006.01) |
| C07D 401/04 | (2006.01) |
| C07D 401/14 | (2006.01) |
| C07D 403/04 | (2006.01) |

(52) U.S. Cl.
CPC ......... *C07D 231/14* (2013.01); *C07D 401/04* (2013.01); *C07D 401/12* (2013.01); *C07D 401/14* (2013.01); *C07D 403/04* (2013.01); *C07D 403/12* (2013.01); *C07D 405/12* (2013.01); *C07D 413/04* (2013.01); *C07D 413/12* (2013.01); *C07D 417/12* (2013.01)

(58) Field of Classification Search
None
See application file for complete search history.

(56) References Cited

U.S. PATENT DOCUMENTS

| 6,020,357 A | 2/2000 | Pinto et al. |
|---|---|---|
| 6,339,099 B1 | 1/2002 | Lam et al. |
| 6,548,525 B2 | 4/2003 | Galemmo, Jr. et al. |
| 2004/0171649 A1 | 9/2004 | Annis et al. |
| 2010/0256195 A1 | 10/2010 | Fischer et al. |
| 2018/0258049 A1 | 9/2018 | Kotian et al. |

FOREIGN PATENT DOCUMENTS

| CN | 103467380 A | 12/2013 |
|---|---|---|
| JP | 2001-526268 A | 12/2001 |
| JP | 2002/505686 A | 2/2002 |
| JP | 2004/538327 A | 12/2004 |
| JP | 2005/504084 A | 2/2005 |
| JP | 2005/532367 A | 10/2005 |
| JP | 2005/535630 A | 11/2005 |
| JP | 2007/182422 A | 7/2007 |
| JP | 2010/509349 A | 3/2010 |
| JP | 2010/512342 A | 4/2010 |
| WO | WO-9828269 A1 | 7/1998 |
| WO | WO-2000/047558 A1 | 8/2000 |
| WO | WO-02/00652 A1 | 1/2002 |
| WO | WO-2002/00651 A2 | 1/2002 |
| WO | WO-2003/045912 A1 | 6/2003 |

(Continued)

OTHER PUBLICATIONS

Extended European Search Report issued by the European Patent Office in corresponding European Application No. 15759254.4, completed on Jul. 24, 2017.

(Continued)

*Primary Examiner* — Kamal A Saeed
(74) *Attorney, Agent, or Firm* — Dana M. Gordon; Foley Hoag LLP

(57) ABSTRACT

Disclosed are compounds of formula I (I)

as described herein, and pharmaceutically acceptable salts thereof. The compounds are inhibitors of plasma kallikrein. Also disclosed are pharmaceutical compositions comprising at least one such compound, and methods involving use of the compounds and compositions in the treatment and prevention of diseases and conditions characterized by unwanted plasma kallikrein activity.

45 Claims, No Drawings

(56) References Cited

FOREIGN PATENT DOCUMENTS

| WO | WO-2005/094805 A1 | 10/2005 |
| WO | WO-2007020050 A2 | 2/2007 |
| WO | WO-2008058037 A1 | 5/2008 |
| WO | WO-2008073825 A1 | 6/2008 |

OTHER PUBLICATIONS

International Search Report and Written Opinion issued in PCT/US2015/019535 dated Jul. 30, 2015.
Pinto et al., "Factor Xa inhibitors: next-generation antithrombotic agents," J Med Chem, 53(17): 6243-6274 (2010).
Pubchem, Compound Summary for CID 46245112, Create Date: Jul. 19, 2010. [retrieved on Apr. 29, 2015]. Retrieved from the Internet. <URL: https://pubchem.ncbi.nlm.nih.gov/compound/46245112?from=summary>.
Quan et al., "Discovery of 1-(3'-aminobenzisoxazol-5'-yl)-3-trifluoromethyl-N-[2-fluoro-4-[(2'-dimethylaminomethyl)imidazol-1-yl]phenyl]-1H-pyrazole-5-carboxyamide hydrochloride (razaxaban), a highly potent, selective, and orally bioavailable factor Xa inhibitor," J Med Chem, 48(6): 1729-1744 (2005).
Search Report and Written Opinion issued by the Intellectual Property Office of Singapore in corresponding Application No. 11201607267S, dated Dec. 5, 2017.

HUMAN PLASMA KALLIKREIN INHIBITORS

RELATED APPLICATIONS

This application is a continuation of U.S. patent application Ser. No. 15/123,059, filed Sep. 1, 2016, which is the U.S. national phase of International Patent Application No. PCT/US2015/019535, filed Mar. 9, 2015, which claims the benefit of priority to U.S. Provisional Patent Application Ser. No. 61/949,808, filed Mar. 7, 2014; and U.S. Provisional Patent Application Ser. No. 61/981,515, filed Apr. 18, 2014.

BACKGROUND

Serine proteases make up the largest and most extensively studied group of proteolytic enzymes. Their critical roles in physiological processes extend over such diverse areas as blood coagulation, fibrinolysis, complement activation, reproduction, digestion, and the release of physiologically active peptides. Many of these vital processes begin with cleavage of a single peptide bond or a few peptide bonds in precursor protein or peptides. Sequential limited proteolytic reactions or cascades are involved in blood clotting, fibrinolysis, and complement activation. The biological signals to start these cascades can be controlled and amplified as well. Similarly, controlled proteolysis can shut down or inactivate proteins or peptides through single bond cleavages.

Kallikreins are a subgroup of serine proteases. In humans, plasma kallikrein (KLKB1) has no known homologue, while tissue kallikrein-related peptidases (KLKs) encode a family of fifteen closely related serine proteases. Plasma kallikrein participates in a number of pathways relating to the intrinsic pathway of coagulation, inflammation, and the complement system.

Coagulation is the process by which blood forms clots, for example to stop bleeding. The physiology of coagulation is somewhat complex insofar as it includes two separate initial pathways, which converge into a final common pathway leading to clot formation. In the final common pathway, prothrombin is converted into thrombin, which in turn converts fibrinogen into fibrin, the latter being the principal building block of cross-linked fibrin polymers which form a hemostatic plug. Of the two initial pathways upstream of the final common pathway, one is known as the contact activation or intrinsic pathway, and the other is known as the tissue factor or extrinsic pathway.

The intrinsic pathway begins with formation of a primary complex on collagen by high-molecular-weight kininogen (HMWK), prekallikrein, and FXII (Factor XII; Hageman factor). Prekallikrein is converted to kallikrein, and FXII is activated to become FXIIa. FXIIa then converts Factor XI (FXI) into FXIa, and FXIa in turn activates Factor IX (FIX), which with its co-factor FVIIIa form the "tenase" complex, which activates Factor X (FX) to FXa. It is FXa which is responsible for the conversion of prothrombin into thrombin within the final common pathway.

Prekallikrein, the inactive precursor of plasma kallikrein, is synthesized in the liver and circulates in the plasma bound to HMWK or as a free zymogen. Prekallikrein is cleaved by activated factor XII (FXIIa) to release activated plasma kallikrein (PK). Activated plasma kallikrein displays endopeptidase activity towards peptide bonds after arginine (preferred) and lysine. PK then generates additional FXIIa in a feedback loop which in turn activates factor XI (FXI) to FXIa to connect to the common pathway. Although the initial activation of the intrinsic pathway is through a small amount of FXIIa activating a small amount of PK, it is the subsequent feedback activation of FXII by PK that controls the extent of activation of the intrinsic pathway and hence downstream coagulation. Hathaway, W. E., et al. (1965) *Blood* 26:521-32.

Activated plasma kallikrein also cleaves HMWK to release the potent vasodilator peptide bradykinin. It is also able to cleave a number of inactive precursor proteins to generate active products, such as plasmin (from plasminogen) and urokinase (from prourokinase). Plasmin, a regulator of coagulation, proteolytically cleaves fibrin into fibrin degradation products that inhibit excessive fibrin formation.

Patients who have suffered acute myocardial infarction (MI) show clinical evidence of being in a hypercoagulable (clot-promoting) state. This hypercoagulability is paradoxically additionally aggravated in those receiving fibrinolytic therapy. Increased generation of thrombin, as measured by thrombin-antithrombin III (TAT) levels, is observed in patients undergoing such treatment compared to the already high levels observed in those receiving heparin alone. Hoffmeister, H. M. et al. (1998) *Circulation* 98:2527-33. The increase in thrombin has been proposed to result from plasmin-mediated activation of the intrinsic pathway by direct activation of FXII by plasmin.

Not only does the fibrinolysis-induced hypercoagulability lead to increased rates of reocclusion, but it is also probably responsible, at least in part, for failure to achieve complete fibrinolysis of the clot (thrombus), a major shortcoming of fibrinolytic therapy (Keeley, E. C. et al. (2003) Lancet 361: 13-20). Another problem in fibrinolytic therapy is the accompanying elevated risk of intracranial hemorrhage. Menon, V. et al. (2004) *Chest* 126:549S-575S; Fibrinolytic Therapy Trialists' Collaborative Group (1994) *Lancet* 343: 311-22. Hence, an adjunctive anti-coagulant therapy that does not increase the risk of bleeding, but inhibits the formation of new thrombin, would be greatly beneficial.

Therefore, a need exists to develop inhibitors of PK that can tip the balance of fibrinolysis/thrombosis at the occluding thrombus toward dissolution, thereby promoting reperfusion and also attenuating the hypercoagulable state, thus preventing thrombus from reforming and reoccluding the vessel.

SUMMARY OF THE INVENTION

Provided are compounds, pharmaceutical compositions comprising the compounds, and methods useful for inhibiting plasma kallikrein and treating or preventing plasma kallikrein-related diseases and conditions. The compounds and their pharmaceutically acceptable salts are specifically useful as inhibitors of human plasma kallikrein.

In certain aspects, the invention provides a compound, or a pharmaceutically acceptable salt thereof, represented by formula I:

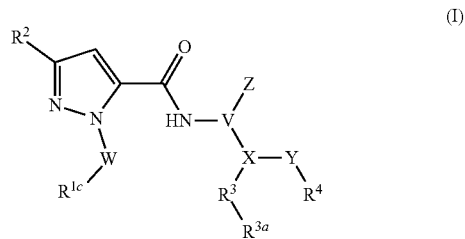

wherein:

V is optionally substituted aryl or heteroaryl;

W is optionally substituted aryl or heteroaryl;

X represents CH, C(OH), C(O($C_1$-$C_6$)alkyl), —C($NH_2$), —C($NR^aR^b$), —C($N_3$), —C(CN), —C($NO_2$), —C(S(O)$_n R^a$), —C[—C(=O)$R^c$], —C[—C(=O)$R^c$], —C[—C(=O)$NR^cR^d$], —C[—C(=O)$SR^c$], —C[—S(O)$R^c$], —C[—S(O)$_2R^c$], —C[S(O)(O$R^c$)], —C[—S(O)$_2$(O$R^c$)], —C[—SO$_2NR^cR^d$], —C(halogen), —C[($C_1$-$C_8$)alkyl], —C[($C_4$-$C_8$)carbocyclylalkyl], —C[($C_1$-$C_8$)substituted alkyl], —C[($C_2$-$C_8$)alkenyl], —C[($C_2$-$C_8$)substituted alkenyl], —C[($C_2$-$C_8$)alkynyl], —C[($C_2$-$C_8$)substituted alkynyl], —C[aryl($C_1$-$C_8$)alkyl], C(O)N, $CH_2$N, N, C(O), P(O), —O—, S(O)N, or S(O)$_2$N; provided that:

if X represents CH, then —Y—$R^4$ represents —H or —OH, or both Y and $R^4$ are present;

if X represents C(OH), C(O($C_1$-$C_6$)alkyl), —C($NH_2$), —C($NR^aR^b$), —C($N_3$), —C(CN), —C($NO_2$), —C(S(O)$_n R^a$), —C[—C(=O)$R^c$], —C[—C(=O)$R^c$], —C[—C(=O)$NR^cR^d$], —C[—C(=O)$SR^c$], —C[—S(O)$R^c$], —C[—S(O)$_2R^c$], —C[S(O)(O$R^c$)], —C[—S(O)$_2$(O$R^c$)], —C[—SO$_2NR^cR^d$], —C(halogen), —C[($C_1$-$C_8$)alkyl], —C[($C_4$-$C_8$)carbocyclylalkyl], —C[($C_1$-$C_8$)substituted alkyl], —C[($C_2$-$C_8$) alkenyl], —C[($C_2$-$C_8$)substituted alkenyl], —C[($C_2$-$C_8$)alkynyl], —C[($C_2$-$C_8$)substituted alkynyl], or —C[aryl($C_1$-$C_8$)alkyl], then —Y—$R^4$ is present;

if X represents C(O)N, then —Y—$R^4$ represents H; or —Y—$R^4$ represents H, and —$R^3$—$R^{3a}$ represents H;

if X represents $CH_2$N, then —Y—$R^4$ represents ($C_1$-$C_6$)alkyl;

if X represents N, then —Y—$R^4$ represents H, or both Y and $R^4$ are present; and if X represents C(O) or —O—, then —Y—$R^4$ is absent;

—Y—$R^4$, when present, represents —(($C_1$-$C_6$)alkyl)-$R^4$, —$CH_2$C(O)—$R^4$, —$CH_2$NH—$R^4$, —$CH_2$N(($C_1$-$C_6$)alkyl)-$R^4$, —$CR^aR^b$—$R^4$, —NH—$R^4$, —NH$CH_2$—$R^4$, —NHC(O)—$R^4$, —N(($C_1$-$C_6$)alkyl)-$R^4$, —N(($C_1$-$C_6$)alkyl)$CH_2$—$R^4$, —N(($CH_2$)$_2$OH)—$R^4$, —N[($C_3$-$C_8$)cycloalkyl($C_1$-$C_6$)alkyl]$R^4$, -heterocyclyl-$R^4$, —O$R^4$, —O$CH_2$—$R^4$, —OC(O)—$R^4$, —OC(O)$NR^aR^b$, —S$CH_2R^4$, or —S$R^4$, wherein the ($C_1$-$C_6$)alkyl moiety of —(($C_1$-$C_6$)alkyl)-$R^4$ is optionally substituted;

Z is absent or represents one or more substituents independently selected from the group consisting of halo, hydroxy, ($C_1$-$C_6$)alkyl, —$CF_3$, —$OCF_3$, ($C_1$-$C_6$)alkoxy, aryl, aryloxy, amino, amino($C_1$-$C_6$)alkyl, —C(O)$NH_2$, cyano, —NHC(O)($C_1$-$C_6$)alkyl, —$SO_2$($C_1$-$C_6$)alkyl, —$SO_2NH_2$, ($C_3$-$C_8$)cycloalkyl, ($CH_2$)$_r$O$R^a$, $NO_2$, ($CH_2$)$_r NR^aR^b$, ($CH_2$)$_r$C(O)$R^a$, $NR^a$C(O)$R^b$, C(O)$NR^cR^d$, $NR^a$C(O)$NR^cR^d$, —C(=$NR^a$)$NR^cR^d$, NHC(=$NR^a$)$NR^cR^d$, $NR^aR^b$, $SO_2NR^cR^d$, $NR^a SO_2 NR^cR^d$, $NR^a SO_2$—($C_1$-$C_6$)alkyl, $NR^a SO_2 R^a$, S(O)$_p R^a$, ($CF_2$)$_r CF_3$, NH$CH_2 R^a$, O$CH_2 R^a$, S$CH_2 R^a$, NH($CH_2$)$_2$($CH_2$)$_r R^a$, O($CH_2$)$_2$($CH_2$)$_r R^a$, and S($CH_2$)$_2$($CH_2$)$_r R^a$; or alternatively Z is a 5- or 6-membered aromatic heterocycle containing from 1 to 4 heteroatoms selected from the group consisting of N, O, and S;

$R^{1c}$ represents halo, amino($C_1$-$C_6$)alkyl, ($C_1$-$C_6$)alkoxy, cyano, —C(=NH)$NH_2$, —CON$R^aR^b$, —($C_1$-$C_6$)alkylCON$R^aR^b$, —$SO_2 CH_3$, formyl, acyl, —$NH_2$, —C(=NH)NH(OH), —C(=NH)NH(C(O)O—($C_1$-$C_6$)alkyl), —C(=NH)NH(C(O)O—($C_1$-$C_6$)haloalkyl), —C(=NH)NH(C(O)S—($C_1$-$C_6$)alkyl), —C(=NH) NH(C(O)(OCH($C_1$-$C_6$)alkyl)OC(O)($C_1$-$C_6$)alkyl), optionally substituted aryl, or optionally substituted heteroaryl;

$R^2$ represents halo, ($C_1$-$C_6$)alkyl, ($C_3$-$C_8$)cycloalkyl, ($C_1$-$C_6$)fluoroalkyl, —$OCH_3$, —Si($CH_3$)$_3$, —$CONH_2$, —C(O)OH, cyano, or phenyl;

$R^3$, when present, represents —NH—, —O—, optionally substituted aryl, heteroaryl, phenyl, carbocyclyl, or heterocyclyl;

$R^{3a}$ is absent or represents one or more substituents independently selected from the group consisting of halo, hydroxy, ($C_1$-$C_6$)alkyl, —$CF_3$, —$OCF_3$, ($C_1$-$C_6$)alkoxy, aryl, aryloxy, amino, amino($C_1$-$C_6$)alkyl, —C(O)$NH_2$, cyano, —NHC(O)($C_1$-$C_6$)alkyl, —$SO_2$($C_1$-$C_6$)alkyl, —$SO_2NH_2$, ($C_3$-$C_8$)cycloalkyl, ($CH_2$)$_r$O$R^a$, $NO_2$, ($CH_2$)$_r NR^aR^b$, ($CH_2$)$_r$C(O)$R^a$, $NR^a$C(O)$R^b$, C(O)$NR^cR^d$, $NR^a$C(O)$NR^cR^d$, —C(=$NR^a$)$NR^cR^d$, NHC(=$NR^a$)$NR^cR^d$, $NR^aR^b$ $SO_2NR^cR^d$, $NR^a SO_2 NR^cR^d$, $NR^a SO_2$—($C_1$-$C_6$)alkyl, $NR^a SO_2 R^a$, S(O)$_p R^a$, ($CF_2$)$_r CF_3$, NH$CH_2 R^a$, O$CH_2 R^a$, S$CH_2 R^a$, NH($CH_2$)$_2$($CH_2$)$_r R^a$, O($CH_2$)$_2$($CH_2$)$_r R^a$, or S($CH_2$)$_2$($CH_2$)$_r R^a$; or alternatively $R^{3a}$ is a 5- or 6-membered aromatic heterocycle containing from 1 to 4 heteroatoms selected from the group consisting of N, O, and S;

$R^4$ represents hydrogen, hydroxy, optionally substituted ($C_1$-$C_6$)alkyl, optionally substituted ($C_3$-$C_8$)cycloalkyl, heterocyclyl($C_1$-$C_6$)alkyl, ($C_3$-$C_8$)cycloalkyl($C_1$-$C_6$)alkyl, —$CH_2$OH, —CH(($C_1$-$C_6$)alkyl)OH, —CH($NH_2$)CH(($C_1$-$C_6$)alkyl)$_2$, optionally substituted aryl, optionally substituted aryl($C_1$-$C_6$)alkyl, heteroaryl, optionally substituted heteroaryl($C_1$-$C_6$)alkyl, —$CH_2$S($C_1$-$C_6$)alkyl, amino, or cyano; or —($CR^aR^b$)$_r$($CR^aR^b$)$_p$— fused to the 4-position of the ring bearing Z to form a 5- to 7-membered heterocyclic ring with optional substituents; or, when $R^3$ is phenyl, can represent —$NR^a$— fused to the position ortho to X on that phenyl;

each $R^a$ and $R^b$ is independently H, ($C_1$-$C_8$)alkyl, ($C_2$-$C_8$)alkenyl, ($C_2$-$C_8$)alkynyl, aryl($C_1$-$C_8$)alkyl, ($C_3$-$C_8$)carbocyclylalkyl, —C(=O)$R^c$, —C(=O)O$R^c$, —C(=O)$NR^cR^d$, —C(=O)$SR^c$, S(O)$R^c$, —S(O)$_2 R^c$, —S(O)(O$R^c$), or —$SO_2 NR^cR^d$;

each $R^c$ and $R^d$ is independently H, ($C_1$-$C_8$)alkyl, ($C_2$-$C_8$)alkenyl, ($C_2$-$C_8$)alkynyl, ($C_4$-$C_8$) carbocyclylalkyl, optionally substituted aryl, optionally substituted heteroaryl, —C(=O)($C_1$-$C_8$)alkyl, —S(O)$_n$($C_1$-$C_8$)alkyl, or aryl($C_1$-$C_8$)alkyl; or when R and $R^d$ are bonded to a common nitrogen atom, then they may form a 3- to 7-membered heterocyclic ring wherein optionally a carbon atom of said heterocyclic ring may be replaced with —O—, —S— or —$NR^a$—;

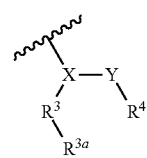

can represent

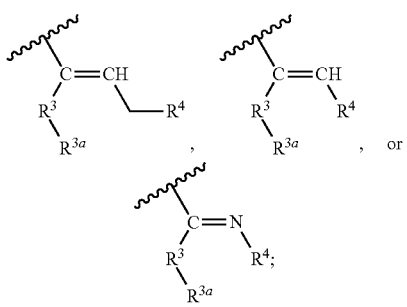

n is 2 or 3;
r is independently for each occurrence 0, 1, 2, or 3;
p is independently for each occurrence 0, 1, or 2; and
the stereochemical configuration at any chiral center is R, S, or a mixture of R and S.

In certain embodiments, the compound is represented by formula II:

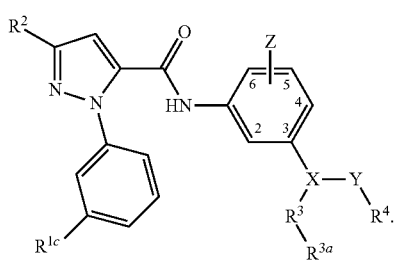

(II)

In certain embodiments, the compound is represented by formula III:

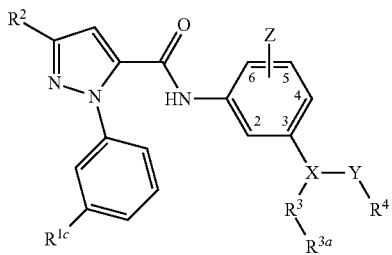

(III)

wherein:
X represents CH, C(OH), C(O($C_1$-$C_6$)alkyl), C(O)N, $CH_2$N, N, C(O), or —O—;
—Y—$R^4$, when present, represents —(($C_1$-$C_6$)alkyl)-$R^4$, —$CH_2$C(O)—$R^4$, —$CH_2$NH—$R^4$, —$CH_2$N(($C_1$-$C_6$)alkyl)-$R^4$, —$CR^aR^b$—$R^4$, —NH—$R^4$, —$NHCH_2$—$R^4$, —NHC(O)—$R^4$, —N(($C_1$-$C_6$)alkyl)-$R^4$, —N(($C_1$-$C_6$)alkyl)$CH_2$—$R^4$, —N(($CH_2$)$_2$OH)—$R^4$, —N[($C_3$-$C_8$)cycloalkyl($C_1$-$C_6$)alkyl]$R^4$, -heterocyclyl-$R^4$, —O$R^4$, —O$CH_2$—$R^4$, —OC(O)—$R^4$, —OC(O)N$R^aR^b$, —SC$H_2R^4$, or —S$R^4$, wherein the ($C_1$-$C_6$)alkyl moiety of —(($C_1$-$C_6$)alkyl)-$R^4$ is optionally substituted;
Z is absent or represents halo, hydroxy, ($C_1$-$C_6$)alkyl, —$CF_3$, —$OCF_3$, ($C_1$-$C_6$)alkoxy, aryl, aryloxy, amino, amino($C_1$-$C_6$)alkyl, —C(O)$NH_2$, cyano, —NHC(O)($C_1$-$C_6$)alkyl, —$SO_2$($C_1$-$C_6$)alkyl, —$SO_2NH_2$, or ($C_3$-$C_8$)cycloalkyl;
$R^{1c}$ represents halo, amino($C_1$-$C_6$)alkyl, ($C_1$-$C_6$)alkoxy, cyano, —$SO_2CH_3$, formyl, acyl, or optionally substituted aryl;
$R^{3a}$ is absent or represents one or more substituents independently selected from the group consisting of halo, hydroxy, ($C_1$-$C_6$)alkyl, —$CF_3$, —$OCF_3$, ($C_1$-$C_6$)alkoxy, aryl, aryloxy, amino, amino($C_1$-$C_6$)alkyl, —C(O)$NH_2$, cyano, —NHC(O)($C_1$-$C_6$)alkyl, —$SO_2$($C_1$-$C_6$)alkyl, and —$SO_2NH_2$;
$R^4$ represents hydrogen, hydroxy, optionally substituted ($C_1$-$C_6$)alkyl, optionally substituted ($C_3$-$C_8$)cycloalkyl, heterocyclyl($C_1$-$C_6$)alkyl, ($C_3$-$C_8$)cycloalkyl($C_1$-$C_6$)alkyl, —$CH_2$OH, —CH(($C_1$-$C_6$)alkyl)OH, —CH($NH_2$)CH(($C_1$-$C_6$)alkyl)$_2$, optionally substituted aryl, optionally substituted aryl($C_1$-$C_6$)alkyl, heteroaryl, optionally substituted heteroaryl($C_1$-$C_6$)alkyl, —$CH_2$S($C_1$-$C_6$)alkyl, amino, or cyano; or —$CH_2$— fused to the 4-position of the ring bearing Z to form a 5- to 7-membered heterocyclic ring with optional substituents;
or, when $R^3$ is phenyl, can represent —NH— fused to the position ortho to X on that phenyl; and

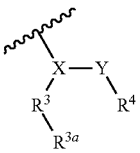

can represent

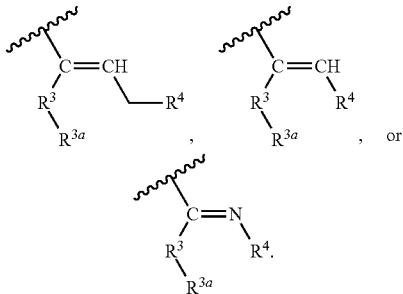

In certain embodiments, the compound is represented by formula IV:

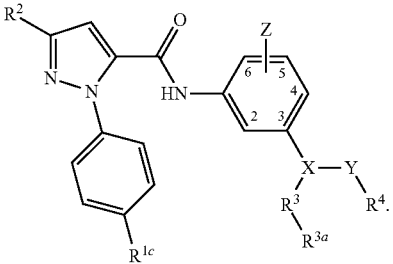

(IV)

In certain embodiments, the compound is represented by formula V:

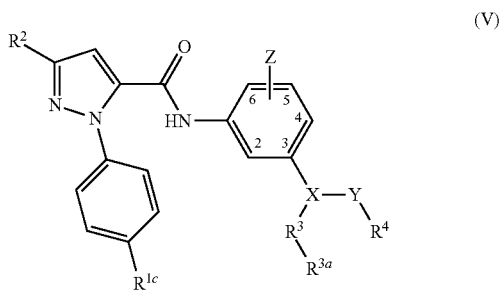

(V)

wherein:

X represents CH, C(OH), C(O(C$_1$-C$_6$)alkyl), C(O)N, CH$_2$N, N, C(O), or —O—;

—Y—R$^4$, when present, represents —((C$_1$-C$_6$)alkyl)-R$^4$, —CH$_2$C(O)—R$^4$, —CH$_2$NH—R$^4$, —CH$_2$N((C$_1$-C$_6$)alkyl)-R$^4$, —CR$^a$R$^b$—R$^4$, —NH—R$^4$, —NHCH$_2$—R$^4$, —NHC(O)—R$^4$, —N((C$_1$-C$_6$)alkyl)-R$^4$, —N((C$_1$-C$_6$)alkyl)CH$_2$—R$^4$, —N((CH$_2$)$_2$OH)—R$^4$, —N[(C$_3$-C$_8$)cycloalkyl(C$_1$-C$_6$)alkyl]R$^4$, -heterocyclyl-R$^4$, —OR$^4$, —OCH$_2$—R$^4$, —OC(O)—R$^4$, —OC(O)NR$^a$R$^b$, —SCH$_2$R$^4$, or —SR$^4$, wherein the (C$_1$-C$_6$)alkyl moiety of —((C$_1$-C$_6$)alkyl)-R$^4$ is optionally substituted;

Z is absent or represents halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, —SO$_2$NH$_2$, or (C$_3$-C$_8$)cycloalkyl;

R$^{1c}$ represents halo, amino(C$_1$-C$_6$)alkyl, (C$_1$-C$_6$)alkoxy, cyano, —SO$_2$CH$_3$, formyl, acyl, or optionally substituted aryl;

R$^{3a}$ is absent or represents one or more substituents independently selected from the group consisting of halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, and —SO$_2$NH$_2$;

R$^4$ represents hydrogen, hydroxy, optionally substituted (C$_1$-C$_6$)alkyl, optionally substituted (C$_3$-C$_8$)cycloalkyl, heterocyclyl(C$_1$-C$_6$)alkyl, (C$_3$-C$_8$)cycloalkyl(C$_1$-C$_6$)alkyl, —CH$_2$OH, —CH((C$_1$-C$_6$)alkyl)OH, —CH(NH$_2$)CH((C$_1$-C$_6$)alkyl)$_2$, optionally substituted aryl, optionally substituted aryl(C$_1$-C$_6$)alkyl, heteroaryl, optionally substituted heteroaryl(C$_1$-C$_6$)alkyl, —CH$_2$S(C$_1$-C$_6$)alkyl, amino, or cyano; or —CH$_2$— fused to the 4-position of the ring bearing Z to form a 5- to 7-membered heterocyclic ring with optional substituents;

or, when R$^3$ is phenyl, can represent —NH— fused to the position ortho to X on that phenyl; and

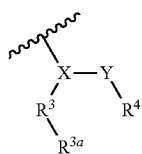

can represent

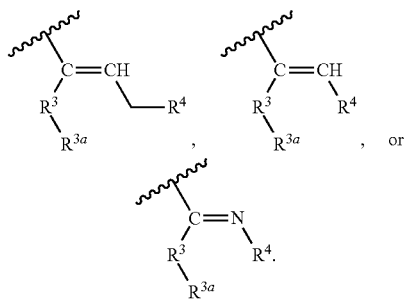

In certain embodiments, the compound is represented by formula VI:

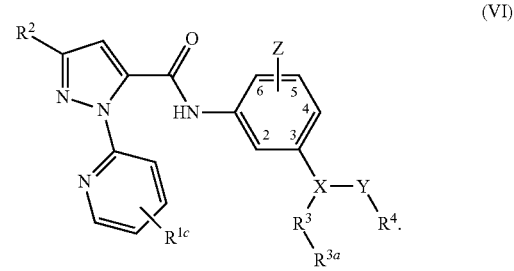

(VI)

In certain embodiments, the compound is represented by formula VII:

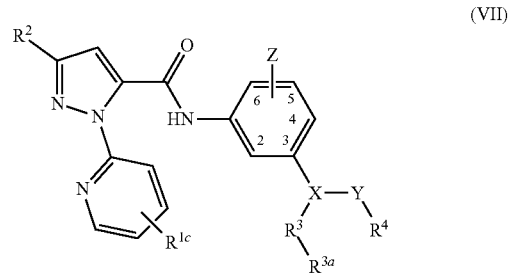

(VII)

wherein:

X represents CH, C(OH), C(O(C$_1$-C$_6$)alkyl), C(O)N, CH$_2$N, N, C(O), or —O—;

—Y—R$^4$, when present, represents —((C$_1$-C$_6$)alkyl)-R$^4$, —CH$_2$C(O)—R$^4$, —CH$_2$NH—R$^4$, —CH$_2$N((C$_1$-C$_6$)alkyl)-R$^4$, —CR$^a$R$^b$—R$^4$, —NH—R$^4$, —NHCH$_2$—R$^4$, —NHC(O)—R$^4$, —N((C$_1$-C$_6$)alkyl)-R$^4$, —N((C$_1$-C$_6$)alkyl)CH$_2$—R$^4$, —N((CH$_2$)$_2$OH)—R$^4$, —N[(C$_3$-C$_8$)cycloalkyl(C$_1$-C$_6$)alkyl]R$^4$, -heterocyclyl-R$^4$, —OR$^4$, —OCH$_2$—R$^4$, —OC(O)—R$^4$, —OC(O)NR$^a$R$^b$, —SCH$_2$R$^4$, or —SR$^4$, wherein the (C$_1$-C$_6$)alkyl moiety of —((C$_1$-C$_6$)alkyl)-R$^4$ is optionally substituted;

Z is absent or represents halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, —SO$_2$NH$_2$, or (C$_3$-C$_8$)cycloalkyl;

R$^{1c}$ represents halo, amino(C$_1$-C$_6$)alkyl, (C$_1$-C$_6$)alkoxy, cyano, —SO$_2$CH$_3$, formyl, acyl, or optionally substituted aryl;

R$^{3a}$ is absent or represents one or more substituents independently selected from the group consisting of halo, hydroxy, $(C_1\text{-}C_6)$alkyl, —$CF_3$, —$OCF_3$, $(C_1\text{-}C_6)$alkoxy, aryl, aryloxy, amino, amino$(C_1\text{-}C_6)$alkyl, —$C(O)NH_2$, cyano, —$NHC(O)(C_1\text{-}C_6)$alkyl, —$SO_2(C_1\text{-}C_6)$alkyl, and —$SO_2NH_2$;

$R^4$ represents hydrogen, hydroxy, optionally substituted $(C_1\text{-}C_6)$alkyl, optionally substituted $(C_3\text{-}C_8)$cycloalkyl, heterocyclyl$(C_1\text{-}C_6)$alkyl, $(C_3\text{-}C_8)$cycloalkyl$(C_1\text{-}C_6)$alkyl, —$CH_2OH$, —$CH((C_1\text{-}C_6)\text{alkyl})OH$, —$CH(NH_2)CH((C_1\text{-}C_6)\text{alkyl})_2$, optionally substituted aryl, optionally substituted aryl$(C_1\text{-}C_6)$alkyl, heteroaryl, optionally substituted heteroaryl$(C_1\text{-}C_6)$alkyl, —$CH_2S(C_1\text{-}C_6)$alkyl, amino, or cyano; or —$CH_2$— fused to the 4-position of the ring bearing Z to form a 5- to 7-membered heterocyclic ring with optional substituents;

or, when $R^3$ is phenyl, can represent —NH— fused to the position ortho to X on that phenyl; and

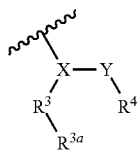

can represent

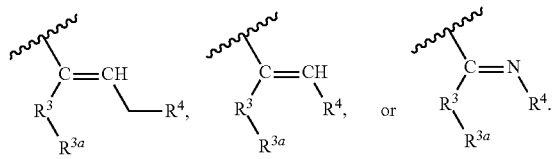

In certain embodiments, the compound is represented by formula VIII:

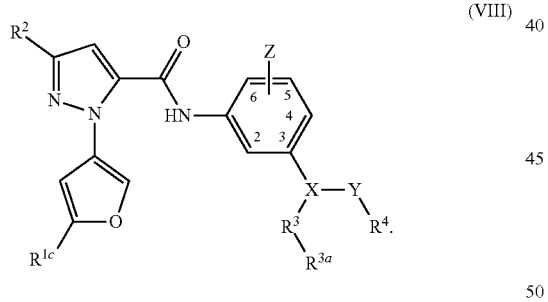

(VIII)

In certain embodiments, the compound is represented by formula IX:

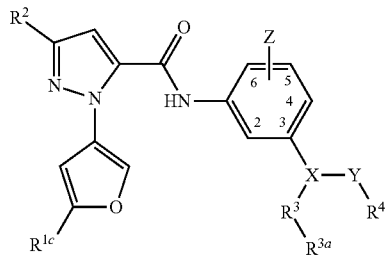

(IX)

wherein:

X represents CH, C(OH), C(O(C_1-C_6)alkyl), C(O)N, $CH_2N$, N, C(O), or —O—;

—Y—$R^4$, when present, represents —$((C_1\text{-}C_6)\text{alkyl})\text{-}R^4$, —$CH_2C(O)\text{—}R^4$, —$CH_2NH\text{—}R^4$, —$CH_2N((C_1\text{-}C_6)\text{alkyl})\text{-}R^4$, —$CR^aR^b\text{—}R^4$, —$NH\text{—}R^4$, —$NHCH_2\text{—}R^4$, —$NHC(O)\text{—}R^4$, —$N((C_1\text{-}C_6)\text{alkyl})\text{-}R^4$, —$N((C_1\text{-}C_6)\text{alkyl})CH_2\text{—}R^4$, —$N((CH_2)_2OH)\text{—}R^4$, —$N[(C_3\text{-}C_8)\text{cycloalkyl}(C_1\text{-}C_6)\text{alkyl}]R^4$, -heterocyclyl-$R^4$, —$OR^4$, —$OCH_2\text{—}R^4$, —$OC(O)\text{—}R^4$, —$OC(O)NR^aR^b$, —$SCH_2R^4$, or —$SR^4$, wherein the $(C_1\text{-}C_6)$alkyl moiety of —$((C_1\text{-}C_6)\text{alkyl})\text{-}R^4$ is optionally substituted;

Z is absent or represents halo, hydroxy, $(C_1\text{-}C_6)$alkyl, —$CF_3$, —$OCF_3$, $(C_1\text{-}C_6)$alkoxy, aryl, aryloxy, amino, amino$(C_1\text{-}C_6)$alkyl, —$C(O)NH_2$, cyano, —$NHC(O)(C_1\text{-}C_6)$alkyl, —$SO_2(C_1\text{-}C_6)$alkyl, —$SO_2NH_2$, or $(C_3\text{-}C_8)$cycloalkyl;

$R^{1c}$ represents halo, amino$(C_1\text{-}C_6)$alkyl, $(C_1\text{-}C_6)$alkoxy, cyano, —$SO_2CH_3$, formyl, acyl, or optionally substituted aryl;

$R^{3a}$ is absent or represents one or more substituents independently selected from the group consisting of halo, hydroxy, $(C_1\text{-}C_6)$alkyl, —$CF_3$, —$OCF_3$, $(C_1\text{-}C_6)$alkoxy, aryl, aryloxy, amino, amino$(C_1\text{-}C_6)$alkyl, —$C(O)NH_2$, cyano, —$NHC(O)(C_1\text{-}C_6)$alkyl, —$SO_2(C_1\text{-}C_6)$alkyl, and —$SO_2NH_2$;

$R^4$ represents hydrogen, hydroxy, optionally substituted $(C_1\text{-}C_6)$alkyl, optionally substituted $(C_3\text{-}C_8)$cycloalkyl, heterocyclyl$(C_1\text{-}C_6)$alkyl, $(C_3\text{-}C_8)$cycloalkyl$(C_1\text{-}C_6)$alkyl, —$CH_2OH$, —$CH((C_1\text{-}C_6)\text{alkyl})OH$, —$CH(NH_2)CH((C_1\text{-}C_6)\text{alkyl})_2$, optionally substituted aryl, optionally substituted aryl$(C_1\text{-}C_6)$alkyl, heteroaryl, optionally substituted heteroaryl$(C_1\text{-}C_6)$alkyl, —$CH_2S(C_1\text{-}C_6)$alkyl, amino, or cyano; or —$CH_2$— fused to the 4-position of the ring bearing Z to form a 5- to 7-membered heterocyclic ring with optional substituents;

or, when $R^3$ is phenyl, can represent —NH— fused to the position ortho to X on that phenyl; and

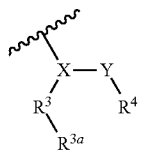

can represent

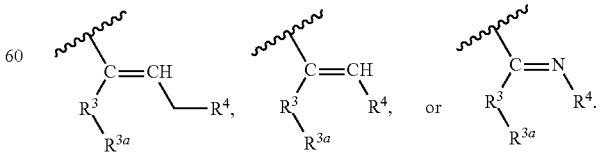

In certain embodiments, the compound is represented by formula X:

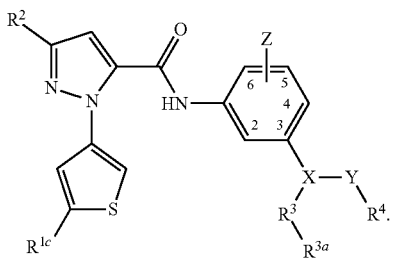

(X)

In certain embodiments, the compound is represented by formula XI:

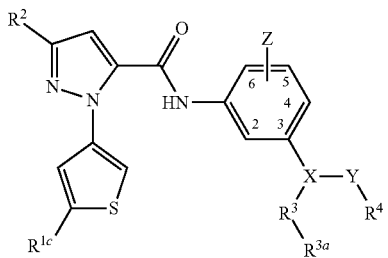

(XI)

wherein:
X represents CH, C(OH), C(O($C_1$-$C_6$)alkyl), C(O)N, $CH_2$N, N, C(O), or —O—;
—Y—$R^4$, when present, represents —(($C_1$-$C_6$)alkyl)-$R^4$, —$CH_2$C(O)—$R^4$, —$CH_2$NH—$R^4$, —$CH_2$N(($C_1$-$C_6$)alkyl)-$R^4$, —$CR^aR^b$—$R^4$, —NH—$R^4$, —NHCH$_2$—$R^4$, —NHC(O)—$R^4$, —N(($C_1$-$C_6$)alkyl)-$R^4$, —N(($C_1$-$C_6$)alkyl)CH$_2$—$R^4$, —N(($CH_2$)$_2$OH)—$R^4$, —N[($C_3$-$C_8$)cycloalkyl($C_1$-$C_6$)alkyl]$R^4$, -heterocyclyl-$R^4$, —O$R^4$, —OCH$_2$—$R^4$, —OC(O)—$R^4$, —OC(O)NR$^a$R$^b$, —SCH$_2$R$^4$, or —SR$^4$, wherein the ($C_1$-$C_6$)alkyl moiety of —(($C_1$-$C_6$)alkyl)-$R^4$ is optionally substituted;
Z is absent or represents halo, hydroxy, ($C_1$-$C_6$)alkyl, —CF$_3$, —OCF$_3$, ($C_1$-$C_6$)alkoxy, aryl, aryloxy, amino, amino($C_1$-$C_6$)alkyl, —C(O)NH$_2$, cyano, —NHC(O)($C_1$-$C_6$)alkyl, —SO$_2$($C_1$-$C_6$)alkyl, —SO$_2$NH$_2$, or ($C_3$-$C_8$)cycloalkyl;
$R^{1c}$ represents halo, amino($C_1$-$C_6$)alkyl, ($C_1$-$C_6$)alkoxy, cyano, —SO$_2$CH$_3$, formyl, acyl, or optionally substituted aryl;
$R^{3a}$ is absent or represents one or more substituents independently selected from the group consisting of halo, hydroxy, ($C_1$-$C_6$)alkyl, —CF$_3$, —OCF$_3$, ($C_1$-$C_6$)alkoxy, aryl, aryloxy, amino, amino($C_1$-$C_6$)alkyl, —C(O)NH$_2$, cyano, —NHC(O)($C_1$-$C_6$)alkyl, —SO$_2$($C_1$-$C_6$)alkyl, and —SO$_2$NH$_2$;
$R^4$ represents hydrogen, hydroxy, optionally substituted ($C_1$-$C_6$)alkyl, optionally substituted ($C_3$-$C_8$)cycloalkyl, heterocyclyl($C_1$-$C_6$)alkyl, ($C_3$-$C_8$)cycloalkyl($C_1$-$C_6$)alkyl, —CH$_2$OH, —CH(($C_1$-$C_6$)alkyl)OH, —CH(NH$_2$)CH(($C_1$-$C_6$)alkyl)$_2$, optionally substituted aryl, optionally substituted aryl($C_1$-$C_6$)alkyl, heteroaryl, optionally substituted heteroaryl($C_1$-$C_6$)alkyl, —CH$_2$S($C_1$-$C_6$)alkyl, amino, or cyano; or —CH$_2$— fused to the 4-position of the ring bearing Z to form a 5- to 7-membered heterocyclic ring with optional substituents;

or, when $R^3$ is phenyl, can represent —NH— fused to the position ortho to X on that phenyl; and

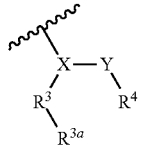

can represent

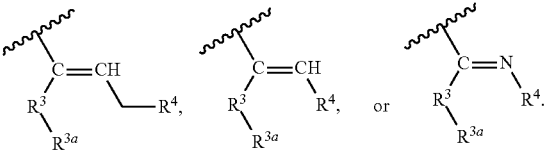

In certain embodiments, the compound is represented by formula XII:

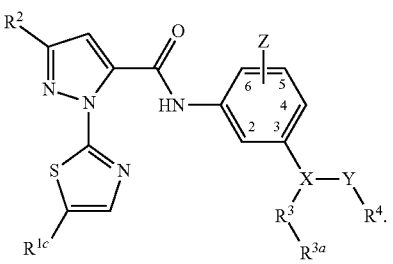

(XII)

In certain embodiments, the compound is represented by formula XIII:

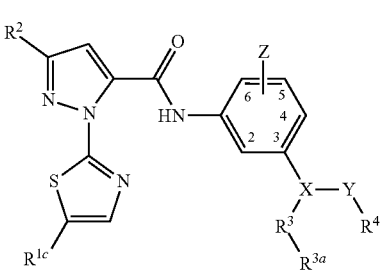

(XIII)

wherein:
X represents CH, C(OH), C(O($C_1$-$C_6$)alkyl), C(O)N, $CH_2$N, N, C(O), or —O—;
—Y—$R^4$, when present, represents —(($C_1$-$C_6$)alkyl)-$R^4$, —$CH_2$C(O)—$R^4$, —$CH_2$NH—$R^4$, —$CH_2$N(($C_1$-$C_6$)alkyl)-$R^4$, —$CR^aR^b$—$R^4$, —NH—$R^4$, —NHCH$_2$—$R^4$, —NHC(O)—$R^4$, —N(($C_1$-$C_6$)alkyl)-$R^4$, —N(($C_1$-$C_6$)alkyl)CH$_2$—$R^4$, —N(($CH_2$)$_2$OH)—$R^4$, —N[($C_3$-$C_8$)cycloalkyl($C_1$-$C_6$)alkyl]$R^4$, -heterocyclyl-$R^4$, —O$R^4$, —OCH$_2$—$R^4$, —OC(O)—$R^4$, —OC(O)NR$^a$R$^b$, —SCH$_2$R$^4$, or —SR$^4$, wherein the ($C_1$-$C_6$)alkyl moiety of —(($C_1$-$C_6$)alkyl)-$R^4$ is optionally substituted;
Z is absent or represents halo, hydroxy, ($C_1$-$C_6$)alkyl, —CF$_3$, —OCF$_3$, ($C_1$-$C_6$)alkoxy, aryl, aryloxy, amino, amino($C_1$-$C_6$)alkyl, —C(O)NH$_2$, cyano, —NHC(O)($C_1$-$C_6$)alkyl, —SO$_2$($C_1$-$C_6$)alkyl, —SO$_2$NH$_2$, or ($C_3$-$C_8$)cycloalkyl;

$R^{1c}$ represents halo, amino($C_1$-$C_6$)alkyl, ($C_1$-$C_6$)alkoxy, cyano, —SO$_2$CH$_3$, formyl, acyl, or optionally substituted aryl;

$R^{3a}$ is absent or represents one or more substituents independently selected from the group consisting of halo, hydroxy, ($C_1$-$C_6$)alkyl, —CF$_3$, —OCF$_3$, ($C_1$-$C_6$)alkoxy, aryl, aryloxy, amino, amino($C_1$-$C_6$)alkyl, —C(O)NH$_2$, cyano, —NHC(O)($C_1$-$C_6$)alkyl, —SO$_2$($C_1$-$C_6$)alkyl, and —SO$_2$NH$_2$;

$R^4$ represents hydrogen, hydroxy, optionally substituted ($C_1$-$C_6$)alkyl, optionally substituted ($C_3$-$C_8$)cycloalkyl, heterocyclyl($C_1$-$C_6$)alkyl, ($C_3$-$C_8$)cycloalkyl($C_1$-$C_6$)alkyl, —CH$_2$OH, —CH(($C_1$-$C_6$)alkyl)OH, —CH(NH$_2$)CH(($C_1$-$C_6$)alkyl)$_2$, optionally substituted aryl, optionally substituted aryl($C_1$-$C_6$)alkyl, heteroaryl, optionally substituted heteroaryl($C_1$-$C_6$)alkyl, —CH$_2$S($C_1$-$C_6$)alkyl, amino, or cyano; or —CH$_2$— fused to the 4-position of the ring bearing Z to form a 5- to 7-membered heterocyclic ring with optional substituents;

or, when $R^3$ is phenyl, can represent —NH— fused to the position ortho to X on that phenyl; and

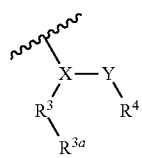

can represent

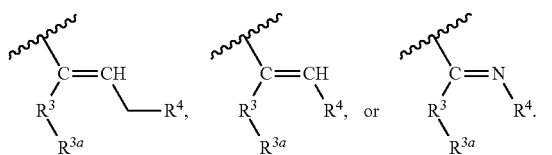

In certain embodiments, the compound is represented by formula XIV:

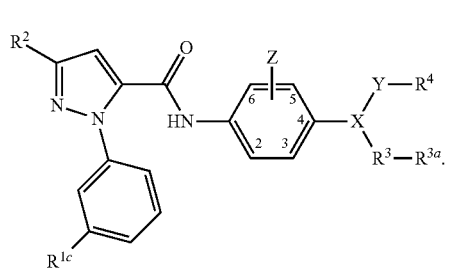

(XIV)

In certain embodiments, the compound is represented by formula XV:

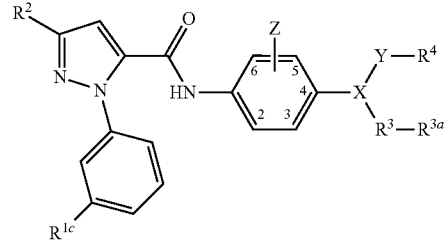

(XV)

wherein:

X represents CH, C(OH), C(O($C_1$-$C_6$)alkyl), C(O)N, CH$_2$N, N, C(O), or —O—;

—Y—$R^4$, when present, represents —(($C_1$-$C_6$)alkyl)-$R^4$, —CH$_2$C(O)—$R^4$, —CH$_2$NH—$R^4$, —CH$_2$N(($C_1$-$C_6$)alkyl)-$R^4$, —CR$^a$R$^b$—$R^4$, —NH—$R^4$, —NHCH$_2$—$R^4$, —NHC(O)—$R^4$, —N(($C_1$-$C_6$)alkyl)-$R^4$, —N(($C_1$-$C_6$)alkyl)CH$_2$—$R^4$, —N((CH$_2$)$_2$OH)—$R^4$, —N[($C_3$-$C_8$)cycloalkyl($C_1$-$C_6$)alkyl]$R^4$, -heterocyclyl-$R^4$, —OR$^4$, —OCH$_2$—$R^4$, —OC(O)—$R^4$, —OC(O)NR$^a$R$^b$, —SCH$_2$R$^4$, or —SR$^4$, wherein the ($C_1$-$C_6$)alkyl moiety of —(($C_1$-$C_6$)alkyl)-$R^4$ is optionally substituted;

Z is absent or represents halo, hydroxy, ($C_1$-$C_6$)alkyl, —CF$_3$, —OCF$_3$, ($C_1$-$C_6$)alkoxy, aryl, aryloxy, amino, amino($C_1$-$C_6$)alkyl, —C(O)NH$_2$, cyano, —NHC(O)($C_1$-$C_6$)alkyl, —SO$_2$($C_1$-$C_6$)alkyl, —SO$_2$NH$_2$, or ($C_3$-$C_8$)cycloalkyl;

$R^{1c}$ represents halo, amino($C_1$-$C_6$)alkyl, ($C_1$-$C_6$)alkoxy, cyano, —SO$_2$CH$_3$, formyl, acyl, or optionally substituted aryl;

$R^{3a}$ is absent or represents one or more substituents independently selected from the group consisting of halo, hydroxy, ($C_1$-$C_6$)alkyl, —CF$_3$, —OCF$_3$, ($C_1$-$C_6$)alkoxy, aryl, aryloxy, amino, amino($C_1$-$C_6$)alkyl, —C(O)NH$_2$, cyano, —NHC(O)($C_1$-$C_6$)alkyl, —SO$_2$($C_1$-$C_6$)alkyl, and —SO$_2$NH$_2$;

$R^4$ represents hydrogen, hydroxy, optionally substituted ($C_1$-$C_6$)alkyl, optionally substituted ($C_3$-$C_8$)cycloalkyl, heterocyclyl($C_1$-$C_6$)alkyl, ($C_3$-$C_8$)cycloalkyl($C_1$-$C_6$)alkyl, —CH$_2$OH, —CH(($C_1$-$C_6$)alkyl)OH, —CH(NH$_2$)CH(($C_1$-$C_6$)alkyl)$_2$, optionally substituted aryl, optionally substituted aryl($C_1$-$C_6$)alkyl, heteroaryl, optionally substituted heteroaryl($C_1$-$C_6$)alkyl, —CH$_2$S($C_1$-$C_6$)alkyl, amino, or cyano; or —CH$_2$— fused to the 4-position of the ring bearing Z to form a 5- to 7-membered heterocyclic ring with optional substituents;

or, when $R^3$ is phenyl, can represent —NH— fused to the position ortho to X on that phenyl; and

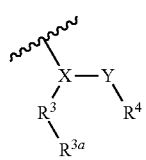

can represent

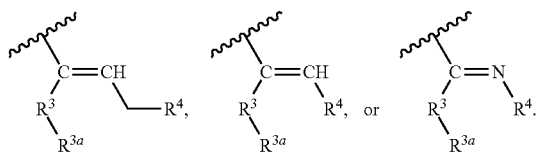

In certain embodiments, the compound is represented by formula XVI:

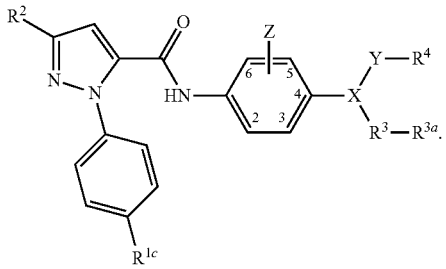

(XVI)

In certain embodiments, the compound is represented by formula XVII:

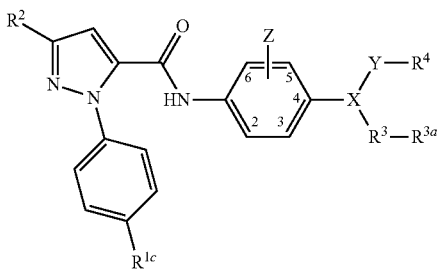

(XVII)

wherein:
X represents CH, C(OH), C(O($C_1$-$C_6$)alkyl), C(O)N, $CH_2$N, N, C(O), or —O—;
—Y—$R^4$, when present, represents —(($C_1$-$C_6$)alkyl)-$R^4$, —$CH_2$C(O)—$R^4$, —$CH_2$NH—$R^4$, —$CH_2$N(($C_1$-$C_6$)alkyl)-$R^4$, —$CR^aR^b$—$R^4$, —NH—$R^4$, —NH$CH_2$—$R^4$, —NHC(O)—$R^4$, —N(($C_1$-$C_6$)alkyl)-$R^4$, —N(($C_1$-$C_6$)alkyl)$CH_2$—$R^4$, —N(($CH_2$)$_2$OH)—$R^4$, —N[($C_3$-$C_8$)cycloalkyl($C_1$-$C_6$)alkyl]$R^4$, -heterocyclyl-$R^4$, —O$R^4$, —O$CH_2$—$R^4$, —OC(O)—$R^4$, —OC(O)N$R^aR^b$, —S$CH_2R^4$, or —S$R^4$, wherein the ($C_1$-$C_6$)alkyl moiety of —(($C_1$-$C_6$)alkyl)-$R^4$ is optionally substituted;
Z is absent or represents halo, hydroxy, ($C_1$-$C_6$)alkyl, —$CF_3$, —$OCF_3$, ($C_1$-$C_6$)alkoxy, aryl, aryloxy, amino, amino($C_1$-$C_6$)alkyl, —C(O)$NH_2$, cyano, —NHC(O)($C_1$-$C_6$)alkyl, —$SO_2$($C_1$-$C_6$)alkyl, —$SO_2NH_2$, or ($C_3$-$C_8$)cycloalkyl;
$R^{1c}$ represents halo, amino($C_1$-$C_6$)alkyl, ($C_1$-$C_6$)alkoxy, cyano, —$SO_2CH_3$, formyl, acyl, or optionally substituted aryl; and
$R^{3a}$ is absent or represents one or more substituents independently selected from the group consisting of halo, hydroxy, ($C_1$-$C_6$)alkyl, —$CF_3$, —$OCF_3$, ($C_1$-$C_6$)alkoxy, aryl, aryloxy, amino, amino($C_1$-$C_6$)alkyl, —C(O)$NH_2$, cyano, —NHC(O)($C_1$-$C_6$)alkyl, —$SO_2$($C_1$-$C_6$)alkyl, and —$SO_2NH_2$;

$R^4$ represents hydrogen, hydroxy, optionally substituted ($C_1$-$C_6$)alkyl, optionally substituted ($C_3$-$C_8$)cycloalkyl, heterocyclyl($C_1$-$C_6$)alkyl, ($C_3$-$C_8$)cycloalkyl($C_1$-$C_6$)alkyl, —$CH_2$OH, —CH(($C_1$-$C_6$)alkyl)OH, —CH($NH_2$)CH(($C_1$-$C_6$)alkyl)$_2$, optionally substituted aryl, optionally substituted aryl($C_1$-$C_6$)alkyl, heteroaryl, optionally substituted heteroaryl($C_1$-$C_6$)alkyl, —$CH_2$S($C_1$-$C_6$)alkyl, amino, or cyano; or —$CH_2$— fused to the 4-position of the ring bearing Z to form a 5- to 7-membered heterocyclic ring with optional substituents;
or, when $R^3$ is phenyl, can represent —NH— fused to the position ortho to X on that phenyl; and

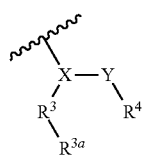

can represent

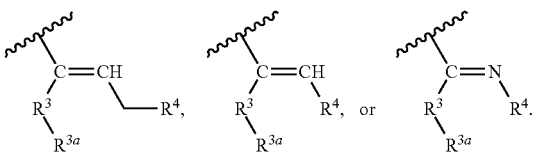

the stereochemical configuration at any chiral center is R, S, or a mixture of R and S.

In certain embodiments, the compound is represented by formula XVIII:

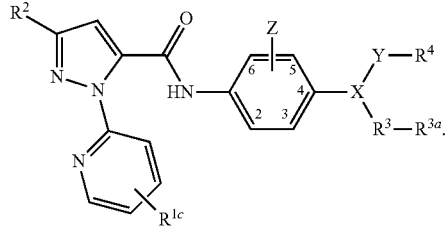

(XVIII)

In certain embodiments, the compound is represented by formula XIX:

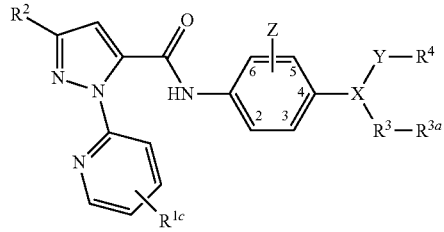

(XIX)

wherein:
X represents CH, C(OH), C(O($C_1$-$C_6$)alkyl), C(O)N, $CH_2$N, N, C(O), or —O—;

—Y—R⁴, when present, represents —((C₁-C₆)alkyl)-R⁴, —CH₂C(O)—R⁴, —CH₂NH—R⁴, —CH₂N((C₁-C₆)alkyl)-R⁴, —CRᵃRᵇ—R⁴, —NH—R⁴, —NHCH₂—R⁴, —NHC(O)—R⁴, —N((C₁-C₆)alkyl)-R⁴, —N((C₁-C₆)alkyl)CH₂—R⁴, —N((CH₂)₂OH)—R⁴, —N[(C₃-C₈)cycloalkyl(C₁-C₆)alkyl]R⁴, -heterocyclyl-R⁴, —OR⁴, —OCH₂—R⁴, —OC(O)—R⁴, —OC(O)NRᵃRᵇ, —SCH₂R⁴, or —SR⁴, wherein the (C₁-C₆)alkyl moiety of —((C₁-C₆)alkyl)-R⁴ is optionally substituted;

Z is absent or represents halo, hydroxy, (C₁-C₆)alkyl, —CF₃, —OCF₃, (C₁-C₆)alkoxy, aryl, aryloxy, amino, amino(C₁-C₆)alkyl, —C(O)NH₂, cyano, —NHC(O)(C₁-C₆)alkyl, —SO₂(C₁-C₆)alkyl, —SO₂NH₂, or (C₃-C₈)cycloalkyl;

R¹ᶜ represents halo, amino(C₁-C₆)alkyl, (C₁-C₆)alkoxy, cyano, —SO₂CH₃, formyl, acyl, or optionally substituted aryl; and R³ᵃ is absent or represents one or more substituents independently selected from the group consisting of halo, hydroxy, (C₁-C₆)alkyl, —CF₃, —OCF₃, (C₁-C₆)alkoxy, aryl, aryloxy, amino, amino(C₁-C₆)alkyl, —C(O)NH₂, cyano, —NHC(O)(C₁-C₆)alkyl, —SO₂(C₁-C₆)alkyl, and —SO₂NH₂;

R⁴ represents hydrogen, hydroxy, optionally substituted (C₁-C₆)alkyl, optionally substituted (C₃-C₈)cycloalkyl, heterocyclyl(C₁-C₆)alkyl, (C₃-C₈)cycloalkyl(C₁-C₆)alkyl, —CH₂OH, —CH((C₁-C₆)alkyl)OH, —CH(NH₂)CH((C₁-C₆)alkyl)₂, optionally substituted aryl, optionally substituted aryl(C₁-C₆)alkyl, heteroaryl, optionally substituted heteroaryl(C₁-C₆)alkyl, —CH₂S(C₁-C₆)alkyl, amino, or cyano; or —CH₂— fused to the 4-position of the ring bearing Z to form a 5- to 7-membered heterocyclic ring with optional substituents;

or, when R³ is phenyl, can represent —NH— fused to the position ortho to X on that phenyl; and

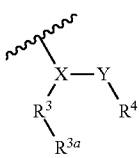

can represent

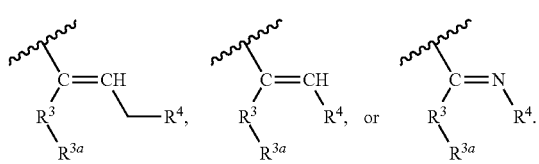

In certain embodiments, the compound is represented by formula XX:

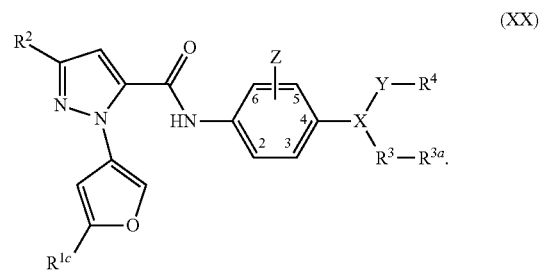

In certain embodiments, the compound is represented by formula XXI:

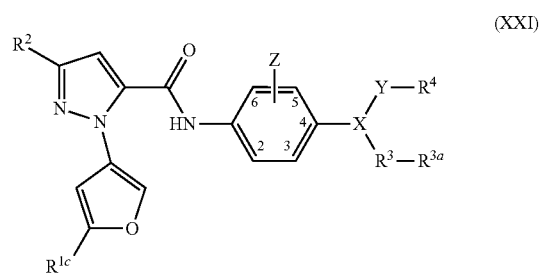

wherein:

X represents CH, C(OH), C(O(C₁-C₆)alkyl), C(O)N, CH₂N, N, C(O), or —O—;

—Y—R⁴, when present, represents —((C₁-C₆)alkyl)-R⁴, —CH₂C(O)—R⁴, —CH₂NH—R⁴, —CH₂N((C₁-C₆)alkyl)-R⁴, —CRᵃRᵇ—R⁴, —NH—R⁴, —NHCH₂—R⁴, —NHC(O)—R⁴, —N((C₁-C₆)alkyl)-R⁴, —N((C₁-C₆)alkyl)CH₂—R⁴, —N((CH₂)₂OH)—R⁴, —N[(C₃-C₈)cycloalkyl(C₁-C₆)alkyl]R⁴, -heterocyclyl-R⁴, —OR⁴, —OCH₂—R⁴, —OC(O)—R⁴, —OC(O)NRᵃRᵇ, —SCH₂R⁴, or —SR⁴, wherein the (C₁-C₆)alkyl moiety of —((C₁-C₆)alkyl)-R⁴ is optionally substituted;

Z is absent or represents halo, hydroxy, (C₁-C₆)alkyl, —CF₃, —OCF₃, (C₁-C₆)alkoxy, aryl, aryloxy, amino, amino(C₁-C₆)alkyl, —C(O)NH₂, cyano, —NHC(O)(C₁-C₆)alkyl, —SO₂(C₁-C₆)alkyl, —SO₂NH₂, or (C₃-C₈)cycloalkyl;

R¹ᶜ represents halo, amino(C₁-C₆)alkyl, (C₁-C₆)alkoxy, cyano, —SO₂CH₃, formyl, acyl, or optionally substituted aryl; and R³ᵃ is absent or represents one or more substituents independently selected from the group consisting of halo, hydroxy, (C₁-C₆)alkyl, —CF₃, —OCF₃, (C₁-C₆)alkoxy, aryl, aryloxy, amino, amino(C₁-C₆)alkyl, —C(O)NH₂, cyano, —NHC(O)(C₁-C₆)alkyl, —SO₂(C₁-C₆)alkyl, and —SO₂NH₂;

R⁴ represents hydrogen, hydroxy, optionally substituted (C₁-C₆)alkyl, optionally substituted (C₃-C₈)cycloalkyl, heterocyclyl(C₁-C₆)alkyl, (C₃-C₈)cycloalkyl(C₁-C₆)alkyl, —CH₂OH, —CH((C₁-C₆)alkyl)OH, —CH(NH₂)CH((C₁-C₆)alkyl)₂, optionally substituted aryl, optionally substituted aryl(C₁-C₆)alkyl, heteroaryl, optionally substituted heteroaryl(C₁-C₆)alkyl, —CH₂S(C₁-C₆)alkyl, amino, or cyano; or —CH₂— fused to the 4-position of the ring bearing Z to form a 5- to 7-membered heterocyclic ring with optional substituents;

or, when R³ is phenyl, can represent —NH— fused to the position ortho to X on that phenyl; and

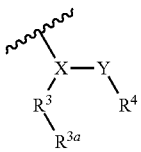

can represent

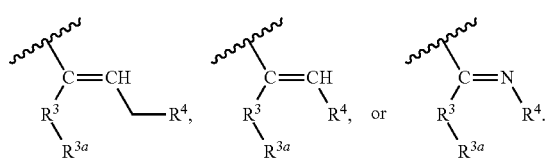

In certain embodiments, the compound is represented by formula XXII:

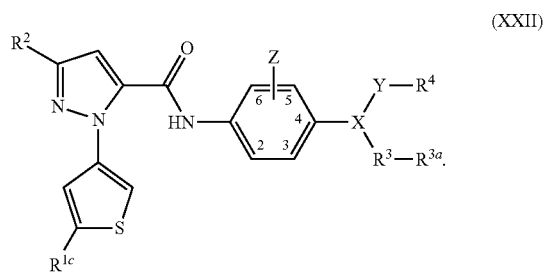

(XXII)

In certain embodiments, the compound is represented by formula XXIII:

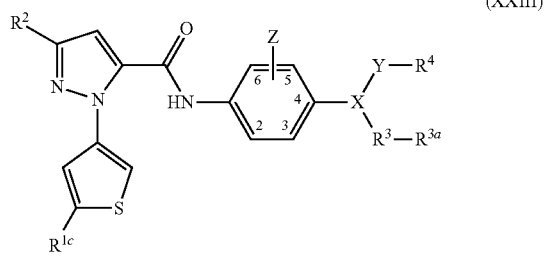

(XXIII)

wherein:
X represents CH, C(OH), C(O(C₁-C₆)alkyl), C(O)N, CH₂N, N, C(O), or —O—;
—Y—R⁴, when present, represents —((C₁-C₆)alkyl)-R⁴, —CH₂C(O)—R⁴, —CH₂NH—R⁴, —CH₂N((C₁-C₆)alkyl)-R⁴, —CRᵃRᵇ—R⁴, —NH—R⁴, —NHCH₂—R⁴, —NHC(O)—R⁴, —N((C₁-C₆)alkyl)-R⁴, —N((C₁-C₆)alkyl)CH₂—R⁴, —N((CH₂)₂OH)—R⁴, —N[(C₃-C₈)cycloalkyl(C₁-C₆)alkyl]R⁴, -heterocyclyl-R⁴, —OR⁴, —OCH₂—R⁴, —OC(O)—R⁴, —OC(O)NRᵃRᵇ, —SCH₂R⁴, or —SR⁴, wherein the (C₁-C₆)alkyl moiety of —((C₁-C₆)alkyl)-R⁴ is optionally substituted;
Z is absent or represents halo, hydroxy, (C₁-C₆)alkyl, —CF₃, —OCF₃, (C₁-C₆)alkoxy, aryl, aryloxy, amino, amino(C₁-C₆)alkyl, —C(O)NH₂, cyano, —NHC(O)(C₁-C₆)alkyl, —SO₂(C₁-C₆)alkyl, —SO₂NH₂, or (C₃-C₈)cycloalkyl;
R¹ᶜ represents halo, amino(C₁-C₆)alkyl, (C₁-C₆)alkoxy, cyano, —SO₂CH₃, formyl, acyl, or optionally substituted aryl; and
R³ᵃ is absent or represents one or more substituents independently selected from the group consisting of halo, hydroxy, (C₁-C₆)alkyl, —CF₃, —OCF₃, (C₁-C₆)alkoxy, aryl, aryloxy, amino, amino(C₁-C₆)alkyl, —C(O)NH₂, cyano, —NHC(O)(C₁-C₆)alkyl, —SO₂(C₁-C₆)alkyl, and —SO₂NH₂;
R⁴ represents hydrogen, hydroxy, optionally substituted (C₁-C₆)alkyl, optionally substituted (C₃-C₈)cycloalkyl, heterocyclyl(C₁-C₆)alkyl, (C₃-C₈)cycloalkyl(C₁-C₆)alkyl, —CH₂OH, —CH((C₁-C₆)alkyl)OH, —CH(NH₂)CH((C₁-C₆)alkyl)₂, optionally substituted aryl, optionally substituted aryl(C₁-C₆)alkyl, heteroaryl, optionally substituted heteroaryl(C₁-C₆)alkyl, —CH₂S(C₁-C₆)alkyl, amino, or cyano; or —CH₂— fused to the 4-position of the ring bearing Z to form a 5- to 7-membered heterocyclic ring with optional substituents;
or, when R³ is phenyl, can represent —NH— fused to the position ortho to X on that phenyl; and

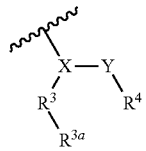

can represent

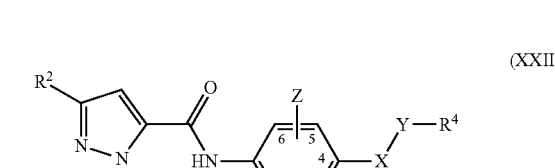

In certain embodiments, the compound is represented by formula XXIV:

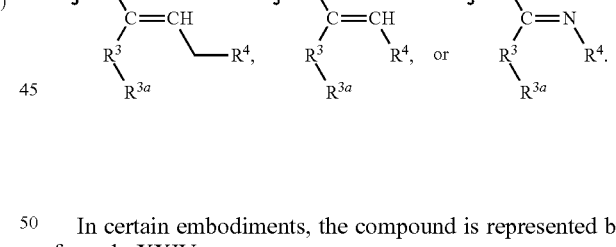

(XXIV)

In certain embodiments, the compound is represented by formula XXV:

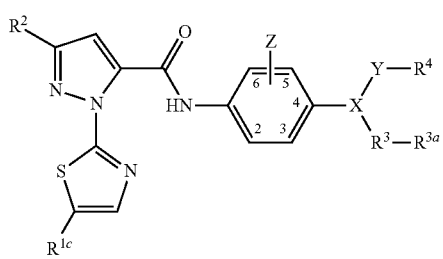

(XXV)

wherein:
X represents CH, C(OH), C(O(C$_1$-C$_6$)alkyl), C(O)N, CH$_2$N, N, C(O), or —O—;

—Y—R$^4$, when present, represents —((C$_1$-C$_6$)alkyl)-R$^4$, —CH$_2$C(O)—R$^4$, —CH$_2$NH—R$^4$, —CH$_2$N((C$_1$-C$_6$)alkyl)-R$^4$, —CR$^a$R$^b$—R$^4$, —NH—R$^4$, —NHCH$_2$—R$^4$, —NHC(O)—R$^4$, —N((C$_1$-C$_6$)alkyl)-R$^4$, —N((C$_1$-C$_6$)alkyl)CH$_2$—R$^4$, —N((CH$_2$)$_2$OH)—R$^4$, —N[(C$_3$-C$_8$)cycloalkyl(C$_1$-C$_6$)alkyl]R$^4$, -heterocyclyl-R$^4$, —OR$^4$, —OCH$_2$—R$^4$, —OC(O)—R$^4$, —OC(O)NR$^a$R$^b$, —SCH$_2$R$^4$, or —SR$^4$, wherein the (C$_1$-C$_6$)alkyl moiety of —((C$_1$-C$_6$)alkyl)-R$^4$ is optionally substituted;

Z is absent or represents halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, —SO$_2$NH$_2$, or (C$_3$-C$_8$)cycloalkyl;

R$^{1c}$ represents halo, amino(C$_1$-C$_6$)alkyl, (C$_1$-C$_6$)alkoxy, cyano, —SO$_2$CH$_3$, formyl, acyl, or optionally substituted aryl;

R$^{3a}$ is absent or represents one or more substituents independently selected from the group consisting of halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, and —SO$_2$NH$_2$;

R$^4$ represents hydrogen, hydroxy, optionally substituted (C$_1$-C$_6$)alkyl, optionally substituted (C$_3$-C$_8$)cycloalkyl, heterocyclyl(C$_1$-C$_6$)alkyl, (C$_3$-C$_8$)cycloalkyl(C$_1$-C$_6$)alkyl, —CH$_2$OH, —CH((C$_1$-C$_6$)alkyl)OH, —CH(NH$_2$)CH((C$_1$-C$_6$)alkyl)$_2$, optionally substituted aryl, optionally substituted aryl(C$_1$-C$_6$)alkyl, heteroaryl, optionally substituted heteroaryl(C$_1$-C$_6$)alkyl, —CH$_2$S(C$_1$-C$_6$)alkyl, amino, or cyano; or —CH$_2$— fused to the 4-position of the ring bearing Z to form a 5- to 7-membered heterocyclic ring with optional substituents;

or, when R$^3$ is phenyl, can represent —NH— fused to the position ortho to X on that phenyl; and

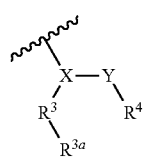

can represent

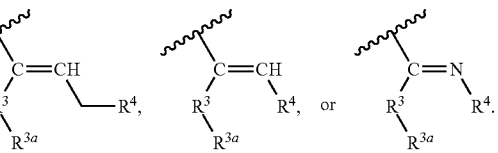

In other embodiments, the compound is represented by formula XXVI:

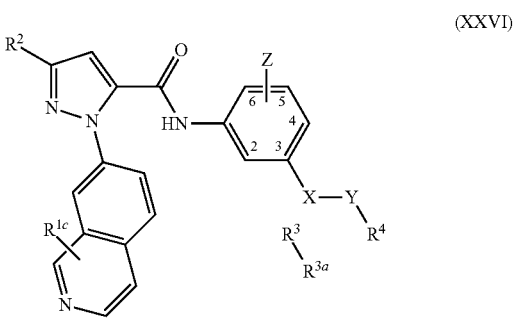

(XXVI)

wherein:
X represents CH, C(OH), —C(NH$_2$), or —C(NR$^a$R$^b$);

—Y—R$^4$, when present, represents —((C$_1$-C$_6$)alkyl)-R$^4$, —CH$_2$C(O)—R$^4$, —CH$_2$NH—R$^4$, —CH$_2$N((C$_1$-C$_6$)alkyl)-R$^4$, —CR$^a$R$^b$—R$^4$, —NH—R$^4$, —NHCH$_2$—R$^4$, —NHC(O)—R$^4$, —N((C$_1$-C$_6$)alkyl)-R$^4$, —N((C$_1$-C$_6$)alkyl)CH$_2$—R$^4$, —N((CH$_2$)$_2$OH)—R$^4$, —N[(C$_3$-C$_8$)cycloalkyl(C$_1$-C$_6$)alkyl]R$^4$, -heterocyclyl-R$^4$, —OR$^4$, —OCH$_2$—R$^4$, —OC(O)—R$^4$, —OC(O)NR$^a$R$^b$, —SCH$_2$R$^4$, or —SR$^4$, wherein the (C$_1$-C$_6$)alkyl moiety of —((C$_1$-C$_6$)alkyl)-R$^4$ is optionally substituted;

Z is absent or represents halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, —SO$_2$NH$_2$, or (C$_3$-C$_8$)cycloalkyl;

R$^{1c}$ represents halo, amino(C$_1$-C$_6$)alkyl, (C$_1$-C$_6$)alkoxy, cyano, —SO$_2$CH$_3$, formyl, acyl, —NH$_2$, or optionally substituted aryl;

R$^{3a}$ is absent or represents one or more substituents independently selected from the group consisting of halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, and —SO$_2$NH$_2$; and R$^4$ represents hydrogen, hydroxy, optionally substituted (C$_1$-C$_6$)alkyl, optionally substituted (C$_3$-C$_8$)cycloalkyl, heterocyclyl(C$_1$-C$_6$)alkyl, (C$_3$-C$_8$)cycloalkyl(C$_1$-C$_6$)alkyl, —CH$_2$OH, —CH((C$_1$-C$_6$)alkyl)OH, —CH(NH$_2$)CH((C$_1$-C$_6$)alkyl)$_2$, optionally substituted aryl, optionally substituted aryl(C$_1$-C$_6$)alkyl, heteroaryl, optionally substituted heteroaryl(C$_1$-C$_6$)alkyl, —CH$_2$S(C$_1$-C$_6$)alkyl, amino, or cyano; or —CH$_2$— fused to the 4-position of the ring bearing Z to form a 5- to 7-membered heterocyclic ring with optional substituents;

or, when R$^3$ is phenyl, can represent —NH— fused to the position ortho to X on that phenyl.

In certain aspects, the invention provides a pharmaceutical composition, comprising a compound of the invention, or a pharmaceutically acceptable salt thereof; and a pharmaceutically acceptable carrier.

In certain aspects, the invention provides a method of treating or preventing a disease or condition characterized by unwanted plasma kallikrein activity. The method comprises the step of administering to a subject in need thereof a therapeutically effective amount of a compound of the invention, or a pharmaceutically acceptable salt thereof, thereby treating or preventing the disease or condition characterized by unwanted plasma kallikrein activity. In one embodiment, the disease or condition characterized by unwanted plasma kallikrein activity is selected from the group consisting of stroke, inflammation, reperfusion injury, acute myocardial infarction, deep vein thrombosis, post fibrinolytic treatment condition, angina, edema, angioedema, hereditary angioedema, sepsis, arthritis, hemorrhage, blood loss during cardiopulmonary bypass, inflammatory bowel disease, diabetes mellitus, retinopathy, diabetic retinopathy, diabetic macular edema, diabetic macular degeneration, age-related macular edema, age-related macular degeneration, proliferative retinopathy, neuropathy, hypertension, brain edema, increased albumin excretion, macroalbuminuria, and nephropathy.

DETAILED DESCRIPTION

Inhibitors of plasma kallikrein have been reported and are useful in therapeutic methods and compositions suitable for use in eliminating or reducing various forms of ischemia, including but not limited to perioperative blood loss, cerebral ischemia, the onset of systemic inflammatory response, and/or reperfusion injury, e.g., reperfusion injury associated with cerebral ischemia or a focal brain ischemia. Perioperative blood loss results from invasive surgical procedures that lead to contact activation of complement components and the coagulation/fibrinolysis systems.

Kallikrein inhibitors can be used to reduce or prevent perioperative blood loss and a systemic inflammatory response in patients subjected to invasive surgical procedures, especially cardiothoracic surgeries. Kallikrein inhibitors can also be used to reduce or prevent cerebral ischemia and stroke, and/or reperfusion injury associated with cerebral ischemia. They can also prevent neurological and cognitive deficits associated with stroke, blood loss, and cerebral ischemia, e.g., events that are not associated with surgical intervention. Further examples of applications for kallikrein inhibitors include pediatric cardiac surgery, lung transplantation, total hip replacement, and orthotopic liver transplantation, to reduce or prevent stroke during these procedures, as well as to reduce or prevent stroke during coronary artery bypass grafting (CABG) and extracorporeal membrane oxygenation (ECMO).

Definitions

The term "alkyl" as used herein is a term of art and refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight-chain or branched-chain alkyl has about 30 or fewer carbon atoms in its backbone (e.g., $C_1$-$C_{30}$ for straight chain, $C_3$-$C_{30}$ for branched chain), and alternatively, about 20 or fewer. In one embodiment, the term "alkyl" refers to a $C_1$-$C_{10}$ straight-chain alkyl group. In one embodiment, the term "alkyl" refers to a $C_1$-$C_6$ straight-chain alkyl group. In one embodiment, the term "alkyl" refers to a $C_3$-$C_{12}$ branched-chain alkyl group. In one embodiment, the term "alkyl" refers to a $C_3$-$C_8$ branched-chain alkyl group. Cycloalkyls have from about 3 to about 10 carbon atoms in their ring structure, and alternatively about 5, 6, or 7 carbons in the ring structure.

The term "heterocyclyl" as used herein refers to a radical of a non-aromatic ring system, including, but not limited to, monocyclic, bicyclic, and tricyclic rings, which can be completely saturated or which can contain one or more units of unsaturation, for the avoidance of doubt, the degree of unsaturation does not result in an aromatic ring system, and having 3 to 12 atoms including at least one heteroatom, such as nitrogen, oxygen, or sulfur. For purposes of exemplification, which should not be construed as limiting the scope of this invention, the following are examples of heterocyclic rings: aziridinyl, azirinyl, oxiranyl, thiiranyl, thiirenyl, dioxiranyl, diazirinyl, azetyl, oxetanyl, oxetyl, thietanyl, thietyl, diazetidinyl, dioxetanyl, dioxetenyl, dithietanyl, dithietyl, furyl, dioxalanyl, pyrrolyl, oxazolyl, thiazolyl, imidazolyl, oxadiazolyl, thiadiazolyl, triazolyl, triazinyl, isothiazolyl, isoxazolyl, thiophenyl, pyrazolyl, tetrazolyl, pyridyl, pyridazinyl, pyrimidinyl, pyrazinyl, triazinyl, tetrazinyl, quinolinyl, isoquinolinyl, quinoxalinyl, quinazolinyl, pyridopyrazinyl, benzoxazolyl, benzothiophenyl, benzimidazolyl, benzothiazolyl, benzoxadiazolyl, benzthiadiazolyl, indolyl, benztriazolyl, naphthyridinyl, azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl.

The term "heteroatom" is art-recognized, and includes an atom of any element other than carbon or hydrogen. Illustrative heteroatoms include boron, nitrogen, oxygen, phosphorus, sulfur and selenium, and alternatively oxygen, nitrogen or sulfur.

The term "cycloalkylalkyl" as used herein refers to an alkyl group substituted with one or more cycloalkyl groups.

The term "heterocycloalkylalkyl" as used herein refers to an alkyl group substituted with one or more heterocycloalkyl (i.e., heterocyclyl) groups.

The term "alkenyl" as used herein means a straight or branched chain hydrocarbon radical containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein means a straight or branched chain hydrocarbon radical containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "alkylene" is art-recognized, and as used herein pertains to a diradical obtained by removing two hydrogen atoms of an alkyl group, as defined above. In one embodiment an alkylene refers to a disubstituted alkane, i.e., an alkane substituted at two positions with substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. That is, in one embodiment, a "substituted alkyl" is an "alkylene".

The term "amino" is a term of art and as used herein refers to both unsubstituted and substituted amines, e.g., a moiety that may be represented by the general formulas:

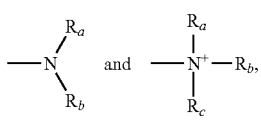

wherein $R_a$, $R_b$, and $R_c$ each independently represent a hydrogen, an alkyl, an alkenyl, —$(CH_2)_x$—$R_d$, or $R_a$ and $R_b$, taken together with the N atom to which they are attached complete a heterocycle having from 4 to 8 atoms in the ring structure; $R_d$ represents an aryl, a cycloalkyl, a cycloalkenyl, a heterocyclyl or a polycyclyl; and x is zero or an integer in the range of 1 to 8. In certain embodiments, only one of $R_a$ or $R_b$ may be a carbonyl, e.g., $R_a$, $R_b$, and the nitrogen together do not form an imide. In other embodiments, $R_a$ and $R_b$ (and optionally $R_c$) each independently represent a hydrogen, an alkyl, an alkenyl, or —$(CH_2)_x$—$R_d$. In one embodiment, the term "amino" refers to —$NH_2$.

The term "acyl" is a term of art and as used herein refers to any group or radical of the form RCO— where R is any organic group, e.g., alkyl, aryl, heteroaryl, aralkyl, and heteroaralkyl. Representative acyl groups include acetyl, benzoyl, and malonyl.

The term "aminoalkyl" as used herein refers to an alkyl group substituted with one or more one amino groups. In one embodiment, the term "aminoalkyl" refers to an aminomethyl group.

The term "aminoacyl" is a term of art and as used herein refers to an acyl group substituted with one or more amino groups.

The term "aminothionyl" as used herein refers to an analog of an aminoacyl in which the O of RC(O)— has been replaced by sulfur, hence is of the form RC(S)—.

The term "phosphoryl" is a term of art and as used herein may in general be represented by the formula:

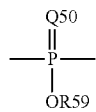

wherein Q50 represents S or O, and R59 represents hydrogen, a lower alkyl or an aryl; for example, —P(O)(OMe)- or —P(O)(OH)$_2$. When used to substitute, e.g., an alkyl, the phosphoryl group of the phosphorylalkyl may be represented by the general formulas:

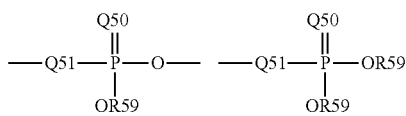

wherein Q50 and R59, each independently, are defined above, and Q51 represents O, S or N; for example, —O—P(O)(OH)OMe or —NH—P(O)(OH)$_2$. When Q50 is S, the phosphoryl moiety is a "phosphorothioate."

The term "aminophosphoryl" as used herein refers to a phosphoryl group substituted with at least one amino group, as defined herein; for example, —P(O)(OH)NMe$_2$.

The term "carbonyl" as used herein refers to —C(O)—.

The term "thiocarbonyl" as used herein refers to —C(S)—.

The term "alkylphosphoryl" as used herein refers to a phosphoryl group substituted with at least one alkyl group, as defined herein; for example, —P(O)(OH)Me.

The term "alkylthio" as used herein refers to alkyl-S—.

The term "aryl" is a term of art and as used herein refers to includes monocyclic, bicyclic and polycyclic aromatic hydrocarbon groups, for example, benzene, naphthalene, anthracene, and pyrene. The aromatic ring may be substituted at one or more ring positions with one or more substituents, such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "aryl" also includes polycyclic ring systems having two or more cyclic rings in which two or more carbons are common to two adjoining rings (the rings are "fused rings") wherein at least one of the rings is an aromatic hydrocarbon, e.g., the other cyclic rings may be cycloalkyls, cycloalkenyls, cycloalkynyls, aryls, heteroaryls, and/or heterocyclyls. In one embodiment, the term "aryl" refers to a phenyl group.

The term "heteroaryl" is a term of art and as used herein refers to a monocyclic, bicyclic, and polycyclic aromatic group having one or more heteroatoms in the ring structure, for example, pyrrole, furan, thiophene, imidazole, oxazole, thiazole, triazole, pyrazole, pyridine, pyrazine, pyridazine and pyrimidine, and the like. The "heteroaryl" may be substituted at one or more ring positions with one or more substituents such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. The term "heteroaryl" also includes polycyclic ring systems having two or more cyclic rings in which two or more carbons are common to two adjoining rings (the rings are "fused rings") wherein at least one of the rings is an aromatic group having one or more heteroatoms in the ring structure, e.g., the other cyclic rings may be cycloalkyls, cycloalkenyls, cycloalkynyls, aryls, heteroaryls, and/or heterocyclyls.

The term "aralkyl" or "arylalkyl" is a term of art and as used herein refers to an alkyl group substituted with an aryl group.

The term "heteroaralkyl" or "heteroarylalkyl" is a term of art and as used herein refers to an alkyl group substituted with a heteroaryl group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "aryloxy" as used herein means an aryl group, as defined herein, appended to the parent molecular moiety through an oxygen atom.

The term "heteroaryloxy" as used herein means a heteroaryl group, as defined herein, appended to the parent molecular moiety through an oxygen atom.

The term "carbocyclyl" as used herein means a monocyclic or multicyclic (e.g., bicyclic, tricyclic, etc.) hydrocarbon radical containing from 3 to 12 carbon atoms that is completely saturated or has one or more unsaturated bonds, and for the avoidance of doubt, the degree of unsaturation does not result in an aromatic ring system (e.g., phenyl).

Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "cyano" is a term of art and as used herein refers to —CN.

The term "fluoroalkyl" as used herein refers to an alkyl group, as defined herein, wherein some or all of the hydrogens are replaced with fluorines.

The term "halo" is a term of art and as used herein refers to —F, —Cl, —Br, or —I.

The term "hydroxy" is a term of art and as used herein refers to —OH.

Certain compounds contained in compositions of the present invention may exist in particular geometric or stereoisomeric forms. In addition, compounds of the present invention may also be optically active. The present invention contemplates all such compounds, including cis- and trans-isomers, (R)- and (S)-enantiomers, diastereoisomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, fragmentation, decomposition, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of the invention, the chemical elements are identified in accordance with the Periodic Table of the Elements, CAS version, Handbook of Chemistry and Physics, 67th Ed., 1986-87, inside cover.

Other chemistry terms herein are used according to conventional usage in the art, as exemplified by The McGraw-Hill Dictionary of Chemical Terms (ed. Parker, S., 1985), McGraw-Hill, San Francisco, incorporated herein by reference). Unless otherwise defined, all technical and scientific terms used herein have the same meaning as commonly understood by one of ordinary skill in the art to which this invention pertains.

The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I. As another example, the salt may comprise less than one inorganic or organic acid molecule per molecule of base, such as two molecules of compound of Formula I per molecule of tartaric acid.

The terms "carrier" and "pharmaceutically acceptable carrier" as used herein refer to a diluent, adjuvant, excipient, or vehicle with which a compound is administered or formulated for administration. Non-limiting examples of such pharmaceutically acceptable carriers include liquids, such as water, saline, and oils; and solids, such as gum acacia, gelatin, starch paste, talc, keratin, colloidal silica, urea, and the like. In addition, auxiliary, stabilizing, thickening, lubricating, flavoring, and coloring agents may be used. Other examples of suitable pharmaceutical carriers are described in *Remington's Pharmaceutical Sciences* by E. W. Martin, herein incorporated by reference in its entirety.

The term "treat" as used herein means prevent, halt or slow the progression of, or eliminate a disease or condition in a subject. In one embodiment "treat" means halt or slow the progression of, or eliminate a disease or condition in a subject. In one embodiment, "treat" means reduce at least one objective manifestation of a disease or condition in a subject.

The term "effective amount" as used herein refers to an amount that is sufficient to bring about a desired biological effect.

The term "therapeutically effective amount" as used herein refers to an amount that is sufficient to bring about a desired therapeutic effect.

The term "inhibit" as used herein means decrease by an objectively measurable amount or extent. In various embodiments "inhibit" means decrease by at least 5, 10, 20, 30, 40, 50, 60, 70, 80, 90, or 95 percent compared to relevant control. In one embodiment "inhibit" means decrease 100 percent, i.e., halt or eliminate.

The term "subject" as used herein refers to a mammal. In various embodiments, a subject is a mouse, rat, rabbit, cat, dog, pig, sheep, horse, cow, or non-human primate. In one embodiment, a subject is a human.

Compounds

In some aspects, the invention provides a compound, or a pharmaceutically acceptable salt thereof, represented by formula I:

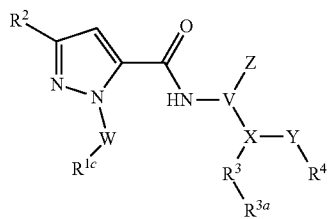

(I)

wherein:
V is optionally substituted aryl or heteroaryl;
W is optionally substituted aryl or heteroaryl;
X represents CH, C(OH), C(O(C$_1$-C$_6$)alkyl), —C(NH$_2$), —C(NR$^a$R$^b$), —C(N$_3$), —C(CN), —C(NO$_2$), —C(S(O)$_n$R$^a$), —C[—C(=O)R$^c$], —C[—C(=O)R$^c$], —C[—C(=O)NR$^c$R$^d$], —C[—C(=O)SR$^c$], —C[—S(O)R$^c$], —C[—S(O)$_2$R$^c$], —C[S(O)(OR$^c$)], —C[—S(O)$_2$(OR$^c$)], —C[—SO$_2$NR$^c$R$^d$], —C(halogen), —C[(C$_1$-C$_8$)alkyl], —C[(C$_4$-C$_8$)carbocyclylalkyl], —C[(C$_1$-C$_8$)substituted alkyl], —C[(C$_2$-C$_8$)alkenyl], —C[(C$_2$-C$_8$)substituted alkenyl], —C[(C$_2$-C$_8$)alkynyl], —C[(C$_2$-C$_8$)substituted alkynyl], —C[aryl(C$_1$-C$_8$)alkyl], C(O)N, CH$_2$N, N, C(O), P(O), —O—, S(O)N, or S(O)$_2$N; provided that:
  if X represents CH, then —Y—R$^4$ represents —H or —OH, or both Y and R$^4$ are present;
  if X represents C(OH), C(O(C$_1$-C$_6$)alkyl), —C(NH$_2$), —C(NR$^a$R$^b$), —C(N$_3$), —C(CN), —C(NO$_2$), —C(S(O)$_n$R$^a$), —C[—C(=O)R$^c$], —C[—C(=O)R$^c$], —C[—C(=O)NR$^c$R$^d$], —C[—C(=O)SR$^c$], —C[—S(O)R$^c$], —C[—S(O)$_2$R$^c$], —C[S(O)(OR$^c$)], —C[—S(O)$_2$(OR$^c$)], —C[—SO$_2$NR$^c$R$^d$], —C(halogen), —C[(C$_1$-C$_8$)alkyl], —C[(C$_4$-C$_8$)carbocyclylalkyl], —C[(C$_1$-C$_8$)substituted alkyl], —C[(C$_2$-C$_8$)alkenyl], —C[(C$_2$-C$_8$)substituted alkenyl], —C[(C$_2$-C$_8$)alkynyl], —C[(C$_2$-C$_8$)substituted alkynyl], or —C[aryl(C$_1$-C$_8$)alkyl], then —Y—R$^4$ is present;
  if X represents C(O)N, then —Y—R$^4$ represents H; or —Y—R$^4$ represents H, and —R$^3$—R$^{3a}$ represents H;
  if X represents CH$_2$N, then —Y—R$^4$ represents (C$_1$-C$_6$)alkyl;
  if X represents N, then —Y—R$^4$ represents H, or both Y and R$^4$ are present; and
  if X represents C(O) or —O—, then —Y—R$^4$ is absent;
—Y—R$^4$, when present, represents —((C$_1$-C$_6$)alkyl)-R$^4$, —CH$_2$C(O)—R$^4$, —CH$_2$NH—R$^4$, —CH$_2$N((C$_1$-C$_6$)alkyl)-R$^4$, —CR$^a$R$^b$—R$^4$, —NH—R$^4$, —NHCH$_2$—R$^4$, —NHC(O)—R$^4$, —N((C$_1$-C$_6$)alkyl)-R$^4$, —N((C$_1$-C$_6$)alkyl)CH$_2$—R$^4$, —N((CH$_2$)$_2$OH)—R$^4$, —N[(C$_3$-C$_8$)cycloalkyl(C$_1$-C$_6$)alkyl]R$^4$, -heterocyclyl-R$^4$, —OR$^4$, —OCH$_2$—R$^4$, —OC(O)—R$^4$, —OC(O)NR$^a$R$^b$, —SCH$_2$R$^4$, or —SR$^4$, wherein the (C$_1$-C$_6$)alkyl moiety of —((C$_1$-C$_6$)alkyl)-R$^4$ is optionally substituted;
Z is absent or represents one or more substituents independently selected from the group consisting of halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, —SO$_2$NH$_2$, (C$_3$-C$_8$)cycloalkyl, (CH$_2$)$_r$OR$^a$, NO$_2$, (CH$_2$)$_r$NR$^a$R$^b$, (CH$_2$)$_r$C(O)R$^a$, NR$^a$C(O)R$^b$, C(O)NR$^c$R$^d$, NR$^a$C(O)NR$^c$R$^d$, —C(=NR$^a$)NR$^c$R$^d$, NHC(=NR$^a$)NR$^c$R$^d$, NR$^a$R$^b$SO$_2$NR$^c$R$^d$, NR$^a$SO$_2$NR$^c$R$^d$, NR$^a$SO$_2$—(C$_1$-C$_6$)alkyl, NR$^a$SO$_2$R$^a$, S(O)$_p$R$^a$, (CF$_2$)$_r$CF$_3$, NHCH$_2$R$^a$, OCH$_2$R$^a$, SCH$_2$R$^a$, NH(CH$_2$)$_2$(CH$_2$)$_r$R$^a$, O(CH$_2$)$_2$(CH$_2$)$_r$R$^a$, and S(CH$_2$)$_2$(CH$_2$)$_r$R$^a$; or alternatively Z is a 5- or 6-membered aromatic heterocycle containing from 1 to 4 heteroatoms selected from the group consisting of N, O, and S;

R$^{1c}$ represents halo, amino(C$_1$-C$_6$)alkyl, (C$_1$-C$_6$)alkoxy, cyano, —C(=NH)NH$_2$, —CONR$^a$R$^b$, —(C$_1$-C$_6$)alkylCONR$^a$R$^b$, —SO$_2$CH$_3$, formyl, acyl, —NH$_2$, —C(=NH)NH(OH), —C(=NH)NH(C(O)O—(C$_1$-C$_6$)alkyl), —C(=NH)NH(C(O)O—(C$_1$-C$_6$)haloalkyl), —C(=NH)NH(C(O)S—(C$_1$-C$_6$)alkyl), —C(=NH)NH(C(O)(OCH(C$_1$-C$_6$)alkyl)OC(O)(C$_1$-C$_6$)alkyl), optionally substituted aryl, or optionally substituted heteroaryl;

R$^2$ represents halo, (C$_1$-C$_6$)alkyl, (C$_3$-C$_8$)cycloalkyl, (C$_1$-C$_6$)fluoroalkyl, —OCH$_3$, —Si(CH$_3$)$_3$, —CONH$_2$, —C(O)OH, cyano, or phenyl;

R$^3$, when present, represents —NH—, —O—, optionally substituted aryl, heteroaryl, phenyl, carbocyclyl, or heterocyclyl;

R$^{3a}$ is absent or represents one or more substituents independently selected from the group consisting of halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, —SO$_2$NH$_2$, (C$_3$-C$_8$)cycloalkyl, (CH$_2$)$_r$OR$^a$, NO$_2$, (CH$_2$)$_r$NR$^a$R$^b$, (CH$_2$)$_r$C(O)R$^a$, NR$^a$C(O)R$^b$, C(O)NR$^c$R$^d$, NR$^a$C(O)NR$^c$R$^d$, —C(=NR$^a$)NR$^c$R$^d$, NHC(=NR$^a$)NR$^c$R$^d$, NR$^a$R$^b$SO$_2$NR$^c$R$^d$, NR$^a$SO$_2$NR$^c$R$^d$, NR$^a$SO$_2$—(C$_1$-C$_6$)alkyl, NR$^a$SO$_2$R$^a$, S(O)$_p$R$^a$, (CF$_2$)$_r$CF$_3$, NHCH$_2$R$^a$, OCH$_2$R$^a$, SCH$_2$R$^a$, NH(CH$_2$)$_2$(CH$_2$)$_r$R$^a$, O(CH$_2$)$_2$(CH$_2$)$_r$R$^a$, or S(CH$_2$)$_2$(CH$_2$)$_r$R$^a$; or alternatively R$^{3a}$ is a 5- or 6-membered aromatic heterocycle containing from 1 to 4 heteroatoms selected from the group consisting of N, O, and S;

R$^4$ represents hydrogen, hydroxy, optionally substituted (C$_1$-C$_6$)alkyl, optionally substituted (C$_3$-C$_8$)cycloalkyl, heterocyclyl(C$_1$-C$_6$)alkyl, (C$_3$-C$_8$)cycloalkyl(C$_1$-C$_6$)alkyl, —CH$_2$OH, —CH((C$_1$-C$_6$)alkyl)OH, —CH(NH$_2$)CH((C$_1$-C$_6$)alkyl)$_2$, optionally substituted aryl, optionally substituted aryl(C$_1$-C$_6$)alkyl, heteroaryl, optionally substituted heteroaryl(C$_1$-C$_6$)alkyl, —CH$_2$S(C$_1$-C$_6$)alkyl, amino, or cyano; or —(CR$^a$R$^b$)$_r$(CR$^a$R$^b$)$_p$— fused to the 4-position of the ring bearing Z to form a 5- to 7-membered heterocyclic ring with optional substituents; or, when R$^3$ is phenyl, can represent —NR$^a$— fused to the position ortho to X on that phenyl;

each R$^a$ and R$^b$ is independently H, (C$_1$-C$_8$)alkyl, (C$_2$-C$_8$)alkenyl, (C$_2$-C$_8$)alkynyl, aryl(C$_1$-C$_8$)alkyl, (C$_3$-C$_8$)carbocyclylalkyl, —C(=O)R$^c$, —C(=O)OR$^c$, —C(=O)NR$^c$R$^d$, —C(=O)SR$^c$, S(O)R$^c$, —S(O)$_2$R$^c$, —S(O)(OR$^c$), or —SO$_2$NR$^c$R$^d$;

each R$^c$ and R$^d$ is independently H, (C$_1$-C$_8$)alkyl, (C$_2$-C$_8$)alkenyl, (C$_2$-C$_8$)alkynyl, (C$_4$-C$_8$) carbocyclylalkyl, optionally substituted aryl, optionally substituted heteroaryl, —C(=O)(C$_1$-C$_8$)alkyl, —S(O)$_n$(C$_1$-C$_8$)alkyl, or aryl(C$_1$-C$_8$)alkyl; or when R and R$^d$ are bonded to a common nitrogen atom, then they may form a 3- to 7-membered heterocyclic ring wherein optionally a carbon atom of said heterocyclic ring may be replaced with —O—, —S— or —NR$^a$—;

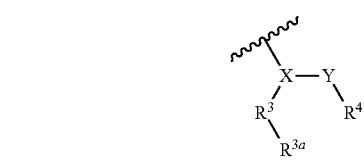

can represent

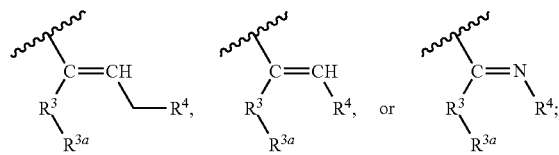

n is 2 or 3;

r is independently for each occurrence 0, 1, 2, or 3;

p is independently for each occurrence 0, 1, or 2; and the stereochemical configuration at any chiral center is R, S, or a mixture of R and S.

In certain embodiments, X represents CH, and both Y and $R^4$ are present.

In certain embodiments, —X—Y— represents —CHN-HCH$_2$—.

In certain embodiments, —X—Y— represents —C(OH)CH$_2$CH$_2$—.

In certain embodiments, —X—Y— represents —CHOCH$_2$—.

In certain embodiments, $R^3$ represents phenylene-$R^{3a}$.

In certain embodiments, —$R^3$—$R^{3a}$ represents

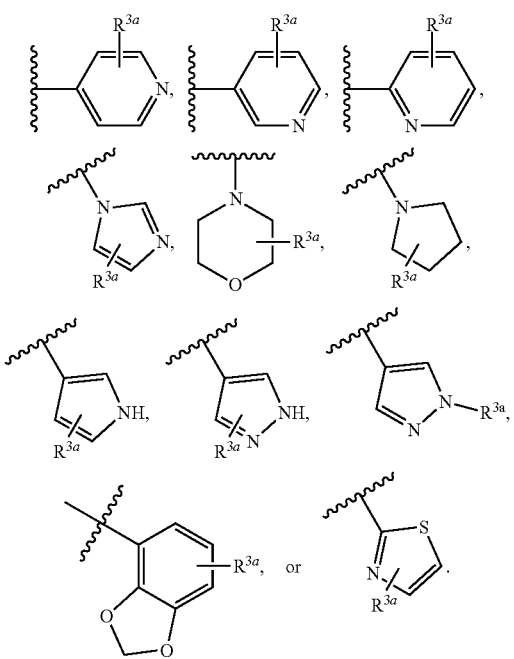

In certain embodiments, —$R^3$—$R^{3a}$ represents

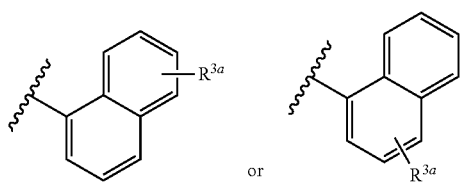

In certain embodiments, —$R^3$—$R^{3a}$ represents

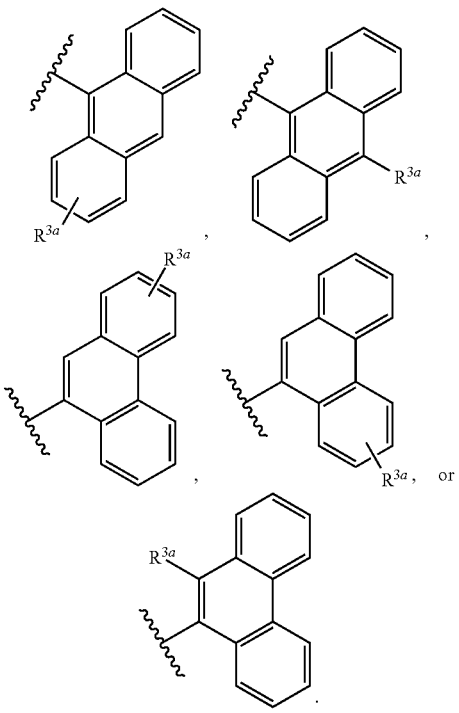

In certain embodiments, $R^{3a}$ is absent.

In certain embodiments, $R^4$ is cyclopropyl.

In certain embodiments, $R^3$ is phenyl, and $R^{3a}$ is ortho, meta, or para —OH.

In certain embodiments, $R^3$ is phenyl, and $R^{3a}$ is meta or para —NH$_2$.

In certain embodiments, $R^3$ is phenyl, and $R^{3a}$ is meta or para —CN.

In certain embodiments, Z is absent.

In certain embodiments, Z represents fluoro.

In certain embodiments, Z represents chloro.

In certain embodiments, Z represents 2-F, 4-F, 5-F, 6-F, 6-Cl, or 5-($C_3$-$C_8$)cycloalkyl.

In certain embodiments, Z represents 6-F.

In certain embodiments, $R^{1c}$ represents aminomethyl.

In certain embodiments, $R^{1c}$ represents cyano.

In certain embodiments, $R^{1c}$ represents —SO$_2$CH$_3$.

In certain embodiments, wherein $R^2$ is —CH$_3$ or —CF$_3$.

In certain embodiments, $R^2$ is —CF$_3$.

In certain embodiments, $R^2$ is tert-butyl.

In certain embodiments, $R^2$ is cyclopropyl.

In certain embodiments, $R^2$ is —OCH$_3$.

In certain embodiments, $R^2$ is —Si(CH$_3$)$_3$.

In certain embodiments, $R^2$ is —CONH$_2$.

In certain embodiments, $R^2$ is cyano.

In certain embodiments, $R^2$ is phenyl.

In certain embodiments, the compound is represented by formula II:

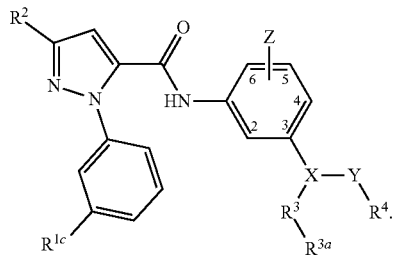

(II)

In certain embodiments, the compound is represented by formula IV:

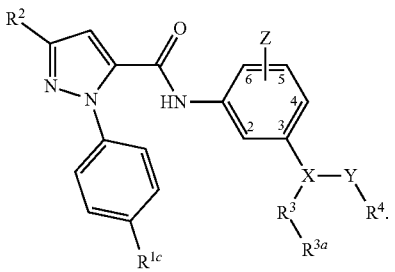

(IV)

In certain embodiments, the compound is represented by formula VI:

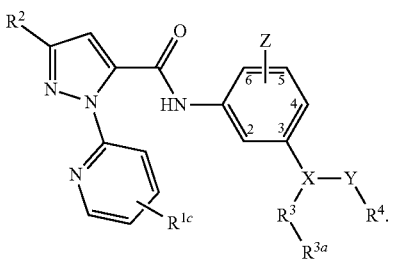

(VI)

In certain embodiments, the compound is represented by formula VIII:

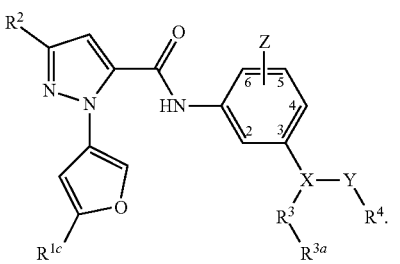

(VIII)

In certain embodiments, the compound is represented by formula X:

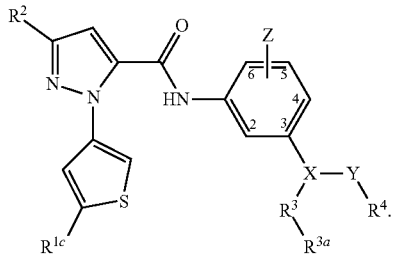

(X)

In certain embodiments, the compound is represented by formula XII:

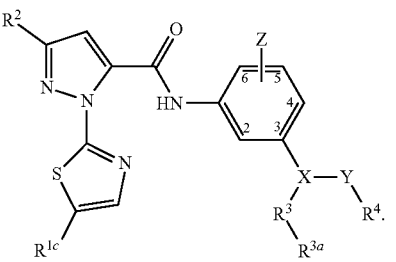

(XII)

In certain embodiments, the compound is represented by formula XIV:

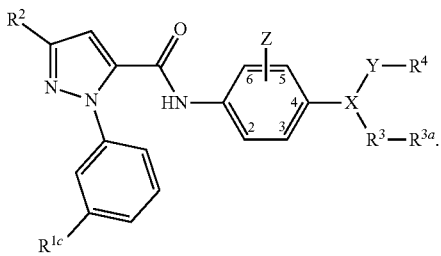

(XIV)

In certain embodiments, the compound is represented by formula XVI:

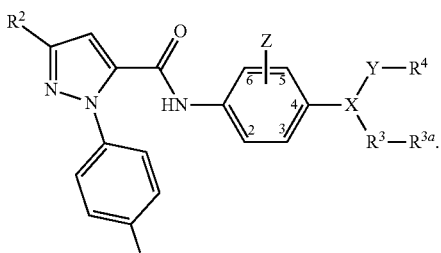

(XVI)

In certain embodiments, the compound is represented by formula XVIII:

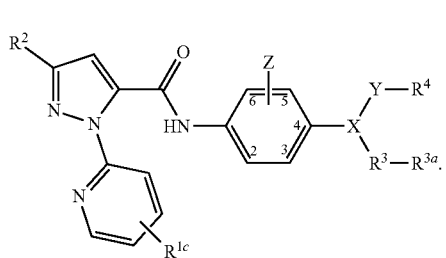

(XVIII)

In certain embodiments, the compound is represented by formula XX:

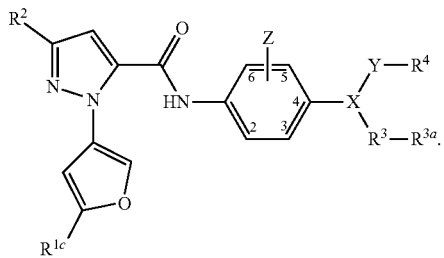

(XX)

In certain embodiments, the compound is represented by formula XXII:

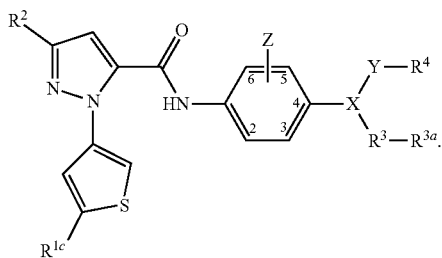

(XXII)

In certain embodiments, the compound is represented by formula XXIV:

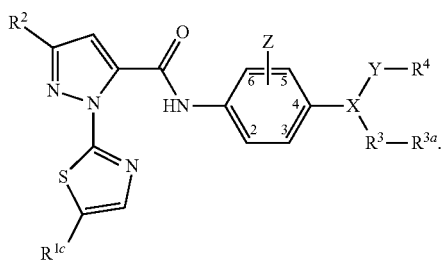

(XXIV)

In certain aspects, the invention provides a compound, or a pharmaceutically acceptable salt thereof, represented by formula III:

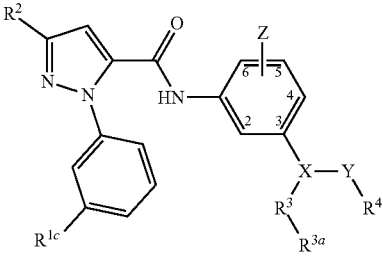

(III)

wherein:
X represents CH, C(OH), C(O(C$_1$-C$_6$)alkyl), C(O)N, CH$_2$N, N, C(O), or —O—; provided that:
  if X represents CH, then —Y—R$^4$ represents —H or —OH, or both Y and R$^4$ are present;
  if X represents C(OH) or C(O(C$_1$-C$_6$)alkyl), then —Y—R$^4$ is present;
  if X represents C(O)N, then —Y—R$^4$ represents H; or —Y—R$^4$ represents H, and —R$^3$—R$^{3a}$ represents H;
  if X represents CH$_2$N, then —Y—R$^4$ represents (C$_1$-C$_6$)alkyl;
  if X represents N, then —Y—R$^4$ represents H, or both Y and R$^4$ are present; and
  if X represents C(O) or —O—, then —Y—R$^4$ is absent;
—Y—R$^4$, when present, represents —((C$_1$-C$_6$)alkyl)-R$^4$, —CH$_2$C(O)—R$^4$, —CH$_2$NH—R$^4$, —CH$_2$N((C$_1$-C$_6$)alkyl)-R$^4$, —CR$^a$R$^b$—R$^4$, —NH—R$^4$, —NHCH$_2$—R$^4$, —NHC(O)—R$^4$, —N((C$_1$-C$_6$)alkyl)-R$^4$, —N((C$_1$-C$_6$)alkyl)CH$_2$—R$^4$, —N((CH$_2$)$_2$OH)—R$^4$, —N[(C$_3$-C$_8$)cycloalkyl(C$_1$-C$_6$)alkyl]R$^4$, -heterocyclyl-R$^4$, —OR$^4$, —OCH$_2$—R$^4$, —OC(O)—R$^4$, —OC(O)NR$^a$R$^b$, —SCH$_2$R$^4$, or —SR$^4$, wherein the (C$_1$-C$_6$)alkyl moiety of —((C$_1$-C$_6$)alkyl)-R$^4$ is optionally substituted;
Z is absent or represents halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, —SO$_2$NH$_2$, or (C$_3$-C$_8$)cycloalkyl;
R$^{1c}$ represents halo, amino(C$_1$-C$_6$)alkyl, (C$_1$-C$_6$)alkoxy, cyano, —SO$_2$CH$_3$, formyl, acyl, or optionally substituted aryl;
R$^2$ represents halo, (C$_1$-C$_6$)alkyl, (C$_3$-C$_8$)cycloalkyl, (C$_1$-C$_6$)fluoroalkyl, —OCH$_3$, —Si(CH$_3$)$_3$, —CONH$_2$, —C(O)OH, cyano, or phenyl;
R$^3$, when present, represents —NH—, —O—, optionally substituted aryl, heteroaryl, phenyl, carbocyclyl, or heterocyclyl;
R$^{3a}$ is absent or represents one or more substituents independently selected from the group consisting of halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, and —SO$_2$NH$_2$;
R$^4$ represents hydrogen, hydroxy, optionally substituted (C$_1$-C$_6$)alkyl, optionally substituted (C$_3$-C$_8$)cycloalkyl, heterocyclyl(C$_1$-C$_6$)alkyl, (C$_3$-C$_8$)cycloalkyl(C$_1$-C$_6$)alkyl, —CH$_2$OH, —CH((C$_1$-C$_6$)alkyl)OH, —CH(NH$_2$)CH((C$_1$-C$_6$)alkyl)$_2$, optionally substituted aryl, optionally substituted aryl(C$_1$-C$_6$)alkyl, heteroaryl, optionally substituted heteroaryl(C$_1$-C$_6$)alkyl, —CH$_2$S(C$_1$-C$_6$)alkyl, amino, or cyano; or —CH$_2$— fused to the 4-position of the ring bearing Z to form a 5- to 7-membered heterocyclic ring with optional substituents;

or, when R³ is phenyl, can represent —NH— fused to the position ortho to X on that phenyl;

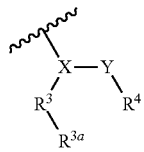

can represent

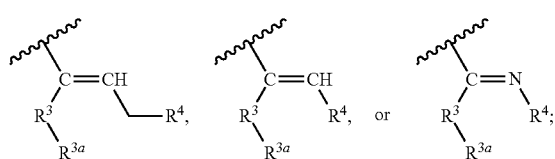

and
the stereochemical configuration at any chiral center is R, S, or a mixture of R and S.

In certain embodiments, X represents CH, and both Y and R⁴ are present.

In certain embodiments, —X—Y— represents —CHNHCH₂—.

In certain embodiments, —X—Y— represents —C(OH)CH₂CH₂—.

In certain embodiments, —X—Y— represents —CHOCH₂—.

In accordance with any one of the foregoing embodiments, in certain embodiments R³ represents phenylene-$R^{3a}$.

In accordance with any one of the foregoing embodiments, in certain embodiments —R³—$R^{3a}$ represents

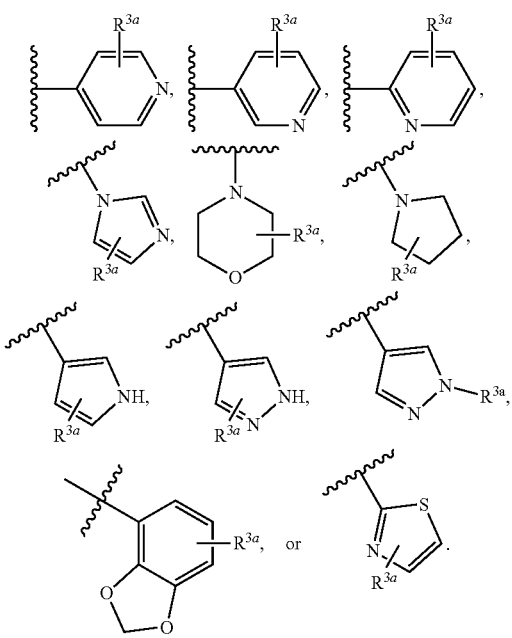

In accordance with any one of the foregoing embodiments, in certain embodiments —R³—$R^{3a}$ represents

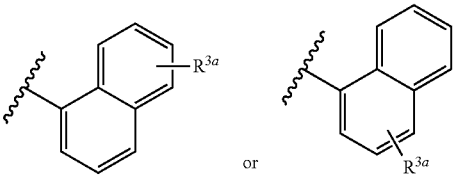

In accordance with any one of the foregoing embodiments, in certain embodiments —R³—$R^{3a}$ represents

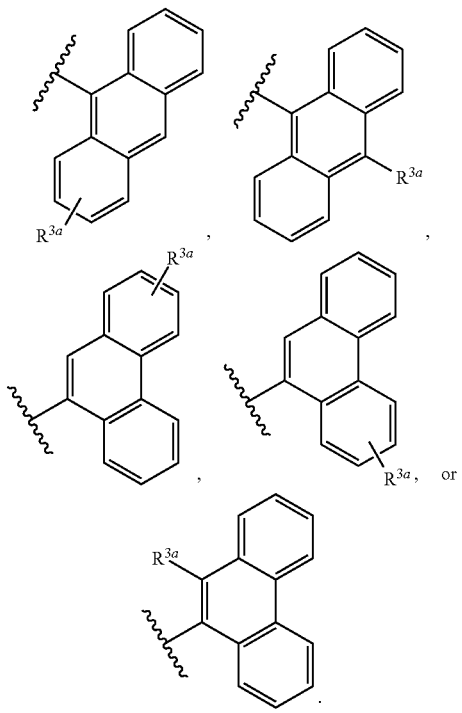

In accordance with any one of the foregoing embodiments, in certain embodiments $R^{3a}$ is absent.

In accordance with any one of the foregoing embodiments, in certain embodiments R⁴ is cyclopropyl.

In accordance with any one of the foregoing embodiments, in certain embodiments R³ is phenyl, and $R^{3a}$ is ortho, meta, or para —OH.

In accordance with any one of the foregoing embodiments, in certain embodiments R³ is phenyl, and $R^{3a}$ is meta or para —NH₂.

In accordance with any one of the foregoing embodiments, in certain embodiments R³ is phenyl, and $R^{3a}$ is meta or para —CN.

In accordance with any one of the foregoing embodiments, in certain embodiments Z is absent.

In accordance with any one of the foregoing embodiments, in certain embodiments Z represents fluoro.

In accordance with any one of the foregoing embodiments, in certain embodiments Z represents chloro.

In accordance with any one of the foregoing embodiments, in certain embodiments Z represents 2-F, 4-F, 5-F, 6-F, 6-Cl, or 5-(C₃-C₈)cycloalkyl.

In accordance with any one of the foregoing embodiments, in certain embodiments Z represents 6-F.

In accordance with any one of the foregoing embodiments, in certain embodiments $R^{1c}$ represents aminomethyl.

In accordance with any one of the foregoing embodiments, in certain embodiments $R^{1c}$ represents cyano.

In accordance with any one of the foregoing embodiments, in certain embodiments $R^{1c}$ represents —SO$_2$CH$_3$.

In accordance with any one of the foregoing embodiments, in certain embodiments $R^2$ is —CH$_3$ or —CF$_3$.

In accordance with any one of the foregoing embodiments, in certain embodiments $R^2$ is —CF$_3$.

In accordance with any one of the foregoing embodiments, in certain embodiments $R^2$ is tert-butyl.

In accordance with any one of the foregoing embodiments, in certain embodiments $R^2$ is cyclopropyl.

In accordance with any one of the foregoing embodiments, in certain embodiments $R^2$ is —OCH$_3$.

In accordance with any one of the foregoing embodiments, in certain embodiments $R^2$ is —Si(CH$_3$)$_3$.

In accordance with any one of the foregoing embodiments, in certain embodiments $R^2$ is —CONH$_2$.

In accordance with any one of the foregoing embodiments, in certain embodiments $R^2$ is cyano.

In accordance with any one of the foregoing embodiments, in certain embodiments $R^2$ is phenyl.

In certain embodiments, the compound is selected from the group consisting of:

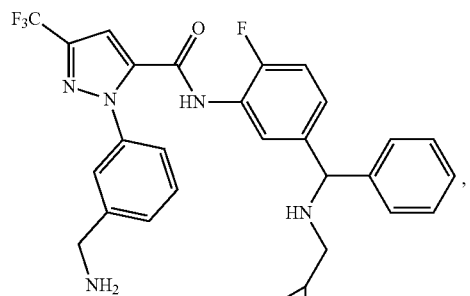

,

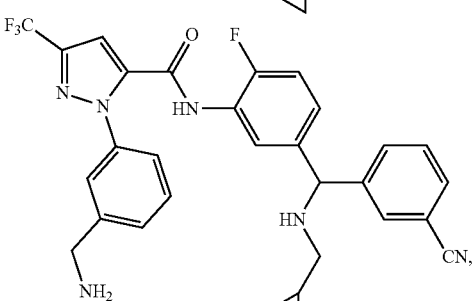

,

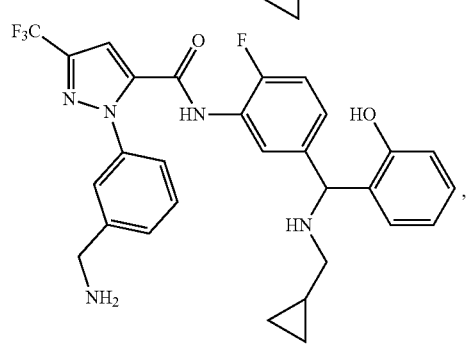

,

-continued

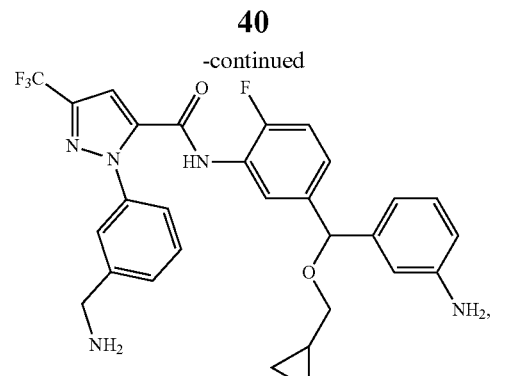

,

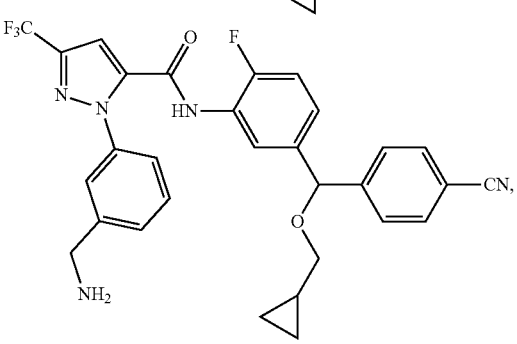

,

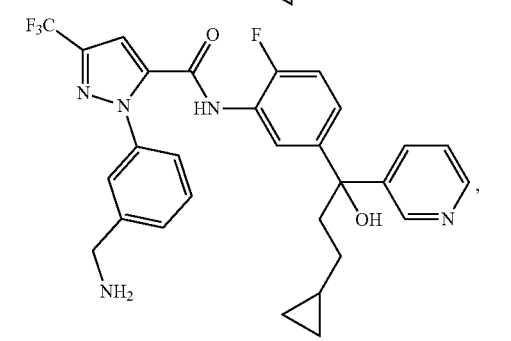

,

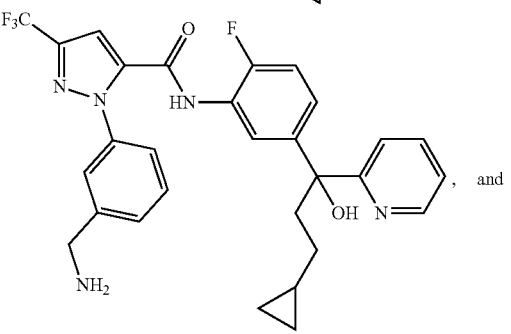

, and

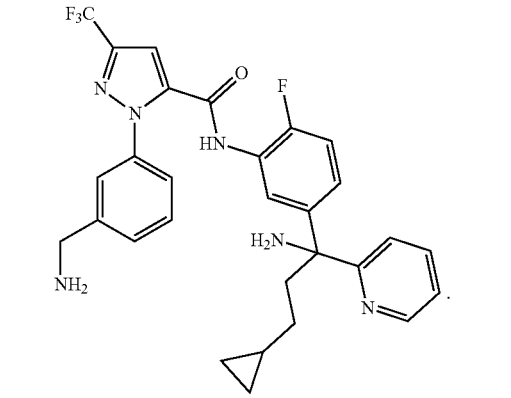

.

In certain embodiments, the compound is selected from the group consisting of:
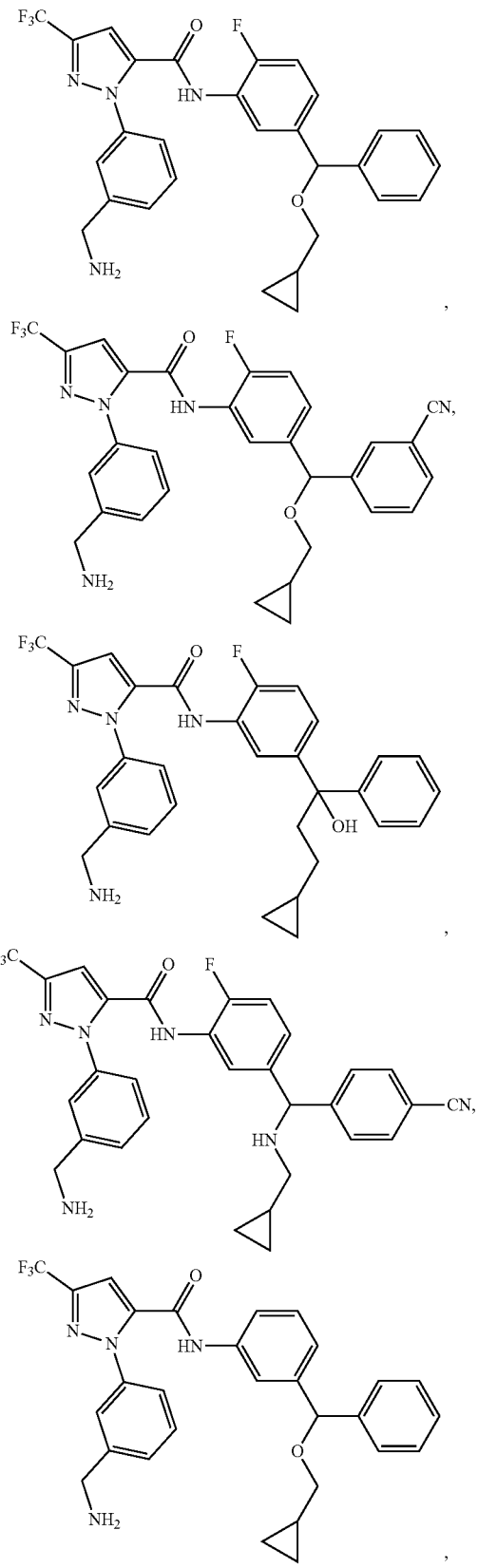
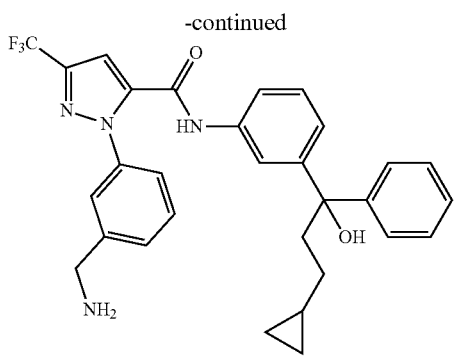
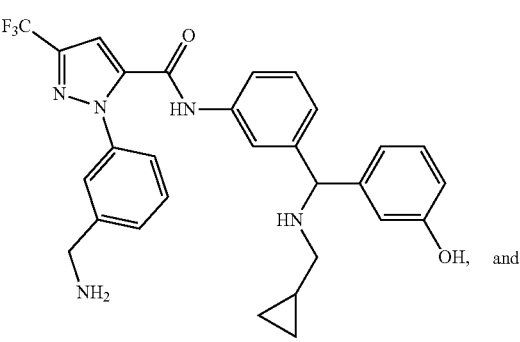
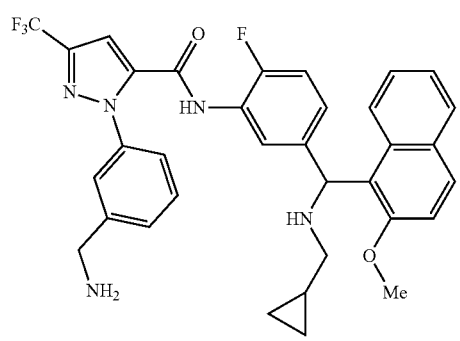
In certain embodiments, the compound is selected from the group consisting of:
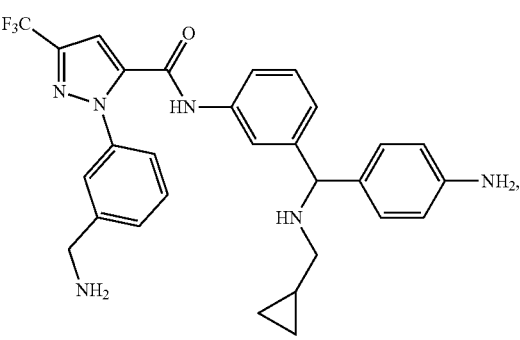

43
-continued

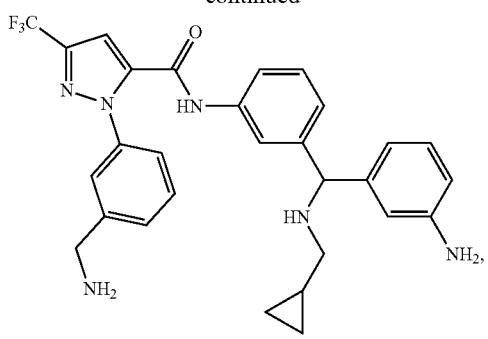

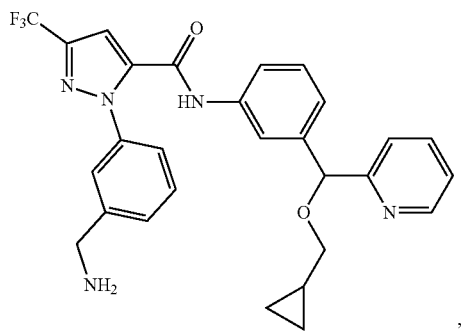

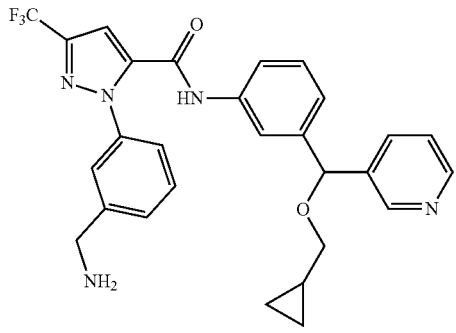

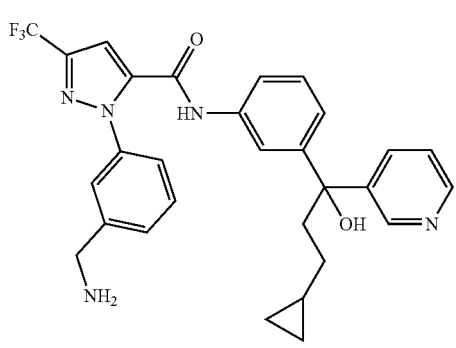

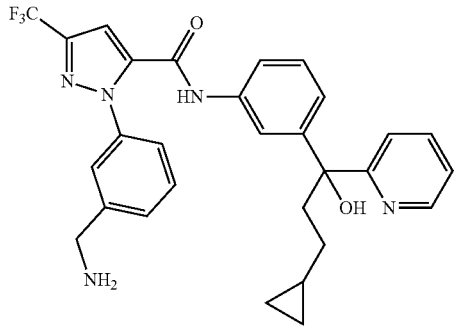

44
-continued

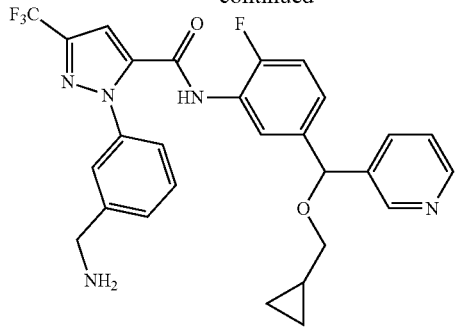
, and

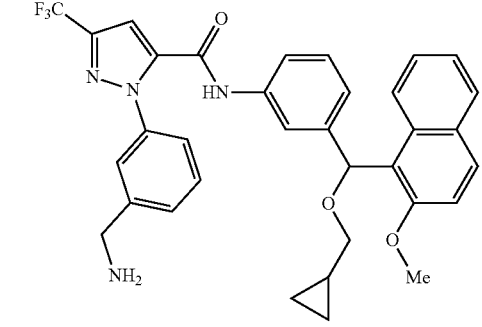
,

In certain aspects, the invention provides a compound, or a pharmaceutically acceptable salt thereof, represented by formula V:

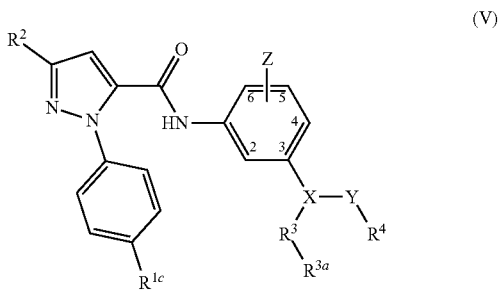

(V)

wherein:
X represents CH, C(OH), C(O(C₁-C₆)alkyl), C(O)N, CH₂N, N, C(O), or —O—; provided that:
  if X represents CH, then —Y—R⁴ represents —H or —OH, or both Y and R⁴ are present;
  if X represents C(OH) or C(O(C₁-C₆)alkyl), then —Y—R⁴ is present;
  if X represents C(O)N, then —Y—R⁴ represents H; or —Y—R⁴ represents H, and —R³—R³ᵃ represents H;
  if X represents CH₂N, then —Y—R⁴ represents (C₁-C₆)alkyl;
  if X represents N, then —Y—R⁴ represents H, or both Y and R⁴ are present; and
  if X represents C(O) or —O—, then —Y—R⁴ is absent;
—Y—R⁴, when present, represents —((C₁-C₆)alkyl)-R⁴, —CH₂C(O)—R⁴, —CH₂NH—R⁴, —CH₂N((C₁-C₆)alkyl)-R⁴, —CRᵃRᵇ—R⁴, —NH—R⁴, —NHCH₂—R⁴, —NHC(O)—R⁴, —N((C₁-C₆)alkyl)-R⁴, —N((C₁-C₆)alkyl)CH₂—R⁴, —N((CH₂)₂OH)—R⁴, —N[(C₃-C₈)cycloalkyl(C₁-C₆)alkyl]R⁴, -heterocyclyl-R⁴, —OR⁴, —OCH₂—R⁴, —OC(O)—R⁴, —OC(O)NRᵃRᵇ, —SCH₂R⁴, or —SR⁴, wherein the (C₁-C₆)alkyl moiety of —((C₁-C₆)alkyl)-R⁴ is optionally substituted;

Z is absent or represents halo, hydroxy, $(C_1-C_6)$alkyl, —$CF_3$, —$OCF_3$, $(C_1-C_6)$alkoxy, aryl, aryloxy, amino, amino$(C_1-C_6)$alkyl, —$C(O)NH_2$, cyano, —$NHC(O)(C_1-C_6)$alkyl, —$SO_2(C_1-C_6)$alkyl, —$SO_2NH_2$, or $(C_3-C_8)$cycloalkyl;

$R^{1c}$ represents halo, amino$(C_1-C_6)$alkyl, $(C_1-C_6)$alkoxy, cyano, —$SO_2CH_3$, formyl, acyl, or optionally substituted aryl;

$R^2$ represents halo, $(C_1-C_6)$alkyl, $(C_3-C_8)$cycloalkyl, $(C_1-C_6)$fluoroalkyl, —$OCH_3$, —$Si(CH_3)_3$, —$CONH_2$, —$C(O)OH$, cyano, or phenyl;

$R^3$, when present, represents —NH—, —O—, optionally substituted aryl, heteroaryl, phenyl, carbocyclyl, or heterocyclyl;

$R^{3a}$ is absent or represents one or more substituents independently selected from the group consisting of halo, hydroxy, $(C_1-C_6)$alkyl, —$CF_3$, —$OCF_3$, $(C_1-C_6)$alkoxy, aryl, aryloxy, amino, amino$(C_1-C_6)$alkyl, —$C(O)NH_2$, cyano, —$NHC(O)(C_1-C_6)$alkyl, —$SO_2(C_1-C_6)$alkyl, and —$SO_2NH_2$;

$R^4$ represents hydrogen, hydroxy, optionally substituted $(C_1-C_6)$alkyl, optionally substituted $(C_3-C_8)$cycloalkyl, heterocyclyl$(C_1-C_6)$alkyl, $(C_3-C_8)$cycloalkyl$(C_1-C_6)$alkyl, —$CH_2OH$, —$CH((C_1-C_6)$alkyl$)OH$, —$CH(NH_2)CH((C_1-C_6)$alkyl$)_2$, optionally substituted aryl, optionally substituted aryl$(C_1-C_6)$alkyl, heteroaryl, optionally substituted heteroaryl$(C_1-C_6)$alkyl, —$CH_2S(C_1-C_6)$alkyl, amino, or cyano; or —$CH_2$— fused to the 4-position of the ring bearing Z to form a 5- to 7-membered heterocyclic ring with optional substituents;

or, when $R^3$ is phenyl, can represent —NH— fused to the position ortho to X on that phenyl;

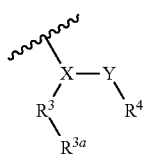

can represent

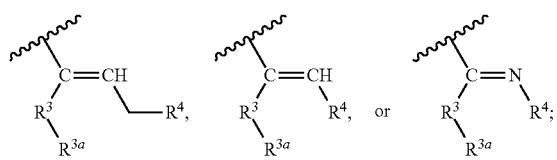

and the stereochemical configuration at any chiral center is R, S, or a mixture of R and S.

In certain embodiments, X represents CH, and both Y and $R^4$ are present.

In certain embodiments, —X—Y— represents —CHNHCH$_2$—.

In certain embodiments, —X—Y— represents —C(OH)CH$_2$CH$_2$—.

In certain embodiments, —X—Y— represents —CHOCH$_2$—.

In accordance with any one of the foregoing embodiments, in certain embodiments $R^3$ represents phenylene-$R^{3a}$.

In accordance with any one of the foregoing embodiments, in certain embodiments —$R^3$—$R^{3a}$ represents

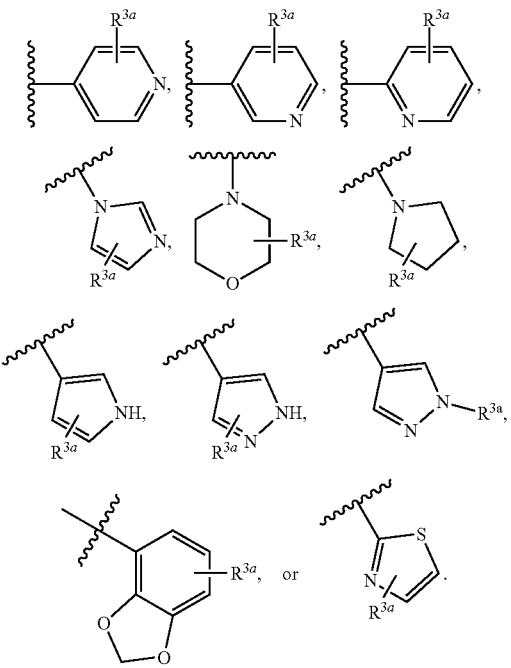

In accordance with any one of the foregoing embodiments, in certain embodiments —$R^3$—$R^{3a}$ represents

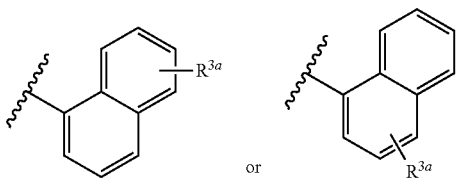

In accordance with any one of the foregoing embodiments, in certain embodiments —$R^3$—$R^{3a}$ represents

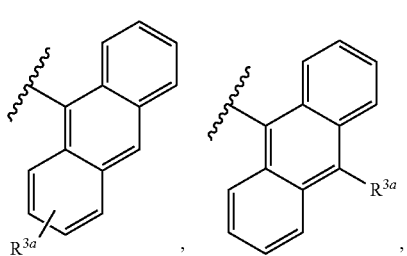

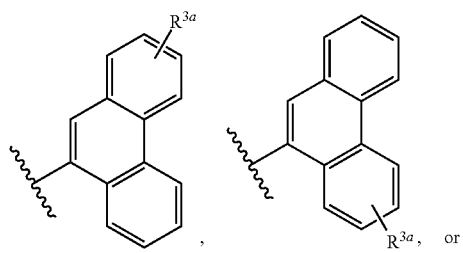

-continued

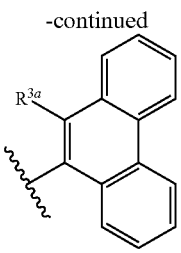

In accordance with any one of the foregoing embodiments, in certain embodiments $R^{3a}$ is absent.

In accordance with any one of the foregoing embodiments, in certain embodiments $R^4$ is cyclopropyl.

In accordance with any one of the foregoing embodiments, in certain embodiments $R^3$ is phenyl, and $R^{3a}$ is ortho, meta, or para —OH.

In accordance with any one of the foregoing embodiments, in certain embodiments $R^3$ is phenyl, and $R^{3a}$ is meta or para —NH$_2$.

In accordance with any one of the foregoing embodiments, in certain embodiments $R^3$ is phenyl, and $R^{3a}$ is meta or para —CN.

In accordance with any one of the foregoing embodiments, in certain embodiments Z is absent.

In accordance with any one of the foregoing embodiments, in certain embodiments Z represents fluoro.

In accordance with any one of the foregoing embodiments, in certain embodiments Z represents chloro.

In accordance with any one of the foregoing embodiments, in certain embodiments Z represents 2-F, 4-F, 5-F, 6-F, 6-Cl, or 5-(C$_3$-C$_8$)cycloalkyl.

In accordance with any one of the foregoing embodiments, in certain embodiments Z represents 6-F.

In accordance with any one of the foregoing embodiments, in certain embodiments $R^{1c}$ represents aminomethyl.

In accordance with any one of the foregoing embodiments, in certain embodiments $R^{1c}$ represents cyano.

In accordance with any one of the foregoing embodiments, in certain embodiments $R^{1c}$ represents —SO$_2$CH$_3$.

In accordance with any one of the foregoing embodiments, in certain embodiments $R^2$ is —CH$_3$ or —CF$_3$.

In accordance with any one of the foregoing embodiments, in certain embodiments $R^2$ is —CF$_3$.

In accordance with any one of the foregoing embodiments, in certain embodiments $R^2$ is tert-butyl.

In accordance with any one of the foregoing embodiments, in certain embodiments $R^2$ is cyclopropyl.

In accordance with any one of the foregoing embodiments, in certain embodiments $R^2$ is —OCH$_3$.

In accordance with any one of the foregoing embodiments, in certain embodiments $R^2$ is —Si(CH$_3$)$_3$.

In accordance with any one of the foregoing embodiments, in certain embodiments $R^2$ is —CONH$_2$.

In accordance with any one of the foregoing embodiments, in certain embodiments $R^2$ is cyano.

In accordance with any one of the foregoing embodiments, in certain embodiments $R^2$ is phenyl.

In other aspects, the invention provides a compound, or a pharmaceutically acceptable salt thereof, represented by formula VII:

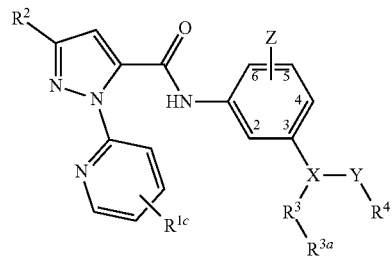

(VII)

wherein:

X represents CH, C(OH), C(O(C$_1$-C$_6$)alkyl), C(O)N, CH$_2$N, N, C(O), or —O—; provided that:
if X represents CH, then —Y—R$^4$ represents —H or —OH, or both Y and R$^4$ are present;
if X represents C(OH) or C(O(C$_1$-C$_6$)alkyl), then —Y—R$^4$ is present;
if X represents C(O)N, then —Y—R$^4$ represents H; or —Y—R$^4$ represents H, and —R$^3$—R$^{3a}$ represents H;
if X represents CH$_2$N, then —Y—R$^4$ represents (C$_1$-C$_6$)alkyl;
if X represents N, then —Y—R$^4$ represents H, or both Y and R$^4$ are present; and
if X represents C(O) or —O—, then —Y—R$^4$ is absent;
—Y—R$^4$, when present, represents —((C$_1$-C$_6$)alkyl)-R$^4$, —CH$_2$C(O)—R$^4$, —CH$_2$NH—R$^4$, —CH$_2$N((C$_1$-C$_6$)alkyl)-R$^4$, —CR$^a$R$^b$—R$^4$, —NH—R$^4$, —NHCH$_2$—R$^4$, —NHC(O)—R$^4$, —N((C$_1$-C$_6$)alkyl)-R$^4$, —N((C$_1$-C$_6$)alkyl)CH$_2$—R$^4$, —N((CH$_2$)$_2$OH)—R$^4$, —N[(C$_3$-C$_8$)cycloalkyl(C$_1$-C$_6$)alkyl]R$^4$, -heterocyclyl-R$^4$, —OR$^4$, —OCH$_2$—R$^4$, —OC(O)—R$^4$, —OC(O)NR$^a$R$^b$, —SCH$_2$R$^4$, or —SR$^4$, wherein the (C$_1$-C$_6$)alkyl moiety of —((C$_1$-C$_6$)alkyl)-R$^4$ is optionally substituted;

Z is absent or represents halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, —SO$_2$NH$_2$, or (C$_3$-C$_8$)cycloalkyl;

R$^{1c}$ represents halo, amino(C$_1$-C$_6$)alkyl, (C$_1$-C$_6$)alkoxy, cyano, —SO$_2$CH$_3$, formyl, acyl, or optionally substituted aryl;

R$^2$ represents halo, (C$_1$-C$_6$)alkyl, (C$_3$-C$_8$)cycloalkyl, (C$_1$-C$_6$)fluoroalkyl, —OCH$_3$, —Si(CH$_3$)$_3$, —CONH$_2$, —C(O)OH, cyano, or phenyl;

R$^3$, when present, represents —NH—, —O—, optionally substituted aryl, heteroaryl, phenyl, carbocyclyl, or heterocyclyl;

R$^{3a}$ is absent or represents one or more substituents independently selected from the group consisting of halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, and —SO$_2$NH$_2$;

R$^4$ represents hydrogen, hydroxy, optionally substituted (C$_1$-C$_6$)alkyl, optionally substituted (C$_3$-C$_8$)cycloalkyl, heterocyclyl(C$_1$-C$_6$)alkyl, (C$_3$-C$_8$)cycloalkyl(C$_1$-C$_6$)alkyl, —CH$_2$OH, —CH((C$_1$-C$_6$)alkyl)OH, —CH(NH$_2$)CH((C$_1$-C$_6$)alkyl)$_2$, optionally substituted aryl, optionally substituted aryl(C$_1$-C$_6$)alkyl, heteroaryl, optionally substituted heteroaryl(C$_1$-C$_6$)alkyl, —CH$_2$S(C$_1$-C$_6$)alkyl, amino, or cyano; or —CH$_2$— fused to the 4-position of the ring bearing Z to form a 5- to 7-membered heterocyclic ring with optional substituents;

or, when R³ is phenyl, can represent —NH— fused to the position ortho to X on that phenyl;

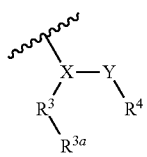

can represent

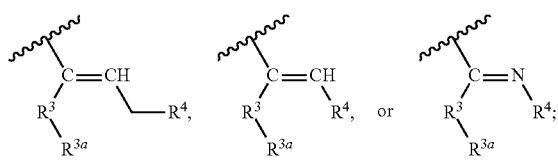

and
the stereochemical configuration at any chiral center is R, S, or a mixture of R and S.

In certain embodiments, X represents CH, and both Y and R⁴ are present.

In certain embodiments, —X—Y— represents —CHNHCH₂—.

In certain embodiments, —X—Y— represents —C(OH)CH₂CH₂—.

In certain embodiments, —X—Y— represents —CHOCH₂—.

In accordance with any one of the foregoing embodiments, in certain embodiments R³ represents phenylene-$R^{3a}$.

In accordance with any one of the foregoing embodiments, in certain embodiments —R³—$R^{3a}$ represents

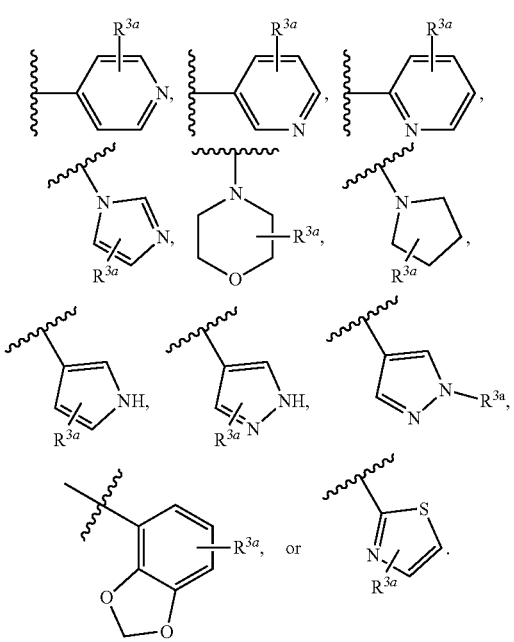

In accordance with any one of the foregoing embodiments, in certain embodiments —R³—$R^{3a}$ represents

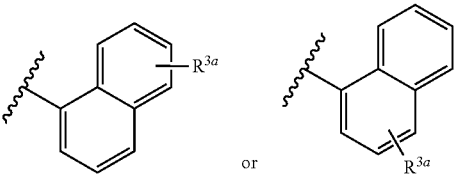

In accordance with any one of the foregoing embodiments, in certain embodiments —R³—$R^{3a}$ represents

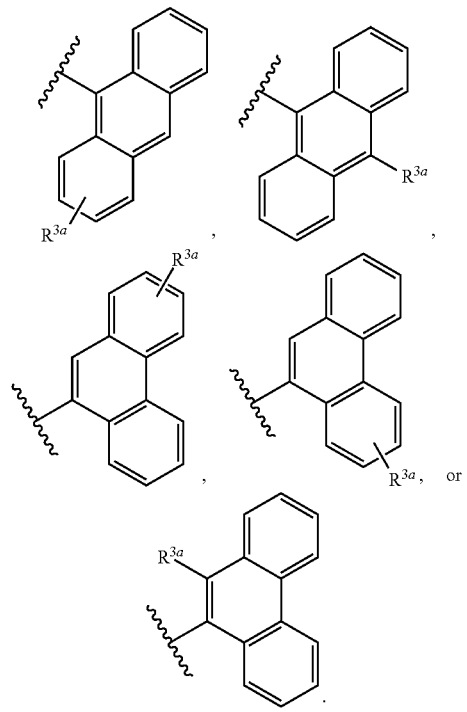

In accordance with any one of the foregoing embodiments, in certain embodiments $R^{3a}$ is absent.

In accordance with any one of the foregoing embodiments, in certain embodiments R⁴ is cyclopropyl.

In accordance with any one of the foregoing embodiments, in certain embodiments R³ is phenyl, and $R^{3a}$ is ortho, meta, or para —OH.

In accordance with any one of the foregoing embodiments, in certain embodiments R³ is phenyl, and $R^{3a}$ is meta or para —NH₂.

In accordance with any one of the foregoing embodiments, in certain embodiments R³ is phenyl, and $R^{3a}$ is meta or para —CN.

In accordance with any one of the foregoing embodiments, in certain embodiments Z is absent.

In accordance with any one of the foregoing embodiments, in certain embodiments Z represents fluoro.

In accordance with any one of the foregoing embodiments, in certain embodiments Z represents chloro.

In accordance with any one of the foregoing embodiments, in certain embodiments Z represents 2-F, 4-F, 5-F, 6-F, 6-Cl, or 5-(C₃-C₈)cycloalkyl.

In accordance with any one of the foregoing embodiments, in certain embodiments Z represents 6-F.

In accordance with any one of the foregoing embodiments, in certain embodiments $R^{1c}$ represents aminomethyl.

In accordance with any one of the foregoing embodiments, in certain embodiments $R^{1c}$ represents cyano.

In accordance with any one of the foregoing embodiments, in certain embodiments $R^{1c}$ represents —$SO_2CH_3$.

In accordance with any one of the foregoing embodiments, in certain embodiments $R^2$ is —$CH_3$ or —$CF_3$.

In accordance with any one of the foregoing embodiments, in certain embodiments $R^2$ is —$CF_3$.

In accordance with any one of the foregoing embodiments, in certain embodiments $R^2$ is tert-butyl.

In accordance with any one of the foregoing embodiments, in certain embodiments $R^2$ is cyclopropyl.

In accordance with any one of the foregoing embodiments, in certain embodiments $R^2$ is —$OCH_3$.

In accordance with any one of the foregoing embodiments, in certain embodiments $R^2$ is —$Si(CH_3)_3$.

In accordance with any one of the foregoing embodiments, in certain embodiments $R^2$ is —$CONH_2$.

In accordance with any one of the foregoing embodiments, in certain embodiments $R^2$ is cyano.

In accordance with any one of the foregoing embodiments, in certain embodiments $R^2$ is phenyl.

In other aspects, the invention provides a compound, or a pharmaceutically acceptable salt thereof, represented by formula IX:

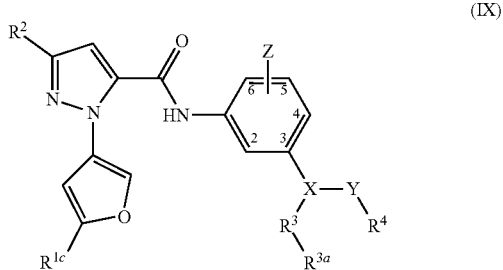

(IX)

wherein:

X represents CH, C(OH), C(O($C_1$-$C_6$)alkyl), C(O)N, $CH_2$N, N, C(O), or —O—; provided that:
  if X represents CH, then —Y—$R^4$ represents —H or —OH, or both Y and $R^4$ are present;
  if X represents C(OH) or C(O($C_1$-$C_6$)alkyl), then —Y—$R^4$ is present;
  if X represents C(O)N, then —Y—$R^4$ represents H; or —Y—$R^4$ represents H, and —$R^3$—$R^{3a}$ represents H;
  if X represents $CH_2$N, then —Y—$R^4$ represents ($C_1$-$C_6$)alkyl;
  if X represents N, then —Y—$R^4$ represents H, or both Y and $R^4$ are present; and
  if X represents C(O) or —O—, then —Y—$R^4$ is absent;

—Y—$R^4$, when present, represents —(($C_1$-$C_6$)alkyl)-$R^4$, —$CH_2$C(O)—$R^4$, —$CH_2$NH—$R^4$, —$CH_2$N(($C_1$-$C_6$)alkyl)-$R^4$, —$CR^aR^b$—$R^4$, —NH—$R^4$, —$NHCH_2$—$R^4$, —NHC(O)—$R^4$, —N(($C_1$-$C_6$)alkyl)-$R^4$, —N(($C_1$-$C_6$)alkyl)$CH_2$—$R^4$, —N(($CH_2$)$_2$OH)—$R^4$, —N[($C_3$-$C_8$)cycloalkyl($C_1$-$C_6$)alkyl]$R^4$, -heterocyclyl-$R^4$, —$OR^4$, —$OCH_2$—$R^4$, —OC(O)—$R^4$, —OC(O)$NR^aR^b$, —$SCH_2R^4$, or —$SR^4$, wherein the ($C_1$-$C_6$)alkyl moiety of —(($C_1$-$C_6$)alkyl)-$R^4$ is optionally substituted;

Z is absent or represents halo, hydroxy, ($C_1$-$C_6$)alkyl, —$CF_3$, —$OCF_3$, ($C_1$-$C_6$)alkoxy, aryl, aryloxy, amino, amino($C_1$-$C_6$)alkyl, —$C(O)NH_2$, cyano, —NHC(O)($C_1$-$C_6$)alkyl, —$SO_2$($C_1$-$C_6$)alkyl, —$SO_2NH_2$, or ($C_3$-$C_8$)cycloalkyl;

$R^{1c}$ represents halo, amino($C_1$-$C_6$)alkyl, ($C_1$-$C_6$)alkoxy, cyano, —$SO_2CH_3$, formyl, acyl, or optionally substituted aryl;

$R^2$ represents halo, ($C_1$-$C_6$)alkyl, ($C_3$-$C_8$)cycloalkyl, ($C_1$-$C_6$)fluoroalkyl, —$OCH_3$, —$Si(CH_3)_3$, —$CONH_2$, —C(O)OH, cyano, or phenyl;

$R^3$, when present, represents —NH—, —O—, optionally substituted aryl, heteroaryl, phenyl, carbocyclyl, or heterocyclyl;

$R^{3a}$ is absent or represents one or more substituents independently selected from the group consisting of halo, hydroxy, ($C_1$-$C_6$)alkyl, —$CF_3$, —$OCF_3$, ($C_1$-$C_6$)alkoxy, aryl, aryloxy, amino, amino($C_1$-$C_6$)alkyl, —$C(O)NH_2$, cyano, —NHC(O)($C_1$-$C_6$)alkyl, —$SO_2$($C_1$-$C_6$)alkyl, and —$SO_2NH_2$;

$R^4$ represents hydrogen, hydroxy, optionally substituted ($C_1$-$C_6$)alkyl, optionally substituted ($C_3$-$C_8$)cycloalkyl, heterocyclyl($C_1$-$C_6$)alkyl, ($C_3$-$C_8$)cycloalkyl($C_1$-$C_6$)alkyl, —$CH_2$OH, —CH(($C_1$-$C_6$)alkyl)OH, —CH($NH_2$)CH(($C_1$-$C_6$)alkyl)$_2$, optionally substituted aryl, optionally substituted aryl($C_1$-$C_6$)alkyl, heteroaryl, optionally substituted heteroaryl($C_1$-$C_6$)alkyl, —$CH_2$S($C_1$-$C_6$)alkyl, amino, or cyano; or —$CH_2$— fused to the 4-position of the ring bearing Z to form a 5- to 7-membered heterocyclic ring with optional substituents;

or, when $R^3$ is phenyl, can represent —NH— fused to the position ortho to X on that phenyl;

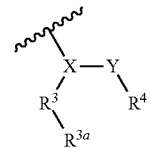

can represent

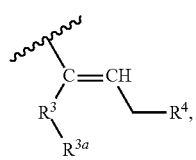 , 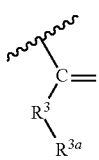 , or 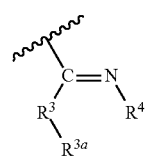 ;

and the stereochemical configuration at any chiral center is R, S, or a mixture of R and S.

In certain embodiments, X represents CH, and both Y and $R^4$ are present.

In certain embodiments, —X—Y— represents —CHNHCH$_2$—.

In certain embodiments, —X—Y— represents —C(OH)CH$_2$CH$_2$—.

In certain embodiments, —X—Y— represents —CHOCH$_2$—.

In accordance with any one of the foregoing embodiments, in certain embodiments $R^3$ represents phenylene-$R^{3a}$.

In accordance with any one of the foregoing embodiments, in certain embodiments —$R^3$—$R^{3a}$ represents In accordance with any one of the foregoing embodiments, in certain embodiments —R³—R³ᵃ represents In accordance with any one of the foregoing embodiments, in certain embodiments —R³—R³ᵃ represents In accordance with any one of the foregoing embodiments, in certain embodiments R³ᵃ is absent.

In accordance with any one of the foregoing embodiments, in certain embodiments R⁴ is cyclopropyl.

In accordance with any one of the foregoing embodiments, in certain embodiments R³ is phenyl, and R³ᵃ is ortho, meta, or para —OH.

In accordance with any one of the foregoing embodiments, in certain embodiments R³ is phenyl, and R³ᵃ is meta or para —NH₂.

In accordance with any one of the foregoing embodiments, in certain embodiments R³ is phenyl, and R³ᵃ is meta or para —CN.

In accordance with any one of the foregoing embodiments, in certain embodiments Z is absent.

In accordance with any one of the foregoing embodiments, in certain embodiments Z represents fluoro.

In accordance with any one of the foregoing embodiments, in certain embodiments Z represents chloro.

In accordance with any one of the foregoing embodiments, in certain embodiments Z represents 2-F, 4-F, 5-F, 6-F, 6-Cl, or 5-(C₃-C₈)cycloalkyl.

In accordance with any one of the foregoing embodiments, in certain embodiments Z represents 6-F.

In accordance with any one of the foregoing embodiments, in certain embodiments $R^{1c}$ represents aminomethyl.

In accordance with any one of the foregoing embodiments, in certain embodiments $R^{1c}$ represents cyano.

In accordance with any one of the foregoing embodiments, in certain embodiments $R^{1c}$ represents —SO₂CH₃.

In accordance with any one of the foregoing embodiments, in certain embodiments R² is —CH₃ or —CF₃.

In accordance with any one of the foregoing embodiments, in certain embodiments R² is —CF₃.

In accordance with any one of the foregoing embodiments, in certain embodiments R² is tert-butyl.

In accordance with any one of the foregoing embodiments, in certain embodiments R² is cyclopropyl.

In accordance with any one of the foregoing embodiments, in certain embodiments R² is —OCH₃.

In accordance with any one of the foregoing embodiments, in certain embodiments R² is —Si(CH₃)₃.

In accordance with any one of the foregoing embodiments, in certain embodiments R² is —CONH₂.

In accordance with any one of the foregoing embodiments, in certain embodiments R² is cyano.

In accordance with any one of the foregoing embodiments, in certain embodiments R² is phenyl.

In certain aspects, the invention provides a compound, or a pharmaceutically acceptable salt thereof, represented by formula XI:

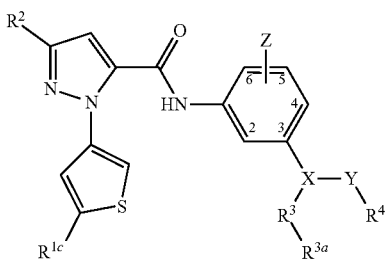

(XI)

wherein:
X represents CH, C(OH), C(O(C$_1$-C$_6$)alkyl), C(O)N, CH$_2$N, N, C(O), or —O—; provided that:
  if X represents CH, then —Y—R$^4$ represents —H or —OH, or both Y and R$^4$ are present;
  if X represents C(OH) or C(O(C$_1$-C$_6$)alkyl), then —Y—R$^4$ is present;
  if X represents C(O)N, then —Y—R$^4$ represents H; or —Y—R$^4$ represents H, and —R$^3$—R$^{3a}$ represents H;
  if X represents CH$_2$N, then —Y—R$^4$ represents (C$_1$-C$_6$)alkyl;
  if X represents N, then —Y—R$^4$ represents H, or both Y and R$^4$ are present; and
  if X represents C(O) or —O—, then —Y—R$^4$ is absent;
—Y—R$^4$, when present, represents —((C$_1$-C$_6$)alkyl)-R$^4$, —CH$_2$C(O)—R$^4$, —CH$_2$NH—R$^4$, —CH$_2$N((C$_1$-C$_6$)alkyl)-R$^4$, —CR$^a$R$^b$—R$^4$, —NH—R$^4$, —NHCH$_2$—R$^4$, —NHC(O)—R$^4$, —N((C$_1$-C$_6$)alkyl)-R$^4$, —N((C$_1$-C$_6$)alkyl)CH$_2$—R$^4$, —N((CH$_2$)$_2$OH)—R$^4$, —N[(C$_3$-C$_8$)cycloalkyl(C$_1$-C$_6$)alkyl]R$^4$, -heterocyclyl-R$^4$, —OR$^4$, —OCH$_2$—R$^4$, —OC(O)—R$^4$, —OC(O)NR$^a$R$^b$, —SCH$_2$R$^4$, or —SR$^4$, wherein the (C$_1$-C$_6$)alkyl moiety of —((C$_1$-C$_6$)alkyl)-R$^4$ is optionally substituted;
Z is absent or represents halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, —SO$_2$NH$_2$, or (C$_3$-C$_8$)cycloalkyl;
R$^{1c}$ represents halo, amino(C$_1$-C$_6$)alkyl, (C$_1$-C$_6$)alkoxy, cyano, —SO$_2$CH$_3$, formyl, acyl, or optionally substituted aryl;
R$^2$ represents halo, (C$_1$-C$_6$)alkyl, (C$_3$-C$_8$)cycloalkyl, (C$_1$-C$_6$)fluoroalkyl, —OCH$_3$, —Si(CH$_3$)$_3$, —CONH$_2$, —C(O)OH, cyano, or phenyl;
R$^3$, when present, represents —NH—, —O—, optionally substituted aryl, heteroaryl, phenyl, carbocyclyl, or heterocyclyl;
R$^{3a}$ is absent or represents one or more substituents independently selected from the group consisting of halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, and —SO$_2$NH$_2$;
R$^4$ represents hydrogen, hydroxy, optionally substituted (C$_1$-C$_6$)alkyl, optionally substituted (C$_3$-C$_8$)cycloalkyl, heterocyclyl(C$_1$-C$_6$)alkyl, (C$_3$-C$_8$)cycloalkyl(C$_1$-C$_6$)alkyl, —CH$_2$OH, —CH((C$_1$-C$_6$)alkyl)OH, —CH(NH$_2$)CH((C$_1$-C$_6$)alkyl)$_2$, optionally substituted aryl, optionally substituted aryl(C$_1$-C$_6$)alkyl, heteroaryl, optionally substituted heteroaryl(C$_1$-C$_6$)alkyl, —CH$_2$S(C$_1$-C$_6$)alkyl, amino, or cyano; or —CH$_2$— fused to the 4-position of the ring bearing Z to form a 5- to 7-membered heterocyclic ring with optional substituents;
or, when R$^3$ is phenyl, can represent —NH— fused to the position ortho to X on that phenyl;

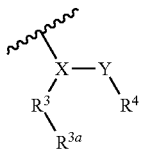

can represent

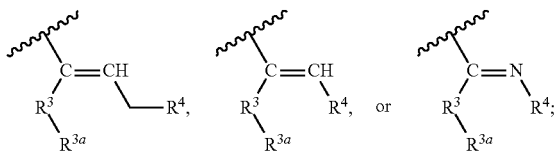

and
the stereochemical configuration at any chiral center is R, S, or a mixture of R and S.

In certain embodiments, X represents CH, and both Y and R$^4$ are present.

In certain embodiments, —X—Y— represents —CHNHCH$_2$—.

In certain embodiments, —X—Y— represents —C(OH)CH$_2$CH$_2$—.

In certain embodiments, —X—Y— represents —CHOCH$_2$—.

In accordance with any one of the foregoing embodiments, in certain embodiments R$^3$ represents phenylene-R$^{3a}$.

In accordance with any one of the foregoing embodiments, in certain embodiments —R$^3$—R$^{3a}$ represents

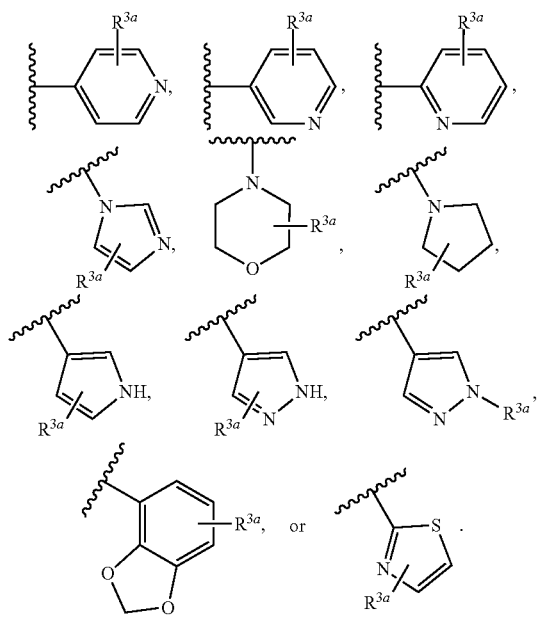

In accordance with any one of the foregoing embodiments, in certain embodiments —R$^3$—R$^{3a}$ represents

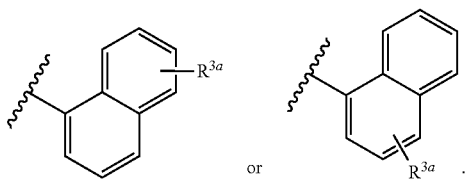

In accordance with any one of the foregoing embodiments, in certain embodiments —R³—R³ᵃ represents

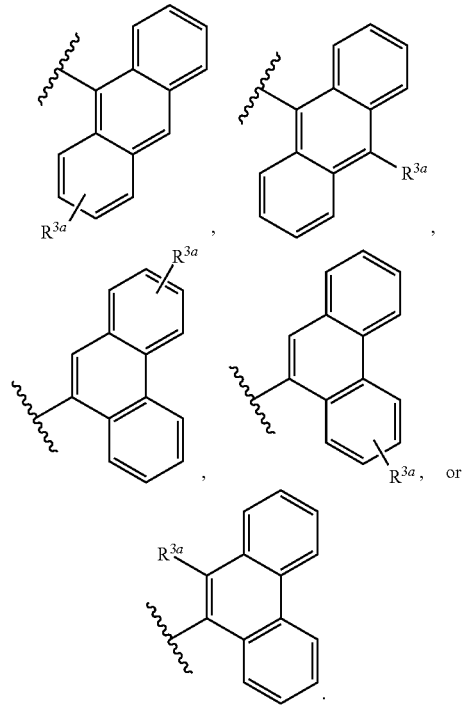

In accordance with any one of the foregoing embodiments, in certain embodiments R³ᵃ is absent.

In accordance with any one of the foregoing embodiments, in certain embodiments R⁴ is cyclopropyl.

In accordance with any one of the foregoing embodiments, in certain embodiments R³ is phenyl, and R³ᵃ is ortho, meta, or para —OH.

In accordance with any one of the foregoing embodiments, in certain embodiments R³ is phenyl, and R³ᵃ is meta or para —NH₂.

In accordance with any one of the foregoing embodiments, in certain embodiments R³ is phenyl, and R³ᵃ is meta or para —CN.

In accordance with any one of the foregoing embodiments, in certain embodiments Z is absent.

In accordance with any one of the foregoing embodiments, in certain embodiments Z represents fluoro.

In accordance with any one of the foregoing embodiments, in certain embodiments Z represents chloro.

In accordance with any one of the foregoing embodiments, in certain embodiments Z represents 2-F, 4-F, 5-F, 6-F, 6-Cl, or 5-(C₃-C₈)cycloalkyl.

In accordance with any one of the foregoing embodiments, in certain embodiments Z represents 6-F.

In accordance with any one of the foregoing embodiments, in certain embodiments R¹ᶜ represents aminomethyl.

In accordance with any one of the foregoing embodiments, in certain embodiments R¹ᶜ represents cyano.

In accordance with any one of the foregoing embodiments, in certain embodiments R¹ᶜ represents —SO₂CH₃.

In accordance with any one of the foregoing embodiments, in certain embodiments R² is —CH₃ or —CF₃.

In accordance with any one of the foregoing embodiments, in certain embodiments R² is —CF₃.

In accordance with any one of the foregoing embodiments, in certain embodiments R² is tert-butyl.

In accordance with any one of the foregoing embodiments, in certain embodiments R² is cyclopropyl.

In accordance with any one of the foregoing embodiments, in certain embodiments R² is —OCH₃.

In accordance with any one of the foregoing embodiments, in certain embodiments R² is —Si(CH₃)₃.

In accordance with any one of the foregoing embodiments, in certain embodiments R² is —CONH₂.

In accordance with any one of the foregoing embodiments, in certain embodiments R² is cyano.

In accordance with any one of the foregoing embodiments, in certain embodiments R² is phenyl.

In certain aspects, the invention provides a compound, or a pharmaceutically acceptable salt thereof, represented by formula XIII:

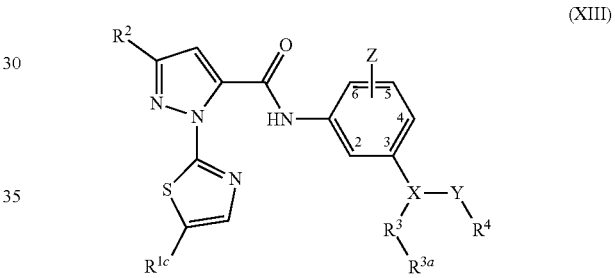

(XIII)

wherein:
X represents CH, C(OH), C(O(C₁-C₆)alkyl), C(O)N, CH₂N, N, C(O), or —O—; provided that:
  if X represents CH, then —Y—R⁴ represents —H or —OH, or both Y and R⁴ are present;
  if X represents C(OH) or C(O(C₁-C₆)alkyl), then —Y—R⁴ is present;
  if X represents C(O)N, then —Y—R⁴ represents H; or —Y—R⁴ represents H, and —R³—R³ᵃ represents H;
  if X represents CH₂N, then —Y—R⁴ represents (C₁-C₆)alkyl;
  if X represents N, then —Y—R⁴ represents H, or both Y and R⁴ are present; and
  if X represents C(O) or —O—, then —Y—R⁴ is absent;
—Y—R⁴, when present, represents —((C₁-C₆)alkyl)-R⁴, —CH₂C(O)—R⁴, —CH₂NH—R⁴, —CH₂N((C₁-C₆)alkyl)-R⁴, —CRᵃRᵇ—R⁴, —NH—R⁴, —NHCH₂—R⁴, —NHC(O)—R⁴, —N((C₁-C₆)alkyl)-R⁴, —N((C₁-C₆)alkyl)CH₂—R⁴, —N((CH₂)₂OH)—R⁴, —N[(C₃-C₈)cycloalkyl(C₁-C₆)alkyl]R⁴, -heterocyclyl-R⁴, —OR⁴, —OCH₂—R⁴, —OC(O)—R⁴, —OC(O)NRᵃRᵇ, —SCH₂R⁴, or —SR⁴, wherein the (C₁-C₆)alkyl moiety of —((C₁-C₆)alkyl)-R⁴ is optionally substituted;
Z is absent or represents halo, hydroxy, (C₁-C₆)alkyl, —CF₃, —OCF₃, (C₁-C₆)alkoxy, aryl, aryloxy, amino, amino(C₁-C₆)alkyl, —C(O)NH₂, cyano, —NHC(O)(C₁-C₆)alkyl, —SO₂(C₁-C₆)alkyl, —SO₂NH₂, or (C₃-C₈)cycloalkyl;

$R^{1c}$ represents halo, amino($C_1$-$C_6$)alkyl, ($C_1$-$C_6$)alkoxy, cyano, —$SO_2CH_3$, formyl, acyl, or optionally substituted aryl;

$R^2$ represents halo, ($C_1$-$C_6$)alkyl, ($C_3$-$C_8$)cycloalkyl, ($C_1$-$C_6$)fluoroalkyl, —$OCH_3$, —$Si(CH_3)_3$, —$CONH_2$, —$C(O)OH$, cyano, or phenyl;

$R^3$, when present, represents —NH—, —O—, optionally substituted aryl, heteroaryl, phenyl, carbocyclyl, or heterocyclyl;

$R^{3a}$ is absent or represents one or more substituents independently selected from the group consisting of halo, hydroxy, ($C_1$-$C_6$)alkyl, —$CF_3$, —$OCF_3$, ($C_1$-$C_6$)alkoxy, aryl, aryloxy, amino, amino($C_1$-$C_6$)alkyl, —$C(O)NH_2$, cyano, —$NHC(O)(C_1$-$C_6)$alkyl, —$SO_2(C_1$-$C_6)$alkyl, and —$SO_2NH_2$;

$R^4$ represents hydrogen, hydroxy, optionally substituted ($C_1$-$C_6$)alkyl, optionally substituted ($C_3$-$C_8$)cycloalkyl, heterocyclyl($C_1$-$C_6$)alkyl, ($C_3$-$C_8$)cycloalkyl($C_1$-$C_6$)alkyl, —$CH_2OH$, —$CH((C_1$-$C_6)$alkyl)OH, —$CH(NH_2)CH((C_1$-$C_6)$alkyl)_2$, optionally substituted aryl, optionally substituted aryl($C_1$-$C_6$)alkyl, heteroaryl, optionally substituted heteroaryl($C_1$-$C_6$)alkyl, —$CH_2S(C_1$-$C_6)$alkyl, amino, or cyano; or —$CH_2$— fused to the 4-position of the ring bearing Z to form a 5- to 7-membered heterocyclic ring with optional substituents;

or, when $R^3$ is phenyl, can represent —NH— fused to the position ortho to X on that phenyl;

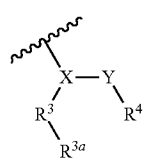

can represent

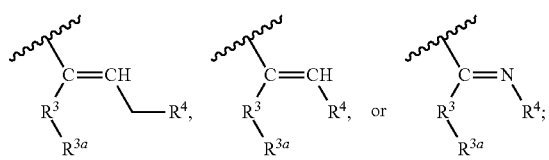

and the stereochemical configuration at any chiral center is R, S, or a mixture of R and S.

In certain embodiments, X represents CH, and both Y and $R^4$ are present.

In certain embodiments, —X—Y— represents —CHNHCH_2—.

In certain embodiments, —X—Y— represents —C(OH)CH_2CH_2—.

In certain embodiments, —X—Y— represents —CHOCH_2—.

In accordance with any one of the foregoing embodiments, in certain embodiments $R^3$ represents phenylene-$R^{3a}$.

In accordance with any one of the foregoing embodiments, in certain embodiments —$R^3$—$R^{3a}$ represents

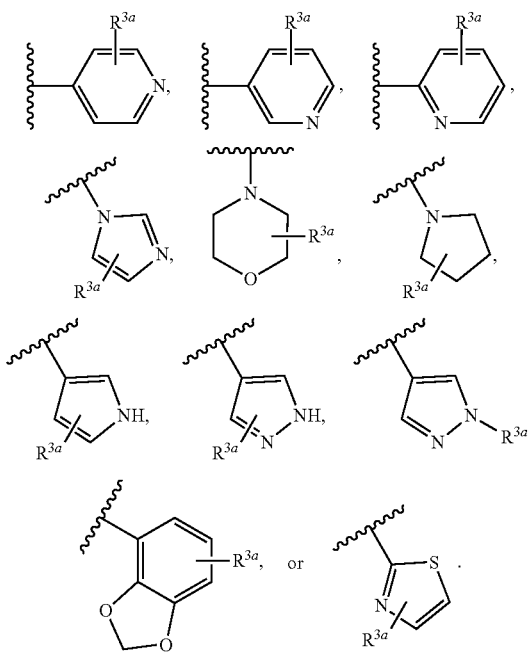

In accordance with any one of the foregoing embodiments, in certain embodiments —$R^3$—$R^{3a}$ represents

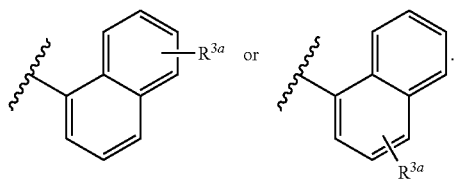

In accordance with any one of the foregoing embodiments, in certain embodiments —$R^3$—$R^{3a}$ represents

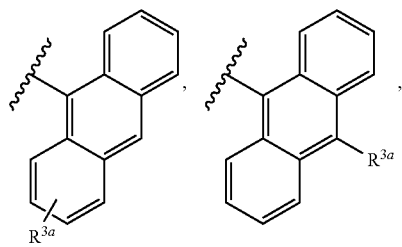

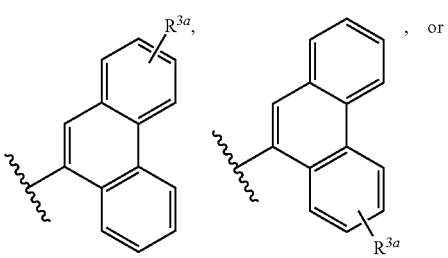

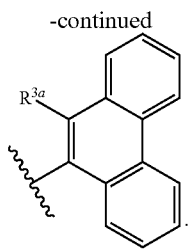

In accordance with any one of the foregoing embodiments, in certain embodiments $R^{3a}$ is absent.

In accordance with any one of the foregoing embodiments, in certain embodiments $R^4$ is cyclopropyl.

In accordance with any one of the foregoing embodiments, in certain embodiments $R^3$ is phenyl, and $R^{3a}$ is ortho, meta, or para —OH.

In accordance with any one of the foregoing embodiments, in certain embodiments $R^3$ is phenyl, and $R^{3a}$ is meta or para —$NH_2$.

In accordance with any one of the foregoing embodiments, in certain embodiments $R^3$ is phenyl, and $R^{3a}$ is meta or para —CN.

In accordance with any one of the foregoing embodiments, in certain embodiments Z is absent.

In accordance with any one of the foregoing embodiments, in certain embodiments Z represents fluoro.

In accordance with any one of the foregoing embodiments, in certain embodiments Z represents chloro.

In accordance with any one of the foregoing embodiments, in certain embodiments Z represents 2-F, 4-F, 5-F, 6-F, 6-Cl, or 5-$(C_3$-$C_8)$cycloalkyl.

In accordance with any one of the foregoing embodiments, in certain embodiments Z represents 6-F.

In accordance with any one of the foregoing embodiments, in certain embodiments $R^{1c}$ represents aminomethyl.

In accordance with any one of the foregoing embodiments, in certain embodiments $R^{1c}$ represents cyano.

In accordance with any one of the foregoing embodiments, in certain embodiments $R^{1c}$ represents —$SO_2CH_3$.

In accordance with any one of the foregoing embodiments, in certain embodiments $R^2$ is —$CH_3$ or —$CF_3$.

In accordance with any one of the foregoing embodiments, in certain embodiments $R^2$ is —$CF_3$.

In accordance with any one of the foregoing embodiments, in certain embodiments $R^2$ is tert-butyl.

In accordance with any one of the foregoing embodiments, in certain embodiments $R^2$ is cyclopropyl.

In accordance with any one of the foregoing embodiments, in certain embodiments $R^2$ is —$OCH_3$.

In accordance with any one of the foregoing embodiments, in certain embodiments $R^2$ is —$Si(CH_3)_3$.

In accordance with any one of the foregoing embodiments, in certain embodiments $R^2$ is —$CONH_2$.

In accordance with any one of the foregoing embodiments, in certain embodiments $R^2$ is cyano.

In accordance with any one of the foregoing embodiments, in certain embodiments $R^2$ is phenyl.

In some aspects, the invention provides a compound, or a pharmaceutically acceptable salt thereof, represented by formula XV:

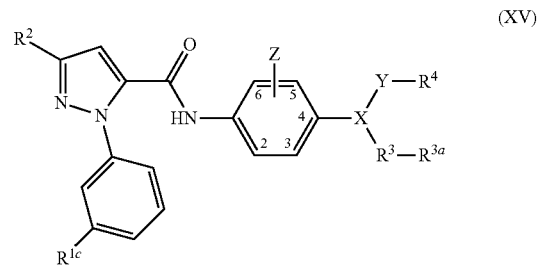

(XV)

wherein:

X represents CH, C(OH), C(O($C_1$-$C_6$)alkyl), C(O)N, $CH_2N$, N, C(O), or —O—; provided that:
if X represents CH, then —Y—$R^4$ represents —H or —OH, or both Y and $R^4$ are present;
if X represents C(OH) or C(O($C_1$-$C_6$)alkyl), then —Y—$R^4$ is present;
if X represents C(O)N, then —Y—$R^4$ represents H; or —Y—$R^4$ represents H, and —$R^3$—$R^{3a}$ represents H;
if X represents $CH_2N$, then —Y—$R^4$ represents ($C_1$-$C_6$)alkyl;
if X represents N, then —Y—$R^4$ represents H, or both Y and $R^4$ are present; and
if X represents C(O) or —O—, then —Y—$R^4$ is absent;
—Y—$R^4$, when present, represents —(($C_1$-$C_6$)alkyl)-$R^4$, —$CH_2C(O)$—$R^4$, —$CH_2NH$—$R^4$, —$CH_2N(($C_1$-$C_6$)alkyl)-$R^4$, —$CR^aR^b$—$R^4$, —NH—$R^4$, —$NHCH_2$—$R^4$, —NHC(O)—$R^4$, —N(($C_1$-$C_6$)alkyl)-$R^4$, —N(($C_1$-$C_6$)alkyl)$CH_2$—$R^4$, —N(($CH_2)_2OH$)—$R^4$, —N[($C_3$-$C_8$)cycloalkyl($C_1$-$C_6$)alkyl]$R^4$, -heterocyclyl-$R^4$, —$OR^4$, —$OCH_2$—$R^4$, —OC(O)—$R^4$, —OC(O)$NR^aR^b$, —$SCH_2R^4$, or —$SR^4$, wherein the ($C_1$-$C_6$)alkyl moiety of —(($C_1$-$C_6$)alkyl)-$R^4$ is optionally substituted;

Z is absent or represents halo, hydroxy, ($C_1$-$C_6$)alkyl, —$CF_3$, —$OCF_3$, ($C_1$-$C_6$)alkoxy, aryl, aryloxy, amino, amino($C_1$-$C_6$)alkyl, —$C(O)NH_2$, cyano, —NHC(O)($C_1$-$C_6$)alkyl, —$SO_2$($C_1$-$C_6$)alkyl, —$SO_2NH_2$, or ($C_3$-$C_8$)cycloalkyl;

$R^{1c}$ represents halo, amino($C_1$-$C_6$)alkyl, ($C_1$-$C_6$)alkoxy, cyano, —$SO_2CH_3$, formyl, acyl, or optionally substituted aryl;

$R^2$ represents halo, ($C_1$-$C_6$)alkyl, ($C_3$-$C_8$)cycloalkyl, ($C_1$-$C_6$)fluoroalkyl, —$OCH_3$, —$Si(CH_3)_3$, —$CONH_2$, —C(O)OH, cyano, or phenyl;

$R^3$, when present, represents —NH—, —O—, optionally substituted aryl, heteroaryl, phenyl, carbocyclyl, or heterocyclyl;

$R^{3a}$ is absent or represents one or more substituents independently selected from the group consisting of halo, hydroxy, ($C_1$-$C_6$)alkyl, —$CF_3$, —$OCF_3$, ($C_1$-$C_6$)alkoxy, aryl, aryloxy, amino, amino($C_1$-$C_6$)alkyl, —$C(O)NH_2$, cyano, —NHC(O)($C_1$-$C_6$)alkyl, —$SO_2$($C_1$-$C_6$)alkyl, and —$SO_2NH_2$;

$R^4$ represents hydrogen, hydroxy, optionally substituted ($C_1$-$C_6$)alkyl, optionally substituted ($C_3$-$C_8$)cycloalkyl, heterocyclyl($C_1$-$C_6$)alkyl, ($C_3$-$C_8$)cycloalkyl($C_1$-$C_6$)alkyl, —$CH_2OH$, —CH(($C_1$-$C_6$)alkyl)OH, —CH($NH_2$)CH(($C_1$-$C_6$)alkyl)$_2$, optionally substituted aryl, optionally substituted aryl($C_1$-$C_6$)alkyl, heteroaryl, optionally substituted heteroaryl($C_1$-$C_6$)alkyl, —$CH_2S$($C_1$-$C_6$)alkyl, amino, or cyano; or —$CH_2$— fused to the 4-position of the ring bearing Z to form a 5- to 7-membered heterocyclic ring with optional substituents;

or, when $R^3$ is phenyl, can represent —NH— fused to the position ortho to X on that phenyl;

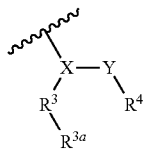

can represent

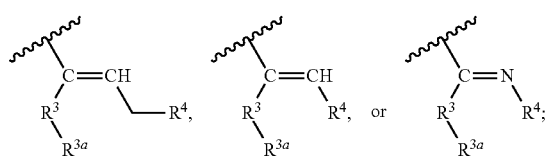

and the stereochemical configuration at any chiral center is R, S, or a mixture of R and S.

In certain embodiments, X represents CH, and both Y and $R^4$ are present.

In certain embodiments, —X—Y— represents —CHN-HCH$_2$—.

In certain embodiments, —X—Y— represents —C(OH)CH$_2$CH$_2$—.

In certain embodiments, —X—Y— represents —CHOCH$_2$—.

In accordance with any one of the foregoing embodiments, in certain embodiments $R^3$ represents phenylene-$R^{3a}$.

In accordance with any one of the foregoing embodiments, in certain embodiments —$R^3$—$R^{3a}$ represents

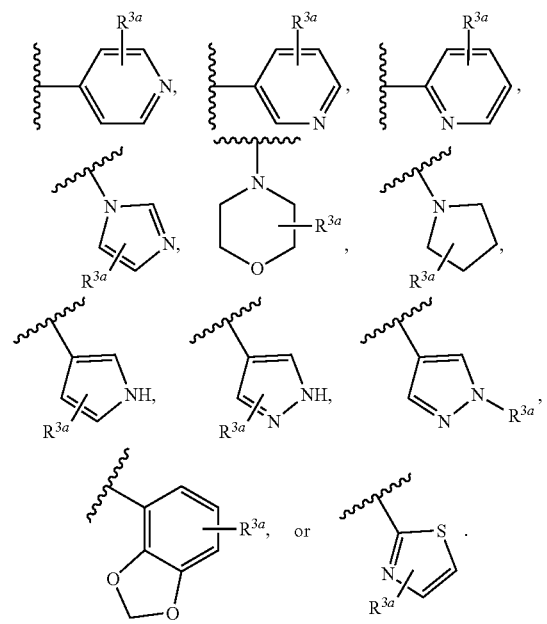

In accordance with any one of the foregoing embodiments, in certain embodiments —$R^3$—$R^{3a}$ represents

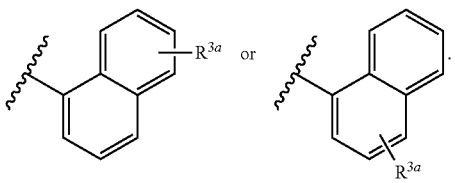

In accordance with any one of the foregoing embodiments, in certain embodiments —$R^3$—$R^{3a}$ represents

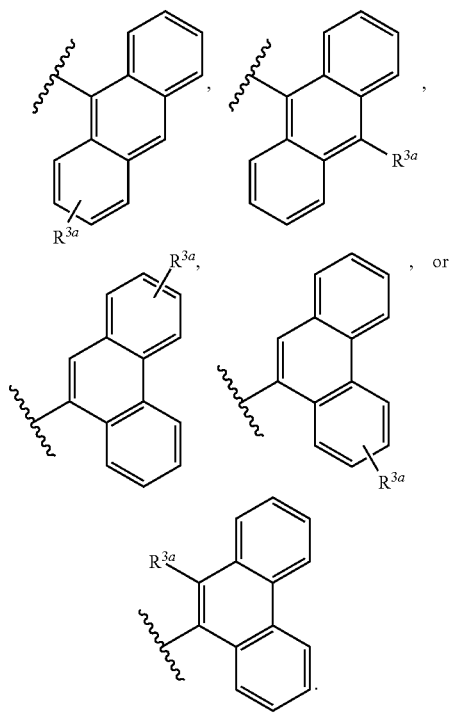

In accordance with any one of the foregoing embodiments, in certain embodiments $R^{3a}$ is absent.

In accordance with any one of the foregoing embodiments, in certain embodiments $R^4$ is cyclopropyl.

In accordance with any one of the foregoing embodiments, in certain embodiments $R^3$ is phenyl, and $R^{3a}$ is ortho, meta, or para —OH.

In accordance with any one of the foregoing embodiments, in certain embodiments $R^3$ is phenyl, and $R^{3a}$ is meta or para —NH$_2$.

In accordance with any one of the foregoing embodiments, in certain embodiments $R^3$ is phenyl, and $R^{3a}$ is meta or para —CN.

In accordance with any one of the foregoing embodiments, in certain embodiments Z is absent.

In accordance with any one of the foregoing embodiments, in certain embodiments Z represents fluoro.

In accordance with any one of the foregoing embodiments, in certain embodiments Z represents chloro.

In accordance with any one of the foregoing embodiments, in certain embodiments Z represents 2-F, 3-F, 5-F, 6-F, 6-Cl, or 5-(C$_3$-C$_8$)cycloalkyl.

In accordance with any one of the foregoing embodiments, in certain embodiments Z represents 6-F.

In accordance with any one of the foregoing embodiments, in certain embodiments $R^{1c}$ represents aminomethyl.

In accordance with any one of the foregoing embodiments, in certain embodiments $R^{1c}$ represents cyano.

In accordance with any one of the foregoing embodiments, in certain embodiments $R^{1c}$ represents —SO$_2$CH$_3$.

In accordance with any one of the foregoing embodiments, in certain embodiments $R^2$ is —CH$_3$ or —CF$_3$.

In accordance with any one of the foregoing embodiments, in certain embodiments $R^2$ is —CF$_3$.

In accordance with any one of the foregoing embodiments, in certain embodiments $R^2$ is tert-butyl.

In accordance with any one of the foregoing embodiments, in certain embodiments $R^2$ is cyclopropyl.

In accordance with any one of the foregoing embodiments, in certain embodiments $R^2$ is —OCH$_3$.

In accordance with any one of the foregoing embodiments, in certain embodiments $R^2$ is —Si(CH$_3$)$_3$.

In accordance with any one of the foregoing embodiments, in certain embodiments $R^2$ is —CONH$_2$.

In accordance with any one of the foregoing embodiments, in certain embodiments $R^2$ is cyano.

In accordance with any one of the foregoing embodiments, in certain embodiments $R^2$ is phenyl.

In certain aspects, the invention provides a compound, or a pharmaceutically acceptable salt thereof, represented by formula XVII:

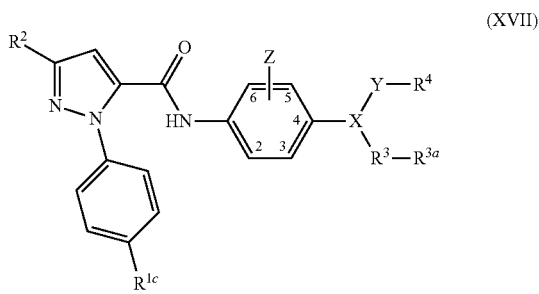

(XVII)

wherein:

X represents CH, C(OH), C(O(C$_1$-C$_6$)alkyl), C(O)N, CH$_2$N, N, C(O), or —O—; provided that:
if X represents CH, then —Y—R$^4$ represents —H or —OH, or both Y and R$^4$ are present;
if X represents C(OH) or C(O(C$_1$-C$_6$)alkyl), then —Y—R$^4$ is present;
if X represents C(O)N, then —Y—R$^4$ represents H; or —Y—R$^4$ represents H, and —R$^3$—R$^{3a}$ represents H;
if X represents CH$_2$N, then —Y—R$^4$ represents (C$_1$-C$_6$)alkyl;
if X represents N, then —Y—R$^4$ represents H, or both Y and R$^4$ are present; and
if X represents C(O) or —O—, then —Y—R$^4$ is absent;
—Y—R$^4$, when present, represents —((C$_1$-C$_6$)alkyl)-R$^4$, —CH$_2$C(O)—R$^4$, —CH$_2$NH—R$^4$, —CH$_2$N((C$_1$-C$_6$) alkyl)-R$^4$, —CR$^a$R$^b$—R$^4$, —NH—R$^4$, —NHCH$_2$—R$^4$, —NHC(O)—R$^4$, —N((C$_1$-C$_6$)alkyl)-R$^4$, —N((C$_1$-C$_6$) alkyl)CH$_2$—R$^4$, —N((CH$_2$)$_2$OH)—R$^4$, —N[(C$_3$-C$_8$) cycloalkyl(C$_1$-C$_6$)alkyl]R$^4$, -heterocyclyl-R$^4$, —OR$^4$, —OCH$_2$—R$^4$, —OC(O)—R$^4$, —OC(O)NR$^a$R$^b$, —SCH$_2$R$^4$, or —SR$^4$, wherein the (C$_1$-C$_6$)alkyl moiety of —((C$_1$-C$_6$)alkyl)-R$^4$ is optionally substituted;
Z is absent or represents halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O) (C$_1$-C$_6$)alkyl, —SO$_2$(C$_1$-C$_6$)alkyl, —SO$_2$NH$_2$, or (C$_3$-C$_8$)cycloalkyl;

$R^{1c}$ represents halo, amino(C$_1$-C$_6$)alkyl, (C$_1$-C$_6$)alkoxy, cyano, —SO$_2$CH$_3$, formyl, acyl, or optionally substituted aryl;

$R^2$ represents halo, (C$_1$-C$_6$)alkyl, (C$_3$-C$_8$)cycloalkyl, (C$_1$-C$_6$)fluoroalkyl, —OCH$_3$, —Si(CH$_3$)$_3$, —CONH$_2$, —C(O)OH, cyano, or phenyl;

$R^3$, when present, represents —NH—, —O—, optionally substituted aryl, heteroaryl, phenyl, carbocyclyl, or heterocyclyl;

$R^{3a}$ is absent or represents one or more substituents independently selected from the group consisting of halo, hydroxy, (C$_1$-C$_6$)alkyl, —CF$_3$, —OCF$_3$, (C$_1$-C$_6$) alkoxy, aryl, aryloxy, amino, amino(C$_1$-C$_6$)alkyl, —C(O)NH$_2$, cyano, —NHC(O)(C$_1$-C$_6$)alkyl, —SO$_2$ (C$_1$-C$_6$)alkyl, and —SO$_2$NH$_2$;

$R^4$ represents hydrogen, hydroxy, optionally substituted (C$_1$-C$_6$)alkyl, optionally substituted (C$_3$-C$_8$)cycloalkyl, heterocyclyl(C$_1$-C$_6$)alkyl, (C$_3$-C$_8$)cycloalkyl(C$_1$-C$_6$) alkyl, —CH$_2$OH, —CH((C$_1$-C$_6$)alkyl)OH, —CH (NH$_2$)CH((C$_1$-C$_6$)alkyl)$_2$, optionally substituted aryl, optionally substituted aryl(C$_1$-C$_6$)alkyl, heteroaryl, optionally substituted heteroaryl(C$_1$-C$_6$)alkyl, —CH$_2$S (C$_1$-C$_6$)alkyl, amino, or cyano; or —CH$_2$— fused to the 4-position of the ring bearing Z to form a 5- to 7-membered heterocyclic ring with optional substituents;

or, when R$^3$ is phenyl, can represent —NH— fused to the position ortho to X on that phenyl;

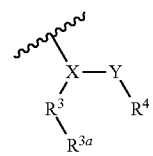

can represent

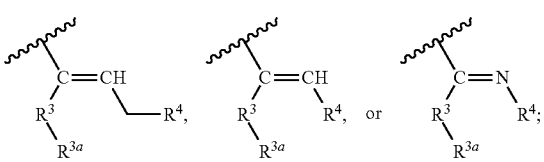

and the stereochemical configuration at any chiral center is R, S, or a mixture of R and S.

In certain embodiments, X represents CH, and both Y and R$^4$ are present.

In certain embodiments, —X—Y— represents —CHN-HCH$_2$—.

In certain embodiments, —X—Y— represents —C(OH) CH$_2$CH$_2$—.

In certain embodiments, —X—Y— represents —CHOCH$_2$—.

In accordance with any one of the foregoing embodiments, in certain embodiments R$^3$ represents phenylene-R$^{3a}$.

In accordance with any one of the foregoing embodiments, in certain embodiments —R$^3$—R$^{3a}$ represents In accordance with any one of the foregoing embodiments, in certain embodiments —R³—R³ᵃ represents

[chemical structures]

In accordance with any one of the foregoing embodiments, in certain embodiments —R³—R³ represents

[chemical structures]

In accordance with any one of the foregoing embodiments, in certain embodiments R³ᵃ is absent.

In accordance with any one of the foregoing embodiments, in certain embodiments R⁴ is cyclopropyl.

In accordance with any one of the foregoing embodiments, in certain embodiments R³ is phenyl, and R³ᵃ is ortho, meta, or para —OH.

In accordance with any one of the foregoing embodiments, in certain embodiments R³ is phenyl, and R³ᵃ is meta or para —NH₂.

In accordance with any one of the foregoing embodiments, in certain embodiments R³ is phenyl, and R³ᵃ is meta or para —CN.

In accordance with any one of the foregoing embodiments, in certain embodiments Z is absent.

In accordance with any one of the foregoing embodiments, in certain embodiments Z represents fluoro.

In accordance with any one of the foregoing embodiments, in certain embodiments Z represents chloro.

In accordance with any one of the foregoing embodiments, in certain embodiments Z represents 2-F, 3-F, 5-F, 6-F, 6-Cl, or 5-(C₃-C₈)cycloalkyl.

In accordance with any one of the foregoing embodiments, in certain embodiments Z represents 6-F.

In accordance with any one of the foregoing embodiments, in certain embodiments R¹ᶜ represents aminomethyl.

In accordance with any one of the foregoing embodiments, in certain embodiments R¹ᶜ represents cyano.

In accordance with any one of the foregoing embodiments, in certain embodiments R¹ᶜ represents —SO₂CH₃.

In accordance with any one of the foregoing embodiments, in certain embodiments R² is —CH₃ or —CF₃.

In accordance with any one of the foregoing embodiments, in certain embodiments R² is —CF₃.

In accordance with any one of the foregoing embodiments, in certain embodiments R² is tert-butyl.

In accordance with any one of the foregoing embodiments, in certain embodiments R² is cyclopropyl.

In accordance with any one of the foregoing embodiments, in certain embodiments R² is —OCH₃.

In accordance with any one of the foregoing embodiments, in certain embodiments R² is —Si(CH₃)₃.

In accordance with any one of the foregoing embodiments, in certain embodiments R² is —CONH₂.

In accordance with any one of the foregoing embodiments, in certain embodiments R² is cyano.

In accordance with any one of the foregoing embodiments, in certain embodiments R² is phenyl.

In certain aspects, the invention provides a compound, or a pharmaceutically acceptable salt thereof, represented by formula XIX:

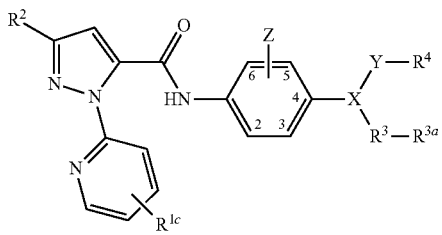

(XIX)

wherein:

X represents CH, C(OH), C(O(C$_1$-C$_6$)alkyl), C(O)N, CH$_2$N, N, C(O), or —O—; provided that:
  if X represents CH, then —Y—R$^4$ represents —H or —OH, or both Y and R$^4$ are present;
  if X represents C(OH) or C(O(C$_1$-C$_6$)alkyl), then —Y—R$^4$ is present;
  if X represents C(O)N, then —Y—R$^4$ represents H; or —Y—R$^4$ represents H, and —R$^3$—R$^{3a}$ represents H;
  if X represents CH$_2$N, then —Y—R$^4$ represents (C$_1$-C$_6$)alkyl;
  if X represents N, then —Y—R$^4$ represents H, or both Y and R$^4$ are present; and
  if X represents C(O) or —O—, then —Y—R$^4$ is absent;

—Y—R$^4$, when present, represents —((C$_1$-C$_6$)alkyl)-R$^4$, —CH$_2$C(O)—R$^4$, —CH$_2$NH—R$^4$, —CH$_2$N((C$_1$-C$_6$)alkyl)-R$^4$, —CR$^a$R$^b$—R$^4$, —NH—R$^4$, —NHCH$_2$—R$^4$, —NHC(O)—R$^4$, —N((C$_1$-C$_6$)alkyl)-R$^4$, —N((C$_1$-C$_6$)alkyl)CH$_2$—R$^4$, —N((CH$_2$)$_2$OH)—R$^4$, —N[(C$_3$-C$_8$)cycloalkyl(C$_1$-C$_6$)alkyl]R$^4$, -heterocyclyl-R$^4$, —OR$^4$, —OCH$_2$—R$^4$, —OC(O)—R$^4$, —OC(O)NR$^a$R$^b$, —SCH$_2$R$^4$, or —SR$^4$, wherein the (C$_1$-C$_6$)alkyl moiety of —((C$_1$-C$_6$)alkyl)-R$^4$ is optionally substituted;

Z is absent or represents halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, —SO$_2$NH$_2$, or (C$_3$-C$_8$)cycloalkyl;

R$^{1c}$ represents halo, amino(C$_1$-C$_6$)alkyl, (C$_1$-C$_6$)alkoxy, cyano, —SO$_2$CH$_3$, formyl, acyl, or optionally substituted aryl;

R$^2$ represents halo, (C$_1$-C$_6$)alkyl, (C$_3$-C$_8$)cycloalkyl, (C$_1$-C$_6$)fluoroalkyl, —OCH$_3$, —Si(CH$_3$)$_3$, —CONH$_2$, —C(O)OH, cyano, or phenyl;

R$^3$, when present, represents —NH—, —O—, optionally substituted aryl, heteroaryl, phenyl, carbocyclyl, or heterocyclyl;

R$^{3a}$ is absent or represents one or more substituents independently selected from the group consisting of halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, and —SO$_2$NH$_2$;

R$^4$ represents hydrogen, hydroxy, optionally substituted (C$_1$-C$_6$)alkyl, optionally substituted (C$_3$-C$_8$)cycloalkyl, heterocyclyl(C$_1$-C$_6$)alkyl, (C$_3$-C$_8$)cycloalkyl(C$_1$-C$_6$)alkyl, —CH$_2$OH, —CH((C$_1$-C$_6$)alkyl)OH, —CH(NH$_2$)CH((C$_1$-C$_6$)alkyl)$_2$, optionally substituted aryl, optionally substituted aryl(C$_1$-C$_6$)alkyl, heteroaryl, optionally substituted heteroaryl(C$_1$-C$_6$)alkyl, —CH$_2$S(C$_1$-C$_6$)alkyl, amino, or cyano; or —CH$_2$— fused to the 4-position of the ring bearing Z to form a 5- to 7-membered heterocyclic ring with optional substituents;

or, when R$^3$ is phenyl, can represent —NH— fused to the position ortho to X on that phenyl;

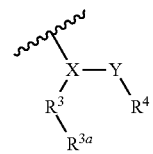

can represent

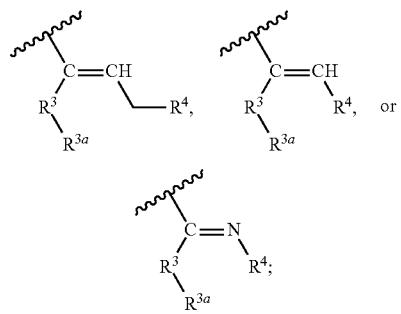

and the stereochemical configuration at any chiral center is R, S, or a mixture of R and S.

In certain embodiments, X represents CH, and both Y and R$^4$ are present.

In certain embodiments, —X—Y— represents —CHNHCH$_2$—.

In certain embodiments, —X—Y— represents —C(OH)CH$_2$CH$_2$—.

In certain embodiments, —X—Y— represents —CHOCH$_2$—.

In accordance with any one of the foregoing embodiments, in certain embodiments R$^3$ represents phenylene-R$^{3a}$.

In accordance with any one of the foregoing embodiments, in certain embodiments —R$^3$—R$^{3a}$ represents

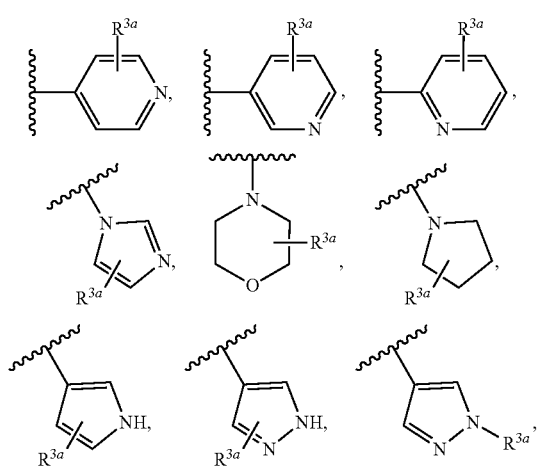

-continued

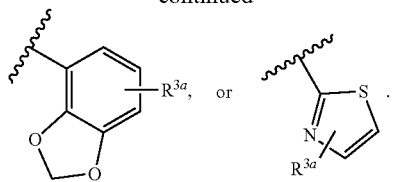

In accordance with any one of the foregoing embodiments, in certain embodiments —R³—R³ᵃ represents

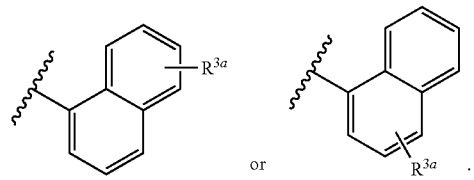

In accordance with any one of the foregoing embodiments, in certain embodiments —R³—R³ᵃ represents

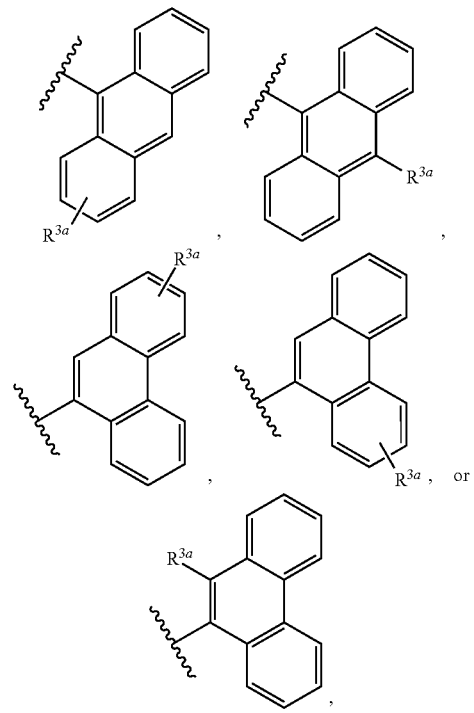

In accordance with any one of the foregoing embodiments, in certain embodiments R³ᵃ is absent.

In accordance with any one of the foregoing embodiments, in certain embodiments R⁴ is cyclopropyl.

In accordance with any one of the foregoing embodiments, in certain embodiments R³ is phenyl, and R³ᵃ is ortho, meta, or para —OH.

In accordance with any one of the foregoing embodiments, in certain embodiments R³ is phenyl, and R³ᵃ is meta or para —NH₂.

In accordance with any one of the foregoing embodiments, in certain embodiments R³ is phenyl, and R³ᵃ is meta or para —CN.

In accordance with any one of the foregoing embodiments, in certain embodiments Z is absent.

In accordance with any one of the foregoing embodiments, in certain embodiments Z represents fluoro.

In accordance with any one of the foregoing embodiments, in certain embodiments Z represents chloro.

In accordance with any one of the foregoing embodiments, in certain embodiments Z represents 2-F, 3-F, 5-F, 6-F, 6-Cl, or 5-(C₃-C₈)cycloalkyl.

In accordance with any one of the foregoing embodiments, in certain embodiments Z represents 6-F.

In accordance with any one of the foregoing embodiments, in certain embodiments R¹ᶜ represents aminomethyl.

In accordance with any one of the foregoing embodiments, in certain embodiments R¹ᶜ represents cyano.

In accordance with any one of the foregoing embodiments, in certain embodiments R¹ᶜ represents —SO₂CH₃.

In accordance with any one of the foregoing embodiments, in certain embodiments R² is —CH₃ or —CF₃.

In accordance with any one of the foregoing embodiments, in certain embodiments R² is —CF₃.

In accordance with any one of the foregoing embodiments, in certain embodiments R² is tert-butyl.

In accordance with any one of the foregoing embodiments, in certain embodiments R² is cyclopropyl.

In accordance with any one of the foregoing embodiments, in certain embodiments R² is —OCH₃.

In accordance with any one of the foregoing embodiments, in certain embodiments R² is —Si(CH₃)₃.

In accordance with any one of the foregoing embodiments, in certain embodiments R² is —CONH₂.

In accordance with any one of the foregoing embodiments, in certain embodiments R² is cyano.

In accordance with any one of the foregoing embodiments, in certain embodiments R² is phenyl.

In certain aspects, the invention provides a compound, or a pharmaceutically acceptable salt thereof, represented by formula XXI:

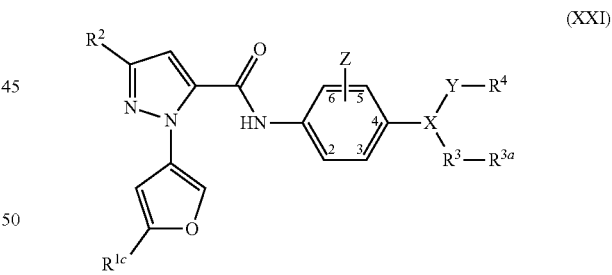

(XXI)

wherein:
X represents CH, C(OH), C(O(C₁-C₆)alkyl), C(O)N, CH₂N, N, C(O), or —O—; provided that:
  if X represents CH, then —Y—R⁴ represents —H or —OH, or both Y and R⁴ are present;
  if X represents C(OH) or C(O(C₁-C₆)alkyl), then —Y—R⁴ is present;
  if X represents C(O)N, then —Y—R⁴ represents H; or —Y—R⁴ represents H, and —R³—R³ᵃ represents H;
  if X represents CH₂N, then —Y—R⁴ represents (C₁-C₆)alkyl;
  if X represents N, then —Y—R⁴ represents H, or both Y and R⁴ are present; and
  if X represents C(O) or —O—, then —Y—R⁴ is absent;

—Y—R$^4$, when present, represents —((C$_1$-C$_6$)alkyl)-R$^4$, —CH$_2$C(O)—R$^4$, —CH$_2$NH—R$^4$, —CH$_2$N((C$_1$-C$_6$)alkyl)-R$^4$, —CR$^a$R$^b$—R$^4$, —NH—R$^4$, —NHCH$_2$—R$^4$, —NHC(O)—R$^4$, —N((C$_1$-C$_6$)alkyl)-R$^4$, —N((C$_1$-C$_6$)alkyl)CH$_2$—R$^4$, —N((CH$_2$)$_2$OH)—R$^4$, —N[(C$_3$-C$_8$)cycloalkyl(C$_1$-C$_6$)alkyl]R$^4$, -heterocyclyl-R$^4$, —OR$^4$, —OCH$_2$—R$^4$, —OC(O)—R$^4$, —OC(O)NR$^a$R$^b$, —SCH$_2$R$^4$, or —SR$^4$, wherein the (C$_1$-C$_6$)alkyl moiety of —((C$_1$-C$_6$)alkyl)-R$^4$ is optionally substituted;

Z is absent or represents halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, —SO$_2$NH$_2$, or (C$_3$-C$_8$)cycloalkyl;

R$^{1c}$ represents halo, amino(C$_1$-C$_6$)alkyl, (C$_1$-C$_6$)alkoxy, cyano, —SO$_2$CH$_3$, formyl, acyl, or optionally substituted aryl;

R$^2$ represents halo, (C$_1$-C$_6$)alkyl, (C$_3$-C$_8$)cycloalkyl, (C$_1$-C$_6$)fluoroalkyl, —OCH$_3$, —Si(CH$_3$)$_3$, —CONH$_2$, —C(O)OH, cyano, or phenyl;

R$^3$, when present, represents —NH—, —O—, optionally substituted aryl, heteroaryl, phenyl, carbocyclyl, or heterocyclyl;

R$^{3a}$ is absent or represents one or more substituents independently selected from the group consisting of halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, and —SO$_2$NH$_2$;

R$^4$ represents hydrogen, hydroxy, optionally substituted (C$_1$-C$_6$)alkyl, optionally substituted (C$_3$-C$_8$)cycloalkyl, heterocyclyl(C$_1$-C$_6$)alkyl, (C$_3$-C$_8$)cycloalkyl(C$_1$-C$_6$)alkyl, —CH$_2$OH, —CH((C$_1$-C$_6$)alkyl)OH, —CH(NH$_2$)CH((C$_1$-C$_6$)alkyl)$_2$, optionally substituted aryl, optionally substituted aryl(C$_1$-C$_6$)alkyl, heteroaryl, optionally substituted heteroaryl(C$_1$-C$_6$)alkyl, —CH$_2$S(C$_1$-C$_6$)alkyl, amino, or cyano; or —CH$_2$— fused to the 4-position of the ring bearing Z to form a 5- to 7-membered heterocyclic ring with optional substituents;

or, when R$^3$ is phenyl, can represent —NH— fused to the position ortho to X on that phenyl;

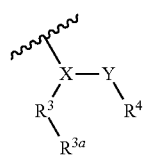

can represent

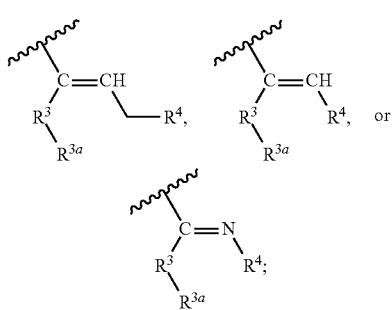

and the stereochemical configuration at any chiral center is R, S, or a mixture of R and S.

In certain embodiments, X represents CH, and both Y and R$^4$ are present.

In certain embodiments, —X—Y— represents —CHNHCH$_2$—.

In certain embodiments, —X—Y— represents —C(OH)CH$_2$CH$_2$—.

In certain embodiments, —X—Y— represents —CHOCH$_2$—.

In accordance with any one of the foregoing embodiments, in certain embodiments R$^3$ represents phenylene-R$^{3a}$.

In accordance with any one of the foregoing embodiments, in certain embodiments —R$^3$—R$^{3a}$ represents

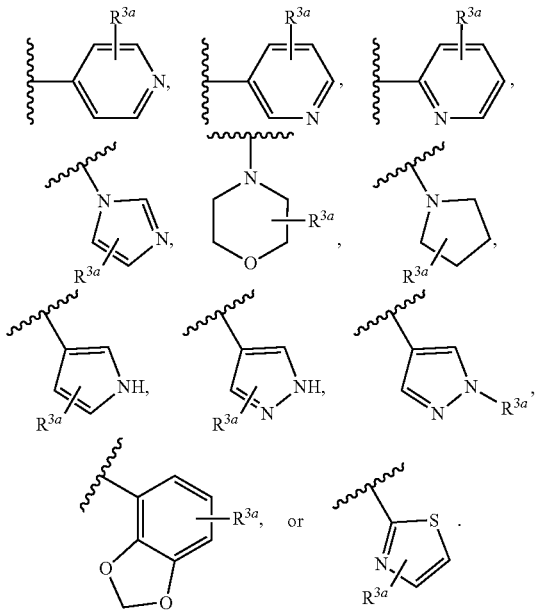

In accordance with any one of the foregoing embodiments, in certain embodiments —R$^3$—R$^{3a}$ represents

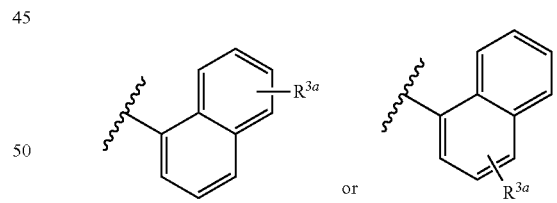

In accordance with any one of the foregoing embodiments, in certain embodiments —R$^3$—R$^{3a}$ represents

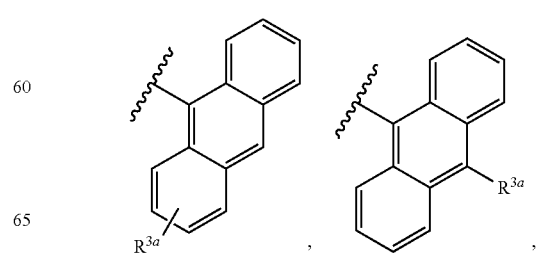

75

-continued

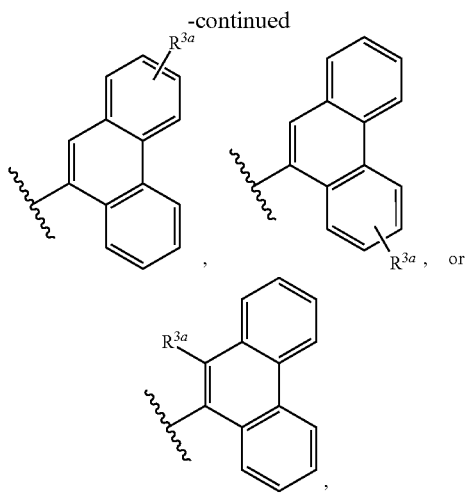

In accordance with any one of the foregoing embodiments, in certain embodiments $R^{3a}$ is absent.

In accordance with any one of the foregoing embodiments, in certain embodiments $R^4$ is cyclopropyl.

In accordance with any one of the foregoing embodiments, in certain embodiments $R^3$ is phenyl, and $R^{3a}$ is ortho, meta, or para —OH.

In accordance with any one of the foregoing embodiments, in certain embodiments $R^3$ is phenyl, and $R^{3a}$ is meta or para —NH$_2$.

In accordance with any one of the foregoing embodiments, in certain embodiments $R^3$ is phenyl, and $R^{3a}$ is meta or para —CN.

In accordance with any one of the foregoing embodiments, in certain embodiments Z is absent.

In accordance with any one of the foregoing embodiments, in certain embodiments Z represents fluoro.

In accordance with any one of the foregoing embodiments, in certain embodiments Z represents chloro.

In accordance with any one of the foregoing embodiments, in certain embodiments Z represents 2-F, 3-F, 5-F, 6-F, 6-Cl, or 5-($C_3$-$C_8$)cycloalkyl.

In accordance with any one of the foregoing embodiments, in certain embodiments Z represents 6-F.

In accordance with any one of the foregoing embodiments, in certain embodiments $R^{1c}$ represents aminomethyl.

In accordance with any one of the foregoing embodiments, in certain embodiments $R^{1c}$ represents cyano.

In accordance with any one of the foregoing embodiments, in certain embodiments $R^{1c}$ represents —SO$_2$CH$_3$.

In accordance with any one of the foregoing embodiments, in certain embodiments $R^2$ is —CH$_3$ or —CF$_3$.

In accordance with any one of the foregoing embodiments, in certain embodiments $R^2$ is —CF$_3$.

In accordance with any one of the foregoing embodiments, in certain embodiments $R^2$ is tert-butyl.

In accordance with any one of the foregoing embodiments, in certain embodiments $R^2$ is cyclopropyl.

In accordance with any one of the foregoing embodiments, in certain embodiments $R^2$ is —OCH$_3$.

In accordance with any one of the foregoing embodiments, in certain embodiments $R^2$ is —Si(CH$_3$)$_3$.

In accordance with any one of the foregoing embodiments, in certain embodiments $R^2$ is —CONH$_2$.

In accordance with any one of the foregoing embodiments, in certain embodiments $R^2$ is cyano.

76

In accordance with any one of the foregoing embodiments, in certain embodiments $R^2$ is phenyl.

In certain aspects, the invention provides a compound, or a pharmaceutically acceptable salt thereof, represented by formula XXIII:

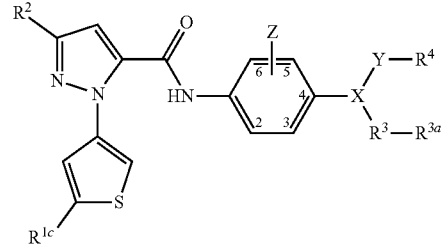

(XXIII)

wherein:
X represents CH, C(OH), C(O(C$_1$-C$_6$)alkyl), C(O)N, CH$_2$N, N, C(O), or —O—; provided that:
  if X represents CH, then —Y—R$^4$ represents —H or —OH, or both Y and R$^4$ are present;
  if X represents C(OH) or C(O(C$_1$-C$_6$)alkyl), then —Y—R$^4$ is present;
  if X represents C(O)N, then —Y—R$^4$ represents H; or —Y—R$^4$ represents H, and —R$^3$—R$^{3a}$ represents H;
  if X represents CH$_2$N, then —Y—R$^4$ represents (C$_1$-C$_6$)alkyl;
  if X represents N, then —Y—R$^4$ represents H, or both Y and R$^4$ are present; and
  if X represents C(O) or —O—, then —Y—R$^4$ is absent;
—Y—R$^4$, when present, represents —((C$_1$-C$_6$)alkyl)-R$^4$, —CH$_2$C(O)—R$^4$, —CH$_2$NH—R$^4$, —CH$_2$N((C$_1$-C$_6$)alkyl)-R$^4$, —CR$^a$R$^b$—R$^4$, —NH—R$^4$, —NHCH$_2$—R$^4$, —NHC(O)—R$^4$, —N((C$_1$-C$_6$)alkyl)-R$^4$, —N((C$_1$-C$_6$)alkyl)CH$_2$—R$^4$, —N((CH$_2$)$_2$OH)—R$^4$, —N[(C$_3$-C$_8$)cycloalkyl(C$_1$-C$_6$)alkyl]R$^4$, -heterocyclyl-R$^4$, —OR$^4$, —OCH$_2$—R$^4$, —OC(O)—R$^4$, —OC(O)NR$^a$R$^b$, —SCH$_2$R$^4$, or —SR$^4$, wherein the (C$_1$-C$_6$)alkyl moiety of —((C$_1$-C$_6$)alkyl)-R$^4$ is optionally substituted;
Z is absent or represents halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, —SO$_2$NH$_2$, or (C$_3$-C$_8$)cycloalkyl;
$R^{1c}$ represents halo, amino(C$_1$-C$_6$)alkyl, (C$_1$-C$_6$)alkoxy, cyano, —SO$_2$CH$_3$, formyl, acyl, or optionally substituted aryl;
$R^2$ represents halo, (C$_1$-C$_6$)alkyl, (C$_3$-C$_8$)cycloalkyl, (C$_1$-C$_6$)fluoroalkyl, —OCH$_3$, —Si(CH$_3$)$_3$, —CONH$_2$, —C(O)OH, cyano, or phenyl;
$R^3$, when present, represents —NH—, —O—, optionally substituted aryl, heteroaryl, phenyl, carbocyclyl, or heterocyclyl;
$R^{3a}$ is absent or represents one or more substituents independently selected from the group consisting of halo, hydroxy, (C$_1$-C$_6$)alkyl, —CF$_3$, —OCF$_3$, (C$_1$-C$_6$)alkoxy, aryl, aryloxy, amino, amino(C$_1$-C$_6$)alkyl, —C(O)NH$_2$, cyano, —NHC(O)(C$_1$-C$_6$)alkyl, —SO$_2$(C$_1$-C$_6$)alkyl, and —SO$_2$NH$_2$;
$R^4$ represents hydrogen, hydroxy, optionally substituted (C$_1$-C$_6$)alkyl, optionally substituted (C$_3$-C$_8$)cycloalkyl, heterocyclyl(C$_1$-C$_6$)alkyl, (C$_3$-C$_8$)cycloalkyl(C$_1$-C$_6$)alkyl, —CH$_2$OH, —CH((C$_1$-C$_6$)alkyl)OH, —CH (NH$_2$)CH((C$_1$-C$_6$)alkyl)$_2$, optionally substituted aryl, optionally substituted aryl(C$_1$-C$_6$)alkyl, heteroaryl, optionally substituted heteroaryl(C$_1$-C$_6$)alkyl, —CH$_2$S(C$_1$-C$_6$)alkyl, amino, or cyano; or —CH$_2$— fused to the 4-position of the ring bearing Z to form a 5- to 7-membered heterocyclic ring with optional substituents;

or, when R$^3$ is phenyl, can represent —NH— fused to the position ortho to X on that phenyl;

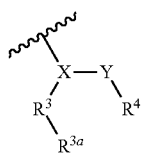

can represent

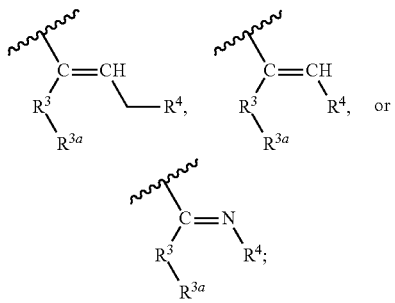

and
the stereochemical configuration at any chiral center is R, S, or a mixture of R and S.

In certain embodiments, X represents CH, and both Y and R$^4$ are present.

In certain embodiments, —X—Y— represents —CHNHCH$_2$—.

In certain embodiments, —X—Y— represents —C(OH)CH$_2$CH$_2$—.

In certain embodiments, —X—Y— represents —CHOCH$_2$—.

In accordance with any one of the foregoing embodiments, in certain embodiments R$^3$ represents phenylene-R$^{3a}$.

In accordance with any one of the foregoing embodiments, in certain embodiments —R$^3$—R$^{3a}$ represents

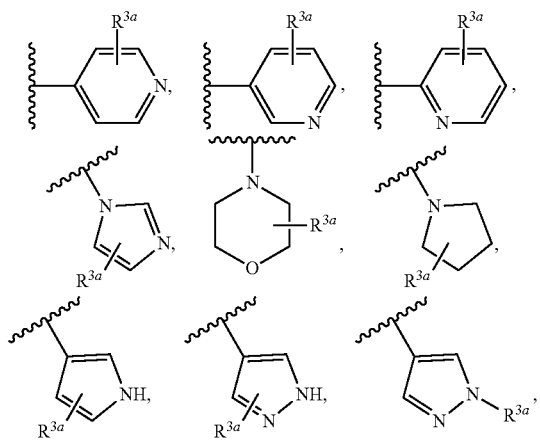

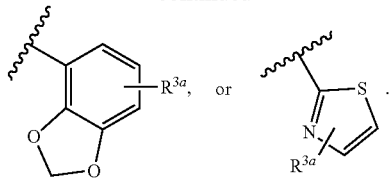

In accordance with any one of the foregoing embodiments, in certain embodiments —R$^3$—R$^{3a}$ represents

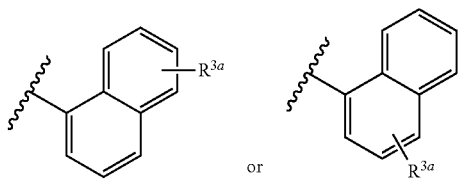

In accordance with any one of the foregoing embodiments, in certain embodiments —R$^3$—R$^{3a}$ represents

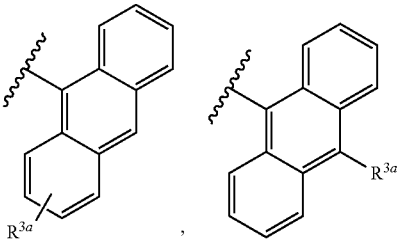

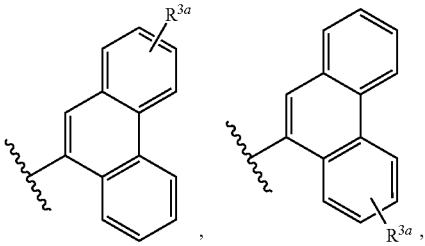

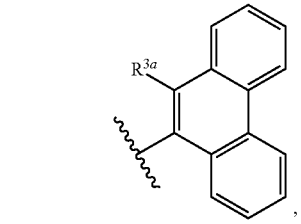

In accordance with any one of the foregoing embodiments, in certain embodiments R$^{3a}$ is absent.

In accordance with any one of the foregoing embodiments, in certain embodiments R$^4$ is cyclopropyl.

In accordance with any one of the foregoing embodiments, in certain embodiments R$^3$ is phenyl, and R$^{3a}$ is ortho, meta, or para —OH.

In accordance with any one of the foregoing embodiments, in certain embodiments R$^3$ is phenyl, and R$^{3a}$ is meta or para —NH$_2$.

In accordance with any one of the foregoing embodiments, in certain embodiments R$^3$ is phenyl, and R$^{3a}$ is meta or para —CN.

In accordance with any one of the foregoing embodiments, in certain embodiments Z is absent.

In accordance with any one of the foregoing embodiments, in certain embodiments Z represents fluoro.

In accordance with any one of the foregoing embodiments, in certain embodiments Z represents chloro.

In accordance with any one of the foregoing embodiments, in certain embodiments Z represents 2-F, 3-F, 5-F, 6-F, 6-Cl, or 5-$(C_3$-$C_8)$cycloalkyl.

In accordance with any one of the foregoing embodiments, in certain embodiments Z represents 6-F.

In accordance with any one of the foregoing embodiments, in certain embodiments $R^{1c}$ represents aminomethyl.

In accordance with any one of the foregoing embodiments, in certain embodiments $R^{1c}$ represents cyano.

In accordance with any one of the foregoing embodiments, in certain embodiments $R^{1c}$ represents —$SO_2CH_3$.

In accordance with any one of the foregoing embodiments, in certain embodiments $R^2$ is —$CH_3$ or —$CF_3$.

In accordance with any one of the foregoing embodiments, in certain embodiments $R^2$ is —$CF_3$.

In accordance with any one of the foregoing embodiments, in certain embodiments $R^2$ is tert-butyl.

In accordance with any one of the foregoing embodiments, in certain embodiments $R^2$ is cyclopropyl.

In accordance with any one of the foregoing embodiments, in certain embodiments $R^2$ is —$OCH_3$.

In accordance with any one of the foregoing embodiments, in certain embodiments $R^2$ is —$Si(CH_3)_3$.

In accordance with any one of the foregoing embodiments, in certain embodiments $R^2$ is —$CONH_2$.

In accordance with any one of the foregoing embodiments, in certain embodiments $R^2$ is cyano.

In accordance with any one of the foregoing embodiments, in certain embodiments $R^2$ is phenyl.

In certain aspects, the invention provides a compound, or a pharmaceutically acceptable salt thereof, represented by formula XXV:

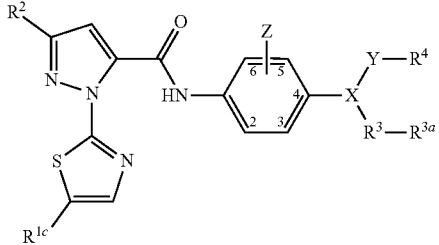

(XXV)

wherein:

X represents CH, C(OH), C(O($C_1$-$C_6$)alkyl), C(O)N, $CH_2$N, N, C(O), or —O—; provided that:
if X represents CH, then —Y—$R^4$ represents —H or —OH, or both Y and $R^4$ are present;
if X represents C(OH) or C(O($C_1$-$C_6$)alkyl), then —Y—$R^4$ is present;
if X represents C(O)N, then —Y—$R^4$ represents H; or —Y—$R^4$ represents H, and —$R^3$—$R^{3a}$ represents H;
if X represents $CH_2$N, then —Y—$R^4$ represents ($C_1$-$C_6$)alkyl;
if X represents N, then —Y—$R^4$ represents H, or both Y and $R^4$ are present; and
if X represents C(O) or —O—, then —Y—$R^4$ is absent;

—Y—$R^4$, when present, represents —(($C_1$-$C_6$)alkyl)-$R^4$, —$CH_2C(O)$—$R^4$, —$CH_2NH$—$R^4$, —$CH_2N(($C_1$-$C_6$)alkyl)-$R^4$, —$CR^aR^b$—$R^4$, —NH—$R^4$, —$NHCH_2$—$R^4$, —NHC(O)—$R^4$, —N(($C_1$-$C_6$)alkyl)-$R^4$, —N(($C_1$-$C_6$)alkyl)$CH_2$—$R^4$, —N(($CH_2)_2OH$)—$R^4$, —N[($C_3$-$C_8$)cycloalkyl($C_1$-$C_6$)alkyl]$R^4$, -heterocyclyl-$R^4$, —$OR^4$, —$OCH_2$—$R^4$, —OC(O)—$R^4$, —OC(O)$NR^aR^b$, —$SCH_2R^4$, or —$SR^4$, wherein the ($C_1$-$C_6$)alkyl moiety of —(($C_1$-$C_6$)alkyl)-$R^4$ is optionally substituted;

Z is absent or represents halo, hydroxy, ($C_1$-$C_6$)alkyl, —$CF_3$, —$OCF_3$, ($C_1$-$C_6$)alkoxy, aryl, aryloxy, amino, amino($C_1$-$C_6$)alkyl, —$C(O)NH_2$, cyano, —NHC(O)($C_1$-$C_6$)alkyl, —$SO_2(C_1$-$C_6)$alkyl, —$SO_2NH_2$, or ($C_3$-$C_8$)cycloalkyl;

$R^{1c}$ represents halo, amino($C_1$-$C_6$)alkyl, ($C_1$-$C_6$)alkoxy, cyano, —$SO_2CH_3$, formyl, acyl, or optionally substituted aryl;

$R^2$ represents halo, ($C_1$-$C_6$)alkyl, ($C_3$-$C_8$)cycloalkyl, ($C_1$-$C_6$)fluoroalkyl, —$OCH_3$, —$Si(CH_3)_3$, —$CONH_2$, —C(O)OH, cyano, or phenyl;

$R^3$, when present, represents —NH—, —O—, optionally substituted aryl, heteroaryl, phenyl, carbocyclyl, or heterocyclyl;

$R^{3a}$ is absent or represents one or more substituents independently selected from the group consisting of halo, hydroxy, ($C_1$-$C_6$)alkyl, —$CF_3$, —$OCF_3$, ($C_1$-$C_6$)alkoxy, aryl, aryloxy, amino, amino($C_1$-$C_6$)alkyl, —$C(O)NH_2$, cyano, —NHC(O)($C_1$-$C_6$)alkyl, —$SO_2$($C_1$-$C_6$)alkyl, and —$SO_2NH_2$;

$R^4$ represents hydrogen, hydroxy, optionally substituted ($C_1$-$C_6$)alkyl, optionally substituted ($C_3$-$C_8$)cycloalkyl, heterocyclyl($C_1$-$C_6$)alkyl, ($C_3$-$C_8$)cycloalkyl($C_1$-$C_6$)alkyl, —$CH_2OH$, —CH(($C_1$-$C_6$)alkyl)OH, —CH($NH_2$)CH(($C_1$-$C_6$)alkyl)$_2$, optionally substituted aryl, optionally substituted aryl($C_1$-$C_6$)alkyl, heteroaryl, optionally substituted heteroaryl($C_1$-$C_6$)alkyl, —$CH_2S$($C_1$-$C_6$)alkyl, amino, or cyano; or —$CH_2$— fused to the 4-position of the ring bearing Z to form a 5- to 7-membered heterocyclic ring with optional substituents;

or, when $R^3$ is phenyl, can represent —NH— fused to the position ortho to X on that phenyl;

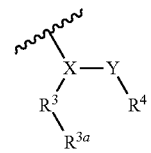

can represent

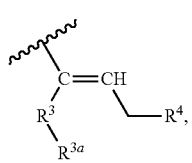 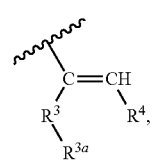 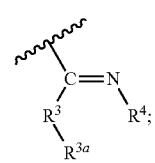

and the stereochemical configuration at any chiral center is R, S, or a mixture of R and S.

In certain embodiments, X represents CH, and both Y and $R^4$ are present.

In certain embodiments, —X—Y— represents —CHNHCH$_2$—.

In certain embodiments, —X—Y— represents —C(OH)CH$_2$CH$_2$—.

In certain embodiments, —X—Y— represents —CHOCH$_2$—.

In accordance with any one of the foregoing embodiments, in certain embodiments R$^3$ represents phenylene-R$^{3a}$.

In accordance with any one of the foregoing embodiments, in certain embodiments —R$^3$—R$^{3a}$ represents

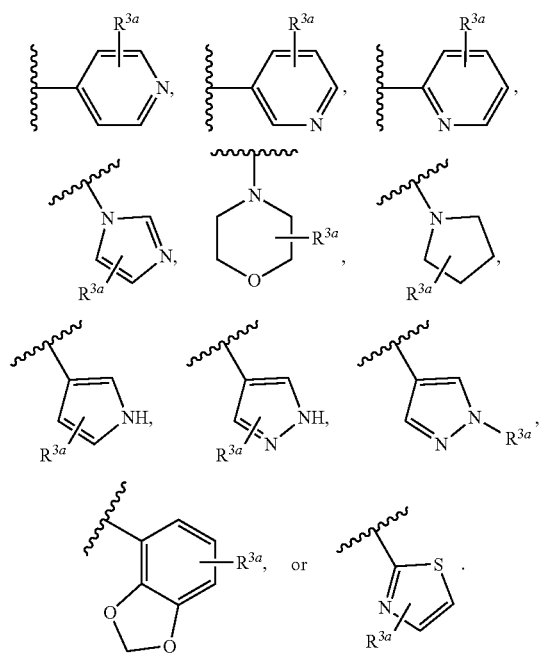

In accordance with any one of the foregoing embodiments, in certain embodiments —R$^3$—R$^{3a}$ represents

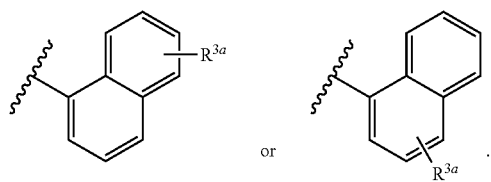

In accordance with any one of the foregoing embodiments, in certain embodiments —R$^3$—R$^{3a}$ represents

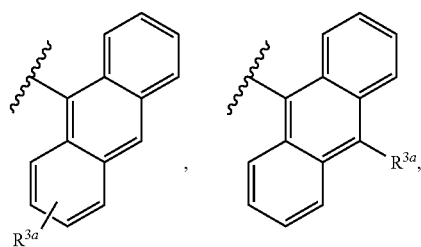

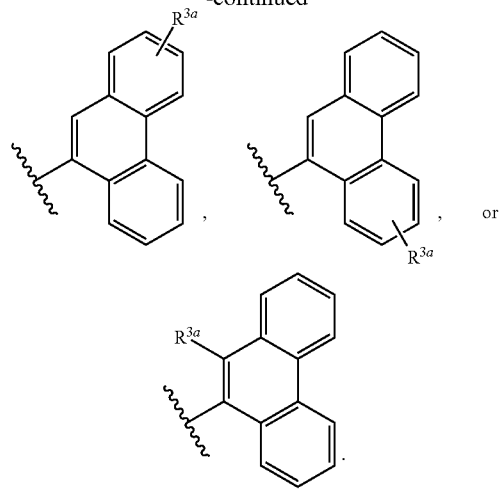

In accordance with any one of the foregoing embodiments, in certain embodiments R$^{3a}$ is absent.

In accordance with any one of the foregoing embodiments, in certain embodiments R$^4$ is cyclopropyl.

In accordance with any one of the foregoing embodiments, in certain embodiments R$^3$ is phenyl, and R$^{3a}$ is ortho, meta, or para —OH.

In accordance with any one of the foregoing embodiments, in certain embodiments R$^3$ is phenyl, and R$^{3a}$ is meta or para —NH$_2$.

In accordance with any one of the foregoing embodiments, in certain embodiments R$^3$ is phenyl, and R$^{3a}$ is meta or para —CN.

In accordance with any one of the foregoing embodiments, in certain embodiments Z is absent.

In accordance with any one of the foregoing embodiments, in certain embodiments Z represents fluoro.

In accordance with any one of the foregoing embodiments, in certain embodiments Z represents chloro.

In accordance with any one of the foregoing embodiments, in certain embodiments Z represents 2-F, 3-F, 5-F, 6-F, 6-Cl, or 5-(C$_3$-C$_8$)cycloalkyl.

In accordance with any one of the foregoing embodiments, in certain embodiments Z represents 6-F.

In accordance with any one of the foregoing embodiments, in certain embodiments R$^{1c}$ represents aminomethyl.

In accordance with any one of the foregoing embodiments, in certain embodiments R$^{1c}$ represents cyano.

In accordance with any one of the foregoing embodiments, in certain embodiments R$^{1c}$ represents —SO$_2$CH$_3$.

In accordance with any one of the foregoing embodiments, in certain embodiments R$^2$ is —CH$_3$ or —CF$_3$.

In accordance with any one of the foregoing embodiments, in certain embodiments R$^2$ is —CF$_3$.

In accordance with any one of the foregoing embodiments, in certain embodiments R$^2$ is tert-butyl.

In accordance with any one of the foregoing embodiments, in certain embodiments R$^2$ is cyclopropyl.

In accordance with any one of the foregoing embodiments, in certain embodiments R$^2$ is —OCH$_3$.

In accordance with any one of the foregoing embodiments, in certain embodiments R$^2$ is —Si(CH$_3$)$_3$.

In accordance with any one of the foregoing embodiments, in certain embodiments R$^2$ is —CONH$_2$.

In accordance with any one of the foregoing embodiments, in certain embodiments R$^2$ is cyano.

In accordance with any one of the foregoing embodiments, in certain embodiments R² is phenyl.

In certain aspects, the invention provides a compound, or a pharmaceutically acceptable salt thereof, represented by formula (XXVI):

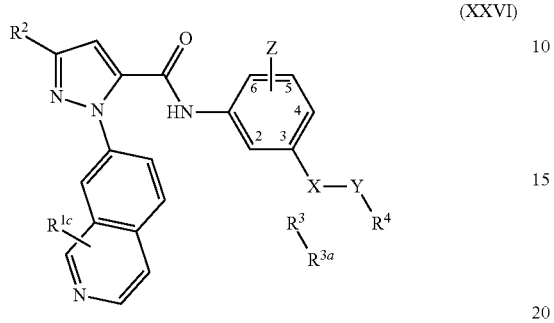

(XXVI)

wherein:

X represents CH, C(OH), —C(NH₂), or —C(NRᵃRᵇ);

—Y—R⁴, when present, represents —((C₁-C₆)alkyl)-R⁴, —CH₂C(O)—R⁴, —CH₂NH—R⁴, —CH₂N((C₁-C₆)alkyl)-R⁴, —CRᵃRᵇ—R⁴, —NH—R⁴, —NHCH₂—R⁴, —NHC(O)—R⁴, —N((C₁-C₆)alkyl)-R⁴, —N((C₁-C₆)alkyl)CH₂—R⁴, —N((CH₂)₂OH)—R⁴, —N[(C₃-C₈)cycloalkyl(C₁-C₆)alkyl]R⁴, -heterocyclyl-R⁴, —OR⁴, —OCH₂—R⁴, —OC(O)—R⁴, —OC(O)NRᵃRᵇ, —SCH₂R⁴, or —SR⁴, wherein the (C₁-C₆)alkyl moiety of —((C₁-C₆)alkyl)-R⁴ is optionally substituted;

Z is absent or represents halo, hydroxy, (C₁-C₆)alkyl, —CF₃, —OCF₃, (C₁-C₆)alkoxy, aryl, aryloxy, amino, amino(C₁-C₆)alkyl, —C(O)NH₂, cyano, —NHC(O)(C₁-C₆)alkyl, —SO₂(C₁-C₆)alkyl, —SO₂NH₂, or (C₃-C₈)cycloalkyl; R1c represents halo, amino(C₁-C₆)alkyl, (C₁-C₆)alkoxy, cyano, —SO₂CH₃, formyl, acyl, —NH₂, or optionally substituted aryl;

R³ᵃ is absent or represents one or more substituents independently selected from the group consisting of halo, hydroxy, (C₁-C₆)alkyl, —CF₃, —OCF₃, (C₁-C₆)alkoxy, aryl, aryloxy, amino, amino(C₁-C₆)alkyl, —C(O)NH₂, cyano, —NHC(O)(C₁-C₆)alkyl, —SO₂(C₁-C₆)alkyl, and —SO₂NH₂; and R⁴ represents hydrogen, hydroxy, optionally substituted (C₁-C₆)alkyl, optionally substituted (C₃-C₈)cycloalkyl, heterocyclyl(C₁-C₆)alkyl, (C₃-C₈)cycloalkyl(C₁-C₆)alkyl, —CH₂OH, —CH((C₁-C₆)alkyl)OH, —CH(NH₂)CH((C₁-C₆)alkyl)₂, optionally substituted aryl, optionally substituted aryl(C₁-C₆)alkyl, heteroaryl, optionally substituted heteroaryl(C₁-C₆)alkyl, —CH₂S(C₁-C₆)alkyl, amino, or cyano; or —CH₂— fused to the 4-position of the ring bearing Z to form a 5- to 7-membered heterocyclic ring with optional substituents;

or, when R³ is phenyl, can represent —NH— fused to the position ortho to X on that phenyl.

In certain embodiments, the compound is selected from the group consisting of:

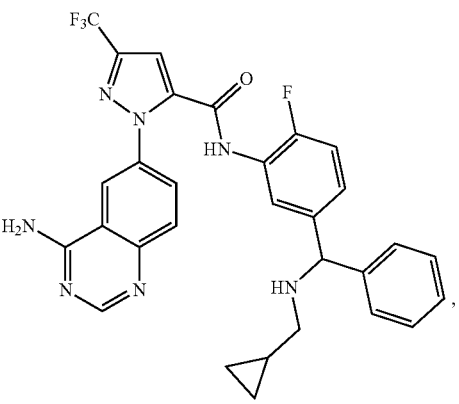

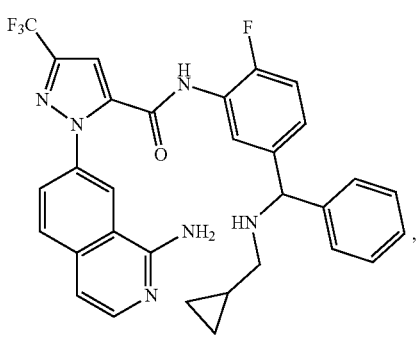

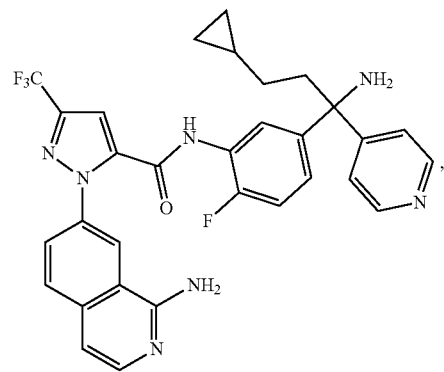

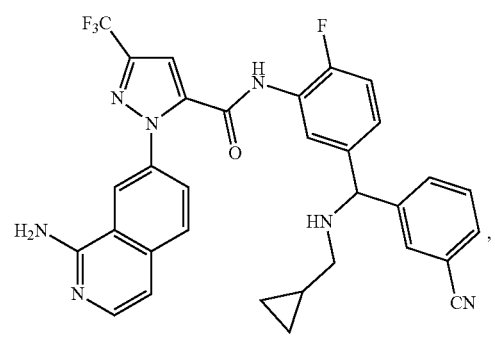

85
-continued
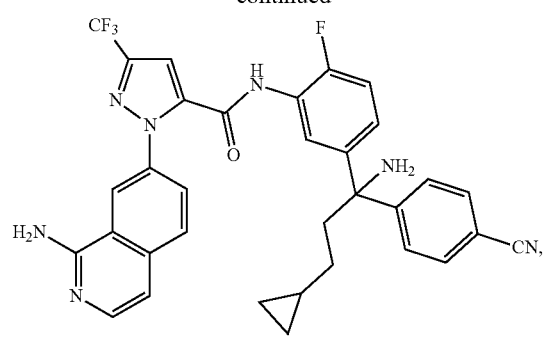
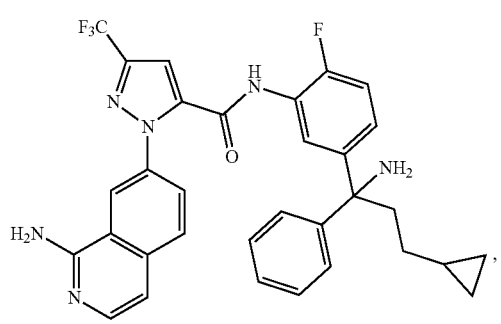
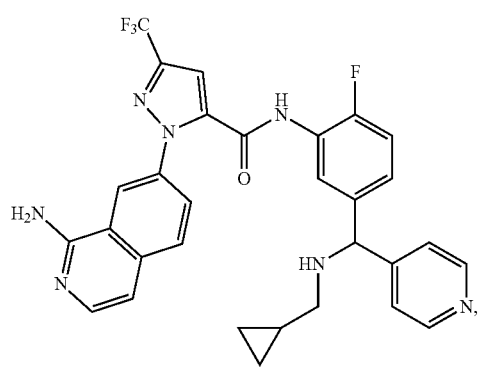
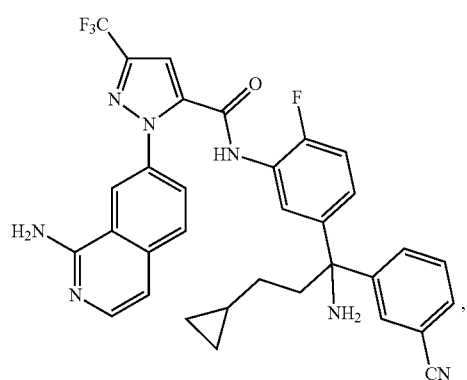
86
-continued
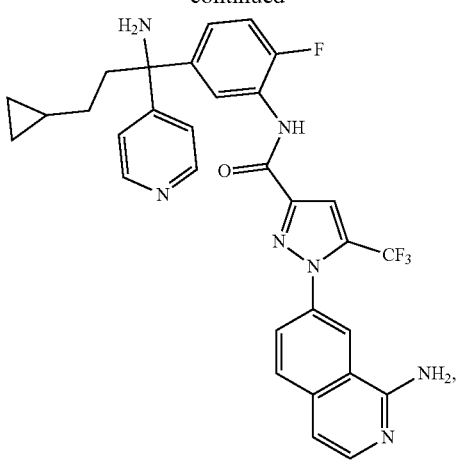
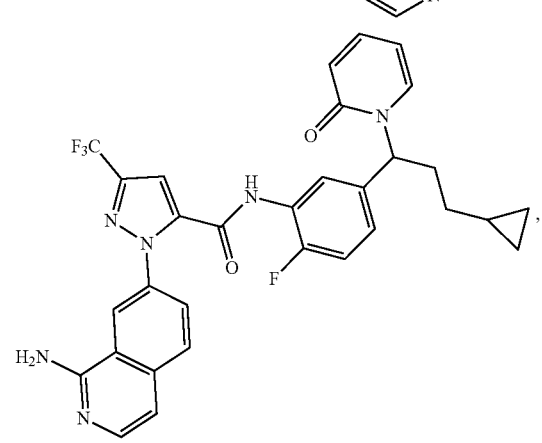
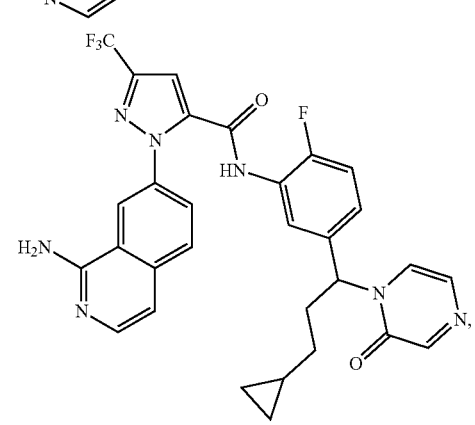
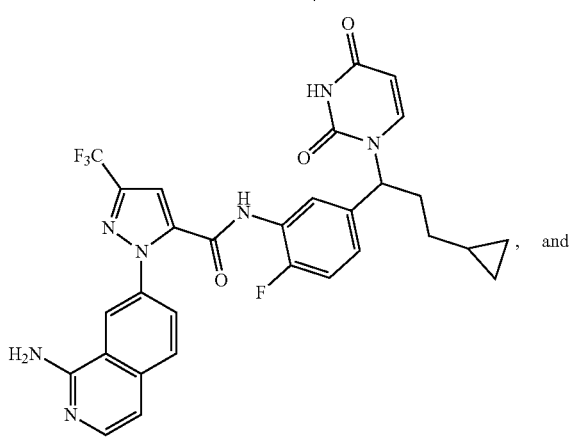
, and

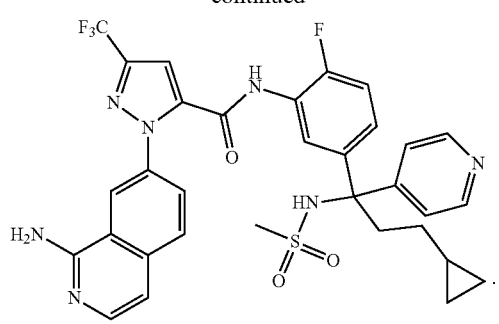
In certain embodiments, the compound is selected from the group consisting of:
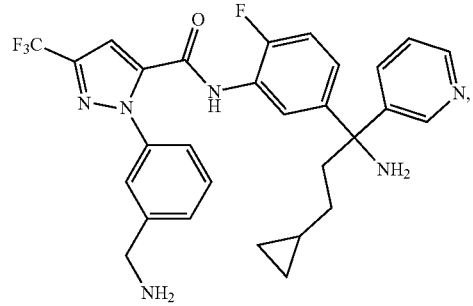
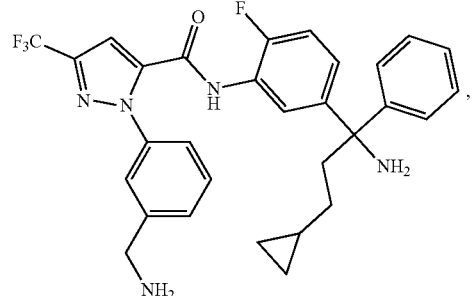
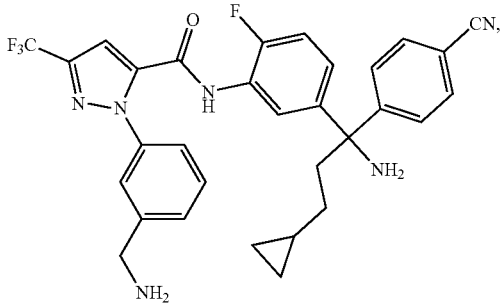
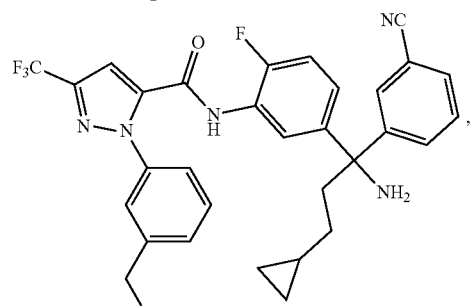
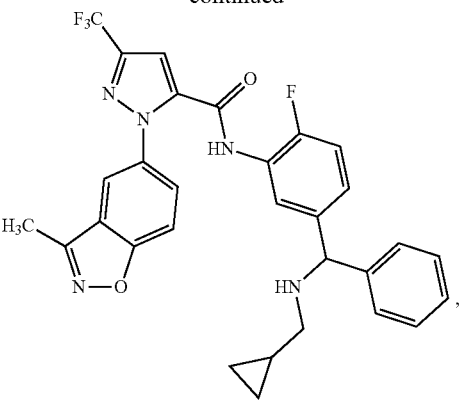
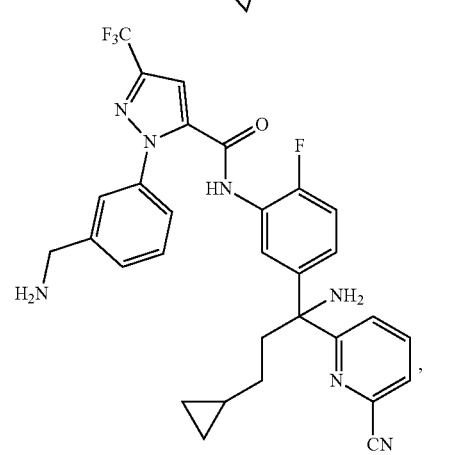
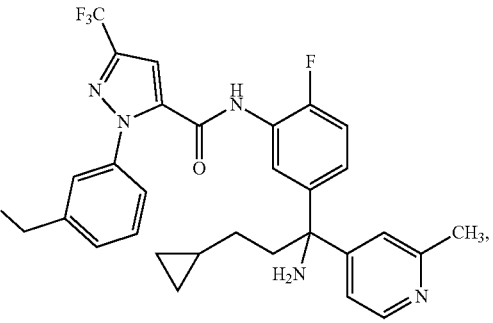
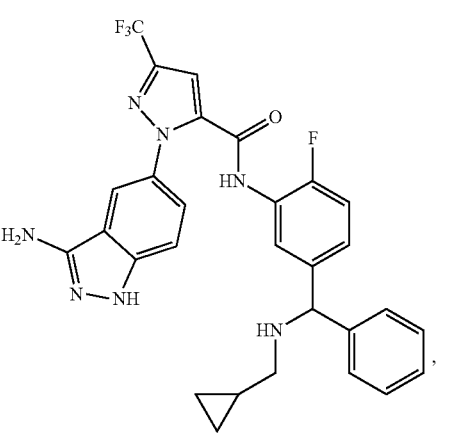

89
-continued
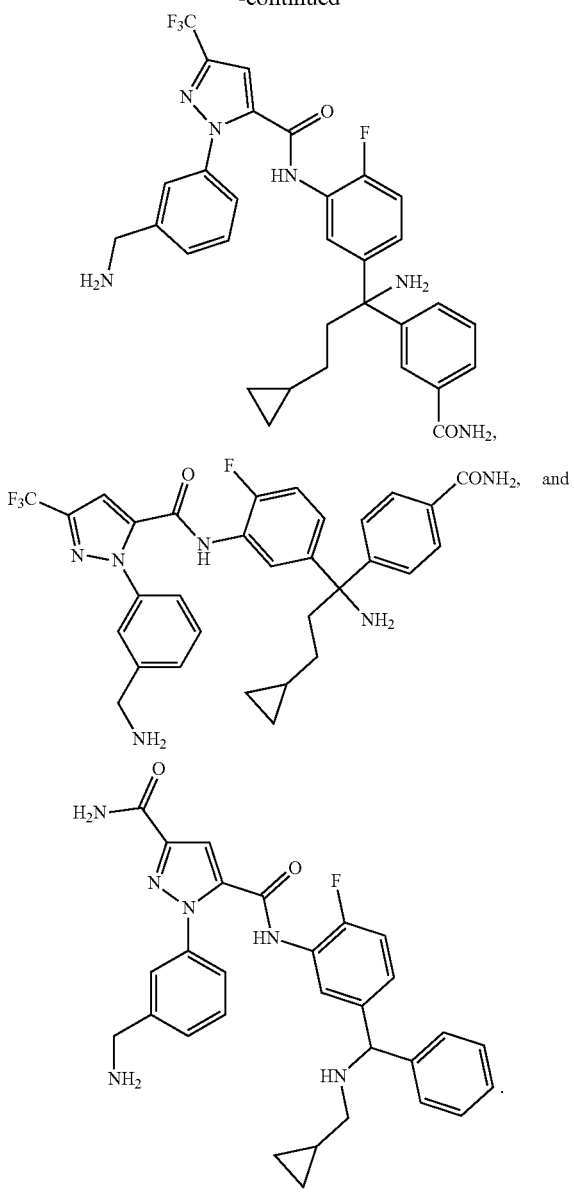
90
-continued
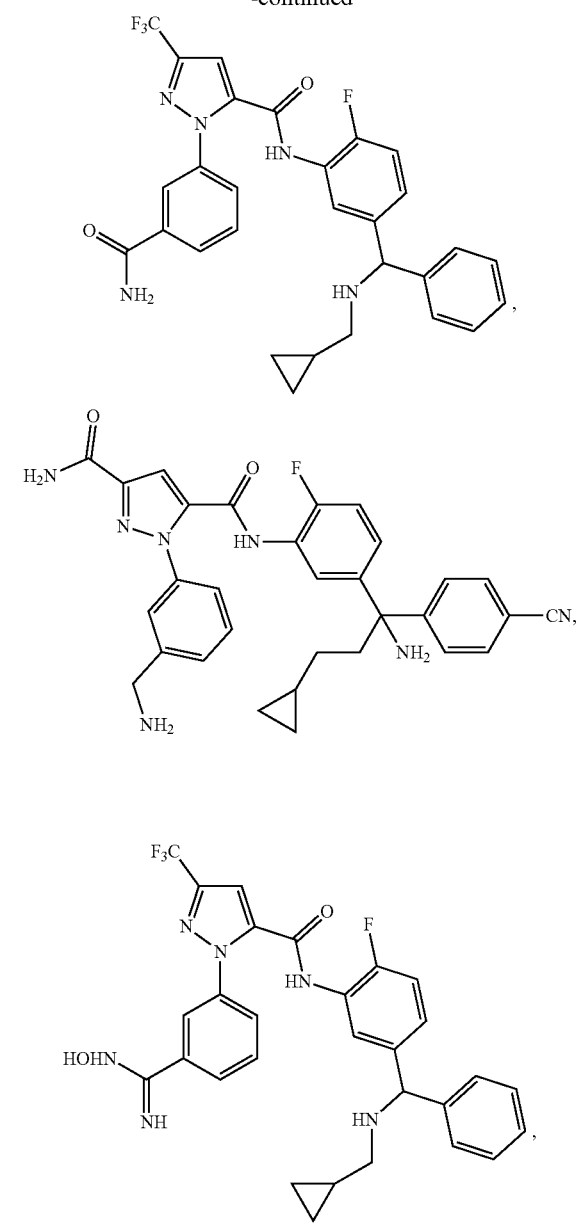
In certain embodiments, the compound is selected from the group consisting of:
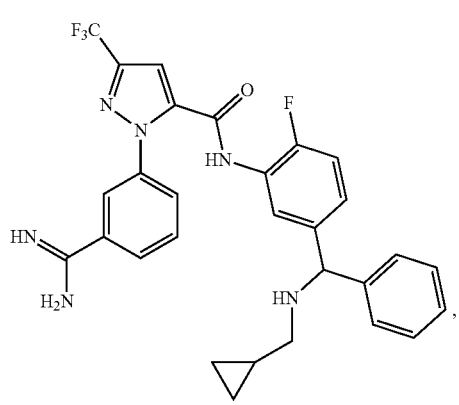
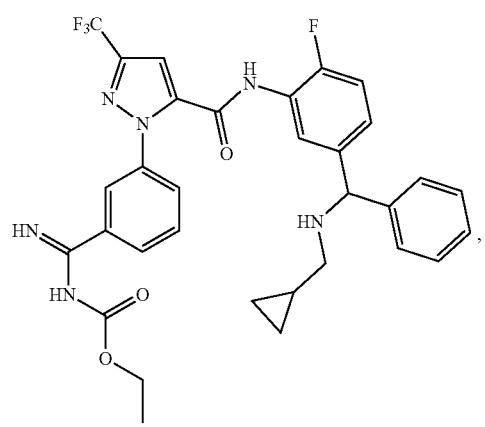

91
-continued
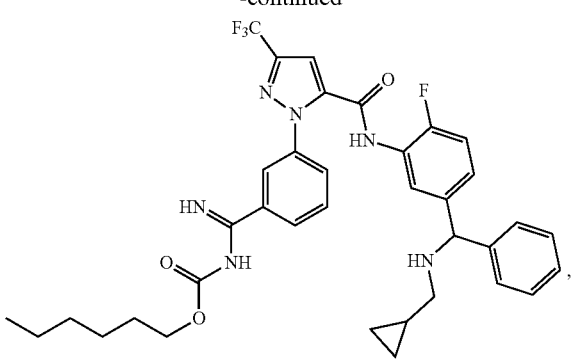
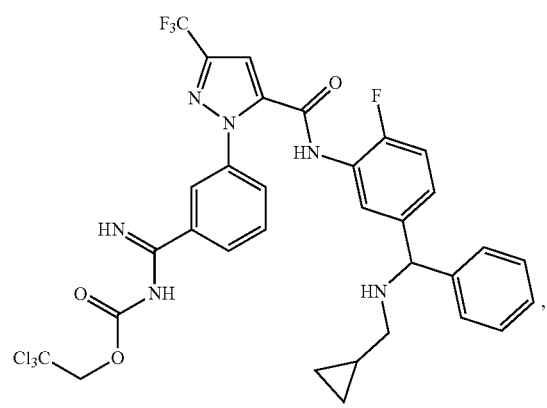
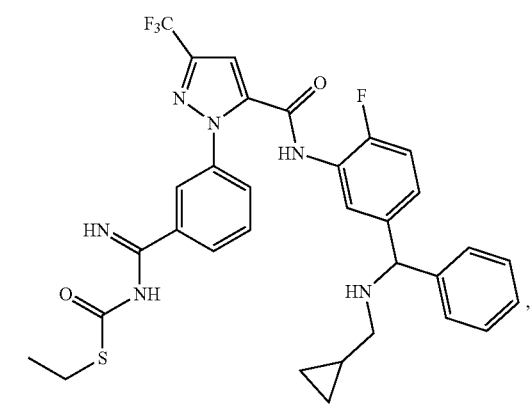
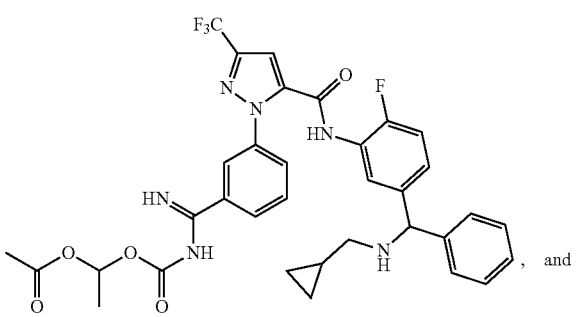
, and
92
-continued
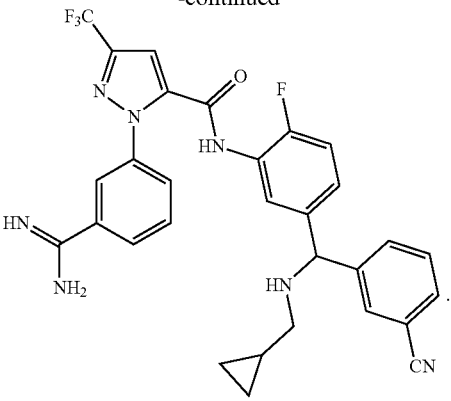
In certain embodiments, the compound is selected from the group consisting of:
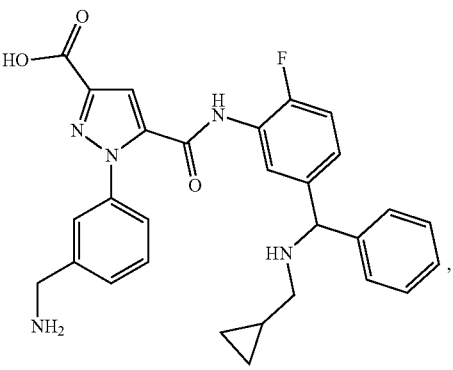
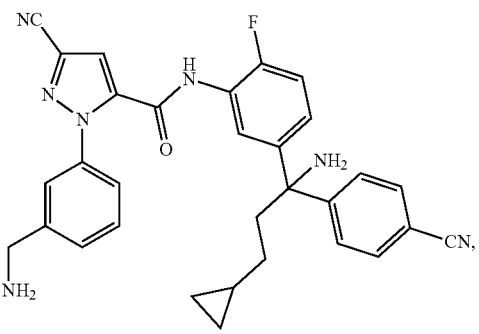
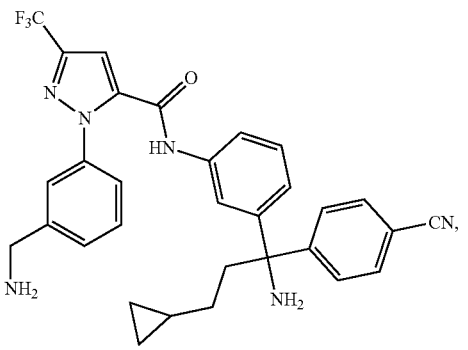

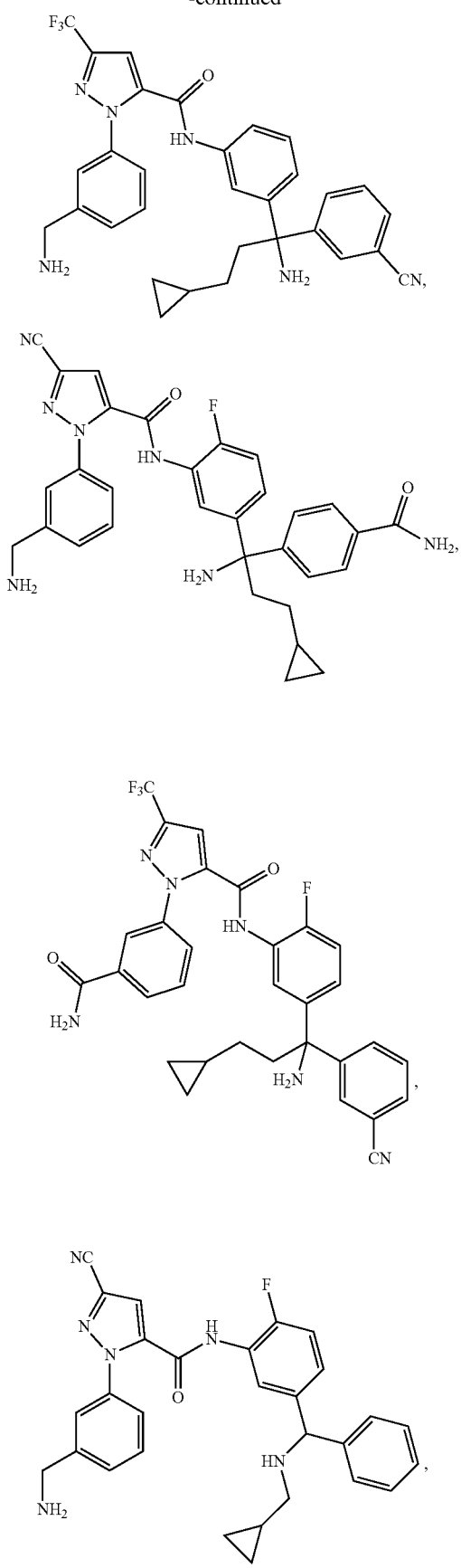
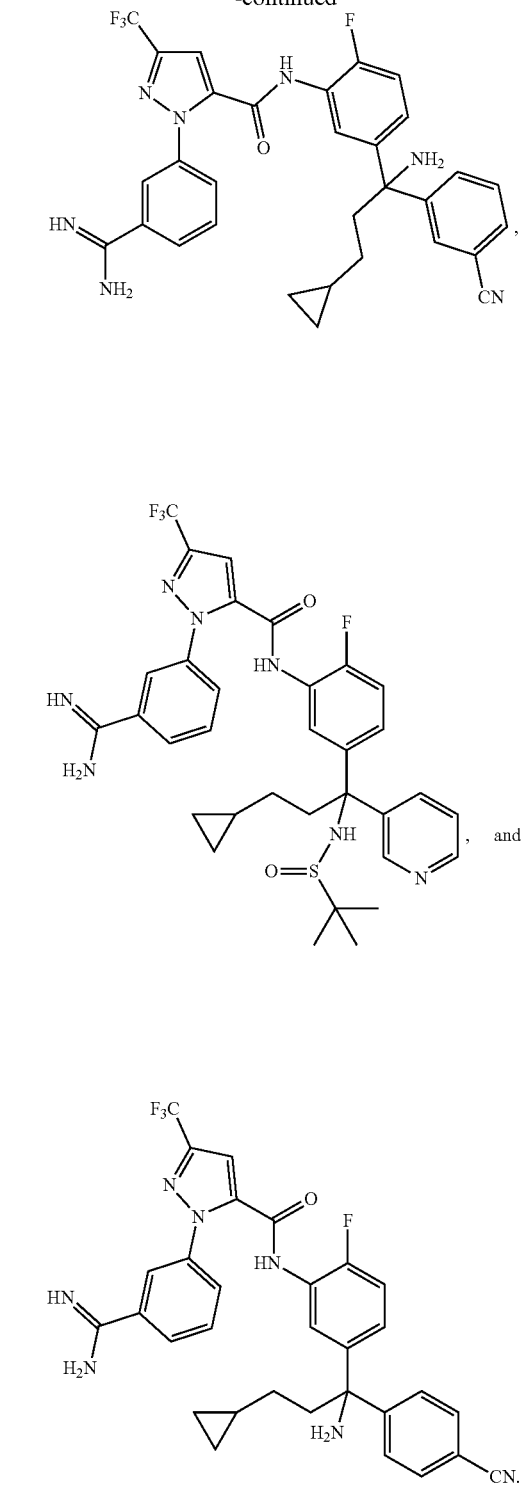
In certain embodiments, the compound is selected from the group consisting of:

95
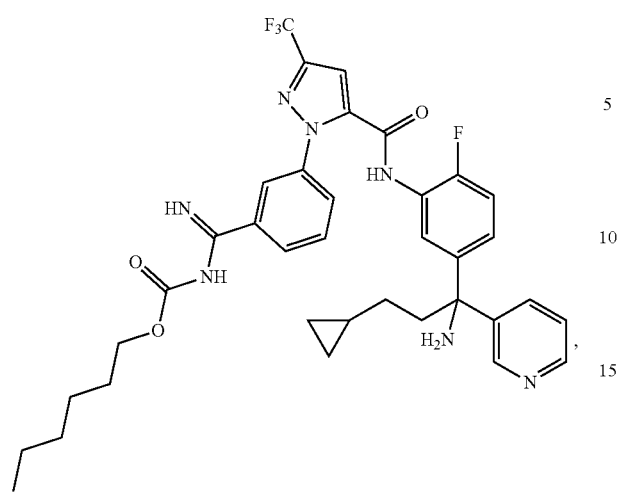
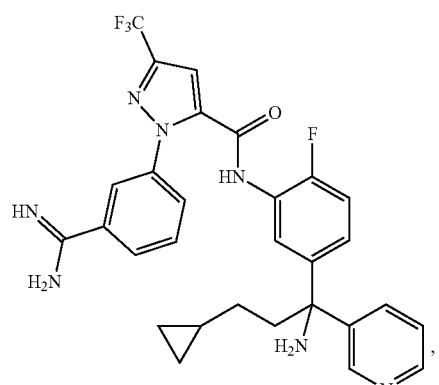
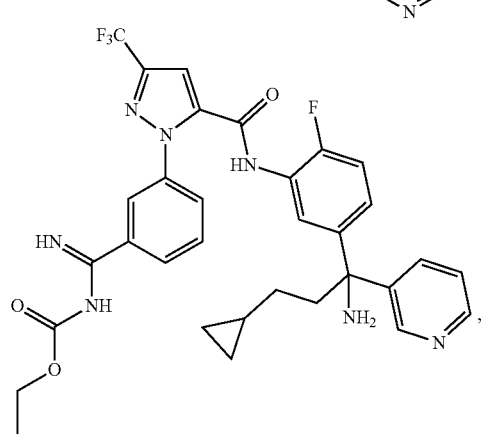
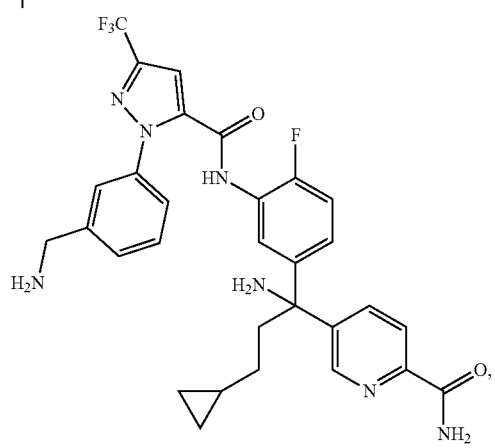
96
-continued
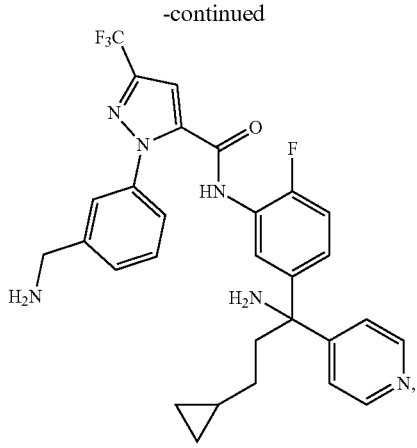
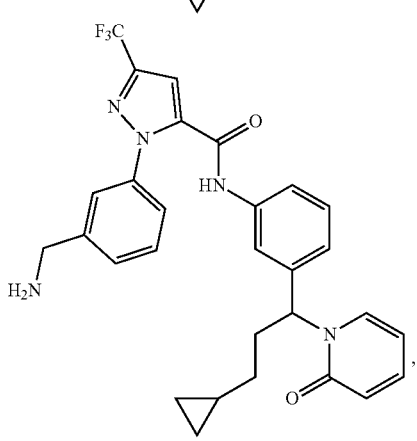
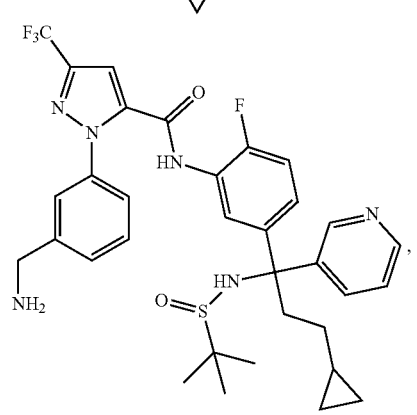
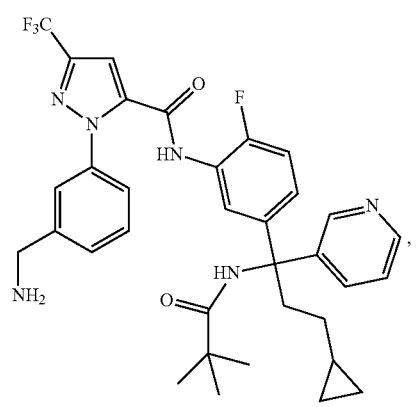

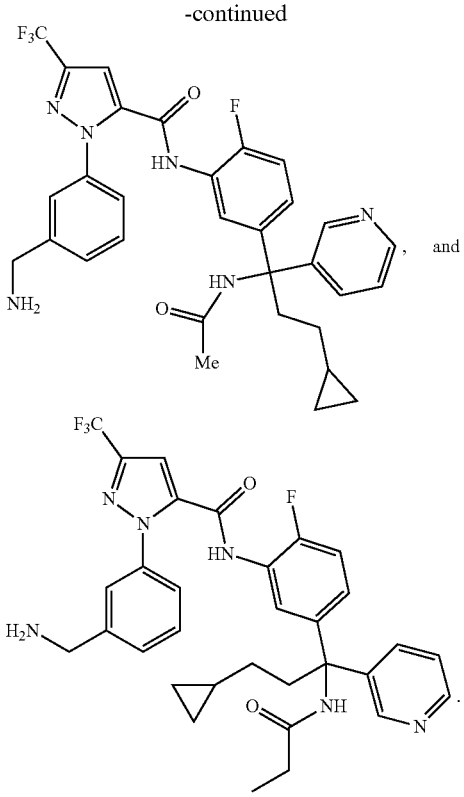
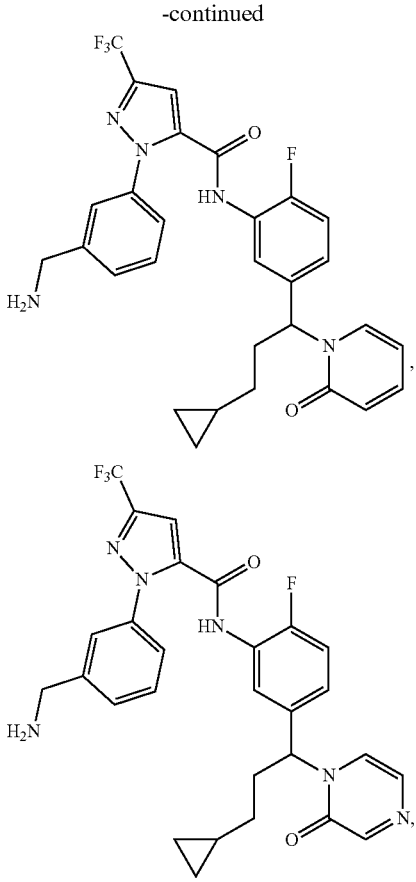
In certain embodiments, the compound is selected from the group consisting of:
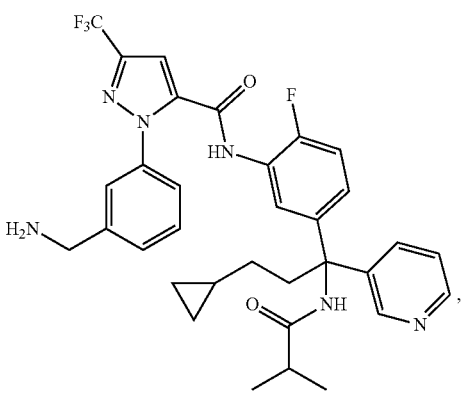
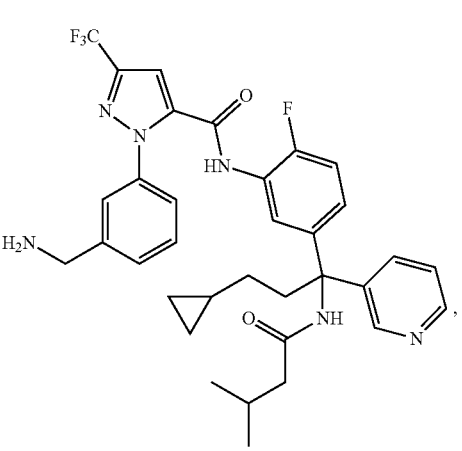

99
-continued
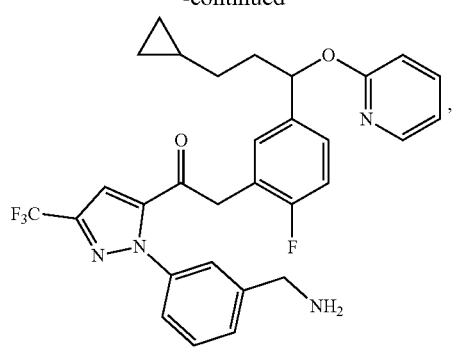
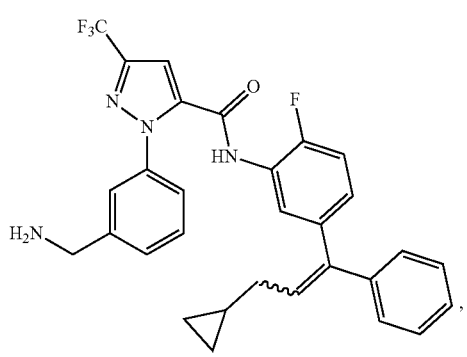
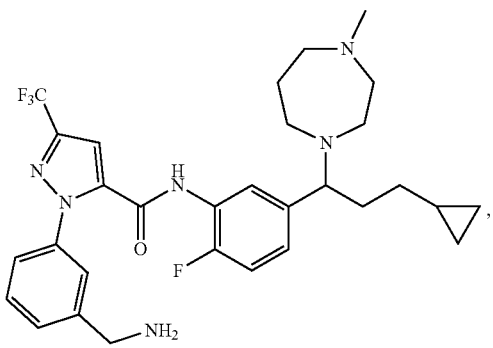
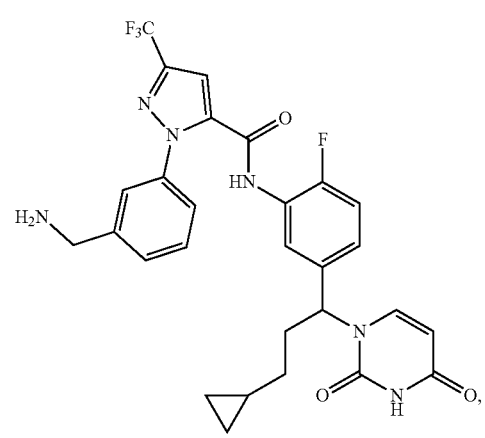
100
-continued
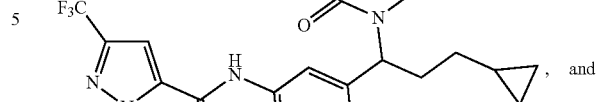, and
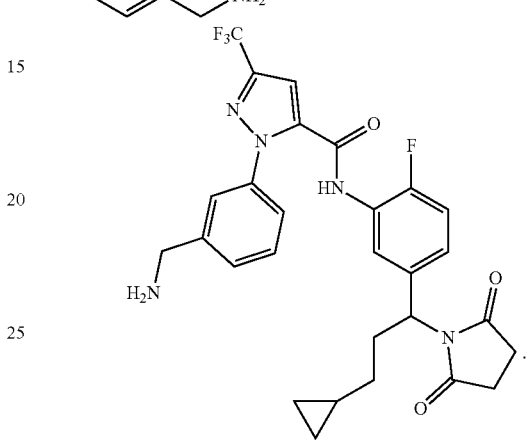
In certain embodiments, the compound is selected from the group consisting of:
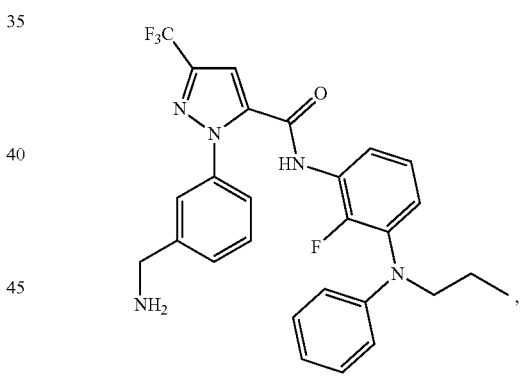
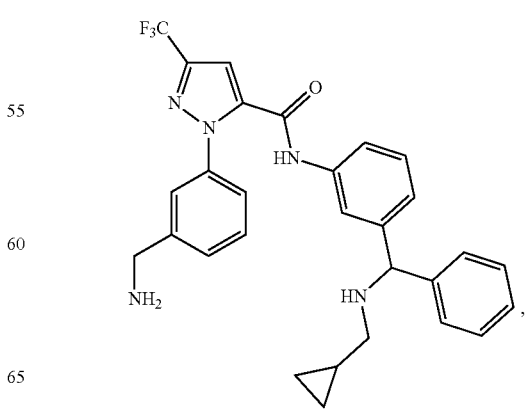

101
-continued
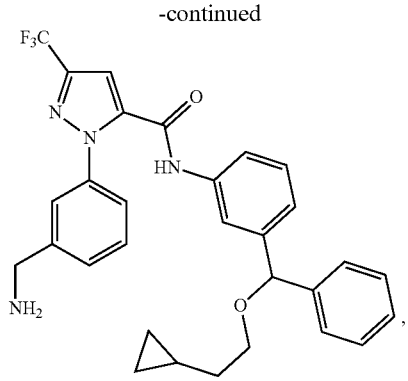
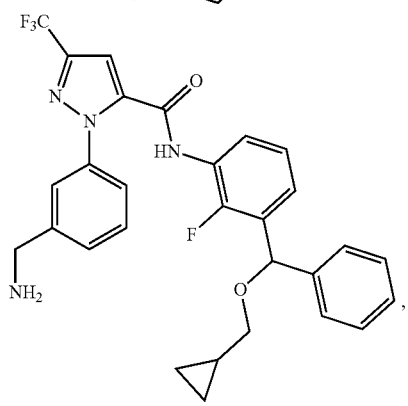
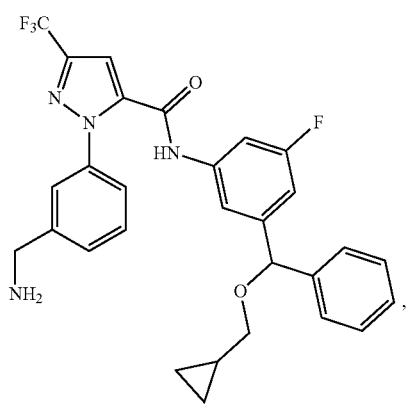
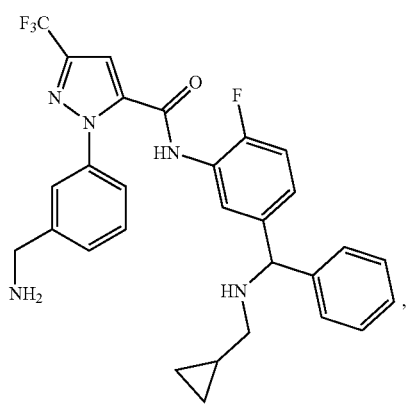
102
-continued
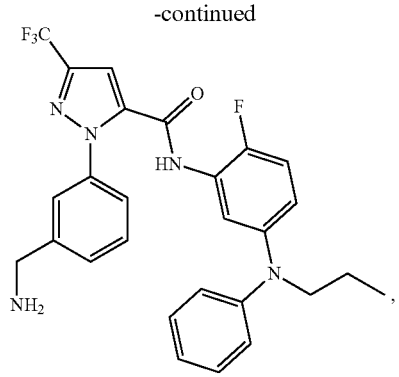
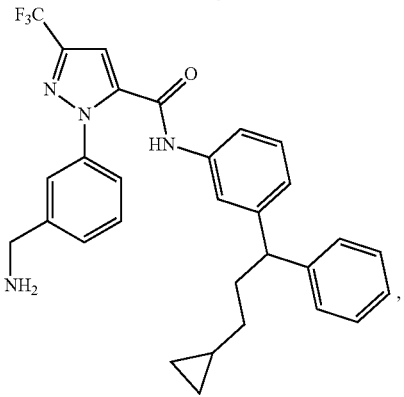
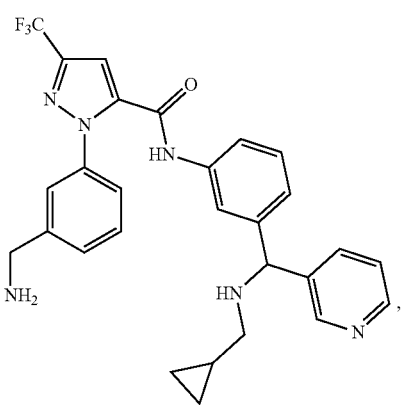
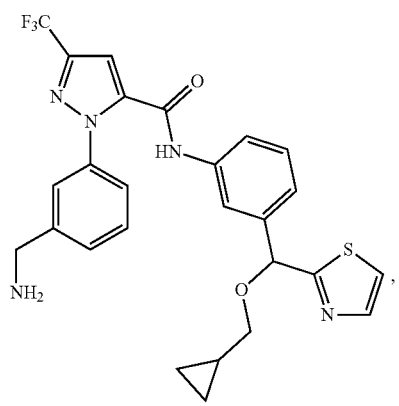

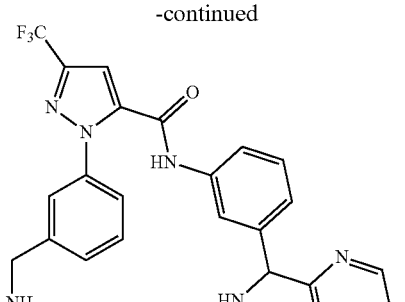
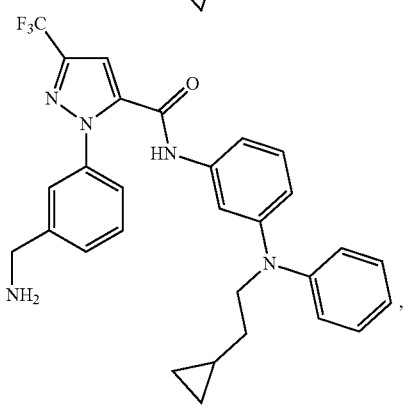
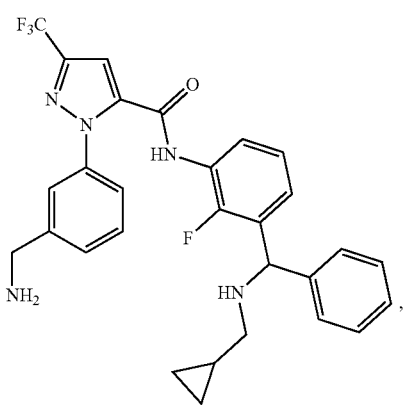
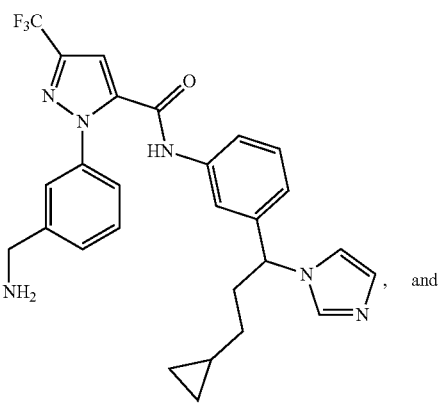
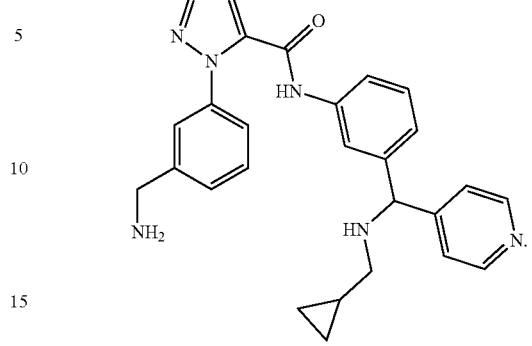
In certain embodiments, the compound is selected from the group consisting of:
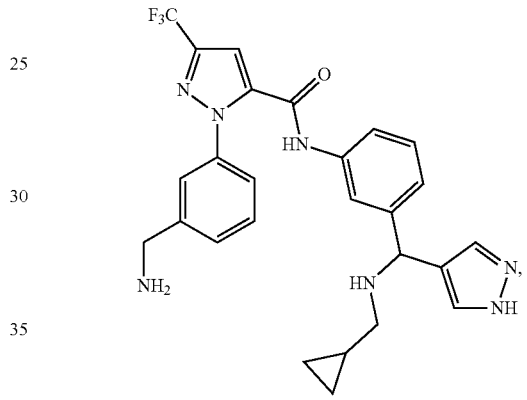
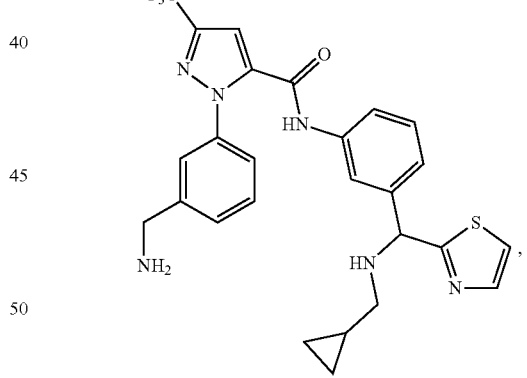
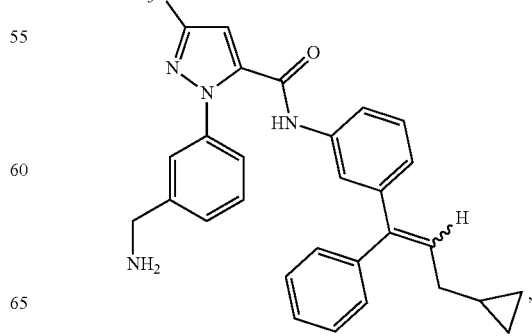

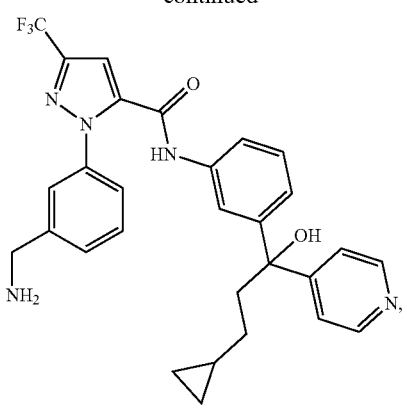
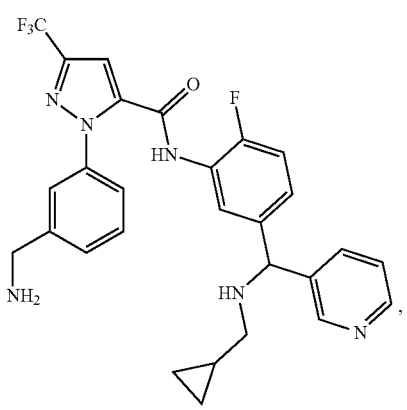
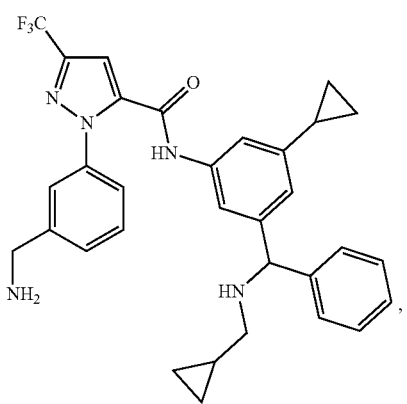
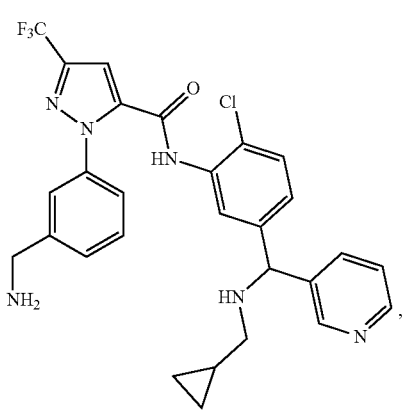
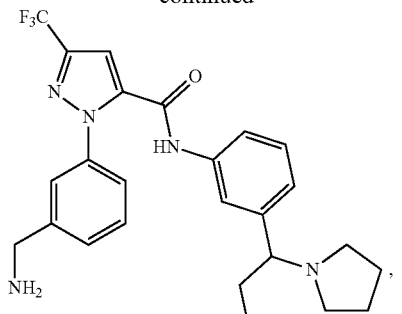
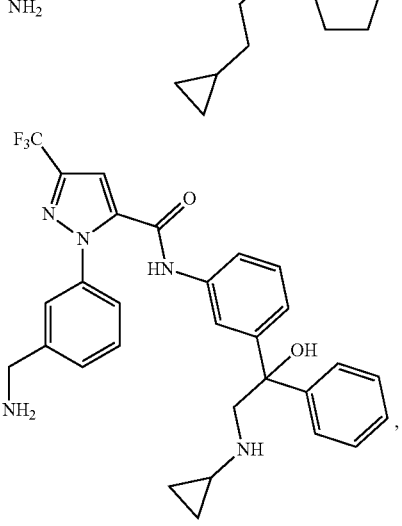
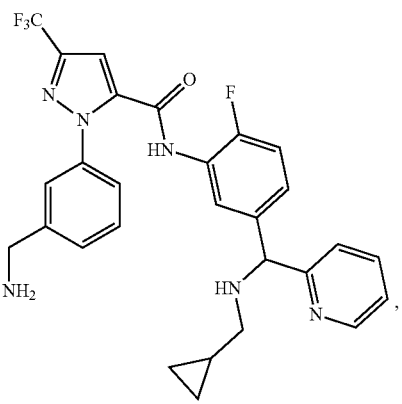
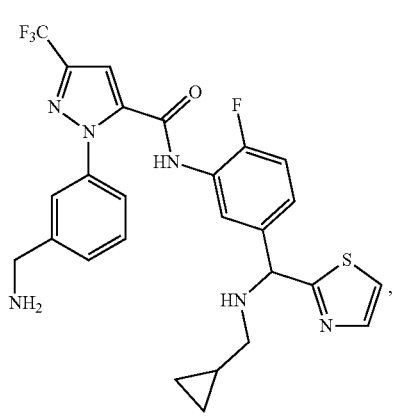

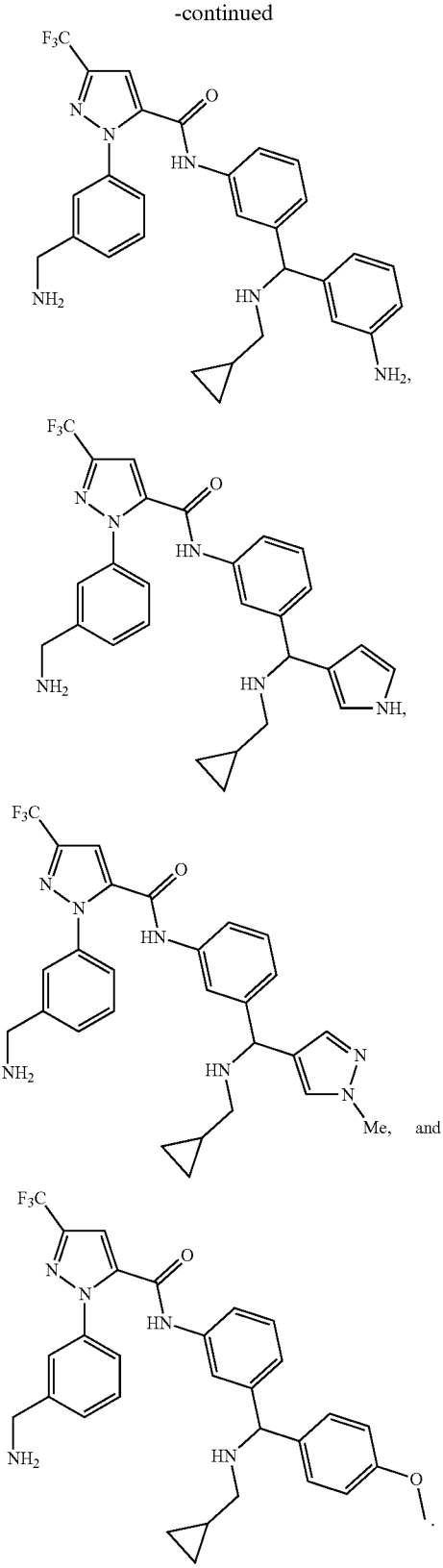
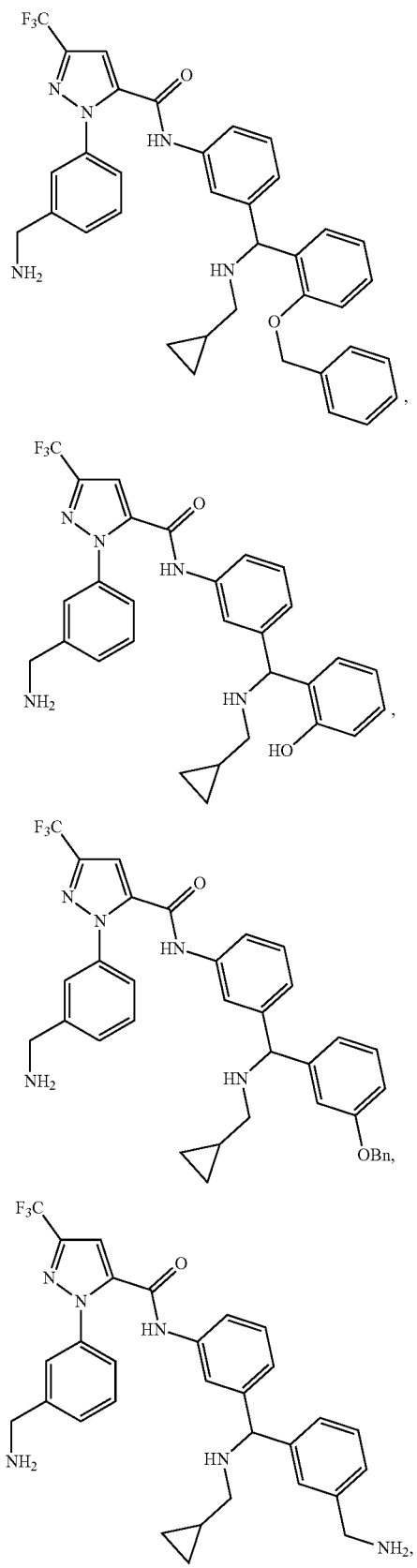
In certain embodiments, the compound is selected from the group consisting of:

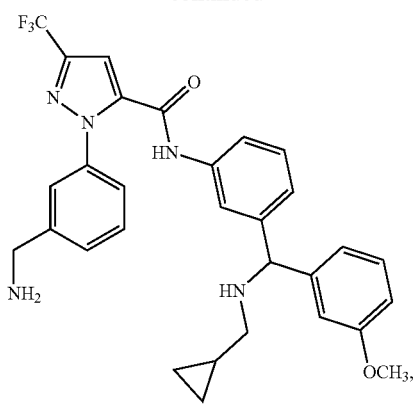
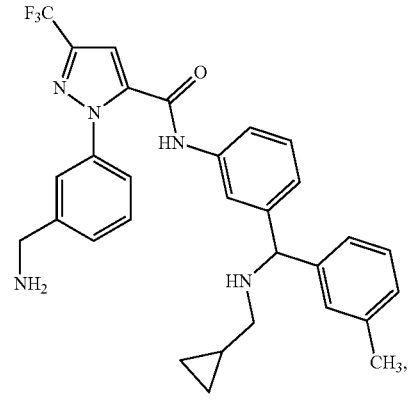 [SMILES: N#Cc1cccc(C(NCC2CC2)c2cccc(NC(=O)c3cc(C(F)(F)F)nn3-c3cccc(CN)c3)c2)c1]
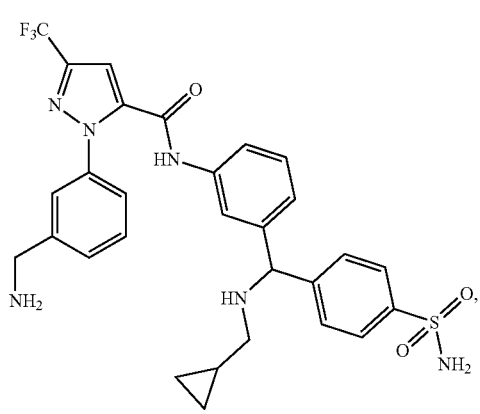
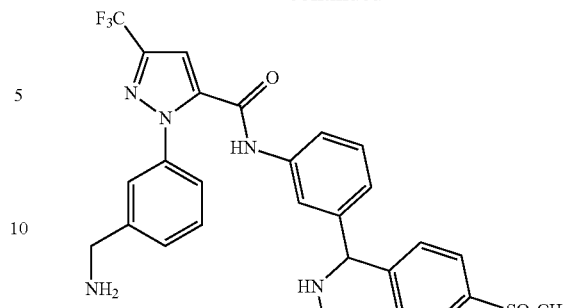
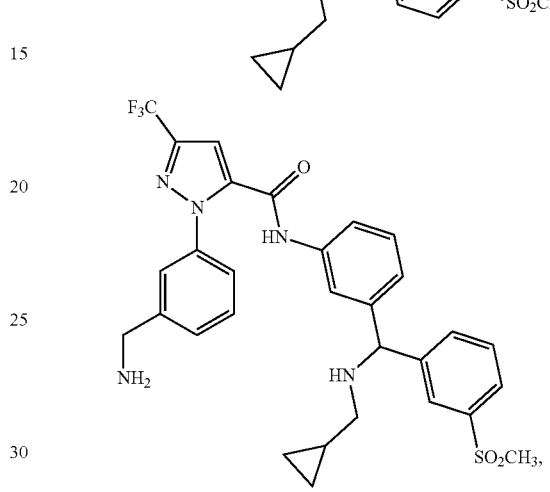
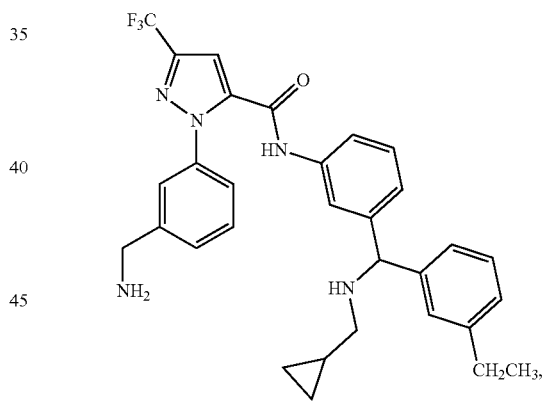
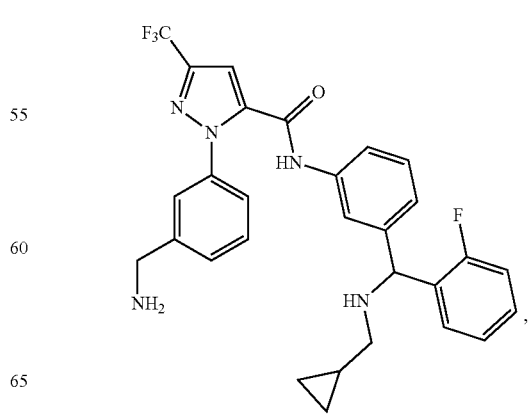

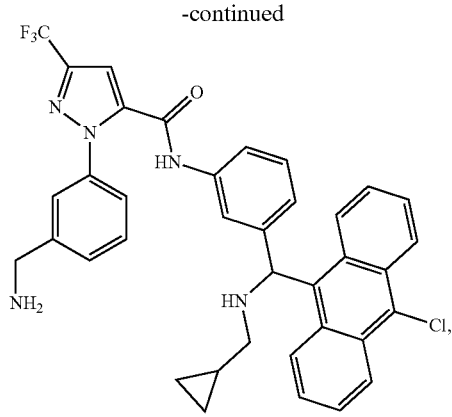
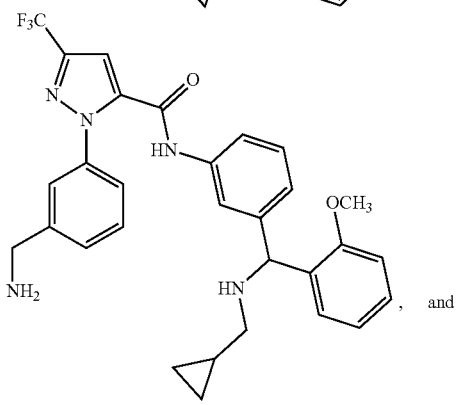
, and
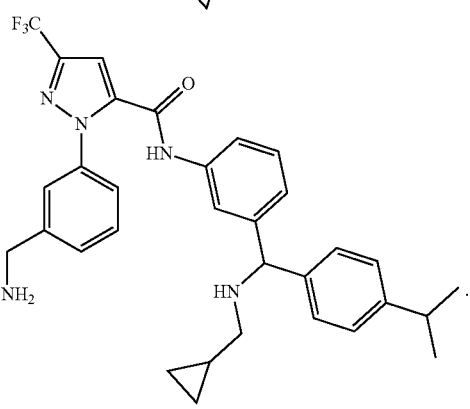
In certain embodiments, the compound is selected from the group consisting of:
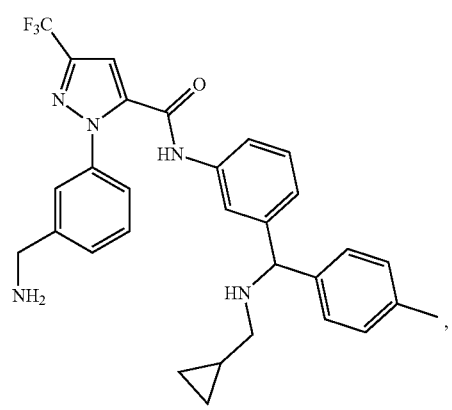
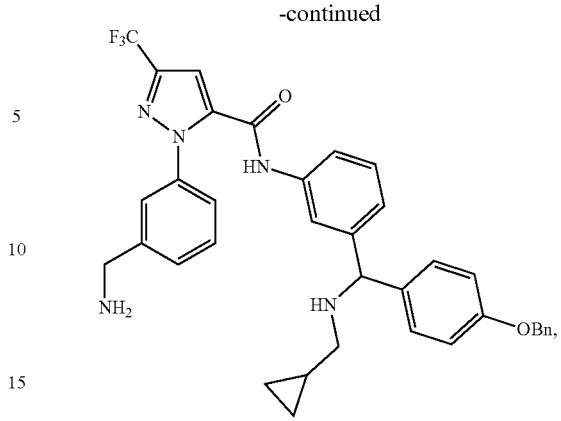
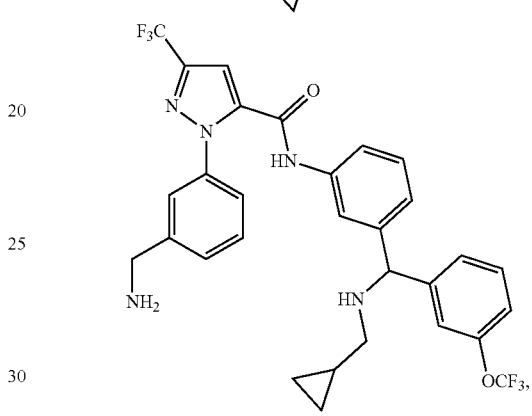
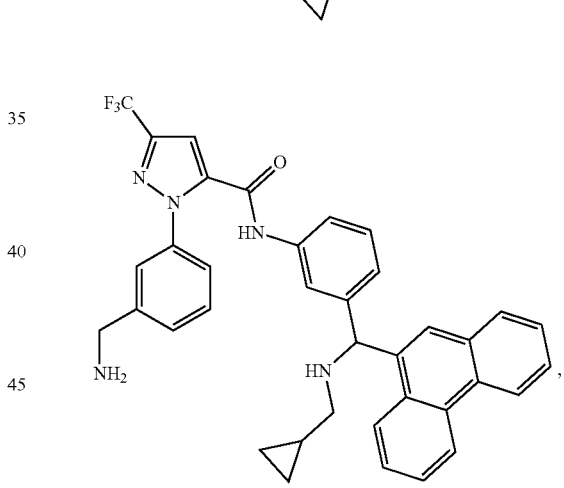
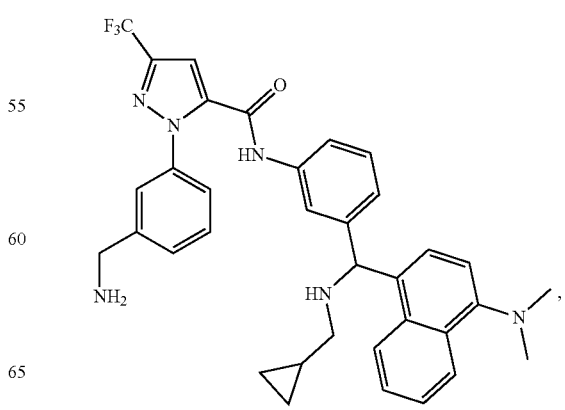

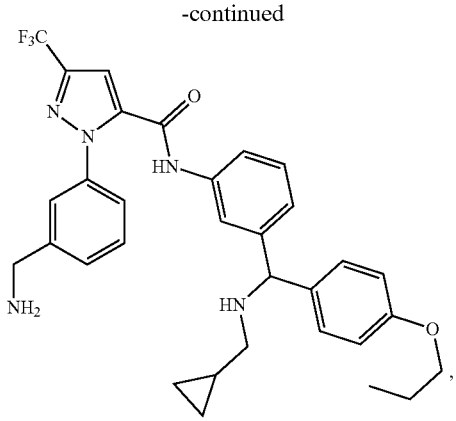
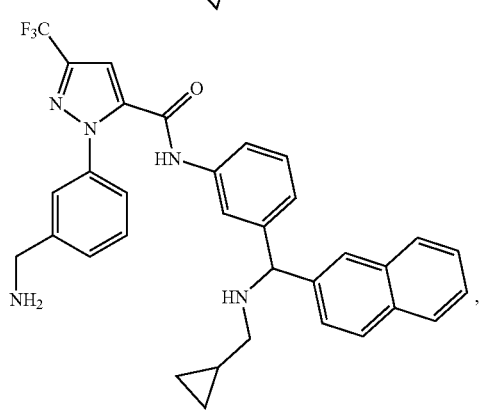
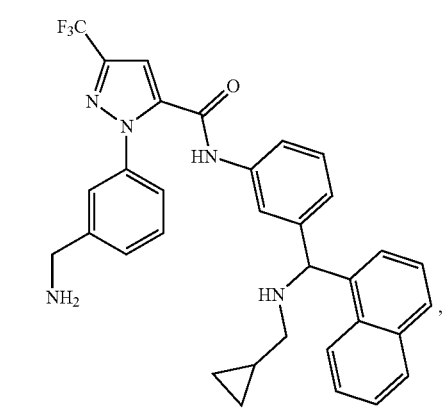
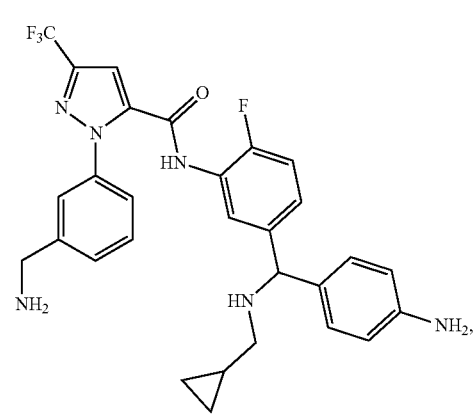
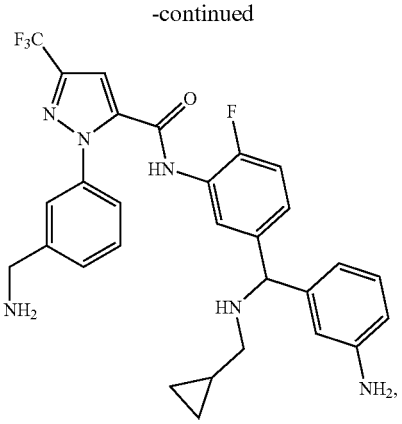
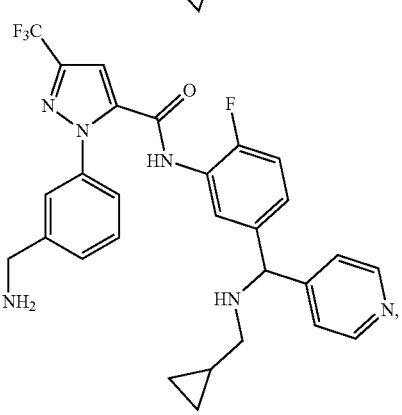
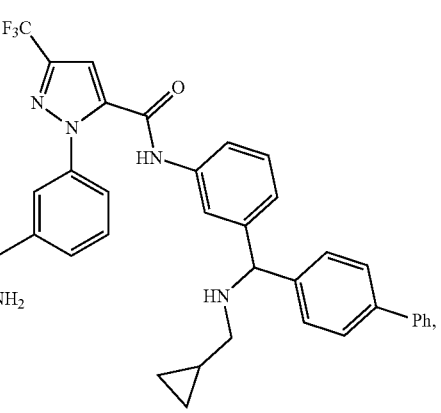
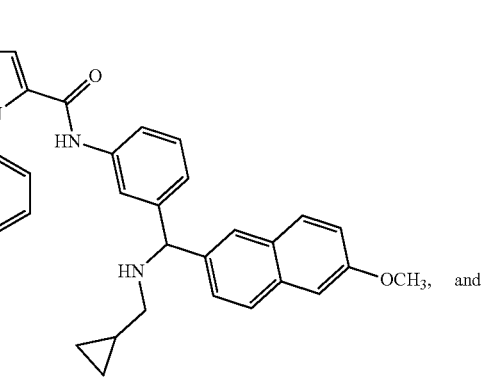

-continued
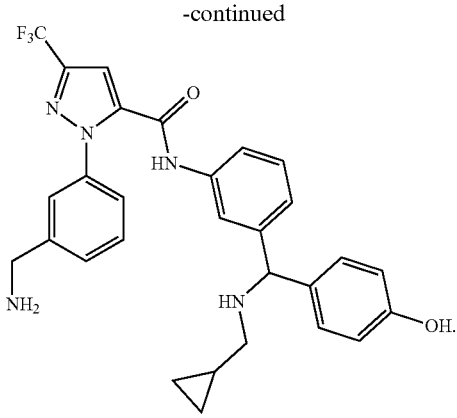
In certain embodiments, the compound is selected from the group consisting of:
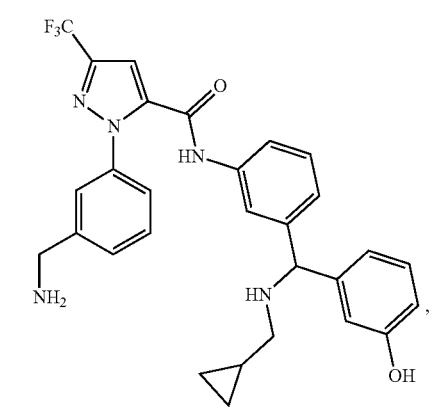
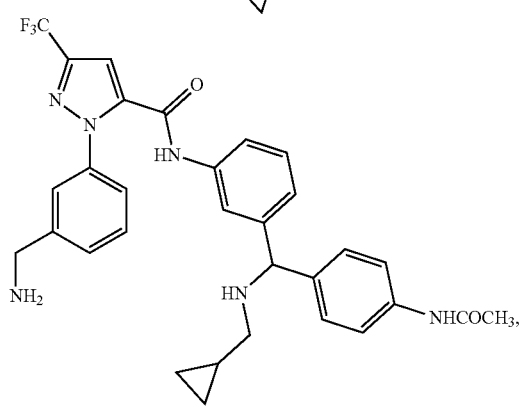
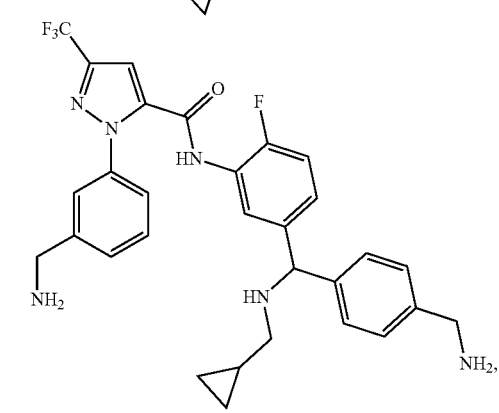
-continued
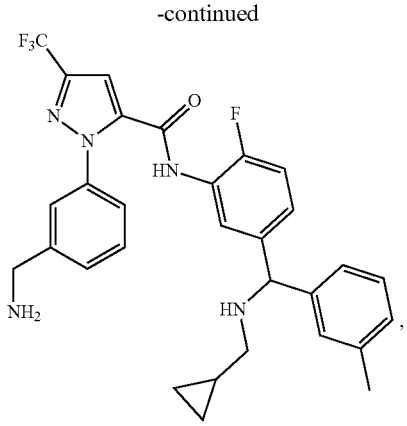
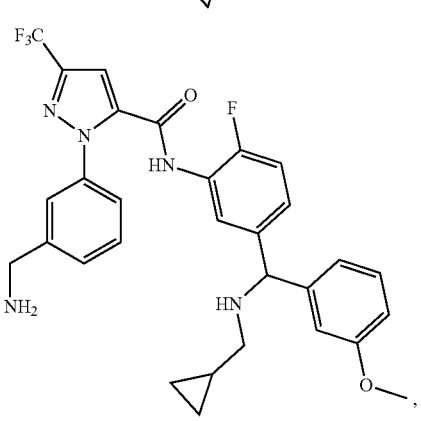
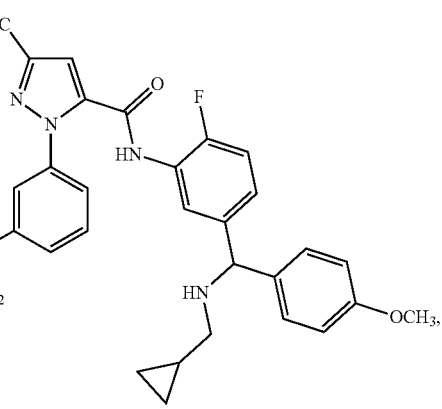
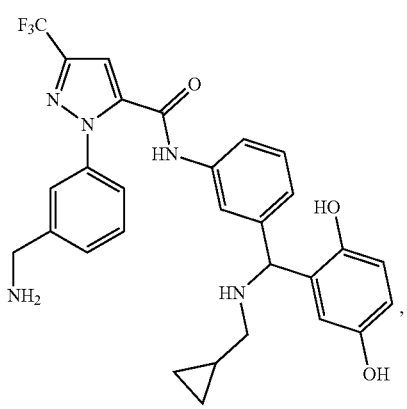

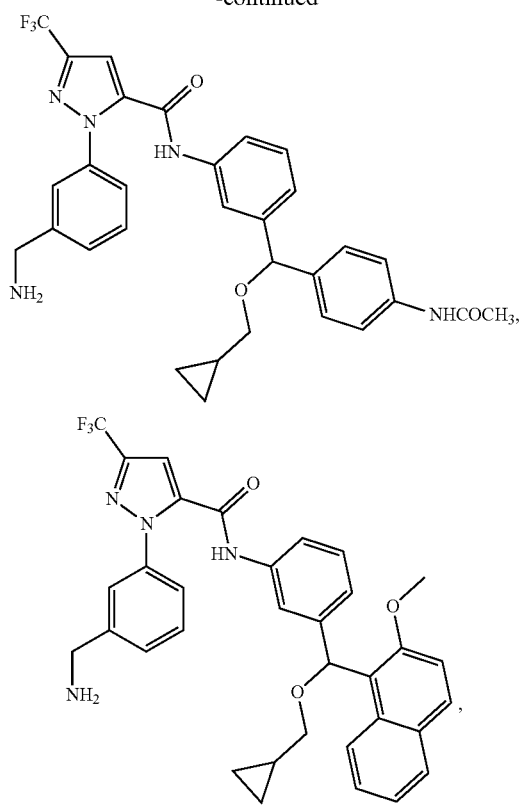
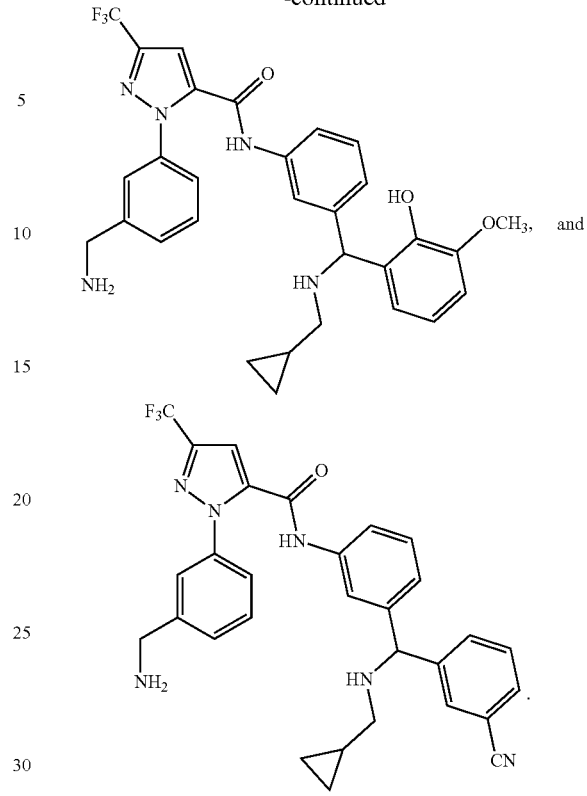
In certain embodiments, the compound is selected from the group consisting of:
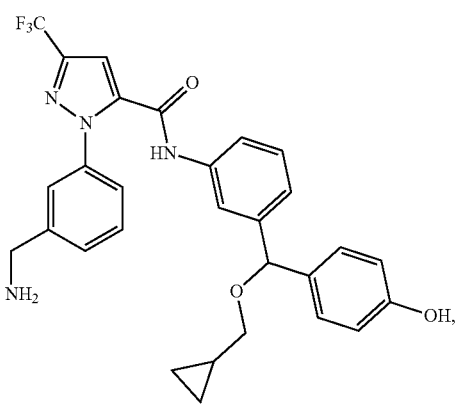
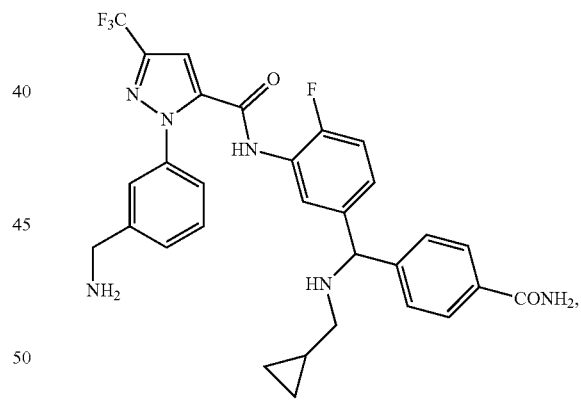
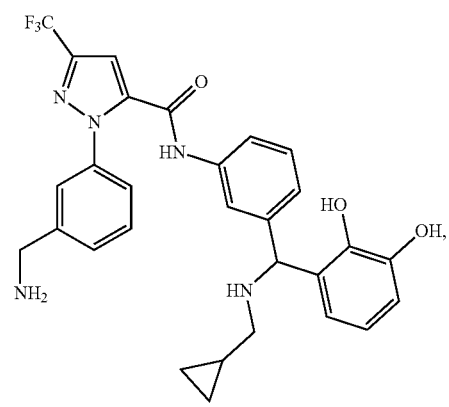
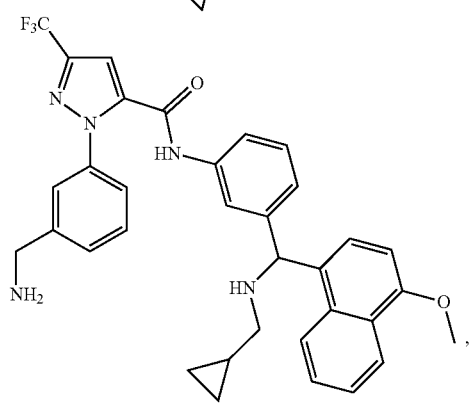

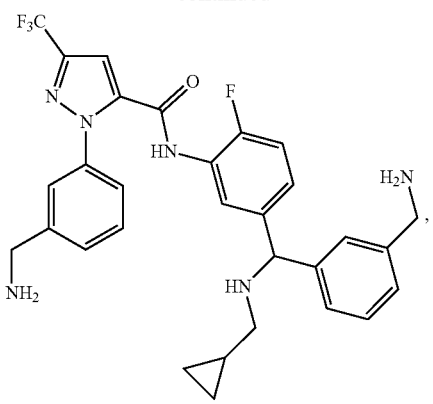
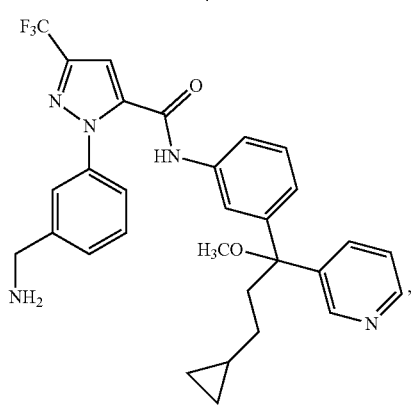
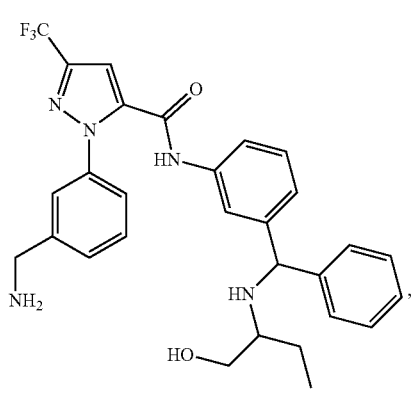
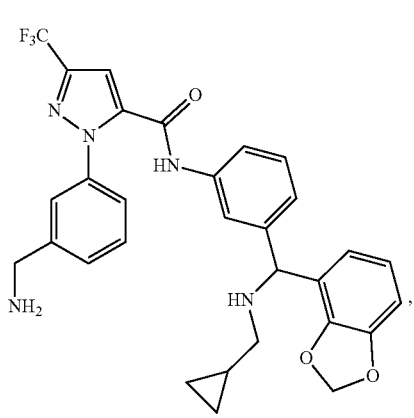
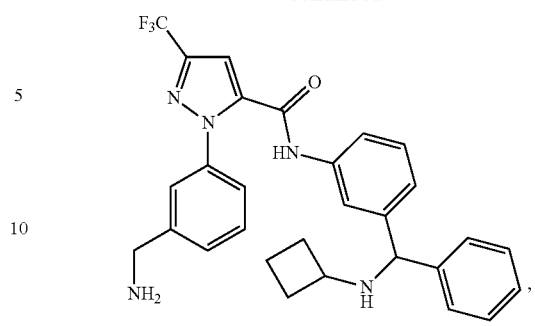
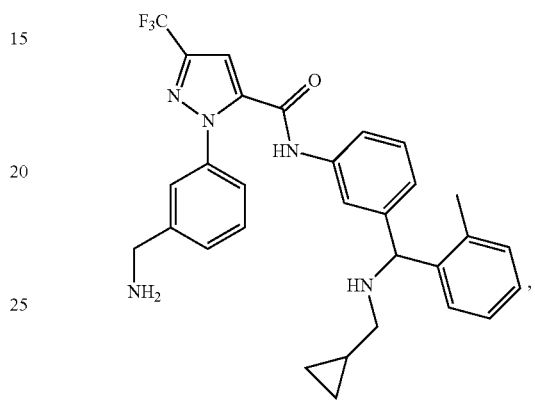
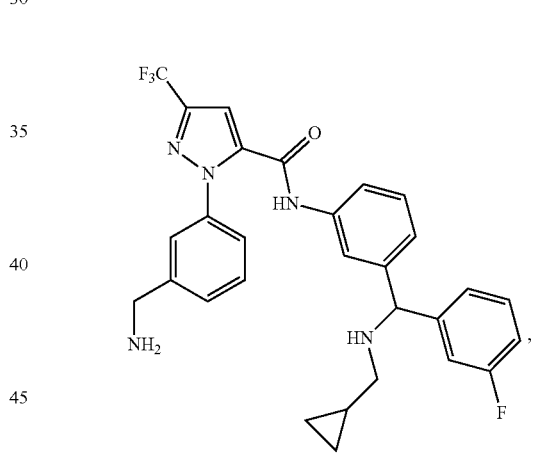
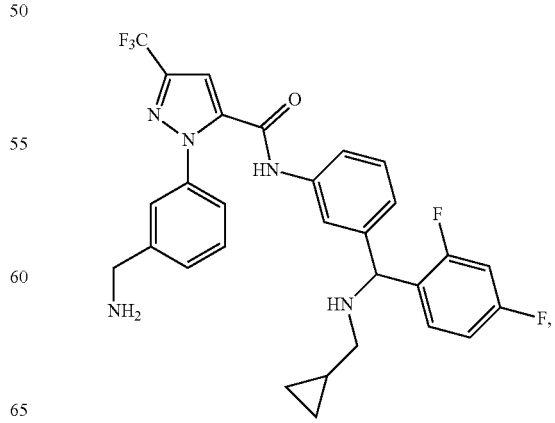

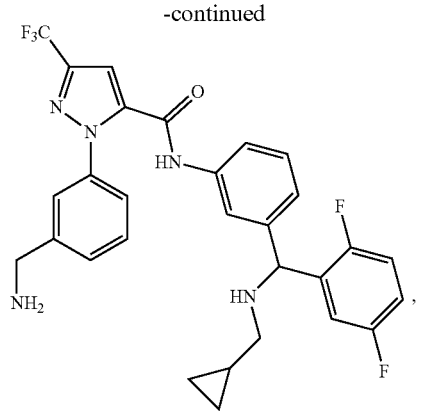
,
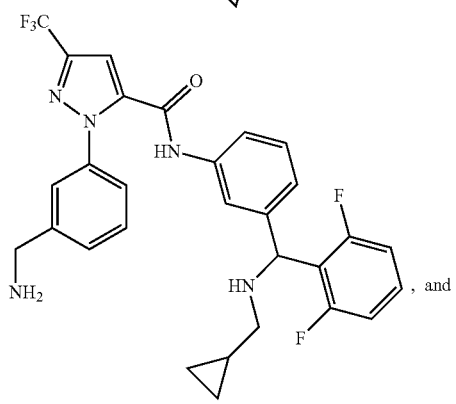
, and
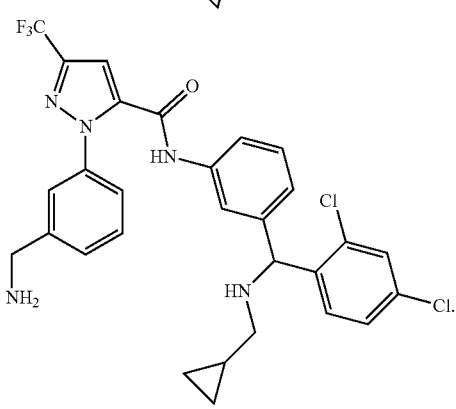
.
In certain embodiments, the compound is selected from the group consisting of:
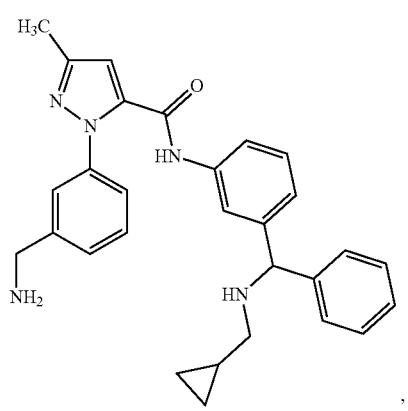
,
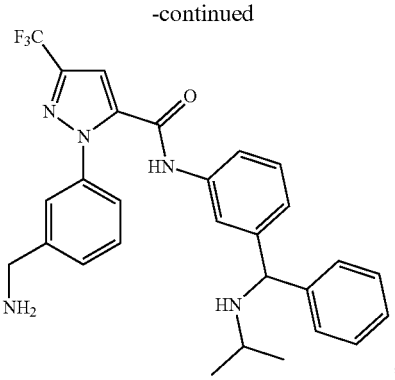
,
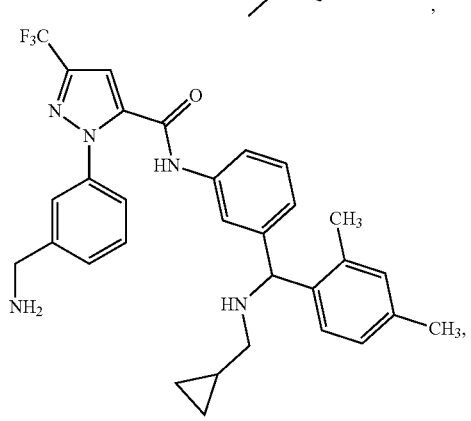
,
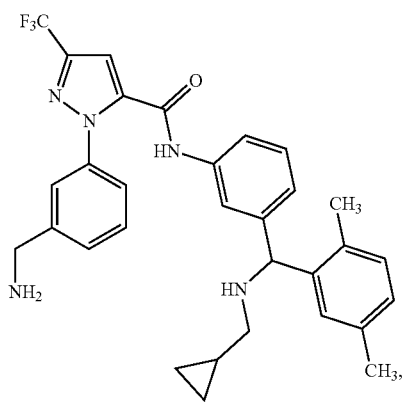
,
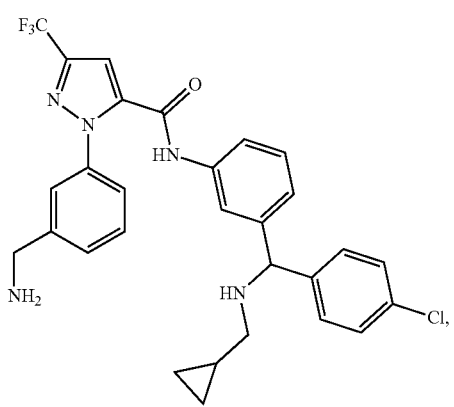
,

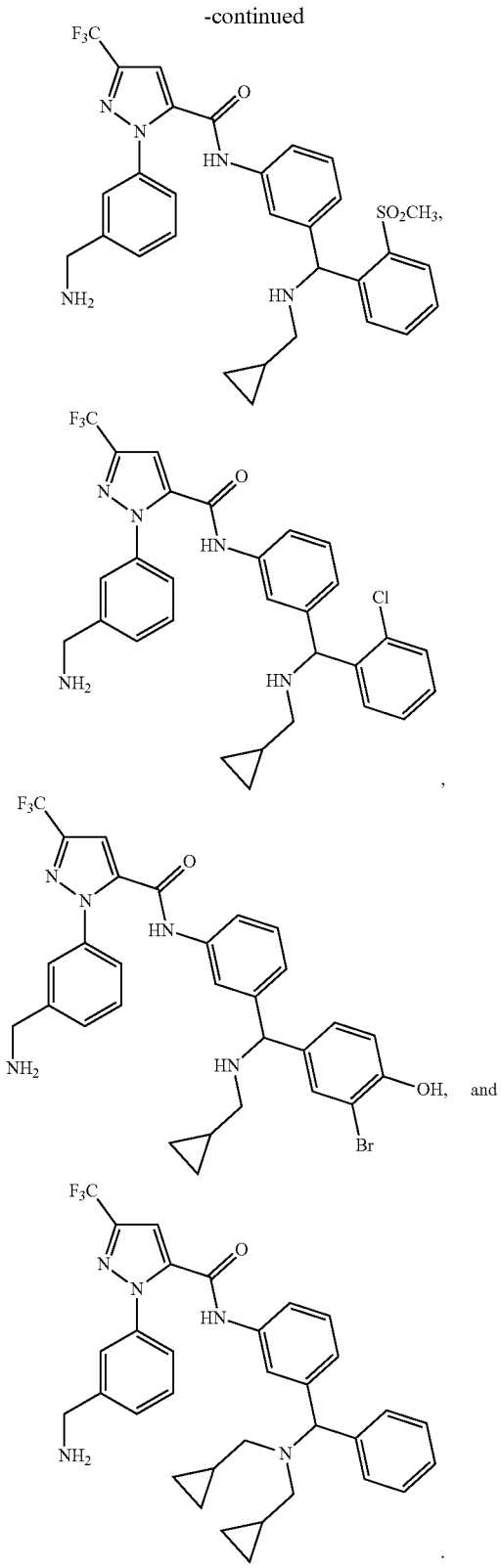

Pharmaceutical Compositions

The invention provides pharmaceutical compositions, each comprising one or more compounds of the invention and a pharmaceutically acceptable carrier. In certain embodiments, the pharmaceutical composition comprises a compound of the invention and a pharmaceutically acceptable carrier. In certain embodiments, the pharmaceutical composition comprises a plurality of compounds of the invention and a pharmaceutically acceptable carrier.

In certain embodiments, a pharmaceutical composition of the invention further comprises at least one additional pharmaceutically active agent other than a compound of the invention. The at least one additional pharmaceutically active agent can be an agent useful in the treatment of a disease or condition characterized by unwanted plasma kallikrein activity. For example, the at least one additional pharmaceutically active agent can be an anticoagulation agent, an anti-platelet agent, or a thrombolytic agent.

Anticoagulation agents prevent the coagulation of blood components and thus prevent clot formation, for example in atrial fibrillation. Anticoagulants include, but are not limited to, heparin, warfarin, coumadin, dicumarol, phenprocoumon, acenocoumarol, ethyl biscoumacetate, hirudin, bivalarutin, direct thrombin inhibitors, and indandione derivatives.

Anti-platelet agents inhibit platelet aggregation and are often used to prevent thromboembolic stroke in patients who have experienced a transient ischemic attack, stroke, or atrial fibrillation. Anti-platelet agents include, but are not limited to, aspirin, thienopyridine derivatives such as ticlopodine and clopidogrel, dipyridamole, and sulfinpyrazone, as well as RGD mimetics.

Thrombolytic agents lyse clots that cause thromboembolic phenomena such as stroke, myocardial infarction, and pulmonary thromboembolism. Thrombolytic agents include, but are not limited to, plasminogen, a2-antiplasmin, streptokinase, antistreplase, TNK, tissue plasminogen activator (tPA), and urokinase. Tissue plasminogen activator includes native tPA and recombinant tPA, as well as modified forms of tPA that retain the enzymatic or fibrinolytic activities of native tPA.

Pharmaceutical compositions of the invention can be prepared by combining one or more compounds of the invention with a pharmaceutically acceptable carrier and, optionally, one or more additional pharmaceutically active agents.

Methods of Use

The present invention provides compounds that inhibit the formation of thrombin via the intrinsic pathway and thus reduce the risk of new pathogenic thrombus formation (vessel occlusion or reocclusion) and also improve fibrinolytic-induced reperfusion when given as adjunctive therapy with a fibrinolytic regimen. Diseases and conditions that can be treated using the compounds of the present invention include, but are not limited to, stroke, inflammation, reperfusion injury, acute myocardial infarction, deep vein thrombosis, post fibrinolytic treatment condition, angina, edema, angioedema, hereditary angioedema, sepsis, arthritis, hemorrhage, blood loss during cardiopulmonary bypass, inflammatory bowel disease, diabetes mellitus, retinopathy, diabetic retinopathy, diabetic macular edema, diabetic macular degeneration, age-related macular edema, age-related macular degeneration, proliferative retinopathy, neuropathy, hypertension, brain edema, increased albumin excretion, macroalbuminuria, and nephropathy.

For example, in patients with angioedema conditions, small polypeptide PK inhibitor DX-88 (ecallantide) alleviates edema in patients with hereditary angioedema (HAE). Williams, A. et al. (2003) *Transfus. Apher. Sci.* 29:255-8; Schneider, L. et al. (2007) *J Allergy Clin Immunol.* 120:416-22; and Levy, J. H. et al. (2006) *Expert Opin. Invest. Drugs* 15:1077-90. A bradykinin B2 receptor antagonist, Icatibant, is also effective in treating HAE. Bork, K. et al. (2007) *J. Allergy Clin. Immunol.* 119:1497-1503. Because plasma kallikrein generates bradykinin, inhibition of plasma kallikrein is expected to inhibit bradykinin production.

For example, in coagulation resulting from fibrinolytic treatment (e.g., treatment with tissue plasminogen activator or streptokinase), higher levels of plasma kallikrein are found in patients undergoing fibrinolysis. Hoffmeister, H. M. et al. (1998) *J. Cardiovasc. Pharmacol.* 31:764-72. Plasmin-mediated activation of the intrinsic pathway has been shown to occur in plasma and blood and was markedly attenuated in plasma from individuals deficient in any of the intrinsic pathway components. Ewald, G. A. et al. (1995) *Circulation* 91:28-36.

Individuals who have had an acute MI were found to have elevated levels of activated plasma kallikrein and thrombin. Hoffmeister, H. M., et al. (1998) *Circulation* 98:2527-33.

DX-88 reduced brain edema, infarct volume, and neurological deficits in an animal model of ischemic stroke. Storini, C. et al. (2006)*J. Pharm. Exp. Ther.* 318:849-854. $C_1$-inhibitor reduced infarct size in a mouse model of middle cerebral artery occlusion (MCAO). De Simoni, M. G. et al. (2004) *Am. J. Pathol.* 164:1857-1863; and Akita, N. et al. (2003) *Neurosurgery* 52:395-400). B2 receptor antagonists were found to reduce the infarct volume, brain swelling, and neutrophil accumulation and were neuroprotective in an MCAO animal model. Zausinger, S. et al. (2003) *Acta Neurochir*. Suppl. 86:205-7; Lumenta, D. B. et al. (2006) *Brain Res.* 1069:227-34; Ding-Zhou, L. et al. (2003) *Br. J Pharmacol.* 139:1539-47.

Regarding blood loss during cardiopulmonary bypass (CPB), it has been found that the kallikrein-kinin (i.e., contact) system is activated during CABG. Wachtfogel, Y. T. (1989) *Blood* 73:468. Activation of the contact system during CPB results in up to a 20-fold increase in plasma bradykinin. Cugno, M. et al. (2006) *Chest* 120:1776-82; and Campbell, D. J. et al. (2001) *Am. J. Physiol. Reg. Integr. Comp. Physiol.* 281:1059-70.

Plasma kallikrein inhibitors P8720 and PKSI-527 have also been found to reduce joint swelling in rat models of arthritis. De La Cadena, R. A. et al. (1995) *FASEB J.* 9:446-52; Fujimori, Y. (1993) *Agents Action* 39:42-8. It has also been found that inflammation in animal models of arthritis was accompanied by activation of the contact system. Blais, C. Jr. et al. (1997) *Arthritis Rheum.* 40:1327-33.

Additionally, plasma kallikrein inhibitor P8720 has been found to reduce inflammation in an acute and chronic rat model of inflammatory bowel disease (IBD). Stadnicki, A. et al. (1998) *FASEB J.* 12:325-33; Stadnicki, A. et al. (1996) *Dig. Dis. Sci.* 41:912-20; and De La Cadena, R. A., et al. (1995) *FASEB J.* 9:446-52. The contact system is activated during acute and chronic intestinal inflammation. Sartor, R. B. et al. (1996) *Gastroenterology* 110:1467-81. It has been found that B2 receptor antagonist, an antibody to high molecular weight kininogen, or reduction in levels of kininogen reduced clinicopathology in animal models of IBD. Ibid.; Arai, Y. et al. (1999) *Dig. Dis. Sci.* 44:845-51; and Keith, J. C. et al. (2005) *Arthritis Res. Therapy* 7:R769-76.

H-D-Pro-Phe-Arg-chloromethylketone (CMK), an inhibitor of PK and FXII and a physiological inhibitor (Cl-inhibitor), has been found to reduce vascular permeability in multiple organs and reduce lesions in lipopolysaccharide (LPS)- or bacterial-induced sepsis in animals. Liu, D. et al. (2005) *Blood* 105:2350-5; Persson, K. et al. (2000)*J. Exp. Med.* 192:1415-24. Clinical improvement was observed in sepsis patients treated with Cl-inhibitor. Zeerleder, S. et al. (2003) *Clin. Diagnost. Lab. Immunol.* 10:529-35; Caliezi, C., et al. (2002) *Crit. Care Med.* 30:1722-8; and Marx, G. et al. (1999) *Intensive Care Med.* 25:1017-20. Fatal cases of septicemia are found to have a higher degree of contact activation. Martinez-Brotons, F. et al. (1987) *Thromb. Haemost.* 58:709-713; and Kalter, E. S. et al. (1985) *J. Infect. Dis.* 151:1019-27.

It has also been found that prePK levels are higher in diabetics, especially those with proliferative retinopathy, and correlate with fructosamine levels. Gao, B.-B., et al. (2007) *Nature Med.* 13:181-8; and Kedzierska, K. et al. (2005) *Archives Med. Res.* 36:539-43. PrePK is also found to be highest in those with a sensorimotor neuropathy. Christie, M. et al. (1984) *Thromb. Haemostas.* (Stuttgart) 52:221-3. PrePK levels are elevated in diabetics and are associated with increased blood pressure. PrePK levels independently correlate with the albumin excretion rate and are elevated in diabetics with macroalbuminuria, suggesting prePK may be a marker for progressive nephropathy. Jaffa, A. A. et al. (2003) *Diabetes* 52:1215-21. B1 receptor antagonists have been found to decrease plasma leakage in rats treated with streptozotocin. Lawson, S. R. et al. (2005) *Eur. J. Pharmacol.* 514:69-78. B1 receptor antagonists can also prevent streptozotocin-treated mice from developing hyperglycemia and renal dysfunction. Zuccollo, A. et al. (1996) *Can. J. Physiol. Pharmacol.* 74:586-9.

In certain aspects, the invention provides a compound of the invention, or a pharmaceutically acceptable salt thereof, for use as a medicament.

In certain aspects, the invention provides methods of treating or preventing a disease or condition characterized by unwanted plasma kallikrein activity. The method includes the step of administering to a subject in need thereof a therapeutically effective amount of a compound of the invention, or a pharmaceutically acceptable salt thereof, thereby treating or preventing the disease or condition characterized by unwanted plasma kallikrein activity. By reducing plasma kallikrein activity in the subject, the disease or condition characterized by unwanted plasma kallikrein activity is treated.

Alternatively, in certain aspects, the invention provides a compound of the invention, or a pharmaceutically acceptable salt thereof, for treatment of a disease or condition characterized by unwanted plasma kallikrein activity.

Alternatively, in certain aspects, the invention provides the use of a compound of the invention, or a pharmaceutically acceptable salt thereof, for the manufacture of a medicament for use in treatment of a disease or condition characterized by unwanted plasma kallikrein activity.

As used herein, a "disease or condition characterized by unwanted plasma kallikrein activity" refers to any disease or condition in which it is desirable to reduce plasma kallikrein activity. For example, it may be desirable to reduce plasma kallikrein activity in the setting of a hypercoagulable state. As another example, it may be desirable to reduce plasma kallikrein activity in the setting of tissue ischemia that is associated with the presence or formation of thrombus.

In certain embodiments, the disease or condition characterized by unwanted plasma kallikrein activity is selected from the group consisting of stroke, inflammation, reperfusion injury, acute myocardial infarction, deep vein thrombosis, post fibrinolytic treatment condition, angina, edema, angioedema, hereditary angioedema, sepsis, arthritis, hemorrhage, blood loss during cardiopulmonary bypass, inflammatory bowel disease, diabetes mellitus, retinopathy, diabetic retinopathy, diabetic macular edema, diabetic macular degeneration, age-related macular edema, age-related macular degeneration, proliferative retinopathy, neuropathy, hypertension, brain edema, increased albumin excretion, macroalbuminuria, and nephropathy.

In certain embodiments, the disease or condition characterized by unwanted plasma kallikrein activity is angioedema.

In certain embodiments, the disease or condition characterized by unwanted plasma kallikrein activity is hereditary angioedema (HAE).

In certain embodiments, the disease or condition characterized by unwanted plasma kallikrein activity is stroke.

In certain embodiments, the disease or condition characterized by unwanted plasma kallikrein activity is reperfusion injury.

In certain embodiments, the disease or condition characterized by unwanted plasma kallikrein activity is acute myocardial infarction.

In certain embodiments, the disease or condition characterized by unwanted plasma kallikrein activity is hemorrhage.

In certain embodiments, the disease or condition characterized by unwanted plasma kallikrein activity is blood loss during cardiopulmonary bypass.

In certain embodiments, the disease or condition characterized by unwanted plasma kallikrein activity is selected from the group consisting of retinopathy, diabetic retinopathy, diabetic macular edema, diabetic macular degeneration, age-related macular edema, age-related macular degeneration, and proliferative retinopathy.

Formulations, Routes of Administration, and Dosing

The compounds of the invention can be formulated as pharmaceutical compositions and administered to a mammalian host, such as a human patient, in a variety of forms adapted to the chosen route of administration, e.g., orally or parenterally, by intravenous, intraperitoneal, intramuscular, topical, or subcutaneous routes. Additional routes of administration are also contemplated by the invention.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of a given unit dosage form. The amount of active compound in such therapeutically useful compositions is such that an effective dosage level will be obtained.

The tablets, troches, pills, capsules, and the like may also contain the following diluents and carriers: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water or physiologically acceptable aqueous solution, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, methods of preparation can include vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the invention to the skin are known in the art; for example, see Jacquet et al. (U.S. Pat. No. 4,608,392; incorporated herein by reference), Geria (U.S. Pat. No. 4,992,478; incorporated herein by reference), Smith et al. (U.S. Pat. No. 4,559,157; incorporated herein by reference), and Wortzman (U.S. Pat. No. 4,820,508; incorporated herein by reference).

Useful dosages of the compounds of the invention can be determined, at least initially, by comparing their in vitro activity and in vivo activity in animal models. Methods for the extrapolation of effective dosages in mice, and other animals, to humans are known in the art; for example, see U.S. Pat. No. 4,938,949 (incorporated herein by reference).

The amount of the compound, or an active salt thereof, required for use in treatment will vary not only with the particular compound or salt selected but also with the route of administration, the nature of the condition being treated, and the age and condition of the patient and will be ultimately at the discretion of the attendant physician or clinician.

In general, however, a suitable dose will be in the range of from about 0.5 to about 100 mg/kg body weight of the recipient per day, e.g., from about 3 to about 90 mg/kg of body weight per day, from about 6 to about 75 mg per kilogram of body weight per day, from about of 10 to about 60 mg/kg of body weight per day, or from about 15 to about 50 mg/kg of body weight per day.

Compounds of the invention can be conveniently formulated in unit dosage form; for example, containing 5 to 1000 mg, 10 to 750 mg, or 50 to 500 mg of active ingredient per unit dosage form. In one embodiment, the invention provides a composition comprising a compound of the invention formulated in such a unit dosage form. The desired dose may conveniently be presented in a single dose or as divided doses to be administered at appropriate intervals, for example, as two, three, four or more sub-doses per day. The sub-dose itself may be further divided, e.g., into a number of discrete loosely spaced administrations.

Compounds of the invention can also be administered in combination with other therapeutic agents, for example, other agents that are useful for treating or preventing ischemia, blood loss, or reperfusion injury.

Other delivery systems can include time-release, delayed release, or sustained release delivery systems such as are well-known in the art. Such systems can avoid repeated administrations of the active compound, increasing convenience to the subject and the physician. Many types of release delivery systems are available and known to those of ordinary skill in the art. Use of a long-term sustained release implant may be desirable. Long-term release, as used herein, means that the delivery system or is implant constructed and arranged to deliver therapeutic levels of the active ingredient for at least 30 days, and preferably 60 days.

In certain embodiments, a compound of the invention is formulated for intraocular administration, for example direct injection or insertion within or in association with an intraocular medical device.

The compounds of the invention may be formulated for depositing into a medical device, which may include any of a variety of conventional grafts, stents, including stent grafts, catheters, balloons, baskets, or other device that can be deployed or permanently implanted within a body lumen. As a particular example, it would be desirable to have devices and methods which can deliver compounds of the invention to the region of a body which has been treated by interventional technique.

In exemplary embodiment, a compound of the invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also be used to deliver a drug at the site of contact with the vasculature, as disclosed in U.S. Pat. No. 5,102,417 (Palmaz), U.S. Pat. No. 5,419,760 (Narciso, Jr.), U.S. Pat. No. 5,429,634 (Narciso, Jr.), and in International Patent Application Nos. WO 91/12779 (Medtronic, Inc.) and WO 90/13332 (Cedars-Sanai Medical Center), for example.

The term "deposited" means that the compound is coated, adsorbed, placed, or otherwise incorporated into the device by methods known in the art. For example, the compound may be embedded and released from within ("matrix type") or surrounded by and released through ("reservoir type") polymer materials that coat or span the medical device. In the latter example, the compound may be entrapped within the polymer materials or coupled to the polymer materials using one or more the techniques for generating such materials known in the art. In other formulations, the compound may be linked to the surface of the medical device without the need for a coating, for example by means of detachable bonds, and release with time or can be removed by active mechanical or chemical processes. In other formulations, the compound may be in a permanently immobilized form that presents the compound at the implantation site.

In certain embodiments, the compound may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but frequently a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D,L-lactic acid), poly(D,L-lactide) (PLA), poly (L-lactide) (PLLA), poly(glycolic acid-co-trimethylene carbonate) (PGA/PTMC), polyethylene oxide (PEO), polydioxanone (PDS), polyphosphoester, polyphosphoester urethane, poly (amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable polymers known in the art. Also, biostable polymers with a relatively low chronic tissue response such as polyurethanes, silicones, and polyesters could be used, and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In certain embodiments of the invention, the compound of the invention is coupled to a polymer or semipermeable polymer matrix that is formed as a stent or stent-graft device.

Typically, polymers are applied to the surface of an implantable device by spin coating, dipping, or spraying. Additional methods known in the art can also be utilized for this purpose.

Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In certain embodiments of the invention, the compound is formulated for release from the polymer coating into the environment in which the medical device is placed. Preferably, the compound is released in a controlled manner over an extended time frame (e.g., months) using at least one of several well-known techniques involving polymer carriers or layers to control elution. Some of these techniques are described in U.S. Patent Application 2004/0243225A1, the entire disclosure of which is incorporated herein in its entirety.

Moreover, as described for example in U.S. Pat. No. 6,770,729, which is incorporated herein in its entirety, the reagents and reaction conditions of the polymer compositions can be manipulated so that the release of the compound from the polymer coating can be controlled. For example, the diffusion coefficient of the one or more polymer coatings can be modulated to control the release of the compound from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the compound from the polymer coating). Yet another embodiment of the invention includes a device having a plurality of polymer coatings, each having a plurality of diffusion coefficients. In such embodiments of the invention, the release of the compound from the polymer coating can be modulated by the plurality of polymer coatings.

In yet another embodiment of the invention, the release of the compound from the polymer coating is controlled by modulating one or more of the properties of the polymer composition, such as the presence of one or more endogenous or exogenous compounds, or alternatively, the pH of the polymer composition. For example, certain polymer compositions can be designed to release a compound in response to a decrease in the pH of the polymer composition.

Kits

The invention also provides a kit, comprising a compound of the invention, or a pharmaceutically acceptable salt thereof; at least one other therapeutic agent, packaging material, and instructions for administering the compound of the invention or the pharmaceutically acceptable salt thereof and the other therapeutic agent or agents to a mammal to treat or prevent ischemia, blood loss, or reperfusion injury in the mammal. In one embodiment, the mammal is a human.

EXAMPLES

The present invention is further illustrated by the following examples, which in no way should be construed as further limiting. The entire contents of all the references (including literature references, issued patents, published patent applications, and co-pending patent applications) cited throughout this application are hereby expressly incorporated by reference.

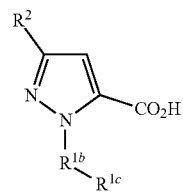

Appropriately substituted pyrazole carboxylic acid can be prepared by various methods as reported in the following references 1. Substituted pyrazolyl-based carboxamide and urea derivatives bearing a phenyl moiety substituted with an SO2-containing group as vanilloid receptor ligands; Frank, Robert et al; PCT Int. Appl., 2013/068464, 16 May 2013 (incorporated by reference)
2. Design, synthesis and biological activity of E-β-farnesene analogues containing pyrazole-carboxamide; Sun, Yufeng et al; Youji Huaxue, 31(9), 1425-1432; 2011
3. Preparation of heterocyclic urea derivatives as kinase inhibitors useful for the treatment of myeloproliferative diseases and other proliferative diseases; Flynn, Daniel L. et al; PCT Int. Appl., 2013/036232 (incorporated by reference).
4. Substituted phenylureas and phenylamides as vanilloid receptor ligands and their preparation; By Frank, Robert et al; U.S. Pat. Appl. Publ., 2012/0258946 (incorporated by reference)
5. Substituted cyclic carboxamide and urea derivatives as ligands of the vanilloid receptor; Frank, Robert et al; PCT Int. Appl., 2012/022487 (incorporated by reference)
6. Preparation of heterocyclic urea derivatives as kinase inhibitors useful for the treatment of hyperproliferative and other diseases; Flynn, Daniel L. and Kaufman, Michael D; U.S. Pat. Appl. Publ., 2012/0225057 (incorporated by reference).
7. Preparation of pyrazolylpyrimidine derivatives for use as protein kinase modulators; Casuscelli, Francesco et al; PCT Int. Appl., 2012/139930 (incorporated by reference)
8. Preparation of substituted heteroaromatic carboxamide and urea compounds as vanilloid receptor ligands; Frank, Robert et al; U.S. Pat. Appl. Publ., 2012/0115903 (incorporated by reference)
9. Preparation of pyrazole derivatives as modulators of calcium release-activated calcium channel for treatment of non-small cell lung cancer; Muthuppalaniappan, Meyyappan et al; Indian Pat. Appl., 2009CH02439
10. 3-methoxy pyridine amides with good insecticidal activity and their preparation; Li, Bin et al; Faming Zhuanli Shenqing, 102285963
11. Preparation of amidinoaneline derivatives with inhibitory activity to activated blood coagulation factor X; Matsumoto, Kayo et al; PCT Int. Appl., 2011/118818 (incorporated by reference)
12. Preparation of 1-(5-tert-butyl-2-phenyl-2H-pyrazol-3-yl)-3-[2-fluoro-4-(1-methyl-2-oxo-2,3-dihydro-1H-imidazo[4,5-b]pyridin-7-yloxy)phenyl]urea and related compounds as antitumor agents; Springer, Caroline et al; PCT Int. Appl., 2011/092469 (incorporated by reference)
13. 3-(1-aminoalkyl)pyrazole- and 4,5-dihydropyrazole-5-carboxylic acids as peptide bond replacements; Jones, Raymond C. F. et al; Synlett, (2), 211-214; 2011
14. New Analogues of (E)-β-Farnesene with Insecticidal Activity and Binding Affinity to Aphid Odorant-Binding Proteins; Sun, Yufeng et al; Journal of Agricultural and Food Chemistry, 59(6), 2456-2461; 2011
15. 1,2-Diamines as inhibitors of co-activator associated arginine methyltransferase 1 (CARM1); Therrien, Eric et al; Bioorganic & Medicinal Chemistry Letters, 19(23), 6725-6732; 2009
16. Preparation of benzamide compounds as pesticides; Li, Bin et al; Faming Zhuanli Shenqing Gongkai Shuomingshu, 101298451
17. Optimization of pyrazole inhibitors of coactivator associated arginine methyltransferase 1 (CARM1); Huynh, Tram et al; Bioorganic & Medicinal Chemistry Letters, 19(11), 2924-2927; 2009
18. Pyrazole derivatives as LXR and FXR modulators and their preparation, pharmaceutical compositions and use in the treatment of diseases; Boren, Brant Clayton et al; PCT Int. Appl., 2008/073825 (incorporated by reference)
19. Preparation of N-(pyridylpyrimidinylaminophenyl)amides as protein kinase inhibitors; Chianelli, Donatella et al; PCT Int. Appl., 2008/058037 (incorporated by reference)
20. Preparation of heterocyclic ureas as kinase inhibitors useful for the treatment of proliferative and inflammatory diseases; Flynn, Daniel L. et al; PCT Int. Appl., 2008/034008 (incorporated by reference)
21. Heterocyclic derivatives as inhibitors of protein arginine methyltransferases and their preparation, pharmaceutical compositions and use in the treatment of diseases, Wahhab, Amal et al; PCT Int. Appl., 2008/104077 (incorporated by reference)
22. Preparation of heterocyclic ureas as kinase inhibitors useful for the treatment of proliferative and inflammatory diseases; Flynn, Daniel L. et al; PCT Int. Appl., 2008/034008 (incorporated by reference)
23. Novel N-heterocyclic phosphonates and phosphinates as glucokinase activators for treatment of Type II diabetes; Ryono, Dennis E. et al; PCT Int. Appl., 2008/005964 (incorporated by reference)
24. Reductive isoxazole ring opening of the anticoagulant razaxaban is the major metabolic clearance pathway in rats and dogs; Zhang, Donglu et al; Drug Metabolism and Disposition, 36(2), 303-315; 2008
25. Structure-activity relationship and pharmacokinetic profile of 5-ketopyrazole factor Xa inhibitors; Varnes, Jeffrey G. et al; Bioorganic & Medicinal Chemistry Letters, 18(2), 749-754; 2008
26. Preparation of (pyrazolecarbonylamino)benzamide derivatives as insecticides and fungicides; Li, Bin et al; PCT Int. Appl., 2008/134969 (incorporated by reference)
27. Pyrazole inhibitors of coactivator associated arginine methyltransferase 1 (CARM1); Purandare, Ashok V. et al; Bioorganic & Medicinal Chemistry Letters, 18(15), 4438-4441; 2008
28. Potent Non-Nucleoside Inhibitors of the Measles Virus RNA-Dependent RNA Polymerase Complex; Sun, Aiming et al; Journal of Medicinal Chemistry, 51(13), 3731-3741; 2008
29. Design, structure-activity relationship, and pharmacokinetic profile of pyrazole-based indoline factor Xa inhibitors; Varnes, Jeffrey G. et al; Bioorganic & Medicinal Chemistry Letters, 17(23), 6481-6488; 2007
30. Preparation of pyrazoles for the treatment of obesity and other CNS disorders; Bennani, Youseff L. et al; PCT Int. Appl., 2007/094962 (incorporated by reference)
31. Preparation of ureidopyrazoles as kinase inhibitors, particularly as p38 kinase inhibitors; Bastian, Jolie Anne et al; PCT Int. Appl., 2007/053394, 10 May 2007
32. Hydrazide compound and their preparation, formulation and pesticidal use; Ikegami, Hiroshi et al; PCT Int. Appl., 2007/043677 (incorporated by reference)
33. Trimethylsilylpyrazoles as novel inhibitors of p38 MAP kinase: A new use of silicon bioisosteres in medicinal chemistry; Barnes, Matthew J. et al; Bioorganic & Medicinal Chemistry Letters, 17(2), 354-357; 2007
34. Preparation of anthranilamide derivative insecticides and acaricides; Lahm, George Philip et al; PCT Int. Appl., 2006/055922 (incorporated by reference)
35. Preparation of amino acid derivatives as inhibitors of protein arginine methyl transferases; Purandare, Ashok Vinayak and Chen, Zhong; PCT Int. Appl., 2006/069155 (incorporated by reference)
36. Preparation of azole carboxamides as inhibitors of bacterial type III protein secretion systems; Li, Xiaobing et al; PCT Int. Appl., 2005/113522 (incorporated by reference)
37. Preparation of pyrazolylbenzamides and pyrazolopyridinylbenzamides as factor Xa inhibitors for the treatment of thromboembolic disorders; Lam, Patrick Y. et al; U.S. Pat. Appl. Publ., 2006/0089496 (incorporated by reference)

38. Preparation of pyrazolylcarbonyl anthranilamides as insecticides; Lahm, George Philip and Selby, Thomas Paul; PCT Int. Appl., 2005/118552 (incorporated by reference)
39. Insecticidal anthranilic diamides: A new class of potent ryanodine receptor activators; Lahm, George P. et al; Bioorganic & Medicinal Chemistry Letters, 15(22), 4898-4906; 2005
40. Process for the preparation of 1,3,5-trisubstituted pyrazoles via [3+2] cycloaddition; Shapiro, Rafael et al; U.S. Pat. Appl. Publ., 2006/0069270 (incorporated by reference)
41. Preparation of amides of pyrazolamines and anilines as well as analogs as cytokine inhibitors for the treatment of inflammatory diseases; Boman, Erik et al; PCT Int. Appl., 2005/023761 (incorporated by reference)
42. Discovery of 1-(3'-Aminobenzisoxazol-5'-yl)-3-trifluoromethyl-N-[2-fluoro-4-[(2'-dimethylaminomethyl)imidazol-1-yl]phenyl]-1H-pyrazole-5-carboxyamide Hydrochloride (Razaxaban), a Highly Potent, Selective, and Orally Bioavailable Factor Xa Inhibitor; Quan, Mimi L. et al; Journal of Medicinal Chemistry, 48(6), 1729-1744; 2005
43. Preparation of N-arylheteroaryls, in particular N-phenylpiperazinyl methanones, as inhibitors of tubulin polymerization and their compositions for treatment of cancer; Le-Brun, Alain et al; PCT Int. Appl., 2004/078732 (incorporated by reference)
44. Preparation of 1,2-azole derivatives with hypoglycemic and hypolipidemic activity; Maekawa, Tsuyoshi et al; PCT Int. Appl., 2003/099793 (incorporated by reference)
45. Discovery of 1-(2-Aminomethylphenyl)-3-trifluoromethyl-N-[3-fluoro-2'-(aminosulfonyl)[1,1'-biphenyl)]-4-yl]-1H-pyrazole-5-carboxamide (DPC602), a Potent, Selective, and Orally Bioavailable Factor Xa Inhibitor; Pruitt, James R. et al; Journal of Medicinal Chemistry, 46(25), 5298-5315; 2003
46. 1-(2-Naphthyl)-1H-pyrazole-5-carboxylamides as potent factor Xa inhibitors. Part 3: Design, synthesis and SAR of orally bioavailable benzamidine-P4 inhibitors; Jia, Zhaozhong J. et al; Bioorganic & Medicinal Chemistry Letters, 14(5), 1229-1234; 2004
47. Preparation of novel N-[4-(1H-imidazol-1-yl)-2-fluorophenyl]-3-(trifluoromethyl)-1H-pyrazole-5-carboxamides as factor Xa inhibitors; Quan, Mimi L; PCT Int. Appl., 2003/047517 (incorporated by reference)
48. Preparation of imidazolylphenylpyrazolopyridinones as factor Xa inhibitors; Quan, Mimi L. and Wexler, Ruth R; PCT Int. Appl., 2003/047520 (incorporated by reference)
49. Preparation of novel substituted 1H-dihydropyrazoles; Annis, Gary David et al; PCT Int. Appl., 2003/016282 (incorporated by reference)
50. Pesticidal compositions for coating plant propagation material containing anthranilamides; Berger, Richard Alan and Flexner, John Lindsey; PCT Int. Appl., 2003/024222 (incorporated by reference)
51. Method for controlling particular insect pests by applying anthranilamide compounds; Lahm, George Philip et al; PCT Int. Appl., 2003/015518 (incorporated by reference)
52. Design, synthesis and biological activity of novel nonamidine factor Xa inhibitors. Part 1: P1 structure-activity relationships of the substituted 1-(2-Naphthyl)-1H-pyrazole-5-carboxylamides; Jia, Zhaozhong J. et al; Bioorganic & Medicinal Chemistry Letters, 12(12), 1651-1655; 2002
53. Efficient process for the preparation of a factor Xa inhibitor; Sunkara, Hari Babu and Yang, Yali; PCT Int. Appl., 2002/024690 (incorporated by reference), 28 Mar. 2002
54. Preparation of pyrazolecarboxamides as inhibitors of factor Xa; Zhu, Bing-yan et al; U.S. Pat. Appl. Publ., 2002/0091116 (incorporated by reference)
55. Preparation of dihydrobenzo[b][1,4]diazepin-2-ones as mGluR2 antagonists for treatment of neurological disorders; Adam, Geo et al; PCT Int. Appl., 2002/083652 (incorporated by reference)
56. Preparation of azole inhibitors of cytokine production; Bamaung, Nwe Y. et al; U.S. Pat. Appl. Publ., 2001/0044445 (incorporated by reference)
57. Parallel Synthesis of Potent, Pyrazole-Based Inhibitors of *Helicobacter pylori* Dihydroorotate Dehydrogenase; Haque, Tasir S. et al; Journal of Medicinal Chemistry, 45(21), 4669-4678; 2002
58. Preparation of 1,3,5-trisubstituted pyrazoles for pharmaceutical use as factor Xa inhibitors; Zhou, Jiacheng et al; PCT Int. Appl., 2001/029006 (incorporated by reference)
59. Discovery of 1-[3-(Aminomethyl)phenyl]-N-[3-fluoro-2'-(methylsulfonyl)-[1,1'-biphenyl]-4-yl]-3-(trifluoromethyl)-1H-pyrazole-5-carboxamide (DPC423), a Highly Potent, Selective, and Orally Bioavailable Inhibitor of Blood Coagulation Factor Xa; Pinto, Donald J. P. et al; Journal of Medicinal Chemistry, 44(4), 566-578; 2001
60. Preparation of novel guanidine mimics as factor Xa inhibitors; Lam, Patrick Y. et al; PCT Int. Appl., 98/57951 (incorporated by reference)
61. Some reactions of β-aroylacrylic acid epoxide; By El-Sawy, A. A. et al; Journal of the Serbian Chemical Society, 56(10), 587-94; 1991
62. The effect of 1,3-diphenylpyrazolecarboxylic acid derivatives on the hepatic cytochrome P-450 system; Khlopushina, T. G. et al; Khimiko-Farmatsevticheskii Zhurnal, 25(11), 10-13; 1991
63. Preparation and testing of phenylpyrazolecarboxylates as plant growth regulators and protectants; Sohn, Erich et al; Ger. Offen., 3633840
64. Action of nitrogen nucleophiles on oxiranes of β-aroylacrylic acids; Omran, S. A. et al; Egyptian Journal of Chemistry, 28(5), 399-410; 1986
65. The sequential lithiation of 1-phenylpyrazoles; Micetich, Ronald G. et al; Heterocycles, 23(4), 943-51; 1985

Scheme 1

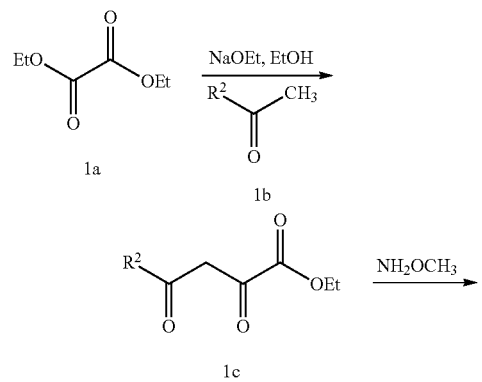

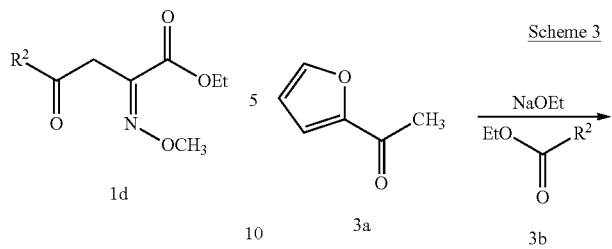
Scheme 3
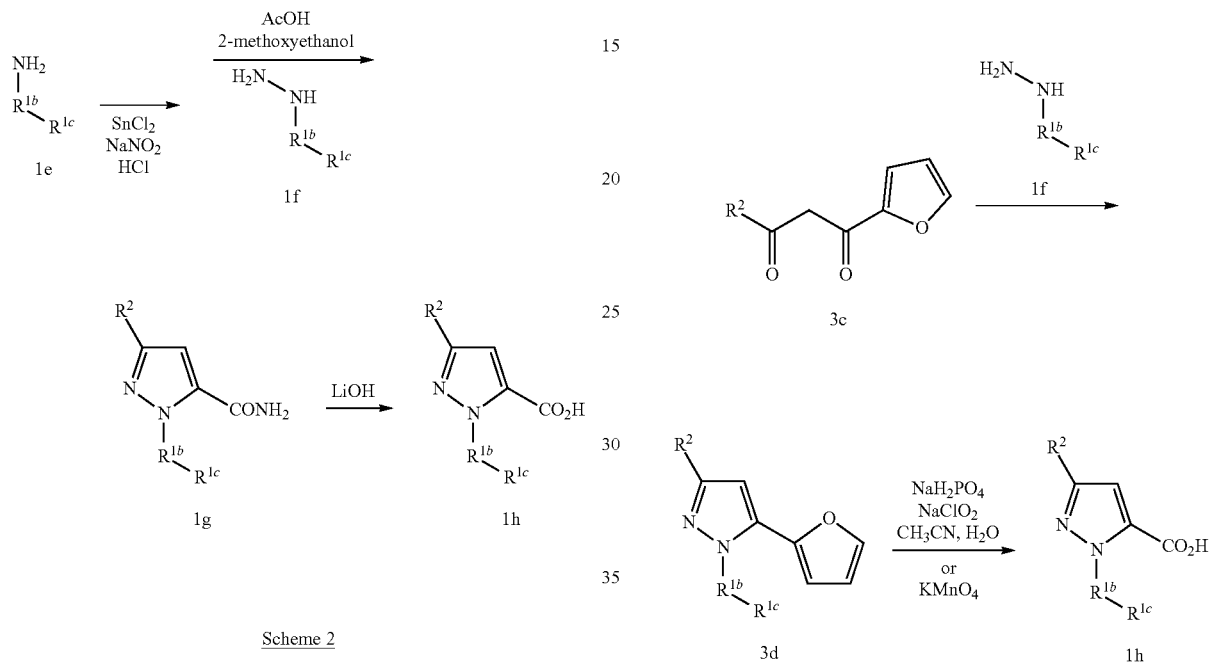
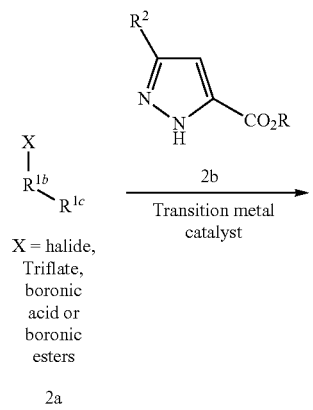
Scheme 2
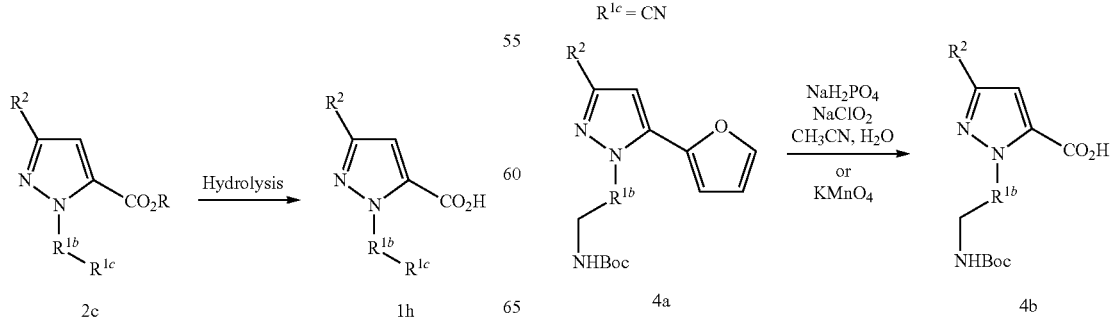

Scheme 5
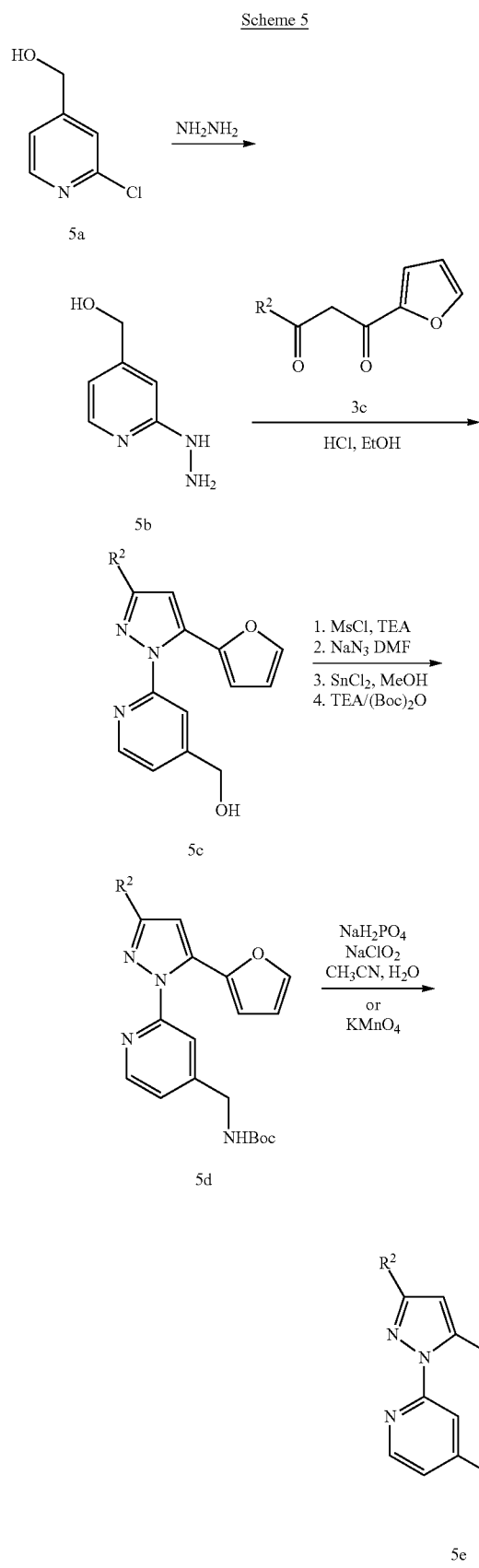
Scheme 6
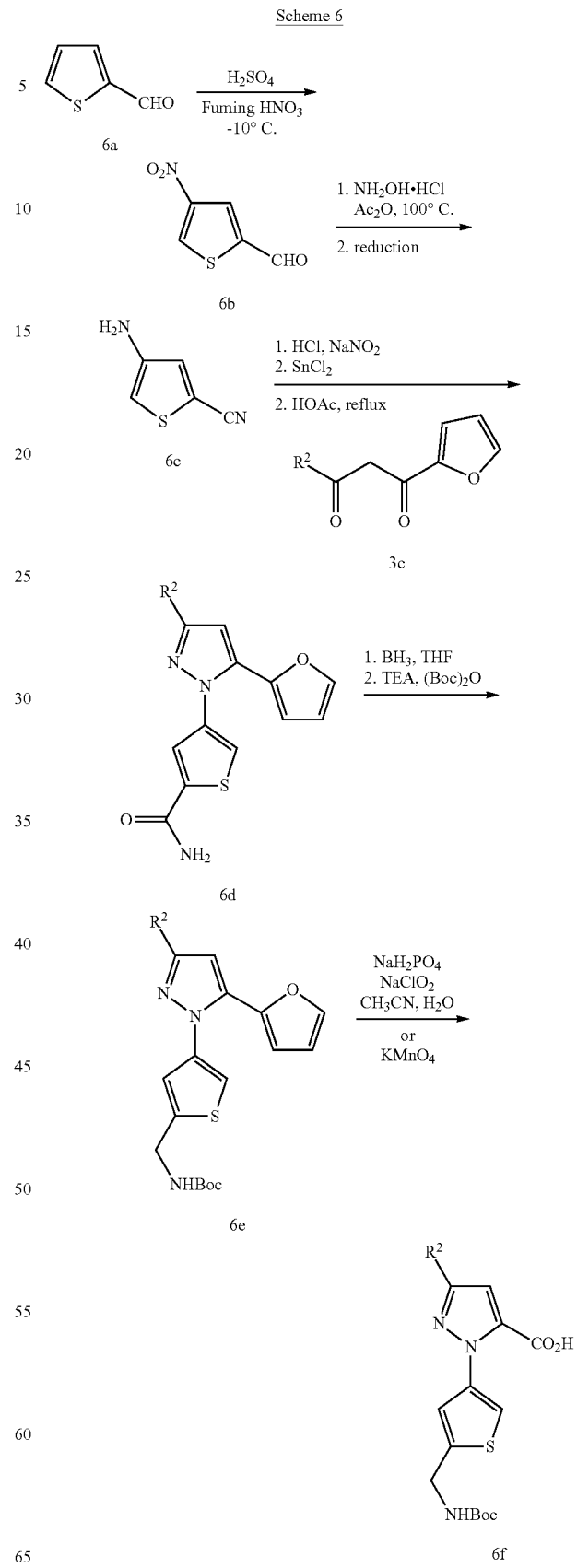

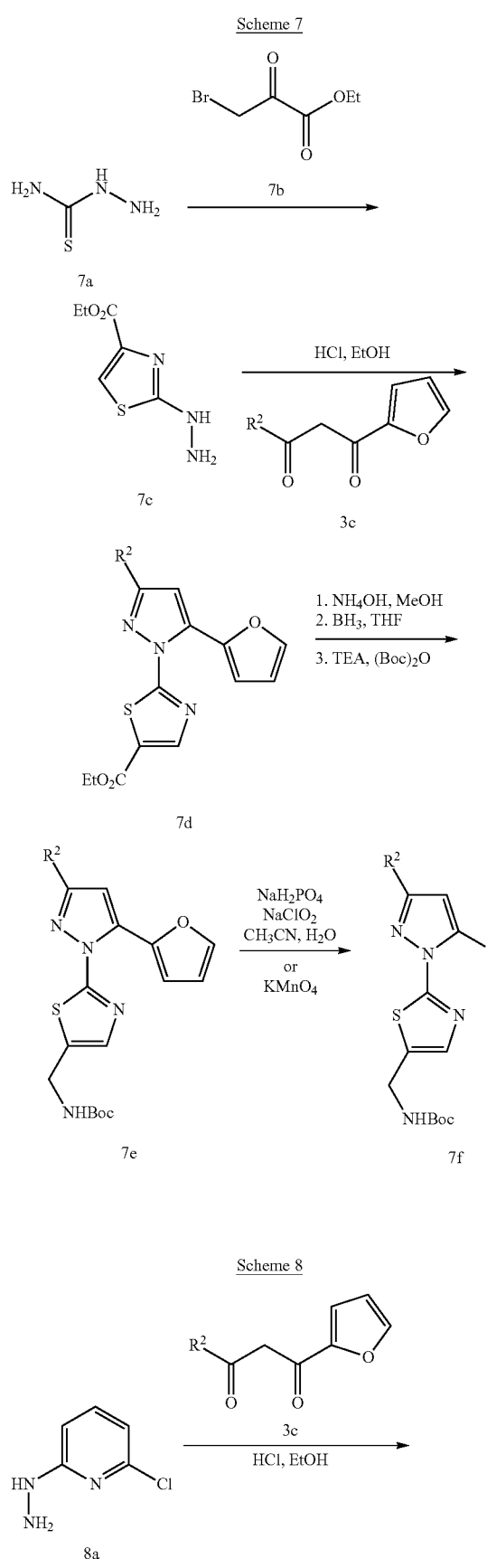
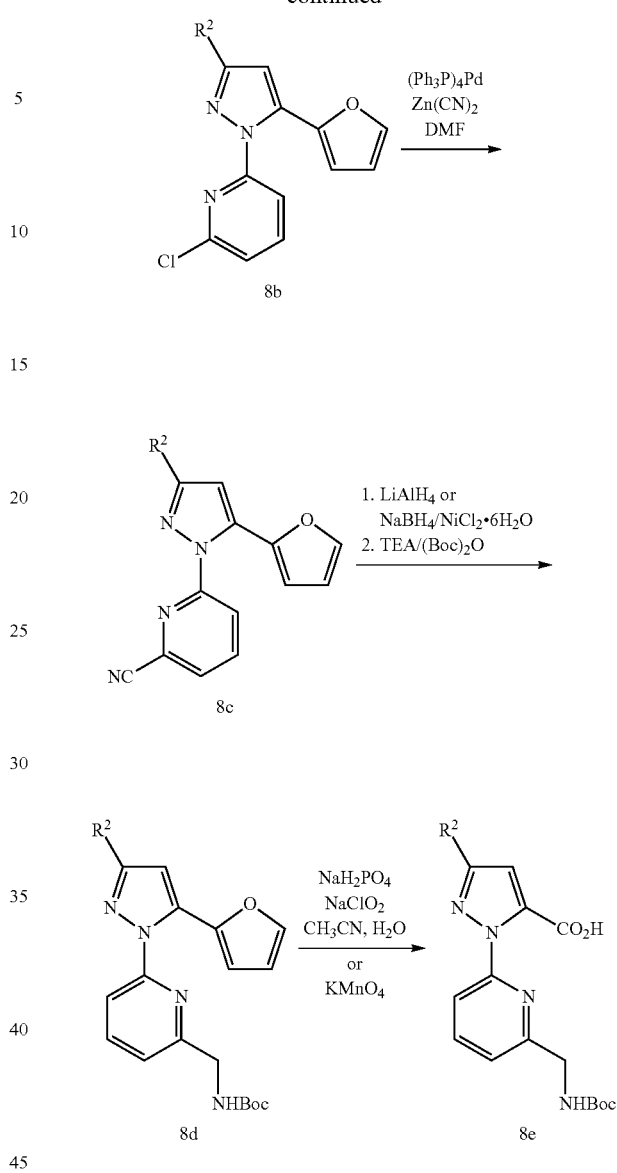
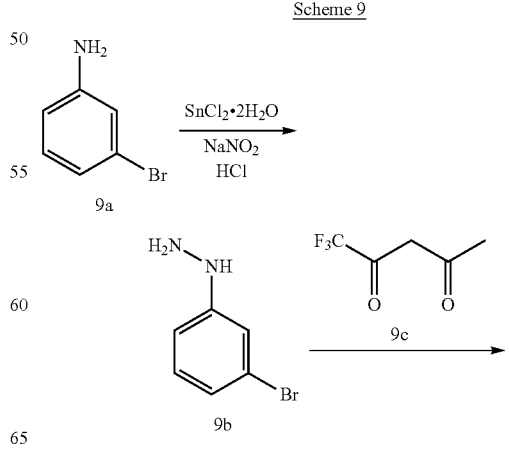

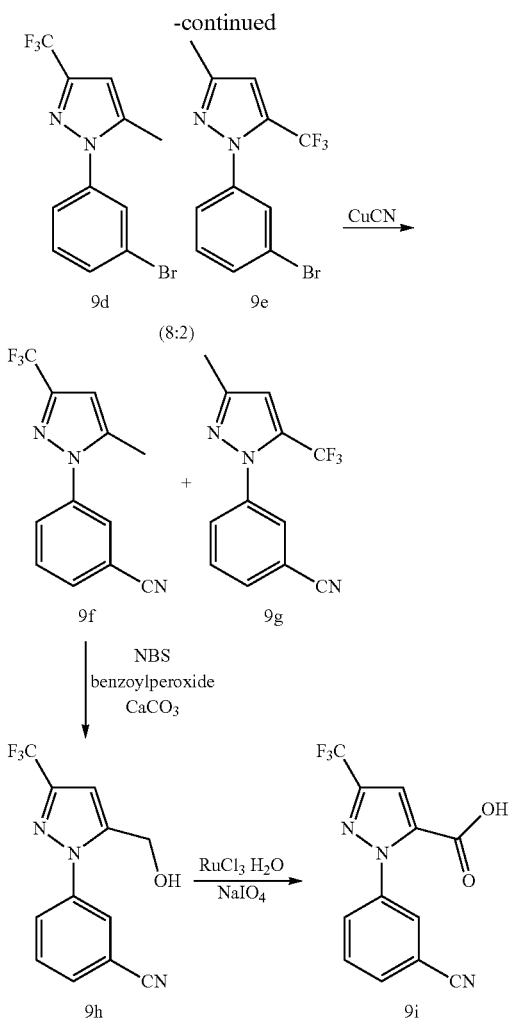

Preparation of 1-(3-cyanophenyl)-3-(trifluoromethyl)-1H-pyrazole-5-carboxylic Acid (9i)

Step-1: Preparation of 3-(5-methyl-3-(trifluoromethyl)-1H-pyrazol-1-yl)benzonitrile (9f)

To a suspension of 3-bromoaniline (9a) (30.8 mL, 283 mmol) in 12 N hydrogen chloride (85 mL, 1017 mmol) was added a solution of sodium nitrite (23.39 g, 339 mmol) in water (160 mL) at 0° C. slowly. After stirring for 1 h, to the mixture was added tin(II) chloride dihydrate (127 g, 565 mmol) pre-dissolved in 12 N hydrogen chloride (85 mL, 1017 mmol) at such a rate that the temperature was not allowed to cross 5 OC. After stirring for 2 h, a solution of 1,1,1-trifluoropentane-2,4-dione (9c) (39.4 mL, 325 mmol) in ethanol (650 mL) was added to the crude reaction mixture containing (3-bromophenyl)hydrazine (9b) and the mixture was heated at 60° C. overnight. After cooling to room temperature, the solvent was removed and the aqueous solution was basified with solid NaHCO₃ and diluted with water (300 mL), partitioned with ethyl acetate (3×500 mL). Organic phase was dried over MgSO₄, concentrated to afford mixtures of 1-(3-bromophenyl)-5-methyl-3-(trifluoromethyl)-1H-pyrazole (9d) and 1-(3-bromophenyl)-3-methyl-5-(trifluoromethyl)-1H-pyrazole (9e) (81.6 g, 94.6% yield) as crude. The reaction mixture was taken as such to next step.

A mixture of 1-(3-bromophenyl)-5-methyl-3-(trifluoromethyl)-1H-pyrazole (9d) and 1-(3-bromophenyl)-3-methyl-5-(trifluoromethyl)-1H-pyrazole (9e) (6.1 g, 20 mmol) in DMF (15 mL) was added copper cyanide (2.24 g, 25 mmol) and heated to refluxed overnight. TLC (ethyl acetate/hexanes, 20%) showed reaction complete. The reaction mixture was diluted with ethyl acetate (200 mL), and filtered. The filtrate was washed with water (200 mL) and brine (100 mL) and dried. The crude mixture was purified with a 80 g silica gel flash column with (ethyl acetate/hexanes, 0-50%) as eluent to furnish
1. 3-(3-methyl-5-(trifluoromethyl)-1H-pyrazol-1-yl)benzonitrile (9g) (0.5 g, 20% yield, higher running spot) as yellow oil. $^1$H NMR (300 MHz, DMSO-d₆) δ 8.10-8.02 (m, 2H), 7.92-7.76 (m, 2H), 7.03 (s, 1H), 2.32 (s, 3H); IR (KBr) 3143, 3084, 2934, 2236, 1565, 1498, 1463, 1366, 1302, 1238, 1194, 1147, 1008, 800, 685, 507 cm-1; Analysis, calculated for $C_{12}H_8F_3N_3$: C, 57.37; H, 3.21; N, 16.73; Found: C, 57.58; H, 3.35; N, 16.83.
2. 3-(5-methyl-3-(trifluoromethyl)-1H-pyrazol-1-yl)benzonitrile (9f) (1.2 g, 4.78 mmol, 48% yield, lower running spot) as a white solid. $^1$HNMR (300 MHz, DMSO-d₆) δ 8.17 (t, J=1.7 Hz, 1H), 8.06-7.92 (m, 2H), 7.79 (t, J=8.0 Hz, 1H), 6.83 (s, 1H), 2.40 (d, J=0.5 Hz, 3H). IR (KBr) 3153, 3082, 2928, 2231, 1588, 1488, 1434, 1379, 1252, 1189, 1126, 969, 890, 812, 701. cm-1; Analysis, calculated for $C_{12}H_8F_3N_3$: C, 57.37; H, 3.21; N, 16.73; Found: C, 57.58; H, 3.35; N, 16.83.

Step-2: Preparation of 3-(5-(hydroxymethyl)-3-(trifluoromethyl)-1H-pyrazol-1-yl)benzonitrile (9h)

To a solution of 3-(5-methyl-3-(trifluoromethyl)-1H-pyrazol-1-yl)benzonitrile (9f) (2.66 g, 10.59 mmol) in carbon tetrachloride (80 mL) was added 1-bromopyrrolidine-2,5-dione (NBS, 1.98 g, 11.12 mmol) and benzoylperoxide (0.077 g, 0.318 mmol). The reaction mixture was refluxed for 4 h, cooled, filtered, and concentrated to give the crude bromide. The crude bromide was dissolved in a mixture of dioxane (40 mL) and water (40 mL), and calcium carbonate (1.91 g, 19.06 mmol) was added. The solution was heated at 60° C. overnight under constant stirring. The reaction mixture was cooled to room temperature, filtered and the filtercake was washed with ethyl acetate, the filtrate was concentrated to remove volatile solvent, the aqueous solution was extracted with ethyl acetate (2×150 mL). The organic layers were combined, dried over MgSO₄, concentrated to give crude 3-(5-(hydroxymethyl)-3-(trifluoromethyl)-1H-pyrazol-1-yl)benzonitrile (9h). The crude was purified by purified by flash column chromatography [silica gel 40 g, eluting with 0-50% ethyl acetate/hexanes) to furnish 3-(5-(hydroxymethyl)-3-(trifluoromethyl)-1H-pyrazol-1-yl)benzonitrile (9h) (520 mg, 1.946 mmol, 18.38% yield) as a white solid. $^1$H NMR (300 MHz, CDCl₃) δ 8.06 (t, J=1.7 Hz, 1H), 7.99 (ddd, J=8.1, 2.1, 1.2 Hz, 1H), 7.75 (dt, J=7.7, 1.3 Hz, 1H), 7.65 (t, J=7.9 Hz, 1H), 6.76 (s, 1H), 4.72 (t, J=9.8 Hz, 2H), 2.13 (t, J=5.5 Hz 1H); IR(KBr) 3370, 3076, 2946, 2235, 1484, 1463, 1256, 1192, 1127, 1019, 805, 691, 503 cm$^{-1}$; Analysis calculated for $C_{12}H_8F_3N_3O$: C, 53.94; H, 3.02; N, 15.73; Found: C, 53.96; H, 3.07; N, 15.48.

Step-3: Preparation of 1-(3-cyanophenyl)-3-(trifluoromethyl)-1H-pyrazole-5-carboxylic acid (9i)

To 3-(5-(hydroxymethyl)-3-(trifluoromethyl)-1H-pyrazol-1-yl)benzonitrile (9h) (20.21 g, 76 mmol) in acetonitrile (100 mL) was added sodium periodate (32.4 g, 151 mmol), water (100 mL), and ruthenium(III) chloride hydrate (0.341 g, 1.513 mmol). The reaction mixture was stirred at room temperature for 16 h. The reaction mixture was filtered and concentrated to remove acetonitrile. The aqueous layer was basified with 1 N NaOH followed by ether washings (2×100 mL) to remove organic impurities. The basic aqueous layer was acidified with 1 N HCl, extracted with ether (2×150 mL), ether layer was concentrated to approx. 75 mL then hexanes were added until turbidity was seen then stirred at room temperature overnight. The solid obtained was collected by filtration dried in vacuum to afford 1-(3-cyanophenyl)-3-(trifluoromethyl)-1H-pyrazole-5-carboxylic acid (9i) (7.48 g, 35% yield) as a pale yellow solid. $^1$H NMR (300 MHz, DMSO-d$_6$) δ 13.84 (bs, 1H), 8.22 (t, J=1.7 Hz, 1H), 8.06-8.00 (m, 1H), 7.96 (ddd, J=8.2, 2.1, 1.1 Hz, 1H), 7.74 (t, J=8.0 Hz, 1H), 7.57 (d, J=0.4 Hz, 1H); $^{19}$F NMR (282 MHz, DMSO) δ −60.96 (s); Analysis calculated for: $C_{12}H_6F_3N_3O_2$: C, 51.26; H, 2.15; N, 14.94; Found: C, 51.19; H, 2.14; N, 14.58.

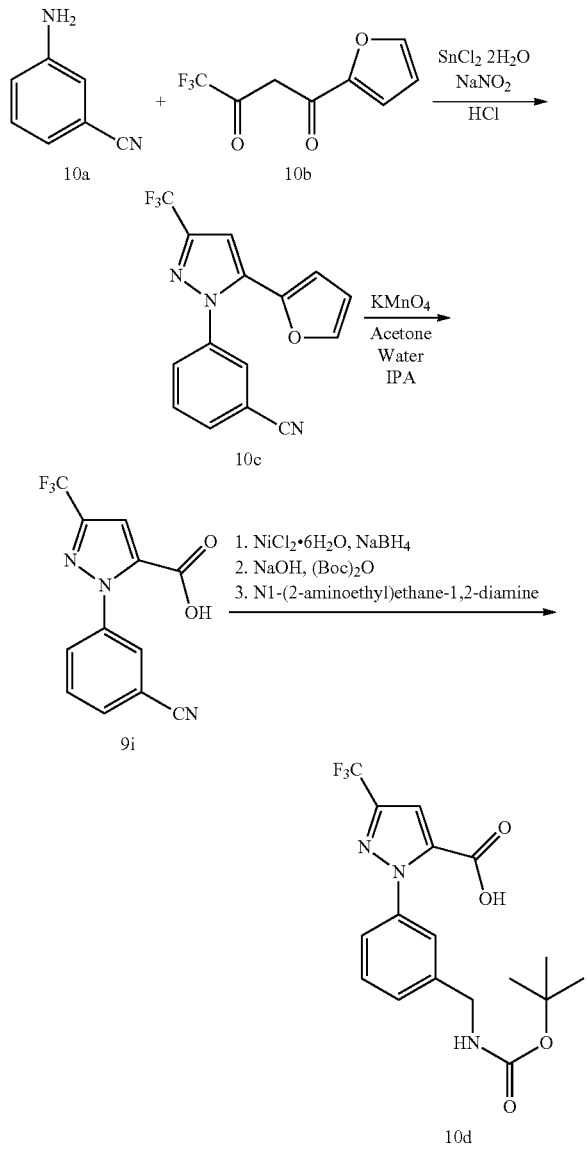

Preparation of 1-(3-(((tert-butoxycarbonyl)amino) methyl)phenyl)-3-(trifluoromethyl)-1H-pyrazole-5-carboxylic Acid (10d)

Step-1: Preparation of 3-(5-(furan-2-yl)-3-(trifluoromethyl)-1H-pyrazol-1-yl)benzonitrile (10c)

To a 1.0 L three-neck flask containing a suspension of 3-aminobenzonitrile (5 g, 42.3 mmol) in 12 N HCl (12.70 mL, 152 mmol) was added slowly at 0° C. an aqueous solution of sodium nitrite (3.50 g, 50.8 mmol) in water (15 mL). The solid suspension was stirred for 1 h and to this was added a pre-dissolved solution of tin(II) chloride dihydrate (19.10 g, 85 mmol) in 12 N HCl (12.70 mL, 152 mmol) at such a rate that the internal temperature was not allowed to exceed 5° C. After stirring for 2 h at 0-5° C. a solution of 4,4,4-trifluoro-1-(furan-2-yl)butane-1,3-dione (10b) (10.47 g, 50.8 mmol) in ethanol (61 mL) was added to the mixture and the mixture was heated at 60° C. overnight. The reaction mixture was cooled to room temperature, concentrated in vacuum to remove ethanol, basified with aqueous NaHCO$_3$ (25 g in 250 mL), diluted with water (250 mL) and extracted with ethyl acetate (3×50 mL). Organic layers were combined dried over MgSO$_4$, filtered, and concentrated in vacuum to dryness. The residue obtained was purified by flash column chromatography [silica gel 120 g, eluting with ethyl acetate in hexanes, 0-100%] to furnish afford 3-(5-(furan-2-yl)-3-(trifluoromethyl)-1H-pyrazol-1-yl)benzonitrile (10c) (8.91 g, 69.4% yield) as a white solid.

Step-2: Preparation of 1-(3-cyanophenyl)-3-(trifluoromethyl)-1H-pyrazole-5-carboxylic acid (9i)

To a solution of 3-(5-(furan-2-yl)-3-(trifluoromethyl)-1H-pyrazol-1-yl)benzonitrile (10c) (4.15 g, 13.69 mmol) in acetone (75 mL) was added an aqueous solution of potassium permanganate (15.14 g, 96 mmol) in water (75 mL). This mixture was heated at 60° C. for 2 h and cooled to room temperature. The reaction mixture was quenched with 2-propanol (75 mL) and stirred at room temperature overnight. The reaction mixture was filtered through Celite and solid cake was washed with acetone/water mixture (2×50 mL), methanol (2×50 mL). The filtrate was evaporated under reduced pressure to remove organic solvents. The aqueous was basified with 1 N NaOH, and washed with ether (2×100 mL). The aqueous layer was poured on to crushed ice, acidified very carefully with aqueous 2 N HCl under constant stirring. The solid obtained was collected by filtration, washed with hexanes (2×50 mL), dried over P2O5 to furnish 1-(3-cyanophenyl)-3-(trifluoromethyl)-1H-pyrazole-5-carboxylic (9i) (2.68 g, 69.6% yield) as a white solid; $^1$H NMR (300 MHz, DMSO-d$_6$) δ 14.01 (s, 1H), 8.22 (t, J=1.8 Hz, 1H), 8.03 (dt, J=7.7, 1.3 Hz, 1H), 7.96 (ddd, J=8.2, 2.2, 1.1 Hz, 1H), 7.75 (t, J=7.9 Hz, 1H), 7.58 (d, J=0.7 Hz, 1H); $^{19}$F NMR (282 MHz, DMSO-d$_6$) δ −60.95.

Step-3: Preparation of 1-(3-(((tert-butoxycarbonyl) amino)methyl)phenyl)-3-(trifluoromethyl)-1H-pyrazole-5-carboxylic acid (10d)

To a stirred solution of 1-(3-cyanophenyl)-3-(trifluoromethyl)-1H-pyrazole-5-carboxylic (9i) (100 g, 356 mmol) in anhydrous methanol (1000 mL), cooled to 0° C. was added, nickel(II) chloride hexahydrate (8.45 g, 35.6 mmol), followed by sodium borohydride (53.8 g, 1423 mmol) in small portions over a period of 70 mins maintaining internal temperature between 0-5° C. The reaction mixture was stirred for additional 15 mins. A cold solution of NaOH (28.4 g, 711 mmol) in water (250 mL), di-tert-butyl dicarbonate (124 g, 569 mmol) and THF (500 mL) was added at 0° C. After 2 h additional di-tert-butyl dicarbonate (15.52 g, 71.1 mmol) in THF (100 mL) was added and continued stirring for 10 h. The reaction mixture was quenched with N1-(2-aminoethyl)ethane-1,2-diamine (38 mL, 356 mmol) stirred for 30 minutes and concentrated in vacuum. The solid obtained was dissolved in water (3000 mL) and insoluble material was removed by filtration over a pad of celite. The filtrate was acidified by dropwise addition of 1 N Potassium bisulfate (2134 mL, 2134 mmol, pH ~2) over a period of 1 h maintaining the internal temperature between 0-5° C. The solid separated was collected by filtration washed with water (500 mL) and dissolved in dichloromethane (4000 mL). The dichloromethane layer was washed with water (1000 mL), brine (1000 mL), dried (MgSO$_4$), filtered and concentrated in vacuum. The residue obtained was purified by flash chromatography {2 Kg silicagel eluting with CMA 80 in chloroform (0%, 5% and 10% [4000 mL each], 20%, 30% and 40% [2000 mL each] 50% 10,000 mL and 60% 4000 mL)} to afford 1-(3-(((tert-butoxycarbonyl)amino)methyl) phenyl)-3-(trifluoromethyl)-1H-pyrazole-5-carboxylic acid (10d) (97 g, 252 mmol, 70.8% yield) as light green solid; $^1$H NMR (300 MHz, DMSO-d$_6$) δ 7.49 (t, J=6.3 Hz, 1H), 7.36 (m, 5H), 4.20 (d, J=6.0 Hz, 2H), 1.38 (s, 9H); $^{19}$F NMR (282 MHz, DMSO-d$_6$) δ −60.75.

dissolved in hydrogen chloride (7.50 mL, 90 mmol) at such a rate that the temperature was not allowed to exceed 5° C. After stirring for 2 h, a solution of 4,4,4-trifluoro-1-(furan-2-yl)butane-1,3-dione (10b) (5.67 g, 27.5 mmol) in ethanol (52 mL) was added to the mixture and the mixture was heated at 60° C. overnight. After cooling to room temperature, the solid obtained was collected by filtration washed with water and dried in vacuo to furnish 5-(furan-2-yl)-1-(4-methoxyphenyl)-3-(trifluoromethyl)-1H-pyrazole (11b) (5.93 g, 19.22 mmol, 77% yield) as a grey solid; MP: 81.1° C.; $^1$HNMR (300 MHz, DMSO-d$_6$) δ 7.78 (dd, J=1.8, 0.7 Hz, 1H), 7.46-7.42 (m, 2H), 7.22 (s, 1H), 7.12-7.08 (m, 2H), 6.54 (dd, J=3.5, 1.8 Hz, 1H), 6.12 (dd, J=3.5, 0.7 Hz, 1H), 3.85 (s, 3H); $^{19}$F NMR (300 MHz, DMSO-d$_6$) δ −60.39; MS (ES+) 309.0.

Step-2: Preparation of 1-(4-Methoxyphenyl)-3-(trifluoromethyl)-1H-pyrazole-5-carboxylic Acid (11c)

To a solution of 5-(furan-2-yl)-1-(4-methoxyphenyl)-3-(trifluoromethyl)-1H-pyrazole (11b) (5 g, 16.22 mmol) dissolved in acetone (180 mL) was added a solution of KMnO$_4$ (17.94 g, 114 mmol) in water (200 mL). The reaction mixture was heated at 60° C. for 3 h and cooled to room temperature. The reaction mixture was quenched with IPA (180 mL) and stirred at room temperature overnight. The reaction mixture was filtered through a pad of Celite washed with acetone and water. The filtrate was concentrated to remove organic solvent. The aqueous solution was acidified with acetic acid to pH 4-5, and extracted with ether. The organic phase was dried over MgSO$_4$, filtered and concentrated in vacuum to give 1-(4-Methoxyphenyl)-3-(trifluoromethyl)-1H-pyrazole-5-carboxylic acid (11c) (3.965 g, 13.85 mmol, 85% yield) as light yellow solid, an analytical sample was obtained by column purification of a small portion of the crude. $^1$H NMR (300 MHz, DMSO-d$_6$) δ 13.34 (s, 1H), 7.50-7.38 (m, 3H), 7.10-6.99 (m, 2H), 3.83 (s, 3H); MS (ES+) 287.0 (M+1).

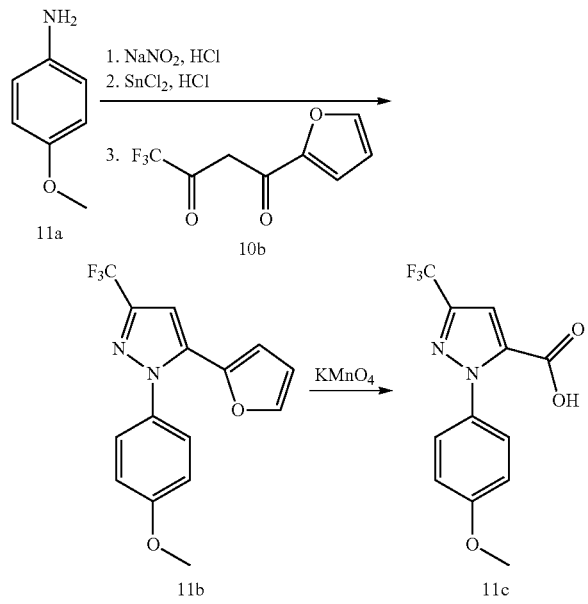

Preparation of 1-(4-Methoxyphenyl)-3-(trifluoromethyl)-1H-pyrazole-5-carboxylic Acid (11c)

Step-1: Preparation of 5-(furan-2-yl)-1-(4-methoxyphenyl)-3-(trifluoromethyl)-1H-pyrazole (11b)

To a suspension of 4-methoxyaniline (3.08 g, 25 mmol) in hydrogen chloride (7.50 mL, 90 mmol) was added dropwise a solution of sodium nitrite (2.070 g, 30.0 mmol) in water (13 mL) at 0° C. After stirring for 1 h, to this mixture was added tin(II) chloride dihydrate (11.28 g, 50.0 mmol) pre-

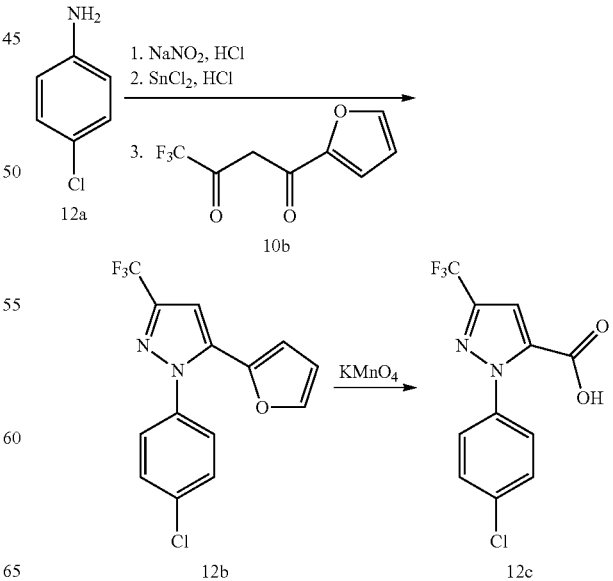

Preparation of 1-(4-Chlorophenyl)-3-(trifluoromethyl)-1H-pyrazole-5-carboxylic Acid (12c)

Step-1: Preparation of 1-(4-chlorophenyl)-5-(furan-2-yl)-3-(trifluoromethyl)-1H-pyrazole (12b)

To a suspension of 4-chloroaniline (12a) (3.19 g, 25 mmol) in hydrogen chloride (7.50 mL, 90 mmol) was added dropwise a solution of sodium nitrite (2.070 g, 30.0 mmol) in water (13 mL) at 0° C. After stirring for 1 h, to this mixture was added tin(II) chloride dihydrate (11.28 g, 50.0 mmol) pre-dissolved in hydrogen chloride (7.50 mL, 90 mmol) at such a rate that the temperature was not allowed to exceed 5° C. After stirring for 2 h, a solution of 4,4,4-trifluoro-1-(furan-2-yl)butane-1,3-dione (10b) (5.67 g, 27.5 mmol) in ethanol (52 mL) was added to the mixture and the mixture was heated at 60° C. overnight. After cooling to room temperature, the reaction mixture was neutralized to pH=4 using 10 N NaOH (18 mL) and 1 N NaOH. The reaction mixture was concentrated in vacuum to remove ethanol. The solid obtained was collected by filtration washed with water and dried under vacuum. The residue was taken in 100 mL Saturated aqueous NaHCO₃ and extracted with ethyl acetate (300 mL). The organic layer was dried and concentrated in vacuum. The residue obtained was purified by flash column chromatography (Silica gel 40 g, eluting with 0-50% ethyl acetate in hexane) to furnish 1-(4-chlorophenyl)-5-(furan-2-yl)-3-(trifluoromethyl)-1H-pyrazole (12b) (6.238 g, 19.95 mmol, 80% yield) as a white solid; MP 62° C.; $^1$H NMR (300 MHz, DMSO-$d_6$) δ 7.79 (dd, J=1.9, 0.7 Hz, 1H), 7.68-7.61 (m, 2H), 7.59-7.52 (m, 2H), 7.31 (d, J=0.6 Hz, 1H), 6.58 (dd, J=3.5, 1.8 Hz, 1H), 6.40 (dd, J=3.5, 0.7 Hz, 1H); $^{19}$F NMR (300 MHz, DMSO-$d_6$) D D 060.90; MS (ES+) 314.9 (M+1).

Step-2: Preparation of 1-(4-Chlorophenyl)-3-(trifluoromethyl)-1H-pyrazole-5-carboxylic Acid (12c)

To a solution of 1-(4-chlorophenyl)-5-(furan-2-yl)-3-(trifluoromethyl)-1H-pyrazole (12b) (6.23 g, 19.92 mmol) dissolved in acetone (200 mL) was added a solution of KMnO₄ (22.04 g, 139 mmol) in water (220 mL). The reaction mixture was stirred at 60° C. for 3 h and cooled to room temperature. The reaction mixture was quenched with IPA (200 mL) and stirred at room temperature overnight. The reaction mixture was filtered through a pad of Celite, washed with acetone and water. The filtrate was concentrated to remove organic solvent. The aqueous solution was acidified with acetic acid to pH 4-5, and extracted with ether. The organic layer was dried, filtered and concentrated in vacuum to give 6.7 g of crude material, which was purified by flash column chromatography (silica gel 80 g, eluting with methanol in chloroform) to furnish 1-(4-Chlorophenyl)-3-(trifluoromethyl)-1H-pyrazole-5-carboxylic acid (12c) (2.5 g, 8.60 mmol, 43.2% yield) as a white solid. $^1$H NMR (300 MHz, DMSO-$d_6$) δ 14.06 (bs, 1H), 7.61-7.56 (m, 3H), 7.53-7.48 (m, 1H), 7.42 (d, J=3.2 Hz, 1H); MS (ES+) 328.8 (M+K).

Scheme 13

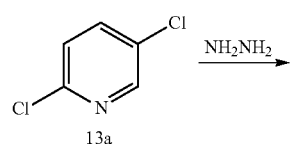

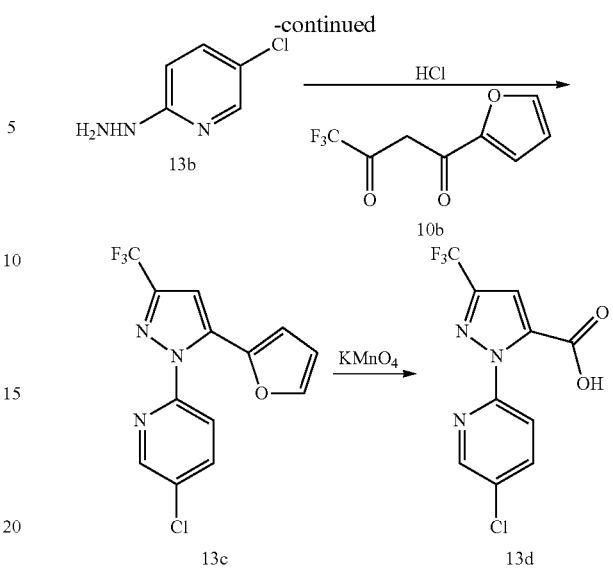

Preparation of 1-(5-chloropyridin-2-yl)-3-(trifluoromethyl)-1H-pyrazole-5-carboxylic Acid (13d)

Step-1: Preparation of 5-chloro-2-hydrazinylpyridine (13b)

A solution of 2,5-dichloropyridine (13a) (7.4 g, 50.0 mmol) and hydrazine hydrate (101 mL, 3250 mmol) in Pyridine (100 mL) was heated at reflux for 6 h and concentrated in vacuum to dryness. The residue obtained was dissolved in DCM (500 mL), washed with 1 N aqueous NaOH (500 mL), water (3×500 mL). The organic layer was dried over MgSO₄ filtered and concentrated in vacuum to dryness to furnish 5-chloro-2-hydrazinylpyridine (13b) (2.95 g, 20.55 mmol, 41% yield) as light yellow solid. $^1$H NMR (300 MHz, DMSO-$d_6$) δ 7.97 (d, J=2.5 Hz, 1H), 7.67 (s, 1H), 7.50 (dd, J=9.0, 2.6 Hz, 1H), 6.73 (dd, J=9.0, 0.6 Hz, 1H), 4.17 (s, 2H); MS (ES+) 144.2 (M+1).

Step-2: Preparation of 5-chloro-2-(5-(furan-2-yl)-3-(trifluoromethyl)-1H-pyrazol-1-yl)pyridine (13c)

To a solution of 5-Chloro-2-hydrazinylpyridine (13b) (717.87 mg, 5.00 mmol) in EtOH (12 mL) was added 4,4,4-trifluoro-1-(furan-2-yl)butane-1,3-dione (10b) (1134 mg, 5.50 mmol), Water (3 mL), and hydrogen chloride (conc. HCl, 1.667 mL, 20.00 mmol). The resulting mixture was stirred at reflux overnight and concentrated in vacuum to remove organic solvent. The aqueous was basified with 1 N NaOH, and then partitioned twice with ethyl acetate. The organic layers were combined, dried filtered and concentrated in vacuum to dryness. The residue obtained was purified by flash column chromatography (silica gel 12 g, eluting with 0-50% ethyl acetate in hexane) to furnish 5-chloro-2-(5-(furan-2-yl)-3-(trifluoromethyl)-1H-pyrazol-1-yl)pyridine (13c) (795 mg, 2.53 mmol, 50.7% yield) as light yellow solid, $^1$H NMR showed a mixture of 2 compound, with a ratio of 2:1. MS (ES+) 314.0 (M+1), 335.9 (M+Na).

Step-3: Preparation of 1-(5-chloropyridin-2-yl)-3-(trifluoromethyl)-1H-pyrazole-5-carboxylic Acid (13d)

To a solution of 5-chloro-2-(5-(furan-2-yl)-3-(trifluoromethyl)-1H-pyrazol-1-yl)pyridine (13c) (750 mg, 2.39 mmol)

in acetone (25 mL) and water (27.5 mL) was added KMnO$_4$ (2645 mg, 16.74 mmol). The reaction mixture was heated at 60° C. for 3 h. The reaction mixture was cooled to room temperature, quenched with isopropanol (25 mL) and stirred at room temperature overnight. The reaction mixture was filtered through a pad of Celite and the filter-cake was washed with 50 mL of acetone-water (1:1). The filtrate was concentrated to remove organic solvents, and the resulting aqueous solution was acidified with 1 N HCl to pH 2-3. The solution became cloudy; the solid obtained was collected by filtration washed with some additional water, hexanes, and dried under vacuum to furnish 5-chloro-2-(5-(furan-2-yl)-3-(trifluoromethyl)-1H-pyrazol-1-yl)pyridine (13c) (345 mg, 1.183 mmol, 49.5% yield) as off-white solid. $^1$H NMR (300 MHz, DMSO-d$_6$) δ 13.67 (s, 1H), 8.68 (d, J=2.5 Hz, 1H), 8.26 (dd, J=8.7, 2.6 Hz, 1H), 7.94 (d, J=8.8 Hz, 1H), 7.54 (s, 1H); $^{19}$F NMR (282 MHz, DMSO-d$_6$) δ −56; MS (ES+) 292.0 (M+1), 313.9 (M+Na), 329.9 (M+K).

Scheme 14

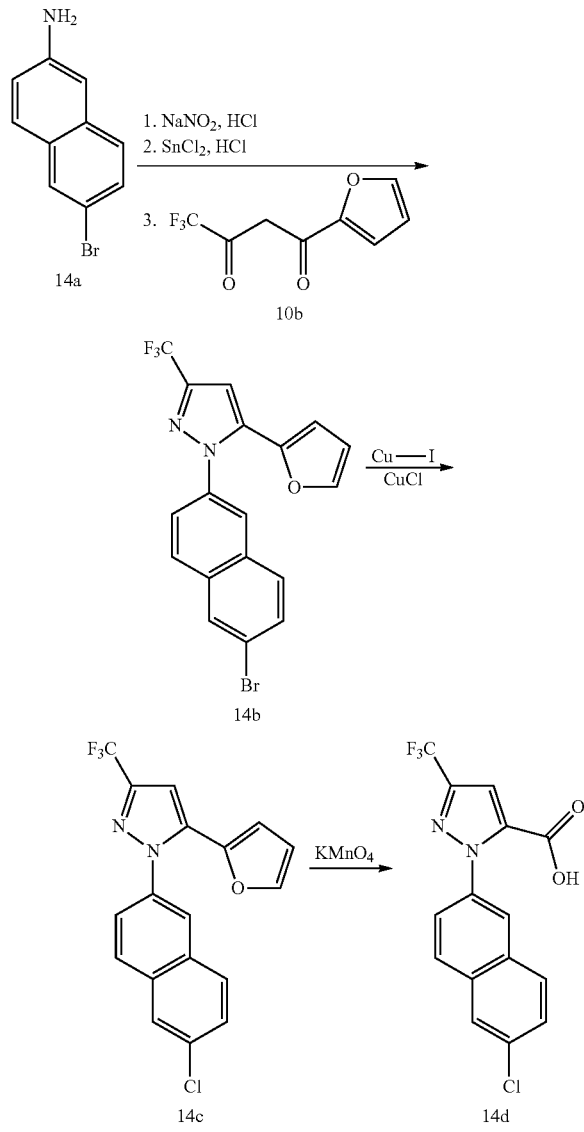

Preparation of 1-(6-chloronaphthalen-2-yl)-3-(trifluoromethyl)-1H-pyrazole-5-carboxylic Acid (14d)

Step-1: Preparation of 1-(6-Bromonaphthalen-2-yl)-5-(furan-2-yl)-3-(trifluoromethyl)-1H-pyrazole (14b)

To a suspension of 6-bromonaphthalen-2-amine (14a) (2.6 g, 11.71 mmol) in hydrogen chloride (7.02 mL, 84 mmol) was added a solution of sodium nitrite (0.969 g, 14.05 mmol) in water (12 mL) at 0° C. slowly. After stirring for 1 h, to this mixture was added tin(II) chloride dihydrate (5.28 g, 23.41 mmol) pre-dissolved in hydrogen chloride (7.02 mL, 84 mmol) at such a rate that the temperature was not allowed to exceed 5° C. After stirring for 2 h, a solution of 4,4,4-trifluoro-1-(furan-2-yl)butane-1,3-dione (10b) (2.65 g, 12.88 mmol) in ethanol (24 mL) was added to the mixture and heated at 60° C. overnight. After cooling to room temperature, the reaction mixture was basified to pH=8 using 10 N aqueous NaOH (15 mL) and saturated NaHCO$_3$. The reaction mixture was diluted with ethyl acetate and filtered through a pad of celite. The organic layer was separated and the aqueous layer was extracted with ethyl acetate (50 mL). The organic layers were combined dried, filtered and concentrated in vacuum to furnish crude residue which was purified by flash column chromatography (silica gel 12 g, eluting 0-100% ethyl acetate in hexane) to afford 1-(6-Bromonaphthalen-2-yl)-5-(furan-2-yl)-3-(trifluoromethyl)-1H-pyrazole (14b) (1.3 g, 3.19 mmol, 27.3% yield) as a semisolid; $^1$H NMR (300 MHz, DMSO-d$_6$) δ 8.39 (d, J=2.0 Hz, 1H), 8.22 (d, J=2.1 Hz, 1H), 8.10 (d, J=8.8 Hz, 1H), 8.02 (d, J=8.8 Hz, 1H), 7.78 (dd, J=8.8, 2.0 Hz, 1H), 7.75 (dd, J=1.8, 0.8 Hz, 1H), 7.64 (dd, J=8.8, 2.2 Hz, 1H), 7.35 (s, 1H), 6.53 (dd, J=3.5, 1.8 Hz, 1H), 6.32 (dd, J=3.5, 0.7 Hz, 1H); $^{19}$F NMR (300 MHz, DMSO-d$_6$) δ −60.85; MS (ES+) 406.9, 408.8 (M+1).

Step-2: Preparation of 1-(6-Chloronaphthalen-2-yl)-5-(furan-2-yl)-3-(trifluoromethyl)-1H-pyrazole (14c)

To a solution of 1-(6-Bromonaphthalen-2-yl)-5-(furan-2-yl)-3-(trifluoromethyl)-1H-pyrazole (14b) (1.73 g, 4.25 mmol) in DMF (25 mL) was added copper(I)iodide (0.809 g, 4.25 mmol), copper(I) chloride (4.21 g, 42.5 mmol) and heated at reflux overnight. The mixture was cooled to room temperature diluted with water (35 mL) and stirred for 1 h. The precipitated solid was collected by filtration, washed several times with water and dried under vacuum to afford 1-(6-Chloronaphthalen-2-yl)-5-(furan-2-yl)-3-(trifluoromethyl)-1H-pyrazole (14c) (22 gms) contaminated with copper salts. The solid was suspended in ethyl acetate (100 mL) and filtered. The filtrate was concentrated in vacuum to dryness to yield 1-(6-Chloronaphthalen-2-yl)-5-(furan-2-yl)-3-(trifluoromethyl)-1H-pyrazole (14c) (1.2 g, 3.31 mmol, 78% yield) as a light yellow solid after purification by column chromatography (silica gel 40 g, eluting with 0-100% ethyl acetate in hexane); $^1$HNMR (300 MHz, DMSO-d$_6$) δ 8.23 (t, J=1.6 Hz, 2H), 8.10 (dd, J=9.0, 1.5 Hz, 2H), 7.75 (dd, J=1.9, 0.7 Hz, 1H), 7.66 (ddd, J=8.7, 6.6, 2.2 Hz, 2H), 7.35 (s, 1H), 6.53 (dd, J=3.5, 1.8 Hz, 1H), 6.32 (dd, J=3.5, 0.8 Hz, 1H); Analysis calculated for C$_{18}$H$_{10}$ClF$_3$N$_2$O: C, 59.60; H, 2.78; N, 7.72; Cl, 9.77; Found: C, 59.34; H, 2.60; N, 7.70; Cl, 9.96.

Step-3: Preparation of 1-(6-chloronaphthalen-2-yl)-3-(trifluoromethyl)-1H-pyrazole-5-carboxylic Acid (14d)

To a solution of 1-(6-chloronaphthalen-2-yl)-5-(furan-2-yl)-3-(trifluoromethyl)-1H-pyrazole (14c) (4.42 g, 12.19 mmol) in acetone (120 mL) was added a solution of KMnO₄ (13.48 g, 85 mmol) in water (120 mL). The reaction mixture was stirred at 60° C. for 3 h, cooled to room temperature, quenched with isopropanol (120 mL) and stirred at room temperature overnight. The reaction mixture was filtered through a pad of Celite, washed with acetone and water. The filtrate was concentrated in vacuum to remove organic solvents. The aqueous solution was washed with ether then acidified with 1 N aqueous HCl to pH 4. The aqueous layer was extracted partitioned with ethyl acetate dried, filtered and concentrated in vacuum to furnish 1-(6-chloronaphthalen-2-yl)-3-(trifluoromethyl)-1H-pyrazole-5-carboxylic acid (14d) (0.86 g, 2.52 mmol, 21% yield) as light yellow solid; ¹H NMR (300 MHz, DMSO-d₆) δ 13.95 (s, 1H), 8.22 (dd, J=8.0, 2.1 Hz, 2H), 8.08 (dd, J=13.5, 8.9 Hz, 2H), 7.75 (dd, J=8.8, 2.2 Hz, 1H), 7.66 (dd, J=8.8, 2.1 Hz, 1H), 7.58 (s, 1H); MS (ES+) 340.9 (M+1); 338.7 (M−1).

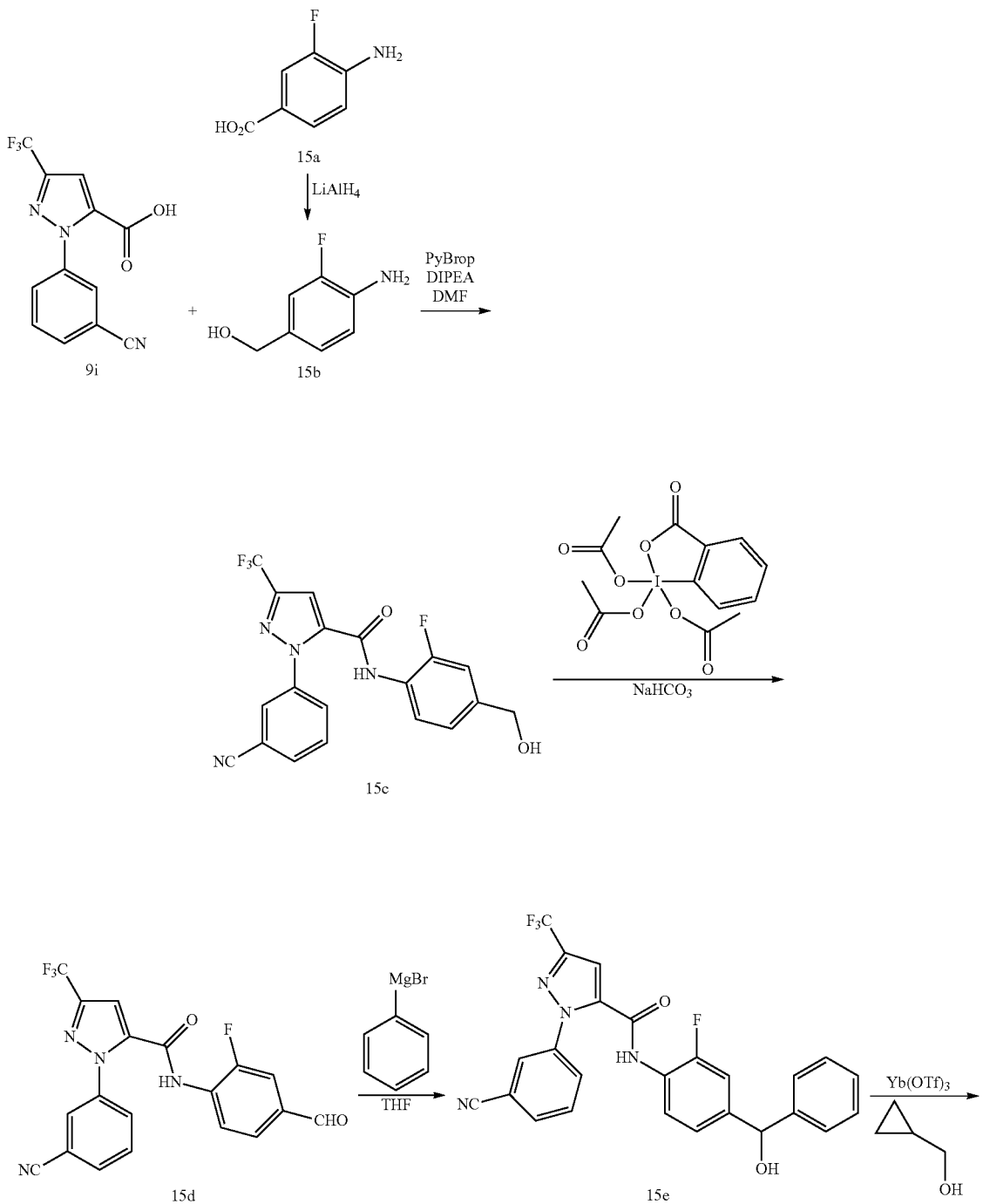

Scheme 15

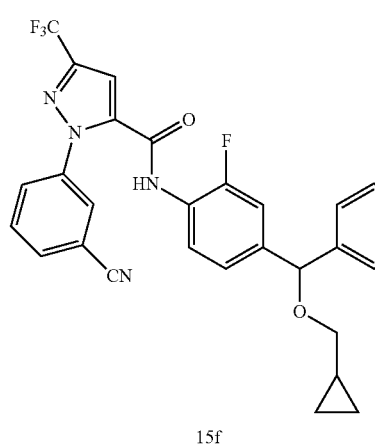 15f

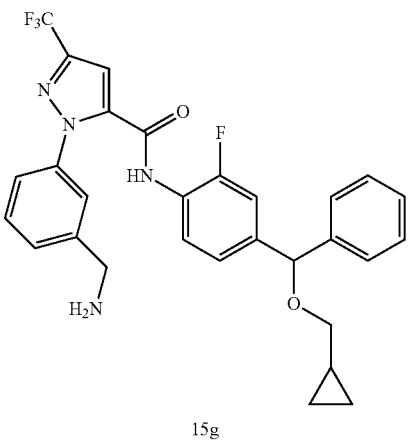 15g

Preparation of 1-(3-(aminomethyl)phenyl)-N-(4-((cyclopropylmethoxy)(phenyl)methyl)-2-fluorophenyl)-3-(trifluoromethyl)-1H-pyrazole-5-carboxamide (15g)

Step-1: Preparation of (4-Amino-3-fluorophenyl)methanol (15b)

To a suspension of lithium aluminum hydride (1.835 g, 48.3 mmol) in THF (20 mL) was added dropwise at 0° C. a solution of 4-amino-3-fluorobenzoic acid (5 g, 32.2 mmol) in THF (20 mL). The reaction mixture was stirred at room temperature overnight. The mixture was then cooled down to 0° C., quenched with ethyl acetate (30 mL) and water (10 mL). The slurry obtained was filtered through Celite and washed with ethyl acetate (50 mL). The aqueous layer was separated and organic layer was dried, filtered and concentrated in vacuum to dryness to give crude product. The crude was purified by flash column chromatography (silica gel 80 g, eluting with 0-100% ethyl acetate in hexane) to furnish (4-Amino-3-fluorophenyl)methanol (15b) (2.2 g, 48.4% yield) as a tan solid; $^1$H NMR (300 MHz, DMSO-$d_6$) δ 6.91 (dd, J=12.5, 1.8 Hz, 1H), 6.81 (dd, J=8.1, 1.8 Hz, 1H), 6.70 (dd, J=9.3, 8.0 Hz, 1H), 5.03-4.93 (m, 3H), 4.31 (d, J=5.5 Hz, 2H); MS (ES+) 142.0 (M+1); (ES−) 140.0 (M−1).

Step-2: Preparation of 1-(3-cyanophenyl)-N-(2-fluoro-4-(hydroxymethyl)phenyl)-3-(trifluoromethyl)-1H-pyrazole-5-carboxamide (15c)

In a 100 mL single-necked flask was charged with 1-(3-cyanophenyl)-3-(trifluoromethyl)-1H-pyrazole-5-carboxylic acid (9i) (1.99 g, 7.09 mmol), (4-amino-3-fluorophenyl)methanol (15b) (1 g, 7.09 mmol), bromo-tris-pyrrolidino phosphoniumhexafluorophosphate (PyBrop) (3.3 g, 7.09 mmol) was treated with N,N-dimethylformamide (42.8 mL, 553 mmol) and N-ethyl-N-isopropylpropan-2-amine (6.17 mL, 35.4 mmol) successively in a positive flow of nitrogen at room temperature. The resulting reaction mixture was stirred at room temperature for 16 h under nitrogen atmosphere. The reaction was diluted with water (150 mL), and extracted with ethyl acetate (2×150 mL), washed with brine (75 mL), the combined organic layer was dried over anhydrous MgSO$_4$, filtered, and evaporated to dryness. The residue was purified by flash column chromatography [silica gel 40 g, eluting with ethyl acetate in hexanes from 0-100%] to furnish 1-(3-cyanophenyl)-N-(2-fluoro-4-(hydroxymethyl)phenyl)-3-(trifluoromethyl)-1H-pyrazole-5-carboxamide (15c) (1.151 g, 2.85 mmol, 40.2% yield) as a pale yellow solid; MS (ES$^+$): MS (ES+) 405.2 (M+1), MS (ES−) 403.2 (M−1).

Step-3: Preparation of 1-(3-cyanophenyl)-N-(2-fluoro-4-formylphenyl)-3-(trifluoromethyl)-1H-pyrazole-5-carboxamide (15d)

To a stirred solution of 1-(3-cyanophenyl)-N-(2-fluoro-4-(hydroxymethyl)phenyl)-3-(trifluoromethyl)-1H-pyrazole-5-carboxamide (15c) (1.106 g, 2.74 mmol) in dichloromethane (20 mL) was added sodium bicarbonate (1.149 g, 13.68 mmol), Dess-Martin Periodinane (1.74 g, 4.10 mmol) and stirred at room temperature for 5 h. Additional Dess-Martin Periodinane (1.74 g, 4.10 mmol), was added to the reaction and stirred for 30 min. Excess solvent was pumped-off under reduced pressure. The reaction mixture was diluted with water (50 mL), and extracted with ethyl acetate (2×75 mL). The combined organic layer was dried over anhydrous MgSO$_4$, filtered and evaporated to dryness. The residue obtained was purified by flash column chromatography [(silica gel 25 g, eluting with ethyl acetate/hexanes from 0 to 100%)] to furnish 1-(3-cyanophenyl)-N-(2-fluoro-4-formylphenyl)-3-(trifluoromethyl)-1H-pyrazole-5-carboxamide (15d) (0.418 g, 38.0% yield) as a white solid.
$^1$H NMR (300 MHz, DMSO-$d_6$) δ 10.85 (s, 1H, D$_2$O exchangeable), 9.95 (d, J=1.7 Hz, 1H), 8.18 (t, J=1.8 Hz, 1H), 8.04-7.98 (m, 1H), 7.97-7.90 (m, 2H), 7.85-7.78 (m, 3H), 7.74 (t, J=8.0 Hz, 1H); $^{19}$F NMR (282 MHz, DMSO-$d_6$) δ −60.97, −120.36; MS (ES$^+$): MS (ES+) 425.08 (M+Na), MS (ES−) 401.1 (M−1).

Step-4: Preparation of: 1-(3-cyanophenyl)-N-(2-fluoro-4-(hydroxy(phenyl)methyl)phenyl)-3-(trifluoromethyl)-1H-pyrazole-5-carboxamide (15e)

To a solution of 1-(3-cyanophenyl)-N-(2-fluoro-4-formylphenyl)-3-(trifluoromethyl)-1H-pyrazole-5-carboxamide (15d) (0.4 g, 0.994 mmol) in THF (10 mL) cooled to 0° C. was added dropwise phenyl magnesium bromide (2.018 mL, 2.018 mmol). The reaction mixture was stirred at room temperature for 16 h and with quenched with saturated aqueous NH$_4$Cl (60 mL). The product was extracted twice with ethyl acetate (100 mL, 75 mL). The combined organic extracts were dried over anhydrous MgSO$_4$, filtered, and concentrated in vacuum. The residue obtained was purified by flash column chromatography [(silica gel 25 g, eluting with ethyl acetate in hexanes from 0 to 100%)] to afford 1-(3-cyanophenyl)-N-(2-fluoro-4-(hydroxy(phenyl)methyl)phenyl)-3-(trifluoromethyl)-1H-pyrazole-5-carboxamide (15e) (0.377 g, 0.785 mmol, 79% yield) as a waxy solid; $^1$H NMR (300 MHz, DMSO-$d_6$) δ 10.54 (s, 1H, $D_2O$ exchangeable), 8.12 (t, J=1.8 Hz, 1H), 7.99 (dt, J=7.7, 1.4 Hz, 1H), 7.89 (ddd, J=8.2, 2.2, 1.1 Hz, 1H), 7.77-7.67 (m, 2H), 7.47 (t, J=8.1 Hz, 1H), 7.39 (d, J=1.8 Hz, 1H), 7.36 (d, J=1.3 Hz, 1H), 7.34-7.28 (m, 2H), 7.27-7.22 (m, 1H), 7.20 (dt, J=8.6, 2.4 Hz, 2H), 6.06 (d, J=4.0 Hz, 1H, $D_2O$ exchangeable), 5.71 (d, J=4.0 Hz, 1H); $^{19}$F NMR (282 MHz, DMSO-$d_6$) δ −60.98, −121.26; IR (KBr, cm$^{-1}$): 2236 cm$^{-1}$ (C—N stretching); MS (ES$^+$): MS (ES+) 503.15 (M+Na), MS (ES−) 479.24 (M−1).

Step-5: Preparation of 1-(3-cyanophenyl)-N-(4-((cyclopropylmethoxy)(phenyl)methyl)-2-fluorophenyl)-3-(trifluoromethyl)-1H-pyrazole-5-carboxamide (15f)

To a solution of 1-(3-cyanophenyl)-N-(2-fluoro-4-(hydroxy(phenyl)methyl)phenyl)-3-(trifluoromethyl)-1H-pyrazole-5-carboxamide (15e) (0.453 g, 0.943 mmol) in cyclopropylmethanol (6.77 mL, 94 mmol) was added Ytterbium (III) trifluoromethanesulfonate (1.170 g, 1.886 mmol) and heated at 80° C. for 16 h. The reaction mixture was concentrated in vacuum to dryness and the residue obtained was diluted with chloroform (2×50 mL), filtered through small Celite pad. The filtrate was concentrated in vacuum to dryness and the residue obtained was purified by flash column chromatography [silica gel 25 g, eluting with ethyl acetate in hexanes from 0-100%] to furnish 1-(3-cyanophenyl)-N-(4-((cyclopropylmethoxy)(phenyl)methyl)-2-fluorophenyl)-3-(trifluoromethyl)-1H-pyrazole-5-carboxamide (15f) (0.076 g, 15% yield) as a white solid; $^1$H NMR (300 MHz, DMSO-$d_6$) δ 10.55 (s, 1H, $D_2O$ exchangeable), 8.11 (t, J=1.8 Hz, 1H), 7.99 (dt, J=7.7, 1.3 Hz, 1H), 7.89 (ddd, J=8.5, 1.8 Hz, 1H), 7.77-7.68 (m, 2H), 7.51 (t, J=8.0 Hz, 1H), 7.40-7.32 (m, 4H), 7.32-7.24 (m, 2H), 7.19 (dd, J=8.3, 1.9 Hz, 1H), 5.49 (s, 1H), 3.24 (d, J=6.8 Hz, 2H), 1.11-1.02 (m, 1H), 0.53-0.41 (m, 2H), 0.20-0.12 (m, 2H); $^{19}$F NMR (282 MHz, DMSO-$d_6$) δ −60.98, −120.92; MS (ES$^+$): MS (ES+) 557.1 (M+1), MS (ES−) 533.1 (M−1).

Step-6: Preparation of 1-(3-(aminomethyl)phenyl)-N-(4-((cyclopropylmethoxy)(phenyl)methyl)-2-fluorophenyl)-3-(trifluoromethyl)-1H-pyrazole-5-carboxamide (15g)

To a stirred solution of 1-(3-cyanophenyl)-N-(4-((cyclopropylmethoxy)(phenyl)methyl)-2-fluorophenyl)-3-(trifluoromethyl)-1H-pyrazole-5-carboxamide (15f) (0.071 g, 0.133 mmol) in anhydrous methanol (10 mL) at 0° C., was added nickel(II) chloride hexahydrate (0.047 g, 0.199 mmol) and sodium borohydride (0.060 g, 1.594 mmol) in small portions over a period of 5 min. The reaction mixture was stirred for 10 min, quenched with N1-(2-aminoethyl)ethane-1,2-diamine (0.143 mL, 1.328 mmol) and stirred for additional 30 min. Excess methanol was pumped-off under reduced pressure. The reaction mixture was treated with sat. NH$_4$Cl (50 mL), and product was extracted with chloroform (2×50 mL). The combined organic layers were dried over MgSO$_4$, filtered, evaporated to dryness. The residue was purified by flash column chromatography [(silica gel 12 g, eluting with methanol in chloroform from 0 to 50%)] to furnish 1-(3-(aminomethyl)phenyl)-N-(4-((cyclopropylmethoxy)(phenyl)methyl)-2-fluorophenyl)-3-(trifluoromethyl)-1H-pyrazole-5-carboxamide (15g) (48 mg, 67% yield) as a white solid; $^1$H NMR (300 MHz, DMSO-$d_6$) δ 10.58 (s, 1H), 7.55 (d, J=4.6 Hz, 2H), 7.51 (d, J=3.8 Hz, 1H), 7.45-7.40 (m, 2H), 7.39-7.28 (m, 6H), 7.26 (dd, J=6.0, 2.1 Hz, 1H), 7.19 (dd, J=8.3, 1.8 Hz, 1H), 5.49 (s, 1H), 3.76 (s, 2H), 3.24 (d, J=6.7 Hz, 2H), 1.13-1.00 (m, 1H), 0.53-0.41 (m, 2H), 0.21-0.11 (m, 2H); $^1$H NMR (300 MHz, DMSO-$d_6$ $D_2O$) δ 7.55 (s, 2H), 7.53-7.48 (m, 1H), 7.45-7.40 (m, 2H), 7.39-7.28 (m, 6H), 7.27-7.23 (m, 1H), 7.19 (dd, J=8.3, 1.9 Hz, 1H), 5.49 (s, 1H), 3.75 (s, 2H), 3.24 (d, J=6.7 Hz, 2H), 1.06 (m, 1H), 0.56-0.41 (m, 2H), 0.20-0.11 (m, 2H); $^{19}$F NMR (282 MHz, DMSO-$d_6$) δ −60.74, −121.19; MS (ES$^+$): MS (ES+) 539.2 (M+1), MS (ES−) 537.2 (M−1).

Scheme 16

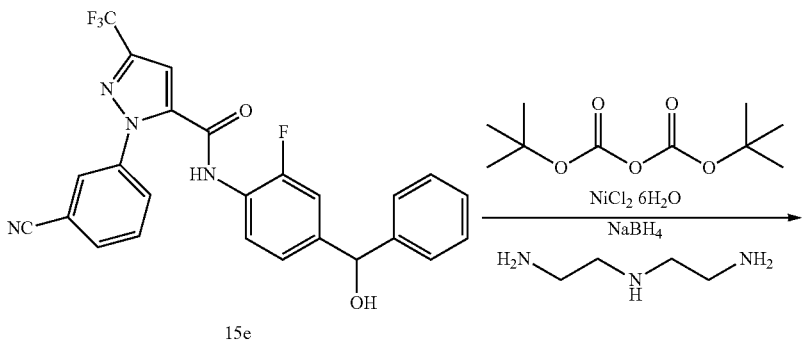

15e

-continued

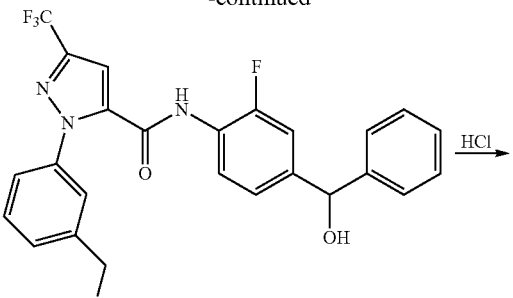

16a

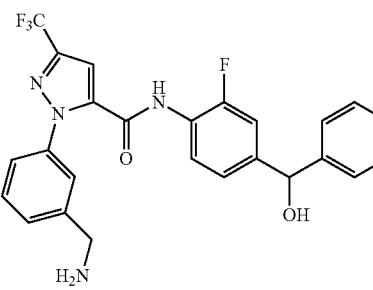

16b

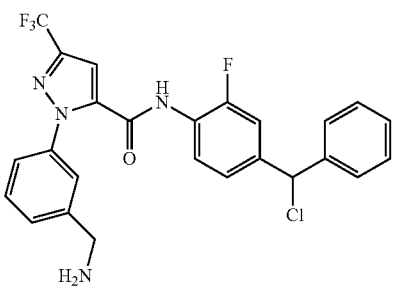

16c

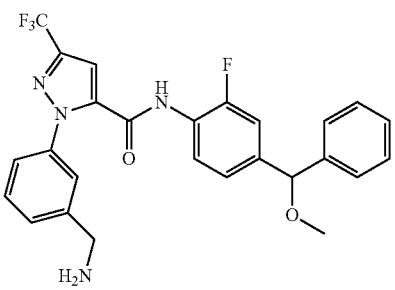

16d

Preparation of 1-(3-(Aminomethyl)phenyl)-N-(2-fluoro-4-(hydroxy(phenyl)methyl)phenyl)-3-(trifluoromethyl)-1H-pyrazole-5-carboxamide (16b)

Step-1: Preparation of tert-Butyl 3-(5-(2-fluoro-4-(hydroxy(phenyl)methyl)phenylcarbamoyl)-3-(trifluoromethyl)-1H-pyrazol-1-yl)benzylcarbamate (16a)

To a stirred solution of 1-(3-cyanophenyl)-N-(2-fluoro-4-(hydroxy(phenyl)methyl)phenyl)-3-(trifluoromethyl)-1H-pyrazole-5-carboxamide (15e), (0.284 g, 0.59 mmol) in anhydrous methanol (5 mL), cooled to 0° C., was added di-tert-butyl dicarbonate (0.258 g, 1.182 mmol) and nickel (II) chloride (0.035 g, 0.148 mmol), Sodium borohydride (0.134 g, 3.55 mmol) was added to the reaction mixture in small portions over a 15 min period. The reaction mixture was stirred for 15 min at 0° C. TLC (50% EtOAc in hexanes) shows all starting material was consumed. The reaction mixture was quenched with N1-(2-aminoethyl)ethane-1,2-diamine (0.128 mL, 1.182 mmol) stirred for 30 mins and concentrated in vacuum to dryness. The residue obtained was dissolved in dichloromethane (20 mL) and water (20 mL). The organic layer was separated, dried, filtered and concentrated in vacuum. The residue obtained was purified by flash column chromatography (silica gel 12 g, eluting with 0-100% ethyl acetate in hexane) to furnish tert-Butyl 3-(5-(2-fluoro-4-(hydroxy(phenyl)methyl)phenylcarbamoyl)-3-(trifluoromethyl)-1H-pyrazol-1-yl)benzylcarbamate (16a) (0.185 g, 0.316 mmol, 53.5% yield) as a white solid.

$^1$H NMR (300 MHz, DMSO-d$_6$) δ 10.55 (s, 1H), 7.57 (s, 1H), 7.50 (q, J=7.7 Hz, 2H), 7.44-7.37 (m, 3H), 7.37-7.31 (m, 4H), 7.29 (dt, J=6.3, 0.8 Hz, 2H), 7.25-7.15 (m, 2H), 6.04 (d, J=4.0 Hz, 1H), 5.70 (d, J=4.1 Hz, 1H), 4.18 (d, J=6.2 Hz, 2H), 1.36 (s, 9H); $^{19}$F NMR (282 MHz, DMSO-d$_6$) δ -60.82, -121.61; MS (ES+) 607.3 (M+Na); (ES-) 583.2 (M-1).

Step-2: Preparation of 1-(3-(Aminomethyl)phenyl)-N-(2-fluoro-4-(hydroxy(phenyl)methyl)phenyl)-3-(trifluoromethyl)-1H-pyrazole-5-carboxamide (16b)

To a stirred solution of tert-Butyl 3-(5-(2-fluoro-4-(hydroxy(phenyl)methyl)phenylcarbamoyl)-3-(trifluoromethyl)-1H-pyrazol-1-yl)benzylcarbamate (16a) (0.17 g, 0.291 mmol) in acetonitrile (5 mL) at room temperature was added conc. HCl (1.212 mL, 14.54 mmol) and water (1.25 mL). The reaction mixture was stirred at room temperature overnight and concentrated in vacuum to dryness. The residue obtained was purified by flash column chromatography (silica gel 12 g, eluting with 0-100% ethyl acetate in hexane) to furnish 1-(3-(aminomethyl)phenyl)-N-(2-fluoro-4-(methoxy(phenyl)methyl)phenyl)-3-(trifluoromethyl)-1H-pyrazole-5-carboxamide (16c) (0.040 g, 0.080 mmol, 27.6% yield) as a white solid, this was contaminated by 1-(3-(aminomethyl)phenyl)-N-(4-(chloro(phenyl)methyl)-2-fluorophenyl)-3-(trifluoromethyl)-1H-pyrazole-5-carboxamide (16d) impurity. Further elution gave 1-(3-(Aminomethyl)phenyl)-N-(2-fluoro-4-(hydroxy(phenyl)methyl)phenyl)-3-(trifluoromethyl)-1H-pyrazole-5-carboxamide (16b) (0.022 g, 0.045 mmol, 15.62% yield) as a white solid; $^1$H NMR (300 MHz, DMSO-d$_6$) δ 10.64 (s, 1H), 8.34 (s, 3H), 7.71 (d, J=2.0 Hz, 1H), 7.67 (s, 1H), 7.59 (td, J=5.4, 2.6 Hz, 1H), 7.55-7.46 (m, 3H), 7.40-7.35 (m, 2H), 7.34-7.27 (m, 2H), 7.26-7.16 (m, 3H), 6.07 (d, J=4.0 Hz, 1H), 5.71 (d, J=4.0 Hz, 1H); $^{19}$F NMR (282 MHz, DMSO-d$_6$) δ -60.82, -121.23; MS (ES+) 485.1 (M+1); (ES-) 483.2 (M-1).

Scheme 17

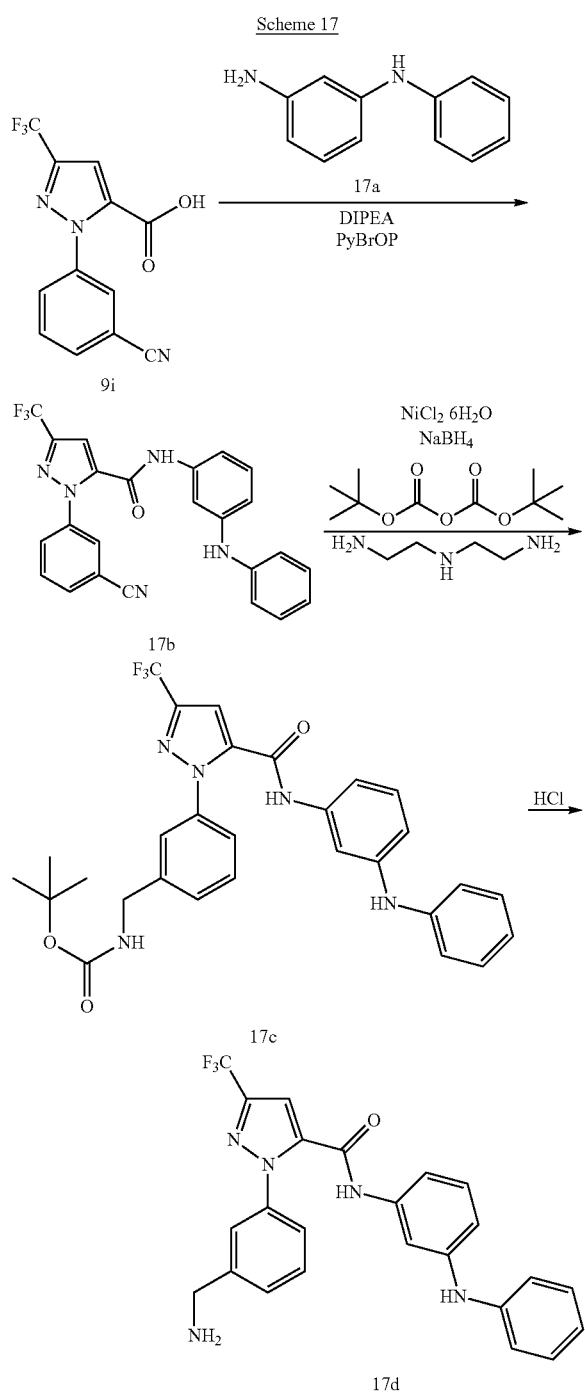

Preparation of 1-(3-(aminomethyl)phenyl)-N-(3-(phenylamino)phenyl)-3-(trifluoromethyl)-1H-pyrazole-5-carboxamide (17d)

Step-1: Preparation of 1-(3-cyanophenyl)-N-(3-(phenylamino)phenyl)-3-(trifluoromethyl)-1H-pyrazole-5-carboxamide (17b)

To a solution of 1-(3-cyanophenyl)-3-(trifluoromethyl)-1H-pyrazole-5-carboxylic acid (9i) (400 mg, 1.423 mmol) in DMF (10 mL) was added $N_1$-phenylbenzene-1,3-diamine (17a) (262 mg, 1.423 mmol), N-ethyl-N-isopropylpropan-2-amine (2.0 mL, 11.48 mmol) and bromotripyrrolidin-1-ylphosphonium hexafluorophosphate(V) (PyBrOP, 682 mg, 1.434 mmol) followed by stirring at room temperature for 15 h. The reaction mixture was diluted with ethyl acetate (200 mL), washed with water (2×75 mL), brine (75 mL), dried, filtered and concentrated in vacuum to dryness. The residue obtained was purified by flash column chromatography [silica gel eluting with hexanes/ethyl acetate (1:0 to 3:1)] to furnish 1-(3-cyanophenyl)-N-(3-(phenylamino)phenyl)-3-(trifluoromethyl)-1H-pyrazole-5-carboxamide (17b) (316 mg, 50%) as a brown gum. $^1$H NMR (300 MHz, DMSO-$d_6$) δ 10.57 (s, 1H), 8.31-6.73 (m, 14H); MS (ES+) 448.3 (M+1).

Step-2: Preparation of tert-butyl 3-(5-((3-(phenylamino)phenyl)carbamoyl)-3-(trifluoromethyl)-1H-pyrazol-1-yl)benzylcarbamate (17c)

A solution of 1-(3-cyanophenyl)-N-(3-(phenylamino)phenyl)-3-(trifluoromethyl)-1H-pyrazole-5-carboxamide (17b) (200 mg, 0.447 mmol) in methanol (4 mL) was cooled with ice/water and treated with di-tert-butyl dicarbonate (296 mg, 1.341 mmol) and nickel(II) chloride hexahydrate (21.85 mg, 0.092 mmol) followed by addition of sodium borohydride (104 mg, 2.68 mmol) slowly over 5 min and stirring at room temperature for 1 h. The reaction mixture was quenched with N1-(2-aminoethyl)ethane-1,2-diamine (0.104 mL, 0.952 mmol) followed by stirring at room temperature for 0.5 h. The reaction mixture was concentrated in vacuum to dryness. The residue obtained was treated with ethyl acetate (100 mL), washed with water (50 mL). The aqueous phase was extracted again with ethyl acetate (50 mL). The combined extracts were washed with brine (60 mL), dried over $MgSO_4$ followed by filtration and concentration. The crude residue was purified by flash column chromatography [silica gel, eluting with hexanes/ethyl acetate (1:0 to 3:1)] to furnish tert-butyl 3-(5-((3-(phenylamino)phenyl)carbamoyl)-3-(trifluoromethyl)-1H-pyrazol-1-yl)benzylcarbamate (17c) (160 mg, 65%) as a brown solid. $^1$H NMR (300 MHz, DMSO-$d_6$) δ 10.63 (s, 1H), 8.24 (s, 1H), 7.67-6.51 (m, 14H), 4.20 (d, J=6.3 Hz, 2H), 1.37 (s, 9H); MS (ES+) 552.4 (M+1).

Step-3: Preparation of 1-(3-(aminomethyl)phenyl)-N-(3-(phenylamino)phenyl)-3-(trifluoromethyl)-1H-pyrazole-5-carboxamide (17d)

To a solution of tert-butyl 3-(5-((3-(phenylamino)phenyl)carbamoyl)-3-(trifluoromethyl)-1H-pyrazol-1-yl)benzylcarbamate (17c) (127 mg, 0.230 mmol) in 1,4-Dioxane (12 mL) was treated with hydrogen chloride (2.4 mL, 9.60 mmol, 4 M in 1,4-dioxane) dropwise followed by stirring at room temperature for 13 h. The reaction mixture was diluted with hexanes, decanted, washed with hexanes, and decanted again. The insoluble part was purified by flash column chromatography [silica gel 4 g, eluting with chloroform/CMA80 (1:0 to 2:1)] to afford 1-(3-(aminomethyl)phenyl)-N-(3-(phenylamino)phenyl)-3-(trifluoromethyl)-1H-pyrazole-5-carboxamide (17d) (23 mg, 22%) as a white solid, mp: 73.8° C.; $^1$H NMR (300 MHz, DMSO-$d_6$) δ 10.62 (s, 1H), 8.25 (s, 1H), 7.55 (s, 1H), 7.53 (s, 1H), 7.48 (t, J=2.1 Hz, 1H), 7.45-7.41 (m, 2H), 7.35-7.29 (m, 1H), 7.23 (t, J=7.9 Hz, 2H), 7.16 (d, J=8.0 Hz, 1H), 7.08 (d, J=2.2 Hz, 2H), 7.05 (s, 1H), 6.87-6.78 (m, 2H), 3.78 (s, 2H); $^{19}$F NMR (282 MHz, DMSO-$d_6$) δ −60.70; MS (ES+) 452.3 (M+1).

Scheme 18
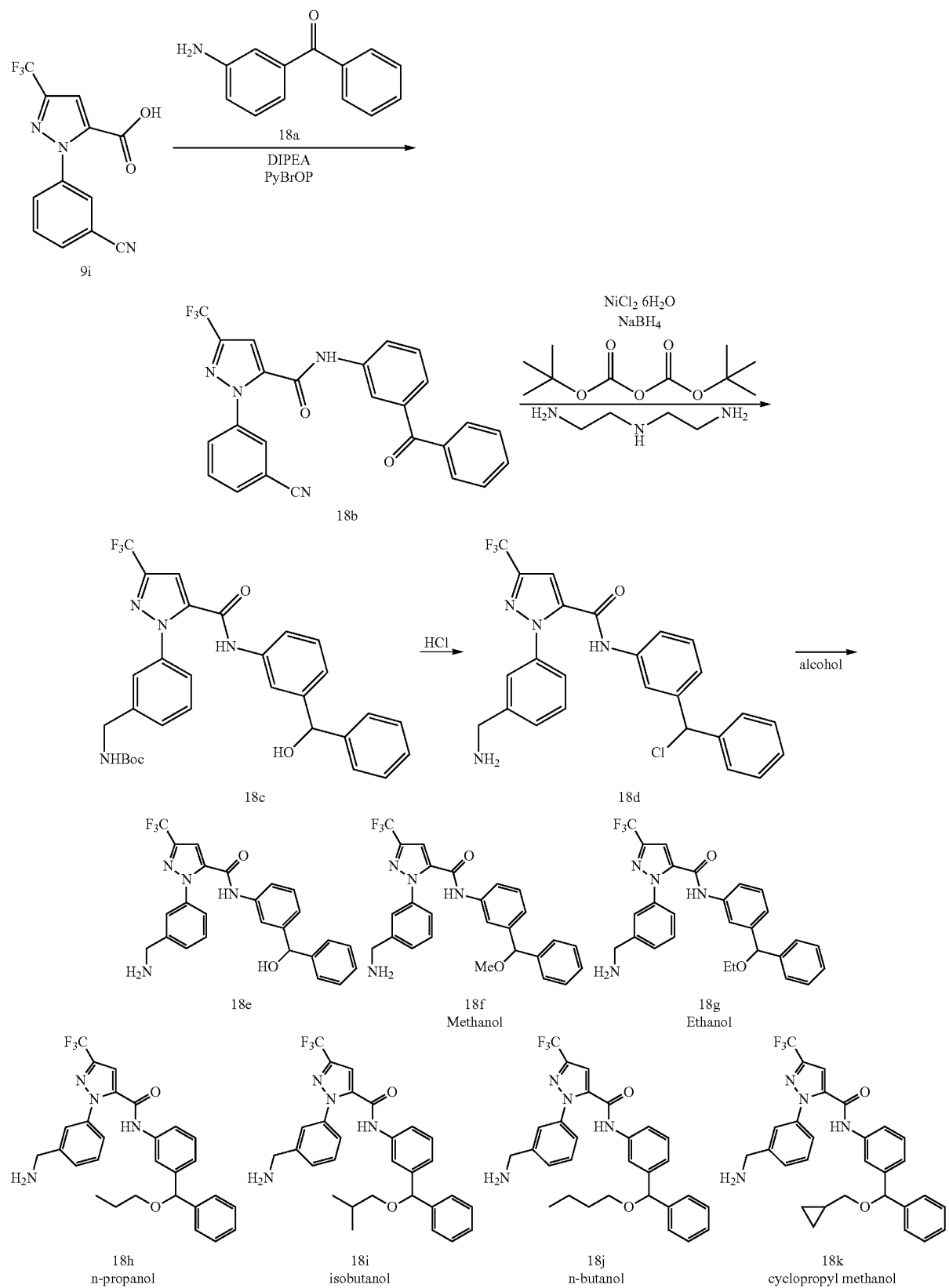

Preparation of 1-(3-(aminomethyl)phenyl)-N-(3-(ethoxy(phenyl)methyl)phenyl)-3-(trifluoromethyl)-1H-pyrazole-5-carboxamide (18g)

Preparation of 1-(3-(aminomethyl)phenyl)-N-(3-(phenyl(propoxy)methyl)phenyl)-3 methanol-(trifluoromethyl)-1H-pyrazole-5-carboxamide (18h)

Preparation of 1-(3-(aminomethyl)phenyl)-N-(3-(isobutoxy(phenyl)methyl)phenyl)-3-(trifluoromethyl)-1H-pyrazole-5-carboxamide (18i)

Preparation of 1-(3-(aminomethyl)phenyl)-N-(3-(butoxy(phenyl)methyl)phenyl)-3-(trifluoromethyl)-1H-pyrazole-5-carboxamide (18j)

Preparation of 1-(3-(aminomethyl)phenyl)-N-(3-((cyclopropylmethoxy)(phenyl)methyl)phenyl)-3-(trifluoromethyl)-1H-pyrazole-5-carboxamide (18k)

Step-1: Preparation of N-(3-benzoylphenyl)-1-(3-cyanophenyl)-3-(trifluoromethyl)-3H-pyrazole-5-carboxamide (18b)

To a solution of 1-(3-cyanophenyl)-3-(trifluoromethyl)-1H-pyrazole-5-carboxylic acid (9i) (5.42 g, 19.27 mmol) in DMF (100 mL) was added 3-aminobenzophenone (18a) (3.8 g, 19.27 mmol), N-ethyl-N-isopropylpropan-2-amine (27 mL, 155 mmol) and bromo-tris-pyrrolidino phosphonium-hexafluorophosphate(PyBrop) (9.24 g, 19.42 mmol) at room temperature. The reaction mixture was stirred at room temperature for 39 h under nitrogen atmosphere. The reaction was diluted with ethyl acetate (600 mL) washed with water (2×300 mL), brine (200 mL), dried, filtered, and evaporated to dryness. The residue obtained was purified by flash column chromatography [silica gel 120 g, eluting with ethyl acetate in hexanes from 0-25%] to furnish N-(3-benzoylphenyl)-1-(3-cyanophenyl)-3-(trifluoromethyl)-1H-pyrazole-5-carboxamide (18b) (5.633 g, 63% yield) as a yellow solid; $^1$H NMR (300 MHz, DMSO-d$_6$) δ 10.89 (s, 1H), 8.19 (t, J=1.8 Hz, 1H), 8.07-7.98 (m, 3H), 7.93 (ddd, J=8.2, 2.2, 1.1 Hz, 1H), 7.79-7.67 (m, 6H), 7.61-7.55 (m, 2H), 7.50 (dt, J=7.7, 1.5 Hz, 1H); $^{19}$F NMR (282 MHz, DMSO-d$_6$) δ −60.98; MS (ES+) 461.162 (M+1), 483.134 (M+Na).

Step-2: Preparation of tert-butyl 3-(5-((3-(hydroxy(phenyl)methyl)phenyl)carbamoyl)-3-(trifluoromethyl)-1H-pyrazol-1-yl)benzylcarbamate (18c)

To a stirred solution of N-(3-benzoylphenyl)-1-(3-cyanophenyl)-3-(trifluoromethyl)-1H-pyrazole-5-carboxamide (18b) (4.704 g, 10.22 mmol) in anhydrous methanol (100 mL), cooled to 0° C., was added di-tert-butyl dicarbonate (6.76 g, 30.7 mmol), nickel(II) chloride hexahydrate (0.5 g, 2.103 mmol) followed by sodium borohydride (2.367 g, 61.3 mmol) portionwise over a 5 mins period. The reaction mixture was stirred for 30 min at room temperature, quenched with N1-(2-aminoethyl)ethane-1,2-diamine (2.3 mL, 21.08 mmol) stirred for 30 minutes and concentrated in vacuum to dryness. The residue was dissolved in ethyl acetate (400 mL), washed with water (200 mL), brine (200 mL), dried, filtered and concentrated in vacuum. The residue obtained was purified by flash column chromatography (silica gel 80 g, eluting with ethyl acetate/hexanes from 0 to 50%)] to furnish tert-butyl 3-(5-(3-(hydroxy(phenyl)methyl)phenylcarbamoyl)-3-(trifluoromethyl)-1H-pyrazol-1-yl) benzylcarbamate (18c) (2.71 g, 46.8% yield) as a white solid; $^1$H NMR (300 MHz, DMSO-d$_6$) δ 10.70 (s, 1H), 7.62 (t, J=1.8 Hz, 1H), 7.59-7.46 (m, 3H), 7.45-7.40 (m, 2H), 7.38-7.25 (m, 7H), 7.23-7.20 (m, 1H), 7.13 (dt, J=7.7, 1.3 Hz, 1H), 5.94 (d, J=3.9 Hz, 1H), 5.66 (d, J=3.8 Hz, 1H), 4.19 (d, J=6.2 Hz, 2H), 1.37 (s, 9H); $^{19}$F NMR (282 MHz, DMSO-d$_6$) δ −60.80; MS (ES+) 589.3 (M+1), (ES−) 565.3 (M−1).

Step-3: Preparation of 1-(3-(aminomethyl)phenyl)-N-(3-(chloro(phenyl)methyl)phenyl)-3-(trifluoromethyl)-1H-pyrazole-5-carboxamide (18d)

To a solution of tert-butyl 3-(5-(3-(hydroxy(phenyl)methyl)phenylcarbamoyl)-3-(trifluoromethyl)-1H-pyrazol-1-yl)benzylcarbamate (18c) (65 mg, 0.115 mmol) in 1,4-Dioxane (6 mL) was added hydrogen chloride (1.2 mL, 4.80 mmol, 4 M in 1,4-dioxane) dropwise and stirred at room temperature for 13 h. The reaction mixture was diluted with hexanes and decanted. The residue was triturated with hexanes, decanted to obtain 1-(3-(aminomethyl)phenyl)-N-(3-(chloro(phenyl)methyl)phenyl)-3-(trifluoromethyl)-1H-pyrazole-5-carboxamide (18d) as a white solid.

Preparation of 1-(3-(aminomethyl)phenyl)-N-(3-(methoxy(phenyl)methyl)phenyl)-3-(trifluoromethyl)-1H-pyrazole-5-carboxamide (18f)

To a solution of 1-(3-(aminomethyl)phenyl)-N-(3-(chloro(phenyl)methyl)phenyl)-3-(trifluoromethyl)-1H-pyrazole-5-carboxamide (18d) in chloroform/methanol (40 mL/15 mL) was added silica gel 2 g and concentrated in vacuum to obtain a slurry which was purified by flash column chromatography [silica gel 2×4 g, eluting with chloroform/CMA80 (1:0 to 2:1)] to furnish 1-(3-(aminomethyl)phenyl)-N-(3-(methoxy(phenyl)methyl)phenyl)-3-(trifluoromethyl)-1H-pyrazole-5-carboxamide (18f) (26 mgs, 47%) as a white solid, mp: 89.5° C.; $^1$H NMR (300 MHz, DMSO-d$_6$) δ 10.71 (s, 1H), 7.65-7.62 (m, 1H), 7.60-7.49 (m, 3H), 7.46-7.38 (m, 2H), 7.33 (d, J=4.3 Hz, 5H), 7.31-7.23 (m, 2H), 7.12 (d, J=7.7 Hz, 1H), 5.30 (s, 1H), 3.78 (s, 2H), 3.26 (s, 3H); $^{19}$F NMR (282 MHz, DMSO-d$_6$) δ −60.74. MS (ES+) 481.3 (M+1).

Preparation of 1-(3-(aminomethyl)phenyl)-N-(3-(ethoxy(phenyl)methyl)phenyl)-3-(trifluoromethyl)-1H-pyrazole-5-carboxamide (18g)

To a solution of tert-butyl 3-(5-(3-(hydroxy(phenyl)methyl)phenylcarbamoyl)-3-(trifluoromethyl)-1H-pyrazol-1-yl)benzylcarbamate (18c) (193 mg, 0.341 mmol) in 1,4-Dioxane (18 mL) was added hydrogen chloride (3.60 mL, 14.39 mmol, 4 M in 1,4-dioxane) dropwise followed by stirring at room temperature for 21 h. The reaction mixture was diluted with hexanes, decanted, and the residue obtained was washed with hexanes with decantation. To the residue of 1-(3-(aminomethyl)phenyl)-N-(3-(chloro(phenyl)methyl) phenyl)-3-(trifluoromethyl)-1H-pyrazole-5-carboxamide (18d) dissolved in chloroform/ethanol (40 mL/15 mL) was added silica gel 2 g and concentrated in vacuum to obtain a slurry which was purified by flash column chromatography (silica gel 2×4 g, eluting with chloroform/CMA 80 (1:0 to 2:1) to afford 1-(3-(aminomethyl)phenyl)-N-(3-(ethoxy(phenyl)methyl)phenyl)-3-(trifluoromethyl)-1H-pyrazole-5-carboxamide (18g) as a white solid (24 mg, 14%); $^1$H NMR (300 MHz, DMSO-d$_6$) δ 7.61 (s, 1H), 7.57 (s, 2H), 7.52 (s, 1H), 7.42 (d, J=6.2 Hz, 2H), 7.35-7.31 (m, 5H), 7.27 (d, J=7.9 Hz, 2H), 7.12 (d, J=7.8 Hz, 1H), 5.41 (s, 1H), 3.76 (s, 2H), 3.47-3.37 (m, 2H), 1.17 (t, J=7.0 Hz, 3H); $^{19}$F NMR (282 MHz, DMSO-d$_6$) δ −60.73. MS (ES+) 495.3 (M+1).

Preparation of 1-(3-(aminomethyl)phenyl)-N-(3-(phenyl(propoxy)methyl)phenyl)-3-(trifluoromethyl)-1H-pyrazole-5-carboxamide (18h)

To a solution of tert-butyl 3-(5-(3-(hydroxy(phenyl)methyl)phenylcarbamoyl)-3-(trifluoromethyl)-1H-pyrazol-1-yl)benzylcarbamate (18c) (80 mg, 0.141 mmol) in 1,4-Dioxane (8 mL) was added hydrogen chloride (1.5 mL, 6 mmol, 4 M in 1,4-dioxane) dropwise followed by stirring at room temperature for 16 h. The reaction mixture was diluted with hexanes, decanted, and the residue obtained was washed with hexanes with decantation. To the residue of 1-(3-(aminomethyl)phenyl)-N-(3-(chloro(phenyl)methyl)phenyl)-3-(trifluoromethyl)-1H-pyrazole-5-carboxamide (18d) dissolved in chloroform/1-propanol (40 mL/15 mL) was added silica gel 2 g and concentrated in vacuum to obtain a slurry which was purified by flash column chromatography (silica gel 2×4 g, eluting with chloroform/CMA 80 (1:0 to 2:1) to afford 1-(3-(aminomethyl)phenyl)-N-(3-(phenyl(propoxy)methyl)phenyl)-3-(trifluoromethyl)-1H-pyrazole-5-carboxamide (18h) (31 mgs, 43%) as a colorless oil; $^1$H NMR (300 MHz, DMSO-d$_6$) δ 10.71 (s, 1H), 7.61 (t, J=1.8 Hz, 1H), 7.59-7.51 (m, 3H), 7.45-7.38 (m, 2H), 7.36-7.28 (m, 6H), 7.27-7.22 (m, 1H), 7.12 (d, J=7.6 Hz, 1H), 5.39 (s, 1H), 3.77 (s, 2H), 3.47-3.39 (m, 2H), 1.64-1.50 (m, 2H), 0.89 (t, J=7.4 Hz, 3H); $^1$H NMR (300 MHz, Methanol-d$_4$) δ 7.57 (t, J=1.9 Hz, 1H), 7.53 (s, 1H), 7.52-7.45 (m, 3H), 7.40 (dt, J=4.5, 2.4 Hz, 1H), 7.35-7.22 (m, 7H), 7.17-7.11 (m, 1H), 5.34 (s, 1H), 3.86 (s, 2H), 3.40 (td, J=6.4, 1.0 Hz, 2H), 1.64 (dtd, J=13.8, 7.4, 6.5 Hz, 2H), 0.95 (t, J=7.4 Hz, 3H); $^{19}$F NMR (282 MHz, Methanol-d$_4$) δ −63.73; MS (ES+): 509.3 (M+1); (ES−) 507.3 (M−1).

Preparation of 1-(3-(aminomethyl)phenyl)-N-(3-(isobutoxy(phenyl)methyl)phenyl)-3-(trifluoromethyl)-1H-pyrazole-5-carboxamide (18i)

To a solution of tert-butyl 3-(5-(3-(hydroxy(phenyl)methyl)phenylcarbamoyl)-3-(trifluoromethyl)-1H-pyrazol-1-yl)benzylcarbamate (18c) (80 mg, 0.141 mmol) in 1,4-Dioxane (8 mL) was added hydrogen chloride (1.5 mL, 6 mmol, 4 M in 1,4-dioxane) dropwise followed by stirring at room temperature for 16 h. The reaction mixture was diluted with hexanes, decanted, and the residue obtained was washed with hexanes with decantation. The residue of 1-(3-(aminomethyl)phenyl)-N-(3-(chloro(phenyl)methyl)phenyl)-3-(trifluoromethyl)-1H-pyrazole-5-carboxamide (18d) dissolved in chloroform/iso-butanol (40 mL/15 mL) was added silica gel 2 g and concentrated in vacuum to obtain a slurry which was purified by flash column chromatography (silica gel 2×4 g, eluting with chloroform/CMA 80 (1:0 to 2:1) to afford 1-(3-(aminomethyl)phenyl)-N-(3-(isobutoxy(phenyl)methyl)phenyl)-3-(trifluoromethyl)-1H-pyrazole-5-carboxamide (18i) (14 mgs, 19%) as a white solid; $^1$H NMR (300 MHz, DMSO-d$_6$) δ 10.71 (s, 1H), 7.61 (d, J=1.9 Hz, 1H), 7.59-7.50 (m, 3H), 7.42 (d, J=6.7 Hz, 2H), 7.32 (t, J=6.4 Hz, 5H), 7.27-7.21 (m, 1H), 7.12 (d, J=7.7 Hz, 1H), 5.38 (s, 1H), 3.77 (s, 2H), 3.20-3.10 (m, 2H), 1.87 (dq, J=13.3, 6.6 Hz, 1H), 0.88 (dd, J=6.6, 1.3 Hz, 6H); 19F NMR (282 MHz, DMSO-d$_6$) δ −60.71; MS (ES+) 523.3 (M+1); (ES−) 521.4 (M−1).

Preparation of 1-(3-(aminomethyl)phenyl)-N-(3-(butoxy(phenyl)methyl)phenyl)-3-(trifluoromethyl)-1H-pyrazole-5-carboxamide (18j)

To a solution of tert-butyl 3-(5-(3-(hydroxy(phenyl)methyl)phenylcarbamoyl)-3-(trifluoromethyl)-1H-pyrazol-1-yl)benzylcarbamate (18c) (80 mg, 0.141 mmol) in 1,4-Dioxane (8 mL) was added hydrogen chloride (1.5 mL, 6 mmol, 4 M in 1,4-dioxane) dropwise followed by stirring at room temperature for 16 h. The reaction mixture was diluted with hexanes, decanted, and the residue obtained was washed with hexanes with decantation. The residue of 1-(3-(aminomethyl)phenyl)-N-(3-(chloro(phenyl)methyl)phenyl)-3-(trifluoromethyl)-1H-pyrazole-5-carboxamide (18d) dissolved in chloroform/1-butanol (40 mL/15 mL) was added silica gel 2 g and concentrated in vacuum to obtain a slurry which was purified by flash column chromatography (silica gel 2×4 g, eluting with chloroform/CMA 80 (1:0 to 2:1) to afford 1-(3-(aminomethyl)phenyl)-N-(3-(butoxy(phenyl)methyl)phenyl)-3-(trifluoromethyl)-1H-pyrazole-5-carboxamide (18j) (14 mgs, 19%) as a colorless semisolid; $^1$H NMR (300 MHz, DMSO-d$_6$) δ 10.72 (s, 1H), 7.64-7.49 (m, 4H), 7.44-7.37 (m, 2H), 7.36-7.20 (m, 7H), 7.12 (d, J=8.0 Hz, 1H), 5.39 (s, 1H), 3.77 (s, 2H), 3.43-3.34 (m, 2H), 1.54 (dq, J=8.3, 6.3 Hz, 2H), 1.36 (dq, J=9.4, 7.2 Hz, 2H), 0.85 (t, J=7.3 Hz, 3H); $^{19}$F NMR (282 MHz, DMSO-d$_6$) δ −60.73; MS (ES+): 523.4 (M+1).

Preparation of 1-(3-(aminomethyl)phenyl)-N-(3-((cyclopropylmethoxy)(phenyl)methyl)phenyl)-3-(trifluoromethyl)-1H-pyrazole-5-carboxamide (18k)

To a solution of tert-butyl 3-(5-(3-(hydroxy(phenyl)methyl)phenylcarbamoyl)-3-(trifluoromethyl)-1H-pyrazol-1-yl)benzylcarbamate (18c) (1 g, 1.765 mmol) in 1,4-Dioxane (90 mL) was added a 4 M solution of hydrogen chloride in dioxane (19.00 mL, 76 mmol). The reaction mixture was stirred at room temperature 16 h and diluted with hexanes. The organic solution was decanted and the residue washed with hexanes. The residue was dissolved in chloroform/cyclopropanemethanol (120 mL/7 mL) and stirred at room temperature for 68 h. Silica gel (3 gm) was added to the reaction mixture and the mixture was concentrated in vacuum to dryness. The slurry was purified twice by combiflash column chromatography (silica gel 12 g, eluting with chloroform/CMA80 0-25%) to afford 1-(3-(aminomethyl)phenyl)-N-(3-((cyclopropylmethoxy)(phenyl)methyl)phenyl)-3-(trifluoromethyl)-1H-pyrazole-5-carboxamide (18k) (124 mg, 13.5%) as a white solid; $^1$H NMR (300 MHz, DMSO-d$_6$) δ 10.72 (s, 1H), 7.64-7.50 (m, 4H), 7.46-7.38 (m, 2H), 7.36-7.27 (m, 6H), 7.27-7.20 (m, 1H), 7.13 (d, J=7.7 Hz, 1H), 5.44 (s, 1H), 3.77 (s, 2H), 3.23 (dd, J=6.7, 1.3 Hz, 2H), 1.14-0.97 (m, 1H), 0.50-0.42 (m, 2H), 0.19-0.10 (m, 2H); 19F NMR (300 MHz, DMSO-d$_6$) δ −60.73; MS (ES+) 521.3 (M+1).

Scheme 19

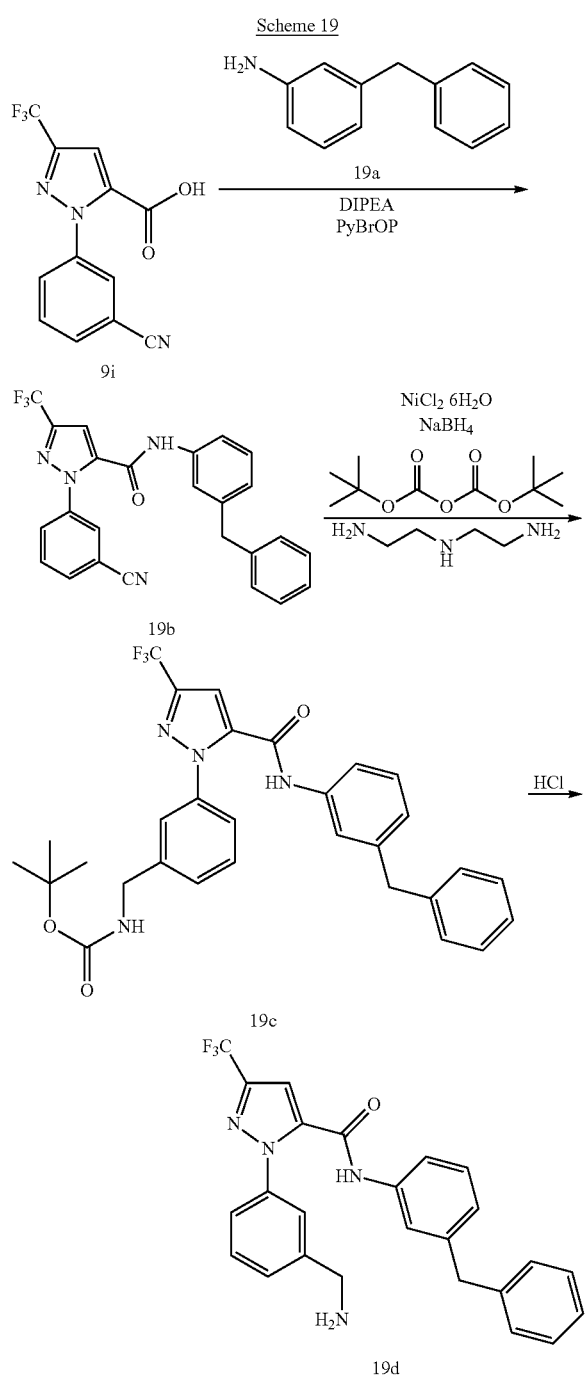

Preparation of 1-(3-(aminomethyl)phenyl)-N-(3-benzylphenyl)-3-(trifluoromethyl)-1H-pyrazole-5-carboxamide (19d)

Step-1: Preparation of N-(3-benzylphenyl)-1-(3-cyanophenyl)-3-(trifluoromethyl)-1H-pyrazole-5-carboxamide (19b)

To a solution of 1-(3-cyanophenyl)-3-(trifluoromethyl)-1H-pyrazole-5-carboxylic acid (400 mg, 1.423 mmol) in DMF (10 mL) was added 3-benzylaniline (19a) (261 mg, 1.423 mmol), N-ethyl-N-isopropylpropan-2-amine (2.0 mL, 11.48 mmol) and bromotripyrrolidin-1-ylphosphonium hexafluorophosphate(V) (PyBrOP, 682 mg, 1.434 mmol) and stirred at room temperature for 14 h. The reaction mixture was diluted with ethyl acetate (200 mL), washed with water (2×75 mL), brine (75 mL), dried over MgSO$_4$, filtered and concentrated in vacuum to dryness. The residue obtained was purified by flash column chromatography [silica gel, eluting with hexanes/ethyl acetate (1:0 to 3:1)] to furnish N-(3-benzylphenyl)-1-(3-cyanophenyl)-3-(trifluoromethyl)-1H-pyrazole-5-carboxamide (19b) (330 mg) as a yellow gum, which was used as such for next step; MS (ES+) 469.3 (M+23).

Step-2: Preparation of tert-butyl 3-(5-((3-benzylphenyl)carbamoyl)-3-(trifluoromethyl)-1H-pyrazol-1-yl)benzylcarbamate (19c)

To a solution of N-(3-benzylphenyl)-1-(3-cyanophenyl)-3-(trifluoromethyl)-1H-pyrazole-5-carboxamide (19b) (200 mg, 0.448 mmol) in methanol (4 mL) cooled with ice/water was added di-tert-butyl dicarbonate (296 mg, 1.344 mmol), nickel(II)chloride hexahydrate (22.00 mg, 0.093 mmol) followed by portion-wise addition of sodium borohydride (104 mg, 2.69 mmol) over a period of 5 min. The reaction mixture was stirred at room temperature for 1 h, quenched with N1-(2-aminoethyl)ethane-1,2-diamine (0.100 mL, 0.914 mmol), stirred at room temperature for 0.5 h and concentrated in vacuum to dryness. The residue was dissolved in ethyl acetate (100 mL), washed with water (50 mL). The aqueous phase was extracted again with ethyl acetate (50 mL). The combined extracts were washed with brine (60 mL), dried over MgSO$_4$, filtered and concentrated in vacuum to dryness. The crude product obtained was purified by flash column chromatography [silica gel 12 g, eluting with hexanes/ethyl acetate (1:0 to 4:1)] to afford tert-butyl 3-(5-(3-benzylphenylcarbamoyl)-3-(trifluoromethyl)-1H-pyrazol-1-yl)benzylcarbamate (19c) (121 mg, 26% for two steps) as a white solid; $^1$H NMR (300 MHz, DMSO-d$_6$) δ 10.68 (s, 1H), 7.72-6.87 (m, 15H), 4.19 (d, J=6.4 Hz, 2H), 3.91 (s, 2H), 1.37 (s, 9H); MS (ES+) 473.4 (M+23).

Step-3: Preparation of 1-(3-(aminomethyl)phenyl)-N-(3-benzylphenyl)-3-(trifluoromethyl)-1H-pyrazole-5-carboxamide (19d)

To a solution of tert-butyl 3-(5-(3-benzylphenylcarbamoyl)-3-(trifluoromethyl)-1H-pyrazol-1-yl)benzylcarbamate (19c) (105 mg, 0.191 mmol) in 1,4-Dioxane (9 mL) was added drop-wise hydrogen chloride (2.0 mL, 8.0 mmol, 4 M in 1,4-dioxane) and stirred at room temperature for 18 h. The reaction mixture was treated with hexanes, decanted, washed with hexanes, and decanted again. The insoluble part was purified by flash column chromatography on [silica gel 4 g, eluting with chloroform/CMA80 (1:0 to 2:1)] to afford 1-(3-(aminomethyl)phenyl)-N-(3-benzylphenyl)-3-(trifluoromethyl)-1H-pyrazole-5-carboxamide (19d) (33 mg, 38%) as an off-white solid; MP 69.9° C.; $^1$H NMR (300 MHz, DMSO-d$_6$) δ 10.66 (s, 1H), 7.56-7.41 (m, 6H), 7.33-7.25 (m, 4H), 7.24-7.17 (m, 3H), 7.01 (d, J=7.6 Hz, 1H), 3.91 (s, 2H), 3.77 (s, 2H); $^{19}$F NMR (282 MHz, DMSO-d$_6$) δ −60.73; MS (ES+) 451.3 (M+1)

Scheme 20

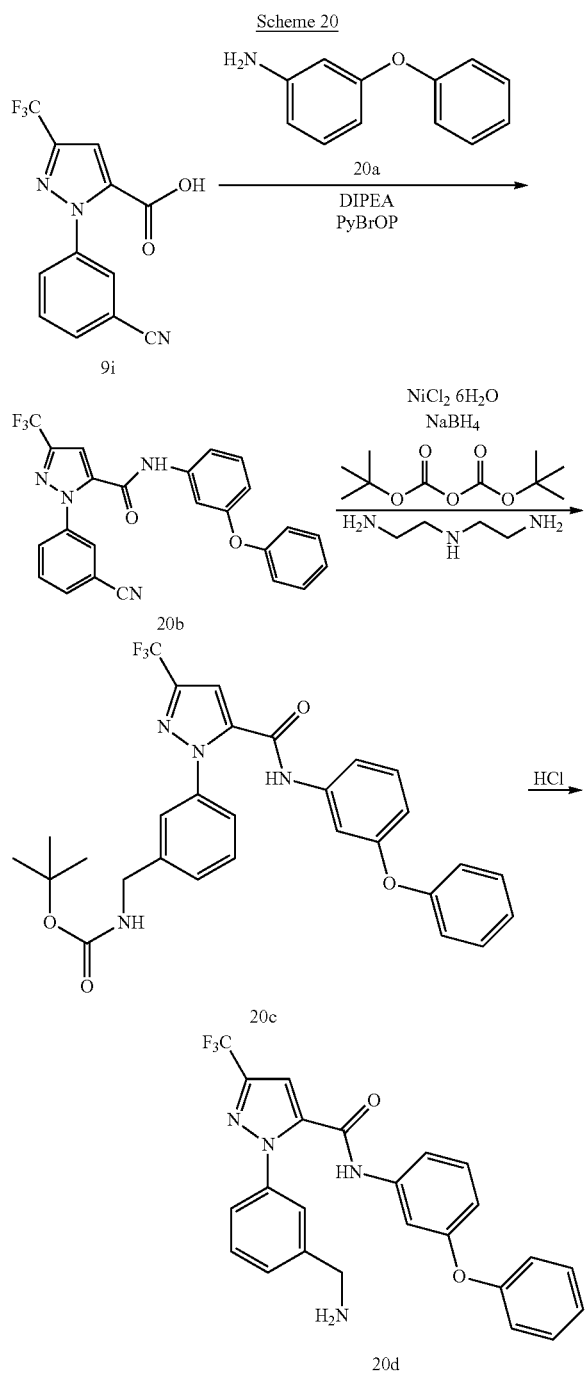

Preparation of 1-(3-(aminomethyl)phenyl)-N-(3-phenoxyphenyl)-3-(trifluoromethyl)-1H-pyrazole-5-carboxamide (20d)

Step-1: Preparation of 1-(3-cyanophenyl)-N-(3-phenoxyphenyl)-3-(trifluoromethyl)-1H-pyrazole-5-carboxamide (20b)

To a solution of 1-(3-cyanophenyl)-3-(trifluoromethyl)-1H-pyrazole-5-carboxylic acid (9i) (400 mg, 1.423 mmol) in DMF (10 mL) was added 3-phenoxyaniline (20a) (263 mg, 1.423 mmol), N-ethyl-N-isopropylpropan-2-amine (2.0 mL, 11.48 mmol) and bromotripyrrolidin-1-ylphosphonium hexafluorophosphate(V) (PyBrOP, 682 mg, 1.434 mmol) and stirred at room temperature for 14 h. The reaction mixture was diluted with ethyl acetate (200 mL), washed with water (2×75 mL), brine (75 mL), dried over MgSO$_4$, filtered and concentrated in vacuum. The residue obtained was purified by flash column chromatography [silica gel, eluting with hexanes/ethyl acetate (1:0 to 3:1)] to afford 1-(3-cyanophenyl)-N-(3-phenoxyphenyl)-3-(trifluoromethyl)-1H-pyrazole-5-carboxamide (20b) (296 mg, 46%) as an off-white solid; $^1$H NMR (300 MHz, DMSO-d$_6$) δ 10.73 (s, 1H), 8.17 (t, J=1.9 Hz, 1H), 8.00 (dt, J=7.7, 1.3 Hz, 1H), 7.94-7.87 (m, 1H), 7.78-7.64 (m, 2H), 7.51-7.27 (m, 5H), 7.22-7.11 (m, 1H), 7.08-6.99 (m, 2H), 6.83-6.78 (m, 1H); MS (ES+) 471.2 (M+23).

Step-2: Preparation of tert-butyl 3-(5-((3-phenoxyphenyl)carbamoyl)-3-(trifluoromethyl)-1H-pyrazol-1-yl)benzylcarbamate (20c)

To a solution of 1-(3-cyanophenyl)-N-(3-phenoxyphenyl)-3-(trifluoromethyl)-1H-pyrazole-5-carboxamide (20b) (200 mg, 0.446 mmol) in methanol (4 mL) cooled with ice/water was added di-tert-butyl dicarbonate (295 mg, 1.338 mmol), nickel(II) chloride hexahydrate (22.00 mg, 0.093 mmol) followed by portion wise addition of sodium borohydride (103 mg, 2.68 mmol) slowly over a period of 5 min. The reaction mixture was stirred at room temperature for 1 h, quenched with N1-(2-aminoethyl)ethane-1,2-diamine (0.100 mL, 0.912 mmol), stirred at room temperature for 0.5 h. and concentrated in vacuum to dryness. The residue was dissolved in ethyl acetate (100 mL), washed with water (50 mL). The aqueous phase was extracted again with ethyl acetate (50 mL). The combined extracts were washed with brine (60 mL), dried over MgSO$_4$, filtered and concentrated in vacuum to dryness. The crude product was purified by flash column chromatography [silica gel 12 g, eluting with hexanes/ethyl acetate (1:0 to 3:1)] to afford tert-butyl 3-(5-(3-phenoxyphenylcarbamoyl)-3-(trifluoromethyl)-1H-pyrazol-1-yl)benzylcarbamate (20c) (173 mg, 70%) as a white solid; $^1$H NMR (300 MHz, DMSO-d$_6$) δ 10.78 (s, 1H), 7.57 (s, 1H), 7.53-6.75 (m, 14H), 4.19 (d, J=6.3 Hz, 2H), 1.37 (s, 9H); MS (ES+) 475.4 (M+23).

Step-3: Preparation of 1-(3-(aminomethyl)phenyl)-N-(3-phenoxyphenyl)-3-(trifluoromethyl)-1H-pyrazole-5-carboxamide (20d)

To a solution of tert-butyl 3-(5-(3-phenoxyphenylcarbamoyl)-3-(trifluoromethyl)-1H-pyrazol-1-yl)benzylcarbamate (20c) (115 mg, 0.208 mmol) in 1,4-Dioxane (9 mL) was added drop-wise hydrogen chloride (2.2 mL, 8.8 mmol, 4 M in 1,4-dioxane) and stirred at room temperature for 18 h. The reaction mixture was treated with hexanes, decanted, washed with hexanes, and decanted again. The insoluble part was purified by flash column chromatography [silica gel 4 g, eluting with chloroform/CMA80 (1:0 to 2:1)] to afford 1-(3-(aminomethyl)phenyl)-N-(3-phenoxyphenyl)-3-(trifluoromethyl)-1H-pyrazole-5-carboxamide (20d) (70 mg, 74%) as an off-white solid; MP 89.0° C.; $^1$H NMR (300 MHz, DMSO-d$_6$) δ 10.80 (s, 1H), 7.60 (s, 2H), 7.52-7.48 (m, 2H), 7.46-7.32 (m, 6H), 7.16 (t, J=7.4 Hz, 1H), 7.06-7.01 (m, 2H), 6.82-6.77 (m, 1H), 5.71 (s, 2H), 3.95 (s, 2H); $^{19}$F NMR (282 MHz, DMSO-d$_6$) δ −60.78; MS (ES+) 453.3 (M+1).

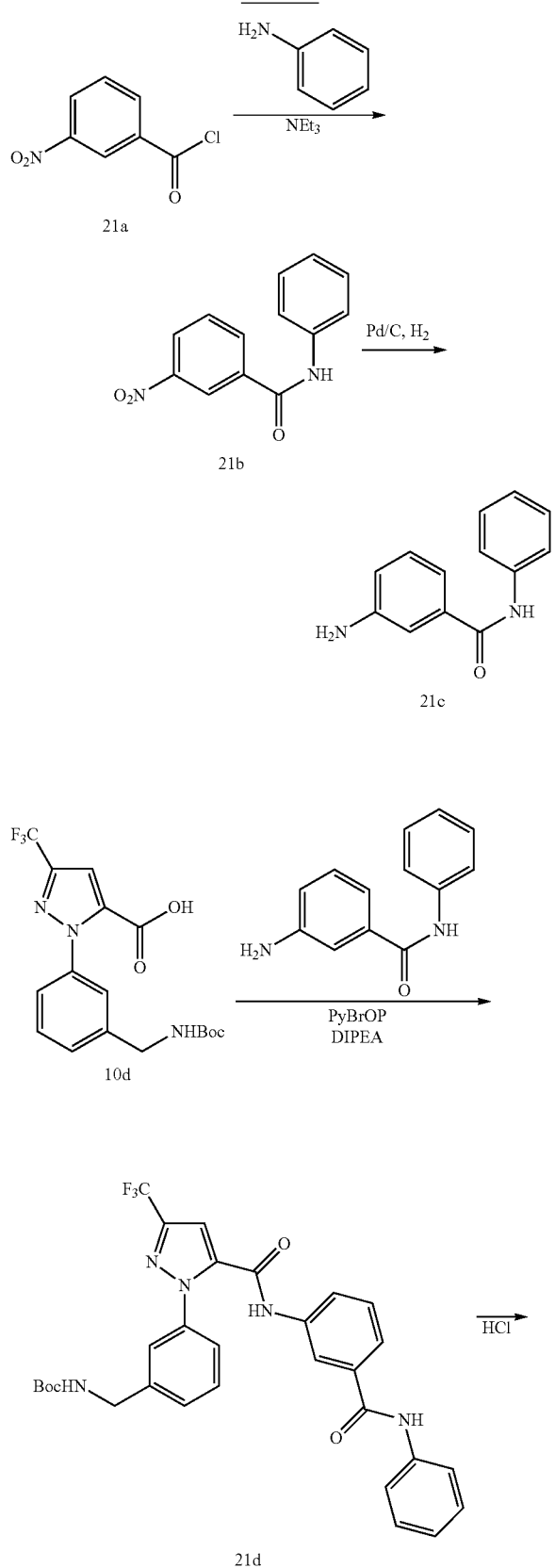
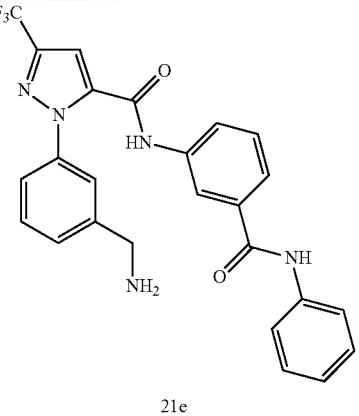

Preparation of 1-(3-(aminomethyl)phenyl)-N-(3-(phenylcarbamoyl)phenyl)-3-(trifluoromethyl)-1H-pyrazole-5-carboxamide (21e)

Step-1: Preparation of 3-nitro-N-phenylbenzamide (21b)

To a solution of aniline (2.94 mL, 32.2 mmol) in ethyl acetate (30 mL) at room temperature was added triethylamine (5.39 mL, 38.7 mmol) followed by a solution of 3-nitrobenzoyl chloride (5.98 g, 32.2 mmol) in ethyl acetate (30 mL). The reaction was stirred at room temperature for 20 h and quenched with water (30 mL). The aqueous layer was separated extracted with ethyl acetate (2×30 mL). The combined organic layers was washed with brine (30 mL), dried over anhydrous MgSO$_4$, filtered and concentrated in vacuum to dryness. The residue obtained was purified by flash column chromatography (silica gel 25 g, eluting with ethyl acetate in hexanes from 0-100%) to furnish 3-nitro-N-phenylbenzamide (21b) (2.93 g, 12.1 mmol, 37.5% yield) as white solid; $^1$H NMR (300 MHz, DMSO-d$_6$) δ 10.60 (s, 1H, D$_2$O exchangeable), 8.79 (t, J=2.0 Hz, 1H), 8.43 (dddd, J=12.0, 7.8, 2.1, 1.1 Hz, 2H), 7.85 (t, J=8.0 Hz, 1H), 7.82-7.75 (m, 2H), 7.44-7.35 (m, 2H), 7.20-7.10 (m, 1H).

Step-2: Preparation of 3-amino-N-phenylbenzamide (21c)

To a suspension of palladium on carbon (5%) (0.149 g, 1.404 mmol) in ethanol (120 mL) was added 3-nitro-N-phenylbenzamide (3.4 g, 14.04 mmol) and hydrogenated at 45 psi in Parr apparatus for 3 h. The reaction was filtered through Celite and concentrated in vacuum. The residue was dried to give compound 3-amino-N-phenylbenzamide (21c) (2.872 g, 13.53 mmol, 96% yield) as a colorless solid; $^1$H NMR (300 MHz, DMSO-d$_6$) δ 10.09 (s, 1H), 7.84-7.71 (m, 2H), 7.43-7.25 (m, 2H), 7.15 (t, J=7.7 Hz, 1H), 7.12-7.04 (m, 3H), 6.75 (ddd, J=7.9, 2.3, 1.1 Hz, 1H), 5.35 (s, 2H, D$_2$O exchangeable).

Step-3: Preparation of tert-butyl 3-(5-((3-(phenylcarbamoyl)phenyl)carbamoyl)-3-(trifluoromethyl)-1H-pyrazol-1-yl)benzylcarbamate (21d)

To a solution of 1-(3-((tert-butoxycarbonylamino)methyl)phenyl)-3-(trifluoromethyl)-1H-pyrazole-5-carboxylic acid (10d) (0.1 g, 0.26 mmol) in N,N-dimethylformamide (2 mL) was added 3-amino-N-phenylbenzamide (0.066 g, 0.311 mmol), N-ethyl-N-isopropylpropan-2-amine (0.362 mL, 2.076 mmol) and Bromo-tris-pyrrolidino phosphonium-hexafluorophosphate (PyBroP, 0.133 g, 0.285 mmol) at room temperature. The reaction mixture was stirred at 25° C. for 16 h. The reaction mixture was diluted with water (10 mL) extracted with ethyl acetate (2×20 mL). The organic layers were combined, washed with water (10 mL) dried over anhydrous MgSO$_4$, filtered, and concentrated under reduced pressure to dryness. The residue obtained was purified by flash column chromatography (silica gel 12 g, eluting with hexanes in ethyl acetate/hexanes from 0-100%) to furnish tert-butyl 3-(5-(3-(phenylcarbamoyl)phenylcarbamoyl)-3-(trifluoromethyl)-1H-pyrazol-1-yl)benzylcarbamate (21d) (77 mg, 0.133 mmol, 51.2% yield); $^1$H NMR (300 MHz, DMSO-d$_6$) δ 10.92 (s, 1H), 10.29 (s, 1H), 8.17 (t, J=1.9 Hz, 1H), 7.87 (d, J=7.9 Hz, 1H), 7.79-7.69 (m, 3H), 7.65 (s, 1H), 7.56-7.31 (m, 8H), 7.16-7.06 (m, 1H), 4.20 (d, J=6.2 Hz, 2H), 1.37 (s, 9H); MS (ES+) 580.3 (M+1), 602.3 (M+23), (ES−) 578.3 (M−1).

Step-4: Preparation of 1-(3-(aminomethyl)phenyl)-N-(3-(phenylcarbamoyl)phenyl)-3-(trifluoromethyl)-1H-pyrazole-5-carboxamide (21e)

To a stirred solution of tert-butyl 3-(5-(3-(phenylcarbamoyl)phenylcarbamoyl)-3-(trifluoromethyl)-1H-pyrazol-1-yl)benzylcarbamate (21d) (50 mg, 0.086 mmol) in methanol (5 mL) was added conc hydrochloric acid (0.052 mL, 1.725 mmol) and stirred the reaction overnight. Additional 20 eq. of HCl was added and stirred at reflux for 30 minutes. The reaction mixture was concentrated in vacuum to dryness. The residue was dried in vacuum overnight suspended in ether (25 mL), heated at reflux for 30 mins and stirred at room temperature overnight. The solid separated was collected by filtration dried to give 1-(3-(aminomethyl)phenyl)-N-(3-(phenylcarbamoyl)phenyl)-3-(trifluoromethyl)-1H-pyrazole-5-carboxamide dihydrochloride (21e) (45 mg, 0.081 mmol, 94% yield) as a white solid; $^1$H NMR (300 MHz, DMSO-d$_6$) δ 10.99 (s, 1H, D$_2$O exchangeable), 10.32 (s, 1H, D$_2$O exchangeable), 8.34 (s, 3H, D$_2$O exchangeable), 8.23 (t, J=1.9 Hz, 1H), 7.92-7.82 (m, 1H), 7.80-7.71 (m, 5H), 7.65-7.47 (m, 4H), 7.40-7.30 (m, 2H), 7.15-7.06 (m, 1H), 4.14 (s, 2H); MS (ES+) 480.2 (M+1); (ES−) 478.2 (M−1), 514.12 (M+35); Analysis calculated for C$_{25}$H$_{20}$F$_3$N$_5$O$_2$(HCl)$_2$: C, 54.43; H, 4.02; N, 12.72; Found C, 54.59; H, 4.55; N, 12.52.

Scheme 22

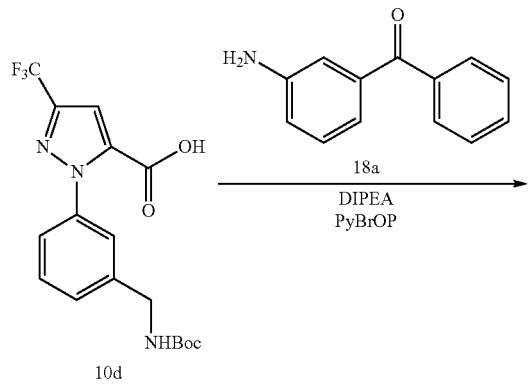

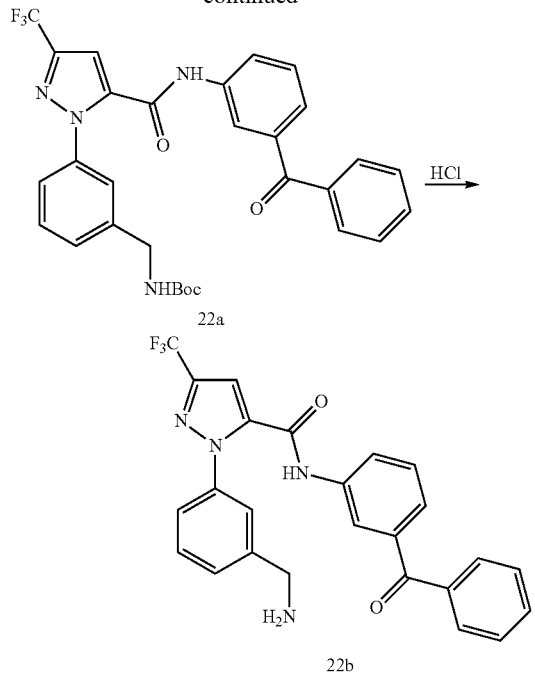

Preparation of 1-(3-(aminomethyl)phenyl)-N-(3-benzoylphenyl)-3-(trifluoromethyl)-1H-pyrazole-5-carboxamide (22b)

Step-1: Preparation of tert-butyl 3-(5-((3-benzoylphenyl)carbamoyl)-3-(trifluoromethyl)-1H-pyrazol-1-yl)benzylcarbamate (22a)

To a solution of 1-(3-((tert-butoxycarbonylamino)methyl)phenyl)-3-(trifluoromethyl)-1H-pyrazole-5-carboxylic acid (10d) (200 mg, 0.519 mmol) in DMF (5 mL) was added (3-aminophenyl)(phenyl)methanone (18a) (102 mg, 0.518 mmol), N-ethyl-N-isopropylpropan-2-amine (0.730 mL, 4.19 mmol), bromotripyrrolidin-1-ylphosphonium hexafluorophosphate(V) (PyBrOP, 248 mg, 0.522 mmol) and stirred at room temperature for 13 h. The reaction mixture was diluted with ethyl acetate (200 mL), washed with water (100, 75 mL), brine (100 mL), dried over MgSO$_4$, filtered and concentrated in vacuum. The residue obtained was purified by flash column chromatography [silica gel, eluting with hexanes/ethyl acetate (1:0 to 2:1)] to afford tert-butyl 3-(5-(3-benzoylphenylcarbamoyl)-3-(trifluoromethyl)-1H-pyrazol-1-yl)benzylcarbamate (22a) (182 mg, 62%) as a light yellow gum. $^1$H NMR (300 MHz, DMSO-d$_6$) δ 10.95 (s, 1H), 8.04 (t, J=1.8 Hz, 1H), 7.99 (d, J=8.0 Hz, 1H), 7.78-7.28 (m, 13H), 4.19 (d, J=6.2 Hz, 2H), 1.36 (s, 9H); MS (ES+) 587.3 (M+23).

Step-2: Preparation of 1-(3-(aminomethyl)phenyl)-N-(3-benzoylphenyl)-3-(trifluoromethyl)-1H-pyrazole-5-carboxamide (22b)

To a solution of tert-butyl 3-(5-(3-benzoylphenylcarbamoyl)-3-(trifluoromethyl)-1H-pyrazol-1-yl)benzylcarbamate (22a) (0.15 g, 0.266 mmol) in 1,4-Dioxane (14 mL) was added dropwise hydrogen chloride (2.80 mL, 11.21 mmol, 4 M in 1,4-dioxane) and stirred at room temperature for 17 h. The reaction mixture was diluted with hexanes and the solid obtained was collected by filtration. The light yellow solid was purified by flash column chromatography on 2×4 g of [silica gel 2×4 g, eluting with chloroform/CMA 80 (1:0 to 2:1)] to afford tert-butyl 3-(5-(3-benzoylphenylcarbamoyl)-3-(trifluoromethyl)-1H-pyrazol-1-yl)benzylcarbamate (22b) (75 mg, 61%) as an off-white solid; $^1$H NMR (300 MHz, DMSO-$d_6$) δ 10.92 (s, 1H), 8.04 (t, J=1.8 Hz, 1H), 7.97 (d, J=7.9 Hz, 1H), 7.75 (d, J=1.7 Hz, 1H), 7.73 (d, J=1.6 Hz, 1H), 7.71-7.65 (m, 1H), 7.61 (s, 1H), 7.60 (s, 1H), 7.57 (s, 1H), 7.56-7.52 (m, 2H), 7.51-7.47 (m, 1H), 7.45-7.41 (m, 2H), 7.33 (dt, J=5.3, 2.5 Hz, 1H), 3.78 (s, 2H); $^{19}$F NMR (282 MHz, DMSO-$d_6$) δ −60.75; MS (ES+) 465.2 (M+1).

Preparation of 1-(3-(aminomethyl)phenyl)-N-(2-fluoro-3-phenoxyphenyl)-3-(trifluoromethyl)-1H-pyrazole-5-carboxamide (23c)

Step-1: Preparation of tert-butyl 3-(5-((2-fluoro-3-phenoxyphenyl)carbamoyl)-3-(trifluoromethyl)-1H-pyrazol-1-yl)benzylcarbamate (23b)

To a solution of 1-(3-((tert-butoxycarbonylamino)methyl)phenyl)-3-(trifluoromethyl)-1H-pyrazole-5-carboxylic acid (10d) (200 mg, 0.519 mmol) in DMF (5 mL) was added 2-fluoro-3-phenoxyaniline (23a) (105 mg, 0.519 mmol), N-ethyl-N-isopropylpropan-2-amine (0.730 mL, 4.19 mmol), bromotripyrrolidin-1-ylphosphonium hexafluorophosphate(V) (PyBrOP, 249 mg, 0.523 mmol) and stirred at room temperature for 15 h. The reaction mixture was diluted with ethyl acetate (150 mL), washed with water (2×75 mL), brine (750 mL), dried over MgSO$_4$, filtered and concentrated in vacuum. The residue obtained was purified by flash column chromatography [silica gel, eluting with hexanes/ethyl acetate (1:0 to 2:1)] to afford 1-(3-(aminomethyl)phenyl)-N-(3-benzoylphenyl)-3-(trifluoromethyl)-1H-pyrazole-5-carboxamide (23b) (72 mg, 24%) as a colorless gum; $^1$H NMR (300 MHz, DMSO-$d_6$) δ 7.80-6.72 (m, 13H), 3.78 (s, 2H); MS (ES+): 593.2 (M+23).

Step-2: Preparation of 1-(3-(aminomethyl)phenyl)-N-(2-fluoro-3-phenoxyphenyl)-3-(trifluoromethyl)-1H-pyrazole-5-carboxamide (23c)

To a solution of tert-butyl 3-(5-(2-fluoro-3-phenoxyphenylcarbamoyl)-3-(trifluoromethyl)-1H-pyrazol-1-yl)benzylcarbamate (23b) (70 mg, 0.123 mmol) in 1,4-Dioxane (5 mL) was added dropwise hydrogen chloride (1.3 mL, 5.2 mmol, 4 M in 1,4-dioxane) and stirred at room temperature for 16 h. The reaction mixture was diluted with hexanes and the solid obtained was collected by filtration. The light yellow solid was purified by flash column chromatography on [silica gel 2×4 g, eluting with chloroform/CMA 80 (1:0 to 2:1)] to afford 1-(3-(aminomethyl)phenyl)-N-(2-fluoro-3-phenoxyphenyl)-3-(trifluoromethyl)-1H-pyrazole-5-carboxamide (23c) (32 mg, 55%) as a white solid; $^1$H NMR (300 MHz, DMSO-$d_6$) δ 7.60 (s, 1H), 7.53 (s, 1H), 7.48-7.32 (m, 6H), 7.24-7.11 (m, 2H), 7.06-6.97 (m, 3H), 3.78 (s, 2H); $^{19}$F NMR (282 MHz, DMSO-$d_6$) δ −60.76, −139.25; MS (ES+), 471.2 (M+1).

Scheme 23

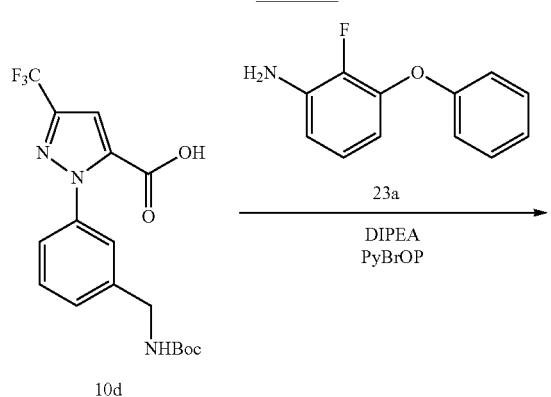

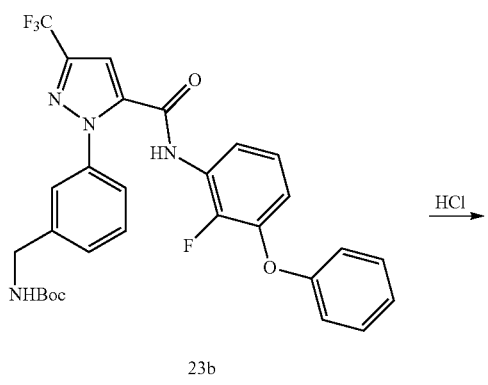

Scheme 24

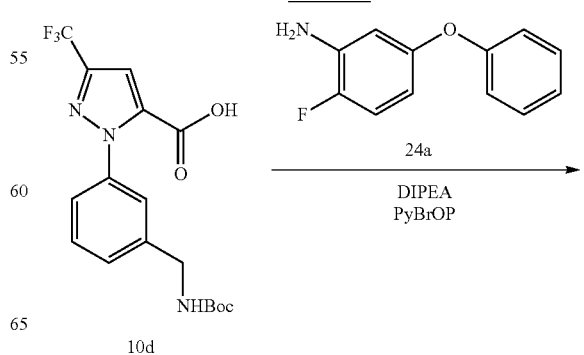

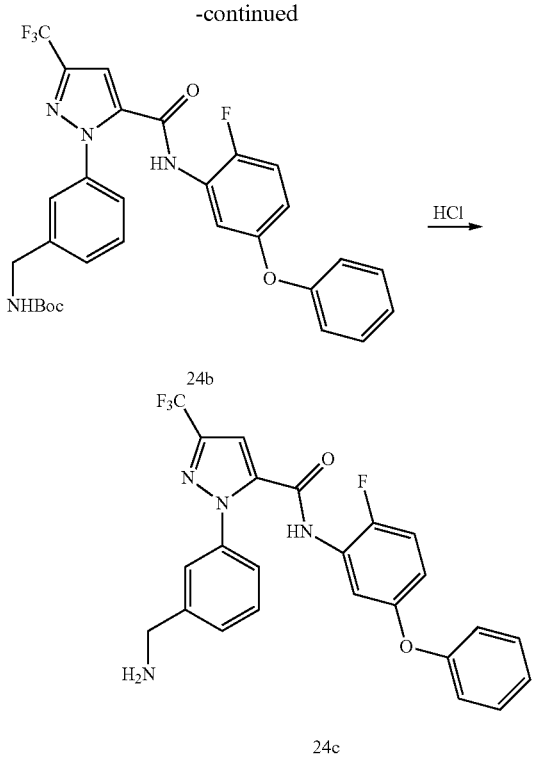

Preparation of 1-(3-(aminomethyl)phenyl)-N-(2-fluoro-5-phenoxyphenyl)-3-(trifluoromethyl)-1H-pyrazole-5-carboxamide (24c)

Step-1: Preparation of tert-butyl 3-(5-((2-fluoro-5-phenoxyphenyl)carbamoyl)-3-(trifluoromethyl)-1H-pyrazol-1-yl)benzylcarbamate (24b)

To a solution of 1-(3-((tert-butoxycarbonylamino)methyl)phenyl)-3-(trifluoromethyl)-1H-pyrazole-5-carboxylic acid (10d) (152 mg, 0.394 mmol) in DMF (3.5 mL) was treated with 2-fluoro-5-phenoxyaniline (24a) (80 mg, 0.394 mmol), N-ethyl-N-isopropylpropan-2-amine (0.550 mL, 3.16 mmol) bromotripyrrolidin-1-ylphosphonium hexafluorophosphate(V) (PyBrOP, 189 mg, 0.398 mmol) and stirred at room temperature for 15 h. The reaction mixture was diluted with ethyl acetate (100 mL), washed with water (2×50 mL), brine (50 mL), dried over MgSO$_4$, filtered and concentrated in vacuum. The residue obtained was purified by flash column chromatography [silica gel, eluting with hexanes/ethyl acetate (1:0 to 3:1)] to afford tert-butyl 3-(5-(2-fluoro-5-phenoxyphenylcarbamoyl)-3-(trifluoromethyl)-1H-pyrazol-1-yl)benzylcarbamate (24b) (57 mg, 25%) as a white solid; $^1$H NMR (300 MHz, DMSO-d$_6$) δ 10.65 (s, 1H), 7.58 (s, 1H), 7.53-6.86 (m, 13H), 4.18 (d, J=6.3 Hz, 2H), 1.37 (s, 9H); (ES+) 593.3 (M+23).

Step-2: Preparation of 1-(3-(aminomethyl)phenyl)-N-(2-fluoro-5-phenoxyphenyl)-3-(trifluoromethyl)-1H-pyrazole-5-carboxamide (24c)

To a solution of tert-butyl 3-(5-(2-fluoro-5-phenoxyphenylcarbamoyl)-3-(trifluoromethyl)-1H-pyrazol-1-yl)benzylcarbamate (24b) (55 mg, 0.096 mmol) in 1,4-Dioxane (4 mL) was added dropwise hydrogen chloride (1.0 mL, 4.0 mmol, 4 M in 1,4-dioxane) and stirred at room temperature for 16 h. The reaction mixture was diluted with hexanes and the solid obtained was collected by filtration. The solid obtained was purified by flash column chromatography [silica gel 4 g, eluting with chloroform/CMA 80 (1:0 to 2:1)] to afford 1-(3-(aminomethyl)phenyl)-N-(2-fluoro-5-phenoxyphenyl)-3-(trifluoromethyl)-1H-pyrazole-5-carboxamide (24c) (20 mg, 44%) as a white solid; $^1$H NMR (300 MHz, DMSO-d$_6$) δ 10.68 (s, 1H), 7.65-7.55 (m, 2H), 7.52-7.30 (m, 7H), 7.15 (tt, J=6.9, 1.2 Hz, 1H), 7.03-6.98 (m, 2H), 6.96-6.89 (m, 1H), 3.95 (s, 2H); $^{19}$F NMR (282 MHz, DMSO-d$_6$) δ −60.80, −127.85; MS (ES+) 471.2 (M+1); (ES−) 469.1 (M−1)

Scheme 25

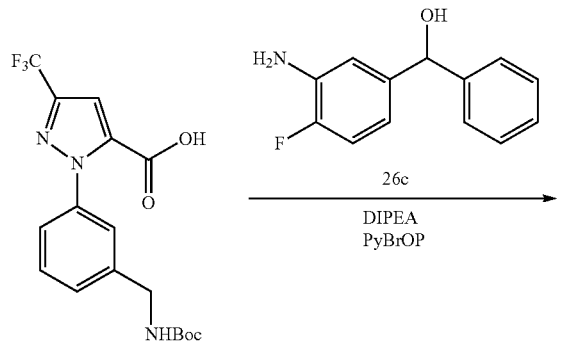

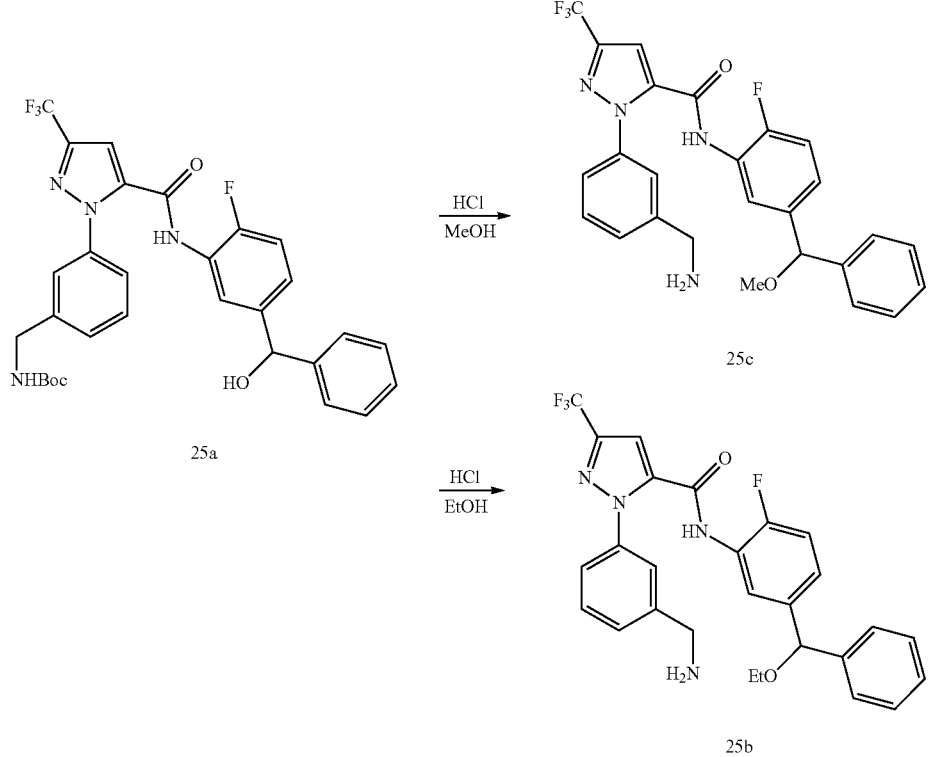

Preparation of 1-(3-(aminomethyl)phenyl)-N-(5-(ethoxy(phenyl)methyl)-2-fluorophenyl)-3-(trifluoromethyl)-1H-pyrazole-5-carboxamide (25b) and 1-(3-(aminomethyl)phenyl)-N-(2-fluoro-5-(methoxy(phenyl)methyl)phenyl)-3-(trifluoromethyl)-1H-pyrazole-5-carboxamide (25c)

Step-1: Preparation of tert-butyl 3-(5-((2-fluoro-5-(hydroxy(phenyl)methyl)phenyl)carbamoyl)-3-(trifluoromethyl)-1H-pyrazol-1-yl)benzylcarbamate (25a)

To a solution of 1-(3-(((tert-butoxycarbonylamino)methyl)phenyl)-3-(trifluoromethyl)-1H-pyrazole-5-carboxylic acid (10d) (284 mg, 0.737 mmol) in DMF (6.5 mL) was added (3-amino-4-fluorophenyl)(phenyl)methanol (26c) (160 mg, 0.737 mmol), N-ethyl-N-isopropylpropan-2-amine (1.05 mL, 6.03 mmol) bromotripyrrolidin-1-ylphosphonium hexafluorophosphate(V) (PyBrOP, 353 mg, 0.742 mmol) and stirred at room temperature for 12 h. The reaction mixture was diluted with ethyl acetate (150 mL), washed with water (2×75 mL), brine (60 mL), dried over MgSO$_4$, filtered and concentrated in vacuum. The residue obtained was purified by flash column chromatography [silica gel, eluting with hexanes/ethyl acetate (1:0 to 1:1)] to afford tert-butyl 3-(5-(2-fluoro-5-(hydroxy(phenyl)methyl)phenylcarbamoyl)-3-(trifluoromethyl)-1H-pyrazol-1-yl)benzylcarbamate (25a) (196 mg, 46%) as a white solid; $^1$H NMR (300 MHz, DMSO-d$_6$) δ 10.56 (s, 1H), 7.64-7.14 (m, 14H), 6.00 (d, J=3.9 Hz, 1H), 5.69 (d, J=4.0 Hz, 1H), 4.19 (d, J=6.2 Hz, 2H), 1.38 (s, 9H); MS (ES+) 607.3 (M+23).

Step-2: Preparation of 1-(3-(aminomethyl)phenyl)-N-(5-(ethoxy(phenyl)methyl)-2-fluorophenyl)-3-(trifluoromethyl)-1H-pyrazole-5-carboxamide (25b) and 1-(3-(aminomethyl)phenyl)-N-(2-fluoro-5-(methoxy(phenyl)methyl)phenyl)-3-(trifluoromethyl)-1H-pyrazole-5-carboxamide (25c)

To a solution of tert-butyl 3-(5-((2-fluoro-5-(hydroxy(phenyl)methyl)phenyl)carbamoyl)-3-(trifluoromethyl)-1H-pyrazol-1-yl)benzylcarbamate (25a) (0.18 g, 0.308 mmol) in 1,4-Dioxane (16 mL) was added dropwise hydrogen chloride (3.2 mL, 12.81 mmol, 4 M in 1,4-dioxane) and stirred at room temperature for 26 h. The reaction mixture was diluted with hexanes (~80 mL) and decanted to obtain yellow oil. Part of the insoluble yellow oil was dissolved in ethanol and converted to a silica gel slurry. The slurry was purified by flash column chromatography [silica gel 4 g, eluting with chloroform/CMA 80 (1:0 to 3:1)] to afford 1-(3-(aminomethyl)phenyl)-N-(5-(ethoxy(phenyl)methyl)-2-fluorophenyl)-3-(trifluoromethyl)-1H-pyrazole-5-carboxamide (25b) (61 mg, 39%) as a white solid; $^1$H NMR (300 MHz, DMSO-d$_6$) δ 10.57 (s, 1H), 7.54 (d, J=18.4 Hz, 3H), 7.45-7.38 (m, 2H), 7.33 (M, 5H), 7.27-7.22 (m, 3H), 5.45 (s, 1H), 3.77 (s, 2H), 3.42 (q, J=7.0 Hz, 2H), 1.16 (t, J=7.0 Hz, 3H); $^{19}$F NMR (282 MHz, DMSO-d$_6$) δ −60.76, −122.95; MS (ES+) 513.3 (M+1); (ES−) 511.2 (M−1).

Another part of the insoluble yellow oil was dissolved in methanol and converted to silica gel The slurry was purified by flash column chromatography [silica gel 4 g, eluting with chloroform/CMA 80 (1:0 to 1:1)] to afford 1-(3-(aminomethyl)phenyl)-N-(2-fluoro-5-(methoxy(phenyl)methyl)phenyl)-3-(trifluoromethyl)-1H-pyrazole-5-carboxamide (25c) (11 mg, 7.2%) as a white solid; $^1$H NMR (300 MHz, DMSO-d$_6$) δ 10.58 (s, 1H), 7.61-7.52 (m, 3H), 7.52-7.34 (m, 2H), 7.40-7.29 (m, 6H), 7.29-7.21 (m, 4H), 5.34 (s, 1H), 3.80 (s, 2H), 3.25 (s, 3H); $^{19}$F NMR (282 MHz, DMSO-$d_6$) δ −60.77, −122.99; MS (ES+) 499.3 (M+1); (ES−) 497.3 (M−1); 533.3 (M+Cl).

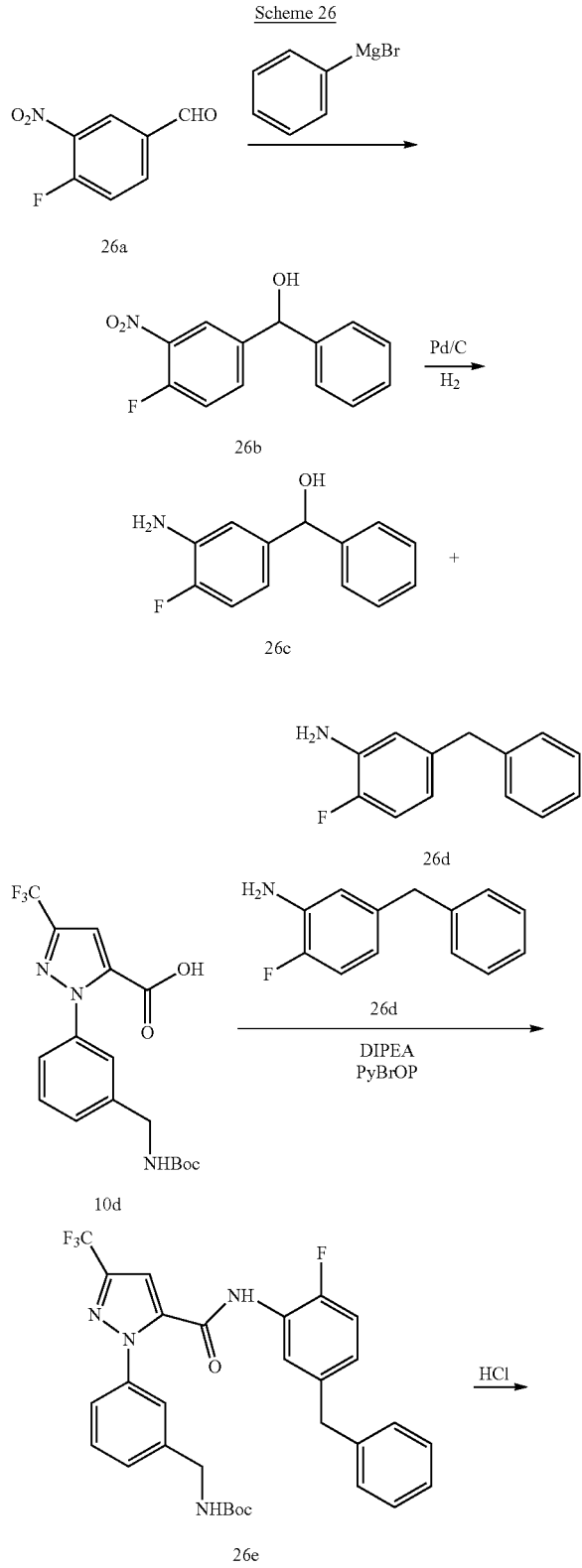

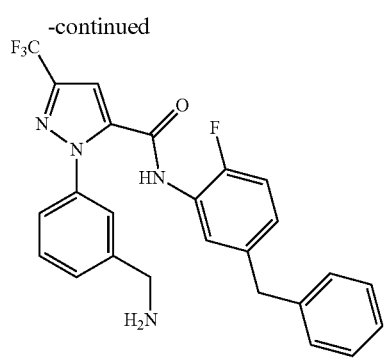

Preparation of 1-(3-(aminomethyl)phenyl)-N-(5-benzyl-2-fluorophenyl)-3-(trifluoromethyl)-1H-pyrazole-5-carboxamide (26f)

Step-1: Preparation of (4-fluoro-3-nitrophenyl)(phenyl)methanol (26b)

To a solution of 4-fluoro-3-nitrobenzaldehyde (26a) (4 g, 23.65 mmol) in THF (60 mL) cooled to 0° C. was added dropwise phenylmagnesium bromide (48.0 mL, 48.0 mmol) and stirred at room temperature for 14 h. The reaction mixture was quenched with saturated aqueous NH$_4$Cl (240 mL), extracted with ethyl acetate (300 mL, 150 mL). The combined extracts were washed with brine (150 mL), dried over MgSO$_4$, filtered and concentrated in vacuum. The crude product was purified by flash column chromatography [silica gel 80 g, eluting with hexanes/ethyl acetate (1:0 to 2:1)] to afford (4-fluoro-3-nitrophenyl)(phenyl)methanol (26b) (3.265 g, 56%) as a brown gum. $^1$H NMR (300 MHz, DMSO-$d_6$) δ 10.63 (s, 1H), 8.24 (s, 1H), 7.67-6.51 (m, 14H), 4.20 (d, J=6.3 Hz, 2H), 1.37 (s, 9H); MS (ES+) 270.1 (M+1).

Step-2: Preparation of (3-amino-4-fluorophenyl)(phenyl)methanol (26c) and 5-benzyl-2-fluoroaniline (26d)

A solution of (4-fluoro-3-nitrophenyl)(phenyl)methanol (26b) (2 g, 8.09 mmol) in ethanol (70 mL) and ethyl acetate (35 mL) was added Pd/C 10% (0.440 g, 0.413 mmol) followed by hydrogenation (~50 Psi) for 4.5 h. The reaction mixture was filtered through a pad of Celite and the filtrate was treated with 4 M HCl in 1,4-dioxane (~0.2 mL) and 4 N HCl (aq., ~0.2 mL) to pH=~5. The filtrate was concentrated in vacuum and the residue obtained was purified by flash column chromatography [silica gel 25 g, eluting with hexanes/ethyl acetate (1:0 to 3:1)] to afford
1. (3-amino-4-fluorophenyl)(phenyl)methanol (26c) (175 mg, 10%) as a light brown gum; $^1$H NMR (300 MHz, DMSO-$d_6$) δ 7.37-7.14 (m, 5H), 6.87 (dd, J=11.5, 8.3 Hz, 1H), 6.76 (dd, J=9.0, 2.2 Hz, 1H), 6.50 (176 dd, J=8.3, 4.6, 2.2, 0.6 Hz, 1H), 5.75 (d, J=3.9 Hz, 1H), 5.52 (d, J=3.9 Hz, 1H), 5.06 (s, 2H); $^{19}$F NMR (282 MHz, DMSO-$d_6$) δ −137.89; MS (ES+): 218.2 (M+1).
2. 5-benzyl-2-fluoroaniline (26d) (1.084 g, 67%) as a brown gum; $^1$H NMR (300 MHz, DMSO-$d_6$) δ 7.34-7.11 (m, 5H), 6.86 (dd, J=11.6, 8.2 Hz, 1H), 6.57 (dd, J=8.9, 2.2 Hz, 1H), 6.36 (ddd, J=8.2, 4.5, 2.2 Hz, 1H), 5.04 (s, 2H), 3.76 (s, 2H); $^{19}$F NMR (282 MHz, DMSO-$d_6$) δ −139.01; MS (ES+): 202.1 (M+1).

185

Step-3: Preparation of tert-butyl 3-(5-(5-benzyl-2-fluorophenylcarbamoyl)-3-(trifluoromethyl)-1H-pyrazol-1-yl)benzylcarbamate (26e)

To a solution of 1-(3-(((tert-butoxycarbonylamino)methyl)phenyl)-3-(trifluoromethyl)-1H-pyrazole-5-carboxylic acid (10d) (303 mg, 0.786 mmol) in DMF (7 mL) was added 5-benzyl-2-fluoroaniline (26d) (158 mg, 0.786 mmol), N-ethyl-N-isopropylpropan-2-amine (1.1 mL, 6.31 mmol) bromotripyrrolidin-1-ylphosphonium hexafluorophosphate (V) (PyBrOP, 377 mg, 0.793 mmol) and stirred at room temperature for 19 h. The reaction mixture was diluted with ethyl acetate (150 mL), washed with water (2×75 mL), brine (60 mL), dried over MgSO₄, filtered and concentrated in vacuum. The residue obtained was purified by flash column chromatography [silica gel, eluting with hexanes/ethyl acetate (1:0 to 3:1)] to afford tert-butyl 3-(5-(5-benzyl-2-fluorophenylcarbamoyl)-3-(trifluoromethyl)-1H-pyrazol-1-yl)benzylcarbamate (26e)(228 mg) as a white solid, which was used as such for next step; MS (ES+) 591.3 (M+23);

Step-4: Preparation of 1-(3-(aminomethyl)phenyl)-N-(5-benzyl-2-fluorophenyl)-3-(trifluoromethyl)-1H-pyrazole-5-carboxamide (26f)

To a solution of tert-butyl 3-(5-(5-benzyl-2-fluorophenylcarbamoyl)-3-(trifluoromethyl)-1H-pyrazol-1-yl)benzylcarbamate (26e) (0.202 g, 0.355 mmol) in 1,4-Dioxane (18 mL) was added dropwise hydrogen chloride (3.7 mL, 14.78 mmol, 4 M in 1,4-dioxane) and stirred at room temperature for 21 h. The reaction mixture was diluted with hexanes and the yellow solid obtained was collected by filtration. The yellow solid was purified by flash column chromatography [silica gel 12 g, eluting with chloroform/methanol (1:0 to 9:1)] to afford 1-(3-(aminomethyl)phenyl)-N-(5-benzyl-2-fluorophenyl)-3-(trifluoromethyl)-1H-pyrazole-5-carboxamide (26f) (99 mg) as a colorless gum; ¹H NMR (300 MHz, DMSO-d₆) δ 10.54 (s, 1H), 7.56 (s, 1H), 7.51 (s, 1H), 7.47-7.40 (m, 3H), 7.35-7.25 (m, 3H), 7.27-7.15 (m, 4H), 7.13 (ddt, J=8.5, 5.0, 2.2 Hz, 1H), 3.92 (s, 2H), 3.78 (s, 2H); ¹⁹F NMR (282 MHz, DMSO-d₆) δ −60.75, −125.06; MS (ES+) 469.3 (M+1); (ES−) 467.2 (M−1).

186

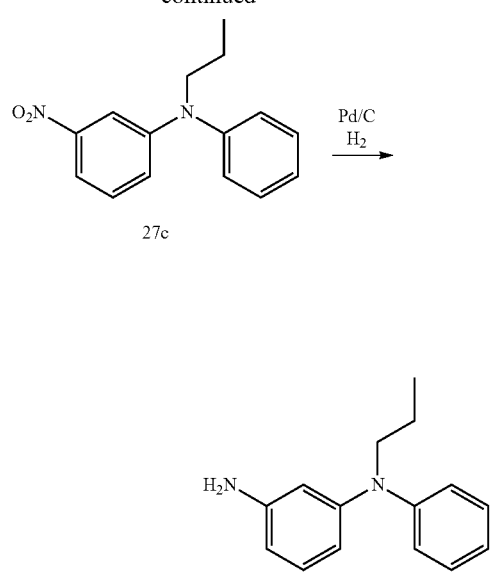

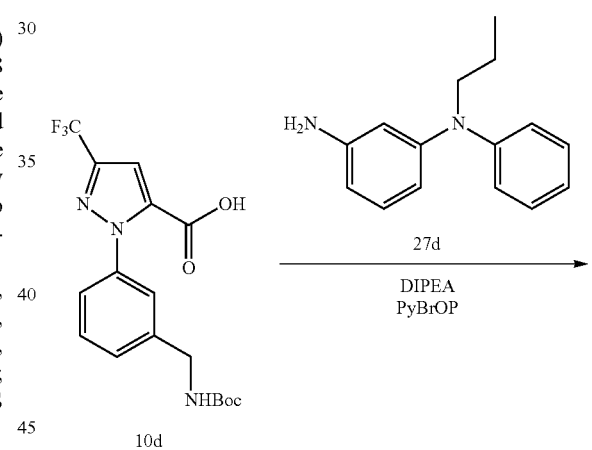

Scheme 27

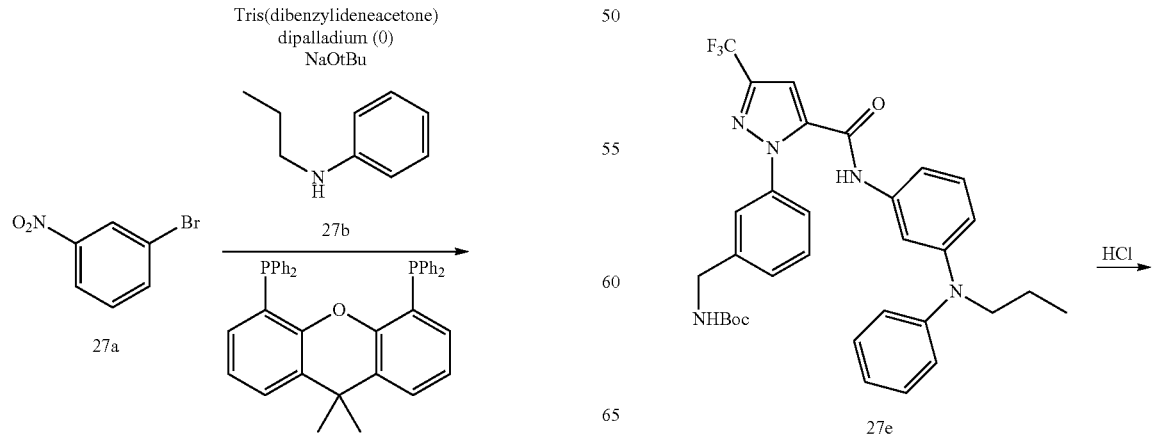

187

-continued

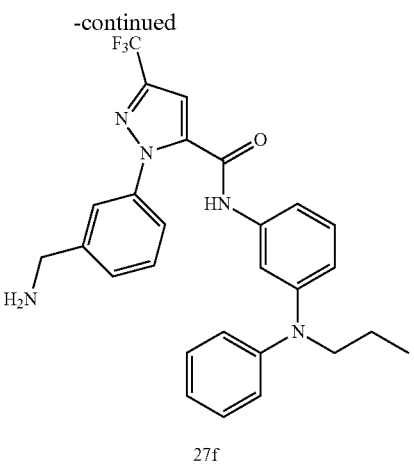

27f

Preparation of 1-(3-(aminomethyl)phenyl)-N-(3-(phenyl(propyl)amino)phenyl)-3-(trifluoromethyl)-1H-pyrazole-5-carboxamide (27f)

Step-1: Preparation of 3-nitro-N-phenyl-N-propylaniline (27c)

To a solution of 1-bromo-3-nitrobenzene (27a) (3 g, 14.85 mmol) and N-propylaniline (27b) (2.41 g, 17.82 mmol) in toluene (15 mL) was added sodium 2-methylpropan-2-olate (1.142 g, 11.88 mmol), (9,9-dimethyl-9H-xanthene-4,5-diyl)bis(diphenylphosphine) (0.859 g, 1.485 mmol) and Tris(dibenzylideneacetone)dipalladium (0) (0.408 g, 0.446 mmol). The reaction mixture was stirred at 110° C. for 16 h under a positive flow of nitrogen. Reaction mixture was cooled to room temperature, quenched with water (75 mL), extracted with ethyl acetate (2×100 mL). The organic layers were combined dried over MgSO$_4$, filtered and evaporated to dryness. The residue obtained was purified by flash column chromatography [(silica gel 80 g, eluting with ethyl acetate in hexanes from 0 to 100%)] to afford 3-nitro-N-phenyl-N-propylaniline (27c) (2.931 g, 11.44 mmol, 77% yield) as a brown-yellow oil. Isolated product was not very pure but good enough to be used as such for next step; MS (ES+) 257.2 (M+1).

Step-2: Preparation of N$_1$-phenyl-N$_1$-propylbenzene-1,3-diamine (27d)

To a solution of 3-nitro-N-phenyl-N-propylaniline (27c) (2.9 g, 11.31 mmol) in methanol (30 mL) was added palladium (10% Pd on carbon, 0.241 g). The mixture was hydrogenated for 2 h, filtered through a pad of Celite and the filtrate was concentrated in vacuum to dryness. The residue was purified by flash column chromatography (silica gel 80 g, eluting with ethyl acetate in hexanes from 0 to 100%) to afford N$_1$-phenyl-N$_1$-propylbenzene-1,3-diamine (27d) (1.195 g, 5.28 mmol, 46.7% yield) as a dark-green oil; MS (ES+) 227.2 (M+1).

Step-3: Preparation of tert-butyl 3-(5-((3-(phenyl(propyl)amino)phenyl)carbamoyl)-3-(trifluoromethyl)-1H-pyrazol-1-yl)benzylcarbamate (27e)

To a solution of 1-(3-((tert-butoxycarbonylamino)methyl)phenyl)-3-(trifluoromethyl)-1H-pyrazole-5-carboxylic acid (10d) (0.19 g, 0.493 mmol) in DMF (3 mL) was added N$_1$-phenyl-N$_1$-propylbenzene-1,3-diamine (27d) (0.134 g, 0.592 mmol), N-ethyl-N-isopropylpropan-2-amine (0.687 mL, 3.94 mmol) and bromo-tris-pyrrolidino phosphonium-hexafluorophosphate (PyBrop, 0.253 g, 0.542 mmol) at room temperature. The reaction mixture was stirred at room temperature for 17 h and concentrated in vacuum to dryness. The reaction was diluted with water (25 mL) and extracted with ethyl acetate (50, 20 mL). The organic layers were combined, dried, filtered, and evaporated to dryness. The residue obtained was purified by flash column chromatography [silica gel 12 g, eluting with ethyl acetate in hexanes from 0-25%] to afford tert-butyl 3-(5-(3-(phenyl(propyl)amino)phenylcarbamoyl)-3-(trifluoromethyl)-1H-pyrazol-1-yl)benzylcarbamate (27e) (0.199 g, 0.335 mmol, 68.0% yield) as a white solid; MS (ES+) 616.3 (M+Na), (ES−) 592.3 (M−1).

Step-4: Preparation of 1-(3-(aminomethyl)phenyl)-N-(3-(phenyl(propyl)amino)phenyl)-3-(trifluoromethyl)-1H-pyrazole-5-carboxamide (27f)

To a solution of tert-butyl 3-(5-(3-(phenyl(propyl)amino) phenylcarbamoyl)-3-(trifluoromethyl)-1H-pyrazol-1-yl) benzylcarbamate (27e) (0.183 g, 0.308 mmol) in dioxane (4 mL) was added drop-wise hydrogen chloride (4M in dioxane, 4.32 mL, 17.26 mmol) and stirred at room temperature for 15 h. The reaction mixture was concentrated in vacuum to dryness and the residue obtained was purified by flash column chromatography (silica gel 25 g, eluting with methanol in chloroform from 0-100%) to furnish 1-(3-(aminomethyl)phenyl)-N-(3-(phenyl(propyl)amino)phenyl)-3-(trifluoromethyl)-1H-pyrazole-5-carboxamide (27f) (0.086 g, 0.174 mmol, 56.5% yield) as a pale yellow solid.

$^1$H NMR (300 MHz, DMSO-d$_6$) δ 10.61 (s, 1H, D$_2$O exchangeable), 7.53 (s, 2H), 7.49-7.42 (m, 2H), 7.34-7.23 (m, 4H), 7.22-7.17 (m, 2H), 7.05-6.93 (m, 3H), 6.71-6.67 (m, 1H), 3.81 (s, 2H), 3.68-3.54 (m, 2H), 1.57 (h, J=7.5 Hz, 2H), 0.88 (t, J=7.4 Hz, 3H); $^{19}$F NMR (282 MHz, DMSO-d$_6$) δ −60.73; MS (ES+) 494.3 (M+1), (ES−) 492.2 (M−1), 528.2 (M+Cl).

Scheme 28

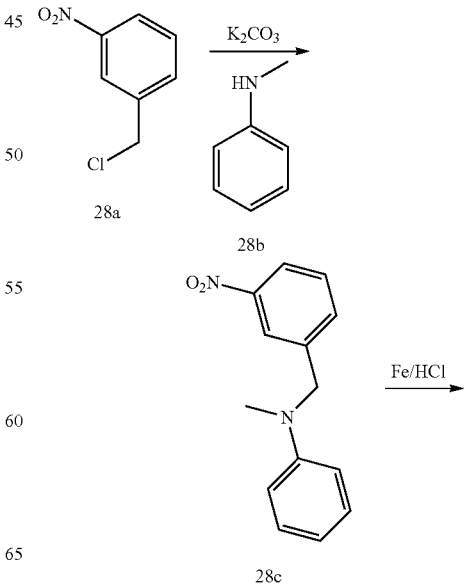

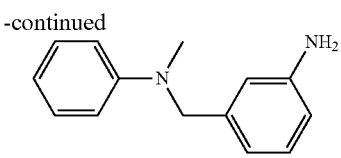

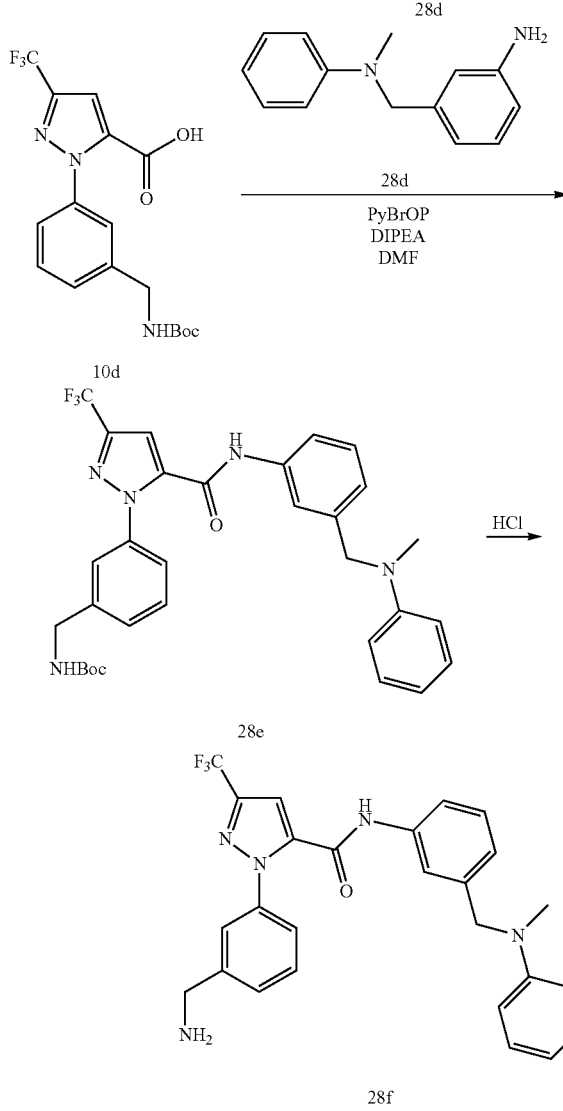

Preparation of 1-(3-(aminomethyl)phenyl)-N-(3-((methyl(phenyl)amino)methyl)phenyl)-3-(trifluoromethyl)-1H-pyrazole-5-carboxamide (28f)

Step-1: Preparation of N-methyl-N-(3-nitrobenzyl)aniline (28c)

To a solution of 1-(chloromethyl)-3-nitrobenzene (28a) (4 g, 23.31 mmol) in DMF (50 mL) was added N-methylaniline (28b) (2.53 mL, 23.31 mmol) followed by potassium carbonate (20.94 g, 152 mmol). The reaction mixture stirred at room temperature for 20 h, poured into water (200 mL) and extracted with ethyl acetate (2×50 mL). The organic layers were combined washed with water (100 mL), brine (50 mL), dried, filtered and concentrated in vacuum to furnish crude product. The crude was purified by flash column chromatography (silica gel 40 gm eluting with 0-100% ethyl acetate in hexane) to furnish N-methyl-N-(3-nitrobenzyl)aniline (28c) which was pure enough to be used for next step; MS (ES+) 243.2 (M+1).

Step-2: Preparation of N-(3-aminobenzyl)-N-methylaniline (28d)

To a stirred solution of N-methyl-N-(3-nitrobenzyl)aniline (28c) (1.5 g, 6.19 mmol) in acetic acid (20 mL) was added iron powder (1.729 g, 31.0 mmol), heated to 60° C. and stirred for 30 minutes. The reaction was quenched by adding water (100 mL) and filtered. The filtrate was extracted with ethyl acetate (2×100 mL). The ethyl acetate layers were combined, washed with water (2×100 mL), brine (50 mL) dried and concentrated in vacuum. The residue obtained was purified by flash column chromatography to afford N-(3-aminobenzyl)-N-methylaniline (28d) (533 mg, 2.51 mmol, 40.6% yield); $^1$H NMR (300 MHz, DMSO-$d_6$) δ 7.19-7.06 (m, 2H), 7.02-6.92 (m, 1H), 6.73-6.64 (m, 2H), 6.58 (tt, J=7.2, 1.0 Hz, 1H), 6.49-6.36 (m, 3H), 5.46 (s, 2H, $D_2O$ exchangeable), 4.39 (s, 2H), 2.98 (s, 3H); MS (ES+) 213.2 (M+1).

Step-3: Preparation of tert-butyl 3-(5-((3-((methyl(phenyl)amino)methyl)phenyl)carbamoyl)-3-(trifluoromethyl)-1H-pyrazol-1-yl)benzylcarbamate (28e)

To a solution of 1-(3-((tert-butoxycarbonylamino)methyl)phenyl)-3-(trifluoromethyl)-1H-pyrazole-5-carboxylic acid (10d) (193 mg, 0.5 mmol) in N,N-dimethylformamide (3 mL) was added N-ethyl-N-isopropylpropan-2-amine (0.697 mL, 4.00 mmol), N-ethyl-N-isopropylpropan-2-amine (0.697 mL, 4.00 mmol) and Bromo-tris-pyrrolidino phosphoniumhexafluorophosphate (PyBroP, 256 mg, 0.55 mmol) at room temperature. The reaction mixture was stirred at 25° C. for 16 h, diluted with water (20 mL) and extracted with ethyl acetate (2×50 mL). The organic layers were combined dried over anhydrous MgSO$_4$, filtered, concentrated under reduced pressure to dryness. The residue obtained was purified by flash column chromatography (silica gel 12 g, eluting with hexanes in ethyl acetate/hexanes 0-100%) to furnish tert-butyl 3-(5-((3-((methyl(phenyl)amino)methyl)phenyl)carbamoyl)-3-(trifluoromethyl)-1H-pyrazol-1-yl)benzylcarbamate (28e) (110 mg, 0.190 mmol, 37.9% yield) as colorless sticky material; $^1$H NMR (300 MHz, DMSO-$d_6$) δ 10.71 (s, 1H, $D_2O$ exchangeable), 7.59-7.45 (m, 4H), 7.45-7.38 (m, 2H), 7.34 (d, J=7.7 Hz, 2H), 7.27 (t, J=7.9 Hz, 1H), 7.20-7.07 (m, 2H), 6.97 (d, J=7.7 Hz, 1H), 6.69 (d, J=8.1 Hz, 2H), 6.60 (t, J=7.2 Hz, 1H), 4.52 (s, 2H), 4.19 (d, J=6.2 Hz, 2H), 3.01 (s, 3H), 1.37 (s, 9H); MS (ES+) 580.4 (M+1), 602.4 (M+23), (ES−) 578.4 (M−1).

Step-4: Preparation of 1-(3-(aminomethyl)phenyl)-N-(3-((methyl(phenyl)amino)methyl)phenyl)-3-(trifluoromethyl)-1H-pyrazole-5-carboxamide (28f)

To a stirred solution of tert-butyl 3-(5-((3-((methyl(phenyl)amino)methyl)phenyl)carbamoyl)-3-(trifluoromethyl)-1H-pyrazol-1-yl)benzylcarbamate (28e) (100 mg, 0.173 mmol) in methanol (10 mL) was added HCl (0.575 mL, 6.90 mmol) and stirred at room temperature overnight. The reaction was heated to reflux for 30 mins and concentrated in vacuum to dryness. The residue was dried in vacuum overnight, suspended in ether (25 mL), heated for 30 mins and stirred at room temperature overnight. The solid separated was collected by filtration dried to give 1-(3-(aminomethyl)phenyl)-N-(3-((methyl(phenyl)amino)methyl)phenyl)-3-(trifluoromethyl)-1H-pyrazole-5-carboxamide hydrochloride (28f) (75 mg, 0.145 mmol, 84% yield).

<sup>1</sup>H NMR (300 MHz, DMSO-d<sub>6</sub>) δ 10.79 (s, 1H), 8.38 (s, 3H), 7.72 (s, 1H), 7.66 (s, 1H), 7.61 (d, J=7.5 Hz, 1H), 7.58-7.54 (m, 1H), 7.54-7.47 (m, 2H), 7.28 (t, J=7.8 Hz, 1H), 7.16 (t, J=7.7 Hz, 2H), 7.00 (d, J=7.5 Hz, 1H), 6.70 (d, J=25.7 Hz, 3H), 4.54 (s, 2H), 4.13 (d, J=5.7 Hz, 3H), 3.02 (s, 3H); MS (ES+) 480.3 (M+1); (ES−) 478.2 (M−1), 514.2 (M+35).

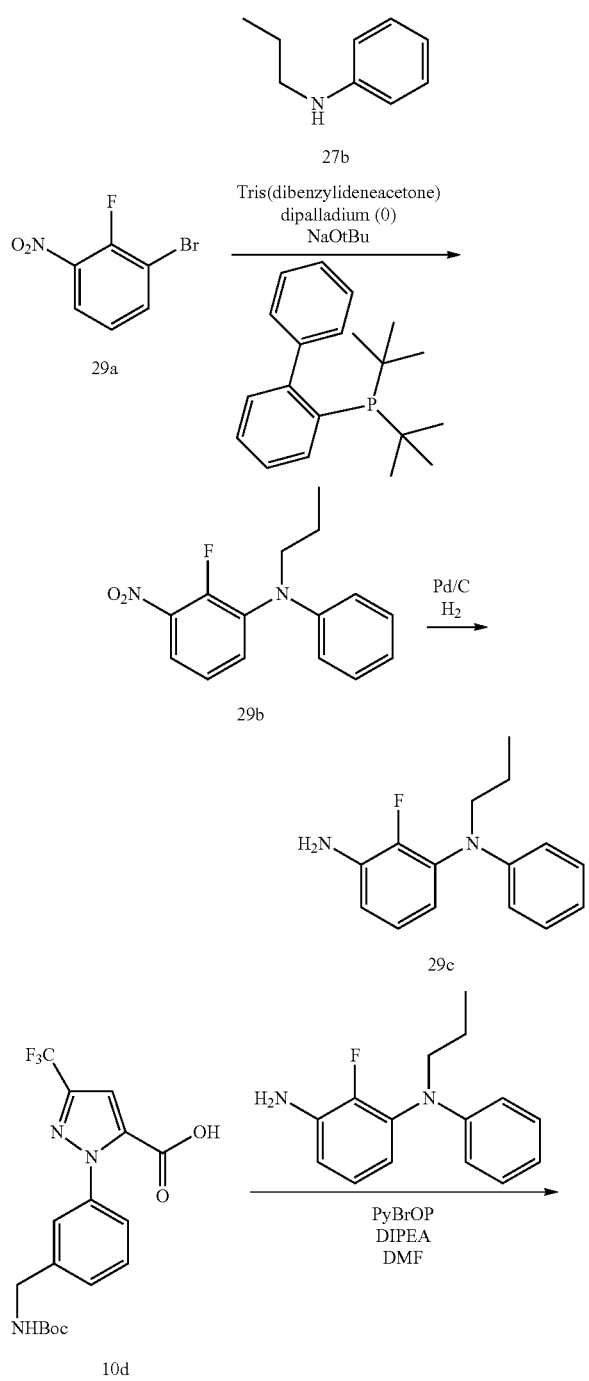

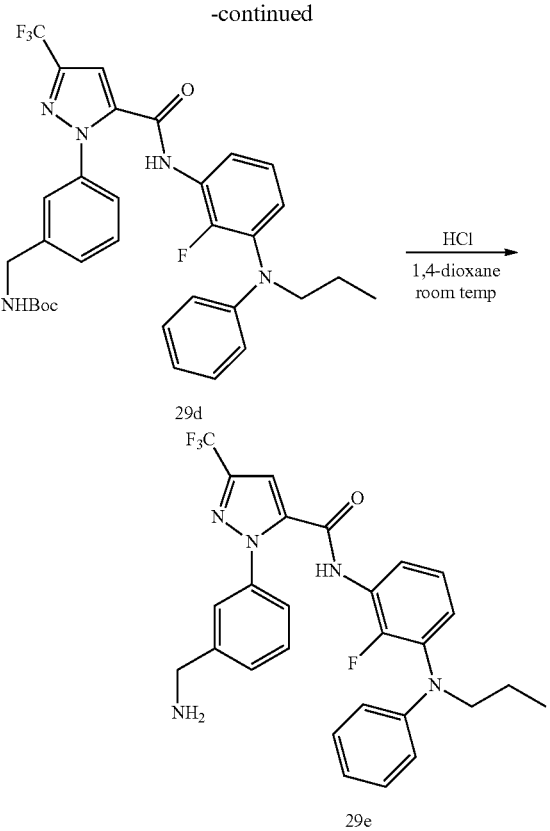

Preparation of 1-(3-(aminomethyl)phenyl)-N-(2-fluoro-3-(phenyl(propyl)amino)phenyl)-3-(trifluoromethyl)-1H-pyrazole-5-carboxamide (29e)

Step-1: Preparation of 2-fluoro-3-nitro-N-phenyl-N-propylaniline (29b)

To a solution of 1-bromo-2-fluoro-3-nitrobenzene (29a) (3 g, 13.64 mmol) and N-propylaniline (27b) (2.213 g, 16.36 mmol) in toluene (80 mL) was added sodium 2-methylpropan-2-olate (1.048 g, 10.91 mmol), biphenyl-2-yldi-tert-butylphosphine (0.407 g, 1.364 mmol) and Tris(dibenzylideneacetone)dipalladium (0) (0.375 g, 0.409 mmol). The reaction mixture was stirred at 110° C. for 16 h under a positive flow of nitrogen. Reaction was quenched with water (75 mL), extracted with ethyl acetate (2×100 mL). The combined organics were dried over MgSO<sub>4</sub>, filtered, evaporated to dryness. The residue was purified by flash column chromatography (silica gel 80 g, eluting with ethyl acetate in hexanes from 0 to 100%) to afford 2-fluoro-3-nitro-N-phenyl-N-propylaniline (29b) (3.451 g, 12.58 mmol, 92% yield) as a brown-yellow oil; which was pure enough to be taken to next step; MS (ES+) 275.2 (M+1).

Step-2: Preparation of 2-fluoro-N<sub>1</sub>-phenyl-N<sub>1</sub>-propylbenzene-1,3-diamine (29c)

To a solution of 2-fluoro-3-nitro-N-phenyl-N-propylaniline (29b) (3.4 g, 12.40 mmol) in methanol (30 mL) was added palladium (10% Pd on carbon, 0.264 g, 2.479 mmol). The mixture was hydrogenated for 2.5 h, filtered through a pad of Celite and concentrated to dryness. The residue was purified by flash column chromatography (silica gel 80 g, eluting with ethyl acetate in hexanes from 0 to 100%) to afford 2-fluoro-N₁-phenyl-N₁-propylbenzene-1,3-diamine (29c) (0.295 g, 1.207 mmol, 9.74% yield) as a brown oil; MS (ES+) 245.2 (M+1); (ES−) 243.2 (M−1).

Step-3: Preparation of tert-butyl 3-(5-(2-fluoro-3-(phenyl(propyl)amino)phenylcarbamoyl)-3-(trifluoromethyl)-1H-pyrazol-1-yl)benzylcarbamate (29d)

To a solution of 1-(3-(((tert-butoxycarbonylamino)methyl)phenyl)-3-(trifluoromethyl)-1H-pyrazole-5-carboxylic acid (10d) (0.190 g, 0.493 mmol) in N,N-dimethylformamide (2.98 mL, 38.5 mmol) was added 2-fluoro-N₁-phenyl-N₁-propylbenzene-1,3-diamine (29c) (0.145 g, 0.592 mmol), N-ethyl-N-isopropylpropan-2-amine (0.687 mL, 3.94 mmol) and Bromo-tris-pyrrolidino phosphoniumhexafluorophosphate (PyBroP, 0.253 g, 0.542 mmol) at room temperature. The resulting reaction mixture was stirred at 25° C. for 17 h. Excess DMF was pumped-off under reduced pressure. The reaction mixture was extracted with ethyl acetate (50 mL, 20 mL). The organic layers were combined dried over anhydrous MgSO₄, filtered, concentrated under reduced pressure to dryness. The residue was purified by flash column chromatography (silica gel 120 g, eluting with hexanes in ethyl acetate/hexanes from 0-100%) to furnish tert-butyl 3-(5-(2-fluoro-3-(phenyl(propyl)amino)phenylcarbamoyl)-3-(trifluoromethyl)-1H-pyrazol-1-yl)benzylcarbamate (29d) (0.182 g, 0.298 mmol, 60.3% yield) as a white solid.

¹H NMR (300 MHz, DMSO-d₆) δ 10.54 (s, 1H, D₂O exchangeable), 7.57 (s, 1H), 7.53-7.31 (m, 4H), 7.28-7.15 (m, 4H), 6.94-6.83 (m, 4H), 4.18 (d, J=6.2 Hz, 2H), 3.68-3.51 (m, 2H), 1.55 (q, J=7.5 Hz, 2H), 1.37 (s, 9H), 0.87 (t, J=7.4 Hz, 3H); ¹⁹F NMR (282 MHz, DMSO-d₆) δ −60.82, −129.49; MS (ES+) 634.33 (M+Na), MS (ES−) 610.31 (M−1).

Step-4: Preparation of 1-(3-(aminomethyl)phenyl)-N-(2-fluoro-3-(phenyl(propyl)amino)phenyl)-3-(trifluoromethyl)-1H-pyrazole-5-carboxamide (29e)

To a solution of tert-butyl 3-(5-(2-fluoro-3-(phenyl(propyl)amino)phenylcarbamoyl)-3-(trifluoromethyl)-1H-pyrazol-1-yl)benzylcarbamate (29d) (0.166 g, 0.271 mmol) in dioxane (4 mL) was added drop-wise hydrogen chloride (4 N in dioxane) (3.80 mL, 15.20 mmol) and stirred at room temperature for 15 h. TLC analysis (CHCl₃/MeOH, 8/2, v/v) shows reaction was complete. Excess solvent was pumped-off under reduced pressure, the residue was purified by flash column chromatography (silica gel 25 g, eluting with methanol in chloroform 0-100%) to furnish 1-(3-(aminomethyl)phenyl)-N-(2-fluoro-3-(phenyl(propyl)amino)phenyl)-3-(trifluoromethyl)-1H-pyrazole-5-carboxamide (29e) as a pale yellow solid.

¹H NMR (300 MHz, DMSO-d₆) δ 7.57 (s, 1H), 7.52 (s, 1H), 7.48-7.40 (m, 2H), 7.37-7.30 (m, 1H), 7.29-7.16 (m, 4H), 6.95-6.82 (m, 4H), 3.79 (s, 2H), 3.65-3.51 (m, 2H), 1.54 (h, J=7.3 Hz, 2H), 0.87 (t, J=7.3 Hz, 3H); ¹⁹F NMR (282 MHz, DMSO-d₆) δ −60.75, −129.55; MS (ES+): MS (ES+) 512.3 (M+1), (ES−) 510.3 (M−1), 546.2 (M+Cl).

Scheme 30

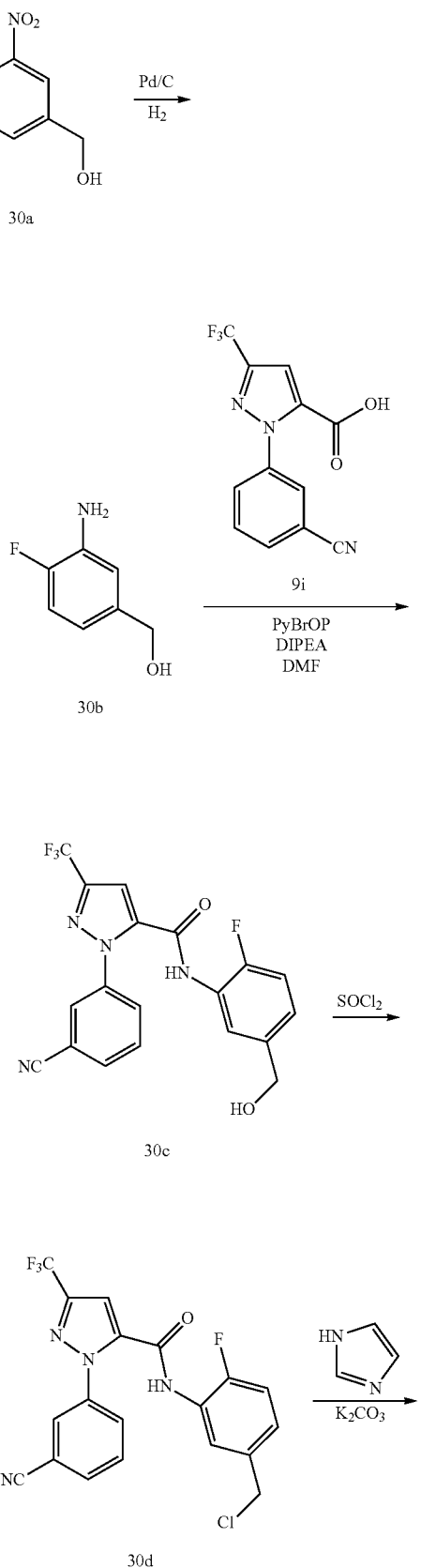

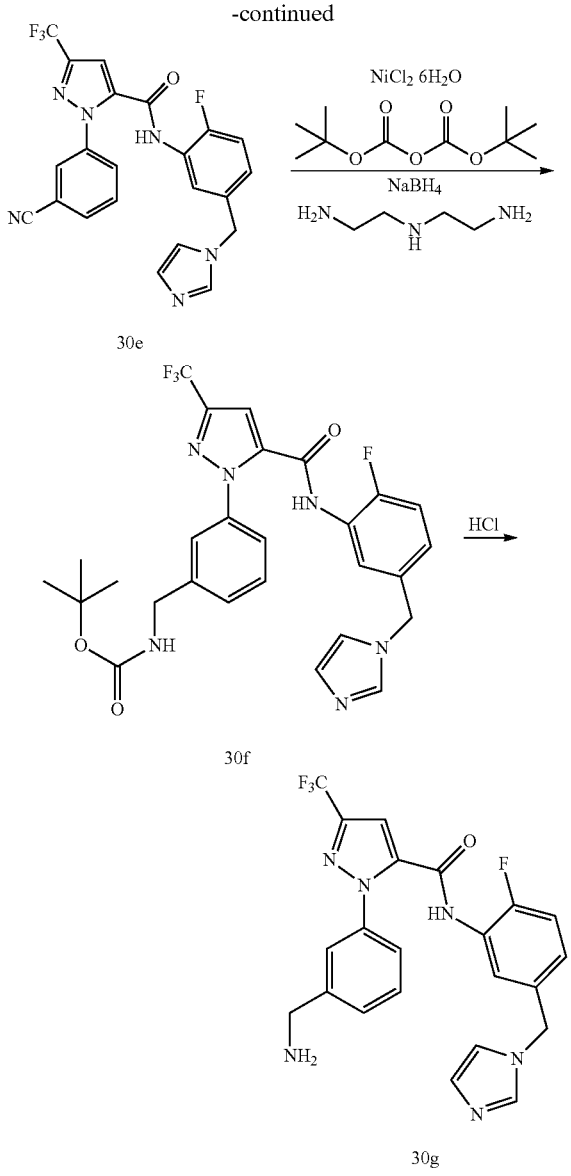

Preparation of N-(5-(((1H-imidazol-1-yl)methyl)-2-fluorophenyl)-1-(3-(aminomethyl)phenyl)-3-(trifluoromethyl)-1H-pyrazole-5-carboxamide (30g)

Step-1: Preparation of (3-amino-4-fluorophenyl)methanol (30b)

To a solution of (4-fluoro-3-nitrophenyl)methanol (30a) (3.81 g, 22.24 mmol) in methanol (30 mL) was added palladium on carbon (10%) (0.39 g, 3.67 mmol) and hydrogenated at 60 PSI for 1 h. The catalyst was removed by filtration through Celite and the filtrate was concentrated in vacuum. The residue obtained was purified by flash column chromatography [silica gel 40 g, eluting with 0-100% ethyl acetate/methanol (9:1) in hexanes] to furnish (3-amino-4-fluorophenyl)methanol (30b) (3.05 g, 21.61 mmol, 97% yield) as a white solid; $^1$H NMR (300 MHz, DMSO-d$_6$) δ 6.89 (dd, J=11.6, 8.2 Hz, 1H), 6.73 (dd, J=9.1, 2.1 Hz, 1H), 6.52-6.33 (m, 1H), 5.20-4.91 (m, 3H), 4.32 (dd, J=5.8, 0.9 Hz, 2H); $^{19}$F NMR (282 MHz, DMSO-d$_6$) δ −138.13.

Step-2: Preparation of 1-(3-cyanophenyl)-N-(2-fluoro-5-(hydroxymethyl)phenyl)-3-(trifluoromethyl)-1H-pyrazole-5-carboxamide (30c)

To a solution of 1-(3-cyanophenyl)-3-(trifluoromethyl)-1H-pyrazole-5-carboxylic acid (9i) (5.67 g, 20.15 mmol) in DMF (50 mL) was added (3-amino-4-fluorophenyl)methanol (30b) (2.37 g, 16.79 mmol), N-ethyl-N-isopropylpropan-2-amine (14.62 mL, 84 mmol) and bromo-tris-pyrrolidino phosphoniumhexafluorophosphate(PyBrop) (8.61 g, 18.47 mmol) at room temperature. The resulting reaction mixture was stirred at room temperature for 16 h under nitrogen atmosphere. The reaction mixture diluted with water (25 mL) was extracted with ethyl acetate (2×50 mL), washed with brine (25 mL), the combined organic layer was dried over anhydrous MgSO$_4$, filtered, and evaporated to dryness. The residue obtained was purified by flash column chromatography [silica gel 40 g, eluting with 0-100% ethyl acetate/methanol (9/1) in hexanes] to furnish 1-(3-cyanophenyl)-N-(2-fluoro-5-(hydroxymethyl)phenyl)-3-(trifluoromethyl)-1H-pyrazole-5-carboxamide (30c) (1.66 g, 4.11 mmol, 24.45% yield) as a white solid; $^1$HNMR (300 MHz, DMSO-d$_6$) δ 10.57 (s, 1H), 8.18-8.09 (m, 1H), 8.00 (dt, J=7.8, 1.3 Hz, 1H), 7.91 (ddd, J=8.1, 2.3, 1.1 Hz, 1H), 7.78-7.69 (m, 2H), 7.57-7.45 (m, 1H), 7.33-7.15 (m, 2H), 5.30 (t, J=5.7 Hz, 1H), 4.46 (d, J=5.7 Hz, 2H); $^{19}$F NMR (282 MHz, DMSO-d$_6$) δ −60.98, −124.32; MS (ES+) 427.2 (M+Na), (ES−) 403.2 (M−1).

Step-3: Preparation of N-(5-(chloromethyl)-2-fluorophenyl)-1-(3-cyanophenyl)-3-(trifluoromethyl)-1H-pyrazole-5-carboxamide (30d)

To a solution of 1-(3-cyanophenyl)-N-(2-fluoro-5-(hydroxymethyl)phenyl)-3-(trifluoromethyl)-1H-pyrazole-5-carboxamide (30c) (1.66 g, 4.11 mmol) in dichloromethane (30 mL) was added at 0° C. thionyl chloride (1.798 mL, 24.63 mmol) and stirred for 2.5 h. The reaction mixture was concentrated in vacuo to give a white residue. Residue was dissolved in CHCl$_3$ and treated with silica gel (2 g). The slurry obtained was purified by flash column chromatography (silica gel 40 g, eluting with ethyl acetate in hexanes from 0-50%) to furnish N-(5-(chloromethyl)-2-fluorophenyl)-1-(3-cyanophenyl)-3-(trifluoromethyl)-1H-pyrazole-5-carboxamide (30d) (1.353 g, 78% yield) as a white solid; $^1$H NMR (300 MHz, DMSO-d$_6$) δ 10.63 (s, 1H), 8.18-8.11 (m, 1H), 8.01 (dt, J=7.7, 1.3 Hz, 1H), 7.91 (ddd, J=8.1, 2.2, 1.1 Hz, 1H), 7.80-7.65 (m, 3H), 7.43-7.22 (m, 2H), 4.77 (s, 2H); $^{19}$F NMR (282 MHz, DMSO-d$_6$) δ −60.98 (d, J=6.8 Hz), −121.36.

Step-4: Preparation of N-(5-((1H-imidazol-1-yl)methyl)-2-fluorophenyl)-1-(3-cyanophenyl)-3-(trifluoromethyl)-1H-pyrazole-5-carboxamide (30e)

To a stirred solution of N-(5-(chloromethyl)-2-fluorophenyl)-1-(3-cyanophenyl)-3-(trifluoromethyl)-1H-pyrazole-5-carboxamide (30d) (0.15 g, 0.355 mmol) in N,N-dimethylformamide (4 mL) was added imidazole (0.121 g, 1.774 mmol) and potassium carbonate (0.343 g, 2.484 mmol) and stirred at room temperature for 5 days. The reaction was concentrated in vacuum and the residue obtained was dissolved in methanol and filtered through a Celite® pad. The filtrate was evaporated to dryness and the crude residue obtained was purified by flash column chromatography (silica gel 12 g, eluting with 0-100% methanol in chloroform) to furnish N-(5-((1H-imidazol-1-yl)methyl)-2-fluorophenyl)-1-(3-cyanophenyl)-3-(trifluoromethyl)-1H-pyrazole-5-carboxamide (30e) (0.107 g, 66.4% yield) as white foamy solid; $^1$H NMR (300 MHz, DMSO-d$_6$) δ 10.59 (s, 1H), 8.13 (t, J=1.8 Hz, 1H), 8.00 (dt, J=7.7, 1.3 Hz, 1H), 7.94-7.86 (m, 1H), 7.77-7.71 (m, 3H), 7.43 (d, J=7.1 Hz, 1H), 7.31 (dd, J=10.4, 8.5 Hz, 1H), 7.23-7.14 (m, 2H), 6.90 (t, J=1.1 Hz, 1H), 5.19 (s, 2H); $^{19}$F NMR (282 MHz, DMSO-d$_6$) δ −60.98 (d, J=5.4 Hz), −122.18; MS (ES+) 455.2 (M+1), (ES−) 453.2 (M−1).

Step-5: Preparation of tert-butyl 3-(5-(5-((1H-imidazol-1-yl)methyl)-2-fluorophenylcarbamoyl)-3-(trifluoromethyl)-1H-pyrazol-1-yl)benzylcarbamate (30f)

To a stirred solution of N-(5-((1H-imidazol-1-yl)methyl)-2-fluorophenyl)-1-(3-cyanophenyl)-3-(trifluoromethyl)-1H-pyrazole-5-carboxamide (30e) (0.1 g, 0.22 mmol) in anhydrous methanol (10 mL), cooled to 0° C., were added, di-tert-butyl dicarbonate [(Boc)$_2$O)](0.144 g, 0.66 mmol), nickel(II) chloride hexahydrate (10.46 mg, 0.044 mmol), sodium borohydride (0.050 g, 1.320 mmol) was then added in small portions over 5 min. The reaction mixture was quenched with N1-(2-aminoethyl)ethane-1,2-diamine (0.048 mL, 0.440 mmol) stirred at room temperature 30 minutes and concentrated in vacuum to dryness. The residue was dissolved in water/ethyl acetate (1:1 25 mL each. The organic layer was separated and concentrated in vacuum to dryness, the residue obtained was purified by flash column chromatography (silica gel 12 g, eluting with 0 to 50% ethyl acetate/hexanes) to furnish tert-butyl 3-(5-(5-((1H-imidazol-1-yl)methyl)-2-fluorophenylcarbamoyl)-3-(trifluoromethyl)-1H-pyrazol-1-yl)benzylcarbamate (30f) (0.042 g, 0.075 mmol, 34.2% yield) as a white solid; MS (ES+) 559.3 (M+1), (ES−) 557.2 (M−1).

Step-6: Preparation of N-(5-((1H-imidazol-1-yl)methyl)-2-fluorophenyl)-1-(3-(aminomethyl)phenyl)-3-(trifluoromethyl)-1H-pyrazole-5-carboxamide (30g)

To a solution of tert-butyl 3-(5-(5-((1H-imidazol-1-yl)methyl)-2-fluorophenylcarbamoyl)-3-(trifluoromethyl)-1H-pyrazol-1-yl)benzylcarbamate (30f) (0.022 g, 0.039 mmol) in dioxane (4 mL) was added hydrogen chloride (4 N in dioxane, 0.551 mL, 2.206 mmol) drop-wise and stirred at room temperature for 15 h. The reaction mixture was concentrated in vacuum to dryness and the residue obtained was purified by flash column chromatography (silica gel 12 g, eluting with 0-100% methanol in chloroform) to furnish N-(5-((1H-imidazol-1-yl)methyl)-2-fluorophenyl)-1-(3-(aminomethyl)phenyl)-3-(trifluoromethyl)-1H-pyrazole-5-carboxamide (30g) (0.016 g, 0.035 mmol, 89% yield) as a pale yellow solid; $^1$H NMR (300 MHz, DMSO-d$_6$) δ 14.58 (s, 1H, D$_2$O exchangeable), 10.77 (s, 1H, D$_2$O exchangeable), 9.21 (s, 1H), 8.37 (s, 3H, D$_2$O exchangeable), 7.75 (t, J=1.6 Hz, 1H), 7.69 (ddd, J=11.3, 3.6, 1.7 Hz, 4H), 7.64-7.54 (m, 2H), 7.54-7.48 (m, 1H), 7.40-7.33 (m, 2H), 5.42 (s, 2H), 4.12 (d, J=5.7 Hz, 2H); $^{19}$F NMR (282 MHz, DMSO-d$_6$) δ −60.82, −121.10; MS (ES+): MS (ES+) 459.3 (M+1), (ES−) 457.3 (M−1), 493.2 (M+Cl).

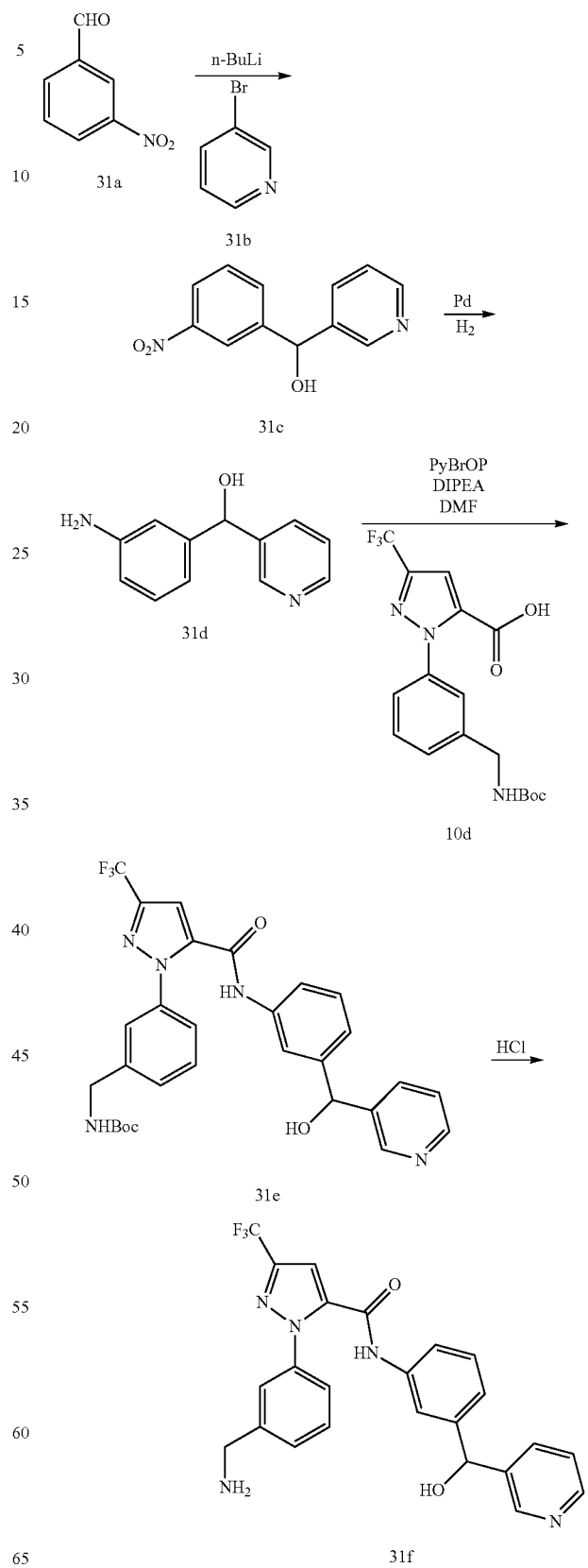

Scheme 31

Preparation of 1-(3-(aminomethyl)phenyl)-N-(3-(hydroxy(pyridin-3-yl)methyl)phenyl)-3-(trifluoromethyl)-1H-pyrazole-5-carboxamide (31f)

Step-1: Preparation of (3-Nitrophenyl)(pyridin-3-yl)methanol (31c)

To a solution of 3-bromopyridine (31b) (2.89 mL, 30.0 mmol) in ether (20 mL) at −78° C. was added dropwise n-BuLi (15.94 mL, 25.5 mmol) and stirred for 30 mins at −78° C. To the 3-lithiated pyridine was added dropwise a solution of 3-nitrobenzaldehyde (31a) (4.53 g, 30 mmol) in THF (30 mL) at −78° C. and stirred at −78° C. for 2 h and at room temperature for 2 h.

The reaction mixture was quenched with saturated ammonium chloride (50 mL). The organic layer was separated, dried, filtered and concentrated in vacuum to dryness. The residue obtained was purified by flash column chromatography (silica gel 80 g, eluting with 0-100% ethyl acetate in hexane) to afford (3-Nitrophenyl)(pyridin-3-yl)methanol (31c) (2.842 g, 12.34 mmol, 41.1% yield) as a yellow solid.

1H NMR (300 MHz, DMSO-$d_6$) δ 8.66 (d, J=2.2 Hz, 1H), 8.47 (dd, J=4.8, 1.7 Hz, 1H), 8.30 (t, J=2.0 Hz, 1H), 8.12 (ddd, J=8.2, 2.5, 1.1 Hz, 1H), 7.85 (d, J=7.5 Hz, 1H), 7.78 (dt, J=7.9, 2.0 Hz, 1H), 7.64 (t, J=7.9 Hz, 1H), 7.36 (ddd, J=7.9, 4.7, 0.9 Hz, 1H), 6.45 (d, J=4.2 Hz, 1H), 5.99 (d, J=4.0 Hz, 1H); MS (ES+) 231.1 (M+1), (ES−) 459.4 (2M−1).

Step-2: Preparation of (3-aminophenyl)(pyridin-3-yl)methanol (31d)

To a solution of (3-nitrophenyl)(pyridin-3-yl)methanol (31c) (1 g, 4.34 mmol) in ethanol (36 mL) and ethyl acetate (18 mL) was added Pd/C 10% (0.1 g) and hydrogenated at ~50 Psi for 2 h. The reaction mixture was filtered through a pad of Celite and filtrate was concentrated in vacuo. The crude product was purified by flash column chromatography [silica gel 2×12 g, eluting with chloroform/methanol (1:0 to 9:1)] to afford (3-aminophenyl)(pyridin-3-yl)methanol (31d) (209 mg, 24%) as a yellow solid; $^1$H NMR (300 MHz, DMSO-$d_6$) δ 8.55 (dt, J=2.2, 0.7 Hz, 1H), 8.40 (dd, J=4.8, 1.7 Hz, 1H), 7.68 (dddd, J=7.8, 2.3, 1.7, 0.6 Hz, 1H), 7.31 (ddd, J=7.8, 4.7, 0.9 Hz, 1H), 6.94 (t, J=7.7 Hz, 1H), 6.61-6.56 (m, 1H), 6.55-6.48 (m, 1H), 6.40 (ddd, J=8.0, 2.3, 1.1 Hz, 1H), 5.89 (d, J=3.9 Hz, 1H), 5.58 (d, J=3.9 Hz, 1H), 5.05 (s, 2H); MS (ES+) 201.1 (M+1).

Step-3: Preparation of tert-butyl 3-(5-(3-(hydroxy(pyridin-3-yl)methyl)phenylcarbamoyl)-3-(trifluoromethyl)-1H-pyrazol-1-yl)benzylcarbamate (31e)

To a solution of (3-aminophenyl)(pyridin-3-yl)methanol (31d) (80 mg, 0.400 mmol) in N,N-dimethylformamide (4 mL) was added 1-(3-((tert-butoxycarbonylamino)methyl)phenyl)-3-(trifluoromethyl)-1H-pyrazole-5-carboxylic acid (10d) (154 mg, 0.400 mmol), N-ethyl-N-isopropylpropan-2-amine (0.560 mL, 3.22 mmol) and bromotripyrrolidin-1-ylphosphonium hexafluorophosphate (V) (PyBroP, 192 mg, 0.403 mmol) at room temperature. The reaction mixture was stirred at 25° C. for 22 h and diluted with ethyl acetate (120 mL). The reaction mixture was washed with water (2×60 mL), brine (60 mL), dried over anhydrous MgSO$_4$, filtered and concentrated in vacuum to dryness. The residue obtained was purified by flash column chromatography [silica gel 12 g, eluting with chloroform/methanol (1:0 to 9:1)] to furnish tert-butyl 3-(5-(3-(hydroxy(pyridin-3-yl)methyl)phenylcarbamoyl)-3-(trifluoromethyl)-1H-pyrazol-1-yl)benzylcarbamate (31e) (153 mg, 68%) as a white solid; $^1$H NMR (300 MHz, DMSO-$d_6$) δ 10.71 (s, 1H), 8.58 (d, J=2.2 Hz, 1H), 8.43 (dd, J=4.8, 1.7 Hz, 1H), 7.70 (dt, J=8.1, 2.1 Hz, 1H), 7.64 (t, J=1.9 Hz, 1H), 7.60-7.11 (m, 10H), 6.14 (d, J=4.0 Hz, 1H), 5.76 (d, J=4.0 Hz, 1H), 4.19 (d, J=6.2 Hz, 2H), 1.36 (s, 9H); $^{19}$F NMR (282 MHz, DMSO-$d_6$) δ −60.80; MS (ES+) 568.3 (M+1).

Step-4: Preparation of 1-(3-(aminomethyl)phenyl)-N-(3-(hydroxy(pyridin-3-yl)methyl)phenyl)-3-(trifluoromethyl)-1H-pyrazole-5-carboxamide (31f)

To a stirred solution of tert-butyl 3-(5-(3-(hydroxy(pyridin-3-yl)methyl)phenylcarbamoyl)-3-(trifluoromethyl)-1H-pyrazol-1-yl)benzylcarbamate (31e) (135 mg, 0.238 mmol) in 1,4-Dioxane (12 mL) was added 4 M HCl in dioxane (2.5 mL, 10.0 mmol) and stirred at room temperature for 17 h. The reaction was diluted with hexanes and decanted. The residue was washed with hexanes, and decanted again. The insoluble product was dissolved in chloroform (40 mL)/ethanol (10.00 mL) and converted to a slurry with 2 g of silica gel. The slurry was purified by flash column chromatography [silica gel, eluting with chloroform/CMA 80 (1:0 to 1:1)] to afford 1-(3-cyanophenyl)-N-(3-(hydroxy(pyridin-4-yl)methyl)phenyl)-3-(trifluoromethyl)-1H-pyrazole-5-carboxamide (31f) (93 mg, 84%) as a white solid; $^1$H NMR (300 MHz, DMSO-$d_6$) δ 10.70 (s, 1H), 8.57 (d, J=2.2 Hz, 1H), 8.43 (dd, J=4.8, 1.7 Hz, 1H), 7.70 (dt, J=8.0, 2.0 Hz, 1H), 7.66 (t, J=1.8 Hz, 1H), 7.56 (d, J=3.2 Hz, 1H), 7.55-7.49 (m, 2H), 7.46-7.38 (m, 2H), 7.37-7.26 (m, 3H), 7.16 (d, J=7.6 Hz, 1H), 6.15 (d, J=4.0 Hz, 1H), 5.76 (s, 1H), 3.77 (s, 2H); $^{19}$F NMR (282 MHz, DMSO-$d_6$) δ −60.73; MS (ES+) 468.3 (M+1).

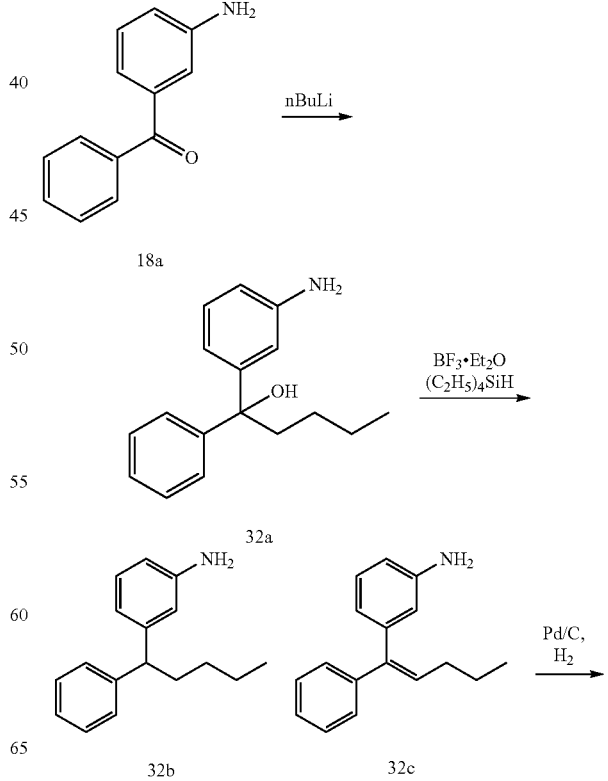

Scheme 32

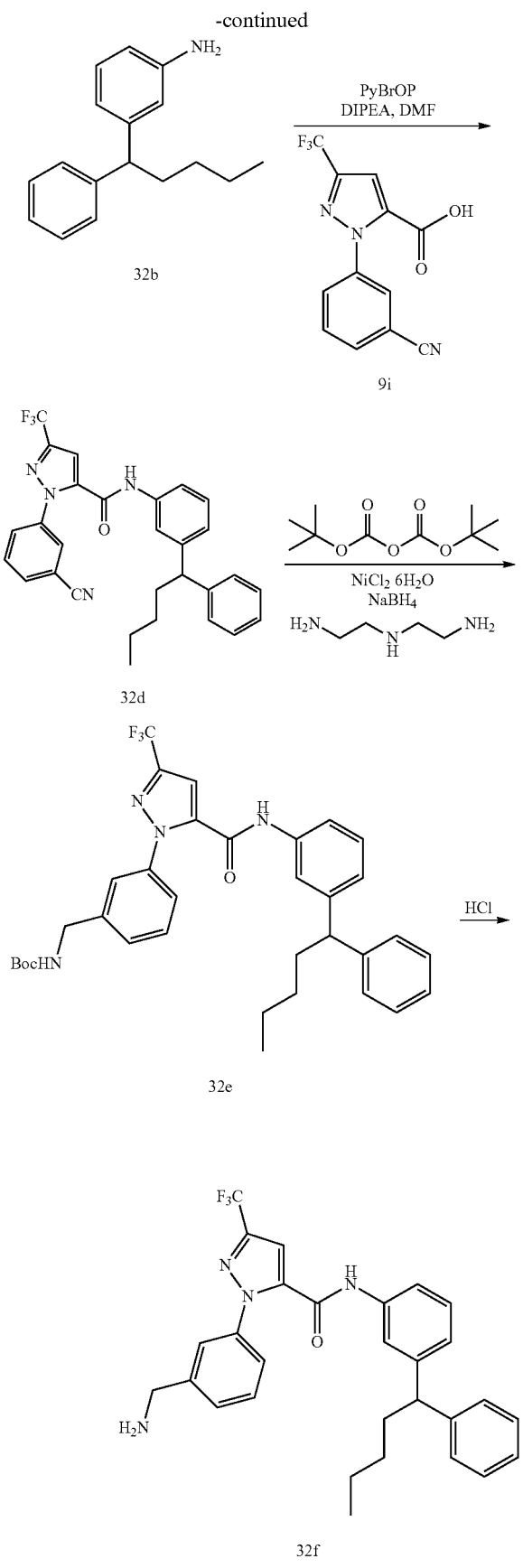

Preparation of 1-(3-(aminomethyl)phenyl)-N-(3-(1-phenylpentyl)phenyl)-3-(trifluoromethyl)-1H-pyrazole-5-carboxamide (32f)

Step 1: Preparation of 1-(3-aminophenyl)-1-phenylpentan-1-ol (32a)

To a stirred solution of (3-aminophenyl)(phenyl)methanone (18a) (2 g, 10.14 mmol) in tetrahydrofuran (40 mL) was added n-BuLi (19.01 mL, 30.4 mmol, 1.6 M in hexanes) at 0° C. The reaction was allowed to warm to room temperature overnight, quenched by adding ammonium chloride solution (50 mL) and extracted with ethyl acetate (2×150 mL). The combined organic layers were washed with water (2×50 mL), brine (50 mL), dried, filtered and concentrated in vacuum to dryness. The crude residue of 1-(3-aminophenyl)-1-phenylpentan-1-ol (32a) was used as such in next step without further purification; MS (ES−) 254.1 (M−1).

Step 2: Preparation of 3-(1-phenylpentyl)aniline (32b) and (Z)-3-(1-phenylpent-1-en-1-yl)aniline (32c)

To the solution of 1-(3-aminophenyl)-1-phenylpentan-1-ol (32a) (0.7 g, 2.74 mmol) in dichloromethane (10 mL) was added at 0° C. boron trifluoride etherate (0.695 mL, 5.48 mmol), triethylsilane (1.751 mL, 10.97 mmol) and stirred at room temperature overnight. The reaction mixture was quenched by adding ammonium chloride solution and extracted with dichloromethane (2×50 mL). The organic layers were combined washed with water, brine, dried, filtered and concentrated in vacuum. The residue was purified by flash column chromatography to afford compound containing a inseparable mixture of 3-(1-phenylpentyl)aniline (32b) and (Z)-3-(1-phenylpent-1-enyl)aniline (32c). This mixture was used as such for next step; MS (ES+) 238.2 (M+1) (32c) and 240.2 (M+1, 32b), (ES−) 239.1 (M−1, 32b).

Step 3: Preparation of pure 3-(1-phenylpentyl)aniline (32b)

To a suspension of Pd—C (10% on carbon) (10.76 mg, 0.101 mmol) in methanol (30 mL) was added a mixture of 3-(1-phenylpentyl)aniline (32b) and (Z)-3-(1-phenylpent-1-enyl)aniline (32c) (240 mg, 1.011 mmol) and hydrogenated at 60 psi for 3 h. The reaction mixture was filtered and concentrated in vacuum. The crude residue was purified by flash column chromatography to furnish 3-(1-phenylpentyl)aniline (155 mg, 0.648 mmol, 64.0% yield) as an oil; $^1$H NMR (300 MHz, DMSO-$d_6$) δ 7.25 (d, J=4.9 Hz, 4H), 7.18-7.09 (m, 1H), 6.89 (t, J=7.7 Hz, 1H), 6.49-6.41 (m, 2H), 6.34 (ddd, J=7.9, 2.2, 1.0 Hz, 1H), 4.96 (s, 2H), 3.69 (t, J=7.8 Hz, 1H), 2.00-1.86 (m, 2H), 1.37-1.22 (m, 2H), 1.22-1.05 (m, 2H), 0.82 (t, J=7.2 Hz, 3H); MS (ES+) 240.2 (M+1).

Step 4: Preparation of 1-(3-cyanophenyl)-N-(3-(1-phenylpentyl)phenyl)-3-(trifluoromethyl)-1H-pyrazole-5-carboxamide (32d)

To a solution of 1-(3-cyanophenyl)-3-(trifluoromethyl)-1H-pyrazole-5-carboxylic acid (9i) (147 mg, 0.522 mmol) in N,N-dimethylformamide (3.16 mL, 40.8 mmol) was added a solution of 3-(1-phenylpentyl)aniline (32b) (150 mg, 0.627 mmol) in N,N-dimethylformamide (3.16 mL, 40.8 mmol), Bromo-tris-pyrrolidino phosphoniumhexafluorophosphate (PyBroP, 268 mg, 0.575 mmol) at room temperature. The reaction mixture was stirred at 25° C. for 16 h and quenched with water (25 mL). The reaction mixture was extracted with ethyl acetate (100 mL, 50 mL) and the combined organic layers were dried over anhydrous MgSO$_4$, filtered, concentrated in vacuum to dryness. The residue obtained was purified by flash column chromatography (silica gel 12 g, eluting with hexanes in ethyl acetate/hexanes from 0-20%) to afford 1-(3-cyanophenyl)-N-(3-(1-phenylpentyl)phenyl)-3-(trifluoromethyl)-1H-pyrazole-5-carboxamide (32d) (155 mg, 0.308 mmol, 59.0% yield) as an oil; $^1$H NMR (300 MHz, DMSO-d$_6$) δ 10.61 (s, 1H), 8.17 (t, J=1.8 Hz, 1H), 8.00 (dt, J=7.8, 1.3 Hz, 1H), 7.90 (ddd, J=8.1, 2.3, 1.2 Hz, 1H), 7.77-7.68 (m, 2H), 7.55-7.48 (m, 2H), 7.32-7.22 (m, 5H), 7.21-7.13 (m, 1H), 7.12-7.06 (m, 1H), 3.88 (t, J=7.8 Hz, 1H), 1.95 (d, J=8.0 Hz, 2H), 1.36-1.25 (m, 2H), 1.16 (d, J=7.1 Hz, 2H), 0.82 (t, J=7.2 Hz, 3H); MS (ES+) 525.3, (ES−) 501.2 (M−1).

Step 5: Preparation of tert-butyl 3-(5-((3-(1-phenylpentyl)phenyl)carbamoyl)-3-(trifluoromethyl)-1H-pyrazol-1-yl)benzylcarbamate (32e)

To a stirred solution of 1-(3-cyanophenyl)-N-(3-(1-phenylpentyl)phenyl)-3-(trifluoromethyl)-1H-pyrazole-5-carboxamide (32d) (137 mg, 0.273 mmol) in anhydrous methanol (20 mL), cooled to 0° C., were added di-tert-butyl dicarbonate (178 mg, 0.818 mmol), nickel(II) chloride (12.96 mg, 0.055 mmol) and portion wise sodium borohydride (61.9 mg, 1.636 mmol) over a period of 5 mins. The reaction mixture was stirred for 36 min at room temperature, quenched with N1-(2-aminoethyl)ethane-1,2-diamine (0.059 mL, 0.545 mmol).

The mixture was allowed to stir for 30 minutes and concentrated in vaccum to dryness. To the residue was added water (25 mL) and with ethyl acetate (2×25 mL). The organic layer was combined dried, filtered and concentrated in vacuum to dryness. The residue obtained was purified by flash column chromatography [(silica gel 12 g, eluting with ethyl acetate/hexanes from 0 to 50%)] to furnish tert-butyl 3-(5-(3-(1-phenylpentyl)phenylcarbamoyl)-3-(trifluoromethyl)-1H-pyrazol-1-yl)benzylcarbamate (32e) (75 mg, 45.3% yield) as a white solid; $^1$H NMR (300 MHz, DMSO-d$_6$) δ 10.65 (s, 1H), 7.56 (s, 1H), 7.49 (d, J=2.2 Hz, 3H), 7.45-7.38 (m, 2H), 7.35 (d, J=7.6 Hz, 2H), 7.31-7.21 (m, 5H), 7.15 (dt, J=8.6, 4.0 Hz, 1H), 7.08 (d, J=7.7 Hz, 1H), 4.19 (d, J=6.2 Hz, 2H), 3.87 (t, J=7.8 Hz, 1H), 1.98 (d, J=8.3 Hz, 2H), 1.36 (s, 9H), 1.28 (d, J=7.2 Hz, 2H), 1.22-1.10 (m, 2H), 0.82 (t, J=7.2 Hz, 3H); MS (ES+) 629.3 (M+Na), (ES−) 605.2 (M−1), 641.3 (M+Cl).

Step 6: Preparation of 1-(3-(aminomethyl)phenyl)-N-(3-(1-phenylpentyl)phenyl)-3-(trifluoromethyl)-1H-pyrazole-5-carboxamide (32f)

To a stirred solution of tert-butyl 3-(5-(3-(1-phenylpentyl) phenylcarbamoyl)-3-(trifluoromethyl)-1H-pyrazol-1-yl) benzylcarbamate (32e)(0.065 g, 0.107 mmol) in methanol (5 mL) was added 4 M HCl in dioxane (0.357 mL, 4.29 mmol) and heated to reflux for 30 minutes.

The reaction was cooled to room temperature and concentrated in vacuum to dryness. To the residue was added methanol (50 mL) and concentrated in vacuum to dryness. The residue was triturated with ether (25 mL) and the solid separated was collected by filtration, dried in vacuum to afford 1-(3-(aminomethyl)phenyl)-N-(3-(1-phenylpentyl) phenyl)-3-(trifluoromethyl)-1H-pyrazole-5-carboxamide (32f) (60 mg) as a colorless solid; $^1$H NMR (300 MHz, DMSO-d$_6$) δ 10.71 (s, 1H, D$_2$O exchangeable), 8.31 (s, 3H, D$_2$O exchangeable), 7.71 (d, J=1.9 Hz, 1H), 7.66 (s, 1H), 7.62-7.57 (m, 1H), 7.56-7.48 (m, 4H), 7.32-7.20 (m, 5H), 7.20-7.13 (m, 1H), 7.10 (d, J=7.8 Hz, 1H), 4.13 (s, 2H), 3.87 (t, J=7.8 Hz, 1H), 1.98 (d, J=7.5 Hz, 2H), 1.29 (p, J=7.3 Hz, 2H), 1.16 (d, J=7.7 Hz, 2H), 0.82 (t, J=7.2 Hz, 3H); MS (ES+) 507.3 (M+1), 508.3 (M+2), (ES−) 505.2 (M−1), 541.2 (M+35).

Scheme 33

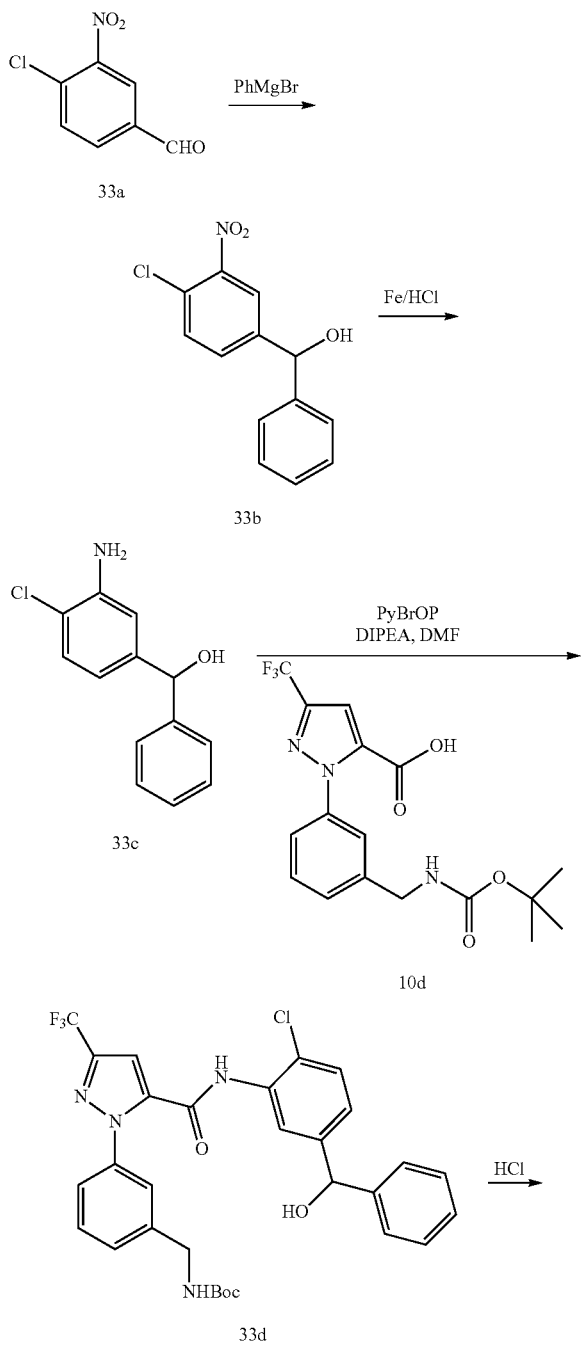

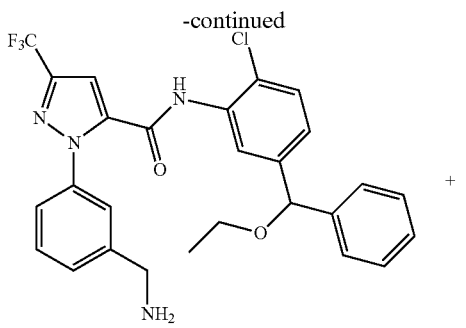

33e

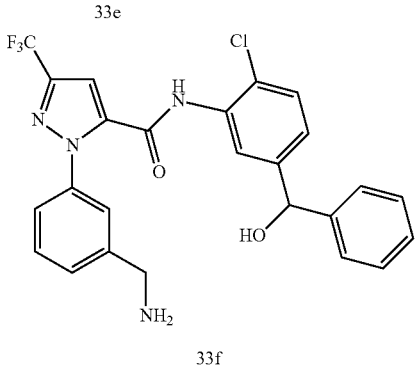

33f

Preparation of 1-(3-(aminomethyl)phenyl)-N-(2-chloro-5-(ethoxy(phenyl)methyl)phenyl)-3-(trifluoromethyl)-1H-pyrazole-5-carboxamide (33e) and 1-(3-(aminomethyl)phenyl)-N-(2-chloro-5-(hydroxy(phenyl)methyl)phenyl)-3-(trifluoromethyl)-1H-pyrazole-5-carboxamide (33f)

Step-1: Preparation of (4-chloro-3-nitrophenyl)(phenyl)methanol (33b)

To a solution of 4-chloro-3-nitrobenzaldehyde (33a) (1 g, 5.39 mmol) in tetrahydrofuran (20 mL) cooled to 0° C. was added phenylmagnesium bromide (8.08 mL, 8.08 mmol, 1 M solution in THF) dropwise over a period of 2 mins. The reaction mixture was allowed to warm to room temperature for 14 h, quenched with saturated ammonium chloride (50 mL) and extracted with ethyl acetate (100 mL, 50 mL). The combined extracts were washed with brine (50 mL), dried over $MgSO_4$, filtered and concentrated in vacuum to dryness. The residue obtained was purified by flash column chromatography (silica gel 40 g, eluting with hexanes/ethyl acetate 0-100%) to afford pure (4-chloro-3-nitrophenyl)(phenyl)methanol (33b) (653 mg, 46.0% yield) as a yellow semisolid; $^1$H NMR (300 MHz, DMSO-$d_6$) δ 8.09 (d, J=1.8 Hz, 1H), 7.72 (d, J=8.3 Hz, 1H), 7.67 (dd, J=8.4, 1.9 Hz, 1H), 7.45-7.38 (m, 2H), 7.38-7.29 (m, 2H), 7.28-7.21 (m, 1H), 6.31 (d, J=4.0 Hz, 1H), 5.84 (d, J=4.0 Hz, 1H); MS (ES+) 286.1 (M+23), 262.1 (M−1), 308.1 (M+35).

Step-2: Preparation of (3-amino-4-chlorophenyl)(phenyl)methanol (33c)

To a stirred solution of (4-chloro-3-nitrophenyl)(phenyl)methanol (33b) (600 mg, 2.276 mmol) in acetic Acid (10 mL) was added iron powder (762 mg, 13.65 mmol) and heated at 60° C. for 3 h. The reaction mixture was diluted with ethanol (100 mL) and filtered through celite. The filtrate was concentrated in vacuum and purified by flash column chromatography (silica gel, 12 g, eluting with 0-1005 CMA 80 in chloroform) to afford (3-amino-4-chlorophenyl)(phenyl)methanol (33c) (383 mg, 1.639 mmol, 72.0% yield) as an oil; $^1$H NMR (300 MHz, DMSO-$d_6$) δ 7.37-7.25 (m, 4H), 7.23-7.16 (m, 1H), 7.07 (d, J=8.2 Hz, 1H), 6.82 (d, J=2.0 Hz, 1H), 6.53 (dd, J=8.3, 2.1 Hz, 1H), 5.82 (s, 1H, $D_2O$ exchangeable), 5.53 (s, 1H), 5.29 (s, 2H, $D_2O$ exchangeable); MS (ES+) 234.1 (M+1), 236.1 (M+3).

Step-3: Preparation of tert-butyl 3-(5-(2-chloro-5-(hydroxy(phenyl)methyl)phenylcarbamoyl)-3-(trifluoromethyl)-1H-pyrazol-1-yl)benzylcarbamate (33d)

To a solution of 1-(3-((tert-butoxycarbonylamino)methyl)phenyl)-3-(trifluoromethyl)-1H-pyrazole-5-carboxylic acid (10d) (0.193 g, 0.5 mmol) in N,N-dimethylformamide (3.02 mL, 39.0 mmol) was added 3(3-amino-4-chlorophenyl)(phenyl)methanol (33c) (0.140 g, 0.6 mmol), N-ethyl-N-isopropylpropan-2-amine (0.697 mL, 4.0 mmol), Bromo-tris-pyrrolidino phosphoniumhexafluorophosphate (PyBroP) (0.256 g, 0.55 mmol) and at room temperature for 16 h. The reaction mixture was diluted with water (50 mL) and extracted with ethyl acetate (100 mL and 50 mL). The organic layers were combined dried over anhydrous $MgSO_4$, filtered, and concentrated under reduced pressure to dryness. The residue was purified by flash column chromatography (silica gel 12 g, eluting with hexanes in ethyl acetate/ hexanes from 0-100%) to afford tert-butyl 3-(5-(2-chloro-5-(hydroxy(phenyl)methyl)phenylcarbamoyl)-3-(trifluoromethyl)-1H-pyrazol-1-yl)benzylcarbamate (33d) (0.059 g, 19.63% yield) as an oil. MS (ES−) 599.2, 601.2 (M−1).

Step-4: Preparation of 1-(3-(aminomethyl)phenyl)-N-(2-chloro-5-(ethoxy(phenyl)methyl)phenyl)-3-(trifluoromethyl)-1H-pyrazole-5-carboxamide (33e) and 1-(3-(aminomethyl)phenyl)-N-(2-chloro-5-(hydroxy(phenyl)methyl)phenyl)-3-(trifluoromethyl)-1H-pyrazole-5-carboxamide (33f)

To a stirred solution of tert-butyl 3-(5-(2-chloro-5-(hydroxy(phenyl)methyl)phenylcarbamoyl)-3-(trifluoromethyl)-1H-pyrazol-1-yl)benzylcarbamate (33d) (0.053 g, 0.088 mmol) in ethanol (5 mL) was added conc. HCl (0.294 mL, 3.53 mmol) and stirred overnight at room temperature overnight. The reaction was heated at reflux for 2 h and concentrated in vacuum to remove excess hydrochloric acid. The residue was dissolved in ethanol and adsorbed on silica gel. The silica gel slurry was purified by flash column chromatography (eluting with methanol in chloroform 0 to 20%) to afford:

1. 1-(3-(aminomethyl)phenyl)-N-(2-chloro-5-(ethoxy(phenyl)methyl)phenyl)-3-(trifluoromethyl)-1H-pyrazole-5-carboxamide (33e) (7 mg, 15.01%) as a white solid; $^1$H NMR (300 MHz, DMSO-$d_6$) δ 10.52 (s, 1H, $D_2O$ exchangeable), 7.53 (t, J=8.9 Hz, 4H), 7.49-7.40 (m, 3H), 7.34 (t, J=4.5 Hz, 6H), 7.30-7.23 (m, 2H), 5.47 (s, 1H), 3.78 (s, 2H), 3.42 (q, J=7.1 Hz, 2H), 1.16 (t, J=7.0 Hz, 3H); MS (ES+) 529.2 (M), 531.2 (M+2); (ES−) 529.1 (M), 527.1 (M−2).
2. 1-(3-(aminomethyl)phenyl)-N-(2-chloro-5-(hydroxy(phenyl)methyl)phenyl)-3-(trifluoromethyl)-1H-pyrazole-5-carboxamide (33f) (8 mg, 18.11% yield) as a white solid; $^1$H NMR (300 MHz, DMSO-$d_6$) δ 10.19 (d, J=190.4 Hz, 1H, $D_2O$ exchangeable), 7.55 (d, J=7.6 Hz, 3H), 7.49-7.40 (m, 3H), 7.39-7.16 (m, 9H), 6.08 (d, J=4.2 Hz, 1H, D₂O exchangeable), 5.70 (s, 1H), 3.80 (s, 2H); MS (ES+) 501.1 (M), 503.1 (M+2); (ES−) 499.1 (M−1).
Scheme 34
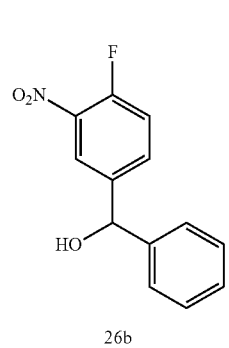
26b
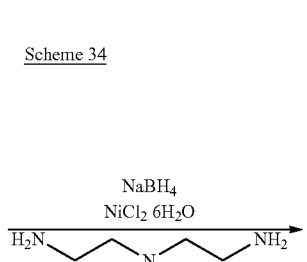
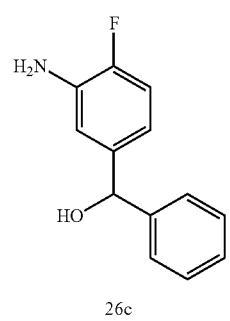
26c
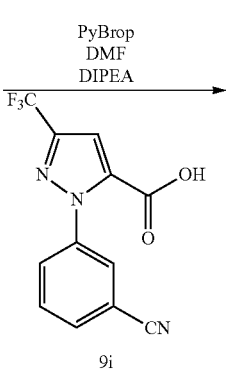
9i
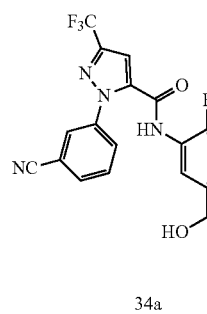
34a
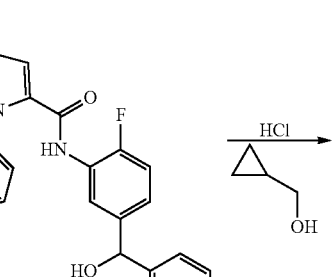
34b
-continued
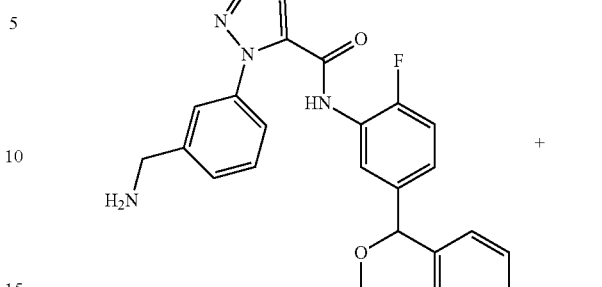
34c
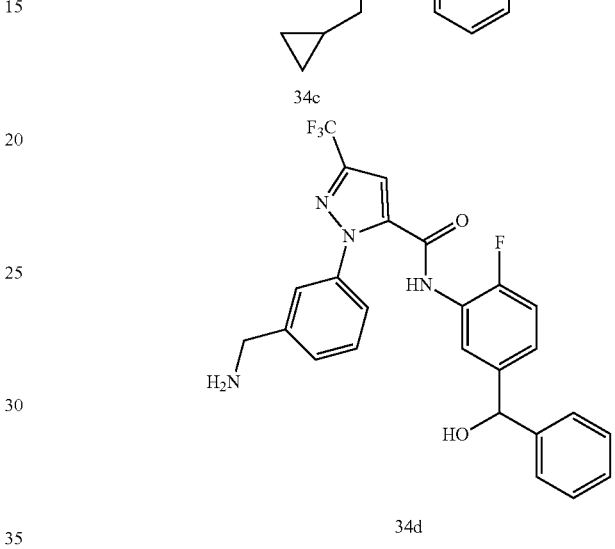
34d
Alternative method
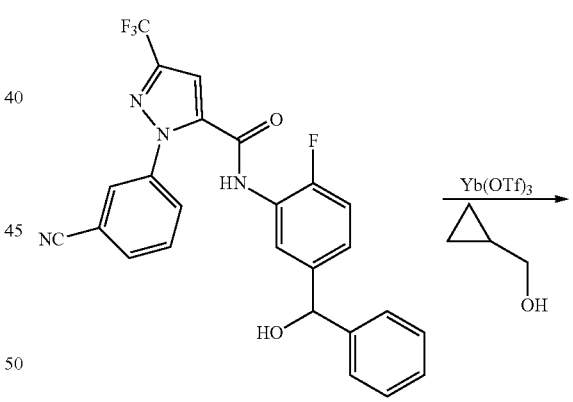
34a
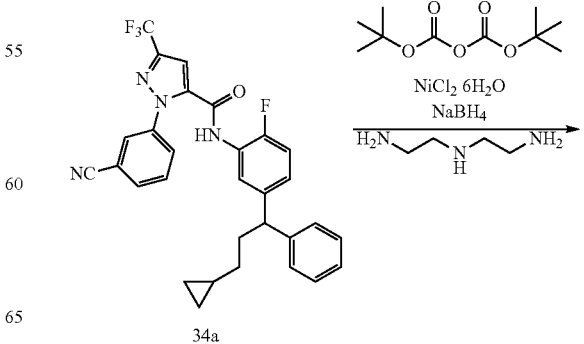
34a

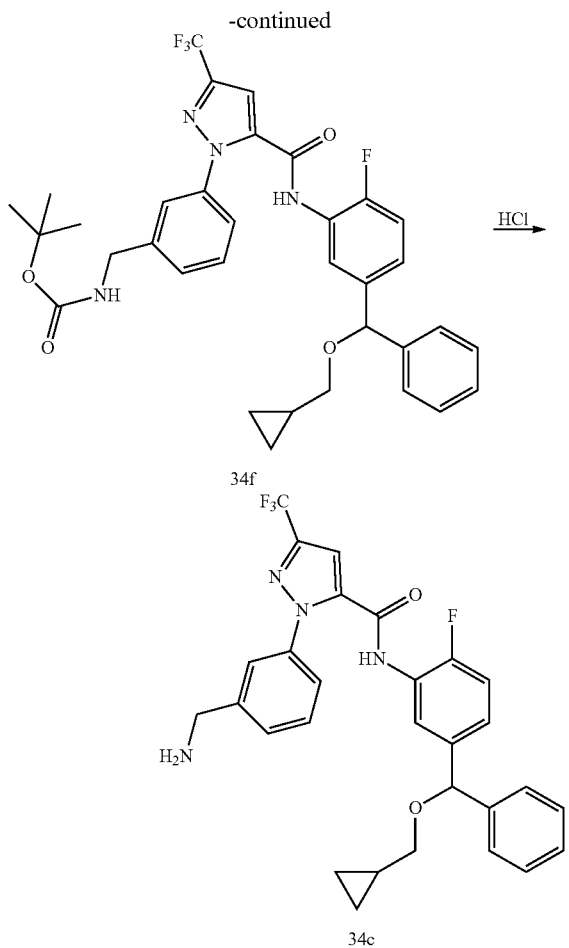

34f

34c

Preparation of 1-(3-(aminomethyl)phenyl)-N-(5-((cyclopropylmethoxy)(phenyl)methyl)-2-fluorophenyl)-3-(trifluoromethyl)-1H-pyrazole-5-carboxamide (34c) and 1-(3-(aminomethyl)phenyl)-N-(2-fluoro-5-(hydroxy(phenyl)methyl)phenyl)-3-(trifluoromethyl)-1H-pyrazole-5-carboxamide (34d)

Step 1: Preparation of (3-Amino-4-fluorophenyl)(phenyl)methanol (26c)

To a stirred solution of (4-fluoro-3-nitrophenyl)(phenyl)methanol (26b) (1.077 g, 4.36 10 mmol) in anhydrous methanol (20 mL), cooled to 0° C., was added nickel(II) chloride hexahydrate (0.259 g, 1.089 mmol) followed by sodium borohydride (0.989 g, 26.1 mmol) portionwise over a 30 mins period. The reaction mixture was stirred for 15 min at room temperature. The reaction mixture was quenched with N1-(2-aminoethyl)ethane-1,2-diamine (0.941 mL, 8.71 mmol) stirred for 30 minutes and concentrated in vacuum to dryness. The residue was dissolved in ethyl acetate (25 mL), washed with water (25 mL), brine (25 mL), dried, filtered and concentrated in vacuum. The residue obtained was purified by flash column chromatography (silica gel 12 g, eluting with ethyl acetate/hexanes from 0 to 50%)] to furnish (3-Amino-4-fluorophenyl)(phenyl)methanol (26c) (0.813 g, 86% yield) as an oil; $^1$H NMR (300 MHz, DMSO-$d_6$) δ 7.36-7.25 (m, 4H), 7.22-7.14 (m, 1H), 6.87 (dd, J=11.5, 8.2 Hz, 1H), 6.76 (dd, J=8.9, 2.2 Hz, 1H), 6.50 (ddd, J=8.2, 4.5, 2.2 Hz, 1H), 5.76 (d, J=3.9 Hz, 1H), 5.52 (d, J=3.9 Hz, 1H), 5.06 (s, 2H); 19F NMR (282 MHz, DMSO-$d_6$) δ -137.80--137.95 (m); MS (ES+) 218 (M+1); (ES-) 216 (M-1).

Step 2: Preparation of 1-(3-cyanophenyl)-N-(2-fluoro-5-(hydroxy(phenyl)methyl)phenyl)-3-(trifluoromethyl)-1H-pyrazole-5-carboxamide (34a)

In a 100 mL single-necked flask containing 1-(3-cyanophenyl)-3-(trifluoromethyl)-1H-pyrazole-5-carboxylic acid (9i) (1 g, 3.56 mmol) in N,N-dimethylformamide (21.48 mL) was added (3-amino-4-fluorophenyl)(phenyl)methanol (26c) (0.773 g, 3.56 mmol), bromo-tris-pyrrolidino phosphoniumhexafluorophosphate(PyBrop) (1.658 g, 3.56 mmol) and N-ethyl-N-isopropylpropan-2-amine (3.10 mL, 17.78 mmol) successively under a positive flow of nitrogen at room temperature. The resulting reaction mixture was stirred at room temperature for 16 h and quenched with water (100 mL). The reaction was extracted with ethyl acetate (2×100 mL) and the combined organic layers were washed with brine (50 mL), dried over anhydrous MgSO$_4$, filtered, and evaporated to dryness. The residue was purified by flash column chromatography [silica gel 40 g, eluting with ethyl acetate in hexanes from 0-100%] to furnish (34a) (0.763 g, 45% yield) as a white solid; $^1$H NMR (300 MHz, DMSO-$d_6$) δ 10.55 (s, 1H, D$_2$O exchangeable), 8.12 (t, J=1.8 Hz, 1H), 8.00 (dt, J=7.7, 1.3 Hz, 1H), 7.94-7.86 (m, 1H), 7.76-7.68 (m, 2H), 7.52 (dd, J=7.6, 2.1 Hz, 1H), 7.37 (d, J=1.9 Hz, 1H), 7.35-7.31 (m, 2H), 7.30 (d, J=1.0 Hz, 1H), 7.27 (q, J=1.9 Hz, 1H), 7.25 (d, J=1.6 Hz, 1H), 7.24-7.17 (m, 1H), 6.01 (d, J=3.9 Hz, 1H, D$_2$O exchangeable), 5.69 (d, J=4.0 Hz, 1H); $^{19}$F NMR (282 MHz, DMSO-$d_6$) δ -60.99, -123.32; MS (ES$^+$): MS (ES+) 503.1 (M+Na), (ES-) 479.1 (M-1), 959.3 (2M-1).

Step 3: Preparation of tert-butyl 3-(5-(2-fluoro-5-(hydroxy(phenyl)methyl)phenylcarbamoyl)-3-(trifluoromethyl)-1H-pyrazol-1-yl)benzylcarbamate (34b)

To a stirred solution of 1-(3-cyanophenyl)-N-(2-fluoro-5-(hydroxy(phenyl)methyl)phenyl)-3-(trifluoromethyl)-1H-pyrazole-5-carboxamide (34a) (0.730 g, 1.520 mmol) in anhydrous methanol (15 mL), cooled to 0° C. were added di-tert-butyl dicarbonate [(Boc)$_2$O)] (0.995 g, 4.56 mmol), nickel(II) chloride hexahydrate (0.072 g, 0.304 mmol) and sodium borohydride (0.345 g, 9.12 mmol) in small portions over 5 mins. The reaction mixture was stirred for 20 min at room temperature, quenched with N1-(2-aminoethyl)ethane-1,2-diamine (0.328 mL, 3.04 mmol) and stirred for 30 mins. The reaction mixture was concentrated in vacuum and the residue was treated with water (50 mL) and extracted with ethyl acetate (2×25 mL). Organic layers were combined, dried over MgSO$_4$ and excess solvents were pumped-off under reduced pressure. The residue was purified by flash column chromatography [(silica gel 25 g, eluting with ethyl acetate/hexanes from 0 to 50%)] to furnish tert-butyl 3-(5-(2-fluoro-5-(hydroxy(phenyl)methyl)phenylcarbamoyl)-3-(trifluoromethyl)-1H-pyrazol-1-yl)benzylcarbamate (34b) (0.458 g, 52% yield) as a greasy solid; $^1$H NMR (300 MHz, DMSO-$d_6$) δ 10.56 (s, 1H, D$_2$O exchangeable), 7.57 (m, 2H), 7.51 (t, J=6.2 Hz, 1H), 7.46-7.39 (m, 2H), 7.38-7.31 (m, 4H), 7.30 (d, J=0.9 Hz, 1H), 7.29-7.17 (m, 3H), 6.00 (d, J=4.0 Hz, 1H, D$_2$O exchangeable), 5.69 (d, J=3.9 Hz, 1H), 4.19 (d, J=6.2 Hz, 2H), 1.38 (s, 9H); $^{19}$F NMR (282 MHz, DMSO-d$_6$) δ −60.82, −123.71; MS (ES+) 607.2 (M+Na), (ES−) 583.2 (M−1).

Step 4: Preparation of 1-(3-(aminomethyl)phenyl)-N-(5-((cyclopropylmethoxy)(phenyl)methyl)-2-fluorophenyl)-3-(trifluoromethyl)-1H-pyrazole-5-carboxamide (34c) and 1-(3-(aminomethyl)phenyl)-N-(2-fluoro-5-(hydroxy(phenyl)methyl)phenyl)-3-(trifluoromethyl)-1H-pyrazole-5-carboxamide (34d)

To a solution of tert-butyl 3-(5-(2-fluoro-5-(hydroxy(phenyl)methyl)phenylcarbamoyl)-3-(trifluoromethyl)-1H-pyrazol-1-yl)benzylcarbamate (34b) (0.277 g, 0.474 mmol) in 1,4-dioxane (10 mL) was added at room temperature dropwise hydrogen chloride (4 M in 1,4-dioxane, 6.87 mL, 27.5 mmol) and stirred at room temperature for 14 h. The reaction mixture was diluted with 75 mL of hexanes and the resulting greasy solid was collected by filtration. The residue (greasy solid) was re-dissolved in chloroform (40 mL)/cyclopropylmethanol (1.880 mL, 22.75 mmol) added 3 g of silica gel and stirred at room temperature for 30 min. The mixture was concentrated in vacuum to dryness and the slurry obtained was purified by flash column chromatography [(silica gel 25 g, eluting with CMA80 in chloroform from 0-100%)] to afford:
1. 1-(3-(aminomethyl)phenyl)-N-(2-fluoro-5-(hydroxy(phenyl)methyl)phenyl)-3-(trifluoromethyl)-1H-pyrazole-5-carboxamide (34d) (19 mg, 8% yield); $^1$H NMR (300 MHz, DMSO-d$_6$) δ 10.55 (s, 1H), 7.58 (d, J=4.2 Hz, 2H), 7.52 (s, 1H), 7.47-7.40 (m, 2H), 7.38-7.17 (m, 8H), 6.01 (d, J=4.0 Hz, 1H), 5.68 (d, J=2.1 Hz, 1H), 3.78 (s, 2H); $^1$HNMR (300 MHz, DMSO-d$_6$ D$_2$O) δ 7.62-7.54 (m, 2H), 7.53-7.42 (m, 3H), 7.38-7.18 (m, 8H), 5.68 (s, 1H), 3.77 (s, 2H); $^{19}$F NMR (282 MHz, DMSO-d$_6$) δ −60.75, −123.78; MS (ES$^+$): MS (ES+) 485.2 (M+1), 969.4 (2M+1), (ES−) 483.2 (M−1), 519.2 (M+Cl), 967.3 (2M−1).
2. Second column purification of impure fractions [(silica gel 12 g, eluting with methanol in chloroform from 0 to 100%)] afforded 1-(3-(aminomethyl)phenyl)-N-(5-((cyclopropylmethoxy)(phenyl)methyl)-2-fluorophenyl)-3-(trifluoromethyl)-1H-pyrazole-5-carboxamide (34c) (39 mg, 15% yield) as a white solid; $^1$H NMR (300 MHz, DMSO-d$_6$) δ 10.59 (s, 1H), 7.58 (d, J=5.1 Hz, 2H), 7.52 (d, J=2.0 Hz, 1H), 7.47-7.38 (m, 2H), 7.33 (d, J=4.4 Hz, 5H), 7.28-7.20 (m, 3H), 5.47 (s, 1H), 3.77 (s, 2H), 3.22 (d, J=6.7 Hz, 2H), 1.05 (m, 1H), 0.54-0.38 (m, 2H), 0.21-0.09 (m, 2H); $^{19}$F NMR (282 MHz, DMSO-d$_6$) δ −60.75, −122.96; MS (ES$^+$): MS (ES+) 539.3 (M+1), (ES−) 537.2 (M−1); Analysis calculated for C$_{29}$H$_{26}$F$_4$N$_4$O$_2$: C, 64.68; H, 4.87; N, 10.40; found: C, 64.58; H, 5.07; N, 10.19.

Alternative Method for Preparation of Racemic 1-(3-(aminomethyl)phenyl)-N-(5-((cyclopropylmethoxy)(phenyl)methyl)-2-fluorophenyl)-3-(trifluoromethyl)-1H-pyrazole-5-carboxamide (34c)

Step-1: Preparation of 1-(3-Cyanophenyl)-N-(5-((cyclopropylmethoxy)(phenyl)methyl)-2-fluorophenyl)-3-(trifluoromethyl)-1H-pyrazole-5-carboxamide (34e)

To a solution of 1-(3-cyanophenyl)-N-(2-fluoro-5-(hydroxy(phenyl)methyl)phenyl)-3-(trifluoromethyl)-1H-pyrazole-5-carboxamide (34a) (1.1 g, 2.290 mmol) in cyclopropylmethanol (14.80 mL, 206 mmol) was added Ytterbium (III) trifluoromethanesulfonate (1.065 g, 1.717 mmol) and heated with stirring at 80° C. for 16 h. Excess solvent was pumped-off, and residue was dried under reduced pressure. The residue obtained was purified by flash column chromatography [silica gel 40 g, eluting with ethyl acetate in hexanes from 0-100%] to furnish 1-(3-cyanophenyl)-N-(5-((cyclopropylmethoxy)(phenyl)methyl)-2-fluorophenyl)-3-(trifluoromethyl)-1H-pyrazole-5-carboxamide (34e) (1.014 g, 83% yield) as an off-white solid; $^1$H NMR (300 MHz, DMSO-d$_6$) δ 10.57 (s, 1H, D$_2$O exchangeable), 8.18-8.09 (m, 1H), 8.00 (dt, J=7.7, 1.3 Hz, 1H), 7.95-7.86 (m, 1H), 7.79-7.67 (m, 2H), 7.59-7.48 (m, 1H), 7.38-7.31 (m, 4H), 7.29-7.20 (m, 3H), 5.48 (s, 1H), 3.22 (d, J=6.7 Hz, 2H), 1.04 (dddd, J=12.2, 8.1, 4.0, 2.6 Hz, 1H), 0.53-0.39 (m, 2H), 0.14 (tq, J=4.6, 2.1 Hz, 2H); $^{19}$F NMR (282 MHz, DMSO-d$_6$) δ −60.99, −122.52; MS (ES$^+$): MS (ES+) 557.2 (M+Na), MS (ES−) 533.1 (M−1); IR (KBr, cm$^{-1}$): 2235 cm$^{-1}$ (C—N stretching).

Step-2: Preparation of tert-butyl 3-(5-(5-((cyclopropylmethoxy)(phenyl)methyl)-2-fluorophenylcarbamoyl)-3-(trifluoromethyl)-1H-pyrazol-1-yl)benzylcarbamate (34f)

To a stirred solution of 1-(3-cyanophenyl)-N-(5-((cyclopropylmethoxy)(phenyl)methyl)-2-fluorophenyl)-3-(trifluoromethyl)-1H-pyrazole-5-carboxamide (34e) (0.996 g, 1.863 mmol) in anhydrous methanol (10 mL) cooled to 0° C., were added di-tert-butyl dicarbonate [(Boc)$_2$O)](1.220 g, 5.59 mmol), sodium borohydride (0.423 g, 11.18 mmol) in small portions over a period of 5 min. The reaction was exothermic and effervescent. The reaction mixture was stirred for 15 min and concentrated in vacuum. The residue was treated with water (15 mL), and extracted with ethyl acetate (2×25 mL). Organic layers were combined dried over anhydrous MgSO$_4$, filtered, and excess solvents were pumped-off under reduced pressure. The residue was purified by flash column chromatography [(silica gel 25 g, eluting with ethyl acetate/hexanes from 0 to 50%)] to furnish tert-butyl 3-(5-(5-((cyclopropylmethoxy)(phenyl)methyl)-2-fluorophenylcarbamoyl)-3-(trifluoromethyl)-1H-pyrazol-1-yl)benzylcarbamate (34f) (445 mg, 37% yield) as a white solid; $^1$H NMR (300 MHz, DMSO-d$_6$) δ 10.59 (s, 1H, D$_2$O exchangeable), 7.58 (d, J=5.9 Hz, 2H), 7.51 (t, J=6.2 Hz, 1H), 7.45-7.30 (m, 7H), 7.29-7.21 (m, 3H), 5.47 (s, 1H), 4.19 (d, J=6.3 Hz, 2H), 3.22 (d, J=6.8 Hz, 2H), 1.38 (s, 9H), 1.10-0.99 (m, 1H), 0.51-0.41 (m, 2H), 0.19-0.10 (m, 2H); $^{19}$F NMR (282 MHz, DMSO-d$_6$) δ −60.83, −122.90; MS (ES$^+$): MS (ES+) 661.29 (M+Na), MS (ES−) 637.2 (M−1).

Step-3: Preparation of 1-(3-(Aminomethyl)phenyl)-N-(5-((cyclopropylmethoxy)(phenyl)methyl)-2-fluorophenyl)-3-(trifluoromethyl)-1H-pyrazole-5-carboxamide (34c)

To a solution of tert-butyl 3-(5-(5-((cyclopropylmethoxy)(phenyl)methyl)-2-fluorophenylcarbamoyl)-3-(trifluoromethyl)-1H-pyrazol-1-yl)benzylcarbamate (34f) (0.431 g, 0.675 mmol) in 1,4-Dioxane (20 mL) was added a solution of 4M hydrogen chloride in 1,4-dioxane (9.79 mL, 39.1 mmol) and stirred at room temperature for 14 h. The reaction mixture was evaporated to dryness and the residue obtained was purified by flash column chromatography [(silica gel 40 g, eluting with methanol in chloroform from 0-100%)] to furnish 1-(3-(Aminomethyl)phenyl)-N-(5-((cyclopropylmethoxy)(phenyl)methyl)-2-fluorophenyl)-3-(trifluoromethyl)-1H-pyrazole-5-carboxamide (34c) (0.209 g, 0.388 mmol, 57.5% yield) as a white solid; $^1$H NMR (300 MHz, DMSO-d$_6$) δ 10.59 (s, 1H, D$_2$O exchangeable), 7.58 (d, J=5.1 Hz, 2H), 7.52 (d, J=2.0 Hz, 1H), 7.47-7.38 (m, 2H), 7.33 (d, J=4.4 Hz, 5H), 7.28-7.20 (m, 3H), 5.47 (s, 1H), 3.77 (s, 2H), 3.22 (d, J=6.7 Hz, 2H), 1.05 (m, 1H), 0.54-0.38 (m, 2H), 0.21-0.09 (m, 2H); 19F NMR (282 MHz, DMSO-d$_6$) δ −60.75, −122.96; MS (ES+) 539.3 (M+1), (ES−) 537.2 (M−1). Analysis calculated for C$_{29}$H$_{26}$F$_4$N$_4$O$_2$: C, 64.68; H, 4.87; N, 10.40; Found: C, 64.58; H, 5.07; N, 10.19.

Scheme 35

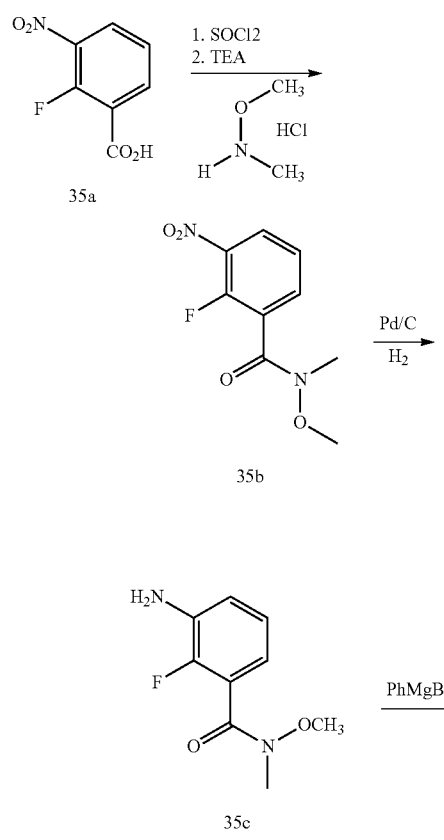

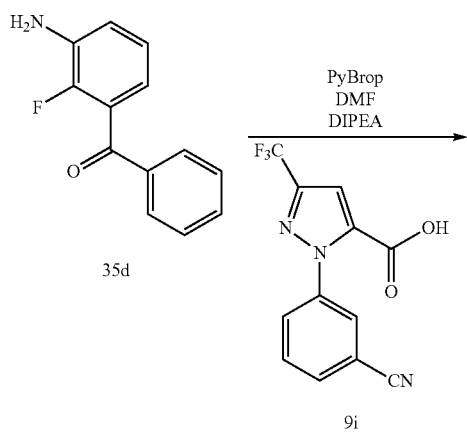

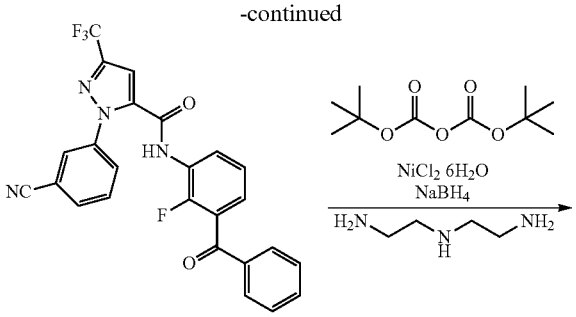

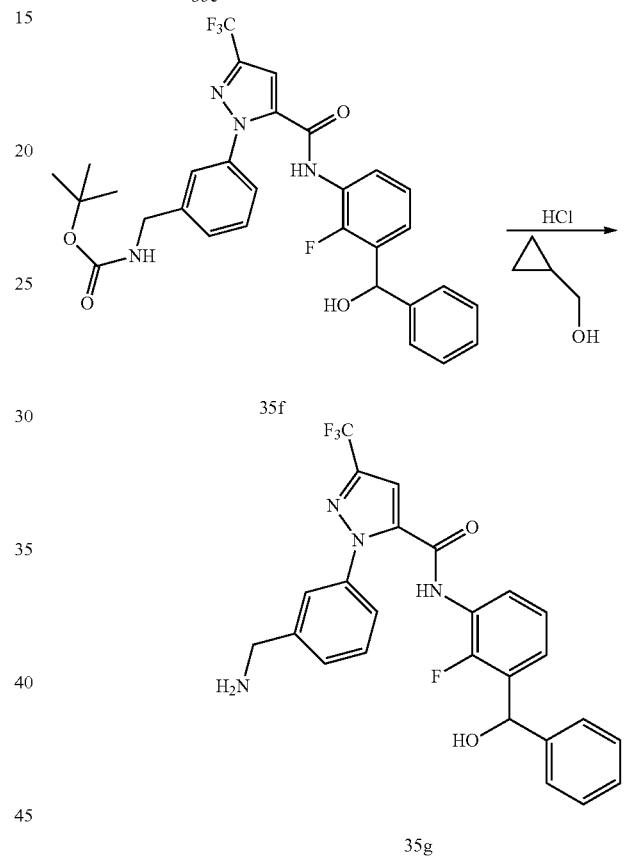

Preparation of 1-(3-(aminomethyl)phenyl)-N-(2-fluoro-3-(hydroxy(phenyl)methyl)phenyl)-3-(trifluoromethyl)-1H-pyrazole-5-carboxamide (35g)

Step-1: Preparation of 2-fluoro-N-methoxy-N-methyl-3-nitrobenzamide (35b)

To a solution of 2-fluoro-3-nitrobenzoic acid (35a) (5.0 g, 27.0 mmol) in toluene (20.0 mL) was added thionyl chloride (19.71 mL, 270 mmol), one drop of DMF and heated at reflux for 1 h. The reaction mixture was concentrated in vacuum to dryness, co-distilled with toluene (10 mL) once and dried under vacuum to remove traces of thionyl chloride. The acid chloride obtained was dissolved in dichloromethane (40 mL) and to it was added at room temperature N,O-dimethylhydroxylamine hydrochloride (3.95 g, 40.5 mmol) and triethylamine (18.82 mL, 135 mmol). The reaction mixture was stirred at room temperature overnight, washed with water (25 mL), brine (25 mL), dried, filtered and concentrated in vacuum. The residue obtained was purified by flash column chromatography (silica gel 40 g, eluting with 0-100%, ethyl acetate in hexane) to furnish 2-Fluoro-N-methoxy-N-methyl-3-nitrobenzamide (35b) (5.062 g, 82% yield) as a yellow solid; $^1$H NMR (300 MHz, DMSO-d$_6$) δ 8.25 (ddd, J=8.3, 7.4, 1.7 Hz, 1H), 7.93 (ddd, J=7.5, 5.6, 1.7 Hz, 1H), 7.54 (ddd, J=8.5, 7.7, 1.0 Hz, 1H), 3.50 (s, 3H), 3.32 (s, 3H); $^{19}$F NMR (282 MHz, DMSO-d$_6$) δ −123.00 (t, J=6.6 Hz); MS (ES+) 251.1 (M+Na).

Step-2: Preparation of methyl 3-amino-2-fluoro-N-methoxy-N-methylbenzamide (35c)

To a solution of 2-fluoro-N-methoxy-N-methyl-3-nitrobenzamide (35b) (3.792 g, 16.62 mmol) in methanol (30 mL) was added Palladium on carbon (0.8 g) and the mixture was hydrogenated at 50 psi for 4 h. The reaction mixture was filtered through Celite and the filtrate was concentrated in vacuum. The residue obtained was purified by flash column chromatography (silica gel 40 g, eluting with 0-100% ethyl acetate in hexane) to furnish methyl 3-amino-2-fluoro-N-methoxy-N-methylbenzamide (35c) (3.072 g, 15.50 mmol, 93% yield) as a light brown solid; $^1$H NMR (300 MHz, DMSO-d$_6$) δ 6.90 (t, J=7.7 Hz, 1H), 6.80 (td, J=8.3, 1.8 Hz, 1H), 6.49 (ddd, J=7.5, 5.7, 1.8 Hz, 1H), 5.30 (s, 2H), 3.62-3.43 (m, 3H), 3.22 (s, 3H); $^{19}$F NMR (282 MHz, DMSO-d$_6$) δ −138.16; MS (ES+) 221.1 (M+Na).

Step-3: Preparation of (3-amino-2-fluorophenyl)(phenyl)methanone (35d)

A solution of 3-amino-2-fluoro-N-methoxy-N-methylbenzamide (35c) (2.8 g, 14.13 mmol) in THF (60 mL) was cooled to 0° C. and treated with phenyl magnesium bromide (28.7 mL, 28.7 mmol) slowly followed by warming up to room temperature and stirring at room temperature for 14 h. Reaction was quenched with sat. ammonium chloride (120 mL) and extracted with ethyl acetate (2×100 mL). The combined extracts were dried over MgSO$_4$, filtered, evaporated under reduced pressure. The residue was purified by flash column chromatography [(silica gel 80 g, eluting with ethyl acetate in hexanes from 0 to 50%)] to furnish (3-amino-2-fluorophenyl)(phenyl)methanone (35d) (1.297 g, 43% yield) as a pale yellow oil; $^1$H NMR (300 MHz, DMSO-d$_6$) δ 7.80-7.73 (m, 2H), 7.73-7.66 (m, 1H), 7.62-7.52 (m, 2H), 7.08-6.92 (m, 2H), 6.67-6.55 (m, 1H), 5.44 (s, 2H); $^{19}$F NMR (282 MHz, DMSO-d$_6$) δ −135.94; MS (ES+): MS (ES+) 238.1 (M+Na), MS (ES−) 214.0 (M−1).

Step-4: Preparation of N-(3-benzoyl-2-fluorophenyl)-1-(3-cyanophenyl)-3-(trifluoromethyl)-1H-pyrazole-5-carboxamide (35e)

In a 100 mL single-necked flask containing a solution of 1-(3-cyanophenyl)-3-(trifluoromethyl)-1H-pyrazole-5-carboxylic acid (9i) (1.38 g, 4.91 mmol), (3-amino-2-fluorophenyl)(phenyl)methanone (35d) (1.056 g, 4.91 mmol) in N,N-dimethylformamide (30 mL) was added bromo-tris-pyrrolidino phosphoniumhexafluorophosphate(PyBrop) (2.288 g, 4.91 mmol), N-ethyl-N-isopropylpropan-2-amine (4.27 mL, 24.54 mmol) successively in a positive flow of nitrogen at room temperature. The resulting reaction mixture was stirred at room temperature for 16 h under nitrogen atmosphere. The reaction was quenched with water (100 mL) and extracted with ethyl acetate (2×100 mL). The organic layers were combined washed with brine (50 mL), dried over anhydrous MgSO$_4$, filtered, and evaporated to dryness. The residue was purified by flash column chromatography twice [silica gel 40 g, eluting with ethyl acetate in hexanes from 0-100%] to furnish N-(3-benzoyl-2-fluorophenyl)-1-(3-cyanophenyl)-3-(trifluoromethyl)-1H-pyrazole-5-carboxamide (35e) (0.287 g, 12% yield) as a white solid; $^1$H NMR (300 MHz, DMSO-d$_6$) δ 10.73 (s, 1H, D$_2$O exchangeable), 8.16 (t, J=1.8 Hz, 1H), 8.00 (dt, J=7.7, 1.3 Hz, 1H), 7.91 (ddd, J=8.2, 2.2, 1.1 Hz, 1H), 7.85 (td, J=7.4, 2.1 Hz, 1H), 7.78 (d, J=2.6 Hz, 2H), 7.76 (d, J=1.9 Hz, 2H), 7.73 (s, 1H), 7.58 (dd, J=8.3, 7.0 Hz, 2H), 7.48-7.35 (m, 2H); $^1$H NMR (300 MHz, DMSO-d$_6$ D$_2$O) δ 8.13 (t, J=1.8 Hz, 1H), 8.00 (dt, J=7.7, 1.3 Hz, 1H), 7.91 (ddd, J=8.1, 2.3, 1.2 Hz, 1H), 7.84 (td, J=7.3, 2.5 Hz, 1H), 7.80-7.70 (m, 5H), 7.59 (t, J=7.7 Hz, 2H), 7.48-7.36 (m, 2H); $^{19}$F NMR (282 MHz, DMSO-d$_6$) δ −61.00, −122.24; IR (KBr, cm$^{-1}$): 2233 cm$^{-1}$ (C—N stretching); MS (ES$^+$): MS (ES+) 479.1 (M+1), 501.1 (M+Na), (ES−) 477.1 (M−1), 955.2 (M+Cl).

Step-5: Preparation of tert-butyl 3-(5-(2-fluoro-3-(hydroxy(phenyl)methyl)phenylcarbamoyl)-3-(trifluoromethyl)-1H-pyrazol-1-yl)benzylcarbamate (35f)

To a stirred solution of N-(3-benzoyl-2-fluorophenyl)-1-(3-cyanophenyl)-3-(trifluoromethyl)-1H-pyrazole-5-carboxamide (35e) (0.276 g, 0.577 mmol) in anhydrous methanol (20 mL) cooled to 0° C., were added, di-tert-butyl dicarbonate [(Boc)$_2$O)] (0.378 g, 1.731 mmol), nickel(II) chloride hexahydrate (0.027 g, 0.115 mmol), sodium borohydride (0.131 g, 3.46 mmol) was then added in small portions over a period of 5 min. The reaction mixture was stirred for 50 min at 0° C., quenched with N1-(2-aminoethyl)ethane-1,2-diamine (0.125 mL, 1.154 mmol), stirred for 30 minutes and concentrated in vacuum to dryness. The residue was treated with water (25 mL) and extracted with ethyl acetate (2×25 mL). Combined organic layers were dried over MgSO$_4$, filtered, and excess solvents were pumped-off under reduced pressure. The residue was purified by flash column chromatography [(silica gel 25 g, eluting with ethyl acetate/hexanes from 0 to 50%)] to furnish tert-butyl 3-(5-(2-fluoro-3-(hydroxy(phenyl)methyl)phenylcarbamoyl)-3-(trifluoromethyl)-1H-pyrazol-1-yl)benzylcarbamate (35f) (0.212 g, 63% yield) as a white solid; $^1$H NMR (300 MHz, DMSO-d$_6$) δ 10.54 (s, 1H, D$_2$O exchangeable), 7.58 (s, 1H), 7.54-7.46 (m, 3H), 7.46-7.38 (m, 2H), 7.38-7.30 (m, 5H), 7.26-7.15 (m, 2H), 6.08 (d, J=4.3 Hz, 1H, D$_2$O exchangeable), 5.93 (d, J=4.2 Hz, 1H), 4.18 (d, J=6.2 Hz, 2H), 1.37 (s, 9H); $^{19}$F NMR (282 MHz, DMSO-d$_6$) δ −60.83, −127.57; MS (ES$^+$): MS (ES+) 607.2 (M+Na), (ES−) 583.2 (M−1).

Step-6: Preparation of 1-(3-(aminomethyl)phenyl)-N-(2-fluoro-3-(hydroxy(phenyl)methyl)phenyl)-3-(trifluoromethyl)-1H-pyrazole-5-carboxamide (35g)

To a solution of tert-butyl 3-(5-(2-fluoro-3-(hydroxy(phenyl)methyl)phenylcarbamoyl)-3-(trifluoromethyl)-1H-pyrazol-1-yl)benzylcarbamate (35f) (0.151 g, 0.258 mmol) in 1,4-dioxane (18 mL) was added dropwise hydrogen chloride (2.78 mL, 11.11 mmol, 4 M in 1,4-dioxane) and stirred at room temperature for 14 h. Excess solvent was pumped-off under reduced pressure. The residue was dissolved in chloroform/cyclopropylmethanol (1.452 mL, 17.57 mmol) and slurried with 2 g of silica gel, then the residue was purified by flash column chromatography [(silica gel 25 g, eluting with methanol in chloroform from 0 to 100%)] to furnish BCX-6967 (0.109 g, 87% yield) as a white solid; $^1$H NMR (300 MHz, DMSO-$d_6$) δ 10.56 (s, 1H, D$_2$O exchangeable), 7.64 (s, 2H), 7.55-7.43 (m, 5H), 7.32 (d, J=6.5 Hz, 4H), 7.26-7.14 (m, 2H), 6.10 (d, J=4.2 Hz, 1H, D$_2$O exchangeable), 5.92 (d, J=3.9 Hz, 1H), 4.00 (s, 2H); $^{19}$F NMR (282 MHz, DMSO-$d_6$) δ −60.81, −127.34; MS (ES$^+$): MS (ES+) 485.2 (M+1), (ES−) 483.2 (M−1), 519.1 (M+Cl).

Scheme 36

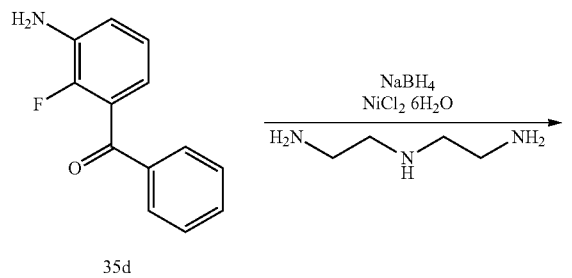

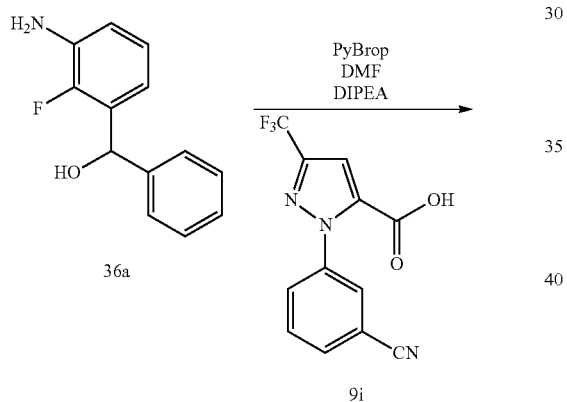

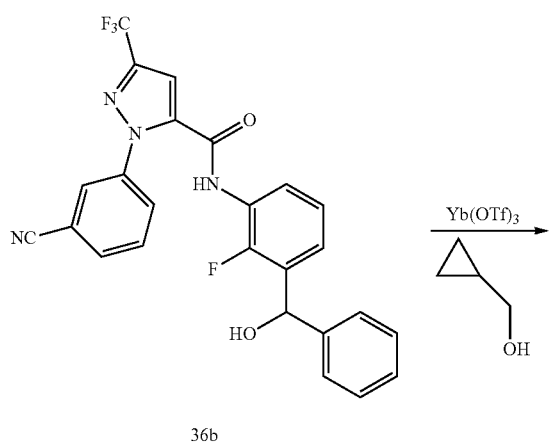

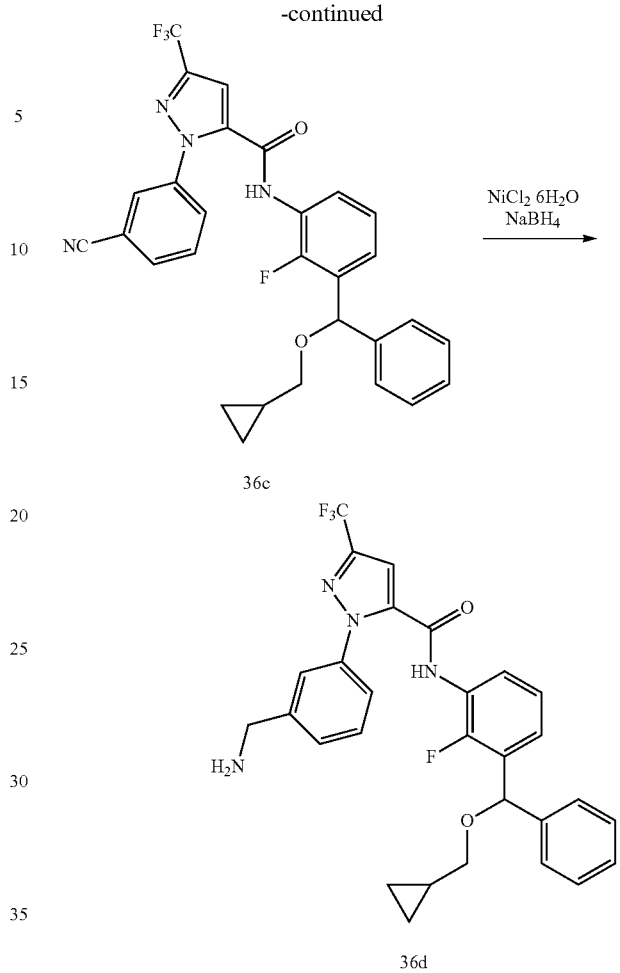

Preparation of 1-(3-(aminomethyl)phenyl)-N-(3-((cyclopropylmethoxy)(phenyl)methyl)-2-fluorophenyl)-3-(trifluoromethyl)-1H-pyrazole-5-carboxamide (36d)

Step-1: Preparation of (3-amino-2-fluorophenyl)(phenyl)methanol (36a)

To a stirred solution of (3-amino-2-fluorophenyl)(phenyl)methanone (35d) (1.25 g, 5.81 mmol) in anhydrous methanol (50 mL) cooled to 0° C. was added nickel(II) chloride (0.345 g, 1.452 mmol) and sodium borohydride (0.879 g, 23.23 mmol) in small portions over a period of 5 min. The reaction mixture was stirred for 15 min, quenched with N1-(2-aminoethyl)ethane-1,2-diamine (1.255 mL, 11.62 mmol) stirred for additional 30 mins and concentrated in vacuum to dryness. The residue obtained was treated with water (50 mL), and extracted with ethyl acetate (2×75 mL). Organic layers were combined, dried over MgSO$_4$, filtered and concentrated in vacuum to dryness. The residue obtained was purified by flash column chromatography [(silica gel 40 g, eluting with ethyl acetate in hexanes from 0 to 50%)] to furnish (3-amino-2-fluorophenyl)(phenyl)methanol (36a) (0.834 g, 66% yield) as a white solid; $^1$H NMR (300 MHz, DMSO-$d_6$) δ 7.37-7.24 (m, 4H), 7.23-7.16 (m, 1H), 6.88-6.78 (m, 1H), 6.64 (dddd, J=18.3, 9.3, 7.1, 1.8 Hz, 2H), 5.94-5.74 (m, 2H), 5.03 (s, 2H, D$_2$O exchangeable); $^{19}$F NMR (282 MHz, DMSO-d$_6$) δ −140.94; MS (ES$^+$): MS (ES+) 240.1 (M+Na), MS (ES−) 216.1 (M−1).

Step-2: Preparation of 1-(3-cyanophenyl)-N-(2-fluoro-3-(hydroxy(phenyl)methyl)phenyl)-3-(trifluoromethyl)-1H-pyrazole-5-carboxamide (36b)

In a 250 mL single-necked flask containing a solution of 1-(3-cyanophenyl)-3-(trifluoromethyl)-1H-pyrazole-5-carboxylic acid (9i) (1.263 g, 4.49 mmol), (3-amino-2-fluorophenyl)(phenyl)methanol (36a) (0.813 g, 3.74 mmol) in N,N-dimethylformamide (DMF) (22.60 mL, 292 mmol) was added bromo-tris-pyrrolidino phosphoniumhexafluorophosphate (PyBrop, 2.094 g, 4.49 mmol) and N-ethyl-N-isopropylpropan-2-amine (DIPEA) (3.26 mL, 18.71 mmol) successively in a positive flow of nitrogen at room temperature. The resulting reaction mixture was stirred at room temperature for 16 h, diluted with water (100 mL) and extracted with ethyl acetate (2×100 mL). The organic layers were combined, washed with brine (50 mL), dried over anhydrous MgSO$_4$, filtered, and evaporated to dryness. The residue obtained was purified by flash column chromatography twice [silica gel 40 g, eluting with ethyl acetate in hexanes from 0-100%] to furnish 1-(3-cyanophenyl)-N-(2-fluoro-3-(hydroxy(phenyl)methyl)phenyl)-3-(trifluoromethyl)-1H-pyrazole-5-carboxamide (36b) (1.378 g, 77% yield) as a white solid; $^1$H NMR (300 MHz, DMSO-d$_6$) δ 10.50 (s, 1H), 8.17-8.10 (m, 1H), 7.99 (dt, J=7.7, 1.3 Hz, 1H), 7.89 (ddd, J=8.2, 2.3, 1.1 Hz, 1H), 7.77-7.68 (m, 2H), 7.46 (t, J=7.1 Hz, 2H), 7.39-7.27 (m, 4H), 7.26-7.15 (m, 2H), 6.09 (d, J=4.3 Hz, 1H, D$_2$O exchangeable), 5.93 (d, J=3.7 Hz, 1H); $^{19}$F NMR (282 MHz, DMSO-d$_6$) δ −61.00, −127.24; MS (ES$^+$): MS (ES+) 503.1 (M+Na), MS (ES−) 479.1 (M−1); IR (KBr, cm$^{-1}$): 2235 cm$^{-1}$ (C—N stretching).

Step-3: Preparation of 1-(3-cyanophenyl)-N-(3-((cyclopropylmethoxy)(phenyl)methyl)-2-fluorophenyl)-3-(trifluoromethyl)-1H-pyrazole-5-carboxamide (36c)

To a solution of 1-(3-cyanophenyl)-N-(2-fluoro-3-(hydroxy(phenyl)methyl)phenyl)-3-(trifluoromethyl)-1H-pyrazole-5-carboxamide (36b) (0.193 g, 0.402 mmol) in cyclopropylmethanol (2.89 mL, 40.2 mmol) was added Ytterbium (III) trifluoromethanesulfonate (0.498 g, 0.803 mmol) and heated at 80° C. for 16 h. Excess solvent was pumped-off, diluted with chloroform (2×50 mL), and filtered through a Celite pad. The filtrate was concentrated in vacuum and the residue obtained was purified by flash column chromatography [silica gel 25 g, eluting with ethyl acetate in hexanes from 0-100%] to furnish 1-(3-cyanophenyl)-N-(3-((cyclopropylmethoxy)(phenyl)methyl)-2-fluorophenyl)-3-(trifluoromethyl)-1H-pyrazole-5-carboxamide (36c) (63 mg, 29% yield) as a pale yellow solid; $^1$HNMR (300 MHz, DMSO-d$_6$) δ 10.52 (s, 1H), 8.17-8.08 (m, 1H), 7.99 (dt, J=7.8, 1.3 Hz, 1H), 7.94-7.87 (m, 1H), 7.78-7.68 (m, 2H), 7.49 (t, J=7.5 Hz, 1H), 7.42-7.31 (m, 5H), 7.29-7.17 (m, 2H), 5.72 (s, 1H), 3.27 (d, J=6.8 Hz, 2H), 1.09-1.02 (m, 1H), 0.52-0.42 (m, 2H), 0.20-0.11 (m, 2H); $^{19}$F NMR (282 MHz, DMSO-d$_6$) δ −60.99, −126.92; MS (ES$^+$): MS (ES+) 557.16 (M+Na), (ES−) 533.22 (M−1).

Step-4: Preparation of 1-(3-(aminomethyl)phenyl)-N-(3-((cyclopropylmethoxy)(phenyl)methyl)-2-fluorophenyl)-3-(trifluoromethyl)-1H-pyrazole-5-carboxamide (36d)

To a stirred solution of 1-(3-cyanophenyl)-N-(3-((cyclopropylmethoxy)(phenyl)methyl)-2-fluorophenyl)-3-(trifluoromethyl)-1H-pyrazole-5-carboxamide (36c) (0.060 g, 0.112 mmol) in anhydrous methanol (10 mL), cooled to 0° C., were added nickel(II) chloride hexahydrate (0.027 g, 0.112 mmol) and sodium borohydride (0.025 g, 0.674 mmol) in small portions over 5 min. The reaction mixture was stirred for 15 min and concentrated in vacuum to dryness. The residue obtained was purified by flash column chromatography [(silica gel 2×12 g, eluting with methanol/chloroform from 0 to 100%)] to furnish 1-(3-(aminomethyl)phenyl)-N-(3-((cyclopropylmethoxy)(phenyl)methyl)-2-fluorophenyl)-3-(trifluoromethyl)-1H-pyrazole-5-carboxamide (36d) (24 mg, 40% yield) as a white solid; $^1$H NMR (300 MHz, DMSO-d$_6$) δ 7.58 (s, 1H), 7.55-7.49 (m, 2H), 7.46-7.40 (m, 2H), 7.40-7.30 (m, 6H), 7.30-7.18 (m, 2H), 5.72 (s, 1H), 3.78 (s, 2H), 3.27 (d, J=6.8 Hz, 2H), 1.12-0.98 (m, 1H), 0.54-0.41 (m, 2H), 0.15 (ddd, J=5.5, 4.7, 3.6 Hz, 2H); $^1$H NMR (300 MHz, DMSO-d$_6$ D$_2$O) δ 7.54 (s, 1H), 7.51-7.44 (m, 4H), 7.43-7.39 (m, 1H), 7.36 (d, J=4.5 Hz, 5H), 7.31-7.21 (m, 2H), 5.72 (s, 1H), 3.76 (s, 2H), 3.27 (d, J=6.8 Hz, 2H), 1.13-0.98 (m, 1H), 0.56-0.40 (m, 2H), 0.15 (dt, J=4.4, 2.8 Hz, 2H); $^{19}$F NMR (282 MHz, DMSO-d$_6$) δ −60.76, −127.15; MS (ES$^+$): MS (ES+) 539.2 (M+1), MS (ES−) 537.2 (M−1), 573.1 (M+Cl).

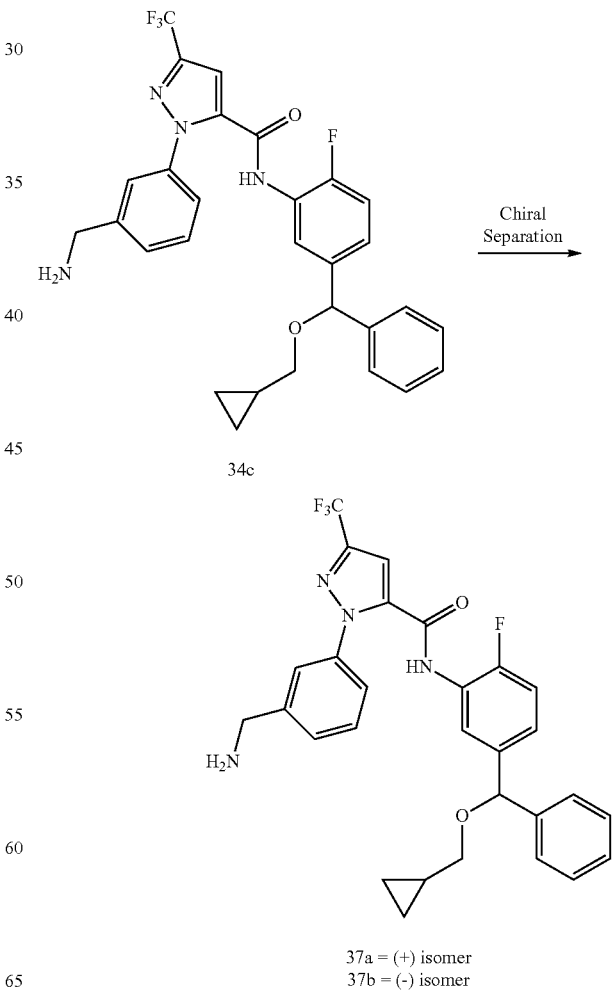

Scheme 37

34c

Chiral Separation →

37a = (+) isomer
37b = (−) isomer

221

Preparation of (+)-1-(3-(aminomethyl)phenyl)-N-(5-((cyclopropylmethoxy)(phenyl)methyl)-2-fluorophenyl)-3-(trifluoromethyl)-1H-pyrazole-5-carboxamide (37a) and (−)-1-(3-(aminomethyl)phenyl)-N-(5-((cyclopropylmethoxy)(phenyl)methyl)-2-fluorophenyl)-3-(trifluoromethyl)-1H-pyrazole-5-carboxamide (37b)

Racemic 1-(3-(aminomethyl)phenyl)-N-(5-((cyclopropylmethoxy)(phenyl)methyl)-2-fluorophenyl)-3-(trifluoromethyl)-1H-pyrazole-5-carboxamide (34c) (1.24 gms) was purified by chiral preparation HPLC using Chiral AD-H column 80/20/0.1 (Hexane/ethanol/TEA) 0.8 mL/min UV 260 nM, 20 mins run time (Temp 20° C.) to obtain:

1. (+)-1-(3-(aminomethyl)phenyl)-N-(5-((cyclopropylmethoxy)(phenyl)methyl)-2-fluorophenyl)-3-(trifluoromethyl)-1H-pyrazole-5-carboxamide (37a) (213 mgs, ee=18.32%) Rt=14.453 [40.8415%, (−)-isomer]; Rt=15.713 [59.1585% (+)-isomer]. This material was repurified by flash column chromatography (silica gel 2×12 g, eluting with 0-100% ethyl cetate/methanol (9:1) in hexanes) to furnish (45 mg) pure product; $^1$H NMR (300 MHz, DMSO-$d_6$) δ 10.58 (s, 1H, $D_2O$ exchangeable), 7.58 (d, J=7.0 Hz, 2H), 7.51 (s, 1H), 7.47-7.40 (m, 2H), 7.33 (d, J=4.3 Hz, 5H), 7.25 (dd, J=8.3, 3.8 Hz, 3H), 5.47 (s, 1H), 3.77 (s, 2H), 3.22 (d, J=6.8 Hz, 2H), 1.03 (dd, J=11.7, 5.5 Hz, 1H), 0.56-0.39 (m, 2H), 0.22-0.06 (m, 2H); $^{19}$F NMR (282 MHz, DMSO-$d_6$) δ −60.73, −122.98; MS (ES+) 539.2 (M+1), 537.2 (M−1), 573.1 (M+Cl).

2. (−)-1-(3-(aminomethyl)phenyl)-N-(5-((cyclopropylmethoxy)(phenyl)methyl)-2-fluorophenyl)-3-(trifluoromethyl)-1H-pyrazole-5-carboxamide (37b) (55 mg, ee=37.8%) Rt=14.433 [68.9002%, (−)-isomer] Rt=15.793 [31.0998%, (+)-isomer]. This material was repurified by flash column chromatography (silica gel 4 g, eluting with chloroform/methanol (1:0 to 9:1) to furnish (12.3 mg) pure product, [α]$_D$=−3.90 [CH$_3$OH, 0.615].

Scheme 38

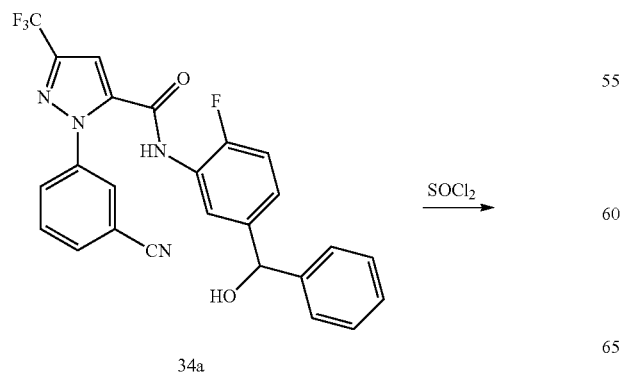

34a

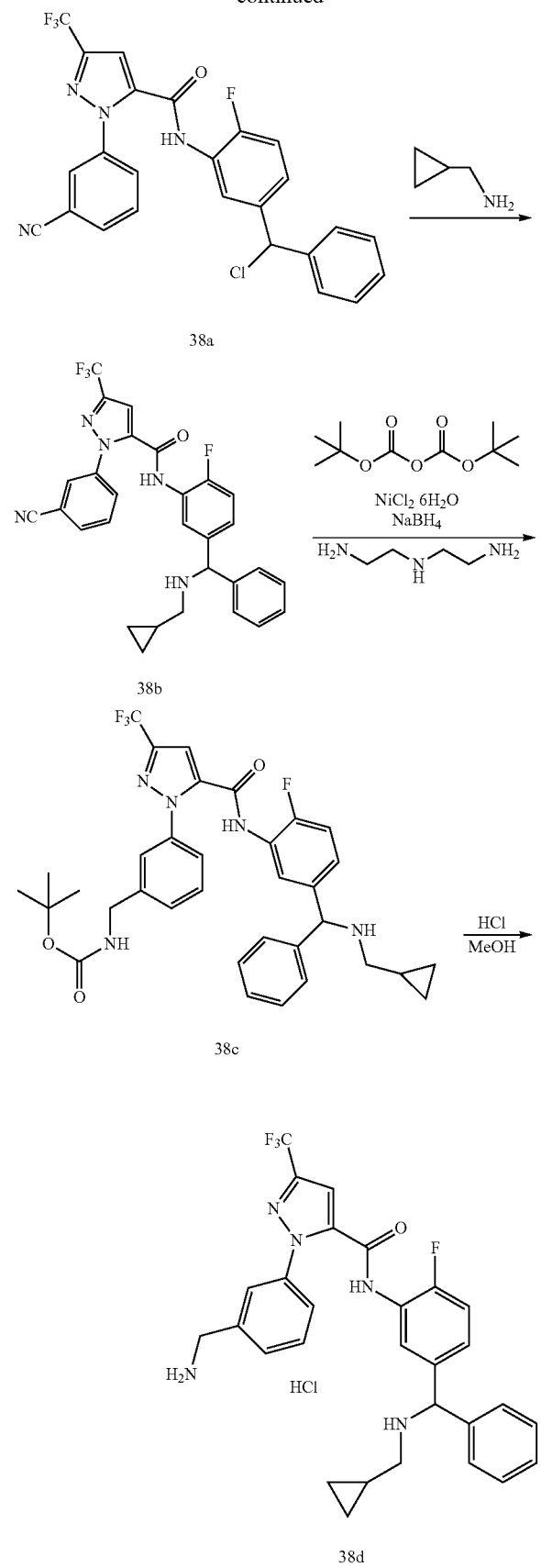

Preparation of Racemic 1-(3-(aminomethyl)phenyl)-N-(5-(((cyclopropylmethyl)amino)(phenyl)methyl)-2-fluorophenyl)-3-(trifluoromethyl)-1H-pyrazole-5-carboxamide (38d)

Step-1: Preparation of N-(5-(chloro(phenyl)methyl)-2-fluorophenyl)-1-(3-cyanophenyl)-3-(trifluoromethyl)-1H-pyrazole-5-carboxamide (38a)

To a solution of 1-(3-cyanophenyl)-N-(2-fluoro-5-(hydroxy(phenyl)methyl)phenyl)-3-(trifluoromethyl)-1H-pyrazole-5-carboxamide (34a) (0.462 g, 0.962 mmol) in dichloromethane (10 mL) at 0° C. was added thionyl chloride (0.211 mL, 2.89 mmol) and allowed to warm to room temperature over 3 h. To the reaction mixture was concentrated in vacuum to dryness. The residue was purified by flash column chromatography (silica gel 25 g, eluting with ethyl acetate in hexanes from 0-100%) to afford N-(5-(chloro(phenyl)methyl)-2-fluorophenyl)-1-(3-cyanophenyl)-3-(trifluoromethyl)-1H-pyrazole-5-carboxamide (38a) (0.208 g, 0.417 mmol, 43.4% yield) as a pale yellow greasy solid; $^1$H NMR (300 MHz, DMSO-d$_6$) δ 8.05 (t, J=1.6 Hz, 1H), 8.02 (d, J=1.8 Hz, 2H), 7.88 (dd, J=7.2, 2.3 Hz, 1H), 7.83-7.78 (m, 3H), 7.77-7.73 (m, 1H), 7.64 (ddd, J=8.9, 4.9, 2.3 Hz, 1H), 7.48 (dd, J=10.0, 8.7 Hz, 1H), 7.32 (dt, J=4.3, 1.1 Hz, 4H), 6.57 (s, 1H); $^{19}$F NMR (282 MHz, DMSO-d$_6$) δ −61.09, −121.678; MS (ES+) 534.2 (M+1); (ES−) 533.2 (M−1).

Step-2: Preparation of 1-(3-cyanophenyl)-N-(5-(((cyclopropylmethyl)amino)(phenyl)methyl)-2-fluorophenyl)-3-(trifluoromethyl)-1H-pyrazole-5-carboxamide (38b)

To a solution of N-(5-(chloro(phenyl)methyl)-2-fluorophenyl)-1-(3-cyanophenyl)-3-(trifluoromethyl)-1H-pyrazole-5-carboxamide (38a) (0.17 g, 0.341 mmol) in THF (10 mL) was added cyclopropylmethanamine (0.591 mL, 6.82 mmol) and heat at reflux overnight. An additional amount of cyclopropylmethanamine (0.591 mL, 6.82 mmol) and heated at reflux for 48h. The reaction mixture was quenched with water (10 mL) and extracted with ethyl acetate (2×10 mL). The combined organic layer was washed with brine (10 mL), dried, filtered and concentrated in vacuum. The residue was purified by flash column chromatography (silica gel 12 g, eluting 0-100% ethyl acetate in hexane) to afford 1-(3-cyanophenyl)-N-(5-(((cyclopropylmethyl)amino)(phenyl)methyl)-2-fluorophenyl)-3-(trifluoromethyl)-1H-pyrazole-5-carboxamide (38b) (0.12 g, 0.225 mmol, 66.0% yield) as a white solid; $^1$H NMR (300 MHz, DMSO-d$_6$) δ 10.53 (s, 1H), 8.15-8.10 (m, 1H), 8.00 (dt, J=7.7, 1.3 Hz, 1H), 7.94-7.86 (m, 1H), 7.77-7.69 (m, 2H), 7.57 (d, J=7.0 Hz, 1H), 7.42-7.37 (m, 2H), 7.36-7.15 (m, 6H), 4.84 (s, 1H), 2.26 (d, J=6.3 Hz, 2H), 0.98-0.83 (m, 1H), 0.43-0.31 (m, 2H), 0.04 (dd, J=5.3, 3.9 Hz, 2H); 19F NMR (282 MHz, DMSO-d$_6$) δ −61.06, −123.36; MS (ES+) 534.2 (M+1); (ES−) 533.2 (M−1).

Step-3: Preparation of tert-Butyl 3-(5-(5-((cyclopropylmethylamino)(phenyl)methyl)-2-fluorophenylcarbamoyl)-3-(trifluoromethyl)-1H-pyrazol-1-yl)benzylcarbamate (38c)

To a stirred solution of 1-(3-cyanophenyl)-N-(5-((cyclopropylmethylamino)(phenyl)methyl)-2-fluorophenyl)-3-(trifluoromethyl)-1H-pyrazole-5-carboxamide (38b) (0.12 g, 0.225 mmol) in anhydrous methanol (10 mL), cooled to 0° C., was added di-tert-butyl dicarbonate [(Boc)$_2$O)] (0.196 g, 0.900 mmol), nickel(II) chloride hexahydrate (0.013 g, 0.056 mmol). Sodium borohydride (0.051 g, 1.350 mmol) was added to the reaction mixture in small portions over 15 min. The reaction mixture was stirred for 15 min, quenched with N1-(2-aminoethyl)ethane-1,2-diamine (0.126 mL, 1.163 mmol) and stirred for 30 minutes before solvent was evaporated under vacuum. The residue was treated with water (15 mL), and extrated with ethyl acetate (2×25 mL). The organic layers were combined dried over MgSO$_4$ filtered and concentrated in vacuum to dryness. The residue obtained was purified by flash column chromatography [(silica gel 12 g, eluting with ethyl acetate/hexanes from 0 to 50%)] to furnish tert-butyl 3-(5-(5-((cyclopropylmethylamino)(phenyl)methyl)-2-fluorophenylcarbamoyl)-3-(trifluoromethyl)-1H-pyrazol-1-yl)benzylcarbamate (38c) (0.12 g, 0.188 mmol, 32.4% yield) as a colorless oil; $^1$H NMR (300 MHz, DMSO-d$_6$) δ 10.55 (s, 1H), 7.62 (d, J=8.2 Hz, 1H), 7.58 (s, 1H), 7.50 (dd, J=12.6, 6.1 Hz, 1H), 7.45-7.25 (m, 10H), 7.22-7.15 (m, 2H), 4.84 (s, 1H), 4.19 (d, J=6.2 Hz, 2H), 2.26 (d, J=6.5 Hz, 2H), 1.39 (s, 9H), 0.92 (dd, J=13.7, 5.7 Hz, 1H), 0.43-0.31 (m, 2H), 0.04 (td, J=5.6, 4.9, 2.1 Hz, 2H); 19F NMR (282 MHz, DMSO-d$_6$) δ −60.82, −123.76; MS (ES+) 638.3 (M+1); (ES−) 636.3 (M−1).

Step-4: Preparation of 1-(3-(aminomethyl)phenyl)-N-(5-(((cyclopropylmethyl)amino)(phenyl)methyl)-2-fluorophenyl)-3-(trifluoromethyl)-1H-pyrazole-5-carboxamide (38d)

To a solution of tert-butyl 3-(5-(5-((cyclopropylmethylamino)(phenyl)methyl)-2-fluorophenylcarbamoyl)-3-(trifluoromethyl)-1H-pyrazol-1-yl)benzylcarbamate (38c) (0.12 g, 0.188 mmol) in methanol (5 mL) was added HCl (0.286 mL, 9.41 mmol) and stirred at reflux for 2 h. The reaction mixture was concentrated in vacuum to dryness. Trace amounts of HCl and water was removed by azeotropic distillation under vacuum using ethanol (10 mL) and Toluene (10 mL). The residue was dried in a vacuum pump and purified by flash column chromatography (silica gel 8 g, eluting with 0-25% methanol in chloroform) to afford 1-(3-(aminomethyl)phenyl)-N-(5-(((cyclopropylmethyl)amino)(phenyl)methyl)-2-fluorophenyl)-3-(trifluoromethyl)-1H-pyrazole-5-carboxamide (38d) (0.044 g, 0.082 mmol, 43.5% yield) as a light yellow solid; $^1$H NMR (300 MHz, DMSO-d$_6$) δ 10.63 (s, 1H), 7.71 (s, 1H), 7.70-7.58 (m, 2H), 7.60-7.48 (m, 3H), 7.47-7.33 (m, 3H), 7.34-7.25 (m, 3H), 7.20 (dd, J=8.4, 5.7 Hz, 2H), 4.94 (s, 1H), 4.12 (s, 2H), 2.32 (d, J=6.7 Hz, 2H), 1.01-0.86 (m, 1H), 0.45-0.34 (m, 2H), 0.13-0.03 (m, 2H); $^{19}$F NMR (282 MHz, DMSO-d$_6$) δ −60.83; −123.36; MS (ES+) 538.3 (M+1); (ES−) 536.1 (M−1), 572.2 (M+Cl); Analysis calculated for C$_{29}$H$_{27}$F$_4$N$_5$O1.25HCl.H$_2$O: C, 57.94; H, 5.07; Cl, 7.37; N, 11.65; Found: C, 58.12; H, 4.99; Cl, 7.40; N, 11.34.

Scheme 39

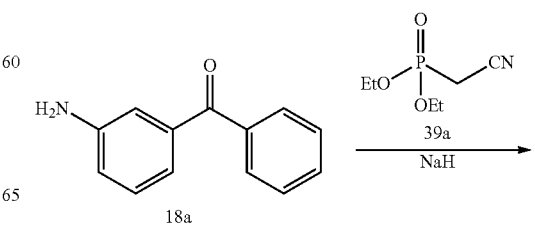

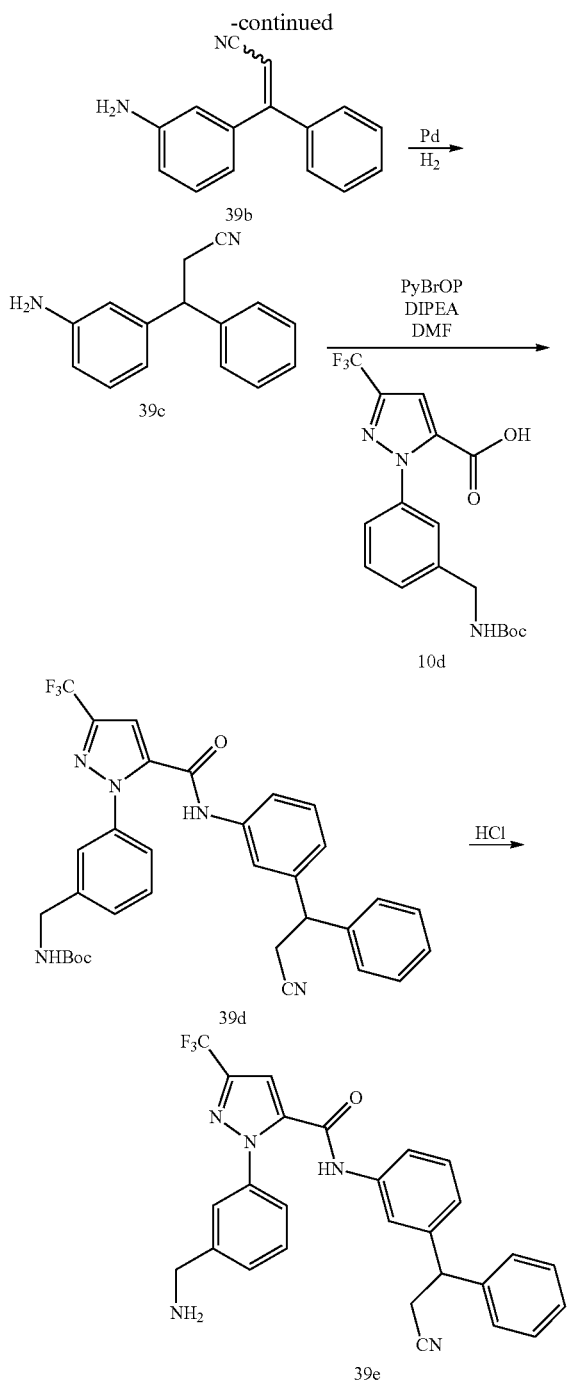

Preparation of 1-(3-(aminomethyl)phenyl)-N-(3-(2-cyano-1-phenylethyl)phenyl)-3-(trifluoromethyl)-1H-pyrazole-5-carboxamide (39e)

Step-1: Preparation of (E/Z)-3-(3-aminophenyl)-3-phenylacrylonitrile (39b)

To a suspension of NaH (0.507 g, 12.68 mmol) in DME (10 mL) was added diethyl cyanomethylphosphonate (39a) (1.835 mL, 11.66 mmol) at 0° C. The reaction was warmed to room temperature and stirred for 1 hr. To the reaction mixture was added a solution of (3-aminophenyl)(phenyl) methanone (18a) (1 g, 5.07 mmol) in DME (10.00 mL) at 0° C. and stirred at room temperature overnight. The reaction was quenched with saturated aqueous ammonium chloride (50 mL) at 0° C., extracted with ethyl acetate (2×100 mL). The organic layers were combined washed with water (2×50 mL), brine (50 mL), dried, filtered and concentrated in vacuum. The residue was purified by flash column chromatography (silicagel, 40 g) to afford (E/Z)-3-(3-aminophenyl)-3-phenylacrylonitrile (39b) (1.1 g, 98%); MS (ES+) 243.1 (M+Na); (ES−) 219.1 (M−1).

Step-2: Preparation of 3-(3-aminophenyl)-3-phenylpropanenitrile (39c)

To a suspension of Pd/C (10%) (0.012 g, 0.113 mmol) in methanol (30 mL) was added (E/Z)-3-(3-aminophenyl)-3-phenylacrylonitrile (39b) (0.25 g, 1.135 mmol) and hydrogenated at 60 psi for 14 h. The reaction mixture was filtered through a Celite pad and concentrated in vacuum to dryness. The crude residue was purified by flash column chromatography (silica gel, 12 g, eluting with ethyl acetate in hexanes 0 to 100%) to afford 3-(3-aminophenyl)-3-phenylpropanenitrile (39c) (180 mg, 71.3%); MS (ES+) 245.1 (M+Na); (ES−) 221.1 (M−1).

Step-3: Preparation of tert-butyl 3-(5-(3-(2-cyano-1-phenylethyl)phenylcarbamoyl)-3-(trifluoromethyl)-1H-pyrazol-1-yl)benzylcarbamate (39d)

To a solution of 1-(3-((tert-butoxycarbonylamino)methyl) phenyl)-3-(trifluoromethyl)-1H-pyrazole-5-carboxylic acid (10d) (144 mg, 0.375 mmol) in N,N-dimethylformamide (2.5 mL) was added 3-(3-aminophenyl)-3-phenylpropanenitrile (39c) (100 mg, 0.45 mmol), N-ethyl-N-isopropylpropan-2-amine (0.522 mL, 3.00 mmol) and Bromo-tris-pyrrolidino phosphoniumhexafluorophosphate (PyBroP, 192 mg, 0.412 mmol) at room temperature. The reaction mixture was stirred at 25° C. for 16 h. The reaction mixture was diluted with water (25 mL) and extracted with ethyl acetate (100 mL, 50 mL). The organic layers were combined dried over anhydrous MgSO$_4$, filtered, concentrated in vacuum. The residue was purified by flash column chromatography (silica gel 12 g, eluting with ethyl acetate in hexane 0-100%) to afford tert-butyl 3-(5-(3-(2-cyano-1-phenylethyl)phenylcarbamoyl)-3-(trifluoromethyl)-1H-pyrazol-1-yl)benzylcarbamate (39d) (180 mg, 81% yield) as colorless solid; MS (ES+) 612.2 (M+Na); (ES−) 588.8 (M−1).

Step-4: Preparation of 1-(3-(aminomethyl)phenyl)-N-(3-(2-cyano-1-phenylethyl)phenyl)-3-(trifluoromethyl)-1H-pyrazole-5-carboxamide (39e)

To a stirred solution of tert-butyl 3-(5-(3-(2-cyano-1-phenylethyl)phenylcarbamoyl)-3-(trifluoromethyl)-1H-pyrazol-1-yl)benzylcarbamate (39d) (0.090 g, 0.153 mmol) in acetonitrile (4 mL) was added hydrochloric acid, 4 N in 1,4-dioxane (0.763 mL, 3.05 mmol), stirred at room temperature for 3 h and concentrated in vacuum to dryness. The residue was suspended in ether (30 mL) and the solid that separated was collected by filtration, dried under vacuum to afford 1-(3-(aminomethyl)phenyl)-N-(3-(2-cyano-1-phenylethyl)phenyl)-3-(trifluoromethyl)-1H-pyrazole-5-carboxamide (39e) (70 mg, 94% yield); $^1$HNMR (300 MHz, DMSO-d$_6$) δ 10.81 (s, 1H,), 8.38 (s, 3H, D$_2$O exchangeable), 7.72 (t, J=1.7 Hz, 1H), 7.66 (s, 1H), 7.64-7.47 (m, 5H), 7.33 (d, J=4.1 Hz, 5H), 7.26-7.19 (m, 2H), 4.42 (t, J=8.0 Hz, 1H), 4.12 (q, J=5.8 Hz, 2H), 3.31 (d, J=8.0 Hz, 2H); MS (ES+) 490.3 (M+1), (ES−) 488.2 (M−1), 524.2 (M+35).

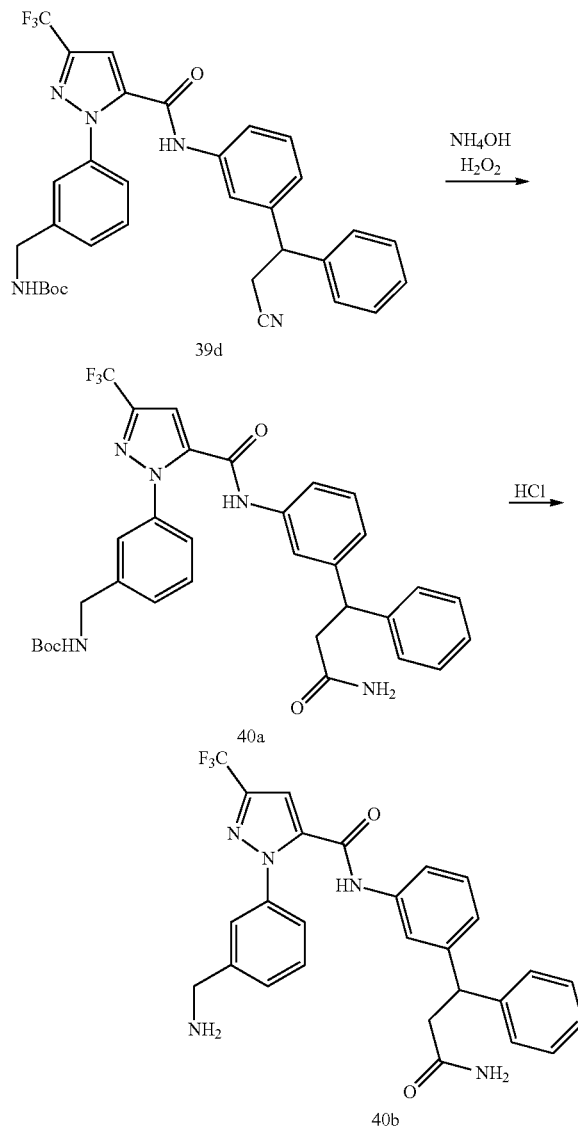

Preparation of N-(3-(3-amino-3-oxo-1-phenylpropyl)phenyl)-1-(3-(aminomethyl)phenyl)-3-(trifluoromethyl)-1H-pyrazole-5-carboxamide (40b)

Step-1: Preparation of tert-butyl 3-(5-((3-(3-amino-3-oxo-1-phenylpropyl)phenyl)carbamoyl)-3-(trifluoromethyl)-1H-pyrazol-1-yl)benzylcarbamate (40a)

To a stirred solution of tert-butyl 3-(5-(3-(2-cyano-1-phenylethyl)phenylcarbamoyl)-3-(trifluoromethyl)-1H-pyrazol-1-yl)benzylcarbamate (39d) (0.07 g, 0.119 mmol) in MeOH (4 mL) cooled to 0° C. was added conc NH$_4$OH (0.826 mL, 5.94 mmol), hydrogen peroxide 35% solution (1.559 mL, 17.81 mmol) and stirred for 16 h at room temperature. The reaction mixture was concentrated in vacuum and the residue obtained was purified by flash column chromatography [silica gel 12 g, eluting with 0-100% (9:1) mixture of ethyl acetate and methanol in hexanes] to afford tert-butyl 3-(5-(3-(3-amino-3-oxo-1-phenylpropyl)phenylcarbamoyl)-3-(trifluoromethyl)-1H-pyrazol-1-yl)benzylcarbamate (40a) (47 mg, 65.2% yield); MS (ES+) 630.3 (M+Na); (ES−) 606.3 (M−1).

Step-2: Preparation of N-(3-(3-amino-3-oxo-1-phenylpropyl)phenyl)-1-(3-(aminomethyl)phenyl)-3-(trifluoromethyl)-1H-pyrazole-5-carboxamide (40b)

To a stirred solution of tert-butyl 3-(5-(3-(3-amino-3-oxo-1-phenylpropyl)phenylcarbamoyl)-3-(trifluoromethyl)-1H-pyrazol-1-yl)benzylcarbamate (40a) (0.040 g, 0.066 mmol) in methanol (3 mL) was added conc HCl (0.110 mL, 1.317 mmol) and heated at reflux for 30 minutes. The reaction mixture was concentrated in vacuum to dryness.

The residue was suspended in ether and solid separated was collected by filtration, dried in vacuum. The solid was purified by flash column chromatography (silica gel 4 g, eluting with methanol in chloroform 0 to 20%) to afford N-(3-(3-amino-3-oxo-1-phenylpropyl)phenyl)-1-(3-(aminomethyl)phenyl)-3-(trifluoromethyl)-1H-pyrazole-5-carboxamide (40b) (15 mg, 44.9% yield) as a white solid; $^1$HNMR (300 MHz, DMSO-d$_6$) δ 10.72 (s, 1H, D$_2$O exchangeable), 7.67 (s, 1H), 7.62 (s, 1H), 7.60-7.43 (m, 5H), 7.39 (s, 1H), 7.30-7.21 (m, 5H), 7.17 (d, J=6.7 Hz, 1H), 7.08 (d, J=7.3 Hz, 1H), 6.77 (s, 1H), 4.42 (s, 1H), 4.05 (s, 2H), 2.78 (dd, J=7.9, 3.6 Hz, 2H); MS (ES+) 508.3 (M+1), (ES−) 542.2 (M+35).

Scheme 41

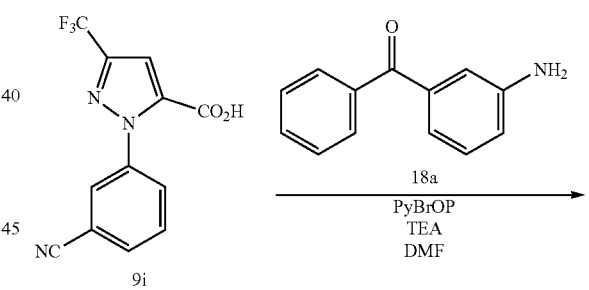

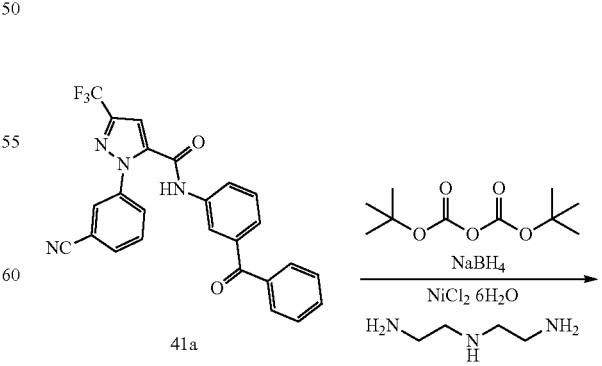

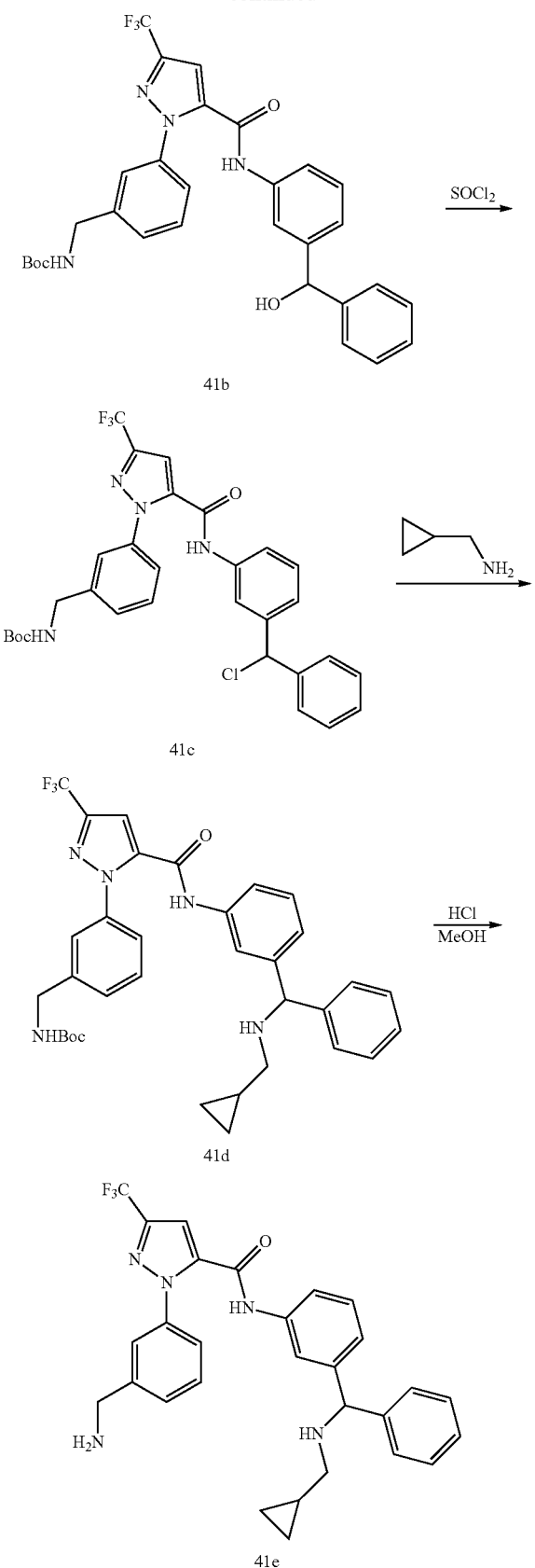

Preparation of 1-(3-(Aminomethyl)phenyl)-N-(3-(((cyclopropylmethyl)amino)(phenyl)methyl)phenyl)-3-(trifluoromethyl)-1H-pyrazole-5-carboxamide (41e)

Step-1: Preparation of N-(3-benzoylphenyl)-1-(3-cyanophenyl)-3-(trifluoromethyl)-1H-pyrazole-5-carboxamide (41a)

To a solution of 1-(3-cyanophenyl)-3-(trifluoromethyl)-1H-pyrazole-5-carboxylic acid (9i) (5.42 g, 19.27 mmol) in DMF (100 mL) was added at room temperature (3-aminophenyl)(phenyl)methanone (18a) (3.8 g, 19.27 mmol) N-ethyl-N-isopropylpropan-2-amine (27 mL, 155 mmol) and bromo-tris-pyrrolidino phosphoniumhexafluorophosphate (PyBrop) (9.42 g, 19.42 mmol). The resulting reaction mixture was stirred at room temperature for 39 h under nitrogen atmosphere and diluted with ethyl acetate (600 mL). The reaction mixture was washed with water (2×300 mL), brine (200 mL), dried, filtered and concentrated in vacuum. The residue obtained was purified by flash column chromatography (silica gel 120 g, eluting with ethyl acetate in hexanes from 0-100%] to afford N-(3-benzoylphenyl)-1-(3-cyanophenyl)-3-(trifluoromethyl)-1H-pyrazole-5-carboxamide (41a) (4.704 g, 53%) as a white solid, contaminated with (3-aminophenyl)(phenyl)methanone; $^1$H NMR (300 MHz, DMSO-$d_6$) δ 10.89 (s, 1H), 8.20 (t, J=1.9 Hz, 1H), 8.07-7.98 (m, 3H), 7.93 (ddd, J=8.2, 2.2, 1.1 Hz, 1H), 7.78-7.71 (m, 4H), 7.62-7.57 (m, 2H), 7.56 (d, J=3.2 Hz, 1H), 7.53 (d, J=2.5 Hz, 1H), 7.50 (dt, J=7.7, 1.5 Hz, 1H); $^{19}$F NMR (282 MHz, DMSO-$d_6$) δ −60.98.

Step-2: Preparation of N-(3-benzoylphenyl)-1-(3-cyanophenyl)-3-(trifluoromethyl)-1H-pyrazole-5-carboxamide (41b)

To a stirred solution of N-(3-benzoylphenyl)-1-(3-cyanophenyl)-3-(trifluoromethyl)-1H-pyrazole-5-carboxamide (41a) (4.704 g, 10.22 mmol) in anhydrous methanol (100 mL), cooled to 0° C. were added di-tert-butyl dicarbonate [(Boc)$_2$O] (6.76 g, 30.7 mmol), nickel(II) chloride hexahydrate (0.5 g, 2.103 mmol). To the reaction mixture was added sodium borohydride (2.367 g, 61.3 mmol) portionwise over 45 mins. The reaction mixture was stirred for 15 min at room temperature and quenched with N1-(2-aminoethyl)ethane-1,2-diamine (2.3 mL, 21.08 mmol). The mixture was stirred for 30 minutes and concentrated in vacuum to dryness. The residue obtained was treated with water (200 mL) and extracted with ethyl acetate (400 and 150 mL). Organic layer was combined dried, filtered and concentrated in vacuum to dryness. The residue was purified by flash column chromatography [(silica gel 120 g, eluting with ethyl acetate/hexanes from 0 to 100%)] to furnish N-(3-benzoylphenyl)-1-(3-cyanophenyl)-3-(trifluoromethyl)-1H-pyrazole-5-carboxamide (41b) (2.71 g, 46.8%) as a white solid; $^1$H NMR (300 MHz, DMSO-$d_6$) δ 10.69 (s, 1H), 7.62 (d, J=1.8 Hz, 1H), 7.59-7.39 (m, 5H), 7.38-7.17 (m, 8H), 7.13 (dt, J=7.6, 1.3 Hz, 1H), 5.94 (d, J=3.8 Hz, 1H), 5.66 (d, J=3.9 Hz, 1H), 4.19 (d, J=6.3 Hz, 2H), 1.37 (s, 9H); $^{19}$F NMR (282 MHz, DMSO-$d_6$) δ −60.81; MS (ES+) 589.26 (M+Na)

Step-3: Preparation of tert-butyl 3-(5-(3-((cyclopropylmethylamino)(phenyl)methyl)phenylcarbamoyl)-3-(trifluoromethyl)-1H-pyrazol-1-yl)benzylcarbamate (41d)

To a solution of N-(3-benzoylphenyl)-1-(3-cyanophenyl)-3-(trifluoromethyl)-1H-pyrazole-5-carboxamide (41b)

(0.142 g, 0.25 mmol) in dichloromethane (2.5 mL) at 0° C. was added thionyl chloride (0.073 mL, 0.999 mmol) and allowed to warm to room temperature over 3 h. To the reaction mixture containing tert-butyl 3-(5-((3-(chloro(phenyl)methyl)phenyl)carbamoyl)-3-(trifluoromethyl)-1H-pyrazol-1-yl)benzylcarbamate (41c) was added cyclopropylmethanamine (0.217 mL, 2.500 mmol) and stirred at room temperature overnight. TLC analysis shows only tert-butyl 3-(5-((3-(chloro(phenyl)methyl)phenyl)carbamoyl)-3-(trifluoromethyl)-1H-pyrazol-1-yl)benzylcarbamate (41c). To the reaction mixture was added dichloromethane (5 mL) and additional cyclopropylmethanamine (0.217 mL, 2.5 mmol) and heat at reflux overnight. The reaction mixture was cooled to room temperature diluted with dichloromethane (10 mL), washed with water (10 mL), dried, filtered and concentrated in vacuum. The residue was purified by flash column chromatography (silica gel 12 g, eluting 0-100% ethyl acetate in hexane) to afford tert-butyl 3-(5-(3-((cyclopropylmethylamino)(phenyl)methyl)phenylcarbamoyl)-3-(trifluoromethyl)-1H-pyrazol-1-yl)benzylcarbamate (41d) (0.07 g, 0.113 mmol, 45.2% yield) which was good enough to be used as such for next step; $^1$H NMR (300 MHz, DMSO-d$_6$) δ 10.69 (s, 1H), 7.65 (d, J=2.1 Hz, 1H), 7.58 (s, 1H), 7.56-7.48 (m, 2H), 7.44-7.33 (m, 7H), 7.31-7.23 (m, 2H), 7.22-7.16 (m, 2H), 4.81 (s, 1H), 4.19 (d, J=6.2 Hz, 2H), 2.24 (d, J=6.6 Hz, 2H), 1.36 (d, J=2.1 Hz, 9H), 0.94 (d, J=10.3 Hz, 1H), 0.41-0.34 (m, 2H), 0.09-0.03 (m, 2H); $^{19}$F NMR (282 MHz, DMSO-d$_6$) δ −60.80; MS (ES+) 620.4 (M+1); (ES−) 618.3 (M−1).

Step-4: Preparation of 1-(3-(Aminomethyl)phenyl)-N-(3-(((cyclopropylmethyl)amino)(phenyl) methyl)phenyl)-3-(trifluoromethyl)-1H-pyrazole-5-carboxamide (41e)

To a solution of tert-butyl 3-(5-(3-((cyclopropylmethylamino)(phenyl)methyl)phenylcarbamoyl)-3-(trifluoromethyl)-1H-pyrazol-1-yl)benzylcarbamate (41d) (0.07 g, 0.113 mmol) in methanol (5 mL) was added conc HCl (0.069 mL, 2.259 mmol) and stirred at room temperature overnight followed by heating at reflux for 1 h. The reaction mixture was concentrated in vacuum to dryness. Trace amount of HCl and water was removed by azeotropic distillation under vacuum using ethanol (10 mL) and Toluene (10 mL). The residue was dried in a vacuum pump and purified by flash column chromatography (silica gel 8 g, eluting with 0-25% methanol in chloroform) to afford 1-(3-(Aminomethyl)phenyl)-N-(3-(((cyclopropylmethyl)amino)(phenyl) methyl)phenyl)-3-(trifluoromethyl)-1H-pyrazole-5-carboxamide (41e) (0.031 g, 0.060 mmol, 52.8% yield) as a yellow hygroscopic solid; $^1$H NMR (300 MHz, DMSO-d$_6$) δ 10.68 (s, 1H), 7.66 (d, J=1.8 Hz, 1H), 7.59-7.48 (m, 3H), 7.47-7.36 (m, 4H), 7.36-7.23 (m, 4H), 7.23-7.14 (m, 2H), 4.81 (s, 1H), 3.79 (s, 2H), 2.38 (d, J=6.7 Hz, 2H), 0.99-0.86 (m, 1H), 0.42-0.34 (m, 2H), 0.04 (td, J=5.5, 3.9 Hz, 2H); $^{19}$F NMR (282 MHz, DMSO-d$_6$) δ −60.72; MS (ES+) 520.3 (M+1); (ES−) 518.2 (M−1).

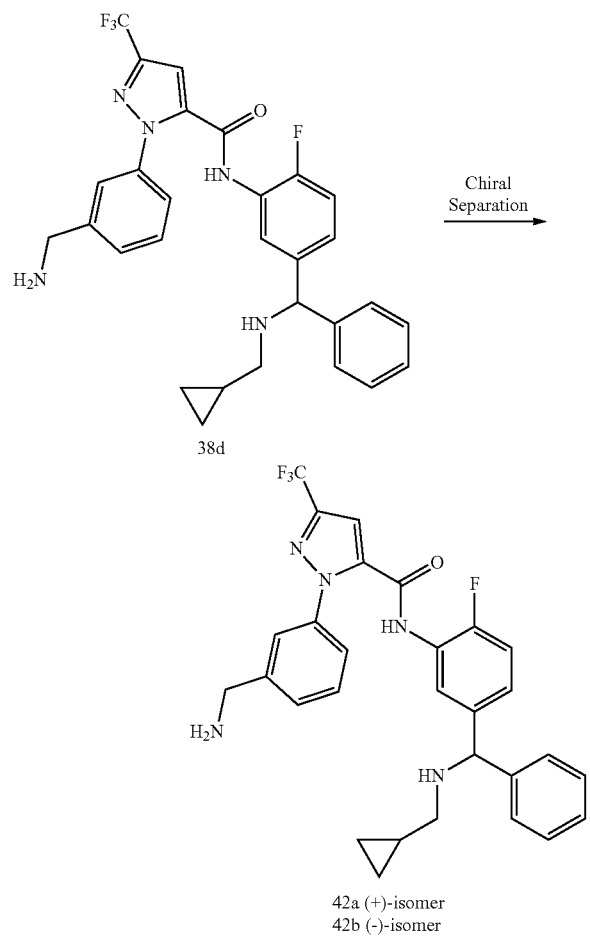

Scheme 42

38d

Chiral Separation →

42a (+)-isomer
42b (−)-isomer

Preparation of (+)-1-(3-(aminomethyl)phenyl)-N-(5-(((cyclopropylmethyl)amino)(phenyl)methyl)-2-fluorophenyl)-3-(trifluoromethyl)-1H-pyrazole-5-carboxamide (42a) and (−)-1-(3-(aminomethyl)phenyl)-N-(5-(((cyclopropylmethyl)amino)(phenyl)methyl)-2-fluorophenyl)-3-(trifluoromethyl)-1H-pyrazole-5-carboxamide (42b)

Preparation of (+)-1-(3-(aminomethyl)phenyl)-N-(5-(((cyclopropylmethyl)amino)(phenyl)methyl)-2-fluorophenyl)-3-(trifluoromethyl)-1H-pyrazole-5-carboxamide (42a) and (−)-1-(3-(aminomethyl)phenyl)-N-(5-(((cyclopropylmethyl)amino)(phenyl)methyl)-2-fluorophenyl)-3-(trifluoromethyl)-1H-pyrazole-5-carboxamide (42b)

Racemic 1-(3-(aminomethyl)phenyl)-N-(5-(((cyclopropylmethyl)amino)(phenyl)methyl)-2-fluorophenyl)-3-(trifluoromethyl)-1H-pyrazole-5-carboxamide (38d) (1.09 gms) was purified by preparative SFC Method using the following condition.

| Column | 3.0 × 25.0 cm ChiralPak AD-H from Chiral Technologies (West Chester, PA) |

-continued

| | |
|---|---|
| CO₂ Co-solvent (Solvent B) | Methanol:Acetonitrile(1:1) with 1% Isopropylamine |
| Isocratic Method | 30% Co-solvent at 80 mL/min |
| System Pressure | 200 bar |
| Column Temperature | 40° C. |
| Sample Diluent | Methanol:Acetonitrile (~2:1) |

Purification afforded;

1. (−)-1-(3-(aminomethyl)phenyl)-N-(5-(((cyclopropylmethyl)amino)(phenyl)methyl)-2-fluorophenyl)-3-(trifluoromethyl)-1H-pyrazole-5-carboxamide (42b) (463 mg 99.9% ee); $^1$H NMR (300 MHz, Methanol-d$_4$) δ 7.74 (d, J=7.3 Hz, 1H), 7.54 (s, 1H), 7.47 (d, J=4.9 Hz, 2H), 7.43-7.26 (m, 6H), 7.24-7.17 (m, 1H), 7.12 (t, J=9.4 Hz, 1H), 3.85 (s, 2H), 3.21 (s, 1H), 2.37 (d, J=6.9 Hz, 2H), 1.04-0.90 (m, 1H), 0.51-0.42 (m, 2H), 0.11-0.03 (m, 2H); $^{19}$F NMR (282 MHz, Methanol-d$_4$) δ −63.73, −127.27; $^1$H NMR (300 MHz, DMSO-d$_6$) δ 10.50 (s, 1H), 7.61 (d, J=7.4 Hz, 1H), 7.56 (s, 1H), 7.51 (s, 1H), 7.47-7.36 (m, 4H), 7.35-7.25 (m, 4H), 7.19 (tt, J=7.3, 2.7 Hz, 2H), 4.83 (s, 1H), 3.77 (s, 2H), 2.26 (d, J=6.6 Hz, 2H), 1.03-0.72 (m, 1H), 0.46-0.25 (m, 2H), 0.12-0.00 (m, 2H); $^{19}$F NMR (282 MHz, DMSO-d$_6$) δ −60.73, −123.86; MS (ES+) 538.3 (M+1); (ES−) 536.3 (M−1); Optical Rotation −4.95 (MeOH, 1.415).

To a solution of (−)-1-(3-(aminomethyl)phenyl)-N-(5-(((cyclopropylmethyl)amino)(phenyl)methyl)-2-fluorophenyl)-3-(trifluoromethyl)-1H-pyrazole-5-carboxamide (42b) free base (0.44 mgs, 0.82 mmol) in methanol (4 mL) was added 2 N methanolic HCl (4 mL, prepared from methanol and conc HCl, 4 mmol). The mixture was allowed to stay for 15 mins at room temperature concentrated in vacuum to dryness to furnish (−)-1-(3-(aminomethyl)phenyl)-N-(5-(((cyclopropylmethyl)amino)(phenyl)methyl)-2-fluorophenyl)-3-(trifluoromethyl)-1H-pyrazole-5-carboxamide (42b) (0.46 gm) as a dihydrochloride; $^1$H NMR (300 MHz, DMSO-d$_6$) δ 10.84 (s, 1H), 10.30 (d, J=16.0 Hz, 2H), 8.52 (s, 3H), 7.95 (dd, J=7.2, 2.3 Hz, 1H), 7.80-7.69 (m, 5H), 7.64 (dt, J=7.2, 1.7 Hz, 1H), 7.60-7.49 (m, 2H), 7.47-7.33 (m, 4H), 5.74-5.59 (m, 1H), 4.12 (d, J=5.0 Hz, 2H), 2.69 (d, J=6.6 Hz, 2H), 1.24-1.09 (m, 1H), 0.61-0.50 (m, 2H), 0.36-0.23 (m, 2H); $^{19}$F NMR (282 MHz, DMSO-d$_6$) δ −60.81, −120.59; MS (ES+) 538.3 (M+1); (ES−) 536.2 (M−1); Analysis calculated for C$_{29}$H$_{27}$F$_3$N$_5$O.2HCl.H$_2$O: C, 55.42; H, 4.97; Cl, 11.28; N, 11.14; Found: C, 55.45; H, 5.13; Cl, 11.12; N, 11.15.

2. (+)-1-(3-(aminomethyl)phenyl)-N-(5-(((cyclopropylmethyl)amino)(phenyl)methyl)-2-fluorophenyl)-3-(trifluoromethyl)-1H-pyrazole-5-carboxamide (42a) (461 mg 95.1% ee). contaminated with isopropylamine; $^1$H NMR (300 MHz, DMSO-d$_6$) δ 7.59 (d, J=7.3 Hz, 1H), 7.51 (s, 1H), 7.45-7.09 (m, 11H), 4.81 (d, J=3.2 Hz, 1H), 3.76 (s, 2H), 2.26 (d, J=6.6 Hz, 2H), 0.92 (d, J=7.7 Hz, 1H), 0.44-0.31 (m, 2H), 0.04 (td, J=5.5, 5.0, 1.9 Hz, 2H); $^{19}$F NMR (282 MHz, DMSO-d$_6$) δ −60.68, −124.17; $^1$H NMR (300 MHz, Methanol-d$_4$) δ 7.65 (d, J=7.3 Hz, 1H), 7.51 (s, 1H), 7.45-7.39 (m, 3H), 7.34 (d, J=7.2 Hz, 2H), 7.29-7.23 (m, 4H), 7.19-7.14 (m, 1H), 7.11-7.02 (m, 1H), 4.84 (s, 1H), 3.81 (s, 2H), 2.33 (d, J=6.9 Hz, 2H), 1.02-0.85 (m, 1H), 0.49-0.38 (m, 2H), 0.09-−0.00 (m, 2H); $^{19}$F NMR (282 MHz, Methanol-d$_4$) δ −63.71, −127.26; MS (ES+) 538.2 (M+1); (ES−) 536.2 (M−1); Optical Rotation+2.77 (MeOH, 1.95).

To a solution of above (+)-1-(3-(aminomethyl)phenyl)-N-(5-(((cyclopropylmethyl)amino)(phenyl)methyl)-2-fluorophenyl)-3-(trifluoromethyl)-1H-pyrazole-5-carboxamide (42a) free base (0.44 mgs, 0.82 mmol) in methanol (4 mL) was added 2 N methanolic HCl (4 mL, prepared from methanol and conc HCl, 4 mmol). The mixture was allowed to stay for 15 mins at room temperature concentrated in vacuum to dryness to furnish (+)-1-(3-(aminomethyl)phenyl)-N-(5-(((cyclopropylmethyl)amino)(phenyl)methyl)-2-fluorophenyl)-3-(trifluoromethyl)-1H-pyrazole-5-carboxamide (42a) (0.46 gm) as a dihydrochloride; $^1$H NMR (300 MHz, DMSO-d$_6$) δ 10.84 (s, 1H), 10.24 (d, J=20.4 Hz, 2H), 8.52 (s, 3H), 7.95 (dd, J=7.1, 2.3 Hz, 1H), 7.79-7.69 (m, 5H), 7.64 (dt, J=7.2, 1.8 Hz, 1H), 7.59-7.48 (m, 2H), 7.47-7.33 (m, 4H), 5.66 (t, J=6.3 Hz, 1H), 4.12 (q, J=5.7 Hz, 2H), 2.68 (d, J=10.8 Hz, 2H), 2.12 (s, 1H), 1.24-1.12 (m, 1H), 0.63-0.48 (m, 2H), 0.36-0.24 (m, 2H); $^{19}$F NMR (282 MHz, DMSO-d$_6$) δ −60.81, −120.62; MS (ES+) 538.3 (M+1); (ES−) 536.2 (M−1); Analysis calculated for C$_{29}$H$_{27}$F$_3$N$_5$O.2.25HCl.1.25H$_2$O.0.5C$_3$H$_9$N: C, 54.54; H, 5.44; Cl, 11.88; N, 11.47; Found: C, 54.34; H, 5.64; Cl, 12.12; N, 11.78.

The following analytical SFC Method was used to check purity of compounds 42a and 42b

| | |
|---|---|
| Column | 4.6 × 100 mm ChiralPak AD-H from Chiral Technologies (West Chester, PA) |
| CO₂ Co-solvent (Solvent B) | Methanol:Acetonitrile (1:1) with 0.1% Isopropylamine |
| Isocratic Method | 20% Co-solvent at 4 mL/min |
| System Pressure | 150 bar |
| Column Temperature | 40° C. |
| Sample Diluent | Methanol |

| | | | | |
|---|---|---|---|---|
| Fraction 1 (42b) | 1.6 min (Rt) | 463 mg | 99.9% (ee) | 97.1% (Purity) |
| Fraction 2 (42a) | 2.9 min (Rt) | 461 mg | 95.1% (ee) | 96.5% (Purity) |

Scheme 43

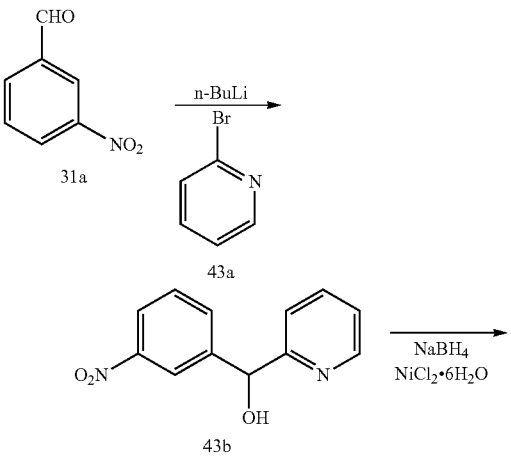

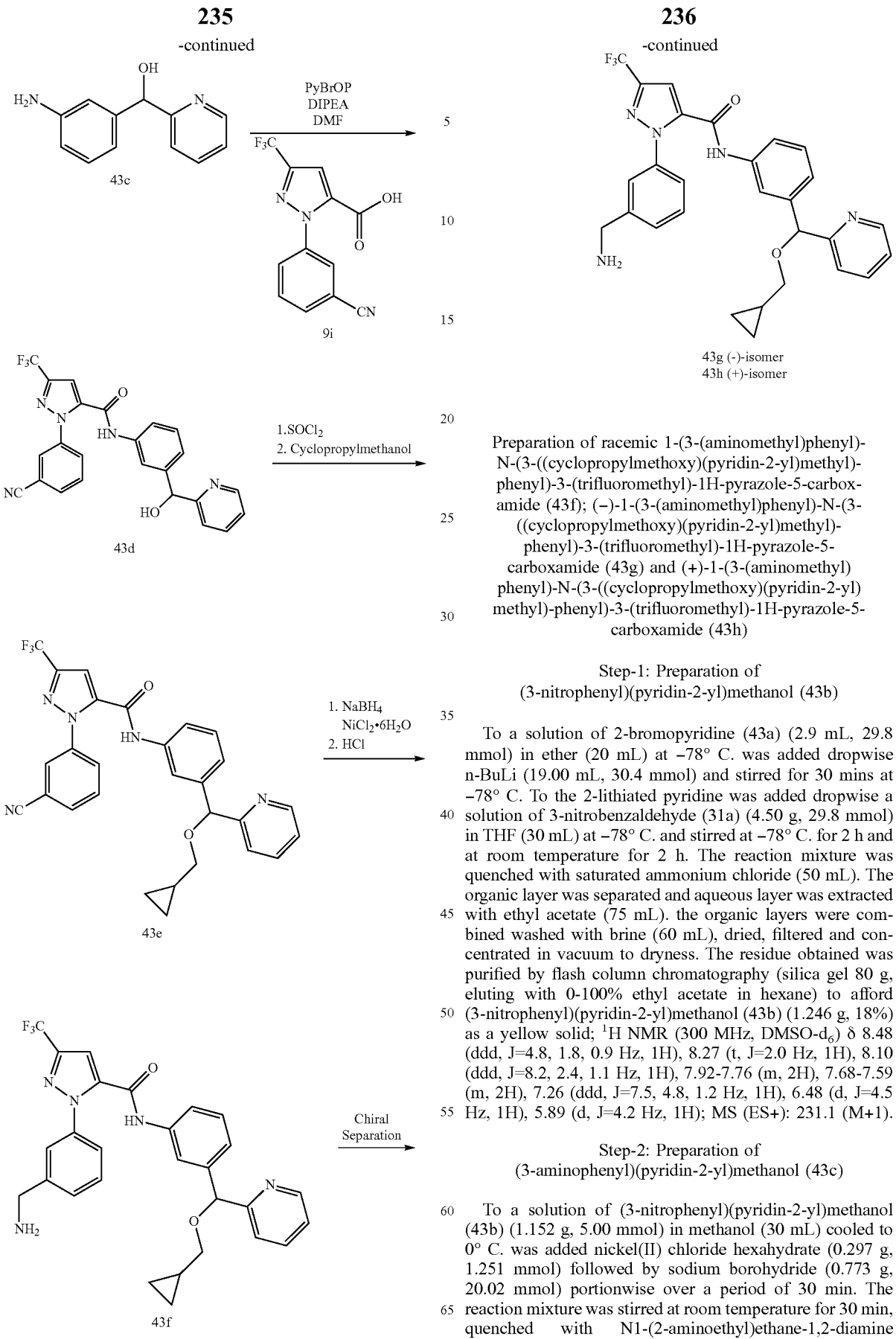

Preparation of racemic 1-(3-(aminomethyl)phenyl)-N-(3-((cyclopropylmethoxy)(pyridin-2-yl)methyl)-phenyl)-3-(trifluoromethyl)-1H-pyrazole-5-carboxamide (43f); (−)-1-(3-(aminomethyl)phenyl)-N-(3-((cyclopropylmethoxy)(pyridin-2-yl)methyl)-phenyl)-3-(trifluoromethyl)-1H-pyrazole-5-carboxamide (43g) and (+)-1-(3-(aminomethyl)phenyl)-N-(3-((cyclopropylmethoxy)(pyridin-2-yl)methyl)-phenyl)-3-(trifluoromethyl)-1H-pyrazole-5-carboxamide (43h)

Step-1: Preparation of (3-nitrophenyl)(pyridin-2-yl)methanol (43b)

To a solution of 2-bromopyridine (43a) (2.9 mL, 29.8 mmol) in ether (20 mL) at −78° C. was added dropwise n-BuLi (19.00 mL, 30.4 mmol) and stirred for 30 mins at −78° C. To the 2-lithiated pyridine was added dropwise a solution of 3-nitrobenzaldehyde (31a) (4.50 g, 29.8 mmol) in THF (30 mL) at −78° C. and stirred at −78° C. for 2 h and at room temperature for 2 h. The reaction mixture was quenched with saturated ammonium chloride (50 mL). The organic layer was separated and aqueous layer was extracted with ethyl acetate (75 mL). the organic layers were combined washed with brine (60 mL), dried, filtered and concentrated in vacuum to dryness. The residue obtained was purified by flash column chromatography (silica gel 80 g, eluting with 0-100% ethyl acetate in hexane) to afford (3-nitrophenyl)(pyridin-2-yl)methanol (43b) (1.246 g, 18%) as a yellow solid; $^1$H NMR (300 MHz, DMSO-$d_6$) δ 8.48 (ddd, J=4.8, 1.8, 0.9 Hz, 1H), 8.27 (t, J=2.0 Hz, 1H), 8.10 (ddd, J=8.2, 2.4, 1.1 Hz, 1H), 7.92-7.76 (m, 2H), 7.68-7.59 (m, 2H), 7.26 (ddd, J=7.5, 4.8, 1.2 Hz, 1H), 6.48 (d, J=4.5 Hz, 1H), 5.89 (d, J=4.2 Hz, 1H); MS (ES+): 231.1 (M+1).

Step-2: Preparation of (3-aminophenyl)(pyridin-2-yl)methanol (43c)

To a solution of (3-nitrophenyl)(pyridin-2-yl)methanol (43b) (1.152 g, 5.00 mmol) in methanol (30 mL) cooled to 0° C. was added nickel(II) chloride hexahydrate (0.297 g, 1.251 mmol) followed by sodium borohydride (0.773 g, 20.02 mmol) portionwise over a period of 30 min. The reaction mixture was stirred at room temperature for 30 min, quenched with N1-(2-aminoethyl)ethane-1,2-diamine (1.100 mL, 10.18 mmol), stirred for additional 30 min and concentrated in vacuum to dryness. The residue was treated with ethyl acetate (150 mL), washed with water (75 mL). The aqueous phase was extracted again with ethyl acetate (75 mL). The combined extracts were washed with brine (75 mL), dried over MgSO$_4$, filtered and concentrated in vacuum to dryness. The crude residue was purified by flash column chromatography [silica gel eluting with hexanes/ethyl acetate (1:0 to 0:1)] to afford (3-aminophenyl)(pyridin-2-yl)methanol (43c) (746 mg, 75%) as a light yellow gum. $^1$H NMR (300 MHz, DMSO-d$_6$) δ 8.43 (ddd, J=4.8, 1.8, 0.9 Hz, 1H), 7.75 (td, J=7.7, 1.8 Hz, 1H), 7.50 (dt, J=8.0, 1.1 Hz, 1H), 7.21 (ddd, J=7.5, 4.8, 1.2 Hz, 1H), 6.90 (t, J=7.7 Hz, 1H), 6.60 (dd, J=2.3, 1.6 Hz, 1H), 6.56-6.50 (m, 1H), 6.37 (ddd, J=7.9, 2.4, 1.1 Hz, 1H), 5.88 (d, J=4.0 Hz, 1H), 5.51 (d, J=4.0 Hz, 1H), 5.00 (s, 2H); MS (ES+): 223.1 (M+23).

Step-3: Preparation of 1-(3-cyanophenyl)-N-(3-(hydroxy(pyridin-2-yl)methyl)phenyl)-3-(trifluoromethyl)-1H-pyrazole-5-carboxamide (43d)

To a solution of (3-aminophenyl)(pyridin-2-yl)methanol (43c) (0.983 g, 3.50 mmol) in N,N-dimethylformamide (30 mL) was added 1-(3-cyanophenyl)-3-(trifluoromethyl)-1H-pyrazole-5-carboxylic acid (9i) (0.983 g, 3.50 mmol), N-ethyl-N-isopropylpropan-2-amine (4.90 mL, 28.1 mmol) and bromotripyrrolidin-1-ylphosphonium hexafluorophosphate(V) (1.676 g, 3.52 mmol) at room temperature. The reaction mixture was stirred at 25° C. for 13 h and diluted with ethyl acetate (200 mL). The reaction mixture was washed with water (2×100 mL), brine (75 mL), dried over anhydrous MgSO$_4$, filtered and concentrated in vacuum to dryness. The residue obtained was purified by flash column chromatography [silica gel 12 g, eluting with hexanes/ethyl acetate (1:0 to 0:1) to afford 1-(3-cyanophenyl)-N-(3-(hydroxy(pyridin-2-yl)methyl)phenyl)-3-(trifluoromethyl)-1H-pyrazole-5-carboxamide (43d) (1.049 g, 65%) as a off-white solid; $^1$H NMR (300 MHz, DMSO-d$_6$) δ 10.65 (s, 1H), 8.44 (ddd, J=4.9, 1.8, 0.9 Hz, 1H), 8.16 (dd, J=2.1, 1.4 Hz, 1H), 8.01 (dt, J=7.8, 1.3 Hz, 1H), 7.90 (ddd, J=8.2, 2.2, 1.1 Hz, 1H), 7.81-7.65 (m, 4H), 7.59-7.52 (m, 2H), 7.30-7.15 (m, 3H), 6.16 (d, J=4.0 Hz, 1H), 5.68 (d, J=4.0 Hz, 1H); $^{19}$F NMR (282 MHz, DMSO-d$_6$) δ −60.95; MS (ES+): 464.2 (M+1).

Step-4: Preparation of 1-(3-cyanophenyl)-N-(3-((cyclopropylmethoxy)(pyridin-2-yl)methyl)phenyl)-3-(trifluoromethyl)-1H-pyrazole-5-carboxamide (43e)

To a solution of 1-(3-cyanophenyl)-N-(3-(hydroxy(pyridin-2-yl)methyl)phenyl)-3-(trifluoro-methyl)-1H-pyrazole-5-carboxamide (43d) (0.48 g, 1.036 mmol) in dichloromethane (20 mL) at 0° C. was added thionyl chloride (0.240 mL, 3.29 mmol) and allowed to warm to room temperature over 2 h. The reaction mixture was quenched with triethyl amine (1.3 mL, 9.33 mmol) and stirred at room temperature for 1 h. To the chloro compound was added cyclopropylmethanol (8.00 mL, 97 mmol), triethyl amine (1.300 mL, 9.33 mmol) and concentrated in vacuum to remove most of dichloromethane. Triethyl amine (1.3 mL, 9.33 mmol) was added to reaction mixture and heated at 70° C. for 14 h and 100° C. for 6 h. The reaction mixture was diluted with ethyl acetate and filtered. The filtrate was concentrated in vacuum and the residue was purified by flash column chromatography [silica gel eluting with hexanes/ethyl acetate (1:0 to 2:1)] to afford 1-(3-cyanophenyl)-N-(3-((cyclopropyl-methoxy)(pyridin-2-yl)methyl)phenyl)-3-(trifluoromethyl)-1H-pyrazole-5-carboxamide (43e) (231 mg, 43%) as a light brown solid; $^1$H NMR (300 MHz, DMSO-d$_6$) δ 10.51 (s, 1H), 8.29 (ddd, J=4.9, 1.8, 0.9 Hz, 1H), 8.00 (t, J=1.8 Hz, 1H), 7.89-6.95 (m, 11H), 5.30 (s, 1H), 3.11 (d, J=6.8 Hz, 2H), 0.98-0.80 (m, 1H), 0.38-0.21 (m, 2H), 0.08-−0.08 (m, 2H); $^{19}$F NMR (282 MHz, DMSO-d$_6$) δ −60.97; MS (ES+): 540.2 (M+23).

Step-5: Preparation of Racemic 1-(3-(aminomethyl) phenyl)-N-(3-((cyclopropylmethoxy)(pyridin-2-yl) methyl)-phenyl)-3-(trifluoromethyl)-1H-pyrazole-5-carboxamide (43f)

To a solution of 1-(3-cyanophenyl)-N-(3-((cyclopropylmethoxy)(pyridin-2-yl)methyl)phenyl)-3-(trifluoromethyl)-1H-pyrazole-5-carboxamide (43e) (30 mg, 0.058 mmol) in MeOH (2 mL) cooled with ice/water was added nickel(II) chloride hexahydrate (3.0 mg, 0.013 mmol) followed by sodium borohydride (14.00 mg, 0.363 mmol) over a period of 5 min. the reaction mixture was stirred at room temperature for 1 h quenched with N1-(2-aminoethyl)ethane-1,2-diamine (0.015 mL, 0.133 mmol) stirred at room temperature for 0.5 h and concentrated in vacuum to dryness. The residue was treated with ethyl acetate (100 mL), washed with water (50 mL). The aqueous phase was extracted again with ethyl acetate (50 mL). The organic extracts were combined washed with brine (50 mL), dried over MgSO$_4$, filtered and concentrated in vacuum. The crude product was purified by flash column chromatography [silica gel 4 g, eluting with chloroform/methanol (1:0 to 9:1)] to afford Racemic 1-(3-(aminomethyl)phenyl)-N-(3-((cyclopropylmethoxy)(pyridin-2-yl)methyl)phenyl)-3-(trifluoromethyl)-1H-pyrazole-5-carboxamide (43f) (14 mg, 46%) as a off-white solid; $^1$H NMR (300 MHz, DMSO-d$_6$) δ 10.72 (s, 1H), 8.48-8.44 (m, 1H), 7.93-7.04 (m, 12H), 5.46 (s, 1H), 3.77 (s, 2H), 1.14-0.99 (m, 1H), 0.53-0.41 (m, 2H), 0.20-0.11 (m, 2H); $^1$H NMR (300 MHz, DMSO-d$_6$, with D$_2$O exchange) δ 8.48-8.43 (m, 1H), 7.91-7.03 (m, 12H), 5.46 (s, 1H), 3.77 (s, 2H), 3.28 (d, J=6.8 Hz, 2H), 1.14-0.96 (m, 1H), 0.53-0.43 (m, 2H), 0.22-0.09 (m, 2H); $^{19}$F NMR (282 MHz, DMSO-d$_6$) δ −60.73; MS (ES+): 522.3 (M+1).

To a solution of 1-(3-(aminomethyl)phenyl)-N-(3-((cyclopropylmethoxy)(pyridin-2-yl)methyl)phenyl)-3-(trifluoromethyl)-1H-pyrazole-5-carboxamide (43f) (193 mg, 0.37 mmol) in acetone (10 mL) was added conc. HCl (0.123 mL, 1.480 mmol) and concentrated in vacuum to dryness. The residue was dried in vacuum to remove excess HCl and dissolved in IPA (2 mL) with heating to solubilize. To the homogenous solution was added ether (40 mL) and heated at reflux for 30 mins. After cooling to room temperature the solid obtained was collected by filtration, washed with ether and dried under vacuum to furnish 1-(3-(aminomethyl) phenyl)-N-(3-((cyclopropylmethoxy)(pyridin-2-yl)methyl) phenyl)-3-(trifluoromethyl)-1H-pyrazole-5-carboxamide dihydrochloride (43f) (0.227 g, 0.382 mmol, 103% yield) as a white solid; $^1$H NMR (300 MHz, Deuterium Oxide) δ 8.54-8.48 (m, 1H), 8.25 (td, J=8.0, 1.6 Hz, 1H), 7.72 (ddd, J=7.6, 5.8, 1.3 Hz, 1H), 7.67 (d, J=8.1 Hz, 1H), 7.44 (t, J=2.5 Hz, 4H), 7.42-7.35 (m, 1H), 7.34-7.24 (m, 3H), 7.14 (dt, J=7.0, 1.8 Hz, 1H), 5.82 (s, 1H), 4.07 (s, 2H), 3.46-3.31 (m, 1H), 3.28 (m, 1H), 0.99-0.88 (m, 1H), 0.41-0.25 (m, 2H), 0.07-−0.07 (m, 2H); $^{19}$F NMR (282 MHz, D$_2$O) δ −62.34; MS (ES−) 520.3 (M−1); Analysis calculated for C$_{28}$H$_{26}$F$_3$N$_5$O$_2$·1.9HCl·H$_2$O: C, 55.24; H, 4.95; Cl, 11.06; N, 11.50; Found: C, 55.59; H, 5.19; Cl, 10.91; N, 10.83.

Step-6: Preparation of (−)-1-(3-(aminomethyl)phenyl)-N-(3-((cyclopropylmethoxy)(pyridin-2-yl)methyl)-phenyl)-3-(trifluoromethyl)-1H-pyrazole-5-carboxamide (43g) and (+)-1-(3-(aminomethyl)phenyl)-N-(3-((cyclopropylmethoxy)(pyridin-2-yl)methyl)-phenyl)-3-(trifluoromethyl)-1H-pyrazole-5-carboxamide (43h)

Racemic 1-(3-(aminomethyl)phenyl)-N-(3-((cyclopropylmethoxy)(pyridin-2-yl)methyl)phenyl)-3-(trifluoromethyl)-1H-pyrazole-5-carboxamide (43f) (158 mgs) was separated by chiral preparative HPLC using CHIRALPAK AD-H, 5μ, 4.6×250 mm chiral column, flow rate 1 mL/min, Solvent: 90% Hexane/10% EtOH/0.1% DEA, UV=254 nM, to furnish:

1. (−)-1-(3-(aminomethyl)phenyl)-N-(3-((cyclopropylmethoxy)(pyridin-2-yl)methyl)-phenyl)-3-(trifluoromethyl)-1H-pyrazole-5-carboxamide (43g) (0.066 g, 98.2% ee, Rt=10.432 min. This product was repurified by flash column chromatography (silica gel 12 g, eluting 0-25% methanol in chloroform for 13 mins) to afford 50 mgs pure (−)-1-(3-(aminomethyl)phenyl)-N-(3-((cyclopropylmethoxy)(pyridin-2-yl)methyl)-phenyl)-3-(trifluoromethyl)-1H-pyrazole-5-carboxamide (43g); $^1$H NMR (300 MHz, DMSO-d$_6$) δ 10.72 (s, 1H), 8.50-8.43 (m, 1H), 7.81 (td, J=7.7, 1.8 Hz, 1H), 7.65 (t, J=1.8 Hz, 1H), 7.61-7.49 (m, 4H), 7.47-7.38 (m, 2H), 7.34-7.23 (m, 3H), 7.19-7.10 (m, 1H), 5.46 (s, 1H), 3.78 (s, 2H), 3.28 (dd, J=6.8, 1.2 Hz, 2H), 2.37-2.09 (m, 2H), 1.15-0.98 (m, 1H), 0.56-0.33 (m, 2H), 0.27-0.05 (m, 2H); $^{19}$F NMR (282 MHz, DMSO) δ −60.71; MS (ES+) 522.3 (M+1); (ES−) 556.3 (M+Cl); Optical Rotation −11.04 (MeOH, 2.5); Analysis calculated for C$_{28}$H$_{26}$F$_3$N$_5$O$_2$.0.5H$_2$O: C, 63.39; H, 5.13; N, 13.20; Found: C, 63.18; H, 5.13; N, 12.83; Chiral purity checked by performing chiral HPLC using CHIRALPAK AD-H, 5μ, 25 cm, 0.8 mL/min, Solvent: 75% Hexane/24% EtOH/0.1% TEA, UV=260 nM, 14 min run time Rt=6.157 min (peak-1, 43 g, 100%) 9.32 (peak-2, 43h, 0%).

2. (+)-1-(3-(aminomethyl)phenyl)-N-(3-((cyclopropylmethoxy)(pyridin-2-yl)methyl)-phenyl)-3-(trifluoromethyl)-1H-pyrazole-5-carboxamide (43h) (0.071 g, 98.8% ee, Rt=18.373 min). This product was repurified by flash column chromatography (silica gel 12 g, eluting 0-25% methanol in chloroform for 13 mins) to afford 40 mgs pure (+)-1-(3-(aminomethyl)phenyl)-N-(3-((cyclopropylmethoxy)(pyridin-2-yl)methyl)-phenyl)-3-(trifluoromethyl)-1H-pyrazole-5-carboxamide (43h); $^1$H NMR (300 MHz, DMSO-d$_6$) δ 10.56 (s, 1H), 8.37-8.24 (m, 1H), 7.64 (td, J=7.7, 1.8 Hz, 1H), 7.52-7.45 (m, 1H), 7.44-7.32 (m, 4H), 7.31-7.21 (m, 2H), 7.19-7.05 (m, 3H), 6.98 (d, J=7.6 Hz, 1H), 5.29 (s, 1H), 3.61 (s, 2H), 1.00-0.79 (m, 1H), 0.44-0.18 (m, 2H), 0.13--0.14 (m, 2H); $^{19}$F NMR (282 MHz, DMSO-d$_6$) δ −60.71; MS (ES+) 522.3 (M+1); (ES−) 556.3 (M+Cl); Analysis calculated for C$_{28}$H$_{26}$F$_3$N$_5$O$_2$.0.75H$_2$O: C, 62.85; H, 5.18; N, 13.09; Found: C, 63.17; H, 5.24; N, 12.70; Optical Rotation+ 11.51 (MeOH, 2.05); Chiral purity checked by performing chiral HPLC using CHIRALPAK AD-H, 5μ, 25 cm, 0.8 mL/min, Solvent: 75% Hexane/24% EtOH/0.1% TEA, UV=260 nM, 14 min run time Rt=6.157 min (peak-1, 43 g, 0% ee) 9.313 (peak-2, 43h, 100% ee).

Scheme 44

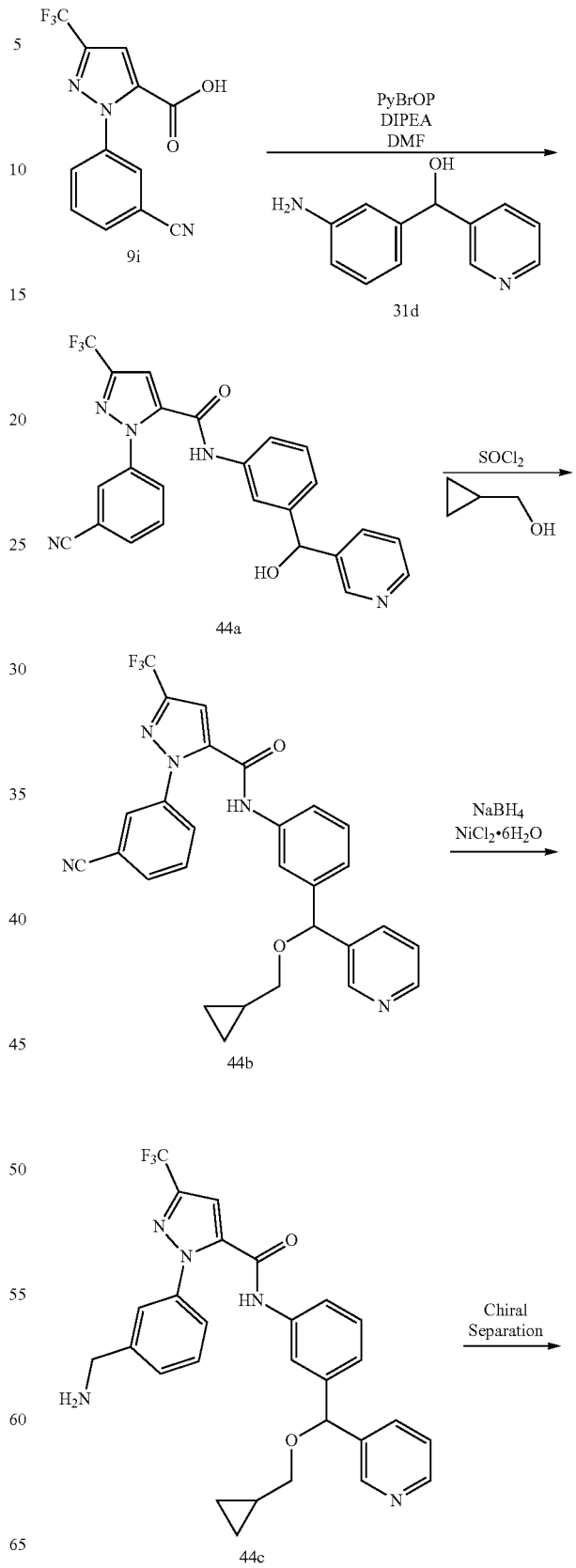

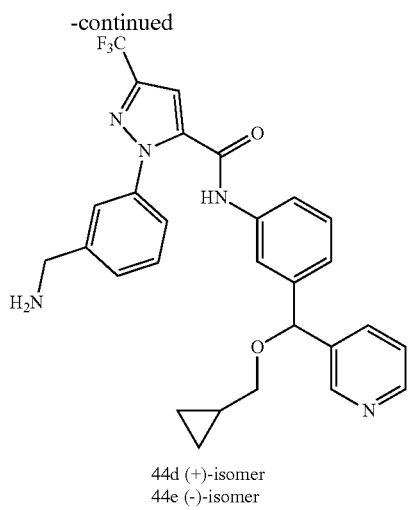

44d (+)-isomer
44e (−)-isomer

Preparation of Racemic 1-(3-(aminomethyl)phenyl)-N-(3-((cyclopropylmethoxy)(pyridin-3-yl)methyl)phenyl)-3-(trifluoromethyl)-1H-pyrazole-5-carboxamide (44c); (+)-1-(3-(aminomethyl)phenyl)-N-(3-((cyclopropylmethoxy)(pyridin-3-yl)methyl)phenyl)-3-(trifluoromethyl)-1H-pyrazole-5-carboxamide (44d) and (−)-1-(3-(aminomethyl)phenyl)-N-(3-((cyclopropylmethoxy)(pyridin-3-yl)methyl)phenyl)-3-(trifluoromethyl)-1H-pyrazole-5-carboxamide (44e)

Step-1: Preparation of 1-(3-Cyanophenyl)-N-(3-(hydroxy(pyridin-3-yl)methyl)phenyl)-3-(trifluoromethyl)-1H-pyrazole-5-carboxamide (44a)

To a solution of 1-(3-cyanophenyl)-3-(trifluoromethyl)-1H-pyrazole-5-carboxylic acid (9i) (0.463 g, 1.648 mmol) in DMF (10 mL) was added (3-aminophenyl)(pyridin-3-yl)methanol (31d) (0.33 g, 1.648 mmol) N-ethyl-N-isopropylpropan-2-amine (1.435 mL, 8.24 mmol) and bromo-trispyrrolidinophosphoniumhexafluorophosphate (PyBrop) (0.922 g, 1.978 mmol) at room temperature. The reaction mixture was stirred at room temperature for 37 h under nitrogen atmosphere. The reaction was diluted with water (25 mL) and extracted with ethyl acetate (2×100 mL). The combined organic layer was washed with brine (50 mL), dried, filtered, and evaporated to dryness. The residue obtained was purified by flash column chromatography [silica gel 40 g, eluting with ethyl acetate in hexanes from 0-100%] to furnish 1-(3-Cyanophenyl)-N-(3-(hydroxy(pyridin-3-yl)methyl)phenyl)-3-(trifluoromethyl)-1H-pyrazole-5-carboxamide (44a) (0.653 g, 1.409 mmol, 86% yield) as a yellow oil; $^1$H NMR (300 MHz, DMSO-d$_6$) δ 10.67 (s, 1H), 8.58 (d, J=2.2 Hz, 1H), 8.43 (dd, J=4.8, 1.7 Hz, 1H), 8.17 (t, J=1.8 Hz, 1H), 8.00 (dt, J=7.7, 1.3 Hz, 1H), 7.90 (ddd, J=8.3, 2.2, 1.1 Hz, 1H), 7.77-7.64 (m, 4H), 7.62-7.52 (m, 1H), 7.37-7.25 (m, 2H), 7.21-7.14 (m, 1H), 6.15 (d, J=3.9 Hz, 1H), 5.77 (d, J=4.0 Hz, 1H); $^{19}$F NMR (282 MHz, DMSO-d$_6$) δ −60.98; MS (ES−) 462.2 (M−1).

Step-2: Preparation of 1-(3-cyanophenyl)-N-(3-((cyclopropylmethoxy)(pyridin-3-yl)methyl)-phenyl)-3-(trifluoromethyl)-1H-pyrazole-5-carboxamide (44b)

To a solution of 1-(3-cyanophenyl)-N-(3-(hydroxy(pyridin-3-yl)methyl)phenyl)-3-(trifluoro-methyl)-1H-pyrazole-5-carboxamide (44a) (0.24 g, 0.518 mmol) in dichloromethane (10 mL) at 0° C. was added thionyl chloride (0.12 mL, 1.647 mmol) and allowed to warm to room temperature over 3 h. The reaction mixture was quenched with triethyl amine (0.22 mL, 1.58 mmol), stirred at room temperature for 1 h, added cyclopropylmethanol (5.00 mL, 60.4 mmol), triethylamine (0.5 mL, 3.59 mmol), concentrated to remove most of dichloromethane followed by addition of more triethylamine (0.5 mL, 3.59 mmol). The reaction mixture was heated at 70° C. for 2 h, 100° C. for 6 h and concentrated in vacuum to dryness. The residue obtained was purified by flash column chromatography [silica gel eluting with hexanes/ethyl acetate (1:0 to 1:1)] to afford 1-(3-cyanophenyl)-N-(3-((cyclopropylmethoxy)(pyridin-3-yl)methyl)-phenyl)-3-(trifluoromethyl)-1H-pyrazole-5-carboxamide (44b) (124 mg, 46%) as a light yellow gum; $^1$H NMR (300 MHz, DMSO-d$_6$) δ 10.70 (s, 1H), 8.60-8.55 (m, 1H), 8.46 (dd, J=4.8, 1.7 Hz, 1H), 8.17 (t, J=1.8 Hz, 1H), 8.01 (dt, J=7.8, 1.3 Hz, 1H), 7.91 (ddd, J=8.2, 2.2, 1.1 Hz, 1H), 7.78-7.58 (m, 5H), 7.42-7.28 (m, 2H), 7.20-7.13 (m, 1H), 5.56 (s, 1H), 3.28-3.24 (m, 2H), 1.13-0.97 (m, 1H), 0.54-0.41 (m, 2H), 0.20-0.12 (m, 2H); $^{19}$F NMR (282 MHz, DMSO-d$_6$) δ −60.97; MS (ES+): 518.3 (M+1).

Step-3: Preparation of Racemic 1-(3-(aminomethyl)phenyl)-N-(3-((cyclopropylmethoxy)(pyridin-3-yl)methyl)phenyl)-3-(trifluoromethyl)-1H-pyrazole-5-carboxamide (44c)

To a solution of 1-(3-cyanophenyl)-N-(3-((cyclopropylmethoxy)(pyridin-3-yl)methyl)-phenyl)-3-(trifluoromethyl)-1H-pyrazole-5-carboxamide (44b) (108 mg, 0.209 mmol) in MeOH (6 mL) cooled with ice/water was added nickel(II) chloride hexahydrate (11.00 mg, 0.046 mmol) followed by portionwise addition of Sodium Borohydride (50 mg, 1.296 mmol) over a period of 5 min. The reaction mixture was stirred at room temperature for 1 h and quenched with N1-(2-aminoethyl)ethane-1,2-diamine (0.05 mL, 1.296 mmol) followed by stirring for additional 0.5 h.

The reaction mixture was concentrated in vacuum to dryness and the residue obtained was dissolved in ethyl acetate (150 mL) and water (75 mL). The aqueous layer was separated extracted with ethyl acetate (75 mL). The combined extracts were washed with brine (75 mL), dried over MgSO$_4$ filtered and concentrated in vacuum. The residue obtained was purified by flash column chromatography [silica gel twice with 4 g, eluting with chloroform/methanol (1:0 to 9:1)] to furnish Racemic 1-(3-(aminomethyl)phenyl)-N-(3-((cyclopropylmethoxy)(pyridin-3-yl)methyl)phenyl)-3-(trifluoromethyl)-1H-pyrazole-5-carboxamide (44c) (0.042 g, 39%) as a white solid; $^1$H NMR (300 MHz, DMSO-d$_6$) δ 10.74 (s, 1H), 8.57 (d, J=1.8 Hz, 1H), 8.46 (dd, J=4.8, 1.7 Hz, 1H), 7.75-7.13 (m, 11H), 5.55 (s, 1H), 3.80 (s, 2H), 3.26 (dd, J=6.8, 2.5 Hz, 2H), 1.12-1.00 (m, 1H), 0.53-0.35 (m, 2H), 0.22-0.06 (m, 2H); $^{19}$F NMR (282 MHz, DMSO-d$_6$) δ −60.74; MS (ES+): 522.3 (M+1).

Step-4: Preparation of (+)-1-(3-(aminomethyl)phenyl)-N-(3-((cyclopropylmethoxy)(pyridin-3-yl)methyl)phenyl)-3-(trifluoromethyl)-1H-pyrazole-5-carboxamide (44d) and (−)-1-(3-(aminomethyl)phenyl)-N-(3-((cyclopropylmethoxy)(pyridin-3-yl)methyl)phenyl)-3-(trifluoromethyl)-1H-pyrazole-5-carboxamide (44e)

Racemic 1-(3-(aminomethyl)phenyl)-N-(3-((cyclopropylmethoxy)(pyridin-3-yl)methyl)phenyl)-3-(trifluoromethyl)-1H-pyrazole-5-carboxamide (44c) (231 mgs) was separated using chiral preparative HPLC using CHIRALPAK AD-H, 5μ, 4.6×250 mm, flow rate 1 mL/min, Solvent: 80% Hexane/20% EtOH/0.1% DEA, UV=254 nM to furnish:

1. (+)-1-(3-(aminomethyl)phenyl)-N-(3-((cyclopropylmethoxy)(pyridin-3-yl)methyl)phenyl)-3-(trifluoromethyl)-1H-pyrazole-5-carboxamide (44d) (0.0791 g, Rt=6.28 min, 99.8% ee). This product was repurified by flash column chromatography (silica gel 12 g, eluting 0-25% methanol in chloroform for 13 mins at a flow rate of 50 mL/min) to afford pure (+)-1-(3-(aminomethyl)phenyl)-N-(3-((cyclopropylmethoxy)(pyridin-3-yl)methyl)phenyl)-3-(trifluoromethyl)-1H-pyrazole-5-carboxamide (44d) (60 mgs) as a white solid; $^1$H NMR (300 MHz, DMSO-$d_6$) δ 10.74 (s, 1H), 8.57 (d, J=2.2 Hz, 1H), 8.46 (dd, J=4.8, 1.7 Hz, 1H), 7.75-7.26 (m, 11H), 7.21-7.11 (m, 1H), 5.55 (s, 1H), 3.77 (s, 2H), 3.26 (dd, J=6.8, 2.3 Hz, 2H), 1.16-0.96 (m, 1H), 0.56-0.37 (m, 2H), 0.27-0.02 (m, 2H); $^{19}$F NMR (282 MHz, DMSO-$d_6$) δ −60.71; MS (ES+) 522.3 (M+1); (ES−) 520.3 (M+1); Optical rotation=+10.86 (methanol, 3.0). Chiral purity checked by performing chiral HPLC using AD-H column 76/24/0.1 (Hexane/ethanol/TEA) 0.8 mL/min UV 260 nM, 14 mins run time (Temp 25° C.). Rt=6.817 (100%, peak-1, 44d), Rt=10.043 (0%, peak-2, 44e); Analysis calculated for $C_{28}H_{26}F_3N_5O_2 \cdot 0.75H_2O$: C, 62.85; H, 5.18; N, 13.09; found: C, 62.90; H, 5.11; N, 12.73.

2. (−)-1-(3-(aminomethyl)phenyl)-N-(3-((cyclopropylmethoxy)(pyridin-3-yl)methyl)phenyl)-3-(trifluoromethyl)-1H-pyrazole-5-carboxamide (44e) (0.083 g, Rt=8.961 min, 99.0% ee). This product was repurified by flash column chromatography (silica gel 12 g, eluting 0-25% methanol in chloroform for 13 mins at a flow rate of 50 mL/min) to afford (−)-1-(3-(aminomethyl)phenyl)-N-(3-((cyclopropylmethoxy)(pyridin-3-yl)methyl)phenyl)-3-(trifluoromethyl)-1H-pyrazole-5-carboxamide (44e) (60 mgs) as a white solid; $^1$H NMR (300 MHz, DMSO-$d_6$) δ 10.74 (s, 1H), 8.57 (d, J=2.2 Hz, 1H), 8.46 (dd, J=4.8, 1.7 Hz, 1H), 7.70 (dt, J=8.0, 2.0 Hz, 1H), 7.64 (t, J=1.8 Hz, 1H), 7.61-7.50 (m, 3H), 7.43 (d, J=2.7 Hz, 1H), 7.40 (d, J=8.6 Hz, 1H), 7.37-7.28 (m, 3H), 7.16 (d, J=7.6 Hz, 1H), 5.55 (s, 1H), 3.77 (s, 2H), 3.25 (dd, J=6.9, 2.4 Hz, 2H), 1.16-0.96 (m, 1H), 0.56-0.34 (m, 2H), 0.27-0.04 (m, 2H); $^{19}$F NMR (282 MHz, DMSO-$d_6$) δ −60.71; MS (ES+) 522.3 (M+1); (ES−) 520.3 (M+1); Optical rotation=−11.33 (methanol, 3.0); Chiral purity checked by performing chiral HPLC using AD-H column 76/24/0.1 (Hexane/ethanol/TEA) 0.8 mL/min UV 260 nM, 14 mins run time (Temp 25° C.). $R_t$=6.817 (0% ee, peak-1, 44d), $R_t$=9.943 (100%, peak-2, 44e); Analysis calculated for $C_{28}H_{26}F_3N_5O_2 \cdot 0.75H_2O$: C, 62.85; H, 5.18; N, 13.09; Found: C, 62.88; H, 5.12; N, 12.70.

Scheme 45

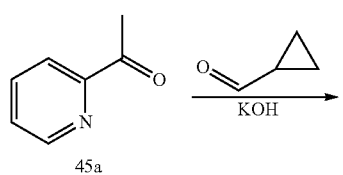

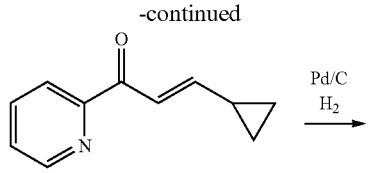

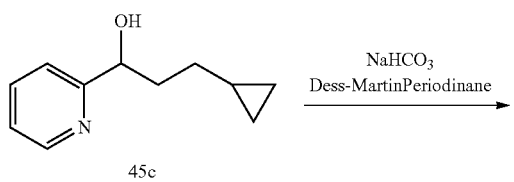

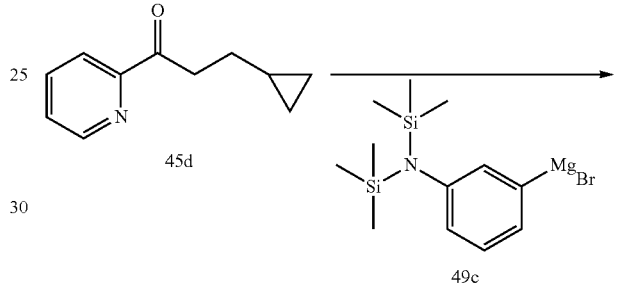

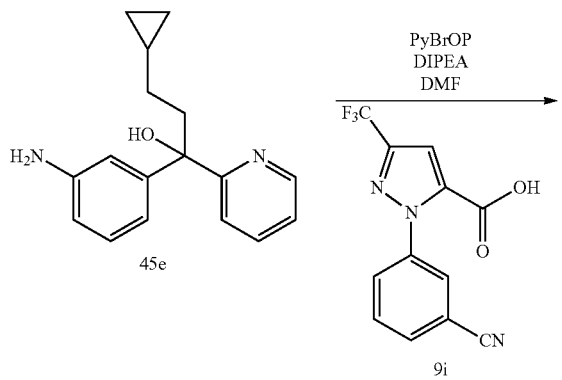

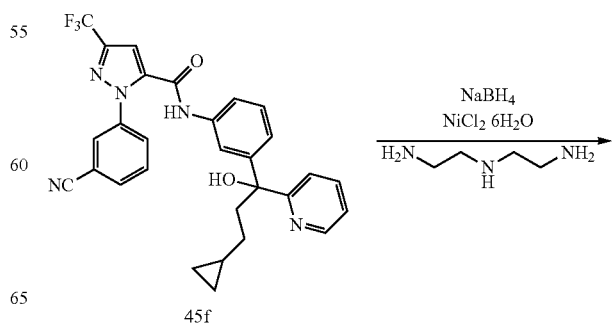

245

-continued

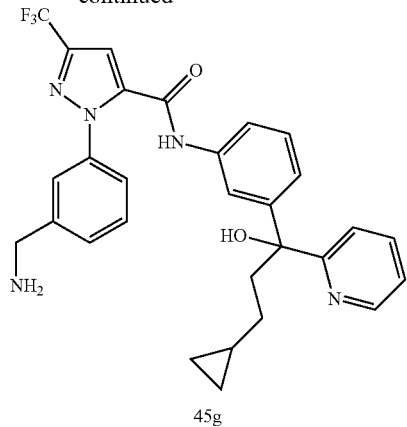

45g

Preparation of 1-(3-(aminomethyl)phenyl)-N-(3-(3-cyclopropyl-1-hydroxy-1-(pyridin-2-yl)propyl)phenyl)-3-(trifluoromethyl)-1H-pyrazole-5-carboxamide (45g)

Step-1: Preparation of (E)-3-cyclopropyl-1-(pyridin-2-yl)prop-2-en-1-one (45b)

To a stirred solution of 1-(pyridin-2-yl)ethanone (45a) (1.516 mL, 13.27 mmol) in methanol (100 mL) cooled to 0° C. was added cyclopropanecarboxaldehyde (1.5 mL, 19.90 mmol) and aqueous potassium hydroxide (1N, 2.65 mL, 2.65 mmol). The reaction was allowed to warm to room temperature overnight. The reaction was acidified with 1 N hydrochloric acid and concentrated in vacuum to remove methanol. The crude residue was dissolved in ethyl acetate (100 mL) washed with sodium carbonate solution, water (2×50 mL), brine (50 mL), dried, filtered and concentrated in vacuum. The crude residue was purified by flash column chromatography (silicagel, 12 g, eluting with ethyl acetate in hexanes 0 to 100%) to afford afford pure (E)-3-cyclopropyl-1-(pyridin-2-yl)prop-2-en-1-one (45b) (479 mg, 20.85%), which was good to be used as such for next, MS (ES+) 174.1 (M+1).

Step-2: Preparation of 3-cyclopropyl-1-(pyridin-2-yl)propan-1-ol (45c)

To Pd/C (10%, 0.230 g, 0.216 mmol) in methanol (50 mL) was added (E)-3-cyclopropyl-1-(pyridin-2-yl)prop-2-en-1-one (45b) (1.5 g, 8.66 mmol) and hydrogenated at 60 psi for 2 h. The reaction mixture was filtered through Celite and filtrate concentrated in vacuum. The crude residue was purified by flash column chromatography (silicagel, 12 g, eluting with CMA 80 in chloroform 0-100%) to afford 3-cyclopropyl-1-(pyridin-2-yl)propan-1-ol (45c) (1.02 g, 66.5%) as an oil. $^1$H NMR (300 MHz, DMSO-$d_6$) δ 8.46 (ddd, J=4.9, 1.8, 0.9 Hz, 1H), 7.76 (td, J=7.7, 1.8 Hz, 1H), 7.46 (dt, J=8.1, 1.2 Hz, 1H), 7.22 (ddd, J=7.5, 4.8, 1.2 Hz, 1H), 5.29 (d, J=5.0 Hz, 1H), 4.58 (dt, J=8.2, 4.8 Hz, 1H), 1.83 (dddd, J=13.6, 9.2, 7.2, 4.6 Hz, 1H), 1.66 (dtd, J=13.3, 8.1, 6.7 Hz, 1H), 1.22 (dt, J=8.1, 6.5 Hz, 2H), 0.73-0.58 (m, 1H), 0.41-0.29 (m, 2H), 0.03--0.06 (m, 2H); MS (ES+) 200.1 (M+23).

Step-3: Preparation of 3-cyclopropyl-1-(pyridin-2-yl)propan-1-one (45d)

To a stirred solution of 3-cyclopropyl-1-(pyridin-2-yl)propan-1-ol (45c) (1 g, 5.64 mmol) in dichloromethane (10

246 mL) at 0° C. was added NaHCO$_3$ (1.422 g, 16.93 mmol) and Dess-MartinPeriodinane (4.79 g, 11.28 mmol). The reaction mixture was stirred at 0° C. for 30 minutes and warmed to room temperature in 15 mins. The reaction was stirred at room temperature for 1 hr and quenched by adding aqueous saturated sodium bicarbonate (25 mL), extracted with dichloromethane (2×50 mL). The organic layers were combined, washed with water (2×25 mL), brine (25 mL), dried, filtered and concentrated in vacuum. The crude residue was purified by column chromatography (silicagel, 12 g, eluting with 0-1005 ethyl acetate in hexane) to afford 3-cyclopropyl-1-(pyridin-2-yl)propan-1-one (45d) (836 mg, 85%) as an oil; $^1$H NMR (300 MHz, DMSO-$d_6$) δ 8.73 (ddd, J=4.8, 1.7, 1.0 Hz, 1H), 8.13-7.87 (m, 2H), 7.77-7.56 (m, 1H), 3.26 (t, J=7.3 Hz, 2H), 1.54 (q, J=7.2 Hz, 2H), 0.83-0.67 (m, 1H), 0.45-0.32 (m, 2H), 0.08-0.01 (m, 2H); MS (ES+) 176.1 (M+1).

Step-4: Preparation of 1-(3-aminophenyl)-3-cyclopropyl-1-(pyridin-2-yl)propan-1-ol (45e)

To a stirred solution of 3-cyclopropyl-1-(pyridin-2-yl)propan-1-one (45d) (400 mg, 2.283 mmol) in tetrahydrofuran (15 mL) was added (3-(bis(trimethylsilyl)amino)phenyl)magnesium bromide (49c) (2.283 mL, 2.283 mmol) at 0° C. Reaction was allowed to warm to room temperature and stirred for 2 h. The reaction was quenched with ammonium chloride solution (25 mL), extracted with ethyl acetate (2×50 mL). the organic layers were combined, washed with water (2×25 mL), brine (25 mL), dried, filtered and concentrated in vacuum. The crude residue was purified by flash column chromatography (silicagel, 25 g eluting with CMA 80 in chloroform 0-100%) to afford 1-(3-aminophenyl)-3-cyclopropyl-1-(pyridin-2-yl)propan-1-ol (45e) (365 mg, 59.6%). This was pure enough to be used as such in next step; $^1$H NMR (300 MHz, DMSO-$d_6$) δ 8.47 (ddd, J=4.9, 1.8, 0.9 Hz, 1H), 7.70 (ddd, J=8.0, 7.3, 1.8 Hz, 1H), 7.58 (dt, J=8.0, 1.1 Hz, 1H), 7.17 (ddd, J=7.4, 4.8, 1.2 Hz, 1H), 6.86 (t, J=7.8 Hz, 1H), 6.75 (t, J=1.9 Hz, 1H), 6.64 (ddd, J=7.7, 1.8, 1.1 Hz, 1H), 6.31 (ddd, J=7.8, 2.2, 1.0 Hz, 1H), 5.51 (s, 1H), 4.93 (s, 2H), 2.36 (ddd, J=13.3, 11.1, 5.2 Hz, 2H), 1.17-0.89 (m, 2H), 0.60 (dqd, J=11.9, 7.0, 3.9 Hz, 1H), 0.39-0.26 (m, 2H), -0.04--0.17 (m, 2H); MS (ES+) 291.2 (M+23).

Step-5: Preparation of 1-(3-cyanophenyl)-N-(3-(3-cyclopropyl-1-hydroxy-1-(pyridin-2-yl)propyl)phenyl)-3-(trifluoromethyl)-1H-pyrazole-5-carboxamide (45f)

To a solution of 1-(3-cyanophenyl)-3-(trifluoromethyl)-1H-pyrazole-5-carboxylic acid (9i) (297 mg, 1.056 mmol) in DMF (6 mL) was added 1-(3-aminophenyl)-3-cyclopropyl-1-(pyridin-2-yl)propan-1-ol (45e) (340 mg, 1.267 mmol), N-ethyl-N-isopropylpropan-2-amine (1.471 mL, 8.45 mmol) and Bromo-tris-pyrrolidino phosphoniumhexafluorophosphate (PyBroP, 541 mg, 1.161 mmol) at room temperature and stirred at 25° C. for 16 h. The reaction mixture was diluted with water (50 mL) and extracted with ethyl acetate (100 mL, 50 mL). The organic layers were combined and dried over anhydrous MgSO$_4$, filtered, concentrated under reduced pressure to dryness. The residue obtained was purified by flash column chromatography (silica gel 12 g, eluting with CMA 80 in chloroform 0-100%) to furnish 1-(3-cyanophenyl)-N-(3-(3-cyclopropyl-1-hydroxy-1-(pyridin-2-yl)propyl)phenyl)-3-(trifluoromethyl)-1H-pyrazole-5-carboxamide (45f) (328 mg, 58.4%); MS (ES+) 532.2 (M+1).

Step-6: Preparation of 1-(3-(aminomethyl)phenyl)-N-(3-(3-cyclopropyl-1-hydroxy-1-(pyridin-2-yl)propyl)phenyl)-3-(trifluoromethyl)-1H-pyrazole-5-carboxamide (45g)

To a stirred solution of 1-(3-cyanophenyl)-N-(3-(3-cyclopropyl-1-hydroxy-1-(pyridin-2-yl)propyl)phenyl)-3-(trifluoromethyl)-1H-pyrazole-5-carboxamide (45f) (300 mg, 0.564 mmol) in methanol (25 mL) at 0° C. was added nickel(II) chloride hexahydrate (29.2 mg, 0.123 mmol), To this sodium tetrahydroborate (133 mg, 3.53 mmol) was added in small portions over a period of 15 minutes. The reaction was stirred for 15 minutes, quenched by adding N1-(2-aminoethyl)ethane-1,2-diamine (0.135 mL, 1.298 mmol) and stirred for 30 minutes at room temperature. The reaction mixture was concentrated in vacuum to remove methanol. The residue was adsorbed on silicagel and purified twice by flash column chromatography (silica gel, 12 g, eluting with CMA 80 in chloroform 0 to 100%) and (silica gel 2×4 g, eluting with methanol in chloroform 0 to 30%) to afford 1-(3-(aminomethyl)phenyl)-N-(3-(3-cyclopropyl-1-hydroxy-1-(pyridin-2-yl)propyl)phenyl)-3-(trifluoromethyl)-1H-pyrazole-5-carboxamide (70 mg, 0.131 mmol, 23.16% yield) as a colorless solid; $^1$HNMR (300 MHz, DMSO-$d_6$) δ 10.75 (s, 1H, $D_2O$ exchangeable), 8.68-8.48 (m, 1H), 7.87-7.77 (m, 2H), 7.73-7.68 (m, 1H), 7.67 (s, 1H), 7.65-7.60 (m, 2H), 7.54-7.47 (m, 2H), 7.40 (ddd, J=7.5, 3.9, 1.9 Hz, 1H), 7.37-7.31 (m, 1H), 7.31-7.25 (m, 2H), 5.84 (s, 1H, $D_2O$ exchangeable), 3.87 (s, 2H), 2.56-2.44 (m, 2H), 2.33 (s, 2H, $D_2O$ exchangeable), 1.12 (m, 2H), 0.78-0.56 (m, 1H), 0.49-0.32 (m, 2H), −0.01 (m, 2H); MS (ES+) 536.3 (M+1), (ES−) 534.1 (M−1), 570.0 (M+23).

Scheme 46

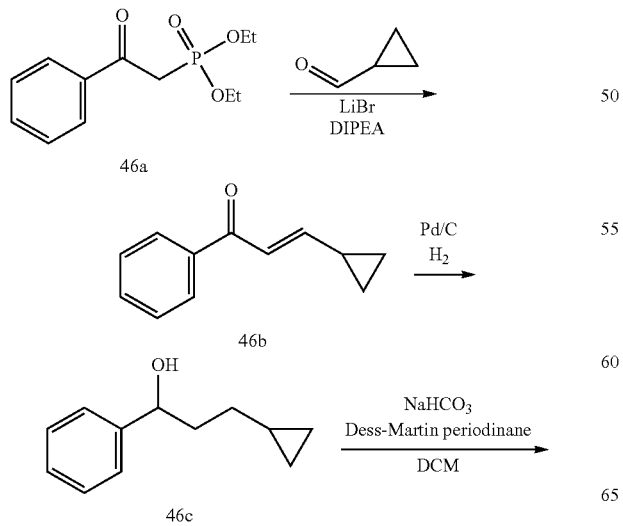

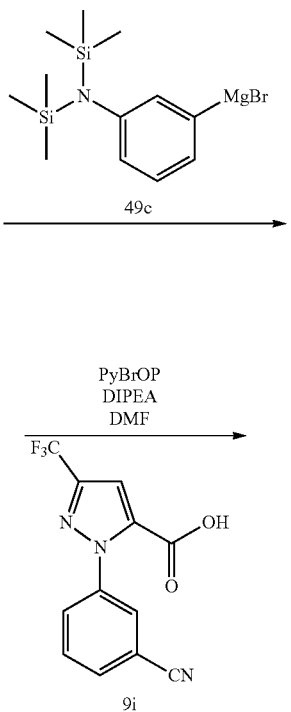

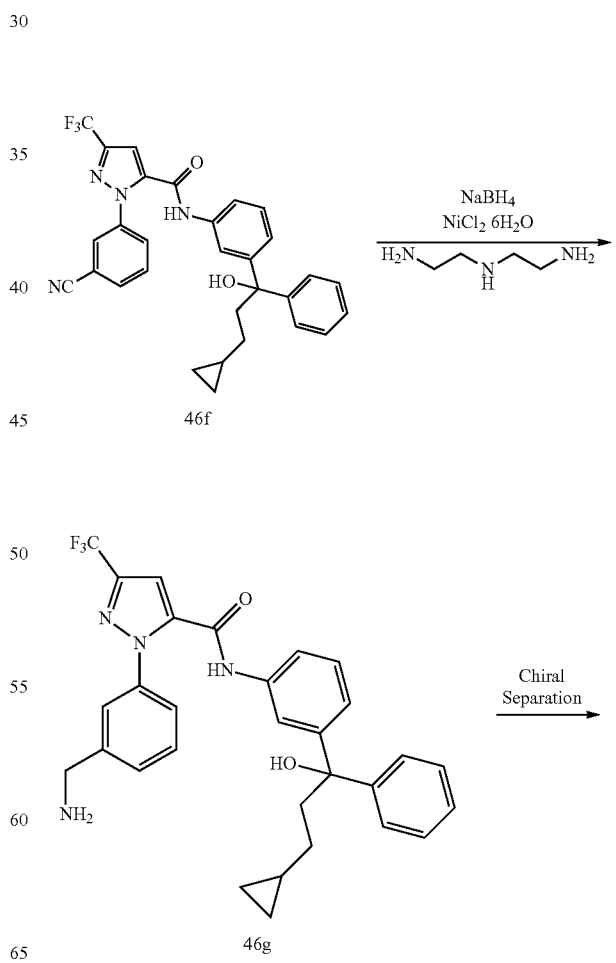

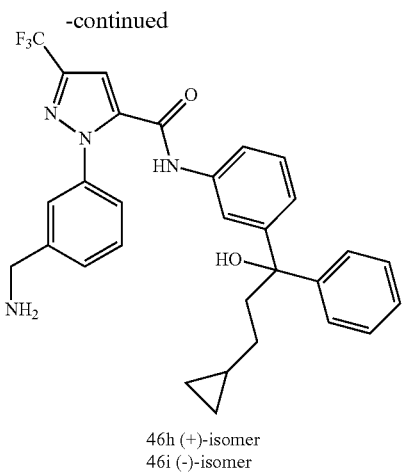

46h (+)-isomer
46i (−)-isomer

Preparation of Racemic 1-(3-(aminomethyl)phenyl)-N-(3-(3-cyclopropyl-1-hydroxy-1-phenylpropyl)phenyl)-3-(trifluoromethyl)-1H-pyrazole-5-carboxamide (46g), (+)-1-(3-(aminomethyl)phenyl)-N-(3-(3-cyclopropyl-1-hydroxy-1-phenylpropyl)phenyl)-3-(trifluoromethyl)-1H-pyrazole-5-carboxamide (46h) and (−)-1-(3-(aminomethyl)phenyl)-N-(3-(3-cyclopropyl-1-hydroxy-1-phenylpropyl)phenyl)-3-(trifluoromethyl)-1H-pyrazole-5-carboxamide (46i)

Step-1: Preparation of (E)-3-cyclopropyl-1-phenyl-prop-2-en-1-one (46b)

To a stirred solution of diethyl 2-oxo-2-phenylethylphosphonate (46a) (1.8 g, 7.02 mmol) in acetonitrile (50 mL) was added LiBr (0.610 g, 7.02 mmol) and diisopropylethylamine (DIPEA, 2.454 mL, 14.05 mmol), cyclopropanecarboxaldehyde (0.529 mL, 7.02 mmol) was added drop-wise at room temperature and reaction stirred at room temperature for 16 h. The reaction mixture was filtered through Celite and concentrated in vacuum. The crude residue was purified by flash column chromatography (silica gel, 24 g, eluting with ethyl acetate in hexanes 0-100%) to afford (E)-3-cyclopropyl-1-phenylprop-2-en-1-one (46b) (315 mg, 26.0%) as an oil; $^1$H NMR (300 MHz, Chloroform-d) δ 8.00-7.87 (m, 2H), 7.63-7.42 (m, 3H), 7.03 (d, J=15.1 Hz, 1H), 6.56 (dd, J=15.1, 10.3 Hz, 1H), 1.83-1.59 (m, 1H), 1.14-0.94 (m, 2H), 0.84-0.65 (m, 2H); MS (ES+): 173.1 (M+1).

Step-2: Preparation of 3-cyclopropyl-1-phenylpropan-1-ol (46c)

To a suspension of Pd/C (10%, 97 mg, 0.091 mmol) in ethyl acetate (35 mL) was added (E)-3-cyclopropyl-1-phenylprop-2-en-1-one (46b) (315 mg, 1.829 mmol) and hydrogenated at 60 psi for 1 h. The reaction was filtered through Celite and concentrated in vacuum. The crude residue was purified by flash column chromatography (silica gel, 24 g, eluting with ethyl acetate in hexanes 0-30%) to afford (46c) (260 mg, 81%) as an oil; $^1$H NMR (300 MHz, DMSO-d$_6$) δ 7.40-7.14 (m, 5H), 5.10 (d, J=4.4 Hz, 1H), 4.52 (ddd, J=7.3, 5.7, 4.4 Hz, 1H), 1.76-1.55 (m, 2H), 1.35-1.08 (m, 2H), 0.72-0.59 (m, 1H), 0.43-0.28 (m, 2H), −0.04 (ddt, J=5.2, 4.2, 2.0 Hz, 2H); MS (ES+): 199.1 (M+Na).

Step-3: Preparation of 3-cyclopropyl-1-phenylpropan-1-one (46d)

To a stirred solution of 3-cyclopropyl-1-phenylpropan-1-ol (46c) (0.250 g, 1.418 mmol) in dichloromethane (30 mL) at 0° C. was added sodium bicarbonate (0.336 g, 4.00 mmol), Dess-Martin periodinane (1.191 g, 2.67 mmol) and stirred for 30 mins. The reaction mixture was warmed to room temperature in 15 mins, filtered through a Celite pad and concentrated in vacuum. The crude residue was purified by flash column chromatography (silica gel, 24 g, eluting with ethyl acetate in hexanes 0-30%) to afford 3-cyclopropyl-1-phenylpropan-1-one (46d)(150 mg, 60.7%) as an oil; $^1$H NMR (300 MHz, DMSO-d$_6$) δ 7.98-7.87 (m, 2H), 7.63-7.53 (m, 1H), 7.47 (ddt, J=8.2, 6.6, 1.2 Hz, 2H), 3.04 (t, J=7.2 Hz, 2H), 1.46 (q, J=7.1 Hz, 2H), 0.81-0.59 (m, 1H), 0.41-0.24 (m, 2H), 0.04−−0.05 (m, 2H); MS (ES+): 197.1 (M+Na).

Step-4: Preparation of 1-(3-aminophenyl)-3-cyclopropyl-1-phenylpropan-1-ol (46e)

To a stirred solution of 3-cyclopropyl-1-phenylpropan-1-one (46d) (150 mg, 0.861 mmol) in tetrahydrofuran (10 mL) was added (3-(bis(trimethylsilyl)amino)phenyl)magnesium bromide (49c) (1.722 mL, 1.722 mmol) at 0° C. The reaction was allowed to stir for 2 h at 0° C., quenched with saturated aqueous ammonium chloride solution (25 mL) and extracted with ethyl acetate (2×50 mL). The organic layers were combined, washed with water (2×25 mL), brine (25 mL), dried, filtered and concentrated in vacuum. The crude residue was purified by flash column chromatography (silica gel, 24 g, eluting with ethyl acetate in hexanes 0-100%) to afford 1-(3-aminophenyl)-3-cyclopropyl-1-phenylpropan-1-ol (46e) (180 mg, 78%); $^1$H NMR (300 MHz, DMSO-d6) δ 7.44-7.33 (m, 2H), 7.30-7.18 (m, 2H), 7.17-7.07 (m, 1H), 6.88 (t, J=7.8 Hz, 1H), 6.68 (t, J=1.9 Hz, 1H), 6.55 (dt, J=7.7, 1.3 Hz, 1H), 6.32 (ddd, J=7.8, 2.2, 0.9 Hz, 1H), 5.21 (s, 1H), 4.93 (s, 2H), 2.23 (t, J=8.2 Hz, 2H), 1.07 (ddd, J=28.3, 13.6, 6.4 Hz, 2H), 0.61 (dd, J=11.7, 6.1 Hz, 1H), 0.40-0.26 (m, 2H), −0.09 (td, J=5.2, 3.5 Hz, 2H); MS (ES+): 290.2 (M+Na), MS (ES−): 266.1 (M−1).

Step-5: Preparation of 1-(3-cyanophenyl)-N-(3-(3-cyclopropyl-1-hydroxy-1-phenylpropyl)phenyl)-3-(trifluoromethyl)-1H-pyrazole-5-carboxamide (46f)

To a solution of 1-(3-cyanophenyl)-3-(trifluoromethyl)-1H-pyrazole-5-carboxylic acid (9i) (1.008 g, 3.58 mmol) in N,N-dimethylformamide (20 mL) was added 1-(3-aminophenyl)-3-cyclopropyl-1-phenylpropan-1-ol (46e) (1.15 g, 4.30 mmol), N-ethyl-N-isopropylpropan-2-amine (5.01 mL, 28.7 mmol) and Bromo-tris-pyrrolidino phosphoniumhexafluorophosphate (PyBrOP, 1.838 g, 3.94 mmol) at room temperature. The reaction mixture was stirred at 25° C. for 16 h quenched with water (100 mL) and extracted with ethyl acetate (2×150 mL). The organic layers were combined dried over anhydrous MgSO$_4$, filtered, and concentrated in under reduced pressure to dryness. The residue was purified by flash column chromatography (silica gel 25 g, eluting with hexanes in ethyl acetate/hexanes from 0-40 to 100%) to afford 1-(3-cyanophenyl)-N-(3-(3-cyclopropyl-1-hydroxy-1-phenylpropyl)phenyl)-3-(trifluoromethyl)-1H-pyrazole-5-carboxamide (46f) (1.6 g, 84%) which was taken as such for next step; $^1$H NMR (300 MHz, DMSO-d$_6$) δ 10.61 (s, 1H), 8.21-8.13 (m, 1H), 8.00 (dt, J=7.7, 1.3 Hz, 1H), 7.90 (ddd, J=8.3, 2.3, 1.2 Hz, 1H), 7.78-7.66 (m, 3H), 7.62-7.54 (m, 1H), 7.46-7.36 (m, 2H), 7.29-7.23 (m, 3H), 7.19-7.14 (m, 2H), 5.49 (s, 1H), 2.36-2.24 (m, 2H), 1.08 (d, J=8.7 Hz, 2H), 0.63 (s, 1H), 0.43-0.26 (m, 2H), −0.04−−0.14 (m, 2H); MS (ES−) 529.2 (M−1).

Step-6: Preparation of Racemic 1-(3-(aminomethyl)phenyl)-N-(3-(3-cyclopropyl-1-hydroxy-1-phenylpropyl)phenyl)-3-(trifluoromethyl)-1H-pyrazole-5-carboxamide (46g)

To a stirred solution of 1-(3-cyanophenyl)-N-(3-(3-cyclopropyl-1-hydroxy-1-phenylpropyl)phenyl)-3-(trifluoromethyl)-1H-pyrazole-5-carboxamide (46f) (0.77 g, 1.451 mmol) in methanol (75 mL) at 0° C. was added nickel(II) chloride hexahydrate (0.075 g, 0.316 mmol) followed by sodium tetrahydroborate (0.549 g, 14.51 mmol) in small portions over a period of 15 mins. The reaction was stirred for 15 mins, quenched by adding N1-(2-aminoethyl)ethane-1,2-diamine (0.076 mL, 0.737 mmol), stirred for additional 30 mins at room temperature and concentrated in vacuum to remove methanol. The reaction mixture was diluted water (25 mL) and extracted with ethyl acetate (3×50 mL). the organic layers were combined washed with water (2×20 mL), brine (20 mL), dried and concentrated. The crude residue was purified by flash column chromatography (silica gel 12 g, eluting with CMA 80 in chloroform 0 100%) to afford Racemic 1-(3-(aminomethyl)phenyl)-N-(3-(3-cyclopropyl-1-hydroxy-1-phenylpropyl)phenyl)-3-(trifluoromethyl)-1H-pyrazole-5-carboxamide (46g) as a colorless solid; $^1$H NMR (300 MHz, DMSO-$d_6$) δ 10.65 (s, 1H, $D_2O$ exchangeable), 7.71-7.66 (m, 1H), 7.60-7.50 (m, 3H), 7.45-7.38 (m, 4H), 7.34-7.11 (m, 6H), 5.48 (s, 1H, $D_2O$ exchangeable), 3.78 (s, 2H), 2.30 (dd, J=10.5, 5.8 Hz, 4H, 2H $D_2O$ exchangeable), 1.06 (dd, J=10.7, 5.7 Hz, 2H), 0.62 (q, J=9.4, 7.3 Hz, 1H), 0.41-0.25 (m, 2H), −0.08 (tt, J=5.4, 2.8 Hz, 2H); Mass spec (ES+) 535.3 (M+1), 557.3 (M+23), (ES−) 533.3 (M−1), 569.3 (M+35).

Step-7: Preparation of (+)-1-(3-(aminomethyl)phenyl)-N-(3-(3-cyclopropyl-1-hydroxy-1-phenylpropyl)phenyl)-3-(trifluoromethyl)-1H-pyrazole-5-carboxamide (46h) and (−)-1-(3-(aminomethyl)phenyl)-N-(3-(3-cyclopropyl-1-hydroxy-1-phenylpropyl)phenyl)-3-(trifluoromethyl)-1H-pyrazole-5-carboxamide (46i)

Racemic 1-(3-(aminomethyl)phenyl)-N-(3-(3-cyclopropyl-1-hydroxy-1-phenylpropyl)phenyl)-3-(trifluoromethyl)-1H-pyrazole-5-carboxamide (46g) (367 mg) was separated using chiral preparative HPLC using Purified by chiral preparative HPLC using CHIRALPAK IC, 5µ, 4.6×250 mm, flow rate 1 mL/min, Solvent: 50% Hexane/49% DCM/1% EtOH/0.1% DEA, UV=280 nM, 25° C., to furnish:
1. Peak-1 corresponding to (+)-1-(3-(aminomethyl)phenyl)-N-(3-(3-cyclopropyl-1-hydroxy-1-phenylpropyl)phenyl)-3-(trifluoromethyl)-1H-pyrazole-5-carboxamide (46h) (101.9 mg, 97.1% ee); Chiral HPLC (Rt=8.975 min, 98.5689% peak-, 1 compound 46h), (Rt=10.075 min, 1.4311% peak-2, compound 46i). This compound was repurified by flash column chromatography (silica gel 4 g, eluting 0-25-100% CMA-80 in chloroform for 25 mins) to afford (+)-1-(3-(aminomethyl)phenyl)-N-(3-(3-cyclopropyl-1-hydroxy-1-phenylpropyl)phenyl)-3-(trifluoromethyl)-1H-pyrazole-5-carboxamide (46h) (84 mg, 91.49 ee); Optical rotation: $[α]_D$=+1.674 [$CH_3OH$]; $^1$H NMR (300 MHz, DMSO-$d_6$) δ 10.65 (s, 1H, $D_2O$ exchangeable), 7.68 (s, 1H), 7.60-7.50 (m, 3H), 7.48-7.37 (m, 4H), 7.35-7.21 (m, 4H), 7.16 (q, J=7.1 Hz, 2H), 5.48 (s, 1H, $D_2O$ exchangeable), 3.78 (s, 2H), 2.39-2.21 (m, 2H), 1.14-1.00 (m, 2H), 0.61 (h, J=6.4 Hz, 1H), 0.34 (dq, J=8.1, 4.0 Hz, 2H), −0.08 (t, J=4.8 Hz, 2H); MS (ES+) 535.3 (M+1), (ES−) 533.3 (M−1); Analysis calculated for $C_{30}H_{29}F_3N_4O_2 \cdot 0.75H_2O$: C, 65.74; H, 5.61; N, 10.22; Found C, 66.10; H, 5.82; N, 9.78.

2. Peak-2 corresponding to (−)-1-(3-(aminomethyl)phenyl)-N-(3-(3-cyclopropyl-1-hydroxy-1-phenylpropyl)phenyl)-3-(trifluoromethyl)-1H-pyrazole-5-carboxamide (46i) (98.8 mg, 97.5% ee); Chiral HPLC (Rt=9.039 min, 1.2741% peak-1, compound 46h) (Rt=10.052, 98.7259% peak-2, compound 46i). This compound was repurified by flash column chromatography (silica gel 12 g, eluting 0-30% MeOH in chloroform for 25 mins) to afford (−)-1-(3-(aminomethyl)phenyl)-N-(3-(3-cyclopropyl-1-hydroxy-1-phenylpropyl)phenyl)-3-(trifluoromethyl)-1H-pyrazole-5-carboxamide (46i) (45 mgs, 87.3% ee) as a white solid; Optical rotation: $[α]_D$=(−)2.00 [$CH_3OH$, 0.505]; $^1$H NMR (300 MHz, DMSO-$d_6$) δ 10.66 (s, 1H, $D_2O$ exchangeable), 7.72-7.66 (m, 1H), 7.61-7.50 (m, 3H), 7.47-7.37 (m, 4H), 7.35-7.11 (m, 6H), 5.48 (s, 1H, $D_2O$ exchangeable), 3.78 (s, 2H), 2.38-2.23 (m, 2H), 1.36-1.00 (m, 3H), 0.62 (ddt, J=10.5, 7.3, 3.7 Hz, 1H), 0.47-0.30 (m, 2H), −0.08 (td, J=5.4, 3.8 Hz, 2H); $^{19}$F NMR (282 MHz, DMSO-$d_6$) δ −60.70; MS (ES+) 557.3 (M+Na); Analysis calculated for $C_{30}H_{29}F_3N_4O_2 \cdot 0.25H_2O$: C, 66.84; H, 5.52; N, 10.39; Found: C, 66.90; H, 5.74; N, 10.04.

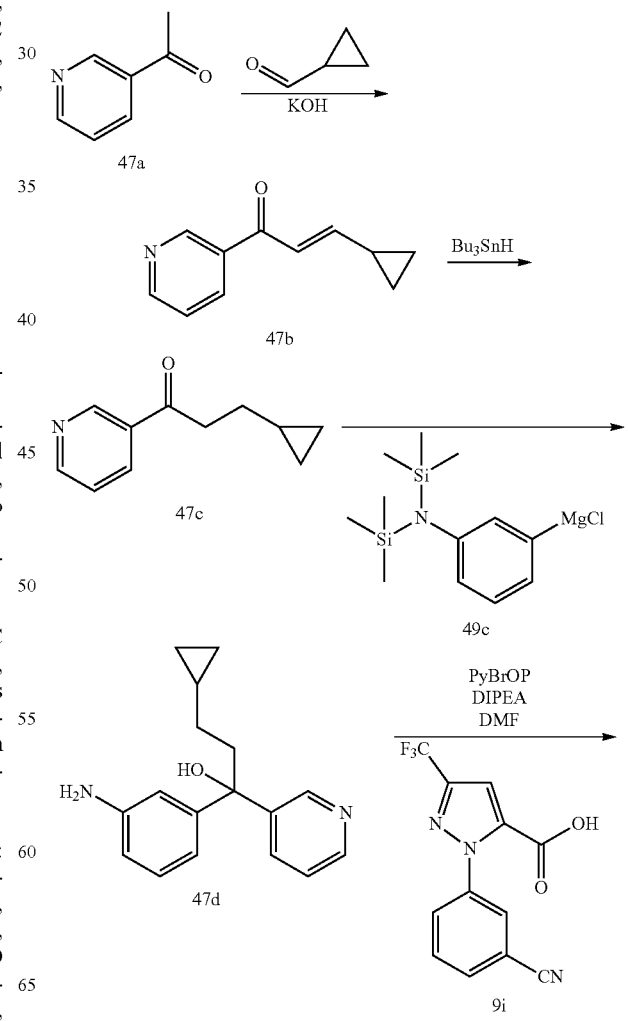

Scheme 47

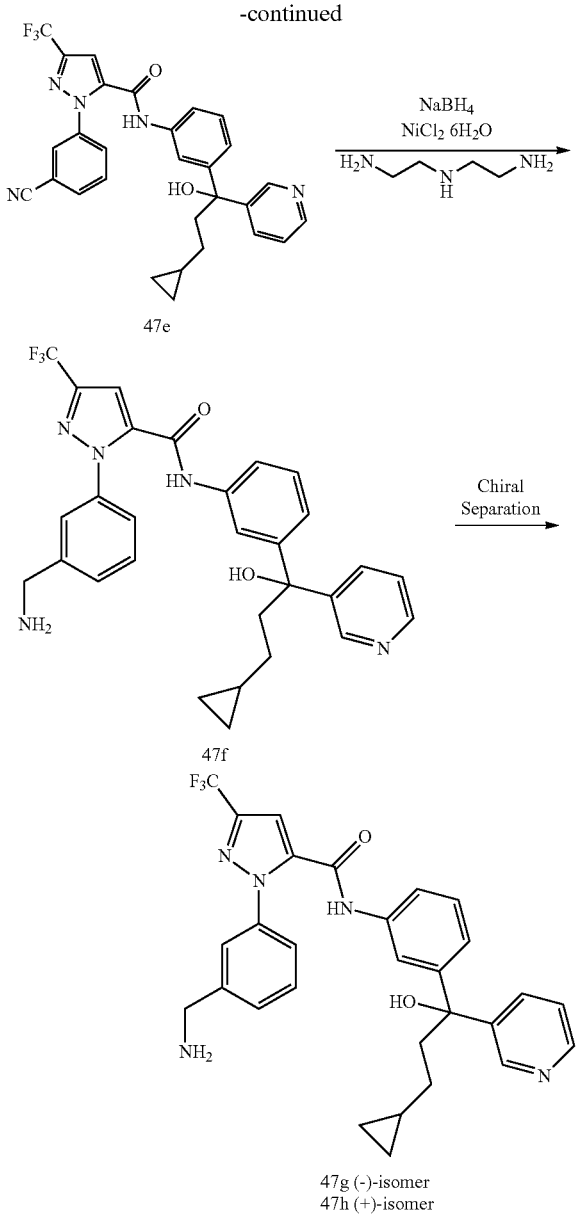

Preparation of Racemic 1-(3-(aminomethyl)phenyl)-N-(3-(3-cyclopropyl-1-hydroxy-1-(pyridin-3-yl)propyl)phenyl)-3-(trifluoromethyl)-1H-pyrazole-5-carboxamide (47f); (−)-1-(3-(aminomethyl)phenyl)-N-(3-(3-cyclopropyl-1-hydroxy-1-(pyridin-3-yl)propyl)phenyl)-3-(trifluoromethyl)-1H-pyrazole-5-carboxamide (47g) and (+)-1-(3-(aminomethyl)phenyl)-N-(3-(3-cyclopropyl-1-hydroxy-1-(pyridin-3-yl)propyl)phenyl)-3-(trifluoromethyl)-1H-pyrazole-5-carboxamide (47h)

Step-1: Preparation of (E)-3-cyclopropyl-1-(pyridin-3-yl)prop-2-en-1-one (47b)

To a stirred solution of 3-acetylpyridine (47a) (9.07 mL, 83 mmol) in methanol (200 mL) cooled to 0° C. was added cyclopropanecarboxaldehyde (9.95 mL, 132 mmol) and aqueous potassium hydroxide (1N solution, 16.51 mL, 16.51 mmol). The reaction was allowed to warm to room temperature overnight. The reaction was acidified with 1 N hydrochloric acid and concentrated in vacuum to remove methanol. The crude residue was dissolved in ethyl acetate (300 mL) washed with sodium carbonate solution, water (2×100 mL), brine (50 mL), dried, filtered and concentrated in vacuum. The crude residue was purified by flash column chromatography (silicagel, 80 g, eluting with ethyl acetate in hexanes 0 to 100%) to afford (E)-3-cyclopropyl-1-(pyridin-3-yl)prop-2-en-1-one (47b) (5.99 g, 41.9%); $^1$H NMR (300 MHz, DMSO-d$_6$) δ 9.14 (td, J=2.7, 0.9 Hz, 1H), 8.80 (ddd, J=4.9, 3.3, 1.7 Hz, 1H), 8.36-8.27 (m, 1H), 7.57 (ddt, J=8.0, 4.8, 1.2 Hz, 1H), 7.28 (d, J=15.1 Hz, 1H), 6.58 (dd, J=15.1, 10.3 Hz, 1H), 1.80 (dddd, J=12.5, 10.4, 7.8, 4.5 Hz, 1H), 1.08-0.99 (m, 2H), 0.85-0.76 (m, 2H); MS (ES+) 196.1 (M+Na).

Step-2: Preparation of 3-cyclopropyl-1-(pyridin-3-yl)propan-1-one (47c)

To a stirred solution of (E)-3-cyclopropyl-1-(pyridin-3-yl)prop-2-en-1-one (47b) (5.93 g, 34.2 mmol) in benzene (150 mL) was added tributylstannane (18.42 mL, 68.5 mmol) and heated to reflux. The reaction was stirred at reflux for 5 h and cooled to room temperature. Benzene was evaporated and the residue was purified by flash column chromatography (silica gel, 80 g, eluting with ethyl acetate in hexanes 0 to 100%) to afford 3-cyclopropyl-1-(pyridin-3-yl)propan-1-one (47c) (5.29 g, 88%); $^1$H NMR (300 MHz, DMSO-d$_6$) δ 9.07 (dd, J=2.3, 0.9 Hz, 1H), 8.72 (dd, J=4.8, 1.7 Hz, 1H), 8.24 (ddd, J=8.0, 2.4, 1.8 Hz, 1H), 7.50 (ddd, J=8.0, 4.9, 0.9 Hz, 1H), 3.09 (t, J=7.2 Hz, 2H), 1.47 (q, J=7.1 Hz, 2H), 0.70 (dddd, J=12.0, 8.1, 5.1, 2.2 Hz, 1H), 0.40-0.21 (m, 2H), 0.06--0.05 (m, 2H).

Step-3: Preparation of 1-(3-aminophenyl)-3-cyclopropyl-1-(pyridin-3-yl)propan-1-ol (47d)

To a stirred solution of 3-cyclopropyl-1-(pyridin-3-yl)propan-1-one (47c) (2 g, 11.41 mmol) in tetrahydrofuran (20 mL) was added (3-(bis(trimethylsilyl)amino)phenyl)magnesium chloride (49c) (4.23 g, 14.27 mmol) at 0° C. The reaction was allowed to come to room temperature for 12 h, quenched by adding ammonium chloride solution (25 mL) and ethyl acetate (50 mL). The reaction was acidified with hydrochloric acid (10 mL, 3N) and stirred for 15 minutes and basified with saturated potassium carbonate solution (20 mL), extracted with ethyl acetate (3×100 mL). the organic layers were combined washed with water (2×50 mL), brine (25 mL), dried and concentrated in vacuum. The crude residue was purified by by flash column chromatography (silica gel, 80 g, eluting with CMA 80 in chloroform) to afford 1-(3-aminophenyl)-3-cyclopropyl-1-(pyridin-3-yl)propan-1-ol (47d) (3.0 g, 11.18 mmol, 98% yield) as a colorless solid; $^1$H NMR (300 MHz, DMSO-d$_6$) δ 8.59 (dd, J=2.4, 0.9 Hz, 1H), 8.38-8.31 (m, 1H), 7.74 (ddd, J=8.0, 2.4, 1.7 Hz, 1H), 7.27 (ddd, J=8.0, 4.7, 0.8 Hz, 1H), 6.91 (t, J=7.8 Hz, 1H), 6.69 (t, J=2.0 Hz, 1H), 6.61-6.51 (m, 1H), 6.35 (ddd, J=7.9, 2.2, 0.9 Hz, 1H), 5.46 (s, 1H, D$_2$O exchangeable), 4.98 (s, 2H, D$_2$O exchangeable), 2.35-2.18 (m, 2H), 1.21-0.94 (m, 2H), 0.62 (qt, J=7.2, 3.8 Hz, 1H), 0.41-0.28 (m, 2H), −0.07 (td, J=5.3, 3.7 Hz, 2H).

Step-4: Preparation of 1-(3-cyanophenyl)-N-(3-(3-cyclopropyl-1-hydroxy-1-(pyridin-3-yl)propyl)phenyl)-3-(trifluoromethyl)-1H-pyrazole-5-carboxamide (47e)

To a solution of 1-(3-cyanophenyl)-3-(trifluoromethyl)-1H-pyrazole-5-carboxylic acid (9i) (2.148 g, 7.64 mmol) in N,N-dimethylformamide (46.1 mL, 596 mmol) was added 1-(3-aminophenyl)-3-cyclopropyl-1-(pyridin-3-yl)propan-1-ol (47d) (2.46 g, 9.17 mmol), N-ethyl-N-isopropylpropan-2-amine (10.64 mL, 61.1 mmol) and Bromo-tris-pyrrolidino phosphoniumhexafluorophosphate (PyBrOP, 3.92 g, 8.40 mmol) at room temperature. The resulting reaction mixture was stirred at 25° C. for 16 h. The reaction mixture was diluted with water (200 mL) and extracted with ethyl acetate (3×300 mL). The combined organic layers were washed with water (2×100 mL), brine (100 mL), dried over anhydrous $MgSO_4$, filtered, and concentrated in under reduced pressure to dryness. The residue was purified by flash column chromatography (silica gel 80 g, eluting with CMA 80 in chloroform 0-100%) to afford 1-(3-cyanophenyl)-N-(3-(3-cyclopropyl-1-hydroxy-1-(pyridin-3-yl)propyl)phenyl)-3-(trifluoromethyl)-1H-pyrazole-5-carboxamide (47e) (3.63 g, 89%); $^1$H NMR (300 MHz, DMSO-$d_6$) δ 10.63 (s, 1H), 8.62 (d, J=2.3 Hz, 1H), 8.37 (dd, J=4.7, 1.6 Hz, 1H), 8.16 (t, J=1.9 Hz, 1H), 8.00 (dt, J=7.7, 1.3 Hz, 1H), 7.90 (ddd, J=8.2, 2.3, 1.1 Hz, 1H), 7.82-7.66 (m, 4H), 7.65-7.55 (m, 1H), 7.38-7.06 (m, 3H), 5.74 (s, 1H), 2.34 (t, J=8.1 Hz, 2H), 1.10 (t, J=6.1 Hz, 2H), 0.64 (s, 1H), 0.41-0.27 (m, 2H), −0.06 (dd, J=5.8, 4.1 Hz, 2H); MS (ES−) 530.2 (M−1).

Step-5: Preparation of Racemic 1-(3-(aminomethyl)phenyl)-N-(3-(3-cyclopropyl-1-hydroxy-1-(pyridin-3-yl)propyl)phenyl)-3-(trifluoromethyl)-1H-pyrazole-5-carboxamide (47f)

To a stirred solution of 1-(3-cyanophenyl)-N-(3-(3-cyclopropyl-1-hydroxy-1-(pyridin-3-yl)propyl)phenyl)-3-(trifluoromethyl)-1H-pyrazole-5-carboxamide (47e) (2.038 g, 3.83 mmol) in methanol (100 mL) at 0° C. was added nickel(II) chloride hexahydrate (1.139 g, 4.79 mmol) followed by sodium tetrahydroborate (1.451 g, 38.3 mmol) in small portions over a period of 15 minutes. The reaction was stirred for 30 minutes quenched with N1-(2-aminoethyl)ethane-1,2-diamine (3.18 mL, 30.7 mmol) and stirred for 30 mins at room temperature. The reaction mixture was concentrated to remove methanol, diluted water (200 mL) and stirred for 30 minutes. The solid separated was collected by filtration. The solid was suspended in ethanol (100 mL) and concentrated to remove water. The residue was dissolved in methanol and purified by flash column chromatography (silica gel 80 g, eluting with CMA 80 in chloroform 0-50%) to afford Racemic 1-(3-(aminomethyl)phenyl)-N-(3-(3-cyclopropyl-1-hydroxy-1-(pyridin-3-yl)propyl)phenyl)-3-(trifluoromethyl)-1H-pyrazole-5-carboxamide (47f) (575 mg, 1.074 mmol, 28.0% yield) as a colorless solid.

$^1$HNMR (300 MHz, DMSO-$d_6$) δ 10.67 (s, 1H, $D_2O$ exchangeable), 8.62 (dd, J=2.4, 0.9 Hz, 1H), 8.37 (dd, J=4.7, 1.6 Hz, 1H), 7.77 (dt, J=8.0, 2.0 Hz, 1H), 7.69 (d, J=2.0 Hz, 1H), 7.56 (d, J=6.6 Hz, 1H), 7.54-7.49 (m, 1H), 7.47-7.37 (m, 2H), 7.34-7.27 (m, 2H), 7.24 (d, J=7.7 Hz, 1H), 7.19 (dt, J=8.0, 1.5 Hz, 1H), 5.73 (s, 1H, $D_2O$ exchangeable), 3.77 (s, 2H), 2.42-2.27 (m, 2H), 2.04 (s, 2H, $D_2O$ exchangeable), 1.09 (h, J=6.7, 6.3 Hz, 2H), 0.73-0.54 (m, 1H), 0.44-0.28 (m, 2H), −0.07 (dd, J=4.8, 1.6 Hz, 2H); Mass spec (ES+) 536.3 (M+1), (ES−) 534.3 (M−1), 570.4 (M+35).

Step-6: Preparation of (−)-1-(3-(aminomethyl)phenyl)-N-(3-(3-cyclopropyl-1-hydroxy-1-(pyridin-3-yl)propyl)phenyl)-3-(trifluoromethyl)-1H-pyrazole-5-carboxamide (47g) and (+)-1-(3-(aminomethyl)phenyl)-N-(3-(3-cyclopropyl-1-hydroxy-1-(pyridin-3-yl)propyl)phenyl)-3-(trifluoromethyl)-1H-pyrazole-5-carboxamide (47h)

Racemic 1-(3-(aminomethyl)phenyl)-N-(3-(3-cyclopropyl-1-hydroxy-1-(pyridin-3-yl)propyl)phenyl)-3-(trifluoromethyl)-1H-pyrazole-5-carboxamide (47f) (317 mgs) was separated by chiral preparative HPLC using CHIRALPAK AD-H, 5μ, 4.6×250 mm, flow rate 1 mL/min, Solvent: 85% Hexane/15% EtOH/0.1% DEA, UV=254 nM, 25° C.; to furnish:

1. Peak-1 corresponding to (−)-1-(3-(aminomethyl)phenyl)-N-(3-(3-cyclopropyl-1-hydroxy-1-(pyridin-3-yl)propyl)phenyl)-3-(trifluoromethyl)-1H-pyrazole-5-carboxamide (47g) (0.193 g, 98.9% ee); Chiral HPLC (Rt=9.426 min, 99.4471% peak-1 for 47g), (Rt=11.592, 0.5529% peak-2 for 47h); Peak-1 or compound 47g was repurified by flash column chromatography (silica gel 12 g, eluting 0-100% CMA-80 in chloroform for 13 mins) to afford (−)-1-(3-(aminomethyl)phenyl)-N-(3-(3-cyclopropyl-1-hydroxy-1-(pyridin-3-yl)propyl)phenyl)-3-(trifluoromethyl)-1H-pyrazole-5-carboxamide (47g) (124 mgs pure Peak-1); Optical Rotation −4.87 (MeOH, 0.945); $^1$H NMR (300 MHz, DMSO-$d_6$) δ 10.67 (s, 1H), 8.62 (dd, J=2.5, 0.9 Hz, 1H), 8.37 (dd, J=4.7, 1.6 Hz, 1H), 7.81-7.74 (m, 1H), 7.70 (t, J=1.9 Hz, 1H), 7.60-7.54 (m, 2H), 7.51 (t, J=1.6 Hz, 1H), 7.46-7.38 (m, 2H), 7.33-7.27 (m, 2H), 7.24 (d, J=7.8 Hz, 1H), 7.19 (dt, J=7.9, 1.5 Hz, 1H), 5.72 (s, 1H), 3.77 (s, 2H), 2.41-2.27 (m, 2H), 1.94 (s, 2H), 1.13-1.06 (m, 2H), 0.63 (dt, J=8.4, 5.4 Hz, 1H), 0.40-0.30 (m, 2H), −0.03-−0.11 (m, 2H); $^{19}$F NMR (282 MHz, DMSO-$d_6$) δ −60.71. Free base of compound 47g was dissolved in methanol and added (0.05 mL) of 2 N HCl in methanol. The mixture was concentrated in vacuum to dryness to furnish (−)-1-(3-(aminomethyl)phenyl)-N-(3-(3-cyclopropyl-1-hydroxy-1-(pyridin-3-yl)propyl)phenyl)-3-(trifluoromethyl)-1H-pyrazole-5-carboxamide (47g) (105 mg, 98.93% ee) as a HCl salt; $^1$H NMR (300 MHz, DMSO-$d_6$) δ 10.70 (s, 1H), 8.62 (d, J=2.3 Hz, 1H), 8.38 (dd, J=4.7, 1.6 Hz, 1H), 7.77 (dt, J=8.0, 2.0 Hz, 1H), 7.71 (t, J=1.9 Hz, 1H), 7.64-7.55 (m, 3H), 7.54-7.44 (m, 2H), 7.40 (dt, J=7.2, 2.1 Hz, 1H), 7.34-7.29 (m, 1H), 7.27 (d, J=7.5 Hz, 1H), 7.24-7.16 (m, 1H), 5.73 (s, 1H), 3.94 (s, 2H), 2.38-2.27 (m, 2H), 1.18-0.99 (m, 2H), 0.72-0.53 (m, 1H), 0.41-0.25 (m, 2H), −0.07 (dt, J=5.5, 2.7 Hz, 2H); 19F NMR (282 MHz, DMSO-$d_6$) δ −60.75; MS (ES+) 536.3 (M+1); (ES−) 570.3 (M+Cl); Chiral HPLC purity check using CHIRALPAK AD-H, 0.8 mL/min, Solvent: 85% Hexane/15% EtOH/0.1% TEA, UV=260 nM, 40° C.; Chiral HPLC (Rt=13.443 min, 99.4653% for peak-1 compound 47g), (Rt=16.433, 0.5347% for peak-2 compound 47h); Analysis calculated for $C_{29}H_{28}F_3N_5O_2 \cdot 0.75HCl$: C, 61.88; H, 5.15; Cl, 4.72; N, 12.44; Found: C, 62.02; H, 5.31; Cl, 4.55; N, 12.30

2. Peak-2 corresponding to (+)-1-(3-(aminomethyl)phenyl)-N-(3-(3-cyclopropyl-1-hydroxy-1-(pyridin-3-yl)propyl)phenyl)-3-(trifluoromethyl)-1H-pyrazole-5-carboxamide (47h) (0.248 g, 94.25 ee); Chiral HPLC (Rt=9.347, 2.88% peak-1 for 47g) (Rt=11.47, 97.11% peak2 for 47h). Peak-2 or compound 47h was purified twice by flash column chromatography (silica gel 24 gm and 12 g, eluting 0-100% CMA-80 in chloroform for 13 mins) to afford (+)-1-(3-(aminomethyl)phenyl)-N-(3-(3-cyclopropyl-1-hydroxy-1-(pyridin-3-yl)propyl)phenyl)-3-(trifluoromethyl)-1H-pyrazole-5-carboxamide (47h) (105 mgs pure Peak-2) as free base; Optical Rotation+4.76 (MeOH, 0.84); $^1$H NMR (300 MHz, DMSO-$d_6$) δ 10.67 (s, 1H), 8.62 (dd, J=2.4, 0.9 Hz, 1H), 8.37 (dd, J=4.7, 1.6 Hz, 1H), 7.77 (ddd, J=8.0, 2.4, 1.6 Hz, 1H), 7.70 (t, J=1.8 Hz, 1H), 7.56 (d, J=6.4 Hz, 2H), 7.53-7.50 (m, 1H), 7.46-7.37 (m, 2H), 7.34-

7.27 (m, 2H), 7.24 (d, J=7.8 Hz, 1H), 7.22-7.16 (m, 1H), 5.72 (s, 1H), 3.77 (s, 2H), 2.34 (t, J=8.0 Hz, 2H), 1.99 (s, 2H), 1.08 (dt, J=13.2, 6.6 Hz, 2H), 0.72-0.55 (m, 1H), 0.43-0.28 (m, 2H), −0.03-−0.12 (m, 2H); 19F NMR (282 MHz, DMSO-$d_6$) δ −60.71. Free base of compound 47h was dissolved in methanol and added (0.05 mL) of 2 N HCl in methanol. The mixture was concentrated in vacuum to dryness to furnish (+)-1-(3-(aminomethyl)phenyl)-N-(3-(3-cyclopropyl-1-hydroxy-1-(pyridin-3-yl)propyl)phenyl)-3-(trifluoromethyl)-1H-pyrazole-5-carboxamide (47h) (95 mg, 95.39% ee) as HCl salt; $^1$H NMR (300 MHz, DMSO-$d_6$) δ 10.78 (s, 1H), 8.68 (d, J=2.3 Hz, 1H), 8.44 (dd, J=4.7, 1.6 Hz, 1H), 7.84 (dt, J=8.0, 2.0 Hz, 1H), 7.78 (t, J=1.9 Hz, 1H), 7.71-7.51 (m, 5H), 7.47 (dt, J=7.6, 2.0 Hz, 1H), 7.40-7.24 (m, 3H), 5.80 (s, 1H), 4.02 (s, 2H), 2.46-2.34 (m, 2H), 1.22-1.05 (m, 2H), 0.78-0.60 (m, 1H), 0.48-0.30 (m, 2H), −0.01 (dt, J=5.5, 2.7 Hz, 2H); $^{19}$F NMR (282 MHz, DMSO-$d_6$) δ −60.74; MS (ES+) 536.3 (M+1); (ES−) 570.3 (M+Cl); Chiral HPLC purity check using CHIRALPAK AD-H, 0.8 mL/min, Solvent: 85% Hexane/15% EtOH/0.1% TEA, UV=260 nM, 40° C.; Chiral HPLC ($R_f$=13.617 min, 2.3061% for peak-1 compound 47g), (Rt=16.35, 97.6939% for peak-2 compound 47h); Analysis calculated for $C_{29}H_{28}F_3N_5O_2 \cdot 0.65HCl \cdot 0.5H_2P$: C, 61.29; H, 5.26; Cl, 4.06; N, 12.32; Found: C, 61.20; H, 5.30; Cl, 4.04; N, 12.05.

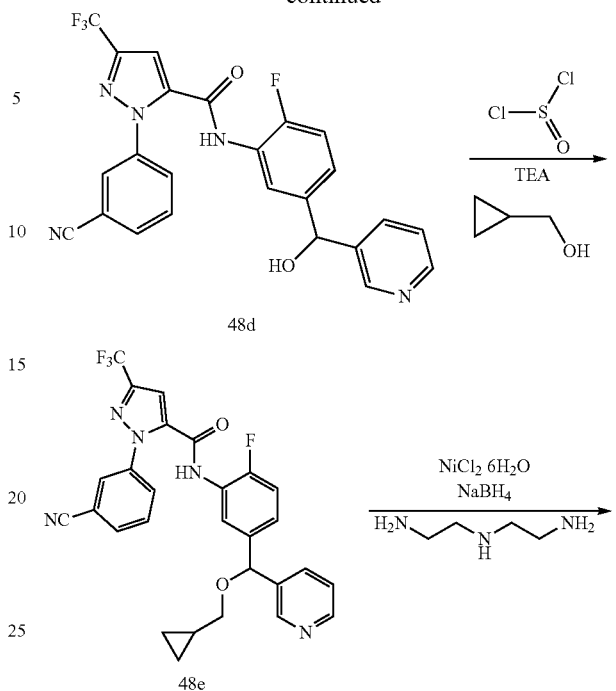

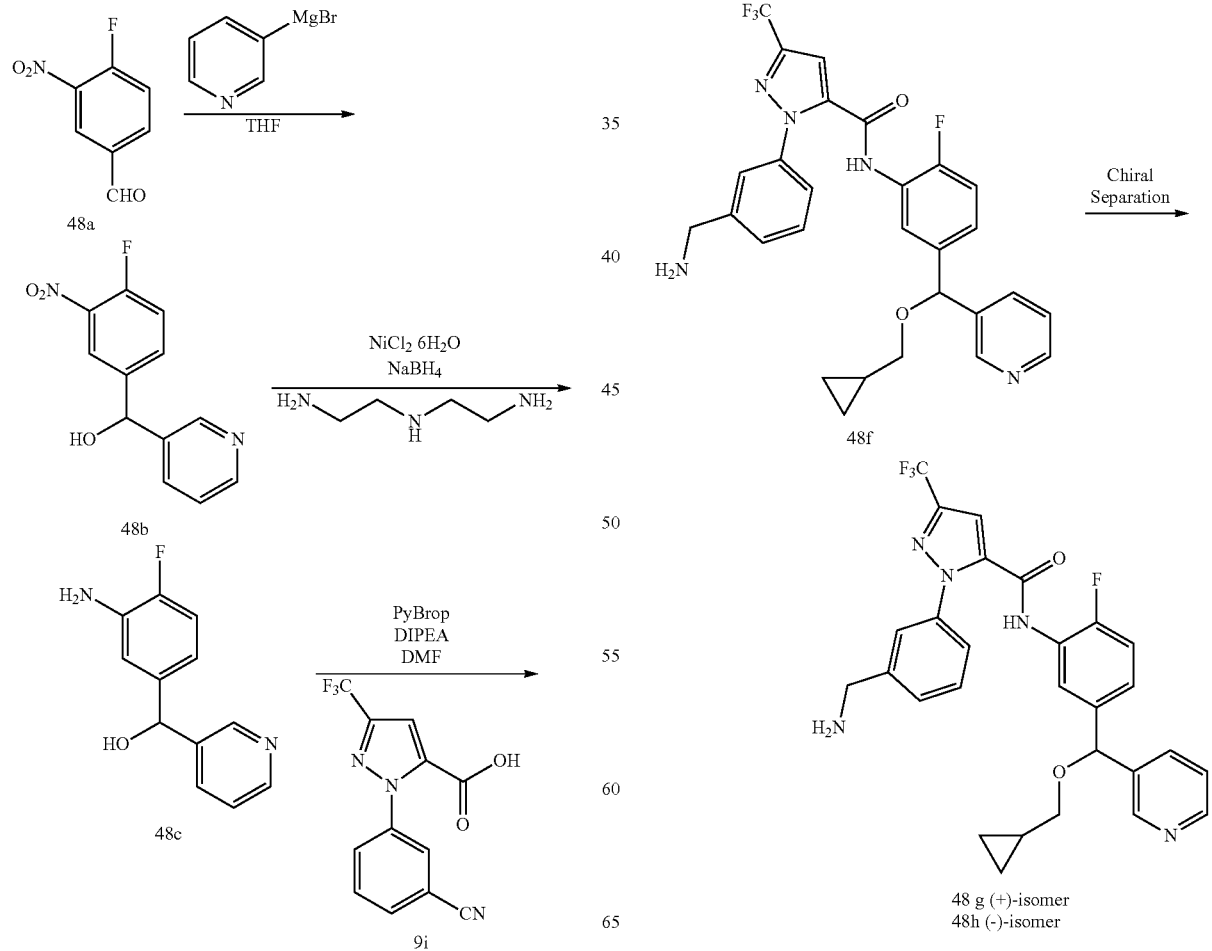

Preparation of Racemic 1-(3-(aminomethyl)phenyl)-N-(5-((cyclopropylmethoxy)(pyridin-3-yl)methyl)-2-fluorophenyl)-3-(trifluoromethyl)-1H-pyrazole-5-carboxamide (48f); (+)-1-(3-(aminomethyl)phenyl)-N-(5-((cyclopropylmethoxy)(pyridin-3-yl)methyl)-2-fluorophenyl)-3-(trifluoromethyl)-1H-pyrazole-5-carboxamide (48g) and (−)-1-(3-(aminomethyl)phenyl)-N-(5-((cyclopropylmethoxy)(pyridin-3-yl)methyl)-2-fluorophenyl)-3-(trifluoromethyl)-1H-pyrazole-5-carboxamide (48h)

Step-1: Preparation of (4-Fluoro-3-nitrophenyl)(pyridin-3-yl)methanol (48b)

A solution of 4-fluoro-3-nitrobenzaldehyde (48a) (4.2 g, 24.84 mmol) in tetrahydrofuran (100 mL) was cooled to 0° C. and treated with pyridin-3-ylmagnesium bromide (99 mL, 24.84 mmol, 0.25 M solution in 2-methyl THF), stirred at 0° C. for 3 h and room temperature for 14 h. The reaction mixture was quenched with saturated aqueous $NH_4Cl$ (60 mL) and extracted with EtOAc (2×75 mL). The organic extracts were combined washed with brine (50 mL), dried over anhydrous $MgSO_4$, filtered, and evaporated to dryness. The residue was purified by flash column chromatography [(silica gel 40 g, eluting with ethyl acetate/hexanes from 0 to 50%)] to furnish (4-Fluoro-3-nitrophenyl)(pyridin-3-yl)methanol (48b) (3.104 g, 50% yield) as a yellow solid; $^1H$ NMR (300 MHz, DMSO-$d_6$) δ 8.64 (d, J=2.2 Hz, 1H), 8.46 (dd, J=4.8, 1.7 Hz, 1H), 8.20 (dd, J=7.4, 2.3 Hz, 1H), 7.79 (ddt, J=15.0, 8.0, 2.2 Hz, 2H), 7.56 (dd, J=11.3, 8.7 Hz, 1H), 7.36 (ddd, J=7.9, 4.7, 0.9 Hz, 1H), 6.45 (d, J=4.2 Hz, 1H, $D_2O$ exchangeable), 5.94 (d, J=4.2 Hz, 1H); $^{19}F$ NMR (282 MHz, DMSO-$d_6$) δ −121.35; MS (ES$^+$): MS (ES+) 249.1 (M+1), MS (ES−) 495.1 (2M−1).

Step-2: Preparation of (3-amino-4-fluorophenyl)(pyridin-3-yl)methanol (48c)

To a stirred solution of (4-Fluoro-3-nitrophenyl)(pyridin-3-yl)methanol (48b) (3.456 g, 13.92 mmol) in anhydrous methanol (120 mL) cooled to 0° C. was added nickel(II) chloride hexahydrate (0.827 g, 3.48 mmol) followed by sodium borohydride (1.054 g, 27.8 mmol) was in small portions over a period of 5 min. The reaction was exothermic and effervescent. The reaction mixture was stirred for 20 min at 0° C. TLC analysis (ethyl acetate/hexanes, 2/8, v/v) shows reaction was complete at this point N1-(2-aminoethyl)ethane-1,2-diamine (15.04 mL, 139 mmol) was added. The mixture was allowed to stir for 30 minutes and concentrated in vacuum to dryness. The residue was treated water (75 mL), and extracted with ethyl acetate (2×75 mL). Organic layer were combined dried over anhydrous $MgSO_4$, filtered, and excess solvents were pumped-off under reduced pressure. The residue was purified by flash column chromatography [(silica gel 80 g, eluting with ethyl acetate/hexanes from 0 to 50%)] to furnish (3-amino-4-fluorophenyl)(pyridin-3-yl)methanol (48c) (1.889 g, 62% yield) as a orange yellow oil.

$^1H$ NMR (300 MHz, DMSO-$d_6$) δ 8.59-8.50 (m, 1H), 8.42 (dd, J=4.8, 1.7 Hz, 1H), 7.74-7.58 (m, 1H), 7.32 (ddd, J=7.9, 4.8, 0.9 Hz, 1H), 6.90 (dd, J=11.5, 8.3 Hz, 1H), 6.78 (dd, J=8.9, 2.2 Hz, 1H), 6.52 (ddd, J=8.3, 4.5, 2.2 Hz, 1H), 5.97 (d, J=3.9 Hz, 1H, $D_2O$ exchangeable), 5.61 (d, J=3.9 Hz, 1H), 5.11 (s, 2H, $D_2O$ exchangeable); $^{19}F$ NMR (282 MHz, DMSO-$d_6$) δ −137.43; MS (ES$^+$): MS (ES+) 219.1 (M+1), 241.1 (M+Na), MS (ES+) 217.1 (M−1).

Step-3: Preparation of 1-(3-Cyanophenyl)-N-(2-fluoro-5-(hydroxy(pyridin-3-yl)methyl)phenyl)-3-(trifluoromethyl)-1H-pyrazole-5-carboxamide (48d)

In a 100 mL single-necked flask containing 1-(3-cyanophenyl)-3-(trifluoromethyl)-1H-pyrazole-5-carboxylic acid (9i) (2.88 g, 10.23 mmol), (3-amino-4-fluorophenyl)(pyridin-3-yl)methanol (48c) (1.861 g, 8.53 mmol), bromo-tris-pyrrolidino phosphoniumhexafluorophosphate(PyBrop) (4.77 g, 10.23 mmol) was added N,N-dimethylformamide (DMF) (52 mL) and N-ethyl-N-isopropylpropan-2-amine (DIPEA) (7.43 mL, 42.6 mmol) successively in a positive flow of nitrogen at room temperature. The resulting reaction mixture was stirred at room temperature for 16 h under a positive flow of nitrogen atmosphere. Excess DMF was pumped-off under reduced pressure. The residue was treated with water (50 mL), and extracted with ethyl acetate (2×50 mL). Combined organic layers were dried over anhydrous $MgSO_4$, filtered, evaporated to dryness. The residue was purified by flash column chromatography [silica gel 40 g, eluting with methanol in chloroform from 0-80%] to furnish 1-(3-Cyanophenyl)-N-(2-fluoro-5-(hydroxy(pyridin-3-yl)methyl)phenyl)-3-(trifluoromethyl)-1H-pyrazole-5-carboxamide (48d) (2.707 g, 5.62 mmol, 66% yield) as a pale yellow solid; $^1H$ NMR (300 MHz, DMSO-$d_6$) δ 10.56 (s, 1H, $D_2O$ exchangeable), 8.58 (d, J=2.2 Hz, 1H), 8.43 (dd, J=4.8, 1.7 Hz, 1H), 8.17-8.09 (m, 1H), 8.00 (dt, J=7.8, 1.3 Hz, 1H), 7.90 (ddd, J=8.2, 2.3, 1.2 Hz, 1H), 7.77-7.68 (m, 3H), 7.56 (dd, J=7.5, 2.0 Hz, 1H), 7.38-7.20 (m, 3H), 6.20 (d, J=4.0 Hz, 1H, $D_2O$ exchangeable), 5.79 (d, J=4.0 Hz, 1H); $^{19}F$ NMR (282 MHz, DMSO-$d_6$) δ −60.98, −122.90; IR (KBr, cm$^{-1}$): 2235 cm$^{-1}$ (—CN stretching); MS (ES$^+$): MS (ES+) 482.2 (M+1), MS (ES−) 480.2 (M−1).

Step-4: Preparation of 1-(3-cyanophenyl)-N-(5-((cyclopropylmethoxy)(pyridin-3-yl)methyl)-2-fluorophenyl)-3-(trifluoromethyl)-1H-pyrazole-5-carboxamide (48e)

To a solution of 1-(3-Cyanophenyl)-N-(2-fluoro-5-(hydroxy(pyridin-3-yl)methyl)phenyl)-3-(trifluoromethyl)-1H-pyrazole-5-carboxamide (48d) (0.784 g, 1.629 mmol) in dichloromethane (20 mL) at 0° C. was added thionyl chloride (0.356 mL, 4.89 mmol), reaction mixture allowed to warm to room temperature and stirred for 12 h. The reaction mixture was quenched with cyclopropylmethanol (0.585 mL, 8.14 mmol), added acetonitrile (20 mL), stirred for 1 h at room temperature and concentrated in vacuum to dryness. The residue was dissolved in cyclopropylmethanol (5.97 mL, 81 mmol) added acetonitrile (20 mL), triethylamine (0.681 mL, 4.89 mmol) and heated at 100° C. for 24 h. The reaction mixture was cooled to room temperature and evaporated to dryness. The residue was purified by flash column chromatography (silica gel 40 g, eluting with methanol in chloroform from 0-100%) to afford 1-(3-cyanophenyl)-N-(5-((cyclopropylmethoxy)(pyridin-3-yl)methyl)-2-fluorophenyl)-3-(trifluoromethyl)-1H-pyrazole-5-carboxamide (48e) (378 mg, 43% yield) as a white solid.

$^1H$ NMR (300 MHz, DMSO-$d_6$) δ 10.58 (s, 1H, $D_2O$ exchangeable), 8.58 (d, J=2.1 Hz, 1H), 8.47 (dd, J=4.8, 1.7 Hz, 1H), 8.17-8.10 (m, 1H), 8.00 (dt, J=7.7, 1.3 Hz, 1H), 7.95-7.86 (m, 1H), 7.78-7.67 (m, 3H), 7.62-7.54 (m, 1H), 7.43-7.25 (m, 3H), 5.59 (s, 1H), 3.25 (d, J=6.8 Hz, 2H), 1.05 (dddd, J=14.8, 6.8, 5.0, 2.6 Hz, 1H), 0.53-0.39 (m, 2H), 0.15

(dtd, J=5.5, 3.7, 3.3, 1.5 Hz, 2H); $^{19}$F NMR (282 MHz, DMSO-d$_6$) δ −60.99, −122.10; MS (ES$^+$): MS (ES+) 536.2 (M+1), MS (ES−) 534.2 (M−1).

Step-5: Preparation of Racemic 1-(3-(aminomethyl) phenyl)-N-(5-((cyclopropylmethoxy)(pyridin-3-yl) methyl)-2-fluorophenyl)-3-(trifluoromethyl)-1H-pyrazole-5-carboxamide (48f)

To a stirred solution of 1-(3-cyanophenyl)-N-(5-((cyclopropylmethoxy)(pyridin-3-yl)methyl)-2-fluorophenyl)-3-(trifluoromethyl)-1H-pyrazole-5-carboxamide (48e) (0.238 g, 0.444 mmol) in anhydrous methanol (30 mL) cooled to 0° C. was added nickel(II) chloride hexahydrate (0.158 g, 0.667 mmol), sodium borohydride (0.135 g, 3.56 mmol) was added in small portions over a period of 5 min. The reaction was stirred for 25 min quenched with N1-(2-aminoethyl) ethane-1,2-diamine (0.480 mL, 4.44 mmol), stirred for 30 mins and concentrated in vacuum. The reaction mixture was treated with saturated aqueous NH$_4$Cl (60 mL), and product was extracted with chloroform (2×60 mL). The combined organic layers were dried over MgSO$_4$, filtered and evaporated to dryness. The residue was purified by flash column chromatography [(silica gel 25 g, eluting with methanol/chloroform from 0 to 50%)] to furnish Racemic 1-(3-(aminomethyl)phenyl)-N-(5-((cyclopropylmethoxy)(pyridin-3-yl)methyl)-2-fluorophenyl)-3-(trifluoromethyl)-1H-pyrazole-5-carboxamide (48f) (0.129 g, 0.239 mmol, 53.8% yield) as white solid; $^1$H NMR (300 MHz, DMSO-d$_6$) δ 8.57 (d, J=2.2 Hz, 1H), 8.47 (dd, J=4.8, 1.7 Hz, 1H), 7.71 (dt, J=8.0, 2.0 Hz, 1H), 7.62 (d, J=7.4 Hz, 1H), 7.58 (s, 1H), 7.52 (s, 1H), 7.47-7.41 (m, 2H), 7.40-7.25 (m, 4H), 5.59 (s, 1H), 3.77 (s, 2H), 3.25 (d, J=6.8 Hz, 2H), 1.15-0.96 (m, 1H), 0.56-0.35 (m, 2H), 0.23-0.08 (m, 2H); $^{19}$F NMR (282 MHz, DMSO-d$_6$) δ −60.75, −122.56; MS (ES$^+$): MS (ES+) 540.2 (M+1), MS (ES−) 538.2 (M−1), 574.1 (M+Cl); Analysis calculated for C$_{28}$H$_{25}$F$_4$N$_5$O$_2$.0.25H$_2$O: C, 61.82; H, 4.72; N, 12.87; Found: C, 61.89; H, 4.91; N, 12.75.

Step-6: Preparation of (+)-1-(3-(aminomethyl)phenyl)-N-(5-((cyclopropylmethoxy)(pyridin-3-yl) methyl)-2-fluorophenyl)-3-(trifluoromethyl)-1H-pyrazole-5-carboxamide (48g) and (−)-1-(3-(aminomethyl)phenyl)-N-(5-((cyclopropylmethoxy) (pyridin-3-yl)methyl)-2-fluorophenyl)-3-(trifluoromethyl)-1H-pyrazole-5-carboxamide (48h)

Racemic 1-(3-(aminomethyl)phenyl)-N-(5-((cyclopropylmethoxy)(pyridin-3-yl)methyl)-2-fluorophenyl)-3-(trifluoromethyl)-1H-pyrazole-5-carboxamide (48f) (725 mgs) was separated using chiral preparative HPLC using CHIRALPAK IC, 5μ, 4.6×250 mm, flow rate 1 mL/min, Solvent: 80% Hexane/20% EtOH/0.1% DEA, UV=320 nM, 25° C., to furnish:

1. (+)-1-(3-(aminomethyl)phenyl)-N-(5-((cyclopropylmethoxy)(pyridin-3-yl)methyl)-2-fluorophenyl)-3-(trifluoromethyl)-1H-pyrazole-5-carboxamide (48g) (358.5 mg as peak-1, R$_t$=6.758 min, 99.2473% for peak-1 (compound 48g), R$_t$=9.193 min, 0.7527% for peak-2 (compound 48h), 97.1% ee for 48g. This was repurified by flash column chromatography (silica gel 25 g, eluting methanol in chloroform for 25 mins) to afford pure (+)-1-(3-(aminomethyl)phenyl)-N-(5-((cyclopropylmethoxy)(pyridin-3-yl)methyl)-2-fluorophenyl)-3-(trifluoromethyl)-1H-pyrazole-5-carboxamide (48g) (180 mg) as a white solid; The free base of pure (+)-1-(3-(aminomethyl)phenyl)-N-(5-((cyclopropylmethoxy)(pyridin-3-yl)methyl)-2-fluorophenyl)-3-(trifluoromethyl)-1H-pyrazole-5-carboxamide (48g) was dissolved in methanol and added (4 mL) of 2 N HCl in methanol. The mixture was concentrated in vacuum to dryness to furnish pure (+)-1-(3-(aminomethyl)phenyl)-N-(5-((cyclopropylmethoxy)(pyridin-3-yl)methyl)-2-fluorophenyl)-3-(trifluoromethyl)-1H-pyrazole-5-carboxamide (48g) (180 mg) as dihydrochloride salt; $^1$H NMR (300 MHz, DMSO-d$_6$) δ 10.78 (s, 1H, D$_2$O exchangeable), 8.86 (d, J=2.0 Hz, 1H), 8.78 (dd, J=5.5, 1.5 Hz, 1H), 8.53 (s, 3H, D$_2$O exchangeable), 8.37-8.28 (m, 1H), 7.89 (dd, J=8.1, 5.4 Hz, 1H), 7.77-7.61 (m, 4H), 7.59-7.47 (m, 2H), 7.40-7.25 (m, 2H), 5.80 (s, 1H), 4.11 (q, J=5.9 Hz, 2H), 3.31 (s, 2H), 1.06 (ddt, J=9.3, 7.5, 2.8 Hz, 1H), 0.56-0.33 (m, 2H), 0.26-0.09 (m, 2H); MS (ES+) 541.3 (M+1), (ES−) 538.3 (M−1), 574.3 (M+35); Optical Rotation [c]D=+10.228 [CH$_3$OH, 1.095]; Chiral purity checked by performing chiral HPLC using chiral AD-H column, 0.8 mL/min, Solvent: 85% Hexane/15% EtOH/0.1% TEA, UV=260 nM, 40° C.; C (Rt=8.860 min, 99.1567% for peak-1 compound 48g), (Rt=14.127, 0.8433% for peak-2, compound 48h) (98.31% ee for 48g HCl salt); Analysis calculated for C$_{28}$H$_{25}$F$_4$N$_5$O$_2$.2.05HCl.1.75H$_2$O: C, 52.08; H, 4.77; Cl, 11.25; N, 10.84; Found: C, 52.07; H, 4.80; Cl, 11.46; N, 10.60

2. (−)-1-(3-(aminomethyl)phenyl)-N-(5-((cyclopropylmethoxy)(pyridin-3-yl)methyl)-2-fluorophenyl)-3-(trifluoromethyl)-1H-pyrazole-5-carboxamide (48h) (382.5 mg as peak-2, R$_t$=6.861 min, 3.7692% for peak-1 (compound 48g) R$_t$=9.131 min, 96.2308% for-peak 2 (compound 48h), 92.4% ee for compound 48h. This was repurified by flash column chromatography (silica gel 12 g, eluting 0-30% MeOH in chloroform for 25 mins) to afford (−)-1-(3-(aminomethyl)phenyl)-N-(5-((cyclopropylmethoxy)(pyridin-3-yl)methyl)-2-fluorophenyl)-3-(trifluoromethyl)-1H-pyrazole-5-carboxamide (48h) (0.255 g) as a white solid. The free base of pure (−)-1-(3-(aminomethyl)phenyl)-N-(5-((cyclopropylmethoxy)(pyridin-3-yl)methyl)-2-fluorophenyl)-3-(trifluoromethyl)-1H-pyrazole-5-carboxamide (48h) (245 mg) was dissolved in methanol (8 mL) and added 2 N HCl (in methanol, 2.25 mL, 10 eq). The solution was and stirred at room temperature for 30 min, evaporated to dryness to afford (−)-1-(3-(aminomethyl)phenyl)-N-(5-((cyclopropylmethoxy)(pyridin-3-yl)methyl)-2-fluorophenyl)-3-(trifluoromethyl)-1H-pyrazole-5-carboxamide (48h) (238 mg) hydrochloride salt as an yellow solid; $^1$H NMR (300 MHz, DMSO-d$_6$) δ 10.76 (s, 1H, D$_2$O exchangeable), 8.83 (d, J=2.0 Hz, 1H), 8.75 (dd, J=5.4, 1.5 Hz, 1H), 8.49 (bs, 3H, D$_2$O exchangeable), 8.27 (d, J=8.1 Hz, 1H), 7.85 (dd, J=8.1, 5.4 Hz, 1H), 7.76-7.60 (m, 4H), 7.59-7.48 (m, 2H), 7.40-7.25 (m, 2H), 5.78 (s, 1H), 4.11 (q, J=5.8 Hz, 2H), 3.29 (d, J=6.8 Hz, 2H), 1.17-0.97 (m, 1H), 0.59-0.37 (m, 2H), 0.25-0.11 (m, 2H); $^1$H NMR (300 MHz, DMSO d6, D$_2$O) δ 8.81 (d, J=2.0 Hz, 1H), 8.71 (dd, J=5.5, 1.5 Hz, 1H), 8.29 (d, J=8.1 Hz, 1H), 7.87 (dd, J=8.1, 5.5 Hz, 1H), 7.70 (s, 1H), 7.67 (d, J=7.0 Hz, 1H), 7.63 (s, 1H), 7.60 (d, J=2.1 Hz, 1H), 7.57 (s, 1H), 7.52 (td, J=4.9, 2.5 Hz, 1H), 7.41-7.28 (m, 2H), 5.76 (s, 1H), 4.12 (s, 2H), 3.30 (dd, J=6.9, 2.0 Hz, 2H), 1.05 (dq, J=8.6, 5.2, 4.3 Hz, 1H), 0.57-0.40 (m, 2H), 0.26-0.10 (m, 2H); $^{19}$F NMR (282 MHz, DMSO-d$_6$) δ −60.80 (d, J=2.5 Hz), −121.44; MS (ES+) 540.3

(M+1), MS (ES−) 538.3 (M−1), 574.2 (M+Cl); Optical Rotation [α]$_D$=−9.16 [CH$_3$OH, 0.83].
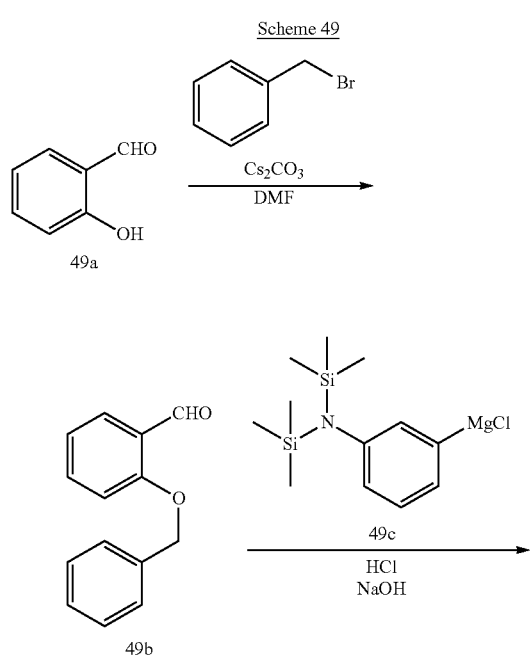
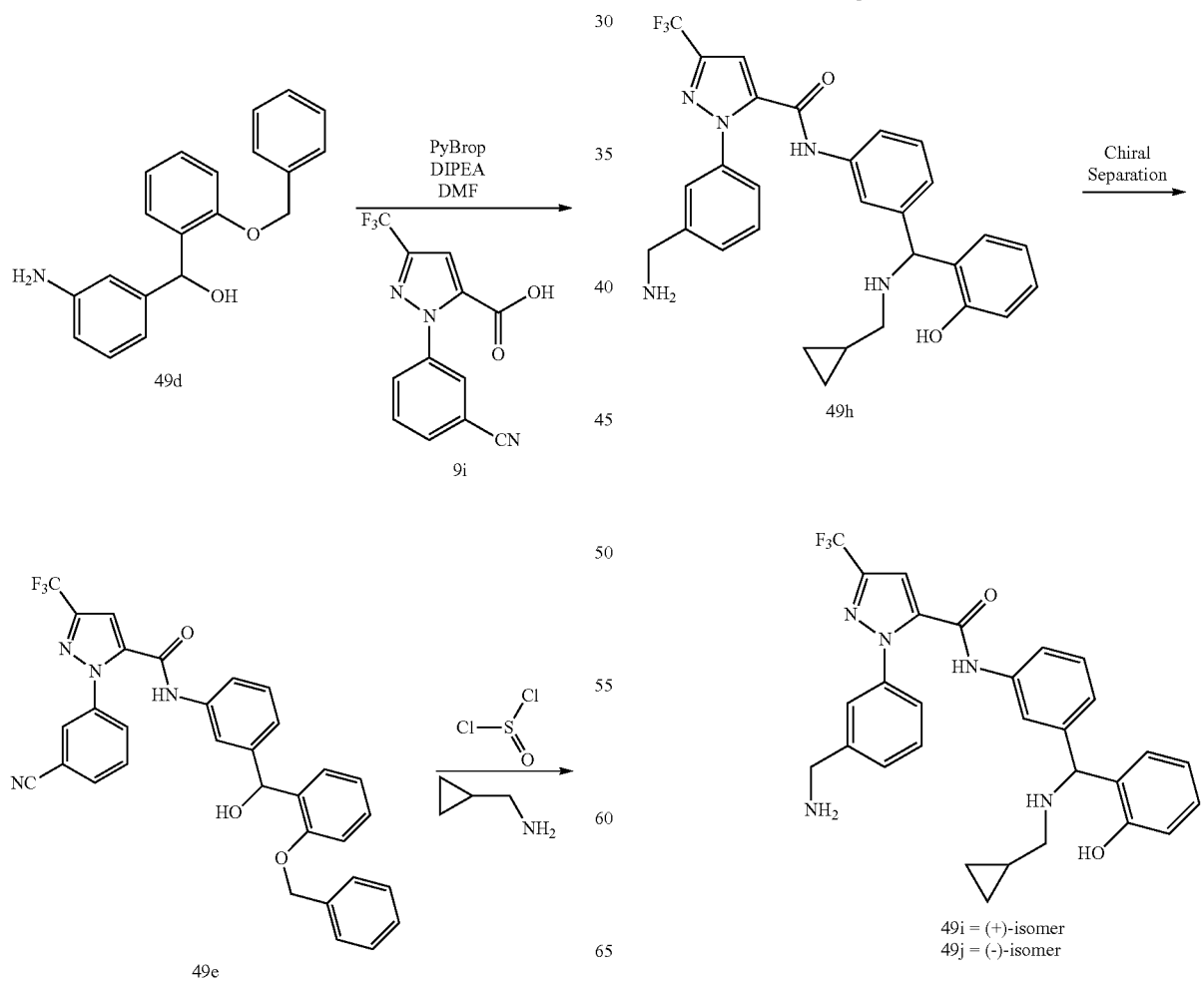

Preparation of Racemic 1-(3-(aminomethyl)phenyl)-N-(3-((cyclopropylmethylamino)(2-hydroxyphenyl)methyl)phenyl)-3-(trifluoromethyl)-1H-pyrazole-5-carboxamide (49h), (+)-1-(3-(aminomethyl)phenyl)-N-(3-((cyclopropylmethylamino)(2-hydroxyphenyl)methyl)phenyl)-3-(trifluoromethyl)-1H-pyrazole-5-carboxamide (49i) and (−)-1-(3-(aminomethyl)phenyl)-N-(3-((cyclopropylmethylamino)(2-hydroxyphenyl)methyl)phenyl)-3-(trifluoromethyl)-1H-pyrazole-5-carboxamide (49j)

Step-1: Preparation of 2-(benzyloxy)benzaldehyde (49b)

To a solution of 2-hydroxybenzaldehyde (49a) (3.98 mL, 38 mmol) in DMF (12 mL) was added cesium carbonate (15.48 g, 47.5 mmol) and benzyl bromide (4.97 mL, 41.8 mmol). The reaction mixture was stirred at room temperature for 36 h and quenched with cold water (50 mL). The solid obtained was collected by filtration washed with water (2×50 mL) and dried under reduced pressure over P2O5 to furnish 2-(benzyloxy)benzaldehyde (49b)(6.524 g, 81%) as white solid; $^1$H NMR (300 MHz, DMSO-$d_6$) δ 10.43 (d, J=0.8 Hz, 1H), 7.75-7.62 (m, 2H), 7.56-7.49 (m, 2H), 7.46-7.30 (m, 4H), 7.10 (tt, J=7.5, 0.9 Hz, 1H), 5.30 (s, 2H); MS (ES$^+$): MS (ES+) 235.2 (M+Na).

Step-2: Preparation of (3-aminophenyl)(2-(benzyloxy)phenyl)methanol (49d)

To a solution of 2-(benzyloxy)benzaldehyde (3 g, 14.13 mmol) in tetrahydrofuran (10 mL) was added 3-[bis(trimethyl silyl)amino]phenylmagnesium chloride solution (49c) (16.96 mL, 16.96 mmol, 1 M solution in THF) at 0° C. The reaction was stirred for 14 h at room temperature and quenched at 0° C. with hydrogen chloride (17.67 mL, 35.3 mmol), stirred for 6 h. The reaction mixture was treated with sodium hydroxide (21.20 mL, 42.4 mmol) and extracted with ethyl acetate (2×75 mL). The organic layers were combined washed with saturated aqueous NH$_4$Cl (75 mL), dried over anhydrous MgSO$_4$, filtered, evaporated to dryness. The crude residue was purified by flash column chromatography (silica gel 80 g, eluting with 0-100% ethyl acetate in hexane) to furnish (3-aminophenyl)(2-(benzyloxy)phenyl)methanol (49d) (4.02 g, 93%) as a white solid; $^1$H NMR (300 MHz, DMSO-$d_6$) δ 7.47 (dd, J=7.5, 1.8 Hz, 1H), 7.41-7.28 (m, 5H), 7.16 (ddd, J=8.9, 7.3, 1.8 Hz, 1H), 7.03-6.82 (m, 3H), 6.56 (t, J=1.9 Hz, 1H), 6.46 (dt, J=7.6, 1.3 Hz, 1H), 6.37 (ddd, J=7.9, 2.3, 1.1 Hz, 1H), 5.90 (d, J=4.3 Hz, 1H), 5.48 (d, J=4.3 Hz, 1H, D$_2$O exchangeable), 5.09 (s, 2H), 4.93 (s, 2H, D$_2$O exchangeable); MS (ES+): MS (ES+) 328.3 (M+Na), MS (ES−) 304.16 (M−1).

Step-3: Preparation of N-(3-((2-(benzyloxy)phenyl)(hydroxy)methyl)phenyl)-1-(3-cyanophenyl)-3-(trifluoromethyl)-1H-pyrazole-5-carboxamide (49e)

In a 100 mL single-necked flask containing 1-(3-cyanophenyl)-3-(trifluoromethyl)-1H-pyrazole-5-carboxylic acid (9i) (1.381 g, 4.91 mmol), (3-aminophenyl)(2-(benzyloxy)phenyl)methanol (49d) (1.5 g, 4.91 mmol), bromo-tris-pyrrolidino phosphoniumhexafluorophosphate(PyBrop) (2.75 g, 5.89 mmol) was added N,N-dimethylformamide (28.5 mL, 368 mmol) and N-ethyl-N-isopropylpropan-2-amine (4.28 mL, 24.56 mmol) successively in a positive flow of nitrogen at room temperature. The resulting reaction mixture was stirred at room temperature for 16 h under a positive flow of nitrogen atmosphere. Excess DMF was pumped-off under reduced pressure. The residue was treated with water (50 mL), and extracted with chloroform (2×50 mL). The combined organics layers were dried over anhydrous MgSO$_4$, filtered, evaporated to dryness. The residue was then purified by flash column chromatography [silica gel 40 g, eluting with ethyl acetate in hexanes from 0-100%] to furnish N-(3-((2-(benzyloxy)phenyl)(hydroxy)methyl)phenyl)-1-(3-cyanophenyl)-3-(trifluoromethyl)-1H-pyrazole-5-carboxamide (49e) (2.568 g, 92% yield) as a white solid; $^1$H NMR (300 MHz, DMSO-$d_6$) δ 10.62 (s, 1H, D$_2$O exchangeable), 8.16 (t, J=1.8 Hz, 1H), 7.99 (dt, J=7.8, 1.3 Hz, 1H), 7.89 (ddd, J=8.2, 2.2, 1.1 Hz, 1H), 7.76-7.68 (m, 2H), 7.64 (t, J=1.8 Hz, 1H), 7.50 (ddd, J=9.6, 8.1, 1.8 Hz, 2H), 7.34-7.29 (m, 4H), 7.25-7.15 (m, 2H), 7.09-6.91 (m, 4H), 6.01 (d, J=4.2 Hz, 1H), 5.76 (d, J=4.2 Hz, 1H, D$_2$O exchangeable), 5.09 (s, 2H); $^{19}$F NMR (282 MHz, DMSO-$d_6$) δ −60.95; IR (KBr, cm$^{-1}$): 2235 cm$^{-1}$ (—CN stretching); MS (ES$^+$): MS (ES+) 591.2 (M+Na), MS (ES−) 567.2 (M−1).

Step-4: Preparation of N-(3-((2-(benzyloxy)phenyl)(cyclopropylmethylamino)methyl)phenyl)-1-(3-cyanophenyl)-3-(trifluoromethyl)-1H-pyrazole-5-carboxamide (49f)

To a solution of N-(3-((2-(benzyloxy)phenyl)(hydroxy)methyl)phenyl)-1-(3-cyanophenyl)-3-(trifluoromethyl)-1H-pyrazole-5-carboxamide (49e) (2.491 g, 4.38 mmol) in dichloromethane (20 mL) at 0° C. was added thionyl chloride (0.959 mL, 13.14 mmol) and allowed to warm to room temperature, after 13 h additional thionyl chloride (0.959 mL, 13.14 mmol) was added and stirred for 1.5 h. The reaction mixture was quenched with cyclopropylmethanamine (2.63 mL, 30.7 mmol) stirred for 1 h at room temperature, and concentrated in vacuum to dryness. The residue was dissolved in cyclopropylmethanamine (7.51 mL, 88 mmol) and acetonitrile (20 mL) and heated at 80° C. for 16 h. The reaction mixture was concentrated in vacuum and residue obtained was treated with water (50 mL), extracted with ethyl acetate (2×50 mL). The organic layers were combined dried over anhydrous MgSO$_4$, filtered and excess solvents were pumped-off under reduced pressure. The residue was purified by flash column chromatography (silica gel 40 g, eluting 0-100% ethyl acetate in hexanes from 0-100%) to afford N-(3-((2-(benzyloxy)phenyl)(cyclopropylmethylamino)methyl)phenyl)-1-(3-cyanophenyl)-3-(trifluoromethyl)-1H-pyrazole-5-carboxamide (49f) (1.168 g, 43% yield) as a yellow solid; $^1$H NMR (300 MHz, DMSO-$d_6$) δ 10.61 (s, 1H, D$_2$O exchangeable), 8.16 (t, J=1.8 Hz, 1H), 7.99 (dt, J=7.7, 1.3 Hz, 1H), 7.89 (ddd, J=8.2, 2.3, 1.2 Hz, 1H), 7.76-7.64 (m, 3H), 7.53 (dd, J=8.3, 1.9 Hz, 1H), 7.44 (dd, J=7.6, 1.7 Hz, 1H), 7.41-7.27 (m, 5H), 7.26-7.07 (m, 3H), 7.01 (dd, J=8.2, 1.1 Hz, 1H), 6.93 (td, J=7.4, 1.1 Hz, 1H), 5.21 (s, 1H), 5.08 (s, 2H), 2.30 (d, J=7.6 Hz, 1H), 2.24 (s, 1H), 2.22 (s, 1H), 0.88 (q, J=6.7 Hz, 1H), 0.41-0.29 (m, 2H), 0.02-−0.01 (m, 2H); MS (ES$^+$): MS (ES+) 622.3 (M+1), MS (ES−) 620.3 (M−1).

Step-5: Preparation of tert-butyl 3-(5-(3-((2-(benzyloxy)phenyl)(cyclopropylmethylamino)methyl)phenylcarbamoyl)-3-(trifluoromethyl)-1H-pyrazol-1-yl)benzylcarbamate (49g)

To a stirred solution of N-(3-((2-(benzyloxy)phenyl)(cyclopropylmethylamino)methyl)phenyl)-1-(3-cyanophenyl)-3-(trifluoromethyl)-1H-pyrazole-5-carboxamide (49f) (1.11 g, 1.786 mmol) in anhydrous methanol (20 mL), cooled to 0° C., were added nickel(II) chloride hexahydrate (0.531 g, 2.232 mmol), sodium borohydride (0.540 g, 14.28 mmol) was then added in small portions over 5 min. The reaction mixture was stirred for 45 min at 0° C., quenched with N1-(2-aminoethyl)ethane-1,2-diamine (1.929 mL, 17.86 mmol), stirred for additional 30 minutes and concentrated in vacuum.

The residue was treated with water (50 mL) and extracted with chloroform (2×50 mL). The organic layers were combined dried over anhydrous $MgSO_4$, filtered, excess solvents were pumped-off under reduced pressure. The residue was purified by flash column chromatography [(silica gel 40 g, eluting with methanol/chloroform from 0 to 100%)] to furnish tert-butyl 3-(5-(3-((2-(benzyloxy)phenyl)(cyclopropylmethylamino)methyl)phenylcarbamoyl)-3-(trifluoromethyl)-1H-pyrazol-1-yl)benzylcarbamate (49g) (525 mg, 40% yield) as a white solid; $^1$H NMR (300 MHz, DMSO-$d_6$) δ 10.65 (s, 1H, $D_2O$ exchangeable), 7.62 (s, 2H), 7.58-7.28 (m, 12H), 7.07 (dd, J=50.3, 30.3 Hz, 4H), 5.21 (s, 1H), 5.09 (s, 2H), 4.18 (d, J=6.2 Hz, 2H), 2.25 (d, J=15.2 Hz, 3H), 1.36 (s, 9H), 0.87 (s, 1H), 0.34 (s, 2H), −0.00 (s, 2H); $^{19}$F NMR (282 MHz, DMSO-$d_6$) δ −60.77; MS (ES$^+$): MS (ES+) 726.5 (M+1), MS (ES−) 724.4 (M−1).

Step-6: Preparation of 1-(3-(aminomethyl)phenyl)-N-(3-((cyclopropylmethylamino)(2-hydroxyphenyl)methyl)phenyl)-3-(trifluoromethyl)-1H-pyrazole-5-carboxamide (49h)

To a solution of tert-butyl 3-(5-(3-((2-(benzyloxy)phenyl)(cyclopropylmethylamino)methyl)phenylcarbamoyl)-3-(trifluoromethyl)-1H-pyrazol-1-yl)benzylcarbamate (49g) (0.496 g, 0.683 mmol) in methanol (30 mL) was added hydrogen chloride (4N in dioxane) (4.27 mL, 17.08 mmol) and palladium (10% Pd on carbon) (0.218 g, 0.205 mmol). The reaction mixture was hydrogenated at 60 psi for 14 h at room temperature. The reaction mixture was filtered through a small Celite pad, Celite pad was subsequently washed with methanol (2×25 mL), and ethyl acetate (25 mL). Excess solvents were pumped-off under reduced pressure. The residue was dissolved in isopropanol (15 mL), then the solution was treated with ethyl ether (30 mL), refluxed for 1 h, cooled to room temperature. The solid obtained was collected by filtration. Solid was dissolved in methanol, filtered through a syringe filter, and pumped-off the excess solvent, this cycle was repeated thrice, after these steps, compound was dried under reduced pressure to afford 1-(3-(aminomethyl)phenyl)-N-(3-((cyclopropylmethylamino)(2-hydroxyphenyl)methyl)phenyl)-3-(trifluoromethyl)-1H-pyrazole-5-carboxamide (49h) (211 mg, 58% yield) as an off-white solid.

$^1$H NMR (300 MHz, DMSO-$d_6$) δ 10.98 (s, 1H), 10.36 (s, 1H, $D_2O$ exchangeable), 10.02 (s, 1H, $D_2O$ exchangeable), 9.76 (s, 1H, $D_2O$ exchangeable), 8.56 (s, 3H, $D_2O$ exchangeable), 7.83 (t, J=1.7 Hz, 1H), 7.77-7.69 (m, 3H), 7.68-7.47 (m, 5H), 7.40 (t, J=7.9 Hz, 1H), 7.23-7.12 (m, 1H), 6.97 (dd, J=8.3, 1.2 Hz, 1H), 6.87 (t, J=7.2 Hz, 1H), 5.83-5.65 (m, 1H), 4.11 (q, J=5.7, 5.2 Hz, 2H), 2.83-2.64 (m, 2H), 1.22-1.07 (m, 1H), 0.54 (dt, J=7.9, 3.0 Hz, 2H), 0.31 (t, J=5.0 Hz, 2H); $^1$H NMR (300 MHz, DMSO-$d_6$, $D_2O$) δ 10.96 (s, 1H), 7.80 (s, 1H), 7.72 (t, J=1.8 Hz, 1H), 7.69-7.38 (m, 8H), 7.27-7.17 (m, 1H), 6.99-6.86 (m, 2H), 5.71 (s, 1H), 4.13 (s, 2H), 2.75 (d, J=7.3 Hz, 2H), 1.09 (tt, J=8.1, 4.8 Hz, 1H), 0.69-0.45 (m, 2H), 0.40-0.17 (m, 2H); $^{19}$F NMR (282 MHz, DMSO-$d_6$) δ −60.75; MS (ES$^+$): MS (ES+) 536.3 (M+1), 534.3 (M−1), 570.3 (M+Cl); Analysis calculated for: $C_{29}H_{28}F_3N_5O_2 \cdot 6H_2O \cdot 2.75HCl$: C, 46.82; H, 5.79; Cl, 13.11; N, 9.41; Found: C, 47.02; H, 5.49; Cl, 12.78; N, 9.37.

Step-7: Preparation of (+)-1-(3-(aminomethyl)phenyl)-N-(3-((cyclopropylmethylamino)(2-hydroxyphenyl)methyl)phenyl)-3-(trifluoromethyl)-1H-pyrazole-5-carboxamide (49i) and (−)-1-(3-(aminomethyl)phenyl)-N-(3-((cyclopropylmethylamino)(2-hydroxyphenyl)methyl)phenyl)-3-(trifluoromethyl)-1H-pyrazole-5-carboxamide (49j)

Racemic 1-(3-(aminomethyl)phenyl)-N-(3-((cyclopropylmethylamino)(2-hydroxyphenyl)methyl)phenyl)-3-(trifluoromethyl)-1H-pyrazole-5-carboxamide (49h) (1.09 g) was separated using chiral preparative HPLC using CHIRALPAK AY-H, 5μ, 4.6×250 mm, flow rate 1 mL/min, Solvent: 90% ACN/10% MeOH/0.1% DEA, UV=320 nM, to furnish:
1. (+)-1-(3-(aminomethyl)phenyl)-N-(3-((cyclopropylmethylamino)(2-hydroxyphenyl)methyl)phenyl)-3-(trifluoromethyl)-1H-pyrazole-5-carboxamide (49i) (0.5415 g, >99% ee) Rt=4.672 min (100%) (as peak-1, for 49i) Rt=5.448 (0% peak-2, for 49j). This product was repurified by flash column chromatography (silica gel 25 g, eluting 0-25% methanol in chloroform for 13 mins) to furnish pure (+)-1-(3-(aminomethyl)phenyl)-N-(3-((cyclopropylmethylamino)(2-hydroxyphenyl)methyl)phenyl)-3-(trifluoromethyl)-1H-pyrazole-5-carboxamide (49i) (0.31 g) as a white solid. Optical rotation +52.03 (MeOH, 1.18); $^1$H NMR (300 MHz, DMSO-$d_6$) δ 11.64 (s, 1H), 10.73 (s, 1H), 7.67-7.61 (m, 1H), 7.59-7.50 (m, 3H), 7.46-7.40 (m, 2H), 7.31 (dq, J=4.9, 2.6 Hz, 1H), 7.26 (d, J=7.8 Hz, 1H), 7.20 (dt, J=7.9, 1.4 Hz, 1H), 7.02 (dtd, J=7.4, 4.5, 4.0, 1.7 Hz, 2H), 6.73-6.64 (m, 2H), 5.00 (s, 1H), 3.77 (s, 2H), 2.47-2.37 (m, 1H), 2.33-2.21 (m, 1H), 1.00-0.90 (m, 1H), 0.40 (dt, J=9.0, 2.9 Hz, 2H), 0.17-0.05 (m, 2H); $^{19}$F NMR (282 MHz, DMSO) δ −60.68; MS (ES+) 536.3 (M+1); (ES−) 534.3 (M−1). The free base of (+)-1-(3-(aminomethyl)phenyl)-N-(3-((cyclopropylmethylamino)(2-hydroxyphenyl)methyl)phenyl)-3-(trifluoromethyl)-1H-pyrazole-5-carboxamide (49i) was dissolved in methanol and added (2.5 mL) of 2 N HCl in methanol. The mixture was concentrated in vacuum to dryness to furnish (+)-1-(3-(aminomethyl)phenyl)-N-(3-((cyclopropylmethylamino)(2-hydroxyphenyl)methyl)phenyl)-3-(trifluoromethyl)-1H-pyrazole-5-carboxamide (49i) (300 mgs) as a HCl salt; $^1$H NMR (300 MHz, DMSO-$d_6$) δ 10.94 (s, 1H), 10.32 (s, 1H), 9.88 (d, J=11.6 Hz, 1H), 9.63 (s, 1H), 8.44 (s, 3H), 7.81 (s, 1H), 7.72 (t, J=1.7 Hz, 1H), 7.70-7.59 (m, 4H), 7.59-7.48 (m, 3H), 7.41 (t, J=7.9 Hz, 1H), 7.24-7.14 (m, 1H), 6.97-6.84 (m, 2H), 5.72 (d, J=6.6 Hz, 1H), 4.12 (q, J=5.8, 5.4 Hz, 2H), 2.73 (d, J=6.4 Hz, 2H), 1.19-1.01 (m, 1H), 0.65-0.46 (m, 2H), 0.38-0.21 (m, 2H); $^{19}$F NMR (282 MHz, DMSO) δ −60.75; MS (ES+) 536.3 (M+1); (ES−) 570.3 (M+Cl); Analysis calculated for $C_{29}H_{28}F_3N_5O_2 \cdot 2HCl \cdot 1.25H_2O$: C, 55.20; H, 5.19; Cl, 11.24; N, 11.10; Found: C, 55.37; H, 5.20; Cl, 10.80; N, 10.61.
2. (−)-1-(3-(aminomethyl)phenyl)-N-(3-((cyclopropylmethylamino)(2-hydroxyphenyl)methyl)phenyl)-3-(trifluoromethyl)-1H-pyrazole-5-carboxamide (49j) (0.670 g, 76.341% ee) Rt=4.668 min (11.8295%) (peak-1, for 49i) Rt=5.447 (88.1705% peak-2, for 49j). This product was repurified by flash column chromatography (silica gel 25 g, eluting 0-30% methanol in chloroform for 30 mins) to furnish pure (−)-1-(3-(aminomethyl)phenyl)-N-(3-((cyclopropylmethylamino)(2-hydroxyphenyl)methyl)phenyl)-3-(trifluoromethyl)-1H-pyrazole-5-carboxamide (49j) (0.461 g) as a yellow waxy solid. Optical rotation −40.85 (MeOH, 2.11); $^1$H NMR (300 MHz, DMSO-$d_6$) δ 10.73 (s, 1H, $D_2O$ exchangeable), 7.65 (d, J=2.2 Hz, 1H), 7.56 (q, J=2.7, 1.6 Hz, 2H), 7.52 (s, 1H), 7.47-7.41 (m, 2H), 7.33-7.27 (m, 3H), 7.22 (dd, J=10.0, 8.5 Hz, 1H), 7.03 (ddd, J=7.1, 4.2, 2.4 Hz, 2H), 6.72-6.65 (m, 2H), 5.00 (s, 1H), 3.78 (s, 2H), 2.46-2.39 (m, 1H), 2.26 (dd, J=12.3, 7.0 Hz, 1H), 0.94 (d, J=7.3 Hz, 1H), 0.40 (dt, J=8.7, 2.8 Hz, 2H), 0.17-0.03 (m, 2H); 1H NMR (300 MHz, DMSO-$d_6$ $D_2O$) δ 7.65 (d, J=2.0 Hz, 1H), 7.60-7.50 (m, 2H), 7.45-7.41 (m, 2H), 7.36-7.27 (m, 3H), 7.26-7.17 (m, 1H), 7.03 (t, J=7.5 Hz, 2H), 6.71 (d, J=1.5 Hz, 1H), 6.70-6.68 (m, 1H), 5.00 (s, 1H), 3.76 (s, 2H), 2.45-2.38 (m, 1H), 2.25 (dd, J=12.2, 7.0 Hz, 1H), 0.96 (dd, J=14.1, 7.1 Hz, 1H), 0.51-0.29 (m, 2H), 0.08 (dt, J=5.3, 2.6 Hz, 2H); $^{19}$F NMR (282 MHz, DMSO-$d_6$) δ −60.70; MS (ES+) 536.3 (M+1), 534.3 (M−1). The free base of (−)-1-(3-(aminomethyl)phenyl)-N-(3-((cyclopropylmethylamino)(2-hydroxyphenyl)methyl)phenyl)-3-(trifluoromethyl)-1H-pyrazole-5-carboxamide (49j) (0.451 g) was dissolved in methanol (15 mL) and added (4.21 mL of 2 N HCl in methanol, 10 equi). The mixture was concentrated in vacuum to dryness to furnish (−)-1-(3-(aminomethyl)phenyl)-N-(3-((3-aminophenyl)(cyclopropylmethoxy)methyl)phenyl)-3-(trifluoromethyl)-1H-pyrazole-5-carboxamide (49j) (386 mg) HCl salt as an off-white solid; $^1$H NMR (300 MHz, DMSO-$d_6$) δ 10.96 (s, 1H), 10.35 (s, 1H), 9.95 (s, 1H), 9.70 (s, 1H), 8.50 (s, 3H), 7.82 (t, J=1.8 Hz, 1H), 7.75-7.67 (m, 3H), 7.64 (dt, J=7.7, 1.8 Hz, 2H), 7.60-7.48 (m, 3H), 7.45-7.26 (m, 4H), 7.18 (ddd, J=8.6, 7.3, 1.6 Hz, 1H), 6.96 (dd, J=8.2, 1.2 Hz, 1H), 6.93-6.83 (m, 1H), 6.73 (s, 2H), 6.10 (s, 6H), 5.72 (t, J=6.6 Hz, 1H), 4.12 (d, J=5.8 Hz, 2H), 2.73 (d, J=6.1 Hz, 2H), 1.12 (s, 1H), 0.67-0.47 (m, 2H), 0.30 (h, J=4.0 Hz, 2H); 1H NMR (300 MHz, DMSO-$d_6$, $D_2O$) δ 10.95 (s, 1H), 7.79 (s, 1H), 7.71 (t, J=1.8 Hz, 1H), 7.63 (d, J=4.8 Hz, 2H), 7.60 (dd, J=3.7, 2.0 Hz, 1H), 7.56 (td, J=4.5, 2.1 Hz, 2H), 7.52 (t, J=2.0 Hz, 1H), 7.50-7.43 (m, 3H), 7.22 (ddd, J=8.6, 7.3, 1.6 Hz, 1H), 7.01-6.85 (m, 2H), 5.71 (s, 1H), 4.13 (s, 2H), 2.75 (d, J=7.2 Hz, 2H), 1.18-0.99 (m, 1H), 0.71-0.47 (m, 2H), 0.40-0.16 (m, 2H); $^{19}$F NMR (282 MHz, DMSO-$d_6$) δ −60.76; MS (ES+) 536.3 (M+1), 534.3 (M−1), 570.3 (M+Cl).

Scheme 50

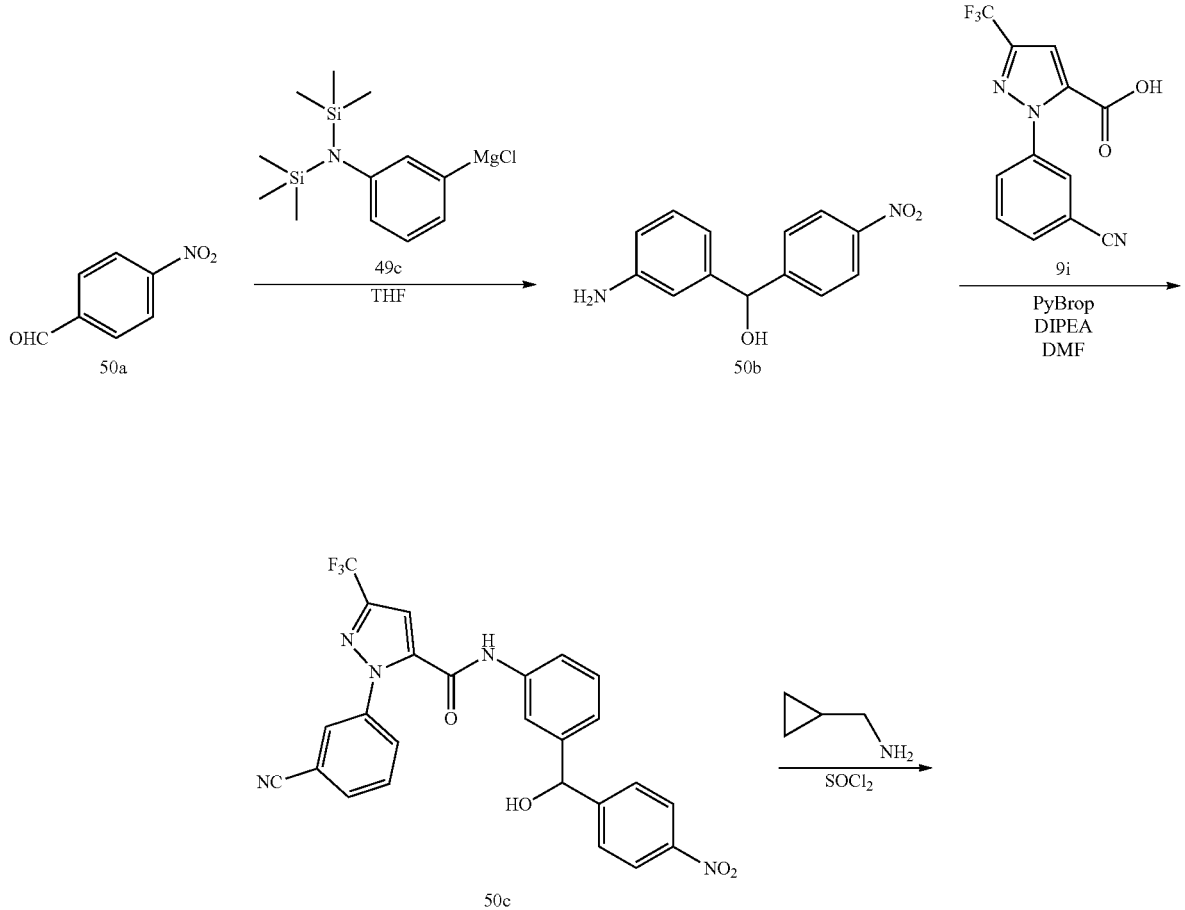

-continued

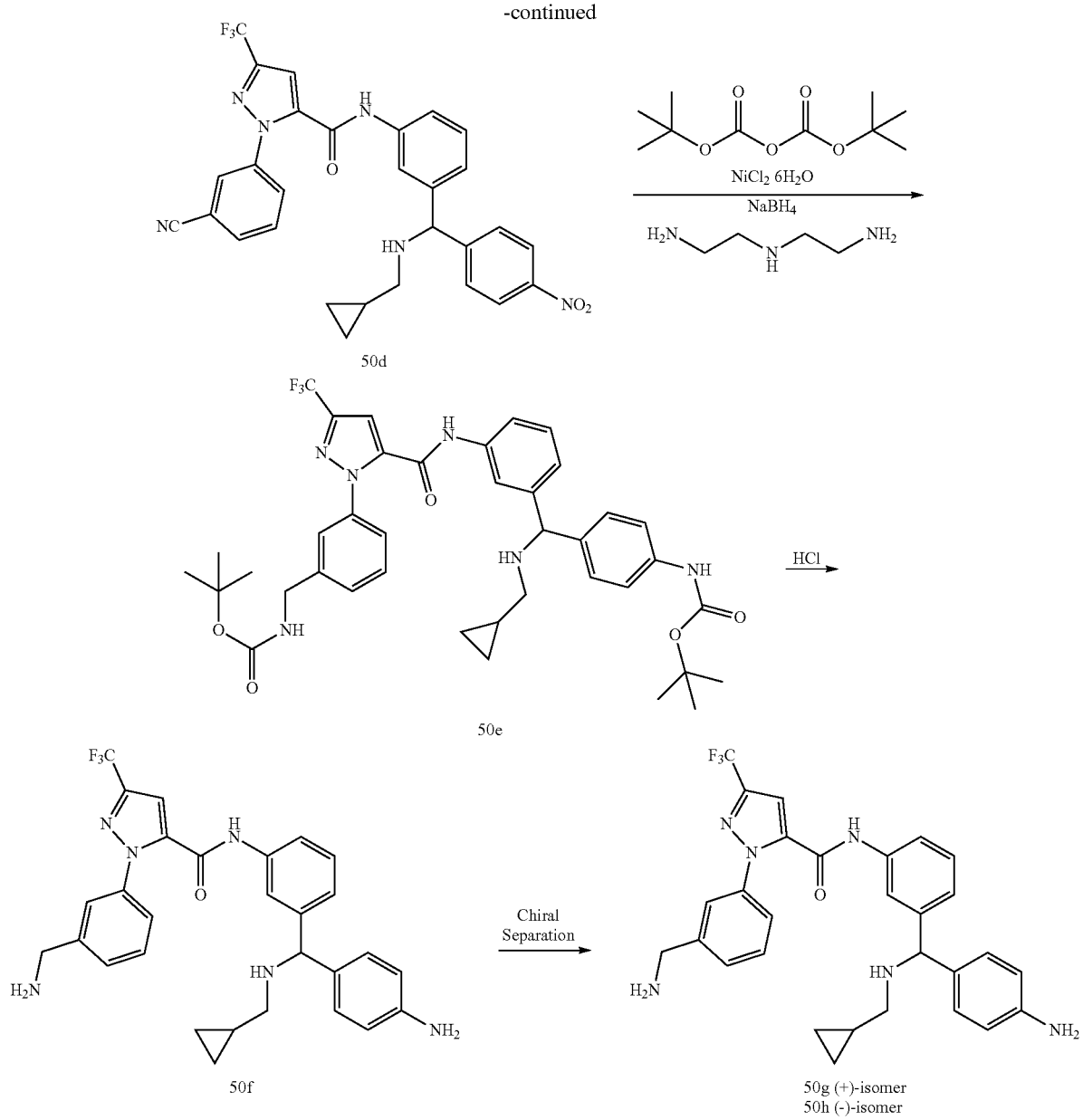

Preparation of Racemic 1-(3-(aminomethyl)phenyl)-N-(3-((4-aminophenyl)(cyclopropylmethyl-amino)methyl)phenyl)-3-(trifluoromethyl)-1H-pyrazole-5-carboxamide (50f); (+)-1-(3-(aminomethyl)phenyl)-N-(3-((4-aminophenyl)(cyclopropylmethyl-amino)methyl)phenyl)-3-(trifluoromethyl)-1H-pyrazole-5-carboxamide (50g) and (−)-1-(3-(aminomethyl)phenyl)-N-(3-((4-aminophenyl)(cyclopropylmethyl-amino)methyl)phenyl)-3-(trifluoromethyl)-1H-pyrazole-5-carboxamide (50h)

Step-1: Preparation of (3-aminophenyl)(4-nitrophenyl)methanol (50b)

To a solution of 4-nitrobenzaldehyde (50a) (5 g, 32.4 mmol) in tetrahydrofuran (60 mL) was added 3-[bis(trimethylsilyl)amino]phenylmagnesium chloride solution (49c) (36.0 g, 36 mmol) at 0° C. The reaction was stirred for 2 h at at 0° C. room and quenched with saturated aqueous NH$_4$Cl (100 mL). The reaction mixture was extracted with ethyl acetate (2×120 mL).

The organic layers were combined washed with brine (100 mL), dried over anhydrous MgSO$_4$, filtered and evaporated to dryness. The crude residue was purified by flash column chromatography [silica gel 120 g, eluting with chloroform/CMA80 (1:0 to 2:1)] to give (3-aminophenyl)(4-nitrophenyl)methanol (50b) (3.524 g, 45%) as a dark brown gum; $^1$H NMR (300 MHz, DMSO-d$_6$) δ 8.22-8.14 (m, 2H), 7.68-7.57 (m, 2H), 6.94 (t, J=7.7 Hz, 1H), 6.59-6.49 (m, 2H), 6.40 (ddd, J=8.0, 2.3, 1.0 Hz, 1H), 6.06 (d, J=3.8 Hz, 1H), 5.65 (d, J=3.8 Hz, 1H), 5.05 (s, 2H); MS (ES+) 245.2 (M+1).

Step-2: Preparation of 1-(3-cyanophenyl)-N-(3-(hydroxy(4-nitrophenyl)methyl)phenyl)-3-(trifluoromethyl)-1H-pyrazole-5-carboxamide (50c)

In a 100 mL single-necked flask containing 1-(3-cyanophenyl)-3-(trifluoromethyl)-1H-pyrazole-5-carboxylic acid (9i) (1.381 g, 4.91 mmol), (3-aminophenyl)(4-nitrophenyl)methanol (50b) (1.19 g, 4.91 mmol), bromo-tris-pyrrolidino phosphoniumhexafluorophosphate(PyBrop) (6.65 g, 13.98 mmol) was added N,N-dimethylformamide (80 mL) and N-ethyl-N-isopropylpropan-2-amine (20.00 mL, 115 mmol) successively in a positive flow of nitrogen at room temperature. The resulting reaction mixture was stirred at room temperature for 14 h under a positive flow of nitrogen atmosphere. The reaction mixture was diluted with ethyl acetate (300 mL), washed with water (2×120 mL), brine (120 mL), dried over MgSO$_4$, filtered and concentrated in vacuum. The crude product was purified by flash column chromatography [silica gel 120 g, eluting with hexanes/ethyl acetate (1:0 to 1:1)] to give 1-(3-cyanophenyl)-N-(3-(hydroxy(4-nitrophenyl)methyl)phenyl)-3-(trifluoromethyl)-1H-pyrazole-5-carboxamide (50c) (3.8 g, 54%) as a light brown solid; $^1$H NMR (300 MHz, DMSO-d$_6$) δ 10.66 (s, 1H), 8.23-8.14 (m, 3H), 8.00 (dt, J=7.8, 1.3 Hz, 1H), 7.90 (ddd, J=8.2, 2.2, 1.1 Hz, 1H), 7.78-7.61 (m, 5H), 7.57 (dt, J=8.1, 1.4 Hz, 1H), 7.30 (t, J=7.9 Hz, 1H), 7.21-7.15 (m, 1H), 6.31 (d, J=3.9 Hz, 1H), 5.85 (d, J=3.9 Hz, 1H); $^{19}$F NMR (282 MHz, DMSO-d$_6$) δ −60.97; MS (ES+) 530.3 (M+23).

Step-3: Preparation of 1-(3-cyanophenyl)-N-(3-((cyclopropylmethylamino)(4-nitrophenyl)-methyl)phenyl)-3-(trifluoromethyl)-1H-pyrazole-5-carboxamide (50d)

To a solution of 1-(3-cyanophenyl)-N-(3-(hydroxy(4-nitrophenyl)methyl)phenyl)-3-(trifluoromethyl)-1H-pyrazole-5-carboxamide (50c) (1.9 g, 3.74 mmol) in dichloromethane (60 mL) at 0° C. was added thionyl chloride (0.790 mL, 10.67 mmol) and warmed to room temperature over 2 h. The reaction mixture was quenched with triethyl amine (4.60 mL, 33.0 mmol) stirred at room temperature for 1 h. It was then treated with cyclopropylmethanamine (5.49 g, 74.9 mmol), concentrated to remove most of dichloromethane followed by addition of acetonitrile (45 mL), stirring at 70° C. for 19 h, and concentration in vacuum to dryness. The residue was treated with chloroform (200 mL), washed with water (100 mL), dried over MgSO$_4$ followed by filtration and concentration. The crude product was purified by flash column chromatography [silica gel eluting with hexanes/ethyl acetate (1:0 to 2:1)] to afford 1-(3-cyanophenyl)-N-(3-((cyclopropylmethylamino)(4-nitrophenyl)-methyl)phenyl)-3-(trifluoromethyl)-1H-pyrazole-5-carboxamide (50d) (466 mg) as a brown gum, which was pure enough to be taken to next step; MS (ES+) 561.3 (M+1).

Step-4: Preparation of tert-butyl 3-(5-((3-((4-tert-butyloxycarbonyl aminophenyl)((cyclopropylmethyl)amino)methyl)phenyl)carbamoyl)-3-(trifluoromethyl)-1H-pyrazol-1-yl)benzylcarbamate (50e)

To a stirred solution of afford 1-(3-cyanophenyl)-N-(3-((cyclopropylmethylamino)(4-nitrophenyl)-methyl)phenyl)-3-(trifluoromethyl)-1H-pyrazole-5-carboxamide (50d) (458 mg, 0.817 mmol) in anhydrous methanol (12 mL), cooled to 0° C., were added di-tert-butyl dicarbonate (540 mg, 2.451 mmol) and nickel(II) chloride hexahydrate (105 mg, 0.442 mmol) and sodium borohydride (0.540 g, 14.28 mmol) was then added in small portions over 5 min. The reaction mixture was stirred for 45 min at 0° C., quenched with N1-(2-aminoethyl)ethane-1,2-diamine (0.410 mL, 3.75 mmol), stirred for additional 30 minutes and concentrated in vacuum. The residue was treated with ethyl acetate (120 mL) washed with water (60 mL). the aqueous layer was extracted again with ethyl acetate (80 mL). The organic layers were combined, washed with brine (80 mL) dried over anhydrous MgSO$_4$, filtered and concentrated in vacuum. The residue was purified by flash column chromatography [silica gel 40 g, eluting with hexanes/ethyl acetate (1:0 to 1:1)] to afford tert-butyl 3-(5-((3-((4-tert-butyloxycarbonyl aminophenyl)((cyclopropylmethyl)amino)methyl)phenyl)carbamoyl)-3-(trifluoromethyl)-1H-pyrazol-1-yl)benzylcarbamate (50e) (81 mg, 3% for 2 steps) as a white solid, MS (ES+) 735.5 (M+1).

Step-5: Preparation of 1-(3-(aminomethyl)phenyl)-N-(3-((4-aminophenyl)(cyclopropylmethyl-amino)methyl)phenyl)-3-(trifluoromethyl)-1H-pyrazole-5-carboxamide (50f)

To a solution of tert-butyl 3-(5-((3-((4-tert-butyloxycarbonyl aminophenyl)((cyclopropylmethyl)amino)methyl)phenyl)carbamoyl)-3-(trifluoromethyl)-1H-pyrazol-1-yl)benzylcarbamate (50e) (79 mg, 0.108 mmol) in 1,4-Dioxane (8 mL) was added dropwise hydrogen chloride (1.2 mL, 4.8 mmol, 4 M in 1,4-dioxane) and stirred at room temperature for 15 h. The reaction mixture was diluted with hexanes, decanted, washed with hexanes, and decanted again. The insoluble crude product was purified by flash column chromatography [silica gel, eluting with chloroform/CMA80 (1:0 to 2:1)] to give 1-(3-(aminomethyl)phenyl)-N-(3-((4-aminophenyl)(cyclopropylmethyl-amino)methyl)phenyl)-3-(trifluoromethyl)-1H-pyrazole-5-carboxamide (50f) (41 mg) as a light yellow gum; $^1$H NMR (300 MHz, DMSO-d$_6$) δ 10.65 (s, 1H), 7.60 (t, J=1.8 Hz, 1H), 7.56 (s, 1H), 7.54-7.46 (m, 2H), 7.46-7.38 (m, 2H), 7.31 (dt, J=6.5, 2.5 Hz, 1H), 7.22 (t, J=7.8 Hz, 1H), 7.16-7.10 (m, 1H), 7.03-6.96 (m, 2H), 6.51-6.41 (m, 2H), 4.90 (s, 2H), 4.61 (s, 1H), 2.26 (d, J=6.7 Hz, 2H), 2.05 (s, 2H), 0.90 (p, J=7.0 Hz, 1H), 0.44-0.22 (m, 2H), 0.09-0.00 (m, 2H); $^{19}$F NMR (282 MHz, DMSO-d$_6$) δ −60.70; MS (ES+) 535.3 (M+1), (ES−) 533.3 (M−1); IR (KBr pellet, cm$^{-1}$): 3441, 3005, 1616, 1558, 1243; Analysis calculated for C$_{29}$H$_{29}$F$_3$N$_6$O.1.0H$_2$O: C, 63.03; H, 5.65; N, 15.21; Found: C, 63.42; H, 5.41; N, 14.83.

Step-6: Preparation of (+)-1-(3-(aminomethyl)phenyl)-N-(3-((4-aminophenyl)(cyclopropylmethyl-amino)methyl)phenyl)-3-(trifluoromethyl)-1H-pyrazole-5-carboxamide (50g) and (−)-1-(3-(aminomethyl)phenyl)-N-(3-((4-aminophenyl)(cyclopropylmethyl-amino)methyl)phenyl)-3-(trifluoromethyl)-1H-pyrazole-5-carboxamide (50h)

Racemic 1-(3-(aminomethyl)phenyl)-N-(3-((4-aminophenyl)(cyclopropylmethyl-amino)methyl)phenyl)-3-(trifluoromethyl)-1H-pyrazole-5-carboxamide (50f) (0.201 g) was separated using chiral preparative HPLC using CHIRALPAK IC column, 5µ, 4.6×250 mm, flow rate 1 mL/min, Solvent: 70% Hexane/30% EtOH/0.1% DEA, UV=254 nM, to furnish:
1. (+)-1-(3-(aminomethyl)phenyl)-N-(3-((4-aminophenyl)(cyclopropylmethyl-amino)methyl)phenyl)-3-(trifluoromethyl)-1H-pyrazole-5-carboxamide (50g) (0.091 g, Rt=7.73 min (100%), >99.9% ee), Optical rotation +10.37 (MeOH, 0.54); $^1$H NMR (300 MHz, Methanol-d$_4$) δ 7.55-7.50 (m, 2H), 7.48-7.42 (m, 3H), 7.45-7.34 (m, 1H), 7.32 (s, 1H), 7.26 (t, J=7.8 Hz, 1H), 7.18 (dt, J=7.7, 1.4 Hz, 1H), 7.13-7.06 (m, 2H), 6.70-6.62 (m, 2H), 4.75 (s, 1H), 3.83 (s, 2H), 2.36 (d, J=6.9 Hz, 2H), 1.03-0.88 (m, 1H), 0.52-0.40 (m, 2H), 0.06 (qd, J=4.5, 2.9 Hz, 2H); $^1$H NMR (300 MHz, DMSO-d$_6$) δ 10.65 (s, 1H), 7.60 (t, J=1.8 Hz, 1H), 7.57 (s, 1H), 7.54-7.40 (m, 4H), 7.31 (dt, J=6.2, 2.4 Hz, 1H), 7.22 (t, J=7.8 Hz, 1H), 7.16-7.10 (m, 1H), 7.04-6.95 (m, 2H), 6.49-6.42 (m, 2H), 4.91 (s, 2H), 4.61 (s, 1H), 3.78 (s, 2H), 2.26 (d, J=6.7 Hz, 2H), 0.97-0.84 (m, 1H), 0.40-0.31 (m, 2H), 0.09--0.02 (m, 2H); $^{19}$F NMR (282 MHz, MeOD) δ -63.72; $^{19}$F NMR (282 MHz, DMSO) δ -60.71; MS (ES+) 557.3 (M+Na); (ES-) 533.3 (M-1). The free base (+)-1-(3-(aminomethyl)phenyl)-N-(3-((4-aminophenyl)(cyclopropylmethyl-amino)methyl)phenyl)-3-(trifluoromethyl)-1H-pyrazole-5-carboxamide (50g) (0.085 g, 0.159 mmol) was dissolved in methanol (5 mL) and added HCl (0.133 mL, 1.590 mmol). The reaction mixture was concentrated in vacuum to dryness and co-distilled twice with chloroform dried in vacuum to furnish (+)-1-(3-(aminomethyl)phenyl)-N-(3-((4-aminophenyl)(cyclopropyl-methyl-amino)methyl)phenyl)-3-(trifluoromethyl)-1H-pyrazole-5-carboxamide (50g) (0.07 g, 0.109 mmol) trihydrochloride as a yellow solid; $^1$H NMR (300 MHz, DMSO-d$_6$) δ 10.98 (s, 1H), 10.08 (s, 2H), 8.50 (s, 3H), 7.91-7.81 (m, 1H), 7.73 (d, J=2.0 Hz, 1H), 7.71 (s, 1H), 7.66-7.57 (m, 5H), 7.56-7.49 (m, 2H), 7.44 (t, J=7.9 Hz, 1H), 7.15 (d, J=7.9 Hz, 2H), 5.54 (t, J=6.2 Hz, 1H), 4.12 (q, J=5.8 Hz, 2H), 2.88-2.59 (m, 2H), 1.21-1.09 (m, 1H), 0.65-0.45 (m, 2H), 0.40-0.19 (m, 2H); $^{19}$F NMR (282 MHz, DMSO-d$_6$) δ -60.78; MS (ES+) 535.4 (M+1), 557.3 (M+Na); (ES-) 533.3 (M-1), 569.3 (M+Cl); Analysis calculated for C$_{29}$H$_{29}$F$_3$N$_6$O.3HCl.1.75H$_2$O: C, 51.56; H, 5.30; N, 12.44; Found; C, 51.68; H, 5.61; N, 11.54.

2. (-)-1-(3-(aminomethyl)phenyl)-N-(3-((4-aminophenyl)(cyclopropylmethyl-amino)methyl)phenyl)-3-(trifluoromethyl)-1H-pyrazole-5-carboxamide (50h) (0.132 g, Rt=10.449 min (99.6604%), >99.4% ee); $^1$H NMR (300 MHz, Methanol-d$_4$) δ 7.72 (t, J=1.8 Hz, 1H), 7.66 (d, J=1.8 Hz, 1H), 7.55 (ddq, J=13.2, 6.1, 1.6 Hz, 4H), 7.44-7.34 (m, 2H), 7.28 (dt, J=7.9, 1.4 Hz, 1H), 7.21-7.13 (m, 2H), 6.75-6.60 (m, 2H), 5.14 (s, 1H), 4.14 (s, 2H), 2.65 (d, J=7.2 Hz, 2H), 1.12-0.98 (m, 1H), 0.67-0.52 (m, 2H), 0.27-0.14 (m, 2H); $^{19}$F NMR (282 MHz, Methanol-d$_4$) δ -63.80; MS (ES+) 535.4 (M+1); 557.3 (M+Na); (ES-) 569.3 (M+Cl). This product was repurified by flash column chromatography (silica gel 4 g, eluting with 0-100% CMA-80 in chloroform) to furnish pure (-)-1-(3-(aminomethyl)phenyl)-N-(3-((4-aminophenyl)(cyclopropylmethyl-amino)methyl)phenyl)-3-(trifluoromethyl)-1H-pyrazole-5-carboxamide (50h) (36 mgs) of free base as a white solid. Optical rotation -11.5 (MeOH, 1.8); The above free base of (-)-1-(3-(aminomethyl)phenyl)-N-(3-((4-aminophenyl)(cyclopropylmethyl-amino)methyl)phenyl)-3-(trifluoromethyl)-1H-pyrazole-5-carboxamide (50h) (0.036 g, 0.067 mmol) was dissolved in methanol (5 mL) and added HCl (0.056 mL, 0.673 mmol).

The reaction mixture was concentrated in vacuum to dryness and co-distilled twice with chloroform dried in vacuum to furnish (-)-1-(3-(aminomethyl)phenyl)-N-(3-((4-aminophenyl)(cyclopropylmethyl-amino)methyl)phenyl)-3-(trifluoromethyl)-1H-pyrazole-5-carboxamide (50h) (0.04 g) trihydrochloride as a yellow solid; $^1$H NMR (300 MHz, DMSO-d$_6$) δ 10.97 (s, 1H), 10.12-9.91 (m, 2H), 8.47 (s, 3H), 7.88-7.81 (m, 1H), 7.74-7.71 (m, 1H), 7.70 (s, 1H), 7.66-7.48 (m, 7H), 7.44 (t, J=7.9 Hz, 1H), 7.08 (d, J=7.8 Hz, 2H), 5.51 (d, J=6.6 Hz, 1H), 4.12 (q, J=5.7 Hz, 2H), 2.69 (q, J=6.4 Hz, 2H), 1.23-1.05 (m, 1H), 0.65-0.44 (m, 2H), 0.39-0.20 (m, 2H); $^{19}$F NMR (282 MHz, DMSO-d$_6$) δ -60.78; MS (ES+) 535.4 (M+1); 557.4 (M+Na); (ES-) 569.3 (M+Cl); Analysis calculated for C$_{29}$H$_{29}$F$_3$N$_6$O.3HCl.3H$_2$O: C, 49.90; H, 5.49; N, 12.04; Found: C, 49.85; H, 5.49; N, 11.45.

Scheme 51

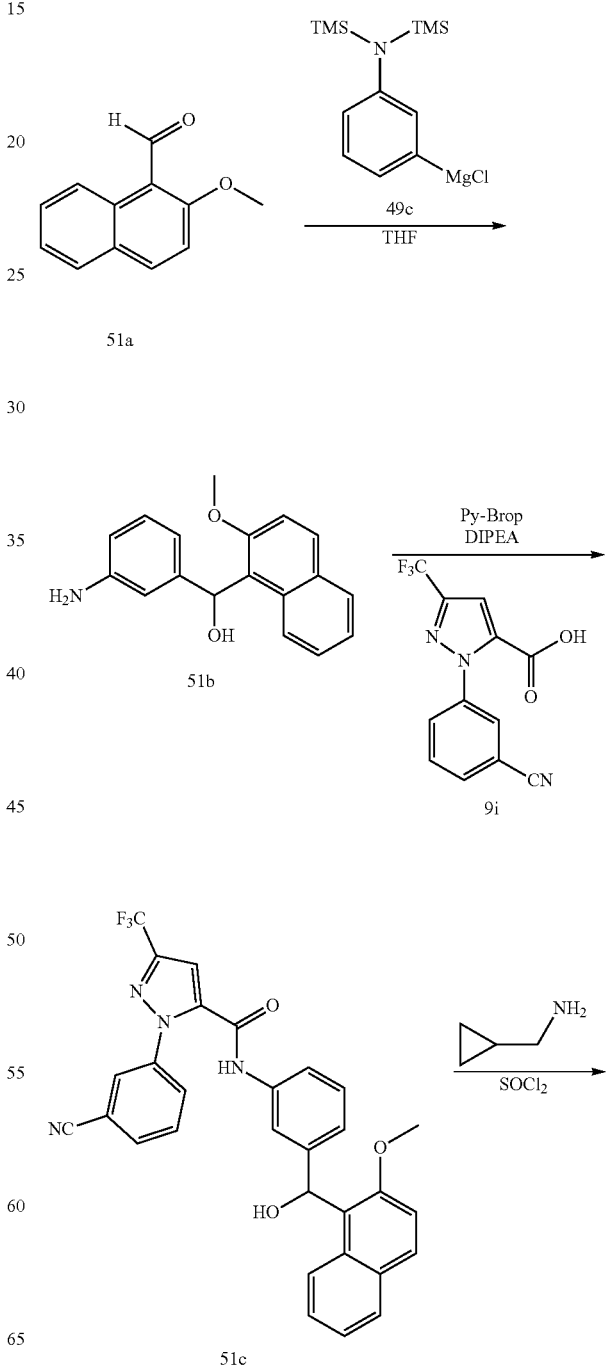

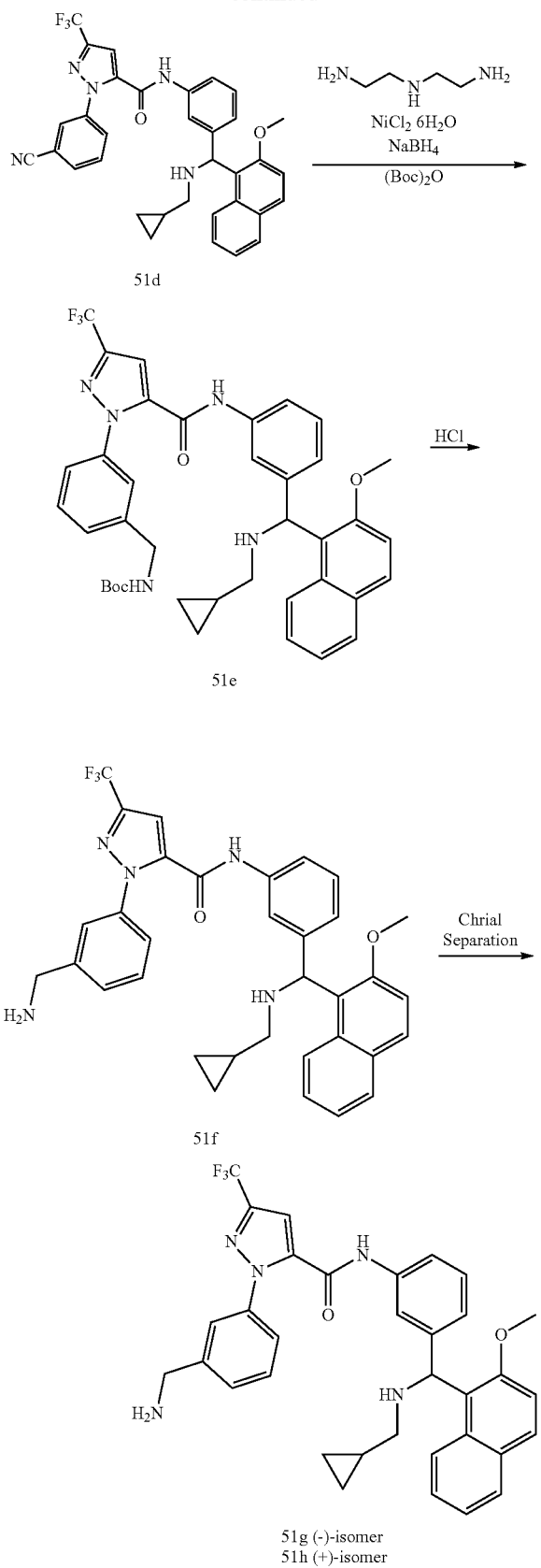

Preparation of Racemic 1-(3-(Aminomethyl)phenyl)-N-(3-((cyclopropylmethylamino)(2-methoxynaphthalen-1-yl)methyl)phenyl)-3-(trifluoromethyl)-1H-pyrazole-5-carboxamide (51f); (−)-1-(3-(Aminomethyl)phenyl)-N-(3-((cyclopropylmethylamino)(2-methoxynaphthalen-1-yl)methyl)phenyl)-3-(trifluoromethyl)-1H-pyrazole-5-carboxamide (51g) and (+)-1-(3-(Aminomethyl)phenyl)-N-(3-((cyclopropylmethylamino)(2-methoxynaphthalen-1-yl)methyl)phenyl)-3-(trifluoromethyl)-1H-pyrazole-5-carboxamide (51h)

Step-1: Preparation of (3-Amino-phenyl)-(2-methoxy-naphthalen-1-yl)-methanol (51b)

To a stirred solution of 2-Methoxy-naphthalene-1-carbaldehyde (51a) (1.2 g, 10 mmol) in tetrahydrofuran (5 mL) was added (3-(bis(trimethylsilyl)amino)phenyl)magnesium chloride (49c) (12.00 mL, 12.00 mmol) at 0° C. The reaction was stirred for 14 h at room temperature, quenched by adding 2 N HCl (12.50 mL) and stirred for 6 h. The reaction mixture was nuetralized with 2 N NaOH (15 mL) and extracted with ethyl acetate (2×50 mL). The organic layers were combined washed with brine (50 mL), dried over anhydrous MgSO$_4$, filtered and concentrated in vacuum to dryness. The crude residue obtained was purified by flash column chromatography (silica gel 40 g, eluting with 0-100% ethyl acetate in hexane) to furnish (3-amino-phenyl)-(4-methoxy-naphthalen-1-yl)-methanol (51b) (1.7 g, 94% yield) as a white solid; $^1$H NMR (300 MHz, DMSO-d$_6$) δ 8.26-8.18 (m, 1H), 7.86 (d, J=9.0 Hz, 1H), 7.81-7.74 (m, 1H), 7.48 (d, J=9.1 Hz, 1H), 7.29-7.16 (m, 2H), 6.86 (t, J=7.7 Hz, 1H), 6.67-6.60 (m, 1H), 6.56 (dt, J=2.3, 1.2 Hz, 1H), 6.49 (dq, J=7.7, 1.1 Hz, 1H), 6.31 (ddt, J=7.8, 2.0, 0.9 Hz, 1H), 5.82 (d, J=4.6 Hz, 1H), 4.90 (s, 2H), 3.96 (s, 3H); MS (ES+) 302.2 (M+Na), MS (ES−) 557.2 (2M−1).

Step-2: Preparation of 2-(3-Cyano-phenyl)-5-trifluoromethyl-2H-pyrazole-3-carboxylic acid{3-[hydroxy-(2-methoxy-naphthalen-1-yl)-methyl]-phenyl}-amide (51c)

To a solution of 1-(3-cyanophenyl)-3-(trifluoromethyl)-1H-pyrazole-5-carboxylic acid (9i) (1.71 g, 6.085 mmol) in DMF (40 mL) was added (3-Amino-phenyl)-(2-methoxy-naphthalen-1-yl)-methanol (51b) (1.7 g, 6.085 mmol), N-ethyl-N-isopropylpropan-2-amine (8.5 mL, 48.68 mmol) and bromo-tris-pyrrolidino phosphoniumhexafluorophosphate (PyBrOP, 2.836 g, 6.085 mmol) at room temperature. The reaction mixture was stirred at room temperature for 42 h under nitrogen atmosphere. The reaction was diluted with ethyl acetate (40 mL) washed with water (2×40 mL), brine (100 mL), dried, filtered, and evaporated to dryness. The residue obtained was purified by flash column chromatography (silica gel 120 g, eluting with ethyl acetate in hexanes from 0-30%) to furnish 2-(3-Cyano-phenyl)-5-trifluoromethyl-2H-pyrazole-3-carboxylic acid {3-[hydroxy-(2-methoxy-naphthalen-1-yl)-methyl]-phenyl}-amide (51c) (1.8 g, 54.5% yield) as a pale sticky liquid; $^1$H NMR (300 MHz, DMSO-d$_6$) δ 10.59 (s, 1H), 8.21-8.11 (m, 2H), 7.99 (dt, J=7.8, 1.3 Hz, 1H), 7.93-7.86 (m, 2H), 7.83-7.77 (m, 1H), 7.73 (d, J=8.0 Hz, 1H), 7.69 (s, 1H), 7.65-7.60 (m, 1H), 7.53 (dd, J=11.8, 8.1 Hz, 2H), 7.29-7.17 (m, 3H), 7.11-7.04 (m, 1H), 6.75 (d, J=4.4 Hz, 1H), 6.10 (d, J=4.6 Hz, 1H), 3.98 (s, 3H).

Step-3: Preparation of 2-(3-Cyano-phenyl)-5-trifluoromethyl-2H-pyrazole-3-carboxylic acid {3-[(cyclopropylmethyl-amino)-(2-methoxy-naphthalen-1-yl)-methyl]-phenyl}-amide (51d)

To a solution of 2-(3-Cyano-phenyl)-5-trifluoromethyl-2H-pyrazole-3-carboxylic acid {3-[hydroxy-(2-methoxy-naphthalen-1-yl)-methyl]-phenyl}-amide (51c) (1.8 g, 3.317 mmol) in dichloromethane (50 mL) at 0° C. was added thionyl chloride (0.74 g, 6.635 mmol) and stirred at room temperature for 4 h. The reaction mixture was concentrated in vacuum to dryness. The residue obtained was dissolved in acetonitrile (40 mL) and added cyclopropylmethanamine (3.54 g, 49.77 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum. The residue obtained was purified by flash column chromatography (silica gel 40 g, eluting 0-100% ethyl acetate in hexane) to afford 2-(3-Cyano-phenyl)-5-trifluoromethyl-2H-pyrazole-3-carboxylic acid {3-[(cyclopropylmethyl-amino)-(2-methoxy-naphthalen-1-yl)-methyl]-phenyl}-amide (51d) (1.05 g, 53%) as pale liquid; $^1$H NMR (300 MHz, DMSO-d$_6$) δ 10.70 (s, 1H), 8.44-8.36 (m, 1H), 8.24 (t, J=1.8 Hz, 1H), 8.09 (dt, J=7.7, 1.4 Hz, 1H), 7.96 (dd, J=11.7, 8.1 Hz, 3H), 7.83 (d, J=7.9 Hz, 1H), 7.76 (d, J=7.4 Hz, 2H), 7.63 (d, J=8.2 Hz, 1H), 7.57 (d, J=9.0 Hz, 1H), 7.52-7.34 (m, 2H), 7.29 (t, J=7.8 Hz, 1H), 7.21 (d, J=7.8 Hz, 1H), 5.99 (s, 1H), 3.96 (s, 3H), 2.72-2.62 (m, 2H), 2.29-2.13 (m, 1H), 1.11-0.85 (m, 1H), 0.51-0.37 (m, 2H), 0.20-0.06 (m, 1H), 0.05--0.07 (m, 1H).

Step-4: Preparation of tert-butyl ((3-(1-(3-(((tert-butoxycarbonyl)amino)methyl)phenyl)-3-(trifluoromethyl)-1H-pyrazole-5-carboxamido)phenyl)(2-methoxynaphthalen-1-yl)methyl)(cyclopropylmethyl)carbamate (51e)

To a solution of 2-(3-Cyano-phenyl)-5-trifluoromethyl-2H-pyrazole-3-carboxylic acid {3-[(cyclopropylmethyl-amino)-(2-methoxy-naphthalen-1-yl)-methyl]-phenyl}-amide (51d) (1.0 g, 1.678 mmol) in MeOH (20 mL) cooled with ice/water was added nickel(II) chloride hexahydrate (0.48 g, 2.01 mmol) and Boc anhydride (1.1 g, 5.036 mmol) followed by portionwise addition of Sodium Borohydride (0.38 g, 10.073 mmol) over a period of 15 min. The reaction mixture was stirred at room temperature for 2 hrs and quenched with N$^1$-(2-aminoethyl)ethane-1,2-diamine (0.5 mL, 4.197 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over MgSO$_4$ filtered and concentrated in vacuum. The residue obtained was purified by flash column chromatography (silica gel 24 g, eluting with 0-25% Ethyl acetate/hexane) to furnish tert-butyl ((3-(1-(3-(((tert-butoxycarbonyl)amino)methyl)phenyl)-3-(trifluoromethyl)-1H-pyrazole-5-carboxamido)phenyl)(2-methoxynaphthalen-1-yl)methyl)(cyclopropylmethyl)carbamate (51e) (0.8 g, 68.13%) as a white solid; $^1$H NMR (300 MHz, DMSO-d$_6$) δ 10.59 (s, 1H), 7.99 (d, J=9.1 Hz, 1H), 7.96-7.89 (m, 2H), 7.62-7.54 (m, 1H), 7.55-7.40 (m, 3H), 7.43-7.37 (m, 3H), 7.35-7.24 (m, 4H), 7.15 (s, 1H), 6.91-6.81 (m, 1H), 4.17 (d, J=6.2 Hz, 2H), 3.42 (s, 3H), 3.07 (dd, J=14.6, 6.8 Hz, 1H), 1.38 (d, J=5.3 Hz, 18H), 0.34 (p, J=6.7 Hz, 1H), 0.00 (td, J=8.8, 4.5 Hz, 1H), −0.08--0.25 (m, 1H), −0.21--0.39 (m, 1H), −0.65--0.87 (m, 1H).

Step-5: Preparation of Racemic 1-(3-(aminomethyl)phenyl)-N-(3-(((cyclopropylmethyl)amino)(2-methoxynaphthalen-1-yl)methyl)phenyl)-3-(trifluoromethyl)-1H-pyrazole-5-carboxamide (51f)

To a solution of tert-butyl ((3-(1-(3-(((tert-butoxycarbonyl)amino)methyl)phenyl)-3-(trifluoromethyl)-1H-pyrazole-5-carboxamido)phenyl)(2-methoxynaphthalen-1-yl)methyl)(cyclopropylmethyl)carbamate (51e) (0.8 g, 1.143 mmol) in methanol (16 mL) was added conc. HCl (0.5 mL). The reaction mixture was stirred at room temperature overnight and concentrated in vacuum to dryness. The residue was azeotroped with toluene (2×10 mL) and ethanol (10 mL), dried in vacuum pump to furnish a white solid residue. The product were purified by flash column chromatography (silica gel 12 g, eluting with 0-15% methanol in Dichloromethane) to obtain free base of 1-(3-(aminomethyl)phenyl)-N-(3-(((cyclopropylmethyl)amino)(2-methoxynaphthalen-1-yl)methyl)phenyl)-3-(trifluoromethyl)-1H-pyrazole-5-carboxamide (51f) (170 mg, 24.8%) as a white solid; $^1$H NMR (300 MHz, DMSO-d$_6$) δ 10.82 (s, 1H), 8.25 (d, J=8.6 Hz, 1H), 7.98 (d, J=9.0 Hz, 1H), 7.90 (d, J=8.1 Hz, 1H), 7.82-7.68 (m, 2H), 7.66-7.43 (m, 6H), 7.42-7.24 (m, 3H), 6.12 (s, 1H), 4.11 (s, 2H), 3.95 (s, 3H), 2.78-2.70 (m, 1H), 2.66 (d, J=7.4 Hz, 2H), 0.92-0.69 (m, 1H), 0.48-0.35 (m, 2H), 0.10 (s, 2H); $^{19}$F NMR (282 MHz, DMSO-d$_6$) δ −60.77; MS (ES+) 600.4 (M+1); (ES−) 634.3 (M+Cl); 1-(3-(aminomethyl)phenyl)-N-(3-(((cyclopropylmethyl)amino)(2-methoxynaphthalen-1-yl)methyl)phenyl)-3-(trifluoromethyl)-1H-pyrazole-5-carboxamide (51f) (160 mg) was converted to hydrochloride salt by dissolving the free base in methanol (5 mL) and treating it with 10 equivalents of conc HCl. The solution obtained was concentrated in vacuum to dryness dried in vacuum to furnish Racemic 1-(3-(aminomethyl)phenyl)-N-(3-(((cyclopropylmethyl)amino)(2-methoxynaphthalen-1-yl)methyl)phenyl)-3-(trifluoromethyl)-1H-pyrazole-5-carboxamide dihydrochloride (51f) (100 mg, 53%) hydrochloride as a pale yellow solid; $^1$H NMR (300 MHz, DMSO-d$_6$) δ 10.98 (s, 1H), 9.87 (s, 1H), 9.27 (d, J=10.4 Hz, 1H), 8.58 (s, 3H), 8.20 (d, J=8.7 Hz, 1H), 8.07 (d, J=9.2 Hz, 1H), 7.95 (dd, J=8.3, 1.4 Hz, 1H), 7.91 (s, 1H), 7.72 (t, J=1.8 Hz, 1H), 7.69-7.36 (m, 10H), 6.35 (t, J=6.4 Hz, 1H), 4.10 (q, J=5.9 Hz, 2H), 4.03 (s, 3H), 2.89 (dt, J=7.5, 4.4 Hz, 1H), 2.80-2.64 (m, 1H), 1.12 (ddd, J=12.4, 8.1, 4.9 Hz, 1H), 0.51 (dtt, J=17.5, 9.3, 4.6 Hz, 2H), 0.34-0.10 (m, 2H); $^{19}$F NMR (282 MHz, DMSO-d$_6$) δ −60.77; MS (ES+) 600.4 (M+1); (ES−) 634.3 (M+Cl); Analysis calculated for C$_{34}$H$_{32}$F$_3$N$_5$O$_2$·2HCl 1.75H$_2$O: C, 58.00; H, 5.37; Cl, 10.07; N, 9.95; Found: C, 58.06; H, 5.45; Cl, 9.93; N, 9.74.

Step-6: Preparation of (−)-1-(3-(Aminomethyl)phenyl)-N-(3-((cyclopropylmethylamino)(2-methoxynaphthalen-1-yl)methyl)phenyl)-3-(trifluoromethyl)-1H-pyrazole-5-carboxamide (51g) and (+)-1-(3-(Aminomethyl)phenyl)-N-(3-((cyclopropylmethylamino)(2-methoxynaphthalen-1-yl)methyl)phenyl)-3-(trifluoromethyl)-1H-pyrazole-5-carboxamide (51h)

Racemic 1-(3-(aminomethyl)phenyl)-N-(3-(((cyclopropylmethyl)amino)(2-methoxynaphthalen-1-yl)methyl)phenyl)-3-(trifluoromethyl)-1H-pyrazole-5-carboxamide (51f)

(2 g) was separated using chiral preparative HPLC using CHIRALPAK AD-H column, 5 t, 4.6×250 mm, flow rate 1 mL/min, Solvent: 80% Hexane/20% IPA/0.1% DEA, UV=320 nM, 25° C., to furnish:

1. Peak-1 (−)-1-(3-(Aminomethyl)phenyl)-N-(3-((cyclopropylmethylamino)(2-methoxynaphthalen-1-yl)methyl)phenyl)-3-(trifluoromethyl)-1H-pyrazole-5-carboxamide (51g) (904 mg, Rt=5.191 min, peak-1 for compound 51 g, 99.4822%, Rt=8.194, peak-2 for compound 51h, 0.5178, 98.96% ee). This was repurified by flash column chromatography (silica gel 25 g, eluting 0-30% MeOH in chloroform for 25 mins) to afford (−)-1-(3-(Aminomethyl)phenyl)-N-(3-((cyclopropylmethylamino)(2-methoxynaphthalen-1-yl)methyl)phenyl)-3-(trifluoromethyl)-1H-pyrazole-5-carboxamide (51g) (730 mg, 99.38% ee) as a free base; Optical Rotation −137.78 (MeOH, 1.645). To (−)-1-(3-(Aminomethyl)phenyl)-N-(3-((cyclopropylmethylamino)(2-methoxynaphthalen-1-yl)methyl)phenyl)-3-(trifluoromethyl)-1H-pyrazole-5-carboxamide (51g) free base (720 mg) was dissolved in methanol (8 mL) and added 2 N HCl (in methanol, 2.25 mL, 10 eq.). The solution was stirred at room temperature for 30 min, evaporated to dryness to afford (−)-1-(3-(Aminomethyl)phenyl)-N-(3-((cyclopropylmethylamino)(2-methoxynaphthalen-1-yl)methyl)phenyl)-3-(trifluoromethyl)-1H-pyrazole-5-carboxamide (51g) (780 mg) hydrochloride salt as an off-white solid; $^1$H NMR (300 MHz, DMSO-d$_6$) δ 10.64 (s, 1H), 8.31 (d, J=8.4 Hz, 1H), 7.86 (dd, J=11.1, 8.1 Hz, 2H), 7.63 (s, 1H), 7.52 (q, J=3.1, 1.6 Hz, 3H), 7.47 (d, J=9.1 Hz, 1H), 7.43-7.26 (m, 5H), 7.18 (t, J=7.8 Hz, 1H), 7.11 (d, J=7.9 Hz, 1H), 5.89 (s, 1H), 3.86 (s, 3H), 3.76 (s, 2H), 2.11 (t, J=9.5 Hz, 1H), 0.92 (d, J=7.3 Hz, 1H), 0.42-0.27 (m, 2H), 0.08-0.02 (m, 1H), −0.04-−0.16 (m, 1H); Analysis calculated for $C_{34}H_{32}F_3N_5O_2.2HCl.2.5H_2O$: C, 56.91; H, 5.48; Cl, 9.88; N, 9.76; Found; C, 57.14; H, 5.42; Cl, 9.47; N, 9.98.

2. Peak-2 (+)-1-(3-(Aminomethyl)phenyl)-N-(3-((cyclopropylmethylamino)(2-methoxynaphthalen-1-yl)methyl)phenyl)-3-(trifluoromethyl)-1H-pyrazole-5-carboxamide (51h) (922 mg, Rt=5.271 min, peak-1 for compound 51 g, 0.25785%, Rt=8.049, peak-2 for compound 51h, 99.4215, 97.67% ee). This was repurified by flash column chromatography (silica gel 40 g, eluting 0-30% MeOH in chloroform for 25 min) to afford (+)-1-(3-(Aminomethyl)phenyl)-N-(3-((cyclopropylmethylamino)(2-methoxynaphthalen-1-yl)methyl)phenyl)-3-(trifluoromethyl)-1H-pyrazole-5-carboxamide (51h) (0.753 g) free base as a white solid; Optical Rotation+131.32 (MeOH, 2.695). To (+)-1-(3-(Aminomethyl)phenyl)-N-(3-((cyclopropylmethylamino)(2-methoxynaphthalen-1-yl)methyl)phenyl)-3-(trifluoromethyl)-1H-pyrazole-5-carboxamide (51h) (770 mg) of free base in methanol (25 mL) was added 2 N HCl (in methanol, 6.5 mL, 10 eq.) stirred at room temperature for 30 min and concentrated in vacuum to dryness to afford (+)-1-(3-(Aminomethyl)phenyl)-N-(3-((cyclopropylmethylamino)(2-methoxynaphthalen-1-yl)methyl)phenyl)-3-(trifluoromethyl)-1H-pyrazole-5-carboxamide (51h) (753 mg) hydrochloride as an off-white solid; $^1$H NMR (300 MHz, DMSO-d$_6$) δ 10.98 (s, 1H, D$_2$O exchangeable), 9.88 (s, 1H, D$_2$O exchangeable), 9.25 (s, 1H, D$_2$O exchangeable), 8.58 (s, 3H, D$_2$O exchangeable), 8.20 (d, J=8.7 Hz, 1H), 8.07 (d, J=9.2 Hz, 1H), 7.99-7.87 (m, 2H), 7.72 (t, J=1.8 Hz, 1H), 7.70-7.54 (m, 6H), 7.53-7.39 (m, 3H), 6.50-6.19 (m, 1H), 4.10 (d, J=5.4 Hz, 2H), 4.03 (s, 3H), 2.89 (d, J=11.1 Hz, 1H), 2.73 (s, 1H), 1.13 (h, J=7.3, 6.8 Hz, 1H), 0.50 (ttd, J=13.2, 8.9, 4.3 Hz, 2H), 0.23 (ddq, J=18.4, 9.2, 4.6 Hz, 2H); 1H NMR (300 MHz, DMSO-d$_6$ D$_2$O) δ 8.19 (d, J=8.8 Hz, 1H), 8.08 (d, J=9.2 Hz, 1H), 7.96 (dd, J=8.3, 1.4 Hz, 1H), 7.88 (d, J=2.4 Hz, 1H), 7.71 (t, J=1.8 Hz, 1H), 7.66-7.55 (m, 6H), 7.54-7.38 (m, 4H), 6.34 (s, 1H), 4.12 (s, 2H), 4.03 (s, 3H), 2.91 (dd, J=12.9, 6.8 Hz, 1H), 2.73 (dd, J=13.0, 7.6 Hz, 1H), 1.08 (q, J=6.1, 5.0 Hz, 1H), 0.53 (dtd, J=17.3, 9.4, 8.9, 4.7 Hz, 2H), 0.23 (dhept, J=18.0, 4.7 Hz, 2H); $^{19}$F NMR (282 MHz, DMSO-d$_6$) δ −60.74; MS (ES+) 600.3 (M+1), MS (ES−) 598.3 (M−1), 634.3 (M+Cl); Analysis calculated for $C_{34}H_{32}F_3N_5O_2.2HCl.2.75H_2O$: C, 56.55; H, 5.51; Cl, 9.82; N, 9.70; Found; C, 56.42; H, 5.40; Cl, 10.26; N, 9.66.

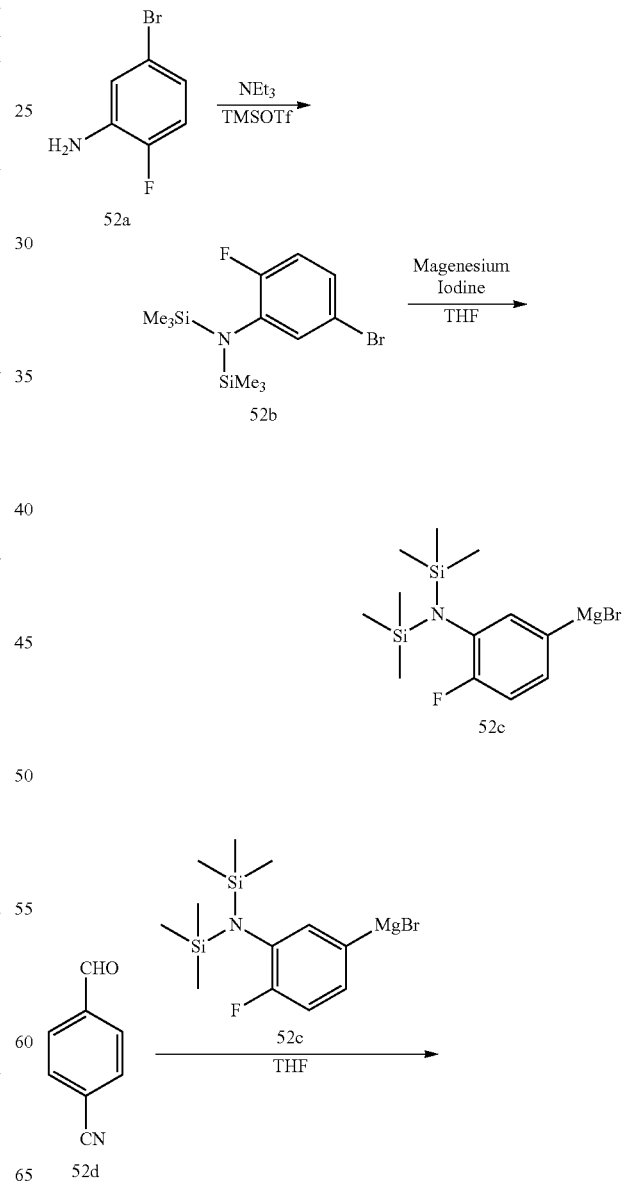

Scheme 52

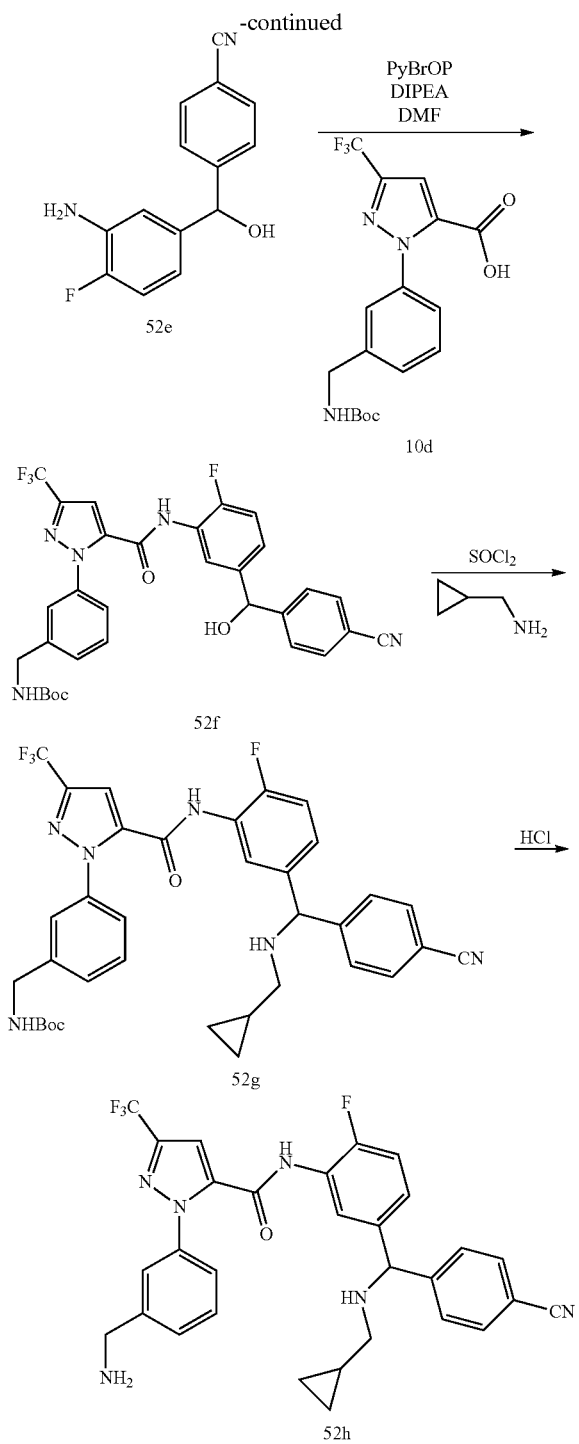

Preparation of 1-(3-(aminomethyl)phenyl)-N-(5-((4-cyanophenyl)(cyclopropyl-methylamino)methyl)-2-fluorophenyl)-3-(trifluoromethyl)-1H-pyrazole-5-carboxamide (52h)

Step-1: Preparation of N-(5-bromo-2-fluorophenyl)-1,1,1-trimethyl-N-(trimethylsilyl)silanamine (52b)

To a stirred solution of 5-bromo-2-fluoroaniline (52a) (225 g, 1184 mmol) in triethylamine (3301 mL, 20 eq) was added trimethylsilyl trifluoromethanesulfonate (481 mL, 2664 mmol) at room temperature [Note: during the addition heat was generated but, was not needed to cool the flask]. The mixture was heated at reflux for 16 h and cooled to room temperature. The two layers were separated. [Note: avoid exposing the solution to air or moisture during the separation]. Dark bottom solution was discarded and the upper layer was concentrated in vacuum to remove excess triethylamine. The oily residue was transferred to 1000 mL flask and distilled under high vacuum. The compound starts to distill at 100° C. at 0.5 mm/Hg. First fraction (about 15 mL) was discarded the second fraction was collected steadily at 100° C., 0.5 mm/Hg, to furnish N-(5-bromo-2-fluorophenyl)-1,1,1-trimethyl-N-(trimethylsilyl)silanamine (52b) (364 g, 1089 mmol, 92% yield). This was always freshly prepared for next step; $^1$H NMR (300 MHz, Chloroform-d) δ 7.17-7.11 (m, 1H), 7.09 (dd, J=7.5, 2.5 Hz, 1H), 6.89 (d, J=0.9 Hz, 1H), 0.08 (d, J=0.6 Hz, 18H).

Step-2: Preparation of (3-(bis(trimethylsilyl)amino)-4-fluorophenyl)magnesium Bromide (52c)

To magnesium turnings (33.1 g, 1361 mmol) in tetrahydrofuran (15 mL) was added iodine (1.381 g, 5.44 mmol) followed by N-(5-bromo-2-fluorophenyl)-1,1,1-trimethyl-N-(trimethylsilyl)silanamine (52b) (4g) to activate the reaction for about 5 minutes (Iodine color was decolorized). At this point rest of the solution of N-(5-bromo-2-fluorophenyl)-1,1,1-trimethyl-N-(trimethylsilyl)silanamine (52b) (364 g, 1089 mmol) in tetrahydrofuran (1000 mL) was added slowly in over a period of 3 h (reaction temperature was around 60° C. during the addition. The resulting dark grey solution was stirred overnight to furnish (3-(bis(trimethylsilyl)amino)-4-fluorophenyl)magnesium bromide (52c) (397 g, 1107 mmol, 102% yield, approximately 1 M solution) which was used fresh in the next step.

Step-3: Preparation of 4-((3-amino-4-fluorophenyl)(hydroxy)methyl)benzonitrile (52e)

To a solution of 4-formylbenzonitrile (52d) (6.56 g, 50 mmol) in tetrahydrofuran (50 mL) cooled to 0° C. was added Grignard reagent (52c) (63.0 mL, 50.4 mmol, ~0.8 M in THF) stirred at 0° C. for 1 h, and room temperature for 17 h. The reaction mixture was quenched with 1 N HCl (aq. 100 mL), stirred for 3 h, neutralized with NaOH (2 N, aq.) to pH=~8. The reaction mixture was extracted with ethyl acetate (200, 150 mL). The combined extracts were washed with brine (120 mL), dried over MgSO$_4$, filtered and concentrated in vacuum. The crude product was purified by flash column chromatography [silica gel, eluting with chloroform/methanol (1:0 to 19:1)] to afford 4-((3-amino-4-fluorophenyl)(hydroxy)methyl)benzonitrile (52e) (6.37 g) as a brown gum, which was used as such for next step). MS (ES+): 265.2 (M+23).

Step-4: Preparation of tert-butyl 3-(5-(5-((4-cyanophenyl)(hydroxy)methyl)-2-fluorophenylcarbamoyl)-3-(trifluoromethyl)-1H-pyrazol-1-yl)benzylcarbamate (52f)

To a solution of 4-((3-amino-4-fluorophenyl)(hydroxy)methyl)benzonitrile (52e) (3 g, 12.38 mmol) in DMF (80 mL) was added 1-(3-((tert-butoxycarbonylamino)methyl)phenyl)-3-(trifluoromethyl)-1H-pyrazole-5-carboxylic acid (10d) (4.77 g, 12.38 mmol), N-ethyl-N-isopropylpropan-2-amine (18.00 mL, 103 mmol), bromotripyrrolidin-1-ylphosphonium hexafluorophosphate(V) (PyBrOP, 5.94 g, 12.48 mmol) and stirred at room temperature for 19 h. The reaction mixture was diluted with ethyl acetate (400 mL), washed with water (200, 150 mL), brine (150 mL), dried over MgSO$_4$, filtered and concentrated in vacuum. The crude product was purified by flash column chromatography [silica gel 120 g, eluting with hexanes/ethyl acetate (1:0 to 1:1)] to afford tert-butyl 3-(5-(5-((4-cyanophenyl)(hydroxy)methyl)-2-fluorophenylcarbamoyl)-3-(trifluoromethyl)-1H-pyrazol-1-yl)benzylcarbamate (52f) (1.998 g) as a light yellow solid, which was used as such for next step; MS (ES+): 632.3 (M+23).

Step-5: Preparation of tert-butyl 3-(5-(5-((4-cyanophenyl)(cyclopropylmethylamino)methyl)-2-fluorophenylcarbamoyl)-3-(trifluoromethyl)-1H-pyrazol-1-yl)benzylcarbamate (52g)

To a solution of tert-butyl 3-(5-(5-((4-cyanophenyl)(hydroxy)methyl)-2-fluorophenylcarbamoyl)-3-(trifluoromethyl)-1H-pyrazol-1-yl)benzylcarbamate (52f) (1.007 g, 1.652 mmol) in dichloromethane (32 mL) at 0° C. was added thionyl chloride (0.260 mL, 3.52 mmol) and warmed to room temperature over 2 h. The reaction mixture was quenched with triethyl amine (1.5 mL, 10.76 mmol) stirred at room temperature for 1 h. It was then treated with cyclopropylmethanamine (3.20 mL, 35.8 mmol), concentrated to remove most of dichloromethane followed by addition of acetonitrile (24 mL), stirring at 70° C. for 19 h, and concentration in vacuum to dryness. The residue was treated with chloroform (200 mL), washed with water (100 mL), dried over MgSO$_4$ followed by filtration and concentration. The crude product was purified by flash column chromatography [silica gel eluting with hexanes/ethyl acetate (1:0 to 2:1)] to afford tert-butyl 3-(5-(5-((4-cyanophenyl)(cyclopropylmethylamino)methyl)-2-fluorophenylcarbamoyl)-3-(trifluoromethyl)-1H-pyrazol-1-yl)benzylcarbamate (52g) (244 mg, 3% for three steps) as a yellow solid; $^1$H NMR (300 MHz, DMSO-d$_6$) δ 10.56 (s, 1H), 7.80-7.73 (m, 2H), 7.67-7.29 (m, 10H), 7.26-7.17 (m, 1H), 4.95 (s, 1H), 4.19 (d, J=6.2 Hz, 2H), 2.25 (d, J=6.9 Hz, 2H), 1.37 (s, 9H), 0.98-0.79 (m, 1H), 0.43-0.27 (m, 2H), 0.09--0.02 (m, 2H); $^{19}$F NMR (282 MHz, DMSO-d$_6$) δ -60.81, -123.20; MS (ES+): 663.4 (M+1).

Step-6: Preparation of 1-(3-(aminomethyl)phenyl)-N-(5-((4-cyanophenyl)(cyclopropyl-methylamino)methyl)-2-fluorophenyl)-3-(trifluoromethyl)-1H-pyrazole-5-carboxamide (52h)

To a solution of tert-butyl 3-(5-(5-((4-cyanophenyl)(cyclopropylmethylamino)methyl)-2-fluorophenylcarbamoyl)-3-(trifluoromethyl)-1H-pyrazol-1-yl)benzylcarbamate (52g) (85 mg, 0.128 mmol) in 1,4-Dioxane (9 mL) was added hydrogen chloride (1.400 mL, 5.60 mmol, 4 M in 1,4-dioxane) and stirred at room temperature for 18 h. the reaction mixture was treated with hexanes, decanted, washed with hexanes, and decanted again. The insoluble crude product was purified by flash column chromatography [silica gel, eluting with chloroform/CMA80 (1:0 to 2:1)] to afford 1-(3-(aminomethyl)phenyl)-N-(5-((4-cyanophenyl)(cyclopropyl-methylamino)methyl)-2-fluorophenyl)-3-(trifluoromethyl)-1H-pyrazole-5-carboxamide (52h) (40 mg, 55%) as a colorless gum; $^1$H NMR (300 MHz, DMSO-d$_6$) δ 10.82 (s, 1H), 10.43 (s, 2H), 8.42 (s, 3H), 7.95 (s, 5H), 7.78-7.66 (m, 3H), 7.62 (dt, J=7.3, 1.8 Hz, 1H), 7.57 (d, J=7.8 Hz, 1H), 7.55-7.49 (m, 1H), 7.48-7.36 (m, 1H), 5.81 (d, J=6.9 Hz, 1H), 4.13 (d, J=5.3 Hz, 2H), 2.84-2.63 (m, 2H), 1.28-1.03 (m, 1H), 0.66-0.45 (m, 2H), 0.44-0.14 (m, 2H); $^1$H NMR (300 MHz, DMSO-d$_6$, D$_2$O ex NMR) δ 7.95 (d, J=8.2 Hz, 2H), 7.90-7.78 (m, 3H), 7.70 (s, 1H), 7.65 (s, 1H), 7.62-7.48 (m, 4H), 7.43 (t, J=9.4 Hz, 1H), 5.77 (s, 1H), 4.12 (s, 2H), 2.74 (d, J=7.3 Hz, 2H), 1.15-1.00 (m, 1H), 0.58 (d, J=7.6 Hz, 2H), 0.29 (d, J=4.9 Hz, 2H); $^{19}$F NMR (282 MHz, DMSO-d$_6$) δ -60.82, -120.00; MS (ES+): 563.3 (M+1). 1-(3-(aminomethyl)phenyl)-N-(5-((4-cyanophenyl)(cyclopropyl-methylamino)methyl)-2-fluorophenyl)-3-(trifluoromethyl)-1H-pyrazole-5-carboxamide (52h) (21 mg) was dissolved in methanol (10 mL) and treated with 4 N HCl (aq. 0.04 mL) followed by concentration to dryness to give HCl salt of 1-(3-(aminomethyl)phenyl)-N-(5-((4-cyanophenyl)(cyclopropyl-methylamino)methyl)-2-fluorophenyl)-3-(trifluoromethyl)-1H-pyrazole-5-carboxamide (52h) (21 mg) as a white solid; $^1$H NMR (300 MHz, DMSO-d$_6$) δ 7.98-7.91 (m, 2H), 7.90-7.79 (m, 3H), 7.73-7.49 (m, 7H), 7.43 (dd, J=10.2, 8.6 Hz, 1H), 5.77 (s, 1H), 4.12 (s, 2H), 2.75 (d, J=7.0 Hz, 2H), 1.14-1.00 (m, 1H), 0.64-0.54 (m, 2H), 0.33-0.23 (m, 2H); $^{19}$F NMR (282 MHz, DMSO-d$_6$) δ -60.81, -119.99; MS (ES+): 563.3 (M+1); Analysis calculated for C$_{30}$H$_{26}$F$_4$N$_6$O.2.0HCl.2.5H$_2$O: C, 52.95; H, 4.89; N, 12.35; Found: C, 53.21; H, 4.95; N, 11.71.

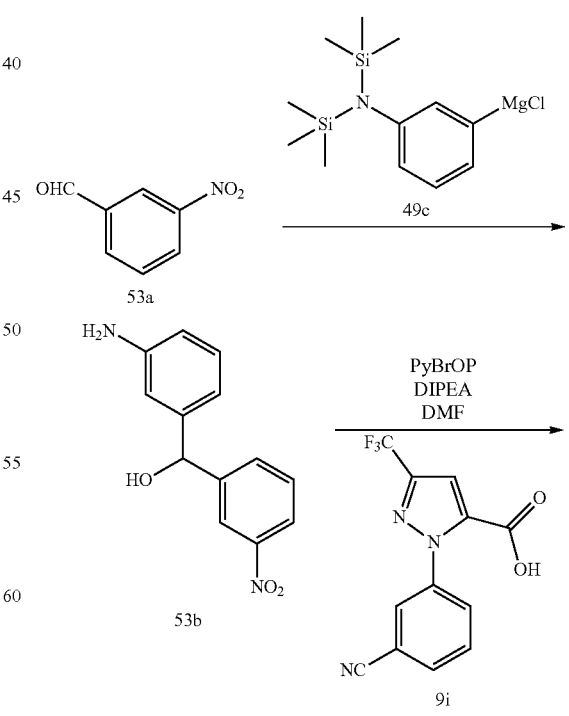

Scheme 53

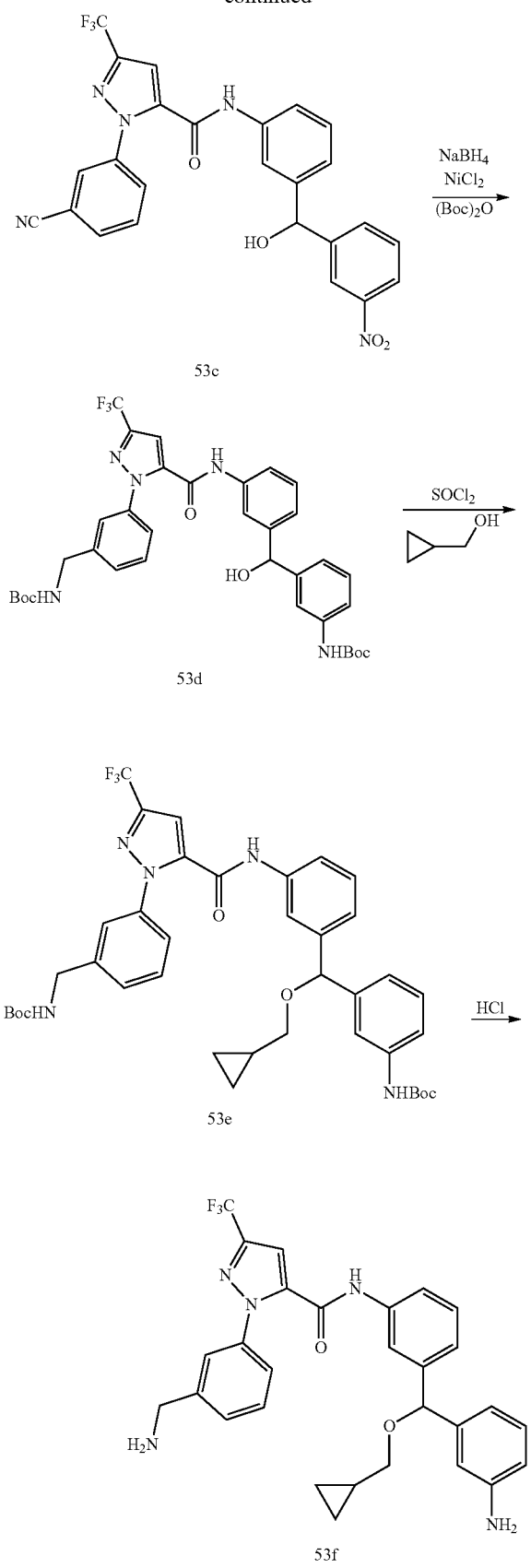

Preparation of 1-(3-(aminomethyl)phenyl)-N-(3-((3-aminophenyl)(cyclopropyl-methoxy)methyl)phenyl)-3-(trifluoromethyl)-1H-pyrazole-5-carboxamide (53f)

Step-1: Preparation of (3-aminophenyl)(3-nitrophenyl)methanol (53b)

To a stirred solution of 3-nitrobenzaldehyde (53a) (3.02 g, 20 mmol) in tetrahydrofuran (20 mL) was added (3-(bis(trimethylsilyl)amino)phenyl)magnesium chloride (49c) (24.00 mL, 24.00 mmol) at 0° C. The reaction was stirred for 14 h at room temperature and quenched by adding hydrogen chloride (12N) (4.17 mL, 50.0 mmol), stirred for 1 h. The reaction mixture was treated with sodium hydroxide (2N) (30.0 mL, 60.0 mmol) and extracted with ethyl acetate (2×50 mL). The organic layers were combined washed with sat. NH$_4$Cl (50 mL), dried over anhydrous MgSO$_4$, filtered and evaporated to dryness. The crude residue was purified by flash column chromatography (silica gel 120 g, eluting with 0-100% ethyl acetate in hexane) to furnish (3-aminophenyl)(3-nitrophenyl)methanol (53b) (966 mg) as a brown solid; $^1$H NMR (300 MHz, DMSO-d$_6$) δ 8.21 (t, J=2.0 Hz, 1H), 8.08 (ddd, J=8.2, 2.4, 1.1 Hz, 1H), 7.78 (ddt, J=7.6, 1.6, 0.8 Hz, 1H), 7.60 (t, J=7.9 Hz, 1H), 6.95 (t, J=7.7 Hz, 1H), 6.62-6.51 (m, 2H), 6.41 (ddd, J=7.9, 2.3, 1.0 Hz, 1H), 6.07 (d, J=3.9 Hz, 1H), 5.68 (d, J=3.9 Hz, 1H), 5.06 (s, 2H); MS (ES+) 245.2 (M+1).

Step-2: Preparation of 1-(3-cyanophenyl)-N-(3-(hydroxy(3-nitrophenyl)methyl)phenyl)-3-(trifluoromethyl)-1H-pyrazole-5-carboxamide (53c)

In a 100 mL single-necked flask containing 1-(3-cyanophenyl)-3-(trifluoromethyl)-1H-pyrazole-5-carboxylic acid (9i) (1101 mg, 3.91 mmol), (3-aminophenyl)(3-nitrophenyl)methanol (53b) (956 mg, 3.91 mmol), bromo-tris-pyrrolidino phosphoniumhexafluorophosphate(PyBrop) (1862 mg, 3.91 mmol) was added N,N-dimethylformamide (DMF) (22 mL) and N-ethyl-N-isopropylpropan-2-amine (DIPEA) (5.50 mL, 31.6 mmol) successively in a positive flow of nitrogen at room temperature. The resulting reaction mixture was stirred at room temperature for 13 h under a positive flow of nitrogen atmosphere. The reaction mixture was diluted with ethyl acetate (180 mL), washed with water (2×80 mL), brine (80 mL), dried over MgSO$_4$ filtered and and concentrated in vacuum to dryness. The crude product was purified by flash column chromatography [silica gel 40 g, eluting with hexanes/ethyl acetate (1:0 to 1:1)] to give 1-(3-cyanophenyl)-N-(3-(hydroxy(3-nitrophenyl)methyl)phenyl)-3-(trifluoromethyl)-1H-pyrazole-5-carboxamide (53c) (1.102 g, 56%) as a brown gum; $^1$H NMR (300 MHz, DMSO-d$_6$) δ 10.66 (s, 1H), 8.24 (t, J=1.9 Hz, 1H), 8.16 (t, J=1.8 Hz, 1H), 8.10 (ddd, J=8.1, 2.4, 1.1 Hz, 1H), 8.00 (dt, J=7.8, 1.3 Hz, 1H), 7.90 (ddd, J=8.2, 2.2, 1.1 Hz, 1H), 7.83-7.55 (m, 6H), 7.31 (t, J=7.8 Hz, 1H), 7.20 (dt, J=7.8, 1.3 Hz, 1H), 6.32 (d, J=4.0 Hz, 1H), 5.88 (d, J=4.0 Hz, 1H); $^{19}$F NMR (282 MHz, DMSO-d$_6$) δ −60.98; MS (ES+) 530.2 (M+23).

Step-3: Preparation of tert-butyl 3-(5-((3-((3-tert-butyloxycarbonylaminophenyl) (hydroxy)methyl)phenyl)carbamoyl)-3-(trifluoromethyl)-1H-pyrazol-1-yl)benzylcarbamate (53d)

A solution of 1-(3-cyanophenyl)-N-(3-(hydroxy(3-nitrophenyl)methyl)phenyl)-3-(trifluoromethyl)-1H-pyrazole-5- carboxamide (53c) (0.865 g, 1.705 mmol) in MeOH (30 mL) was cooled with ice/water and treated with di-tert-butyl dicarbonate (1.503 g, 6.82 mmol) and nickel(II) chloride hexahydrate (0.218 g, 0.917 mmol) followed by addition of sodium borohydride (0.658 g, 17.05 mmol) slowly over 5 min and stirring at room temperature for 1 h. The reaction mixture was treated N1-(2-aminoethyl)ethane-1,2-diamine (0.840 mL, 7.70 mmol) followed by stirring at room temperature for 0.5 h and concentration to dryness. The residue was treated with ethyl acetate (120 mL), washed with water (80 mL). The aqueous phase was extracted again with ethyl acetate (80 mL). The combined extracts were washed with brine (80 mL), dried over $MgSO_4$ followed by filtration and concentration. The crude product was purified by flash column chromatography [silica gel with hexanes/ethyl acetate (1:0 to 1:1)] to afford tert-butyl 3-(5-((3-((3-tert-butyloxycarbonylaminophenyl) (hydroxy)methyl)phenyl) carbamoyl)-3-(trifluoromethyl)-1H-pyrazol-1-yl)benzylcarbamate (53d) (547 mg, 47%) as a colorless gum; $^1$H NMR (300 MHz, DMSO-$d_6$) δ 10.70 (s, 1H), 9.30 (s, 1H), 7.57 (s, 2H), 7.55-7.08 (m, 11H), 6.93 (d, J=7.5 Hz, 1H), 5.90 (d, J=3.7 Hz, 1H), 5.57 (d, J=3.7 Hz, 1H), 4.19 (d, J=6.2 Hz, 2H), 1.45 (s, 9H), 1.36 (s, 9H); $^{19}$F NMR (282 MHz, DMSO-$d_6$) δ −60.79; (ES+) 704.4 (M+23).

Step-4: Preparation of tert-butyl 3-(5-((3-((3-tert-butyloxycarbonylaminophenyl)(cyclopropyl-methoxy)methyl)phenyl)carbamoyl)-3-(trifluoromethyl)-1H-pyrazol-1-yl)benzylcarbamate (53e)

To a solution of tert-butyl 3-(5-((3-((3-tert-butyloxycarbonylaminophenyl) (hydroxy)methyl)phenyl)carbamoyl)-3-(trifluoromethyl)-1H-pyrazol-1-yl)benzylcarbamate (53d) (531 mg, 0.779 mmol) in dichloromethane (15 mL) at 0° C. was added thionyl chloride (0.110 mL, 1.511 mmol), reaction mixture allowed to warm to room temperature and stirred for 12 h. The reaction mixture was quenched with cyclopropylmethanol (5.80 mL, 70.1 mmol), stirred for 1 h at room temperature and concentrated in vacuum to dryness. The residue was dissolved in cyclopropylmethanol (5.80 mL, 70.1 mmol) added triethylamine (0.660 mL, 4.74 mmol) and heated at 100° C. for 13 h. The reaction mixture was cooled to room temperature and evaporated to dryness. The residue was dissolved in ethyl acetate (150 mL) and washed with water (80 mL), brine (70 mL), dried over $MgSO_4$ followed by filtration and concentration. The residue was purified by flash column chromatography [(silica gel 12 g, eluting with hexanes/ethyl acetate (1:0 to 2:1)] to give tert-butyl 3-(5-((3-((3-tert-butyloxycarbonylaminophenyl)(cyclopropylmethoxy)methyl)phenyl)carbamoyl)-3-(trifluoromethyl)-1H-pyrazol-1-yl)benzylcarbamate (53e) (243 mg, 42%) as a colorless gum; $^1$H NMR (300 MHz, DMSO-$d_6$) δ 10.74 (s, 1H), 9.34 (s, 1H), 7.62-7.25 (m, 11H), 7.19 (t, J=7.8 Hz, 1H), 7.10 (d, J=7.7 Hz, 1H), 6.94 (d, J=7.5 Hz, 1H), 5.36 (s, 1H), 4.19 (d, J=6.2 Hz, 2H), 3.27-3.15 (m, 2H), 1.45 (s, 9H), 1.36 (s, 9H), 1.12-0.97 (m, 1H), 0.52-0.39 (m, 2H), 0.21-0.10 (m, 2H); $^{19}$F NMR (282 MHz, DMSO-$d_6$) δ −60.79; (ES+) 758.4 (M+23).

Step-5: Preparation of 1-(3-(aminomethyl)phenyl)-N-(3-((3-aminophenyl)(cyclopropyl-methoxy)methyl)phenyl)-3-(trifluoromethyl)-1H-pyrazole-5-carboxamide (53f)

To a solution of tert-butyl 3-(5-((3-((3-tert-butyloxycarbonylaminophenyl)(cyclopropylmethoxy)methyl)phenyl)carbamoyl)-3-(trifluoromethyl)-1H-pyrazol-1-yl)benzylcarbamate (53e) in methanol (20 mL) was added conc. hydrogen chloride (0.230 mL, 2.76 mmol) and stirred at room temperature for 13 h. The reaction mixture was concentrated to dryness under vacuum (at <30° C.). The residue was purified by flash column chromatography [silica gel eluting with chloroform/CMA80 (1:0 to 3:1)] to 1-(3-(aminomethyl)phenyl)-N-(3-((3-aminophenyl)(cyclopropyl-methoxy)methyl)phenyl)-3-(trifluoromethyl)-1H-pyrazole-5-carboxamide (53f) (84 mg) as free base. The purified product was dissolved in methanol (10 mL) and treated with 4 N HCl (aq. 0.16 mL) followed by concentration to dryness to give HCl salt of 1-(3-(aminomethyl)phenyl)-N-(3-((3-aminophenyl)(cyclopropyl-methoxy)methyl)phenyl)-3-(trifluoromethyl)-1H-pyrazole-5-carboxamide (53f) (91 mg, 55%) as a white solid; $^1$H NMR ($D_2O$ ex NMR, 300 MHz, DMSO-d6) δ 7.56-7.33 (m, 7H), 7.21-7.10 (m, 2H), 6.98 (d, J=7.6 Hz, 1H), 6.90 (bs, 2H), 6.78 (d, J=8.1 Hz, 1H), 5.26 (s, 1H), 3.97 (s, 2H), 3.08 (dd, J=6.9, 1.3 Hz, 2H), 0.97-0.81 (m, 1H), 0.40-0.26 (m, 2H), 0.08--0.07 (m, 2H); $^{19}$F NMR (282 MHz, DMSO-$d_6$) δ −60.77; MS (ES+) 536.3 (M+1); Analysis calculated for $C_{29}H_{28}F_3N_5O_2 \cdot 2.0HCl \cdot 2.0H_2O$: C, 54.04; H, 5.32; N, 10.87; Found: C, 53.63; H, 5.19; N, 10.78.

Scheme 54

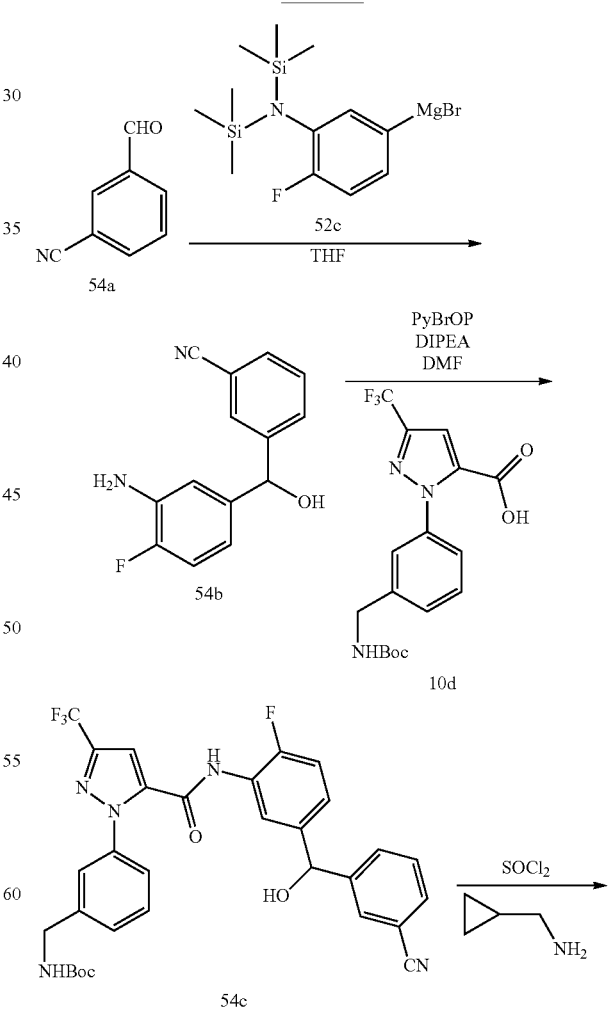

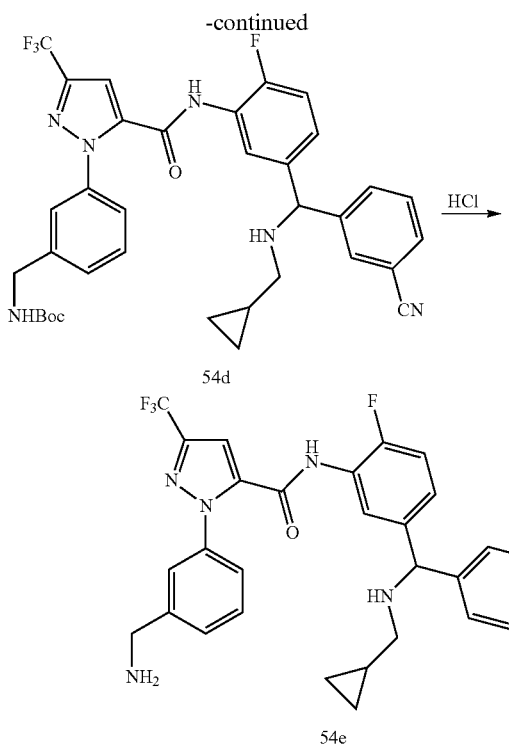

Preparation of 1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (54e)

Step-1: Preparation of 3-((3-amino-4-fluorophenyl)(hydroxy)methyl)benzonitrile (54b)

To a solution of 3-formylbenzonitrile (54a) (29 g, 217 mmol) in tetrahydrofuran (200 mL) cooled to 0° C. was added freshly prepared Grignard reagent (52c) (245 mL, 221 mmol, 0.9 M in THF) stirred at 0° C. for 1 h, and room temperature for 18 h. The reaction mixture was quenched with 1 N HCl (aq. 440 mL), stirred for 3 h, neutralized with NaOH (2 N, aq.) to pH=8. The reaction mixture was extracted with ethyl acetate (600, 300 mL). The combined extracts were washed with brine (120 mL), dried over MgSO₄, filtered and concentrated in vacuum. The crude product was purified by flash column chromatography [silica gel, eluting with hexanes/ethyl acetate (1:0 to 1:1) to give 3-((3-amino-4-fluorophenyl)(hydroxy)methyl)benzonitrile (54b) (36.28 g) as a brown gum which was used as such for next step; MS (ES+) 265.3 (M+23).

Step-2: Preparation of tert-butyl 3-(5-(5-((3-cyanophenyl)(hydroxy)methyl)-2-fluorophenylcarbamoyl)-3-(trifluoromethyl)-1H-pyrazol-1-yl)benzylcarbamate (54c)

To a solution of 3-((3-amino-4-fluorophenyl)(hydroxy)methyl)benzonitrile (54b) (24.682 g, 102 mmol) in DMF (480 mL) was added 1-(3-((tert-butoxycarbonylamino)methyl)phenyl)-3-(trifluoromethyl)-1H-pyrazole-5-carboxylic acid (10d) (35.0 g, 91 mmol), N-ethyl-N-isopropylpropan-2-amine (132 mL, 758 mmol), bromotripyrrolidin-1-ylphosphonium hexafluorophosphate(V) (PyBrOP, 42.8 g, 91 mmol) and stirred at room temperature for 19 h. The reaction mixture was diluted with ethyl acetate (1000 mL), washed with water (500, 400 mL), brine (400 mL), dried over MgSO₄, filtered and concentrated in vacuum. The crude product was purified by flash column chromatography [silica gel, eluting with hexanes/ethyl acetate (1:0 to 1:1)] to afford tert-butyl 3-(5-(5-((3-cyanophenyl)(hydroxy)methyl)-2-fluorophenylcarbamoyl)-3-(trifluoromethyl)-1H-pyrazol-1-yl)benzylcarbamate (54c) (4.583 g, 5% for two steps) as a yellow solid; ¹H NMR (300 MHz, DMSO-d₆) δ 10.57 (s, 1H), 7.81 (t, J=1.7 Hz, 1H), 7.73-7.66 (m, 2H), 7.64-7.19 (m, 10H), 6.25 (d, J=4.0 Hz, 1H), 5.78 (d, J=4.0 Hz, 1H), 4.19 (d, J=6.1 Hz, 2H), 1.37 (s, 9H); ¹⁹F NMR (282 MHz, DMSO-d₆) δ −60.81, −123.09; MS (ES+) 632.3 (M+23).

Step-3: Preparation of tert-butyl 3-(5-(5-((3-cyanophenyl)(cyclopropylmethylamino)methyl)-2-fluorophenylcarbamoyl)-3-(trifluoromethyl)-1H-pyrazol-1-yl)benzylcarbamate (54d)

To a solution of tert-butyl 3-(5-(5-((3-cyanophenyl)(hydroxy)methyl)-2-fluorophenylcarbamoyl)-3-(trifluoromethyl)-1H-pyrazol-1-yl)benzylcarbamate (54c) (1.333 g, 2.187 mmol) in dichloromethane (40 mL) at 0° C. was added thionyl chloride (0.340 mL, 4.59 mmol) and warmed to room temperature over 2 h. The reaction mixture was quenched with triethyl amine (2.0 mL, 14.35 mmol) stirred at room temperature for 1 h. It was then treated with cyclopropylmethanamine (4.30 mL, 48.0 mmol), concentrated to remove most of dichloromethane followed by addition of acetonitrile (30 mL), stirring at 70° C. for 14 h, and concentration in vacuum to dryness. The residue was treated with chloroform (200 mL), washed with water (100 mL), dried over MgSO₄ followed by filtration and concentration. The crude product was purified by flash column chromatography [silica gel eluting with hexanes/ethyl acetate (1:0 to 2:1)] to afford tert-butyl 3-(5-(5-((3-cyanophenyl)(cyclopropylmethylamino)methyl)-2-fluorophenylcarbamoyl)-3-(trifluoromethyl)-1H-pyrazol-1-yl)benzylcarbamate (54d) (184 mg, 13%) as colorless gum; ¹H NMR (300 MHz, DMSO-d₆) δ 10.56 (s, 1H), 7.89 (t, J=1.7 Hz, 1H), 7.77-7.71 (m, 1H), 7.70-7.30 (m, 10H), 7.22 (dd, J=10.3, 8.5 Hz, 1H), 4.93 (s, 1H), 4.19 (d, J=6.2 Hz, 2H), 2.26 (d, J=6.6 Hz, 2H), 1.37 (s, 9H), 1.00-0.80 (m, 1H), 0.45-0.28 (m, 2H), 0.12-−0.01 (m, 2H); ¹⁹F NMR (282 MHz, DMSO-d₆) δ −60.80, −123.20; MS (ES+) 663.4 (M+1).

Step-4: Preparation of 1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (54e)

To a solution of tert-butyl 3-(5-(5-((3-cyanophenyl)(cyclopropylmethylamino)methyl)-2-fluorophenylcarbamoyl)-3-(trifluoromethyl)-1H-pyrazol-1-yl)benzylcarbamate (54d) (161 mg, 0.243 mmol) in 1,4-Dioxane (18 mL) was added hydrogen chloride (2.60 mL, 10.40 mmol, 4 M in 1,4-dioxane) and stirred at room temperature for 16 h. the reaction mixture was treated with hexanes, decanted, washed with hexanes, and decanted again. The insoluble crude product was purified by flash column chromatography [silica gel, eluting with chloroform/CMA80 (1:0 to 2:1)] to afford 1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (54e). The pure product was dissolved in methanol (10 mL) and added 4 N HCl (aq. 0.14 mL) followed by concentration in vacuum to dryness to give HCl salt of 1-(3-(aminomethyl)phenyl)-N-

(5-((3-cyanophenyl)(cyclopropyl-methylamino)methyl)-2-fluorophenyl)-3-(trifluoromethyl)-1H-pyrazole-5-carboxamide (54e) (74 mg, 48%) white solid; $^1$H NMR (300 MHz, DMSO-$d_6$, $D_2O$ ex NMR) δ 8.13 (t, J=1.7 Hz, 1H), 7.98-7.84 (m, 3H), 7.73-7.64 (m, 3H), 7.63-7.48 (m, 4H), 7.44 (dd, J=10.2, 8.6 Hz, 1H), 5.75 (s, 1H), 4.12 (s, 2H), 2.76 (d, J=7.2 Hz, 2H), 1.17-0.94 (m, 1H), 0.68-0.47 (m, 2H), 0.34-0.24 (m, 2H); $^{19}$F NMR (282 MHz, DMSO-$d_6$) δ −60.82, −120.02; MS (ES+): 563.3 (M+1); Analysis calculated for $C_{30}H_{26}F_4N_6O$.2.0HCl.3.0$H_2O$: C, 52.26; H, 4.97; N, 12.19; Found: C, 52.26; H, 5.00; N, 11.72.

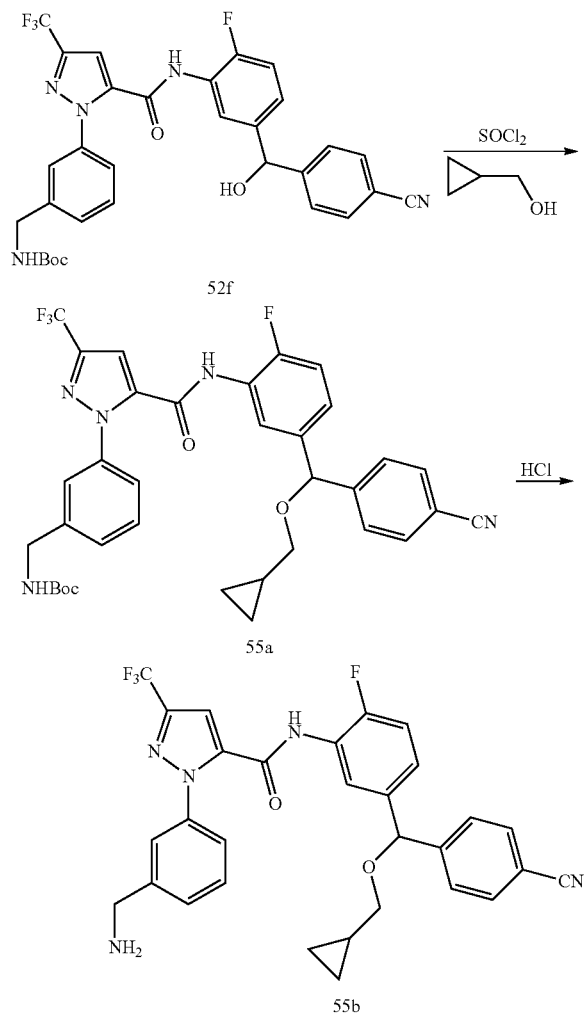

Scheme 55

Preparation of 1-(3-(aminomethyl)phenyl)-N-(5-((4-cyanophenyl)(cyclopropylmethoxy)methyl)-2-fluorophenyl)-3-(trifluoromethyl)-1H-pyrazole-5-carboxamide (55b)

Step-1: Preparation of tert-butyl 3-(5-(5-((4-cyanophenyl)(cyclopropylmethoxy)methyl)-2-fluorophenylcarbamoyl)-3-(trifluoromethyl)-1H-pyrazol-1-yl)benzylcarbamate (55a)

To a solution of tert-butyl 3-(5-(5-((4-cyanophenyl)(hydroxy)methyl)-2-fluorophenylcarbamoyl)-3-(trifluoromethyl)-1H-pyrazol-1-yl)benzylcarbamate (52f) (5.4 g, 8.86 mmol) in dichloromethane (50 mL) and triethylamine (7.51 mL, 53.9 mmol) at 0° C. was added thionyl chloride (1.254 mL, 17.19 mmol), reaction mixture was allowed to warm to room temperature and stirred for 1.5 h. The reaction mixture was quenched with triethylamine (7.51 mL, 53.9 mmol), cyclopropylmethanol (26.4 mL, 319 mmol) and heated with stirring at 105° C. for 13 h. The reaction mixture was cooled to room temperature and evaporated to dryness. To the residue was added water (100 mL) and extracted with chloroform (2×75 mL). The organic layers were combined washed with brine (70 mL), dried over $MgSO_4$ followed by filtration and concentration. The residue obtained was purified by flash column chromatography (silica gel 80 g, eluting with hexanes/ethyl acetate 0 to 100%) to furnish tert-butyl 3-(5-(5-((4-cyanophenyl)(cyclopropylmethoxy)methyl)-2-fluorophenylcarbamoyl)-3-(trifluoromethyl)-1H-pyrazol-1-yl)benzylcarbamate (55a) (0.308 g, 5.24% yield) as a yellow solid. MS (ES+): 632.3 (M+23).

Step-2: Preparation of 1-(3-(aminomethyl)phenyl)-N-(5-((4-cyanophenyl)(cyclopropylmethoxy)methyl)-2-fluorophenyl)-3-(trifluoromethyl)-1H-pyrazole-5-carboxamide (55b)

To a stirred solution of furnish tert-butyl 3-(5-(5-((4-cyanophenyl)(cyclopropylmethoxy)methyl)-2-fluorophenylcarbamoyl)-3-(trifluoromethyl)-1H-pyrazol-1-yl)benzylcarbamate (55a) (43 mg, 0.065 mmol) in methanol (5 mL) was added hydrochloric acid (2 M solution in methanol, 0.648 mL, 1.296 mmol) at room temperature and stirred for 18 h. The reaction was concentrated to remove excess hydrochloric acid. The residue was purified by flash column chromatography (silica gel 12 g, eluting with methanol in chloroform 0-50%) to afford pure 1-(3-(aminomethyl)phenyl)-N-(5-((4-cyanophenyl)(cyclopropylmethoxy)methyl)-2-fluorophenyl)-3-(trifluoromethyl)-1H-pyrazole-5-carboxamide (55b) (18 mg, 49.3%) as a white solid; $^1$H NMR (300 MHz, DMSO-d6) δ 10.62 (s, 1H, $D_2O$ exchangeable), 7.82 (d, J=8.3 Hz, 2H), 7.56 (dt, J=12.3, 6.2 Hz, 5H), 7.44 (d, J=7.0 Hz, 2H), 7.34 (d, J=7.2 Hz, 1H), 7.27 (d, J=7.8 Hz, 2H), 5.61 (s, 1H), 3.80 (s, 2H), 3.24 (d, J=6.8 Hz, 2H), 1.05 (s, 1H), 0.51-0.40 (m, 2H), 0.20-0.08 (m, 2H); MS (ES+) 564.3 (M+1), (ES−) 562.3 (M−1), 598.2 (M+Cl).

Scheme 56

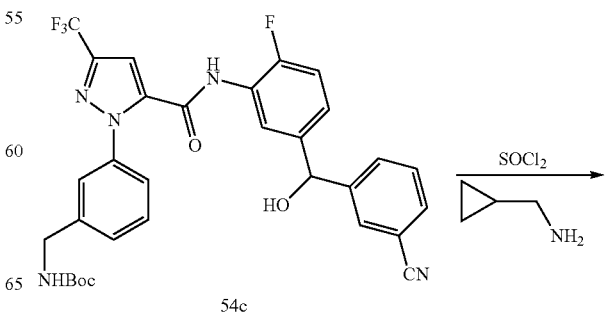

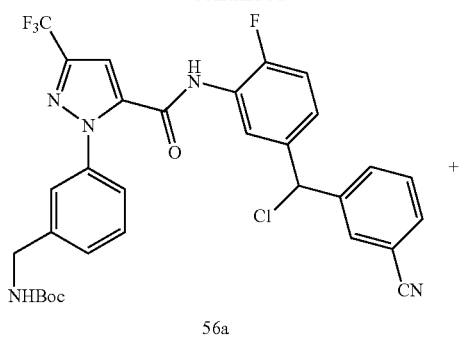
56a

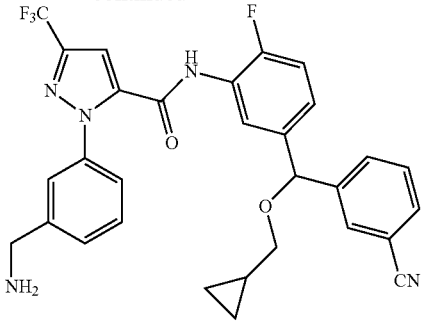
56c

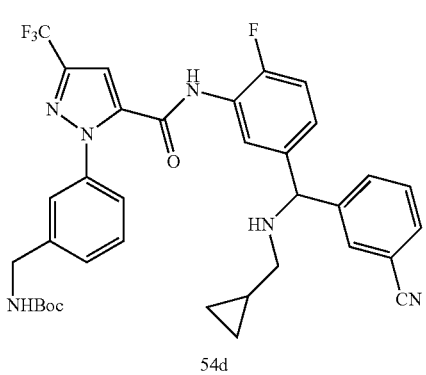 [SMILES: N#Cc1cccc(C(OCC2CC2)c2ccc(F)c(NC(=O)c3cc(C(F)(F)F)nn3-c3cccc(CN)c3)c2)c1]
54d

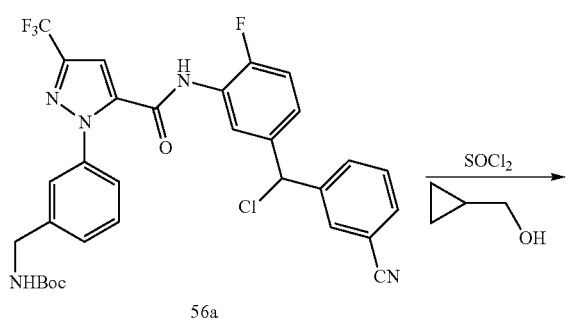
56a

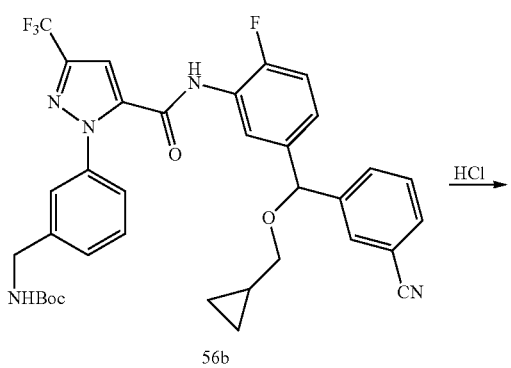
56b

Preparation of 1-(3-(aminomethyl)phenyl)-N-(5-((3-cyanophenyl)(cyclopropylmethoxy)methyl) 2-fluorophenyl)-3-(trifluoromethyl)-1H-pyrazole-5-carboxamide (56c)

Step-1: Preparation of tert-butyl 3-(5-(5-(chloro(3-cyanophenyl)methyl)-2-fluorophenylcarbamoyl)-3-(trifluoromethyl)-1H-pyrazol-1-yl)benzylcarbamate (56a)

To a solution of tert-butyl 3-(5-(5-((3-cyanophenyl)(hydroxy)methyl)-2-fluorophenylcarbamoyl)-3-(trifluoromethyl)-1H-pyrazol-1-yl)benzylcarbamate (54c) (1.333 g, 2.187 mmol) in dichloromethane (40 mL) at 0° C. was added thionyl chloride (0.34 mL, 4.59 mmol) and warmed to room temperature over 2 h. The reaction mixture was treated with triethyl amine (2.000 mL, 14.35 mmol) stirred at room temperature for 1 h. It was then treated with cyclopropylmethanamine (4.30 mL, 48.0 mmol) and concentrated to remove most of dichloromethane followed by addition of acetonitrile (30 mL), stirring at 70° C. for 14 h, and concentration to dryness. The residue was treated with chloroform (200 mL), washed with water (100 mL), dried over MgSO$_4$ followed by filtration and concentration. The crude product was purified by flash column chromatography [silica gel eluting with hexanes/ethyl acetate (1:0 to 2:1)] to afford;

1. tert-butyl 3-(5-(5-((3-cyanophenyl)(cyclopropylmethylamino)methyl)-2-fluorophenylcarbamoyl)-3-(trifluoromethyl)-1H-pyrazol-1-yl)benzylcarbamate (54d) (184 mg, 13%) as a colorless gum; $^1$H NMR (300 MHz, DMSO-d$_6$) δ 10.56 (s, 1H), 7.89 (t, J=1.7 Hz, 1H), 7.77-7.71 (m, 1H), 7.70-7.30 (m, 10H), 7.22 (dd, J=10.3, 8.5 Hz, 1H), 4.93 (s, 1H), 4.19 (d, J=6.2 Hz, 2H), 2.26 (d, J=6.6 Hz, 2H), 1.37 (s, 9H), 1.00-0.80 (m, 1H), 0.45-0.28 (m, 2H), 0.12--0.01 (m, 2H); $^{19}$F NMR (282 MHz, DMSO-d$_6$) δ -60.80, -123.20; MS (ES+) 663.4 (M+1).

2. tert-butyl 3-(5-(5-(chloro(3-cyanophenyl)methyl)-2-fluorophenylcarbamoyl)-3-(trifluoromethyl)-1H-pyrazol-1-yl)benzylcarbamate (56a) (300 mg, 22%) as a white solid; $^1$H NMR (300 MHz, DMSO-d$_6$) δ 10.67 (s, 1H), 7.95 (t, J=1.7 Hz, 1H), 7.86-7.74 (m, 3H), 7.67-7.58 (m, 2H), 7.54-7.28 (m, 7H), 6.64 (s, 1H), 4.19 (d, J=6.2 Hz, 2H), 1.37 (s, 9H); $^{19}$F NMR (282 MHz, DMSO-d$_6$) δ -60.82, -120.97; MS (ES+) 650.3 (M+23).

Step-2: Preparation of tert-butyl 3-(5-(5-((3-cyanophenyl)(cyclopropylmethoxy)methyl)-2-fluorophenylcarbamoyl)-3-(trifluoromethyl)-1H-pyrazol-1-yl)benzylcarbamate (56b)

A solution of tert-butyl 3-(5-(5-(chloro(3-cyanophenyl)methyl)-2-fluorophenylcarbamoyl)-3-(trifluoromethyl)-1H-pyrazol-1-yl)benzylcarbamate (56a) (0.26 g, 0.414 mmol) was treated with cyclopropylmethanol (3.10 mL, 37.5 mmol) and triethylamine (0.470 mL, 3.37 mmol) followed by stirring at 100° C. for 15 h. The reaction mixture was diluted with ethyl acetate (120 mL) and washed with water (75 mL). The organic layer was washed with brine (60 mL), dried over MgSO$_4$ followed by filtration and concentration. The crude product was purified by flash column chromatography [silica gel with hexanes/ethyl acetate (1:0 to 2:1)] to furnish tert-butyl 3-(5-(5-((3-cyanophenyl)(cyclopropylmethoxy)methyl)-2-fluorophenylcarbamoyl)-3-(trifluoromethyl)-1H-pyrazol-1-yl)benzylcarbamate (56b) (243 mg, 88%) as a colorless gum; $^1$H NMR (300 MHz, DMSO-d$_6$) δ 10.60 (s, 1H), 7.82 (t, 1H), 7.74 (dt, J=7.5, 1.5 Hz, 1H), 7.71-7.66 (m, 1H), 7.64-7.22 (m, 10H), 5.59 (s, 1H), 4.19 (d, J=6.3 Hz, 2H), 3.24 (d, J=6.8 Hz, 2H), 1.37 (s, 9H), 1.12-0.99 (m, 1H), 0.54-0.39 (m, 2H), 0.22-0.08 (m, 2H); $^{19}$F NMR (282 MHz, DMSO-d$_6$) δ −60.82, −122.30; MS (ES+) 686.4 (M+23).

Step-3: Preparation of 1-(3-(aminomethyl)phenyl)-N-(5-((3-cyanophenyl)(cyclopropyl-methoxy)methyl)-2-fluorophenyl)-3-(trifluoromethyl)-1H-pyrazole-5-carboxamide (56c)

To a solution of tert-butyl 3-(5-(5-((3-cyanophenyl)(cyclopropylmethoxy)methyl)-2-fluorophenylcarbamoyl)-3-(trifluoromethyl)-1H-pyrazol-1-yl)benzylcarbamate (56b) (220 mg, 0.331 mmol) in methanol (24 mL) was added conc. hydrogen chloride (0.170 mL, 2.039 mmol) followed by stirring at room temperature for 23.5 h and concentration under vacuum (at <30 OC). The residue obtained was purified by flash column chromatography [silica gel 4 g, eluting with chloroform/CMA80 (1:0 to 3:1) to afford 1-(3-(aminomethyl)phenyl)-N-(5-((3-cyanophenyl)(cyclopropylmethoxy)methyl)-2-fluorophenyl)-3-(trifluoromethyl)-1H-pyrazole-5-carboxamide (56c) (133 mg, 71%) free base as a colorless gum. The purified product (69 mg) was dissolved in methanol (10 mL) and then treated with 4 N HCl (aq. 0.12 mL) followed by concentration to dryness to give HCl salt of colorless gum, (78 mg) as a white solid. $^1$H NMR (300 MHz, DMSO-d$_6$) δ 10.67 (s, 1H), 8.38 (s, 3H), 7.81 (t, J=1.7 Hz, 1H), 7.76-7.66 (m, 4H), 7.63-7.47 (m, 6H), 7.37-7.23 (m, 2H), 5.59 (s, 1H), 4.11 (q, J=5.8 Hz, 2H), 3.29-3.20 (m, 2H), 1.15-0.95 (m, 1H), 0.54-0.37 (m, 2H), 0.27-0.04 (m, 2H); $^1$H NMR (300 MHz, DMSO-d$_6$) δ 7.80 (t, J=1.6 Hz, 1H), 7.74 (dt, J=7.6, 1.5 Hz, 1H), 7.72-7.66 (m, 2H), 7.64 (s, 1H), 7.62-7.49 (m, 5H), 7.36-7.23 (m, 2H), 5.59 (s, 1H), 4.12 (s, 2H), 3.26-3.23 (m, 2H), 1.14-0.95 (m, 1H), 0.54-0.39 (m, 2H), 0.18-0.11 (m, 2H). $^{19}$F NMR (282 MHz, DMSO-d$_6$) δ −60.82, −121.88; MS (ES+) 564.3 (M+1); (ES−) 562.3 (M−1); HPLC (94.54%, $t_R$=19.943 min); Analysis calculated for $C_{30}H_{25}F_4N_5O_2 \cdot 1.0HCl \cdot 1.25H_2O$: C, 57.88; H, 4.61; N, 11.25; Found: C, 57.90; H, 4.57; N, 11.19.

Scheme 57

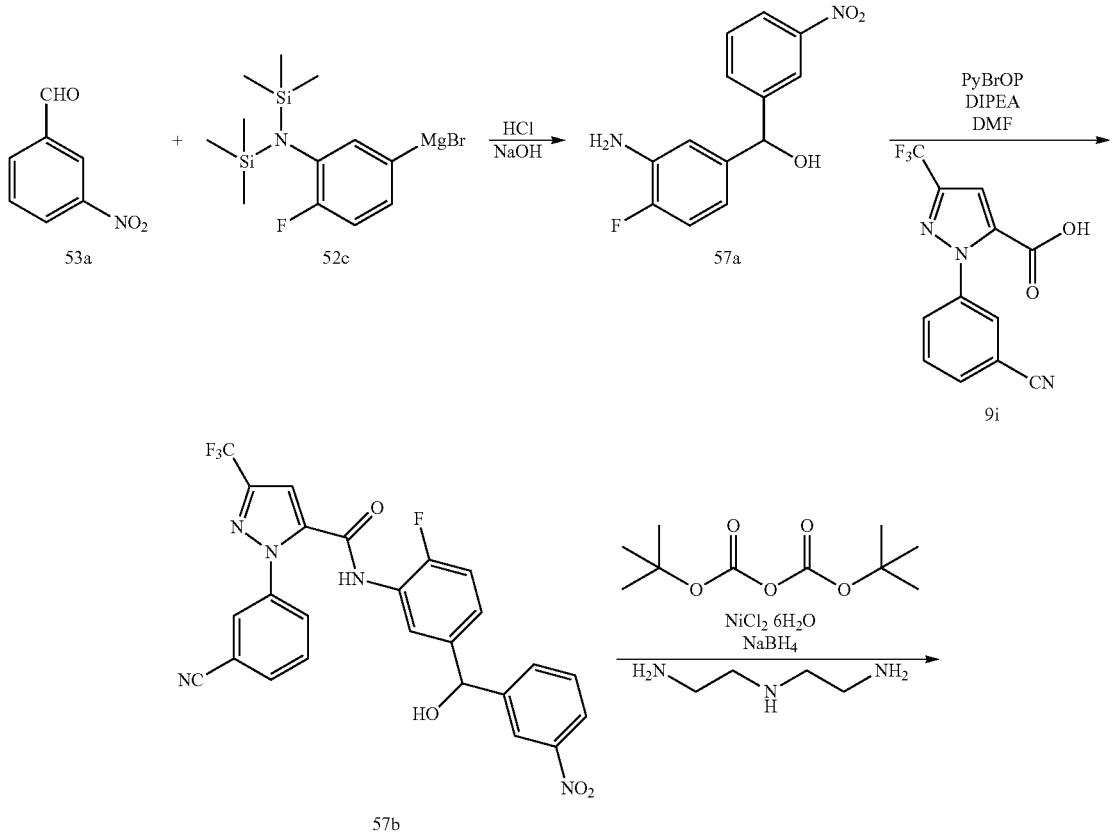

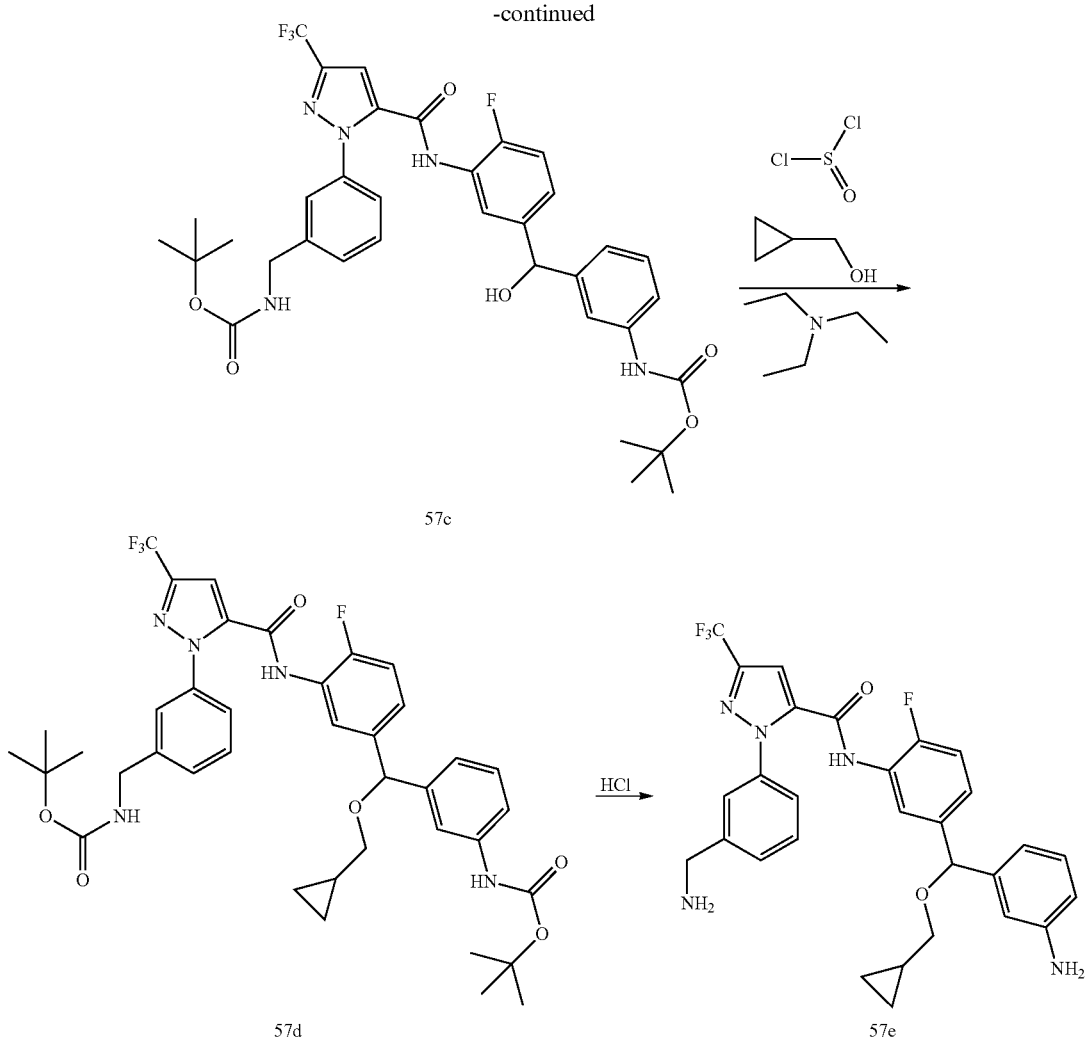

57c

57d

57e

Preparation of 1-(3-(aminomethyl)phenyl)-N-(5-((3-aminophenyl)(cyclopropylmethoxy)methyl)-2-fluorophenyl)-3-(trifluoromethyl)-1H-pyrazole-5-carboxamide (57e)

Step-1: (3-amino-4-fluorophenyl)(3-nitrophenyl)methanol (57a)

To a stirred solution of 3-nitrobenzaldehyde (53a) (25.7 g, 170 mmol) in tetrahydrofuran (150 mL) was added freshly prepared (3-(bis(trimethylsilyl)amino)-4-fluorophenyl)magnesium bromide (52c) (170 mL, 170 mmol) at 0° C. The reaction was stirred for 14 h at room temperature and quenched by adding hydrogen chloride (2N, 213 mL, 425 mmol) at 0° C., stirred for 1 h, TLC analysis (ethyl acetate/hexanes, 1/1, v/v) shows reaction was complete. The reaction mixture was treated with sodium hydroxide (2 N, 255 mL, 510 mmol) and extracted with ethyl acetate (3×750 mL). The organic layers were combined dried over anhydrous MgSO$_4$, filtered, and evaporated to dryness. The crude residue was purified by flash column chromatography (silica gel 1 kg, eluting with 0-70% ethyl acetate in hexane) to furnish (3-amino-4-fluorophenyl)(3-nitrophenyl)methanol (57a) (4.638 g, 10% yield) as a dark brown syrup.

$^1$H NMR (300 MHz, DMSO-d$_6$) δ 8.21 (t, J=2.0 Hz, 1H), 8.08 (ddd, J=8.1, 2.5, 1.1 Hz, 1H), 7.77 (dt, J=7.2, 1.4 Hz, 1H), 7.60 (t, J=7.9 Hz, 1H), 6.91 (dd, J=11.5, 8.3 Hz, 1H), 6.78 (dd, J=8.9, 2.2 Hz, 1H), 6.55 (ddd, J=8.4, 4.4, 2.2 Hz, 1H), 6.13 (d, J=3.9 Hz, 1H), 5.71 (d, J=3.8 Hz, 1H), 5.13 (s, 2H); MS (ES$^+$): MS (ES+) 263.1 (M+1), MS (ES−) 523.2 (2M−1).

Step-2: Preparation of 1-(3-cyanophenyl)-N-(2-fluoro-5-(hydroxy(3-nitrophenyl)methyl)phenyl)-3-(trifluoromethyl)-1H-pyrazole-5-carboxamide (57b)

In a 500 mL single-necked flask 1-(3-cyanophenyl)-3-(trifluoromethyl)-1H-pyrazole-5-carboxylic acid (9i) (5.91 g, 21.00 mmol), (3-amino-4-fluorophenyl)(3-nitrophenyl)methanol (57a) (4.59 g, 17.50 mmol), bromo-tris-pyrrolidino phosphoniumhexafluorophosphate (PyBrOP, 9.79 g, 21.00 mmol) were treated with N,N-dimethylformamide (102 mL,) and N-ethyl-N-isopropylpropan-2-amine (15.24 mL, 88 mmol) successively in a positive flow of nitrogen at room temperature. The resulting reaction mixture was stirred at room temperature for 16 h under a positive flow of nitrogen atmosphere. The residue was diluted with ethyl acetate (250 mL), and layer was separated with water (1 L), aq. layer was again extracted with ethyl acetate (500 mL), combined organics were dried over anhydrous MgSO$_4$, filtered, evaporated to dryness. The residue was purified by flash column chromatography [silica gel 120 g, eluting with ethyl acetate in hexanes from 0-100%] to furnish 1-(3-cyanophenyl)-N-(2-fluoro-5-(hydroxy(3-nitrophenyl)methyl)phenyl)-3-(trifluoromethyl)-1H-pyrazole-5-carboxamide (57b) (2.641 g, 29% yield) as a yellow solid; $^1$H NMR (300 MHz, DMSO-$d_6$) δ 10.56 (s, 1H), 8.24 (t, J=2.0 Hz, 1H), 8.15-8.06 (m, 2H), 7.99 (dt, J=7.8, 1.3 Hz, 1H), 7.93-7.86 (m, 1H), 7.80 (d, J=7.7 Hz, 1H), 7.77-7.68 (m, 2H), 7.67-7.54 (m, 2H), 7.39-7.19 (m, 2H), 6.36 (d, J=4.1 Hz, 1H), 5.90 (d, J=4.0 Hz, 1H); MS (ES$^+$): MS (ES+) 548.2 (M+Na), MS (ES−) 524.7 (M−1); 560.3 (M+Cl).

Step-3: Preparation of tert-butyl 3-(5-((5-((3-tertbutyloxycarbonylaminophenyl)(hydroxy)methyl)-2-fluorophenyl)carbamoyl)-3-(trifluoromethyl)-1H-pyrazol-1-yl)benzylcarbamate (57c)

To a stirred solution of 1-(3-cyanophenyl)-N-(2-fluoro-5-(hydroxy(3-nitrophenyl)methyl)phenyl)-3-(trifluoromethyl)-1H-pyrazole-5-carboxamide (57b) (2.25 g, 4.28 mmol) in anhydrous methanol (60 mL), cooled to 0° C., were added di-tert-butyl dicarbonate (3.74 g, 17.13 mmol) and stirred for 10 min. Nickel(II) chloride hexahydrate (0.763 g, 3.21 mmol), sodium borohydride (1.620 g, 42.8 mmol) was then added in small portions over a period of 4 h. The reaction was exothermic and effervescent. The reaction mixture was stirred for 45 min at 0° C., at this point N1-(2-aminoethyl)ethane-1,2-diamine (4.63 mL, 42.8 mmol) was added. The mixture was allowed to stir for additional 30 mins before solvent was evaporated. The residue was treated with water (75 mL), and extracted with chloroform (2×100 mL) combined organic layers were dried over anhydrous MgSO$_4$, filtered, excess solvents were pumped-off under reduced pressure. The residue was purified by flash column chromatography [(silica gel 40 g, eluting with methanol/chloroform from 0 to 50%)] to furnish tert-butyl 3-(5-((5-((3-tertbutyloxycarbonylaminophenyl)(hydroxy)methyl)-2-fluorophenyl)carbamoyl)-3-(trifluoromethyl)-1H-pyrazol-1-yl)benzylcarbamate (57c) (0.963 g, 1.376 mmol, 32.1% yield) as a light red solid; $^1$H NMR (300 MHz, DMSO-$d_6$) δ 10.55 (s, 1H), 9.30 (s, 1H), 7.61-7.31 (m, 7H), 7.29-7.12 (m, 4H), 6.92 (d, J=7.6 Hz, 1H), 5.96 (d, J=3.8 Hz, 1H), 5.60 (d, J=3.9 Hz, 1H), 4.19 (d, J=6.2 Hz, 2H), 1.45 (s, 9H), 1.38 (s, 9H); $^{19}$F NMR (282 MHz, DMSO-$d_6$) δ −60.79, −123.57; MS (ES$^+$): MS (ES+) 722.3 (M+Na).

Step-4: Preparation of tert-butyl 3-(5-((5-((tert-butoxycarbonyl-3-aminophenyl)(cyclopropylmethoxy)methyl)-2-fluorophenyl)carbamoyl)-3-(trifluoromethyl)-1H-pyrazol-1-yl)benzylcarbamate (57d)

A solution of tert-butyl 3-(5-((5-((3-tertbutyloxycarbonylaminophenyl)(hydroxy)methyl)-2-fluorophenyl)carbamoyl)-3-(trifluoromethyl)-1H-pyrazol-1-yl)benzylcarbamate (57c) (1.1 g, 1.572 mmol) in dichloromethane (20 mL) at 0° C. was treated with thionyl chloride (0.222 mL, 3.05 mmol) and allowed to warm to room temperature and stirred for 2.5 h. The solution was treated with triethylamine (1.332 mL, 9.56 mmol) followed by stirring at room temperature for 30 min, to this cyclopropylmethanol (11.70 mL, 141 mmol) and triethylamine (1.332 mL, 9.56 mmol) was added, concentrated to remove most of dichloromethane followed by addition of more triethylamine (1.332 mL, 9.56 mmol) and stirring at 115° C. for 11 h. The reacuon mixture was cooled and concentrated to dryness. The residue obtained was treated with water (25 mL) and extracted with chloroform (2×30 mL). The combined organic layers were dried over MgSO$_4$, filtered, evaporated to dryness. The residue was purified by flash column chromatography [(silica gel 40 g, eluting with ethyl acetate in hexanes from 0 to 100%)] to furnish tert-butyl 3-(5-((5-(((tert-butoxycarbonyl-3-aminophenyl)(cyclopropylmethoxy)methyl)-2-fluorophenyl)carbamoyl)-3-(trifluoromethyl)-1H-pyrazol-1-yl)benzylcarbamate (57d) (0.521 g, 0.691 mmol, 44.0% yield) as a white solid; $^1$H NMR (300 MHz, DMSO-$d_6$) δ 10.58 (s, 1H, D$_2$O exchangeable), 9.35 (s, 1H), 7.58 (s, 1H), 7.56-7.45 (m, 3H), 7.42 (d, J=7.4 Hz, 2H), 7.38-7.32 (m, 2H), 7.23 (dq, J=20.3, 7.8 Hz, 4H), 6.92 (d, J=7.4 Hz, 1H), 5.39 (s, 1H), 4.19 (d, J=6.2 Hz, 2H), 3.21 (dd, J=6.8, 3.1 Hz, 2H), 1.45 (s, 9H), 1.37 (s, 9H), 1.03 (d, J=7.8 Hz, 1H), 0.45 (dt, J=8.7, 2.9 Hz, 2H), 0.16 (dd, J=5.6, 3.9 Hz, 2H); $^{19}$F NMR (282 MHz, DMSO-$d_6$) δ −60.81, −122.72; MS (ES$^+$): MS (ES+) 776.4 (M+Na), MS (ES−) 752.3 (M−1).

Step-5: Preparation of 1-(3-(aminomethyl)phenyl)-N-(5-((3-aminophenyl)(cyclopropylmethoxy)methyl)-2-fluorophenyl)-3-(trifluoromethyl)-1H-pyrazole-5-carboxamide (57e)

To a solution of tert-butyl 3-(5-((5-(((tert-butoxycarbonyl-3-aminophenyl)(cyclopropylmethoxy)methyl)-2-fluorophenyl)carbamoyl)-3-(trifluoromethyl)-1H-pyrazol-1-yl)benzylcarbamate (57d) (0.511 g, 0.678 mmol) in methanol (20 mL) was added drop-wise conc. hydrogen chloride (12 N HCl) (1.412 mL, 16.95 mmol) followed by stirring at room temperature for 14 h. Excess solvent was pumped-off under reduced pressure. The residue was purified by flash column chromatography [(silica gel 40 g, eluting with CMA80 in chloroform from 0 to 50%)] to furnish 1-(3-(aminomethyl)phenyl)-N-(5-((3-aminophenyl)(cyclopropylmethoxy)methyl)-2-fluorophenyl)-3-(trifluoromethyl)-1H-pyrazole-5-carboxamide (57e) (0.261 g, 70% yield) as a colorless solid; $^1$H NMR (300 MHz, DMSO-$d_6$) δ 10.59 (s, 1H, D$_2$O exchangeable), 7.59 (d, J=8.8 Hz, 2H), 7.55-7.45 (m, 3H), 7.44-7.35 (m, 1H), 7.30-7.15 (m, 2H), 6.94 (t, J=7.7 Hz, 1H), 6.52 (t, J=1.9 Hz, 1H), 6.50-6.36 (m, 2H), 5.26 (s, 1H), 5.08 (s, 2H, D$_2$O exchangeable), 3.89 (s, 2H), 3.19 (dd, J=6.8, 2.7 Hz, 2H), 1.11-0.94 (m, 1H), 0.54-0.38 (m, 2H), 0.23-0.08 (m, 2H); $^{19}$F NMR (282 MHz, DMSO-$d_6$) δ −60.76, −123.05; MS (ES$^+$): MS (ES+) 554.3 (M+1), 588.2 (M−1).

A solution of 1-(3-(aminomethyl)phenyl)-N-(5-((3-aminophenyl)(cyclopropylmethoxy)methyl)-2-fluorophenyl)-3-(trifluoromethyl)-1H-pyrazole-5-carboxamide (57e) freebase (20 mg, 0.036 mmol) in methanol (2 mL) was treated with hydrogen chloride (0.217 mL, 0.434 mmol) followed by stirring at room temperature for 10 min. Excess solvent was pumped-off under reduced pressure to furnish 1-(3-(aminomethyl)phenyl)-N-(5-((3-aminophenyl)(cyclopropylmethoxy)methyl)-2-fluorophenyl)-3-(trifluoromethyl)-1H-pyrazole-5-carboxamide (57e) (22 mg, 97%) hydrochloride salt as a colorless solid; $^1$H NMR (300 MHz, DMSO-$d_6$) δ 10.68 (s, 1H), 8.35 (s, 4H), 7.72 (s, 1H), 7.68 (s, 1H), 7.64-7.47 (m, 5H), 7.36-7.21 (m, 3H), 7.10 (s, 2H), 7.00 (s, 2H), 5.47 (s, 1H), 4.12 (s, 2H), 3.22 (d, J=6.8 Hz, 2H), 1.15-0.97 (m, 1H), 0.55-0.35 (m, 2H), 0.23-0.09 (m, 2H); $^{19}$F NMR (282 MHz, DMSO-$d_6$) δ −60.82, −122.33; MS (ES$^+$): MS (ES+) 554.3 (M+1), 576.3 (M+Na), 552.3 (M−1), 588.2 (M+Cl); Analysis calculated for: $C_{29}H_{27}F_4N_5O_2 \cdot 1.75H_2O \cdot 2HCl$: C, 53.30; H, 4.94; N, 10.72; Found: C, 53.37; H, 4.79; N, 10.67.

Scheme 58

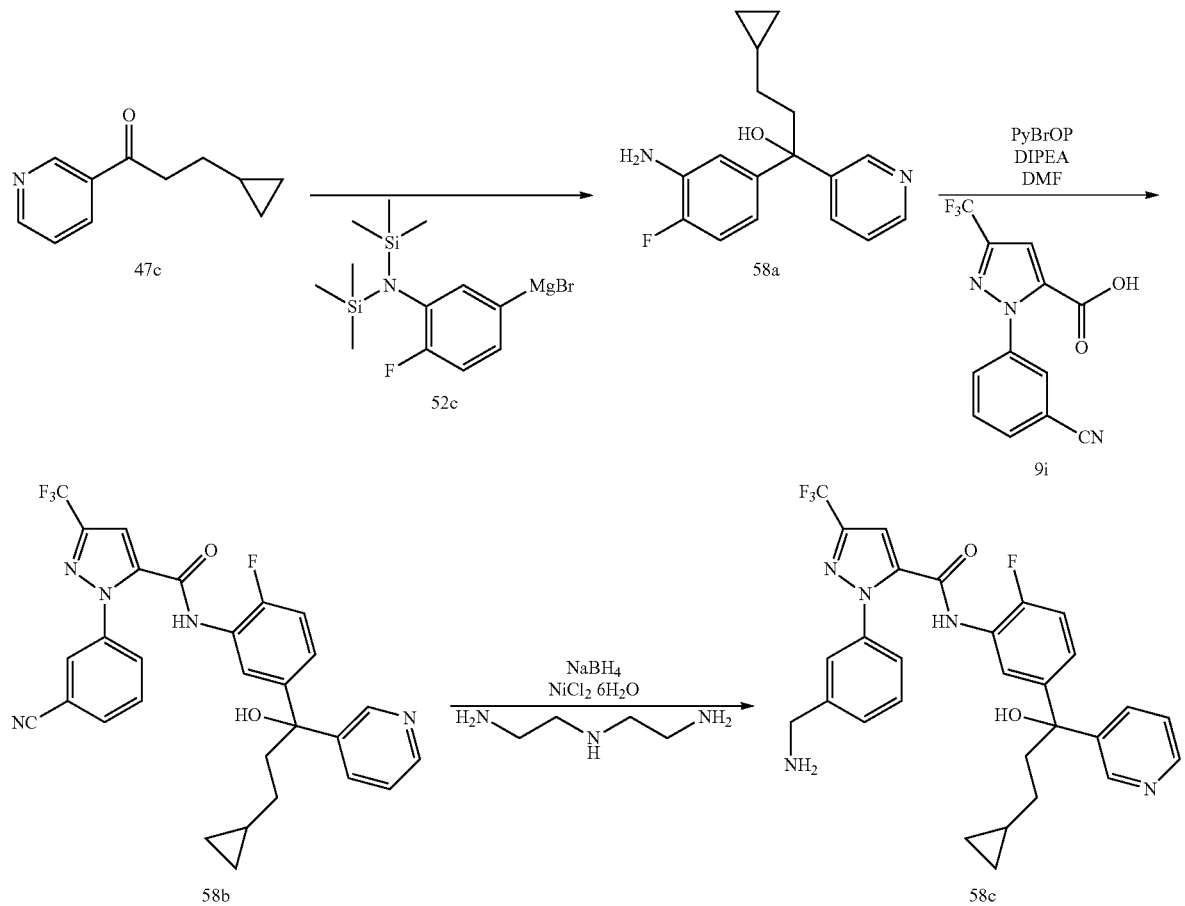

Preparation of 1-(3-(aminomethyl)phenyl)-N-(5-(3-cyclopropyl-1-hydroxy-1-(pyridin-3-yl)propyl)-2-fluorophenyl)-3-(trifluoromethyl)-1H-pyrazole-5-carboxamide (58c)

Step-1: Preparation of 1-(3-amino-4-fluorophenyl)-3-cyclopropyl-1-(pyridin-3-yl)propan-1-ol (58a)

To a stirred solution of 3-cyclopropyl-1-(pyridin-3-yl)propan-1-one (47c) (12 g, 68.5 mmol) in tetrahydrofuran (100 mL) was added freshly prepared (3-(bis(trimethylsilyl)amino)-4-fluorophenyl)magnesium bromide (52c) (88 mL, 79 mmol) at 0° C. The reaction was allowed to come to room temperature for 12 h, quenched by adding hydrogen chloride (2N, 100 mL, 200 mmol) at 0° C., stirred for 1 h, TLC analysis (ethyl acetate/hexanes, 1/1, v/v) shows reaction was complete. The reaction mixture was treated with sodium hydroxide (2N, 105 mL, 210 mmol) and extracted with ethyl acetate (3×150 mL). The organic layers were combined dried over anhydrous MgSO$_4$, filtered, and evaporated to dryness. The crude residue was purified by flash column chromatography (silica gel 120 g, eluting with 0-100% ethyl acetate in hexane) to furnish 1-(3-amino-4-fluorophenyl)-3-cyclopropyl-1-(pyridin-3-yl)propan-1-ol (58a) (15.3 g, 78%) as a brown semisolid; MS (ES+) 309.2 (M+Na), (ES−) 285.2 (M−1).

Step-2: Preparation of 1-(3-cyanophenyl)-N-(5-(3-cyclopropyl-1-hydroxy-1-(pyridin-3-yl)propyl)-2-fluorophenyl)-3-(trifluoromethyl)-1H-pyrazole-5-carboxamide (58b)

To a solution of 1-(3-cyanophenyl)-3-(trifluoromethyl)-1H-pyrazole-5-carboxylic acid (9i) (11.99 g, 42.6 mmol) in N,N-dimethylformamide (257 mL, 3326 mmol) was added 1-(3-amino-4-fluorophenyl)-3-cyclopropyl-1-(pyridin-3-yl)propan-1-ol (58b) (14.65 g, 51.2 mmol), N-ethyl-N-isopropylpropan-2-amine (59.4 mL, 341 mmol) and Bromo-tris-pyrrolidino phosphoniumhexafluorophosphate (PyBroP) (21.86 g, 46.9 mmol) at room temperature. The resulting reaction mixture was stirred at 25° C. for 16 h. The reaction mixture was diluted with water (1000 mL) and extracted with ethyl acetate (3×1000 mL), washed with water (2×500 mL), brine (300 mL). The organic layers were combined dried over anhydrous MgSO$_4$, filtered, concentrated under reduced pressure to dryness. The residue was purified by flash column chromatography [silica gel 80 g, eluting with a (9:1) ethylacetate: methanol mixture in hexanes 0 to 50%] to afford 1-(3-cyanophenyl)-N-(5-(3-cyclopropyl-1-hydroxy-1-(pyridin-3-yl)propyl)-2-fluorophenyl)-3-(trifluoromethyl)-1H-pyrazole-5-carboxamide (58b) (19.9 g, 85% yield) as a yellow solid; $^1$H NMR (300 MHz, DMSO-d$_6$) δ 10.54 (s, 1H), 8.63 (d, J=2.2 Hz, 1H), 8.38 (dd, J=4.7, 1.6 Hz, 1H), 8.12 (t, J=1.8 Hz, 1H), 8.00 (dt, J=7.8, 1.3 Hz, 1H), 7.95-7.86 (m, 1H), 7.82-7.69 (m, 3H), 7.61 (dd, J=7.6, 2.3

Hz, 1H), 7.40-7.27 (m, 2H), 7.21 (dd, J=10.2, 8.7 Hz, 1H), 5.81 (s, 1H), 2.34 (t, J=8.0 Hz, 2H), 1.05 (d, J=13.9 Hz, 2H), 0.64 (h, J=6.6 Hz, 1H), 0.40-0.28 (m, 2H), −0.07 (dd, J=4.9, 1.6 Hz, 2H); MS (ES+): 550.3 (M+1).

Step-3: Preparation of 1-(3-(aminomethyl)phenyl)-N-(5-(3-cyclopropyl-1-hydroxy-1-(pyridin-3-yl)propyl)-2-fluorophenyl)-3-(trifluoromethyl)-1H-pyrazole-5-carboxamide (58c)

To a stirred solution of 1-(3-cyanophenyl)-N-(5-(3-cyclopropyl-1-hydroxy-1-(pyridin-3-yl)propyl)-2-fluorophenyl)-3-(trifluoromethyl)-1H-pyrazole-5-carboxamide (58b) (10 g, 18.20 mmol) in Methanol (300 mL) at 0° C. was added nickel(II) chloride hexahydrate (5.41 g, 22.75 mmol). To this to afford pure 1-(3-(aminomethyl)phenyl)-N-(5-(3-cyclopropyl-1-hydroxy-1-(pyridin-3-yl)propyl)-2-fluorophenyl)-3-(trifluoromethyl)-1H-pyrazole-5-carboxamide (58c) (2.56 g, 25.4% yield) as a colorless solid. $^1$HNMR (300 MHz, DMSO-$d_6$) δ 10.54 (s, 1H, $D_2O$ exchangeable), 8.62 (dd, J=2.4, 0.9 Hz, 1H), 8.38 (dd, J=4.7, 1.6 Hz, 1H), 7.77 (dt, J=8.1, 1.9 Hz, 1H), 7.69-7.62 (m, 1H), 7.57 (s, 1H), 7.51 (s, 1H), 7.48-7.38 (m, 2H), 7.39-7.27 (m, 3H), 7.25-7.15 (m, 1H), 5.80 (s, 1H, $D_2O$ exchangeable), 3.78 (s, 2H), 2.33 (t, J=7.9 Hz, 2H), 1.13-1.02 (m, 2H), 0.63 (p, J=7.3, 6.5 Hz, 1H), 0.39-0.28 (m, 2H), −0.07 (dt, J=5.5, 2.8 Hz, 2H); $^{19}$F NMR (282 MHz, DMSO-$d_6$) δ −60.73, −123.95; MS (ES+): 554.3 (M+1); Analysis calculated for $C_{29}H_{27}F_4N_5O_2 \cdot 1.5H_2O$: C, 59.99; H, 5.21; N, 12.06; Found: C, 60.07; H, 4.86; N, 11.68.

Scheme 59

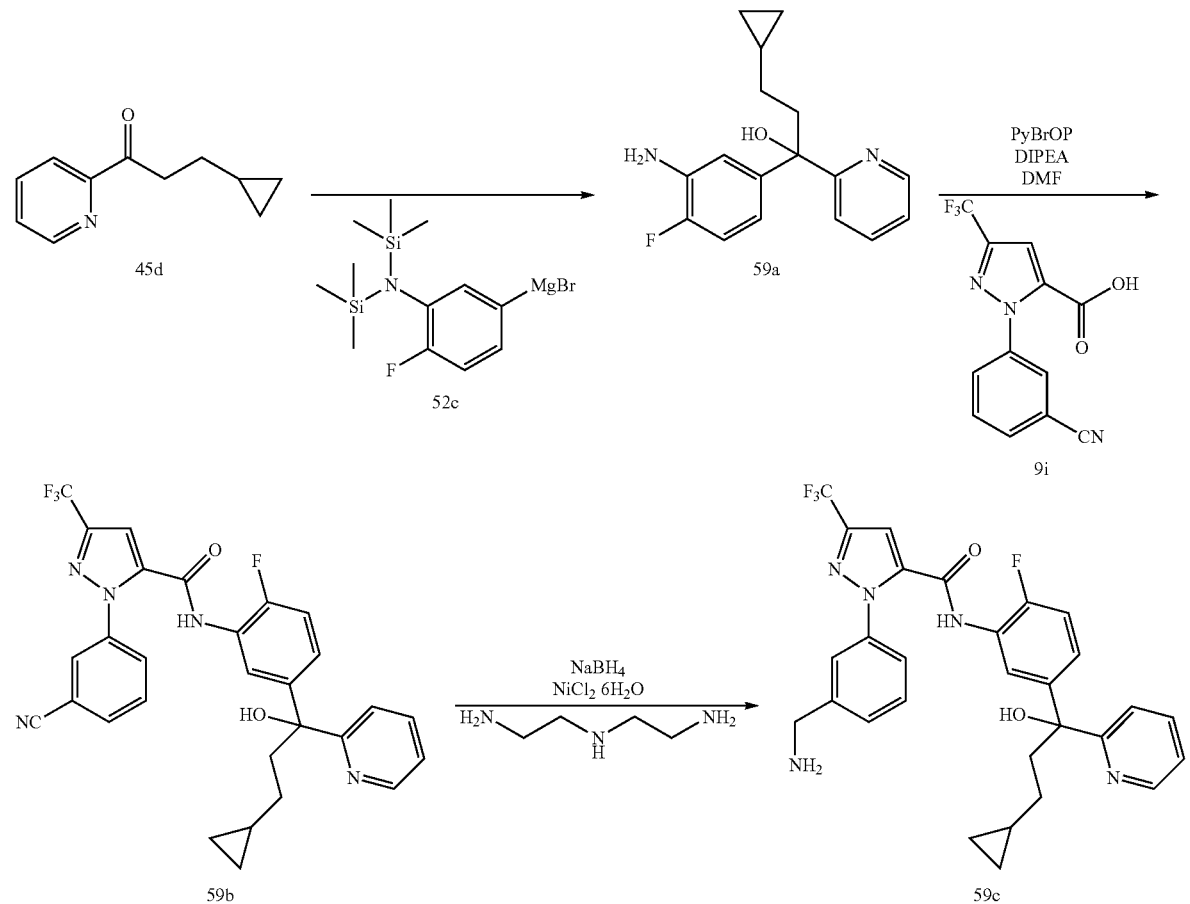

sodium tetrahydroborate (6.88 g, 182 mmol) was added in small portions over a period of 15 minutes. The reaction was stirred for 30 minutes and quenched by adding N1-(2-aminoethyl)ethane-1,2-diamine (15.09 mL, 146 mmol) and stirred for 30 minutes at room temperature. The reaction mixture was concentrated to remove methanol. The reaction mixture was diluted with water (200 mL) and stirred for 30 minutes. The solid separated collected by filtration. The solid was suspended in ethanol (100 mL) and concentrated to dryness to remove water. The residue was dissolved in methanol and purified by flash column chromatography (silica gel 40 g, eluting with CMA 80 in chloroform 0-100%)

Preparation of 1-(3-(aminomethyl)phenyl)-N-(5-(3-cyclopropyl-1-hydroxy-1-(pyridin-2-yl)propyl)-2-fluorophenyl)-3-(trifluoromethyl)-1H-pyrazole-5-carboxamide (59c)

Step-1: Preparation of 1-(3-amino-4-fluorophenyl)-3-cyclopropyl-1-(pyridin-2-yl)propan-1-ol (59a)

To a stirred solution of 3-cyclopropyl-1-(pyridin-2-yl)propan-1-one (45d) (13.09 g, 74.7 mmol) in tetrahydrofuran (50 mL) was added (3-(bis(trimethylsilyl)amino)-4-fluorophenyl)magnesium bromide (52c) (93 mL, 93 mmol) at 0°

C. The reaction was allowed to come to room temperature and stirred for 12 hrs at same temperature. The reaction was quenched by adding ammonium chloride solution (25 mL) and diluted with ethyl acetate (50 mL). The mixture was acidified with hydrochloric acid (10 mL, 3N) and stirred for 15 minutes and basified with saturated potassium carbonate solution (20 mL). The mixture was extracted with ethylacetate (3×100 mL), washed with water (2×50 mL), brine (25 mL), dried and concentrated. The crude residue was purified by combiflash (silicagel 80 g) eluting with CMA 80 in chloroform afforded pure 1-(3-amino-4-fluorophenyl)-3-cyclopropyl-1-(pyridin-2-yl)propan-1-ol (59a) (9.95 g, 46.5%) as a colorless solid; MS (ES+): 309.2 (M+23).

Step-2: Preparation of 1-(3-cyanophenyl)-N-(5-(3-cyclopropyl-1-hydroxy-1-(pyridin-2-yl)propyl)-2-fluorophenyl)-3-(trifluoromethyl)-1H-pyrazole-5-carboxamide (59b)

To a solution of 1-(3-cyanophenyl)-3-(trifluoromethyl)-1H-pyrazole-5-carboxylic acid (9i) (7.32 g, 26.0 mmol) in N,N-dimethylformamide (157 mL, 2032 mmol) was added 1-(3-amino-4-fluorophenyl)-3-cyclopropyl-1-(pyridin-2-yl)propan-1-ol (59a) (8.951 g, 31.3 mmol), N-ethyl-N-isopropylpropan-2-amine (36.3 mL, 208 mmol) and Bromo-tris-pyrrolidino phosphoniumhexafluorophosphate (PyBrOP, 13.36 g, 28.7 mmol) at room temperature. The resulting reaction mixture was stirred at 25° C. for 16 h. The reaction mixture was diluted with water (1000 mL) and extracted with ethyl acetate (3×1000 mL) and washed with water (2×500 mL), brine (300 mL). The organic layers were combined dried over anhydrous $MgSO_4$, filtered, concentrated in under reduced pressure to dryness. The residue was purified by flash column chromatography [silica gel 80 g, eluting with a (9:1) ethyl acetate: methanol mixture in hexanes 0 to 50%] to afford 1-(3-cyanophenyl)-N-(5-(3-cyclopropyl-1-hydroxy-1-(pyridin-2-yl)propyl)-2-fluorophenyl)-3-(trifluoromethyl)-1H-pyrazole-5-carboxamide (59b) (9.42 g, 65.8%) as white solid; $^1$H NMR (300 MHz, DMSO-$d_6$) δ 10.52 (s, 1H, $D_2O$ exchangeable), 8.49 (ddd, J=4.8, 1.8, 0.9 Hz, 1H), 8.12 (t, J=1.9 Hz, 1H), 8.00 (dt, J=7.7, 1.3 Hz, 1H), 7.94-7.86 (m, 1H), 7.79-7.61 (m, 5H), 7.42 (ddd, J=8.8, 4.8, 2.3 Hz, 1H), 7.24-7.12 (m, 2H), 5.84 (s, 1H, $D_2O$ exchangeable), 2.47-2.29 (m, 2H), 1.02 (qt, J=13.7, 7.4 Hz, 2H), 0.59 (ddt, J=10.3, 7.0, 3.7 Hz, 1H), 0.39-0.26 (m, 2H), −0.05−−0.17 (m, 2H); MS (ES+): 572.3 (M+23).

Step-3: Preparation of 1-(3-(aminomethyl)phenyl)-N-(5-(3-cyclopropyl-1-hydroxy-1-(pyridin-2-yl)propyl)-2-fluorophenyl)-3-(trifluoromethyl)-1H-pyrazole-5-carboxamide (59c)

To a stirred solution of 1-(3-cyanophenyl)-N-(5-(3-cyclopropyl-1-hydroxy-1-(pyridin-2-yl)propyl)-2-fluorophenyl)-3-(trifluoromethyl)-1H-pyrazole-5-carboxamide (59b) (8.9 g, 16.20 mmol) in methanol (300 mL) at 0° C. was added nickel(II) chloride hexahydrate (4.81 g, 20.24 mmol). To this sodium tetrahydroborate (6.13 g, 162 mmol) was added in small portions over a period of 15 minutes. The reaction was stirred for 30 minutes and quenched by adding N1-(2-aminoethyl)ethane-1,2-diamine (13.43 mL, 130 mmol) and stirred for 30 minutes at room temperature. The reaction mixture was concentrated to remove methanol. The reaction mixture was diluted water (800 mL) and stirred for 30 minutes. The solid separated was collected by filtration. The solid was dissolved in chloroform (500 mL), washed with water (2×200 mL).

The aqueous layer was extracted with chloroform (2×200 mL). The combined chloroform extracts were washed with brine (2×200 mL), dried and concentrated in vacuum. The residue purified by flash column chromatography (silicagel 120 g, eluting with CMA 80 in chloroform 0-100%) to afford 1-(3-(aminomethyl)phenyl)-N-(5-(3-cyclopropyl-1-hydroxy-1-(pyridin-2-yl)propyl)-2-fluorophenyl)-3-(trifluoromethyl)-1H-pyrazole-5-carboxamide (59c) (4.56 g, 50.9% yield) as a white solid; $^1$H NMR (300 MHz, DMSO-$d_6$) δ 10.51 (s, 1H, $D_2O$ exchangeable), 8.49 (dt, J=4.6, 1.4 Hz, 1H), 7.72 (ddt, J=7.8, 5.5, 2.7 Hz, 2H), 7.63 (d, J=7.9 Hz, 1H), 7.57 (s, 1H), 7.51 (s, 1H), 7.48-7.37 (m, 3H), 7.36-7.30 (m, 1H), 7.24-7.11 (m, 2H), 5.83 (s, 1H, $D_2O$ exchangeable), 3.78 (s, 2H), 3.342 (s, 2H, $D_2O$ exchangeable), 2.42-2.26 (m, 2H), 1.00 (ddd, J=25.9, 14.0, 7.2 Hz, 2H), 0.68-0.49 (m, 1H), 0.40-0.24 (m, 2H), −0.10 (dd, J=5.5, 3.7 Hz, 2H); $^{19}$F NMR (282 MHz, DMSO-$d_6$) δ −60.71, −124.32; MS (ES+): 554.3 (M+1); Analysis calculated for $C_{29}H_{27}F_4N_5O_2$ $(H_2O)_{0.25}$: C, 62.39; H, 4.96; N, 12.55; Found: C, 62.09; H, 5.05; N, 12.51.

Scheme 60

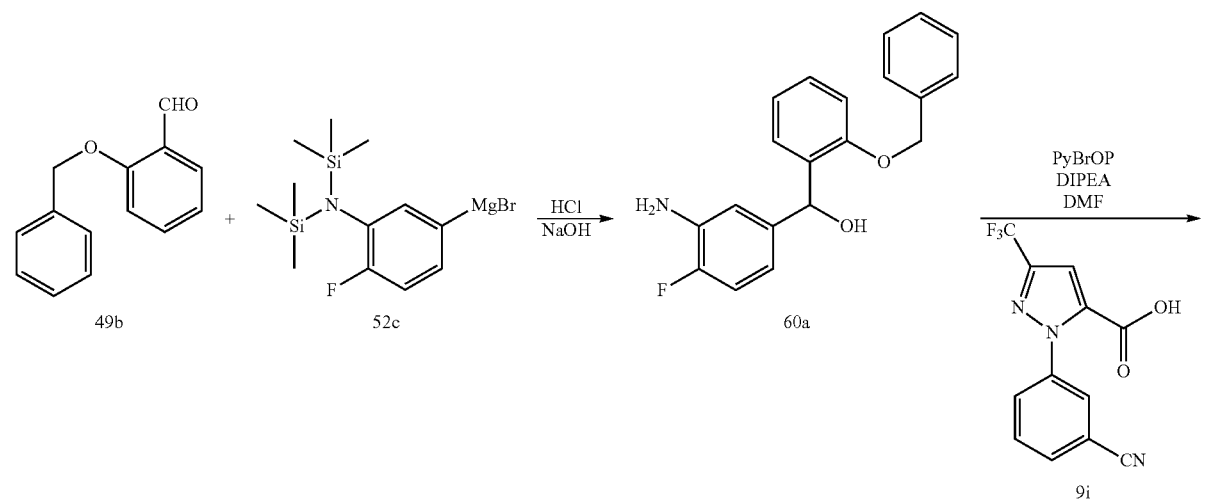

-continued

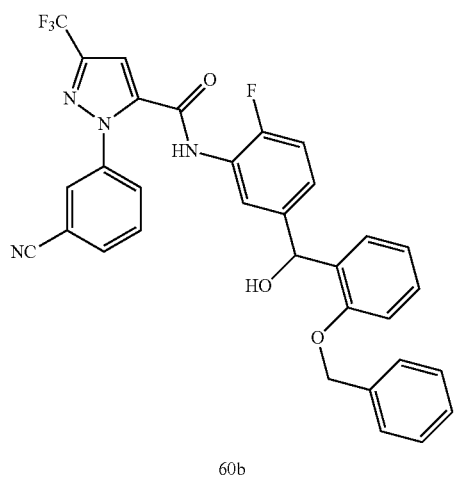
60b

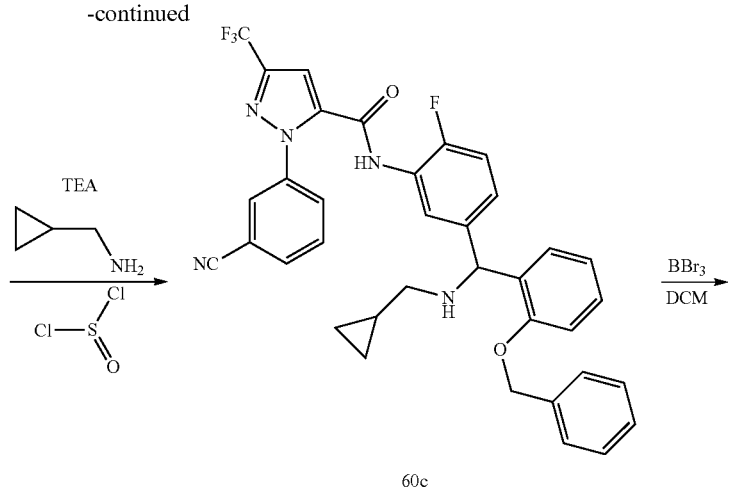
60c

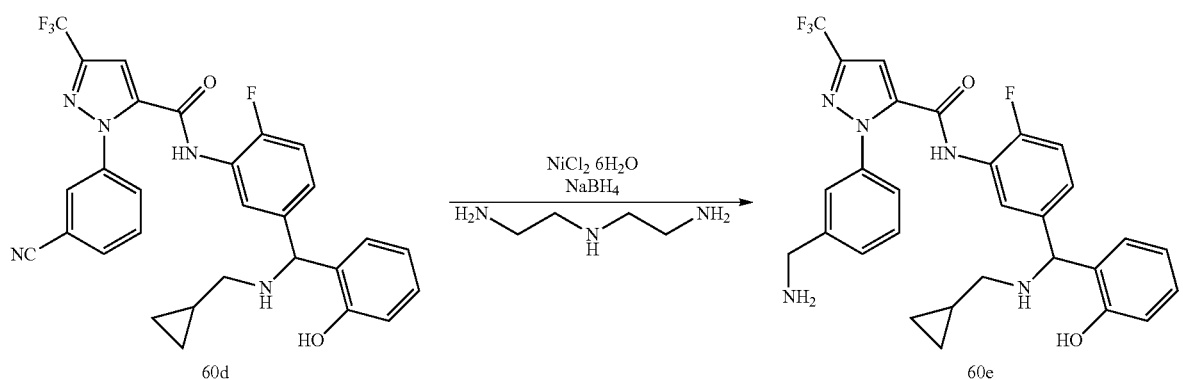
60d → 60e

Preparation of Preparation of 1-(3-(aminomethyl) phenyl)-N-(5-((cyclopropylmethylamino)(2-hydroxyphenyl)methyl)-2-fluorophenyl)-3-(trifluoromethyl)-1H-pyrazole-5-carboxamide (60e)

Step-1: (3-amino-4-fluorophenyl)(2-(benzyloxy)phenyl)methanol (60a)

To a stirred solution of 2-(benzyloxy)benzaldehyde (49b) (31.8 g, 150 mmol) in tetrahydrofuran (150 mL) was added (3-(bis(trimethylsilyl)amino)-4-fluorophenyl)magnesium bromide (52c) (150 mL, 150 mmol) at 0° C. over a period of 30 min. The reaction was stirred for 14 h at room temperature and quenched with 2 N HCl (188 mL, 375 mmol) over a period of 30 min, and stirred for 1 h, TLC analysis (ethyl acetate/hexanes, 3/7, v/v) shows reaction was complete. The reaction mixture was treated with 2 N NaOH (225 mL, 450 mmol) and extracted with ethyl acetate (2×750 mL). The organic layers were combined dried over anhydrous MgSO$_4$, filtered, and evaporated to dryness. The residue was purified by flash column chromatography (silica gel 1 kg, eluting with 0-70% ethyl acetate in hexane) to furnish (3-amino-4-fluorophenyl)(2-(benzyloxy)phenyl) methanol (60a) (19.54 g, 40% yield) as a yellow oil; $^1$H NMR (300 MHz, DMSO-d$_6$) δ 7.48 (dd, J=7.6, 1.7 Hz, 1H), 7.41-7.27 (m, 5H), 7.17 (ddd, J=8.1, 7.2, 1.8 Hz, 1H), 7.04-6.91 (m, 2H), 6.88-6.71 (m, 2H), 6.43 (ddd, J=8.3, 4.5, 2.1 Hz, 1H), 5.90 (d, J=4.2 Hz, 1H), 5.56 (d, J=4.3 Hz, 1H, D$_2$O exchangeable), 5.09 (s, 2H), 5.01 (s, 2H, D$_2$O exchangeable); $^{19}$F NMR (282 MHz, DMSO-d$_6$) δ −137.98; MS (ES+): MS (ES+) 346.2 (M+Na), MS (ES−) 322.1 (M−1).

Step-2: Preparation of N-(5-((2-(benzyloxy)phenyl)(hydroxy)methyl)-2-fluorophenyl)-1-(3-cyanophenyl)-3-(trifluoromethyl)-1H-pyrazole-5-carboxamide (60b)

In a 1 L single-necked flask 1-(3-cyanophenyl)-3-(trifluoromethyl)-1H-pyrazole-5-carboxylic acid (9i) (12.67 g, 45.1 mmol), (3-amino-4-fluorophenyl)(2-(benzyloxy)phenyl) methanol (60a) (12.14 g, 37.5 mmol), bromo-tris-pyrrolidino phosphoniumhexafluorophosphate(PyBrop) (21.00 g, 45.1 mmol) were treated with N,N-dimethylformamide (218 mL, 2816 mmol) and N-ethyl-N-isopropylpropan-2-amine (32.7 mL, 188 mmol) successively in a positive flow of nitrogen at room temperature. The resulting reaction mixture was stirred at room temperature for 16 h under a positive flow of nitrogen atmosphere. The residue was diluted with ethyl acetate (750 mL), and layer was separated with water (2 L), aq. layer was again extracted with ethyl acetate (2×400 mL), combined organics were dried over anhydrous MgSO$_4$, filtered, evaporated to dryness. The residue was then purified by flash column chromatography [silica gel 1 kg, eluting with ethyl acetate in hexanes from 0-100%] to furnish N-(5-((2-(benzyloxy)phenyl)(hydroxy)methyl)-2-fluorophenyl)-1-(3-cyanophenyl)-3-(trifluoromethyl)-1H-pyrazole-5-carboxamide (60b) (15.16 g, 25.8 mmol, 68.8% yield) as a yellow solid; $^1$H NMR (300 MHz, DMSO-d$_6$) δ 10.51 (s, 1H), 8.17-8.09 (m, 1H), 7.99 (dt, J=7.7, 1.3 Hz, 1H), 7.88 (dt, J=8.1, 1.3 Hz, 1H), 7.79-7.66 (m, 2H), 7.56-7.44 (m, 2H), 7.30 (s, 5H), 7.16 (dd, J=7.4, 1.4 Hz, 3H), 7.06-6.92 (m, 2H), 5.98 (d, J=4.3 Hz, 1H), 5.83 (d, J=4.3 Hz, 1H), 5.08 (s, 2H); $^{19}$F NMR (282 MHz, DMSO-d$_6$) δ −60.97, −123.49; MS (ES$^+$): MS (ES+) 609.3 (M+Na); MS (ES+) 585.2 (M−1).

Step-3: Preparation of N-(5-((2-(benzyloxy)phenyl)(cyclopropylmethylamino)methyl)-2-fluorophenyl)-1-(3-cyanophenyl)-3-(trifluoromethyl)-1H-pyrazole-5-carboxamide (60c)

To a solution of N-(5-((2-(benzyloxy)phenyl)(hydroxy)methyl)-2-fluorophenyl)-1-(3-cyanophenyl)-3-(trifluoromethyl)-1H-pyrazole-5-carboxamide (60b) (14.91 g, 25.4 mmol) in dichloromethane (120 mL) at 0° C. was added thionyl chloride (3.71 mL, 50.8 mmol), reaction mixture stirred for for 6 h by maintaining 0° C. TLC analysis shows reaction was incomplete, then added one more eq. of thionyl chloride (3.02 g, 25.4 mmol) at 0° C. and stirred for 1 h. The reaction mixture was quenched with triethylamine (11.35 mL, 81 mmol), and solution was stirred for 30 min at room temperature, and concentrated in vacuum to dryness. The residue was dissolved in cyclopropylmethanamine (22.05 mL, 254 mmol) and acetonitrile (120 mL) and stirred at 80° C. for 16 h, at this time TLC analysis (ethyl acetate/hexanes, 1/1, v/v) shows maximum conversion, reaction mixture was cooled to room temperature, and evaporated to dryness. The residue was purified by flash column chromatography (silica gel 1 kg, eluting with methanol in chloroform from 0-100%) to afford N-(5-((2-(benzyloxy)phenyl)(cyclopropylmethylamino)methyl)-2-fluorophenyl)-1-(3-cyanophenyl)-3-(trifluoromethyl)-1H-pyrazole-5-carboxamide (60c) (9.25 g, 57% yield) as a pale yellow solid. $^1$HNMR (300 MHz, DMSO-d6) δ 10.50 (s, 1H), 8.15-8.10 (m, 1H), 7.99 (dt, J=7.8, 1.3 Hz, 1H), 7.94-7.86 (m, 1H), 7.76-7.67 (m, 2H), 7.56-7.43 (m, 2H), 7.32 (tdd, J=7.4, 5.0, 2.3 Hz, 5H), 7.23-7.14 (m, 3H), 7.05-6.90 (m, 2H), 5.19 (s, 1H), 5.08 (s, 2H), 2.24 (qd, J=12.0, 6.7 Hz, 2H), 0.85 (d, J=11.2 Hz, 1H), 0.32 (dq, J=7.8, 1.7 Hz, 2H), −0.00-−0.05 (m, 2H); MS (ES+) 640.3 (M+1); MS (ES+) 638.3 (M−1).

Step-4: Preparation of 1-(3-cyanophenyl)-N-(5-((cyclopropylmethylamino)(2-hydroxyphenyl)methyl)-2-fluorophenyl)-3-(trifluoromethyl)-1H-pyrazole-5-carboxamide (60d)

To a solution of N-(5-((2-(benzyloxy)phenyl)(cyclopropylmethylamino)methyl)-2-fluorophenyl)-1-(3-cyanophenyl)-3-(trifluoromethyl)-1H-pyrazole-5-carboxamide (60c) (7.59 g, 11.87 mmol) in dichloromethane (150 mL) cooled to −78° C. was added drop-wise under a nitrogen atmosphere tribromoborane (1 M solution in dichloromethane) (13.05 mL, 13.05 mmol). The reaction mixture was allowed to warm to room temperature and stirred at room temperature 15 h. The reaction mixture was treated with methanol (3×100 mL), and co-evaporated, then quenched with water (100 mL) and extracted with chloroform (3×100 mL), combined organic layers were dried over anhydrous MgSO$_4$, filtered, evaporated to dryness. The residue was then purified by flash column chromatography [silica gel 120 g, eluting with methanol in chloroform from 0-50%] to furnish 1-(3-cyanophenyl)-N-(5-(((cyclopropylmethylamino)(2-hydroxyphenyl)methyl)-2-fluorophenyl)-3-(trifluoromethyl)-1H-pyrazole-5-carboxamide (60d) (7.407 g) as a yellow syrup which was taken as such to the next step; MS (ES$^−$): 548.3 (M−1).

Step-5: Preparation of 1-(3-(aminomethyl)phenyl)-N-(5-((cyclopropylmethylamino)(2-hydroxyphenyl)methyl)-2-fluorophenyl)-3-(trifluoromethyl)-1H-pyrazole-5-carboxamide (60e)

To a stirred solution of 1-(3-cyanophenyl)-N-(5-((cyclopropylmethylamino)(2-hydroxyphenyl)methyl)-2-fluorophenyl)-3-(trifluoromethyl)-1H-pyrazole-5-carboxamide (CVR-008-141) (7.35 g, 13.38 mmol) in anhydrous methanol (120 mL), cooled to 0° C., were added and stirred for 10 min, then nickel(II) chloride hexahydrate (2.384 g, 10.03 mmol), sodium borohydride (5.06 g, 134 mmol) was then added in small portions over a period of 4 h. The reaction was exothermic and effervescent. The reaction mixture was stirred for 45 min at 0° C., at this point N1-(2-aminoethyl)ethane-1,2-diamine (14.45 mL, 134 mmol) was added. The mixture was allowed to stir for 1 h more before solvent was evaporated. The residue was treated with water (400 mL), and extracted with chloroform (2×300 mL) combined organic layers were dried over anhydrous MgSO$_4$, filtered, excess solvents were pumped-off under reduced pressure.

The residue was purified by flash column chromatography [(silica gel 120 g, followed by two separate 80 g columns, eluting with methanol/chloroform from 0 to 50%)] to furnish 1-(3-(aminomethyl)phenyl)-N-(5-((cyclopropylmethylamino)(2-hydroxyphenyl)methyl)-2-fluorophenyl)-3-(trifluoromethyl)-1H-pyrazole-5-carboxamide (60e) (0.840 g, 1.517 mmol, 11.35% yield) as a yellow solid; $^1$H NMR (300 MHz, DMSO-d$_6$) δ 10.58 (s, 1H, D$_2$O exchangeable), 7.65-7.55 (m, 2H), 7.51 (s, 1H), 7.47-7.40 (m, 2H), 7.33 (dtt, J=6.8, 4.6, 2.5 Hz, 2H), 7.28-7.13 (m, 1H), 7.03 (ddt, J=8.5, 5.1, 1.7 Hz, 2H), 6.76-6.65 (m, 2H), 5.03 (s, 1H), 3.78 (s, 2H), 2.45-2.37 (m, 1H), 2.25 (dd, J=12.2, 7.0 Hz, 1H), 0.97-0.83 (m, 1H), 0.42-0.38 (m, 2H), 0.07 (d, J=5.1 Hz, 2H); $^{19}$F NMR (282 MHz, DMSO-d$_6$) δ −60.75, −123.06; MS (ES+) 554.3 (M+1), 576.2 (M+Na), 552.2 (M−1), 588.2 (M+Cl).

Scheme 61
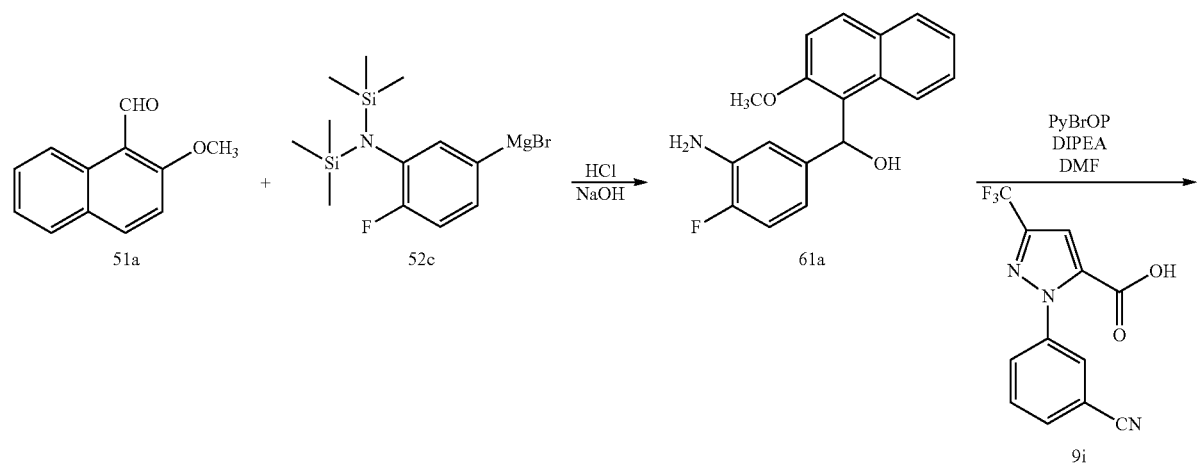
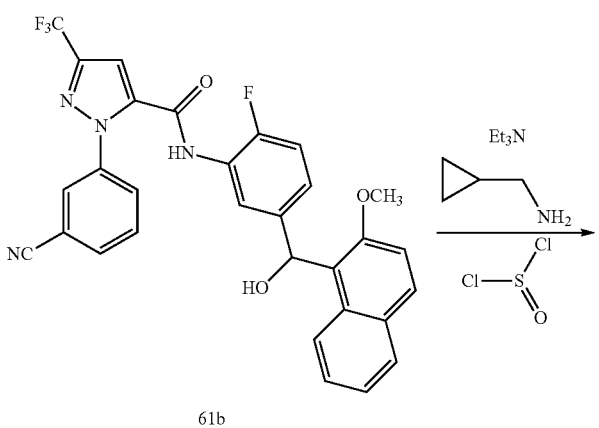
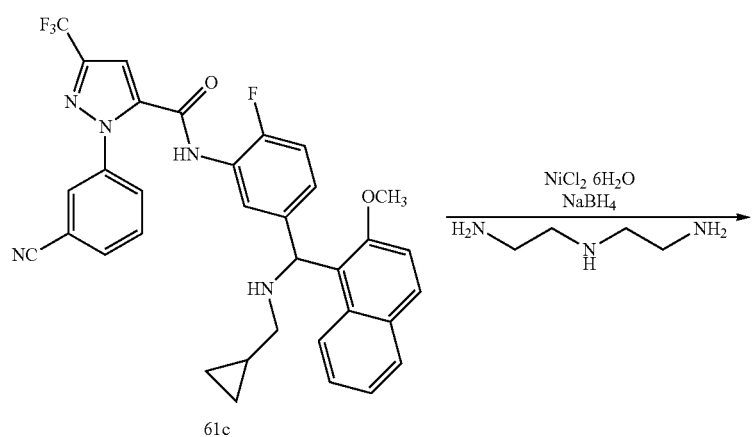

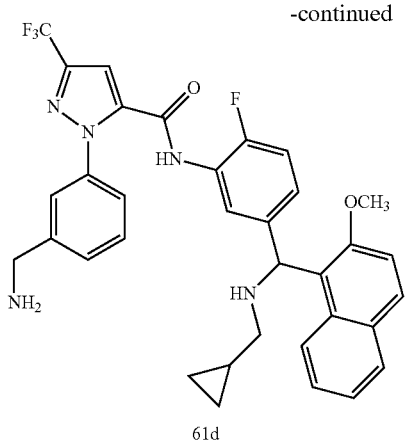 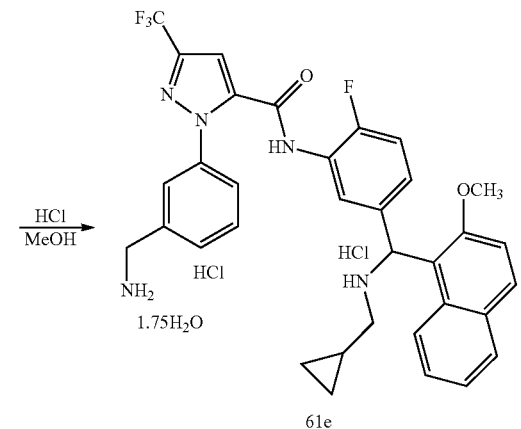

61d → 61e (HCl / MeOH)

Preparation of 1-(3-(aminomethyl)phenyl)-N-(5-((cyclopropylmethylamino)(2-methoxynaphthalen-1-yl)methyl)-2-fluorophenyl)-3-(trifluoromethyl)-1H-pyrazole-5-carboxamide dihydrochloride (61e)

Step-1: Preparation of (3-amino-4-fluorophenyl)(2-methoxynaphthalen-1-yl)methanol (61a)

To a stirred solution of 2-methoxy-1-naphthaldehyde (51a) (24.21 g, 130 mmol) in tetrahydrofuran (100 mL) was added (3-(bis(trimethylsilyl)amino)-4-fluorophenyl)magnesium bromide (52c) (130 mL, 130 mmol) at 0° C. The reaction was stirred for 20 h at room temperature and quenched by adding hydrogen chloride (2N) (163 mL, 325 mmol), stirred for 1 h, TLC analysis (ethyl acetate/hexanes, 3/7, v/v) shows reaction was complete. The reaction mixture was treated with sodium hydroxide (2N) (195 mL, 390 mmol) and extracted with ethyl acetate (2×750 mL). The organic layers were combined dried over anhydrous MgSO$_4$, filtered, and evaporated to dryness. The crude residue was purified by flash column chromatography (silica gel 1.3 kg, eluting with 0-70% ethyl acetate in hexane) to furnish (3-amino-4-fluorophenyl)(2-methoxynaphthalen-1-yl)methanol (61a) (24.84 g, 84 mmol, 64.3% yield) as a yellow solid; $^1$H NMR (300 MHz, DMSO-d$_6$) δ 8.28-8.10 (m, 1H), 7.87 (d, J=9.0 Hz, 1H), 7.84-7.72 (m, 1H), 7.48 (d, J=9.1 Hz, 1H), 7.35-7.17 (m, 2H), 6.91-6.70 (m, 2H), 6.66-6.57 (m, 1H), 6.46 (dddd, J=8.2, 4.6, 2.2, 1.0 Hz, 1H), 5.91 (d, J=4.6 Hz, 1H, D$_2$O exchangeable), 4.98 (s, 2H, D$_2$O exchangeable), 3.96 (s, 3H); $^{19}$F NMR (282 MHz, DMSO-d$_6$) δ −139.08; MS (ES$^+$): MS (ES+) 320.2 (M+Na), MS (ES−) 296.0 (M−1).

Step-2: Preparation of 1-(3-cyanophenyl)-N-(2-fluoro-5-(hydroxy(2-methoxynaphthalen-1-yl)methyl)phenyl)-3-(trifluoromethyl)-1H-pyrazole-5-carboxamide (61b)

A 1 L single-necked flask was charged with 1-(3-cyanophenyl)-3-(trifluoromethyl)-1H-pyrazole-5-carboxylic acid (9i) (16.04 g, 57.0 mmol), (3-amino-4-fluorophenyl)(2-methoxynaphthalen-1-yl)methanol (61a) (14.13 g, 47.5 mmol), bromo-tris-pyrrolidino phosphoniumhexafluorophosphate(PyBrop) (26.6 g, 57.0 mmol) and were treated with N,N-dimethylformamide (276 mL, 3564 mmol) and N-ethyl-N-isopropylpropan-2-amine (41.4 mL, 238 mmol) successively in a positive flow of nitrogen at room temperature. The resulting reaction mixture was stirred at room temperature for 16 h under a positive flow of nitrogen atmosphere. The residue was diluted with ethyl acetate (750 mL), and layer was separated with water (2 L), aq. layer was again extracted with ethyl acetate (500 mL), combined organics were dried over anhydrous MgSO$_4$, filtered, evaporated to dryness. The residue was then purified by flash column chromatography [silica gel 800 g, eluting with ethyl acetate in hexanes from 0-100%] to furnish 1-(3-cyanophenyl)-N-(2-fluoro-5-(hydroxy(2-methoxynaphthalen-1-yl)methyl)phenyl)-3-(trifluoromethyl)-1H-pyrazole-5-carboxamide (61b) (11.819 g, 44% yield) as a yellow solid; $^1$H NMR (300 MHz, DMSO-d$_6$) δ 10.49 (s, 1H, D$_2$O exchangeable), 8.20-8.08 (m, 2H), 8.00 (dt, J=7.7, 1.3 Hz, 1H), 7.95-7.85 (m, 2H), 7.85-7.78 (m, 1H), 7.75-7.65 (m, 2H), 7.56-7.43 (m, 2H), 7.30-7.13 (m, 4H), 6.72 (d, J=4.6 Hz, 1H), 6.19 (d, J=4.6 Hz, 1H, D$_2$O exchangeable), 3.97 (s, 3H); $^{19}$F NMR (282 MHz, DMSO-d$_6$) δ −60.98, −124.01; IR (KBr, cm$^{-1}$): 2235 cm$^{-1}$ (—CN stretching); MS (ES$^+$): MS (ES+) 583.2 (M+Na), MS (ES−) 559.2 (M−1).

Step-3: Preparation of 1-(3-cyanophenyl)-N-(5-((cyclopropylmethylamino)(2-methoxynaphthalen-1-yl)methyl)-2-fluorophenyl)-3-(trifluoromethyl)-1H-pyrazole-5-carboxamide (61c)

To a solution of 1-(3-cyanophenyl)-N-(2-fluoro-5-(hydroxy(2-methoxynaphthalen-1-yl)methyl)phenyl)-3-(trifluoromethyl)-1H-pyrazole-5-carboxamide (61b) (11.61 g, 20.71 mmol) in dichloromethane (120 mL) at 0° C. was added thionyl chloride (3.02 mL, 41.4 mmol), reaction mixture stirred for for 4.5 h from 0° C. to room temperature. The reaction mixture was quenched with triethylamine (9.25 mL, 66.3 mmol), and solution was stirred for 30 min at room temperature, and concentrated in vacuum to dryness. The residue was dissolved in cyclopropylmethanamine (14.37 mL, 166 mmol) and acetonitrile (120 mL) and stirred at 80° C. for 16 h, at this time TLC analysis (ethyl acetate/hexanes, 1/1, v/v) shows maximum conversion, reaction mixture was cooled to room temperature, and evaporated to dryness. The residue was purified by flash column chromatography (two separate silica gel columns, size 120 g, eluting with CMA80 in chloroform from 0-100%) to afford 1-(3-cyanophenyl)-N-(5-((cyclopropylmethylamino)(2-methoxynaphthalen-1-yl)methyl)-2-fluorophenyl)-3-(trifluoromethyl)-1H-pyrazole-5-carboxamide (61c) (10.828 g, 85% yield) as a pale yellow solid; $^1$H NMR (300 MHz, DMSO-d$_6$) δ 10.49 (s, 1H, D₂O exchangeable), 8.29 (d, J=8.5 Hz, 1H), 8.16-8.09 (m, 1H), 7.99 (dt, J=7.7, 1.3 Hz, 1H), 7.94-7.81 (m, 3H), 7.76-7.65 (m, 2H), 7.53 (d, J=7.4 Hz, 1H), 7.47 (d, J=9.1 Hz, 1H), 7.34 (dt, J=14.5, 7.5 Hz, 2H), 7.27-7.10 (m, 2H), 5.87 (s, 1H), 3.85 (s, 3H), 2.12 (s, 1H), 0.90 (s, 1H), 0.45-0.24 (m, 2H), 0.06--0.14 (m, 2H); $^{19}$F NMR (282 MHz, DMSO-d₆) δ −60.97, −123.98; IR (KBr, cm⁻¹): 2234 cm⁻¹ (—CN stretching); MS (ES⁺): MS (ES+) 614.3 (M+1), MS (ES−) 612.3 (M−1).

Step-4: Preparation of 1-(3-(aminomethyl)phenyl)-N-(5-((cyclopropylmethylamino)(2-methoxynaphthalen-1-yl)methyl)-2-fluorophenyl)-3-(trifluoromethyl)-1H-pyrazole-5-carboxamide (61d)

To a stirred solution of 1-(3-cyanophenyl)-N-(5-((cyclopropylmethylamino)(2-methoxynaphthalen-1-yl)methyl)-2-fluorophenyl)-3-(trifluoromethyl)-1H-pyrazole-5-carboxamide (61c) (9.61 g, 15.66 mmol) in anhydrous methanol (180 mL), cooled to 0° C., were added nickel(II) chloride hexahydrate (0.931 g, 3.92 mmol), sodium borohydride (4.74 g, 125 mmol) was then added in small portions over a period of 1 h. The reaction was exothermic and effervescent. The reaction mixture was stirred for 3 h at 0° C., TLC analysis (methanol/chloroform, 9/1) shows partial (approx. 10-20%), again added nickel(II) chloride hexahydrate (0.931 g, 3.92 mmol), and NaBH₄ (1.5 g) was added in small portions over a period of 20 min, and stirred the solution for 30 min at this point N1-(2-aminoethyl)ethane-1,2-diamine (16.92 mL, 157 mmol) was added. The mixture was allowed to stir for 4 h more before solvent was evaporated. The residue was treated with water (200 mL), and extracted with chloroform (2×300 mL), combined organic layers were dried over anhydrous MgSO₄, and filtered, excess solvents were pumped-off under reduced pressure. The residue was purified by flash column chromatography [(silica gel, two separate 120 g (slurry was sliced to half), eluting with methanol/chloroform from 0 to 40%)] to furnish 1-(3-(aminomethyl)phenyl)-N-(5-((cyclopropylmethylamino)(2-methoxynaphthalen-1-yl)methyl)-2-fluorophenyl)-3-(trifluoromethyl)-1H-pyrazole-5-carboxamide (61d) (3.28 g, 34% yield) as a colorless solid; ¹H NMR (300 MHz, DMSO-d₆) δ 10.50 (s, 1H, D₂O exchangeable), 8.29 (d, J=8.4 Hz, 1H), 7.87 (dd, J=11.5, 8.1 Hz, 2H), 7.55 (t, J=9.6 Hz, 3H), 7.49 (s, 1H), 7.47-7.41 (m, 2H), 7.41-7.29 (m, 3H), 7.16 (dt, J=18.7, 9.7 Hz, 2H), 5.86 (s, 1H), 3.84 (s, 3H), 3.80 (s, 2H), 2.11 (m, 1H), 2.08 (dd, J=11.8, 7.3 Hz, 1H), 1.02-0.79 (m, 1H), 0.34 (dq, J=8.1, 1.7 Hz, 2H), 0.10--0.24 (m, 2H); ¹⁹F NMR (282 MHz, DMSO-d₆) δ −60.74, −124.35; MS (ES⁺): MS (ES+) 618.3 (M+1), 652.3 (M+Cl).

Step-5: Preparation of 1-(3-(aminomethyl)phenyl)-N-(5-((cyclopropylmethylamino)(2-methoxynaphthalen-1-yl)methyl)-2-fluorophenyl)-3-(trifluoromethyl)-1H-pyrazole-5-carboxamide dihydrochloride (61e)

To a stirred solution of 1-(3-(aminomethyl)phenyl)-N-(5-((cyclopropylmethylamino)(2-methoxynaphthalen-1-yl)methyl)-2-fluorophenyl)-3-(trifluoromethyl)-1H-pyrazole-5-carboxamide (61d) (0.250 g, 0.405 mmol) in anhydrous methanol (15 mL), was treated with 2 N HCl (in methanol) (1.012 mL, 2.024 mmol) and stirred for 10 min, and evaporated to dryness to furnish 1-(3-(aminomethyl)phenyl)-N-(5-((cyclopropylmethylamino)(2-methoxynaphthalen-1-yl)methyl)-2-fluorophenyl)-3-(trifluoromethyl)-1H-pyrazole-5-carboxamide dihydrochloride (61e) (253 mg, 91% yield) as a yellow solid; ¹H NMR (300 MHz, DMSO-d₆) δ 10.78 (s, 1H), 9.91 (s, 1H), 9.24 (s, 1H), 8.51 (s, 3H), 8.24 (d, J=8.7 Hz, 1H), 8.08 (d, J=9.2 Hz, 1H), 7.95 (dd, J=8.3, 1.4 Hz, 1H), 7.89 (dd, J=7.4, 2.3 Hz, 1H), 7.77-7.54 (m, 5H), 7.53-7.31 (m, 4H), 6.39 (t, J=6.4 Hz, 1H), 4.11 (q, J=5.9 Hz, 2H), 4.03 (s, 3H), 2.98-2.78 (m, 1H), 2.72 (d, J=7.8 Hz, 1H), 1.20-1.01 (m, 1H), 0.51 (ddt, J=16.9, 9.3, 4.7 Hz, 2H), 0.22 (ddt, J=17.7, 9.0, 4.8 Hz, 2H); ¹H NMR (300 MHz, DMSO-d₆ D₂O) δ 8.20 (d, J=8.8 Hz, 1H), 8.09 (d, J=9.3 Hz, 1H), 7.96 (dd, J=8.3, 1.4 Hz, 1H), 7.88 (dd, J=7.3, 2.5 Hz, 1H), 7.75-7.31 (m, 10H), 6.35 (s, 1H), 4.11 (s, 2H), 4.03 (s, 3H), 2.89 (dd, J=12.9, 6.9 Hz, 1H), 2.72 (dd, J=12.9, 7.7 Hz, 1H), 1.08 (d, J=8.3 Hz, 1H), 0.54 (dd, J=13.1, 6.3 Hz, 2H), 0.23 (ddd, J=19.1, 9.3, 5.0 Hz, 2H); ¹⁹F NMR (282 MHz, DMSO-d₆) δ −60.79, −120.01; MS (ES⁺): MS (ES+) 618.3 (M+1), 616.3 (M−1), 652.3 (M+Cl); Analysis calculated for: C₃₄H₃₁F₄N₅O₂.1.75H₂O.2HCl: C, 56.55; H, 5.09; Cl, 9.82; N, 9.70; Found: C, 56.64; H, 5.06; Cl, 9.62; N, 9.56.

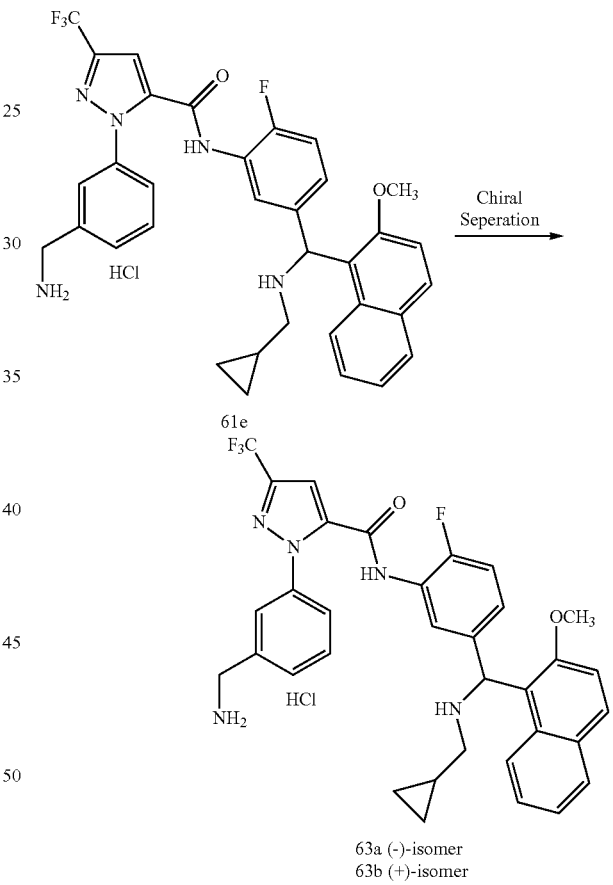

Scheme 63

61e 63a (−)-isomer
63b (+)-isomer

Preparation of (−)-1-(3-(aminomethyl)phenyl)-N-(5-((cyclopropylmethylamino)(2-methoxynaphthalen-1-yl)methyl)-2-fluorophenyl)-3-(trifluoromethyl)-1H-pyrazole-5-carboxamide (63a), (+)-1-(3-(aminomethyl)phenyl)-N-(5-((cyclopropylmethylamino)(2-methoxynaphthalen-1-yl)methyl)-2-fluorophenyl)-3-(trifluoromethyl)-1H-pyrazole-5-carboxamide (63b)

Racemic 1-(3-(aminomethyl)phenyl)-N-(5-((cyclopropylmethylamino)(2-methoxynaphthalen-1-yl)methyl)-2-fluorophenyl)-3-(trifluoromethyl)-1H-pyrazole-5-carboxamide (61e) (2.0 g) was separated using Preparative SFC method. Column: 2.1×25 cm ChiralPak IC SFC from Chiral Technologies; $CO_2$ Co-solvent (Solvent B) Acetonitrile:Isopropanol (4:1) with 1% Isopropylamine; Isocratic Method: 40% Co-solvent at 80 mL/min; System pressure 100 bar; Column temperature 25° C.; sample diluents methanol, to furnish:

1. Peak-1 corresponding to (−)-1-(3-(aminomethyl)phenyl)-N-(5-((cyclopropylmethylamino)(2-methoxynaphthalen-1-yl)methyl)-2-fluorophenyl)-3-(trifluoromethyl)-1H-pyrazole-5-carboxamide (63a) (136 mg, >95% ee); This product (112 mg) was purified by flash column chromatography (silica gel 12 kg, eluting with 0-60% methanol in chloroform) to furnish (−)-1-(3-(aminomethyl)phenyl)-N-(5-((cyclopropylmethylamino)(2-methoxynaphthalen-1-yl)methyl)-2-fluorophenyl)-3-(trifluoromethyl)-1H-pyrazole-5-carboxamide (63a) (0.069 g, 50.7%, >95% ee) as a white solid; $^1$H NMR (300 MHz, DMSO-$d_6$) δ 10.48 (s, 1H, $D_2O$ exchangeable), 8.29 (d, J=8.4 Hz, 1H), 7.87 (dd, J=11.9, 8.5 Hz, 2H), 7.61-7.53 (m, 2H), 7.50 (d, J=5.9 Hz, 1H), 7.47-7.28 (m, 5H), 7.19 (s, 2H), 7.17-7.09 (m, 1H), 5.86 (s, 1H), 3.84 (s, 3H), 3.78 (s, 2H), 2.13 (d, J=8.0 Hz, 1H), 0.89 (d, J=8.5 Hz, 1H), 0.34 (dt, J=8.1, 1.9 Hz, 2H), −0.11 (dd, J=9.7, 4.6 Hz, 2H); $^{19}$F NMR (282 MHz, DMSO-$d_6$) δ −60.73, −124.39; MS (ES+) 618.3 (M+1), 652.3 (M+Cl). Optical rotation: [α]D=(−) 88.88 [$CH_3OH$, 0.75]; Free base of (−)-1-(3-(aminomethyl)phenyl)-N-(5-((cyclopropylmethylamino)(2-methoxynaphthalen-1-yl)methyl)-2-fluorophenyl)-3-(trifluoromethyl)-1H-pyrazole-5-carboxamide dihydrochloride (63a) (69 mg) was dissolved in methanol (15 mL) and added 2 N HCl (0.28 mL, 5 eq.) and stirred at room temperature for 10 min. The solution was evaporated to dryness to afford (−)-1-(3-(aminomethyl)phenyl)-N-(5-((cyclopropylmethylamino)(2-methoxynaphthalen-1-yl)methyl)-2-fluorophenyl)-3-(trifluoromethyl)-1H-pyrazole-5-carboxamide (63a) (0.069 g) hydrochloride salt as an off-white solid; $^1$H NMR (300 MHz, DMSO-$d_6$) δ 10.77 (s, 1H, $D_2O$ exchangeable), 9.89 (s, 1H, $D_2O$ exchangeable), 9.22 (s, 1H, $D_2O$ exchangeable), 8.49 (s, 3H, $D_2O$ exchangeable), 8.24 (d, J=8.7 Hz, 1H), 8.08 (d, J=9.1 Hz, 1H), 7.95 (dd, J=8.3, 1.4 Hz, 1H), 7.89 (dd, J=7.5, 2.3 Hz, 1H), 7.75-7.53 (m, 7H), 7.53-7.32 (m, 4H), 6.37 (d, J=7.0 Hz, 1H), 4.11 (q, J=5.9 Hz, 2H), 4.03 (s, 3H), 2.88 (d, J=11.9 Hz, 1H), 2.72 (d, J=9.6 Hz, 1H), 1.11 (s, 1H), 0.63-0.39 (m, 2H), 0.23 (ddq, J=17.8, 9.4, 4.7 Hz, 2H); $^{19}$F NMR (282 MHz, DMSO-$d_6$) δ −60.81, −120.03; MS (ES$^+$): MS (ES+) 618.3 (M+1), MS (ES−) 652.2 (M+Cl); Analysis calculated for $C_{34}H_{31}F_4N_5O_2\cdot2H_2O\cdot2HCl$: C, 56.20; H, 5.13; Cl, 9.76; N, 9.64; Found: C, 56.64; H, 5.14; Cl, 9.35; N, 9.59.

2. Peak-2 corresponding to (+)-1-(3-(aminomethyl)phenyl)-N-(5-((cyclopropylmethylamino)(2-methoxynaphthalen-1-yl)methyl)-2-fluorophenyl)-3-(trifluoromethyl)-1H-pyrazole-5-carboxamide (63b) (107 mg, >95% ee); This product (107 mg) was purified by flash column chromatography (silica gel 12 g, eluting with 0-60% methanol in chloroform) to furnish 83 mg of BCX-7362 free-base. $^1$H NMR (300 MHz, DMSO-$d_6$) δ 10.49 (s, 1H, $D_2O$ exchangeable), 8.29 (d, J=8.5 Hz, 1H), 7.96-7.79 (m, 2H), 7.61-7.48 (m, 4H), 7.46 (s, 1H), 7.44-7.36 (m, 2H), 7.35-7.29 (m, 2H), 7.24-7.08 (m, 2H), 5.86 (s, 1H), 3.84 (s, 3H), 3.79 (s, 2H), 2.19-2.04 (m, 1H), 0.89 (q, J=6.7 Hz, 1H), 0.34 (dt, J=8.0, 2.0 Hz, 2H), −0.11 (td, J=8.8, 7.6, 4.2 Hz, 2H); $^{19}$F NMR (282 MHz, DMSO-$d_6$) δ −60.74, −124.37; MS (ES+) 618.3 (M+1), 616.2 (M−1), 652.3 (M+Cl); Optical rotation: [α]D=(+) 103.11 [$CH_3OH$, 0.9]; To a solution of free base of (+)-1-(3-(aminomethyl)phenyl)-N-(5-((cyclopropylmethylamino)(2-methoxynaphthalen-1-yl)methyl)-2-fluorophenyl)-3-(trifluoromethyl)-1H-pyrazole-5-carboxamide (63b) (63 mgs) in methanol (15 mL) was added hydrogen chloride (0.336 mL, 0.672 mmol) and stirred at room temperature for 10 min. the solution was evaporated to dryness to afford (+)-1-(3-(aminomethyl)phenyl)-N-(5-((cyclopropylmethylamino)(2-methoxynaphthalen-1-yl)methyl)-2-fluorophenyl)-3-(trifluoromethyl)-1H-pyrazole-5-carboxamide (63b) hydrochloride salt (49 mgs) as an off-white solid with HCl salt. $^1$H NMR (300 MHz, DMSO-$d_6$) δ 10.74 (s, 1H, $D_2O$ exchangeable), 9.81 (s, 1H, $D_2O$ exchangeable), 9.21 (s, 1H, $D_2O$ exchangeable), 8.43 (s, 3H, $D_2O$ exchangeable), 8.24 (d, J=8.7 Hz, 1H), 8.13-8.05 (m, 1H), 7.95 (d, J=8.1 Hz, 1H), 7.88 (d, J=7.0 Hz, 1H), 7.75-7.54 (m, 5H), 7.53-7.32 (m, 3H), 6.39 (s, 1H), 4.11 (d, J=5.7 Hz, 2H), 4.03 (d, J=1.5 Hz, 3H), 2.87 (s, 1H), 2.72 (s, 1H), 1.10 (s, 1H), 0.50 (d, J=9.4 Hz, 2H), 0.22 (s, 2H); $^{19}$F NMR (282 MHz, DMSO-$d_6$) δ −60.82, −120.05; MS (ES$^+$): MS (ES+) 618.3 (M+1), MS (ES−) 652.2 (M+Cl). Analysis calculated for $C_{34}H_{31}F_4N_5O_2\cdot2H_2O\cdot2HCl$: C, 56.20; H, 5.13; Cl, 9.76; N, 9.64; Found: C, 56.67; H, 5.18; Cl, 9.34; N, 9.58.

The following analytical method was used to check chiral purity of compounds 63a and 63b. Analytical SFC Method

| | |
|---|---|
| Column | 4.6 × 100 mm ChiralPak IC SFC from chiral technologies |
| $CO_2$ Co-solvent (Solvent B) | Acetonitrile:Isopropanol (4:1) with .1% Isopropylamine |
| Isocratic Method | 35% Co-solvent at 4 mL/min |
| System Pressure | 150 bar |
| Column Temperature | 40° C. |
| Sample Diluent | Methanol |

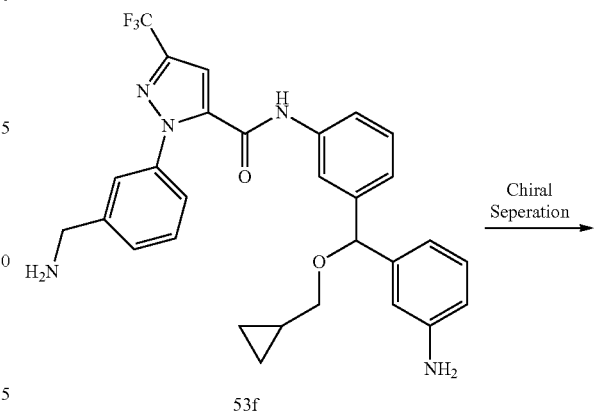

Scheme 64

Chiral Seperation

53f

-continued

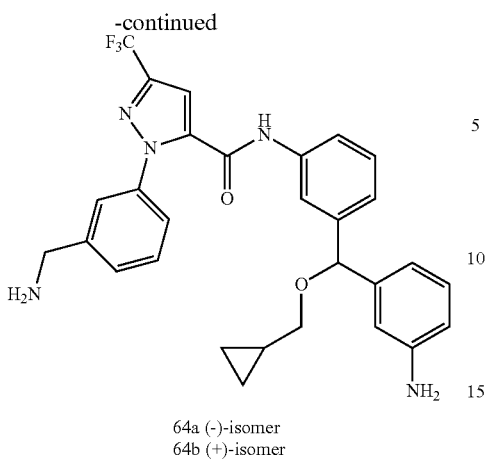

64a (−)-isomer
64b (+)-isomer

Preparation of (−)-1-(3-(aminomethyl)phenyl)-N-(3-((3-aminophenyl)(cyclopropyl-methoxy)methyl) phenyl)-3-(trifluoromethyl)-1H-pyrazole-5-carboxamide (64a) and (+)-1-(3-(aminomethyl)phenyl)-N-(3-((3-aminophenyl)(cyclopropyl-methoxy)methyl) phenyl)-3-(trifluoromethyl)-1H-pyrazole-5-carboxamide (64b)

Racemic 1-(3-(aminomethyl)phenyl)-N-(3-((3-aminophenyl)(cyclopropyl-methoxy)methyl)phenyl)-3-(trifluoromethyl)-1H-pyrazole-5-carboxamide (53f) (660 mg) was purified by preparative chiral HPLC using CHIRALPAK AD-H, 5μ, 4.6×250 mm, flow rate 1 mL/min, Solvent: 80% Hexane/20% EtOH/0.1% DEA, UV=320 nM to furnish 1. Peak-1 corresponding to (−)-1-(3-(aminomethyl)phenyl)-N-(3-((3-aminophenyl)(cyclopropyl-methoxy) methyl)phenyl)-3-(trifluoromethyl)-1H-pyrazole-5-carboxamide (64a) [0.304 g, Rt=7.401 min, 99.6953% for peak-1 (64a), Rt=9.479 0.3047% for peak-2 (64b) 99.4% ee]. This product was purified by flash column chromatography (silica gel 25 g, eluting 0-25% methanol in chloroform for 13 mins) to furnish (−)-1-(3-(aminomethyl)phenyl)-N-(3-((3-aminophenyl)(cyclopropyl-methoxy)methyl)phenyl)-3-(trifluoromethyl)-1H-pyrazole-5-carboxamide (64a) (0.270 g) as a white solid. Optical rotation −6.30 (MeOH, 1.46); $^1$H NMR (300 MHz, DMSO-$d_6$) δ 10.72 (s, 1H), 7.61-7.52 (m, 4H), 7.48-7.40 (m, 2H), 7.33 (dt, J=6.4, 2.5 Hz, 1H), 7.27 (t, J=7.8 Hz, 1H), 7.09 (dd, J=7.6, 1.6 Hz, 1H), 6.93 (t, J=7.7 Hz, 1H), 6.53 (t, J=1.9 Hz, 1H), 6.50-6.44 (m, 1H), 6.40 (ddd, J=7.9, 2.3, 1.0 Hz, 1H), 5.23 (s, 1H), 5.06 (s, 2H), 3.80 (s, 2H), 3.20 (dd, J=6.8, 1.5 Hz, 2H), 1.05-0.98 (m, 1H), 0.51-0.41 (m, 2H), 0.19-0.10 (m, 2H); $^{19}$F NMR (282 MHz, DMSO-$d_6$) δ −60.71; MS (ES+) 536.3 (M+1); (ES−) 570.3 (M+Cl). Free base (−)-1-(3-(aminomethyl)phenyl)-N-(3-((3-aminophenyl)(cyclopropyl-methoxy)methyl)phenyl)-3-(trifluoromethyl)-1H-pyrazole-5-carboxamide (64a) was dissolved in methanol and added (2.5 mL) of 2 N HCl in methanol. The mixture was concentrated in vacuum to dryness to furnish (−)-1-(3-(aminomethyl)phenyl)-N-(3-((3-aminophenyl)(cyclopropyl-methoxy)methyl) phenyl)-3-(trifluoromethyl)-1H-pyrazole-5-carboxamide (64a) (270 mg) as a hydrochloride salt; $^1$H NMR (300 MHz, DMSO-$d_6$) δ 10.85 (s, 1H), 9.80 (s, 3H), 8.46 (s, 3H), 7.74-7.57 (m, 6H), 7.56-7.50 (m, 2H), 7.42-7.22 (m, 4H), 7.17-7.11 (m, 2H), 5.48 (s, 1H), 4.19-4.00 (m, 2H), 3.24 (d, J=6.7 Hz, 2H), 1.15-1.00 (m, 1H), 0.57-0.40 (m, 2H), 0.17 (ddd, J=5.7, 4.7, 3.6 Hz, 2H); $^1$H NMR (300 MHz, DMSO-$d_6$/$D_2$O) δ 10.84 (s, 1H), 7.73-7.65 (m, 3H), 7.64-7.49 (m, 4H), 7.45-7.26 (m, 4H), 7.15 (dd, J=7.9, 5.2 Hz, 2H), 5.49 (s, 1H), 4.13 (s, 2H), 3.25 (d, J=6.8 Hz, 2H), 1.14-0.95 (m, 1H), 0.58-0.38 (m, 2H), 0.29-0.05 (m, 2H); 19F NMR (282 MHz, DMSO) δ −60.77; MS (ES+) 536.3 (M+1); (ES−) 534.3 (M−1), 570.3 (M+Cl); Chiral purity checked by chiral HPLC using AD-H column; isocratic method 85/15/0.1 (Hexane/ethanol/TEA) 0.5 mL/min, UV 260 nM, 40 mins run time, Temp 5° C.) [Rt=20.22 (100% peak-1 for 64a) Rt=27.323 (0%, peak-2 for 64b, >99% ee); Analysis calculated for $C_{29}H_{28}F_3N_5O_2$.2.1HCl.$H_2$O: C, 55.27; H, 5.13; Cl, 11.81; N, 11.11; Found: C, 55.18; H, 5.20; Cl, 11.74; N, 10.93.

2. Peak-2 corresponding to (+)-1-(3-(aminomethyl)phenyl)-N-(3-((3-aminophenyl)(cyclopropyl-methoxy) methyl)phenyl)-3-(trifluoromethyl)-1H-pyrazole-5-carboxamide (64b) (0.308 gm) was purified by flash column chromatography (silica gel 25 g, eluting 0-30% MeOH in chloroform for 25 min) to afford to (+)-1-(3-(aminomethyl)phenyl)-N-(3-((3-aminophenyl)(cyclopropyl-methoxy)methyl)phenyl)-3-(trifluoromethyl)-1H-pyrazole-5-carboxamide (64b) (0.251 g, 92.67% ee) as free-base Optical rotation: [α]$_D$=(+) 6.66 [CH$_3$OH, 1.38]. $^1$H NMR (300 MHz, DMSO-$d_6$) δ 10.72 (s, 1H, $D_2$O exchangeable), 7.56 (dd, J=11.1, 7.1 Hz, 4H), 7.47-7.39 (m, 2H), 7.35-7.22 (m, 2H), 7.09 (d, J=7.7 Hz, 1H), 6.93 (t, J=7.7 Hz, 1H), 6.58-6.37 (m, 3H), 5.23 (s, 1H), 5.06 (s, 2H), 3.77 (s, 2H), 3.20 (dd, J=6.8, 1.5 Hz, 2H), 1.04 (s, 1H), 0.61-0.30 (m, 2H), 0.23-0.09 (m, 2H); $^{19}$F NMR (282 MHz, DMSO-$d_6$) δ −60.70. MS (ES+) 536.3 (M+1), 534.3 (M−1). To a solution of free base of (+)-1-(3-(aminomethyl)phenyl)-N-(3-((3-aminophenyl)(cyclopropyl-methoxy) methyl)phenyl)-3-(trifluoromethyl)-1H-pyrazole-5-carboxamide (64b) (245 mg) in methanol (8 mL) was added 2 N HCl (in methanol, 2.3 mL, 10 eq.) and stirred at room temperature for 30 min. The solution was evaporated to dryness to afford to (+)-1-(3-(aminomethyl)phenyl)-N-(3-((3-aminophenyl)(cyclopropyl-methoxy)methyl)phenyl)-3-(trifluoromethyl)-1H-pyrazole-5-carboxamide (64b) (239 mg, 98%) hydrochloride salt as an off-white solid; $^1$H NMR (300 MHz, DMSO-$d_6$) δ 10.84 (s, 1H, $D_2$O exchangeable), 9.66 (s, 2H, $D_2$O exchangeable), 8.43 (s, 4H, $D_2$O exchangeable), 7.75-7.48 (m, 8H), 7.35 (dt, J=19.9, 7.8 Hz, 2H), 7.24 (s, 2H), 7.13 (d, J=7.7 Hz, 3H), 5.48 (s, 1H), 4.12 (s, 2H), 3.24 (d, J=6.8 Hz, 2H), 1.16-0.98 (m, 1H), 0.59-0.36 (m, 2H), 0.17 (h, J=3.8 Hz, 2H); $^1$H NMR (300 MHz, DMSO-$d_6$ $D_2$O) δ 7.71 (d, J=1.9 Hz, 1H), 7.68 (t, J=2.0 Hz, 1H), 7.65 (s, 1H), 7.61-7.55 (m, 3H), 7.52 (td, J=5.2, 2.5 Hz, 1H), 7.45-7.23 (m, 4H), 7.14 (dd, J=6.9, 3.0 Hz, 2H), 5.48 (s, 1H), 4.13 (s, 2H), 3.25 (d, J=6.8 Hz, 2H), 1.17-0.97 (m, 1H), 0.61-0.36 (m, 2H), 0.27-0.05 (m, 2H); $^{19}$F NMR (282 MHz, DMSO-$d_6$) δ −60.77; MS (ES$^+$): MS (ES+) 536.3 (M+1), 534.3 (M−1), 570.3 (M+Cl); Analysis calculated for: $C_{29}H_{28}F_3N_5O_2$.1.5$H_2O_2$HCl: C, 54.81; H, 5.23; Cl, 11.16; N, 11.02; Found: C, 55.01; H, 5.21; Cl, 11.05; N, 11.01; Chiral purity checked by chiral HPLC using AD-H column; isocratic method 85/15/0.1 (Hexane/ethanol/TEA) 0.5 mL/min, UV 260 nM, 40 mins run time, Temp 5° C.) Rt=20.427 (3.6638% peak-1 for 64a) Rt=27.260 (96.3362%, peak-2, for 64b, 92.67% ee); Analysis calculated for C$_{29}$H$_{28}$F$_3$N$_5$O$_2$.1.5H$_2$O.2HCl: C, 54.81; H, 5.23; Cl, 11.16; N, 11.02; Found: C, 55.01; H, 5.21; Cl, 11.05; N, 11.01.

Scheme 65

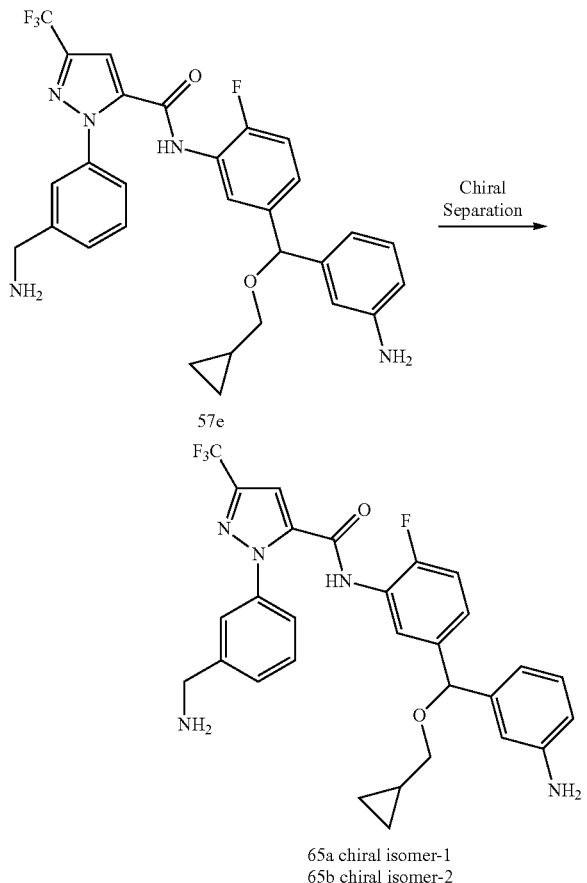

57e 65a chiral isomer-1
65b chiral isomer-2

Preparation of chiral isomer-1 1-(3-(aminomethyl)phenyl)-N-(5-((3-aminophenyl)(cyclopropylmethoxy)methyl)-2-fluorophenyl)-3-(trifluoromethyl)-1H-pyrazole-5-carboxamide (65a) and chiral isomer-2 1-(3-(aminomethyl)phenyl)-N-(5-((3-aminophenyl)(cyclopropylmethoxy)methyl)-2-fluorophenyl)-3-(trifluoromethyl)-1H-pyrazole-5-carboxamide (65b)

Racemic 1-(3-(aminomethyl)phenyl)-N-(5-((3-aminophenyl)(cyclopropylmethoxy)methyl)-2-fluorophenyl)-3-(trifluoromethyl)-1H-pyrazole-5-carboxamide (57e) (240 mg) was separated into pure chiral isomers using preparative chiral HPLC. The condition used was as follows:

| | |
|---|---|
| Column | 3.0 × 25.0 cm RegisPack from Regis Technologies (Morton Grove, IL) |
| Solvent | Hexane:Ethanol:Diethylamine (80:20:0.1) |
| Isocratic Method | 50 mL/min |
| System Pressure | 100 bar |
| Column Temperature | 25° C. |
| Sample Diluent | Methanol |

1. Peak-1 was assigned as chiral isomer-1 1-(3-(aminomethyl)phenyl)-N-(5-((3-aminophenyl)(cyclopropylmethoxy)methyl)-2-fluorophenyl)-3-(trifluoromethyl)-1H-pyrazole-5-carboxamide (65a). The compound was repurified by flash column chromatography (silica gel, 4 g eluting with methanol in chloroform 0 to 25%) to afford pure chiral isomer-1 1-(3-(aminomethyl)phenyl)-N-(5-((3-aminophenyl)(cyclopropylmethoxy)methyl)-2-fluorophenyl)-3-(trifluoromethyl)-1H-pyrazole-5-carboxamide (65a) (17 mg, 62.35% ee); 1H NMR (300 MHz, DMSO-d$_6$) δ 10.58 (s, 1H), 7.58 (s, 1H), 7.52 (d, J=5.7 Hz, 2H), 7.48-7.39 (m, 2H), 7.34 (d, J=7.0 Hz, 1H), 7.26-7.17 (m, 2H), 6.94 (t, J=7.7 Hz, 1H), 6.52 (t, J=2.0 Hz, 1H), 6.50-6.37 (m, 2H), 5.26 (s, 1H), 5.08 (s, 2H), 3.80 (s, 2H), 3.19 (dd, J=6.9, 3.1 Hz, 2H), 1.04 (dd, J=12.3, 6.3 Hz, 1H), 0.45 (dt, J=9.0, 2.8 Hz, 2H), 0.14 (q, J=4.8 Hz, 2H); Mass spec (ES+) 554.3 (M+1). (ES−) 552.2 (M−1); Chiral purity checked by chiral HPLC using chiral AD-H column; solvent isocratic 85/15/0.1 (Hexane/ethanol/TEA); flow rate 0.8 mL/min; UV 243 nM, 25 mins run time (Temp 30° C.). Rt=18.247 (Peak-1 for 65a, 81.1746%); Rt=20.287 (peak-2 for 65b, 18.83%).

2. Peak-2 was assigned as chiral isomer-2 1-(3-(aminomethyl)phenyl)-N-(5-((3-aminophenyl)(cyclopropylmethoxy)methyl)-2-fluorophenyl)-3-(trifluoromethyl)-1H-pyrazole-5-carboxamide (65b). The compound was repurified by flash column chromatography (silica gel, 4 g eluting with methanol in chloroform 0 to 25%) to afford pure chiral isomer-2 1-(3-(aminomethyl)phenyl)-N-(5-((3-aminophenyl)(cyclopropylmethoxy)methyl)-2-fluorophenyl)-3-(trifluoromethyl)-1H-pyrazole-5-carboxamide (65b) (6 mg, 57.4% ee); $^1$H NMR (300 MHz, DMSO-d$_6$) δ 10.60 (s, 1H), 7.67-7.37 (m, 5H), 7.28-7.17 (m, 2H), 6.99-6.90 (m, 1H), 6.52 (t, J=1.9 Hz, 2H), 6.43 (dddd, J=10.3, 7.9, 2.6, 1.1 Hz, 2H), 5.25 (d, J=5.2 Hz, 1H), 5.07 (s, 2H), 3.19 (dd, J=6.7, 2.5 Hz, 2H), 1.10-0.96 (m, 1H), 0.44 (m, 2H), 0.19-0.02 (m, 2H); $^{19}$F NMR (282 MHz, DMSO-d$_6$) δ −60.79, −123.04. Chiral purity checked by chiral HPLC using chiral AD-H column; solvent isocratic 85/15/0.1 (Hexane/ethanol/TEA); flow rate 0.8 mL/min; UV 243 nM, 25 mins run time (Temp 30° C.). R$_f$=18.41 (peak-1 for 65a, 21.30%) R$_f$=20.31 (peak-2 for 65b, 78.70%).

Scheme 66

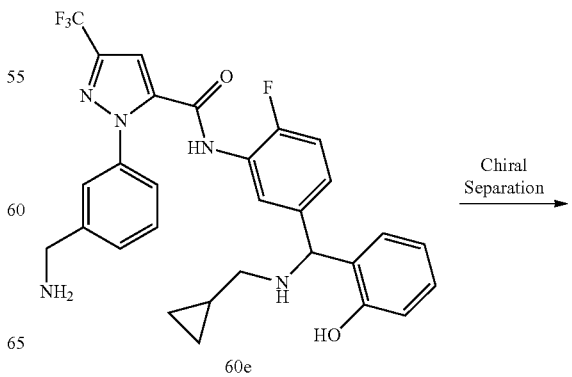

60e

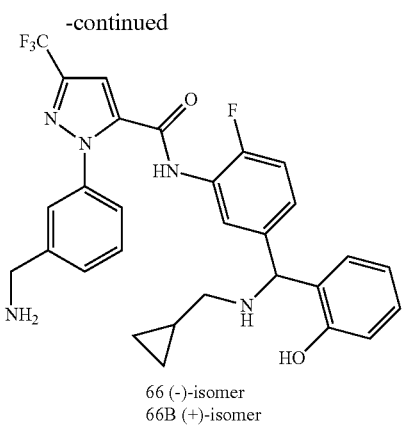

66 (−)-isomer
66B (+)-isomer

Preparation of (−)-1-(3-(aminomethyl)phenyl)-N-(5-((cyclopropylmethylamino)(2-hydroxyphenyl)methyl)-2-fluorophenyl)-3-(trifluoromethyl)-1H-pyrazole-5-carboxamide (66a) and (+)-1-(3-(aminomethyl)phenyl)-N-(5-((cyclopropylmethylamino)(2-hydroxyphenyl)methyl)-2-fluorophenyl)-3-(trifluoromethyl)-1H-pyrazole-5-carboxamide (66b)

Isomers of racemic 1-(3-(aminomethyl)phenyl)-N-(5-((cyclopropylmethylamino)(2-hydroxyphenyl)methyl)-2-fluorophenyl)-3-(trifluoromethyl)-1H-pyrazole-5-carboxamide (60e) (335 mg) were separated using Chiral Preparative SFC. Method used; Column: 3.0×25 cm Regis-Pack from Regis Technologies (Morton Grove, Ill.); Solvent Hexane:ethanol (9:1) with 0.1% diethylamine; Isocratic Method: 60 g/min; System pressure 100 bar; Column temperature 25° C.; sample diluents ethanol, to furnish:

1. Peak-1 was assigned as (−)-1-(3-(aminomethyl)phenyl)-N-(5-((cyclopropylmethylamino)(2-hydroxyphenyl)methyl)-2-fluorophenyl)-3-(trifluoromethyl)-1H-pyrazole-5-carboxamide (66a) (37 mg). This material was repurified by flash column chromatography (silica gel 12 g, eluting with 0-30% methanol in chloroform) to furnish (−)-1-(3-(aminomethyl)phenyl)-N-(5-((cyclopropylmethylamino)(2-hydroxyphenyl)methyl)-2-fluorophenyl)-3-(trifluoromethyl)-1H-pyrazole-5-carboxamide (66a) (2 mg, 44% ee). $^1$H NMR (300 MHz, DMSO-$d_6$) δ 10.58 (s, 1H), 7.58 (d, J=12.0 Hz, 3H), 7.52-7.19 (m, 5H), 7.10-6.96 (m, 2H), 6.78-6.62 (m, 2H), 5.03 (s, 1H), 3.87 (s, 2H), 2.44-2.32 (m, 1H), 2.31-2.19 (m, 1H), 1.00-0.82 (m, 1H), 0.46-0.33 (m, 2H), 0.15-0.03 (m, 2H); $^{19}$F NMR (282 MHz, DMSO-$d_6$) δ −60.77, −122.98; MS (ES+) 554.2 (M+1).

2. Peak-2 was assigned as (+)-1-(3-(aminomethyl)phenyl)-N-(5-((cyclopropylmethylamino)(2-hydroxyphenyl)methyl)-2-fluorophenyl)-3-(trifluoromethyl)-1H-pyrazole-5-carboxamide (66b) (44 mg, 92% ee). This was repurified by flash column chromatography (silica gel 12 g, eluting with 0-30% methanol in chloroform) to furnish free base of (+)-1-(3-(aminomethyl)phenyl)-N-(5-((cyclopropylmethylamino)(2-hydroxyphenyl)methyl)-2-fluorophenyl)-3-(trifluoromethyl)-1H-pyrazole-5-carboxamide (66b) (40 mgs); Optical rotation: $[α]_D$=(+) 61.86 [CH$_3$OH, 0.86]; $^1$H NMR (300 MHz, DMSO-$d_6$) δ 10.57 (s, 1H, D$_2$O exchangeable), 7.64-7.54 (m, 2H), 7.51 (s, 1H), 7.47-7.40 (m, 2H), 7.32 (dq, J=6.8, 2.3 Hz, 2H), 7.23 (dd, J=10.3, 8.5 Hz, 1H), 7.03 (td, J=6.3, 2.4 Hz, 2H), 6.75-6.64 (m, 2H), 5.03 (s, 1H), 3.77 (s, 2H), 2.45-2.35 (m, 2H), 2.31-2.18 (m, 1H), 1.02-0.86 (m, 1H), 0.52-0.29 (m, 2H), 0.14-0.03 (m, 2H); $^{19}$F NMR (282 MHz, DMSO-$d_6$) δ −60.73 (d, J=5.3 Hz), −123.06; MS (ES+) 554.4 (M+1), 552.4 (M−1). To a solution of free base of (+)-1-(3-(aminomethyl)phenyl)-N-(5-((cyclopropylmethylamino)(2-hydroxyphenyl)methyl)-2-fluorophenyl)-3-(trifluoromethyl)-1H-pyrazole-5-carboxamide (66b) (29 mgs) in methanol (4 mL) added 2 N HCl (0.131 mL, 5 eq.), stirred for 30 mins and evaporated to dryness to afford (+)-1-(3-(aminomethyl)phenyl)-N-(5-((cyclopropylmethylamino)(2-hydroxyphenyl)methyl)-2-fluorophenyl)-1H-pyrazole-5-carboxamide (66b) (20 mgs) hydrochloride salt as an off-white solid; $^1$H NMR (300 MHz, DMSO-$d_6$) δ 10.83 (s, 1H, D$_2$O exchangeable), 10.39 (s, 1H, D$_2$O exchangeable), 10.08 (s, 1H, D$_2$O exchangeable), 9.77 (s, 1H, D$_2$O exchangeable), 8.51 (d, J=7.3 Hz, 3H, D$_2$O exchangeable), 7.92-7.46 (m, 8H), 7.37 (dd, J=10.3, 8.5 Hz, 1H), 7.18 (td, J=7.7, 1.6 Hz, 1H), 7.01-6.81 (m, 2H), 5.88-5.58 (m, 1H), 4.12 (q, J=5.8 Hz, 2H), 2.72 (q, J=5.9 Hz, 2H), 1.13 (ddd, J=12.9, 8.7, 3.8 Hz, 1H), 0.64-0.45 (m, 2H), 0.38-0.18 (m, 2H); $^{19}$F NMR (282 MHz, DMSO-$d_6$) δ −60.81, −120.50; MS (ES+) 554.3 (M+1), 552.3 (M−1), 588.3 (M+Cl); Calculated for C$_{29}$H$_{27}$F$_4$N$_5$O$_2$.2.1HCl 1.5H$_2$O: C, 53.00; H, 4.92; Cl, 11.33; N, 10.66; Found: C, 52.90; H, 4.90; Cl, 11.46; N, 10.28.

Scheme 67

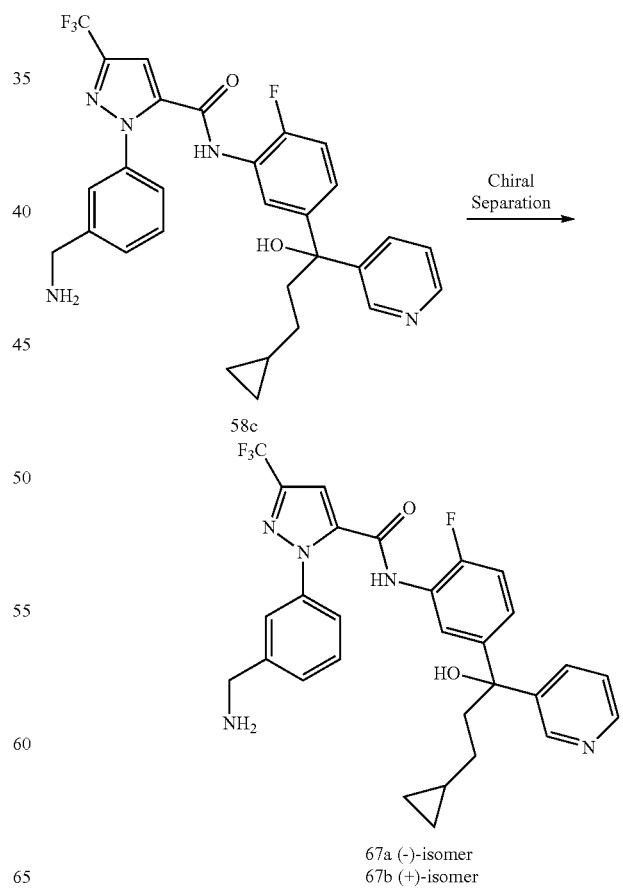

58c 67a (−)-isomer
67b (+)-isomer

Preparation of (−)-1-(3-(aminomethyl)phenyl)-N-(5-(3-cyclopropyl-1-hydroxy-1-(pyridin-3-yl)propyl)-2-fluorophenyl)-3-(trifluoromethyl)-1H-pyrazole-5-carboxamide (67a) and (+)-1-(3-(aminomethyl)phenyl)-N-(5-(3-cyclopropyl-1-hydroxy-1-(pyridin-3-yl)propyl)-2-fluorophenyl)-3-(trifluoromethyl)-1H-pyrazole-5-carboxamide (67b)

Isomers of Racemic 1-(3-(aminomethyl)phenyl)-N-(5-(3-cyclopropyl-1-hydroxy-1-(pyridin-3-yl)propyl)-2-fluorophenyl)-3-(trifluoromethyl)-1H-pyrazole-5-carboxamide (58c) (2.0 g) were separated by using preparative SFC method using the following conditions to furnish:

| Column | 2.1 × 25 cm ChiralPak IC SFC from Chiral Technologies (West Chester, PA) |
|---|---|
| CO2 Co-solvent (Solvent B) | Acetonitrile:Methanol (3:1) with 1% Isopropylamine |
| Isocratic Method | 35% Co-solvent at 80 mL/min |
| System Pressure | 200 bar |
| Column Temperature | 25° C. |
| Sample Diluent | MeOH:ACN (2:1) with a small amount of DCM |

1. Peak-1 assigned as (−)-1-(3-(aminomethyl)phenyl)-N-(5-(3-cyclopropyl-1-hydroxy-1-(pyridin-3-yl)propyl)-2-fluorophenyl)-3-(trifluoromethyl)-1H-pyrazole-5-carboxamide (67a) (755 mg >95 ee); Optical rotation: $[\alpha]_D$=(−) 3.10 [$CH_3OH$, 2.19]; $^1H$ NMR (300 MHz, DMSO-$d_6$) δ 10.54 (s, 1H), 8.67-8.57 (m, 1H), 8.38 (dd, J=4.8, 1.6 Hz, 1H), 7.77 (dt, J=8.2, 2.0 Hz, 1H), 7.69-7.61 (m, 1H), 7.57 (s, 1H), 7.51 (s, 1H), 7.47-7.38 (m, 2H), 7.37-7.27 (m, 3H), 7.25-7.15 (m, 1H), 5.80 (s, 1H), 3.77 (s, 2H), 2.33 (t, J=7.9 Hz, 2H), 1.99 (s, 2H), 1.06 (q, J=9.4, 6.3 Hz, 2H), 0.63 (t, J=7.2 Hz, 1H), 0.41-0.26 (m, 2H), −0.07 (dd, J=4.8, 1.6 Hz, 2H); To a solution of free base of (−)-1-(3-(aminomethyl)phenyl)-N-(5-(3-cyclopropyl-1-hydroxy-1-(pyridin-3-yl)propyl)-2-fluorophenyl)-3-(trifluoromethyl)-1H-pyrazole-5-carboxamide (67a) (700 mg) in methanol (10 mL) was added hydrochloric acid in methanol (2 M, 6.5 mL), stirred for 30 mins and concentrated to remove excess hydrochloric acid. The residue was dried in vacuum to give (−)-1-(3-(aminomethyl)phenyl)-N-(5-(3-cyclopropyl-1-hydroxy-1-(pyridin-3-yl)propyl)-2-fluorophenyl)-3-(trifluoromethyl)-1H-pyrazole-5-carboxamide (67a) hydrochloride salt; $^1H$ NMR (300 MHz, DMSO-$d_6$) δ 10.70 (s, 1H, $D_2O$ exchangeable), 8.85 (d, J=2.1 Hz, 1H), 8.72 (dd, J=5.4, 1.4 Hz, 1H), 8.44 (t, J=7.4 Hz, 4H, 3H $D_2O$ exchangeable), 7.87 (dd, J=8.2, 5.4 Hz, 1H), 7.72 (t, J=8.4 Hz, 3H), 7.63 (dt, J=7.2, 1.8 Hz, 1H), 7.59-7.47 (m, 2H), 7.40 (ddd, J=8.8, 4.5, 2.3 Hz, 1H), 7.25 (dd, J=10.2, 8.7 Hz, 1H), 6.28 (s, 1H, $D_2O$ exchangeable), 4.11 (q, J=5.8 Hz, 2H), 2.43 (dd, J=10.6, 5.8 Hz, 2H), 1.06 (td, J=15.4, 14.2, 6.9 Hz, 2H), 0.71-0.56 (m, 1H), 0.41-0.31 (m, 2H), −0.06 (dd, J=4.1, 1.5 Hz, 2H); $^{19}F$ NMR (282 MHz, DMSO-$d_6$) δ −57.73--63.18 (m), −122.87 (s); Mass spec (ES+) 554.3 (M+1); (ES−) 552.2 (M−1), 588.2 (M+Cl); Analysis calculated for $C_{29}H_{27}F_4N_5O_2.2HCl.H_2O$: C, 54.10; H, 4.85; Cl, 10.87; N, 10.88; Found: C, 53.97; H, 4.88; Cl, 11.19; N, 10.65.

2. Peak-2 assigned as (+)-1-(3-(aminomethyl)phenyl)-N-(5-(3-cyclopropyl-1-hydroxy-1-(pyridin-3-yl)propyl)-2-fluorophenyl)-3-(trifluoromethyl)-1H-pyrazole-5-carboxamide (67b) (816 mg, 97.6% ee) as a free base; Optical rotation: $[\alpha]_D$=(+) 3.23 [$CH_3OH$, 2.04]; $^1H$ NMR (300 MHz, DMSO-$d_6$) δ 10.53 (s, 1H, $D_2O$ exchangeable), 8.62 (dd, J=2.4, 0.9 Hz, 1H), 8.38 (dd, J=4.7, 1.6 Hz, 1H), 7.78 (dt, J=8.0, 2.1 Hz, 1H), 7.65 (dd, J=7.5, 2.4 Hz, 1H), 7.57 (s, 1H), 7.51 (s, 1H), 7.47-7.38 (m, 2H), 7.32 (dddd, J=8.8, 7.9, 4.7, 1.6 Hz, 3H), 7.20 (dd, J=10.3, 8.6 Hz, 1H), 5.80 (s, 1H, $D_2O$ exchangeable), 3.77 (s, 2H), 2.34 (t, J=7.8 Hz, 2H), 1.17-0.99 (m, J=6.8 Hz, 2H), 0.61 (dt, J=12.8, 6.9 Hz, 1H), 0.41-0.25 (m, 2H), −0.07 (dd, J=4.8, 1.6 Hz, 2H); MS (ES+) 554.3 (M+1), 576.3 (M+Na); 552.3 (M−1), 588.2 (M+Cl). To a solution of free base of (+)-1-(3-(aminomethyl)phenyl)-N-(5-(3-cyclopropyl-1-hydroxy-1-(pyridin-3-yl)propyl)-2-fluorophenyl)-3-(trifluoromethyl)-1H-pyrazole-5-carboxamide (67b) (700 mg) in methanol (10 mL) was added hydrochloric acid in methanol (2 M, 6.5 mL), stirred for 30 mins and concentrated in vacuum to remove excess hydrochloric acid. The residue was dried to give (+)-1-(3-(aminomethyl)phenyl)-N-(5-(3-cyclopropyl-1-hydroxy-1-(pyridin-3-yl)propyl)-2-fluorophenyl)-3-(trifluoromethyl)-1H-pyrazole-5-carboxamide (67b) (730 mg) hydrochloride salt as a white solid; $^1H$ NMR (300 MHz, DMSO-$d_6$) δ 10.70 (s, 1H, $D_2O$ exchangeable), 8.86 (s, 1H), 8.73 (d, J=5.0 Hz, 1H), 8.45 (d, J=9.5 Hz, 4H, 3H $D_2O$ exchangeable), 7.99-7.84 (m, 1H), 7.71 (d, J=10.0 Hz, 3H), 7.63 (d, J=7.0 Hz, 1H), 7.59-7.47 (m, 2H), 7.45-7.36 (m, 1H), 7.26 (dd, J=10.2, 8.6 Hz, 1H), 6.30 (s, 1H, $D_2O$ exchangeable), 4.11 (q, J=5.8 Hz, 2H), 2.43 (t, J=8.5 Hz, 2H), 1.06 (dq, J=13.8, 7.8, 6.7 Hz, 2H), 0.70-0.56 (m, 1H), 0.40-0.29 (m, 2H), −0.02--0.09 (m, 2H); Mass spec (ES+) 554.3 (M+1), (ES−) 552.1 (M−1), 588.2 (M+Cl); Analysis calculated for $C_{29}H_{27}F_4N_5O_2.2HCl.H_2O$: C, 54.10; H, 4.85; Cl, 10.87; N, 10.88; Found: C, 53.94; H, 5.00; Cl, 11.09; N, 10.74.

Scheme 68
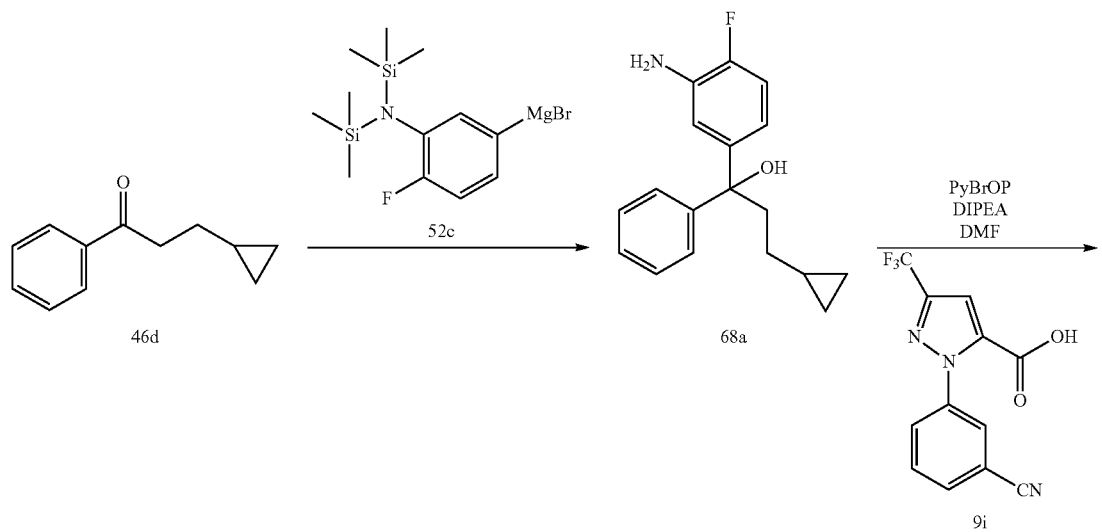
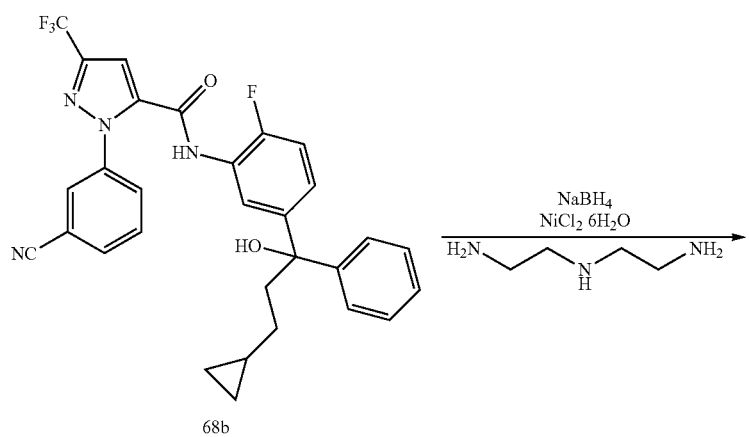
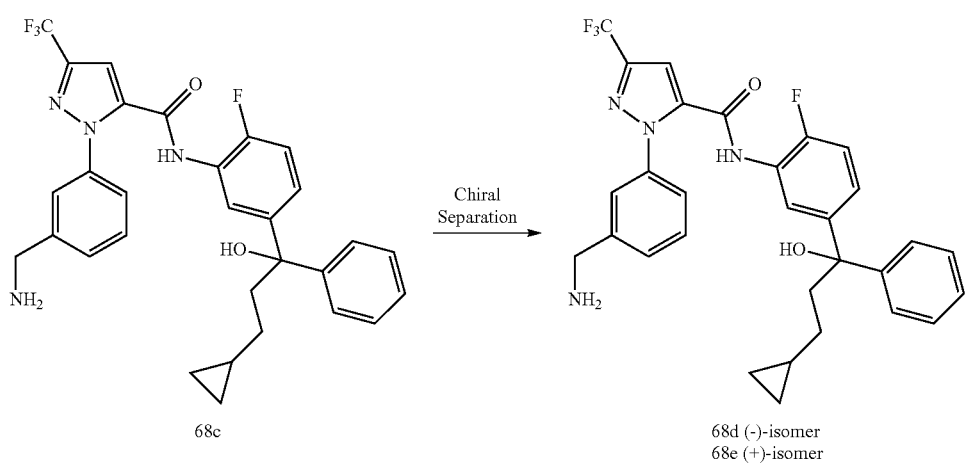

Preparation of Racemic 1-(3-(aminomethyl)phenyl)-N-(5-(3-cyclopropyl-1-hydroxy-1-phenylpropyl)-2-fluorophenyl)-3-(trifluoromethyl)-1H-pyrazole-5-carboxamide (68c), (−)-1-(3-(aminomethyl)phenyl)-N-(5-(3-cyclopropyl-1-hydroxy-1-phenylpropyl)-2-fluorophenyl)-3-(trifluoromethyl)-1H-pyrazole-5-carboxamide (68d) and (+)-1-(3-(aminomethyl)phenyl)-N-(5-(3-cyclopropyl-1-hydroxy-1-phenylpropyl)-2-fluorophenyl)-3-(trifluoromethyl)-1H-pyrazole-5-carboxamide (68e)

Step-1: Preparation of 1-(3-amino-4-fluorophenyl)-3-cyclopropyl-1-phenylpropan-1-ol (68a)

To a stirred solution of 3-cyclopropyl-1-phenylpropan-1-one (46d) (12 g, 68.9 mmol) in tetrahydrofuran (10 mL) was added was added freshly prepared (3-(bis(trimethylsilyl)amino)-4-fluorophenyl)magnesium bromide (52c) (88 mL, 79 mmol, 0.9 M solution in THF) at 0° C. The reaction was allowed to stir for 2 h at 0° C., quenched with saturated aqueous ammonium chloride solution (100 mL), stirred for 2 h and extracted with ethyl acetate (2×100 mL). The organic layers were combined, washed with water (2×100 mL), brine (100 mL), dried, filtered and concentrated in vacuum. The crude residue was purified by flash column chromatography (silica gel, 120 g, eluting with ethyl acetate in hexanes 0-100%) to afford 1-(3-amino-4-fluorophenyl)-3-cyclopropyl-1-phenylpropan-1-ol (68a) (15.6 mg, 79%) as an oil; $^1$H NMR (300 MHz, DMSO-d$_6$) δ 7.42-7.35 (m, 2H), 7.25 (ddd, J=7.7, 6.9, 1.2 Hz, 2H), 7.17-7.09 (m, 1H), 6.92-6.77 (m, 2H), 6.54 (ddd, J=8.5, 4.5, 2.3 Hz, 1H), 5.29 (s, 1H), 4.99 (s, 2H), 2.31-2.17 (m, 2H), 1.14-0.95 (m, 2H), 0.72-0.53 (m, 1H), 0.39-0.27 (m, 2H), −0.09 (td, J=5.3, 3.7 Hz, 2H).

Step-2: Preparation of 1-(3-cyanophenyl)-N-(5-(3-cyclopropyl-1-hydroxy-1-phenylpropyl)-2-fluorophenyl)-3-(trifluoromethyl)-1H-pyrazole-5-carboxamide (68b)

To a solution of 1-(3-cyanophenyl)-3-(trifluoromethyl)-1H-pyrazole-5-carboxylic acid (9i) (12.32 g, 43.8 mmol) in N,N-dimethylformamide (265 mL) was added 1-(3-amino-4-fluorophenyl)-3-cyclopropyl-1-phenylpropan-1-ol (68a) (15 g, 52.6 mmol), N-ethyl-N-isopropylpropan-2-amine (61.0 mL, 350 mmol) and Bromo-tris-pyrrolidino phosphoniumhexafluorophosphate (PyBrOP, 22.46 g, 48.2 mmol) at room temperature. The reaction mixture was stirred at 25° C. for 16 h quenched with water (200 mL) and extracted with ethyl acetate (3×300 mL). The organic layers were combined washed with water (2×100 mL), brine (100 mL), dried over anhydrous MgSO$_4$, filtered, and concentrated in under reduced pressure to dryness. The residue was purified by flash column chromatography (silica gel 120 g, eluting with hexanes in ethyl acetate/hexanes from 0-40 to 100%) to afford 1-(3-cyanophenyl)-N-(5-(3-cyclopropyl-1-hydroxy-1-phenylpropyl)-2-fluorophenyl)-3-(trifluoromethyl)-1H-pyrazole-5-carboxamide (68b) (18.715 g, 34.1 mmol, 78% yield); $^1$H NMR (300 MHz, DMSO-d$_6$) δ 10.52 (s, 1H, D$_2$O exchangeable), 8.12 (t, J=2.0 Hz, 1H), 8.00 (dt, J=7.8, 1.3 Hz, 1H), 7.96-7.85 (m, 1H), 7.78-7.67 (m, 2H), 7.57 (dd, J=7.6, 2.3 Hz, 1H), 7.44-7.37 (m, 2H), 7.35-7.23 (m, 3H), 7.21-7.16 (m, 1H), 7.16-7.11 (m, 1H), 5.57 (s, 1H, D$_2$O exchangeable), 2.35-2.24 (m, 2H), 1.06 (q, J=7.1 Hz, 2H), 0.60 (dt, J=12.1, 7.2 Hz, 1H), 0.40-0.27 (m, 2H), −0.09 (td, J=5.2, 3.6 Hz, 2H).

Step-3: Preparation of Racemic 1-(3-(aminomethyl)phenyl)-N-(5-(3-cyclopropyl-1-hydroxy-1-phenylpropyl)-2-fluorophenyl)-3-(trifluoromethyl)-1H-pyrazole-5-carboxamide (68c)

To a stirred solution of 1-(3-cyanophenyl)-N-(5-(3-cyclopropyl-1-hydroxy-1-phenylpropyl)-2-fluorophenyl)-3-(trifluoromethyl)-1H-pyrazole-5-carboxamide (68b) (10 g, 18.23 mmol) in methanol (300 mL) at 0° C. was added nickel(II) chloride hexahydrate (1.083 g, 4.56 mmol) followed by sodium tetrahydroborate (6.90 g, 182 mmol) in small portions over a period of 15 mins. The reaction was stirred for 15 mins, quenched by adding N1-(2-aminoethyl)ethane-1,2-diamine (4.73 mL, 45.6 mmol), stirred for additional 30 mins at room temperature and concentrated in vacuum to remove methanol. The reaction mixture was diluted water (500 mL) and stirred for 2 h. The solid separated was collected by filtration. The solid was dissolved in dichloromethane (500 mL) washed with water (2×200 mL) extracted with dichloromethane (2×200 mL). The chloroform layers were combined washed with brine (2×200 mL), dried and concentrated in vacuum. The residue was purified by flash column chromatography (silica gel, 120 g, eluting with CMA 80 in chloroform 0-100%) to afford Racemic 1-(3-(aminomethyl)phenyl)-N-(5-(3-cyclopropyl-1-hydroxy-1-phenylpropyl)-2-fluorophenyl)-3-(trifluoromethyl)-1H-pyrazole-5-carboxamide (68c) (6.1 g, 11.04 mmol, 60.6% yield) as a colorless solid.

Step-4: Preparation of (−)-1-(3-(aminomethyl)phenyl)-N-(5-(3-cyclopropyl-1-hydroxy-1-phenylpropyl)-2-fluorophenyl)-3-(trifluoromethyl)-1H-pyrazole-5-carboxamide (68d) and (+)-1-(3-(aminomethyl)phenyl)-N-(5-(3-cyclopropyl-1-hydroxy-1-phenylpropyl)-2-fluorophenyl)-3-(trifluoromethyl)-1H-pyrazole-5-carboxamide (68e)

Isomers of 1-(3-(aminomethyl)phenyl)-N-(5-(3-cyclopropyl-1-hydroxy-1-phenylpropyl)-2-fluorophenyl)-3-(trifluoromethyl)-1H-pyrazole-5-carboxamide (68c) (240 mg) were separated by using preparative SFC method using the following conditions to furnish: Preparative SFC Method

| Column | 2.1 × 25 cm ChiralPak IC SFC from Chiral Technologies (West Chester, PA) |
|---|---|
| CO$_2$ Co-solvent (Solvent B) | Methanol w/1% Isopropylamine |
| Isocratic Method | 25% Co-solvent at 80 mL/min |
| System Pressure | 100 bar |
| Column Temperature | 25° C. |
| Sample Diluent | MeOH:Dichloromethane (3:1) |

1. Peak-1 assigned as (−)-1-(3-(aminomethyl)phenyl)-N-(5-(3-cyclopropyl-1-hydroxy-1-phenylpropyl)-2-fluorophenyl)-3-(trifluoromethyl)-1H-pyrazole-5-carboxamide (68d) (59 mg >95 ee); Optical rotation: [α]$_D$=(−) 0.987 [CH$_3$OH, 0.081]; $^1$H NMR (300 MHz, DMSO-d$_6$) δ 10.52 (s, 1H), 7.62 (dd, J=7.5, 2.4 Hz, 1H), 7.57 (s, 1H), 7.51 (s, 1H), 7.46-7.38 (m, 4H), 7.29 (dt, J=15.0, 7.6 Hz, 4H), 7.21-7.11 (m, 2H), 5.57 (s, 1H), 3.77 (s, 2H), 2.28 (d, J=8.2 Hz, 2H), 1.05 (dd, J=10.4, 5.9 Hz, 2H), 0.62 (dq, J=12.5, 6.0, 5.4 Hz, 1H), 0.41-0.28 (m, 2H), −0.09 (t, J=4.7 Hz, 2H); $^{19}$F NMR (282 MHz, DMSO-d$_6$) δ −60.71, −124.35-−124.46 (m); MS (ES+) 553.3 (M+1) 575.3 (M+Na), (ES−) 551.2

(M−1); Analysis calculated for $C_{30}H_{28}F_4N_4O_2$: C, 65.19; H, 5.11; N, 10.14; Found: C, 65.33; H, 5.37; N, 9.88.

2. Peak-2 assigned as (+)-1-(3-(aminomethyl)phenyl)-N-(5-(3-cyclopropyl-1-hydroxy-1-phenylpropyl)-2-fluorophenyl)-3-(trifluoromethyl)-1H-pyrazole-5-carboxamide (68e) (124 mg >95 ee); This compound was repurified by flash column chromatography (silica gel 12 g, eluting with CMA 80 in chloroform) to afford pure as (+)-1-(3-(aminomethyl)phenyl)-N-(5-(3-cyclopropyl-1-hydroxy-1-phenylpropyl)-2-fluorophenyl)-3-(trifluoromethyl)-1H-pyrazole-5-carboxamide (68e) (77 mg) as a white solid; Optical rotation: $[\alpha]_D$=(+) 1.558 [$CH_3OH$, 0.77]; $^1H$ NMR (300 MHz, DMSO-$d_6$) δ 10.52 (s, 1H), 7.62 (dd, J=7.5, 2.3 Hz, 1H), 7.57 (s, 1H), 7.51 (s, 1H), 7.45-7.38 (m, 4H), 7.35-7.30 (m, 1H), 7.29 (d, J=2.6 Hz, 1H), 7.26 (d, J=7.7 Hz, 2H), 7.20-7.12 (m, 2H), 5.57 (s, 1H), 3.78 (s, 2H), 2.29 (t, J=8.1 Hz, 2H), 1.11-1.02 (m, 2H), 0.69-0.54 (m, 1H), 0.33 (dt, J=8.5, 2.8 Hz, 2H), −0.08 (q, J=4.8 Hz, 2H); MS (ES+) 553.3 (M+1), (ES−) 551.2 (M−1).

Scheme 69

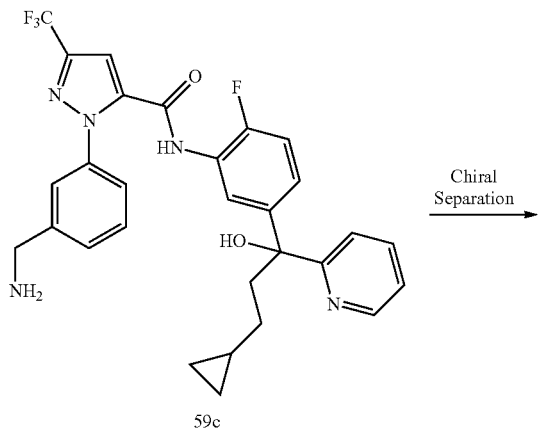

59c

Chiral Separation →

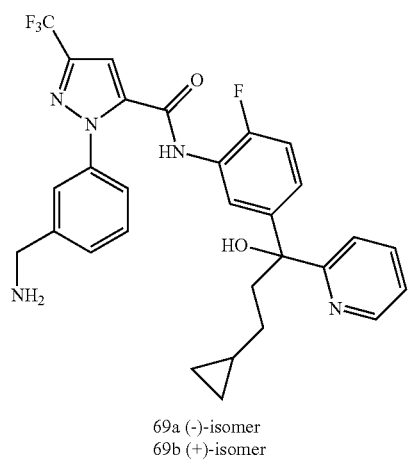

69a (−)-isomer
69b (+)-isomer

Preparation of (−)-1-(3-(aminomethyl)phenyl)-N-(5-(3-cyclopropyl-1-hydroxy-1-(pyridin-2-yl)propyl)-2-fluorophenyl)-3-(trifluoromethyl)-1H-pyrazole-5-carboxamide (69a) and (+)-1-(3-(aminomethyl)phenyl)-N-(5-(3-cyclopropyl-1-hydroxy-1-(pyridin-2-yl)propyl)-2-fluorophenyl)-3-(trifluoromethyl)-1H-pyrazole-5-carboxamide (69b)

Isomers of Racemic 1-(3-(aminomethyl)phenyl)-N-(5-(3-cyclopropyl-1-hydroxy-1-(pyridin-2-yl)propyl)-2-fluorophenyl)-3-(trifluoromethyl)-1H-pyrazole-5-carboxamide (59c) (2.0 g) were separated by using preparative SFC method using the following conditions to furnish:

Preparative SFC Method Used:

| | |
|---|---|
| Column | 2.1 × 25 cm ChiralPak IC SFC from Chiral Technologies (West Chester, PA) |
| $CO_2$ Co-solvent (Solvent B) | Dichloromethane:Methanol (9:1) with 1% Isopropylamine |
| Isocratic Method | 60% Co-solvent at 80 mL/min |
| System Pressure | 100 bar |
| Column Temperature | 25° C. |
| Sample Diluent | Methanol |

Chiral Purity of peaks was determined by following Analytical SFC Method:

| | |
|---|---|
| Column | 4.6 × 100 mm ChiralPak IC SFC from Chiral Technologies (West Chester, PA) |
| $CO_2$ Co-solvent (Solvent B) | Dichloromethane: Methanol (9:1) with 0.1% Isopropylamine |
| Gradient Method | 5-65% Co-solvent at 4 mL/min |
| System Pressure | 100 bar |
| Column Temperature | 25° C. |
| Sample Diluent | Methanol |

| | | | | |
|---|---|---|---|---|
| Peak-1 (69a) | Rt = 2.8 min | 265 mg | >95% ee (UV 254) | 95.3% purity (UV 254) |
| Peak-2 (69b) | Rt = 3.7 min | 464 mg | >95% ee (UV 254) | 98.0% purity (UV 254) |

1. Peak-1 assigned as (−)-1-(3-(aminomethyl)phenyl)-N-(5-(3-cyclopropyl-1-hydroxy-1-(pyridin-2-yl)propyl)-2-fluorophenyl)-3-(trifluoromethyl)-1H-pyrazole-5-carboxamide (69a) (265 mg >95 ee) free base as a white solid. Optical rotation: $[\alpha]_D$=(−) 0.95 [$CH_3OH$, 2.105]; 1H NMR (300 MHz, DMSO-$d_6$) δ 10.54 (s, 1H), 8.67-8.57 (m, 1H), 8.38 (dd, J=4.8, 1.6 $^1$HNMR (300 MHz, DMSO-$d_6$) δ 10.54 (s, 1H, $D_2O$ exchangeable), 8.52-8.46 (m, 1H), 7.77-7.68 (m, 2H), 7.61 (t, J=8.2 Hz, 3H), 7.50-7.46 (m, 2H), 7.40 (ddd, J=7.4, 5.0, 2.2 Hz, 2H), 7.23-7.12 (m, 2H), 5.83 (s, 1H, $D_2O$ exchangeable), 5.00 (s, 2H, $D_2O$ exchangeable), 3.91 (s, 2H), 2.42-2.22 (m, 2H), 1.01 (s, 2H), 0.67-0.51 (m, 1H), 0.37-0.27 (m, 2H), −0.10 (p, J=4.8 Hz, 2H); MS (ES+) 554.3 (M+1), 576.3 (M+Na); (ES−) 552.3 (M−1), 588.3 (M+Cl). To a solution of free base of (−)-1-(3-(aminomethyl)phenyl)-N-(5-(3-cyclopropyl-1-hydroxy-1-(pyridin-2-yl)propyl)-2-fluorophenyl)-3-(trifluoromethyl)-1H-pyrazole-5-carboxamide (69a) (250 mg) in methanol (10 mL) was added hydrochloric acid in methanol (2 M, 2.305 mL) stirred for 30 mins and concentrated in vacuum to remove excess hydrochloric acid. The residue was dried to give (−)-1-(3-(aminomethyl)phenyl)-N-(5-(3-cyclopropyl-1-hydroxy-1-(pyridin-2-yl)propyl)-2-fluorophenyl)-3-(trifluoromethyl)-1H-pyrazole-5-carboxamide (69d) (250 mg, 87% yield) hydrochloride as a white solid; $^1H$ NMR (300 MHz, DMSO-$d_6$) δ 10.69 (s, 1H, $D_2O$ exchangeable), 8.60 (d, J=5.3 Hz, 1H), 8.46 (s, 3H, $D_2O$ exchangeable), 8.11 (s, 1H), 7.89 (s, 1H), 7.77 (d, J=7.3 Hz, 1H), 7.73 (d, J=2.2 Hz, 1H), 7.70 (s, 1H), 7.63 (dt, J=7.2, 1.7 Hz, 1H), 7.59-7.42 (m, 4H), 7.23 (t, J=9.5 Hz, 1H), 4.11 (q, J=5.8 Hz, 2H), 2.47-2.35 (m, 2H), 1.20-1.04 (m, 1H), 1.04-0.86 (m, 1H), 0.60 (q, J=7.3, 6.8 Hz, 1H), 0.33 (dt, J=8.4, 2.8 Hz, 2H), −0.07 (d, J=4.5 Hz, 2H); $^{19}F$ NMR (282 MHz, DMSO-$d_6$) δ −60.80, −123.19; MS (ES+) 554.3 (M+10), (ES−) 552.2 (M−1), 588.3 (M+Cl). Analysis calculated for $C_{29}H_{27}F_4N_5O_2$·2HCl 1.75$H_2O$: C, 52.99; H, 4.98; Cl, 10.65; N, 10.66; Found: C, 53.07; H, 5.06; Cl, 10.88; N, 10.45.

2. Peak-2 assigned as (+)-1-(3-(aminomethyl)phenyl)-N-(5-(3-cyclopropyl-1-hydroxy-1-(pyridin-2-yl)propyl)-2-fluorophenyl)-3-(trifluoromethyl)-1H-pyrazole-5-carboxamide (69e) (464 mg 90% ee) was purified by flash column chromatography (silica gel 12 g, eluting 0-30% MeOH in chloroform for 15 min) to afford 345 mg of (69e) as freebase isolated. $^1H$ NMR (300 MHz, DMSO-$d_6$) δ 10.58 (s, 1H, $D_2O$ exchangeable), 8.54-8.45 (m, 1H), 7.77-7.68 (m, 2H), 7.67-7.61 (m, 3H), 7.59-7.52 (m, 1H), 7.51-7.37 (m, 3H), 7.25-7.11 (m, 2H), 5.84 (s, 1H, $D_2O$ exchangeable), 4.01 (s, 2H), 2.44-2.27 (m, 2H), 1.02 (s, 2H), 0.68-0.50 (m, 1H), 0.41-0.23 (m, 2H), −0.11 (q, J=4.7 Hz, 2H); $^{19}F$ NMR (282 MHz, DMSO-$d_6$) δ −60.78, −124.06; MS (ES$^+$): MS (ES+) 554.3 (M+1), MS (ES−) 552.2 (M−1), 588.2 (M+Cl); Optical rotation: $[α]_D$=(+) 1.81 [$CH_3OH$, 1.1]. To a stirred solution of 69e (303 mg) in methanol (10 mL) to this 2 N HCl (2.74 mL, 5.47 mmol) was added and stirred for 10 min and evaporated to dryness to (S)-1-(3-(aminomethyl)phenyl)-N-(5-(3-cyclopropyl-1-hydroxy-1-(pyridin-2-yl)propyl)-2-fluorophenyl)-3-(trifluoromethyl)-1H-pyrazole-5-carboxamide (69e) (0.269 g, 89% yield) as an off-white solid as HCl salt; $^1H$ NMR (300 MHz, DMSO-$d_6$) δ 10.74 (s, 1H), 8.73-8.44 (m, 4H), 8.24 (s, 1H), 7.99 (s, 1H), 7.87-7.43 (m, 8H), 7.25 (dd, J=10.2, 8.7 Hz, 1H), 4.11 (q, J=5.8 Hz, 2H), 2.50 (d, J=1.9 Hz, 2H), 1.14 (s, 1H), 0.95 (td, J=12.5, 6.0 Hz, 1H), 0.72-0.53 (m, 1H), 0.33 (dt, J=8.4, 2.7 Hz, 2H), −0.06 (h, J=3.6 Hz, 2H); 1H NMR (300 MHz, DMSO-$d_6$, $D_2O$) δ 8.65 (dd, J=5.5, 1.6 Hz, 1H), 8.33 (td, J=7.9, 1.7 Hz, 1H), 8.01 (d, J=8.1 Hz, 1H), 7.83-7.68 (m, 3H), 7.65-7.57 (m, 3H), 7.56-7.44 (m, 2H), 7.35-7.22 (m, 1H), 4.12 (s, 2H), 2.54-2.40 (m, 2H), 1.16 (ddd, J=17.6, 14.4, 8.1 Hz, 1H), 0.96 (tt, J=12.5, 5.7 Hz, 1H), 0.63 (td, J=7.6, 4.0 Hz, 1H), 0.36 (ddt, J=8.6, 5.6, 2.8 Hz, 2H), −0.05 (dd, J=5.7, 3.7 Hz, 2H); 19F NMR (282 MHz, DMSO-$d_6$) δ −60.80, −122.61; MS (ES$^+$): MS (ES+) 554.3 (M+1), MS (ES−) 552.3 (M−1), 588.2 (M+Cl); HPLC: Chiral Purity 90% ee; Chiral HPLC: AD-H column 90/10/0.2 (Hexane/ethanol/TEA) 0.8 mL/min UV 260 nM, 45 mins run time (Temp 40° C.). Rt=16.88 (Peak-1, 95.03%); Rt=19.99 (peak-2 4.96%) 90% ee; Reverse phase HPLC Rt=6.97 (95.01%); Analysis calculated for $C_{29}H_{27}F_4N_5O_2$·2HCl·2$H_2O$: C, 52.57; H, 5.02; Cl, 10.70; N, 10.57; Found: C, 52.95; H, 5.01; Cl, 10.85; N, 10.50.

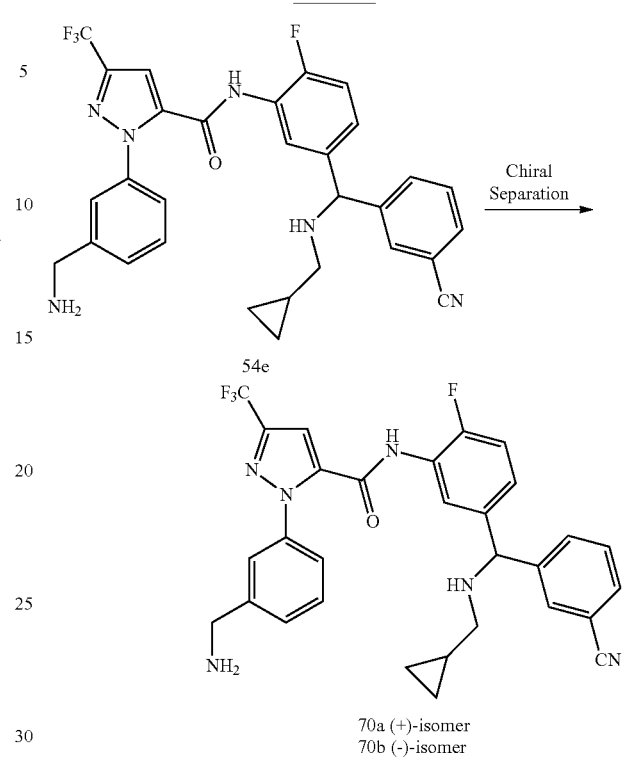

Scheme 70

54e 70a (+)-isomer
70b (−)-isomer

Preparation of (+)-1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (70a) and (−)-1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (70b)

Isomers of Racemic 1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (54e) (0.4 g) were separated by using preparative SFC method using the following conditions to furnish:

Preparative SFC Method Used:

| Column | 20 mm × 25.0 cm ChromegaChiral CCS from Regis Technologies (Morton Grove, IL) |
|---|---|
| $CO_2$ Co-solvent (Solvent B) | Methanol:Isopropanol (1:1) with 1% Isopropylamine |
| Isocratic Method | 20% Co-solvent at 80 mL/min |
| System Pressure | 200 bar |
| Column Temperature | 25° C. |
| Sample Diluent | Methanol:Isopropanol |

Chiral Purity of peaks was determined by following Analytical SFC Method:

| Column | 4.6 × 100 mm ChiralPak AS from Chiral Technologies (West Chester, PA) |
|---|---|
| $CO_2$ Co-solvent (Solvent B) | Methanol:Isopropanol (1:1) with 0.1% Isopropylamine |
| Isocratic Method | 5-65% Co-solvent Gradient at 4 mL/min |

| | | | | |
|---|---|---|---|---|
| System Pressure | 100 bar | | | |
| Column Temperature | 25° C. | | | |
| Sample Diluent | Methanol | | | |
| Peak-1 (70a) | 2.1 min | 144 mg | >95% ee (UV 254) | 98.6% purity (UV 254) |
| Peak-2 (70b) | 2.4 min | 172 mg | 95.5% ee (UV 254) | 96.5% purity (UV 254) |

1. Peak-1 assigned as (+)-1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (70a) (144 mg, >95% ee) free base as white solid; Optical rotation: [α]$_D$=(+) 6.83 [CH$_3$OH, 1.2]; $^1$H NMR (300 MHz, DMSO-d$_6$) δ 10.53 (s, 1H, D$_2$O exchangeable), 7.88 (t, J=1.7 Hz, 1H), 7.77-7.71 (m, 1H), 7.67 (dt, J=7.7, 1.4 Hz, 1H), 7.63 (dd, J=7.5, 2.1 Hz, 1H), 7.56 (s, 1H), 7.54-7.47 (m, 2H), 7.47-7.38 (m, 2H), 7.34 (ddt, J=8.6, 5.9, 2.8 Hz, 2H), 7.22 (dd, J=10.3, 8.5 Hz, 1H), 4.93 (s, 1H), 3.77 (s, 2H), 2.31-2.21 (m, 2H), 0.97-0.80 (m, 1H), 0.42-0.33 (m, 2H), 0.10--0.02 (m, 2H); $^{19}$F NMR (282 MHz, DMSO-d$_6$) δ −60.73, −123.20; MS (ES+) 563.3 (M+1), 561.3 (M−1). To a solution of free base of (+)-1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (70a) (120 mg) in methanol (15 mL) was added hydrogen chloride (0.969 mL, 1.938 mmol), stirred at room temperature for 10 min, evaporated to dryness to afford (+)-1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (70a) (100 mg) hydrochloride salt as white solid; $^1$H NMR (300 MHz, DMSO-d$_6$) δ 10.84 (s, 1H, D$_2$O exchangeable), 10.44 (s, 2H, D$_2$O exchangeable), 8.44 (s, 3H, D$_2$O exchangeable), 8.30 (s, 1H, D$_2$O exchangeable), 8.09 (d, J=7.9 Hz, 1H), 7.99 (d, J=6.8 Hz, 1H), 7.91-7.83 (m, 1H), 7.80-7.50 (m, 7H), 7.42 (dd, J=10.3, 8.6 Hz, 1H), 5.78 (d, J=6.9 Hz, 1H), 4.13 (d, J=5.7 Hz, 2H), 2.88-2.62 (m, 2H), 1.42-0.99 (m, 1H), 0.73-0.46 (m, 2H), 0.32 (d, J=4.4 Hz, 2H); $^{19}$F NMR (282 MHz, DMSO-d$_6$) δ −60.81, −119.99; MS (ES+): MS (ES+) 563.3 (M+1), MS (ES−) 561.3 (M−1), 597.3 (M+Cl); Analysis calculated for C$_{30}$H$_{26}$F$_4$N$_6$O.2HCl.1.75H$_2$O: C, 54.02; H, 4.76; Cl, 10.63; N, 12.60; Found: C, 54.12; H, 4.83; Cl, 10.10; N, 11.97.

2. Peak-2 assigned as (−)-1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (70b) (172 mg, 95.5% ee) as free base was repurified by flash column chromatography (silica gel 12 g, eluting 0-30% MeOH in chloroform for 15 min) to afford (−)-1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (70b) free base as an off-white solid; Optical rotation: [α]$_D$=(−) 5.44 [CH$_3$OH, 1.25]; $^1$H NMR (300 MHz, DMSO-d$_6$) δ 7.88 (t, J=1.6 Hz, 1H), 7.74 (d, J=8.1 Hz, 1H), 7.70-7.61 (m, 2H), 7.57 (s, 1H), 7.54-7.47 (m, 2H), 7.45-7.41 (m, 2H), 7.34 (ddq, J=8.7, 6.1, 3.5, 2.8 Hz, 2H), 7.22 (dd, J=10.3, 8.5 Hz, 1H), 4.93 (s, 1H), 3.78 (s, 2H), 2.25 (d, J=6.9 Hz, 2H), 0.90 (ddd, J=9.8, 8.0, 5.2 Hz, 1H), 0.47-0.29 (m, 2H), 0.04 (dd, J=5.0, 1.5 Hz, 2H); $^{19}$F NMR (282 MHz, DMSO-d$_6$) δ −60.73, −123.19; MS (ES+) 563.3 (M+1), MS (ES−), 561.3 (M−1). To a solution of free base of (−)-1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (70b) (0.124 g, 0.220 mmol) in methanol (15 mL) was added hydrogen chloride (1.102 mL, 2.204 mmol), stirred at room temperature for 10 min, evaporated to dryness to afford (−)-1-(3-(aminomethyl)phenyl)-N-(5-((3-cyanophenyl)(cyclopropyl-methylamino)methyl)-2-fluorophenyl)-3-(trifluoromethyl)-1H-pyrazole-5-carboxamide (70b) (0.121 g) hydrochloride salt as an off-white solid; $^1$H NMR: $^1$H NMR (300 MHz, DMSO-d$_6$) δ 10.82 (s, 1H, D$_2$O exchangeable), 10.36 (s, 2H, D$_2$O exchangeable), 8.38 (s, 3H, D$_2$O exchangeable), 8.27 (s, 1H), 8.06 (d, J=7.9 Hz, 1H), 7.98 (d, J=6.7 Hz, 1H), 7.87 (d, J=7.7 Hz, 1H), 7.78-7.49 (m, 7H), 7.48-7.37 (m, 1H), 5.78 (s, 1H), 4.13 (d, J=5.7 Hz, 2H), 2.72 (s, 2H), 1.14 (s, 1H), 0.56 (d, J=7.7 Hz, 2H), 0.31 (d, J=5.0 Hz, 2H); $^{19}$F NMR (282 MHz, DMSO-d$_6$) δ −60.82, −120.03; MS (ES$^+$): MS (ES+) 563.3 (M+1), MS (ES−), 561.3 (M−1), 597.2 (M+Cl); Analysis calculated for C$_{30}$H$_{26}$F$_4$N$_6$O.2HCl.1.75H$_2$O: C, 54.02; H, 4.76; Cl, 10.63; N, 12.60; Found: C, 54.12; H, 4.83; Cl, 10.10; N, 11.97.

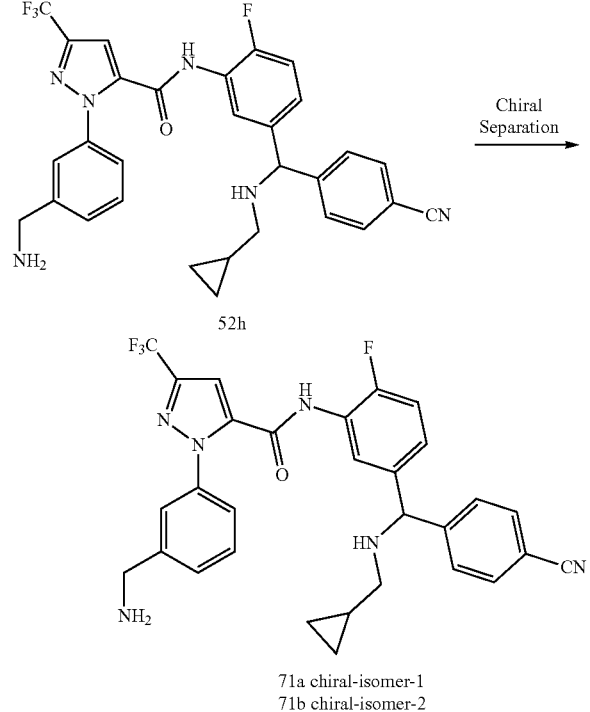

Scheme 71

52h 71a chiral-isomer-1
71b chiral-isomer-2

Preparation of chiral isomer-1 1-(3-(aminomethyl)phenyl)-N-(5-((4-cyanophenyl)(cyclopropyl-methylamino)methyl)-2-fluorophenyl)-3-(trifluoromethyl)-1H-pyrazole-5-carboxamide (71a) and chiral isomer-2 1-(3-(aminomethyl)phenyl)-N-(5-((4-cyanophenyl)(cyclopropyl-methylamino)methyl)-2-fluorophenyl)-3-(trifluoromethyl)-1H-pyrazole-5-carboxamide (71b)

Isomers of Racemic 1-(3-(aminomethyl)phenyl)-N-(5-((4-cyanophenyl)(cyclopropyl-methylamino)methyl)-2- fluorophenyl)-3-(trifluoromethyl)-1H-pyrazole-5-carboxamide (52h) (235 mg) were separated into pure chiral isomers using preparative SFC method using the following conditions to furnish:

Preparative SFC Method:

| Column | 20 mm × 25.0 cm Chromega Chiral CCS from Regis Technologies (Morton Grove, IL) |
| --- | --- |
| CO₂ Co-solvent (Solvent B) | Methanol:Isopropanol (1:1) with 1% Isopropylamine |
| Isocratic Method | 20% Co-solvent at 80 mL/min |
| System Pressure | 100 bar |
| Column Temperature | 25° C. |
| Sample Diluent | Methanol |

Chiral Purity of Peaks was Determined by Following Analytical SFC Method:

| Column | 4.6 × 100 mm ChiralPak AS from Chiral Technologies (West Chester, PA) |
| --- | --- |
| CO₂ Co-solvent (Solvent B) | Methanol:Isopropanol (1:1) with 0.1% Isopropylamine |
| Isocratic Method | 5-65% Co-solvent Gradient at 4 mL/min |
| System Pressure | 100 bar |
| Column Temperature | 25° C. |
| Sample Diluent | Methanol |

| | | | | |
| --- | --- | --- | --- | --- |
| Peak-1 (71a) | 2.2 min | 46 mg | >95% ee (UV 254) | 81.9% purity (UV 254) |
| Peak-2 (71b) | 2.4 min | 57 mg | 97.7% ee (UV 254) | 98.5% purity (UV 254) |

1. Peak-1 assigned as chiral isomer-1 1-(3-(aminomethyl)phenyl)-N-(5-((4-cyanophenyl)(cyclopropyl-methylamino)methyl)-2-fluorophenyl)-3-(trifluoromethyl)-1H-pyrazole-5-carboxamide (71a) (46 mg >95 ee) was repurified by flash column chromatography (silica gel 4 g, eluting with CMA 80 in chloroform 0 to 30%) to afford pure chiral isomer-1 1-(3-(aminomethyl)phenyl)-N-(5-((4-cyanophenyl)(cyclopropyl-methylamino)methyl)-2-fluorophenyl)-3-(trifluoromethyl)-1H-pyrazole-5-carboxamide (71a) (34 mg) free base as white solid; $^1$H NMR (300 MHz, DMSO-$d_6$) δ 7.77 (d, J=7.3 Hz, 2H), 7.66-7.56 (m, 4H), 7.56 (s, 1H), 7.51 (s, 1H), 7.49-7.38 (m, 2H), 7.37-7.27 (m, 3H), 7.21 (dd, J=10.2, 8.5 Hz, 1H), 4.95 (s, 1H), 3.77 (s, 2H), 2.25 (d, J=6.7 Hz, 3H), 0.95-0.84 (m, 1H), 0.43-0.30 (m, 2H), 0.10--0.01 (m, 1H); MS (ES+) 563.3 (M+1), (ES−) 561.3 (M−1). To a solution of free base of chiral isomer-1 1-(3-(aminomethyl)phenyl)-N-(5-((4-cyanophenyl)(cyclopropyl-methylamino)methyl)-2-fluorophenyl)-3-(trifluoromethyl)-1H-pyrazole-5-carboxamide (71a) (34 mgs) in methanol (2 mL) and added hydrochloric acid in methanol (2 M 0.3 mL), stirred for 15 mins and concentrated to remove excess hydrochloric acid. The residue was dried to give chiral isomer-1 1-(3-(aminomethyl)phenyl)-N-(5-((4-cyanophenyl)(cyclopropyl-methylamino)methyl)-2-fluorophenyl)-3-(trifluoromethyl)-1H-pyrazole-5-carboxamide (71a) hydrochloride salt as a white solid; $^1$H NMR (300 MHz, DMSO-$d_6$) δ 10.84 (s, 1H), 10.49 (s, 2H), 8.47 (s, 3H), 8.04-7.90 (m, 5H), 7.82-7.68 (m, 3H), 7.63 (dt, J=7.4, 1.7 Hz, 1H), 7.60-7.49 (m, 2H), 7.41 (dd, J=10.2, 8.6 Hz, 1H), 5.83 (t, J=6.6 Hz, 1H), 4.13 (q, J=5.8 Hz, 2H), 2.71 (q, J=6.0, 4.6 Hz, 2H), 1.18 (td, J=13.9, 12.8, 7.3 Hz, 1H), 0.55 (dt, J=8.3, 3.1 Hz, 2H), 0.32 (t, J=5.0 Hz, 2H); $^{19}$F NMR (282 MHz, DMSO-$d_6$) δ −60.81, −120.01; Analysis calculated for $C_{30}H_{26}F_4N_6O \cdot 2HCl \cdot 2.75H_2O$: C, 52.65; H, 4.93; Cl, 10.22; N, 12.28; Found: C, 52.95; H, 4.87; Cl, 11.61; N, 10.06.

2. Peak-2 assigned as chiral isomer-2 1-(3-(aminomethyl)phenyl)-N-(5-((4-cyanophenyl)(cyclopropyl-methylamino)methyl)-2-fluorophenyl)-3-(trifluoromethyl)-1H-pyrazole-5-carboxamide (71b) (57 mg, 97.7% ee) free base as white solid; $^1$H NMR (300 MHz, DMSO-$d_6$) δ 10.54 (s, 1H), 7.80-7.74 (m, 2H), 7.61 (d, J=7.8 Hz, 3H), 7.57 (s, 1H), 7.52 (s, 1H), 7.43 (d, J=6.9 Hz, 2H), 7.35-7.30 (m, 2H), 7.22 (t, J=9.5 Hz, 1H), 4.95 (s, 1H), 3.79 (s, 2H), 2.25 (d, J=7.0 Hz, 2H), 0.90 (s, 1H), 0.41-0.33 (m, 2H). To a solution of free base of chiral isomer-2 1-(3-(aminomethyl)phenyl)-N-(5-((4-cyanophenyl)(cyclopropyl-methylamino)methyl)-2-fluorophenyl)-3-(trifluoromethyl)-1H-pyrazole-5-carboxamide (71b) in methanol (2 mL) was added hydrochloric acid in methanol (2 M, 0.5 mL), stirred for 15 mins and concentrated in vacuum to remove excess hydrochloric acid. The residue was dried to give chiral isomer-2 1-(3-(aminomethyl)phenyl)-N-(5-((4-cyanophenyl)(cyclopropyl-methylamino)methyl)-2-fluorophenyl)-3-(trifluoromethyl)-1H-pyrazole-5-carboxamide (71b) (50 mgs) hydrochloride salt as a white solid; 1H NMR (300 MHz, DMSO-$d_6$) δ 10.83 (d, J=5.2 Hz, 1H, $D_2O$ exchangeable), 10.45 (s, 2H, $D_2O$ exchangeable), 8.45 (s, 3H, $D_2O$ exchangeable), 8.04-7.89 (m, 5H), 7.81-7.67 (m, 3H), 7.66-7.60 (m, 1H), 7.59-7.48 (m, 2H), 7.47-7.36 (m, 2H), 5.81 (d, J=6.8 Hz, 1H), 4.13 (q, J=5.7 Hz, 2H), 2.71 (q, J=6.2, 5.2 Hz, 2H), 1.15 (td, J=8.1, 5.2 Hz, 1H), 0.64-0.49 (m, 2H), 0.32 (t, J=5.0 Hz, 2H); 19F NMR (282 MHz, DMSO-$d_6$) δ −60.79, −120.01; MS (ES+) 563.3 (M+1), 585.3 (M+Na), 561.3 (M−1), 597.3 (M+Cl); Analysis calculated for $C_{30}H_{26}F_4N_6O \cdot 1.95HCl \cdot 1.75H_2O$: C, 53.80; H, 4.81; Cl, 10.32; N, 12.55; Found: C, 54.09; H, 4.94; Cl, 10.13; N, 11.42.

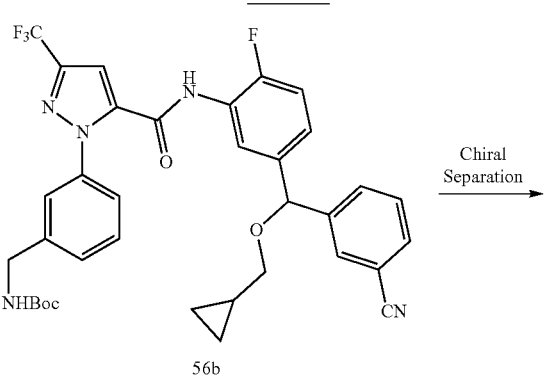

Scheme 72

56b

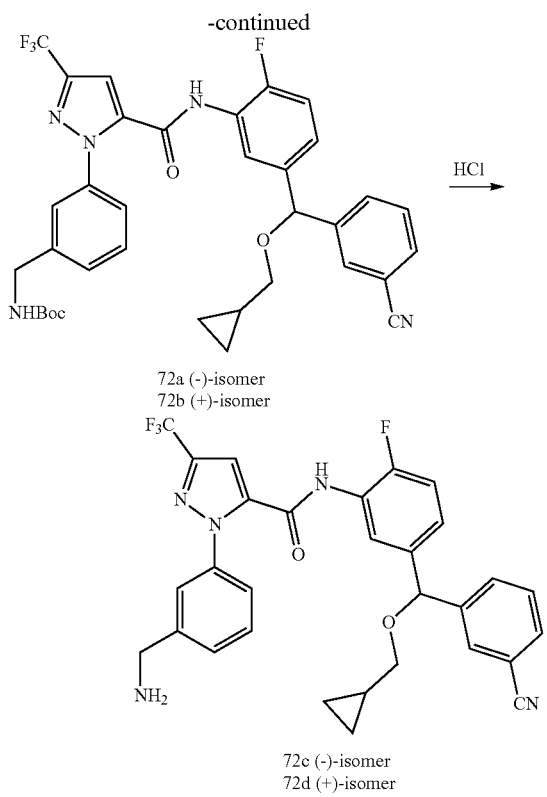

72a (−)-isomer
72b (+)-isomer 72c (−)-isomer
72d (+)-isomer

Preparation of (−)-1-(3-(aminomethyl)phenyl)-N-(5-((3-cyanophenyl)(cyclopropylmethoxy)methyl)-2-fluorophenyl)-3-(trifluoromethyl)-1H-pyrazole-5-carboxamide (72c) and (+)-1-(3-(aminomethyl)phenyl)-N-(5-((3-cyanophenyl)(cyclopropylmethoxy)methyl)-2-fluorophenyl)-3-(trifluoromethyl)-1H-pyrazole-5-carboxamide (72d)

Isomers of Racemic tert-butyl 3-(5-(5-((3-cyanophenyl)(cyclopropylmethoxy)methyl)-2-fluorophenylcarbamoyl)-3-(trifluoromethyl)-1H-pyrazol-1-yl)benzylcarbamate (56b) (0.75 gm) were separated by preparative Chiral HPLC using the following preparative chromatography conditions to furnish:

| Column | CHIRALPAK AD-H; 5μ, 4.6 × 250 mm, flow rate 1 mL/min |
|---|---|
| Eluent | Hexane:Ethanol-Diethylamine (90:10:0.1) |
| Column Temperature | Room temperature |
| UV detection | 270 nm |

| Peak-1 (72a) | 8.849 min | 239 mg | >99% ee |
| Peak-2 (72b) | 11.589 min | 220 mg | 98.0% ee |

1. Peak-1 assigned as (−)-tert-butyl 3-(5-(5-((3-cyanophenyl)(cyclopropylmethoxy)methyl)-2-fluorophenylcarbamoyl)-3-(trifluoromethyl)-1H-pyrazol-1-yl)benzylcarbamate (72a) (239 mg >99% ee); Optical rotation: $[\alpha]_D=(-)$ 17.11 [CH$_3$OH, 0.83]; $^1$H NMR (300 MHz, DMSO-d$_6$) δ 10.60 (s, 1H), 7.82 (s, 1H), 7.74 (dt, J=7.5, 1.4 Hz, 1H), 7.70-7.65 (m, 1H), 7.64-7.23 (m, 10H), 5.58 (s, 1H), 4.19 (d, J=6.2 Hz, 2H), 3.24 (d, J=6.8 Hz, 2H), 1.37 (s, 9H), 1.11-0.95 (m, 1H), 0.52-0.40 (m, 2H), 0.18-0.11 (m, 2H); $^{19}$F NMR (282 MHz, DMSO-d$_6$) δ −60.82, −122.29; (ES+) 686.3 (M+23). To a solution of (−)-tert-butyl 3-(5-(5-((3-cyanophenyl)(cyclopropylmethoxy)methyl)-2-fluorophenylcarbamoyl)-3-(trifluoromethyl)-1H-pyrazol-1-yl)benzylcarbamate (72a) (230 mg, 0.347 mmol) in methanol (25 mL) was added conc. hydrogen chloride (0.180 mL, 2.156 mmol) and stirred at room temperature for 19 h, (~20% conversion by TLC). The reaction mixture was concentrated under vacuum to dryness (at <30° C., ~50% conversion by TLC). To the residue was added conc. HCl (0.15 mL, 1.8 mmol) stirred at room temperature for 0.5 h and concentrated in vacuum to dryness. The residue obtained was purified by flash column chromatography [silica gel 4 g, eluting with chloroform/CMA80 (1:0 to 3:1)] to afford free base of (−)-1-(3-(aminomethyl)phenyl)-N-(5-((3-cyanophenyl)(cyclopropylmethoxy)methyl)-2-fluorophenyl)-3-(trifluoromethyl)-1H-pyrazole-5-carboxamide (72c) (95 mg) as a white solid; Optical rotation: $[\alpha]_D=(-)$ 15.92 [CH$_3$OH, 0.515]; $^1$H NMR (300 MHz, DMSO-d$_6$) δ 10.59 (s, 1H), 7.81 (t, J=1.7 Hz, 1H), 7.74 (dt, J=7.6, 1.5 Hz, 1H), 7.67 (dt, J=8.1, 1.5 Hz, 1H), 7.63-7.50 (m, 4H), 7.43 (q, J=1.5 Hz, 1H), 7.40 (d, J=7.6 Hz, 1H), 7.35-7.22 (m, 3H), 5.59 (s, 1H), 3.77 (s, 2H), 3.23 (d, J=6.8 Hz, 2H), 1.14-0.95 (m, 1H), 0.59-0.34 (m, 2H), 0.26-0.04 (m, 2H); $^{19}$F NMR (282 MHz, DMSO-d$_6$) δ −60.75, −122.42; MS (ES+) 564.2 (M+1); (ES−) 562.1 (M−1). To a solution of free base of (−)-1-(3-(aminomethyl)phenyl)-N-(5-((3-cyanophenyl)(cyclopropylmethoxy)methyl)-2-fluorophenyl)-3-(trifluoromethyl)-1H-pyrazole-5-carboxamide (72c) (70 mg) in methanol (10 mL) was added 4 N HCl (aq. 0.12 mL) and concentrated in vacuum to dryness to furnish (−)-1-(3-(aminomethyl)phenyl)-N-(5-((3-cyanophenyl)(cyclopropylmethoxy)methyl)-2-fluorophenyl)-3-(trifluoromethyl)-1H-pyrazole-5-carboxamide (72c) (78 mg) hydrochloride salt as a white solid; Optical rotation: $[\alpha]_D=(-)$ 9.72 [CH$_3$OH, 0.535]; $^1$H NMR (300 MHz, DMSO-d$_6$) δ 10.49 (s, 1H), 8.08 (s, 3H), 7.66 (t, J=1.7 Hz, 1H), 7.59 (dt, J=7.6, 1.5 Hz, 1H), 7.56-7.50 (m, 3H), 7.46-7.32 (m, 5H), 7.19-7.06 (m, 2H), 5.43 (s, 1H), 3.96 (s, 2H), 3.08 (d, J=6.8 Hz, 2H), 0.97-0.80 (m, 1H), 0.37-0.22 (m, 2H), 0.02 to −0.04 (m, 2H). 19F NMR (282 MHz, DMSO-d$_6$) δ −60.83, −121.94; MS (ES+): 564.2 (M+1); Analysis calculated for C$_{30}$H$_{25}$F$_4$N$_5$O$_2$.1.15HCl.1.25H$_2$O: C, 57.38; H, 4.60; Cl, 6.49; N, 11.15; Found C, 57.01; H, 4.63; Cl, 6.11; N, 10.82.

2. Peak-2 assigned as (+)-tert-butyl 3-(5-(5-((3-cyanophenyl)(cyclopropylmethoxy)methyl)-2-fluorophenylcarbamoyl)-3-(trifluoromethyl)-1H-pyrazol-1-yl)benzylcarbamate (72b) (220 mg, 98.0% ee); Optical rotation: $[\alpha]_D=(+)$ 17.14 [CH$_3$OH, 0.70]; $^1$H NMR (300 MHz, DMSO-d$_6$) δ 10.60 (s, 1H), 7.82 (s, 1H), 7.74 (dt, J=7.6, 1.5 Hz, 1H), 7.70-7.65 (m, 1H), 7.65-7.22 (m, 10H), 5.58 (s, 1H), 4.19 (d, J=6.2 Hz, 2H), 3.24 (d, J=6.8 Hz, 2H), 1.37 (s, 9H), 1.14-0.90 (m, 1H), 0.54-0.38 (m, 2H), 0.18-0.11 (m, 2H); $^{19}$F NMR (282 MHz, DMSO-d$_6$) δ −60.82, −122.34; (ES+) 686.3 (M+23). To a solution of (+)-tert-butyl 3-(5-(5-((3-cyanophenyl)(cyclopropylmethoxy)methyl)-2-fluorophenylcarbamoyl)-3-(trifluoromethyl)-1H-pyrazol-1-yl)benzylcarbamate (72b) (210 mg, 0.316 mmol) in methanol (23 mL) was added conc. hydrogen chloride (0.160 mL, 1.914 mmol) and stirred at room temperature for 19 h, (~20% conversion by TLC). The reaction mixture was concentrated under vacuum to dryness (at <30° C., ~50% conversion by TLC). To the residue was added conc. HCl (0.13 mL, 1.56 mmol) stirred at room temperature for 10 min and concentrated in vacuum to dryness. The residue obtained was purified by flash column chromatography [silica gel 4 g, eluting with chloroform/CMA80 (1:0 to 3:1)] to afford free base (+)-1-(3-(aminomethyl)phenyl)-N-(5-((3-cyanophenyl)(cyclopropylmethoxy)methyl)-2-fluorophenyl)-3-(trifluoromethyl)-1H-pyrazole-5-carboxamide (72d) (88 mg) as a white solid; Optical rotation: $[\alpha]_D$=(+) 19.59 [CH$_3$OH, 0.515]; $^1$H NMR (300 MHz, DMSO-d$_6$) δ 10.58 (s, 1H), 7.82 (t, J=1.7 Hz, 1H), 7.74 (dt, J=7.6, 1.5 Hz, 1H), 7.67 (dt, J=8.0, 1.5 Hz, 1H), 7.63-7.50 (m, 4H), 7.44 (q, J=1.4 Hz, 1H), 7.40 (d, J=7.5 Hz, 1H), 7.36-7.22 (m, 3H), 5.59 (s, 1H), 3.78 (s, 2H), 3.23 (d, J=6.8 Hz, 2H), 1.12-0.96 (m, 1H), 0.56-0.36 (m, 2H), 0.24-0.07 (m, 2H); $^{19}$F NMR (282 MHz, DMSO d$_6$) δ -60.76, -122.38; MS (ES+) 564.2 (M+1); (ES-) 562.2 (M-1); To a solution of free base of (+)-1-(3-(aminomethyl)phenyl)-N-(5-((3-cyanophenyl)(cyclopropylmethoxy)methyl)-2-fluorophenyl)-3-(trifluoromethyl)-1H-pyrazole-5-carboxamide (72d) (62 mg) in methanol (10 mL) was added 4 N HCl (aq. 0.11 mL) and concentrated in vacuum to dryness to (+)-1-(3-(aminomethyl)phenyl)-N-(5-((3-cyanophenyl)(cyclopropylmethoxy)methyl)-2-fluorophenyl)-3-(trifluoromethyl)-1H-pyrazole-5-carboxamide (72d) (68 mg) hydrochloride salt as a white solid; Optical rotation: $[\alpha]_D$=(+) 8.0 [CH$_3$OH, 0.325]; $^1$H NMR (300 MHz, DMSO-d$_6$) δ 10.66 (s, 1H), 8.29 (s, 3H), 7.81 (t, J=1.7 Hz, 1H), 7.77-7.64 (m, 4H), 7.59 (t, J=4.7 Hz, 3H), 7.55 (d, J=4.5 Hz, 1H), 7.54-7.46 (m, 1H), 7.30 (dd, J=4.7, 2.5 Hz, 1H), 7.25 (d, J=8.6 Hz, 1H), 5.59 (s, 1H), 4.12 (s, 2H), 3.23 (d, J=6.8 Hz, 2H), 1.13-0.96 (m, 1H), 0.55-0.36 (m, 2H), 0.26-0.03 (m, 2H); $^{19}$F NMR (282 MHz, DMSO-d$_6$) δ -60.85, -122.03; MS (ES+) 564.2 (M+1); (ES-) 562.2 (M-1); Calculated for $C_{30}H_{25}F_4N_5O_2HCl\cdot1.25H_2O$: C, 57.88; H, 4.61; Cl, 5.70; N, 11.25; Found C, 57.80; H, 4.57; Cl, 5.94; N, 11.05.

Scheme 73

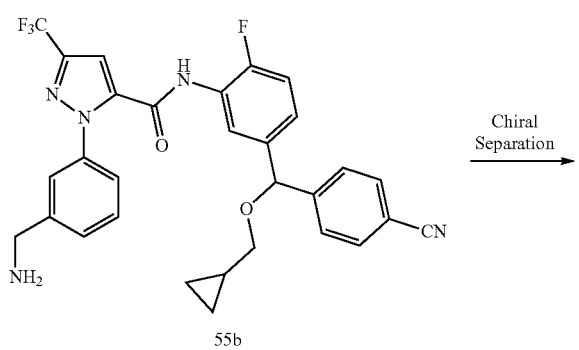

55b

Chiral Separation

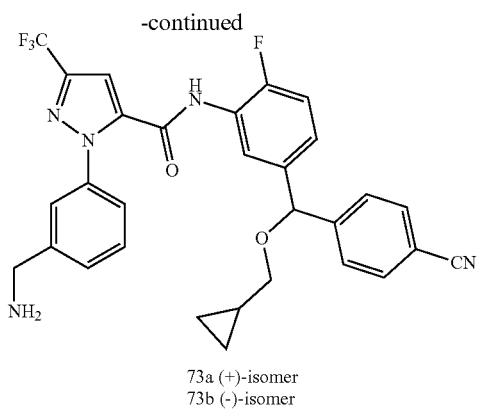

73a (+)-isomer
73b (-)-isomer

Preparation of (+)-1-(3-(aminomethyl)phenyl)-N-(5-((4-cyanophenyl)(cyclopropylmethoxy)methyl)-2-fluorophenyl)-3-(trifluoromethyl)-1H-pyrazole-5-carboxamide (73a) and (-)-1-(3-(aminomethyl)phenyl)-N-(5-((4-cyanophenyl)(cyclopropylmethoxy)methyl)-2-fluorophenyl)-3-(trifluoromethyl)-1H-pyrazole-5-carboxamide (73b)

Isomers of Racemic 1-(3-(aminomethyl)phenyl)-N-(5-((4-cyanophenyl)(cyclopropylmethoxy)methyl)-2-fluorophenyl)-3-(trifluoromethyl)-1H-pyrazole-5-carboxamide (55b) (400 mg) were separated into pure chiral isomers using preparative SFC method using the following method to furnish:

Preparative SFC Method Used:

| Column | 3.0 × 25.0 cm CCS from ES Industries (West Berlin, NJ) |
| --- | --- |
| CO2 Co-solvent (Solvent B) | Acetonitrile:Methanol (1:1) with 1% Isopropylamine |
| Isocratic Method | 25% Co-solvent at 80 mL/min |
| System Pressure | 100 bar |
| Column Temperature | 25° C. |
| Sample Diluent | Methanol |

Chiral Purity of Peaks was Determined by Following Analytical SFC Method:

| Column | 4.6 × 100 mm CCS from ES Industries (West Berlin, NJ) |
| --- | --- |
| CO$_2$ Co-solvent (Solvent B) | Acetonitrile:Methanol (1:1) with 0.1% Isopropylamine |
| Isocratic Method | 20% Co-solvent at 4 mL/min |
| System Pressure | 100 bar |
| Column Temperature | 25° C. |
| Sample Diluent | Methanol |

| | | | | |
| --- | --- | --- | --- | --- |
| Peak-1 (73a) | 4.2 min | 77 mg | >95% ee (UV 254) | 96.4% purity (UV 254) |
| Peak-2 (73b) | 4.9 min | 100 mg | >95% ee (UV 254) | 96.4% purity (UV 254) |

1. Peak-1 assigned as (+)-1-(3-(aminomethyl)phenyl)-N-(5-((4-cyanophenyl)(cyclopropylmethoxy)methyl)-2-fluorophenyl)-3-(trifluoromethyl)-1H-pyrazole-5-carboxamide (73a) (77 mg >95 ee) was repurified by flash column chromatography (silica gel 4 g, eluting with CMA 80 in chloroform 0 to 30%) to afford free base of (+)-1-(3-(aminomethyl)phenyl)-N-(5-((4-cyanophenyl)(cyclopropylmethoxy)methyl)-2-fluorophenyl)-3-

(trifluoromethyl)-1H-pyrazole-5-carboxamide (73a) (43 mg) as a white solid; Optical rotation: [α]$_D$=(+) 15.38 [CH$_3$OH, 1.3]; $^1$H NMR (300 MHz, DMSO-d$_6$) δ 7.85-7.78 (m, 2H), 7.62-7.56 (m, 4H), 7.53 (d, J=4.7 Hz, 2H), 7.48-7.41 (m, 2H), 7.35 (d, J=2.3 Hz, 1H), 7.28 (dd, J=7.0, 1.6 Hz, 2H), 5.61 (s, 1H), 3.80 (s, 2H), 3.24 (d, J=6.8 Hz, 2H), 1.04 (q, J=4.6, 2.7 Hz, 1H), 0.54-0.38 (m, 2H), 0.24-0.09 (m, 2H); $^{19}$F NMR (282 MHz, DMSO-d$_6$) δ −60.75, −122.33. MS (ES+) 564.2 (M+1), 562.2 (M−1); To a solution of free base of (+)-1-(3-(aminomethyl)phenyl)-N-(5-((4-cyanophenyl)(cyclopropylmethoxy)methyl)-2-fluorophenyl)-3-(trifluoromethyl)-1H-pyrazole-5-carboxamide (73a) (26 mg) in methanol (4 mL) was added 2 N HCl (0.11 mL, 5 eq.), stirred for 15 mins and concentrated in vacuum to dryness to afford (+)-1-(3-(aminomethyl)phenyl)-N-(5-((4-cyanophenyl)(cyclopropylmethoxy)methyl)-2-fluorophenyl)-3-(trifluoromethyl)-1H-pyrazole-5-carboxamide (73a) (22 mg) hydrochloride salt as an off-white solid; $^1$H NMR (300 MHz, DMSO-d$_6$) δ 10.68 (s, 1H), 8.38 (s, 4H), 7.83 (d, J=1.8 Hz, 1H), 7.81 (d, J=1.8 Hz, 1H), 7.72 (t, J=1.8 Hz, 1H), 7.67 (s, 1H), 7.64-7.47 (m, 6H), 7.29 (d, J=1.2 Hz, 1H), 7.29-7.25 (m, 1H), 5.61 (s, 1H), 4.12 (s, 2H), 3.24 (d, J=6.8 Hz, 2H), 1.12-0.95 (m, 1H), 0.52-0.36 (m, 2H), 0.22-0.05 (m, 2H); $^{19}$F NMR (282 MHz, DMSO-d$_6$) δ −60.83, −121.91; MS (ES+) 564.3 (M+1), (ES−) 562.2 (M−1); Analysis calculated for C$_{30}$H$_{25}$F$_4$N$_5$O$_2$.HCl.0.75H$_2$O: C, 58.73; H, 4.52; N, 11.42; Found: C, 58.72; H, 4.72; N, 11.10.

2. Peak-2 assigned as (−)-1-(3-(aminomethyl)phenyl)-N-(5-((4-cyanophenyl)(cyclopropylmethoxy)methyl)-2-fluorophenyl)-3-(trifluoromethyl)-1H-pyrazole-5-carboxamide (73b) (100 mg, >95% ee) was repurified by flash column chromatography (silica gel 12 g, eluting with 0-30% methanol in chloroform) to furnish (−)-1-(3-(aminomethyl)phenyl)-N-(5-((4-cyanophenyl)(cyclopropylmethoxy)methyl)-2-fluorophenyl)-3-(trifluoromethyl)-1H-pyrazole-5-carboxamide (73b) (0.063 g) free base as a white solid; Optical rotation: [α]$_D$=(−) 15.9 [CH$_3$OH, 1.3]; $^1$H NMR: $^1$H NMR (300 MHz, DMSO-d$_6$) δ 7.88-7.76 (m, 2H), 7.65-7.49 (m, 5H), 7.47-7.38 (m, 2H), 7.30 (ddd, J=16.1, 5.9, 2.0 Hz, 3H), 5.61 (s, 1H), 3.77 (s, 2H), 3.24 (d, J=6.8 Hz, 2H), 1.05 (dddd, J=11.7, 8.2, 6.8, 2.7 Hz, 1H), 0.56-0.36 (m, 2H), 0.24-0.08 (m, 2H); $^{19}$F NMR (282 MHz, DMSO-d$_6$) δ −60.74, −122.37; MS (ES$^+$): MS (ES+) 564.3 (M+1), MS (ES−) 562.2 (M−1). HPLC: HPLC (Modified 5191 method, Zorbax SB-C3, 3.0×150 mm, 5 mm, with a ZGC SB-C3, 2.1×12.5 mm guard cartridge, "A" Buffer=(98% of 0.1 M Ammonium Acetate in 2% acetonitrile) "B" Buffer=100% Acetonitrile, UV Absorbance 250 nm; Rt=19.89 min (99.33%)]. To a solution of free base of (−)-1-(3-(aminomethyl)phenyl)-N-(5-((4-cyanophenyl)(cyclopropylmethoxy)methyl)-2-fluorophenyl)-3-(trifluoromethyl)-1H-pyrazole-5-carboxamide (73b) (43 mg) in methanol (15 mL) was added 2 N HCl (0.19 mL, 5 eq.), stirred for 15 mins concentrated in vacuum to dryness to afford (−)-1-(3-(aminomethyl)phenyl)-N-(5-((4-cyanophenyl)(cyclopropylmethoxy)methyl)-2-fluorophenyl)-3-(trifluoromethyl)-1H-pyrazole-5-carboxamide (73b) (39 mg) hydrochloride salt as an off-white solid. $^1$H NMR (300 MHz, DMSO-d$_6$) δ 10.55 (s, 1H, D$_2$O exchangeable), 8.31 (s, 4H, D$_2$O exchangeable), 7.70-7.63 (m, 2H), 7.59-7.51 (m, 2H), 7.50-7.31 (m, 6H), 7.17-7.06 (m, 2H), 5.46 (s, 1H), 3.95 (q, J=5.4 Hz, 2H), 3.08 (d, J=6.8 Hz, 2H), 0.89 (dddd, J=14.8, 6.7, 3.4, 2.0 Hz, 1H), 0.41-0.20 (m, 2H), 0.09--0.08 (m, 2H); $^{19}$F NMR (282 MHz, DMSO-d$_6$) δ −60.82, −121.84; MS (ES+) 564.3 (M+1), MS (ES−) 562.3 (M−1), 598.2 (M+Cl). Analysis calculated for: C$_{30}$H$_{25}$F$_4$N$_5$O$_2$.H$_2$O.HCl: C, 58.30; H, 4.57; Cl, 5.74; N, 11.33; Found: C, 58.46; H, 4.71; Cl, 5.93; N, 11.22.

Scheme 74

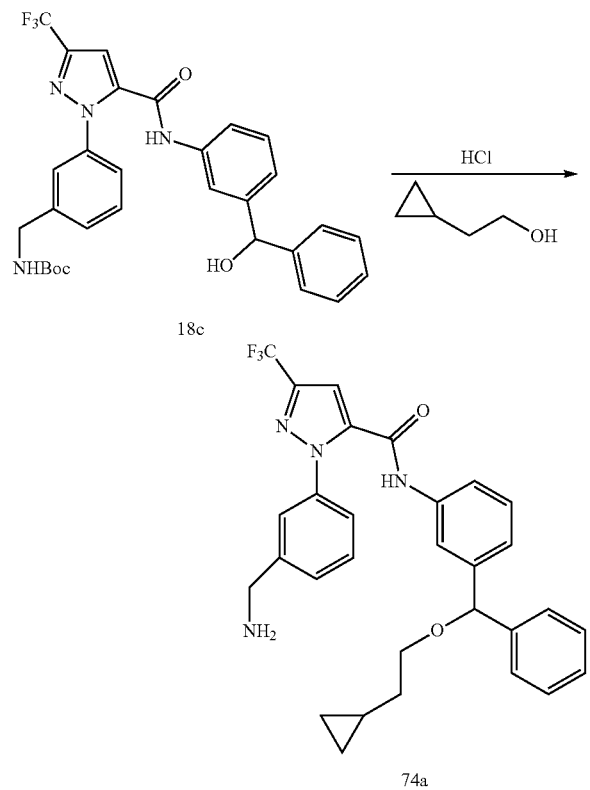

Preparation of 1-(3-(aminomethyl)phenyl)-N-(3-((2-cyclopropylethoxy)(phenyl)methyl)phenyl)-3-(trifluoromethyl)-1H-pyrazole-5-carboxamide (74a)

To a solution of tert-butyl 3-(5-(3-(hydroxy(phenyl)methyl)phenylcarbamoyl)-3-(trifluoromethyl)-1H-pyrazol-1-yl)benzylcarbamate (18c) (0.2 g, 0.353 mmol) in 1,4-Dioxane (18 mL) was added hydrogen chloride (3.80 mL, 15.21 mmol) (4 M in 1,4-dioxane) and stirred at room temperature for 15 h. The reaction mixture was treated with hexanes, decanted, washed with hexanes, and decanted again. To the insoluble crude product added chloroform (40 mL), 2-cyclopropylethanol (1.520 g, 16.94 mmol) and 2 g of silica gel. The mixture was concentrated in vacuum to dryness and the slurry obtained was purified by flash column chromatography [silica gel eluting with chloroform/CMA 80 (1:0 to 3:1)] to give 1-(3-(aminomethyl)phenyl)-N-(3-((2-cyclopropylethoxy)(phenyl)methyl)phenyl)-3-(trifluoromethyl)-1H-pyrazole-5-carboxamide (74a) (25 mg, 13%) as a white solid; $^1$H NMR (300 MHz, DMSO-d$_6$) δ 10.71 (s, 1H), 7.63 (t, J=1.8 Hz, 1H), 7.59-7.50 (m, 3H), 7.46-7.38 (m, 2H), 7.36-7.20 (m, 7H), 7.14 (d, J=7.7 Hz, 1H), 5.42 (s, 1H), 3.77 (s, 2H), 3.49-3.38 (m, 3H), 1.46 (q, J=6.7 Hz, 2H), 0.76 (ddt, J=10.3, 7.4, 3.7 Hz, 1H), 0.41-0.32 (m, 2H), 0.05-0.00 (m, 2H); $^{19}$F NMR (282 MHz, DMSO-d$_6$) δ −60.72; MS (ES+): 535.3 (M+1).

Scheme 75

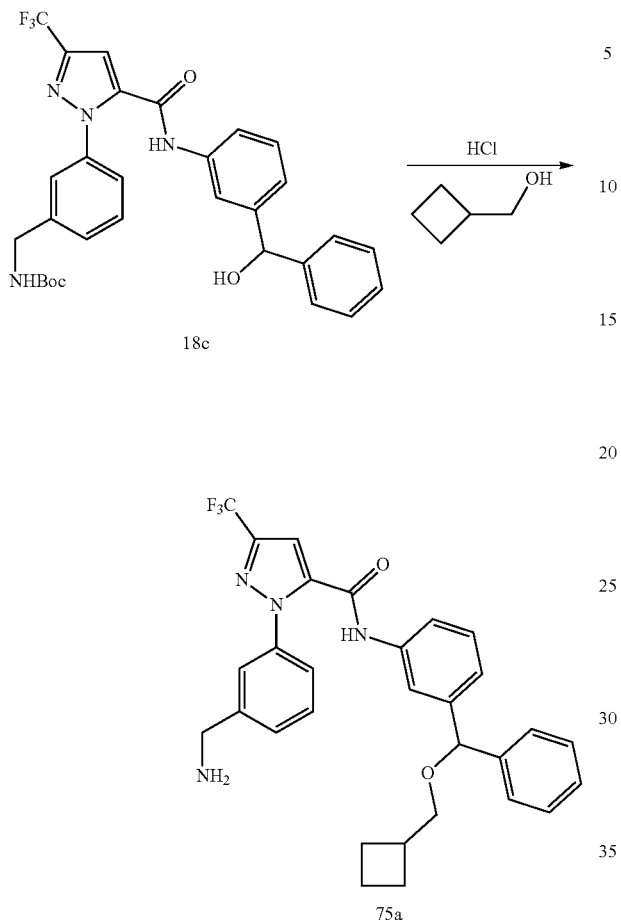

Preparation of 1-(3-(aminomethyl)phenyl)-N-(3-((cyclobutylmethoxy)(phenyl)methyl)phenyl)-3-(trifluoromethyl)-1H-pyrazole-5-carboxamide (75a)

To a solution of tert-butyl 3-(5-(3-(hydroxy(phenyl)methyl)phenylcarbamoyl)-3-(trifluoromethyl)-1H-pyrazol-1-yl)benzylcarbamate (18c) (0.2 g, 0.353 mmol) in 1,4-Dioxane (18 mL) was added hydrogen chloride (3.80 mL, 15.21 mmol) (4 M in 1,4-dioxane) and stirred at room temperature for 15 h. The reaction mixture was treated with hexanes, decanted, washed with hexanes, and decanted again. To the insoluble crude product added chloroform (40 mL), 2-cyclobutylmethanol (1.480 g, 17.01 mmol), and 2 g of silica gel. The mixture was concentrated in vacuum to dryness and the slurry obtained was purified by flash column chromatography [silica gel eluting with chloroform/CMA 80 (1:0 to 3:1)] to give 1-(3-(aminomethyl)phenyl)-N-(3-((cyclobutylmethoxy)(phenyl)methyl)phenyl)-3-(trifluoromethyl)-1H-pyrazole-5-carboxamide (75a) (15 mg, 8%) as a white solid. $^1$H NMR (300 MHz, DMSO-$d_6$) δ 10.71 (s, 1H), 7.61 (s, 1H), 7.55 (d, J=9.4 Hz, 3H), 7.47-7.41 (m, 2H), 7.33 (d, J=4.5 Hz, 5H), 7.24 (dd, J=8.8, 4.3 Hz, 2H), 7.13 (d, J=7.6 Hz, 1H), 5.39 (s, 1H), 3.80 (s, 2H), 3.37 (d, J=6.6 Hz, 2H), 2.05-1.89 (m, 3H), 1.88-1.64 (m, 4H); $^{19}$F NMR (282 MHz, DMSO-$d_6$) δ −60.72; MS (ES+): 535.3 (M+H).

Scheme 76

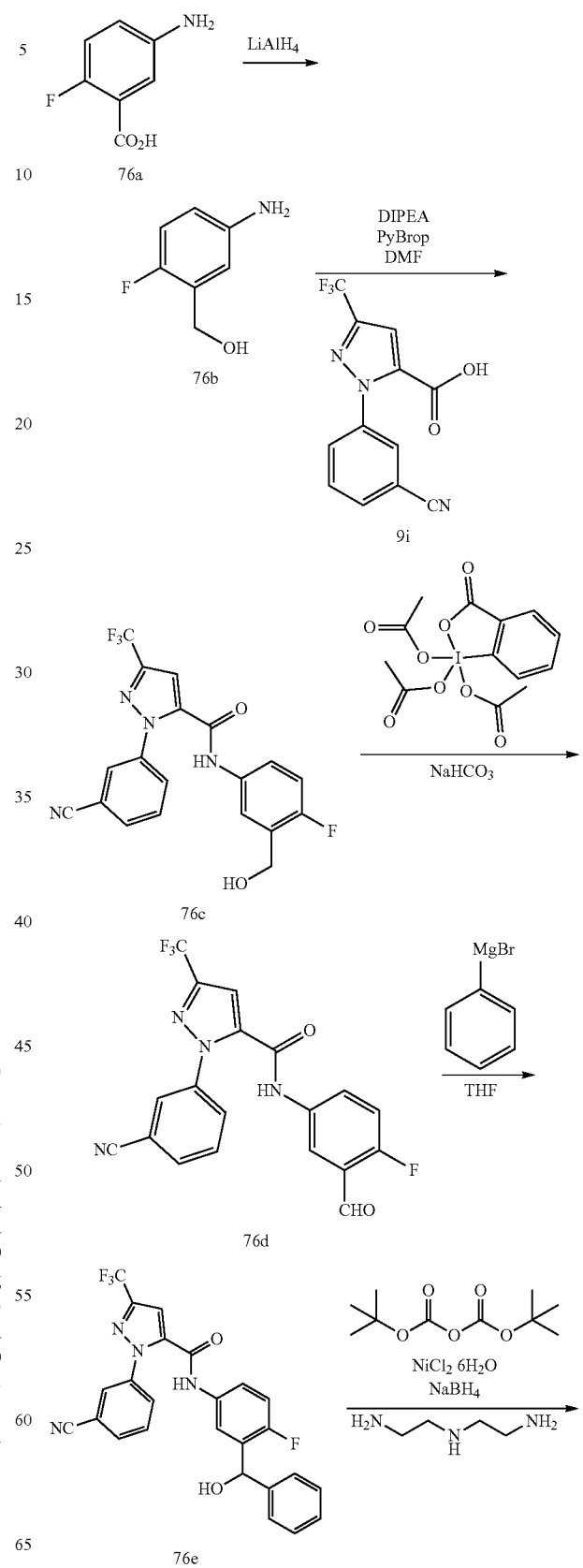

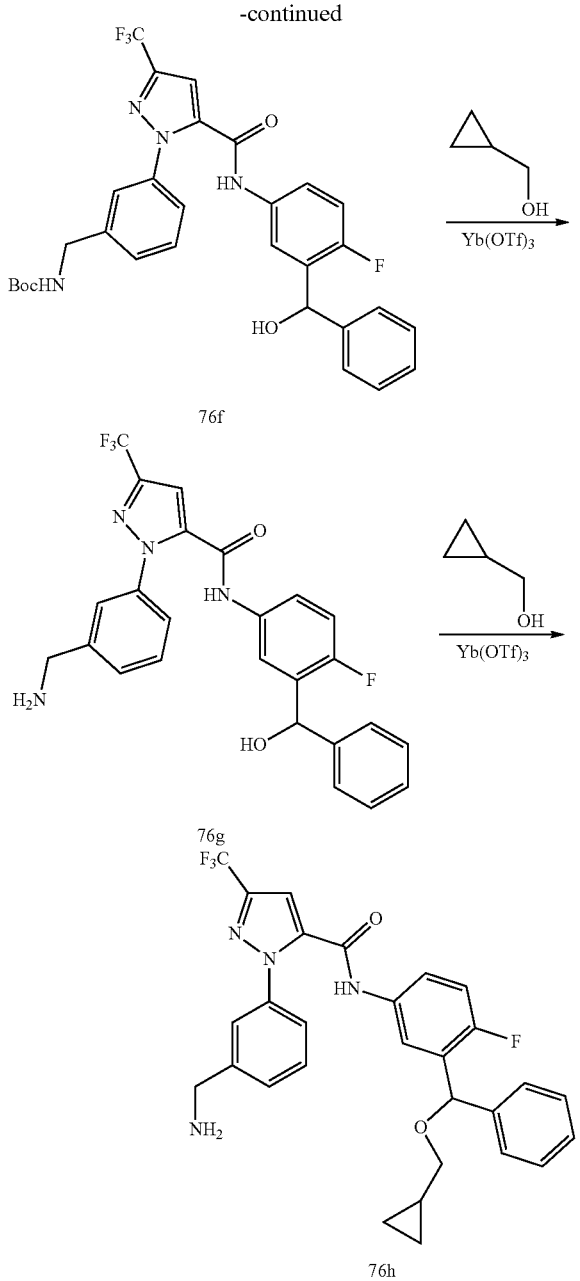

Preparation of 1-(3-(aminomethyl)phenyl)-N-(3-((cyclopropylmethoxy)(phenyl)methyl)-4-fluorophenyl)-3-(trifluoromethyl)-1H-pyrazole-5-carboxamide (76h)

Step-1: Preparation of (5-Amino-3-fluorophenyl)methanol (76b)

To a suspension of lithium aluminum hydride (1.835 g, 48.3 mmol) in THF (50 mL) was added dropwise at 0° C. a solution of 5-amino-3-fluorobenzoic acid (76a) (5 g, 32.2 mmol) in THF (30 mL). The reaction mixture was stirred at room temperature overnight. The mixture was then cooled down to 0° C., quenched with ethyl acetate (30 mL) and water (10 mL). The slurry obtained was filtered through celite and washed with ethyl acetate (50 mL). The aqueous layer was separated and organic layer was dried, filtered and concentrated in vacuum to dryness to give crude product. The crude was purified by flash column chromatography (silica gel 80 g, eluting with 0-100% ethyl acetate in hexane) to furnish (5-amino-2-fluorophenyl)methanol (76b) (1.17 g, 8.29 mmol, 25.7% yield) as a tan solid; $^1$H NMR (300 MHz, DMSO-d$_6$) δ 6.76 (dd, J=10.1, 8.6 Hz, 1H), 6.65 (ddt, J=6.5, 2.9, 0.8 Hz, 1H), 6.39 (ddd, J=8.6, 4.3, 2.9 Hz, 1H), 5.10 (t, J=5.7 Hz, 1H), 4.91 (s, 2H), 4.41 (dt, J=5.8, 0.9 Hz, 2H); MS (ES+) 164.1 (M+23); (ES−) 140.0 (M−1).

Step-2: Preparation of 1-(3-Cyanophenyl)-N-(4-fluoro-3-(hydroxymethyl)phenyl)-3-(trifluoromethyl)-1H-pyrazole-5-carboxamide (76c)

In a 100 mL single-necked flask containing 1-(3-cyanophenyl)-3-(trifluoromethyl)-1H-pyrazole-5-carboxylic acid (9i) (1.992 g, 7.09 mmol), (5-amino-2-fluorophenyl)methanol (76b) (1 g, 7.09 mmol), bromo-tris-pyrrolidino phosphoniumhexafluorophosphate(PyBrop) (3.30 g, 7.09 mmol) was added N,N-dimethylformamide (43 mL) and N-ethyl-N-isopropylpropan-2-amine (6.17 mL) successively in a positive flow of nitrogen at room temperature. The resulting reaction mixture was stirred at room temperature for 37 h under nitrogen atmosphere. TLC analysis (ethyl acetate/hexanes, v/v, 3/7) shows reaction was complete. The reaction was diluted with water (100 mL) and extracted with ethyl acetate (2×100 mL), washed with brine (50 mL), the combined organic layer was dried over anhydrous MgSO$_4$, filtered, and evaporated to dryness. The residue was purified by flash column chromatography (silica gel 40 g, eluting with ethyl acetate in hexanes from 0-100%) to furnish 1-(3-Cyanophenyl)-N-(4-fluoro-3-(hydroxymethyl)phenyl)-3-(trifluoromethyl)-1H-pyrazole-5-carboxamide (76c) (1.213 g, 42% yield) as a white solid; $^1$H NMR (300 MHz, DMSO-d$_6$) δ 10.71 (s, 1H, D$_2$O exchangeable), 8.17 (t, J=1.8 Hz, 1H), 8.01 (dt, J=7.8, 1.3 Hz, 1H), 7.91 (ddd, J=8.2, 2.2, 1.1 Hz, 1H), 7.85-7.69 (m, 3H), 7.56 (ddd, J=7.9, 4.6, 2.8 Hz, 1H), 7.13 (dd, J=9.8, 8.9 Hz, 1H), 5.37 (t, J=5.6 Hz, 1H, D$_2$O exchangeable), 4.53 (d, J=5.6 Hz, 2H); $^{19}$F NMR (282 MHz, DMSO-d$_6$) δ −60.96, −124.39; MS (ES$^+$): MS (ES+) 405.1 (M+1), 427.4 (M+Na), (ES−) 403.1 (M−1), 807.3 (2M−1).

Step-3: Preparation of 1-(3-cyanophenyl)-N-(4-fluoro-3-formylphenyl)-3-(trifluoromethyl)-1H-pyrazole-5-carboxamide (76d)

To a stirred solution of 1-(3-Cyanophenyl)-N-(4-fluoro-3-(hydroxymethyl)phenyl)-3-(trifluoromethyl)-1H-pyrazole-5-carboxamide (76c) (1.205 g, 2.98 mmol) in dichloromethane (20 mL) was added sodium bicarbonate (1.252 g, 14.90 mmol). Dess-Martin Periodinane (1.896 g, 4.47 mmol) was added to the mixture and stirred at room temperature for 5 h, TLC analysis (ethyl acetate/hexanes, 1:1, v/v) shows moderate conversion, at this time Dess-Martin Periodinane (1.896 g, 4.47 mmol) was added and stirred for 30 min. Excess solvent was pumped-off under reduced pressure, residue was diluted with water (50 mL), and extracted with ethyl acetate (2×75 mL). The combined organic solvents were evaporated to dryness. The residue was purified by flash column chromatography [(silica gel 40 g, eluting with ethyl acetate/hexanes from 0 to 50%)] to furnish 1-(3-cyanophenyl)-N-(4-fluoro-3-formylphenyl)-3-(trifluoromethyl)-1H-pyrazole-5-carboxamide (76d) (0.552 g, 46.0% yield) as a white solid; $^1$H NMR (300 MHz, DMSO-d$_6$) δ 10.86 (d, J=37.4 Hz, 1H, D$_2$O exchangeable), 10.22 (d, J=4.9 Hz, 1H), 8.39-8.30 (m, 1H), 8.24-7.82 (m, 5H), 7.80-7.69 (m, 1H), 7.45 (dd, J=10.3, 9.0 Hz, 1H); MS (ES$^+$): MS (ES+) 403.11 (M+1), 425.15 (M+Na), MS (ES−) 401.1 (M−1), 803.1 (2M−1).

Step-4: Preparation of 1-(3-cyanophenyl)-N-(4-fluoro-3-(hydroxy(phenyl)methyl)phenyl)-3-(trifluoromethyl)-1H-pyrazole-5-carboxamide (76e)

To a solution of 1-(3-cyanophenyl)-N-(4-fluoro-3-formylphenyl)-3-(trifluoromethyl)-1H-pyrazole-5-carboxamide (76d) (0.528 g, 1.312 mmol) in THF (15 mL) cooled to 0° C. was added phenyl magnesium bromide (2.66 mL, 2.66 mmol) The reaction mixture was warmed to room temperature stirred for 3 h and quenched with saturated aqueous NH$_4$Cl (100 mL). The product was extracted with ethyl acetate (100 mL, 75 mL). The combined organic extracts were washed with brine (50 mL), dried over anhydrous MgSO$_4$, filtered, evaporated to dryness. The residue obtained was purified by flash column chromatography [(silica gel 25 g, eluting with ethyl acetate in hexanes from 0 to 100%)] to afford 1-(3-cyanophenyl)-N-(4-fluoro-3-(hydroxy(phenyl)methyl)phenyl)-3-(trifluoromethyl)-1H-pyrazole-5-carboxamide (76e) (0.338 g, 54% yield) as an off-white solid; $^1$H NMR (300 MHz, DMSO-d$_6$) δ 10.72 (s, 1H, D$_2$O exchangeable), 8.17 (t, J=1.8 Hz, 1H), 8.01 (dt, J=7.8, 1.3 Hz, 1H), 7.91 (ddd, J=8.2, 2.2, 1.1 Hz, 1H), 7.83 (dd, J=6.6, 2.8 Hz, 1H), 7.79-7.69 (m, 2H), 7.63 (m, 1H), 7.37-7.28 (m, 4H), 7.23 (m, 1H), 7.11 (dd, J=9.9, 8.9 Hz, 1H), 6.11 (d, J=4.0 Hz, 1H, D$_2$O exchangeable), 5.92 (d, J=3.9 Hz, 1H); $^{19}$F NMR (282 MHz, DMSO-d$_6$) δ −60.97, −123.11. MS (ES$^+$): MS (ES+) 503.2 (M+Na), MS (ES−) 479.2 (M−1).

Step-5: Preparation of tert-butyl 3-(5-(4-fluoro-3-(hydroxy(phenyl)methyl)phenylcarbamoyl)-3-(trifluoromethyl)-1H-pyrazol-1-yl)benzylcarbamate (76f)

To a stirred solution of 1-(3-cyanophenyl)-N-(4-fluoro-3-(hydroxy(phenyl)methyl)phenyl)-3-(trifluoromethyl)-1H-pyrazole-5-carboxamide (76e) (0.333 g, 0.693 mmol) in anhydrous methanol (20 mL), cooled to 0° C., was added nickel(II) chloride hexahydrate (0.041 g, 0.173 mmol), (Boc)$_2$O (0.454 g, 2.07 mmol), followed by sodium borohydride (0.157 g, 4.16 mmol) in small portions over 5 min. The reaction was exothermic and effervescent. The reaction mixture was stirred for 1 h at 0° C., TLC analysis (ethyl acetate/hexanes, 2/2, v/v) shows reaction was complete at this point N1-(2-aminoethyl)ethane-1,2-diamine (0.150 mL, 1.386 mmol) was added. The mixture was allowed to stir for 30 minutes and concentrated in vacuum to dryness. The residue was treated with water (50 mL), and extracted with ethyl acetate (2×50 mL). The combined organic layers were dried over anhydrous MgSO$_4$, filtered and excess solvents were pumped-off under reduced pressure. The residue was purified by flash column chromatography (silica gel 25 g, eluting with ethyl acetate/hexanes from 0 to 50%) to furnish tert-butyl 3-(5-(4-fluoro-3-(hydroxy(phenyl)methyl)phenylcarbamoyl)-3-(trifluoromethyl)-1H-pyrazol-1-yl)benzylcarbamate (76f) (0.243 g, 60% yield) as a white solid; $^1$H NMR (300 MHz, DMSO-d$_6$) δ 10.76 (s, 1H), 7.81 (dd, J=6.6, 2.7 Hz, 1H), 7.61 (d, J=8.3 Hz, 2H), 7.49 (d, J=9.0 Hz, 1H), 7.46-7.39 (m, 2H), 7.38-7.28 (m, 6H), 7.23 (q, J=5.7, 4.5 Hz, 1H), 7.09 (t, J=9.4 Hz, 1H), 6.09 (d, J=4.0 Hz, 1H, D$_2$O exchangeable), 5.92 (d, J=4.0 Hz, 1H), 4.19 (d, J=6.3 Hz, 2H), 1.36 (s, 9H); $^1$H NMR (300 MHz, DMSO-d$_6$ D$_2$O) δ 10.77 (s, 1H), 7.81 (dd, J=6.5, 2.7 Hz, 1H), 7.59 (s, 2H), 7.54-7.42 (m, 2H), 7.40 (s, 1H), 7.34 (dd, J=13.1, 3.1 Hz, 5H), 7.27-7.20 (m, 1H), 7.10 (t, J=9.4 Hz, 1H), 5.91 (s, 1H), 4.19 (d, J=6.4 Hz, 2H), 1.36 (s, 9H); $^{19}$F NMR (282 MHz, DMSO-d$_6$) δ −60.81, −123.19; MS (ES$^+$): MS (ES+) 607.2 (M+Na), MS (ES−) 583.3 (M−1).

Step-6: Preparation of 1-(3-(aminomethyl)phenyl)-N-(4-fluoro-3-(hydroxy(phenyl)methyl)phenyl)-3-(trifluoromethyl)-1H-pyrazole-5-carboxamide (76g)

To a solution of tert-butyl 3-(5-(4-fluoro-3-(hydroxy(phenyl)methyl)phenylcarbamoyl)-3-(trifluoromethyl)-1H-pyrazol-1-yl)benzylcarbamate (76f) (0.230 g, 0.393 mmol) in cyclopropylmethanol (3.39 mL, 47.2 mmol) was added ytterbium(III) trifluoromethanesulfonate (0.488 g, 0.787 mmol) and heated at 80° C. overnight. TLC analysis shows (CMA80/CHCl$_3$, 1/2, v/v) reaction was complete. Excess solvent was pumped-off, dried under reduced pressure. The residue was purified by flash column chromatography (silica gel 12 g, eluting with CMA80 in chloroform from 0-100%) to furnish 1-(3-(aminomethyl)phenyl)-N-(4-fluoro-3-(hydroxy(phenyl)methyl)phenyl)-3-(trifluoromethyl)-1H-pyrazole-5-carboxamide (76g) (139 mg, 73% yield) as a white solid; $^1$H NMR (300 MHz, DMSO-d$_6$) δ 10.75 (s, 1H, D$_2$O exchangeable), 7.83 (dd, J=6.6, 2.7 Hz, 1H), 7.64-7.55 (m, 2H), 7.52 (d, J=2.1 Hz, 1H), 7.48-7.40 (m, 2H), 7.32 (d, J=4.3 Hz, 5H), 7.27-7.18 (m, 1H), 7.10 (dd, J=9.9, 8.9 Hz, 1H), 6.09 (d, J=4.0 Hz, 1H, D$_2$O exchangeable), 5.91 (d, J=3.7 Hz, 1H), 3.77 (s, 2H); $^{19}$F NMR (282 MHz, DMSO-d$_6$) δ −60.74, −123.20; MS (ES$^+$): MS (ES+) 485.2 (M+1), MS (ES−) 483.2 (M−1), 967.3 (2M−1).

Step-7: Preparation of 1-(3-(aminomethyl)phenyl)-N-(3-((cyclopropylmethoxy)(phenyl)methyl)-4-fluorophenyl)-3-(trifluoromethyl)-1H-pyrazole-5-carboxamide (76h)

To a solution of 1-(3-(aminomethyl)phenyl)-N-(4-fluoro-3-(hydroxy(phenyl)methyl)phenyl)-3-(trifluoromethyl)-1H-pyrazole-5-carboxamide (76g) (0.131 g, 0.27 mmol) in cyclopropylmethanol (2.330 mL, 32.4 mmol) was added Ytterbium(III) trifluoromethanesulfonate (0.503 g, 0.811 mmol) and heated at 80° C. overnight. TLC analysis shows (CMA80/CHCl$_3$, 1/2, v/v) reaction was completed. Excess solvent was pumped-off, dried under reduced pressure. The residue was purified by flash column chromatography twice [silica gel 25 g, eluting with methanol in chloroform from 0-100%] to furnish 1-(3-(aminomethyl)phenyl)-N-(3-((cyclopropylmethoxy)(phenyl)methyl)-4-fluorophenyl)-3-(trifluoromethyl)-1H-pyrazole-5-carboxamide (76h) (78 mg, 54% yield) as an off-white solid; $^1$H NMR (300 MHz, DMSO-d$_6$) δ 10.80 (s, 1H), 7.76 (dd, J=6.5, 2.7 Hz, 1H), 7.64 (ddd, J=9.1, 4.7, 2.8 Hz, 1H), 7.59 (s, 1H), 7.56-7.51 (m, 1H), 7.43 (m, 2H), 7.39-7.30 (m, 5H), 7.27 (m, 1H), 7.14 (t, J=9.4 Hz, 1H), 5.70 (s, 1H), 3.78 (s, 2H), 3.27 (d, J=6.8 Hz, 2H), 1.05 (dddd, J=11.6, 8.1, 6.8, 2.6 Hz, 1H), 0.58-0.37 (m, 2H), 0.22-0.08 (m, 2H); $^1$H NMR (300 MHz, DMSO-d$_6$ D$_2$O) δ 7.79 (dd, J=6.5, 2.7 Hz, 1H), 7.59 (ddd, J=9.1, 4.7, 2.8 Hz, 1H), 7.55 (s, 1H), 7.54-7.50 (m, 1H), 7.49-7.44 (m, 2H), 7.41-7.27 (m, 6H), 7.15 (dd, J=9.9, 8.9 Hz, 1H), 5.70 (s, 1H), 3.77 (s, 2H), 3.27 (d, J=6.8 Hz, 2H), 1.09-0.99 (m, 1H), 0.55-0.39 (m, 2H), 0.23-0.07 (m, 2H); $^{19}$F NMR (282 MHz, DMSO-d$_6$) δ −60.74, −123.09; MS (ES$^+$): MS (ES+) 539.2 (M+1), MS (ES−) 537.2 (M−1), 573.2 (M+Cl); Analysis calculated for: C$_{29}$H$_{26}$F$_4$N$_4$O$_2$.0.5H$_2$O: C, 63.61; H, 4.97; N, 10.23; Found: C, 63.99; H, 5.20; N, 9.89.

Scheme 77

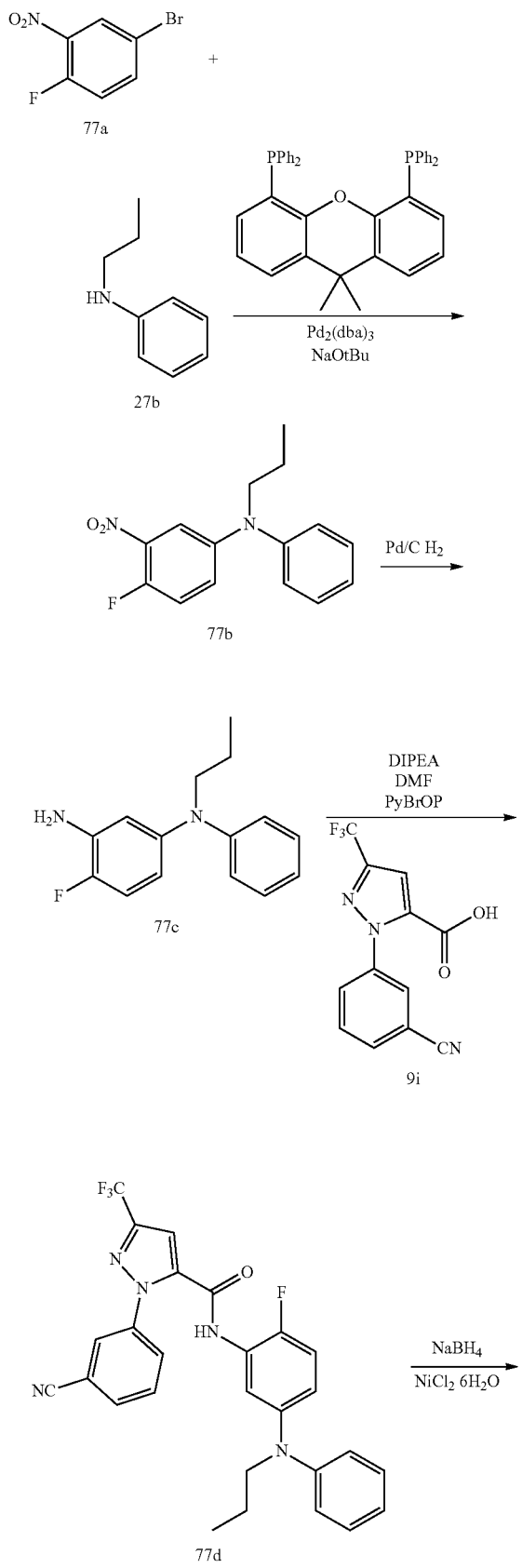

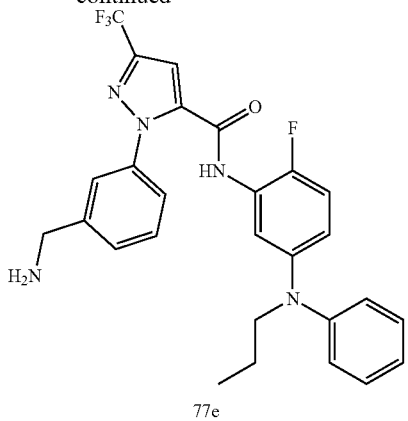

Preparation of 1-(3-(aminomethyl)phenyl)-N-(2-fluoro-5-(phenyl(propyl)amino)phenyl)-3-(trifluoromethyl)-1H-pyrazole-5-carboxamide (77e)

Step-1: Preparation of 4-fluoro-3-nitro-N-phenyl-N-propylaniline (77b)

To a 250 mL single-neck flask with a magnetic stir bar was charged 4-bromo-1-fluoro-2-nitrobenzene (77a) (2.24 mL, 18.18 mmol), N-propylaniline (27a) (3.11 mL, 21.82 mmol), sodium 2-methylpropan-2-olate (1.747 g, 18.18 mmol), (9,9-dimethyl-9H-xanthene-4,5-diyl)bis(diphenylphosphine) (1.052 g, 1.818 mmol) and tris(dibenzylideneacetone)dipalladium(0) (0.499 g, 0.545 mmol). The flask was degassed and refilled with nitrogen, this cycle was repeated three times. To the solid reactants, toluene (50 mL) was injected in a positive flow of nitrogen. The reaction mixture was stirred at 110° C. for 16 h in a positive flow of nitrogen, cooled to room temperature, quenched with water (75 mL) and extracted with ethyl acetate (2×100 mL). The combined organic layers were dried over $MgSO_4$, filtered, evaporated to dryness. The residue was purified by flash column chromatography twice [(silica gel 80 g, eluting with ethyl acetate in hexanes from 0 to 100%)] to afford 4-fluoro-3-nitro-N-phenyl-N-propylaniline (77b) (2.377 g, 8.67 mmol, 47.7% yield) as a brown-yellow oil; MS (ES+): MS (ES+) 297.2 (M+Na).

Step-2: Preparation of 4-fluoro-$N_1$-phenyl-$N_1$-propylbenzene-1,3-diamine (77c)

To a solution of 4-fluoro-3-nitro-N-phenyl-N-propylaniline (77b) (2.35 g, 8.57 mmol) in methanol (30 mL) was added palladium (10% Pd on carbon) (0.182 g, 1.714 mmol). The mixture was hydrogenated at 60 psi for 2.5 h. The reaction was filtered through a Celite pad, Celite pad was subsequently washed with methanol (2×25 mL) and ethyl acetate (25 mL). Excess solvents were pumped-off under reduced pressure. The residue was purified by flash column chromatography [(silica gel 80 g, eluting with ethyl acetate in hexanes from 0 to 100%)] to afford 4-fluoro-$N_1$-phenyl-$N_1$-propylbenzene-1,3-diamine (77c) (0.168 g, 8% yield) as a pale yellow oil; $^1$H NMR (300 MHz, DMSO-$d_6$) δ 7.16 (dd, J=8.7, 7.2 Hz, 2H), 6.93 (dd, J=11.4, 8.6 Hz, 1H), 6.79-6.71 (m, 3H), 6.49 (dd, J=8.3, 2.7 Hz, 1H), 6.21 (ddd, J=8.6, 3.9, 2.7 Hz, 1H), 5.11 (s, 2H, $D_2O$ exchangeable), 3.61-3.44 (m, 2H), 1.67-1.44 (m, 2H), 0.88 (t, J=7.4 Hz, 3H); $^{19}$F NMR (282 MHz, DMSO-d$_6$) δ −140.87; MS (ES$^+$): MS (ES+) 245.2 (M+1).

Step-3: Preparation of 1-(3-cyanophenyl)-N-(2-fluoro-5-(phenyl(propyl)amino)phenyl)-3-(trifluoromethyl)-1H-pyrazole-5-carboxamide (77d)

In a 100 mL single-necked flask containing 1-(3-cyanophenyl)-3-(trifluoromethyl)-1H-pyrazole-5-carboxylic acid (9i) (0.215 g, 0.766 mmol), 4-fluoro-N$_1$-phenyl-N$_1$-propyl-benzene-1,3-diamine (77c) (0.156 g, 0.639 mmol), bromo-tris-pyrrolidino phosphoniumhexafluorophosphate (PyBrop, 0.357 g, 0.766 mmol) was added N,N-dimethylformamide (3.86 mL, 49.8 mmol) and N-ethyl-N-isopropylpropan-2-amine (0.556 mL, 3.19 mmol) successively in a positive flow of nitrogen at room temperature. The resulting reaction mixture was stirred at room temperature for 16 h under nitrogen atmosphere. Excess DMF was removed under reduced pressure. The reaction mixture was treated with water (25 mL) and was extracted with ethyl acetate (2×50 mL). The combined organic layers were washed with brine (50 mL), dried over anhydrous MgSO$_4$, filtered, and evaporated to dryness. The residue was purified by flash column chromatography [silica gel 25 g, eluting with ethyl acetate in hexanes from 0-100%] to furnish 1-(3-cyanophenyl)-N-(2-fluoro-5-(phenyl(propyl)amino)phenyl)-3-(trifluoromethyl)-1H-pyrazole-5-carboxamide (77d) (0.149 g, 46% yield) as a pale yellow solid; $^1$H NMR (300 MHz, DMSO-d$_6$) δ 10.51 (s, 1H, D$_2$O exchangeable), 8.11 (s, 1H), 7.99 (d, J=7.5 Hz, 1H), 7.89 (d, J=7.9 Hz, 1H), 7.79-7.66 (m, 2H), 7.30-7.19 (m, 3H), 7.18-7.12 (m, 2H), 6.96-6.85 (m, 3H), 3.59 (t, J=7.3 Hz, 2H), 1.54 (q, J=8.4, 7.9 Hz, 2H), 0.87 (td, J=7.4, 1.7 Hz, 3H); $^{19}$F NMR (282 MHz, DMSO-d$_6$) δ −60.99, −129.31; IR (KBr, cm$^{-1}$): 2235 cm$^{-1}$ (—CN stretching); MS (ES$^+$): MS (ES+) 530.2 (M+Na), MS (ES−) 506.2 (M−1), 542.2 (M+Cl).

Step-4: Preparation of 1-(3-(aminomethyl)phenyl)-N-(2-fluoro-5-(phenyl(propyl)amino)phenyl)-3-(trifluoromethyl)-1H-pyrazole-5-carboxamide (77e)

To a stirred solution of 1-(3-cyanophenyl)-N-(2-fluoro-5-(phenyl(propyl)amino)phenyl)-3-(trifluoromethyl)-1H-pyrazole-5-carboxamide (77d) (0.132 g, 0.260 mmol) in anhydrous methanol (10 mL) cooled to 0° C., were added nickel(II) chloride hexahydrate (0.062 g, 0.260 mmol) followed by sodium borohydride (0.059 g, 1.561 mmol) in small portions over a period of 5 min. The reaction was exothermic and effervescent. The reaction mixture was stirred for 15 min, TLC analysis (ethyl acetate/hexanes, 3/7, v/v) shows reaction was complete. Excess methanol was pumped-off under reduced pressure. The reaction mixture was treated with water (30 mL), and product was extracted with ethyl acetate (2×50 mL). The combined organic layers were dried over MgSO$_4$, filtered, and evaporated to dryness. The residue was purified by flash column chromatography (silica gel 2×12 g, eluting with methanol/chloroform from 0 to 100%) to furnish 1-(3-(aminomethyl)phenyl)-N-(2-fluoro-5-(phenyl(propyl)amino)phenyl)-3-(trifluoromethyl)-1H-pyrazole-5-carboxamide (77e) (0.039 g, 29% yield) as a white solid; $^1$H NMR (300 MHz, DMSO-d$_6$) δ 10.48 (s, 1H), 7.56 (s, 1H), 7.53-7.48 (m, 1H), 7.47-7.39 (m, 2H), 7.37-7.28 (m, 1H), 7.28-7.10 (m, 4H), 6.96-6.82 (m, 4H), 3.77 (s, 2H), 3.64-3.52 (m, 2H), 1.54 (h, J=7.4 Hz, 2H), 0.87 (t, J=7.3 Hz, 3H); $^1$H NMR (300 MHz, DMSO-d$_6$ D$_2$O) δ 7.55 (s, 1H), 7.53-7.48 (m, 1H), 7.47-7.38 (m, 2H), 7.31 (dt, J=8.8, 2.4 Hz, 1H), 7.28-7.11 (m, 4H), 6.97-6.83 (m, 4H), 3.76 (d, J=4.8 Hz, 2H), 3.58 (t, J=7.5 Hz, 2H), 1.54 (h, J=7.4 Hz, 2H), 0.87 (t, J=7.3 Hz, 3H); $^{19}$F NMR (282 MHz, DMSO-d$_6$) δ −60.75, −129.58; MS (ES+): MS (ES+) 512.2 (M+1), MS (ES−) 510.2 (M−1); Analysis calculated for C$_{27}$H$_{25}$F$_4$N$_5$O.0.75H$_2$O: C, 61.77; H, 5.09; N, 13.34; Found: C, 61.71; H, 5.03; N, 12.80.

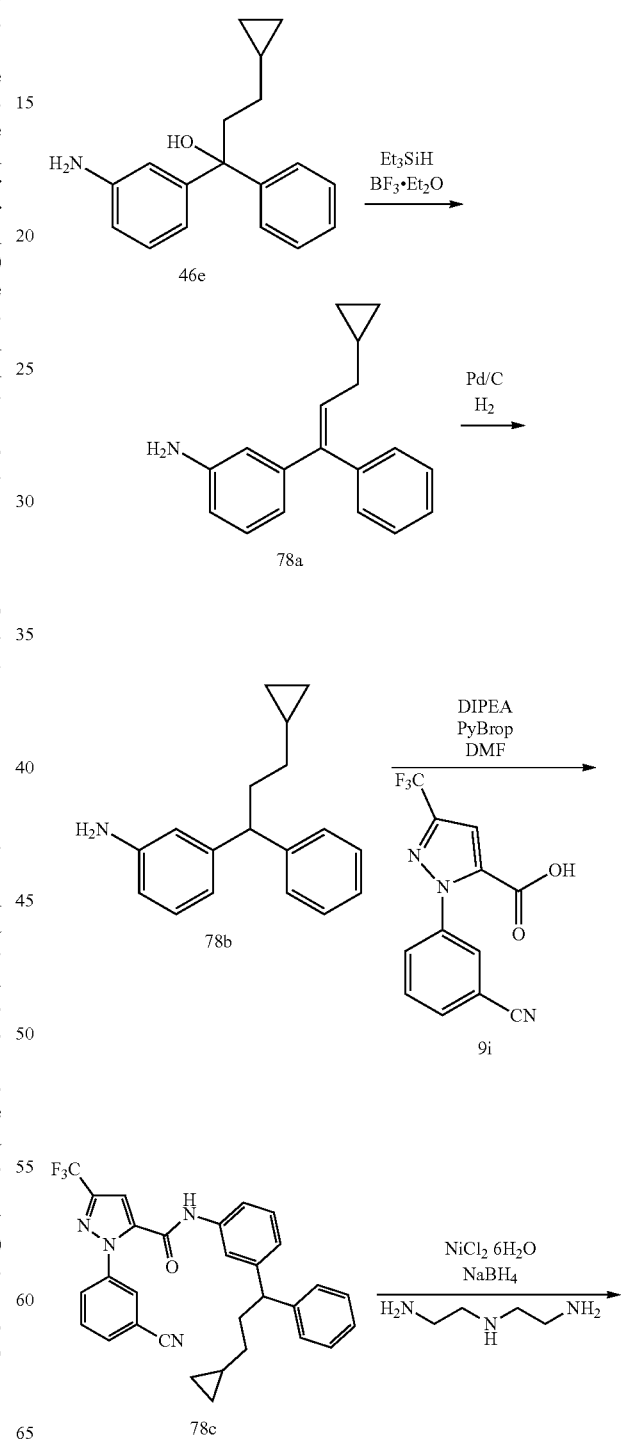

Scheme 78

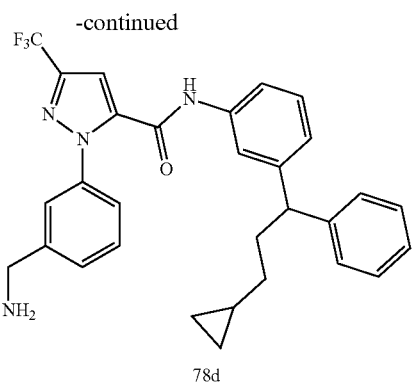

78d

Preparation of 1-(3-(aminomethyl)phenyl)-N-(3-(3-cyclopropyl-1-phenylpropyl)phenyl)-3-(trifluoromethyl)-1H-pyrazole-5-carboxamide (78d)

Step-1: Preparation of (E)- and (Z)-3-(3-cyclopropyl-1-phenylprop-1-enyl)aniline (78a)

To a stirred solution of 1-(3-aminophenyl)-3-cyclopropyl-1-phenylpropan-1-ol (46e) (0.17 g, 0.636 mmol) in dichloromethane (15 mL) at 0° C. was added BF3.Et$_2$O (0.322 mL, 2.54 mmol) and triethylsilane (0.203 mL, 1.272 mmol). The reaction warmed to room temperature stirred for 30 minutes and quenched carefully with saturated sodium bicarbonate solution. The reaction was stirred for 5 mins and diluted with dichloromethane (50 mL). The organic layer was separated, washed with water (2×25 mL), brine (25 mL), dried, filtered and concentrated in vacuum. The crude residue was purified by flash column chromatography (silica gel 12 g, eluting with ethyl acetate in hexanes 0 to 20%) to afford pure (E)- and (Z)-3-(3-cyclopropyl-1-phenylprop-1-enyl)aniline (78a) (151 mg, 95% yield) which was used as such for next step.

Step-2: Preparation of 3-(3-cyclopropyl-1-phenylpropyl)aniline (78b)

To a suspension of Pd on 10% carbon (32.0 mg) in ethyl acetate (25 mL) was added (E)- and (Z)-3-(3-cyclopropyl-1-phenylprop-1-enyl)aniline (78a) (150 mg, 0.602 mmol) and hydrogenated at 60 psi for 1 h. The reaction mixture was filtered through celite and concentrated in vacuum. The crude residue was purified by flash column chromatography (silica gel 12 g, eluting with ethyl acetate in hexanes 0 to 30%) to afford 3-(3-cyclopropyl-1-phenylpropyl)aniline (78b) (133 mg, 88% yield) as an oil; $^1$H NMR (300 MHz, DMSO-d$_6$) δ 7.25 (d, J=5.0 Hz, 4H), 7.19-7.09 (m, 1H), 6.89 (t, J=7.7 Hz, 1H), 6.47 (t, J=1.9 Hz, 1H), 6.43 (dt, J=7.6, 1.3 Hz, 1H), 6.33 (ddd, J=8.0, 2.2, 1.0 Hz, 1H), 4.95 (s, 2H), 3.73 (t, J=7.8 Hz, 1H), 2.02 (td, J=8.4, 6.6 Hz, 2H), 1.07 (qd, J=6.9, 1.9 Hz, 2H), 0.77-0.59 (m, 1H), 0.42-0.30 (m, 2H), −0.03-0.11 (m, 2H).

Step-3: Preparation of 1-(3-cyanophenyl)-N-(3-(3-cyclopropyl-1-phenylpropyl)phenyl)-3-(trifluoromethyl)-1H-pyrazole-5-carboxamide (78c)

To a solution of 1-(3-cyanophenyl)-3-(trifluoromethyl)-1H-pyrazole-5-carboxylic acid (9i) (132 mg, 0.47 mmol) in DMF (5 mL) was added 3-(3-cyclopropyl-1-phenylpropyl)aniline (78b) (130 mg, 0.517 mmol), N-ethyl-N-isopropylpropan-2-amine (0.655 mL, 3.76 mmol) and bromo-tris-pyrrolidino phosphoniumhexafluorophosphate (PyBrOP, 241 mg, 0.517 mmol) at room temperature. The resulting reaction mixture was stirred at 25° C. for 16 h. The reaction mixture was quenched with water (25 mL) extracted and with ethyl acetate (2×50 mL). The organic layers were combined, washed with water (25 mL), brine (25 mL), dried over anhydrous MgSO$_4$, filtered, and concentrated under reduced pressure to dryness. The residue was purified by flash column chromatography (silica gel 12 g, eluting with hexanes in ethyl acetate/hexanes from 0-100%) to furnish 1-(3-cyanophenyl)-N-(3-(3-cyclopropyl-1-phenylpropyl)phenyl)-3-(trifluoromethyl)-1H-pyrazole-5-carboxamide (78c) (194 mg, 0.377 mmol, 80% yield) as an oil; MS (ES+) 537.3 (M+Na).

Step-4: Preparation of 1-(3-(aminomethyl)phenyl)-N-(3-(3-cyclopropyl-1-phenylpropyl)phenyl)-3-(trifluoromethyl)-1H-pyrazole-5-carboxamide (78d)

To a stirred solution of 1-(3-cyanophenyl)-N-(3-(3-cyclopropyl-1-phenylpropyl)phenyl)-3-(trifluoromethyl)-1H-pyrazole-5-carboxamide (78c) (180 mg, 0.350 mmol) in anhydrous methanol (10 mL), cooled to 0° C., was added nickel(II) chloride hexahydrate (18.14 mg, 0.076 mmol), followed by sodium borohydride (83 mg, 2.188 mmol) in small portions over 5 min. The reaction was exothermic and effervescent. The reaction mixture was stirred for 1 h at 0° C., TLC analysis (ethyl acetate/hexanes, 2/2, v/v) shows reaction was complete at this point N1-(2-aminoethyl)ethane-1,2-diamine (0.087 mL, 0.805 mmol) was added. The mixture was allowed to stir for 30 mins and concentrated in vacuum to dryness. The residue was treated with water (25 mL), and extracted with ethyl acetate (2×25 mL). The combined organic layers were dried over anhydrous MgSO$_4$, filtered and excess solvents were pumped-off under reduced pressure. The residue was purified by flash column chromatography (silica gel 12 g, eluting with ethyl acetate/hexanes from 0 to 50%) to furnish 1-(3-(aminomethyl)phenyl)-N-(3-(3-cyclopropyl-1-phenylpropyl)phenyl)-3-(trifluoromethyl)-1H-pyrazole-5-carboxamide (78d) (165 mg, 0.318 mmol, 91% yield) free base as a white semisolid. The semisolid was dissolved in methanol (10 mL), added conc. HCl (0.043 mL, 0.513 mmol), stirred for 15 mins and concentrated in vacuum to dryness to furnish 1-(3-(aminomethyl)phenyl)-N-(3-(3-cyclopropyl-1-phenylpropyl)phenyl)-3-(trifluoromethyl)-1H-pyrazole-5-carboxamide (78d) (100 mgs) as a white solid; $^1$H NMR (300 MHz, DMSO-d$_6$) δ 10.71 (s, 1H), 8.34 (s, 3H), 7.72 (s, 1H), 7.68-7.58 (m, 2H), 7.58-7.48 (m, 4H), 7.34-6.59 (m, 5H), 7.16 (dp, J=8.6, 2.7 Hz, 1H), 7.09 (d, J=7.7 Hz, 1H), 4.13 (d, J=5.7 Hz, 2H), 3.92 (t, J=7.8 Hz, 1H), 2.08 (q, J=7.6 Hz, 2H), 1.07 (dd, J=9.5, 6.3 Hz, 2H), 0.78-0.60 (m, 1H), 0.43-0.29 (m, 2H), −0.07 (td, J=5.4, 3.8 Hz, 2H); $^{19}$FNMR (282 MHz, DMSO-d$_6$) δ −60.80; MS (ES+) 519.57 (M+1), (ES−) 517.2 (M−1); Analysis calculated for $C_{30}H_{29}F_3N_4O.1.5HCl.1.25H_2O$: C, 60.48; H, 5.58; Cl, 8.93; N, 9.40 Found: C, 60.12; H, 5.40; Cl, 8.65; N, 9.80.

Scheme 79
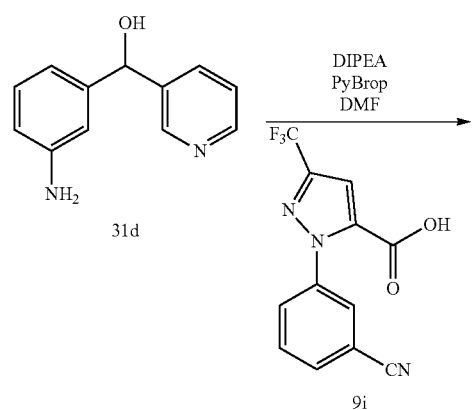
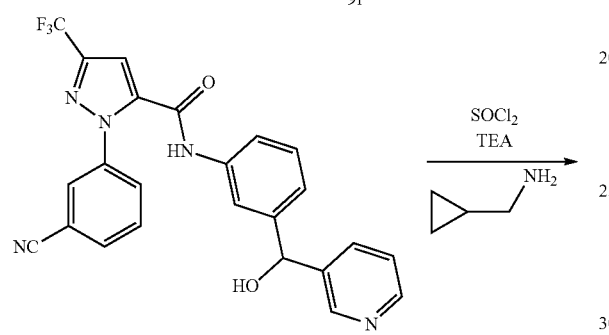
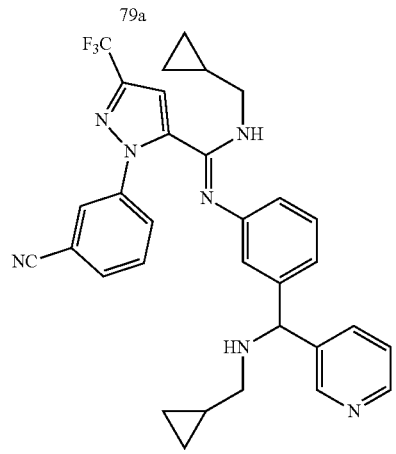
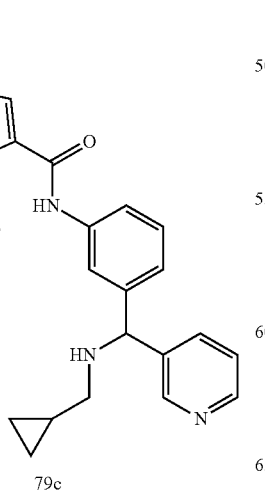
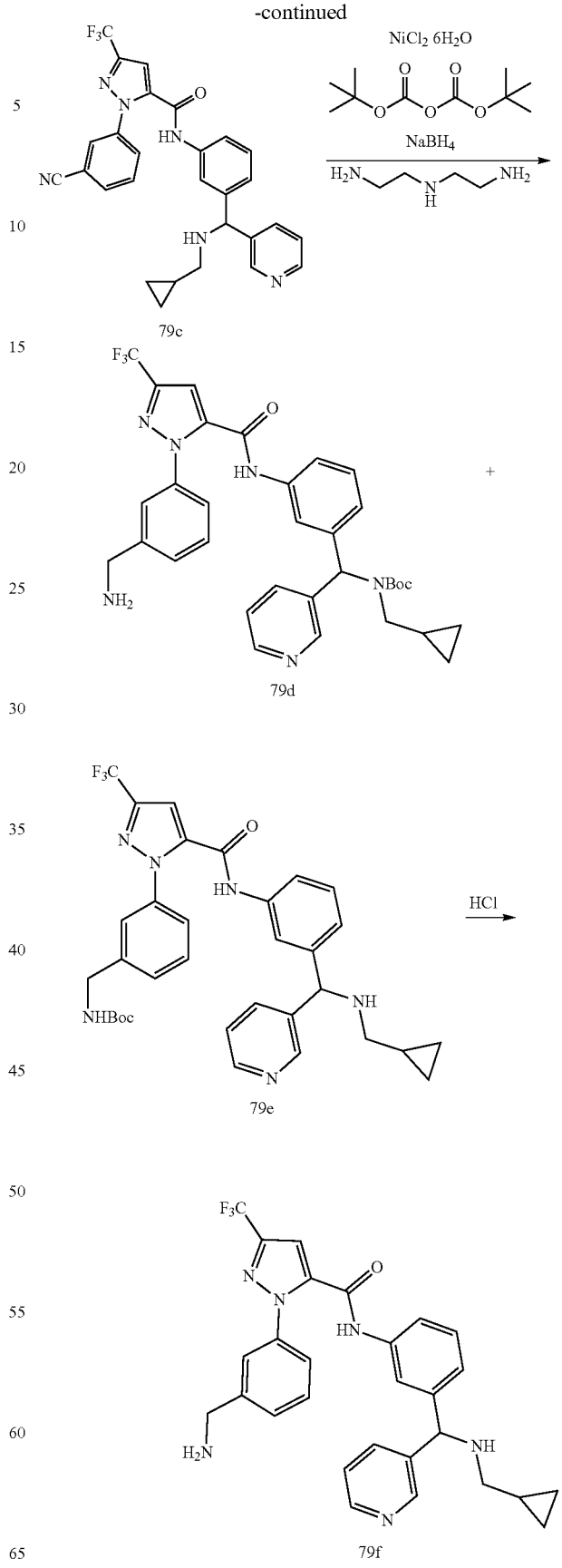

Preparation of 1-(3-(Aminomethyl)phenyl)-N-(3-(((cyclopropylmethyl)amino)(pyridin-3-yl)methyl)phenyl)-3-(trifluoromethyl)-1H-pyrazole-5-carboxamide (79f)

Step-1: Preparation of 1-(3-Cyanophenyl)-N-(3-(hydroxy(pyridin-3-yl)methyl)phenyl)-3-(trifluoromethyl)-1H-pyrazole-5-carboxamide (79a)

To a solution of 1-(3-cyanophenyl)-3-(trifluoromethyl)-1H-pyrazole-5-carboxylic acid (9i) (0.463 g, 1.648 mmol) in DMF (10 mL) was added (3-aminophenyl)(pyridin-3-yl)methanol (31d) (0.33 g, 1.648 mmol) N-ethyl-N-isopropylpropan-2-amine (1.435 mL, 8.24 mmol) and bromo-tris-pyrrolidino phosphoniumhexafluorophosphate (PyBrOP, 0.922 g, 1.978 mmol) at room temperature. The reaction mixture was stirred at room temperature for 37 h under nitrogen atmosphere. The reaction was diluted with water (25 mL) and extracted with ethyl acetate (2×100 mL). The combined organic layer was washed with brine (50 mL), dried, filtered, and evaporated to dryness. The residue obtained was purified by flash column chromatography [silica gel 40 g, eluting with ethyl acetate in hexanes from 0-100%] to furnish 1-(3-Cyanophenyl)-N-(3-(hydroxy(pyridin-3-yl)methyl)phenyl)-3-(trifluoromethyl)-1H-pyrazole-5-carboxamide (79a) (0.653 g, 1.409 mmol, 86% yield) as a yellow oil; $^1$H NMR (300 MHz, DMSO-$d_6$) δ 10.67 (s, 1H), 8.58 (d, J=2.2 Hz, 1H), 8.43 (dd, J=4.8, 1.7 Hz, 1H), 8.17 (t, J=1.8 Hz, 1H), 8.00 (dt, J=7.7, 1.3 Hz, 1H), 7.90 (ddd, J=8.3, 2.2, 1.1 Hz, 1H), 7.77-7.64 (m, 4H), 7.62-7.52 (m, 1H), 7.37-7.25 (m, 2H), 7.21-7.14 (m, 1H), 6.15 (d, J=3.9 Hz, 1H), 5.77 (d, J=4.0 Hz, 1H); $^{19}$F NMR (282 MHz, DMSO-$d_6$) δ −60.98; MS (ES−) 462.2 (M−1).

Step-2: Preparation of (Z)-1-(3-cyanophenyl)-N-(cyclopropylmethyl)-N'-(3-(((cyclopropylmethyl)amino)(pyridin-3-yl)methyl)phenyl)-3-(trifluoromethyl)-1H-pyrazole-5-carboximidamide (79b) and 1-(3-cyanophenyl)-N-(3-(((cyclopropylmethyl)amino)(pyridin-3-yl)methyl)phenyl)-3-(trifluoromethyl)-1H-pyrazole-5-carboxamide (79c)

To a solution of 1-(3-Cyanophenyl)-N-(3-(hydroxy(pyridin-3-yl)methyl)phenyl)-3-(trifluoromethyl)-1H-pyrazole-5-carboxamide (79a) (0.32 g, 0.691 mmol) in dichloromethane (10 mL) at 0° C. was added thionyl chloride (0.151 mL, 2.072 mmol), triethylamine (0.289 mL, 2.072 mmol) and allowed to warm to room temperature over 3 h. The reaction mixture was concentrated in vacuum to dryness. The residue was dissolved in acetonitrile (10.00 mL) and added cyclopropylmethanamine (1.198 mL, 13.81 mmol). The reaction mixture was heated at reflux overnight. The reaction mixture was cooled to room temperature concentrated in vacuum to dryness. The residue was diluted with chloroform (25 mL), washed with water (10 mL), dried, filtered and concentrated in vacuum. The residue was purified by flash column chromatography (silica gel 12 g, eluting 0-100% ethyl acetate/methanol 9; 1 in hexane) to afford (Z)-1-(3-cyanophenyl)-N-(cyclopropylmethyl)-N'-(3-(((cyclopropylmethyl)amino)(pyridin-3-yl)methyl)phenyl)-3-(trifluoromethyl)-1H-pyrazole-5-carboximidamide (79b) (0.05 g, 0.088 mmol, 12.71% yield) as a colorless oil: $^1$H NMR (300 MHz, DMSO-$d_6$) δ 8.46 (d, J=2.2 Hz, 1H), 8.38 (dd, J=4.8, 1.7 Hz, 1H), 7.89 (dt, J=7.8, 1.3 Hz, 1H), 7.84 (t, J=5.4 Hz, 1H), 7.60 (t, J=8.0 Hz, 1H), 7.57-7.51 (m, 1H), 7.41-7.36 (m, 1H), 7.34 (t, J=1.8 Hz, 1H), 7.30-7.22 (m, 2H), 6.80 (q, J=7.7 Hz, 2H), 6.19 (s, 1H), 5.91-5.84 (m, 1H), 4.59 (s, 1H), 3.20 (s, 2H), 2.32-2.05 (m, 3H), 0.82 (d, J=17.1 Hz, 1H), 0.56-0.47 (m, 2H), 0.42-0.33 (m, 2H), 0.27 (q, J=5.1 Hz, 2H), 0.08-0.01 (m, 2H); MS ES(+) 570.3 (M+1), (ES−) 568.3 (ES−). Further elution gave 1-(3-cyanophenyl)-N-(3-(((cyclopropylmethyl)amino)(pyridin-3-yl)methyl)phenyl)-3-(trifluoromethyl)-1H-pyrazole-5-carboxamide (79c) (0.07 g, 0.136 mmol, 19.63% yield) as a white solid; $^1$H NMR (300 MHz, DMSO-$d_6$) δ 10.66 (s, 1H), 8.62 (d, J=2.2 Hz, 1H), 8.44-8.37 (m, 1H), 8.17 (t, J=1.8 Hz, 1H), 8.00 (dt, J=7.8, 1.3 Hz, 1H), 7.90 (ddd, J=8.3, 2.2, 1.1 Hz, 1H), 7.82-7.66 (m, 5H), 7.57 (dt, J=7.9, 1.7 Hz, 1H), 7.39-7.18 (m, 4H), 4.90 (s, 1H), 2.29 (t, J=6.2 Hz, 2H), 0.90 (t, J=12.0 Hz, 1H), 0.38 (td, J=5.7, 3.7 Hz, 2H), 0.13-0.02 (m, 2H); MS (ES+) 517.2 (M+1); (ES−) 515.2 (M−1).

Step-3: Preparation of tert-butyl ((3-(1-(3-(aminomethyl)phenyl)-3-(trifluoromethyl)-1H-pyrazole-5-carboxamido)phenyl)(pyridin-3-yl)methyl)(cyclopropylmethyl)carbamate (79d) and tert-butyl 3-(5-(3-((cyclopropylmethylamino)(pyridin-3-yl)methyl)phenylcarbamoyl)-3-(trifluoromethyl)-1H-pyrazol-1-yl)benzylcarbamate (79e)

To a stirred solution of -(3-cyanophenyl)-N-(3-(((cyclopropylmethyl)amino)(pyridin-3-yl)methyl)phenyl)-3-(trifluoromethyl)-1H-pyrazole-5-carboxamide (79c) (0.25 g, 0.484 mmol) in anhydrous methanol (5 mL), cooled to 0° C., was added di-tert-butyl dicarbonate (0.317 g, 1.452 mmol) and nickel(II) chloride hexahydrate (0.029 g, 0.121 mmol). Sodium borohydride (0.110 g, 2.90 mmol) was added to the reaction mixture in small portions over a 15 min period. The reaction mixture was stirred for 15 min at 0° C. TLC (50% 9; 1 EtOAc/MeOH in hexanes) shows starting material present. To the reaction mixture was added additional nickel (II) chloride hexahydrate (0.029 g, 0.121 mmol) and sodium borohydride (0.110 g, 2.90 mmol) in portions over 15 mins stirred for 30 mins at 0° C. TLC shows no change can see two major product one has Rf same as starting material. The reaction mixture was quenched with N1-(2-aminoethyl)ethane-1,2-diamine (0.105 mL, 0.968 mmol) stirred for 30 mins and concentrated in vacuum to dryness. The residue obtained was dissolved in dichloromethane (25 mL) and water (25 mL). The organic layer was separated and aqueous layer was extracted with dichloromethane (20 mL). The organic layers were combined washed with water (25 mL), brine (25 mL), dried, filtered and concentrated in vacuum. The residue obtained was purified by flash column chromatography (silica gel 24 g, eluting with 0-100% ethyl acetate in hexane to furnish tert-butyl ((3-(1-(3-(aminomethyl)phenyl)-3-(trifluoromethyl)-1H-pyrazole-5-carboxamido)phenyl)(pyridin-3-yl)methyl)(cyclopropylmethyl)carbamate (79d) (0.036 g, 11.98% yield) as a white solid; $^1$H NMR (300 MHz, DMSO-$d_6$) δ 10.73 (s, 1H), 8.62 (s, 1H), 8.43 (d, J=5.6 Hz, 1H), 8.13 (d, J=7.9 Hz, 1H), 7.69-7.54 (m, 4H), 7.53-7.20 (m, 8H), 5.03 (s, 1H), 4.19 (d, J=6.3 Hz, 2H), 2.40-0.90 (m, 2H), 0.93-0.84 (m, 1H), 0.45-0.32 (m, 2H), 0.11-−0.00 (m, 3H)$^{19}$F NMR (282 MHz, DMSO) δ −60.80; MS (ES+) 621.3 (M+1). Further elution gave tert-butyl 3-(5-(3-((cyclopropylmethylamino)(pyridin-3-yl)methyl)phenylcarbamoyl)-3-(trifluoromethyl)-1H-pyrazol-1-yl)benzylcarbamate (79e) (0.030 g, 9.99% yield) as a white solid which has the same Rf as starting material; $^1$H NMR (300 MHz, DMSO-$d_6$) δ 10.71 (s, 1H), 8.61 (s, 1H), 8.40 (d, J=4.9 Hz, 1H), 7.77 (d, J=7.9 Hz, 1H), 7.59-7.19 (m, 11H), 4.88 (s, 1H), 4.19 (d, J=6.2 Hz, 2H), 2.37-2.21 (m, 2H), 1.35 (s, 9H), 1.00-0.79 (m, 1H), 0.43-0.33 (m, 2H), 0.09-0.03 (m, Step-4: Preparation of 1-(3-(Aminomethyl)phenyl)-N-(3-((((cyclopropylmethyl)amino)(pyridin-3-yl)methyl)phenyl)-3-(trifluoromethyl)-1H-pyrazole-5-carboxamide (79f)

A solution of tert-butyl ((3-(1-(3-(aminomethyl)phenyl)-3-(trifluoromethyl)-1H-pyrazole-5-carboxamido)phenyl)(pyridin-3-yl)methyl)(cyclopropylmethyl)carbamate (79d) (0.03 g, 0.048 mmol) and tert-butyl 3-(5-(3-((cyclopropylmethylamino)(pyridin-3-yl)methyl)phenylcarbamoyl)-3-(trifluoromethyl)-1H-pyrazol-1-yl)benzylcarbamate (79e) (0.030 g, 0.048 mmol) were dissolved separately in methanol (2.5 mL) and added conc. HCL (0.073 mL, 2.42 mmol) and water (0.073 mL). The reaction mixture was stirred at room temperature overnight and concentrated in vacuum to dryness. The residue was azeotroped with toluene (2×10 mL) and ethanol (10 mL), dried in vacuum pump to furnish a white solid residue. NMR of both the residue in methanol and TLC shows same compound. The products were combined dried and purified by flash column chromatography (silica gel 4 g, eluting with 0-150% methanol in chloroform to furnish 1-(3-(Aminomethyl)phenyl)-N-(3-(((cyclopropylmethyl)amino)(pyridin-3-yl)methyl)phenyl)-3-(trifluoromethyl)-1H-pyrazole-5-carboxamide (79f) (0.035 g, 66%) as a white solid; $^1$H NMR (300 MHz, DMSO-$d_6$) δ 11.00 (s, 1H), 10.42 (s, 1H), 8.81 (s, 1H), 8.52 (s, 3H), 8.11 (s, 1H), 7.87 (s, 1H), 7.73 (s, 2H), 7.68-7.59 (m, 2H), 7.58-7.48 (m, 2H), 7.42 (d, J=7.6 Hz, 3H), 5.59 (s, 1H), 4.11 (s, 2H), 2.81-2.56 (m, 2H), 1.21-1.01 (m, 1H), 0.63-0.41 (m, 2H), 0.35-0.16 (m, 2H). $^{19}$F NMR (282 MHz, DMSO) δ -60.79; MS (ES+) 521.3 (M+1), (ES-) 555.2 (M+Cl).

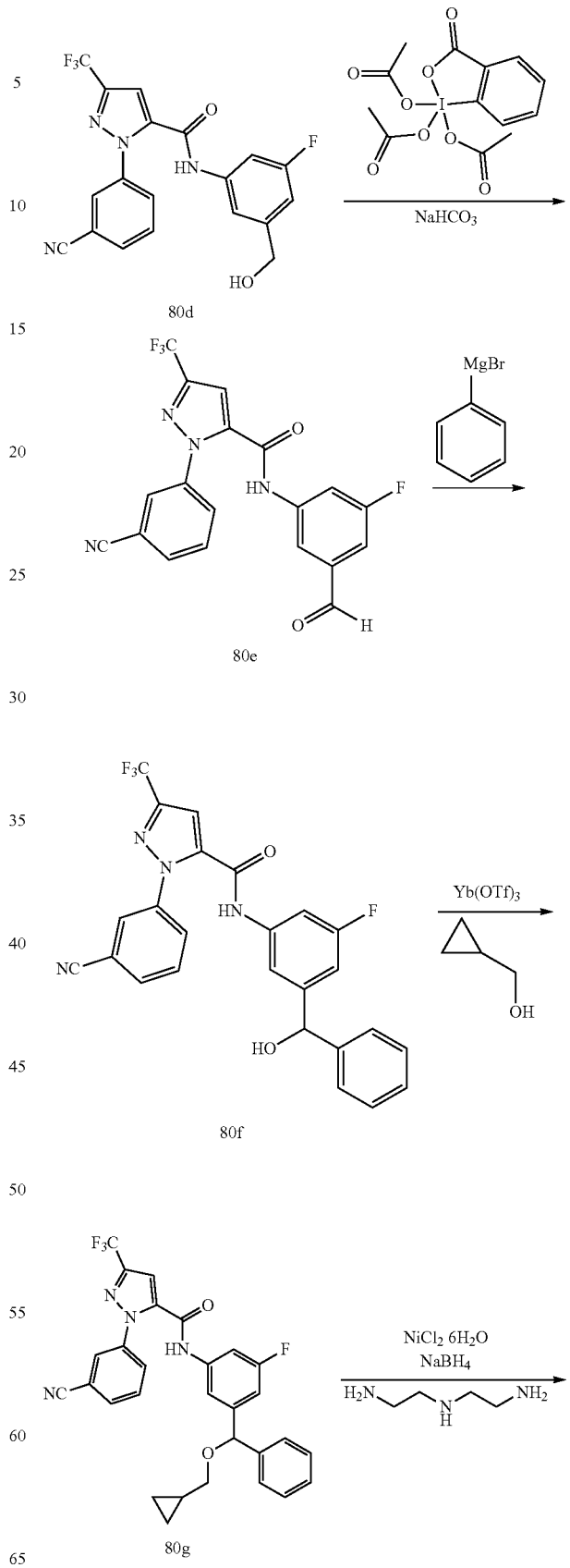

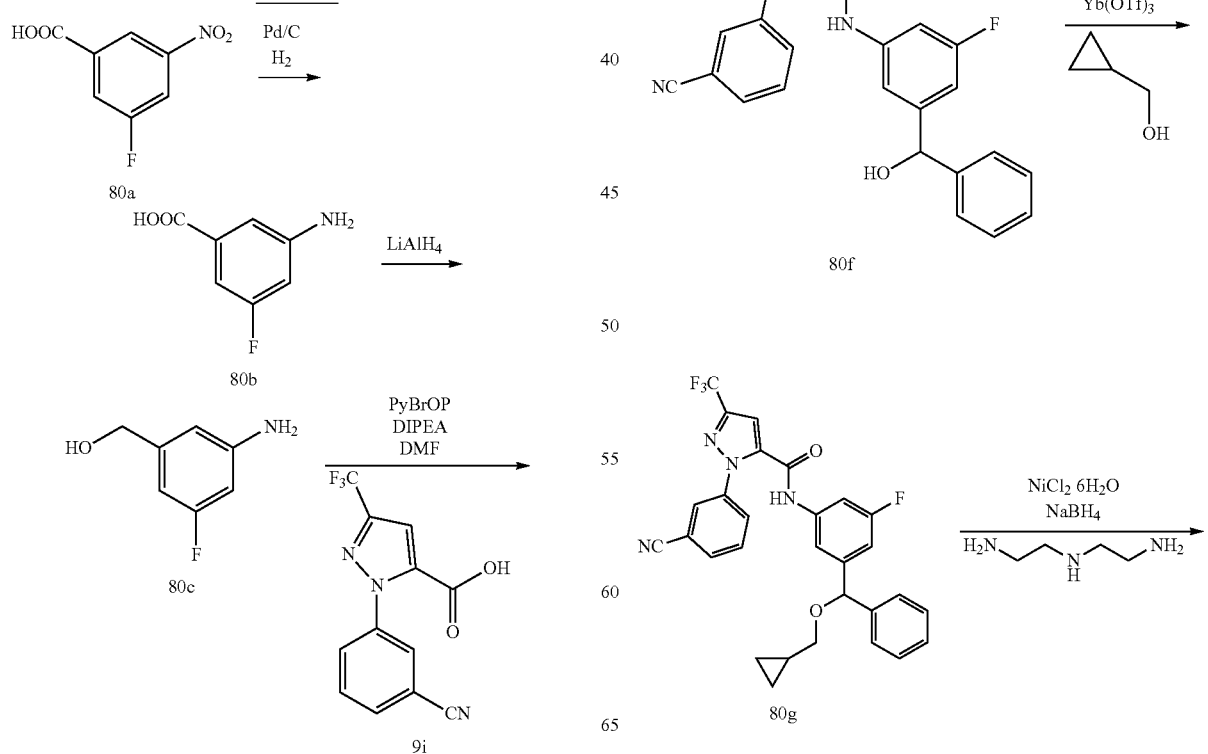

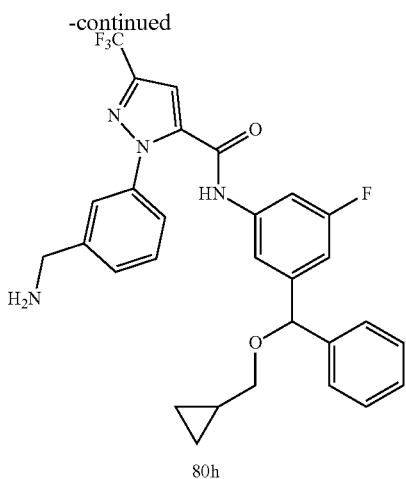

80h

Preparation of 1-(3-(aminomethyl)phenyl)-N-(3-((cyclopropylmethoxy)(phenyl)methyl)-5-fluorophenyl)-3-(trifluoromethyl)-1H-pyrazole-5-carboxamide (80h)

Step-1: Preparation of 3-Amino-5-fluorobenzoic acid (80b)

To a solution of 3-fluoro-5-nitrobenzoic acid (80a) (2.5 g, 13.51 mmol) in methanol (30 mL) was added palladium (10% Pd on carbon) (0.287 g, 2.70 mmol). The reaction mixture was hydrogenated at 60 psi for 2 h. TLC analysis (ethyl acetate/hexanes, 1:1, v/v) shows reaction was complete. The reaction was filtered through a small Celite pad, Celite pad was subsequently washed with methanol (2×25 mL) and ethyl acetate (25 mL). Excess solvents were pumped-off under reduced pressure afford 3-Amino-5-fluorobenzoic acid (80b) (1.903 g, 91% yield) as an off-white solid; $^1$H NMR (300 MHz, DMSO-d$_6$) δ 12.93 (s, 1H, D$_2$O exchangeable), 7.06-6.97 (m, 1H), 6.72 (ddd, J=9.4, 2.5, 1.4 Hz, 1H), 6.52 (dt, J=11.4, 2.3 Hz, 1H), 5.71 (s, 2H, D$_2$O exchangeable); $^{19}$F NMR (282 MHz, DMSO-d$_6$) δ −113.44; MS (ES$^+$): MS (ES+) 156.0 (M+1), MS (ES−) 153.9 (M−1).

Step-2: Preparation of (3-Amino-5-fluorophenyl)methanol (80c)

To a suspension of lithium aluminum hydride (1.209 g, 31.8 mmol), in THF (50 mL) was added drop-wise at 0° C. a solution of 3-amino-5-fluorobenzoic acid (80b) (1.9 g, 12.25 mmol) in THF (30 mL) over a period of 30 min in a positive flow of nitrogen. The reaction mixture was stirred at room temperature for 14 h, cooled down to 0° C., quenched carefully with ethyl acetate (50 mL) and stirred for 1 h. The reaction was carefully quenched with water (50 mL) under a positive flow of nitrogen, filtered through a small Celite pad, and Celite pad was washed with ethyl acetate (2×50 mL). The organic were evaporated to dryness. The residue obtained was purified by flash column chromatography [(silica gel 80 g, eluting with ethyl acetate/hexanes from 0 to 100%)] to furnish (3-Amino-5-fluorophenyl)methanol (80c) (0.594 g, 34% yield) as a pale yellow solid; $^1$H NMR (300 MHz, DMSO-d$_6$) δ 6.33 (dt, J=2.0, 1.1 Hz, 1H), 6.23-6.11 (m, 2H), 5.36 (s, 2H, D$_2$O exchangeable), 5.12 (t, J=5.8 Hz, 1H), 4.33 (d, J=5.8 Hz, 2H); $^{19}$F NMR (282 MHz, DMSO-d$_6$) δ −114.63; MS (ES$^+$): MS (ES+) 142.02 (M+1), MS (ES−) 140.00 (M−1).

Step-3: Preparation of 1-(3-cyanophenyl)-N-(3-fluoro-5-(hydroxymethyl)phenyl)-3-(trifluoromethyl)-1H-pyrazole-5-carboxamide (80d)

In a 100 mL single-necked flask containing 1-(3-cyanophenyl)-3-(trifluoromethyl)-1H-pyrazole-5-carboxylic acid (9i) (1.375 g, 4.89 mmol), (3-amino-5-fluorophenyl)methanol (80c) (0.575 g, 4.07 mmol), bromo-tris-pyrrolidino phosphoniumhexafluorophosphate(PyBrOP, 2.279 g, 4.89 mmol) was N,N-dimethylformamide (24.60 mL, 318 mmol) and N-ethyl-N-isopropylpropan-2-amine (DIPEA) (3.55 mL, 20.37 mmol) successively in a positive flow of nitrogen at room temperature. The resulting reaction mixture was stirred at room temperature for 16 h under nitrogen atmosphere. Excess DMF was pumped-off under reduced pressure. The reaction was diluted with water (75 mL) and extracted with ethyl acetate (2×75 mL), the combined organic layer was dried over anhydrous MgSO$_4$, filtered, and evaporated to dryness. The residue was purified by flash column chromatography [silica gel 25 g, eluting with ethyl acetate in hexanes from 0-100%] to furnish 1-(3-cyanophenyl)-N-(3-fluoro-5-(hydroxymethyl)phenyl)-3-(trifluoromethyl)-1H-pyrazole-5-carboxamide (80d) (1.416 g, 86% yield) as a white solid; $^1$H NMR: (300 MHz, DMSO-d$_6$) δ 10.80 (s, 1H), 8.18 (t, J=1.8 Hz, 1H), 8.02 (dt, J=7.7, 1.3 Hz, 1H), 7.92 (ddd, J=8.2, 2.2, 1.1 Hz, 1H), 7.81-7.71 (m, 2H), 7.50-7.36 (m, 2H), 6.90 (ddd, J=9.7, 2.4, 1.3 Hz, 1H), 5.38 (t, J=5.7 Hz, 1H, D$_2$O exchangeable), 4.49 (d, J=5.7 Hz, 2H); $^{19}$F NMR (282 MHz, DMSO-d$_6$) δ −60.98, −112.56; MS (ES+): MS (ES+) 427.20 (M+Na), MS (ES−) 403.22 (M−1).

Step-4: Preparation of 1-(3-cyanophenyl)-N-(3-fluoro-5-formylphenyl)-3-(trifluoromethyl)-1H-pyrazole-5-carboxamide (80e)

To a stirred solution of 1-(3-cyanophenyl)-N-(3-fluoro-5-(hydroxymethyl)phenyl)-3-(trifluoromethyl)-1H-pyrazole-5-carboxamide (80d) (1.36 g, 3.36 mmol) in dichloromethane (20 mL) was added solid sodium bicarbonate (1.413 g, 16.82 mmol) followed by Dess-MartinPeriodinane (2.140 g, 5.05 mmol) in one portion and stirred at room temperature for 6 h, TLC analysis (ethyl acetate/hexanes, 1:1, v/v) shows moderate conversion. To the reaction was added additional Dess-Martin Periodinane (2.140 g, 5.05 mmol) and stirred for 16 h. Excess solvent was pumped-off under reduced pressure. The reaction mixture was diluted with water (50 mL), and extracted with ethyl acetate (2×50 mL). The combined organic layer was dried over anhydrous MgSO$_4$; filtered, excess solvent was evaporated to dryness. The residue was purified by flash column chromatography [(silica gel 25 g, eluting with ethyl acetate/hexanes from 0 to 100%)] to furnish 1-(3-cyanophenyl)-N-(3-fluoro-5-formylphenyl)-3-(trifluoromethyl)-1H-pyrazole-5-carboxamide (80e) (0.910 g, 67% yield) as a white solid; $^1$H NMR (300 MHz, DMSO-d$_6$) δ 11.09 (s, 1H, D$_2$O exchangeable), 9.97 (d, J=1.5 Hz, 1H), 8.22 (t, J=1.8 Hz, 1H), 8.06 (t, J=1.5 Hz, 1H), 8.03 (dt, J=7.8, 1.4 Hz, 1H), 7.95 (ddd, J=8.2, 2.2, 1.1 Hz, 1H), 7.84 (dt, J=10.8, 2.3 Hz, 1H), 7.80-7.74 (m, 2H), 7.53 (ddd, J=8.4, 2.6, 1.3 Hz, 1H); $^{19}$F NMR (282 MHz, DMSO-d$_6$) δ −60.99, −110.28; IR (KBr, cm$^{-1}$): 2236 cm$^{-1}$ (—CN stretching); MS (ES$^+$): MS (ES+) 425.11 (M+Na), MS (ES−) 401.06 (M−1), 803.15 (2M−1).

Step-5: Preparation of 1-(3-cyanophenyl)-N-(3-fluoro-5-(hydroxy(phenyl)methyl)phenyl)-3-(trifluoromethyl)-1H-pyrazole-5-carboxamide (80f)

A solution of 1-(3-cyanophenyl)-N-(3-fluoro-5-formylphenyl)-3-(trifluoromethyl)-1H-pyrazole-5-carboxamide (80e) (0.413 g, 1.027 mmol) in THF (20 mL) cooled to 0° C. was added phenylmagnesium bromide (2.084 mL, 2.084 mmol). The reaction mixture was allowed to warm to room temperature and stirred at room temperature for 16 h. TLC analysis (ethyl acetate/hexanes, 1:1, v/v) shows reaction was complete. The reaction was quenched with saturated aqueous NH$_4$Cl (30 mL), and extracted with ethyl acetate (50 mL, 25 mL). The combined organic extracts were dried over anhydrous MgSO$_4$, filtered, and evaporated. The residue obtained was purified by flash column chromatography [(silica gel 25 g, eluting with ethyl acetate in hexanes from 0 to 100%)] to afford 1-(3-cyanophenyl)-N-(3-fluoro-5-(hydroxy(phenyl)methyl)phenyl)-3-(trifluoromethyl)-1H-pyrazole-5-carboxamide (80f) (155 mg, 31% yield) as a white solid; $^1$HNMR (300 MHz, DMSO-d$_6$) δ 10.81 (s, 1H, D$_2$O exchangeable), 8.18 (t, J=1.8 Hz, 1H), 8.01 (dt, J=7.8, 1.3 Hz, 1H), 7.95-7.85 (m, 1H), 7.82-7.65 (m, 2H), 7.53-7.41 (m, 2H), 7.41-7.28 (m, 4H), 7.27-7.19 (m, 1H), 7.00 (dt, J=9.8, 1.7 Hz, 1H), 6.10 (d, J=3.8 Hz, 1H, D$_2$O exchangeable), 5.69 (d, J=3.9 Hz, 1H); $^{19}$F NMR (282 MHz, DMSO-d$_6$) δ −61.00, −112.17; IR (KBr, cm$^{-1}$): 2236 cm$^{-1}$ (—CN stretching); MS (ES$^+$): MS (ES+) 503.1 (M+Na), MS (ES−) 479.1 (M−1), 959.1 (2M−1).

Step-6: Preparation of 1-(3-cyanophenyl)-N-(3-((cyclopropylmethoxy)(phenyl)methyl)-5-fluorophenyl)-3-(trifluoromethyl)-1H-pyrazole-5-carboxamide (80g)

To a solution of 1-(3-cyanophenyl)-N-(3-fluoro-5-(hydroxy(phenyl)methyl)phenyl)-3-(trifluoromethyl)-1H-pyrazole-5-carboxamide (80f) (0.113 g, 0.235 mmol) in cyclopropylmethanol (1.689 mL, 23.52 mmol) was added ytterbium(III) trifluoromethanesulfonate (0.292 g, 0.470 mmol) and heated at 80° C. for 16 h. The reaction mixture was cooled to room temperature, excess solvent was pumped-off under reduced pressure, and the residue was treated with water (30 mL), extracted with chloroform (2×30 mL), and filtered through Celite pad, excess solvent was removed under reduced pressure. The residue was purified by flash column chromatography [silica gel 25 g, eluting with ethyl acetate in hexanes from 0-100%] to furnish 1-(3-cyanophenyl)-N-(3-((cyclopropylmethoxy)(phenyl)methyl)-5-fluorophenyl)-3-(trifluoromethyl)-1H-pyrazole-5-carboxamide (80g) (31 mg, 25% yield) as white solid; $^1$H NMR (300 MHz, DMSO-d$_6$) δ 10.86 (s, 1H, D$_2$O exchangeable), 8.18 (t, J=1.8 Hz, 1H), 8.01 (dt, J=7.8, 1.3 Hz, 1H), 7.95-7.87 (m, 1H), 7.79-7.69 (m, 2H), 7.56-7.47 (m, 1H), 7.43 (s, 1H), 7.39-7.32 (m, 4H), 7.27 (dd, J=5.4, 2.9 Hz, 1H), 7.05-6.94 (m, 1H), 5.48 (s, 1H), 3.29-3.21 (m, 2H), 1.13-1.00 (m, 1H), 0.47 (dt, J=8.4, 2.5 Hz, 2H), 0.22-0.11 (m, 2H); $^{19}$F NMR (282 MHz, DMSO-d$_6$) δ −60.98, −111.79; MS (ES$^+$): MS (ES+) 557.2 (M+Na), MS (ES−) 533.2 (M−1), 569.0 (M+Cl).

Step-7: Preparation of 1-(3-(aminomethyl)phenyl)-N-(3-((cyclopropylmethoxy)(phenyl)methyl)-5-fluorophenyl)-3-(trifluoromethyl)-1H-pyrazole-5-carboxamide (80h)

To a stirred solution of 1-(3-cyanophenyl)-N-(3-((cyclopropylmethoxy)(phenyl)methyl)-5-fluorophenyl)-3-(trifluoromethyl)-1H-pyrazole-5-carboxamide (80g) (0.026 g, 0.049 mmol) in anhydrous methanol (10 mL) cooled to 0° C., was added nickel(II) chloride hexahydrate (0.017 g, 0.073 mmol) followed by sodium borohydride (0.022 g, 0.584 mmol) in small portions over a period of 5 min. The reaction mixture was stirred for 10 min quenched with N1-(2-aminoethyl)ethane-1,2-diamine (0.053 mL, 0.486 mmol). Excess methanol was pumped-off under reduced pressure. The reaction mixture was treated with saturated aqueous NH$_4$Cl (30 mL) and the product was extracted with chloroform (2×30 mL). The combined organic layer was dried over anhydrous MgSO$_4$, filtered, evaporated to dryness. The residue obtained was purified by flash column chromatography [(silica gel 2×12 g, eluting with methanol/chloroform from 0 to 50%)] to furnish 1-(3-(aminomethyl)phenyl)-N-(3-((cyclopropylmethoxy)(phenyl)methyl)-5-fluorophenyl)-3-(trifluoromethyl)-1H-pyrazole-5-carboxamide (80h) (18 mg, 69% yield) as a white solid; $^1$H NMR (300 MHz, DMSO-d$_6$) δ 10.91 (s, 1H, D$_2$O exchangeable), 7.60 (s, 1H), 7.50 (dt, J=11.5, 2.1 Hz, 2H), 7.45-7.40 (m, 3H), 7.40-7.22 (m, 6H), 7.09-6.88 (m, 1H), 5.47 (s, 1H), 3.77 (s, 2H), 3.24 (dd, J=6.8, 4.0 Hz, 2H), 1.15-0.98 (m, 1H), 0.57-0.38 (m, 2H), 0.16 (tq, J=4.8, 2.9, 2.5 Hz, 2H); $^1$H NMR (300 MHz, DMSO-d$_6$ D$_2$O) δ 7.58 (s, 1H), 7.50 (dd, J=4.1, 2.2 Hz, 2H), 7.48-7.40 (m, 3H), 7.39-7.23 (m, 6H), 7.06-6.91 (m, 1H), 5.47 (s, 1H), 3.75 (s, 2H), 3.24 (dd, J=6.8, 2.4 Hz, 2H), 1.15-0.99 (m, 1H), 0.47 (dt, J=9.2, 2.8 Hz, 2H), 0.15 (td, J=5.6, 4.9, 3.6 Hz, 2H); $^{19}$F NMR (282 MHz, DMSO-d$_6$) δ −60.76, −111.81; MS (ES$^+$): MS (ES+) 539.2 (M+1), MS (ES−) 537.1 (M−1).

Scheme 81

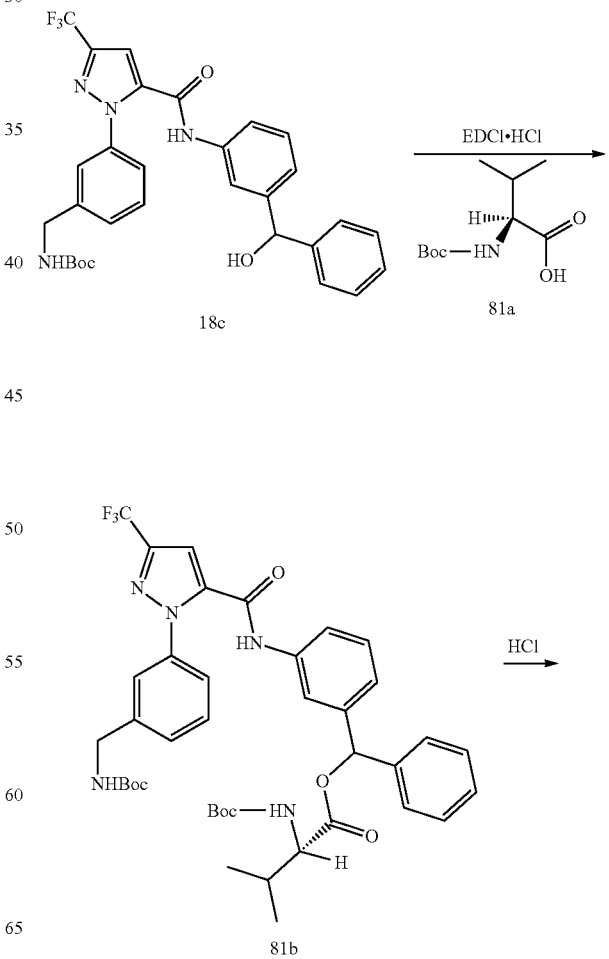

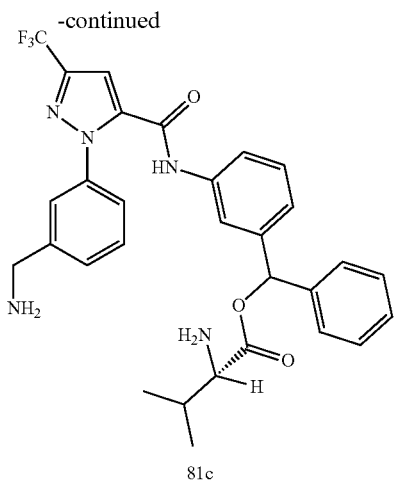

81c

Preparation of (2S)-(3-(1-(3-(aminomethyl)phenyl)-3-(trifluoromethyl)-1H-pyrazole-5-carboxamido)phenyl)(phenyl)methyl 2-amino-3-methylbutanoate (81c)

Step-1: Preparation of (2R)-(3-(1-(3-(((tert-butoxycarbonyl)amino)methyl)phenyl)-3-(trifluoromethyl)-1H-pyrazole-5-carboxamido)phenyl)(phenyl)methyl 2-((tert-butoxycarbonyl)-amino)-3-methylbutanoate (81b)

To a solution of tert-butyl 3-(5-(3-(hydroxy(phenyl)methyl)phenylcarbamoyl)-3-(trifluoromethyl)-1H-pyrazol-1-yl)benzylcarbamate (18c) (132 mg, 0.233 mmol) in DMF (4 mL) was added (S)-2-(tert-butoxycarbonylamino)-3-methylbutanoic acid (81a) (101 mg, 0.466 mmol), N,N-dimethylpyridin-4-amine (29.0 mg, 0.235 mmol) and N1-((ethylimino)methylene)-N3,N3-dimethylpropane-1,3-diamine hydrochloride (90 mg, 0.468 mmol). The reaction mixture was stirred at room temperature for 14 h, diluted with ethyl acetate (150 mL), washed with water (2×75 mL), brine (75 mL), dried over MgSO$_4$, filtered and concentrated in vacuum. The crude product was purified by flash column chromatography [silica gel 4 g, eluting with hexanes/ethyl acetate (1:0 to 2:1)] to afford (2R)-(3-(1-(3-(((tert-butoxycarbonyl)amino)methyl)phenyl)-3-(trifluoromethyl)-1H-pyrazole-5-carboxamido)phenyl)(phenyl)methyl-2-((tert-butoxycarbonyl)-amino)-3-methylbutanoate (81b) (125 mg, 70%) as an off-white solid. $^1$H NMR (300 MHz, DMSO-d$_6$) δ 10.76 (d, J=4.2 Hz, 1H), 7.67-7.12 (m, 16H), 6.78 (s, 1H), 4.19 (d, J=6.2 Hz, 2H), 3.94 (ddd, J=8.1, 6.6, 3.7 Hz, 1H), 2.15-2.02 (m, 1H), 1.36 (d, J=1.6 Hz, 18H), 0.80 (d, J=6.8 Hz, 6H); $^{19}$F NMR (282 MHz, DMSO-d$_6$) δ −60.82; MS (ES+): 766.5 (M+1).

Step-2: Preparation of (2S)-(3-(1-(3-(aminomethyl)phenyl)-3-(trifluoromethyl)-1H-pyrazole-5-carboxamido)phenyl)(phenyl)methyl 2-amino-3-methylbutanoate (81c)

A solution of (2R)-(3-(1-(3-(((tert-butoxycarbonyl)amino)methyl)phenyl)-3-(trifluoromethyl)-1H-pyrazole-5-carboxamido)phenyl)(phenyl)methyl-2-((tert-butoxycarbonyl)-amino)-3-methylbutanoate (81b) (60 mg, 0.078 mmol) in 1,4-Dioxane (4 mL) was treated with hydrogen chloride (0.830 mL, 3.32 mmol) (4 M in 1,4-dioxane) and stirred at room temperature for 14.5 h. The reaction mixture was treated with hexanes, decanted, washed with hexanes, and decanted again. The insoluble crude product was purified by flash column chromatography [silica gel, eluting with chloroform/CMA 80 (1:0 to 2:1)] to afford (2S)-(3-(1-(3-(aminomethyl)phenyl)-3-(trifluoromethyl)-1H-pyrazole-5-carboxamido)phenyl)(phenyl)methyl 2-amino-3-methylbutanoate (81c) (35 mg, 79% yield, as a mixture of diastereoisomers) as a yellow solid; $^1$H NMR (300 MHz, DMSO-d$_6$) δ 10.89 (d, J=3.7 Hz, 1H), 8.38 (s, 4H), 7.79 (d, J=2.0 Hz, 1H), 7.74-7.69 (m, 2H), 7.67-7.49 (m, 4H), 7.47-7.32 (m, 6H), 7.29-7.23 (m, 1H), 6.92 (s, 1H), 4.12 (s, 2H), 4.14-4.04 (m, 1H), 2.30-2.22 (m, 1H), 0.94-0.86 (m, 6H); $^{19}$F NMR (282 MHz, DMSO-d$_6$) δ −60.80, −60.81; MS (ES+): 566.3 (M+1).

Scheme 82

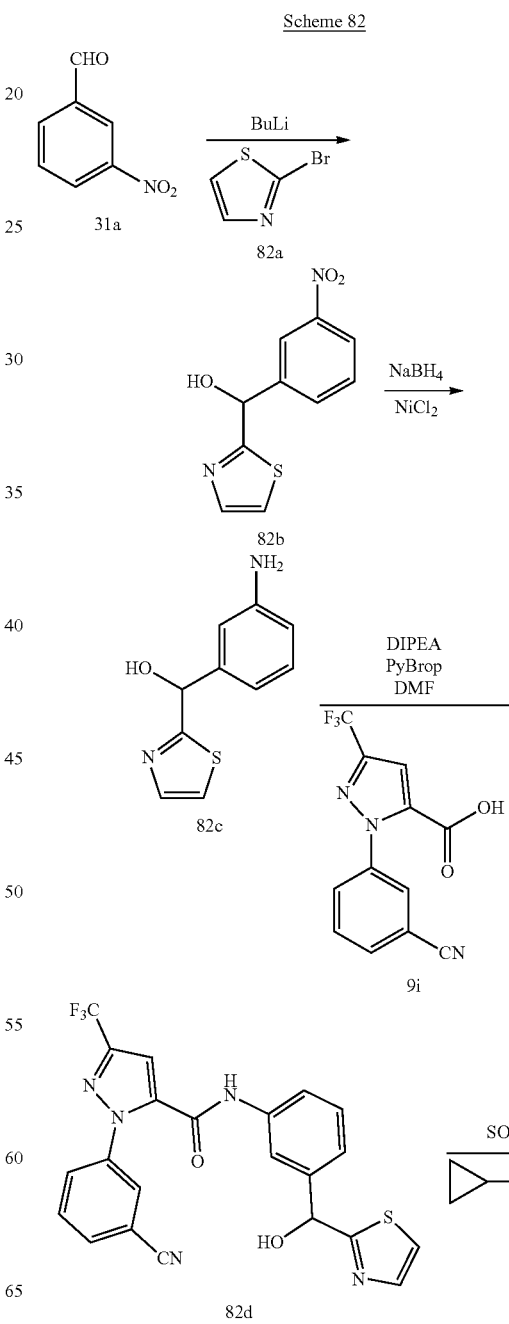

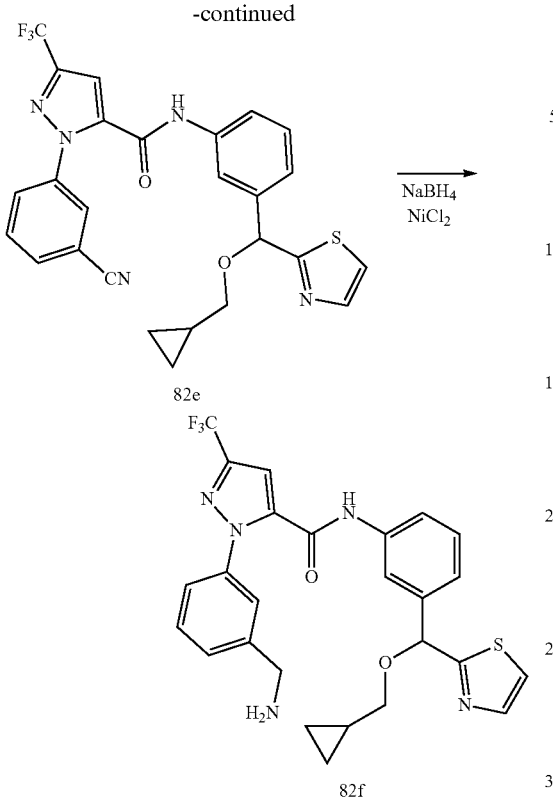

Preparation of 1-(3-(aminomethyl)phenyl)-N-(3-((cyclopropylmethoxy)(thiazol-2-yl)methyl)-phenyl)-3-(trifluoromethyl)-1H-pyrazole-5-carboxamide (82f)

Step-1: Preparation of 3-nitrophenyl)(thiazol-2-yl)methanol (82b)

To a solution of 2-bromothiazole (82a) (1.8 mL, 17.42 mmol) in ether (12 mL) at −78° C. was added dropwise n-BuLi (11.00 mL, 17.60 mmol) and stirred −78° C. for 2 h. To the 2-lithiated thiazole was added dropwise a solution of 3-nitrobenzaldehyde (31a) (2.63 g, 17.42 mmol) in THF (18 mL) at −78° C. and stirred at −78° C. for 2 h and at room temperature for 2 h. The reaction mixture was quenched with saturated ammonium chloride (50 mL). The organic layer was separated and aqueous layer was extracted with ethyl acetate (75 mL). The organic layers were combined washed with brine (60 mL), dried, filtered and concentrated in vacuum to dryness. The residue obtained was purified by flash column chromatography [silica gel 40 g, eluting with ethyl acetate in hexane (1:0 to 2:1)] to give (3-nitrophenyl)(thiazol-2-yl)methanol (82b) (1.1 g, 27%) as a brown solid; $^1$H NMR (300 MHz, DMSO-$d_6$) δ 8.32 (ddd, J=2.2, 1.4, 0.7 Hz, 1H), 8.16 (ddd, J=8.3, 2.4, 1.1 Hz, 1H), 7.93 (dddd, J=7.8, 1.7, 1.1, 0.6 Hz, 1H), 7.74 (d, J=3.2 Hz, 1H), 7.69 (d, J=2.4 Hz, 1H), 7.67 (d, J=2.3 Hz, 1H), 7.20 (d, J=4.8 Hz, 1H), 6.17 (d, J=4.7 Hz, 1H); MS (ES+): 259.1 (M+23).

Step-2: Preparation of (3-aminophenyl)(thiazol-2-yl)methanol (82c)

To a solution of (3-nitrophenyl)(thiazol-2-yl)methanol (82b) (1.072 g, 4.54 mmol) in methanol (27 mL) cooled to 0° C. was added nickel(II) chloride hexahydrate (0.270 g, 1.134 mmol) followed by sodium borohydride (0.701 g, 18.15 mmol) portionwise over a period of 30 min. The reaction mixture was stirred at room temperature for 30 min, quenched with N1-(2-aminoethyl)ethane-1,2-diamine (1.0 mL, 9.26 mmol), stirred for additional 30 min and concentrated in vacuum to dryness. The residue was treated with ethyl acetate (75 mL), washed with water (60 mL). The aqueous phase was extracted again with ethyl acetate (75 mL). The combined extracts were washed with brine (75 mL), dried over MgSO$_4$, filtered and concentrated in vacuum to dryness. The crude residue was purified by flash column chromatography [silica gel 25 g, eluting with hexanes/ethyl acetate (1:0 to 0:1)] to afford (3-aminophenyl)(thiazol-2-yl)methanol (82c) (667 mg, 71%) as a yellow solid; $^1$H NMR (300 MHz, DMSO-$d_6$) δ 7.67 (d, J=3.3 Hz, 1H), 7.60 (d, J=3.3 Hz, 1H), 6.95 (t, J=7.7 Hz, 1H), 6.65-6.62 (m, 1H), 6.59-6.53 (m, 2H), 6.43 (ddd, J=7.9, 2.3, 1.1 Hz, 1H), 5.74 (d, J=4.0 Hz, 1H), 5.07 (s, 2H); MS (ES+): 207.1 (M+1).

Step-3: Preparation of 1-(3-cyanophenyl)-N-(3-(hydroxy(thiazol-2-yl)methyl)phenyl)-3-(trifluoromethyl)-1H-pyrazole-5-carboxamide (82d)

To a solution of (3-aminophenyl)(thiazol-2-yl)methanol (82c) (0.983 g, 3.50 mmol) in N,N-dimethylformamide (26 mL) was added 1-(3-cyanophenyl)-3-(trifluoromethyl)-1H-pyrazole-5-carboxylic acid (9i) (0.872 g, 3.10 mmol), N-ethyl-N-isopropylpropan-2-amine (4.40 mL, 25.3 mmol) and bromotripyrrolidin-1-ylphosphonium hexafluorophosphate(V) (1.476 g, 3.1 mmol) at room temperature. The reaction mixture was stirred at 25° C. for 16 h and diluted with ethyl acetate (200 mL). The reaction mixture was washed with water (2×100 mL), brine (75 mL), dried over anhydrous MgSO$_4$, filtered and concentrated in vacuum to dryness. The residue obtained was purified by flash column chromatography [silica gel 12 g, eluting with hexanes/ethyl acetate (1:0 to 0:1) to afford 1-(3-cyanophenyl)-N-(3-(hydroxy(thiazol-2-yl)methyl)phenyl)-3-(trifluoromethyl)-1H-pyrazole-5-carboxamide (82d) (1.113 g, 76%) as a yellow solid. $^1$H NMR (300 MHz, DMSO-$d_6$) δ 10.69 (s, 1H), 8.17 (t, J=1.7 Hz, 1H), 8.01 (dt, J=7.7, 1.3 Hz, 1H), 7.91 (ddd, J=8.2, 2.2, 1.1 Hz, 1H), 7.77-7.58 (m, 6H), 7.31 (t, J=7.8 Hz, 1H), 7.21 (dt, J=7.8, 1.4 Hz, 1H), 6.86 (d, J=4.2 Hz, 1H), 5.92 (d, J=4.2 Hz, 1H); MS (ES+): 470.1 (M+1).

Step-4: Preparation of 1-(3-cyanophenyl)-N-(3-((cyclopropylmethoxy)(thiazol-2-yl)methyl)phenyl)-3-(trifluoromethyl)-1H-pyrazole-5-carboxamide (82e)

To a solution of 1-(3-cyanophenyl)-N-(3-(hydroxy(thiazol-2-yl)methyl)phenyl)-3-(trifluoromethyl)-1H-pyrazole-5-carboxamide (82d) (500 mg, 1.065 mmol) in dichloromethane (20 mL) at 0° C. was added thionyl chloride (0.240 mL, 3.29 mmol) and allowed to warm to room temperature over 2 h. The reaction mixture was quenched with triethyl amine (1.4 mL, 10.04 mmol) and stirred at room temperature for 1 h. To the chloro compound was added cyclopropylmethanol (8.00 mL, 97 mmol), triethyl amine (1.300 mL, 9.33 mmol) and concentrated in vacuum to remove most of dichloromethane. Triethyl amine (1.4 mL, 10.04 mmol) was added to reaction mixture and heated at 70° C. for 15 h and 120° C. for 4 h. The reaction mixture was diluted with ethyl acetate and filtered. The filtrate was concentrated in vacuum and the residue was purified by flash column chromatography [silica gel eluting with hexanes/ ethyl acetate (1:0 to 2:1)] to afford 1-(3-cyanophenyl)-N-(3-((cyclopropylmethoxy)(thiazol-2-yl)methyl)phenyl)-3-(trifluoromethyl)-1H-pyrazole-5-carboxamide (82e) (296 mg, 53%) as a light brown solid; $^1$H NMR (300 MHz, DMSO-$d_6$) δ 10.53 (s, 1H), 7.98 (dd, J=2.1, 1.4 Hz, 1H), 7.84-7.78 (m, 1H), 7.72 (ddd, J=8.2, 2.2, 1.1 Hz, 1H), 7.58-7.38 (m, 6H), 7.15 (t, J=7.9 Hz, 1H), 6.99 (dt, J=7.6, 1.3 Hz, 1H), 5.60 (s, 1H), 0.95-0.81 (m, 1H), 0.37-0.20 (m, 2H), 0.07--0.08 (m, 2H); MS (ES+): 524.2 (M+1).

Step-5: Preparation of 1-(3-(aminomethyl)phenyl)-N-(3-((cyclopropylmethoxy)(thiazol-2-yl)methyl)phenyl)-3-(trifluoromethyl)-1H-pyrazole-5-carboxamide (82f)

To a solution of 1-(3-cyanophenyl)-N-(3-((cyclopropylmethoxy)(thiazol-2-yl)methyl)phenyl)-3-(trifluoromethyl)-1H-pyrazole-5-carboxamide (82e) (233 mg, 0.445 mmol) in MeOH (10 mL) cooled with ice/water was added nickel(II) chloride hexahydrate (23.00 mg, 0.097 mmol) followed by sodium borohydride (107 mg, 2.78 mmol) over a period of 5 min. the reaction mixture was stirred at room temperature for 1 h quenched with N1-(2-aminoethyl)ethane-1,2-diamine (0.100 mL, 0.912 mmol) stirred at room temperature for 0.5 h and concentrated in vacuum to dryness. The residue was treated with ethyl acetate (120 mL), washed with water (60 mL). The aqueous phase was extracted again with ethyl acetate (60 mL). The organic extracts were combined washed with brine (60 mL), dried over MgSO$_4$, filtered and concentrated in vacuum. The crude product was purified by flash column chromatography [silica gel 12 g, eluting with chloroform/CMA80 (1:0 to 3:1)] to give 1-(3-(aminomethyl)phenyl)-N-(3-((cyclopropylmethoxy)(thiazol-2-yl)methyl)phenyl)-3-(trifluoromethyl)-1H-pyrazole-5-carboxamide (82f) (54 mg, 23%) as a colorless gum. $^1$H NMR (300 MHz, DMSO-$d_6$) δ 10.77 (s, 1H), 7.73-7.68 (m, 3H), 7.65-7.59 (m, 1H), 7.59 (s, 1H), 7.54-7.51 (m, 1H), 7.46-7.40 (m, 2H), 7.40-7.29 (m, 2H), 7.18 (dt, J=7.7, 1.3 Hz, 1H), 5.78 (s, 1H), 3.77 (s, 2H), 3.37 (d, J=6.9 Hz, 2H), 1.10-1.04 (m, 1H), 0.52-0.45 (m, 2H), 0.22-0.15 (m, 2H); 19F NMR (282 MHz, DMSO-$d_6$) δ −60.73; MS (ES+): 528.2 (M+H).

Scheme 83

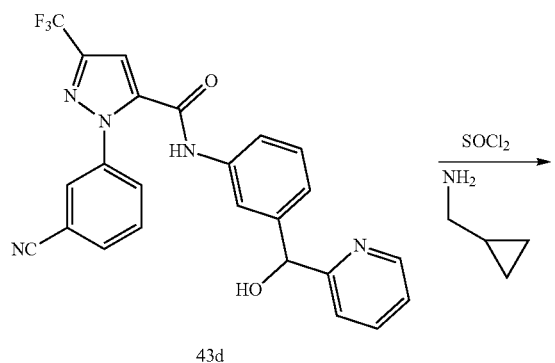

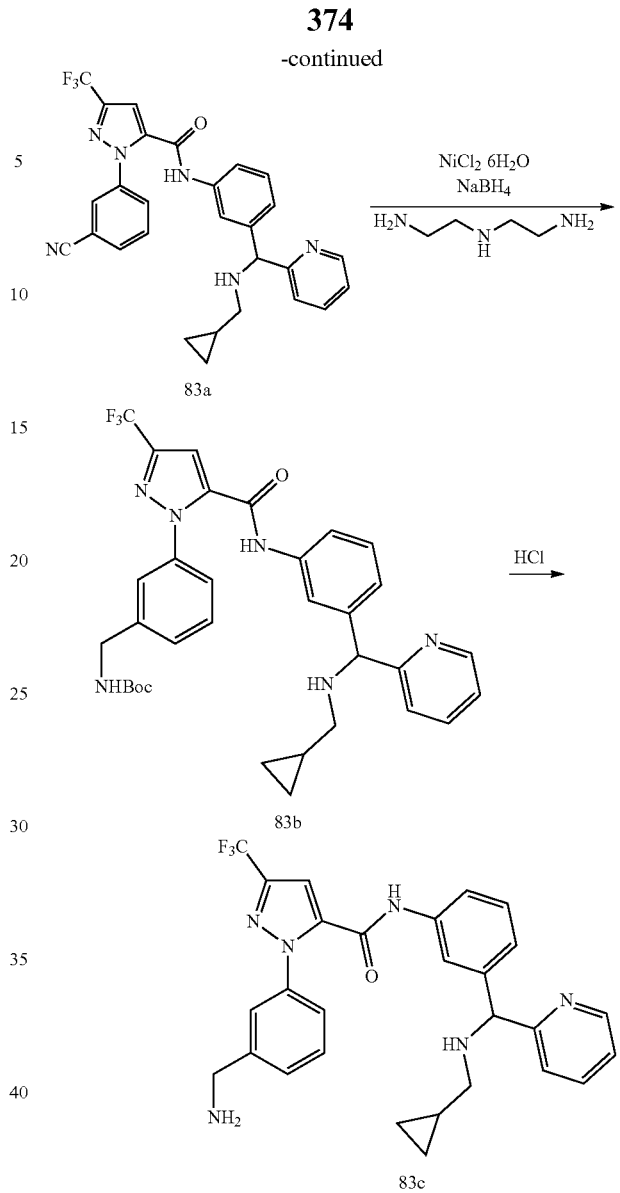

Preparation of 1-(3-(aminomethyl)phenyl)-N-(3-((cyclopropylmethylamino)(pyridin-2-yl)methyl)phenyl)-3-(trifluoromethyl)-1H-pyrazole-5-carboxamide (83c)

Step-1: Preparation of 1-(3-cyanophenyl)-N-(3-((cyclopropylmethylamino)(pyridin-2-yl)methyl)phenyl)-3-(trifluoromethyl)-1H-pyrazole-5-carboxamide (83a)

To a solution of 1-(3-cyanophenyl)-N-(3-(hydroxy(pyridin-2-yl)methyl)phenyl)-3-(trifluoro-methyl)-1H-pyrazole-5-carboxamide (43d) (0.48 g, 1.036 mmol) in dichloromethane (20 mL) at 0° C. was added thionyl chloride (0.240 mL, 3.29 mmol) and allowed to warm to room temperature over 2 h. The reaction mixture was quenched with triethylamine (1.3 mL, 9.33 mmol) and stirred at room temperature for 1 h. To the chloro compound was added cyclopropylmethanamine (1520 mg, 20.74 mmol) and concentrated in vacuum to remove most of dichloromethane. To the residue was added acetonitrile (15 mL) and heated at reflux for 16.5 h and concentrated in vacuum to dryness. The residue was treated with chloroform (150 mL), washed with water (75 mL), dried over MgSO$_4$ followed by filtration and concentration. The crude product was purified by flash column chromatography [silica gel 12 g, eluting with chloroform/CMA80 (1:0 to 4:1)] to give 1-(3-cyanophenyl)-N-(3-((cyclopropylmethylamino)(pyridin-2-yl)methyl)phenyl)-3-(trifluoromethyl)-1H-pyrazole-5-carboxamide (83a) (119 mg, 22%) as a white semisolid; $^1$H NMR (300 MHz, DMSO-d$_6$) δ 10.64 (s, 1H), 8.47 (ddd, J=4.8, 1.8, 0.9 Hz, 1H), 8.16 (t, J=1.8 Hz, 1H), 8.00 (dt, J=7.8, 1.3 Hz, 1H), 7.94-7.87 (m, 1H), 7.79-7.15 (m, 9H), 4.90 (s, 1H), 2.40-2.20 (m, 2H), 0.91 (s, 1H), 0.44-0.30 (m, 2H), 0.09-0.00 (m, 2H); $^{19}$F NMR (282 MHz, DMSO-d$_6$) δ −60.97; MS (ES+): 517.3 (M+1).

Step-2: Preparation of tert-butyl 3-(5-(3-((cyclopropylmethylamino)(pyridin-2-yl)methyl)phenylcarbamoyl)-3-(trifluoromethyl)-1H-pyrazol-1-yl)benzylcarbamate (83b)

To a solution of 1-(3-cyanophenyl)-N-(3-((cyclopropylmethylamino)(pyridin-2-yl)methyl)phenyl)-3-(trifluoromethyl)-1H-pyrazole-5-carboxamide (83a) (72 mg, 0.139 mmol) in MeOH (4 mL) cooled with ice/water was added di-tert-butyl dicarbonate (92 mg, 0.418 mmol), nickel(II) chloride hexahydrate (7.0 mg, 0.029 mmol) followed by sodium borohydride (33.0 mg, 0.856 mmol) over a period of 5 min. The reaction mixture was stirred at room temperature for 1 h followed by the addition of additional nickel(II) chloride hexahydrate (5 mg) and sodium borohydride (23 mg) and stirring at room temperature for 0.5 h The reaction was quenched with N1-(2-aminoethyl)ethane-1,2-diamine (0.03 mL, 0.279 mmol) stirred at room temperature for 0.5 h and concentrated in vacuum to dryness. The residue was treated with ethyl acetate (100 mL), washed with water (60 mL). The aqueous phase was extracted again with ethyl acetate (60 mL). The organic extracts were combined washed with brine (60 mL), dried over MgSO$_4$, filtered and concentrated in vacuum. The crude product was purified by flash column chromatography [silica gel 2×4 g, eluting with chloroform/CMA80 (1:0 to 4:1)] to afford tert-butyl 3-(5-(3-((cyclopropylmethylamino)(pyridin-2-yl)methyl)phenylcarbamoyl)-3-(trifluoromethyl)-1H-pyrazol-1-yl)benzylcarbamate (83b) (13 mg, 15%); MS (ES+): 621.2 (M+H).

Step-3: Preparation of 1-(3-(aminomethyl)phenyl)-N-(3-((cyclopropylmethylamino)(pyridin-2-yl)methyl)phenyl)-3-(trifluoromethyl)-1H-pyrazole-5-carboxamide (83c)

To a solution of tert-butyl 3-(5-(3-((cyclopropylmethylamino)(pyridin-2-yl)methyl)phenylcarbamoyl)-3-(trifluoromethyl)-1H-pyrazol-1-yl)benzylcarbamate (83b) (13 mg, 0.021 mmol) in 1,4-Dioxane (3 mL) was added hydrogen chloride (0.23 mL, 0.922 mmol, 4 M in 1,4-dioxane) and stirred at room temperature for 17.5 h. The reaction mixture was treated with hexanes, decanted, washed with hexanes, and decanted again. The insoluble crude product was purified by flash column chromatography [silica gel, eluting with chloroform/CMA80 (1:0 to 3:1) to afford 1-(3-(aminomethyl)phenyl)-N-(3-((cyclopropylmethylamino)(pyridin-2-yl)methyl)phenyl)-3-(trifluoromethyl)-1H-pyrazole-5-carboxamide (83c) (5.3 mg, 49%) as a white semisolid. $^1$H NMR (300 MHz, Methanol-d$_4$) δ 8.49 (ddd, J=4.9, 1.7, 0.9 Hz, 1H), 7.80-7.13 (m, 13H), 4.97 (s, 1H), 3.86 (s, 2H), 2.46-2.28 (m, 2H), 1.02-0.81 (m, 1H), 0.54-0.39 (m, 2H), 0.12-0.02 (m, 2H); $^{19}$F NMR (282 MHz, Methanol-d$_4$) δ −63.73; MS (ES+): 521.2 (M+1).

Scheme 84

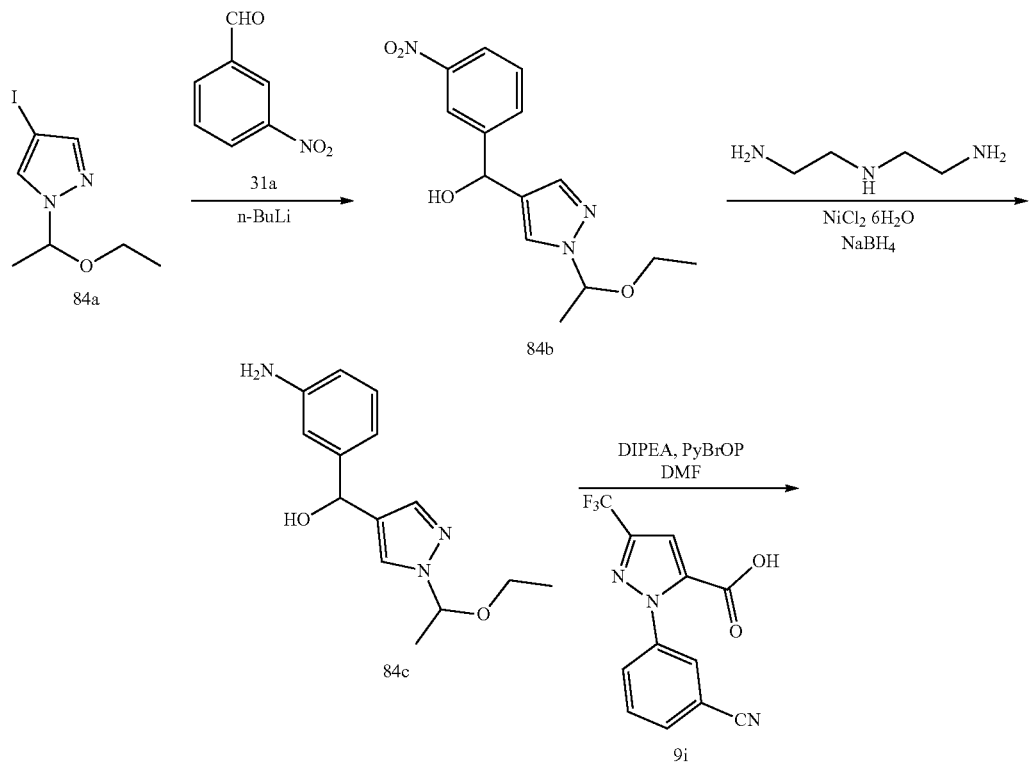

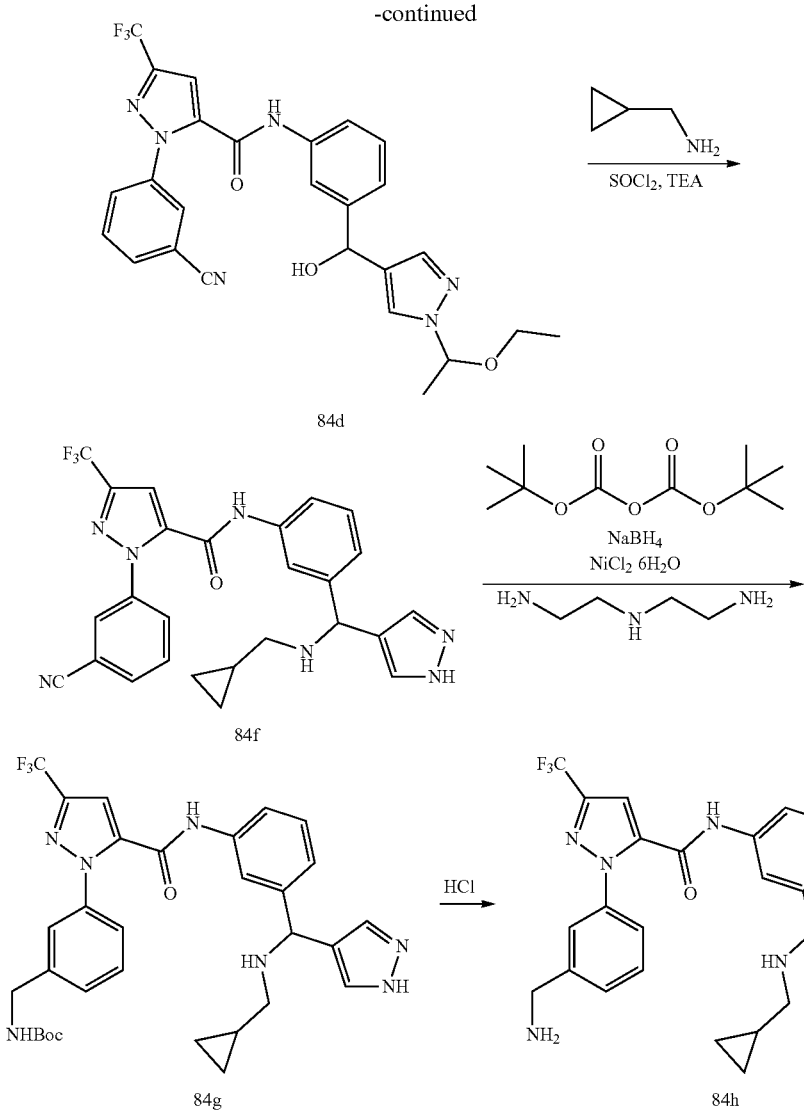

Preparation of 1-(3-(aminomethyl)phenyl)-N-(3-(((cyclopropylmethyl)amino)(1H-pyrazol-4-yl)methyl)phenyl)-3-(trifluoromethyl)-1H-pyrazole-5-carboxamide (84h)

Step-1: Preparation of (1-(1-ethoxyethyl)-1H-pyrazol-4-yl)(3-nitrophenyl)methanol (84b)

To a solution of 1-(1-ethoxyethyl)-4-iodo-1H-pyrazole (84a) (5 g, 18.79 mmol) (Prepared as reported by Lin, Qiyan et al; *Organic Letters* 11(9): 1999-2002 (2009)) in ether (16 mL) cooled to −78° C. was added dropwise a solution of n-butyllithium (12.0 mL, 19.2 mmol) in hexane followed by stirring for 30 mins at −78° C. To the anion formed was added a solution of 3-nitrobenzaldehyde (31a) (2.87 g, 18.79 mmol) in THF (24 mL) slowly at −78° C., stirred at −78° C. for 2 h and then at room temperature for 2 h. The reaction mixture was quenched with saturated ammonium chloride (50 mL). The organic layer was separated and the aqueous phase was extracted with ethyl acetate (75 mL). The organic layers were combined washed with brine (60 mL), dried over MgSO$_4$, filtered and concentrated in vacuum. The residue obtained was purified by flash column chromatography [(silica gel 80 g, eluting with hexanes/ethyl acetate (1:0 to 1:1)] to furnish (1-(1-ethoxyethyl)-1H-pyrazol-4-yl)(3-nitrophenyl)methanol (84b) (3.537 g, 64.6%) as a yellow gum; $^1$H NMR (300 MHz, DMSO-d$_6$) δ 8.24 (s, 1H), 8.11 (ddd, J=8.1, 2.4, 1.1 Hz, 1H), 7.82 (ddq, J=7.8, 1.8, 1.0 Hz, 1H), 7.74 (d, J=0.8 Hz, 1H), 7.63 (t, J=7.9 Hz, 1H), 7.37 (s, 1H), 6.04 (dd, J=4.8, 1.6 Hz, 1H), 5.85 (d, J=4.7 Hz, 1H), 5.47 (q, J=6.0 Hz, 1H), 3.43-3.35 (m, 1H), 3.23-3.05 (m, 1H), 1.54 (d, J=6.0 Hz, 3H), 1.00 (td, J=7.0, 0.6 Hz, 3H); MS (ES+) 314.184 (M+Na).

Step-2: Preparation of (3-Aminophenyl)(1-(1-ethoxyethyl)-1H-pyrazol-4-yl)methanol (84c)

To a solution of (1-(1-ethoxyethyl)-1H-pyrazol-4-yl)(3-nitrophenyl)methanol (84b) (3.437 g, 11.80 mmol) in methanol (70 mL) cooled to 0° C. was added nickel(II) chloride hexahydrate (0.701 g, 2.95 mmol). Sodium borohydride (1.822 g, 47.2 mmol) was added portionwise over a 30 mins period followed by stirring at room temperature for 30 min. The reaction mixture was quenched with N1-(2-aminoethyl)

ethane-1,2-diamine (2.60 mL, 24.07 mmol) and stirred at RT for 0.5 h. The reaction mixture was concentrated to dryness and the residue was dissolved in ethyl acetate (240 mL) and water (100 mL). The aqueous phase was separated and extracted with ethyl acetate (100 mL). The organic layers were combined washed with brine (120 mL), dried over MgSO$_4$, filtered and concentrated in vacuum. The residue obtained was purified by flash column chromatography (Silica gel 40 g, eluting with hexanes/ethyl acetate (1:0 to 0:1)] to afford (3-Aminophenyl)(1-(1-ethoxyethyl)-1H-pyrazol-4-yl)methanol (84c) (3.104 g, 100%) as a colorless oil; $^1$H NMR (300 MHz, DMSO-d$_6$) δ 7.64-7.54 (m, 1H), 7.27 (d, J=0.7 Hz, 1H), 6.94 (t, J=7.7 Hz, 1H), 6.60 (t, J=1.9 Hz, 1H), 6.50 (ddt, J=7.7, 1.7, 0.8 Hz, 1H), 6.45-6.32 (m, 1H), 5.53-5.39 (m, 3H), 4.99 (s, 2H), 3.42-3.36 (m, 1H), 3.14 (dqd, J=9.6, 7.0, 1.3 Hz, 1H), 1.59-1.41 (m, 3H), 1.01 (td, J=7.0, 0.8 Hz, 3H).

Step-3: Preparation of 1-(3-cyanophenyl)-N-(3-((1-(1-ethoxyethyl)-1H-pyrazol-4-yl)(hydroxy)methyl) phenyl)-3-(trifluoromethyl)-1H-pyrazole-5-carboxamide (84d)

To a solution of 1-(3-cyanophenyl)-3-(trifluoromethyl)-1H-pyrazole-5-carboxylic acid (9i) (3.19 g, 11.34 mmol) in DMF (90 mL) was added 1-(3-cyanophenyl)-3-(trifluoromethyl)-1H-pyrazole-5-carboxylic acid (84c) (3.19 g, 11.34 mmol), N-ethyl-N-isopropylpropan-2-amine (16.0 mL, 92 mmol) and bromotripyrrolidin-1-ylphosphonium hexafluorophosphate(V) (PyBrOP, 5.40 g, 11.34 mmol). The reaction mixture was stirred at room temperature for 16 h. The reaction mixture was diluted with ethyl acetate (300 mL), washed with water (2×120 mL), brine (120 mL), dried over MgSO$_4$, filtered and concentrated in vacuum. The residue obtained was purified by flash column chromatography [(silica gel 80 g, eluting with hexanes/ethyl acetate (1:0 to 0:1)] to furnish 1-(3-cyanophenyl)-N-(3-((1-(1-ethoxyethyl)-1H-pyrazol-4-yl)(hydroxy)methyl)phenyl)-3-(trifluoromethyl)-1H-pyrazole-5-carboxamide (84d) (4.766 g, 80%) as a light yellow solid; $^1$H NMR (300 MHz, DMSO-d$_6$) δ 10.65 (s, 1H), 8.17 (t, J=1.8 Hz, 1H), 8.01 (dt, J=7.7, 1.3 Hz, 1H), 7.91 (ddd, J=8.2, 2.2, 1.1 Hz, 1H), 7.77-7.62 (m, 4H), 7.60-7.50 (m, 1H), 7.36-7.24 (m, 2H), 7.18-7.10 (m, 1H), 5.74 (dd, J=4.4, 1.9 Hz, 1H), 5.64 (d, J=4.4 Hz, 1H), 5.46 (q, J=6.0 Hz, 1H), 3.44-3.35 (m, 1H), 3.21-3.05 (m, 1H), 1.60-1.45 (m, 3H), 0.99 (td, J=7.0, 1.1 Hz, 3H).

Step-4: Preparation of 1-(3-cyanophenyl)-N-(3-((cyclopropylmethylamino)(1H-pyrazol-4-yl)methyl) phenyl)-3-(trifluoromethyl)-1H-pyrazole-5-carboxamide (84f)

To a solution of 1-(3-cyanophenyl)-N-(3-((1-(1-ethoxyethyl)-1H-pyrazol-4-yl)(hydroxy)methyl)phenyl)-3-(trifluoromethyl)-1H-pyrazole-5-carboxamide (84d) (559 mg, 1.066 mmol) in dichloromethane (20 mL) at 0° C. was added thionyl chloride (0.16 mL, 2.167 mmol) and allowed to warm to room temperature over a 2 h period. The reaction mixture was treated with triethyl amine (0.91 mL, 6.53 mmol) and stirred at room temperature for 1 h. The reaction mixture was quenched with cyclopropylmethanamine (1600 mg, 21.82 mmol) and concentrated in vacuum to remove most of dichloromethane. To the reaction mixture was added acetonitrile (15 mL), triethylamine (0.45 mL), heated at reflux for 17 h and concentrated in vacuum to dryness. The residue obtained was dissolved in chloroform (150 mL), washed with water (75 mL), dried over MgSO$_4$, filtered and concentrated in vacuum to dryness. The residue obtained was purified by flash column chromatography [silica gel 12 g, eluting with chloroform/methanol (1:0 to 9:1)] to furnish 1-(3-cyanophenyl)-N-(3-((cyclopropylmethylamino)(1H-pyrazol-4-yl)methyl)phenyl)-3-(trifluoromethyl)-1H-pyrazole-5-carboxamide (84f) (264 mg, 49%) as a yellow solid; $^1$H NMR (300 MHz, DMSO-d$_6$) δ 12.60 (s, 1H), 10.64 (s, 1H), 8.17 (t, J=1.8 Hz, 1H), 8.00 (dt, J=7.7, 1.3 Hz, 1H), 7.91 (ddd, J=8.2, 2.2, 1.1 Hz, 1H), 7.78-7.69 (m, 2H), 7.67-7.50 (m, 3H), 7.29 (dd, J=17.4, 9.7 Hz, 2H), 7.18 (d, J=7.6 Hz, 1H), 4.79 (s, 1H), 2.37-2.09 (m, 3H), 0.86 (d, J=22.2 Hz, 1H), 0.37 (d, J=8.1 Hz, 2H), 0.05 (t, J=5.9 Hz, 2H); $^{19}$F NMR (282 MHz, DMSO-d$_6$) δ −60.97; MS (ES) 506 (ES+).

Step-5: Preparation of tert-butyl 3-(5-(3-((cyclopropylmethylamino)(1H-pyrazol-4-yl)methyl)phenylcarbamoyl)-3-(trifluoromethyl)-1H-pyrazol-1-yl) benzylcarbamate (84g)

To a solution of 1-(3-cyanophenyl)-N-(3-((cyclopropylmethylamino)(1H-pyrazol-4-yl)methyl)phenyl)-3-(trifluoromethyl)-1H-pyrazole-5-carboxamide (84f) (236 mg, 0.467 mmol) in MeOH (8 mL) cooled with ice/water was added di-tert-butyl dicarbonate (312 mg, 1.415 mmol) and nickel(II) chloride hexahydrate (60.0 mg, 0.253 mmol). Sodium borohydride (181 mg, 4.69 mmol) was added slowly over 5 min and stirred at RT for 1 h. The reaction mixture was quenched with N1-(2-aminoethyl)ethane-1,2-diamine (0.230 mL, 2.110 mmol), stirred at RT for 0.5 h and concentrated in vacuum to dryness. The residue obtained was dissolved in ethyl acetate (120 mL) and water (60 mL). The aqueous phase was separated and extracted with ethyl acetate (60 mL). The organic layers were combined washed with brine (60 mL), dried over MgSO$_4$, filtered and concentrated in vacuum. The residue obtained was purified by flash column chromatography [silica gel 12 g, eluting with chloroform/methanol (1:0 to 9:1)] to afford tert-butyl 3-(5-(3-((cyclopropylmethylamino)(1H-pyrazol-4-yl)methyl) phenylcarbamoyl)-3-(trifluoromethyl)-1H-pyrazol-1-yl) benzylcarbamate (84g) (154 mg, 54%) as a white solid.

$^1$H NMR (300 MHz, DMSO-d$_6$) δ 12.59 (s, 1H), 10.68 (s, 1H), 7.65-7.56 (m, 2H), 7.56-7.38 (m, 5H), 7.38-7.31 (m, 2H), 7.25 (t, J=7.8 Hz, 1H), 7.16 (d, J=7.6 Hz, 1H), 6.71 (s, 1H), 4.77 (s, 1H), 4.24-4.14 (m, 2H), 2.33-2.19 (m, 2H), 1.37 (s, 9H), 0.95-0.80 (m, 1H), 0.44-0.28 (m, 2H), 0.10-0.00 (m, 2H); $^{19}$F NMR (282 MHz, DMSO-d$_6$) δ −60.81.

Step-6: Preparation of 1-(3-(aminomethyl)phenyl)-N-(3-(((cyclopropylmethyl)amino)(1H-pyrazol-4-yl) methyl)phenyl)-3-(trifluoromethyl)-1H-pyrazole-5-carboxamide (84h)

To a solution of tert-butyl 3-(5-(3-((cyclopropylmethylamino)(1H-pyrazol-4-yl)methyl)phenylcarbamoyl)-3-(trifluoromethyl)-1H-pyrazol-1-yl)benzylcarbamate (84g) (0.134 g, 0.22 mmol) in 1,4-Dioxane (15 mL) was added slowly a solution of 4 M hydrogen chloride in dioxane (2.4 mL, 9.60 mmol) and stirred at RT for 15 h. The reaction mixture was diluted with hexanes and decanted to remove solvent. The residue was treated with hexanes and decanted again. The white residue was concentrated in vacuum to dryness and purified by flash column chromatography [silica gel 8 g, eluting with chloroform/CMA80 (1:0 to 1:1)] to afford 1-(3-(aminomethyl)phenyl)-N-(3-(((cyclopropylmethyl)amino)(1H-pyrazol-4-yl)methyl)phenyl)-3-(trifluoromethyl)-1H-pyrazole-5-carboxamide (84h) (73 mg, 65%)

free base as a white solid; ¹H NMR (300 MHz, DMSO-d₆) δ 12.60 (bs, 1H), 10.68 (s, 1H), 7.62 (t, J=1.8 Hz, 1H), 7.60-7.55 (m, 2H), 7.54-7.33 (m, 6H), 7.26 (t, J=7.8 Hz, 1H), 7.20-7.14 (m, 1H), 4.77 (s, 1H), 4.12 (s, 2H), 3.85 (s, 2H), 2.26 (dd, J=6.7, 3.9 Hz, 2H), 0.96-0.82 (m, 1H), 0.42-0.32 (m, 2H), 0.07-0.01 (m, 2H); 19F NMR (282 MHz, DMSO d₆) δ −60.74; MS (ES−) 507.9 (M−1). To a solution of free base of 1-(3-(aminomethyl)phenyl)-N-(3-(((cyclopropylmethyl)amino)(1H-pyrazol-4-yl)methyl)phenyl)-3-(trifluoromethyl)-1H-pyrazole-5-carboxamide (84h) in methanol (5 mL) was added HCl (0.055 mL, 0.656 mmol) and concentrated in vacuum to dryness. The residue obtained was dissolved in IPA (1 mL) by heating. To the clear solution was added ether (10 mL) and heated at reflux for 15 mins. The white solid obtained was collected by filtration, washed with ether dried in vacuum to furnish 1-(3-(aminomethyl)phenyl)-N-(3-(((cyclopropylmethyl)amino)(1H-pyrazol-4-yl)methyl)phenyl)-3-(trifluoromethyl)-1H-pyrazole-5-carboxamide (84h) (0.062 g, 0.100 mmol, 76% yield) hydrochloride salt as a white solid; ¹H NMR (300 MHz, DMSO-d₆) δ 10.98 (s, 1H), 9.82 (s, 1H), 9.64 (s, 1H), 8.44 (s, 3H), 7.91 (t, J=1.8 Hz, 1H), 7.84-7.70 (m, 4H), 7.66-7.49 (m, 5H), 7.45 (t, J=7.9 Hz, 1H), 5.51 (t, J=6.3 Hz, 1H), 4.13 (q, J=5.8 Hz, 2H), 2.75-2.58 (m, 2H), 1.14-1.00 (m, 1H), 0.59-0.48 (m, 2H), 0.30 (m, 2H); ¹⁹F NMR (282 MHz, DMSO) δ −60.79; MS (ES+) 510.3 (M+1); (ES−) 508.3 (M−1); Analysis calculated for C₂₆H₂₆F₃N₇O.2.25HCl.2.25H₂O: C, 49.40; H, 5.22; Cl, 12.62; N, 15.51; Found: C, 49.09; H, 5.18; Cl, 12.99; N, 15.10.

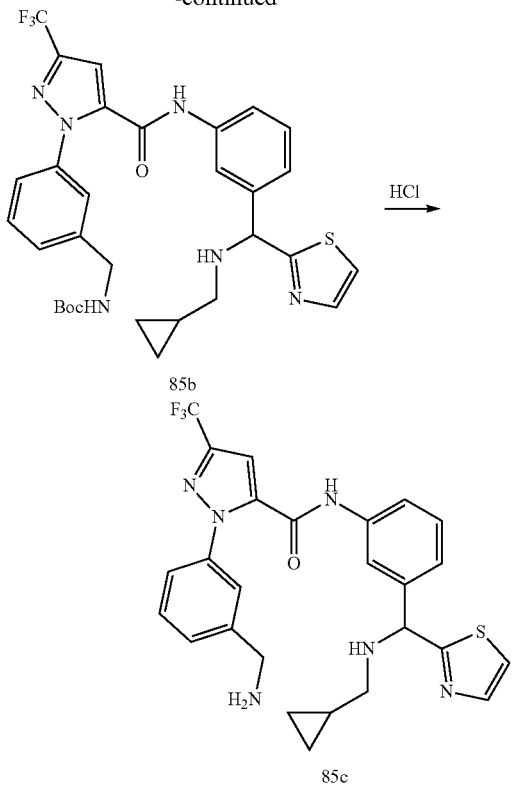

Preparation of 1-(3-(aminomethyl)phenyl)-N-(3-(((cyclopropylmethyl)amino)(thiazol-2-yl)methyl)-phenyl)-3-(trifluoromethyl)-1H-pyrazole-5-carboxamide (85c)

Step-1: Preparation of 1-(3-cyanophenyl)-N-(3-((cyclopropylmethylamino)(thiazol-2-yl)methyl)phenyl)-3-(trifluoromethyl)-1H-pyrazole-5-carboxamide (85a)

To a solution of 1-(3-cyanophenyl)-N-(3-(hydroxy(thiazol-2-yl)methyl)phenyl)-3-(trifluoro-methyl)-1H-pyrazole-5-carboxamide (82d) (500 mg, 1.065 mmol) in dichloromethane (20 mL) at 0° C. was added thionyl chloride (0.240 mL, 3.25 mmol) and allowed to warm to room temperature over 2 h. The reaction mixture was treated with triethyl amine (1.350 mL, 9.69 mmol) stirred at room temperature for 1 h, added cyclopropylmethanamine (1600 mg, 21.82 mmol) and concentrated in vacuum to remove most of dichloromethane. To the reaction mixture was added acetonitrile (15 mL) and triethylamine (0.7 mL). The reaction mixture was refluxed for 15 h and concentrated in vacuum to dryness. The residue was dissolved in chloroform (150 mL), washed with water (75 mL), dried over MgSO₄, filtered and concentrated in vacuum to dryness. The crude product was purified by flash column chromatography [silica gel 2×12 g, eluting with hexanes/ethyl acetate (1:0 to 1:1)] to give 1-(3-cyanophenyl)-N-(3-((cyclopropylmethylamino)(thiazol-2-yl)methyl)phenyl)-3-(trifluoromethyl)-1H-pyrazole-5-carboxamide (85a) (181 mg) as a brown solid. MS (ES+): 523.2 (M+1).

Scheme 85

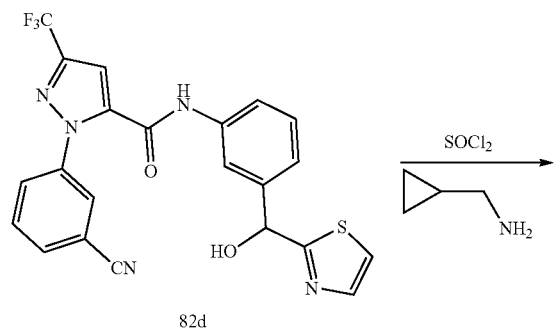

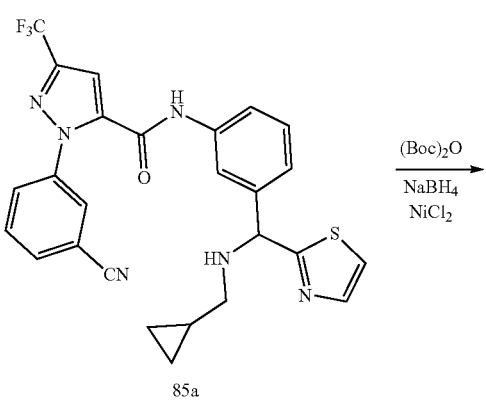

Step-2: Preparation of tert-butyl 3-(5-(3-((cyclopropylmethylamino)(thiazol-2-yl)methyl)phenyl-carbamoyl)-3-(trifluoromethyl)-1H-pyrazol-1-yl)benzylcarbamate (85b)

To a solution of 1-(3-cyanophenyl)-N-(3-((cyclopropylmethylamino)(thiazol-2-yl)methyl)phenyl)-3-(trifluoromethyl)-1H-pyrazole-5-carboxamide (85a) (170 mg, 0.325 mmol) in MeOH (6 mL) cooled with ice/water was added di-tert-butyl dicarbonate (217 mg, 0.986 mmol), nickel(II) chloride hexahydrate (42.0 mg, 0.177 mmol) followed by addition of sodium borohydride (126 mg, 3.26 mmol) slowly over 5 min. The reaction mixture was stirred at room temperature, quenched with N1-(2-aminoethyl)ethane-1,2-diamine (0.160 mL, 1.464 mmol), stirred for 30 mins and concentrated in vacuum to dryness. The residue was treated with ethyl acetate (120 mL), washed with water (60 mL). The aqueous phase was extracted again with ethyl acetate (60 mL). The combined organic extracts were washed with brine (60 mL), dried over MgSO$_4$, filtered and concentrated in vacuum to dryness. The crude product was purified by flash column chromatography [silica gel 2×4 g, eluting with chloroform/CMA80 (1:0 to 4:1)] to give tert-butyl 3-(5-(3-((cyclopropylmethylamino)(thiazol-2-yl)methyl)phenyl-carbamoyl)-3-(trifluoromethyl)-1H-pyrazol-1-yl)benzylcarbamate (85b) (35 mg, 17%) as a colorless gum; $^1$H NMR (300 MHz, DMSO-d$_6$) δ 10.75 (bs, 1H), 7.67 (s, 1H), 7.66 (d, J=3.3 Hz, 1H), 7.63-7.18 (m, 10H), 5.15 (d, J=3.1 Hz, 1H), 4.19 (d, J=6.2 Hz, 2H), 2.45-2.28 (m, 2H), 1.36 (s, 9H), 1.04-0.78 (m, 1H), 0.46-0.32 (m, 2H), 0.11-0.04 (m, 2H); $^{19}$F NMR (282 MHz, DMSO-d$_6$) δ −60.81; MS (ES+): 627.2 (M+1).

Step-3: Preparation of 1-(3-(aminomethyl)phenyl)-N-(3-((cyclopropylmethylamino)(thiazol-2-yl)methyl)phenyl)-3-(trifluoromethyl)-1H-pyrazole-5-carboxamide (85c)

To a solution of tert-butyl 3-(5-(3-((cyclopropylmethylamino)(thiazol-2-yl)methyl)phenylcarbamoyl)-3-(trifluoromethyl)-1H-pyrazol-1-yl)benzylcarbamate (85b) (33 mg, 0.053 mmol) in 1,4-Dioxane (4 mL) was added hydrogen chloride (0.570 mL, 2.280 mmol) (4 M in 1,4-dioxane) and stirred at room temperature for 20.5 h. The reaction mixture was treated with hexanes, decanted, washed with hexanes, and decanted again. The insoluble crude product was purified by flash column chromatography [silica gel with chloroform/CMA80 (1:0 to 3:1)] to give 1-(3-(aminomethyl)phenyl)-N-(3-((cyclopropylmethylamino)(thiazol-2-yl)methyl)phenyl)-3-(trifluoromethyl)-1H-pyrazole-5-carboxamide (85c) (24 mg, 87%) free base as a white solid. $^1$H NMR (300 MHz, DMSO-d$_6$) δ 10.73 (s, 1H), 7.69 (t, J=1.8 Hz, 1H), 7.66 (d, J=3.3 Hz, 1H), 7.61 (d, J=3.3 Hz, 1H), 7.60-7.51 (m, 3H), 7.47-7.41 (m, 2H), 7.35-7.31 (m, 1H), 7.28 (d, J=7.9 Hz, 1H), 7.20 (dt, J=7.8, 1.4 Hz, 1H), 5.15 (s, 1H), 3.79 (s, 2H), 2.88 (s, 2H), 2.38 (t, J=6.9 Hz, 2H), 1.02-0.83 (m, 1H), 0.45-0.32 (m, 2H), 0.14-0.02 (m, 2H); $^{19}$F NMR (282 MHz, DMSO-d$_6$) δ −60.74; MS (ES+) 527.3 (M+1). To a solution of free base of 1-(3-(aminomethyl)phenyl)-N-(3-((cyclopropylmethylamino)(thiazol-2-yl)methyl)phenyl)-3-(trifluoromethyl)-1H-pyrazole-5-carboxamide (85c) (0.3 g, 0.570 mmol) in IPA (10 mL) was added conc. HCl (0.176 mL, 2.117 mmol) and concentrated in vacuum to dryness. The residue was dried in vacuum to remove excess HCl and dissolved in IPA (5 mL) with heating to solubilize. To the homogenous solution was added ether (50 mL) and heated at reflux for 30 mins. After cooling to room temperature the solid obtained was collected by filtration, washed with ether and dried under vacuum to furnish 1-(3-(aminomethyl)phenyl)-N-(3-((cyclopropylmethylamino)(thiazol-2-yl)methyl)phenyl)-3-(trifluoromethyl)-1H-pyrazole-5-carboxamide (85c) (0.27 g, 0.425 mmol, 74.5% yield) hydrochloride as a white solid.

$^1$H NMR (300 MHz, Deuterium Oxide) δ 7.61 (d, J=3.3 Hz, 1H), 7.46 (s, 1H), 7.40 (d, J=3.3 Hz, 1H), 7.38-7.31 (m, 3H), 7.34-7.22 (m, 3H), 7.21-7.12 (m, 2H), 5.76 (s, 1H), 3.97 (s, 2H), 2.80-2.60 (m, 2H), 0.88-0.72 (m, 1H), 0.44-0.32 (m, 2H), 0.11--0.08 (m, 2H); 19F NMR (282 MHz, D$_2$O) 6-62.31; MS (ES+) 527.3 (M+1); (ES−) 525.2 (M−1); Analysis calculated for C$_{26}$H$_{25}$F$_3$N$_6$OS.2.25HCl.2.5H$_2$O: C, 47.77; H, 4.97; Cl, 12.20; N, 12.86; S, 4.91; Found: C, 48.01; H, 5.26; Cl, 11.94; N, 12.34; S, 4.85.

Scheme 86

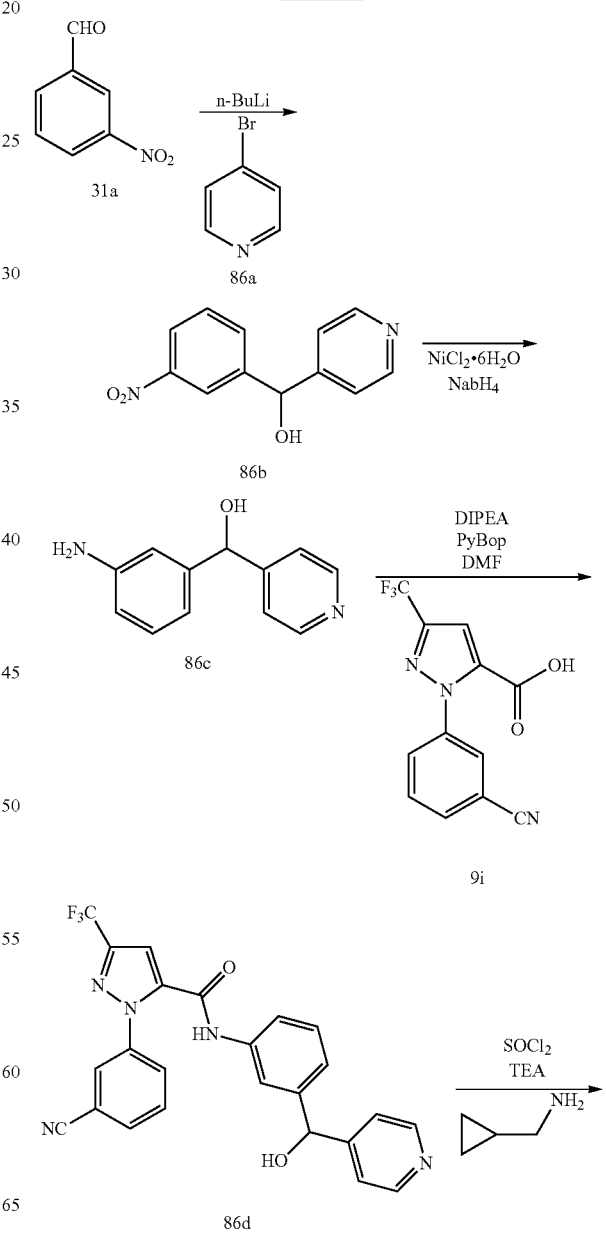

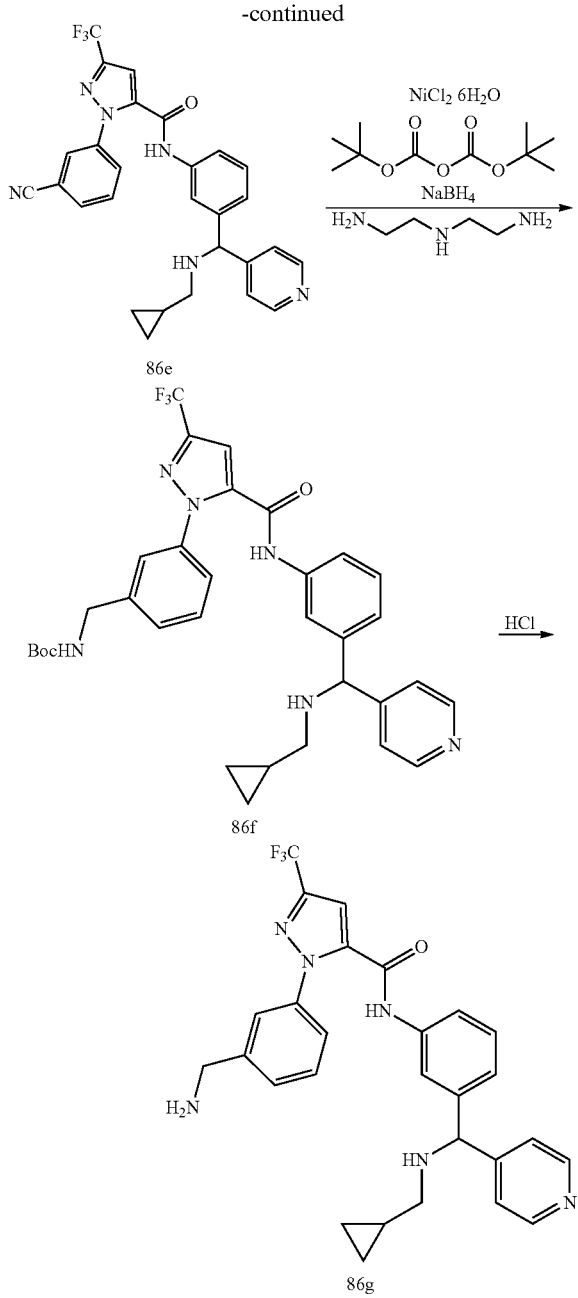

Preparation of 1-(3-(aminomethyl)phenyl)-N-(3-((cyclopropylmethylamino)(pyridin-4-yl)methyl)phenyl)-3-(trifluoromethyl)-1H-pyrazole-5-carboxamide (86g)

Step-1: Preparation of (3-nitrophenyl)(pyridin-4-yl)methanol (86b)

A solution of 4-bromopyridine hydrochloride (4.8 g) in water (50 mL) was neutralized with aq. 6 N NaOH followed by extraction with ethyl acetate (100 mL, 50 mL). The combined extracts were washed with brine (60 mL), dried over MgSO₄ followed by filtration and concentration to give 4-bromopyridine (light brown oil, 1.65 g, low yield due to low boiling point, some loss from concentration). To a solution of 4-bromopyridine (1.58 g, 10.00 mmol) in Ether (8 mL) cooled to −78° C. was added dropwise n-butyl-lithium (6.30 mL, 10.08 mmol) and stirred for 30 mins at −78° C. To the reaction mixture at −78° C. was added a solution of 3-nitrobenzaldehyde (31a) (1.511 g, 10.00 mmol) in THF (12 mL), stirred at −78° C. for 2 h and then at room temperature for 2 h. The reaction mixture was quenched with saturated ammonium chloride (40 mL). The organic layer was separated and the aqueous phase was extracted with ethyl acetate (60 mL). The combined organic extracts were washed with brine (50 mL), dried over MgSO₄, filtered and concentrated in vacuum. The crude product was purified by flash column chromatography [silica gel 40 g, eluting with chloroform/methanol (1:0 to 19:1)] to afford (3-nitrophenyl)(pyridin-4-yl)methanol (86b) (1.005 g, 44%) as a yellow solid. $^1$H NMR (300 MHz, DMSO-$d_6$) δ 8.54-8.50 (m, 2H), 8.29 (t, J=2.0 Hz, 1H), 8.12 (ddd, J=8.2, 2.4, 1.1 Hz, 1H), 7.86 (dt, J=7.8, 1.4 Hz, 1H), 7.64 (t, J=7.9 Hz, 1H), 7.44 (ddd, J=4.6, 1.6, 0.7 Hz, 2H), 6.49 (d, J=4.2 Hz, 1H), 5.93 (d, J=4.1 Hz, 1H); MS (ES+): 231.1 (M+1).

Step-2: Preparation of (3-aminophenyl)(pyridin-4-yl)methanol (86c)

To a solution of (3-nitrophenyl)(pyridin-4-yl)methanol (86b) (953 mg, 4.14 mmol) in methanol (25 mL) was cooled to 0° C. was added nickel(II) chloride hexahydrate (246 mg, 1.035 mmol) followed by sodium borohydride (639 mg, 16.56 mmol) portionwise over a 30 mins period. The reaction was stirred at room temperature for 30 min, quenched with N1-(2-aminoethyl)ethane-1,2-diamine (0.900 mL, 8.33 mmol), stirred for 30 mins at room temperature and concentrated in vacuum to dryness. The residue was treated with ethyl acetate (120 mL), washed with water (60 mL). The aqueous phase was extracted again with ethyl acetate (75 mL). The combined organic extracts were washed with brine (75 mL), dried over MgSO₄, filtered and concentrated in vacuum. The crude product was purified by flash column chromatography [silica gel 25 g, eluting with chloroform/methanol (1:0 to 9:1)] to give (3-aminophenyl)(pyridin-4-yl)methanol (86c) (655 mg, 79%) as a white solid. $^1$H NMR (300 MHz, DMSO-$d_6$) δ 8.50-8.44 (m, 2H), 7.33 (ddd, J=4.4, 1.6, 0.7 Hz, 2H), 6.93 (t, J=7.7 Hz, 1H), 6.60-6.48 (m, 2H), 6.40 (ddd, J=8.0, 2.3, 1.1 Hz, 1H), 5.95 (d, J=3.9 Hz, 1H), 5.51 (d, J=3.9 Hz, 1H), 5.04 (s, 2H).; MS (ES+): 201.1 (M+1).

Step-3: Preparation of 1-(3-cyanophenyl)-N-(3-(hydroxy(pyridin-4-yl)methyl)phenyl)-3-(trifluoromethyl)-1H-pyrazole-5-carboxamide (86d)

To a solution of 1-(3-cyanophenyl)-3-(trifluoromethyl)-1H-pyrazole-5-carboxylic acid (9i) (892 mg, 3.17 mmol) in DMF (26 mL) was added (3-aminophenyl)(pyridin-4-yl)methanol (86c) (634 mg, 3.17 mmol), N-ethyl-N-isopropylpropan-2-amine (4.50 mL, 25.8 mmol) and bromotripyrrolidin-1-ylphosphonium hexafluorophosphate(V) (PyBrOP, 1509 mg, 3.17 mmol) and stirred at room temperature for 20 h. The reaction mixture was diluted with ethyl acetate (200 mL), washed with water (2×100 mL), brine (75 mL), dried over MgSO₄, filtered and concentrated in vacuum. The crude product was purified by flash column chromatography [silica gel 40 g, eluting with chloroform/methanol (1:0 to 9:1)] to give 1-(3-cyanophenyl)-N-(3-(hydroxy(pyridin-4-yl)methyl)phenyl)-3-(trifluoromethyl)-1H-pyrazole-5-carboxamide (86d) (1.09 g, 74%) as a light yellow solid; $^1$H NMR (300 MHz, DMSO-$d_6$) δ 10.66 (s, 1H), 8.52-8.46 (m, 2H), 8.16 (t, J=1.8 Hz, 1H), 8.00 (dt, J=7.8, 1.3 Hz, 1H), 7.90 (ddd, J=8.2, 2.2, 1.1 Hz, 1H), 7.79-7.54 (m, 4H), 7.35 (ddd, J=4.5, 1.6, 0.6 Hz, 2H), 7.30 (t, J=7.8 Hz, 1H), 7.17 (dt, J=7.8, 1.3 Hz, 1H), 6.21 (d, J=3.9 Hz, 1H), 5.70 (d, J=3.9 Hz, 1H); $^{19}$F NMR (282 MHz, DMSO-d$_6$) δ −60.98; MS (ES+): 464.1 (M+1).

Step-4: Preparation of 1-(3-cyanophenyl)-N-(3-((cyclopropylmethylamino)(pyridin-4-yl)methyl)phenyl)-3-(trifluoromethyl)-1H-pyrazole-5-carboxamide (86e)

To a solution of 1-(3-cyanophenyl)-N-(3-(hydroxy(pyridin-4-yl)methyl)phenyl)-3-(trifluoromethyl)-1H-pyrazole-5-carboxamide (86d) (0.4 g, 0.863 mmol) in dichloromethane (18 mL) at 0° C. was added thionyl chloride (0.2 mL, 2.70 mmol) and allowed to warm to room temperature over 2 h. The reaction mixture was treated with triethyl amine (1.1 mL, 7.89 mmol) stirred at room temperature for 1 h, added cyclopropylmethanamine (1.3 g, 17.73 mmol) and concentrated in vacuum to remove most of dichloromethane. To the reaction mixture was added acetonitrile (14 mL) and triethylamine (0.5 mL). The reaction mixture was refluxed for 17.5 h and concentrated in vacuum to dryness. The residue was dissolved in chloroform (120 mL), washed with water (60 mL), dried over MgSO$_4$, filtered and concentrated in vacuum to dryness.

The crude product was purified by flash column chromatography [silica gel 2×12 g, eluting with chloroform/methanol (1:0 to 19:1) to give 1-(3-cyanophenyl)-N-(3-((cyclopropylmethylamino)(pyridin-4-yl)methyl)phenyl)-3-(trifluoromethyl)-1H-pyrazole-5-carboxamide (86e) (26 mg, 5.8%) as a brown solid; $^1$H NMR (300 MHz, DMSO-d$_6$) δ 10.66 (s, 1H), 8.49-8.44 (m, 2H), 8.18-8.15 (m, 1H), 8.01 (dt, J=7.8, 1.3 Hz, 1H), 7.90 (ddd, J=8.2, 2.2, 1.1 Hz, 1H), 7.79-7.62 (m, 3H), 7.56 (dt, J=8.1, 1.6 Hz, 1H), 7.45-7.38 (m, 2H), 7.28 (t, J=7.8 Hz, 1H), 7.21 (dt, J=7.8, 1.4 Hz, 1H), 4.84 (s, 1H), 2.35-2.22 (m, 2H), 0.1.00-0.80 m, 1H), 0.43-0.33 (m, 2H), 0.10-0.01 (m, 2H); $^{19}$F NMR (282 MHz, DMSO-d$_6$) δ −60.98; MS (ES+): 517.3 (M+1).

Step-5: Preparation of tert-butyl 3-(5-(3-((cyclopropylmethylamino)(pyridin-4-yl)methyl)phenylcarbamoyl)-3-(trifluoromethyl)-1H-pyrazol-1-yl)benzylcarbamate (86f)

To a solution of 1-(3-cyanophenyl)-N-(3-((cyclopropylmethylamino)(pyridin-4-yl)methyl)phenyl)-3-(trifluoromethyl)-1H-pyrazole-5-carboxamide (86e) (24 mg, 0.046 mmol) in MeOH (3 mL) cooled with ice/water was added di-tert-butyl dicarbonate (31.0 mg, 0.141 mmol), nickel(II) chloride hexahydrate (6.0 mg, 0.025 mmol) followed by addition of sodium borohydride (18 mg, 0.466 mmol) slowly over 5 min. The reaction mixture was stirred at room temperature, quenched with N1-(2-aminoethyl)ethane-1,2-diamine (0.022 mL, 0.203 mmol), stirred for 30 mins and concentrated in vacuum to dryness. The residue was treated with ethyl acetate (120 mL), washed with water (60 mL). The aqueous phase was extracted again with ethyl acetate (60 mL). The combined organic extracts were washed with brine (60 mL), dried over MgSO$_4$, filtered and concentrated in vacuum to dryness. The crude product was purified by flash column chromatography [silica gel 4 g, eluting with chloroform/CMA80 (1:0 to 4:1)] to afford tert-butyl 3-(5-(3-((cyclopropylmethylamino)(pyridin-4-yl)methyl)phenylcarbamoyl)-3-(trifluoromethyl)-1H-pyrazol-1-yl)benzylcarbamate (86f) (12 mg, 42%) as a colorless gum. $^1$H NMR (300 MHz, Methanol-d$_4$) δ 8.47-8.40 (m, 2H), 7.65 (t, J=1.9 Hz, 1H), 7.52-7.19 (m, 10H), 4.92 (s, 1H), 4.28 (s, 2H), 2.38 (dd, J=6.9, 3.0 Hz, 2H), 1.39 (s, 9H), 1.05-0.90 (m, 1H), 0.51-0.42 (m, 2H), 0.08 (td, J=5.3, 4.8, 3.6 Hz, 2H); $^{19}$F NMR (282 MHz, Methanol-d$_4$) δ −63.71; MS (ES+): 621.2 (M+H).

Step-6: Preparation of 1-(3-(aminomethyl)phenyl)-N-(3-((cyclopropylmethylamino)(pyridin-4-yl)methyl)phenyl)-3-(trifluoromethyl)-1H-pyrazole-5-carboxamide (86g)

To a solution of tert-butyl 3-(5-(3-((cyclopropylmethylamino)(pyridin-4-yl)methyl)phenylcarbamoyl)-3-(trifluoromethyl)-1H-pyrazol-1-yl)benzylcarbamate (86f) (12 mg, 0.019 mmol) in 1,4-Dioxane (3 mL) was added hydrogen chloride (0.210 mL, 0.841 mmol, 4 M in 1,4-dioxane) and stirred at room temperature for 14 h. the reaction mixture was treated with hexanes, decanted, washed with hexanes, and decanted again. The insoluble crude product was purified by flash column chromatography [silica gel 2×4 g, eluting with chloroform/CMA80 (1:0 to 2:1) to afford 1-(3-(aminomethyl)phenyl)-N-(3-((cyclopropylmethylamino)(pyridin-4-yl)methyl)phenyl)-3-(trifluoromethyl)-1H-pyrazole-5-carboxamide (86g) (4.1 mg, 41%) as a colorless gum; $^1$H NMR (300 MHz, Methanol-d$_4$) δ 8.46-8.41 (m, 2H), 7.64 (t, J=1.9 Hz, 1H), 7.56 (s, 1H), 7.52-7.47 (m, 4H), 7.46-7.40 (m, 2H), 7.35 (s, 1H), 7.30 (t, J=7.8 Hz, 1H), 7.22 (dt, J=7.7, 1.5 Hz, 1H), 4.92 (s, 1H), 3.93 (s, 2H), 2.38 (dd, J=6.9, 3.1 Hz, 2H), 1.04-0.91 (m, 1H), 0.55-0.42 (m, 2H), 0.12-0.04 (m, 2H); $^{19}$F NMR (282 MHz, Methanol-d$_4$) δ −63.75; MS (ES+): 521.3 (M+1).

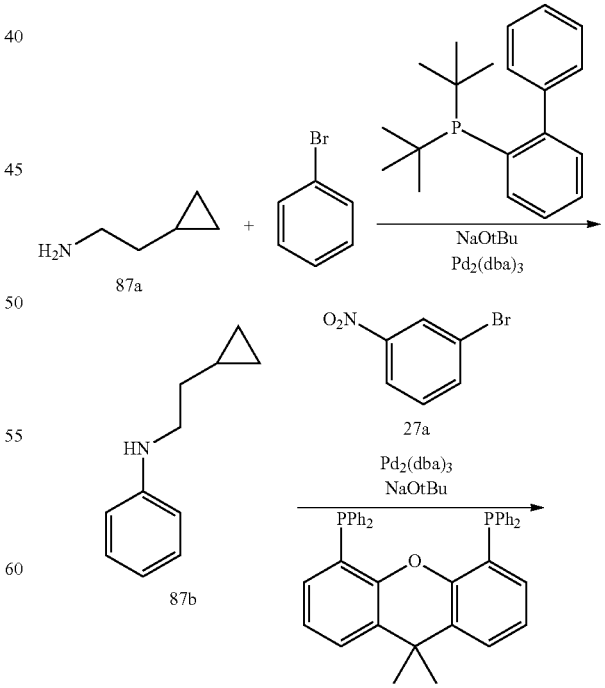

Scheme 87

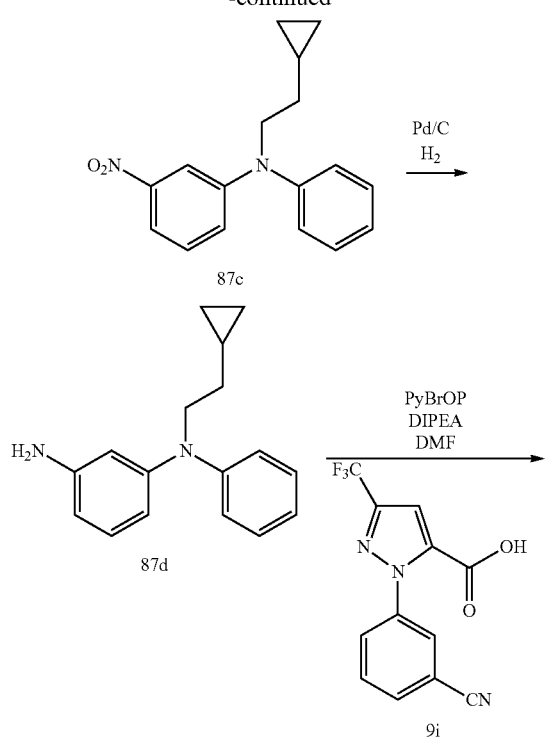

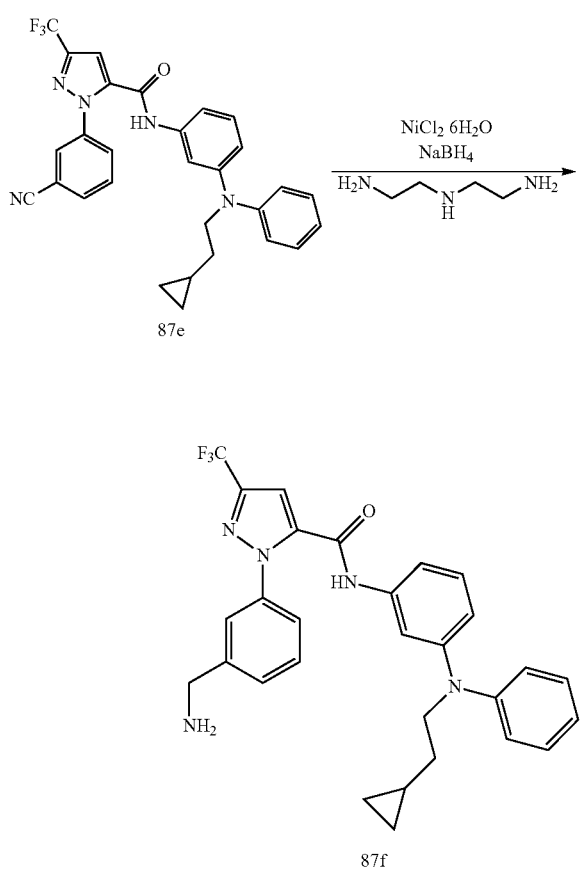

Preparation of 1-(3-(aminomethyl)phenyl)-N-(3-((2-cyclopropylethyl)(phenyl)amino)phenyl)-3-(trifluoromethyl)-1H-pyrazole-5-carboxamide (87f)

Step-1: Preparation of N-(2-cyclopropylethyl)aniline (87b)

To a 50 mL single-neck flask with a magnetic stir bar was charged sodium 2-methylpropan-2-olate (0.673 g, 7.01 mmol), biphenyl-2-yldi-tert-butylphosphine (0.209 g, 0.701 mmol) and tris(dibenzylideneacetone)dipalladium(0) (0.321 g, 0.350 mmol) at this stage flask was degassed and refilled with nitrogen, to this solid mixture 2-cyclopropylethanamine (87a) (0.662 mL, 7.01 mmol), bromobenzene (0.738 mL, 7.01 mmol), and toluene (10 mL) were successively added in a positive flow of nitrogen. The reaction mixture was stirred at room temperature for 16 h under a positive flow of nitrogen. TLC analysis (ethyl acetate/hexanes, 5/95, v/v) shows reaction was complete. Reaction mixture was filtered through a small Celite pad, Celite pad was subsequently washed with ethyl acetate (2×50 mL). The combined organics were dried over anhydrous $MgSO_4$, filtered, evaporated to dryness. The residue was purified by flash column chromatography [(silica gel 40 g, eluting with ethyl acetate in hexanes from 0 to 20%)] to afford N-(2-cyclopropylethyl)aniline (87b) (198 mg, 18% yield) as an yellow oil; $^1H$ NMR (300 MHz, DMSO-$d_6$) δ 6.97 (dd, J=8.5, 7.2 Hz, 2H), 6.59-6.31 (m, 3H), 5.44 (t, J=5.6 Hz, 1H, $D_2O$ exchangeable), 2.97 (td, J=7.2, 5.6 Hz, 2H), 1.36 (q, J=7.0 Hz, 2H), 0.83-0.61 (m, 1H), 0.44-0.24 (m, 2H), 0.06-−0.05 (m, 2H).

Step-2: Preparation of N-(2-cyclopropylethyl)-3-nitro-N-phenylaniline (87c)

To a 50 mL single-neck flask with a magnetic stir bar was charged 1-bromo-3-nitrobenzene (27a) (0.245 g, 1.213 mmol) and N-(2-cyclopropylethyl)aniline (87b) (0.163 g, 1.011 mmol) was dissolved in toluene (15 mL) and sodium 2-methylpropan-2-olate (0.078 g, 0.809 mmol), (9,9-dimethyl-9H-xanthene-4,5-diyl)bis(diphenylphosphine) (0.058 g, 0.101 mmol) and tris(dibenzylideneacetone)dipalladium (0) (0.028 g, 0.030 mmol) were added. The reaction mixture was stirred at 110° C. for 16 h under a positive flow of nitrogen, cooled to room temperature, and excess solvent was evaporated to dryness. Reaction was quenched with water (25 mL), extracted with ethyl acetate (2×50 mL). The combined organics were dried over $MgSO_4$, filtered, evaporated to dryness. The residue was purified by flash column chromatography [(silica gel 25 g, eluting with ethyl acetate in hexanes from 0 to 100%)] to as eluent to afford N-(2-cyclopropylethyl)-3-nitro-N-phenylaniline (87c) (280 mg, 98% yield) as a brown-yellow oil which was used as such in next step.

Step-3: Preparation of N1-(2-cyclopropylethyl)-$N_1$-phenylbenzene-1,3-diamine (87d)

To a solution of N-(2-cyclopropylethyl)-3-nitro-N-phenylaniline (87c) (0.261 g, 0.924 mmol) in methanol (20 mL) was treated with palladium (10% Pd on carbon) (0.039 g, 0.370 mmol). The reaction mixture was hydrogenated at 60 psi for 3 h at room temperature. TLC analysis (ethyl acetate/hexanes, 1:1, v/v) shows reaction was complete. The reaction was filtered through a small Celite pad, Celite pad was subsequently washed with methanol (2×25 mL), and ethyl acetate (25 mL). Excess solvents were pumped-off under reduced pressure. The residue was purified by flash column chromatography [(silica gel 25 g, eluting with ethyl acetate in hexanes from 0 to 100%)] to afford N1-(2-cyclopropylethyl)-N₁-phenylbenzene-1,3-diamine (87d) (0.066 g, 0.262 mmol, 28.3% yield) as a brown waxy solid which was used as such for next step; MS (ES+) 253.2 (M+1).

Step-4: Preparation of 1-(3-cyanophenyl)-N-(3-((2-cyclopropylethyl)(phenyl)amino)phenyl)-3-(trifluoromethyl)-1H-pyrazole-5-carboxamide (87e)

An oven-dried 100 mL round bottomed flask containing 1-(3-cyanophenyl)-3-(trifluoromethyl)-1H-pyrazole-5-carboxylic acid (9i) (105 mg, 0.374 mmol), N1-(2-cyclopropylethyl)-N1-phenylbenzene-1,3-diamine (87d) (63 mg, 0.250 mmol), bromo-tris-pyrrolidino phosphonium-hexafluorophosphate(PyBrOP, 0.140 g, 0.300 mmol) was added N,N-dimethylformamide (1.508 mL, 19.47 mmol) and N-ethyl-N-isopropylpropan-2-amine (0.217 mL, 1.248 mmol) successively in a positive flow of nitrogen at room temperature. The resulting reaction mixture was stirred at room temperature for 16 h under nitrogen atmosphere. Excess DMF was pumped-off under reduced pressure. The residue was purified by flash column chromatography [silica gel 25 g, eluting with ethyl acetate in hexanes from 0-100%] to furnish 1-(3-cyanophenyl)-N-(3-((2-cyclopropylethyl)(phenyl)amino)phenyl)-3-(trifluoromethyl)-1H-pyrazole-5-carboxamide (87e) (93 mg, 72% yield) as a pale yellow solid; ¹H NMR (300 MHz, DMSO-d₆) δ 10.55 (s, 1H), 8.15 (t, J=1.8 Hz, 1H), 8.00 (dt, J=7.7, 1.4 Hz, 1H), 7.94-7.86 (m, 1H), 7.73 (t, J=8.0 Hz, 1H), 7.67 (s, 1H), 7.34-7.15 (m, 5H), 7.07-7.01 (m, 2H), 6.96 (t, J=7.3 Hz, 1H), 6.76-6.66 (m, 1H), 3.75 (t, J=7.5 Hz, 2H), 1.45 (q, J=7.3 Hz, 2H), 0.68 (dd, J=12.8, 6.9 Hz, 1H), 0.44-0.33 (m, 2H), 0.07-0.01 (m, 2H); ¹⁹F NMR (282 MHz, DMSO-d₆) δ −60.95; MS (ES⁺): MS (ES+) 516.22 (M+1), 538.15 (M+Na), MS (ES−) 514.2 (M−1).

Step-5: Preparation of 1-(3-(aminomethyl)phenyl)-N-(3-((2-cyclopropylethyl)(phenyl)amino)phenyl)-3-(trifluoromethyl)-1H-pyrazole-5-carboxamide (87f)

To a stirred solution of 1-(3-cyanophenyl)-N-(3-((2-cyclopropylethyl)(phenyl)amino)phenyl)-3-(trifluoromethyl)-1H-pyrazole-5-carboxamide (87e) (81 mg, 0.157 mmol) in anhydrous methanol (10 mL) cooled to 0° C. was added nickel(II) chloride hexahydrate (0.056 g, 0.236 mmol) followed by sodium borohydride (0.071 g, 1.885 mmol) in small portions over a period of 5 min. The reaction was exothermic and effervescent. The reaction mixture was stirred for 5 min, TLC analysis (ethyl acetate/hexanes, 3/7, v/v) shows reaction was complete at this point N1-(2-aminoethyl)ethane-1,2-diamine (0.170 mL, 1.571 mmol) was added. Excess methanol was pumped-off under reduced pressure. The reaction mixture was treated with saturated. aqueous NH₄Cl (50 mL), and product was extracted with chloroform (2×50 mL). The combined organic layers were combined dried over MgSO₄, filtered, evaporated to dryness. The residue was purified by flash column chromatography [(silica gel 25 g, eluting with methanol in chloroform from 0 to 50%)] to furnish 1-(3-(aminomethyl)phenyl)-N-(3-((2-cyclopropylethyl)(phenyl)amino)phenyl)-3-(trifluoromethyl)-1H-pyrazole-5-carboxamide (87f) (32 mg, 39% yield) as a white solid; ¹H NMR (300 MHz, DMSO-d₆) δ 10.59 (s, 1H), 7.56-7.49 (m, 2H), 7.46-7.40 (m, 2H), 7.34-7.16 (m, 6H), 7.07-6.92 (m, 3H), 6.70 (dt, J=7.4, 2.0 Hz, 1H), 3.76 (d, J=7.9 Hz, 4H), 1.45 (q, J=7.1 Hz, 2H), 0.70 (ddt, J=9.6, 7.5, 4.6 Hz, 1H), 0.47-0.31 (m, 2H), 0.04 (dd, J=4.9, 1.5 Hz, 2H); ¹H NMR (300 MHz, DMSO-d₆ D₂O) δ 7.50 (d, J=2.3 Hz, 2H), 7.48-7.41 (m, 2H), 7.37-7.22 (m, 4H), 7.19 (dd, J=4.8, 2.3 Hz, 2H), 7.10-6.93 (m, 3H), 6.70 (dt, J=6.7, 2.5 Hz, 1H), 3.75 (d, J=3.3 Hz, 4H), 1.45 (q, J=7.2 Hz, 2H), 0.69 (tt, J=7.4, 4.8 Hz, 1H), 0.45-0.35 (m, 2H), 0.08-0.01 (m, 2H); ¹⁹F NMR (282 MHz, DMSO-d₆) δ −60.71; MS (ES⁺): MS (ES+) 520.3 (M+1), MS (ES−) 518.3 (M−1); Analysis calculated for: C₂₉H₂₈F₃N₅O.0.5H₂O: C, 65.90; H, 5.53; N, 13.25; Found: C, 66.12; H, 5.56; N, 12.85.

Scheme 88

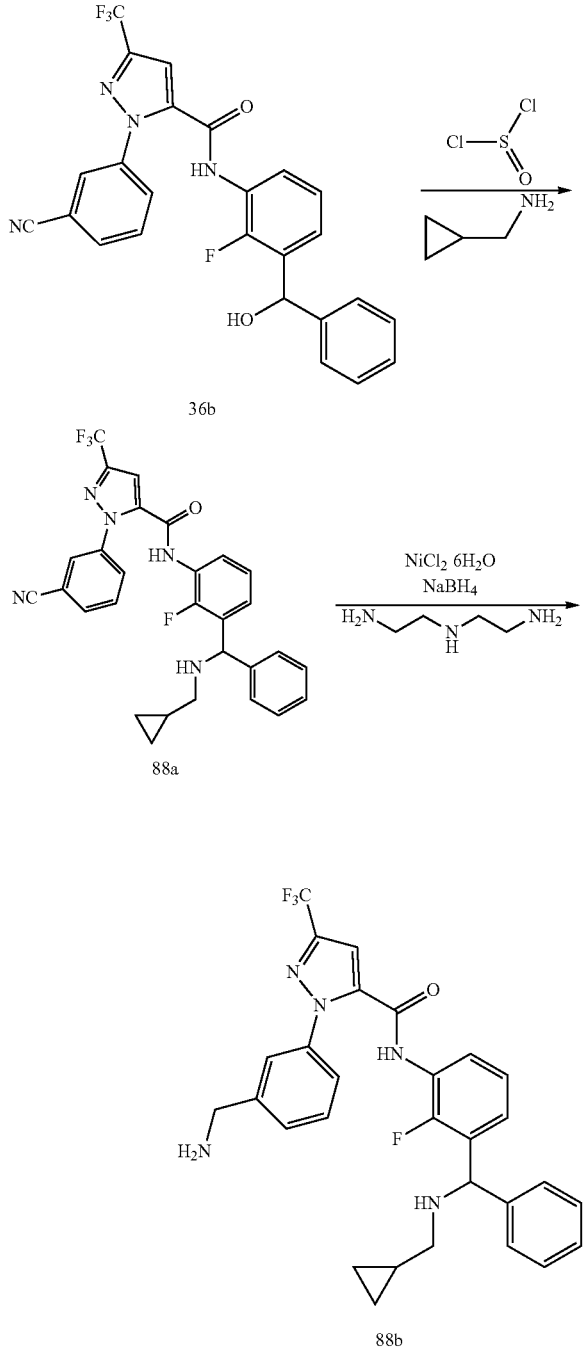

Preparation of 1-(3-(aminomethyl)phenyl)-N-(3-((cyclopropylmethylamino)(phenyl)methyl)-2-fluorophenyl)-3-(trifluoromethyl)-1H-pyrazole-5-carboxamide (88b)

Step-1: Preparation of 1-(3-cyanophenyl)-N-(3-((cyclopropylmethylamino)(phenyl)methyl)-2-fluorophenyl)-3-(trifluoromethyl)-1H-pyrazole-5-carboxamide (88a)

To a solution of 1-(3-cyanophenyl)-N-(2-fluoro-3-(hydroxy(phenyl)methyl)phenyl)-3-(trifluoromethyl)-1H-pyrazole-5-carboxamide (36b) (0.15 g, 0.312 mmol) in dichloromethane (10 mL) at 0° C. was added thionyl chloride (0.046 mL, 0.624 mmol), and allowed to warm to room temperature and stirred for 3 h. The reaction mixture was concentrated in vacuum to dryness. The residue was dissolved in acetonitrile (10 mL) and added cyclopropylmethanamine (0.542 mL, 6.24 mmol). The reaction mixture was heated at reflux overnight. The reaction mixture was cooled to room temperature concentrated in vacuum to dryness. The residue was purified by flash column chromatography (silica gel 25 g, eluting with ethyl acetate in hexanes from 0-100%) to afford 1-(3-(aminomethyl)phenyl)-N-(3-((cyclopropylmethylamino)(phenyl)methyl)-2-fluorophenyl)-3-(trifluoromethyl)-1H-pyrazole-5-carboxamide (88b) (96 mg, 58% yield) as an off-white solid; $^1$H NMR (300 MHz, DMSO-$d_6$) δ 10.47 (s, 1H, $D_2O$ exchangeable), 8.12 (s, 1H), 7.99 (dt, J=7.7, 1.3 Hz, 1H), 7.93-7.86 (m, 1H), 7.77-7.67 (m, 2H), 7.55 (t, J=7.1 Hz, 1H), 7.48-7.34 (m, 3H), 7.29 (dd, J=8.4, 6.6 Hz, 2H), 7.24-7.14 (m, 2H), 5.14 (s, 1H), 2.30 (t, J=6.3 Hz, 2H), 0.91 (s, 1H), 0.47-0.31 (m, 2H), 0.05 (dd, J=5.7, 4.1 Hz, 2H); $^{19}$F NMR (282 MHz, DMSO-$d_6$) δ −60.99, −127.84; MS (ES+): MS (ES+) 534.2 (M+1), MS (ES−) 532.14 (M−1).

Step-2: Preparation of 1-(3-(aminomethyl)phenyl)-N-(3-((cyclopropylmethylamino)(phenyl)methyl)-2-fluorophenyl)-3-(trifluoromethyl)-1H-pyrazole-5-carboxamide (88b)

To a stirred solution of 1-(3-cyanophenyl)-N-(3-((cyclopropylmethylamino)(phenyl)methyl)-2-fluorophenyl)-3-(trifluoromethyl)-1H-pyrazole-5-carboxamide (88a) (0.121 g, 0.227 mmol) in anhydrous methanol (10 mL) cooled to 0° C. was added nickel(II) chloride hexahydrate (0.081 g, 0.340 mmol) followed by sodium borohydride (0.103 g, 2.72 mmol) in small portions over a period of 5 min. The reaction mixture was stirred for 5 min, TLC analysis (ethyl acetate/hexanes, 3/7, v/v) shows reaction was complete at this point N1-(2-aminoethyl)ethane-1,2-diamine (0.245 mL, 2.268 mmol) was added. Excess methanol was pumped-off under reduced pressure. The reaction mixture was treated with saturated aqueous $NH_4Cl$ (30 mL), and product was extracted with chloroform (2×30 mL). The organic layers were combined dried over $MgSO_4$, filtered, evaporated to dryness. The residue was purified by flash column chromatography [(silica gel 25 g, eluting with methanol/chloroform from 0 to 50%)] to furnish 1-(3-(aminomethyl)phenyl)-N-(3-((cyclopropylmethylamino)(phenyl)methyl)-2-fluorophenyl)-3-(trifluoromethyl)-1H-pyrazole-5-carboxamide (88b) (35 mg, 29% yield) as a white solid; $^1$H NMR (300 MHz, DMSO-$d_6$) δ 10.48 (s, 1H, $D_2O$ exchangeable), 7.60-7.40 (m, 6H), 7.40-7.26 (m, 5H), 7.19 (tdd, J=7.9, 4.7, 3.2 Hz, 2H), 5.14 (s, 1H), 3.78 (s, 2H), 2.30 (d, J=6.7 Hz, 2H), 1.03-0.78 (m, 1H), 0.45-0.33 (m, 2H), 0.04 (td, J=5.4, 3.8 Hz, 2H); $^{19}$F NMR (282 MHz, DMSO-$d_6$) δ −60.75, −128.07; MS (ES$^+$): MS (ES+) 538.3 (M+1), 560.2 (M+Na), MS (ES−) 536.2 (M−1), 572.2 (M+Cl); Analysis calculated for: $C_{29}H_{27}F_4N_5O \cdot 0.25H_2O$: C, 64.26; H, 5.11; N, 12.92; Found: C, 64.26; H, 5.22; N, 12.58.

Scheme 89

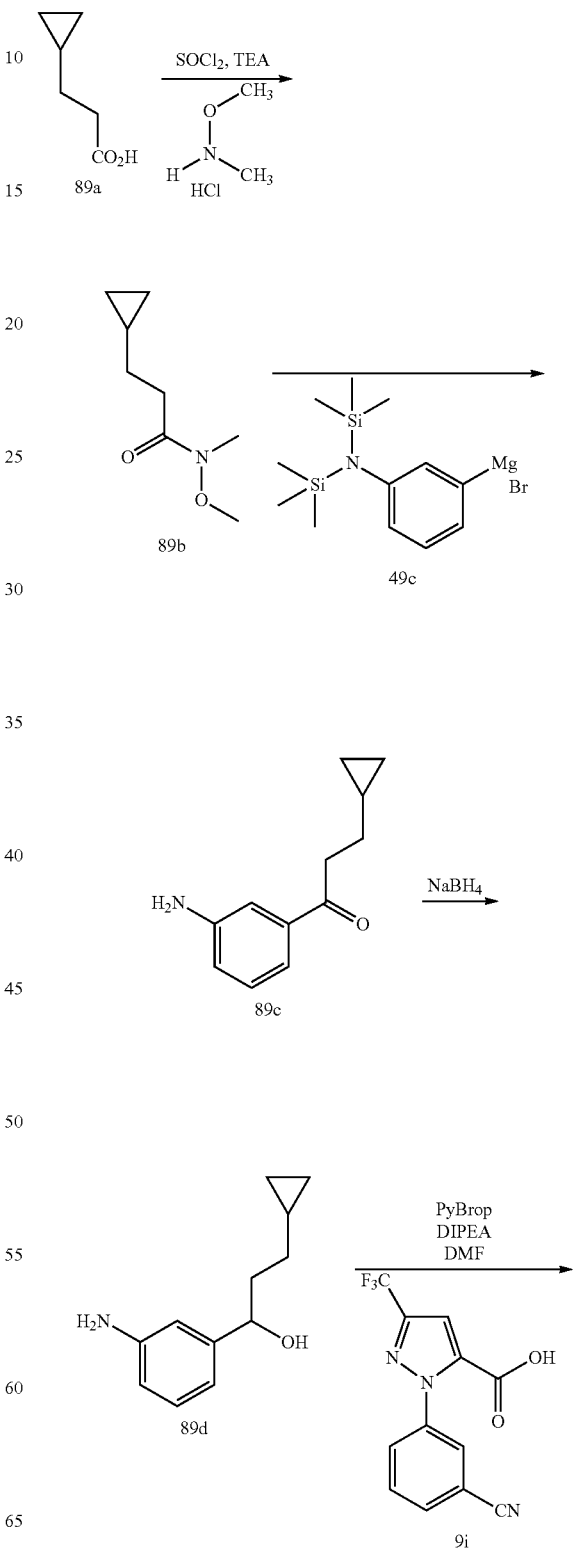

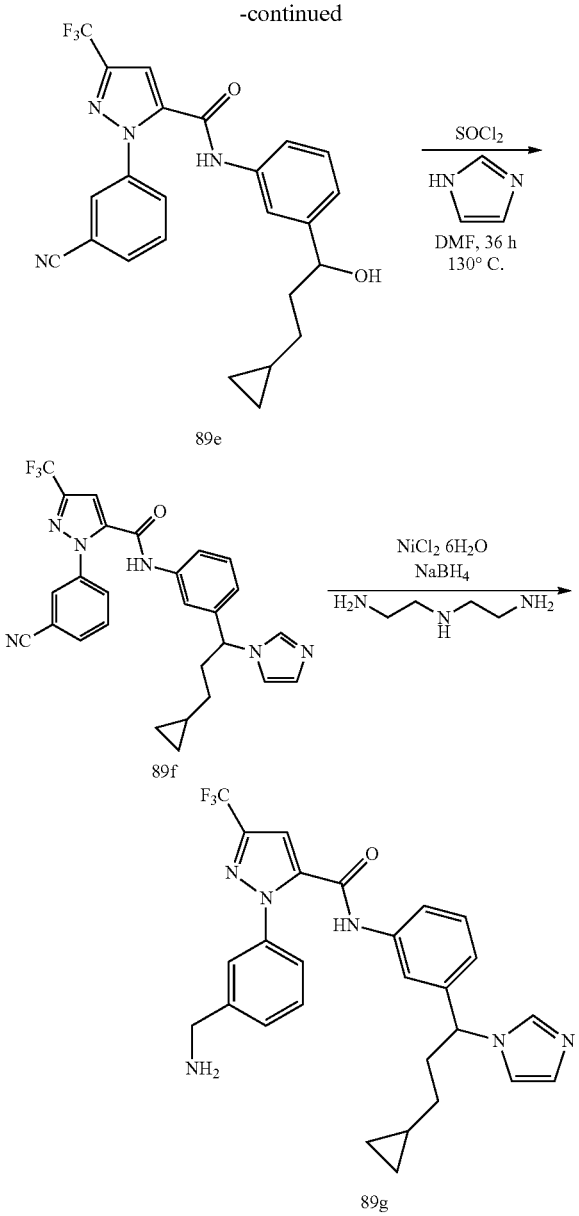

Preparation of 1-(3-(aminomethyl)phenyl)-N-(3-(3-cyclopropyl-1-(1H-imidazol-1-yl)propyl)phenyl)-3-(trifluoromethyl)-1H-pyrazole-5-carboxamide (89g)

Step-1: Preparation of 3-cyclopropyl-N-methoxy-N-methylpropanamide (89b)

To a solution of 3-cyclopropylpropanoic acid (89a) (1 g, 8.76 mmol) in dichloromethane (10 mL) was added thionyl chloride (1.279 mL, 17.52 mmol) at 0° C., one drop of DMF and stirred at room temperature for 3 h. To the reaction mixture was added N,O-dimethylhydroxylamine hydrochloride (1.282 g, 13.14 mmol), triethylamine (12.21 mL, 88 mmol) at room temperature and stirred for 16 h. The reaction mixture was quenched with water (75 mL), and extracted with dichloromethane (75 mL, 50 mL). The combined organics layers were dried MgSO$_4$, filtered, and evaporated to dryness. The residue was purified by flash column chromatography [(silica gel 40 g, eluting with ethyl acetate in hexanes from 0-100%)] to furnish 3-cyclopropyl-N-methoxy-N-methylpropanamide (89b) (0.795 g, 5.06 mmol, 57.7% yield) as a light yellow oil; $^1$H NMR (300 MHz, DMSO-d$_6$) δ 3.63 (s, 3H), 3.05 (s, 3H), 2.42 (t, J=7.5 Hz, 2H), 0.76-0.61 (m, 1H), 0.38-0.30 (m, 2H), 0.04--0.05 (m, 2H).

Step-2: Preparation of 1-(3-Aminophenyl)-3-cyclopropylpropan-1-one (89c)

To a stirred solution of 3-cyclopropyl-N-methoxy-N-methylpropanamide (89b) (0.75 g, 4.77 mmol) in tetrahydrofuran (10 mL) was added (3-(bis(trimethylsilyl)amino)phenyl)magnesium bromide (47c) (7.16 mL, 7.16 mmol) at 0° C. The reaction was stirred for 3 h at same temperature and quenched by adding ammonium chloride solution (10 mL). The reaction was extracted with ethyl acetate (2×25 mL). The organic layers were combined washed with brine (25 mL), dried and concentrated in vacuum. The crude residue was purified by flash column chromatography (silica gel 40 g, eluting with 0-20% ethyl acetate in hexane) to furnish 1-(3-aminophenyl)-3-cyclopropylpropan-1-one (89c) (0.758 g, 84% yield) as a colorless oil; $^1$H NMR (300 MHz, DMSO-d$_6$) δ 7.20-7.06 (m, 3H), 6.84-6.74 (m, 1H), 5.33 (s, 2H), 2.98 (t, J=7.3 Hz, 2H), 1.49 (q, J=7.2 Hz, 2H), 0.74 (dddd, J=13.9, 10.0, 5.1, 2.2 Hz, 1H), 0.42-0.33 (m, 2H), 0.10-0.01 (m, 2H); MS (ES+) 212.2 (M+Na); (ES−) 188.1 (M−1).

Step-3: Preparation of 1-(3-Aminophenyl)-3-cyclopropylpropan-1-ol (89d)

To a stirred solution of 1-(3-aminophenyl)-3-cyclopropylpropan-1-one (89c) (0.671 g, 3.55 mmol) in methanol (20 mL) was added sodium borohydride (0.295 g, 7.80 mmol) at 0° C. and stirred the reaction for 1 h at 0° C. TLC analysis (ethyl acetate/hexanes, 3/7, v/v) shows reaction was complete. Excess methanol was pumped-off under reduced pressure. The reaction mixture was quenched with saturated aqueous sodium carbonate solution (20 mL) and extracted with ethyl acetate (2×30 mL). The organic layers were combined washed with brine (25 mL), dried over anhydrous MgSO$_4$, filtered, and evaporated to dryness. The residue was purified by flash column chromatography [(silica gel 25 g, eluting with ethyl acetate in hexanes from 0 to 50%)] to furnish 1-(3-Aminophenyl)-3-cyclopropylpropan-1-ol (89d) (431 mg, 67% yield) as a white solid; $^1$H NMR (300 MHz, DMSO-d$_6$) δ 6.92 (t, J=7.7 Hz, 1H), 6.53 (t, J=1.8 Hz, 1H), 6.47-6.34 (m, 2H), 4.95 (s, 2H, D$_2$O exchangeable), 4.90 (d, J=4.2 Hz, 1H, D$_2$O exchangeable), 4.35 (m, 1H), 1.74-1.51 (m, 2H), 1.31-1.04 (m, 2H), 0.59-0.69 (m, 1H), 0.43-0.29 (m, 2H), −0.05 (dq, J=3.6, 2.4, 1.8 Hz, 2H); MS (ES$^+$): MS (ES+) 192.1 (M+1), MS (ES−) 190.1 (M−1).

Step-4: Preparation of 1-(3-cyanophenyl)-N-(3-(3-cyclopropyl-1-hydroxypropyl)phenyl)-3-(trifluoromethyl)-1H-pyrazole-5-carboxamide (89e)

In a 100 mL single-necked flask containing 1-(3-cyanophenyl)-3-(trifluoromethyl)-1H-pyrazole-5-carboxylic acid (9i) (0.922 g, 3.28 mmol), 1-(3-aminophenyl)-3-cyclopropylpropan-1-ol (89d) (0.418 g, 2.185 mmol), bromo-trispyrrolidino phosphoniumhexafluorophosphate(PyBrop) (1.223 g, 2.62 mmol) were treated with N,N-dimethylformamide (DMF) (14 mL) and N-ethyl-N-isopropylpropan-2- amine (DIPEA) (1.903 mL, 10.93 mmol) successively in a positive flow of nitrogen at room temperature. The resulting reaction mixture was stirred at room temperature for 16 h under a positive flow of nitrogen atmosphere. Excess DMF was pumped-off under reduced pressure. The residue was treated with water (30 mL), and extracted with ethyl acetate (2×30 mL) combined organics were dried over anhydrous MgSO$_4$, filtered, evaporated to dryness. The residue was then purified by flash column chromatography [silica gel 25 g, eluting with ethyl acetate in hexanes from 0-100%] to furnish 1-(3-cyanophenyl)-N-(3-(3-cyclopropyl-1-hydroxypropyl)phenyl)-3-(trifluoromethyl)-1H-pyrazole-5-carboxamide (89e) (918 mg, 92% yield) as a white solid; $^1$H NMR (300 MHz, DMSO-d$_6$) δ 10.63 (s, 1H, D$_2$O exchangeable), 8.17 (t, J=1.9 Hz, 1H), 8.01 (dt, J=7.8, 1.3 Hz, 1H), 7.92 (ddd, J=8.2, 2.2, 1.1 Hz, 1H), 7.81-7.69 (m, 2H), 7.61 (t, J=1.9 Hz, 1H), 7.53 (dt, J=8.2, 1.4 Hz, 1H), 7.27 (t, J=7.8 Hz, 1H), 7.07 (dt, J=7.8, 1.3 Hz, 1H), 5.18 (d, J=4.6 Hz, 1H, D$_2$O exchangeable), 4.50 (d, J=7.8 Hz, 1H), 1.64 (ddd, J=8.9, 6.4, 3.2 Hz, 2H), 1.18 (td, J=7.0, 2.1 Hz, 2H), 0.73-0.57 (m, 1H), 0.42-0.27 (m, 2H), −0.02--−0.09 (m, 2H); $^{19}$F NMR (282 MHz, DMSO-d$_6$) δ −60.96; IR (KBr, cm$^{-1}$): 2236 cm$^{-1}$ (—CN stretching); MS (ES+): MS (ES+) 455.2 (M+1), 477.19 (M+Na), MS (ES−) 453.02 (M−1), 488.8 (M+Cl).

Step-5: Preparation of 1-(3-cyanophenyl)-N-(3-(3-cyclopropyl-1-(1H-imidazol-1-yl)propyl)phenyl)-3-(trifluoromethyl)-1H-pyrazole-5-carboxamide (89f)

To a solution of 1-(3-cyanophenyl)-N-(3-(3-cyclopropyl-1-hydroxypropyl)phenyl)-3-(trifluoromethyl)-1H-pyrazole-5-carboxamide (89e) (0.406 g, 0.893 mmol) in dichloromethane (20 mL) at 0° C. was added thionyl chloride (0.196 mL, 2.68 mmol), allowed to warm to room temperature and stirred for 3 h. The reaction mixture was treated with 1H-imidazole (0.608 g, 8.93 mmol) followed by stirring at room temperature for 5 h. The reaction mixture was evaporated to dryness. The residue obtained was dissolved in N,N dimethyl acetamide (20 mL) added 1H-imidazole (0.608 g, 8.93 mmol) and heated to 130° C. for 36 h. TLC analysis shows reaction was complete. Excess solvent was pumped-off under reduced pressure. The residue was diluted with water (30 mL) and extracted with ethyl acetate (2×30 mL). The organic layers were combined dried over anhydrous MgSO$_4$, filtered and evaporated to dryness. The residue was purified by flash column chromatography [silica gel 25 g, eluting with ethyl acetate in hexanes from 0-100% then methanol in chloroform from 0-100%] to furnish 1-(3-cyanophenyl)-N-(3-(3-cyclopropyl-1-(1H-imidazol-1-yl)propyl)phenyl)-3-(trifluoromethyl)-1H-pyrazole-5-carboxamide (89f) (44 mg, 10% yield) as a waxy solid. $^1$H NMR (300 MHz, DMSO-d$_6$) δ 10.71 (s, 1H, D$_2$O exchangeable), 8.18 (t, J=1.8 Hz, 1H), 8.01 (dt, J=7.7, 1.3 Hz, 1H), 7.91 (ddd, J=8.1, 2.2, 1.1 Hz, 1H), 7.84-7.68 (m, 3H), 7.63-7.55 (m, 2H), 7.40-7.30 (m, 1H), 7.27 (t, J=1.2 Hz, 1H), 7.15 (dt, J=7.7, 1.4 Hz, 1H), 6.90 (t, J=1.1 Hz, 1H), 5.35 (dd, J=9.2, 6.5 Hz, 1H), 2.38-2.11 (m, 2H), 1.07 (ddq, J=29.2, 15.0, 7.6, 7.1 Hz, 2H), 0.71 (p, J=6.0 Hz, 1H), 0.44-0.33 (m, 2H), −0.04 (ddd, J=6.5, 4.6, 3.3 Hz, 2H); $^{19}$F NMR (282 MHz, DMSO-d$_6$) δ −60.96; MS (ES$^+$): MS (ES+) 505.2 (M+1), MS (ES−) 503.2 (M−1).

Step-6: Preparation of 1-(3-(aminomethyl)phenyl)-N-(3-(3-cyclopropyl-1-(1H-imidazol-1-yl)propyl)phenyl)-3-(trifluoromethyl)-1H-pyrazole-5-carboxamide (89g)

To a stirred solution of 1-(3-cyanophenyl)-N-(3-(3-cyclopropyl-1-(1H-imidazol-1-yl)propyl)phenyl)-3-(trifluoromethyl)-1H-pyrazole-5-carboxamide (89f) (0.039 g, 0.077 mmol) in anhydrous methanol (10 mL) cooled to 0° C. was added nickel(II) chloride hexahydrate (0.028 g, 0.116 mmol) followed by sodium borohydride (0.035 g, 0.928 mmol) in small portions over a period of 5 min. The reaction mixture was stirred for 5 min, TLC analysis (methanol/chloroform, 2/8, v/v) shows reaction was complete at this point N1-(2-aminoethyl)ethane-1,2-diamine (0.084 mL, 0.773 mmol) was added. Excess methanol was pumped-off under reduced pressure. The reaction mixture was treated with saturated aqueous NH$_4$Cl (30 mL), and product was extracted with chloroform (2×30 mL). the organic layers were combined dried over MgSO$_4$, filtered, evaporated to dryness. The residue was purified by flash column chromatography [(silica gel 2×12 g, eluting with methanol/chloroform from 0 to 50%)] to furnish 1-(3-(aminomethyl)phenyl)-N-(3-(3-cyclopropyl-1-(1H-imidazol-1-yl)propyl)phenyl)-3-(trifluoromethyl)-1H-pyrazole-5-carboxamide (89g) (15 mg, 38% yield) as a white solid; $^1$H NMR (300 MHz, DMSO-d$_6$) δ 10.76 (s, 1H, D$_2$O exchangeable), 7.80 (t, J=1.1 Hz, 1H), 7.62-7.51 (m, 4H), 7.48-7.41 (m, 2H), 7.37-7.29 (m, 2H), 7.27 (t, J=1.3 Hz, 1H), 7.13 (dt, J=7.7, 1.3 Hz, 1H), 6.89 (t, J=1.1 Hz, 1H), 5.34 (dd, J=9.2, 6.4 Hz, 1H), 3.80 (s, 2H), 2.38-2.08 (m, 2H), 1.19-0.89 (m, 2H), 0.70 (ddt, J=10.4, 7.3, 4.0 Hz, 1H), 0.45-0.29 (m, 2H), −0.04 (td, J=5.2, 3.7 Hz, 2H); $^{19}$F NMR (282 MHz, DMSO-d$_6$) δ −60.73; MS (ES$^+$): MS (ES+) 509.2 (M+1), MS (ES−) 507.22 (M−1).

Scheme 90

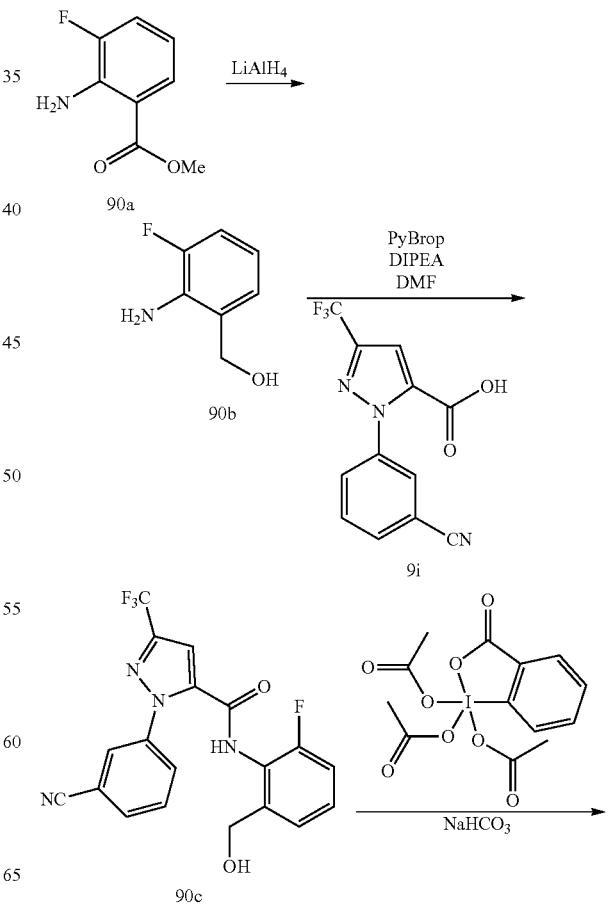

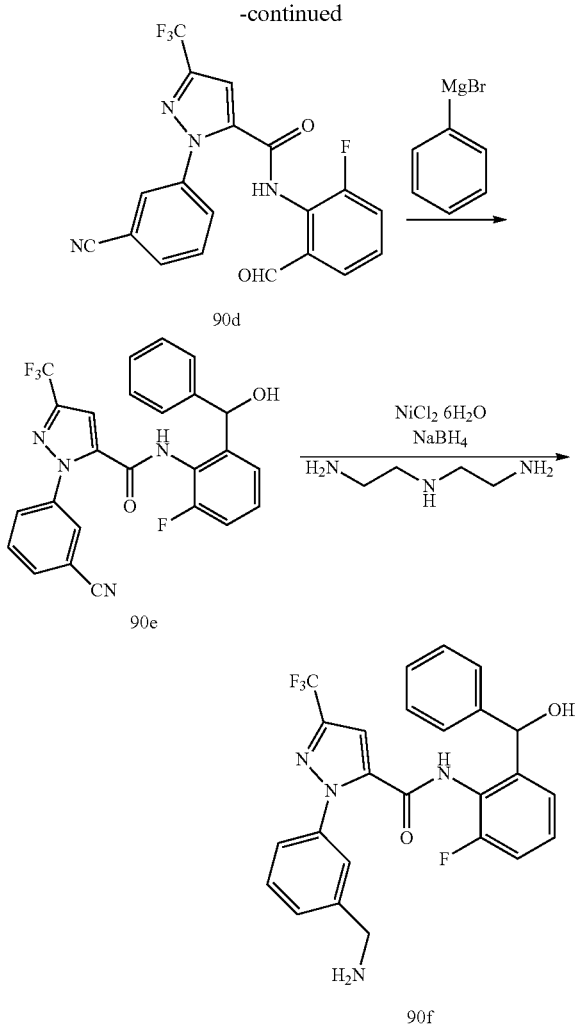

Preparation of 1-(3-(aminomethyl)phenyl)-N-(2-fluoro-6-(hydroxy(phenyl)methyl)phenyl)-3-(trifluoromethyl)-1H-pyrazole-5-carboxamide (90f)

Step-1: Preparation of (2-Amino-3-fluorophenyl)methanol (90b)

To a suspension of lithium aluminum hydride (1.835 g, 48.3 mmol) in THF (20 mL) was added dropwise at 0° C. a solution of methyl 2-amino-3-fluorobenzoate (90a) (5 g, 32.2 mmol) in THF (20 mL). The reaction mixture was stirred at room temperature overnight. The mixture was then cooled down to 0° C., quenched with ethyl acetate (30 mL) and water (10 mL). The slurry obtained was filtered through celite and washed with ethyl acetate (50 mL). The aqueous layer was separated and organic layer was dried, filtered and concentrated in vacuum to dryness to give crude product. The crude was purified by flash column chromatography (silica gel 40 g, eluting with 0-100% ethyl acetate in hexane) to furnish (2-Amino-3-fluorophenyl)methanol (90b) (2.958 g, 65% yield) as a tan solid; $^1$H NMR (300 MHz, DMSO-$d_6$) δ 6.98-6.86 (m, 2H), 6.52 (td, J=7.8, 5.2 Hz, 1H), 5.15 (t, J=5.5 Hz, 1H), 4.88 (s, 2H), 4.43 (d, J=5.5 Hz, 2H); $^{19}$F NMR (282 MHz, DMSO-$d_6$) δ −136.17 (dd, J=11.3, 5.2 Hz); MS (ES+) 165 (M+Na); (ES−) 140.0 (M−1).

Step-2: Preparation of 1-(3-cyanophenyl)-N-(2-fluoro-6-(hydroxymethyl)phenyl)-3-(trifluoromethyl)-1H-pyrazole-5-carboxamide (90c)

To a solution of 1-(3-cyanophenyl)-3-(trifluoromethyl)-1H-pyrazole-5-carboxylic acid (9i) (4 g, 14.23 mmol) in DMF (86 mL) was added (2-amino-3-fluorophenyl)methanol (90b) (2.008 g, 14.23 mmol), N-ethyl-N-isopropylpropan-2-amine (DIPEA, 12.39 mL, 71.1 mmol) and bromo-tris-pyrrolidino phosphoniumhexafluorophosphate (PyBrOP, 6.63 g, 14.23 mmol) at room temperature. The resulting reaction mixture was stirred at room temperature for 37 h under nitrogen atmosphere. The reaction was diluted with water (100 mL) and extracted with ethyl acetate (2×100 mL). The organic layers were combined washed with brine (50 mL), dried over anhydrous MgSO$_4$, filtered, and evaporated to dryness. The residue was purified by flash column chromatography [silica gel 80 g, eluting with ethyl acetate in hexanes from 0-100%] to furnish 1-(3-cyanophenyl)-N-(2-fluoro-6-(hydroxymethyl)phenyl)-3-(trifluoromethyl)-1H-pyrazole-5-carboxamide (90c) (0.709 g, 12% yield) as a white solid; MS (ES−) 403.2 (M−1).

Step-3: Preparation of 1-(3-cyanophenyl)-N-(2-fluoro-6-formylphenyl)-3-(trifluoromethyl)-1H-pyrazole-5-carboxamide (90d)

To a stirred suspension of 1-(3-cyanophenyl)-N-(2-fluoro-6-(hydroxymethyl)phenyl)-3-(trifluoromethyl)-1H-pyrazole-5-carboxamide (90c) (0.879 g, 2.174 mmol) in dichloromethane (20 mL) containing sodium bicarbonate (0.913 g, 10.87 mmol) was added Dess-MartinPeriodinane (1.383 g, 3.26 mmol) and stirred at room temperature for 3h, TLC analysis (ethyl acetate/hexanes, 1:1, v/v) shows good conversion. The reaction mixture was filtered through a Celite pad, and Celite pad was washed with ethyl acetate, filtrate was concentrated in vacuo to dryness. The residue was purified by flash column chromatography [(silica gel 25 g, eluting with ethyl acetate in hexanes from 0 to 100%)] to afford 1-(3-cyanophenyl)-N-(2-fluoro-6-formylphenyl)-3-(trifluoromethyl)-1H-pyrazole-5-carboxamide (90d) (154 mg, 18% yield) as a white solid; MS (ES+) 425.08 (M+1), MS (ES−) 401.1 (M−1).

Step-4: Preparation of 1-(3-cyanophenyl)-N-(2-fluoro-6-(hydroxy(phenyl)methyl)phenyl)-3-(trifluoromethyl)-1H-pyrazole-5-carboxamide (90e)

A solution of 1-(3-cyanophenyl)-N-(2-fluoro-6-formylphenyl)-3-(trifluoromethyl)-1H-pyrazole-5-carboxamide (90d) (0.148 g, 0.368 mmol) in THF (4 mL) cooled to 0° C. was added phenylmagnesium bromide (0.747 mL, 0.747 mmol) and stirred at room temperature for 14 h. Reaction was quenched with saturated aqueous NH$_4$Cl (25 mL), extracted with ethyl acetate (2×25 mL). The combined extracts were dried over MgSO$_4$, filtered, evaporated under reduced pressure. The residue was purified by flash column chromatography [(silica gel 25 g, eluting with ethyl acetate in hexanes from 0 to 50%)] to furnish 1-(3-cyanophenyl)-N-(2-fluoro-6-(hydroxy(phenyl)methyl)phenyl)-3-(trifluoromethyl)-1H-pyrazole-5-carboxamide (90e) (92 mg, 52% yield) as a pale yellow oil; $^1$H NMR (300 MHz, DMSO-$d_6$) δ 10.30 (s, 1H, D$_2$O exchangeable), 7.97 (dt, J=6.9, 1.7 Hz, 1H), 7.90 (d, J=1.9 Hz, 1H), 7.74-7.66 (m, 2H), 7.62 (s, 1H), 7.46-7.34 (m, 2H), 7.28-7.18 (m, 6H), 6.04 (s, 1H, D$_2$O exchangeable), 5.97 (s, 1H); $^{19}$F NMR (282 MHz, DMSO-d$_6$) δ −60.9, −119.75; MS (ES$^+$): MS (ES+) 503.1 (M+Na), MS (ES−) 479.1 (M−1).

Step-5: Preparation of 1-(3-(aminomethyl)phenyl)-N-(2-fluoro-6-(hydroxy(phenyl)methyl)phenyl)-3-(trifluoromethyl)-1H-pyrazole-5-carboxamide (90f)

To a stirred solution of 1-(3-cyanophenyl)-N-(2-fluoro-6-(hydroxy(phenyl)methyl)phenyl)-3-(trifluoromethyl)-1H-pyrazole-5-carboxamide (90e) (0.051 g, 0.106 mmol) in anhydrous methanol (10 mL) cooled to 0° C. was added nickel(II) chloride hexahydrate (0.038 g, 0.159 mmol) followed by sodium borohydride (0.048 g, 1.274 mmol) in small portions over a period of 5 min. TLC analysis (methanol/chloroform, 2/8, v/v) shows reaction was complete at this point N1-(2-aminoethyl)ethane-1,2-diamine (0.115 mL, 1.062 mmol) was added. Excess methanol was pumped-off under reduced pressure. The reaction mixture was treated with saturated aqueous NH$_4$Cl (30 mL), and product was extracted with chloroform (2×30 mL), combined organic layer was dried over MgSO$_4$, filtered, evaporated to dryness. The residue was purified by flash column chromatography [(silica gel 25 g, eluting with methanol/chloroform from 0 to 50%)] to furnish 1-(3-(aminomethyl)phenyl)-N-(2-fluoro-6-(hydroxy(phenyl)methyl)phenyl)-3-(trifluoromethyl)-1H-pyrazole-5-carboxamide (90f) (43 mg, 84% yield) as a white solid; $^1$H NMR (300 MHz, DMSO-d$_6$) δ 7.47-7.40 (m, 3H), 7.40-7.33 (m, 3H), 7.31-7.13 (m, 7H), 5.96 (s, 1H), 3.75 (s, 2H); $^{19}$F NMR (282 MHz, DMSO-d$_6$) δ −60.74, −119.59; MS (ES$^+$): MS (ES+) 485.1 (M+1), 969.2 (2M+1), MS (ES−) 483.1 (M−1), 967.2 (2M−1); Analysis calculated for: C$_{25}$H$_{20}$F$_4$N$_4$O$_2$: C, 61.98; H, 4.16; N, 11.57; Found: C, 61.91; H, 4.43; N, 11.61.

Scheme 91

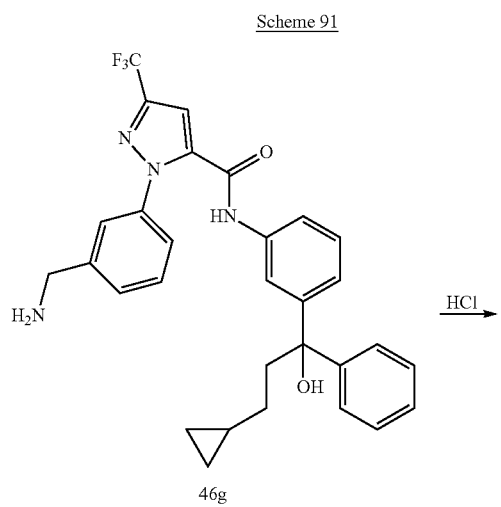

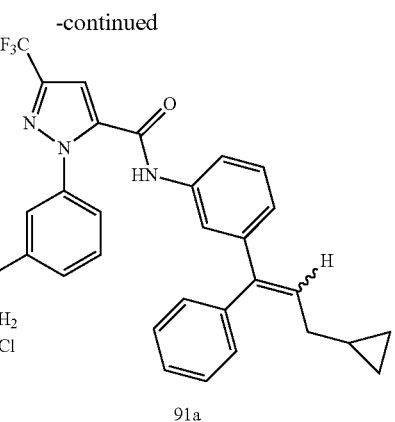

Preparation of (E/Z)-1-(3-(Aminomethyl)phenyl)-N-(3-(3-cyclopropyl-1-phenylprop-1-enyl)phenyl)-3-(trifluoromethyl)-1H-pyrazole-5-carboxamide hydrochloride (91a)

To a stirred solution of 1-(3-(aminomethyl)phenyl)-N-(3-(3-cyclopropyl-1-hydroxy-1-phenylpropyl)phenyl)-3-(trifluoromethyl)-1H-pyrazole-5-carboxamide (46g) (0.33 g, 0.617 mmol) in acetone (10 mL) was added conc. HCl (0.154 mL, 1.852 mmol) and stirred with heating for 15 mins. The reaction mixture was concentrated in vacuum to dryness. The residue obtained was dissolved in IPA (2.0 mL) and heated to reflux, ether (40 mL) was added to the hot solution and continued heating at reflux for 15 mins. The reaction mixture was cooled to room temperature and solid obtained was collected by filtration, dried in vacuum to furnish (E/Z)-1-(3-(aminomethyl)phenyl)-N-(3-(3-cyclopropyl-1-phenylprop-1-enyl)phenyl)-3-(trifluoromethyl)-1H-pyrazole-5-carboxamide hydrochloride (91a) (0.251 g, 0.454 mmol, 73.5% yield) as a white solid; $^1$H NMR (300 MHz, DMSO-d$_6$) δ 10.78 (d, J=13.2 Hz, 1H), 8.38 (s, 3H), 7.74-7.68 (m, 2H), 7.67-7.47 (m, 4H), 7.46-7.22 (m, 5H), 7.15 (ddt, J=16.5, 6.0, 1.6 Hz, 2H), 6.93 (ddt, J=7.6, 2.8, 1.3 Hz, 1H), 6.17 (dt, J=12.0, 7.4 Hz, 1H), 4.12 (s, 2H), 2.00-1.89 (m, 2H), 0.86-0.70 (m, 1H), 0.48-0.36 (m, 2H), 0.06 (td, J=5.0, 1.4 Hz, 2H); 19F NMR (282 MHz, DMSO-d$_6$) δ −60.81, −60.82; MS (ES−) 515.3 (M−1); Analysis calculated for C$_{30}$H$_{27}$F$_3$N$_4$O.HCl: C, 65.16; H, 5.10; Cl, 6.41; N, 10.13; Found: C, 64.75; H, 5.30; Cl, 6.21; N, 9.85.

Scheme 92

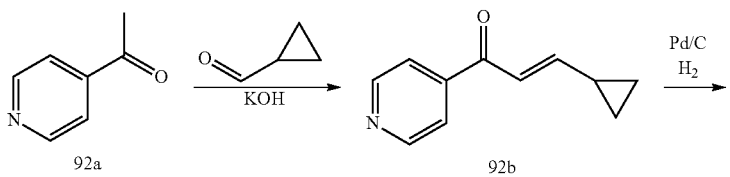

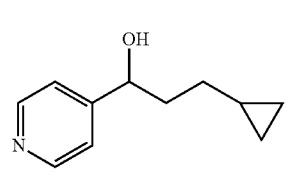
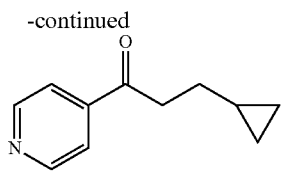
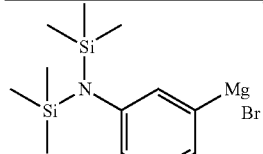
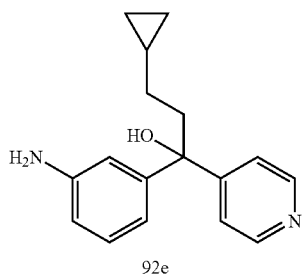
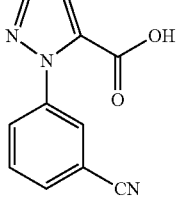
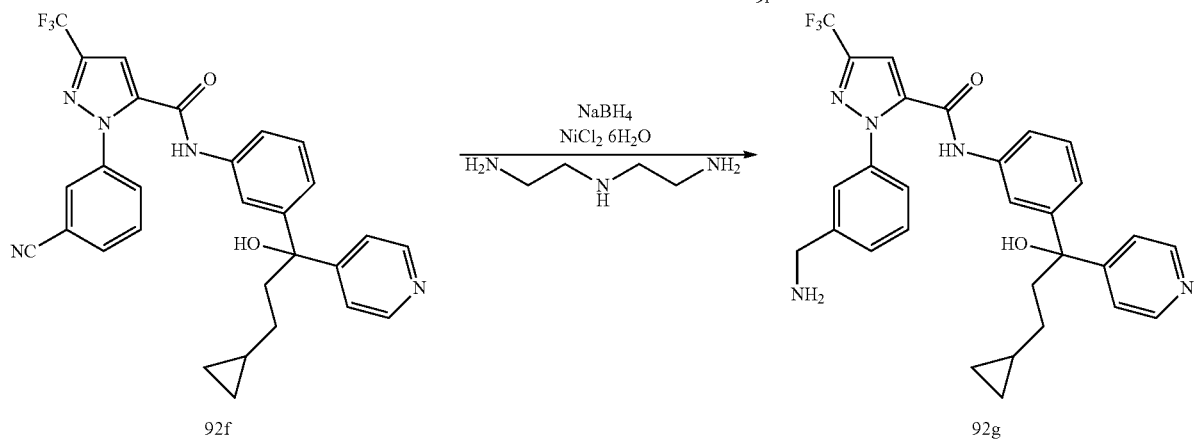
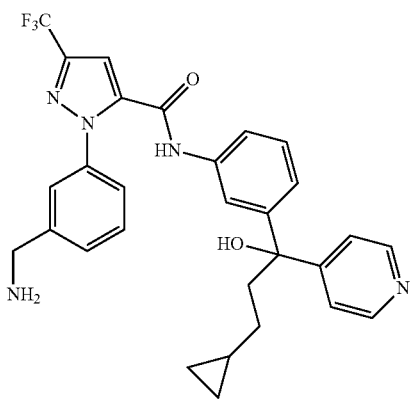

Preparation of 1-(3-(aminomethyl)phenyl)-N-(3-(3-cyclopropyl-1-hydroxy-1-(pyridin-4-yl)propyl)phenyl)-3-(trifluoromethyl)-1H-pyrazole-5-carboxamide (92g)

Step-1: Preparation of (E)-3-cyclopropyl-1-(pyridin-4-yl)prop-2-en-1-one (92b)

To a stirred solution of 1-(pyridin-4-yl)ethanone (92a) (1.516 mL, 13.27 mmol) in methanol (100 mL) cooled to 0° C. was added cyclopropanecarboxaldehyde (1.5 mL, 19.90 mmol) and aqueous potassium hydroxide (1N, 2.65 mL, 2.65 mmol). The reaction was allowed to warm to room temperature overnight. The reaction was acidified with 1N hydrochloric acid and concentrated in vacuum to remove methanol. The crude residue was dissolved in ethyl acetate (100 mL) washed with sodium carbonate solution, water (2×50 mL), brine (50 mL), dried, filtered and concentrated in vacuum. The crude residue was purified by flash column chromatography (silica gel, 12 g, eluting with ethyl acetate in hexanes 0 to 100%) to afford pure (E)-3-cyclopropyl-1-(pyridin-4-yl)prop-2-en-1-one (92b) (479 mg, 20.85%); $^1$H NMR (300 MHz, DMSO-$d_6$) δ 8.89-8.59 (m, 2H), 7.91-7.71 (m, 2H), 7.19 (d, J=15.1 Hz, 1H), 6.58 (dd, J=15.1, 10.4 Hz, 1H), 1.88-1.71 (m, 1H), 1.10-0.96 (m, 2H), 0.87-0.72 (m, 2H).

Step-2: Preparation of 3-cyclopropyl-1-(pyridin-2-yl)propan-1-ol (92c)

To Pd/C (138 mg, 0.130 mmol) in methanol (50 mL) was added (E)-3-cyclopropyl-1-(pyridin-4-yl)prop-2-en-1-one (92b) (450 mg, 2.60 mmol) and hydrogenated at 60 psi for 1 h. The reaction mixture was filtered through celite and filtrate concentrated in vacuum. The crude residue was purified by flash column chromatography (silica gel, 12 g, eluting with ethyl acetate in hexane 0-100%) to afford 3-cyclopropyl-1-(pyridin-4-yl)propan-1-ol (92c) (323 mg, 70.1%) as an oil; $^1$H NMR (300 MHz, DMSO-$d_6$) δ 8.58-8.37 (m, 2H), 7.31 (ddd, J=4.5, 1.6, 0.6 Hz, 2H), 5.36 (d, J=4.7 Hz, 1H), 4.67-4.41 (m, 1H), 1.66 (tdd, J=7.7, 5.7, 3.0 Hz, 2H), 1.28-1.16 (m, 2H), 0.73-0.56 (m, 1H), 0.43-0.25 (m, 2H), 0.06-−0.12 (m, 2H).

Step-3: Preparation of 3-cyclopropyl-1-(pyridin-2-yl)propan-1-one (92d)

To a stirred solution of 3-cyclopropyl-1-(pyridin-4-yl)propan-1-ol (92c) (0.3 g, 1.693 mmol) in dichloromethane (10 mL) at 0° C. was added NaHCO$_3$ (0.427 g, 5.08 mmol) and Dess-MartinPeriodinane (1.436 g, 3.39 mmol). The reaction mixture was stirred at 0° C. for 30 minutes and warmed to room temperature in 15 mins. The reaction was stirred at room temperature for 1 hr and quenched by adding aqueous saturated sodium bicarbonate (25 mL), extracted with dichloromethane (2×50 mL). The organic layers were combined, washed with water (2×25 mL), brine (25 mL), dried, filtered and concentrated in vacuum. The crude residue was purified by column chromatography (silicagel, 12 g, eluting with 0-30% ethyl acetate in hexane) to afford 3-cyclopropyl-1-(pyridin-4-yl)propan-1-one (92d) (290 mg, 98%) as an oil; $^1$H NMR (300 MHz, DMSO-d$_6$) δ 3.14 (t, J=7.2 Hz, 2H), 1.52 (q, J=7.1 Hz, 2H), 0.75 (dddd, J=12.0, 8.1, 7.0, 2.8 Hz, 1H), 0.47-0.28 (m, 2H), 0.14-0.02 (m, 2H).

Step-4: Preparation of 1-(3-aminophenyl)-3-cyclopropyl-1-(pyridin-4-yl)propan-1-ol (92e)

To a stirred solution of 3-cyclopropyl-1-(pyridin-4-yl)propan-1-one (92d) (250 mg, 1.427 mmol) in tetrahydrofuran (20 mL) was added (3-(bis(trimethylsilyl)amino)phenyl)magnesium bromide (49c) (2.2853 mL, 2.2853 mmol) at 0° C. Reaction was allowed to warm to room temperature and stirred for 2 h. The reaction was quenched with ammonium chloride solution (25 mL), extracted with ethyl acetate (2×50 mL). the organic layers were combined, washed with water (2×25 mL), brine (25 mL), dried, filtered and concentrated in vacuum. The crude residue was purified by flash column chromatography (silicagel, 25 g eluting with CMA 80 in chloroform 0-100%) to afford 1-(3-aminophenyl)-3-cyclopropyl-1-(pyridin-4-yl)propan-1-ol (92e) (430 mg, 1.602 mmol, 112% yield). This was pure enough to be used as such in next step; MS (ES+) 269.2 (M+1).

Step-5: Preparation of 1-(3-cyanophenyl)-N-(3-(3-cyclopropyl-1-hydroxy-1-(pyridin-4-yl)propyl)phenyl)-3-(trifluoromethyl)-1H-pyrazole-5-carboxamide (92f)

To a solution of 1-(3-cyanophenyl)-3-(trifluoromethyl)-1H-pyrazole-5-carboxylic acid (9i) (178 mg, 0.633 mmol) in DMF (5 mL) was added 1-(3-aminophenyl)-3-cyclopropyl-1-(pyridin-4-yl)propan-1-ol (92e) (204 mg, 0.760 mmol), N-ethyl-N-isopropylpropan-2-amine (0.883 mL, 5.07 mmol) and Bromo-tris-pyrrolidino phosphoniumhexafluorophosphate (PyBrOP, 325 mg, 0.697 mmol) at room temperature and stirred at 25° C. for 16 h. The reaction mixture was diluted with water (50 mL) and extracted with ethyl acetate (100 mL, 50 mL). The organic layers were combined and dried over anhydrous MgSO$_4$, filtered, concentrated under reduced pressure to dryness. The residue obtained was purified by flash column chromatography (silica gel 12 g, eluting with CMA 80 in chloroform 0-100%) to furnish 1-(3-cyanophenyl)-N-(3-(3-cyclopropyl-1-hydroxy-1-(pyridin-4-yl)propyl)phenyl)-3-(trifluoromethyl)-1H-pyrazole-5-carboxamide (92f) (320 mg, 95% yield) as an oil; $^1$H NMR (300 MHz, DMSO-d$_6$) δ 10.63 (s, 1H), 8.48-8.42 (m, 2H), 8.16 (d, J=2.2 Hz, 1H), 8.00 (d, J=7.8 Hz, 1H), 7.94-7.87 (m, 1H), 7.78-7.68 (m, 3H), 7.59 (d, J=7.7 Hz, 1H), 7.43-7.36 (m, 2H), 7.31-7.15 (m, 2H), 5.76 (s, 1H), 2.31 (t, J=8.2 Hz, 2H), 1.07 (dq, J=15.1, 7.5 Hz, 2H), 0.62 (q, J=6.8 Hz, 1H), 0.42-0.22 (m, 2H), −0.07 (q, J=4.6 Hz, 2H); $^{19}$F NMR (282 MHz, DMSO) δ −60.95.

Step-6: Preparation of 1-(3-(aminomethyl)phenyl)-N-(3-(3-cyclopropyl-1-hydroxy-1-(pyridin-4-yl)propyl)phenyl)-3-(trifluoromethyl)-1H-pyrazole-5-carboxamide (92g)

To a stirred solution of 1-(3-cyanophenyl)-N-(3-(3-cyclopropyl-1-hydroxy-1-(pyridin-4-yl)propyl)phenyl)-3-(trifluoromethyl)-1H-pyrazole-5-carboxamide (92f) (300 mg, 0.564 mmol) in methanol (25 mL) at 0° C. was added nickel(II) chloride hexahydrate (29.2 mg, 0.123 mmol), To this sodium tetrahydroborate (133 mg, 3.53 mmol) was added in small portions over a period of 15 minutes. The reaction was stirred for 15 minutes, quenched by adding N1-(2-aminoethyl)ethane-1,2-diamine (0.135 mL, 1.298 mmol) and stirred for 30 minutes at room temperature. The reaction mixture was concentrated in vacuum to remove methanol. The residue was adsorbed on silicagel and purified twice by flash column chromatography (silica gel, 12 g, eluting with CMA 80 in chloroform 0 to 100%) and (silica gel 2×4 g, eluting with methanol in chloroform 0 to 30%) to afford 1-(3-(aminomethyl)phenyl)-N-(3-(3-cyclopropyl-1-hydroxy-1-(pyridin-4-yl)propyl)phenyl)-3-(trifluoromethyl)-1H-pyrazole-5-carboxamide (92g) (20 mg, 6.62% yield) as a colorless solid; $^1$H NMR (300 MHz, DMSO-d$_6$) δ 10.67 (s, 1H, D$_2$O exchangeable), 8.52-8.41 (m, 2H), 7.70 (s, 1H), 7.54 (d, J=15.9 Hz, 3H), 7.49-7.35 (m, 4H), 7.26 (ddd, J=20.1, 11.6, 7.3 Hz, 3H), 5.76 (s, 1H, D$_2$O exchangeable), 3.77 (s, 2H), 2.31 (t, J=8.3 Hz, 2H), 2.08 (s, 2H, D$_2$O exchangeable), 1.06 (dq, J=21.4, 7.4 Hz, 2H), 0.63 (t, J=6.7 Hz, 1H), 0.40-0.28 (m, 2H), −0.07 (q, J=4.7 Hz, 2H); MS (ES+) 536.2 (M+1), (ES−) 534.2 (M−1); Analysis calculated for C$_{29}$H$_{28}$F$_3$N$_5$O$_5$: C: 65.02, H: 5.27, N: 13.08; Found: C, 64.69; H, 5.40: N, 13.08.

Scheme 93

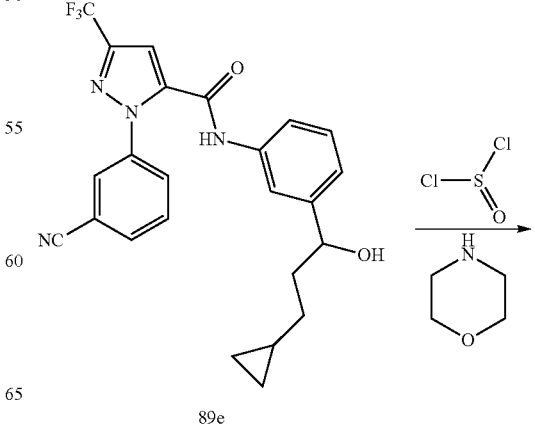

89e

407

-continued

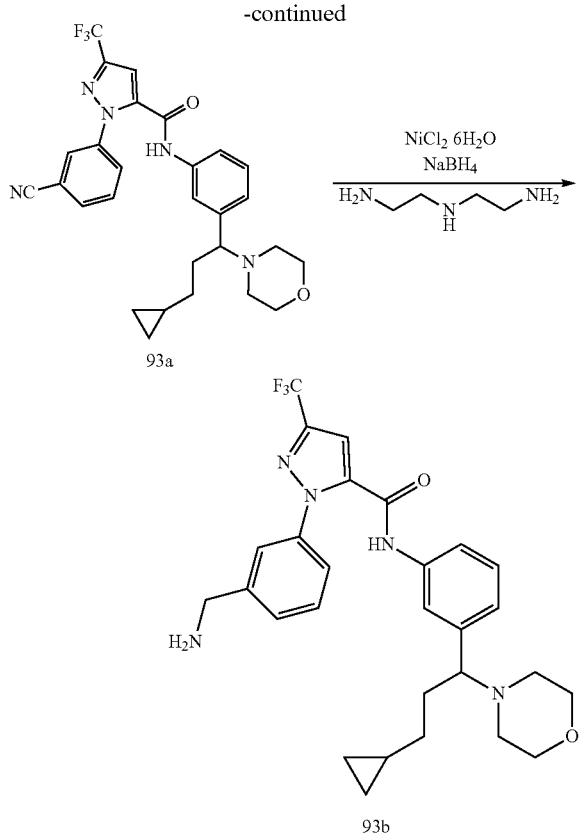

Preparation of 1-(3-(aminomethyl)phenyl)-N-(3-(3-cyclopropyl-1-morpholinopropyl)phenyl)-3-(trifluoromethyl)-1H-pyrazole-5-carboxamide (93b)

Step-1: Preparation of 1-(3-cyanophenyl)-N-(3-(3-cyclopropyl-1-morpholinopropyl)phenyl)-3-(trifluoromethyl)-1H-pyrazole-5-carboxamide (93a)

To a solution of 1-(3-cyanophenyl)-N-(3-(3-cyclopropyl-1-hydroxypropyl)phenyl)-3-(trifluoromethyl)-1H-pyrazole-5-carboxamide (89e) (0.2 g, 0.440 mmol) in dichloromethane (20 mL) at 0° C. was added thionyl chloride (0.096 mL, 1.320 mmol), and allowed to warm to room temperature over a period of 3 h. The reaction mixture was treated with morpholine (1.518 mL, 17.60 mmol) and evaporated to dryness. The residue was dissolved in N,N dimethyl formamide (20 mL), added morpholine (1.518 mL, 17.60 mmol) and heated to reflux for 18 h. Excess solvent was pumped-off under reduced pressure. The residue was diluted with water (30 mL) and extracted with ethyl acetate (2×30 mL). The organic layers were combined dried over anhydrous MgSO$_4$, filtered and evaporated to dryness. The residue was purified by flash column chromatography [silica gel 25 g, eluting with methanol in chloroform from 0-100%] to furnish 1-(3-cyanophenyl)-N-(3-(3-cyclopropyl-1-morpholinopropyl)phenyl)-3-(trifluoromethyl)-1H-pyrazole-5-carboxamide (93a) (200 mg, 87% yield) as a dark yellow waxy solid; MS (ES+): MS (ES+) 524.3 (M+1), MS (ES−) 522.3 (M−1).

Step-2: Preparation of 1-(3-(aminomethyl)phenyl)-N-(3-(3-cyclopropyl-1-morpholinopropyl)phenyl)-3-(trifluoromethyl)-1H-pyrazole-5-carboxamide (93b)

To a stirred solution of 1-(3-cyanophenyl)-N-(3-(3-cyclopropyl-1-morpholinopropyl)phenyl)-3-(trifluoromethyl)-

408

1H-pyrazole-5-carboxamide (93a) (0.192 g, 0.367 mmol) in anhydrous methanol (10 mL) cooled to 0° C., was added nickel(II) chloride hexahydrate (0.131 g, 0.550 mmol) followed by sodium borohydride (0.166 g, 4.40 mmol) in small portions over a period of 5 min. The reaction mixture was stirred for 34 min, TLC analysis (methanol/chloroform, 2/8, v/v) shows reaction was complete at this point N1-(2-aminoethyl)ethane-1,2-diamine (0.396 mL, 3.67 mmol) was added. Excess methanol was pumped-off under reduced pressure. The reaction mixture was treated with saturated aqueous NH$_4$Cl (30 mL), and product was extracted with chloroform (2×30 mL). The organic layers were combined dried over anhydrous MgSO$_4$, filtered and evaporated to dryness. The residue was purified by flash column chromatography [(silica gel 40 g, eluting with methanol/chloroform from 0 to 50%)] to furnish 1-(3-(aminomethyl)phenyl)-N-(3-(3-cyclopropyl-1-morpholinopropyl)phenyl)-3-(trifluoromethyl)-1H-pyrazole-5-carboxamide (93b) (39 mg, 20% yield) as a white solid; $^1$H NMR (300 MHz, DMSO-d$_6$) δ 10.70 (d, J=10.1 Hz, 1H, D$_2$O exchangeable), 7.59 (d, J=7.8 Hz, 2H), 7.56-7.52 (m, 1H), 7.45 (ddt, J=5.7, 4.0, 2.1 Hz, 3H), 7.41-7.33 (m, 1H), 7.29 (t, J=7.8 Hz, 1H), 6.98 (d, J=7.6 Hz, 1H), 3.79 (s, 2H), 3.52 (t, J=4.7 Hz, 4H), 3.27 (dd, J=8.6, 5.3 Hz, 1H), 2.29 (h, J=7.2, 6.6 Hz, 4H), 2.02-1.88 (m, 1H), 1.70 (dtd, J=13.7, 9.3, 5.2 Hz, 1H), 1.07 (ddt, J=12.7, 9.7, 6.2 Hz, 1H), 0.99-0.81 (m, 1H), 0.69-0.54 (m, 1H), 0.42-0.24 (m, 2H), −0.09 (td, J=5.4, 3.7 Hz, 2H); $^{19}$F NMR (282 MHz, DMSO-d$_6$) δ −60.73; MS (ES$^+$): MS (ES+) 528.3 (M+1), MS (ES−) 526.1 (M−1), 562.3 (M+Cl); Analysis calculated for C$_{28}$H$_{32}$F$_3$N$_5$O$_2$.0.25H$_2$O: C, 63.20; H, 6.16; N, 13.16; Found: C, 63.23; H, 6.18; N, 12.73.

Scheme 94

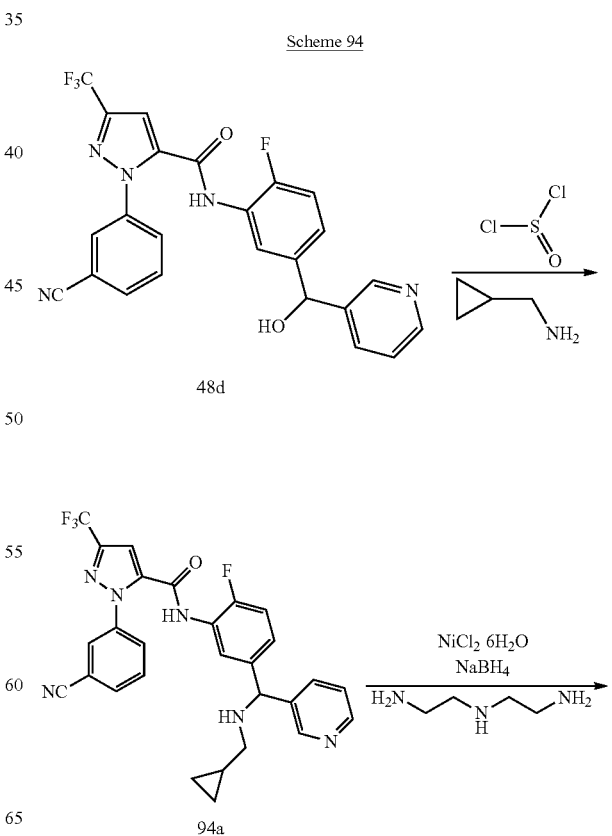

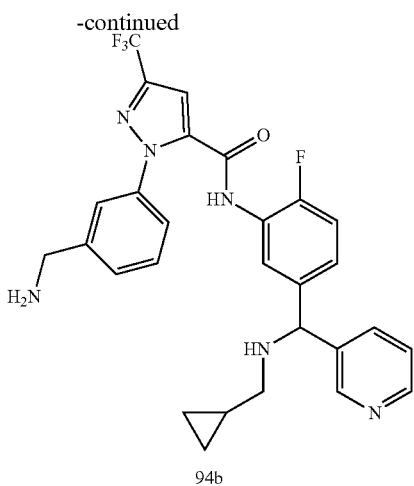

94b

Preparation of 1-(3-(aminomethyl)phenyl)-N-(5-((cyclopropylmethylamino)(pyridin-3-yl)methyl)-2-fluorophenyl)-3-(trifluoromethyl)-1H-pyrazole-5-carboxamide (94b)

Step-1: Preparation of 1-(3-cyanophenyl)-N-(5-((cyclopropylmethylamino)(pyridin-3-yl)methyl)-2-fluorophenyl)-3-(trifluoromethyl)-1H-pyrazole-5-carboxamide (94a)

To a solution of 1-(3-cyanophenyl)-N-(2-fluoro-5-(hydroxy(pyridin-3-yl)methyl)phenyl)-3-(trifluoromethyl)-1H-pyrazole-5-carboxamide (48d) (1.433 g, 2.98 mmol) in dichloromethane (20 mL) at 0° C. was added thionyl chloride (0.651 mL, 8.93 mmol) allowed to warm to room temperature and stirred for 12 h. The reaction mixture was quenched with cyclopropylmethyl amine (1.275 mL, 14.88 mmol) stirred for 1 h at room temperature, and concentrated in vacuum to dryness. The residue was dissolved in cyclopropylmethyl amine (5.10 mL, 59.5 mmol), acetonitrile (20 mL) and heated at 100° C. for 18 h. TLC analysis (CHCl$_3$/MeOH, 9/1, v/v) shows reaction was complete, the reaction mixture was evaporated to dryness. The residue was purified by flash column chromatography (silica gel 40 g, eluting 0-100% ethyl acetate in hexane) to afford 1-(3-cyanophenyl)-N-(5-((cyclopropylmethylamino)(pyridin-3-yl)methyl)-N-(2-fluorophenyl)-3-(trifluoromethyl)-1H-pyrazole-5-carboxamide (94a) (0.841 g, 53% yield) as an orange red solid; $^1$H NMR (300 MHz, DMSO-d$_6$) δ 10.55 (s, 1H, D$_2$O exchangeable), 8.61 (d, J=2.1 Hz, 1H), 8.40 (dd, J=4.8, 1.7 Hz, 1H), 8.13 (t, J=1.7 Hz, 1H), 8.00 (dt, J=7.7, 1.3 Hz, 1H), 7.95-7.86 (m, 1H), 7.80-7.69 (m, 3H), 7.60 (dd, J=7.7, 2.2 Hz, 1H), 7.42-7.19 (m, 3H), 4.92 (s, 1H), 2.69 (s, 1H, D$_2$O exchangeable), 2.27 (dd, J=6.7, 2.3 Hz, 2H), 0.90 (ddt, J=7.7, 5.9, 4.6 Hz, 1H), 0.44-0.31 (m, 2H), 0.04 (tt, J=5.7, 2.9 Hz, 2H); $^{19}$F NMR (282 MHz, DMSO-d$_6$) δ −60.99, −122.96; IR (KBr, cm$^{-1}$): 2234 cm$^{-1}$ (—CN stretching); MS (ES$^+$): MS (ES+) 535.2 (M+1), 557.2 (M+Na), MS (ES−) 533.2 (M−1).

Step-2: Preparation of 1-(3-(aminomethyl)phenyl)-N-(5-((cyclopropylmethylamino)(pyridin-3-yl)methyl)-2-fluorophenyl)-3-(trifluoromethyl)-1H-pyrazole-5-carboxamide (94b)

To a stirred solution of 1-(3-cyanophenyl)-N-(5-((cyclopropylmethylamino)(pyridin-3-yl)methyl)-2-fluorophenyl)- 3-(trifluoromethyl)-1H-pyrazole-5-carboxamide (94a) (0.612 g, 1.145 mmol) in anhydrous methanol (30 mL) cooled to 0° C. was added nickel(II) chloride hexahydrate (0.408 g, 1.717 mmol) followed by sodium borohydride (0.347 g, 9.16 mmol) in small portions over a period of 5 min. The reaction mixture was stirred for 10 min. TLC analysis (methanol/chloroform, 1/9, v/v) shows reaction was complete at this point N1-(2-aminoethyl)ethane-1,2-diamine (1.237 mL, 11.45 mmol) was added. Excess methanol was pumped-off under reduced pressure. The reaction mixture was treated with saturated aqueous NH$_4$Cl (50 mL), and product was extracted with chloroform (2×50 mL). The organic layers were combined organic layer, dried over MgSO$_4$, filtered, and evaporated to dryness. The residue was purified by flash column chromatography [(silica gel 40 g, eluting with methanol/chloroform from 0 to 50%)] to furnish 1-(3-(aminomethyl)phenyl)-N-(5-((cyclopropylmethylamino)(pyridin-3-yl)methyl)-2-fluorophenyl)-3-(trifluoromethyl)-1H-pyrazole-5-carboxamide (94b) (258 mg, 42% yield) as a white solid; $^1$H NMR (300 MHz, DMSO-d$_6$) δ 10.55 (s, 1H, D$_2$O exchangeable), 8.60 (d, J=2.2 Hz, 1H), 8.40 (dd, J=4.7, 1.7 Hz, 1H), 7.77 (dt, J=7.9, 2.0 Hz, 1H), 7.65 (dd, J=7.5, 2.2 Hz, 1H), 7.57 (s, 1H), 7.52 (s, 1H), 7.47-7.41 (m, 2H), 7.39-7.29 (m, 3H), 7.23 (dd, J=10.3, 8.5 Hz, 2H, 1H D$_2$O exchangeable), 4.91 (s, 1H), 3.78 (s, 2H), 2.27 (dd, J=6.5, 2.5 Hz, 2H), 0.97-0.84 (m, 1H), 0.44-0.32 (m, 2H), 0.08-0.01 (m, 2H); $^1$H NMR (300 MHz, DMSO-d$_6$ D$_2$O) δ 8.59 (d, J=2.2 Hz, 1H), 8.40 (dd, J=4.8, 1.6 Hz, 1H), 7.79 (dt, J=8.1, 2.0 Hz, 1H), 7.65 (dd, J=7.4, 2.2 Hz, 1H), 7.55 (s, 1H), 7.51 (d, J=2.1 Hz, 1H), 7.45 (dd, J=4.7, 2.5 Hz, 2H), 7.34 (tt, J=4.8, 2.8 Hz, 3H), 7.23 (dd, J=10.3, 8.6 Hz, 1H), 4.92 (s, 1H), 3.76 (s, 2H), 2.26 (dd, J=6.9, 1.7 Hz, 2H), 1.03-0.76 (m, 1H), 0.48-0.30 (m, 2H), 0.07-0.01 (m, 2H); $^{19}$F NMR (282 MHz, DMSO-d$_6$) δ −60.76, −123.40; MS (ES$^+$): MS (ES+) 539.2 (M+1), MS (ES−) 537.2 (M−1); Analysis calculated for: C$_{28}$H$_{26}$F$_4$N$_6$O.0.25H$_2$O: C, 61.93; H, 4.92; N, 15.48; Found: C, 61.73; H, 5.06; N, 15.16.

Scheme 95

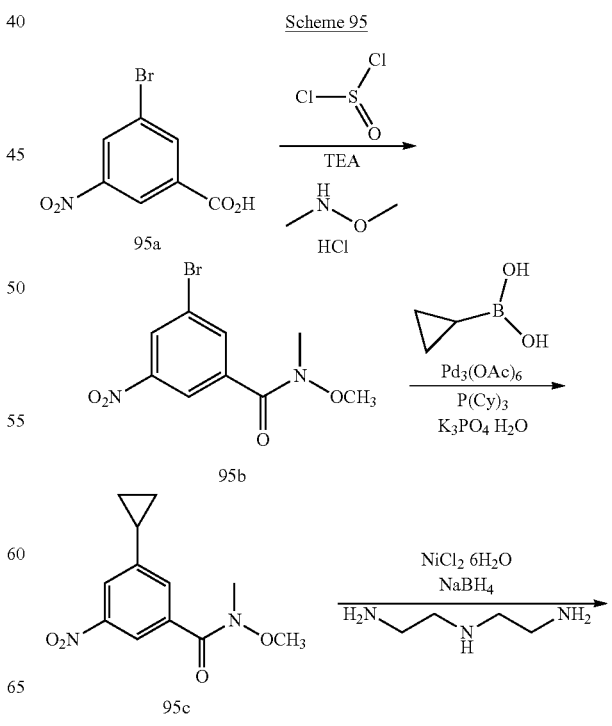

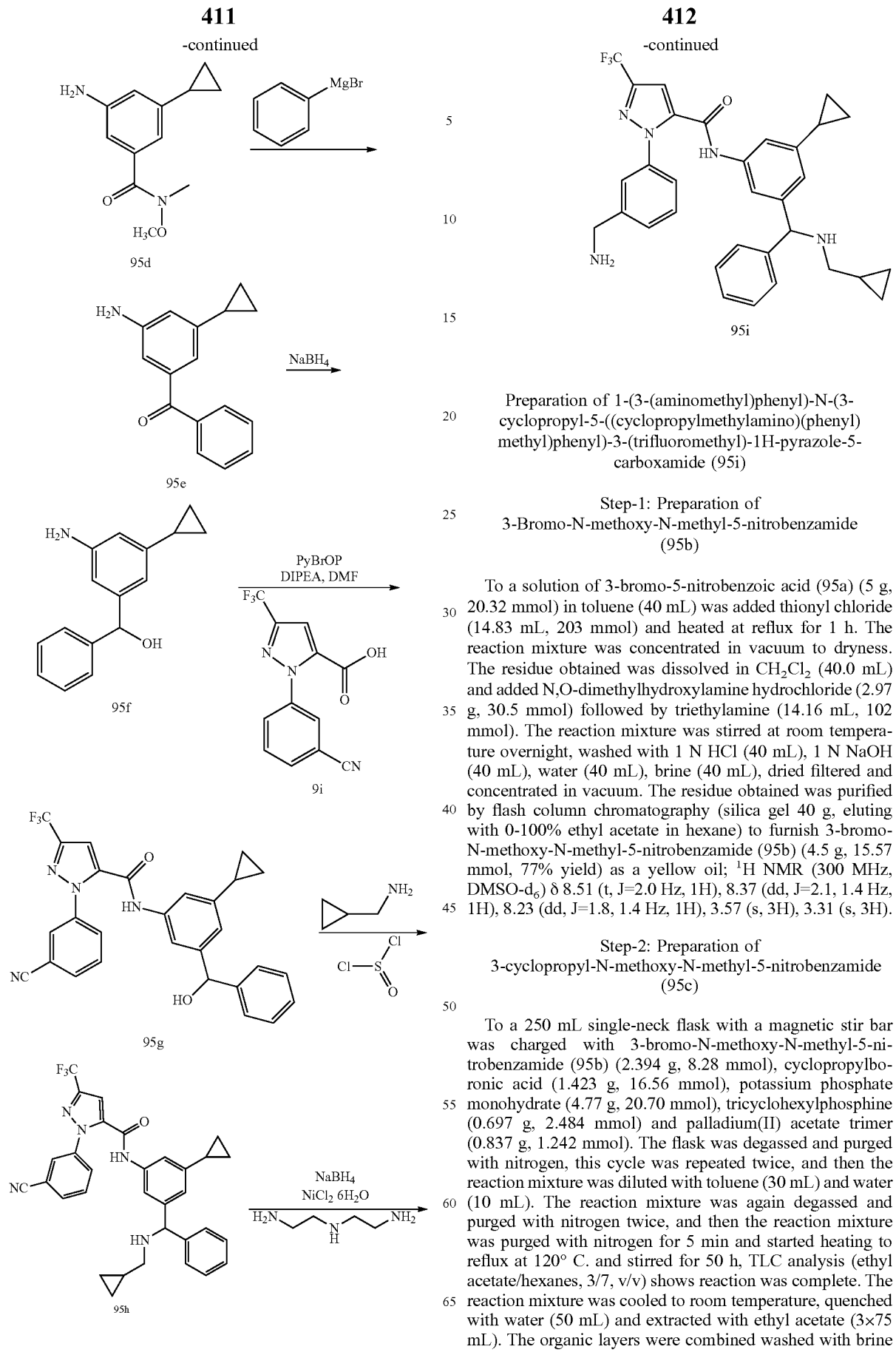

Preparation of 1-(3-(aminomethyl)phenyl)-N-(3-cyclopropyl-5-((cyclopropylmethylamino)(phenyl)methyl)phenyl)-3-(trifluoromethyl)-1H-pyrazole-5-carboxamide (95i)

Step-1: Preparation of 3-Bromo-N-methoxy-N-methyl-5-nitrobenzamide (95b)

To a solution of 3-bromo-5-nitrobenzoic acid (95a) (5 g, 20.32 mmol) in toluene (40 mL) was added thionyl chloride (14.83 mL, 203 mmol) and heated at reflux for 1 h. The reaction mixture was concentrated in vacuum to dryness. The residue obtained was dissolved in $CH_2Cl_2$ (40.0 mL) and added N,O-dimethylhydroxylamine hydrochloride (2.97 g, 30.5 mmol) followed by triethylamine (14.16 mL, 102 mmol). The reaction mixture was stirred at room temperature overnight, washed with 1 N HCl (40 mL), 1 N NaOH (40 mL), water (40 mL), brine (40 mL), dried filtered and concentrated in vacuum. The residue obtained was purified by flash column chromatography (silica gel 40 g, eluting with 0-100% ethyl acetate in hexane) to furnish 3-bromo-N-methoxy-N-methyl-5-nitrobenzamide (95b) (4.5 g, 15.57 mmol, 77% yield) as a yellow oil; $^1$H NMR (300 MHz, DMSO-$d_6$) δ 8.51 (t, J=2.0 Hz, 1H), 8.37 (dd, J=2.1, 1.4 Hz, 1H), 8.23 (dd, J=1.8, 1.4 Hz, 1H), 3.57 (s, 3H), 3.31 (s, 3H).

Step-2: Preparation of 3-cyclopropyl-N-methoxy-N-methyl-5-nitrobenzamide (95c)

To a 250 mL single-neck flask with a magnetic stir bar was charged with 3-bromo-N-methoxy-N-methyl-5-nitrobenzamide (95b) (2.394 g, 8.28 mmol), cyclopropylboronic acid (1.423 g, 16.56 mmol), potassium phosphate monohydrate (4.77 g, 20.70 mmol), tricyclohexylphosphine (0.697 g, 2.484 mmol) and palladium(II) acetate trimer (0.837 g, 1.242 mmol). The flask was degassed and purged with nitrogen, this cycle was repeated twice, and then the reaction mixture was diluted with toluene (30 mL) and water (10 mL). The reaction mixture was again degassed and purged with nitrogen twice, and then the reaction mixture was purged with nitrogen for 5 min and started heating to reflux at 120° C. and stirred for 50 h, TLC analysis (ethyl acetate/hexanes, 3/7, v/v) shows reaction was complete. The reaction mixture was cooled to room temperature, quenched with water (50 mL) and extracted with ethyl acetate (3×75 mL). The organic layers were combined washed with brine (50 mL), dried over anhydrous MgSO$_4$ (10 g), filtered and excess solvent was removed under reduced pressure. The residue and was purified by flash column chromatography (40 g silica gel, eluting with ethyl acetate in hexanes from 0-50%) to furnish 3-cyclopropyl-N-methoxy-N-methyl-5-nitrobenzamide (95c) (1.523 g, 73% yield) as a pale yellow oil; $^1$H NMR (300 MHz, DMSO-d$_6$) δ 8.12 (dd, J=2.2, 1.4 Hz, 1H), 8.03 (t, J=2.0 Hz, 1H), 7.71 (t, J=1.6 Hz, 1H), 3.56 (s, 3H), 3.29 (s, 3H), 2.20 (tt, J=8.3, 5.0 Hz, 1H), 1.14-1.03 (m, 2H), 0.85 (dt, J=6.9, 4.6 Hz, 2H); MS (ES$^+$): MS (ES+) 251.1 (M+1), 273.1 (M+Na).

Step-3: Preparation of
3-Amino-5-cyclopropyl-N-methoxy-N-methylbenzamide
(95d)

To a stirred solution of 3-cyclopropyl-N-methoxy-N-methyl-5-nitrobenzamide (95c) (1.2 g, 4.80 mmol) in anhydrous methanol (25 mL), cooled to 0° C., was added nickel(II) chloride hexahydrate (285 mg, 1.199 mmol) followed by sodium borohydride (499 mg, 13.19 mmol) portionwise over a 30 mins period. The reaction mixture was stirred for 15 min at room temperature. The reaction mixture was quenched with N1-(2-aminoethyl)ethane-1,2-diamine (1.036 mL, 9.59 mmol), stirred for 30 minutes and concentrated in vacuum to dryness. The residue was dissolved in ethyl acetate (25 mL), washed with water (25 mL), brine (25 mL), dried, filtered and concentrated in vacuum. The residue obtained was purified by flash column chromatography (silica gel 12 g, eluting with ethyl acetate/hexanes from 0 to 100%) to furnish 3-Amino-5-cyclopropyl-N-methoxy-N-methylbenzamide (95d) (0.875 g, 3.97 mmol, 83% yield) as a yellow semisolid; $^1$H NMR (300 MHz, DMSO-d$_6$) δ 6.50 (dd, J=2.2, 1.5 Hz, 1H), 6.38 (t, J=1.6 Hz, 1H), 6.34 (t, J=1.9 Hz, 1H), 5.15 (s, 2H), 3.54 (s, 3H), 3.18 (s, 3H), 1.78 (tt, J=8.4, 5.0 Hz, 1H), 0.95-0.82 (m, 2H), 0.67-0.48 (m, 2H); MS (ES+) 221.1 (M+1), 243.1 (M+Na).

Step-4: Preparation of
(3-Amino-5-cyclopropylphenyl)(phenyl)methanone
(95e)

To a stirred solution of 3-amino-5-cyclopropyl-N-methoxy-N-methylbenzamide (95d) (0.875 g, 3.97 mmol) in anhydrous THF (15 mL), cooled to 0° C., was added dropwise phenylmagnesium bromide (8.94 mL, 8.94 mmol). The reaction mixture was stirred at room temperature for 3 h, quenched and with saturated aqueous NH$_4$Cl (25 mL). The reaction mixture was extracted with ethyl acetate (2×25 mL). The organic layers were combined washed brine (25 mL), dried, filtered and concentrated in vacuum. The residue obtained was purified by flash column chromatography (silica gel 12 g, eluting with ethyl acetate/hexanes from 0 to 100%)] to furnish (3-amino-5-cyclopropylphenyl)(phenyl)methanone (95e) (0.15 g, 15.91%) as an yellow oil; $^1$H NMR (300 MHz, DMSO-d$_6$) δ 7.73-7.61 (m, 3H), 7.58-7.51 (m, 2H), 6.70 (dd, J=2.2, 1.5 Hz, 1H), 6.58 (t, J=1.6 Hz, 1H), 6.52 (t, J=1.9 Hz, 1H), 5.31 (s, 2H), 1.84 (tt, J=8.3, 5.0 Hz, 1H), 0.96-0.82 (m, 2H), 0.69-0.52 (m, 2H); MS (ES+) 238.2 (M+1), 260.1 (M+Na); (ES−) 306.1 (M−1).

Step-5: Preparation of
(3-Amino-5-cyclopropylphenyl)(phenyl)methanol
(95f)

To a stirred solution of (3-amino-5-cyclopropylphenyl)(phenyl)methanone (95e) (0.15 g, 0.632 mmol) in methanol (5 mL), cooled to 0° C., was added sodium borohydride (120 mg, 3.16 mmol) portionwise over a 10 mins period. The reaction mixture was stirred for 5 min at room temperature and concentrated in vacuum. The residue obtained was purified by flash column chromatography (silica gel 12 g, eluting with 9:1 ethyl acetate/methanol in hexanes from 0 to 100%)] to furnish (3-amino-5-cyclopropylphenyl)(phenyl)methanol (95f) (0.099 g, 0.414 mmol, 65.4% yield) as a colorless oil; $^1$H NMR (300 MHz, DMSO-d$_6$) δ 7.35-7.23 (m, 4H), 7.23-7.14 (m, 1H), 6.33 (t, J=1.8 Hz, 1H), 6.31 (d, J=1.6 Hz, 1H), 6.06 (t, J=1.9 Hz, 1H), 5.63 (d, J=3.8 Hz, 1H), 5.44 (d, J=3.9 Hz, 1H), 4.88 (s, 2H), 1.70 (tt, J=8.4, 5.1 Hz, 1H), 0.89-0.77 (m, 2H), 0.58-0.39 (m, 2H); MS (ES+) 240.2 (M+1); (ES−) 238.1 (M−1).

Step-6: Preparation of 1-(3-cyanophenyl)-N-(3-cyclopropyl-5-(hydroxy(phenyl)methyl)phenyl)-3-(trifluoromethyl)-1H-pyrazole-5-carboxamide (95g)

To a solution of 1-(3-cyanophenyl)-3-(trifluoromethyl)-1H-pyrazole-5-carboxylic acid (9i) (0.134 g, 0.476 mmol) in DMF (5 mL) was added (3-amino-5-cyclopropylphenyl)(phenyl)methanol (95f) (0.095 g, 0.397 mmol), N-ethyl-N-isopropylpropan-2-amine (0.346 mL, 1.985 mmol) and bromo-tris-pyrrolidino phosphoniumhexafluorophosphate (PyBrop, 0.222 g, 0.476 mmol) at room temperature. The reaction mixture was stirred at room temperature for 37 h under nitrogen atmosphere. The reaction was diluted with water (25 mL) and extracted with ethyl acetate (2×25 mL). The combined organic layer was washed with brine (25 mL), dried, filtered, and evaporated to dryness. The residue obtained was purified by flash column chromatography [silica gel 24 g, eluting with ethyl acetate in hexanes from 0-100%] to furnish 1-(3-cyanophenyl)-N-(3-cyclopropyl-5-(hydroxy(phenyl)methyl)phenyl)-3-(trifluoromethyl)-1H-pyrazole-5-carboxamide (95g) (0.184 g, 0.366 mmol, 92% yield) as a yellow solid; $^1$H NMR (300 MHz, DMSO-d$_6$) δ 10.53 (s, 1H), 8.15 (t, J=1.8 Hz, 1H), 8.00 (dt, J=7.7, 1.3 Hz, 1H), 7.89 (ddd, J=8.2, 2.2, 1.1 Hz, 1H), 7.75 (d, J=8.0 Hz, 1H), 7.70 (d, J=2.6 Hz, 1H), 7.41 (t, J=1.8 Hz, 1H), 7.36-7.25 (m, 4H), 7.25-7.15 (m, 2H), 6.92 (t, J=1.5 Hz, 1H), 5.89 (d, J=3.8 Hz, 1H), 5.61 (d, J=3.7 Hz, 1H), 1.93-1.80 (m, 1H), 0.99-0.82 (m, 2H), 0.63-0.51 (m, 2H); 19F NMR (282 MHz, DMSO) δ −60.99. MS (ES+) 525.2 (M+Na), (ES−) 501.1 (M−1).

Step-7: Preparation of 1-(3-Cyanophenyl)-N-(3-cyclopropyl-5-((cyclopropylmethylamino)(phenyl)methyl)phenyl)-3-(trifluoromethyl)-1H-pyrazole-5-carboxamide (95h)

To a solution of 1-(3-cyanophenyl)-N-(3-cyclopropyl-5-(hydroxy(phenyl)methyl)phenyl)-3-(trifluoromethyl)-1H-pyrazole-5-carboxamide (95g) (0.18 g, 0.358 mmol) in dichloromethane (10 mL) at 0°c was added thionyl chloride (0.065 mL, 0.896 mmol) and allowed to warm to room temperature over 3 h. The reaction mixture was quenched with cyclopropylmethanamine (0.078 mL, 0.896 mmol), stirred for 2 h at room temperature and concentrated in vacuum to dryness. The residue was dissolved in acetonitrile (2.5 mL) and added cyclopropylmethanamine (0.777 mL, 8.96 mmol). The reaction mixture was heated at reflux overnight, cooled to room temperature concentrated in vacuum to dryness. The residue obtained was dissolved in chloroform (25 mL), washed with water (10 mL), dried, filtered and concentrated in vacuum. The residue obtained was purified by flash column chromatography (silica gel 12 g, eluting 0-100% ethyl acetate in hexane) to afford 1-(3-cyanophenyl)-N-(3-cyclopropyl-5-((cyclopropylmethylamino)(phenyl)methyl)phenyl)-3-(trifluoromethyl)-1H-pyrazole-5-carboxamide (95h) (0.122 g, 0.220 mmol, 61.3% yield) as a yellow solid; $^1$H NMR (300 MHz, DMSO-d$_6$) δ 10.53 (s, 1H), 8.15 (t, J=1.8 Hz, 1H), 8.01 (dt, J=7.8, 1.3 Hz, 1H), 7.89 (ddd, J=8.2, 2.2, 1.1 Hz, 1H), 7.75 (d, J=8.0 Hz, 1H), 7.70 (d, J=2.1 Hz, 1H), 7.45 (t, J=1.7 Hz, 1H), 7.42-7.35 (m, 2H), 7.28 (t, J=7.5 Hz, 2H), 7.23-7.13 (m, 2H), 7.00-6.94 (m, 1H), 4.76 (s, 1H), 2.27 (s, 2H), 1.85 (td, J=8.4, 4.3 Hz, 1H), 0.97-0.87 (m, 3H), 0.60-0.54 (m, 2H), 0.42-0.33 (m, 2H), 0.08-0.00 (m, 2H); 19F NMR (282 MHz, DMSO) δ −60.98; MS (ES+) 556.2 (M+1); (ES−) 554.3 (M−1).

Step-8: Preparation of 1-(3-(aminomethyl)phenyl)-N-(3-cyclopropyl-5-((cyclopropylmethylamino)(phenyl) methyl)phenyl)-3-(trifluoromethyl)-1H-pyrazole-5-carboxamide (95i)

To a stirred solution of 1-(3-cyanophenyl)-N-(3-cyclopropyl-5-((cyclopropylmethylamino)(phenyl)methyl)phenyl)-3-(trifluoromethyl)-1H-pyrazole-5-carboxamide (95h) (0.12 g, 0.216 mmol) in anhydrous methanol (10 mL), cooled to 0° C., was added nickel(II) chloride hexahydrate (0.064 g, 0.270 mmol), Sodium borohydride (0.065 g, 1.728 mmol) was added to the reaction mixture in small portions over a 15 min period. The reaction mixture was stirred for 15 min at 0° C. and quenched with N1-(2-aminoethyl)ethane-1,2-diamine (0.07 mL, 0.648 mmol) stirred for 30 mins and concentrated in vacuum to dryness. The residue obtained was dissolved in dichloromethane (25 mL) and water (25 mL). The organic layer was separated, dried, filtered and concentrated in vacuum. The residue obtained was purified by flash column chromatography (silica gel 12 g, eluting with 0-25% methanol in chloroform) to furnish 1-(3-(aminomethyl)phenyl)-N-(3-cyclopropyl-5-((cyclopropylmethylamino)(phenyl)methyl)phenyl)-3-(trifluoromethyl)-1H-pyrazole-5-carboxamide (95i) (0.044 g, 0.079 mmol, 36.4% yield) as a white solid; $^1$H NMR (300 MHz, DMSO-d$_6$) δ 10.57 (s, 1H), 7.55 (s, 1H), 7.51 (d, J=2.2 Hz, 1H), 7.47-7.36 (m, 5H), 7.33-7.23 (m, 3H), 7.22-7.14 (m, 2H), 6.99-6.93 (m, 1H), 4.76 (s, 1H), 3.78 (s, 2H), 2.25 (t, J=8.7 Hz, 4H), 1.85 (tt, J=8.4, 5.0 Hz, 1H), 0.99-0.83 (m, 3H), 0.63-0.51 (m, 2H), 0.48-0.31 (m, 2H), 0.10−−0.01 (m, 2H); MS (ES−) 558.3 (M−1).

Scheme 96

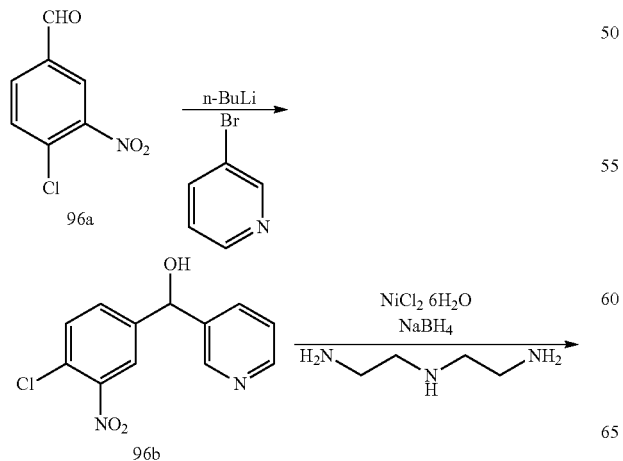

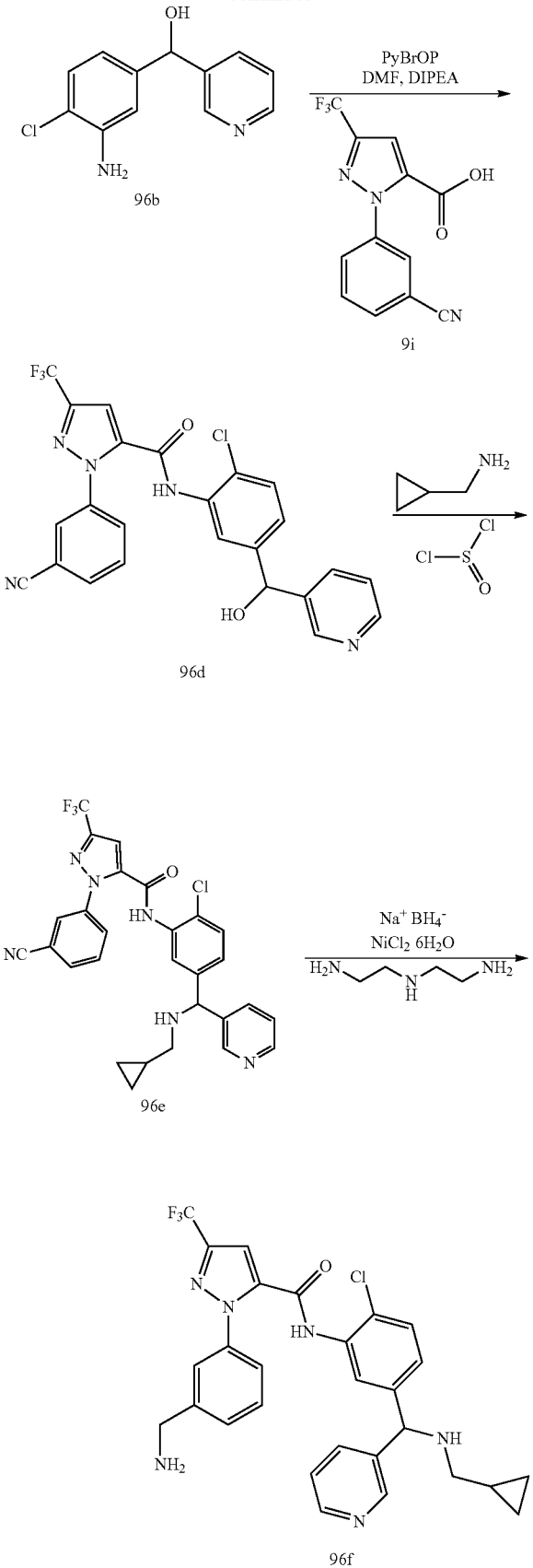

Preparation of 1-(3-(Aminomethyl)phenyl)-N-(2-chloro-5-((cyclopropylmethylamino)(pyridin-3-yl)methyl)phenyl)-3-(trifluoromethyl)-1H-pyrazole-5-carboxamide (96f)

Step-1: Preparation of (4-chloro-3-nitrophenyl)(pyridin-3-yl)methanol (96b)

To a solution of 3-bromopyridine (2.60 mL, 26.9 mmol) in ether (20 mL) at −78° C. was added dropwise n-BuLi (14.31 mL, 22.90 mmol) and stirred for 30 mins at −78° C. To the 3-lithiated pyridine was added dropwise a solution of 4-chloro-3-nitrobenzaldehyde (96a) (5.00 g, 26.9 mmol) in THF (30 mL) at −78° C. and stirred at −78° C. for 2 h and at room temperature for 2 h. The reaction mixture was quenched with saturated ammonium chloride (50 mL). The organic layer was separated, dried, filtered and concentrated in vacuum to dryness. The residue obtained was purified by flash column chromatography (silica gel 80 g, eluting with 0-100% ethyl acetate in hexane) to afford (4-chloro-3-nitrophenyl)(pyridin-3-yl)methanol (96b) (1.5 g, 5.67 mmol, 21.03% yield) as a yellow oil; $^1$H NMR (300 MHz, DMSO-$d_6$) δ 8.66-8.62 (m, 1H), 8.47 (dd, J=4.8, 1.7 Hz, 1H), 8.17-8.11 (m, 1H), 7.79-7.70 (m, 3H), 7.36 (ddd, J=7.9, 4.8, 0.9 Hz, 1H), 6.47 (d, J=4.1 Hz, 1H), 5.93 (d, J=4.1 Hz, 1H); MS (ES+) 265.1 (M+1), (ES−) 263.1 (M−1).

Step-2: Preparation of (3-amino-4-chlorophenyl)(pyridin-3-yl)methanol (96c)

To a stirred solution of (4-chloro-3-nitrophenyl)(pyridin-3-yl)methanol (96b) (1.5 g, 5.67 mmol) in anhydrous methanol (25 mL), cooled to 0° C., was added nickel(II) chloride hexahydrate (0.337 g, 1.417 mmol) followed by sodium borohydride (0.643 g, 17 mmol) portionwise over a 30 mins period. The reaction mixture was stirred for 15 min at room temperature. The reaction mixture was quenched with N1-(2-aminoethyl)ethane-1,2-diamine (1.225 mL, 11.34 mmol) stirred for 30 minutes and concentrated in vacuum to dryness. The residue was dissolved in ethyl acetate (25 mL), washed with water (25 mL), brine (25 mL), dried, filtered and concentrated in vacuum. The residue obtained was purified by flash column chromatography (silica gel 40 g, eluting with ethyl acetate/hexanes from 0 to 100%)] to furnish (3-amino-4-chlorophenyl)(pyridin-3-yl)methanol (96c) (0.119 g, 0.507 mmol, 8.95% yield) as a oil, which was pure enough to be taken to next step; MS (ES+) 235.1 (M+1).

Step-3: Preparation of N-(2-chloro-5-(hydroxy(pyridin-3-yl)methyl)phenyl)-1-(3-cyanophenyl)-3-(trifluoromethyl)-1H-pyrazole-5-carboxamide (96d)

To a solution of 1-(3-cyanophenyl)-3-(trifluoromethyl)-1H-pyrazole-5-carboxylic acid (9i) (0.463 g, 1.648 mmol) in DMF (10 mL) was added (3-amino-4-chlorophenyl)(pyridin-3-yl)methanol (96c) (0.826 g, 3.52 mmol), N-ethyl-N-isopropylpropan-2-amine (3.07 mL, 17.6 mmol) and bromo-tris-pyrrolidino phosphoniumhexafluorophosphate(PyBrOP, 1.969 g, 4.22 mmol) at room temperature. The reaction mixture was stirred at room temperature for 37 h under nitrogen atmosphere. The reaction was diluted with water (25 mL) and extracted with ethyl acetate (2×100 mL). The combined organic layer was washed with brine (50 mL), dried, filtered, and evaporated to dryness. The residue obtained was purified by flash column chromatography (silica gel 40 g, eluting with ethyl acetate in hexanes from 0-100%) to furnish N-(2-chloro-5-(hydroxy(pyridin-3-yl)methyl)phenyl)-1-(3-cyanophenyl)-3-(trifluoromethyl)-1H-pyrazole-5-carboxamide (96d) (0.328 g, 0.659 mmol, 18.72% yield) as a white solid; $^1$H NMR (300 MHz, DMSO-$d_6$) δ 10.54 (s, 1H), 8.61-8.56 (m, 1H), 8.44 (dd, J=4.7, 1.7 Hz, 1H), 8.12 (s, 1H), 8.00 (dt, J=7.8, 1.3 Hz, 1H), 7.95-7.88 (m, 1H), 7.75 (d, J=8.0 Hz, 1H), 7.70 (d, J=3.6 Hz, 2H), 7.55 (s, 1H), 7.51 (d, J=8.3 Hz, 1H), 7.37-7.34 (m, 1H), 7.34-7.31 (m, 1H), 6.26 (d, J=4.1 Hz, 1H), 5.81 (d, J=4.0 Hz, 1H); 19F NMR (282 MHz, DMSO) δ −60.98; MS (ES+) 498.1 (M+1); (ES−) 496.0 (M−1).

Step-4: Preparation of N-(2-Chloro-5-((cyclopropylmethylamino)(pyridin-3-yl)methyl)phenyl)-1-(3-cyanophenyl)-3-(trifluoromethyl)-1H-pyrazole-5-carboxamide (96e)

To a solution of N-(2-chloro-5-(hydroxy(pyridin-3-yl)methyl)phenyl)-1-(3-cyanophenyl)-3-(trifluoromethyl)-1H-pyrazole-5-carboxamide (96d) (0.328 g, 0.659 mmol) in dichloromethane (10 mL) at 0° C. was added thionyl chloride (0.144 mL, 1.976 mmol) and allowed to warm to room temperature over 3 h. The reaction mixture was quenched with cyclopropylmethanamine (0.171 mL, 1.976 mmol), stirred for 2 h at room temperature and concentrated in vacuum to dryness. The residue was dissolved in acetonitrile (5 mL) and added cyclopropylmethanamine (1.429 mL, 16.47 mmol). The reaction mixture was heated at reflux overnight, cooled to room temperature concentrated in vacuum to dryness. The residue obtained was dissolved in chloroform (25 mL), washed with water (10 mL), dried, filtered and concentrated in vacuum. The residue obtained was purified by flash column chromatography (silica gel 24 g, eluting 0-100% ethyl acetate/methanol 9:1 in hexane) to afford N-(2-chloro-5-((cyclopropylmethylamino)(pyridin-3-yl)methyl)phenyl)-1-(3-cyanophenyl)-3-(trifluoromethyl)-1H-pyrazole-5-carboxamide (96e) (0.2 g, 0.363 mmol, 55.1% yield) as a yellow solid; $^1$H NMR (300 MHz, DMSO-$d_6$) δ 10.54 (s, 1H), 8.61 (d, J=2.2 Hz, 1H), 8.45-8.37 (m, 1H), 8.11 (d, J=2.1 Hz, 1H), 8.01 (dt, J=7.7, 1.3 Hz, 1H), 7.92 (d, J=8.3 Hz, 1H), 7.75 (dd, J=15.6, 7.6 Hz, 3H), 7.60 (s, 1H), 7.49 (d, J=8.3 Hz, 1H), 7.41 (dd, J=8.4, 2.0 Hz, 1H), 7.32 (dd, J=7.8, 4.8 Hz, 1H), 4.94 (s, 1H), 2.27 (d, J=6.3 Hz, 2H), 0.97-0.82 (m, 1H), 0.43-0.32 (m, 2H), 0.15-−0.05 (m, 2H); $^{19}$F NMR (282 MHz, DMSO) δ −60.98; MS (ES+) 551.2 (M+1); (ES−) 549.2 (M−1).

Step-5: Preparation of 1-(3-(Aminomethyl)phenyl)-N-(2-chloro-5-((cyclopropylmethylamino)(pyridin-3-yl)methyl)phenyl)-3-(trifluoromethyl)-1H-pyrazole-5-carboxamide (96f)

To a stirred solution of N-(2-chloro-5-((cyclopropylmethylamino)(pyridin-3-yl)methyl)phenyl)-1-(3-cyanophenyl)-3-(trifluoromethyl)-1H-pyrazole-5-carboxamide (96e) (0.2 g, 0.363 mmol) in anhydrous methanol (10 mL), cooled to 0° C., was added nickel(II) chloride hexahydrate (0.108 g, 0.454 mmol), Sodium borohydride (0.11 g, 2.9 mmol) was added to the reaction mixture in small portions over a 15 min period. The reaction mixture was stirred for 15 min at 0° C. and quenched with N1-(2-aminoethyl)ethane-1,2-diamine (0.12 mL, 1.1 mmol) stirred for 30 mins and concentrated in vacuum to dryness. The residue obtained was dissolved in dichloromethane (25 mL) and water (25 mL). The organic layer was separated, dried, filtered and concentrated in vacuum. The residue obtained was purified by flash column chromatography (silica gel 12 g, eluting with 0-25% methanol in chloroform) to furnish 1-(3-(aminomethyl)phenyl)-N-(2-chloro-5-((cyclopropylmethylamino)(pyridin-3-yl)methyl)phenyl)-3-(trifluoromethyl)-1H-pyrazole-5-carboxamide (96f) (0.040 g, 0.072 mmol, 19.85% yield) as a white solid; $^1$H NMR (300 MHz, DMSO-$d_6$) δ 10.38 (s, 1H), 8.67-8.55 (m, 1H), 8.41 (dd, J=4.8, 1.6 Hz, 1H), 7.77 (dt, J=8.0, 1.9 Hz, 1H), 7.66-7.54 (m, 3H), 7.51-7.36 (m, 5H), 7.35-7.28 (m, 1H), 4.93 (s, 1H), 3.87 (s, 2H), 2.27 (d, J=6.6 Hz, 2H), 0.97-0.81 (m, 1H), 0.42-0.31 (m, 2H), 0.11--0.02 (m, 2H); 19F NMR (282 MHz, DMSO) δ -60.77; MS (ES+) 555.2 (M+1); 553.2 (M-1).

Scheme 95

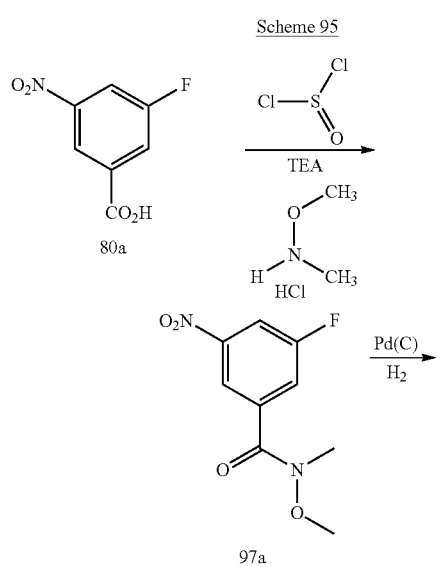

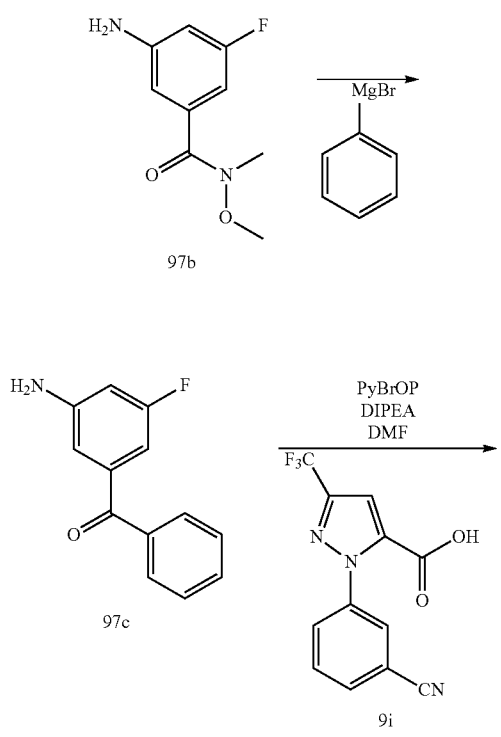

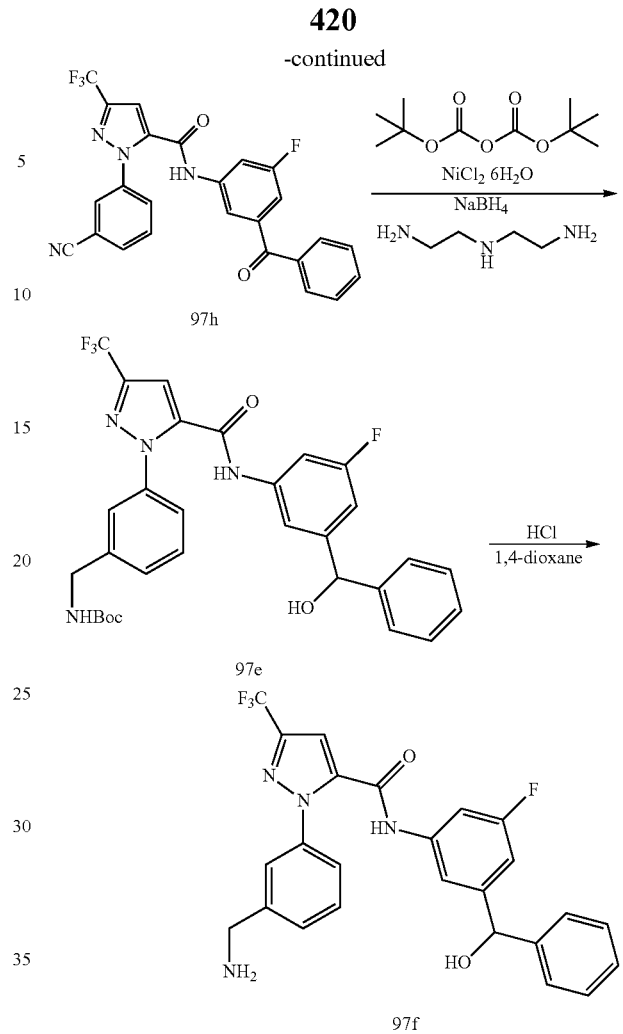

Preparation of 1-(3-(aminomethyl)phenyl)-N-(3-fluoro-5-(hydroxy(phenyl)methyl)phenyl)-3-(trifluoromethyl)-1H-pyrazole-5-carboxamide (97f)

Step-1: Preparation of 3-fluoro-N-methoxy-N-methyl-5-nitrobenzamide (97a)

To a suspension of 3-fluoro-5-nitrobenzoic acid (80a) (2.5 g, 13.51 mmol) in toluene (10 mL) was added thionyl chloride (9.86 mL, 135 mmol) three drops of DMF, heated at reflux for 1 h and evaporated in vacuum to dryness. To this residue was added dichloromethane (10 mL), N,O-dimethylhydroxylamine hydrochloride (1.976 g, 20.26 mmol) and cooled to 0° C. To the solution was added triethylamine (TEA) (9.41 mL, 67.5 mmol) and stirred at room temperature for 16 h. Excess solvent was pumped-off under reduced pressure. The residue was treated with water (75 mL), extracted with ethyl acetate (100 mL, 75 mL). The combined organics were dried over MgSO$_4$ filtered and evaporated to dryness. The residue was purified by flash column chromatography [(silica gel 40 g, eluting with ethyl acetate in hexanes from 0-100%)] furnish (97a) (2.039 g, 66% yield) as light yellow oil; $^1$H NMR (300 MHz, DMSO-$d_6$) δ 8.31-8.23 (m, 2H), 7.97 (ddd, J=8.6, 2.4, 1.4 Hz, 1H), 3.58

(s, 3H), 3.31 (s, 3H); $^{19}$F NMR (282 MHz, DMSO-d$_6$) δ −109.15; MS (ES$^+$): MS (ES+) 229.10 (M+1), 251.1 (M+Na).

Step-2: Preparation of
3-amino-5-fluoro-N-methoxy-N-methylbenzamide
(97b)

To a solution of 3-fluoro-N-methoxy-N-methyl-5-nitrobenzamide (97a) (2 g, 8.77 mmol) in methanol (30 mL) was added palladium (10% Pd on carbon) (0.187 g, 1.753 mmol). The reaction mixture was hydrogenated at 60 psi for 3 h. TLC analysis (ethyl acetate/hexanes, 1:1, v/v) shows reaction was complete. The reaction was filtered through a small Celite© pad, Celite© pad was subsequently washed with methanol (2×25 mL), and ethyl acetate (25 mL). Excess solvents were pumped-off under reduced pressure. The residue was purified by flash column chromatography [(silica gel 80 g, eluting with ethyl acetate in hexanes from 0 to 100%)] to afford 3-amino-5-fluoro-N-methoxy-N-methylbenzamide (97b) (1.624 g, 93% yield) as a colorless oil; $^1$H NMR (300 MHz, DMSO-d$_6$) δ 6.60-6.54 (m, 1H), 6.46-6.42 (m, 1H), 6.41-6.37 (m, 1H), 5.63 (s, 2H, D$_2$O exchangeable), 3.56 (s, 3H), 3.21 (s, 3H); $^{19}$F NMR (282 MHz, DMSO-d$_6$) δ −113.68; MS (ES$^+$): MS (ES+) 199.1 (M+1), 221.1 (M+Na), MS (ES−) 197.1 (M−1).

Step-3: Preparation of
(3-amino-5-fluorophenyl)(phenyl)methanone (97c)

To a solution of 3-amino-5-fluoro-N-methoxy-N-methylbenzamide (97b) (1.6 g, 8.07 mmol) in THF (30 mL) cooled to 0° C. was added dropwise phenylmagnesium bromide (16.39 mL, 16.39 mmol) carefully in a positive flow of nitrogen. The reaction mixture was warmed to room temperature and for 16 h. The reaction was quenched with saturated aqueous NH$_4$Cl (60 mL), product was extracted with ethyl acetate (100 mL, 75 mL). The combined extracts were dried over anhydrous MgSO$_4$, filtered and evaporated to dryness. The residue was purified by flash column chromatography [(silica gel 80 g, eluting with ethyl acetate in hexanes from 0 to 100%)] to afford (3-amino-5-fluorophenyl)(phenyl)methanone (97c) (0.338 g, 19% yield) as a pale yellow solid; $^1$H NMR (300 MHz, DMSO-d$_6$) δ 7.77-7.70 (m, 2H), 7.69-7.64 (m, 1H), 7.56 (tt, J=6.7, 1.5 Hz, 2H), 6.74 (t, J=1.7 Hz, 1H), 6.63-6.51 (m, 2H), 5.79 (s, 2H, D$_2$O exchangeable); $^{19}$F NMR (282 MHz, DMSO-d$_6$) δ −112.89; MS (ES$^+$): MS (ES+) 216.1 (M+1), MS (ES−) 214.1 (M−1).

Step-4: Preparation of N-(3-benzoyl-5-fluorophenyl)-1-(3-cyanophenyl)-3-(trifluoromethyl)-1H-pyrazole-5-carboxamide (97d)

In a 100 mL single-necked flask containing 1-(3-cyanophenyl)-3-(trifluoromethyl)-1H-pyrazole-5-carboxylic acid (9i) (0.510 g, 1.812 mmol), (3-amino-5-fluorophenyl)(phenyl)methanone (97c) (0.325 g, 1.510 mmol), bromo-tris-pyrrolidino phosphoniumhexafluorophosphate(PyBrop) (0.845 g, 1.812 mmol) was added N,N-dimethylformamide (9 mL) and N-ethyl-N-isopropylpropan-2-amine (1.315 mL, 7.55 mmol) successively in a positive flow of nitrogen at room temperature. The resulting reaction mixture was stirred at room temperature for 16 h under nitrogen atmosphere. Excess DMF was pumped-off under reduced pressure. The reaction was diluted with water (50 mL) and extracted with ethyl acetate (2×50 mL); the combined organic layer was dried over anhydrous MgSO$_4$, filtered, and evaporated to dryness. The residue was purified by flash column chromatography [silica gel 25 g, eluting with ethyl acetate in hexanes from 0-100%] to furnish N-(3-benzoyl-5-fluorophenyl)-1-(3-cyanophenyl)-3-(trifluoromethyl)-1H-pyrazole-5-carboxamide (97d) (0.584 g, 1.221 mmol, 81% yield) as a white solid; $^1$H NMR (300 MHz, DMSO-d$_6$) δ 11.04 (s, 1H, D$_2$O exchangeable), 8.21 (t, J=1.9 Hz, 1H), 8.02 (dt, J=7.7, 1.3 Hz, 1H), 7.98-7.89 (m, 2H), 7.83-7.69 (m, 6H), 7.64-7.55 (m, 2H), 7.31 (ddd, J=8.7, 2.5, 1.3 Hz, 1H); $^{19}$F NMR (282 MHz, DMSO-d$_6$) δ −61.00, −110.34; MS (ES$^+$): MS (ES+) 479.2 (M+1), MS (ES−) 512.8 (M+Cl), 955.2 (2M−1).

Step-5: Preparation of tert-butyl 3-(5-(3-fluoro-5-(hydroxy (phenyl) methyl) phenylcarbamoyl)-3-(trifluoromethyl)-1H-pyrazol-1-yl) benzylcarbamate (97e)

To a stirred solution of N-(3-benzoyl-5-fluorophenyl)-1-(3-cyanophenyl)-3-(trifluoromethyl)-1H-pyrazole-5-carboxamide (97d) (0.558 g, 1.166 mmol) in anhydrous methanol (20 mL), cooled to 0° C. was added di-tert-butyl dicarbonate (0.764 g, 3.50 mmol), nickel(II) chloride hexahydrate (0.069 g, 0.292 mmol) followed by sodium borohydride (0.265 g, 7.00 mmol) in small portions over a period of 5 min. The reaction mixture was additionally stirred for 15 min, TLC analysis (ethyl acetate/hexanes, 3/7, v/v) shows reaction was complete at this point N1-(2-aminoethyl) ethane-1; 2-diamine (0.252 mL, 2.333 mmol) was added. The mixture was allowed to stir for 30 minutes and solvent was evaporated under vacuum. The residue was treated with water (25 mL), and extracted with ethyl acetate (2×50 mL). The combined organic layers were dried over MgSO$_4$; filtered and excess solvents were pumped-off under reduced pressure. The residue was purified by flash column chromatography [(silica gel 25 g, eluting with ethyl acetate/hexanes from 0 to 100%)] to furnish tert-butyl 3-(5-(3-fluoro-5-(hydroxy(phenyl)methyl)phenylcarbamoyl)-3-(trifluoromethyl)-1H-pyrazol-1-yl)benzylcarbamate (97e) (0.317 g, 46.5% yield) as a pale yellow solid; $^1$H NMR (300 MHz, DMSO-d$_6$) δ 10.87 (s, 1H, D$_2$O exchangeable), 7.60 (s, 1H), 7.56-7.44 (m, 2H), 7.43-7.27 (m, 9H), 7.27-7.19 (m, 1H), 6.99 (dt, J=9.6, 1.8 Hz, 1H), 6.08 (d, J=3.9 Hz, 1H, D$_2$O exchangeable), 5.68 (d, J=3.8 Hz, 1H), 4.19 (d, J=6.3 Hz, 2H), 1.35 (s, 9H); $^{19}$F NMR (282 MHz, DMSO-d$_6$) δ −60.84, −112.19; MS (ES$^+$): MS (ES+) 607.2 (M+Na), MS (ES−) 583.2 (M−1).

Step-6: Preparation of 1-(3-(aminomethyl)phenyl)-N-(3-fluoro-5-(hydroxy(phenyl)methyl)phenyl)-3-(trifluoromethyl)-1H-pyrazole-5-carboxamide (97f)

To a solution of tert-butyl 3-(5-(3-fluoro-5-(hydroxy(phenyl)methyl)phenylcarbamoyl)-3-(trifluoromethyl)-1H-pyrazol-1-yl)benzylcarbamate (97e) (301 mg, 0.515 mmol) in 1,4-dioxane (5 mL) was added hydrogen chloride (4 M in 1,4-dioxane, 7.47 mL, 29.9 mmol) and stirred at room temperature for 14 h. The reaction was concentrated in vacuum to dryness and the residue was purified by flash column chromatography [(silica gel 25 g, eluting with CMA80 in chloroform from 0-100%)] to furnish 1-(3-(aminomethyl)phenyl)-N-(3-fluoro-5-(hydroxy(phenyl)methyl)phenyl)-3-(trifluoromethyl)-1H-pyrazole-5-carboxamide (97f) (0.177 g, 71% yield) as a white solid; $^1$H NMR (300 MHz, DMSO-d$_6$) δ 10.88 (s, 1H, D$_2$O exchangeable), 7.63 (s, 1H), 7.60 (s, 1H), 7.52-7.47 (m, 2H), 7.46-7.40 (m, 2H), 7.39-7.28 (m, 5H), 7.26-7.19 (m, 1H), 6.99 (d, J=9.5

Hz, 1H), 6.09 (s, 1H, D$_2$O exchangeable), 5.68 (s, 1H), 3.94 (s, 2H); $^{19}$F NMR (282 MHz, DMSO-d$_6$) δ −60.80, −112.18; MS (ES$^+$): MS (ES+) 485.2 (M+1), 969.3 (2M+1), MS (ES−) 483.1 (M−1), 519.2 (M+Cl), 967.3 (2M−1).

Scheme 98

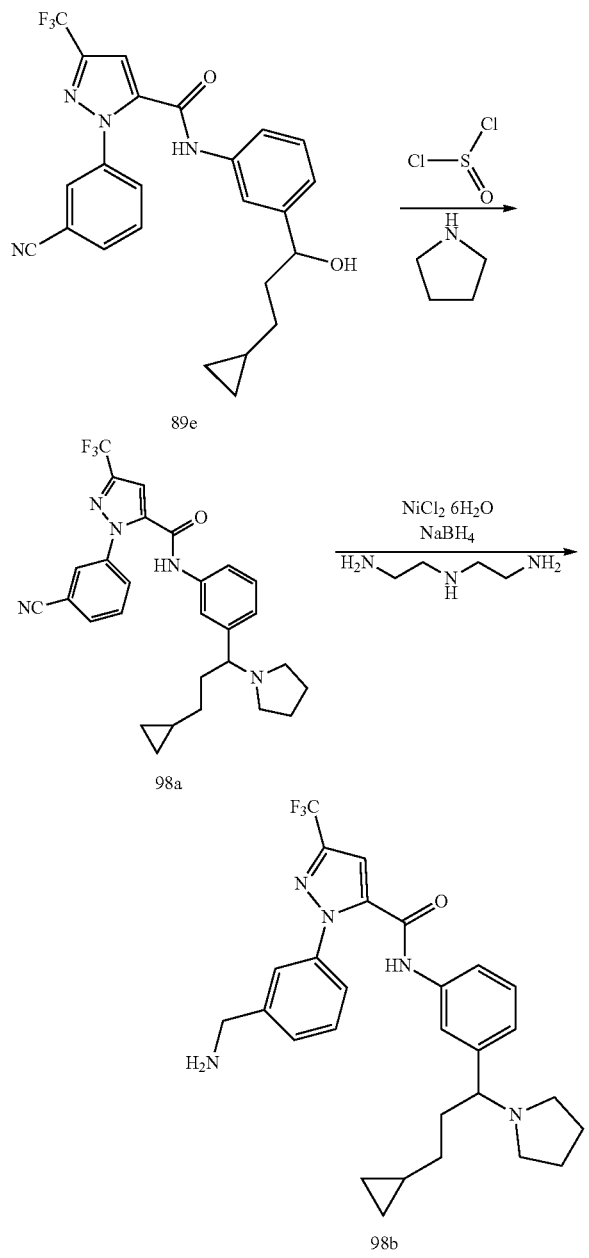

Preparation of 1-(3-cyanophenyl)-N-(3-(3-cyclopropyl-1-(pyrrolidin-1-yl)propyl)phenyl)-3-(trifluoromethyl)-1H-pyrazole-5-carboxamide (98b)

Step-1: Preparation of 1-(3-cyanophenyl)-N-(3-(3-cyclopropyl-1-(pyrrolidin-1-yl)propyl)phenyl)-3-(trifluoromethyl)-1H-pyrazole-5-carboxamide (98a)

To a solution of 1-(3-cyanophenyl)-N-(3-(3-cyclopropyl-1-hydroxypropyl)phenyl)-3-(trifluoromethyl)-1H-pyrazole-5-carboxamide (89e) (0.261 g, 0.574 mmol) in dichloromethane (20 mL) at 0° C. was added thionyl chloride (0.126 mL, 1.723 mmol) and allowed to warm to room temperature over a period of 3 h. The reaction mixture was concentrated in vacuum. The residue was dissolved in N,N dimethyl formamide (20 mL) and added pyrrolidine (1.918 mL, 22.97 mmol). The reaction was heated at reflux for 18 h. TLC analysis shows reaction was complete. Excess solvent was pumped-off under reduced pressure. The residue was diluted with water (30 mL) and extracted with ethyl acetate (2×30 mL). The combined organic layers were dried over anhydrous MgSO$_4$, filtered and evaporated to dryness. The residue was purified by flash column chromatography [silica gel 25 g, eluting with methanol in chloroform from 0-100%] to furnish 1-(3-cyanophenyl)-N-(3-(3-cyclopropyl-1-(pyrrolidin-1-yl)propyl)phenyl)-3-(trifluoromethyl)-1H-pyrazole-5-carboxamide (98a) (97 mg, 33% yield) as a white waxy solid. MS (ES$^+$): MS (ES+) 508.2 (M+1), MS (ES−) 542.2 (M+Na); $^{19}$F NMR (282 MHz, DMSO-d$_6$) δ −60.96.

Step-2: Preparation of 1-(3-(aminomethyl)phenyl)-N-(3-(3-cyclopropyl-1-(pyrrolidin-1-yl)propyl)phenyl)-3-(trifluoromethyl)-1H-pyrazole-5-carboxamide (98b)

To a stirred solution of 1-(3-cyanophenyl)-N-(3-(3-cyclopropyl-1-(pyrrolidin-1-yl)propyl)phenyl)-3-(trifluoromethyl)-1H-pyrazole-5-carboxamide (98a) (0.091 g, 0.179 mmol) in anhydrous methanol (20 mL) cooled to 0° C. was added nickel(II) chloride hexahydrate (0.064 g, 0.269 mmol) followed by sodium borohydride (0.054 g, 1.434 mmol) in small portions over a period of 5 min. The reaction mixture was stirred for 10 min, TLC analysis (methanol/chloroform, 1/9, v/v) shows reaction was complete at this point N1-(2-aminoethyl)ethane-1,2-diamine (0.194 mL, 1.793 mmol) was added. Excess methanol was pumped-off under reduced pressure. The reaction mixture was treated with saturated aqueous NH$_4$Cl (30 mL), and product was extracted with chloroform (2×30 mL). The combined organic layers were dried over MgSO$_4$, filtered and evaporated to dryness. The residue was purified by flash column chromatography [(silica gel 25 g, eluting with methanol/chloroform from 0 to 50%)] to furnish 1-(3-(aminomethyl)phenyl)-N-(3-(3-cyclopropyl-1-(pyrrolidin-1-yl)propyl)phenyl)-3-(trifluoromethyl)-1H-pyrazole-5-carboxamide (98b) (52 mg, 57% yield) as white solid; $^1$H NMR (300 MHz, DMSO-d$_6$) δ 10.65 (s, 1H, D$_2$O exchangeable), 7.65-7.49 (m, 4H), 7.48-7.42 (m, 2H), 7.34 (dt, J=6.2, 2.5 Hz, 1H), 7.25 (t, J=7.8 Hz, 1H), 7.00 (d, J=7.6 Hz, 1H), 3.79 (s, 2H), 3.07 (dd, J=9.4, 3.9 Hz, 1H), 2.27 (s, 3H), 1.92 (s, 1H), 1.64 (d, J=6.1 Hz, 6H), 0.97 (d, J=10.5 Hz, 1H), 0.79 (s, 1H), 0.58 (s, 1H), 0.32 (dd, J=8.2, 1.5 Hz, 2H), −0.08-−0.18 (m, 2H); $^1$H NMR (300 MHz, DMSO-d$_6$ D$_2$O) δ 7.63-7.41 (m, 6H), 7.34 (dt, J=5.3, 2.5 Hz, 1H), 7.27 (t, J=7.8 Hz, 1H), 7.03 (dt, J=7.7, 1.3 Hz, 1H), 3.77 (s, 2H), 3.07 (dd, J=9.7, 4.0 Hz, 1H), 2.28 (d, J=7.7 Hz, 2H), 1.94 (t, J=12.0 Hz, 1H), 1.64 (q, J=6.4, 5.4 Hz, 5H), 0.98 (dt, J=16.5, 6.8 Hz, 1H), 0.77 (s, 1H), 0.58 (p, J=5.9 Hz, 1H), 0.43-0.24 (m, 2H), −0.05-−0.22 (m, 2H); $^{19}$F NMR (282 MHz, DMSO-d$_6$) δ −60.73 (d, J=4.5 Hz); MS (ES+): MS (ES+) 512.3 (M+1), MS (ES−) 510.2 (M−1); Analysis calculated for: C$_{28}$H$_{32}$F$_3$N$_5$O.0.25H$_2$O: C, 65.16; H, 6.35; N, 13.57; Found: C, 64.92; H, 6.24; N, 13.21.

Scheme 99

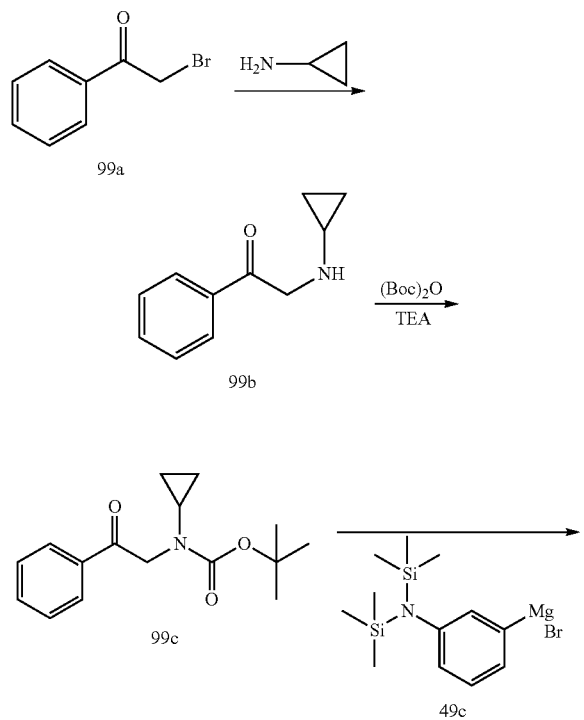

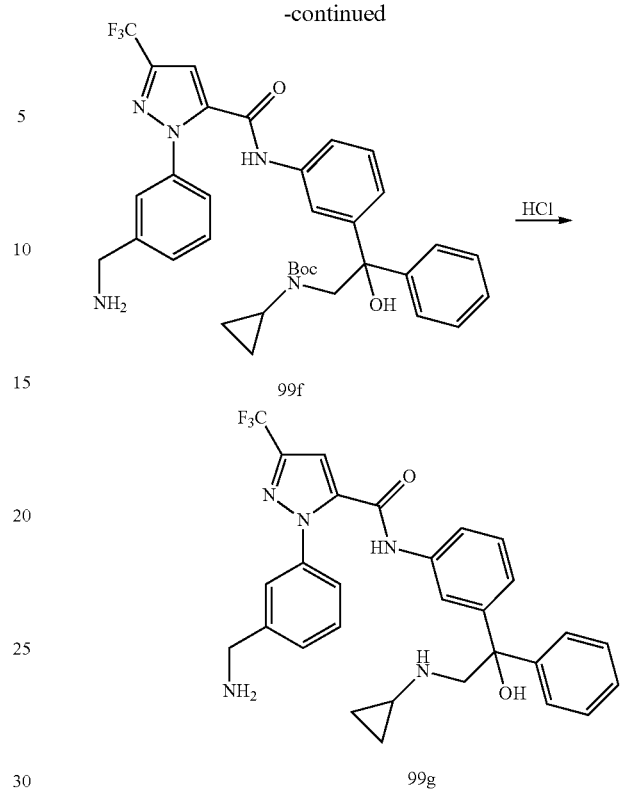

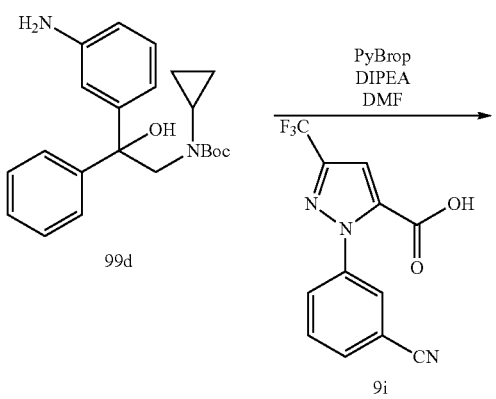

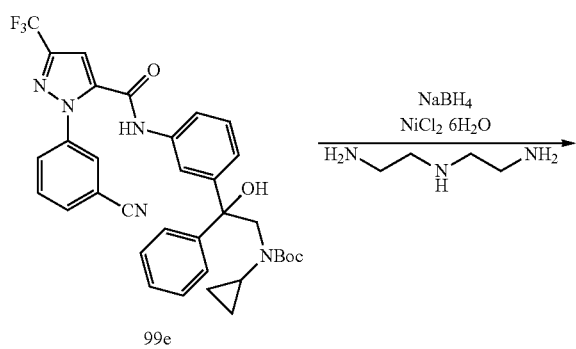

Preparation of 1-(3-(aminomethyl)phenyl)-N-(3-(2-(cyclopropylamino)-1-hydroxy-1-phenylethyl)phenyl)-3-(trifluoromethyl)-1H-pyrazole-5-carboxamide (99g)

Step-1: Preparation of 2-(cyclopropylamino)-1-phenylethanone (99b)

To a stirred solution of 2-bromo-1-phenylethanone (99a) (4 g, 20.10 mmol) in acetonitrile (50 mL) was added cyclopropylamine (2.83 mL, 40.2 mmol) at 0° C. The reaction mixture was allowed to warm to room temperature and stirred overnight. The crude reaction mixture was used as such for next step.

Step-2: Preparation of tert-butyl cyclopropyl(2-oxo-2-phenylethyl)carbamate (99c)

To the solution from Step-1 of 2-(cyclopropylamino)-1-phenylethanone (99b) (3.50 g, 20 mmol) in acetonitrile at 0° C. was added triethylamine (11.15 mL, 80 mmol) and (Boc)$_2$O (4.64 mL, 20.00 mmol). The reaction mixture was stirred for 2 h at room temperature and diluted with water (100 mL). The reaction was extracted with dichloromethane (2×150 mL). The combined organic layer were washed with water (2×50 mL), brine (50 mL) dried and concentrated in vacuum. The crude residue was purified by flash column chromatography (silica gel, 80 g eluting with ethyl acetate in hexanes 0 to 50 to 100%) to afford tert-butyl cyclopropyl (2-oxo-2 phenylethyl)carbamate (99c) (5.5 g, 100%) as a white semisolid; MS (ES+) 298.2 (M+Na).

Step-3: Preparation of tert-butyl 2-(3-aminophenyl)-2-hydroxy-2-phenylethyl(cyclopropyl) carbamate (99d)

To a stirred solution of tert-butyl cyclopropyl(2-oxo-2-phenylethyl)carbamate (99c) (1 g, 3.63 mmol) in tetrahydrofuran (25 mL) cooled to at 0° C. was added (3-(bis(trimethylsilyl)amino) phenyl)magnesium bromide (49c) (4.0 mL, 4.0 mmol). The reaction was allowed to warm to room temperature, stirred for 2 h and quenched by adding ammonium chloride solution (50 mL). The reaction was stirred for 1 h and extracted with ethyl acetate (2×100 mL). The combined organic layer was washed with water (2×50 mL), brine (50 mL), dried, and filtered concentrated in vacuum. The crude residue was purified by flash column chromatography (silica gel 40 g, eluting with ethyl acetate in hexanes 0 to 40% to 100%) to afford tert-butyl 2-(3-aminophenyl)-2-hydroxy-2-phenylethyl(cyclopropyl)carbamate (99d) (460 mg, 34.4%) as a white semisolid; MS (ES+) 391.2 (M+Na), (759.4) (2M+Na).

Step-4: Preparation of tert-butyl 2-(3-(1-(3-cyanophenyl)-3-(trifluoromethyl)-1H-pyrazole-5-carboxamido)phenyl)-2-hydroxy-2-phenylethyl(cyclopropyl)carbamate (99e)

To a solution of 1-(3-cyanophenyl)-3-(trifluoromethyl)-1H-pyrazole-5-carboxylic acid (9i) (0.268 g, 0.954 mmol) in N,N-dimethylformamide (5.76 mL, 74.4 mmol) was added tert-butyl 2-(3-aminophenyl)-2-hydroxy-2-phenylethyl(cyclopropyl)carbamate (99d) (0.422 g, 1.145 mmol), N-ethyl-N-isopropylpropan-2-amine (1.334 mL, 7.64 mmol) and Bromo-tris-pyrrolidino phosphoniumhexafluorophosphate (PyBrOP, 0.489 g, 1.05 mmol) at room temperature. The resulting reaction mixture was stirred at 25° C. for 16 h. The reaction mixture was diluted with water (50 mL). The solid separated was collected by filtration, dried in vacuum and purified by flash column chromatography (silica gel 12 g, eluting with CMA 80 in chloroform 0-100%) to furnish tert-butyl 2-(3-(1-(3-cyanophenyl)-3-(trifluoromethyl)-1H-pyrazole-5-carboxamido)phenyl)-2-hydroxy-2-phenylethyl(cyclopropyl)carbamate (99e) (507 mg, 0.803 mmol, 84% yield) as a white solid; $^1$H NMR (300 MHz, DMSO-$d_6$) δ 10.65 (s, 1H), 8.14 (t, J=1.8 Hz, 1H), 8.00 (dt, J=7.8, 1.3 Hz, 1H), 7.89 (ddd, J=8.2, 2.2, 1.1 Hz, 1H), 7.74 (d, J=8.0 Hz, 1H), 7.70 (d, J=3.0 Hz, 2H), 7.62 (dd, J=7.7, 1.9 Hz, 1H), 7.43 (d, J=7.6 Hz, 2H), 7.33-7.25 (m, 3H), 7.24-7.18 (m, 2H), 5.76 (s, 1H), 4.13-4.00 (m, 2H), 2.27 (s, 1H), 1.21 (s, 9H), 0.50 (d, J=7.2 Hz, 2H), 0.44 (d, J=4.1 Hz, 2H); MS (ES+) 632.3 (M+1), (ES−) 630. 2 (M−1).

Step-5: Preparation of tert-butyl 2-(3-(1-(3-(aminomethyl)phenyl)-3-(trifluoromethyl)-1H-pyrazole-5-carboxamido)phenyl)-2-hydroxy-2-phenylethyl(cyclopropyl)carbamate (99f)

To a stirred solution of tert-butyl 2-(3-(1-(3-cyanophenyl)-3-(trifluoromethyl)-1H-pyrazole-5-carboxamido)phenyl)-2-hydroxy-2-phenylethyl(cyclopropyl)carbamate (99e) (460 mg, 0.728 mmol) in methanol (50 mL) cooled to 0° C. was added nickel(II) chloride hexahydrate (43.3 mg, 0.182 mmol) followed by sodium borohydride (220 mg, 5.83 mmol) in small portions over a period of 15 minutes. Reaction was stirred to cooled to 0° C. for another 15 minutes quenched with N1-(2-aminoethyl)ethane-1,2-diamine (0.787 mL, 7.28 mmol) and stirred for 30 minutes. Reaction was concentrated in vacuum to dryness, diluted with ethyl acetate (50 mL). Ethyl acetate layer was washed with water (50 mL), brine (20 mL), dried and concentrated in vacuum. The crude residue was purified by flash column chromatography (silica gel, 12 g, eluting with CMA 80 in chloroform) to afford tert-butyl 2-(3-(1-(3-(aminomethyl)phenyl)-3-(trifluoromethyl)-1H-pyrazole-5-carboxamido)phenyl)-2-hydroxy-2-phenylethyl(cyclopropyl)carbamate (99f) (0.1 g, 21%) as a white foam; $^1$H NMR (300 MHz, DMSO-$d_6$) δ 10.69 (s, 1H), 7.68 (s, 1H), 7.62-7.57 (m, 1H), 7.54 (s, 1H), 7.51 (s, 1H), 7.46-7.39 (m, 4H), 7.34-7.23 (m, 4H), 7.23-7.17 (m, 2H), 5.74 (s, 1H), 4.04 (q, J=14.1 Hz, 2H), 2.26-2.04 (m, 1H), 1.21 (s, 9H), 0.47 (m, 4H); MS (ES+) 636.3 (M+1); (ES−) 634.2 (M−1).

Step-6: Preparation of 1-(3-(aminomethyl)phenyl)-N-(3-(2-(cyclopropylamino)-1-hydroxy-1-phenylethyl)phenyl)-3-(trifluoromethyl)-1H-pyrazole-5-carboxamide (99g)

To a stirred solution of tert-butyl 2-(3-(1-(3-(aminomethyl)phenyl)-3-(trifluoromethyl)-1H-pyrazole-5-carboxamido)phenyl)-2-hydroxy-2-phenylethyl(cyclopropyl)carbamate (99f) (125 mg, 0.197 mmol) in 1,4-Dioxane (5 mL) was added hydrochloric acid (4 N in 1,4-dioxane, 2.655 mL, 10.62 mmol) at room temperature and stirred overnight at room temperature. Reaction was concentrated, and purified by flash column chromatography (silica gel, 12 g eluting with CMA 80 in chloroform 0-25%) to afford compound (99g) which was repurified by flash column chromatography (silica gel 2×4 g, eluting with CMA 80 in chloroform 0-100%) to afford 1-(3-(aminomethyl)phenyl)-N-(3-(2-(cyclopropylamino)-1-hydroxy-1-phenylethyl)phenyl)-3-(trifluoromethyl)-1H-pyrazole-5-carboxamide (99g) (80 mg, 70.3%) as a colorless solid; $^1$H NMR (300 MHz, DMSO-$d_6$) δ 10.65 (s, 1H, $D_2O$ exchangeable), 7.68 (t, J=2.0 Hz, 1H), 7.53 (dd, J=11.7, 3.1 Hz, 3H), 7.45-7.38 (m, 4H), 7.34-7.21 (m, 4H), 7.17 (q, J=7.2, 5.8 Hz, 2H), 5.50 (s, 1H, $D_2O$ exchangeable), 3.77 (s, 2H), 3.31 (s, 2H), 2.04 (tt, J=6.7, 3.6 Hz, 1H), 0.31 (td, J=6.3, 3.8 Hz, 2H), 0.18 (p, J=3.8 Hz, 2H); MS (ES+) 536.2 (M+1); Analysis calculated for $C_{29}H_{28}F_3N_5O_2$: C, 65.02; H, 5.27; N, 13.08; Found: C, 64.85; H, 5.37; N, 12.74.

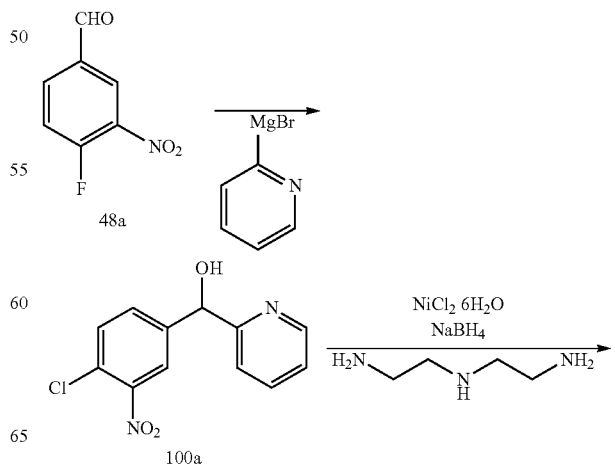

Scheme 100

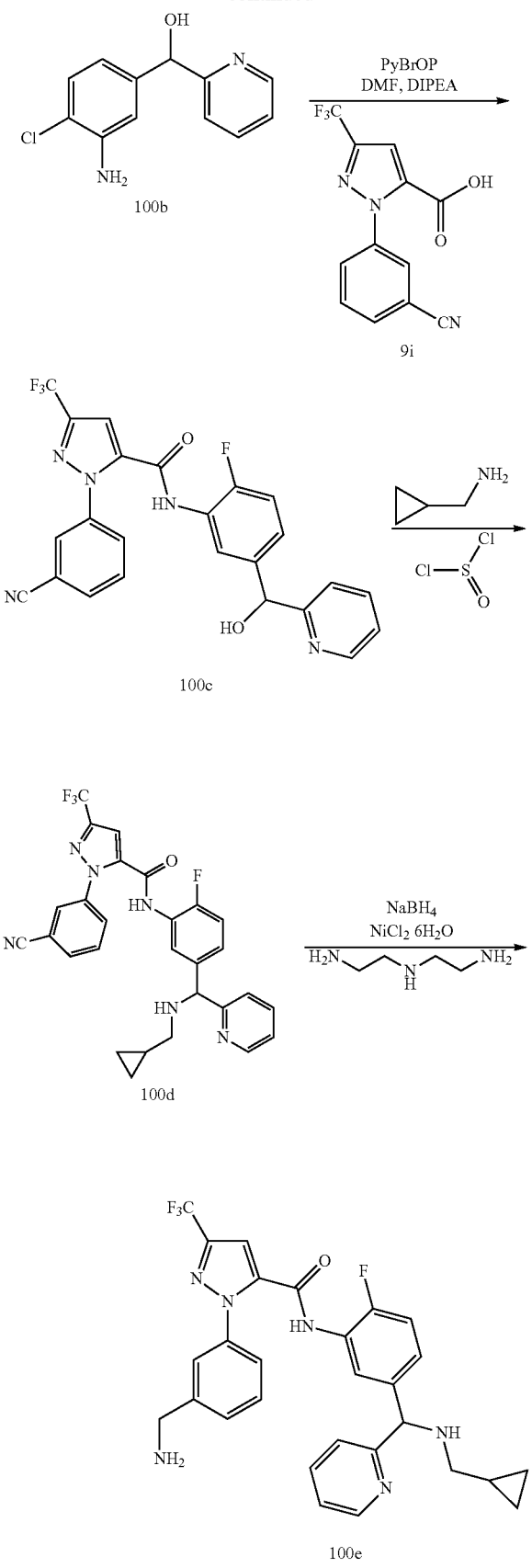

Preparation of 1-(3-(aminomethyl)phenyl)-N-(5-((cyclopropylmethylamino)(pyridin-2-yl)methyl)-2-fluorophenyl)-3-(trifluoromethyl)-1H-pyrazole-5-carboxamide (100e)

Step-1: Preparation of (4-Fluoro-3-nitrophenyl)(pyridin-2-yl)methanol (100a)

To a solution of 4-fluoro-3-nitrobenzaldehyde (48a) (2.1 g, 12.42 mmol) in tetrahydrofuran (50 mL) cooled to 0° C. was added pyridin-2-ylmagnesium bromide (2.264 g, 12.42 mmol), stirred at 0° C. for 3 h and at room temperature for 14 h, TLC analysis (ethyl acetate/hexanes, 1/1, v/v) shows reaction was complete. The reaction mixture was quenched with saturated aqueous NH$_4$Cl (60 mL), extracted with EtOAc (2×75 mL). The combined extracts were washed with brine (50 mL), dried over anhydrous MgSO$_4$, filtered, and evaporated to dryness. The residue was purified by flash column chromatography [(silica gel 40 g, eluting with ethyl acetate/hexanes from 0 to 50%)] to furnish (4-Fluoro-3-nitrophenyl)(pyridin-2-yl)methanol (100a) (0.366 g, 12% yield) as a yellow solid; $^1$H NMR (300 MHz, DMSO-d$_6$) δ 8.49 (ddd, J=4.8, 1.8, 0.9 Hz, 1H), 8.18 (ddd, J=7.4, 2.3, 0.7 Hz, 1H), 7.87-7.77 (m, 2H), 7.66-7.48 (m, 2H), 7.27 (ddd, J=7.6, 4.8, 1.2 Hz, 1H), 6.50 (d, J=4.5 Hz, 1H), 5.85 (d, J=4.5 Hz, 1H); $^{19}$F NMR (282 MHz, DMSO-d$_6$) δ −121.56; MS (ES$^+$): MS (ES+) 271.0 (M+Na), MS (ES−) 247.1 (M−1), 495.1 (2M−1).

Step-2: Preparation of (3-Amino-4-fluorophenyl)(pyridin-2-yl)methanol (100b)

To a stirred solution of (4-fluoro-3-nitrophenyl)(pyridin-2-yl)methanol (100a) (1.345 g, 5.42 mmol) in anhydrous methanol (30 mL) cooled to 0° C. was added nickel(II) chloride hexahydrate (0.322 g, 1.355 mmol) followed by sodium borohydride (0.615 g, 16.26 mmol) in small portions over a period of 5 min. The reaction mixture was stirred for 20 min at 0° C. TLC analysis (methanol/chloroform, 2/8, v/v) shows reaction was complete at this point N1-(2-aminoethyl)ethane-1,2-diamine (5.85 mL, 54.2 mmol) was added. The mixture was allowed to stir for 30 mins and concentrated in vacuum to dryness. The residue was treated water (50 mL), and extracted with ethyl acetate (2×50 mL). The organic layers were combined dried over anhydrous MgSO$_4$, filtered, and excess solvents were pumped-off under reduced pressure. The residue was purified by flash column chromatography [(silica gel 25 g, eluting with ethyl acetate/hexanes from 0 to 50%)] to furnish (3-Amino-4-fluorophenyl)(pyridin-2-yl)methanol (100b) (1.008 g, 85% yield) as a yellow oil; $^1$H NMR (300 MHz, DMSO-d$_6$) δ 8.43 (ddd, J=4.8, 1.8, 0.9 Hz, 1H), 7.76 (td, J=7.7, 1.8 Hz, 1H), 7.50 (dt, J=8.0, 1.1 Hz, 1H), 7.22 (ddd, J=7.5, 4.8, 1.2 Hz, 1H), 6.97-6.71 (m, 2H), 6.53 (ddd, J=8.3, 4.5, 2.1 Hz, 1H), 5.95 (d, J=4.0 Hz, 1H), 5.53 (d, J=4.0 Hz, 1H), 5.07 (s, 2H, D$_2$O exchangeable); $^{19}$F NMR (282 MHz, DMSO-d$_6$) δ −137.67; MS (ES$^+$): MS (ES+) 241.1 (M+Na), MS (ES+) 217.1 (M−1).

Step-3: Preparation of 1-(3-cyanophenyl)-N-(2-fluoro-5-(hydroxy(pyridin-2-yl)methyl)phenyl)-3-(trifluoromethyl)-1H-pyrazole-5-carboxamide (100c)

In a 100 mL single-necked flask containing 1-(3-cyanophenyl)-3-(trifluoromethyl)-1H-pyrazole-5-carboxylic acid (9i) (1.489 g, 5.3 mmol), (3-amino-4-fluorophenyl)(pyridin-2-yl)methanol (100c) (0.963 g, 4.41 mmol), bromo-trispyrrolidino phosphoniumhexafluorophosphate(PyBrop) (2.469 g, 5.30 mmol) was added N,N-dimethylformamide (DMF 27 mL) and N-ethyl-N-isopropylpropan-2-amine (DIPEA) (3.84 mL, 22.06 mmol) successively in a positive flow of nitrogen at room temperature. The resulting reaction mixture was stirred at room temperature for 16 h under a positive flow of nitrogen atmosphere. Excess DMF was pumped-off under reduced pressure. The residue was treated with water (30 mL), and extracted with chloroform (2×50 mL). The combined organic layers were dried over anhydrous $MgSO_4$, filtered, evaporated to dryness. The residue was purified by flash column chromatography [silica gel 40 g, eluting with methanol in chloroform from 0-100%] to furnish 1-(3-cyanophenyl)-N-(2-fluoro-5-(hydroxy(pyridin-2-yl)methyl)phenyl)-3-(trifluoromethyl)-1H-pyrazole-5-carboxamide (100c) (1.114 g, 52% yield) as a yellow solid; $^1$H NMR (300 MHz, DMSO-$d_6$) δ 10.54 (s, 1H, $D_2O$ exchangeable), 8.45 (ddd, J=4.8, 1.9, 0.9 Hz, 1H), 8.19-8.08 (m, 1H), 8.00 (dt, J=7.8, 1.3 Hz, 1H), 7.94-7.86 (m, 1H), 7.83-7.68 (m, 3H), 7.55 (d, J=7.7 Hz, 2H), 7.35-7.17 (m, 3H), 6.22 (d, J=4.2 Hz, 1H, $D_2O$ exchangeable), 5.69 (d, J=4.2 Hz, 1H); $^{19}$F NMR (282 MHz, DMSO-$d_6$) δ −60.98, −123.06; IR (KBr, cm$^{-1}$): 2236 cm$^{-1}$ (—CN stretching); MS (ES$^+$): MS (ES+) 482.1 (M+1), MS (ES−) 480.25 (M−1).

Step-4: Preparation of 1-(3-cyanophenyl)-N-(5-((cyclopropylmethylamino)(pyridin-2-yl)methyl)-2-fluorophenyl)-3-(trifluoromethyl)-1H-pyrazole-5-carboxamide (100d)

To a solution of 1-(3-cyanophenyl)-N-(2-fluoro-5-(hydroxy(pyridin-2-yl)methyl)phenyl)-3-(trifluoromethyl)-1H-pyrazole-5-carboxamide (100c) (0.814 g, 1.691 mmol) in dichloromethane (20 mL) at 0° C. was added thionyl chloride (0.370 mL, 5.07 mmol), warmed to room temperature and stirred for 12 h. The reaction mixture was quenched with cyclopropylmethanamine (0.724 mL, 8.45 mmol) stirred for 1 h at room temperature, and concentrated in vacuum to dryness. The residue was dissolved in cyclopropylmethanamine (2.90 mL, 33.8 mmol) and acetonitrile (20 mL) and the reaction mixture was heated at 100° C. for 16 h TLC analysis (CHCl$_3$/MeOH, 9/1, v/v) shows reaction was complete, reaction mixture was evaporated to dryness. The residue was purified by flash column chromatography (silica gel 40 g, eluting 0-100% methanol in chloroform from 0-100%) to afford 1-(3-cyanophenyl)-N-(5-((cyclopropylmethylamino)(pyridin-2-yl)methyl)-2-fluorophenyl)-3-(trifluoromethyl)-1H-pyrazole-5-carboxamide (100d) (696 mg, 77% yield) as a yellow solid; $^1$H NMR (300 MHz, DMSO-$d_6$) δ 10.54 (s, 1H, $D_2O$ exchangeable), 8.55-8.41 (m, 1H), 8.18-8.08 (m, 1H), 8.00 (dt, J=7.7, 1.4 Hz, 1H), 7.94-7.86 (m, 1H), 7.80-7.69 (m, 3H), 7.57 (dd, J=7.5, 2.2 Hz, 1H), 7.45 (d, J=7.9 Hz, 1H), 7.32 (ddd, J=8.5, 4.9, 2.1 Hz, 1H), 7.27-7.14 (m, 2H), 4.93 (s, 1H), 3.01-2.68 (m, 1H, $D_2O$ exchangeable), 2.29 (qd, J=12.1, 6.6 Hz, 2H), 1.03-0.76 (m, 1H), 0.48-0.30 (m, 2H), 0.03 (dt, J=7.6, 4.4 Hz, 2H); $^{19}$F NMR (282 MHz, DMSO-$d_6$) δ −60.98, −123.05; IR (KBr, cm$^{-1}$): 2235 cm$^{-1}$ (—CN stretching); MS (ES$^+$): MS (ES+) 535.2 (M+1), MS (ES−) 533.2 (M−1).

Step-5: Preparation of 1-(3-(aminomethyl)phenyl)-N-(5-((cyclopropylmethylamino)(pyridin-2-yl)methyl)-2-fluorophenyl)-3-(trifluoromethyl)-1H-pyrazole-5-carboxamide (100e)

To a stirred solution of 1-(3-cyanophenyl)-N-(5-((cyclopropylmethylamino)(pyridin-2-yl)methyl)-2-fluorophenyl)-3-(trifluoromethyl)-1H-pyrazole-5-carboxamide (100d) (0.651 g, 1.218 mmol) in anhydrous methanol (30 mL) cooled to 0° C. was added nickel(II) chloride hexahydrate (0.434 g, 1.827 mmol) followed by sodium borohydride (0.369 g, 9.74 mmol) in small portions over a period of 5 min. The reaction mixture was stirred for 10 min, TLC analysis (methanol/chloroform, 1/9, v/v) shows reaction was complete at this point N1-(2-aminoethyl)ethane-1,2-diamine (1.316 mL, 12.18 mmol) was added. Excess methanol was pumped-off under reduced pressure. The reaction mixture was treated with saturated aqueous $NH_4Cl$ (30 mL), and product was extracted with chloroform (2×30 mL). The combined organic layers were dried over $MgSO_4$, filtered and evaporated to dryness. The residue was purified by flash column chromatography [(silica gel 40 g, eluting with methanol/chloroform from 0 to 50%)] to furnish 1-(3-(aminomethyl)phenyl)-N-(5-((cyclopropylmethylamino)(pyridin-2-yl)methyl)-2-fluorophenyl)-3-(trifluoromethyl)-1H-pyrazole-5-carboxamide (100e) (267 mg, 41% yield) free base as a white solid; $^1$H NMR (300 MHz, DMSO-$d_6$) δ 10.55 (s, 1H, $D_2O$ exchangeable), 8.47 (dt, J=4.6, 1.5 Hz, 1H), 7.74 (td, J=7.7, 1.8 Hz, 1H), 7.60 (d, J=9.2 Hz, 2H), 7.54 (s, 1H), 7.49-7.40 (m, 3H), 7.39-7.26 (m, 2H), 7.26-7.16 (m, 2H), 4.91 (s, 1H), 3.82 (s, 2H), 2.39-2.19 (m, 2H), 0.99-0.79 (m, 1H), 0.51-0.22 (m, 2H), 0.04 (dd, J=5.4, 3.5 Hz, 2H); $^{19}$F NMR (282 MHz, DMSO-$d_6$) δ −60.76, −123.48; MS (ES$^+$): MS (ES+) 539.2 (M+1), MS (ES−) 573.2 (M+Cl), 537.2 (M−1); Analysis calculated for: $C_{28}H_{26}F_4N_6O\cdot0.75H_2O$: C, 60.92; H, 5.02; N, 15.22; Found: C, 60.84; H, 4.99; N, 14.93.

To a solution of free base of 1-(3-(aminomethyl)phenyl)-N-(5-((cyclopropylmethylamino)(pyridin-2-yl)methyl)-2-fluorophenyl)-3-(trifluoromethyl)-1H-pyrazole-5-carboxamide (100e) (0.228 g, 0.423 mmol) in IPA (10 mL) was added conc. HCl (0.176 mL, 2.117 mmol) and concentrated in vacuum to dryness. The residue was dried in vacuum to remove excess HCl and dissolved in IPA (2 mL) with heating to solubilize. To the homogenous solution was added ether (40 mL) and heated at reflux for 30 mins. After cooling to room temperature the solid obtained was collected by filtration, washed with ether and dried under vacuum to furnish 1-(3-(aminomethyl)phenyl)-N-(5-((cyclopropylmethylamino)(pyridin-2-yl)methyl)-2-fluorophenyl)-3-(trifluoromethyl)-1H-pyrazole-5-carboxamide (0.230 g, 84% yield) hydrochloride salt as a white solid; $^1$H NMR (300 MHz, Deuterium Oxide) δ 8.65 (d, J=4.9 Hz, 1H), 7.84 (t, J=7.4 Hz, 1H), 7.77 (d, J=6.4 Hz, 1H), 7.67-7.56 (m, 4H), 7.50-7.29 (m, 5H), 5.71 (s, 1H), 4.27 (s, 2H), 2.93 (d, J=7.4 Hz, 2H), 1.15-1.02 (m, 1H), 0.73-0.56 (m, 2H), 0.37-0.17 (m, 2H); $^{19}$F NMR (282 MHz, $D_2O$) 6-62.36, −121.61; MS (ES+) 539.3 (M+1); (ES−) 537.2 (M−1); Analysis calculated for $C_{28}H_{26}F_4N_6O\cdot2.4HCl\cdot2H_2O$: C, 50.79; H, 4.93; Cl, 12.85; N, 12.69; Found: C, 50.79; H, 5.05; Cl, 12.82; N, 12.33.

Scheme 101

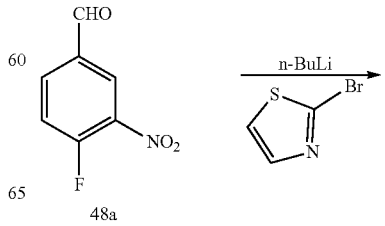

48a

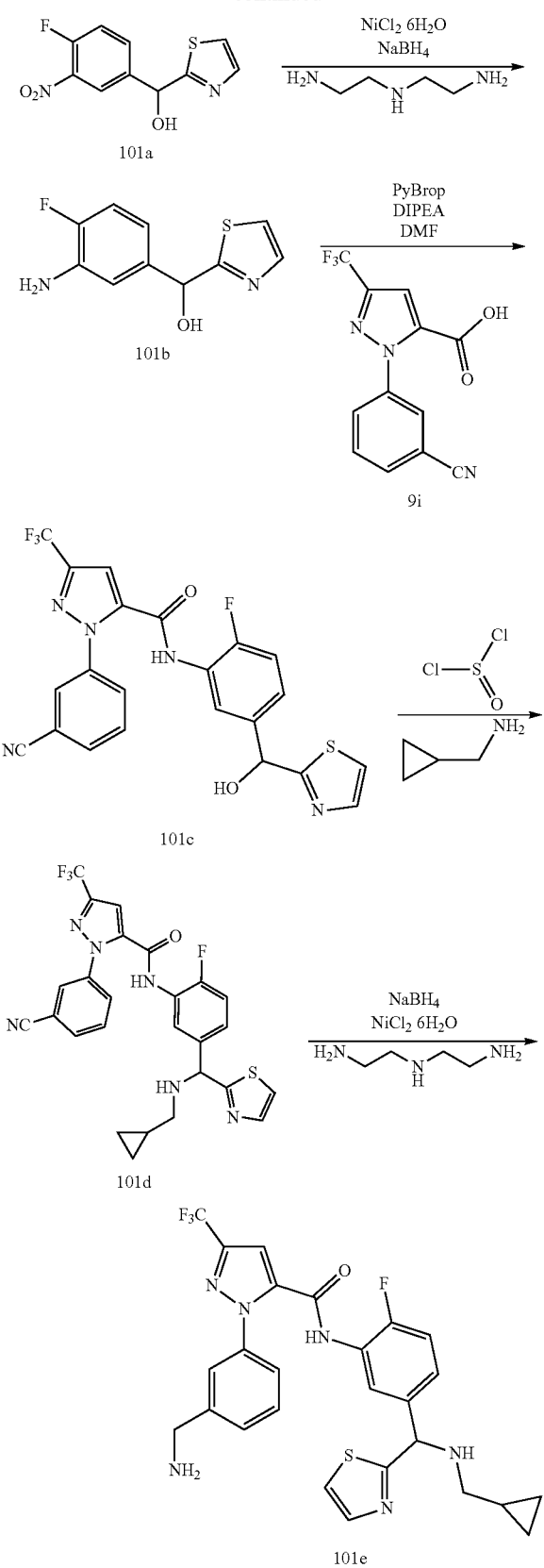

Preparation of 1-(3-(Aminomethyl)phenyl)-N-(5-((cyclopropylmethylamino)(thiazol-2-yl)methyl)-2-fluorophenyl)-3-(trifluoromethyl)-1H-pyrazole-5-carboxamide (101e)

Step-1: Preparation of (4-Fluoro-3-nitrophenyl)(thiazol-2-yl)methanol (101a)

To a solution of 2-bromothiazole (4.8 mL, 52.2 mmol) in ether (36 mL) at −78° C. was added dropwise n-BuLi ((33.0 mL, 52.9 mmol) and stirred for 30 mins at −78° C. To the 2-lithiated thiazole anion was added dropwise a solution of 4-fluoro-3-nitrobenzaldehyde (48a) (8.83 g, 52.2 mmol) in THF (54 mL) at −78° C. and stirred at −78° C. for 2 h and at room temperature for 2 h. The reaction mixture was quenched with saturated ammonium chloride (80 mL). The organic layer was separated, dried, filtered and concentrated in vacuum to dryness. The residue obtained was purified by flash column chromatography (silica gel 120 g, eluting with 0-100% ethyl acetate in hexane) to afford (4-fluoro-3-nitrophenyl)(thiazol-2-yl)methanol (101a) (3.5 g, 26%) as a brown solid; $^1$H NMR (300 MHz, DMSO-d$_6$) δ 8.27-8.19 (m, 1H), 7.89 (dddd, J=8.7, 4.4, 2.3, 0.6 Hz, 1H), 7.75 (d, J=3.2 Hz, 1H), 7.69 (d, J=3.2 Hz, 1H), 7.59 (dd, J=11.3, 8.6 Hz, 1H), 7.22 (d, J=4.9 Hz, 1H), 6.14 (dd, J=4.8, 0.9 Hz, 1H); $^{19}$F NMR (282 MHz, DMSO) δ −120.63; MS (ES+) 277.0 (M+Na), (ES−) 253.0 (M−1).

Step-2: Preparation of (3-Amino-4-fluorophenyl)(thiazol-2-yl)methanol (101b)

To a stirred solution of (4-fluoro-3-nitrophenyl)(thiazol-2-yl)methanol (101a) (2.8 g, 11.01 mmol) in anhydrous methanol (50 mL), cooled to 0° C., was added nickel(II) chloride hexahydrate (3.27 g, 13.77 mmol) followed by sodium borohydride (1.25 g, 33 mmol) portionwise over a 30 mins period. The reaction mixture was stirred for 15 min at room temperature. The reaction mixture was quenched with N1-(2-aminoethyl)ethane-1,2-diamine (3.57 mL, 33 mmol) stirred for 30 minutes and concentrated in vacuum to dryness. The residue was dissolved in ethyl acetate (50 mL) and water (50 mL). The organic layer was separated washed with brine (25 mL), dried, filtered and concentrated in vacuum. The residue obtained was purified by flash column chromatography (silica gel 40 g, eluting with ethyl acetate/hexanes 0 to 100%)] to furnish (3-amino-4-fluorophenyl)(thiazol-2-yl)methanol (101b) (1.234 g, 5.50 mmol, 50.0% yield) as an off white solid; $^1$H NMR (300 MHz, DMSO-d$_6$) δ 7.68 (d, J=3.2 Hz, 1H), 7.61 (d, J=3.2 Hz, 1H), 6.91 (dd, J=11.5, 8.3 Hz, 1H), 6.83 (dd, J=8.9, 2.2 Hz, 1H), 6.63 (d, J=4.1 Hz, 1H), 6.60-6.52 (m, 1H), 5.77 (d, J=4.1 Hz, 1H), 5.14 (s, 2H); 19F NMR (282 MHz, DMSO) δ −136.87; MS(ES+) 247.1 (M+Na); (ES−) 223.0 (M−1).

Step-3: Preparation of 1-(3-Cyanophenyl)-N-(2-fluoro-5-(hydroxy(thiazol-2-yl)methyl)phenyl)-3-(trifluoromethyl)-1H-pyrazole-5-carboxamide (101c)

To a solution of 1-(3-cyanophenyl)-3-(trifluoromethyl)-1H-pyrazole-5-carboxylic acid (9i) (1.547 g, 5.50 mmol) in DMF (32.5 mL) was added (3-amino-4-fluorophenyl)(thiazol-2-yl)methanol (101b) (1.234 g, 5.50 mmol), N-ethyl-N-isopropylpropan-2-amine (4.79 mL, 27.5 mmol) and bromo-tris-pyrrolidino phosphoniumhexafluorophosphate (PyBrOP, 3.08 g, 6.60 mmol) at room temperature. The reaction mixture was stirred at room temperature for 37 h, quenched with water (100 mL) and extracted with ethyl acetate (2×100 mL). The organic layers were combined washed with water (2×50 mL), brine (50 mL), dried, filtered, and evaporated to dryness. The residue obtained was purified by flash column chromatography (silica gel 40 g, eluting with ethyl acetate in hexanes from 0-100%) to furnish 1-(3-cyanophenyl)-N-(2-fluoro-5-(hydroxy(thiazol-2-yl)methyl)phenyl)-3-(trifluoromethyl)-1H-pyrazole-5-carboxamide (101c) (1.01 g, 2.072 mmol, 37.7% yield) as a white solid; $^1$H NMR (300 MHz, DMSO-d$_6$) δ 10.58 (s, 1H), 8.13 (s, 1H), 8.00 (dt, J=7.8, 1.3 Hz, 1H), 7.93-7.87 (m, 1H), 7.76-7.69 (m, 3H), 7.66-7.58 (m, 2H), 7.39-7.21 (m, 2H), 6.92 (d, J=4.4 Hz, 1H), 5.95 (d, J=4.4 Hz, 1H); MS(ES+) 488.1 (M+1); 510.1 (M+Na).

Step-4: Preparation of 1-(3-Cyanophenyl)-N-(5-((cyclopropylmethylamino)(thiazol-2-yl)methyl)-2-fluorophenyl)-3-(trifluoromethyl)-1H-pyrazole-5-carboxamide (101d)

To a solution of 1-(3-cyanophenyl)-N-(2-fluoro-5-(hydroxy(thiazol-2-yl)methyl)phenyl)-3-(trifluoromethyl)-1H-pyrazole-5-carboxamide (101c) (0.75 g, 1.539 mmol) in dichloromethane (25 mL) at 0° C. was added thionyl chloride (0.337 mL, 4.62 mmol) and stirred at room temperature for 2 h. The reaction mixture was quenched with cyclopropylmethanamine (0.4 mL, 4.62 mmol) and stirred at room temperature for additional 5 h. The reaction mixture was concentrated in vacuum to dryness. The residue obtained was dissolved in acetonitrile (10 mL) and added cyclopropylmethanamine (2.67 mL, 30.8 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum. The residue obtained was purified by flash column chromatography (silica gel 40 g, eluting 0-25% methanol in chloroform) to afford 1-(3-cyanophenyl)-N-(5-((cyclopropylmethylamino)(thiazol-2-yl)methyl)-2-fluorophenyl)-3-(trifluoromethyl)-1H-pyrazole-5-carboxamide (101d) (0.22 g, 0.407 mmol, 26.5% yield) as a light yellow solid; $^1$H NMR (300 MHz, DMSO-d$_6$) δ 10.58 (s, 1H), 8.13 (d, J=2.1 Hz, 1H), 8.00 (dt, J=7.8, 1.3 Hz, 1H), 7.94-7.86 (m, 1H), 7.77-7.70 (m, 2H), 7.66 (d, J=3.2 Hz, 1H), 7.61 (d, J=3.3 Hz, 1H), 7.62-7.55 (m, 1H), 7.41-7.30 (m, 1H), 7.26 (dd, J=10.3, 8.5 Hz, 1H), 5.19 (s, 1H), 2.98 (s, 1H), 2.37 (d, J=6.0 Hz, 3H), 0.98-0.82 (m, 1H), 0.43-0.34 (m, 2H), 0.11-0.02 (m, 2H); $^{19}$F NMR (282 MHz, DMSO-d$_6$) δ −60.98, −122.16; MS (ES+) 541.2 (M+1).

Step-5: Preparation of 1-(3-(Aminomethyl)phenyl)-N-(5-((cyclopropylmethylamino)(thiazol-2-yl)methyl)-2-fluorophenyl)-3-(trifluoromethyl)-1H-pyrazole-5-carboxamide (101e)

To a solution of 1-(3-cyanophenyl)-N-(5-((cyclopropylmethylamino)(thiazol-2-yl)methyl)-2-fluorophenyl)-3-(trifluoromethyl)-1H-pyrazole-5-carboxamide (101d) (0.2 g, 0.370 mmol) in MeOH (20 mL) cooled with ice/water was added nickel(II) chloride hexahydrate (0.110 g, 0.463 mmol) followed by portionwise addition of sodium borohydride (0.07 g, 1.85 mmol) over a period of 15 min. The reaction mixture was stirred at room temperature for 1 h and quenched with N1-(2-aminoethyl)ethane-1,2-diamine (0.120 mL, 1.110 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over MgSO$_4$ filtered and concentrated in vacuum. The residue obtained was purified by flash column chromatography (silica gel 24 g, eluting with 0-25% chloroform/methanol) to furnish 1-(3-(aminomethyl)phenyl)-N-(5-((cyclopropylmethylamino)(thiazol-2-yl)methyl)-2-fluorophenyl)-3-(trifluoromethyl)-1H-pyrazole-5-carboxamide (101e) (0.07 g, 0.129 mmol, 34.7% yield) as a yellow solid; $^1$H NMR (300 MHz, DMSO-d$_6$) δ 10.49 (s, 1H), 7.63-7.48 (m, 4H), 7.45 (s, 1H), 7.42-7.23 (m, 5H), 7.25-7.12 (m, 1H), 5.11 (s, 1H), 3.73 (s, 2H), 2.94 (s, 2H), 2.29 (dd, J=6.7, 2.3 Hz, 2H), 0.93-0.77 (m, 1H), 0.37-0.27 (m, 2H), 0.04-−0.05 (m, 2H); $^{19}$F NMR (282 MHz, DMSO) δ −60.75, −122.60; MS (ES+) 545.3 (M+1); (ES−) 543.2 (M−1); Analysis calculated for C$_{26}$H$_{24}$F$_4$N$_6$OS.0.25H$_2$O: C, 56.87; H, 4.50; N, 15.31; S, 5.84; Found: C, 57.04; H, 4.74; N, 14.65; S, 4.86.

Scheme 102

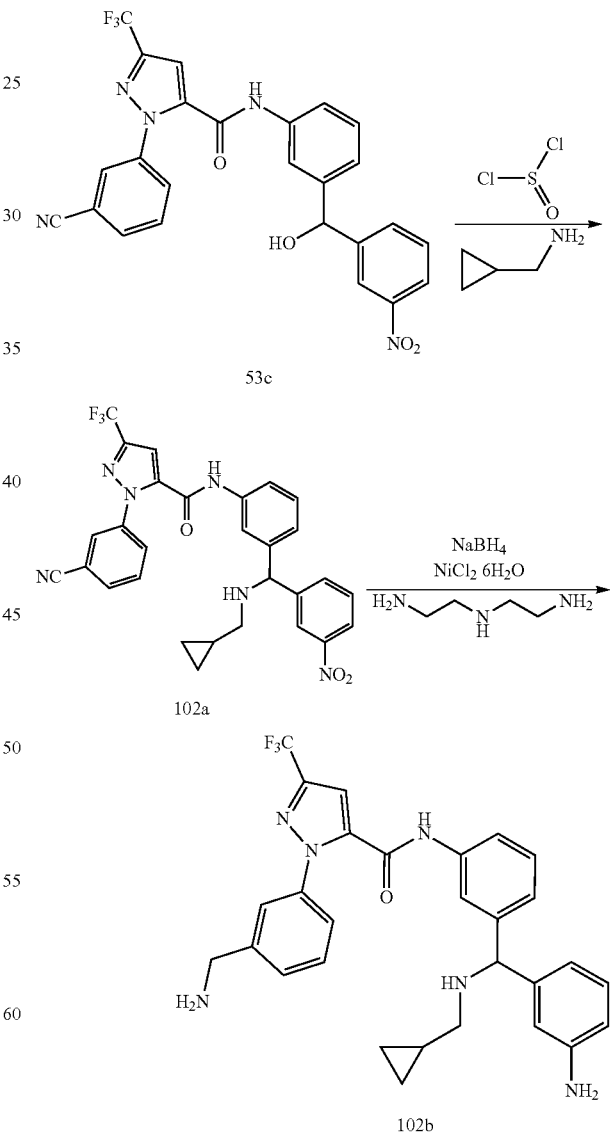

Preparation of 1-(3-(aminomethyl)phenyl)-N-(3-((3-aminophenyl)(cyclopropyl-methylamino)methyl)phenyl)-3-(trifluoromethyl)-1H-pyrazole-5-carboxamide (102b)

Step-1: Preparation of 1-(3-cyanophenyl)-N-(3-((cyclopropylmethylamino)(3-nitrophenyl)methyl)phenyl)-3-(trifluoromethyl)-1H-pyrazole-5-carboxamide (102a)

To a solution of 1-(3-cyanophenyl)-N-(3-(hydroxy(3-nitrophenyl)methyl)phenyl)-3-(trifluoromethyl)-1H-pyrazole-5-carboxamide (53c) (0.6 g, 1.182 mmol) in dichloromethane (20 mL) at 0° C. was added thionyl chloride (0.250 mL, 3.38 mmol) and stirred at room temperature for 2 h. The reaction mixture was quenched with triethyl amine (1.450 mL, 10.41 mmol) stirred at room temperature for 1 h, added cyclopropylmethanamine (1.751 g, 23.89 mmol) and stirred at room temperature for additional 5 h. The reaction mixture was concentrated in vacuum to remove dichloromethane. To the reaction mixture was acetonitrile (10 mL) and added cyclopropylmethanamine (1.751 g, 23.89 mmol). The reaction mixture was heated at reflux overnight, cooled to room temperature and concentrated in vacuum to dryness. The residue was dissolved in chloroform (120 mL), washed with water (60 mL), dried, filtered and concentrated in vacuum. The residue obtained was purified by flash column chromatography (silica gel 40 g, eluting with hexanes/ethyl acetate 1:0 to 2:1) to give 1-(3-cyanophenyl)-N-(3-((cyclopropylmethylamino)(3-nitrophenyl)methyl)phenyl)-3-(trifluoromethyl)-1H-pyrazole-5-carboxamide (102a) (132 mg, 20%) as a yellow gum; $^1$H NMR (300 MHz, DMSO-$d_6$) δ 10.67 (s, 1H), 8.31 (t, J=2.0 Hz, 1H), 8.16 (t, J=1.8 Hz, 1H), 8.07 (ddd, J=8.2, 2.4, 1.0 Hz, 1H), 8.00 (dt, J=7.7, 1.3 Hz, 1H), 7.90 (ddd, J=8.3, 2.2, 1.1 Hz, 1H), 7.88-7.83 (m, 1H), 7.78-7.66 (m, 3H), 7.60 (t, J=8.0 Hz, 2H), 7.33-7.20 (m, 2H), 5.02 (s, 1H), 2.36-2.22 (m, 2H), 1.01-0.87 (m, 1H), 0.45-0.32 (m, 2H), 0.09-0.02 (m, 2H); $^{19}$F NMR (282 MHz, DMSO-$d_6$) δ −60.97; MS (ES+) 561.3 (M+1).

Step-2: Preparation of 1-(3-(aminomethyl)phenyl)-N-(3-((3-aminophenyl)(cyclopropylmethylamino)methyl)phenyl)-3-(trifluoromethyl)-1H-pyrazole-5-carboxamide (102b)

To a solution of 1-(3-cyanophenyl)-N-(3-((cyclopropylmethylamino)(3-nitrophenyl)methyl)phenyl)-3-(trifluoromethyl)-1H-pyrazole-5-carboxamide (102a) (123 mg, 0.219 mmol) in MeOH (5 mL) cooled with ice/water was added nickel(II) chloride (66.0 mg, 0.278 mmol) followed by addition of Sodium borohydride (51.0 mg, 1.321 mmol) in portions over 5 min and stirred at room temperature for 1 h. The reaction mixture was treated N1-(2-aminoethyl)ethane-1,2-diamine (0.08 mL, 0.733 mmol) stirred at room temperature for 0.5 h and concentrated in vacuum to dryness. The residue was treated with ethyl acetate (100 mL), washed with water (60 mL). The aqueous phase was extracted again with ethyl acetate (60 mL). The combined extracts were washed with brine (60 mL), dried over MgSO$_4$ followed by filtration and concentration. The crude product was purified by flash column chromatography [silica gel, eluting with chloroform/CMA80 (1:0 to 1:1)] to give 1-(3-(aminomethyl)phenyl)-N-(3-((3-aminophenyl)(cyclopropylmethylamino)methyl)phenyl)-3-(trifluoromethyl)-1H-pyrazole-5-carboxamide (102b) (47 mg, 40%) as a colorless gum; $^1$H NMR (300 MHz, DMSO-$d_6$) δ 10.65 (s, 1H), 7.59 (s, 1H), 7.53 (s, 1H), 7.49-7.09 (m, 7H), 6.86 (t, J=7.7 Hz, 1H), 6.57-6.52 (m, 1H), 6.49 (d, J=7.8 Hz, 1H), 6.32 (dd, J=7.9, 2.2 Hz, 1H), 4.95 (s, 2H), 4.57 (s, 1H), 3.73 (s, 2H), 2.23 (d, J=6.7 Hz, 2H), 2.06 (bs, 2H), 0.95-0.77 (m, 1H), 0.40-0.25 (m, 2H), 0.04−−0.03 (m, 2H); $^{19}$F NMR (282 MHz, DMSO-$d_6$) δ −60.71; MS (ES+): 535.29 (M+1).

Scheme 103

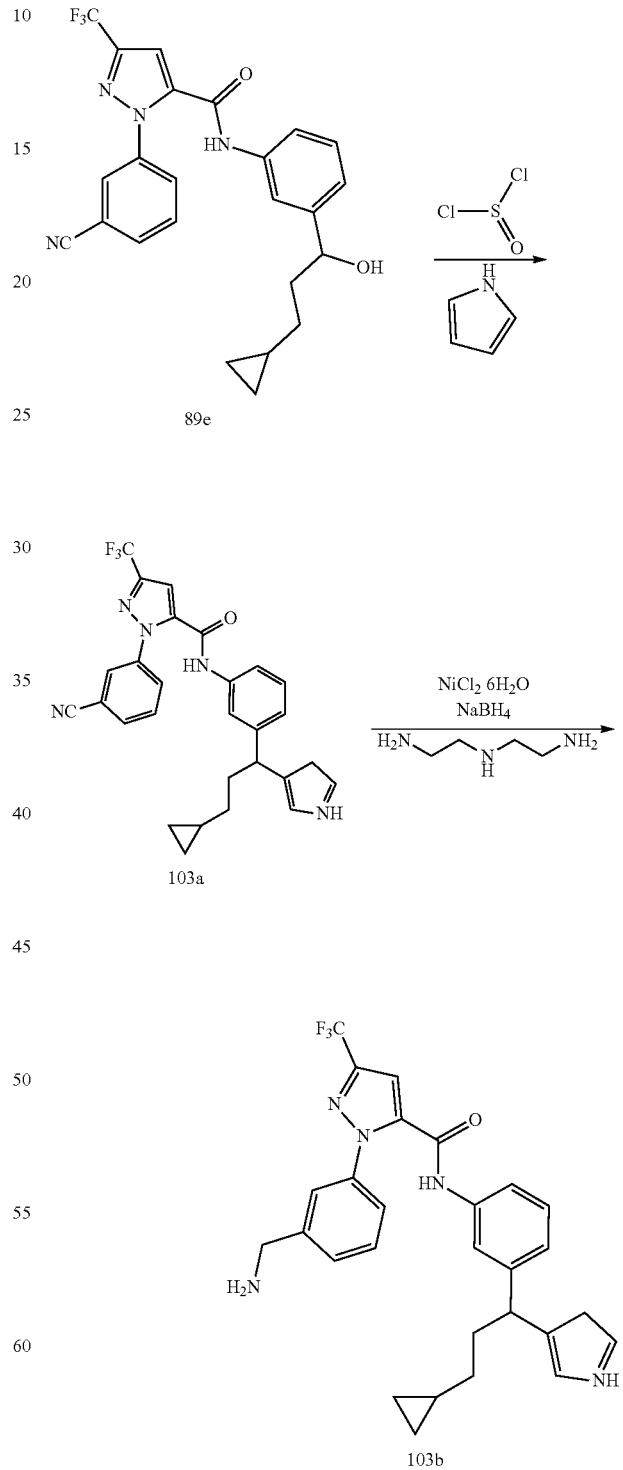

Preparation of 1-(3-(aminomethyl)phenyl)-N-(3-(3-cyclopropyl-1-(1H-pyrrol-3-yl)propyl)phenyl)-3-(trifluoromethyl)-1H-pyrazole-5-carboxamide (103b)

Step-1: Preparation of 1-(3-cyanophenyl)-N-(3-(3-cyclopropyl-1-(1H-pyrrol-3-yl)propyl)phenyl)-3-(trifluoromethyl)-1H-pyrazole-5-carboxamide (103a)

To a solution of 1-(3-cyanophenyl)-N-(3-(3-cyclopropyl-1-hydroxypropyl)phenyl)-3-(trifluoromethyl)-1H-pyrazole-5-carboxamide (89e) (0.602 g, 1.325 mmol) in dichloromethane (20 mL) at 0° C. was added thionyl chloride (0.290 mL, 3.97 mmol) and stirred at room temperature for 3 h. The reaction was evaporated to dryness and residue dissolved in N,N dimethyl formamide (20 mL). To the solution was added 1H-pyrrole (3.68 mL, 53.0 mmol) and heated to reflux for 18 h. Additional 1H-pyrrole (3.68 mL, 53.0 mmol) was added and reaction heated at reflux for 54 h. Excess solvent was pumped-off under reduced pressure. The residue was diluted with water (50 mL) and extracted with chloroform (2×50 mL). The combined organics were dried over anhydrous $MgSO_4$, filtered, evaporated to dryness. The residue was purified by flash column chromatography [silica gel 25 g, eluting with methanol in chloroform from 0-100%] to furnish 1-(3-cyanophenyl)-N-(3-(3-cyclopropyl-1-(1H-pyrrol-3-yl)propyl)phenyl)-3-(trifluoromethyl)-1H-pyrazole-5-carboxamide (103a) (0.063 g, 0.125 mmol, 9.45% yield) as a white waxy solid; MS (ES+) 504.34 (M+1), MS (ES−) 526.30 (M+Na), MS (ES−) 502.03 (M−1); $^{19}F$ NMR (282 MHz, DMSO-$d_6$) δ −60.94.

Step-2: Preparation of 1-(3-(aminomethyl)phenyl)-N-(3-(3-cyclopropyl-1-(1H-pyrrol-3-yl)propyl)phenyl)-3-(trifluoromethyl)-1H-pyrazole-5-carboxamide (103b)

To a stirred solution of 1-(3-cyanophenyl)-N-(3-(3-cyclopropyl-1-(1H-pyrrol-3-yl)propyl)phenyl)-3-(trifluoromethyl)-1H-pyrazole-5-carboxamide (103a) (55 mg, 0.109 mmol) in anhydrous methanol (10 mL) cooled to 0° C. was added nickel(II) chloride hexahydrate (0.039 g, 0.164 mmol) followed by sodium borohydride (0.033 g, 0.874 mmol) in small portions over a period of 5 min. The reaction mixture was stirred for 10 min, quenched with N1-(2-aminoethyl)ethane-1,2-diamine (0.118 mL, 1.092 mmol), stirred for 30 mins and concentrated in vacuum to dryness. The reaction mixture was treated with saturated aqueous $NH_4Cl$ (30 mL), and product was extracted with chloroform (2×30 mL). The combined organic layers were dried over $MgSO_4$, filtered and evaporated to dryness. The residue was purified by flash column chromatography (silica gel 25 g, eluting with methanol/chloroform from 0 to 100%) to furnish 1-(3-(aminomethyl)phenyl)-N-(3-(3-cyclopropyl-1-(1H-pyrrol-3-yl)propyl)phenyl)-3-(trifluoromethyl)-1H-pyrazole-5-carboxamide (103b) (21 mg, 38% yield) as an off-white solid.

$^1H$ NMR (300 MHz, DMSO-$d_6$) δ 10.63 (s, 1H, $D_2O$ exchangeable), 10.53-10.42 (m, 1H, $D_2O$ exchangeable), 7.56 (s, 1H), 7.54-7.51 (m, 1H), 7.49-7.41 (m, 4H), 7.32 (dt, J=6.2, 2.6 Hz, 1H), 7.20 (t, J=8.1 Hz, 1H), 7.00 (dt, J=7.8, 1.3 Hz, 1H), 6.61 (q, J=2.4 Hz, 1H), 6.51 (q, J=2.0 Hz, 1H), 5.86 (q, J=2.3 Hz, 1H), 3.78 (s, 2H), 3.72 (t, J=7.7 Hz, 1H), 2.09-1.80 (m, 2H), 1.08 (tdd, J=16.9, 13.8, 7.2 Hz, 2H), 0.65 (ddt, J=10.1, 7.2, 3.7 Hz, 1H), 0.45-0.25 (m, 2H), −0.02--0.15 (m, 2H); $^{19}F$ NMR (282 MHz, DMSO-$d_6$) δ −60.71; MS (ES+) 508.3 (M+1), MS (ES−) 506.0 (M−1).

Scheme 104

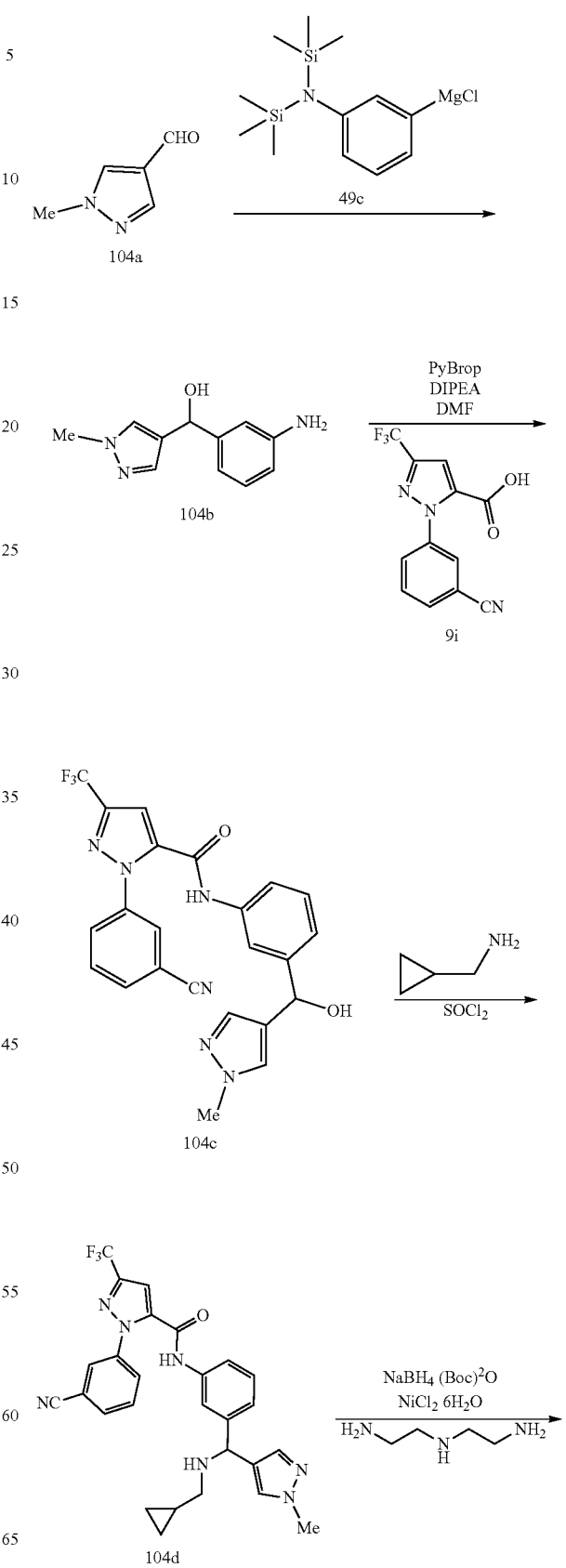

-continued

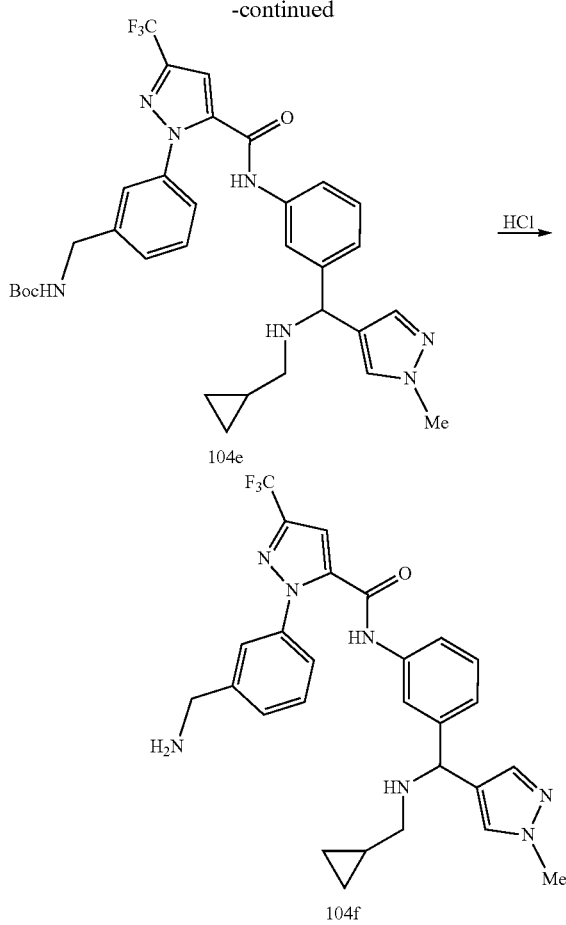

Preparation of 1-(3-(aminomethyl)phenyl)-N-(3-((cyclopropylmethylamino)(1-methyl-1H-pyrazol-4-yl)methyl)phenyl)-3-(trifluoromethyl)-1H-pyrazole-5-carboxamide (104f)

Step-1: Preparation of (3-aminophenyl)(1-methyl-1H-pyrazol-4-yl)methanol (104b)

To a solution of 1-methyl-1H-pyrazole-4-carbaldehyde (104a) (4.8 g, 43.6 mmol) in tetrahydrofuran (80 mL) was cooled to 0° C. was added dropwise (3-(bis(trimethylsilyl)amino)phenyl)magnesium chloride (49c) (49.0 mL, 49.0 mmol) and stirred at 0° C. for 2 h. The reaction was quenched with saturated aqueous NH$_4$Cl (120 mL) and extracted with ethyl acetate (2×120 mL). The combined organic extracts were washed with brine (100 mL), dried over MgSO$_4$ followed by filtration and concentration. The residue was dissolved in ether (200 mL), treated with 4 N HCl in 1,4-dioxane (24 mL) and stirred at room temperature for 2 h. The solid obtained was collected by filtration washed with ether, dried under vacuum to give (3-aminophenyl)(1-methyl-1H-pyrazol-4-yl)methanol (104b) (6.01 g, 68%) as an off-white solid; $^1$H NMR (300 MHz, DMSO-d$_6$) δ 7.47 (s, 1H), 7.46-7.20 (m, 5H), 5.69 (s, 1H), 3.76 (s, 3H); MS (ES+) 204.1 (M+1).

Step-2: Preparation of 1-(3-cyanophenyl)-N-(3-(hydroxy(1-methyl-1H-pyrazol-4-yl)methyl)phenyl)-3-(trifluoromethyl)-1H-pyrazole-5-carboxamide (104c)

To a solution of 1-(3-cyanophenyl)-3-(trifluoromethyl)-1H-pyrazole-5-carboxylic acid (9i) (4.15 g, 14.76 mmol) in DMF (80 mL) was added (3-aminophenyl)(1-methyl-1H-pyrazol-4-yl)methanol (104b) (2.99 g, 14.76 mmol), N-ethyl-N-isopropylpropan-2-amine (21.00 mL, 121 mmol), bromotripyrrolidin-1-ylphosphonium hexafluorophosphate(V) (PyBrOP, 7.02 g, 14.76 mmol) and stirred at room temperature for 13 h. The reaction mixture was diluted with ethyl acetate (300 mL), washed with water (2×120 mL) brine (120 mL), dried over MgSO$_4$, filtered and concentrated in vacuum to dryness. The crude product was purified by flash column chromatography [silica gel 120 g, eluting with hexanes/ethyl acetate (1:0 to 0:1)] to give 1-(3-cyanophenyl)-N-(3-(hydroxy(1-methyl-1H-pyrazol-4-yl)methyl)phenyl)-3-(trifluoromethyl)-1H-pyrazole-5-carboxamide (104c) (2.9 g, 42%) as a light brown gum; $^1$H NMR (300 MHz, DMSO-d$_6$) δ 10.64 (s, 1H), 8.17 (t, J=1.8 Hz, 1H), 8.01 (dt, J=7.8, 1.3 Hz, 1H), 7.95 (s, 1H), 7.91 (ddd, J=8.2, 2.2, 1.1 Hz, 1H), 7.73 (t, J=0.9 Hz, 1H), 7.63 (t, J=1.9 Hz, 1H), 7.59-7.54 (m, 1H), 7.41 (s, 1H), 7.28 (t, J=7.8 Hz, 1H), 7.21 (d, J=0.8 Hz, 1H), 7.16-7.10 (m, 1H), 5.67 (d, J=4.3 Hz, 1H), 5.61 (d, J=4.4 Hz, 1H), 3.75 (s, 3H); $^{19}$F NMR (282 MHz, DMSO-d$_6$) δ −60.97; MS (ES+) 467.2 (M+1).

Step-3: Preparation of 1-(3-cyanophenyl)-N-(3-((cyclopropylmethylamino)(1-methyl-1H-pyrazol-4-yl)methyl)phenyl)-3-(trifluoromethyl)-1H-pyrazole-5-carboxamide (104d)

To a solution of 1-(3-cyanophenyl)-N-(3-(hydroxy(1-methyl-1H-pyrazol-4-yl)methyl)phenyl)-3-(trifluoromethyl)-1H-pyrazole-5-carboxamide (104c) (2.836 g, 6.08 mmol) in dichloromethane (100 mL) at 0° C. was added thionyl chloride (1.100 mL, 14.87 mmol) and stirred at room temperature for 2 h. The reaction mixture was treated with triethyl amine (7.00 mL, 50.2 mmol) and stirred at room temperature for 1 h. It was then treated with cyclopropylmethanamine (8.00 g, 109 mmol) and concentrated to remove most of dichloromethane followed by addition of acetonitrile (75 mL). The reaction mixture was stirred at 70° C. for 20 h and concentrated to dryness. The residue was treated with chloroform (240 mL), washed with water (100 mL), dried over MgSO$_4$ followed by filtration and concentration. The crude product was purified by flash column chromatography [silica gel 40 g, eluting with chloroform/methanol (1:0 to 19:1)] to give 1-(3-cyanophenyl)-N-(3-((cyclopropylmethylamino)(1-methyl-1H-pyrazol-4-yl)methyl)phenyl)-3-(trifluoromethyl)-1H-pyrazole-5-carboxamide (104d) (1.518 g, 48%) as a brown solid, $^1$H NMR (300 MHz, DMSO-d$_6$) δ 10.64 (s, 1H), 8.17 (t, J=1.8 Hz, 1H), 8.01 (dt, J=7.8, 1.3 Hz, 1H), 7.91 (ddd, J=8.2, 2.2, 1.1 Hz, 1H), 7.79-7.69 (m, 2H), 7.63 (s, 1H), 7.58-7.52 (m, 1H), 7.46 (s, 1H), 7.32-7.22 (m, 2H), 7.16 (d, J=7.8 Hz, 1H), 4.74 (s, 1H), 3.74 (s, 3H), 2.35-2.15 (m, 2H), 0.96-0.78 (d, J=9.7 Hz, 1H), 0.43-0.27 (m, 2H), 0.09--0.020-0.00 (m, 2H); $^{19}$F NMR (282 MHz, DMSO-d$_6$) δ −60.96; MS (ES+) 520.3 (M+1).

Step-4: Preparation of tert-butyl 3-(5-(3-((cyclopropylmethylamino)(1-methyl-1H-pyrazol-4-yl)methyl)phenylcarbamoyl)-3-(trifluoromethyl)-1H-pyrazol-1-yl)benzylcarbamate (104e)

To a solution of 1-(3-cyanophenyl)-N-(3-((cyclopropylmethylamino)(1-methyl-1H-pyrazol-4-yl)methyl)phenyl)-

3-(trifluoromethyl)-1H-pyrazole-5-carboxamide (104d) (1.453 g, 2.8 mmol) in MeOH (40 mL) cooled with ice/water was added di-tert-butyl dicarbonate (1.850 g, 8.39 mmol), nickel(II) chloride hexahydrate (0.360 g, 1.513 mmol) followed by addition of Sodium borohydride (1.083 g, 28.1 mmol) slowly over 5 min and stirred at room temperature for 1 h. The reaction mixture quenched with N1-(2-aminoethyl)ethane-1,2-diamine (1.400 mL, 12.83 mmol), stirred at room temperature for 0.5 h and concentrated in vacuum to dryness. The residue was treated with ethyl acetate (200 mL) and washed with water (100 mL). The aqueous phase was extracted again with ethyl acetate (100 mL). The combined organic extracts were washed with brine (100 mL), dried over MgSO$_4$ followed by filtration and concentration. The crude product was purified by flash column chromatography [silica gel, eluting with chloroform/methanol (1:0 to 19:1) to give tert-butyl 3-(5-(3-((cyclopropylmethylamino)(1-methyl-1H-pyrazol-4-yl)methyl)phenylcarbamoyl)-3-(trifluoromethyl)-1H-pyrazol-1-yl)benzylcarbamate (104e) (709 mg, 41%) as a white solid; $^1$H NMR (300 MHz, DMSO-d$_6$) δ 10.69 (s, 1H), 7.61 (s, 1H), 7.58 (s, 1H), 7.56-7.22 (m, 9H), 7.16 (d, J=7.7 Hz, 1H), 4.73 (s, 1H), 4.19 (d, J=6.2 Hz, 2H), 3.74 (s, 3H), 2.27 (t, J=6.4 Hz, 2H), 1.37 (s, 9H), 0.96-0.79 (m, 1H), 0.48-0.27 (m, 2H), 0.09--0.02 (m, 2H); $^{19}$F NMR (282 MHz, DMSO-d$_6$) δ −60.80; MS (ES+) 624.4 (M+1).

Step-5: Preparation of 1-(3-(aminomethyl)phenyl)-N-(3-((cyclopropylmethylamino)(1-methyl-1H-pyrazol-4-yl)methyl)phenyl)-3-(trifluoromethyl)-1H-pyrazole-5-carboxamide (104f)

To a solution of tert-butyl 3-(5-(3-((cyclopropylmethylamino)(1-methyl-1H-pyrazol-4-yl)methyl)phenylcarbamoyl)-3-(trifluoromethyl)-1H-pyrazol-1-yl)benzylcarbamate (104e) (0.614 g, 0.984 mmol) in 1,4-Dioxane (60 mL) was added hydrogen chloride (10.0 mL, 40.0 mmol, 4 M in 1,4-dioxane) stirred at room temperature for 15.5 h. The reaction mixture was treated with hexanes, decanted, washed with hexanes, and decanted again. The insoluble crude product was purified by flash column chromatography [silica gel, eluting with chloroform/CMA80 (1:0 to 1:1)] to give 1-(3-(aminomethyl)phenyl)-N-(3-((cyclopropylmethylamino)(1-methyl-1H-pyrazol-4-yl)methyl)phenyl)-3-(trifluoromethyl)-1H-pyrazole-5-carboxamide (104f) (363 mg, 70%) as a white solid; $^1$H NMR (300 MHz, DMSO-d$_6$) δ 10.67 (s, 1H), 7.61 (t, J=1.8 Hz, 1H), 7.58 (s, 1H), 7.57-7.45 (m, 2H), 7.48-7.39 (m, 3H), 7.37-7.30 (m, 1H), 7.29-7.22 (m, 2H), 7.19-7.12 (m, 1H), 4.72 (s, 1H), 3.79 (s, 2H), 3.74 (s, 3H), 2.36-2.18 (m, 3H), 0.97-0.79 (m, 1H), 0.43-0.30 (m, 2H), 0.10-0.01 (m, 2H); $^{19}$F NMR (282 MHz, DMSO-d$_6$) δ −60.72; MS (ES+) 525.3 (M+1); (ES−) 522.323 (M−1); IR (KBr pellet, cm$^{-1}$): 3429, 2925, 1616, 1559, 1243; Analysis calculated for $C_{27}H_{28}F_3N_7O \cdot 0.25CHCl_3$: C, 59.14; H, 5.15; N, 17.72; Found: C, 59.07; H, 5.24; N, 17.57.

Scheme 105

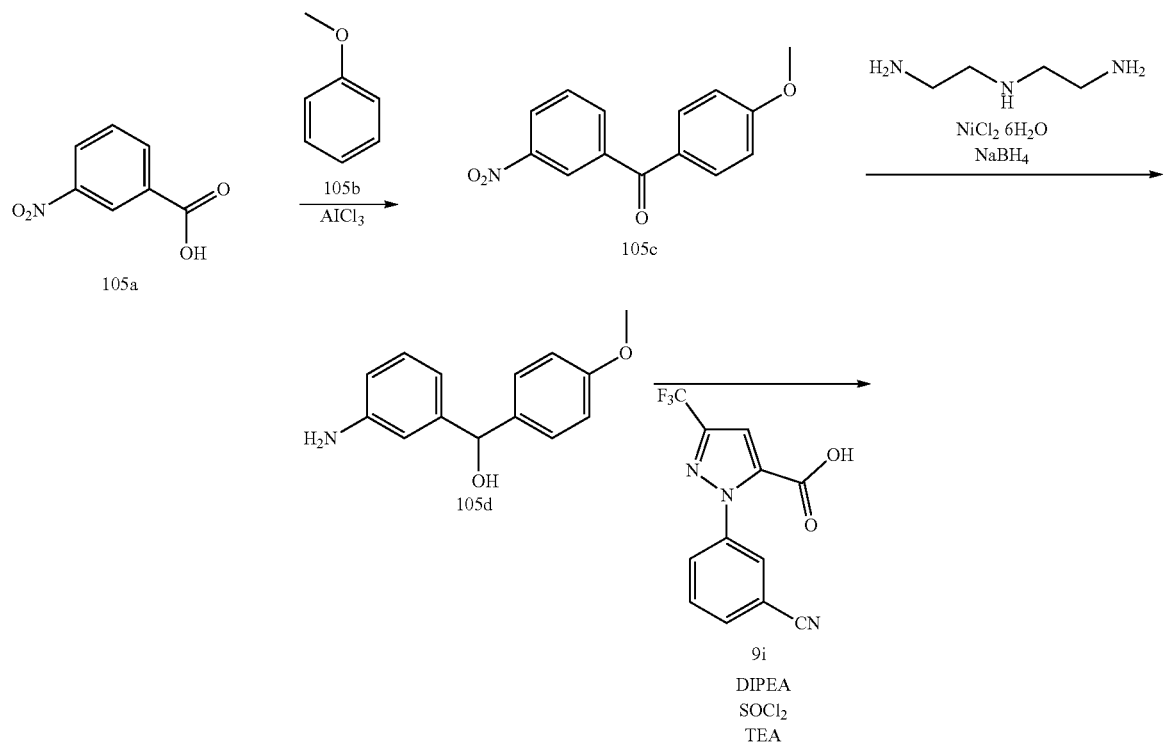

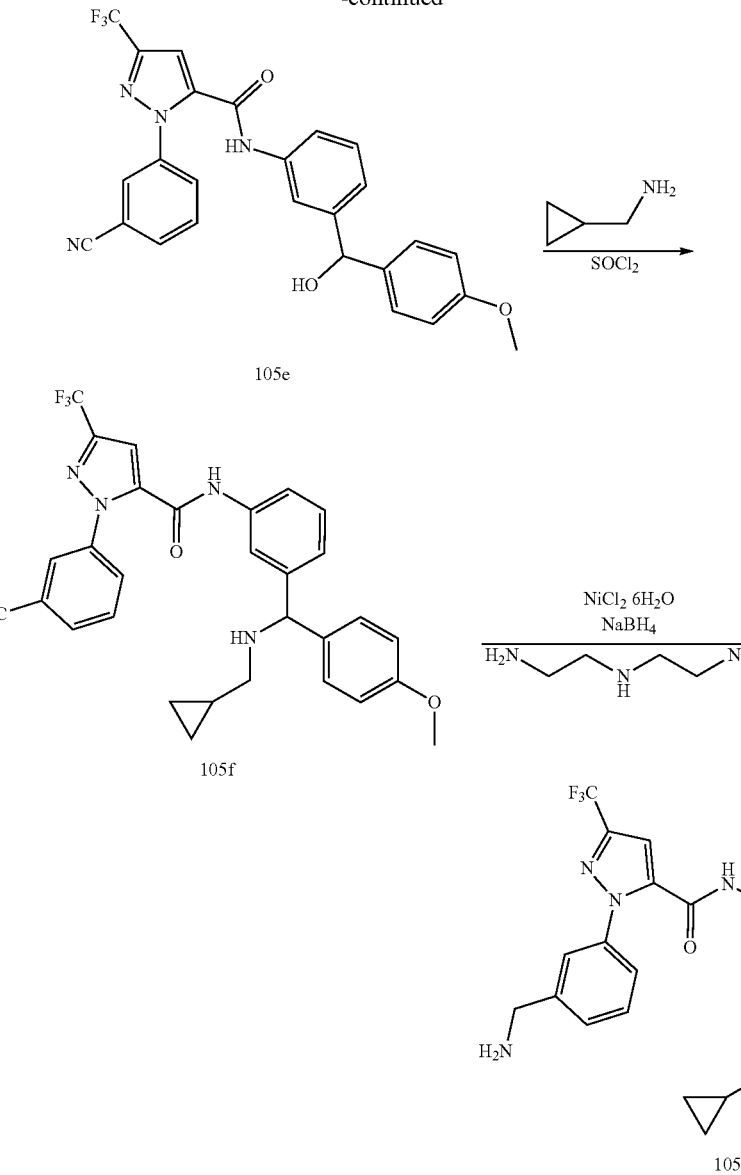

Preparation of 1-(3-(Aminomethyl)phenyl)-N-(3-((((cyclopropylmethyl)amino)(4-methoxyphenyl)methyl)phenyl)-3-(trifluoromethyl)-1H-pyrazole-5-carboxamide (105g)

Step-1: Preparation of (4-methoxyphenyl)(3-nitrophenyl)methanone (105c)

To a stirred solution of 3-nitro-benzoic acid (105a) (5.0 g, 29.92 mmol) in toluene (150 mL) at room temperature was added DMF (5 drops) and SOCl$_2$ (10.67 g, 89.76 mmol). The reaction mixture was heated at 70° C. for 3 h and concentrated in vacuum to dryness. The residue obtained was dissolved in DCM (100 mL), methoxybenzene (105b) (8.2 mL, 76.1 mmol) was added at room temperature and the reaction mixture was heated to 50° C. AlCl$_3$ (15.95 g, 119.672 mmol) was added portion wise to the hot reaction mixture and stirred at 50° C. for 30 min. Completion of the reaction was monitored by TLC (20% EtOAc in n-Hexane), two spots were observed in TLC. Reaction mixture was cooled to room temperature and was poured into crushed Ice. Conc. HCl (6 mL) was added to the mixture and extracted with EtOAc (2×100 mL). The organic layers were combined washed with brine (100 mL), dried over Na$_2$SO$_4$, filtered and concentrated in vacuum. The residue obtained was purified by flash chromatography (silica gel, eluting with 0-40% EtOAc in hexane) to afford (4-Methoxy-phenyl)-(3-nitro-phenyl)methanone (105c) (3.6 g, 46%) as an off-white solid; $^1$H NMR (300 MHz, DMSO-d$_6$) δ 8.48 (ddd, J=8.2, 2.4, 1.1 Hz, 1H), 8.40 (t, J=1.9 Hz, 1H), 8.15-8.09 (m, 1H), 7.86 (d, J=8.0 Hz, 1H), 7.84-7.76 (m, 2H), 7.17-7.09 (m, 2H), 3.88 (s, 3H).

Step-2: Preparation of (3-aminophenyl)(4-methoxyphenyl)methanol (105d)

To a stirred solution of (4-methoxyphenyl)-(3-nitrophenyl)methanone (105c) (3.5 g, 13.61 mmol) in methanol (135 mL) was added NiCl$_2$.6H$_2$O (0.646 g, 2.72 mmol) at room temperature. Reaction mixture was cooled to 0° C. and NaBH$_4$ was added portion wise at this temperature. Reaction mixture was warmed to room temperature and continued stirring for 3 h. Completion of reaction was monitored by TLC (35% EtOAc in n-Hexane). The reaction mixture was quenched with N1-(2-aminoethyl)ethane-1,2-diamine (2.5 mL), stirred for 30 min and concentrated in vacuum to dryness. The residue obtained was dissolved in (1:1) ethyl acetate/water (100 mL). The organic layer was separated and aqueous layer was extracted with ethyl acetate (50 mL). The organic layers were combined, dried, filtered and concentrated in vacuum to dryness. The residue obtained was purified by flash chromatography (silica gel, eluting with EtOAc in hexane 0 to 30%) to afford (3-aminophenyl)-(4-methoxyphenyl)methanol (105d) (1.6 g, 51%) as a light brown oily syrup; $^1$H NMR (300 MHz, DMSO-d$_6$) δ 7.30-7.22 (m, 2H), 6.94 (t, J=7.7 Hz, 1H), 6.90-6.83 (m, 2H), 6.59 (t, J=1.9 Hz, 1H), 6.52 (dt, J=7.6, 1.3 Hz, 1H), 6.41 (ddd, J=7.9, 2.3, 1.0 Hz, 1H), 5.60 (d, J=3.9 Hz, 1H), 5.49 (d, J=3.9 Hz, 1H), 5.00 (s, 2H), 3.74 (s, 3H).

Step-3: Preparation of 1-(3-cyanophenyl)-N-(3-(hydroxy(4-methoxyphenyl)methyl)phenyl)-3-(trifluoromethyl)-1H-pyrazole-5-carboxamide (105e)

To a solution of 2-(3-Cyanophenyl)-5-trifluoromethyl-2H-pyrazole-3-carboxylic acid (9i) (2.24 g, 7.82 mmol) in toluene (50 mL) was added DMF (5 drops), SOCl$_2$ (1.36 mL, 18.77 mmol) at 0° C. Reaction mixture was heated at reflux for 3.5 h and concentrated in vacuum to dryness. The residue obtained was dissolved in dichloromethane (50 mL) and added (3-aminophenyl)-(4-methoxyphenyl)methanol (105d) (1.5 g, 6.54 mmol) followed by drop wise addition of triethylamine (8.8 mL) at room temperature. The reaction mixture was stirred at room temperature overnight. Reaction mixture was concentrated in vacuum to dryness and the residue obtained was purified by flash chromatography (silica gel, eluting with ethyl acetate in hexane 10-50%) to afford 1-(3-cyanophenyl)-N-(3-(hydroxy(4-methoxyphenyl) methyl) phenyl)-3-(trifluoromethyl)-1H-pyrazole-5-carboxamide (105e) (2.6 g, 81%) as a light brown syrup; $^1$H NMR (300 MHz, DMSO-d$_6$) δ 10.62 (s, 1H), 8.16 (t, J=1.8 Hz, 1H), 8.00 (dt, J=7.7, 1.4 Hz, 1H), 7.90 (ddd, J=8.2, 2.2, 1.1 Hz, 1H), 7.77-7.69 (m, 2H), 7.61 (t, J=1.8 Hz, 1H), 7.54 (d, J=8.3 Hz, 1H), 7.31-7.18 (m, 3H), 7.11 (d, J=7.7 Hz, 1H), 6.92-6.80 (m, 2H), 5.84 (d, J=3.9 Hz, 1H), 5.62 (d, J=3.9 Hz, 1H), 3.71 (s, 3H).

Step-4: Preparation of 1-(3-cyanophenyl)-N-(3-(((cyclopropylmethyl)amino)(4-methoxyphenyl) methyl)phenyl)-3-(trifluoromethyl)-1H-pyrazole-5-carboxamide (105f)

To a solution of 1-(3-cyanophenyl)-N-(3-(hydroxy(4-methoxyphenyl)methyl)phenyl)-3-(trifluoromethyl)-1H-pyrazole-5-carboxamide (105e) (2.6 g, 5.28 mmol) in dichloromethane (50 mL) at 0° C. was added thionyl chloride (1.2 g, 10.15 mmol) and allowed to warm to room temperature over 3 h. The reaction mixture was quenched with cyclopropylmethanamine (8 mL), stirred for 1 h at room temperature and heated at 50° C. for 17 h. The reaction mixture was concentrated in vacuum to dryness dissolved in chloroform (50 mL), washed with water (25 mL), dried, filtered and concentrated in vacuum. The residue obtained was purified by flash column chromatography (silica gel 40 g, eluting 0-50% ethyl acetate/methanol 9:1 in hexane) to afford 1-(3-cyanophenyl)-N-(3-(((cyclopropylmethyl) amino)(4-methoxyphenyl)methyl)phenyl)-3-(trifluoromethyl)-1H-pyrazole-5-carboxamide (105f) (1.7 g, 59%) as a light brown semisolid; $^1$H NMR (300 MHz, DMSO-d$_6$) δ 10.59 (s, 1H), 8.11 (t, J=1.9 Hz, 1H), 7.95 (dt, J=7.8, 1.3 Hz, 1H), 7.85 (ddd, J=8.2, 2.2, 1.1 Hz, 1H), 7.73-7.64 (m, 2H), 7.60 (t, J=1.8 Hz, 1H), 7.54-7.46 (m, 1H), 7.29-7.09 (m, 4H), 6.85-6.75 (m, 2H), 4.73 (s, 1H), 3.65 (s, 3H), 2.23 (d, J=6.7 Hz, 2H), 0.94-0.79 (m, 1H), 0.38-0.25 (m, 2H), 0.05--0.06 (m, 2H); $^{19}$F NMR (282 MHz, DMSO) δ -60.97; IR (KBr) 2234 cm$^{-1}$; MS (ES+) 546.3 (M+1); (ES-) 545.4 (M-1); Analysis calculated for C$_{30}$H$_{26}$F$_3$N$_5$O$_2$.0.5CH$_2$Cl$_2$: C, 62.30; H, 4.63; N, 11.91; Found: C, 62.73; H, 4.74; N, 11.60.

Step-5: Preparation of 1-(3-(Aminomethyl)phenyl)-N-(3-(((cyclopropylmethyl)amino)(4-methoxyphenyl)methyl)phenyl)-3-(trifluoromethyl)-1H-pyrazole-5-carboxamide (105g)

To a stirred solution of 1-(3-cyanophenyl)-N-(3-((cyclopropylmethylamino)(4-methoxyphenyl)methyl)phenyl)-3-(trifluoromethyl)-1H-pyrazole-5-carboxamide (105f) (0.5 g, 0.916 mmol) in anhydrous methanol (20 mL), cooled to 0° C., was added nickel(II) chloride hexahydrate (0.272 g, 1.146 mmol), sodium borohydride (0.173 g, 4.58 mmol) was added to the reaction mixture in small portions over a 15 min period. The reaction mixture was stirred for 15 min at 0° C. and quenched with N1-(2-aminoethyl)ethane-1,2-diamine (0.297 mL, 2.75 mmol) stirred for 30 mins and concentrated in vacuum to dryness. The residue obtained was dissolved in dichloromethane (25 mL) and water (25 mL). The organic layer was separated, dried, filtered and concentrated in vacuum. The residue obtained was purified by flash column chromatography (silica gel 24 g, eluting with 0-25% methanol in chloroform) to furnish 1-(3-(aminomethyl)phenyl)-N-(3-((cyclopropylmethylamino)(4-methoxyphenyl) methyl)phenyl)-3-(trifluoromethyl)-1H-pyrazole-5-carboxamide (105g) (0.35 g, 0.637 mmol, 69.5% yield) as a white solid; $^1$H NMR (300 MHz, DMSO-d$_6$) δ 10.78 (s, 1H), 7.72 (t, J=1.7 Hz, 1H), 7.67 (s, 2H), 7.61 (dt, J=7.3, 1.7 Hz, 1H), 7.58-7.47 (m, 3H), 7.37-7.29 (m, 2H), 7.26 (d, J=7.3 Hz, 2H), 6.90-6.83 (m, 2H), 4.88 (s, 1H), 4.12 (s, 2H), 3.70 (s, 3H), 2.34 (d, J=6.8 Hz, 2H), 1.03-0.87 (m, 1H), 0.45-0.35 (m, 2H), 0.07 (dd, J=5.5, 3.7 Hz, 2H); $^{19}$F NMR (282 MHz, DMSO) δ -60.79; MS (ES+) 550.4 (M+1); (ES-) 548.3 (M-1); Analysis Calculated for C$_{30}$H$_{30}$F$_3$N$_5$O$_2$.1.1HCl.H$_2$O: C, 59.29; H, 5.49; Cl, 6.42; N, 11.52; Found: C, 59.08; H, 5.43; Cl, 6.19; N, 11.17.

Scheme 106

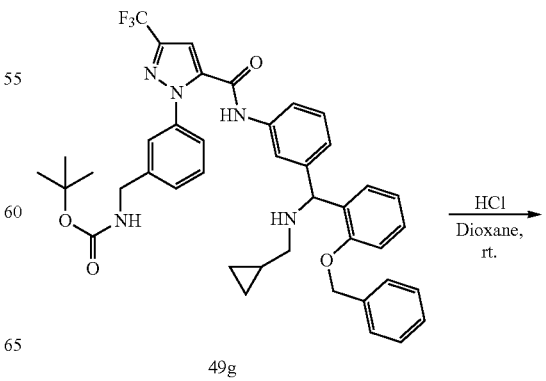

49g

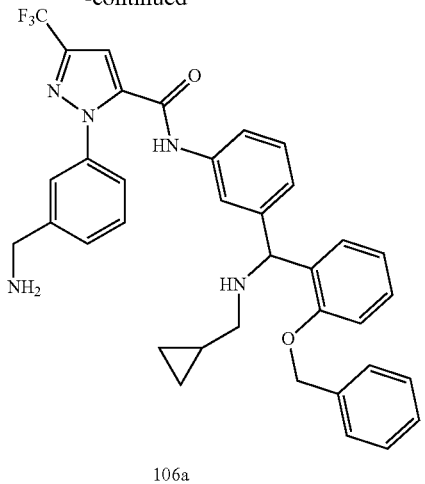

106a

Preparation of 1-(3-(aminomethyl)phenyl)-N-(3-((2-(benzyloxy)phenyl)(cyclopropylmethyl amino)methyl)phenyl)-3-(trifluoromethyl)-1H-pyrazole-5-carboxamide (106a)

To a solution of tert-butyl 3-(5-(3-((2-(benzyloxy)phenyl)(cyclopropylmethylamino)methyl)phenylcarbamoyl)-3-(trifluoromethyl)-1H-pyrazol-1-yl)benzylcarbamate (49g) (0.111 g, 0.153 mmol) in methanol (10 mL) was added hydrogen chloride (4N in dioxane, 1.912 mL, 7.65 mmol) stirred for 14 h at room temperature. Excess solvent was pumped-off under reduced pressure. The residue was purified by flash column chromatography (first column: silica gel 25 g, eluting with CMA80 in chloroform, second column: silica gel 25 g, then 0-100% methanol in chloroform from 0-100%) to afford 1-(3-(aminomethyl)phenyl)-N-(3-((2-(benzyloxy)phenyl)(cyclopropylmethyl amino)methyl)phenyl)-3-(trifluoromethyl)-1H-pyrazole-5-carboxamide (106a) (22 mg, 23% yield) as a white solid; $^1$H NMR (300 MHz, DMSO-$d_6$) δ 10.66 (s, 1H, $D_2O$ exchangeable), 7.67-7.62 (m, 1H), 7.58-7.49 (m, 3H), 7.47-7.28 (m, 9H), 7.24-7.13 (m, 2H), 7.08 (d, J=7.7 Hz, 1H), 7.01 (d, J=8.1 Hz, 1H), 6.93 (t, J=7.4 Hz, 1H), 5.20 (s, 1H), 5.09 (s, 2H), 3.76 (s, 2H), 2.31 (dd, J=12.0, 6.7 Hz, 1H), 2.21 (dd, J=11.9, 7.0 Hz, 1H), 0.87 (p, J=6.5 Hz, 1H), 0.45-0.23 (m, 2H), -0.01 (s, 2H); $^1$H NMR (300 MHz, DMSO-$d_6$, $D_2O$) δ 7.68-7.63 (m, 1H), 7.54-7.49 (m, 3H), 7.49-7.40 (m, 4H), 7.33 (tt, J=5.1, 2.2 Hz, 5H), 7.26-7.14 (m, 2H), 7.10 (d, J=7.7 Hz, 1H), 7.02 (d, J=8.1 Hz, 1H), 6.94 (t, J=7.4 Hz, 1H), 5.20 (s, 1H), 5.08 (s, 2H), 3.74 (s, 2H), 2.37-2.15 (m, 2H), 0.85 (h, J=6.6 Hz, 1H), 0.44-0.28 (m, 2H), -0.01--0.03 (m, 2H); $^{19}$F NMR (282 MHz, DMSO-$d_6$) δ -60.71; MS (ES$^+$): MS (ES+) 626.4 (M+1), MS (ES-) 624.3 (M-1).

Scheme 107

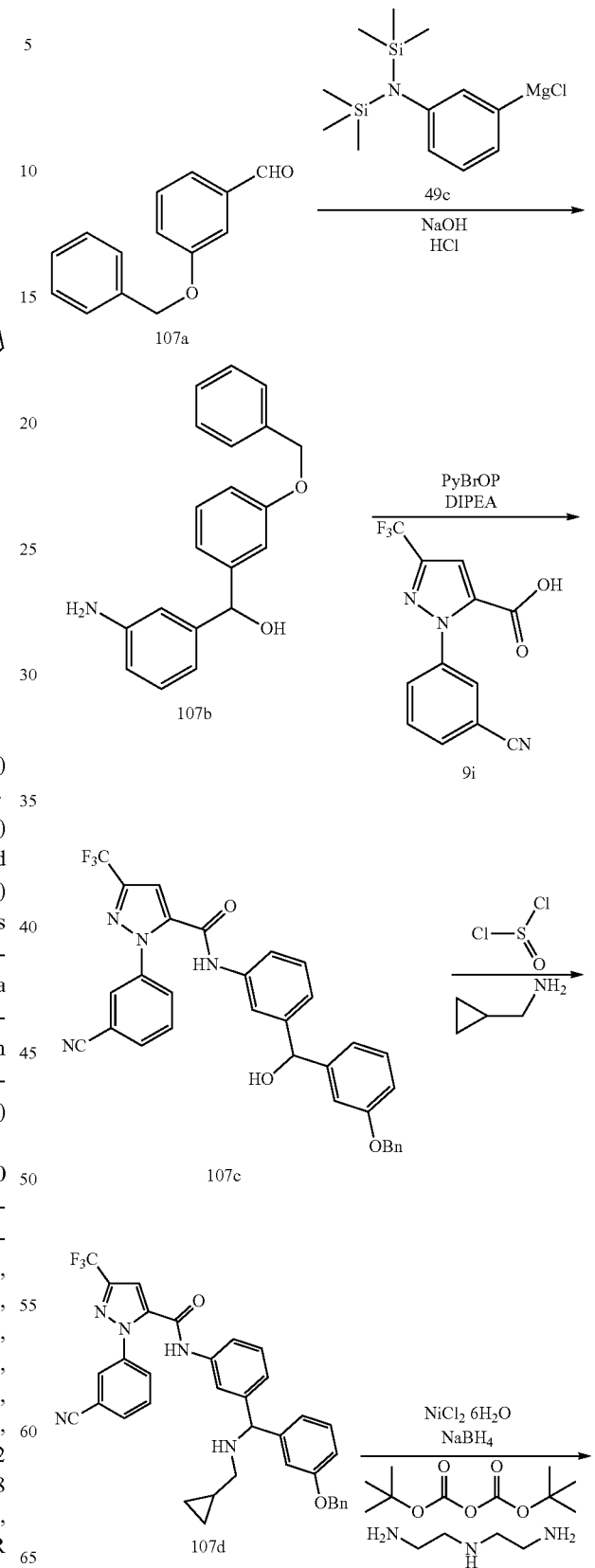

-continued

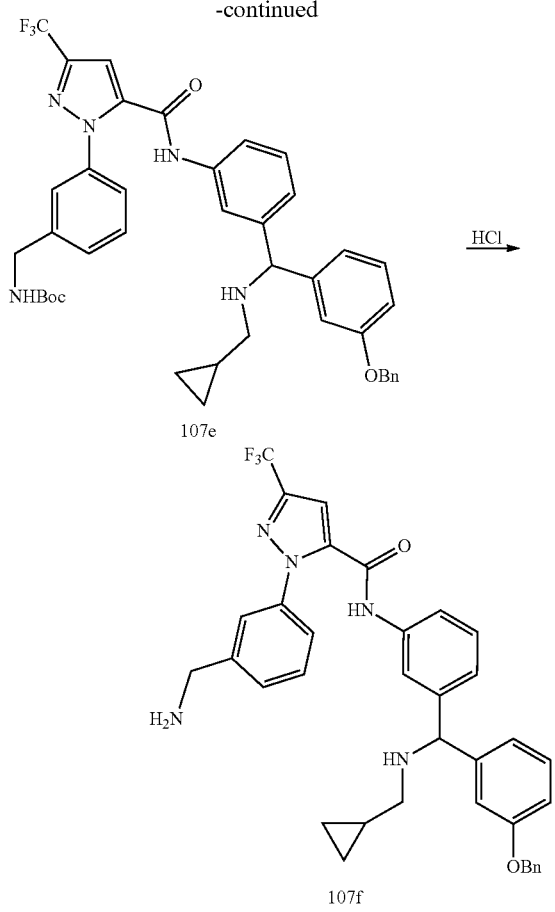

107e

107f

Preparation of 1-(3-(Aminomethyl)phenyl)-N-(3-((3-(benzyloxy)phenyl)(cyclopropylmethylamino) methyl)phenyl)-3-(trifluoromethyl)-1H-pyrazole-5-carboxamide (107f)

Step-1: Preparation of (3-Aminophenyl)(3-(benzyloxy)phenyl)methanol (107b)

To a stirred solution of 3-(benzyloxy) benzaldehyde (107a) (2.122 g, 10 mmol) in tetrahydrofuran (5 mL) was added (3-(bis(trimethylsilyl)amino)phenyl)magnesium chloride (49c) (3.55 g, 12.00 mmol) at 0° C. The reaction was stirred for 14 h at same temperature and quenched by adding 2 N HCl (12.50 mL), stirred for 6 h. The reaction mixture was treated with 2 N NaOH (15 mL) and extracted with ethyl acetate (2×50 mL). The organic layers were combined washed with saturated aqueous NH$_4$Cl (50 mL), dried over anhydrous MgSO$_4$, filtered and evaporated to dryness. The crude residue was purified by flash column chromatography (silica gel 40 g, eluting with ethyl acetate in hexanes from 0-100%) to furnish (3-Aminophenyl)(3-(benzyloxy)phenyl)methanol (107b) (1.258 g, 41% yield) as a thick yellow oil; $^1$H NMR (300 MHz, DMSO-d$_6$) δ 7.47-7.29 (m, 5H), 7.19 (t, J=7.9 Hz, 1H), 7.05-6.97 (m, 1H), 6.96-6.86 (m, 2H), 6.83 (ddd, J=8.2, 2.7, 1.0 Hz, 1H), 6.58 (t, J=1.9 Hz, 1H), 6.50 (dt, J=7.6, 1.3 Hz, 1H), 6.38 (ddd, J=7.9, 2.3, 1.0 Hz, 1H), 5.69 (d, J=3.9 Hz, 1H, D$_2$O exchangeable), 5.46 (d, J=3.9 Hz, 1H), 5.05 (s, 2H), 4.98 (s, 2H, D$_2$O exchangeable); MS (ES$^+$): MS (ES+) 328.2 (M+Cl), MS (ES−) 304.2 (M−1).

Step-2: Preparation of N-(3-((3-(Benzyloxy)phenyl)(hydroxy)methyl)phenyl)-1-(3-cyanophenyl)-3-(trifluoromethyl)-1H-pyrazole-5-carboxamide (107c)

To a solution of 1-(3-cyanophenyl)-3-(trifluoromethyl)-1H-pyrazole-5-carboxylic acid (9i) (1.215 g, 4.32 mmol) in DMF (10 mL) was added (3-aminophenyl)(3-(benzyloxy)phenyl)methanol (107b) (1.2 g, 3.93 mmol), N-ethyl-N-isopropylpropan-2-amine (3.42 mL, 19.65 mmol), and bromo-tris-pyrrolidino phosphoniumhexafluorophosphate (PyBrOP, 2.198 g, 4.72 mmol) at room temperature. The reaction mixture was stirred at room temperature for 37 h under nitrogen atmosphere. The reaction was diluted with water (25 mL) and extracted with ethyl acetate (2×100 mL). The organic layers were combined, washed with brine (50 mL), dried, filtered, and evaporated in vacuum to dryness. The residue obtained was purified by flash column chromatography (silica gel 40 g, eluting with 0-100% ethyl acetate in hexanes) to furnish N-(3-((3-(benzyloxy)phenyl)(hydroxy)methyl)phenyl)-1-(3-cyanophenyl)-3-(trifluoromethyl)-1H-pyrazole-5-carboxamide (107c) (1.637 g, 2.88 mmol, 73.3% yield) as a white solid; $^1$H NMR (300 MHz, DMSO-d$_6$) δ 10.64 (s, 1H), 8.16 (td, J=1.7, 0.9 Hz, 1H), 8.03-7.95 (m, 1H), 7.90 (ddd, J=8.2, 2.3, 1.1 Hz, 1H), 7.77-7.68 (m, 2H), 7.64 (t, J=1.8 Hz, 1H), 7.60-7.52 (m, 1H), 7.46-7.30 (m, 5H), 7.23 (dt, J=15.5, 7.9 Hz, 2H), 7.17-7.10 (m, 1H), 7.02 (dd, J=2.6, 1.5 Hz, 1H), 6.95-6.89 (m, 1H), 6.85 (ddd, J=8.1, 2.7, 1.0 Hz, 1H), 5.95 (d, J=3.8 Hz, 1H), 5.63 (d, J=3.9 Hz, 1H), 5.05 (s, 2H); $^{19}$F NMR (282 MHz, DMSO) δ −60.97; MS (ES−) 567.3 (M−1).

Step-3: Preparation of N-(3-((3-(Benzyloxy)phenyl)(cyclopropylmethylamino)methyl)phenyl)-1-(3-cyanophenyl)-3-(trifluoromethyl)-1H-pyrazole-5-carboxamide (107d)

To a solution of N-(3-((3-(benzyloxy)phenyl)(hydroxy)methyl)phenyl)-1-(3-cyanophenyl)-3-(trifluoromethyl)-1H-pyrazole-5-carboxamide (107c) (1.637 g, 2.88 mmol) in dichloromethane (50 mL) at 0° C. was added thionyl chloride (0.63 mL, 8.64 mmol) and stirred at room temperature for 2 h. The reaction mixture was quenched with cyclopropylmethanamine (0.749 mL, 8.64 mmol) and stirred at room temperature for additional 5 h. The reaction mixture was concentrated in vacuum to dryness. The residue obtained was dissolved in acetonitrile (10 mL) and added cyclopropylmethanamine (4.99 mL, 57.6 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum. The residue obtained was purified by flash column chromatography (silica gel 40 g, eluting 0-100% ethyl acetate in hexane) to afford N-(3-((3-(benzyloxy)phenyl)(cyclopropylmethylamino)methyl)phenyl)-1-(3-cyanophenyl)-3-(trifluoromethyl)-1H-pyrazole-5-carboxamide (107d) (1.16 g, 1.866 mmol, 64.8% yield) as a yellow solid; $^1$HNMR (300 MHz, DMSO-d$_6$) δ 10.63 (s, 1H), 8.16 (t, J=1.8 Hz, 1H), 7.98 (dt, J=7.8, 1.3 Hz, 1H), 7.90 (ddd, J=8.2, 2.2, 1.1 Hz, 1H), 7.75-7.66 (m, 3H), 7.55 (dt, J=7.9, 1.5 Hz, 1H), 7.45-7.40 (m, 3H), 7.39-7.37 (m, 1H), 7.36-7.31 (m, 2H), 7.25-7.16 (m, 3H), 7.09-7.06 (m, 1H), 6.97 (d, J=7.6 Hz, 1H), 6.83 (ddd, J=8.2, 2.6, 1.0 Hz, 1H), 5.04 (s, 2H), 4.79 (s, 1H), 2.35 (s, 1H), 2.27 (s, 2H), 1.01-0.84 (m, 1H), 0.42-0.32 (m, 2H), 0.05 (dd, J=5.2, 3.8 Hz, 2H); $^{19}$F NMR (282 MHz, DMSO-d$_6$) δ −60.95; MS (ES+) 622.4 (M+1); (ES−) 620.3 (M−1).

Step-4: Preparation of tert-Butyl 3-(5-(3-((3-(benzyloxy)phenyl)(cyclopropylmethylamino)methyl) phenylcarbamoyl)-3-(trifluoromethyl)-1H-pyrazol-1-yl) benzylcarbamate (107e)

To a solution of N-(3-((3-(benzyloxy)phenyl)(cyclopropylmethylamino)methyl)phenyl)-1-(3-cyanophenyl)-3-(trifluoromethyl)-1H-pyrazole-5-carboxamide (107d) (1.0 g, 1.609 mmol) in MeOH (10 mL) cooled with ice/water was added di-tert-butyl dicarbonate (1.053 g, 4.83 mmol) and nickel(II) chloride (0.421 g, 1.769 mmol). sodium borohydride (0.497 g, 12.87 mmol) was added slowly over 15 min and reaction mixture was stirred at room temperature for 1 h. The reaction mixture was quenched with N1-(2-aminoethyl)ethane-1,2-diamine (0.527 mL, 4.83 mmol) stirred for 0.5 h and concentrated in vacuum to dryness. The residue obtained was dissolved in dichloromethane (60 mL) and water (60 mL). The aqueous phase was separated and extracted again with dichloromethane (60 mL). The organic extracts were combined, washed with brine (60 mL), dried over MgSO$_4$, filtered and concentrated in vacuum to dryness. The residue obtained was purified by flash column chromatography (silica gel 24 g with 0-100% 9:1 ethyl acetate/methanol in hexane) to afford tert-butyl 3-(5-(3-((3-(benzyloxy)phenyl)(cyclopropylmethylamino)methyl)phenylcarbamoyl)-3-(trifluoromethyl)-1H-pyrazol-1-yl)benzylcarbamate (107e) (0.304 g, 0.419 mmol, 26.0% yield) as a white solid.

$^1$H NMR (300 MHz, DMSO-d$_6$) δ 10.69 (s, 1H), 7.65 (d, J=2.3 Hz, 1H), 7.58 (s, 1H), 7.51 (q, J=7.1, 6.3 Hz, 2H), 7.46-7.30 (m, 9H), 7.27-7.14 (m, 3H), 7.11-7.05 (m, 1H), 6.97 (d, J=7.7 Hz, 1H), 6.83 (ddd, J=8.2, 2.6, 1.0 Hz, 1H), 5.05 (s, 2H), 4.78 (s, 1H), 4.18 (d, J=6.2 Hz, 2H), 2.35 (s, 1H), 2.27 (s, 2H), 1.36 (s, 9H), 0.92 (dd, J=13.2, 6.3 Hz, 1H), 0.42-0.31 (m, 2H), 0.04 (q, J=5.8, 5.3 Hz, 2H); $^{19}$F NMR (282 MHz, DMSO-d$_6$) δ −60.80; MS (ES+) 726.5 (M+1); (ES−) 724.5 (M−1).

Step-5: Preparation of 1-(3-(Aminomethyl)phenyl)-N-(3-((3-(benzyloxy)phenyl)(cyclopropylmethylamino) methyl)phenyl)-3-(trifluoromethyl)-1H-pyrazole-5-carboxamide (107f)

To a solution of tert-butyl 3-(5-(3-((3-(benzyloxy)phenyl)(cyclopropylmethylamino)methyl) phenylcarbamoyl)-3-(trifluoromethyl)-1H-pyrazol-1-yl)benzylcarbamate (107e) (0.125 g, 0.172 mmol) in methanol (Volume: 7.5 mL) was added hydrogen chloride (0.359 mL, 4.31 mmol), stirred at room temperature overnight and concentrated in vacuum to dryness. The residue obtained was purified by flash column chromatography (silica gel 12 g, eluting with 0-50% methanol in chloroform) to afford 1-(3-(aminomethyl)phenyl)-N-(3-((3-(benzyloxy)phenyl)(cyclopropylmethylamino) methyl)phenyl)-3-(trifluoromethyl)-1H-pyrazole-5-carboxamide (107f) (0.05 g, 0.080 mmol, 46.4% yield) as an off-white solid; $^1$H NMR (300 MHz, DMSO-d$_6$) δ 10.84 (s, 1H), 8.50 (d, J=59.1 Hz, 2H), 7.76 (s, 1H), 7.72 (d, J=2.0 Hz, 1H), 7.69 (s, 1H), 7.64-7.49 (m, 4H), 7.46-7.21 (m, 9H), 7.06 (d, J=7.4 Hz, 1H), 6.90 (dd, J=8.0, 2.5 Hz, 1H), 5.08 (s, 3H), 4.11 (s, 2H), 2.47-2.38 (m, 2H), 1.09-0.93 (m, 1H), 0.44 (td, J=5.3, 4.8, 2.8 Hz, 2H), 0.25-0.07 (m, 2H); $^{19}$F NMR (282 MHz, DMSO) δ −60.78; MS (ES+) 626.4 (M+1); (ES−) 624.4 (M−1); Analysis calculated for C$_{36}$H$_{34}$F$_3$N$_5$O$_2$.1.5HCl.H$_2$O: C, 61.91; H, 5.41; Cl, 7.61; N, 10.03: Found: C, 61.51; H, 5.51; Cl, 7.89; N, 9.85.

Scheme 108

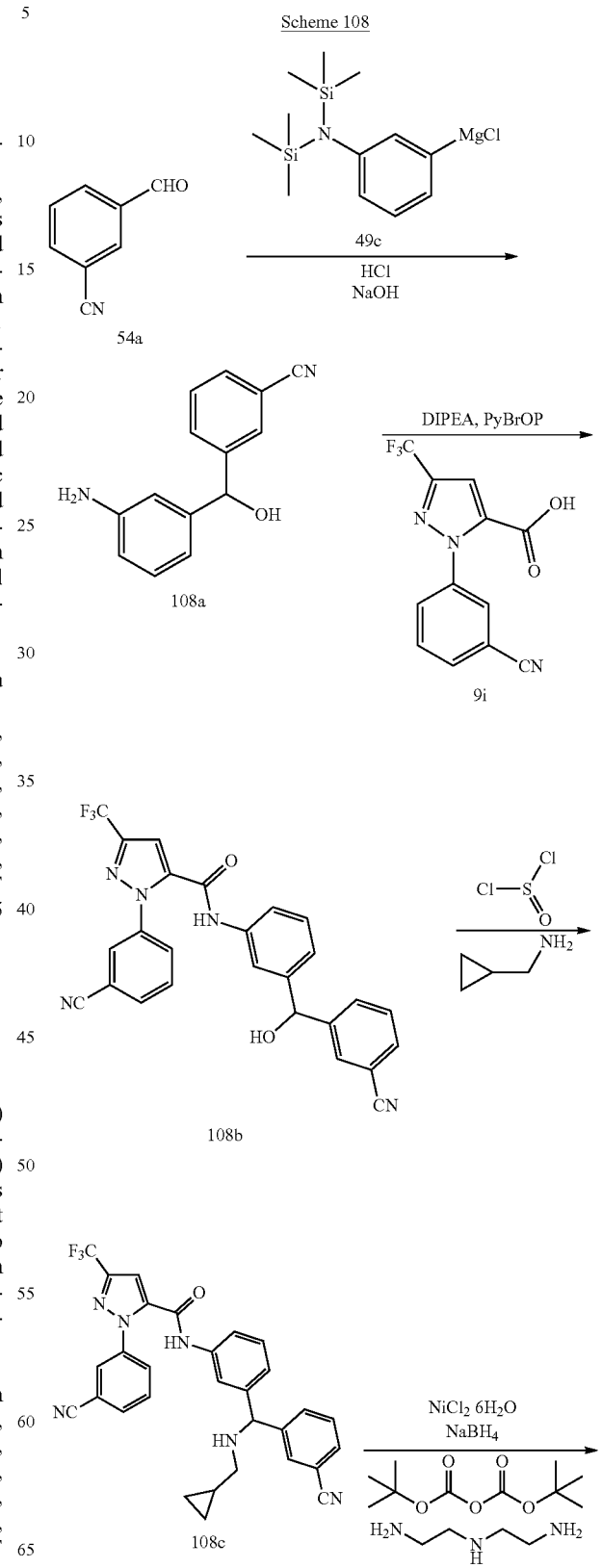

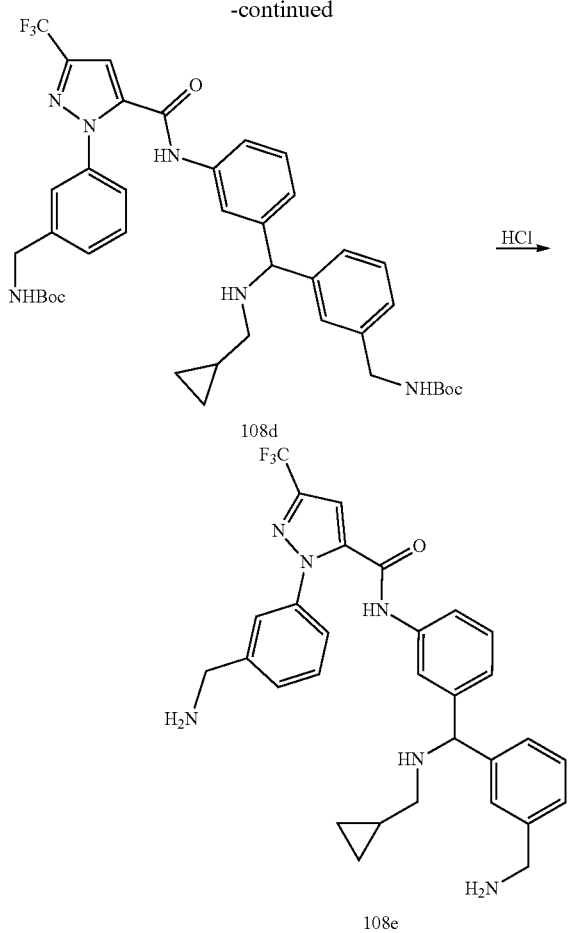

Preparation of 1-(3-(Aminomethyl)phenyl)-N-(3-((3-(aminomethyl)phenyl)(cyclopropylmethylamino)methyl)phenyl)-3-(trifluoromethyl)-1H-pyrazole-5-carboxamide (108e)

Step-1: Preparation of 3-((3-aminophenyl)(hydroxy)methyl)benzonitrile (108a)

To a stirred solution of 3-formylbenzonitrile (54a) (1.311 g, 10 mmol) in tetrahydrofuran (5 mL) was added (3-(bis(trimethylsilyl)amino)phenyl)magnesium chloride (49c) (12.00 mL, 12.00 mmol) at 0° C. The reaction was stirred for 14 h at room temperature and quenched by adding 2 N HCl (12.50 mL), stirred for 6 h. The reaction mixture was treated with 2 N NaOH (15 mL) and extracted with ethyl acetate (2×50 mL). The organic layers were combined washed with sat. NH$_4$Cl (50 mL), dried over anhydrous MgSO$_4$, filtered, evaporated to dryness. The crude residue was purified by flash column chromatography (silica gel 40 g, eluting with 0-100% ethyl acetate in hexane) to furnish 3-((3-aminophenyl)(hydroxy)methyl)benzonitrile (108a) (0.652 g, 29% yield) as a white solid; $^1$H NMR (300 MHz, DMSO-d$_6$) δ 7.76 (t, J=1.7 Hz, 1H), 7.73-7.63 (m, 2H), 7.51 (t, J=7.7 Hz, 1H), 6.94 (t, J=7.7 Hz, 1H), 6.60-6.48 (m, 2H), 6.40 (ddd, J=7.9, 2.3, 1.1 Hz, 1H), 5.97 (d, J=3.9 Hz, 1H, D$_2$O exchangeable), 5.58 (d, J=3.9 Hz, 1H), 5.04 (s, 2H, D$_2$O exchangeable); MS (ES$^+$): MS (ES+) 225.2 (M+1), 247.1 (M+Na), 223.1 (M−1).

Step-2: Preparation of 1-(3-Cyanophenyl)-N-(3-((3-cyanophenyl)(hydroxy)methyl)phenyl)-3-(trifluoromethyl)-1H-pyrazole-5-carboxamide (108b)

To a solution of 1-(3-cyanophenyl)-3-(trifluoromethyl)-1H-pyrazole-5-carboxylic acid (9i) (0.897 g, 3.19 mmol) in DMF (10 mL) was added 3-((3-aminophenyl)(hydroxy)methyl)benzonitrile (108a) (0.65 g, 2.90 mmol), N-ethyl-N-isopropylpropan-2-amine (2.52 mL, 14.5 mmol) and bromotris-pyrrolidino phosphoniumhexafluorophosphate (PyBrop) (1.62 g, 3.48 mmol) at room temperature. The reaction mixture was stirred at room temperature for 37 h under nitrogen atmosphere. The reaction was diluted with water (25 mL) and extracted with ethyl acetate (2×100 mL). The organic layers were combined, washed with brine (50 mL), dried, filtered, and concentrated in vacuum to dryness. The residue obtained was purified by flash column chromatography (silica gel 40 g, eluting with 0-100% ethyl acetate in hexanes) to furnish 1-(3-Cyanophenyl)-N-(3-((3-cyanophenyl)(hydroxy)methyl)phenyl)-3-(trifluoromethyl)-1H-pyrazole-5-carboxamide (108b) (1.057 g, 2.169 mmol, 74.8% yield) as a white solid; $^1$H NMR (300 MHz, DMSO-d$_6$) δ 10.65 (s, 1H), 8.16 (t, J=1.8 Hz, 1H), 8.00 (dt, J=7.7, 1.3 Hz, 1H), 7.90 (ddd, J=8.2, 2.2, 1.1 Hz, 1H), 7.80 (d, J=1.7 Hz, 1H), 7.77-7.62 (m, 5H), 7.61-7.56 (m, 1H), 7.53 (t, J=7.7 Hz, 1H), 7.29 (t, J=7.8 Hz, 1H), 7.22-7.10 (m, 1H), 6.22 (d, J=3.9 Hz, 1H), 5.77 (d, J=4.0 Hz, 1H); $^{19}$F NMR (282 MHz, DMSO-d$_6$) δ −60.96; MS (ES+) 510.2 (M+Na); (ES−) 486.2 (M−1); 973.3 (2M−1).

Step-3: Preparation of 1-(3-Cyanophenyl)-N-(3-((3-cyanophenyl)(cyclopropylmethylamino)methyl)phenyl)-3-(trifluoromethyl)-1H-pyrazole-5-carboxamide (108c)

To a solution of 1-(3-cyanophenyl)-N-(3-((3-cyanophenyl)(hydroxy)methyl)phenyl)-3-(trifluoromethyl)-1H-pyrazole-5-carboxamide (108b) (1.057 g, 2.169 mmol) in dichloromethane (50 mL) at 0° C. was added thionyl chloride (0.48 mL, 6.51 mmol) and stirred at room temperature for 2 h. The reaction mixture was quenched with cyclopropylmethanamine (0.564 mL, 6.51 mmol) and stirred at room temperature for additional 5 h. The reaction mixture was concentrated in vacuum to dryness. The residue obtained was dissolved in acetonitrile (5 mL) and added cyclopropylmethanamine (3.76 mL, 43.4 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum. The residue obtained was purified by flash column chromatography (silica gel 40 g, eluting 0-100% ethyl acetate in hexane) to afford 1-(3-cyanophenyl)-N-(3-((3-cyanophenyl)(cyclopropylmethylamino)methyl)phenyl)-3-(trifluoromethyl)-1H-pyrazole-5-carboxamide (108c) (0.459 g, 0.849 mmol, 39.2% yield) as a yellow oil; $^1$H NMR (300 MHz, DMSO-d$_6$) δ 10.65 (s, 1H), 8.16 (t, J=1.8 Hz, 1H), 8.00 (dt, J=7.8, 1.3 Hz, 1H), 7.94-7.86 (m, 2H), 7.77-7.64 (m, 5H), 7.60-7.46 (m, 2H), 7.32-7.19 (m, 2H), 4.92 (s, 1H), 2.63 (s, 1H), 2.27 (s, 2H), 0.96-0.87 (m, 1H), 0.44-0.39 (m, 2H), 0.08-0.02 (m, 2H); $^{19}$F NMR (282 MHz, DMSO-d$_6$) δ −60.96; MS (ES+) 541.304 (M+1); (ES−) 539.269 (M−1).

Step-4: Preparation of 1-(3-(tert-Butoxycarbonylaminomethyl)phenyl)-N-(3-((3-(tert-butoxycarbonylaminomethyl)phenyl)((cyclopropylmethyl)amino)methyl)phenyl)-3-(trifluoromethyl)-1H-pyrazole-5-carboxamide (108d)

To a solution of 1-(3-cyanophenyl)-N-(3-((3-cyanophenyl)(cyclopropylmethylamino)methyl) phenyl)-3-(trifluoromethyl)-1H-pyrazole-5-carboxamide (108c) (0.425 g, 0.786 mmol) in MeOH (10 mL) cooled with ice/water was added di-tert-butyl dicarbonate (0.867 g, 3.93 mmol) and nickel(II) chloride (0.206 g, 0.865 mmol). Sodium borohydride (0.364 g, 9.44 mmol) was added slowly over 15 min and reaction mixture was stirred at room temperature for 1 h. The reaction mixture was quenched with N1-(2-aminoethyl)ethane-1,2-diamine (0.429 mL, 3.93 mmol) stirred for 0.5 h and concentrated in vacuum to dryness. The residue obtained was dissolved in dichloromethane (60 mL) and water (60 mL). The aqueous phase was separated and extracted again with dichloromethane (60 mL). The organic extracts were combined, washed with brine (60 mL), dried over MgSO$_4$, filtered and concentrated in vacuum to dryness. The residue obtained was purified by flash column chromatography (silica gel 24 g with 0-100% 9:1 ethyl acetate/methanol in hexane) to afford 1-(3-(tert-butoxycarbonylaminomethyl)phenyl)-N-(3-((3-(tert-butoxycarbonylaminomethyl)phenyl)((cyclopropylmethyl)amino)methyl)phenyl)-3-(trifluoro methyl)-1H-pyrazole-5-carboxamide (108d) (0.143 g, 0.191 mmol, 24.29% yield) as a white solid; $^1$H NMR (300 MHz, DMSO-d$_6$) δ 10.69 (s, 1H), 7.64 (s, 1H), 7.57 (s, 1H), 7.55-7.32 (m, 7H), 7.31-7.14 (m, 5H), 7.04 (d, J=7.0 Hz, 1H), 4.78 (s, 1H), 4.19 (d, J=6.2 Hz, 2H), 4.07 (d, J=6.2 Hz, 2H), 2.38-2.19 (m, 3H), 1.37 (d, J=3.2 Hz, 18H), 0.98-0.82 (m, 1H), 0.44-0.31 (m, 2H), 0.11-0.01 (m, 2H); 19F NMR (282 MHz, DMSO-d$_6$) δ −60.81; MS (ES+) 749.5 (M+1); (ES−) 747.5 (M−1).

Step-5: Preparation of 1-(3-(Aminomethyl)phenyl)-N-(3-((3-(aminomethyl)phenyl)(cyclopropylmethylamino) methyl)phenyl)-3-(trifluoromethyl)-1H-pyrazole-5-carboxamide (108e)

To a solution of 1-(3-(tert-Butoxycarbonylaminomethyl)phenyl)-N-(3-((3-(tert-butoxycarbonylaminomethyl)phenyl)((cyclopropylmethyl)amino)methyl)phenyl)-3-(trifluoromethyl)-1H-pyrazole-5-carboxamide (108d) (0.148 g, 0.198 mmol) in methanol (10 mL) was added conc. hydrogen chloride (0.824 mL, 9.88 mmol), stirred at room temperature overnight and concentrated in vacuum to dryness. The residue obtained was purified by flash column chromatography (silica gel 12 g, eluting with 0-100% CMA-80 in chloroform) to afford 1-(3-(aminomethyl)phenyl)-N-(3-((3-(aminomethyl)phenyl)(cyclopropylmethylamino) methyl) phenyl)-3-(trifluoromethyl)-1H-pyrazole-5-carboxamide (108e) (0.05 g, 0.091 mmol, 46.1% yield) as an light yellow solid; $^1$H NMR (300 MHz, DMSO-d$_6$) δ 10.67 (s, 1H), 7.66 (s, 1H), 7.60-7.11 (m, 12H), 4.79 (s, 1H), 3.77 (s, 2H), 3.67 (s, 2H), 2.28 (d, J=6.7 Hz, 2H), 1.05-0.83 (m, 1H), 0.51-0.30 (m, 2H), 0.05 (t, J=4.7 Hz, 2H); $^{19}$F NMR (282 MHz, DMSO) δ −60.51; MS (ES+) 549.4 (M+1); (ES−) 547.4 (M−1); Analysis calculated for C$_{30}$H$_{31}$F$_3$N$_6$O$_2$.0.5H$_2$O: C, 64.62; H, 5.78; N, 15.07; Found: C, 64.34; H, 5.73; N, 14.72.

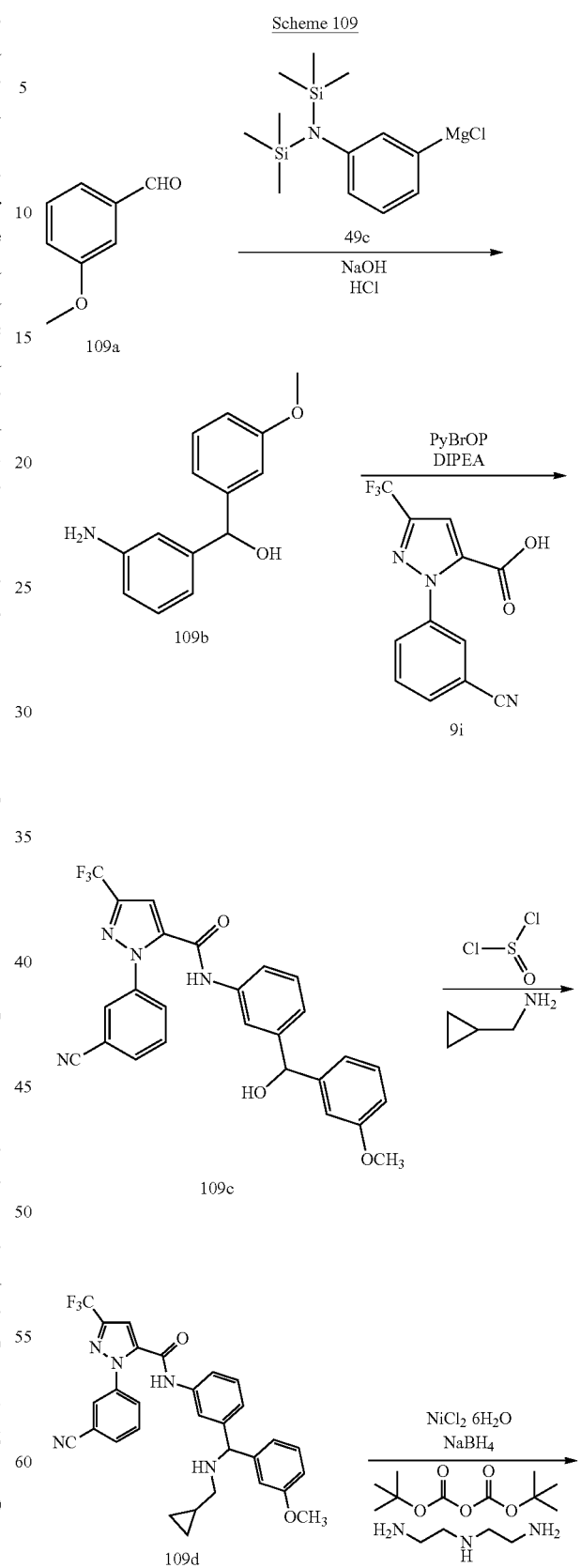

459

-continued

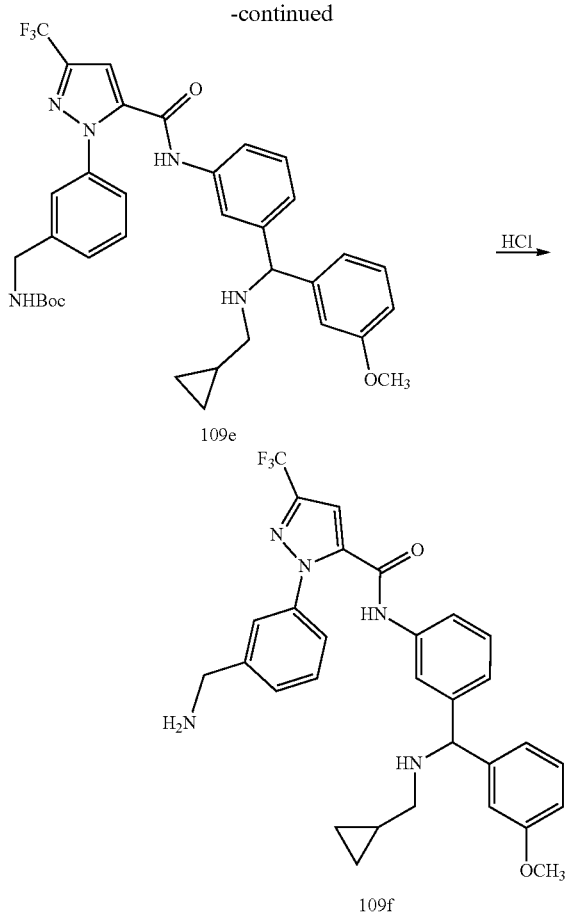

109e

109f

Preparation of 1-(3-(Aminomethyl)phenyl)-N-(3-((cyclopropylmethylamino)(3-methoxyphenyl)methyl)phenyl)-3-(trifluoromethyl)-1H-pyrazole-5-carboxamide (109f)

Step-1: Preparation of (3-aminophenyl)(3-methoxyphenyl)methanol (109b)

To a stirred solution of 3-methoxybenzaldehyde (109a) (1.361 g, 10 mmol) in tetrahydrofuran (5 mL) was added (3-(bis(trimethylsilyl)amino)phenyl)magnesium chloride (49c) (12.0 mL, 12.0 mmol) at 0° C. The reaction was stirred for 14 h at same temperature and quenched by adding 2 N HCl (12.50 mL, 25.00 mmol), stirred for 6 h. The reaction mixture was treated with 2 N NaOH (15.00 mL, 30.0 mmol) and extracted with ethyl acetate (2×50 mL). The organic layers were combined washed with sat. NH$_4$Cl (50 mL), dried over anhydrous MgSO$_4$, filtered, evaporated to dryness. The crude residue was purified by flash column chromatography (silica gel 40 g, eluting with 0-20% ethyl acetate in hexane) to furnish (3-aminophenyl)(3-methoxyphenyl)methanol (109b) (1.327 g, 58% yield) as a yellow oil; $^1$H NMR (300 MHz, DMSO-d$_6$) δ 7.18 (t, J=7.8 Hz, 1H), 7.00-6.85 (m, 3H), 6.75 (ddd, J=8.2, 2.6, 1.0 Hz, 1H), 6.60-6.46 (m, 2H), 6.37 (ddd, J=7.9, 2.3, 1.1 Hz, 1H), 5.68 (d, J=3.9 Hz, 1H, D$_2$O exchangeable), 5.46 (d, J=3.9 Hz, 1H), 4.98 (s, 2H, D$_2$O exchangeable), 3.71 (s, 3H); MS (ES$^+$): MS (ES+) 230.2 (M+1), 252.1 (M+Na), 228.12 (M−1).

460

Step-2: Preparation of 1-(3-Cyanophenyl)-N-(3-(hydroxy(3-methoxyphenyl)methyl)phenyl)-3-(trifluoromethyl)-1H-pyrazole-5-carboxamide (109c)

To a solution of 1-(3-cyanophenyl)-3-(trifluoromethyl)-1H-pyrazole-5-carboxylic acid (9i) (1.754 g, 6.24 mmol) in DMF (10 mL) was added (3-aminophenyl)(3-methoxyphenyl)methanol (109b) (1.3 g, 5.67 mmol), N-ethyl-N-isopropylpropan-2-amine (4.94 mL, 28.4 mmol) and bromo-tris-pyrrolidino phosphoniumhexafluorophosphate (PyBrOP, 3.17 g, 6.80 mmol) at room temperature. The reaction mixture was stirred at room temperature for 37 h under nitrogen atmosphere. The reaction was diluted with water (25 mL) and extracted with ethyl acetate (2×100 mL). The organic layers were combined, washed with brine (50 mL), dried, filtered, and evaporated in vacuum to dryness. The residue obtained was purified by flash column chromatography (silica gel 40 g, eluting with 0-100% ethyl acetate in hexanes) to furnish 1-(3-cyanophenyl)-N-(3-(hydroxy(3-methoxyphenyl)methyl)phenyl)-3-(trifluoromethyl)-1H-pyrazole-5-carboxamide (109c) (2.27 g, 4.61 mmol, 81% yield) as a yellow semisolid; $^1$H NMR (300 MHz, DMSO-d$_6$) δ 10.63 (s, 1H), 8.21-8.12 (m, 1H), 8.00 (dt, J=7.8, 1.3 Hz, 1H), 7.90 (ddd, J=8.3, 2.2, 1.2 Hz, 1H), 7.79-7.68 (m, 2H), 7.67-7.60 (m, 1H), 7.59-7.48 (m, 1H), 7.31-7.10 (m, 3H), 6.94 (t, J=2.0 Hz, 1H), 6.90 (d, J=7.7 Hz, 1H), 6.77 (ddd, J=8.2, 2.7, 1.0 Hz, 1H), 5.95 (d, J=3.8 Hz, 1H), 5.63 (d, J=3.8 Hz, 1H), 3.71 (s, 3H); $^{19}$F NMR (282 MHz, DMSO-d$_6$) δ −60.96; MS (ES−) 491.2 (M−1).

Step-3: Preparation of 1-(3-Cyanophenyl)-N-(3-((cyclopropylmethylamino)(3-methoxyphenyl)methyl)phenyl)-3-(trifluoromethyl)-1H-pyrazole-5-carboxamide (109d)

To a solution of 1-(3-cyanophenyl)-N-(3-(hydroxy(3-methoxyphenyl)methyl)phenyl)-3-(trifluoromethyl)-1H-pyrazole-5-carboxamide (109c) (2.27 g, 4.61 mmol) in dichloromethane (25 mL) at 0° C. was added thionyl chloride (1 mL, 13.83 mmol) and stirred at room temperature for 2 h. The reaction mixture was quenched with cyclopropylmethanamine (1.199 mL, 13.83 mmol) and stirred at room temperature for additional 5 h. The reaction mixture was concentrated in vacuum to dryness. The residue obtained was dissolved in acetonitrile (10 mL) and added cyclopropylmethanamine (8.00 mL, 92 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum. The residue obtained was purified by flash column chromatography (silica gel 40 g, eluting 0-100% ethyl acetate in hexane) to afford 1-(3-cyanophenyl)-N-(3-((cyclopropylmethylamino)(3-methoxyphenyl)methyl)phenyl)-3-(trifluoromethyl)-1H-pyrazole-5-carboxamide (109d) (1.3 g, 2.383 mmol, 51.7% yield) as a white solid; $^1$H NMR (300 MHz, DMSO-d$_6$) δ 10.63 (s, 1H), 8.19-8.14 (m, 1H), 8.00 (dt, J=7.9, 1.3 Hz, 1H), 7.90 (ddd, J=8.2, 2.2, 1.1 Hz, 1H), 7.77-7.69 (m, 2H), 7.67 (t, J=1.9 Hz, 1H), 7.54 (dt, J=8.0, 1.7 Hz, 1H), 7.26 (d, J=7.7 Hz, 1H), 7.23-7.19 (m, 1H), 7.17 (d, J=7.8 Hz, 1H), 6.99 (dd, J=2.6, 1.5 Hz, 1H), 6.95 (d, J=7.9 Hz, 1H), 6.75 (ddd, J=8.2, 2.7, 1.0 Hz, 1H), 4.79 (s, 1H), 3.70 (s, 3H), 2.34 (s, 1H), 2.29 (d, J=7.1 Hz, 2H), 0.99-0.85 (m, 1H), 0.43-0.33 (m, 2H), 0.09-0.02 (m, 2H);

$^{19}$F NMR (282 MHz, DMSO-d$_6$) δ −60.95; IR (KBr) 2234 cm-1; MS (ES+) 546.3 (M+1); (ES−) 544.4 (M−1).

Step-4: Preparation of tert-Butyl 3-(5-(3-(((cyclopropylmethylamino)(3-methoxyphenyl)methyl)phenylcarbamoyl)-3-(trifluoromethyl)-1H-pyrazol-1-yl)benzylcarbamate (109e)

To a solution of 1-(3-cyanophenyl)-N-(3-((cyclopropylmethylamino)(3-methoxyphenyl)methyl)phenyl)-3-(trifluoromethyl)-1H-pyrazole-5-carboxamide (109d) (1.2 g, 2.200 mmol) in MeOH (20 mL) cooled with ice/water was added di-tert-butyl dicarbonate (1.44 g, 6.6 mmol) and nickel(II) chloride (0.575 g, 2.420 mmol). Sodium borohydride (0.679 g, 17.60 mmol) was added slowly over 15 min and reaction mixture was stirred at room temperature for 1 h. The reaction mixture was quenched with N1-(2-aminoethyl)ethane-1,2-diamine (0.720 mL, 6.60 mmol) stirred for 0.5 h and concentrated in vacuum to dryness. The residue obtained was dissolved in dichloromethane (60 mL) and water (60 mL). The aqueous phase was separated and extracted again with dichloromethane (60 mL). The organic extracts were combined, washed with brine (60 mL), dried over MgSO$_4$, filtered and concentrated in vacuum to dryness. The residue obtained was purified by flash column chromatography (silica gel 24 g with 0-100% 9:1 ethyl acetate/methanol in hexane) to afford tert-butyl 3-(5-(3-((cyclopropylmethylamino)(3-methoxyphenyl)methyl)phenylcarbamoyl)-3-(trifluoromethyl)-1H-pyrazol-1-yl)benzylcarbamate (109e) (0.375 g, 0.577 mmol, 26.2% yield) as a white solid; $^1$H NMR (300 MHz, DMSO-d$_6$) δ 10.69 (s, 1H), 7.67-7.62 (m, 1H), 7.58 (s, 1H), 7.52 (t, J=6.6 Hz, 1H), 7.49-7.38 (m, 2H), 7.38-7.31 (m, 2H), 7.28-7.13 (m, 3H), 7.02-6.98 (m, 1H), 6.96 (d, J=7.9 Hz, 1H), 6.75 (ddd, J=8.3, 2.6, 1.0 Hz, 1H), 4.78 (s, 1H), 4.19 (d, J=6.2 Hz, 2H), 3.71 (s, 3H), 2.42-2.31 (m, 1H), 2.29 (d, J=7.3 Hz, 2H), 1.36 (s, 9H), 1.00-0.78 (m, 1H), 0.45-0.29 (m, 2H), 0.12-0.01 (m, 2H); $^{19}$F NMR (282 MHz, DMSO-d$_6$) δ −60.79; MS (ES+) 650.4 (M+1); (ES−) 648.3 (M−1).

Step-5: Preparation of 1-(3-(Aminomethyl)phenyl)-N-(3-((cyclopropylmethylamino)(3-methoxyphenyl)methyl)phenyl)-3-(trifluoromethyl)-1H-pyrazole-5-carboxamide (109f)

To a solution of tert-butyl 3-(5-(3-((cyclopropylmethylamino)(3-methoxyphenyl)methyl)phenylcarbamoyl)-3-(trifluoromethyl)-1H-pyrazol-1-yl)benzylcarbamate (109e) (0.364 g, 0.560 mmol) in methanol (30 mL) was added conc. hydrogen chloride (1.167 mL, 14.01 mmol), stirred at room temperature overnight and concentrated in vacuum to dryness. The residue obtained was purified by flash column chromatography (silica gel 12 g, eluting with 0-50% methanol in chloroform) to afford 1-(3-(aminomethyl)phenyl)-N-(3-((cyclopropylmethylamino)(3-methoxyphenyl)methyl)phenyl)-3-(trifluoromethyl)-1H-pyrazole-5-carboxamide (109f) (0.160 g, 0.291 mmol, 52.0% yield) as a white solid; $^1$H NMR (300 MHz, DMSO-d$_6$) δ 10.83 (s, 1H), 7.76-7.68 (m, 3H), 7.65 (dt, J=7.4, 1.6 Hz, 1H), 7.61-7.46 (m, 3H), 7.30-7.15 (m, 3H), 7.05-7.00 (m, 1H), 6.97 (d, J=7.7 Hz, 1H), 6.81-6.71 (m, 1H), 4.83 (s, 1H), 4.09 (s, 2H), 3.71 (s, 3H), 2.31 (dd, J=6.7, 2.5 Hz, 2H), 1.05-0.79 (m, 1H), 0.51-0.26 (m, 2H), 0.16-−0.02 (m, 2H); $^{19}$F NMR (282 MHz, DMSO-d$_6$) δ −60.59; MS (ES+) 550.4 (M+1); (ES−) 548.3 (M−1); Analysis calculated for C$_{30}$H$_{30}$F$_3$N$_5$O$_2$.HCl.1.25H$_2$O: C, 59.21; H, 5.55; Cl, 5.83; N, 11.51; Found: C, 59.44; H, 5.64; Cl, 5.64; N, 11.15.

Scheme 110

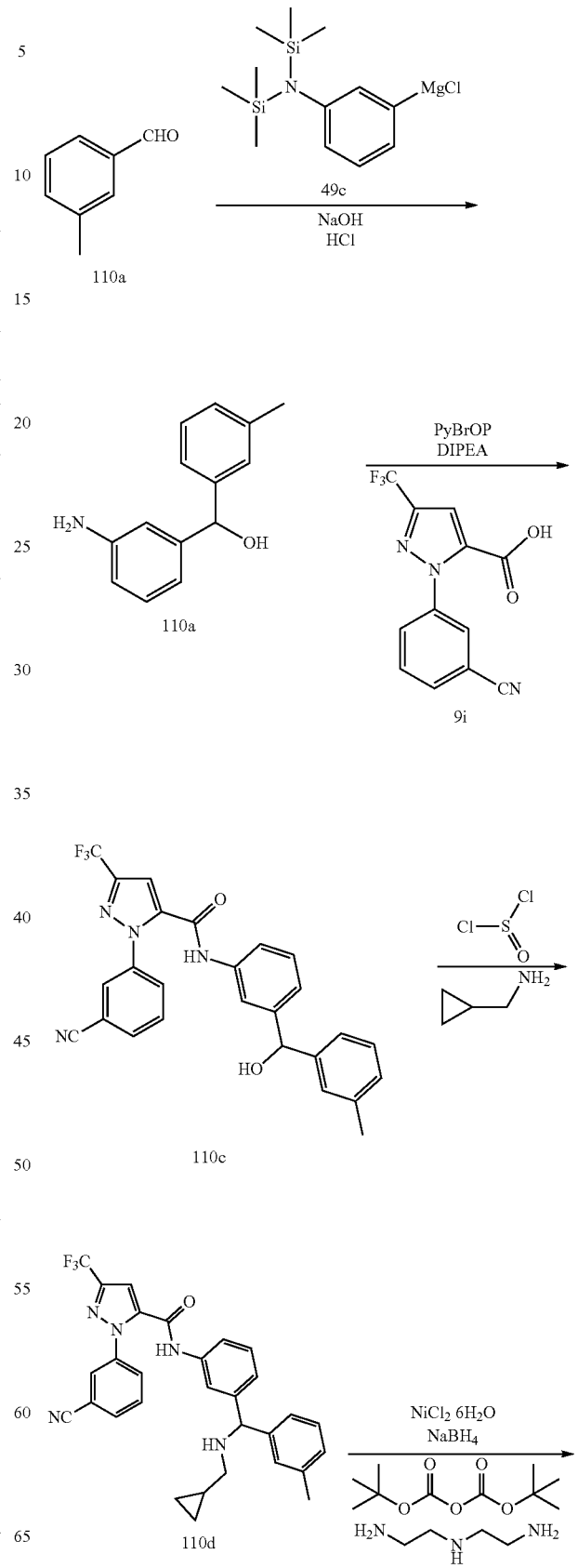

-continued

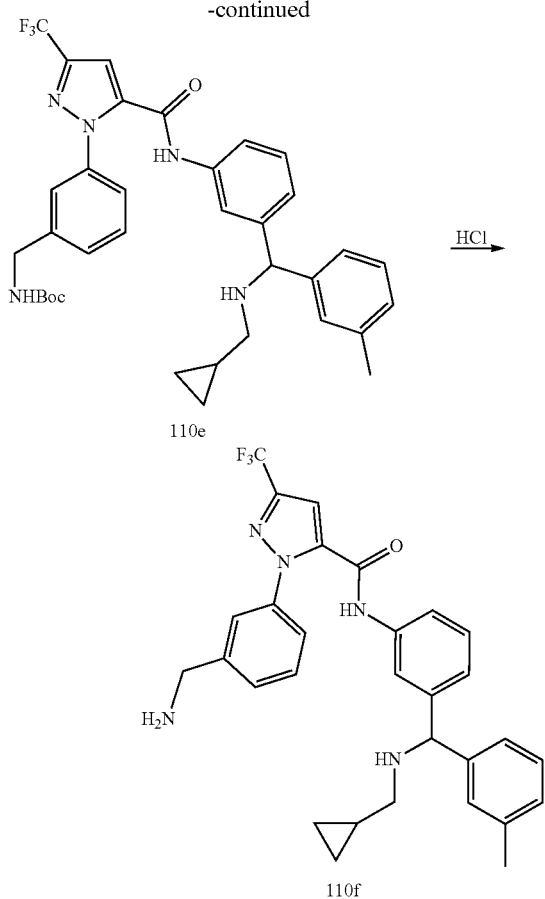

Preparation of 1-(3-(Aminomethyl)phenyl)-N-(3-((cyclopropylmethylamino)(m-tolyl)methyl)phenyl)-3-(trifluoromethyl)-1H-pyrazole-5-carboxamide (110f)

Step-1: Preparation of (3-aminophenyl)(m-tolyl)methanol (110b)

To a stirred solution of 3-methylbenzaldehyde (110a) (1.179 mL, 10 mmol) in tetrahydrofuran (5 mL) was added (3-(bis(trimethylsilyl)amino)phenyl)magnesium chloride (49c) (12.00 mL, 12.00 mmol) at 0° C. The reaction was stirred for 14 h at same temperature and quenched by adding 2 N HCl (12.50 mL, 25 mmol), stirred for 6 h. The reaction mixture was treated with 2 N NaOH (15 mL) and extracted with ethyl acetate (2×50 mL). The organic layers were combined washed with sat. NH$_4$Cl (50 mL), dried over anhydrous MgSO$_4$, filtered, evaporated to dryness. The crude residue was purified by flash column chromatography (silica gel 40 g, eluting with ethyl acetate in hexane from 0-100%) to furnish (3-aminophenyl)(m-tolyl)methanol (110b) (1.393 g, 65% yield) a yellow solid; $^1$H NMR (300 MHz, DMSO-d$_6$) δ 7.22-7.09 (m, 3H), 6.99 (dt, J=6.4, 1.9 Hz, 1H), 6.91 (t, J=7.7 Hz, 1H), 6.56 (t, J=2.0 Hz, 1H), 6.50 (dt, J=7.6, 1.3 Hz, 1H), 6.37 (ddd, J=7.9, 2.4, 1.1 Hz, 1H), 5.64 (d, J=3.8 Hz, 1H, D$_2$O exchangeable), 5.45 (d, J=3.8 Hz, 1H), 4.98 (s, 2H, D$_2$O exchangeable), 2.26 (s, 3H); MS (ES$^+$) 214.2 (M+1), 236.2 (M+Na), MS (ES−) 212.1 (M−1).

Step-2: Preparation of 1-(3-cyanophenyl)-N-(3-(hydroxy(m-tolyl)methyl)phenyl)-3-(trifluoromethyl)-1H-pyrazole-5-carboxamide (110c)

In a 100 mL single-necked flask 1-(3-cyanophenyl)-3-(trifluoromethyl)-1H-pyrazole-5-carboxylic acid (9i) (1.74 (36.0 mL, 465 mmol) and N-ethyl-N-isopropylpropan-2-amine (DIPEA) (5.40 mL, 31.0 mmol) successively in a positive flow of nitrogen at room temperature. The resulting reaction mixture was stirred at room temperature for 16 h under a positive flow of nitrogen atmosphere. Excess DMF was pumped-off under reduced pressure. The residue was treated with water (50 mL), and extracted with chloroform (2×50 mL) combined organics were dried over anhydrous MgSO$_4$, filtered, evaporated to dryness. The residue was then purified by flash column chromatography [silica gel 40 g, eluting with methanol in chloroform from 0-100%] to furnish 1-(3-cyanophenyl)-N-(3-(hydroxy(m-tolyl)methyl)phenyl)-3-(trifluoromethyl)-1H-pyrazole-5-carboxamide (110c) (2.308 g, 78% yield) as a white solid; $^1$H NMR (300 MHz, DMSO-d$_6$) δ 10.63 (s, 1H, D$_2$O exchangeable), 8.16 (t, J=1.8 Hz, 1H), 8.00 (dt, J=7.8, 1.3 Hz, 1H), 7.90 (ddd, J=8.2, 2.2, 1.1 Hz, 1H), 7.79-7.69 (m, 2H), 7.62 (t, J=1.8 Hz, 1H), 7.55 (dd, J=8.1, 1.5 Hz, 1H), 7.26 (t, J=7.8 Hz, 1H), 7.22-7.10 (m, 4H), 7.01 (d, J=7.1 Hz, 1H), 5.90 (d, J=3.8 Hz, 1H, D$_2$O exchangeable), 5.62 (d, J=3.8 Hz, 1H), 2.26 (s, 3H); $^{19}$F NMR (282 MHz, DMSO-d$_6$) δ −60.95; MS (ES$^+$): MS (ES+) 499.2 (M+Na), 975.4 (2M+Na), MS (ES−) 475.3 (M−1); IR (KBr, cm$^{-1}$): 2235 cm$^{-1}$ (—CN stretching).

Step-3: Preparation of 1-(3-Cyanophenyl)-N-(3-((cyclopropylmethylamino)(m-tolyl)methyl)phenyl)-3-(trifluoromethyl)-1H-pyrazole-5-carboxamide (110d)

To a solution of 1-(3-cyanophenyl)-N-(3-(hydroxy(m-tolyl)methyl)phenyl)-3-(trifluoromethyl)-1H-pyrazole-5-carboxamide (110c) (2.31 g, 4.85 mmol) in dichloromethane (25 mL) at 0° C. was added thionyl chloride (1.06 mL, 14.55 mmol) and stirred at room temperature for 2 h. The reaction mixture was quenched with cyclopropylmethanamine (1.262 mL, 14.55 mmol) and stirred at room temperature for additional 5 h. The reaction mixture was concentrated in vacuum to dryness. The residue obtained was dissolved in acetonitrile (10 mL) and added cyclopropylmethanamine (8.41 mL, 97 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum. The residue obtained was purified by flash column chromatography (silica gel 40 g, eluting 0-100% ethyl acetate in hexane) to afford 1-(3-cyanophenyl)-N-(3-((cyclopropylmethylamino)(m-tolyl)methyl)phenyl)-3-(trifluoromethyl)-1H-pyrazole-5-carboxamide (110d) (1.784 g, 3.37 mmol, 69.5% yield) as a white solid; $^1$H NMR (300 MHz, DMSO-d$_6$) δ 10.63 (s, 1H), 8.19-8.13 (m, 1H), 8.00 (dt, J=7.7, 1.3 Hz, 1H), 7.90 (ddd, J=8.3, 2.2, 1.1 Hz, 1H), 7.79-7.69 (m, 2H), 7.68-7.63 (m, 1H), 7.54 (dt, J=8.0, 1.7 Hz, 1H), 7.30-7.12 (m, 5H), 6.99 (dd, J=6.3, 2.1 Hz, 1H), 4.77 (s, 1H), 2.29 (s, 3H), 2.26 (s, 3H), 1.03-0.84 (m, 1H), 0.44-0.31 (m, 2H), 0.09-0.01 (m, 2H); $^{19}$F NMR (282 MHz, DMSO) δ −60.94; IR (KBr) 2234 cm$^{-1}$; MS (ES+) 530.3 (M+1); (ES−) 528.3 (M−1).

Step-4: Preparation of tert-Butyl 3-(5-(3-((cyclopropylmethylamino)(m-tolyl)methyl)phenylcarbamoyl)-3-(trifluoromethyl)-1H-pyrazol-1-yl)benzylcarbamate (110e)

To a solution of 1-(3-cyanophenyl)-N-(3-((cyclopropylmethylamino)(m-tolyl)methyl)phenyl)-3-(trifluoromethyl)-

1H-pyrazole-5-carboxamide (110d) (1.2 g, 2.266 mmol) in MeOH (20 mL) cooled with ice/water was added di-tert-butyl dicarbonate (1.5 g, 6.87 mmol) and nickel(II) chloride (0.599 g, 2.52 mmol). Sodium Borohydride (0.708 g, 18.33 mmol) was added slowly over 15 min and reaction mixture was stirred at room temperature for 1 h. The reaction mixture was quenched with N1-(2-aminoethyl)ethane-1,2-diamine (0.750 mL, 6.87 mmol) stirred for 0.5 h and concentrated in vacuum to dryness. The residue obtained was dissolved in dichloromethane (60 mL) and water (60 mL). The aqueous phase separated and extracted again with dichloromethane (60 mL). The organic extracts were combined, washed with brine (60 mL), dried over MgSO$_4$, filtered and concentrated in vacuum to dryness. The residue obtained was purified by flash column chromatography (silica gel 24 g with 0-100% 9:1 ethyl acetate/methanol in hexane) to afford tert-butyl 3-(5-(3-((cyclopropylmethylamino)(m-tolyl)methyl)phenyl carbamoyl)-3-(trifluoromethyl)-1H-pyrazol-1-yl)benzylcarbamate (110e) (1.0 g, 1.578 mmol, 68.9% yield) as a white solid; $^1$H NMR (300 MHz, DMSO-d$_6$) δ 10.69 (s, 1H), 7.63 (t, J=1.8 Hz, 1H), 7.58 (s, 1H), 7.56-7.46 (m, 2H), 7.45-7.38 (m, 2H), 7.38-7.31 (m, 2H), 7.25 (d, J=7.7 Hz, 1H), 7.22-7.13 (m, 4H), 6.99 (dt, J=6.7, 2.0 Hz, 1H), 4.76 (s, 1H), 4.19 (d, J=6.2 Hz, 2H), 2.29 (s, 3H), 2.26 (s, 3H), 1.36 (d, J=1.9 Hz, 9H), 0.99-0.82 (m, 1H), 0.42-0.33 (m, 2H), 0.10--0.01 (m, 2H); $^{19}$F NMR (282 MHz, DMSO-d$_6$) δ −60.80; MS (ES+) 634.4 (M+1); (ES−) 632.4 (M−1).

Step-5: Preparation of 1-(3-(Aminomethyl)phenyl)-N-(3-((cyclopropylmethylamino)(m-tolyl)methyl)phenyl)-3-(trifluoromethyl)-1H-pyrazole-5-carboxamide (110f)

To a solution of tert-butyl 3-(5-(3-((cyclopropylmethylamino)(m-tolyl)methyl)phenylcarbamoyl)-3-(trifluoromethyl)-1H-pyrazol-1-yl)benzylcarbamate (110e) (0.92 g, 1.452 mmol) in methanol (50 mL) was added conc. hydrogen chloride (3.02 mL, 36.3 mmol), stirred at room temperature overnight and concentrated in vacuum to dryness. The residue obtained was purified by flash column chromatography (silica gel 24 g, eluting with 0-50% methanol in chloroform) to afford 1-(3-(aminomethyl)phenyl)-N-(3-((cyclopropylmethylamino)(m-tolyl)methyl)phenyl)-3-(trifluoromethyl)-1H-pyrazole-5-carboxamide (110f) (0.67 g, 1.256 mmol, 86% yield) as a white solid; $^1$H NMR (300 MHz, DMSO-d$_6$) δ 10.92 (s, 1H), 8.51 (t, J=55.0 Hz, 3H), 7.83 (s, 1H), 7.72 (d, J=1.9 Hz, 1H), 7.71 (s, 1H), 7.64 (dt, J=7.2, 1.8 Hz, 1H), 7.61-7.56 (m, 1H), 7.56-7.48 (m, 2H), 7.47-7.34 (m, 3H), 7.28 (t, J=7.9 Hz, 1H), 7.14 (d, J=7.5 Hz, 1H), 5.36 (s, 1H), 4.12 (s, 2H), 2.70-2.57 (m, 2H), 2.29 (s, 3H), 1.20-1.04 (m, 1H), 0.65-0.41 (m, 2H), 0.38-0.15 (m, 2H); $^{19}$F NMR (282 MHz, DMSO) δ −60.60; MS (ES+) 534.4 (M+1); (ES−) 532.3 (M−1); Analysis calculated for $C_{30}H_{30}F_3N_5O \cdot 2HCl \cdot 1.75H_2O$: C, 56.47; H, 5.61; Cl, 11.11; N, 10.98; Found: C, 56.59; H, 5.45; Cl, 10.93; N, 10.92.

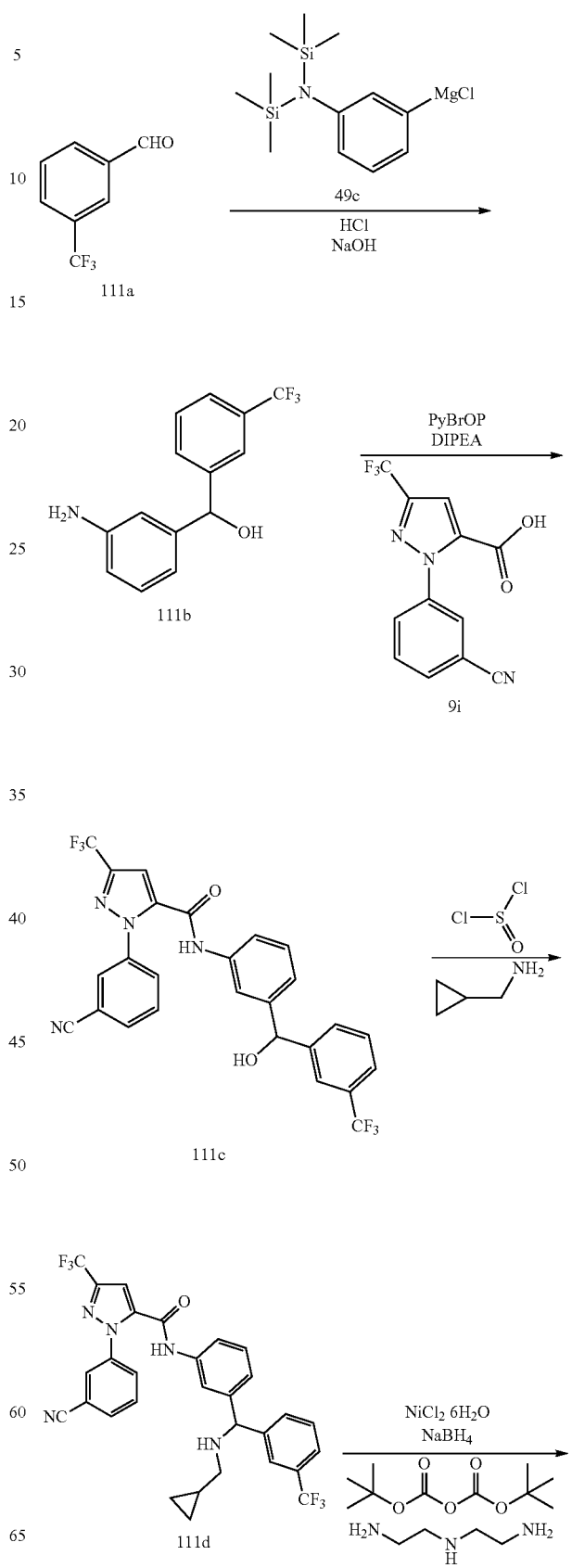

Scheme 111

-continued

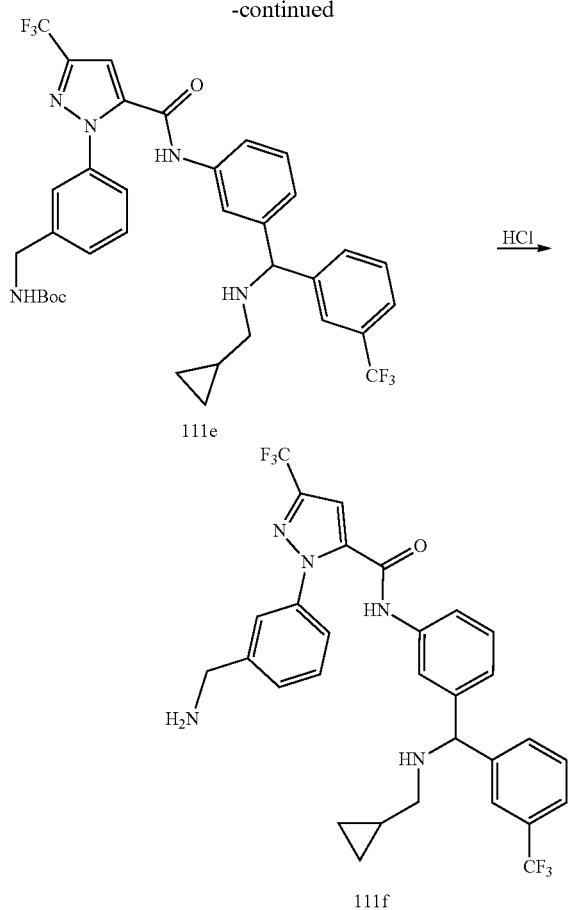

111e

111f

Preparation of 1-(3-(Aminomethyl)phenyl)-N-(3-((cyclopropylmethylamino)(3-(trifluoromethyl) phenyl)methyl)phenyl)-3-(trifluoromethyl)-1H-pyrazole-5-carboxamide (111f)

Step-1: Preparation of (3-Aminophenyl)(3-(trifluoromethyl)phenyl)methanol (111b)

To a stirred solution of 3-(trifluoromethyl) benzaldehyde (111a) (1.741 g, 10 mmol) in tetrahydrofuran (5 mL) was added 3-[bis(trimethylsilyl)amino]phenylmagnesium chloride solution (49c) (12 mL) at 0° C. The reaction was stirred for 14 h at same temperature and quenched by adding 2 N HCl (12.50 mL), stirred for 6 h. The reaction mixture was treated with 2 N NaOH (15 mL) and extracted with ethyl acetate (2×30 mL). The organic layers were combined washed with saturated aqueous NH$_4$Cl (30 mL), dried over anhydrous MgSO$_4$, filtered, evaporated to dryness. The crude residue was purified by flash column chromatography (silica gel 40 g, eluting with ethyl acetate in hexane from 0-100%) to furnish 3-(trifluoromethyl)benzaldehyde (111b) (1.121 g, 42% yield) as yellow solid; $^1$H NMR (300 MHz, DMSO-d$_6$) δ 7.74-7.48 (m, 4H), 6.94 (t, J=7.7 Hz, 1H), 6.64-6.49 (m, 2H), 6.40 (ddd, J=8.0, 2.3, 1.1 Hz, 1H), 5.95 (d, J=3.9 Hz, 1H, D$_2$O exchangeable), 5.62 (d, J=3.9 Hz, 1H), 5.07 (s, 2H, D$_2$O exchangeable); $^{19}$F NMR (282 MHz, DMSO-d$_6$) δ −60.92; MS (ES$^+$): MS (ES+) 268.2 (M+1), 290.1 (M+Na), MS (ES−) 266.15 (M−1).

Step-2: Preparation of 1-(3-cyanophenyl)-N-(3-(hydroxy(3-(trifluoromethyl)phenyl)methyl)phenyl)-3-(trifluoromethyl)-1H-pyrazole-5-carboxamide (111c)

In a 100 mL single-necked flask containing 1-(3-cyanophenyl)-3-(trifluoromethyl)-1H-pyrazole-5-carboxylic acid (9i) (1.075 g, 3.82 mmol), (3-aminophenyl)(3-(trifluoromethyl)phenyl)methanol (111b) (1.022 g, 3.82 mmol), bromo-tris-pyrrolidino phosphoniumhexafluorophosphate (Py-BrOP, 2.139 g, 4.59 mmol) was added N,N-dimethylformamide (22 mL) and N-ethyl-N-isopropylpropan-2-amine (3.33 mL, 19.12 mmol) successively in a positive flow of nitrogen at room temperature. The resulting reaction mixture was stirred at room temperature for 16 h under a positive flow of nitrogen atmosphere. Excess DMF was pumped-off under reduced pressure. The residue was treated with water (30 mL), and extracted with chloroform (2×50 mL). The combined organic layers were dried over anhydrous MgSO$_4$, filtered and evaporated to dryness. The residue was then purified by flash column chromatography [silica gel 40 g, eluting with methanol in chloroform from 0-100%] to furnish 1-(3-cyanophenyl)-N-(3-(hydroxy(3-(trifluoromethyl)phenyl)methyl)phenyl)-3-(trifluoromethyl)-1H-pyrazole-5-carboxamide (111c) (1.293 g, 2.438 mmol, 63.8% yield) as a yellow solid; MS (ES+) 553.2 (M+Na); (ES−) 529.2 (M−1) which was used as such for next step.

Step-3: Preparation of 1-(3-cyanophenyl)-N-(3-((cyclopropylmethylamino)(3-(trifluoromethyl)phenyl)methyl)phenyl)-3-(trifluoromethyl)-1H-pyrazole-5-carboxamide (111d)

To a solution of 1-(3-cyanophenyl)-N-(3-(hydroxy(3-(trifluoromethyl)phenyl)methyl)phenyl)-3-(trifluoromethyl)-1H-pyrazole-5-carboxamide (111c) (1.238 g, 2.334 mmol) in dichloromethane (25 mL) at 0° C. was added thionyl chloride (0.551 mL, 7 mmol) and stirred at room temperature for 2 h. The reaction mixture was quenched with cyclopropylmethanamine (1.4 mL, 16.34 mmol) and stirred at room temperature for additional 5 h. The reaction mixture was concentrated in vacuum to dryness. The residue obtained was dissolved in acetonitrile (10 mL) and added cyclopropylmethanamine (4.0 mL, 46.7 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum. The residue obtained was purified by flash column chromatography (silica gel 40 g, eluting 0-100% ethyl acetate in hexane) to afford 1-(3-cyanophenyl)-N-(3-((cyclopropylmethylamino)(3-(trifluoromethyl)phenyl)methyl)phenyl)-3-(trifluoromethyl)-1H-pyrazole-5-carboxamide (111d) (1.047 g, 77% yield) as a white solid; $^1$H NMR (300 MHz, DMSO-d$_6$) δ 10.65 (s, 1H, D$_2$O exchangeable), 8.16 (t, J=1.8 Hz, 1H), 8.00 (dt, J=7.7, 1.3 Hz, 1H), 7.90 (ddd, J=8.2, 2.2, 1.1 Hz, 1H), 7.82-7.66 (m, 5H), 7.60-7.51 (m, 3H), 7.35-7.19 (m, 2H), 4.96 (s, 1H), 2.30 (dd, J=13.8, 7.0 Hz, 2H), 1.00-0.84 (m, 1H), 0.45-0.31 (m, 2H), 0.04 (td, J=5.4, 3.8 Hz, 2H); 19F NMR (282 MHz, DMSO-d$_6$) δ −60.85, −60.96. MS (ES+) 584.3 (M+1), MS (ES−) 582.2 (M−1).

Step-4: Preparation of tert-Butyl 3-(5-(3-((cyclopropylmethylamino)(3-(trifluoromethyl)phenyl)methyl)phenylcarbamoyl)-3-(trifluoromethyl)-1H-pyrazol-1-yl)benzylcarbamate (111e)

To a solution of 1-(3-cyanophenyl)-N-(3-((cyclopropylmethylamino)(3-(trifluoromethyl)phenyl)methyl)phenyl)-3-

(trifluoromethyl)-1H-pyrazole-5-carboxamide (111 d) (0.996 g, 1.707 mmol) in MeOH (20 mL) cooled with ice/water was added di-tert-butyl dicarbonate (1.5 g, 6.87 mmol) and nickel(II) chloride (0.599 g, 2.52 mmol). Sodium Borohydride (0.708 g, 18.33 mmol) was added slowly over 15 min and reaction mixture was stirred at room temperature for 1 h. The reaction mixture was quenched with N1-(2-aminoethyl)ethane-1,2-diamine (0.750 mL, 6.87 mmol) stirred for 0.5 h and concentrated in vacuum to dryness. The residue obtained was dissolved in dichloromethane (60 mL) and water (60 mL). The aqueous phase was separated and extracted again with dichloromethane (60 mL). The organic extracts were combined, washed with brine (60 mL), dried over $MgSO_4$, filtered and concentrated in vacuum to dryness. The residue obtained was purified by flash column chromatography (silica gel 24 g with 0-100% 9:1 ethyl acetate/methanol in hexane) to afford tert-butyl 3-(5-(3-((cyclopropylmethylamino)(3-(trifluoromethyl)phenyl)methyl)phenylcarbamoyl)-3-(trifluoromethyl)-1H-pyrazol-1-yl)benzylcarbamate (ille) (0.26 g, 16.50% yield) as a white solid; $^1$H NMR (300 MHz, DMSO-$d_6$) δ 10.71 (s, 1H), 7.79 (s, 1H), 7.71 (dd, J=5.3, 3.7 Hz, 1H), 7.66 (t, J=1.8 Hz, 1H), 7.56 (d, J=8.1 Hz, 3H), 7.51 (d, J=7.3 Hz, 1H), 7.45-7.38 (m, 2H), 7.38-7.32 (m, 2H), 7.28 (d, J=7.7 Hz, 1H), 7.24 (s, 1H), 5.03-4.81 (m, 1H), 4.19 (d, J=6.2 Hz, 2H), 2.60 (dd, J=13.6, 3.4 Hz, 1H), 2.37-2.18 (m, 2H), 1.35 (s, 9H), 0.99-0.83 (m, 1H), 0.45-0.32 (m, 2H), 0.09-0.00 (m, 2H); $^{19}$F NMR (282 MHz, DMSO) δ −60.85; MS (ES+) 688.4 (M+1); (ES−) 686.4 (M−1).

Step-5: Preparation of 1-(3-(Aminomethyl)phenyl)-N-(3-((cyclopropylmethylamino)(3-(trifluoromethyl)phenyl)methyl)phenyl)-3-(trifluoromethyl)-1H-pyrazole-5-carboxamide (111f)

To a solution of tert-butyl 3-(5-(3-((cyclopropylmethylamino)(3-(trifluoromethyl)phenyl)methyl)phenylcarbamoyl)-3-(trifluoromethyl)-1H-pyrazol-1-yl)benzylcarbamate (111e) (0.25 g, 0.364 mmol) in methanol (10 mL) was added conc. hydrogen chloride (0.757 mL, 9.09 mmol), stirred at room temperature overnight and concentrated in vacuum to dryness. The residue obtained was purified by flash column chromatography (silica gel 12 g, eluting with 0-50% methanol in chloroform) to afford 1-(3-(aminomethyl)phenyl)-N-(3-((cyclopropylmethylamino)(3-(trifluoromethyl)phenyl)methyl) phenyl)-3-(trifluoromethyl)-1H-pyrazole-5-carboxamide (111f) (0.132 g, 0.225 mmol, 61.8% yield) as a white solid; $^1$H NMR (300 MHz, DMSO-$d_6$) δ 11.02 (s, 1H), 10.40 (s, 2H), 8.78-8.39 (m, 3H), 8.14 (s, 1H), 8.05 (d, J=7.7 Hz, 1H), 7.92 (s, 1H), 7.77-7.60 (m, 7H), 7.59-7.49 (m, 2H), 7.44 (t, J=7.9 Hz, 1H), 5.75 (s, 1H), 4.12 (s, 2H), 2.69 (d, J=6.7 Hz, 2H), 1.16 (dd, J=13.3, 6.6 Hz, 1H), 0.69-0.45 (m, 2H), 0.41-0.21 (m, 2H); $^{19}$F NMR (282 MHz, DMSO-$d_6$) δ −60.60, −60.76; MS (ES+) 588.3 (M+1); (ES−) 586.3 (M−1); Analysis calculated for $C_{30}H_{27}F_6N_5O_2 \cdot HCl \cdot 1.75H_2O$: C, 52.07; H, 4.73; Cl, 10.25; N, 10.12; Found: C, 51.94; H, 4.60; Cl, 10.63; N, 10.05.

Scheme 112

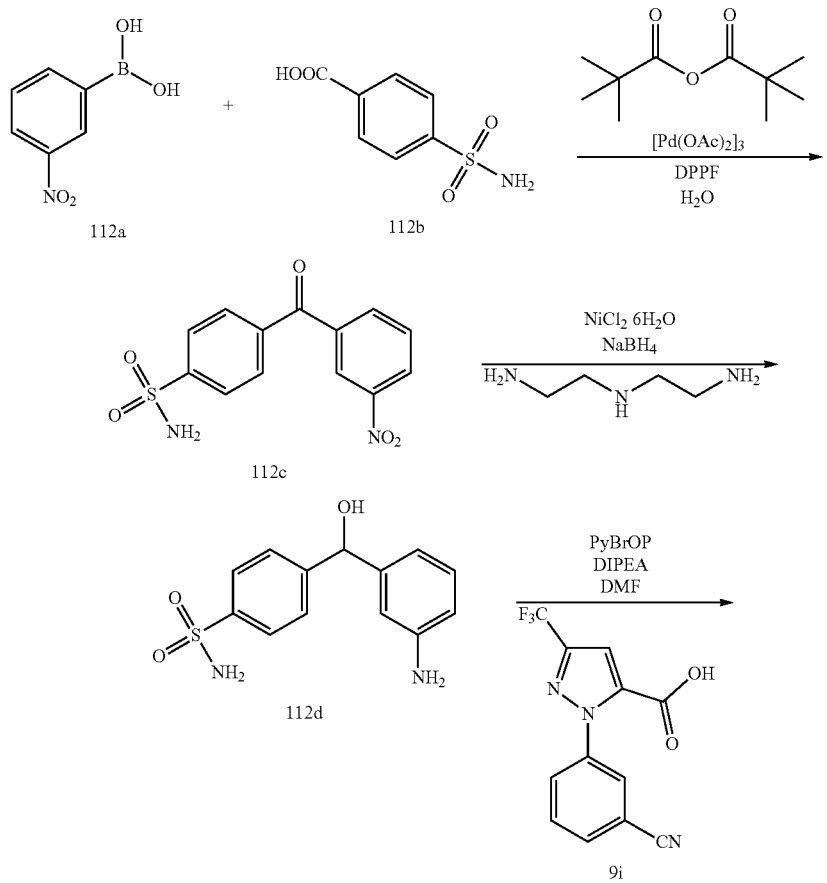

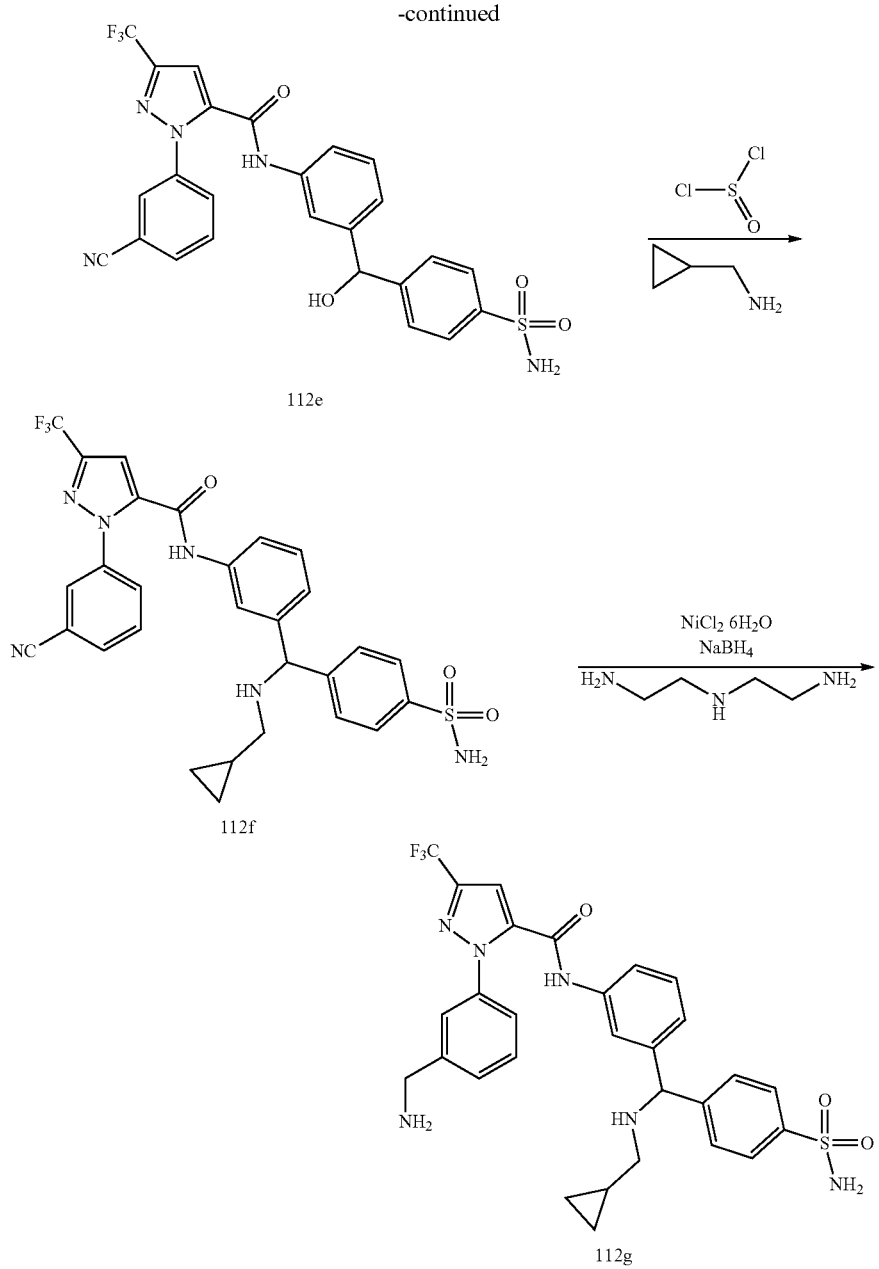

Preparation of 1-(3-(aminomethyl)phenyl)-N-(3-((cyclopropylmethylamino)(4-sulfamoylphenyl)methyl)phenyl)-3-(trifluoromethyl)-1H-pyrazole-5-carboxamide (112g)

Step-1: Preparation of 4-(3-nitrobenzoyl)benzenesulfonamide (112c)

A mixture of 4-sulfamoylbenzoic acid (112b) (1 g, 4.97 mmol), 3-nitrophenylboronic acid (112a) (0.996 g, 5.96 mmol), diacetoxypalladium (0.335 g, 0.497 mmol), 1,1'-bis(diphenylphosphino)ferrocene (DPPF) (0.551 g, 0.994 mmol), pivalic anhydride (1.513 mL, 7.46 mmol) was degassed and purged with nitrogen, treated THF (20 mL) and water (0.224 mL, 12.43 mmol) in a positive flow of nitrogen. The reaction mixture was heated to 60° C. and stirred for 16 h at that temperature in a positive flow of nitrogen. TLC analysis (ethyl acetate/hexanes, v/v/3/7) shows good conversion. The reaction mixture was cooled to room temperature. Excess THF was pumped-off under reduced pressure to dryness, the obtained residue was diluted with saturated aqueous NH$_4$Cl (50 mL). The product was extracted with ethyl acetate (2×50 mL). The combined organics layers were dried over anhydrous MgSO$_4$, filtered and evaporated to dryness. The residue was purified by flash column chromatography [(silica gel 40 g, eluting with ethyl acetate/hexanes from 0 to 50%)] to furnish 4-(3-nitrobenzoyl)benzenesulfonamide (112c) (311 mg, 20% yield) as a white solid; $^1$H NMR (300 MHz, DMSO-d$_6$) δ 8.55 (ddd, J=8.3, 2.4, 1.1 Hz, 1H), 8.46 (t, J=2.0 Hz, 1H), 8.20 (dt, J=7.7, 1.3 Hz, 1H), 8.06-7.95 (m, 4H), 7.89 (t, J=8.0 Hz, 1H), 7.63 (s, 2H, D$_2$O exchangeable); MS (ES$^+$): MS (ES+)

329.1 (M+1), MS (ES−) 305.1 (M−1), 611.0 (2M−1); Analysis calculated for $C_{13}H_{10}N_2O_5S$: C, 50.98; H, 3.29; N, 9.15; S, 10.47; Found: C, 50.93; H, 3.36; N, 9.12; S, 10.27.

Step-2: Preparation of 4-((3-aminophenyl)(hydroxy) methyl)benzenesulfonamide (112d)

To a stirred solution of 4-(3-nitrobenzoyl)benzenesulfonamide (112c) (0.256 g, 0.836 mmol) in anhydrous methanol (20 mL) cooled to 0° C. was added nickel(II) chloride hexahydrate (0.248 g, 1.045 mmol) followed by sodium borohydride (0.253 g, 6.69 mmol) in small portions over a period of 5 min. The reaction mixture was stirred for 45 min at 0° C., TLC analysis (ethyl acetate/hexanes, 2/2, v/v) shows reaction was complete at this point N1-(2-aminoethyl)ethane-1,2-diamine (0.903 mL, 8.36 mmol) was added. The mixture was stirred for 30 minutes and concentrated in vacuum to dryness. The residue was treated with water (50 mL), and extracted with ethyl acetate (2×50 mL). The combined organic layers were dried over anhydrous $MgSO_4$, filtered and excess solvents were pumped-off under reduced pressure. The residue was purified by flash column chromatography [(silica gel 25 g, eluting with ethyl acetate/hexanes from 0 to 50%)] to furnish 4-((3-aminophenyl)(hydroxy)methyl)benzenesulfonamide (112d) (136 mg, 58% yield) as a white solid; $^1H$ NMR (300 MHz, DMSO-$d_6$) δ 7.82-7.69 (m, 2H), 7.55-7.44 (m, 2H), 7.25 (s, 2H), 6.92 (t, J=7.7 Hz, 1H), 6.58-6.47 (m, 2H), 6.39 (ddd, J=7.9, 2.3, 1.0 Hz, 1H), 5.89 (d, J=3.9 Hz, 1H, $D_2O$ exchangeable), 5.58 (d, J=3.8 Hz, 1H), 5.01 (s, 2H, $D_2O$ exchangeable); MS (ES$^+$): MS (ES+) 301.2 (M+Na), 579.2 (2M+Na), MS (ES−) 277.2 (M−1) 555.2 (2M−1).

Step-3: Preparation of 1-(3-cyanophenyl)-N-(3-(hydroxy(4-sulfamoylphenyl)methyl)phenyl)-3-(trifluoromethyl)-1H-pyrazole-5-carboxamide (112e)

In a 100 mL single-necked flask containing 1-(3-cyanophenyl)-3-(trifluoromethyl)-1H-pyrazole-5-carboxylic acid (9i) (0.130 g, 0.462 mmol), 4-((3-aminophenyl)(hydroxy)methyl)benzenesulfonamide (112d) (0.129 g, 0.462 mmol), bromo-tris-pyrrolidino phosphoniumhexafluorophosphate (PyBrOP, 0.259 g, 0.555 mmol) was added N,N-dimethylformamide (3 mL) and N-ethyl-N-isopropylpropan-2-amine (DIPEA) (0.403 mL, 2.312 mmol) successively in a positive flow of nitrogen at room temperature. The resulting reaction mixture was stirred at room temperature for 16 h under a positive flow of nitrogen atmosphere. Excess DMF was pumped-off under reduced pressure. The residue was treated with water (30 mL), and extracted with chloroform (2×30 mL). The combined organics were dried over anhydrous $MgSO_4$, filtered and evaporated to dryness. The residue was purified by flash column chromatography [silica gel 40 g, eluting with methanol in chloroform from 0-100%] to furnish 1-(3-cyanophenyl)-N-(3-(hydroxy(4-sulfamoylphenyl)methyl)phenyl)-3-(trifluoromethyl)-1H-pyrazole-5-carboxamide (112e) (169 mg, 67% yield) as a colorless solid; $^1H$ NMR (300 MHz, DMSO-$d_6$) δ 10.65 (s, 1H), 8.16 (t, J=1.8 Hz, 1H), 8.06-7.85 (m, 2H), 7.74 (ddd, J=10.1, 7.2, 2.8 Hz, 4H), 7.64 (d, J=2.2 Hz, 1H), 7.60-7.48 (m, 3H), 7.35-7.24 (m, 3H), 7.15 (d, J=7.7 Hz, 1H), 6.16 (d, J=3.8 Hz, 1H, $D_2O$ exchangeable), 5.76 (d, J=3.9 Hz, 1H); $^1H$ NMR (300 MHz, DMSO-$d_6$, $D_2O$) δ 10.66 (s, 1H), 8.15 (d, J=2.3 Hz, 1H), 8.04-7.87 (m, 2H), 7.79-7.69 (m, 4H), 7.64 (d, J=2.1 Hz, 1H), 7.60-7.50 (m, 3H), 7.33-7.28 (m, 2H), 5.76 (s, 1H); $^{19}F$ NMR (282 MHz, DMSO-$d_6$) δ −60.95; MS (ES+) 564.18 (M+1), MS (ES−) 540.2 (M−1).

Step-4: Preparation of 1-(3-cyanophenyl)-N-(3-((cyclopropylmethylamino)(4-sulfamoylphenyl)methyl) phenyl)-3-(trifluoromethyl)-1H-pyrazole-5-carboxamide (112f)

To a solution of 1-(3-cyanophenyl)-N-(3-(hydroxy(4-sulfamoylphenyl)methyl)phenyl)-3-(trifluoromethyl)-1H-pyrazole-5-carboxamide (112e) (0.164 g, 0.303 mmol) in dichloromethane (10 mL) at 0° C. was added thionyl chloride (0.066 mL, 0.909 mmol) and stirred at room temperature for 15 h. The reaction mixture was quenched with cyclopropylmethanamine (0.182 mL, 2.120 mmol) stirred for 1 h at room temperature, and concentrated in vacuum to dryness. The residue was dissolved in cyclopropylmethanamine (0.519 mL, 6.06 mmol), acetonitrile (10 mL) and heated at 80° C. for 16 h. TLC analysis ($CHCl_3$/MeOH, 9/1, v/v) shows reaction was complete, reaction mixture was evaporated to dryness. The residue was purified by flash column chromatography (silica gel 40 g, eluting with CMA80 in chloroform from 0-100%) to afford 1-(3-cyanophenyl)-N-(3-((cyclopropylmethylamino)(4-sulfamoylphenyl)methyl) phenyl)-3-(trifluoromethyl)-1H-pyrazole-5-carboxamide (112f) (0.072 g, 40% yield) as a white solid; $^1H$ NMR (300 MHz, DMSO-$d_6$) δ 10.64 (s, 1H, $D_2O$ exchangeable), 8.16 (t, J=1.9 Hz, 1H), 8.00 (dt, J=7.7, 1.3 Hz, 1H), 7.90 (ddd, J=8.3, 2.2, 1.1 Hz, 1H), 7.79-7.69 (m, 4H), 7.66 (s, 1H), 7.63-7.51 (m, 3H), 7.34-7.15 (m, 4H), 4.92 (s, 1H), 2.28 (d, J=4.7 Hz, 3H), 0.92 (s, 1H), 0.46-0.33 (m, 2H), 0.05 (q, J=4.8 Hz, 2H); $^1H$ NMR (300 MHz, DMSO-$d_6$, $D_2O$) δ 8.15 (t, J=1.8 Hz, 1H), 8.00 (dt, J=7.7, 1.3 Hz, 1H), 7.94-7.87 (m, 1H), 7.79-7.70 (m, 4H), 7.66 (d, J=2.1 Hz, 1H), 7.63-7.51 (m, 3H), 7.33-7.17 (m, 2H), 4.91 (s, 1H), 2.28 (dd, J=6.6, 2.5 Hz, 2H), 0.92 (d, J=10.4 Hz, 1H), 0.48-0.32 (m, 2H), 0.05 (tt, J=5.9, 3.3 Hz, 2H); $^{19}F$ NMR (282 MHz, DMSO-$d_6$) δ −60.94; MS (ES$^+$): MS (ES+) 593.24 (M+1), MS (ES−) 595.29 (M−1).

Step-5: Preparation of 1-(3-(aminomethyl)phenyl)-N-(3-((cyclopropylmethylamino)(4-sulfamoylphenyl)methyl)phenyl)-3-(trifluoromethyl)-1H-pyrazole-5-carboxamide (112g)

To a stirred solution of 1-(3-cyanophenyl)-N-(3-((cyclopropylmethylamino)(4-sulfamoylphenyl)methyl)phenyl)-3-(trifluoromethyl)-1H-pyrazole-5-carboxamide (112f) (0.065 g, 0.109 mmol) in anhydrous methanol (10 mL), cooled to 0° C. was added nickel(II) chloride hexahydrate (0.032 g, 0.137 mmol) followed by sodium borohydride (0.033 g, 0.875 mmol) in small portions over 5 min. The reaction mixture was stirred for 15 min at 0° C., at this point $N_1$-(2-aminoethyl)ethane-1,2-diamine (0.118 mL, 1.093 mmol) was added. The mixture was stirred for 30 minutes and concentrated in vacuum to dryness. The residue was treated with water (30 mL), and extracted with chloroform (2×30 mL). The combined organic layers were dried over anhydrous $MgSO_4$, filtered and excess solvents were pumped-off under reduced pressure. The residue was purified by flash column chromatography [(silica gel 25 g, eluting with CMA80 in chloroform from 0 to 100%)] to furnish 1-(3-(aminomethyl)phenyl)-N-(3-((cyclopropylmethylamino)(4-sulfamoylphenyl)methyl)phenyl)-3-(trifluoromethyl)-1H-pyrazole-5-carboxamide (112g) (28 mg, 43% yield) as a white solid; $^1H$ NMR (300 MHz, DMSO-$d_6$) δ 10.68 (s, 1H), 7.78-7.71 (m, 2H), 7.67 (t, J=1.8 Hz, 1H), 7.63-7.54 (m, 3H), 7.54-7.48 (m, 2H), 7.47-7.38 (m, 2H), 7.35-7.28 (m, 1H), 7.27-7.16 (m, 2H), 4.91 (s, 1H), 3.77 (s, 2H), 2.37-2.19 (m, 2H), 1.24 (s, 1H), 0.93 (dd, J=8.7, 4.7 Hz, 1H), 0.52-0.27 (m, 2H), 0.10-0.01 (m, 2H); $^1$H NMR (300 MHz, DMSO-$d_6$, $D_2O$) δ 7.72 (d, J=1.8 Hz, 1H), 7.70 (d, J=2.0 Hz, 1H), 7.63 (t, J=1.8 Hz, 1H), 7.57 (d, J=1.9 Hz, 1H), 7.55 (d, J=1.8 Hz, 1H), 7.52-7.38 (m, 5H), 7.33-7.15 (m, 3H), 4.88 (s, 1H), 3.71 (s, 2H), 2.24 (dd, J=7.0, 1.7 Hz, 2H), 0.88 (ddt, J=10.8, 7.2, 4.3 Hz, 1H), 0.47-0.25 (m, 2H), 0.05--0.03 (m, 2H); $^{19}$F NMR (282 MHz, DMSO-$d_6$) δ −60.52; MS (ES$^+$): MS (ES+) 599.3 (M+1), (ES−) 597.3 (M−1), 633.3 (M+Na); Analysis calculated for: $C_{29}H_{29}F_3N_6O_3S·H_2O·0.15CHCl_3$: C, 55.17; H, 4.95; N, 13.24; Found: C, 55.35; H, 4.66; N, 12.95.
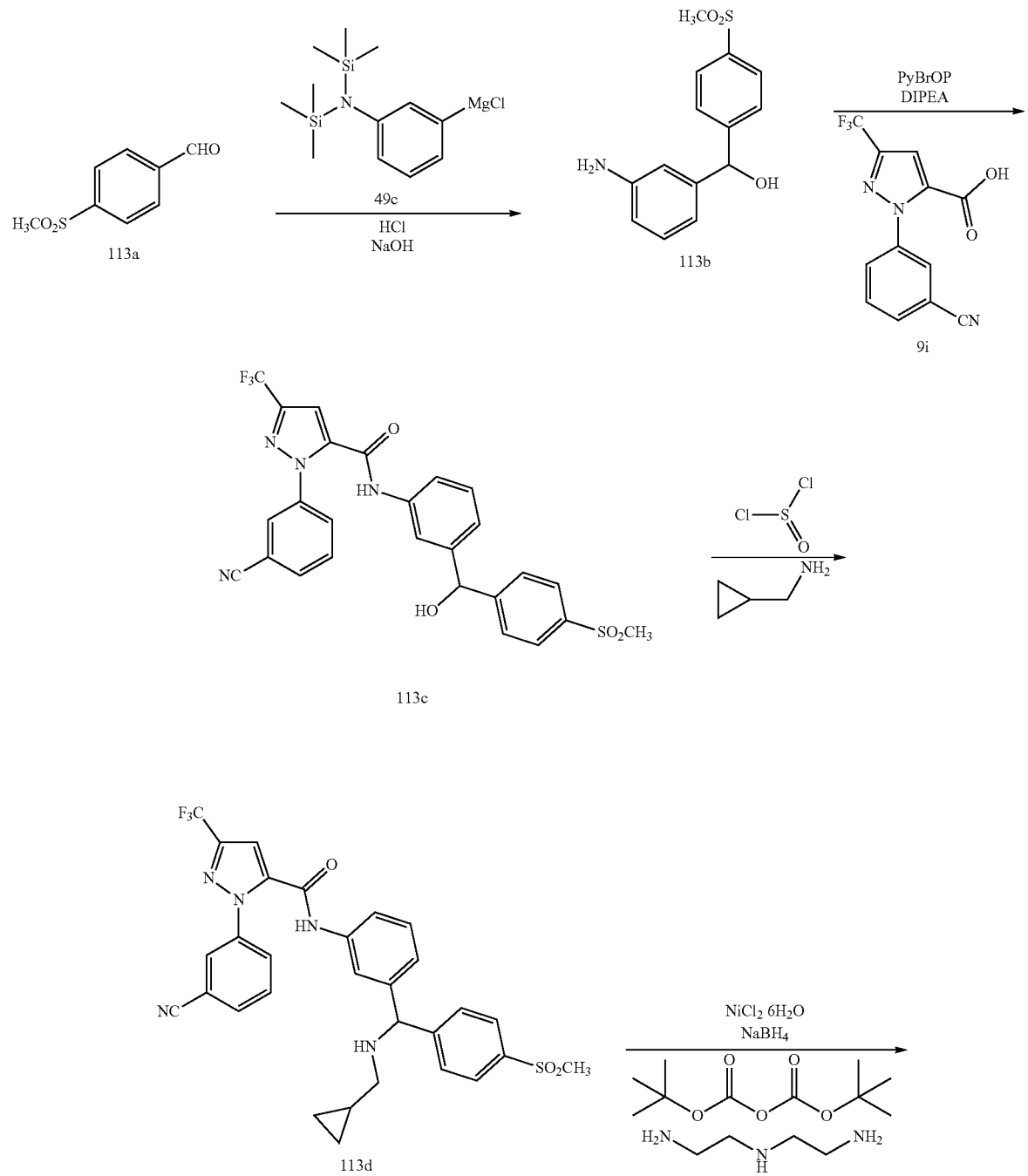
Scheme 113

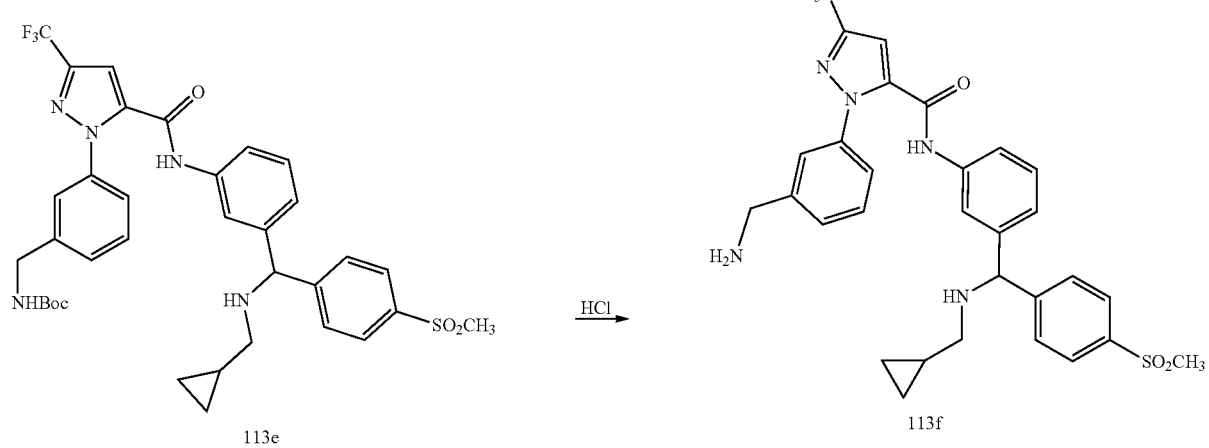

Preparation of 1-(3-(aminomethyl)phenyl)-N-(3-((cyclopropylmethylamino)(4-(methylsulfonyl)phenyl)methyl)phenyl)-3-(trifluoromethyl)-1H-pyrazole-5-carboxamide (113f)

Step-1: Preparation of (3-aminophenyl)(4-(methylsulfonyl)phenyl)methanol (113b)

To a solution of 4-(methylsulfonyl)benzaldehyde (3.68 g, 20 mmol) in tetrahydrofuran (30 mL) cooled to 0° C. was added (3-(bis(trimethylsilyl)amino)phenyl)magnesium chloride (49c) (24.0 mL, 24.0 mmol) stirred at 0° C. for 1 h and room temperature for 12 h. The reaction mixture was treated with 1 N HCl (aq. 50 mL), stirred at room temperature for 1 h, neutralized with NaOH (2 N, aq.) to pH=~8, and extracted with ethyl acetate (2×80 mL). The combined extracts were washed with brine (60 mL), dried over MgSO$_4$ followed by filtration and concentration. The crude product was purified by flash column chromatography [silica gel 80 g, eluting with chloroform/methanol (1:0 to 19:1)] to give (3-aminophenyl)(4-(methylsulfonyl)phenyl)methanol (113b) (3.858 g, 70%) as a off-white solid; $^1$H NMR (300 MHz, DMSO-d$_6$) δ 7.88-7.81 (m, 2H), 7.64-7.58 (m, 2H), 6.93 (t, J=7.7 Hz, 1H), 6.60-6.50 (m, 2H), 6.40 (ddd, J=8.0, 2.3, 1.0 Hz, 1H), 5.98 (d, J=3.8 Hz, 1H), 5.62 (d, J=3.8 Hz, 1H), 5.04 (s, 2H), 3.17 (s, 3H); MS (ES+) 300.1 (M+23).

Step-2: Preparation of 1-(3-cyanophenyl)-N-(3-(hydroxy(4-(methylsulfonyl)-phenyl)methyl)phenyl)-3-(trifluoromethyl)-1H-pyrazole-5-carboxamide (113c)

To a solution of (3-aminophenyl)(4-(methylsulfonyl)phenyl)methanol (113b) (2.5 g, 9.01 mmol) in DMF (48 mL) was added 1-(3-cyanophenyl)-3-(trifluoromethyl)-1H-pyrazole-5-carboxylic acid (9i) (2.53 g, 9.01 mmol), N-ethyl-N-isopropylpropan-2-amine (13.00 mL, 74.6 mmol), bromotripyrrolidin-1-ylphosphonium hexafluorophosphate(V) (PyBrOP, 4.29 g, 9.01 mmol) and stirred at room temperature for 15 h. The reaction mixture was diluted with ethyl acetate (200 mL), washed with water (2×80 mL), brine (80 mL), dried over MgSO$_4$ and concentrated in vacuum to dryness. The crude product was purified by flash column chromatography [silica gel 80 g, eluting with hexanes/10% methanol in ethyl acetate (1:0 to 1:1)] to give 1-(3-cyanophenyl)-N-(3-(hydroxy(4-(methylsulfonyl)phenyl)methyl)phenyl)-3-(trifluoromethyl)-1H-pyrazole-5-carboxamide (113c) (4.15 g, 85%) as a yellow solid; $^1$H NMR (300 MHz, DMSO-d$_6$) δ 10.66 (s, 1H), 8.17-8.15 (m, 1H), 8.00 (dt, J=7.7, 1.3 Hz, 1H), 7.94-7.84 (m, 3H), 7.77-7.69 (m, 2H), 7.68-7.52 (m, 4H), 7.29 (t, J=7.8 Hz, 1H), 7.18 (d, J=7.8 Hz, 1H), 6.23 (d, J=3.8 Hz, 1H), 5.81 (d, J=3.9 Hz, 1H), 3.17 (s, 3H); $^{19}$F NMR (282 MHz, DMSO-d$_6$) δ −60.95; MS (ES+) 563.2 (M+23).

Step-3: Preparation of 1-(3-cyanophenyl)-N-(3-((cyclopropylmethylamino)(4-(methylsulfonyl)phenyl)methyl)phenyl)-3-(trifluoromethyl)-1H-pyrazole-5-carboxamide (113d)

To a solution of 1-(3-cyanophenyl)-N-(3-(hydroxy(4-(methylsulfonyl)phenyl)methyl)phenyl)-3-(trifluoromethyl)-1H-pyrazole-5-carboxamide (113c) (1.984 g, 3.67 mmol) in dichloromethane (50 mL) at 0° C. was added thionyl chloride (0.780 mL, 10.53 mmol) and stirred at room temperature for 2 h. The reaction mixture was treated with triethyl amine (4.50 mL, 32.3 mmol) stirred at room temperature for 1 h. It was then treated with cyclopropylmethanamine (5.38 g, 73.4 mmol), concentrated to remove most of dichloromethane. To the reaction was added acetonitrile (36 mL) heated at 70° C. for 14.5 h, and concentrated in vacuum to dryness. The residue was treated with chloroform (150 mL), washed with water (75 mL), dried over MgSO$_4$ followed by filtration and concentration. The crude product was purified by flash column chromatography [silica gel 40 g, eluting with hexanes/ethyl acetate (1:0 to 1:1)] to give 1-(3-cyanophenyl)-N-(3-((cyclopropylmethylamino)(4-(methylsulfonyl)phenyl)methyl)phenyl)-3-(trifluoromethyl)-1H-pyrazole-5-carboxamide (113d) (329 mg, 15%) as a brown gum; $^1$H NMR (300 MHz, DMSO-d$_6$) δ 10.65 (s, 1H), 8.18-8.13 (m, 1H), 8.01 (dt, J=7.7, 1.3 Hz, 1H), 7.96-7.50 (m, 9H), 7.32-7.18 (m, 2H), 4.96 (s, 1H), 3.16 (s, 3H), 2.35-2.20 (m, 2H), 0.90 (d, J=7.3 Hz, 1H), 0.50-0.25 (m, 2H), 0.11-0.01 (m, 2H); $^{19}$F NMR (282 MHz, DMSO-d$_6$) δ −60.96; MS (ES+) 594.3 (M+1).

Step-4: Preparation of tert-butyl 3-(5-(3-((cyclopropylmethylamino)(4-(methyl sulfonyl)phenyl)methyl)phenylcarbamoyl)-3-(trifluoromethyl)-1H-pyrazol-1-yl)benzylcarbamate (113e)

To a solution of 1-(3-cyanophenyl)-N-(3-((cyclopropylmethylamino)(4-(methylsulfonyl)phenyl)methyl)phenyl)-3-

(trifluoromethyl)-1H-pyrazole-5-carboxamide (113d) (314 mg, 0.529 mmol) in MeOH (9 mL) cooled with ice/water was added di-tert-butyl dicarbonate (350 mg, 1.587 mmol), nickel(II) chloride hexahydrate (68.0 mg, 0.286 mmol) followed by sodium borohydride (204 mg, 5.29 mmol) slowly over 5 min. The reaction mixture was stirred at room temperature for 1 h, quenched with N1-(2-aminoethyl)ethane-1,2-diamine (0.260 mL, 2.380 mmol) stirred at room temperature for 0.5 h and concentrated in vacuum to dryness. The residue was treated with ethyl acetate (120 mL), washed with water (75 mL). The aqueous phase was extracted again with ethyl acetate (75 mL). The combined organic extracts were washed with brine (75 mL), dried over $MgSO_4$ followed by filtration and concentration. The crude product was purified by flash column chromatography [silica gel 4 g, eluting with chloroform/methanol (1:0 to 19:1)] to give tert-butyl 3-(5-(3-((cyclopropylmethylamino)(4-(methylsulfonyl)phenyl)methyl)phenylcarbamoyl)-3-(trifluoromethyl)-1H-pyrazol-1-yl)benzylcarbamate (113e) (215 mg, 58%) as a white solid; $^1$H NMR (300 MHz, DMSO-$d_6$) δ 10.69 (s, 1H), 7.87-7.82 (m, 2H), 7.72-7.64 (m, 3H), 7.57 (s, 1H), 7.55-7.19 (m, 8H), 4.95 (s, 1H), 4.19 (d, J=6.2 Hz, 2H), 3.16 (s, 3H), 2.35-2.22 (m, 2H), 1.36 (s, 9H), 1.00-0.80 (m, 1H), 0.48-0.27 (m, 2H), 0.13-0.00 (m, 2H); $^{19}$F NMR (282 MHz, DMSO-$d_6$) δ −60.78; MS (ES+) 698.4 (M+1).

Step-5: Preparation of 1-(3-(aminomethyl)phenyl)-N-(3-((cyclopropylmethylamino)(4-(methylsulfonyl) phenyl)methyl)phenyl)-3-(trifluoromethyl)-1H-pyrazole-5-carboxamide (113f)

To a solution of tert-butyl 3-(5-(3-((cyclopropylmethylamino)(4-(methyl sulfonyl)phenyl)methyl)phenylcarbamoyl)-3-(trifluoromethyl)-1H-pyrazol-1-yl)benzylcarbamate (113e) (0.188 g, 0.269 mmol) in 1,4-Dioxane (20 mL) was added hydrogen chloride (2.8 mL, 11.21 mmol, 4 M in 1,4-dioxane) and stirred at room temperature for 13 h. The reaction mixture was treated with hexanes, decanted, washed with hexanes, and decanted again. The insoluble crude product was purified by flash column chromatography [silica gel, eluting with chloroform/CMA80 (1:0 to 2:1)] to give 1-(3-(aminomethyl)phenyl)-N-(3-((cyclopropylmethylamino)(4-(methylsulfonyl)phenyl)methyl)phenyl)-3-(trifluoromethyl)-1H-pyrazole-5-carboxamide (113f) (107 mg, 66%) as a white solid; $^1$H NMR (300 MHz, DMSO-$d_6$) δ 10.67 (s, 1H), 7.93-7.12 (m, 13H), 4.95 (s, 1H), 3.77 (s, 2H), 3.16 (s, 3H), 2.36-2.21 (m, 2H), 1.01-0.82 (m, 1H), 0.47-0.31 (m, 2H), 0.13-0.02 (m, 2H); $^{19}$F NMR (282 MHz, DMSO-$d_6$) δ −60.53; MS (ES+): 598.3 (M+1); IR (KBr pellet, cm$^{-1}$): 3365, 3006, 2926, 1683, 1553, 1243, 1148; Analysis calculated for $C_{30}H_{30}F_3N_5O_3S \cdot 1.0H_2O$: C, 58.53; H, 5.24; N, 11.38; Found: C, 58.85; H, 5.21; N, 11.29.

Scheme 114

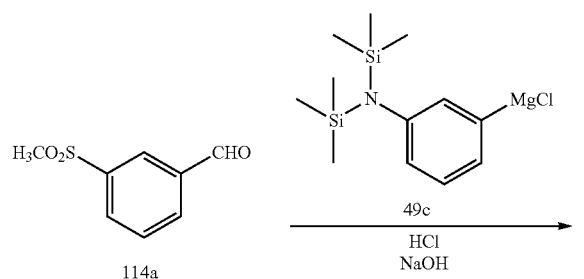

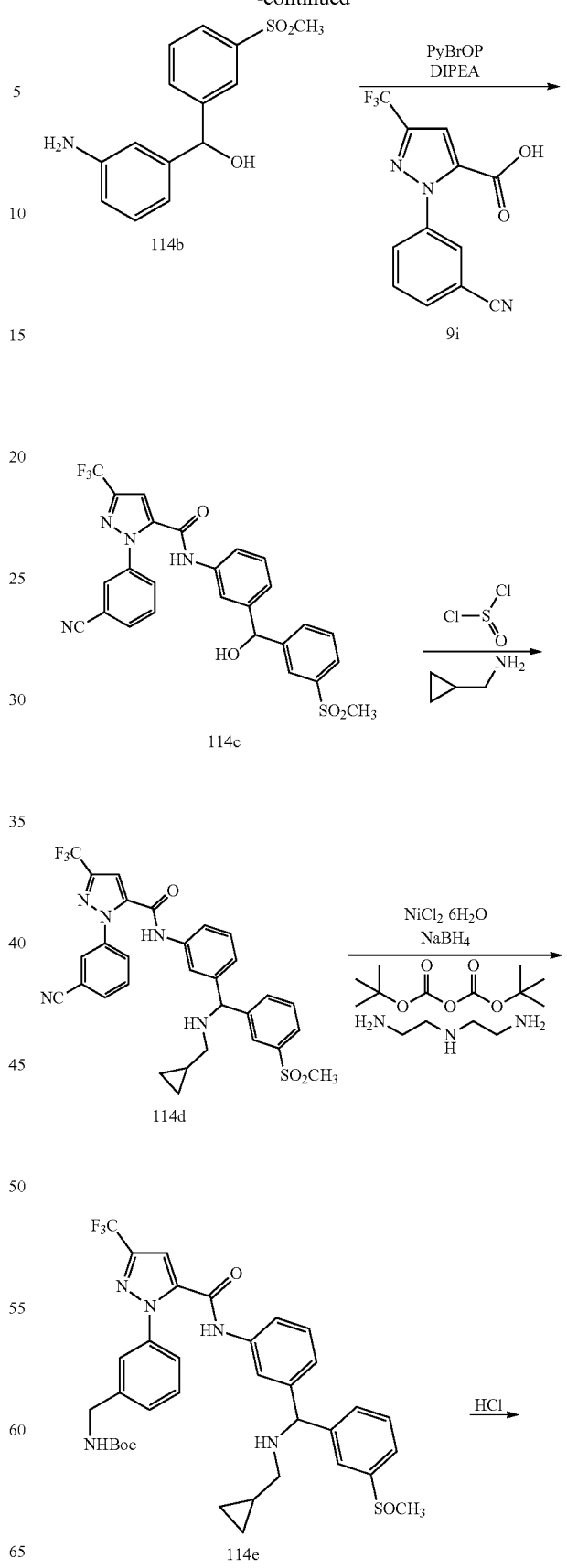

-continued

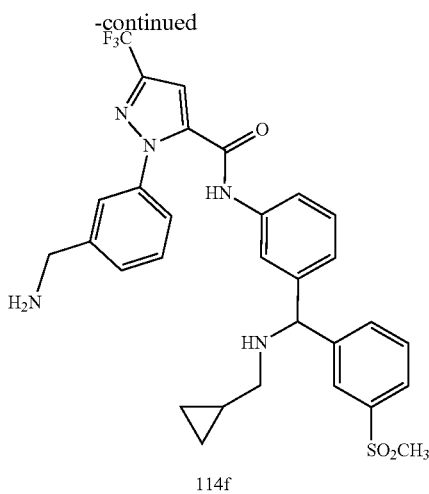

114f

Preparation of 1-(3-(aminomethyl)phenyl)-N-(3-((cyclopropylmethylamino)(3-(methylsulfonyl)phenyl)methyl)phenyl)-3-(trifluoromethyl)-1H-pyrazole-5-carboxamide (114f)

Step-1: Preparation of (3-aminophenyl)(3-(methylsulfonyl)phenyl)methanol (114b)

To a stirred solution of 3-(methylsulfonyl)benzaldehyde (114a) (1 g, 5.43 mmol) in tetrahydrofuran (10 mL) was added (3-(bis(trimethylsilyl)amino)phenyl)magnesium chloride (49c) (6.51 mL, 6.51 mmol) at 0° C. The reaction was stirred for 14 h at same temperature and quenched by adding 2 N HCl (13.57 mL, 13.57 mmol), stirred for 6 h. The reaction mixture was treated with 2 N NaOH (15 mL) and extracted with ethyl acetate (2×50 mL). The organic layers were combined washed with sat. NH$_4$Cl (50 mL), dried over anhydrous MgSO$_4$, filtered, evaporated to dryness. The crude residue was purified by flash column chromatography (silica gel 40 g, eluting with ethyl acetate in hexane from 0-100%) to furnish (3-aminophenyl)(3-(methylsulfonyl)phenyl)methanol (114b) (1.004 g, 67%) as a white gum; $^1$H NMR (300 MHz, DMSO-d$_6$) δ 7.93 (t, J=1.7 Hz, 1H), 7.77 (dt, J=7.6, 1.5 Hz, 1H), 7.66 (dt, J=7.7, 1.5 Hz, 1H), 7.57 (t, J=7.7 Hz, 1H), 6.94 (t, J=7.7 Hz, 1H), 6.58 (t, J=1.9 Hz, 1H), 6.53 (dt, J=7.5, 1.3 Hz, 1H), 6.40 (ddd, J=8.0, 2.3, 1.1 Hz, 1H), 5.99 (d, J=3.8 Hz, 1H), 5.63 (d, J=3.8 Hz, 1H), 5.05 (s, 2H), 3.20 (s, 3H); MS (ES+): 278.1 (M+H).

Step-2: Preparation of 1-(3-cyanophenyl)-N-(3-(hydroxy(3-(methylsulfonyl)phenyl)methyl)phenyl)-3-(trifluoromethyl)-1H-pyrazole-5-carboxamide (114c)

In a 100 mL single-necked flask 1-(3-cyanophenyl)-3-(trifluoromethyl)-1H-pyrazole-5-carboxylic acid (9i) (0.963 g, 3.43 mmol), (3-aminophenyl)(3-(methylsulfonyl)phenyl)methanol (114b) (0.95 g, 3.43 mmol), bromo-tris-pyrrolidino phosphoniumhexafluorophosphate(PyBrop) (1.629 g, 3.43 mmol) were treated with N,N-dimethylformamide (36.0 mL, 465 mmol) and N-ethyl-N-isopropylpropan-2-amine (DIPEA, 4.80 mL, 27.6 mmol) successively in a positive flow of nitrogen at room temperature. The resulting reaction mixture was stirred at room temperature for 16 h under a positive flow of nitrogen atmosphere. The reaction mixture was diluted with ethyl acetate (120 mL), washed with water (2×60 mL) and brine (60 mL), and dried over MgSO$_4$ followed by filtration and concentration. The crude product was purified by flash column chromatography [silica gel with hexanes/10% methanol in ethyl acetate (1:0 to 1:1)] to give 1-(3-cyanophenyl)-N-(3-(hydroxy(3-(methylsulfonyl)phenyl)methyl)phenyl)-3-(trifluoromethyl)-1H-pyrazole-5-carboxamide (114c) (1.228 g, 66%) as a off-white solid; $^1$H NMR (300 MHz, DMSO-d$_6$) δ 10.68 (s, 1H), 8.16 (t, J=1.8 Hz, 1H), 8.00 (dt, J=7.8, 1.3 Hz, 1H), 7.94 (t, J=1.8 Hz, 1H), 7.90 (ddd, J=8.2, 2.2, 1.1 Hz, 1H), 7.82-7.77 (m, 1H), 7.76-7.64 (m, 4H), 7.63-7.55 (m, 2H), 7.30 (t, J=7.8 Hz, 1H), 7.18 (dt, J=7.7, 1.3 Hz, 1H), 6.24 (d, J=3.9 Hz, 1H), 5.82 (d, J=3.9 Hz, 1H), 3.18 (s, 3H); $^{19}$F NMR (282 MHz, DMSO-d$_6$) δ −60.98; MS (ES−): 539.2 (M−1).

Step-3: Preparation of 1-(3-cyanophenyl)-N-(3-((cyclopropylmethylamino)(3-(methylsulfonyl)phenyl)methyl)phenyl)-3-(trifluoromethyl)-1H-pyrazole-5-carboxamide (114d)

To a solution of 1-(3-cyanophenyl)-N-(3-(hydroxy(3-(methylsulfonyl)phenyl)methyl)phenyl)-3-(trifluoromethyl)-1H-pyrazole-5-carboxamide (114c) (1.18 g, 2.19 mmol) in dichloromethane (25 mL) at 0° C. was added thionyl chloride (1.06 mL, 14.55 mmol) and stirred at room temperature for 2 h. The reaction mixture was quenched triethyl amine (2.70 mL, 19.34 mmol), stirred for 1 h. The reaction mixture was concentrated in vacuum to dryness. The residue obtained was dissolved in acetonitrile (22 mL) and added cyclopropylmethanamine (3.21 g, 43.8 mmol). The reaction mixture was heated at 70° C. for 19 h, cooled to room temperature and concentrated in vacuum to dryness. The residue was dissolved in chloroform (120 mL), washed with water (60 mL), dried, filtered and concentrated in vacuum. The residue obtained was purified by flash column chromatography (silica gel 40 g, eluting 0-50% ethyl acetate in hexane) to afford 1-(3-cyanophenyl)-N-(3-((cyclopropylmethylamino)(3-(methylsulfonyl)phenyl)methyl)phenyl)-3-(trifluoromethyl)-1H-pyrazole-5-carboxamide (114d) (208 mg, 16%) as a yellow solid, $^1$H NMR (300 MHz, DMSO-d$_6$) δ 10.66 (s, 1H), 8.16 (t, J=1.9 Hz, 1H), 8.06-7.98 (m, 2H), 7.95-7.87 (m, 1H), 7.80-7.51 (m, 7H), 7.33-7.18 (m, 2H), 4.97 (s, 1H), 3.17 (s, 3H), 2.36-2.22 (m, 2H), 1.02-0.79 (m, 1H), 0.55-0.29 (m, 2H), 0.17--0.02 (m, 2H); $^{19}$F NMR (282 MHz, DMSO-d$_6$) δ −60.94; MS (ES+): 594.3 (M+1).

Step-4: Preparation of tert-butyl 3-(5-(3-((cyclopropylmethylamino)(3-(methylsulfonyl)phenyl)-methyl)phenylcarbamoyl)-3-(trifluoromethyl)-1H-pyrazol-1-yl)benzylcarbamate (114e)

To a solution of 1-(3-cyanophenyl)-N-(3-((cyclopropylmethylamino)(3-(methylsulfonyl)phenyl)methyl)phenyl)-3-(trifluoromethyl)-1H-pyrazole-5-carboxamide (114d) (195 mg, 0.328 mmol) in MeOH (6 mL) cooled with ice/water was added di-tert-butyl dicarbonate (217 mg, 0.985 mmol) and nickel(II) chloride (42.0 mg, 0.177 mmol). Sodium borohydride (127 mg, 3.28 mmol) was added slowly over 15 min and reaction mixture was stirred at room temperature for 1 h. The reaction mixture was quenched with N1-(2-aminoethyl)ethane-1,2-diamine (0.160 mL, 1.462 mmol) stirred for 0.5 h and concentrated in vacuum to dryness. The residue obtained was dissolved in ethyl acetate (60 mL) and water (60 mL). The aqueous phase was separated and extracted again with ethyl acetate (60 mL). The organic extracts were combined, washed with brine (60 mL), dried over MgSO₄, filtered and concentrated in vacuum to dryness. The residue obtained was purified by flash column chromatography [silica gel 4 g, eluting with chloroform/methanol (1:0 to 19:1)] to give tert-butyl 3-(5-(3-((cyclopropylmethylamino)(3-(methylsulfonyl)phenyl)methyl)phenylcarbamoyl)-3-(trifluoromethyl)-1H-pyrazol-1-yl)benzylcarbamate (114e) (135 mg, 59%) as a white solid; ¹H NMR (300 MHz, DMSO-d₆) δ 10.71 (s, 1H), 8.00 (bs, 1H), 7.79-7.71 (m, 2H), 7.68 b (s, 1H), 7.61-7.19 (m, 10H), 4.96 (s, 1H), 4.19 (d, J=6.2 Hz, 2H), 3.16 (s, 3H), 2.33-2.22 (m, 2H), 1.36 (s, 9H), 0.99-0.80 (m, 1H), 0.46-0.31 (m, 2H), 0.10-0.00 (m, 2H); ¹⁹F NMR (282 MHz, DMSO-d₆) δ −60.78; MS (ES+): 698.4 (M+1).

Step-5: Preparation of 1-(3-(aminomethyl)phenyl)-N-(3-((cyclopropylmethylamino)(3-(methylsulfonyl)phenyl)methyl)phenyl)-3-(trifluoromethyl)-1H-pyrazole-5-carboxamide (114f)

To a solution of tert-butyl 3-(5-(3-((cyclopropylmethylamino)(3-(methyl sulfonyl)phenyl)methyl)phenylcarbamoyl)-3-(trifluoromethyl)-1H-pyrazol-1-yl)benzylcarbamate (114e) (120 mg, 0.172 mmol) in 1,4-Dioxane (15 mL) was added hydrogen chloride (1.8 mL, 7.2 mmol, 4 M in 1,4-dioxane) and stirred at room temperature for 15 h. The reaction mixture was treated with hexanes, decanted, washed with hexanes, and decanted again. The insoluble crude product was purified by flash column chromatography [silica gel eluting with chloroform/CMA80 (1:0 to 2:1)] to give 1-(3-(aminomethyl)phenyl)-N-(3-((cyclopropylmethylamino)(3-(methylsulfonyl)phenyl)methyl)phenyl)-3-(trifluoromethyl)-1H-pyrazole-5-carboxamide (114f) (49 mg, 48%) as an off-white solid; ¹H NMR (300 MHz, DMSO-d₆) δ 10.94 (s, 1H), 10.17 (s, 2H), 8.46-7.37 (m, 13H), 5.81 (s, 1H), 4.13 (d, J=5.1 Hz, 2H), 3.22 (s, 3H), 2.83-2.67 (m, 2H), 1.13 (bs, 1H), 0.56 (d, J=7.8 Hz, 2H), 0.31 (bs, 2H); ¹⁹F NMR (282 MHz, DMSO-d₆) δ −60.77; MS (ES+): 598.3 (M+1); IR (KBr pellet, cm⁻¹): 3433, 3013, 1675, 1616, 1558, 1246, 1143.

Scheme 115

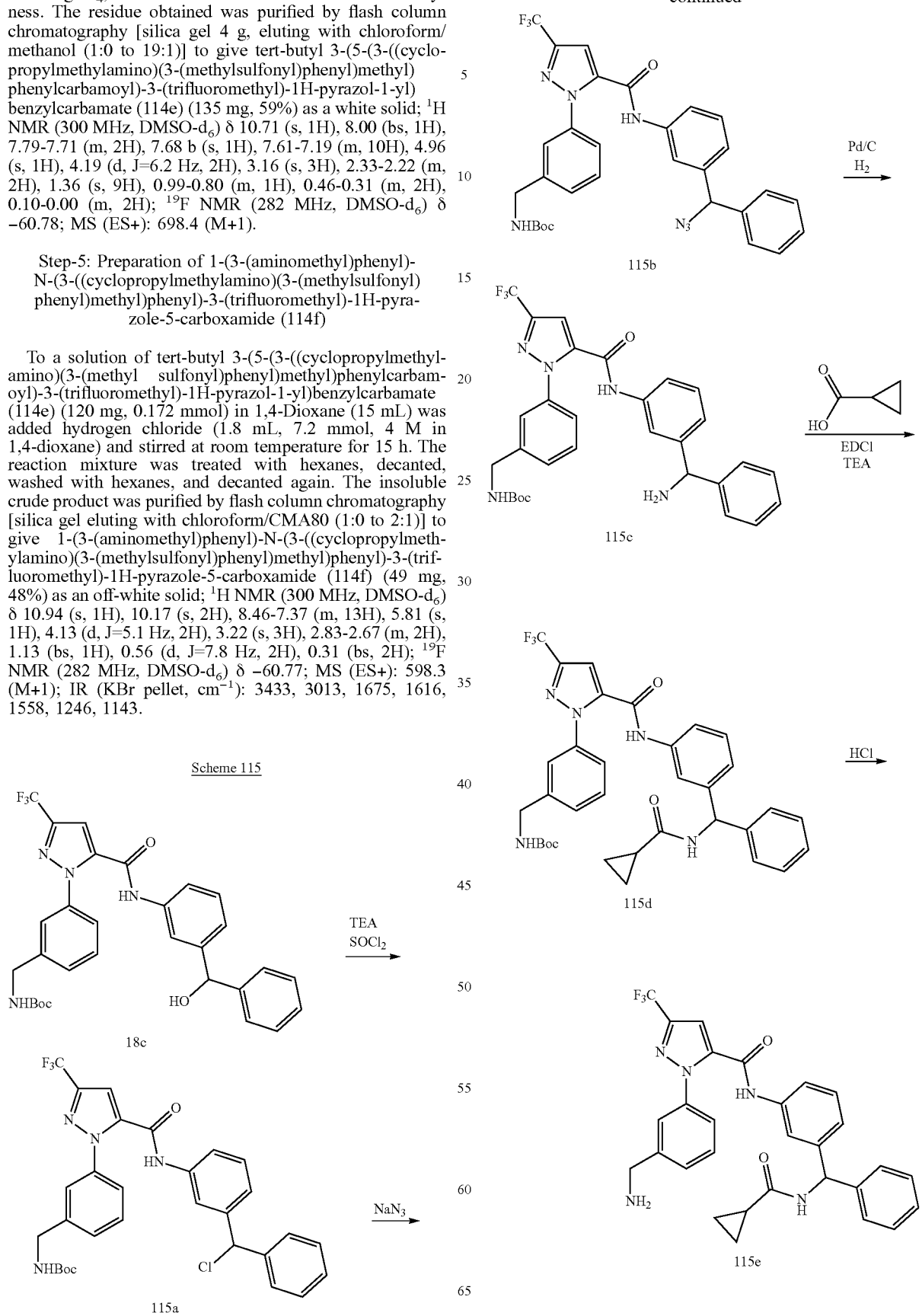

Preparation of 1-(3-(aminomethyl)phenyl)-N-(3-(cyclopropanecarboxamido(phenyl) methyl)phenyl)-3-(trifluoromethyl)-1H-pyrazole-5-carboxamide (115e)

Step-1: Preparation of tert-butyl 3-(5-((3-(chloro (phenyl)methyl)phenyl)carbamoyl)-3-(trifluoromethyl)-1H-pyrazol-1-yl)benzylcarbamate (115a)

To a solution of tert-butyl 3-(5-(3-(hydroxy(phenyl) methyl)phenylcarbamoyl)-3-(trifluoromethyl)-1H-pyrazol-1-yl)benzylcarbamate (18c) (133 mg, 0.235 mmol) in dichloromethane (5 mL) at 0° C. was added triethylamine (0.131 mL, 0.939 mmol), thionyl chloride (0.026 mL, 0.352 mmol) and stirred at room temperature for 2 h. The reaction mixture was concentrated in vacuum to dryness to furnish tert-butyl 3-(5-(3-(chloro(phenyl)methyl)phenylcarbamoyl)-3-(trifluoromethyl)-1H-pyrazol-1-yl)benzylcarbamate (115a) (137 mg, 100%) which was used as such for next step.

Step-2: Preparation of tert-butyl 3-(5-((3-(azido (phenyl)methyl)phenyl)carbamoyl)-3-(trifluoromethyl)-1H-pyrazol-1-yl)benzylcarbamate (115b)

To a stirred solution of tert-butyl 3-(5-(3-(chloro(phenyl) methyl)phenylcarbamoyl)-3-(trifluoromethyl)-1H-pyrazol-1-yl)benzylcarbamate (115a) (137 mg, 0.235 mmol) in acetonitrile (10 mL) was added sodium azide (61.1 mg, 0.94 mmol) and heated at reflux for 16 h. The reaction mixture was concentrated in vacuum, diluted with ethyl acetate (25 mL), and washed with water (2×10 mL). The aqueous layer was extracted with ethyl acetate (2×25 mL). The organic layers were combined washed with water (20 mL), brine (10 mL), dried and concentrated in vacuum. The crude residue was purified by flash column chromatography (silica gel, 4 g eluting with ethyl acetate in hexanes 0-100%) to afford tert-butyl 3-(5-(3-(azido(phenyl)methyl)phenylcarbamoyl)-3-(trifluoromethyl)-1H-pyrazol-1-yl)benzylcarbamate (115b) (75 mg, 0.127 mmol, 53.9% yield) as a colorless solid; MS (ES+) 614.3 (M+Na), 590.3 (ES−) (M−1).

Step-3: Preparation of tert-butyl 3-(5-((3-(amino (phenyl)methyl)phenyl)carbamoyl)-3-(trifluoromethyl)-1H-pyrazol-1-yl)benzylcarbamate (115c)

To a suspension of Pd/C (10%, 12.59 mg) in methanol (20 mL) was added tert-butyl 3-(5-(3-(azido(phenyl)methyl) phenylcarbamoyl)-3-(trifluoromethyl)-1H-pyrazol-1-yl) benzylcarbamate (115b) (70 mg, 0.118 mmol) and hydrogenated at 60 psi for 2 h. The reaction mixture was filtered through celite and concentrated in vacuum. The crude residue was purified by flash column chromatography (silica gel, 4 g eluting with CMA 80 in chloroform 0 to 100%) to afford tert-butyl 3-(5-(3-(amino(phenyl)methyl)phenylcarbamoyl)-3-(trifluoromethyl)-1H-pyrazol-1-yl)benzylcarbamate (115c) (24 mg, 35.9% yield) as a colorless foam; MS (ES+) 566.3 (M+1); (ES−) 564.3 (M−1).

Step-4: Preparation of tert-butyl 3-(5-((3-(cyclopropanecarboxamido(phenyl)methyl) phenyl)carbamoyl)-3-(trifluoromethyl)-1H-pyrazol-1-yl)benzylcarbamate (115d)

To a solution of tert-butyl 3-(5-(3-(amino(phenyl)methyl) phenylcarbamoyl)-3-(trifluoromethyl)-1H-pyrazol-1-yl) benzylcarbamate (115c) (24 mg, 0.042 mmol) in dichloromethane (5 mL) was added cyclopropanecarboxylic acid (5.07 µL, 0.064 mmol), triethylamine (0.024 mL, 0.170 mmol) and EDCI (16.27 mg, 0.085 mmol) at room temperature. The resulting reaction mixture was stirred at 25° C. for 16 h. The reaction mixture was diluted with water (20 mL) and extracted with dichloromethane (2×50 mL). The combined organic layers were washed with water (20 mL), brine (20 mL), dried, filtered and concentrated in vacuum. The crude residue was purified by flash column chromatography (silica gel 12 g, eluting with ethyl acetate in hexanes 0 to 100%) to afford tert-butyl 3-(5-(3-(cyclopropanecarboxamido(phenyl)methyl)phenylcarbamoyl)-3-(trifluoromethyl)-1H-pyrazol-1-yl)benzylcarbamate (115d) (23 mg, 0.036 mmol, 86% yield); MS (ES+) 656.4 (M+Na); (ES−) 632.3 (M−1).

Step-5: Preparation of 1-(3-(aminomethyl)phenyl)-N-(3-(cyclopropanecarboxamido(phenyl) methyl) phenyl)-3-(trifluoromethyl)-1H-pyrazole-5-carboxamide (115e)

To a solution of tert-butyl 3-(5-(3-(cyclopropanecarboxamido(phenyl)methyl)phenylcarbamoyl)-3-(trifluoromethyl)-1H-pyrazol-1-yl)benzylcarbamate (115d) (21 mg, 0.033 mmol) in methanol (5 mL) was added conc. hydrogen chloride (0.033 mL, 0.133 mmol), stirred at room temperature overnight and concentrated in vacuum to dryness. The residue obtained was purified by flash column chromatography (silica gel 4 g, eluting with 0-50% methanol in chloroform) to afford 1-(3-(aminomethyl)phenyl)-N-(3-(cyclopropanecarboxamido(phenyl)methyl)phenyl)-3-(trifluoromethyl)-1H-pyrazole-5-carboxamide (115e) (0.016 g, 0.030 mmol, 90% yield) as a white solid; $^1$HNMR (300 MHz, DMSO) δ 10.78 (s, 1H), 9.02 (d, J=8.7 Hz, 1H), 8.30 (s, 3H), 7.71 (s, 1H), 7.64 (s, 1H), 7.62-7.54 (m, 3H), 7.52 (q, J=2.1 Hz, 2H), 7.39-7.30 (m, 3H), 7.27 (d, J=7.1 Hz, 3H), 7.04 (d, J=7.6 Hz, 1H), 6.69 (s, 1H), 6.08 (d, J=8.4 Hz, 1H), 4.13 (q, J=5.8 Hz, 2H), 0.68 (s, 2H), 0.66 (s, 2H); MS (ES+) 534.4 (M+1); (ES−) 532.3 (M−1).

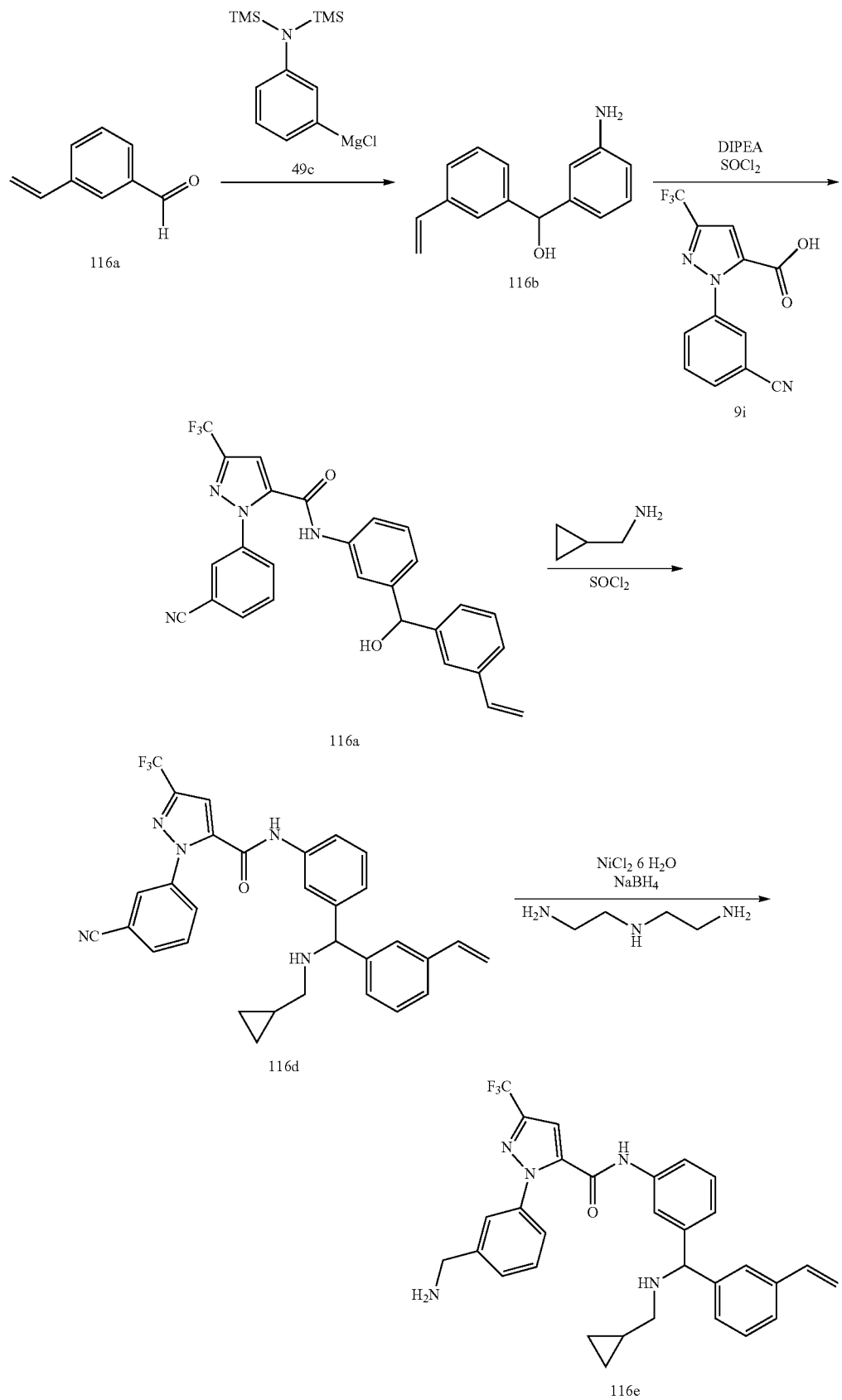

Preparation of 1-(3-(aminomethyl)phenyl)-N-(3-((cyclopropylmethylamino)(3-ethylphenyl)methyl)phenyl)-3-(trifluoromethyl)-1H-pyrazole-5-carboxamide (116e)

Step-1: Preparation of (3-aminophenyl)(3-vinylphenyl)methanol (116b)

To a stirred solution of 3-vinylbenzaldehyde (116a) (1.32 g, 10 mmol) in tetrahydrofuran (5 mL) was added (3-(bis(trimethylsilyl)amino)phenyl)magnesium chloride (49c) (12.0 mL, 12.0 mmol) at 0° C. The reaction was stirred for 14 h at room temperature and quenched by adding 2 N HCl (12.50 mL), stirred for 6 h. The reaction mixture was treated with 2 N NaOH (15 mL) and extracted with ethyl acetate (2×50 mL). The organic layers were combined washed with sat. NH$_4$Cl (50 mL), dried over anhydrous MgSO$_4$, filtered, evaporated to dryness. The crude residue was purified by flash column chromatography (silica gel 40 g, eluting with 0-100% ethyl acetate in hexane) to furnish (3-aminophenyl)-(3-vinylphenyl) methanol (116b) (1.2 g, 53.33% yield) as a red brown oil, which was used as such for next step.

Step-2: Preparation of 1-(3-cyanophenyl)-N-(3-(hydroxy(3-vinylphenyl)methyl)phenyl)-3-(trifluoromethyl)-1H-pyrazole-5-carboxamide (116c)

To a solution of 1-(3-cyanophenyl)-3-(trifluoromethyl)-1H-pyrazole-5-carboxylic acid (9i) (1.947 g, 6.924 mmol) in toluene (50 mL) and DMF 15 drops was added SOCl$_2$ (0.928 mL, 12.78 mmol) at 0° C. Reaction was refluxed for 3.5 hr and concentrated to remove volatile solvent. The residue obtained was dissolved in DCM (50 mL) and added (3-Amino-phenyl)-(3-vinyl-phenyl)-methanol (116b) (1.2 g, 5.326 mmol), triethylamine (7.2 mL) at room temperature. Reaction mixture was stirred overnight at room temp. Reaction mixture was concentrated and purified by flash column chromatography (silica gel, eluting with 10%-70% ethyl acetate in hexane) to afford product 2-(3-Cyano-phenyl)-5-trifluoromethyl-2H-pyrazole-3-carboxylic acid {3-[hydroxy-(3-vinyl-phenyl)-methyl]-phenyl}-amide (116c) (2.1 g, 80.76%) as a red-brown sticky liquid; $^1$H NMR (300 MHz, DMSO-d$_6$) δ 10.63 (s, 1H), 8.15 (t, J=1.8 Hz, 1H), 8.00 (dt, J=7.8, 1.3 Hz, 1H), 7.89 (ddd, J=8.3, 2.2, 1.1 Hz, 1H), 7.74 (d, J=8.0 Hz, 1H), 7.70 (d, J=1.7 Hz, 1H), 7.64 (t, J=1.8 Hz, 1H), 7.55 (d, J=8.3 Hz, 1H), 7.46 (d, J=1.8 Hz, 1H), 7.35-7.22 (m, 4H), 7.15 (d, J=7.6 Hz, 1H), 6.71 (dd, J=17.7, 10.9 Hz, 1H), 5.97 (d, J=3.9 Hz, 1H), 5.78 (dd, J=17.6, 1.1 Hz, 1H), 5.68 (d, J=3.9 Hz, 1H), 5.24 (dd, J=11.0, 1.0 Hz, 1H).

Step-3: Preparation of 1-(3-cyanophenyl)-N-(3-(((cyclopropylmethyl)amino)(3-vinylphenyl)methyl)phenyl)-3-(trifluoromethyl)-1H-pyrazole-5-carboxamide (116d)

To a solution of 1-(3-cyanophenyl)-N-(3-(hydroxy(3-vinylphenyl)methyl)phenyl)-3-(trifluoromethyl)-1H-pyrazole-5-carboxamide (116c) (2.1 g, 4.299 mmol) in dichloromethane (50 mL) at 0° C. was added thionyl chloride (0.65 mL, 8.598 mmol) and stirred at room temperature for 4 h. The reaction mixture was concentrated in vacuum to dryness. The residue obtained was dissolved in acetonitrile (50 mL) and added cyclopropylmethanamine (5.6 mL, 64.485 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum to afford 1-(3-cyanophenyl)-N-(3-(((cyclopropylmethyl)amino)(3-vinylphenyl)methyl)phenyl)-3-(trifluoromethyl)-1H-pyrazole-5-carboxamide (116d) (4.9 g) as a red-brown sticky liquid, which was used as such without further purification.

Step-4: Preparation of 1-(3-(aminomethyl)phenyl)-N-(3-((cyclopropylmethylamino)(3-ethylphenyl)methyl)phenyl)-3-(trifluoromethyl)-1H-pyrazole-5-carboxamide (116e)

To a solution of 1-(3-cyanophenyl)-N-(3-(((cyclopropylmethyl)amino)(3-vinylphenyl)methyl)phenyl)-3-(trifluoromethyl)-1H-pyrazole-5-carboxamide (116d) (4.9 g crude, 8.986 mmol) in MeOH (50 mL) cooled with ice/water was added nickel(II) chloride hexahydrate (2.67 g, 11.233 mmol) followed by portionwise addition of sodium borohydride (2.03 g, 53.916 mmol) over a period of 15 min. The reaction mixture was stirred at room temperature for 1 h and quenched with N1-(2-aminoethyl)ethane-1,2-diamine (4.85 mL, 44.92 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over MgSO$_4$ filtered and concentrated in vacuum. The residue obtained was purified by flash column chromatography (silica gel 24 g, eluting with 0-25% chloroform/methanol) to furnish 1-(3-(aminomethyl)phenyl)-N-(3-((cyclopropylmethylamino)(3-ethylphenyl)methyl)phenyl)-3-(trifluoromethyl)-1H-pyrazole-5-carboxamide (116e) (0.041 g; 1% yield) as a white solid; $^1$H NMR (300 MHz, DMSO-d$_6$) δ 10.74 (s, 1H), 7.70 (d, J=6.3 Hz, 2H), 7.67 (s, 1H), 7.63-7.49 (m, 4H), 7.28-7.17 (m, 5H), 7.04 (q, J=3.2, 2.7 Hz, 1H), 4.83 (s, 1H), 4.11 (s, 2H), 2.56 (d, J=7.7 Hz, 2H), 2.29 (dd, J=7.8, 5.1 Hz, 2H), 1.15 (t, J=7.6 Hz, 3H), 1.01-0.86 (m, 1H), 0.46-0.35 (m, 2H), 0.06 (q, J=4.9 Hz, 2H); 19F NMR (282 MHz, DMSO-d$_6$) δ −60.79; MS (ES+) 548.3 (M+1); (ES−) 546.3 (M−1).

Scheme 117
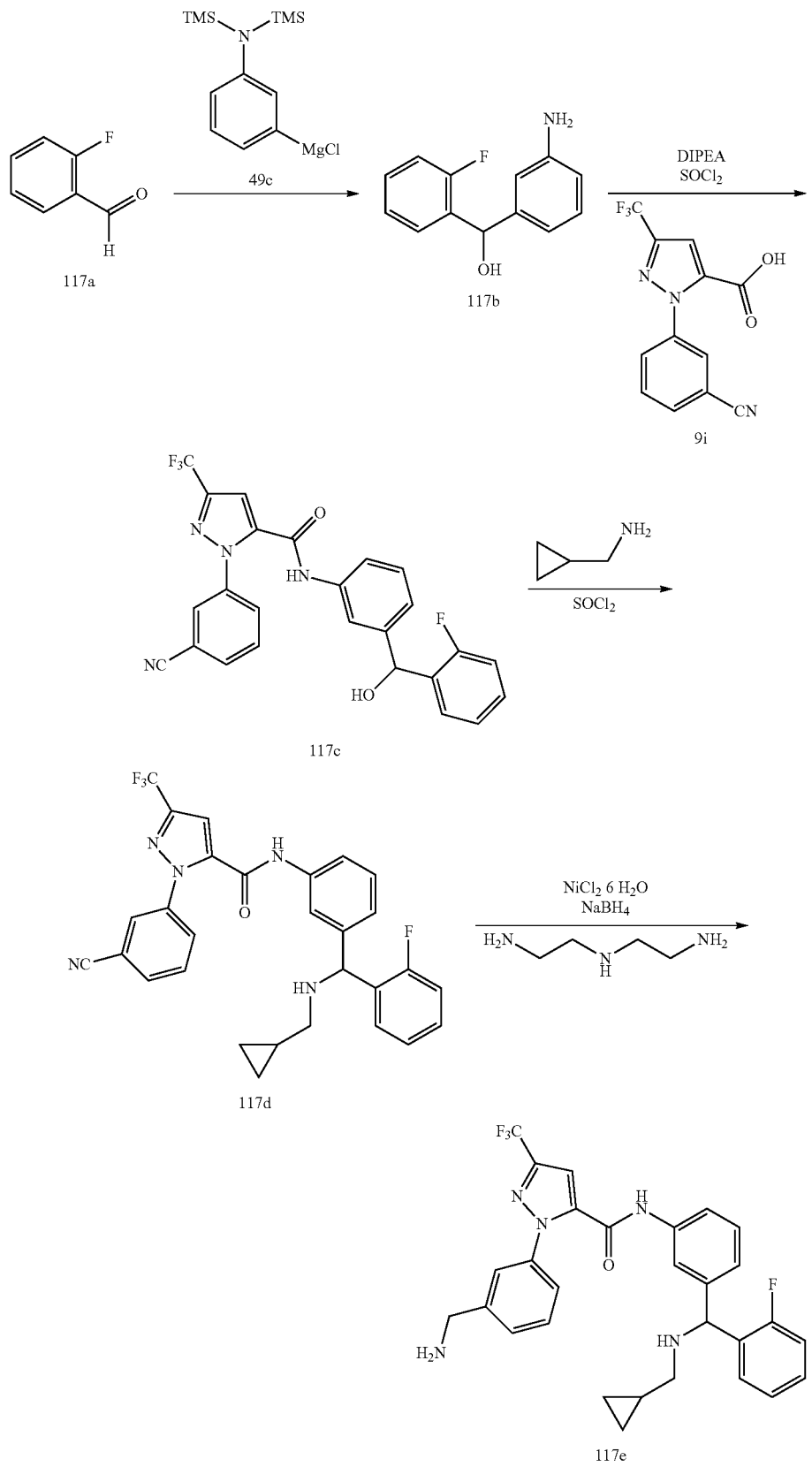

Preparation of 1-(3-(aminomethyl)phenyl)-N-(3-((cyclopropylmethylamino)(2-fluorophenyl)methyl)phenyl)-3-(trifluoromethyl)-1H-pyrazole-5-carboxamide (117e)

Step-1: Preparation of (3-aminophenyl)(2-fluorophenyl)methanol (117b)

To a stirred solution of 2-fluorobenzaldehyde (117a) (1.32 g, 10 mmol) in tetrahydrofuran (5 mL) was added (3-(bis(trimethylsilyl)amino)phenyl)magnesium chloride (49c) (12.0 mL, 12.0 mmol) at 0° C. The reaction was stirred for 14 h at room temperature and quenched by adding 2 N HCl (12.5 mL), stirred for 6 h. The reaction mixture was treated with 2 N NaOH (15 mL) and extracted with ethyl acetate (2×50 mL). The organic layers were combined washed with saturated aqueous $NH_4Cl$ (50 mL), dried over anhydrous $MgSO_4$, filtered and evaporated to dryness. The crude residue was purified by flash column chromatography (silica gel 40 g, eluting with 0-100% ethyl acetate in hexane) to furnish (3-aminophenyl)(2-fluorophenyl)methanol (117b) (1.8 g, 77.92% yield) as a red-brown oil.

Step-2: Preparation of 1-(3-cyanophenyl)-N-(3-(hydroxy(2-fluorophenyl)methyl)phenyl)-3-(trifluoromethyl)-1H-pyrazole-5-carboxamide (117c)

To a stirred solution of 2-(3-Cyano-phenyl)-5-trifluoromethyl-2H-pyrazole-3-carboxylic acid (117b) (3.02 g, 10.770 mmol) in toluene (50 mL) and DMF 15 drops was added $SOCl_2$ (2.365 g, 19.88 mmol) at 0° C. Reaction was refluxed for 3.5 hr and concentrated to remove volatile solvent. The residue obtained was dissolved in dichloromethane (100 mL) and added (3-amino-phenyl)-(2-fluoro-phenyl)-methanol (117b) (1.8 g, 8.284 mmol) was added followed by dropwise addition of triethylamine (10.8 mL) at room temperature. Reaction mixture was stirred overnight at room temp concentrated in vacuum to dryness. The residue obtained was purified by flash chromatography (10%-70% ethyl acetate in hexane) to afford product 2-(3-Cyano-phenyl)-5-trifluoromethyl-2H-pyrazole-3-carboxylic acid {3-[(2-fluoro-phenyl)-hydroxy-methyl]-phenyl}-amide (117c) (2.1 gm) as a red-brown liquid; $^1H$ NMR (300 MHz, DMSO-$d_6$) δ 10.70 (s, 1H), 8.21 (t, J=1.8 Hz, 1H), 8.05 (dt, J=7.8, 1.3 Hz, 1H), 7.95 (ddd, J=8.2, 2.1, 1.1 Hz, 1H), 7.80 (d, J=8.0 Hz, 1H), 7.76 (d, J=1.6 Hz, 1H), 7.69-7.53 (m, 3H), 7.38-7.29 (m, 2H), 7.25 (td, J=7.5, 1.3 Hz, 1H), 7.21-7.12 (m, 2H), 6.12 (d, J=4.2 Hz, 1H), 5.98 (d, J=4.2 Hz, 1H).

Step-3: Preparation of 2-(3-Cyano-phenyl)-5-trifluoromethyl-2H-pyrazole-3-carboxylic acid {3-[(cyclopropylmethyl-amino)-(2-fluoro-phenyl)-methyl]-phenyl}-amide (117d)

To a solution of 2-(3-Cyano-phenyl)-5-trifluoromethyl-2H-pyrazole-3-carboxylic acid {3-[(2-fluoro-phenyl)-hydroxy-methyl]-phenyl}-amide (117c) (2.1 g, 4.371 mmol) in dichloromethane (50 mL) at 0° C. was added thionyl chloride (0.65 mL, 8.742 mmol) and stirred at room temperature for 4 h. The reaction mixture was concentrated in vacuum to dryness. The residue obtained was dissolved in acetonitrile (50 mL) and added cyclopropylmethanamine (5.7 mL, 65.568 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum. The residue obtained was purified by flash column chromatography (silica gel 40 g, eluting 0-100% ethyl acetate in hexane) to afford 2-(3-Cyano-phenyl)-5-trifluoromethyl-2H-pyrazole-3-carboxylic acid {3-[(cyclopropylmethyl-amino)-(2-fluoro-phenyl)-methyl]-phenyl}-amide (117d) (1.05 g, 45.06% yield) as a red-brown sticky liquid.

Step-4: Preparation of 1-(3-(aminomethyl)phenyl)-N-(3-((cyclopropylmethylamino)(2-fluorophenyl)methyl)phenyl)-3-(trifluoromethyl)-1H-pyrazole-5-carboxamide (117e)

To a solution of 2-(3-Cyano-phenyl)-5-trifluoromethyl-2H-pyrazole-3-carboxylic acid {3-[(cyclopropylmethyl-amino)-(2-fluoro-phenyl)-methyl]-phenyl}-amide (117d) (1.05 g, 1.968 mmol) in MeOH (20 mL) cooled with ice/water was added nickel(II) chloride hexahydrate (0.584 g, 2.46 mmol) followed by portionwise addition of sodium borohydride (0.45 g, 11.808 mmol) over a period of 15 min. The reaction mixture was stirred at room temperature for 1 h and quenched with N1-(2-aminoethyl)ethane-1,2-diamine (1.06 mL, 9.84 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over $MgSO_4$ filtered and concentrated in vacuum. The residue obtained was purified by flash column chromatography (silica gel 24 g, eluting with 0-25% chloroform/methanol) to furnish 2-(3-Aminomethyl-phenyl)-5-trifluoromethyl-2H-pyrazole-3-carboxylic acid {3-[(cyclopropylmethyl-amino)-(2-fluoro-phenyl)-methyl]-phenyl}-amide (117e) (0.29 g, 27.43% yield) as a white solid; $^1H$ NMR (300 MHz, DMSO-$d_6$) δ 10.78 (s, 1H), 8.37 (s, 3H), 7.72 (s, 1H), 7.70-7.56 (m, 5H), 7.56-7.47 (m, 1H), 7.28 (t, J=7.8 Hz, 2H), 7.22 (s, 2H), 7.12 (dd, J=10.7, 8.2 Hz, 1H), 5.17 (s, 1H), 4.12 (s, 2H), 2.34 (d, J=6.7 Hz, 2H), 0.94 (d, J=11.1 Hz, 1H), 0.48-0.35 (m, 2H), 0.12-0.02 (m, 2H); $^{19}F$ NMR (282 MHz, DMSO $d_6$) δ −60.79, −118.99; MS (ES+) 538.3 (M+1); (ES−) 536.3 (M−1); Analysis calculated for $C_{30}H_{30}F_3N_5O_2 \cdot 2.75HCl$: C, 54.61; H, 4.70; N, 10.98; Found: C, 54.63; H, 4.50; N, 11.17.

Scheme 118
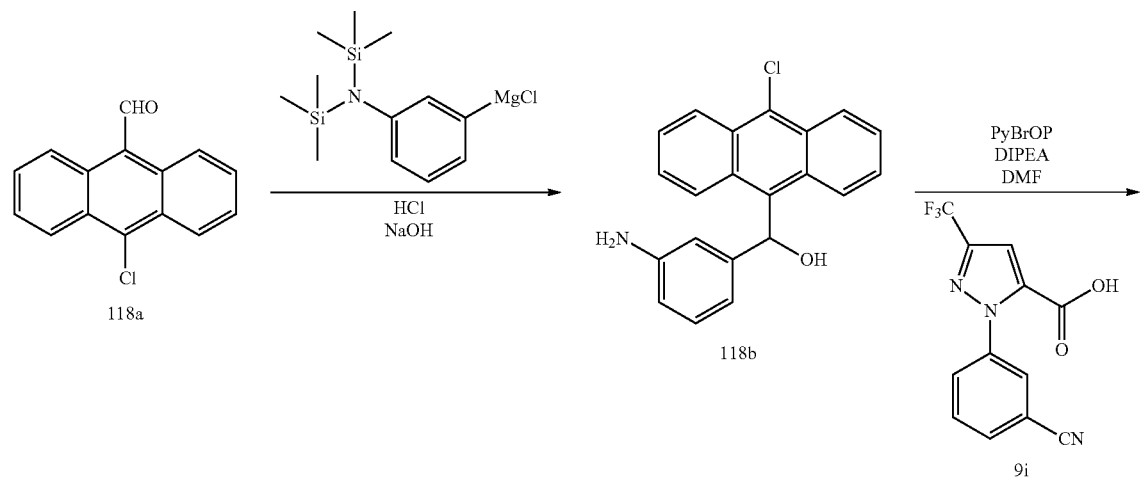
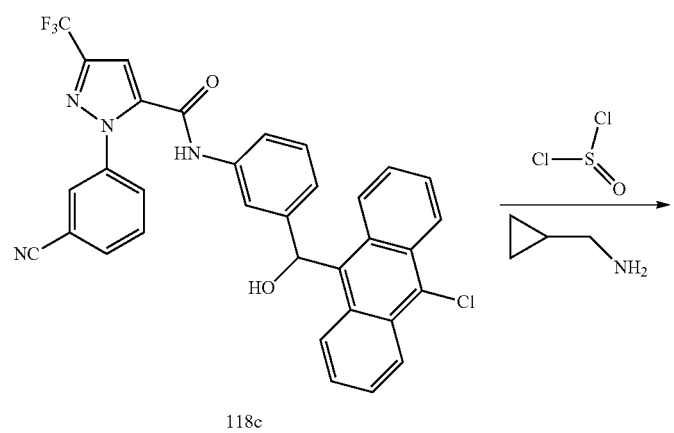
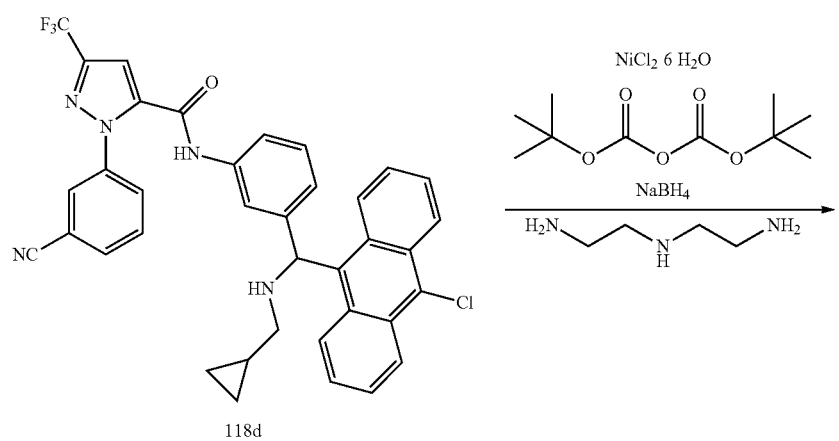

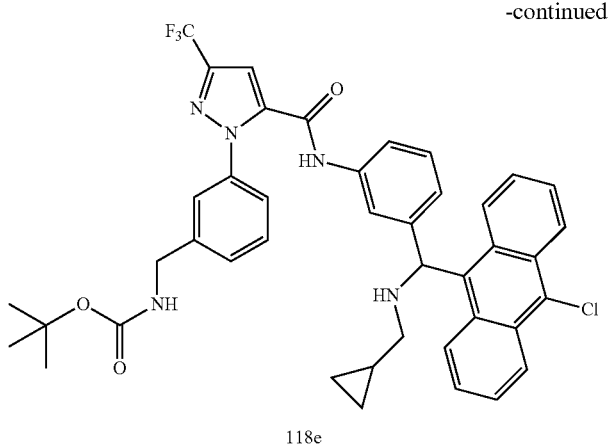

118e

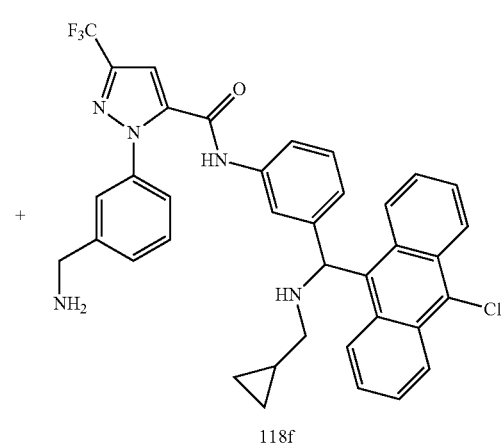

118f

Preparation of 1-(3-(aminomethyl)phenyl)-N-(3-((10-chloroanthracen-9-yl)(cyclopropylmethyl-amino)methyl)phenyl)-3-(trifluoromethyl)-1H-pyrazole-5-carboxamide (118f)

Step-1: Preparation of (3-aminophenyl)(10-chloroanthracen-9-yl)methanol (118b)

To a stirred solution of 10-chloroanthracene-9-carbaldehyde (118a) (2 g, 8.31 mmol) in tetrahydrofuran (20 mL) was added (3-(bis(trimethylsilyl)amino)phenyl)magnesium chloride (49c) (2.95 g, 9.97 mmol) at 0° C. The reaction was stirred for 14 h at same temperature and quenched by adding 2 N HCl (10.39 mL, 20.77 mmol), stirred for 2 h. The reaction mixture was treated with 2 N NaOH (12.46 mL, 24.93 mmol) and extracted with ethyl acetate (2×50 mL). The organic layers were combined washed with sat. NH$_4$Cl (50 mL), dried over anhydrous MgSO$_4$, filtered, evaporated to dryness. The crude residue was purified by flash column chromatography (silica gel 40 g, eluting with 0-100% ethyl acetate in hexane) to furnish (3-aminophenyl)(10-chloroanthracen-9-yl)methanol (118b) (2.375 g, 7.11 mmol, 86% yield) as a yellow solid; $^1$H NMR (300 MHz, DMSO-d$_6$) δ 8.63 (d, J=9.0 Hz, 2H), 8.49 (dd, J=8.8, 1.2 Hz, 2H), 7.78-7.60 (m, 2H), 7.53 (dd, J=8.9, 6.6 Hz, 2H), 7.16 (d, J=4.3 Hz, 1H), 6.90 (t, J=7.8 Hz, 1H), 6.52-6.47 (m, 1H), 6.41 (s, 1H), 6.38-6.31 (m, 2H), 4.91 (s, 2H, D$_2$O exchangeable); $^1$H NMR (300 MHz, DMSO-d$_6$ D$_2$O) δ 8.61 (d, J=9.0 Hz, 2H), 8.51 (dd, J=8.7, 1.2 Hz, 2H), 7.69 (ddd, J=8.9, 6.5, 1.1 Hz, 2H), 7.54 (dd, J=8.9, 6.6 Hz, 2H), 7.16 (s, 1H), 6.92 (t, J=7.7 Hz, 1H), 6.55-6.43 (m, 2H), 6.37 (dd, J=7.7, 2.2 Hz, 1H); MS (ES−): MS (ES−) 332.3 (M−1).

Step-2: Preparation of N-(3-((10-chloroanthracen-9-yl)(hydroxy)methyl)phenyl)-1-(3-cyanophenyl)-3-(trifluoromethyl)-1H-pyrazole-5-carboxamide (118c)

To a single-necked 100 mL flask containing 1-(3-cyanophenyl)-3-(trifluoromethyl)-1H-pyrazole-5-carboxylic acid (9i) (1.264 g, 4.49 mmol), (3-aminophenyl)(10-chloroanthracen-9-yl)methanol (118b) (1.5 g, 4.49 mmol), bromotris-pyrrolidino phosphoniumhexafluorophosphate (PyBrop, 2.51 g, 5.39 mmol) was added N,N-dimethylformamide (26.1 mL, 337 mmol), N-ethyl-N-isopropylpropan-2-amine (3.91 mL, 22.47 mmol) successively in a positive flow of nitrogen at room temperature. The resulting reaction mixture was stirred at room temperature for 16 h under a positive flow of nitrogen atmosphere. Excess DMF was pumped-off under reduced pressure. The residue was treated with water (75 mL) extracted with chloroform (2×75 mL). The combined organic layers were dried over anhydrous MgSO$_4$, filtered and evaporated to dryness. The residue was purified by flash column chromatography [silica gel 40 g, eluting with ethyl acetate in hexanes from 0-100%] to furnish N-(3-((10-chloroanthracen-9-yl)(hydroxy)methyl)phenyl)-1-(3-cyanophenyl)-3-(trifluoromethyl)-1H-pyrazole-5-carboxamide (118c) (1.823 g, 68.0% yield) as a yellow solid. MS (ES−) 595.2 (M−1).

Step-3: Preparation of N-(3-((10-chloroanthracen-9-yl)(cyclopropylmethylamino)methyl)phenyl)-1-(3-cyanophenyl)-3-(trifluoromethyl)-1H-pyrazole-5-carboxamide (118d)

To a solution of N-(3-((10-chloroanthracen-9-yl)(hydroxy)methyl)phenyl)-1-(3-cyanophenyl)-3-(trifluoromethyl)-1H-pyrazole-5-carboxamide (118c) (1.685 g, 2.82 mmol) in dichloromethane (20 mL) at 0° C. was added thionyl chloride (0.618 mL, 8.47 mmol) and stirred at room temperature for 18 h. The reaction mixture was quenched with cyclopropylmethanamine (1.693 mL, 19.76 mmol) stirred for 1 h at room temperature, and concentrated in vacuum to dryness. The residue was dissolved in cyclopropylmethanamine (4.84 mL, 56.5 mmol) and acetonitrile (20 mL) and the reaction mixture was heated at 80° C. for 16 h TLC analysis (ethyl acetate/hexanes, 3/7, v/v) shows reaction was complete; reaction mixture was evaporated to dryness. The residue was purified by flash column chromatography (silica gel 40 g, eluting 0-100% ethyl acetate in hexanes from 0-100%) to afford N-(3-((10-chloroanthracen-9-yl)(cyclopropylmethylamino)methyl)phenyl)-1-(3-cyanophenyl)-3-(trifluoromethyl)-1H-pyrazole-5-carboxamide (118d) (0.903 g, 1.389 mmol, 49.2% yield) as a yellow solid. MS (ES+) 649.19 (M−1).

Step-3: Preparation of 1-(3-(aminomethyl)phenyl)-N-(3-((10-chloroanthracen-9-yl)(cyclopropylmethyl-amino)methyl)phenyl)-3-(trifluoromethyl)-1H-pyrazole-5-carboxamide (118f)

To a stirred solution of N-(3-((10-chloroanthracen-9-yl)(cyclopropylmethylamino)methyl)phenyl)-1-(3-cyanophenyl)-3-(trifluoromethyl)-1H-pyrazole-5-carboxamide (118d) (831 mg, 1.278 mmol) in anhydrous methanol (20 mL), cooled to 0° C. was added, di-tert-butyl dicarbonate (0.837 g, 3.83 mmol), nickel(II) chloride hexahydrate (0.380 g, 1.598 mmol) followed by sodium borohydride (0.283 g, 7.668 mmol) in small portions over a period of 5 min. The reaction was exothermic and effervescent. The reaction mixture was stirred for 45 min at 0° C., at this point N1-(2-aminoethyl)ethane-1,2-diamine (1.381 mL, 12.78 mmol) was added. The mixture was allowed to stir for 30 mins and concentrated in vacuum to dryness. The residue was treated with water (50 mL), and extracted with chloroform (2×50 mL). The organic layers were combined dried over anhydrous $MgSO_4$; filtered and excess solvents were pumped-off under reduced pressure. The residue was purified by flash column chromatography [(silica gel 40 g, eluting with methanol/chloroform from 0 to 100%)] to furnish tert-butyl 3-(5-(3-((10-chloroanthracen-9-yl)(cyclopropylmethylamino)methyl)phenylcarbamoyl)-3-(trifluoromethyl)-1H-pyrazol-1-yl)benzylcarbamate (118e) (0.463 g, 0.614 mmol, 48.0% yield) as a yellow solid and 1-(3-(aminomethyl)phenyl)-N-(3-((10-chloroanthracen-9-yl)(cyclopropylmethylamino)methyl)phenyl)-3-(trifluoromethyl)-1H-pyrazole-5-carboxamide (118f) (0.143 g, 0.219 mmol, 17.10% yield) which was isolated as a free-base. Free base of compound 118f was treated with aqueous 12 N HCl (7 eq, 0.13 mL) in 2 mL of IPA and stirred for 10 min, then triturated with ether, refluxed for 1 h, cooled to room temperature. The solid obtained was collected by filtration dried under reduced pressure for 16 h to afford 1-(3-(aminomethyl)phenyl)-N-(3-((10-chloroanthracen-9-yl)(cyclopropylmethylamino)methyl)phenyl)-3-(trifluoromethyl)-1H-pyrazole-5-carboxamide (118f) (50 mgs) hydrochloride salt as a yellow solid. $^1$H NMR (300 MHz, DMSO-$d_6$) δ 10.79 (s, 1H), 10.66 (s, 1H), 9.79 (s, 1H), 8.83-8.57 (m, 3H), 8.40 (s, 3H), 8.20 (m, 1H), 7.79 (m, 4H), 7.66-7.45 (m, 6H), 7.24 (m, 1H), 7.15 (s, 1H), 4.09 (q, J=5.8 Hz, 2H), 3.03 (m, 1H), 2.64 (m, 1H), 1.21-1.07 (m, 1H), 0.47 (m, 2H), 0.33-0.12 (m, 2H); $^{19}$F NMR (282 MHz, DMSO) δ −60.86; MS (ES+) 654.3 (M+1); (ES−) 652.3 (M−1); Analysis calculated for $C_{37}H_{31}ClF_3N_5O.2.25HCl.2H_2O$: C, 57.55; H, 4.86; Cl, 14.92; N, 9.07; Found: C, 57.29; H, 4.96; Cl, 14.96; N, 8.87.

Scheme 119

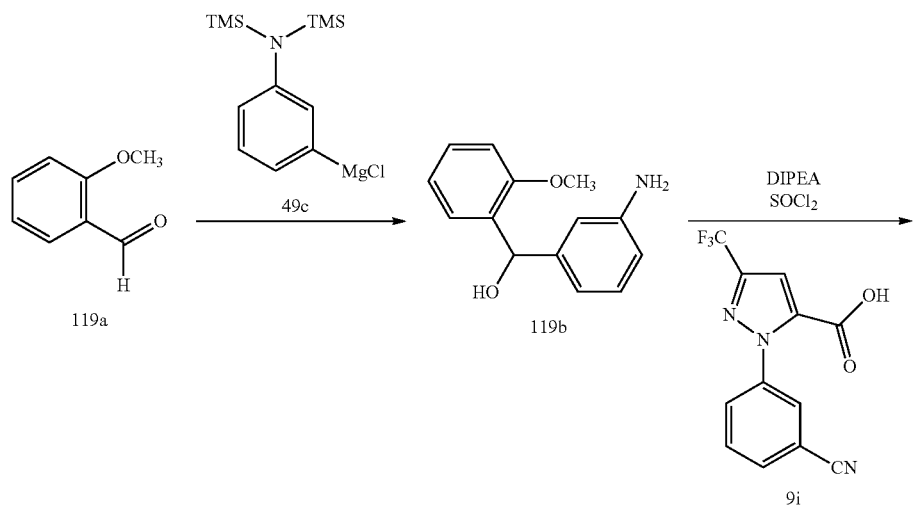

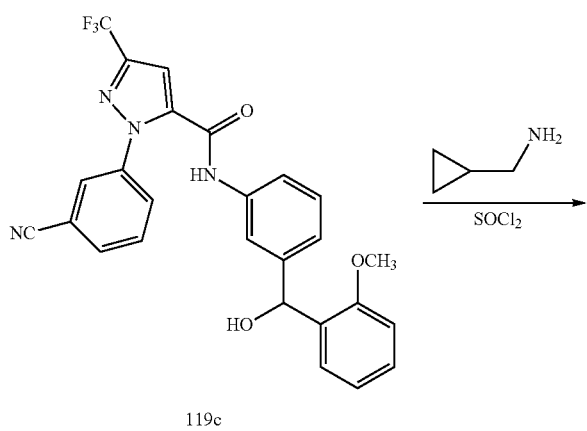

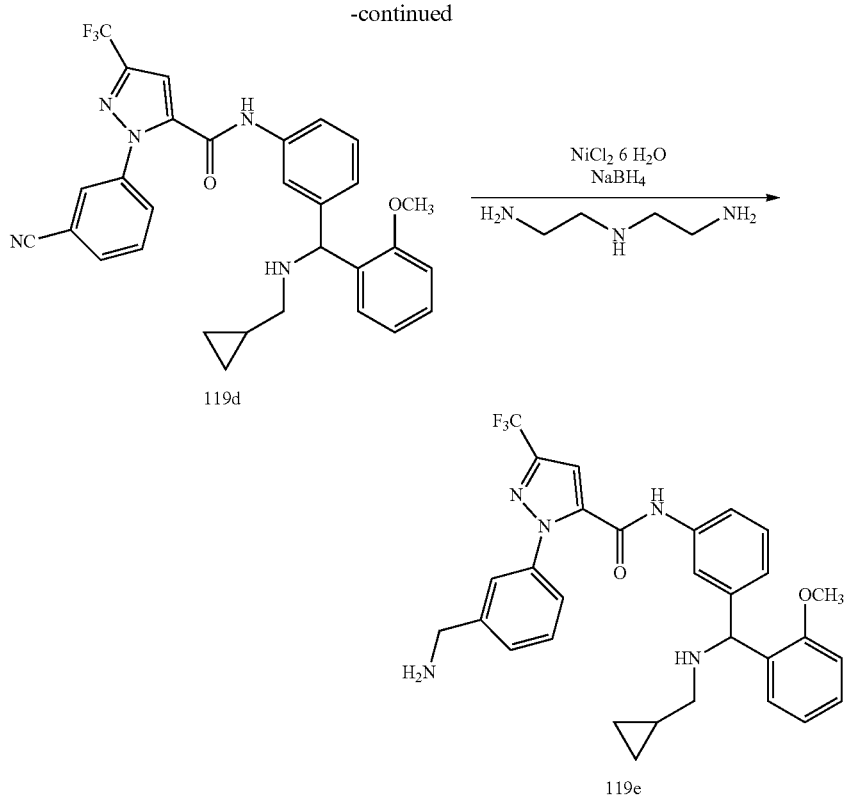

Preparation of 1-(3-(aminomethyl)phenyl)-N-(3-(((cyclopropylmethyl)amino)(2-methoxyphenyl)methyl)phenyl)-3-(trifluoromethyl)-1H-pyrazole-5-carboxamide (119e)

Step-1: Preparation of (3-aminophenyl)(2-methoxyphenyl)methanol (119b)

To a stirred solution of 2-methoxybenzaldehyde (119a) (1.36 g, 10 mmol) in tetrahydrofuran (5 mL) was added (3-(bis(trimethylsilyl)amino)phenyl)magnesium chloride (49c) (12.00 mL, 12.00 mmol) at 0° C. The reaction was stirred for 14 h at room temperature and quenched by adding 2 N HCl (12.50 mL), stirred for 6 h. The reaction mixture was treated with 2 N NaOH (15 mL) and extracted with ethyl acetate (2×50 mL). The organic layers were combined washed with saturated aqueous NH$_4$Cl (50 mL), dried over anhydrous MgSO$_4$, filtered, evaporated to dryness. The crude residue was purified by flash column chromatography (silica gel 40 g, eluting with 0-100% ethyl acetate in hexane) to furnish (3-aminophenyl)(2-methoxyphenyl)methanol (119b) (0.8 g, 35% yield) as a red-brown oil.

Step-2: Preparation of 1-(3-cyanophenyl)-N-(3-(hydroxy(2-methoxyphenyl)methyl)phenyl)-3-(trifluoromethyl)-1H-pyrazole-5-carboxamide (119c)

To a stirred solution of 2-(3-Cyano-phenyl)-5-trifluoromethyl-2H-pyrazole-3-carboxylic acid (9i) (1.275 g, 4.536 mmol) in toluene (50 mL) and DMF 15 drops was added SOCl$_2$ (0.618 mL, 12.78 mmol) at 0° C. Reaction was refluxed for 3.5 hr and concentrated to remove volatile solvent. The residue obtained was dissolved in DCM (100 mL) and (3-aminophenyl)(2-methoxyphenyl)methanol (119b) (0.8 g, 3.5 mmol) was added followed by dropwise addition of triethylamine (4.8 mL) at RT. Reaction mixture was stirred overnight at room temp and concentrated in vacuum to dryness. The residue obtained was purified by flash chromatography (10%-70% ethyl acetate in hexane) to afford 1-(3-cyanophenyl)-N-(3-(hydroxy(2-methoxyphenyl)methyl)phenyl)-3-(trifluoromethyl)-1H-pyrazole-5-carboxamide (119c) (1.8 g, 80.76%) as a red-brown oil which solidified on standing; $^1$H NMR (300 MHz, DMSO-d$_6$) δ 10.66 (s, 1H), 8.20 (t, J=1.9 Hz, 1H), 8.05 (dt, J=7.8, 1.3 Hz, 1H), 7.95 (ddd, J=8.2, 2.2, 1.1 Hz, 1H), 7.79 (d, J=8.0 Hz, 1H), 7.76 (s, 1H), 7.69 (t, J=1.9 Hz, 1H), 7.61-7.54 (m, 1H), 7.49 (dd, J=7.8, 1.8 Hz, 1H), 7.32-7.22 (m, 2H), 7.19-7.11 (m, 1H), 7.03-6.94 (m, 2H), 6.03 (d, J=4.1 Hz, 1H), 3.80 (s, 3H).

Step-3: Preparation of 2-(3-Cyano-phenyl)-5-trifluoromethyl-2H-pyrazole-3-carboxylic acid {3-[(cyclopropylmethyl-amino)-(2-fluoro-phenyl)-methyl]-phenyl}-amide (119d)

To a solution of 1-(3-cyanophenyl)-N-(3-(hydroxy(2-methoxyphenyl)methyl)phenyl)-3-(trifluoromethyl)-1H-pyrazole-5-carboxamide (119c) (1.8 g, 3.655 mmol) in dichloromethane (50 mL) at 0° C. was added thionyl chloride (0.87 g, 7.310 mmol) and stirred at room temperature for 4 h. The reaction mixture was concentrated in vacuum to dryness. The residue obtained was dissolved in acetonitrile (50 mL) and added cyclopropylmethanamine (3.9 g, 54.82 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum. The residue obtained (4.2 gm crude) of 2-(3-Cyano-phenyl)-5-trifluoromethyl-2H-pyrazole-3-carboxylic acid {3-[(cyclopropylmethyl-amino)-(2-fluoro-phenyl)-methyl]-phenyl}-amide (119d) as a red brown oil was used as such for next step.

Step-4: Preparation of 1-(3-(aminomethyl)phenyl)-N-(3-(((cyclopropylmethylamino)(2-fluorophenyl)methyl)phenyl)-3-(trifluoromethyl)-1H-pyrazole-5-carboxamide (119e)

To a solution of 2-(3-Cyano-phenyl)-5-trifluoromethyl-2H-pyrazole-3-carboxylic acid {3-[(cyclopropylmethyl-amino)-(2-fluoro-phenyl)-methyl]-phenyl}-amide (119d) (4.2 gm crude) in MeOH (50 mL) cooled with ice/water was added nickel(II) chloride hexahydrate (2.28 g, 9.628 mmol) followed by portionwise addition of sodium borohydride (1.748 g, 46.212 mmol) over a period of 15 min. The reaction mixture was stirred at room temperature for 1 h and quenched with N1-(2-aminoethyl)ethane-1,2-diamine (4.85 mL, 44.92 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over MgSO₄ filtered and concentrated in vacuum. The residue obtained was purified by flash column chromatography (silica gel 24 g, eluting with 0-25% chloroform/methanol) to furnish 1-(3-(aminomethyl)phenyl)-N-(3-(((cyclopropylmethyl)amino)(2-methoxyphenyl)methyl)phenyl)-3-(trifluoromethyl)-1H-pyrazole-5-carboxamide (119e) (210 mgs, 10%) as a white solid. The solid was repurified by flash column chromatography (silica gel 4 g, eluting with 0-25% chloroform/methanol) to furnish product which was dissolved in methanol added 10 eq of conc. HCL and concentrated in vacuum to dryness to furnish 1-(3-(aminomethyl)phenyl)-N-(3-(((cyclopropylmethyl)amino)(2-methoxyphenyl)methyl)phenyl)-3-(trifluoromethyl)-1H-pyrazole-5-carboxamide (119e) (10 mg) as a HCl salt; $^1$H NMR (300 MHz, DMSO-d₆) δ 10.97 (s, 1H), 10.04 (s, 1H), 9.72 (s, 1H), 8.49 (s, 3H), 7.84 (t, J=1.8 Hz, 1H), 7.78 (dd, J=7.8, 1.6 Hz, 1H), 7.73 (d, J=1.7 Hz, 1H), 7.70 (s, 1H), 7.66-7.60 (m, 2H), 7.59-7.48 (m, 3H), 7.45-7.33 (m, 2H), 7.06 (ddd, J=14.9, 7.9, 1.0 Hz, 2H), 5.74 (s, 1H), 4.12 (s, 2H), 3.82 (s, 3H), 2.81-2.67 (m, 2H), 1.20-0.99 (m, 1H), 0.62-0.49 (m, 2H), 0.32-0.20 (m, 2H); 19F NMR (282 MHz, DMSO-d₆) δ −60.79; MS (ES+) 550.04 (M+1); (ES−) 548.3 (M−1).

Scheme 120

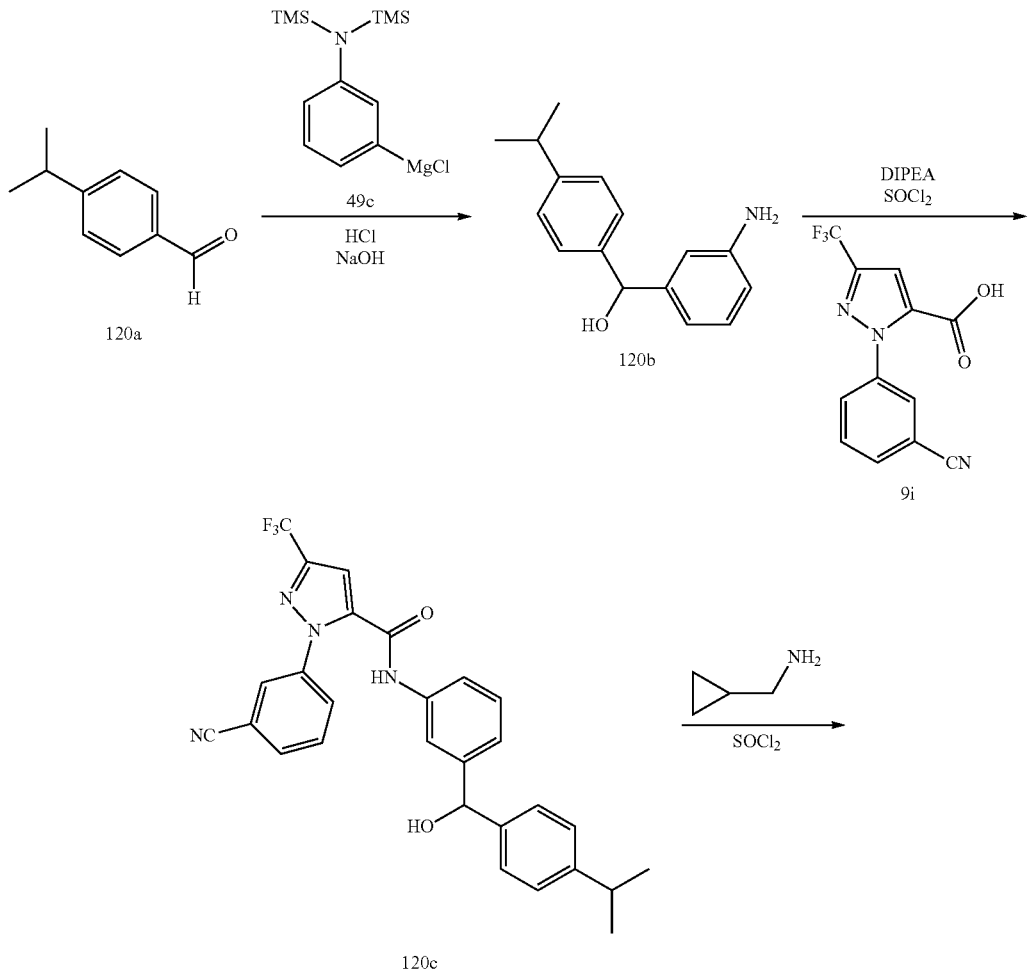

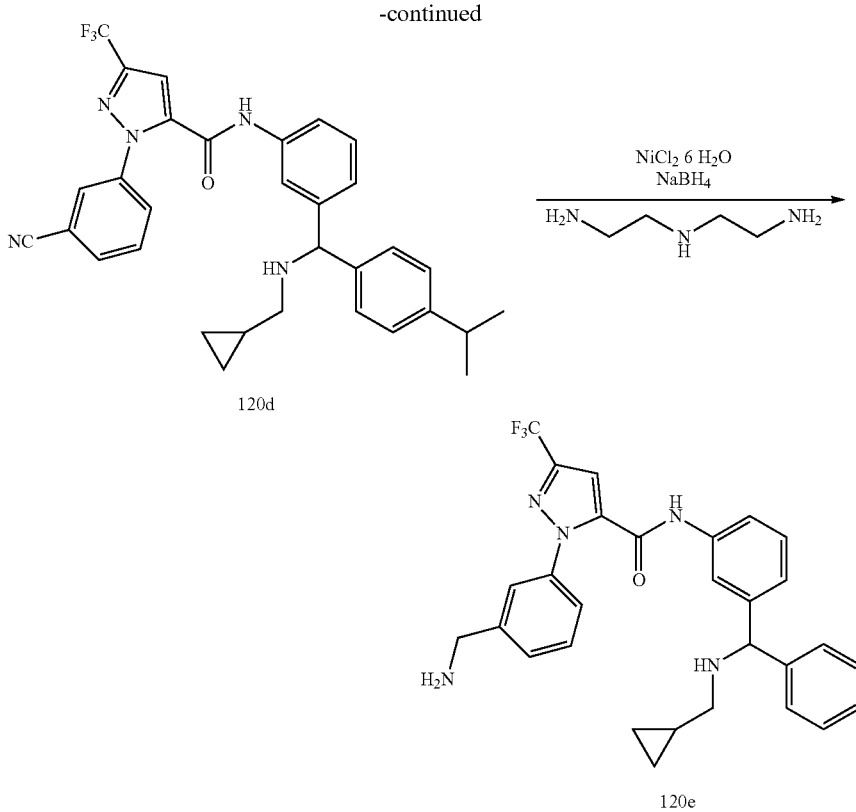

120d

120e

Preparation of 1-(3-(aminomethyl)phenyl)-N-(3-(((cyclopropylmethyl)amino)(4-isopropylphenyl)methyl)phenyl)-3-(trifluoromethyl)-1H-pyrazole-5-carboxamide (120e)

Step-1: Preparation of (3-aminophenyl)(4-isopropylphenyl)methanol (120b)

To a stirred solution of 4-isopropylbenzaldehyde (120a) (1.48 g, 10 mmol) in tetrahydrofuran (5 mL) was added (3-(bis(trimethylsilyl)amino)phenyl)magnesium chloride (49c) (12.0 mL, 12.0 mmol) at 0° C. The reaction was stirred for 14 h at room temperature and quenched by adding 2 N HCl (12.50 mL), stirred for 6 h. The reaction mixture was treated with 2 N NaOH (15 mL) and extracted with ethyl acetate (2×50 mL). The organic layers were combined washed with sat. $NH_4Cl$ (50 mL), dried over anhydrous $MgSO_4$, filtered, evaporated to dryness. The crude residue was purified by flash column chromatography (silica gel 40 g, eluting with 0-100% ethyl acetate in hexane) to furnish (4-aminophenyl)(4-isopropylphenyl)methanol (120b) (1.85 g, 81% yield) as a red-brown sticky liquid.

Step-2: Preparation of 1-(3-cyanophenyl)-N-(3-(hydroxy(4-isopropylphenyl)methyl)phenyl)-3-(trifluoromethyl)-1H-pyrazole-5-carboxamide (120c)

To a stirred solution of 2-(3-Cyano-phenyl)-5-trifluoromethyl-2H-pyrazole-3-carboxylic acid (9i) (2.726 g, 9.696 mmol) in toluene (50 mL) and DMF 15 drops was added $SOCl_2$ (2.129 g, 17.900 mmol) at 0° C. Reaction was refluxed for 3.5 hr and concentrated to remove volatile solvent. The residue obtained was dissolved in DCM (100 mL) and (3-aminophenyl)(4-isopropylphenyl)methanol (120b) (1.85 g, 7.46 mmol) was added followed by dropwise addition of Triethylamine 7.2 mL) at RT. Reaction mixture was stirred overnight at room temp concentrated in vacuum to dryness. The residue obtained was purified by flash chromatography (10%-70% ethyl acetate in hexane) to afford 1-(3-cyanophenyl)-N-(3-(hydroxy(4-isopropylphenyl)methyl)phenyl)-3-(trifluoromethyl)-1H-pyrazole-5-carboxamide (120c) (3.1 g, 82.44%) as a red-brown sticky liquid; $^1H$ NMR (300 MHz, DMSO-$d_6$) δ 10.63 (s, 1H), 8.16 (t, J=1.8 Hz, 1H), 8.00 (dt, J=7.8, 1.3 Hz, 1H), 7.90 (ddd, J=8.2, 2.2, 1.1 Hz, 1H), 7.78-7.69 (m, 2H), 7.64 (t, J=1.8 Hz, 1H), 7.60-7.52 (m, 1H), 7.31-7.22 (m, 3H), 7.15 (dd, J=8.5, 6.8 Hz, 3H), 5.86 (d, J=3.7 Hz, 1H), 5.63 (d, J=3.7 Hz, 1H), 2.83 (p, J=6.9 Hz, 1H), 1.16 (d, J=7.0 Hz, 6H).

Step-3: Preparation of 1-(3-cyanophenyl)-N-(3-(((cyclopropylmethyl)amino)(4-isopropylphenyl)methyl)phenyl)-3-(trifluoromethyl)-1H-pyrazole-5-carboxamide (120d)

To a solution of 1-(3-cyanophenyl)-N-(3-(hydroxy(4-isopropylphenyl)methyl)phenyl)-3-(trifluoromethyl)-1H-pyrazole-5-carboxamide (120c) (3.8 g, 7.53 mmol) in dichloromethane (50 mL) at 0° C. was added thionyl chloride 0.89 mL, 12.288 mmol) and stirred at room temperature for 4 h. The reaction mixture was concentrated in vacuum to dryness. The residue obtained was dissolved in acetonitrile (50 mL) and added cyclopropylmethanamine (8.0 mL, 92.17 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum. The residue obtained was purified by flash column chromatography (silica gel 40 g, eluting 0-100% ethyl acetate in hexane) to afford 1-(3-cyanophenyl)-N-(3-(((cyclopropylmethyl)amino)(4-isopropylphenyl)methyl)phenyl)-3-(trifluoromethyl)-1H-pyrazole-5-carboxamide (120d) (1.05 g, 30.64% yield) as a red-brown sticky liquid which was used as such for next step.

Step-4: Preparation of 1-(3-(aminomethyl)phenyl)-N-(3-(((cyclopropylmethyl)amino)(4-isopropylphenyl)methyl)phenyl)-3-(trifluoromethyl)-1H-pyrazole-5-carboxamide (120e)

To a solution of 1-(3-cyanophenyl)-N-(3-(((cyclopropylmethyl)amino)(4-isopropylphenyl)methyl)phenyl)-3-(trifluoromethyl)-1H-pyrazole-5-carboxamide (120d) (1.05 g, 1.883 mmol) in MeOH (20 mL) cooled with ice/water was added nickel(II) chloride hexahydrate (0.559 g, 2.353 mmol) followed by portionwise addition of Sodium Borohydride (0.427 g, 11.298 mmol) over a period of 15 min. The reaction mixture was stirred at room temperature for 1 h and quenched with N$^1$-(2-aminoethyl)ethane-1,2-diamine (1.2 mL, 11.83 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over MgSO$_4$ filtered and concentrated in vacuum. The residue obtained was purified by flash column chromatography (silica gel 24 g, eluting with 0-25% chloroform/methanol) to furnish 1-(3-(aminomethyl)phenyl)-N-(3-(((cyclopropylmethyl)amino)(2-methoxyphenyl)methyl)phenyl)-3-(trifluoromethyl)-1H-pyrazole-5-carboxamide (120e) (168 mg, 16% yield) free base as a white solid. The solid was repurified by flash column chromatography (silica gel 4 g, eluting with 0-25% chloroform/methanol) to furnish product (120e) as a free base, which was dissolved in methanol added 10 equi of conc. HCL and concentrated in vacuum to dryness to furnish 1-(3-(aminomethyl)phenyl)-N-(3-(((cyclopropylmethyl)amino)(2-methoxyphenyl)methyl)phenyl)-3-(trifluoromethyl)-1H-pyrazole-5-carboxamide (120e) (10 mg) as a HCl salt; $^1$H NMR (300 MHz, DMSO-d$_6$) δ 10.99 (s, 1H), 10.07 (s, 2H), 8.52 (s, 3H), 7.88 (t, J=1.8 Hz, 1H), 7.72 (d, J=3.6 Hz, 2H), 7.69-7.49 (m, 7H), 7.43 (t, J=7.9 Hz, 1H), 7.29 (d, J=8.0 Hz, 2H), 5.58-5.44 (m, 1H), 4.12 (q, J=5.7 Hz, 2H), 2.87 (p, J=6.9 Hz, 1H), 2.70 (q, J=6.1 Hz, 2H), 1.26-1.08 (m, 7H), 0.59-0.49 (m, 2H), 0.35-0.25 (m, 2H); $^{19}$F NMR (282 MHz, DMSO) δ −60.79; MS (ES+) 562.4 (M+1); (ES−) 560.4 (M−1); Analysis calculated for C$_{32}$H$_{34}$F$_3$N$_5$O.1.95HCl.1.75H$_2$O: C, 57.86; H, 5.99; Cl, 10.41; N, 10.54; Found: C, 58.01; H, 6.02; Cl, 10.03; N, 10.06.

Scheme 121

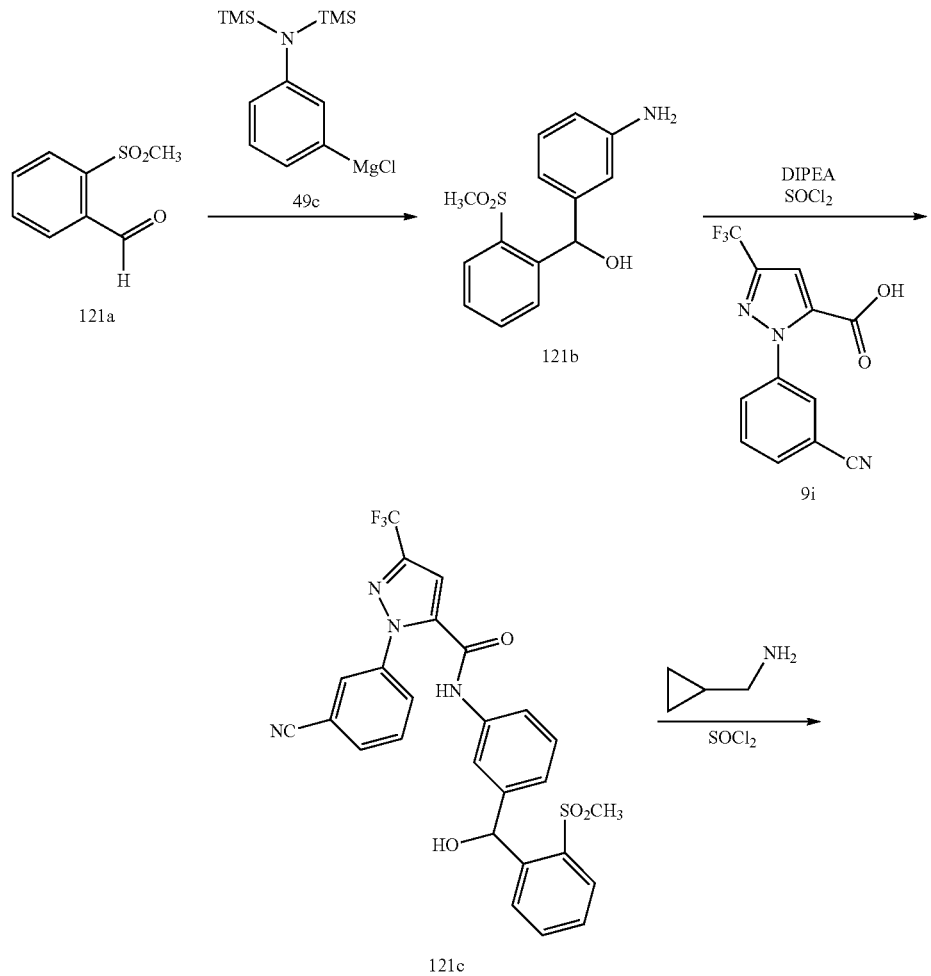

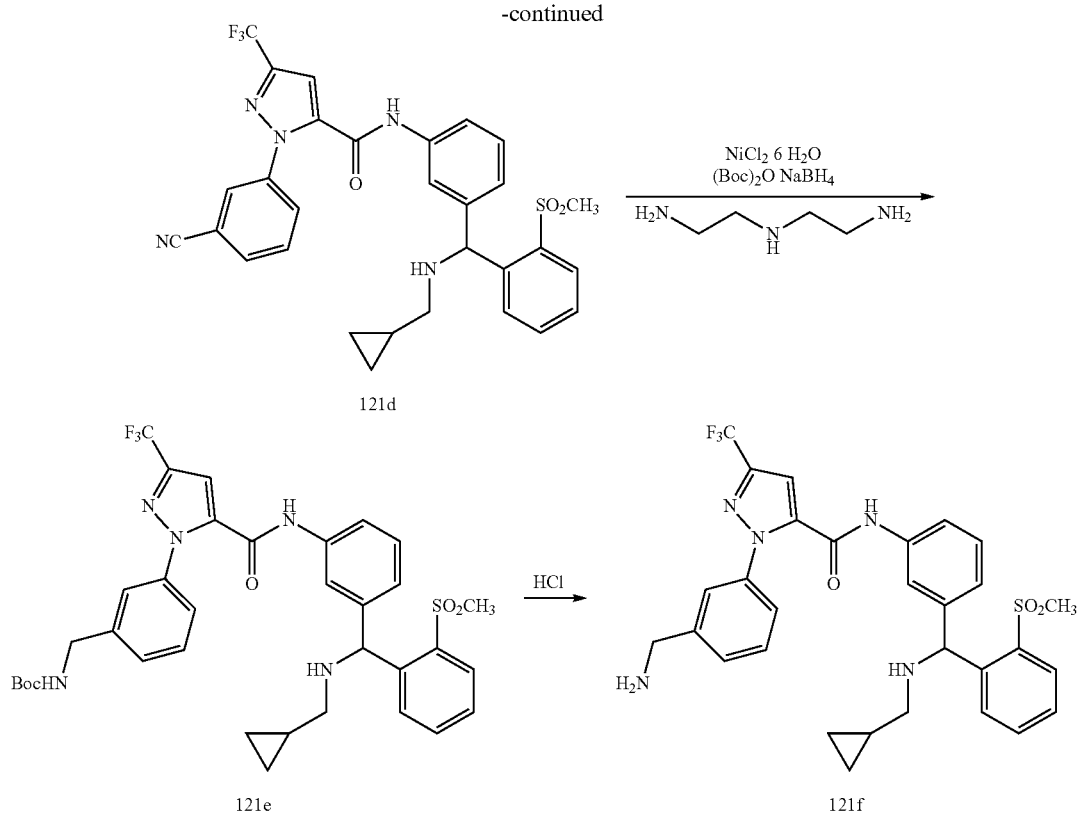

Preparation of 1-(3-(aminomethyl)phenyl)-N-(3-((cyclopropylmethylamino)(2-(methylsulfonyl)phenyl)methyl)phenyl)-3-(trifluoromethyl)-1H-pyrazole-5-carboxamide (121f)

Step-1: Preparation of (3-aminophenyl)(2-(methylsulfonyl)phenyl)methanol (121b)

To a solution of 2-(methylsulfonyl)benzaldehyde (121a) (3.80 g, 20 mmol) in tetrahydrofuran (30 mL) was cooled to 0° C. was added (3-(bis(trimethylsilyl)amino)phenyl)magnesium chloride (49c) (24.00 mL, 24.00 mmol) and stirred at room temperature for 12 h. The reaction mixture was treated with 1 N HCl (aq. 50 mL), stirred at RT for 1 h, neutralized with NaOH (2 N, aq.) to pH=~8, and extracted with ethyl acetate (2×80 mL). The combined extracts were washed with brine (60 mL), dried over MgSO$_4$ followed by filtration and concentration. The crude product was purified by flash column chromatography [silica gel 80 g, eluting with chloroform/methanol (1:0 to 19:1)] to give (3-aminophenyl)(2-(methylsulfonyl)phenyl)methanol (121b) (4.912 g, 89%) as a white foam; $^1$H NMR (300 MHz, DMSO-d$_6$) δ 7.92 (dd, J=7.9, 1.4 Hz, 1H), 7.73-7.47 (m, 3H), 6.94 (t, J=7.7 Hz, 1H), 6.60-6.55 (m, 2H), 6.48 (dt, J=7.4, 1.2 Hz, 1H), 6.41 (ddd, J=8.0, 2.2, 1.0 Hz, 1H), 6.00 (d, J=5.0 Hz, 1H), 5.04 (s, 2H), 3.13 (s, 3H); MS (ES+): 300.2 (M+Na).

Step-2: Preparation of 1-(3-cyanophenyl)-N-(3-(hydroxy(2-(methylsulfonyl)phenyl)methyl)phenyl)-3-(trifluoromethyl)-1H-pyrazole-5-carboxamide (121c)

To a solution of (3-aminophenyl)(2-(methylsulfonyl)phenyl)methanol (121b) (3.46 g, 12.48 mmol) in DMF (60 mL) was added 1-(3-cyanophenyl)-3-(trifluoromethyl)-1H-pyrazole-5-carboxylic acid (9i) (3.51 g, 12.48 mmol), N-ethyl-N-isopropylpropan-2-amine (18.00 mL, 103 mmol), bromotripyrrolidin-1-ylphosphonium hexafluorophosphate(V) (PyBrOP, 5.93 g, 12.48 mmol) and stirred at room temperature for 15 h. The reaction mixture was diluted with ethyl acetate (240 mL), washed with water (2×100 mL) brine (100 mL), dried over MgSO$_4$ followed by filtration and concentration. The crude product was purified by flash column chromatography [silica gel 120 g, eluting with hexanes/10% methanol in ethyl acetate (1:0 to 1:1)] to give 1-(3-cyanophenyl)-N-(3-(hydroxy(2-(methylsulfonyl)phenyl)methyl)phenyl)-3-(trifluoromethyl)-1H-pyrazole-5-carboxamide (121c) (5.302 g, 79%) as a white solid; $^1$H NMR (300 MHz, DMSO-d$_6$) δ 10.67 (s, 1H), 8.16 (t, J=1.8 Hz, 1H), 8.00 (dt, J=7.8, 1.3 Hz, 1H), 7.97-7.87 (m, 2H), 7.77-7.49 (m, 7H), 7.28 (t, J=7.9 Hz, 1H), 7.10 (d, J=7.7 Hz, 1H), 6.71 (d, J=4.9 Hz, 1H), 6.28 (d, J=4.9 Hz, 1H), 3.23 (s, 3H); $^{19}$F NMR (282 MHz, DMSO-d$_6$) δ −60.94; MS (ES+): 563.2 (M+Na).

Step-3: Preparation of 1-(3-cyanophenyl)-N-(3-((cyclopropylmethylamino)(2-(methylsulfonyl)phenyl)methyl)phenyl)-3-(trifluoromethyl)-1H-pyrazole-5-carboxamide (121d)

To a solution of 1-(3-cyanophenyl)-N-(3-(hydroxy(2-(methylsulfonyl)phenyl)methyl)phenyl)-3-(trifluoromethyl)-1H-pyrazole-5-carboxamide (121c) (3.407 g, 6.30 mmol) in dichloromethane (80 mL) at 0° C. was added thionyl chloride (1.2 mL, 16.21 mmol) and stirred at room temperature for 2 h. the reaction mixture was treated with triethyl amine (7.00 mL, 50.2 mmol) and stirred at room temperature for 1 h. It was then treated with cyclopropylmethanamine (8.45 mL, 95 mmol) and concentrated to remove most of dichloromethane followed by addition of acetonitrile (60 mL), stirring at 70° C. for 13 h, and reflux for 5 h. The reaction mixture was treated with additional cyclopropylmethanamine (5 mL, 55.92 mmol), refluxed for 14 h, and concentrated to dryness. The residue was treated with chloroform (240 mL), washed with water (100 mL), dried over MgSO$_4$ followed by filtration and concentration. The crude product was purified by flash column chromatography [silica gel 80 g, eluting with hexanes/ethyl acetate (1:0 to 2:1)] to give 1-(3-cyanophenyl)-N-(3-((cyclopropylmethylamino)(2-(methylsulfonyl)phenyl)methyl)phenyl)-3-(trifluoromethyl)-1H-pyrazole-5-carboxamide (121d) (976 mg, 26%) as a brown gum. $^1$H NMR (300 MHz, DMSO-d$_6$) δ 10.68 (s, 1H), 8.18-8.15 (m, 1H), 8.00 (dt, J=7.8, 1.3 Hz, 1H), 7.95 (dd, J=7.9, 1.3 Hz, 1H), 7.90 (ddd, J=8.2, 2.3, 1.1 Hz, 1H), 7.77-7.46 (m, 7H), 7.36-7.22 (m, 2H), 5.95 (d, J=4.9 Hz, 1H), 3.28 (s, 3H), 2.75-2.60 (m, 1H), 2.30-2.14 (m, 1H), 0.98-0.80 (m, 1H), 0.47-0.26 (m, 2H), 0.16--0.03 (m, 2H); $^{19}$F NMR (282 MHz, DMSO-d$_6$) δ −60.94; MS (ES+): 594.3 (M+H).

Step-4: Preparation of tert-butyl 3-(5-(3-((cyclopropylmethylamino)(2-(methyl sulfonyl)phenyl)methyl)phenylcarbamoyl)-3-(trifluoromethyl)-1H-pyrazol-1-yl)benzylcarbamate (121e)

To a solution of 1-(3-cyanophenyl)-N-(3-((cyclopropylmethylamino)(2-(methylsulfonyl)phenyl)methyl)phenyl)-3-(trifluoromethyl)-1H-pyrazole-5-carboxamide (121d) (700 mg, 1.179 mmol) in MeOH (20 mL) cooled with ice/water was added di-tert-butyl dicarbonate (780 mg, 3.54 mmol), nickel chloride hexahydrate (0.3 mmol), followed by sodium borohydride (455 mg, 11.79 mmol) slowly over 5 min. The reaction mixture was stirred for 1 h, treated with N1-(2-aminoethyl)ethane-1,2-diamine (0.570 mL, 5.22 mmol), stirred at room temperature for 0.5 h and concentrated in vacuum to dryness. The residue was treated with ethyl acetate (150 mL), washed with water (75 mL). The aqueous phase was extracted again with ethyl acetate (75 mL). The combined extracts were washed with brine (75 mL), dried over MgSO$_4$ followed by filtration and concentration. The crude product was purified by flash column chromatography [silica gel 12 g, eluting with hexanes/ethyl acetate (1:0 to 2:1), then chloroform/methanol (1:0 to 9:1)] to give tert-butyl 3-(5-(3-((cyclopropylmethylamino)(2-(methyl sulfonyl)phenyl)methyl)phenylcarbamoyl)-3-(trifluoromethyl)-1H-pyrazol-1-yl)benzylcarbamate (121e) (368 mg, 45%) as a white foam; $^1$H NMR (300 MHz, DMSO-d$_6$) δ 10.64 (s, 1H), 7.93-7.87 (m, 1H), 7.66-7.16 (m, 13H), 5.89 (s, 1H), 4.14 (d, J=6.3 Hz, 2H), 3.22 (s, 3H), 2.44-2.36 (m, 1H), 2.25-2.10 (m, 1H), 1.31 (s, 9H), 0.93-0.70 (m, 1H), 0.42-0.22 (m, 2H), 0.09--0.07 (m, 2H); $^{19}$F NMR (282 MHz, DMSO-d$_6$) δ −60.62; MS (ES+): 698.4 (M+1).

Step-5: Preparation of 1-(3-(aminomethyl)phenyl)-N-(3-((cyclopropylmethylamino)(2-(methylsulfonyl)phenyl)methyl)phenyl)-3-(trifluoromethyl)-1H-pyrazole-5-carboxamide (121f)

To a solution of tert-butyl 3-(5-(3-((cyclopropylmethylamino)(2-(methyl sulfonyl)phenyl)methyl)phenylcarbamoyl)-3-(trifluoromethyl)-1H-pyrazol-1-yl)benzylcarbamate (121e) (0.344 g, 0.493 mmol) in 1,4-Dioxane (40 mL) was added hydrogen chloride (5.2 mL, 20.8 mmol, 4 M in 1,4-dioxane) and stirred at room temperature for 17 h. The reaction mixture was treated with hexanes, decanted, washed with hexanes, and decanted again. The insoluble crude product was purified by flash column chromatography [silica gel, eluting with chloroform/CMA80 (1:0 to 2:1)] to give 1-(3-(aminomethyl)phenyl)-N-(3-((cyclopropylmethylamino)(2-(methylsulfonyl)phenyl)methyl)phenyl)-3-(trifluoromethyl)-1H-pyrazole-5-carboxamide (121e) as a free base. The purified product 121e was dissolved in methanol (10 mL) and treated with 4 N HCl (aq. 0.45 mL) followed by concentration to dryness to give 1-(3-(aminomethyl)phenyl)-N-(3-((cyclopropylmethylamino)(2-(methylsulfonyl)phenyl)methyl)phenyl)-3-(trifluoromethyl)-1H-pyrazole-5-carboxamide (121e) (224 mg, 68%) hydrochloride salt as a white solid. $^1$H NMR (300 MHz, DMSO-d$_6$) δ 10.96 (s, 1H), 10.27 (s, 1H), 10.13 (s, 1H), 8.33 (s, 3H), 8.24 (d, J=8.2 Hz, 1H), 8.07 (dd, J=7.9, 1.4 Hz, 1H), 7.94-7.87 (m, 1H), 7.84 (s, 1H), 7.76-7.66 (m, 3H), 7.66-7.53 (m, 3H), 7.53-7.44 (m, 2H), 6.62 (d, J=7.0 Hz, 1H), 4.13 (q, J=5.9 Hz, 2H), 3.25 (s, 3H), 3.02-2.64 (m, 2H), 1.09 (t, J=7.0 Hz, 1H), 0.58 (t, J=7.4 Hz, 2H), 0.33 (s, 2H); $^1$H NMR (D$_2$O ex NMR, 300 MHz, DMSO-d$_6$) δ 8.13-7.39 (m, 13H), 6.59 (s, 1H), 4.13 (s, 2H), 3.22 (s, 3H), 3.00-2.88 (m, 1H), 2.81-2.67 (m, 1H), 1.15-0.95 (m, 1H), 0.67-0.50 (m, 2H), 0.37-0.22 (m, 2H); $^{19}$F NMR (282 MHz, DMSO-d$_6$) δ −60.77; MS (ES+): 598.3 (M+1); IR (KBr pellet, cm$^{-1}$): 3433, 3015, 1672, 1612, 1553, 1246, 1149; Analysis calculated for C$_{30}$H$_{30}$F$_3$N$_5$O$_3$S.2HCl.2H$_2$O: C, 50.99; H, 5.14; N, 9.91; Found: C, 50.86; H, 5.03; N, 9.73.

Scheme 122

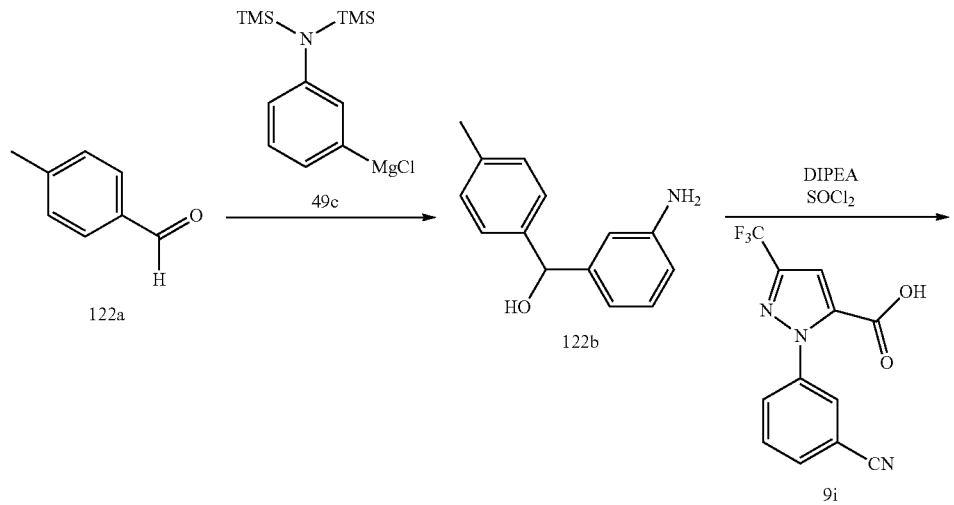

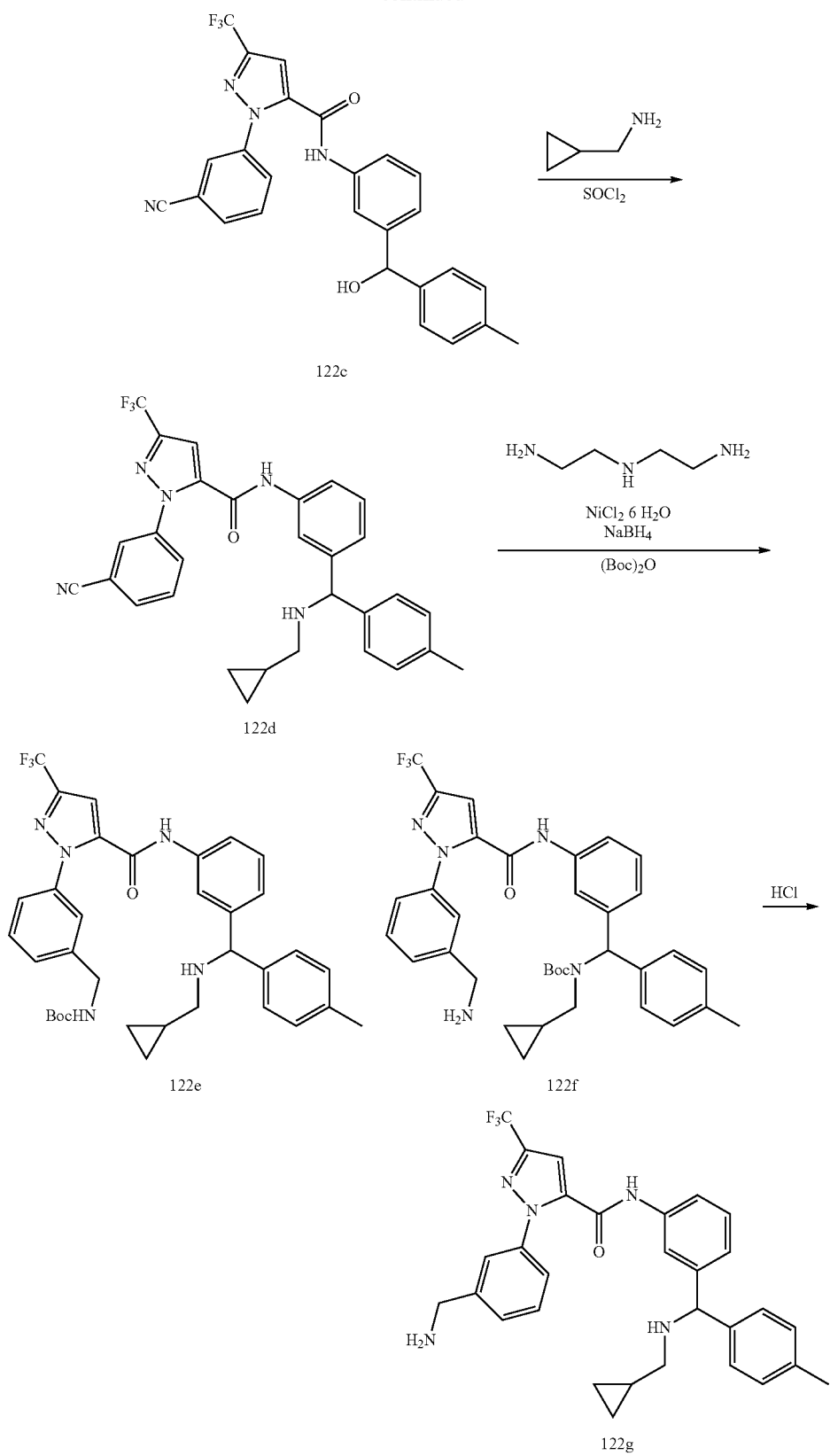

Preparation of 1-(3-(aminomethyl)phenyl)-N-(3-(((cyclopropylmethyl)amino)(p-tolyl)methyl)phenyl)-3-(trifluoromethyl)-1H-pyrazole-5-carboxamide (122g)

Step-1: Preparation of (4-aminophenyl)(p-tolyl)methanol (122b)

To a stirred solution of 4-methylbenzaldehyde (122a) (1.2 g, 10 mmol) in tetrahydrofuran (5 mL) was added (3-(bis(trimethylsilyl)amino)phenyl)magnesium chloride (49c) (12.00 mL, 12.00 mmol) at 0° C. The reaction was stirred for 14 h at room temperature and quenched by adding 2 N HCl (12.50 mL), stirred for 6 h. The reaction mixture was treated with 2 N NaOH (15 mL) and extracted with ethyl acetate (2×50 mL). The organic layers were combined washed with saturated aqueous $NH_4Cl$ (50 mL), dried over anhydrous $MgSO_4$, filtered and evaporated to dryness. The crude residue was purified by flash column chromatography (silica gel 40 g, eluting with 0-100% ethyl acetate in hexane) to furnish (3-aminophenyl)(2-methoxyphenyl)methanol (122b) (1.5 g, 65% yield) as a gray powder.

Step-2: Preparation of 1-(3-cyanophenyl)-N-(3-(hydroxy(p-tolyl)methyl)phenyl)-3-(trifluoromethyl)-1H-pyrazole-5-carboxamide (122c)

To a stirred solution of 2-(3-Cyano-phenyl)-5-trifluoromethyl-2H-pyrazole-3-carboxylic acid (9i) (2.57 g, 9.142 mmol) in toluene (50 mL) and DMF 15 drops was added $SOCl_2$ (2.0 g, 16.879 mmol) at 0° C. Reaction was refluxed for 3.5 hr and concentrated to remove volatile solvent. The residue obtained was dissolved in DCM (100 mL) and (4-aminophenyl)(2-methoxyphenyl)methanol (122b) (1.5 g, 7.033 mmol) was added followed by dropwise addition of triethylamine (7.2 mL) at RT. Reaction mixture was stirred overnight at room temp concentrated in vacuum to dryness. The residue obtained was purified by flash chromatography (10%-70% ethyl acetate in hexane) to afford 1-(3-cyanophenyl)-N-(3-(hydroxy(p-tolyl)methyl)phenyl)-3-(trifluoromethyl)-1H-pyrazole-5-carboxamide (122c) (1.8 g, 53.7%) as a brown sticky liquid.

Step-3: Preparation of 1-(3-cyanophenyl)-N-(3-(((cyclopropylmethyl)amino)(p-tolyl)methyl)phenyl)-3-(trifluoromethyl)-1H-pyrazole-5-carboxamide (122d)

To a solution of 1-(3-cyanophenyl)-N-(3-(hydroxy(p-tolyl)methyl)phenyl)-3-(trifluoromethyl)-1H-pyrazole-5-carboxamide (122c) (1.8 g, 3.777 mmol) in dichloromethane (50 mL) at 0° C. was added thionyl chloride (0.6 mL, 7.555 mmol) and stirred at room temperature for 4 h. The reaction mixture was concentrated in vacuum to dryness. The residue obtained was dissolved in acetonitrile (50 mL) and added cyclopropylmethanamine (4.9 mL, 56.669 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum. The residue obtained was purified by flash column chromatography (silica gel 40 g, eluting 0-100% ethyl acetate in hexane) to afford 1-(3-cyanophenyl)-N-(3-(((cyclopropylmethyl)amino)(p-tolyl)methyl)phenyl)-3-(trifluoromethyl)-1H-pyrazole-5-carboxamide (122d) (1.1 g, 55% yield) as a brown sticky liquid.

Step-4: Preparation of tert-butyl 3-(5-((3-(((cyclopropylmethyl)amino)(p-tolyl)methyl)phenyl)carbamoyl)-3-(trifluoromethyl)-1H-pyrazol-1-yl)benzylcarbamate (122e) and tert-butyl ((3-(1-(3-(aminomethyl)phenyl)-3-(trifluoromethyl)-1H-pyrazole-5-carboxamido)phenyl)(p-tolyl)methyl)(cyclopropylmethyl)carbamate (122f)

To a solution of 1-(3-cyanophenyl)-N-(3-(((cyclopropylmethyl)amino)(p-tolyl)methyl)phenyl)-3-(trifluoromethyl)-1H-pyrazole-5-carboxamide (122d) (1.1 g, 2.077 mmol) in MeOH (20 mL) cooled with ice/water was added nickel(II) chloride hexahydrate (0.542 g, 2.284 mmol) and Boc anhydride (2.4 mL, 10.385 mmol) followed by portionwise addition of Sodium Borohydride (0.94 g, 24.926 mmols) over a period of 15 min. The reaction mixture was stirred at room temperature for 20 hrs and quenched with $N^1$-(2-aminoethyl)ethane-1,2-diamine (1.1 mL, 10.385 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over $MgSO_4$ filtered and concentrated in vacuum. The residue obtained was purified by flash column chromatography (silica gel 24 g, eluting with 0-25% chloroform/methanol) to furnish tert-butyl ((3-(1-(3-(aminomethyl)phenyl)-3-(trifluoromethyl)-1H-pyrazole-5-carboxamido)phenyl)(p-tolyl)methyl)(cyclopropylmethyl)carbamate (0.214 gm) (122f) (0.214 g) as a white solid and tert-butyl 3-(5-((3-(((cyclopropylmethyl)amino)(p-tolyl)methyl)phenyl)carbamoyl)-3-(trifluoromethyl)-1H-pyrazol-1-yl)benzylcarbamate (122e) (0.445 gm) as a white solid.

Step-5: Preparation of 1-(3-(aminomethyl)phenyl)-N-(3-(((cyclopropylmethyl)amino)(p-tolyl)methyl)phenyl)-3-(trifluoromethyl)-1H-pyrazole-5-carboxamide (122g)

A solution of tert-butyl 3-(5-((3-(((cyclopropylmethyl)amino)(p-tolyl)methyl)phenyl)carbamoyl)-3-(trifluoromethyl)-1H-pyrazol-1-yl)benzylcarbamate (122e) (0.445 g, 0.702 mmol) and tert-butyl ((3-(1-(3-(aminomethyl)phenyl)-3-(trifluoromethyl)-1H-pyrazole-5-carboxamido)phenyl)(p-tolyl)methyl)(cyclopropylmethyl)carbamate (122f) (0.214 g, 0.337 mmol) were dissolved separately in methanol (2.5 mL) and added conc. HCL (1.0 mL). The reaction mixture was stirred at room temperature overnight and concentrated in vacuum to dryness. The residue was azeotroped with toluene (2×10 mL) and ethanol (10 mL), dried in vacuum pump to furnish a white solid residue. NMR of the residue in methanol and TLC shows same compound. The products were combined dried and purified by flash column chromatography (silica gel 12 g, eluting with 0-150% methanol in dichloromethane to furnish 1-(3-(aminomethyl)phenyl)-N-(3-(((cyclopropylmethyl)amino)(p-tolyl)methyl)phenyl)-3-(trifluoromethyl)-1H-pyrazole-5-carboxamide (122g) (0.2 g, 36.1%) as a white solid; $^1H$ NMR (300 MHz, DMSO-$d_6$) δ 11.00 (s, 1H), 10.19-10.00 (m, 2H), 8.55 (d, J=5.7 Hz, 3H), 7.88-7.82 (m, 1H), 7.73 (d, J=2.4 Hz, 2H), 7.64 (dq, J=7.8, 2.3 Hz, 3H), 7.60-7.50 (m, 4H), 7.42 (t, J=7.9 Hz, 1H), 7.22 (d, J=7.7 Hz, 2H), 5.53 (d, J=6.4 Hz, 1H), 4.12 (q, J=5.5 Hz, 2H), 2.76-2.62 (m, 2H), 2.28 (s, 3H), 1.22-1.10 (m, 1H), 0.60-0.49 (m, 2H), 0.30 (q, J=3.2, 1.6 Hz, 2H); $^{19}F$ NMR (282 MHz, DMSO $d_6$) δ −60.78; MS (ES+) 534.4 (M+1); 532.3 (M−1); Analysis calculated for $C_{30}H_{30}F_3N_5O.2.75HCl.3H_2O$: C, 52.38; H, 5.68; Cl, 14.17; N, 10.18: Found: C, 52.64; H, 5.74; Cl, 13.95; N, 9.83.

Scheme 123
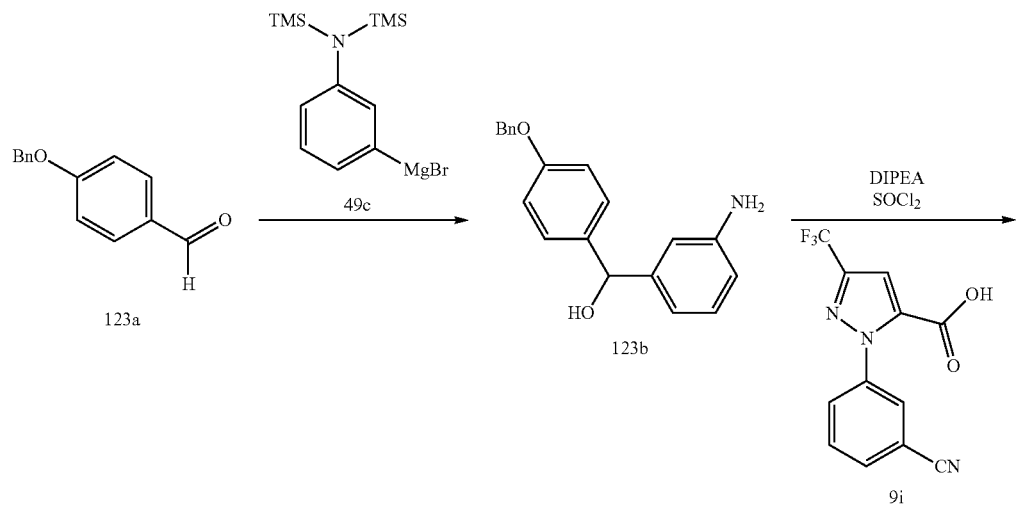
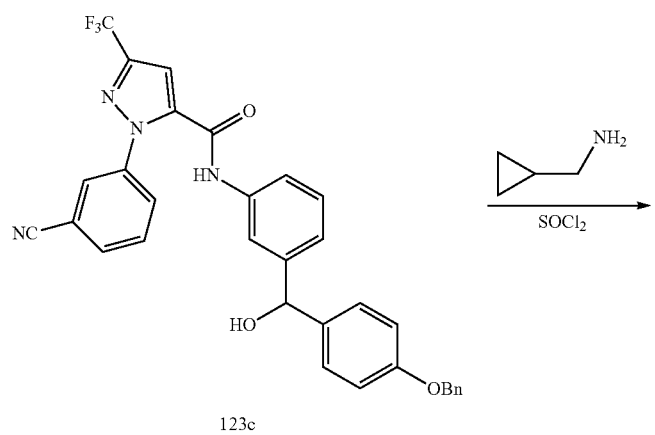
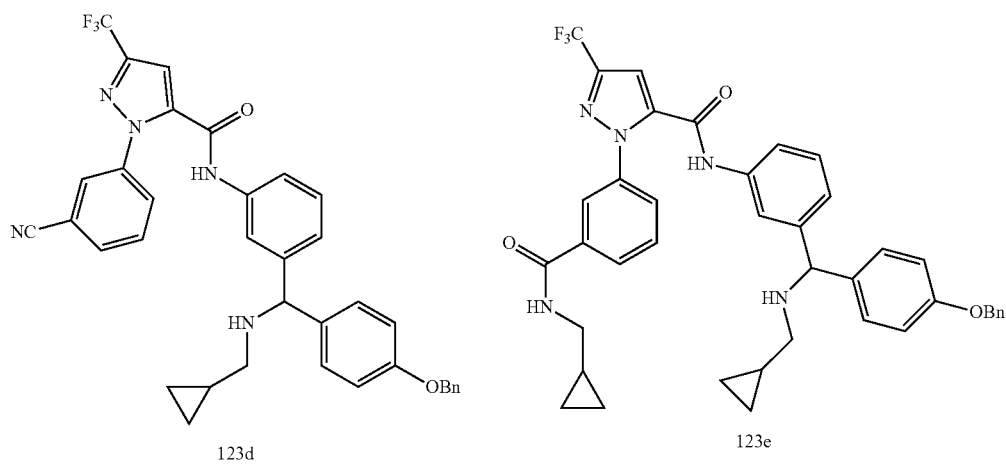

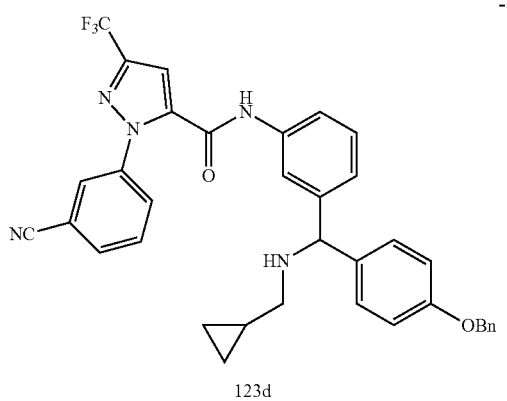

123d

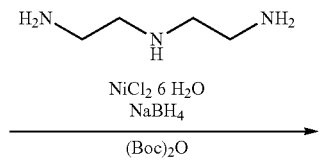

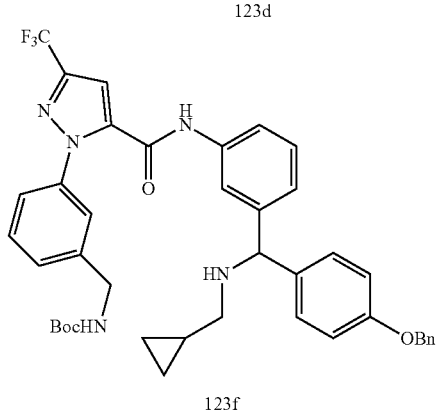

123f

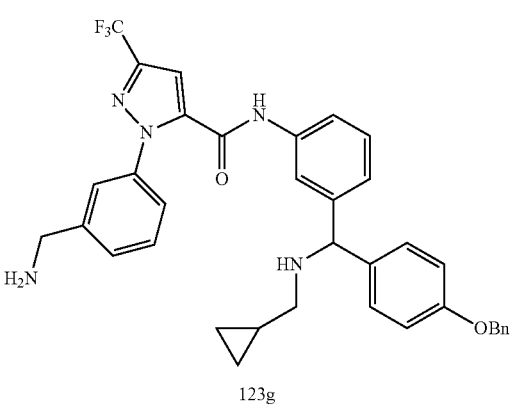

123g

Preparation of 1-(3-(Aminomethyl)phenyl)-N-(3-((4-(benzyloxy)phenyl)(cyclopropylmethylamino) methyl)phenyl)-3-(trifluoromethyl)-1H-pyrazole-5-carboxamide (123g)

Step-1: Preparation of (3-aminophenyl)(4-(benzyloxy)phenyl)methanol (123b)

To a stirred solution of 4-(benzyloxy)benzaldehyde (123a) (2.122 g, 10 mmol) in tetrahydrofuran (10 mL) was added (3-(bis(trimethylsilyl)amino)phenyl)magnesium bromide (49c) (12.0 mL, 12.0 mmol) at 0° C. The reaction was stirred for 14 h at same temperature and quenched by adding hydrogen chloride (25.00 mL, 25.00 mmol), stirred for 6 h. The reaction was neutralized with 2 N NaOH (15 mL) and extracted with ethyl acetate (2×50 mL). The organic layers were combined washed with brine (50 mL), dried over anhydrous MgSO$_4$, filtered, and evaporated to dryness. The crude residue was purified by flash column chromatography (silica gel 40 g, eluting with ethyl acetate in hexanes from 0-100%) to furnish (3-aminophenyl)(4-(benzyloxy)phenyl) methanol (123b) (2.691, 88% yield) as a thick yellow oil; $^1$H NMR (300 MHz, DMSO-d$_6$) δ 7.45-7.28 (m, 5H), 7.28-7.17 (m, 2H), 6.90 (dd, J=8.2, 7.1 Hz, 3H), 6.55 (t, J=1.9 Hz, 1H), 6.48 (dt, J=7.6, 1.3 Hz, 1H), 6.37 (ddd, J=7.9, 2.3, 1.0 Hz, 1H), 5.58 (d, J=3.8 Hz, 1H), 5.45 (d, J=3.9 Hz, 1H), 5.06 (s, 2H), 4.97 (s, 2H).

Step-2: Preparation of N-(3-((4-(benzyloxy)phenyl) (hydroxy)methyl)phenyl)-1-(3-cyanophenyl)-3-(trifluoromethyl)-1H-pyrazole-5-carboxamide (123c)

To a solution of 1-(3-cyanophenyl)-3-(trifluoromethyl)-1H-pyrazole-5-carboxylic acid (9i) (2.73 g, 9.69 mmol) in DMF (10 mL) was added (3-aminophenyl)(4-(benzyloxy) phenyl)methanol (123b) (2.691 g, 8.81 mmol), N-ethyl-N-isopropylpropan-2-amine (7.67 mL, 44.1 mmol) and bromo-tris-pyrrolidino phosphoniumhexafluorophosphate (PyBrOP, 4.93 g, 10.57 mmol) at room temperature. The reaction mixture was stirred at room temperature for 37 h under nitrogen atmosphere. The reaction was diluted with water (25 mL) and extracted with ethyl acetate (2×100 mL). The organic layers were combined, washed with brine (50 mL), dried, filtered, and concentrated in vacuum to dryness. The residue obtained was purified by flash column chromatography (silica gel 40 g, eluting with 0-100% ethyl acetate in hexanes) to furnish N-(3-((4-(benzyloxy)phenyl)(hydroxy)methyl)phenyl)-1-(3-cyanophenyl)-3-(trifluoromethyl)-1H-pyrazole-5-carboxamide (123c) (2.309 g, 4.06 mmol, 46.1% yield) as a white solid; $^1$H NMR (300 MHz, DMSO-d$_6$) δ 10.62 (s, 1H), 8.19-8.12 (m, 1H), 8.00 (dt, J=7.7, 1.3 Hz, 1H), 7.90 (ddd, J=8.2, 2.2, 1.1 Hz, 1H), 7.78-7.69 (m, 2H), 7.61 (d, J=2.0 Hz, 1H), 7.54 (d, J=8.1 Hz, 1H), 7.44-7.21 (m, 9H), 7.11 (d, J=7.6 Hz, 1H), 6.98-6.89 (m, 2H), 5.84 (d, J=3.8 Hz, 1H), 5.61 (d, J=3.9 Hz, 1H), 5.06 (s, 2H); MS (ES+) 591.3 (M+Na); (ES−) 567.3 (M−1).

Step-3: Preparation of N-(3-((4-(benzyloxy)phenyl) (cyclopropylmethylamino)methyl)phenyl)-1-(3-cyanophenyl)-3-(trifluoromethyl)-1H-pyrazole-5-carboxamide (123d)

To a solution of N-(3-((4-(benzyloxy)phenyl)(hydroxy) methyl)phenyl)-1-(3-cyanophenyl)-3-(trifluoromethyl)-1H-pyrazole-5-carboxamide (123c) (2.309 g, 4.06 mmol) in dichloromethane (50 mL) at 0° C. was added thionyl chloride (0.89 mL, 12.18 mmol) and stirred at room temperature for 2 h. The reaction mixture was quenched with cyclopropylmethanamine (1.057 mL, 12.18 mmol)) and stirred at room temperature for additional 5 h. The reaction mixture was concentrated in vacuum to dryness. The residue obtained was dissolved in acetonitrile (10 mL) and added cyclopropylmethanamine (7.04 mL, 81 mmol). The reaction mixture was heated at reflux for 48 h cooled to room temperature and concentrated in vacuum to dryness. The residue was dissolved in dichloromethane (50 mL), washed with water (2×25 mL), dried, filtered and concentrated in vacuum. The residue obtained was purified by flash column chromatography (silica gel 40 g, eluting 0-100% ethyl acetate in hexane) to afford 1. N-(3-((4-(benzyloxy)phenyl)(cyclopropylmethylamino)methyl)phenyl)-1-(3-cyanophenyl)-3-(trifluoromethyl)-1H-pyrazole-5-carboxamide (123d) (0.683 g, 1.099 mmol, 27.1% yield) as a white solid; $^1$H NMR (300 MHz, DMSO-d$_6$) δ 10.63 (s, 1H), 8.16 (t, J=1.8 Hz, 1H), 8.00 (dt, J=7.8, 1.3 Hz, 1H), 7.90 (ddd, J=8.2, 2.2, 1.1 Hz, 1H), 7.77-7.69 (m, 2H), 7.64 (t, J=1.7 Hz, 1H), 7.58-7.51 (m, 1H), 7.44-7.26 (m, 8H), 7.23 (d, J=7.8 Hz, 1H), 7.17 (dt, J=7.7, 1.4 Hz, 1H), 6.95-6.89 (m, 2H), 5.04 (s, 2H), 4.77 (s, 1H), 2.27 (d, J=6.7 Hz, 2H), 0.92 (dt, J=12.8, 4.7 Hz, 1H), 0.44-0.31 (m, 2H), 0.04 (td, J=5.1, 3.4 Hz, 2H); $^{19}$F NMR (282 MHz, DMSO-d$_6$) δ −60.96; MS (ES+) 622.4 (M+1); (ES−) 620.9 (M−1), 656.3 (M+Cl). 2. N-(3-((4-(benzyloxy)phenyl)(cyclopropylmethylamino)methyl)phenyl)-1-(3-(cyclopropylmethylcarbamoyl)phenyl)-3-(trifluoromethyl)-1H-pyrazole-5-carboxamide (123e) (0.6 g, 0.865 mmol, 21.30% yield) as a white solid; $^1$H NMR (300 MHz, DMSO-d$_6$) δ 10.66 (s, 1H), 8.77 (t, J=5.6 Hz, 1H), 8.05-7.95 (m, 2H), 7.68-7.57 (m, 4H), 7.54-7.48 (m, 1H), 7.44-7.25 (m, 7H), 7.22 (d, J=7.8 Hz, 1H), 7.16 (dt, J=7.7, 1.4 Hz, 1H), 6.95-6.89 (m, 2H), 5.04 (s, 2H), 4.76 (s, 1H), 3.15 (dd, J=6.9, 5.5 Hz, 2H), 2.27 (d, J=6.7 Hz, 2H), 1.02 (tdd, J=8.2, 6.0, 3.2 Hz, 1H), 0.96-0.81 (m, 1H), 0.48-0.30 (m, 4H), 0.27-0.16 (m, 2H), 0.09-0.00 (m, 2H); $^{19}$F NMR (282 MHz, DMSO-d$_6$) δ −60.79; MS (ES+) 694.4 (M+1); (ES−) 692.2 (M−1); Analysis calculated for C$_{40}$H$_{38}$F$_3$N$_5$O$_3$.0.5H$_2$O: C, 68.36; H, 5.59; F, 8.11; N, 9.97; Found: C, 68.37; H, 5.55; F, 7.64; N, 9.87.

Step-4 Preparation of tert-Butyl 3-(5-(3-((4-(benzyloxy)phenyl)(cyclopropylmethylamino) methyl) phenylcarbamoyl)-3-(trifluoromethyl)-1H-pyrazol-1-yl)benzylcarbamate (123f)

To a solution of N-(3-((4-(benzyloxy)phenyl)(cyclopropylmethylamino)methyl)phenyl)-1-(3-cyanophenyl)-3-(trifluoromethyl)-1H-pyrazole-5-carboxamide (123d) (0.68 g, 1.094 mmol) in MeOH (20 mL) cooled with ice/water was added di-tert-butyl dicarbonate (0.716 g, 3.28 mmol) and nickel(II) chloride (0.286 g, 1.203 mmol). Sodium Borohydride (0.317 g, 8.20 mmol) was added slowly over 15 min and reaction mixture was stirred at room temperature for 1 h. The reaction mixture was quenched with N1-(2-aminoethyl)ethane-1,2-diamine (0.358 mL, 3.28 mmol) stirred for 0.5 h and concentrated in vacuum to dryness. The residue obtained was dissolved in dichloromethane (60 mL) and water (60 mL). The aqueous phase was separated and extracted again with dichloromethane (60 mL). The organic extracts were combined, washed with brine (60 mL), dried over MgSO$_4$, filtered and concentrated in vacuum to dryness. The residue obtained was purified by flash column chromatography (silica gel 24 g with 0-100% 9:1 ethyl acetate/methanol in hexane) to afford tert-butyl 3-(5-(3-((4-(benzyloxy)phenyl)(cyclopropylmethylamino)methyl)phenylcarbamoyl)-3-(trifluoromethyl)-1H-pyrazol-1-yl)benzylcarbamate (123f) (0.304 g, 0.419 mmol, 38.3% yield) as a white solid; $^1$H NMR (300 MHz, DMSO-d$_6$) δ 10.68 (s, 1H), 7.62 (t, J=1.8 Hz, 1H), 7.57 (s, 1H), 7.52 (d, J=7.6 Hz, 1H), 7.45-7.38 (m, 4H), 7.38-7.32 (m, 4H), 7.32-7.26 (m, 2H), 7.22 (d, J=7.8 Hz, 1H), 7.19-7.14 (m, 1H), 6.98-6.88 (m, 2H), 5.04 (s, 2H), 4.76 (s, 1H), 4.19 (d, J=6.2 Hz, 2H), 2.27 (d, J=6.5 Hz, 3H), 1.00-0.83 (m, 1H), 0.42-0.33 (m, 2H), 0.09-0.01 (m, 2H); $^{19}$F NMR (282 MHz, DMSO) δ −60.79; MS (ES+) 726.4 (M+1).

Step-5: Preparation of 1-(3-(Aminomethyl)phenyl)-N-(3-((4-(benzyloxy)phenyl)(cyclopropylmethylamino) methyl)phenyl)-3-(trifluoromethyl)-1H-pyrazole-5-carboxamide (123g)

To a solution of tert-butyl 3-(5-(3-((4-(benzyloxy)phenyl) (cyclopropylmethylamino) methyl)phenylcarbamoyl)-3-(trifluoromethyl)-1H-pyrazol-1-yl)benzylcarbamate (123f) (0.32 g, 0.441 mmol) in methanol (10 mL) was added hydrogen chloride (0.919 mL, 11.02 mmol) and stirred at room temperature overnight. The reaction mixture was concentrated in vacuum to dryness and was purified by flash column chromatography (silica gel 12 g, eluting with 0-50% methanol in chloroform) to afford 1-(3-(aminomethyl)phenyl)-N-(3-((4-(benzyloxy)phenyl)(cyclopropylmethylamino)methyl)phenyl)-3-(trifluoromethyl)-1H-pyrazole-5-carboxamide (123g) (0.228 g, 0.364 mmol, 83% yield) as an off-white solid; $^1$H NMR (300 MHz, DMSO-d$_6$) δ 10.71 (s, 1H), 7.64 (dd, J=4.2, 2.3 Hz, 3H), 7.56-7.46 (m, 3H), 7.45-7.14 (m, 10H), 6.95-6.89 (m, 2H), 5.05 (s, 2H), 4.76 (s, 1H), 3.98 (s, 2H), 2.27 (d, J=6.7 Hz, 2H), 0.98-0.82 (m, 1H), 0.43-0.32 (m, 2H), 0.04 (m, 2H); 19F NMR (282 MHz, DMSO-d$_6$) δ −60.76; MS (ES+) 626.4 (M+1); (ES−) 660.3 (M−1); Analysis calculated for C$_{36}$H$_{34}$F$_3$N$_5$O$_2$.2H$_2$O: C, 65.34; H, 5.79; N, 10.58; Found: C, 65.39; H, 5.55; N, 10.50.

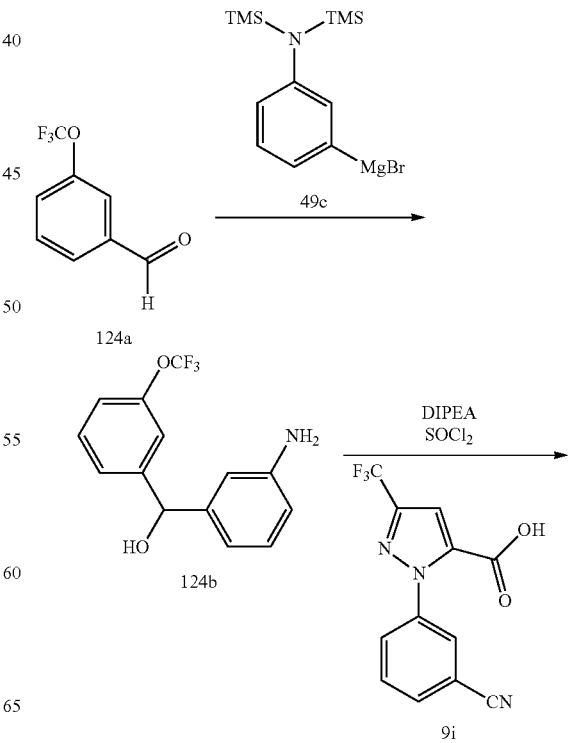

Scheme 124

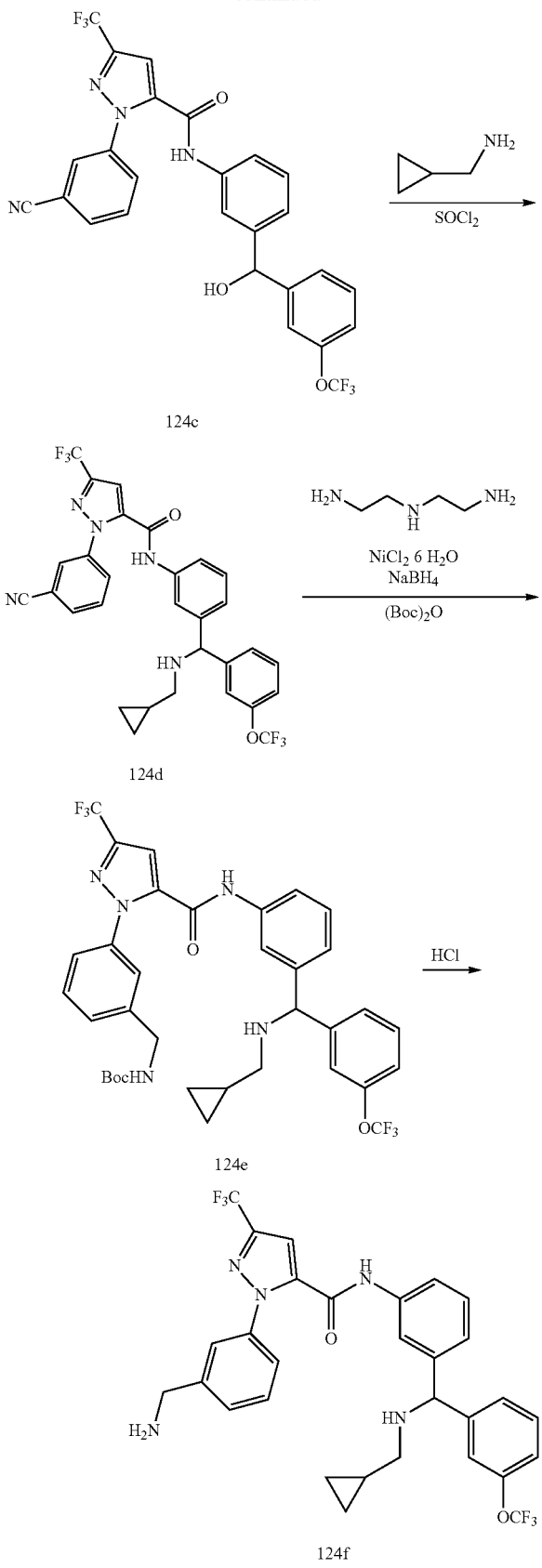

Preparation of 1-(3-(Aminomethyl)phenyl)-N-(3-((cyclopropylmethylamino)(3-(trifluoromethoxy)phenyl)methyl)phenyl)-3-(trifluoromethyl)-1H-pyrazole-5-carboxamide (124f)

Step-1: Preparation of (3-Aminophenyl)(3-(trifluoromethoxy)phenyl)methanol (124b)

To a stirred solution of 3-(trifluoromethoxy)benzaldehyde (124a) (1.9 g, 10 mmol) in tetrahydrofuran (5 mL) was added (3-(bis(trimethylsilyl)amino)phenyl)magnesium bromide (49c) (12.0 mL, 12.0 mmol) at 0° C. The reaction was stirred for 14 h at same temperature and quenched by adding hydrogen chloride (25.00 mL, 25.00 mmol), stirred for 6 h. The reaction was neutralized with 2 N NaOH (15 mL) and extracted with ethyl acetate (2×50 mL). The organic layers were combined washed with brine (50 mL), dried over anhydrous MgSO$_4$, filtered, and evaporated to dryness. The crude residue was purified by flash column chromatography (silica gel 40 g, eluting with ethyl acetate in hexanes from 0-100%) to furnish (3-Aminophenyl)(3-(trifluoromethoxy)phenyl)methanol (124b) (1.5 g, 53% yield) as a thick yellow oil; $^1$H NMR (300 MHz, DMSO-d$_6$) δ 7.47-7.29 (m, 3H), 7.18 (ddt, J=7.9, 2.5, 1.2 Hz, 1H), 6.93 (t, J=7.7 Hz, 1H), 6.58 (t, J=2.0 Hz, 1H), 6.51 (dt, J=7.6, 1.3 Hz, 1H), 6.40 (ddd, J=8.0, 2.3, 1.1 Hz, 1H), 5.91 (d, J=3.9 Hz, 1H), 5.57 (d, J=3.9 Hz, 1H), 5.05 (s, 2H); $^{19}$F NMR (282 MHz, DMSO-d$_6$) δ −56.58; MS (ES+) 284.2 (M+1), 306.2 (M+Na); (ES−) 282.1 (M−1).

Step-2: Preparation of 1-(3-Cyanophenyl)-N-(3-(hydroxy(3-(trifluoromethoxy)phenyl)methyl)phenyl)-3-(trifluoromethyl)-1H-pyrazole-5-carboxamide (124c)

To a solution of 1-(3-cyanophenyl)-3-(trifluoromethyl)-1H-pyrazole-5-carboxylic acid (9i) (1.495 g, 5.32 mmol) in DMF (20 mL) was (3-aminophenyl)(3-(trifluoromethoxy)phenyl)methanol (124b) (1.369 g, 4.83 mmol), N-ethyl-N-isopropylpropan-2-amine (4.21 mL, 24.17 mmol) and bromo-tris-pyrrolidino phosphoniumhexafluorophosphate (PyBrOP, 2.70 g, 5.80 mmol) at room temperature. The reaction mixture was stirred at room temperature for 37 h under nitrogen atmosphere. The reaction was diluted with water (75 mL) and extracted with ethyl acetate (2×75 mL). The organic layers were combined, washed with brine (50 mL), dried, filtered, and evaporated in vacuum to dryness. The residue obtained was purified by flash column chromatography (silica gel 40 g, eluting with 0-100% ethyl acetate in hexanes) to furnish 1-(3-cyanophenyl)-N-(3-(hydroxy(3-(trifluoromethoxy)phenyl)methyl)phenyl)-3-(trifluoromethyl)-1H-pyrazole-5-carboxamide (124c) (2.081 g, 3.81 mmol, 79% yield) as a yellow semisolid; 1H NMR (300 MHz, DMSO-d$_6$) δ 10.66 (s, 1H), 8.17 (t, J=1.8 Hz, 1H), 8.00 (dt, J=7.8, 1.3 Hz, 1H), 7.91 (ddd, J=8.2, 2.2, 1.1 Hz, 1H), 7.77-7.70 (m, 2H), 7.67 (t, J=1.8 Hz, 1H), 7.58 (ddd, J=8.1, 2.2, 1.1 Hz, 1H), 7.44 (t, J=8.0 Hz, 1H), 7.40-7.31 (m, 2H), 7.29 (t, J=7.8 Hz, 1H), 7.23-7.13 (m, 2H), 6.18 (d, J=3.9 Hz, 1H), 5.76 (d, J=3.9 Hz, 1H); $^{19}$F NMR (282 MHz, DMSO-d$_6$) δ −56.62, −60.98; MS (ES+) 569.2 (M+Na); (ES−) 545.2 (M−1).

Step-3: Preparation of tert-Butyl 3-(5-(3-((cyclopropylmethylamino)(3-(trifluoromethoxy)phenyl)methyl) phenylcarbamoyl)-3-(trifluoromethyl)-1H-pyrazol-1-yl)benzylcarbamate (124d)

To a solution of 1-(3-cyanophenyl)-N-(3-((cyclopropylmethylamino)(3-(trifluoromethoxy)phenyl)methyl)phenyl)-3-(trifluoromethyl)-1H-pyrazole-5-carboxamide (124c)

(0.44 g, 0.734 mmol) in MeOH (10 mL) cooled with ice/water was added di-tert-butyl dicarbonate (0.481 g, 2.202 mmol) and nickel(II) chloride (0.192 g, 0.807 mmol). Sodium Borohydride (0.212 g, 5.50 mmol) was added slowly over 15 min and reaction mixture was stirred at room temperature for 1 h. The reaction mixture was quenched with N1-(2-aminoethyl)ethane-1,2-diamine (0.240 mL, 2.202 mmol) stirred for 0.5 h and concentrated in vacuum to dryness. The residue obtained was dissolved in dichloromethane (60 mL) and water (60 mL). The aqueous phase was separated and extracted again with dichloromethane (60 mL). The organic extracts were combined, washed with brine (60 mL), dried over MgSO₄, filtered and concentrated in vacuum to dryness. The residue obtained was purified by flash column chromatography (silica gel 24 g with 0-100% 9:1 ethyl acetate/methanol in hexane) to afford tert-butyl 3-(5-(3-((cyclopropylmethylamino)(3-(trifluoromethoxy)phenyl)methyl)phenylcarbamoyl)-3-(trifluoromethyl)-1H-pyrazol-1-yl)benzylcarbamate (124d) (0.304 g, 0.432 mmol, 58.9% yield) as a white solid; $^1$H NMR (300 MHz, DMSO-d₆) δ 10.70 (s, 1H), 7.66 (d, J=2.2 Hz, 1H), 7.57 (s, 1H), 7.57-7.38 (m, 6H), 7.37-7.35 (m, 1H), 7.33 (s, 1H), 7.29-7.17 (m, 3H), 4.89 (s, 1H), 4.19 (d, J=6.2 Hz, 2H), 2.59-2.54 (m, 1H), 2.39-2.16 (m, 2H), 1.35 (s, 9H), 0.99-0.83 (m, 1H), 0.43-0.30 (m, 2H), 0.09--0.01 (m, 3H); $^{19}$F NMR (282 MHz, DMSO-d₆) δ −56.60, −60.80; MS (ES+) 704.4 (M+1), 727.5 (M+Na), (ES−) 703.3 (M−1).

Step-4: Preparation of 1-(3-Cyanophenyl)-N-(3-((cyclopropylmethylamino)(3-(trifluoromethoxy)phenyl)methyl)phenyl)-3-(trifluoromethyl)-1H-pyrazole-5-carboxamide (124e)

To a solution of 1-(3-cyanophenyl)-N-(3-(hydroxy(3-(trifluoromethoxy)phenyl)methyl)phenyl)-3-(trifluoromethyl)-1H-pyrazole-5-carboxamide (124d) (0.769 g, 1.407 mmol) in dichloromethane (25 mL) at 0° C. was added thionyl chloride (0.308 mL, 4.22 mmol) and stirred at room temperature for 2 h. The reaction mixture was quenched with cyclopropylmethanamine (0.366 mL, 4.22 mmol) and stirred at room temperature for additional 5 h. The reaction mixture was concentrated in vacuum to dryness. The residue obtained was dissolved in acetonitrile (5 mL) and added cyclopropylmethanamine (2.441 mL, 28.1 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum. The residue obtained was purified by flash column chromatography (silica gel 24 g, eluting 0-100% ethyl acetate in hexane) to afford 1-(3-cyanophenyl)-N-(3-((cyclopropylmethylamino)(3-(trifluoromethoxy)phenyl)methyl)phenyl)-3-(trifluoromethyl)-1H-pyrazole-5-carboxamide (124e) (0.449 g, 0.749 mmol, 53.2% yield) as a white solid; $^1$H NMR (300 MHz, DMSO-d₆) δ 10.65 (s, 1H), 8.16 (t, J=1.8 Hz, 1H), 8.00 (dt, J=7.8, 1.3 Hz, 1H), 7.90 (ddd, J=8.2, 2.3, 1.1 Hz, 1H), 7.79-7.66 (m, 3H), 7.60-7.47 (m, 1H), 7.46-7.37 (m, 3H), 7.32-7.14 (m, 3H), 4.90 (s, 1H), 2.38-2.15 (m, 3H), 1.00-0.80 (m, 1H), 0.44-0.32 (m, 2H), 0.08-0.01 (m, 2H); $^{19}$F NMR (282 MHz, DMSO) δ −56.60, −60.96; MS (ES+) 600.3 (M+1); (ES−) 634.1 (M+Cl).

Step-5: Preparation of 1-(3-(Aminomethyl)phenyl)-N-(3-((cyclopropylmethylamino)(3-(trifluoromethoxy) phenyl)methyl)phenyl)-3-(trifluoromethyl)-1H-pyrazole-5-carboxamide (124f)

To a solution of tert-butyl 3-(5-(3-((cyclopropylmethylamino)(3-(trifluoromethoxy)phenyl)methyl)phenylcarbamoyl)-3-(trifluoromethyl)-1H-pyrazol-1-yl) benzylcarbamate (124e) (0.194 g, 0.276 mmol) in methanol (10 mL) was added hydrogen chloride (0.574 mL, 6.89 mmol), stirred at room temperature overnight and concentrated in vacuum to dryness. The residue obtained was purified by flash column chromatography (silica gel 12 g, eluting with 0-50% methanol in chloroform) to afford 1-(3-(aminomethyl)phenyl)-N-(3-((cyclopropylmethylamino)(3-(trifluoromethoxy)phenyl)methyl)phenyl)-3-(trifluoromethyl)-1H-pyrazole-5-carboxamide (124f) (0.05 g, 0.083 mmol, 30.0% yield) as an off-white solid; $^1$H NMR (300 MHz, DMSO-d₆) δ 10.85 (s, 1H), 8.49 (s, 3H), 7.79-7.68 (m, 3H), 7.66-7.44 (m, 6H), 7.29 (dd, J=25.9, 7.6 Hz, 3H), 5.13 (s, 1H), 4.12 (s, 2H), 2.46-2.34 (m, 2H), 0.98 (d, J=8.9 Hz, 1H), 0.43 (d, J=7.6 Hz, 2H), 0.26-0.05 (m, 2H); $^{19}$F NMR (282 MHz, DMSO-d₆) δ −56.61, −60.79; MS (ES+) 604.3 (M+1); (ES−) 602.3 (M−1); Analysis calculated for C₃₀H₂₇F₆N₅O₂.1.25HCl.0.5H₂O: C, 54.75; H, 4.48; Cl, 6.73; N, 10.64; Found: C, 54.61; H, 4.51; Cl, 6.81; N, 10.50.

Scheme 125

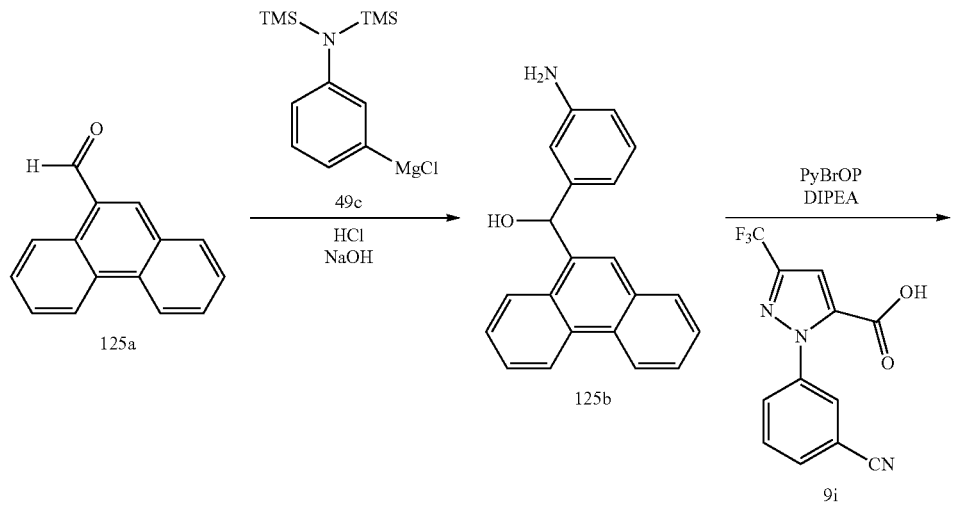

-continued
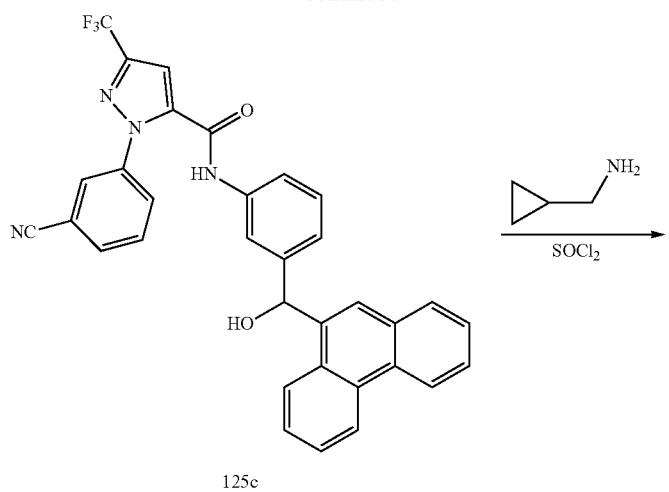
125c
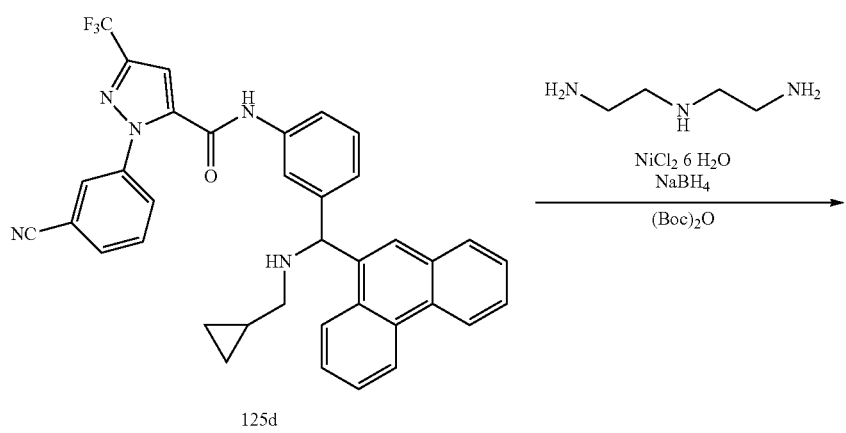
125d
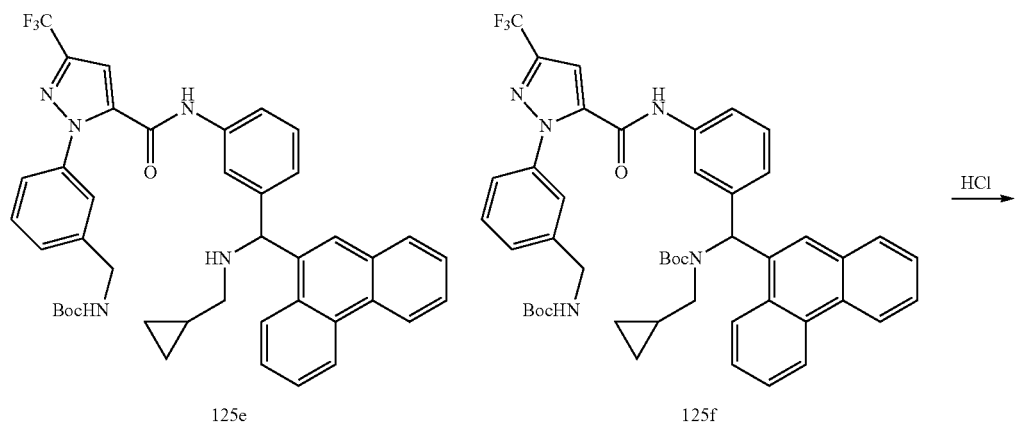
125e    125f

-continued

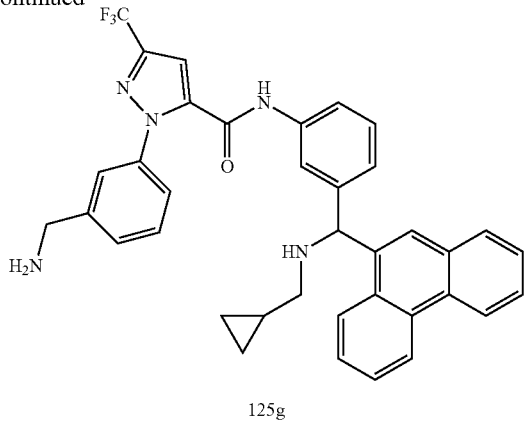

125g

Preparation of 1-(3-(Aminomethyl)phenyl)-N-(3-((cyclopropylmethylamino)(phenanthren-9-yl)methyl)phenyl)-3-(trifluoromethyl)-1H-pyrazole-5-carboxamide (125g)

Step-1: Preparation of (3-Amino-phenyl)-phenanthren-9-yl-methanol (125b)

To a stirred solution of Phenanthrene-9-carbaldehyde (125a) (1.2 g, 10 mmol) in tetrahydrofuran (5 mL) was added (3-(bis(trimethylsilyl)amino)phenyl)magnesium chloride (49c) (12.00 mL, 12.00 mmol) at 0° C. The reaction was stirred for 14 h at room temperature, quenched by adding 2 N HCl (12.50 mL) and stirred for 6 h. The reaction mixture was neutralized with 2 N NaOH (15 mL) and extracted with ethyl acetate (2×50 mL). The organic layers were combined washed with saturated aqueous NH$_4$Cl (50 mL), dried over anhydrous MgSO$_4$, filtered, evaporated to dryness. The crude residue was purified by flash column chromatography (silica gel 40 g, eluting with 0-100% ethyl acetate in hexane) to furnish (3-Amino-phenyl)-phenanthren-9-yl-methanol (125b) (2.5 g, 83.5%) as a light brown sticky liquid; $^1$H NMR (300 MHz, DMSO-d$_6$) δ 8.82 (ddd, J=9.3, 7.3, 2.3 Hz, 2H), 8.16-8.07 (m, 1H), 8.06-7.97 (m, 2H), 7.74-7.58 (m, 3H), 7.52 (ddd, J=8.2, 6.9, 1.3 Hz, 1H), 6.94 (t, J=7.7 Hz, 1H), 6.63 (d, J=7.5 Hz, 1H), 6.54 (t, J=1.9 Hz, 1H), 6.39 (ddd, J=8.0, 2.3, 1.1 Hz, 1H), 6.19 (d, J=4.4 Hz, 1H), 5.97 (d, J=4.4 Hz, 1H), 4.95 (s, 2H).

Step-2: Preparation of 2-(3-Cyano-phenyl)-5-trifluoromethyl-2H-pyrazole-3-carboxylic acid [3-(hydroxy-phenanthren-9-yl-methyl)-phenyl]-amide (125c)

To a solution of 1-(3-cyanophenyl)-3-(trifluoromethyl)-1H-pyrazole-5-carboxylic acid (9i) (2.348 g, 8.35 mmol) in DMF (45 mL) was added (3-Amino-phenyl)-phenanthren-9-yl-methanol (125b) (2.5 g, 8.35 mmol), N-ethyl-N-isopropylpropan-2-amine (11.0 mL, 66.8 mmol) and bromo-tris-pyrrolidino phosphoniumhexafluorophosphate (PyBrOP, 3.89 g, 8.350 mmol) at room temperature. The reaction mixture was stirred at room temperature for 21 h under nitrogen atmosphere. The reaction was diluted with ethyl acetate (350 mL) washed with water (2×150 mL), brine (120 mL), dried, filtered, and evaporated to dryness. The residue obtained was purified by flash column chromatography [silica gel 120 g, eluting with ethyl acetate in hexanes from 0-30%] to furnish 2-(3-Cyano-phenyl)-5-trifluoromethyl-2H-pyrazole-3-carboxylic acid [3-(hydroxy-phenanthren-9-yl-methyl)-phenyl]-amide (125c) (2.1 g, 44.77% yield) as a red brown sticky liquid; $^1$H NMR (300 MHz, DMSO-d$_6$) δ 10.59 (s, 1H), 8.92-8.76 (m, 2H), 8.15-8.00 (m, 4H), 7.98 (dt, J=7.7, 1.3 Hz, 1H), 7.86 (ddd, J=8.2, 2.2, 1.1 Hz, 1H), 7.73-7.59 (m, 6H), 7.56 (s, 1H), 7.51 (ddd, J=8.2, 6.9, 1.2 Hz, 1H), 7.32-7.25 (m, 2H), 6.34 (d, J=4.3 Hz, 1H), 6.25 (d, J=4.3 Hz, 1H).

Step-3: Preparation of 2-(3-Cyano-phenyl)-5-trifluoromethyl-2H-pyrazole-3-carboxylic acid {3-[(cyclopropylmethyl-amino)-phenanthren-9-yl-methyl]-phenyl}-amide (125d)

To a solution of 2-(3-Cyano-phenyl)-5-trifluoromethyl-2H-pyrazole-3-carboxylic acid [3-(hydroxy-phenanthren-9-yl-methyl)-phenyl]-amide (125c) (2.0 g, 3.56 mmol) in dichloromethane (40 mL) at 0° C. was added thionyl chloride (0.85 g, 7.11 mmol) and stirred at room temperature for 4 h. The reaction mixture was concentrated in vacuum to dryness. The residue obtained was dissolved in acetonitrile (40 mL) and added cyclopropylmethanamine (3.79 g, 53.33 mmol). The reaction mixture was heated at reflux overnight, cooled to room temperature and concentrated in vacuum to dryness. The residue obtained was dissolved in dichloromethane (40 mL), washed with water (2×25 mL), dried, filtered and concentrated in vacuum. The residue obtained was purified by flash column chromatography (silica gel 40 g, eluting 0-40% ethyl acetate in hexane) to afford 2-(3-Cyano-phenyl)-5-trifluoromethyl-2H-pyrazole-3-carboxylic acid {3-[(cyclopropylmethyl-amino)-phenanthren-9-yl-methyl]-phenyl}-amide (125d) (1.22 g, 55.66%) as pale solid; $^1$H NMR (300 MHz, DMSO-d$_6$) δ 10.51 (s, 1H), 8.81-8.74 (m, 1H), 8.74-8.68 (m, 1H), 8.22-8.16 (m, 1H), 8.06 (s, 1H), 8.04 (t, J=1.9 Hz, 1H), 7.90 (ddt, J=7.7, 6.7, 1.6 Hz, 2H), 7.77 (ddd, J=8.3, 2.2, 1.1 Hz, 1H), 7.61-7.58 (m, 2H), 7.57-7.54 (m, 3H), 7.51 (dt, J=6.7, 1.4 Hz, 3H), 7.28 (dt, J=7.6, 1.4 Hz, 1H), 7.24-7.16 (m, 1H), 5.54 (s, 1H), 2.38 (d, J=6.8 Hz, 3H), 1.01-0.87 (m, 1H), 0.42-0.26 (m, 2H), 0.09--0.08 (m, 2H).

Step-4: Preparation of [3-(5-{3-[(Cyclopropylmethyl-amino)-phenanthren-9-yl-methyl]-phenylcarbamoyl}-3-trifluoromethyl-pyrazol-1-yl)-benzyl]-carbamic acid tert-butyl ester (125e) and [(3-{[2-(3-Aminomethyl-phenyl)-5-trifluoromethyl-2H-pyrazole-3-carbonyl]-amino}-phenyl)-phenanthren-9-yl-methyl]-cyclopropylmethyl-carbamic acid tert-butyl ester (125f)

To a solution of 2-(3-Cyano-phenyl)-5-trifluoromethyl-2H-pyrazole-3-carboxylic acid {3-[(cyclopropylmethyl-amino)-phenanthren-9-yl-methyl]-phenyl}-amide (125d) (1.2 g, 1.95 mmol) in MeOH (24 mL) cooled with ice/water was added nickel(II) chloride hexahydrate (0.556 g, 2.338 mmol) and Boc anhydride (1.3 mL, 5.847 mmol) followed by portionwise addition of sodium borohydride (0.44 g, 11.694 mmol) over a period of 15 min. The reaction mixture was stirred at room temperature for 2 hrs and quenched with $N^1$-(2-aminoethyl)ethane-1,2-diamine (0.5 mL, 4.872 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over $MgSO_4$ filtered and concentrated in vacuum. The residue obtained was purified by flash column chromatography (silica gel 24 g, eluting with 0-25% Ethyl acetate/hexane) to furnish 1. [3-(5-{3-[(Cyclopropylmethyl-amino)-phenanthren-9-yl-methyl]-phenylcarbamoyl}-3-trifluoromethyl-pyrazol-1-yl)-benzyl]-carbamic acid tert-butyl ester (125e) (0.3 g, 18.79%) as a white solid; $^1$H NMR (300 MHz, DMSO-$d_6$) δ 10.69 (s, 1H), 8.91 (d, J=8.1 Hz, 1H), 8.84 (d, J=8.3 Hz, 1H), 7.98 (d, J=8.0 Hz, 1H), 7.88 (d, J=7.6 Hz, 1H), 7.75-7.66 (m, 4H), 7.63 (d, J=8.3 Hz, 2H), 7.49 (d, J=15.4 Hz, 4H), 7.50-7.43 (m, 3H), 7.40-7.32 (m, 4H), 7.30 (t, J=1.9 Hz, 1H), 7.05 (d, J=7.8 Hz, 1H), 4.16 (d, J=6.3 Hz, 2H), 3.19 (dt, J=27.1, 7.8 Hz, 2H), 1.36 (s, 18H), 0.86-0.70 (m, 1H), 0.01--0.06 (m, 2H), −0.15--0.33 (m, 2H).

2. [(3-{[2-(3-Aminomethyl-phenyl)-5-trifluoromethyl-2H-pyrazole-3-carbonyl]-amino}-phenyl)-phenanthren-9-yl-methyl]-cyclopropylmethyl-carbamic acid tert-butyl ester (125f) (0.62 g, 38.82%) as a white solid. $^1$H NMR (300 MHz, DMSO-$d_6$) δ 10.55 (s, 1H), 8.80-8.74 (m, 1H), 8.74-8.65 (m, 1H), 8.25-8.15 (m, 1H), 8.06 (s, 1H), 7.91 (dt, J=6.3, 2.6 Hz, 1H), 7.60-7.55 (m, 2H), 7.54-7.48 (m, 2H), 7.40 (d, J=8.3 Hz, 2H), 7.34-7.15 (m, 7H), 5.53 (s, 1H), 4.08 (d, J=6.3 Hz, 2H), 2.36 (s, 2H), 1.25 (s, 9H), 1.00-0.86 (m, 1H), 0.40-0.25 (m, 2H), −0.01 (dd, J=9.1, 4.7 Hz, 2H).

Step-5: Preparation of 2-(3-Aminomethyl-phenyl)-5-trifluoromethyl-2H-pyrazole-3-carboxylic acid {3-[(cyclopropylmethyl-amino)-phenanthren-9-yl-methyl]-phenyl}-amide (125g)

To a solution of [3-(5-{3-[(Cyclopropylmethyl-amino)-phenanthren-9-yl-methyl]-phenylcarbamoyl}-3-trifluoromethyl-pyrazol-1-yl)-benzyl]-carbamic acid tert-butyl ester (125e) (0.250 g, 0.35 mmol) and [(3-{[2-(3-Aminomethyl-phenyl)-5-trifluoromethyl-2H-pyrazole-3-carbonyl]-amino}-phenyl)-phenanthren-9-yl-methyl]-cyclopropylmethyl-carbamic acid tert-butyl ester (125f) (0.5 g, 0.695 mmol) were dissolved separately in methanol (10 mL) and added conc. HCL (0.5 mL). The reaction mixture was stirred at room temperature overnight and concentrated in vacuum to dryness. The residue was azeotroped with toluene (2×10 mL) and ethanol (10 mL), dried in vacuum pump to furnish a white solid residue. NMR of the residue in methanol and TLC shows same compound. The products were combined dried and purified by flash column chromatography (silica gel 12 g, eluting with 0-15% methanol in dichloromethane to furnish 2-(3-Aminomethyl-phenyl)-5-trifluoromethyl-2H-pyrazole-3-carboxylic acid {3-[(cyclopropylmethyl-amino)-phenanthren-9-yl-methyl]-phenyl}-amide (125g) (0.3 g, 46%) free base as an off white solid; $^1$H NMR (300 MHz, DMSO-$d_6$) δ 10.90 (s, 1H), 10.09 (s, 1H), 8.98-8.90 (m, 1H), 8.89-8.83 (m, 1H), 8.54 (s, 1H), 8.42 (s, 3H), 8.24-8.15 (m, 1H), 8.07-7.99 (m, 1H), 7.87 (s, 1H), 7.81-7.57 (m, 10H), 7.46 (ddt, J=17.2, 15.4, 7.8 Hz, 3H), 6.43 (s, 1H), 4.10 (s, 2H), 3.12-2.74 (m, 2H), 1.31-1.13 (m, 1H), 0.57 (d, J=7.8 Hz, 2H), 0.31 (d, J=26.4 Hz, 2H); $^1$H NMR (300 MHz, DMSO-$d_6$/$D_2O$) δ 8.96-8.90 (m, 1H), 8.87 (d, J=8.0 Hz, 1H), 8.41 (s, 1H), 8.18 (dd, J=8.4, 1.5 Hz, 1H), 8.09-8.03 (m, 1H), 7.86-7.55 (m, 12H), 7.54-7.42 (m, 3H), 6.41 (s, 1H), 4.10 (s, 2H), 3.13-2.76 (m, 2H), 1.26-1.16 (m, 1H), 0.59 (d, J=8.0 Hz, 2H), 0.31 (d, J=25.2 Hz, 2H); $^{19}$F NMR (282 MHz, DMSO-$d_6$) δ −60.81; MS (ES+) 620.4 (M+1); (ES−) 654.3 (M+Cl). Free base of 1-(3-(aminomethyl)phenyl)-N-(3-((cyclopropylmethylamino)(phenanthren-9-yl)methyl)phenyl)-3-(trifluoromethyl)-1H-pyrazole-5-carboxamide (125g) (250 mg) from above was purified by flash column chromatography (silica gel 24 g, eluting with 0-25% methanol in chloroform) and converted to hydrochloride by dissolving the product obtained in methanol (5 mL) and treating it with 10 equivalents of conc. HCl. The solution obtained was concentrated in vacuum to dryness dried in vacuum to furnish 2-(3-Aminomethyl-phenyl)-5-trifluoromethyl-2H-pyrazole-3-carboxylic acid {3-[(cyclopropylmethyl-amino)-(4-dimethylamino-naphthalen-1-yl)-methyl]-phenyl}-amide (125 g) (70 mg, 99%) hydrochloride salt as a pale yellow solid; $^1$H NMR (300 MHz, DMSO-$d_6$) δ 10.97 (s, 1H), 10.39 (d, J=10.4 Hz, 1H), 10.19 (s, 1H), 8.93 (dd, J=8.4, 1.5 Hz, 1H), 8.90-8.81 (m, 1H), 8.66 (s, 1H), 8.53 (s, 3H), 8.21 (dd, J=8.3, 1.5 Hz, 1H), 8.08-8.00 (m, 1H), 7.96-7.90 (m, 1H), 7.80-7.61 (m, 9H), 7.56-7.37 (m, 3H), 6.46 (t, J=6.2 Hz, 1H), 4.10 (q, J=6.0 Hz, 2H), 3.11-2.98 (m, 1H), 2.84 (td, J=9.5, 8.9, 4.2 Hz, 1H), 1.26 (ddd, J=12.6, 6.2, 3.6 Hz, 1H), 0.57 (dd, J=8.2, 4.0 Hz, 2H), 0.43-0.23 (m, 2H); $^{19}$F NMR (282 MHz, DMSO-$d_6$) δ −60.80; MS (ES+) 620.4 (M+1); (ES−) 618.4 (M−1); Analysis calculated for $C_{37}H_{32}F_3N_5O.2HCl.2H_2O$: C, 60.99; H, 5.26; Cl, 9.73; N, 9.61; Found: C, 60.82; H, 5.24; Cl, 9.92; N, 9.66.

Scheme 126
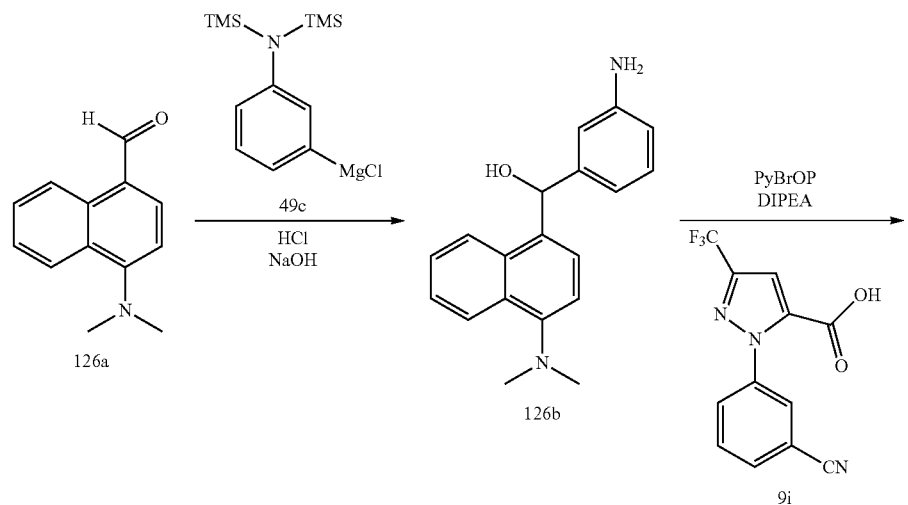
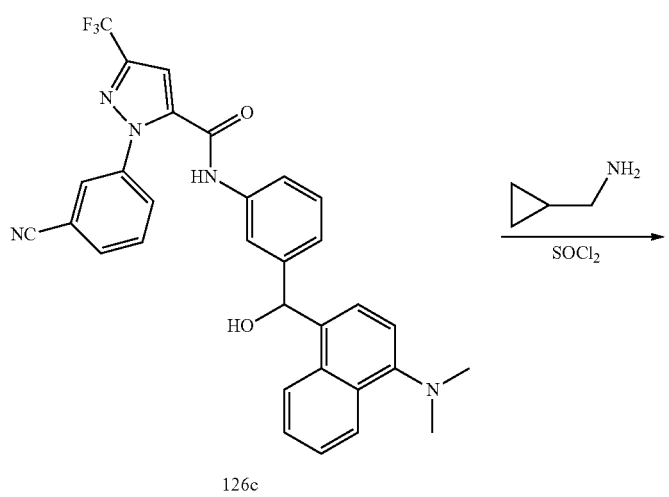
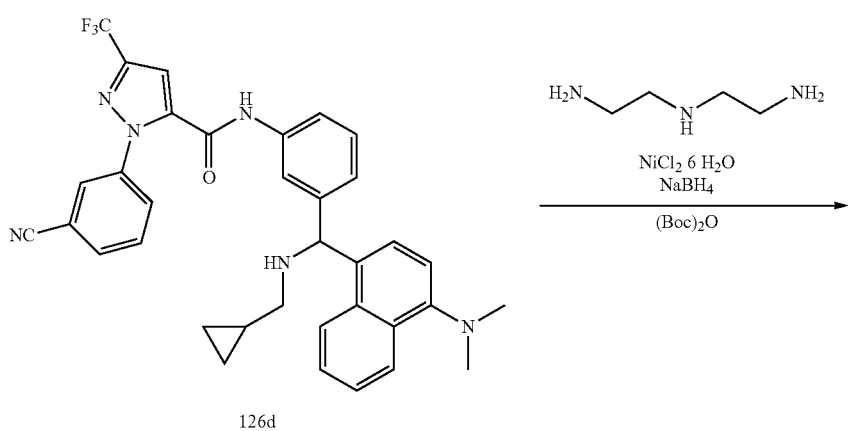

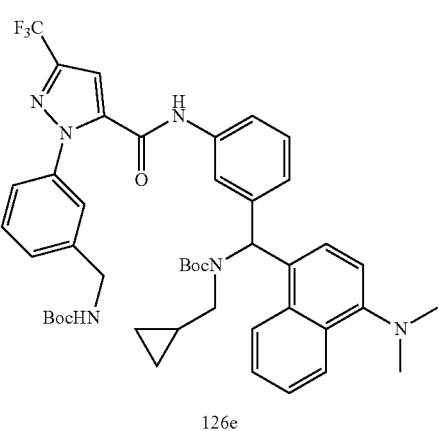

126e

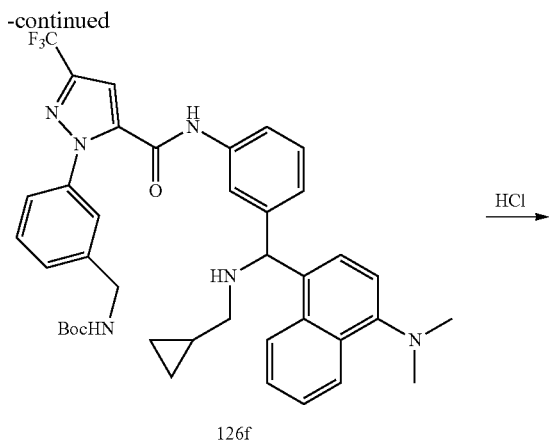

126f

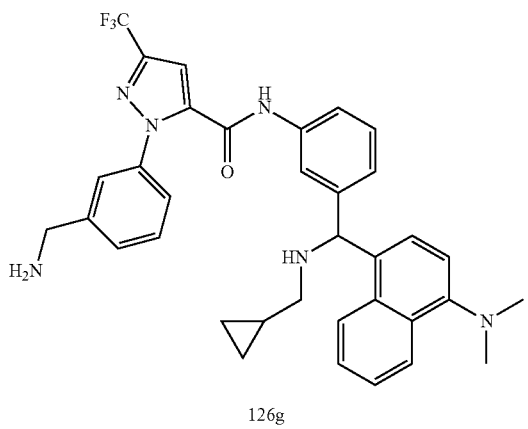

126g

Preparation of 1-(3-(Aminomethyl)phenyl)-N-(3-((cyclopropylmethylamino)(4-(dimethylamino)naphthalen-1-yl)methyl)phenyl)-3-(trifluoromethyl)-1H-pyrazole-5-carboxamide (126g)

Step-1: Preparation of (3-Amino-phenyl)-(4-dimethylamino-naphthalen-1-yl)-methanol (126b)

To a stirred solution of 4-Dimethylamino-naphthalene-1-carbaldehyde (126a) (1.2 g, 10 mmol) in tetrahydrofuran (5 mL) was added (3-(bis(trimethylsilyl)amino)phenyl)magnesium chloride (49c) (12.0 mL, 12.0 mmol) at 0° C. The reaction was stirred for 14 h at room temperature and quenched by adding 2 N HCl (12.5 mL). The reaction mixture was stirred for 6 h and basified with 2 N NaOH (15 mL) and extracted with ethyl acetate (2×50 mL). The organic layers were combined washed with saturated aqueous NH₄Cl (50 mL), dried over anhydrous MgSO₄, filtered and evaporated to dryness. The crude residue was purified by flash column chromatography (silica gel 40 g, eluting with 0-100% ethyl acetate in hexane) to (3-Amino-phenyl)-(4-dimethylamino-naphthalen-1-yl)-methanol (126b) (1.9 g, 65%) as a light brown oil; $^1$H NMR (300 MHz, DMSO-d$_6$) δ 8.17-8.11 (m, 1H), 8.11-8.06 (m, 1H), 7.50 (d, J=7.8 Hz, 1H), 7.40 (dqd, J=10.0, 6.7, 1.5 Hz, 2H), 7.09 (d, J=7.7 Hz, 1H), 6.94-6.84 (m, 1H), 6.57-6.49 (m, 2H), 6.40-6.32 (m, 1H), 6.08 (d, J=4.4 Hz, 1H), 5.73 (t, J=2.2 Hz, 1H), 4.93 (s, 2H), 2.78 (s, 6H).

Step-2: Preparation of 2-(3-Cyano-phenyl)-5-trifluoromethyl-2H-pyrazole-3-carboxylic Acid {3-[(4-dimethylamino-naphthalen-1-yl)-hydroxy-methyl]-phenyl}-amide (126c)

To a solution of 1-(3-cyanophenyl)-3-(trifluoromethyl)-1H-pyrazole-5-carboxylic acid (9i) (1.9 g, 6.756 mmol) in DMF (22 mL) was added (3-Amino-phenyl)-(4-dimethylamino-naphthalen-1-yl)-methanol (126b) (1.9 g 6.756 mmol), N-ethyl-N-isopropylpropan-2-amine (6.98 g, 54.048 mmol) and bromo-tris-pyrrolidino phosphoniumhexafluorophosphate (PyBrOP, 3.065 g, 6.756 mmol) at room temperature. The reaction mixture was stirred at room temperature for 39 h under nitrogen atmosphere. The reaction was diluted with ethyl acetate (200 mL) washed with water (2×300 mL), brine (200 mL), dried, filtered, and evaporated to dryness. The residue obtained was purified by flash column chromatography [silica gel 120 g, eluting with ethyl acetate in hexanes from 0-25%] to furnish 2-(3-Cyano-phenyl)-5-trifluoromethyl-2H-pyrazole-3-carboxylic acid {3-[hydroxy-(4-methoxy-naphthalen-1-yl)-methyl]-phenyl}-amide (126c) (0.7 g,) as a light brown liquid; $^1$H NMR (300 MHz, DMSO-d$_6$) δ 10.58 (s, 1H), 8.16-8.09 (m, 2H), 8.09-8.04 (m, 1H), 7.95 (dt, J=7.7, 1.3 Hz, 1H), 7.85 (ddd, J=8.3, 2.2, 1.1 Hz, 1H), 7.69 (d, J=7.9 Hz, 1H), 7.65 (s, 1H), 7.58 (d, J=2.0 Hz, 1H), 7.57-7.51 (m, 1H), 7.47 (d, J=7.8 Hz, 1H), 7.39 (dddd, J=17.3, 8.2, 6.8, 1.5 Hz, 2H), 7.23 (t, J=7.8 Hz, 1H), 7.13 (d, J=7.7 Hz, 1H), 7.08 (d, J=7.8 Hz, 1H), 6.21 (d, J=4.3 Hz, 1H), 5.97 (d, J=4.2 Hz, 1H), 2.77 (s, 6H).

Step-3: Preparation of 2-(3-Cyano-phenyl)-5-trifluoromethyl-2H-pyrazole-3-carboxylic acid {3-[(cyclopropylmethyl-amino)-(4-dimethylamino-naphthalen-1-yl)-methyl]-phenyl}-amide (126d)

To a solution of 2-(3-Cyano-phenyl)-5-trifluoromethyl-2H-pyrazole-3-carboxylic acid {3-[(4-dimethylamino-naphthalen-1-yl)-hydroxy-methyl]-phenyl}-amide (126c) (0.7 g, 1.260 mmol) in dichloromethane (50 mL) at 0° C. was added thionyl chloride (0.299 g, 2.520 mmol) and stirred at room temperature for 4 h. The reaction mixture was concentrated in vacuum to dryness. The residue obtained was dissolved in acetonitrile (30 mL) and added cyclopropylmethanamine (1.34 g, 18.9 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum. The residue obtained was purified by flash column chromatography (silica gel 40 g, eluting 0-100% ethyl acetate in hexane) to afford 2-(3-Cyano-phenyl)-5-trifluoromethyl-2H-pyrazole-3-carboxylic acid {3-[(cyclopropylmethyl-amino)-(4-dimethylamino-naphthalen-1-yl)-methyl]-phenyl}-amide (126d) (0.4 g) as a brown sticky liquid; $^1$HNMR (300 MHz, DMSO-$d_6$) δ 10.55 (s, 1H), 8.18 (dd, J=6.7, 3.2 Hz, 1H), 8.14-8.08 (m, 1H), 8.07 (t, J=1.9 Hz, 1H), 7.92 (dt, J=7.7, 1.3 Hz, 1H), 7.81 (ddd, J=8.3, 2.2, 1.2 Hz, 1H), 7.66 (d, J=7.9 Hz, 1H), 7.62 (d, J=3.6 Hz, 1H), 7.59-7.52 (m, 2H), 7.52-7.45 (m, 1H), 7.44-7.35 (m, 2H), 7.24-7.14 (m, 2H), 7.06 (d, J=7.9 Hz, 1H), 5.47 (s, 1H), 2.72 (s, 6H), 2.32 (d, J=6.6 Hz, 2H), 1.00-0.82 (m, 1H), 0.32 (dd, J=7.7, 1.3 Hz, 2H), 0.07--0.08 (m, 2H).

Step-4: Preparation of [3-(5-{3-[(Cyclopropylmethyl-amino)-(4-dimethylamino-naphthalen-1-yl)-methyl]-phenylcarbamoyl}-3-trifluoromethyl-pyrazol-1-yl)-benzyl]-carbamic Acid tert-butyl ester (126f) and [(3-{[2-(3-Aminomethyl-phenyl)-5-trifluoromethyl-2H-pyrazole-3-carbonyl]-amino}-phenyl)-(4-dimethylamino-naphthalen-1-yl)-methyl]-cyclopropylmethyl-carbamic Acid tert-butyl ester (126e)

To a solution of 2-(3-Cyano-phenyl)-5-trifluoromethyl-2H-pyrazole-3-carboxylic acid {3-[(cyclopropylmethyl-amino)-(4-dimethylamino-naphthalen-1-yl)-methyl]-phenyl}-amide (126d) (0.4 g, 0.656 mmol) in MeOH (10 mL) cooled with ice/water was added nickel(II) chloride hexahydrate (0.195 g, 0.821 mmol) and Boc anhydride (0.429 g, 1.968 mmol) followed by portionwise addition of Sodium Borohydride (0.148 g, 3.936 mmol) over a period of 15 min. The reaction mixture was stirred at room temperature for 2 hrs and quenched with N1-(2-aminoethyl)ethane-1,2-diamine (0.270 mL, 2.624 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over MgSO$_4$ filtered and concentrated in vacuum. The residue obtained was purified by flash column chromatography (silica gel 24 g, eluting with 0-25% chloroform/methanol) to furnish [3-(5-{3-[(Cyclopropylmethyl-amino)-(4-dimethylamino-naphthalen-1-yl)-methyl]-phenylcarbamoyl}-3-trifluoromethyl-pyrazol-1-yl)-benzyl]-carbamic acid tert-butyl ester (126f) (0.170 g, 32%) as a white solid; $^1$H NMR (300 MHz, DMSO-$d_6$) δ 10.74 (s, 1H), 8.25 (dt, J=7.8, 2.7 Hz, 1H), 8.05-7.93 (m, 1H), 7.71 (d, J=8.1 Hz, 1H), 7.61-7.48 (m, 5H), 7.44 (dd, J=7.0, 2.1 Hz, 2H), 7.40-7.34 (m, 3H), 7.07 (d, J=7.9 Hz, 1H), 6.97 (t, J=8.7 Hz, 2H), 4.21 (d, J=6.2 Hz, 2H), 3.36-3.23 (m, 2H), 2.84 (s, 6H), 1.48-1.35 (bs, 18H), 0.34 (m, 1H), -0.00 (m, 1H), -0.27 (m, 2H), -0.87 (m, 1H)} and [(3-{[2-(3-Aminomethyl-phenyl)-5-trifluoromethyl-2H-pyrazole-3-carbonyl]-amino}-phenyl)-(4-dimethylamino-naphthalen-1-yl)-methyl]-cyclopropylmethyl-carbamic acid tert-butyl ester (126e) (0.140 g, 30%) as a white solid; $^1$H NMR (300 MHz, DMSO-$d_6$) δ 10.60 (s, 1H), 8.31-8.05 (m, 2H), 7.66-7.13 (m, 12H), 7.07 (d, J=7.9 Hz, 1H), 6.93 (dt, J=35.7, 8.2 Hz, 1H), 5.47 (s, 1H), 4.12 (d, J=6.2 Hz, 2H), 2.73 (s, 6H), 2.33 (d, J=6.8 Hz, 2H), 1.29 (s, 9H), 1.00-0.84 (m, 1H), 0.40-0.27 (m, 2H), 0.05--0.07 (m, 3H).

Step-5: Preparation of 2-(3-Aminomethyl-phenyl)-5-trifluoromethyl-2H-pyrazole-3-carboxylic acid {3-[(cyclopropylmethyl-amino)-(4-dimethylamino-naphthalen-1-yl)-methyl]-phenyl}-amide (126g)

A solution of [3-(5-{3-[(Cyclopropylmethyl-amino)-(4-dimethylamino-naphthalen-1-yl)-methyl]-phenylcarbamoyl}-3-trifluoromethyl-pyrazol-1-yl)-benzyl]-carbamic acid tert-butyl ester (126f) (0.160 g, 0.197 mmol) and [(3-{[2-(3-Aminomethyl-phenyl)-5-trifluoromethyl-2H-pyrazole-3-carbonyl]-amino}-phenyl)-(4-dimethylamino-naphthalen-1-yl)-methyl]-cyclopropylmethyl-carbamic acid tert-butyl ester (126e) (0.13 g, 0.182 mmol) were dissolved separately in methanol (2.5 mL) and added conc. HCl (0.5 mL). The reaction mixture was stirred at room temperature overnight and concentrated in vacuum to dryness. The residue was azeotroped with toluene (2×10 mL) and ethanol (10 mL), dried in vacuum pump to furnish a white solid residue. NMR of the residue in methanol and TLC shows same compound. The products were combined dried and purified by flash column chromatography (silica gel 12 g, eluting with 0-150% methanol in dichloromethane to furnish 2-(3-Aminomethyl-phenyl)-5-trifluoromethyl-2H-pyrazole-3-carboxylic acid {3-[(cyclopropylmethyl-amino)-(4-dimethylamino-naphthalen-1-yl)-methyl]-phenyl}-amide (126g) (0.135 g, 28%) as an off white solid; $^1$H NMR (300 MHz, DMSO-$d_6$) δ 11.06 (d, J=4.5 Hz, 1H), 10.46 (s, 1H), 10.17 (s, 1H), 8.68 (s, 3H), 8.26 (q, J=4.9 Hz, 2H), 7.94 (s, 1H), 7.75-7.64 (m, 5H), 7.63-7.35 (m, 6H), 6.50-6.25 (m, 1H), 4.10 (q, J=5.8 Hz, 2H), 2.93 (s, 8H), 1.25 (d, J=7.5 Hz, 1H), 0.62-0.48 (m, 2H), 0.30 (qd, J=9.4, 4.2 Hz, 2H); 1H NMR (300 MHz, DMSO-$d_6$) δ 8.37-8.30 (m, 1H), 8.28-8.21 (m, 1H), 8.18 (d, J=8.0 Hz, 1H), 7.90 (t, J=1.8 Hz, 1H), 7.73-7.38 (m, 12H), 6.38 (s, 1H), 4.11 (s, 2H), 3.00-2.76 (m, 8H), 1.24-1.14 (m, 1H), 0.56 (d, J=8.2 Hz, 2H), 0.42-0.20 (m, 2H); $^{19}$F NMR (282 MHz, DMSO-$d_6$) δ -60.77; MS (ES+) 613.3 (M+1), 635.3 (M+Na); (ES-) 647.3 (M+Cl); Analysis calculated for $C_{35}H_{35}F_3N_6O.3HCl.12H_2O.6.5NaCl$: C, 31.89; H, 4.74; Cl, 25.55; N, 6.38 Found: C, 32.28; H, 4.39; Cl, 25.46; N, 6.10. 2-(3-Aminomethyl-phenyl)-5-trifluoromethyl-2H-pyrazole-3-carboxylic acid {3-[(cyclopropylmethyl-amino)-(4-dimethylamino-naphthalen-1-yl)-methyl]-phenyl}-amide (126g) (170 mg) from above was purified by flash column chromatography (silica gel 12 g, eluting with 0-25% methanol in chloroform) and converted to hydrochloride salt by dissolving the product obtained in methanol (5 mL) and treating it with 10 equivalents of conc HCl. The solution obtained was concentrated in vacuum to dryness dried in vacuum to furnish 2-(3-Aminomethyl-phenyl)-5-trifluoromethyl-2H-pyrazole-3-carboxylic acid {3-[(cyclopropylmethyl-amino)-(4-dimethylamino-naphthalen-1-yl)-methyl]-phenyl}-amide (126g) (70 mg, 99%) hydrochloride salt as a pale yellow solid. $^1$H NMR (300 MHz, DMSO-d$_6$) δ 10.98 (d, J=1.6 Hz, 1H), 10.34 (s, 1H), 10.08 (s, 1H), 8.54 (s, 2H), 8.38 (s, 1H), 8.31-8.17 (m, 2H), 7.94-7.84 (m, 1H), 7.72 (d, J=1.9 Hz, 1H), 7.70-7.57 (m, 6H), 7.54 (d, J=7.8 Hz, 1H), 7.53-7.46 (m, 1H), 7.41 (td, J=7.9, 1.3 Hz, 1H), 6.39 (t, J=6.3 Hz, 1H), 4.97 (d, J=5.4 Hz, 1H), 4.11 (q, J=5.9 Hz, 2H), 2.97 (s, 6H), 2.43 (d, J=14.0 Hz, 2H), 1.31-1.17 (m, 1H), 0.65-0.47 (m, 2H), 0.41-0.19 (m, 2H); $^{19}$F NMR (282 MHz, DMSO) δ −60.78; MS (ES−) 647.3 (M+Cl); Analysis calculated for C$_{35}$H$_{35}$F$_3$N$_6$O.2.75HCl.3H$_2$O: C, 54.81; H, 5.75; Cl, 12.71; N, 10.96: Found: C, 55.22; H, 5.78; Cl, 12.77; N, 10.28.
Scheme 127
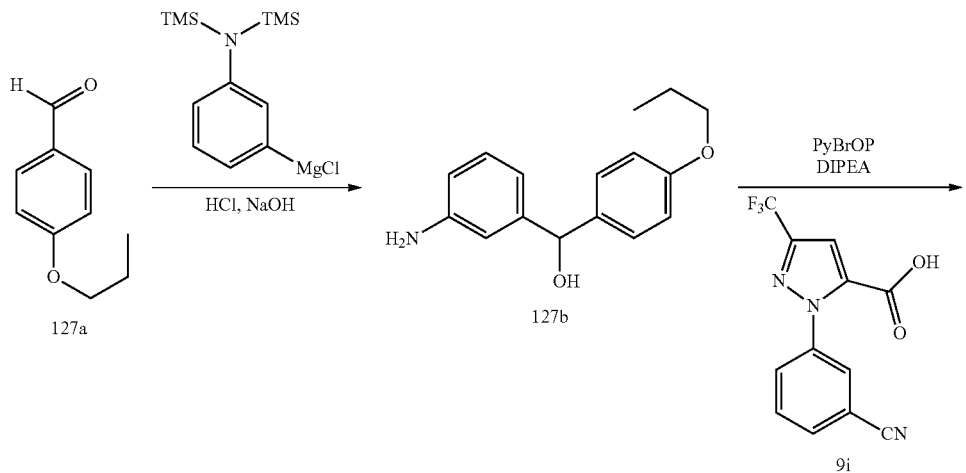
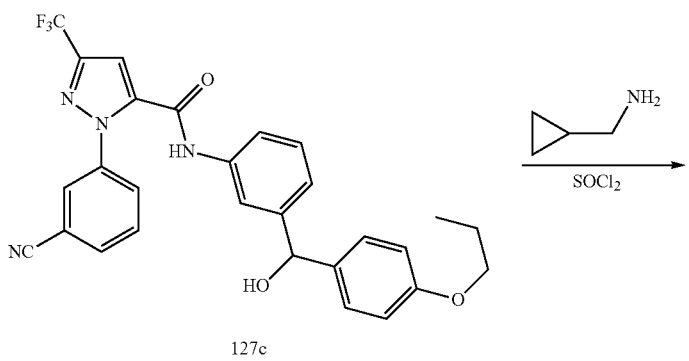
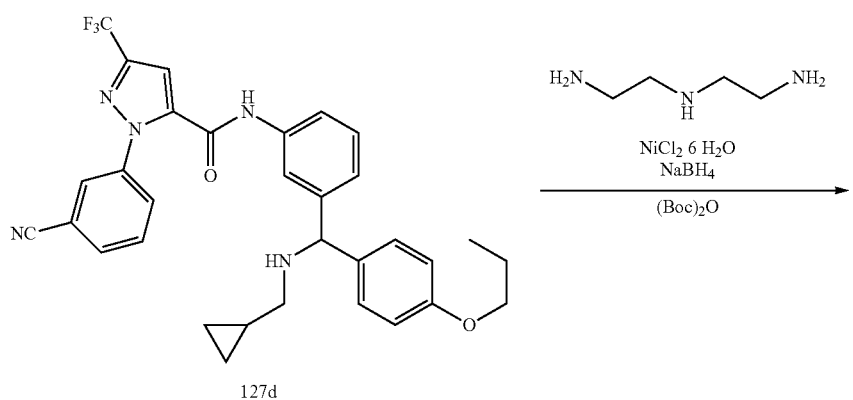

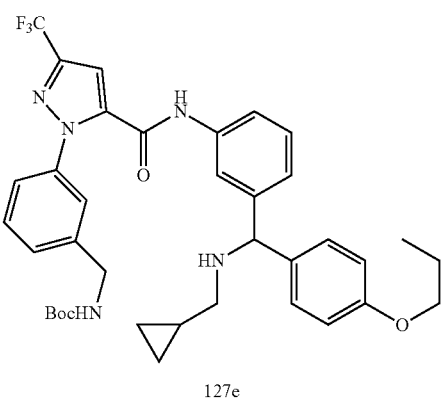

127e

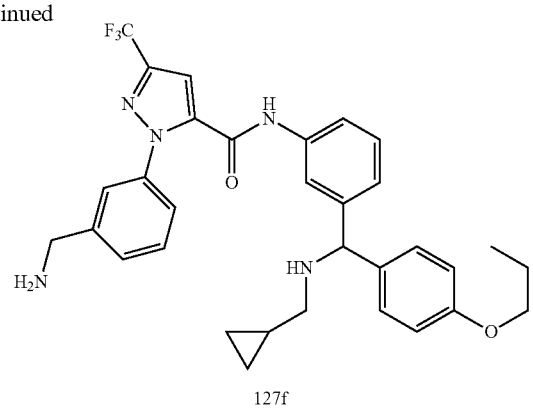

127f

Preparation of 1-(3-(Aminomethyl)phenyl)-N-(3-((cyclopropylmethylamino)(4-propoxyphenyl)methyl)phenyl)-3-(trifluoromethyl)-1H-pyrazole-5-carboxamide (127f)

Step-1: Preparation of (3-Amino-phenyl)-(4-propoxy-phenyl)-methanol (127b)

To a stirred solution of 4-Propoxy-benzaldehyde (127a) (1.2 g, 10 mmol) in tetrahydrofuran (5 mL) was added (3-(bis(trimethylsilyl)amino)phenyl)magnesium chloride (49c) (12.00 mL, 12.00 mmol) at 0° C. The reaction was stirred for 14 h at room temperature quenched by adding 2 N HCl (12.50 mL) and stirred for 6 h. The reaction mixture was treated with 2 N NaOH (15 mL) and extracted with ethyl acetate (2×50 mL). The organic layers were combined washed with sat. NH$_4$Cl (50 mL), dried over anhydrous MgSO$_4$, filtered, evaporated to dryness. The crude residue was purified by flash column chromatography (silica gel 40 g, eluting with 0-100% ethyl acetate in hexane) to afford (3-Amino-phenyl)-(4-propoxy-phenyl)-methanol (127b) (2.0 g, 77.72%) as a light brown sticky liquid; $^1$H NMR (300 MHz, DMSO-d$_6$) δ 7.24-7.18 (m, 2H), 6.90 (t, J=7.7 Hz, 1H), 6.85-6.80 (m, 2H), 6.55 (t, J=1.9 Hz, 1H), 6.48 (dt, J=7.7, 1.3 Hz, 1H), 6.37 (ddd, J=7.9, 2.4, 1.0 Hz, 1H), 5.57 (d, J=3.9 Hz, 1H), 5.44 (d, J=3.9 Hz, 1H), 4.97 (s, 2H), 3.86 (td, J=6.6, 3.3 Hz, 2H), 1.77-1.59 (m, 2H), 0.95 (t, J=7.4 Hz, 3H).

Step-2: Preparation of 2-(3-Cyano-phenyl)-5-trifluoromethyl-2H-pyrazole-3-carboxylic acid {3-[hydroxy-(4-propoxy-phenyl)-methyl]-phenyl}-amide (127c)

To a solution of 1-(3-cyanophenyl)-3-(trifluoromethyl)-1H-pyrazole-5-carboxylic acid (9i) (2.16 g, 7.69 mmol) in DMF (40 mL) was added (3-Amino-phenyl)-(4-propoxyphenyl)-methanol (127b) (1.80 g, 6.99 mmol), N-ethyl-N-isopropylpropan-2-amine (9.8 mL, 55.96 mmol) and bromotris-pyrrolidino phosphoniumhexafluorophosphate (PyBrOP, 3.59 g, 7.69 mmol) at room temperature. The reaction mixture was stirred at room temperature for 19 h under nitrogen atmosphere. The reaction was diluted with ethyl acetate (50 mL) washed with water (2×50 mL), brine (50 mL), dried, filtered, and evaporated to dryness. The residue obtained was purified by flash column chromatography [silica gel 120 g, eluting with ethyl acetate in hexanes from 0-25%] to furnish 2-(3-Cyano-phenyl)-5-trifluoromethyl-2H-pyrazole-3-carboxylic acid {3-[hydroxy-(4-propoxy-phenyl)-methyl]-phenyl}-amide (127c) (2.0 g, 55%) as a light brown liquid; $^1$H NMR (300 MHz, DMSO-d$_6$) δ 10.69 (s, 1H), 8.21 (t, J=1.9 Hz, 1H), 8.06 (dt, J=7.8, 1.3 Hz, 1H), 7.96 (ddd, J=8.2, 2.2, 1.1 Hz, 1H), 7.84-7.73 (m, 2H), 7.67 (t, J=1.8 Hz, 1H), 7.64-7.54 (m, 1H), 7.31 (s, 1H), 7.31-7.24 (m, 2H), 7.17 (d, J=7.8 Hz, 1H), 6.95-6.85 (m, 2H), 5.89 (d, J=3.9 Hz, 1H), 5.67 (d, J=3.9 Hz, 1H), 3.93 (t, J=6.5 Hz, 2H), 1.75 (h, J=7.1 Hz, 2H), 1.01 (t, J=7.4 Hz, 3H).

Step-3: Preparation of 2-(3-Cyano-phenyl)-5-trifluoromethyl-2H-pyrazole-3-carboxylic acid {3-[(cyclopropylmethyl-amino)-(4-propoxy-phenyl)-methyl]-phenyl}-amide (127d)

To a solution of 2-(3-Cyano-phenyl)-5-trifluoromethyl-2H-pyrazole-3-carboxylic acid {3-[hydroxy-(4-propoxy-phenyl)-methyl]-phenyl}-amide (127c) (2.0 g, 3.84 mmol) in dichloromethane (40 mL) at 0° C. was added thionyl chloride (0.914 g, 7.68 mmol) and stirred at room temperature for 4 h. The reaction mixture was concentrated in vacuum to dryness. The residue obtained was dissolved in acetonitrile (40 mL) and added cyclopropylmethanamine (5.0 g, 57.636 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum. The residue obtained was purified by flash column chromatography (silica gel 40 g, eluting 0-50% ethyl acetate in hexane) to afford 2-(3-Cyano-phenyl)-5-trifluoromethyl-2H-pyrazole-3-carboxylic acid {3-[(cyclopropylmethyl-amino)-(4-propoxy-phenyl)-methyl]-phenyl}-amide (127d) (1.14 g, 51.76%) as a pale sticky liquid; $^1$H NMR (300 MHz, DMSO-d$_6$) δ 10.59 (s, 1H), 8.11 (t, J=1.8 Hz, 1H), 7.96 (dt, J=7.8, 1.3 Hz, 1H), 7.86 (ddd, J=8.2, 2.2, 1.1 Hz, 1H), 7.70 (d, J=7.9 Hz, 1H), 7.67 (s, 1H), 7.60 (d, J=2.0 Hz, 1H), 7.53-7.45 (m, 1H), 7.26-7.16 (m, 3H), 7.16-7.09 (m, 1H), 6.82-6.75 (m, 2H), 4.72 (s, 1H), 3.81 (t, J=6.5 Hz, 2H), 2.23 (d, J=6.6 Hz, 2H), 1.74-1.53 (m, 2H), 0.90 (t, J=7.4 Hz, 3H), 0.87-0.74 (m, 1H), 0.39-0.28 (m, 2H), 0.00 (m, 2H).

Step-4: Preparation of [3-(5-{3-[(Cyclopropylmethyl-amino)-(4-propoxy-phenyl)-methyl]-phenyl-carbamoyl}-3-trifluoromethyl-pyrazol-1-yl)-benzyl]-carbamic Acid Tert-Butyl Ester (127e)

To a solution of 2-(3-Cyano-phenyl)-5-trifluoromethyl-2H-pyrazole-3-carboxylic acid {3-[(cyclopropylmethyl-amino)-(4-propoxy-phenyl)-methyl]-phenyl}-amide (127d) (1.0 g, 1.74 mmol) in MeOH (24 mL) cooled with ice/water was added nickel(II) chloride hexahydrate (0.49 g, 2.09 mmol) and Boc anhydride (1.2 mL, 5.23 mmol) followed by portion-wise addition of sodium borohydride (0.395 g, 10.46 mmol) over a period of 15 min. The reaction mixture was stirred at room temperature for 2 hrs and quenched with $N^1$-(2-aminoethyl)ethane-1,2-diamine (0.5 mL, 4.36 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over $MgSO_4$ filtered and concentrated in vacuum. The residue obtained was purified by flash column chromatography (silica gel 24 g, eluting with 0-40% Ethyl acetate/n-hexane) to furnish [3-(5-{3-[(Cyclopropylmethyl-amino)-(4-propoxy-phenyl)-methyl]-phenylcarbamoyl}-3-trifluoromethyl-pyrazol-1-yl)-benzyl]-carbamic acid tert-butyl ester (127e) (0.5 g, 42.40%) as a white solid; $^1$H NMR (300 MHz, DMSO-$d_6$) δ 10.63 (s, 1H), 7.64-7.55 (m, 1H), 7.52 (s, 1H), 7.50-7.42 (m, 2H), 7.41-7.33 (m, 2H), 7.33-7.27 (m, 2H), 7.26-7.17 (m, 3H), 7.17-7.09 (m, 1H), 6.82-6.74 (m, 2H), 4.71 (s, 1H), 4.15 (d, J=6.2 Hz, 2H), 3.81 (t, J=6.5 Hz, 2H), 2.23 (d, J=6.7 Hz, 2H), 1.64 (q, J=6.9 Hz, 2H), 1.31 (s, 9H), 0.90 (t, J=7.4 Hz, 3H), 0.85-0.74 (m, 1H), 0.39-0.27 (m, 2H), 0.00 (dd, J=5.5, 3.8 Hz, 2H).

Step-5: Preparation of 2-(3-Aminomethyl-phenyl)-5-trifluoromethyl-2H-pyrazole-3-carboxylic acid {3-[(cyclopropylmethyl-amino)-(4-propoxy-phenyl)-methyl]-phenyl}-amide (127f)

A solution of [3-(5-{3-[(Cyclopropylmethyl-amino)-(4-propoxy-phenyl)-methyl]-phenylcarbamoyl}-3-trifluoromethyl-pyrazol-1-yl)-benzyl]-carbamic acid tert-butyl ester (127e) (0.500 g, 0.74 mmol) was dissolved in methanol (10 mL) and added conc. HCl (0.5 mL). The reaction mixture was stirred at room temperature overnight and concentrated in vacuum to dryness. The residue was azeotroped with toluene (2×10 mL) and ethanol (10 mL), dried in vacuum pump to furnish a white solid residue. The product was purified by flash column chromatography (silica gel 12 g, eluting with 0-15% methanol in dichloromethane to furnish 2-(3-Aminomethyl-phenyl)-5-trifluoromethyl-2H-pyrazole-3-carboxylic acid {3-[(cyclopropylmethyl-amino)-(4-propoxy-phenyl)-methyl]-phenyl}-amide (127f) (120 mg, 20.87%) as a pale white powder; $^1$H NMR (300 MHz, DMSO-$d_6$) δ 10.96 (s, 1H), 9.96 (s, 2H), 8.47 (s, 3H), 7.83 (s, 1H), 7.73 (s, 1H), 7.70 (s, 1H), 7.58 (dtt, J=17.6, 6.3, 3.9 Hz, 7H), 7.43 (t, J=7.8 Hz, 1H), 6.96 (d, J=8.2 Hz, 2H), 5.64-5.37 (m, 1H), 4.12 (q, J=5.7, 5.3 Hz, 2H), 3.91 (t, J=6.4 Hz, 2H), 2.68 (q, J=9.4, 6.4 Hz, 2H), 1.70 (q, J=6.9 Hz, 2H), 1.20-1.05 (m, 1H), 0.95 (t, J=7.3 Hz, 3H), 0.60-0.48 (m, 2H), 0.30 (t, J=4.7 Hz, 2H); $^1$H NMR (300 MHz, DMSO-$d_6$) δ 10.95 (s, 1H), 7.82 (s, 1H), 7.72 (s, 1H), 7.67 (s, 1H), 7.64-7.41 (m, 8H), 6.98 (d, J=8.3 Hz, 2H), 5.52 (s, 1H), 4.13 (s, 2H), 3.92 (t, J=6.4 Hz, 2H), 2.70 (dd, J=7.1, 3.4 Hz, 2H), 1.70 (q, J=6.9 Hz, 2H), 1.09 (q, J=6.8, 6.1 Hz, 1H), 0.95 (t, J=7.3 Hz, 3H), 0.64-0.50 (m, 2H), 0.29 (d, J=4.7 Hz, 2H); $^{19}$F NMR (282 MHz, DMSO-$d_6$) δ −60.77; MS (ES+) 578.4 (M+1); (ES−) 612.4 (M+Cl); Analysis calculated for $C_{32}H_{34}F_3N_5O_2 \cdot 2.75HCl \cdot 5.5H_2O$: C, 49.47; H, 6.19; Cl, 12.55; N, 9.01; Found: C, 49.44; H, 5.81; Cl, 12.47; N, 8.83.

Scheme 128

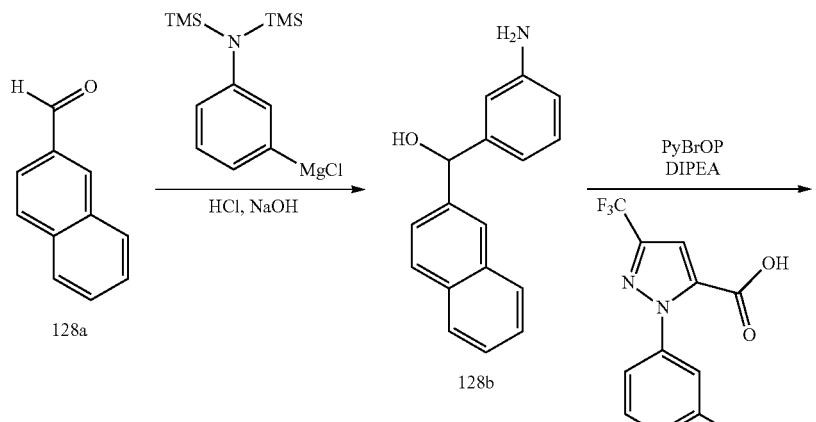

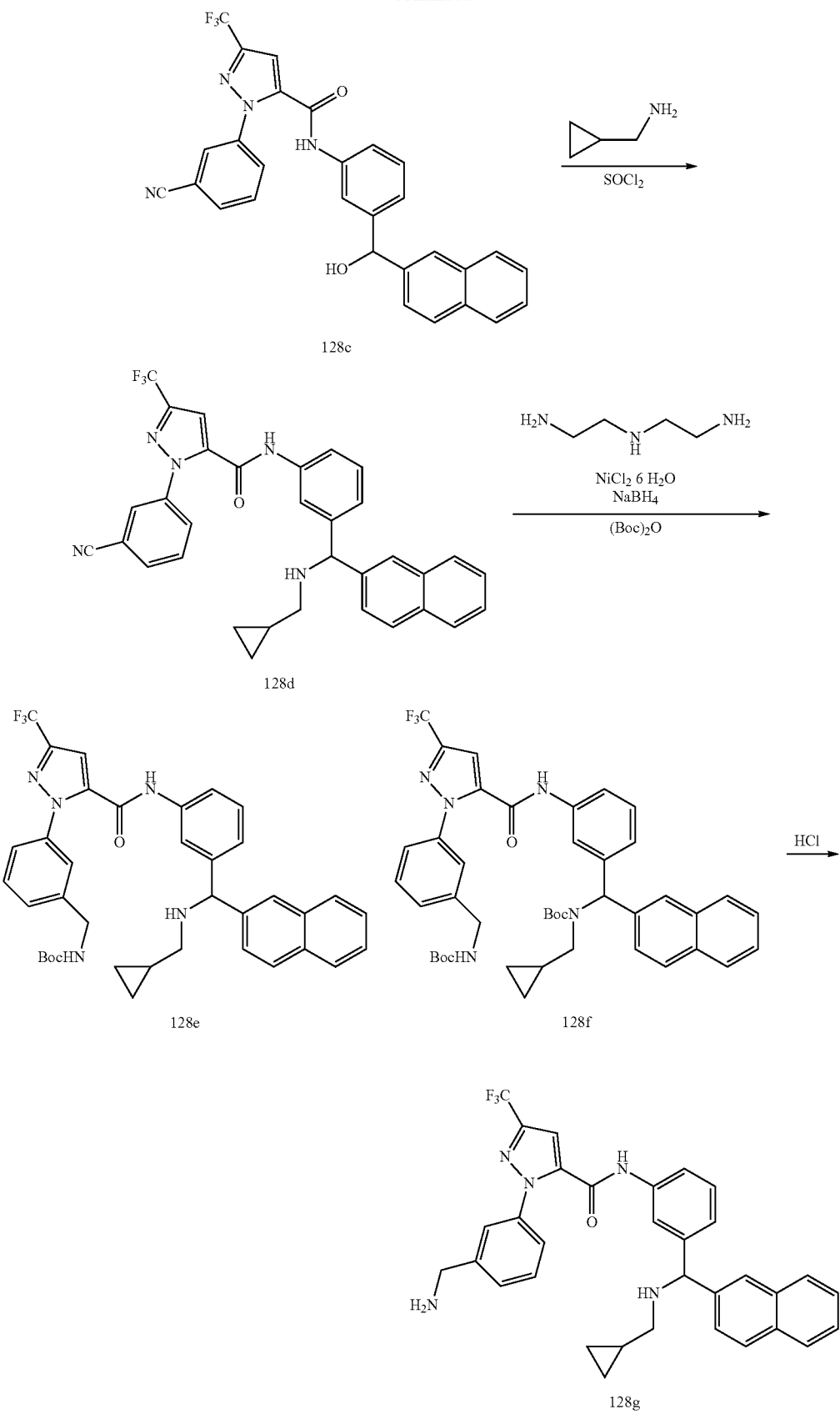
-continued

Preparation of 1-(3-(aminomethyl)phenyl)-N-(3-((cyclopropylmethylamino)(naphthalen-2-yl)methyl)phenyl)-3-(trifluoromethyl)-1H-pyrazole-5-carboxamide (128g)

Step-1: Preparation of (3-Amino-phenyl)-naphthalen-2-yl-methanol (128b)

To a stirred solution of naphthalene-2-carbaldehyde (128a) (1.2 g, 10 mmol) in tetrahydrofuran (5 mL) was added (3-(bis(trimethylsilyl)amino)phenyl)magnesium chloride (49c) (12.00 mL, 12.00 mmol) at 0° C. The reaction was stirred for 14 h at room temperature quenched by adding 2 N HCl (12.50 mL) and stirred for 6 h. The reaction mixture was treated with 2 N NaOH (15 mL) and extracted with ethyl acetate (2×50 mL). The organic layers were combined washed with sat. NH$_4$Cl (50 mL), dried over anhydrous MgSO$_4$, filtered, evaporated to dryness. The crude residue was purified by flash column chromatography (silica gel 40 g, eluting with 0-100% ethyl acetate in hexane) to furnish (3-Amino-phenyl)-naphthalen-2-yl-methanol (128b) (2.4 g, 96.27%) as a light brown sticky liquid; $^1$H NMR (300 MHz, DMSO-d$_6$) δ 7.82 (dd, J=8.1, 1.6 Hz, 3H), 7.75 (d, J=8.6 Hz, 1H), 7.45-7.36 (m, 3H), 6.87 (t, J=7.7 Hz, 1H), 6.58-6.48 (m, 2H), 6.33 (ddd, J=7.9, 2.3, 1.0 Hz, 1H), 5.79 (d, J=3.8 Hz, 1H), 5.62 (d, J=3.8 Hz, 1H), 4.93 (s, 2H).

Step-2: Preparation of 2-(3-Cyano-phenyl)-5-trifluoromethyl-2H-pyrazole-3-carboxylic acid [3-(hydroxy-naphthalen-2-yl-methyl)-phenyl]-amide (128c)

To a solution of 1-(3-cyanophenyl)-3-(trifluoromethyl)-1H-pyrazole-5-carboxylic acid (9i) (2.4 g, 8.54 mmol) in DMF (48 mL) was added 3-Amino-phenyl)-naphthalen-2-yl-methanol (128b) (2.12 g, 8.535 mmol), N-ethyl-N-isopropylpropan-2-amine (11.8 g, 68.24 mmol) and bromo-tris-pyrrolidino phosphoniumhexafluorophosphate (PyBrOP; 3.97 g, 8.54 mmol) at room temperature. The reaction mixture was stirred at room temperature for 42 h under nitrogen atmosphere. The reaction was diluted with ethyl acetate (350 mL) washed with water (2×150 mL), brine (120 mL), dried, filtered, and evaporated to dryness. The residue obtained was purified by flash column chromatography [silica gel 120 g, eluting with ethyl acetate in hexanes from 0-30%] to furnish 2-(3-Cyano-phenyl)-5-trifluoromethyl-2H-pyrazole-3-carboxylic acid [3-(hydroxy-naphthalen-2-yl-methyl)-phenyl]-amide (128c) (2.6 g, 59.4% yield) as a brown sticky liquid; $^1$H NMR (300 MHz, DMSO-d$_6$) δ 10.63 (s, 1H), 8.15 (t, J=1.9 Hz, 1H), 7.99 (dt, J=7.7, 1.3 Hz, 1H), 7.95-7.86 (m, 4H), 7.83 (d, J=8.4 Hz, 1H), 7.73 (d, J=8.0 Hz, 1H), 7.69 (s, 1H), 7.66 (t, J=1.8 Hz, 1H), 7.60-7.55 (m, 1H), 7.51-7.46 (m, 2H), 7.43 (dd, J=8.7, 1.6 Hz, 1H), 7.28 (t, J=7.8 Hz, 1H), 7.21 (dt, J=7.8, 1.4 Hz, 1H), 6.11 (d, J=3.8 Hz, 1H), 5.85 (d, J=3.8 Hz, 1H).

Step-3: Preparation of 2-(3-Cyano-phenyl)-5-trifluoromethyl-2H-pyrazole-3-carboxylic acid {3-[(cyclopropylmethyl-amino)-naphthalen-2-yl-methyl]-phenyl}-amide (128d)

To a solution of 2-(3-Cyano-phenyl)-5-trifluoromethyl-2H-pyrazole-3-carboxylic acid [3-(hydroxy-naphthalen-2-yl-methyl)-phenyl]-amide (128c) (2.6 g, 5.07 mmol) in dichloromethane (50 mL) at 0° C. was added thionyl chloride (1.2 g, 10.14 mmol) and stirred at room temperature for 4 h. The reaction was concentrated in vacuum to dryness. The residue obtained was dissolved in acetonitrile (40 mL) and added cyclopropylmethanamine (5.41 g, 76.05 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum. The residue obtained was purified by flash column chromatography (silica gel 40 g, eluting 0-40% ethyl acetate in hexane) to afford 2-(3-Cyano-phenyl)-5-trifluoromethyl-2H-pyrazole-3-carboxylic acid {3-[(cyclopropylmethyl-amino)-naphthalen-2-yl-methyl]-phenyl}-amide (128d) (0.90 g, 31.39%) as brown liquid; $^1$H NMR (300 MHz, DMSO-d$_6$) δ 10.58 (s, 1H), 8.09 (t, J=1.9 Hz, 1H), 7.92 (dt, J=7.7, 1.3 Hz, 1H), 7.89-7.86 (m, 1H), 7.85-7.73 (m, 4H), 7.69-7.62 (m, 3H), 7.45 (dddd, J=19.3, 9.5, 5.3, 2.4 Hz, 4H), 7.24-7.16 (m, 2H), 4.94 (s, 1H), 2.36-2.17 (m, 2H), 0.99-0.83 (m, 1H), 0.38-0.24 (m, 2H), −0.01 (m, 2H).

Step-4: Preparation of [3-(5-{3-[(Cyclopropylmethyl-amino)-naphthalen-2-yl-methyl]-phenylcarbamoyl}-3-trifluoromethyl-pyrazol-1-yl)-benzyl]-carbamic acid tert-butyl ester (128e) and [(3-{[2-(3-Aminomethyl-phenyl)-5-trifluoromethyl-2H-pyrazole-3-carbonyl]-amino}-phenyl)-naphthalen-2-yl-methyl]-cyclopropylmethyl-carbamic acid tert-butyl ester (128f)

To a solution of 2-(3-Cyano-phenyl)-5-trifluoromethyl-2H-pyrazole-3-carboxylic acid {3-[(cyclopropylmethyl-amino)-naphthalen-2-yl-methyl]-phenyl}-amide (128d) (0.90 g, 1.59 mmol) in MeOH (20 mL) cooled with ice/water was added nickel(II) chloride hexahydrate (0.47 g, 1.99 mmol) and Boc anhydride (1.04 g, 4.77 mmol) followed by portionwise addition of sodium borohydride (0.36 g, 9.55 mmol) over a period of 15 min. The reaction mixture was stirred at room temperature for 2 hrs and quenched with N1-(2-aminoethyl)ethane-1,2-diamine (0.7 mL, 6.36 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL).

The combined extracts were washed with brine (25 mL), dried over MgSO$_4$ filtered and concentrated in vacuum. The residue obtained was purified by flash column chromatography (silica gel 24 g, eluting with 0-25% Ethyl acetate/hexane) to furnish 1. [3-(5-{3-[(Cyclopropylmethyl-amino)-naphthalen-2-yl-methyl]-phenylcarbamoyl}-3-trifluoromethyl-pyrazol-1-yl)-benzyl]-carbamic acid tert-butyl ester (128e) (0.42 g, 34.31%)$^1$H NMR (300 MHz, DMSO-d$_6$) δ 10.56 (s, 1H), 7.75 (dd, J=9.2, 3.2 Hz, 2H), 7.70 (d, J=3.4 Hz, 1H), 7.53 (d, J=8.4 Hz, 2H), 7.38-7.34 (m, 4H), 7.31 (s, 1H), 7.25-7.20 (m, 1H), 7.20-7.16 (m, 5H), 6.83 (d, J=7.8 Hz, 1H), 6.30 (s, 1H), 4.02 (d, J=6.2 Hz, 2H), 3.06-2.94 (m, 2H), 1.15 (s, 18H), 0.45 (s, 1H), 0.01 (d, J=8.6 Hz, 2H), −0.32 (s, 2H).

2. [(3-{[2-(3-Aminomethyl-phenyl)-5-trifluoromethyl-2H-pyrazole-3-carbonyl]-amino}-phenyl)-naphthalen-2-yl-methyl]-cyclopropylmethyl-carbamic acid tert-butyl ester (128f) (0.26 g, 24.42%); $^1$H NMR (300 MHz, DMSO-d$_6$) δ 10.62 (s, 1H), 7.87 (d, J=1.5 Hz, 1H), 7.81 (d, J=9.8 Hz, 2H), 7.77-7.72 (m, 3H), 7.62 (s, 1H), 7.49-7.38 (m, 6H), 7.34 (dd, J=8.9, 2.2 Hz, 2H), 7.30-7.25 (m, 2H), 7.19 (d, J=6.5 Hz, 2H), 4.93 (s, 1H), 4.12 (d, J=6.2 Hz, 2H), 2.24 (d, J=18.8 Hz, 2H), 1.29

(d, J=4.5 Hz, 9H), 0.99-0.79 (m, 1H), 0.41-0.26 (m, 2H), −0.01 (q, J=4.9 Hz, 2H).

Step-5: Preparation of 2-(3-Aminomethyl-phenyl)-5-trifluoromethyl-2H-pyrazole-3-carboxylic acid {3-[(cyclopropylmethyl-amino)-naphthalen-2-yl-methyl]-phenyl}-amide (128g)

A solution of [3-(5-{3-[(Cyclopropylmethyl-amino)-naphthalen-2-yl-methyl]-phenylcarbamoyl}-3-trifluoromethyl-pyrazol-1-yl)-benzyl]-carbamic acid tert-butyl ester (128e) (0.42 g, 0.55 mmol) and [(3-{[2-(3-Aminomethyl-phenyl)-5-trifluoromethyl-2H-pyrazole-3-carbonyl]-amino}-phenyl)-naphthalen-2-yl-methyl]-cyclopropylmethyl-carbamic acid tert-butyl ester (128g) (0.26 g, 0.39 mmol) were dissolved separately in methanol (10 mL) and added conc. HCl (0.5 mL). The reaction mixture was stirred at room temperature overnight and concentrated in vacuum to dryness. The residue was azeotroped with toluene (2×10 mL) and ethanol (10 mL), dried in vacuum pump to furnish a white solid residue. NMR of the residue in methanol and TLC shows same compound. The products were combined dried and purified by flash column chromatography (silica gel 12 g, eluting with 0-15% methanol in dichloromethane to furnish 2-(3-Aminomethyl-phenyl)-5-trifluoromethyl-2H-pyrazole-3-carboxylic acid {3-[(cyclopropylmethyl-amino)-naphthalen-2-yl-methyl]-phenyl}-amide (128g) (0.6 g, 95.42%) as white solid; $^1$H NMR (300 MHz, DMSO-$d_6$) δ 10.94 (s, 1H), 10.14 (s, 2H), 8.41 (s, 3H), 8.22 (d, J=1.7 Hz, 1H), 7.98 (d, J=8.6 Hz, 1H), 7.92 (dt, J=5.8, 3.2 Hz, 3H), 7.76 (dd, J=8.6, 1.8 Hz, 1H), 7.72 (d, J=1.9 Hz, 1H), 7.69-7.42 (m, 10H), 5.77 (d, J=3.4 Hz, 1H), 4.12 (d, J=5.6 Hz, 3H), 2.75 (d, J=12.4 Hz, 3H), 1.18 (dd, J=8.1, 3.8 Hz, 1H), 0.66-0.50 (m, 2H), 0.38-0.22 (m, 2H); $^{19}$F NMR (282 MHz, DMSO-$d_6$) δ −60.80; MS (ES+) 570.3 (M+1); (ES−) 604.3 (M+Cl); Analysis calculated for $C_{33}H_{30}F_3N_5O.2.05HCl.2H_2O$: C, 58.25; H, 5.34; Cl, 10.68; N, 10.29; Found: C, 58.14; H, 5.58; Cl, 11.02; N, 9.90.

Scheme 129

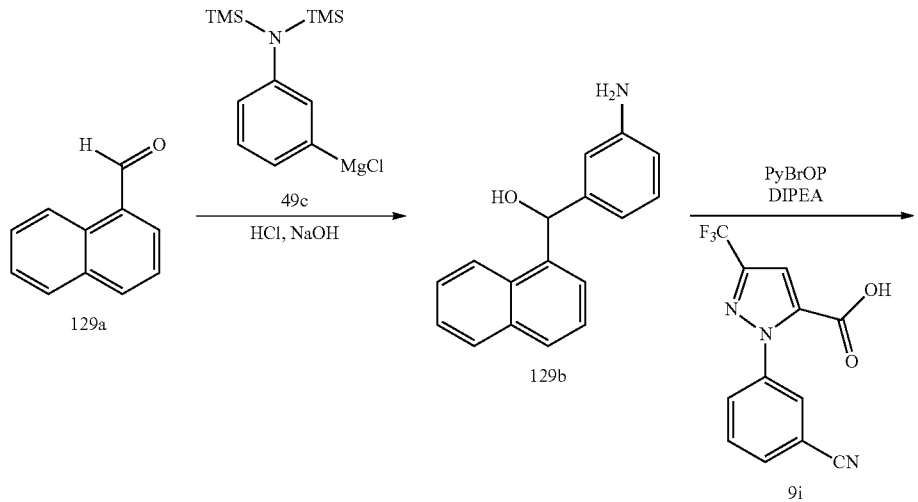

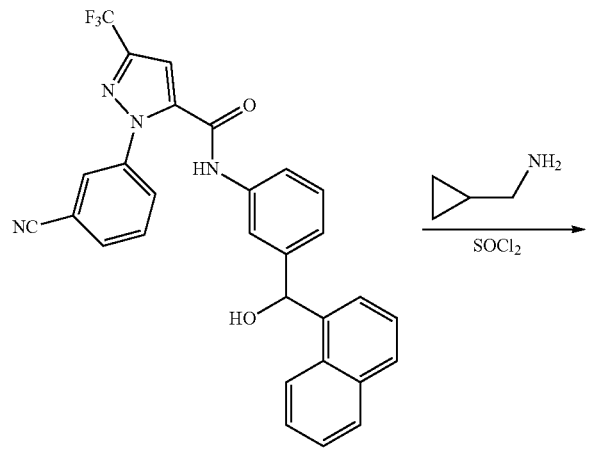

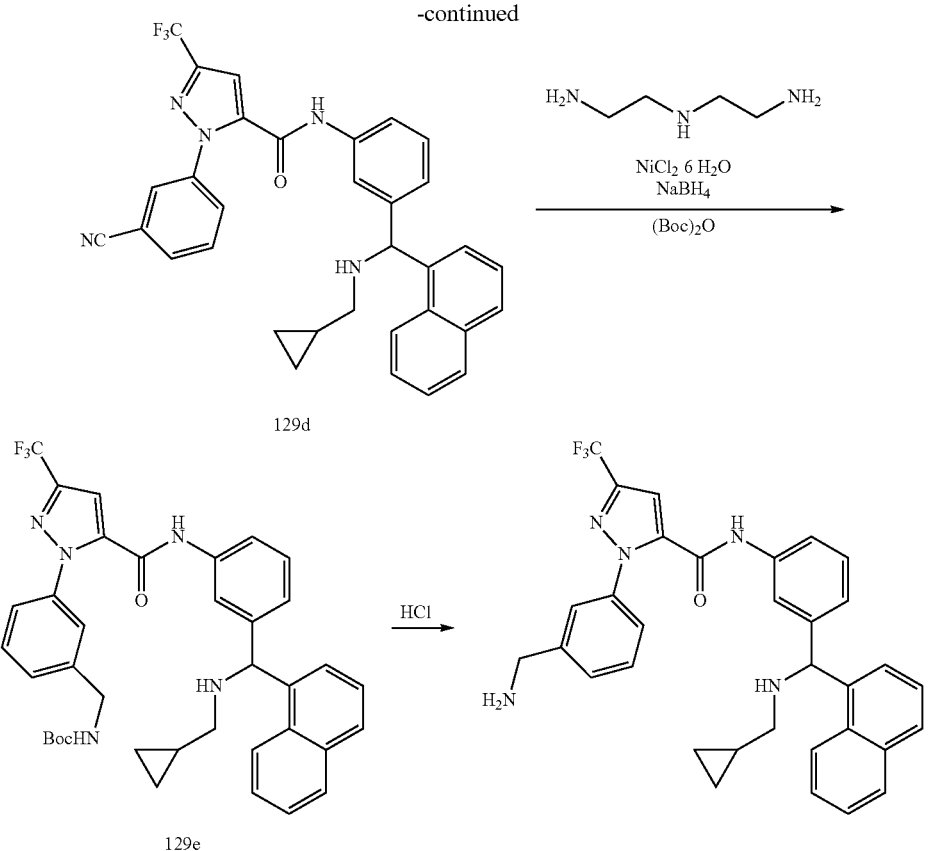

Preparation of 1-(3-(aminomethyl)phenyl)-N-(3-((cyclopropylmethylamino)(naphthalen-1-yl)methyl)phenyl)-3-(trifluoromethyl)-1H-pyrazole-5-carboxamide (129f)

Step-1: Preparation of (3-Amino-phenyl)-naphthalen-1-yl-methanol (129b)

To a stirred solution of naphthalene-1-carbaldehyde (129a) (1.2 g, 10 mmol) in tetrahydrofuran (5 mL) was added (3-(bis(trimethylsilyl)amino)phenyl)magnesium chloride (49c) (12.0 mL, 12.0 mmol) at 0° C. The reaction was stirred for 14 h at room temperature, quenched by adding 2 N HCl (12.50 mL) and stirred for 6 h. The reaction mixture was treated with 2 N NaOH (15 mL) and extracted with ethyl acetate (2×50 mL). The organic layers were combined washed with sat. NH$_4$Cl (50 mL), dried over anhydrous MgSO$_4$, filtered, evaporated to dryness. The crude residue was purified by flash column chromatography (silica gel 40 g, eluting with 0-100% ethyl acetate in hexane) to furnish (3-Amino-phenyl)-naphthalen-1-yl-methanol (129b) (2.45 g, 98.27%) as a light brown sticky liquid; $^1$H NMR (300 MHz, DMSO-d$_6$) δ 8.16-8.06 (m, 1H), 7.93-7.86 (m, 1H), 7.82 (d, J=8.1 Hz, 1H), 7.71-7.66 (m, 1H), 7.51 (dd, J=8.2, 7.1 Hz, 1H), 7.48-7.39 (m, 2H), 6.91 (t, J=7.9 Hz, 1H), 6.63-6.49 (m, 2H), 6.38 (ddd, J=7.9, 2.2, 1.1 Hz, 1H), 6.19 (d, J=4.4 Hz, 1H), 5.85 (d, J=4.4 Hz, 1H), 4.96 (s, 2H).

Step-2: Preparation of 2-(3-Cyano-phenyl)-5-trifluoromethyl-2H-pyrazole-3-carboxylicacid [3-(hydroxy-naphthalen-1-yl-methyl)-phenyl]-amide (129c)

To a solution of 1-(3-cyanophenyl)-3-(trifluoromethyl)-1H-pyrazole-5-carboxylic acid (9i) (2.47 g, 8.8 mmol) in DMF (40 mL) was added (3-Amino-phenyl)-naphthalen-1-yl-methanol (129b) (2.0 g, 8.8 mmol), N-ethyl-N-isopropylpropan-2-amine (12.26 mL, 70.42 mmol) and bromo-tris-pyrrolidino phosphoniumhexafluorophosphate (PyBrOP, 4.1 g, 8.8 mmol) at room temperature. The reaction mixture was stirred at room temperature for 42 h under nitrogen atmosphere. The reaction was diluted with ethyl acetate (350 mL) washed with water (2×150 mL), brine (120 mL), dried, filtered, and evaporated to dryness. The residue obtained was purified by flash column chromatography [silica gel 120 g, eluting with ethyl acetate in hexanes from 0-30%] to furnish 2-(3-Cyano-phenyl)-5-trifluoromethyl-2H-pyrazole-3-carboxylicacid [3-(hydroxy-naphthalen-1-yl-methyl)-phenyl]-amide (129c) (1.0 g, 22.17%) as a brown sticky liquid; $^1$H NMR (300 MHz, DMSO-d$_6$) δ 10.61 (s, 1H), 8.17-8.08 (m, 2H), 7.99 (dt, J=7.8, 1.3 Hz, 1H), 7.94-7.82 (m, 3H), 7.73 (d, J=7.9 Hz, 1H), 7.70-7.50 (m, 5H), 7.50-7.39 (m, 2H), 7.26 (t, J=7.8 Hz, 1H), 7.21-7.12 (m, 1H), 6.34 (d, J=4.3 Hz, 1H), 6.13 (d, J=4.3 Hz, 1H).

Step-3: Preparation of 2-(3-Cyano-phenyl)-5-trifluoromethyl-2H-pyrazole-3-carboxylic acid {3-[(cyclopropylmethyl-amino)-naphthalen-1-yl-methyl]-phenyl}-amide (129d)

To a solution of 2-(3-Cyano-phenyl)-5-trifluoromethyl-2H-pyrazole-3-carboxylicacid [3-(hydroxy-naphthalen-1-yl-methyl)-phenyl]-amide (129c) (1.0 g, 1.95 mmol) in dichloromethane (50 mL) at 0° C. was added thionyl chloride (0.28 mL, 3.902 mmol) and stirred at room temperature for 4 h. The reaction mixture was concentrated in vacuum to dryness. The residue obtained was dissolved in acetonitrile (40 mL) and added cyclopropylmethanamine (2.053 g, 29.265 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum. The residue obtained was purified by flash column chromatography (silica gel 40 g, eluting 0-40% ethyl acetate in hexane) to afford 2-(3-Cyano-phenyl)-5-trifluoromethyl-2H-pyrazole-3-carboxylic acid {3-[(cyclopropylmethyl-amino)-naphthalen-1-yl-methyl]-phenyl}-amide (129d) (0.60 g, 54.40%) as brown liquid; $^1$H NMR (300 MHz, DMSO-d$_6$) δ 10.57 (s, 1H), 8.29-8.17 (m, 1H), 8.12-8.06 (m, 1H), 7.94 (dt, J=7.8, 1.3 Hz, 1H), 7.89-7.81 (m, 2H), 7.78-7.56 (m, 5H), 7.55-7.40 (m, 4H), 7.27-7.17 (m, 2H), 5.58 (s, 1H), 2.35 (d, J=6.7 Hz, 2H), 1.02-0.87 (m, 1H), 0.44-0.24 (m, 2H), 0.11--0.07 (m, 2H).

Step-4: Preparation of [(3-{[2-(3-Aminomethyl-phenyl)-5-trifluoromethyl-2H-pyrazole-3-carbonyl]-amino}-phenyl)-naphthalen-1-yl-methyl]-cyclopropylmethyl-carbamic Acid Tert-Butyl Ester (129e)

To a solution of 2-(3-Cyano-phenyl)-5-trifluoromethyl-2H-pyrazole-3-carboxylic acid {3-[(cyclopropylmethyl-amino)-naphthalen-1-yl-methyl]-phenyl}-amide (129d) (0.60 g, 1.04 mmol) in MeOH (12 mL) cooled with ice/water was added nickel(II) chloride hexahydrate (0.29 g, 1.24 mmol) and Boc anhydride (0.713 g, 3.11 mmol) followed by portionwise addition of sodium borohydride (0.23 g, 6.21 mmol) over a period of 15 min. The reaction mixture was stirred at room temperature for 2 hrs and quenched with N$^1$-(2-aminoethyl)ethane-1,2-diamine (0.28 mL, 2.59 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over MgSO$_4$ filtered and concentrated in vacuum. The residue obtained was purified by flash column chromatography (silica gel 24 g, eluting with 0-25% Ethyl acetate/hexane) to furnish [3-(5-{3-[(Cyclopropylmethyl-amino)-naphthalen-1-yl-methyl]-phenyl-carbamoyl}-3-trifluoromethyl-pyrazol-1-yl)-benzyl]-carbamic acid tert-butyl ester (129e) (0.24 g, 34.46%).

Step-5: Preparation of 2-(3-Aminomethyl-phenyl)-5-trifluoromethyl-2H-pyrazole-3-carboxylic acid {3-[(cyclopropylmethyl-amino)-naphthalen-1-yl-methyl]-phenyl}-amide (129f)

To a solution of [3-(5-{3-[(Cyclopropylmethyl-amino)-naphthalen-1-yl-methyl]-phenylcarbamoyl}-3-trifluoromethyl-pyrazol-1-yl)-benzyl]-carbamic acid tert-butyl ester (129e) (0.240 g, 0.358 mmol) in methanol (10 mL) and added conc. HCl (0.5 mL). The reaction mixture was stirred at room temperature overnight and concentrated in vacuum to dryness. The residue was azeotroped with toluene (2×10 mL) and ethanol (10 mL), dried in vacuum pump to furnish a white solid residue. The residue was purified by flash column chromatography (silica gel 12 g, eluting with 0-15% methanol in dichloromethane to furnish 2-(3-Aminomethyl-phenyl)-5-trifluoromethyl-2H-pyrazole-3-carboxylic acid {3-[(cyclopropylmethyl-amino)-naphthalen-1-yl-methyl]-phenyl}-amide (129f) (0.08 g, 39.28%) free base as Light cream solid; $^1$H NMR (300 MHz, DMSO-d$_6$) δ 10.93 (s, 1H), 10.25 (s, 1H), 10.00 (s, 1H), 8.46 (s, 3H), 8.20 (d, J=7.8 Hz, 1H), 8.01 (d, J=1.8 Hz, 1H), 7.88 (t, J=1.9 Hz, 1H), 7.73-7.47 (m, 13H), 7.43-7.38 (m, 1H), 6.44 (t, J=6.1 Hz, 1H), 4.11 (q, J=5.6 Hz, 2H), 3.03-2.74 (m, 2H), 1.20-1.14 (m, 1H), 0.55 (dd, J=7.8, 3.4 Hz, 2H), 0.39-0.20 (m, 2H); $^{19}$F NMR (282 MHz, DMSO-d$_6$) δ -60.79; MS (ES+) 570.3 (M+1); (ES-) 604.3 (M+Cl); 1-(3-(aminomethyl)phenyl)-N-(3-((cyclopropylmethylamino)(naphthalen-1-yl)methyl)phenyl)-3-(trifluoromethyl)-1H-pyrazole-5-carboxamide (129f) (0.28 g, 0.492 mmol) from above was purified by flash column chromatography (silica gel 12 g, eluting with 0-100% methanol in chloroform) and converted to hydrochloride salt by dissolving the product obtained in methanol (5 mL) and treating it with 10 equivalents of conc HCl. The solution obtained was concentrated in vacuum to dryness dried in vacuum to furnish 1-(3-(aminomethyl)phenyl)-N-(3-((cyclopropylmethylamino)(naphthalen-1-yl)methyl)phenyl)-3-(trifluoromethyl)-1H-pyrazole-5-carboxamide (129f) hydrochloride as a pale yellow solid. $^1$H NMR (300 MHz, DMSO-d$_6$) δ 10.99 (s, 1H), 10.38 (s, 1H), 10.10 (d, J=10.5 Hz, 1H), 8.56 (s, 4H), 8.30-8.20 (m, 2H), 8.00 (dd, J=7.0, 3.2 Hz, 2H), 7.91 (t, J=1.9 Hz, 1H), 7.75-7.62 (m, 7H), 7.61-7.46 (m, 4H), 7.41 (t, J=7.9 Hz, 1H), 6.44 (t, J=6.2 Hz, 1H), 4.11 (q, J=5.6 Hz, 2H), 2.97-2.68 (m, 3H), 1.30-1.17 (m, 1H), 0.55 (dd, J=7.9, 3.6 Hz, 2H), 0.41-0.21 (m, 2H); $^{19}$F NMR (282 MHz, DMSO) δ -60.78; MS (ES+) 570.3 (M+1); (ES-) 604.3 (M+Cl); Analysis calculated for C$_{33}$H$_{30}$F$_3$N$_5$O.2HCl.2.25H$_2$O: C, 58.02; H, 5.39; Cl, 10.38; N, 10.25; Found; C, 57.93; H, 5.30; Cl, 10.28; N, 10.01.

Scheme 130

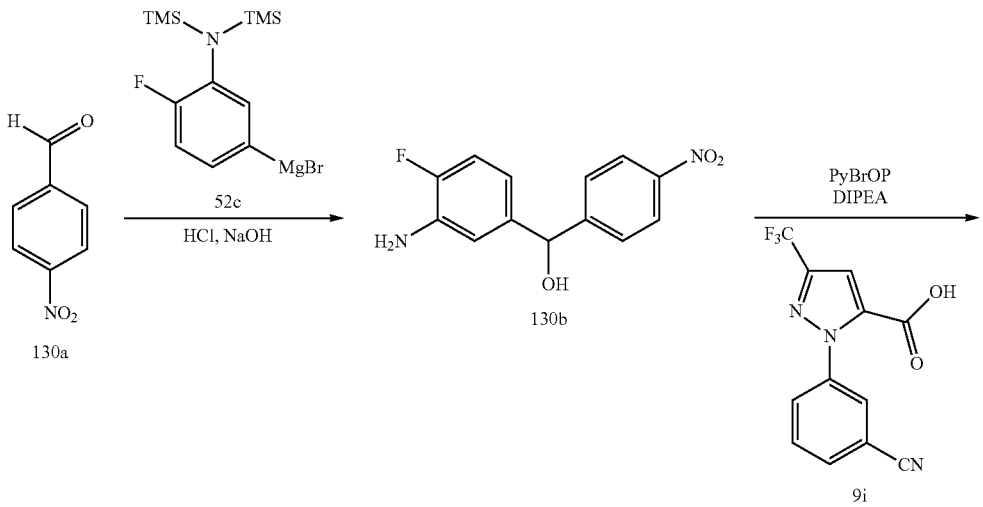

-continued

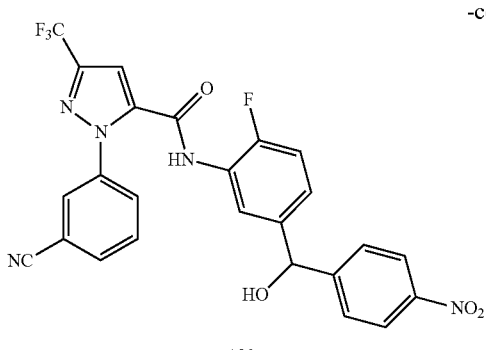

130c

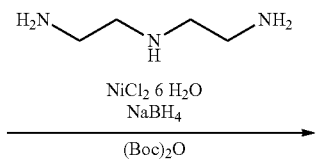

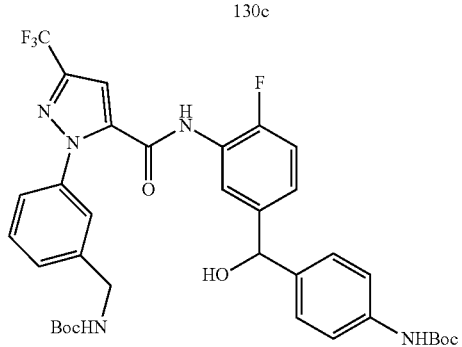

130d

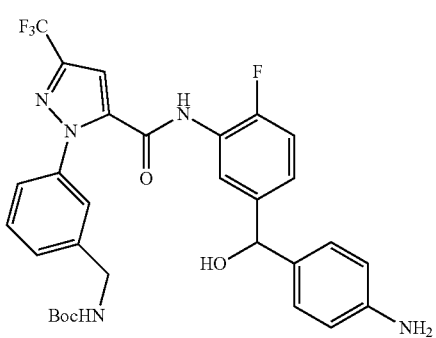

130e

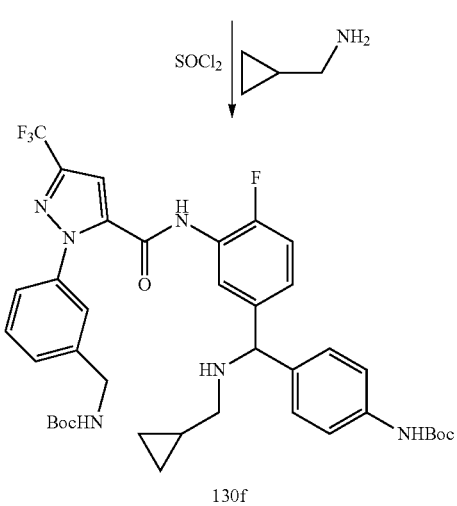

130f

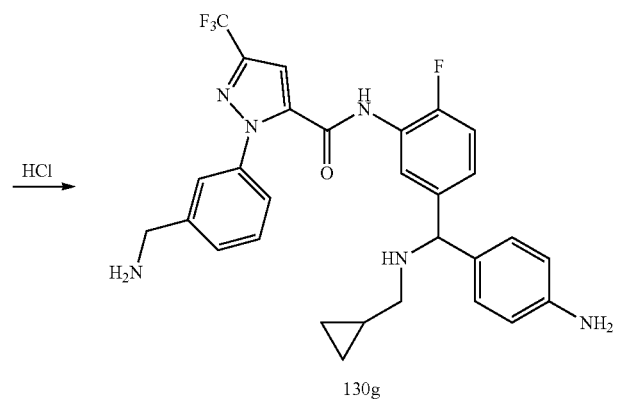

130g

Preparation of 1-(3-(aminomethyl)phenyl)-N-(5-((4-aminophenyl)(cyclopropylmethylamino)methyl)-2-fluorophenyl)-3-(trifluoromethyl)-1H-pyrazole-5-carboxamide (130g)

Step-1: Preparation of (3-amino-4-fluorophenyl)(4-nitrophenyl)methanol (130b)

To a stirred solution of 4-nitrobenzaldehyde (130a) (1.813 g, 12 mmol) in tetrahydrofuran (15 mL) cooled to 0° C. was added (3-(bis(trimethylsilyl)amino)-4-fluorophenyl)magnesium bromide (52c) (18.00 mL, 18.00 mmol) and stirred at room temperature for 3 h. Reaction was quenched with hydrochloric acid (10 mL, 2N) and stirred for 30 mins. To the reaction was basified with sodium bicarbonate solution and extracted with ethyl acetate (2×250 mL). The organic layers were combined washed with water (2×50 mL), brine (50 mL) dried and concentrated in vacuum. The crude residue was purified by flash column chromatography (silica gel 80 g, eluting with ethyl acetate in hexanes 0-100%) to afford (3-amino-4-fluorophenyl)(4-nitrophenyl)methanol (130b) (1.71 g, 6.52 mmol, 54.3% yield) as an oil; $^1$HNMR (300 MHz, DMSO-$d_6$) δ 8.22-8.14 (m, 2H), 7.65-7.58 (m, 2H), 6.90 (dd, J=11.5, 8.2 Hz, 1H), 6.76 (dd, J=9.0, 2.2 Hz, 1H), 6.12 (d, J=3.9 Hz, 1H, $D_2O$ exchangeable), 5.69 (d, J=3.8 Hz, 1H), 5.13 (s, 2H, $D_2O$ exchangeable). MS (ES−) 261.1 (M−1).

Step-2: Preparation of 1-(3-Cyanophenyl)-N-(2-fluoro-5-(hydroxy(4-nitrophenyl)methyl)phenyl)-3-(trifluoromethyl)-1H-pyrazole-5-carboxamide (130c)

To a solution of 1-(3-cyanophenyl)-3-(trifluoromethyl)-1H-pyrazole-5-carboxylic acid (9i) (2.011 g, 7.15 mmol) in DMF (20 mL) was (3-amino-4-fluorophenyl)(4-nitrophenyl)methanol (130b) (1.705 g, 6.50 mmol), N-ethyl-N-isopropylpropan-2-amine (5.66 mL, 32.5 mmol) and bromo-tris-pyrrolidino phosphoniumhexafluorophosphate (PyBrOP, 3.64 g, 7.80 mmol) at room temperature. The reaction mixture was stirred at room temperature for 37 h under nitrogen atmosphere. The reaction was diluted with water (75 mL) and extracted with ethyl acetate (2×75 mL). The organic layers were combined, washed with brine (50 mL), dried, filtered, and evaporated in vacuum to dryness. The residue obtained was purified by flash column chromatography (silica gel 40 g, eluting with 0-100% ethyl acetate in hexanes) to furnish 1-(3-cyanophenyl)-N-(2-fluoro-5-(hydroxy(4-nitrophenyl)methyl)phenyl)-3-(trifluoromethyl)-1H-pyrazole-5-carboxamide (130c) (2.081 g, 3.96 mmol, 60.9% yield) as a brown semisolid; $^1$H NMR (300 MHz, DMSO-$d_6$) δ 10.56 (s, 1H), 8.19 (dd, J=8.9, 2.5 Hz, 2H), 8.12 (t, J=1.8 Hz, 1H), 8.02-7.97 (m, 1H), 7.93-7.87 (m, 1H), 7.78-7.69 (m, 2H), 7.68-7.63 (m, 2H), 7.63-7.53 (m, 1H), 7.35-7.20 (m, 2H), 6.36 (d, J=4.0 Hz, 1H), 5.88 (d, J=3.9 Hz, 1H); $^{19}$F NMR (282 MHz, DMSO-$d_6$) δ −60.98, −122.64; MS (ES+) 548.2 (M+Na); (ES−) 524.2 (M−1).

Step-3: Preparation of tert-butyl 3-(5-((5-((4-tertbutyloxycarbonylaminophenyl)(hydroxy)methyl)-2-fluorophenyl)carbamoyl)-3-(trifluoromethyl)-1H-pyrazol-1-yl)benzylcarbamate (130d)

A solution of 1-(3-cyanophenyl)-N-(2-fluoro-5-(hydroxy(4-nitrophenyl)methyl)phenyl)-3-(trifluoromethyl)-1H-pyrazole-5-carboxamide (130c) (2.119 g, 4.03 mmol) in MeOH (60 mL) cooled with ice/water was added di-tert-butyl dicarbonate (3.56 g, 16.13 mmol), nickel(II) chloride hexahydrate (0.516 g, 2.170 mmol) followed by portionwise addition of sodium borohydride (1.557 g, 40.3 mmol) slowly over 5 min. the reaction was stirred at room temperature for 3 h, quenched with N1-(2-aminoethyl)ethane-1,2-diamine (1.995 mL, 18.28 mmol) and stirred for 30 mins. Reaction was concentrated to dryness. The residue was diluted with water (200 mL). The solid separated was collected by filtration and purified by flash column chromatography [silica gel 40 g, eluting with hexanes/ethyl acetate (1:0 to 2:1)] to afford tert-butyl 3-(5-((5-((4-tertbutyloxycarbonylaminophenyl)(hydroxy)methyl)-2-fluorophenyl)carbamoyl)-3-(trifluoromethyl)-1H-pyrazol-1-yl)benzylcarbamate (130d) (0.815 g, 1.165 mmol, 28.9% yield) as a colorless foam; MS (ES+) 722.4 (M+Na), (ES−) 698.3 (M−1) and tert-butyl 3-(5-(5-((4-aminophenyl)(hydroxy)methyl)-2-fluorophenylcarbamoyl)-3-(trifluoromethyl)-1H-pyrazol-1-yl)benzylcarbamate (130e) (0.35 g, 0.584 mmol, 14.47% yield) as a colorless foam; MS (ES+) 622.3 (M+Na), (ES−) 598.3 (M−1).

Step-4: Preparation of tert-butyl 3-(5-((5-((4-tertbutoxycarbonylaminophenyl)((cyclopropylmethyl)amino)methyl)-2-fluorophenyl)carbamoyl)-3-(trifluoromethyl)-1H-pyrazol-1-yl)benzylcarbamate (130f)

To a solution of 3-(5-((5-((4-tertbutyloxycarbonylaminophenyl)(hydroxy)methyl)-2-fluorophenyl)carbamoyl)-3-(trifluoromethyl)-1H-pyrazol-1-yl)benzylcarbamate (130d) (0.798 g, 1.141 mmol) in dichloromethane (25 mL) at 0° C. added thionyl chloride (0.178 mL, 2.435 mmol) and stirred at room temperature for 2 h. The reaction was treated with triethyl amine (1.7 mL, 12.19 mmol) stirred at room temperature for 1 h. The reaction was diluted with cyclopropylmethanamine (2.084 mL, 24.32 mmol) and concentrated to remove most of dichloromethane followed by addition of acetonitrile (25.00 mL) and stirring at reflux for 16 h. Reaction was concentrated to dryness treated with chloroform (240 mL), washed with water (100 mL), dried over MgSO$_4$ followed by filtration and concentration. Reaction was purified by flash column chromatography (silica gel, eluting with methanol in chloroform 0 to 20%) to afford tert-butyl 3-(5-((5-((4-tertbutoxycarbonylaminophenyl)((cyclopropylmethyl)amino)methyl)-2-fluorophenyl)carbamoyl)-3-(trifluoromethyl)-1H-pyrazol-1-yl)benzylcarbamate (130f) (297 mg, 0.395 mmol, 34.6% yield) as a yellow oil; MS (ES+) 753.5 (M+1), (ES−) 751.3 (M−1).

Step-5: Preparation of 1-(3-(aminomethyl)phenyl)-N-(5-((4-aminophenyl)(cyclopropylmethylamino)methyl)-2-fluorophenyl)-3-(trifluoromethyl)-1H-pyrazole-5-carboxamide (130g)

To a solution of afford tert-butyl 3-(5-((5-((4-tertbutoxycarbonylaminophenyl)((cyclopropylmethyl)amino)methyl)-2-fluorophenyl)carbamoyl)-3-(trifluoromethyl)-1H-pyrazol-1-yl)benzylcarbamate (130f) (290 mg, 0.385 mmol) in methanol (5 mL) was added hydrochloric acid (1.170 mL, 38.5 mmol) and stirred at room temperature over night. The reaction mixture was concentrated in vacuum to dryness. The residue was dried in a vacuum pump and purified by flash column chromatography (silica gel 12 g, eluting with 0-100% CMA 80 in chloroform) to afford compound 1-(3-(aminomethyl)phenyl)-N-(5-((4-aminophenyl)(cyclopropylmethylamino)methyl)-2-fluorophenyl)-3-(trifluoromethyl)-1H-pyrazole-5-carboxamide (130g) (60 mg, 0.109 mmol, 28.2% yield) free base as a white solid. To a stirred solution of free base of 1-(3-(aminomethyl)phenyl)-N-(5-((4-aminophenyl)(cyclopropylmethylamino)methyl)-2-fluorophenyl)-3-(trifluoromethyl)-1H-pyrazole-5-carboxamide (130g) (60 mg, 0.109 mmol) in methanol (5 mL) was added conc. hydrochloric acid (0.045 mL, 0.543 mmol) and concentrated to remove excess solvents and dried under vacuum to afford 1-(3-(aminomethyl)phenyl)-N-(5-((4-aminophenyl)(cyclopropylmethylamino)methyl)-2-fluorophenyl)-3-(trifluoromethyl)-1H-pyrazole-5-carboxamide 130 g (67.5 mg, 0.108 mmol, 99% yield) hydrochloride salt as a white solid; $^1$H NMR (300 MHz, DMSO-$d_6$) δ 10.85 (s, 1H, D$_2$O exchangeable), 10.28 (s, 2H, D$_2$O exchangeable), 8.54 (s, 3H, D$_2$O exchangeable), 7.93 (dd, J=7.2, 2.3 Hz, 1H), 7.79-7.68 (m, 5H), 7.65 (dt, J=7.3, 1.8 Hz, 1H), 7.60-7.51 (m, 2H), 7.44-7.34 (m, 1H), 7.22 (d, J=8.1 Hz, 2H), 5.71-5.58 (m, 1H), 4.12 (q, J=5.7 Hz, 2H), 2.70 (d, J=9.0 Hz, 2H), 1.17 (ddt, J=12.8, 8.1, 4.1 Hz, 1H), 0.59-0.50 (m, 2H), 0.31 (td, J=5.8, 4.2 Hz, 2H).

Scheme 131

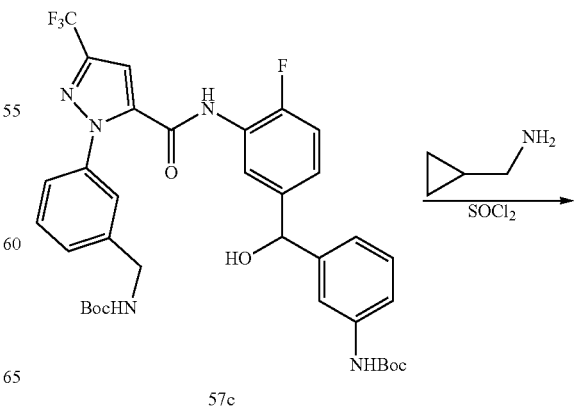

57c

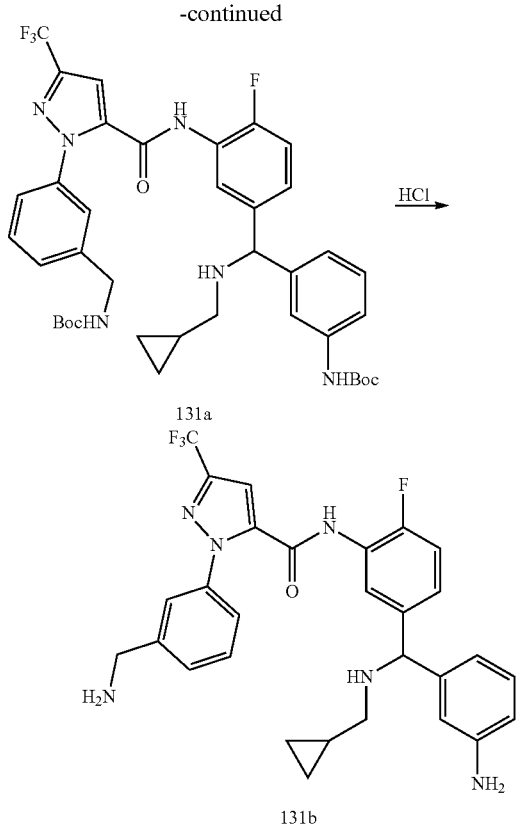

131a

131b

Preparation of 1-(3-(aminomethyl)phenyl)-N-(5-((3-aminophenyl)(cyclopropylmethylamino)methyl)-2-fluorophenyl)-3-(trifluoromethyl)-1H-pyrazole-5-carboxamide (131b)

Step-1: Preparation of tert-butyl 3-(5-((5-((3-tert-butyloxycarbonylaminophenyl)((cyclopropylmethyl)amino)methyl)-2-fluorophenyl)carbamoyl)-3-(trifluoromethyl)-1H-pyrazol-1-yl)benzylcarbamate (131a)

To a solution of tert-butyl 3-(5-((5-((3-tertbutyloxycarbonylaminophenyl)(hydroxy)methyl)-2-fluorophenyl)carbamoyl)-3-(trifluoromethyl)-1H-pyrazol-1-yl)benzylcarbamate (57c) (0.582 g, 0.832 mmol) in dichloromethane (20 mL) at 0° C. was added thionyl chloride (0.130 mL, 1.776 mmol) and stirred at room temperature for 2 h. The reaction was treated with triethyl amine (0.771 mL, 5.53 mmol) and stirred at room temperature for 1 h. The reaction was treated with cyclopropylmethanamine (1.520 mL, 17.73 mmol) and concentrated in vacuum to remove most of dichloromethane followed by addition of acetonitrile (20.00 mL) and stirring at reflux for 16 h. Reaction was concentrated in vacuum to dryness dissolved in chloroform (300 mL), washed with water (100 mL), dried over MgSO$_4$ followed by filtration and concentration. Reaction was purified by flash column chromatography (silica gel 25 g, eluting with methanol in chloroform 0 to 20%) to afford tert-butyl 3-(5-((5-((3-tert-butyloxycarbonylaminophenyl)((cyclopropylmethyl)amino)methyl)-2-fluorophenyl)carbamoyl)-3-(trifluoromethyl)-1H-pyrazol-1-yl)benzylcarbamate (131a) (115 mg, 0.153 mmol, 18.37% yield) as a white foam; MS (ES+) 753.5 (M+1); (ES−) 751.4 (M−1).

Step-2: Preparation of 1-(3-(aminomethyl)phenyl)-N-(5-((3-aminophenyl)(cyclopropylmethylamino)methyl)-2-fluorophenyl)-3-(trifluoromethyl)-1H-pyrazole-5-carboxamide (131b)

To a solution of tert-butyl 3-(5-((5-((3-tert-butyloxycarbonylaminophenyl)((cyclopropylmethyl)amino)methyl)-2-fluorophenyl)carbamoyl)-3-(trifluoromethyl)-1H-pyrazol-1-yl)benzylcarbamate (131a) (115 mg, 0.153 mmol) in methanol (5 mL) was added hydrochloric acid (0.464 mL, 15.27 mmol) and stirred at room temperature overnight. The reaction mixture was concentrated in vacuum to dryness. The residue was dried in vacuum pump and purified by flash column chromatography (silica gel 12 g, eluting with 0-100% CMA 80 in chloroform) to afford 1-(3-(aminomethyl)phenyl)-N-(5-((3-aminophenyl)(cyclopropylmethylamino)methyl)-2-fluorophenyl)-3-(trifluoromethyl)-1H-pyrazole-5-carboxamide (131b) as a free base. To a stirred solution of free base of compound 131b (80 mg, 0.145 mmol) in methanol (5 mL) was added conc. hydrochloric acid (0.060 mL, 0.724 mmol) stirred for 30 mins and concentrated in vacuum to dryness to afford pure 1-(3-(aminomethyl)phenyl)-N-(5-((3-aminophenyl)(cyclopropylmethylamino)methyl)-2-fluorophenyl)-3-(trifluoromethyl)-1H-pyrazole-5-carboxamide (131b) (19 mg, 20.98% yield) hydrochloride salt as a white solid; $^1$H NMR (300 MHz, DMSO-d$_6$) δ 10.87 (s, 1H, D$_2$O exchangeable), 10.30 (s, 2H, D$_2$O exchangeable), 8.55 (s, 3H, D$_2$O exchangeable), 7.91 (dd, J=7.4, 2.3 Hz, 1H), 7.79-7.70 (m, 3H), 7.70-7.61 (m, 2H), 7.60-7.48 (m, 2H), 7.46 (d, J=8.5 Hz, 1H), 7.43-7.34 (m, 2H), 7.18 (d, J=7.9 Hz, 1H), 5.81-5.56 (m, 1H), 4.11 (d, J=5.6 Hz, 2H), 2.77-2.66 (m, 2H), 1.17 (td, J=9.7, 7.6, 4.3 Hz, 1H), 0.60-0.51 (m, 2H), 0.31 (dt, J=6.6, 4.6 Hz, 2H); MS (ES+) 553.3 (M+1), 575.3 (M+23), (ES−) 587.3 (M+35).

Scheme 132

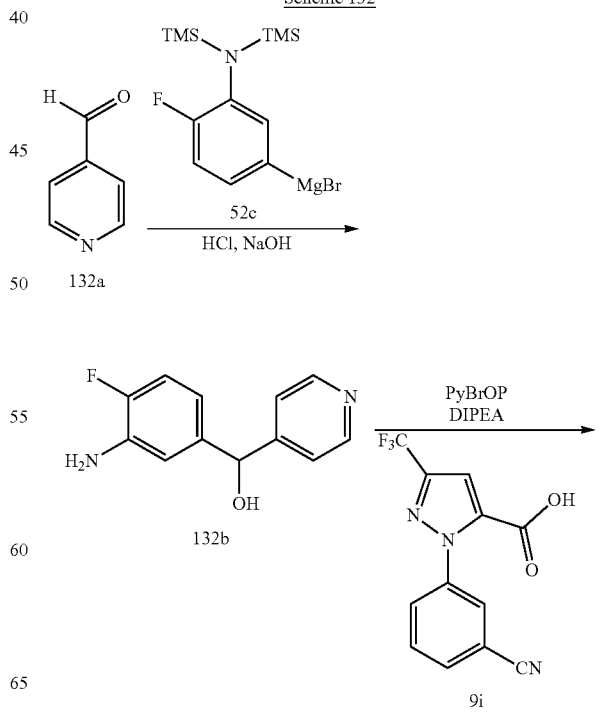

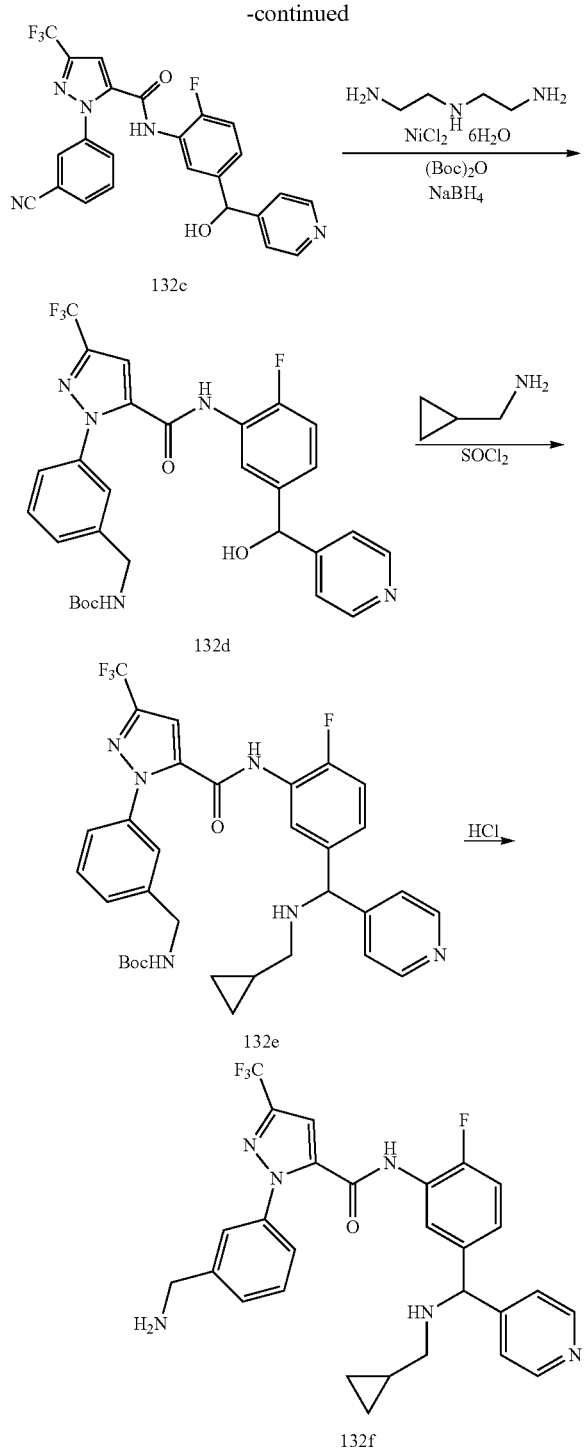

Preparation of 1-(3-(aminomethyl)phenyl)-N-(5-((((cyclopropylmethyl)amino)(pyridin-4-yl)methyl)-2-fluorophenyl)-3-(trifluoromethyl)-1H-pyrazole-5-carboxamide (132f)

Step-1: Preparation of (3-amino-4-fluorophenyl)(pyridin-4-yl)methanol (132b)

To a stirred solution of isonicotinaldehyde (132a) (1.285 g, 12 mmol) in Tetrahydrofuran (15 mL) at 0° C. was added (3-(bis(trimethylsilyl)amino)-4-fluorophenyl)magnesium bromide (52c) (6.46 g, 18.0 mmol) and stirred at room temperature for 3 h. The reaction was quenched with hydrochloric acid (10 mL, 2N) and stirred for 30 mins. The reaction was basified with sodium bicarbonate solution and extracted with ethyl acetate (2×250 mL). The combined organic layers was washed with water (2×50 mL), brine (50 mL) dried and concentrated in vacuum. The crude residue was purified by flash column chromatography (silica gel 80 g, eluting with CMA 80 in chloroform) to afford (3-amino-4-fluorophenyl)(pyridin-4-yl)methanol (132b) (2.1 g, 80% yield) as a pale yellow solid; $^1$HNMR (300 MHz, DMSO-d$_6$) δ 8.58-8.53 (m, 1H), 8.42 (dd, J=4.8, 1.7 Hz, 1H), 7.71-7.64 (m, 1H), 7.32 (ddd, J=7.8, 4.8, 0.9 Hz, 1H), 6.90 (dd, J=11.5, 8.3 Hz, 1H), 6.78 (dd, J=9.0, 2.2 Hz, 1H), 6.53 (ddd, J=8.3, 4.4, 2.2 Hz, 1H), 5.97 (d, J=3.9 Hz, 1H, D$_2$O exchangeable), 5.62 (d, J=3.7 Hz, 1H), 5.12 (s, 2H, D$_2$O exchangeable); Mass spec (ES+) 219.2, 241.1 (M+23), (ES−) 217.1 (M−1).

Step-2: Preparation of 1-(3-Cyanophenyl)-N-(2-fluoro-5-(hydroxy(pyridin-4-yl)methyl)phenyl)-3-(trifluoromethyl)-1H-pyrazole-5-carboxamide (132c)

To a solution of 1-(3-cyanophenyl)-3-(trifluoromethyl)-1H-pyrazole-5-carboxylic acid (9i) (2.88 g, 10.25 mmol) in DMF (20 mL) was added (3-amino-4-fluorophenyl)(pyridin-4-yl)methanol (132b) (2.034 g, 9.32 mmol), N-ethyl-N-isopropylpropan-2-amine (8.12 mL, 46.6 mmol) and bromotris-pyrrolidino phosphoniumhexafluorophosphate(PyBrOP, 5.21 g, 11.18 mmol) at room temperature. The reaction mixture was stirred at room temperature for 37 h under nitrogen atmosphere. The reaction was diluted with water (75 mL) and extracted with ethyl acetate (2×75 mL). The organic layers were combined, washed with brine (50 mL), dried, filtered, and evaporated in vacuum to dryness. The residue obtained was purified by flash column chromatography (silica gel 40 g, eluting with 0-100% ethyl acetate in hexanes) to furnish 1-(3-cyanophenyl)-N-(2-fluoro-5-(hydroxy(pyridin-4-yl)methyl)phenyl)-3-(trifluoromethyl)-1H-pyrazole-5-carboxamide (132c) (2.081 g, 4.32 mmol, 46.4% yield) as a yellow oil; $^1$H NMR (300 MHz, DMSO-d$_6$) δ 10.57 (s, 1H), 8.51-8.47 (m, 2H), 8.15-8.10 (m, 1H), 8.00 (dt, J=7.8, 1.3 Hz, 1H), 7.93-7.87 (m, 1H), 7.76-7.69 (m, 2H), 7.55 (dd, J=7.4, 2.1 Hz, 1H), 7.38-7.35 (m, 2H), 7.34-7.21 (m, 2H), 6.27 (d, J=4.0 Hz, 1H), 5.73 (d, J=4.1 Hz, 1H); $^{19}$F NMR (282 MHz, DMSO-d$_6$) δ −60.99, −122.63; MS (ES+) 482.2 (M+Na).

Step-3: Preparation of tert-butyl 3-(5-((2-fluoro-5-(hydroxy(pyridin-4-yl)methyl)phenyl)carbamoyl)-3-(trifluoromethyl)-1H-pyrazol-1-yl)benzylcarbamate (132d)

To a solution of 1-(3-cyanophenyl)-N-(2-fluoro-5-(hydroxy(pyridin-4-yl)methyl)phenyl)-3-(trifluoromethyl)-1H-pyrazole-5-carboxamide (132c) (3.44 g, 7.15 mmol) in MeOH (100 mL) cooled with ice/water was added di-tert-butyl dicarbonate (6.30 g, 28.6 mmol) and nickel(II) chloride hexahydrate (2.123 g, 8.93 mmol) followed by addition of sodium borohydride (1.655 g, 42.9 mmol) slowly over 5 min and stirred at room temperature for 3 h. The reaction was quenched with N1-(2-aminoethyl)ethane-1,2-diamine (9.36 mL, 86 mmol) stirred at room temperature for 0.5 h and concentrated in vacuum to dryness. The residue was diluted with water (200 mL). The solid separated was collected by filtration purified by flash column chromatography (silica gel 40 g, eluting with ethyl acetate in hexane 0-100%) to furnish tert-butyl 3-(5-((2-fluoro-5-(hydroxy (pyridin-4-yl)methyl)phenyl)carbamoyl)-3-(trifluoromethyl)-1H-pyrazol-1-yl)benzylcarbamate (132d) (1.172 g, 2.002 mmol, 27%) as an off white solid; MS (ES+) 586.3 (M+1); (ES−) 584.3 (M−1).

Step-4: Preparation of tert-butyl 3-(5-(5-((cyclopropylmethylamino)(pyridin-4-yl)methyl)-2-fluorophenylcarbamoyl)-3-(trifluoromethyl)-1H-pyrazol-1-yl)benzylcarbamate (132e)

To a solution of tert-butyl 3-(5-((2-fluoro-5-(hydroxy (pyridin-4-yl)methyl)phenyl)carbamoyl)-3-(trifluoromethyl)-1H-pyrazol-1-yl)benzylcarbamate (132d) (1.172 g, 2.002 mmol) in dichloromethane (40 mL) at 0° C. was added thionyl chloride (0.312 mL, 4.27 mmol) and stirred at room temperature for 2 h. The reaction mixture was quenched with triethylamine (1.855 mL, 13.31 mmol) concentrated in vacuum to dryness. The residue obtained was dissolved in acetonitrile (40 mL) and added cyclopropylmethanamine (3.66 mL, 42.7 mmol). The reaction mixture was heated at reflux overnight, cooled to room temperature and concentrated in vacuum to dryness. The residue was dissolved in chloroform (100 mL), washed with water (100 mL), dried, filtered and concentrated in vacuum. The residue obtained was purified by flash column chromatography (silica gel 40 g, eluting 0-20% methanol in chloroform) afforded tert-butyl 3-(5-(5-(((cyclopropylmethylamino)(pyridin-4-yl)methyl)-2-fluorophenylcarbamoyl)-3-(trifluoromethyl)-1H-pyrazol-1-yl)benzylcarbamate (132e) (127 mg, 0.199 mmol, 9.94% yield) as a white foam; MS (ES+) 639.4 (M+1), (ES−) 637.4 (M−1).

Step-5: Preparation of 1-(3-(aminomethyl)phenyl)-N-(5-((((cyclopropylmethyl)amino)(pyridin-4-yl) methyl)-2-fluorophenyl)-3-(trifluoromethyl)-1H-pyrazole-5-carboxamide (132f)

To a solution of tert-butyl 3-(5-(5-((cyclopropylmethylamino)(pyridin-4-yl)methyl)-2-fluorophenylcarbamoyl)-3-(trifluoromethyl)-1H-pyrazol-1-yl)benzylcarbamate (132e) in methanol (5 mL) was added hydrochloric acid (0.571 mL, 18.79 mmol) and stirred at room temperature over night. The reaction mixture was concentrated in vacuum to dryness. The residue was purified by flash column chromatography (silica gel 12 g, eluting with 0-100% CMA 80 in chloroform) to afford compound free base of 1-(3-(aminomethyl)phenyl)-N-(5-((((cyclopropylmethyl)amino)(pyridin-4-yl) methyl)-2-fluorophenyl)-3-(trifluoromethyl)-1H-pyrazole-5-carboxamide (132f). To a stirred solution of free base of 1-(3-(aminomethyl)phenyl)-N-(5-(((cyclopropylmethylamino)(pyridin-4-yl)methyl)-2-fluorophenyl)-3-(trifluoromethyl)-1H-pyrazole-5-carboxamide (36 mg, 0.067 mmol) in methanol (5 mL) was added conc. hydrochloric acid (0.028 mL, 0.334 mmol) stirred for 30 mins and concentrated in vacuum to dryness to afford 1-(3-(aminomethyl)phenyl)-N-(5-((((cyclopropylmethyl)amino)(pyridin-4-yl)methyl)-2-fluorophenyl)-3-(trifluoromethyl)-1H-pyrazole-5-carboxamide (132f) (30 mg, 0.049 mmol, 73.4% yield) hydrochloride salt as a yellow solid; $^1$H NMR (300 MHz, DMSO-$d_6$) δ 10.91 (s, 3H, D$_2$O exchangeable), 8.95-8.84 (m, 2H), 8.56 (s, 3H, D$_2$O exchangeable), 8.33-8.21 (m, 2H), 8.06 (dd, J=7.1, 2.3 Hz, 1H), 7.85 (ddd, J=8.6, 4.5, 2.3 Hz, 1H), 7.72 (d, J=1.9 Hz, 2H), 7.65 (dt, J=7.3, 1.8 Hz, 1H), 7.60-7.49 (m, 2H), 7.44 (dd, J=10.3, 8.6 Hz, 1H), 6.01 (s, 1H), 4.12 (q, J=5.8 Hz, 2H), 2.75 (d, J=6.9 Hz, 2H), 1.28-1.14 (m, 1H), 0.55 (m, 2H), 0.41-0.28 (m, 2H); MS (ES+) 539.3 (M+1), (ES−) 537.3 (M−1), 573.3 (M+35); Analysis calculated for C$_{28}$H$_{26}$F$_4$N$_6$O.3HCl.3H$_2$O: C, 47.98; H, 5.03; N, 11.99; Cl, 14.98; Found: C, 48.20; H, 5.00; N, 11.57; Cl, 14.20.

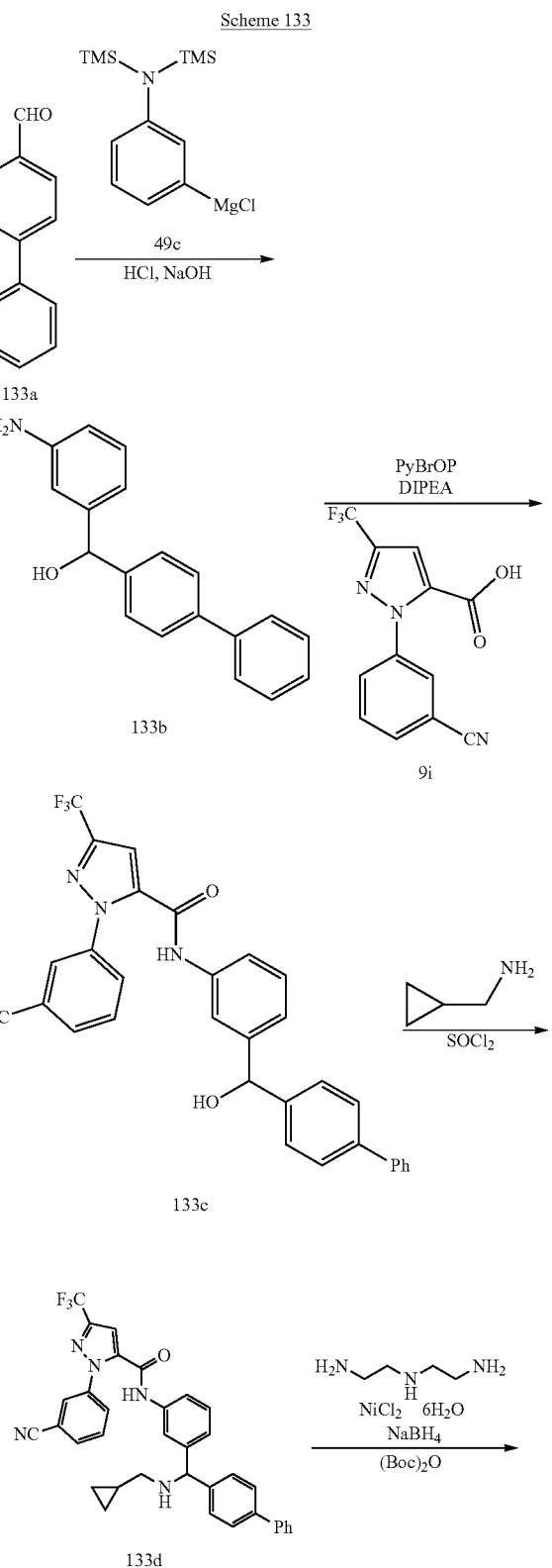

Scheme 133

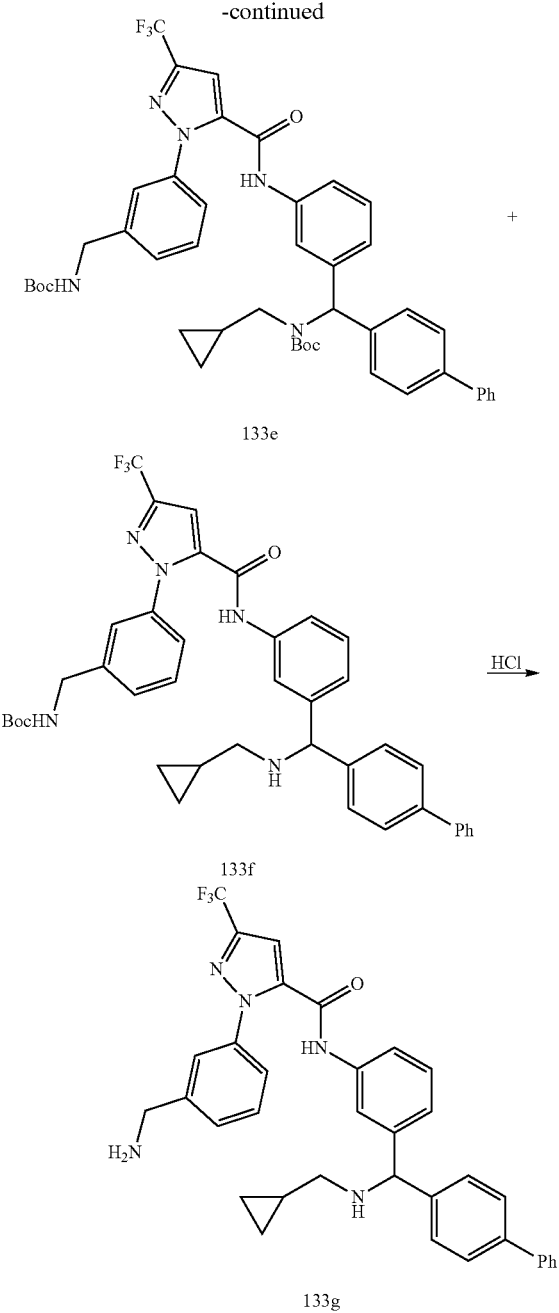

with ethyl acetate (2×50 mL). The organic layers were combined washed with saturated aqueous NH$_4$Cl (50 mL), dried over anhydrous MgSO$_4$, filtered, evaporated to dryness. The crude residue obtained was purified by flash column chromatography (silica gel 40 g, eluting with 0-100% ethyl acetate in hexane) to furnish (3-Amino-phenyl)-biphenyl-4-yl-methanol (133b) (2.0 g, 72.64%) as a light brown sticky liquid. $^1$H NMR (300 MHz, DMSO-d$_6$) δ 7.64-7.55 (m, 4H), 7.44 (ddt, J=8.4, 6.4, 1.8 Hz, 4H), 7.37-7.28 (m, 1H), 6.93 (t, J=7.7 Hz, 1H), 6.61 (t, J=1.9 Hz, 1H), 6.55 (dt, J=7.7, 1.3 Hz, 1H), 6.39 (ddd, J=8.0, 2.4, 1.0 Hz, 1H), 5.74 (d, J=3.8 Hz, 1H), 5.55 (d, J=3.8 Hz, 1H), 5.00 (s, 2H).

Step-2: Preparation of 2-(3-Cyano-phenyl)-5-trifluoromethyl-2H-pyrazole-3-carboxylic acid [3-(biphenyl-4-yl-hydroxy-methyl)-phenyl]-amide (133c)

To a solution of 1-(3-cyanophenyl)-3-(trifluoromethyl)-1H-pyrazole-5-carboxylic acid (9i) (2.04 g, 7.263 mmol) in DMF (40 mL) was added ((3-Amino-phenyl)-biphenyl-4-yl-methanol (133b) (2.0 g, 7.26 mmol), N-ethyl-N-isopropylpropan-2-amine (10 mL, 58.10 mmol) and bromo-trispyrrolidino phosphoniumhexafluorophosphate(PyBrOP, 3.38 g, 7.26 mmol) at room temperature. The reaction mixture was stirred at room temperature for 42 h and diluted with ethyl acetate (350 mL). The reaction mixture was washed with water (2×150 mL), brine (120 mL), dried, filtered, and evaporated to dryness. The residue obtained was purified by flash column chromatography (silica gel 120 g, eluting with ethyl acetate in hexanes from 0-30% to furnish 2-(3-Cyano-phenyl)-5-trifluoromethyl-2H-pyrazole-3-carboxylic acid [3-(biphenyl-4-yl-hydroxy-methyl)-phenyl]-amide (133c) (2.0 g, 51.13%) as a red brown sticky liquid; $^1$H NMR (300 MHz, DMSO-d$_6$) δ 10.66 (s, 1H), 8.16 (t, J=1.9 Hz, 1H), 8.00 (dt, J=7.8, 1.3 Hz, 1H), 7.90 (ddd, J=8.2, 2.2, 1.1 Hz, 1H), 7.74 (d, J=8.0 Hz, 1H), 7.71 (d, J=4.8 Hz, 1H), 7.67 (d, J=1.8 Hz, 1H), 7.64-7.54 (m, 5H), 7.44 (dd, J=8.4, 6.5 Hz, 4H), 7.37-7.30 (m, 1H), 7.27 (d, J=7.9 Hz, 1H), 7.21-7.15 (m, 1H), 6.01 (d, J=3.8 Hz, 1H), 5.73 (d, J=3.8 Hz, 1H).

Step-3: Preparation of 2-(3-Cyano-phenyl)-5-trifluoromethyl-2H-pyrazole-3-carboxylic Acid {3-[biphenyl-4-yl-(cyclopropylmethyl-amino)-methyl]-phenyl}-amide (133d)

To a solution of 2-(3-Cyano-phenyl)-5-trifluoromethyl-2H-pyrazole-3-carboxylic acid [3-(biphenyl-4-yl-hydroxy-methyl)-phenyl]-amide (133c) (2.0 g, 3.71 mmol) in dichloromethane (20 mL) at 0° C. was added thionyl chloride (0.883 g, 7.43 mmol) and stirred at room temperature for 4 h. The reaction mixture was concentrated in vacuum to dryness. The residue obtained was dissolved in acetonitrile (40 mL) and added cyclopropylmethanamine (4.2 mL, 55.71 mmol). The reaction mixture was heated at reflux overnight, cooled to room temperature and concentrated in vacuum to dryness. The residue was dissolved in dichloromethane (40 mL), washed with water (2×25 mL), dried, filtered and concentrated in vacuum. The residue obtained was purified by flash column chromatography (silica gel 40 g, eluting 0-40% ethyl acetate in hexane) to afford 2-(3-Cyano-phenyl)-5-trifluoromethyl-2H-pyrazole-3-carboxylic acid {3-[biphenyl-4-yl-(cyclopropylmethyl-amino)-methyl]-phenyl}-amide (133d) (1.0 g, 45.56%) as pale gummy liquid; $^1$H NMR (300 MHz, DMSO-d$_6$) δ 10.66 (s, 1H), 8.20-8.11 (m, 1H), 7.99 (dd, J=7.7, 1.6 Hz, 1H), 7.93-7.87 (m, 1H), Preparation of 1-(3-(aminomethyl)phenyl)-N-(3-(biphenyl-4-yl(cyclopropylmethylamino)methyl)phenyl)-3-(trifluoromethyl)-1H-pyrazole-5-carboxamide (133g)

Step-1: Preparation of (3-Amino-phenyl)-biphenyl-4-yl-methanol (133b)

To a stirred solution of biphenyl-4-carbaldehyde (133a) (1.2 g, 10 mmol) in tetrahydrofuran (5 mL) was added (3-(bis(trimethylsilyl)amino)phenyl)magnesium chloride (49c) (12.00 mL, 12.00 mmol) at 0° C. The reaction was stirred for 14 h at room temperature, quenched with 2 N HCl (12.50 mL) and stirred for additional 6 h. The reaction mixture was nuetralized with 2 N NaOH (15 mL), extracted 7.74 (d, J=8.0 Hz, 1H), 7.70 (d, J=3.3 Hz, 2H), 7.63-7.52 (m, 5H), 7.51-7.45 (m, 2H), 7.42 (d, J=7.7 Hz, 1H), 7.37-7.32 (m, 1H), 7.31-7.22 (m, 2H), 4.87 (s, 1H), 2.32 (d, J=6.7 Hz, 2H), 1.03-0.87 (m, 1H), 0.50-0.29 (m, 2H), 0.18--0.04 (m, 2H).

Step-4: Preparation of tert-butyl ([1,1'-biphenyl]-4-yl(3-(1-(3-(((tert-butoxycarbonyl)amino)methyl) phenyl)-3-(trifluoromethyl)-1H-pyrazole-5-carboxamido)phenyl)methyl)(cyclopropylmethyl)carbamate (133e) and tert-butyl 3-(5-((3-([1,1'-biphenyl]-4-yl ((cyclopropylmethyl)amino)methyl)phenyl)carbamoyl)-3-(trifluoromethyl)-1H-pyrazol-1-yl)benzylcarbamate (133f)

To a solution of 2-(3-Cyano-phenyl)-5-trifluoromethyl-2H-pyrazole-3-carboxylic acid {3-[biphenyl-4-yl-(cyclopropylmethyl-amino)-methyl]-phenyl}-amide (133d) (1.0 g, 1.69 mmol) in MeOH (24 mL) cooled with ice/water was added nickel(II) chloride hexahydrate (0.48 g, 2.03 mmol) and Boc anhydride (1.16 mL, 5.07 mmol) followed by portion-wise addition of Sodium Borohydride (0.44 g, 10.14 mmol) over a period of 15 min. The reaction mixture was stirred at room temperature for 2 hrs and quenched with N¹-(2-aminoethyl)ethane-1,2-diamine (0.5 mL, 4.23 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over MgSO₄ filtered and concentrated in vacuum. The residue obtained was purified by flash column chromatography (silica gel 24 g, eluting with 0-40% Ethyl acetate/hexane) to furnish.

1. tert-butyl ([1,1'-biphenyl]-4-yl(3-(1-(3-(((tert-butoxycarbonyl)amino)methyl)phenyl)-3-(trifluoromethyl)-1H-pyrazole-5-carboxamido)phenyl)methyl)(cyclopropylmethyl)carbamate (133e) (300 mg, 22.3%) as a white solid; ¹H NMR (300 MHz, DMSO-d₆) δ 10.73 (s, 1H), 7.72-7.63 (m, 5H), 7.55 (s, 1H), 7.52-7.38 (m, 7H), 7.38-7.30 (m, 3H), 7.26 (d, J=8.2 Hz, 2H), 7.01-6.93 (m, 1H), 6.33 (s, 1H), 4.18 (d, J=6.2 Hz, 2H), 3.12 (t, J=6.3 Hz, 2H), 1.37 (s, 9H), 1.32 (s, 9H), 0.92-0.77 (m, 1H), 0.20 (d, J=8.1 Hz, 2H), −0.15 (s, 2H).

2. tert-butyl 3-(5-((3-([1,1'-biphenyl]-4-yl((cyclopropylmethyl)amino)methyl)phenyl)carbamoyl)-3-(trifluoromethyl)-1H-pyrazol-1-yl)benzylcarbamate (133f) (280 mg, 23.81%) as a white solid; ¹H NMR (300 MHz, DMSO-d₆) δ 10.71 (s, 1H), 7.71-7.67 (m, 1H), 7.63-7.55 (m, 5H), 7.53-7.46 (m, 3H), 7.45-7.39 (m, 4H), 7.38-7.32 (m, 3H), 7.25 (d, J=6.7 Hz, 2H), 4.87 (s, 1H), 4.19 (d, J=6.2 Hz, 2H), 2.32 (d, J=6.7 Hz, 2H), 1.35 (s, 9H), 0.99-0.89 (m, 1H), 0.47-0.32 (m, 2H), 0.12--0.02 (m, 2H).

Step-5: Preparation of 2-(3-Aminomethyl-phenyl)-5-trifluoromethyl-2H-pyrazole-3-carboxylic Acid {3-[biphenyl-4-yl-(cyclopropylmethyl-amino)-methyl]-phenyl}-amide (133g)

A solution of tert-butyl ([1,1'-biphenyl]-4-yl(3-(1-(3-(((tert-butoxycarbonyl)amino)methyl)phenyl)-3-(trifluoromethyl)-1H-pyrazole-5-carboxamido)phenyl)methyl)(cyclopropylmethyl)carbamate (133e) (300 mg, 0.37 mmol) and tert-butyl 3-(5-((3-([1,1'-biphenyl]-4-yl((cyclopropylmethyl)amino)methyl)phenyl)carbamoyl)-3-(trifluoromethyl)-1H-pyrazol-1-yl)benzylcarbamate (133f) (280 mg, 0.4 mmol) were dissolved separately in methanol (10 mL) and added conc. HCl (0.5 mL). The reaction mixture was stirred at room temperature overnight and concentrated in vacuum to dryness. The residue was azeotroped with toluene (2×10 mL) and ethanol (10 mL), dried in vacuum pump to furnish a white solid residue. NMR of the residue in methanol and TLC shows same compound. The products were combined dried and purified by flash column chromatography (silica gel 24 g, eluting with 0-15% methanol in dichloromethane to furnish 2-(3-Aminomethyl-phenyl)-5-trifluoromethyl-2H-pyrazole-3-carboxylic acid {3-[biphenyl-4-yl-(cyclopropylmethyl-amino)-methyl]-phenyl}-amide (133g) (0.250 g, 54.56%) as pale white solid. This was repurified by flash column chromatography (silica gel 4 g, eluting 0-25% methanol in chloroform) to afford 2-(3-Aminomethyl-phenyl)-5-trifluoromethyl-2H-pyrazole-3-carboxylic acid {3-[biphenyl-4-yl-(cyclopropylmethyl-amino)-methyl]-phenyl}-amide (133g) (0.14 gm) as a white solid; ¹H NMR (300 MHz, DMSO-d₆) δ 11.00 (s, 1H), 10.19 (d, J=6.8 Hz, 2H), 8.51 (s, 3H), 7.92 (s, 1H), 7.81-7.59 (m, 12H), 7.56-7.43 (m, 4H), 7.39 (d, J=7.2 Hz, 1H), 5.75-5.56 (m, 1H), 4.12 (q, J=5.6 Hz, 2H), 2.75 (q, J=5.7, 4.9 Hz, 2H), 1.19 (td, J=13.0, 10.7, 5.7 Hz, 1H), 0.57 (d, J=7.6 Hz, 2H), 0.42-0.20 (m, 2H); ¹⁹F NMR (282 MHz, DMSO) δ −60.77; MS (ES+) 596.4 (M+1); (ES−) 630.3 (M+Cl); Analysis calculated for C₃₅H₃₂F₃N₅O.2.5HCl.2H₂O: C, 58.16; H, 5.37; Cl, 12.26; N, 9.69; Found; C, 58.11; H, 5.19; Cl, 11.86; N, 9.47.

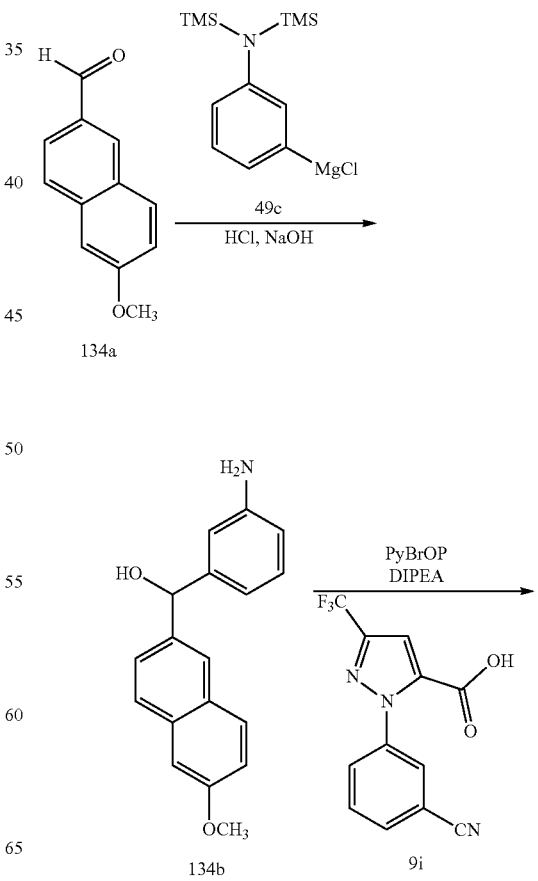

Scheme 134

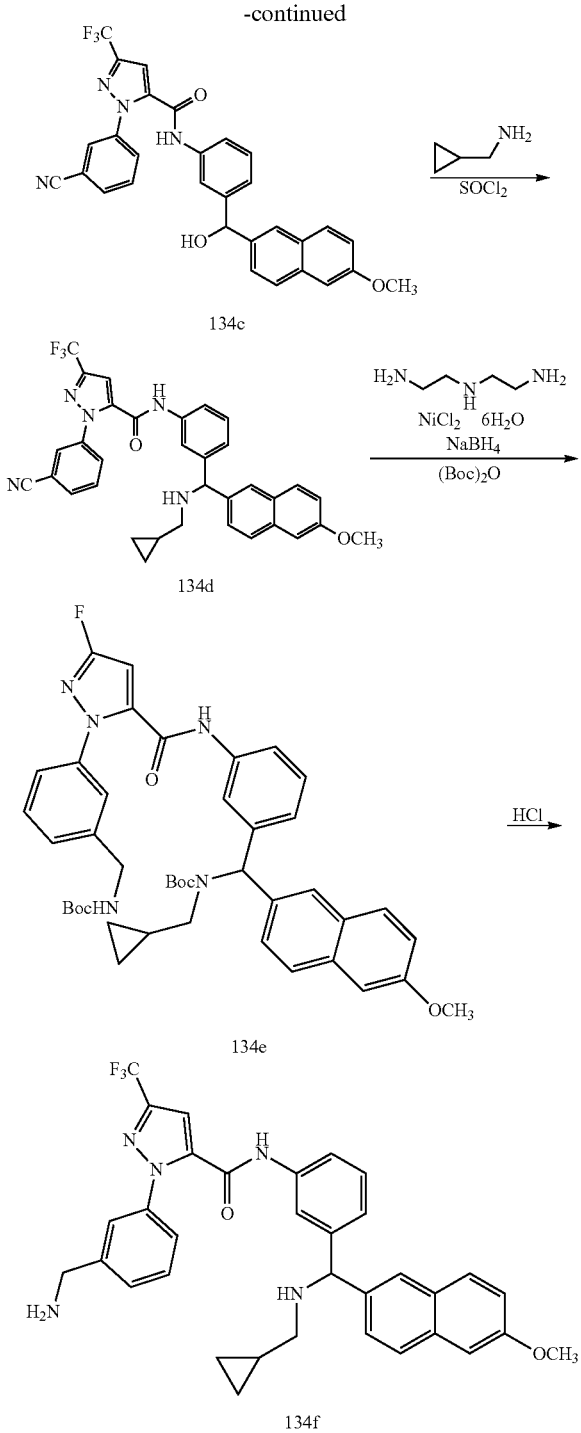

Preparation of 1-(3-(aminomethyl)phenyl)-N-(3-((cyclopropylmethylamino)(6-methoxynaphthalen-2-yl)methyl)phenyl)-3-(trifluoromethyl)-1H-pyrazole-5-carboxamide (134f)

Step-1: Preparation of (3-Amino-phenyl)-(6-methoxy-naphthalen-2-yl)-methanol (134b)

To a stirred solution of 6-Methoxy-naphthalene-2-carbaldehyde (134a) (1.2 g, 10 mmol) in tetrahydrofuran (5 mL) was added (3-(bis(trimethylsilyl)amino)phenyl)magnesium chloride (49c) (12.00 mL, 12.00 mmol) at 0° C. The reaction was stirred for 14 h quenched with 2 N HCl (12.50 mL) and stirred for additional 6 h at room temperature. The reaction mixture was basified with 2 N NaOH (15 mL) and extracted with ethyl acetate (2×50 mL). The organic layers were combined washed with saturated NH$_4$Cl (50 mL), dried over anhydrous MgSO$_4$, filtered, evaporated to dryness. The crude residue was purified by flash column chromatography (silica gel 40 g, eluting with 0-100% ethyl acetate in hexane) to furnish (3-Amino-phenyl)-(6-methoxy-naphthalen-2-yl)-methanol (134b) (2.4 g, 85.92%) as a light brown sticky liquid; $^1$H NMR (300 MHz, DMSO-d$_6$) δ 7.82-7.75 (m, 2H), 7.71 (d, J=8.6 Hz, 1H), 7.38 (dd, J=8.5, 1.7 Hz, 1H), 7.25 (d, J=2.5 Hz, 1H), 7.12 (dd, J=9.0, 2.5 Hz, 1H), 6.92 (t, J=7.7 Hz, 1H), 6.60 (t, J=1.9 Hz, 1H), 6.56 (dt, J=7.6, 1.3 Hz, 1H), 6.38 (ddd, J=8.0, 2.3, 1.1 Hz, 1H), 5.77 (d, J=3.7 Hz, 1H), 5.63 (d, J=3.8 Hz, 1H), 4.97 (s, 2H), 3.85 (s, 3H).

Step-2: Preparation of 2-(3-Cyano-phenyl)-5-trifluoromethyl-2H-pyrazole-3-carboxylic acid {3-[hydroxy-(6-methoxy-naphthalen-2-yl)-methyl]-phenyl}-amide (134c)

To a solution of 1-(3-cyanophenyl)-3-(trifluoromethyl)-1H-pyrazole-5-carboxylic acid (9i) (2.6 g, 9.45 mmol) in DMF (48 mL) was added (3-Amino-phenyl)-(6-methoxy-naphthalen-2-yl)-methanol (134b) (2.4 g, 8.59 mmol), N-ethyl-N-isopropylpropan-2-amine (8.88 g, 68.72 mmol) and bromo-tris-pyrrolidino phosphoniumhexafluorophosphate (PyBrOP, 4.40 g, 9.451 mmol) at room temperature. The reaction mixture was stirred at room temperature for 42 h under nitrogen atmosphere. The reaction was diluted with ethyl acetate (200 mL) washed with water (2×100 mL), brine (100 mL), dried, filtered, and evaporated to dryness. The residue obtained was purified by flash column chromatography [silica gel 120 g, eluting with ethyl acetate in hexanes from 0-30%] to furnish 2-(3-Cyano-phenyl)-5-trifluoromethyl-2H-pyrazole-3-carboxylic acid {3-[hydroxy-(6-methoxy-naphthalen-2-yl)-methyl]-phenyl}-amide (134c) (2.4 g, 51.50% yield) as a red brown sticky liquid; $^1$H NMR (300 MHz, DMSO-d$_6$) δ 10.63 (s, 1H), 8.14 (t, J=1.9 Hz, 1H), 7.99 (dt, J=7.8, 1.3 Hz, 1H), 7.88 (ddd, J=8.2, 2.2, 1.1 Hz, 1H), 7.84-7.82 (m, 1H), 7.79 (d, J=9.0 Hz, 1H), 7.76-7.67 (m, 3H), 7.65 (t, J=1.8 Hz, 1H), 7.56 (dt, J=8.2, 1.5 Hz, 1H), 7.37 (dd, J=8.5, 1.7 Hz, 1H), 7.29 (d, J=7.8 Hz, 1H), 7.27-7.23 (m, 1H), 7.19 (dt, J=7.9, 1.4 Hz, 1H), 7.14 (dd, J=8.9, 2.5 Hz, 1H), 6.03 (d, J=3.8 Hz, 1H), 5.80 (d, J=3.8 Hz, 1H), 3.85 (s, 3H).

Step-3: Preparation of 2-(3-Cyano-phenyl)-5-trifluoromethyl-2H-pyrazole-3-carboxylic Acid {3-[(cyclopropylmethyl-amino)-(6-methoxy-naphthalen-2-yl)-methyl]-phenyl}-amide (134d)

To a solution of 2-(3-Cyano-phenyl)-5-trifluoromethyl-2H-pyrazole-3-carboxylic acid {3-[hydroxy-(6-methoxy-naphthalen-2-yl)-methyl]-phenyl}-amide (134c) (2.4 g, 4.42 mmol) in dichloromethane (50 mL) at 0° C. was added thionyl chloride (1.05 g, 8.85 mmol) and stirred at room temperature for 4 h. The reaction mixture was concentrated in vacuum to dryness. The residue obtained was dissolved in acetonitrile (40 mL) and added cyclopropylmethanamine (4.72 g, 66.3 mmol). The reaction mixture was heated at reflux overnight, cooled to room temperature and concentrated in vacuum to dryness. The residue was dissolved in dichloromethane (40 mL), washed with water (2×25 mL), dried, filtered and concentrated in vacuum. The residue obtained was purified by flash column chromatography (silica gel 40 g, eluting 0-40% ethyl acetate in hexane) to afford 2-(3-Cyano-phenyl)-5-trifluoromethyl-2H-pyrazole-3-carboxylic acid {3-[(cyclopropylmethyl-amino)-(6-methoxy-naphthalen-2-yl)-methyl]-phenyl}-amide (134d) (1.3 g, 49.38%) as light brown sticky liquid; $^1$H NMR (300 MHz, DMSO-$d_6$) δ 10.63 (s, 1H), 8.15 (t, J=1.8 Hz, 1H), 7.99 (dt, J=7.8, 1.3 Hz, 1H), 7.89 (ddd, J=8.2, 2.2, 1.1 Hz, 1H), 7.84 (d, J=1.5 Hz, 1H), 7.77 (d, J=9.0 Hz, 1H), 7.74 (d, J=5.0 Hz, 1H), 7.72-7.68 (m, 4H), 7.55 (td, J=4.7, 2.1 Hz, 1H), 7.46 (dd, J=8.5, 1.7 Hz, 1H), 7.25 (t, J=4.0 Hz, 3H), 7.13 (dd, J=8.9, 2.6 Hz, 1H), 4.95 (s, 1H), 3.84 (s, 3H), 2.33 (d, J=6.7 Hz, 2H), 1.24 (s, 1H), 0.89-0.79 (m, 1H), 0.44-0.31 (m, 2H), 0.05 (q, J=4.8 Hz, 2H).

Step-4: Preparation of tert-butyl ((3-(1-(3-(((tert-butoxycarbonyl)amino)methyl)phenyl)-3-(trifluoromethyl)-1H-pyrazole-5-carboxamido)phenyl)(6-methoxynaphthalen-2-yl)methyl)(cyclopropylmethyl)carbamate (134e)

To a solution of 2-(3-Cyano-phenyl)-5-trifluoromethyl-2H-pyrazole-3-carboxylic acid {3-[(cyclopropylmethyl-amino)-(6-methoxy-naphthalen-2-yl)-methyl]-phenyl}-amide (134d) (1.3 g, 2.18 mmol) in MeOH (26 mL) cooled with ice/water was added nickel(II) chloride hexahydrate (0.62 g, 2.619 mmol) and Boc anhydride (1.5 mL, 6.547 mmol) followed by portion-wise addition of sodium borohydride (0.500 g, 13.095 mmol) over a period of 15 min. The reaction mixture was stirred at room temperature for 2 hrs and quenched with $N^1$-(2-aminoethyl)ethane-1,2-diamine (0.6 mL, 5.456 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over MgSO$_4$ filtered and concentrated in vacuum. The residue obtained was purified by flash column chromatography (silica gel 24 g, eluting with 0-25% Ethyl acetate/hexane) to furnish tert-butyl ((3-(1-(3-(((tert-butoxycarbonyl)amino)methyl)phenyl)-3-(trifluoromethyl)-1H-pyrazole-5-carboxamido)phenyl)(6-methoxynaphthalen-2-yl)methyl)(cyclopropylmethyl)carbamate (134e) (0.90 g, 51.57%) as a white solid; $^1$H NMR (300 MHz, DMSO-$d_6$) δ 10.71 (s, 1H), 7.80 (d, J=5.7 Hz, 1H), 7.77 (d, J=6.1 Hz, 1H), 7.67 (d, J=8.1 Hz, 1H), 7.58 (d, J=1.7 Hz, 1H), 7.53 (s, 1H), 7.47 (q, J=6.4 Hz, 2H), 7.39 (t, J=3.7 Hz, 2H), 7.33 (dd, J=7.4, 2.3 Hz, 4H), 7.14 (dd, J=9.0, 2.5 Hz, 1H), 6.97 (d, J=7.9 Hz, 1H), 6.43 (s, 1H), 4.17 (d, J=6.1 Hz, 2H), 3.87 (s, 3H), 3.14 (d, J=6.6 Hz, 2H), 1.37 (s, 9H), 1.32-1.29 (m, 9H), 0.68-0.50 (m, 1H), 0.23-0.04 (m, 2H), −0.06-−0.21 (m, 1H), −0.18-−0.31 (m, 1H).

Step-5: Preparation of 2-(3-Aminomethyl-phenyl)-5-trifluoromethyl-2H-pyrazole-3-carboxylic Acid {3-[(cyclopropylmethyl-amino)-(6-methoxy-naphthalen-2-yl)-methyl]-phenyl}-amide (134f)

To a solution of tert-butyl ((3-(1-(3-(((tert-butoxycarbonyl)amino)methyl)phenyl)-3-(trifluoromethyl)-1H-pyrazole-5-carboxamido)phenyl)(6-methoxynaphthalen-2-yl)methyl)(cyclopropylmethyl)carbamate (134e) (0.90 g, 1.13 mmol) in methanol (10 mL) was added conc. HCl (0.5 mL). The reaction mixture was stirred at room temperature overnight and concentrated in vacuum to dryness. The residue was azeotroped with toluene (2×10 mL) and ethanol (10 mL), dried in vacuum pump to furnish a white solid residue. The product was purified by flash column chromatography (silica gel 12 g, eluting with 0-15% methanol in dichloromethane to furnish 2-(3-Aminomethyl-phenyl)-5-trifluoromethyl-2H-pyrazole-3-carboxylic acid {3-[(cyclopropylmethyl-amino)-(6-methoxy-naphthalen-2-yl)-methyl]-phenyl}-amide (BCX-7246, 155 mg, 20.5%) as off white solid. This was repurified by flash column chromatography (silica gel 4 g, eluting 0-25% methanol in chloroform) to afford pure 1-(3-(aminomethyl)phenyl)-N-(3-((cyclopropylmethylamino)(6-methoxynaphthalen-2-yl)methyl)phenyl)-3-(trifluoromethyl)-1H-pyrazole-5-carboxamide (134f) (0.085 g) as a white solid; $^1$H NMR (300 MHz, DMSO-$d_6$) δ 10.99 (s, 1H), 10.30-10.12 (m, 2H), 8.52 (s, 3H), 8.14 (d, J=2.0 Hz, 1H), 7.91 (t, J=1.8 Hz, 1H), 7.84 (dd, J=16.4, 8.9 Hz, 2H), 7.77-7.68 (m, 4H), 7.63 (tt, J=5.8, 1.7 Hz, 2H), 7.57-7.42 (m, 3H), 7.34 (d, J=2.6 Hz, 1H), 7.22 (dd, J=8.9, 2.5 Hz, 1H), 5.82-5.57 (m, 1H), 4.11 (d, J=5.6 Hz, 2H), 3.87 (s, 3H), 2.81-2.66 (m, 2H), 1.20 (td, J=8.0, 3.9 Hz, 1H), 0.62-0.45 (m, 2H), 0.40-0.21 (m, 2H); $^{19}$F NMR (282 MHz, DMSO) δ −60.79; MS (ES+) (ES−) 634.3 (M+Cl); Analysis calculated for $C_{34}H_{32}F_3N_5O_2$·2HCl·2H$_2$O: C, 57.63; H, 5.41; Cl, 10.01; N, 9.88; Found: C, 57.50; H, 5.11; Cl, 9.86; N, 9.68.

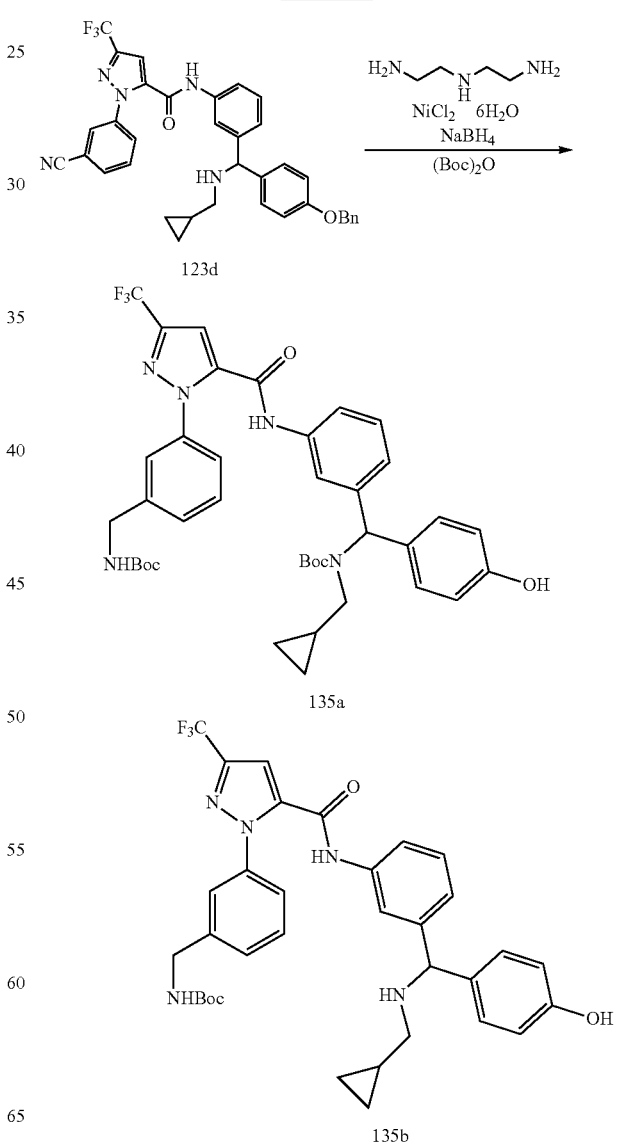

Scheme 135

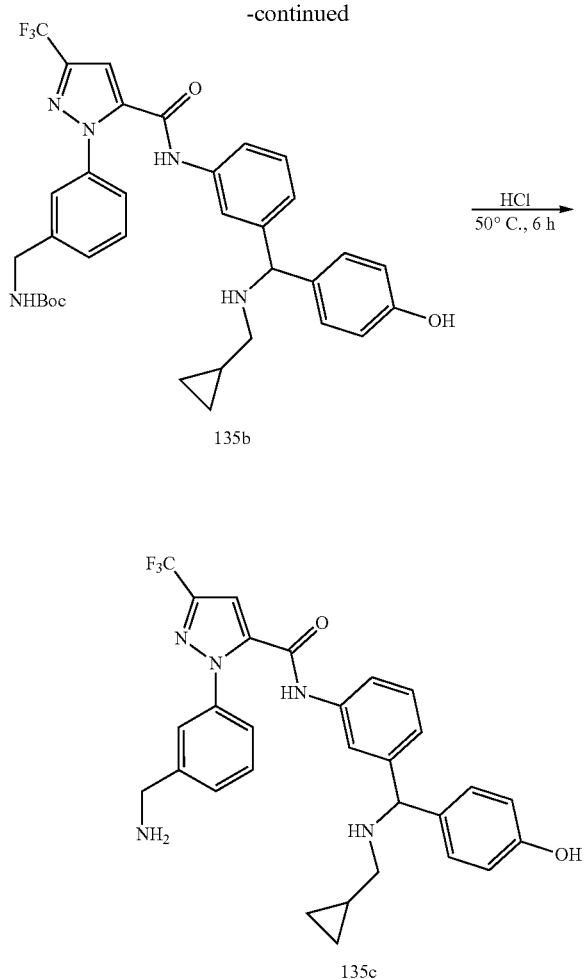

Preparation of 1-(3-(aminomethyl)phenyl)-N-(3-(((cyclopropylmethyl)amino)(4-hydroxyphenyl)methyl)phenyl)-3-(trifluoromethyl)-1H-pyrazole-5-carboxamide (135c)

Step-1: Preparation of tert-Butyl ((3-(1-(3-(((tert-butoxycarbonyl)amino)methyl)phenyl)-3-(trifluoromethyl)-1H-pyrazole-5-carboxamido)phenyl)(4-hydroxyphenyl)methyl)(cyclopropylmethyl) carbamate (135a) and tert-Butyl 3-(5-((3-(((cyclopropylmethyl)amino)(4-hydroxyphenyl)methyl)phenyl)carbamoyl)-3-(trifluoromethyl)-1H-pyrazol-1-yl)benzylcarbamate (135b)

To a solution of 1-(3-cyanophenyl)-N-(3-(((cyclopropylmethyl)amino)(4-hydroxyphenyl)methyl)phenyl)-3-(trifluoromethyl)-1H-pyrazole-5-carboxamide (123d) (1.2 g, 2.26 mmol) in MeOH (20 mL) cooled with ice/water was added nickel(II) chloride hexahydrate (0.57 g, 2.4 mmol) and Boc anhydride (1.26 g, 5.79 mmol) followed by portionwise addition of sodium borohydride (0.44 g, 11.58 mmol) over a period of 15 min. The reaction mixture was stirred at room temperature for 2 hrs and quenched with N1-(2-aminoethyl)ethane-1,2-diamine (1.1 mL, 7.72 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over MgSO$_4$ filtered and concentrated in vacuum. The residue obtained was purified by flash column chromatography (silica gel 24 g, eluting with 0-60% Ethyl acetate/hexane) to furnish:

1. tert-Butyl ((3-(1-(3-(((tert-butoxycarbonyl)amino)methyl)phenyl)-3-(trifluoromethyl)-1H-pyrazole-5-carboxamido)phenyl)(4hydroxyphenyl)methyl)(cyclopropylethyl) carbamate (135a) (0.167 g, 7.55%) as a white solid; $^1$H NMR (300 MHz, DMSO-d$_6$) δ 10.70 (s, 1H), 9.47 (s, 1H), 7.68-7.58 (m, 1H), 7.55 (s, 1H), 7.53-7.45 (m, 1H), 7.46-7.37 (m, 2H), 7.37-7.25 (m, 3H), 6.97 (dd, J=8.4, 6.5 Hz, 2H), 6.92-6.85 (m, 1H), 6.77-6.70 (m, 2H), 6.22 (s, 1H), 4.25-4.13 (m, 2H), 3.12 (dd, J=14.5, 6.7 Hz, 1H), 2.95 (dd, J=14.5, 6.6 Hz, 1H), 1.37 (s, 9H), 1.31 (s, 9H), 0.58 (d, J=25.7 Hz, 1H), 0.17 (ddt, J=13.6, 9.2, 4.4 Hz, 2H), −0.11 (dd, J=9.0, 4.6 Hz, 1H), −0.30 (s, 1H); $^{19}$F NMR (282 MHz, DMSO) δ −60.78; MS (ES+) 736.5 (M+1); (ES−) 734.1 (M−1).

2. tert-Butyl 3-(5-((3-(((cyclopropylmethyl)amino)(4-hydroxyphenyl)methyl)phenyl) carbamoyl)-3-(trifluoromethyl)-1H-pyrazol-1-yl)benzylcarbamate (135b) (0.209 g, 10.93%) as a white solid; $^1$H NMR (300 MHz, DMSO-d$_6$) δ 10.67 (s, 1H), 9.23 (s, 1H), 7.60 (d, J=2.1 Hz, 1H), 7.57 (s, 1H), 7.55-7.46 (m, 1H), 7.42 (dd, J=9.9, 3.1 Hz, 2H), 7.37-7.31 (m, 2H), 7.22 (t, J=7.8 Hz, 1H), 7.18-7.13 (m, 3H), 6.68-6.62 (m, 2H), 4.69 (s, 1H), 4.19 (d, J=6.2 Hz, 2H), 2.26 (d, J=6.7 Hz, 2H), 1.36 (s, 9H), 1.00-0.81 (m, 1H), 0.41-0.32 (m, 2H), 0.07-0.00 (m, 2H); $^{19}$F NMR (282 MHz, DMSO) δ −60.79; MS (ES+) 636.4 (M+1); (ES−) 634.4 (M−1).

Step-2: Preparation of 1-(3-(aminomethyl)phenyl)-N-(3-(((cyclopropylmethyl)amino)(4-hydroxyphenyl)methyl)phenyl)-3-(trifluoromethyl)-1H-pyrazole-5-carboxamide (135c)

To a solution of tert-butyl 3-(5-(3-((cyclopropylmethyl-amino)(4-hydroxyphenyl)methyl)phenylcarbamoyl)-3-(trifluoromethyl)-1H-pyrazol-1-yl)benzylcarbamate (135b) (0.199 g, 0.313 mmol) in methanol (3 mL) was added aq. 12 N HCl (0.652 mL, 7.83 mmol), the solution was stirred at 50° C. for 6 h and concentrated in vacuum to dryness. The residue obtained was purified by flash column chromatography (silica gel 12 g, eluting with 0-50% methanol in chloroform) to afford (135c) (39 mg, 23% yield) as a white solid.

$^1$H NMR (300 MHz, DMSO-d$_6$) δ 10.92 (s, 1H, D$_2$O exchangeable), 9.74 (s, 1H, D$_2$O exchangeable), 8.43 (s, 3H, D$_2$O exchangeable), 7.80 (s, 1H), 7.73 (d, J=2.1 Hz, 1H), 7.69 (s, 1H), 7.66-7.48 (m, 5H), 7.47-7.33 (m, 3H), 6.78 (d, J=8.4 Hz, 2H), 5.40 (s, 1H), 4.12 (s, 2H), 2.65 (s, 2H), 1.11 (d, J=11.2 Hz, 1H), 0.54 (d, J=8.0 Hz, 2H), 0.27 (s, 2H); $^{19}$F NMR (282 MHz, DMSO-d$_6$) δ −60.78; MS (ES$^+$): MS (ES+) 536.3 (M+1), MS (ES−) 570.2 (M+Cl); Analysis calculated for: $C_{29}H_{28}F_3N_5O_2 \cdot 2.5H_2O \cdot 2.35HCl$: C, 52.28; H, 5.35; Cl, 12.50; N, 10.51; Found: C, 52.16; H, 5.25; Cl, 12.39; N, 10.30.

Scheme 136

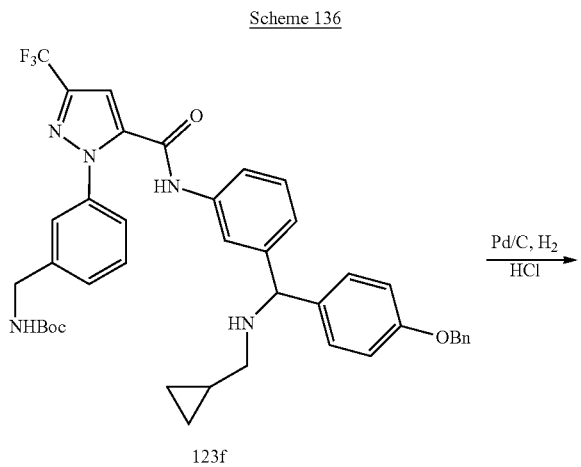

123f

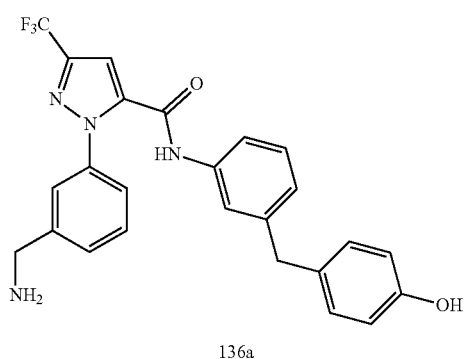

136a

Preparation of 1-(3-(Aminomethyl)phenyl)-N-(3-(4-hydroxybenzyl)phenyl)-3-(trifluoromethyl)-1H-pyrazole-5-carboxamide (136a)

To a solution of 1-(3-(aminomethyl)phenyl)-N-(3-((4-(benzyloxy)phenyl)(cyclopropylmethylamino)methyl)phenyl)-3-(trifluoromethyl)-1H-pyrazole-5-carboxamide (123f) (0.2 g, 0.320 mmol) in methanol (30 mL) was added hydrogen chloride (4N in dioxane, 0.799 mL, 3.20 mmol) and palladium (10% Pd on carbon) (0.102 g, 0.096 mmol). The reaction mixture was hydrogenated at 60 psi for 14 h. The reaction mixture was filtered through a small Celite pad and concentrated in vacuum. The residue obtained was purified by flash column chromatography (silica gel, 12 gm eluting with 0-25% methanol in chloroform) to afford 1-(3-(aminomethyl)phenyl)-N-(3-(4-hydroxybenzyl)phenyl)-3-(trifluoromethyl)-1H-pyrazole-5-carboxamide (136a) (0.211 g) hydrochloride salt as an off-white solid; $^1$H NMR (300 MHz, DMSO-$d_6$) δ 10.73 (s, 1H), 9.26 (s, 1H), 8.39 (s, 3H), 7.71 (t, J=1.7 Hz, 1H), 7.65 (d, J=0.7 Hz, 1H), 7.62 (dt, J=7.4, 1.6 Hz, 1H), 7.56 (d, J=7.8 Hz, 1H), 7.51 (ddd, J=5.7, 3.5, 1.5 Hz, 2H), 7.44 (t, J=1.9 Hz, 1H), 7.24 (t, J=7.8 Hz, 1H), 7.02-6.94 (m, 3H), 6.74-6.63 (m, 2H), 4.12 (s, 2H), 3.79 (s, 2H); $^{19}$F NMR (282 MHz, DMSO) δ −60.79; MS (ES+) 467.3 (M+1); (ES−) 501.2 (M−1); Analysis calculated for $C_{25}H_{21}F_3N_4O_2 \cdot HCl \cdot H_2O$: C, 57.64; H, 4.64; Cl, 6.81; N, 10.76; Found; C, 57.91; H, 4.75; Cl, 6.96; N, 10.64.

Scheme 137

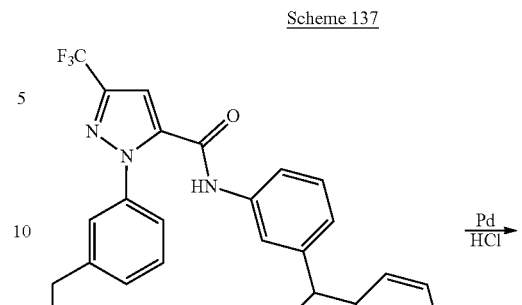

107f

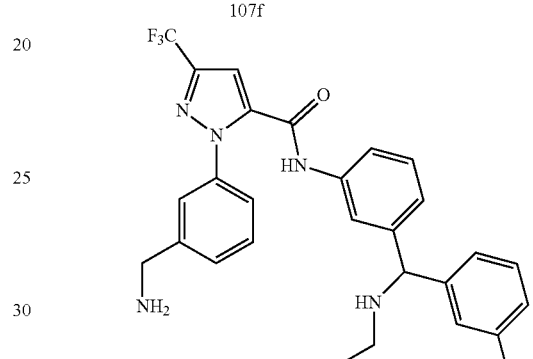

137a

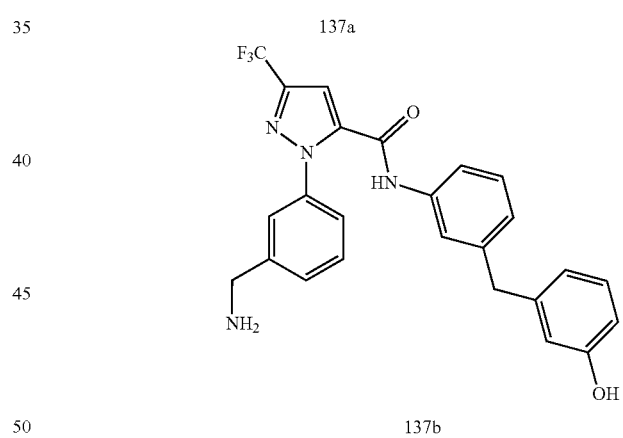

137b

Preparation of 1-(3-(Aminomethyl)phenyl)-N-(3-((cyclopropylmethylamino)(3-hydroxyphenyl)methyl)phenyl)-3-(trifluoromethyl)-1H-pyrazole-5-carboxamide (137a) and 1-(3-(aminomethyl)phenyl)-N-(3-(3-hydroxybenzyl)phenyl)-3-(trifluoromethyl)-1H-pyrazole-5-carboxamide (137b)

To a solution of 1-(3-(aminomethyl)phenyl)-N-(3-((3-(benzyloxy)phenyl)(cyclopropylmethylamino)methyl)phenyl)-3-(trifluoromethyl)-1H-pyrazole-5-carboxamide (107f) (0.31 g, 0.495 mmol) in methanol (30 mL) was added hydrogen chloride (4N in dioxane, 1.239 mL, 4.95 mmol) and palladium (10% Pd on carbon) (0.158 g, 0.149 mmol). The reaction mixture was hydrogenated at 60 psi for 14 h at room temperature. The reaction mixture was filtered through a small Celite pad and concentrated in vacuum to dryness.

The residue obtained was purified by flash column chromatography (silica gel, 12 gm eluting with 0-25% methanol in chloroform) to afford 1. 1-(3-(aminomethyl)phenyl)-N-(3-(3-hydroxybenzyl)phenyl)-3-(trifluoromethyl)-1H-pyrazole-5-carboxamide (137b) (0.211 g, 0.452 mmol, 91% yield) as a white solid; $^1$H NMR (300 MHz, DMSO-$d_6$) δ 10.76 (s, 1H), 9.34 (s, 1H), 8.49-8.32 (m, 3H), 7.72 (t, J=1.7 Hz, 1H), 7.66 (s, 1H), 7.64-7.57 (m, 1H), 7.56-7.45 (m, 4H), 7.26 (t, J=7.8 Hz, 1H), 7.11-6.97 (m, 2H), 6.66-6.51 (m, 3H), 4.12 (q, J=5.8 Hz, 2H), 3.81 (s, 2H); $^{19}$F NMR (282 MHz, DMSO) δ −60.79; MS (ES+) 467.3 (M+1); 489.2 (M+Na), (ES−) 465.3 (M−1); 501.2 (M+Cl); Analysis calculated for $C_{25}H_{21}F_3N_4O_2 \cdot HCl \cdot H_2O$: C, 57.64; H, 4.64; Cl, 6.81; N, 10.76; Found: C, 57.65; H, 4.64; Cl, 7.21; N, 10.68.

2. 1-(3-(aminomethyl)phenyl)-N-(3-((cyclopropylmethylamino)(3-hydroxyphenyl)methyl)phenyl)-3-(trifluoromethyl)-1H-pyrazole-5-carboxamide (137a) (0.02 g, 0.037 mmol, 7.54% yield) as a hygroscopic solid; $^1$H NMR (300 MHz, DMSO-$d_6$) δ 11.05 (s, 1H), 10.09 (s, 2H), 9.80 (s, 1H), 8.62 (s, 4H), 7.88-7.83 (m, 1H), 7.76 (s, 1H), 7.74 (d, J=2.1 Hz, 1H), 7.69-7.60 (m, 3H), 7.58-7.48 (m, 2H), 7.42 (t, J=7.9 Hz, 1H), 7.25-7.10 (m, 2H), 7.03-6.97 (m, 1H), 6.78 (ddd, J=7.9, 2.4, 1.1 Hz, 1H), 5.44 (d, J=6.2 Hz, 1H), 4.11 (s, 3H), 2.78-2.59 (m, 2H), 1.17 (tt, J=7.8, 4.5 Hz, 1H), 0.63-0.44 (m, 2H), 0.32 (dt, J=6.5, 4.4 Hz, 2H); $^{19}$F NMR (282 MHz, DMSO) δ −60.77; MS (ES+) 536.3 (M+1); (ES−) 570.3 (M−1); Analysis calculated for $C_{29}H_{28}F_3N_5O_2 \cdot 2.5C_4H_9 \cdot 2.5HCl \cdot 2.25HCl \cdot 3.25H_2O$: C, 49.56; H, 6.59; Cl, 17.82; N, 11.12; Found: C, 49.81; H, 6.58; Cl, 17.65; N, 10.70 (From NMR analysis and integration the sample is contaminated with 2.5 equivalents of cyclopropylmethylamine hydrochloride).

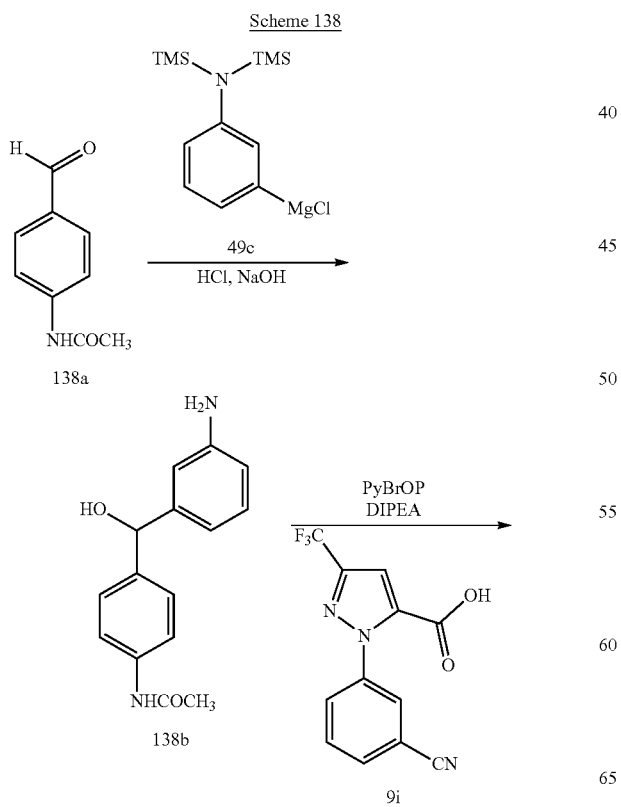

Scheme 138

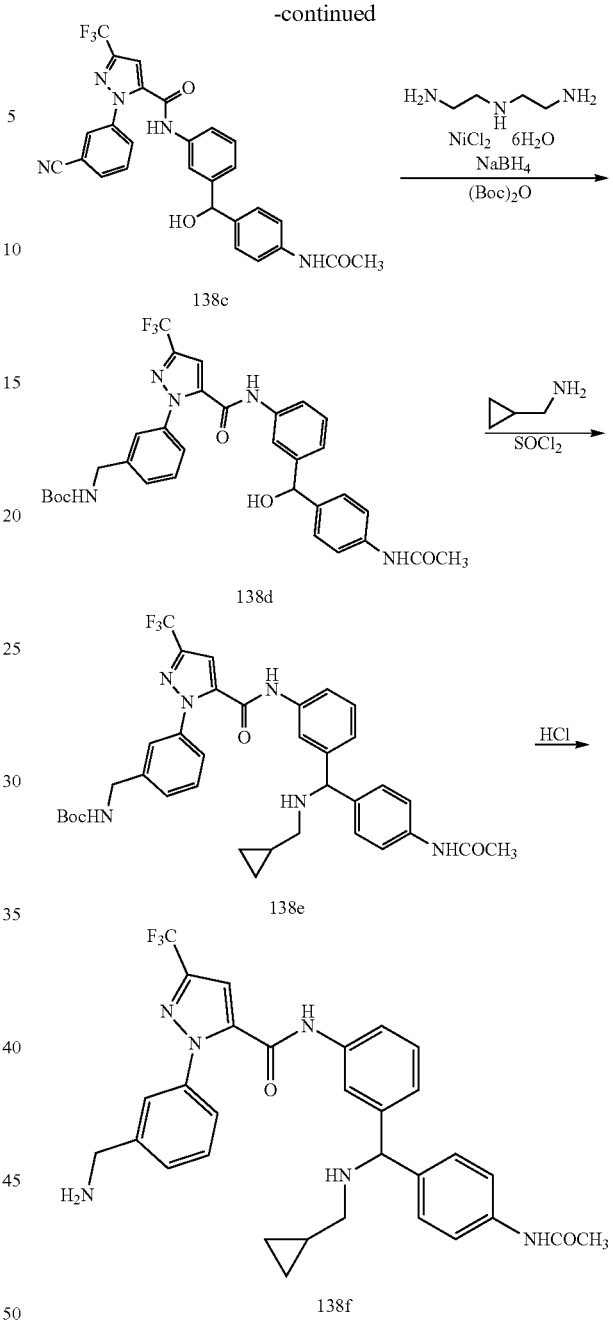

Preparation of N-(3-((4-acetamidophenyl)(cyclopropylmethylamino)methyl)phenyl)-1-(3-(aminomethyl)phenyl)-3-(trifluoromethyl)-1H-pyrazole-5-carboxamide (138f)

Step-1: Preparation of N-(4-((3-aminophenyl)(hydroxy)methyl)phenyl)acetamide (138b)

To a stirred solution of N-(4-formylphenyl)acetamide (138a) (1 g, 6.13 mmol) in tetrahydrofuran (7 mL) was added (3-(bis(trimethylsilyl)amino)phenyl)magnesium chloride (49c) (7.40 mL, 7.40 mmol) at 0° C. The reaction was stirred for 12 h quenched with 2 N HCl (15 mL) and stirred for additional 6 h at room temperature. The reaction mixture was basified with 2 N NaOH (15 mL) and extracted with ethyl acetate (2×50 mL). The organic layers were combined washed with saturated NH$_4$Cl (50 mL), dried over anhydrous MgSO$_4$, filtered, evaporated to dryness. The crude residue was purified by flash column chromatography [silica gel 40 g, eluting with chloroform/methanol (1:0 to 9:1)] to give N-(4-((3-aminophenyl)(hydroxy)methyl)phenyl)acetamide (138b) (1.455 g, 93%) as a yellow solid; $^1$H NMR (300 MHz, DMSO-d$_6$) δ 9.86 (s, 1H), 7.50-7.41 (m, 2H), 7.29-7.18 (m, 2H), 6.90 (t, J=7.7 Hz, 1H), 6.54 (t, J=2.0 Hz, 1H), 6.51-6.46 (m, 1H), 6.37 (ddd, J=7.9, 2.3, 1.1 Hz, 1H), 5.61 (d, J=3.8 Hz, 1H), 5.44 (d, J=3.8 Hz, 1H), 4.97 (s, 2H), 2.00 (s, 3H); MS (ES+): 279.2 (M+Na).

Step-2: Preparation of N-(3-((4-acetamidophenyl)(hydroxy)methyl)phenyl)-1-(3-cyanophenyl)-3-(trifluoromethyl)-1H-pyrazole-5-carboxamide (138c)

To a solution of 1-(3-cyanophenyl)-3-(trifluoromethyl)-1H-pyrazole-5-carboxylic acid (9i) (1.514 g, 5.38 mmol) in DMF (27 mL) was added N-(4-((3 aminophenyl)(hydroxy)methyl)phenyl)acetamide (138b) (1.38 g, 5.38 mmol), N-ethyl-N-isopropylpropan-2-amine (7.70 mL, 44.2 mmol) and bromo-tris-pyrrolidino phosphoniumhexafluorophosphate (PyBrOP, 2.56 g, 5.38 mmol) at room temperature. The reaction mixture was stirred at room temperature for 22 h under nitrogen atmosphere. The reaction was diluted with ethyl acetate (200 mL) washed with water (2×80 mL), brine (80 mL), dried, filtered, and evaporated to dryness. The residue obtained was purified by flash column chromatography [silica gel 40 g, eluting with hexanes/10% methanol in ethyl acetate (1:0 to 1:1)] to furnish N-(3-((4-acetamidophenyl)(hydroxy)methyl)phenyl)-1-(3-cyanophenyl)-3-(trifluoromethyl)-1H-pyrazole-5-carboxamide (138c) (2.28 g) as a yellow solid, which was used as such for next step. MS (ES+): 542.2 (M+Na).

Step-3: Preparation of tert-butyl 3-(5-(3-((4-acetamidophenyl)-(hydroxy)methyl)phenylcarbamoyl)-3-(trifluoromethyl)-1H-pyrazol-1-yl)benzylcarbamate (138d)

To a solution of N-(3-((4-acetamidophenyl)(hydroxy)methyl)phenyl)-1-(3-cyanophenyl)-3-(trifluoromethyl)-1H-pyrazole-5-carboxamide (138c) (2.13 g, 4.10 mmol) in MeOH (70 mL) cooled with ice/water was added nickel(II) chloride hexahydrate (0.524 g, 2.206 mmol) and di-tert-butyl dicarbonate (3.62 g, 16.40 mmol) followed by portionwise addition of sodium borohydride (1.583 g, 41.0 mmol) over a period of 15 min. The reaction mixture was stirred at room temperature for 2 hrs and quenched with N$^1$-(2-aminoethyl)ethane-1,2-diamine (2.0 mL, 18.33 mmol) followed by stirring for additional 0.5 h. The reaction mixture was concentrated in vacuum to dryness and the residue obtained was dissolved in ethyl acetate (200 mL) and water (200 mL). The aqueous layer was separated extracted with ethyl acetate (200 mL). The combined extracts were washed with brine (100 mL), dried over MgSO$_4$ filtered and concentrated in vacuum. The residue obtained was purified by flash column chromatography [silica gel 40 g, eluting with chloroform/methanol (1:0 to 9:1)] to give tert-butyl 3-(5-(3-((4-acetamidophenyl)-(hydroxy)methyl)phenylcarbamoyl)-3-(trifluoromethyl)-1H-pyrazol-1-yl)benzylcarbamate (138d) (1.284 g, 41% for 2 steps). $^1$H NMR (300 MHz, DMSO-d$_6$) δ 10.68 (s, 1H), 9.88 (s, 1H), 7.60-7.20 (m, 13H), 7.11 (d, J=7.7 Hz, 1H), 5.86 (d, J=3.8 Hz, 1H), 5.60 (d, J=3.8 Hz, 1H), 4.19 (d, J=6.2 Hz, 2H), 2.01 (s, 3H), 1.37 (s, 9H); $^{19}$F NMR (282 MHz, DMSO-d$_6$) δ −60.79; MS (ES+): 646.3 (M+Na).

Step-4: Preparation of tert-butyl 3-(5-(3-((4-acetamidophenyl)(cyclopropyl-methylamino)methyl)phenylcarbamoyl)-3-(trifluoromethyl)-1H-pyrazol-1-yl)benzylcarbamate (138e)

To a solution of tert-butyl 3-(5-(3-((4-acetamidophenyl)-(hydroxy)methyl)phenylcarbamoyl)-3-(trifluoromethyl)-1H-pyrazol-1-yl)benzylcarbamate (138d) (0.218 g, 1.953 mmol) in dichloromethane (36 mL) at 0° C. was added thionyl chloride (0.3 mL, 4.05 mmol) and stirred at room temperature for 2 h. The reaction mixture was quenched with triethyl amine (1.800 mL, 12.92 mmol), stirred for 1 h and concentrated in vacuum to dryness. The residue obtained was dissolved in acetonitrile (27 mL) and added cyclopropylmethanamine (3.70 mL, 41.4 mmol). The reaction mixture was heated at 70° C. for 14 h, cooled to room temperature and concentrated in vacuum to dryness. The residue was dissolved in chloroform (240 mL), washed with water (100 mL), dried, filtered and concentrated in vacuum. The residue obtained was purified by flash column chromatography [silica gel 40 g, eluting with chloroform/methanol (1:0 to 19:1)] to give tert-butyl 3-(5-(3-((4-acetamidophenyl)(cyclopropyl-methylamino)methyl)phenylcarbamoyl)-3-(trifluoromethyl)-1H-pyrazol-1-yl)benzylcarbamate (138e) (240 mg) as a white solid; MS (ES+): 677.4 (M+H).

Step-5: Preparation of N-(3-((4-acetamidophenyl)(cyclopropylmethylamino)methyl)phenyl)-1-(3-(aminomethyl)phenyl)-3-(trifluoromethyl)-1H-pyrazole-5-carboxamide (138f)

To a solution of tert-butyl 3-(5-(3-((4-acetamidophenyl)(cyclopropyl-methylamino)methyl)phenylcarbamoyl)-3-(trifluoromethyl)-1H-pyrazol-1-yl)benzylcarbamate (138e) (227 mg, 0.335 mmol) in 1,4-Dioxane (22 mL) was added hydrogen chloride (3.70 mL, 14.79 mmol, 4 M in 1,4-dioxane). The reaction mixture was stirred at room temperature for 16 h. The reaction mixture was treated with hexanes, decanted, washed with hexanes, and decanted again. The insoluble crude product was purified by combiflash column chromatography on silica gel with chloroform/CMA80 (1:0 to 2:1) to give N-(3-((4-acetamidophenyl)(cyclopropylmethylamino)methyl)phenyl)-1-(3-(aminomethyl)phenyl)-3-(trifluoromethyl)-1H-pyrazole-5-carboxamide (138f) (43 mg) free base as a white solid. The purified product (138f) (41 mg) was dissolved in methanol (10 mL) and treated with 4 N HCl (aq. 0.08 mL) followed by concentration to dryness to N-(3-((4-acetamidophenyl)(cyclopropylmethylamino)methyl)phenyl)-1-(3-(aminomethyl)phenyl)-3-(trifluoromethyl)-1H-pyrazole-5-carboxamide (43 mg, 3.8% for 2 steps) hydrochloride salt as a light yellow solid; $^1$H NMR (300 MHz, DMSO-d$_6$) δ 10.92 (s, 1H), 10.14 (s, 1H), 9.85 (s, 2H), 8.37 (s, 3H), 7.83 (s, 1H), 7.73 (d, J=1.9 Hz, 1H), 7.67 (s, 1H), 7.64-7.48 (m, 9H), 7.44 (t, J=7.9 Hz, 1H), 5.51 (t, J=5.5 Hz, 1H), 4.13 (d, J=5.3 Hz, 2H), 2.78-2.63 (m, 3H), 2.04 (s, 3H), 1.12 (td, J=13.2, 12.5, 7.0 Hz, 1H), 0.64-0.47 (m, 2H), 0.37-0.22 (m, 2H); $^1$H NMR (300 MHz, DMSO-d$_6$, D$_2$O exchange) δ 7.79 (t, 1H), 7.70 (t, 1H), 7.64-7.40 (m, 11H), 5.51 (s, 1H), 4.13 (s, 2H), 2.73 (t, J=7.0 Hz, 2H), 2.05 (s, 3H), 1.16-0.98 (m, 1H), 0.64-0.54 (m, 2H), 0.32-0.24 (m, 2H); $^{19}$F NMR (282 MHz, DMSO-d$_6$) δ −60.79; MS (ES+): 577.3 (M+H); Analysis calculated for $C_{31}H_{31}F_3N_6O_2 \cdot 2HCl \cdot 3H_2O$: C, 52.92; H, 5.59; N, 11.94; Found: 52.66; H, 5.51; N, 11.56; C, 52.66; H, 5.51; N, 11.56.

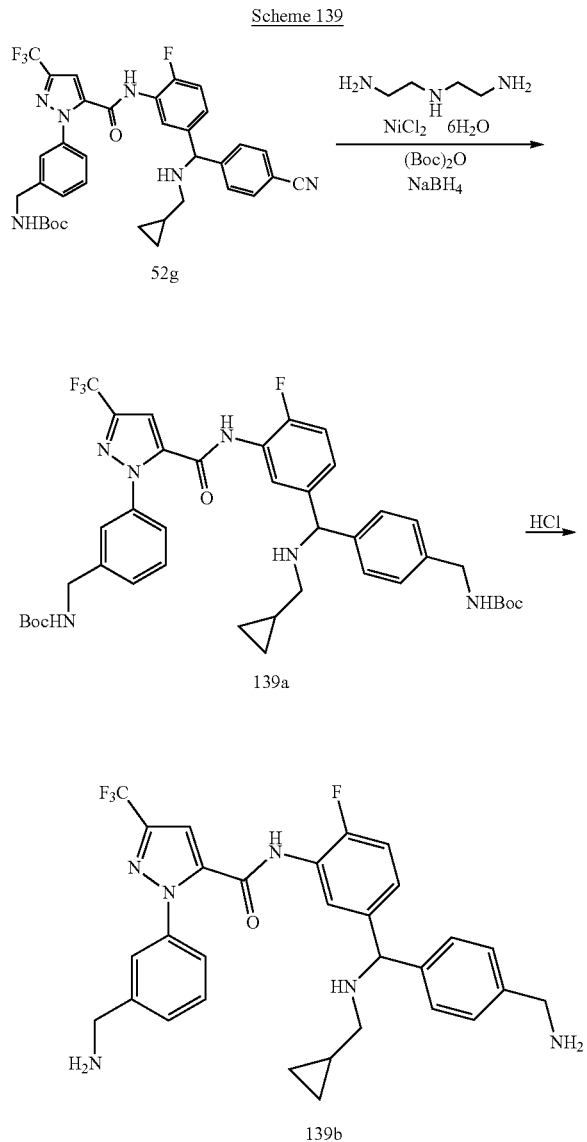

Scheme 139

Preparation of 1-(3-(aminomethyl)phenyl)-N-(5-((4-(aminomethyl)phenyl)(cyclopropyl-methylamino)methyl)-2-fluorophenyl)-3-(trifluoromethyl)-1H-pyrazole-5-carboxamide (139b)

Step-1: Preparation of tert-butyl 3-(5-((5-((4-(tert-butyloxycarbonylaminomethyl)phenyl)((cyclopropylmethyl)amino)methyl)-2-fluorophenyl)carbamoyl)-3-(trifluoromethyl)-1H-pyrazol-1-yl)benzylcarbamate (139a)

To a solution of tert-butyl 3-(5-(5-((4-cyanophenyl)(cyclopropylmethylamino)methyl)-2-fluorophenylcarbamoyl)-3-(trifluoromethyl)-1H-pyrazol-1-yl)benzylcarbamate (52g) (155 mg, 0.234 mmol) in MeOH (5 mL) cooled with ice/water was added nickel(II) chloride hexahydrate (30.0 mg, 0.126 mmol) and di-tert-butyl dicarbonate (206 mg, 0.936 mmol) followed by portion-wise addition of sodium borohydride (90 mg, 2.339 mmol) over a period of 15 min. The reaction mixture was stirred at room temperature for 2 hrs and quenched with $N^1$-(2-aminoethyl)ethane-1,2-diamine (0.110 mL, 1.006 mmol) followed by stirring for additional 0.5 h. The reaction mixture was concentrated in vacuum to dryness and the residue obtained was dissolved in ethyl acetate (100 mL) and water (60 mL). The aqueous layer was separated extracted with ethyl acetate (60 mL). The combined extracts were washed with brine (60 mL), dried over $MgSO_4$ filtered and concentrated in vacuum. The residue obtained was purified by flash column chromatography [silica gel 40 g, eluting with hexanes/ethyl acetate (1:0 to 1:1)] to give tert-butyl 3-(5-((5-((4-(tert-butyloxycarbonylaminomethyl)phenyl)((cyclopropylmethyl) amino) methyl)-2-fluorophenyl)carbamoyl)-3-(trifluoromethyl)-1H-pyrazol-1-yl)benzylcarbamate (139a) (70 mg, 39%) as a colorless gum; $^1$H NMR (300 MHz, DMSO-$d_6$) δ 10.54 (s, 1H), 7.68-7.10 (m, 14H), 4.81 (s, 1H), 4.19 (d, J=6.4 Hz, 2H), 4.05 (d, J=6.7 Hz, 2H), 2.29-2.23 (m, 2H), 1.38 (s, 18H), 1.00-0.80 (m, 1H), 0.43-0.28 (m, 2H), 0.07-0.00 (m, 2H); $^{19}$F NMR (282 MHz, DMSO-$d_6$) δ −60.81, −123.76; MS (ES+): 767.5 (M+H).

Step-2: Preparation of 1-(3-(aminomethyl)phenyl)-N-(5-((4-(aminomethyl)phenyl)(cyclopropylmethylamino)methyl)-2-fluorophenyl)-3-(trifluoromethyl)-1H-pyrazole-5-carboxamide (139b)

To a solution of give tert-butyl 3-(5-((5-((4-(tert-butyloxycarbonylaminomethyl)phenyl)((cyclopropylmethyl)amino)methyl)-2-fluorophenyl)carbamoyl)-3-(trifluoromethyl)-1H-pyrazol-1-yl)benzylcarbamate (139a) (60 mg) in 1,4-Dioxane (7 mL) was added hydrogen chloride (0.970 mL, 3.88 mmol, 4 M in 1,4-dioxane) and stirred at room temperature for 21 h. The reaction mixture was treated with hexanes, decanted, washed with hexanes, and decanted again. The insoluble crude product was purified by flash column chromatography [silica gel, eluting with chloroform/CMA80 (1:0 to 1:1)] to give 1-(3-(aminomethyl)phenyl)-N-(5-((4-(aminomethyl)phenyl)(cyclopropylmethylamino)methyl)-2-fluorophenyl)-3-(trifluoromethyl)-1H-pyrazole-5-carboxamide (139b) (23 mg, 46%) free base as a colorless gum. The purified free base (139b) was dissolved in methanol (10 mL) and added 4 N HCl (aq. 0.04 mL), stirred for 30 mins followed by concentration to dryness to give 1-(3-(aminomethyl)phenyl)-N-(5-((4-(aminomethyl)phenyl)(cyclopropylmethylamino)methyl)-2-fluorophenyl)-3-(trifluoromethyl)-1H-pyrazole-5-carboxamide (139b) (31 mg) hydrochloride salt as a white solid; $^1$H NMR (300 MHz, DMSO-$d_6$) δ 10.83 (s, 1H), 10.29 (d, J=38.5 Hz, 0H), 8.40 (s, 6H), 7.95 (s, 1H), 7.77 (d, J=8.2 Hz, 2H), 7.71 (d, J=4.4 Hz, 3H), 7.65-7.60 (m, 1H), 7.57 (d, J=7.8 Hz, 1H), 7.55-7.50 (m, 3H), 7.40 (t, J=9.3 Hz, 1H), 5.68 (s, 1H), 4.13 (s, 2H), 4.00 (s, 2H), 2.75-2.63 (m, 2H), 1.23-1.09 (m, 1H), 0.56 (m, 2H), 0.30 (m, 2H); $^1$H NMR ($D_2O$ ex NMR, 300 MHz, DMSO-$d_6$) δ 7.89 (d, J=6.9 Hz, 1H), 7.74-7.48 (m, 10H), 7.42 (t, J=9.5 Hz, 1H), 5.66 (s, 1H), 4.12 (s, 2H), 4.02 (s, 2H), 2.78-2.67 (m, 2H), 1.14-1.00 (m, 1H), 0.59 (d, J=7.8 Hz, 2H), 0.28 (s, 2H); $^{19}$F NMR (282 MHz, DMSO-$d_6$) δ −60.82, −120.56; MS (ES+): 567.3 (M+1); Analysis calculated for $C_{30}H_{30}F_4N_6O \cdot 3HCl \cdot 4H_2O$: C, 48.17; H, 5.52; N, 11.23.; Found: C, 47.79; H, 5.78; N, 10.84.

Scheme 140

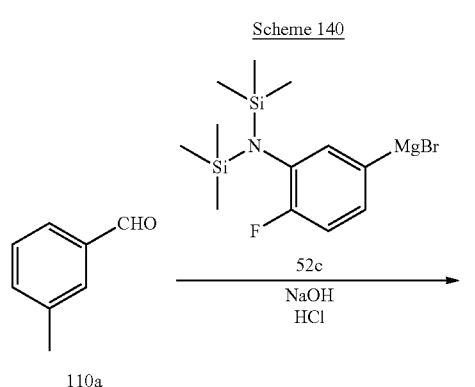

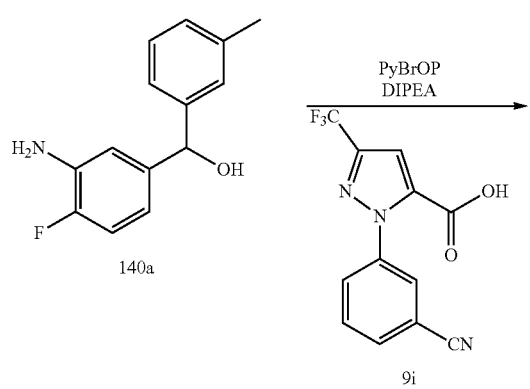

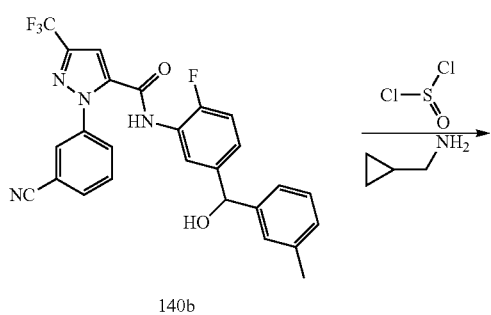

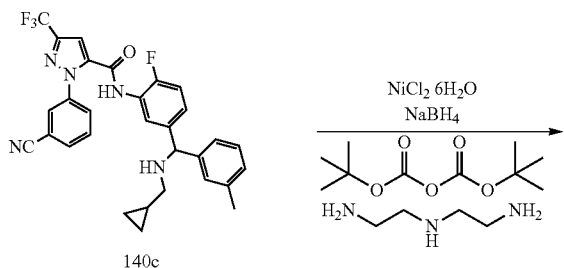

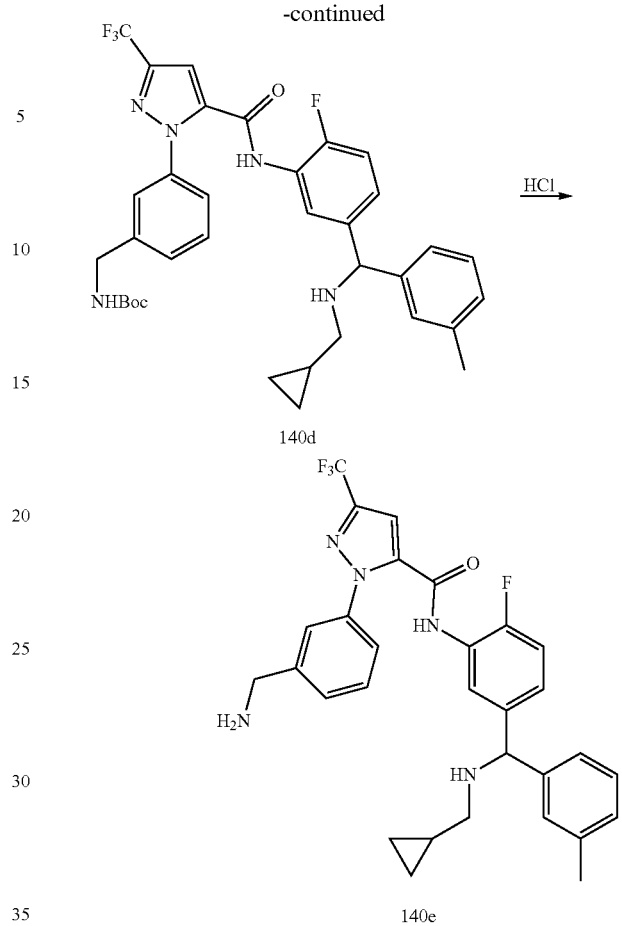

Preparation of 1-(3-(aminomethyl)phenyl)-N-(5-((((cyclopropylmethyl)amino)(m-tolyl)methy)-2-fluorophenyl)-3-(trifluoromethyl)-1H-pyrazole-5-carboxamide (140e)

Step-1: Preparation of (3-amino-4-fluorophenyl)(m-tolyl)methanol (140a)

To a stirred solution of 3-methylbenzaldehyde (110a) (1.179 mL, 10 mmol) in tetrahydrofuran (5 mL) was added (3-(bis(trimethylsilyl)amino)-4-fluorophenyl)magnesium bromide (52c) (18.00 mL, 18.00 mmol) at 0° C. The reaction was stirred for 14 h at same temperature and quenched by adding 2 N HCl (10 mL, 20 mmol), stirred for 0.5 h. The reaction mixture was basified by aqueous NaHCO$_3$ and extracted with ethyl acetate (2×250 mL). The organic layers were combined washed with water (2×50 mL), brine (50 mL) dried over anhydrous MgSO$_4$, filtered, evaporated to dryness. The crude residue was purified by flash column chromatography (silica gel 80 g, eluting with ethyl acetate in hexane from 0-100%) to afforded (3-amino-4-fluorophenyl)(m-tolyl)methanol (140a) (1.771 g, 7.66 mmol, 51.1% yield) as a light yellow oil; $^1$H NMR (300 MHz, DMSO-d$_6$) δ 7.23-7.06 (m, 3H), 7.00 (dt, J=7.1, 1.7 Hz, 1H), 6.86 (dd, J=11.5, 8.3 Hz, 1H), 6.75 (dd, J=9.0, 2.1 Hz, 1H), 6.49 (ddd, J=8.3, 4.5, 2.2 Hz, 1H), 5.70 (d, J=3.8 Hz, 1H, D$_2$O exchangeable), 5.48 (d, J=3.7 Hz, 1H), 5.05 (s, 2H, D$_2$O exchangeable), 2.26 (s, 3H); Mass spec (ES+) 254.1 (M+24); (ES−) 230.1 (M−1).

Step-2: Preparation of 1-(3-cyanophenyl)-N-(2-fluoro-5-(hydroxy(m-tolyl)methyl)phenyl)-3-(trifluoromethyl)-1H-pyrazole-5-carboxamide (140b)

In a 100 mL single-necked flask containing 1-(3-cyanophenyl)-3-(trifluoromethyl)-1H-pyrazole-5-carboxylic acid (9i) (2.341 g, 8.32 mmol), (3-amino-4-fluorophenyl)(m-tolyl)methanol (140a) (1.75 g, 7.57 mmol), bromo-tris-pyrrolidino phosphoniumhexafluorophosphate(PyBrop) (4.23 g, 9.08 mmol) was added N,N-dimethylformamide (20 mL) and N-ethyl-N-isopropylpropan-2-amine (DIPEA, 6.59 mL, 37.8 mmol) successively in a positive flow of nitrogen at room temperature. The resulting reaction mixture was stirred at room temperature for 20 h under a positive flow of nitrogen atmosphere. The reaction was diluted with water (100 mL) and extracted with ethyl acetate (2×200 mL). The organic layers were combined, washed with water (2×100 mL), brine (50 mL), dried, filtered, and evaporated in vacuum to dryness. The residue obtained was purified by flash column chromatography (silica gel 40 g, eluting with 0-100% ethyl acetate in hexanes) to afford 1-(3-cyanophenyl)-N-(2-fluoro-5-(hydroxy(m-tolyl)methyl)phenyl)-3-(trifluoromethyl)-1H-pyrazole-5-carboxamide (140b) (2.29 g, 4.63 mmol, 61.2% yield) as a yellow semisolid; $^1$H NMR (300 MHz, DMSO-$d_6$) δ 10.54 (s, 1H, $D_2O$ exchangeable), 8.16-8.10 (m, 1H), 8.00 (dt, J=7.7, 1.3 Hz, 1H), 7.93-7.86 (m, 1H), 7.77-7.68 (m, 2H), 7.50 (d, J=7.2 Hz, 1H), 7.30-7.10 (m, 5H), 7.05-6.98 (m, 1H), 5.96 (d, J=3.9 Hz, 1H, $D_2O$ exchangeable), 5.64 (d, J=3.9 Hz, 1H), 2.26 (s, 3H); MS (ES+) 517.2 (M+Na), (ES−) 493.2 (M−1).

Step-3: Preparation of 1-(3-cyanophenyl)-N-(5-(((cyclopropylmethyl)amino)(m-tolyl)methyl)-2-fluorophenyl)-3-(trifluoromethyl)-1H-pyrazole-5-carboxamide (140c)

To a solution of 1-(3-cyanophenyl)-N-(2-fluoro-5-(hydroxy(m-tolyl)methyl)phenyl)-3-(trifluoromethyl)-1H-pyrazole-5-carboxamide (140b) (2.12 g, 4.29 mmol) in dichloromethane (50 mL) at 0° C. was added thionyl chloride (0.668 mL, 9.15 mmol), stirred at room temperature for 2 h and quenched with triethylamine (3.97 mL, 28.5 mmol). The reaction mixture was stirred for 1 h and added cyclopropylmethanamine (7.83 mL, 91 mmol) and concentrated in vacuum to remove dichloromethane. The residue obtained was dissolved in acetonitrile (20 mL) and added cyclopropylmethanamine (7.83 mL, 91 mmol). The reaction mixture was heated at reflux overnight, cooled to room temperature and concentrated in vacuum to dryness. The residue was dissolved in chloroform (300 mL), washed with water (100 mL), dried, filtered and concentrated in vacuum. The residue obtained was purified by flash column chromatography (silica gel 25 g, eluting with CMA 80 in chloroform 0 to 20%) to afford 1-(3-cyanophenyl)-N-(5-((cyclopropylmethylamino)(m-tolyl)methyl)-2-fluorophenyl)-3-(trifluoromethyl)-1H-pyrazole-5-carboxamide (140c) (1.3 g, 2.374 mmol, 55.4% yield) as an oil; MS (ES+) 548.3 (M+1), (ES−) 546.3 (M−1).

Step-4: Preparation of tert-butyl 3-(5-((5-(((cyclopropylmethyl)amino)(m-tolyl)methyl)-2-fluorophenyl)carbamoyl)-3-(trifluoromethyl)-1H-pyrazol-1-yl)benzylcarbamate (140d)

To a solution of 1-(3-cyanophenyl)-N-(5-((cyclopropylmethylamino)(m-tolyl)methyl)-2-fluorophenyl)-3-(trifluoromethyl)-1H-pyrazole-5-carboxamide (140c) (1.25 g, 2.283 mmol) in MeOH (25 mL) cooled with ice/water was added di-tert-butyl dicarbonate (1.993 g, 9.13 mmol) and nickel(II) chloride (0.136 g, 0.571 mmol). Sodium Borohydride (0.818 g, 22.83 mmol) was added slowly over 15 min and reaction mixture was stirred at room temperature for 1 h. The reaction mixture was quenched with N1-(2-aminoethyl)ethane-1,2-diamine (1.110 mL, 10.27 mmol) stirred for 0.5 h and concentrated in vacuum to dryness. The residue obtained was diluted with water (200 mL). The solid separated was collected by filtration and purified by flash column chromatography [silica gel 40 g, eluting with hexanes/ethyl acetate (1:0 to 2:1)] to afford tert-butyl 3-(5-((5-(((cyclopropylmethyl)amino)(m-tolyl)methyl)-2-fluorophenyl)carbamoyl)-3-(trifluoromethyl)-1H-pyrazol-1-yl)benzylcarbamate (140d) (0.864 g, 1.326 mmol, 58.1% yield) as a white solid.

Step-5: Preparation of 1-(3-(aminomethyl)phenyl)-N-(5-(((cyclopropylmethyl)amino)(m-tolyl)methyl)-2-fluorophenyl)-3-(trifluoromethyl)-1H-pyrazole-5-carboxamide (140e)

To a solution of tert-butyl 3-(5-((5-(((cyclopropylmethyl)amino)(m-tolyl)methyl)-2-fluorophenyl)carbamoyl)-3-(trifluoromethyl)-1H-pyrazol-1-yl)benzylcarbamate (140d) (0.8 g, 1.228 mmol) in methanol (10 mL) was added conc. hydrogen chloride (3.73 mL, 123 mmol), stirred at room temperature overnight and concentrated in vacuum to dryness. The residue obtained was purified by flash column chromatography (silica gel 24 g, eluting with 0-100% CMA-80 in chloroform) to afford 1-(3-(aminomethyl)phenyl)-N-(5-(((cyclopropylmethyl)amino)(m-tolyl)methyl)-2-fluorophenyl)-3-(trifluoromethyl)-1H-pyrazole-5-carboxamide (140e) as a free base. To a solution of free base of compound 140e in methanol (10 mL) was added conc. hydrochloric acid (0.121 mL, 1.450 mmol), stirred for 30 mins and concentrated in vacuum to dryness to afford 1-(3-(aminomethyl)phenyl)-N-(5-((cyclopropylmethylamino)(m-tolyl)methyl)-2-fluorophenyl)-3-(trifluoromethyl)-1H-pyrazole-5-carboxamide (140e) (110 mg, 60.7% yield) hydrochloride salt as a white solid. $^1$HNMR (300 MHz, DMSO-$d_6$) δ 10.82 (s, 1H, $D_2O$ exchangeable), 10.12 (s, 2H, $D_2O$ exchangeable), 8.45 (s, 3H, $D_2O$ exchangeable), 7.92 (dd, J=7.3, 2.3 Hz, 1H), 7.76-7.66 (m, 3H), 7.63 (dt, J=7.3, 1.8 Hz, 1H), 7.57 (d, J=7.8 Hz, 1H), 7.55-7.48 (m, 3H), 7.40 (dd, J=10.3, 8.6 Hz, 1H), 7.32 (t, J=7.9 Hz, 1H), 7.18 (d, J=7.5 Hz, 1H), 5.59 (s, 1H), 4.13 (s, 2H), 2.69 (s, 2H), 2.30 (s, 3H), 1.14 (dd, J=10.1, 5.5 Hz, 1H), 0.60-0.51 (m, 2H), 0.29 (dd, J=5.8, 4.1 Hz, 2H). MS (ES+) 552.3 (M+1), (ES−) 550.2 (M−1), 586.3 (M+35); Analysis calculated for $C_{30}H_{29}F_4N_5O.2HCl.2H_2O$: C, 56.14; H, 5.18; N, 10.91; Cl, 10.90; Found: C, 56.01; H, 5.27; N, 10.72; Cl, 11.14.

Scheme 141

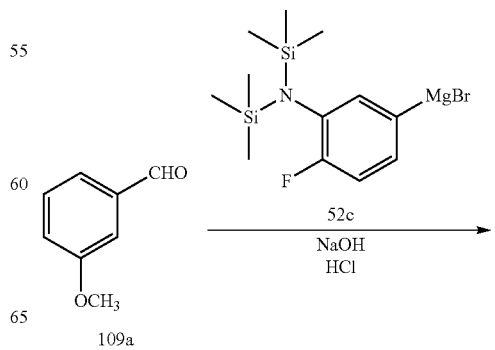

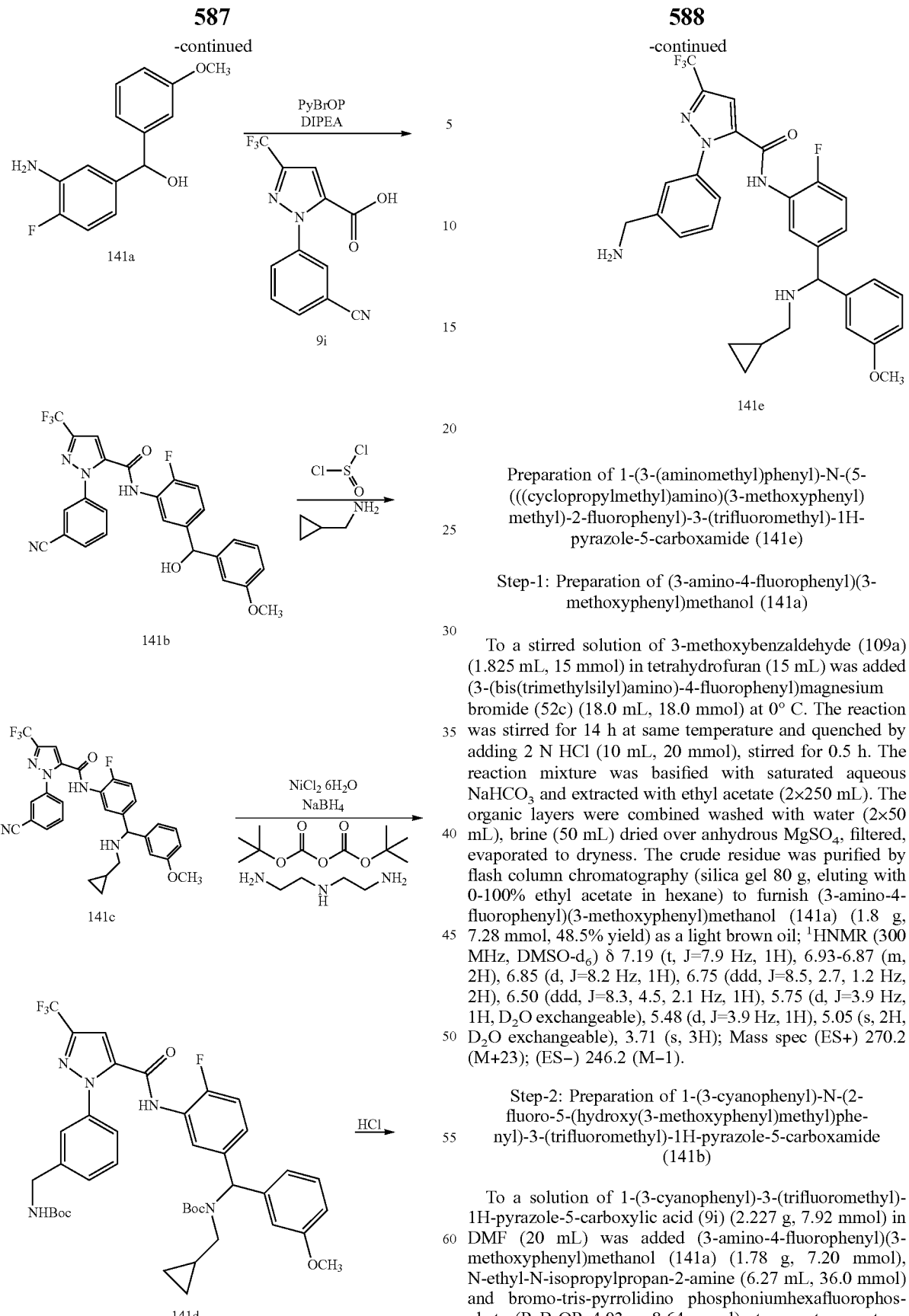

Preparation of 1-(3-(aminomethyl)phenyl)-N-(5-((((cyclopropylmethyl)amino)(3-methoxyphenyl)methyl)-2-fluorophenyl)-3-(trifluoromethyl)-1H-pyrazole-5-carboxamide (141e)

Step-1: Preparation of (3-amino-4-fluorophenyl)(3-methoxyphenyl)methanol (141a)

To a stirred solution of 3-methoxybenzaldehyde (109a) (1.825 mL, 15 mmol) in tetrahydrofuran (15 mL) was added (3-(bis(trimethylsilyl)amino)-4-fluorophenyl)magnesium bromide (52c) (18.0 mL, 18.0 mmol) at 0° C. The reaction was stirred for 14 h at same temperature and quenched by adding 2 N HCl (10 mL, 20 mmol), stirred for 0.5 h. The reaction mixture was basified with saturated aqueous NaHCO₃ and extracted with ethyl acetate (2×250 mL). The organic layers were combined washed with water (2×50 mL), brine (50 mL) dried over anhydrous MgSO₄, filtered, evaporated to dryness. The crude residue was purified by flash column chromatography (silica gel 80 g, eluting with 0-100% ethyl acetate in hexane) to furnish (3-amino-4-fluorophenyl)(3-methoxyphenyl)methanol (141a) (1.8 g, 7.28 mmol, 48.5% yield) as a light brown oil; $^1$HNMR (300 MHz, DMSO-$d_6$) δ 7.19 (t, J=7.9 Hz, 1H), 6.93-6.87 (m, 2H), 6.85 (d, J=8.2 Hz, 1H), 6.75 (ddd, J=8.5, 2.7, 1.2 Hz, 2H), 6.50 (ddd, J=8.3, 4.5, 2.1 Hz, 1H), 5.75 (d, J=3.9 Hz, 1H, D₂O exchangeable), 5.48 (d, J=3.9 Hz, 1H), 5.05 (s, 2H, D₂O exchangeable), 3.71 (s, 3H); Mass spec (ES+) 270.2 (M+23); (ES−) 246.2 (M−1).

Step-2: Preparation of 1-(3-cyanophenyl)-N-(2-fluoro-5-(hydroxy(3-methoxyphenyl)methyl)phenyl)-3-(trifluoromethyl)-1H-pyrazole-5-carboxamide (141b)

To a solution of 1-(3-cyanophenyl)-3-(trifluoromethyl)-1H-pyrazole-5-carboxylic acid (9i) (2.227 g, 7.92 mmol) in DMF (20 mL) was added (3-amino-4-fluorophenyl)(3-methoxyphenyl)methanol (141a) (1.78 g, 7.20 mmol), N-ethyl-N-isopropylpropan-2-amine (6.27 mL, 36.0 mmol) and bromo-tris-pyrrolidino phosphoniumhexafluorophosphate (PyBrOP, 4.03 g, 8.64 mmol) at room temperature. The reaction mixture was stirred at room temperature for 20 h under nitrogen atmosphere. The reaction was diluted with water (100 mL) and extracted with ethyl acetate (2×100 mL). The organic layers were combined, washed with water (2×100 mL), brine (50 mL), dried, filtered, and evaporated in vacuum to dryness. The residue obtained was purified by flash column chromatography (silica gel 40 g, eluting with 0-100% ethyl acetate in hexanes) to furnish 1-(3-cyanophenyl)-N-(2-fluoro-5-(hydroxy(3-methoxyphenyl)methyl) phenyl)-3-(trifluoromethyl)-1H-pyrazole-5-carboxamide (141b) (2.105 g, 4.12 mmol, 57.3% yield) as a yellow semisolid; $^1$H NMR (300 MHz, DMSO-$d_6$) δ 10.54 (s, 1H, $D_2O$ exchangeable), 8.12 (t, J=1.8 Hz, 1H), 8.00 (dt, J=7.8, 1.3 Hz, 1H), 7.90 (dt, J=8.4, 1.3 Hz, 1H), 7.79-7.63 (m, 2H), 7.52 (d, J=7.2 Hz, 1H), 7.35-7.09 (m, 3H), 6.95-6.88 (m, 2H), 6.83-6.68 (m, 1H), 6.00 (d, J=4.0 Hz, 1H, $D_2O$ exchangeable), 5.66 (d, J=3.9 Hz, 1H), 3.70 (s, 3H); MS (ES+) 533.2 (M+Na) (ES−) 509.2 (M−1).

Step-3: Preparation of 1-(3-cyanophenyl)-N-(5-(((cyclopropylmethyl)amino)(3-methoxyphenyl) methyl)-2-fluorophenyl)-3-(trifluoromethyl)-1H-pyrazole-5-carboxamide (141c)

To a solution of 1-(3-cyanophenyl)-N-(2-fluoro-5-(hydroxy(3-methoxyphenyl)methyl)phenyl)-3-(trifluoromethyl)-1H-pyrazole-5-carboxamide (141b) (2.05 g, 4.02 mmol) in dichloromethane (50 mL) at 0° C. was added thionyl chloride (0.626 mL, 8.57 mmol) and stirred at room temperature for 2 h. The reaction mixture was quenched with triethylamine (3.72 mL, 26.7 mmol), stirred for 1 h, added cyclopropylmethanamine (1.52 mL, 17.73 mmol) and concentrated in vacuum to remove dichloromethane. The reaction mixture was diluted with acetonitrile (10 mL) and added cyclopropylmethanamine (8.00 mL, 92 mmol). The reaction mixture was heated at reflux overnight, cooled to room temperature and concentrated in vacuum to dryness. The residue was dissolved in chloroform (300 mL), washed with water (100 mL), dried, filtered and concentrated in vacuum. The residue obtained was purified by flash column chromatography (silica gel 40 g, eluting with CMA 80 in chloroform (0 to 20%) to afford 1-(3-cyanophenyl)-N-(5-((cyclopropylmethylamino)(3-methoxyphenyl)methyl)-2-fluorophenyl)-3-(trifluoromethyl)-1H-pyrazole-5-carboxamide (141c) (0.838 g, 37.0% yield) as a off white semisolid; MS (ES+) 564.3 (M+1) (ES−) 562.3 (M−1).

Step-4: Preparation of tert-butyl 3-(5-((5-(((cyclopropylmethyl)amino)(3-methoxyphenyl)methyl)-2-fluorophenyl)carbamoyl)-3-(trifluoromethyl)-1H-pyrazol-1-yl)benzylcarbamate (141d)

To a solution of 1-(3-cyanophenyl)-N-(5-((cyclopropylmethylamino)(3-methoxyphenyl)methyl)-2-fluorophenyl)-3-(trifluoromethyl)-1H-pyrazole-5-carboxamide (141c) (0.8 g, 1.42 mmol) in MeOH (25 mL) cooled with ice/water was added di-tert-butyl dicarbonate (1.239 g, 5.68 mmol) and nickel(II) chloride (0.084 g, 0.355 mmol). Sodium borohydride (0.508 g, 14.20 mmol) was added slowly over 15 min and reaction mixture was stirred at room temperature for 1 h. The reaction mixture was quenched with N1-(2-aminoethyl)ethane-1,2-diamine (0.690 mL, 6.39 mmol) stirred for 0.5 h and concentrated in vacuum to dryness. The residue obtained was diluted with water (200 mL). The solid obtained was collected by filtration, dried in vacuum and purified by flash column chromatography (silica gel 40 g with 0-100% 9:1 ethyl acetate/methanol in hexane) to afford tert-butyl 3-(5-((5-(((cyclopropylmethyl)amino)(3-methoxyphenyl)methyl)-2-fluorophenyl)carbamoyl)-3-(trifluoromethyl)-1H-pyrazol-1-yl)benzylcarbamate (141d) (0.35 g, 14.47% yield) as a white solid.

Step-5: Preparation of 1-(3-(aminomethyl)phenyl)-N-(5-(((cyclopropylmethyl)amino)(3-methoxyphenyl)methyl)-2-fluorophenyl)-3-(trifluoromethyl)-1H-pyrazole-5-carboxamide (141e)

To a solution of tert-butyl 3-(5-((5-(((cyclopropylmethyl)amino)(3-methoxyphenyl)methyl)-2-fluorophenyl)carbamoyl)-3-(trifluoromethyl)-1H-pyrazol-1-yl)benzylcarbamate (141d) 0.69 g, 1.033 mmol) in methanol (10 mL) was added hydrogen chloride (3.14 mL, 103 mmol), stirred at room temperature overnight and concentrated in vacuum to dryness. The residue obtained was purified by flash column chromatography (silica gel 12 g, eluting with 0-100% CMA 80 in chloroform) to afford 1-(3-(aminomethyl)phenyl)-N-(5-(((cyclopropylmethyl)amino)(3-methoxyphenyl) methyl)-2-fluorophenyl)-3-(trifluoromethyl)-1H-pyrazole-5-carboxamide (141e) free base as a white solid; To a solution of free base of tert-butyl 3-(5-(5-(((cyclopropylmethylamino)(3-methoxyphenyl)methyl)-2-fluorophenylcarbamoyl)-3-(trifluoromethyl)-1H-pyrazol-1-yl)benzylcarbamate (141e) in methanol (10 mL) was added hydrochloric acid (10 eq) and stirred at room temperature for 30 mins and concentrated in vacuum to dryness to afford 1-(3-(aminomethyl)phenyl)-N-(5-(((cyclopropylmethyl)amino)(3-methoxyphenyl)methyl)-2-fluorophenyl)-3-(trifluoromethyl)-1H-pyrazole-5-carboxamide (141e) (200 mgs) hydrochloride salt as a white solid. $^1$H NMR (300 MHz, DMSO-$d_6$) δ 10.79 (s, 1H, $D_2O$ exchangeable), 10.09 (s, 2H, $D_2O$ exchangeable), 8.36 (d, J=16.1 Hz, 3H, $D_2O$ exchangeable), 7.94 (s, 1H), 7.75-7.48 (m, 6H), 7.36 (dt, J=16.4, 9.2 Hz, 3H), 7.21 (s, 1H), 6.92 (d, J=8.3 Hz, 1H), 5.58 (s, 1H), 4.13 (s, 2H), 3.75 (s, 3H), 2.68 (s, 2H), 1.17-1.07 (m, 1H), 0.54 (d, J=7.5 Hz, 2H), 0.28 (s, 2H); MS (ES+) 568.3 (M+1), 590.3 (M+23); (ES−) 566.3 (M−1), 602.3 (M+35); Analysis calculated for $C_{30}H_{29}F_4N_5O_2$·3HCl·1.25$H_2O$: C, 51.60; H, 4.98; N, 10.03; Cl, 15.03; Found: C, 51.02; H, 4.85; N, 9.63; Cl, 15.63.

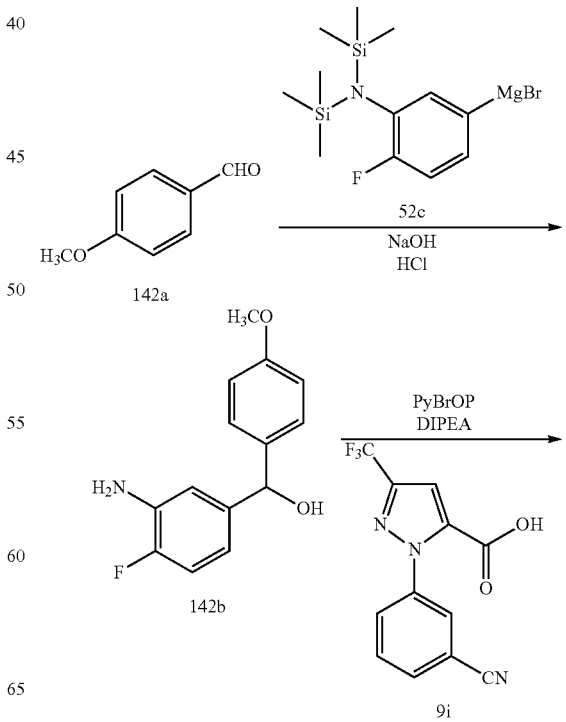

Scheme 142

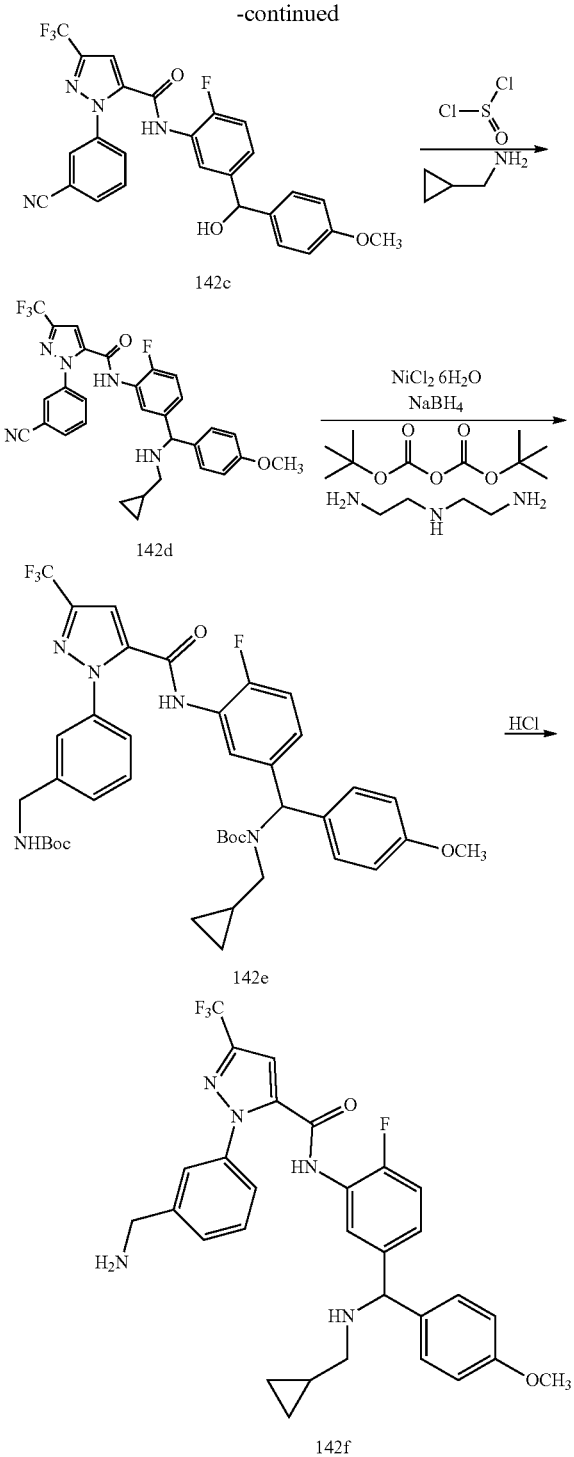

Preparation of 1-(3-(aminomethyl)phenyl)-N-(5-(((cyclopropylmethyl)amino)(4-methoxyphenyl)methyl)-2-fluorophenyl)-3-(trifluoromethyl)-1H-pyrazole-5-carboxamide (141f)

Step-1: Preparation of (3-amino-4-fluorophenyl)(4-methoxyphenyl)methanol (142b)

To a stirred solution of 4-anisaldehyde (142a) (1.825 mL, 15 mmol) in tetrahydrofuran (15 mL) was added (3-(bis (trimethylsilyl)amino)-4-fluorophenyl)magnesium bromide (52c) (20.25 mL, 20.25 mmol) at 0° C. The reaction was stirred for 14 h at same temperature and quenched by adding 2 N HCl (10 mL, 20 mmol), stirred for 0.5 h. The reaction mixture was basified with saturated aqueous NaHCO$_3$ and extracted with ethyl acetate (2×250 mL). The organic layers were combined washed with water (2×50 mL), brine (50 mL) dried over anhydrous MgSO$_4$, filtered, evaporated to dryness. The crude residue was purified by flash column chromatography (silica gel 80 g, eluting with 0-100% ethyl acetate in hexane) to furnish (3-amino-4-fluorophenyl)(4-methoxyphenyl)methanol (142b) (2.125 g, 8.59 mmol, 57.3% yield).

$^1$H NMR (300 MHz, DMSO-d$_6$) δ 7.28-7.13 (m, 2H), 6.86 (dd, J=11.2, 8.4 Hz, 3H), 6.74 (dd, J=9.1, 2.2 Hz, 1H), 6.47 (ddd, J=8.3, 4.5, 2.2 Hz, 1H), 5.65 (d, J=3.9 Hz, 1H, D$_2$O exchangeable), 5.47 (d, J=3.9 Hz, 1H), 5.04 (s, 2H, D$_2$O exchangeable), 3.71 (s, 3H).

MS (ES+) 270.2 (M+23); (ES−) 246.2 (M−1).

Step-2: Preparation of 1-(3-cyanophenyl)-N-(2-fluoro-5-(hydroxy(4-methoxyphenyl)methyl)phenyl)-3-(trifluoromethyl)-1H-pyrazole-5-carboxamide (142c)

To a solution of 1-(3-cyanophenyl)-3-(trifluoromethyl)-1H-pyrazole-5-carboxylic acid (9i) (2.63 g, 9.34 mmol) in DMF (20 mL) was added (3-amino-4-fluorophenyl)(4-methoxyphenyl)methanol (142b) (2.1 g, 8.49 mmol), N-ethyl-N-isopropylpropan-2-amine (7.40 mL, 42.5 mmol) and bromo-tris-pyrrolidino phosphoniumhexafluorophosphate (PyBrOP, 4.75 g, 10.19 mmol) at room temperature. The reaction mixture was stirred at room temperature for 20 h under nitrogen atmosphere. The reaction was diluted with water (100 mL) and extracted with ethyl acetate (2×100 mL). The organic layers were combined, washed with water (2×100 mL), brine (50 mL), dried, filtered, and evaporated in vacuum to dryness. The residue obtained was purified by flash column chromatography (silica gel 40 g, eluting with 0-100% ethyl acetate in hexanes) to furnish 1-(3-cyanophenyl)-N-(2-fluoro-5-(hydroxy(4-methoxyphenyl)methyl)phenyl)-3-(trifluoromethyl)-1H-pyrazole-5-carboxamide (142c) (3.23 g, 6.33 mmol, 74.5% yield) as a yellow semisolid; $^1$H NMR (300 MHz, DMSO-d$_6$) δ 10.54 (s, 1H, D$_2$O exchangeable), 8.12 (t, J=1.8 Hz, 1H), 8.00 (dt, J=7.8, 1.3 Hz, 1H), 7.92-7.86 (m, 1H), 7.76-7.69 (m, 2H), 7.52-7.45 (m, 1H), 7.26-7.22 (m, 3H), 6.88-6.82 (m, 3H), 5.90 (d, J=4.0 Hz, 1H, D$_2$O exchangeable), 5.64 (dd, J=4.0, 2.3 Hz, 1H), 3.71 (s, 3H); MS (ES+) 533.2 (M+Na), (ES−) 509.2 (M−1).

Step-3: Preparation of 1-(3-cyanophenyl)-N-(5-(((cyclopropylmethyl)amino)(4-methoxyphenyl)methyl)-2-fluorophenyl)-3-(trifluoromethyl)-1H-pyrazole-5-carboxamide (142d)

To a solution of 1-(3-cyanophenyl)-N-(2-fluoro-5-(hydroxy(4-methoxyphenyl)methyl)phenyl)-3-(trifluoromethyl)-1H-pyrazole-5-carboxamide (142c) (2.75 g, 5.39 mmol) in dichloromethane (50 mL) at 0° C. was added thionyl chloride (0.840 mL, 11.50 mmol) and stirred at room temperature for 2 h. The reaction mixture was quenched with triethylamine (0.771 mL, 5.53 mmol), stirred for 1 h, added cyclopropylmethanamine (1.52 mL, 17.73 mmol) and concentrated in vacuum to remove dichloromethane. The reaction mixture was diluted with acetonitrile (10 mL) and added cyclopropylmethanamine (1.520 mL, 17.73 mmol).

The reaction mixture was heated at reflux overnight, cooled to room temperature and concentrated in vacuum to dryness. The residue was dissolved in chloroform (300 mL), washed with water (100 mL), dried, filtered and concentrated in vacuum. The residue obtained was purified by flash column chromatography (silica gel 40 g, eluting with CMA 80 in chloroform (0 to 20%) to afford 1-(3-cyanophenyl)-N-(5-((cyclopropylmethylamino)(4-methoxyphenyl)methyl)-2-fluorophenyl)-3-(trifluoromethyl)-1H-pyrazole-5-carboxamide (142d) (1.448 g, 47.7% yield) as an white semisolid; MS (ES+) 564.3 (M+1), (ES−) 562.3 (M−1).

Step-4: Preparation of tert-butyl ((3-(1-(3-(((tert-butoxycarbonyl)amino)methyl)phenyl)-3-(trifluoromethyl)-1H-pyrazole-5-carboxamido)-4-fluorophenyl)(4-methoxyphenyl)methyl)(cyclopropylmethyl)carbamate (142e)

To a solution of 1-(3-cyanophenyl)-N-(5-((cyclopropylmethylamino)(4-methoxyphenyl)methyl)-2-fluorophenyl)-3-(trifluoromethyl)-1H-pyrazole-5-carboxamide (142d) (1.4 g, 2.484 mmol) in MeOH (25 mL) cooled with ice/water was added di-tert-butyl dicarbonate (2.169 g, 9.94 mmol) and nickel(II) chloride (0.148 g, 0.621 mmol). Sodium borohydride (0.890 g, 24.84 mmol) was added slowly over 15 min and reaction mixture was stirred at room temperature for 1 h. The reaction mixture was quenched with N1-(2-aminoethyl)ethane-1,2-diamine (1.208 mL, 11.18 mmol) stirred for 0.5 h and concentrated in vacuum to dryness. The residue obtained was diluted with water (200 mL). The solid obtained was collected by filtration, dried in vacuum and purified by flash column chromatography (silica gel 40 g with 0-100% 9:1 ethyl acetate/methanol in hexane) to afford tert-butyl ((3-(1-(3-(((tert-butoxycarbonyl)amino)methyl)phenyl)-3-(trifluoromethyl)-1H-pyrazole-5-carboxamido)-4-fluorophenyl)(4-methoxyphenyl)methyl)(cyclopropylmethyl)carbamate (142e) (0.906 g, 47.5% yield) as a white solid.

Step-5: Preparation of 1-(3-(aminomethyl)phenyl)-N-(5-(((cyclopropylmethyl)amino)(4-methoxyphenyl)methyl)-2-fluorophenyl)-3-(trifluoromethyl)-1H-pyrazole-5-carboxamide (142f)

To a solution of tert-butyl ((3-(1-(3-(((tert-butoxycarbonyl)amino)methyl)phenyl)-3-(trifluoromethyl)-1H-pyrazole-5-carboxamido)-4-fluorophenyl)(4-methoxyphenyl)methyl)(cyclopropylmethyl)carbamate (142e) (0.88 g, 1.146 mmol) in methanol (5 mL) was added hydrogen chloride (3.48 mL, 115 mmol), stirred at room temperature overnight and concentrated in vacuum to dryness. The residue obtained was purified by flash column chromatography (silica gel 12 g, eluting with 0-100% CMA 80 in chloroform) to afford 1-(3-(aminomethyl)phenyl)-N-(5-(((cyclopropylmethyl)amino)(4-methoxyphenyl)methyl)-2-fluorophenyl)-3-(trifluoromethyl)-1H-pyrazole-5-carboxamide (142f) (0.487 g, 74%) free base as a white solid; To a solution of free base of tert-butyl 3-(5-(5-((cyclopropylmethylamino)(4-methoxyphenyl)methyl)-2-fluorophenylcarbamoyl)-3-(trifluoromethyl)-1H-pyrazol-1-yl)benzylcarbamate (142f) (0.46 g, 0.81 mmol) in methanol (10 mL) was added hydrochloric acid (10 eq) and stirred at room temperature for 30 mins and concentrated in vacuum to dryness to afford 1-(3-(aminomethyl)phenyl)-N-(5-(((cyclopropylmethyl)amino)(3-methoxyphenyl)methyl)-2-fluorophenyl)-3-(trifluoromethyl)-1H-pyrazole-5-carboxamide (142f) (80 mgs) hydrochloride salt as a white solid; $^1$H NMR (300 MHz, DMSO-$d_6$) δ 10.78 (s, 1H, $D_2O$ exchangeable), 9.99 (s, 1H, $D_2O$ exchangeable), 8.45 (s, 2H, $D_2O$ exchangeable), 7.85 (s, 1H), 7.71 (d, J=7.1 Hz, 2H), 7.57 (dq, J=17.6, 9.1, 8.4 Hz, 6H), 7.37 (t, J=9.6 Hz, 1H), 6.96 (d, J=8.2 Hz, 2H), 5.48 (s, 1H), 4.12 (s, 2H), 3.74 (s, 3H), 2.62 (s, 2H), 1.10 (s, 1H), 0.53 (d, J=7.8 Hz, 2H), 0.26 (s, 2H); Mass spec (ES−) 566.3 (M−1), 602.2 (M+35); Analysis calculated for $C_{30}H_{29}F_4N_5O_2 \cdot 2HCl \cdot 2H_2O$: C, 53.31; H, 5.22; N, 10.36; Cl, 10.35; Found: C, 53.53; H, 5.12; N, 10.11; Cl, 10.59.

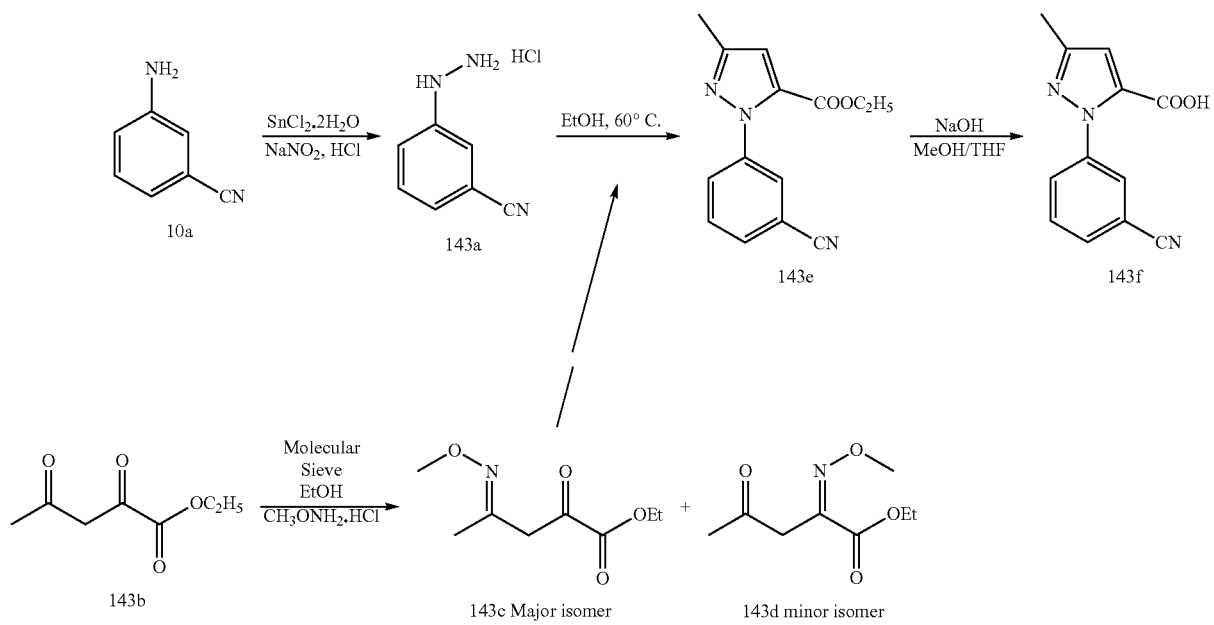

Scheme 143

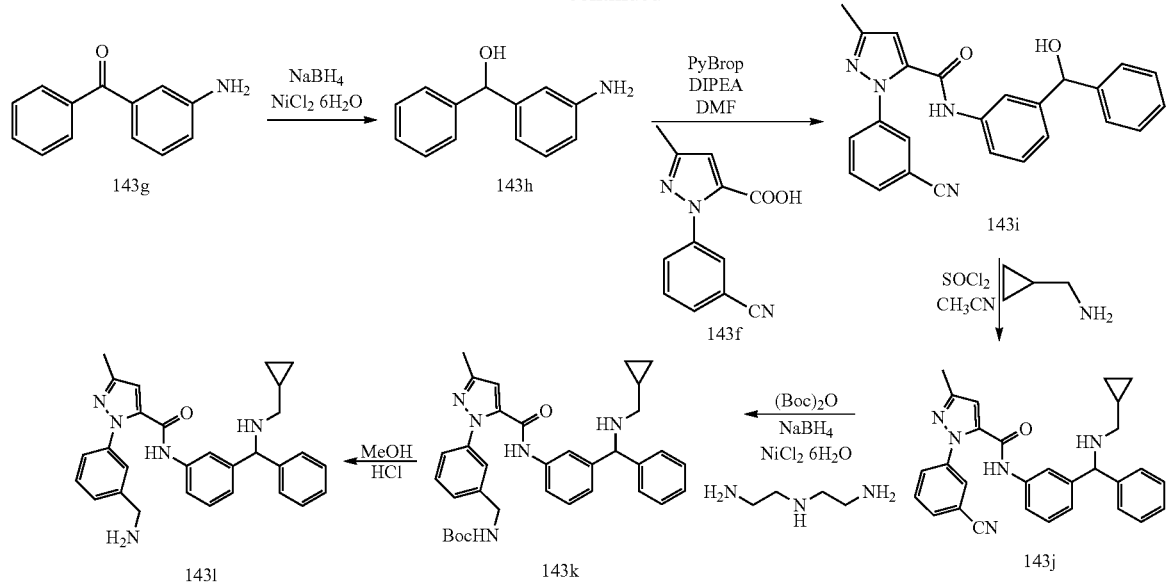

Preparation of 1-(3-(Aminomethyl)phenyl)-N-(3-((cyclopropylmethylamino)(phenyl)methyl) phenyl)-3-methyl-1H-pyrazole-5-carboxamide (143l)

Step-1: Preparation of 4-Methoxyimino-2-oxo-pentaneperoxoic acid ethyl ester (143c) and 2-Methoxyimino-4-oxo-pentaneperoxoic Acid Ethyl Ester (143d)

To a suspension of 2,4-Dioxo-pentanoic acid ethyl ester (143b) (25 g, 158.07 mmol) in ethanol (325 mL) was added methoxylaminehydrochloride (13.86 g, 165.97 mmol) and Molecular sieves (125 gm). The reaction mixture was stirred at room temperature overnight and filtered through hyflow bed. The reaction mixture was concentrated in vacuum and the residue obtained was dissolved in diethyl ether (600 mL). The organic layer was washed with brine (300 mL), dried, filtered and concentrated in vacuum to afford crude product. The crude was purified by flash column chromatography (silica gel 400 g, eluting with 0-20% ethyl acetate in hexane) to furnish:
1. 2-Methoxyimino-4-oxo-pentaneperoxoic acid ethyl ester (143d) (8 g, 27%); $^1$H NMR (300 MHz, DMSO-$d_6$) δ 4.28-4.16 (m, 2H), 3.96 (s, 3H), 3.65 (s, 2H), 1.76 (d, J=1.4 Hz, 3H), 1.30-1.16 (m, 3H).
2. 4-Methoxyimino-2-oxo-pentaneperoxoic acid ethyl ester (143c) (12 g, 41%); $^1$H NMR (300 MHz, DMSO-$d_6$) δ 4.20 (q, J=7.1 Hz, 2H), 3.95 (s, 3H), 3.71 (s, 2H), 2.15 (s, 3H), 1.23 (t, J=7.1 Hz, 3H).

Step-2: Preparation of 3-hydrazinylbenzonitrile Hydrochloride (143a)

To 3-Amino-benzonitrile (10a) (34 g, 287.79 mmol) at 0° C. was added slowly dropwise HCl (136 mL). To this was added a pre-dissolved solution of Sodium nitrite (25.81 g, 374.13 mmol) in 50 mL $H_2O$ drop wise at a rate so as to maintain internal temperature between 0 to 5° C. The reaction was stirred for 1 hour at 0° C. followed by the dropwise addition of a freshly prepared solution of stannous chloride dihydrate (142.8 g, 633.147 mmol) in conc. HCl (95.2 mL) maintaining internal temperature between 0 to 10° C. The reaction mixture was allowed to warm to room temperature and stirred for 2 h. The crude 3-hydrazinylbenzonitrile Hydrochloride (143a) obtained as a creamish colored liquid was used directly as such for next step.

Step-3: Preparation of 2-(3-Cyano-phenyl)-5-methyl-2H-pyrazole-3-carboxylic Acid Ethyl Ester (143e)

To a suspension of 4-Methoxyimino-2-oxo-pentaneperoxoic acid ethyl ester (143c) (12 g, 64.11 mmol) in ethanol (120 mL) was added 3-Hydrazino-benzonitrile hydrochloride salt prepared in step-2 (288 mL) with stirring. The reaction mixture was heated at reflux overnight. Progress of reaction was checked by TLC (EtOAc/n-Hex=2:8). After completion of reaction the reaction mixture was concentrated in vacuum to remove ethanol. The residue obtained was solvent was extracted with ethyl acetate (200×3). The organic layers were combined washed with brine (300 mL), dried, filtered and concentrated in vacuum to afford crude product. The crude was purified by flash column chromatography (silica gel 250 g, eluting with 0-16% ethyl acetate in hexane) to furnish 2-(3-Cyano-phenyl)-5-methyl-2H-pyrazole-3-carboxylic acid ethyl ester (143e) (9 g, 55%); $^1$H NMR (300 MHz, DMSO-$d_6$) δ 8.06-8.03 (m, 1H), 7.92 (dt, J=7.7, 1.4 Hz, 1H), 7.83 (ddd, J=8.2, 2.2, 1.2 Hz, 1H), 7.73-7.64 (m, 1H), 6.96 (d, J=0.6 Hz, 1H), 4.19 (q, J=7.1 Hz, 2H), 2.28 (s, 3H), 1.17 (t, J=7.1 Hz, 3H).

Step-4: Preparation of 2-(3-Cyano-phenyl)-5-methyl-2H-pyrazole-3-carboxylic Acid (143f)

To a suspension of 2-(3-Cyano-phenyl)-5-methyl-2H-pyrazole-3-carboxylic acid ethyl ester (143e) (8.5 g, 33.3 mmol) in MeOH/THF (⅓, 21+63 mL) was added 3 N NaOH (4 g, 100 mmol) with stirring. The reaction mixture was stirred for 2 h (Progress of reaction was checked by TLC (MeOH/CHCl$_{3=1/9}$). The reaction mixture was concentrated in vacuum to remove THF and methanol. The aqueous layer was acidified using conc. HCl at 5-15° C. temperature and extracted with ethyl acetate (3×100). The organic layers were combined washed with brine (300 mL), dried, filtered and concentrated in vacuum to afford crude 2-(3-Cyano-phenyl)-5-methyl-2H-pyrazole-3-carboxylic acid (143f) (6.7 g, 89%); $^1$H NMR (300 MHz, DMSO-d$_6$) δ 8.01 (t, J=1.9 Hz, 1H), 7.89 (dt, J=7.7, 1.4 Hz, 1H), 7.81 (ddd, J=8.2, 2.2, 1.2 Hz, 1H), 7.66 (t, J=7.9 Hz, 1H), 6.88 (s, 1H), 2.27 (s, 3H).

Step-5: Preparation of (3-Amino-phenyl)-phenyl-methanol (143h)

To a stirred solution of (3-aminophenyl)(phenyl)methanone (143g) (0.97 g, 4.89 mmol) in methanol (25 mL), cooled to 0° C., were added, nickel(II) chloride hexahydrate (0.29 g, 1.22 mmol), followed by portion wise addition of sodium borohydride (1.11 g, 29.4 mmol) over 45 min. The reaction mixture was stirred for 15 min at room temperature and quenched with N1-(2-aminoethyl)ethane-1,2-diamine (1.057 mL, 9.79 mmol. The reaction mixture was stirred for 30 minutes and concentrated in vacuum to dryness. The residue was treated with water (25 mL) extracted with ethyl acetate (2×25 mL). The organic layers were combined washed with brine (25 mL), dried filtered and concentrated in vacuum to dryness. The residue obtained was purified by flash column chromatography [(silica gel 25 g, eluting with ethyl acetate/hexanes from 0 to 100%)] to furnish (3-Amino-phenyl)-phenyl-methanol (143h) (772 mg, 3.87 mmol, 79% yield) as a white solid; $^1$H NMR (300 MHz, DMSO-d$_6$) δ 7.36-7.24 (m, 4H), 7.21-7.14 (m, 1H), 6.91 (t, J=7.7 Hz, 1H), 6.57 (t, J=2.0 Hz, 1H), 6.51 (dt, J=7.5, 1.3 Hz, 1H), 6.37 (ddd, J=8.0, 2.4, 1.1 Hz, 1H), 5.69 (d, J=3.8 Hz, 1H), 5.50 (d, J=3.8 Hz, 1H), 4.99 (s, 2H); MS (ES+) 222.1 (M+1), (ES−) 198.0 (M−1).

Step-6: Preparation of 2-(3-Cyano-phenyl)-5-methyl-2H-pyrazole-3-carboxylic acid [3-(hydroxy-phenyl-methyl)-phenyl]-amide (143i)

To a stirred solution of 2-(3-Cyano-phenyl)-5-methyl-2H-pyrazole-3-carboxylic acid (143f) (2.5 g, 11.002 mmol) in DMF (50 mL) was added (3-Amino-phenyl)-phenyl-methanol (143h) (2.19 g, 11.00 mmol), DIPEA (11.38 g, 88.02 mmol) and PyBrop (5.13 g, 11.00 mmol). The reaction mixture was stirred at room temperature overnight. Progress of reaction was checked by TLC (EtOAc/n-Hex=4:6). After completion of reaction the reaction, the mixture was diluted with water (200 mL) and extracted with ethyl acetate (3×200 mL). The organic layers were combined washed with water (2×200 mL), brine (200 mL), dried, filtered and concentrated in vacuum to afford crude product. The crude was purified by flash column chromatography (silica gel 100 g, eluting with 15-35% ethyl acetate in hexane) to furnish 2-(3-Cyano-phenyl)-5-methyl-2H-pyrazole-3-carboxylic acid [3-(hydroxy-phenyl-methyl)-phenyl]-amide (143i) (0.55 gm), which was used as such for next step.

Step-7: Preparation of 2-(3-Cyano-phenyl)-5-methyl-2H-pyrazole-3-carboxylic acid {3-[(cyclopropylmethyl-amino)-phenyl-methyl]-phenyl}-amide (143j)

To an ice cold solution of 2-(3-Cyano-phenyl)-5-methyl-2H-pyrazole-3-carboxylic acid [3-(hydroxy-phenyl-methyl)-phenyl]-amide (143i) (0.5 g, 1.22 mmol) in acetonitrile (10 mL) was added dropwise thionyl chloride (0.29 g, 2.45 mmol) maintaining internal temperature between 5-10° C. The reaction mixture was allowed to warm to room temperature over a period of 3.5 h. The reaction mixture was concentrated in vacuum to dryness and to the residue was added acetonitrile (5 mL), cyclopropyl methylamine (1.31 g, 18.36 mmol). The reaction mixture was heated at reflux overnight the reaction mass for overnight. Progress of reaction was checked by TLC (EtOAc/n-Hex=4:6). The reaction mixture on completion was concentrated in vacuum to dryness. To the residue was added water (50 mL) and extracted with ethyl acetate (3×50 mL). The organic layers were combined washed with brine (50 mL), dried, filtered and concentrated in vacuum to afford crude product. The crude was purified by flash column chromatography (silica gel 40 g, eluting with 20-45% ethyl acetate in hexane) to furnish 2-(3-Cyano-phenyl)-5-methyl-2H-pyrazole-3-carboxylic acid {3-[(cyclopropylmethyl-amino)-phenyl-methyl]-phenyl}-amide (143j) (0.4 g, 71%); $^1$H NMR (300 MHz, DMSO-d$_6$) δ 10.46 (s, 1H), 7.95 (t, J=1.9 Hz, 1H), 7.87 (dq, J=2.4, 1.5, 1.1 Hz, 1H), 7.85-7.80 (m, 1H), 7.78-7.73 (m, 1H), 7.72-7.66 (m, 2H), 7.66-7.60 (m, 1H), 7.53 (d, J=8.0 Hz, 1H), 7.41 (d, J=1.7 Hz, 1H), 7.38 (s, 1H), 7.29 (d, J=7.2 Hz, 2H), 7.21-7.17 (m, 2H), 6.98 (s, 1H), 6.67 (s, 1H), 3.45 (dd, J=12.8, 6.3 Hz, 2H), 1.87-1.82 (m, 3H), 0.91-0.77 (m, 1H), 0.46-0.25 (m, 2H), 0.11--0.05 (m, 2H).

Step-8: Preparation of [3-(5-{3-[(Cyclopropylmethyl-amino)-phenyl-methyl]-phenylcarbamoyl}-3-methyl-pyrazol-1-yl)-benzyl]-carbamic acid tert-butyl ester (143k)

To a solution of 2-(3-Cyano-phenyl)-5-methyl-2H-pyrazole-3-carboxylic acid {3-[(cyclopropylmethyl-amino)-phenyl-methyl]-phenyl}-amide (143j) (0.36 g, 0.78 mmol) in MeOH (10 mL) cooled with ice/water was added nickel(II) chloride hexahydrate (0.22 g, 0.94 mmol) and Boc anhydride (0.51 g, 2.34 mmol) followed by portionwise addition of sodium borohydride (0.17 g, 4.67 mmol) over a period of 15 min. The reaction mixture was stirred at room temperature for 0.5 hrs and quenched with N$^1$-(2-aminoethyl)ethane-1,2-diamine (0.17 mL, 1.56 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over MgSO$_4$ filtered and concentrated in vacuum. The residue obtained was purified by flash column chromatography (silica gel 40 g, eluting with 30-45% Ethyl acetate/hexane) to furnish [3-(5-{3-[(Cyclopropylmethyl-amino)-phenyl-methyl]-phenylcarbamoyl}-3-methyl-pyrazol-1-yl)-benzyl]-carbamic acid tert-butyl ester (143k) (0.19 g, 43%); $^1$H NMR (300 MHz, DMSO-d$_6$) δ 10.46 (s, 1H), 7.67 (s, 1H), 7.55-7.10 (m, 12H), 6.83 (s, 1H), 4.80 (s, 1H), 4.15 (d, J=6.2 Hz, 2H), 3.23 (d, J=6.5 Hz, 2H), 2.26 (s, 3H), 1.39 (d, J=1.7 Hz, 9H), 0.99-0.87 (m, 1H), 0.38 (dt, J=8.1, 2.9 Hz, 2H), 0.04 (q, J=4.8 Hz, 2H).

Step-9: Preparation of 2-(3-Aminomethyl-phenyl)-5-methyl-2H-pyrazole-3-carboxylic acid {3-[(cyclopropylmethyl-amino)-phenyl-methyl]-phenyl}-amide (143l)

To a solution of [3-(5-{3-[(Cyclopropylmethyl-amino)-phenyl-methyl]-phenylcarbamoyl}-3-methyl-pyrazol-1-yl)-benzyl]-carbamic acid tert-butyl ester (143k) (0.18 g, 0.32 mmol) in methanol (10 mL) and added conc. HCl (1 mL). The reaction mixture was stirred at room temperature overnight and concentrated in vacuum to dryness. The residue was azeotroped with toluene (2×10 mL) and ethanol (10 mL), dried in vacuum pump to furnish a residue. The residue was purified by flash column chromatography (silica gel 40 g, eluting with 0-6% methanol in dichloromethane to furnish (0.08 g, 54%) as a yellow solid. This was again repurified by flash column chromatography (silica gel 12 g, eluting with 0-100% cma-80 in chloroform) to furnish 1-(3-(aminomethyl)phenyl)-N-(3-((cyclopropylmethylamino)(phenyl)methyl)phenyl)-3-methyl-1H-pyrazole-5-carboxamide (143l) (10.74 μmol, 6.67% yield) as a yellow solid; $^1$H NMR (300 MHz, DMSO-d$_6$) δ 10.46 (s, 1H), 7.69 (s, 1H), 7.50 (d, J=7.9 Hz, 1H), 7.45-7.42 (m, 1H), 7.42-7.37 (m, 2H), 7.35-7.29 (m, 2H), 7.29-7.24 (m, 1H), 7.23-7.14 (m, 4H), 6.83 (s, 1H), 4.80 (s, 1H), 3.76 (s, 2H), 2.29 (s, 3H), 2.27 (d, J=2.9 Hz, 2H), 1.00-0.88 (m, 1H), 0.44-0.30 (m, 2H), 0.08-0.01 (m, 2H); MS (ES+) 466.4 (M+1); (ES-) 464.4 (M-1); 500.3 (M+Cl).

Scheme 144

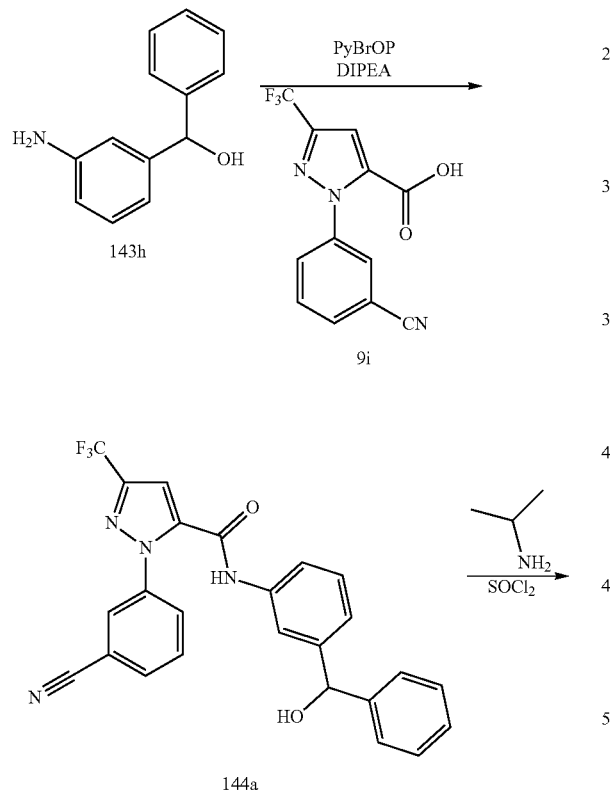

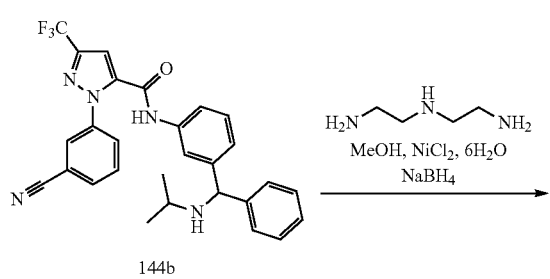

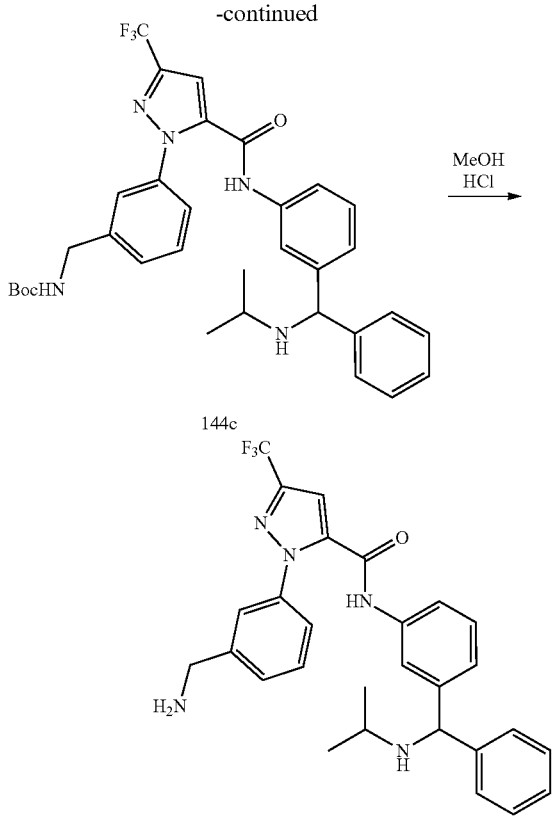

Preparation of 1-(3-(Aminomethyl)phenyl)-N-(3-((isopropylamino)(phenyl)methyl)phenyl)-3-(trifluoromethyl)-1H-pyrazole-5-carboxamide (144d)

Step-1: Preparation of 2-(3-Cyano-phenyl)-5-trifluoromethyl-2H-pyrazole-3-carboxylic Acid [3-(hydroxyphenylmethyl)phenyl]amide (144a)

In a 100 mL single-necked flask 1-(3-cyanophenyl)-3-(trifluoromethyl)-1H-pyrazole-5-carboxylic acid (9i) (0.682 g, 2.427 mmol), 3-aminophenyl)(phenyl)methanol (143h) (0.403 g, 2.023 mmol), bromo-tris-pyrrolidino phosphoniumhexafluorophosphate(PyBrop, 1.131 g, 2.427 mmol) was added N,N-dimethylformamide (DMF, 12 mL) and N-ethyl-N-isopropylpropan-2-amine (DIPEA, 1.762 mL, 10.11 mmol) successively in a positive flow of nitrogen at room temperature. The resulting reaction mixture was stirred at room temperature for 16 h under a positive flow of nitrogen atmosphere. Excess DMF was pumped-off under reduced pressure. The residue was treated with water (30 mL) and extracted with ethyl acetate (2×30 mL). The organic layers were combined, washed with water (30 mL), brine (30 mL), dried over anhydrous MgSO$_4$, filtered and concentrated in vacuum to dryness. The residue was purified by flash column chromatography [silica gel 40 g, eluting with methanol in chloroform from 0-80%] to furnish 1-(3-cyanophenyl)-N-(3-(hydroxy(phenyl)methyl)phenyl)-3-(trifluoromethyl)-1H-pyrazole-5-carboxamide (144a) (0.853 g, 1.845 mmol, 91% yield) as a white solid; 1H NMR (300 MHz, DMSO-d$_6$) δ 10.64 (s, 1H, D$_2$O exchangeable), 8.16 (t, J=1.8 Hz, 1H), 8.00 (dt, J=7.8, 1.3 Hz, 1H), 7.90 (ddd, J=8.2, 2.2, 1.1 Hz, 1H), 7.78-7.69 (m, 2H), 7.64 (t, J=1.8 Hz, 1H), 7.55 (dt, J=8.1, 1.5 Hz, 1H), 7.38-7.31 (m, 3H), 7.30 (t, J=1.3 Hz, 1H), 7.27 (d, J=1.7 Hz, 1H), 7.25-7.17 (m, 1H), 7.16-7.12 (m, 1H), 5.95 (d, J=3.8 Hz, 1H, D$_2$O exchangeable), 5.67 (d, J=3.8 Hz, 1H); 19F NMR (282 MHz, DMSO d$_6$) δ −60.96; MS (ES+) 485.2 (M+Na), MS (ES−) 590.3923 (M+Cl), 959.2 (2M−1).

Step-2: Preparation of 2-(3-Cyano-phenyl)-5-trifluoromethyl-2H-pyrazole-3-carboxylic Acid [3-(isopropylamino-phenyl-methyl)-phenyl]-amide (144b)

To a solution of 2-(3-Cyano-phenyl)-5-trifluoromethyl-2H-pyrazole-3-carboxylic acid [3-(hydroxyphenylmethyl)phenyl]amide (144a) (1.0 g, 2.162 mmol) in dichloromethane (50 mL) at 0° C. was added thionyl chloride (0.514 g, 4.325 mmol) and stirred at room temperature for 3 h. Isopropylamine (0.638 g, 10.81 mmol) was added and stirred for 30 min. The reaction mixture was concentrated in vacuum to dryness. The residue obtained was dissolved in acetonitrile (20 mL) and added Isopropylamine (0.638 g, 10.81 mmol)). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 2-(3-Cyano-phenyl)-5-trifluoromethyl-2H-pyrazole-3-carboxylic acid [3-(isopropylamino-phenyl-methyl)-phenyl]-amide (144b) (0.65 g, 60%) as colorless liquid; $^1$H NMR (300 MHz, DMSO-d$_6$) δ 10.64 (s, 1H), 8.15 (t, J=1.9 Hz, 1H), 7.99 (dt, J=7.8, 1.3 Hz, 1H), 7.89 (ddd, J=8.2, 2.2, 1.1 Hz, 1H), 7.74 (d, J=7.9 Hz, 1H), 7.70 (s, 1H), 7.63 (s, 1H), 7.54 (dt, J=7.9, 1.8 Hz, 1H), 7.43-7.37 (m, 2H), 7.28 (dd, J=8.2, 6.6 Hz, 2H), 7.24-7.14 (m, 3H), 4.91 (s, 1H), 2.59-2.52 (m, 1H), 1.01 (d, J=6.2 Hz, 6H); MS (ES−) 502.3 (M−1).

Step-3: Preparation of (3-{5-[3-(Isopropylamino-phenyl-methyl)-phenylcarbamoyl]-3-trifluoromethyl-pyrazol-1-yl}-benzyl)-carbamic Acid Tert-Butyl Ester (144c)

To a solution of 2-(3-Cyano-phenyl)-5-trifluoromethyl-2H-pyrazole-3-carboxylic acid [3-(isopropylamino-phenyl-methyl)-phenyl]-amide (144b) (0.6 g, 1.19 mmol) in MeOH (15 mL) cooled with ice/water was added nickel(II) chloride hexahydrate (0.35 g, 1.49 mmol) and Boc anhydride (0.779 g, 3.57 mmol) followed by portion-wise addition of Sodium Borohydride (0.27 g, 7.15 mmol) over a period of 5 min. The reaction mixture was stirred at room temperature for 2 h and quenched with N$^1$-(2-aminoethyl)ethane-1,2-diamine (0.49 g, 4.764 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over MgSO$_4$ filtered and concentrated in vacuum. The residue obtained was purified by flash column chromatography (silica gel 24 g, eluting with 0-25% Ethyl acetate/hexane) to furnish (3-{5-[3-(Isopropylamino-phenyl-methyl)-phenylcarbamoyl]-3-trifluoromethyl-pyrazol-1-yl}-benzyl)-carbamic acid tert-butyl ester (144c) (0.420 gm) as an off white solid; $^1$H NMR (300 MHz, DMSO-d$_6$) δ 10.69 (s, 1H), 7.69-7.16 (m, 14H), 4.19 (d, J=6.2 Hz, 1H), 1.36 (s, 9H), 1.21-1.09 (m, 6H); MS (ES−) 606.3 (M−1).

Step-4: Preparation of 2-(3-Aminomethyl-phenyl)-5-trifluoromethyl-2H-pyrazole-3-carboxylic Acid [3-(isopropylamino-phenyl-methyl)-phenyl]-amide (114d)

To a solution of (3-{5-[3-(Isopropylamino-phenyl-methyl)-phenylcarbamoyl]-3-trifluoromethyl-pyrazol-1-yl}-benzyl)-carbamic acid tert-butyl ester (144c) (0.4 gm 1.65 mmol) in MeOH (10 mL) was added conc. HCl (0.5 mL). The reaction mixture was stirred at room temperature for 19 h. The reaction mass was concentrated in vacuum. The residue obtained was purified by flash column chromatography (silica gel 24 g, eluting with 0-15% MeOH/DCM) to furnish 2-(3-Aminomethyl-phenyl)-5-trifluoromethyl-2H-pyrazole-3-carboxylic acid [3-(isopropylamino-phenyl-methyl)-phenyl]-amide (0.250 g, 30%) as a yellowish solid. This was repurified by flash column chromatography (silica gel 12 g, eluting with 0-100% CMA-80 in chloroform) to afford 1-(3-(aminomethyl)phenyl)-N-(3-((isopropylamino)(phenyl)methyl)phenyl)-3-(trifluoromethyl)-1H-pyrazole-5-carboxamide (144d) (0.092 g, 36.8% yield) as a white solid; $^1$H NMR (300 MHz, DMSO-d$_6$) δ 10.98 (s, 1H), 9.80 (s, 2H), 8.50 (s, 3H), 7.98-7.92 (m, 1H), 7.81-7.75 (m, 2H), 7.74-7.70 (m, 3H), 7.66-7.36 (m, 7H), 5.65 (s, 1H), 4.12 (s, 2H), 3.03 (s, 1H), 1.43-1.21 (m, 7H); $^{19}$F NMR (282 MHz, DMSO) δ −60.78; MS (ES+) 508.3 (M+1); 530.3 (M+Na); (ES−) 506.3 (M−1); 542.3 (M+Cl); Analysis calculated for C$_{28}$H$_{28}$F$_3$N$_5$O.1.95HCl.2.25H$_2$O: C, 54.31; H, 5.61; Cl, 11.17; N, 11.31; Found: C, 54.55; H, 5.37; Cl, 10.98; N, 11.00.

Scheme 145

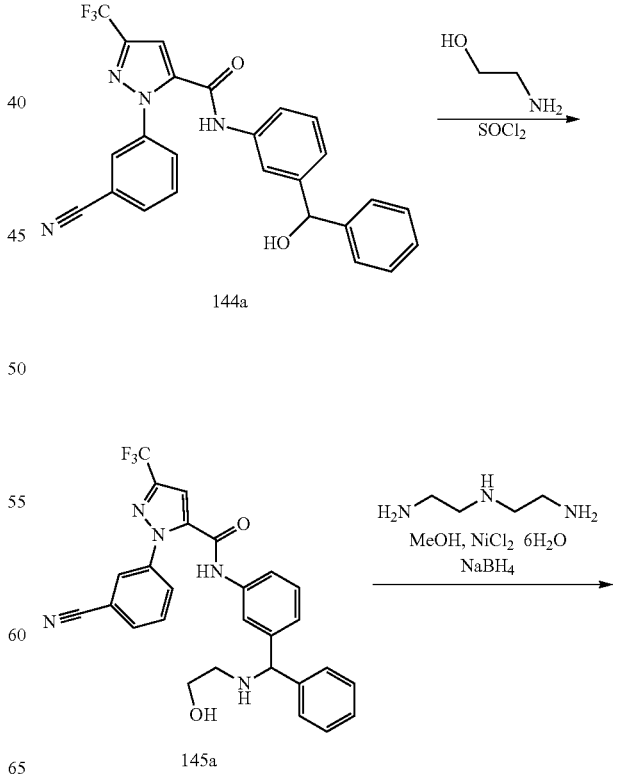

144a

145a

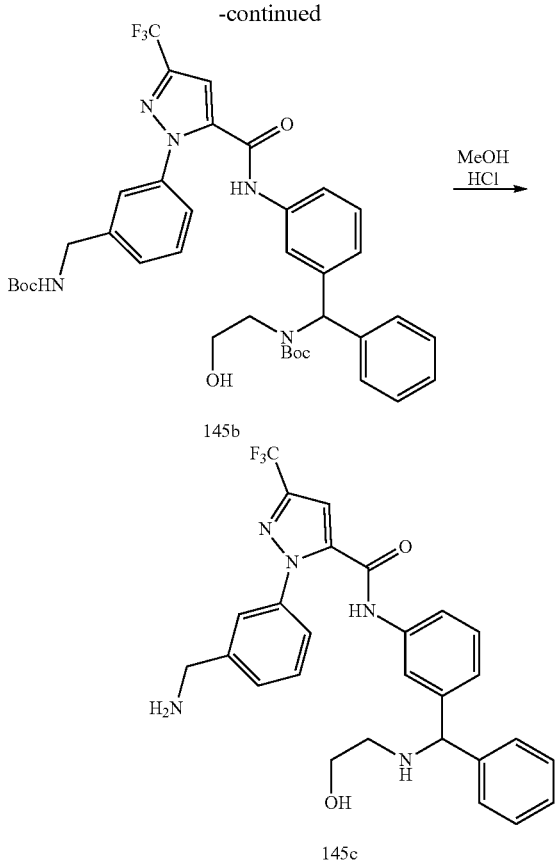

Preparation of 1-(3-(Aminomethyl)phenyl)-N-(3-((2-hydroxyethylamino)(phenyl)methyl)phenyl)-3-(trifluoromethyl)-1H-pyrazole-5-carboxamide (145c)

Step-1: Preparation of 2-(3-Cyano-phenyl)-5-trifluoromethyl-2H-pyrazole-3-carboxylic Acid{3-[(2-hydroxy-ethylamino)-phenyl-methyl]-phenyl}-amide (145a)

To a solution of 2-(3-Cyano-phenyl)-5-trifluoromethyl-2H-pyrazole-3-carboxylic acid [3-(hydroxyphenylmethyl)phenyl]amide (144a) (1.0 g, 2.162 mmol) in dichloromethane (50 mL) at 0° C. was added thionyl chloride (0.514 g, 4.325 mmol) and stirred at room temperature for 3 h. 2-Amino-ethanol (0.660 gm, 10.81 mmol) was added and stirred for 30 min. The reaction mixture was concentrated in vacuum to dryness. The residue obtained was dissolved in acetonitrile (20 mL) and added 2-Amino-ethanol (0.660 gm, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 2-(3-Cyano-phenyl)-5-trifluoromethyl-2H-pyrazole-3-carboxylic acid {3-[(2-hydroxy-ethylamino)-phenyl-methyl]-phenyl}-amide (145a) (0.75 g, 69%) as a colorless liquid; $^1$H NMR (300 MHz, DMSO-d$_6$) δ 10.64 (s, 1H), 8.18-8.11 (m, 1H), 7.99 (dt, J=7.8, 1.3 Hz, 1H), 7.89 (ddd, J=8.1, 2.2, 1.1 Hz, 1H), 7.74 (d, J=8.0 Hz, 1H), 7.70 (s, 1H), 7.64 (s, 1H), 7.54 (dd, J=8.0, 1.9 Hz, 1H), 7.39 (d, J=7.2 Hz, 1H), 7.33-7.23 (m, 3H), 7.22-7.18 (m, 2H), 4.79 (d, J=4.6 Hz, 1H), 4.56 (t, J=5.4 Hz, 1H), 3.85-3.68 (m, 1H), 3.54-3.49 (m, 2H); MS (ES−) 504.3 (M−1).

Step-2: Preparation of tert-butyl ((3-(1-(3-(((tert-butoxycarbonyl)amino)methyl)phenyl)-3-(trifluoromethyl)-1H-pyrazole-5-carboxamido)phenyl)(phenyl)methyl)(2-hydroxyethyl)carbamate (145b)

To a solution of 2-(3-Cyano-phenyl)-5-trifluoromethyl-2H-pyrazole-3-carboxylic acid {3-[(2-hydroxy-ethylamino)-phenyl-methyl]-phenyl}-amide (145b) (0.7 g, 1.38 mmol) in MeOH (15 mL) cooled with ice/water was added nickel(II) chloride hexahydrate (0.41 g, 1.73 mmol) and Boc anhydride (0.91 g, 4.15 mmol) followed by portion-wise addition of Sodium Borohydride (0.31 g, 8.30 mmol) over a period of 5 min. The reaction mixture was stirred at room temperature for 2 hrs and quenched with N$^1$-(2-aminoethyl)ethane-1,2-diamine (0.57 g, 5.54 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over MgSO$_4$ filtered and concentrated in vacuum. The residue obtained was purified by flash column chromatography (silica gel 24 g, eluting with 0-25% Ethyl acetate/hexane) to furnish tert-butyl ((3-(1-(3-(((tert-butoxycarbonyl)amino)methyl)phenyl)-3-(trifluoromethyl)-1H-pyrazole-5-carboxamido)phenyl)(phenyl)methyl)(2-hydroxyethyl)carbamate (145b) (0.35 g, 36%) as a brown solid; $^1$H NMR (300 MHz, DMSO-d$_6$) δ 10.75 (s, 1H), 7.72-7.66 (m, 1H), 7.57 (s, 1H), 7.50 (t, J=6.3 Hz, 1H), 7.44-7.39 (m, 3H), 7.38-7.34 (m, 3H), 7.32 (d, J=7.5 Hz, 3H), 7.18-7.11 (m, 2H), 6.93-6.87 (m, 1H), 6.29 (s, 1H), 4.46 (t, J=5.3 Hz, 1H), 4.19 (d, J=6.2 Hz, 2H), 3.31-3.10 (m, 2H), 3.09-2.83 (m, 2H), 1.32 (s, 18H); MS (ES−) 708.3 (M−1).

Step-3 Preparation of 2-(3-Aminomethyl-phenyl)-5-trifluoromethyl-2H-pyrazole-3-carboxylic acid {3-[(2-hydroxy-ethylamino)-phenyl-methyl]-phenyl}-amide (145c)

To a solution of tert-butyl ((3-(1-(3-(((tert-butoxycarbonyl)amino)methyl)phenyl)-3-(trifluoromethyl)-1H-pyrazole-5-carboxamido)phenyl)(phenyl)methyl)(2-hydroxyethyl)carbamate (145b) (0.32 gm 0.45 mmol) in MeOH (10 mL) was added conc. HCl (0.4 mL). The reaction mixture was stirred at room temperature for 19 hrs. The reaction mass was concentrated in vacuum. The residue obtained was purified by flash column chromatography (silica gel 24 g, eluting with 0-15% MeOH/DCM) to furnish 2-(3-Aminomethyl-phenyl)-5-trifluoromethyl-2H-pyrazole-3-carboxylic acid {3-[(2-hydroxy-ethylamino)-phenyl-methyl]-phenyl}-amide (145c) (0.06 g, 26%) as a yellowish solid. The product were repurified by flash column chromatography (silica gel 12 g, eluting with 0-100% cma-80 in chloroform) to afford pure (145c) (0.02 gm) as an off white solid; $^1$H NMR (300 MHz, DMSO-d$_6$) δ 10.94 (s, 1H), 9.97 (s, 2H), 8.41 (s, 3H), 7.85 (s, 1H), 7.73 (d, J=2.1 Hz, 1H), 7.70-7.48 (m, 7H), 7.47-7.33 (m, 4H), 5.62 (s, 1H), 5.24 (s, 1H), 4.13 (s, 2H), 3.71 (d, J=5.5 Hz, 2H), 2.89 (s, 2H); $^{19}$F NMR (282 MHz, DMSO) δ −60.79; MS (ES+) 510.3 (M+1); (ES−) 508.3 (M−1); 544.2 (M+Cl).

Scheme 146
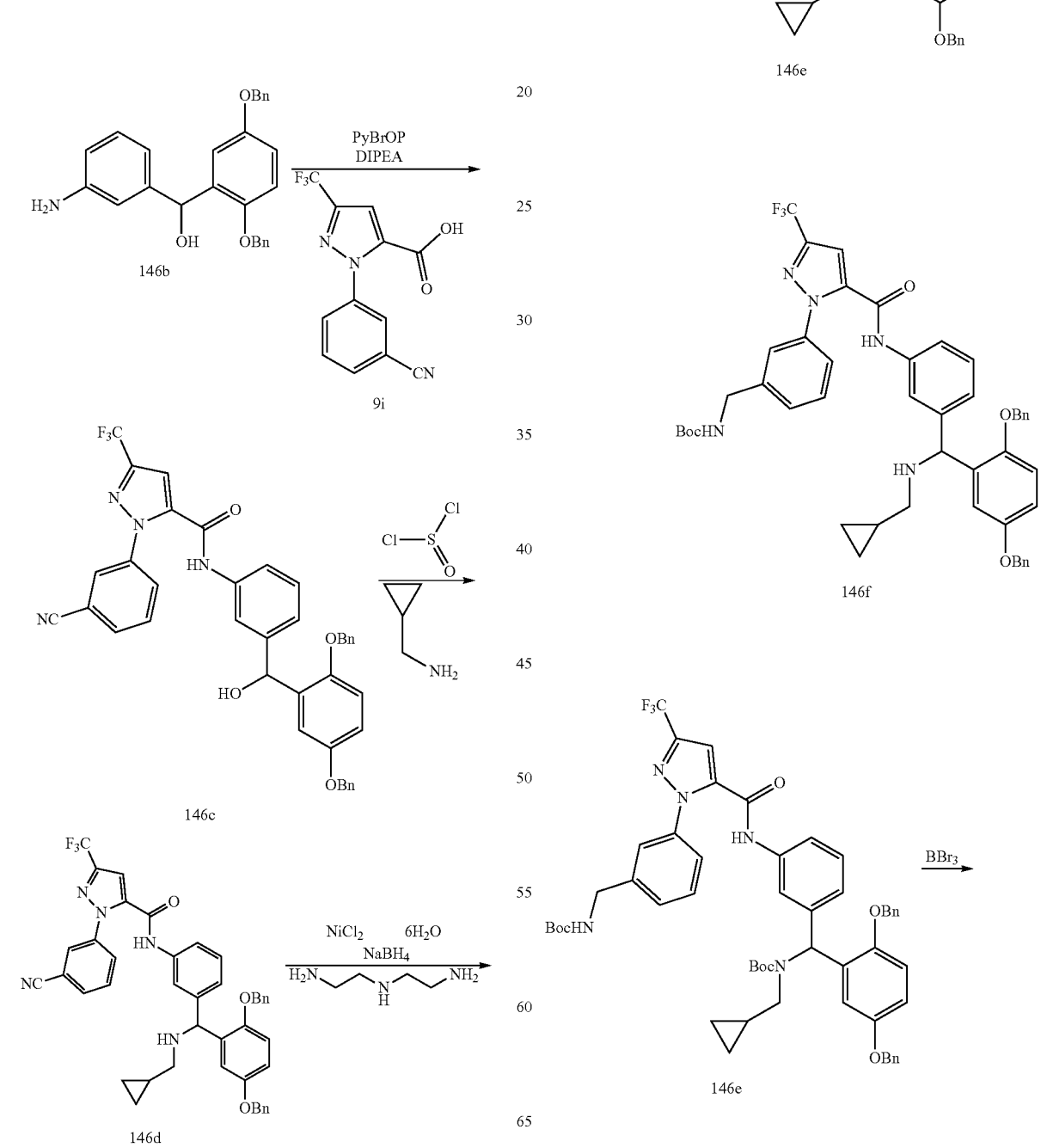

-continued

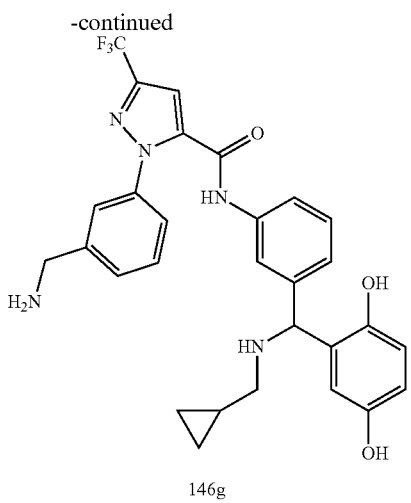

146g

Preparation of 1-(3-(Aminomethyl)phenyl)-N-(3-((cyclopropylmethylamino)(2, 5-dihydroxyphenyl)methyl) phenyl)-3-methyl-1H-pyrazole-5-carboxamide (146g)

Step-1: Preparation of (3-aminophenyl)(2,3-bis(benzyloxy)phenyl)methanol (146b)

To a stirred solution of 2,5-bis(benzyloxy)benzaldehyde (146a) (3.2 g, 10 mmol) in tetrahydrofuran (5 mL) was added (3-(bis(trimethylsilyl)amino)phenyl)magnesium chloride (49c) (12.00 mL, 12.00 mmol) at 0° C. The reaction was stirred for 14 h at room temperature, quenched by adding 2 N HCl (12.50 mL) and stirred for 6 h. The reaction mixture was treated with 2 N NaOH (15 mL) and extracted with ethyl acetate (2×50 mL). The organic layers were combined washed with sat. NH$_4$Cl (50 mL), dried over anhydrous MgSO$_4$, filtered, evaporated to dryness. The crude residue was purified by flash column chromatography (silica gel 40 g, eluting with 0-100% ethyl acetate in hexane) to furnish (3-aminophenyl)(2,5-bis(benzyloxy)phenyl)methanol (146b) (2.4 g, 58.32%) as a light brown solid; $^1$H NMR (300 MHz, DMSO-d$_6$) δ 7.46-7.29 (m, 10H), 7.14 (d, J=3.1 Hz, 1H), 6.94-6.84 (m, 2H), 6.80 (dd, J=8.9, 3.1 Hz, 1H), 6.57 (t, J=1.9 Hz, 1H), 6.50-6.44 (m, 1H), 6.38 (ddd, J=8.0, 2.3, 1.0 Hz, 1H), 5.86 (d, J=4.4 Hz, 1H), 5.52 (d, J=4.4 Hz, 1H), 5.01 (d, J=1.2 Hz, 4H), 4.93 (s, 2H).

Step-2: Preparation of N-(3-((2,5-bis(benzyloxy)phenyl)(hydroxy)methyl)phenyl)-1-(3-cyanophenyl)-3-(trifluoromethyl)-1H-pyrazole-5-carboxamide (146c)

To a solution of 1-(3-cyanophenyl)-3-(trifluoromethyl)-1H-pyrazole-5-carboxylic acid (9i) (1.57 g, 5.589 mmol) in DMF (40 mL) was added (3-aminophenyl)(2,5-bis(benzyloxy)phenyl)methanol (146b) (2.3 gm, 5.589 mmol), N-ethyl-N-isopropylpropan-2-amine (5.8 g, 44.93 mmol) and bromo-tris-pyrrolidino phosphoniumhexafluorophosphate (PyBrop 2.6 g, 5.589 mmol) at room temperature. The reaction mixture was stirred at room temperature for 42 h under nitrogen atmosphere. The reaction was diluted with ethyl acetate (350 mL) washed with water (2×150 mL), brine (120 mL), dried, filtered, and evaporated to dryness. The residue obtained was purified by flash column chromatography [silica gel 120 g, eluting with ethyl acetate in hexanes from 0-30%] to furnish N-(3-((2,5-bis(benzyloxy)phenyl)(hydroxy)methyl)phenyl)-1-(3-cyanophenyl)-3-(trifluoromethyl)-1H-pyrazole-5-carboxamide (146c) (2.55 g, 67.62%) as a off white solid; $^1$H NMR (300 MHz, DMSO-d$_6$) δ 10.61 (s, 1H), 8.15 (t, J=1.8 Hz, 1H), 7.96 (dt, J=7.8, 1.3 Hz, 1H), 7.88 (ddd, J=8.2, 2.2, 1.1 Hz, 1H), 7.75-7.66 (m, 2H), 7.64 (d, J=1.9 Hz, 1H), 7.56-7.49 (m, 1H), 7.45-7.27 (m, 10H), 7.21 (t, J=7.8 Hz, 1H), 7.13 (d, J=3.1 Hz, 1H), 7.04 (d, J=7.7 Hz, 1H), 6.92 (d, J=9.0 Hz, 1H), 6.82 (dd, J=8.9, 3.1 Hz, 1H), 5.96 (d, J=4.3 Hz, 1H), 5.79 (d, J=4.3 Hz, 1H), 5.00 (d, J=1.9 Hz, 4H).

Step-3: Preparation of N-(3-((2,5-bis(benzyloxy)phenyl)((cyclopropylmethyl)amino)methyl)phenyl)-1-(3-cyanophenyl)-3-(trifluoromethyl)-1H-pyrazole-5-carboxamide (146d)

To a solution of N-(3-((2,5-bis(benzyloxy)phenyl)(hydroxy)methyl)phenyl)-1-(3-cyanophenyl)-3-(trifluoromethyl)-1H-pyrazole-5-carboxamide (146c) (2.5 gm, 3.705 mmol) in dichloromethane (50 mL) at 0° C. was added thionyl chloride (0.53 g, 7.41 mmol) and stirred at room temperature for 4 h. The reaction mixture was concentrated in vacuum to dryness. The residue obtained was dissolved in acetonitrile (40 mL) and added cyclopropylmethanamine (4.826 g, 55.57 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum. The residue obtained was purified by flash column chromatography (silica gel 40 g, eluting 0-40% ethyl acetate in hexane) to afford N-(3-((2,5-bis(benzyloxy)phenyl)((cyclopropylmethyl)amino)methyl)phenyl)-1-(3-cyanophenyl)-3-(trifluoromethyl)-1H-pyrazole-5-carboxamide (146d) (0.9 gm, 33.37%) as brown sticky liquid; $^1$HNMR (300 MHz, DMSO-d$_6$) δ 10.60 (s, 1H), 8.14 (t, J=1.8 Hz, 1H), 7.95 (dt, J=7.7, 1.3 Hz, 1H), 7.88 (ddd, J=8.2, 2.2, 1.1 Hz, 1H), 7.69 (s, 1H), 7.66 (d, J=2.4 Hz, 1H), 7.54-7.48 (m, 1H), 7.46-7.24 (m, 11H), 7.21 (t, J=7.8 Hz, 1H), 7.13 (d, J=3.1 Hz, 1H), 7.08 (dt, J=7.8, 1.3 Hz, 1H), 6.93 (d, J=8.9 Hz, 1H), 6.80 (dd, J=8.9, 3.1 Hz, 1H), 5.17 (s, 1H), 5.00 (d, J=3.3 Hz, 4H), 2.24 (qd, J=12.0, 6.7 Hz, 2H), 1.86 (dt, J=4.9, 2.4 Hz, 1H), 0.93-0.74 (m, 1H), 0.38-0.27 (m, 2H), 0.09--0.20 (m, 2H).

Step-4: tert-butyl 3-(5-((3-((2,5-bis(benzyloxy)phenyl)((cyclopropylmethyl)amino)methyl) phenyl)carbamoyl)-3-(trifluoromethyl)-1H-pyrazol-1-yl)benzylcarbamate (146f)

To a solution of N-(3-((2,5-bis(benzyloxy)phenyl)((cyclopropylmethyl)amino)methyl)phenyl)-1-(3-cyanophenyl)-3-(trifluoromethyl)-1H-pyrazole-5-carboxamide (146d) (0.9 gm, 1.236 mmol) in MeOH (12 mL) cooled with ice/water was added nickel(II) chloride hexahydrate (0.367 g, 1.548 mmol) and Boc anhydride (0.809 g, 3.708 mmol) followed by portionwise addition of sodium borohydride (0.280 g, 7.416 mmol) over a period of 15 min. The reaction mixture was stirred at room temperature for 2 hrs and quenched with N$^1$-(2-aminoethyl)ethane-1,2-diamine (0.510 mL, 4.944 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over MgSO$_4$ filtered and concentrated in vacuum. The residue obtained was purified by flash column chromatography (silica gel 24 g, eluting with 0-25% Ethyl acetate/hexane) to furnish
1. tert-butyl ((2,5-bis(benzyloxy)phenyl)(3-(1-(3-(((tert-butoxycarbonyl)amino)methyl) phenyl)-3-(trifluoromethyl)-1H-pyrazole-5-carboxamido)phenyl) methyl)(cyclopropylmethyl)carbamate (146e) (0.08 g, 6.94%)

¹H NMR (300 MHz, DMSO-d₆) δ 10.71 (s, 1H), 7.65 (s, 2H), 7.56 (s, 1H), 7.51-7.24 (m, 17H), 7.10-6.83 (m, 2H), 6.63-6.47 (m, 2H), 5.02 (t, J=11.7 Hz, 4H), 4.18 (d, J=5.1 Hz, 2H), 3.23-2.82 (m, 1H), 1.37 (s, 18H), 0.93-0.82 (m, 1H), 0.23-0.04 (m, 2H), −0.13−−0.42 (m, 2H); ¹⁹F NMR (282 MHz, DMSO) δ −60.65; MS (ES+) 954.5 (M+Na); (ES−) 930.5 (M−1).

2. tert-butyl 3-(5-((3-((2,5-bis(benzyloxy)phenyl)((cyclopropylmethyl)amino) methyl)phenyl)carbamoyl)-3-(trifluoromethyl)-1H-pyrazol-1-yl)benzylcarbamate (146f) (0.12 g, 0.12 g, 11.67%) ¹H NMR (300 MHz, DMSO-d₆) δ 10.66 (s, 1H), 7.63 (s, 1H), 7.56 (d, J=3.5 Hz, 1H), 7.49 (t, J=8.1 Hz, 1H), 7.34 (dtq, J=11.8, 9.6, 4.8 Hz, 13H), 7.20 (t, J=7.8 Hz, 1H), 7.15-6.75 (m, 2H), 5.01 (d, J=4.7 Hz, 2H), 4.17 (d, J=6.0 Hz, 2H), 1.36 (d, J=4.1 Hz, 9H), 1.23-1.13 (m, 1H), 0.85 (s, 2H), 0.36 (dd, J=21.4, 8.4 Hz, 2H); ¹⁹F NMR (282 MHz, DMSO) δ −60.784; MS (ES+) 832.5 (M+1); (ES) 830.4 (M−1).

Step-5: Preparation of 1-(3-(Aminomethyl)phenyl)-N-(3-((cyclopropylmethylamino)(2,5-dihydroxyphenyl)methyl) phenyl)-3-methyl-1H-pyrazole-5-carboxamide (146g)

To a solution of tert-butyl 3-(5-(3-((2,5-bis(benzyloxy) phenyl)(cyclopropylmethylamino)methyl)phenylcarbamoyl)-3-(trifluoromethyl)-1H-pyrazol-1-yl)benzylcarbamate (146f) (0.12 g, 0.144 mmol) in dichloromethane (10 mL) cooled to 0° C. was added dropwise under a nitrogen atmosphere tribromoborane (1 M solution in dichloromethane) (0.577 mL, 0.577 mmol). The reaction mixture was allowed to warm to room temperature and stirred at room temperature 2 h. The reaction mixture was quenched with methanol (5 mL) and concentrated in vacuo to dryness. The residue obtained was triturated with methanol and dried under vacuum, this step was repeated four times to furnish crude product. The residue obtained was purified twice by flash column chromatography [silica gel 12 g and 4 g, eluting with CMA-80 in chloroform from 0-100%] to furnish 1-(3-(aminomethyl)phenyl)-N-(3-((cyclopropylmethylamino)(2,5-dihydroxyphenyl)methyl)phenyl)-3-(trifluoromethyl)-1H-pyrazole-5-carboxamide (146g) (0.045 g, 56.6%) as a yellow solid; ¹H NMR (300 MHz, DMSO-d₆) δ 10.74 (s, 1H), 8.63 (s, 1H), 7.62 (d, J=2.0 Hz, 1H), 7.59-7.50 (m, 3H), 7.46-7.40 (m, 2H), 7.32 (dd, J=6.4, 2.7 Hz, 1H), 7.27 (d, J=7.8 Hz, 1H), 7.23-7.16 (m, 1H), 6.50 (d, J=8.3 Hz, 1H), 6.47-6.40 (m, 2H), 4.91 (s, 1H), 3.78 (s, 2H), 2.43-2.18 (m, 2H), 0.94 (m, 1H), 0.40 (m, 2H), 0.08 (m, 2H); ¹⁹F NMR (282 MHz, DMSO) δ −60.70; MS (ES+) 552.3 (M+1); (ES−) 550.3 (M+1); Analysis calculated for C₂₉H₃₁N₅O₃·0.75HBr: C, 62.39; H, 5.73; N, 12.54; Found: C, 62.23; H, 5.44; N, 12.16.

Scheme 147

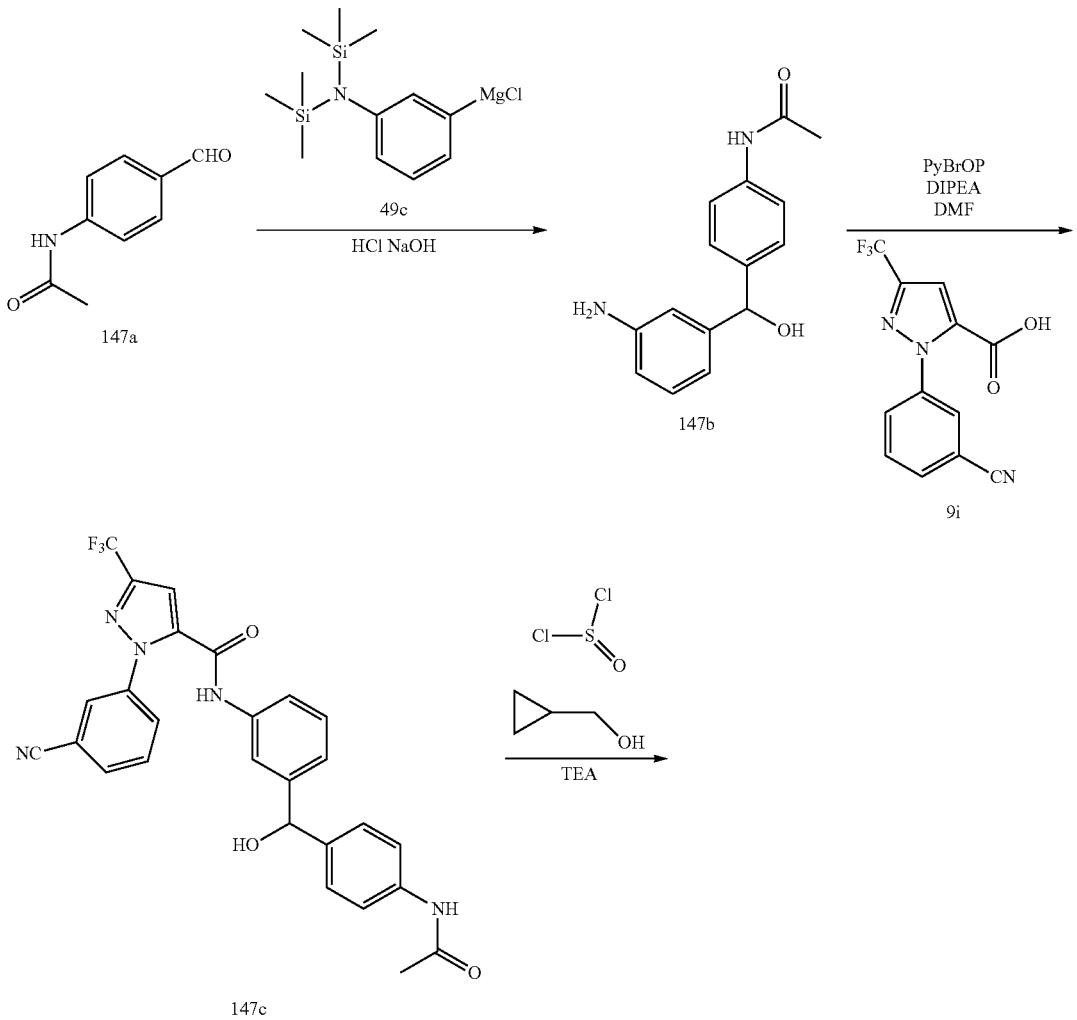

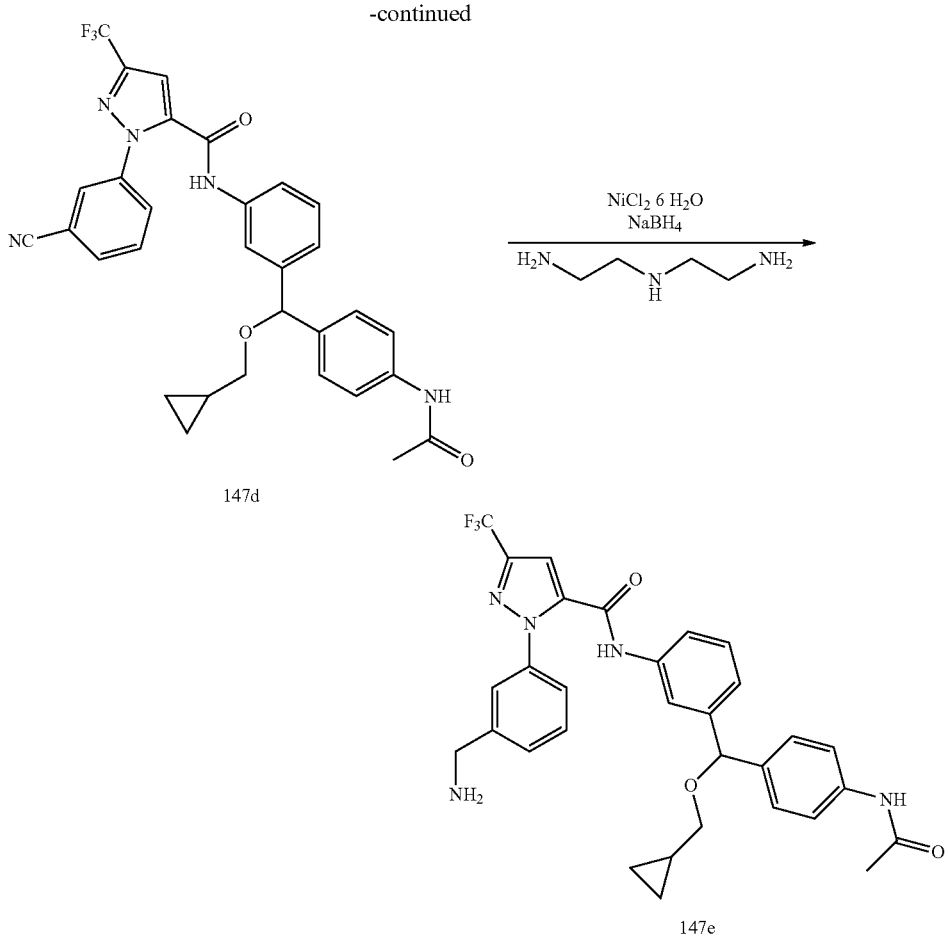

Preparation of N-(3-((4-acetamidophenyl)(cyclopropylmethoxy)methyl)phenyl)-1-(3-(aminomethyl)phenyl)-3-(trifluoromethyl)-1H-pyrazole-5-carboxamide (147e)

Step-1: Preparation of N-(4-((3-aminophenyl)(hydroxy)methyl)phenyl)acetamide (147b)

To a stirred solution of N-(4-formylphenyl)acetamide (147a) (3.26 g, 20 mmol) in tetrahydrofuran (30 mL) was added (3-(bis(trimethylsilyl)amino)phenyl)magnesium chloride (49c) (24 mL, 24.00 mmol) at 0° C. The reaction was stirred for 14 h at same temperature and quenched by adding 12 N HCl (4.17 mL, 50.0 mmol), stirred for 1 h. The reaction mixture was treated with 2 N NaOH (30.0 mL, 60.0 mmol) and extracted with ethyl acetate (2×50 mL). The organic layers were combined washed with sat. NH$_4$Cl (50 mL), dried over anhydrous MgSO$_4$, filtered, evaporated to dryness. The crude residue was purified by flash column chromatography (silica gel 120 g, eluting with 0-100% ethyl acetate in hexane) to furnish N-(4-((3-aminophenyl)(hydroxy)methyl)phenyl)acetamide (147b) (2.098 g, 41% yield) as a yellow solid which was used as such in the next step; MS (ES−): 255.2 (M−1).

Step-2: Preparation of N-(3-((4-acetamidophenyl)(hydroxy)methyl)phenyl)-1-(3-cyanophenyl)-3-(trifluoromethyl)-1H-pyrazole-5-carboxamide (147c)

A single-necked 100 mL flask containing 1-(3-cyanophenyl)-3-(trifluoromethyl)-1H-pyrazole-5-carboxylic acid (9i) (2.61 g, 9.28 mmol), N-(4-((3-aminophenyl)(hydroxy)methyl)phenyl)acetamide (147b) (1.983 g, 7.74 mmol), bromo-tris-pyrrolidino phosphoniumhexafluorophosphate (PyBrOP, 4.33 g, 9.28 mmol) was added N,N-dimethylformamide (44.9 mL, 580 mmol) and N-ethyl-N-isopropylpropan-2-amine (6.74 mL, 38.7 mmol) successively in a positive flow of nitrogen at room temperature. The resulting reaction mixture was stirred at room temperature for 16 h under a positive flow of nitrogen atmosphere. Excess DMF was pumped-off under reduced pressure. The residue was treated with water (250 mL), and extracted with chloroform (2×250 mL) combined organics were dried over anhydrous MgSO$_4$, filtered, evaporated to dryness. The residue was then purified by flash column chromatography [silica gel 40 g, eluting with methanol in chloroform from 0-100%] to furnish N-(3-((4-acetamidophenyl)(hydroxy)methyl)phenyl)-1-(3-cyanophenyl)-3-(trifluoromethyl)-1H-pyrazole-5-carboxamide (147c) (1.159 g, 29% yield) as a yellow solid; MS (ES−): 518.2 (M−1).

Step-3: Preparation of N-(3-((4-acetamidophenyl)(cyclopropylmethoxy)methyl)phenyl)-1-(3-cyanophenyl)-3-(trifluoromethyl)-1H-pyrazole-5-carboxamide (147d)

To a solution of N-(3-((4-acetamidophenyl)(hydroxy)methyl)phenyl)-1-(3-cyanophenyl)-3-(trifluoromethyl)-1H-pyrazole-5-carboxamide (147c) (1.139 g, 2.193 mmol) in dichloromethane (20 mL) at 0° C. was added thionyl chloride (0.480 mL, 6.58 mmol), reaction mixture allowed to warm to room temperature and stirred for 3 h. The reaction mixture was quenched with triethylamine (1.528 mL, 10.96 mmol), and solution was stirred for 30 min at room temperature, and concentrated in vacuum to dryness. The residue was dissolved in acetonitrile (20 mL) to this was cyclopropylmethanol (18.64 mL, 254 mmol) and triethylamine (1.528 mL, 10.96 mmol) were added and stirred at 100° C. for 18 h. The reaction mixture was cooled to room temperature evaporated under reduced pressure. The residue was purified by flash column chromatography (silica gel 40 g, eluting with methanol in chloroform from 0-100%) to afford N-(3-((4-acetamidophenyl)(cyclopropylmethoxy) methyl)phenyl)-1-(3-cyanophenyl)-3-(trifluoromethyl)-1H-pyrazole-5-carboxamide (147d) (0.494 g, 39% yield) as a brown solid; $^1$H NMR (300 MHz, DMSO-d$_6$) δ 10.67 (s, 1H), 9.92 (s, 1H), 8.17 (t, J=1.9 Hz, 1H), 8.00 (dt, J=7.8, 1.3 Hz, 1H), 7.90 (ddd, J=8.2, 2.2, 1.1 Hz, 1H), 7.78-7.70 (m, 2H), 7.59 (t, J=3.3 Hz, 2H), 7.54-7.47 (m, 2H), 7.35-7.20 (m, 3H), 7.11 (d, J=7.7 Hz, 1H), 5.38 (s, 1H), 3.21 (d, J=6.8 Hz, 2H), 2.01 (s, 3H), 1.04 (d, J=5.2 Hz, 1H), 0.49-0.42 (m, 2H), 0.17-0.12 (m, 2H); $^{19}$F NMR (282 MHz, DMSO-d$_6$) δ −60.93; MS (ES$^+$): MS (ES+) 574.4 (M+1), 596.4 (M+Na), MS (ES−) 572.2 (M−1).

Step-4: Preparation of N-(3-((4-acetamidophenyl) (cyclopropylmethoxy)methyl)phenyl)-1-(3-(aminomethyl)phenyl)-3-(trifluoromethyl)-1H-pyrazole-5-carboxamide (147e)

To a stirred solution of N-(3-((4-acetamidophenyl)(cyclopropylmethoxy)methyl)phenyl)-1-(3-cyanophenyl)-3-(trifluoromethyl)-1H-pyrazole-5-carboxamide (147d) (0.481 g, 0.839 mmol) in anhydrous methanol (10 mL), cooled to 0° C., were added nickel(II) chloride hexahydrate (0.100 g, 0.419 mmol), sodium borohydride (0.254 g, 6.71 mmol) was then added in small portions over 5 min. The reaction was exothermic and effervescent. The reaction mixture was stirred for 15 min at 0° C., at this point N1-(2-aminoethyl) ethane-1,2-diamine (0.906 mL, 8.39 mmol) was added. The mixture was allowed to stir for 30 minutes more before solvent was evaporated. The residue was treated with water (30 mL), and extracted with chloroform (2×30 mL), then ethyl acetate (2×30 mL), combined organic layers were dried over anhydrous MgSO$_4$, and filtered, excess solvents were pumped-off under reduced pressure. The residue was purified by flash column chromatography [(silica gel 40 g, eluting with CMA80/chloroform from 0 to 100%)] to furnish N-(3-((4-acetamidophenyl)(cyclopropylmethoxy) methyl)phenyl)-1-(3-(aminomethyl)phenyl)-3-(trifluoromethyl)-1H-pyrazole-5-carboxamide (147e) (203 mg, 42% yield) as a colorless solid; $^1$H NMR (300 MHz, DMSO-d$_6$) δ 10.71 (s, 1H,), 9.93 (s, 1H, D$_2$O exchangeable), 7.62-7.48 (m, 6H), 7.47-7.41 (m, 2H), 7.36-7.20 (m, 4H), 7.10 (d, J=7.6 Hz, 1H), 5.37 (s, 1H), 3.79 (s, 2H), 3.21 (dd, J=6.8, 1.3 Hz, 2H), 2.01 (s, 3H), 1.04 (ddd, J=12.7, 8.5, 5.3 Hz, 1H), 0.55-0.38 (m, 2H), 0.14 (tq, J=4.5, 2.3, 1.9 Hz, 2H); $^1$H NMR (300 MHz, DMSO-d$_6$, D$_2$O) δ 7.62-7.41 (m, 8H), 7.37-7.21 (m, 4H), 7.11 (d, J=7.7 Hz, 1H), 5.37 (s, 1H), 3.78 (s, 2H), 3.21 (d, J=6.8 Hz, 2H), 2.01 (s, 3H), 1.13-0.96 (m, 1H), 0.46 (dd, J=7.6, 2.3 Hz, 2H), 0.13 (dd, J=4.5, 2.3 Hz, 2H); $^{19}$F NMR (282 MHz, DMSO-d$_6$) δ −60.71; MS (ES+): MS (ES+) 578.3 (M+1), MS (ES−) 612.3 (M+Cl); Analysis calculated for: C$_{31}$H$_{30}$F$_3$N$_5$O$_3$: C, 64.46; H, 5.24; N, 12.12; Found: C, 64.03; H, 5.24; N, 11.77.

Scheme 148

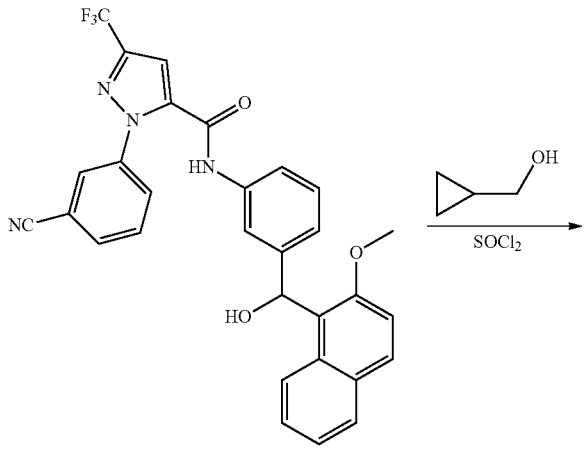

51c

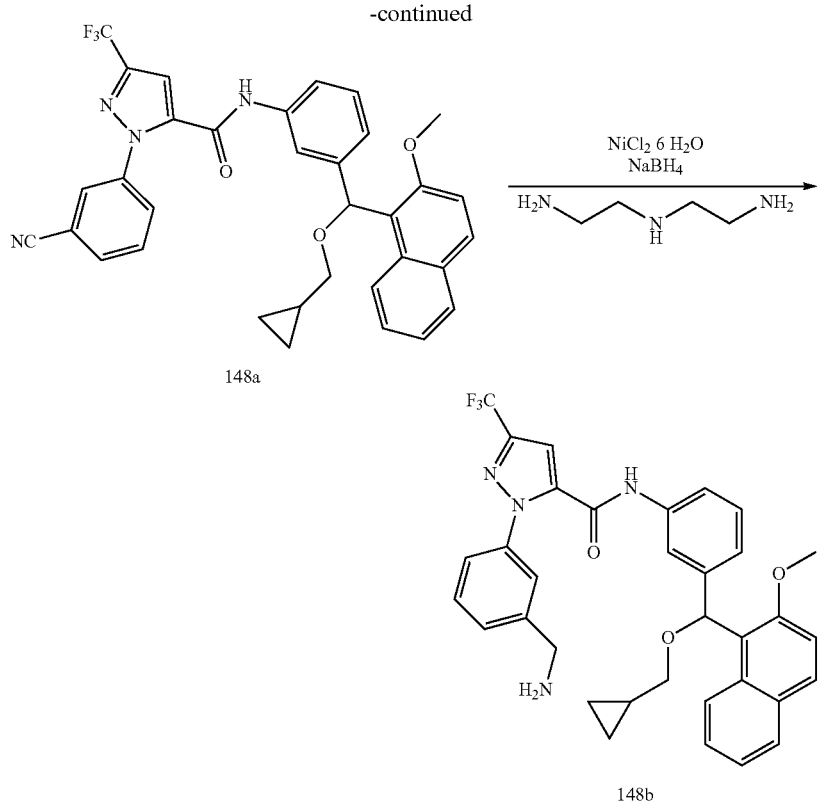

Preparation of 1-(3-(aminomethyl)phenyl)-N-(3-((cyclopropylmethoxy)(2-methoxynaphthalen-1-yl)methyl)phenyl)-3-(trifluoromethyl)-1H-pyrazole-5-carboxamide (148b)

Step-1: Preparation of 1-(3-cyanophenyl)-N-(3-((cyclopropylmethoxy)(2-methoxynaphthalen-1-yl)methyl)phenyl)-3-(trifluoromethyl)-1H-pyrazole-5-carboxamide (148a)

To a solution of 2-(3-Cyano-phenyl)-5-trifluoromethyl-2H-pyrazole-3-carboxylic acid {3-[hydroxy-(2-methoxy-naphthalen-1-yl)-methyl]-phenyl}-amide (51c) (3.5 g, 6.45 mmol) in dichloromethane (50 mL) at 0° C. was added thionyl chloride (1.413 mL, 19.35 mmol) and stirred at room temperature for 2 h. The reaction was treated with triethylamine (5.40 mL, 38.7 mmol) and stirred at room temperature for 8 h. The reaction was treated with cyclopropanemethanol (10.22 mL, 129 mmol), concentrated to remove most of dichloromethane followed by addition of acetonitrile (50.0 mL) and heating at reflux for 16 h. Reaction was concentrated to dryness, diluted water (200 mL) and extracted with ethylacetate (3×300 mL). The organic layers were combined washed with water (100 mL), brine (100 mL) dried over MgSO$_4$ followed by filtration and concentration. Residue was purified by flash column chromatography (silica gel, 120 g eluting with ethyl acetate in hexanes 0 to 30%) to afford pure 1-(3-cyanophenyl)-N-(3-((cyclopropylmethoxy)(2-methoxynaphthalen-1-yl)methyl)phenyl)-3-(trifluoromethyl)-1H-pyrazole-5-carboxamide (145a) (2.5 g, 65.0% yield) as a white solid.

Step-2: Preparation of 1-(3-(aminomethyl)phenyl)-N-(3-((cyclopropylmethoxy)(2-methoxynaphthalen-1-yl)methyl)phenyl)-3-(trifluoromethyl)-1H-pyrazole-5-carboxamide (148b)

To a stirred solution of 1-(3-cyanophenyl)-N-(3-((cyclopropylmethoxy)(2-methoxynaphthalen-1-yl)methyl)phenyl)-3-(trifluoromethyl)-1H-pyrazole-5-carboxamide (145a) (1.862 g, 3.12 mmol) in methanol (70 mL) at 0° C. was added nickel(II) chloride hexahydrate (0.162 g, 0.680 mmol). To this sodium tetrahydroborate (1.181 g, 31.2 mmol) was added in small portions over a period of 10 minutes. The reaction was stirred for 1 h, quenched by adding N1-(2-aminoethyl)ethane-1,2-diamine (0.805 g, 7.80 mmol) and stirred for 1 h. The reaction mixture was concentrated to remove methanol, diluted with water (150 mL) and stirred for 30 minutes. The solid separated was collected by filtration, dried in vacuum and purified by flash column chromatography (silica gel, 40 g eluting with ethyl acetate in hexanes 0 to 100%) to afford 1-(3-(aminomethyl)phenyl)-N-(3-((cyclopropylmethoxy)(2-methoxynaphthalen-1-yl)methyl)phenyl)-3-(trifluoromethyl)-1H-pyrazole-5-carboxamide (148b) (0.91 g, 48.5% yield) as a colorless solid; $^1$H NMR (300 MHz, DMSO-d$_6$) δ 10.71 (s, 1H,), 9.93 (s, 1H, D$_2$O exchangeable), 7.62-7.48 (m, 6H), 7.47-7.41 (m, 2H), 7.36-7.20 (m, 4H), 7.10 (d, J=7.6 Hz, 1H), 5.37 (s, 1H), 3.79 (s, 2H), 3.21 (dd, J=6.8, 1.3 Hz, 2H), 2.01 (s, 3H), 1.04 (ddd, J=12.7, 8.5, 5.3 Hz, 1H), 0.55-0.38 (m, 2H), 0.14 (tq, J=4.5, 2.3, 1.9 Hz, 2H); 1H NMR (300 MHz, DMSO-d$_6$, D$_2$O) δ 7.62-7.41 (m, 8H), 7.37-7.21 (m, 4H), 7.11 (d, J=7.7 Hz, 1H), 5.37 (s, 1H), 3.78 (s, 2H), 3.21 (d, J=6.8 Hz, 2H), 2.01 (s, 3H), 1.13-0.96 (m, 1H), 0.46 (dd, J=7.6, 2.3 Hz, 2H), 0.13 (dd, J=4.5, 2.3 Hz, 2H); 19F NMR (282 MHz, DMSO-d$_6$) δ −60.71. MS (ES+) 578.3 (M+1), MS (ES−) 612.3 (M+Cl).; Analysis calculated for C$_{31}$H$_{30}$F$_3$N$_5$O$_3$:C, 64.46; H, 5.24; N, 12.12; Found: C, 64.03; H, 5.24; N, 11.77.

Scheme 149

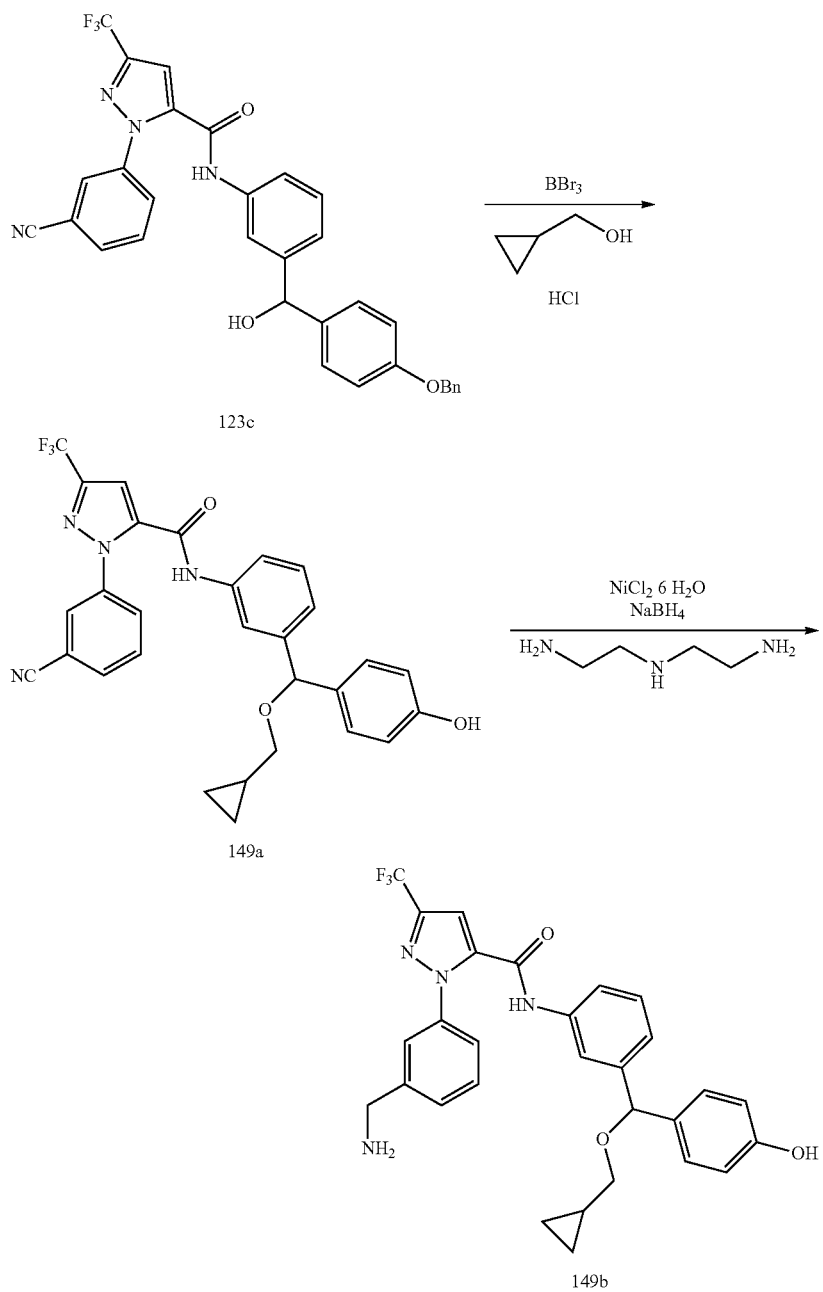

Preparation of 1-(3-(aminomethyl)phenyl)-N-(3-((cyclopropylmethoxy)(4-hydroxyphenyl)methyl)phenyl)-3-(trifluoromethyl)-1H-pyrazole-5-carboxamide (149b)

Step-1: Preparation of 1-(3-cyanophenyl)-N-(3-((cyclopropylmethoxy)(4-hydroxyphenyl)methyl)phenyl)-3-(trifluoromethyl)-1H-pyrazole-5-carboxamide (149a)

To a solution of N-(3-((4-(benzyloxy)phenyl)(hydroxy)methyl)phenyl)-1-(3-cyanophenyl)-3-(trifluoromethyl)-1H-pyrazole-5-carboxamide (123c) (1.0 g, 1.759 mmol) in dichloromethane (30 mL) cooled to −78° C. was added drop-wise under a positive flow nitrogen tribromoborane (1 M solution in dichloromethane) (5.28 mL, 5.28 mmol) over a period of 10 min. The reaction mixture was allowed to warm to room temperature and stirred at room temperature for 1.5 h. The reaction mixture was quenched with cyclopropylmethanol (6.44 mL, 88 mmol), evaporated, this cycle repeated twice then to dryness. To this residue cyclopropylmethanol (6.44 mL, 88 mmol) and hydrogen chloride (8.79 mL, 35.2 mmol) was added and refluxed for 16 h. Excess solvent was evaporated, to the flask 5 g silica gel and chloroform (30 mL) was added and evaporated to dryness. The residue was then purified by flash column chromatography [silica gel 40 g, eluting with ethyl acetate in hexanes from 0-100%] to furnish 1-(3-cyanophenyl)-N-(3-((cyclopropylmethoxy)(4-hydroxyphenyl)methyl)phenyl)-3-(trifluoromethyl)-1H-pyrazole-5-carboxamide (149a)(0.485 g, 52% yield) as a white solid which was used as such in the next step; MS (ES−) 531.1 (M−1), 567.1 (M+Cl);

Step-2: Preparation of 1-(3-(aminomethyl)phenyl)-N-(3-((cyclopropylmethoxy)(4-hydroxyphenyl)methyl)phenyl)-3-(trifluoromethyl)-1H-pyrazole-5-carboxamide (149b)

To a stirred solution of 1-(3-cyanophenyl)-N-(3-((cyclopropylmethoxy)(4-hydroxyphenyl)methyl)phenyl)-3-(trifluoromethyl)-1H-pyrazole-5-carboxamide (149a) (0.430 g, 0.807 mmol) in anhydrous methanol (10 mL), cooled to 0° C., were added nickel(II) chloride hexahydrate (0.096 g, 0.404 mmol), sodium borohydride (0.244 g, 6.46 mmol) was then added in small portions over a period of 5 min. The reaction was exothermic and effervescent. The reaction mixture was stirred for 15 min at 0° C., at this point N1-(2-aminoethyl)ethane-1,2-diamine (0.872 mL, 8.07 mmol) was added. The mixture was allowed to stir for 30 minutes and concentrated in vacuum to dryness. The residue was treated with water (50 mL), and extracted with chloroform (2×50 mL), then ethyl acetate (2×50 mL), combined organic layers were dried over anhydrous MgSO$_4$, and filtered, excess solvents were pumped-off under reduced pressure. The residue was purified by flash column chromatography [(silica gel 40 g, eluting with CMA80/chloroform from 0 to 100%)] to furnish 1-(3-(aminomethyl)phenyl)-N-(3-((cyclopropylmethoxy)(4-hydroxyphenyl)methyl)phenyl)-3-(trifluoromethyl)-1H-pyrazole-5-carboxamide (149b) (51 mg, 12% yield) as a colorless solid. $^1$H NMR (300 MHz, DMSO-d$_6$) δ 10.70 (s, 1H, D$_2$O exchangeable), 9.37 (s, 1H, D$_2$O exchangeable), 7.59-7.51 (m, 4H), 7.45-7.41 (m, 2H), 7.35-7.23 (m, 2H), 7.15-7.05 (m, 3H), 6.71 (s, 1H), 6.68 (s, 1H), 5.31 (s, 1H), 3.79 (s, 2H), 3.19 (d, J=6.7 Hz, 2H), 2.39 (s, 2H, D$_2$O exchangeable), 1.11-0.96 (m, 1H), 0.44 (ddd, J=7.9, 3.7, 2.5 Hz, 2H), 0.13 (ddd, J=6.7, 3.3, 2.0 Hz, 2H); $^1$H NMR (300 MHz, DMSO-d$_6$ D$_2$O) δ 7.62-7.49 (m, 4H), 7.45 (dd, J=4.8, 2.3 Hz, 2H), 7.36-7.25 (m, 2H), 7.15-7.08 (m, 3H), 6.75-6.68 (m, 2H), 5.32 (s, 1H), 3.77 (s, 2H), 3.19 (d, J=6.8 Hz, 2H), 1.11-0.96 (m, 1H), 0.45 (ddd, J=7.8, 3.7, 2.4 Hz, 2H), 0.13 (ddd, J=6.7, 3.3, 2.0 Hz, 2H); $^{19}$F NMR (282 MHz, DMSO-d$_6$) δ −60.71; MS (ES$^+$): MS (ES+) 537.3 (M+1), MS (ES−) 535.3 (M−1), 571.3 (M+Cl); Analysis calculated for: C$_{29}$H$_{27}$F$_3$N$_4$O$_3$.0.5H$_2$O: C, 63.85; H, 5.17; N, 10.27; Found: C, 63.91; H, 5.30; N, 10.24.

Scheme 150

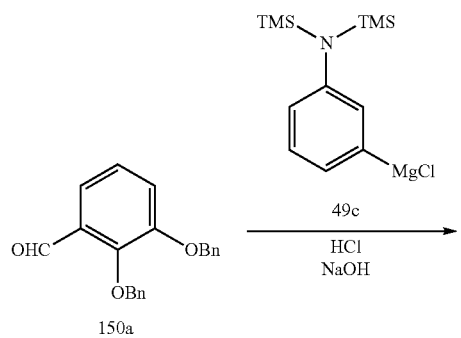

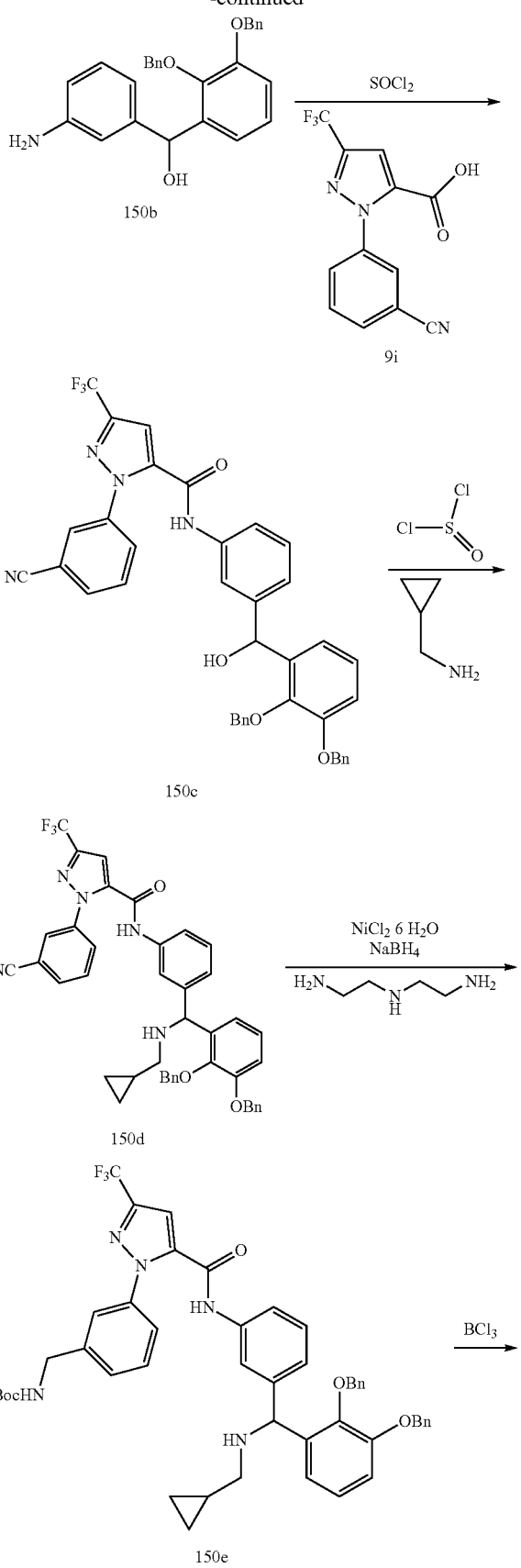

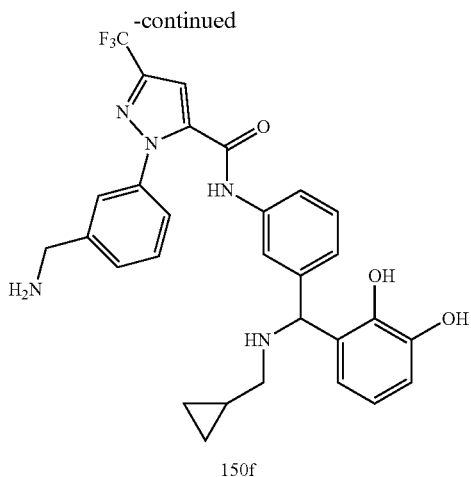

150f

Preparation of 1-(3-(Aminomethyl)phenyl)-N-(3-((cyclopropylmethylamino)(2,3-dihydroxyphenyl)methyl) phenyl)-3-methyl-1H-pyrazole-5-carboxamide (150f)

Step-1: Preparation of (3-aminophenyl)(2,3-bis(benzyloxy)phenyl)methanol (150b)

To a stirred solution of 2,3-bis(benzyloxy)benzaldehyde (150a) (3.2 g, 10 mmol) in tetrahydrofuran (5 mL) was added (3-(bis(trimethylsilyl)amino)phenyl)magnesium chloride (49c) (12.00 mL, 12.00 mmol) at 0° C. The reaction was stirred for 14 h at room temperature, quenched by adding 2 N HCl (12.50 mL) and stirred for 6 h. The reaction mixture was treated with 2 N NaOH (15 mL) and extracted with ethyl acetate (2×50 mL). The organic layers were combined washed with saturated aqueous $NH_4Cl$ (50 mL), dried over anhydrous $MgSO_4$, filtered, evaporated to dryness. The crude residue was purified by flash column chromatography (silica gel 40 g, eluting with 0-100% ethyl acetate in hexane) to furnish (3-aminophenyl)(2,3-bis(benzyloxy)phenyl)methanol (150b) (2.5 g, 60.75%) as a light brown solid; $^1$H NMR (300 MHz, DMSO-$d_6$) δ 7.53-7.46 (m, 2H), 7.41-7.30 (m, 8H), 7.05 (s, 3H), 6.89 (t, J=7.7 Hz, 1H), 6.54 (t, J=1.9 Hz, 1H), 6.45 (dt, J=7.7, 1.3 Hz, 1H), 6.37 (ddd, J=8.0, 2.3, 1.1 Hz, 1H), 5.90 (d, J=4.4 Hz, 1H), 5.55 (d, J=4.5 Hz, 1H), 5.15 (s, 2H), 4.96 (s, 2H), 4.91 (d, J=10.5 Hz, 1H), 4.75 (d, J=10.5 Hz, 1H).

Step-2: N-(3-((2,3-bis(benzyloxy)phenyl)(hydroxy)methyl)phenyl)-1-(3-cyanophenyl)-3-(trifluoromethyl)-1H-pyrazole-5-carboxamide (150c)

To a solution of 1-(3-cyanophenyl)-3-(trifluoromethyl)-1H-pyrazole-5-carboxylic acid (9i) (1.2 g, 4.26 mmol) in toluene (30 mL) and DMF (15 drops) was added at 0° C. $SOCl_2$ (1.16 g, 9.79 mmol) and heated at reflux for 3.5 h. The reaction mixture was cooled to room temperature and concentrated in vacuum to dryness. The residue was dissolved in dichloromethane (100 mL) and added (3-aminophenyl)(2,3-bis(benzyloxy)phenyl)methanol (150b) (2.5 g, 3.58 mmol), and triethylamine (5 mL). The reaction mixture was stirred at room temperature for 18 h under nitrogen atmosphere. The reaction was diluted with ethyl acetate (350 mL) washed with water (2×150 mL), brine (120 mL), dried, filtered, and evaporated to dryness. The residue obtained was purified by flash column chromatography [silica gel 120 g, eluting with ethyl acetate in hexanes from 0-30%] to furnish N-(3-((2,3-bis(benzyloxy)phenyl)(hydroxy)methyl)phenyl)-1-(3-cyanophenyl)-3-(trifluoromethyl)-1H-pyrazole-5-carboxamide (150c) (2.4 g, 83.50%) as a brown solid; $^1$H NMR (300 MHz, DMSO-$d_6$) δ 10.62 (s, 1H), 8.15 (t, J=1.8 Hz, 1H), 7.98 (dt, J=7.8, 1.3 Hz, 1H), 7.89 (ddd, J=8.2, 2.2, 1.1 Hz, 1H), 7.76-7.67 (m, 2H), 7.61 (t, J=1.8 Hz, 1H), 7.58-7.44 (m, 3H), 7.39 (s, 2H), 7.37-7.24 (m, 6H), 7.22 (t, J=7.9 Hz, 1H), 7.11-6.97 (m, 4H), 6.01 (d, J=4.2 Hz, 1H), 5.81 (d, J=4.3 Hz, 1H), 5.15 (s, 2H), 4.99-4.77 (m, 2H).

Step-3: N-(3-((2,3-bis(benzyloxy)phenyl)((cyclopropylmethyl)amino)methyl)phenyl)-1-(3-cyanophenyl)-3-(trifluoromethyl)-1H-pyrazole-5-carboxamide (150d)

To a solution of N-(3-((2,3-bis(benzyloxy)phenyl)(hydroxy)methyl)phenyl)-1-(3-cyanophenyl)-3-(trifluoromethyl)-1H-pyrazole-5-carboxamide (3.0 g, 4.44 mmol) in dichloromethane (50 mL) at 0° C. was added thionyl chloride (1.0 g, 8.40 mmol) and stirred at room temperature for 4 h. The reaction mixture was concentrated in vacuum to dryness. The residue obtained was dissolved in acetonitrile (40 mL) and added cyclopropylmethanamine (1.26 g, 17.76 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum. The residue obtained was purified by flash column chromatography (silica gel 40 g, eluting 0-40% ethyl acetate in hexane) to afford N-(3-((2,3-bis(benzyloxy)phenyl)((cyclopropylmethyl)amino)methyl)phenyl)-1-(3-cyanophenyl)-3-(trifluoromethyl)-1H-pyrazole-5-carboxamide (150d) (2.0 g, 61.8%) as brown sticky liquid; $^1$H NMR (300 MHz, DMSO-$d_6$) δ 10.62 (s, 1H), 8.15 (t, J=1.8 Hz, 1H), 7.97 (dt, J=7.8, 1.3 Hz, 1H), 7.89 (ddd, J=8.3, 2.3, 1.2 Hz, 1H), 7.75-7.67 (m, 2H), 7.64 (t, J=1.9 Hz, 1H), 7.55-7.47 (m, 3H), 7.42-7.27 (m, 8H), 7.22 (t, J=7.9 Hz, 1H), 7.07 (d, J=14.4 Hz, 4H), 5.14 (d, J=2.3 Hz, 3H), 4.90 (d, J=2.7 Hz, 2H), 2.24 (dt, J=11.4, 5.6 Hz, 1H), 2.18-2.07 (m, 2H), 0.84 (dq, J=9.7, 6.1 Hz, 1H), 0.37-0.25 (m, 2H), 0.09--0.11 (m, 2H).

Step-4: Preparation of tert-butyl 3-(5-((3-((2,3-bis(benzyloxy)phenyl)((cyclopropylmethyl)amino)methyl) phenyl)carbamoyl)-3-(trifluoromethyl)-1H-pyrazol-1-yl)benzylcarbamate (150e)

To a solution of N-(3-((2,3-bis(benzyloxy)phenyl)((cyclopropylmethyl)amino)methyl)phenyl)-1-(3-cyanophenyl)-3-(trifluoromethyl)-1H-pyrazole-5-carboxamide (150d) (2.0, 2.748 mmol) in MeOH (12 mL) cooled with ice/water was added nickel(II) chloride hexahydrate (0.78 g, 3.297 mmol) and Boc anhydride (1.8 g, 8.244 mmol) followed by portionwise addition of sodium borohydride (0.623 g, 16.488 mmol) over a period of 15 min. The reaction mixture was stirred at room temperature for 2 hrs and quenched with $N^1$-(2-aminoethyl)ethane-1,2-diamine (0.75 mL, 6.870 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over $MgSO_4$ filtered and concentrated in vacuum. The residue obtained was purified by flash column chromatography (silica gel 24 g, eluting with 0-25% Ethyl acetate/hexane) to furnish tert-butyl 3-(5-((3-((2,3-bis(benzyloxy)phenyl)((cyclopropylmethyl)amino)methyl) phenyl)carbamoyl)-3-(trifluoromethyl)-1H-pyrazol-1-yl)benzylcarbamate (150e) (0.530 g, 23.18%) as a white solid; $^1$H NMR (300 MHz, DMSO-d$_6$) δ 10.67 (s, 1H), 7.59 (s, 1H), 7.55 (s, 1H), 7.50 (dt, J=7.8, 2.3 Hz, 4H), 7.43-7.39 (m, 3H), 7.37-7.28 (m, 8H), 7.20 (t, J=7.8 Hz, 1H), 7.08 (s, 1H), 7.05 (s, 3H), 5.18-5.08 (m, 2H), 4.89 (d, J=2.7 Hz, 2H), 4.18 (d, J=6.2 Hz, 2H), 2.29-2.18 (m, 1H), 2.11 (s, 2H), 1.36 (s, 9H), 1.30-1.20 (m, 2H), 0.90-0.78 (m, 2H), 0.36-0.28 (m, 2H); $^{19}$F NMR (282 MHz, DMSO) δ −60.79; MS (ES+) 832.5 (M+1); (ES−) 830.4 (M−1).

Step-5: Preparation of 1-(3-(Aminomethyl)phenyl)-N-(3-((cyclopropylmethylamino)(2,3-dihydroxyphenyl)methyl)phenyl)-3-methyl-1H-pyrazole-5-carboxamide (150f)

To a solution of tert-butyl 3-(5-(3-((2,3-bis(benzyloxy)phenyl)(cyclopropylmethylamino)methyl)phenylcarbamoyl)-3-(trifluoromethyl)-1H-pyrazol-1-yl)benzylcarbamate (150e) (0.375 g, 0.451 mmol) in dichloromethane (10 mL) cooled to 0° C. was added dropwise under a nitrogen atmosphere borontrichloride (1 M solution in dichloromethane, 1.8 mL, 1.8 mmol). The reaction mixture was allowed to warm to room temperature and stirred at room temperature 2 h. The reaction mixture was quenched with methanol (5 mL) and concentrated in vacuum to dryness. The residue obtained was triturated with methanol and dried under vacuum, this step was repeated four times to furnish crude product. The residue obtained was purified twice by flash column chromatography [silica gel 12 g and 4 g, eluting with CMA-80 in chloroform from 0-100%] to furnish 1-(3-(aminomethyl)phenyl)-N-(3-((cyclopropylmethylamino)(2,3-dihydroxyphenyl)methyl)phenyl)-3-(trifluoromethyl)-1H-pyrazole-5-carboxamide (150f) (0.02 g, 0.036 mmol, 8.04% yield) as a yellow solid; $^1$H NMR (300 MHz, DMSO-d$_6$) δ 10.75 (s, 1H), 7.65 (t, J=1.8 Hz, 1H), 7.59-7.50 (m, 3H), 7.46-7.38 (m, 2H), 7.36-7.24 (m, 2H), 7.24-7.16 (m, 1H), 6.59 (dd, J=7.6, 1.9 Hz, 1H), 6.49 (t, J=7.6 Hz, 1H), 6.43 (dd, J=7.7, 1.9 Hz, 1H), 4.96 (s, 1H), 3.78 (s, 2H), 2.42 (m, 1H), 2.27 (m, 1H), 1.02-0.88 (m, 1H), 0.53-0.29 (m, 2H), 0.22-0.02 (m, 3H); $^{19}$F NMR (282 MHz, DMSO) δ −60.70; $^{13}$C NMR (75 MHz, DMSO) δ 191.41, 173.39, 156.44, 145.17, 145.04, 144.57, 143.73, 139.01, 137.92, 128.75, 127.74, 127.15, 123.40, 123.38, 123.27, 122.64, 118.82, 118.72, 118.43, 114.03, 64.03, 51.75, 44.67, 10.46, 3.49, 3.28; MS (ES+) 552.3 (M+1); (ES−) 550.3 (M−1); Analysis calculated for C$_{29}$H$_{28}$F$_3$N$_5$O$_3$·0.75H$_2$O: C, 61.64; H, 5.26; N, 12.39; Found: C, 62.01; H, 5.23; N, 11.92.

Scheme 151

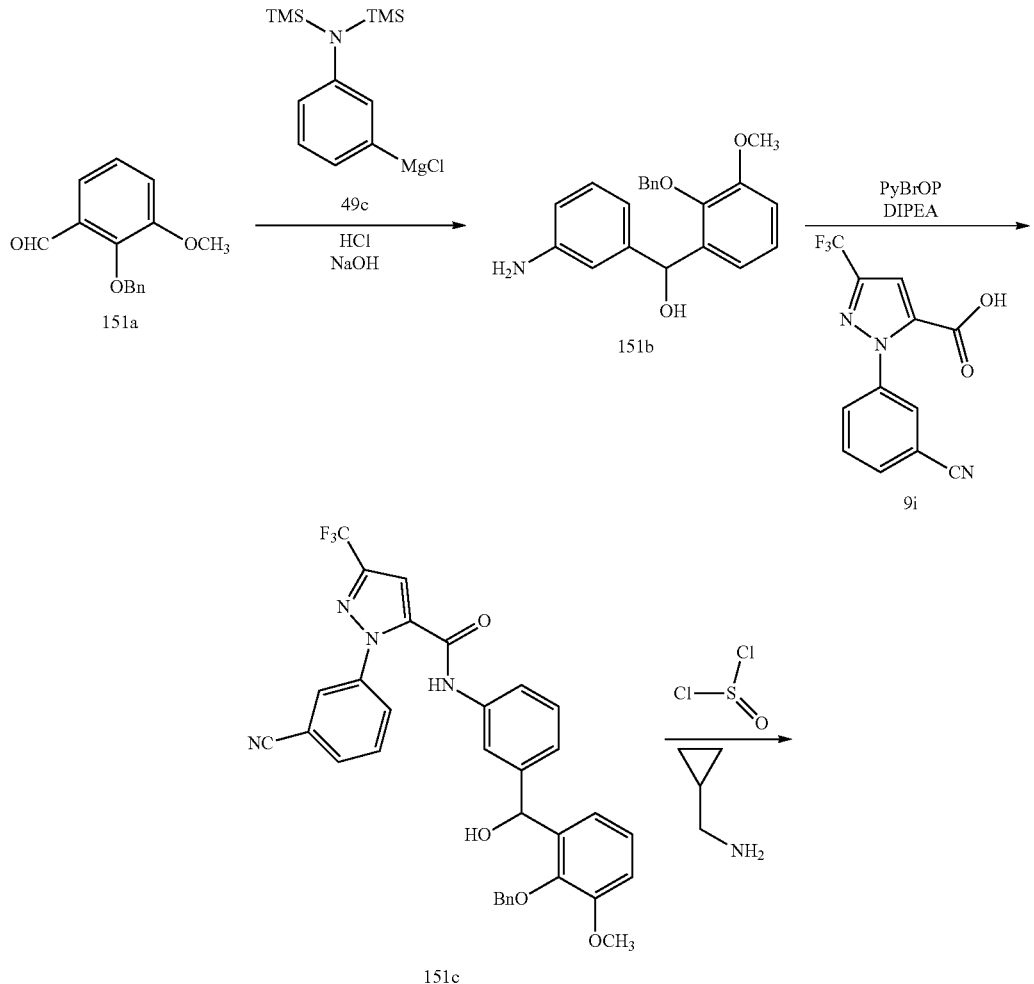

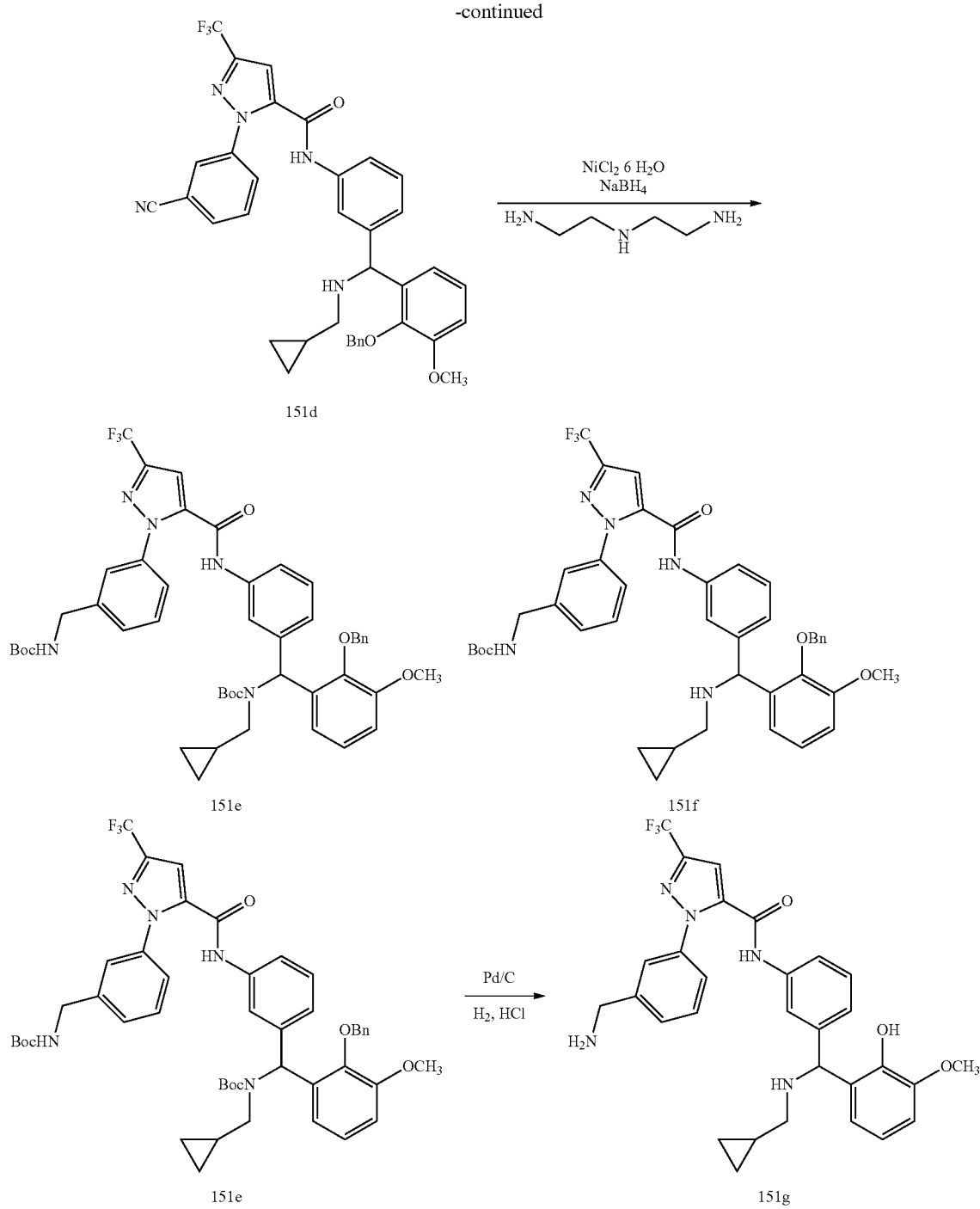

Preparation of 1-(3-(Aminomethyl)phenyl)-N-(3-((cyclopropylmethylamino)(2-hydroxy-3-methoxyphenyl)methyl)phenyl)-3-(trifluoromethyl)-1H-pyrazole-5-carboxamide (151g)

Step-1: Preparation of (3-aminophenyl)(2-(benzyloxy)-3-methoxyphenyl)methanol (151b)

To a stirred solution of 2-(benzyloxy)-3-methoxybenzaldehyde (151a) (3.2 g, 10 mmol) in tetrahydrofuran (5 mL) was added (3-(bis(trimethylsilyl)amino)phenyl)magnesium chloride (49c) (12.00 mL, 12.00 mmol) at 0° C. The reaction was stirred for 14 h at room temperature, quenched by adding 2 N HCl (12.50 mL) and stirred for 6 h. The reaction mixture was treated with 2 N NaOH (15 mL) and extracted with ethyl acetate (2×50 mL). The organic layers were combined washed with saturated aqueous NH₄Cl (50 mL), dried over anhydrous MgSO₄, filtered, evaporated to dryness. The crude residue was purified by flash column chromatography (silica gel 40 g, eluting with 0-100% ethyl acetate in hexane) to furnish (3-aminophenyl)(2-(benzyloxy)-3-methoxyphenyl)methanol (151b) (3.2 g, 86.97%) as a light brown sticky liquid; $^1$H NMR (300 MHz, DMSO-d$_6$) δ 7.49-7.30 (m, 5H), 7.10-6.99 (m, 2H), 6.94 (dd, J=7.5, 2.2 Hz, 1H), 6.88 (t, J=7.7 Hz, 1H), 6.53 (t, J=1.9 Hz, 1H), 6.44 (dt, J=7.7, 1.3 Hz, 1H), 6.37 (ddd, J=8.0, 2.4, 1.0 Hz, 1H), 5.89 (d, J=4.4 Hz, 1H), 5.52 (d, J=4.4 Hz, 1H), 4.95 (s, 2H), 4.89 (d, J=10.8 Hz, 1H), 4.77 (d, J=10.8 Hz, 1H), 3.82 (s, 3H); MS (ES−) 334.3 (M−1).

Step-2: Preparation of N-(3-((2-(benzyloxy)-3-methoxyphenyl)(hydroxy)methyl)phenyl)-1-(3-cyanophenyl)-3-(trifluoromethyl)-1H-pyrazole-5-carboxamide (151c)

To a solution of 1-(3-cyanophenyl)-3-(trifluoromethyl)-1H-pyrazole-5-carboxylic acid (9i) (3.018, 10.73 mmol) in in DMF (72 mL) was added (3-Amino-phenyl)-(2-benzyloxy-3-methoxy-phenyl)-methanol (151b) (3.2 g, 9.54 mmol), N-ethyl-N-isopropylpropan-2-amine (11.097 g, 85.864 mmol) and bromo-tris-pyrrolidino phosphonium-hexafluorophosphate (PyBrOP, 5.003 g, 10.73 mmol) at room temperature. The reaction mixture was stirred at room temperature for 42 h under nitrogen atmosphere. The reaction was diluted with ethyl acetate (350 mL) washed with water (2×150 mL), brine (120 mL), dried, filtered, and evaporated to dryness. The residue obtained was purified by flash column chromatography [silica gel 120 g, eluting with ethyl acetate in hexanes from 0-30%] to furnish N-(3-((2-(benzyloxy)-3-methoxyphenyl)(hydroxy)methyl)phenyl)-1-(3-cyanophenyl)-3-(trifluoromethyl)-1H-pyrazole-5-carboxamide (151c) (2.4 g, 37.36%) as a yellow sticky liquid; $^1$H NMR (300 MHz, DMSO-d$_6$) δ 10.63 (s, 1H), 8.14 (t, J=1.8 Hz, 1H), 7.98 (dt, J=7.7, 1.4 Hz, 1H), 7.94 (s, 1H), 7.88 (ddd, J=8.2, 2.2, 1.1 Hz, 1H), 7.72 (d, J=8.0 Hz, 1H), 7.69 (d, J=1.3 Hz, 1H), 7.60 (t, J=1.8 Hz, 1H), 7.54-7.48 (m, 1H), 7.43 (dd, J=5.2, 1.6 Hz, 3H), 7.38-7.34 (m, 2H), 7.22 (t, J=7.9 Hz, 1H), 7.06-6.99 (m, 3H), 6.00 (d, J=4.4 Hz, 1H), 5.81 (d, J=4.3 Hz, 1H), 4.93 (s, 2H), 4.85 (d, J=8.6 Hz, 1H), 4.76 (d, J=10.8 Hz, 1H), 3.82 (s, 3H).

Step-3: Preparation of N-(3-((2-(benzyloxy)-3-methoxyphenyl)((cyclopropylmethyl)amino)methyl)phenyl)-1-(3-cyanophenyl)-3-(trifluoromethyl)-1H-pyrazole-5-carboxamide (151d)

To a solution of N-(3-((2-(benzyloxy)-3-methoxyphenyl)(hydroxy)methyl)phenyl)-1-(3-cyanophenyl)-3-(trifluoromethyl)-1H-pyrazole-5-carboxamide (151c) (2.0 g, 3.34 mmol) in dichloromethane (50 mL) at 0° C. was added thionyl chloride (0.795 g, 6.68 mmol) and stirred at room temperature for 4 h. The reaction mixture was concentrated in vacuum to dryness. The residue obtained was dissolved in acetonitrile (40 mL) and added cyclopropylmethanamine (3.56 g, 50.1 mmol). The reaction mixture was heated at reflux overnight, cooled to room temperature and concentrated in vacuum to dryness. The residue was dissolved in dichloromethane (50 mL), washed with water (2×25 mL), dried, filtered and concentrated in vacuum. The residue obtained was purified by flash column chromatography (silica gel 40 g, eluting 0-40% ethyl acetate in hexane) to afford N-(3-((2-(benzyloxy)-3-methoxyphenyl)((cyclopropylmethyl)amino)methyl)phenyl)-1-(3-cyanophenyl)-3-(trifluoromethyl)-1H-pyrazole-5-carboxamide (151d) (1.01 g, 46.40%) as brown liquid.

Step-4: Preparation of tert-butyl ((2-(benzyloxy)-3-methoxyphenyl)(3-(1-(3-(((tert-butoxycarbonyl)amino)methyl)phenyl)-3-(trifluoromethyl)-1H-pyrazole-5-carboxamido)phenyl)methyl)(cyclopropylmethyl)carbamate (151e) tert-butyl 3-(5-((3-((2-(benzyloxy)-3-methoxyphenyl)((cyclopropylmethyl)amino)methyl)phenyl)carbamoyl)-3-(trifluoromethyl)-1H-pyrazol-1-yl)benzylcarbamate (151f)

To a solution of N-(3-((2-(benzyloxy)-3-methoxyphenyl)((cyclopropylmethyl)amino) methyl)phenyl)-1-(3-cyanophenyl)-3-(trifluoromethyl)-1H-pyrazole-5-carboxamide (151d) (1.0 g, 1.53 mmol) in MeOH (12 mL) cooled with ice/water was added nickel(II) chloride hexahydrate (0.40 g, 1.683 mmol) and Boc anhydride (1.00 g, 4.59 mmol) followed by portionwise addition of sodium borohydride (0.34 g, 9.18 mmol) over a period of 15 min. The reaction mixture was stirred at room temperature for 2 hrs and quenched with N1-(2-aminoethyl)ethane-1,2-diamine (0.4 mL, 3.825 mmol) followed by stirring for additional 0.5 h. The reaction mixture was concentrated in vacuum to dryness and the residue obtained was dissolved in chloroform (25 mL) and water (25 mL). The aqueous layer was separated extracted with chloroform (25 mL). The combined extracts were washed with brine (25 mL), dried over MgSO$_4$ filtered and concentrated in vacuum. The residue obtained was purified by flash column chromatography (silica gel 24 g, eluting with 0-25% Ethyl acetate/hexane) to furnish:

1. tert-butyl ((2-(benzyloxy)-3-methoxyphenyl)(3-(1-(3-(((tert-butoxycarbonyl)amino)methyl)phenyl)-3-(trifluoromethyl)-1H-pyrazole-5-carboxamido)phenyl)methyl)(cyclopropylmethyl)carbamate (151e) (0.130 g, 9.9%) as an off-white solid; $^1$H NMR (300 MHz, DMSO-d$_6$) δ 10.68 (s, 1H), 7.61 (d, J=7.9 Hz, 1H), 7.55 (s, 1H), 7.49 (t, J=6.2 Hz, 1H), 7.44-7.27 (m, 9H), 7.26 (d, J=8.0 Hz, 1H), 7.13-6.99 (m, 2H), 6.77 (d, J=7.7 Hz, 1H), 6.52 (dd, J=6.5, 2.7 Hz, 1H), 4.96 (d, J=10.8 Hz, 1H), 4.83 (d, J=10.8 Hz, 1H), 4.17 (d, J=6.2 Hz, 2H), 3.86 (s, 3H), 3.82-3.76 (m, 1H), 3.25-3.17 (m, 1H), 2.94 (dd, J=14.5, 6.9 Hz, 1H), 1.36 (d, J=1.6 Hz, 18H), 0.62-0.46 (m, 1H), 0.27-0.06 (m, 2H), −0.09--0.23 (m, 1H), −0.32--0.55 (m, 1H); $^{19}$F NMR (282 MHz, DMSO) δ −60.79; MS (ES+) 878.5 (M+Na); (ES−) 854.5 (M−1).

2. tert-butyl 3-(5-((3-((2-(benzyloxy)-3-methoxyphenyl)((cyclopropylmethyl)amino) methyl)phenyl)carbamoyl)-3-(trifluoromethyl)-1H-pyrazol-1-yl)benzylcarbamate (151f) (0.020 g, 1.72% as a white solid; 1H NMR (300 MHz, DMSO-d$_6$) δ 10.66 (s, 1H), 7.57 (s, 1H), 7.55 (s, 1H), 7.50 (d, J=7.3 Hz, 1H), 7.44-7.39 (m, 5H), 7.39-7.28 (m, 5H), 7.19 (t, J=7.8 Hz, 1H), 7.05 (d, J=4.5 Hz, 1H), 7.02 (s, 1H), 6.93 (dd, J=7.0, 2.6 Hz, 1H), 5.11 (s, 1H), 4.88 (s, 2H), 4.18 (d, J=6.2 Hz, 3H), 3.82 (s, 3H), 2.16-2.04 (m, 3H), 1.36 (s, 9H), 0.91-0.71 (m, 1H), 0.34-0.28 (m, 2H), −0.03 (dd, J=9.1, 2.7 Hz, 2H); $^{19}$F NMR (282 MHz, DMSO) δ −60.78; MS (ES+) 756.5 (M+1); (ES−) 754.5 (M−1).

Step-5: Preparation of 1-(3-(Aminomethyl)phenyl)-N-(3-((cyclopropylmethylamino)(2-hydroxy-3-methoxyphenyl)methyl)phenyl)-3-(trifluoromethyl)-1H-pyrazole-5-carboxamide (151g)

To a solution of tert-butyl ((2-(benzyloxy)-3-methoxyphenyl)(3-(1-(3-(((tert-butoxycarbonyl)amino)methyl)phenyl)-3-(trifluoromethyl)-1H-pyrazole-5-carboxamido)phenyl)methyl)(cyclopropylmethyl)carbamate (151e) (0.012 g, 0.014 mmol) in methanol (10 mL) was added Palladium on carbon (10%, 0.037 mg) and conc. HCl (0.023 mL, 0.280 mmol). The mixture was hydrogenated for 2 h at 50 psi and filtered through a pad of celite. The filtrate was concentrated in vacuum to dryness. The residue obtained was purified twice by flash column chromatography (silica gel 12 g, eluting 0-100% CMA-80 in chloroform) to afford 1-(3-(aminomethyl)phenyl)-N-(3-((cyclopropylmethylamino)(2-hydroxy-3-methoxyphenyl)methyl)phenyl)-3-(trifluoromethyl)-1H-pyrazole-5-carboxamide (151g) (0.013 g, 0.023 mmol, 16.4% yield) as a white solid; $^1$H NMR (300 MHz, DMSO-d$_6$) δ 10.73 (s, 1H), 7.66-7.61 (m, 1H), 7.60-7.49 (m, 3H), 7.48-7.38 (m, 2H), 7.35-7.23 (m, 2H), 7.19 (dt, J=7.9, 1.4 Hz, 1H), 6.77 (dd, J=6.5, 3.1 Hz, 1H), 6.64 (d, J=6.6 Hz, 2H), 5.01 (s, 1H), 3.77 (s, 2H), 3.72 (s, 3H), 2.44-2.20 (m, 2H), 1.03-0.87 (m, 1H), 0.49-0.30 (m, 2H), 0.17-0.02 (m, 2H); $^{19}$F NMR (282 MHz, DMSO) δ −60.70; MS (ES+) 566.3 (M+1); (ES−) 564.3 (M−1); Analysis calculated for C$_{30}$H$_{30}$F$_3$N$_5$O$_3$.2H$_2$O: C, 59.89; H, 5.70; N, 11.64; Found: C, 59.69; H, 5.27; N, 11.36.

Scheme 152

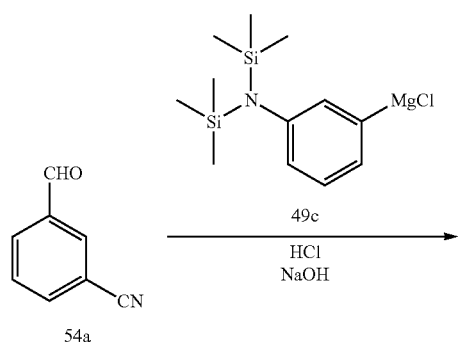

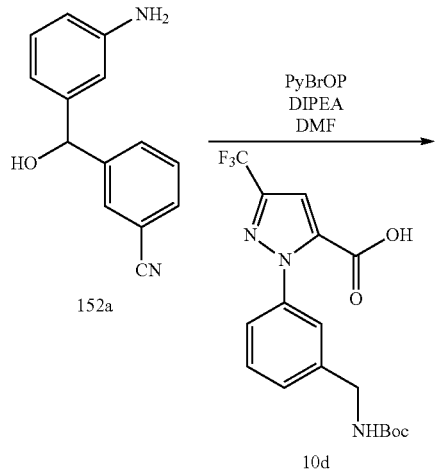

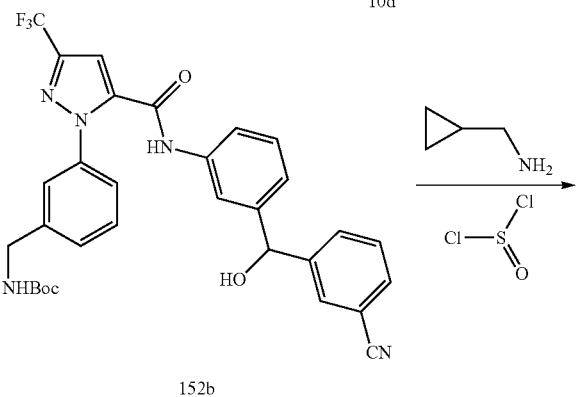

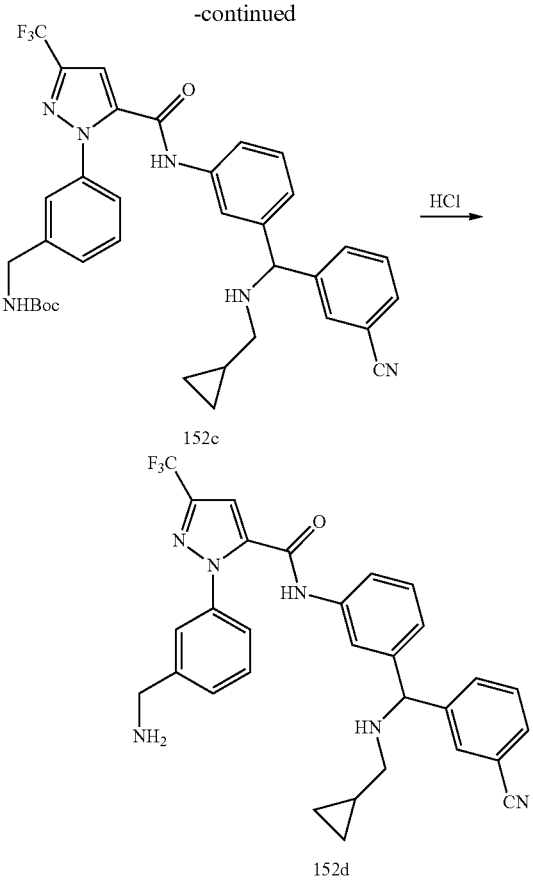

Preparation of 1-(3-(aminomethyl)phenyl)-N-(3-((3-cyanophenyl)(cyclopropylmethylamino) methyl)phenyl)-3-(trifluoromethyl)-1H-pyrazole-5-carboxamide (152d)

Step-1: Preparation of 3-((3-aminophenyl)(hydroxy)methyl)benzonitrile (152a)

To a stirred solution of 3-formylbenzonitrile (54a) (3.93 g, 30 mmol) in tetrahydrofuran (50 mL) was added (3-(bis(trimethylsilyl)amino)phenyl)magnesium chloride (49c) (36.0 mL, 36.0 mmol) at 0° C. The reaction was stirred for 14 h at room temperature and quenched by adding 2 N HCl (37.5 mL, 75 mmol), stirred for additional 1 h at room temperature. The reaction mixture was treated with 2 N NaOH (45 mL, 90 mmol) and extracted with ethyl acetate (2×100 mL). The organic layers were combined washed with sat. NH$_4$Cl (100 mL), dried over anhydrous MgSO$_4$, filtered, evaporated to dryness. The crude residue was purified by flash column chromatography (silica gel 120 g, eluting with 0-100% ethyl acetate in hexane) to furnish 3-((3-aminophenyl)(hydroxy)methyl)benzonitrile (152a) (3.56 g, 15.87 mmol, 52.9% yield) as a yellow solid; $^1$H NMR (300 MHz, DMSO-d$_6$) δ 7.76 (t, J=1.6 Hz, 1H), 7.72-7.63 (m, 2H), 7.51 (t, J=7.7 Hz, 1H), 6.94 (t, J=7.7 Hz, 1H), 6.61-6.48 (m, 2H), 6.41 (ddd, J=8.0, 2.4, 1.1 Hz, 1H), 5.96 (d, J=3.9 Hz, 1H, D$_2$O exchangeable), 5.59 (d, J=3.9 Hz, 1H), 5.04 (s, 2H, D$_2$O exchangeable); MS (ES+) 225.2 (M+1), 247.1 (M+Na); MS (ES−) 223.1 (M−1), 447.2 (2M−1).

Step-2: Preparation of tert-butyl 3-(5-(3-((3-cyanophenyl)(hydroxy)methyl)phenylcarbamoyl)-3-(trifluoromethyl)-1H-pyrazol-1-yl)benzylcarbamate (152b)

A single-necked 100 mL flask was charged with 1-(3-((tert-butoxycarbonylamino)methyl)phenyl)-3-(trifluoromethyl)-1H-pyrazole-5-carboxylic acid (10d) (7.27 g, 18.86 mmol), 3-((3-aminophenyl)(hydroxy)methyl)benzonitrile (152a) (3.524 g, 15.71 mmol), bromo-tris-pyrrolidino phosphoniumhexafluorophosphate(PyBrOP, 8.79 g, 18.86 mmol) were treated N,N-dimethylformamide (91 mL) and N-ethyl-N-isopropylpropan-2-amine (13.69 mL, 79 mmol) successively in a positive flow of nitrogen at room temperature. The resulting reaction mixture was stirred at room temperature for 16 h under a positive flow of nitrogen atmosphere. The residue was treated with water (75 mL), and extracted with ethyl acetate (2×75 mL) combined organics were dried over anhydrous MgSO$_4$, filtered, evaporated to dryness. The residue was then purified by flash column chromatography [silica gel 80 g, eluting with ethyl acetate in hexanes from 0-100%] to furnish tert-butyl 3-(5-(3-((3-cyanophenyl)(hydroxy)methyl)phenylcarbamoyl)-3-(trifluoromethyl)-1H-pyrazol-1-yl)benzylcarbamate (152b) (3.799 g, 6.42 mmol, 40.9% yield) as a yellow solid; $^1$H NMR: 1H NMR (300 MHz, DMSO-d$_6$) δ 10.70 (s, 1H, D$_2$O exchangeable), 7.80 (t, J=1.7 Hz, 1H), 7.69 (ddt, J=8.6, 5.7, 1.5 Hz, 2H), 7.62 (t, J=1.7 Hz, 1H), 7.60-7.55 (m, 2H), 7.54-7.39 (m, 3H), 7.38-7.25 (m, 3H), 7.16 (dt, J=7.7, 1.3 Hz, 1H), 6.20 (d, J=3.9 Hz, 1H, D$_2$O exchangeable), 5.76 (d, J=3.9 Hz, 1H), 4.19 (d, J=6.2 Hz, 2H), 1.36 (s, 9H); 19F NMR (282 MHz, DMSO-d$_6$) δ −60.78; IR (KBr, cm$^{-1}$): 2232 cm$^{-1}$ (—CN stretching); MS (ES$^+$): MS (ES+) 614.3 (M+Na), MS (ES−) 590.3 (M−1), 626.3 (M+Cl).

Step-3: Preparation of tert-butyl 3-(5-(3-((3-cyanophenyl)(cyclopropylmethylamino)methyl) phenylcarbamoyl)-3-(trifluoromethyl)-1H-pyrazol-1-yl) benzylcarbamate (152c)

To a solution of tert-butyl 3-(5-(3-((3-cyanophenyl)(hydroxy)methyl)phenylcarbamoyl)-3-(trifluoromethyl)-1H-pyrazol-1-yl)benzylcarbamate (152b) (3.71 g, 6.27 mmol) in dichloromethane (40 mL) at 0° C. was added thionyl chloride (1.372 mL, 18.81 mmol), reaction mixture allowed to warm to room temperature and stirred for 3 h. The reaction mixture was quenched with cyclopropylmethanamine (3.81 mL, 43.9 mmol), and solution was stirred for 30 min at room temperature, and concentrated in vacuum to dryness. The residue was dissolved in acetonitrile (40 mL) then added cyclopropylmethanamine (3.81 mL, 43.9 mmol) stirred at 80° C. for 16 h, TLC analysis (ethyl acetate/hexanes, 1:1, v/v) shows complete conversion, reaction mixture was cooled to room temperature. The reaction mixture treated silica gel (6 g), evaporated under reduced pressure until become dry slurry. The residue was purified by flash column chromatography (silica gel 40 g, performed two separate columns, eluting with ethyl acetate in hexanes from 0-100%) to afford tert-butyl 3-(5-(3-((3-cyanophenyl)(cyclopropylmethylamino)methyl) phenylcarbamoyl)-3-(trifluoromethyl)-1H-pyrazol-1-yl)benzylcarbamate (152c) (0.704 g, 17% yield) as a white solid which was used as such in the next step; MS (ES+) 645.1 (M+1); MS (ES−) 643.2 (M−1).

Step-4: Preparation of 1-(3-(aminomethyl)phenyl)-N-(3-((3-cyanophenyl)(cyclopropylmethyl amino)methyl)phenyl)-3-(trifluoromethyl)-1H-pyrazole-5-carboxamide (152d)

To a solution of tert-butyl 3-(5-(3-((3-cyanophenyl)(cyclopropylmethylamino) methyl)phenylcarbamoyl)-3-(trifluoromethyl)-1H-pyrazol-1-yl)benzylcarbamate (152c) (0.285 g, 0.442 mmol) in dioxane (9 mL) was added hydrogen chloride (4 N) (3.17 mL, 19.01 mmol), reaction mixture stirred at room temperature and stirred for 16 h. The reaction mixture was concentrated in vacuum and residue obtained was purified by flash column chromatography (silica gel 25 g, eluting with methanol in chloroform from 0-100%) to afford 1-(3-(aminomethyl)phenyl)-N-(3-((3-cyanophenyl)(cyclopropylmethyl amino)methyl)phenyl)-3-(trifluoromethyl)-1H-pyrazole-5-carboxamide (152d) (39 mg, 16% yield) as a white solid; $^1$H NMR (300 MHz, DMSO-d$_6$) δ 10.76 (s, 1H, D$_2$O exchangeable), 7.87 (t, J=1.7 Hz, 1H), 7.74 (dt, J=7.8, 1.5 Hz, 1H), 7.67 (ddd, J=7.9, 3.6, 2.2 Hz, 4H), 7.61-7.43 (m, 5H), 7.32-7.18 (m, 2H), 4.91 (s, 1H), 4.04 (s, 2H), 2.26 (dt, J=9.4, 4.8 Hz, 2H), 1.02-0.83 (m, 1H), 0.44-0.33 (m, 2H), 0.05 (tt, J=5.8, 3.2 Hz, 2H); $^1$H NMR (300 MHz, DMSO-d$_6$, D$_2$O) δ 7.86 (t, J=1.7 Hz, 1H), 7.78-7.73 (m, 1H), 7.70-7.62 (m, 3H), 7.60-7.49 (m, 5H), 7.46 (dt, J=6.3, 2.5 Hz, 1H), 7.34-7.19 (m, 2H), 4.92 (s, 1H), 4.02 (s, 2H), 2.34-2.21 (m, 2H), 0.98-0.84 (m, 1H), 0.44-0.35 (m, 2H), 0.07-0.01 (m, 2H); $^{19}$F NMR (282 MHz, DMSO-d$_6$) δ −60.76; IR (KBr, cm$^{-1}$): 2230 cm$^{-1}$ (—CN stretching); MS (ES$^+$): MS (ES+) 545.3 (M+1), MS (ES−) 543.3 (M−1); Analysis calculated for: C$_{30}$H$_{27}$F$_3$N$_6$O.2H$_2$O.2HCl: C, 55.14; H, 5.09; N, 12.86; Found: C, 55.41; H, 5.30; N, 12.20.

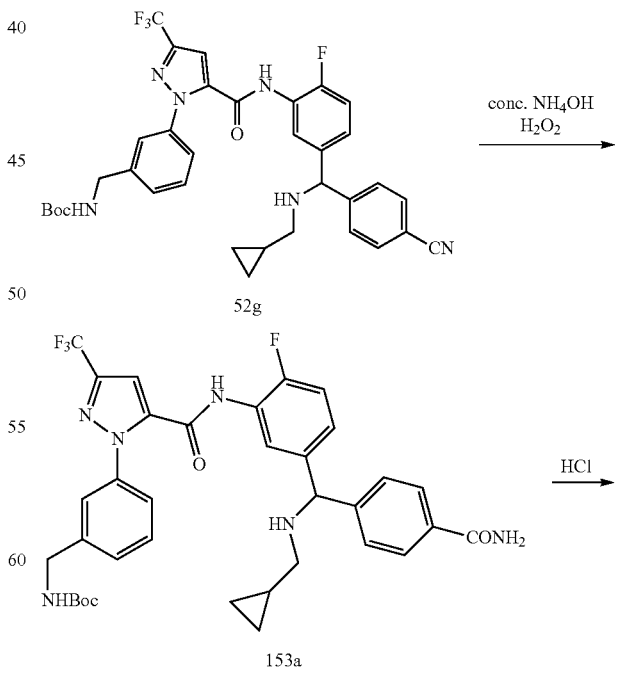

Scheme 153

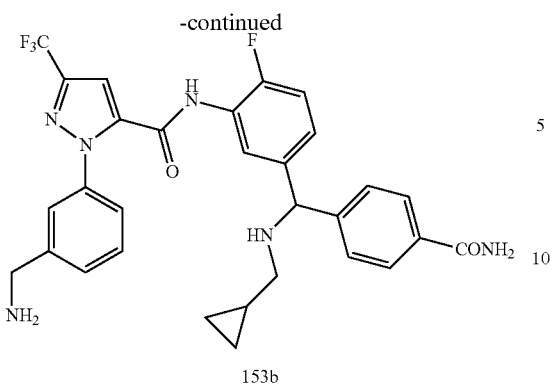

153b

Preparation of 1-(3-(aminomethyl)phenyl)-N-(5-((4-carbamoylphenyl)(cyclopropylmethyl-amino)methyl)-2-fluorophenyl)-3-(trifluoromethyl)-1H-pyrazole-5-carboxamide (153b)

Step-1: Preparation of tert-butyl 3-(5-(5-((4-carbamoylphenyl)(cyclopropylmethyl-amino)methyl)-2-fluorophenylcarbamoyl)-3-(trifluoromethyl)-1H-pyrazol-1-yl)benzylcarbamate (153a)

To a solution of tert-butyl 3-(5-(5-((4-cyanophenyl)(cyclopropylmethylamino)methyl)-2-fluorophenylcarbamoyl)-3-(trifluoromethyl)-1H-pyrazol-1-yl)benzylcarbamate (52g) (161 mg, 0.243 mmol) in ethanol (6 mL) was added conc. aqueous ammonia (2.4 mL) followed by dropwise addition of hydrogen peroxide (30% aq. solution, 0.09 mL). The reaction mixture was stirred at room temperature for 21 h and concentrated in vacuum to dryness. The residue was purified by flash column chromatography [silica gel 4 g, eluting with chloroform/methanol (1:0 to 19:1)] to give tert-butyl 3-(5-(5-((4-carbamoylphenyl)(cyclopropylmethyl-amino)methyl)-2-fluorophenylcarbamoyl)-3-(trifluoromethyl)-1H-pyrazol-1-yl)benzylcarbamate (153a) (17 mg, 10%) as a colorless gum; $^1$H NMR (300 MHz, DMSO-$d_6$) δ 10.55 (s, 1H), 7.88 (s, 1H), 7.78 (d, J=8.1 Hz, 2H), 7.66-7.26 (m, 9H), 7.20 (t, J=9.6 Hz, 1H), 4.90 (s, 1H), 4.19 (d, J=6.1 Hz, 2H), 2.30-2.22 (m, 2H), 1.37 (s, 9H), 0.99-0.80 (m, 1H), 0.46-0.31 (m, 2H), 0.10--0.03 (m, 2H); $^{19}$F NMR (282 MHz, DMSO-$d_6$) δ −60.81, −123.53; MS (ES+): 681.4 (M+H).

Step-2: Preparation of 1-(3-(aminomethyl)phenyl)-N-(5-((4-carbamoylphenyl)(cyclopropylmethyl-amino)methyl)-2-fluorophenyl)-3-(trifluoromethyl)-1H-pyrazole-5-carboxamide (153b)

To a solution of tert-butyl 3-(5-(5-((4-carbamoylphenyl)(cyclopropylmethylamino)methyl)-2-fluorophenylcarbamoyl)-3-(trifluoromethyl)-1H-pyrazol-1-yl)benzylcarbamate (153a) (15 mg, 0.022 mmol) in 1,4-Dioxane (4 mL) was added hydrogen chloride (0.240 mL, 0.961 mmol, 4 M in 1,4-dioxane) and stirred at room temperature for 16 h. The reaction mixture was treated with hexanes, decanted, washed with hexanes, and decanted again. The insoluble crude product was purified by flash column chromatography [silica gel eluting with chloroform/CMA80 (1:0 to 2:1)] to give 1-(3-(aminomethyl)phenyl)-N-(5-((4-carbamoylphenyl)(cyclopropylmethylamino)methyl)-2-fluorophenyl)-3-(trifluoromethyl)-1H-pyrazole-5-carboxamide (153b). The purified product was dissolved in methanol (10 mL) and treated with 4 N HCl (aq. 0.03 mL) followed by concentration to dryness to give 1-(3-(aminomethyl)phenyl)-N-(5-((4-carbamoylphenyl)(cyclopropylmethylamino)methyl)-2-fluorophenyl)-3-(trifluoromethyl)-1H-pyrazole-5-carboxamide (153b) (19 mg) hydrochloride salt as a off-white solid; $^1$H NMR (300 MHz, DMSO-$d_6$) δ 10.81 (s, 1H), 10.26 (s, 2H), 8.43 (s, 3H), 8.04 (s, 1H), 7.95 (s, 1H), 7.94-7.87 (m, 2H), 7.79 (d, J=8.2 Hz, 2H), 7.74-7.68 (m, 3H), 7.64-7.51 (m, 2H), 7.47 (s, 1H), 7.41 (dd, J=10.3, 8.6 Hz, 1H), 5.73 (t, J=6.3 Hz, 1H), 4.12 (q, J=5.9 Hz, 2H), 2.72 (d, J=8.9 Hz, 2H), 1.23-1.08 (m, 2H), 0.64-0.46 (m, 2H), 0.41-0.20 (m, 1H); $^1$H NMR (D$_2$O ex NMR, 300 MHz, DMSO-$d_6$) δ 7.95-7.82 (m, 3H), 7.73-7.48 (m, 8H), 7.43 (dd, J=10.2, 8.6 Hz, 1H), 5.70 (s, 1H), 4.12 (s, 2H), 2.78-2.72 (m, 2H), 1.21-0.97 (m, 1H), 0.66-0.54 (m, 2H), 0.33-0.24 (m, 2H); $^{19}$F NMR (282 MHz, DMSO-$d_6$) δ −60.81, −120.35; MS (ES+): 581.3 (M+1); Analysis calculated for $C_{30}H_{28}F_4N_6O_2 \cdot 2HCl \cdot 3H_2O$: C, 50.93; H, 5.13; N, 11.88; Found: C, 50.56; H, 5.23; N, 11.55.

Scheme 154

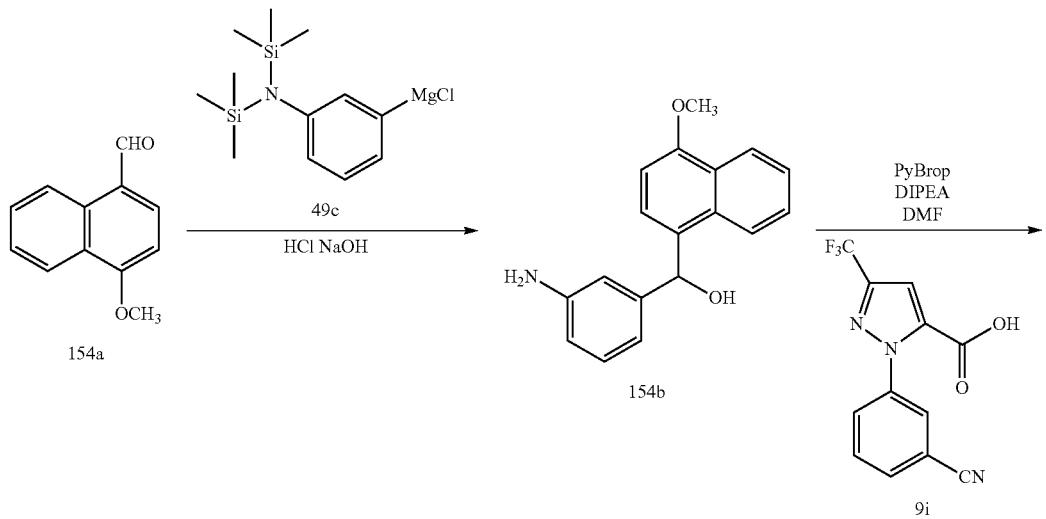

-continued
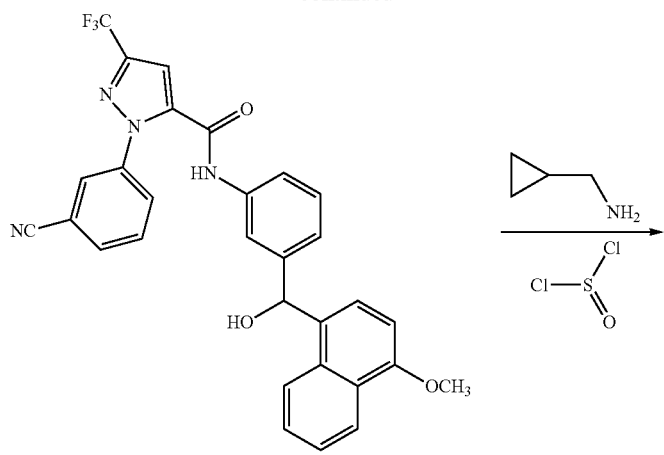
154c
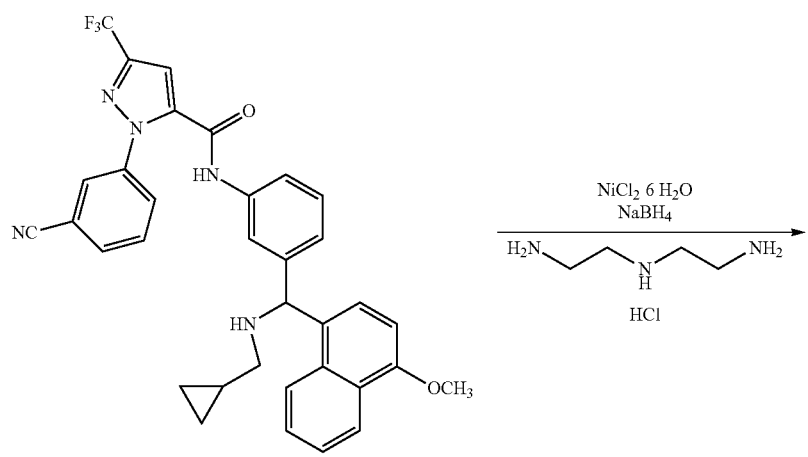
154d
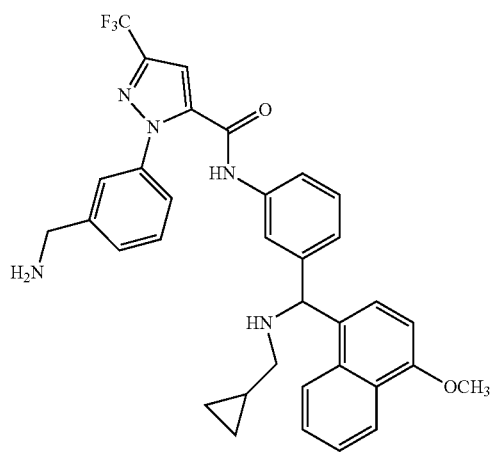
154e

Preparation of 1-(3-(aminomethyl)phenyl)-N-(3-((cyclopropylmethylamino)(4-methoxynaphthalen-1-yl)methyl)phenyl)-3-(trifluoromethyl)-1H-pyrazole-5-carboxamide (154e)

Step-1: Preparation of (3-aminophenyl)(4-methoxynaphthalen-1-yl)methanol (154b)

To a stirred solution of 4-methoxy-1-naphthaldehyde (154a) (2.048 g, 11 mmol) in tetrahydrofuran (30 mL) was added (3-(bis(trimethylsilyl)amino)phenyl)magnesium chloride (49c) (13.20 mL, 13.20 mmol) at 0° C. The reaction was stirred for 15 h at temperature and quenched by slowly adding aq. 12 N HCl (2.292 mL, 27.5 mmol), and stirred for 1 h. The reaction mixture was treated with 1 N NaOH (16.50 mL, 33.0 mmol) and extracted with ethyl acetate (2×50 mL). The organic layers were combined, dried over anhydrous MgSO$_4$, filtered, and evaporated to dryness. The residue was purified by flash column chromatography (silica gel 40 g, eluting with 0-100% ethyl acetate in hexane) to furnish (3-aminophenyl)(4-methoxynaphthalen-1-yl)methanol (154b) (2.818 g, 92% yield) as a off-white solid; $^1$H NMR (300 MHz, DMSO-d$_6$) δ 8.25-8.00 (m, 2H), 7.52 (d, J=8.0 Hz, 1H), 7.43 (dt, J=6.5, 3.4 Hz, 2H), 7.01-6.85 (m, 2H), 6.54 (dp, J=3.4, 1.4 Hz, 2H), 6.37 (ddd, J=7.9, 2.2, 1.0 Hz, 1H), 6.08 (d, J=4.4 Hz, 1H), 5.74 (d, J=4.4 Hz, 1H, D$_2$O exchangeable), 4.95 (s, 2H, D$_2$O exchangeable), 3.96 (s, 3H); MS (ES$^+$): MS (ES+) 302.2 (M+Na), MS (ES−) 278.3 (M−1).

Step-2: Preparation of 1-(3-cyanophenyl)-N-(3-(hydroxy(4-methoxynaphthalen-1-yl)methyl)phenyl)-3-(trifluoromethyl)-1H-pyrazole-5-carboxamide (154c)

In a 250 mL single-necked flask containing 1-(3-cyanophenyl)-3-(trifluoromethyl)-1H-pyrazole-5-carboxylic acid (9i) (3.30 g, 11.73 mmol), (3-aminophenyl)(4-methoxynaphthalen-1-yl)methanol (154b) (2.73 g, 9.77 mmol), bromo-tris-pyrrolidino phosphoniumhexafluorophosphate(PyBrOP, 5.47 g, 11.73 mmol) was added N,N-dimethylformamide (56.8 mL, 733 mmol) and N-ethyl-N-isopropylpropan-2-amine (DIPEA, 8.51 mL, 48.9 mmol) successively in a positive flow of nitrogen at room temperature. The resulting reaction mixture was stirred for 16 h at room temperature under a positive flow of nitrogen. The reaction mixture was treated with water (150 mL), and extracted with chloroform (2×100 mL), combined organics were dried over anhydrous MgSO$_4$, filtered, evaporated to dryness. The residue was purified by flash column chromatography [silica gel 40 g, eluting with ethyl acetate in hexanes from 0-100%] to furnish 1-(3-cyanophenyl)-N-(3-(hydroxy(4-methoxynaphthalen-1-yl)methyl)phenyl)-3-(trifluoromethyl)-1H-pyrazole-5-carboxamide (154c) (4.274 g, 81% yield) as a colorless solid; $^1$H NMR (300 MHz, DMSO-d$_6$) δ 10.60 (s, 1H, D$_2$O exchangeable), 8.21-8.13 (m, 2H), 8.06 (dt, J=7.7, 2.7 Hz, 1H), 7.99 (dt, J=7.7, 1.3 Hz, 1H), 7.88 (ddd, J=8.2, 2.2, 1.1 Hz, 1H), 7.77-7.66 (m, 2H), 7.58 (dd, J=6.7, 1.4 Hz, 2H), 7.52 (d, J=8.0 Hz, 1H), 7.48-7.38 (m, 2H), 7.26 (t, J=8.2 Hz, 1H), 7.20-7.13 (m, 1H), 6.97 (d, J=8.0 Hz, 1H), 6.23 (d, J=4.3 Hz, 1H), 6.02 (d, J=4.3 Hz, 1H, D$_2$O exchangeable), 3.97 (s, 3H); $^{19}$F NMR (282 MHz, DMSO-d$_6$) δ −60.96; MS (ES$^+$): MS (ES+) 565.3 (M+Na), MS (ES−) 541.2 (M−1); IR (KBr, cm$^{-1}$): 2235 cm$^{-1}$ (—CN stretching).

Step-3: Preparation of 1-(3-cyanophenyl)-N-(3-((cyclopropylmethylamino)(4-methoxynaphthalen-1-yl)methyl)phenyl)-3-(trifluoromethyl)-1H-pyrazole-5-carboxamide (154d)

To a solution of 1-(3-cyanophenyl)-N-(3-(hydroxy(4-methoxynaphthalen-1-yl)methyl)phenyl)-3-(trifluoromethyl)-1H-pyrazole-5-carboxamide (154c) (2.693 g, 4.96 mmol) in dichloromethane (40 mL) at 0° C. was added thionyl chloride (1.086 mL, 14.89 mmol) and allowed to warm to room temperature and stirred for 3 h. The reaction mixture was quenched with cyclopropylmethanamine (2.98 mL, 34.7 mmol) and stirred for 1 h at room temperature, and then concentrated in vacuum to dryness. The residue was dissolved in cyclopropylmethanamine (8.51 mL, 99 mmol) and acetonitrile (40 mL) and the reaction mixture was heated at 80° C. for 16 h. TLC analysis (CHCl$_3$/MeOH, 9/1, v/v) shows reaction was complete, reaction mixture was evaporated to dryness. The residue was purified by flash column chromatography (First column silica gel 40 g, second column 80 g, eluting methanol in chloroform from 0-50%) to afford 1-(3-cyanophenyl)-N-(3-((cyclopropylmethylamino)(4-methoxynaphthalen-1-yl)methyl)phenyl)-3-(trifluoromethyl)-1H-pyrazole-5-carboxamide (154d) (1.64 g, 55% yield) as a colorless solid; $^1$H NMR (300 MHz, DMSO-d$_6$) δ 10.61 (s, 1H, D$_2$O exchangeable), 8.24-8.12 (m, 3H), 7.99 (dt, J=7.7, 1.3 Hz, 1H), 7.93-7.84 (m, 1H), 7.78-7.41 (m, 8H), 7.26 (q, J=3.7, 2.5 Hz, 2H), 6.98 (d, J=8.2 Hz, 1H), 5.52 (s, 1H), 3.95 (s, 3H), 2.39 (d, J=6.6 Hz, 2H), 1.08-0.89 (m, 1H), 0.38 (dd, J=7.6, 6.0 Hz, 2H), 0.06 (td, J=4.5, 3.8, 2.5 Hz, 2H); $^{19}$F NMR (282 MHz, DMSO-d$_6$) δ −60.94; MS (ES$^+$): MS (ES+) 596.3 (M+1), MS (ES−) 594.3 (M−1); IR (KBr, cm$^{-1}$): 2234 cm$^{-1}$ (—CN stretching).

Step-4: Preparation of 1-(3-(aminomethyl)phenyl)-N-(3-((cyclopropylmethylamino)(4-methoxynaphthalen-1-yl)methyl)phenyl)-3-(trifluoromethyl)-1H-pyrazole-5-carboxamide (154e)

To a stirred solution of 1-(3-cyanophenyl)-N-(3-((cyclopropylmethylamino)(4-methoxynaphthalen-1-yl)methyl)phenyl)-3-(trifluoromethyl)-1H-pyrazole-5-carboxamide (154d) (1.51 g, 2.54 mmol) in anhydrous methanol (10 mL), cooled to 0° C., were added nickel(II) chloride hexahydrate (0.301 g, 1.268 mmol), sodium borohydride (0.767 g, 20.28 mmol) was then added in small portions over 5 min. The reaction was exothermic and effervescent. The reaction mixture was stirred for 15 min at 0° C., at this point N1-(2-aminoethyl)ethane-1,2-diamine (2.74 mL, 25.4 mmol) was added. The mixture was allowed to stir for 30 minutes more before solvent was evaporated. The residue was treated with water (30 mL), and extracted with chloroform (2×30 mL), then ethyl acetate (2×30 mL), combined organic layers were dried over anhydrous MgSO$_4$, and filtered, excess solvents were pumped-off under reduced pressure. The residue was purified by flash column chromatography [(silica gel 40 g, eluting with CMA80/chloroform from 0 to 100%)] to furnish 430 mg 1-(3-(aminomethyl)phenyl)-N-(3-((cyclopropylmethylamino)(4-methoxynaphthalen-1-yl)methyl)phenyl)-3-(trifluoromethyl)-1H-pyrazole-5-carboxamide (154e) free-base as a yellow oil which was taken and dissolved in methanol, to this solution 2 N HCl (1.901 mL, 3.80 mmol) was added drop-wise, stirred for 30 min evaporated to dryness to afford 1-(3-(aminomethyl)phenyl)-N-(3-((cyclopropylmethylamino)(4-methoxynaphthalen-1-yl)methyl)phenyl)-3-(trifluoromethyl)-1H-pyrazole-5-carboxamide (154e) (483 mg, 32% yield) hydrochloride as a yellow solid; $^1$H NMR (300 MHz, DMSO-$d_6$) δ 10.95 (s, 1H), 10.23 (s, 1H, D$_2$O exchangeable), 10.02 (s, 1H, D$_2$O exchangeable), 8.53 (s, 3H, D$_2$O exchangeable), 8.29-8.10 (m, 3H,), 7.86 (t, J=1.8 Hz, 1H), 7.77-7.35 (m, 11H), 7.13 (d, J=8.2 Hz, 1H), 6.45-6.19 (m, 1H), 4.11 (q, J=6.2 Hz, 2H), 4.01 (s, 3H), 3.01-2.72 (m, 2H), 1.19 (ddt, J=10.6, 7.4, 3.5 Hz, 1H), 0.55 (dd, J=8.0, 3.7 Hz, 2H), 0.41-0.16 (m, 2H); $^1$H NMR (300 MHz, DMSO-$d_6$, D$_2$O) δ 10.93 (s, 1H), 8.30-8.22 (m, 1H), 8.19-8.11 (m, 1H), 7.93 (d, J=8.1 Hz, 1H), 7.80 (d, J=2.3 Hz, 1H), 7.71-7.61 (m, 3H), 7.61-7.56 (m, 4H), 7.54 (s, 1H), 7.51-7.42 (m, 2H), 7.14 (d, J=8.2 Hz, 1H), 6.31 (s, 1H), 4.12 (s, 2H), 4.02 (s, 3H), 3.07-2.73 (m, 2H), 1.14 (tt, J=8.6, 4.7 Hz, 1H), 0.71-0.47 (m, 2H), 0.42-0.14 (m, 2H); $^{19}$F NMR (282 MHz, DMSO-$d_6$) δ −60.77; MS (ES$^+$): MS (ES+) 600.3 (M+1), MS (ES−) 598.3 (M−1); Analysis calculated for: C$_{34}$H$_{32}$F$_3$N$_5$O$_2$·2.5HCl 1.75H$_2$O·0.17CHCl$_3$: C, 55.26; H, 5.18; Cl, 14.37; N, 9.43; Found: C, 55.33; H, 5.04; Cl, 14.59; N, 9.28.

Scheme 155

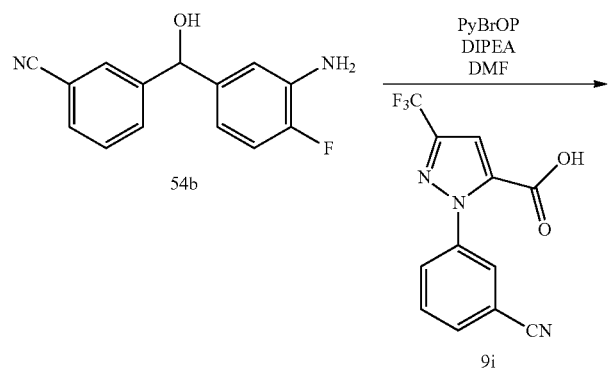

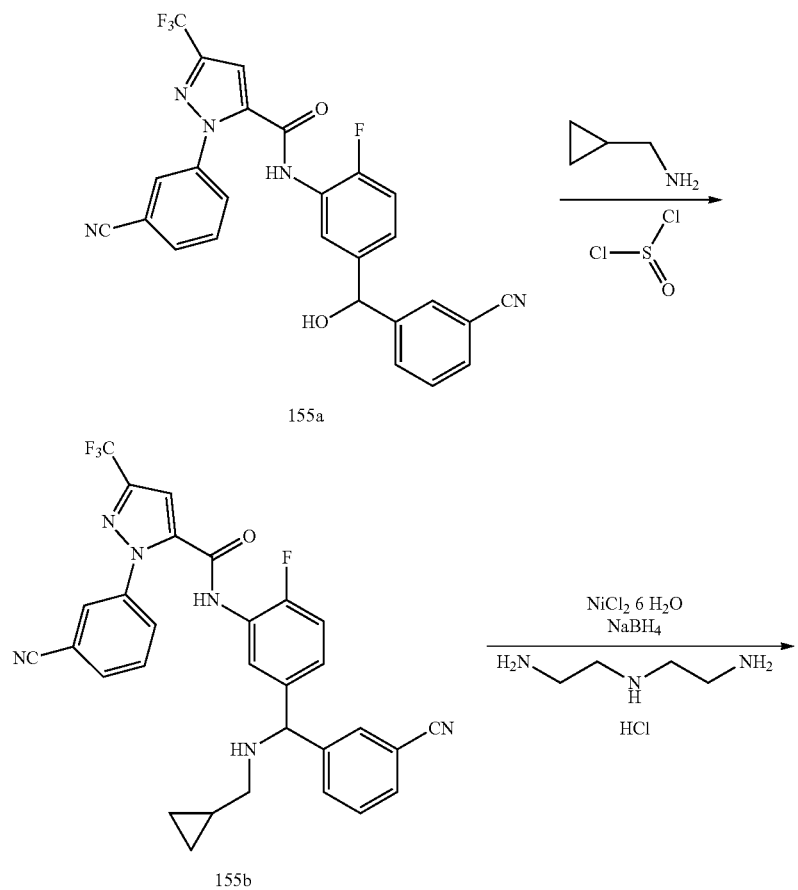

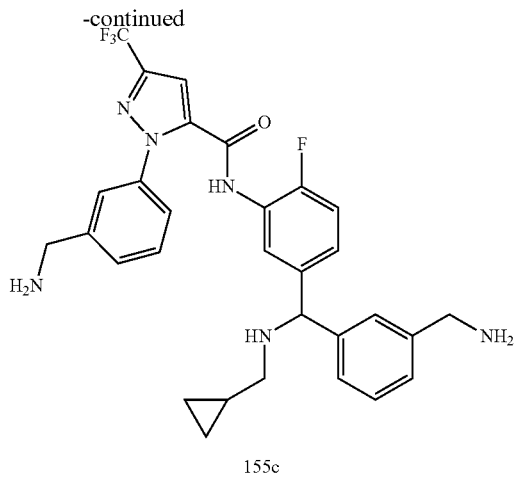

155c

Preparation of 1-(3-(aminomethyl)phenyl)-N-(5-((3-(aminomethyl)phenyl)(cyclopropylmethylamino)methyl)-2-fluorophenyl)-3-(trifluoromethyl)-1H-pyrazole-5-carboxamide (155c)

Step-1: Preparation of 1-(3-cyanophenyl)-N-(5-((3-cyanophenyl)(hydroxy)methyl)-2-fluorophenyl)-3-(trifluoromethyl)-1H-pyrazole-5-carboxamide (155a)

A single-necked 100 mL flask containing 1-(3-cyanophenyl)-3-(trifluoromethyl)-1H-pyrazole-5-carboxylic acid (9i) (3.42 g, 12.16 mmol), 3-((3-amino-4-fluorophenyl)(hydroxy)methyl)benzonitrile (54b) (1.964 g, 8.11 mmol), bromo-tris-pyrrolidino phosphoniumhexafluorophosphate (PyBrOP, 4.54 g, 9.73 mmol) was added N,N-dimethylformamide (47 mL) and N-ethyl-N-isopropylpropan-2-amine (7.06 mL, 40.5 mmol) successively in a positive flow of nitrogen at room temperature. The resulting reaction mixture was stirred at room temperature for 16 h under a positive flow of nitrogen atmosphere. Excess DMF was pumped-off under reduced pressure. The residue was treated with sat. NH₄Cl (30 mL), and extracted with ethyl acetate (2×50 mL) combined organics were dried over anhydrous MgSO₄, filtered, evaporated to dryness. The residue was then purified by flash column chromatography [silica gel 40 g, eluting with methanol in chloroform from 0-100%] to furnish 1-(3-cyanophenyl)-N-(5-((3-cyanophenyl)(hydroxy)methyl)-2-fluorophenyl)-3-(trifluoromethyl)-1H-pyrazole-5-carboxamide (155a) (1.479 g, 2.93 mmol, 36.1% yield) as a white solid; MS (ES⁺): MS (ES+) 265.2 (M+Na), MS (ES−) 504.2 (M−1).

Step-2: Preparation of 1-(3-cyanophenyl)-N-(5-((3-cyanophenyl)(cyclopropylmethylamino)methyl)-2-fluorophenyl)-3-(trifluoromethyl)-1H-pyrazole-5-carboxamide (155b)

To a solution of 1-(3-cyanophenyl)-N-(5-((3-cyanophenyl)(hydroxy)methyl)-2-fluorophenyl)-3-(trifluoromethyl)-1H-pyrazole-5-carboxamide (155a) (1.003 g, 1.984 mmol) in dichloromethane (20 mL) at 0° C. was added thionyl chloride (0.434 mL, 5.95 mmol), reaction mixture allowed to warm to room temperature and stirred for 3 h. The reaction mixture was quenched with cyclopropylmethanamine (1.205 mL, 13.89 mmol), and solution was stirred for 30 min at room temperature, and concentrated in vacuum to dryness. The residue was dissolved acetonitrile (20 mL), added cyclopropylmethanamine (1.205 mL, 13.89 mmol) and stirred at 80° C. for 16 h. The reaction mixture was cooled to room temperature, concentrated in vacuum and the residue obtained was purified by flash column chromatography (silica gel 40 g, eluting with methanol in chloroform from 0-100%) to afford 1-(3-cyanophenyl)-N-(5-((3-cyanophenyl)(cyclopropylmethylamino)methyl)-2-fluorophenyl)-3-(trifluoromethyl)-1H-pyrazole-5-carboxamide (155b) (376 mg, 34% yield) as a yellow solid; ¹H NMR (300 MHz, DMSO-d₆) δ 10.54 (s, 1H, D₂O exchangeable), 8.16-8.09 (m, 1H), 8.00 (dt, J=7.7, 1.3 Hz, 1H), 7.95-7.86 (m, 2H), 7.79-7.64 (m, 4H), 7.62-7.55 (m, 1H), 7.51 (t, J=7.7 Hz, 1H), 7.36 (ddd, J=7.4, 4.8, 2.2 Hz, 1H), 7.23 (dd, J=10.3, 8.5 Hz, 1H), 4.94 (d, J=3.2 Hz, 1H), 2.72 (d, J=4.8 Hz, 1H, D₂O exchangeable), 2.25 (t, J=6.0 Hz, 2H), 1.01-0.82 (m, 1H), 0.44-0.31 (m, 2H), 0.05 (td, J=5.1, 1.6 Hz, 2H); ¹⁹F NMR (282 MHz, DMSO-d₆) δ −60.97, −122.76; MS (ES⁺): MS (ES+) 559.3 (M+1), MS (ES−) 557.2 (M−1).

Step-3: Preparation of 1-(3-(aminomethyl)phenyl)-N-(5-((3-(aminomethyl)phenyl)(cyclopropylmethylamino)methyl)-2-fluorophenyl)-3-(trifluoromethyl)-1H-pyrazole-5-carboxamide (155c)

To a stirred solution of 1-(3-cyanophenyl)-N-(5-((3-cyanophenyl)(cyclopropylmethylamino)methyl)-2-fluorophenyl)-3-(trifluoromethyl)-1H-pyrazole-5-carboxamide (155b) (351 mg, 0.628 mmol) in anhydrous methanol (10 mL), cooled to 0° C., were added nickel(II) chloride hexahydrate (0.149 g, 0.628 mmol), sodium borohydride (0.380 g, 10.05 mmol) was then added in small portions over 5 min. The reaction was stirred for 15 min at 0° C., quenched with N1-(2-aminoethyl)ethane-1,2-diamine (1.358 mL, 12.57 mmol), stirred for additional 30 mins and concentrated in vacuum. The residue was treated with water (30 mL), and extracted with chloroform (2×30 mL), then ethyl acetate (2×30 mL), combined organic layers were dried over anhydrous MgSO₄, and filtered, excess solvents were pumped-off under reduced pressure. The residue was purified by flash column chromatography [(silica gel 40 g, eluting with CMA80/chloroform from 0 to 100%)] to furnish 1-(3-(aminomethyl)phenyl)-N-(5-((3-(aminomethyl)phenyl)(cyclopropylmethylamino)methyl)-2-fluorophenyl)-3-(trifluoromethyl)-1H-pyrazole-5-carboxamide (155c) (83 mg) freebase as a waxy solid which was dissolved in methanol and added 2 N HCl (0.566 mL, 1.131 mmol) (7.5 eq), stirred for 30 min evaporated to dryness to afford 1-(3-(aminomethyl)phenyl)-N-(5-((3-(aminomethyl)phenyl)(cyclopropylmethylamino)methyl)-2-fluorophenyl)-3-(trifluoromethyl)-1H-pyrazole-5-carboxamide (155c) (78 mg, 22% yield) hydrochloride salt as a white solid; $^1$H NMR (300 MHz, DMSO-d$_6$) δ 10.90 (s, 1H, D$_2$O exchangeable), 10.21 (s, 2H, D$_2$O exchangeable), 8.46 (s, 7H, D$_2$O exchangeable), 8.02-7.91 (m, 1H), 7.87-7.68 (m, 5H), 7.67-7.46 (m, 5H), 7.40 (dd, J=10.3, 8.6 Hz, 1H), 5.73-5.51 (m, 1H), 4.12 (d, J=5.8 Hz, 2H), 4.00 (d, J=5.7 Hz, 2H), 2.71 (d, J=7.6 Hz, 2H), 1.16 (s, 1H), 0.67-0.44 (m, 2H), 0.40-0.22 (m, 2H); $^1$H NMR (300 MHz, DMSO-d$_6$, D$_2$O) δ 7.90 (d, J=6.8 Hz, 1H), 7.76-7.48 (m, 10H), 7.47-7.37 (m, 1H), 5.63 (s, 1H), 4.12 (s, 2H), 4.03 (s, 2H), 2.74 (d, J=7.5 Hz, 2H), 1.10 (s, 1H), 0.58 (d, J=7.6 Hz, 2H), 0.41-0.23 (m, 2H); $^{19}$F NMR (282 MHz, DMSO-d$_6$) δ −60.59, −119.65. MS (ES$^+$): MS (ES+) 567.3 (M+1), MS (ES−) 565.3 (M−1), 601.3 (M+Cl); Analysis calculated for C$_{30}$H$_{30}$F$_4$N$_6$O.4.25H$_2$O.3.05HCl: C, 47.76; H, 5.55; Cl, 14.33; N, 11.14; Found: C, 47.58; H, 5.16; Cl, 14.65; N, 10.96.

Scheme 156

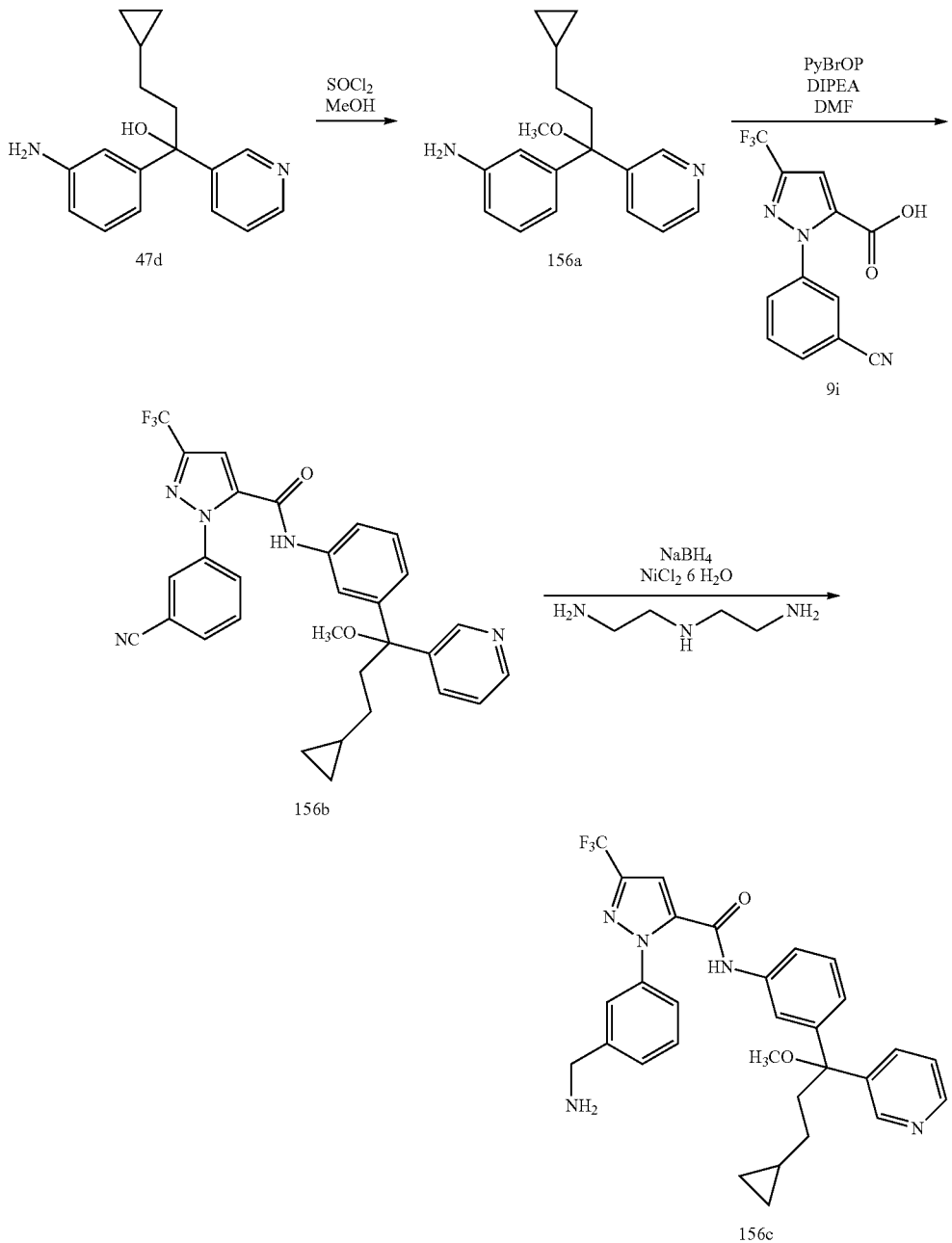

Preparation of 1-(3-(aminomethyl)phenyl)-N-(3-(3-cyclopropyl-1-methoxy-1-(pyridin-3-yl)propyl)phenyl)-3-(trifluoromethyl)-1H-pyrazole-5-carboxamide (156c)

Step-1: Preparation of 3-(3-cyclopropyl-1-methoxy-1-(pyridin-3-yl)propyl)aniline (156a)

To a stirred solution of 1-(3-aminophenyl)-3-cyclopropyl-1-(pyridin-3-yl)propan-1-ol (47d) (0.955 g, 3.56 mmol) in dichloromethane (40 mL) was added thionyl chloride (1.039 mL, 14.23 mmol) at room temperature. The reaction was stirred overnight at room temperature and quenched with methanol (2.88 mL, 71.2 mmol) and triethylamine (4.96 mL, 35.6 mmol). The mixture was stirred at room temperature for 1 h and concentrated in vacuum. The crude residue was purified twice by flash column chromatography [silica gel 40 g, eluting with methanol in chloroform (0 to 10% to 100%)] to afford 3-(3-cyclopropyl-1-methoxy-1-(pyridin-3-yl)propyl)aniline (156a) (491 mg, 48.9% yield). MS (ES+): 283.3 (M+H) and (E)-3-(3-cyclopropyl-1-(pyridin-3-yl)prop-1-enyl)aniline (250 mg, 0.999 mmol, 28.1% yield). MS (ES+): 251.2 (M+H).

Step-2: Preparation of 1-(3-cyanophenyl)-N-(3-(3-cyclopropyl-1-methoxy-1-(pyridin-3-yl)propyl)phenyl)-3-(trifluoromethyl)-1H-pyrazole-5-carboxamide (156b)

To a solution of 1-(3-cyanophenyl)-3-(trifluoromethyl)-1H-pyrazole-5-carboxylic acid (9i) (0.526 g, 1.870 mmol) in N,N-Dimethylformamide (10 mL) was added 3-(3-cyclopropyl-1-methoxy-1-(pyridin-3-yl)propyl)aniline (156a) (0.48 g, 1.700 mmol), N-ethyl-N-isopropylpropan-2-amine (1.480 mL, 8.50 mmol) and bromo-tris-pyrrolidino phosphoniumhexafluorophosphate(PyBrOP, 0.792 g, 1.700 mmol) at room temperature. The reaction mixture was stirred at room temperature for 20 h under nitrogen atmosphere. The reaction mixture was diluted with water (100 mL) and extracted with ethyl acetate (2×200 mL). The organic layers were combined, washed with water (2×100 mL), brine (50 mL), dried, filtered, and evaporated in vacuum to dryness. The residue obtained was purified by flash column chromatography (silica gel 40 g, eluting with CMA 80 in chloroform) to give 1-(3-cyanophenyl)-N-(3-(3-cyclopropyl-1-methoxy-1-(pyridin-3-yl)propyl)phenyl)-3-(trifluoromethyl)-1H-pyrazole-5-carboxamide (156b) (332 mg, 36%); MS (ES+), 546.3 (M+1).

Step-3: Preparation of 1-(3-(aminomethyl)phenyl)-N-(3-(3-cyclopropyl-1-methoxy-1-(pyridin-3-yl)propyl)phenyl)-3-(trifluoromethyl)-1H-pyrazole-5-carboxamide (156c)

To a stirred solution of 1-(3-cyanophenyl)-N-(3-(3-cyclopropyl-1-methoxy-1-(pyridin-3-yl)propyl)phenyl)-3-(trifluoromethyl)-1H-pyrazole-5-carboxamide (156b) (0.295 g, 0.541 mmol) in methanol (20 mL) at 0° C. was added nickel(II) chloride (0.088 g, 0.676 mmol). To this solution sodium tetrahydroborate (0.205 g, 5.41 mmol) was added in small portions over a period of 15 minutes. The reaction was stirred for 30 minutes and quenched by adding N1-(2-aminoethyl)ethane-1,2-diamine (0.449 mL, 4.33 mmol) and stirred for additional 30 minutes at room temperature. The reaction mixture was concentrated to remove methanol. The reaction mixture was diluted with water (50 mL) and stirred for 12 hours. The solid separated was collected by filtration. The solid was suspended in ethanol (100 mL) and concentrated to remove water. The residue was purified by flash column chromatography (silica gel, 12 g eluting with CMA 80 in chloroform) to afford 1-(3-(aminomethyl)phenyl)-N-(3-(3-cyclopropyl-1-methoxy-1-(pyridin-3-yl)propyl)phenyl)-3-(trifluoromethyl)-1H-pyrazole-5-carboxamide (156c) (89 mg, 0.162 mmol, 29.9% yield) free base as a colorless solid. $^1$HNMR (300 MHz, DMSO-d$_6$) δ 10.69 (s, 1H, D$_2$O exchangeable), 8.52 (d, J=2.2 Hz, 1H), 8.41 (dd, J=4.7, 1.6 Hz, 1H), 7.72-7.56 (m, 4H), 7.51 (s, 1H), 7.42 (d, J=6.6 Hz, 2H), 7.37-7.24 (m, 3H), 7.09 (d, J=8.0 Hz, 1H), 3.77 (s, 2H), 3.01 (s, 3H), 2.46-2.40 (m, 2H), 1.99 (s, 2H, D$_2$O exchangeable), 0.92 (h, J=8.1 Hz, 2H), 0.66 (t, J=7.0 Hz, 1H), 0.35 (dt, J=8.2, 3.0 Hz, 2H), −0.02−0.21 (m, 2H); Mass spec (ES+) 550.4; (ES−) 548.3 (M−1), 584.3 (M+35); Analysis calculated for C$_{30}$H$_{30}$F$_3$N$_5$O$_2$(H$_2$O)$_{0.5}$: C, 64.48; H, 5.51; N, 12.54; Found: C, 64; 79 H, 5.51; N, 12.27.

To a solution of 1-(3-(aminomethyl)phenyl)-N-(3-(3-cyclopropyl-1-methoxy-1-(pyridin-3-yl)propyl)phenyl)-3-(trifluoromethyl)-1H-pyrazole-5-carboxamide (156c) free base (50 mgs) suspended in hydrogen chloride (3 M solution in isopropanol, 2 mL, 6.00 mmol) was stirred for 30 mins and concentrated in vacuum to dryness to afford 1-(3-(aminomethyl)phenyl)-N-(3-(3-cyclopropyl-1-methoxy-1-(pyridin-3-yl)propyl)phenyl)-3-(trifluoromethyl)-1H-pyrazole-5-carboxamide (156c) hydrochloride salt as a white solid. $^1$H NMR (300 MHz, DMSO-d$_6$) δ 10.81 (s, 1H), 8.71 (s, 1H), 8.67 (d, J=5.4 Hz, 1H), 8.39 (s, 3H, D$_2$O exchangeable), 8.11 (d, J=7.9 Hz, 1H), 7.79-7.47 (m, 9H), 7.32 (t, J=7.9 Hz, 1H), 7.13 (d, J=7.8 Hz, 1H), 4.13 (q, J=5.8 Hz, 2H), 3.04 (s, 3H), 2.44 (dt, J=3.9, 2.3 Hz, 2H), 1.00-0.75 (m, 2H), 0.67 (s, 1H), 0.46-0.29 (m, 2H), −0.07 (q, J=3.7, 3.1 Hz, 2H); Analysis calculated for C$_{30}$H$_{30}$F$_3$N$_5$O$_2$.2.25HCl.2H$_2$O.0.5C$_3$H$_8$O: C, 54.29; H, 5.82; N, 10.05; Cl, 11.30; Found: C, 54.73; H, 5.65; N, 10.00; Cl, 11.48.

Scheme 157

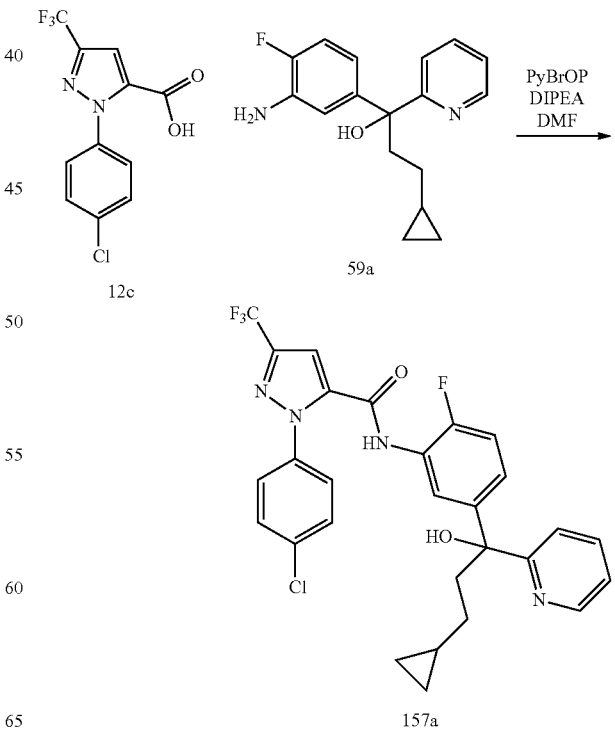

Preparation of 1-(4-chlorophenyl)-N-(5-(3-cyclopropyl-1-hydroxy-1-(pyridin-2-yl)propyl)-2-fluorophenyl)-3-(trifluoromethyl)-1H-pyrazole-5-carboxamide (157a)

In a 50 mL single-necked flask containing 1-(4-chlorophenyl)-3-(trifluoromethyl)-1H-pyrazole-5-carboxylic acid (12c) (0.291 g, 1.001 mmol), 1-(3-amino-4-fluorophenyl)-3-cyclopropyl-1-(pyridin-2-yl)propan-1-ol (59a) (0.344 g, 1.202 mmol), bromo-tris-pyrrolidino phosphoniumhexafluorophosphate(PyBrop) (0.560 g, 1.202 mmol) was added N,N-dimethylformamide (10 mL) and N-ethyl-N-isopropylpropan-2-amine (0.872 mL, 5.01 mmol) successively in a positive flow of nitrogen at room temperature. The resulting reaction mixture was stirred at room temperature for 16 h under a positive flow of nitrogen atmosphere. The reaction was diluted with ethyl acetate (50 mL) washed with water (50 mL). The aqueous layer was extracted with ethyl acetate (2×50 mL). The organics layers were combined dried over anhydrous $MgSO_4$, filtered and evaporated to dryness. The residue was purified by flash column chromatography [silica gel 25 g, eluting with ethyl acetate in hexanes from 0-100%] to furnish 1-(4-chlorophenyl)-N-(5-(3-cyclopropyl-1-hydroxy-1-(pyridin-2-yl)propyl)-2-fluorophenyl)-3-(trifluoromethyl)-1H-pyrazole-5-carboxamide (157a) (436 mg, 78% yield) as a yellow solid; $^1$H NMR (300 MHz, DMSO-$d_6$) δ 10.50 (s, 1H, $D_2O$ exchangeable), 8.49 (ddd, J=4.9, 1.8, 0.9 Hz, 1H), 7.78-7.68 (m, 2H), 7.67-7.53 (m, 6H), 7.41 (ddd, J=8.7, 4.8, 2.3 Hz, 1H), 7.24-7.11 (m, 2H), 5.83 (s, 1H, $D_2O$ exchangeable), 2.46-2.27 (m, 2H), 1.03 (ddt, J=18.2, 12.4, 7.1 Hz, 2H), 0.57 (d, J=12.5 Hz, 1H), 0.42-0.20 (m, 2H), −0.04-−0.18 (m, 2H); $^{19}$F NMR (282 MHz, DMSO-$d_6$) δ −60.88, −124.19; MS (ES$^+$): MS (ES+) 559.2 (M+1), MS (ES−) 557.3 (M−1).

Preparation of 1-(6-chloronaphthalen-2-yl)-N-(5-(3-cyclopropyl-1-hydroxy-1-(pyridin-2-yl)propyl)-2-fluorophenyl)-3-(trifluoromethyl)-1H-pyrazole-5-carboxamide (158a)

In a 50 mL single-necked flask containing 1-(6-chloronaphthalen-2-yl)-3-(trifluoromethyl)-1H-pyrazole-5-carboxylic acid (14d) (0.200 g, 0.587 mmol), 1-(3-amino-4-fluorophenyl)-3-cyclopropyl-1-(pyridin-2-yl)propan-1-ol (59a) (0.202 g, 0.704 mmol), bromo-tris-pyrrolidino phosphoniumhexafluorophosphate(PyBrop) (0.328 g, 0.704 mmol) was added N,N-dimethylformamide (6 mL) and N-ethyl-N-isopropylpropan-2-amine (0.511 mL, 2.94 mmol) successively in a positive flow of nitrogen at room temperature. The resulting reaction mixture was stirred at room temperature for 16 h under a positive flow of nitrogen atmosphere. The reaction was diluted with ethyl acetate (30 mL) and washed with water (30 mL). The aqueous layer was again extracted with ethyl acetate (2×30 mL). The organics layers were combined washed with water (30 mL), dried over anhydrous $MgSO_4$, filtered and evaporated to dryness. The residue was purified by flash column chromatography [silica gel 25 g, eluting with ethyl acetate in hexanes from 0-100%] to furnish 1-(6-chloronaphthalen-2-yl)-N-(5-(3-cyclopropyl-1-hydroxy-1-(pyridin-2-yl)propyl)-2-fluorophenyl)-3-(trifluoromethyl)-1H-pyrazole-5-carboxamide (158a) (0.235 g, 0.386 mmol, 65.7% yield) as a yellow solid; $^1$H NMR (300 MHz, DMSO-$d_6$) δ 10.56 (s, 1H, $D_2O$ exchangeable), 8.48 (d, J=4.7 Hz, 1H), 8.18 (s, 2H), 8.06 (t, J=10.0 Hz, 2H), 7.67 (dq, J=17.8, 8.7 Hz, 6H), 7.39 (s, 1H), 7.26-7.08 (m, 2H), 5.81 (s, 1H, $D_2O$ exchangeable), 2.44-2.27 (m, 2H), 1.00 (s, 2H), 0.57 (s, 1H), 0.30 (d, J=7.7 Hz, 2H), −0.13 (d, J=4.6 Hz, 2H); $^{19}$F NMR (282 MHz, DMSO-$d_6$) δ −60.67, −123.96; $^1$H NMR (300 MHz, DMSO-$d_6$) $D_2O$ δ 8.48 (dt, J=4.7, 1.4 Hz, 1H), 8.18 (t, J=2.0 Hz, 2H), 8.07 (t, J=8.9 Hz, 2H), 7.80-7.56 (m, 6H), 7.40 (ddd, J=8.8, 4.8, 2.4 Hz, 1H), 7.27-7.10 (m, 2H), 2.45-2.28 (m, 2H), 0.98 (ddt, J=19.9, 14.0, 7.2 Hz, 2H), 0.57 (q, J=6.8, 6.2 Hz, 1H), 0.38-0.24 (m, 2H), −0.13 (h, J=3.6 Hz, 2H); MS (ES$^+$): MS (ES+) 609.3 (M+), 632.2 (M+Na), MS (ES−) 608.1 (M−1).

Scheme 158

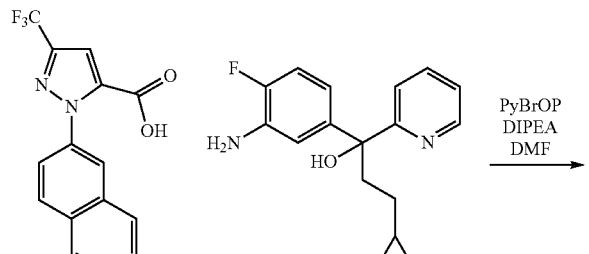

Scheme 159

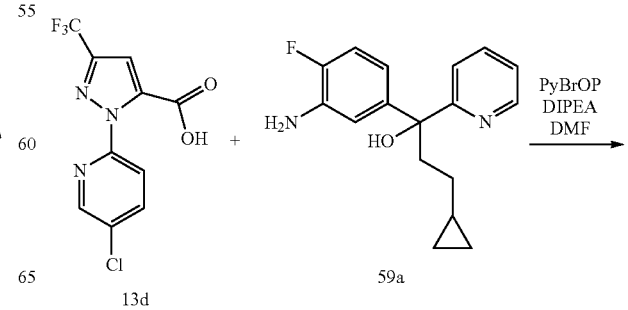

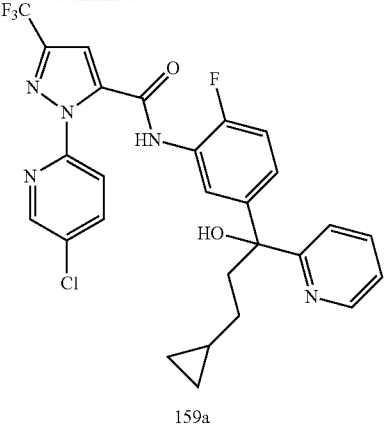

159a

Preparation of 1-(5-chloropyridin-2-yl)-N-(5-(3-cyclopropyl-1-hydroxy-1-(pyridin-2-yl)propyl)-2-fluorophenyl)-3-(trifluoromethyl)-1H-pyrazole-5-carboxamide (159a)

In a 50 mL single-necked flask containing 1-(5-chloropyridin-2-yl)-3-(trifluoromethyl)-1H-pyrazole-5-carboxylic acid (13d) (7 mg, 0.024 mmol), 1-(3-amino-4-fluorophenyl)-3-cyclopropyl-1-(pyridin-2-yl)propan-1-ol (59a) (10.31 mg, 0.036 mmol), bromo-tris-pyrrolidino phosphoniumhexafluorophosphate(PyBrOP, 0.013 g, 0.029 mmol) was added N,N-dimethylformamide (0.232 mL) and N-ethyl-N-isopropylpropan-2-amine (0.021 mL, 0.120 mmol) successively in a positive flow of nitrogen at room temperature. The resulting reaction mixture was stirred at room temperature for 16 h under a positive flow of nitrogen atmosphere. The reaction was diluted with ethyl acetate (25 mL) and washed with water (25 mL). The aqueous layer was extracted with ethyl acetate (2×25 mL). The combined organics layers were washed with water (25 mL), brine (25 mL) dried over anhydrous MgSO$_4$, filtered, evaporated to dryness. The residue was purified by flash column chromatography [silica gel 4 g, eluting with ethyl acetate in hexanes from 0-100%] to furnish 1-(5-chloropyridin-2-yl)-N-(5-(3-cyclopropyl-1-hydroxy-1-(pyridin-2-yl)propyl)-2-fluorophenyl)-3-(trifluoromethyl)-1H-pyrazole-5-carboxamide (159a) (5 mg, 37% yield) as an off-white solid; $^1$H NMR (300 MHz, DMSO-d$_6$) δ 10.29 (s, 1H, D$_2$O exchangeable), 8.70 (d, J=2.5 Hz, 1H), 8.51 (dt, J=4.9, 1.4 Hz, 1H), 8.34 (dd, J=8.8, 2.6 Hz, 1H), 8.15 (d, J=8.8 Hz, 1H), 7.81-7.72 (m, 2H), 7.70-7.64 (m, 2H), 7.44 (ddd, J=8.7, 4.7, 2.3 Hz, 1H), 7.28-7.15 (m, 2H), 5.86 (s, 1H, D$_2$O exchangeable), 2.45-2.34 (m, 2H), 1.11-1.01 (m, 2H), 0.61 (td, J=7.5, 3.9 Hz, 1H), 0.37-0.31 (m, 2H), −0.08 (dt, J=4.7, 2.0 Hz, 2H); $^{19}$F NMR (282 MHz, DMSO-d$_6$) δ −56.83, −124.52; MS (ES$^+$): MS (ES+) 560.2 (M+1); MS (ES−) 558.2 (M−1).

Scheme 160

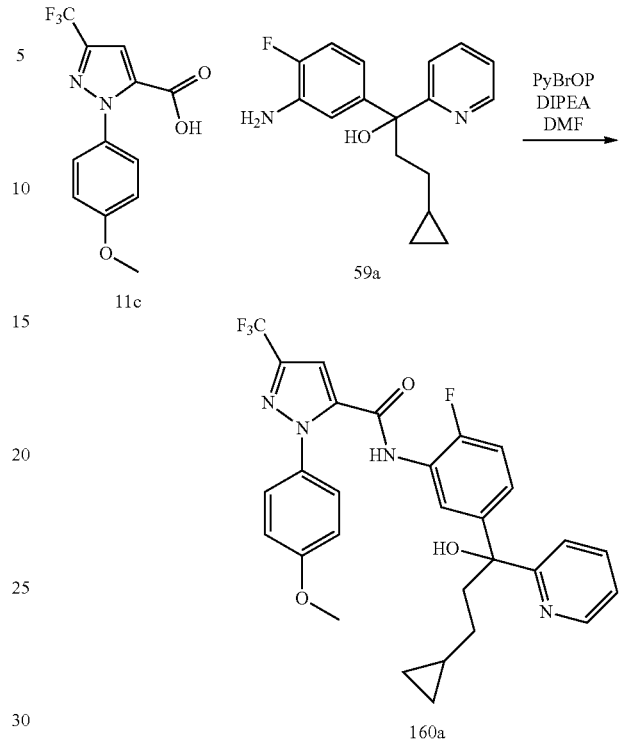

160a

Preparation of N-(5-(3-cyclopropyl-1-hydroxy-1-(pyridin-2-yl)propyl)-2-fluorophenyl)-1-(4-methoxyphenyl)-3-(trifluoromethyl)-1H-pyrazole-5-carboxamide (160a)

A single-necked 50 mL flask containing 1-(4-methoxyphenyl)-3-(trifluoromethyl)-1H-pyrazole-5-carboxylic acid (11c) (100 mg, 0.349 mmol), 1-(3-amino-4-fluorophenyl)-3-cyclopropyl-1-(pyridin-2-yl)propan-1-ol (59a) (0.120 g, 0.419 mmol), bromo-tris-pyrrolidino phosphoniumhexafluorophosphate(PyBrOP, 0.195 g, 0.419 mmol) were treated N,N-dimethylformamide (3.38 mL, 43.7 mmol) and N-ethyl-N-isopropylpropan-2-amine (0.304 mL, 1.747 mmol) successively in a positive flow of nitrogen at room temperature. The resulting reaction mixture was stirred at room temperature for 16 h under a positive flow of nitrogen atmosphere. The reaction was diluted with ethyl acetate (30 mL) and washed with water (30 mL). The aqueous layer was again extracted with ethyl acetate (2×30 mL). The combined organics layers were washed with water (30 mL), brine (30 mL), dried over anhydrous MgSO$_4$, filtered and evaporated to dryness. The residue was purified by flash column chromatography [first column: silica gel 12 g, eluting with ethyl acetate in hexanes from 0-100%, second column: silica gel 12 g, eluting with ethyl acetate in hexanes from 0-20%] to furnish N-(5-(3-cyclopropyl-1-hydroxy-1-(pyridin-2-yl)propyl)-2-fluorophenyl)-1-(4-methoxyphenyl)-3-(trifluoromethyl)-1H-pyrazole-5-carboxamide (160a) (31 mg, 16% yield) as a yellow solid; $^1$H NMR (300 MHz, DMSO-d$_6$) δ 10.43 (s, 1H, D$_2$O exchangeable), 8.49 (ddd, J=4.8, 1.8, 0.9 Hz, 1H), 7.73 (td, J=7.7, 1.9 Hz, 2H), 7.63 (dt, J=8.0, 1.1 Hz, 1H), 7.55 (s, 1H), 7.48-7.35 (m, 3H), 7.25-7.11 (m, 2H), 7.07-6.99 (m, 2H), 5.82 (s, 1H, D$_2$O exchangeable), 3.81 (s, 3H), 2.45-2.25 (m, 2H), 1.01 (dddd, J=25.1, 13.6, 9.9, 6.3

Hz, 2H), 0.71-0.50 (m, 1H), 0.39-0.25 (m, 2H), −0.10 (h, J=3.4 Hz, 2H); $^{19}$F NMR (282 MHz, DMSO-$d_6$) δ −60.71, −124.38; MS (ES$^+$): MS (ES+) 555.3 (M+1), 577.3 (M+Na), 553.3 (M−1).

column chromatography [silica gel 12 g, eluting with ethyl acetate in hexanes from 0-100%] to furnish tert-butyl 6-amino-7-fluoro-3,4-dihydroisoquinoline-2(1H)-carboxylate (161b) (0.256 g, 57% yield) as a white solid; $^1$H NMR

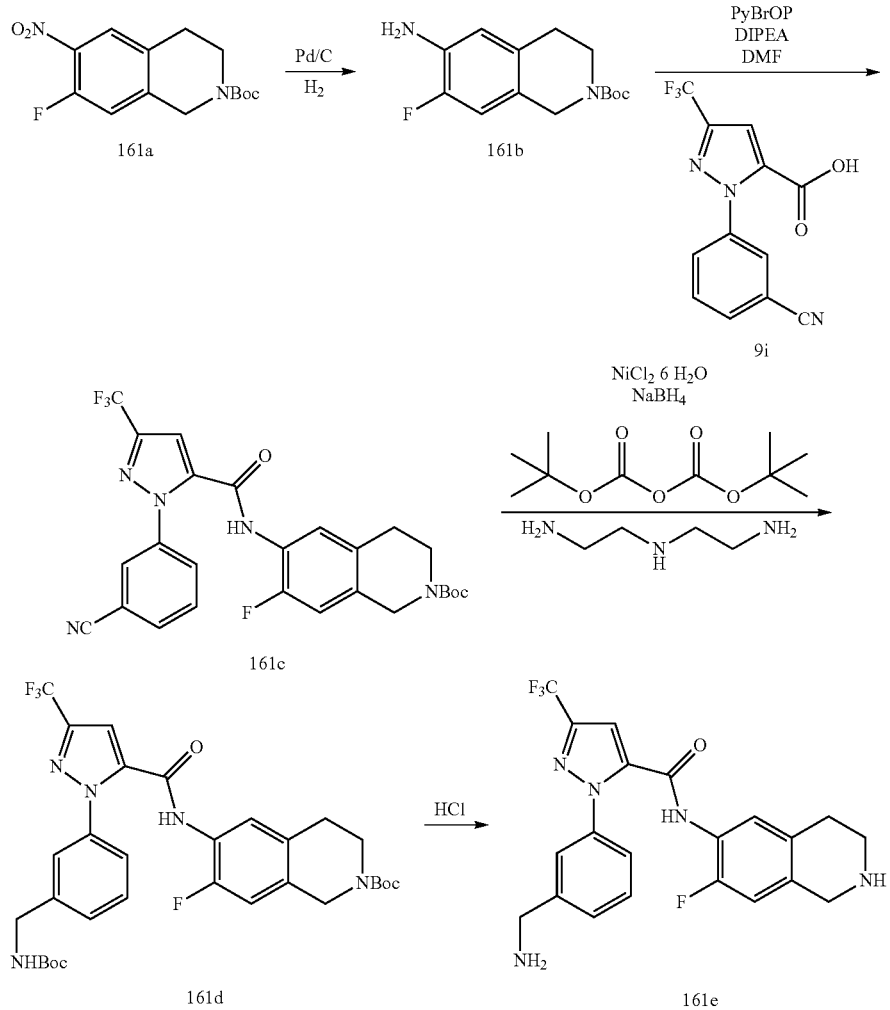

Scheme 161

Preparation of 1-(3-(aminomethyl)phenyl)-N-(7-fluoro-1,2,3,4-tetrahydroisoquinolin-6-yl)-3-(trifluoromethyl)-1H-pyrazole-5-carboxamide (161e)

Step-1: Preparation of tert-butyl 6-amino-7-fluoro-3,4-dihydroisoquinoline-2(1H)-carboxylate (161b)

To a solution of tert-butyl 7-fluoro-6-nitro-3,4-dihydroisoquinoline-2(1H)-carboxylate (161a) (0.5 g, 1.688 mmol) (Prepared as described in the literature (a) Harling, J. D; Watson, N. S.; Young, R. J. WO 2006/108709 A1 Oct. 19, 2006; (b) Watson, N. S.; Adams, C.; Belton, D.; Brown, D.; Burns-Kurtis, C. L.; Chaudry, L.; Chan, C.; Convery, Maire A.; Davies, D. E.; Exall, A. M. et al, *Bioorganic & Medicinal Chemistry Letters* (2011), 21(6), 1588-1592) in methanol (20 mL) was added palladium on carbon (10%) (0.359 g, 3.38 mmol) and hydrogenated for 3 h at 60 psi. The catalyst was removed by filtration through Celite and the filtrate was concentrated in vacuum. The residue was purified by flash (300 MHz, DMSO-$d_6$) δ 6.81 (d, J=12.0 Hz, 1H), 6.51 (d, J=9.1 Hz, 1H), 4.98 (s, 2H, D$_2$O exchangeable), 4.31 (s, 2H), 3.47 (t, J=5.9 Hz, 2H), 2.59 (t, J=5.9 Hz, 2H), 1.41 (s, 9H); $^{19}$F NMR (282 MHz, DMSO-$d_6$) δ −137.71; MS (ES$^+$): MS (ES+) 289.2 (M+Na), 555.4 (2M+Na), MS (ES−) 265.1 (M−1); Analysis calculated for $C_{14}H_{19}FN_2O_2$: C, 63.14; H, 7.19; N, 10.52; Found: C, 63.41; H, 7.27; N, 10.43.

Step-2: Preparation of tert-butyl 6-(1-(3-cyanophenyl)-3-(trifluoromethyl)-1H-pyrazole-5-carboxamido)-7-fluoro-3,4-dihydroisoquinoline-2(1H)-carboxylate (161c)

To a solution of 1-(3-cyanophenyl)-3-(trifluoromethyl)-1H-pyrazole-5-carboxylic acid (9i) (0.250 g, 0.889 mmol) in N,N-dimethylformamide (6 mL) was added tert-butyl 6-amino-7-fluoro-3,4-dihydroisoquinoline-2(1H)-carboxylate (161b) (0.237 g, 0.889 mmol), N-ethyl-N-isopropylpropan-2-amine (1.239 mL, 7.11 mmol) and Bromo-tris-pyrrolidino phosphoniumhexafluorophosphate (PyBroP) (0.456 g, 0.978 mmol) at room temperature. The resulting reaction mixture was stirred at 20° C. for 16 h. The reaction mixture was quenched with water (25 mL) and extracted with ethyl acetate (50 mL, 20 mL, 20 mL). The organic layers were combined washed with water (25 mL), brine (25 mL), dried over MgSO$_4$, filtered, concentrated in vacuum to dryness. The residue purified by flash column chromatography (silica gel 25 g, eluting with hexanes in ethyl acetate from 0-100%) to furnish tert-butyl 6-(1-(3-cyanophenyl)-3-(trifluoromethyl)-1H-pyrazole-5-carboxamido)-7-fluoro-3,4-dihydroisoquinoline-2(1H)-carboxylate (161c) (235 mg, 50% yield) as a white solid; $^1$H NMR (300 MHz, DMSO-d$_6$) δ 10.51 (s, 1H, D$_2$O exchangeable), 8.12 (t, J=1.9 Hz, 1H), 8.00 (dt, J=7.7, 1.3 Hz, 1H), 7.95-7.85 (m, 1H), 7.80-7.68 (m, 2H), 7.35 (d, J=7.7 Hz, 1H), 7.18 (d, J=11.2 Hz, 1H), 4.48 (s, 2H), 3.53 (t, J=5.9 Hz, 2H), 2.72 (t, J=5.8 Hz, 2H), 1.42 (s, 9H); $^{19}$F NMR (282 MHz, DMSO-d$_6$) δ −59.40-−62.27 (m), −125.03; MS (ES−): 527.7 (M−1).

Step-3: Preparation of tert-butyl 6-(1-(3-((tert-butoxycarbonylamino)methyl)phenyl)-3-(trifluoromethyl)-1H-pyrazole-5-carboxamido)-7-fluoro-3,4-dihydroisoquinoline-2(1H)-carboxylate (161d)

To a stirred solution of tert-butyl 6-(1-(3-cyanophenyl)-3-(trifluoromethyl)-1H-pyrazole-5-carboxamido)-7-fluoro-3,4-dihydroisoquinoline-2(1H)-carboxylate (161c) (0.223 g, 0.421 mmol) in anhydrous methanol (10 mL), cooled to 0° C., was added di-tert-butyl dicarbonate [Boc anhydride] (0.184 g, 0.842 mmol), nickel(II) chloride hexahydrate (0.020 g, 0.084 mmol), followed by the addition of sodium borohydride (0.159 g, 4.21 mmol) in small portions over a period of 5 min. The reaction mixture was stirred for 15 min at room temperature, quenched with N1-(2-aminoethyl)ethane-1,2-diamine (0.091 mL, 0.842 mmol), stirred for 30 mins and concentrated in vacuum to dryness. The residue was treated with ethyl acetate (25 mL), washed with water (25 mL, brine (25 mL), dried over MgSO$_4$ and concentrated in vacuum. The residue was purified by flash column chromatography (silica gel 25 g, eluting with 0-20% ethyl acetate in hexanes) to afford tert-butyl 6-(1-(3-((tert-butoxycarbonylamino)methyl)phenyl)-3-(trifluoromethyl)-1H-pyrazole-5-carboxamido)-7-fluoro-3,4-dihydroisoquinoline-2(1H)-carboxylate (161d) (98 mg, 37% yield) as a white solid; $^1$H NMR (300 MHz, DMSO-d$_6$) δ 10.56 (s, 1H, D$_2$O exchangeable), 7.58 (s, 1H), 7.49 (dd, J=14.5, 7.5 Hz, 1H), 7.41 (d, J=8.6 Hz, 2H), 7.35 (t, J=6.2 Hz, 2H), 7.17 (d, J=11.1 Hz, 1H), 4.47 (s, 2H), 4.19 (d, J=6.4 Hz, 2H), 3.52 (t, J=5.8 Hz, 2H), 2.72 (t, J=5.6 Hz, 2H), 1.41 (s, 9H), 1.38 (s, 9H); $^{19}$F NMR (282 MHz, DMSO-d$_6$) δ −60.82, −125.28; MS (ES$^+$): MS (ES+) 656.3 (M+Na), MS (ES−) 632.4 (M−1). Analysis calculated for: C$_{31}$H$_{35}$F$_4$N$_5$O$_5$: C, 58.76; H, 5.57; N, 11.05; Found: C, 58.65; H, 5.86; N, 10.69.

Step-4: Preparation of 1-(3-(aminomethyl)phenyl)-N-(7-fluoro-1,2,3,4-tetrahydroisoquinolin-6-yl)-3-(trifluoromethyl)-1H-pyrazole-5-carboxamide (161e)

To a solution of tert-butyl 6-(1-(3-((tert-butoxycarbonylamino)methyl)phenyl)-3-(trifluoromethyl)-1H-pyrazole-5-carboxamido)-7-fluoro-3,4-dihydroisoquinoline-2(1H)-carboxylate (161d) (0.086 g, 0.136 mmol) in dioxane (4 mL), was added hydrogen chloride (4M in dioxane, 1.9 mL, 7.60 mmol) and stirred at room temperature for 14 h. The reaction mixture was diluted with hexanes, filtered, dried under vacuum to furnish 1-(3-(aminomethyl)phenyl)-N-(7-fluoro-1,2,3,4-tetrahydroisoquinolin-6-yl)-3-(trifluoromethyl)-1H-pyrazole-5-carboxamide (161e) (28 mg, 48% yield) as a pale yellow solid; $^1$H NMR (300 MHz, DMSO-d$_6$) δ 10.75 (s, 1H, D$_2$O exchangeable), 9.64 (s, 2H, D$_2$O exchangeable), 8.47 (s, 3H, D$_2$O exchangeable), 7.72 (s, 2H), 7.67-7.61 (m, 2H), 7.56 (s, 1H), 7.52 (m, 1H), 7.50-7.43 (m, 1H), 7.23 (d, J=11.0 Hz, 1H), 4.22 (s, 2H), 4.12 (s, 2H), 3.35 (m, 2H), 2.97 (m, 2H); $^1$H NMR (300 MHz, DMSO-d$_6$ D$_2$O) δ 7.71 (s, 1H), 7.67 (m, 1H), 7.60 (m, 1H), 7.58-7.45 (m, 3H), 7.23 (d, J=11.0 Hz, 1H), 4.25 (s, 2H), 4.12 (s, 2H), 3.39-3.31 (m, 2H), 2.98 (m, 2H); $^{19}$F NMR (282 MHz, DMSO-d$_6$) δ −60.82, −124.02; MS (ES$^+$): MS (ES+) 434 (M+1), (ES−) 431.8 (M−1); Analysis calculated for C$_{21}$H$_{19}$F$_4$N$_5$O.2.25HCl.3H$_2$O: C, 44.29; H, 4.82; N, 12.30; Found: C, 44.29; H, 4.82; N, 12.30.

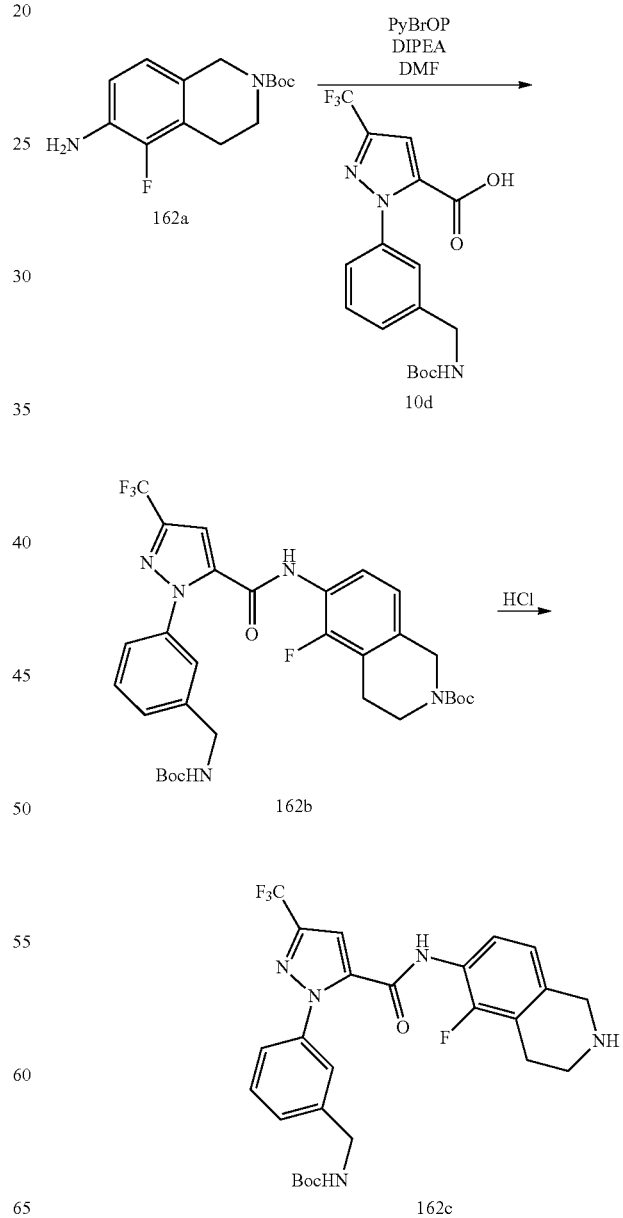

Scheme 162

Preparation of 1-(3-(aminomethyl)phenyl)-N-(5-fluoro-1,2,3,4-tetrahydroisoquinolin-6-yl)-3-(trifluoromethyl)-1H-pyrazole-5-carboxamide (162c)

Step-1: Preparation of tert-butyl 6-(1-(3-((tert-butoxycarbonylamino)methyl)phenyl)-3-(trifluoromethyl)-1H-pyrazole-5-carboxamido)-5-fluoro-3,4-dihydroisoquinoline-2(1H)-carboxylate (162b)

To a solution of 1-(3-((tert-butoxycarbonylamino)methyl)phenyl)-3-(trifluoromethyl)-1H-pyrazole-5-carboxylic acid (10d) (58.0 mg, 0.151 mmol) in DMF (1.4 mL) was added tert-butyl 6-amino-5-fluoro-3,4-dihydroisoquinoline-2(1H)-carboxylate (162a) (40 mg, 0.150 mmol) (prepared according to procedure reported in literature (a) Watson, Nigel S. et al; *Bioorganic & Medicinal Chemistry Letters*, 21(6), 1588-1592; 2011 (b) *Preparation of 3-sulfonylaminopyrrolidin-2-ones as factor Xa inhibitors*. Harling, John David et al; WO 2006/108709, 19 Oct. 2006), N-ethyl-N-isopropylpropan-2-amine (0.210 mL, 1.206 mmol) and bromotripyrrolidin-1-ylphosphonium hexafluorophosphate(V) (72.0 mg, 0.151 mmol) and stirred at room temperature for 14 h. The reaction mixture was diluted with ethyl acetate (75 mL), washed with water (2×30 mL), brine (30 mL), and dried over MgSO$_4$ followed by filtration and concentration. The crude product was purified by flash column chromatography [silica gel 4 g, eluting with hexanes/ethyl acetate (1:0 to 2:1)] to give tert-butyl 6-(1-(3-((tert-butoxycarbonylamino)methyl)phenyl)-3-(trifluoromethyl)-1H-pyrazole-5-carboxamido)-5-fluoro-3,4-dihydroisoquinoline-2(1H)-carboxylate (162b) (49 mg, 52%) as a colorless film; $^1$H NMR (300 MHz, CDCl$_3$) δ 7.95 (s, 1H), 7.87 (d, J=2.7 Hz, 1H), 7.53-7.33 (m, 5H), 7.16 (s, 1H), 6.86 (d, J=8.5 Hz, 1H), 4.53 (s, 2H), 4.37 (d, J=6.1 Hz, 2H), 3.63 (t, J=5.9 Hz, 2H), 2.77 (t, J=5.9 Hz, 2H), 1.48 (s, 9H), 1.43 (s, 9H); MS (ES+): 655.9 (M+23).

Step-2: Preparation of 1-(3-(aminomethyl)phenyl)-N-(5-fluoro-1,2,3,4-tetrahydroisoquinolin-6-yl)-3-(trifluoromethyl)-1H-pyrazole-5-carboxamide (162c)

To a solution of tert-butyl 6-(1-(3-((tert-butoxycarbonylamino)methyl)phenyl)-3-(trifluoromethyl)-1H-pyrazole-5-carboxamido)-5-fluoro-3,4-dihydroisoquinoline-2(1H)-carboxylate (162b) (48 mg, 0.076 mmol) in 1,4-Dioxane (5 mL) was added hydrogen chloride (1.100 mL, 4.40 mmol, 4 M in 1,4-dioxane) and stirred at room temperature for 17 h. The reaction mixture was treated with hexanes, filtered, washed with hexanes. The insoluble crude product was purified by flash column chromatography [silica gel 4 g, eluting with chloroform/CMA80 (1:0 to 1:1)] to give 1-(3-(aminomethyl)phenyl)-N-(5-fluoro-1,2,3,4-tetrahydroisoquinolin-6-yl)-3-(trifluoromethyl)-1H-pyrazole-5-carboxamide (27.5 mg, 84%) as a white solid; $^1$HNMR (300 MHz, Methanol-d4) δ 7.58-7.28 (m, 6H), 6.88 (d, J=8.3 Hz, 1H), 3.93-3.89 (m, 2H), 3.85 (s, 2H), 3.06 (t, J=6.1 Hz, 2H), 2.76 (t, J=6.1 Hz, 2H); $^{19}$FNMR (282 MHz, Methanol-d$_4$) δ −63.69, −130.74; MS (ES+): 434.08 (M+H).

Scheme 163

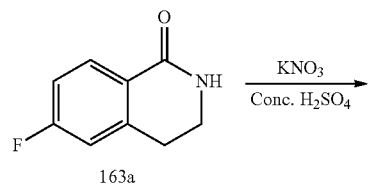

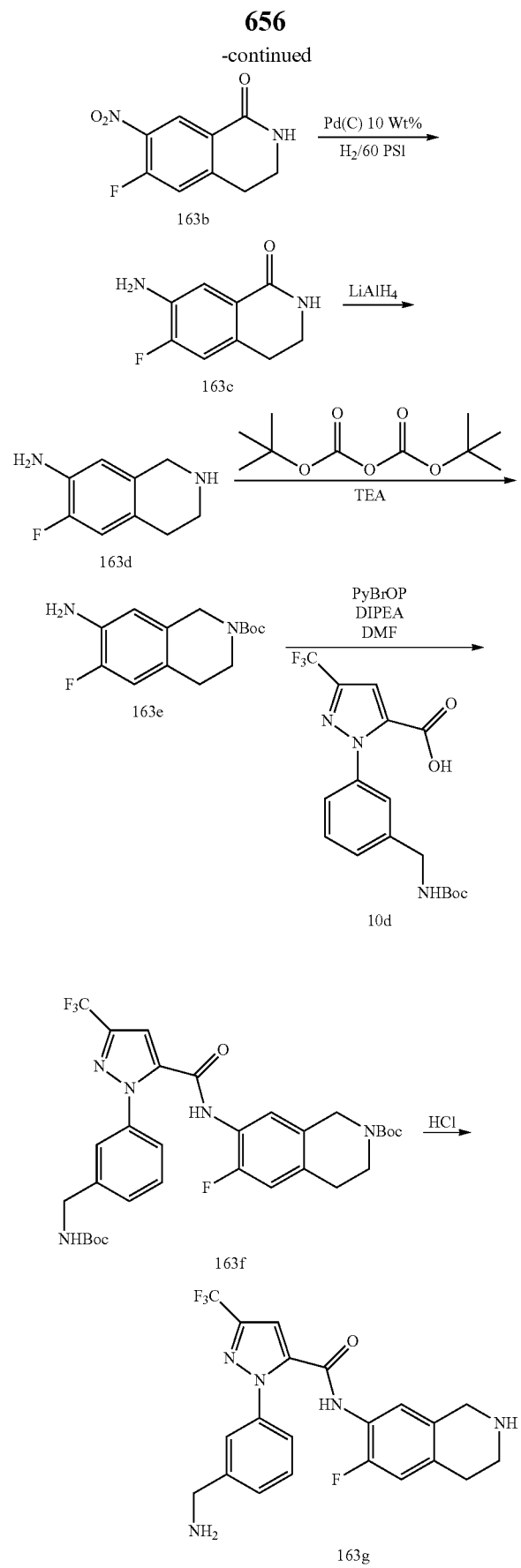

Preparation of 1-(3-(aminomethyl)phenyl)-N-(6-fluoro-1,2,3,4-tetrahydroisoquinolin-7-yl)-3-(trifluoromethyl)-1H-pyrazole-5-carboxamide (163g)

Step-1: Preparation of 6-fluoro-7-nitro-3,4-dihydroisoquinolin-1(2H)-one (163b)

A cold solution of potassium nitroperoxous acid (4.50 g, 44.5 mmol) in Conc. sulfuric acid (22 mL) was added 6-fluoro-3,4-dihydroisoquinolin-1(2H)-one (163a) (prepared according to the literature: Kurouchi, H.; Kawamoto, K.; Sugimoto, H.; Nakamura, S. Otani, Y.; Ohwada, T. *Journal of Organic Chemistry* (2012), 77(20), 9313-9328) (5.45 g, 33.0 mmol) was added drop-wise over a period of ten minutes. The reaction stirred for 17 h at room temperature, then solution was poured on to a mixture of 104 g ice and 120 mL water. The precipitate was collected by filtration, washed with cold water (300 mL) and dried under reduced pressure over P2O5 to afford 6-fluoro-7-nitro-3,4-dihydroisoquinolin-1(2H)-one (163b) (6.42 g, 93% yield) as a colorless solid; $^1$H NMR (300 MHz, DMSO-$d_6$) δ 8.47 (d, J=7.9 Hz, 1H), 8.33 (s, 1H), 7.64 (d, J=11.8 Hz, 1H), 3.43 (td, J=6.6, 2.9 Hz, 2H), 3.04 (t, J=6.6 Hz, 2H); $^{19}$F NMR (282 MHz, DMSO-$d_6$) δ −114.89; MS (ES$^+$): MS (ES+) 211.1 (M+1), 233.1 (M+Na), 443.3 (2M+Na), MS (ES−) 209.1 (M−1). Analysis calculated for $C_9H_7FN_2O_3$: C, 51.43; H, 3.36; N, 13.33; Found: C, 51.27; H, 3.27; N, 13.14.

Step-2: Preparation of 7-amino-6-fluoro-3,4-dihydroisoquinolin-1(2H)-one (163c)

To a solution of 6-fluoro-7-nitro-3,4-dihydroisoquinolin-1(2H)-one (163b) (1.86 g, 8.85 mmol) in methanol (20 mL) was added palladium on carbon (10%) (0.471 g, 4.43 mmol) and hydrogenated at 60 Psi for 3 h. The catalyst was removed by filtration through Celite and the filtrate was concentrated in vacuum. The residue was purified by flash column chromatography [silica gel 40 g, eluting with ethyl acetate/methanol (9:1) in hexanes from 0-100%] to furnish 7-amino-6-fluoro-3,4-dihydroisoquinolin-1(2H)-one (163c) (1.011 g, 63% yield) as a white solid; $^1$H NMR (300 MHz, DMSO-$d_6$) δ 7.84-7.65 (m, 1H), 7.30 (d, J=9.4 Hz, 1H), 6.94 (d, J=11.6 Hz, 1H), 5.17 (s, 2H, D$_2$O exchangeable), 3.33-3.26 (m, 2H), 2.71 (t, J=6.6 Hz, 2H); $^{19}$F NMR (282 MHz, DMSO-$d_6$) δ −130.21; MS (ES$^+$): MS (ES+) 181.2 (M+1), 360.08 (2M+1), 383.01 (2M+1).

Step-3: Preparation of 6-fluoro-1,2,3,4-tetrahydroisoquinolin-7-amine (163d)

A suspension of 7-amino-6-fluoro-3,4-dihydroisoquinolin-1(2H)-one (163c) (0.8 g, 4.44 mmol) in THF (30 mL) was treated with lithium aluminum hydride (22.20 mL, 22.20 mmol) (1 M in THF) at room temperature followed by reflux for 15 h. TLC analysis show reaction was incomplete, then cooled to room temperature, and added a additional lithium aluminum hydride (22.20 mL, 22.20 mmol) at room temperature followed by reflux for 16 h, cooled to room temperature and very carefully treated with aq. 20% Na$_2$SO$_4$ (30 mL) over a period of 10 min at 10-15° C. followed by dilution with CMA50 (150 mL), filtered through Celite, washed with CMA50 (50 mL), methanol (50 mL), filtrate was evaporated to dryness. The residue was purified by flash column chromatography (40 g silica gel, eluting with CMA80 in chloroform from 0-100%) to furnish 6-fluoro-1,2,3,4-tetrahydroisoquinolin-7-amine (163d) (0.557 g, 3.35 mmol, 75% yield) as a white solid, which used as such in next step; MS (ES$^+$): MS (ES+) 167.3 (M+1).

Step-4: tert-butyl 7-amino-6-fluoro-3,4-dihydroisoquinoline-2(1H)-carboxylate (163e)

A solution of 6-fluoro-1,2,3,4-tetrahydroisoquinolin-7-amine (163d) (532 mg, 3.20 mmol) in dichloromethane (20 mL) and MeOH (10 mL) was treated with di-tert-butyl dicarbonate (0.710 g, 3.22 mmol) and triethylamine (TEA; 0.892 mL, 6.40 mmol) drop-wise followed by stirring at room temperature for 12 h. Excess solvent was pumped-off, extracted with chloroform (2×75 mL), washed with water (50 mL), dried over MgSO$_4$ followed by filtration and concentration. The crude residue and was purified by flash column chromatography (25 g silica gel, ethyl acetate in hexanes from 0-100%) to furnish tert-butyl 7-amino-6-fluoro-3,4-dihydroisoquinoline-2(1H)-carboxylate (163e) (0.289 g, 1.085 mmol, 33.9% yield) as a white solid; $^1$H NMR (300 MHz, DMSO-$d_6$) δ 6.77 (d, J=12.0 Hz, 1H), 6.50 (d, J=9.0 Hz, 1H), 4.96 (s, 2H, D$_2$O exchangeable), 4.31 (s, 2H), 3.47 (t, J=5.9 Hz, 2H), 2.59 (t, J=5.9 Hz, 2H), 1.41 (s, 9H); $^{19}$F NMR (282 MHz, DMSO-$d_6$) δ −137.46; Analysis calculated for $C_{14}H_{19}FN_2O_2$: C, 63.14; H, 7.19; N, 10.52; Found: C, 63.13; H, 7.23; N, 10.47.

Step-5: Preparation of tert-butyl 7-(1-(3-((tert-butoxycarbonylamino)methyl)phenyl)-3-(trifluoromethyl)-1H-pyrazole-5-carboxamido)-6-fluoro-3,4-dihydroisoquinoline-2(1H)-carboxylate (163f)

To a solution of 1-(3-((tert-butoxycarbonylamino)methyl)phenyl)-3-(trifluoromethyl)-1H-pyrazole-5-carboxylic acid (10d) (150 mg, 0.389 mmol) in N,N-dimethylformamide (2.5 mL) was added tert-butyl 7-amino-6-fluoro-3,4-dihydroisoquinoline-2(1H)-carboxylate (163e) (104 mg, 0.389 mmol), N-ethyl-N-isopropylpropan-2-amine (0.542 mL, 3.11 mmol) and bromo-tris-pyrrolidino phosphonium-hexafluorophosphate (PyBroP) (0.218 g, 0.467 mmol) at room temperature. The resulting reaction mixture was stirred at 25° C. for 16 h. Excess DMF was completely removed under reduced pressure, reaction mixture was diluted with water (30 mL), and extracted with ethyl acetate (50 mL, 25 mL). The organic layers were combined dried over anhydrous MgSO$_4$, filtered, and concentrated in vacuum to dryness. The residue was purified by flash column chromatography (silica gel 25 g, eluting with hexanes in ethyl acetate/hexanes from 0-100%) to furnish product tert-butyl 7-(1-(3-((tert-butoxycarbonylamino)methyl)phenyl)-3-(trifluoromethyl)-1H-pyrazole-5-carboxamido)-6-fluoro-3,4-dihydroisoquinoline-2(1H)-carboxylate (163f) (116 mg, 47% yield) as a white solid; $^1$H NMR (300 MHz, DMSO-$d_6$) δ 10.56 (s, 1H), 7.58 (s, 1H), 7.42 (m, 6H), 7.12 (d, J=11.0 Hz, 1H), 4.45 (s, 2H), 4.19 (s, 2H), 3.52 (t, J=5.9 Hz, 2H), 2.75 (t, J=6.0 Hz, 2H), 1.42 (s, 9H), 1.37 (s, 9H); MS (ES$^+$): MS (ES+) 656.0 (M+Na), (ES−) 631.7 (M−1); Analysis calculated for $C_{31}H_{35}F_4N_5O_5$: C, 58.76; H, 5.57; N, 11.05; Found: C, 58.65; H, 5.65; N, 10.75.

Step-6: Preparation of 1-(3-(aminomethyl)phenyl)-N-(6-fluoro-1,2,3,4-tetrahydroisoquinolin-7-yl)-3-(trifluoromethyl)-1H-pyrazole-5-carboxamide (163g)

To a solution of tert-butyl 7-(1-(3-((tert-butoxycarbonylamino)methyl)phenyl)-3-(trifluoromethyl)-1H-pyrazole-5-carboxamido)-6-fluoro-3,4-dihydroisoquinoline-2(1H)- carboxylate (163f) (95 mg, 0.150 mmol) in dioxane (4 mL) was added hydrogen chloride (4M in dioxane) (2.099 mL, 8.40 mmol) and stirred at room temperature for 14 h. The reaction mixture was diluted with hexanes, filtered, dried under vacuum to furnish 1-(3-(aminomethyl)phenyl)-N-(6-fluoro-1,2,3,4-tetrahydroisoquinolin-7-yl)-3-(trifluoromethyl)-1H-pyrazole-5-carboxamide (163g) (46 mg, 71% yield) as a pale yellow solid; $^1$H NMR (300 MHz, DMSO-$d_6$) δ 10.75 (s, 1H, $D_2O$ exchangeable), 9.61 (s, 2H, $D_2O$ exchangeable), 8.48 (s, 2H, $D_2O$ exchangeable), 7.72 (s, 2H), 7.67-7.43 (m, 4H), 7.21 (d, J=11.0 Hz, 1H), 4.20 (s, 2H), 4.16-4.07 (m, 2H), 3.33 (d, J=6.0 Hz, 2H), 3.00 (d, J=6.3 Hz, 2H); $^1$H NMR (300 MHz, DMSO-$d_6$-$D_2O$) δ 7.71 (s, 1H), 7.67 (s, 1H), 7.64-7.44 (m, 4H), 7.23 (d, J=11.0 Hz, 1H), 4.22 (s, 2H), 4.12 (s, 2H), 3.36 (t, J=6.1 Hz, 2H), 3.00 (t, J=6.3 Hz, 2H); $^{19}$F NMR (282 MHz, DMSO-$d_6$) δ −60.81, −123.09; MS (ES$^+$): MS (ES+) 434.0 (M+1), (ES−) 431.7 (M−1); Analysis calculated for $C_{21}H_{19}F_4N_5O \cdot 2HCl \cdot 1.25H_2O$: C, 47.69; H, 4.48; Cl, 13.41; N, 13.24; Found: C, 47.39; H, 4.23; Cl, 13.78; N, 13.84.

Scheme 164

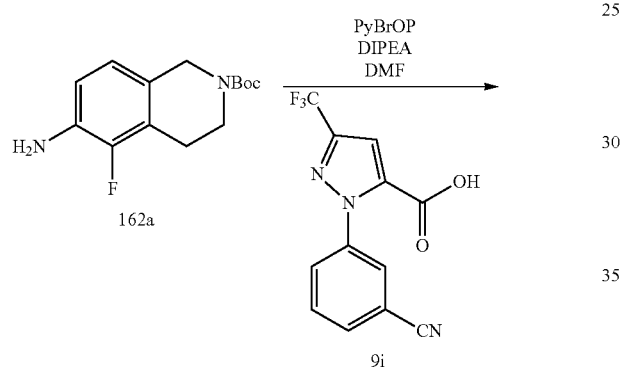

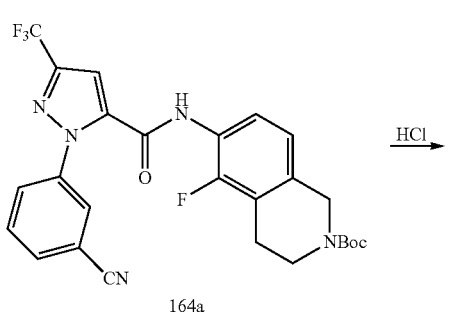

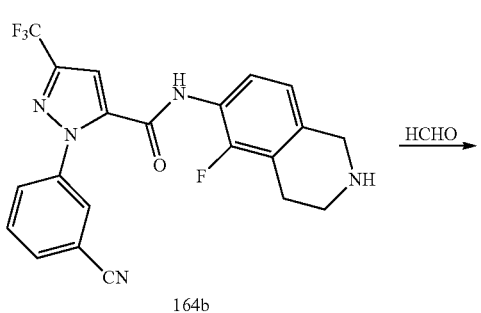

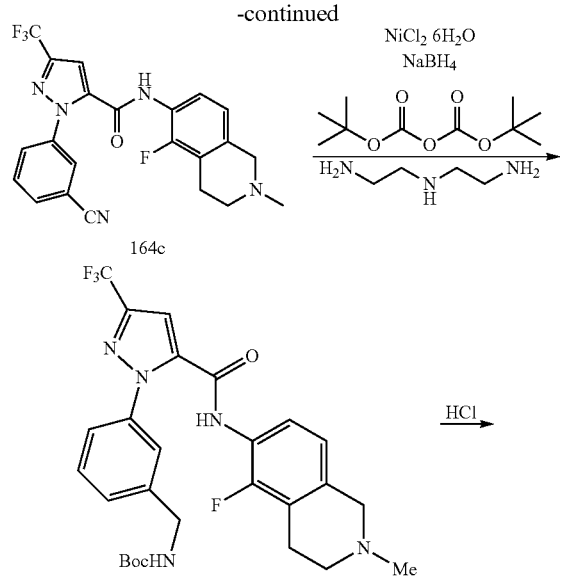

Preparation of 1-(3-(aminomethyl)phenyl)-N-(5-fluoro-2-methyl-1,2,3,4-tetrahydroisoquinolin-6-yl)-3-(trifluoromethyl)-1H-pyrazole-5-carboxamide (164e)

Step-1: Preparation of tert-butyl 6-(1-(3-cyanophenyl)-3-(trifluoromethyl)-1H-pyrazole-5-carboxamido)-5-fluoro-3,4-dihydroisoquinoline-2(1H)-carboxylate (164a)

A solution of 1-(3-cyanophenyl)-3-(trifluoromethyl)-1H-pyrazole-5-carboxylic acid (9i) (180 mg, 0.640 mmol) in DMF (6 mL) was treated with tert-butyl 6-amino-5-fluoro-3,4-dihydroisoquinoline-2(1H)-carboxylate (162a) (170 mg, 0.638 mmol), N-ethyl-N-isopropylpropan-2-amine (0.890 mL, 5.11 mmol) and bromotripyrrolidin-1-ylphosphonium hexafluorophosphate(V) (PyBrOP, 306 mg, 0.643 mmol) followed by stirring at RT for 15 h. The reaction mixture was diluted with ethyl acetate (150 mL), washed with water (2×75 mL) and brine (75 mL), and dried over MgSO$_4$ followed by filtration and concentration. The crude product was purified by flash column chromatography [silica gel 4 g, eluting with hexanes/ethyl acetate (1:0 to 2:1)] to give tert-butyl 6-(1-(3-cyanophenyl)-3-(trifluoromethyl)-1H-pyrazole-5-carboxamido)-5-fluoro-3,4-dihydroisoquinoline-2(1H)-carboxylate (164a) (166 mg, 49%) as a yellow solid. $^1$H NMR (300 MHz, DMSO-$d_6$) δ 10.55 (s, 1H), 8.16-8.10 (m, 1H), 8.02-7.98 (m, 1H), 7.90 (ddd, J=8.1, 2.1, 1.1 Hz, 1H), 7.76-7.70 (m, 2H), 7.35 (t, J=7.9 Hz, 1H), 7.04 (d, J=8.3 Hz, 1H), 4.51 (s, 2H), 3.58 (t, J=5.9 Hz, 2H), 2.73 (t, J=5.8 Hz, 2H), 1.42 (s, 9H); MS (ES+): 552.2 (M+23).

Step-2: Preparation of 1-(3-cyanophenyl)-N-(5-fluoro-1,2,3,4-tetrahydroisoquinolin-6-yl)-3-(trifluoromethyl)-1H-pyrazole-5-carboxamide (164b)

A solution of tert-butyl 6-(1-(3-cyanophenyl)-3-(trifluoromethyl)-1H-pyrazole-5-carboxamido)-5-fluoro-3,4-dihydroisoquinoline-2(1H)-carboxylate (164a) (100 mg, 0.189 mmol) in 1,4-Dioxane (10 mL) was treated with hydrogen chloride (2.0 mL, 8.00 mmol, 4 M in 1,4-dioxane) and stirred at RT for 17 h. The reaction mixture was treated with hexanes, decanted, washed with hexanes, and decanted again. The insoluble crude product was purified by flash column chromatography [silica gel, eluting with chloroform/CMA 80 (1:0 to 2:1)] to give 1-(3-cyanophenyl)-N-(5-fluoro-1,2,3,4-tetrahydroisoquinolin-6-yl)-3-(trifluoromethyl)-1H-pyrazole-5-carboxamide (164b) (74 mg, 91%) as a white solid; $^1$H NMR (300 MHz, DMSO-$d_6$) δ 10.48 (s, 1H), 8.14-8.10 (m, 1H), 8.00 (dt, J=7.7, 1.3 Hz, 1H), 7.93-7.87 (m, 1H), 7.80-7.67 (m, 2H), 7.26 (t, J=8.0 Hz, 1H), 6.88 (d, J=8.2 Hz, 1H), 3.82 (s, 2H), 2.94 (t, J=5.9 Hz, 2H), 2.60 (t, J=6.9 Hz, 2H); $^{19}$F NMR (282 MHz, DMSO-$d_6$) δ −60.97, −127.51; MS (ES+): 430.2 (M+1).

Step-3: Preparation of 1-(3-cyanophenyl)-N-(5-fluoro-2-methyl-1,2,3,4-tetrahydroisoquinolin-6-yl)-3-(trifluoromethyl)-1H-pyrazole-5-carboxamide (164c)

A solution of 1-(3-cyanophenyl)-N-(5-fluoro-1,2,3,4-tetrahydroisoquinolin-6-yl)-3-(trifluoromethyl)-1H-pyrazole-5-carboxamide (164b) (35 mg, 0.082 mmol) in formic acid (0.3 mL) was treated with formaldehyde (7.00 μL, 0.094 mmol) followed by stirring at 70° C. for 6 h. The reaction mixture was concentrated to dryness. The residue was treated with ethanol followed by concentration again (this process was repeated two more times). The crude product was purified by flash column chromatography [silica gel, eluting with chloroform/CMA 80 (1:0 to 4:1)] to give 1-(3-cyanophenyl)-N-(5-fluoro-2-methyl-1,2,3,4-tetrahydroisoquinolin-6-yl)-3-(trifluoromethyl)-1H-pyrazole-5-carboxamide (164c) (34 mg, 94%) as a light yellow gum; $^1$H NMR (300 MHz, DMSO-$d_6$) δ 10.50 (s, 1H), 8.16-7.68 (m, 5H), 7.29 (t, J=7.9 Hz, 1H), 6.92 (d, J=8.2 Hz, 1H), 3.49 (s, 2H), 2.75 (t, 2H), 2.62 (t, 2H), 2.35 (s, 3H); $^{19}$F NMR (282 MHz, DMSO-$d_6$) δ −60.98, −126.90; MS (ES+): 444.2 (M+1).

Step-4: Preparation of tert-butyl 3-(5-(5-fluoro-2-methyl-1,2,3,4-tetrahydroisoquinolin-6-ylcarbamoyl)-3-(trifluoromethyl)-1H-pyrazol-1-yl)benzylcarbamate (164d)

To a solution of 1-(3-cyanophenyl)-N-(5-fluoro-2-methyl-1,2,3,4-tetrahydroisoquinolin-6-yl)-3-(trifluoromethyl)-1H-pyrazole-5-carboxamide (164c) (30 mg, 0.068 mmol) in MeOH (2 mL) cooled with ice/water was added di-tert-butyl dicarbonate (45.0 mg, 0.204 mmol), nickel(II) chloride hexahydrate (4.0 mg, 0.017 mmol) followed by portionwise addition of sodium borohydride (16.00 mg, 0.414 mmol) and stirred at RT for 1 h. The reaction mixture was treated N1-(2-aminoethyl)ethane-1,2-diamine (0.015 mL, 0.140 mmol) followed by stirring at RT for 0.5 h and concentration to dryness. The residue was treated with chloroform (120 mL), washed with water (60 mL). The aqueous phase was extracted again with chloroform (60 mL). The combined extracts were dried over MgSO$_4$ followed by filtration and concentration. The crude product was purified by flash column chromatography [silica gel, eluting with chloroform/methanol (1:0 to 19:1)] to give tert-butyl 3-(5-(5-fluoro-2-methyl-1,2,3,4-tetrahydroisoquinolin-6-ylcarbamoyl)-3-(trifluoromethyl)-1H-pyrazol-1-yl)benzylcarbamate (164d) (13 mg, 35%) as a colorless foam; $^1$H NMR (300 MHz, Methanol-$d_4$) δ 7.55-7.28 (m, 6H), 6.95-6.86 (m, 1H), 4.29 (s, 2H), 3.59 (s, 2H), 2.89 (dt, J=7.1, 3.6 Hz, 2H), 2.74 (t, J=5.8 Hz, 2H), 2.45 (s, 3H), 1.42 (s, 9H); $^{19}$F NMR (282 MHz, Methanol-$d_4$) δ −63.71, −130.50; MS (ES+): 548.3 (M+1).

Step-5: Preparation of 1-(3-(aminomethyl)phenyl)-N-(5-fluoro-2-methyl-1,2,3,4-tetrahydroisoquinolin-6-yl)-3-(trifluoromethyl)-1H-pyrazole-5-carboxamide (164e)

A solution of tert-butyl 3-(5-(5-fluoro-2-methyl-1,2,3,4-tetrahydroisoquinolin-6-ylcarbamoyl)-3-(trifluoromethyl)-1H-pyrazol-1-yl)benzylcarbamate (164d) (13 mg, 0.024 mmol) in 1,4-Dioxane (2 mL) was treated with hydrogen chloride (0.250 mL, 1.002 mmol, 4 M in 1,4-dioxane) followed by stirring at RT for 14 h. The reaction mixture was treated with hexanes, decanted, washed with hexanes, and decanted again. The insoluble crude product was purified by flash column chromatography [silica gel 4 g, eluting with chloroform/CMA 80 (1:0 to 1:2)] to give (3.9 mg, 37%) as a light yellow gum; $^1$H NMR (300 MHz, Methanol-$d_4$) δ 7.55-7.28 (m, 6H), 6.95-6.86 (m, 1H), 4.29 (s, 2H), 3.59 (s, 2H), 2.89 (dt, J=7.1, 3.6 Hz, 2H), 2.74 (t, J=5.8 Hz, 2H), 2.45 (s, 3H), 1.42 (s, 9H); $^{19}$F NMR (282 MHz, Methanol-$d_4$) δ −63.71, −130.50; MS (ES+): 448.09 (M+1).

Scheme 165

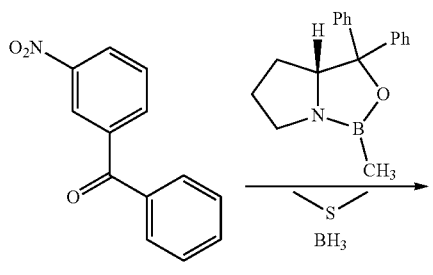

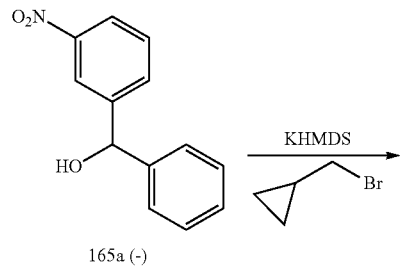

-continued

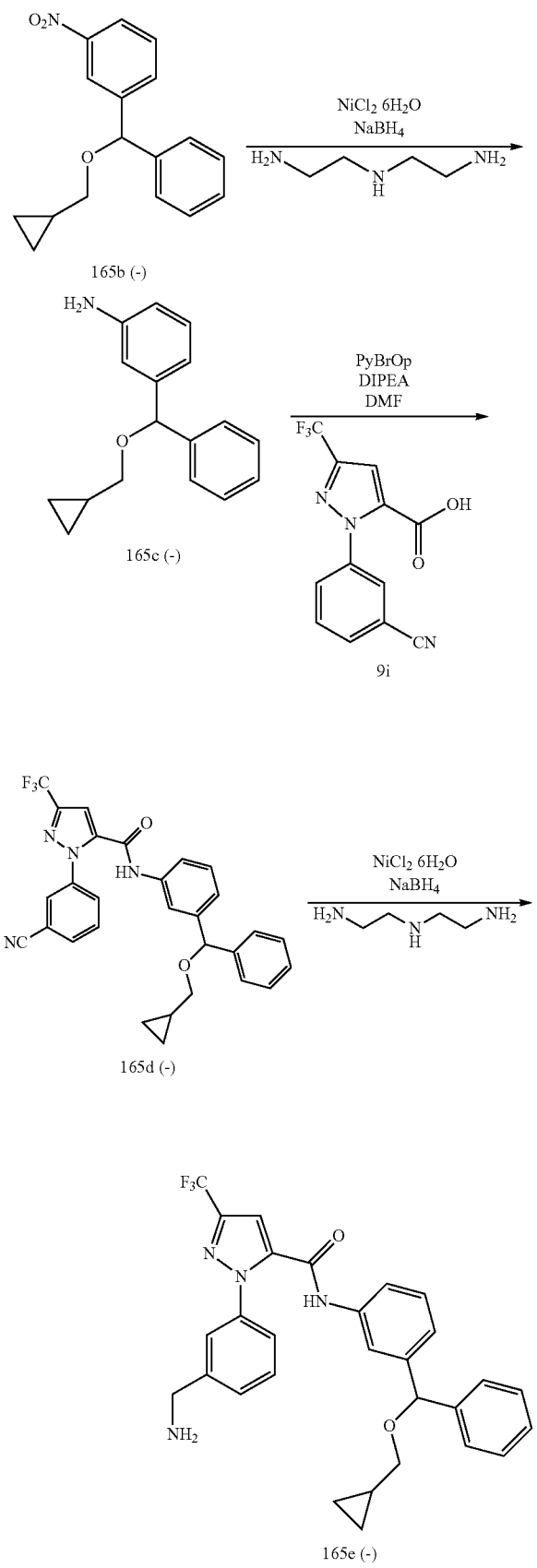

Preparation of (−)-1-(3-(aminomethyl)phenyl)-N-(3-((cyclopropylmethoxy)(phenyl)methyl)phenyl)-3-(trifluoromethyl)-1H-pyrazole-5-carboxamide (165e)

Step-1: Preparation of (−)-(3-nitrophenyl)(phenyl)methanol (165a)

To a cold [(−40° C. (acetonitrile/dry ice)] stirred solution of (3-nitrophenyl)(phenyl)methanone (18a) (4 g, 17.60 mmol) in THF (150 mL) was added (R)-1-methyl-3,3-diphenylhexahydropyrrolo[1,2-c][1,3,2]oxazaborole (4.40 mL, 4.40 mmol) drop-wise and stirred at room temperature for 1 h in a positive flow of nitrogen then borane-methyl sulfide complex (17.60 mL, 35.2 mmol) was added slowly in a positive flow of nitrogen over a period of 1 h. The reaction was stirred at −40° C. for 2 h. TLC analysis shows reaction was complete. Reaction mixture was carefully quenched with 60 mL methanol at −40° C. and stirred for 12 h at room temperature, and then the reaction mixture was treated with silica gel, prepared the slurry under reduced pressure. The residue was purified by flash column chromatography [(silica gel 120 g, eluting with ethyl acetate/hexanes from 0 to 50%)] to furnish (−)-(3-nitrophenyl)(phenyl)methanol (165a) (3.808 g, 94% yield) as a pale yellow solid; $^1$H NMR (300 MHz, DMSO-$d_6$) δ 8.25 (t, J=2.0 Hz, 1H), 8.09 (ddd, J=8.2, 2.5, 1.1 Hz, 1H), 7.86-7.78 (m, 1H), 7.61 (t, J=7.9 Hz, 1H), 7.45-7.39 (m, 2H), 7.37-7.29 (m, 2H), 7.28-7.20 (m, 1H), 6.25 (d, J=4.1 Hz, 1H), 5.88 (d, J=4.1 Hz, 1H); MS (ES−) 457.3 (2M−1); Optical rotation: $[α]_D$=(−) 40.65 [CHCl$_3$, 1.23].

Lit: For absolute stereochemistry, see, Truppo, M.; Morley, K.; Pollard, D.; Devine, P.; Edited by Whittall, J.; Sutton, P.; *Practical Methods for Biocatalysis and Biotransformations* (2010), 288-290.

Step-2: Preparation of (−)-1-((cyclopropylmethoxy)(phenyl)methyl)-3-nitrobenzene (165b)

To a stirred solution of (−)-(3-nitrophenyl)(phenyl)methanol (165a) (3.8 g, 16.58 mmol) in THF (60 mL) at 0° C. was added KHMDS (0.5M in toluene) (39.8 mL, 19.89 mmol) (bromomethyl)cyclopropane (6.43 mL, 66.3 mmol) and stirred at 0° C. for 3 h in a positive flow of nitrogen. TLC analysis (ethyl acetate/hexanes, 2/8, v/v) shows complete conversion. The reaction was carefully quenched with sat. NH$_4$Cl (100 mL), and extracted with ethyl acetate (2×100 mL), combined organics were dried over anhydrous MgSO$_4$, filtered, evaporated to dryness. The residue was purified by flash column chromatography [(silica gel 40 g, eluting with ethyl acetate/hexanes from 0 to 50%)] to furnish (−)-1-((cyclopropylmethoxy)(phenyl)methyl)-3-nitrobenzene (165b) (0.224 g, 5% yield) as a clear oil; $^1$H NMR (300 MHz, DMSO-$d_6$) δ 8.17 (t, J=2.0 Hz, 1H), 8.05 (ddd, J=8.2, 2.4, 1.1 Hz, 1H), 7.76 (dt, J=7.7, 1.3 Hz, 1H), 7.57 (t, J=7.9 Hz, 1H), 7.40-7.17 (m, 5H), 5.63 (s, 1H), 3.21 (d, J=6.8 Hz, 2H), 1.02 (dddd, J=10.0, 6.7, 4.0, 1.6 Hz, 1H), 0.41 (ddd, J=8.0, 3.9, 2.0 Hz, 2H), 0.10 (ddd, J=6.0, 4.7, 3.2 Hz, 2H); Optical rotation: $[α]_D$=(−) 28.57 [CHCl$_3$, 1.905].

Step-3: Preparation of (−)-3-((cyclopropylmethoxy)(phenyl)methyl)aniline (165c)

To a stirred solution of (−)-1-((cyclopropylmethoxy)(phenyl)methyl)-3-nitrobenzene (165b) (0.211 g, 0.745 mmol) in anhydrous methanol (30 mL), cooled to 0° C., was added nickel(II) chloride hexahydrate (0.089 g, 0.372 mmol) followed by sodium borohydride (0.169 g, 4.47 mmol) in small portions over a period of 5 min. The reaction mixture was stirred for 15 min at 0° C. TLC analysis (ethyl acetate/hexanes, 2/8, v/v) shows reaction was complete at this point N1-(2-aminoethyl)ethane-1,2-diamine (0.805 mL, 7.45 mmol) was added. The mixture was allowed to stir for 30 minutes more before solvent evaporated. The residue was treated sat NH$_4$Cl (25 mL), and extracted with ethyl acetate (2×25 mL). Organic layer was dried over anhydrous MgSO$_4$, filtered, and excess solvents were pumped-off under reduced pressure. The residue was purified by flash column chromatography [(silica gel 25 g, eluting with ethyl acetate/hexanes from 0 to 50%)] to furnish (−)-3-((cyclopropylmethoxy)(phenyl)methyl)aniline (165c) (0.141 g, 75% yield) as a yellow solid; $^1$H NMR (300 MHz, DMSO-d$_6$) δ 7.23-7.12 (m, 4H), 7.09-7.00 (m, 1H), 6.78 (t, J=7.7 Hz, 1H), 6.42 (t, J=1.9 Hz, 1H), 6.34 (dt, J=7.5, 1.3 Hz, 1H), 6.25 (ddd, J=8.0, 2.3, 1.1 Hz, 1H), 5.10 (s, 1H), 4.90 (s, 2H, D$_2$O exchangeable), 3.14-2.98 (m, 2H), 1.01-0.80 (m, 1H), 0.40-0.25 (m, 2H), 0.06--0.07 (m, 2H); MS (ES+) 254.2 (M+1), 276.2 (M+Na); Optical rotation: [α]$_D$=(−) 5.68 [CHCl$_3$, 1.055].

Step-4: Preparation of (−)-1-(3-cyanophenyl)-N-(3-((cyclopropylmethoxy)(phenyl)methyl)phenyl)-3-(trifluoromethyl)-1H-pyrazole-5-carboxamide (165d)

A single-necked 100 mL flask was charged with 1-(3-cyanophenyl)-3-(trifluoromethyl)-1H-pyrazole-5-carboxylic acid (9i) (0.210 g, 0.746 mmol), (−)-3-((cyclopropylmethoxy)(phenyl)methyl)aniline (165c) (0.126 g, 0.497 mmol), bromo-tris-pyrrolidino phosphoniumhexafluorophosphate(PyBrOP, 0.278 g, 0.597 mmol) was added N,N-dimethylformamide (6 mL) and N-ethyl-N-isopropylpropan-2-amine (0.433 mL, 2.487 mmol) successively in a positive flow of nitrogen at room temperature. The resulting reaction mixture was stirred at room temperature for 12 h under a positive flow of nitrogen atmosphere. Excess DMF was pumped-off under reduced pressure. The residue was treated with sat. NH$_4$Cl solution (30 mL), and extracted with ethyl acetate (2×50 mL) combined organics were dried over anhydrous MgSO$_4$, filtered, evaporated to dryness. The residue was then purified by flash column chromatography [silica gel 40 g, eluting with ethyl acetate in hexanes from 0-100%] to furnish (−)-1-(3-cyanophenyl)-N-(3-((cyclopropylmethoxy)(phenyl)methyl)phenyl)-3-(trifluoromethyl)-1H-pyrazole-5-carboxamide (165d) (0.234 g, 91% yield) as a colorless waxy solid; $^1$H NMR (300 MHz, DMSO-d$_6$) δ 10.68 (s, 1H, D$_2$O exchangeable), 8.17 (t, J=1.8 Hz, 1H), 8.00 (dt, J=7.7, 1.3 Hz, 1H), 7.91 (ddd, J=8.2, 2.2, 1.1 Hz, 1H), 7.79-7.69 (m, 2H), 7.67-7.56 (m, 2H), 7.40-7.19 (m, 6H), 7.14 (dt, J=7.6, 1.3 Hz, 1H), 5.45 (s, 1H), 3.24 (d, J=6.7 Hz, 2H), 1.06 (m, 1H), 0.55-0.38 (m, 2H), 0.15 (m, 2H); $^{19}$F NMR (282 MHz, DMSO-d$_6$) δ −60.97; MS (ES$^+$): MS (ES+) 517.3 (M+1), 539.2 (M+Cl), MS (ES−) 515.2 (M−1); Optical rotation: Optical rotation: [α]$_D$=(−) 1.24 [CHCl$_3$, 1.285].

Step-5: Preparation of (−)-1-(3-(aminomethyl)phenyl)-N-(3-((cyclopropylmethoxy)(phenyl)methyl)phenyl)-3-(trifluoromethyl)-1H-pyrazole-5-carboxamide (165e)

To a stirred solution of (−)-1-(3-cyanophenyl)-N-(3-((cyclopropylmethoxy)(phenyl)methyl)phenyl)-3-(trifluoromethyl)-1H-pyrazole-5-carboxamide (165d) (0.183 g, 0.354 mmol) in anhydrous methanol (30 mL) cooled to 0° C., was added nickel(II) chloride hexahydrate (0.105 g, 0.443 mmol) followed by sodium borohydride (0.107 g, 2.83 mmol) in small portions over a period of 5 min. The reaction mixture was stirred for 10 min, TLC analysis (methanol/chloroform, 1/9, v/v) shows reaction was complete at this point N1-(2-aminoethyl)ethane-1,2-diamine (0.383 mL, 3.54 mmol) was added. Excess methanol was pumped-off under reduced pressure. The reaction mixture was treated with sat. NH$_4$Cl (30 mL), and product was extracted with chloroform (2×30 mL), combined organic layer was dried over MgSO$_4$, filtered, evaporated to dryness. The residue was purified by flash column chromatography [(silica gel 40 g, eluting with methanol/chloroform from 0 to 50%)] to furnish (−)-1-(3-(aminomethyl)phenyl)-N-(3-((cyclopropylmethoxy)(phenyl)methyl)phenyl)-3-(trifluoromethyl)-1H-pyrazole-5-carboxamide (165e) (122 mg, 66% yield) as a white solid; $^1$H NMR (300 MHz, DMSO-d$_6$) δ 10.72 (s, 1H, D$_2$O exchangeable), 7.63 (t, J=1.9 Hz, 1H), 7.60-7.50 (m, 3H), 7.47-7.39 (m, 2H), 7.37-7.20 (m, 7H), 7.13 (dt, J=7.6, 1.3 Hz, 1H), 5.44 (s, 1H), 3.79 (s, 2H), 3.23 (dd, J=6.7, 1.4 Hz, 2H), 2.73 (s, 2H, D$_2$O exchangeable), 1.15-0.97 (m, 1H), 0.46 (ddd, J=8.5, 3.2, 2.1 Hz, 2H), 0.15 (dt, J=4.2, 3.1 Hz, 2H); $^{19}$F NMR (282 MHz, DMSO-d$_6$) δ −60.72; MS (ES$^+$): MS (ES+) 521.3 (M+1), MS (ES−) 519.3 (M−1); Chiral HPLC: 59.69% ee determined by HPLC with a Chiralpak AD-H column (isopropanol/hexanes=80:20, 0.8 mL/min, eluting with 0.1% triethyl amine, uv 250 nM): Rt=6.58 min (minor), Rt=5.90 min (major); Optical rotation: [α]$_D$=(−) 2.64 [CHCl$_3$, 1.06]; Analysis calculated for C$_{29}$H$_{27}$F$_3$N$_4$O$_2$.0.5H$_2$O: C, 65.77; H, 5.33; N, 10.58; Found: C, 65.81; H, 5.30; N, 10.70.

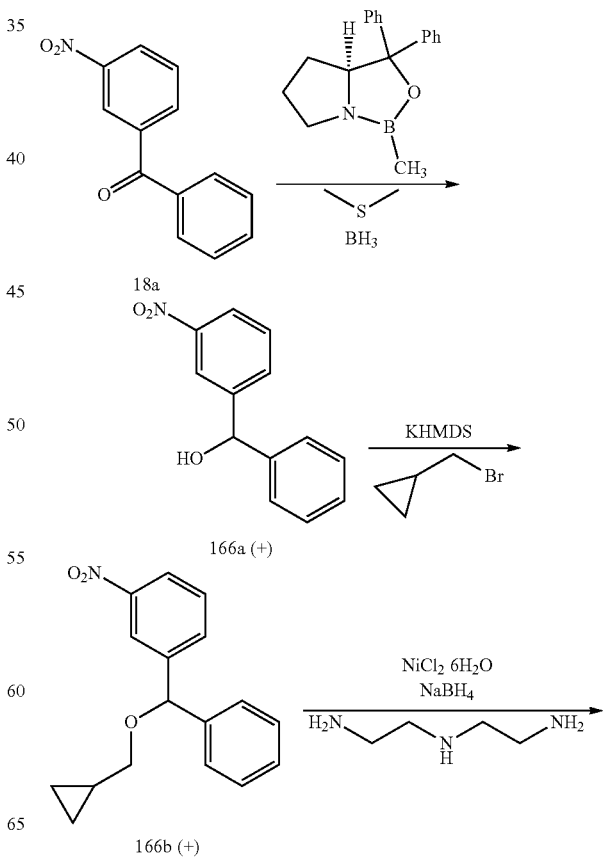

Scheme 166

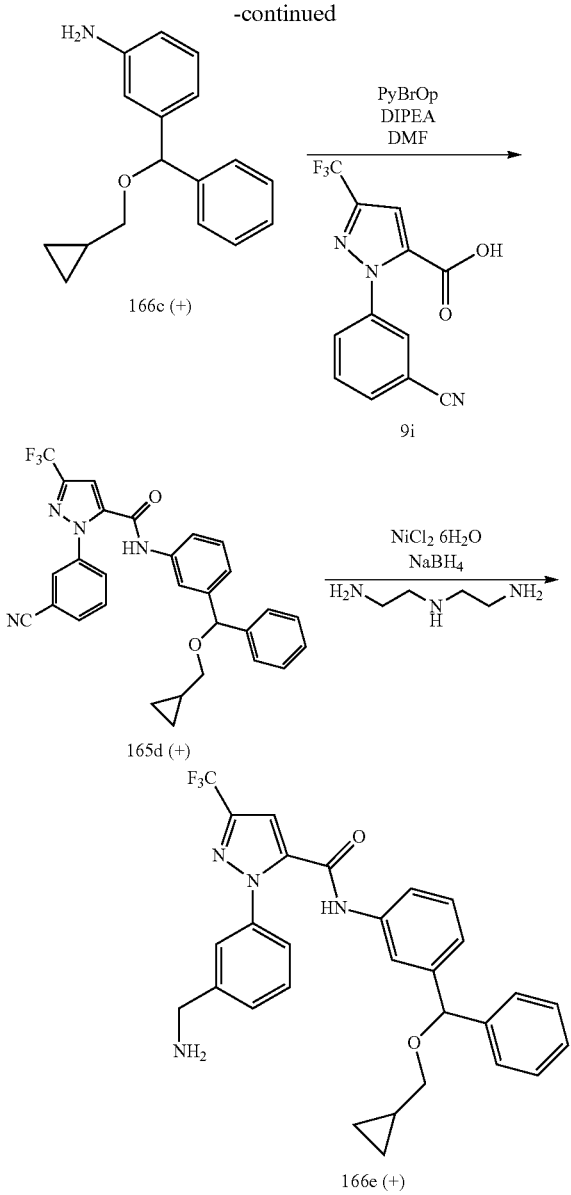

Preparation of (+)-1-(3-(aminomethyl)phenyl)-N-(3-((cyclopropylmethoxy)(phenyl)methyl)phenyl)-3-(trifluoromethyl)-1H-pyrazole-5-carboxamide (166e)

Step-1: Preparation of (+)-(3-nitrophenyl)(phenyl)methanol (166a)

To a stirred solution of (3-nitrophenyl)(phenyl)methanone (18a) (3.95 g, 17.38 mmol) in THF (60 mL) cooled to −40° C. (acetonitrile/dry ice) under a positive flow of nitrogen was added (S)-1-methyl-3,3-diphenylhexahydropyrrolo[1,2-c][1,3,2]oxazaborole (4.35 mL, 4.35 mmol) and stirred for 1 h, then borane-methyl sulfide complex (17.38 mL, 34.8 mmol) was added slowly under a positive flow of nitrogen. The reaction was stirred at −40° C. for 3 h. TLC analysis shows reaction was complete. Reaction mixture was carefully quenched with 60 mL of methanol at 0° C. and stirred for 12 h at room temperature, and then the reaction mixture was treated with silica gel, prepared the slurry under reduced pressure. The residue was purified by flash column chromatography [(silica gel 120 g, eluting with ethyl acetate/hexanes from 0 to 50%)] to furnish (+)-(3-nitrophenyl)(phenyl)methanol (166a) (3.73 g, 94% yield) as a yellow oil; $^1$H NMR (300 MHz, DMSO-$d_6$) δ 8.25 (t, J=2.0 Hz, 1H), 8.08 (ddd, J=8.2, 2.4, 1.1 Hz, 1H), 7.82 (ddt, J=7.7, 1.6, 0.8 Hz, 1H), 7.61 (t, J=7.9 Hz, 1H), 7.46-7.39 (m, 2H), 7.37-7.29 (m, 2H), 7.28-7.20 (m, 1H), 6.25 (d, J=4.1 Hz, 1H, $D_2O$ exchangeable), 5.88 (d, J=4.1 Hz, 1H); Optical rotation: $[α]_D$=(+) 45.97 [$CHCl_3$, 1.34].

Step-2: Preparation of (+)-1-((cyclopropylmethoxy)(phenyl)methyl)-3-nitrobenzene (166b)

To a stirred solution of (+)-(3-nitrophenyl)(phenyl)methanol (166a) (1.885 g, 8.22 mmol) in THF (60 mL) at 0° C. was added KHMDS (0.5M in toluene) (19.74 mL, 9.87 mmol), (bromomethyl)cyclopropane (3.19 mL, 32.9 mmol) and stirred at 0° C. for 3h under a positive flow of nitrogen. TLC analysis (ethyl acetate/hexanes, 2/8, v/v) shows complete conversion. The reaction was carefully quenched with sat. $NH_4Cl$ (60 mL), and extracted with ethyl acetate (2×60 mL), combined organics were dried over anhydrous $MgSO_4$, filtered, evaporated to dryness. The residue was purified by flash column chromatography [(silica gel 40 g, eluting with ethyl acetate/hexanes from 0 to 50%)] to furnish (+)-1-((cyclopropylmethoxy)(phenyl)methyl)-3-nitrobenzene (166b) (137 mg, 6% yield) as a clear oil; $^1$H NMR (300 MHz, Chloroform-d) δ 8.27 (t, J=1.9 Hz, 1H), 8.10 (ddd, J=8.2, 2.4, 1.1 Hz, 1H), 7.68 (ddt, J=7.8, 1.6, 0.8 Hz, 1H), 7.48 (t, J=7.9 Hz, 1H), 7.36 (d, J=4.3 Hz, 4H), 7.33-7.28 (m, 1H), 5.48 (s, 1H), 3.33 (d, J=6.8 Hz, 2H), 1.13 (dddd, J=13.3, 6.8, 5.0, 2.6 Hz, 1H), 0.67-0.46 (m, 2H), 0.29-0.12 (m, 2H); MS (ES+) 306.2 (M+Na); Optical rotation: $[α]_D$=(+) 36.07 [$CHCl_3$, 0.755].

Step-3: Preparation of (+)-3-((cyclopropylmethoxy)(phenyl)methyl)aniline (166c)

To a stirred solution of (−)-1-((cyclopropylmethoxy)(phenyl)methyl)-3-nitrobenzene (166b) (133 mg, 0.469 mmol) in anhydrous methanol (30 mL), cooled to 0° C., was added nickel(II) chloride hexahydrate (0.056 g, 0.235 mmol) followed by sodium borohydride (0.107 g, 2.82 mmol) small portions over a period of 5 min. The reaction mixture was stirred for 23 min at 0° C. TLC analysis (ethyl acetate/hexanes, 5/95, v/v) shows reaction was complete at this point N1-(2-aminoethyl)ethane-1,2-diamine (0.507 mL, 4.69 mmol) was added. The mixture was allowed to stir for 30 minutes before solvent was evaporated. The residue was treated sat $NH_4Cl$ (25 mL), and extracted with ethyl acetate (2×25 mL). Organic layer were combined dried over anhydrous $MgSO_4$, filtered, and excess solvents were pumped-off under reduced pressure. The residue was purified by flash column chromatography [(silica gel 12 g, eluting with ethyl acetate/hexanes from 0 to 50%)] to furnish (+)-3-((cyclopropylmethoxy)(phenyl)methyl)aniline (166c) (101 mg, 85% yield) as a yellow solid; $^1$H NMR (300 MHz, Chloroform-d) δ 7.38-7.30 (m, 3H), 7.29-7.21 (m, 2H), 7.09 (t, J=7.7 Hz, 1H), 6.79-6.69 (m, 2H), 6.56 (ddd, J=7.9, 2.3, 1.0 Hz, 1H), 5.31 (s, 1H), 3.31 (dd, J=6.8, 3.1 Hz, 2H), 1.12 (ttt, J=8.0, 6.7, 4.8 Hz, 1H), 0.62-0.45 (m, 2H), 0.18 (dt, J=6.0, 4.4 Hz, 2H); MS (ES$^+$): MS (ES+) 254.2 (M+1), 276.2 (M+Na), MS (ES−) 515.2 (M−1); Optical rotation: $[α]_D$=(+) 6.868 [$CHCl_3$, 1.19].

Step-4: Preparation of (+)-1-(3-cyanophenyl)-N-(3-((cyclopropylmethoxy)(phenyl)methyl)phenyl)-3-(trifluoromethyl)-1H-pyrazole-5-carboxamide (166d)

A single-necked 100 mL flask containing 1-(3-cyanophenyl)-3-(trifluoromethyl)-1H-pyrazole-5-carboxylic acid (9i) (155 mg, 0.551 mmol), (+)-3-((cyclopropylmethoxy)(phenyl)methyl)aniline (166c) (0.093 g, 0.367 mmol), bromo-tris-pyrrolidino phosphoniumhexafluorophosphate(PyBrOP, 0.205 g, 0.441 mmol) was added N,N-dimethylformamide (4.26 mL) and N-ethyl-N-isopropylpropan-2-amine (0.320 mL, 1.835 mmol) successively under a positive flow of nitrogen at room temperature. The resulting reaction mixture was stirred at room temperature for 16 h under a positive flow of nitrogen atmosphere. Excess DMF was pumped-off under reduced pressure. The residue was treated with water (30 mL), and extracted with chloroform (2×50 mL). Combined organics were dried over anhydrous $MgSO_4$, filtered and evaporated to dryness. The residue was then purified by flash column chromatography [silica gel 40 g, eluting with ethyl acetate in hexanes from 0-50%] to furnish (+)-1-(3-cyanophenyl)-N-(3-((cyclopropylmethoxy)(phenyl)methyl)phenyl)-3-(trifluoromethyl)-1H-pyrazole-5-carboxamide (166d) (172 mg, 91% yield) as a yellow solid.

$^1$H NMR (300 MHz, DMSO-$d_6$) δ 10.68 (s, 1H, $D_2O$ exchangeable), 8.17 (t, J=1.8 Hz, 1H), 8.00 (dt, J=7.7, 1.3 Hz, 1H), 7.91 (ddd, J=8.2, 2.3, 1.2 Hz, 1H), 7.81-7.69 (m, 2H), 7.68-7.55 (m, 2H), 7.46-7.21 (m, 6H), 7.18-7.09 (m, 1H), 5.45 (s, 1H), 3.23 (d, J=6.8 Hz, 2H), 1.12-0.99 (m, 1H), 0.57-0.40 (m, 2H), 0.15 (tdd, J=4.2, 2.6, 1.6 Hz, 2H); $^{19}$F NMR (282 MHz, DMSO-$d_6$) δ −60.96; MS (ES$^+$): MS (ES+) 539.3 (M+1), MS (ES−) 515.2 (M−1); Optical rotation: [α]$_D$=(+) 0.84 [CHCl$_3$, 0.955].

Step-5: Preparation of (+)-1-(3-(aminomethyl)phenyl)-N-(3-((cyclopropylmethoxy)(phenyl)methyl)phenyl)-3-(trifluoromethyl)-1H-pyrazole-5-carboxamide To a stirred solution of (+)-1-(3-cyanophenyl)-N-(3-((cyclopropylmethoxy)(phenyl)methyl)phenyl)-3-(trifluoromethyl)-1H-pyrazole-5-carboxamide (166e)

To a solution of (+)-1-(3-cyanophenyl)-N-(3-((cyclopropylmethoxy)(phenyl)methyl)phenyl)-3-(trifluoromethyl)-1H-pyrazole-5-carboxamide (166d) (0.151 g, 0.292 mmol) in anhydrous methanol (30 mL) cooled to 0° C., was added nickel(II) chloride hexahydrate (0.087 g, 0.365 mmol) followed by sodium borohydride (0.088 g, 2.339 mmol) in small portions over a period of 5 min. The reaction mixture was stirred for 10 min, TLC analysis (methanol/chloroform, 1/9, v/v) shows reaction was complete at this point N1-(2-aminoethyl)ethane-1,2-diamine (0.316 mL, 2.92 mmol) was added. Excess methanol was pumped-off under reduced pressure. The reaction mixture was treated with sat. NH$_4$Cl (30 mL), and product was extracted with chloroform (2×30 mL), combined organic layer was dried over MgSO$_4$, filtered, evaporated to dryness. The residue was purified by flash column chromatography [(silica gel 25 g, eluting with methanol/chloroform from 0 to 50%)] to furnish (+)-1-(3-cyanophenyl)-N-(3-((cyclopropylmethoxy)(phenyl)methyl)phenyl)-3-(trifluoromethyl)-1H-pyrazole-5-carboxamide (166e) (107 mg, 70% yield) as a white solid; $^1$H NMR (300 MHz, DMSO-$d_6$) δ 10.72 (s, 1H, $D_2O$ exchangeable), 7.63 (t, J=1.8 Hz, 1H), 7.60-7.50 (m, 3H), 7.42 (d, J=6.6 Hz, 2H), 7.37-7.20 (m, 7H), 7.16-7.10 (m, 1H), 5.44 (s, 1H), 3.77 (s, 2H), 3.23 (dd, J=6.8, 1.3 Hz, 2H), 1.05 (m, 1H), 0.46 (dq, J=8.5, 3.5, 2.6 Hz, 2H), 0.19-0.09 (m, 2H). $^{19}$F NMR (282 MHz, DMSO-$d_6$) δ −60.72. MS (ES$^+$): MS (ES+) 521.3 (M+1), MS (ES−) 519.3 (M−1); Chiral HPLC: 72.95% ee determined by HPLC with a Chiralpak AD-H column (isopropanol/hexanes=20:80, 0.8 mL/min, eluting with 0.1% triethyl amine, uv 250 nM): Rt=5.97 min (minor), Rt=6.52 min (major). Optical rotation: [α]$_D$=(+) 3.018 [CHCl$_3$, 1.06]; Analysis calculated for $C_{29}H_{27}F_3N_4O_2 \cdot 0.25H_2O$: C, 66.34; H, 5.28; N, 10.67; Found: C, 66.23; H, 5.30; N, 10.38.

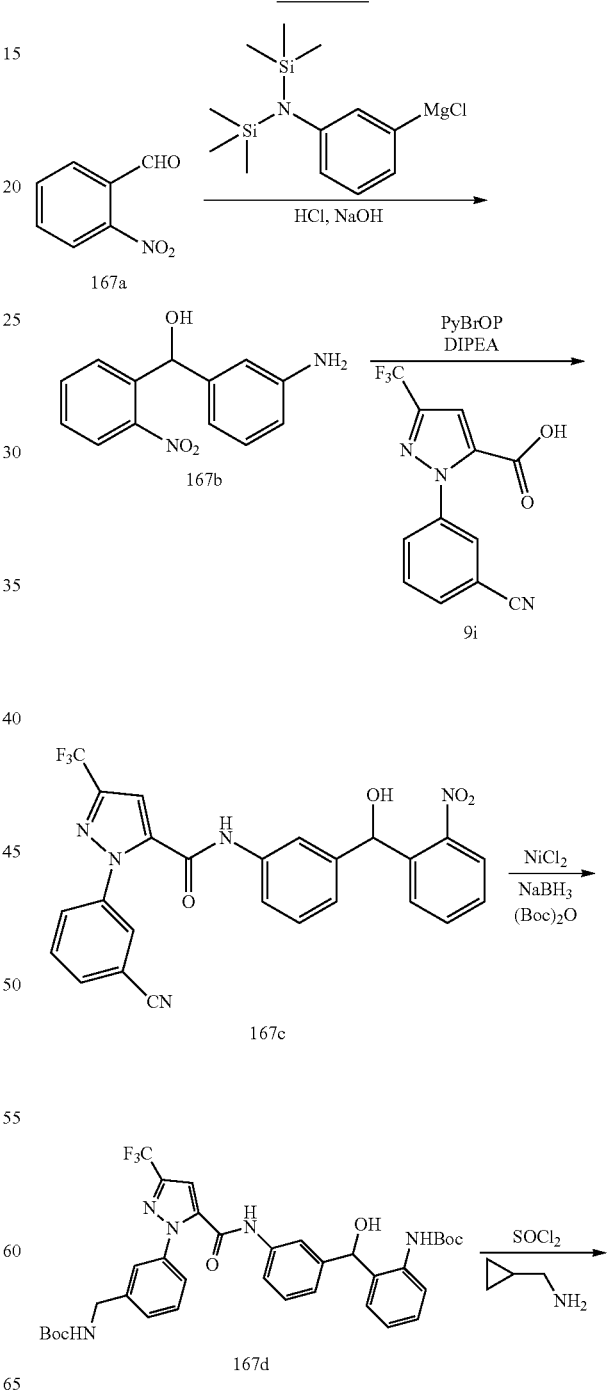

Scheme 167

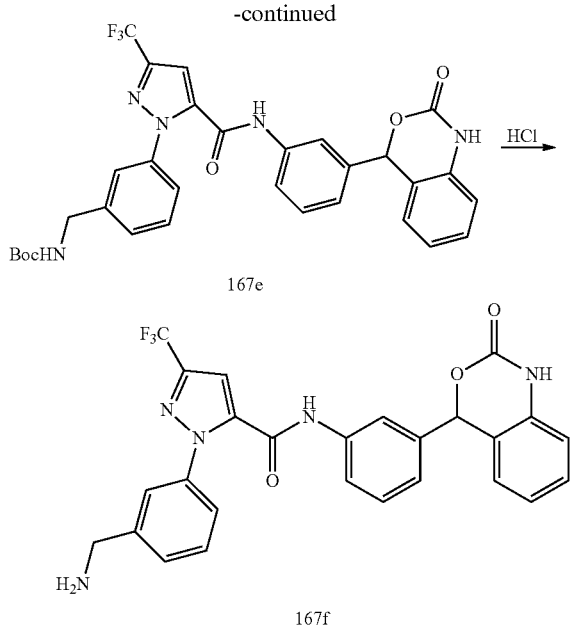

Preparation of 1-(3-(aminomethyl)phenyl)-N-(3-(2-oxo-2,4-dihydro-1H-benzo[d] [1,3]oxazin-4-yl)phenyl)-3-(trifluoromethyl)-1H-pyrazole-5-carboxamide (167f)

Step-1: Preparation of (3-aminophenyl)(2-nitrophenyl)methanol (167b)

To a solution of 2-nitrobenzaldehyde (167a) (4.63 g, 30 mmol) in tetrahydrofuran (30 mL) cooled to 0° C. was added (3-(bis(trimethylsilyl)amino)phenyl)magnesium chloride (49c) (36.0 mL, 36.0 mmol) and stirred at room temperature for 12 h. The reaction mixture was treated with 1 N HCl (aq. 75 mL), stirred at room temperature for 3 h, neutralized with NaOH (2 N, aq.) to pH=~8, and extracted with ethyl acetate (2×100 mL). The combined extracts were washed with brine (80 mL), dried over MgSO$_4$ followed by filtration and concentration. The crude product was purified by flash column chromatography [silica gel 120 g, eluting with chloroform/methanol (1:0 to 19:1)] to give (3-aminophenyl)(2-nitrophenyl)methanol (167b) (3.76 g, 51%). $^1$H NMR (300 MHz, DMSO-d$_6$) δ 7.87-7.82 (m, 1H), 7.77-7.67 (m, 2H), 7.50 (ddd, J=8.0, 6.6, 2.2 Hz, 1H), 6.92 (t, J=7.7 Hz, 1H), 6.46 (t, J=1.9 Hz, 1H), 6.41 (ddd, J=7.9, 2.3, 1.0 Hz, 1H), 6.36 (dt, J=7.6, 1.3 Hz, 1H), 6.05 (s, 2H), 5.04 (s, 2H); MS (ES+): 267.2 (M+Na).

Step-2: Preparation of 1-(3-cyanophenyl)-N-(3-(hydroxy(2-nitrophenyl)methyl)phenyl)-3-(trifluoromethyl)-1H-pyrazole-5-carboxamide (167c)

A solution of (3-aminophenyl)(2-nitrophenyl)methanol (167b) (3.6 g, 14.74 mmol) in DMF (75 mL) was treated with 1-(3-cyanophenyl)-3-(trifluoromethyl)-1H-pyrazole-5-carboxylic acid (9i) (4.14 g, 14.74 mmol), N-ethyl-N-isopropylpropan-2-amine (21.00 mL, 121 mmol) and bromotripyrrolidin-1-ylphosphonium hexafluorophosphate(V) (PyBrOP, 7.01 g, 14.74 mmol) followed by stirring at RT for 16 h. The reaction mixture was diluted with ethyl acetate (400 mL), washed with water (2×120 mL) and brine (120 mL), and dried over MgSO$_4$ followed by filtration and concentration. The crude product was purified by flash column chromatography [silica gel 120 g, eluting with hexanes/ethyl acetate (1:0 to 1:1)] to give 1-(3-cyanophenyl)-N-(3-(hydroxy(2-nitrophenyl)methyl)phenyl)-3-(trifluoromethyl)-1H-pyrazole-5-carboxamide (167c) (3.45 g, 46%) yellow solid; $^1$H NMR (300 MHz, DMSO-d$_6$) δ 10.66 (s, 1H), 8.16 (t, J=1.8 Hz, 1H), 8.00 (dt, J=7.7, 1.3 Hz, 1H), 7.93-7.87 (m, 2H), 7.78-7.69 (m, 4H), 7.65-7.49 (m, 3H), 7.28 (t, J=7.9 Hz, 1H), 7.01 (d, J=7.7 Hz, 1H), 6.30 (d, J=4.7 Hz, 1H), 6.18 (d, J=4.6 Hz, 1H); $^{19}$F NMR (282 MHz, DMSO-d$_6$) δ −60.96; MS (ES+): 530.2 (M+Na).

Step-3: Preparation of tert-butyl 3-(5-((3-((2-tert-butyloxycarbonylaminophenyl)(hydroxy)methyl)phenyl)carbamoyl)-3-(trifluoromethyl)-1H-pyrazol-1-yl)benzylcarbamate (167d)

A solution of 1-(3-cyanophenyl)-N-(3-(hydroxy(2-nitrophenyl)methyl)phenyl)-3-(trifluoromethyl)-1H-pyrazole-5-carboxamide (167c) (3.309 g, 6.52 mmol) in MeOH (110 mL) cooled with ice/water was added di-tert-butyl dicarbonate (5.75 g, 26.1 mmol), nickel(II) chloride hexahydrate (0.834 g, 3.51 mmol), followed by addition of Sodium Borohydride (2.52 g, 65.2 mmol) slowly over 5 min and stirring at RT for 1 h. The reaction mixture was treated N$_1$-(2-aminoethyl)ethane-1,2-diamine (3.30 mL, 30.3 mmol) followed by stirring at RT for 0.5 h and concentration to dryness. The residue was treated with ethyl acetate (300 mL), washed with water (120 mL). The aqueous phase was extracted again with ethyl acetate (150 mL). The combined extracts were washed with brine (150 mL), dried over MgSO$_4$ followed by filtration and concentration. The crude product was purified by flash column chromatography [silica gel 80 g, eluting with hexanes/ethyl acetate (1:0 to 1:1)] to give tert-butyl 3-(5-((3-((2-tert-butyloxycarbonylaminophenyl)(hydroxy)methyl)phenyl)carbamoyl)-3-(trifluoromethyl)-1H-pyrazol-1-yl)benzylcarbamate (167d) (975 mg, 22%) as a light yellow solid; $^1$H NMR (300 MHz, DMSO-d$_6$) δ 10.70 (s, 1H), 8.58 (s, 1H), 7.61 (s, 1H), 7.59-7.18 (m, 11H), 7.08-7.00 (m, 2H), 6.49 (d, J=4.0 Hz, 1H), 5.88 (d, J=3.9 Hz, 1H), 4.19 (d, J=6.2 Hz, 2H), 1.37 (s, 9H), 1.36 (s, 9H); $^{19}$F NMR (282 MHz, DMSO-d$_6$) δ −60.82; MS (ES+): 704.4 (M+Na).

Step-4: Preparation of tert-butyl 3-(5-(3-(2-oxo-2,4-dihydro-1H-benzo[d][1,3]oxazin-4-yl)phenylcarbamoyl)-3-(trifluoromethyl)-1H-pyrazol-1-yl)benzylcarbamate (167e)

A solution of tert-butyl 3-(5-((3-((2-tert-butyloxycarbonylaminophenyl)(hydroxy)methyl)phenyl)carbamoyl)-3-(trifluoromethyl)-1H-pyrazol-1-yl)benzylcarbamate (167d) (970 mg, 1.402 mmol) in dichloromethane (28 mL) at 0° C. was treated with thionyl chloride (0.220 mL, 2.97 mmol) and allowed to warm to room temperature over 2 h. The reaction mixture was treated with triethyl amine (1.30 mL, 9.33 mmol) followed by stirring at RT for 1 h. It was then treated with cyclopropylmethanamine (2.70 mL, 30.2 mmol) and concentrated to remove most of dichloromethane followed by addition of acetonitrile (21 mL), stirring at 70° C. for 14 h, and concentration to dryness. The residue was treated with chloroform (200 mL), washed with water (100 mL), dried over MgSO$_4$ followed by filtration and concentration. The crude product was purified by flash column chromatography on 25 g of silica gel with hexanes/ethyl acetate (1:0 to 1:1) to give tert-butyl 3-(5-(3-(2-oxo-2,4- dihydro-1H-benzo[d] [1,3]oxazin-4-yl)phenylcarbamoyl)-3-(trifluoromethyl)-1H-pyrazol-1-yl)benzylcarbamate (167e) (255 mg, 30%) off-white solid; ¹H NMR (300 MHz, DMSO-d₆) δ 10.83 (s, 1H), 10.35 (s, 1H), 8.12-7.25 (m, 10H), 7.09 (d, J=7.6 Hz, 1H), 7.04-6.87 (m, 3H), 6.53 (s, 1H), 4.19 (d, J=6.2 Hz, 2H), 1.36 (s, 9H); MS (ES+): 630.3 (M+Na).

Step-5: Preparation of 1-(3-(aminomethyl)phenyl)-N-(3-(2-oxo-2,4-dihydro-1H-benzo[d][1,3]oxazin-4-yl)phenyl)-3-(trifluoromethyl)-1H-pyrazole-5-carboxamide (167f)

A solution of tert-butyl 3-(5-(3-(2-oxo-2,4-dihydro-1H-benzo[d][1,3]oxazin-4-yl)phenylcarbamoyl)-3-(trifluoromethyl)-1H-pyrazol-1-yl)benzylcarbamate (167e) (120 mg, 0.198 mmol) in 1,4-Dioxane (12 mL) was treated with hydrogen chloride (2.2 mL, 8.8 mmol, 4 M in 1,4-dioxane) slowly followed by stirring at RT for 14.5 h. The reaction mixture was treated with hexanes, decanted, washed with hexanes, and decanted again. The insoluble crude product was purified by flash column chromatography [silica gel with chloroform/CMA80 (1:0 to 1:1)] to give 1-(3-(aminomethyl)phenyl)-N-(3-(2-oxo-2,4-dihydro-1H-benzo[d][1,3]oxazin-4-yl)phenyl)-3-(trifluoromethyl)-1H-pyrazole-5-carboxamide (167f) (33 mg) as a colorless gum as a free base; The purified product (167f) (31 mg, 33%) was dissolved in methanol (10 mL) and treated with 4 N HCl (aq. 0.06 mL) followed by concentration to dryness to furnish 1-(3-(aminomethyl)phenyl)-N-(3-(2-oxo-2,4-dihydro-1H-benzo[d] [1,3] oxazin-4-yl)phenyl)-3-(trifluoromethyl)-1H-pyrazole-5-carboxamide (33 mg) hydrochloride salt as an off-white solid; ¹H NMR (D₂O ex NMR, 300 MHz, DMSO-d₆) δ 7.73-7.49 (m, 7H), 7.42 (t, J=7.9 Hz, 1H), 7.35-7.27 (m, 1H), 7.11 (d, J=7.7 Hz, 1H), 7.03 (td, J=7.5, 1.2 Hz, 1H), 6.97 (d, J=8.0 Hz, 1H), 6.92 (d, J=7.5 Hz, 1H), 6.53 (s, 1H), 4.13 (s, 2H); ¹⁹F NMR (282 MHz, DMSO-d₆) δ −60.80; MS (ES+): 508.2 (M+H); IR (KBr pellet cm⁻¹): 3441, 3256, 1700, 1601, 1558, 1491, 1246; Analysis calculated for $C_{26}H_{20}F_3N_5O_3 \cdot HCl \cdot 2.5H_2O$: C, 53.02; H, 4.45; N, 11.89; Found: C, 53.22; H, 4.37; N, 11.33.

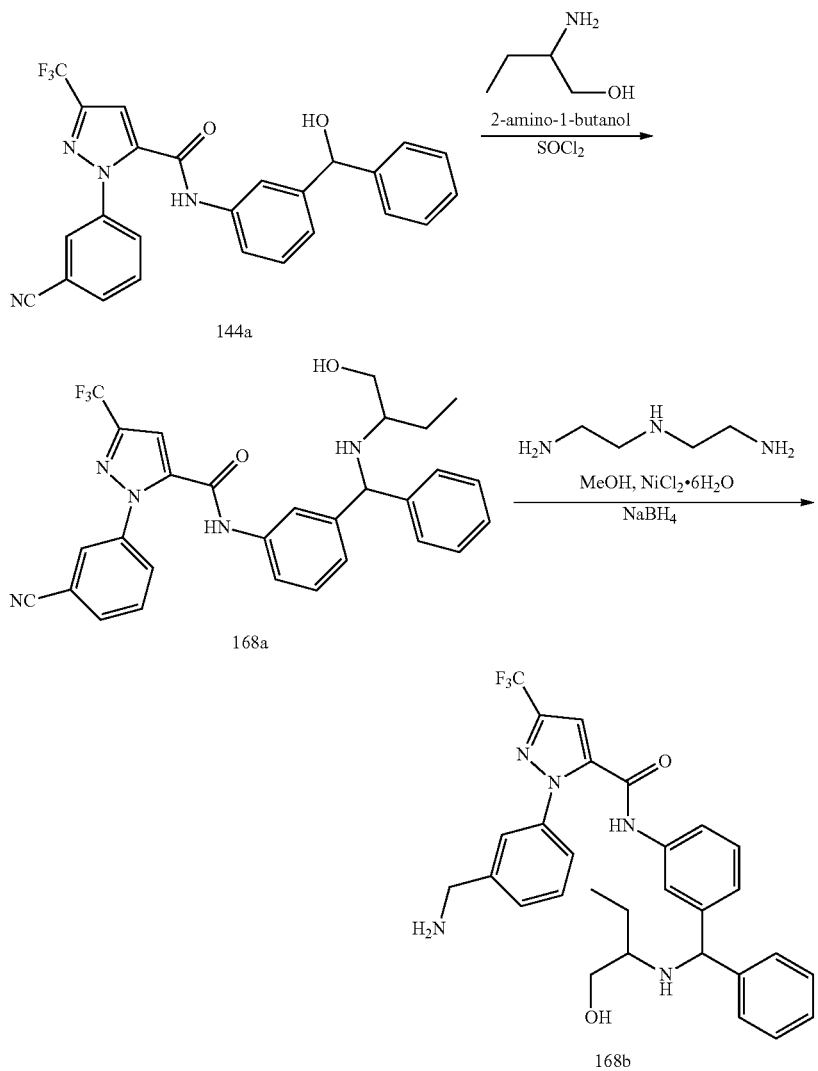

Scheme 168

Preparation of 1-(3-(Aminomethyl)phenyl)-N-(3-(((1-hydroxybutan-2-yl)amino)(phenyl)methyl)phenyl)-3-(trifluoromethyl)-1H-pyrazole-5-carboxamide (168b)

Step-1: Preparation of 1-(3-cyanophenyl)-N-(3-(((1-hydroxybutan-2-yl)amino)(phenyl)methyl)phenyl)-3-(trifluoromethyl)-1H-pyrazole-5-carboxamide (168a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.16 mmol) in dichloromethane (50 mL) at 0° C. was added thionyl chloride (0.5 g, 4.33 mmol) and stirred at room temperature for 3 h. 2-amino-1-butanol (0.96 g, 10.81 mmol) was added and mixture stirred at room temperature for 30 min. The reaction mixture was concentrated in vacuum to dryness. The residue obtained was dissolved in acetonitrile (20 mL) and added 2-amino-1-butanol (0.964 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 1-(3-cyanophenyl)-N-(3-(((1-hydroxybutan-2-yl)amino)(phenyl)methyl)phenyl)-3-(trifluoromethyl)-1H-pyrazole-5-carboxamide (168a) (0.42 g, 36%) as an off white semi-solid.

$^1$H NMR (300 MHz, DMSO-$d_6$) δ 10.64 (d, J=2.2 Hz, 1H), 8.15 (dd, J=2.1, 1.2 Hz, 1H), 7.99 (dt, J=7.8, 1.3 Hz, 1H), 7.89 (ddd, J=8.2, 2.2, 1.1 Hz, 1H), 7.76-7.71 (m, 1H), 7.70 (d, J=1.2 Hz, 1H), 7.65 (d, J=14.3 Hz, 1H), 7.58-7.51 (m, 1H), 7.40 (td, J=8.2, 1.4 Hz, 2H), 7.32-7.27 (m, 2H), 7.26 (d, J=1.5 Hz, 1H), 7.24-7.19 (m, 2H), 4.96 (s, 1H), 4.48 (dt, J=6.5, 5.3 Hz, 1H), 3.56-3.40 (m, 1H), 3.34-3.27 (m, 1H), 2.34-2.26 (m, 1H), 1.43-1.36 (m, 2H), 0.80 (dd, J=7.6, 1.7 Hz, 3H); MS (ES-) 532.8 (M-1).

Step-2: Preparation of 1-(3-(aminomethyl)phenyl)-N-(3-(((1-hydroxybutan-2-yl)amino)(phenyl)methyl)phenyl)-3-(trifluoromethyl)-1H-pyrazole-5-carboxamide (168b)

To a solution of 1-(3-cyanophenyl)-N-(3-(((1-hydroxybutan-2-yl)amino)(phenyl)methyl)phenyl)-3-(trifluoromethyl)-1H-pyrazole-5-carboxamide (168a) (0.42 g, 0.74 mmol) in MeOH (20 mL) cooled with ice/water was added nickel(II) chloride hexahydrate (0.21 g, 0.89 mmol) and followed by portion-wise addition of Sodium Borohydride (0.16 g, 4.44 mmol) over a period of 5 min. The reaction mixture was stirred at room temperature for 2 hrs and quenched with $N^1$-(2-aminoethyl)ethane-1,2-diamine (0.19 g, 1.85 mmol) followed by stirring for additional 0.5 h. The reaction mixture was concentrated in vacuum to dryness, and the residue obtained was purified by flash column chromatography (silica gel 65 g, eluting with 0-12% MeOH/DCM) to furnish 1-(3-(aminomethyl)phenyl)-N-(3-(((1-hydroxybutan-2-yl)amino)(phenyl)methyl)phenyl)-3-(trifluoromethyl)-1H-pyrazole-5-carboxamide (168b) (0.2 g, 50%) as a yellow powder. This material was repurified by flash column chromatography (silica gel 12 g, eluting with methanol in chloroform) to furnish 1-(3-(aminomethyl)phenyl)-N-(3-(((1-hydroxybutan-2-yl)amino)(phenyl)methyl)phenyl)-3-(trifluoromethyl)-1H-pyrazole-5-carboxamide (168b) as a white solid; $^1$H NMR (300 MHz, DMSO-$d_6$) δ 10.80-10.57 (m, 1H), 7.66 (dd, J=9.9, 2.2 Hz, 1H), 7.59-7.48 (m, 3H), 7.41 (dd, J=8.4, 6.7 Hz, 4H), 7.35-7.13 (m, 6H), 4.96 (s, 1H), 3.77 (s, 2H), 3.49-3.30 (m, 2H), 2.28 (q, J=5.5 Hz, 1H), 1.40 (p, J=7.1 Hz, 2H), 0.82 (t, J=7.4 Hz, 3H); $^{19}$F NMR (282 MHz, DMSO) δ -60.71; MS (ES+) 538.04 (M+1); (ES-) 536.4 (M-1); Analysis calculated for $C_{29}H_{30}F_3N_5O_2 \cdot 0.5H_2O$: C, 63.72; H, 5.72; N, 12.81; Found: C, 64.02; H, 5.69; N, 12.63.

Scheme 169

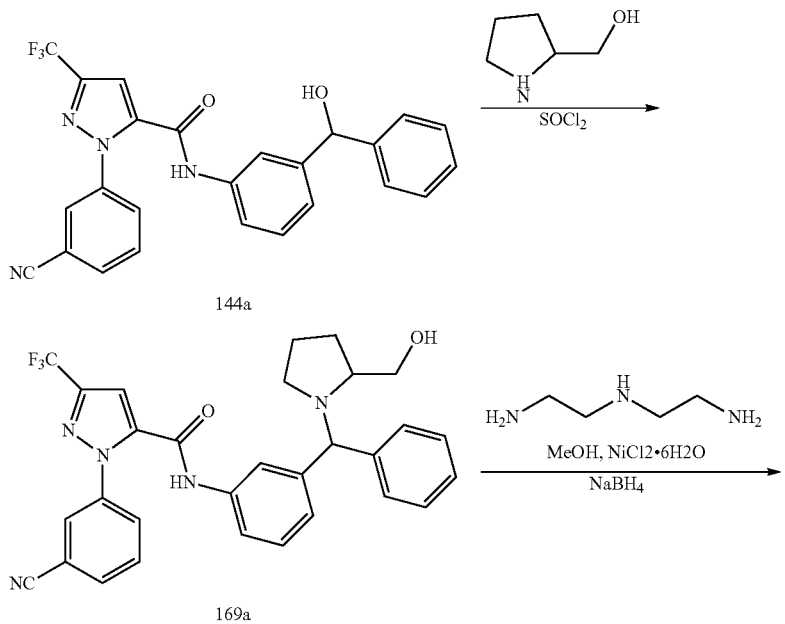

144a

169a

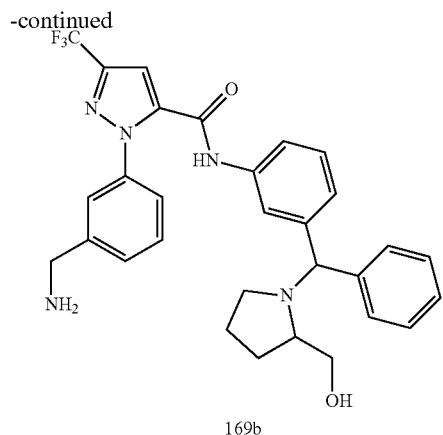

169b

Preparation of 1-(3-(Aminomethyl)phenyl)-N-(3-((2-(hydroxymethyl)pyrrolidin-1-yl)(phenyl)methyl)phenyl)-3-(trifluoromethyl)-1H-pyrazole-5-carboxamide (169b)

Step-1: 1-(3-cyanophenyl)-N-(3-((2-(hydroxymethyl)pyrrolidin-1-yl)(phenyl)methyl)phenyl)-3-(trifluoromethyl)-1H-pyrazole-5-carboxamide (169a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.16 mmol) in dichloromethane (50 mL) at 0° C. was added thionyl chloride (0.514 g, 4.325 mmol) and stirred at room temperature for 3 h. Pyrrolidin-2-yl-methanol (1.093 g, 10.81 mmol) was added and stirred for 30 min. The reaction mixture was concentrated in vacuum to dryness. The residue obtained was dissolved in acetonitrile (20 mL) and added Pyrrolidin-2-yl-methanol (1.093 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 1-(3-cyanophenyl)-N-(3-((2-(hydroxymethyl)pyrrolidin-1-yl)(phenyl)methyl)phenyl)-3-(trifluoromethyl)-1H-pyrazole-5-carboxamide (169a) (1.0 g, 83%) as a brownish oil; $^1$H NMR (300 MHz, DMSO-d$_6$) δ 10.64 (d, J=2.1 Hz, 1H), 8.20-8.12 (m, 1H), 8.00 (dq, J=7.7, 1.2 Hz, 1H), 7.90 (ddt, J=8.2, 2.3, 1.3 Hz, 1H), 7.77-7.62 (m, 3H), 7.61-7.50 (m, 1H), 7.41 (dd, J=8.0, 6.3 Hz, 2H), 7.31-7.17 (m, 5H), 4.73 (d, J=6.3 Hz, 1H), 4.30 (dt, J=7.8, 5.3 Hz, 1H), 3.23-2.98 (m, 2H), 2.76 (ddd, J=22.8, 10.8, 5.9 Hz, 2H), 2.37-2.20 (m, 1H), 1.81-1.59 (m, 4H); MS (ES−) 544.3 (M−1).

Step-2: Preparation of 1-(3-(aminomethyl)phenyl)-N-(3-((2-(hydroxymethyl)pyrrolidin-1-yl)(phenyl)methyl)phenyl)-3-(trifluoromethyl)-1H-pyrazole-5-carboxamide (169b)

To a solution of 1-(3-cyanophenyl)-N-(3-((2-(hydroxymethyl)pyrrolidin-1-yl)(phenyl)methyl)phenyl)-3-(trifluoromethyl)-1H-pyrazole-5-carboxamide (169a) (1.0 g, 1.834 mmol) in MeOH (20 mL) cooled with ice/water was added nickel(II) chloride hexahydrate (0.547 g, 2.303 mmol) and followed by portion-wise addition of sodium borohydride (0.416 g, 11.0 mmol) over a period of 5 min. The reaction mixture was stirred at room temperature for 2 hrs and quenched with N$^1$-(2-aminoethyl)ethane-1,2-diamine (0.473 g, 4.585 mmol) followed by stirring for additional 0.5 h. The reaction mixture was concentrated in vacuum to dryness, and the residue obtained was purified by flash column chromatography (silica gel 60 g, eluting with 0-12% MeOH/DCM) to furnish 1-(3-(aminomethyl)phenyl)-N-(3-((2-(hydroxymethyl)pyrrolidin-1-yl)(phenyl)methyl)phenyl)-3-(trifluoromethyl)-1H-pyrazole-5-carboxamide (169b) (0.25 g, 25%) as an off white solid; $^1$H NMR (300 MHz, DMSO-d$_6$) δ 10.69 (s, 1H), 7.67 (d, J=16.9 Hz, 1H), 7.62-7.46 (m, 4H), 7.41 (td, J=7.4, 3.6 Hz, 3H), 7.24 (dddd, J=17.1, 10.8, 7.4, 3.2 Hz, 6H), 4.72 (d, J=5.7 Hz, 1H), 3.90 (s, 2H), 3.03 (dd, J=22.4, 9.8 Hz, 1H), 2.89-2.66 (m, 2H), 2.33-2.21 (m, 2H), 1.69 (d, J=22.5 Hz, 4H); $^{19}$F NMR (282 MHz, DMSO) δ −60.73, −60.74; MS (ES+) 550.4 (M+1); (ES−) 548.4 (M−1) 584.4, (M+Cl); Analysis calculated for $C_{30}H_{30}F_3N_5O_2 \cdot HCl \cdot 1.5H_2O$: C, 58.77; H, 5.59; N, 11.42; Found: C, 59.10; H, 5.54; N, 11.25.

Scheme 170

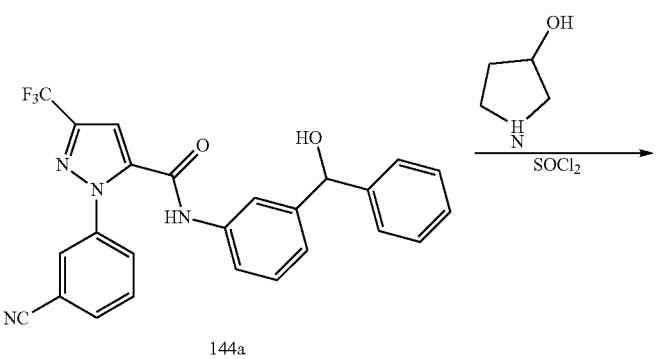

144a

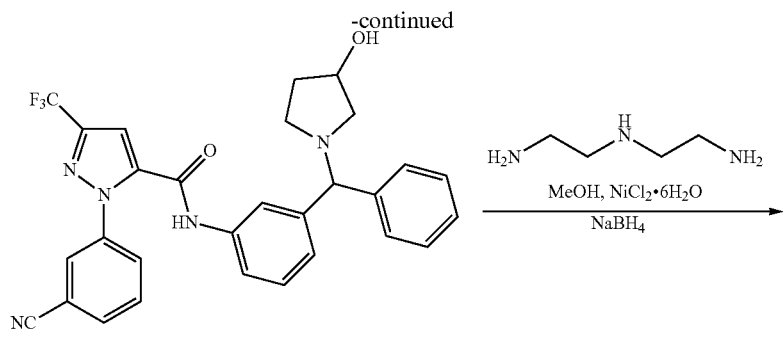

170a

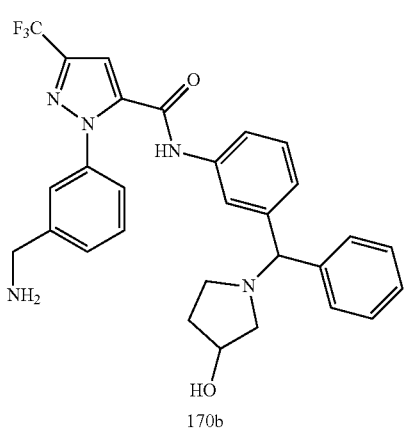

170b

Preparation of 1-(3-(Aminomethyl)phenyl)-N-(3-((3-hydroxypyrrolidin-1-yl)(phenyl)methyl)phenyl)-3-(trifluoromethyl)-1H-pyrazole-5-carboxamide (170b)

Step-1: Preparation of 1-(3-cyanophenyl)-N-(3-((3-hydroxypyrrolidin-1-yl)(phenyl)methyl)phenyl)-3-(trifluoromethyl)-1H-pyrazole-5-carboxamide (170a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.16 mmol) in dichloromethane (50 mL) at 0° C. was added thionyl chloride (0.514 g, 4.325 mmol) and stirred at room temperature for 3 h. Pyrrolidin-3-ol (0.94 g, 10.81 mmol) was added and stirred for 30 min. The reaction mixture was concentrated in vacuum to dryness. The residue obtained was dissolved in acetonitrile (20 mL) and added Pyrrolidin-3-ol (0.94 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 1-(3-cyanophenyl)-N-(3-((3-hydroxypyrrolidin-1-yl)(phenyl)methyl)phenyl)-3-(trifluoromethyl)-1H-pyrazole-5-carboxamide (170a) (0.6 g, 52%) as a brownish oil; $^1$H NMR (300 MHz, DMSO-$d_6$) δ 10.65 (s, 1H), 8.20-8.13 (m, 1H), 8.03-7.97 (m, 1H), 7.93-7.87 (m, 1H), 7.78-7.66 (m, 3H), 7.56 (dt, J=7.1, 2.2 Hz, 1H), 7.46-7.42 (m, 1H), 7.41 (s, 1H), 7.31-7.23 (m, 4H), 7.17 (t, J=7.2 Hz, 1H), 4.72 (dd, J=4.1, 2.4 Hz, 1H), 4.25-4.14 (m, 2H), 2.59 (dt, J=11.0, 6.0 Hz, 1H), 2.45-2.15 (m, 2H), 2.03 (d, J=8.0 Hz, 1H), 1.56 (d, J=8.7 Hz, 1H), 1.22 (d, J=1.9 Hz, 1H); MS (ES-) 530.3 (M-1).

Step-2: Preparation of 1-(3-(aminomethyl)phenyl)-N-(3-((3-hydroxypyrrolidin-1-yl)(phenyl)methyl)phenyl)-3-(trifluoromethyl)-1H-pyrazole-5-carboxamide (170b)

To a solution of 1-(3-cyanophenyl)-N-(3-((3-hydroxypyrrolidin-1-yl)(phenyl)methyl)phenyl)-3-(trifluoromethyl)-1H-pyrazole-5-carboxamide (170a) (0.6 gm 1.28 mmol) in MeOH (20 mL) cooled with ice/water was added nickel(II) chloride hexahydrate (0.32 g, 1.35 mmol) and followed by portion-wise addition of Sodium Borohydride (0.25 g, 6.77 mmol) over a period of 5 min. The reaction mixture was stirred at room temperature for 2 hrs and quenched with $N^1$-(2-aminoethyl)ethane-1,2-diamine (0.29 g, 2.822 mmol) followed by stirring for additional 0.5 h. The reaction mixture was concentrated in vacuum to dryness, and the residue obtained was purified by flash column chromatography (silica gel 60 g, eluting with 0-12% MeOH/DCM) to furnish 1-(3-(aminomethyl)phenyl)-N-(3-((3-hydroxypyrrolidin-1-yl)(phenyl)methyl)phenyl)-3-(trifluoromethyl)-1H-pyrazole-5-carboxamide (170b) (0.15 g, 22%) as a white solid; $^1$H NMR (300 MHz, DMSO-$d_6$) δ 10.75-10.66 (m, 1H), 7.68 (s, 1H), 7.66-7.60 (m, 2H), 7.52 (t, J=6.5 Hz, 3H), 7.49-7.38 (m, 3H), 7.30-7.21 (m, 4H), 7.19 (d, J=7.3 Hz, 1H), 6.61 (s, 2H), 4.71 (s, 1H), 4.20 (s, 2H), 4.00 (s, 2H), 2.66-2.58 (m, 1H), 2.44 (dd, J=3.8, 1.9 Hz, 1H), 2.38-2.17 (m, 1H), 1.98 (dd, J=13.4, 6.8 Hz, 1H), 1.56 (s, 1H); $^{19}$F NMR (282 MHz, DMSO) δ −60.76; MS (ES+) 536.4 (M+1); (ES−) 535.1 (M−1); 570.4 (M+Cl); Analysis calculated for $C_{29}H_{28}F_3N_5O_2$·HCl·1.5H$_2$O: C, 58.14; H, 5.38; N, 11.69; Found: C, 58.37; H, 5.27; N, 11.82.

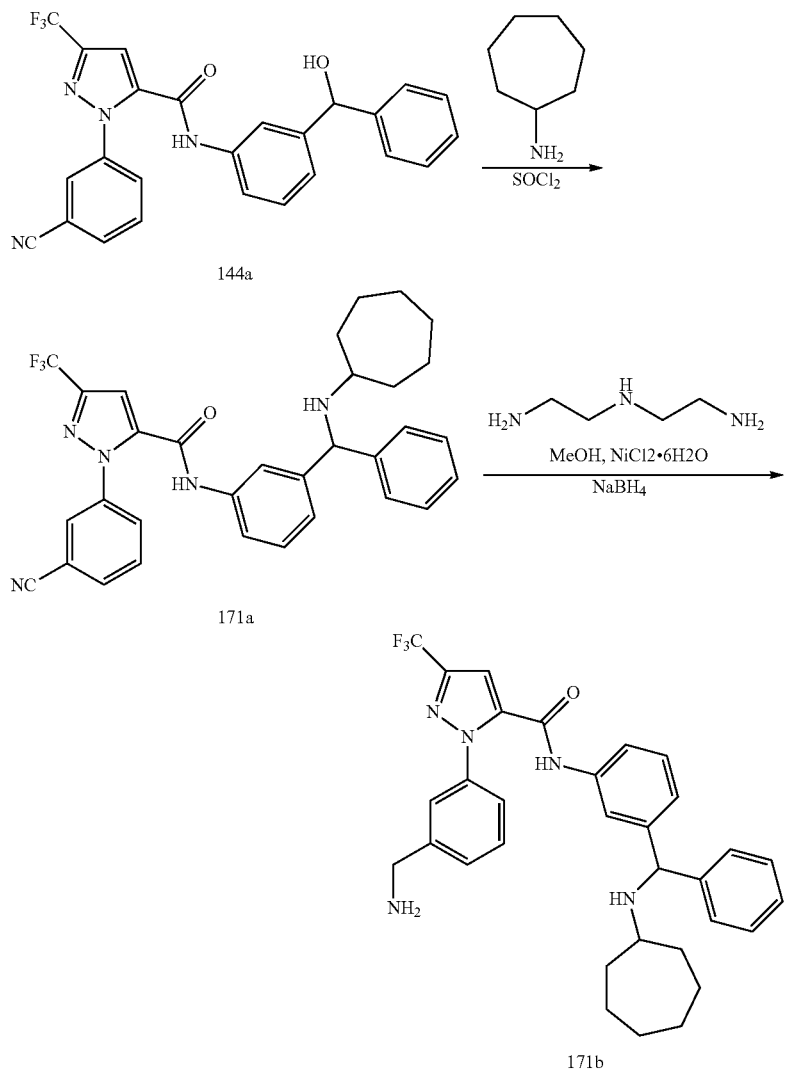

Preparation of 1-(3-(Aminomethyl)phenyl)-N-(3-((cycloheptylamino)(phenyl)methyl)phenyl)-3-(trifluoromethyl)-1H-pyrazole-5-carboxamide (171b)

Step-1: Preparation of 1-(3-cyanophenyl)-N-(3-((cycloheptylamino)(phenyl)methyl)phenyl)-3-(trifluoromethyl)-1H-pyrazole-5-carboxamide (171a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.16 mmol) in dichloromethane (50 mL) at 0° C. was added thionyl chloride (0.514 g, 4.325 mmol) and stirred at room temperature for 3 h. Cycloheptylamine (1.2 g, 10.81 mmol) was added and stirred for 30 min. The reaction mixture was concentrated in vacuum to dryness. The residue obtained was dissolved in acetonitrile (20 mL) and added Cycloheptylamine (1.2 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to 1-(3-cyanophenyl)-N-(3-((cycloheptylamino)(phenyl)methyl)phenyl)-3-(trifluoromethyl)-1H-pyrazole-5-carboxamide (171a) (1.01 g, 84%) as a yellow powder; $^1$H NMR (300 MHz, DMSO-$d_6$) δ 10.62 (s, 1H), 8.15 (t, J=1.8 Hz, 1H), 7.99 (dt, J=7.8, 1.3 Hz, 1H), 7.89 (ddd, J=8.2, 2.2, 1.1 Hz, 1H), 7.74 (d, J=8.0 Hz, 1H), 7.70 (s, 1H), 7.61 (t, J=1.7 Hz, 1H), 7.56-7.49 (m, 1H), 7.40-7.34 (m, 2H), 7.32-7.21 (m, 3H), 7.21-7.13 (m, 2H), 4.89 (s, 1H), 2.48-2.38 (m, 1H), 1.88-1.73 (m, 2H), 1.64-1.48 (m, 2H), 1.50-1.34 (m, 4H), 1.28-1.19 (m, 4H); MS (ES−) 556.3 (M−1).

Step-2: Preparation of 1-(3-(aminomethyl)phenyl)-N-(3-((cycloheptylamino)(phenyl)methyl)phenyl)-3-(trifluoromethyl)-1H-pyrazole-5-carboxamide (171b)

To a solution of 1-(3-cyanophenyl)-N-(3-((cycloheptylamino)(phenyl)methyl)phenyl)-3-(trifluoromethyl)-1H- pyrazole-5-carboxamide (171a) (1.0 g, 1.783 mmol) in MeOH (25 mL) cooled with ice/water was added nickel(II) chloride hexahydrate (0.532 g, 2.241 mmol) and followed by portion-wise addition of Sodium Borohydride (0.406 g, 10.758 mmol) over a period of 5 min. The reaction mixture was stirred at room temperature for 2 hrs and quenched with $N^1$-(2-aminoethyl)ethane-1,2-diamine (0.739 g, 7.172 mmol) followed by stirring for additional 0.5 h. The reaction mixture was concentrated in vacuum to dryness, and the residue obtained was purified by flash column chromatography (silica gel 60 g, eluting with 0-12% MeOH/DCM) to furnish 1-(3-(aminomethyl)phenyl)-N-(3-((cycloheptylamino)(phenyl)methyl)phenyl)-3-(trifluoromethyl)-1H-pyrazole-5-carboxamide (171b) (0.41 g, 41%) as a Off white solid.

$^1$H NMR (300 MHz, DMSO-$d_6$) δ 10.67 (s, 1H), 7.63-7.54 (m, 4H), 7.55-7.48 (m, 1H), 7.50-7.39 (m, 2H), 7.42-7.31 (m, 3H), 7.31-7.23 (m, 2H), 7.25-7.09 (m, 2H), 4.88 (s, 1H), 3.87 (s, 2H), 2.43 (dd, J=3.7, 1.7 Hz, 1H), 1.79 (s, 2H), 1.66-1.49 (m, 4H), 1.44-1.27 (m, 6H); $^{19}$F NMR (282 MHz, DMSO) δ -60.74; MS(ES+) 562.5 (M+1); (ES-) 596.3 (M+Cl); Analysis calculated for $C_{32}H_{34}F_3N_5O\cdot H_2O$: C, 66.31; H, 6.26; N, 12.08; Found: C, 66.47; H, 6.26; N, 11.76.

Preparation of 1-(3-(Aminomethyl)phenyl)-N-(3-((pentylamino)(phenyl)methyl)phenyl)-3-(trifluoromethyl)-1H-pyrazole-5-carboxamide (172b)

Step-1: Preparation of 2-(3-Cyano-phenyl)-5-trifluoromethyl-2H-pyrazole-3-carboxylic acid [3-(pentylamino-phenyl-methyl)-phenyl]-amide (172a)

To a solution of 2-(3-Cyano-phenyl)-5-trifluoromethyl-2H-pyrazole-3-carboxylic acid [3-(hydroxy-phenyl-methyl)-phenyl]-amide (144a) (1.0 g, 2.162 mmol) in dichloromethane (50 mL) at 0° C. was added thionyl chloride (0.514 g, 4.325 mmol) and stirred at room temperature for 3 h. Amyl amine (0.941 g, 10.81 mmol) was added and stirred for 30 min. The reaction mixture was concentrated in vacuum to dryness. The residue obtained was dissolved in acetonitrile (20 mL) and added Amyl amine (0.941 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting

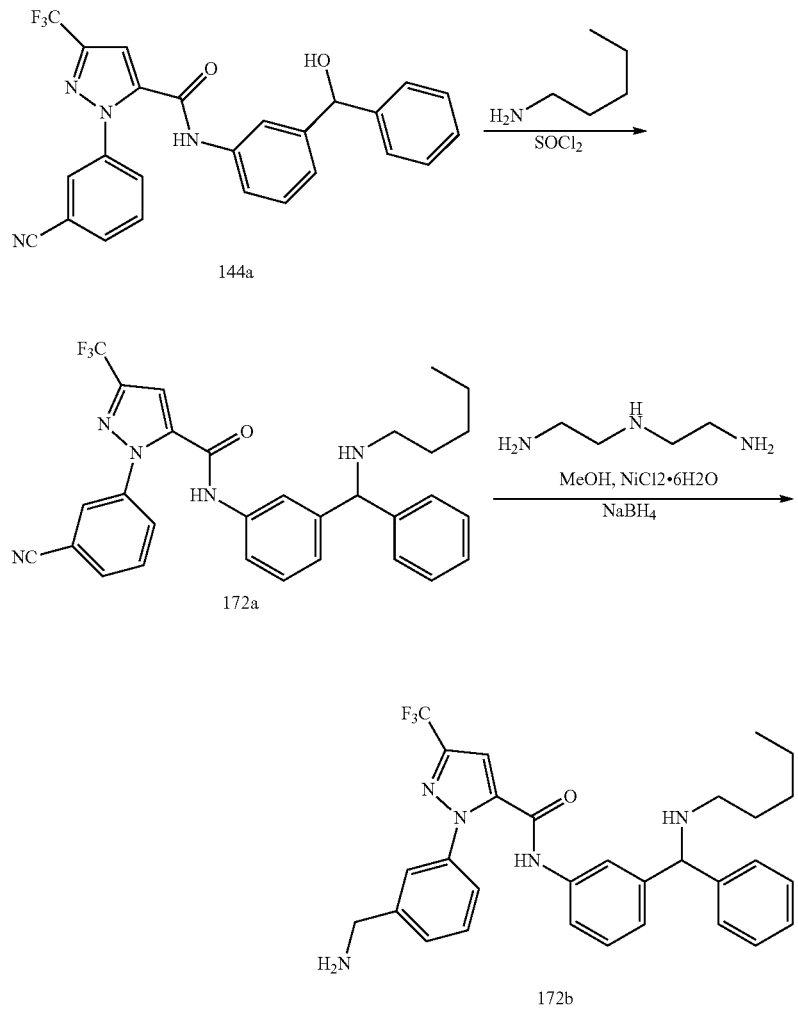

Scheme 172

0-25% ethyl acetate in hexane) to afford 2-(3-Cyano-phenyl)-5-trifluoromethyl-2H-pyrazole-3-carboxylic acid [3-(pentylamino-phenyl-methyl)-phenyl]-amide (172a) (1.050 gm) as Yellow powder; MS (ES) 530.3 (M−1).

Step-2: Preparation of 1-(3-(Aminomethyl)phenyl)-N-(3-((pentylamino)(phenyl)methyl)phenyl)-3-(trifluoromethyl)-1H-pyrazole-5-carboxamide (172b)

To a solution of 2-(3-Cyano-phenyl)-5-trifluoromethyl-2H-pyrazole-3-carboxylic acid [3-(pentylamino-phenyl-methyl)-phenyl]-amide (172a) (1.0 g, 1.882 mmol) in MeOH (20 mL) cooled with ice/water was added nickel(II) chloride hexahydrate (0.53 g, 2.258 mmol) and followed by portion-wise addition of Sodium Borohydride (0.42 g, 11.292 mmol) over a period of 5 min. The reaction mixture was stirred at room temperature for 2 hrs and quenched with N₁-(2-aminoethyl)ethane-1,2-diamine (0.48 g, 4.705 mmol) followed by stirring for additional 0.5 h. The reaction mixture was concentrated in vacuum to dryness, and the residue obtained was purified by flash column chromatography two times (silica gel 66 g, eluting with 0-12% MeOH/DCM) to furnish 1-(3-(Aminomethyl)phenyl)-N-(3-((pentylamino)(phenyl)methyl)phenyl)-3-(trifluoromethyl)-1H-pyrazole-5-carboxamide (172b) (0.020 gm) as a yellow solid; $^1$H NMR (300 MHz, DMSO-d$_6$) δ 10.68 (s, 1H), 7.63 (s, 1H), 7.59 (s, 4H), 7.55-7.42 (m, 2H), 7.45-7.32 (m, 3H), 7.32-7.23 (m, 2H), 7.25-7.13 (m, 2H), 4.73 (s, 1H), 3.92 (s, 1H), 2.39 (t, J=7.2 Hz, 2H), 1.43 (d, J=7.7 Hz, 2H), 1.22 (q, J=3.5 Hz, 4H), 0.90-0.77 (m, 3H); $^{19}$F NMR (282 MHz, DMSO) δ −60.75; MS(ES+) 536.4 (M+1); (ES−) 534.4 (M−1), 570.4 (M+Cl); Analysis calculated for C$_{30}$H$_{32}$F$_3$N$_5$O.1.25H$_2$O: C, 64.04; H, 6.27; N, 12.45; Found: C, 64.08; H, 6.13; N, 11.73.

Scheme 173

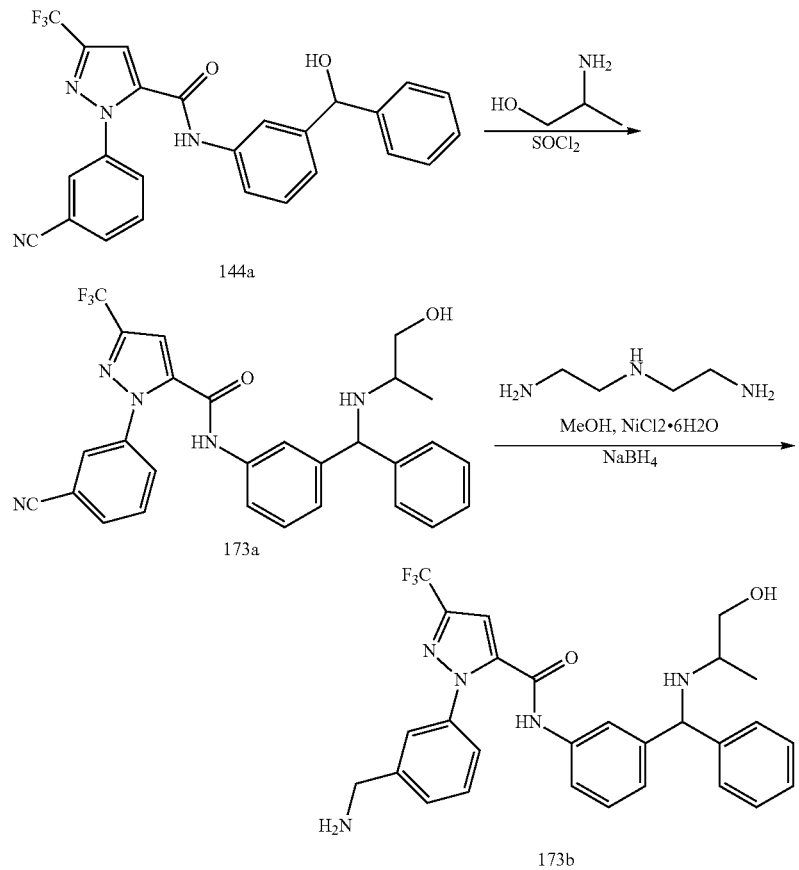

Preparation of 1-(3-(aminomethyl)phenyl)-N-(3-(((1-hydroxypropan-2-yl)amino)(phenyl)methyl)phenyl)-3-(trifluoromethyl)-1H-pyrazole-5-carboxamide (173b)

Step-1: Preparation of 1-(3-cyanophenyl)-N-(3-(((1-hydroxypropan-2-yl)amino)(phenyl)methyl)phenyl)-3-(trifluoromethyl)-1H-pyrazole-5-carboxamide (173a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.162 mmol) in dichloromethane (50 mL) at 0° C. was added thionyl chloride (0.514 g, 4.325 mmol) and stirred at room temperature for 3 h. Check TLC and 2-methyl ethanolamine (0.812 g, 10.81 mmol) was added and stirred for 30 min. Then reaction mixture was concentrated in vacuum to dryness. The residue obtained was dissolved in acetonitrile (20 mL) and added 2-methyl ethanolamine (0.812 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 1-(3-cyanophenyl)-N-(3-(((1-hydroxypropan-2-yl)amino)(phenyl)methyl)phenyl)-3-(trifluoromethyl)-1H-pyrazole-5-carboxamide (173a) (0.88 gm) as off-white sticky liquid; MS (ES−) 518.3.

Step-2: Preparation of 1-(3-(aminomethyl)phenyl)-N-(3-(((1-hydroxypropan-2-yl)amino)(phenyl)methyl)phenyl)-3-(trifluoromethyl)-1H-pyrazole-5-carboxamide (173b)

To a solution of 2-(3-Cyano-phenyl)-5-trifluoromethyl-2H-pyrazole-3-carboxylic acid {3-[(2-hydroxy-1-methyl-ethylamino)-phenyl-methyl]-phenyl}-amide (0.8 g, 1.539 mmol) in MeOH (20 mL) cooled with ice/water was added nickel(II) chloride hexahydrate (0.491 g, 2.068 mmol) and followed by portion-wise addition of Sodium Borohydride (0.349 g, 9.234 mmol) over a period of 5 min. The reaction mixture was stirred at room temperature for 2 hrs and quenched with $N^1$-(2-aminoethyl)ethane-1,2-diamine (0.635 g, 6.156 mmol) followed by stirring for additional 0.5 h. The reaction mixture was concentrated in vacuum to dryness, and the residue obtained was purified by flash column chromatography two times (silica gel 70 g, eluting with 0-12% MeOH/DCM) to furnish 1-(3-(aminomethyl)phenyl)-N-(3-(((1-hydroxypropan-2-yl)amino)(phenyl)methyl)phenyl)-3-(trifluoromethyl)-1H-pyrazole-5-carboxamide (173b) (0.180 gm) as a Light yellowish solid; $^1$H NMR (300 MHz, DMSO-$d_6$) δ 10.70 (s, 1H), 7.67 (s, 1H), 7.61 (d, J=2.1 Hz, 2H), 7.56-7.44 (m, 3H), 7.40 (ddd, J=7.9, 3.6, 1.7 Hz, 3H), 7.34-7.14 (m, 5H), 5.64 (s, 2H), 4.36 (s, 1H), 3.94 (s, 2H), 3.51 (t, J=6.7 Hz, 2H), 2.37 (dd, J=7.9, 5.7 Hz, 2H), 2.11 (s, 3H) $^{19}$F NMR (282 MHz, DMSO) δ −60.76; MS(ES+) 524.4 (M+1); (ES−) 558.3 (M+Cl); Analysis calculated for $C_{28}H_{28}F_3N_5O_2 \cdot 2H_2O$: C, 60.10; H, 5.76; N, 12.52; Found: C, 60.07; H, 5.70; N, 12.03.

Scheme 174

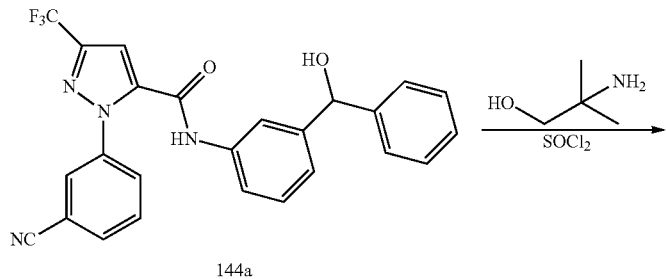

144a

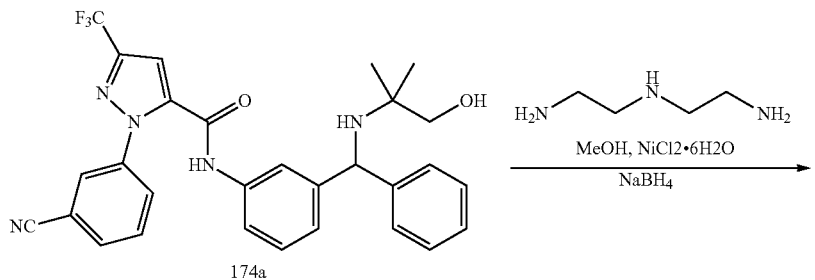

174a

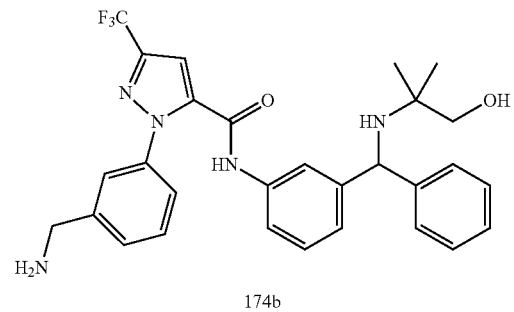

174b

Preparation of 1-(3-(aminomethyl)phenyl)-N-(3-(((1-hydroxy-2-methylpropan-2-yl)amino)(phenyl)methyl)phenyl)-3-(trifluoromethyl)-1H-pyrazole-5-carboxamide (174b)

Step-1: Preparation of 1-(3-cyanophenyl)-N-(3-(((1-hydroxy-2-methylpropan-2-yl)amino)(phenyl)methyl)phenyl)-3-(trifluoromethyl)-1H-pyrazole-5-carboxamide (174a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.162 mmol) in dichloromethane (50 mL) at 0° C. was added thionyl chloride (0.514 g, 4.325 mmol) and stirred at room temperature for 3 h. Check TLC and 2-amino-2-methyl-1-propanol (0.964 g, 10.81 mmol) was added and stirred for 30 min. Then reaction mixture was concentrated in vacuum to dryness. The residue obtained was dissolved in acetonitrile (20 mL) and added 2-amino-2-methyl-1-propanol (0.964 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 1-(3-cyanophenyl)-N-(3-(((1-hydroxy-2-methylpropan-2-yl)amino)(phenyl)methyl)phenyl)-3-(trifluoromethyl)-1H-pyrazole-5-carboxamide (174a) (0.9 gm) as yellow sticky semi-solid; MS (ES−) 532.3 (M−1).

Step-2: Preparation of 1-(3-(aminomethyl)phenyl)-N-(3-(((1-hydroxy-2-methylpropan-2-yl)amino)(phenyl)methyl)phenyl)-3-(trifluoromethyl)-1H-pyrazole-5-carboxamide (174b)

To a solution of 1-(3-cyanophenyl)-N-(3-(((1-hydroxy-2-methylpropan-2-yl)amino)(phenyl)methyl)phenyl)-3-(trifluoromethyl)-1H-pyrazole-5-carboxamide (174a) (0.9 g, 1.68 mmol) in MeOH (20 mL) cooled with ice/water was added nickel(II) chloride hexahydrate (0.479 g, 2.016 mmol) and followed by portion-wise addition of sodium borohydride (0.38 g, 10.08 mmol) over a period of 5 min. The reaction mixture was stirred at room temperature for 2 hrs and quenched with $N^1$-(2-aminoethyl)ethane-1,2-diamine (0.46 g, 4.5 mmol) followed by stirring for additional 0.5 h. The reaction mixture was concentrated in vacuum to dryness, and the residue obtained was purified by flash column chromatography (silica gel 65 g, eluting with 0-12% MeOH/DCM) to furnish 1-(3-(aminomethyl)phenyl)-N-(3-(((1-hydroxy-2-methylpropan-2-yl)amino)(phenyl)methyl)phenyl)-3-(trifluoromethyl)-1H-pyrazole-5-carboxamide (174b) (0.100 gm) as a white crystal; $^1$H NMR (300 MHz, DMSO-$d_6$) δ 10.66 (s, 1H), 7.65 (s, 1H), 7.57 (s, 1H), 7.55 (s, 1H), 7.52-7.47 (m, 1H), 7.46-7.42 (m, 2H), 7.42-7.27 (m, 4H), 7.27-7.19 (m, 3H), 7.19-7.11 (m, 1H), 4.97 (s, 1H), 4.64 (s, 1H), 3.20 (s, 2H), 0.86 (s, 6H); $^{19}$F NMR (282 MHz, DMSO) δ −60.73; MS(ES+) 538.4 (M+1); (ES−) 536.4 (M−1), 572.3 (M+Cl); Analysis calculated for $C_{29}H_{30}F_3N_5O_2 \cdot 0.75H_2O$: C, 63.20; H, 5.76; N, 12.71; Found: C, 63.11; H, 5.79; N, 12.02.

Scheme 175

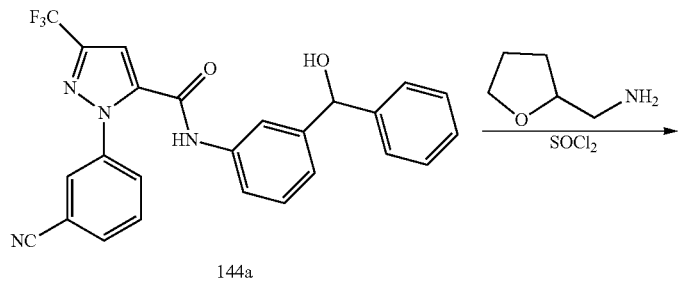

144a

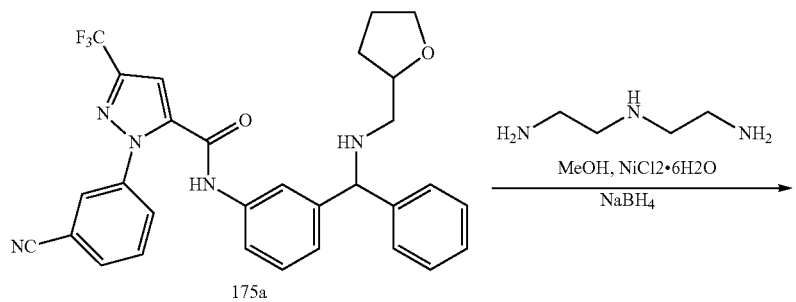

175a

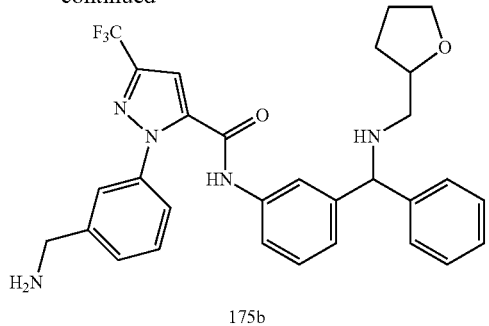

175b

Preparation of 1-(3-(aminomethyl)phenyl)-N-(3-(phenyl(((tetrahydrofuran-2-yl)methyl)amino) methyl)phenyl)-3-(trifluoromethyl)-1H-pyrazole-5-carboxamide (175b)

Step-1: Preparation of 1-(3-cyanophenyl)-N-(3-(phenyl(((tetrahydrofuran-2-yl)methyl)amino) methyl)phenyl)-3-(trifluoromethyl)-1H-pyrazole-5-carboxamide (175a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.162 mmol) in dichloromethane (50 mL) at 0° C. was added thionyl chloride (0.514 g, 4.325 mmol) and stirred at room temperature for 3 h. Check TLC and C-(Tetrahydro-furan-2-yl)-methylamine (1.093 g, 10.81 mmol) was added and stirred for 30 min. Then reaction mixture was concentrated in vacuum to dryness. The residue obtained was dissolved in acetonitrile (20 mL) and added C-(Tetrahydro-furan-2-yl)-methylamine (1.093 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 1-(3-cyanophenyl)-N-(3-(phenyl(((tetrahydrofuran-2-yl)methyl)amino)methyl)phenyl)-3-(trifluoromethyl)-1H-pyrazole-5-carboxamide (175a) (1.1 gm) as yellow-brown oil MS (ES−) 544.3 (M−1).

Step-2: Preparation of 1-(3-(aminomethyl)phenyl)-N-(3-(phenyl(((tetrahydrofuran-2-yl)methyl)amino) methyl)phenyl)-3-(trifluoromethyl)-1H-pyrazole-5-carboxamide (175b)

To a solution of 1-(3-cyanophenyl)-N-(3-(phenyl(((tetrahydrofuran-2-yl)methyl)amino)methyl)phenyl)-3-(trifluoromethyl)-1H-pyrazole-5-carboxamide (175a) (1.0 g, 1.833 mmol) in MeOH (20 mL) cooled with ice/water was added nickel(II) chloride hexahydrate (0.544 g, 2.291 mmol) and followed by portion-wise addition of Sodium Borohydride (0.416 g, 10.998 mmol) over a period of 5 min. The reaction mixture was stirred at room temperature for 2 hrs and quenched with $N^1$-(2-aminoethyl)ethane-1,2-diamine (0.756 g, 7.332 mmol) followed by stirring for additional 0.5 h. The reaction mixture was concentrated in vacuum to dryness, and the residue obtained was purified by flash column chromatography (silica gel 70 g, eluting with 0-12% MeOH/DCM) to furnish 1-(3-(aminomethyl)phenyl)-N-(3-(phenyl (((tetrahydrofuran-2-yl)methyl)amino)methyl)phenyl)-3-(trifluoromethyl)-1H-pyrazole-5-carboxamide (175b) (0.280 gm) as a Off white solid; $^1$H NMR (300 MHz, DMSO-$d_6$) δ 10.69 (s, 1H), 7.73-7.07 (m, 14H), 4.79 (s, 1H), 3.91 (d, J=6.9 Hz, 3H), 3.74-3.64 (m, 1H), 3.65-3.51 (m, 1H), 2.51-2.40 (m, 2H), 1.82 (ddt, J=33.3, 13.6, 6.8 Hz, 3H), 1.51 (dq, J=10.9, 7.1 Hz, 1H); $^{19}$F NMR (282 MHz, DMSO) δ −60.75; MS(ES+) 550.4 (M+1); (ES−) 548.4 (M−1), 584.4 (M+Cl); Analysis calculated for $C_{30}H_{30}F_3N_5O_2 \cdot 1.25H_2O$: C, 62.98; H, 5.73; N, 12.24; Found: C, 62.85; H, 5.57; N, 12.03.

Scheme 176

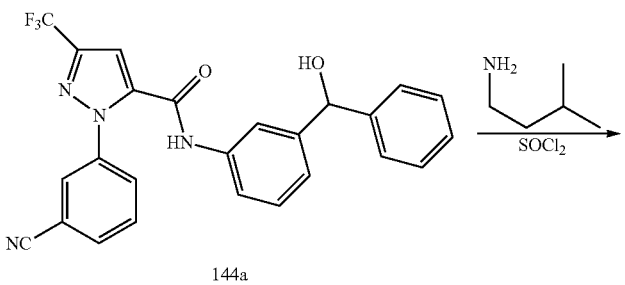

144a

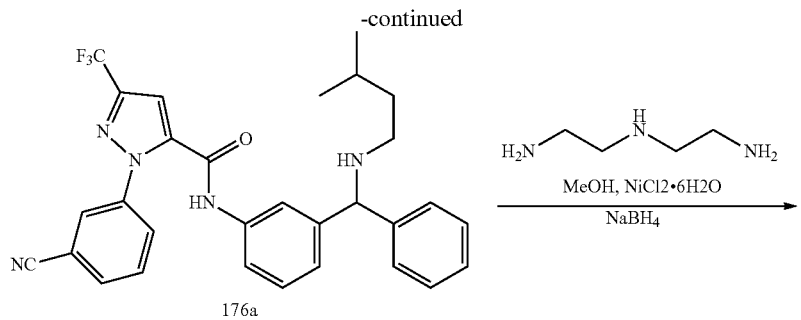

176a

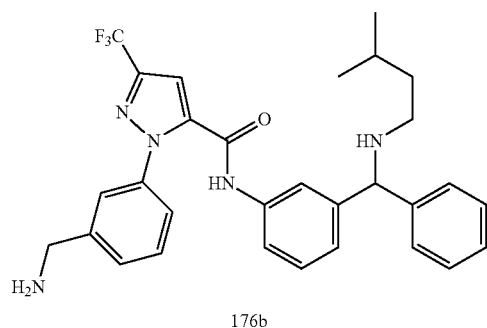

176b

Preparation of 1-(3-(aminomethyl)phenyl)-N-(3-((isopentylamino)(phenyl)methyl)phenyl)-3-(trifluoromethyl)-1H-pyrazole-5-carboxamide (176b)

Step-1: Preparation of 1-(3-cyanophenyl)-N-(3-((isopentylamino)(phenyl)methyl)phenyl)-3-(trifluoromethyl)-1H-pyrazole-5-carboxamide (176a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.162 mmol) in dichloromethane (50 mL) at 0° C. was added thionyl chloride (0.514 g, 4.325 mmol) and stirred at room temperature for 3 h. Check TLC and isoamyl amine (0.94 g, 10.81 mmol) was added and stirred for 30 min. Then reaction mixture was concentrated in vacuum to dryness. The residue obtained was dissolved in acetonitrile (20 mL) and added isoamyl amine (0.94 gm, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 1-(3-cyanophenyl)-N-(3-((isopentylamino)(phenyl)methyl)phenyl)-3-(trifluoromethyl)-1H-pyrazole-5-carboxamide (176a) (1.0 gm) as yellow oil; MS (ES−) 530.3 (M−1).

Step-2: Preparation of 1-(3-(aminomethyl)phenyl)-N-(3-((isopentylamino)(phenyl)methyl)phenyl)-3-(trifluoromethyl)-1H-pyrazole-5-carboxamide (176b)

To a solution of 1-(3-cyanophenyl)-N-(3-((isopentylamino)(phenyl)methyl)phenyl)-3-(trifluoromethyl)-1H-pyrazole-5-carboxamide (176a) (1.0 g, 1.882 mmol) in MeOH (20 mL) cooled with ice/water was added nickel(II) chloride hexahydrate (0.53 g, 2.258 mmol) and followed by portion-wise addition of Sodium Borohydride (42 g, 11.292 mmol) over a period of 5 min. The reaction mixture was stirred at room temperature for 2 hrs and quenched with $N^1$-(2-aminoethyl)ethane-1,2-diamine (0.48 g, 4.705 mmol) followed by stirring for additional 0.5 h. The reaction mixture was concentrated in vacuum to dryness, and the residue obtained was purified by flash column chromatography (silica gel 70 g, eluting with 0-12% MeOH/DCM) to furnish 1-(3-(aminomethyl)phenyl)-N-(3-((isopentylamino)(phenyl)methyl)phenyl)-3-(trifluoromethyl)-1H-pyrazole-5-carboxamide (176b) (0.350 gm) as a white solid; $^1$H NMR (300 MHz, DMSO-$d_6$) δ 10.68 (s, 1H), 7.63 (t, J=1.8 Hz, 1H), 7.58 (d, J=2.6 Hz, 2H), 7.52 (dt, J=7.8, 1.7 Hz, 1H), 7.48 (d, J=1.7 Hz, 1H), 7.44 (d, J=7.5 Hz, 1H), 7.37 (ddt, J=5.0, 3.9, 1.9 Hz, 3H), 7.31-7.12 (m, 5H), 4.73 (s, 1H), 3.89 (s, 2H), 2.45-2.35 (m, 2H), 1.60 (dq, J=13.2, 6.6 Hz, 1H), 1.40-1.28 (m, 2H), 0.80 (d, J=6.6 Hz, 6H); $^{19}$F NMR (282 MHz, DMSO) δ −60.73; MS(ES+) 536.4 (M+1); (ES−) 570.4 (M+Cl); Analysis calculated for $C_{30}H_{32}F_3N_5O \cdot 1.25H_2O$: C, 64.56; H, 6.23; N, 12.55; Found: C, 64.42; H, 6.00; N, 12.53.

Scheme 177

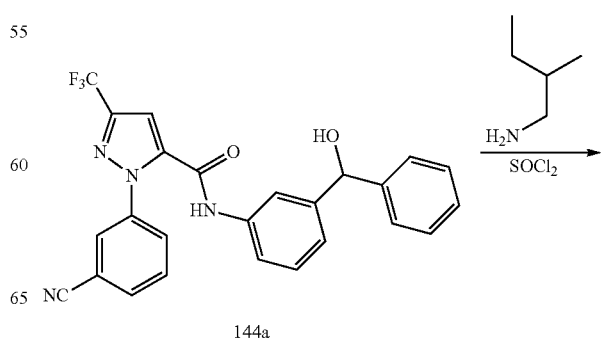

144a

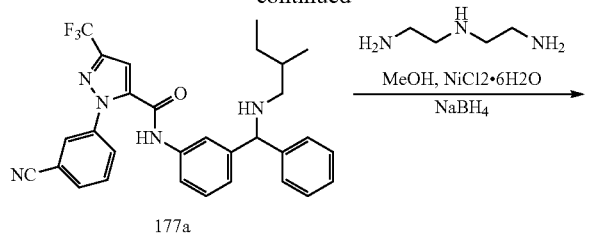

177a

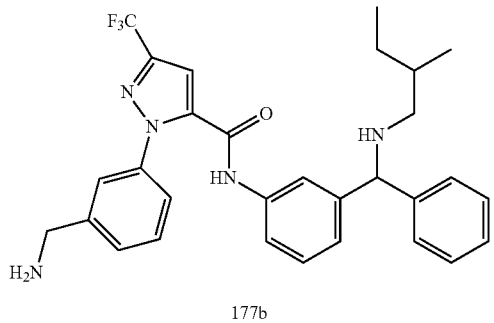

177b

Preparation of 1-(3-(Aminomethyl)phenyl)-N-(3-(((2-methylbutyl)amino)(phenyl)methyl)phenyl)-3-(trifluoromethyl)-1H-pyrazole-5-carboxamide (177b)

Step-1: Preparation of 1-(3-cyanophenyl)-N-(3-(((2-methylbutyl)amino)(phenyl)methyl)phenyl)-3-(trifluoromethyl)-1H-pyrazole-5-carboxamide (177a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.162 mmol) in dichloromethane (50 mL) at 0° C. was added thionyl chloride (0.514 g, 4.325 mmol) and stirred at room temperature for 3 h. Check TLC and 2-Methyl-butylamine (0.942 g, 10.81 mmol) was added and stirred for 30 min. Then reaction mixture was concentrated in vacuum to dryness. The residue obtained was dissolved in acetonitrile (20 mL) and added 2-Methyl-butylamine (0.942 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 1-(3-cyanophenyl)-N-(3-(((2-methylbutyl)amino)(phenyl)methyl)phenyl)-3-(trifluoromethyl)-1H-pyrazole-5-carboxamide (177a) (0.8 gm) as yellow oil; MS (ES−) 530.3 (M−1).

Step-2: Preparation of 1-(3-(Aminomethyl)phenyl)-N-(3-(((2-methylbutyl)amino)(phenyl)methyl)phenyl)-3-(trifluoromethyl)-1H-pyrazole-5-carboxamide (177b)

To a solution of afford 1-(3-cyanophenyl)-N-(3-(((2-methylbutyl)amino)(phenyl)methyl)phenyl)-3-(trifluoromethyl)-1H-pyrazole-5-carboxamide (177a) (0.8 g, 1.505 mmol) in MeOH (20 mL) cooled with ice/water was added nickel(II) chloride hexahydrate (0.43 g, 1.806 mmol) and followed by portion-wise addition of Sodium Borohydride (0.34 g, 9.03 mmol) over a period of 5 min. The reaction mixture was stirred at room temperature for 2 hrs and quenched with $N^1$-(2-aminoethyl)ethane-1,2-diamine (0.388 g, 3.762 mmol) followed by stirring for additional 0.5 h. The reaction mixture was concentrated in vacuum to dryness, and the residue obtained was purified by flash column chromatography (silica gel 60 g, eluting with 0-12% MeOH/DCM) to furnish 1-(3-(Aminomethyl)phenyl)-N-(3-(((2-methylbutyl)amino)(phenyl)methyl)phenyl)-3-(trifluoromethyl)-1H-pyrazole-5-carboxamide (177b) pure (0.400 gm) as a colorless oil; $^1$H NMR (300 MHz, DMSO-$d_6$) δ 10.65 (s, 1H), 7.67-7.11 (m, 14H), 4.71 (s, 1H), 3.88 (s, 2H), 2.39-2.14 (m, 2H), 1.57-1.32 (m, 2H), 1.07 (dt, J=13.8, 7.3 Hz, 1H), 0.92-0.71 (m, 6H); $^{19}$F NMR (282 MHz, DMSO) δ −60.35; MS(ES+) 536.4 (M+1); (ES−) 570.3 (M+Cl); Analysis calculated for $C_{30}H_{32}F_3N_5O \cdot 0.75H_2O$: C, 65.62; H, 6.15; N, 12.75; Found: C, 65.62; H, 6.25; N, 12.03.

Scheme 178

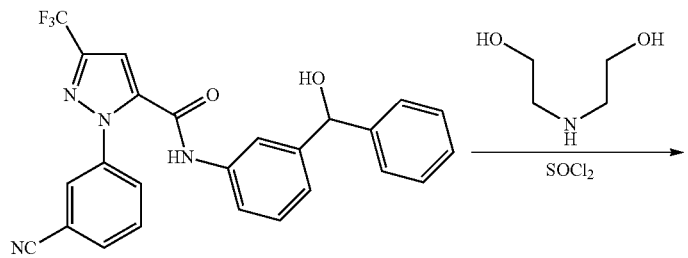

144a

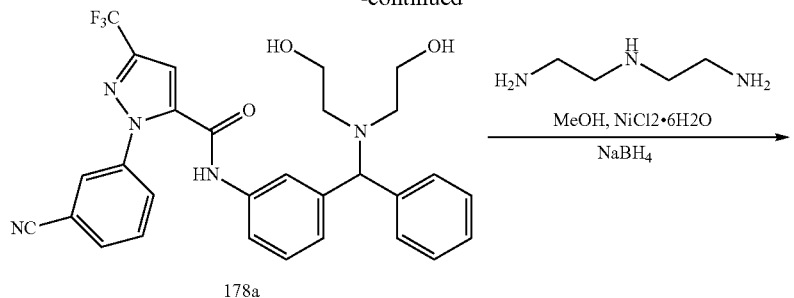

178a

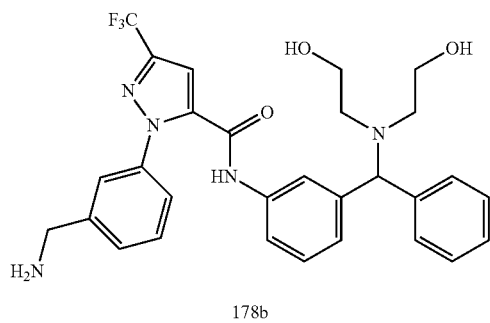

178b

Preparation of 1-(3-(aminomethyl)phenyl)-N-(3-((bis(2-hydroxyethyl)amino)(phenyl)methyl)phenyl)-3-(trifluoromethyl)-1H-pyrazole-5-carboxamide (178b)

Step-1: Preparation of N-(3-((bis(2-hydroxyethyl)amino)(phenyl)methyl)phenyl)-1-(3-cyanophenyl)-3-(trifluoromethyl)-1H-pyrazole-5-carboxamide (178a)

To a solution of (144a) (1.0 g, 2.162 mmol) in dichloromethane (50 mL) at 0° C. was added thionyl chloride (0.514 g, 4.325 mmol) and stirred at room temperature for 3 h. Check TLC and 2-(2-Hydroxy-ethylamino)-ethanol (1.13 g, 10.81 mmol) was added and stirred for 30 min. Then reaction mixture was concentrated in vacuum to dryness. The residue obtained was dissolved in acetonitrile (20 mL) and added 2-(2-Hydroxy-ethylamino)-ethanol (1.13 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford N-(3-((bis(2-hydroxyethyl)amino)(phenyl)methyl)phenyl)-1-(3-cyanophenyl)-3-(trifluoromethyl)-1H-pyrazole-5-carboxamide (178a) (0.500 gm) as yellow oil. (MS) (ES-) 548.3 (M-1).

Step-2: Preparation of 1-(3-(aminomethyl)phenyl)-N-(3-((bis(2-hydroxyethyl)amino)(phenyl)methyl)phenyl)-3-(trifluoromethyl)-1H-pyrazole-5-carboxamide (178b)

To a solution of N-(3-((bis(2-hydroxyethyl)amino)(phenyl)methyl)phenyl)-1-(3-cyanophenyl)-3-(trifluoromethyl)-1H-pyrazole-5-carboxamide (178a) (0.5 g, 0.910 mmol) in MeOH (20 mL) cooled with ice/water was added nickel(II) chloride hexahydrate (0.25 g, 1.092 mmol) and followed by portion-wise addition of Sodium Borohydride (0.20 g, 5.46 mmol) over a period of 5 min. The reaction mixture was stirred at room temperature for 2 hrs and quenched with $N^1$-(2-aminoethyl)ethane-1,2-diamine (0.23 g, 2.275 mmol) followed by stirring for additional 0.5 h. The reaction mixture was concentrated in vacuum to dryness, and the residue obtained was purified by flash column chromatography (silica gel 60 g, eluting with 0-12% MeOH/DCM) to furnish 1-(3-(aminomethyl)phenyl)-N-(3-((bis(2-hydroxyethyl)amino)(phenyl)methyl)phenyl)-3-(trifluoromethyl)-1H-pyrazole-5-carboxamide (178b) (0.080 gm) as a white crystal; $^1$H NMR (300 MHz, DMSO-$d_6$) δ 10.69 (s, 1H), 7.74-7.33 (m, 10H), 7.36-7.22 (m, 2H), 7.27-7.14 (m, 2H), 4.84 (s, 1H), 3.97 (s, 2H), 3.44 (t, J=6.9 Hz, 4H), 2.55 (t, J=6.9 Hz, 4H); $^{19}$F NMR (282 MHz, DMSO) δ -60.57; MS (ES+) 554.4 (M+1); (ES-) 552.3 (M-1), 588.3 (M+Cl); Analysis calculated for $C_{29}H_{30}F_3N_5O_3 \cdot HCl \cdot 3H_2O$: C, 54.08; H, 5.79; N, 10.87; Found: C, 54.03; H, 5.78; N, 11.01.

Scheme 179

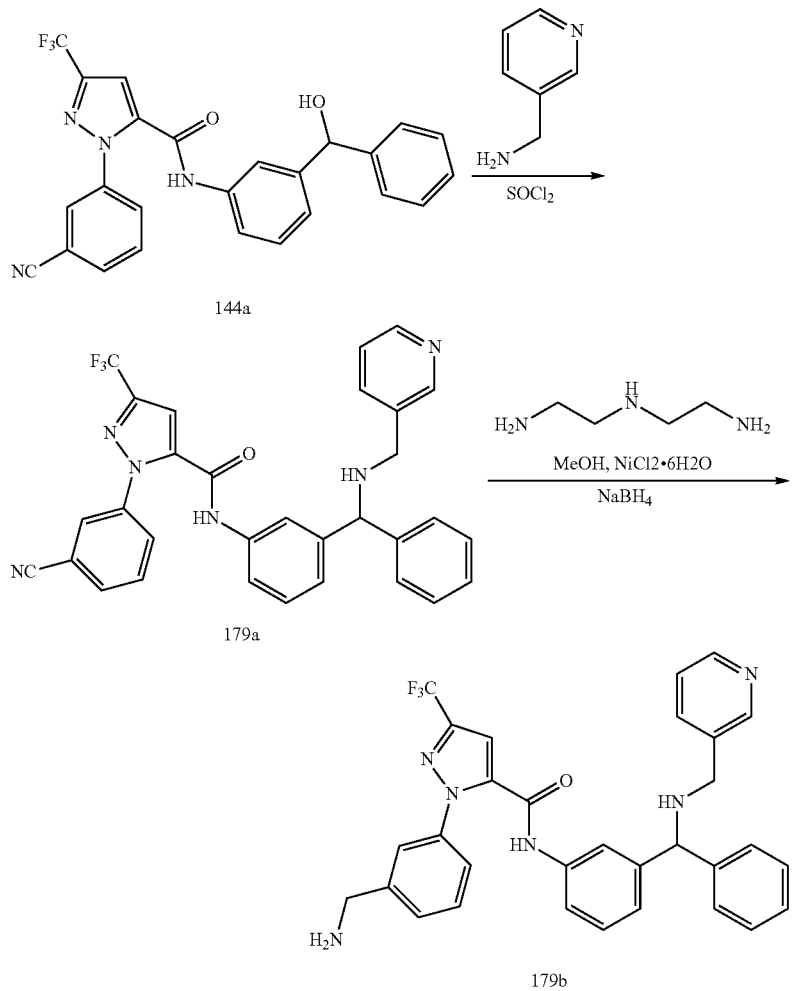

Preparation of 1-(3-(Aminomethyl)phenyl)-N-(3-(phenyl((pyridin-3-ylmethyl)amino)methyl)phenyl)-3-(trifluoromethyl)-1H-pyrazole-5-carboxamide (179b)

Step-1: Preparation of 1-(3-cyanophenyl)-N-(3-(phenyl((pyridin-3-ylmethyl)amino)methyl)phenyl)-3-(trifluoromethyl)-1H-pyrazole-5-carboxamide (179a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.162 mmol) in dichloromethane (50 mL) at 0° C. was added thionyl chloride (0.514 g, 4.325 mmol) and stirred at room temperature for 3 h. Check TLC and C-Pyridin-3-yl-methylamine (1.168 g, 10.81 mmol) was added and stirred for 30 min. Then reaction mixture was concentrated in vacuum to dryness. The residue obtained was dissolved in acetonitrile (20 mL) and added C-Pyridin-3-yl-methylamine (1.168 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 1-(3-cyanophenyl)-N-(3-(phenyl((pyridin-3-ylmethyl)amino)methyl)phenyl)-3-(trifluoromethyl)-1H-pyrazole-5-carboxamide (179a) (0.580 gm) as a white solid; MS (ES−) 551.2 (M−1).

Step-2: Preparation of 1-(3-(Aminomethyl)phenyl)-N-(3-(phenyl((pyridin-3-ylmethyl)amino)methyl)phenyl)-3-(trifluoromethyl)-1H-pyrazole-5-carboxamide (179b)

To a solution of 1-(3-cyanophenyl)-N-(3-(phenyl((pyridin-3-ylmethyl)amino)methyl)phenyl)-3-(trifluoromethyl)-1H-pyrazole-5-carboxamide (179a) (0.5 g, 0.9048 mmol) in MeOH (20 mL) cooled with ice/water was added nickel(II) chloride hexahydrate (0.25 g, 1.085 mmol) and followed by portion-wise addition of Sodium Borohydride (0.26 g, 5.428 mmol) over a period of 5 min. The reaction mixture was stirred at room temperature for 2 hrs and quenched with N1-(2-aminoethyl)ethane-1,2-diamine (0.23 g, 2.262 mmol) followed by stirring for additional 0.5 h. The reaction mixture was concentrated in vacuum to dryness, and the residue obtained was purified by flash column chromatography (silica gel 60 g, eluting with 0-12% MeOH/DCM) to furnish 1-(3-(Aminomethyl)phenyl)-N-(3-(phenyl((pyridin-3-ylmethyl)amino)methyl)phenyl)-3-(trifluoromethyl)-1H-pyrazole-5-carboxamide (179b) (0.055 gm) as a white solid; $^1$H NMR (300 MHz, DMSO-$d_6$) δ 10.68 (s, 1H), 8.48 (s, 1H), 8.44 (d, J=4.9 Hz, 1H), 7.78-7.71 (m, 1H), 7.68 (s, 1H), 7.62-7.57 (m, 2H), 7.58-7.51 (m, 1H), 7.48 (d, J=6.5 Hz, 2H), 7.41 (d, J=6.1 Hz, 3H), 7.36-7.26 (m, 3H), 7.28-7.16 (m, 3H), 4.74 (s, 1H), 3.93 (s, 2H), 3.62 (s, 2H); $^{19}$F NMR (282 MHz, DMSO) δ −60.43; MS (ES+) 557.4 (M+1); (ES−) 555.4 (M−1), 591.3 (M+Cl); Analysis calculated for $C_{31}H_{27}F_3N_6O \cdot HCl \cdot 3.25H_2O$: C, 57.14; H, 5.34; N, 12.90; Found: C, 57.37; H, 5.14; N, 12.33.

for 30 min. Then reaction mixture was concentrated in vacuum to dryness. The residue obtained was dissolved in acetonitrile (20 mL) and added Butylamine (0.79 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford N-(3-((butylamino)(phenyl)methyl)phenyl)-1-(3-cyanophenyl)-3-(trifluoromethyl)-1H-pyrazole-5-carboxamide (180a) (0.960 gm) as a brown oil; MS (ES−) 516.3 (M−1).

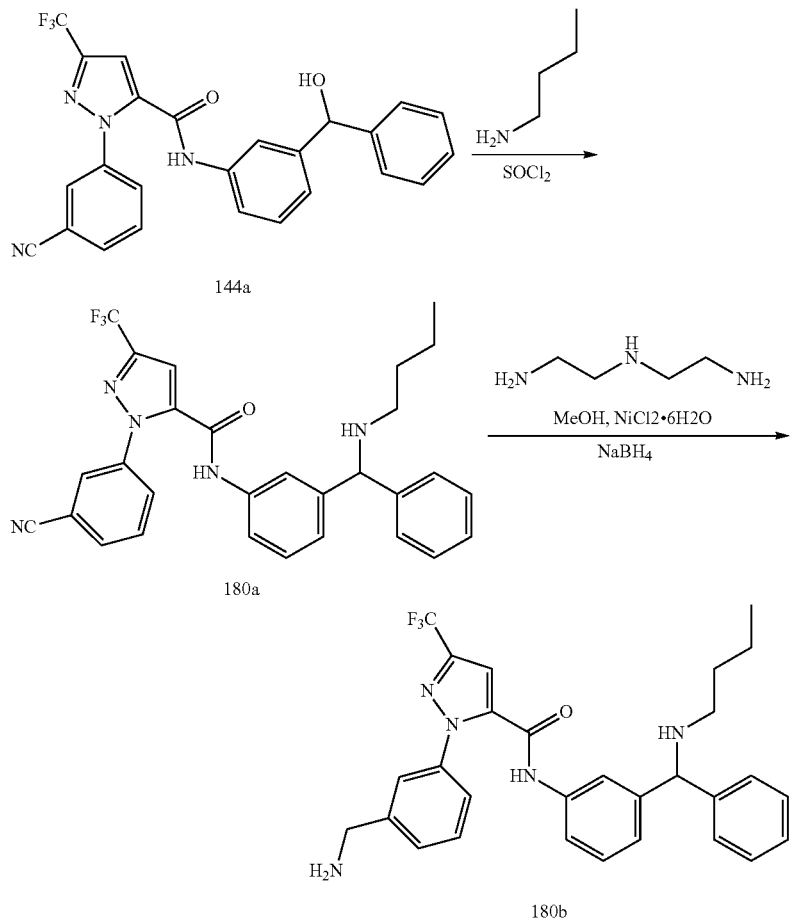

Scheme 180

Preparation of 1-(3-(Aminomethyl)phenyl)-N-(3-((butylamino)(phenyl)methyl)phenyl)-3-(trifluoromethyl)-1H-pyrazole-5-carboxamide (180b)

Step-1: Preparation of N-(3-((butylamino)(phenyl)methyl)phenyl)-1-(3-cyanophenyl)-3-(trifluoromethyl)-1H-pyrazole-5-carboxamide (180a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.162 mmol) in dichloromethane (50 mL) at 0° C. was added thionyl chloride (0.514 g, 4.325 mmol) and stirred at room temperature for 3 h. Check TLC and Butylamine (0.79 g, 10.81 mmol) was added and stirred Step-2: Preparation of 1-(3-(Aminomethyl)phenyl)-N-(3-((butylamino)(phenyl)methyl)phenyl)-3-(trifluoromethyl)-1H-pyrazole-5-carboxamide (180b)

To a solution of N-(3-((butylamino)(phenyl)methyl)phenyl)-1-(3-cyanophenyl)-3-(trifluoromethyl)-1H-pyrazole-5-carboxamide (180a) (0.960 g, 1.856 mmol) in MeOH (20 mL) cooled with ice/water was added nickel(II) chloride hexahydrate (0.551 g, 2.32 mmol) and followed by portionwise addition of Sodium Borohydride (0.421 g, 11.136 mmol) over a period of 5 min. The reaction mixture was stirred at room temperature for 2 hrs and quenched with $N^1$-(2-aminoethyl)ethane-1,2-diamine (0.478 g, 4.527 mmol) followed by stirring for additional 0.5 h. The reaction mixture was concentrated in vacuum to dryness, and the residue obtained was purified by flash column chromatography (silica gel 60 g, eluting with 0-12% MeOH/DCM) to furnish 1-(3-(Aminomethyl)phenyl)-N-(3-((butylamino)(phenyl)methyl)phenyl)-3-(trifluoromethyl)-1H-pyrazole-5-carboxamide (180b) (0.040 gm) as a off white solid; $^1$H NMR (300 MHz, DMSO-$d_6$) δ 10.76 (s, 1H), 7.70 (d, J=1.8 Hz, 1H), 7.66 (d, J=2.7 Hz, 2H), 7.63-7.45 (m, 4H), 7.39 (d, J=7.1 Hz, 2H), 7.34-7.12 (m, 5H), 4.76 (s, 1H), 4.09 (s, 2H), 2.41 (t, J=7.0 Hz, 2H), 1.43 (q, J=7.3 Hz, 2H), 1.28 (q, J=7.3 Hz, 2H), 0.83 (t, J=7.2 Hz, 3H); $^{19}$F NMR (282 MHz, DMSO) δ −60.77; MS (ES+) 522.4 (M+1); (ES−) 520.3 (M−1), 556.4 (M+Cl); Analysis calculated for $C_{29}H_{30}F_3N_5O·HCl·1.25H_2O$: C, 60.00; H, 5.82; N, 12.06; Found: C, 60.34; H, 5.95; N, 11.52.

Preparation of 1-(3-(Aminomethyl)phenyl)-N-(3-((((trans)-4-hydroxycyclohexyl)amino)(phenyl)methyl)phenyl)-3-(trifluoromethyl)-1H-pyrazole-5-carboxamide (181b)

Step-1: Preparation of 1-(3-cyanophenyl)-N-(3-((((trans)-4-hydroxycyclohexyl)amino)(phenyl)methyl)phenyl)-3-(trifluoromethyl)-1H-pyrazole-5-carboxamide (181a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.162 mmol) in dichloromethane (50 mL) at 0° C. was added thionyl chloride (0.514 g, 4.325 mmol) and stirred at room temperature for 3 h. Check TLC

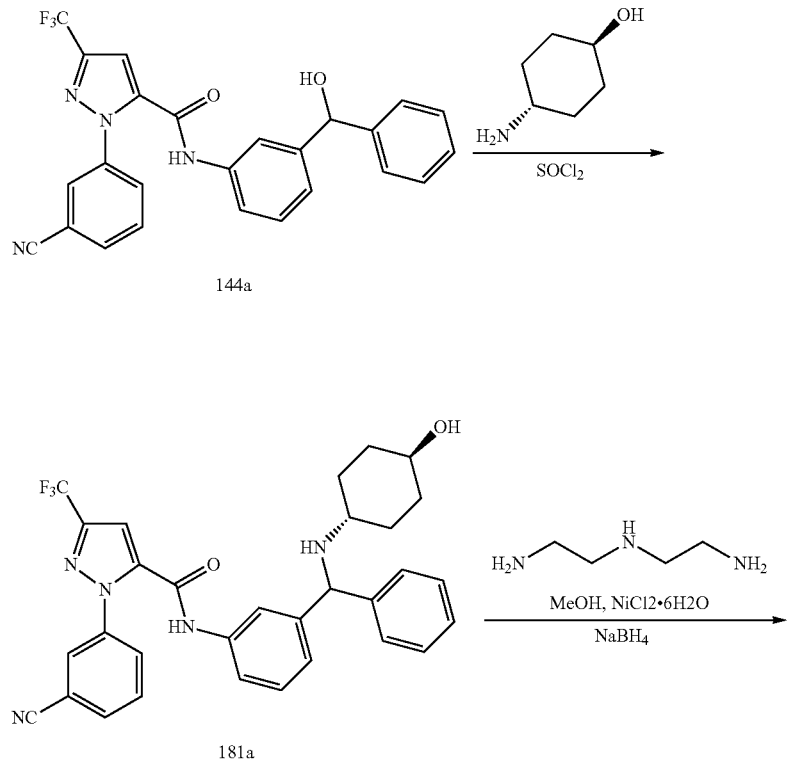

Scheme 181

144a

181a

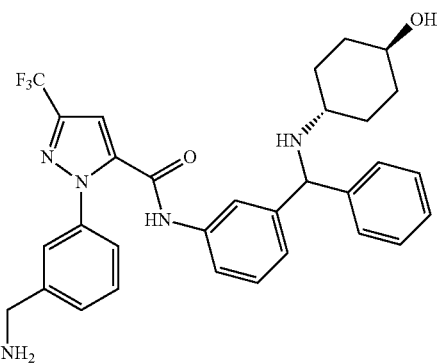

181b and 4-Amino-cyclohexanol (1.25 g, 10.81 mmol) was added and stirred for 30 min. Then reaction mixture was concentrated in vacuum to dryness. The residue obtained was dissolved in acetonitrile (20 mL) and added trans-4-Amino-cyclohexanol (1.25 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 1-(3-cyanophenyl)-N-(3-((((trans)-4-hydroxycyclohexyl)amino)(phenyl)methyl)phenyl)-3-(trifluoromethyl)-1H-pyrazole-5-carboxamide (181a) (0.600 gm) as a brownish solid; MS (ES−) 558.3 (M−1).

Step-2: Preparation of 1-(3-(Aminomethyl)phenyl)-N-(3-((((trans)-4-hydroxycyclohexyl)amino)(phenyl)methyl)phenyl)-3-(trifluoromethyl)-1H-pyrazole-5-carboxamide (181b)

To a solution of 1-(3-cyanophenyl)-N-(3-((((trans)-4-hydroxycyclohexyl)amino)(phenyl)methyl)phenyl)-3-(trifluoromethyl)-1H-pyrazole-5-carboxamide (181a) (0.600 g, 1.072 mmol) in MeOH (20 mL) cooled with ice/water was added nickel(II) chloride hexahydrate (0.3 g, 2.32 mmol) and followed by portion-wise addition of Sodium Borohydride (0.2 g, 6.432 mmol) over a period of 5 min. The reaction mixture was stirred at room temperature for 2 hrs and quenched with $N^1$-(2-aminoethyl)ethane-1,2-diamine (0.276 g, 2.68 mmol) followed by stirring for additional 0.5 h. The reaction mixture was concentrated in vacuum to dryness, and the residue obtained was purified by flash column chromatography (silica gel 60 g, eluting with 0-12% MeOH/DCM) to furnish 1-(3-(Aminomethyl)phenyl)-N-(3-((((trans)-4-hydroxycyclohexyl)amino)(phenyl)methyl)phenyl)-3-(trifluoromethyl)-1H-pyrazole-5-carboxamide (181b) pure (0.140 gm) as a white solid; $^1$H NMR (300 MHz, DMSO-$d_6$) δ 10.68 (s, 1H), 7.60 (s, 1H), 7.57 (s, 1H), 7.58-7.47 (m, 3H), 7.39-7.29 (m, 3H), 7.48-7.30 (m, 4H), 7.31-7.22 (m, 2H), 7.24-7.06 (m, 3H), 4.93 (s, 1H), 4.43 (s, 1H), 3.82 (s, 2H), 2.31-2.11 (m, 1H), 1.94-1.83 (m, 1H), 1.79-1.66 (m, 2H), 1.18-0.86 (m, 4H); $^{19}$F NMR (282 MHz, DMSO) δ −60.73; MS (ES+) 564.4 (M+1); (ES−) 562.5 (M−1), 598.4 (M+Cl); Analysis calculated for $C_{31}H_{32}F_3N_5O_2 \cdot 2.25H_2O$: C, 61.63; H, 6.09; N, 11.59; Found: C, 61.69; H, 5.89; N, 11.38.

Scheme 182

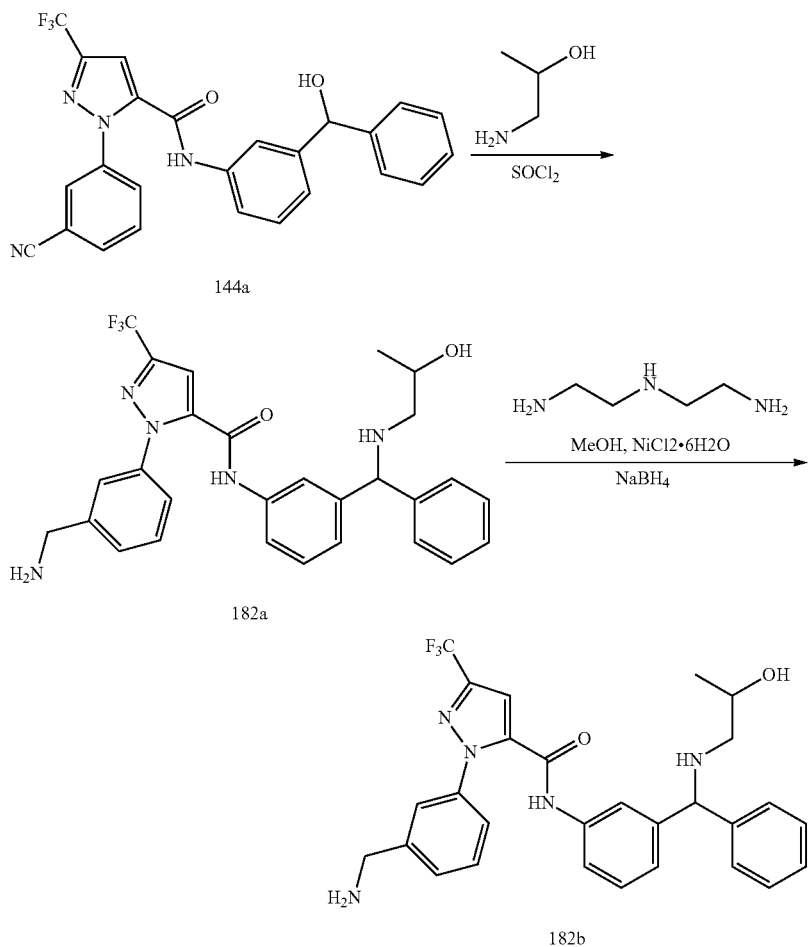

Step-1: Preparation of 1-(3-(aminomethyl)phenyl)-N-(3-(((2-hydroxypropyl)amino)(phenyl)methyl) phenyl)-3-(trifluoromethyl)-1H-pyrazole-5-carboxamide (182a)

To a solution of 1-(3-cyanophenyl)-N-(3-(hydroxy(phenyl)methyl)phenyl)-3-(trifluoromethyl)-1H-pyrazole-5-carboxamide (1.0 g, 2.162 mmol) in dichloromethane (50 mL) at 0° C. was added thionyl chloride (0.514 g, 4.325 mmol) and stirred at room temperature for 3 h. Check TLC and 1-Amino-propan-2-ol (0.811 g, 10.81 mmol) was added and stirred for 30 min. Then reaction mixture was concentrated in vacuum to dryness. The residue obtained was dissolved in acetonitrile (20 mL) and added 1-Amino-propan-2-ol (0.811 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 1-(3-(aminomethyl)phenyl)-N-(3-(((2-hydroxypropyl)amino)(phenyl)methyl)phenyl)-3-(trifluoromethyl)-1H-pyrazole-5-carboxamide (182a) (0.600 gm) as a brownish oil; MS (ES−) 518.3 (M−1).

Step-2: Preparation of 1-(3-(aminomethyl)phenyl)-N-(3-(((2-hydroxypropyl)amino)(phenyl)methyl) phenyl)-3-(trifluoromethyl)-1H-pyrazole-5-carboxamide (182b)

To a solution of afford 1-(3-(aminomethyl)phenyl)-N-(3-(((2-hydroxypropyl)amino)(phenyl)methyl)phenyl)-3-(trifluoromethyl)-1H-pyrazole-5-carboxamide (182a) (0.600 g, 1.154 mmol) in MeOH (20 mL) cooled with ice/water was added nickel(II) chloride hexahydrate (0.32 g, 1.38 mmol) and followed by portion-wise addition of Sodium Borohydride (0.26 g, 6.924 mmol) over a period of 5 min. The reaction mixture was stirred at room temperature for 2 hrs and quenched with $N^1$-(2-aminoethyl)ethane-1,2-diamine (0.29 g, 2.885 mmol) followed by stirring for additional 0.5 h. The reaction mixture was concentrated in vacuum to dryness, and the residue obtained was purified by flash column chromatography (silica gel 60 g, eluting with 0-12% MeOH/DCM) to furnish 1-(3-(aminomethyl)phenyl)-N-(3-(((2-hydroxypropyl)amino)(phenyl)methyl)phenyl)-3-(trifluoromethyl)-1H-pyrazole-5-carboxamide (182b) pure (0.020 gm) as a white solid; $^1$H NMR (300 MHz, DMSO-$d_6$) δ 10.70 (d, J=1.8 Hz, 1H), 7.64 (s, 1H), 7.61-7.34 (m, 8H), 7.33-7.15 (m, 5H), 4.75 (s, 1H), 4.68-4.40 (m, 1H), 3.89 (s, 2H), 3.73 (q, J=6.7, 6.3 Hz, 1H), 2.35 (d, J=6.0 Hz, 2H), 1.02 (d, J=6.1 Hz, 3H); $^{19}$F NMR (282 MHz, DMSO) δ −60.74; MS (ES+) 524.4 (M+1); (ES−) 522.3 (M−1), 558.3 (M+Cl); Analysis calculated for $C_{28}H_{28}F_3N_5O_2 \cdot 2.75H_2O$: C, 58.68; H, 5.89; N, 12.22; Found: C, 59.01; H, 5.60; N, 11.89.

Scheme 183

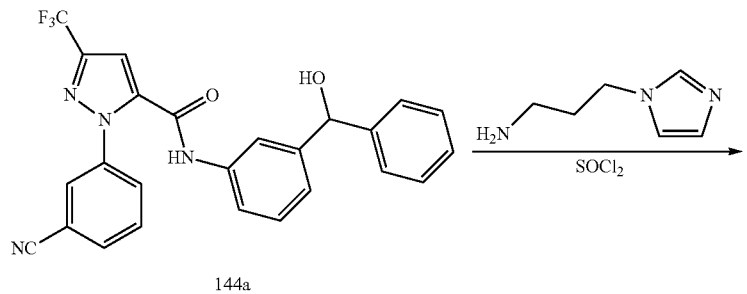

144a

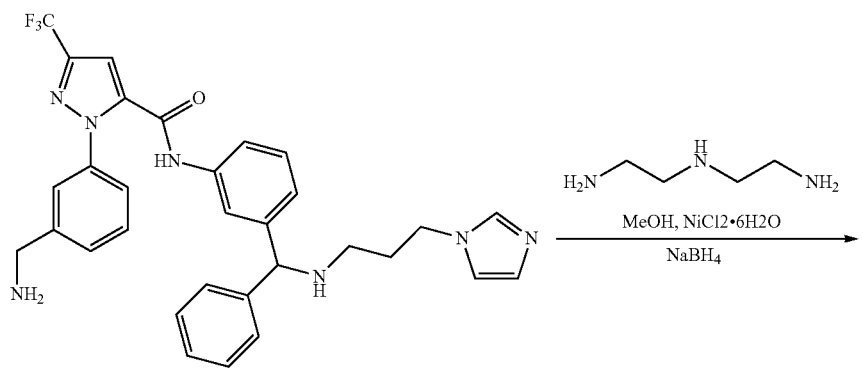

183a

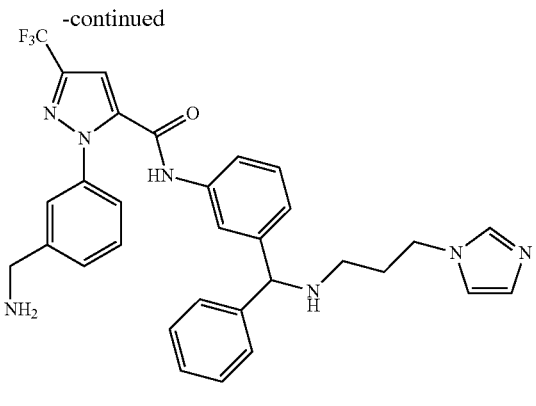

183b

Preparation of N-(3-(((3-(1H-Imidazol-1-yl)propyl) amino)(phenyl)methyl)phenyl)-1-(3-(aminomethyl) phenyl)-3-(trifluoromethyl)-1H-pyrazole-5-carboxamide (183b)

Step-1: Preparation of N-(3-(((3-(1H-imidazol-1-yl) propyl)amino)(phenyl)methyl)phenyl)-1-(3-(aminomethyl)phenyl)-3-(trifluoromethyl)-1H-pyrazole-5-carboxamide (183a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.162 mmol) in dichloromethane (50 mL) at 0° C. was added thionyl chloride (0.514 g, 4.325 mmol) and stirred at room temperature for 3 h. Check TLC and 3-Imidazol-1-yl-propylamine (1.35 g, 10.81 mmol) was added and stirred for 30 min. Then reaction mixture was concentrated in vacuum to dryness. The residue obtained was dissolved in acetonitrile (20 mL) and added 3-Imidazol-1-yl-propylamine (1.35 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford N-(3-(((3-(1H-imidazol-1-yl)propyl) amino)(phenyl)methyl)phenyl)-1-(3-(aminomethyl)phenyl)-3-(trifluoromethyl)-1H-pyrazole-5-carboxamide (183a) (0.350 gm) as a brownish oil; MS (ES−) 568.3 (M−1).

Step-2: Preparation of N-(3-(((3-(1H-Imidazol-1-yl) propyl)amino)(phenyl)methyl)phenyl)-1-(3-(aminomethyl)phenyl)-3-(trifluoromethyl)-1H-pyrazole-5-carboxamide (183b)

To a solution of N-(3-(((3-(1H-imidazol-1-yl)propyl) amino)(phenyl)methyl)phenyl)-1-(3-(aminomethyl)phenyl)-3-(trifluoromethyl)-1H-pyrazole-5-carboxamide (183a) (0.350 g, 0.6144 mmol) in MeOH (20 mL) cooled with ice/water was added nickel (II) chloride hexahydrate (0.17 g, 0.737 mmol) and followed by portion-wise addition of Sodium Borohydride (0.139 g, 3.686 mmol) over a period of 5 min. The reaction mixture was stirred at room temperature for 2 hrs and quenched with $N^1$-(2-aminoethyl)ethane-1,2-diamine (0.15 g, 1.536 mmol) followed by stirring for additional 0.5 h. The reaction mixture was concentrated in vacuum to dryness, and the residue obtained was purified by flash column chromatography (silica gel 60 g, eluting with 0-12% MeOH/DCM) to furnish N-(3-(((3-(1H-Imidazol-1-yl)propyl)amino)(phenyl)methyl)phenyl)-1-(3-(aminomethyl)phenyl)-3-(trifluoromethyl)-1H-pyrazole-5-carboxamide (183b) (0.050 gm) as a white solid; $^1$H NMR (300 MHz, DMSO-$d_6$) δ 10.71 (s, 1H), 7.66 (s, 1H), 7.62 (s, 1H), 7.55-7.35 (m, 8H), 7.33-7.24 (m, 3H), 7.19 (q, J=7.0, 6.5 Hz, 2H), 7.10 (t, J=1.1 Hz, 1H), 6.83 (t, J=1.1 Hz, 1H), 5.90 (s, 2H), 4.71 (s, 1H), 4.02 (t, J=7.0 Hz, 2H), 3.96 (s, 2H), 2.37-2.34 (m, 2H), 1.88 (q, J=6.5 Hz, 2H); $^{19}$F NMR (282 MHz, DMSO) δ −60.76; MS (ES+) 574.4 (M+1); (ES−) 572.4 (M−1), 608.3 (M+Cl); Analysis calculated for $C_{31}H_{30}F_3N_7O \cdot HCl \cdot 0.75H_2O$: C, 59.71; H, 5.25; N, 15.72; Found: C, 60.09; H, 5.43; N, 15.48.

Scheme 184

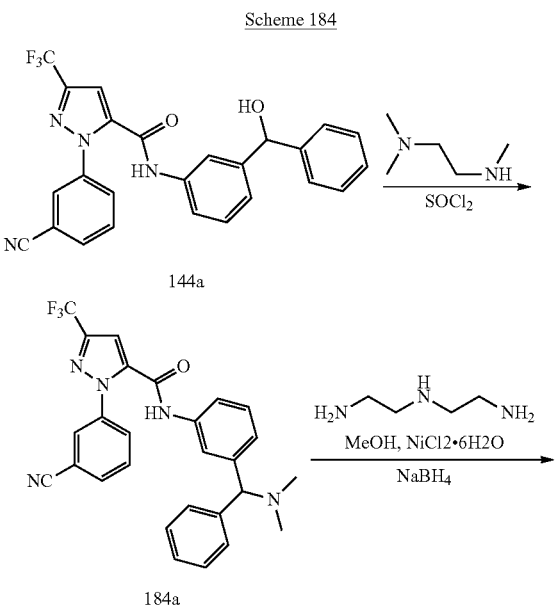

144a

184a

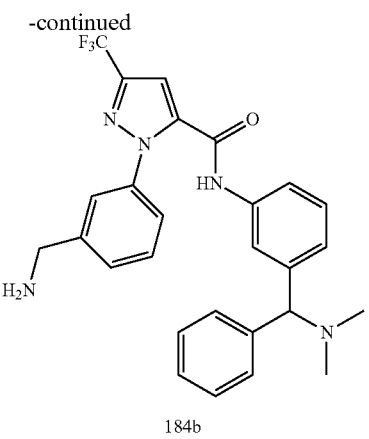

184b

Preparation of 1-(3-(Aminomethyl)phenyl)-N-(3-((dimethylamino)(phenyl)methyl)phenyl)-3-(trifluoromethyl)-1H-pyrazole-5-carboxamide (184b)

Step-1: Preparation of 1-(3-cyanophenyl)-N-(3-((dimethylamino)(phenyl)methyl)phenyl)-3-(trifluoromethyl)-1H-pyrazole-5-carboxamide (184a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.162 mmol) in dichloromethane (50 mL) at 0° C. was added thionyl chloride (0.514 g, 4.325 mmol) and stirred at room temperature for 3 h. Check TLC and N,N,N'-Trimethyl-ethane-1,2-diamine (1.104 g, 10.81 mmol) was added and stirred for 30 min. Then reaction mixture was concentrated in vacuum to dryness. The residue obtained was dissolved in acetonitrile (20 mL) and added N,N,N'-Trimethyl-ethane-1,2-diamine (1.104 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 1-(3-cyanophenyl)-N-(3-((dimethylamino)(phenyl)methyl)phenyl)-3-(trifluoromethyl)-1H-pyrazole-5-carboxamide (184a) (0.200 gm) as a brownish oil; MS (ES−) 488.3 (M−1).

Step-2: Preparation of 1-(3-(Aminomethyl)phenyl)-N-(3-((dimethylamino)(phenyl)methyl)phenyl)-3-(trifluoromethyl)-1H-pyrazole-5-carboxamide (184b)

To a solution of 1-(3-cyanophenyl)-N-(3-((dimethylamino)(phenyl)methyl)phenyl)-3-(trifluoromethyl)-1H-pyrazole-5-carboxamide (184a) (0.190 g, 0.347 mmol) in MeOH (20 mL) cooled with ice/water was added nickel(II) chloride hexahydrate (0.103 g, 0.433 mmol) and followed by portion-wise addition of Sodium Borohydride (0.078 g, 2.082 mmol) over a period of 5 min. The reaction mixture was stirred at room temperature for 2 hrs and quenched with N¹-(2-aminoethyl)ethane-1,2-diamine (0.089 g, 0.867 mmol) followed by stirring for additional 0.5 h. The reaction mixture was concentrated in vacuum to dryness, and the residue obtained was purified by flash column chromatography (silica gel 60 g, eluting with 0-12% MeOH/DCM) to furnish 1-(3-(Aminomethyl)phenyl)-N-(3-((dimethylamino)(phenyl)methyl)phenyl)-3-(trifluoromethyl)-1H-pyrazole-5-carboxamide (184b) (0.025 gm) as an off white solid; ¹H NMR (300 MHz, DMSO-d₆) δ 10.69 (s, 1H), 7.72 (s, 1H), 7.66-7.09 (m, 13H), 4.06 (s, 1H), 3.86 (s, 2H), 2.10 (s, 6H); ¹⁹F NMR (282 MHz, DMSO) δ −60.75; MS (ES+) 494.3 (M+1); (ES−) 492.3 (M−1), 528.3 (M+Cl); Analysis calculated for C₂₇H₂₆F₃N₅O.1.5H₂O: C, 62.30; H, 5.62; N, 13.45; Found: C, 62.27; H, 6.18; N, 11.54.

Scheme 185

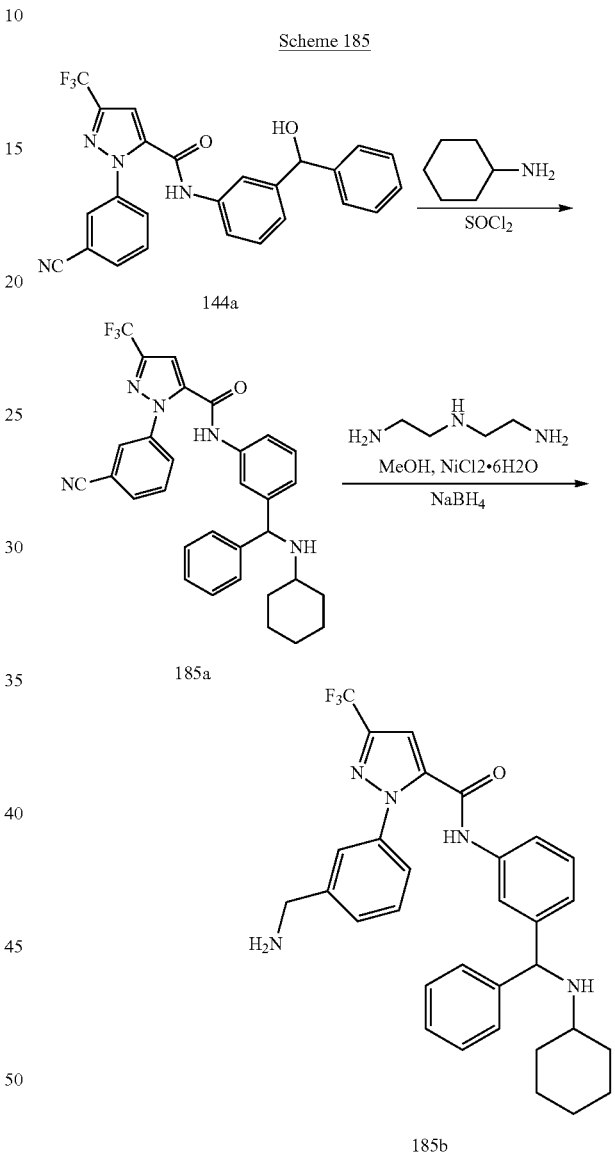

Preparation of 1-(3-(Aminomethyl)phenyl)-N-(3-((cyclohexylamino)(phenyl)methyl)phenyl)-3-(trifluoromethyl)-1H-pyrazole-5-carboxamide (185b)

Step-1: Preparation of 1-(3-cyanophenyl)-N-(3-((cyclohexylamino)(phenyl)methyl)phenyl)-3-(trifluoromethyl)-1H-pyrazole-5-carboxamide (185a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.162 mmol) in dichloromethane (50 mL) at 0° C. was added thionyl chloride (0.514 g, 4.325 mmol) and stirred at room temperature for 3 h. Check TLC and Cyclohexylamine (1.07 g, 10.81 mmol) was added and stirred for 30 min. Then reaction mixture was concentrated in vacuum to dryness. The residue obtained was dissolved in acetonitrile (20 mL) and added Cyclohexylamine (1.07 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 1-(3-cyanophenyl)-N-(3-((cyclohexylamino)(phenyl)methyl)phenyl)-3-(trifluoromethyl)-1H-pyrazole-5-carboxamide (185a) (0.9 gm) as yellow-brown sticky liquid; MS (ES−) 542.3 (M−1).

Step-2: Preparation of 1-(3-(Aminomethyl)phenyl)-N-(3-((cyclohexylamino)(phenyl)methyl)phenyl)-3-(trifluoromethyl)-1H-pyrazole-5-carboxamide (185b)

To a solution of 1-(3-cyanophenyl)-N-(3-((cyclohexylamino)(phenyl)methyl)phenyl)-3-(trifluoromethyl)-1H-pyrazole-5-carboxamide (185a) (0.9 g, 1.655 mmol) in MeOH (20 mL) cooled with ice/water was added nickel(II) chloride hexahydrate (0.491 g, 2.069 mmol) and followed by portion-wise addition of Sodium Borohydride (0.375 g, 9.93 mmol) over a period of 5 min. The reaction mixture was stirred at room temperature for 2 hrs and quenched with $N^1$-(2-aminoethyl)ethane-1,2-diamine (0.682 g, 6.62 mmol) followed by stirring for additional 0.5 h. The reaction mixture was concentrated in vacuum to dryness, and the residue obtained was purified by flash column chromatography (silica gel 70 g, eluting with 0-12% MeOH/DCM) to furnish 1-(3-(Aminomethyl)phenyl)-N-(3-((cyclohexylamino)(phenyl)methyl)phenyl)-3-(trifluoromethyl)-1H-pyrazole-5-carboxamide (185b) (0.160 gm) as a Off white solid; $^1$H NMR (300 MHz, DMSO-$d_6$) δ 10.71 (s, 1H), 7.65-7.57 (m, 3H), 7.57-7.42 (m, 3H), 7.42-7.12 (m, 8H), 4.97 (s, 1H), 3.91 (s, 2H), 2.20 (d, J=11.9 Hz, 1H), 1.89 (d, J=8.1 Hz, 2H), 1.63 (s, 2H), 1.49 (s, 1H), 1.16-0.97 (m, 5H); $^{19}$F NMR (282 MHz, DMSO) δ −60.76; MS (ES+) 548.4 (M+1); (ES−) 546.4 (M−1), 582.3 (M+Cl); Analysis calculated for $C_{31}H_{32}F_3N_5O\cdot1.5H_2O$: C, 64.79; H, 6.14; N, 12.19; Found: C, 64.97; H, 5.85; N, 11.81.

Scheme 186

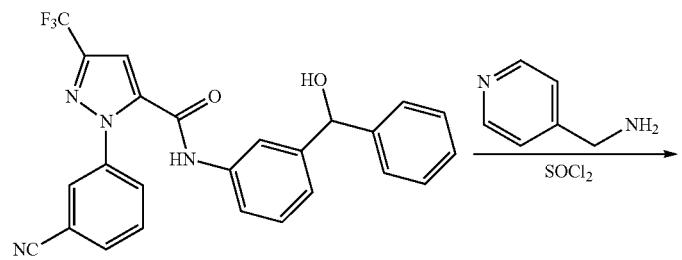

144a

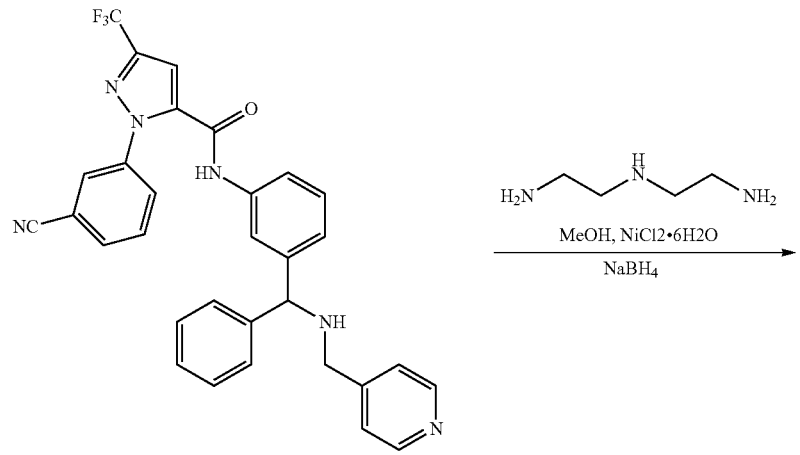

186a

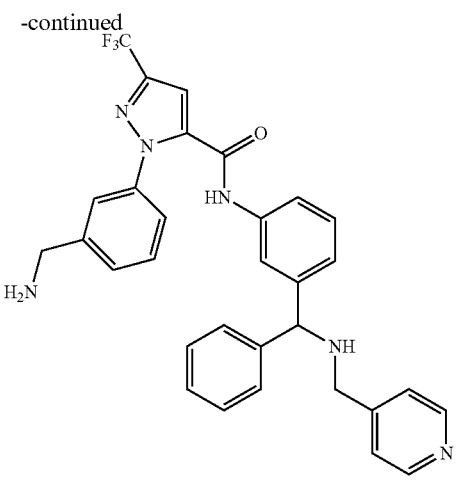

186b

Preparation of 1-(3-(Aminomethyl)phenyl)-N-(3-(phenyl((pyridin-4-ylmethyl)amino)methyl)phenyl)-3-(trifluoromethyl)-1H-pyrazole-5-carboxamide (186b)

Step-1: Preparation of 1-(3-cyanophenyl)-N-(3-(phenyl((pyridin-4-ylmethyl)amino)methyl)phenyl)-3-(trifluoromethyl)-1H-pyrazole-5-carboxamide (186a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.162 mmol) in dichloromethane (50 mL) at 0° C. was added thionyl chloride (0.514 g, 4.325 mmol) and stirred at room temperature for 3 h. Check TLC and Pyridin-4-yl-methylamine (1.168 g, 10.81 mmol) was added and stirred for 30 min. Then reaction mixture was concentrated in vacuum to dryness. The residue obtained was dissolved in acetonitrile (20 mL) and added C-Pyridin-4-yl-methylamine (1.168 g, 10.805 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 1-(3-cyanophenyl)-N-(3-(phenyl((pyridin-4-ylmethyl)amino)methyl)phenyl)-3-(trifluoromethyl)-1H-pyrazole-5-carboxamide (186a) (0.3 gm) as red oil; MS (ES−) 551.2 (M−1).

Step-2: Preparation of 1-(3-(Aminomethyl)phenyl)-N-(3-(phenyl((pyridin-4-ylmethyl)amino)methyl)phenyl)-3-(trifluoromethyl)-1H-pyrazole-5-carboxamide (186b)

To a solution of 1-(3-cyanophenyl)-N-(3-(phenyl((pyridin-4-ylmethyl)amino)methyl)phenyl)-3-(trifluoromethyl)-1H-pyrazole-5-carboxamide (186a) (0.3 g, 0.543 mmol) in MeOH (20 mL) cooled with ice/water was added nickel(II) chloride hexahydrate (0.170 g, 0.716 mmol) and followed by portion-wise addition of Sodium Borohydride (0.123 g, 3.258 mmol) over a period of 5 min. The reaction mixture was stirred at room temperature for 2 hrs and quenched with $N^1$-(2-aminoethyl)ethane-1,2-diamine (0.140 g, 1.357 mmol) followed by stirring for additional 0.5 h. The reaction mixture was concentrated in vacuum to dryness, and the residue obtained was purified by flash column chromatography (silica gel 70 g, eluting with 0-12% MeOH/DCM) to furnish 1-(3-(Aminomethyl)phenyl)-N-(3-(phenyl((pyridin-4-ylmethyl)amino)methyl)phenyl)-3-(trifluoromethyl)-1H-pyrazole-5-carboxamide (186b) (0.065 gm) as a off white Solid; $^1$H NMR (300 MHz, DMSO-$d_6$) δ 10.70 (s, 1H), 8.56-8.43 (m, 1H), 7.73-7.15 (m, 17H), 4.73 (s, 1H), 3.93 (s, 2H), 3.62 (d, J=5.7 Hz, 2H); $^{19}$F NMR (282 MHz, DMSO) δ −60.51; MS (ES+) 557.4 (M+1); (ES−) 555.4 (M−1), 591.3 (M+Cl); Analysis calculated for $C_{31}H_{27}F_3N_6O.2.25H_2O$: C, 62.36; H, 5.32; N, 14.07; Found: C, 62.58; H, 5.30; N, 13.36.

Scheme 187

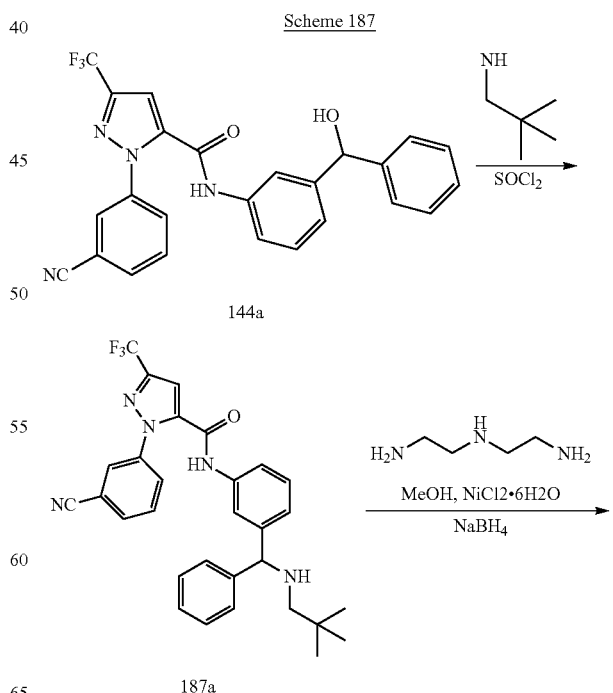

-continued

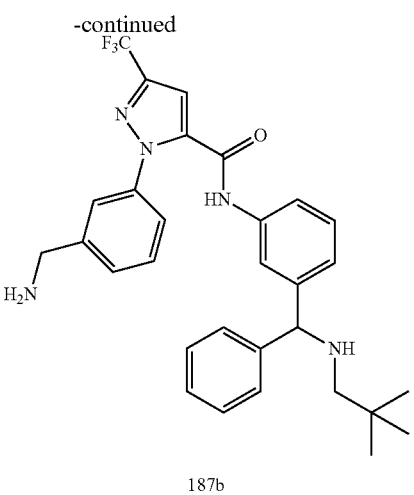

187b

Preparation of 1-(3-(Aminomethyl)phenyl)-N-(3-((neopentylamino)(phenyl)methyl)phenyl)-3-(trifluoromethyl)-1H-pyrazole-5-carboxamide (187b)

Step-1: Preparation of 1-(3-cyanophenyl)-N-(3-((neopentylamino)(phenyl)methyl)phenyl)-3-(trifluoromethyl)-1H-pyrazole-5-carboxamide (187a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.162 mmol) in dichloromethane (50 mL) at 0° C. was added thionyl chloride (0.514 g, 4.325 mmol) and stirred at room temperature for 3 h. Check TLC and 1,1-Dimethyl-propylamine (0.942 g, 10.81 mmol) was added and stirred for 30 min. Then reaction mixture was concentrated in vacuum to dryness. The residue obtained was dissolved in acetonitrile (20 mL) and added 1,1-Dimethyl-propylamine (0.942 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 1-(3-cyanophenyl)-N-(3-((neopentylamino)(phenyl)methyl)phenyl)-3-(trifluoromethyl)-1H-pyrazole-5-carboxamide (187a) (0.480 gm) as yellow sticky oil; MS (ES−) 530.3 (M−1).

Step-2: Preparation of 1-(3-(Aminomethyl)phenyl)-N-(3-((neopentylamino)(phenyl)methyl)phenyl)-3-(trifluoromethyl)-1H-pyrazole-5-carboxamide (187b)

To a solution of 1-(3-cyanophenyl)-N-(3-((neopentylamino)(phenyl)methyl)phenyl)-3-(trifluoromethyl)-1H-pyrazole-5-carboxamide (187a) (0.480 g, 0.910 mmol) in MeOH (20 mL) cooled with ice/water was added nickel(II) chloride hexahydrate (0.268 g, 1.128 mmol) and followed by portion-wise addition of Sodium Borohydride (0.204 g, 5.41 mmol) over a period of 5 min. The reaction mixture was stirred at room temperature for 2 hrs and quenched with N$^1$-(2-aminoethyl)ethane-1,2-diamine (0.372 g, 3.612 mmol) followed by stirring for additional 0.5 h. The reaction mixture was concentrated in vacuum to dryness, and the residue obtained was purified by flash column chromatography (silica gel 60 g, eluting with 0-12% MeOH/DCM) to furnish 1-(3-(Aminomethyl)phenyl)-N-(3-((neopentylamino)(phenyl)methyl)phenyl)-3-(trifluoromethyl)-1H-pyrazole-5-carboxamide (187b) pure (0.080 gm) as a white crystal; $^1$H NMR (300 MHz, DMSO-$d_6$) δ 10.70 (s, 1H), 7.70-7.07 (m, 14H), 4.94 (s, 1H), 4.04 (s, 2H), 0.90 (s, 9H); $^{19}$F NMR (282 MHz, DMSO) δ −60.79; MS (ES+) 536.3 (M+1); (ES−) 534.3 (M−1), 570.1 (M+Cl).

Scheme 188

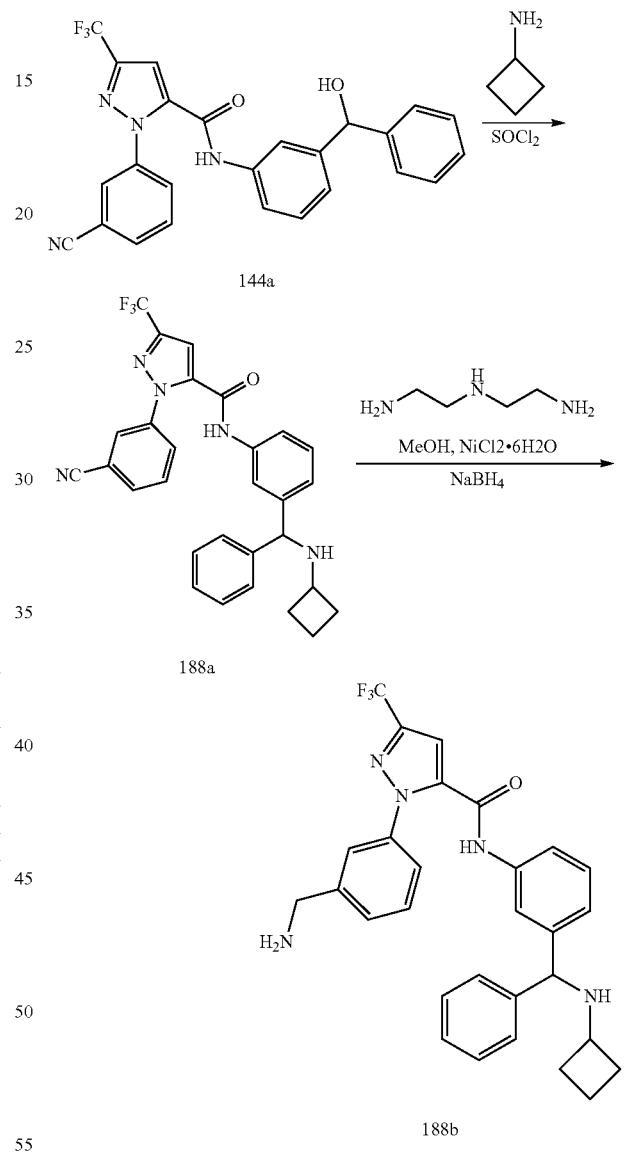

Preparation of 1-(3-(Aminomethyl)phenyl)-N-(3-((cyclobutylamino)(phenyl)methyl)phenyl)-3-(trifluoromethyl)-1H-pyrazole-5-carboxamide (188b)

Step-1: Preparation of 1-(3-cyanophenyl)-N-(3-((cyclobutylamino)(phenyl)methyl)phenyl)-3-(trifluoromethyl)-1H-pyrazole-5-carboxamide (188a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.162 mmol) in dichloromethane (50 mL) at 0° C. was added thionyl chloride (0.514 g, 4.325 mmol) and stirred at room temperature for 3 h. Check TLC and Cyclobutylamine (0.768 g, 10.81 mmol) was added and stirred for 30 min. Then reaction mixture was concentrated in vacuum to dryness. The residue obtained was dissolved in acetonitrile (20 mL) and added Cyclobutylamine (0.768 g, 10.805 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 1-(3-cyanophenyl)-N-(3-((cyclobutylamino)(phenyl)methyl)phenyl)-3-(trifluoromethyl)-1H-pyrazole-5-carboxamide (188a) (0.7 gm) as red oil; MS (ES−) 514.3 (M−1).

Step-2: Preparation of 1-(3-(Aminomethyl)phenyl)-N-(3-((cyclobutylamino)(phenyl)methyl)phenyl)-3-(trifluoromethyl)-1H-pyrazole-5-carboxamide (188b)

To a solution of 1-(3-cyanophenyl)-N-(3-((cyclobutylamino)(phenyl)methyl)phenyl)-3-(trifluoromethyl)-1H-pyrazole-5-carboxamide (188a) (0.7 g, 1.032 mmol) in MeOH (20 mL) cooled with ice/water was added nickel(II) chloride hexahydrate (0.29 g, 1.23 mmol) and followed by portion-wise addition of Sodium Borohydride (0.23 g, 6.192 mmol) over a period of 5 min. The reaction mixture was stirred at room temperature for 2 hrs and quenched with $N^1$-(2-aminoethyl)ethane-1,2-diamine (0.266 g, 2.58 mmol) followed by stirring for additional 0.5 h. The reaction mixture was concentrated in vacuum to dryness, and the residue obtained was purified by flash column chromatography (silica gel 70 g, eluting with 0-12% MeOH/DCM) to furnish 1-(3-(Aminomethyl)phenyl)-N-(3-((cyclobutylamino)(phenyl)methyl)phenyl)-3-(trifluoromethyl)-1H-pyrazole-5-carboxamide (188b) (0.120 gm) as a Light Yellow Solid; $^1$H NMR (300 MHz, DMSO-$d_6$) δ 10.68 (s, 1H), 7.63 (t, J=1.8 Hz, 1H), 7.58 (s, 1H), 7.56-7.50 (m, 2H), 7.51-7.12 (m, 10H), 4.72 (s, 1H), 3.82 (s, 2H), 3.07-2.89 (m, 1H), 1.99 (dt, J=13.1, 7.4 Hz, 2H), 1.74 (dp, J=18.1, 9.3, 8.8 Hz, 2H), 1.60-1.35 (m, 2H); $^{19}$F NMR (282 MHz, DMSO) δ −60.75; MS (ES+) 520.3 (M+1); (ES−) 518.3 (M−1), 554.2 (M+Cl): Analysis calculated for $C_{28}H_{28}F_3N_5O.H_2O$: C, 64.79; H, 5.62; N, 13.03; Found: C, 64.99; H, 5.58; N, 12.95.

Scheme 189

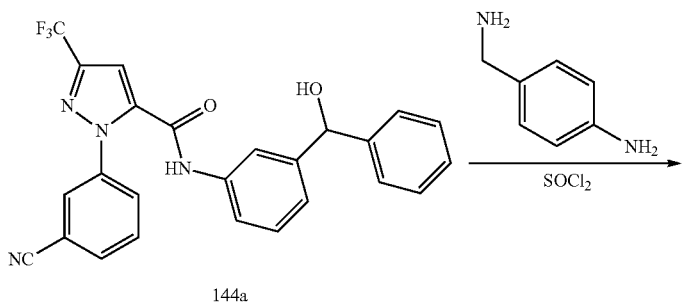

144a

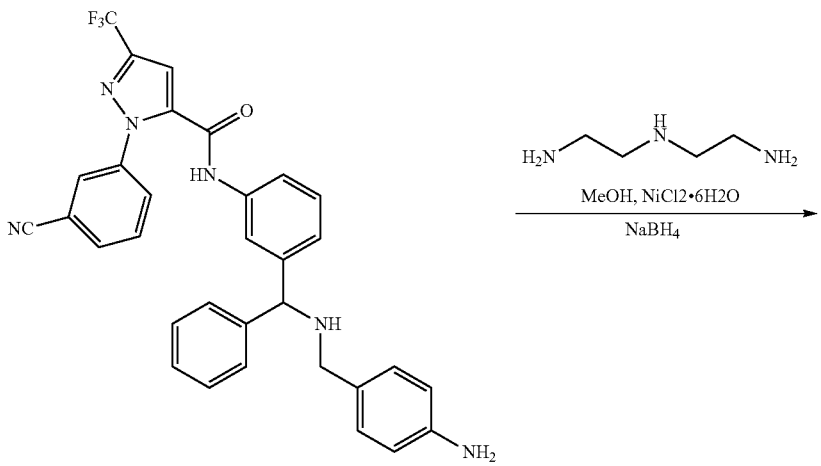

189a

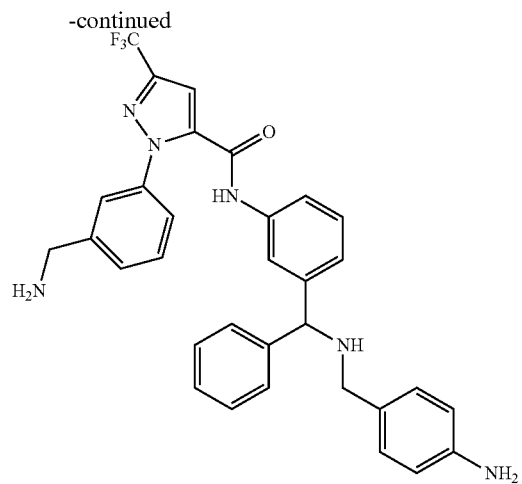

189b

Preparation of N-(3-(((4-Aminobenzyl)amino)(phenyl)methyl)phenyl)-1-(3-(aminomethyl)phenyl)-3-(trifluoromethyl)-1H-pyrazole-5-carboxamide (189b)

Step-1: Preparation of N-(3-(((4-aminobenzyl)amino)(phenyl)methyl)phenyl)-1-(3-cyanophenyl)-3-(trifluoromethyl)-1H-pyrazole-5-carboxamide (189a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.162 mmol) in dichloromethane (50 mL) at 0° C. was added thionyl chloride (0.514 g, 4.325 mmol) and stirred at room temperature for 3 h. Check TLC and 4-Aminomethyl-phenylamine (1.31 g, 10.81 mmol) was added and stirred for 30 min. Then reaction mixture was concentrated in vacuum to dryness. The residue obtained was dissolved in acetonitrile (20 mL) and added 4-Aminomethyl-phenylamine (1.31 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford N-(3-(((4-aminobenzyl)amino)(phenyl)methyl)phenyl)-1-(3-cyanophenyl)-3-(trifluoromethyl)-1H-pyrazole-5-carboxamide (189a) (0.5 gm) as yellow oil; MS (ES−) 565.3 (M−1).

Step-2: Preparation of N-(3-(((4-Aminobenzyl)amino)(phenyl)methyl)phenyl)-1-(3-(aminomethyl)phenyl)-3-(trifluoromethyl)-1H-pyrazole-5-carboxamide (189b)

To a solution of 2 afford 2-(3-Cyano-phenyl)-5-trifluoromethyl-2H-pyrazole-3-carboxylic acid {3-[(4-amino-benzylamino)-phenyl-methyl]-phenyl}-amide (0.5 g, 0.884 mmol) in MeOH (20 mL) cooled with ice/water was added nickel(II) chloride hexahydrate (0.26 g, 1.105 mmol) and followed by portion-wise addition of Sodium Borohydride (0.200 g, 5.304 mmol) over a period of 5 min. The reaction mixture was stirred at room temperature for 2 hrs and quenched with $N^1$-(2-aminoethyl)ethane-1,2-diamine (0.364 g, 3.536 mmol) followed by stirring for additional 0.5 h. The reaction mixture was concentrated in vacuum to dryness, and the residue obtained was purified by flash column chromatography (silica gel 60 g, eluting with 0-12% MeOH/DCM) to furnish -(3-Aminomethyl-phenyl)-5-trifluoromethyl-2H-pyrazole-3-carboxylic acid {3-[(4-amino-benzylamino)-phenyl-methyl]-phenyl}-amide pure (0.020 gm) as a white Solid and mix (0.060 gm) as a off white solid; $^1$H NMR (300 MHz, DMSO-$d_6$) δ 10.79 (s, 1H), 8.34 (s, 3H), 7.77-7.68 (m, 2H), 7.66 (s, 1H), 7.62-7.17 (m, 11H), 6.96 (d, J=8.1 Hz, 2H), 6.57-6.43 (m, 2H), 5.05 (s, 3H), 4.12 (s, 2H), 3.67-3.43 (m, 2H); $^{19}$F NMR (282 MHz, DMSO) δ −60.80; MS (ES+) 571.3 (M+1); (ES−) 569.3 (M−1), 605.3 (M+Cl); Analysis calculated for $C_{32}H_{29}F_3N_6O \cdot HCl \cdot 1.5H_2O$: C, 60.61; H, 5.25; N, 13.25; Found: C, 60.56; H, 5.20; N, 13.31.

Scheme 190

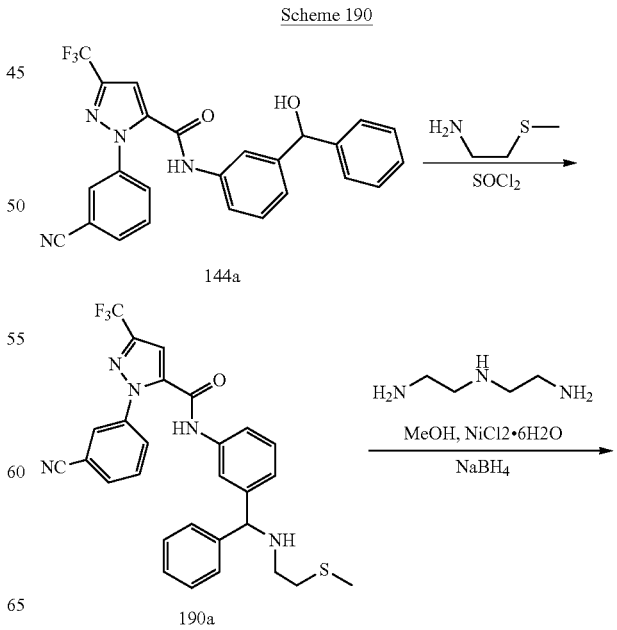

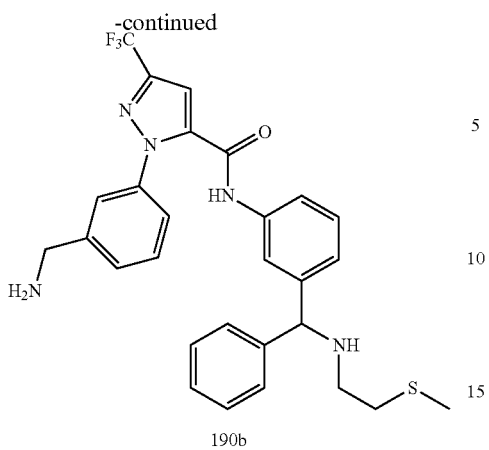

190b

Preparation of 1-(3-(aminomethyl)phenyl)-N-(3-(((2-(methylthio)ethyl)amino)(phenyl)methyl)phenyl)-3-(trifluoromethyl)-1H-pyrazole-5-carboxamide (190b)

Step-1: Preparation of 1-(3-cyanophenyl)-N-(3-(((2-(methylthio)ethyl)amino)(phenyl)methyl)phenyl)-3-(trifluoromethyl)-1H-pyrazole-5-carboxamide (190a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.162 mmol) in dichloromethane (50 mL) at 0° C. was added thionyl chloride (0.514 g, 4.325 mmol) and stirred at room temperature for 3 h. Check TLC and 2-Methylsulfanyl-ethylamine (0.985 g, 10.81 mmol) was added and stirred for 30 min. Then reaction mixture was concentrated in vacuum to dryness. The residue obtained was dissolved in acetonitrile (20 mL) and added 2-Methylsulfanyl-ethylamine (0.985 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 1-(3-cyanophenyl)-N-(3-(((2-(methylthio)ethyl)amino)(phenyl)methyl)phenyl)-3-(trifluoromethyl)-1H-pyrazole-5-carboxamide (190a) (0.81 gm) as Light brown oil; MS (ES−) 534.3 (M−1).

Step-2: Preparation of 1-(3-(aminomethyl)phenyl)-N-(3-(((2-(methylthio)ethyl)amino)(phenyl)methyl)phenyl)-3-(trifluoromethyl)-1H-pyrazole-5-carboxamide (190b)

To a solution of 1-(3-cyanophenyl)-N-(3-(((2-(methylthio)ethyl)amino)(phenyl)methyl)phenyl)-3-(trifluoromethyl)-1H-pyrazole-5-carboxamide (190a) (0.8 g, 1.493 mmol) in MeOH (20 mL) cooled with ice/water was added nickel(II) chloride hexahydrate (0.443 g, 1.866 mmol) and followed by portion-wise addition of Sodium Borohydride (0.338 g, 8.958 mmol) over a period of 5 min. The reaction mixture was stirred at room temperature for 2 hrs and quenched with $N^1$-(2-aminoethyl)ethane-1,2-diamine (0.616 g, 5.972 mmol) followed by stirring for additional 0.5 h. The reaction mixture was concentrated in vacuum to dryness, and the residue obtained was purified by flash column chromatography (silica gel 60 g, eluting with 0-12% MeOH/DCM) to furnish 1-(3-(aminomethyl)phenyl)-N-(3-(((2-(methylthio)ethyl)amino)(phenyl)methyl)phenyl)-3-(trifluoromethyl)-1H-pyrazole-5-carboxamide (190b) (0.075 gm) as a Light yellowish solid; $^1$H NMR (300 MHz, DMSO-$d_6$) δ 10.72 (s, 1H), 7.75-7.13 (m, 14H), 6.04 (s, 2H), 4.81 (s, 1H), 3.97 (s, 2H), 2.60 (s, 4H), 1.98 (s, 3H); $^{19}$F NMR (282 MHz, DMSO) δ −60.77; MS (ES+) 540.3 (M+1); (ES−) 538.2 (M−1), 601.3 (M+Cl); Analysis calculated for $C_{28}H_{28}F_3N_5OS\cdot 0.5H_2O$: C, 61.30; H, 5.33; N, 12.77; Found: C, 61.20; H, 5.27; N, 12.01.

Scheme 191

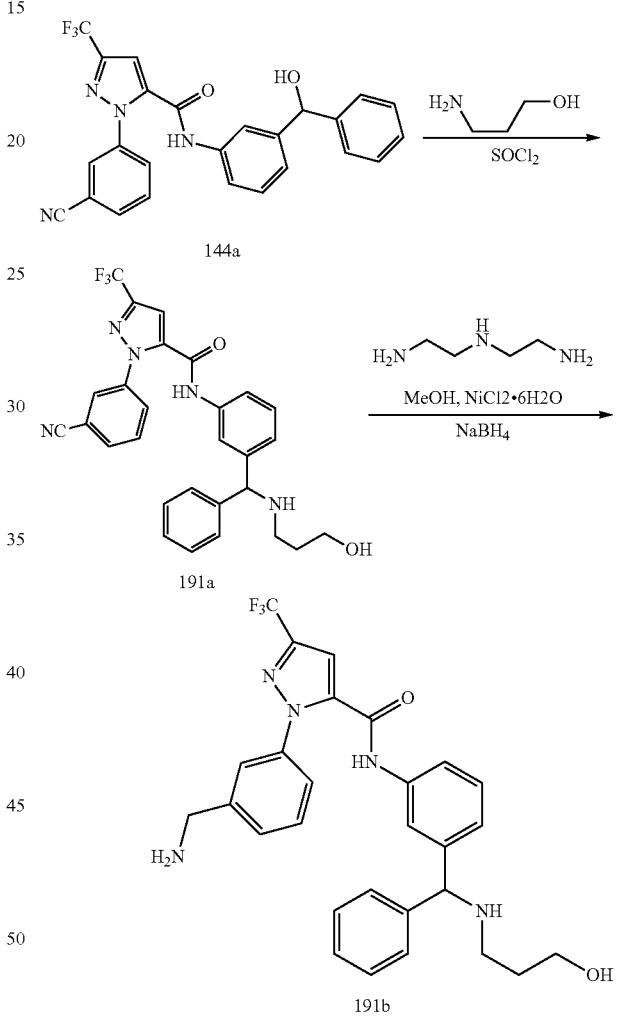

Preparation of 1-(3-(Aminomethyl)phenyl)-N-(3-(((3-hydroxypropyl)amino)(phenyl)methyl)phenyl)-3-(trifluoromethyl)-1H-pyrazole-5-carboxamide (191b)

Step-1: Preparation of 1-(3-cyanophenyl)-N-(3-(((3-hydroxypropyl)amino)(phenyl)methyl)phenyl)-3-(trifluoromethyl)-1H-pyrazole-5-carboxamide (191a)

To a solution of 1-(3-cyanophenyl)-N-(3-(hydroxy(phenyl)methyl)phenyl)-3-(trifluoromethyl)-1H-pyrazole-5-carboxamide (144a) (1.0 g, 2.162 mmol) in dichloromethane (50 mL) at 0° C. was added thionyl chloride (0.514 g, 4.325 mmol) and stirred at room temperature for 3 h. Check TLC and 3-Amino-propan-1-ol (0.811 g, 10.81 mmol) was added and stirred for 30 min. Then reaction mixture was concentrated in vacuum to dryness. The residue obtained was dissolved in acetonitrile (20 mL) and added 3-Amino-propan-1-ol (0.811 g, 10.81 mmol). The reaction mixture was heated at reflux overnight, cooled to room temperature and concentrated in vacuum to dryness. The residue was dissolved in dichloromethane (20 mL), washed with water (2×25 mL), dried, filtered and concentrated in vacuum. The residue obtained was purified by flash column chromatography (silica gel 40 g, eluting 0-25% ethyl acetate in hexane) to afford 1-(3-cyanophenyl)-N-(3-(((3-hydroxypropyl)amino)(phenyl)methyl)phenyl)-3-(trifluoromethyl)-1H-pyrazole-5-carboxamide (191a) (0.65 gm) as Brown syrup; MS (ES−) 518.3 (M−1).

Step-2: Preparation of 1-(3-(Aminomethyl)phenyl)-N-(3-(((3-hydroxypropyl)amino)(phenyl)methyl)phenyl)-3-(trifluoromethyl)-1H-pyrazole-5-carboxamide (191b)

To a solution of 1-(3-cyanophenyl)-N-(3-(((3-hydroxypropyl)amino)(phenyl)methyl)phenyl)-3-(trifluoromethyl)-1H-pyrazole-5-carboxamide (191a) (0.6 g, 1.154 mmol) in MeOH (20 mL) cooled with ice/water was added nickel(II) chloride hexahydrate (0.343 g, 1.443 mmol) and followed by portion-wise addition of sodium borohydride (0.261 g, 6.924 mmol) over a period of 5 min. The reaction mixture was stirred at room temperature for 2 hrs and quenched with N-(2-aminoethyl)ethane-1,2-diamine (0.476 g, 4.616 mmol) followed by stirring for additional 0.5 h. The reaction mixture was concentrated in vacuum to dryness, and the residue obtained was purified by flash column chromatography (silica gel 60 g, eluting with 0-12% MeOH/DCM) to furnish 1-(3-(Aminomethyl)phenyl)-N-(3-(((3-hydroxypropyl)amino)(phenyl)methyl)phenyl)-3-(trifluoromethyl)-1H-pyrazole-5-carboxamide (191b) (0.060 gm) as a light yellowish solid; $^1$H NMR (300 MHz, DMSO-$d_6$) δ 10.73 (s, 1H), 7.69 (s, 1H), 7.64 (d, J=2.8 Hz, 2H), 7.60-7.45 (m, 4H), 7.40 (d, J=1.7 Hz, 1H), 7.37 (s, 1H), 7.33-7.24 (m, 3H), 7.20 (dt, J=8.9, 5.6 Hz, 2H), 4.74 (s, 1H), 4.09 (s, 2H), 3.43 (m, 2H), 2.46 (m, 2H), 1.60 (p, J=6.8 Hz, 2H); $^{19}$F NMR (282 MHz, DMSO) δ −60.80, MS (ES+) 524.3 (M+1); (ES−) 558.2 (M+Cl); Analysis calculated for $C_{28}H_{28}F_3N_5O_2 \cdot HCl \cdot 1.5H_2O$: C, 57.29; H, 5.49; N, 11.93; Found: C, 57.37; H, 5.35; N, 12.31.

Scheme 192

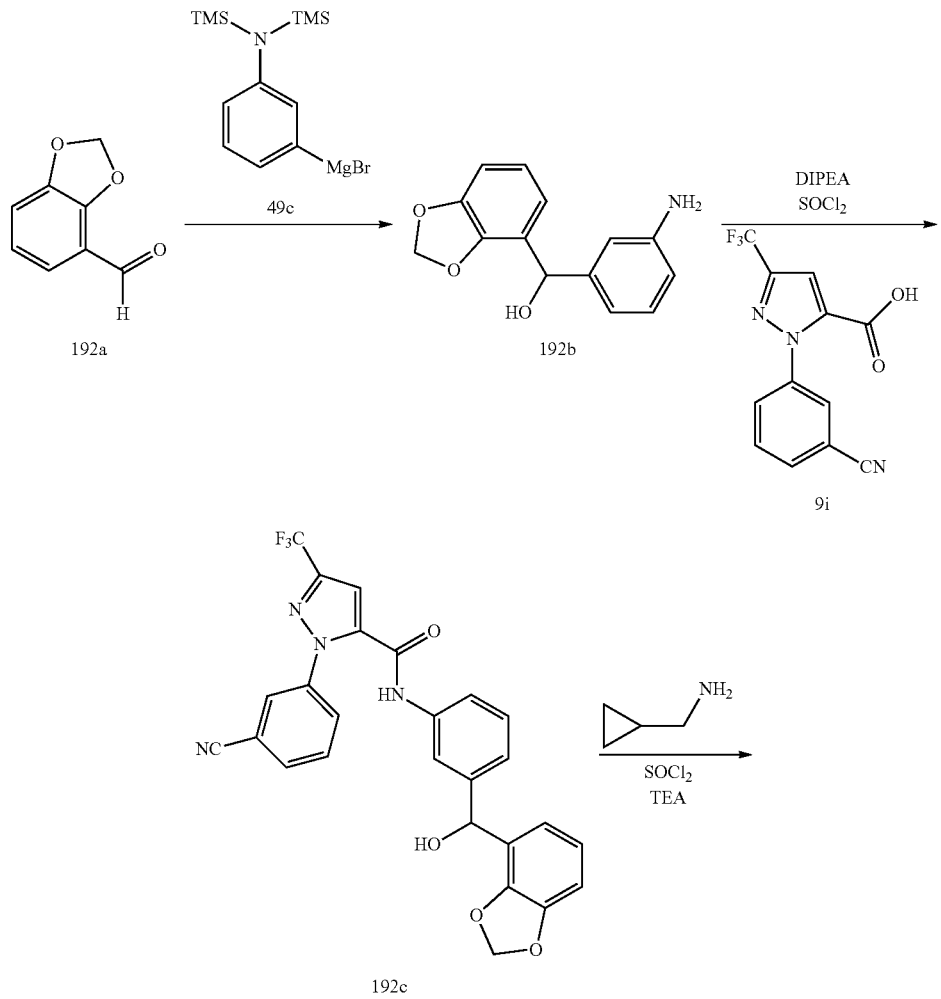

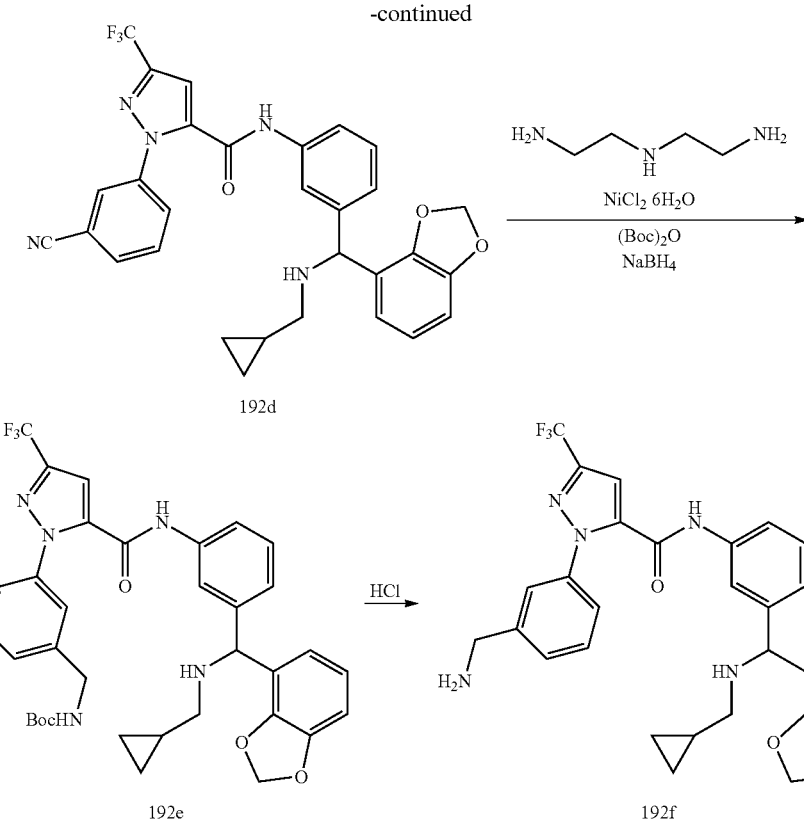

Preparation of 1-(3-(aminomethyl)phenyl)-N-(3-(benzo[d][1,3]dioxol-4-yl(cyclopropylmethylamino)methyl)phenyl)-3-(trifluoromethyl)-1H-pyrazole-5-carboxamide (192f)

Compound (192f) was prepared starting from benzo[d][1,3]dioxole-4-carbaldehyde (192a) (10 mmol) in five steps as shown in scheme 192 using procedure as reported in scheme-109 to furnish 1-(3-(aminomethyl)phenyl)-N-(3-(benzo[d] [1,3] dioxol-4-yl(cyclopropylmethylamino)methyl)phenyl)-3-(trifluoromethyl)-1H-pyrazole-5-carboxamide (192f) (30 mg) as an off white solid; $^1$H NMR (300 MHz, Methanol-$d_4$) δ 7.66 (t, J=1.9 Hz, 1H), 7.61-7.55 (m, 1H), 7.53-7.41 (m, 4H), 7.35 (s, 1H), 7.30-7.17 (m, 2H), 6.84 (dd, J=8.0, 1.4 Hz, 1H), 6.75 (t, J=7.8 Hz, 1H), 6.67 (dd, J=7.6, 1.4 Hz, 1H), 5.87 (s, 2H), 4.99 (s, 1H), 4.04 (s, 2H), 2.44-2.28 (m, 2H), 1.01-0.83 (m, 1H), 0.50-0.38 (m, 2H), 0.10--0.01 (m, 2H); $^{19}$F NMR (282 MHz, MeOD) δ -63.76; MS (ES+) 564.3 (M+1); (ES-) 598.3 (M+Cl); Analysis calculated for $C_{30}H_{28}F_3N_5O_3 \cdot HCl \cdot 1.75H_2O$: C, 57.05; H, 5.19; N, 11.09; Found: C, 57.31; H, 5.25; N, 10.74.

Scheme 193

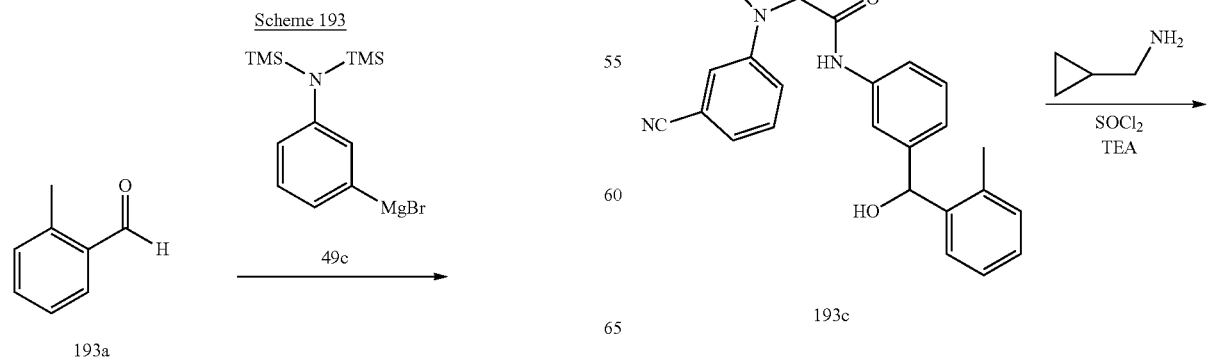

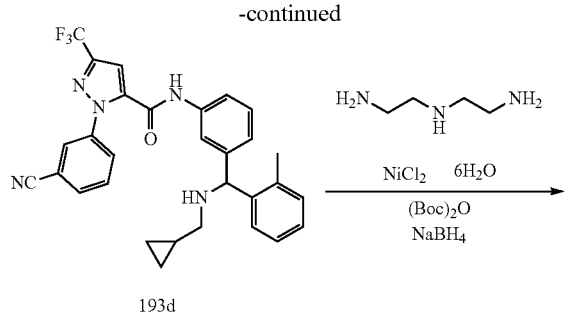

193d

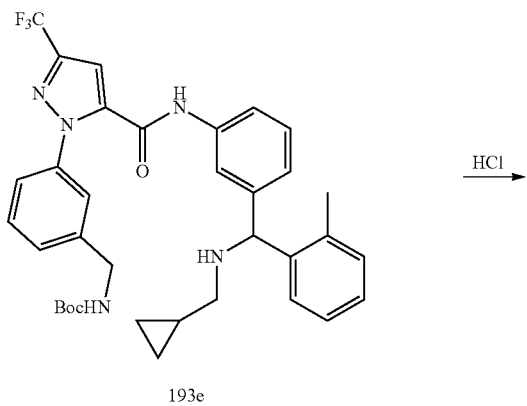

193e

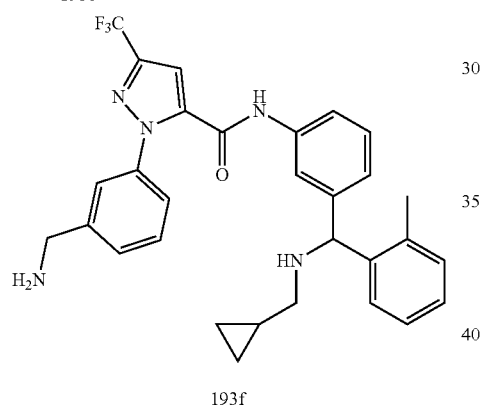

193f

Preparation of 1-(3-(Aminomethyl)phenyl)-N-(3-((((cyclopropylmethyl)amino)(o-tolyl)methyl)phenyl)-3-(trifluoromethyl)-1H-pyrazole-5-carboxamide (193f)

Compound (193f) was prepared starting from 2-methylbenzaldehyde (193a) (10 mmol) in five steps as shown in scheme 193 using procedure as reported in scheme-109 to furnish 1-(3-(Aminomethyl)phenyl)-N-(3-((((cyclopropylmethyl)amino)(o-tolyl)methyl)phenyl)-3-(trifluoromethyl)-1H-pyrazole-5-carboxamide (193f) (30 mgs) as a light green solid; $^1$H NMR (300 MHz, DMSO-d$_6$) δ 10.94 (s, 1H), 9.84 (s, 2H), 8.41 (s, 3H), 7.92-7.17 (m, 13H), 5.61 (s, 1H), 4.22-4.03 (m, 2H), 2.83-2.67 (m, 2H), 2.31 (s, 3H), 1.19-1.01 (m, 1H), 0.54 (d, J=8.2 Hz, 2H), 0.36-0.14 (m, 2H); $^{19}$F NMR (282 MHz, DMSO) δ −60.80; MS (ES+) 534.3 (M+1); (ES−) 532.3 (M−1), 568.2 (M+Cl); Analysis calculated for C$_{30}$H$_{30}$F$_3$N$_5$O.2HCl.2.75H$_2$O: C, 54.92; H, 5.76; N, 10.68; Found: C, 55.08; H, 5.54; N, 10.50.

Scheme 194

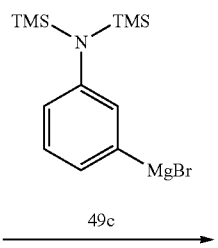

194a

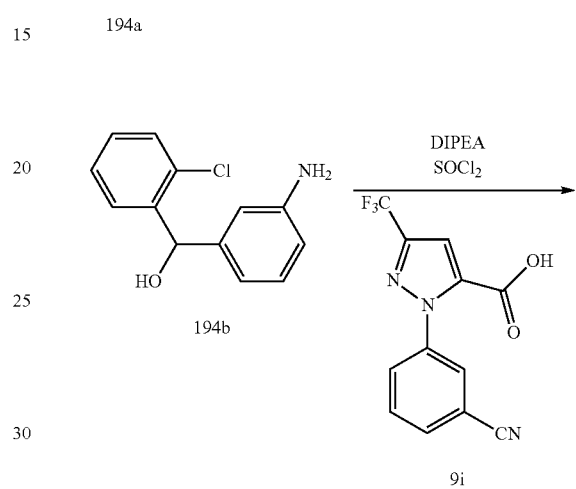

194b

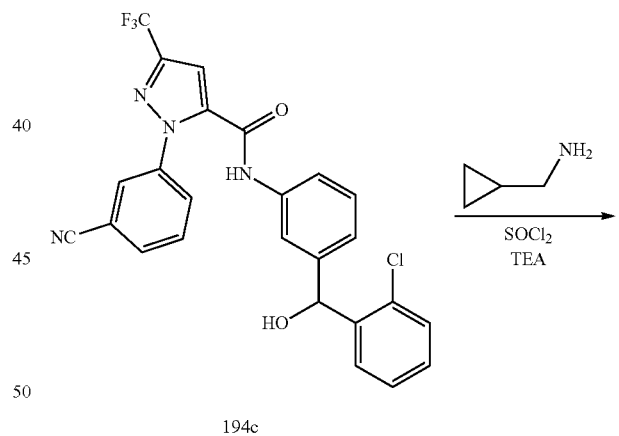

194c

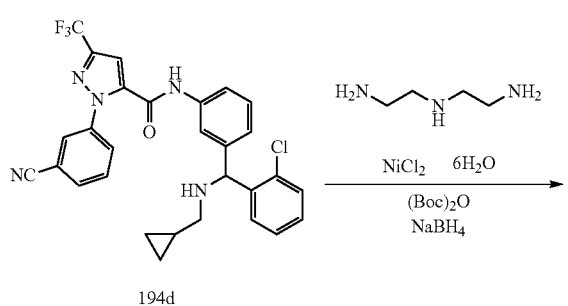

194d

731
-continued

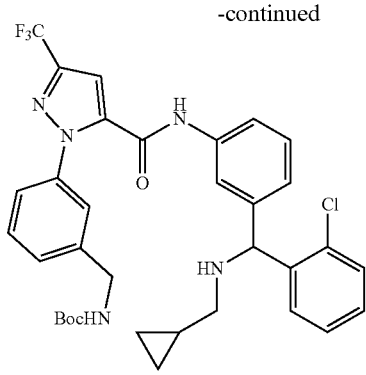

194e

↓ HCl

194f

Preparation of 1-(3-(aminomethyl)phenyl)-N-(3-((2-chlorophenyl)((cyclopropylmethyl)amino)methyl)phenyl)-3-(trifluoromethyl)-1H-pyrazole-5-carboxamide (194f)

Compound (194f) was prepared starting from 2-chlorobenzaldehyde (194a) (10 mmol) in five steps as shown in scheme 194 using procedure as reported in scheme-109 to furnish 1-(3-(aminomethyl)phenyl)-N-(3-((2-chlorophenyl)((cyclopropylmethyl)amino)methyl)phenyl)-3-(trifluoromethyl)-1H-pyrazole-5-carboxamide (194f) (20 mgs) as a white solid; $^1$H NMR (300 MHz, DMSO-d$_6$) δ 10.70 (s, 1H), 7.77-7.65 (m, 1H), 7.64-7.49 (m, 4H), 7.49-7.10 (m, 8H), 5.24 (s, 1H), 3.78 (s, 2H), 2.28 (dd, J=6.8, 2.6 Hz, 2H), 0.99-0.83 (m, 1H), 0.49-0.30 (m, 2H), 0.11--0.02 (m, 2H); $^{19}$F NMR (282 MHz, DMSO) δ -60.72; MS (ES+) 554.3 (M+1); (ES-) 552.3 (M-1); Analysis calculated for C$_{29}$H$_{27}$ClF$_3$N$_5$O.0.5H$_2$O: C, 61.87; H, 5.01; N, 12.44; Found: C, 61.68; H, 5.01; N, 12.43.

Scheme 195

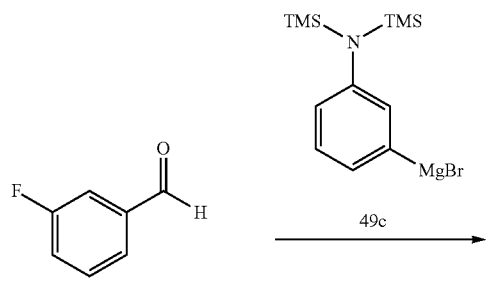

732
-continued

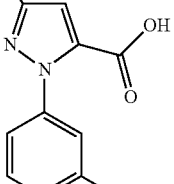

195b

9i

DIPEA
SOCl$_2$
→

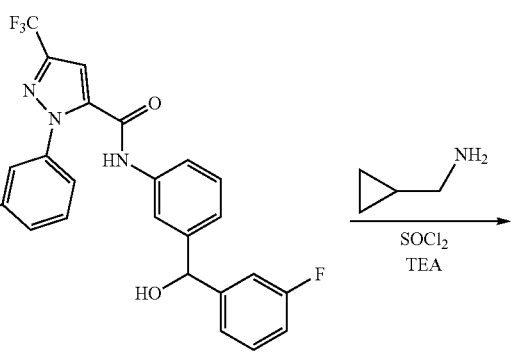

195c cyclopropylmethylamine
SOCl$_2$
TEA
→

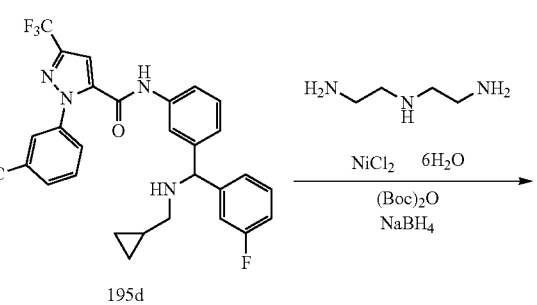

195d

H$_2$N-CH$_2$CH$_2$-NH-CH$_2$CH$_2$-NH$_2$
NiCl$_2$ · 6H$_2$O
(Boc)$_2$O
NaBH$_4$
→

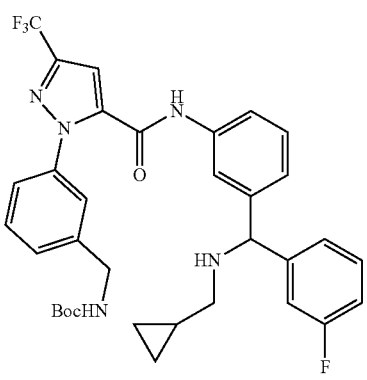

195e

↓ HCl

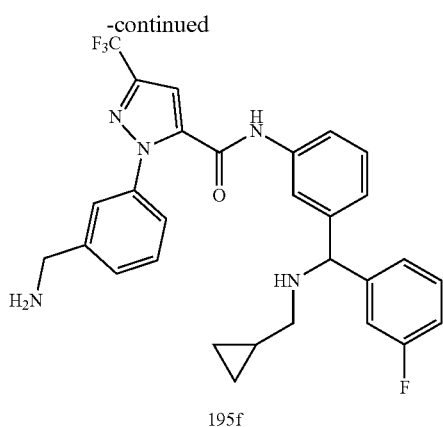

195f

Preparation of 1-(3-(aminomethyl)phenyl)-N-(3-(((cyclopropylmethyl)amino)(3-fluorophenyl)methyl)phenyl)-3-(trifluoromethyl)-1H-pyrazole-5-carboxamide (195f)

Compound (195f) was prepared starting from 3-fluorobenzaldehyde (195a) (10 mmol) in five steps as shown in scheme 195 using procedure as reported in scheme-109 to furnish 1-(3-(aminomethyl)phenyl)-N-(3-(((cyclopropylmethyl)amino)(3-fluorophenyl)methyl)phenyl)-3-(trifluoromethyl)-1H-pyrazole-5-carboxamide (195f) (40 mgs) as a white solid; $^1$H NMR (300 MHz, DMSO-d$_6$) δ 10.95 (s, 1H), 10.11 (s, 2H), 8.39 (s, 3H), 7.88 (s, 1H), 7.73 (s, 1H), 7.68 (s, 1H), 7.67-7.39 (m, 9H), 7.23 (dt, J=8.0, 4.8 Hz, 1H), 5.65 (d, J=7.0 Hz, 1H), 4.13 (d, J=5.7 Hz, 2H), 2.79-2.65 (m, 2H), 1.26-1.05 (m, 1H), 0.65-0.48 (m, 2H), 0.44-0.21 (m, 2H); $^{19}$F NMR (282 MHz, DMSO) δ −60.80, −111.69; MS (ES+) 538.4 (M+1); (ES−) 572.3 (M+Cl); Analysis calculated for C$_{29}$H$_{27}$F$_4$N$_5$O.2HCl.3.5H$_2$O: C, 51.71; H, 5.39; N, 10.40; Found: C, 51.94; H, 5.24; N, 10.33.

Scheme 196

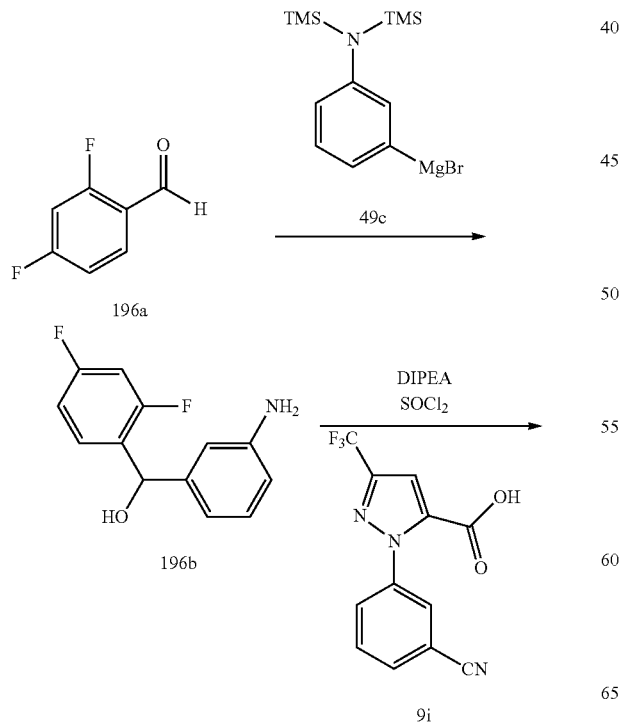

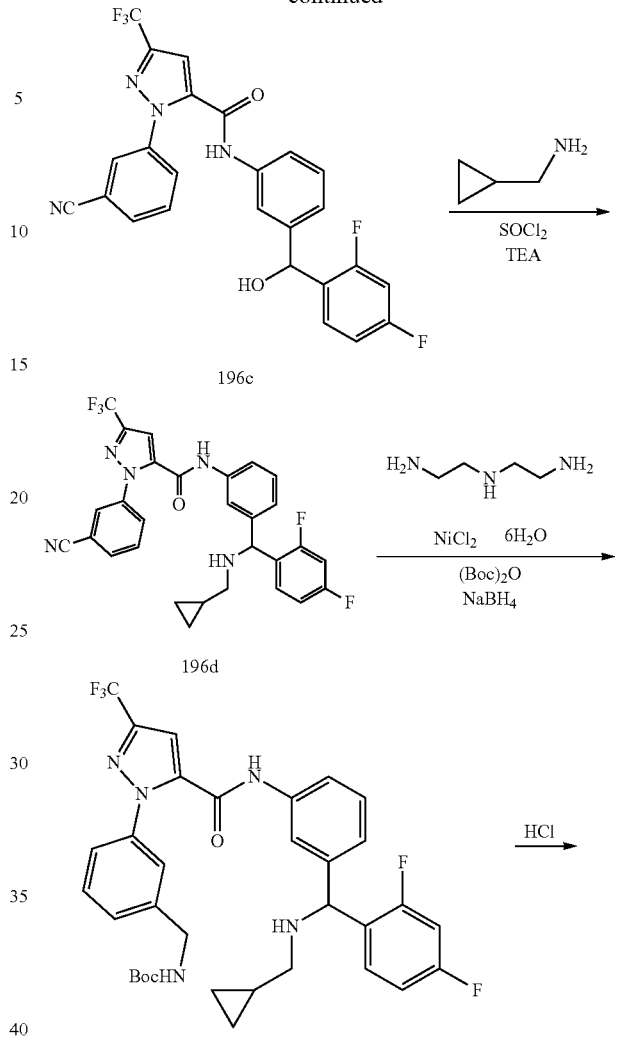

Preparation of 1-(3-(aminomethyl)phenyl)-N-(3-(((cyclopropylmethyl)amino)(2,4-difluorophenyl)methyl)phenyl)-3-(trifluoromethyl)-1H-pyrazole-5-carboxamide (196f)

Compound (196f) was prepared starting from 2,4-difluorobenzaldehyde (196a) (10 mmol) in five steps as shown in scheme 196 using procedure as reported in scheme-109 to furnish 1-(3-(aminomethyl)phenyl)-N-(3-(((cyclopropylmethyl)amino)(2,4-difluorophenyl)methyl)phenyl)-3-(trifluoromethyl)-1H-pyrazole-5-carboxamide (196f) (40 mgs) as a pale orange solid. H NMR (300 MHz, DMSO-$d_6$) δ 10.95 (s, 1H), 10.19 (s, 1H), 8.42 (s, 3H), 8.07 (d, J=13.3 Hz, 1H), 7.85-7.22 (m, 11H), 5.72 (s, 1H), 4.13 (s, 2H), 2.87-2.65 (m, 2H), 1.21-1.00 (m, 1H), 0.67-0.40 (m, 2H), 0.38-0.14 (m, 2H); $^{19}$F NMR (282 MHz, DMSO) δ −60.80, −108.86, −111.97; MS (ES+) 556.3 (M+1); (ES−) 554.4 (M−1), 590.4 (M+Cl); Analysis calculated for $C_{29}H_{26}F_5N_5O·2HCl·1.5H_2O$: C, 53.14; H, 4.77; N, 10.68; Found: C, 53.05; H, 4.68; N, 11.21.

Scheme 197

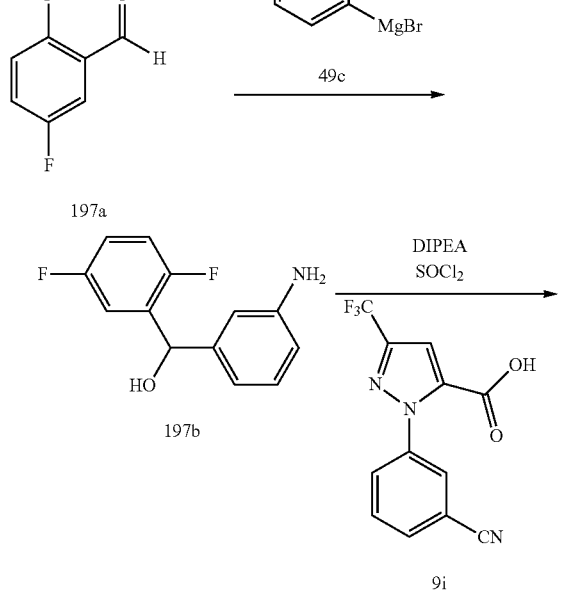

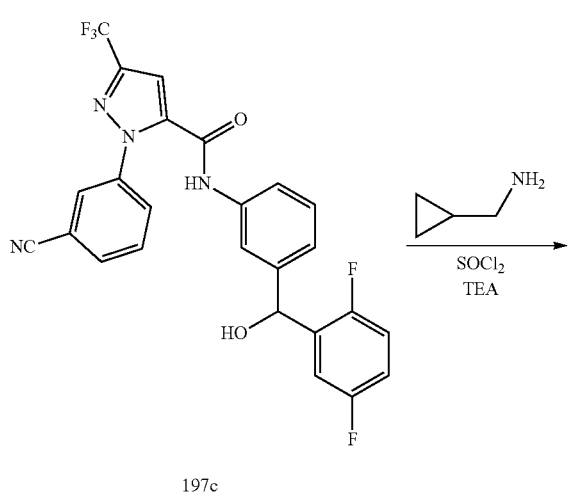

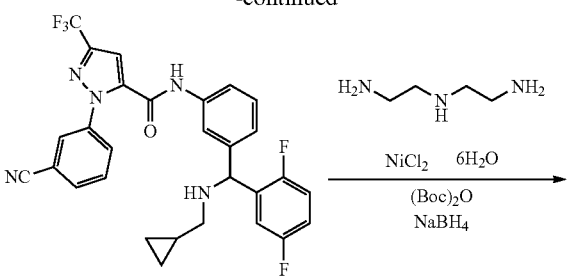

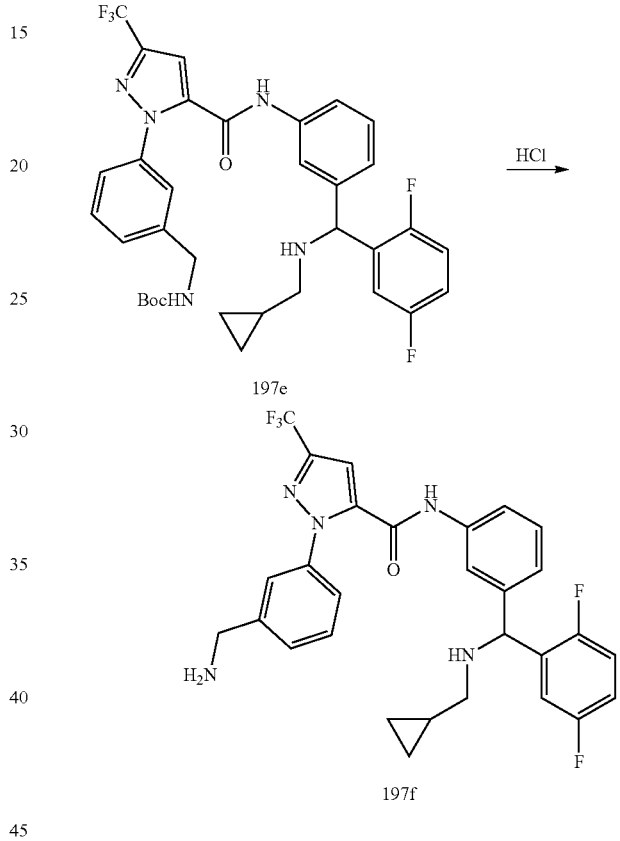

Preparation of 1-(3-(aminomethyl)phenyl)-N-(3-(((cyclopropylmethyl)amino)(2,5-difluorophenyl)methyl)phenyl)-3-(trifluoromethyl)-1H-pyrazole-5-carboxamide (197f)

Compound (197f) was prepared starting from 2,5-difluorobenzaldehyde (197a) (10 mmol) in five steps as shown in scheme 197 using procedure as reported in scheme-109 to furnish 1-(3-(aminomethyl)phenyl)-N-(3-(((cyclopropylmethyl)amino)(2,5-difluorophenyl)methyl)phenyl)-3-(trifluoromethyl)-1H-pyrazole-5-carboxamide (197f) (40 mgs) as a yellow solid; $^1$H NMR (300 MHz, DMSO-$d_6$) δ 10.79 (s, 1H), 8.35 (s, 3H), 7.72 (d, J=1.9 Hz, 1H), 7.71-7.41 (m, 6H), 7.42-7.07 (m, 5H), 5.15 (s, 1H), 4.13 (s, 2H), 2.42-2.27 (m, 2H), 1.00-0.89 (m, 1H), 0.41 (m, 2H), 0.06 (m, 2H); $^{19}$F NMR (282 MHz, DMSO) δ −60.80, −118.15, −124.26. MS (ES+) 556.3 (M+1); (ES−) 590.3 (M+Cl); Analysis calculated for $C_{29}H_{26}F_5N_5O·HCl·2H_2O$: C, 55.46; H, 4.98; N, 11.15; Found: C, 55.18; H, 4.82; N, 11.39.

Scheme 198

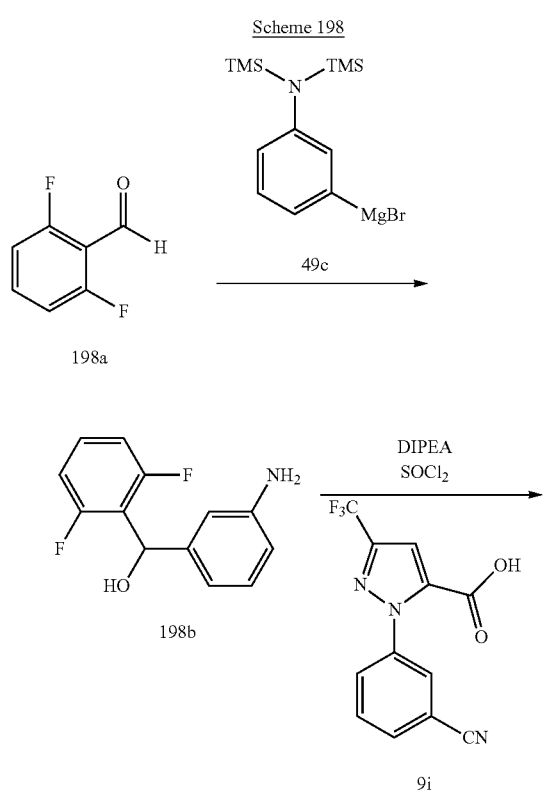

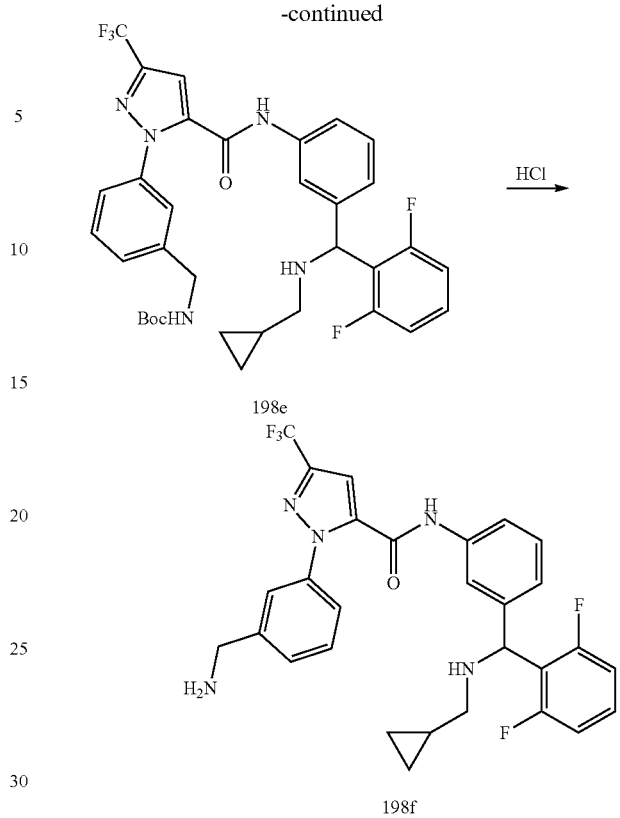

Preparation of 1-(3-(aminomethyl)phenyl)-N-(3-((((cyclopropylmethyl)amino)(2,6-difluorophenyl)methyl)phenyl)-3-(trifluoromethyl)-1H-pyrazole-5-carboxamide (198f)

Compound (198f) was prepared starting from 2,6-difluorobenzaldehyde (198a) (10 mmol) in five steps as shown in scheme 198 using procedure as reported in scheme-109 to furnish 1-(3-(aminomethyl)phenyl)-N-(3-(((cyclopropylmethyl)amino)(2,6-difluorophenyl)methyl)phenyl)-3-(trifluoromethyl)-1H-pyrazole-5-carboxamide (198f) (10 mgs) as a white solid; $^1$H NMR (300 MHz, DMSO-d$_6$) δ 10.72 (s, 1H), 7.65-7.49 (m, 4H), 7.47-7.40 (m, 3H), 7.42-7.23 (m, 3H), 7.09 (dd, J=19.0, 8.0 Hz, 2H), 5.24 (s, 1H), 3.77 (d, J=2.1 Hz, 2H), 2.48-2.22 (m, 2H), 0.90 (dp, J=13.0, 6.1 Hz, 1H), 0.44-0.33 (m, 2H), 0.21-0.03 (m, 2H); $^{19}$F NMR (282 MHz, DMSO) δ −60.71, −114.27; MS (ES+) 556.4 (M+1); (ES−) 554.4 (M−1), 590.3 (M+Cl).

Scheme 199

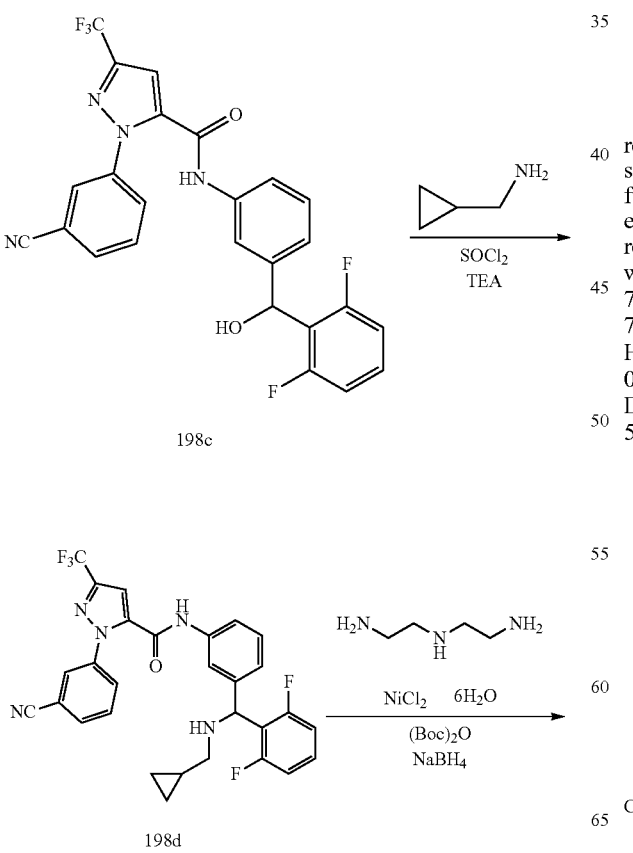

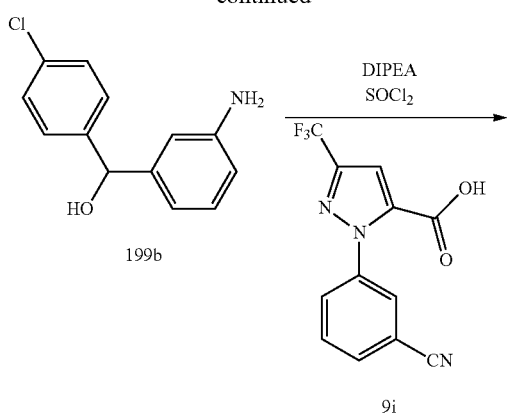

199b

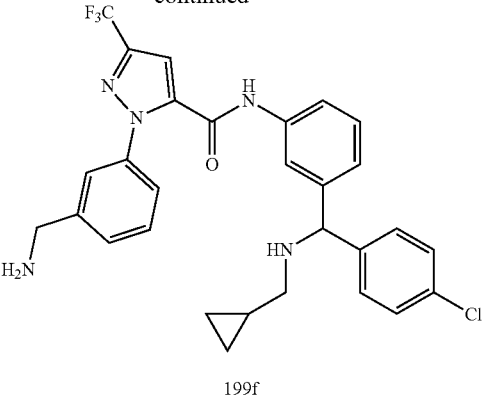

199f

Preparation of 1-(3-(aminomethyl)phenyl)-N-(3-((6-chlorophenyl)((cyclopropylmethyl)amino)methyl)phenyl)-3-(trifluoromethyl)-1H-pyrazole-5-carboxamide (199f)

Compound (199f) was prepared starting from 4-chlorobenzaldehyde (199a) (10 mmol) in five steps as shown in scheme 199 using procedure as reported in scheme-109 to furnish 1-(3-(aminomethyl)phenyl)-N-(3-((6-chlorophenyl)((cyclopropylmethyl)amino)methyl)phenyl)-3-(trifluoromethyl)-1H-pyrazole-5-carboxamide (199f) (15 mgs) as a white solid; $^1$H NMR (300 MHz, DMSO-$d_6$) δ 10.68 (s, 1H), 7.63 (t, J=1.8 Hz, 1H), 7.59-7.49 (m, 3H), 7.44-7.14 (m, 9H), 4.82 (s, 1H), 3.77 (s, 2H), 2.27 (d, J=6.6 Hz, 2H), 1.00-0.81 (m, 1H), 0.49-0.28 (m, 2H), 0.12--0.00 (m, 2H); $^{19}$F NMR (282 MHz, DMSO) δ −60.72; MS (ES+) 556.3 (M+1); Analysis calculated for $C_{29}H_{27}ClF_3N_5O$: C, 62.87; H, 4.91; N, 12.64; Found: C, 62.63; H, 5.01; N, 12.55.

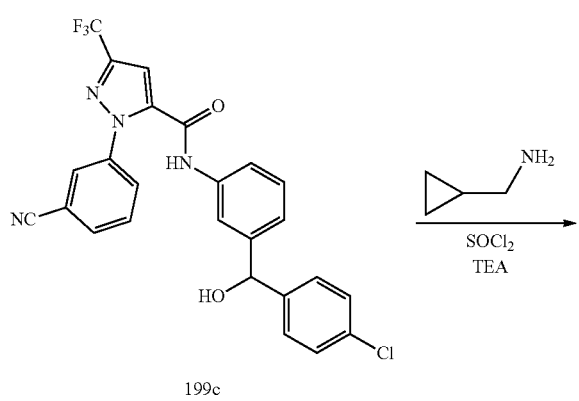

199c

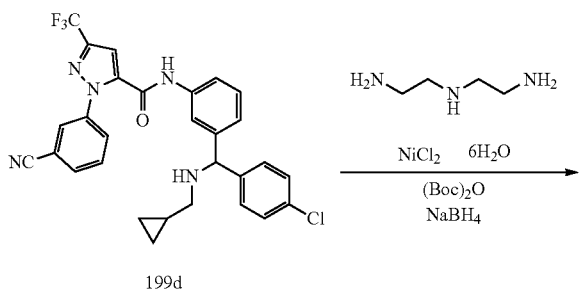

199d

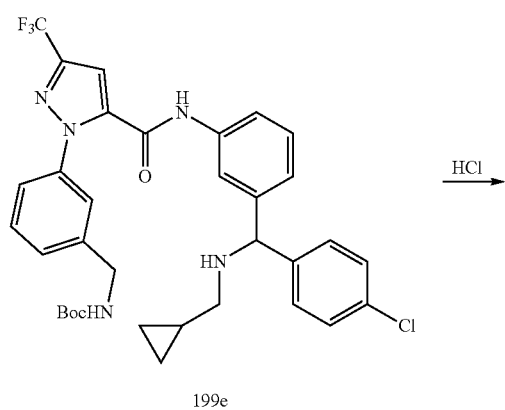

199e

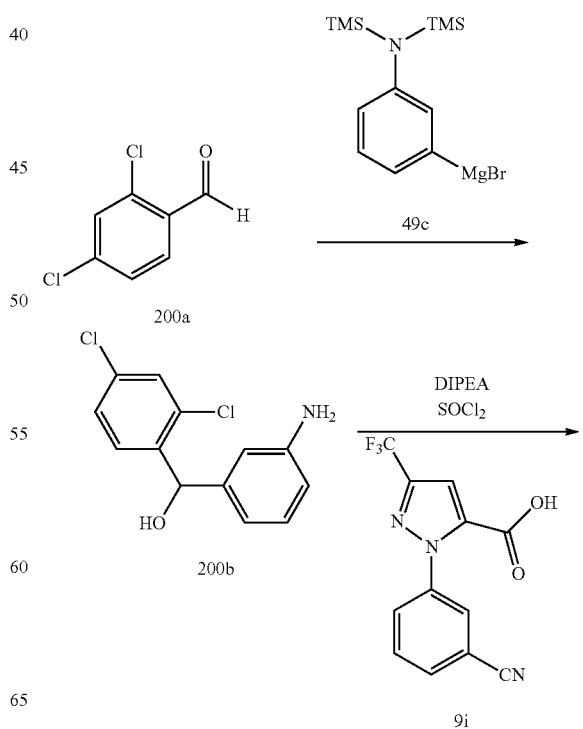

Scheme 200

200a

200b

9i

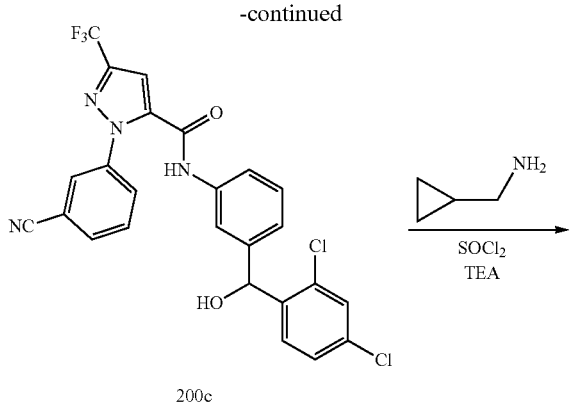
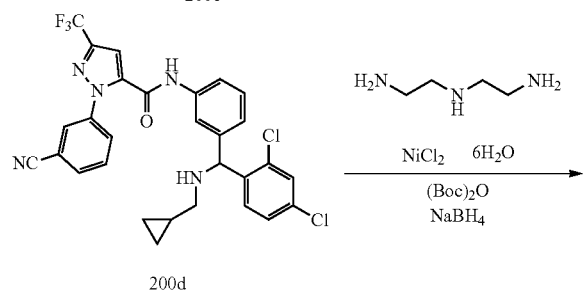
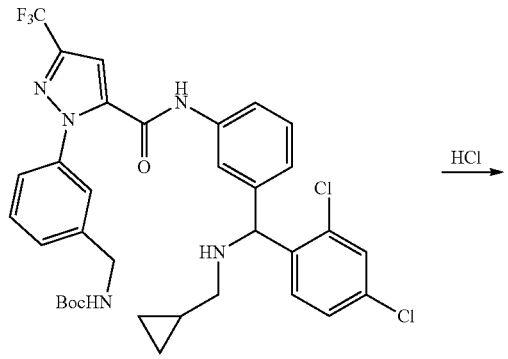
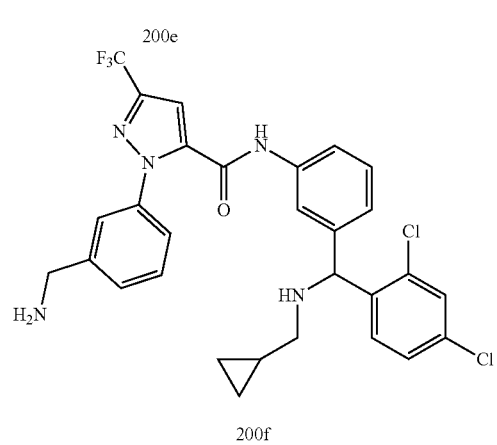

Preparation of 1-(3-(aminomethyl)phenyl)-N-(3-((2,4-dichlorophenyl)((cyclopropylmethyl)amino)methyl)phenyl)-3-(trifluoromethyl)-1H-pyrazole-5-carboxamide (200f)

Compound (200f) was prepared starting from 2,4-dichlorobenzaldehyde (200a) (10 mmol) in five steps as shown in scheme 200 using procedure as reported in scheme-109 to furnish 1-(3-(aminomethyl)phenyl)-N-(3-((2,4-dichlorophenyl)((cyclopropylmethyl)amino)methyl)phenyl)-3-(trifluoromethyl)-1H-pyrazole-5-carboxamide (200f) (30 mgs) as a tan solid; $^1$H NMR (300 MHz, DMSO-d$_6$) δ 10.72 (s, 1H), 7.73 (d, J=8.4 Hz, 1H), 7.66-7.41 (m, 9H), 7.27 (t, J=7.7 Hz, 1H), 7.15 (d, J=7.8 Hz, 1H), 6.67 (s, 2H), 5.20 (s, 1H), 4.01 (s, 2H), 2.27 (dd, J=6.3, 3.4 Hz, 2H), 0.99-0.77 (m, 1H), 0.47-0.31 (m, 2H), 0.10--0.01 (m, 2H); $^{19}$F NMR (282 MHz, DMSO) δ −60.78; MS (ES+) 588.3, 590.3 (M+1); Analysis calculated for C$_{29}$H$_{26}$C$_{12}$F$_3$N$_5$O.1.5H$_2$O: C, 56.59; H, 4.75; N, 11.38; Found: C, 56.67; H, 4.87; N, 10.99.

Scheme 201

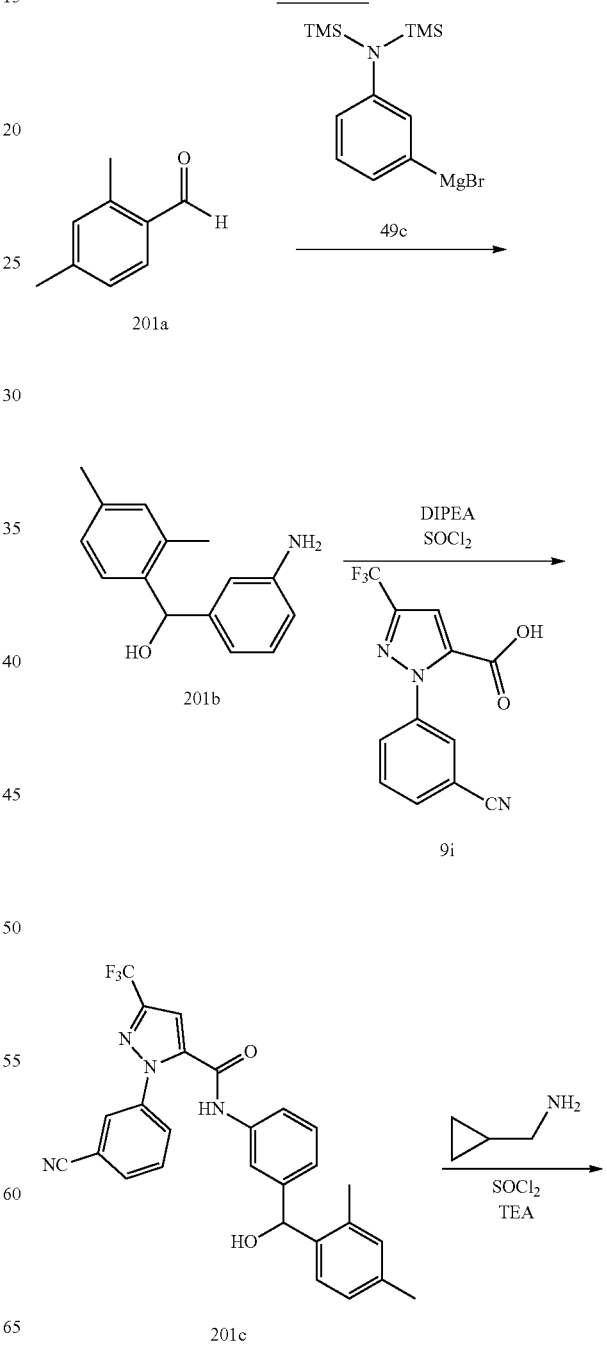

743

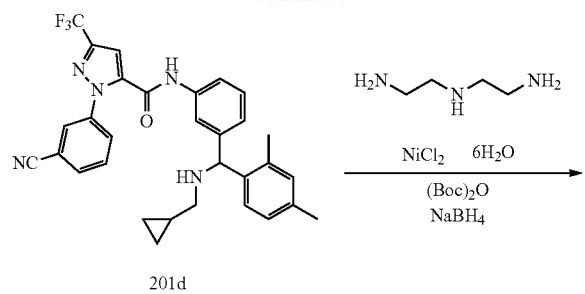

201d

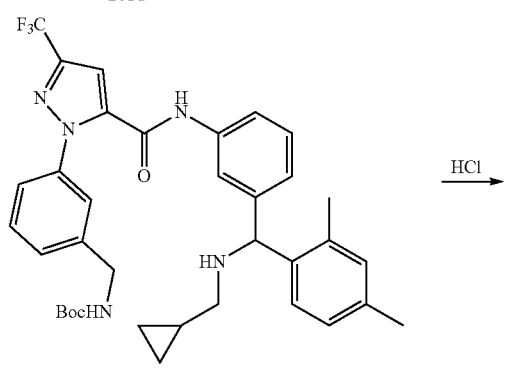

201e

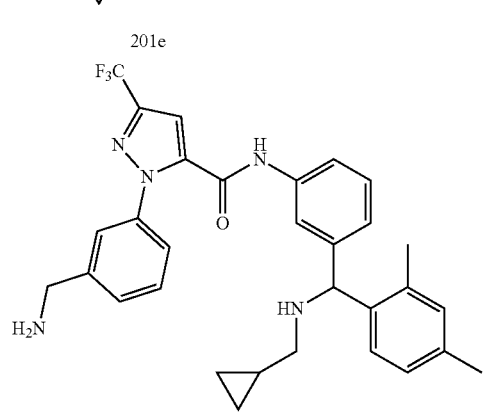

201f

Preparation of 1-(3-(aminomethyl)phenyl)-N-(3-((((cyclopropylmethyl)amino)(2,4-dimethylphenyl)methyl)phenyl)-3-(trifluoromethyl)-1H-pyrazole-5-carboxamide (201f)

Compound (201f) was prepared starting from 2,4-dimethylbenzaldehyde (201a) (10 mmol) in five steps as shown in scheme 201 using procedure as reported in scheme-109 to furnish 1-(3-(aminomethyl)phenyl)-N-(3-(((cyclopropylmethyl)amino)(2,4-dimethylphenyl)methyl)phenyl)-3-(trifluoromethyl)-1H-pyrazole-5-carboxamide (201f) (110 mgs) as a yellow solid; $^1$H NMR (300 MHz, DMSO-$d_6$) δ 10.91 (s, 1H), 9.71 (s, 1H), 8.34 (s, 3H), 7.78-7.37 (m, 10H), 7.14 (d, J=7.8 Hz, 1H), 7.05 (s, 1H), 5.59 (s, 1H), 4.13 (s, 2H), 2.85-2.67 (m, 2H), 2.32-2.21 (m, 6H), 1.17-0.96 (m, 1H), 0.64-0.48 (m, 2H), 0.23 (d, J=19.7 Hz, 2H). $^{19}$F NMR (282 MHz, DMSO) δ -60.80; MS (ES+) 548.4 (M+1); (ES-) 582.3 (M+Cl); Analysis calculated for $C_{31}H_{32}F_3N_5O.2HCl$ 3.25$H_2O$: C, 54.83; H, 6.01; N, 10.31; Found: C, 54.90; H, 6.02; N, 9.64.

744

Scheme 202

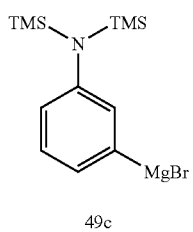

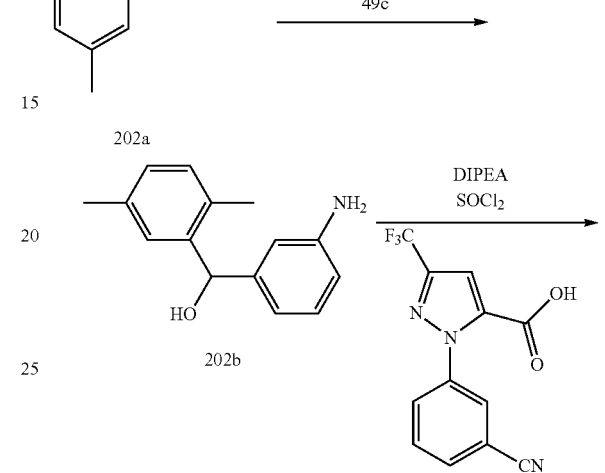

202b

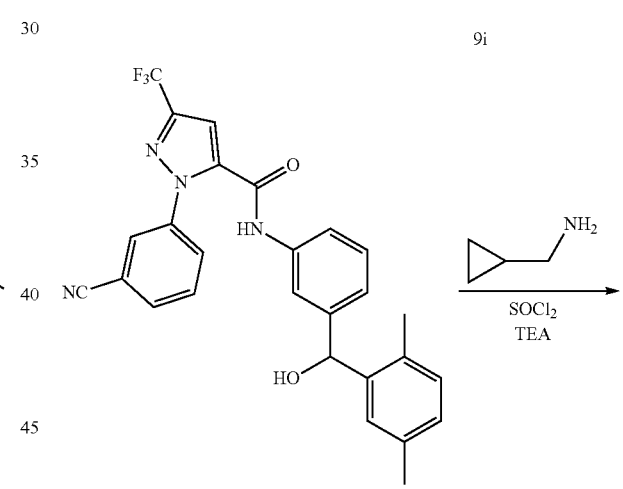

202c

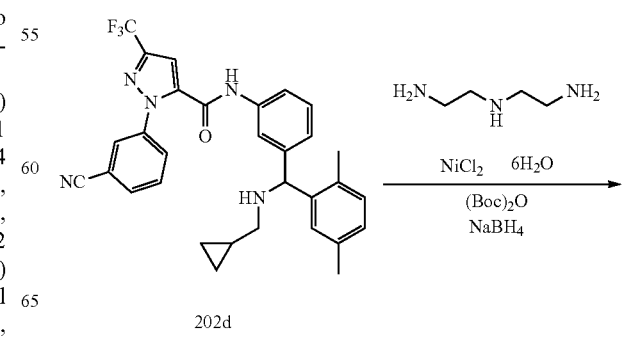

202d

745

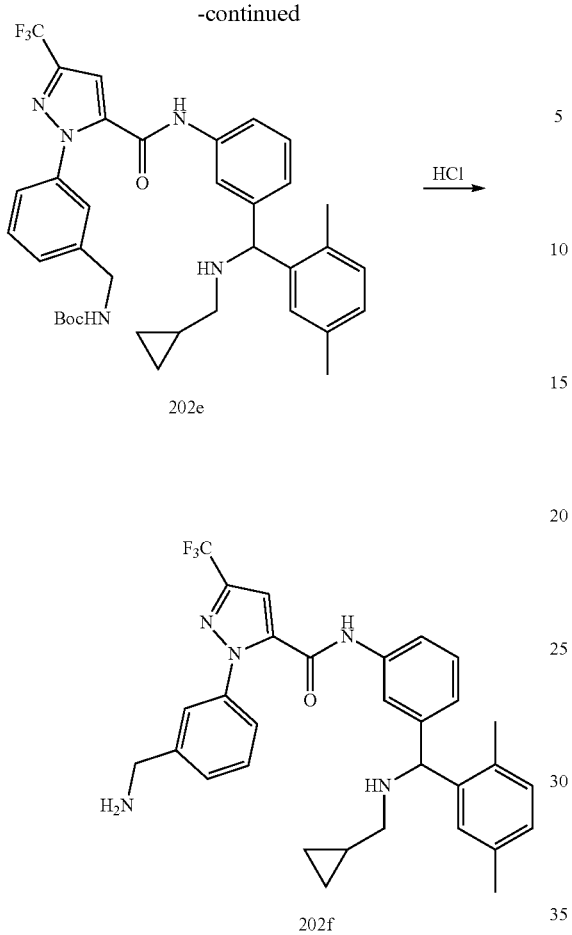

202e

202f

Preparation of 1-(3-(aminomethyl)phenyl)-N-(3-((((cyclopropylmethyl)amino)(2,5-dimethylphenyl)methyl)phenyl)-3-(trifluoromethyl)-1H-pyrazole-5-carboxamide (202f)

Compound (202f) was prepared starting from 2,5-dimethylbenzaldehyde (202a) (10 mmol) in five steps as shown in scheme 202 using procedure as reported in scheme-109 to furnish 1-(3-(aminomethyl)phenyl)-N-(3-(((cyclopropylmethyl)amino)(2,5-dimethylphenyl)methyl)phenyl)-3-(trifluoromethyl)-1H-pyrazole-5-carboxamide (202f) (60 mgs) as a light green solid; $^1$H NMR (300 MHz, DMSO-$d_6$) δ 10.95 (s, 1H), 9.73 (s, 2H), 8.35 (d, J=14.1 Hz, 3H), 7.80 (s, 1H), 7.73 (s, 1H), 7.69-7.42 (m, 8H), 7.15-7.05 (m, 2H), 5.59 (s, 1H), 4.12 (d, J=5.1 Hz, 2H), 2.96-2.63 (m, 2H), 2.31 (s, 3H), 2.25 (s, 3H), 1.21-1.01 (m, 1H), 0.56 (d, J=8.0 Hz, 2H), 0.28 (s, 2H); $^{19}$F NMR (282 MHz, DMSO) δ −60.80; MS (ES+) 548.4 (M+1); Analysis calculated for $C_{31}H_{32}F_3N_5O.4HCl.2H_2O$: C, 49.81; H, 5.66; N, 9.37; Found: C, 49.85; H, 5.53; N, 8.86.

746

Scheme 203

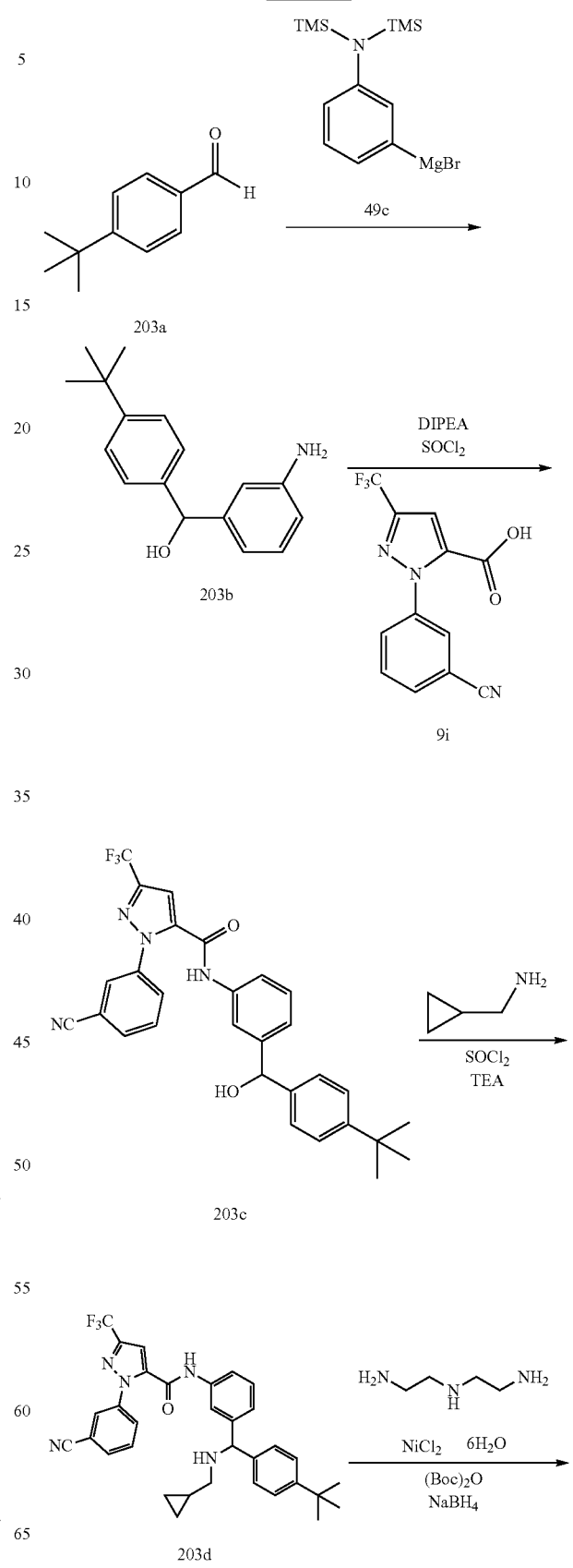

747 | 748

-continued

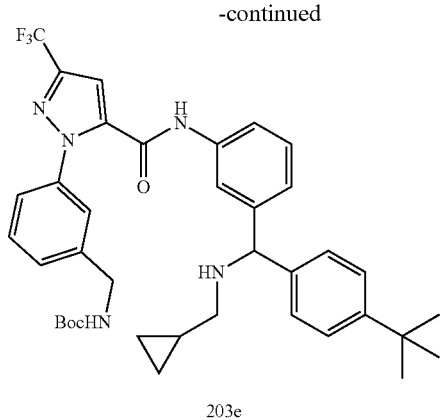

203e

→ HCl

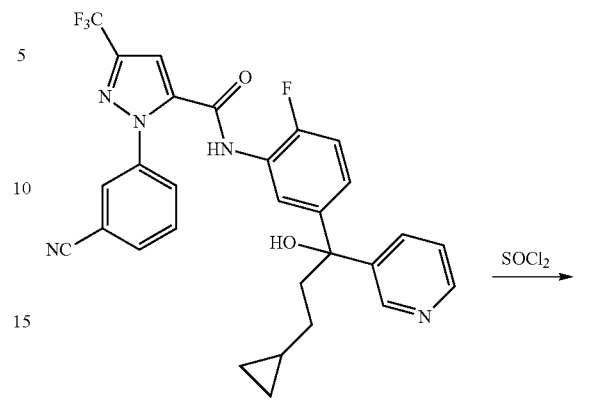

Scheme 204

58b → SOCl₂

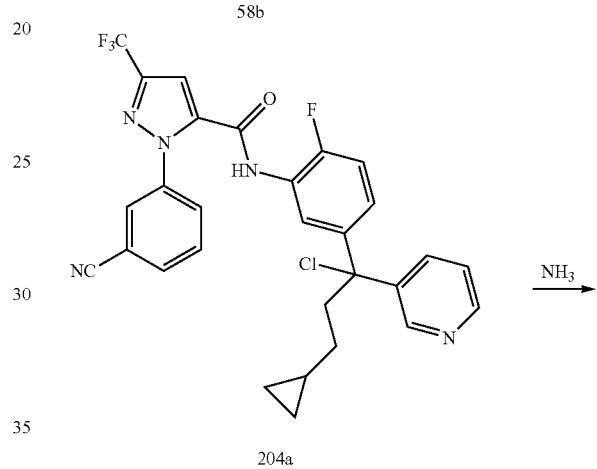

204a → NH₃

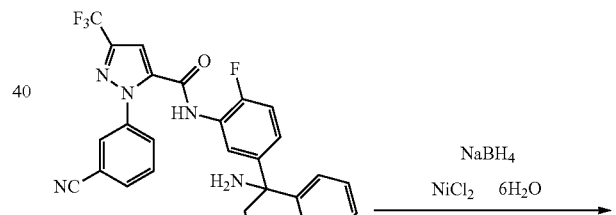

204b

NaBH₄
NiCl₂  6H₂O
H₂N-CH₂CH₂-NH-CH₂CH₂-NH₂

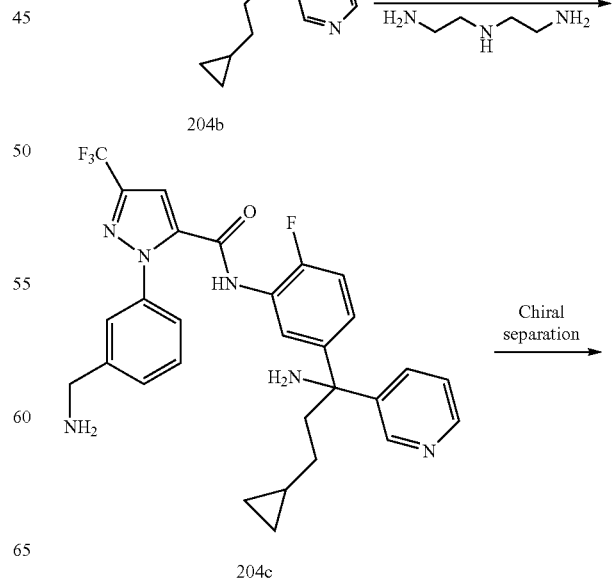

204c

Chiral separation →

Preparation of 1-(3-(aminomethyl)phenyl)-N-(3-((4-(tert-butyl)phenyl)((cyclopropylmethyl)amino)methyl)phenyl)-3-(trifluoromethyl)-1H-pyrazole-5-carboxamide (203f)

Compound (203f) was prepared starting from 4-(tert-butyl)benzaldehyde (203a) (10 mmol) in five steps as shown in scheme 203 using procedure as reported in scheme-109 to furnish 1-(3-(aminomethyl)phenyl)-N-(3-((4-(tert-butyl)phenyl)((cyclopropylmethyl)amino)methyl)phenyl)-3-(trifluoromethyl)-1H-pyrazole-5-carboxamide (203f) (20 mgs) as a light yellow solid. $^1$H NMR (300 MHz, DMSO-$d_6$) δ 10.70 (s, 1H), 7.66 (s, 1H), 7.61 (s, 2H), 7.57-7.34 (m, 4H), 7.30 (s, 4H), 7.24-7.18 (m, 2H), 4.77 (s, 1H), 3.95 (s, 2H), 2.27 (d, J=6.5 Hz, 2H), 1.23 (s, 9H), 1.02-0.70 (m, 1H), 0.46-0.29 (m, 2H), 0.08-0.02 (m, 2H); $^{19}$F NMR (282 MHz, DMSO) δ −60.77; MS (ES+) 576.4 (M+1); Analysis calculated for $C_{33}H_{36}F_3N_5O.2H_2O$: C, 64.80; H, 6.59; N, 11.45; Found: C, 65.10; H, 6.38; N, 10.61.

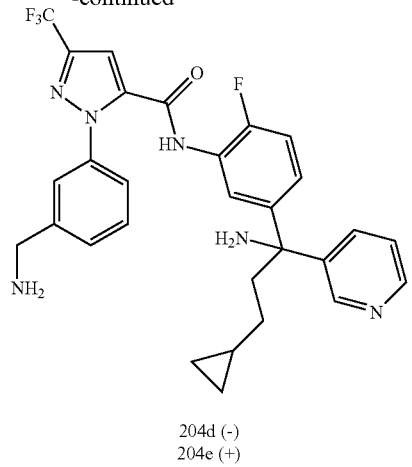

204d (−)
204e (+)

Preparation of (−)-N-(5-(1-amino-3-cyclopropyl-1-(pyridin-3-yl)propyl)-2-fluorophenyl)-1-(3-(aminomethyl)phenyl)-3-(trifluoromethyl)-1H-pyrazole-5-carboxamide (204d) and (+)-N-(5-(1-amino-3-cyclopropyl-1-(pyridin-3-yl)propyl)-2-fluorophenyl)-1-(3-(aminomethyl)phenyl)-3-(trifluoromethyl)-1H-pyrazole-5-carboxamide (204e)

Compounds 204d and 204e can be prepared as shown in scheme 205 from compound 58b.

Analytical data for (−)-N-(5-(1-amino-3-cyclopropyl-1-(pyridin-3-yl)propyl)-2-fluorophenyl)-1-(3-(aminomethyl)phenyl)-3-(trifluoromethyl)-1H-pyrazole-5-carboxamide (204d), free base as a white solid; $^1$HNMR (300 MHz, DMSO-$d_6$) δ 10.53 (bs, 1H) 8.58 (d, J=2.4 Hz, 1H), 8.36 (dd, J=4.7, 1.6 Hz, 1H), 7.75 (dt, J=8.1, 2.0 Hz, 1H), 7.63-7.54 (m, 2H), 7.50 (s, 1H), 7.47-7.36 (m, 2H), 7.30 (m, 3H), 7.18 (t, J=9.4 Hz, 1H), 3.77 (s, 2H), 2.37-2.03 (m, 2H), 1.03 (m, 2H), 0.63 (m, 1H), 0.41-0.24 (m, 2H), −0.08 (m, 2H); $^{19}$F NMR (282 MHz, DMSO) δ −60.74, −124.19; MS (ES+) 553.4 (M+1), (ES−) 551.4 (M−1); Optical rotation: $[α]_D$=(−) 1.87 [CH$_3$OH, 0.535].

Analytical data for (+)-N-(5-(1-amino-3-cyclopropyl-1-(pyridin-3-yl)propyl)-2-fluorophenyl)-1-(3-(aminomethyl)phenyl)-3-(trifluoromethyl)-1H-pyrazole-5-carb oxamide (204e), free base as a white solid; $^1$H NMR (300 MHz, DMSO-$d_6$) δ 10.57 (bs, 1H), 8.61 (m, 1H), 8.35 (m, 1H), 7.87-7.08 (m, 10H), 3.73 (s, 2H), 2.38-2.05 (m, 2H), 1.07 (m, 2H), 0.65 (m, 1H), 0.36 (m, 2H), 0.00 (m, 2H); $^{19}$F NMR (282 MHz, DMSO) δ −60.43, −124.00; MS (ES+) 553.4 (M+1); $[α]_D$=(+) 0.685 [CH$_3$OH, 1.75].

Scheme 205

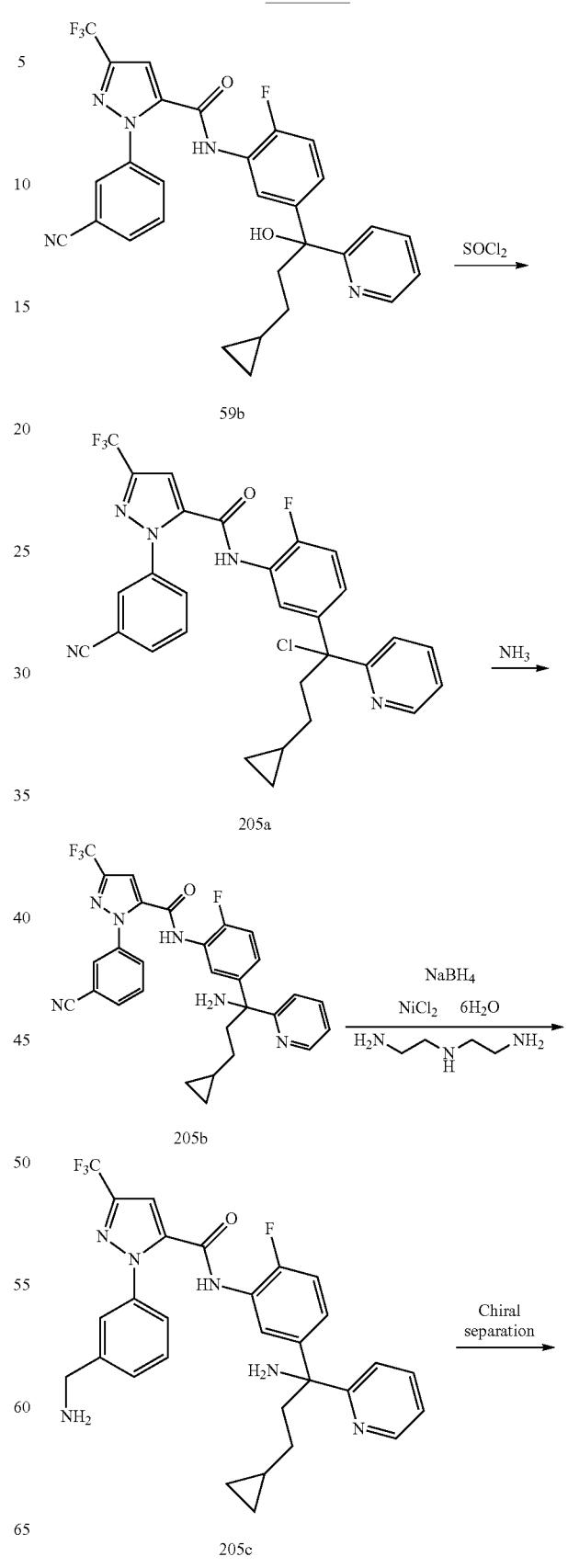

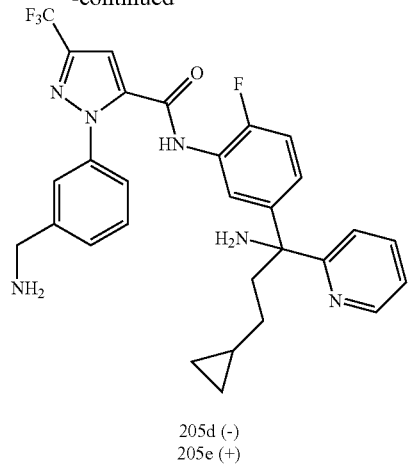

205d (−)
205e (+)

Preparation of (−)-N-(5-(1-amino-3-cyclopropyl-1-(pyridin-2-yl)propyl)-2-fluorophenyl)-1-(3-(aminomethyl)phenyl)-3-(trifluoromethyl)-1H-pyrazole-5-carboxamide (205d) and (+)-N-(5-(1-amino-3-cyclopropyl-1-(pyridin-2-yl)propyl)-2-fluorophenyl)-1-(3-(aminomethyl)phenyl)-3-(trifluoromethyl)-1H-pyrazole-5-carboxamide (205e)

Compounds 205d and 205e can be prepared as shown in scheme 205. Chiral purity was checked using Chiral HPLC: AD-H column 90/10/0.2 (Hexane/ethanol/TEA) 0.8 mL/min UV 260 nM, 45 mins run time (Temp 40° C.). Rt=20.976 (peak-1 for 205d); Rt=26.044 (peak-2 for 205e).

Analytical data for (−)-N-(5-(1-amino-3-cyclopropyl-1-(pyridin-2-yl)propyl)-2-fluorophenyl)-1-(3-(aminomethyl)phenyl)-3-(trifluoromethyl)-1H-pyrazole-5-carboxamide (205d), White solid as hydrochloride salt; MP: 252.6° C.; $^1$H NMR (300 MHz, DMSO-d$_6$) δ 10.85 (s, 1H), 9.08 (s, 3H), 8.69-8.62 (m, 1H), 8.53 (s, 3H), 7.89 (td, J=7.8, 1.9 Hz, 1H), 7.78-7.69 (m, 2H), 7.64 (m, 2H), 7.55 (d, J=7.9 Hz, 1H), 7.51 (dd, J=3.6, 1.7 Hz, 1H), 7.49-7.43 (m, 1H), 7.41 (m, 1H), 7.38 (m, 1H), 7.36-7.27 (m, 1H), 4.11 (q, J=5.5 Hz, 2H), 2.67-2.50 (m, 2H), 1.27-1.15 (m, 1H), 1.03-0.89 (m, 1H), 0.75-0.58 (m, 1H), 0.37 (m, 2H), 0.04-−0.09 (m, 2H); $^{19}$F NMR (282 MHz, DMSO) δ −60.82, −120.56; MS (ES+) 553.4 (M+1), (ES−) 551.6 (M−1); Chiral Purity >99.9% ee; HPLC purity 98.4034%; Optical rotation: $[α]_D$=(−) 19.234 [CH$_3$OH, 1.175].

Analytical data for (+)-N-(5-(1-amino-3-cyclopropyl-1-(pyridin-2-yl)propyl)-2-fluorophenyl)-1-(3-(aminomethyl)phenyl)-3-(trifluoromethyl)-1H-pyrazole-5-carboxamide (205e), White solid as hydrochloride salt; MP 227.9° C.; $^1$H NMR (300 MHz, DMSO-d$_6$) δ 10.81 (s, 1H), 9.02 (s, 3H), 8.66 (m, 1H), 8.42 (s, 3H), 7.89 (td, J=7.8, 1.8 Hz, 1H), 7.73 (m, 1H), 7.70 (m, 1H), 7.67-7.59 (m, 2H), 7.56 (d, J=7.9 Hz, 1H), 7.51 (dd, J=3.9, 2.0 Hz, 1H), 7.44 (m, 1H), 7.39 (m, 1H), 7.36 (m, 1H), 7.34-7.28 (m, 1H), 4.12 (d, J=5.9 Hz, 2H), 2.57-2.40 (m, 2H), 1.21 (m, 1H), 0.96 (m, 1H), 0.66 (m, 1H), 0.42-0.32 (m, 2H), −0.03 (m, 2H); $^{19}$F NMR (282 MHz, DMSO) δ −60.82, −120.56; MS (ES+) 553.4 (M+1), (ES−) 587.2 (M+Cl); Chiral Purity >99.9% ee; HPLC purity >99.9%; Optical rotation: $[α]_D$=(+) 19.43 [CH$_3$OH, 0.525].

Scheme 206

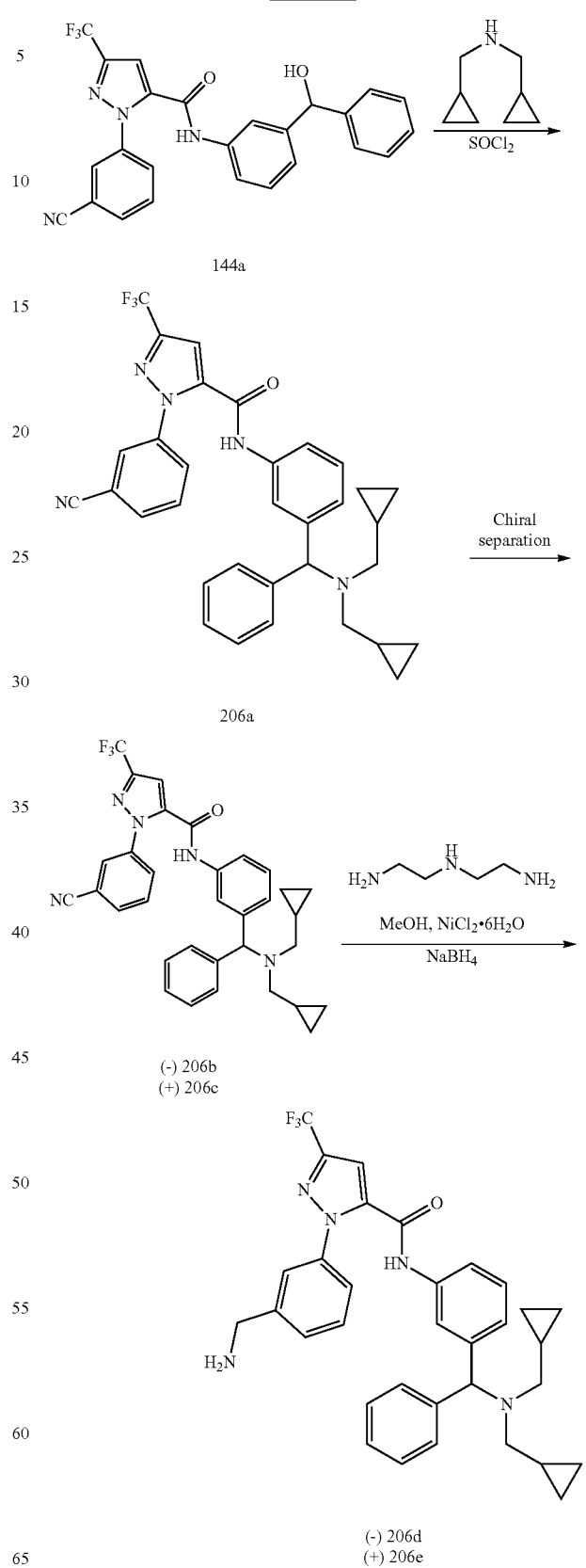

Preparation of (−)-1-(3-(aminomethyl)phenyl)-N-(5-((bis(cyclopropylmethyl)amino)(phenyl)methyl)-2-fluorophenyl)-3-(trifluoromethyl)-1H-pyrazole-5-carboxamide (206d)

Step-1: Preparation of N-(3-((bis(cyclopropylmethyl)amino)(phenyl)methyl)phenyl)-1-(3-cyanophenyl)-3-(trifluoromethyl)-1H-pyrazole-5-carboxamide (206a)

Compound 206a can be prepared from compound 144a as reported in step-1 of Scheme-168 using bis-cyclopropylmethyl-amine (preparation reported by Baruah, Anima et al. in Preparation of novel benzylamine derivatives as CETP inhibitors; WO 2006/073973).

Step-2: Preparation of (−)-N-(3-((bis(cyclopropylmethyl)amino)(phenyl)methyl)phenyl)-1-(3-cyanophenyl)-3-(trifluoromethyl)-1H-pyrazole-5-carboxamide (206b)

Compound 206b can be obtained by preparative Chiral HPLC separation of compound 206a prepared in step-1; $^1$H NMR (300 MHz, DMSO-$d_6$) δ 10.51 (s, 1H), 8.11 (s, 1H), 8.00 (dt, J=7.7, 1.3 Hz, 1H), 7.90 (d, J=8.2 Hz, 1H), 7.76-7.68 (m, 2H), 7.60 (d, J=7.5 Hz, 1H), 7.41-7.14 (m, 7H), 4.92 (s, 1H), 2.44 (d, J=3.9 Hz, 4H), 0.90 (t, J=7.5 Hz, 2H), 0.47-0.30 (m, 4H), −0.04−−0.14 (m, 4H); $^{19}$F NMR (282 MHz, DMSO) δ −60.95, −123.40; IR 2237 cm$^{-1}$ (for —CN); MS (ES+) 588.3 (M+1); Optical rotation: [α]$_D$=(−) 18.97 [CH$_3$OH, 2.52]; Analysis calculated for C$_{33}$H$_{29}$F$_4$N$_5$O: C, 67.45; H, 4.97; N, 11.92; Found: C, 67.32; H, 5.08; N, 11.75.

Step-3: Preparation of (−)-1-(3-(aminomethyl)phenyl)-N-(5-((bis(cyclopropylmethyl)amino)(phenyl)methyl)-2-fluorophenyl)-3-(trifluoromethyl)-1H-pyrazole-5-carboxamide (206d)

To a stirred solution of (−)-N-(5-((bis(cyclopropylmethyl)amino)(phenyl)methyl)-2-fluorophenyl)-1-(3-cyanophenyl)-3-(trifluoromethyl)-1H-pyrazole-5-carboxamide (206b) (6.0 g, 10.21 mmol) in anhydrous methanol (100 mL), cooled to 0° C., was added nickel(II) chloride hexahydrate (0.607 g, 2.55 mmol), sodium borohydride (2.90 g, 77 mmol) was added to the reaction mixture in small portions over a 45 min period. The reaction mixture was stirred for 30 min at 0° C. and quenched with N1-(2-aminoethyl)ethane-1,2-diamine (2.206 mL, 20.42 mmol) stirred for 30 mins and concentrated in vacuum to dryness. The residue obtained was stirred in water overnight. The solid was dissolved by adding conc. HCl (25.00 mL, 300 mmol). Insoluble solid was removed by filtration. The filtrate was nuetralized with solid NaOH (12 g, 300 mmol) and further basified to pH=12 using 3 N NaOH. The pink solution was extracted with chloroform (2×100 mL). The organic layer was combined, dried, filtered and concentrated in vacuum. The residue obtained was purified by flash column chromatography (silica gel 80 g, eluting with 0-25% methanol in chloroform) to furnish (−)-1-(3-(aminomethyl)phenyl)-N-(5-((bis(cyclopropylmethyl)amino)(phenyl)methyl)-2-fluorophenyl)-3-(trifluoromethyl)-1H-pyrazole-5-carboxamide free base (206d) (2.18 g, 3.68 mmol, 36.1% yield) as a white foam; $^1$H NMR (300 MHz, DMSO-$d_6$) δ 10.54 (s, 1H), 7.70-7.62 (m, 1H), 7.57 (s, 1H), 7.52 (s, 1H), 7.47-7.25 (m, 8H), 7.24-7.15 (m, 2H), 4.91 (s, 1H), 3.79 (s, 2H), 2.45 (dd, J=6.2, 2.3 Hz, 4H), 0.90 (tq, J=11.4, 6.5, 5.7 Hz, 2H), 0.50-0.26 (m, 4H), −0.03−−0.18 (m, 4H); $^{19}$F NMR (282 MHz, DMSO) δ −60.74, −123.73; MS (ES+) 592.4 (M+1); (ES−) 590.4 (M−1); HPLC (Rt=5.047, 98.4644); Optical rotation: [α]$_D$=(−) 1.51 [CH$_3$OH, 1.565]; Analysis calculated for C$_{33}$H$_{33}$F$_4$N$_5$O.0.5H$_2$O: C, 65.99; H, 5.71; N, 11.66; Found: C, 66.29; H, 5.75; N, 11.57. The above solid (1.68 g, 2.8 mmol) was dissolved in ethanol (5 mL) and added conc. HCl (1.17 mL, 14 mmol), water (5 mL), stirred for 30 mins and concentrated in vacuum to dryness to afford 1.7 gm (−)-1-(3-(aminomethyl)phenyl)-N-(5-((bis(cyclopropylmethyl)amino)(phenyl)methyl)-2-fluorophenyl)-3-(trifluoromethyl)-1H-pyrazole-5-carboxamide (206d) HCl salt as a white solid; MP 199° C.; $^1$H NMR (300 MHz, DMSO-$d_6$) δ 11.61 (s, 1H), 10.86 (s, 1H), 8.52 (d, J=7.1 Hz, 3H), 8.20 (dd, J=7.0, 2.3 Hz, 1H), 8.08-7.92 (m, 3H), 7.76-7.69 (m, 2H), 7.67-7.51 (m, 3H), 7.46-7.31 (m, 4H), 5.81 (d, J=9.8 Hz, 1H), 4.12 (q, J=5.8 Hz, 2H), 3.08 (dtt, J=17.1, 8.4, 4.5 Hz, 4H), 1.20 (ddt, J=12.6, 8.5, 5.0 Hz, 2H), 0.58 (ddq, J=7.4, 3.3, 1.9 Hz, 4H), 0.36-0.04 (m, 4H); $^{19}$F NMR (282 MHz, DMSO) δ −60.81, −120.39; MS (ES+) 592.4 (M+1); (ES−) 626.4 (M+Cl); Optical rotation: [α]$_D$= (−) 11.11 [CH$_3$OH, 1.17]; Analysis calculated for C$_{33}$H$_{33}$F$_4$N$_5$O.2HCl 1.75H$_2$O: C, 56.94; H, 5.57; Cl, 10.19; N, 10.06; Found: C, 56.98; H, 5.47; Cl, 10.44; N, 9.99.

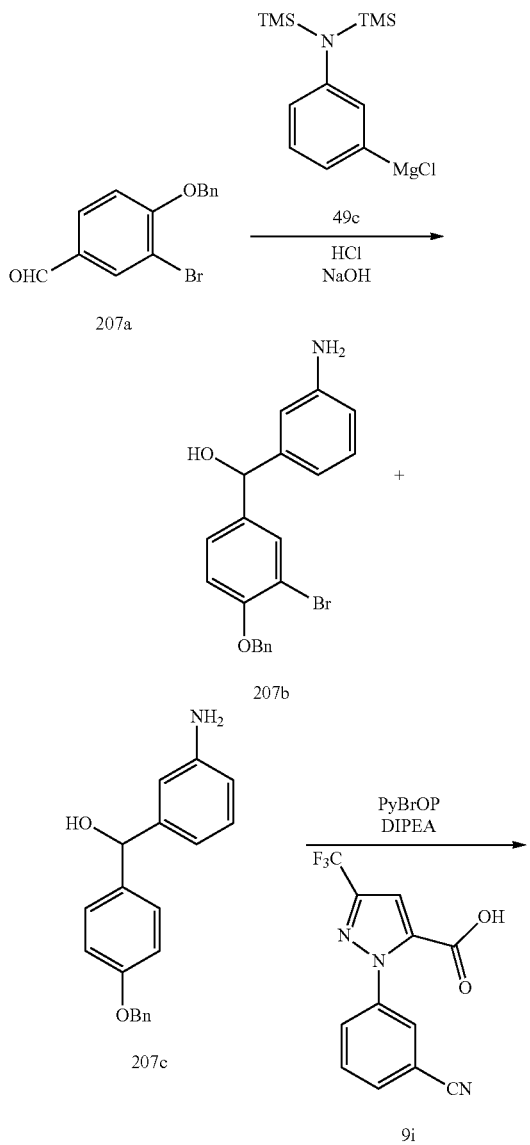

Scheme 207

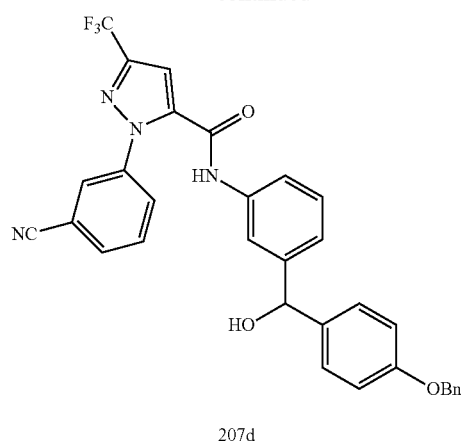
207d
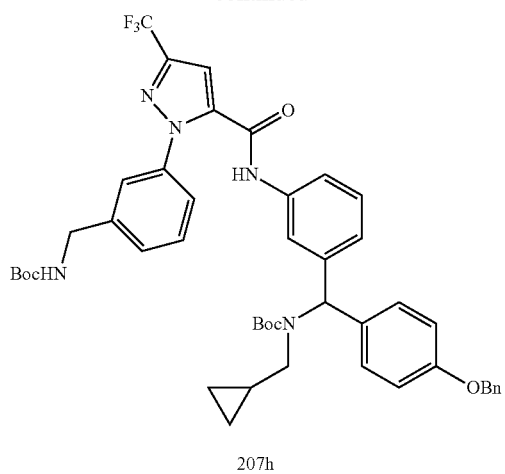
207h
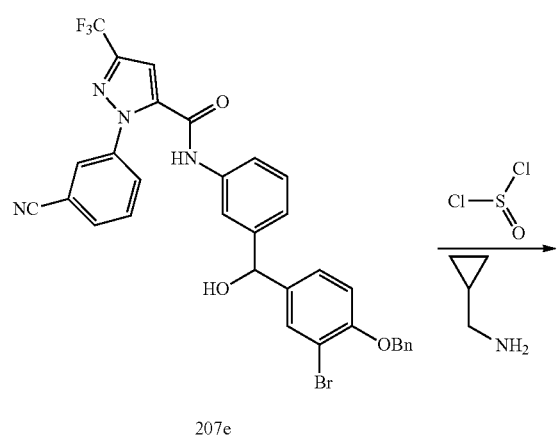
207e
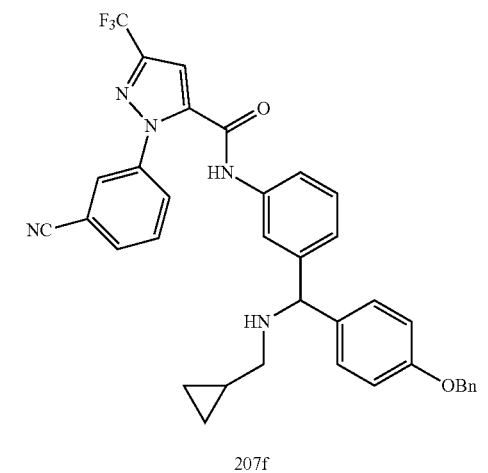
207f
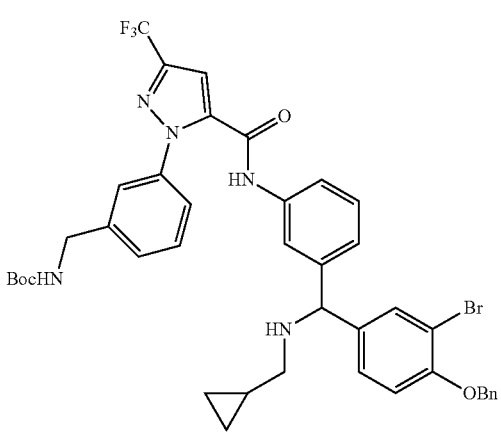
207i
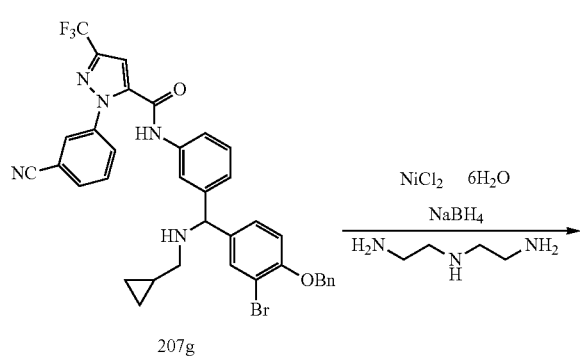
207g
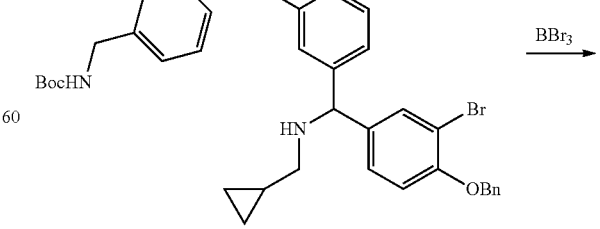
207i

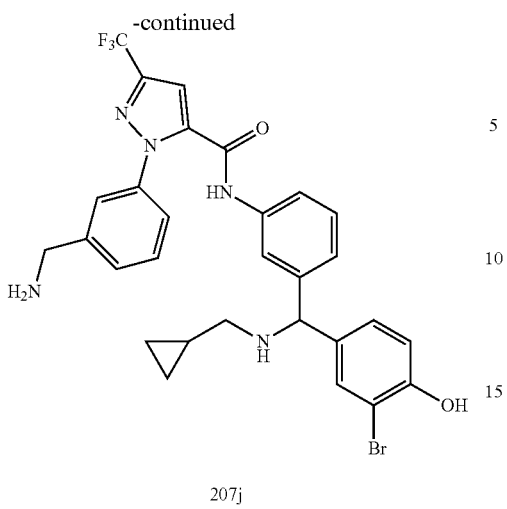

207j

Preparation of 1-(3-(Aminomethyl)phenyl)-N-(3-((3-bromo-4-hydroxyphenyl)(cyclopropylmethylamino)methyl)phenyl)-3-(trifluoromethyl)-1H-pyrazole-5-carboxamide (207j)

Step-1: (3-aminophenyl)(4-(benzyloxy)-3-bromophenyl)methanol (207b) and (3-aminophenyl)(4-(benzyloxy)phenyl)methanol (207c)

To a stirred solution of 4-(benzyloxy)-3-bromobenzaldehyde (207a) (3.2 g, 10 mmol) in THF (5 mL) was added (3-(bis(trimethylsilyl)amino)phenyl)magnesium chloride (49c) (12.00 mL, 12.00 mmol) at 0° C. The reaction was stirred for 14 h at room temperature, quenched by adding 2 N HCl (12.50 mL) and stirred for 6 h. The reaction mixture was treated with 2 N NaOH (15 mL) and extracted with ethyl acetate (2×50 mL). The organic layers were combined washed with saturated aqueous NH$_4$Cl (50 mL), dried over anhydrous MgSO$_4$, filtered, evaporated to dryness. The crude residue was purified by flash column chromatography (silica gel 40 g, eluting with 0-100% ethyl acetate in hexane) to furnish a mixture of (3-aminophenyl)(4-(benzyloxy)-3-bromophenyl)methanol (207b) and (3-aminophenyl)(4-(benzyloxy)phenyl)methanol (207c) (3.0 gm).

Step-2: Preparation of N-(3-((4-(benzyloxy)-3-bromophenyl)(hydroxy)methyl)phenyl)-1-(3-cyanophenyl)-3-(trifluoromethyl)-1H-pyrazole-5-carboxamide (207e) and N-(3-((4-(benzyloxy)phenyl)(hydroxy)methyl)phenyl)-1-(3-cyanophenyl)-3-(trifluoromethyl)-1H-pyrazole-5-carboxamide (207d)

To a solution of 1-(3-cyanophenyl)-3-(trifluoromethyl)-1H-pyrazole-5-carboxylic acid (9i) (1.1 mmol) in DMF (10 mL) was added a mixture of (3-aminophenyl)(4-(benzyloxy)-3-bromophenyl)methanol (207e) and (3-aminophenyl)(4-(benzyloxy)phenyl)methanol (207d) (1 mmol), N-ethyl-N-isopropylpropan-2-amine (6 eq) and bromo-tris-pyrrolidino phosphoniumhexafluorophosphate (PyBrOP, 1.1 eq) at room temperature. The reaction mixture was stirred at room temperature for 24 h under nitrogen atmosphere. The reaction was diluted with ethyl acetate washed with water, brine, dried, filtered, and evaporated to dryness. The residue obtained was purified by flash column chromatography [silica gel, eluting with ethyl acetate in hexanes] to furnish a mixture of N-(3-((4-(benzyloxy)-3-bromophenyl)(hydroxy)methyl)phenyl)-1-(3-cyanophenyl)-3-(trifluoromethyl)-1H-pyrazole-5-carboxamide (207e) and N-(3-((4-(benzyloxy)phenyl)(hydroxy)methyl)phenyl)-1-(3-cyanophenyl)-3-(trifluoromethyl)-1H-pyrazole-5-carboxamide (207d).

Step-3: Preparation of N-(3-((3-(benzyloxy)-4-methoxyphenyl)((cyclopropylmethyl)amino)methyl)phenyl)-1-(3-cyanophenyl)-3-(trifluoromethyl)-1H-pyrazole-5-carboxamide (207f) and N-(3-((4-(benzyloxy)phenyl)((cyclopropylmethyl)amino)methyl)phenyl)-1-(3-cyanophenyl)-3-(trifluoromethyl)-1H-pyrazole-5-carboxamide (207g)

To a solution of mixture of N-(3-((4-(benzyloxy)-3-bromophenyl)(hydroxy)methyl)phenyl)-1-(3-cyanophenyl)-3-(trifluoromethyl)-1H-pyrazole-5-carboxamide (207e) and N-(3-((4-(benzyloxy)phenyl)(hydroxy)methyl)phenyl)-1-(3-cyanophenyl)-3-(trifluoromethyl)-1H-pyrazole-5-carboxamide (207d) (1.0 mmol) in dichloromethane (10 mL) at 0° C. was added thionyl chloride (3 mmol) and stirred at room temperature for 4 h. The reaction mixture was concentrated in vacuum to dryness. The residue obtained was dissolved in acetonitrile (10 mL) and added cyclopropylmethanamine (10 mmol). The reaction mixture was heated at reflux overnight, cooled to room temperature and concentrated in vacuum to dryness. The residue was dissolved in dichloromethane, washed with water, dried, filtered and concentrated in vacuum. The residue obtained was purified by flash column chromatography (silica gel, eluting with ethyl acetate in hexane) to afford mixture (0.77 g) of N-(3-((3-(benzyloxy)-4-methoxyphenyl)((cyclopropylmethyl)amino)methyl)phenyl)-1-(3-cyanophenyl)-3-(trifluoromethyl)-1H-pyrazole-5-carboxamide (207f) and N-(3-((4-(benzyloxy)phenyl)((cyclopropylmethyl)amino)methyl)phenyl)-1-(3-cyanophenyl)-3-(trifluoromethyl)-1H-pyrazole-5-carboxamide (207g).

Step-4: Preparation of tert-butyl ((4-(benzyloxy)phenyl)(3-(1-(3-(((tert-butoxycarbonyl)amino)methyl)phenyl)-3-(trifluoromethyl)-1H-pyrazole-5-carboxamido)phenyl)methyl)(cyclopropylmethyl)carbamate (207h) and tert-butyl 3-(5-((3-((4-(benzyloxy)-3-bromophenyl)((cyclopropylmethyl)amino)methyl)phenyl)carbamoyl)-3-(trifluoromethyl)-1H-pyrazol-1-yl)benzylcarbamate (207i)

To a solution of mixture of N-(3-((3-(benzyloxy)-4-methoxyphenyl)((cyclopropylmethyl)amino)methyl)phenyl)-1-(3-cyanophenyl)-3-(trifluoromethyl)-1H-pyrazole-5-carboxamide (207f) and N-(3-((4-(benzyloxy)phenyl)((cyclopropylmethyl)amino)methyl)phenyl)-1-(3-cyanophenyl)-3-(trifluoromethyl)-1H-pyrazole-5-carboxamide (207g) (0.77 g) in MeOH (10 mL) cooled with ice/water was added nickel(II) chloride hexahydrate (0.25 eq) and Boc anhydride (4 eq) followed by portionwise addition of sodium borohydride (6 eq) over a period of 15 min. The reaction mixture was stirred at room temperature for 2 hrs and quenched with N1-(2-aminoethyl)ethane-1,2-diamine (2 eq) followed by stirring for additional 0.5 h. The reaction mixture was concentrated in vacuum to dryness and the residue obtained was dissolved in chloroform and water. The aqueous layer was separated extracted again with chloroform. The combined extracts were washed with brine, dried over MgSO₄ filtered and concentrated in vacuum. The residue obtained was purified by flash column chromatography (silica gel, eluting with Ethyl acetate/hexane) to furnish:

1. tert-butyl ((4-(benzyloxy)phenyl)(3-(1-(3-(((tert-butoxycarbonyl)amino)methyl)phenyl)-3-(trifluoromethyl)-1H-pyrazole-5-carboxamido)phenyl)methyl)(cyclopropylmethyl)carbamate (207h) (0.24 g, 22%) as an off-white solid; $^1$H NMR (300 MHz, DMSO-d₆) δ 10.72 (s, 1H), 7.64 (d, J=8.5 Hz, 1H), 7.56 (s, 1H), 7.49-7.38 (m, 9H), 7.34 (d, J=7.2 Hz, 4H), 7.17 (q, J=8.6 Hz, 2H), 6.93 (d, J=7.9 Hz, 1H), 6.16 (s, 1H), 5.21 (s, 2H), 4.18 (d, J=6.2 Hz, 2H), 3.22-2.91 (m, 2H), 1.37 (s, 9H), 1.30-1.23 (m, 9H), 0.75-0.56 (m, 1H), 0.23 (d, J=8.2 Hz, 2H), −0.04-−0.14 (m, 2H); $^{19}$F NMR (282 MHz, DMSO) δ −60.71; MS (ES+) 848.8.5 (M+Na); (ES−) 824.5 (M−1).

2. tert-butyl 3-(5-((3-((4-(benzyloxy)-3-bromophenyl)((cyclopropylmethyl)amino)methyl)phenyl)carbamoyl)-3-(trifluoromethyl)-1H-pyrazol-1-yl)benzylcarbamate (207i) (0.35 g, 39.6%) as a white solid; $^1$H NMR (300 MHz, DMSO-d₆) δ 10.69 (s, 1H), 7.61 (d, J=2.0 Hz, 2H), 7.57 (s, 1H), 7.53 (s, 1H), 7.45-7.39 (m, 6H), 7.37-7.32 (m, 4H), 7.25 (t, J=7.8 Hz, 1H), 7.18 (d, J=7.7 Hz, 1H), 7.11 (d, J=8.5 Hz, 1H), 5.15 (s, 2H), 4.77 (s, 1H), 4.19 (d, J=6.3 Hz, 2H), 2.26 (d, J=6.4 Hz, 2H), 1.35 (s, 9H), 0.94-0.84 (m, 1H), 0.46-0.28 (m, 2H), 0.05 (t, J=4.7 Hz, 2H); $^{19}$F NMR (282 MHz, DMSO) δ −60.79; MS (ES+) 804.4, 806.3 (M+1).

Step-5: Preparation of 1-(3-(Aminomethyl)phenyl)-N-(3-((3-bromo-4-hydroxyphenyl)(cyclopropylmethylamino)methyl)phenyl)-3-(trifluoromethyl)-1H-pyrazole-5-carboxamide (207j)

To a solution of tert-butyl 3-(5-(3-((4-(benzyloxy)-3-bromophenyl)(cyclopropylmethylamino) methyl)phenylcarbamoyl)-3-(trifluoromethyl)-1H-pyrazol-1-yl)benzylcarbamate (207i) (0.120 g, 0.149 mmol) in dichloromethane (10 mL) cooled to 0° C. was added dropwise under a nitrogen atmosphere tribromoborane (1 M solution in dichloromethane, 0.596 mL, 0.596 mmol). The reaction mixture was allowed to warm to room temperature and stirred at room temperature 2 h. The reaction mixture was quenched with methanol (5 mL) and concentrated in vacuum to dryness. The residue obtained was triturated with methanol and dried under vacuum, this step was repeated four times to furnish crude product. The residue obtained was purified twice by flash column chromatography [silica gel 12 g and 4 g, eluting with CMA-80 in chloroform from 0-100%] to furnish 1-(3-(aminomethyl)phenyl)-N-(3-((3-bromo-4-hydroxyphenyl) (cyclopropylmethylamino) methyl)phenyl)-3-(trifluoromethyl)-1H-pyrazole-5-carboxamide (207j) (0.045 g, 0.073 mmol, 49.1% yield) as a brownish orange solid; $^1$H NMR (300 MHz, DMSO-d₆) δ 10.89 (s, 1H), 10.62 (s, 1H), 9.58 (s, 2H), 8.26 (s, 3H), 7.81 (s, 1H), 7.76-7.71 (m, 2H), 7.67 (s, 1H), 7.62-7.46 (m, 6H), 7.38 (dd, J=8.5, 2.2 Hz, 1H), 6.98 (d, J=8.4 Hz, 1H), 5.56 (d, J=6.4 Hz, 1H), 4.24-4.06 (m, 2H), 2.72 (d, J=6.3 Hz, 2H), 1.08 (ddt, J=12.7, 8.3, 4.1 Hz, 1H), 0.56 (dt, J=9.4, 3.0 Hz, 2H), 0.30 (t, J=4.9 Hz, 2H); $^{19}$F NMR (282 MHz, DMSO) δ −60.80; MS (ES+) 616.3 (M+2); (ES−) 612.4 (M−2); HPLC purity (95.8256%); Analysis calculated for $C_{29}H_{27}BrF_3N_5O_2 \cdot 2.1HBr \cdot 2H_2O$: C, 42.46; H, 4.07; Br, 30.19; N, 8.54; Found: C, 42.22; H, 3.99; Br, 30.56; N, 8.35.

Scheme 208

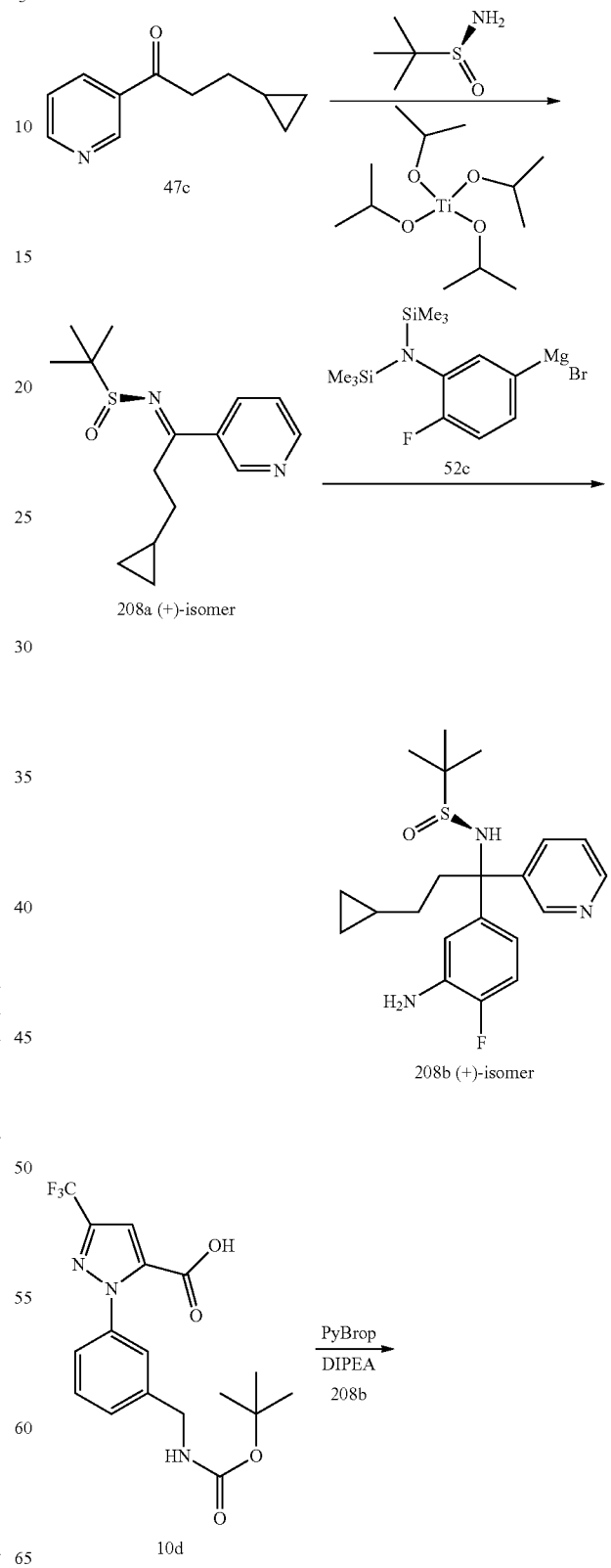

208a (+)-isomer 208b (+)-isomer

10d

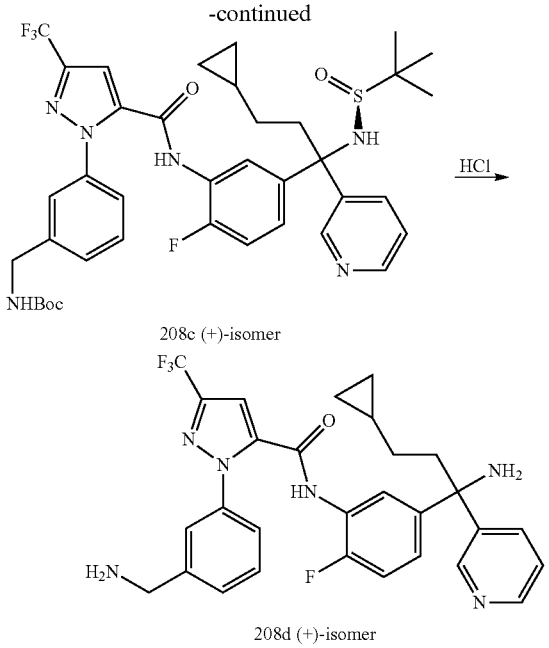

208c (+)-isomer 208d (+)-isomer

Preparation of (+)-N-(5-(1-amino-3-cyclopropyl-1-(pyridin-3-yl)propyl)-2-fluorophenyl)-1-(3-(aminomethyl)phenyl)-3-(trifluoromethyl)-1H-pyrazole-5-carboxamide (208d)

Step-1: Preparation of (+)-N-(3-cyclopropyl-1-(pyridin-3-yl)propylidene)-2-methylpropane-2-sulfinamide (208a)

To a stirred solution of 3-cyclopropyl-1-(pyridin-3-yl)propan-1-one (47c) (3.98 g, 22.69 mmol) in tetrahydrofuran (30 mL) was added (S)-2-methylpropane-2-sulfinamide (2.5 g, 20.63 mmol), tetraisopropoxytitanium (12.34 mL, 41.3 mmol) and heated at reflux for 16 h. The reaction mixture was allowed to cool to room temperature, diluted with brine (20 mL) and tetrahydrofuran (100 mL). The solid separated was removed by filtration and filtrate was concentrated in vacuum. The residue was suspended in dichloromethane (300 mL), washed with brine (50 mL) dried, filtered and concentrated in vacuum. The crude residue was purified by flash column chromatography (silica gel 40 g, eluting with ethyl acetate in hexanes) to afford (+)-N-(3-cyclopropyl-1-(pyridin-3-yl)propylidene)-2-methylpropane-2-sulfinamide (208a) (1.32 g, 4.74 mmol, 22.99% yield) as a yellow syrup; $^1$H NMR (300 MHz, DMSO-$d_6$) δ 9.25 (d, J=2.3 Hz, 1H), 8.93 (dd, J=4.8, 1.7 Hz, 1H), 8.46 (d, J=8.1 Hz, 1H), 7.75 (dd, J=8.0, 4.8 Hz, 1H), 3.69-3.41 (m, 2H), 1.68 (q, J=7.4 Hz, 2H), 1.45 (s, 9H), 0.96 (m, 1H), 0.67-0.48 (m, 2H), 0.30-0.22 (m, 2H); Optical Rotation $[α]_D$=(+) 25.77 [0.52, MeOH].

Step-2: Preparation of (S)—N-((+)-1-(3-amino-4-fluorophenyl)-3-cyclopropyl-1-(pyridin-3-yl)propyl)-2-methylpropane-2-sulfinamide (208b)

To a stirred solution of (+)-N-(3-cyclopropyl-1-(pyridin-3-yl)propylidene)-2-methylpropane-2-sulfinamide (208a) (4.12 g, 14.80 mmol) in toluene (30 mL) at −20° C. was added dropwise a freshly prepared solution of (3-(bis(trimethylsilyl)amino)-4-fluorophenyl)magnesium bromide (52c) (29.6 mL, 29.6 mmol) over a period of 10 mins. The reaction mixture was stirred at −20° C. for 1 h and quenched with 1N aqueous KHSO4 (25 mL). The reaction mixture was stirred for 1 h at room temperature and extracted with ethyl acetate (2×200 mL). The organic layers were combined washed with water (2×50 mL), brine (50 mL), dried and concentrated in vacuum to dryness. The crude residue was purified by flash column chromatography (silica gel, 50 g eluting with ethyl acetate in hexanes 0 to 100%) to afford (S)—N-((+)-1-(3-amino-4-fluorophenyl)-3-cyclopropyl-1-(pyridin-3-yl)propyl)-2-methylpropane-2-sulfinamide (208b) (1.15 g, 2.95 mmol, 19.95% yield) as a white solid; $^1$H NMR (300 MHz, DMSO-$d_6$) δ 8.51 (dd, J=2.5, 0.8 Hz, 1H), 8.40 (dd, J=4.7, 1.5 Hz, 1H), 7.70 (dt, J=8.1, 2.0 Hz, 1H), 7.32 (ddd, J=8.1, 4.7, 0.8 Hz, 1H), 6.90 (dd, J=11.3, 8.5 Hz, 1H), 6.73 (dd, J=8.8, 2.4 Hz, 1H), 6.50 (ddd, J=8.5, 4.3, 2.4 Hz, 1H), 5.27 (s, 1H), 5.11 (s, 2H), 2.67-2.54 (m, 2H), 1.12 (s, 10H), 0.90 (m, 1H), 0.65 (m, 1H), 0.41-0.29 (m, 2H), −0.01--0.17 (m, 2H); $^{19}$F NMR (282 MHz, DMSO-$d_6$) δ −137.66; MS (ES+) 390.4 (M+1), 412.4 (M+Na), 779.6 (2M+1), 801.6 (2M+Na), (ES−) 388.3 (M−1); Optical Rotation $[α]_D$=(+) 110.34 [0.145, MeOH].

Step-3: Preparation of tert-butyl 3-(5-(5-((+)-3-cyclopropyl-1-((S)-1,1-dimethylethylsulfinamido)-1-(pyridin-3-yl)propyl)-2-fluorophenylcarbamoyl)-3-(trifluoromethyl)-1H-pyrazol-1-yl)benzylcarbamate (208c)

To a solution of 1-(3-((tert-butoxycarbonylamino)methyl)phenyl)-3-(trifluoromethyl)-1H-pyrazole-5-carboxylic acid (10d) (1.251 g, 3.25 mmol) in DMF (17 mL) was added (S)—N-((+)-1-(3-amino-4-fluorophenyl)-3-cyclopropyl-1-(pyridin-3-yl)propyl)-2-methylpropane-2-sulfinamide (208b) (1.15 g, 2.95 mmol), N-ethyl-N-isopropylpropan-2-amine (2.57 mL, 14.76 mmol) and bromo-tris-pyrrolidino phosphoniumhexafluorophosphate(PyBrop, 1.514 g, 3.25 mmol) at room temperature. The reaction mixture was stirred at room temperature for 6 h, diluted with water (40 mL) and extracted with ethyl acetate (2×100 mL). The organic layers were combined, washed with brine (50 mL), dried, filtered, and concentrated in vacuum to dryness. The residue obtained was purified by flash column chromatography (silica gel 40 g, eluting with 0-100% ethyl acetate in hexanes) to furnish tert-butyl 3-(5-(5-((+)-3-cyclopropyl-1-((S)-1,1-dimethylethylsulfinamido)-1-(pyridin-3-yl)propyl)-2-fluorophenylcarbamoyl)-3-(trifluoromethyl)-1H-pyrazol-1-yl)benzylcarbamate (208c) (1.2 g, 0.696 mmol, 53% yield) as a white solid; $^1$H NMR (300 MHz, DMSO-$d_6$) δ 10.61 (s, 1H), 8.55-8.45 (m, 1H), 8.41 (dd, J=4.7, 1.5 Hz, 1H), 7.69 (d, J=8.2 Hz, 1H), 7.59 (d, J=8.4 Hz, 2H), 7.51 (t, J=6.3 Hz, 1H), 7.42 (d, J=4.9 Hz, 2H), 7.38-7.30 (m, 3H), 7.25 (d, J=10.0 Hz, 2H), 5.58 (s, 1H), 4.19 (d, J=6.2 Hz, 2H), 2.73-2.54 (m, 2H), 1.38 (s, 9H), 1.12 (s, 10H), 0.92 (m, 1H), 0.64 (m, 1H), 0.41-0.24 (m, 2H), −0.02--0.19 (m, 2H); $^{19}$F NMR (282 MHz, DMSO-$d_6$) δ −60.81, −123.10; MS (ES+) 757.4 (M+1), 779.4 (M+Na), (ES−) 755.4 (M−1) (+) 67.17 (0.265, methanol). Optical Rotation $[α]_D$=(+) 67.17 (0.265, methanol).

Step-4: Preparation of (+)-N-(5-(1-amino-3-cyclopropyl-1-(pyridin-3-yl)propyl)-2-fluorophenyl)-1-(3-(aminomethyl)phenyl)-3-(trifluoromethyl)-1H-pyrazole-5-carboxamide (208d)

To a stirred solution of furnish tert-butyl 3-(5-(5-((+)-3-cyclopropyl-1-((S)-1,1-dimethylethylsulfinamido)-1-(pyridin-3-yl)propyl)-2-fluorophenylcarbamoyl)-3-(trifluoromethyl)-1H-pyrazol-1-yl)benzylcarbamate (208c) (1 g, 1.321 mmol) in ethanol (20 mL) was added conc. HCl (1.101 mL, 13.21 mmol) and heated at reflux for 1 h. The reaction mixture was concentrated in vacuum to dryness and the residue obtained was purified by flash column chromatography (silica gel, 24 g eluting with CMA 80 in chloroform 0 to 100%) to afford product which was repurified by flash column chromatography (silica gel, 24 g eluting with methanol in chloroform 0 to 50%) to afford (+)-N-(5-(1-amino-3-cyclopropyl-1-(pyridin-3-yl)propyl)-2-fluorophenyl)-1-(3-(aminomethyl)phenyl)-3-(trifluoromethyl)-1H-pyrazole-5-carboxamide (208d) (560 mg, 1.013 mmol, 77% yield) free base as a white solid; $^1$H NMR (300 MHz, DMSO-$d_6$) δ 8.58 (d, J=2.4 Hz, 1H), 8.36 (dd, J=4.7, 1.6 Hz, 1H), 7.75 (dt, J=8.1, 2.0 Hz, 1H), 7.63-7.54 (m, 2H), 7.50 (s, 1H), 7.47-7.36 (m, 2H), 7.30 (td, J=8.0, 7.4, 3.6 Hz, 3H), 7.18 (t, J=9.4 Hz, 1H), 3.77 (s, 2H), 2.37-2.03 (m, 2H), 1.03 (t, J=6.4 Hz, 2H), 0.63 (td, J=9.0, 8.0, 4.3 Hz, 1H), 0.41-0.24 (m, 2H), −0.08 (td, J=5.3, 3.7 Hz, 2H); 19F NMR (282 MHz, DMSO-$d_6$) δ −60.73, −124.20; MS (ES+) 553.4 (M+1), (ES−) 551.4 (M−1).

To a stirred solution of (+)-N-(5-(1-amino-3-cyclopropyl-1-(pyridin-3-yl)propyl)-2-fluorophenyl)-1-(3-(aminomethyl)phenyl)-3-(trifluoromethyl)-1H-pyrazole-5-carboxamide (208d) (495 mg, 0.896 mmol) free base in ethanol (5 mL) was added conc. HCl (0.373 mL, 4.48 mmol), water (3 mL) stirred for 10 mins and concentrated to dryness to afford (+)-N-(5-(1-amino-3-cyclopropyl-1-(pyridin-3-yl)propyl)-2-fluorophenyl)-1-(3-(aminomethyl)phenyl)-3-(trifluoromethyl)-1H-pyrazole-5-carboxamide (208d) (0.491 g, 0.785 mmol, 88% yield, >99.99 ee) hydrochloride salt as a white solid; $^1$H NMR (300 MHz, DMSO-$d_6$) δ 10.84 (s, 1H), 9.60 (s, 3H), 8.72-8.63 (m, 2H), 8.45 (s, 3H), 8.02 (d, J=8.4 Hz, 1H), 7.75-7.32 (m, 9H), 4.11 (q, J=5.8 Hz, 2H), 2.64-2.54 (m, 2H), 1.10 (dd, J=17.8, 7.7 Hz, 2H), 0.68 (d, J=8.0 Hz, 1H), 0.43-0.33 (m, 2H), 0.07-0.01 (m, 2H); $^{19}$F NMR (282 MHz, DMSO-$d_6$) δ −60.80, −120.42 (d, J=10.5 Hz); MS (ES+) 553.5 (M+1), (ES−) 551.5 (M−1); Optical Rotation [α]$_D$=(+) 2.55 [1.02, MeOH]; Chiral purity checked by performing chiral HPLC using chiral AD-H column, 1 mL/min, Solvent: 85% Hexane, 20% EtOH, 0.1% TEA, UV=260 nM, 20° C. (>99.99 ee).

Scheme 209

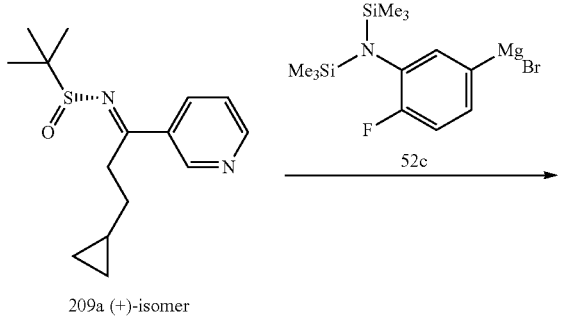

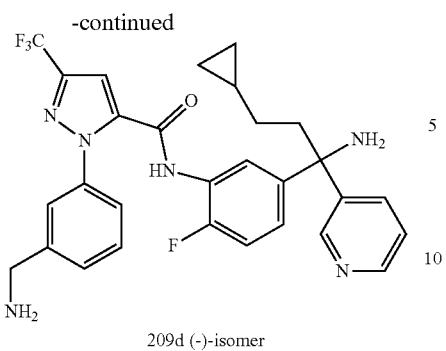

209d (-)-isomer

Preparation of (-)-N-(5-(1-amino-3-cyclopropyl-1-(pyridin-3-yl)propyl)-2-fluorophenyl)-1-(3-(aminomethyl)phenyl)-3-(trifluoromethyl)-1H-pyrazole-5-carboxamide (209d)

Step-1: Preparation of (-)-N-(3-cyclopropyl-1-(pyridin-3-yl)propylidene)-2-methylpropane-2-sulfinamide (209a)

Compound (209a) was prepared from 3-cyclopropyl-1-(pyridin-3-yl)propan-1-one (47c) (3.98 g, 22.69 mmol) and (R)-2-methylpropane-2-sulfinamide (2.5 g, 20.63 mmol) according to the procedure described in step-1 of scheme 208 for preparation of compound 208a to afford (-)-N-(5-(1-amino-3-cyclopropyl-1-(pyridin-3-yl)propyl)-2-fluorophenyl)-1-(3-(aminomethyl)phenyl)-3-(trifluoromethyl)-1H-pyrazole-5-carboxamide (209a) (2.5 g, 8.98 mmol, 43.5% yield) as a yellow syrup; $^{1}$H NMR (300 MHz, DMSO-$d_6$) δ 9.04 (s, 1H), 8.72 (dd, J=4.8, 1.6 Hz, 1H), 8.24 (d, J=8.1 Hz, 1H), 7.53 (dd, J=8.1, 4.8 Hz, 1H), 3.40 (m, 1H), 3.30 (m, 1H), 1.47 (q, J=7.4 Hz, 2H), 1.24 (s, 9H), 0.82-0.66 (m, 1H), 0.44-0.29 (m, 2H), 0.12-0.01 (m, 2H); Optical Rotation $[α]_D$=(-) 17.29 [0.59, MeOH].

Step-2: Preparation of (R)—N-((-)-1-(3-amino-4-fluorophenyl)-3-cyclopropyl-1-(pyridin-3-yl)propyl)-2-methylpropane-2-sulfinamide (209b)

To a stirred solution of (-)-N-(5-(1-amino-3-cyclopropyl-1-(pyridin-3-yl)propyl)-2-fluorophenyl)-1-(3-(aminomethyl)phenyl)-3-(trifluoromethyl)-1H-pyrazole-5-carboxamide (209a) (82 g, 295 mmol) in Toluene (1700 mL) at -20° C. was added dropwise a freshly prepared solution of (3-(bis(trimethylsilyl)amino)-4-fluorophenyl)magnesium bromide (920 mL, 736 mmol) over a period of 120 mins. The reaction mixture was stirred at -20° C. for 1 h and quenched with 1N aqueous KHSO$_4$ (1600 mL). The reaction mixture was stirred for 1 h at room temperature, basified with 2 N NaOH to pH~8 and extracted with ethyl acetate (1500, 700 mL). The organic layers were combined washed with water (2×700 mL), brine (700 mL), dried and concentrated in vacuum. The crude residue was purified by flash column chromatography (silica gel, eluting with (9:1) ethyl acetate/methanol in hexanes 0 to 50%) to afford (R)—N-((-)-1-(3-amino-4-fluorophenyl)-3-cyclopropyl-1-(pyridin-3-yl)propyl)-2-methylpropane-2-sulfinamide (209b) (54.155 g, 139 mmol, 47.2% yield) as a white solid; $^{1}$H NMR (300 MHz, DMSO-$d_6$) δ 8.53-8.48 (m, 1H), 8.39 (dd, J=4.7, 1.5 Hz, 1H), 7.70 (dt, J=8.1, 2.0 Hz, 1H), 7.32 (dd, J=8.0, 4.7 Hz, 1H), 6.90 (dd, J=11.2, 8.5 Hz, 1H), 6.73 (dd, J=8.8, 2.4 Hz, 1H), 6.56-6.45 (m, 1H), 5.26 (s, 1H), 5.10 (s, 2H), 2.67-2.54 (m, 2H), 1.28-1.11 (m, 1H), 1.12 (s, 9H), 0.91 (m, 1H), 0.64 (m, 1H), 0.40-0.30 (m, 2H), -0.02--0.14 (m, 2H); 19F NMR (282 MHz, DMSO d6) 6-137.67; MS (ES+) 390.4 (M+1); (ES-) 388.4 (M-1); Optical Rotation $[α]_D$=(-) 105.71 [0.28, MeOH].

Step-3: Preparation of tert-butyl 3-(5-(5-((-)-3-cyclopropyl-1-((R)-1,1-dimethylethylsulfinamido)-1-(pyridin-3-yl)propyl)-2-fluorophenylcarbamoyl)-3-(trifluoromethyl)-1H-pyrazol-1-yl)benzylcarbamate (209c)

Compound (209c) was prepared using 1-(3-((tert-butoxycarbonylamino)methyl)phenyl)-3-(trifluoromethyl)-1H-pyrazole-5-carboxylic acid (10d) (21.76 g, 56.5 mmol) and (R)—N-((-)-1-(3-amino-4-fluorophenyl)-3-cyclopropyl-1-(pyridin-3-yl)propyl)-2-methylpropane-2-sulfinamide (209b) (20 g, 51.3 mmol) using procedure as reported in step-3 of scheme 208 for preparation of compound 208c to afford tert-butyl 3-(5-(5-((-)-3-cyclopropyl-1-((R)-1,1-dimethylethylsulfinamido)-1-(pyridin-3-yl)propyl)-2-fluorophenylcarbamoyl)-3-(trifluoromethyl)-1H-pyrazol-1-yl)benzylcarbamate (209c) (16 g, 21.4 mmol, 41.2% yield) as a white solid; $^{1}$H NMR (300 MHz, DMSO-$d_6$) δ 10.61 (s, 1H), 8.49 (d, J=2.3 Hz, 1H), 8.41 (dd, J=4.7, 1.5 Hz, 1H), 7.69 (d, J=8.2 Hz, 1H), 7.63-7.15 (m, 10H), 5.57 (s, 1H), 4.18 (d, J=6.3 Hz, 2H), 2.75-2.40 (m, 2H), 1.38 (s, 9H), 1.22-1.01 (m, 1H), 1.12 (s, 9H), 1.00-0.80 (m, 1H), 0.72-0.54 (m, 1H), 0.40-0.28 (m, 2H), -0.02--0.16 (m, 2H); 19F NMR (282 MHz, DMSO-$d_6$) δ -60.61, -122.92; MS (ES+) 757.6 (M+1); (ES-) 755.6 (M-1); Optical Rotation $[α]_D$ (-) 66.4 [0.25, MeOH].

Step-4: Preparation of (-)-N-(5-(1-amino-3-cyclopropyl-1-(pyridin-3-yl)propyl)-2-fluorophenyl)-1-(3-(aminomethyl)phenyl)-3-(trifluoromethyl)-1H-pyrazole-5-carboxamide (209d)

To a stirred solution of tert-butyl 3-(5-(5-((-)-3-cyclopropyl-1-((R)-1,1-dimethylethylsulfinamido)-1-(pyridin-3-yl)propyl)-2-fluorophenylcarbamoyl)-3-(trifluoromethyl)-1H-pyrazol-1-yl)benzylcarbamate (209c) (15.76 g, 20.82 mmol) in ethanol (720 mL) was added conc. hydrochloric acid (17.40 mL, 209 mmol) and heated at reflux for 1 h. The reaction mixture was concentrated in vacuum to dryness and the residue obtained was dissolved in ethanol (50 mL), triturated with t-butyl methyl ether (300 mL, 200 mL), and decanted. The solid was dried under vacuum, dissolved in water (100 mL) and concentrated in vacuum. The off-white solid was again dissolved in water (30 mL) and concentrated under vacuum to dryness to afford (-)-N-(5-(1-amino-3-cyclopropyl-1-(pyridin-3-yl)propyl)-2-fluorophenyl)-1-(3-(aminomethyl)phenyl)-3-(trifluoromethyl)-1H-pyrazole-5-carboxamide (209d) (11.966 g) HCl salt as an of white solid; $^{1}$H NMR (300 MHz, DMSO-$d_6$) δ 10.87 (s, 1H), 9.73 (s, 3H), 8.80-8.73 (m, 2H), 8.63-8.38 (m, 3H), 8.21 (dt, J=8.5, 1.7 Hz, 1H), 7.81 (dd, J=8.2, 5.2 Hz, 1H), 7.75-7.32 (m, 8H), 4.09 (q, J=5.8 Hz, 2H), 2.71-2.37 (m, 2H), 1.22-1.04 (m, 2H), 0.74-0.58 (m, 1H), 0.48-0.25 (m, 2H), 0.08--0.15 (m, 2H); 19F NMR (282 MHz, DMSO-$d_6$) δ -60.63, -120.00; MS (ES+): 553.5 (M+1); Optical Rotation $[α]_D$=(-) 2.82 [1.065, MeOH]; Chiral purity checked by performing chiral HPLC using chiral AD-H column, 1 mL/min, Solvent: 85% Hexane, 20% EtOH, 0.1% TEA, UV=260 nM, 20° C. (>99.99 ee).

Scheme 210

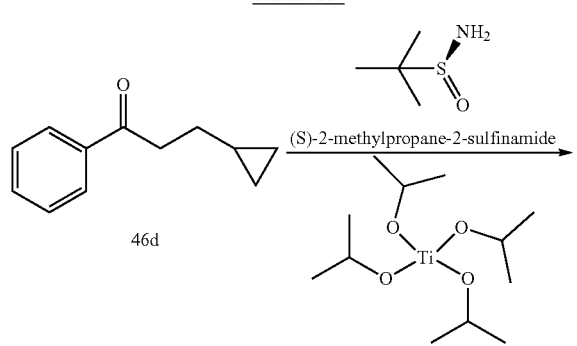

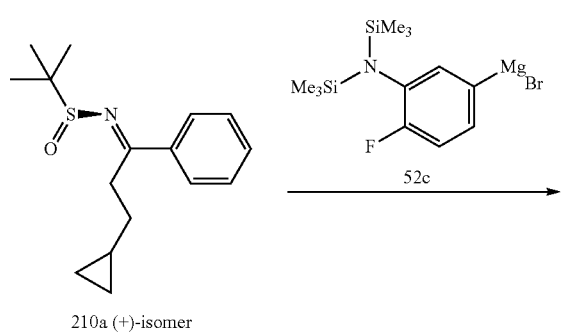

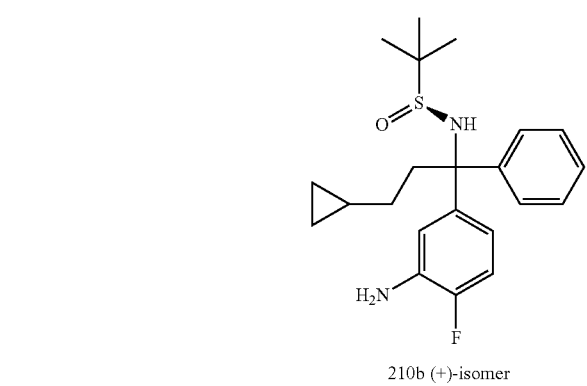

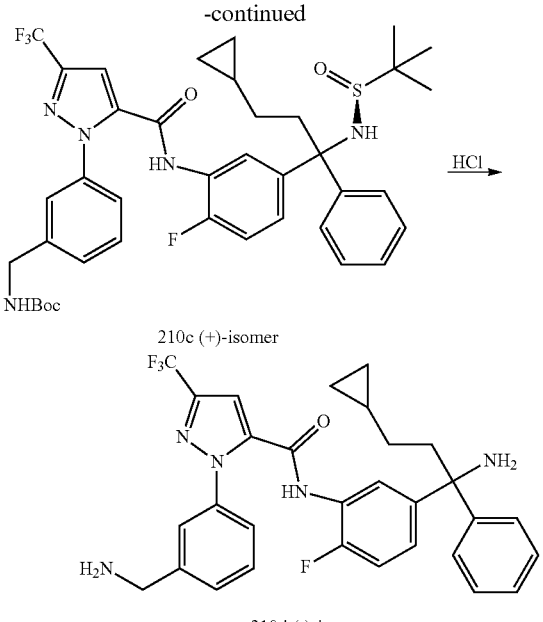

210c (+)-isomer 210d (-)-isomer

Preparation of (−)-N-(5-(1-amino-3-cyclopropyl-1-phenylpropyl)-2-fluorophenyl)-1-(3-(aminomethyl)phenyl)-3-(trifluoromethyl)-1H-pyrazole-5-carboxamide (210d)

Step-1: Preparation (+)-N-(3-cyclopropyl-1-phenylpropylidene)-2-methylpropane-2-sulfinamide (210a)

Compound (210a) was prepared from 3-cyclopropyl-1-phenylpropan-1-one (46d) (3.95 g, 22.69 mmol) using (S)-2-methylpropane-2-sulfinamide (2.5 g, 20.63 mmol), using procedure as reported in step-1 of scheme 208 to afford (+)-N-(3-cyclopropyl-1-phenylpropylidene)-2-methylpropane-2-sulfinamide (210a) (1.22 g, 4.40 mmol, 21.32% yield) as a light brownish yellow syrup; $^1$H NMR (300 MHz, DMSO-$d_6$) δ 7.89 (d, J=7.4 Hz, 2H), 7.61-7.42 (m, 3H), 3.36 (m, 1H), 3.31-3.13 (m, 1H), 1.46 (q, J=7.4 Hz, 2H), 1.23 (s, 9H), 0.76 (m, 1H), 0.38 (m, 2H), 0.05 (m, 2H); MS (ES+) 278.2 (M+1), 300.3 (M+Na), 555.4 (2M+1), 577.4 (2M+Na); Optical Rotation [α]$_D$=(+) 22.22 [0.27, MeOH].

Step-2: Preparation of (S)—N-((+)-1-(3-amino-4-fluorophenyl)-3-cyclopropyl-1-phenylpropyl)-2-methylpropane-2-sulfinamide (210b)

Compound (210b) was prepared from (+)-N-(3-cyclopropyl-1-phenylpropylidene)-2-methylpropane-2-sulfinamide (210a) (2 g, 7.21 mmol)), using procedure as reported in step-2 of scheme 208 to afford (S)—N-((+)-1-(3-amino-4-fluorophenyl)-3-cyclopropyl-1-phenylpropyl)-2-methylpropane-2-sulfinamide (210b) (2.16 g, 5.56 mmol, 77% yield) as light yellow syrup.

$^1$H NMR (300 MHz, DMSO-$d_6$) δ 7.36-7.24 (m, 4H), 7.23-7.15 (m, 1H), 6.87 (dd, J=11.3, 8.5 Hz, 1H), 6.71 (dd, J=8.9, 2.4 Hz, 1H), 6.48 (ddd, J=8.5, 4.3, 2.3 Hz, 1H), 5.06 (s, 2H), 4.94 (s, 1H), 2.57 (m, 2H), 1.06 (s, 10H), 1.05 (m, 1H), 0.87 (m, 1H), 0.45-0.24 (m, 2H), 0.04-−0.19 (m, 2H); $^{19}$F NMR (282 MHz, DMSO-$d_6$) δ −138.17; MS (ES+) 389.3 (M+1), 777.6 (2M+1), 799.6 (2M+23), (ES−) 387.3 (M−H); Optical Rotation [α]$_D$=(+) 112.56 [0.215, MeOH].

Step-3: Preparation of tert-butyl 3-(5-(5-((+)-3-cyclopropyl-1-((S)-1,1-dimethylethylsulfinamido)-1-phenylpropyl)-2-fluorophenylcarbamoyl)-3-(trifluoromethyl)-1H-pyrazol-1-yl)benzylcarbamate (210c)

Compound (210c) was prepared from 1-(3-((tert-butoxycarbonylamino)methyl)phenyl)-3-(trifluoromethyl)-1H-pyrazole-5-carboxylic acid (10d) (1.473 g, 3.82 mmol) and (S)—N-((+)-1-(3-amino-4-fluorophenyl)-3-cyclopropyl-1-phenylpropyl)-2-methylpropane-2-sulfinamide (210b) (1.35 g, 3.47 mmol) using the procedure as reported in step-3 of scheme 208 to afford tert-butyl 3-(5-(5-((+)-3-cyclopropyl-1-((S)-1,1-dimethylethylsulfinamido)-1-phenylpropyl)-2-fluorophenylcarbamoyl)-3-(trifluoromethyl)-1H-pyrazol-1-yl)benzylcarbamate (210c) (1.532 g, 2.027 mmol, 58.3% yield) as a white solid; $^1$H NMR (300 MHz, DMSO-$d_6$) δ 10.58 (s, 1H), 7.63-7.16 (m, 13H), 5.29 (s, 1H), 4.19 (d, J=6.2 Hz, 2H), 2.57 (m, 2H), 1.38 (s, 10H), 1.12 (s, 10H), 0.87 (m, 1H), 0.62 (m, 1H), 0.43-0.23 (m, 2H), −0.09 (m, 2H); $^{19}$F NMR (282 MHz, DMSO-$d_6$) δ −60.79, −123.61; MS (ES+) 756.6 (M+1), 778.6 (M+Na); Optical Rotation $[α]_D$=(+) 72.14 [0.28, MeOH].

Step-4: Preparation of (−)-N-(5-(1-amino-3-cyclopropyl-1-phenylpropyl)-2-fluorophenyl)-1-(3-(aminomethyl)phenyl)-3-(trifluoromethyl)-1H-pyrazole-5-carboxamide (210d)

Compound (210d) free base was prepared from tert-butyl 3-(5-(5-((+)-3-cyclopropyl-1-((S)-1,1-dimethylethylsulfinamido)-1-phenylpropyl)-2-fluorophenylcarbamoyl)-3-(trifluoromethyl)-1H-pyrazol-1-yl)benzylcarbamate (210c) (1.454 g, 1.924 mmol) as reported in step-4 of scheme 208 to afford (−)-N-(5-(1-amino-3-cyclopropyl-1-phenylpropyl)-2-fluorophenyl)-1-(3-(aminomethyl)phenyl)-3-(trifluoromethyl)-1H-pyrazole-5-carboxamide (210d) (0.830 g, 1.505 mmol, 78% yield) free base as a white solid; $^1$H NMR (300 MHz, DMSO-$d_6$) δ 10.53 (s, 1H), 7.55 (d, J=14.1 Hz, 3H), 7.49-7.31 (m, 5H), 7.30-7.21 (m, 3H), 7.21-7.09 (m, 2H), 3.81 (s, 2H), 3.34 (s, 2H), 2.73-2.55 (m, 2H), 2.31-2.10 (m, 2H), 1.03 (m, 2H), 0.61 (m, 1H), 0.43-0.23 (m, 2H), −0.09 (m, 2H); $^{19}$F NMR (282 MHz, DMSO-$d_6$) δ −60.66, −124.51; MS (ES−) 550.4 (M−1).

To a stirred solution of (−)-N-(5-(1-amino-3-cyclopropyl-1-phenylpropyl)-2-fluorophenyl)-1-(3-(aminomethyl)phenyl)-3-(trifluoromethyl)-1H-pyrazole-5-carboxamide (210d) (682 mg, 1.236 mmol) free base in ethanol (10 mL) was added conc. HCl (0.515 mL, 6.18 mmol), water (5 mL) stirred for 10 mins and concentrated in vacuum to dryness to afford (−)-N-(5-(1-amino-3-cyclopropyl-1-phenylpropyl)-2-fluorophenyl)-1-(3-(aminomethyl)phenyl)-3-(trifluoromethyl)-1H-pyrazole-5-carboxamide (210d) (666 mg, 1.066 mmol, 86% yield) hydrochloride salt as a white solid; $^1$H NMR (300 MHz, DMSO-$d_6$) δ 10.82 (s, 1H), 9.29 (s, 3H), 8.51 (s, 3H), 7.72 (dd, J=5.4, 3.6 Hz, 2H), 7.63 (dt, J=7.2, 1.7 Hz, 1H), 7.60-7.47 (m, 3H), 7.47-7.30 (m, 7H), 4.11 (s, 2H), 2.41-2.55 (m, 2H), 1.22-0.99 (m, 2H), 0.67 (m, 1H), 0.46-0.28 (m, 2H). 0.01-0.05 (m, 2H); 19F NMR (282 MHz, DMSO-$d_6$) δ −60.81, −120.90; MS (ES+) 550.4 (M−1), 586.4 (M+Cl); Optical Rotation $[α]_D$=(−) 3.51 [1.025, MeOH]; Analysis calculated for $C_{30}H_{29}F_4N_5O.2HCl.1.5H_2O$: C: 55.36, H: 5.27, N: 10.76, Cl: 11.68; Found: C: 55.35, H: 5.45, N: 10.63, Cl: 11.45.

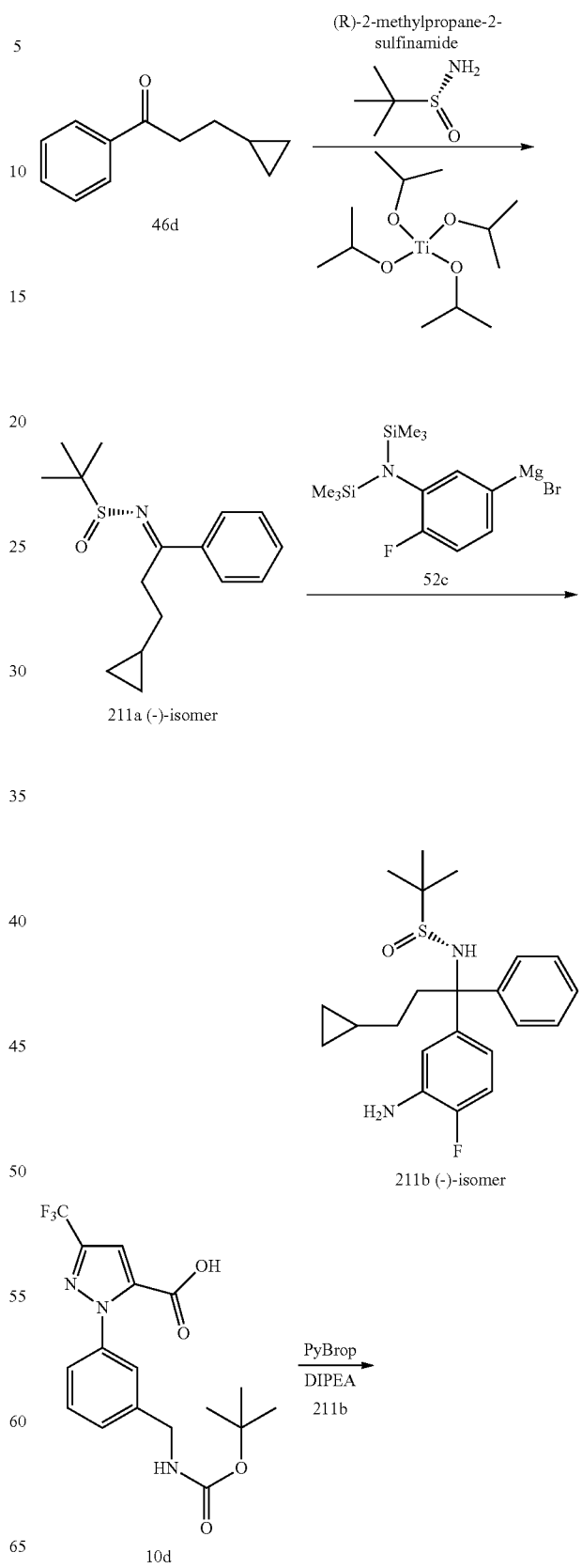

Scheme 211

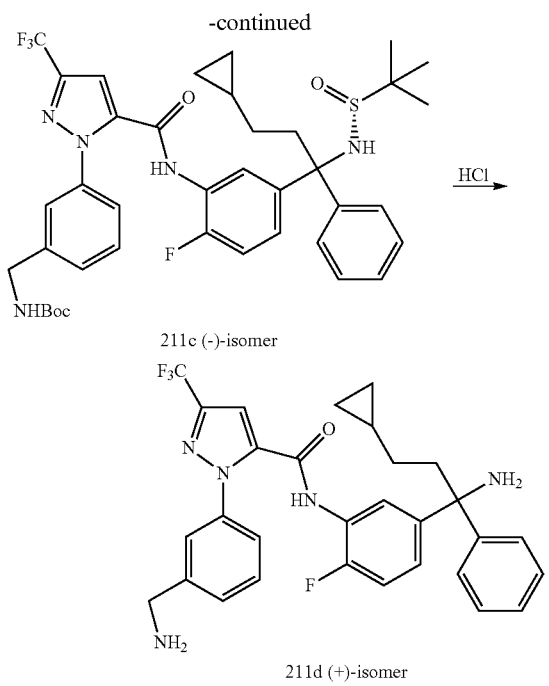

Preparation of (+)-N-(5-(1-amino-3-cyclopropyl-1-phenylpropyl)-2-fluorophenyl)-1-(3-(aminomethyl)phenyl)-3-(trifluoromethyl)-1H-pyrazole-5-carboxamide (211d)

Step-1: Preparation (−)-N-(3-cyclopropyl-1-phenylpropylidene)-2-methylpropane-2-sulfinamide (211a)

Compound (211a) was prepared from 3-cyclopropyl-1-phenylpropan-1-one (46d) (3.95 g, 22.69 mmol) and (R)-2-methylpropane-2-sulfinamide (2.5 g, 20.63 mmol), using procedure as reported in step-1 of scheme 208 to afford (−)-N-(3-cyclopropyl-1-phenylpropylidene)-2-methylpropane-2-sulfinamide (211a) (3.247 g, 11.70 mmol, 56.7% yield) as a light brownish yellow syrup; $^1$H NMR (300 MHz, DMSO-$d_6$) δ 7.89 (d, J=7.6 Hz, 2H), 7.51 (qd, J=8.7, 7.8, 3.6 Hz, 3H), 3.45-3.15 (m, 2H), 1.46 (m, 2H), 1.23 (s, 9H), 0.82-0.67 (m, 1H), 0.43-0.32 (m, 2H), 0.06 (m, 2H); MS (ES+) 278.3 (M+1), 300.3 (M+Na), 577.5 (2M+Na); Optical Rotation [α]$_D$=(−) 36.32 [0.76, CHCl$_3$].

Step-2: Preparation of (R)—N-((−)-1-(3-amino-4-fluorophenyl)-3-cyclopropyl-1-phenylpropyl)-2-methylpropane-2-sulfinamide (211b)

Compound (211b) was prepared from (−)-N-(3-cyclopropyl-1-phenylpropylidene)-2-methylpropane-2-sulfinamide (211a) (3.065 g, 11.05 mmol), using procedure as reported in step-2 of scheme 208 to afford (R)—N-((−)-1-(3-amino-4-fluorophenyl)-3-cyclopropyl-1-phenylpropyl)-2-methylpropane-2-sulfinamide (211b) (2.62 g, 6.74 mmol, 61.0% yield) as a light brown oil; $^1$H NMR (300 MHz, DMSO-$d_6$) δ 7.35-7.25 (m, 4H), 7.22-7.15 (m, 1H), 6.87 (dd, J=11.3, 8.5 Hz, 1H), 6.71 (dd, J=8.8, 2.4 Hz, 1H), 6.49 (m, 1H), 5.06 (s, 2H), 4.94 (s, 1H), 2.61-2.52 (m, 2H), 1.14 (m, 10H), 0.97-0.80 (m, 1H), 0.75-0.52 (m, 1H), 0.36 (m, 2H), −0.01-−0.16 (m, 2H); $^{19}$F NMR (282 MHz, DMSO-$d_6$) δ −138.17; MS (ES+) 389.4 (M+1), 777.6 (2M+1), 799.6 (2M+Na); Optical Rotation [α]$_D$=(−) 100.41 [0.245, MeOH].

Step-3: Preparation of tert-butyl 3-(5-(5-((−)-3-cyclopropyl-1-((R)-1,1-dimethylethylsulfinamido)-1-phenylpropyl)-2-fluorophenylcarbamoyl)-3-(trifluoromethyl)-1H-pyrazol-1-yl)benzylcarbamate (211c)

Compound (211c) was prepared from 1-(3-((tert-butoxycarbonylamino)methyl)phenyl)-3-(trifluoromethyl)-1H-pyrazole-5-carboxylic acid (10d) (2.73 g, 7.08 mmol) and (R)—N-((−)-1-(3-amino-4-fluorophenyl)-3-cyclopropyl-1-phenylpropyl)-2-methylpropane-2-sulfinamide (211b) (2.5 g, 6.43 mmol) using the procedure as reported in step-3 of scheme 208 to afford tert-butyl 3-(5-(5-((−)-3-cyclopropyl-1-((R)-1,1-dimethylethylsulfinamido)-1-phenylpropyl)-2-fluorophenylcarbamoyl)-3-(trifluoromethyl)-1H-pyrazol-1-yl)benzylcarbamate (211c) (1.532 g, 2.027 mmol, 31.5% yield) as a white solid; $^1$H NMR (300 MHz, DMSO-$d_6$) δ 10.58 (s, 1H), 7.57 (d, J=6.9 Hz, 2H), 7.53-7.47 (m, 1H), 7.42 (dd, J=5.7, 2.8 Hz, 2H), 7.39-7.15 (m, 9H), 5.29 (s, 1H), 4.19 (d, J=6.3 Hz, 2H), 2.77-2.55 (m, 2H), 1.38 (s, 9H), 1.12 (s, 9H), 1.05 (s, 1H), 0.96-0.80 (m, 1H), 0.62 (m, 1H), 0.43-0.26 (m, 2H), −0.02-−0.17 (m, 2H); $^{19}$F NMR (282 MHz, DMSO-$d_6$) δ −60.79, −123.62; MS (ES+) 756.6 (M+H), 778.5 (M+Na), (ES−) 754.5 (M−H), 790.4 (M+Cl); Optical Rotation [α]$_D$=(−) 72.94 [0.255, MeOH].

Step-4: Preparation of (+)-N-(5-(1-amino-3-cyclopropyl-1-phenylpropyl)-2-fluorophenyl)-1-(3-(aminomethyl)phenyl)-3-(trifluoromethyl)-1H-pyrazole-5-carboxamide (211d)

Compound (211d) free base was prepared from of tert-butyl 3-(5-(5-((−)-3-cyclopropyl-1-((R)-1,1-dimethylethylsulfinamido)-1-phenylpropyl)-2-fluorophenylcarbamoyl)-3-(trifluoromethyl)-1H-pyrazol-1-yl)benzylcarbamate (211c) (1.49 g, 1.971 mmol) as reported in step-4 of scheme 208 to afford (+)-N-(5-(1-amino-3-cyclopropyl-1-phenylpropyl)-2-fluorophenyl)-1-(3-(aminomethyl)phenyl)-3-(trifluoromethyl)-1H-pyrazole-5-carboxamide (211d) (1.0 g, 1.813 mmol, 92% yield) free base as a white solid; $^1$H NMR (300 MHz, DMSO-$d_6$) δ 10.51 (s, 1H), 8.32 (s, 2H), 7.57 (d, J=5.1 Hz, 2H), 7.50 (s, 1H), 7.47-7.40 (m, 2H), 7.39-7.30 (m, 2H), 7.29-7.22 (m, 2H), 7.20-7.10 (m, 2H), 3.77 (s, 2H), 3.35 (s, 2H), 2.29-1.97 (m, 4H), 1.10-0.94 (m, 2H), 0.62 (m, 1H), 0.39-0.28 (m, 2H), −0.09 (m, 2H); $^{19}$F NMR (282 MHz, DMSO-$d_6$) δ −60.72, −124.61; MS (ES+) 552.4 (M+1), (ES−) 550.4 (M−1).

To a stirred solution of (+)-N-(5-(1-amino-3-cyclopropyl-1-phenylpropyl)-2-fluorophenyl)-1-(3-(aminomethyl)phenyl)-3-(trifluoromethyl)-1H-pyrazole-5-carboxamide (211d) (0.9 g, 1.632 mmol) free base in ethanol (10 mL) was added conc. HCl (0.680 mL, 8.16 mmol), water (5 mL) stirred for 10 mins and concentrated to dryness to afford (+)-N-(5-(1-amino-3-cyclopropyl-1-phenylpropyl)-2-fluorophenyl)-1-(3-(aminomethyl)phenyl)-3-(trifluoromethyl)-1H-pyrazole-5-carboxamide (211d) (700 mg, 1.121 mmol, 68.7% yield) hydrochloride salt as a white solid.

$^1$H NMR (300 MHz, DMSO-$d_6$) δ 10.84 (d, J=4.1 Hz, 1H), 9.38 (d, J=33.2 Hz, 3H), 8.55 (s, 3H), 7.72 (dd, J=4.6, 2.8 Hz, 2H), 7.68-7.61 (m, 1H), 7.60-7.47 (m, 3H), 7.45-7.31 (m, 7H), 4.10 (s, 2H), 2.3-2.6 (m, 2H), 1.09 (m, 2H), 0.68 (m, 1H), 0.36 (m, 2H), −0.01 (m, 2H); $^{19}$F NMR (282 MHz, DMSO-$d_6$) δ −60.63, −120.68; MS(ES−) 550.4, 586.4 (M+Cl); [α]$_D$=(+) 4.77 [1.09, MeOH]; Analysis calculated for $C_{30}H_{29}F_4N_5O \cdot 2HCl \cdot 1.75H_2O$: C, 54.92; H, 5.30; N, 10.68; Cl, 10.81; Found: C: 54.76, H: 5.33, N: 10.52, Cl: 11.04.

773

Scheme 212

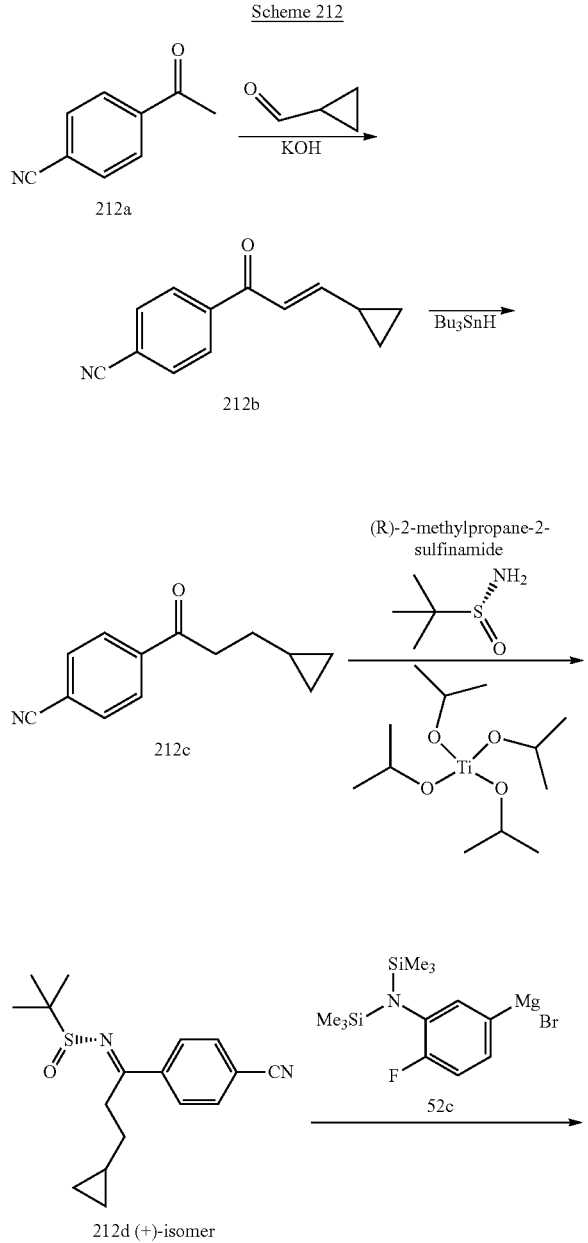

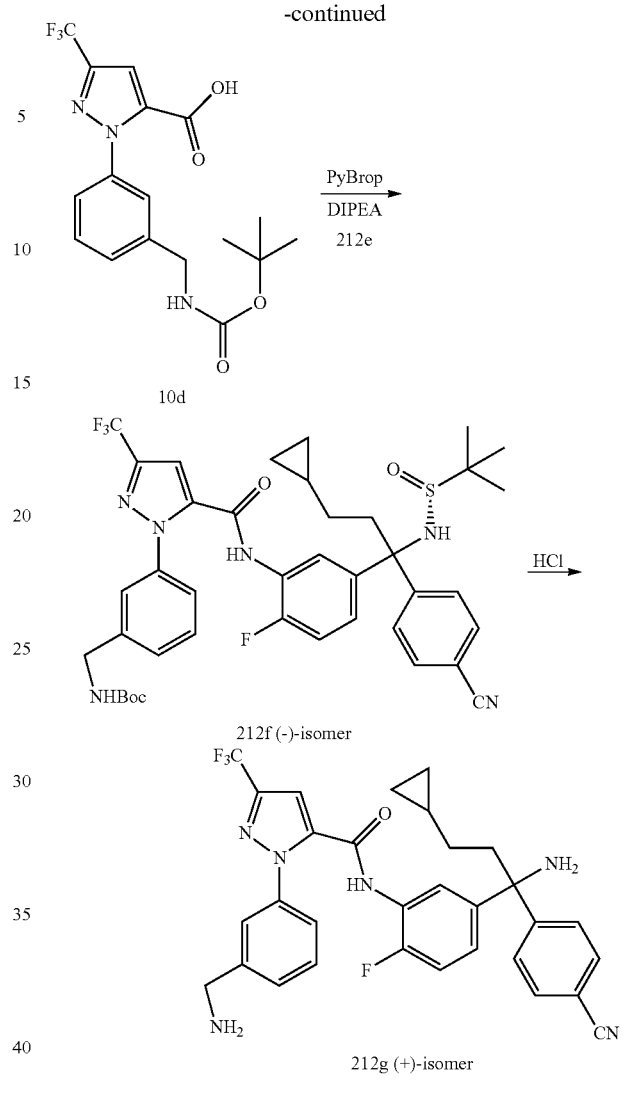

Preparation of (+)-N-(5-(1-amino-1-(4-cyanophenyl)-3-cyclopropylpropyl)-2-fluorophenyl)-1-(3-(aminomethyl)phenyl)-3-(trifluoromethyl)-1H-pyrazole-5-carboxamide (212g)

Step: 1 Preparation of (E)-4-(3-cyclopropylacryloyl)benzonitrile (212b)

To a stirred solution of 4-acetylbenzonitrile (212a) (5 g, 34.4 mmol) in ethanol (100 mL) at 0° C. was added cyclopropanecarboxaldehyde (4.15 mL, 55.1 mmol) followed by potassium hydroxide (2 M aqueous solution, 3.44 mL, 6.89 mmol). The reaction mixture allowed to attain room temperature and stirred for 24h. The reaction was acidified with HCl to pH-6 and concentrated in vacuum maintaining bath temperature below 35° C. The residue obtained was purified by flash column chromatography (silica gel eluting with ethyl acetate in hexanes 0 to 20%) to afford (E)-4-(3-cyclopropylacryloyl)benzonitrile (212b) (512 mg, 2.60 mmol, 7.54% yield) as a colorless liquid; $^1$H NMR (300 MHz, DMSO-d$_6$) δ 8.12-8.08 (m, 2H), 8.02-7.99 (m, 2H), 7.25 (d, J=15.0 Hz, 1H), 6.57 (dd, J=15.1, 10.4 Hz, 1H), 1.80 (dddd, J=12.4, 10.4, 7.9, 4.5 Hz, 1H), 1.08-0.99 (m, 2H), 0.79 (tt, J=4.8, 2.4 Hz, 2H); MS (ES−) 196.1 (M−1).

Step 2: Preparation of 4-(3-cyclopropylpropanoyl)benzonitrile (212c)

To a stirred solution of (E)-4-(3-cyclopropylacryloyl) benzonitrile (212b) (1.1 g, 5.58 mmol) in acetonitrile (10 mL) was added tri-n-butyltin hydride (1.489 mL, 5.58 mmol) and heated at reflux for 6 h. The reaction mixture was cooled to room temperature and concentrated in vacuum. The residue obtained was purified by flash column chromatography (silica gel eluting with ethyl acetate in hexanes 0 to 100%) to afford 4-(3-cyclopropylpropanoyl)benzonitrile (212c) (457 mg, 2.294 mmol, 41.1% yield) as a colorless oil; $^1$H NMR (300 MHz, DMSO-$d_6$) δ 8.08-8.03 (m, 2H), 7.98-7.91 (m, 2H), 3.09 (t, J=7.2 Hz, 2H), 1.46 (q, J=7.1 Hz, 2H), 0.77-0.59 (m, 1H), 0.38-0.26 (m, 2H), 0.06--0.04 (m, 2H); MS (ES−) 198.2 (M−1).

Step-3: Preparation of (+)-N-(1-(4-cyanophenyl)-3-cyclopropylpropylidene)-2-methylpropane-2-sulfinamide (212d)

Compound (212d) was prepared from 4-(3-cyclopropylpropanoyl)benzonitrile (212c) (0.814 g, 4.08 mmol) and (R)-2-methylpropane-2-sulfinamide (0.45 g, 3.71 mmol), using procedure as reported in step-1 of scheme 208 to afford (+)-N-(1-(4-cyanophenyl)-3-cyclopropylpropylidene)-2-methylpropane-2-sulfinamide (212d) (720 mg, 2.38 mmol, 64.1% yield) as a light yellow syrup; $^1$H NMR (300 MHz, DMSO-$d_6$) δ 8.11-7.93 (m, 4H), 3.34 (m, 2H), 1.44 (m, 1H), 1.24 (s, 10H), 0.73 (m, 1H), 0.45-0.29 (m, 2H), 0.03 (m, 2H).; Optical rotation: [α]$_D$=(+) 16.55 [0.29, MeOH].

Step-4: Preparation of (R)—N-((−)-1-(3-amino-4-fluorophenyl)-1-(4-cyanophenyl)-3-cyclopropylpropyl)-2-methylpropane-2-sulfinamide (212e)

Compound (212e) was prepared from (+)-N-(1-(4-cyanophenyl)-3-cyclopropylpropylidene)-2-methylpropane-2-sulfinamide (212d) (0.5 g, 1.653 mmol), using procedure as reported in step-2 of scheme 208 to afford (R)—N-((−)-1-(3-amino-4-fluorophenyl)-1-(4-cyanophenyl)-3-cyclopropylpropyl)-2-methylpropane-2-sulfinamide (212e) (538 mg, 1.301 mmol, 79% yield) as a white solid; $^1$H NMR (300 MHz, DMSO-$d_6$) δ 7.83-7.66 (m, 2H), 7.61-7.44 (m, 2H), 6.90 (dd, J=11.3, 8.5 Hz, 1H), 6.70 (dd, J=8.7, 2.4 Hz, 1H), 6.47 (ddd, J=8.6, 4.3, 2.4 Hz, 1H), 5.27 (s, 1H), 5.11 (s, 2H), 2.62-2.55 (m, 1H), 2.46-2.39 (m, 1H), 1.12 (s, 9H), 1.06 (s, 1H), 0.99-0.80 (m, 1H), 0.64 (s, 1H), 0.36 (m, 2H), −0.02--0.14 (m, 2H); $^{19}$F NMR (282 MHz, DMSO-$d_6$) δ −137.54; MS (ES+) 414.396 (M+1); Optical rotation: [α]$_D$=(−) 83.24 [0.185, MeOH].

Step-5: Preparation of tert-butyl 3-(5-(5-((−)-1-(4-cyanophenyl)-3-cyclopropyl-1-((R)-1,1-dimethylethylsulfinamido)propyl)-2-fluorophenylcarbamoyl)-3-(trifluoromethyl)-1H-pyrazol-1-yl)benzylcarbamate (212f)

Compound (212f) was prepared from 1-(3-((tert-butoxycarbonylamino)methyl)phenyl)-3-(trifluoromethyl)-1H-pyrazole-5-carboxylic acid (10d) (0.512 g, 1.330 mmol) and (R)—N-((−)-1-(3-amino-4-fluorophenyl)-1-(4-cyanophenyl)-3-cyclopropylpropyl)-2-methylpropane-2-sulfinamide (212e) (0.5 g, 1.209 mmol) using the procedure as reported in step-3 of scheme 208 to afford tert-butyl 3-(5-(5-((−)-1-(4-cyanophenyl)-3-cyclopropyl-1-((R)-1,1-dimethylethylsulfinamido)propyl)-2-fluorophenylcarbamoyl)-3-(trifluoromethyl)-1H-pyrazol-1-yl)benzylcarbamate (212f) (557 mg, 0.713 mmol, 59.0% yield) as a colorless solid; $^1$H NMR (300 MHz, DMSO-$d_6$) δ 10.61 (s, 1H), 7.78 (d, J=8.5 Hz, 2H), 7.58 (m, 2H), 7.49 (m, 2H), 7.42 (m, 2H), 7.38-7.30 (m, 2H), 7.24 (d, J=7.8 Hz, 2H), 5.57 (s, 1H), 4.19 (d, J=6.2 Hz, 2H), 3.10-2.95 (m, 1H), 2.65-2.54 (m, 1H), 2.44 (m, 1H), 1.38 (s, 9H), 1.12 (s, 10H), 1.03-0.76 (m, 1H), 0.62 (m, 1H), 0.34 (m, 2H), −0.08 (m, 2H); $^{19}$F NMR (282 MHz, DMSO-$d_6$) δ −60.78, −122.98; MS (ES+) 803.6 (M+Na); Optical rotation: [α]$_D$=(−) 56 [0.15, MeOH].

Step-6: Preparation of (+)-N-(5-(1-amino-1-(4-cyanophenyl)-3-cyclopropylpropyl)-2-fluorophenyl)-1-(3-(aminomethyl)phenyl)-3-(trifluoromethyl)-1H-pyrazole-5-carboxamide (212g)

To a stirred solution of tert-butyl 3-(5-(5-((−)-1-(4-cyanophenyl)-3-cyclopropyl-1-((R)-1,1-dimethylethylsulfinamido)propyl)-2-fluorophenylcarbamoyl)-3-(trifluoromethyl)-1H-pyrazol-1-yl)benzylcarbamate (212f) (0.51 g, 0.653 mmol) in ethanol (25 mL) was added conc. HCl (0.544 mL, 6.53 mmol) and heated at reflux for 1 h. The reaction mixture was concentrated in vacuum to dryness, triturated with ether, stirred overnight at room temperature, collected by filtration and washed with ether. This residue was dissolved in ethanol (20 mL) and concentrated in vacuum to dryness to afford of (+)-N-(5-(1-amino-1-(4-cyanophenyl)-3-cyclopropylpropyl)-2-fluorophenyl)-1-(3-(aminomethyl)phenyl)-3-(trifluoromethyl)-1H-pyrazole-5-carboxamide (212g) (410 mg, 0.631 mmol, 97% yield) hydrochloride as a white solid.

$^1$H NMR (300 MHz, DMSO-$d_6$) δ 10.81 (s, 1H), 9.48 (s, 3H), 8.43 (s, 3H), 7.94 (d, J=8.0 Hz, 2H), 7.71 (d, J=12.1 Hz, 2H), 7.66-7.46 (m, 6H), 7.45-7.28 (m, 2H), 4.12 (s, 2H), 2.60-2.49 (m, 2H), 1.29-1.08 (m, 2H), 0.67 (m, 1H), 0.46-0.29 (m, 2H), 0.02-001 (m, 2H); $^{19}$F NMR (282 MHz, DMSO-$d_6$) δ −60.79, −120.37; MS (ES+) 577.4 (M+1), (ES−) 575.5 (M−1), 611.4 (M+Cl); Optical rotation: [α]$_D$= (+) 16.43 [CH$_3$OH, 0.28]; Analysis calculated for $C_{31}H_{28}F_4N_6O.2HCl.2H_2O$: C, 54.31; H, 5.00; Cl, 10.34; N, 12.26; Found: C, 53.95; H, 5.01; Cl, 9.94; N, 12.01.

Scheme 213

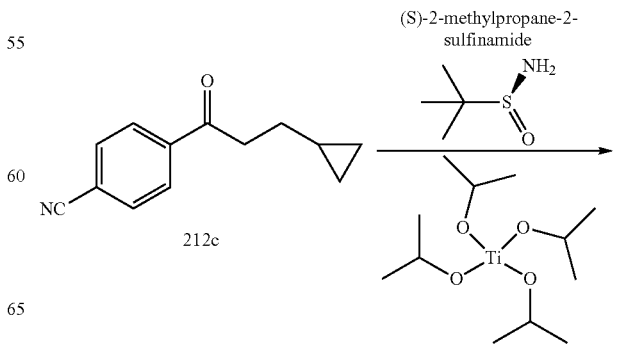

777
-continued

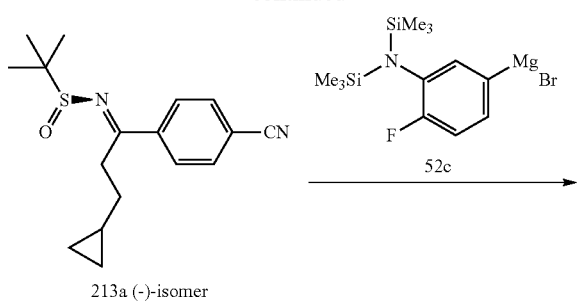

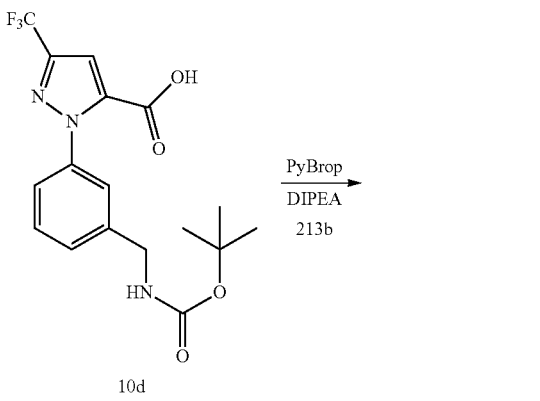

778
-continued

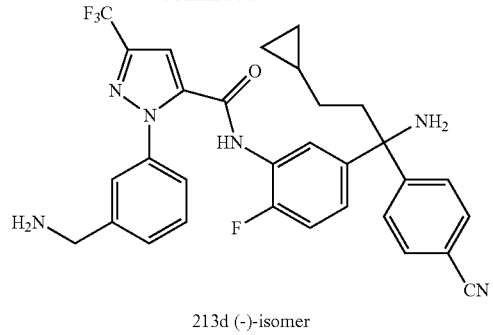 [SMILES: N#Cc1ccc(C(N)(CCC2CC2)c2ccc(F)c(NC(=O)c3cc(C(F)(F)F)nn3-c3cccc(CN)c3)c2)cc1]

Preparation of (−)-N-(5-(1-amino-1-(4-cyanophenyl)-3-cyclopropylpropyl)-2-fluorophenyl)-1-(3-(aminomethyl)phenyl)-3-(trifluoromethyl)-1H-pyrazole-5-carboxamide (213d)

Step-1: Preparation of (−)-N-(1-(4-cyanophenyl)-3-cyclopropylpropylidene)-2-methylpropane-2-sulfinamide (213a)

Compound (213a) was prepared from 4-(3-cyclopropylpropanoyl)benzonitrile (212c) (1.21 g, 6.07 mmol) and (S)-2-methylpropane-2-sulfinamide (0.743 g, 6.07 mmol), using procedure as reported in step-1 of scheme 208 to afford (−)-N-(1-(4-cyanophenyl)-3-cyclopropylpropylidene)-2-methylpropane-2-sulfinamide (213a) (1.252 g, 4.14 mmol, 68.2% yield) as a light yellow syrup; $^1$H NMR (300 MHz, DMSO-$d_6$) δ 8.04-7.89 (m, 4H), 3.47-3.16 (m, 2H), 1.41 (q, J=7.5 Hz, 2H), 1.21 (s, 9H), 0.80-0.60 (m, 1H), 0.40-0.27 m, 2H), 0.08--0.10 (m, 2H); MS (ES+) 303.3 (M+1); (ES−) 301.3 (M−1).

Step-2: Preparation of (S)—N-((+)-1-(3-amino-4-fluorophenyl)-1-(4-cyanophenyl)-3-cyclopropylpropyl)-2-methylpropane-2-sulfinamide (213b)

Compound (213b) was prepared from (−)-N-(1-(4-cyanophenyl)-3-cyclopropylpropylidene)-2-methylpropane-2-sulfinamide (213a) (1.197 g, 3.96 mmol), using procedure as reported in step-2 of scheme 208 to afford (S)—N-((+)-1-(3-amino-4-fluorophenyl)-1-(4-cyanophenyl)-3-cyclopropylpropyl)-2-methylpropane-2-sulfinamide (213b) (968 mg, 2.341 mmol, 59.1% yield) as a white solid; $^1$H NMR (300 MHz, DMSO-$d_6$) δ 7.80-7.73 (m, 2H), 7.55-7.49 (m, 2H), 6.89 (dd, J=11.3, 8.5 Hz, 1H), 6.71 (dd, J=8.7, 2.4 Hz, 1H), 6.47 (ddd, J=8.5, 4.3, 2.4 Hz, 1H), 5.23 (s, 1H), 5.09 (s, 2H), 2.65-2.40 (m, 2H), 1.13 (s, 9H), 1.25-1.00 (m, 1H), 1.00-0.80 (m, 1H), 0.72-0.55 (m, 1H), 0.45-0.25 (m, 2H), 0.04--0.21 (m, 2H); $^{19}$F NMR (282 MHz, DMSO-$d_6$) δ −137.37; MS (ES+); 436.3 (M+Na); Optical rotation: $[α]_D$=(+) 104.62 [0.295, MeOH].

Step-3: Preparation of tert-butyl 3-(5-(5-((+)-1-(4-cyanophenyl)-3-cyclopropyl-1-((S)-1,1-dimethylethylsulfinamido)propyl)-2-fluorophenylcarbamoyl)-3-(trifluoromethyl)-1H-pyrazol-1-yl)benzylcarbamate (213c)

Compound (213c) was prepared from 1-(3-((tert-butoxycarbonylamino)methyl)phenyl)-3-(trifluoromethyl)-1H-pyrazole-5-carboxylic acid (10d) (0.933 g, 2.42 mmol) and (S)—N-((+)-1-(3-amino-4-fluorophenyl)-1-(4-cyanophenyl)-3-cyclopropylpropyl)-2-methylpropane-2-sulfinamide (213b) (0.91 g, 2.2 mmol) using the procedure as reported in step-3 of scheme 208 to afford tert-butyl 3-(5-(5-((+)-1-(4-cyanophenyl)-3-cyclopropyl-1-((S)-1,1-dimethylethylsulfinamido)propyl)-2-fluorophenylcarbamoyl)-3-(trifluoromethyl)-1H-pyrazol-1-yl)benzylcarbamate (213c) (1.126 g, 1.442 mmol, 65.5% yield) as a colorless solid; $^1$H NMR (300 MHz, DMSO-$d_6$) δ 10.61 (s, 1H), 7.93-7.09 (m, 13H), 5.58 (s, 1H), 4.19 (d, J=6.2 Hz, 2H), 2.75-2.40 (m, 2H), 1.38 (s, 9H), 1.13 (s, 9H), 1.20-1.00 (m, 1H), 0.87 (d, J=23.9 Hz, 1H), 070-0.55 (m, 1H), 0.43-0.26 (m, 2H), −0.01−−0.18 (m, 2H); $^{19}$F NMR (282 MHz, DMSO-$d_6$) δ −61.16, −122.81; MS (ES+) 781.6 (M+1); ES (−) 779.5 (M−1) Optical rotation: $[α]_D$=(+) 65.38 [0.26, MeOH].

Step-4: Preparation of (−)-N-(5-(1-amino-1-(4-cyanophenyl)-3-cyclopropylpropyl)-2-fluorophenyl)-1-(3-(aminomethyl)phenyl)-3-(trifluoromethyl)-1H-pyrazole-5-carboxamide (213d)

To a stirred solution of tert-butyl 3-(5-(5-((+)-1-(4-cyanophenyl)-3-cyclopropyl-1-((S)-1,1-dimethylethylsulfinamido)propyl)-2-fluorophenylcarbamoyl)-3-(trifluoromethyl)-1H-pyrazol-1-yl)benzylcarbamate (213c) (0.609 g, 0.78 mmol) in ethanol (6 mL) was added conc. HCl (0.65 mL, 7.8 mmol) and heated at reflux for 1 h. The reaction mixture was concentrated in vacuum to dryness and purified by flash column chromatography (silica gel, 25 g, eluting with CMA-80 in chloroform 0-25%) to furnish product. The product was dissolved in methanol (10 mL) and added 4 N aqueous HCl (0.52 mL) and concentrated in vacuum to dryness to afford (−)-N-(5-(1-amino-1-(4-cyanophenyl)-3-cyclopropylpropyl)-2-fluorophenyl)-1-(3-(aminomethyl)phenyl)-3-(trifluoromethyl)-1H-pyrazole-5-carboxamide (213d) (330 mg, 0.508 mmol, 65.1% yield) hydrochloride salt as a white solid.

$^1$H NMR (300 MHz, DMSO-$d_6$) δ 10.80 (s, 1H), 9.48 (s, 3H), 8.42 (s, 3H), 7.94 (d, J=8.4 Hz, 2H), 7.75-7.66 (m, 2H), 7.64-7.46 (m, 6H), 7.40 (t, J=9.3 Hz, 1H), 7.36-7.28 (m, 1H), 4.11 (q, J=5.8 Hz, 2H), 2.55 (d, J=9.7 Hz, 2H), 1.22-0.99 (m, 2H), 0.77-0.53 (m, 1H), 0.44-0.26 (m, 2H), −0.00 (s, 2H); $^{19}$F NMR (282 MHz, DMSO $d_6$) δ −60.64, −120.16. MS (ES+) 577.5 (M+1); (ES−) 576.8 (M−1); IR 2234 cm$^{-1}$; Optical rotation: $[α]_D$=(−) 10.84 [1.07, MeOH].

Scheme 214

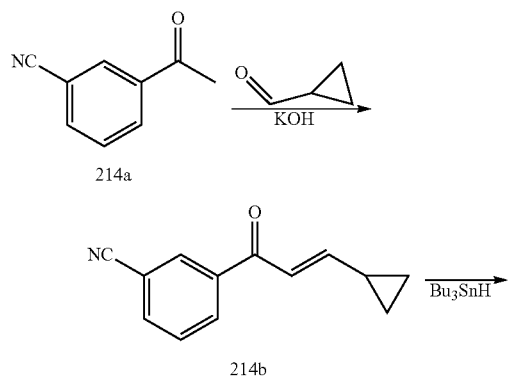

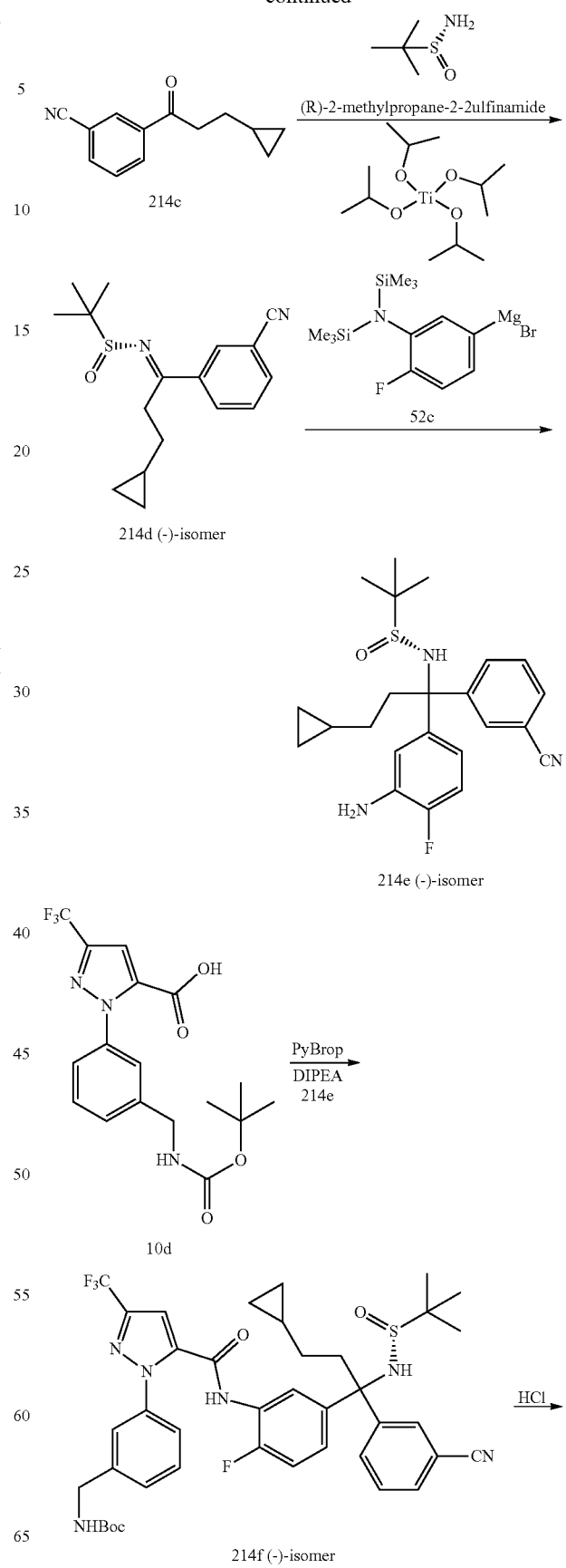

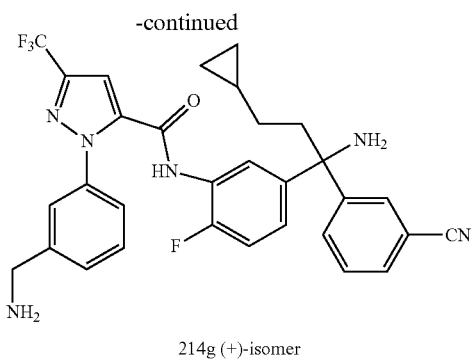

214g (+)-isomer

Preparation of (+)-N-(5-(1-amino-1-(3-cyanophenyl)-3-cyclopropylpropyl)-2-fluorophenyl)-1-(3-(aminomethyl)phenyl)-3-(trifluoromethyl)-1H-pyrazole-5-carboxamide (214g)

Step: 1 Preparation of 3-(3-cyclopropylacryloyl)benzonitrile (214b)

To a stirred solution of 3-acetylbenzonitrile (214a) (50 g, 344 mmol) in methanol (800 mL) at 0° C. was added cyclopropanecarboxaldehyde (41 mL, 549 mmol) followed by potassium hydroxide (1M aqueous solution, 67 mL, 67 mmol). The reaction mixture allowed to attain room temperature and stirred for 14h. The reaction was acidified with HCl to pH-6 (75 mL, 1 N) and concentrated in vacuum maintaining bath temperature below 35° C. The residue was diluted with ethyl acetate (1200 mL) and washed with water (800 mL). The aqueous layer was extracted with ethyl acetate (800 mL) and organic layers were combined washed with brine, dried, filtered and concentrated in vacuum to afford 3-(3-cyclopropylacryloyl)benzonitrile (214b) (72.42 gm) crude as a colorless liquid, which was used as such in next step; $^1$H NMR (300 MHz, DMSO-d$_6$) δ 8.19 (dp, J=7.8, 1.6 Hz, 1H), 8.11 (dddt, J=6.3, 3.7, 2.6, 1.4 Hz, 1H), 7.80-7.65 (m, 2H), 7.32 (dd, J=15.1, 7.6 Hz, 1H), 6.60 (ddd, J=15.0, 11.3, 10.4 Hz, 1H), 1.91-1.74 (m, 1H), 1.04 (m, 2H), 0.85-0.75 (m, 2H).

Step 2: Preparation of 3-(3-cyclopropylpropanoyl)benzonitrile (214c)

To a stirred solution of 3-(3-cyclopropylacryloyl)benzonitrile (214b) (65.7 g, 333 mmol) in benzene (750 mL) was added tri-n-butyltin hydride (185 mL, 666 mmol) and heated at reflux for 14 h. The reaction mixture was cooled to room temperature and concentrated in vacuum. The residue was purified by flash column chromatography (silica gel eluting with ethyl acetate in hexanes 0 to 100%) to afford 3-(3-cyclopropylpropanoyl)benzonitrile (214c) (23.3, 116.9 mmol, 34% yield) as a colorless oil; $^1$H NMR (300 MHz, DMSO-d$_6$) δ 8.41 (td, J=1.8, 0.6 Hz, 1H), 8.24 (ddd, J=7.9, 1.8, 1.2 Hz, 1H), 8.09 (dt, J=7.7, 1.4 Hz, 1H), 7.73 (td, J=7.8, 0.6 Hz, 1H), 3.15 (t, J=7.2 Hz, 2H), 1.52 (q, J=7.1 Hz, 2H), 0.81-0.64 (m, 1H), 0.46-0.26 (m, 2H), 0.13-0.00 (m, 2H); MS (ES−) 198.2 (M−1).

Step-3: Preparation of (−)-N-(1-(3-cyanophenyl)-3-cyclopropylpropylidene)-2-methylpropane-2-sulfinamide (214d)

Compound (214d) was prepared from 3-(3-cyclopropylpropanoyl)benzonitrile (214c) (22.8 g, 114 mmol) and (R)-2-methylpropane-2-sulfinamide (13.95 g, 114 mmol), using procedure as reported in step-1 of scheme 208 to afford (−)-N-(1-(3-cyanophenyl)-3-cyclopropylpropylidene)-2-methylpropane-2-sulfinamide (214d) (21.8 g, 72.1 mmol, 63% yield) as a light yellow syrup;
$^1$H NMR (300 MHz, DMSO-d$_6$) δ 8.29 (s, 1H), 8.21-8.12 (m, 1H), 8.01 (d, J=7.7 Hz, 1H), 7.70 (t, J=7.9 Hz, 1H), 3.54-3.13 (m, 2H), 1.44 (q, J=7.5 Hz, 2H), 1.23 (s, 9H), 0.82-0.65 (m, 1H), 0.44-0.29 (m, 2H), 0.11-0.00 (m, 2H); MS (ES+) 303.3 (M+1); (ES−) 301.3 (M−1); Optical rotation: [α]$_D$ (−) 66.92 (0.26, MeOH).

Step-4: Preparation of (R)—N-((−)-1-(3-amino-4-fluorophenyl)-1-(3-cyanophenyl)-3-cyclopropylpropyl)-2-methylpropane-2-sulfinamide (214e)

To a stirred solution of (−)-N-(1-(3-cyanophenyl)-3-cyclopropylpropylidene)-2-methylpropane-2-sulfinamide (214d) (17.72 g, 58.6 mmol) in toluene (350 mL) at −20° C. was added dropwise a freshly prepared solution of (3-(bis(trimethylsilyl)amino)-4-fluorophenyl)magnesium bromide (52c) (160 mL, 120 mmol, 0.75N) over a period of 30 mins. The reaction mixture was stirred at −20° C. for 1 h and quenched with 1N aqueous KHSO$_4$ (275 mL). The reaction mixture was stirred for 1 h at room temperature, diluted with water (100 mL) basified with 2 N NaOH to pH 8 and extracted with ethyl acetate (600 mL, 300 mL). The organic layers were combined washed with water (2×300 mL), brine (300 mL), dried and concentrated in vacuum to dryness. The crude residue was triturated with ethyl acetate and solid obtained was collected by filtration to obtain on drying under vacuum (R)—N-((−)-1-(3-amino-4-fluorophenyl)-1-(3-cyanophenyl)-3-cyclopropylpropyl)-2-methylpropane-2-sulfinamide (214e) (10.4 g, 42.91% yield) as a white solid. The filtrate was concentrated in vacuum and purified by flash column chromatography (silica gel, eluting with ethyl acetate in hexanes 0 to 50%) to (R)—N-((−)-1-(3-amino-4-fluorophenyl)-1-(3-cyanophenyl)-3-cyclopropylpropyl)-2-methylpropane-2-sulfinamide (214e) (4.11 g, 16.95% yield) as a white solid; $^1$H NMR (300 MHz, DMSO-d$_6$) δ 7.78 (t, J=1.6 Hz, 1H), 7.70 (dt, J=7.5, 1.4 Hz, 1H), 7.62 (dt, J=8.1, 1.5 Hz, 1H), 7.50 (t, J=7.8 Hz, 1H), 6.90 (dd, J=11.3, 8.5 Hz, 1H), 6.72 (dd, J=8.7, 2.4 Hz, 1H), 6.47 (ddd, J=8.5, 4.3, 2.4 Hz, 1H), 5.27 (s, 1H), 5.10 (s, 2H), 2.66-2.40 (m, 2H), 1.20-1.03 (m, 1H), 1.12 (s, 9H), 1.01-0.81 (m, 1H), 0.72-0.57 (m, 1H), 0.36 (m, 2H), 0.03-0.15 (m, 2H); 19F NMR (282 MHz, DMSO-d$_6$) δ −137.34; MS (ES+): 436.4 (M+Na); IR (KBr) 2235 cm$^{-1}$; Optical rotation: [α]$_D$ (−) 107.95 (0.78, MeOH); Analysis calculated for C$_{23}$H$_{28}$FN$_3$OS: C, 66.80; H, 6.82; N, 10.16; Found: C, 67.06; H, 6.82; N, 10.28.

Step-5: Preparation of tert-butyl 3-(5-(5-((−)-1-(3-cyanophenyl)-3-cyclopropyl-1-((R)-1,1-dimethylethylsulfinamido)propyl)-2-fluorophenylcarbamoyl)-3-(trifluoromethyl)-1H-pyrazol-1-yl)benzylcarbamate (214f)

Compound (214f) was prepared from 1-(3-((tert-butoxycarbonylamino)methyl)phenyl)-3-(trifluoromethyl)-1H-pyrazole-5-carboxylic acid (10d) (9.74 g, 25.3 mmol) and (R)—N-((−)-1-(3-amino-4-fluorophenyl)-1-(3-cyanophenyl)-3-cyclopropylpropyl)-2-methylpropane-2-sulfinamide (214e) (9.5 g, 22.97 mmol) using the procedure as reported in step-3 of scheme 208 to afford tert-butyl 3-(5-(5-((−)-1-(3-cyanophenyl)-3-cyclopropyl-1-((R)-1,1-dimethylethylsulfinamido)propyl)-2-fluorophenylcarbamoyl)-3-(trifluoromethyl)-1H-pyrazol-1-yl)benzylcarbamate (214f) (10.00 g, 12.8 mmol, 55.7% yield) as a white solid; $^1$H NMR (300 MHz, DMSO-$d_6$) δ 10.60 (s, 1H), 7.78 (s, 1H), 7.71 (dt, J=7.3, 1.4 Hz, 1H), 7.64-7.30 (m, 8H), 7.23 (d, J=7.5 Hz, 2H), 5.56 (s, 1H), 4.18 (d, J=6.2 Hz, 2H), 2.74-2.39 (m, 2H), 1.38 (s, 9H), 1.12 (s, 9H), 1.09-0.82 (m, 2H), 0.72-0.54 (m, 1H), 0.34 (d, J=8.0 Hz, 2H), −0.01−−0.16 (m, 2H); $^{19}$F NMR (282 MHz, DMSO) δ −60.80, −122.94; MS (ES+) 803.6 (M+Na), (ES−) 779.6 (M−1); Optical rotation: $[α]_D$=(−) 75.09 (0.285, MeOH).

Step-6: Preparation of (+)-N-(5-(1-amino-1-(3-cyanophenyl)-3-cyclopropylpropyl)-2-fluorophenyl)-1-(3-(aminomethyl)phenyl)-3-(trifluoromethyl)-1H-pyrazole-5-carboxamide (214g)

To a stirred solution of tert-butyl 3-(5-(5-((−)-1-(3-cyanophenyl)-3-cyclopropyl-1-((R)-1,1-dimethylethylsulfinamido)propyl)-2-fluorophenylcarbamoyl)-3-(trifluoromethyl)-1H-pyrazol-1-yl)benzylcarbamate (214f) (0.75 g, 0.960 mmol) in ethanol (7.5 mL) was added conc. HCl (0.8 mL, 9.6 mmol) and heated at reflux for 1 h. The reaction mixture was concentrated in vacuum to dryness and the residue obtained was purified by flash column chromatography (silica gel, 24 g eluting with CMA 80 in chloroform 0 to 100%) to afford product which was repurified by flash column chromatography (silica gel, 24 g eluting with methanol in chloroform 0 to 50%) to afford (+)-N-(5-(1-amino-1-(3-cyanophenyl)-3-cyclopropylpropyl)-2-fluorophenyl)-1-(3-(aminomethyl)phenyl)-3-(trifluoromethyl)-1H-pyrazole-5-carboxamide (214g) (0.36 g, 0.624 mmol, 65.0% yield) free base as a white solid; $^1$H NMR (300 MHz, DMSO-$d_6$) δ 10.53 (s, 1H), 7.86 (t, J=1.7 Hz, 1H), 7.70-7.55 (m, 5H), 7.54-7.43 (m, 3H), 7.39 (dt, J=7.2, 2.0 Hz, 1H), 7.28 (ddd, J=8.7, 4.8, 2.4 Hz, 1H), 7.18 (dd, J=10.2, 8.7 Hz, 1H), 3.92 (s, 2H), 2.23 (t, J=8.2 Hz, 2H), 1.08-0.94 (m, 2H), 0.62 (qq, J=7.0, 4.7, 3.5 Hz, 1H), 0.40-0.27 (m, 2H), −0.08 (td, J=5.2, 4.6, 3.4 Hz, 2H); $^{19}$F NMR (282 MHz, DMSO) δ −60.39, −123.77; MS (ES+) 577.5 (M+1); (ES−) 575.5 (M−1); IR (KBr) 2230 cm$^{-1}$; Optical rotation: $[α]_D$=(+) 9.18 [1.59, MeOH].

To a stirred solution of free base of (+)-N-(5-(1-amino-1-(3-cyanophenyl)-3-cyclopropylpropyl)-2-fluorophenyl)-1-(3-(aminomethyl)phenyl)-3-(trifluoromethyl)-1H-pyrazole-5-carboxamide (214g) (0.3 g, 0.52 mmol) in methanol (10 mL) was added conc. HCl (0.217 mL, 2.60 mmol) stirred for 30 mins and concentrated to dryness to afford (+)-N-(5-(1-amino-1-(3-cyanophenyl)-3-cyclopropylpropyl)-2-fluorophenyl)-1-(3-(aminomethyl)phenyl)-3-(trifluoromethyl)-1H-pyrazole-5-carboxamide (214g) (0.31 g, 0.477 mmol, 92% yield) hydrochloride as a white solid; $^1$H NMR (300 MHz, DMSO-$d_6$) δ 10.81 (s, 1H), 9.49 (s, 3H), 8.46 (s, 3H), 7.93-7.80 (m, 1H), 7.74-7.68 (m, 3H), 7.67-7.49 (m, 5H), 7.44-7.29 (m, 2H), 4.11 (d, J=3.8 Hz, 2H), 2.55 (d, J=10.8 Hz, 3H), 1.37-1.16 (m, 1H), 0.67 (q, J=6.5 Hz, 1H), 0.47-0.25 (m, 2H), 0.07−−0.02 (m, 2H); $^{19}$F NMR (282 MHz, DMSO-$d_6$) δ −60.64, −120.22; MS (ES+) 577.4 (M+1); (ES−) 575.5 (M−1); IR (KBr) 2235 cm$^{-1}$.

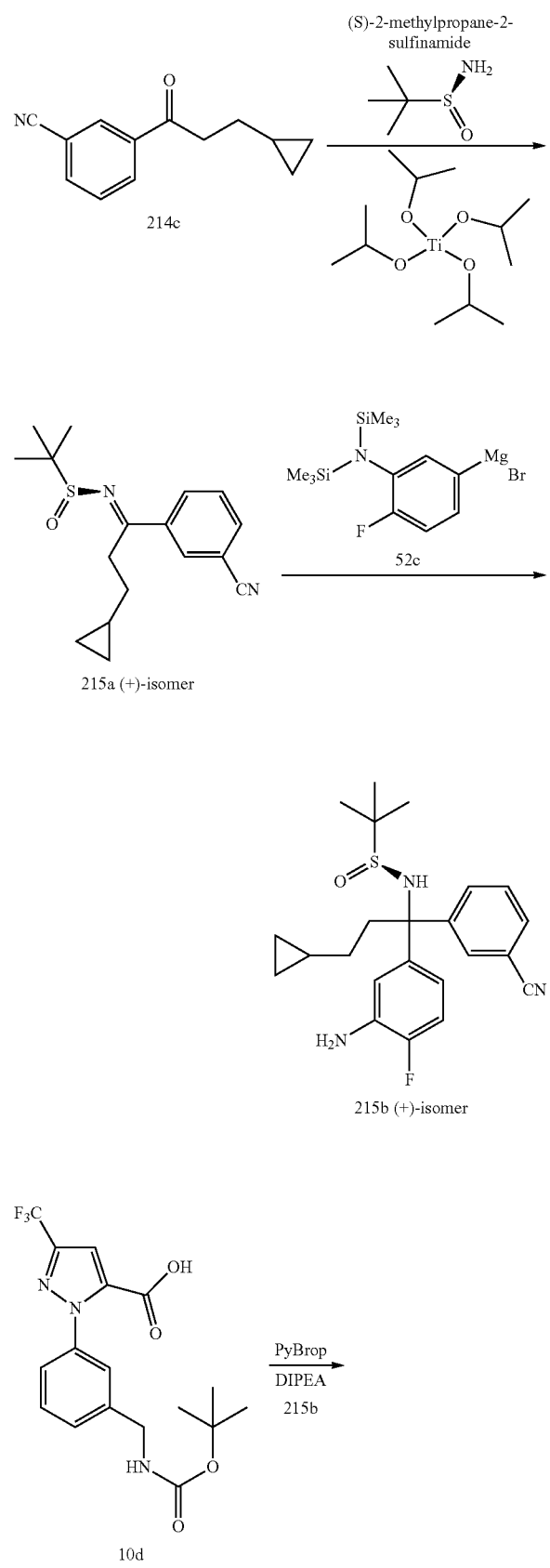

Scheme 215

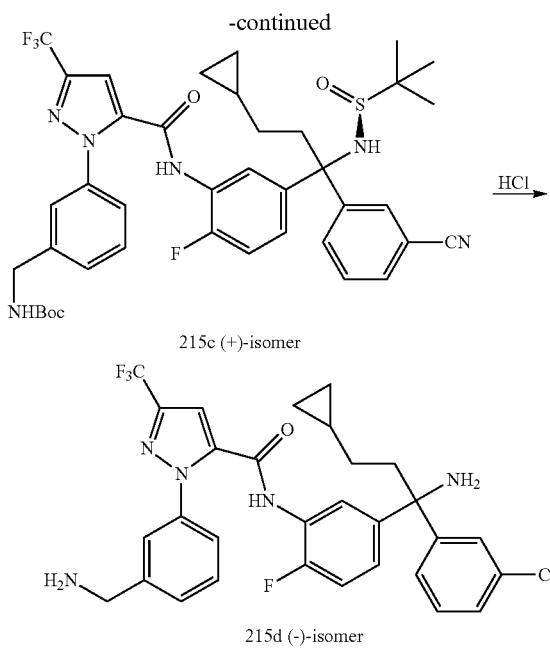

215c (+)-isomer 215d (−)-isomer

Preparation of (−)-N-(5-(1-amino-1-(3-cyanophenyl)-3-cyclopropylpropyl)-2-fluorophenyl)-1-(3-(aminomethyl)phenyl)-3-(trifluoromethyl)-1H-pyrazole-5-carboxamide (215d)

Step-1: Preparation of (+)-N-(1-(3-cyanophenyl)-3-cyclopropylpropylidene)-2-methylpropane-2-sulfinamide (215a)

Compound (215a) was prepared from 3-(3-cyclopropylpropanoyl)benzonitrile (212c) (2.33 g, 11.69 mmol) and (S)-2-methylpropane-2-sulfinamide (1.432 g, 11.69 mmol), using procedure as reported in step-1 of scheme 208 to afford (+)-N-(1-(3-cyanophenyl)-3-cyclopropylpropylidene)-2-methylpropane-2-sulfinamide (215a) (2.186 g, 7.23 mmol, 61.8% yield) as a light yellow syrup; $^1$H NMR (300 MHz, DMSO-$d_6$) δ 8.29 (s, 1H), 8.19 (d, J=8.0 Hz, 1H), 8.02 (d, J=7.7 Hz, 1H), 7.71 (t, J=7.9 Hz, 1H), 3.54-3.13 (m, 2H), 1.45 (q, J=7.5 Hz, 2H), 1.24 (s, 9H), 0.85-0.65 (m, 1H), 0.43-0.27 (m, 2H), 0.13--0.09 (m, 2H); MS (ES+) 303.3 (M+1); 325.3 (M+Na) Optical rotation: $[α]_D$=(+) 27.74 [0.31, MeOH].

Step-2: Preparation of (S)—N-((+)-1-(3-amino-4-fluorophenyl)-1-(3-cyanophenyl)-3-cyclopropylpropyl)-2-methylpropane-2-sulfinamide (215b)

Compound (215b) was prepared from (+)-N-(1-(3-cyanophenyl)-3-cyclopropylpropylidene)-2-methylpropane-2-sulfinamide (215a) (0.93 g, 3.08 mmol), using procedure as reported in step-2 of scheme 208 to afford (S)—N-((+)-1-(3-amino-4-fluorophenyl)-1-(3-cyanophenyl)-3-cyclopropylpropyl)-2-methylpropane-2-sulfinamide (215b) (370 mg, 0.895 mmol, 29.1% yield) as a white solid; $^1$H NMR (300 MHz, DMSO-$d_6$) δ 7.78 (t, J=1.7 Hz, 1H), 7.70 (dt, J=7.5, 1.3 Hz, 1H), 7.62 (dt, J=8.2, 1.5 Hz, 1H), 7.50 (t, J=7.8 Hz, 1H), 6.90 (dd, J=11.3, 8.5 Hz, 1H), 6.72 (dd, J=8.8, 2.4 Hz, 1H), 6.47 (ddd, J=8.6, 4.4, 2.4 Hz, 1H), 5.26 (s, 1H), 5.10 (s, 2H), 2.65-2.40 (m, 2H), 1.30-1.00 (m, 1H), 1.12 (s, 9H), 1.00-0.80 (m, 1H), 0.72-0.56 (m, 1H), 0.42-0.28 (m, 2H), 0.06--0.14 (m, 2H); MS (ES+) 414.4 (M+1); 436.4 (M+Na) (ES−) 412.4 (M−1); Optical rotation: $[α]_D$=(+) 101.13 [0.265, MeOH].

Step-3: Preparation of tert-butyl 3-(5-(5-((+)-1-(3-cyanophenyl)-3-cyclopropyl-1-((S)-1,1-dimethylethylsulfinamido)propyl)-2-fluorophenylcarbamoyl)-3-(trifluoromethyl)-1H-pyrazol-1-yl)benzylcarbamate (215c)

Compound (215c) was prepared from 1-(3-((tert-butoxycarbonylamino)methyl)phenyl)-3-(trifluoromethyl)-1H-pyrazole-5-carboxylic acid (10d) (321 mg, 0.833 mmol) and (S)—N-((+)-1-(3-amino-4-fluorophenyl)-1-(3-cyanophenyl)-3-cyclopropylpropyl)-2-methylpropane-2-sulfinamide (215b) (313 mg, 0.757 mmol) using the procedure as reported in step-3 of scheme 208 to afford tert-butyl 3-(5-(5-((+)-1-(3-cyanophenyl)-3-cyclopropyl-1-((S)-1,1-dimethylethylsulfinamido)propyl)-2-fluorophenylcarbamoyl)-3-(trifluoromethyl)-1H-pyrazol-1-yl)benzylcarbamate (215c) (358 mg, 458 mmol, 60.6% yield) as a white solid; $^1$H NMR (300 MHz, DMSO-$d_6$) δ 10.62 (s, 1H), 7.78 (bs, 1H), 7.72 (dt, J=7.4, 1.4 Hz, 1H), 7.63-7.32 (m, 9H), 7.24 (d, J=7.6 Hz, 2H), 5.58 (s, 1H), 4.19 (d, J=6.2 Hz, 2H), 2.75-2.40 (m, 2H), 1.38 (s, 9H), 1.20-1.00 (m, 1H), 1.12 (s, 9H), 0.97-0.79 (m, 1H), 0.70-0.55 (m, 1H), 0.42-0.24 (m, 2H), 0.01--0.17 (m, 2H); $^{19}$F NMR (282 MHz, DMSO-$d_6$) δ −61.11, −122.89; MS (ES+) 781.6 (M+1); 803.6 (M+Na), ES (−) 779.6 (M−1) Optical rotation: $[α]_D$=(+) 75.29 [0.255, MeOH].

Step-4: Preparation of (−)-N-(5-(1-amino-1-(3-cyanophenyl)-3-cyclopropylpropyl)-2-fluorophenyl)-1-(3-(aminomethyl)phenyl)-3-(trifluoromethyl)-1H-pyrazole-5-carboxamide (215d)

To a stirred solution of tert-butyl 3-(5-(5-((+)-1-(3-cyanophenyl)-3-cyclopropyl-1-((S)-1,1-dimethylethylsulfinamido)propyl)-2-fluorophenylcarbamoyl)-3-(trifluoromethyl)-1H-pyrazol-1-yl)benzylcarbamate (215c) (0.152 g, 0.195 mmol) in ethanol (15 mL) was added conc. HCl (0.16 mL, 1.917 mmol) and heated at reflux for 1 h. The reaction mixture was concentrated in vacuum to dryness and residue was triturated with t-butyl methyl ether (2×20 mL) and decanted. The solid was dried under vacuum, dissolved in water (5 mL) and concentrated in vacuum to dryness to afford (−)-N-(5-(1-amino-1-(3-cyanophenyl)-3-cyclopropylpropyl)-2-fluorophenyl)-1-(3-(aminomethyl)phenyl)-3-(trifluoromethyl)-1H-pyrazole-5-carboxamide (215d) (96 mg) hydrochloride salt as a white solid; $^1$H NMR (300 MHz, DMSO-$d_6$) δ 10.78 (s, 1H), 9.40 (s, 3H), 8.35 (s, 3H), 7.92-7.82 m, 2H), 7.74-7.23 (m, 10H), 4.13 (s, 2H), 2.60-2.40 (m, 2H), 1.20-0.95 (m, 2H), 0.75-0.60 (m, 1H), 0.42-0.32 (m, 2H), 0.05 to −0.05 (m, 2H); $^{19}$F NMR (282 MHz, DMSO-$d_6$) δ −60.64, −120.25; MS (ES+): 599.5 (M+Na); Optical rotation: $[α]_D$=(−) 7.84 [0.255, methanol]; Analysis calculated for $C_{31}H_{28}F_4N_6O\cdot 2HCl\cdot 2.5H_2O$: C, 53.61; H, 5.08; Cl, 10.21; N, 12.10; Found: C, 53.49; H, 4.92; Cl, 10.21; N, 11.77.

Scheme 216

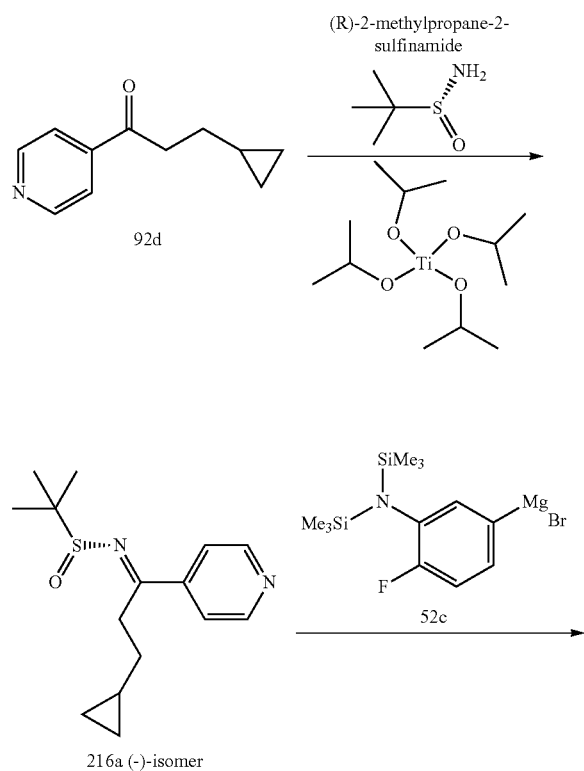

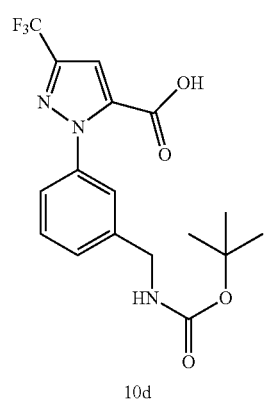

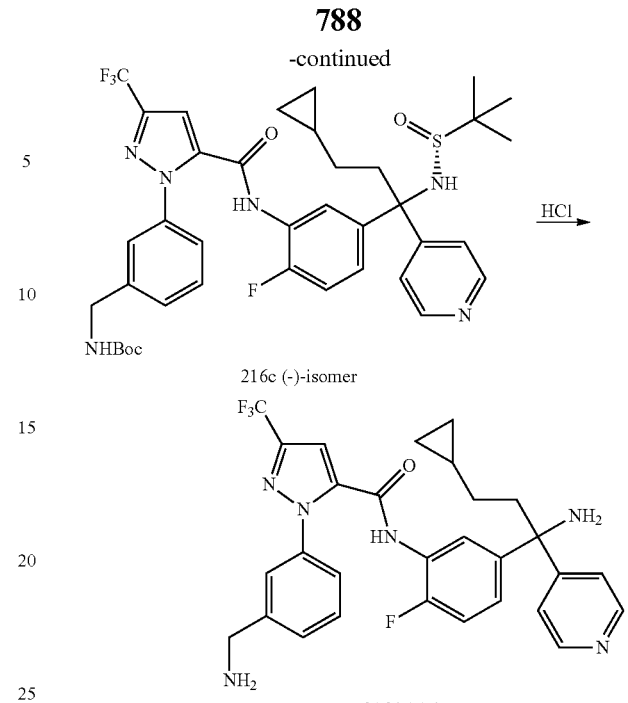

Preparation of (+)-N-(5-(1-amino-3-cyclopropyl-1-(pyridin-4-yl)propyl)-2-fluorophenyl)-1-(3-(aminomethyl)phenyl)-3-(trifluoromethyl)-1H-pyrazole-5-carboxamide (216d)

Step-1: Preparation of (−)-N-(3-cyclopropyl-1-(pyridin-4-yl)propylidene)-2-methylpropane-2-sulfinamide (216a)

Compound (216a) was prepared from 3-cyclopropyl-1-(pyridin-4-yl)propan-1-one (92d) (1.8 g, 10.27 mmol) and (R)-2-methylpropane-2-sulfinamide (1.566 g, 12.84 mmol) using procedure as reported in step-1 of scheme 208 to afford (−)-N-(3-cyclopropyl-1-(pyridin-4-yl)propylidene)-2-methylpropane-2-sulfinamide (216a) (1.838 g, 6.57 mmol, 63.9% yield) as a yellow syrup; $^1$H NMR (300 MHz, DMSO-$d_6$) δ 8.76-8.69 (m, 2H), 7.80-7.73 (m, 2H), 3.49-3.15 (m, 2H), 1.45 (q, J=7.4 Hz, 2H), 1.24 (s, 9H), 0.84-0.65 (m, 1H), 0.43-0.30 (m, 2H), 0.10-−0.03 (m, 2H); MS (ES+) 301.3, (M+Na); (ES−) 277.3 (M−1); Optical Rotation $[α]_D$= (−) 27.61 [0.355, MeOH].

Step-2: Preparation of (R)—N-((−)-1-(3-amino-4-fluorophenyl)-3-cyclopropyl-1-(pyridin-4-yl)propyl)-2-methylpropane-2-sulfinamide (216b)

Compound (216b) was prepared from (−)-N-(3-cyclopropyl-1-(pyridin-4-yl)propylidene)-2-methylpropane-2-sulfinamide (216a) (1.7 g, 6.11 mmol), using procedure as reported in step-2 of scheme 208 to afford (R)—N-((−)-1-(3-amino-4-fluorophenyl)-3-cyclopropyl-1-(pyridin-4-yl)propyl)-2-methylpropane-2-sulfinamide (216b) (1.443 g, 3.7 mmol, 60.7% yield) as a white solid; $^1$H NMR (300 MHz, DMSO-$d_6$) δ 8.77-8.68 (m, 2H), 7.62-7.53 (m, 2H), 7.15 (dd, J=11.3, 8.5 Hz, 1H), 7.00-6.94 (m, 1H), 6.77-6.70 (m, 1H), 5.50 (s, 1H), 5.35 (s, 2H), 2.90-2.60 (m, 2H), 1.47-1.27 (m, 1H), 1.38 (s, 9H), 1.25-1.05 (m, 1H), 0.97-0.80 (m, 1H), 0.65-0.55 (m, 2H), 0.32-0.10 (m, 2H); $^{19}$F NMR (282 MHz, DMSO-$d_6$) −137.30; MS (ES+): 390.4 (M+1); Chiral purity

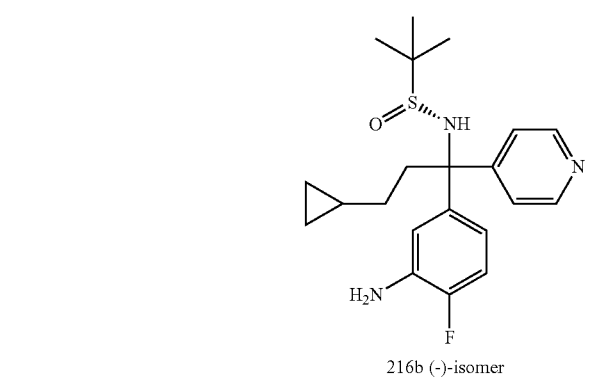

checked by performing chiral HPLC using chiral AD-H column, 1 mL/min, Solvent: 90% Hexane, 10% EtOH, 0.1% TEA, UV=260 nM, 25° C. (>99.99 ee); Optical Rotation [α]$_D$=(−) 78.49 [0.265, MeOH].

Step-3: Preparation of tert-butyl 3-(5-(5-((−)-3-cyclopropyl-1-((R)-1,1-dimethylethylsulfinamido)-1-(pyridin-4-yl)propyl)-2-fluorophenylcarbamoyl)-3-(trifluoromethyl)-1H-pyrazol-1-yl)benzylcarbamate (216c)

Compound (216c) was prepared using 1-(3-((tert-butoxycarbonylamino)methyl)phenyl)-3-(trifluoromethyl)-1H-pyrazole-5-carboxylic acid (10d) (0.866 g, 2.246 mmol) and (R)—N-((−)-1-(3-amino-4-fluorophenyl)-3-cyclopropyl-1-(pyridin-4-yl)propyl)-2-methylpropane-2-sulfinamide (216b) (700 mg, 1.797 mmol) using procedure as reported in step-3 of scheme 208 to afford tert-butyl 3-(5-(5-((−)-3-cyclopropyl-1-((R)-1,1-dimethylethylsulfinamido)-1-(pyridin-4-yl)propyl)-2-fluorophenylcarbamoyl)-3-(trifluoromethyl)-1H-pyrazol-1-yl)benzylcarbamate (216c) (688 mg, 0.909 mmol, 50.6% yield) as a white solid; $^1$H NMR (300 MHz, DMSO-d$_6$) δ 10.60 (s, 1H), 8.53-8.44 (m, 2H), 7.64-7.19 (m, 11H), 5.57 (s, 1H), 4.19 (d, J=6.2 Hz, 2H), 2.70-2.40 (m, 2H), 1.38 (s, 9H), 1.13 (s, 9H), 1.05-0.80 (m, 1H), 0.70-0.50 (m, 1H), 0.39-0.29 (m, 2H), −0.01-−0.23 (m, 2H); $^{19}$F NMR (282 MHz, DMSO-d$_6$) δ −60.61, −122.74; MS (ES+) 757.6 (M+1); 779.6 (M+Na), (ES−) 755.6 (M−1); Optical Rotation [α]$_D$ (−) 46.92 [0.26, MeOH].

Step-4: Preparation of (+)-N-(5-(1-amino-3-cyclopropyl-1-(pyridin-4-yl)propyl)-2-fluorophenyl)-1-(3-(aminomethyl)phenyl)-3-(trifluoromethyl)-1H-pyrazole-5-carboxamide (216d)

To a stirred solution of tert-butyl 3-(5-(5-((−)-3-cyclopropyl-1-((R)-1,1-dimethylethylsulfinamido)-1-(pyridin-4-yl)propyl)-2-fluorophenylcarbamoyl)-3-(trifluoromethyl)-1H-pyrazol-1-yl)benzylcarbamate (216c) (627 mg, 0.828 mmol) in ethanol (30 mL) was added conc. HCl (0.69 mL, 8.28 mmol) and heated at reflux for 1 h. The reaction mixture was concentrated in vacuum to dryness and residue was dissolved in ethanol (5 mL) triturated with t-butyl methyl ether (2×20 mL) and decanted. The solid was dried under vacuum, dissolved in water (20 mL) and concentrated in vacuum to dryness to afford (+)-N-(5-(1-amino-3-cyclopropyl-1-(pyridin-4-yl)propyl)-2-fluorophenyl)-1-(3-(aminomethyl)phenyl)-3-(trifluoromethyl)-1H-pyrazole-5-carboxamide (216d) (406 mg, 0.56 mmol, 67.6% yield) hydrochloride salt as an off white solid; $^1$H NMR (300 MHz, DMSO-d$_6$) δ 10.88 (s, 1H), 9.74 (s, 3H), 8.91-8.76 (m, 2H), 8.49 (d, J=7.1 Hz, 3H), 7.75-7.60 (m, 6H), 7.56 (d, J=7.9 Hz, 1H), 7.53-7.44 (m, 1H), 7.40 (dd, J=6.8, 2.3 Hz, 2H), 4.16-4.07 (m, 2H), 2.60-2.54 (m, 2H), 1.33-1.15 (m, 1H), 1.14-0.96 (m, 1H), 0.78-0.52 (m, 1H), 0.45-0.30 (m, 2H), 0.09-−0.05 (m, 2H); $^{19}$F NMR (282 MHz, DMSO-d$_6$) δ −60.63, −119.70; MS (ES+) 554.5 (M+1), 576.5 (M+Na), (ES−) 587.5 (M+Cl); Analysis calculated for $C_{29}H_{28}F_4N_6O.3HCl.3.5H_2O$; C: 48.04, H: 5.28; N: 11.59; Found: C: 48.06; H: 5.39; N: 11.66; Optical Rotation [α]$_D$=(+) 12.43 [0.575, MeOH].

Scheme 217

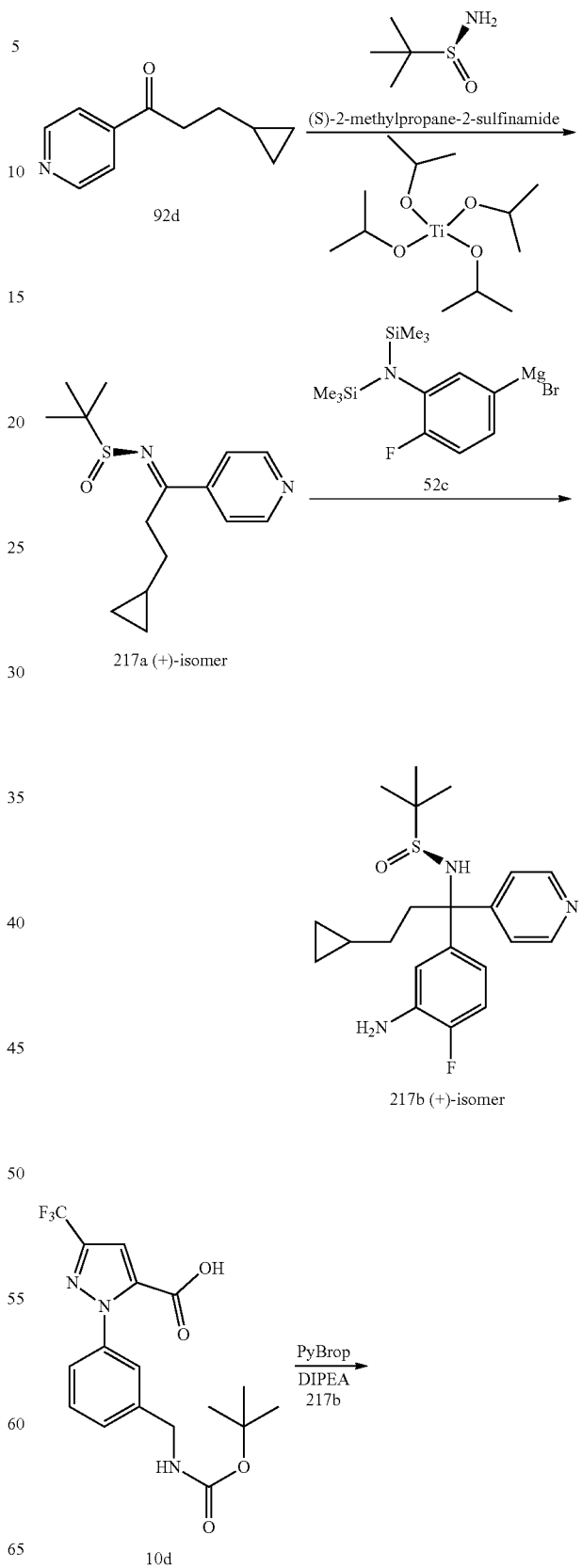

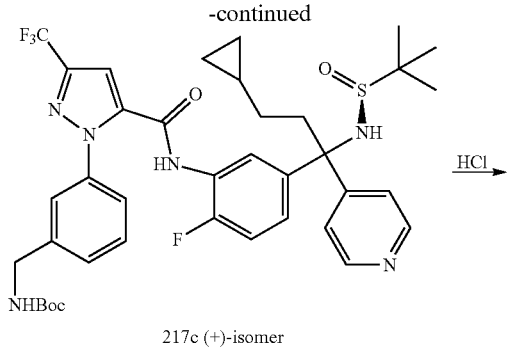

217c (+)-isomer

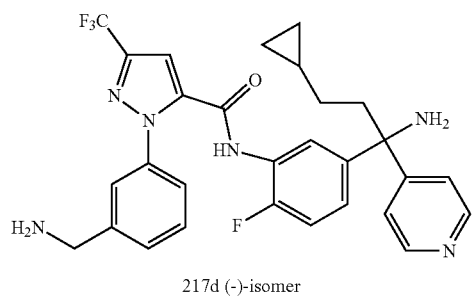

217d (-)-isomer

Preparation of (−)-N-(5-(1-amino-3-cyclopropyl-1-(pyridin-4-yl)propyl)-2-fluorophenyl)-1-(3-(aminomethyl)phenyl)-3-(trifluoromethyl)-1H-pyrazole-5-carboxamide (217d)

Step-1: Preparation of (+)-N-(3-cyclopropyl-1-(pyridin-4-yl)propylidene)-2-methylpropane-2-sulfinamide (217a)

Compound (217a) was prepared from 3-cyclopropyl-1-(pyridin-4-yl)propan-1-one (92d) (1.0 g, 5.71 mmol) and (S)-2-methylpropane-2-sulfinamide (0.838 g, 6.85 mmol) using procedure as reported in step-1 of scheme 208 to afford (+)-N-(3-cyclopropyl-1-(pyridin-4-yl)propylidene)-2-methylpropane-2-sulfinamide (217a) (0.973 g, 3.49 mmol, 61.2% yield) as a yellow syrup; $^1$HNMR (300 MHz, DMSO-d$_6$) δ 9.08-9.01 (m, 2H), 8.08 (m, 2H), 3.78-3.51 (m, 2H), 1.77 (m, 2H), 1.57 (s, 9H), 1.06 (m, 1H), 0.7-0.65 (m, 2H), 0.43-0.23 (m, 2H); MS (ES+) 279.3 (M+1); 301.3, (M+Na); (ES−) 277.4 (M−1); Optical Rotation [α]$_D$=(+) 33.96 [0.265, MeOH].

Step-2: Preparation of (S)—N-((+)-1-(3-amino-4-fluorophenyl)-3-cyclopropyl-1-(pyridin-4-yl)propyl)-2-methylpropane-2-sulfinamide (217b)

Compound (217b) was prepared from (+)-N-(3-cyclopropyl-1-(pyridin-4-yl)propylidene)-2-methylpropane-2-sulfinamide (217a) (0.928 g, 3.33 mmol), using procedure as reported in step-2 of scheme 208 to afford (S)—N-((+)-1-(3-amino-4-fluorophenyl)-3-cyclopropyl-1-(pyridin-4-yl)propyl)-2-methylpropane-2-sulfinamide (217b) (0.766 g, 1.966 mmol, 59% yield) as a white solid; $^1$H NMR (300 MHz, DMSO-d$_6$) δ 8.55-8.42 (m, 2H), 7.39-7.25 (m, 2H), 6.89 (dd, J=11.3, 8.5 Hz, 1H), 6.72 (dd, J=8.8, 2.4 Hz, 1H), 6.48 (ddd, J=8.5, 4.4, 2.4 Hz, 1H), 5.26 (s, 1H), 5.10 (s, 2H), 2.66-2.54 (m, 1H), 2.49-2.36 (m, 1H), 1.13 (s, 9H), 1.12 (m, 1H), 0.92 (m Hz, 1H), 0.71-0.56 (m, 1H), 0.42-0.27 (m, 2H), −0.02--0.14 (m, 2H); $^{19}$F NMR (282 MHz, DMSO-d$_6$) δ −137.32; MS (ES+) 390.4 (M+1); (ES−) 388.5 (M−1); Chiral purity checked by performing chiral HPLC using chiral AD-H column, 1 mL/min, Solvent: 90% Hexane, 10% EtOH, 0.1% TEA, UV=260 nM, 25° C. (99.355% ee); Optical Rotation [α]$_D$=(+) 82.4 [0.25, MeOH].

Step-3: Preparation of tert-butyl 3-(5-(5-((+)-3-cyclopropyl-1-((S)-1,1-dimethylethylsulfinamido)-1-(pyridin-4-yl)propyl)-2-fluorophenylcarbamoyl)-3-(trifluoromethyl)-1H-pyrazol-1-yl)benzylcarbamate (217c)

Compound (217c) was prepared using 1-(3-((tert-butoxycarbonylamino)methyl)phenyl)-3-(trifluoromethyl)-1H-pyrazole-5-carboxylic acid (10d) (0.61 g, 1.582 mmol) and (S)—N-((+)-1-(3-amino-4-fluorophenyl)-3-cyclopropyl-1-(pyridin-4-yl)propyl)-2-methylpropane-2-sulfinamide (217b) (493 mg, 1.266 mmol) using procedure as reported in step-3 of scheme 208 to afford tert-butyl 3-(5-(5-((+)-3-cyclopropyl-1-((S)-1,1-dimethylethylsulfinamido)-1-(pyridin-4-yl)propyl)-2-fluorophenylcarbamoyl)-3-(trifluoromethyl)-1H-pyrazol-1-yl)benzylcarbamate (217c) (637 mg, 0.841 mmol, 66.48% yield) as a white semisolid; $^1$H NMR (300 MHz, DMSO-d$_6$) δ 10.61 (s, 1H), 8.54-8.44 (m, 2H), 7.63-7.16 (m, 11H), 5.58 (s, 1H), 4.19 (d, J=6.3 Hz, 2H), 2.70-2.40 (m, 2H), 1.38 (s, 9H), 1.30-0.80 (m, 2H), 1.13 (s, 9H), 0.70-0.55 (m, 1H), 0.40-0.27 (m, 2H), −0.01--0.20 (m, 2H); $^{19}$F NMR (282 MHz, DMSO-d$_6$) δ −60.75, −122.85; MS (ES+) 757.6 (M+1); 779.6 (M+Na), (ES−) 755.5 (M−1); Optical Rotation [α]$_D$ (+) 50.37 [0.27, MeOH].

Step-4: Preparation of (−)-N-(5-(1-amino-3-cyclopropyl-1-(pyridin-4-yl)propyl)-2-fluorophenyl)-1-(3-(aminomethyl)phenyl)-3-(trifluoromethyl)-1H-pyrazole-5-carboxamide (217d)

To a stirred solution of tert-butyl 3-(5-(5-((+)-3-cyclopropyl-1-((R)-1,1-dimethylethylsulfinamido)-1-(pyridin-4-yl)propyl)-2-fluorophenylcarbamoyl)-3-(trifluoromethyl)-1H-pyrazol-1-yl)benzylcarbamate (217c) (119 mg, 0.157 mmol) in ethanol (10 mL) was added conc. HCl (0.13 mL, 1.557 mmol) and heated at reflux for 1 h. The reaction mixture was concentrated in vacuum to dryness and residue was dissolved in ethanol (5 mL) triturated with t-butyl methyl ether (30 mL) and decanted. The solid was dried under vacuum, dissolved in water (10 mL) and concentrated in vacuum to dryness to afford (−)-N-(5-(1-amino-3-cyclopropyl-1-(pyridin-4-yl)propyl)-2-fluorophenyl)-1-(3-(aminomethyl)phenyl)-3-(trifluoromethyl)-1H-pyrazole-5-carboxamide (217d) (78 mg, 0.141 mmol, 90% yield) hydrochloride as a white solid; $^1$H NMR (300 MHz, DMSO-d$_6$) δ 10.84 (s, 1H), 9.63 (s, 3H), 8.84-8.73 (m, 2H), 8.44 (s, 3H), 7.75-7.68 (m, 2H), 7.66-7.31 (m, 8H), 4.12 (q, J=6.0 Hz, 2H), 2.60-2.40 (m, 2H), 1.35-0.93 (m, 2H), 0.79-0.56 (m, 1H), 0.45-0.28 (m, 2H), 0.06 to −0.06 (m, 2H); $^{19}$F NMR (282 MHz, DMSO-d$_6$) δ −60.63, −119.88; MS (ES+): 575.5 (M+Na); Optical Rotation [α]$_D$=(−) 10.32 [0.32, MeOH]; Analysis calculated for $C_{29}H_{28}F_4N_6O.3HCl.3.25H_2O$; C, 48.34; H, 5.25; N, 11.66: Found: C, 48.20; H, 5.31; N, 11.59.

Scheme 218

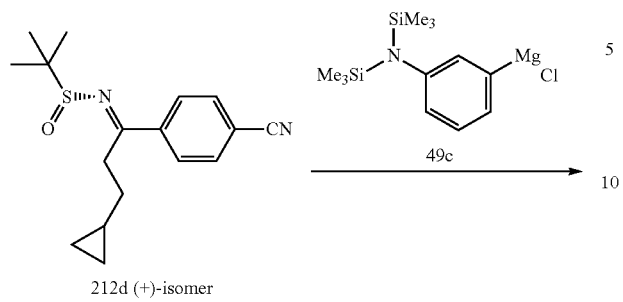

212d (+)-isomer

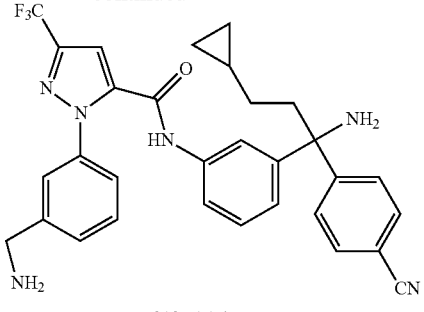

218c (+)-isomer

Preparation of (+)-N-(3-(1-amino-1-(4-cyanophenyl)-3-cyclopropylpropyl)phenyl)-1-(3-(aminomethyl)phenyl)-3-(trifluoromethyl)-1H-pyrazole-5-carboxamide (218c)

Step: 1 Preparation of (R)—N-((−)-1-(3-aminophenyl)-1-(4-cyanophenyl)-3-cyclopropylpropyl)-2-methylpropane-2-sulfinamide (218a)

Compound (218a) was prepared from (+)-N-(1-(4-cyanophenyl)-3-cyclopropylpropylidene)-2-methylpropane-2-sulfinamide (212d) (2 g, 6.64 mmol), using procedure as reported in step-2 of scheme 208 to afford (R)—N-((−)-1-(3-aminophenyl)-1-(4-cyanophenyl)-3-cyclopropylpropyl)-2-methylpropane-2-sulfinamide (218a) (1.65 g, 4.17 mmol, 63.1% yield) as a white solid; $^1$H NMR (300 MHz, DMSO-$d_6$) δ 7.80-7.71 (m, 2H), 7.58-7.50 (m, 2H), 6.93 (t, J=7.8 Hz, 1H), 6.50 (t, J=1.9 Hz, 1H), 6.48-6.43 (m, 1H), 6.41-6.35 (m, 1H), 5.15 (s, 1H), 5.05 (s, 2H), 2.70-2.35 (m, 2H), 1.13 (s, 9H), 1.21-1.05 (m, 1H), 1.00-0.8 (m, 1H), 0.72-0.55 (s, 1H), 0.45-0.21 (m, 2H), 0.07--0.22 (m, 2H); MS (ES+) 396.4 (M+1) 418.4 (M+Na); (ES−) 394.3 (M−1); Optical rotation: [α]$_D$=(−) 103.57 [0.28, MeOH].

Step-2: Preparation of tert-butyl 3-(5-(3-((−)-1-(4-cyanophenyl)-3-cyclopropyl-1-((R)-1,1-dimethylethylsulfinamido)propyl)phenylcarbamoyl)-3-(trifluoromethyl)-1H-pyrazol-1-yl)benzylcarbamate (218b)

Compound (218b) was prepared from 1-(3-((tert-butoxycarbonylamino)methyl)phenyl)-3-(trifluoromethyl)-1H-pyrazole-5-carboxylic acid (10d) (1.607 g, 4.17 mmol) and (R)—N-((−)-1-(3-aminophenyl)-1-(4-cyanophenyl)-3-cyclopropylpropyl)-2-methylpropane-2-sulfinamide (218a) (1.5 g, 3.79 mmol) using the procedure as reported in step-3 of scheme 208 to afford tert-butyl 3-(5-(3-((−)-1-(4-cyanophenyl)-3-cyclopropyl-1-((R)-1,1-dimethylethylsulfinamido)propyl) phenylcarbamoyl)-3-(trifluoromethyl)-1H-pyrazol-1-yl)benzylcarbamate (218b) (1.96 g, 2.57 mmol, 67.8% yield) as a colorless solid; $^1$H NMR (300 MHz, DMSO-$d_6$) δ 10.72 (s, 1H), 7.78 (d, J=8.4 Hz, 2H), 7.62 (d, J=8.1 Hz, 1H), 7.58-7.32 (m, 9H), 7.28 (t, J=8.0 Hz, 1H), 7.12 (d, J=7.9 Hz, 1H), 5.39 (s, 1H), 4.19 (d, J=6.2 Hz, 2H), 2.75-2.40 (m, 2H), 1.37 (s, 9H), 1.13 (s, 9H), 1.20-1.00 (m, 1H), 0.97-0.77 (m, 1H), 0.70-0.55 (m, 1H), 0.40-0.27 (m, 2H), −0.01--0.18 (m, 2H); MS (ES+) 763.5 (M+1), 785.6 (M+Na); (ES−) 761.5 (M−1); Optical rotation: [α]$_D$=(−) 65.96 [0.285, MeOH].

Step-3: Preparation of (+)-N-(3-(1-amino-1-(4-cyanophenyl)-3-cyclopropylpropyl)phenyl)-1-(3-(aminomethyl)phenyl)-3-(trifluoromethyl)-1H-pyrazole-5-carboxamide (218c)

To a stirred solution of tert-butyl 3-(5-(3-(((−)-1-(4-cyanophenyl)-3-cyclopropyl-1-((R)-1,1-dimethylethylsulfinamido)propyl) phenylcarbamoyl)-3-(trifluoromethyl)-1H-pyrazol-1-yl)benzylcarbamate (218b) (1.014 g, 1.329 mmol) in ethanol (15 mL) was added conc. HCl (1.10 mL, 13.2 mmol) and heated at reflux for 1 h. The reaction mixture was concentrated in vacuum to dryness and the residue obtained was purified twice by flash column chromatography (silica gel 40 g, first column eluting with 0-50% CMA-80 in chloroform, second column eluting with methanol in chloroform 0-30%) to obtain compound 218c (479 mgs, 0.699 mmol, 52.6% yield) free base as a white solid. The free base was dissolved in ethanol (5 mL) added conc. HCl (0.18 mL) and concentrated in vacuum to dryness to afford a white residue, which was dissolved in water (5 mL) and concentrated in vacuum to dryness to afford (+)-N-(3-(1-amino-1-(4-cyanophenyl)-3-cyclopropylpropyl)phenyl)-1-(3-(aminomethyl)phenyl)-3-(trifluoromethyl)-1H-pyrazole-5-carboxamide (218c) (276 mg, 0.417 mmol, 31.39% yield) hydrochloride salt as a white solid; $^1$H NMR (300 MHz, DMSO-$d_6$) δ 10.93 (s, 1H), 9.39 (s, 3H), 8.42 (s, 3H), 7.94 (d, J=8.4 Hz, 2H), 7.78-7.47 (m, 9H), 7.43 (t, J=8.0 Hz, 1H), 7.21 (d, J=8.0 Hz, 1H), 4.18-4.08 (m, 2H), 2.60-2.40 (m, 2H), 1.23-1.01 (m, 2H), 0.68 (s, 1H), 0.37 (dd, J=8.0, 4.1 Hz, 2H), 0.11-0.14 (m, 2H); $^{19}$F NMR (282 MHz, DMSO-$d_6$) δ −60.59; MS (ES+): 559.5 (M+1); IR (KBr) 2233 cm$^{−1}$; Optical rotation: [α]$_D$=(+) 16.72 [0.335, MeOH]; Analysis calculated for $C_{31}H_{29}F_3N_6O·2HCl·3H_2O$: C: 54.31; H: 5.44; N: 12.26; Found C: 54.20; H: 5.44; N: 12.11.

Scheme 219

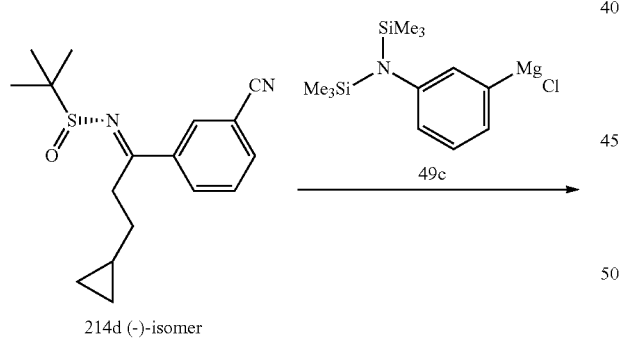

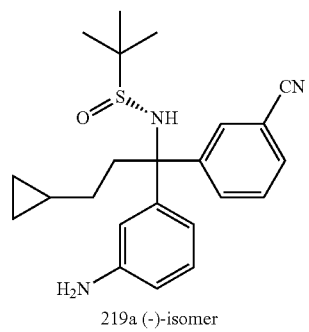

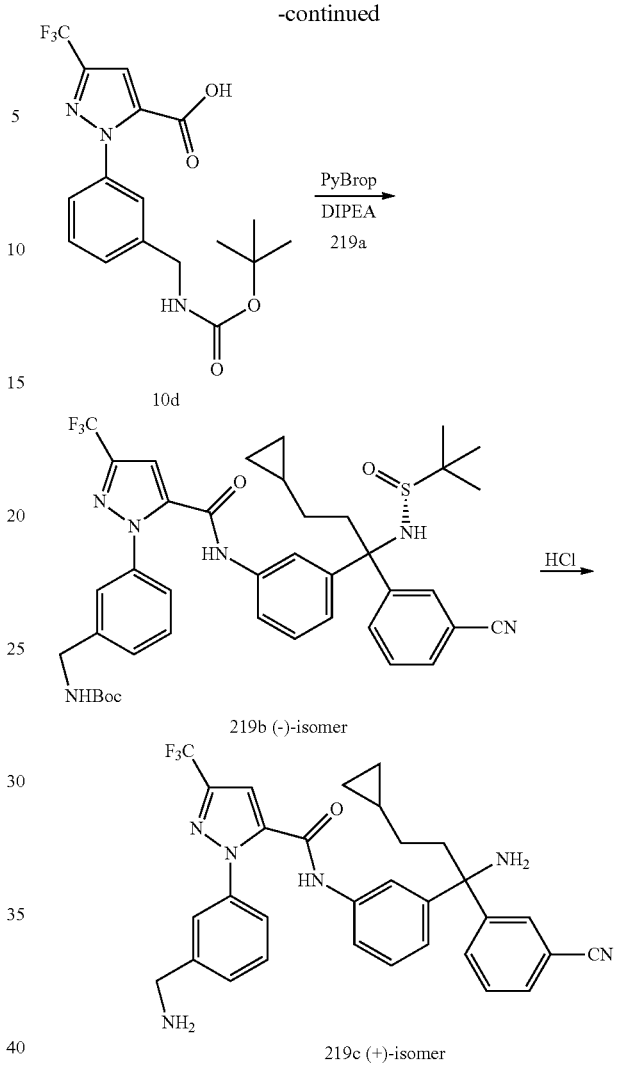

Preparation of (+)-N-(3-(1-amino-1-(3-cyanophenyl)-3-cyclopropylpropyl)phenyl)-1-(3-(aminomethyl)phenyl)-3-(trifluoromethyl)-1H-pyrazole-5-carboxamide (219c)

Step: 1 Preparation of (R)—N-((−)-1-(3-aminophenyl)-1-(4-cyanophenyl)-3-cyclopropylpropyl)-2-methylpropane-2-sulfinamide (219a)

Compound (219a) was prepared from (−)-N-(1-(3-cyanophenyl)-3-cyclopropylpropylidene)-2-methylpropane-2-sulfinamide (214d) (2 g, 6.64 mmol), using procedure as reported in step-2 of scheme 208 to afford (R)—N-((−)-1-(3-aminophenyl)-1-(3-cyanophenyl)-3-cyclopropylpropyl)-2-methylpropane-2-sulfinamide (219a) (1.939 g, 4.9 mmol, 74.1% yield) as a white solid; $^1$H NMR (300 MHz, DMSO-$d_6$) δ 7.78 (t, J=1.6 Hz, 1H), 7.72-7.61 (m, 2H), 7.50 (t, J=7.8 Hz, 1H), 6.94 (t, J=7.8 Hz, 1H), 6.52 (t, J=2.0 Hz, 1H), 6.46 (dt, J=7.9, 1.2 Hz, 1H), 6.39 (ddd, J=8.0, 2.2, 0.9 Hz, 1H), 5.16 (s, 1H), 5.05 (s, 2H), 2.73-2.36 (m, 2H), 1.13 (s, 9H), 1.25-1.05 (m, 1H), 0.99-0.79 (m, 1H), 0.73-0.56 (m, 1H), 0.45-0.24 (m, 2H), 0.05-−0.19 (m, 2H); MS (ES+) 396.4 (M+1) 418.4 (M+Na); (ES−) 394.6 (M−1) 430.4 (M+Cl); Optical rotation: [α]$_D$=(−) 117.6 [0.25, MeOH].

Step-2: Preparation of tert-butyl 3-(5-(3-((−)-1-(3-cyanophenyl)-3-cyclopropyl-1-((R)-1,1-dimethylethylsulfinamido)propyl)phenylcarbamoyl)-3-(trifluoromethyl)-1H-pyrazol-1-yl)benzylcarbamate (219b)

Compound (219b) was prepared from 1-(3-((tert-butoxycarbonylamino)methyl)phenyl)-3-(trifluoromethyl)-1H-pyrazole-5-carboxylic acid (10d) (1.286 g, 3.34 mmol) and (R)—N-((−)-1-(3-aminophenyl)-1-(3-cyanophenyl)-3-cyclopropylpropyl)-2-methylpropane-2-sulfinamide (219a) (1.2 g, 3.03 mmol) using the procedure as reported in step-3 of scheme 208 to afford tert-butyl 3-(5-(3-((−)-1-(3-cyanophenyl)-3-cyclopropyl-1-((R)-1,1-dimethylethylsulfinamido)propyl)phenylcarbamoyl)-3-(trifluoromethyl)-1H-pyrazol-1-yl)benzylcarbamate (219b) (1.081 g, 1.417 mmol, 46.7% yield) as a white solid; $^1$H NMR (300 MHz, DMSO-$d_6$) δ 10.72 (s, 1H), 7.79 (d, J=1.9 Hz, 1H), 7.71 (d, J=7.5 Hz, 1H), 7.66-7.32 (m, 10H), 7.28 (t, J=8.0 Hz, 1H), 7.11 (d, J=7.9 Hz, 1H), 5.39 (s, 1H), 4.19 (d, J=6.1 Hz, 2H), 2.73-2.36 (m, 2H), 1.37 (s, 9H), 1.13 (s, 9H), 1.12 (m, 1H), 1.00-0.80 (m, 1H), 0.70-0.55 (m, 1H), 0.40-0.31 (m, 2H), −0.00 (m, 2H); $^{19}$F NMR (282 MHz, DMSO-$d_6$) δ −60.58; MS (ES+) 785.6 (M+Na); (ES−) 761.5 (M−1); Optical rotation: $[α]_D$=(−) 73.68 [0.285, MeOH].

Step-3: Preparation of (+)-N-(3-(1-amino-1-(3-cyanophenyl)-3-cyclopropylpropyl)phenyl)-1-(3-(aminomethyl)phenyl)-3-(trifluoromethyl)-1H-pyrazole-5-carboxamide (219c)

To a stirred solution of tert-butyl 3-(5-(3-((−)-1-(3-cyanophenyl)-3-cyclopropyl-1-((R)-1,1-dimethylethylsulfinamido)propyl)phenylcarbamoyl)-3-(trifluoromethyl)-1H-pyrazol-1-yl)benzylcarbamate (219b) (0.7 g, 0.918 mmol) in ethanol (12 mL) was added conc. HCl (0.76 mL, 9.12 mmol) and heated at reflux for 1 h. The reaction mixture was concentrated in vacuum to dryness and the residue obtained was purified twice by flash column chromatography (silica gel 25 g, first column eluting with 0-30% CMA-80 in chloroform, second column eluting with methanol in chloroform 0-10%) to afford compound 219c (297 mgs, 0.532 mmol, 57.9% yield) free base as a white solid. The free base (126 mgs, 0.23 mmol) was dissolved in ethanol (5 mL) added conc. HCl (0.095 mL) and concentrated in vacuum to dryness to afford a white residue, which was dissolved in water (5 mL) and concentrated in vacuum to dryness to afford (+)-N-(3-(1-amino-1-(3-cyanophenyl)-3-cyclopropylpropyl)phenyl)-1-(3-(aminomethyl)phenyl)-3-(trifluoromethyl)-1H-pyrazole-5-carboxamide (219c) (130 mg, 0.192 mmol, 83.54% yield) hydrochloride salt as a white solid; $^1$H NMR (300 MHz, DMSO-$d_6$) δ 10.93 (s, 1H), 9.37 (s, 3H), 8.41 (s, 3H), 7.91-7.84 (m, 2H), 7.76-7.48 (m, 9H), 7.43 (t, J=8.0 Hz, 1H), 7.21 (d, J=7.9 Hz, 1H), 4.13 (bs, 2H), 2.6-0-2.40 (m, 2H), 1.19-0.99 (m, 2H), 0.77-0.60 (m, 1H), 0.46-0.30 (m, 2H), 0.14-0.12 (m, 2H); $^{19}$F NMR (282 MHz, DMSO-$d_6$) δ −60.60; MS (ES+): 559.5 (M+1); IR (KBr) 2235 cm$^{-1}$; Optical rotation: $[α]_D$=(+) 7.59 [CH$_3$OH, 0.29]; Analysis calculated for C$_{31}$H$_{29}$F$_3$N$_6$O.2HCl.2.5H$_2$O: C: 55.03; H: 5.36; N: 12.42; Found C: 55.07; H: 5.15; N: 12.30.

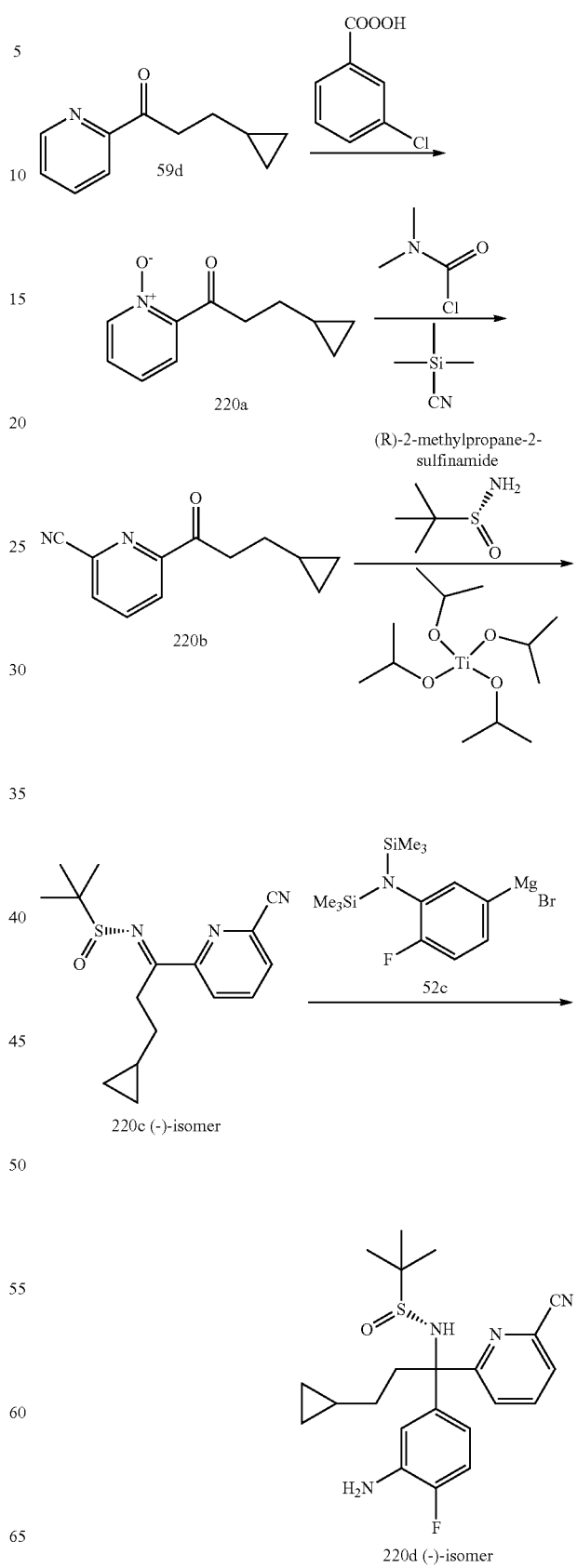

Scheme 220

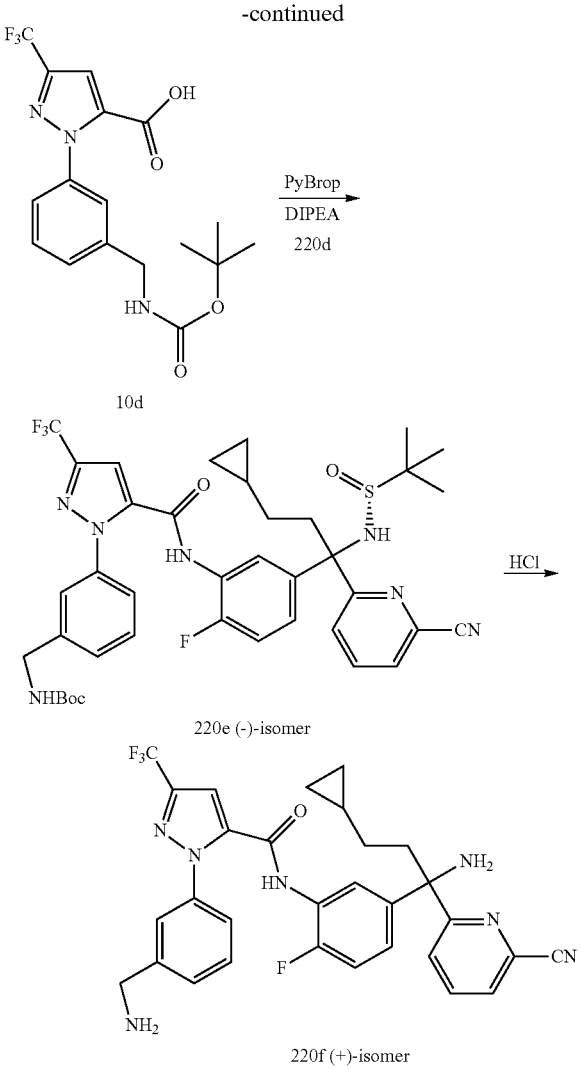

Preparation of (+)-N-(5-(1-amino-1-(6-cyanopyridin-2-yl)-3-cyclopropylpropyl)-2-fluorophenyl)-1-(3-(aminomethyl)phenyl)-3-(trifluoromethyl)-1H-pyrazole-5-carboxamide (220f)

Step-1: Preparation of 2-(3-cyclopropylpropanoyl)pyridine 1-oxide (220a)

To solution of 3-cyclopropyl-1-(pyridin-2-yl)propan-1-one (59d) (2.98 g, 17.01 mmol) in $CH_2Cl_2$ (120 mL) cooled to ~0° C. was added 3-chlorobenzoperoxoic acid (11.43 g, 51.0 mmol), stirred at ~0° C. for 3 h and allowed to warm to room temperature overnight. The reaction mixture was concentrated in vacuum and purified by flash column chromatography [silica gel, eluting with hexanes/10% methanol in ethyl acetate (1:0 to 1:1)] to afford 2-(3-cyclopropylpropanoyl)pyridine 1-oxide (220a) (1.115 g, 5.83 mmol, 34.3% yield) as a light brown oil; $^1$H NMR (300 MHz, DMSO-$d_6$) δ 8.30 (dt, J=6.4, 0.8 Hz, 1H), 7.62-7.51 (m, 2H), 7.42 (td, J=7.7, 1.1 Hz, 1H), 3.13-3.06 (m, 2H), 1.48 (q, J=7.2 Hz, 2H), 0.79-0.59 (m, 1H), 0.45-0.25 (m, 2H), 0.09--0.07 (m, 2H); MS (ES+) 214.2 (M+Na); (ES−) 190.2 (M−1).

Step-2: Preparation of 6-(3-cyclopropylpropanoyl)picolinonitrile (220b)

To a solution of 2-(3-cyclopropylpropanoyl)pyridine 1-oxide (220a) (1.026 g, 5.37 mmol) and trimethylsilanecarbonitrile (3.22 mL, 23.66 mmol) in $CH_2Cl_2$ (25 mL) cooled to 0 OC was added dimethylcarbamic chloride (2.110 mL, 22.06 mmol) and stirred at room temperature for 86 h. The reaction mixture was concentrated in vacuum and purified by flash column chromatography [silica gel, eluting with hexanes/ethyl acetate (1:0 to 1:1)] to afford 6-(3-cyclopropylpropanoyl)picolinonitrile (220b) (117 mg, 0.584 mmol, 10.89% yield) as a yellow oil; $^1$H NMR (300 MHz, DMSO-$d_6$) δ 8.34-8.19 (m, 3H), 3.25 (t, J=7.3 Hz, 2H), 1.54 (q, J=7.2 Hz, 2H), 0.87-0.60 (m, 1H), 0.50-0.30 (m, 2H), 0.11-0.01 (m, 2H); MS (ES+) 223.2 (M+Na), (ES−) 199.1 (M−1).

Step-3: Preparation of (−)-N-(1-(6-cyanopyridin-2-yl)-3-cyclopropylpropylidene)-2-methylpropane-2-sulfinamide (220c)

Compound (220c) was prepared from 6-(3-cyclopropylpropanoyl)picolinonitrile (220b) (1 g, 4.99 mmol) and (R)-2-methylpropane-2-sulfinamide (608 mg, 5.02 mmol) using procedure as reported in step-1 of scheme 208 to afford (−)-N-(1-(6-cyanopyridin-2-yl)-3-cyclopropylpropylidene)-2-methylpropane-2-sulfinamide (220c) (782 mg, 2.58 mmol, 51.6% 30 yield) as a yellow solid; $^1$H NMR (300 MHz, DMSO-$d_6$) δ 8.33-8.16 (m, 3H), 3.55-3.20 (m, 2H), 1.57-1.43 (m, 2H), 1.26 (s, 9H), 0.85-0.63 (m, 1H), 0.45-0.27 (m, 2H), 0.08--0.01 (m, 2H); MS (ES+) 304.3, (M+1), 326.3 (M+Na); (ES−) 338.2 (M+Cl); Optical Rotation $[α]_D$=(−) 79.35 [0.31, MeOH].

Step-4: Preparation of (R)—N-((−)-1-(3-amino-4-fluorophenyl)-1-(6-cyanopyridin-2-yl)-3-cyclopropylpropyl)-2-methylpropane-2-sulfinamide (220d)

Compound (220d) was prepared from (−)-N-(1-(6-cyanopyridin-2-yl)-3-cyclopropylpropylidene)-2-methylpropane-2-sulfinamide (220c) (0.695 g, 2.291 mmol), using procedure as reported in step-2 of scheme 208 to afford (R)—N-((−)-1-(3-amino-4-fluorophenyl)-1-(6-cyanopyridin-2-yl)-3-cyclopropylpropyl)-2-methylpropane-2-sulfinamide (220d) (0.345 g, 0.832 mmol, 36.3% yield) as a white solid; $^1$H NMR (300 MHz, DMSO-$d_6$) δ 8.01-7.88 (m, 2H), 7.61 (dd, J=7.1, 2.2 Hz, 1H), 6.90 (dd, J=11.3, 8.5 Hz, 1H), 6.66 (dd, J=8.8, 2.4 Hz, 1H), 6.49 (ddd, J=8.5, 4.2, 2.3 Hz, 1H), 5.56 (s, 1H), 5.12 (s, 2H), 2.75-2.30 (m, 2H), 1.26-0.87 (m, 2H), 1.14 (s, 9H), 0.72-0.56 (m, 1H), 0.42-0.30 (m, 2H), 0.06 to −0.14 (s, 2H); $^{19}$F NMR (282 MHz, DMSO-$d_6$) δ −137.02; MS (ES+): 437.4 (M+Na); (ES−) 413.4 (M−1), 449.4 (M+Cl); Optical Rotation $[α]_D$=(−) 7.80 [0.205, MeOH].

Step-5: Preparation of tert-butyl 3-(5-(5-((−)-1-(6-cyanopyridin-2-yl)-3-cyclopropyl-1-((R)-1,1-dimethylethylsulfinamido)propyl)-2-fluorophenylcarbamoyl)-3-(trifluoromethyl)-1H-pyrazol-1-yl) benzylcarbamate (220e)

Compound (220e) was prepared using 1-(3-((tert-butoxycarbonylamino)methyl)phenyl)-3-(trifluoromethyl)-1H-pyrazole-5-carboxylic acid (10d) (0.34 g, 0.882 mmol) and (R)—N-((−)-1-(3-amino-4-fluorophenyl)-1-(6-cyanopyridin-2-yl)-3-cyclopropylpropyl)-2-methylpropane-2-sulfinamide (220d) (323 mg, 0.779 mmol) using procedure as reported in step-3 of scheme 208 to afford tert-butyl 3-(5-(5-((−)-1-(6-cyanopyridin-2-yl)-3-cyclopropyl-1-((R)-1,1-dimethylethylsulfinamido)propyl)-2-fluorophenylcarbamoyl)-3-(trifluoromethyl)-1H-pyrazol-1-yl)benzylcarbamate (220e) (273 mg, 0.349 mmol, 44.8% yield) as a white solid; $^1$H NMR (300 MHz, DMSO-d$_6$) δ 10.59 (s, 1H), 8.05-7.91 (m, 2H), 7.67 (d, J=7.9 Hz, 1H), 7.61-7.16 (m, 9H), 5.80 (s, 1H), 4.19 (d, J=6.2 Hz, 2H), 2.80-2.54 (m, 2H), 1.38 (s, 9H), 1.13 (s, 9H), 1.10-0.85 (m, 2H), 0.75-0.55 (m, 1H), 0.40-0.30 (m, 2H), 0.05 to −0.15 (m, 2H); $^{19}$F NMR (282 MHz, DMSO-d$_6$) δ −60.62, −122.28; MS (ES+) 804.7 (M+Na); Optical Rotation [α]$_D$ (−) 7.46 [0.295, MeOH].

Step-6: Preparation of (+)-N-(5-(1-amino-1-(6-cyanopyridin-2-yl)-3-cyclopropylpropyl)-2-fluorophenyl)-1-(3-(aminomethyl)phenyl)-3-(trifluoromethyl)-1H-pyrazole-5-carboxamide (220f)

To a stirred solution of tert-butyl 3-(5-(5-((−)-1-(6-cyanopyridin-2-yl)-3-cyclopropyl-1-((R)-1,1-dimethylethylsulfinamido)propyl)-2-fluorophenylcarbamoyl)-3-(trifluoromethyl)-1H-pyrazol-1-yl)benzylcarbamate (220e) (144 mg, 0.184 mmol) in ethanol (15 mL) was added conc. HCl (0.15 mL, 1.808 mmol) and heated at reflux for 1 h. The reaction mixture was concentrated in vacuum to dryness and the residue obtained was purified twice by flash column chromatography (silica gel 25 g, first column eluting with 0-30% CMA-80 in chloroform, second column eluting with methanol in chloroform 0-10%) to afford compound 220f (41 mg, 0.071 mmol, 38.5% yield) free base as a white solid. The free base (41 mg, 0.071 mmol) was dissolved in ethanol (10 mL) added conc. HCl (0.03 mL) and concentrated in vacuum to dryness to afford a white residue, which was dissolved in water (2 mL) and concentrated in vacuum to dryness to afford (+)-N-(5-(1-amino-1-(6-cyanopyridin-2-yl)-3-cyclopropylpropyl)-2-fluorophenyl)-1-(3-(aminomethyl)phenyl)-3-(trifluoromethyl)-1H-pyrazole-5-carboxamide (220f) (50 mg, 0.071 mmol, 38.57% yield) hydrochloride salt as a white solid; $^1$H NMR (300 MHz, DMSO-d$_6$) δ 10.78 (s, 1H), 9.12 (s, 3H), 8.32 (s, 3H), 8.14 (s, 1H), 7.89-7.16 (m, 10H), 4.13 (s, 2H), 1.32-1.10 (m, 1H), 1.00-0.75 (m, 1H), 0.75-0.57 (m, 1H), 0.42-0.32 (m, 2H), 0.08 to −0.08 (s, 2H); $^{19}$F NMR (282 MHz, DMSO-d$_6$) δ −60.64, −119.69; MS (ES+): 600.5 (M+Na); Optical Rotation [α]$_D$=(+) 57.39 [0.23, MeOH]; Analysis calculated for C$_{30}$H$_{27}$F$_4$N$_7$O.2HCl.3H$_2$O: C: 51.14; H: 5.01; N: 13.92; Cl: 10.06; Found: C: 51.40; H: 4.90; N: 13.58; Cl: 10.00.

Scheme 221

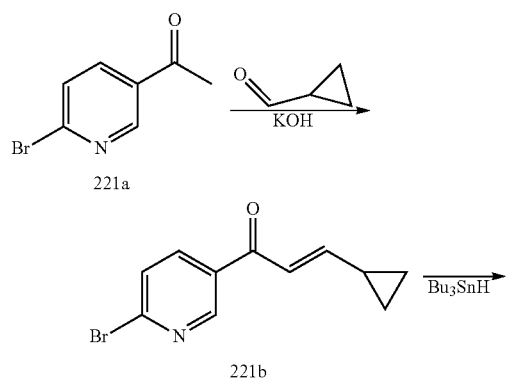

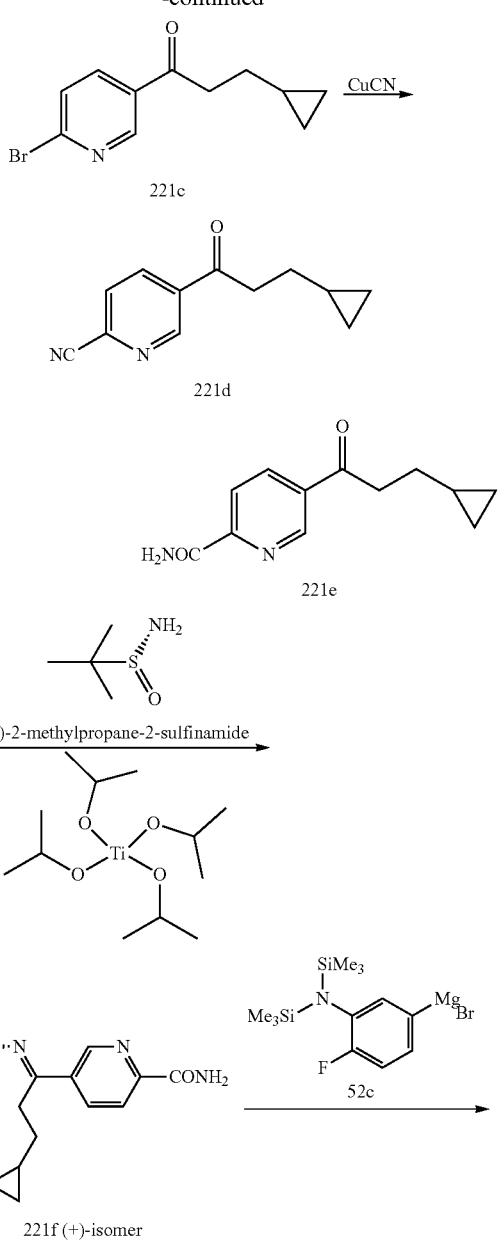

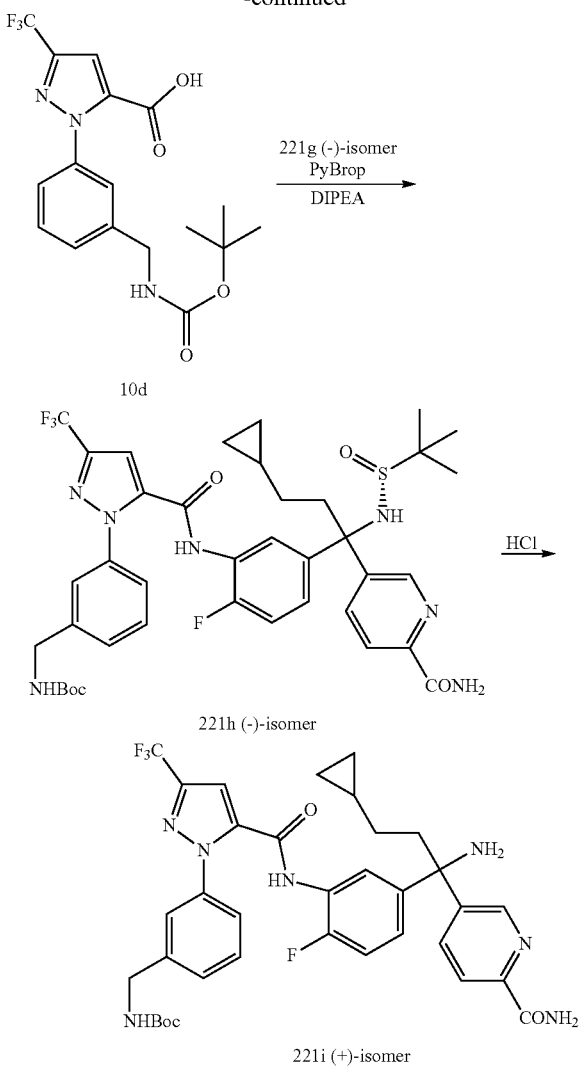

221g (−)-isomer
PyBrop
DIPEA

10d 221h (−)-isomer 221i (+)-isomer

Preparation of (+)-5-(1-amino-1-(3-(1-(3-(aminomethyl)phenyl)-3-(trifluoromethyl)-1H-pyrazole-5-carboxamido)-4-fluorophenyl)-3-cyclopropylpropyl)picolinamide (221i)

Step: 1 Preparation of 1-(6-bromopyridin-3-yl)-3-cyclopropylprop-2-en-1-one (221b)

To a stirred solution of 1-(6-bromopyridin-3-yl)ethanone (221a) (35 g, 171 mmol) in methanol (400 mL) at 0° C. was added cyclopropanecarboxaldehyde (21 mL, 281 mmol) followed by potassium hydroxide (1 M aqueous solution, 35 mL, 35 mmol). The reaction mixture allowed to attain room temperature and stirred for 13 h. The reaction was acidified with 1 N HCl (40 mL) to pH-6 and concentrated in vacuum maintaining bath temperature below 35° C. The residue was dissolved in ethyl acetate (700 mL) washed with water (300 mL), dried, filtered and concentrated in vacuum to furnish crude 1-(6-bromopyridin-3-yl)-3-cyclopropylprop-2-en-1-one (221b) (40.45 g) as a colorless liquid which was used as such for next step.

Step 2: Preparation of 1-(6-bromopyridin-3-yl)-3-cyclopropylpropan-1-one (221c)

To a stirred solution of crude 1-(6-bromopyridin-3-yl)-3-cyclopropylprop-2-en-1-one (221b) (40.45 g) from above step in acetonitrile (300 mL) was added tri-n-butyltin hydride (88 mL, 319 mmol) and heated at reflux for 13 h. The reaction mixture was cooled to room temperature and the layers separated. The lower layer was extracted with acetonitrile (150 mL) and both acetonitrile layers were combined and concentrated in vacuum. The residue obtained was purified by flash column chromatography (silica gel eluting with ethyl acetate in hexanes 0 to 100%) to afford 1-(6-bromopyridin-3-yl)-3-cyclopropylpropan-1-one (221c) (11.57 g, 45.5 mmol, 28.5% yield) as a white solid; $^1$H NMR (300 MHz, DMSO-$d_6$) δ 8.94 (dd, J=2.6, 0.8 Hz, 1H), 8.22 (dd, J=8.3, 2.5 Hz, 1H), 7.83 (dd, J=8.3, 0.8 Hz, 1H), 3.14 (t, J=7.2 Hz, 2H), 1.52 (q, J=7.1 Hz, 2H), 0.84-0.66 (m, 1H), 0.44-0.25 (m, 2H), 0.15--0.17 (m, 2H); MS (ES−) 252.2 (M−1).

Step-3: Preparation of 5-(3-cyclopropylpropanoyl)picolinonitrile (221d) and 5-(3-cyclopropylpropanoyl)picolinamide (221e)

A mixture of 1-(6-bromopyridin-3-yl)-3-cyclopropylpropan-1-one (221c) (11.23 g, 44.2 mmol) and cyanocopper (7.92 g, 88 mmol) in DMF (150 mL) was stirred at 110° C. for 45 h. The reaction mixture was cooled to room temperature, diluted with water (200 mL) and ethyl acetate (500 mL). The mixture was filtered and aqueous layer was separated, extracted with ethyl acetate. The organic layers were combined washed with saturated aqueous NaHCO$_3$ (150 mL), brine (150 mL), dried, filtered and concentrated in vacuum. The residue obtained was purified by flash column chromatography [silica gel eluting with ethyl acetate in hexanes (1:0 to 4:1 to 1:1)] to furnish:

1. 5-(3-cyclopropylpropanoyl)picolinonitrile (221d) (3.642 g, 18.19 mmol, 41.2%) as a yellow oil): $^1$H NMR (300 MHz, DMSO-$d_6$) δ 9.23 (dd, J=2.2, 0.9 Hz, 1H), 8.53 (dd, J=8.1, 2.2 Hz, 1H), 8.22 (dd, J=8.1, 0.9 Hz, 1H), 3.20 (t, J=7.2 Hz, 2H), 1.53 (q, J=7.1 Hz, 2H), 0.91-0.61 (m, 1H), 0.53-0.23 (m, 2H), 0.15-0.00 (m, 2H); MS (ES+) 201.2 (M+1); (ES−) 199.2 (M−1).
2. 5-(3-cyclopropylpropanoyl)picolinamide (221e) (481 mg, 2.204 mmol, 4.99% yield) as a white solid; $^1$H NMR (300 MHz, DMSO-$d_6$) δ 9.12 (dd, J=2.2, 0.9 Hz, 1H), 8.48 (dd, J=8.2, 2.2 Hz, 1H), 8.27 (s, 1H), 8.15 (dd, J=8.2, 0.8 Hz, 1H), 7.84 (s, 1H), 3.20 (t, J=7.2 Hz, 2H), 1.54 (q, J=7.1 Hz, 2H), 0.87-0.63 (m, 1H), 0.46-0.32 (m, 2H), 0.13-0.03 (m, 2H); MS (ES+) 219.2 (M+1); 241.2 (M+Na).

Step-4: Preparation of (R)-(−)-5-(1-(tert-butylsulfinylimino)-3-cyclopropylpropyl)picolinamide (221f)

Compound 212f was prepared from 5-(3-cyclopropylpropanoyl)picolinamide (221e) (458 mg, 2.098 mmol) and (R)-2-methylpropane-2-sulfinamide (331 mg, 2.73 mmol), using procedure as reported in step-1 of scheme 208 to afford (R)-(−)-5-(1-(tert-butylsulfinylimino)-3-cyclopropylpropyl)picolinamide (221f) (393 mg, 1.223 mmol, 58.3% yield) as a light yellow syrup; $^1$H NMR (300 MHz, DMSO-$d_6$) δ 9.03 (s, 1H), 8.40 (d, J=7.9 Hz, 1H), 8.20 (s, 1H), 8.11 (d, J=8.2 Hz, 1H), 7.80 (s, 1H), 3.52-3.27 (m, 2H), 1.59-1.37 (m, 2H), 1.25 (s, 9H), 0.87-0.62 (m, 1H), 0.50-0.28 (m, 2H), 0.12--0.00 (m, 2H); MS (ES+) 344.3 (M+Na) Optical rotation: $[\alpha]_D$=(+) 7.27 [0.11, MeOH].

Step-5: Preparation of 5-((−)-1-(3-amino-4-fluorophenyl)-3-cyclopropyl-1-((R)-1,1-dimethylethylsulfinamido)propyl)picolinamide (221g)

Compound (221g) was prepared from (R)-(−)-5-(1-(tert-butylsulfinylimino)-3-cyclopropylpropyl)picolinamide (221f) (373 mg, 1.16 mmol), using procedure as reported in step-2 of scheme 208 to afford 5-((−)-1-(3-amino-4-fluorophenyl)-3-cyclopropyl-1-((R)-1,1-dimethylethylsulfinamido)propyl)picolinamide (221g) (287 mg, 0.663 mmol, 57.2% yield) as a white solid; $^1$H NMR (300 MHz, DMSO-$d_6$) δ 8.53-8.49 (m, 1H), 8.08 (s, 1H), 8.00-7.87 (m, 2H), 7.62 (s, 1H), 6.92 (dd, J=11.2, 8.5 Hz, 1H), 6.72 (dd, J=8.8, 2.3 Hz, 1H), 6.56-6.46 (m, 1H), 5.42 (s, 1H), 5.12 (s, 2H), 2.62-2.38 (m, 2H), 1.30-0.77 (m, 2H), 1.13 (s, 9H), 0.75-0.55 (m, 1H), 0.42-0.30 (d, J=8.0 Hz, 2H), 0.02 to −0.15 (s, 2H); $^{19}$F NMR (282 MHz, DMSO-$d_6$) δ −137.37; MS (ES+) 455.4 (M+Na); Optical rotation: $[\alpha]_D$=(−) 78.75 [0.16, MeOH].

Step-6: Preparation of tert-butyl 3-(5-(5-((−)-1-(6-carbamoylpyridin-3-yl)-3-cyclopropyl-1-((R)-1,1-dimethylethylsulfinamido)propyl)-2-fluorophenylcarbamoyl)-3-(trifluoromethyl)-1H-pyrazol-1-yl)benzylcarbamate (221h)

Compound (221h) was prepared from 1-(3-((tert-butoxycarbonylamino)methyl)phenyl)-3-(trifluoromethyl)-1H-pyrazole-5-carboxylic acid (10d) (290 mg, 0.751 mmol) and 5-((−)-1-(3-amino-4-fluorophenyl)-3-cyclopropyl-1-((R)-1,1-dimethylethylsulfinamido)propyl)picolinamide (221g) (260 mg, 0.601 mmol) using the procedure as reported in step-3 of scheme 208 to afford tert-butyl 3-(5-(5-((−)-1-(6-carbamoylpyridin-3-yl)-3-cyclopropyl-1-((R)-1,1-dimethylethylsulfinamido)propyl)-2-fluorophenylcarbamoyl)-3-(trifluoromethyl)-1H-pyrazol-1-yl)benzylcarbamate (221h) (115 mg, 0.144 mmol, 19.17% yield) as a colorless solid; $^1$H NMR (300 MHz, DMSO-$d_6$) δ 10.62 (s, 1H), 8.50 (d, J=2.2 Hz, 1H), 8.09 (d, J=2.7 Hz, 1H), 7.97 (d, J=8.2 Hz, 1H), 7.92-7.84 (m, 1H), 7.69-7.20 (m, 10H), 5.71 (s, 1H), 4.19 (d, J=6.2 Hz, 2H), 2.75-2.40 (m, 2H), 1.38 (s, 9H), 1.13 (s, 9H), 1.15-1.13 (m, 1H), 1.00-0.80 (m, 1H), 0.70-0.55 (m, 1H), 0.40-0.27 (m, 2H), 0.00 to −0.15 (m, 2H); $^{19}$F NMR (282 MHz, DMSO-$d_6$) δ −60.81, −122.88; MS (ES+) 822.5 (M+Na), (ES−) 798.5 (M−1); Optical rotation: $[\alpha]_D$=(−) 44.71 [0.085, MeOH].

Step-7: Preparation of (+)-5-(1-amino-1-(3-(1-(3-(aminomethyl)phenyl)-3-(trifluoromethyl)-1H-pyrazole-5-carboxamido)-4-fluorophenyl)-3-cyclopropylpropyl)picolinamide (221i)

To a stirred solution of tert-butyl 3-(5-(5-((−)-1-(6-carbamoylpyridin-3-yl)-3-cyclopropyl-1-((R)-1,1-dimethylethylsulfinamido)propyl)-2-fluorophenylcarbamoyl)-3-(trifluoromethyl)-1H-pyrazol-1-yl)benzylcarbamate (221h) (100 mg, 0.125 mmol) in ethanol (15 mL) was added conc. HCl (0.11 mL, 1.325 mmol) and heated at reflux for 1 h. The reaction mixture was concentrated in vacuum to dryness and the residue obtained was suspended in ethanol (2 mL) and triturated with t-butyl methyl ether (20 mL). The solid obtained was collected by filtration and washed with ether. This residue was dissolved in water (1 mL) and lyophilized to afford of (+)-5-(1-amino-1-(3-(1-(3-(aminomethyl)phenyl)-3-(trifluoromethyl)-1H-pyrazole-5-carboxamido)-4-fluorophenyl)-3-cyclopropylpropyl)picolinamide (221i) (42 mg, 0.059 mmol, 47.38% yield) hydrochloride as a white solid; $^1$H NMR (300 MHz, DMSO-$d_6$) δ 10.81 (s, 1H), 9.60 (s, 3H), 8.68-8.62 (m, 1H), 8.43 (s, 3H), 8.18 (d, J=2.9 Hz, 1H), 8.07 (d, J=8.3 Hz, 1H), 7.94 (dd, J=8.4, 2.4 Hz, 1H), 7.75 (s, 1H), 7.72 (d, J=1.9 Hz, 1H), 7.68 (s, 1H), 7.61 (dt, J=7.3, 1.7 Hz, 1H), 7.58-7.48 (m, 3H), 7.40 (dd, J=8.5, 3.7 Hz, 2H), 4.11 (q, J=5.8 Hz, 2H), 2.64-2.53 (m, 2H), 1.27-0.99 (m, 2H), 0.69 (m, 1H), 0.43-0.32 (m, 2H), 0.00 (m, 2H); $^{19}$F NMR (282 MHz, DMSO-$d_6$) δ −60.83, −120.35; MS (ES+) 618.462 (M+Na), (ES−) 594.458 (M−1); Optical rotation: $[\alpha]_D$=(+) 7.55 [0.265, MeOH]; Analysis calculated for $C_{30}H_{29}F_4N_7O_2 \cdot 2HCl \cdot 2.25H_2O$: C, 50.82; H, 5.05; Cl, 10.00; N, 13.83; Found: C, 50.87; H, 5.41; Cl, 10.23; N, 13.44.

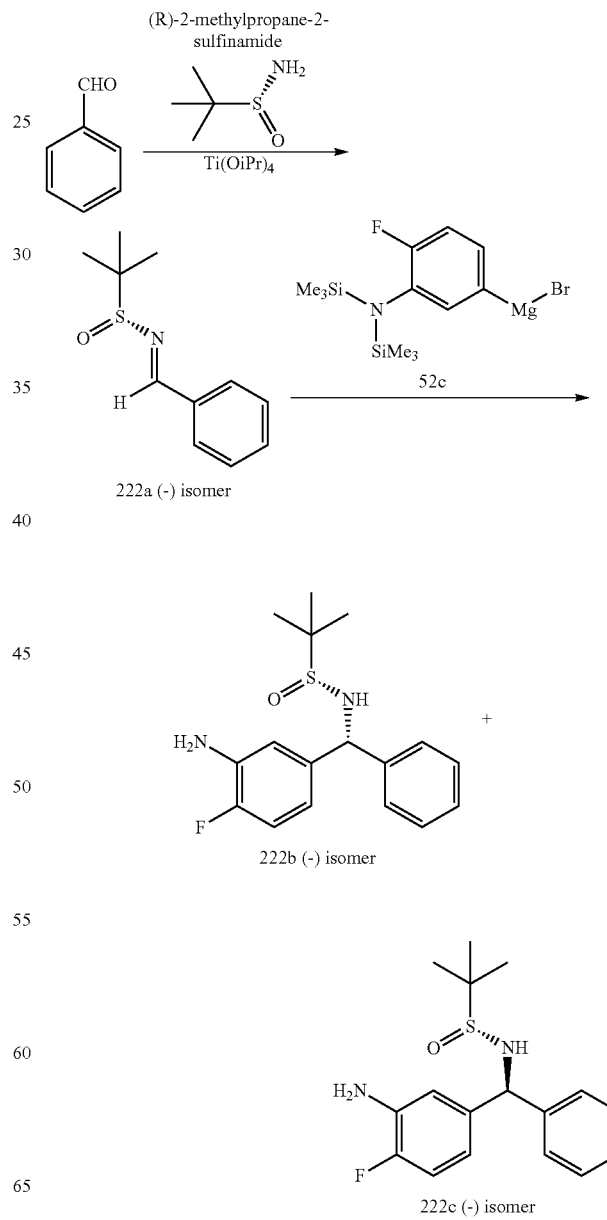

Scheme 222

807
-continued
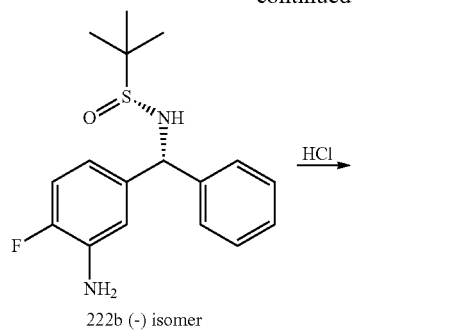
222b (−) isomer
HCl →
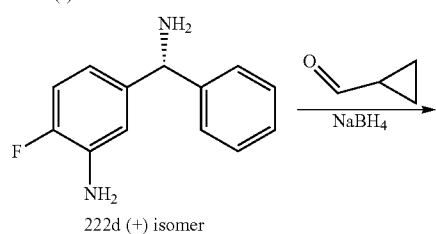
222d (+) isomer
→ (cyclopropanecarboxaldehyde) / NaBH₄
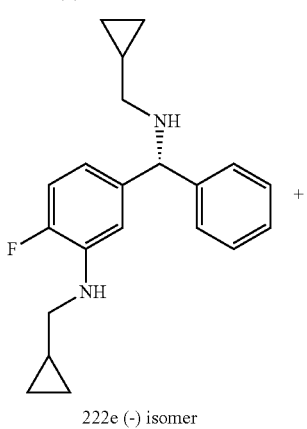
222e (−) isomer
+
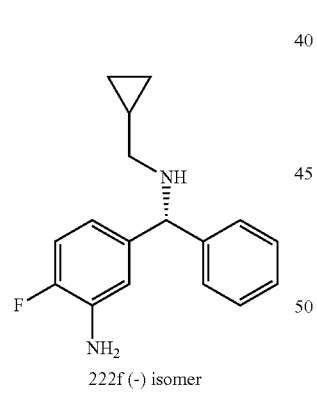
222f (−) isomer
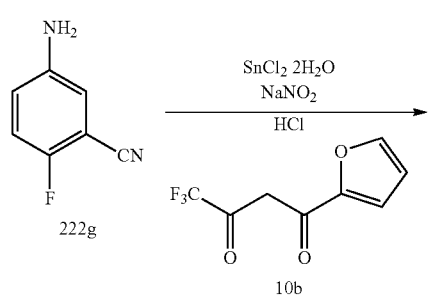
222g
SnCl₂ 2H₂O
NaNO₂
HCl
→
(F₃C-CO-CH₂-CO-furan)
10b
808
-continued
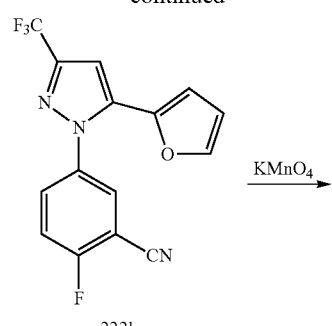
222h
KMnO₄ →
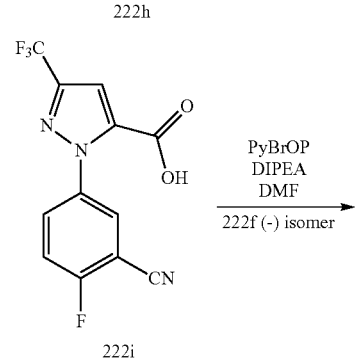
222i
PyBrOP
DIPEA
DMF
222f (−) isomer
→
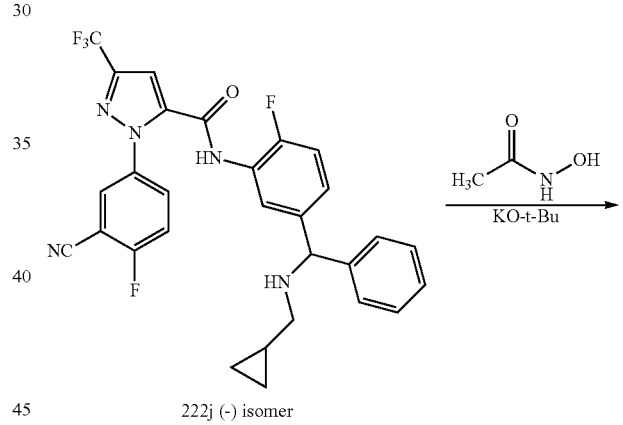
222j (−) isomer
H₃C-C(O)-N(H)-OH
KO-t-Bu
→
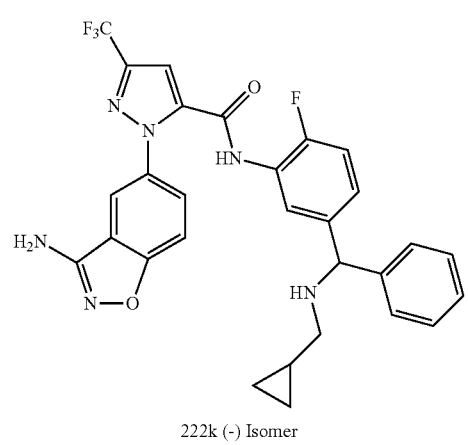
222k (−) Isomer Preparation of (−)-1-(3-aminobenzo[d]isoxazol-5-yl)-N-(5-((cyclopropylmethylamino)(phenyl)methyl)-2-fluorophenyl)-3-(trifluoromethyl)-1H-pyrazole-5-carboxamide (222j)

Step-1: Preparation of (R)-(−)-N-benzylidene-2-methylpropane-2-sulfinamide (222a)

To a stirred solution of benzaldehyde (259 mL, 2541 mmol) in tetrahydrofuran (2500 mL) was added (R)-2,4,6-triisopropylbenzenesulfinamide (280 g, 2310 mmol), tetraisopropoxytitanium (1382 mL, 4620 mmol) and stirred at room temperature for 36 h. The reaction mixture was diluted with 1 L of brine with vigorous stirring, followed by ethyl acetate (6 L) and stirred for 4 h. The reaction mixture was filtered washed with ethyl acetate (6×2 L). The organic layers were combined washed with a solution of sodium metabisulfite (329 mL, 1733 mmol), water (462 mL) dried over $MgSO_4$, filtered, evaporated to dryness. The crude residue was purified by flash column chromatography (silica gel 1.5 kg, eluting with 20% ethyl acetate in hexane) to furnish (R)-(−)-N-benzylidene-2-methylpropane-2-sulfinamide (222a) (472.51 g, 2257 mmol, 98% yield) as a pale yellow oil; $^1$H NMR (300 MHz, DMSO-$d_6$) δ 8.57 (s, 1H), 8.03-7.89 (m, 2H), 7.70-7.48 (m, 3H), 1.19 (s, 9H); MS (ES+) 232.18 (M+Na); Optical rotation: $[α]_D$=(−) 112.11 [4.155, $CHCl_3$].

Step-2: Preparation of (R)—N—((R)-(3-amino-4-fluorophenyl)(phenyl)methyl)-2-methylpropane-2-sulfinamide (222b) and (R)—N—((S)-(3-amino-4-fluorophenyl)(phenyl)methyl)-2-methylpropane-2-sulfinamide (222c)

Batch-1:
To a solution of (R)-(−)-N-benzylidene-2-methylpropane-2-sulfinamide (222a) (475 g, 2269 mmol) in toluene (4 L) cooled to −11° C. was added dropwise freshly prepared Grignard reagent (3-(bis(trimethylsilyl)amino)-4-fluorophenyl)magnesium bromide (52c) (4.75 L, 3563 mmol) over a period of 70 minutes, maintaining internal between temp (−11.1 to −10° C.). Reaction mixture was stirred at the same temperature until complete (check TLC for reaction completion).

Reaction was quenched with 1N $KHSO_4$ at −10° C. The reaction was warmed to room temperature over a 30 mins period and organic layer was separated. The aqueous layer was extracted with ethyl acetate (2×2 L). The organic layers were combined washed water (2×2 L), brine (3.5 L), dried filtered and concentrated in vacuum to afford crude oil containing mixture of diastereoisomers of (R)—N—((R)-(3-amino-4-fluorophenyl)(phenyl)methyl)-2-methylpropane-2-sulfinamide (222b) and (R)—N—((S)-(3-amino-4-fluorophenyl)(phenyl)methyl)-2-methylpropane-2-sulfinamide (222c) [(de=72/28) 727 g, 2269 mmol]. To crude in a 22 L flask was added IPA (2000 mL) and heated at reflux with stirring (30 mins to completely solubilize). The reaction mixture was cooled to 27° C. over a period of 5 h with gentle stirring. The solid obtained was collected by filtration washed with IPA (5×100 mL), air dried for 24 h to furnish (R)—N—((R)-(3-amino-4-fluorophenyl)(phenyl)methyl)-2-methylpropane-2-sulfinamide (222b) (351 g, 48.3% yield, de=94.63%.) as a white crystalline solid.

Batch-2:
The above procedure was repeated using (R)-(−)-N-benzylidene-2-methylpropane-2-sulfinamide (222a) (0.500 kg, 2.389 mol) to furnish (R)—N—((R)-(3-amino-4-fluorophenyl)(phenyl)methyl)-2-methylpropane-2-sulfinamide (222b) (329 g, 43% yield, de=93.58%.) as a white crystalline solid.

Batch-3:
The above procedure was repeated using (R)-(−)-N-benzylidene-2-methylpropane-2-sulfinamide (222a) (409 g, 1953 mmol) to furnish (R)—N—((R)-(3-amino-4-fluorophenyl)(phenyl)methyl)-2-methylpropane-2-sulfinamide (222b) (264 g, 42% yield, de=94.33%.) as a white crystalline solid.

Second Crystallization:
The above three batches were combined In a 22 L wide mouth rotary evaporator flash fitted with a mechanical stirrer containing mixture of diastereoisomers of (222b) and (222c) (batch-1, 351 g, 48.3% yield, de=94.63%), (batch-2, 329 g, 43% yield, de=93.58%) and (batch-3, 264 g, 42% yield, de=94.33%) was added IPA (4000 mL) and heated at reflux with stirring (50 mins to completely solubilize). The reaction mixture was cooled to room temperature overnight with gentle stirring (13° C.). The solid crystallized after about 1 h of cooling and stirring was continued overnight. The solid obtained was collected by filtration washed with IPA (1×100 mL and 2×200 mL), dried in high vacuum for 24 h to furnish (R)—N—((R)-(3-amino-4-fluorophenyl)(phenyl)methyl)-2-methylpropane-2-sulfinamide (222b) (872 g, 92% yield, de=99.2852%.) as a white crystalline solid; $^1$H NMR (300 MHz, DMSO-$d_6$) δ 7.40-7.26 (m, 4H), 7.25-7.15 (m, 1H), 6.90 (dd, J=11.5, 8.3 Hz, 1H), 6.75 (dd, J=8.9, 2.2 Hz, 1H), 6.57 (ddd, J=8.4, 4.4, 2.2 Hz, 1H), 5.77 (d, J=5.4 Hz, 1H), 5.33 (d, J=5.3 Hz, 1H), 5.11 (s, 2H), 1.13 (s, 9H); $^{19}$F NMR (282 MHz, DMSO) δ −137.36; $^{13}$C NMR (75 MHz, DMSO) δ 151.32, 148.19, 143.13, 139.74, 139.70, 128.22, 127.63, 126.93, 115.04, 114.98, 114.91, 114.82, 114.60, 114.35, 61.88, 55.42, 22.77; Optical rotation: $[α]_D$=(−) 70.70 (MeOH, 1.065); Analysis calculated for $C_{17}H_{21}FN_2OS$: C, 63.72; H, 6.61; N, 8.74; Found: C, 63.74; H, 6.74; N, 8.74.

Data for (R)—N—((S)-(3-amino-4-fluorophenyl)(phenyl)methyl)-2-methylpropane-2-sulfinamide (222c); $^1$H NMR (300 MHz, DMSO-$d_6$) δ 7.41-7.36 (m, 2H), 7.36-7.27 (m, 2H), 7.26-7.18 (m, 1H), 6.89 (dd, J=11.5, 8.3 Hz, 1H), 6.71 (dd, J=8.9, 2.2 Hz, 1H), 6.51 (ddd, J=8.4, 4.5, 2.2 Hz, 1H), 5.82 (d, J=5.5 Hz, 1H), 5.32 (d, J=5.5 Hz, 1H), 5.09 (s, 2H, 1H $D_2O$ exchangeable), 1.14 (s, 9H); $^{19}$F NMR (282 MHz, DMSO-$d_6$) δ −137.32; MS (ES+) 321.3 (M+1), 343.3 (M+Na), 663.5 (2M+Na); MS (ES−) 319.3 (M−1). Optical rotation: $[α]_D$=(−) 73.21 (MeOH, 2.505).

Step-3: Preparation of (+)-5-(amino(phenyl)methyl)-2-fluoroaniline (222d)

To a mechanically stirred slurry of (R)—N—((R)-(3-amino-4-fluorophenyl)(phenyl)methyl)-2-methylpropane-2-sulfinamide (222b) (99.13 g, 309 mmol) in MTBE (600 mL) was added 4M HCl (dioxane) (162 mL, 650 mmol) and stirred at room temperature for 11 h. Solid starts forming as soon as HCl addition is started. TLC analysis shows unreacted starting material, additional 4M HCl (dioxane) (162 mL, 650 mmol) was added at room temperature for 16 h. Excess methanol was evaporated, mixture basified with 3N NaOH (455 mL) and compound was extracted with ethyl acetate (2×750 mL). The combined organic layers were dried over anhydrous $MgSO_4$, filtered, evaporated to dryness. The solid was triturated with hexanes, stirred for 1 h and solid obtained was collected by filtration to afford (+)-5-(amino(phenyl)methyl)-2-fluoroaniline (222d) (38.0 g, 57% yield) as a pale yellow solid; $^1$H NMR (300 MHz, DMSO-$d_6$) δ 7.39-7.33 (m, 2H), 7.27 (ddd, J=7.6, 6.6, 1.2 Hz, 2H), 7.21-7.13 (m, 1H), 6.86 (dd, J=11.5, 8.3 Hz, 1H), 6.77 (dd, J=9.0, 2.2 Hz, 1H), 6.54 (ddd, J=8.3, 4.4, 2.2 Hz, 1H), 5.03 (s, 2H, D$_2$O exchangeable), 4.96 (s, 1H), 2.71 (s, 2H, D$_2$O exchangeable); $^{19}$F NMR (282 MHz, DMSO-d$_6$) δ −138.12; MS (ES+) 217.2 (M+1); 215.1 (M−1); Optical rotation: [α]$_D$=(+) 1.47 (0.545, MeOH).

Step-4: Preparation of (−)-N-(cyclopropylmethyl)-5-((cyclopropylmethylamino)(phenyl)methyl)-2-fluoroaniline (222e) and (−)-5-((cyclopropylmethylamino)(phenyl)methyl)-2-fluoroaniline (222f)

To a stirred solution of (+)-5-(amino(phenyl)methyl)-2-fluoroaniline (222d) (5.312 g, 24.56 mmol) in MeOH (80 mL) was added cyclopropanecarboxaldehyde (1.944 mL, 25.8 mmol) at 0° C. for a period of 10 min and stirred for 30 mins. To this sodium borohydride (1.859 g, 49.1 mmol) was added in multiple portions and stirred for 1 h at 0° C. Excess solvent was evaporated and residue was treated with water (100 mL), and extracted with ethyl acetate (2×100 mL). The organic layers were combined dried over anhydrous MgSO$_4$, filtered and evaporated to dryness. The residue was purified by flash column chromatography (silica gel 80 g, eluting with 0-100% ethyl acetate in hexanes) to furnish
1. (−)-N-(cyclopropylmethyl)-5-((cyclopropylmethylamino)(phenyl)methyl)-2-fluoroaniline (222e) (0.663 g, 8% yield) as an yellow oil as a yellow oil; $^1$H NMR (300 MHz, DMSO-d$_6$) δ 7.44-7.35 (m, 2H), 7.30-7.21 (m, 2H), 7.19-7.08 (m, 1H), 6.96-6.75 (m, 2H), 6.55 (ddd, J=8.3, 4.6, 2.0 Hz, 1H), 5.26 (td, J=6.0, 2.3 Hz, 1H, D$_2$O exchangeable), 4.71 (s, 1H), 2.93 (t, J=6.2 Hz, 2H), 2.27 (d, J=7.1 Hz, 3H, 1H, D$_2$O exchangeable), 1.09-0.84 (m, 2H), 0.39 (m, 4H), 0.25-0.15 (m, 2H), 0.09--0.02 (m, 2H); $^{19}$F NMR (282 MHz, DMSO-d$_6$) δ −137.56; MS (ES+) 325.4 (M+1); Optical rotation: [α]$_D$=(−) 6.67 [0.27, methanol]
2. (−)-5-((cyclopropylmethylamino)(phenyl)methyl)-2-fluoroaniline (222f) (4.84 g, 73% yield) as a yellow oil; $^1$H NMR (300 MHz, DMSO-d$_6$) δ 7.42-7.34 (m, 2H), 7.32-7.23 (m, 2H), 7.22-7.11 (m, 1H), 6.92-6.78 (m, 2H), 6.55 (ddd, J=8.3, 4.5, 2.2 Hz, 1H), 5.04 (s, 2H, D$_2$O exchangeable), 4.67 (s, 1H), 2.25 (td, J=9.6, 5.3 Hz, 3H; 1H D$_2$O exchangeable), 1.04-0.80 (m, 1H), 0.50-0.28 (m, 2H), 0.11-0.02 (m, 2H); $^{19}$F NMR (282 MHz, DMSO-d$_6$) δ −137.92; MS (ES−) 269.3 (M−1); Optical rotation: [α]$_D$=(−) 12.24 [1.275, CHCl$_3$]; Chiral purity checked by performing chiral HPLC using chiral AD-H column, 1 mL/min, Solvent: 95% Hexane, 5% isopropanol, UV=260 nM, 25° C. (>99.99 ee).

Step-5: Preparation of 5-(5-(furan-2-yl)-3-(trifluoromethyl)-1H-pyrazol-1-yl)benzonitrile (222h)

To a suspension of 5-amino-2-fluorobenzonitrile (222g) (25 g, 184 mmol) in 12N HCl (55.1 mL, 661 mmol) was added a solution of sodium nitrite (15.21 g, 220 mmol) in water (75 mL) at 0° C. After stirring for 1 h, to the mixture was added tin(II) chloride dihydrate (83 g, 367 mmol) pre-dissolved in 12N HCl (55.1 mL, 661 mmol) at such a rate that the temperature was not allowed to go above 5 OC. After stirring for 2 h, a solution of 4,4,4-trifluoro-1-(furan-2-yl)butane-1,3-dione (10b) (37.9 g, 184 mmol) in ethanol (305 mL) was added and heated at 60° C. for 21 h. The reaction mixture was cooled to room temperature and concentrated in vacuum to remove ethanol. The aqueous was basified with saturated NaHCO$_3$ and extracted with ethyl acetate (3×500 mL). The organic layers were combined dried over MgSO$_4$, filtered, and concentrated to dryness. The residue obtained was purified by flash column chromatography [silica gel 750 g, eluting with ethyl acetate in hexanes, from 0-100%] to furnish 5-(5-(furan-2-yl)-3-(trifluoromethyl)-1H-pyrazol-1-yl)benzonitrile (222h) (11.5 g, 35.8 mmol, 19.49% yield) as a white solid; $^1$H NMR (300 MHz, DMSO-d$_6$) δ 8.30 (dd, J=5.7, 2.7 Hz, 1H), 8.06-7.98 (m, 1H), 7.82-7.70 (m, 2H), 7.34 (s, 1H), 6.59 (dd, J=3.5, 1.8 Hz, 1H), 6.49 (d, J=3.5 Hz, 1H); MS (ES$^+$): MS (ES+) 665.3 (2M+Na).

Step-6: Preparation of 1-(3-cyano-4-fluorophenyl)-3-(trifluoromethyl)-1H-pyrazole-5-carboxylic Acid (222i)

To a stirred solution of 5-(5-(furan-2-yl)-3-(trifluoromethyl)-1H-pyrazol-1-yl)benzonitrile (222h) (11.1 g, 34.6 mmol) in acetone (200 mL) was added a solution of potassium permanganate (38.2 g, 242 mmol) in water (100 mL) drop-wise over a period of 30 min. This mixture was heated at 60° C. for 2 h, cooled to room temperature and quenched with 2-propanol (200 mL). The reaction mixture was stirred at room temperature overnight and filtered through Celite washed with acetone/water mixture (2×50 mL), methanol (2×75 mL). The organic solvent was removed by evaporation under reduced pressure. The reaction mixture was basified with 1N NaOH, washed with ether (2×150 mL). Aqueous layer was poured on to crushed ice, acidified very carefully with aq. 1N HCl under constant stirring. The solid obtained was collected by filtration, washed with hexanes (2×50 mL), dried over P$_2$O$_5$ to furnish 1-(3-cyano-4-fluorophenyl)-3-(trifluoromethyl)-1H-pyrazole-5-carboxylic acid (222i) (8.384 g, 81% yield) as a white solid; $^1$H NMR (300 MHz, DMSO-d$_6$) δ 14.03 (s, 1H, D$_2$O exchangeable), 8.36 (dd, J=5.7, 2.7 Hz, 1H), 8.07 (ddd, J=9.0, 4.7, 2.7 Hz, 1H), 7.72 (t, J=9.0 Hz, 1H), 7.57 (s, 1H); $^{19}$F NMR (282 MHz, DMSO-d$_6$) δ −60.77, −106.91; MS (ES$^+$): MS (ES+) 300.2 (M+1); MS (ES+) 298.2 (M−1), 597.3 (2M−1).

Step-7: Preparation of (−)-1-(3-cyano-4-fluorophenyl)-N-(5-((cyclopropylmethylamino)(phenyl)methyl)-2-fluorophenyl)-3-(trifluoromethyl)-1H-pyrazole-5-carboxamide (222j)

Compound 222j was prepared from 1-(3-cyano-4-fluorophenyl)-3-(trifluoromethyl)-1H-pyrazole-5-carboxylic acid (222i) (1.461 g, 4.88 mmol) and (−)-5-((cyclopropylmethylamino)(phenyl)methyl)-2-fluoroaniline (222f) (1.1 g, 4.07 mmol) using the procedure reported in scheme 208 step-3 gave (−)-1-(3-cyano-4-fluorophenyl)-N-(5-((cyclopropylmethylamino)(phenyl)methyl)-2-fluorophenyl)-3-(trifluoromethyl)-1H-pyrazole-5-carboxamide (222j) (2.239 g, 100% yield) as white solid; $^1$H NMR (300 MHz, DMSO-d$_6$) δ 10.50 (s, 1H, D$_2$O exchangeable), 8.28 (dd, J=5.7, 2.7 Hz, 1H), 8.00 (ddd, J=9.2, 4.7, 2.8 Hz, 1H), 7.76-7.65 (m, 2H), 7.55 (dd, J=7.5, 2.1 Hz, 1H), 7.42-7.30 (m, 4H), 7.30-7.23 (m, 1H), 7.22-7.14 (m, 2H), 4.84 (s, 1H), 2.44 (s, 1H), 2.34-2.22 (m, 2H), 1.02-0.84 (m, 1H), 0.47-0.28 (m, 2H), 0.08-0.01 (m, 2H); $^{19}$F NMR (282 MHz, DMSO-d$_6$) δ −60.82, −107.26, −123.06; MS (ES+): MS (ES−) 550.04 (M−1); Optical rotation: [α]$_D$=(−) 5.6 [0.25, CH$_3$OH].

Step-8: Preparation of (−)-1-(3-aminobenzo[d]isoxazol-5-yl)-N-(5-((cyclopropylmethylamino)(phenyl)methyl)-2-fluorophenyl)-3-(trifluoromethyl)-1H-pyrazole-5-carboxamide (222k)

To a stirred solution of potassium tert-butoxide (1.481 g, 13.20 mmol) and acetohydroxamic acid (0.991 g, 13.20 mmol) in DMF (20 mL) stirred for 35 min at room temperature was added (−)-1-(3-cyano-4-fluorophenyl)-N-(5-((cyclopropylmethylamino)(phenyl)methyl)-2-fluorophenyl)-3-(trifluoromethyl)-1H-pyrazole-5-carboxamide (222j) (2.206 g, 4 mmol) in DMF (20 mL). The mixture was stirred at room temperature for 16 h. The mixture was poured into a separatory funnel containing 100 mL of aqueous ammonium chloride and 100 mL of EtOAc. Aqueous layer was separated and extracted with EtOAc (100 mL). The organic layers were combined dried over anhydrous MgSO$_4$, filtered and evaporated to dryness. The residue was purified by flash column chromatography (First column: silica gel 40 g, eluting with 0-100% ethyl acetate in hexanes; second column: silica gel 40 g, eluting with 0-50% CMA80 in chloroform; third column: silica gel 40 g) to furnish (−)-1-(3-aminobenzo[d]isoxazol-5-yl)-N-(5-((cyclopropylmethylamino)(phenyl)methyl)-2-fluorophenyl)-3-(trifluoromethyl)-1H-pyrazole-5-carboxamide (222k) (0.221 g, 10% yield) as a white solid; $^1$H NMR (300 MHz, DMSO-d$_6$) δ 10.49 (s, 1H, D$_2$O exchangeable), 8.07 (d, J=2.1 Hz, 1H), 7.71-7.51 (m, 4H), 7.41-7.35 (m, 2H), 7.34-7.24 (m, 3H), 7.22-7.13 (m, 2H), 6.59 (s, 2H, D$_2$O exchangeable), 4.82 (s, 1H), 2.42 (s, 1H), 2.26 (d, J=6.0 Hz, 2H), 0.89 (td, J=7.4, 3.8 Hz, 1H), 0.45-0.27 (m, 2H), 0.03 (dt, J=5.0, 2.7 Hz, 2H); $^{19}$F NMR (282 MHz, DMSO-d$_6$) δ −60.59, −123.45; MS (ES$^+$): MS (ES+) 565.5 (M+1); Optical rotation: [α]$_D$=(−) 8.3 [0.265, CH$_3$OH].

Scheme 223

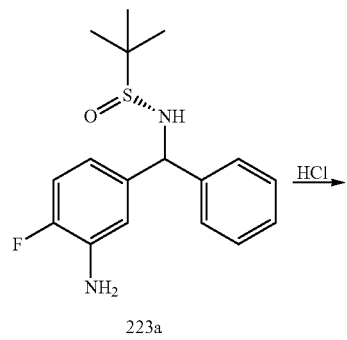

223a

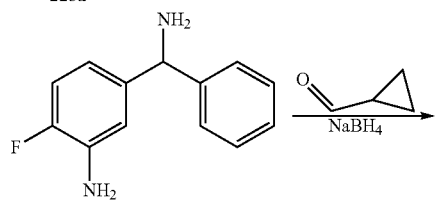

223b

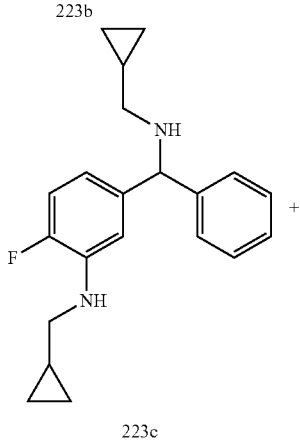

223c

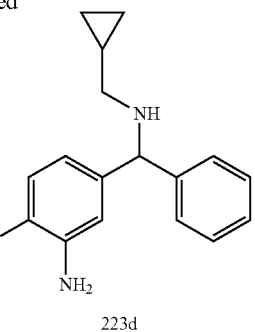

223d

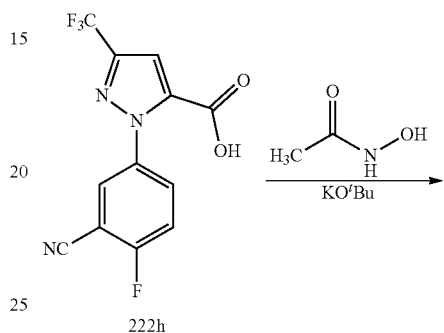

222h

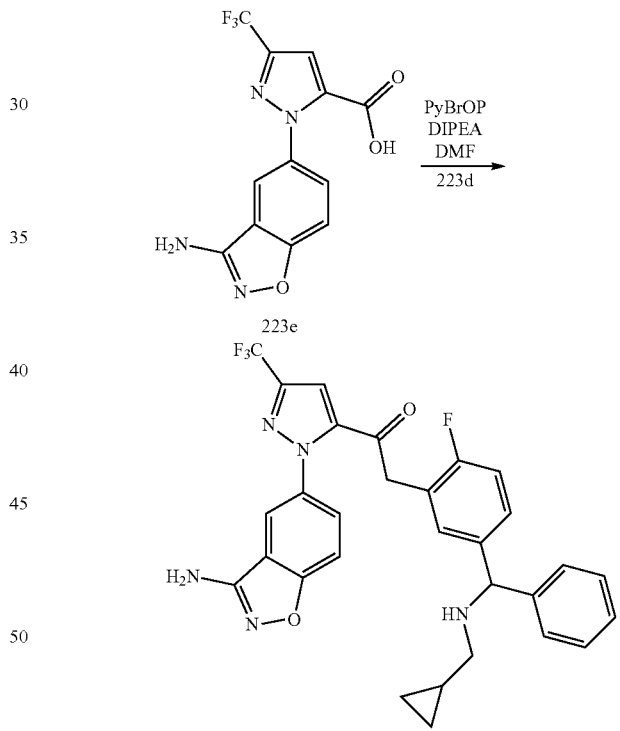

223e

223f

Preparation of 1-(3-aminobenzo[d]isoxazol-5-yl)-N-(5-((cyclopropylmethylamino)(phenyl)methyl)-2-fluorophenyl)-3-(trifluoromethyl)-1H-pyrazole-5-carboxamide (223f)

Step-1: Preparation of 5-(amino(phenyl)methyl)-2-fluoroaniline (223b)

Compound (R)—N-((3-amino-4-fluorophenyl)(phenyl)methyl)-2-methylpropane-2-sulfinamide (223a) was obtained from the mother liquor from crystallization of mixture of diastereoisomers of (R)—N—((R)-(3-amino-4-fluorophenyl)(phenyl)methyl)-2-methylpropane-2-sulfinamide (222b) and (R)—N—((S)-(3-amino-4-fluorophenyl)(phenyl)methyl)-2-methylpropane-2-sulfinamide (222c) in scheme-222. Compound 223b was prepared from (R)—N-((3-amino-4-fluorophenyl)(phenyl)methyl)-2-methylpropane-2-sulfinamide (223a) (27.8 g, 87 mmol) using procedure reported in step-3 of scheme-222 to furnish 5-(amino(phenyl)methyl)-2-fluoroaniline (223b) (14 g, 75%) as a light brown solid; $^1$H NMR (300 MHz, DMSO-$d_6$) δ 7.40-7.32 (m, 2H), 7.27 (ddd, J=7.6, 6.7, 1.2 Hz, 2H), 7.21-7.11 (m, 1H), 6.86 (dd, J=11.5, 8.3 Hz, 1H), 6.78 (dd, J=9.0, 2.2 Hz, 1H), 6.54 (ddd, J=8.3, 4.5, 2.2 Hz, 1H), 5.00 (s, 2H), 4.93 (s, 1H), 2.13 (s, 2H); $^{19}$F NMR (282 MHz, DMSO) δ −138.30; MS (ES) 215.1 (M−1).

Step-2: Preparation of N-(cyclopropylmethyl)-5-((cyclopropylmethylamino)(phenyl)methyl)-2-fluoroaniline (223c) and 5-((cyclopropylmethylamino)(phenyl)methyl)-2-fluoroaniline (223d)

Compounds 223c and 223d was prepared from 5-(amino(phenyl)methyl)-2-fluoroaniline (223b) (1.081 g, 5.00 mmol) according to procedure reported in step-4 of scheme-222 to furnish:
1. N-(cyclopropylmethyl)-5-((cyclopropylmethylamino)(phenyl)methyl)-2-fluoroaniline (223c) (0.194 g, 0.598 mmol, 11.96% yield) as a colorless oil; $^1$H NMR (300 MHz, DMSO-$d_6$) δ 7.44-7.35 (m, 2H), 7.30-7.21 (m, 2H), 7.19-7.11 (m, 1H), 6.94-6.79 (m, 2H), 6.56 (ddd, J=8.2, 4.6, 2.1 Hz, 1H), 5.29 (td, J=5.9, 2.3 Hz, 1H), 4.72 (s, 1H), 2.94 (t, J=6.2 Hz, 2H), 2.38-2.20 (m, 3H), 1.10-0.97 (m, 1H), 0.91 (m, 1H), 0.40 (m, 4H), 0.21 (m, 2H), 0.03 (m, 2H); $^{19}$F NMR (282 MHz, DMSO) δ −137.78; MS (ES+) 325.3 (M+1); (ES−) 323.2 (M−1).
2. 5-((cyclopropylmethylamino)(phenyl)methyl)-2-fluoroaniline (223d) (0.795 g, 2.94 mmol, 58.8% yield) as a colorless oil; $^1$H NMR (300 MHz, DMSO-$d_6$) δ 7.40-7.33 (m, 2H), 7.27 (tt, J=6.6, 0.9 Hz, 2H), 7.20-7.12 (m, 1H), 6.90-6.78 (m, 2H), 6.54 (ddd, J=8.3, 4.5, 2.1 Hz, 1H), 5.04 (s, 2H), 4.67 (s, 1H), 2.34-2.22 (m, 3H), 0.91 (m, 1H), 0.44-0.30 (m, 2H), 0.09-0.00 (m, 2H); $^{19}$F NMR (282 MHz, DMSO) δ −137.95; MS (ES+) 271.2 (M+1).

Step-3: Preparation of 1-(3-aminobenzo[d]isoxazol-5-yl)-3-(trifluoromethyl)-1H-pyrazole-5-carboxylic acid (223e)

Compound 223 e was prepared from 1-(3-cyano-4-fluorophenyl)-3-(trifluoromethyl)-1H-pyrazole-5-carboxylic acid (222h) (2 g, 6.68 mmol) using procedure reported in step-8 of scheme-222 to furnish 1-(3-aminobenzo[d]isoxazol-5-yl)-3-(trifluoromethyl)-1H-pyrazole-5-carboxylic acid (223e) (1.823 g, 87% yield) as a white solid; $^1$H NMR (300 MHz, DMSO-$d_6$) δ 8.03 (d, J=2.1 Hz, 1H), 7.73 (dd, J=8.8, 2.2 Hz, 1H), 7.63-7.51 (m, 2H), 6.57 (s, 2H, D$_2$O exchangeable); $^{19}$F NMR (282 MHz, DMSO-$d_6$) δ −60.63; MS (ES$^+$): MS (ES+) 313.2 (M+1), MS (ES−) 311.1 (M−1), 623.3 (2M−1).

Step-4: Preparation of 1-(3-aminobenzo[d]isoxazol-5-yl)-N-(5-((cyclopropylmethylamino)(phenyl)methyl)-2-fluorophenyl)-3-(trifluoromethyl)-1H-pyrazole-5-carboxamide (223f)

Compound 223f was prepared from 1-(3-aminobenzo[d]isoxazol-5-yl)-3-(trifluoromethyl)-1H-pyrazole-5-carboxylic acid (223e) (0.577 g, 1.849 mmol) and 5-((cyclopropylmethylamino)(phenyl)methyl)-2-fluoroaniline (223d) (0.5 g, 1.849 mmol) according to procedure reported in step-3 of scheme-208 to furnish 1-(3-aminobenzo[d]isoxazol-5-yl)-N-(5-((cyclopropylmethylamino)(phenyl)methyl)-2-fluorophenyl)-3-(trifluoromethyl)-1H-pyrazole-5-carboxamide (223f) (0.171 g, 16% yield) as a white solid; $^1$H NMR (300 MHz, DMSO-$d_6$) δ 10.79 (s, 1H), 8.37 (t, J=2.2 Hz, 1H), 8.03-7.80 (m, 4H), 7.72-7.42 (m, 7H), 6.88 (s, 2H), 5.12 (d, J=1.8 Hz, 1H), 2.73 (m, 1H), 2.62-2.50 (m, 2H), 1.18 (m, 1H), 0.66 (m, 2H), 0.39-0.27 (m, 2H); $^{19}$F NMR (282 MHz, DMSO-$d_6$) δ −60.53 (d, J=2.4 Hz), −123.40; MS (ES$^+$): MS (ES+) 565.4 (M+1).

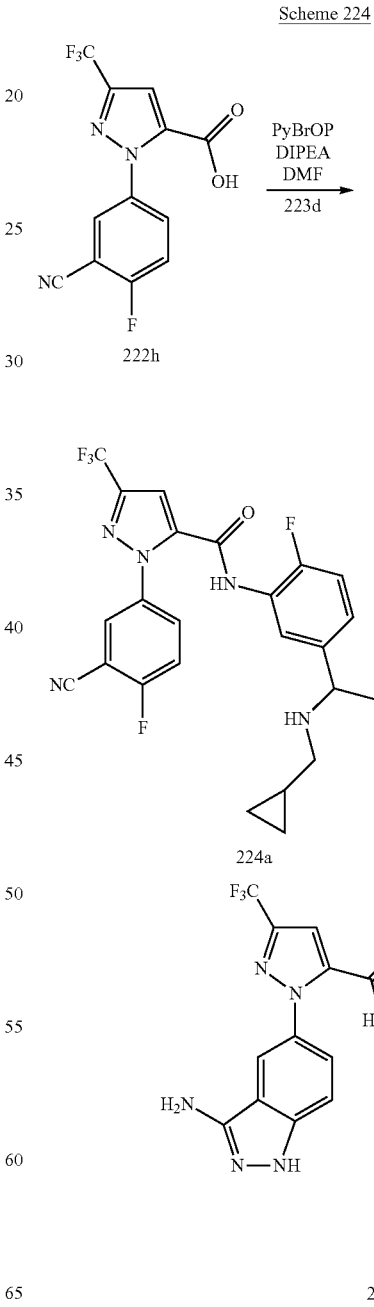

Scheme 224

817

Preparation of 1-(3-amino-1H-indazol-5-yl)-N-(5-((cyclopropylmethylamino)(phenyl)methyl)-2-fluorophenyl)-3-(trifluoromethyl)-1H-pyrazole-5-carboxamide (224b)

Step-1: Preparation of 1-(3-cyano-4-fluorophenyl)-N-(5-((cyclopropylmethylamino)(phenyl)methyl)-2-fluorophenyl)-3-(trifluoromethyl)-1H-pyrazole-5-carboxamide (224a)

Compound 224a was prepared from 1-(3-cyano-4-fluorophenyl)-3-(trifluoromethyl)-1H-pyrazole-5-carboxylic acid (222h) (1.217 g, 4.07 mmol) and 5-((cyclopropylmethylamino)(phenyl)methyl)-2-fluoroaniline (223d) (1.1 g, 4.07 mmol) as reported in step-3 of scheme-208 to furnish 1-(3-cyano-4-fluorophenyl)-N-(5-((cyclopropylmethylamino)(phenyl)methyl)-2-fluorophenyl)-3-(trifluoromethyl)-1H-pyrazole-5-carboxamide (224a) (1.38 g, 2.502 mmol, 61.5% yield) as a white solid which was used such in the next step; MS (ES+) 552.4 (M+1); MS (ES−) 550.3 (M−1).

Step-2: Preparation of 1-(3-amino-1H-indazol-5-yl)-N-(5-((cyclopropylmethylamino)(phenyl)methyl)-2-fluorophenyl)-3-(trifluoromethyl)-1H-pyrazole-5-carboxamide (224b)

To a stirred solution of 1-(3-cyano-4-fluorophenyl)-N-(5-((cyclopropylmethylamino)-(phenyl)methyl)-2-fluorophenyl)-3-(trifluoromethyl)-1H-pyrazole-5-carboxamide (224a) (0.7 g, 1.269 mmol) in n-butanol (20 mL) was added hydrazine hydrate (1.539 mL, 31.7 mmol) and heated at refluxed overnight. Reaction mixture was cooled to room temperature and evaporated in vacuum to dryness. The residue obtained was purified by flash column chromatography [silica gel 24 g, eluting with CMA80 in chloroform, 0-100%] to afford 1-(3-amino-1H-indazol-5-yl)-N-(5-((cyclopropylmethylamino)(phenyl)methyl)-2-fluorophenyl)-3-(trifluoromethyl)-1H-pyrazole-5-carboxamide (224b) (0.197 g, 27% yield) as a light yellow solid; $^1$H NMR (300 MHz, DMSO-$d_6$) δ 11.69 (s, 1H), 10.44 (s, 1H), 7.90 (t, J=1.4 Hz, 1H), 7.65-7.52 (m, 2H), 7.41-7.34 (m, 2H), 7.33-7.23 (m, 5H), 7.22-7.12 (m, 2H), 5.54 (s, 2H), 4.81 (s, 1H), 2.43 (s, 1H), 2.25 (m, 2H), 0.97-0.80 (m, 1H), 0.41-0.30 (m, 2H), 0.02 (m, 2H); $^{19}$F NMR (282 MHz, DMSO-$d_6$) δ −60.62, −123.79; MS (ES$^+$): MS (ES+) 564.4 (M+1); MS (ES−) 562.3 (M−1).

Scheme 225

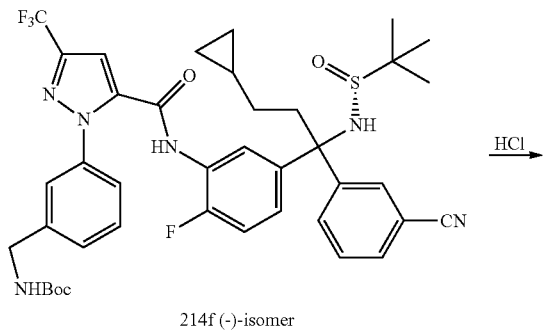

214f (−)-isomer

-continued

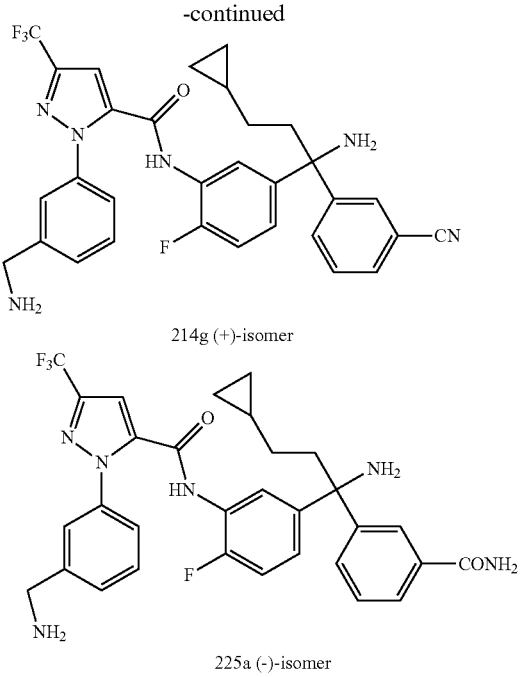

214g (+)-isomer 225a (−)-isomer

Preparation of (−)-N-(5-(1-amino-1-(3-carbamoylphenyl)-3-cyclopropylpropyl)-2-fluorophenyl)-1-(3-(aminomethyl)phenyl)-3-(trifluoromethyl)-1H-pyrazole-5-carboxamide (225a)

To a stirred solution of tert-butyl 3-(5-(5-((−)-1-(3-cyanophenyl)-3-cyclopropyl-1-((R)-1,1-dimethylethylsulfinamido)propyl)-2-fluorophenylcarbamoyl)-3-(trifluoromethyl)-1H-pyrazol-1-yl)benzylcarbamate (214f) (7.268 g, 9.31 mmol) in ethanol (70 mL) was added conc. HCl (7.80 mL, 94 mmol) and heated at reflux for 1 h. The reaction mixture was concentrated in vacuum to dryness to obtain white solid (7.173g). The white solid was purified by flash column chromatography (silica gel, 24 g eluting with CMA 80 in chloroform 0 to 100%) to afford (+)-N-(5-(1-amino-1-(3-cyanophenyl)-3-cyclopropylpropyl)-2-fluorophenyl)-1-(3-(aminomethyl)phenyl)-3-(trifluoromethyl)-1H-pyrazole-5-carboxamide (214g) contaminated with NH$_4$C$_1$. This was repurified by flash column chromatography (silica gel, 24 g eluting with methanol in chloroform 0 to 50%) to afford 214 g (4.567 g) free base as a white solid.

The free base of (214g) (4.45 g) was dissolved in methanol (150 mL) and added 4 N HCl (aq. 8.0 mL) followed by concentration in vacuum to dryness to furnish (214g) (4.622 g) white solid as a HCl salt contaminated with, (−)-N-(5-(1-amino-1-(3-carbamoylphenyl)-3-cyclopropylpropyl)-2-fluorophenyl)-1-(3-(aminomethyl)phenyl)-3-(trifluoromethyl)-1H-pyrazole-5-carboxamide (225a) due to use of dilute HCl; The solid was purified by flash column chromatography (silica gel, 120 g eluting with CMA 80 in chloroform 0 to 100%) to furnish (214g) (3.8 g) freebase followed by (225a) (150 mg, 0.252 mmol, 3.64% yield) as a white solid; $^1$H NMR (300 MHz, DMSO-$d_6$) δ 10.52 (s, 1H), 8.05-7.84 (m, 2H), 7.66 (dt, J=7.7, 1.3 Hz, 1H), 7.57 (d, J=5.3 Hz, 2H), 7.49 (d, J=8.5 Hz, 1H), 7.44-7.37 (m, 2H), 7.36-7.22 (m, 3H), 7.18 (d, J=9.6 Hz, 1H), 3.78 (s, 2H), 2.30-2.17 (m, 6H), 1.02 (m, 2H), 0.64 (m, 1H), 0.43-0.29 (m, 2H), −0.04--0.12 (m, 2H); $^{19}$F NMR (282 MHz, DMSO-$d_6$) δ −60.72, −124.42; MS (ES+) 595.5 (M+1), 617.5 (M+Na), (ES−) 593.4 (M−1); Analysis calculated for $C_{31}H_{30}F_4N_6O_2 \cdot H_2O$: C, 61.23; H, 5.22; N, 13.82; Found: C, 61.29; H, 5.40; N, 13.82; Optical rotation: [c]d=(−) 0.54 [1.15, methanol].

Hz, 2H), 7.57 (dd, J=7.5, 2.2 Hz, 1H), 7.38 (dt, J=6.5, 1.4 Hz, 2H), 7.35-7.23 (m, 3H), 7.22-7.13 (m, 2H), 4.82 (s, 1H), 2.43 (s, 1H), 2.25 (m, 2H), 0.88 (m, 1H), 0.45-0.25 (m, 2H), 0.03 (m, 2H); $^{19}$F NMR (282 MHz, DMSO-$d_6$) δ −60.76, −123.39; MS (ES+) 576.4 (M+1); MS (ES−) 574.4 (M−1).

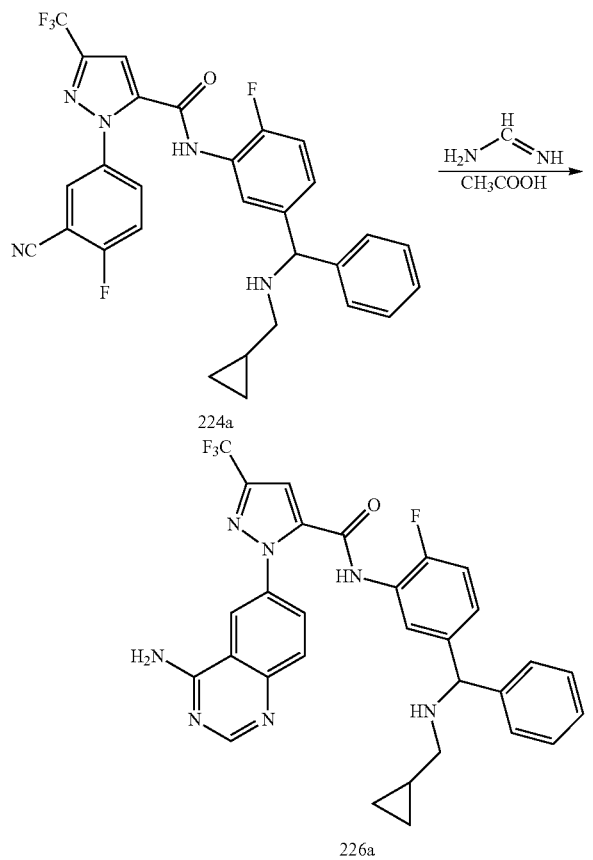

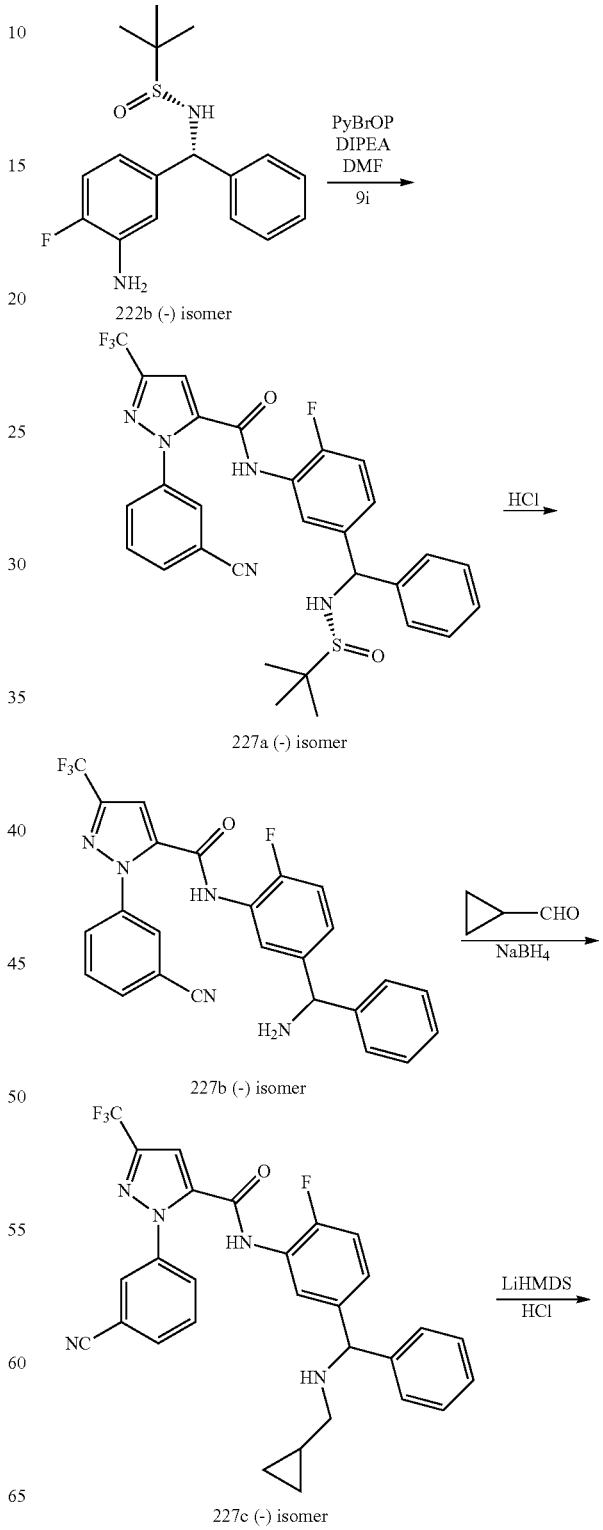

Preparation of 1-(4-aminoquinazolin-6-yl)-N-(5-((cyclopropylmethylamino)(phenyl)methyl)-2-fluorophenyl)-3-(trifluoromethyl)-1H-pyrazole-5-carboxamide (224b)

To a stirred solution of 1-(3-cyano-4-fluorophenyl)-N-(5-((cyclopropylmethylamino)(phenyl)methyl)-2-fluorophenyl)-3-(trifluoromethyl)-1H-pyrazole-5-carboxamide (224a) (0.7 g, 1.269 mmol) in N,N-dimethyl acetamide (20 mL) was added formimidamide acetate (1.321 g, 12.69 mmol) and heated at reflux overnight. Reaction mixture was cooled to room temperature, diluted with water (50 mL) and extracted with ethyl acetate (2×50 mL). Combined organics were dried over anhydrous MgSO₄, filtered and evaporated to dryness. The residue obtained was purified by flash column chromatography [First column: silica gel 24 g, eluting with CMA80 in chloroform, 0-100%; second column: silica gel 24 g, eluting with ethyl acetate/methanol (9:1) in hexanes from 0-100%] to furnish 1-(4-aminoquinazolin-6-yl)-N-(5-((cyclopropylmethylamino)(phenyl)methyl)-2-fluorophenyl)-3-(trifluoromethyl)-1H-pyrazole-5-carboxamide (224b) (0.113 g, 15% yield) as a pale yellow solid; $^1$H NMR (300 MHz, DMSO-$d_6$) δ 10.52 (s, 1H, D₂O exchangeable), 8.47 (d, J=5.6 Hz, 2H), 7.97 (s, 2H, D₂O exchangeable), 7.83 (dd, J=9.0, 2.2 Hz, 1H), 7.73 (d, J=9.2

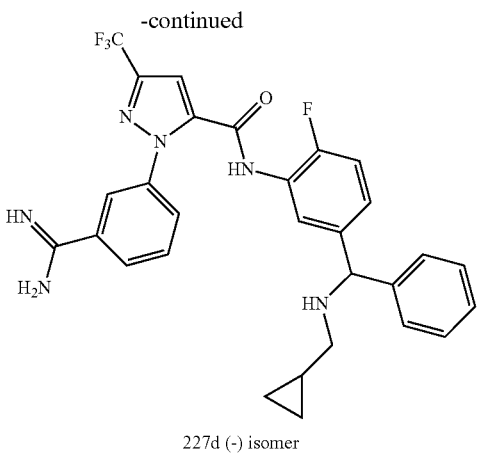

227d (−) isomer

Preparation of (−)-1-(3-carbamimidoylphenyl)-N-(5-((cyclopropylmethylamino)(phenyl)methyl)-2-fluorophenyl)-3-(trifluoromethyl)-1H-pyrazole-5-carboxamide (227d)

Step-1: Preparation of 1-(3-cyanophenyl)-N-(5-((−)-((R)-1,1-dimethylethylsulfinamido)-(phenyl)methyl)-2-fluorophenyl)-3-(trifluoromethyl)-1H-pyrazole-5-carboxamide (227a)

To a solution of (−)-N—((R)-(3-amino-4-fluorophenyl)(phenyl)methyl)-2-methylpropane-2-sulfinamide (222b) (0.872 kg, 2.72 mol) in DMF (10 mL) was added 1-(3-cyanophenyl)-3-(trifluoromethyl)-1H-pyrazole-5-carboxylic acid (9i) (0.765 kg, 2.72 mol), N-ethyl-N-isopropylpropan-2-amine (2.37 L, 13.61 mol) and bromo-tris-pyrrolidino phosphoniumhexa-fluorophosphate (PyBrOP, 1.4 kg, 2.99 mol) and stirred at room temperature for 24 h. Additional (9i) (153 g, 0.54 mol), N-ethyl-N-isopropylpropan-2-amine (470 mL) and bromo-tris-pyrrolidino phosphoniumhexafluorophosphate (PyBrOP, 280 g), DMF (500 mL) was added and stirred at room temperature for 24 h. Additional (9i) (77 g, 0.274 mol), N-ethyl-N-isopropylpropan-2-amine (470 mL) and bromo-tris-pyrrolidino phosphoniumhexafluorophosphate (PyBrOP, 140 g), DMF (500 mL) and stirred at room temperature for 24 h. After 72 h stirring at room temperature the reaction was diluted with ethyl acetate (8 L), washed with water (14 L), brine, dried, filtered, and evaporated to dryness to afford 1-(3-cyanophenyl)-N-(5-((−)-((R)-1, 1-dimethylethylsulfinamido)(phenyl)methyl)-2-fluorophenyl)-3-(trifluoromethyl)-1H-pyrazole-5-carboxamide (227a) (3108.6 g) as an off white solid, which was pure enough to be taken to next step. An analytical sample was prepared dissolving (1.6 gm) of crude in isopropanol (24 mL) by heating. The mixture was cooled to room temperature overnight with stirring and solid obtained was collected by filtration washed with isopropanol and dried under vacuum overnight to furnish 0.6 gms compound 227a as a white solid; $^1$H NMR (300 MHz, DMSO-d$_6$) δ 10.59 (s, 1H), 8.15-8.08 (m, 1H), 7.99 (dt, J=7.8, 1.3 Hz, 1H), 7.92-7.85 (m, 1H), 7.76-7.68 (m, 2H), 7.51 (dd, J=6.9, 2.2 Hz, 1H), 7.41-7.18 (m, 7H), 6.08 (d, J=6.2 Hz, 1H), 5.53 (d, J=6.1 Hz, 1H), 1.12 (s, 9H); $^{13}$C NMR (75 MHz, DMSO) δ 156.11, 152.88, 142.57, 140.13, 140.09, 139.81, 138.41, 132.99, 130.48, 130.35, 129.27, 127.66, 127.18, 126.71, 126.61, 125.31, 123.85, 123.68, 117.76, 115.93, 115.66, 111.83, 108.09, 61.71, 55.55, 22.75; $^{19}$F NMR (282 MHz, DMSO) δ −60.99, −122.46; MS (ES+) 584.1 (M+1); (ES−) 582.2 (M−1); Optical rotation: [α]$_D$=(−) 49.20 (1.065, Methanol); Analysis calculated for C$_{29}$H$_{25}$F$_4$N$_5$O$_2$S: C, 59.68; H, 4.32; N, 12.00; Found: C, 59.37; H, 4.61; N, 11.96.

Step-2: Preparation of (−)-N-(5-(amino(phenyl)methyl)-2-fluorophenyl)-1-(3-cyanophenyl)-3-(trifluoromethyl)-1H-pyrazole-5-carboxamide hydrochloride (227b)

To a solution of 1-(3-cyanophenyl)-N-(5-((−)-((R)-1,1-dimethylethylsulfinamido)(phenyl)methyl)-2-fluorophenyl)-3-(trifluoromethyl)-1H-pyrazole-5-carboxamide (227a) (550 g, 942 mmol) in MeOH (6 L) was added drop-wise at room temperature hydrogen chloride (0.415 L, 1659 mmol, 4 N in 1,4-dioxane) over a period of 30 min and stirred for 30 mins. Additional hydrogen chloride (70 mL, 4N in 1,4-dioxane) and (65 mL, 4N in 1,4-dioxane) was added in 30 mins interval stirred at room temperature. The reaction mixture after completion (1 h) was concentrated in vacuum to dryness. The residue obtained was triturated with hexanes (2 L) and solid obtained was collected by filtration, washed with hexanes and dried under vacuum to afford (−)-N-(5-(amino(phenyl)methyl)-2-fluorophenyl)-1-(3-cyanophenyl)-3-(trifluoromethyl)-1H-pyrazole-5-carboxamide hydrochloride (227b) (489.3 g). An analytical sample was prepared by recrystallization from isopropanol to furnish (227b) as a white solid; $^1$H NMR (300 MHz, DMSO-d$_6$) δ 10.70 (s, 1H), 9.02 (s, 3H), 8.13 (d, J=2.1 Hz, 1H), 8.00 (dt, J=7.7, 1.3 Hz, 1H), 7.90 (dd, J=7.2, 2.3 Hz, 1H), 7.77 (s, 1H), 7.73 (t, J=8.0 Hz, 1H), 7.67 (d, J=7.0 Hz, 1H), 7.49-7.36 (m, 7H), 5.70 (s, 1H); $^{19}$F NMR (282 MHz, DMSO) δ −60.99, −120.98; MS (ES+) 480.2 (M+1); (ES−) 478.2 (M−1); Optical rotation: [α]$_D$=(−) 3.60 [1.11, CH$_3$OH], Analysis calculated for C$_{25}$H$_{17}$F$_4$N$_5$O.HCl.1.25H$_2$O: C, 55.77; H, 3.84; Cl, 6.58; N, 13.01; Found: C, 55.87; H, 3.98; Cl, 6.46; N, 12.91.

Step-3: Preparation of (−)-1-(3-cyanophenyl)-N-(5-((cyclopropylmethylamino)(phenyl)methyl)-2-fluorophenyl)-3-(trifluoromethyl)-1H-pyrazole-5-carboxamide (227c)

To a stirred solution of (−)-N-(5-(amino(phenyl)methyl)-2-fluorophenyl)-1-(3-cyanophenyl)-3-(trifluoromethyl)-1H-pyrazole-5-carboxamide (227b) [(50.52 g, 105 mmol), which was converted to free base using aqueous NaHCO$_3$, extracting with ethyl acetate and drying in vacuum prior to use in reaction)] in methanol (530 mL) was added cyclopropanecarbaldehyde (9.84 mL, 132 mmol) and stirred at room temperature for 5 h. The reaction mixture was quenched with sodium borohydride (8.14 g, 211 mmol) carefully with ice/water cooling (inside temp. was between 6° C. and 10° C. during addition) followed by stirring at room temperature for 60 min. Methanol was evaporated in vacuum and residue was treated with water (1 L) and extracted with ethyl acetate (2×1 L, 0.5 L). The combined organic layers were dried over MgSO$_4$, filtered and evaporated to dryness. The residue was purified by flash column chromatography (silica gel 2 kg, eluting with ethyl acetate in hexanes from 0-60%) to afford (−)-1-(3-cyanophenyl)-N-(5-((cyclopropylmethylamino)(phenyl)methyl)-2-fluorophenyl)-3-(trifluoromethyl)-1H-pyrazole-5-carboxamide (227c) (39.85 g, 71% yield) as a colorless oil; $^1$H NMR (300 MHz, DMSO-d$_6$) δ 10.54 (s, 1H, D$_2$O exchangeable), 8.14-8.07 (m, 1H), 7.97 (dt, J=7.7, 1.3 Hz, 1H), 7.93-7.85 (m, 1H), 7.75-7.66 (m, 2H), 7.58 (dd, J=7.6, 2.2 Hz, 1H), 7.45-7.12

(m, 7H), 4.83 (s, 1H), 2.42 (s, 1H), 2.26 (m, 2H), 0.90 (m, 1H), 0.45-0.28 (m, 2H), 0.03 (m, 2H); $^{19}$F NMR (282 MHz, DMSO-d$_6$) δ −60.86, −123.17; MS (ES$^+$): MS (ES+) 534.2 (M+1); 532.2 (M−1); Optical rotation: [α]$_D$=(−) 7.83 [0.23, MeOH].

Step-4: Preparation of (−)-1-(3-carbamimidoylphenyl)-N-(5-((cyclopropylmethylamino)(phenyl)methyl)-2-fluorophenyl)-3-(trifluoromethyl)-1H-pyrazole-5-carboxamide (227d)

To a solution of (−)-1-(3-cyanophenyl)-N-(5-((cyclopropylmethylamino)(phenyl)methyl)-2-fluorophenyl)-3-(trifluoromethyl)-1H-pyrazole-5-carboxamide (227c) (1.0 g, 1.874 mmol) in THF (15 mL) was added LiHMDS (1 M in THF, 4.00 mL, 4.00 mmol) and stirred at room temperature for 24 h. Additional LiHMDS (1 M in THF, 4.00 mL, 4.00 mmol) was added and reaction was heated at reflux for 5.5 h. The reaction mixture was cooled to room temperature and concentrated in vacuum to dryness. The residue was acidified with 1N KHSO$_4$ (15 mL) and extracted with ethyl acetate (2×30 mL). The organic layers were combined, dried over anhydrous MgSO$_4$, filtered and evaporated to dryness. The residue obtained was purified by flash column chromatography (silica gel 25 g, eluting with CMA80 in CHCl$_3$ from 0 to 100%)] to (−)-1-(3-carbamimidoylphenyl)-N-(5-((cyclopropylmethylamino)(phenyl)methyl)-2-fluorophenyl)-3-(trifluoromethyl)-1H-pyrazole-5-carboxamide (227d) (0.205 g, 20% yield) free base as a yellow solid; $^1$H NMR (300 MHz, DMSO-d$_6$) δ 7.97 (t, J=1.8 Hz, 1H), 7.91 (dt, J=7.6, 1.5 Hz, 1H), 7.59 (dd, J=15.0, 7.7 Hz, 4H), 7.43-7.36 (m, 2H), 7.35-7.25 (m, 3H), 7.23-7.14 (m, 2H), 4.83 (s, 1H), 2.26 (d, J=6.1 Hz, 2H), 0.90 (m, 1H), 0.42-0.32 (m, 2H), 0.07-0.01 (m, 2H); MS (ES+): 551.4 (M+1); 549.4 (M−1).

Preparation of HCl salt of (−)-1-(3-carbamimidoylphenyl)-N-(5-((cyclopropylmethylamino)(phenyl)methyl)-2-fluorophenyl)-3-(trifluoromethyl)-1H-pyrazole-5-carboxamide (227d)

To a stirred solution of free base of 227d (0.152 g, 0.276 mmol) in ethanol (5 mL) was added conc. HCl (0.115 mL, 1.380 mmol) and stirred at room for 10 min. The solution was evaporated to dryness to afford (−)-1-(3-carbamimidoylphenyl)-N-(5-((cyclopropylmethylamino)(phenyl)methyl)-2-fluorophenyl)-3-(trifluoromethyl)-1H-pyrazole-5-carboxamide (227d) (0.165 g, 0.248 mmol, 90% yield) hydrochloride salt as a yellow solid.

$^1$H NMR (300 MHz, DMSO-d$_6$) δ 10.84 (s, 1H, D$_2$O exchangeable), 10.20 (s, 2H, D$_2$O exchangeable), 9.53 (s, 2H, D$_2$O exchangeable), 9.29 (s, 2H, D$_2$O exchangeable), 8.03 (t, J=1.9 Hz, 1H), 7.97 (dt, J=8.0, 1.4 Hz, 1H), 7.89 (ddd, J=9.2, 7.3, 2.1 Hz, 2H), 7.82 (s, 1H), 7.80-7.67 (m, 4H), 7.50-7.32 (m, 4H), 5.65 (t, J=6.5 Hz, 1H), 2.71 (d, J=11.3 Hz, 2H), 1.18-1.13 (m, 1H), 0.65-0.45 (m, 2H), 0.30 (m, 2H); $^{19}$F NMR (282 MHz, DMSO-d$_6$) δ −60.87, −120.21; MS (ES+) 551.4 (M+1); MS (ES−) 549.34 (M−1), 585.36 (M+Cl); Optical rotation: [α]$_D$=(−) 1.57 [0.51, CH$_3$OH]; Analysis calculated for C$_{29}$H$_{26}$F$_4$N$_6$O.2HCl.2.25H$_2$O: C, 52.46; H, 4.93; N, 12.66; Found: C, 52.62; H, 4.89; N, 12.27.

Scheme 228

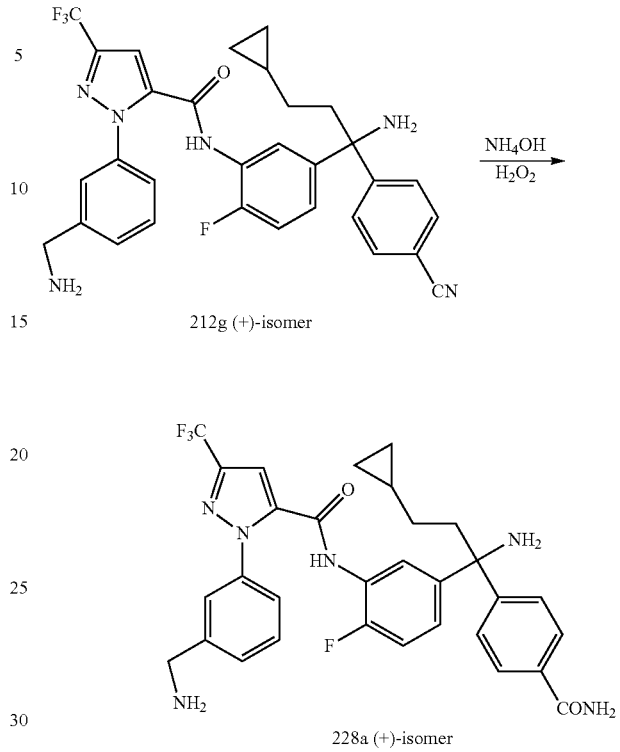

212g (+)-isomer 228a (+)-isomer

Preparation of (+)-N-(5-(1-amino-1-(4-carbamoylphenyl)-3-cyclopropylpropyl)-2-fluorophenyl)-1-(3-(aminomethyl)phenyl)-3-(trifluoromethyl)-1H-pyrazole-5-carboxamide (228a)

To a stirred solution of (+)-N-(5-(1-amino-1-(4-cyanophenyl)-3-cyclopropylpropyl)-2-fluorophenyl)-1-(3-(aminomethyl)phenyl)-3-(trifluoromethyl)-1H-pyrazole-5-carboxamide (212g) (80 mg, 0.123 mmol) in ethanol (10 mL) was added ammonium hydroxide (10 mL, 257 mmol) hydrogen peroxide (1 mL, 32.6 mmol) and stirred at room temperature overnight. Additional hydrogen peroxide (1 mL, 32.6 mmol) was added to the reaction mixture and continued stirring for 24 h. The reaction was concentrated in vacuum; residual water was removed by azeotropic distillation with ethanol (50 mL). The crude residue obtained was purified by flash column chromatography (silica gel 12 g, eluting with CMA 80 in chloroform) to afford (+)-N-(5-(1-amino-1-(4-carbamoylphenyl)-3-cyclopropylpropyl)-2-fluorophenyl)-1-(3-(aminomethyl)phenyl)-3-(trifluoromethyl)-1H-pyrazole-5-carboxamide (228a) (32 mg, 0.054 mmol, 43.7% yield) as a white solid; $^1$H NMR (300 MHz, DMSO-d$_6$) δ 10.52 (s, 1H), 7.90 (s, 1H), 7.79-7.72 (m, 2H), 7.55 (d, J=5.9 Hz, 2H), 7.50 (s, 1H), 7.42 (dd, J=7.9, 2.6 Hz, 4H), 7.36-7.24 (m, 3H), 7.16 (t, J=9.4 Hz, 1H), 3.77 (s, 2H), 2.32-2.11 (m, 4H), 1.13-0.90 (m, 2H), 0.62 (m, 1H), 0.42-0.25 (m, 2H), −0.09 (m, 2H); 19F NMR (282 MHz, DMSO-d$_6$) δ −60.72, −124.35 (q, J=9.8, 7.8 Hz); MS (ES+) 595.5 (M+1), 617.5 (M+Na); Optical rotation: [α]$_D$=(+) 8.57 [0.21, CH$_3$OH].

825

Scheme 229

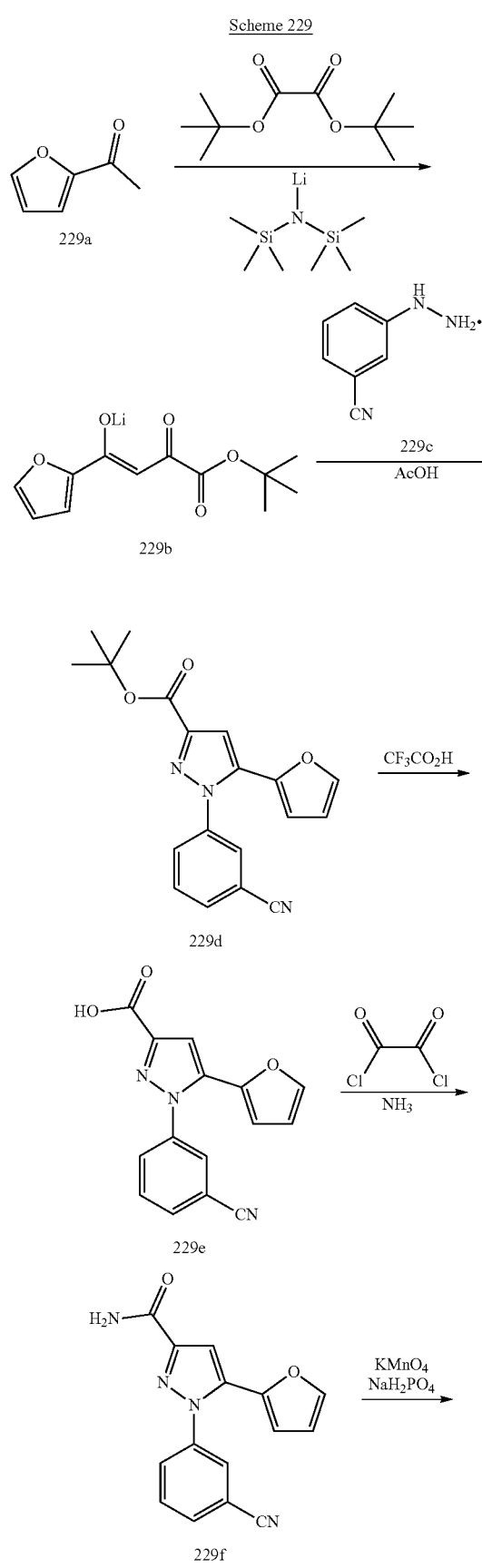

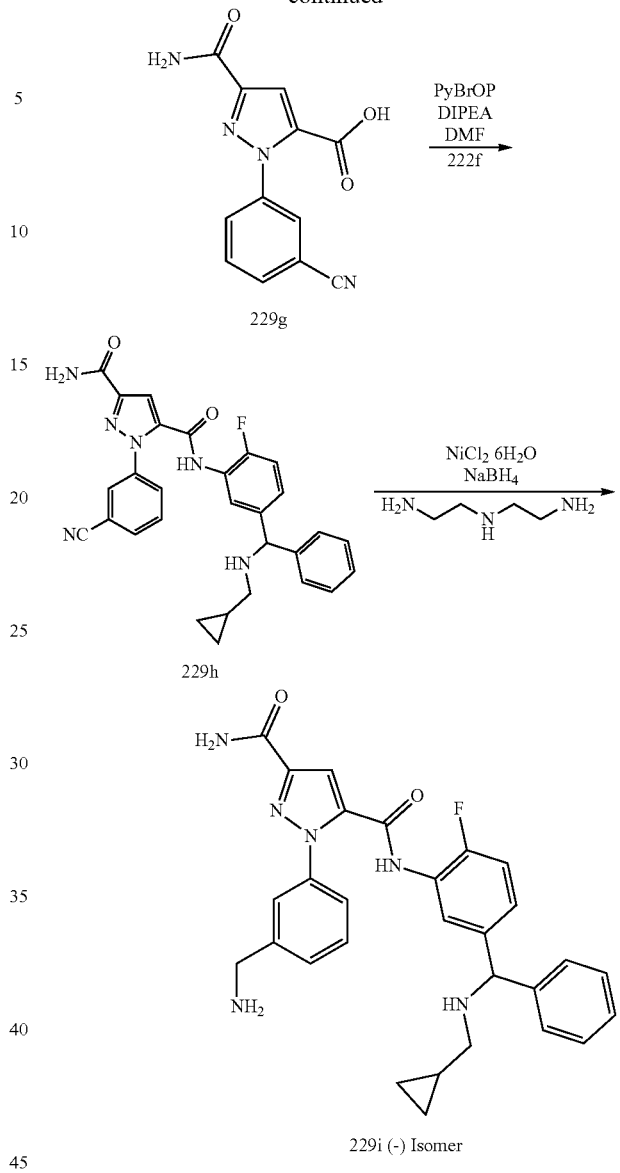

Preparation of (−)-1-(3-(aminomethyl)phenyl)-N₅-(5-((cyclopropylmethylamino)(phenyl)-methyl)-2-fluorophenyl)-1H-pyrazole-3,5-dicarboxamide (229i)

Step-1: Preparation of Lithium (Z)-4-tert-butoxy-1-(furan-2-yl)-3,4-dioxobut-1-en-1-olate (229b)

To LiHMDS (134 mL, 134 mmol, 1 M solution in THF) in diethyl ether (410 mL) cooled to −78° C. was added 1-(furan-2-yl)ethanone (229a) (14 g, 127 mmol) in one portion and stirred for 5 mins. To this was added a solution of di-tert-butyl oxalate (25.7 g, 127 mmol) in diethyl ether (100 mL). The reaction mixture was allowed to warm to room temperature overnight. The mixture was filtered and the resulting yellow solid was washed with ether (100 mL), dried in vacuum to afford lithium (Z)-4-tert-butoxy-1-(furan-2-yl)-3,4-dioxobut-1-en-1-olate (229b) (23.6 g, 97 mmol, 76% yield) which was used as such for next step; $^1$H NMR (300 MHz, DMSO-d$_6$) δ 7.75 (dd, J=1.7, 0.8 Hz, 1H), 6.95 (dd, J=3.4, 0.9 Hz, 1H), 6.56 (dd, J=3.4, 1.7 Hz, 1H), 6.24 (s, 1H), 1.46 (s, 9H); MS (ES−) 237.059 (M−1).

Step-2: Preparation of tert-Butyl 1-(3-cyanophenyl)-5-(furan-2-yl)-1H-pyrazole-3-carboxylate (229d)

To lithium (Z)-4-tert-butoxy-1-(furan-2-yl)-3,4-dioxobut-1-en-1-olate (229b) (21.59 g, 88 mmol) and 3-hydrazinyl-benzonitrile hydrochloride (229c) (15 g, 88 mmol) was added AcOH (400 mL) and stirred at room temperature overnight. The mixture was concentrated in vacuum and the residue obtained was purified by flash column chromatography (silica gel 300 g, eluting with 25% ethyl acetate in hexane) to furnish tert-butyl 1-(3-cyanophenyl)-5-(furan-2-yl)-1H-pyrazole-3-carboxylate (229d) (24.658 g, 73.5 mmol, 83% yield) as an yellow oil, which solidified on standing; $^1$H NMR (300 MHz, DMSO-$d_6$) δ 8.10-7.98 (m, 2H), 7.88-7.72 (m, 3H), 7.15 (s, 1H), 6.56 (dd, J=3.5, 1.8 Hz, 1H), 6.41 (dd, J=3.4, 0.8 Hz, 1H), 1.55 (s, 9H); MS (ES+) 358.3 (M+Na).

Step-3: Preparation of 1-(3-Cyanophenyl)-5-(furan-2-yl)-1H-pyrazole-3-carboxylic Acid (229e)

To a solution of tert-butyl 1-(3-cyanophenyl)-5-(furan-2-yl)-1H-pyrazole-3-carboxylate (229d) (23 g, 68.6 mmol) in dichloromethane (250 mL) was added trifluoroacetic acid (211 mL, 2743 mmol) and stirred at room temperature for 5 h. The reaction was concentrated in vacuum to dryness to furnish 1-(3-cyanophenyl)-5-(furan-2-yl)-1H-pyrazole-3-carboxylic acid (229e) (19.0 g, 68.0 mmol, 99% yield) as an off white solid; $^1$H NMR (300 MHz, DMSO-$d_6$) δ 8.07-8.00 (m, 2H), 7.87-7.71 (m, 3H), 7.19 (s, 1H), 6.58 (dd, J=3.5, 1.8 Hz, 1H), 6.46 (dd, J=3.5, 0.8 Hz, 1H); MS (ES+) 280.3 (M+1); 302.2 (M+Na).

Step-4: Preparation of 1-(3-Cyanophenyl)-5-(furan-2-yl)-1H-pyrazole-3-carboxamide (229f)

To a solution of 1-(3-cyanophenyl)-5-(furan-2-yl)-1H-pyrazole-3-carboxylic acid (229e) (13 g, 46.6 mmol) in dichloromethane (75 mL) was added oxalyl chloride (2 M solution in dichloromethane, 46.6 mL, 93 mmol) followed by DMF (10 drops). The reaction mixture was stirred at room temperature for 5 h and concentrated in vacuum to dryness. The residue obtained was dissolved in dichloromethane (250 mL), added ammonia in dioxane (0.5 M solution, 233 mL, 116 mmol) and stirred at room temperature overnight. The reaction mixture was concentrated in vacuum and the residue was poured into water. The aqueous layer was extracted with ethyl acetate (3×100 mL). The organic layers were combined washed with brine (100 mL), dried, filtered and concentrated in vacuum to afford 1-(3-cyanophenyl)-5-(furan-2-yl)-1H-pyrazole-3-carboxamide (229f) (10.2 g, 36.7 mmol, 79% yield) as a brown solid; $^1$H NMR (300 MHz, DMSO-$d_6$) δ 8.08 (ddd, J=2.2, 1.6, 0.6 Hz, 1H), 8.01 (dt, J=7.4, 1.5 Hz, 1H), 7.85-7.72 (m, 4H), 7.52-7.40 (m, 1H), 7.12 (s, 1H), 6.58 (dd, J=3.5, 1.8 Hz, 1H), 6.44 (dd, J=3.5, 0.8 Hz, 1H); MS (ES+) 279.3 (M+1); 301.3 (M+Na); (ES−) 277.4 (M−1).

Step-5: Preparation of 3-Carbamoyl-1-(3-cyanophenyl)-1H-pyrazole-5-carboxylic acid (229g)

To a solution of 1-(3-cyanophenyl)-5-(furan-2-yl)-1H-pyrazole-3-carboxamide (229f) (7.5 g, 27.0 mmol) in Water (150 mL) and t-BuOH (150 mL) was added sodium dihydrogen phosphate (5% aqueous, 105 mL, 53.6 mmol). The resulting solution was warmed to 60° C. and added potassium permanganate (20.31 g, 129 mmol) in small portions over a period of 30 mins. The slurry was stirred for 30 mins cooled to 0° C. and quenched with saturated aqueous sodium bisulfite (428 mL, 2142 mmol). The resulting mixture was filtered, washed with water (300 mL), and filtrate was acidified with Conc. HCl. The solid obtained was collected by filtration to afford on drying 3-carbamoyl-1-(3-cyanophenyl)-1H-pyrazole-5-carboxylic acid (229g) (2.48 g, 9.68 mmol, 45.2% yield) as a white solid. The aqueous layer was concentrated in vacuum to about 50 mL and extracted with ethyl acetate (5×50 mL). The organic layers were combined dried, filtered and concentrated in vacuum to afford 3-carbamoyl-1-(3-cyanophenyl)-1H-pyrazole-5-carboxylic acid (229g) (2.9 g, 11.32 mmol, 52.8% yield) as a second crop which was pure enough to be used for next step; $^1$H NMR (300 MHz, DMSO-$d_6$) δ 8.17 (s, 1H), 8.01-7.86 (m, 3H), 7.72 (t, J=7.8 Hz, 1H), 7.53 (s, 1H), 7.33 (s, 1H); MS (ES−) 255.1 (M−1).

Step-6: Preparation of 1-(3-cyanophenyl)-N5-(5-((cyclopropylmethylamino)(phenyl)methyl)-2-fluorophenyl)-1H-pyrazole-3,5-dicarboxamide (229h)

Compound 229h was prepared from 3-carbamoyl-1-(3-cyanophenyl)-1H-pyrazole-5-carboxylic acid (229g) (0.606 g, 2.364 mmol) and (−)-5-((cyclopropylmethylamino)-(phenyl)methyl)-2-fluoroaniline (222f) (0.581 g, 2.149 mmol) as described in step-3 of scheme-208 to afford 1-(3-cyanophenyl)-N$_5$-(5-((cyclopropylmethylamino)(phenyl)methyl)-2-fluorophenyl)-1H-pyrazole-3,5-dicarboxamide (229h) (0.706 g, 65% yield) as a yellow syrup which was used as such in the next step; $^1$H NMR (300 MHz, DMSO-$d_6$) δ 10.46 (s, 1H), 8.10 (s, 1H), 7.95 (dt, J=7.7, 1.3 Hz, 1H), 7.87 (d, J=7.1 Hz, 2H), 7.70 (t, J=7.9 Hz, 1H), 7.62-7.49 (m, 3H), 7.44-7.13 (m, 7H), 4.84 (s, 1H), 2.35-2.20 (m, 2H), 1.02-0.85 (m, 1H), 0.51-0.28 (m, 2H), 0.05 (m, 2H); $^{19}$F NMR (282 MHz, DMSO-$d_6$) δ −123.18; MS (ES+): 509.4.

Step-7: Preparation of (−)-1-(3-(aminomethyl)phenyl)-N$_5$-(5-((cyclopropylmethylamino)-(phenyl)methyl)-2-fluorophenyl)-1H-pyrazole-3,5-dicarboxamide (229i)

Compound 229i was prepared from 1-(3-cyanophenyl)-N$_5$-(5-((cyclopropylmethylamino)(phenyl)methyl)-2-fluorophenyl)-1H-pyrazole-3,5-dicarboxamide (229h) (0.681 g, 1.339 mmol) according to the procedure reported for preparation of compound 15g in step-6 of scheme-15 to furnish (−)-1-(3-(aminomethyl)phenyl)-N5-(5-((cyclopropyl-methylamino)(phenyl)methyl)-2-fluorophenyl)-1H-pyrazole-3,5-dicarboxamide (229i) (89 mg, 13% yield) as a white solid; $^1$H NMR (300 MHz, DMSO-$d_6$) δ 10.42 (s, 1H, D$_2$O exchangeable), 7.79 (s, 1H), 7.64-7.55 (m, 1H), 7.49 (d, J=7.0 Hz, 2H), 7.45-7.36 (m, 5H), 7.35-7.24 (m, 4H), 7.18 (td, J=8.5, 2.3 Hz, 2H), 4.83 (s, 1H), 3.79 (s, 2H), 2.27 (m, 2H), 0.91 (m, 1H), 0.47-0.27 (m, 2H), 0.04 (m, 2H); $^{19}$F NMR (282 MHz, DMSO-$d_6$) δ −123.40; MS (ES+) 513.4 (M+1); MS (ES−) 511.5 (M−1); Optical rotation: [α]$_D$=(−) 4.17 [0.24, CH$_3$OH]; Analysis calculated for: C$_{29}$H$_{29}$FN$_6$O$_2$.1.5H$_2$O: C, 64.55; H, 5.98; F, 3.52; N, 15.57; Found: C, 64.34; H, 5.95; F, 4.40; N, 15.62.

Scheme 230

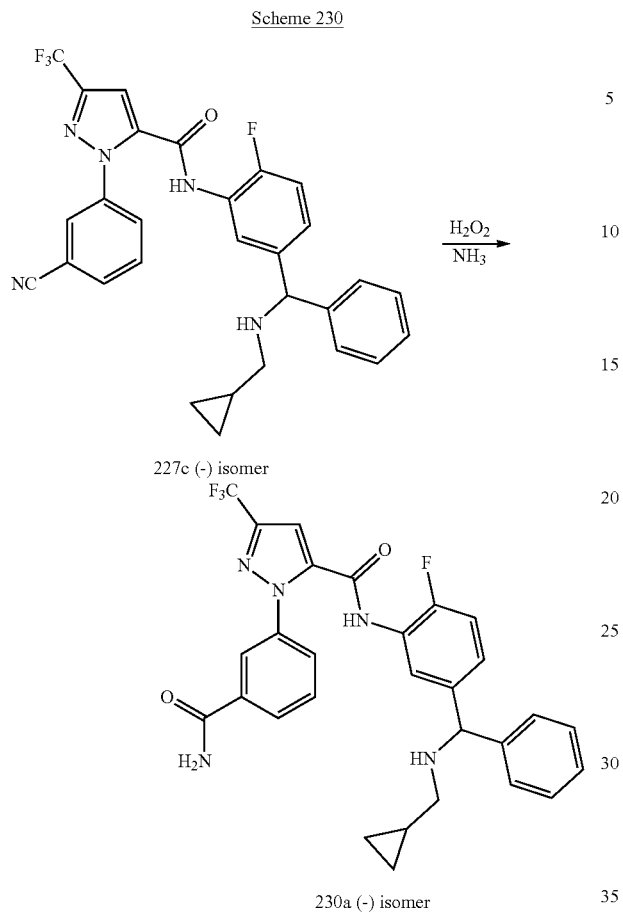

Preparation of (−)-1-(3-carbamoylphenyl)-N-(5-((cyclopropylmethylamino)(phenyl)methyl)-2-fluorophenyl)-3-(trifluoromethyl)-1H-pyrazole-5-carboxamide (230a)

To a stirred solution of (−)-1-(3-cyanophenyl)-N-(5-((cyclopropylmethylamino)(phenyl)methyl)-2-fluorophenyl)-3-(trifluoromethyl)-1H-pyrazole-5-carboxamide (227c) (1.067 g, 2.0 mmol) in ethanol (50 mL) was added ammonium hydroxide (19 mL, 257 mmol) hydrogen peroxide (0.700 mL, 7.92 mmol) and stirred at room temperature for 22 h. The reaction was concentrated in vacuum and crude residue obtained was purified by flash column chromatography (silica gel 25 g, eluting with CMA 80 in chloroform) to afford (−)-1-(3-carbamoylphenyl)-N-(5-((cyclopropylmethylamino)(phenyl)methyl)-2-fluorophenyl)-3-(trifluoromethyl)-1H-pyrazole-5-carboxamide (230a) (108 mg, 0.196 mmol, 9.79% yield) as a white solid; $^1$H NMR (300 MHz, DMSO-$d_6$) δ 10.53 (s, 1H), 8.15 (s, 1H), 8.04-7.97 (m, 2H), 7.70-7.52 (m, 5H), 7.42-7.36 (m, 2H), 7.35-7.13 (m, 5H), 4.83 (s, 1H), 2.32-2.20 (m, 2H), 0.97-0.78 (m, 1H), 0.44-0.29 (m, 2H), 0.07-0.00 (m, 2H); $^{19}$F NMR (282 MHz, DMSO) δ −60.63, −123.40; MS (ES+): 552.4 (M+H); Optical rotation: $[α]_D$=(−) 6.51 (0.215, Methanol); Analysis calculated for $C_{29}H_{25}F_4N_5O_2$: C, 63.15; H, 4.57; N, 12.70. Found: C, 62.97; H, 4.57; N, 12.72.

Scheme 231

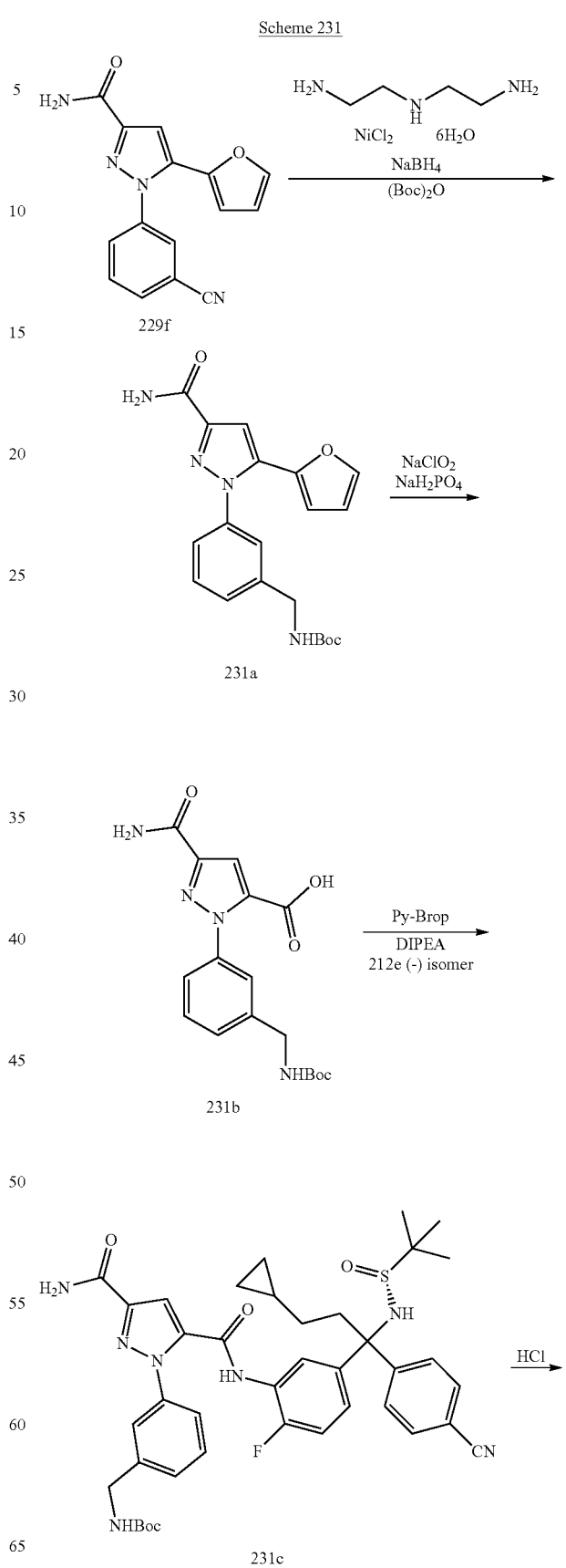

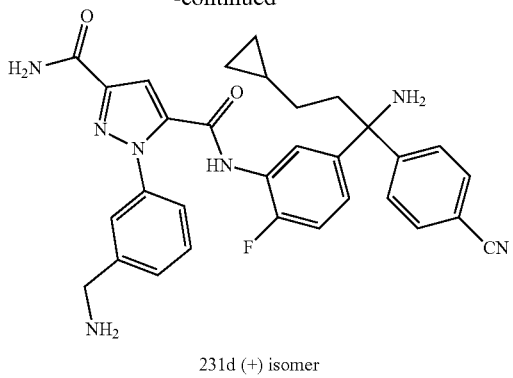

231d (+) isomer

Preparation of (+)-N$^5$-(5-(1-amino-1-(4-cyanophenyl)-3-cyclopropylpropyl)-2-fluorophenyl)-1-(3-(aminomethyl)phenyl)-1H-pyrazole-3,5-dicarboxamide (231d)

Step-1 Preparation of tert-butyl 3-(3-carbamoyl-5-(furan-2-yl)-1H-pyrazol-1-yl)benzylcarbamate (231a)

To a solution of 1-(3-Cyanophenyl)-5-(furan-2-yl)-1H-pyrazole-3-carboxamide (229f) in methanol (100 mL) cooled with ice/water was added nickel(II) chloride hexahydrate (0.322 g, 1.353 mmol) and Boc anhydride (3.14 mL, 13.53 mmol) followed by portionwise addition of sodium borohydride (2.56 g, 67.6 mmol) over a period of 15 min. The reaction mixture was stirred at room temperature for 2 h and quenched with N1-(2-aminoethyl)ethane-1,2-diamine (4.38 mL, 40.6 mmol) followed by stirring for additional 0.5 h. The reaction mixture was concentrated in vacuum to dryness. The residue was treated with water (50 mL), and extracted with ethyl acetate (2×100 mL). The organic layers were combined dried, filtered and concentrated in vacuum to dryness. The residue was purified by flash column chromatography (silica gel 25 g, eluting with methanol in chloroform from 0 to 25%) to furnish tert-butyl 3-(3-carbamoyl-5-(furan-2-yl)-1H-pyrazol-1-yl)benzylcarbamate (231a) (1.8 g, 4.71 mmol, 69.6% yield) as a colorless solid. $^1$H NMR (300 MHz, DMSO-d$_6$) δ 7.73 (dd, J=1.9, 0.8 Hz, 2H), 7.49 (dd, J=9.0, 6.4 Hz, 2H), 7.45-7.38 (m, 2H), 7.36 (d, J=1.8 Hz, 1H), 7.31 (dd, J=7.8, 1.7 Hz, 1H), 7.06 (s, 1H), 6.50 (dd, J=3.5, 1.8 Hz, 1H), 6.13 (d, J=3.5 Hz, 1H), 4.19 (d, J=6.2 Hz, 2H), 1.37 (s, 9H).

Step-2 Preparation of 1-(3-((tert-butoxycarbonylamino)methyl)phenyl)-3-carbamoyl-1H-pyrazole-5-carboxylic Acid (231b)

To a solution of furnish tert-butyl 3-(3-carbamoyl-5-(furan-2-yl)-1H-pyrazol-1-yl)benzylcarbamate (231a) (0.65 g, 1.70 mmol), sodium dihydrogen phosphate (1.02 g, 8.50 mmol) in acetonitrile (10 mL) and water (2 mL) was added a solution of sodium chlorite (1.537 g, 17.00 mmol) in water (10.00 mL) and stirred at room temperature overnight. The reaction was evaporated to dryness. The residue was treated with sat. NaHCO$_3$, extracted with chloroform (2×50 mL). The combined organics were dried, filtered, evaporated to dryness. The residue was purified by flash chromatography {silica gel 24 g, eluting with CMA80 in chloroform, 0-100%) to afford 1-(3-(((tert-butoxycarbonylamino)methyl)phenyl)-3-carbamoyl-1H-pyrazole-5-carboxylic acid (231b) (225 mg, 0.624 mmol, 36.7% yield) as a white solid.

$^1$H NMR (300 MHz, DMSO-d$_6$) δ 7.83 (s, 1H), 7.49 (td, J=18.8, 17.7, 8.7 Hz, 3H), 7.39-7.34 (m, 2H), 4.19 (d, J=6.3 Hz, 2H), 1.39 (s, 9H); MS (ES+) 383.3 (M+Na), (ES−) 359.3 (M−1).

Step-3 Preparation of tert-butyl 3-(3-carbamoyl-5-(5-(1-(4-cyanophenyl)-3-cyclopropyl-1-((R)-1,1-dimethylethylsulfinamido)propyl)-2-fluorophenylcarbamoyl)-1H-pyrazol-1-yl)benzylcarbamate (231c)

To a solution of 1-(3-((tert-butoxycarbonylamino)methyl)phenyl)-3-carbamoyl-1H-pyrazole-5-carboxylic acid (231b) (210 mg, 0.582 mmol) in N,N-dimethylformamide (4.10 mL, 52.9 mmol) was added (R)—N-((−)-1-(3-amino-4-fluorophenyl)-1-(4-cyanophenyl)-3-cyclopropylpropyl)-2-methylpropane-2-sulfinamide (212e) (219 mg, 0.529 mmol), N-ethyl-N-isopropylpropan-2-amine (0.461 mL, 2.65 mmol) and bromo-tris-pyrrolidino phosphoniumhexafluorophosphate(PyBrop) (296 mg, 0.635 mmol) at room temperature. The reaction mixture was stirred at room temperature for 12 h under nitrogen atmosphere. The reaction was diluted with water (40 mL) and extracted with ethyl acetate (2×50 mL). The organic layers were combined, washed with brine (25 mL), dried, filtered, and concentrated in vacuum to dryness. The residue obtained was purified by flash column chromatography (silica gel 25 g, eluting with 0-100% ethyl acetate in hexanes) to furnish tert-butyl 3-(3-carbamoyl-5-(5-(1-(4-cyanophenyl)-3-cyclopropyl-1-((R)-1,1-dimethylethylsulfinamido)propyl)-2-fluorophenylcarbamoyl)-1H-pyrazol-1-yl)benzylcarbamate (231c) (78 mg, 0.103 mmol, 19.49% yield) as a colorless solid; $^1$H NMR (300 MHz, DMSO-d$_6$) δ 10.48 (s, 1H), 7.82 (s, 1H), 7.77 (d, J=8.3 Hz, 2H), 7.64-7.46 (m, 2H), 7.48-7.27 (m, 6H), 7.21 (d, J=7.6 Hz, 2H), 5.56 (s, 1H), 4.17 (d, J=6.3 Hz, 2H), 2.71-2.39 (m, 2H), 1.37 (s, 9H), 1.35-1.13 (m, 1H), 1.12 (s, 9H), 0.98-0.77 (m, 1H), 0.72-0.51 (m, 1H), 0.42-0.25 (m, 2H), −0.03-−0.19 (m, 2H); $^{19}$F NMR (282 MHz, DMSO-d$_6$) δ −122.74; MS (ES+) 778.6 (M+Na).

Step-4 Preparation of (+)-N$^5$-(5-(1-amino-1-(4-cyanophenyl)-3-cyclopropylpropyl)-2-fluorophenyl)-1-(3-(aminomethyl)phenyl)-1H-pyrazole-3,5-dicarboxamide (231d)

To a solution of tert-butyl 3-(3-carbamoyl-5-(5-(1-(4-cyanophenyl)-3-cyclopropyl-1-((R)-1,1-dimethylethylsulfinamido)propyl)-2-fluorophenylcarbamoyl)-1H-pyrazol-1-yl)benzylcarbamate (231c) (70 mg, 0.093 mmol) in ethanol (5 mL) was added Conc. HCl (0.077 mL, 0.924 mmol), stirred for 1 h and concentrated in vacuum to dryness. The residue was purified by flash column chromatography (silica gel) to afford 231d (50 mg, 0.091 mmol, 98% yield) free base an off white solid; $^1$H NMR (300 MHz, DMSO-d$_6$) δ 10.41 (s, 1H), 7.86-7.69 (m, 3H), 7.57 (d, J=8.1 Hz, 3H), 7.48 (s, 2H), 7.40 (dd, J=6.3, 4.1 Hz, 3H), 7.27 (ddt, J=15.5, 4.7, 2.4 Hz, 2H), 7.17 (t, J=9.4 Hz, 1H), 3.76 (s, 2H), 2.57 (m, 2H), 2.23 (m, 2H), 1.06-0.89 (m, 2H), 0.5-0.6 (m, 1H), 0.44-0.28 (m, 2H), −0.08 (m, 2H); $^{19}$F NMR (282 MHz, DMSO-d$_6$) δ −123.86; MS (ES−) 550.4, 551.5 (M−1).

To a solution of free base was in ethanol (5 mL) was added Conc. HCl (0.077 mL, 0.924 mmol), stirred for 5 mins and concentrated in vacuum to dryness. The residue was dissolved in water (1 mL) and dried under vacuum to furnish (+)-N$^5$-(5-(1-amino-1-(4-cyanophenyl)-3-cyclopropylpropyl)-2-fluorophenyl)-1-(3-(aminomethyl)phenyl)-1H-pyrazole-3, 5-dicarboxamide (231d) (0.046 g, 0.074 mmol, 80% yield) hydrochloride as an off white solid; $^1$H NMR (300 MHz, DMSO-d$_6$) δ 10.65 (s, 1H), 9.48 (s, 3H), 8.48 (s, 3H), 7.97-7.91 (m, 2H), 7.80-7.75 (m, 1H), 7.71 (t, J=1.8 Hz, 1H), 7.63-7.45 (m, 8H), 7.43-7.26 (m, 2H), 4.09 (q, J=5.7 Hz, 2H), 2.65-2.52 (m, 2H), 1.26-0.95 (m, 2H), 0.77-0.60 (m, 1H), 0.47-0.27 (m, 2H), 0.00 (m, 2H); $^{19}$F NMR (282 MHz, DMSO) δ −120.20; MS (ES+) 552.5 (M+1); (ES−) 550.3 (M−1); Optical rotation: [α]$_D$=(+) 18.67 [0.225, MeOH].

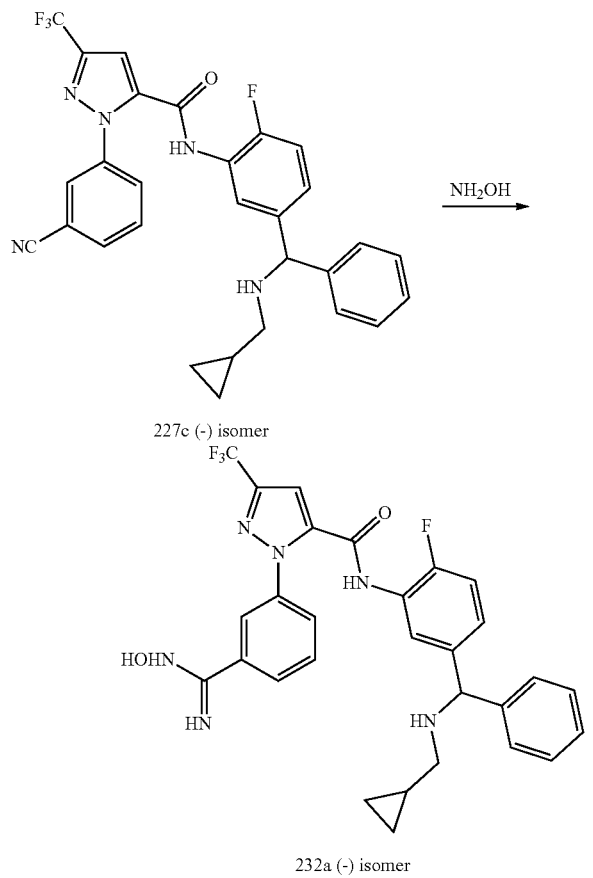

Scheme 232

227c (−) isomer 232a (−) isomer

Preparation of (−)-N-(5-((cyclopropylmethylamino)(phenyl)methyl)-2-fluorophenyl)-1-(3-(N-hydroxycarbamimidoyl)phenyl)-3-(trifluoromethyl)-1H-pyrazole-5-carboxamide (232a)

To a stirred solution of (−)-1-(3-cyanophenyl)-N-(5-((cyclopropylmethylamino)(phenyl)methyl)-2-fluorophenyl)-3-(trifluoromethyl)-1H-pyrazole-5-carboxamide (227c) (1 g, 1.874 mmol) in ethanol (15 mL) was added hydroxylamine (1.10 mL, 18.65 mmol) and heated at reflux for 1 h. The reaction was concentrated in vacuum and crude residue obtained was purified by flash column chromatography [silica gel 25 g, eluting with hexanes/ethyl acetate (1:0 to 1:1)] to afford compound 232a (873 mg, 1.1541 mmol, 82% yield) free base as a white solid; $^1$H NMR (300 MHz, DMSO-d$_6$) δ 10.51 (s, 1H), 9.84 (s, 1H), 7.87-7.83 (m, 1H), 7.80 (td, J=4.4, 1.7 Hz, 1H), 7.65-7.58 (m, 2H), 7.51-7.48 (m, 2H), 7.41-7.13 (m, 7H), 5.93 (s, 2H), 4.83 (s, 1H), 2.32-2.21 (m, 2H), 0.98-0.80 (m, 1H), 0.44-0.28 (m, 2H), 0.10-−0.05 (m, 2H); $^{19}$F NMR (282 MHz, DMSO-d$_6$) δ −60.61, −123.51; MS (ES+) 567.4 (M+1), 565.3 (M−1).

To a solution of free base of 232a (400 mg, 0.71 mmol) in methanol (10 mL) was added 4 N aqueous HCl (aqueous 0.71 mL) and concentrated in vacuum to dryness to afford (−)-N-(5-((cyclopropylmethylamino)(phenyl)methyl)-2-fluorophenyl)-1-(3-(N-hydroxycarbamimidoyl)phenyl)-3-(trifluoromethyl)-1H-pyrazole-5-carboxamide (232a) (427 mg, 89.53% yield) hydrochloride salt as a white solid; $^1$H NMR (300 MHz, DMSO-d$_6$) δ 11.25 (s, 1H), 10.81 (s, 1H), 10.14 (s, 2H), 8.98 (s, 1H), 7.94 (t, J=1.9 Hz, 1H), 7.91-7.80 (m, 3H), 7.80-7.66 (m, 5H), 7.48-7.31 (m, 4H), 5.69-5.62 (m, 1H), 2.77-2.60 (m, 2H), 1.23-1.09 (m, 1H), 0.62-0.47 (m, 2H), 0.37-0.23 (m, 2H); $^{19}$F NMR (282 MHz, DMSO) δ −60.70, −120.13; MS (ES−) 565.4 (M−1), 601.3 (M+Cl); Optical rotation: [α]$_D$=(−) 0.38 (0.52, Methanol); Analysis calculated for $C_{29}H_{26}F_4N_6O_2 \cdot 2HCl \cdot 2H_2O$: C: 51.56; H: 4.77; N: 12.44; Found C: 51.21; H: 4.82; N: 12.00.

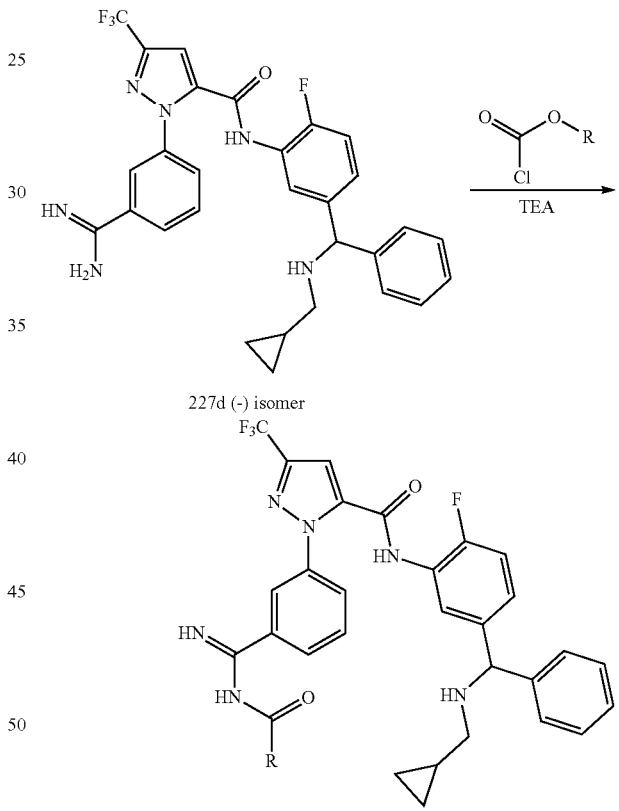

Scheme 233

227d (−) isomer

R = OCH$_2$CH$_3$ 233a (−) isomer
R = OCH$_2$(CH$_2$)$_4$CH$_3$ 233b (−) isomer
R = OCH$_2$CCl$_3$ 233c (−) isomer
R = SCH$_2$CH$_3$ 233d (−) isomer
R = OCH(CH$_3$)OCOCH$_3$ 233e (−) isomer Preparation of (−)-ethyl (3-(5-(5-((cyclopropylmethylamino)(phenyl)methyl)-2-fluorophenylcarbamoyl)-3-(trifluoromethyl)-1H-pyrazol-1-yl)phenyl)(imino)methylcarbamate (233a)

To a solution of (−)-1-(3-carbamimidoylphenyl)-N-(5-((cyclopropylmethylamino)(phenyl)methyl)-2-fluorophenyl)-3-(trifluoromethyl)-1H-pyrazole-5-carboxamide (227d) (200 mg, 0.363 mmol) in acetonitrile (10 mL) was added triethylamine (0.160 mL, 1.148 mmol), ethyl carbonochloridate (0.036 mL, 0.363 mmol) and stirred at room temperature for 14 h. The reaction was diluted with ethyl acetate (120 mL) washed with water (60 mL). The aqueous layer was extracted again with ethyl acetate (60 mL). The combined organic layers were washed with brine (60 mL), dried over MgSO$_4$, filtered and concentrated in vacuum. The residue obtained was purified by flash column chromatography [silica gel, 12 g eluting with hexanes/ethyl acetate (1:0 to 1:1)] to afford compound 233a (130 mg, 0.209 mmol, 57.5%) free base as an off white solid. The solid (55 mg, 0.088 mmol) was dissolved in methanol (8 mL) added 4 N aqueous HCl (0.088 mL) and concentrated in vacuum to dryness to afford (−)-ethyl (3-(5-(5-((cyclopropylmethyl-amino)(phenyl)methyl)-2-fluorophenylcarbamoyl)-3-(trifluoromethyl)-1H-pyrazol-1-yl)phenyl)(imino)methylcarbamate (233a) (60 mg, 92.23%) as an off white solid; $^1$H NMR (300 MHz, DMSO-d$_6$) δ 11.29 (s, 1H), 10.84 (s, 1H), 10.67-10.36 (m, 2H), 10.18 (d, 2H), 8.05 (t, J=1.9 Hz, 1H), 7.94 (d, J=7.9 Hz, 1H), 7.88 (dd, J=7.3, 2.2 Hz, 2H), 7.80 (s, 1H), 7.78-7.66 (m, 4H), 7.48-7.31 (m, 4H), 5.68-5.62 (m, 1H), 4.30 (q, J=7.1 Hz, 2H), 2.76-2.63 (m, 2H), 1.30 (t, J=7.1 Hz, 3H), 1.22-1.02 (m, 1H), 0.66-0.45 (m, 2H), 0.30 (dt, J=6.1, 4.4 Hz, 2H); $^{19}$F NMR (282 MHz, DMSO-d$_6$) δ −60.86, −120.22; MS (ES+): 623.5 (M+1); Optical rotation: $[α]_D$=(−) 13 [0.2, CH$_3$OH]; Analysis calculated for C$_{32}$H$_{30}$F$_4$N$_6$O$_3$.2HCl.2.25H$_2$O: C, 52.22; H, 5.00; Cl, 9.63; N, 11.42; Found C: 52.29; H: 4.85 N: 11.66; Cl: 9.27.

Preparation of (−)-Hexyl (3-(5-(5-((cyclopropylmethylamino)(phenyl)methyl)-2-fluorophenylcarbamoyl)-3-(trifluoromethyl)-1H-pyrazol-1-yl)phenyl)(imino)methylcarbamate (233b)

To a solution of (−)-1-(3-carbamimidoylphenyl)-N-(5-((cyclopropylmethylamino)-(phenyl)methyl)-2-fluorophenyl)-3-(trifluoromethyl)-1H-pyrazole-5-carboxamide (227d) (150 mg, 0.27 mmol) in anhydrous acetonitrile (10 mL) was added triethylamine (88 mg, 0.87 mmol) followed by a solution of hexyl chloroformate (45 mg, 0.27 mmol) in anhydrous acetonitrile (3.0 mL). The reaction mixture was stirred for 11 h at room temperature, diluted with EtOAc (40 mL) and washed with water (20 mL). The aqueous layer was extracted again with EtOAc (20 mL) and combined organic layers were dried over MgSO$_4$, filtered and concentrated in vacuum. The residue obtained was purified by flash column chromatography [silica gel 12 g, eluting with 0-50% (ethyl acetate/MeOH (9:1, v/v) in hexanes) to obtain free base of 233b as a free base. The free base was dissolved MeOH added 3N HCl in MeOH (5.0 mL), stirred for 4 h at room temperature and concentrated in vacuum to furnish (−)-Hexyl (3-(5-(5-((cyclopropylmethylamino)-(phenyl)methyl)-2-fluorophenylcarbamoyl)-3-(trifluoromethyl)-1H-pyrazol-1-yl)phenyl)(imino)methylcarbamate (233b) (126 mg, 59% yield) hydrochloride as a white solid.

$^1$H NMR (300 MHz, DMSO-d$_6$) δ 10.85 (s, 1H), 10.23 (d, J=23.1 Hz, 2H), 8.05 (t, J=2.0 Hz, 1H), 7.98-7.69 (m, 7H), 7.53-7.27 (m, 4H), 5.65 (s, 1H), 4.23 (s, 2H), 2.69 (s, 2H), 1.66 (s, 2H), 1.46-1.22 (m, 6H), 0.93-0.79 (m, 3H), 0.62-0.47 (m, 2H), 0.30 (d, J=5.1 Hz, 2H), 0.00 (s, 2H); MS (ES+) 304.9 (M/2-2H$_2$O), 340.4 (M/2+1), 679.5 (M+1); Optical rotation: $[t]_D$=(−) 7.77 [0.515, CH$_3$OH]; Analysis calculated for C$_{36}$H$_{38}$F$_4$N$_6$O$_3$.2HCl.2H$_2$O: C, 54.89; H, 5.63; Cl, 9.00; N, 10.67; Found: C, 54.92; H, 5.51; Cl, 8.80; N, 10.60.

Preparation of (−)-2,2,2-trichloroethyl ((3-(5-((5-(((cyclopropylmethyl)amino)(phenyl)methyl)-2-fluoro-phenyl)carbamoyl)-3-(trifluoromethyl)-1H-pyrazol-1-yl)phenyl)(imino)methyl)carbamate (233c)

To a solution of (−)-1-(3-carbamimidoylphenyl)-N-(5-((cyclopropylmethylamino)-(phenyl)methyl)-2-fluorophenyl)-3-(trifluoromethyl)-1H-pyrazole-5-carboxamide (227d) (150 mg, 0.27 mmol) in anhydrous acetonitrile (10 mL) was added triethylamine (88 mg, 0.87 mmol) followed by addition of a solution of 2,2,2-trichloroethyl chloroformate (57.6 mg, 0.27 mmol) in anhydrous acetonitrile (3.0 mL). The resulting reaction mixture was stirred for 11 h at room temperature. Work up, purification and conversion to hydrochloride salt as reported in preparation for compound 233b gave (−)-2,2,2-trichloroethyl ((3-(5-((5-(((cyclopropylmethyl)amino)-(phenyl)methyl)-2-fluoro-phenyl)carbamoyl)-3-(trifluoromethyl)-1H-pyrazol-1-yl)phenyl)(imino) methyl)carbamate (233c) (106 mg, 54% yield) hydrochloride salt as a white solid. $^1$H NMR (300 MHz, DMSO-d$_6$ one drop of D$_2$O) δ 8.22-7.96 (m, 2H), 7.87 (dq, J=6.1, 3.0 Hz, 1H), 7.83-7.60 (m, 6H), 7.40 (dt, J=13.3, 7.7 Hz, 4H), 5.64 (s, 1H), 4.99 (s, 1H), 4.90 (s, 1H), 2.70 (d, J=7.0 Hz, 2H), 1.19-1.02 (m, 1H), 0.67-0.41 (m, 2H), 0.37-0.15 (m, 2H); $^{19}$F NMR (282 MHz, DMSO) δ −60.63, −60.65, −120.48; MS (ES+) 727.4 (M+1); Optical rotation: $[α]_D$=(−) 12.63 [0.285, CH$_3$OH]; Analysis calculated for C$_{32}$H$_{27}$C$_{13}$F$_4$N$_6$O$_3$.1.8HCl.2H$_2$O: C, 46.44; H, 3.99; Cl, 20.56; N, 10.15; Found: C, 46.39; H, 4.0; Cl, 20.60; N, 10.16.

Preparation of (−)-S-ethyl ((3-(5-((5-(((cyclopropylmethyl)amino)(phenyl)methyl)-2-fluoro phenyl)carbamoyl)-3-(trifluoromethyl)-1H-pyrazol-1-yl)phenyl)(imino)methyl)carbamothioate (233d)

Compound 233d was prepared from (−)-1-(3-carbamimidoylphenyl)-N-(5-((cyclopropylmethylamino)(phenyl)methyl)-2-fluorophenyl)-3-(trifluoromethyl)-1H-pyrazole-5-carboxamide (227d) (220.0 mg, 0.40 mmol) and ethyl chlorothioformate (49.8 mg, 0.40 mmol) according to the procedure described in preparation of compound 233b afforded (−)-S-ethyl ((3-(5-((5-(((cyclopropylmethyl)amino)(phenyl)methyl)-2-fluorophenyl) carbamoyl)-3-(trifluoromethyl)-1H-pyrazol-1-yl)phenyl)(imino)methyl)carbamothioate (233d) (120 mg, 47% yield) hydrochloride salt as a white solid; $^1$H NMR (300 MHz, DMSO-d$_6$) δ 11.90 (s, 1H), 10.89 (s, 1H), 10.29 (bs, 2H), 8.13-7.98 (m, 2H), 7.92-7.62 (m, 7H), 7.49-7.30 (m, 4H), 5.77-5.52 (m, 1H), 2.87 (m, 2H), 2.77-2.59 (m, 2H), 1.29-1.22 (m, 3H), 1.22-1.11 (m, 1H), 0.64-0.42 (m, 2H), 0.40-0.17 (m, 2H); $^{19}$F NMR (282 MHz, DMSO) δ −60.66, −60.68, −120.13; MS (ES+) 639.4 (M+1); Optical rotation: $[α]_D$=(−) 5.44 [0.515, CH$_3$OH]; Analysis calculated for C$_{32}$H$_{30}$F$_4$N$_6$O$_2$S.2HCl.2H$_2$O: C, 51.41; H, 4.85; Cl, 9.48; N, 11.24; S, 4.29; Found: C, 51.33; H, 4.76; Cl, 9.21; N, 11.41; S, 4.15.

Preparation of (−)-1-((3-(5-(5-((−)-cyclopropylmethylamino)(phenyl)methyl)-2-fluorophenylcarbamoyl)-3-(trifluoromethyl)-1H-pyrazol-1-yl)phenyl)(imino)methyl carbamoyloxy)ethyl acetate (233e)

To (−)-1-(3-carbamimidoylphenyl)-N-(5-((cyclopropylmethylamino)(phenyl)methyl)-2-fluorophenyl)-3-(trifluoromethyl)-1H-pyrazole-5-carboxamide (227d) (245 mg, 0.445 mmol) was added to NaOH (0.1N, 5.3 mL) and resulting mixture was stirred for 10 min at room temperature. The reaction mixture was concentrated in vacuum and residue obtained dissolved in HMPA (10 mL). To the solution was added 1-((4-nitrophenoxy)carbonyloxy)ethyl acetate [prepared as reported by Rahrmathullah, Syed M. et al in Journal of Medicinal Chemistry, 42(19), 3994-4000; 1999), 240 mg, 0.89 mmol] and stirred at room temperature overnight. The reaction mixture was quenched with water and extracted with EtOAc (3×30 mL). The organic layers were combined washed with brine (20 mL), dried and concentrated in vacuum. The residue obtained was purified by flash column chromatography (silica gel, eluting with 0-100% EtOAc in hexane) to afford (−)-1-((3-(5-(5-((−)-(cyclopropylmethyl-amino)(phenyl)methyl)-2-fluorophenylcarbamoyl)-3-(trifluoromethyl)-1H-pyrazol-1-yl)phenyl)(imino)methyl carbamoyloxy)ethyl acetate (233e) (212 mg, 0.311 mmol, 70.0% yield) as a white solid; $^1$H NMR (300 MHz, DMSO-$d_6$) δ 10.54 (s, 1H), 9.47-9.34 (m, 2H), 8.21-8.08 (m, 2H), 7.82-7.54 (m, 4H), 7.39 (d, J=7.0 Hz, 2H), 7.28 (t, J=7.5 Hz, 2H), 7.24-7.14 (m, 2H), 6.77 (q, J=5.4 Hz, 1H), 4.84 (s, 1H), 2.27 (m, 2H), 2.02 (s, 3H), 1.43 (d, J=5.4 Hz, 3H), 0.88 (m, 1H), 0.43-0.26 (m, 2H), 0.04 (m, 2H); $^{19}$F NMR (282 MHz, DMSO) δ −60.64, −123.32; MS (ES+) 681.5 (M+1); Optical rotation: [α]$_D$=(−) 5.37 [0.335, MeOH].

Scheme 234

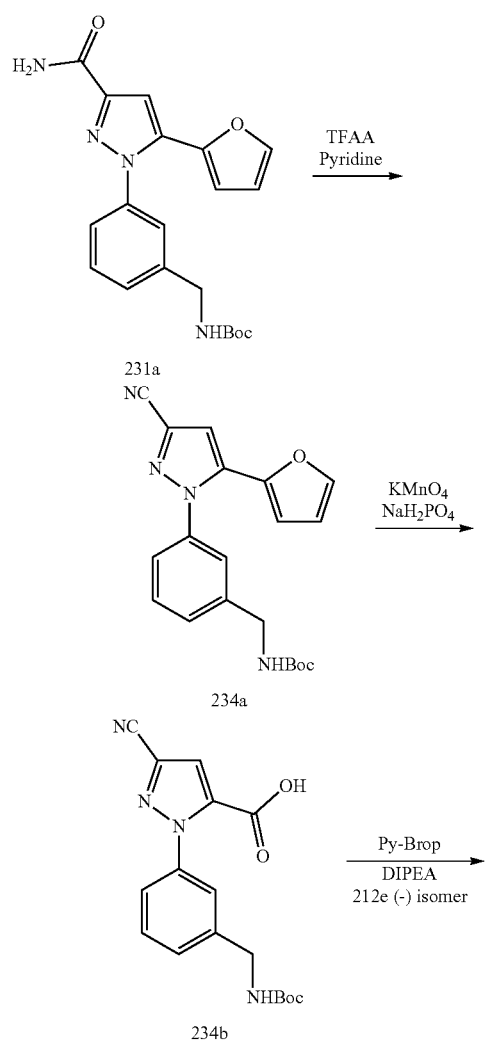

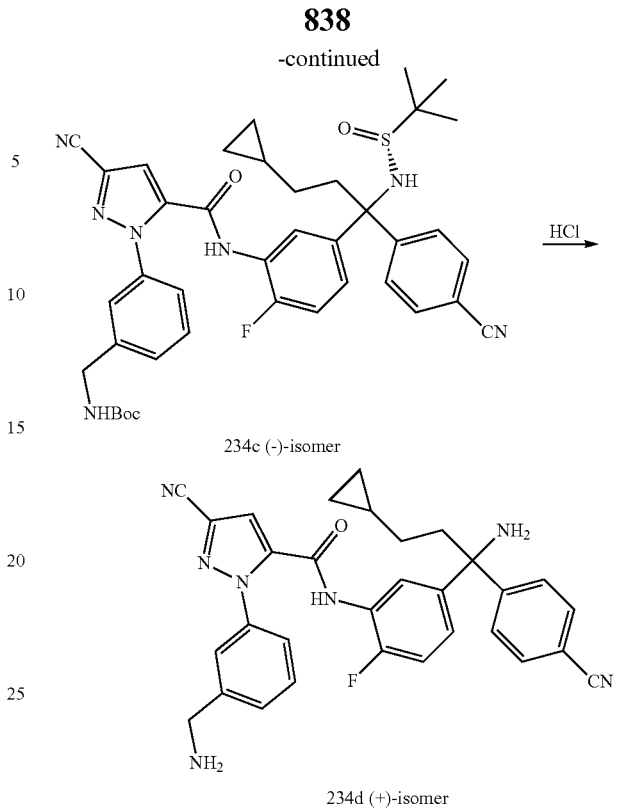

Preparation of (+)-N-(5-(1-amino-1-(4-cyanophenyl)-3-cyclopropylpropyl)-2-fluorophenyl)-1-(3-(aminomethyl)phenyl)-3-cyano-1H-pyrazole-5-carboxamide (234d)

Step-1 Preparation of tert-butyl 3-(3-cyano-5-(furan-2-yl)-1H-pyrazol-1-yl)benzylcarbamate (234a)

To a solution of furnish tert-butyl 3-(3-carbamoyl-5-(furan-2-yl)-1H-pyrazol-1-yl)benzylcarbamate (231a) (200 mg, 0.523 mmol) in THF (4 mL) was added pyridine (0.085 mL, 1.046 mmol), 2,2,2-trifluoroacetic anhydride (0.089 mL, 0.628 mmol) dropwise and stirred at room temperature for 30 mins. The reaction was quenched with water (1 mL) and concentrated in vacuum to dryness. To the residue was added saturated aqueous NaHCO$_3$ (20 mL) and extracted with chloroform (2×30 mL). The combined chloroform layers were washed with brine (30 mL), dried over MgSO$_4$ filtered and concentrated in vacuum. The residue was purified by flash column chromatography (silica gel 12 g, eluting with ethyl acetate in hexane 0 to 100%) to furnish tert-butyl 3-(3-cyano-5-(furan-2-yl)-1H-pyrazol-1-yl)benzylcarbamate (234a) (120 mg, 0.329 mg, 63.0%) as a white solid. $^1$H NMR (300 MHz, DMSO-$d_6$) δ 7.79 (dd, J=1.8, 0.8 Hz, 1H), 7.57-7.42 (m, 4H), 7.40-7.31 (m, 2H), 6.53 (dd, J=3.5, 1.8 Hz, 1H), 6.15 (d, J=3.5 Hz, 1H), 4.20 (d, J=6.2 Hz, 2H), 1.37 (s, 9H); MS (ES+): 387.3 (M+Na).

Step-2 Preparation of 1-(3-((tert-butoxycarbonylamino)methyl)phenyl)-3-cyano-1H-pyrazole-5-carboxylic Acid (234b)

Compound 234b was prepared from tert-butyl 3-(3-cyano-5-(furan-2-yl)-1H-pyrazol-1-yl)benzylcarbamate (234a) (115 mg, 0.316 mmol) as described in step-5 of scheme-229 to furnish 1-(3-((tert-butoxycarbonylamino)methyl)phenyl)-3-cyano-1H-pyrazole-5-carboxylic acid (234b) (135 mg) as a yellow solid, which was used as such for next step; MS (ES−) 341.3 (M−1), 683.3 (2M−1).

Step-3: Preparation of tert-butyl 3-(3-cyano-5-(5-((−)-1-(4-cyanophenyl)-3-cyclopropyl-1-((R)-1,1-dimethylethylsulfinamido)propyl)-2-fluorophenylcarbamoyl)-1H-pyrazol-1-yl)benzylcarbamate (234c)

Compound 234c was prepared from 1-(3-((tert-butoxycarbonylamino)methyl)phenyl)-3-cyano-1H-pyrazole-5-carboxylic acid (234b) (0.117 g, 0.341 mmol) and (R)—N-((−)-1-(3-amino-4-fluorophenyl)-1-(4-cyanophenyl)-3-cyclopropylpropyl)-2-methylpropane-2-sulfinamide (212e) (0.103 g, 0.249 mmol) as described in step-3 of scheme-208 to furnish tert-butyl 3-(3-cyano-5-(5-((−)-1-(4-cyanophenyl)-3-cyclopropyl-1-((R)-1,1-dimethylethylsulfinamido)propyl)-2-fluorophenylcarbamoyl)-1H-pyrazol-1-yl)benzylcarbamate (234c) (90 mg, 0.122 mmol, 49.0%) as an off white solid; $^1$H NMR (300 MHz, DMSO-$d_6$) δ 10.64 (s, 1H), 7.81-7.32 (m, 11H), 7.23 (d, J=7.5 Hz, 2H), 5.55 (s, 1H), 4.18 (d, J=6.1 Hz, 2H), 2.65-2.40 (m, 2H), 1.38 (s, 9H), 1.12 (s, 9H), 1.08-0.76 (m, 2H), 0.63 (s, 1H), 0.39-0.30 (m, 2H), −0.02--0.21 (m, 2H); MS (ES+): 760.6 (M+Na); Optical rotation: [α]$_D$=(−) 43.81 [0.105, MeOH].

Step-4: Preparation of (+)-N-(5-(1-amino-1-(4-cyanophenyl)-3-cyclopropylpropyl)-2-fluorophenyl)-1-(3-(aminomethyl)phenyl)-3-cyano-1H-pyrazole-5-carboxamide (234d)

To a solution of tert-butyl 3-(3-cyano-5-(5-((−)-1-(4-cyanophenyl)-3-cyclopropyl-1-((R)-1,1-dimethylethylsulfinamido)propyl)-2-fluorophenylcarbamoyl)-1H-pyrazol-1-yl)benzylcarbamate (234c) (78 mg, 0.106 mmol) in ethanol (10 mL) was added conc. HCl (0.090 mL, 1.078 mmol) heated at reflux for 1 h and concentrated in vacuum to dryness. The residue was purified twice by flash column chromatography [silica gel, first column, eluting with chloroform/CMA80 (1:0 to 3:1), second column eluting with chloroform/methanol (1:0 to 9:1)] to afford 234d (25 mg, 0.047 mmol, 44.3% yield) free base an off white solid; Free base (25 mg, 0.047 mmol) was dissolved in ethanol (3 mL), added conc. HCl (aq. 0.020 mL) and concentrated in vacuum to dryness. The residue was dissolved in 3 mL of water and concentrated in vacuum to dryness to furnish (+)-N-(5-(1-amino-1-(4-cyanophenyl)-3-cyclopropylpropyl)-2-fluorophenyl)-1-(3-(aminomethyl)phenyl)-3-cyano-1H-pyrazole-5-carboxamide (234d) (28 mg, 95.69%) hydrochloride salt as a white solid; $^1$H NMR (300 MHz, DMSO-$d_6$) δ 10.83 (s, 1H), 9.33 (s, 3H), 8.31 (s, 3H), 7.96 (d, J=8.3 Hz, 2H), 7.90-7.20 (m, 10H), 4.17-4.07 (m, 2H), 2.60-2.40 (m, 2H), 1.35-0.93 (m, 2H), 0.75-0.60 (m, 1H), 0.42-0.32 (m, 2H), 0.04--0.06 (m, 2H); $^{19}$F NMR (282 MHz, DMSO-$d_6$) δ −120.21; MS (ES+): 534.5 (M+1); Optical rotation: [α]$_D$=(+) 15.85 [0.265, MeOH].

Scheme 235

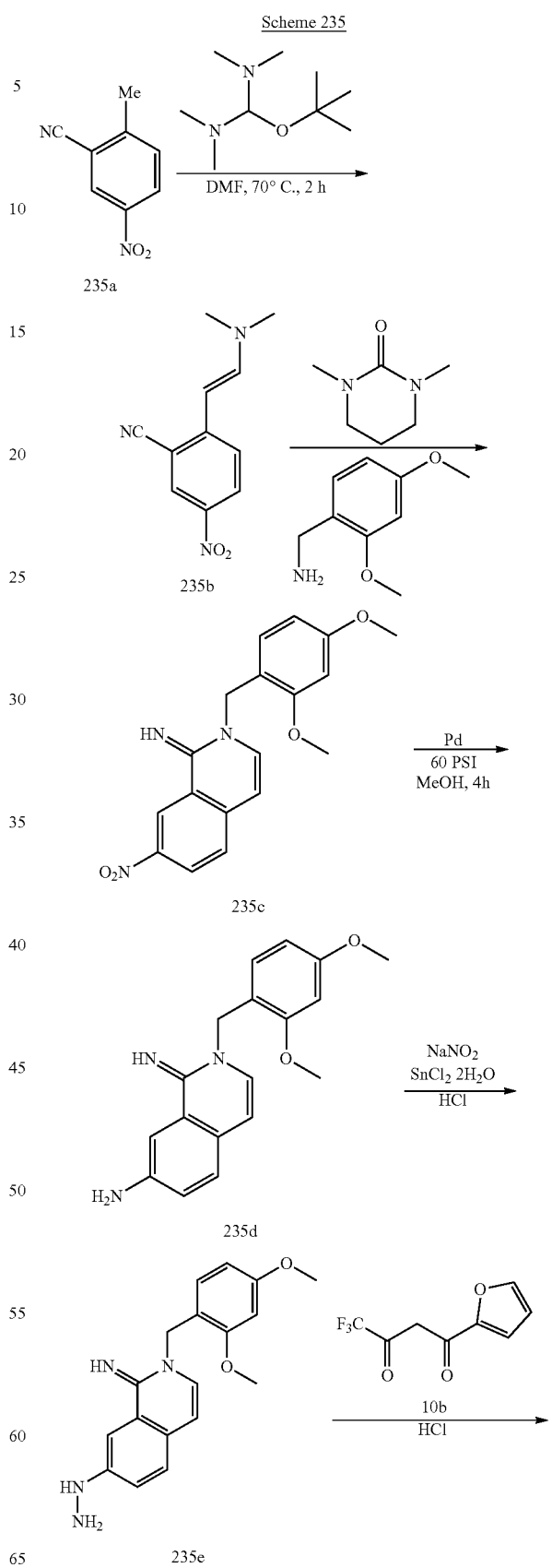

841
-continued

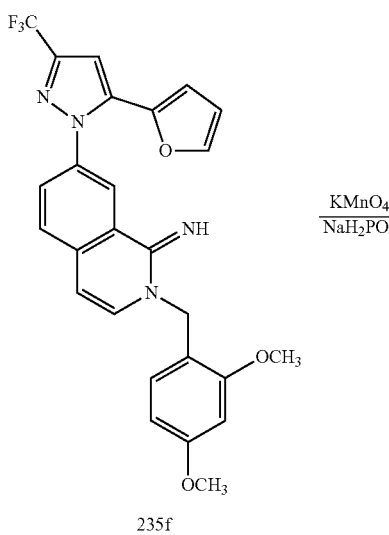

235f

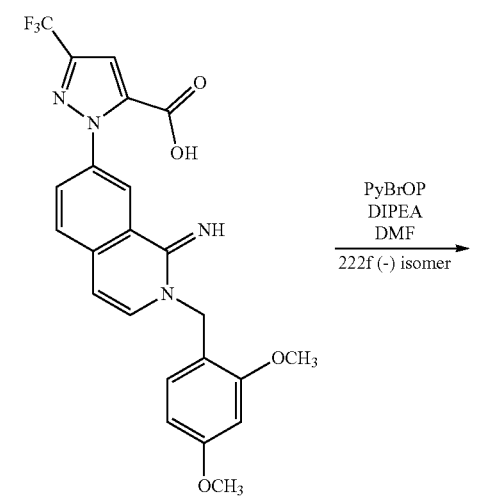

235e

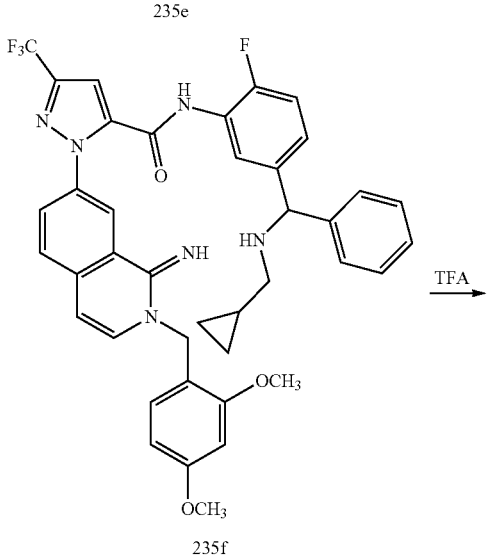

235f

842
-continued

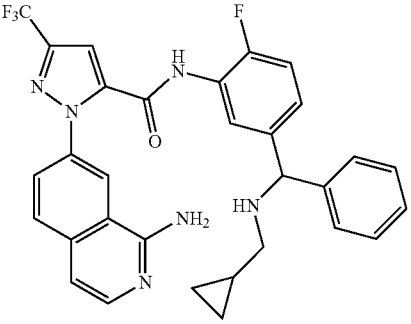

235g (−)-isomer

Preparation of (−)-1-(1-aminoisoquinolin-7-yl)-N-(5-((cyclopropylmethylamino)(phenyl)methyl)-2-fluorophenyl)-3-(trifluoromethyl)-1H-pyrazole-5-carboxamide (235)

Step-1: Preparation of (E)-2-(2-(dimethylamino)vinyl)-5-nitrobenzonitrile (235b)

A mixture of 2-methyl-5-nitrobenzonitrile (235a) (5 g, 30.8 mmol) and 1-tert-butoxy-N,N,N',N'-tetramethylmethanediamine (Bredereck's reagent) (10.19 mL, 49.3 mmol) in dry DMF (10 mL) was heated at 70° C. for 2 h. The reaction was cooled to room temperature and concentrated in vacuum; the crude product was triturated with 120 mL of hexanes/ethyl acetate (5:1), and stirred for 10 min. The solid obtained was collected by filtration washed with hexanes (2×75 mL), dried under vacuum to afford (E)-2-(2-(dimethylamino)vinyl)-5-nitrobenzonitrile (235b) (6.07 g, 91% yield) as a light brown solid; $^1$H NMR: $^1$H NMR (300 MHz, DMSO-$d_6$) δ 8.35 (d, J=2.5 Hz, 1H), 8.06 (ddd, J=9.2, 2.6, 0.7 Hz, 1H), 7.93 (d, J=13.0 Hz, 1H), 7.70 (d, J=9.4 Hz, 1H), 5.29 (d, J=12.9 Hz, 1H), 3.04 (s, 6H); MS (ES−) 252.1 (M+Cl).

Step-2: Preparation of 2-(2,4-Dimethoxybenzyl)-7-nitroisoquinolin-1(2H)-imine (235c)

A mixture of (E)-2-(2-(dimethylamino)vinyl)-5-nitrobenzonitrile (235b) (6.01 g, 27.7 mmol) and (2,4-dimethoxyphenyl)methanamine (5.45 mL, 34.6 mmol) in 1,3-dimethyltetrahydropyrimidin-2(1H)-one (DMPU) (10 mL, 80 mmol) was heated at 140° C. for 3 h. The solvent was removed by vacuum distillation and residue obtained was purified by flash column chromatography [silica gel 120 g, eluting with methanol in chloroform, 0-100%] to furnish 2-(2,4-Dimethoxybenzyl)-7-nitroisoquinolin-1(2H)-imine (235c) (4.26 g, 45% yield) as a brown solid; $^1$H NMR (300 MHz, DMSO-$d_6$) δ 9.07 (d, J=2.4 Hz, 1H), 8.26 (dd, J=8.7, 2.3 Hz, 1H), 7.61 (d, J=8.8 Hz, 1H), 7.38 (d, J=7.4 Hz, 1H), 7.06 (d, J=8.4 Hz, 1H), 6.60 (d, J=2.4 Hz, 1H), 6.48 (dd, J=8.4, 2.4 Hz, 1H), 6.22 (d, J=7.4 Hz, 1H), 4.96 (s, 2H), 3.83 (s, 3H), 3.74 (s, 3H); MS (ES$^+$): MS (ES+) 340.27 (M+1).

Step-3: Preparation of 2-(2,4-dimethoxybenzyl)-1-imino-1,2-dihydroisoquinolin-7-amine (235d)

To a solution of 2-(2,4-dimethoxybenzyl)-7-nitroisoquinolin-1(2H)-imine (4.18 g, 12.32 mmol) in methanol (50 mL) was added palladium (10% Pd on carbon; 0.787 g). The reaction mixture was hydrogenated at 60 psi for 4 h at room temperature. The reaction mixture was filtered through a small Celite pad rinsed with methanol (2×75 mL) and concentrated under reduced pressure to afford 2-(2,4-dimethoxybenzyl)-1-imino-1,2-dihydroisoquinolin-7-amine (235d) (3.786 g, 99% yield) as a brown solid; $^1$H NMR (300 MHz, DMSO-$d_6$) δ 7.21 (s, 1H), 7.14 (d, J=8.4 Hz, 1H), 6.92 (d, J=8.4 Hz, 1H), 6.87-6.75 (m, 2H), 6.58 (d, J=2.4 Hz, 1H), 6.44 (dd, J=8.4, 2.4 Hz, 1H), 5.97 (d, J=7.4 Hz, 1H), 5.32 (s, 2H, $D_2O$ exchangeable), 4.94 (s, 2H), 3.82 (s, 3H), 3.72 (s, 3H), 3.17 (d, J=4.9 Hz, 1H); MS (ES$^+$): MS (ES+) 310.3 (M+1).

Step-4: Preparation of 2-(2,4-dimethoxybenzyl)-7-hydrazinylisoquinolin-1(2H)-imine hydrochloride (235e)

To a suspension of 2-(2,4-dimethoxybenzyl)-1-imino-1,2-dihydroisoquinolin-7-amine (235d) (3.21 g, 10.38 mmol) in conc. HCl (9.51 mL, 114 mmol) at 0° C. was added drop-wise a solution of Sodium nitrite (0.716 g, 10.38 mmol) in water (15 mL). The reaction mixture was stirred for 30 min at 0° C. and added at 0° C. a solution of Tin(II) chloride dihydrate (7.02 g, 31.1 mmol) in 12N HCl (6.05 mL, 72.6 mmol). The reaction mixture was stirred at 0° C. for 10 mins and placed in refrigerator overnight. The solid obtained was collected by filtration, washed with cold brine, cold water and hexanes. The solid was dried over P2O5 to afford 2-(2,4-dimethoxybenzyl)-7-hydrazinylisoquinolin-1(2H)-imine hydrochloride (235e) as a light brown solid which was used as such for next step; $^1$H NMR (300 MHz, DMSO-$d_6$) δ 10.30 (s, 3H, $D_2O$ exchangeable), 9.15 (d, J=29.9 Hz, 3H, $D_2O$ exchangeable), 8.32 (d, J=2.2 Hz, 1H), 7.87 (d, J=8.8 Hz, 1H), 7.56 (dd, J=8.7, 2.0 Hz, 1H), 7.46 (d, J=7.2 Hz, 1H), 7.20 (d, J=7.3 Hz, 1H), 7.04 (d, J=8.4 Hz, 1H), 6.67 (d, J=2.3 Hz, 1H), 6.55 (dd, J=8.4, 2.4 Hz, 1H), 5.33 (s, 2H), 3.79 (s, 3H), 3.77 (s, 3H); MS (ES$^+$): MS (ES+) 325.3 (M+1).

Step-5: Preparation of 2-(2,4-dimethoxybenzyl)-7-(5-(furan-2-yl)-3-(trifluoromethyl)-1H-pyrazol-1-yl)isoquinolin-1(2H)-imine (235f)

To a solution of 2-(2,4-dimethoxybenzyl)-7-hydrazinylisoquinolin-1(2H)-imine hydrochloride (235e) (3.59 g, 11.07 mmol) in ethanol (50 mL), and conc. HCl (2.77 mL, 33.2 mmol) was added 4,4,4-trifluoro-1-(furan-2-yl)butane-1,3-dione (2.509 g, 12.17 mmol) and stirred the at room temperature overnight. The reaction mixture was concentrated in vacuum and residue was treated with sat. NaHCO$_3$, extracted with chloroform (2×150 mL). The combined organics were dried over anhydrous MgSO$_4$, filtered, evaporated to dryness to afford 2-(2,4-dimethoxybenzyl)-7-(5-(furan-2-yl)-3-(trifluoromethyl)-1H-pyrazol-1-yl)isoquinolin-1(2H)-imine (235f) (2.582 g, 47% yield) as a dark yellow waxy solid; $^1$H NMR (300 MHz, DMSO-$d_6$) δ 8.43 (s, 1H), 8.32 (s, 1H), 7.77 (dd, J=1.8, 0.7 Hz, 1H), 7.61 (d, J=1.3 Hz, 2H), 7.31 (s, 1H), 7.26 (d, J=7.5 Hz, 1H), 7.05 (d, J=8.4 Hz, 1H), 6.60 (d, J=2.4 Hz, 1H), 6.53 (dd, J=3.5, 1.8 Hz, 1H), 6.47 (dd, J=8.4, 2.4 Hz, 1H), 6.32-6.19 (m, 2H), 4.99 (s, 2H), 3.83 (s, 3H), 3.74 (s, 3H); $^{19}$F NMR (282 MHz, DMSO-$d_6$) δ −60.60; MS (ES$^+$): MS (ES+) 495.3 (M+1).

Step-6: Preparation of 1-(2-(2,4-dimethoxybenzyl)-1-imino-1,2-dihydroisoquinolin-7-yl)-3-(trifluoromethyl)-1H-pyrazole-5-carboxylic Acid (235e)

To a suspension of 2-(2,4-dimethoxybenzyl)-7-(5-(furan-2-yl)-3-(trifluoromethyl)-1H-pyrazol-1-yl)isoquinolin-1 (2H)-imine (235f) (15.13 g, 30.6 mmol) in tert-BuOH (200 mL) containing 5% aq. sodium dihydrogenphosphate (6.98 g, 58.2 mmol) in water (140 mL) was added solid potassium permanganate (4.84 g, 30.6 mmol) slowly in portions and stirred at room temperature for 4 h. Additional potassium permanganate (4.84 g, 30.6 mmol) was added and reaction mixture was stirred for 2 h. The reaction mixture was quenched with 2-propanol (250 mL), stirred for 6 h, filtered through a Celite pad, washed with 2-propanol, and acetone. The excess solvents were evaporated and aq. layer was acidified with 1M KHSO$_4$, crude product extracted with ethyl acetate (2×300 mL). The combined organic layers were dried over anhydrous MgSO$_4$, filtered and evaporated to dryness. The residue obtained was purified by flash column chromatography [silica gel 120 g, eluting with CMA80 in chloroform, 0-100%] to furnish 235e (1.103 g, 2.335 mmol, 7.63% yield) as a yellow solid. Compound 235e was dissolved in chloroform (50 mL) and treated with 30 mL of (1M KHSO$_4$), the solid obtained was collected by filtration, and dried under vacuum to afford 1-(2-(2,4-dimethoxybenzyl)-1-imino-1,2-dihydroisoquinolin-7-yl)-3-(trifluoromethyl)-1H-pyrazole-5-carboxylic acid (235e) as a yellow solid; $^1$H NMR (300 MHz, DMSO-$d_6$) δ 9.39 (s, 2H, $D_2O$ exchangeable), 8.83 (d, J=1.9 Hz, 1H), 8.19-7.96 (m, 2H), 7.67 (d, J=7.3 Hz, 1H), 7.35 (d, J=7.3 Hz, 1H), 7.22 (s, 1H), 7.09 (d, J=8.4 Hz, 1H), 6.67 (d, J=2.3 Hz, 1H), 6.56 (dd, J=8.5, 2.4 Hz, 1H), 5.33 (s, 2H), 3.81 (s, 3H), 3.77 (s, 3H); $^{19}$F NMR (282 MHz, DMSO-$d_6$) δ −60.67; MS (ES$^+$): MS (ES+) 473.3 (M+1); MS (ES−) 471.3 (M−1); Analysis calculated for: $C_{23}H_{19}F_3N_4O_4 \cdot 0.5KHSO_4 \cdot 1.5H_2O$: C, 48.68; H, 4.00; N, 9.87; Found: C, 48.96; H, 4.09; N, 9.91.

Step-7: Preparation of N-(5-((cyclopropylmethylamino)(phenyl)methyl)-2-fluorophenyl)-1-(2-(2,4-dimethoxybenzyl)-1-imino-1,2-dihydroisoquinolin-7-yl)-3-(trifluoromethyl)-1H-pyrazole-5-carboxamide (235f)

Compound 235f was prepared from 1-(2-(2,4-dimethoxybenzyl)-1-imino-1,2-dihydroisoquinolin-7-yl)-3-(trifluoromethyl)-1H-pyrazole-5-carboxylic acid (235e) (0.269 g, 0.569 mmol) and (−)-5-((cyclopropylmethylamino)(phenyl)methyl)-2-fluoroaniline (222f) (0.185 g, 0.683 mmol) using procedure reported in step-3 of scheme-208 to furnish N-(5-((cyclopropylmethylamino)(phenyl)methyl)-2-fluorophenyl)-1-(2-(2,4-dimethoxybenzyl)-1-imino-1,2-dihydroisoquinolin-7-yl)-3-(trifluoromethyl)-1H-pyrazole-5-carboxamide (235f) (0.118 g, 0.163 mmol, 28.6% yield) as a yellow waxy solid which was used as such in the next step; MS (ES+): 725.5 (M+1), MS (ES−): 723.3 (M−1).

Step-8: Preparation of (−)-1-(1-aminoisoquinolin-7-yl)-N-(5-((cyclopropylmethylamino)(phenyl)methyl)-2-fluorophenyl)-3-(trifluoromethyl)-1H-pyrazole-5-carboxamide (235)

To a solution of N-(5-((cyclopropylmethylamino)(phenyl)methyl)-2-fluorophenyl)-1-(2-(2,4-dimethoxybenzyl)-1-imino-1,2-dihydroisoquinolin-7-yl)-3-(trifluoromethyl)-1H-pyrazole-5-carboxamide (235f) (0.113 g, 0.156 mmol) in anisole (2 mL) was added trifluoroacetic acid (0.120 mL, 1.559 mmol) and heated at 90° C. for 6 h. The reaction mixture was cooled to room temperature and concentrated in vacuum to dryness. The residue was suspended in water (50 mL) basified with sat aqueous NaHCO$_3$ to pH 8.0 and extracted with ethyl acetate (2×50 mL). The combined organic layers were dried over anhydrous MgSO$_4$, filtered and evaporated to dryness. The residue obtained was purified by flash column chromatography [First column: silica gel 12 g, eluting with CMA80 in chloroform; Second column: silica gel 12 g, eluting with ethyl acetate/methanol (9:1) in hexanes from 0-100%] to furnish (−)-1-(1-aminoisoquinolin-7-yl)-N-(5-((cyclopropylmethylamino)(phenyl)methyl)-2-fluorophenyl)-3-(trifluoromethyl)-1H-pyrazole-5-carboxamide (235) (4 mg, 4% yield) as a colorless solid; $^1$H NMR (300 MHz, CD$_3$OD) δ 8.35 (d, J=2.4 Hz, 1H), 7.82 (d, J=6.2 Hz, 2H), 7.78-7.69 (m, 2H), 7.45 (s, 1H), 7.39-7.31 (m, 2H), 7.31-7.22 (m, 3H), 7.22-7.02 (m, 3H), 4.86 (s, 1H), 2.34 (d, J=6.9 Hz, 2H), 1.03-0.84 (m, 1H), 0.53-0.35 (m, 2H), 0.04 (m, 2H). $^{19}$F NMR (282 MHz, DMSO-d$_6$) δ −64.53, −128.12; MS (ES$^+$): MS (ES+) 575.4 (M+1); MS (ES−) 573.3 (M−1), 609.3 (M+Cl); Optical rotation: [α]$_D$=(−) 0.21 [0.095, MeOH].

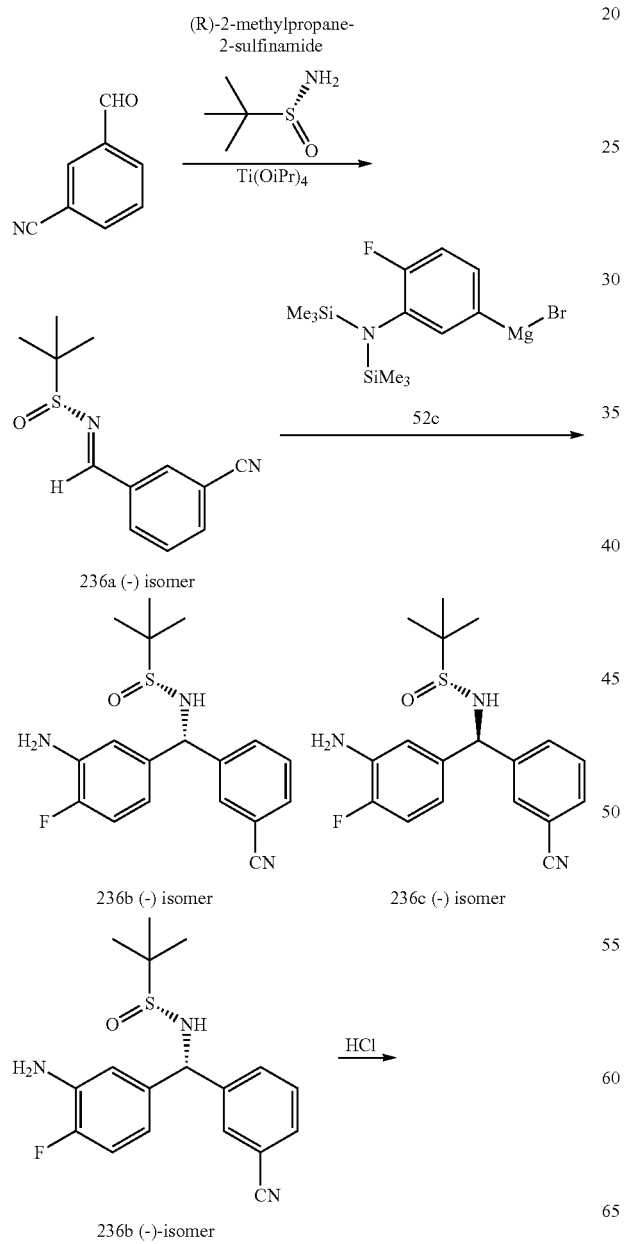

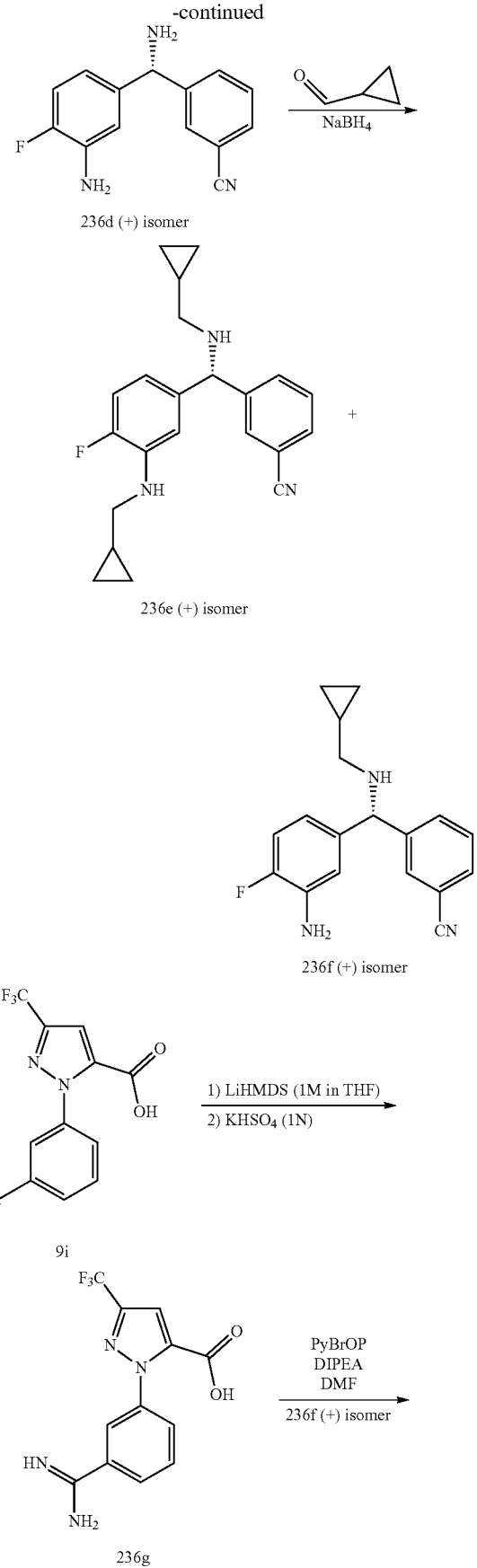

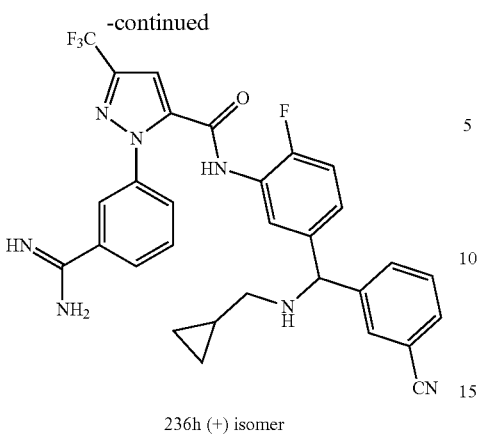

236h (+) isomer

Preparation of (+)-1-(3-carbamimidoylphenyl)-N-(5-((3-cyanophenyl)(cyclopropylmethylamino)methyl)-2-fluorophenyl)-3-(trifluoromethyl)-1H-pyrazole-5-carboxamide (236h)

Step-1: Preparation of (−)-N-(3-cyanobenzylidene)-2-methylpropane-2-sulfinamide (236a)

To a stirred solution of 3-formylbenzonitrile (45.4 g, 347 mmol) in tetrahydrofuran (460 mL) was added (R)-2,4,6-triisopropylbenzenesulfinamide (35 g, 289 mmol), tetraisopropoxytitanium (173 mL, 578 mmol) and heated at reflux for 10 h. Work up was performed as reported in step-1 of scheme-222 to furnish after column chromatography (silica gel 1.5 kg, eluting with 20% ethyl acetate in hexane) (−)-N-(3-cyanobenzylidene)-2-methylpropane-2-sulfinamide (236a) (37.4 g, 160 mmol, 55.3% yield) as a colorless solid; $^1$H NMR (300 MHz, DMSO-d$_6$) δ 8.63 (s, 1H), 8.42 (dd, J=1.9, 1.3 Hz, 1H), 8.28 (dt, J=7.9, 1.4 Hz, 1H), 8.07 (dt, J=7.7, 1.4 Hz, 1H), 7.76 (t, J=7.8 Hz, 1H), 1.21 (s, 9H); MS (ES+) 257.2 (M+Na); Optical rotation: [α]$_D$=(−) 83.21 [2.55, CHCl$_3$].

Step-2: Preparation of (R)—N—((R)-(3-amino-4-fluorophenyl)(3-cyanophenyl)methyl)-2-methylpropane-2-sulfinamide (236b) and (R)—N—((S)-(3-amino-4-fluorophenyl)(3-cyanophenyl)methyl)-2-methylpropane-2-sulfinamide (R)—N—((S)-(3-amino-4-fluorophenyl)(3-cyanophenyl)methyl)-2-methylpropane-2-sulfinamide (236c)

Compound 236b was prepared from (−)-N-(3-cyanobenzylidene)-2-methylpropane-2-sulfinamide (236a) (72 g, 307 mmol) and 3-(bis(trimethylsilyl)amino)-4-fluorophenyl)magnesium bromide (52c) (430 mL, 430 mmol) as described in step-2 of scheme-222 for preparation of compounds 222d and 222c to afforded mixture of diastereoisomers 236b and 236c. The crude mixture was purified by flash column chromatography [silica gel 4.5 kg, eluting with ethyl acetate in hexanes from 0-60%] to afford;
1. (R)—N—((R)-(3-amino-4-fluorophenyl)(3-cyanophenyl)methyl)-2-methylpropane-2-sulfinamide (236b) (47.32 g, 45% yield) isolated as an off-white solid; $^1$H NMR (300 MHz, DMSO-d$_6$) δ 7.83 (t, J=1.6 Hz, 1H), 7.76-7.64 (m, 2H), 7.54 (t, J=7.7 Hz, 1H), 6.93 (dd, J=11.4, 8.3 Hz, 1H), 6.73 (dd, J=8.8, 2.2 Hz, 1H), 6.57 (ddd, J=8.4, 4.4, 2.2 Hz, 1H), 6.01 (d, J=6.0 Hz, 1H), 5.48 (d, J=6.0 Hz, 1H), 5.15 (s, 2H), 1.13 (s, 9H); $^{19}$F NMR (282 MHz, DMSO-d$_6$) δ −136.86; MS (ES$^+$): MS (ES+) 346.3 (M+1), 368.3 (M+Na); MS (ES−) 725.3 (M+Cl); Chiral HPLC method: Column AD-H; Solvent 90:10:1.0 (hexane/isopropanol/TEA), 25° C., 1.0 ml/min, UV=260 nm; R$_f$=26.207 (peak-1 for compound 236b) >99.99% ee; Optical rotation: [α]$_D$=(−) 52.31 [0.845, MeOH]; Analysis calculated for C$_{18}$H$_{20}$FN$_3$OS: C, 62.59; H, 5.84; N, 12.16; Found: C, 62.44; H, 5.90; N, 11.93.
2. (R)—N—((S)-(3-amino-4-fluorophenyl)(3-cyanophenyl)methyl)-2-methylpropane-2-sulfinamide (236c) (13.51 g, 13% yield) as a white solid; $^1$H NMR (300 MHz, DMSO-d$_6$) δ 7.88 (t, J=1.7 Hz, 1H), 7.77-7.65 (m, 2H), 7.54 (t, J=7.7 Hz, 1H), 6.92 (dd, J=11.5, 8.3 Hz, 1H), 6.69 (dd, J=8.9, 2.2 Hz, 1H), 6.50 (ddd, J=8.4, 4.4, 2.2 Hz, 1H), 6.07 (d, J=6.5 Hz, 1H), 5.44 (d, J=6.4 Hz, 1H), 5.15 (s, 2H), 1.15 (s, 9H); $^{19}$F NMR (282 MHz, DMSO-d$_6$) δ −136.88; MS (ES$^+$): MS (ES+) 346.3 (M+1), 368.2 (M+Na), MS (ES−) 344.2 (M−1); HPLC: Chiral HPLC method: Column AD-H; Solvent 90:10:1.0 (hexane/isopropanol/TEA), 25° C., 1.0 ml/min, UV=260 nm; R$_f$=26.497 (peak-1 for compound 236b, 2.5953%), R$_f$=28.253 (peak-2 for compound 236c, 97.4047%); 94.8094% ee. Optical rotation: [α]$_D$=(−) 77.82 [1.19, MeOH]; Analysis calculated for C$_{18}$H$_{20}$FN$_3$OS: C, 62.59; H, 5.84; N, 12.16; S, 9.28. Found: C, 62.58; H, 5.71; N, 12.15; S, 9.20.

Step-3: Preparation of (+)-3-(amino(3-amino-4-fluorophenyl)methyl)benzonitrile (236d)

Compound (236d) was prepared from (R)—N—((R)-(3-amino-4-fluorophenyl)(3-cyanophenyl)methyl)-2-methylpropane-2-sulfinamide (236b) according to the procedure reported in step-3 of scheme-222 as described for preparation of compound 222d gave (+)-3-(amino(3-amino-4-fluorophenyl)methyl)benzonitrile (236d) hydrochloride salt as a white solid; $^1$H NMR (300 MHz, DMSO-d$_6$) δ 9.39-9.10 (m, 3H), 7.57-7.49 (m, 2H), 7.45-7.34 (m, 3H), 7.26 (d, J=5.8 Hz, 1H), 7.15 (dd, J=8.0, 2.0 Hz, 1H), 5.58 (d, J=5.5 Hz, 1H); $^{19}$F NMR (282 MHz, DMSO) δ −129.75; MS (ES−) 240.2 (M−1). The above solid was dissolved in water, basified by addition of NaOH (3 N). extracted with ethyl acetate. The organic layer was washed with brine, dried, filtered and concentrated in vacuum to furnish (+)-3-(amino(3-amino-4-fluorophenyl)methyl)benzonitrile (236d) free base as a brown oil; $^1$H NMR (300 MHz, DMSO-d6) 1H NMR (300 MHz, DMSO-DMSO-d$_6$) δ 7.84 (t, J=1.7 Hz, 1H), 7.66 (ddt, J=7.7, 6.2, 1.4 Hz, 2H), 7.48 (t, J=7.7 Hz, 1H), 6.88 (dd, J=11.5, 8.3 Hz, 1H), 6.76 (dd, J=9.0, 2.2 Hz, 1H), 6.55 (ddd, J=8.4, 4.5, 2.2 Hz, 1H), 5.06 (s, 2H), 5.00 (s, 1H), 2.27 (s, 2H); $^{19}$F NMR (282 MHz, DMSO) δ −138.23; 19F NMR (282 MHz, DMSO-d$_6$) δ −137.59; Chiral HPLC purity 99.8838% ee; MS (ES−) 240.3 (M−1), 276.1 (M+Cl); Optical rotation: [α]$_D$=(+) 27.99 [1.665, MeOH].

Step-4: Preparation of (+)-3-((cyclopropylmethylamino)(3-(cyclopropylmethylamino)-4-fluorophenyl)methyl)benzonitrile (236e) and (+)-3-((3-amino-4-fluorophenyl)(cyclopropyl methylamino)methyl)benzonitrile (236f)

To a stirred solution of (+)-3-(amino(3-amino-4-fluorophenyl)methyl)benzonitrile (236d) (8.321 g, 34.5 mmol) free base in MeOH (20 mL) was added cyclopropanecarboxaldehyde (3.25 mL, 43.1 mmol) at 0° C. and stirred for 30 mins. To this sodium borohydride (2.61 g, 69.0 mmol) was added and stirred at 0° C. for 1 hr. The reaction was concentrated in vacuum to remove methanol and residue was dissolved in ethyl acetate (200 mL), washed with water (2×50 mL), brine (50 mL), dried and concentrated. The crude residue was purified by flash column chromatography (silica gel 120 g, eluting with ethyl acetate in hexanes 0-100%) to afford 1. (+)-3-((cyclopropylmethylamino)(3-(cyclopropylmethylamino)-4-fluorophenyl)methyl)benzonitrile (236e) (1.087 g, 3.11 mmol, 9.02% yield) as a colorless syrup; $^1$H NMR (300 MHz, DMSO-d$_6$) δ 7.88 (t, J=1.7 Hz, 1H), 7.75 (dt, J=7.9, 1.5 Hz, 1H), 7.64 (dt, J=7.7, 1.4 Hz, 1H), 7.48 (t, J=7.7 Hz, 1H), 6.90 (dd, J=11.9, 8.2 Hz, 1H), 6.84 (dd, J=8.9, 2.1 Hz, 1H), 6.57 (ddd, J=8.2, 4.5, 2.0 Hz, 1H), 5.34 (td, J=6.0, 2.4 Hz, 1H), 4.81 (d, J=4.2 Hz, 1H), 2.96 (t, J=6.3 Hz, 2H), 2.59 (m, 1H), 2.27 (m, 2H), 1.03 (m, 1H), 0.98-0.84 (m, 1H), 0.40 (m, 4H), 0.26-0.17 (m, 2H), 0.05 (m, 2H); $^{19}$F NMR (282 MHz, DMSO-d$_6$) δ −137.04; MS (ES−) 348.4 (M−1); Optical rotation: $[α]_D$=(+) 17.96 [0.245, MeOH].

2. (+)-3-((3-amino-4-fluorophenyl)(cyclopropylmethylamino)methyl)benzonitrile (236f) (7.891 g, 26.7 mmol, 77% yield) as colorless syrup; $^1$H NMR (300 MHz, DMSO-d$_6$) δ 7.84 (t, J=1.6 Hz, 1H), 7.71 (dt, J=7.9, 1.5 Hz, 1H), 7.68-7.63 (m, 1H), 7.49 (t, J=7.7 Hz, 1H), 6.88 (dd, J=11.5, 8.3 Hz, 1H), 6.81 (dd, J=9.0, 2.2 Hz, 1H), 6.56 (ddd, J=8.3, 4.5, 2.1 Hz, 1H), 5.08 (s, 2H), 4.76 (d, J=2.8 Hz, 1H), 2.48 (m, 1H), 2.26 (m, 2H), 0.91 (m, 1H), 0.42-0.34 (m, 2H), 0.09-0.01 (m, 2H); $^{19}$F NMR (282 MHz, DMSO-d$_6$) δ −137.18; MS (ES+) 296.3 (M+1), (ES−) 294.3 (M−1); Optical rotation: $[α]_D$=(+) 22.05 [0.88, CHCl$_3$].

Step-5: Preparation of 1-(3-carbamimidoylphenyl)-3-(trifluoromethyl)-1H-pyrazole-5-carboxylic Acid (236g)

To a stirred solution of 1-(3-cyanophenyl)-3-(trifluoromethyl)-1H-pyrazole-5-carboxylic acid (9i) (1.0 g, 3.55 mmol) in THF (10 mL) was added LiHMDS (14 mL, 1M in THF) and heated at reflux overnight. The reaction mixture was cooled to room temperature and pH was adjusted to 2-3 using KHSO$_4$ (1N aqueous solution). The organic solvent was removed under vacuum and the aqueous layer was extracted with EtOAc (5×50 mL). The organic layers were combined dried over MgSO$_4$, filtered and concentrated in vacuum. The residue obtained was purified by flash column chromatography (silica gel, eluting with CMA-80 in chloroform 0-100%, followed by 0-100% chloroform in CMA 50) to give 1-(3-cyanophenyl)-3-(trifluoromethyl)-1H-pyrazole-5-carboxylic acid (236g) (250 mg, 23%) as a white solid; $^1$H NMR (300 MHz, DMSO-d$_6$) δ 10.63-8.88 (m, 4H), 8.03-7.92 (m, 2H), 7.87 (dt, J=8.1, 1.3 Hz, 1H), 7.74 (t, J=7.9 Hz, 1H), 7.03 (d, J=0.6 Hz, 1H); MS (ES+) 299.3 (M+1); 297.3 (M−1).

Step-6: Preparation of (+)-1-(3-carbamimidoylphenyl)-N-(5-((3-cyanophenyl)(cyclopropylmethylamino)methyl)-2-fluorophenyl)-3-(trifluoromethyl)-1H-pyrazole-5-carboxamide (236h)

To a solution of 1-(3-carbamimidoylphenyl)-3-(trifluoromethyl)-1H-pyrazole-5-carboxylic acid hydrochloride (236g) (200 mg, 0.671 mmol) in DMF (10 mL) was added bromo-tris-pyrrolidino phosphoniumhexafluorophosphate (PyBrop, 375 mg, 0.805 mmol), pyridine (265 mg, 3.35 mmol), and stirred at room temperature for 10 min. To the reaction mixture was added (+)-3-((3-amino-4-fluorophenyl)(cyclopropylmethylamino)methyl)benzonitrile (236f) (198 mg, 0.671 mmol) and stirred at room temperature overnight under nitrogen atmosphere. The reaction was quenched with aqueous HCl (6 N, 20 mL) and washed with ethyl acetate (4×50 mL). The aqueous layer was basified to pH 9 using 1 N NaOH and extracted with ethyl acetate (4×40 mL). The organic layers were combined dried, filtered, and concentrated in vacuum to dryness. The residue obtained was purified by flash column chromatography (silica gel, eluting with 0-100% CMA-80 in chloroform) to furnish compound 236h as a free base. The free base was dissolved in dioxane (5 mL) added HCl (4N in dioxane, 4 mL) and stirred at room temperature for 1 h. The solution was concentrated and dried under vacuum to (+)-1-(3-carbamimidoylphenyl)-N-(5-((3-cyanophenyl)(cyclopropylmethylamino)methyl)-2-fluorophenyl)-3-(trifluoromethyl)-1H-pyrazole-5-carboxamide (236h) (74 mg, 0.129 mmol, 19.17% yield) salt as a white solid; $^1$H NMR (300 MHz, DMSO-d$_6$) δ 10.87 (s, 1H), 10.43 (s, 2H), 9.51 (s, 2H), 9.31 (s, 2H), 8.28 (s, 1H), 8.07 (d, J=8.3 Hz, 1H), 8.03 (d, J=2.0 Hz, 1H), 8.01-7.69 (m, 6H), 7.65 (t, J=7.8 Hz, 1H), 7.41 (t, J=9.4 Hz, 1H), 5.97-5.59 (m, 1H), 2.80-2.60 (m, 2H), 1.32-1.01 (m, 2H), 0.99-0.72 (m, 1H), 0.66-0.43 (m, 2H), 0.41-0.16 (m, 2H); MS (ES$^+$): MS (ES+) 576.4 (M+1); Optical rotation: $[α]_D$=(+) 2.31 [0.26, MeOH].

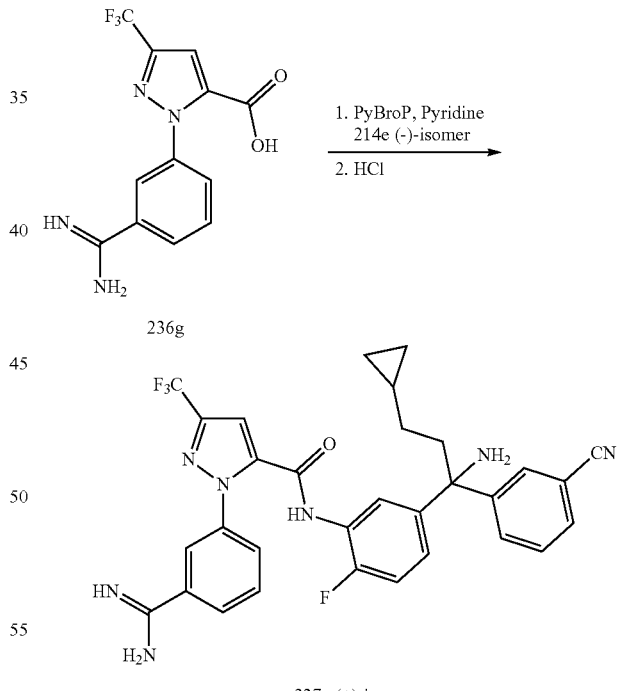

Scheme 237

236g 237a (+)-isomer

Preparation of (+)-N-(5-(1-amino-1-(3-cyanophenyl)-3-cyclopropylpropyl)-2-fluorophenyl)-1-(3-carbamimidoylphenyl)-3-(trifluoromethyl)-1H-pyrazole-5-carboxamide (237a)

To a solution of 1-(3-carbamimidoylphenyl)-3-(trifluoromethyl)-1H-pyrazole-5-carboxylic acid (236g) (300 mg, 1.006 mmol) in DMF (10 mL) was added bromo-tris-pyrrolidino phosphoniumhexafluorophosphate(PyBrop, 563 mg, 1.207 mmol), pyridine (398 mg, 5.03 mmol) stirred at room temperature for 10 min and added ((R)—N-((−)-1-(3-amino-4-fluorophenyl)-1-(3-cyanophenyl)-3-cyclopropyl-propyl)-2-methylpropane-2-sulfinamide (214e) (416 mg, 1.006 mmol). The reaction mixture was stirred at room temperature overnight, quenched with aqueous HCl (6 N, 20 mL) and washed with ethyl acetate (4×30 mL). The aqueous layer was basified to pH 9 using 1 N NaOH and extracted with ethyl acetate (4×40 mL). The organic layers were combined dried, filtered, and concentrated in vacuum to dryness. The residue obtained was purified by flash column chromatography (silica gel, eluting with 0-100% CMA-80 in chloroform) to furnish 237a free base a white solid; $^1$H NMR (300 MHz, DMSO-d$_6$) δ 10.67 (s, 1H), 9.64-9.38 (m, 2H), 9.22 (s, 2H), 8.01 (m, 1H), 7.95 (m, 1H), 7.92-7.85 (m, 2H), 7.79-7.64 (m, 4H), 7.54 (m, 2H), 7.37-7.16 (m, 2H), 2.39-2.19 (m, 2H), 1.15-0.90 (m, 2H), 0.72-0.55 (m, 1H), 0.41-0.28 (m, 2H), −0.01−−0.11 (m, 2H); $^{19}$F NMR (282 MHz, DMSO) δ −60.84, −123.70; MS (ES+) 590.5 (M+1); IR (KBr) 2235 cm$^{-1}$; Optical rotation: [α]$_D$=(+) 6.53 (0.245, methanol); The free base was dissolved in dioxane (5 mL) added HCl (4 N in dioxane, 10 eq) and stirred at room temperature for 1 h. The solution was concentrated and dried under vacuum to afford furnish (+)-N-(5-(1-amino-1-(3-cyanophenyl)-3-cyclopropylpropyl)-2-fluorophenyl)-1-(3-carbamimidoylphenyl)-3-(trifluoromethyl)-1H-pyrazole-5-carboxamide (237a) (60 mg) as a white solid; $^1$H NMR (300 MHz, DMSO-d$_6$) δ 10.85 (s, 1H), 9.54 (s, 5H), 9.33 (s, 3H), 8.12-7.06 (m, 12H), 3.77-3.58 (m, 2H), 2.74-2.21 (m, 2H), 0.78-0.51 (m, 1H), 0.47-0.22 (m, 2H), −0.00 (s, 2H); $^{19}$F NMR (282 MHz, DMSO) δ −60.84, −123.62; MS (ES+) 590.5 (M+1), (ES−) 624.5 (M+Cl); IR (KBr) 2232 cm$^1$.

Scheme 238

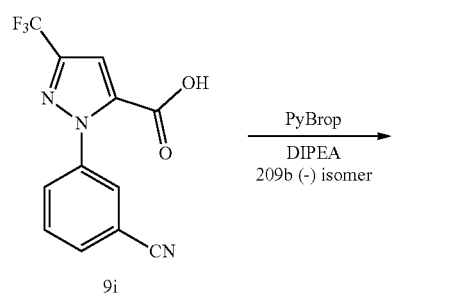

9i

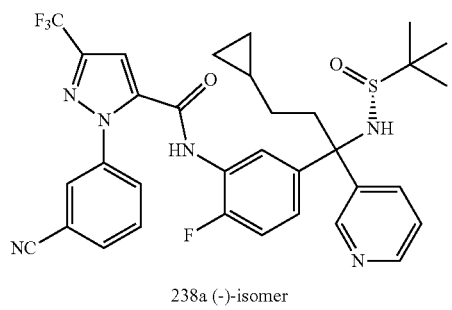

238a (−)-isomer

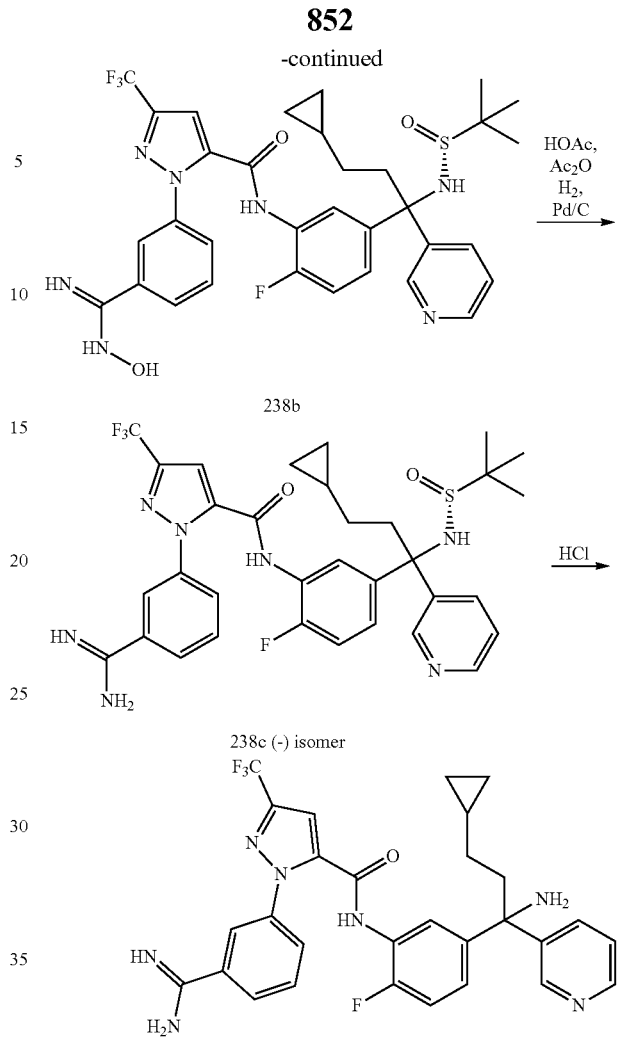

Preparation of 1-(3-carbamimidoylphenyl)-N-(5-((−)-3-cyclopropyl-1-((R)-1,1-dimethylethylsulfinamido)-1-(pyridin-3-yl)propyl)-2-fluorophenyl)-3-(trifluoromethyl)-1H-pyrazole-5-carboxamide (238c)

Step-1: Preparation of 1-(3-cyanophenyl)-N-(5-((−)-3-cyclopropyl-1-((R)-1,1-dimethylethylsulfinamido)-1-(pyridin-3-yl)propyl)-2-fluorophenyl)-3-(trifluoromethyl)-1H-pyrazole-5-carboxamide (238a)

Compound 238a was prepared from 1-(3-cyanophenyl)-3-(trifluoromethyl)-1H-pyrazole-5-carboxylic acid (9i) and (R)—N-((−)-1-(3-amino-4-fluorophenyl)-3-cyclopropyl-1-(pyridin-3-yl)propyl)-2-methylpropane-2-sulfinamide (209b) (3 g, 7.70 mmol) according to the procedure reported in step-3 of scheme 208 to afford after flash column chromatography [silica gel 80 g, eluting with 0-50% ethyl acetate/methanol (9:1) in hexanes] 1-(3-cyanophenyl)-N-(5-((−)-3-cyclopropyl-1-((R)-1,1-dimethylethylsulfinamido)-1-(pyridin-3-yl)propyl)-2-fluorophenyl)-3-(trifluoromethyl)-1H-pyrazole-5-carboxamide (238a) (3.518 g, 69.9% yield) as a white solid; $^1$H NMR (300 MHz, DMSO-d$_6$) δ 8.55-8.45 (m, 1H), 8.40 (td, J=5.0, 1.5 Hz, 2H), 10.58 (s, 1H), 8.11 (t, J=1.9 Hz, 1H), 8.00 (dt, J=7.8, 1.3 Hz, 1H), 7.92-7.85 (m, 1H), 7.75-7.67 (m, 3H), 7.55 (d, J=7.0 Hz, 1H), 7.39-7.18 (m, 3H), 5.57 (s, 1H), 2.70-2.50 (m, 2H), 1.12 (s, 9H), 0.98-0.78 (m, 1H), 0.73-0.51 (m, 1H), 0.35 (m, 2H), −0.10 (m, 2H); $^{19}$F NMR (282 MHz, DMSO) δ −60.78, −122.81; MS (ES+) 653.5 (M+1); (ES−) 651.5 (M−1); Optical Rotation $[α]_D$=(−) 21.82 [0.55, MeOH].

Step-2: Preparation of 1-(3-carbamimidoylphenyl)-N-(5-((−)-3-cyclopropyl-1-((R)-1,1-dimethylethylsulfinamido)-1-(pyridin-3-yl)propyl)-2-fluorophenyl)-3-(trifluoromethyl)-1H-pyrazole-5-carboxamide (238c)

To a solution of 1-(3-cyanophenyl)-N-(5-((−)-3-cyclopropyl-1-((R)-1,1-dimethylethylsulfinamido)-1-(pyridin-3-yl)propyl)-2-fluorophenyl)-3-(trifluoromethyl)-1H-pyrazole-5-carboxamide (238a) (490 mg, 0.751 mmol) in ethanol (50 mL) was added hydroxylamine (124 mg, 3.75 mmol) and heated at reflux overnight. The reaction was cooled to room temperature and concentrated in vacuum to dryness. The residue of N-(5-(3-cyclopropyl-1-((−)-1,1-dimethylethylsulfinamido)-1-(pyridin-3-yl)propyl)-2-fluorophenyl)-1-(3-(N-hydroxycarbamimidoyl)phenyl)-3-(trifluoromethyl)-1H-pyrazole-5-carboxamide (238b) was dissolved in acetic acid (50 mL) and added Ac$_2$O (10 mL). The reaction mixture was stirred at room temperature for 2 h, added Pd/C (200 mg) and hydrogenated at 65 psi for 12 h at room temperature. The reaction mixture was filtered through a Celite Pad and filtrate was concentrated in vacuum. The residue obtained was purified by flash column chromatography (silica gel, 12 g eluting with CMA80/CHCl$_3$, 0-100%) to furnish 1-(3-carbamimidoylphenyl)-N-(5-((−)-3-cyclopropyl-1-((R)-1,1-dimethylethylsulfinamido)-1-(pyridin-3-yl)propyl)-2-fluorophenyl)-3-(trifluoromethyl)-1H-pyrazole-5-carboxamide (238c) (256 mg, 0.382 mmol, 50.9% yield) as a white solid; $^1$H NMR (300 MHz, DMSO-d$_6$) δ 9.78 (s, 4H), 8.48 (d, J=2.4 Hz, 1H), 8.41 (dd, J=4.8, 1.5 Hz, 1H), 8.01-7.96 (m, 1H), 7.92 (d, J=7.9 Hz, 1H), 7.81-7.74 (m, 1H), 7.73-7.62 (m, 3H), 7.59-7.53 (m, 1H), 7.37-7.18 (m, 3H), 5.55 (s, 1H), 2.76-2.54 (m, 2H), 1.12 (s, 9H), 0.92 (m, 2H), 0.63 (m, 1H), 0.34 (m, 2H), −0.09 (m, 2H). $^{19}$F NMR (282 MHz, DMSO) δ −60.65, −122.63; MS (ES+) 670.5 (M+1), (ES−) 668.5 (M−1); Optical Rotation $[α]_D$=(−) 63.85 [0.26, MeOH].

Preparation of (+)-N-(5-(1-amino-3-cyclopropyl-1-(pyridin-3-yl)propyl)-2-fluorophenyl)-1-(3-carbamimidoylphenyl)-3-(trifluoromethyl)-1H-pyrazole-5-carboxamide (238d)

To a solution of 1-(3-carbamimidoylphenyl)-N-(5-((−)-3-cyclopropyl-1-((R)-1,1-dimethylethylsulfinamido)-1-(pyridin-3-yl)propyl)-2-fluorophenyl)-3-(trifluoromethyl)-1H-pyrazole-5-carboxamide (238c) (100 mg, 0.149 mmol) in MeOH (5 mL) was added HCl (0.070 mL, 0.280 mmol, 4 N in 1,4-dioxane) and stirred at room temperature for 2 h. Additional HCl (4 N in 1,4-dioxane, 0.12 mL) was added and continued stirring until reaction was complete. The reaction mixture was concentrated to dryness and purified twice by flash column chromatography [silica gel, eluting with chloroform/CMA80 (1:0 to 0:1)] to afford compound 238d (30 mg, 0.053 mmol, 35.5%) free base as an oil. The free base (30 mg, 0.053 mmol) was dissolved in methanol (8 mL) added 4 N HCl (aq. 0.053 mL) and concentrated in vacuum to furnish (+)-N-(5-(1-amino-3-cyclopropyl-1-(pyridin-3-yl)propyl)-2-fluorophenyl)-1-(3-carbamimidoylphenyl)-3-(trifluoromethyl)-1H-pyrazole-5-carboxamide (238d) (35 mg, 92.8%) hydrochloride salt as a white solid; $^1$H NMR (300 MHz, DMSO-d$_6$) δ 10.85 (s, 1H), 9.58 (s, 3H), 9.52 (s, 3H), 9.27 (s, 2H), 8.70-8.60 (m, 2H), 8.06-7.93 (m, 3H), 7.92-7.85 (m, 1H), 7.80 (s, 1H), 7.76 (m, 1H), 7.64 (m, 1H), 7.54 (m, 1H), 7.47-7.32 (m, 2H), 2.75-2.40 (m, 2H), 1.12 (m, 2H), 0.77-0.57 (m, 1H), 0.44-0.30 (m, 2H), 0.08 to −0.08 (m, 2H); $^{19}$F NMR (282 MHz, DMSO-d$_6$) δ −60.50, −119.76; MS (ES−): 564.5 (M−1); Optical Rotation $[α]_D$=(+) 2.22 [0.18, MeOH].

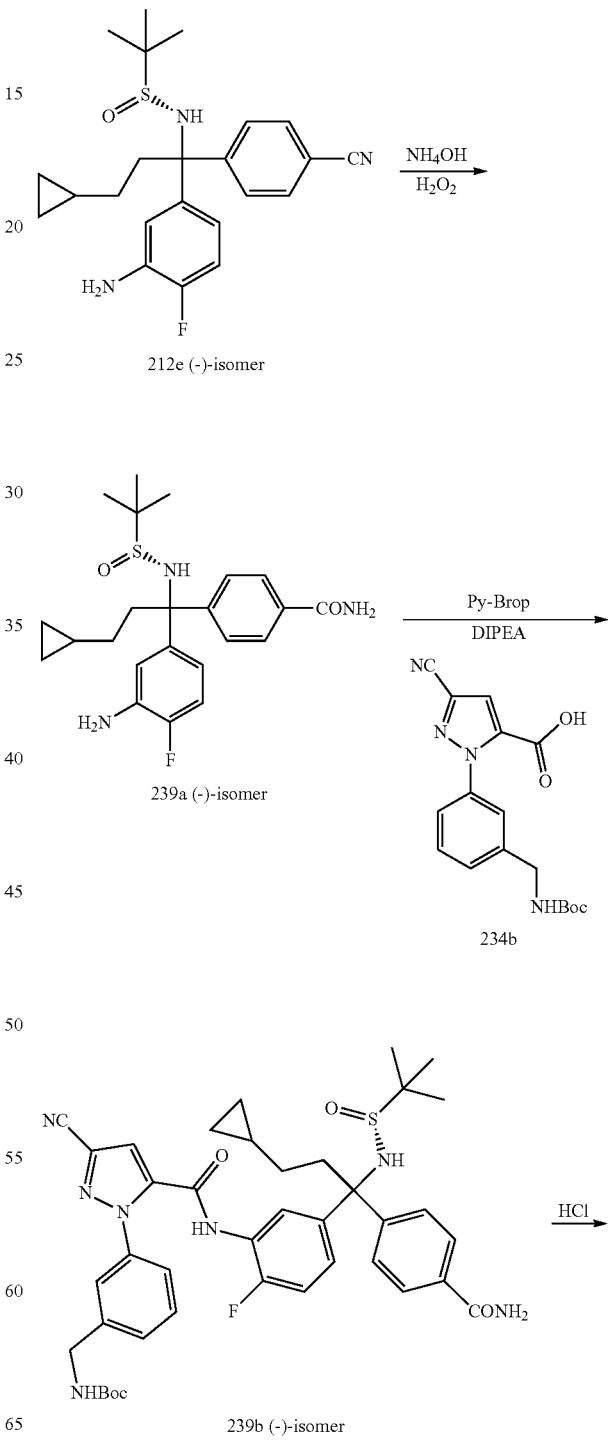

Scheme 239

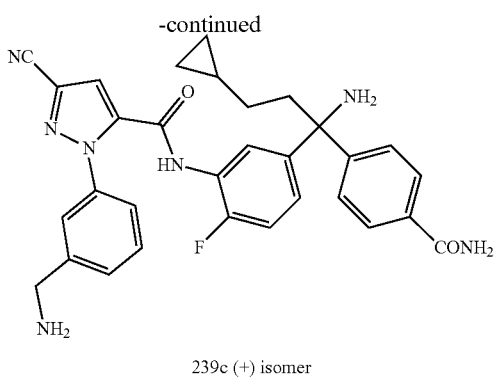

239c (+) isomer

Preparation of: (+)-N-(5-(1-amino-1-(4-carbamoyl-phenyl)-3-cyclopropylpropyl)-2-fluorophenyl)-1-(3-(aminomethyl)phenyl)-3-cyano-1H-pyrazole-5-carboxamide (239c)

Step 1: Preparation of 4-((−)-1-(3-amino-4-fluorophenyl)-3-cyclopropyl-1-((R)-1,1-dimethylethylsulfinamido)propyl)benzamide (239a)

To a solution of (R)—N-((−)-1-(3-amino-4-fluorophenyl)-1-(4-cyanophenyl)-3-cyclopropylpropyl)-2-methylpropane-2-sulfinamide (212e) (1.41 g, 3.41 mmol) in ethanol (80 mL) was added conc. NH₄OH (30 mL) hydrogen peroxide (1.200 mL, 13.59 mmol) and stirred at room temperature for 22 h. The reaction mixture was concentrated in vacuum to dryness and purified by flash column chromatography [silica gel with chloroform/methanol (1:0 to 9:1)] to afford 4-((−)-(1-(3-amino-4-fluorophenyl)-3-cyclopropyl-1-((R)-1,1-dimethylethylsulfinamido)propyl)benzamide (239a) (335 mg, 22.77%) as a brown solid. $^1$H NMR (300 MHz, DMSO-d$_6$) δ 7.93 (s, 1H), 7.82-7.72 (m, 2H), 7.43-7.36 (m, 2H), 7.33 (s, 1H), 6.88 (dd, J=11.2, 8.5 Hz, 1H), 6.70 (dd, J=8.8, 2.3 Hz, 1H), 6.48 (ddd, J=8.5, 4.2, 2.3 Hz, 1H), 5.14-4.98 (m, 3H), 2.65-2.40 (m, 2H), 1.20-1.05 (m, 1H), 1.13 (s, 9H), 0.97-0.80 (m, 1H), 0.72-0.55 (m, 1H), 0.42-0.29 (m, 2H), 0.07--0.20 (m, 2H); $^{19}$F NMR (282 MHz, DMSO-d$_6$) δ −137.75; MS (ES+): 432.4 (M+1); Optical rotation: [α]$_D$=(−) 77.82 [0.275, MeOH].

Step 2: Preparation of tert-butyl 3-(5-(5-((−)-1-(4-carbamoylphenyl)-3-cyclopropyl-1-((R)-1,1-dimethylethylsulfinamido)propyl)-2-fluorophenylcarbamoyl)-3-cyano-1H-pyrazol-1-yl)benzylcarbamate (239b)

Compound 239b was prepared from 4-((−)-(1-(3-amino-4-fluorophenyl)-3-cyclopropyl-1-((R)-1,1-dimethylethylsulfinamido)propyl)benzamide (239a) (275 mg, 0.636 mmol) and 1-(3-((tert-butoxycarbonylamino)methyl)phenyl)-3-cyano-1H-pyrazole-5-carboxylic acid (234b) (240 mg, 0.7 mmol) using procedure as reported in step-3 of scheme-208 gave after purification by flash column chromatography [silica gel with chloroform/methanol (1:0 to 19:1)] tert-butyl 3-(5-(5-((−)-1-(4-carbamoylphenyl)-3-cyclopropyl-1-((R)-1,1-dimethylethylsulfinamido)propyl)-2-fluorophenylcarbamoyl)-3-cyano-1H-pyrazol-1-yl)benzylcarbamate (239b) (188 mg, 39.1%) as an off-white solid. $^1$H NMR (300 MHz, DMSO-d$_6$) δ 10.62 (s, 1H), 7.93 (s, 1H), 7.81-7.70 (m, 3H), 7.61-7.14 (m, 11H), 5.39 (s, 1H), 4.19 (d, J=6.2 Hz, 2H), 2.60-2.40 (m, 2H), 1.38 (s, 9H), 1.12 (s, 9H), 1.18-1.02 (m, 1H), 0.98-0.78 (m, 1H), 0.72-0.55 (m, 1H), 0.40-0.25 (m, 2H), 0.08 to −0.20 (s, 2H); $^{19}$F NMR (282 MHz, DMSO-d$_6$) δ −123.20; MS (ES+): 756.6 (M+1); Optical rotation: [α]$_D$=(−) 62.04 [0.245, MeOH].

Step 3: (+)-N-(5-(1-amino-1-(4-carbamoylphenyl)-3-cyclopropylpropyl)-2-fluorophenyl)-1-(3-(aminomethyl)phenyl)-3-cyano-1H-pyrazole-5-carboxamide (239c)

To a solution of tert-butyl 3-(5-(5-((−)-1-(4-carbamoylphenyl)-3-cyclopropyl-1-((R)-1,1-dimethylethylsulfinamido)propyl)-2-fluorophenylcarbamoyl)-3-cyano-1H-pyrazol-1-yl)benzylcarbamate (239b) (161 mg, 0.213 mmol) in ethanol (15 mL) was added conc. HCl (0.180 mL, 2.162 mmol) heated at reflux for 1 h, cooled to room temperature and concentrated in vacuum to dryness. The residue was purified twice by column chromatography [silica gel, eluting with chloroform/CMA80 (1:0 to 2:1) for first column and chloroform/methanol (1:0 to 3:1) for second column] to afford 239c (50 mg, 33.7%) free base as a white solid. The free base (46 mg, 0.083 mmol) was dissolved in ethanol (5 mL) added conc. HCl (aqueous 0.035 mL) and concentrated in vacuum to dryness. The residue was dissolved in 5 mL of water and concentrated to give (+)-N-(5-(1-amino-1-(4-carbamoylphenyl)-3-cyclopropylpropyl)-2-fluorophenyl)-1-(3-(aminomethyl)phenyl)-3-cyano-1H-pyrazole-5-carboxamide (239c) (58 mg, 91.85%) hydrochloride salt as a white solid. $^1$H NMR (300 MHz, DMSO-d$_6$) δ 10.84 (s, 1H), 9.25 (s, 3H), 8.36 (s, 3H), 8.06 (s, 1H), 7.91 (d, J=8.2 Hz, 2H), 7.82 (s, 1H), 7.73 (s, 1H), 7.64-7.25 (m, 9H), 4.12 (q, J=5.9 Hz, 2H), 2.70-2.40 (m, 2H), 1.20-0.95 (m, 2H), 0.75-0.60 (m, 1H), 0.49-0.28 (m, 2H), 0.03-0.06 (m, 2H); $^{19}$F NMR (282 MHz, DMSO-d$_6$) δ −120.45; MS (ES+): 574.5 (M+Na); Optical rotation: [α]$_D$=(+) 12.5 [0.24, MeOH].

Scheme 240

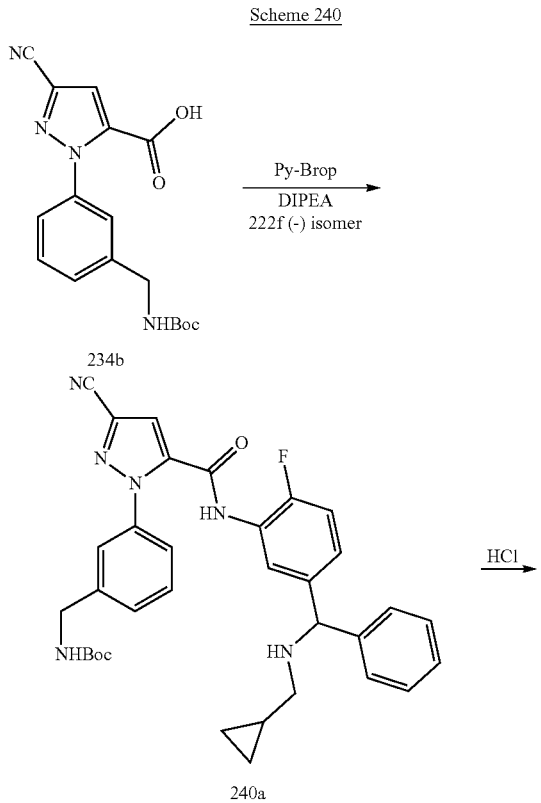

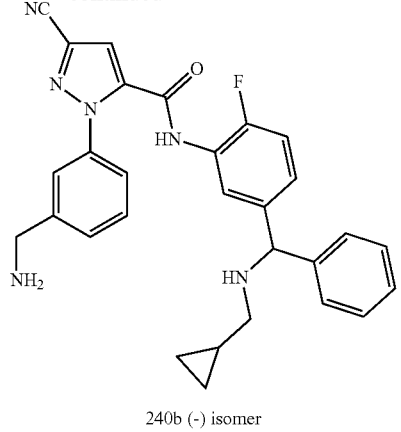

240b (-) isomer

Preparation of: (−)-1-(3-(aminomethyl)phenyl)-3-cyano-N-(5-((cyclopropylmethylamino)(phenyl)methyl)-2-fluorophenyl)-1H-pyrazole-5-carboxamide (240b)

Step 1: Preparation of tert-butyl 3-(3-cyano-5-(5-((cyclopropylmethylamino)(phenyl)methyl)-2-fluorophenylcarbamoyl)-1H-pyrazol-1-yl)benzylcarbamate (240a)

Compound 240a was prepared from (−)-5-((cyclopropylmethylamino)(phenyl)methyl)-2-fluoroaniline (222f) (147 mg, 0.545 mmol) and 1-(3-((tert-butoxycarbonylamino)methyl)-phenyl)-3-cyano-1H-pyrazole-5-carboxylic acid (234b) (205 mg, 0.6 mmol) using procedure as reported in step-3 of scheme-208 to afford after purification by flash column chromatography [silica gel with chloroform/methanol (1:0 to 19:1)] tert-butyl 3-(3-cyano-5-(5-((cyclopropylmethylamino)(phenyl)methyl)-2-fluorophenylcarbamoyl)-1H-pyrazol-1-yl)benzylcarbamate (240a) (161 mg, 49.6%) as a yellow gum. $^1$H NMR (300 MHz, DMSO-$d_6$) δ 10.59 (s, 1H), 7.73 (s, 1H), 7.61 (d, J=7.4 Hz, 1H), 7.53-7.12 (m, 12H), 4.83 (s, 1H), 4.19 (d, J=6.2 Hz, 2H), 2.32-2.20 (m, 2H), 1.38 (s, 9H), 0.97-0.83 (m, 1H), 0.44-0.29 (m, 2H), 0.08 to −0.08 (m, 2H); $^{19}$F NMR (282 MHz, DMSO-$d_6$) δ −123.61; MS (ES+): 595.5 (M+1).

Step 2: Preparation of (−)-1-(3-(aminomethyl)phenyl)-3-cyano-N-(5-((cyclopropylmethylamino)(phenyl)methyl)-2-fluorophenyl)-1H-pyrazole-5-carboxamide (240b)

To a solution of tert-butyl 3-(3-cyano-5-(5-((cyclopropylmethylamino)(phenyl)methyl)-2-fluorophenylcarbamoyl)-1H-pyrazol-1-yl)benzylcarbamate (240a) (150 mg, 0.252 mmol) in ethanol (15 mL) was added conc. HCl (0.210 mL, 2.52 mmol) heated at reflux for 1 h, cooled to room temperature and concentrated in vacuum to dryness. The residue was purified twice by column chromatography [silica gel, eluting with chloroform/CMA80 (1:0 to 2:1) for first column and chloroform/methanol (1:0 to 9:1) for second column] to afford (−)-1-(3-(aminomethyl)phenyl)-3-cyano-N-(5-((cyclopropylmethylamino)(phenyl)methyl)-2-fluorophenyl)-1H-pyrazole-5-carboxamide (240b) (44 mg, 35.3%) free base as a white solid. $^1$H NMR (300 MHz, DMSO-$d_6$) δ 7.71 (s, 1H), 7.65-7.12 (m, 12H), 4.83 (s, 1H), 3.77 (s, 2H), 2.26 (m, 2H), 0.90 (s, 1H), 0.44-0.29 (m, 2H), 0.12-−0.06 (m, 2H); (ES+): 517.5 (M+Na); IR 2244 cm$^{-1}$; Optical rotation: [α]$_D$=(−) 7.62 [0.105, CH$_3$OH].

Scheme 241

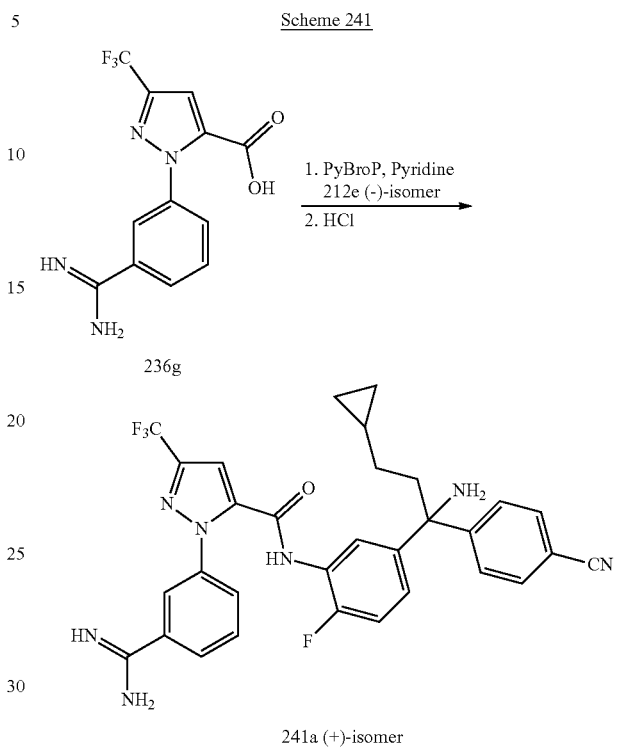

241a (+)-isomer

Preparation of (+)-N-(5-(1-amino-1-(4-cyanophenyl)-3-cyclopropylpropyl)-2-fluorophenyl)-1-(3-carbamimidoylphenyl)-3-(trifluoromethyl)-1H-pyrazole-5-carboxamide (241a)

Compound 241a was prepared from 1-(3-carbamimidoylphenyl)-3-(trifluoromethyl)-1H-pyrazole-5-carboxylic acid hydrochloride (236g) (500 mg, 1.677 mmol) and (R)—N-((−)-1-(3-amino-4-fluorophenyl)-1-(4-cyanophenyl)-3-cyclopropylpropyl)-2-methylpropane-2-sulfinamide (212e) (693 mg, 1.677 mmol) according to procedure described in scheme-237 for preparation of compound 237a gave after purification by flash column chromatography (silica gel, eluting with 0-100% CMA-80 in chloroform) compound 241a (235 mg, 0.399 mmol, 23.77% yield) free base as a white solid; $^1$H NMR (300 MHz, DMSO-$d_6$) δ 8.91 (s, 4H), 8.26 (s, 1H), 8.20 (d, J=7.7 Hz, 1H), 8.04-7.81 (m, 8H), 7.55 (m, 1H), 7.45 (t, J=9.4 Hz, 1H), 2.60 (s, 2H), 2.55-2.45 (m, 2H), 1.42-1.19 (m, 2H), 0.90 (m, 1H), 0.70-0.46 (m, 2H), 0.19 (m, 2H). The free base was dissolved in dioxane (5 mL) added HCl (4N in dioxane, 0.4 mL) and stirred at room temperature for 1 h. The solution was concentrated and dried under vacuum to afford (+)-N-(5-(1-amino-1-(4-cyanophenyl)-3-cyclopropylpropyl)-2-fluorophenyl)-1-(3-carbamimidoylphenyl)-3-(trifluoromethyl)-1H-pyrazole-5-carboxamide (241a) hydrochloride salt as a white solid; $^1$H NMR (300 MHz, DMSO-$d_6$) δ 10.77 (s, 1H), 9.50 (s, 3H), 9.22 (s, 2H), 8.10-7.68 (m, 7H), 7.54 (t, J=7.6 Hz, 3H), 7.33 (s, 2H), 1.20-0.94 (m, 2H), 0.71-0.57 (m, 1H), 0.36 (d, J=7.4 Hz, 2H), −0.00-−0.14 (m, 2H); MS (ES+): 590.5 (M+1); IR (KBr) 2233 cm$^{-1}$; optical rotation (+) 14.81 (0.27, methanol).

Scheme 242

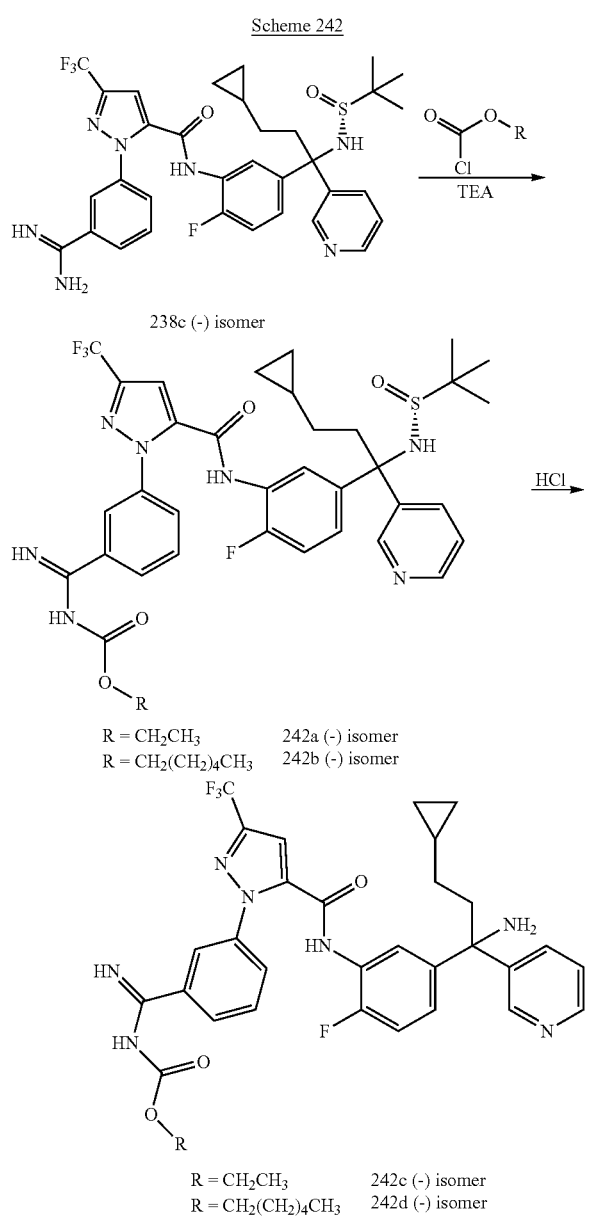

R = CH₂CH₃     242a (-) isomer
R = CH₂(CH₂)₄CH₃     242b (-) isomer

R = CH₂CH₃     242c (-) isomer
R = CH₂(CH₂)₄CH₃     242d (-) isomer

Preparation of (−)-ethyl (3-(5-(5-(1-amino-3-cyclo-propyl-1-(pyridin-3-yl)propyl)-2-fluorophenylcarbamoyl)-3-(trifluoromethyl)-1H-pyrazol-1-yl)phenyl)(imino)methylcarbamate (242c)

Step-1: Preparation of ethyl (3-(5-(5-((−)-3-cyclopropyl-1-((R)-1,1-dimethylethylsulfinamido)-1-(pyridin-3-yl)propyl)-2-fluorophenylcarbamoyl)-3-(trifluoromethyl)-1H-pyrazol-1-yl)phenyl)(imino)methylcarbamate (242a)

Compound 242a was prepared from 1-(3-carbamimidoyl-phenyl)-N-(5-((−)-3-cyclopropyl-1-((R)-1,1-dimethylethyl-sulfinamido)-1-(pyridin-3-yl)propyl)-2-fluorophenyl)-3-(trifluoromethyl)-1H-pyrazole-5-carboxamide (238c) (109 mg, 0.163 mmol) and ethyl carbonochloridate (0.016 mL, 0.163 mmol) according to the procedure reported for preparation of compound 233a in scheme-233 to furnish after purification by flash column chromatography [silica gel eluting with hexanes/10% methanol in ethyl acetate (1:0 to 1:1)] ethyl (3-(5-(5-((−)-3-cyclopropyl-1-((R)-1,1-dimethylethylsulfinamido)-1-(pyridin-3-yl)propyl)-2-fluorophenyl-carbamoyl)-3-(trifluoromethyl)-1H-pyrazol-1-yl)phenyl)(imino)methylcarbamate (242a) (50 mg, 0.067 mmol, 41.4%) as a white solid; ¹H NMR (300 MHz, DMSO-d₆) δ 10.59 (s, 1H), 9.20 (s, 2H), 8.51-8.47 (m, 1H), 8.41 (dd, J=4.7, 1.5 Hz, 1H), 8.15 (t, J=1.9 Hz, 1H), 8.11 (d, J=7.8 Hz, 1H), 7.74-7.53 (m, 5H), 7.32 (dd, J=8.0, 4.7 Hz, 1H), 7.28-7.16 (m, 2H), 5.55 (s, 1H), 4.06 (q, J=7.1 Hz, 2H), 2.75-2.40 (m, 2H), 1.20-1.00 (m, 1H), 1.21 (t, J=7.1 Hz, 3H), 1.11 (s, 9H), 0.97-0.81 (m, 1H), 0.70-0.52 (m, 1H), 0.40-0.22 (m, 2H), −0.02 to −0.18 (m, 2H); ¹⁹F NMR (282 MHz, DMSO-d₆) δ −60.62, −122.82; MS (ES+): 742.6 (M+1); Optical rotation: [α]_D=(−) 68.09 [0.235, MeOH].

Step-2: Preparation of (−)-ethyl (3-(5-(5-(1-amino-3-cyclopropyl-1-(pyridin-3-yl)propyl)-2-fluorophenylcarbamoyl)-3-(trifluoromethyl)-1H-pyrazol-1-yl)phenyl)(imino)methylcarbamate (242c)

To a solution of ethyl (3-(5-(5-((−)-3-cyclopropyl-1-((R)-1,1-dimethylethylsulfinamido)-1-(pyridin-3-yl)propyl)-2-fluorophenylcarbamoyl)-3-(trifluoromethyl)-1H-pyrazol-1-yl)phenyl)(imino)methylcarbamate (242a) (48 mg, 0.065 mmol) in MeOH (5 mL) was added HCl (0.065 mL, 0.259 mmol, 4 N in 1,4-dioxane) stirred at room temperature and concentrated in vacuum to dryness. The residue was purified by flash column chromatography [silica gel, eluting with chloroform/CMA80 (1:0 to 2:1)] to afford compound 242c (24 mg, 0.038 mmol) free base as a white syrup. The free base was dissolved in methanol (8 mL) added 4 N HCl (aq. 0.038 mL) and concentrated in vacuum to dryness to afford (−)-ethyl (3-(5-(5-(1-amino-3-cyclopropyl-1-(pyridin-3-yl)propyl)-2-fluorophenylcarbamoyl)-3-(trifluoromethyl)-1H-pyrazol-1-yl)phenyl)(imino)methylcarbamate (242c) (38 mg) hydrochloride as a white solid; ¹H NMR (300 MHz, DMSO-d₆) δ 11.44 (s, 1H), 10.88 (s, 1H), 10.60 (s, 1H), 9.61 (s, 3H), 8.73-8.56 (m, 2H), 8.06-7.85 (m, 4H), 7.80 (s, 1H), 7.73 (m, 1H), 7.64 (m, 1H), 7.57-7.51 (m, 1H), 7.46-7.36 (m, 2H), 4.33 (q, J=7.1 Hz, 2H), 2.65-2.40 (m, 2H), 1.31 (t, J=7.1 Hz, 3H), 1.13 (m, 2H), 0.75-0.60 (m, 1H), 0.37 (m, 2H), 0.05 to −0.04 (m, 2H); ¹⁹F NMR (282 MHz, DMSO-d₆) δ −60.71, −119.86; MS (ES+): 638.5 (M+1); Optical rotation: [α]_D=(−) 9.78 [0.225, MeOH].

Preparation of (−)-hexyl (3-(5-(5-(1-amino-3-cyclo-propyl-1-(pyridin-3-yl)propyl)-2-fluorophenylcarbamoyl)-3-(trifluoromethyl)-1H-pyrazol-1-yl)phenyl)(imino)methylcarbamate (242d)

Step-1: Preparation of hexyl (3-(5-(5-((−)-3-cyclopropyl-1-((R)-1,1-dimethylethylsulfinamido)-1-(pyridin-3-yl)propyl)-2-fluorophenylcarbamoyl)-3-(trifluoromethyl)-1H-pyrazol-1-yl)phenyl)(imino)methylcarbamate (242b)

Compound 242b was prepared from 1-(3-carbamimidoyl-phenyl)-N-(5-((−)-3-cyclopropyl-1-((R)-1,1-dimethylethyl-sulfinamido)-1-(pyridin-3-yl)propyl)-2-fluorophenyl)-3-(trifluoromethyl)-1H-pyrazole-5-carboxamide (238c) (80 mg, 0.119 mmol) and hexyl chloroformate (19.7 mg, 0.119 mmol) according to the procedure reported for preparation of compound 233b in scheme-233 to furnish after purification by flash column chromatography (silica gel, 12 g, eluting with CMA80/CHCl₃, 0-60%) hexyl (3-(5-(5-((−)-3- cyclopropyl-1-((R)-1,1-dimethylethylsulfinamido)-1-(pyridin-3-yl)propyl)-2-fluorophenylcarbamoyl)-3-(trifluoromethyl)-1H-pyrazol-1-yl)phenyl)(imino)methylcarbamate (242b) (88 mg, 92.68% yield) as an off white solid; ¹H NMR (300 MHz, CDCl₃) δ 8.54 (s, 3H), 8.33-8.15 (m, 1H), 8.16-7.88 (m, 2H), 7.86-7.62 (m, 2H), 7.20-6.99 (m, 2H), 4.24 (td, J=7.0, 5.1 Hz, 2H), 4.17 (d, J=8.7 Hz, 1H), 2.74 (m, 2H), 1.87-1.69 (m, 2H), 1.50-1.22 (m, 16H), 1.07-0.92 (m, 6H), 0.80-0.63 (m, 1H), 0.47 (m, 2H), −0.00 (m, 2H); ¹⁹F NMR (282 MHz, CDCl3) δ −62.20, −129.62; MS (ES⁺): MS (ES+) 798.6 (M+1); Optical rotation: [α]$_D$=(−) 59.59 [0.245, CH₃OH].

Step-2: Preparation of (−)-hexyl (3-(5-(5-(1-amino-3-cyclopropyl-1-(pyridin-3-yl)propyl)-2-fluorophenylcarbamoyl)-3-(trifluoromethyl)-1H-pyrazol-1-yl)phenyl)(imino)methylcarbamate (242d)

To a solution of hexyl (3-(5-(5-((−)-3-cyclopropyl-1-((R)-1,1-dimethylethylsulfinamido)-1-(pyridin-3-yl)propyl)-2-fluorophenylcarbamoyl)-3-(trifluoromethyl)-1H-pyrazol-1-yl)phenyl)(imino)methylcarbamate (242b) (70.0 mg, 0.09 mmol) in anhydrous dioxane (3.0 mL) at room temperature was added HCl (0.1 mL, 4N in dioxane). The resulting mixture was stirred for 1 h and concentrated in vacuum. The residue obtained was purified twice by flash column chromatography (silica gel, first column (12g) eluting with CMA-80 in CHCl₃ 0-100%, second column (4g) MeOH in chloroform 0-40%) to furnish 242b as a free base. The free base was dissolved in MTBE (4 mL), added HCl (4N HCl in dioxane, 0.5 mL) and stirred for 30 min at room temperature. The slurry was concentrated in vacuum and dried to furnish (−)-hexyl (3-(5-(5-(1-amino-3-cyclopropyl-1-(pyridin-3-yl)propyl)-2-fluorophenylcarbamoyl)-3-(trifluoromethyl)-1H-pyrazol-1-yl)phenyl)(imino)methylcarbamate (242d) (45 mg, 74%) as an off white solid.
¹H NMR (300 MHz, DMSO-d₆) δ 11.44 (s, 1H), 10.87 (s, 1H), 10.59 (s, 1H), 9.60 (s, 3H), 8.66 (m, 2H), 8.06-7.96 (m, 3H), 7.95-7.86 (m, 2H), 7.80 (m, 1H), 7.73 (m, 1H), 7.62 (m, 1H), 7.58-7.50 (m, 1H), 7.41 (m, 2H), 4.27 (m, 2H), 2.56 (m, 2H), 1.67 (m, 2H), 1.44-1.21 (m, 8H), 1.20-1.03 (m, 3H), 0.68 (s, 1H), 0.49-0.31 (m, 2H), 0.00 (m, 2H); ¹⁹F NMR (282 MHz, DMSO) δ −60.63, −119.82; MS (ES+) 694.6 (M+1); Optical rotation: [α]$_D$=(−) 10.0 [0.26, MeOH].

Preparation of 1-(3-(aminomethyl)phenyl)-N-(5-((−)-3-cyclopropyl-1-((R)-1,1-dimethylethylsulfinamido)-1-(pyridin-3-yl)propyl)-2-fluorophenyl)-3-(trifluoromethyl)-1H-pyrazole-5-carboxamide (243a)

Compound 243a was prepared from 1-(3-cyanophenyl)-N-(5-((−)-3-cyclopropyl-1-((R)-1,1-dimethylethylsulfinamido)-1-(pyridin-3-yl)propyl)-2-fluorophenyl)-3-(trifluoromethyl)-1H-pyrazole-5-carboxamide (238a) (40 mg, 0.061 mmol) according to the procedure reported for preparation of compound 15g in step-6 of scheme-15 to furnish after purification by flash column chromatography [silica gel with chloroform/methanol (1:0 to 9:1)] 1-(3-(aminomethyl)phenyl)-N-(5-((−)-3-cyclopropyl-1-((R)-1,1-dimethylethylsulfinamido)-1-(pyridin-3-yl)propyl)-2-fluorophenyl)-3-(trifluoromethyl)-1H-pyrazole-5-carboxamide (243a) (13 mg, 32.3%) as an off-white solid; ¹H NMR (300 MHz, DMSO-d₆) δ 10.60 (s, 1H), 8.49 (d, J=2.3 Hz, 1H), 8.41 (dd, J=4.8, 1.5 Hz, 1H), 7.69 (d, J=8.1 Hz, 1H), 7.62-7.18 (m, 9H), 5.57 (s, 1H), 3.77 (s, 2H), 2.75-2.40 (m, 2H), 1.20-1.00 (m, 1H), 1.12 (s, 9H), 0.98-0.79 (m, 1H), 0.70-0.55 (m, 1H), 0.40-0.28 (m, 2H), 0.02-−0.20 (m, 2H); ¹⁹F NMR (282 MHz, DMSO-d₆) δ −60.54, −122.96; MS (ES+): 679.7 (M+Na); Optical Rotation [α]$_D$=(−) 81.90 [0.105, MeOH].

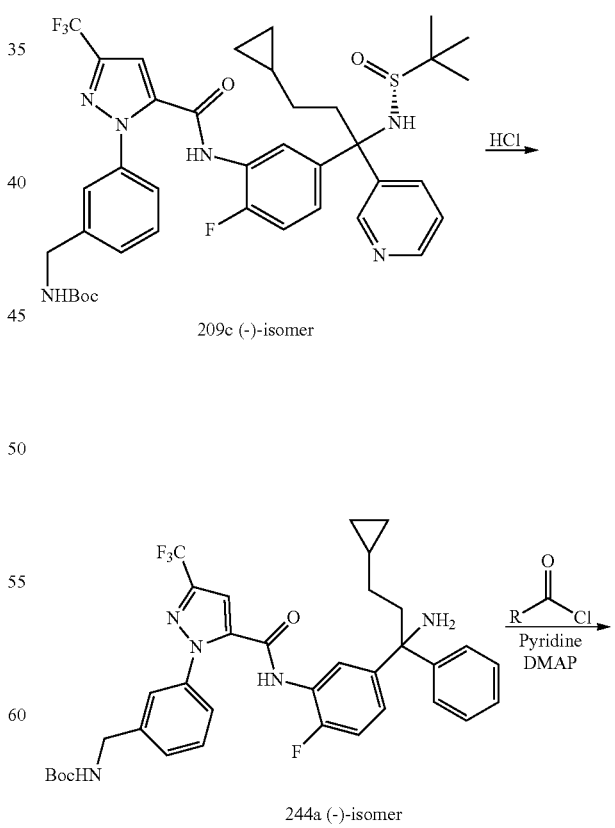

Scheme 244

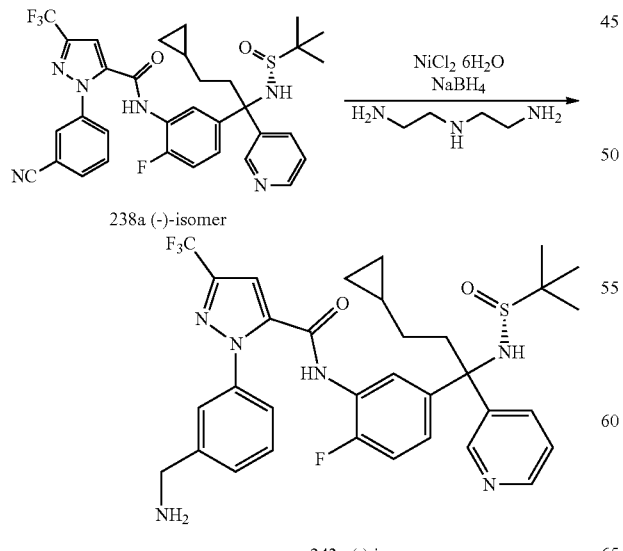

Scheme 243

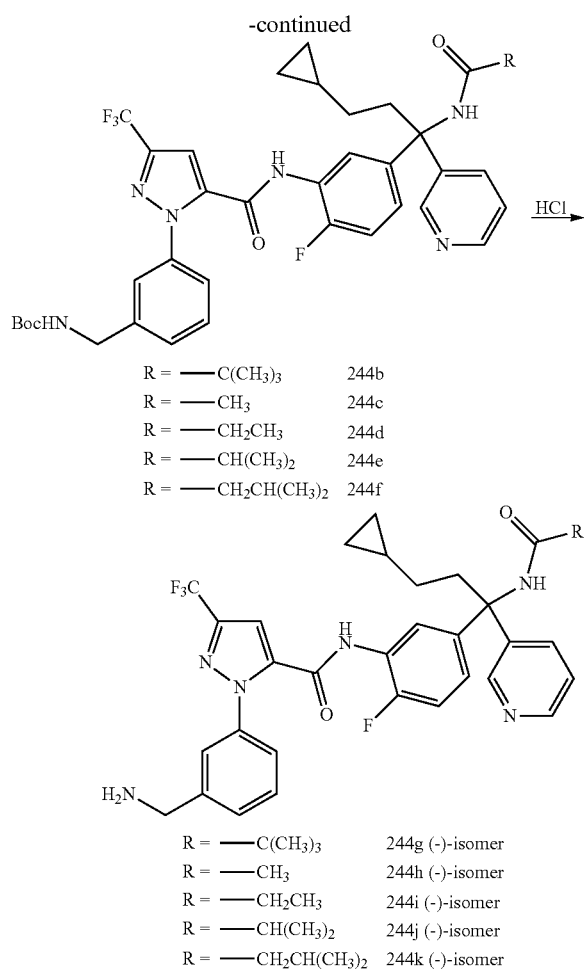

Preparation of (−)-1-(3-(aminomethyl)phenyl)-N-(5-(3-cyclopropyl-1-pivalamido-1-(pyridin-3-yl)propyl)-2-fluorophenyl)-3-(trifluoromethyl)-1H-pyrazole-5-carboxamide (244g)

Step-1: Preparation of (−)-tert-butyl 3-(5-(5-(1-amino-3-cyclopropyl-1-(pyridin-3-yl)propyl)-2-fluorophenylcarbamoyl)-3-(trifluoromethyl)-1H-pyrazol-1-yl)benzylcarbamate (244a)

To a stirred solution of tert-butyl 3-(5-(5-((−)-3-cyclopropyl-1-((R)-1,1-dimethylethylsulfinamido)-1-(pyridin-3-yl)propyl)-2-fluorophenylcarbamoyl)-3-(trifluoromethyl)-1H-pyrazol-1-yl)benzylcarbamate (209c) (1.603 g, 2.118 mmol) in methanol (18 mL) cooled to 0° C. was added 4 N hydrochloric acid in dioxane (1.60 mL, 6.40 mmol) and stirred at 0° C. for 2.5 h. The reaction mixture was quenched with triethylamine (1.10 mL, 7.89 mmol) and concentrated in vacuum to dryness. The residue obtained was purified by flash column chromatography [silica gel, eluting with hexanes/10% methanol in ethyl acetate (1:0 to 1:1)] to furnish (−)-tert-butyl 3-(5-(5-(1-amino-3-cyclopropyl-1-(pyridin-3-yl)propyl)-2-fluorophenylcarbamoyl)-3-(trifluoromethyl)-1H-pyrazol-1-yl)benzylcarbamate (244a) (658 mg, 47.6%) as a white solid; $^1$H NMR (300 MHz, DMSO-$d_6$) δ 10.60 (s, 1H), 8.46-8.38 (m, 1H), 7.82 (d, J=7.9 Hz, 1H), 7.71-7.60 (m, 2H), 7.59-7.32 (m, 8H), 7.25 (t, J=9.5 Hz, 1H), 4.29-4.19 (m, 2H), 2.42 (s, 2H), 2.37-2.22 (m, 2H), 1.44 (s, 9H), 1.19-1.02 (m, 2H), 0.78-0.61 (m, 1H), 0.50-0.34 (m, 2H), 0.04--0.06 (m, 2H); 19F NMR (282 MHz, DMSO) δ −60.60, −123.99; MS (ES+) 653.3 (M+1), (ES−) 651.5 (M−1); Optical rotation: [α]$_D$=(−) 1.45 [0.275, CH$_3$OH].

Step-2: Preparation of tert-butyl 3-(5-(5-(3-cyclopropyl-1-pivalamido-1-(pyridin-3-yl)propyl)-2-fluorophenylcarbamoyl)-3-(trifluoromethyl)-1H-pyrazol-1-yl)benzylcarbamate (244b)

To a solution of (−)-tert-butyl 3-(5-(5-(1-amino-3-cyclopropyl-1-(pyridin-3-yl)propyl)-2-fluorophenylcarbamoyl)-3-(trifluoromethyl)-1H-pyrazol-1-yl)benzylcarbamate (244a) (132 mg, 0.202 mmol) in pyridine (5 mL) was added N,N-dimethylpyridin-4-amine (30.0 mg, 0.246 mmol), pivaloyl chloride (0.030 mL, 0.243 mmol) and stirred at room temperature for 5 h. Additional pivaloyl chloride (0.060 mL) was added and stirred at room temperature for 22 h. Additional pivaloyl chloride (0.060 mL) was added and heated at 70° C. for 15 h. The reaction mixture was cooled to room temperature, quenched with methanol (5 mL) and concentrated in vacuum to dryness. The residue was diluted with ethyl acetate (150 mL), washed with water (75 mL), brine (75 mL), dried over MgSO$_4$, filtered and concentrated in vacuum to dryness. The residue was purified by flash column chromatography [silica gel with chloroform/methanol (1:0 to 19:1)] to furnish tert-butyl 3-(5-(5-(3-cyclopropyl-1-pivalamido-1-(pyridin-3-yl)propyl)-2-fluorophenylcarbamoyl)-3-(trifluoromethyl)-1H-pyrazol-1-yl)benzylcarbamate (244b) (29 mg, 19.5%) as a white solid. $^1$H NMR (300 MHz, DMSO-$d_6$) δ 10.58 (s, 1H), 8.49 (s, 1H), 8.38 (dd, J=4.7, 1.5 Hz, 1H), 7.67-7.16 (m, 12H), 4.18 (d, J=6.2 Hz, 2H), 2.70-2.40 (m, 2H), 1.38 (s, 9H), 1.11 (s, 9H), 1.00-0.80 (m, 2H), 0.70-0.55 (m, 1H), 0.40-0.27 (m, 2H), −0.05 to −0.20 (m, 2H); $^{19}$F NMR (282 MHz, DMSO-$d_6$) δ −60.60, −123.86; MS (ES+) 759.7 (M+Na).

Step-3: Preparation of (−)-1-(3-(aminomethyl)phenyl)-N-(5-(3-cyclopropyl-1-pivalamido-1-(pyridin-3-yl)propyl)-2-fluorophenyl)-3-(trifluoromethyl)-1H-pyrazole-5-carboxamide (244g)

To a solution of tert-butyl 3-(5-(5-(3-cyclopropyl-1-pivalamido-1-(pyridin-3-yl)propyl)-2-fluorophenylcarbamoyl)-3-(trifluoromethyl)-1H-pyrazol-1-yl)benzylcarbamate (244b) (26 mg, 0.035 mmol) in ethanol (6 mL) was added conc. HCl (0.030 mL, 0.360 mmol) and heated at reflux for 1 h. The solution was cooled to room temperature and concentrated in vacuum to dryness to give (−)-1-(3-(aminomethyl)phenyl)-N-(5-(3-cyclopropyl-1-pivalamido-1-(pyridin-3-yl)propyl)-2-fluorophenyl)-3-(trifluoromethyl)-1H-pyrazole-5-carboxamide (244g) (24 mg, 0.034 mmol, 96%) as a white solid. $^1$H NMR (300 MHz, DMSO-$d_6$) δ 10.69 (s, 1H), 8.65-8.58 (s, 2H), 8.33 (s, 3H), 8.11 (s, 1H), 7.75-7.45 (m, 8H), 7.32-7.18 (m, 2H), 4.12 (q, J=5.8 Hz, 2H), 2.65-2.40 (m, 2H), 1.11 (s, 9H), 1.02-0.84 (m, 2H), 0.70-0.56 (m, 1H), 0.40-0.28 (m, 2H), −0.06 to −0.16 (m, 2H); $^{19}$F NMR (282 MHz, DMSO-$d_6$) δ −60.62, −123.06; MS (ES+): 637.5 (M+1); Optical rotation: [α]$_D$=(−) 0.39 [1.55, CH$_3$OH].

Preparation of (−)-N-(5-(1-acetamido-3-cyclopropyl-1-(pyridin-3-yl)propyl)-2-fluorophenyl)-1-(3-(aminomethyl)phenyl)-3-(trifluoromethyl)-1H-pyrazole-5-carboxamide (244h)

Step-1: Preparation of tert-butyl 3-(5-(5-(1-acetamido-3-cyclopropyl-1-(pyridin-3-yl)propyl)-2-fluorophenylcarbamoyl)-3-(trifluoromethyl)-1H-pyrazol-1-yl)benzylcarbamate (244c)

To a solution of (−)-tert-butyl 3-(5-(5-(1-amino-3-cyclopropyl-1-(pyridin-3-yl)propyl)-2-fluorophenylcarbamoyl)-3-(trifluoromethyl)-1H-pyrazol-1-yl)benzylcarbamate (244a) (170 mg, 0.260 mmol) in pyridine (5 mL) was added N,N-dimethylpyridin-4-amine (38.0 mg, 0.311 mmol), acetic anhydride (0.030 mL, 0.313 mmol) and stirred at room temperature for 5 h. Additional acetic anhydride (0.060 mL) was added and stirred at room temperature for 22 h. Additional acetic anhydride (0.060 mL) was added and stirred at room temperature for 15 h. The reaction was quenched with methanol (5 mL) and concentrated in vacuum to dryness. The residue was diluted with ethyl acetate (150 mL), washed with water (75 mL), brine (75 mL), dried over MgSO$_4$, filtered and concentrated in vacuum to dryness. The residue was purified by flash column chromatography [silica gel with chloroform/methanol (1:0 to 19:1)] to afford tert-butyl 3-(5-(5-(1-acetamido-3-cyclopropyl-1-(pyridin-3-yl)propyl)-2-fluorophenylcarbamoyl)-3-(trifluoromethyl)-1H-pyrazol-1-yl)benzylcarbamate (244c) (53 mg, 29.3%) as a white solid. $^1$H NMR (300 MHz, DMSO-d$_6$) δ 10.59 (s, 1H), 8.49 (d, J=2.2 Hz, 1H), 8.38 (dd, J=4.8, 1.5 Hz, 1H), 8.31 (s, 1H), 7.69-7.17 (m, 11H), 4.19 (d, J=6.2 Hz, 2H), 2.65-02.40 (m, 2H), 1.89 (s, 3H), 1.38 (s, 9H), 1.05-0.80 (m, 2H), 0.70-0.50 (m, 1H), 0.40-0.25 (m, 2H), −0.05 to −0.17 (m, 2H); $^{19}$F NMR (282 MHz, DMSO-d$_6$) δ −60.62, −123.29; MS (ES−): 693.6 (M−1).

Step-2: preparation of (−)-N-(5-(1-acetamido-3-cyclopropyl-1-(pyridin-3-yl)propyl)-2-fluorophenyl)-1-(3-(aminomethyl)phenyl)-3-(trifluoromethyl)-1H-pyrazole-5-carboxamide (244h)

Compound 244h was prepared from tert-butyl 3-(5-(5-(1-acetamido-3-cyclopropyl-1-(pyridin-3-yl)propyl)-2-fluorophenylcarbamoyl)-3-(trifluoromethyl)-1H-pyrazol-1-yl)benzylcarbamate (244c) (45 mg, 0.065 mmol) and conc. HCl (0.054 mL, 0.648 mmol) using the procedure as described for preparation of compound 244g in step-3 of scheme-244 to afford (−)-N-(5-(1-acetamido-3-cyclopropyl-1-(pyridin-3-yl)propyl)-2-fluorophenyl)-1-(3-(aminomethyl)phenyl)-3-(trifluoromethyl)-1H-pyrazole-5-carboxamide (244h) (44 mg) hydrochloride salt as an off-white solid. $^1$H NMR (300 MHz, DMSO-d$_6$) δ 10.72 (s, 1H), 8.70-8.62 (m, 2H), 8.55 (s, 1H), 8.39 (bs, 3H), 8.22 (d, J=8.2 Hz, 1H), 7.83-7.21 (m, 9H), 4.12 (q, J=5.7 Hz, 2H), 2.60-2.40 (m, 2H), 1.91 (s, 3H), 1.11-0.77 (m, 2H), 0.70--0.54 (m, 1H), 0.41-0.23 (m, 2H), −0.04 to −0.12 (m, 2H); $^{19}$F NMR (282 MHz, DMSO-d$_6$) δ −60.63, −122.26; MS (ES+): 595.4 (M+1); Optical rotation: [α]$_D$=(−) 1.51 [0.265, CH$_3$OH].

Preparation of (−)-1-(3-(aminomethyl)phenyl)-N-(5-(3-cyclopropyl-1-propionamido-1-(pyridin-3-yl)propyl)-2-fluorophenyl)-3-(trifluoromethyl)-1H-pyrazole-5-carboxamide (244i)

Step-1: Preparation of tert-butyl 3-(5-(5-(3-cyclopropyl-1-propionamido-1-(pyridin-3-yl)propyl)-2-fluorophenylcarbamoyl)-3-(trifluoromethyl)-1H-pyrazol-1-yl)benzylcarbamate (244d)

To a solution of (−)-tert-butyl 3-(5-(5-(1-amino-3-cyclopropyl-1-(pyridin-3-yl)propyl)-2-fluorophenylcarbamoyl)-3-(trifluoromethyl)-1H-pyrazol-1-yl)benzylcarbamate (244a) (175 mg, 0.27 mmol) in anhydrous pyridine/THF (10 mL, 1:1, v/v) was added DMAP (33.0 mg, 0.27 mmol), followed by addition of isobutyryl chloride (142.8 mg, 1.34 mmol, 5.0 eq) in anhydrous THF (2.0 mL). The resulting reaction mixture was stirred for 11 h at room temperature and concentrated in vacuum to dryness. The residue was dissolved in EtOAc (100 mL), washed with water (2×50 mL), brine, dried over MgSO$_4$, filtered and concentrated. The residue obtained was purified by flash column chromatography (silica gel, 12 g, eluting with EtOAc/MeOH (9:1) and hex, 0-50%) to furnish tert-butyl 3-(5-(5-(3-cyclopropyl-1-propionamido-1-(pyridin-3-yl)propyl)-2-fluorophenylcarbamoyl)-3-(trifluoromethyl)-1H-pyrazol-1-yl)benzylcarbamate (244d) (150 mg, 78.47% yield) as a white solid; $^1$H NMR (300 MHz, CD$_3$OD) δ 8.52 (d, J=2.4 Hz, 1H), 8.36 (dd, J=4.9, 1.5 Hz, 1H), 7.81 (dt, J=7.8, 2.2 Hz, 2H), 7.48-7.29 (m, 5H), 7.26-7.10 (m, 3H), 4.29 (s, 2H), 2.74-2.53 (m, 2H), 2.28 (q, J=7.6 Hz, 2H), 1.43 (s, 9H), 1.05 (m, 3H), 0.95-0.82 (m, 2H), 0.69-0.61 (m, 1H), 0.42-0.34 (m, 2H), −0.03--0.12 (m, 2H); MS (ES+) 709.5 (M+1).

Step-2: Preparation of (−)-1-(3-(aminomethyl)phenyl)-N-(5-(3-cyclopropyl-1-propionamido-1-(pyridin-3-yl)propyl)-2-fluorophenyl)-3-(trifluoromethyl)-1H-pyrazole-5-carboxamide (244i)

To a solution of tert-butyl 3-(5-(5-(3-cyclopropyl-1-propionamido-1-(pyridin-3-yl)propyl)-2-fluorophenylcarbamoyl)-3-(trifluoromethyl)-1H-pyrazol-1-yl)benzylcarbamate (244d) (150 mg, 0.211 mmol) in ethanol (20 mL) was added HCl (4N in dioxane, 0.35 mL, 10 eq) and heated at reflux for 2 h. The reaction was concentrated in vacuum and the residue obtained was purified by flash column chromatography (silica gel 12 g, eluting with CHCl$_3$ in CMA-80 0-60%) to furnish compound 244i (71 mg) free base as a white solid. The free base was dissolved in methanol (5 mL), added HCl (0.2 mL, 4N in dioxane) at room temperature and concentrated in vacuum to dryness. The residue was dissolved in water (2 mL) and two drops of acetonitrile, lyophilized to furnish (−)-1-(3-(aminomethyl)phenyl)-N-(5-(3-cyclopropyl-1-propionamido-1-(pyridin-3-yl)propyl)-2-fluorophenyl)-3-(trifluoromethyl)-1H-pyrazole-5-carboxamide (244i) (72 mg, 84%) hydrochloride salt as a white solid; $^1$H NMR (300 MHz, DMSO-d$_6$) δ 10.82 (s, 1H), 8.80-8.66 (bs, 2H), 8.60 (bs, 3H), 8.39 (d, J=8.1 Hz, 1H), 7.91 (m, 1H), 7.73 (m, 2H), 7.65 (d, J=7.2 Hz, 1H), 7.59-7.48 (m, 4H), 7.35-7.20 (m, 3H), 4.10 (d, J=5.8 Hz, 2H), 2.54 (m, 2H), 2.24 (q, J=7.4 Hz, 2H), 0.92 (m, 5H), 0.70-0.55 (m, 1H), 0.33 (m, 2H), −0.07 (m, 2H); 19F NMR (282 MHz, DMSO) δ −60.77, −122.21; MS (ES$^+$): MS (ES+) 609.5 (M+1); Optical rotation: [α]$_D$=(−) 1.57 [0.255, CH$_3$OH].

Preparation of (−)-1-(3-(aminomethyl)phenyl)-N-(5-(3-cyclopropyl-1-isobutyramido-1-(pyridin-3-yl)propyl)-2-fluorophenyl)-3-(trifluoromethyl)-1H-pyrazole-5-carboxamide (244j)

Step-1: Preparation of tert-butyl 3-(5-(5-(3-cyclopropyl-1-isobutyramido-1-(pyridin-3-yl)propyl)-2-fluorophenylcarbamoyl)-3-(trifluoromethyl)-1H-pyrazol-1-yl)benzylcarbamate (244e)

Compound 244e was prepared from (−)-tert-butyl 3-(5-(5-(1-amino-3-cyclopropyl-1-(pyridin-3-yl)propyl)-2-fluorophenylcarbamoyl)-3-(trifluoromethyl)-1H-pyrazol-1-yl)benzylcarbamate (244a) (175 mg, 0.27 mmol) and isobutyryl chloride (142.8 mg, 1.34 mmol, 5.0 eq) using the procedure as described for preparation of compound 244d in scheme-244 to furnish after purification by flash column chromatography [silica gel, 12 g column, eluting with EtOAc/MeOH (9:1) and hexane 0-50%] tert-butyl 3-(5-(5-(3-cyclopropyl-1-isobutyramido-1-(pyridin-3-yl)propyl)-2-fluorophenylcarbamoyl)-3-(trifluoromethyl)-1H-pyrazol-1-yl)benzylcarbamate (244e) (150 mg, 76.86% yield) as a white solid; MS (ES+) 723.5 (M+1); (ES−) 721.5 (M−1).

Step-2: Preparation of (−)-1-(3-(aminomethyl)phenyl)-N-(5-(3-cyclopropyl-1-isobutyramido-1-(pyridin-3-yl)propyl)-2-fluorophenyl)-3-(trifluoromethyl)-1H-pyrazole-5-carboxamide (244j)

Free base of compound 244j was prepared from tert-butyl 3-(5-(5-(3-cyclopropyl-1-isobutyramido-1-(pyridin-3-yl)propyl)-2-fluorophenylcarbamoyl)-3-(trifluoromethyl)-1H-pyrazol-1-yl)benzylcarbamate (244e) (150 mg, 0.208 mmol) and HCl (4N in dioxane, 0.35 mL, 10 eq) using the procedure as described for preparation of free base of compound 244i in scheme-244 to afford after purification by flash column chromatography (silica gel 12 g, eluting with CHCl₃ in CMA-80 0-60%) compound 244j (63 mg) free base as a white solid. The free base was converted to hydrochloride salt as described in preparation of hydrochloride salt of compound 244i from its free base in scheme-244 to afford (−)-1-(3-(aminomethyl)phenyl)-N-(5-(3-cyclopropyl-1-isobutyramido-1-(pyridin-3-yl)propyl)-2-fluorophenyl)-3-(trifluoromethyl)-1H-pyrazole-5-carboxamide (244j) (64 mg) hydrochloride salt as a white solid; $^1$H NMR (300 MHz, DMSO-$d_6$) δ 10.75 (s, 1H), 8.68 (m, 2H), 8.48 (m, 3H), 8.28 (d, J=8.1 Hz, 1H), 7.83 (t, J=7.1 Hz, 1H), 7.77-7.66 (m, 2H), 7.67-7.47 (m, 4H), 7.42 (s, 1H), 7.31-7.21 (m, 3H), 7.08 (s, 1H), 4.11 (d, J=5.8 Hz, 2H), 2.75-2.63 (m, 1H), 2.58 (m, 2H), 0.93 (t, J=7.2 Hz, 8H), 0.64 (m, 1H)), 0.39-0.29 (m, 2H), −0.09 (m, 2H); $^{19}$F NMR (282 MHz, DMSO) δ −60.79, −122.69; MS (ES+) 623.5 (M+1); 621.9 (M−1); Optical rotation: $[\alpha]_D$=(−) 0.73 [0.055, CH₃OH]; Analysis calculated for $C_{33}H_{34}F_4N_6O_2 \cdot 3.5HCl \cdot 3.5H_2O$: C, 48.73; H, 5.51; Cl, 15.26; N, 10.33; Found: C, 48.32; H, 5.79; Cl, 15.29; N, 10.73.

Preparation of (−)-1-(3-(aminomethyl)phenyl)-N-(5-(3-cyclopropyl-1-(3-methylbutanamido)-1-(pyridin-3-yl)propyl)-2-fluorophenyl)-3-(trifluoromethyl)-1H-pyrazole-5-carboxamide (244k)

Step-1: Preparation of tert-butyl 3-(5-(5-(3-cyclopropyl-1-(3-methylbutanamido)-1-(pyridin-3-yl)propyl)-2-fluorophenylcarbamoyl)-3-(trifluoromethyl)-1H-pyrazol-1-yl)benzylcarbamate (244f)

Compound 244f was prepared from (−)-tert-butyl 3-(5-(5-(1-amino-3-cyclopropyl-1-(pyridin-3-yl)propyl)-2-fluorophenylcarbamoyl)-3-(trifluoromethyl)-1H-pyrazol-1-yl)benzylcarbamate (244a) (175 mg, 0.27 mmol) and isovaleryl chloride (139 mg, 1.149 mmol) using the procedure as described for preparation of compound 244d in scheme-244 to furnish tert-butyl 3-(5-(5-(3-cyclopropyl-1-(3-methylbutanamido)-1-(pyridin-3-yl)propyl)-2-fluorophenylcarbamoyl)-3-(trifluoromethyl)-1H-pyrazol-1-yl)benzylcarbamate (244f) (190 mg); MS (ES+) 737.6 (M+1), (ES−) 735.5 (M−1).

Step-2: Preparation of (−)-1-(3-(aminomethyl)phenyl)-N-(5-(3-cyclopropyl-1-(3-methylbutanamido)-1-(pyridin-3-yl)propyl)-2-fluorophenyl)-3-(trifluoromethyl)-1H-pyrazole-5-carboxamide (244k)

Free base of compound 244k was prepared from tert-butyl 3-(5-(5-(3-cyclopropyl-1-(3-methylbutanamido)-1-(pyridin-3-yl)propyl)-2-fluorophenylcarbamoyl)-3-(trifluoromethyl)-1H-pyrazol-1-yl)benzylcarbamate (244f) (190 mg) and HCl (4N in dioxane, 0.35 mL) using the procedure as described for preparation of free base of compound 244i in scheme-244 to afford after purification by flash column chromatography (silica gel 12 g, eluting with CHCl₃ in CMA-80 0-60%) (44 mg) free base of 244k as a white solid. The free base was converted to hydrochloride salt as described in preparation of hydrochloride salt of compound 244i from its free base in scheme-244 to afford (−)-1-(3-(aminomethyl)phenyl)-N-(5-(3-cyclopropyl-1-(3-methylbutanamido)-1-(pyridin-3-yl)propyl)-2-fluorophenyl)-3-(trifluoromethyl)-1H-pyrazole-5-carboxamide (244k) (46 mg, 31% for 2 steps) hydrochloride salt as a white solid; $^1$H NMR (300 MHz, DMSO-$d_6$) δ 10.73 (s, 1H), 8.72-8.62 (m, 2H), 8.51 (s, 1H), 8.43 (bs, 3H), 8.25 (d, J=8.2 Hz, 1H), 7.87-7.77 (m, 1H), 7.73 (t, J=1.7 Hz, 1H), 7.68 (s, 1H), 7.62 (m, 1H), 7.57-7.46 (m, 3H), 7.40-7.01 (m, 3H), 4.11 (q, J=5.8 Hz, 2H), 2.60-2.54 (m, 2H), 2.17-2.05 (m, 2H), 1.88 (m, 1H), 0.97 (m, 2H), 0.79 (m, 6H), 0.61 (m, 1H), 0.44-0.28 (m, 2H), −0.05-−0.14 (m, 2H); $^{19}$F NMR (282 MHz, DMSO) δ −60.80, −122.48; MS (ES+) 637.6 (M+1); Optical rotation: $[\alpha]_D$=(−) 2.61 [0.23, CH₃OH]; Analysis calculated for $C_{34}H_{36}FN_6O_2 \cdot 2HCl \cdot 2.5H_2O$: C, 54.11; H, 5.74; Cl, 9.40; N, 11.14; Found: C, 53.98; H, 5.70; Cl, 9.78; N, 11.09.

Scheme 245

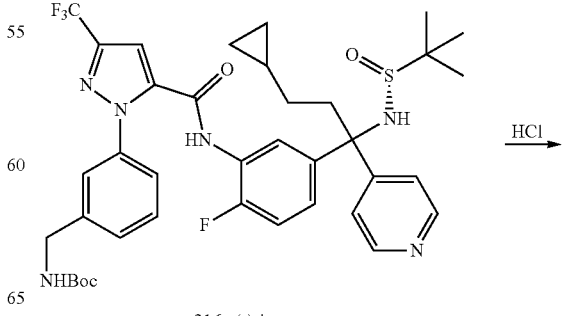

216c (−)-isomer

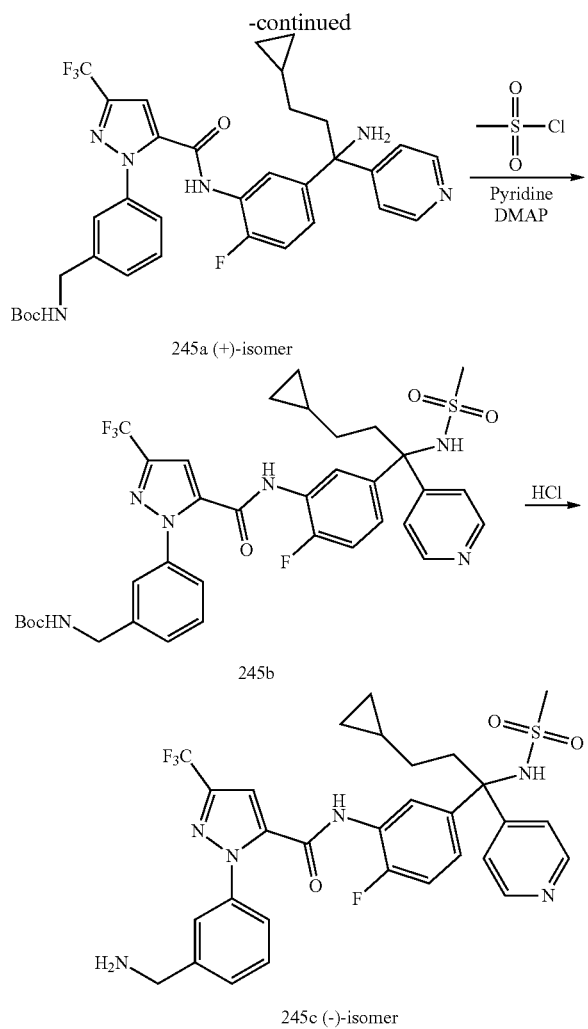

Preparation of (−)-1-(3-(aminomethyl)phenyl)-N-(5-(3-cyclopropyl-1-(methyl sulfonamido)-1-(pyridin-4-yl)propyl)-2-fluorophenyl)-3-(trifluoromethyl)-1H-pyrazole-5-carboxamide (245c)

Step-1: Preparation of tert-butyl 3-(5-(5-(1-amino-3-cyclopropyl-1-(pyridin-4-yl)propyl)-2-fluorophenylcarbamoyl)-3-(trifluoromethyl)-1H-pyrazol-1-yl)benzylcarbamate (245a)

To a solution of tert-butyl 3-(5-(5-((−)-3-cyclopropyl-1-((R)-1,1-dimethylethylsulfinamido)-1-(pyridin-4-yl)propyl)-2-fluorophenylcarbamoyl)-3-(trifluoromethyl)-1H-pyrazol-1-yl)benzylcarbamate (216c) (893 mg, 1.180 mmol) in MeOH (15 mL) cooled to 0° C. was added HCl (0.89 mL, 3.56 mmol, 4 N in 1,4-dioxane) and stirred at about 0° C. for 2 h. The reaction mixture was quenched with triethylamine (0.610 mL, 4.38 mmol) at 0° C. and concentrated in vacuum to dryness. The residue was purified by flash column chromatography [silica gel, eluting with hexanes/10% methanol in ethyl acetate (1:0 to 1:1), then chloroform/CMA8 0 1:1) to give tert-butyl 3-(5-(5-(1-amino-3-cyclopropyl-1-(pyridin-4-yl)propyl)-2-fluorophenylcarbamoyl)-3-(trifluoromethyl)-1H-pyrazol-1-yl)benzylcarbamate (245a) (140 mg, 18.2%) as a colorless gum; $^1$H NMR (300 MHz, DMSO-$d_6$) δ 10.55 (s, 1H), 8.48-8.40 (m, 2H), 7.64-7.25 (m, 10H), 7.18 (t, J=9.4 Hz, 1H), 4.19 (d, J=6.2 Hz, 2H), 2.21 (m, 2H), 1.38 (s, 9H), 1.15-0.90 (m, 2H), 0.70-0.55 (m, 1H), 0.42-0.26 (m, 2H), −0.04 to −0.12 (m, 2H); $^{19}$F NMR (282 MHz, DMSO-$d_6$) δ −60.63, −123.81; MS (ES+): 653.5 (M+1).

Step-2: Preparation of tert-butyl 3-(5-(5-(3-cyclopropyl-1-(methylsulfonamido)-1-(pyridin-4-yl)propyl)-2-fluorophenylcarbamoyl)-3-(trifluoromethyl)-1H-pyrazol-1-yl)benzylcarbamate (245b)

To a solution of tert-butyl 3-(5-(5-(1-amino-3-cyclopropyl-1-(pyridin-4-yl)propyl)-2-fluorophenylcarbamoyl)-3-(trifluoromethyl)-1H-pyrazol-1-yl)benzylcarbamate (245a) (126 mg, 0.193 mmol) in pyridine (5 mL) was added N,N-dimethylpyridin-4-amine (24.00 mg, 0.196 mmol), methanesulfonyl chloride (0.018 mL, 0.232 mmol) and stirred at room temperature for 19 h. Additional methanesulfonyl chloride (0.03 mL, 0.03 mL, 0.08 mL, 0.15 mL, 0.15 mL) was added every day for five consecutive days and continued heating at 70° C. overnight. The reaction mixture was diluted with ethyl acetate (120 mL), washed with water (2×50 mL), brine (50 mL), dried over MgSO$_4$ filtered and concentrated in vacuum. The crude product was purified by flash column chromatography [silica gel eluting with hexanes/10% methanol in ethyl acetate (1:0 to 1:1)] to give tert-butyl 3-(5-(5-(3-cyclopropyl-1-(methylsulfonamido)-1-(pyridin-4-yl)propyl)-2-fluorophenylcarbamoyl)-3-(trifluoromethyl)-1H-pyrazol-1-yl)benzylcarbamate (245b) (30 mg, 21.3%) as an off-white solid; $^1$H NMR (300 MHz, DMSO-$d_6$) δ 10.64 (s, 1H), 8.54-8.50 (m, 2H), 7.85 (s, 1H), 7.65-7.17 (m, 11H), 4.18 (d, J=6.2 Hz, 2H), 2.65-2.35 (m, 2H), 2.28 (s, 3H), 1.38 (s, 9H), 1.15-0.90 (m, 1H), 0.93-0.71 (m, 1H), 0.64-0.48 (m, 1H), 0.39-0.20 (m, 2H), −0.03--0.21 (m, 2H); $^{19}$F NMR (282 MHz, DMSO-$d_6$) δ −60.80, −121.96; MS (ES+): 753.4 (M+23).

Step-3: Preparation of (−)-1-(3-(aminomethyl)phenyl)-N-(5-(3-cyclopropyl-1-(methylsulfonamido)-1-(pyridin-4-yl)propyl)-2-fluorophenyl)-3-(trifluoromethyl)-1H-pyrazole-5-carboxamide (245c)

To a solution of tert-butyl 3-(5-(5-(3-cyclopropyl-1-(methylsulfonamido)-1-(pyridin-4-yl)propyl)-2-fluorophenylcarbamoyl)-3-(trifluoromethyl)-1H-pyrazol-1-yl)benzylcarbamate (245b) (27 mg, 0.037 mmol) in ethanol (6 mL) was added conc. HCl (0.03 mL, 0.366 mmol) and heated at reflux for 45 mins. The reaction mixture was cooled to room temperature and concentrated to give 1-(3-(aminomethyl)phenyl)-N-(5-(3-cyclopropyl-1-(methylsulfonamido)-1-(pyridin-4-yl)propyl)-2-fluorophenyl)-3-(trifluoromethyl)-1H-pyrazole-5-carboxamide (245c) (23 mg, 88%) hydrochloride salt as an off-white solid; $^1$H NMR (300 MHz, DMSO-$d_6$) δ 10.77 (s, 1H), 8.75 (s, 2H), 8.39 (s, 3H), 8.10 (s, 1H), 7.77-7.45 (m, 8H), 7.33 (t, J=9.3 Hz, 1H), 7.29-7.20 (m, 1H), 4.12 (d, J=5.6 Hz, 2H), 2.76-2.25 (m, 2H), 2.38 (s, 3H), 1.15-0.95 (m, 1H), 0.90-0.70 (m, 1H), 0.65-0.50 (m, 1H), 0.40-0.25 (m, 2H), −0.01--0.20 (m, 2H); $^{19}$F NMR (282 MHz, DMSO-$d_6$) δ −60.79, −121.16; MS (ES+): 631.4 (M+1); Optical rotation: [α]$_D$=(−) 7.62 [0.105, CH$_3$OH]; Analysis calculated for $C_{30}H_{30}F_4N_6O_3S.2HCl.2H_2O$: C, 48.72; H, 4.91; N, 11.36; Found: C, 48.61; H, 4.91; N, 10.99.

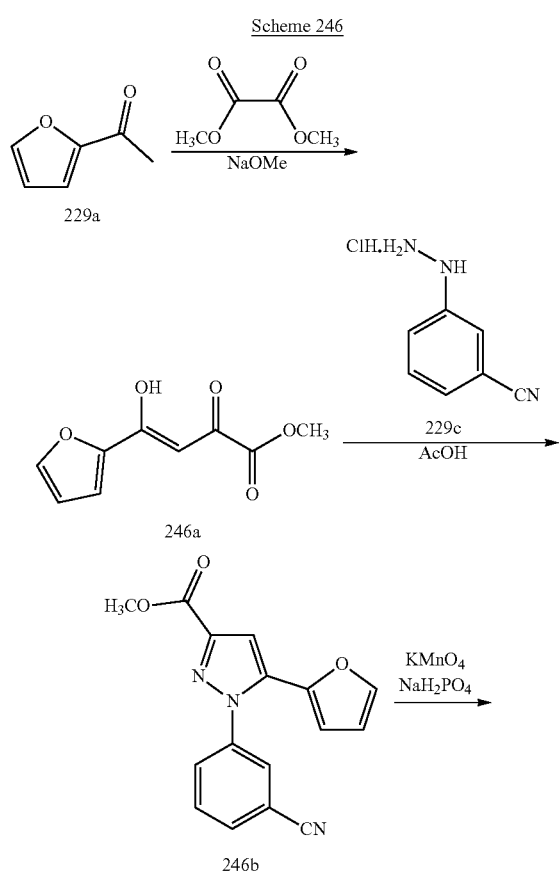

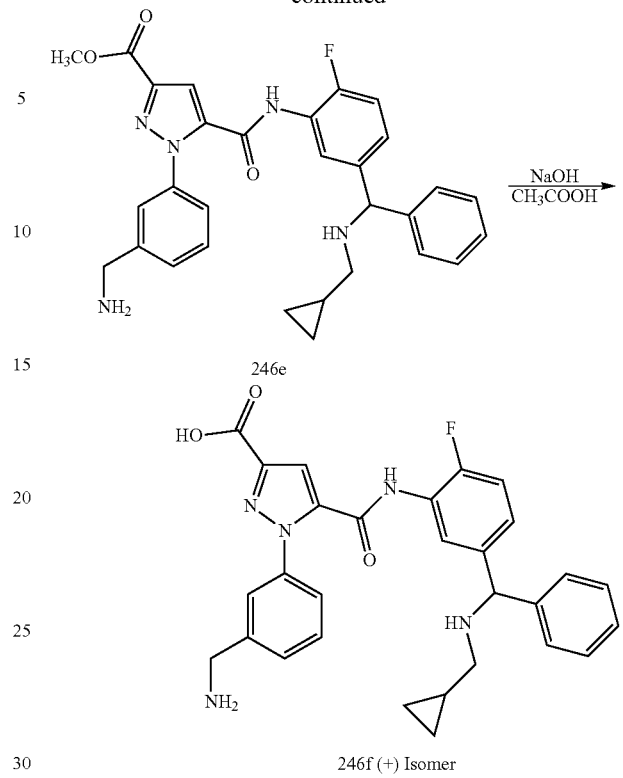

Preparation of (+)-1-(3-(aminomethyl)phenyl)-5-(5-((cyclopropylmethylamino)(phenyl)methyl)-2-fluorophenylcarbamoyl)-1H-pyrazole-3-carboxylic acid (246f)

Step-1: Preparation of methyl 4-(furan-2-yl)-4-hydroxy-2-oxobut-3-enoate (246a)

To a solution of 1-(furan-2-yl)ethanone (229a) (13.76 g, 125 mmol) and dimethyl oxalate (14.76 g, 125 mmol) in THF (500 mL) was added dropwise sodium methoxide (25% in methanol, 29.7 g, 137 mmol). The resulting suspension was stirred at room temperature for 18 h. The solid obtained was collected by filtration washed with ether to afford methyl 4-(furan-2-yl)-4-hydroxy-2-oxobut-3-enoate (246a) (11.7 g, 59.6 mmol, 47.7% yield) as a brown solid, which was taken as such for next step; $^1$H NMR (300 MHz, DMSO-$d_6$) δ 8.33 (d, J=2.2 Hz, 1H), 7.81-7.73 (m, 2H), 7.56 (dd, J=8.6, 2.2 Hz, 1H), 5.19 (d, J=13.2 Hz, 1H), 2.95 (s, 3H).

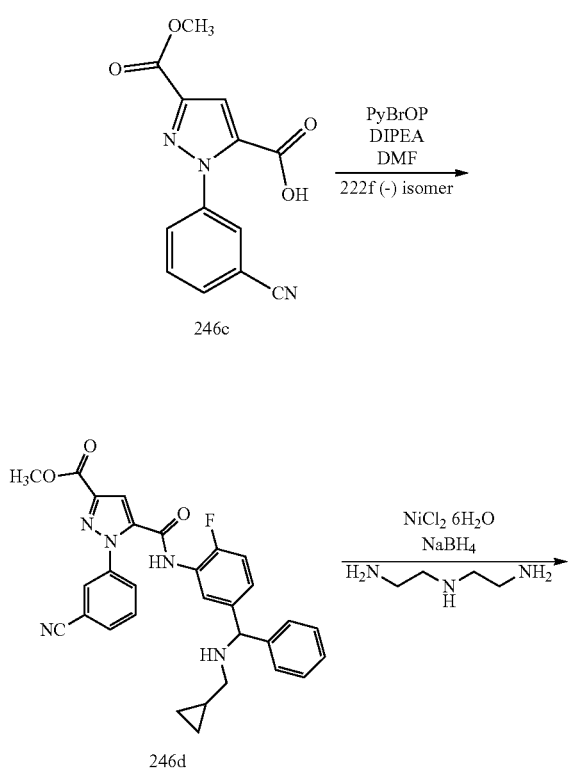

Step-2: Preparation of methyl 1-(3-cyanophenyl)-5-(furan-2-yl)-1H-pyrazole-3-carboxylate (246b)

To methyl 4-(furan-2-yl)-4-hydroxy-2-oxobut-3-enoate (246a) (4 g, 20.39 mmol) and 3-hydrazinylbenzonitrile hydrochloride (229c) (2.94 g, 17.33 mmol) was added AcOH (40 mL) and stirred at room temperature overnight. The mixture was concentrated in vacuum and the residue obtained was purified by flash column chromatography (silica gel 300 g, eluting 25% ethyl acetate in hexane) to furnish methyl 1-(3-cyanophenyl)-5-(furan-2-yl)-1H-pyrazole-3-carboxylate (246b) as an yellow oil; $^1$H NMR (300 MHz, DMSO-$d_6$) δ 8.10-8.01 (m, 2H), 7.89-7.82 (m, 1H), 7.81-7.71 (m, 2H), 7.27 (s, 1H), 6.59 (dd, J=3.5, 1.8 Hz, 1H), 6.50 (dd, J=3.5, 0.8 Hz, 1H), 3.87 (s, 3H); MS (ES+) 294.2 (M+1), 316.2 (M+Na).

Step-3: Preparation of 1-(3-cyanophenyl)-3-(methoxycarbonyl)-1H-pyrazole-5-carboxylic acid (246c)

Compound 246c was prepared by oxidation of methyl 1-(3-cyanophenyl)-5-(furan-2-yl)-1H-pyrazole-3-carboxylate (246b) (2 g, 6.82 mmol) according to the procedure reported in step-5 of scheme-229 to afford after purification by flash column chromatography (silica gel 25 g, eluting with CMA80 in chloroform 0-100%) 1-(3-cyanophenyl)-3-(methoxycarbonyl)-1H-pyrazole-5-carboxylic acid (246c) (0.753 g, 41% yield) as an yellow solid; $^1$H NMR (300 MHz, DMSO-$d_6$) δ 8.02 (s, 1H), 7.94-7.77 (m, 2H), 7.72-7.59 (m, 1H), 7.01 (s, 1H), 3.83 (s, 3H); MS (ES$^+$): MS (ES+) 272.2 (M+1), 294.2 (M+Na), 565.3 (2M+Na); MS (ES−) 270.2 (M−1), 541.3 (2M−1).

Step-4: Preparation of methyl 1-(3-cyanophenyl)-5-(5-((cyclopropylmethylamino)(phenyl)methyl)-2-fluorophenylcarbamoyl)-1H-pyrazole-3-carboxylate (246d)

Compound 246d was prepared from 1-(3-cyanophenyl)-3-(methoxycarbonyl)-1H-pyrazole-5-carboxylic acid (246c) (0.706 g, 2.60 mmol) and (−)-5-((cyclopropylmethylamino)(phenyl) methyl)-2-fluoroaniline (222f) (0.844 g, 3.12 mmol) as described in step-3 of scheme-208 to afford methyl 1-(3-cyanophenyl)-5-(5-((cyclopropylmethylamino)(phenyl)methyl)-2-fluorophenylcarbamoyl)-1H-pyrazole-3-carboxylate (246d) which was used as such without purification in the next step; MS (ES+) 524.4 (M+1); MS (ES−) 522.5 (M−1).

Step-5: Preparation methyl 1-(3-(aminomethyl)phenyl)-5-(5-((cyclopropylmethylamino)(phenyl) methyl)-2-fluorophenylcarbamoyl)-1H-pyrazole-3-carboxylate (246e)

Compound 246e was prepared from methyl 1-(3-cyanophenyl)-5-(5-((cyclopropylmethyllamino)(phenyl)methyl)-2-fluorophenylcarbamoyl)-1H-pyrazole-3-carboxylate (246d) (1.66 g, 3.17 mmol) according to the procedure reported for preparation of compound 15g in step-6 of scheme-15 to furnish after purification by flash column chromatography (silica gel, eluting with CMA80 in chloroform from 0-100%) methyl 1-(3-(aminomethyl)phenyl)-5-(5-((cyclopropylmethylamino)(phenyl)methyl)-2-fluorophenylcarbamoyl)-1H-pyrazole-3-carboxylate (246e) (0.126 g, 8% yield) as a white solid; MS (ES$^+$): MS (ES+) 528.4 (M+1); MS (ES−) 526.5 (M−1).

Step-6: Preparation of (+)-1-(3-(aminomethyl)phenyl)-5-(5-((cyclopropylmethylamino)(phenyl) methyl)-2-fluorophenylcarbamoyl)-1H-pyrazole-3-carboxylic acid (246f)

To a solution of methyl 1-(3-(aminomethyl)phenyl)-5-(5-((cyclopropylmethylamino)(phenyl) methyl)-2-fluorophenylcarbamoyl)-1H-pyrazole-3-carboxylate (246e) (0.119 g, 0.226 mmol) in methanol (2.4 mL) and THF (2.4 mL) at room temperature was added aq. sodium hydroxide (2.256 mL, 2.256 mmol) and stirred at room temperature for 2 h. Reaction mixture was quenched with acetic acid (0.155 mL, 2.71 mmol), stirred for 10 min and evaporated to dryness. The residue obtained was purified twice by flash column chromatography [silica gel 25 g, eluting with CMA80 in chloroform, 0-100%, second column: silica gel 12 g, eluting with methanol in chloroform from 0-100%] to (+)-1-(3-(aminomethyl)phenyl)-5-(5-((cyclopropylmethylamino) (phenyl)methyl)-2-fluorophenylcarbamoyl)-1H-pyrazole-3-carboxylic acid (246f) (19 mg, 16% yield) as a colorless solid; $^1$H NMR (300 MHz, DMSO-$d_6$) δ 10.37 (s, 1H, D$_2$O exchangeable), 8.13 (s, 1H), 7.58 (dd, J=7.4, 2.2 Hz, 1H), 7.44-7.09 (m, 12H), 4.81 (s, 1H), 4.15 (s, 2H), 2.26 (d, J=6.7 Hz, 2H), 0.90 (dq, J=13.0, 6.9, 6.0 Hz, 1H), 0.42-0.28 (m, 2H), 0.03 (dt, J=5.0, 2.7 Hz, 2H); $^{19}$F NMR (282 MHz, DMSO-$d_6$) δ −123.25; MS (ES$^+$): MS (ES+) 514.4 (M+1); MS (ES−) 512.4 (M−1); Optical rotation: [α]$_D$=(+) 2.86 [0.07, MeOH].

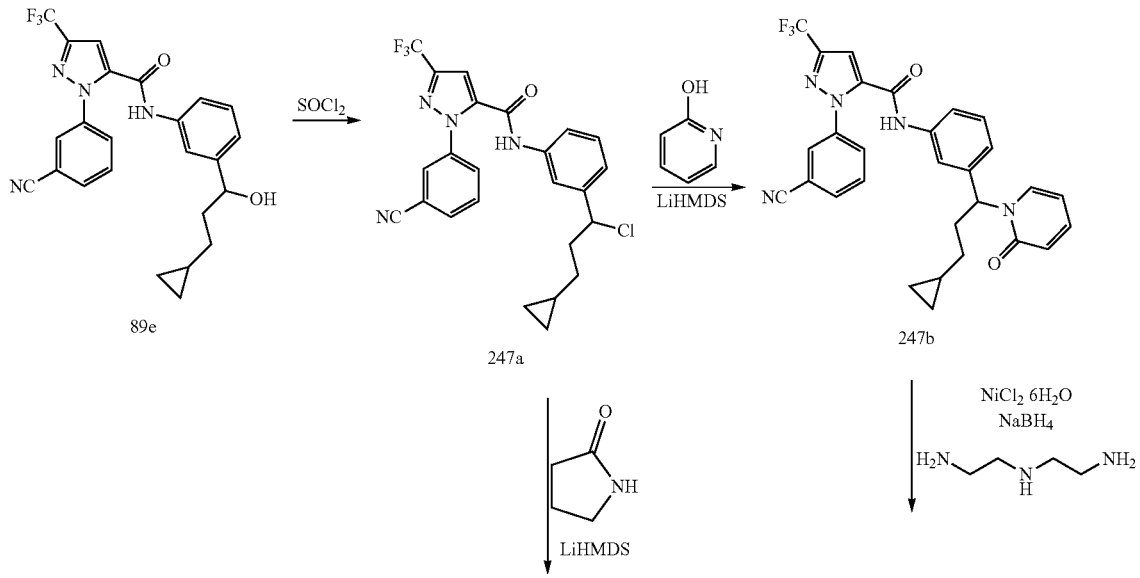

Scheme 247

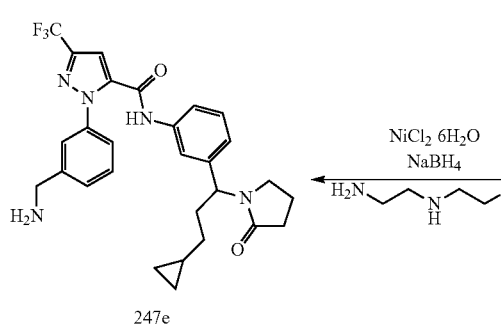
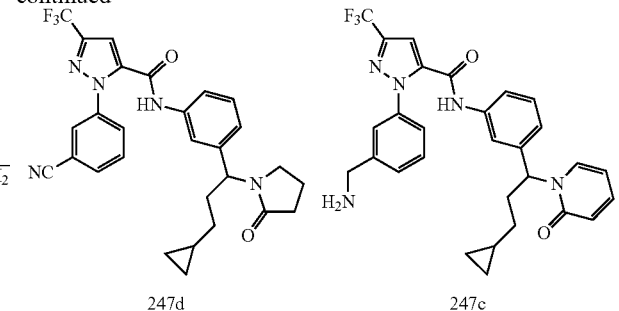

247e            247d            247c

Preparation of 1-(3-(aminomethyl)phenyl)-N-(3-(3-cyclopropyl-1-(2-oxopyridin-1(2H)-yl)propyl)phenyl)-3-(trifluoromethyl)-1H-pyrazole-5-carboxamide (247c)

Step-1: Preparation of N-(3-(1-chloro-3-cyclopropylpropyl)phenyl)-1-(3-cyanophenyl)-3-(trifluoromethyl)-1H-pyrazole-5-carboxamide (247a)

To a solution of 1-(3-cyanophenyl)-N-(3-(3-cyclopropyl-1-hydroxypropyl)phenyl)-3-(trifluoromethyl)-1H-pyrazole-5-carboxamide (89e) (200 mg, 0.440 mmol) in dichloromethane (12 mL) at 0° C. was added sulfurous dichloride (0.070 mL, 0.946 mmol) and allowed to warm to room temperature over 2 h. The reaction mixture was concentrated in vacuum to furnish N-(3-(1-chloro-3-cyclopropylpropyl)phenyl)-1-(3-cyanophenyl)-3-(trifluoromethyl)-1H-pyrazole-5-carboxamide (247a) which was used as such without further purification.

Step-2: Preparation of 1-(3-cyanophenyl)-N-(3-(3-cyclopropyl-1-(2-oxopyridin-1(2H)-yl)propyl)phenyl)-3-(trifluoromethyl)-1H-pyrazole-5-carboxamide (247b)

To a solution of pyridin-2-ol (216 mg, 2.200 mmol) in THF (5 mL) was added Lithium bis(dimethylsilyl)amide (2.20 mL, 2.200 mmol, 1 M in THF) stirred at room temperature for 0.5 h and concentrated in vacuum to dryness. To this was added a solution of N-(3-(1-chloro-3-cyclopropylpropyl)phenyl)-1-(3-cyanophenyl)-3-(trifluoromethyl)-1H-pyrazole-5-carboxamide (247a) in DMF (10 mL) and heated at 70° C. for 14 h. The reaction mixture was diluted with ethyl acetate (200 mL), washed with water (2×75 mL), brine (75 mL), dried over MgSO$_4$ filtered and concentrated in vacuum. The crude product was purified by flash column chromatography [silica gel, eluting with hexanes/ethyl acetate (1:0 to 1:1)] to afford 1-(3-cyanophenyl)-N-(3-(3-cyclopropyl-1-(2-oxopyridin-1(2H)-yl)propyl)phenyl)-3-(trifluoromethyl)-1H-pyrazole-5-carboxamide (247b) (49 mg, 21%) as an off-white solid. $^1$H NMR (300 MHz, DMSO-d$_6$) δ 10.70 (s, 1H), 8.17 (t, J=1.8 Hz, 1H), 8.00 (dt, J=7.8, 1.4 Hz, 1H), 7.91 (m, 1H), 7.79-7.60 (m, 4H), 7.55 (t, J=1.8 Hz, 1H), 7.41-7.30 (m, 2H), 7.17 (d, J=7.8 Hz, 1H), 6.44-6.38 (m, 1H), 6.23 (td, J=6.7, 1.5 Hz, 1H), 6.13-6.05 (m, 1H), 2.30-2.14 (m, 2H), 1.29-0.92 (m, 2H), 0.80-0.61 (m, 1H), 0.42-0.26 (m, 2H), 0.06--0.15 (m, 2H); $^{19}$F NMR (282 MHz, DMSO-d$_6$) δ -60.76; MS (ES+): 532.5 (M+1).

Step-3: Preparation of 1-(3-(aminomethyl)phenyl)-N-(3-(3-cyclopropyl-1-(2-oxopyridin-1(2H)-yl)propyl)phenyl)-3-(trifluoromethyl)-1H-pyrazole-5-carboxamide (247c)

Compound 247c was prepared from 1-(3-cyanophenyl)-N-(3-(3-cyclopropyl-1-(2-oxopyridin-1(2H)-yl)propyl)phenyl)-3-(trifluoromethyl)-1H-pyrazole-5-carboxamide (247b) (44 mg, 0.083 mmol) according to the procedure reported in step-6 of scheme-89 for compound 89f to furnish after purification by flash column chromatography [silica gel, eluting with chloroform/methanol (1:0 to 9:1)] 1-(3-(aminomethyl)phenyl)-N-(3-(3-cyclopropyl-1-(2-oxopyridin-1(2H)-yl)propyl)phenyl)-3-(trifluoromethyl)-1H-pyrazole-5-carboxamide (247c) (25 mg, 56.4%) free base as a white solid; $^1$H NMR (300 MHz, DMSO-d$_6$) δ 10.75 (s, 1H), 7.67-7.54 (m, 4H), 7.52 (s, 1H), 7.47-7.27 (m, 5H), 7.19-7.12 (m, 1H), 6.43-6.37 (m, 1H), 6.27-6.20 (m, 1H), 6.08 (t, J=8.1 Hz, 1H), 3.77 (s, 2H), 2.30-2.10 (m, 2H), 1.27-0.93 (m, 2H), 0.77-0.60 (m, 1H), 0.37 (m, 2H), -0.05 to -0.10 (m, 2H); $^{19}$F NMR (282 MHz, DMSO-d$_6$) δ -60.51; MS (ES+) 536.5 (M+1).

Free base of compound 247c (18 mg, 0.034 mmol) was dissolved in methanol (1 mL), added 4 N HCl (aq. 0.034 mL) and concentrated in vacuum to dryness. The residue was dissolved in water (0.5 mL) followed by lyopholization to obtain 1-(3-(aminomethyl)phenyl)-N-(3-(3-cyclopropyl-1-(2-oxopyridin-1(2H)-yl)propyl)phenyl)-3-(trifluoromethyl)-1H-pyrazole-5-carboxamide (247c) hydrochloride as a white solid; $^1$H NMR (300 MHz, DMSO-d$_6$) δ 10.80 (s, 1H), 8.31 (s, 3H), 7.71 (t, J=1.7 Hz, 1H), 7.66 (s, 2H), 7.65-7.51 (m, 5H), 7.41-7.29 (m, 2H), 7.18 (d, J=7.8 Hz, 1H), 6.39 (dd, J=9.0, 1.4 Hz, 1H), 6.23 (td, J=6.7, 1.5 Hz, 1H), 6.08 (t, J=8.0 Hz, 1H), 4.13 (q, J=5.8 Hz, 2H), 2.21 (m, 2H), 1.09 (m, 2H), 0.71 (m, 1H), 0.37 (m, 2H), -0.03 (m, 2H); $^{19}$F NMR (282 MHz, DMSO-d$_6$) δ -60.60; MS (ES+) 536.5 (M+1), (ES-) 534.5 (M-1), 570.5 (M+Cl).

Preparation of 1-(3-(aminomethyl)phenyl)-N-(3-(3-cyclopropyl-1-(2-oxopyrrolidin-1-yl)propyl)phenyl)-3-(trifluoromethyl)-1H-pyrazole-5-carboxamide (247e)

Step-1: Preparation of 1-(3-cyanophenyl)-N-(3-(3-cyclopropyl-1-(2-oxopyrrolidin-1-yl)propyl)phenyl)-3-(trifluoromethyl)-1H-pyrazole-5-carboxamide (247d)

Compound 247d was prepared from N-(3-(1-chloro-3-cyclopropylpropyl)phenyl)-1-(3-cyanophenyl)-3-(trifluoromethyl)-1H-pyrazole-5-carboxamide (247a) (0.44 mmol)

and pyrrolidin-2-one (0.169 mL, 2.200 mmol) according to the procedure reported for compound 247b in above step-2 of this scheme to furnish after purification by flash column chromatography [silica gel with hexanes/ethyl acetate (1:0 to 1:1)]. Preparation of 1-(3-cyanophenyl)-N-(3-(3-cyclopropyl-1-(2-oxopyrrolidin-1-yl)propyl)phenyl)-3-(trifluoromethyl)-1H-pyrazole-5-carboxamide (247d) (11 mg, 4.8%) as a colorless gum; $^1$H NMR (300 MHz, DMSO-d$_6$) δ 10.68 (s, 1H), 8.18 (t, J=1.9 Hz, 1H), 8.01 (dt, J=7.9, 1.3 Hz, 1H), 7.95-7.89 (m, 1H), 7.75 (d, J=8.0 Hz, 1H), 7.72 (d, J=1.7 Hz, 1H), 7.65 (d, J=8.0 Hz, 1H), 7.51 (s, 1H), 7.36-7.28 (m, 1H), 7.07 (d, J=7.6 Hz, 1H), 5.09 (t, J=8.0 Hz, 1H), 2.39-2.16 (m, 2H), 2.07-1.70 (m, 6H), 1.24-0.98 (m, 2H), 0.73 (m, 1H), 0.51-0.24 (m, 2H), 0.12--0.15 (m, 2H); MS 522.4 (M+1), 544.5 (M+Na); (ES-) 520.4 (M-1).

Step-2: Preparation of 1-(3-(aminomethyl)phenyl)-N-(3-(3-cyclopropyl-1-(2-oxopyrrolidin-1-yl)propyl)phenyl)-3-(trifluoromethyl)-1H-pyrazole-5-carboxamide (247e)

Compound 247e was prepared from 1-(3-cyanophenyl)-N-(3-(3-cyclopropyl-1-(2-oxopyrrolidin-1-yl)propyl)phenyl)-3-(trifluoromethyl)-1H-pyrazole-5-carboxamide (247d) (10 mg, 0.019 mmol) according to the procedure reported in step-6 of scheme-89 for compound 89f to furnish after purification by flash column chromatography [silica gel, eluting with chloroform/methanol (1:0 to 9:1)] 1-(3-(aminomethyl)phenyl)-N-(3-(3-cyclopropyl-1-(2-oxopyrrolidin-1-yl)propyl)phenyl)-3-(trifluoromethyl)-1H-pyrazole-5-carboxamide (247e) (3 mg) as an off white solid; $^1$H NMR (300 MHz, MeOD) δ 7.55-7.35 (m, 6H), 7.33-7.27 (m, 2H), 7.10 (m, 1H), 5.24-5.13 (m, 1H), 3.60 (s, 2H), 3.45-3.30 (m, 1H), 3.05 (m, 1H), 2.49-2.32 (m, 2H), 2.09-1.84 (m, 2H), 1.26-1.05 (m, 3H), 0.86 (m, 1H), 0.80-0.65 (m, 1H), 0.41 (m, 2H), 0.06--0.02 (m, 2H); $^{19}$F NMR (282 MHz, MeOD) δ -64.55; MS (ES+) 526.4 (M+1).

Scheme 248

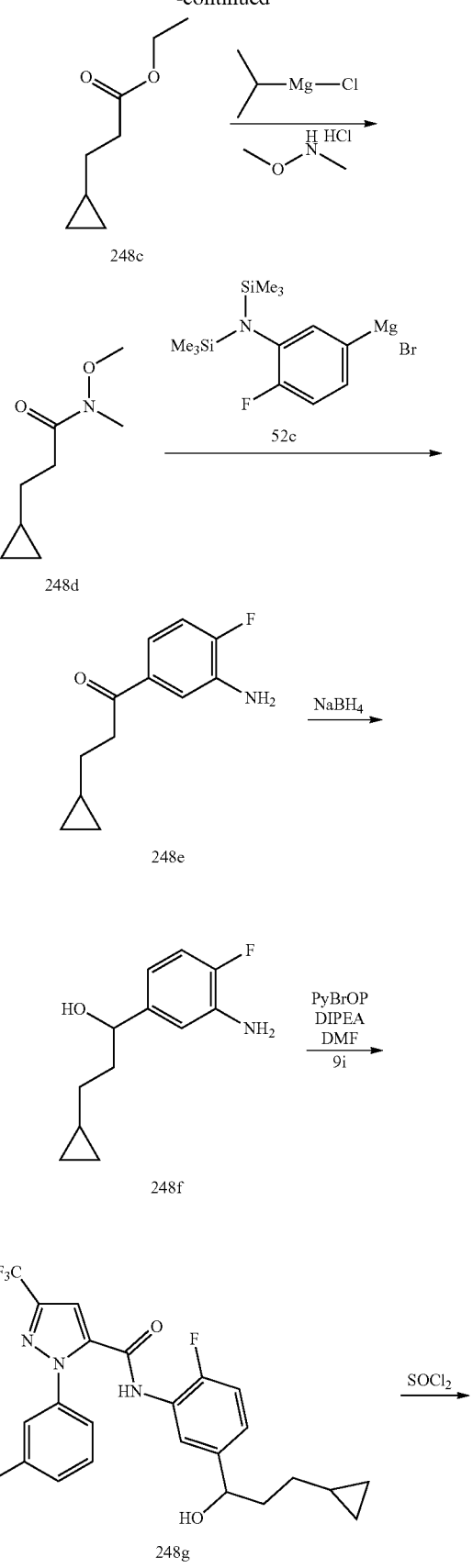

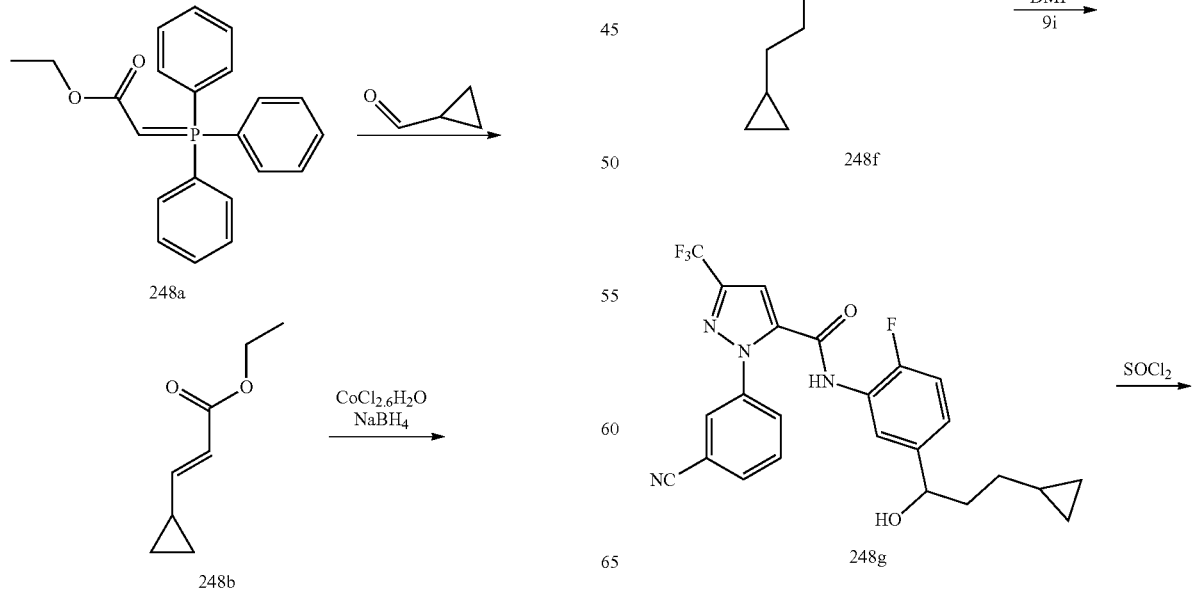

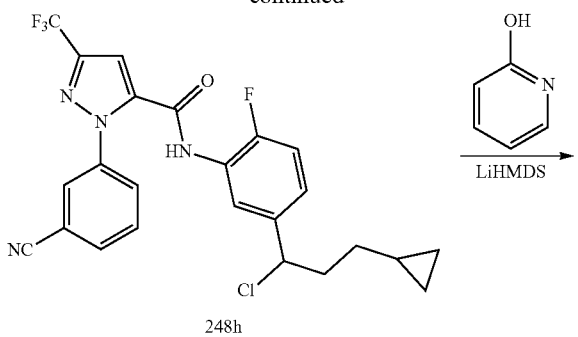

248h

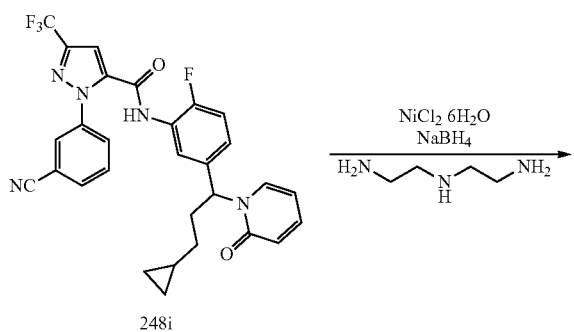

248i

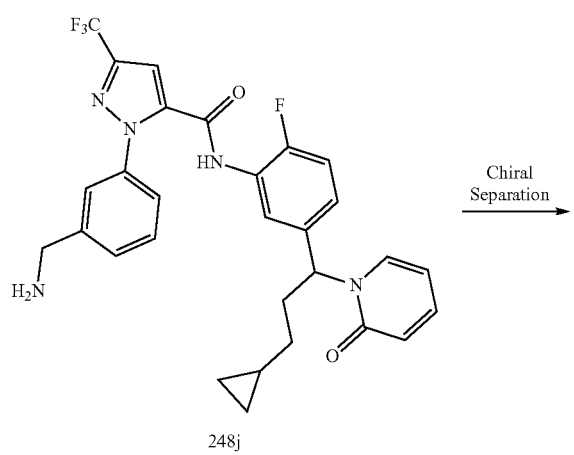

248j

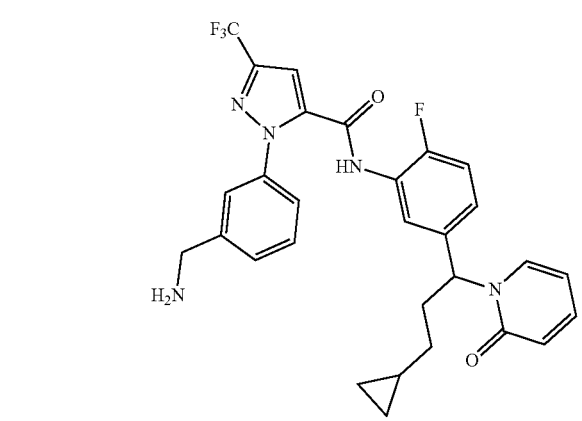

248k (+)-isomer
248l (−)-isomer

Preparation of 1-(3-(aminomethyl)phenyl)-N-(5-(3-cyclopropyl-1-(2-oxopyridin-1(2H)-yl)propyl)-2-fluorophenyl)-3-(trifluoromethyl)-1H-pyrazole-5-carboxamide (248j)

Step-1: Preparation of (E)-ethyl 3-cyclopropylacrylate (248b)

To a solution of 1-(triphenylphosphoranylidene)pentan-2-one (248a) (994 g, 2853 mmol) in dichloromethane (3000 mL) was added cyclopropanecarbaldehyde (200 g, 2853 mmol) and stirred at room temperature for 20 h. The reaction mixture was concentrated to ⅓ volume diluted with hexane (1000 mL) and concentrated in vacuum. The reaction mixture was diluted with hexane (3000 mL) stirred for 10 mins. The solid obtained of triphenylphospine oxide was removed by filtration. The filtrate was concentrated to afford (E)-ethyl 3-cyclopropylacrylate (248b) (410 g, 2925 mmol, 103% yield) as a colorless oil, which was used as such for next step without purification; $^1$H NMR (300 MHz, DMSO-$d_6$) δ 6.38 (dd, J=15.4, 10.2 Hz, 1H), 5.93 (d, J=15.4 Hz, 1H), 4.08 (q, J=7.1 Hz, 2H), 1.64 (dtt, J=10.2, 8.0, 4.6 Hz, 1H), 1.19 (td, J=7.1, 1.0 Hz, 3H), 0.98-0.82 (m, 2H), 0.75-0.62 (m, 2H).

Step-2: Preparation of ethyl 3-cyclopropylpropanoate (248c)

To a solution of (E)-ethyl 3-cyclopropylacrylate (248b) (290 g, 2069 mmol) in methanol (2000 mL) cooled to 5° C. was added cobalt(II) chloride hexahydrate (24.61 g, 103 mmol) followed by dropwise addition of a solution of sodium tetrahydroborate (157 g, 4138 mmol) in DMF (500 mL) at such a rate that internal temperature was not allowed to raise above 10° C. The reaction mixture was stirred for 1 h at 5° C., poured into water (5000 mL) and stirred for 15 mins. The resultant black suspended solution was filtered over celite pad, washed with dichloromethane (3×800 mL). The aqueous layer was separated and extracted with dichloromethane (2×600 mL). The dichloromethane layers were combined, washed with water (2×1500 mL), brine, dried over MgSO$_4$, filtered and concentrated under vacuum with bath temperature below 40° C. to afford ethyl 3-cyclopropylpropanoate (248c) (260 g, 88% yield) as colorless liquid; $^1$H NMR (300 MHz, DMSO-$d_6$) δ 4.03 (q, J=7.1 Hz, 2H), 2.33 (t, J=7.3 Hz, 2H), 1.41 (q, J=7.2 Hz, 2H), 1.16 (t, J=7.1 Hz, 3H), 0.75-0.59 (m, 1H), 0.40-0.31 (m, 2H), 0.06-−0.06 (m, 2H).

Step-3: Preparation of 3-cyclopropyl-N-methoxy-N-methylpropanamide (248d)

To a solution of ethyl 3-cyclopropylpropanoate (248c) (260 g, 1828 mmol) in THF (2000 mL) cooled to −10° C. was added N,O-dimethylhydroxylamine hydrochloride (268 g, 2743 mmol), followed by drop-wise addition of isopropylmagnesiumchloride (2743 mL, 5485 mmol, 2 M in THF). The mixture was stirred at −10° C. for 2 h, quenched with sat. NH$_4$Cl solution (4000 mL) and allowed to warm to room temperature. The THF layer was separated and aqueous layer was extracted with EtOAc (2×1000 mL). The organic layers were combined washed with brine, dried over MgSO$_4$, filtered and concentrated in vacuum to afford 3-cyclopropyl-N-methoxy-N-methylpropanamide (248d) (240 g, 1527 mmol, 83% yield) as an orange liquid; $^1$H NMR (300 MHz, DMSO-$d_6$) δ 3.66 (s, 3H), 3.07 (s, 3H), 2.44 (t, J=7.6

Hz, 2H), 1.39 (q, J=7.3 Hz, 2H), 0.76-0.62 (m, 1H), 0.42-0.31 (m, 2H), 0.08--0.09 (m, 2H).

Step-4: Preparation of 1-(3-amino-4-fluorophenyl)-3-cyclopropylpropan-1-one (248e)

To a solution of 3-cyclopropyl-N-methoxy-N-methylpropanamide (248d) (240 g, 1527 mmol) in THF (2000 mL) cooled to 5° C. was added drop-wise a freshly prepared solution of (3-(bis(trimethylsilyl)amino)-4-fluorophenyl) magnesium bromide (52c) (1908 mL, 1527 mmol, 1 M in THF) maintaining internal temperature around 5° C. during addition. The reaction was stirred at 5° C. for 2 h, quenched with 3N HCl (1000 mL) and stirred for 2 h. The mixture was basified with solid NaHCO$_3$ and extracted with ethyl acetate (2×500 mL). The combined organic layers were washed with brine, dried over MgSO$_4$, filtered and concentrated in vacuum to afford crude 248e. The crude material was dissolved in isopropanol (150 mL) and stirred over night. The solid obtained was collected by filtration washed with isopropanol and dried to afford 1-(3-amino-4-fluorophenyl)-3-cyclopropylpropan-1-one (248e) (90 g, 28.46% first crop) as a white solid. The filtrate was concentrated, kept at room temperature for 6 h and the solid obtained was collected by filtration to afford 1-(3-amino-4-fluorophenyl)-3-cyclopropylpropan-1-one (248e) (50 g, 15.81%, second crop) as a white solid; $^1$H NMR (300 MHz, DMSO-d$_6$) δ 7.38 (dd, J=8.9, 2.2 Hz, 1H), 7.18 (ddd, J=8.4, 4.7, 2.2 Hz, 1H), 7.09 (dd, J=11.1, 8.4 Hz, 1H), 5.41 (s, 2H), 2.98 (t, J=7.3 Hz, 2H), 1.48 (q, J=7.2 Hz, 2H), 0.82-0.65 (m, 1H), 0.41-0.33 (m, 2H), 0.10--0.02 (m, 2H); MS (ES+) 208.2 (M+1), (ES-) 206.2 (M-1); 19F NMR (282 MHz, DMSO-d$_6$) δ -128.24;

Step-5: Preparation of 1-(3-amino-4-fluorophenyl)-3-cyclopropylpropan-1-ol (248f)

To a solution of 1-(3-amino-4-fluorophenyl)-3-cyclopropylpropan-1-one (248e) (13.63 g, 65.8 mmol) in THF (150 mL) and methanol (300 mL) at 0° C. was added sodium borohydride (5.08 g, 132 mmol) and stirred at 0° C. for 1 h. The reaction mixture was allowed to warm to room temperature overnight. The reaction mixture was diluted with ethyl acetate (800 mL), neutralized with acetic acid, washed with water (2×300 mL), brine (300 mL), dried over MgSO$_4$, filtered and concentrated in vacuum. The residue was purified by flash column chromatography [silica gel, eluting with hexanes/ethyl acetate (1:0 to 4:1)] to afford 1-(3-amino-4-fluorophenyl)-3-cyclopropylpropan-1-ol (248f) (11.47 g, 53.8 mmol, 83% yield) as a white solid; $^1$H NMR (300 MHz, DMSO-d$_6$) δ 6.86 (dd, J=11.5, 8.2 Hz, 1H), 6.72 (dd, J=9.1, 2.1 Hz, 1H), 6.42 (ddd, J=8.3, 4.5, 2.1 Hz, 1H), 5.03 (s, 2H), 4.98 (d, J=4.1 Hz, 1H), 4.40-4.30 (m, 1H), 1.71-1.48 (m, 2H), 1.26-1.01 (m, 2H), 0.73-0.54 (m, 1H), 0.45-0.24 (m, 2H), 0.02--0.14 (m, 2H); $^{19}$F NMR (282 MHz, DMSO) δ -138.16; MS (ES+) 210.1 (M+1); (ES-) 208.1 (M-1).

Step-6: Preparation of 1-(3-cyanophenyl)-N-(5-(3-cyclopropyl-1-hydroxypropyl)-2-fluorophenyl)-3-(trifluoromethyl)-1H-pyrazole-5-carboxamide (248g)

To a solution of 1-(3-cyanophenyl)-3-(trifluoromethyl)-1H-pyrazole-5-carboxylic acid (9i) (2.419 g, 8.60 mmol) in DMF (40 mL) was added 1-(3-amino-4-fluorophenyl)-3-cyclopropylpropan-1-ol (248f) (1.5 g, 7.17 mmol) N-ethyl-N-isopropylpropan-2-amine (7.50 mL, 43.1 mmol) and bromo-tris-pyrrolidino phosphoniumhexafluorophosphate (PyBrOP, 4.02 g, 8.60 mmol) at room temperature. The reaction mixture was stirred at room temperature for 19 h under nitrogen atmosphere. The reaction was diluted with water (200 mL) and extracted with ethyl acetate (2×100 mL). The organic layers were combined, washed with brine (50 mL), dried, filtered, and concentrated in vacuum to dryness. The residue obtained was purified by flash column chromatography [silica gel 40 g, eluting with hexanes/ethyl acetate (1:0 to 4:1)] to furnish 1-(3-cyanophenyl)-N-(5-(3-cyclopropyl-1-hydroxypropyl)-2-fluorophenyl)-3-(trifluoromethyl)-1H-pyrazole-5-carboxamide (248g) (2.22 g, 66%) as a yellow solid.
$^1$H NMR (300 MHz, DMSO-d$_6$) δ 10.54 (s, 1H), 8.13 (t, J=1.8 Hz, 1H), 8.00 (dt, J=7.7, 1.3 Hz, 1H), 7.94-7.88 (m, 1H), 7.79-7.68 (m, 2H), 7.49 (d, J=7.4 Hz, 1H), 7.27-7.16 (m, 2H), 5.22 (d, J=4.4 Hz, 1H), 4.52 (q, J=5.8 Hz, 1H), 1.73-1.55 (m, 2H), 1.16 (m, 2H), 0.72-0.54 (m, 1H), 0.41-0.28 (m, 2H), -0.02--0.09 (m, 2H); $^{19}$F NMR (282 MHz, DMSO) δ -60.94, -124.07; MS (ES-) 471.5 (M-1).

Step-7: N-(5-(1-chloro-3-cyclopropylpropyl)-2-fluorophenyl)-1-(3-cyanophenyl)-3-(trifluoromethyl)-1H-pyrazole-5-carboxamide (248h)

To a solution of 1-(3-cyanophenyl)-N-(5-(3-cyclopropyl-1-hydroxypropyl)-2-fluorophenyl)-3-(trifluoromethyl)-1H-pyrazole-5-carboxamide (248g) (645 mg, 1.365 mmol) in dichloromethane (36 mL) at 0° C. was added sulfurous dichloride (0.220 mL, 2.98 mmol) and allowed to warm to room temperature over 2 h. The reaction mixture was concentrated in vacuum to furnish N-(5-(1-chloro-3-cyclopropylpropyl)-2-fluorophenyl)-1-(3-cyanophenyl)-3-(trifluoromethyl)-1H-pyrazole-5-carboxamide (248h) which was used as such without further purification.

Step-8: Preparation of 1-(3-cyanophenyl)-N-(5-(3-cyclopropyl-1-(2-oxopyridin-1(2H)-yl)propyl)-2-fluorophenyl)-3-(trifluoromethyl)-1H-pyrazole-5-carboxamide (248i)

To a solution of pyridin-2-ol (669 mg, 6.83 mmol) in THF (15 mL) was added Lithium bis(dimethylsilyl)amide (6.90 mL, 6.90 mmol, 1 M in THF) stirred at room temperature for 0.5 h and concentrated in vacuum to dryness. To this was added a solution of N-(5-(1-chloro-3-cyclopropylpropyl)-2-fluorophenyl)-1-(3-cyanophenyl)-3-(trifluoromethyl)-1H-pyrazole-5-carboxamide (248h) (1.365 mmol) in DMF (10 mL) and heated at 70° C. for 14 h. The reaction mixture was diluted with ethyl acetate (200 mL), washed with water (2×75 mL), brine (75 mL), dried over MgSO$_4$ filtered and concentrated in vacuum. The crude product was purified by flash column chromatography [silica gel, eluting with hexanes/ethyl acetate (1:0 to 1:1)] to furnish 1-(3-cyanophenyl)-N-(5-(3-cyclopropyl-1-(2-oxopyridin-1(2H)-yl)propyl)-2-fluorophenyl)-3-(trifluoromethyl)-1H-pyrazole-5-carboxamide (248i) (81 mg, 0.147 mmol, 10.8%) as an off-white solid; $^1$H NMR (300 MHz, DMSO-d$_6$) δ 10.60 (s, 1H), 8.13 (s, 1H), 8.00 (dt, J=7.8, 1.3 Hz, 1H), 7.90 (d, J=8.4 Hz, 1H), 7.77-7.67 (m, 3H), 7.51 (d, J=7.1 Hz, 1H), 7.41-7.23 (m, 3H), 6.42-6.37 (m, 1H), 6.24 (td, J=6.7, 1.5 Hz, 1H), 6.06 (t, J=8.1 Hz, 1H), 2.22 (m, 2H), 1.32-0.92 (m, 2H), 0.75-0.60 (m, 1H), 0.43-0.30 (m, 2H), -0.05 to -0.15 (m, 2H); $^{19}$F NMR (282 MHz, DMSO-d$_6$) δ -60.95, -121.40; MS (ES+) 550.3 (M+1), 572.3 (M+Na), 548.3 (M-1).

Step-9: Preparation of 1-(3-(aminomethyl)phenyl)-N-(5-(3-cyclopropyl-1-(2-oxopyridin-1(2H)-yl)propyl)-2-fluorophenyl)-3-(trifluoromethyl)-1H-pyrazole-5-carboxamide (248j)

Compound 248j was prepared from 1-(3-cyanophenyl)-N-(5-(3-cyclopropyl-1-(2-oxopyridin-1(2H)-yl)propyl)-2- fluorophenyl)-3-(trifluoromethyl)-1H-pyrazole-5-carboxamide (248i) (45 mg, 0.082 mmol) according to the procedure reported in step-6 of scheme-89 for compound 89f to furnish after purification by flash column chromatography [silica gel, eluting with chloroform/methanol (1:0 to 9:1)] 1-(3-(aminomethyl)phenyl)-N-(5-(3-cyclopropyl-1-(2-oxopyridin-1(2H)-yl)propyl)-2-fluorophenyl)-3-(trifluoromethyl)-1H-pyrazole-5-carboxamide (248j) (28 mg, 0.051 mmol, 61.8%) free base as a colorless gum; $^1$H NMR (300 MHz, DMSO-$d_6$) δ 7.74-7.66 (m, 1H), 7.54 (d, J=18.6 Hz, 3H), 7.45-7.38 (m, 2H), 7.37-7.32 (m, 2H), 7.32-7.27 (m, 2H), 6.43-6.35 (m, 1H), 6.23 (td, J=6.7, 1.4 Hz, 1H), 6.05 (t, J=8.0 Hz, 1H), 3.77 (s, 2H), 2.31-2.07 (m, 2H), 1.21-0.90 (m, 2H), 0.77-0.59 (m, 1H), 0.44-0.22 (m, 2H), 0.10--0.12 (m, 2H); $^{19}$F NMR (282 MHz, DMSO-$d_6$) δ -60.72, -121.87.

The free base was dissolved in methanol (5 mL) added 4 N HCl (aq. 0.050 mL) and concentrated in vacuum to afford 1-(3-(aminomethyl)phenyl)-N-(5-(3-cyclopropyl-1-(2-oxopyridin-1(2H)-yl)propyl)-2-fluorophenyl)-3-(trifluoromethyl)-1H-pyrazole-5-carboxamide (248j) (29 mg, 89%) hydrochloride as an off white solid; $^1$H NMR (300 MHz, DMSO-$d_6$) δ 10.74 (s, 1H), 8.44 (s, 3H), 7.80-7.26 (m, 10H), 6.43 (d, J=9.1 Hz, 1H), 6.28 (t, J=6.7 Hz, 1H), 6.08 (t, J=8.0 Hz, 1H), 4.15 (q, J=5.9 Hz, 2H), 2.25 (q, J=8.2, 6.8 Hz, 2H), 1.25-0.95 (m, 2H), 0.80-0.65 (m, 1H), 0.45-0.35 (m, 2H), 0.13--0.10 (m, 2H); $^{19}$F NMR (282 MHz, DMSO-$d_6$) δ -60.63, -121.38; MS (ES+): 554.4 (M+1).

Preparation of (+)-1-(3-(aminomethyl)phenyl)-N-(5-(3-cyclopropyl-1-(2-oxopyridin-1(2H)-yl)propyl)-2-fluorophenyl)-3-(trifluoromethyl)-1H-pyrazole-5-carboxamide (248k), (−)-1-(3-(aminomethyl) phenyl)-N-(5-(3-cyclopropyl-1-(2-oxopyridin-1(2H)-yl)propyl)-2-fluorophenyl)-3-(trifluoromethyl)-1H-pyrazole-5-carboxamide (248l)

Racemic 1-(3-(aminomethyl)phenyl)-N-(5-(3-cyclopropyl-1-(2-oxopyridin-1(2H)-yl)propyl)-2-fluorophenyl)-3-(trifluoromethyl)-1H-pyrazole-5-carboxamide (248j) (350 mg) was separated using Preparative SFC method. Column: 2.1×25 cm ChiralPak AD-H from Chiral Technologies; CO$_2$ Co-solvent (Solvent B) Isopropanol with 1% Isopropylamine; Isocratic Method: 25% Co-solvent at 80 g/min; System pressure 100 bar; Column temperature 40° C.; sample diluents methanol, to furnish:

1. Peak-1 corresponding to (−)-1-(3-(aminomethyl)phenyl)-N-(5-(3-cyclopropyl-1-(2-oxopyridin-1(2H)-yl)propyl)-2-fluorophenyl)-3-(trifluoromethyl)-1H-pyrazole-5-carboxamide (248l) (91.4 mg, >99.99% ee) as a white solid. $^1$H NMR (300 MHz, MeOD) δ 7.76 (d, J=7.4 Hz, 1H), 7.59 (dd, J=7.0, 1.9 Hz, 1H), 7.51 (s, 1H), 7.48-7.36 (m, 4H), 7.32 (s, 1H), 7.26 (m, 1H), 7.16 (t, J=9.5 Hz, 1H), 6.52 (ddd, J=9.1, 1.4, 0.7 Hz, 1H), 6.35 (td, J=6.8, 1.4 Hz, 1H), 6.19 (t, J=8.0 Hz, 1H), 3.84 (s, 2H), 2.35-2.13 (m, 2H), 1.36-0.97 (m, 2H), 0.79-0.62 (m, 1H), 0.49-0.31 (m, 2H), 0.01--0.10 (m, 2H); $^{19}$F NMR (282 MHz, MeOD) δ -64.56, -126.36; MS (ES+) 554.3 (M+1); (ES−) 552.3 (M−1); Optical rotation: [α]$_D$=(−) 138.95 (MeOH, 0.535). Free base of compound (248l) (87 mg, 0.157 mmol) was dissolved in methanol (10 mL), filtered, added 4 N HCl (aq. 0.16 mL) and concentrated in vacuum to dryness. The residue was dissolved in water (5 mL), and lyophilized to afford HCl salt (59 mgs) as a white solid. H NMR (300 MHz, DMSO-$d_6$) δ 10.67 (s, 1H), 8.30 (s, 3H, D$_2$O exchangeable), 7.77-7.65 (m, 3H), 7.64-7.48 (m, 4H), 7.35 (m, 3H), 6.39 (dd, J=9.2, 1.4 Hz, 1H), 6.24 (td, J=6.7, 1.5 Hz, 1H), 6.05 (t, J=8.1 Hz, 1H), 4.13 (d, J=5.8 Hz, 2H), 2.22 (m, 2H), 1.06 (m, 2H), 0.69 (m, 1H), 0.37 (m, 2H), −0.01--0.07 (m, 2H); $^{19}$F NMR (282 MHz, DMSO-$d_6$) δ -60.83, -121.63; MS (ES$^+$): MS (ES+) 554.3 (M+1); MS (ES−) 588.3 (M+Cl); Chiral Purity >99.99% ee;

2. Peak-2 corresponding to (+)-1-(3-(aminomethyl)phenyl)-N-(5-(3-cyclopropyl-1-(2-oxopyridin-1(2H)-yl)propyl)-2-fluorophenyl)-3-(trifluoromethyl)-1H-pyrazole-5-carboxamide (248k) (89.4 mgs, 98.2% ee); $^1$H NMR (300 MHz, MeOD) δ 7.75 (s, 1H), 7.59 (d, J=6.9 Hz, 1H), 7.52 (s, 1H), 7.49-7.23 (m, 6H), 7.17 (t, J=9.5 Hz, 1H), 6.57-6.48 (m, 1H), 6.39-6.30 (m, 1H), 6.24-6.13 (m, 1H), 3.86 (s, 2H), 2.43-2.15 (m, 2H), 1.35-1.16 (m, 1H), 1.14-0.99 (m, 1H), 0.96-0.65 (m, 1H), 0.47-0.26 (m, 2H), −0.04--0.09 (m, 2H); 19F NMR (282 MHz, MeOD) δ -64.57, -126.35; Optical rotation: [α]$_D$=(+) 144.61 (MeOH, 0.52); Free base of compound (248k) (82 mg, 0.148 mmol) was dissolved in methanol (10 mL), filtered, added 4 N HCl (aq. 0.16 mL) and concentrated in vacuum to dryness. The residue was dissolved in water (5 mL), and lyophilized to afford HCl salt (65 mgs) as a white solid; $^1$H NMR (300 MHz, DMSO-$d_6$) δ 10.68 (s, 1H), 8.36 (s, 3H), 7.75-7.66 (m, 3H), 7.64-7.48 (m, 4H), 7.41-7.25 (m, 3H), 6.39 (dd, J=9.1, 1.3 Hz, 1H), 6.24 (td, J=6.7, 1.4 Hz, 1H), 6.05 (t, J=8.1 Hz, 1H), 4.13 (t, J=5.5 Hz, 2H), 2.30-2.14 (m, 2H), 1.25-0.91 (m, 2H), 0.77-0.59 (m, 1H), 0.46-0.28 (m, 2H), 0.05--0.12 (m, 2H); $^{19}$F NMR (282 MHz, DMSO) δ -60.82, -121.62; Chiral Purity 98.87% ee.

The following analytical method was used to check chiral purity of compounds 248k and 2431; Column: ChiraCel AD-H 250 mm/5 μm 4.6 mm; Solvent system: 80:20 Hexane/Ethanol with 0.1 TEA; Flow rate: 1.0 mL/mL; Column temperature: 25° C.; Injection volume: 5 μl; UV detection: 260 nm.

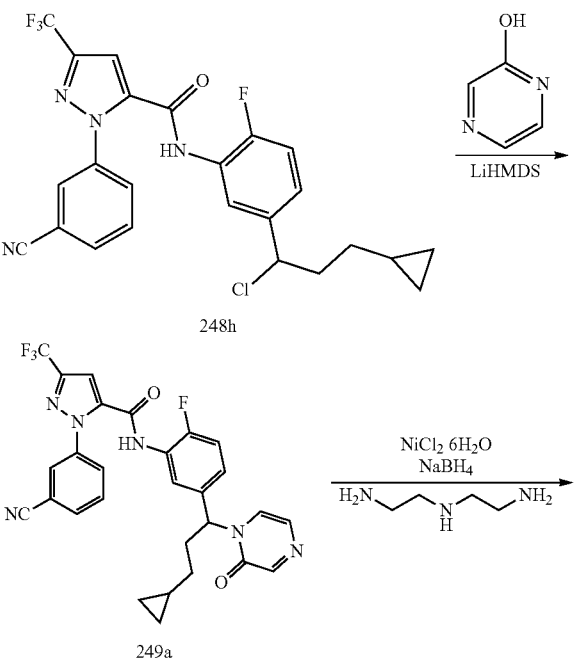

Scheme 249

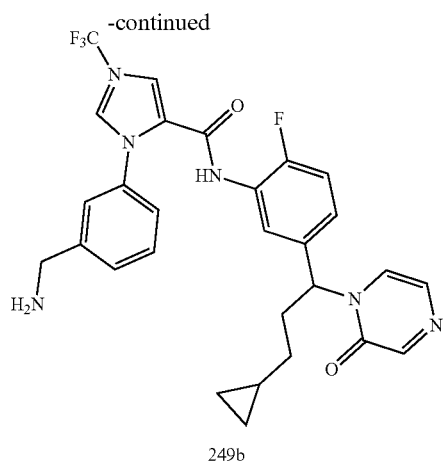

249b

Preparation of 1-(3-(aminomethyl)phenyl)-N-(5-(3-cyclopropyl-1-(2-oxopyrazin-1(2H)-yl)propyl)-2-fluorophenyl)-3-(trifluoromethyl)-1H-pyrazole-5-carboxamide (249b)

Step-1: Preparation of 1-(3-cyanophenyl)-N-(5-(3-cyclopropyl-1-(2-oxopyrazin-1(2H)-yl)propyl)-2-fluorophenyl)-3-(trifluoromethyl)-1H-pyrazole-5-carboxamide (249a)

To a solution of pyrazin-2-ol (431 mg, 4.40 mmol) in THF (10 mL) was added LiHMDS (4.40 mL, 4.40 mmol, 1 M in THF), stirred at room temperature for 0.5 h and concentrated in vacuum to dryness. To this was added a solution of N-(5-(1-chloro-3-cyclopropylpropyl)-2-fluorophenyl)-1-(3-cyanophenyl)-3-(trifluoromethyl)-1H-pyrazole-5-carboxamide (248h) (0.88 mmol) in DMF (18 mL) and heated at 70° C. for 14 h. The reaction mixture was diluted with ethyl acetate (200 mL), washed with water (2×75 mL), brine (75 mL), dried over MgSO$_4$, filtered and concentrated in vacuum. The crude product was purified by flash column chromatography [silica gel, eluting with hexanes/ethyl acetate (1:0 to 1:1)] to afford 1-(3-cyanophenyl)-N-(5-(3-cyclopropyl-1-(2-oxopyrazin-1(2H)-yl)propyl)-2-fluorophenyl)-3-(trifluoromethyl)-1H-pyrazole-5-carboxamide (249a) (141 mg, 0.256 mmol, 29.1%) as an off-white solid; $^1$H NMR (300 MHz, DMSO-d$_6$) δ 10.62 (s, 1H), 8.13 (d, J=2.1 Hz, 1H), 8.02 (d, J=1.1 Hz, 1H), 8.02-7.97 (m, 1H), 7.90 (dd, J=8.9, 1.8 Hz, 1H), 7.77 (dd, J=4.6, 1.2 Hz, 1H), 7.76-7.70 (m, 2H), 7.55 (d, J=6.8 Hz, 1H), 7.40-7.27 (m, 3H), 5.88 (t, J=8.0 Hz, 1H), 2.35-2.15 (m, 2H), 1.15-0.96 (m, 2H), 0.75-0.60 (m, 1H), 0.44-0.25 (m, 2H), 0.05--0.17 (m, 2H); $^{19}$F NMR (282 MHz, DMSO-d$_6$) δ -60.79, -120.66; MS (ES+) 551.4 (M+1); 573.4 (M+Na).

Step-2: Preparation of 1-(3-(aminomethyl)phenyl)-N-(5-(3-cyclopropyl-1-(2-oxopyrazin-1(2H)-yl)propyl)-2-fluorophenyl)-3-(trifluoromethyl)-1H-pyrazole-5-carboxamide (249b)

Compound 249b was prepared from 1-(3-cyanophenyl)-N-(5-(3-cyclopropyl-1-(2-oxopyrazin-1(2H)-yl)propyl)-2-fluorophenyl)-3-(trifluoromethyl)-1H-pyrazole-5-carboxamide (249a) (124 mg, 0.225 mmol) according to the procedure reported in step-6 of scheme-89 for compound 89f to furnish after purification by flash column chromatography [silica gel, eluting with chloroform/methanol (1:0 to 9:1)] compound 248j (20 mg, 0.036 mmol, 16.01%) free base as a brown solid. The free base was dissolved in methanol (5 mL), added 4 N HCl (aq. 0.050 mL) and concentrated in vacuum to afford 1-(3-cyanophenyl)-N-(5-(3-cyclopropyl-1-(2-oxopyrazin-1(2H)-yl)propyl)-2-fluorophenyl)-3-(trifluoromethyl)-1H-pyrazole-5-carboxamide (249a) (21 mg, 92.19%) hydrochloride as an off white solid; $^1$H NMR (300 MHz, DMSO-d$_6$) δ 10.72 (s, 1H), 8.41 (s, 3H), 8.02 (d, J=1.1 Hz, 1H), 7.79 (dd, J=4.5, 1.2 Hz, 1H), 7.72 (d, J=2.0 Hz, 1H), 7.68 (s, 1H), 7.65-7.48 (m, 4H), 7.40-7.28 (m, 3H), 5.88 (dd, J=9.1, 7.0 Hz, 1H), 4.12 (q, J=5.8 Hz, 2H), 2.37-2.13 (m, 2H), 1.21-0.96 (m, 2H), 0.78-0.60 (m, 1H), 0.45-0.27 (m, 2H), 0.02--0.07 (m, 2H); $^{19}$F NMR (282 MHz, DMSO-d$_6$) δ -60.84, -121.00; MS (ES+) 555.4 (M+1), (ES-) 553.4 (M-1).

Scheme 250

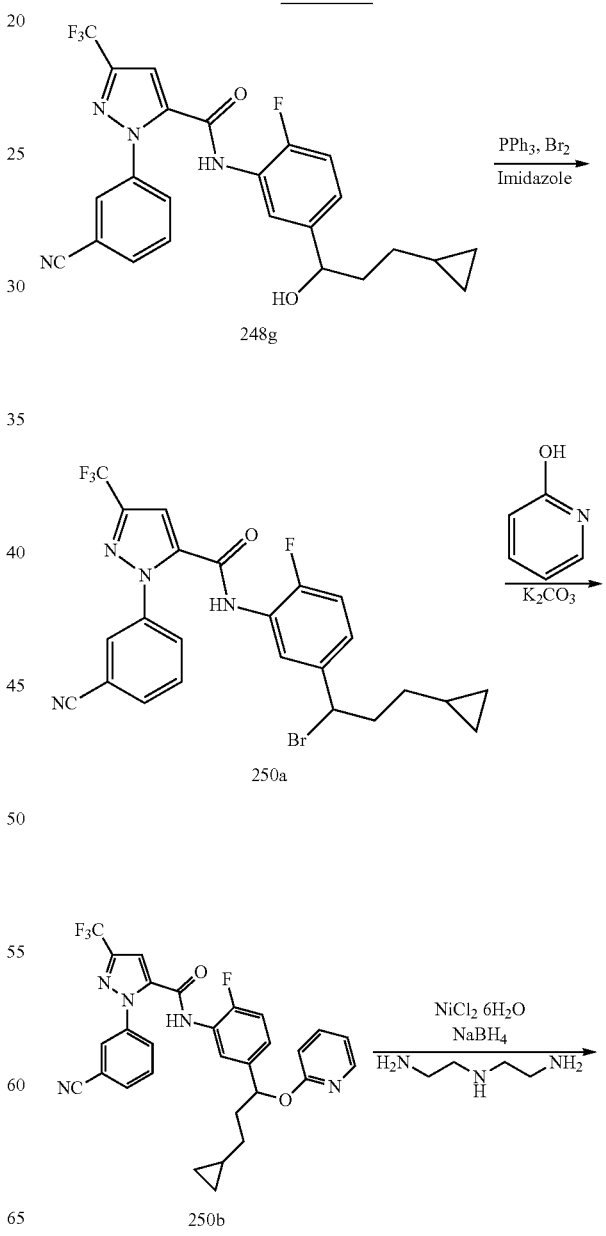

-continued

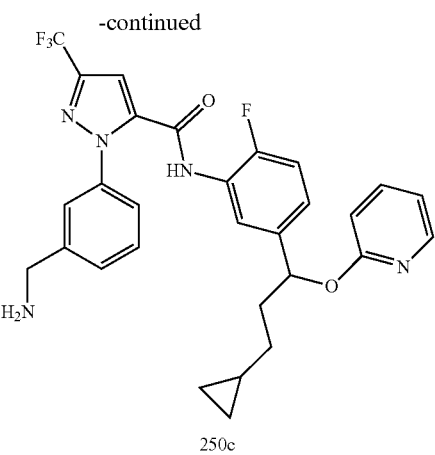

250c

Preparation of 1-(3-cyanophenyl)-N-(5-(3-cyclopropyl-1-(pyridin-2-yloxy)propyl)-2-fluorophenyl)-3-(trifluoromethyl)-1H-pyrazole-5-carboxamide (250b)

Step-1: Preparation of N-(5-(1-bromo-3-cyclopropylpropyl)-2-fluorophenyl)-1-(3-cyanophenyl)-3-(trifluoromethyl)-1H-pyrazole-5-carboxamide (250a)

To a solution of triphenylphosphine (0.833 g, 3.18 mmol) in dichloromethane (30 mL) at 0° C. was added bromine (0.131 mL, 2.54 mmol) over a period of 2 mins. To the reaction at 0° C. was added dropwise a premixed solution of 1-(3-cyanophenyl)-N-(5-(3-cyclopropyl-1-hydroxypropyl)-2-fluorophenyl)-3-(trifluoromethyl)-1H-pyrazole-5-carboxamide (0.6 g, 1.270 mmol) and imidazole (0.216 g, 3.18 mmol) in dichloromethane (30 mL). The reaction was stirred at 0° C. for 15 mins, allowed to warm to room temperature over a period of 1 h and diluted with dichloromethane (100 mL). The solution was passed through silica gel pad eluting with ethyl acetate in hexanes (20 to 30%) to afford N-(5-(1-bromo-3-cyclopropylpropyl)-2-fluorophenyl)-1-(3-cyanophenyl)-3-(trifluoromethyl)-1H-pyrazole-5-carboxamide (250a) (680 mg, 1.270 mmol, 100% yield) as a colorless semi solid.

$^1$H NMR (300 MHz, DMSO-d$_6$) δ 10.63 (s, 1H), 8.15 (t, J=1.9 Hz, 1H), 8.01 (dt, J=7.7, 1.4 Hz, 1H), 7.92 (dt, J=8.5, 1.3 Hz, 1H), 7.79-7.71 (m, 2H), 7.71-7.66 (m, 1H), 7.41 (m, 1H), 7.31 (m, 1H), 5.32 (t, J=7.5 Hz, 1H), 2.39-2.09 (m, 2H), 1.37-1.20 (m, 2H), 0.70 (m, 1H), 0.38 (m, 2H), 0.03--0.06 (m, 2H); $^{19}$F NMR (282 MHz, DMSO-d$_6$) δ -60.97, -119.88, -122.84.

Step-2: Preparation of 1-(3-cyanophenyl)-N-(5-(3-cyclopropyl-1-(pyridin-2-yloxy)propyl)-2-fluorophenyl)-3-(trifluoromethyl)-1H-pyrazole-5-carboxamide (250b)

To a solution of pyridin-2-ol (604 mg, 6.35 mmol) in acetonitrile (25 mL) was added potassium carbonate (913 mg, 6.60 mmol) and heated to reflux for 1 h. The reaction was cooled to room temperature and added a solution of N-(5-(1-bromo-3-cyclopropylpropyl)-2-fluorophenyl)-1-(3-cyanophenyl)-3-(trifluoromethyl)-1H-pyrazole-5-carboxamide (250a) (680 mg, 1.27 mmol) in acetonitrile (15 mL) and heated at 70° C. for 8 h. The reaction mixture was suspended in water (50 mL) and extracted with ethyl acetate (3×100 mL). The ethyl acetate layers were combined washed with water (2×25 mL), brine (25 mL), dried, filtered and concentrated in vacuum. The crude residue obtained was purified by flash column chromatography [silica gel 12 g, eluting with a (9:1) mixture of ethyl acetate and methanol in hexanes (0 to 60%)] to afford 1-(3-cyanophenyl)-N-(5-(3-cyclopropyl-1-(pyridin-2-yloxy)propyl)-2-fluorophenyl)-3-(trifluoromethyl)-1H-pyrazole-5-carboxamide (250b) (151 mg, 0.275 mmol, 21.64% yield) as a syrup; $^1$H NMR (300 MHz, DMSO-d$_6$) δ 10.55 (s, 1H), 8.13 (s, 1H), 8.05 (ddd, J=5.0, 2.0, 0.8 Hz, 1H), 8.00 (dt, J=7.7, 1.3 Hz, 1H), 7.91 (d, J=8.4 Hz, 1H), 7.78-7.69 (m, 2H), 7.69-7.64 (m, 1H), 7.57 (d, J=7.0 Hz, 1H), 7.38-7.18 (m, 2H), 6.91 (ddd, J=7.1, 5.1, 0.9 Hz, 1H), 6.84 (dd, J=8.3, 1.0 Hz, 1H), 6.06 (dd, J=8.0, 5.3 Hz, 1H), 1.99 (s, 1H), 1.87 (s, 1H), 1.34-1.20 (m, 2H), 0.66 (s, 1H), 0.36 (m, 2H), -0.01--0.10 (m, 2H); $^{19}$F NMR (282 MHz, DMSO-d$_6$) δ -60.94, -120.42--124.83.

Step-3: Preparation of 1-(3-cyanophenyl)-N-(5-(3-cyclopropyl-1-(pyridin-2-yloxy)propyl)-2-fluorophenyl)-3-(trifluoromethyl)-1H-pyrazole-5-carboxamide (250b)

To a solution of 1-(3-cyanophenyl)-1-(pyridin-2-yloxy)propyl)-2-fluorophenyl)-3-(trifluoromethyl)-1H-pyrazole-5-carboxamide (250b) (145 mg, 0.264 mmol) in methanol (5 mL) cooled with ice/water was added nickel(II) chloride hexahydrate (16.12 mg, 0.068 mmol), sodium borohydride (64.4 mg, 1.669 mmol) in portions followed by stirring at room temperature for 1 h. The reaction mixture was quenched with N1-(2-aminoethyl)ethane-1,2-diamine (0.064 mL, 0.609 mmol) and stirred at room temperature for 0.5 h. The reaction mixture was concentrated in vacuum to remove methanol. The mixture was suspended in water (20 mL). The solid obtained was collected by filtration and purified by flash column chromatography (silica gel 4 g, eluting with CMA 80 in chloroform 0 to 100%) to afford 1-(3-cyanophenyl)-N-(5-(3-cyclopropyl-1-(pyridin-2-yloxy)propyl)-2-fluorophenyl)-3-(trifluoromethyl)-1H-pyrazole-5-carboxamide (250b) (61 mg, 0.110 mmol, 41.8% yield) as a light yellow solid; $^1$H NMR (300 MHz, DMSO-d$_6$) δ 10.56 (s, 1H), 8.14-8.00 (m, 1H), 7.72-7.64 (m, 1H), 7.62 (d, J=7.1 Hz, 1H), 7.55 (d, J=17.3 Hz, 2H), 7.48-7.37 (m, 2H), 7.33 (d, J=7.1 Hz, 1H), 7.30-7.16 (m, 2H), 6.91 (ddd, J=7.2, 5.0, 0.9 Hz, 1H), 6.84 (dd, J=8.3, 0.9 Hz, 1H), 6.05 (dd, J=8.2, 5.4 Hz, 1H), 3.78 (s, 2H), 1.98 (m, 1H), 1.86 (m, 1H), 1.25 (m, 2H), 0.79-0.56 (m, 1H), 0.41-0.24 (m, 2H), -0.02--0.08 (m, 2H); $^{19}$F NMR (282 MHz, DMSO-d$_6$) δ -60.73, -123.02; MS (ES+) 554.3 (M+1), (ES-) 552.3 (M-1).

Scheme 251

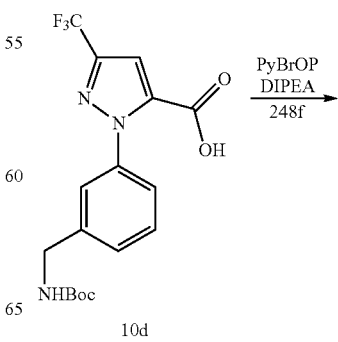

10d

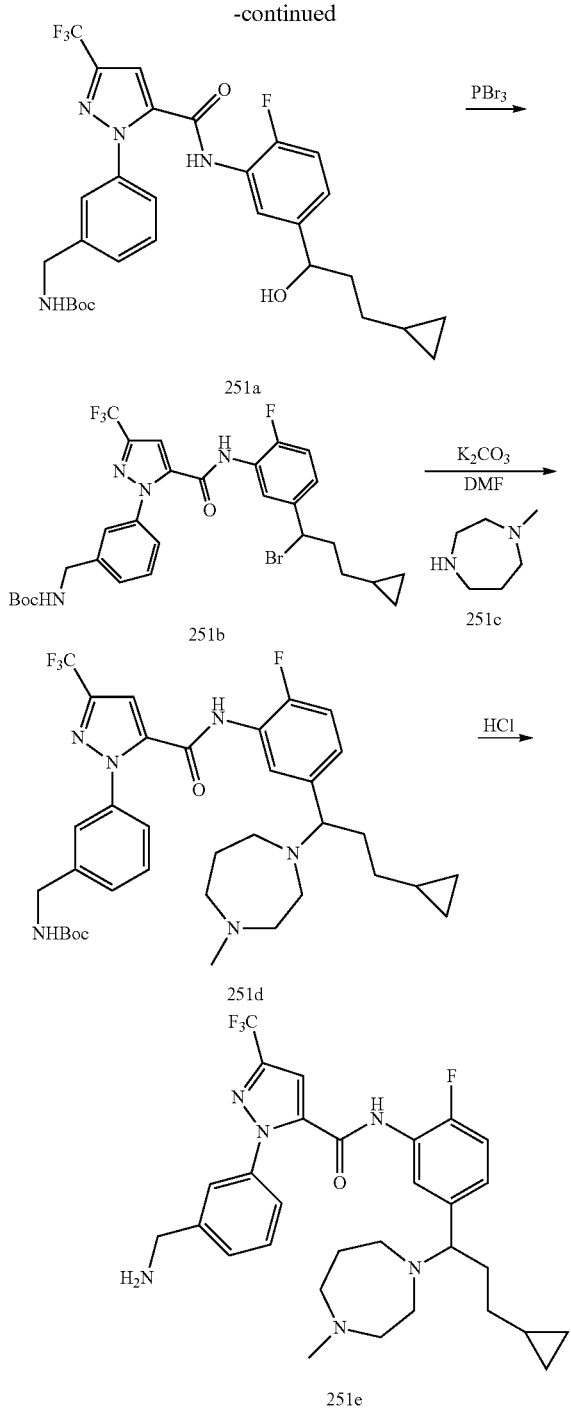

Preparation of 1-(3-(aminomethyl)phenyl)-N-(5-(3-cyclopropyl-1-(4-methyl-1,4-diazepan-1-yl)propyl)-2-fluorophenyl)-3-(trifluoromethyl)-1H-pyrazole-5-carboxamide (251e)

Step-1: Preparation of tert-butyl 3-(5-(5-(3-cyclopropyl-1-hydroxypropyl)-2-fluorophenylcarbamoyl)-3-(trifluoromethyl)-1H-pyrazol-1-yl)benzylcarbamate (251a)

To a solution of 1-(3-(((tert-butoxycarbonylamino)methyl)phenyl)-3-(trifluoromethyl)-1H-pyrazole-5-carboxylic acid (10d) (4.42 g, 11.47 mmol) in DMF (25 mL) was added 1-(3-amino-4-fluorophenyl)-3-cyclopropylpropan-1-ol (248f) (2 g, 9.56 mmol), N-ethyl-N-isopropylpropan-2-amine (8.32 mL, 47.8 mmol) and Bromo-tris-pyrrolidino phosphoniumhexafluorophosphate (PyBrOP) (4.92 g, 10.51 mmol) at room temperature. The reaction mixture was stirred at room temperature for 48 h under nitrogen atmosphere. The reaction was diluted with ethyl acetate (100 mL) washed with water (2×75 mL), brine (75 mL), dried, filtered, and evaporated to dryness. The residue obtained was purified by flash column chromatography [silica gel 40 g, eluting with ethyl acetate in hexanes from 0-25%] to furnish tert-butyl 3-(5-(5-(3-cyclopropyl-1-hydroxypropyl)-2-fluorophenylcarbamoyl)-3-(trifluoromethyl)-1H-pyrazol-1-yl) benzylcarbamate (251a) (4.04 g, 7.01 mmol, 73.3% yield) as a white foam; $^1$H NMR (300 MHz, DMSO-$d_6$) δ 10.56 (s, 1H), 7.60 (s, 1H), 7.51 (dd, J=14.3, 7.0 Hz, 2H), 7.46-7.32 (m, 4H), 7.23-7.16 (m, 2H), 5.21 (d, J=4.4 Hz, 1H), 4.51 (q, J=5.8 Hz, 1H), 4.19 (d, J=6.2 Hz, 2H), 1.71-1.53 (m, 2H), 1.38 (s, 9H), 1.34-1.07 (m, 2H), 0.74-0.56 (m, 1H), 0.43-0.24 (m, 2H), 0.03--0.12 (m, 2H); $^{19}$F NMR (282 MHz, DMSO) δ −60.80, −124.41; MS (ES+) 599.3 (M+Na); (ES−) 575.2 (M−1).

Step-2: Preparation of tert-butyl 3-(5-(5-(1-bromo-3-cyclopropylpropyl)-2-fluorophenylcarbamoyl)-3-(trifluoromethyl)-1H-pyrazol-1-yl)benzylcarbamate (251b)

To a cold solution (ice-water bath) of tert-butyl 3-(5-(5-(3-cyclopropyl-1-hydroxypropyl)-2-fluorophenylcarbamoyl)-3-(trifluoromethyl)-1H-pyrazol-1-yl)benzylcarbamate (251a) (2.04 g, 3.54 mmol) in THF (20 mL) was added PBr$_3$ (0.112 mL, 1.185 mmol). The resulting mixture was stirred for 40 min at 0° C. and quenched with water (50 mL). The reaction mixture was extracted with ethyl acetate (2×25 mL). The organic layers were combined washed with water and brine (50 mL), dried over anhydrous MgSO$_4$, filtered, and evaporated to dryness. The residue obtained was purified by flash column chromatography [silica gel 40 g, eluting with ethyl acetate in hexanes from 0-25%] to furnish tert-butyl 3-(5-(5-(1-bromo-3-cyclopropylpropyl)-2-fluorophenylcarbamoyl)-3-(trifluoromethyl)-1H-pyrazol-1-yl)benzylcarbamate (251b) (1.4 g, 2.189 mmol, 61.9% yield) as a White solid; $^1$H NMR (300 MHz, DMSO-$d_6$) δ 10.64 (s, 1H), 7.73 (d, J=7.6 Hz, 1H), 7.61 (s, 1H), 7.53-7.47 (m, 1H), 7.46-7.36 (m, 5H), 7.28 (d, J=9.0 Hz, 1H), 5.32 (t, J=7.5 Hz, 1H), 4.19 (d, J=6.2 Hz, 2H), 2.37-2.07 (m, 2H), 1.37 (s, 9H), 1.34-1.16 (m, 2H), 0.79-0.57 (m, 1H), 0.47-0.29 (m, 2H), 0.07--0.10 (m, 2H); $^{19}$F NMR (282 MHz, DMSO) δ −60.82, −121.25; MS (ES+) 661.2, 663.2 (M+Na).

Step-3: Preparation of tert-butyl 3-(5-(5-(3-cyclopropyl-1-(4-methyl-1,4-diazepan-1-yl)propyl)-2-fluorophenylcarbamoyl)-3-(trifluoromethyl)-1H-pyrazol-1-yl)benzylcarbamate (251d)

To a solution of tert-butyl 3-(5-(5-(1-bromo-3-cyclopropylpropyl)-2-fluorophenylcarbamoyl)-3-(trifluoromethyl)-1H-pyrazol-1-yl)benzylcarbamate (251b) (200 mg, 0.313 mmol) and N-methylhomopiperazine (251c) (143 mg, 1.251 mmol) in N,N-dimethylformamide (2 mL) was added K$_2$CO$_3$ (173 mg, 1.251 mmol). The reaction mixture was stirred at room temperature for 12 h, quenched with water (10 mL) and extracted with EtOAc (3×50 mL). The organic layers were combined washed with water (50 mL), brine (25 mL), dried over MgSO$_4$, filtered and concentrated. The residue was purified by flash column chromatography (silica gel 24 g, eluting with 0-90% EtOAc in hexane then 0-40% CMA80 in CHCl₃) to furnish tert-butyl 3-(5-(5-(3-cyclopropyl-1-(4-methyl-1,4-diazepan-1-yl)propyl)-2-fluorophenylcarbamoyl)-3-(trifluoromethyl)-1H-pyrazol-1-yl)benzylcarbamate (251d) (160 mg, 0.238 mmol, 76% yield) as white solid; $^1$H NMR (300 MHz, DMSO-d$_6$) δ 10.56 (s, 1H), 7.60 (s, 1H), 7.54-7.29 (m, 6H), 7.26-7.10 (m, 2H), 4.19 (d, J=6.3 Hz, 2H), 3.34 (s, 2H), 2.69-2.53 (m, 4H), 2.46-2.31 (m, 2H), 2.19 (s, 3H), 1.98-1.80 (m, 1H), 1.71-1.53 (m, 2H), 1.38 (s, 9H), 1.31-1.16 (m, 2H), 1.19-0.97 (m, 2H), 0.88-0.76 (m, 1H), 0.40-0.29 (m, 2H), −0.01--0.14 (m, 2H); $^{19}$F NMR (282 MHz, DMSO-d$_6$) δ −60.80, −124.05.

Step 4: Preparation of 1-(3-(aminomethyl)phenyl)-N-(5-(3-cyclopropyl-1-(4-methyl-1,4-diazepan-1-yl) propyl)-2-fluorophenyl)-3-(trifluoromethyl)-1H-pyrazole-5-carboxamide (251e)

To a solution of tert-butyl 3-(5-(5-(3-cyclopropyl-1-(4-methyl-1,4-diazepan-1-yl)propyl)-2-fluorophenylcarbamoyl)-3-(trifluoromethyl)-1H-pyrazol-1-yl)benzylcarbamate (251d) (156 mg, 0.232 mmol) in MeOH (3 mL) was added HCl (3N in MeOH, 1.546 mL, 4.64 mmol), stirred at room temperature overnight and concentrated in vacuum. The residue obtained was purified by flash column chromatography (silica gel 12 g, eluting with 0-80% CMA80 in CHCl₃), followed by reverse phase column chromatography (C$_{18}$ column 30 g, eluting with 0-50% MeOH in H$_2$O) to furnish compound 251e (110 mg, 0.192 mmol, 83% yield) free base as a white solid; $^1$H NMR (300 MHz, DMSO-d$_6$) δ 10.58 (s, 1H), 7.60 (s, 1H), 7.55 (s, 1H), 7.49-7.40 (m, 3H), 7.41-7.32 (m, 2H), 7.27-7.09 (m, 2H), 3.82 (s, 2H), 3.59 (d, J=7.2 Hz, 1H), 3.33-3.03 (m, 2H), 2.68-2.54 (m, 3H), 2.18 (s, 3H), 1.95-1.81 (m, 1H), 1.76-1.47 (m, 4H), 1.33-0.92 (m, 5H), 0.70-0.57 (m, 1H), 0.41-0.22 (m, 2H), −0.01--0.14 (m, 2H); $^{19}$F NMR (282 MHz, DMSO-d$_6$) δ −60.75, −124.00.

To a solution of free base of compound 251e (89 mg, 0.155 mmol) in MeOH (10 mL) was added HCl (3N in MeOH, 0.389 mL, 1.554 mmol), stirred at room temperature for 2 h and concentrated in vacuum. The residue was dissolved in H$_2$O/ACN (10 mL, 9.5:0.5, v/v) and freeze-dried to give 1-(3-(aminomethyl)phenyl)-N-(5-(3-cyclopropyl-1-(4-methyl-1,4-diazepan-1-yl)propyl)-2-fluorophenyl)-3-(trifluoromethyl)-1H-pyrazole-5-carboxamide (251e) (72 mg, 0.126 mmol, 81% yield) hydrochloride as a white solid; $^1$H NMR (300 MHz, DMSO-d$_6$) δ 12.30-11.90 (m, 1H), 11.68-11.29 (m, 1H), 11.07-10.81 (m, 1H), 8.58 (s, 3H), 7.88 (t, J=6.8 Hz, 1H), 7.82-7.70 (m, 3H), 7.69-7.50 (m, 4H), 7.52-7.36 (m, 1H), 4.54 (s, 1H), 4.12 (d, J=5.3 Hz, 2H), 3.97-3.48 (m, 4H), 3.47-3.20 (m, 3H), 2.82-2.62 (m, 3H), 2.45-2.04 (m, 3H), 1.09-0.89 (m, 1H), 0.81-0.51 (m, 2H), 0.38-0.27 (m, 2H), −0.04--0.15 (m, 2H); $^{19}$F NMR (282 MHz, DMSO-d$_6$) δ −60.81, −119.00; MS (ES$^+$): MS (ES+) 573.3 (M+1).

Scheme 252

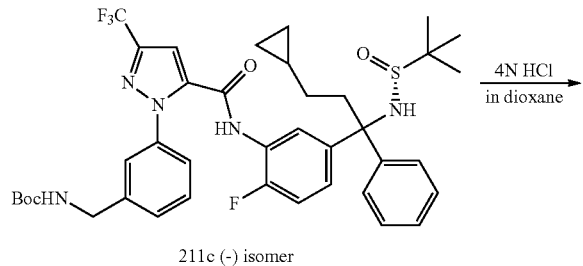

211c (−) isomer

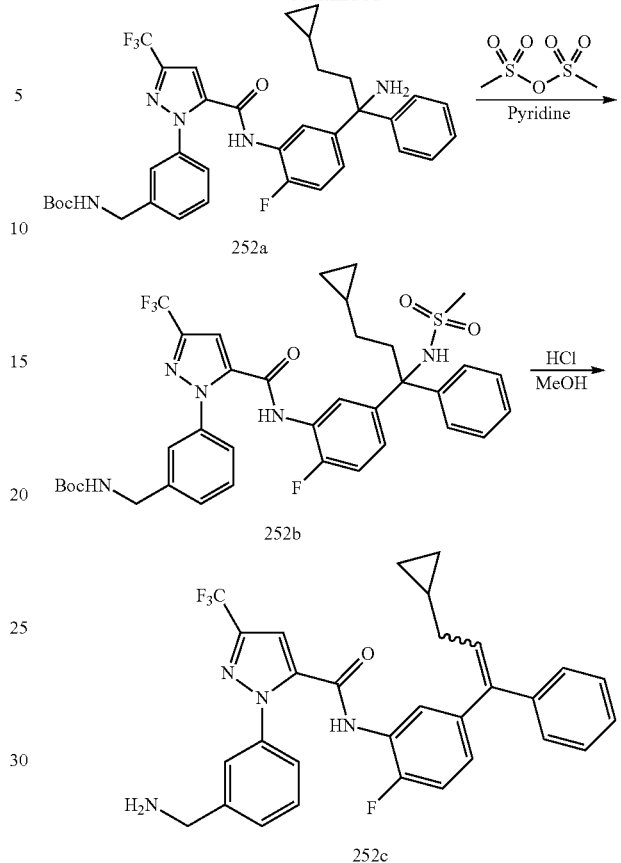

Preparation of 1-(3-(aminomethyl)phenyl)-N-(5-(3-cyclopropyl-1-phenylprop-1-enyl)-2-fluorophenyl)-3-(trifluoromethyl)-1H-pyrazole-5-carboxamide (252c)

Step-1: Preparation of tert-butyl 3-(5-(5-(1-amino-3-cyclopropyl-1-phenylpropyl)-2-fluorophenylcarbamoyl)-3-(trifluoromethyl)-1H-pyrazol-1-yl)benzylcarbamate (252a)

To a stirred solution of tert-butyl 3-(5-(5-((−)-3-cyclopropyl-1-((R)-1,1-dimethylethylsulfinamido)-1-phenylpropyl)-2-fluorophenylcarbamoyl)-3-(trifluoromethyl)-1H-pyrazol-1-yl)benzylcarbamate (211c) (1.603 g, 2.118 mmol) in methanol (18 mL) cooled to 0° C. was added 4 N hydrochloric acid in dioxane (1.6 mL, 6.40 mmol) and stirred at 0° C. for 2.5 h. The reaction mixture was quenched with triethylamine (1.100 mL, 7.89 mmol) and concentrated in vacuum to dryness. The residue obtained was purified by flash column chromatography [silica gel, eluting with hexanes/10% methanol in ethyl acetate (1:0 to 1:1)] to furnish tert-butyl 3-(5-(5-(1-amino-3-cyclopropyl-1-phenylpropyl)-2-fluorophenylcarbamoyl)-3-(trifluoromethyl)-1H-pyrazol-1-yl)benzylcarbamate (252a) (658 mg, 47.6%) as a white solid; $^1$H NMR (300 MHz, DMSO-d$_6$) δ 10.52 (s, 1H), 7.62-7.07 (m, 12H), 4.19 (d, J=6.2 Hz, 2H), 2.31-2.07 (m, 4H), 1.38 (s, 9H), 1.11-0.90 (m, 2H), 0.91-0.74 (m, 1H), 0.71-0.53 (m, 1H), 0.40-0.26 (m, 2H), −0.05--0.16 (m, 2H); $^{19}$F NMR (282 MHz, DMSO-d$_6$) δ −60.79, −123.62; MS (ES+) 652.4 (M+1), (ES−) 650.4 (M−1).

Step-2: Preparation of tert-butyl 3-(5-(5-(3-cyclopropyl-1-(methylsulfonamido)-1-phenylpropyl)-2-fluorophenylcarbamoyl)-3-(trifluoromethyl)-1H-pyrazol-1-yl)benzylcarbamate (252b)

To a solution of tert-butyl 3-(5-(5-(1-amino-3-cyclopropyl-1-phenylpropyl)-2-fluorophenylcarbamoyl)-3-(trifluoromethyl)-1H-pyrazol-1-yl)benzylcarbamate (252a) (145 mg, 0.222 mmol) in dichloromethane (10 mL) and pyridine (70.4 mg, 0.890 mmol) at 0° C. was added methanesulfonic anhydride (78 mg, 0.445 mmol). The resulting reaction mixture was stirred at room temperature overnight. Additional DIPEA (0.078 mL, 0.445 mmol) and methanesulfonic anhydride (78 mg, 0.445 mmol) was added and the mixture was stirred at room temperature for 2 h. The reaction mixture was diluted with water (10 mL) extracted with dichloromethane (3×10 mL) The organic layers were combined dried over MgSO$_4$, filtered and concentrated. The residue obtained was purified by flash column chromatography (silica gel, 12 g eluting with EtOAc/hex, 0-50%) to furnish tert-butyl 3-(5-(5-(3-cyclopropyl-1-(methyl sulfonamido)-1-phenylpropyl)-2-fluorophenylcarbamoyl)-3-(trifluoromethyl)-1H-pyrazol-1-yl)benzylcarbamate (252b) (86 mg) as a white solid; MS (ES+) 752.4 (M+23), (ES−) 728.5 (M−1).

Step-3: Preparation of 1-(3-(aminomethyl)phenyl)-N-(5-(3-cyclopropyl-1-phenylprop-1-enyl)-2-fluorophenyl)-3-(trifluoromethyl)-1H-pyrazole-5-carboxamide (252c)

To a solution of tert-butyl 3-(5-(5-(3-cyclopropyl-1-(methylsulfonamido)-1-phenylpropyl)-2-fluorophenylcarbamoyl)-3-(trifluoromethyl)-1H-pyrazol-1-yl)benzylcarbamate (252b) (86 mg, 0.118 mmol) in methanol (20 mL) was added HCl (3N anhydrous in MeOH, 2 mL) and heated at reflux for 30 min. The reaction was concentrated in vacuum and the residue obtained was purified by flash column chromatography (silica gel 12 g, eluting with CHCl$_3$ in CMA-80 0-60%) to furnish compound 252c (40 mg) free base as a white solid. The free base was dissolved in methanol (10 mL) and added HCl (3N anhydrous in MeOH, 2 mL) at room temperature. The Solution was concentrated in vacuum to dryness and the residue was dissolved in water (2 mL) and two drops of acetonitrile, lyophilized to furnish 1-(3-(aminomethyl)phenyl)-N-(5-(3-cyclopropyl-1-phenylprop-1-enyl)-2-fluorophenyl)-3-(trifluoromethyl)-1H-pyrazole-5-carboxamide (252c) (42 mg, 0.079 mmol, 35.3% yield over 2 steps) hydrochloride salt as a white solid; $^1$H NMR (300 MHz, DMSO-d$_6$) δ 10.68 (2s, 1H), 8.38 (bs, 3H), 7.75-7.64 (m, 2H), 7.66-7.56 (m, 1H), 7.56-7.21 (m, 7H), 7.20-7.09 (m, 2H), 7.11-7.00 (m, 1H), 6.17 (dt, J=15.1, 7.5 Hz, 1H), 3.36 (s, 2H), 1.94 (q, J=7.4 Hz, 2H), 0.87-0.68 (m, 1H), 0.49-0.29 (m, 2H), 0.14--0.01 (m, 2H); $^{19}$F NMR (282 MHz, DMSO) δ −60.63, −60.64, −122.32, −122.64. (E and Z mixture); MS (ES$^+$): MS (ES+) 535.4 (M+1); 533.3.4 (M−1); Analysis calculated for $C_{30}H_{26}F_4N_4O\cdot HCl\cdot H_2O$: C; 61.17, H; 4.96, N; 9.51; Found: C; 61.39, H; 5.02, N; 9.52.

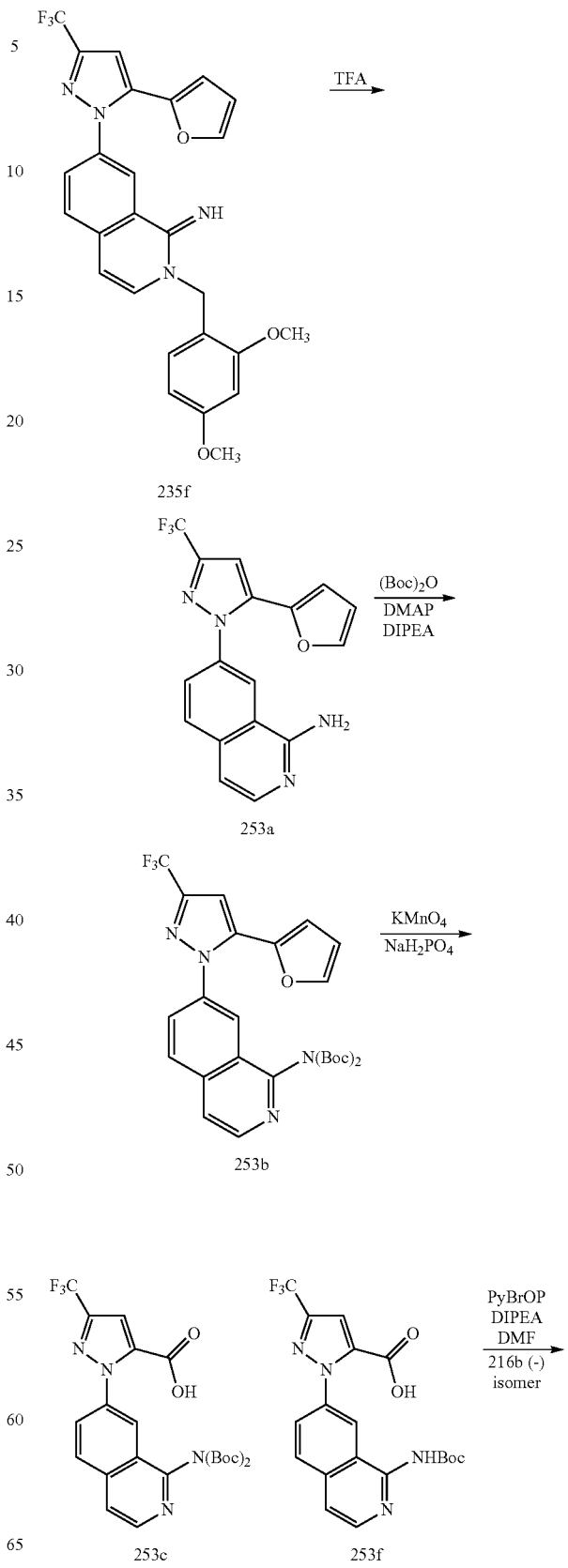

Scheme 253

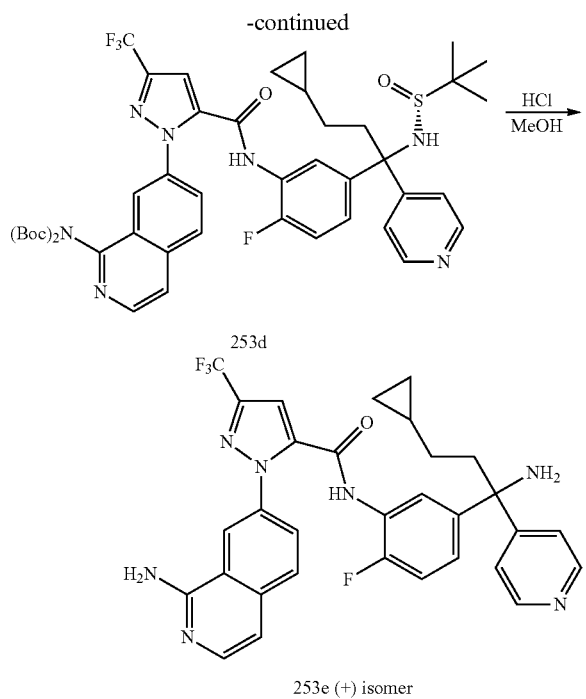

253d 253e (+) isomer

Preparation of (+)-N-(5-(1-amino-3-cyclopropyl-1-(pyridin-4-yl)propyl)-2-fluorophenyl)-1-(1-aminoisoquinolin-7-yl)-3-(trifluoromethyl)-1H-pyrazole-5-carboxamide (253e)

Step-1: Preparation of 7-(5-(furan-2-yl)-3-(trifluoromethyl)-1H-pyrazol-1-yl)isoquinolin-1-amine (253a)

A solution of 2-(2,4-dimethoxybenzyl)-7-(5-(furan-2-yl)-3-(trifluoromethyl)-1H-pyrazol-1-yl)isoquinolin-1(2H)-imine (235f) (2.88 g, 5.82 mmol) in TFA (10 mL) and anisole (5 mL) was heated to 90° C. for 19 h, cooled to room temperature and concentrated in vacuum. The residue was taken twice in MeOH (50 mL) and evaporated. The pH of the residue was adjusted to 8.0 using saturated aqueous NaHCO₃, diluted with water (50 mL) and extracted with ethyl acetate (2×50 mL). The combined organic layers were dried over anhydrous MgSO₄, filtered, evaporated to dryness. The residue obtained was purified by flash column chromatography [silica gel 40 g, eluting with ethyl acetate/methanol in hexanes from 0-100%] to furnish 7-(5-(furan-2-yl)-3-(trifluoromethyl)-1H-pyrazol-1-yl)isoquinolin-1-amine (253a) (0.994 g, 49% yield) as a pale yellow solid; $^1$H NMR (300 MHz, DMSO-d₆) δ 8.47 (d, J=2.1 Hz, 1H), 7.97-7.83 (m, 2H), 7.79-7.72 (m, 1H), 7.67 (dd, J=8.7, 2.0 Hz, 1H), 7.34 (s, 1H), 7.03 (d, J=5.8 Hz, 1H), 6.98 (s, 2H, D₂O exchangeable), 6.52 (dd, J=3.5, 1.8 Hz, 1H), 6.20 (dd, J=3.6, 0.8 Hz, 1H); $^{19}$F NMR (282 MHz, DMSO-d₆) δ −60.73; MS (ES−): MS (ES+) 345.2 (M+1); MS (ES−) 379.2 (M+Cl).

Step-2: Preparation of di-tert-butyl 7-(5-(furan-2-yl)-3-(trifluoromethyl)-1H-pyrazol-1-yl)isoquinolin-1-yliminodicarbonate (253b)

To a solution of 7-(5-(furan-2-yl)-3-(trifluoromethyl)-1H-pyrazol-1-yl)isoquinolin-1-amine (253a) (12.177 g, 35.4 mmol) in acetonitrile (150 mL) was added DIPEA (14.83 mL, 85 mmol), (BOC)₂O (61.6 mL, 265 mmol) and DMAP (1.080 g, 8.84 mmol). The mixture was heated at 50° C. overnight, cooled to room temperature and concentrated in vacuum. The residue was treated with brine/water (100 mL/400 mL) and extracted with ethyl acetate (2×750 mL). The combined organics were dried over anhydrous MgSO₄, filtered, evaporated to dryness. The residue was purified by flash column chromatography (silica gel 120 g, eluting with ethyl acetate in hexanes from 0-80%) to afford di-tert-butyl 7-(5-(furan-2-yl)-3-(trifluoromethyl)-1H-pyrazol-1-yl)isoquinolin-1-yliminodicarbonate (253b) (13.621 g, 71% yield) as a brown solid; $^1$H NMR (300 MHz, DMSO-d₆) δ 8.56 (d, J=5.7 Hz, 1H), 8.28 (d, J=8.8 Hz, 1H), 8.10-7.99 (m, 2H), 7.91 (dd, J=8.8, 2.1 Hz, 1H), 7.73 (d, J=1.8 Hz, 1H), 7.37 (s, 1H), 6.54 (dd, J=3.5, 1.8 Hz, 1H), 6.39 (d, J=3.5 Hz, 1H), 1.27 (s, 18H); $^{19}$F NMR (282 MHz, DMSO-d₆) δ −60.99. MS (ES⁺): MS (ES+): 567.2 (M+Na).

Step-3: Preparation of 1-(1-(bis(tert-butoxycarbonyl)amino)isoquinolin-7-yl)-3-(trifluoromethyl)-1H-pyrazole-5-carboxylic acid (253c) and 1-(1-(tert-butoxycarbonylamino)isoquinolin-7-yl)-3-(trifluoromethyl)-1H-pyrazole-5-carboxylic Acid (253f)

To a solution of di-tert-butyl 7-(5-(furan-2-yl)-3-(trifluoromethyl)-1H-pyrazol-1-yl)isoquinolin-1-yliminodicarbonate (253b) (5.70 g, 10.47 mmol) in t-BuOH (220 mL) was added 5% aq. sodium dihydrogenphosphate (2.387 g, 19.90 mmol) in water (50 mL) followed by potassium permanganate (3.31 g, 20.94 mmol). The reaction mixture was stirred at room temperature for 13 h, quenched with 2-propanol (350 mL) and stirred at room temperature overnight. The reaction mixture was filtered through Celite washed with 2-propanol. The filtrate was evaporated to dryness and purified by flash column chromatography (silica gel 80 g, eluting with CMA80 in chloroform from 0-100%) to furnish compound 253c and 253f. Each compound were separately acidified with 1N KHSO₄ (10 mL), extracted with ethyl acetate (2×30 mL), dried over anhydrous MgSO₄, filtered, concentrated in vacuum and dried over P2O5 to afford:

1. 1-(1-(bis(tert-butoxycarbonyl)amino)isoquinolin-7-yl)-3-(trifluoromethyl)-1H-pyrazole-5-carboxylic acid (253c) (1.161 g, 2.222 mmol, 21% yield) as a yellow solid; $^1$H NMR (300 MHz, DMSO-d₆) δ 8.53 (d, J=5.7 Hz, 1H), 8.21 (d, J=8.7 Hz, 1H), 8.09-7.97 (m, 3H), 7.59 (s, 1H), 1.29 (s, 18H); $^{19}$F NMR (282 MHz, DMSO-d₆) δ −60.97; MS (ES⁺): MS (ES+) 545.3 (M+Na); MS (ES−) 521.3 (M−1).
2. 1-(1-(tert-butoxycarbonylamino)isoquinolin-7-yl)-3-(trifluoromethyl)-1H-pyrazole-5-carboxylic acid (253f) (0.481 g, 11% yield) as an yellow solid; $^1$H NMR (300 MHz, DMSO-d₆) δ 8.36 (t, J=2.8 Hz, 1H), 8.29 (d, J=3.5 Hz, 1H), 8.10 (dd, J=8.8, 4.3 Hz, 1H), 7.99 (dd, J=8.5, 2.1 Hz, 1H), 7.76-7.66 (m, 1H), 7.60 (s, 1H), 1.46 (d, J=1.7 Hz, 9H); MS (ES−) 421.2 (M−1), 843.2 (2M−1).

Step-4: Preparation di-tert-butyl 7-(5-(5-(-3-cyclopropyl-1-((R)-1,1-dimethylethylsulfinamido)-1-(pyridin-4-yl)propyl)-2-fluorophenylcarbamoyl)-3-(trifluoromethyl)-1H-pyrazol-1-yl)isoquinolin-1-ylcarbamate (253d)

Compound 253d was prepared from 1-(1-(bis(tert-butoxycarbonyl)amino)isoquinolin-7-yl)-3-(trifluoromethyl)-

1H-pyrazole-5-carboxylic acid (253c) (0.261 g, 0.500 mmol) and (R)—N-((−)-1-(3-amino-4-fluorophenyl)-3-cyclopropyl-1-(pyridin-4-yl)propyl)-2-methylpropane-2-sulfinamide (216b) (0.234 g, 0.599 mmol) according to the procedure reported in step-3 of scheme-208 for compound 208c gave after workup crude 253d was used as such in the next step; MS (ES⁺): MS (ES+) 916.6 (M+Na); MS (ES−) 892.6 (M−1).

Step-5: Preparation of (+)-N-(5-(1-amino-3-cyclopropyl-1-(pyridin-4-yl)propyl)-2-fluorophenyl)-1-(1-aminoisoquinolin-7-yl)-3-(trifluoromethyl)-1H-pyrazole-5-carboxamide (253e)

To a stirred solution of di-tert-butyl 7-(5-(5-(-3-cyclopropyl-1-((R)-1,1-dimethylethylsulfinamido)-1-(pyridin-4-yl)propyl)-2-fluorophenylcarbamoyl)-3-(trifluoromethyl)-1H-pyrazol-1-yl)isoquinolin-1-ylcarbamate (253d) (0.671 g, 0.751 mmol) in methanol (10 mL) was added 3M HCl (in MeOH, 3.75 mL) and heated at reflux for 1 h. The reaction mixture was cooled to room temperature and evaporated to dryness. The residue was dissolved in water (25 mL) washed with MTBE (2×50 mL), the aqueous layer was basified with 1N NaOH and extracted with ethyl acetate (2×50 mL). The ethyl acetate layers were combined dried over anhydrous MgSO₄, filtered, and evaporated to dryness. The residue obtained was purified by flash chromatography [silica gel 12 g (four separate columns), eluting with CMA80 in chloroform, 0-50%] to afford 253e (9 mg, 2% yield) free base as a light brown solid; ¹H NMR (300 MHz, DMSO-d₆) δ 10.50 (s, 1H, D₂O exchangeable), 8.50-8.34 (m, 3H), 7.88 (d, J=5.8 Hz, 1H), 7.78 (d, J=8.8 Hz, 1H), 7.73-7.62 (m, 2H), 7.55 (dd, J=7.4, 2.4 Hz, 1H), 7.39-7.32 (m, 2H), 7.28 (ddd, J=8.7, 4.8, 2.3 Hz, 1H), 7.16 (dd, J=10.1, 8.7 Hz, 1H), 7.03-6.90 (m, 3H, D₂O exchangeable, 2H), 2.32 (s, 2H), 2.19 (m, 2H), 1.02 (m, 2H), 0.61 (m, 1H), 0.39-0.19 (m, 2H), −0.11 (m, 2H); ¹H NMR (300 MHz, DMSO-d₆, D₂O) δ 8.38 (td, J=5.6, 5.1, 1.8 Hz, 3H), 7.90-7.75 (m, 2H), 7.71-7.59 (m, 2H), 7.49 (dd, J=7.2, 2.2 Hz, 1H), 7.37-7.30 (m, 2H), 7.25 (ddd, J=9.0, 4.8, 2.4 Hz, 1H), 7.14 (t, J=9.4 Hz, 1H), 7.00 (d, J=5.8 Hz, 1H), 2.26-2.07 (m, 2H), 0.97 (m, 2H), 0.57 (m, 1H), 0.41-0.14 (m, 2H), −0.15 (m, 2H); ¹⁹F NMR (282 MHz, DMSO-d₆) δ −60.71, −123.61; MS (ES+): MS (ES⁺): MS (ES+) 590.4 (M+1); (ES−) 588.4 (M−1).

Compound 253e was treated with methanolic 3N HCl which afforded on evaporation and lyopholization (+)-N-(5-(1-amino-3-cyclopropyl-1-(pyridin-4-yl)propyl)-2-fluorophenyl)-1-(1-aminoisoquinolin-7-yl)-3-(trifluoromethyl)-1H-pyrazole-5-carboxamide (253e) hydrochloride salt as a white solid; ¹H NMR (300 MHz, DMSO-d₆) δ 13.74 (s, 1H, D₂O exchangeable), 11.02 (s, 1H, D₂O exchangeable), 9.80 (s, 3H, D₂O exchangeable), 9.42 (s, 3H, D₂O exchangeable), 8.95 (s, 1H), 8.87 (m, 2H), 8.13 (d, J=1.8 Hz, 2H), 7.85 (d, J=7.0 Hz, 1H), 7.72 (m, 3H), 7.46 (d, J=7.8 Hz, 2H), 7.37 (d, J=7.0 Hz, 1H), 2.60 (m, 2H), 1.17 (m, 2H), 0.69 (m, 1H), 0.34 (m, 2H), −0.00 (m, 2H); ¹H NMR (300 MHz, DMSO/D2O-d₆) δ 8.91 (s, 1H), 8.87-8.80 (m, 2H), 8.15 (d, J=1.5 Hz, 2H), 7.89 (s, 1H), 7.82 (d, J=7.0 Hz, 1H), 7.66 (m, 3H), 7.49 (t, J=9.4 Hz, 1H), 7.41 (d, J=7.1 Hz, 1H), 7.35 (m, 1H), 2.56 (m, 2H), 1.14 (m, 2H), 0.73 (m, 1H), 0.38 (m, 2H), 0.12-−0.09 (m, 2H); ¹⁹F NMR (282 MHz, DMSO-d₆) δ −60.89, −119.82; Analysis calculated for C₃₁H₂₇F₄N₇O.3HCl.3.5H₂O: C, 48.86; H, 4.89; Cl, 13.96; N, 12.87; Found; C, 48.62; H, 4.90; Cl, 14.37; N, 12.97; Optical rotation: [α]_D=(+) 19.31 [0.29, MeOH].

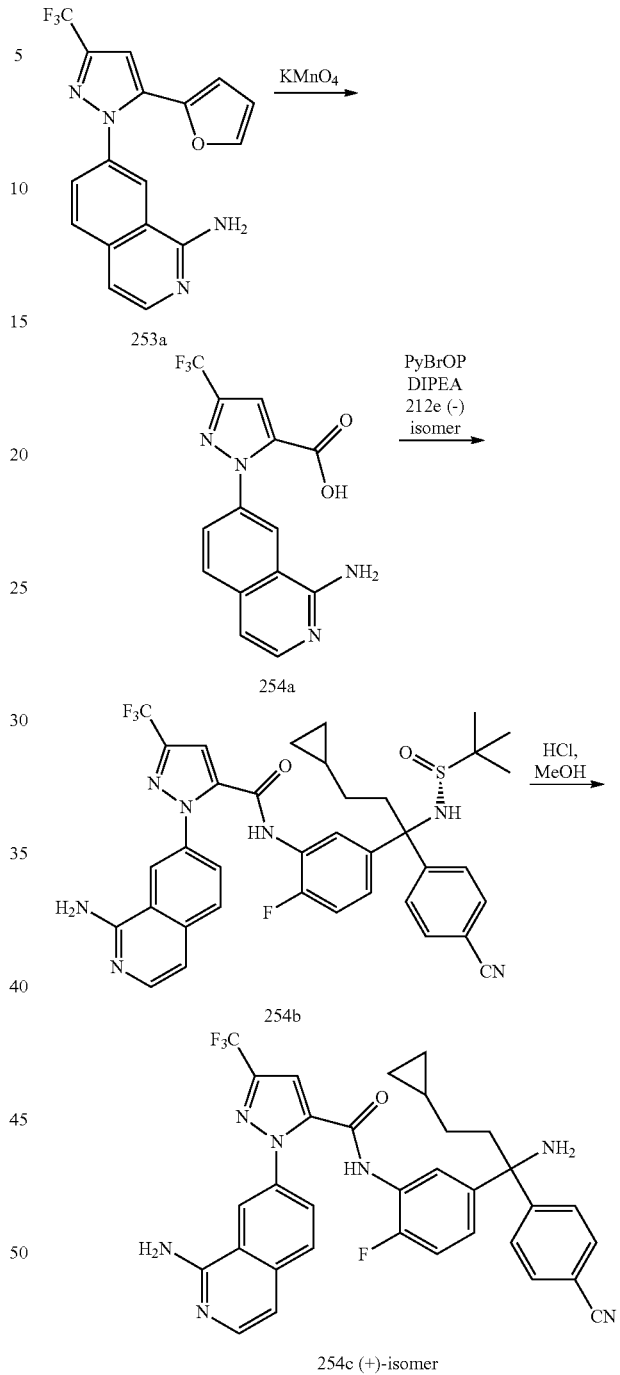

Scheme 254

Preparation of (+)-N-(5-(1-amino-1-(4-cyanophenyl)-3-cyclopropylpropyl)-2-fluorophenyl)-1-(1-aminoisoquinolin-7-yl)-3-(trifluoromethyl)-1H-pyrazole-5-carboxamide (254c)

Step-1: Preparation of 1-(1-aminoisoquinolin-7-yl)-3-(trifluoromethyl)-1H-pyrazole-5-carboxylic Acid (254a)

Compound 254a was prepared from 7-(5-(furan-2-yl)-3-(trifluoromethyl)-1H-pyrazol-1-yl)isoquinolin-1-amine (253a) (0.275 g, 0.799 mmol) according to the procedure reported in step-2 of scheme-10 for preparation of compound 9i gave 1-(1-aminoisoquinolin-7-yl)-3-(trifluoromethyl)-1H-pyrazole-5-carboxylic acid (254a) (0.077 g, 0.239 mmol, 29.9% yield) as a white solid; MS (ES+) 323.2 (M+1), 321.1 (M−1).

Step-2: Preparation of 1-(1-aminoisoquinolin-7-yl)-N-(5-(1-(4-cyanophenyl)-3-cyclopropyl-1-((R)-1,1-dimethylethylsulfinamido)propyl)-2-fluorophenyl)-3-(trifluoromethyl)-1H-pyrazole-5-carboxamide (254b)

Compound 254b was prepared from 1-(1-aminoisoquinolin-7-yl)-3-(trifluoromethyl)-1H-pyrazole-5-carboxylic acid (254a) [322 mg, 0.999 mmol, which was converted to HCl salt using HCl (3N in MeOH, 3 mL) and concentrating in vacuum to dryness prior to use] and (R)—N-((−)-1-(3-amino-4-fluorophenyl)-1-(4-cyanophenyl)-3-cyclopropylpropyl)-2-methylpropane-2-sulfinamide (212e) (248 mg, 0.600 mmol) according to the procedure reported in scheme-237 for preparation of compound 237a gave after workup crude 254b which was used as such for next step.

Step-3: Preparation of (+)-N-(5-(1-amino-1-(4-cyanophenyl)-3-cyclopropylpropyl)-2-fluorophenyl)-1-(1-aminoisoquinolin-7-yl)-3-(trifluoromethyl)-1H-pyrazole-5-carboxamide (254c)

A solution of above crude containing 1-(1-aminoisoquinolin-7-yl)-N-(5-(1-(4-cyanophenyl)-3-cyclopropyl-1-((R)-1,1-dimethylethylsulfinamido)propyl)-2-fluorophenyl)-3-(trifluoromethyl)-1H-pyrazole-5-carboxamide (254b) in dioxane (5 mL) was added HCl (4N in dioxane, 2 mL) and heated to reflux for 15 min. The solution was concentrated in vacuum and the residue was taken in water washed with EtOAc (50 mL) to remove organic impurities. The aqueous layer was basified with NaOH (1N) and extracted with EtOAc (2×50 mL). The organic layer were combined, dried, filtered and concentrated in vacuum. The residue obtained was purified by flash column chromatography (silica gel 40 g, eluting with 0-40% CMA-80 in chloroform) to furnish (+)-N-(5-(1-amino-1-(4-cyanophenyl)-3-cyclopropylpropyl)-2-fluorophenyl)-1-(1-aminoisoquinolin-7-yl)-3-(trifluoromethyl)-1H-pyrazole-5-carboxamide (254c) (17 mg, 0.028 mmol, 2.77% yield) free base as a white solid; $^1$H NMR (300 MHz, DMSO-d$_6$) δ 10.53 (s, 1H), 8.45-8.38 (m, 1H), 7.88 (d, J=5.8 Hz, 1H), 7.81-7.69 (m, 4H), 7.66 (dd, J=8.7, 2.0 Hz, 1H), 7.59-7.48 (m, 3H), 7.30-7.13 (m, 2H), 7.03-6.93 (m, 3H), 2.31-2.17 (m, 2H), 1.13-0.79 (m, 2H), 0.74-0.51 (m, 1H), 0.42-0.23 (m, 2H), −0.01−−0.24 (m, 2H); $^{19}$F NMR (282 MHz, DMSO-d$_6$) δ −60.74, −123.59; IR (KBr) 2230 cm$^{-1}$; Optical rotation: [α]$_D$=(+) 11.61 (0.155, methanol).

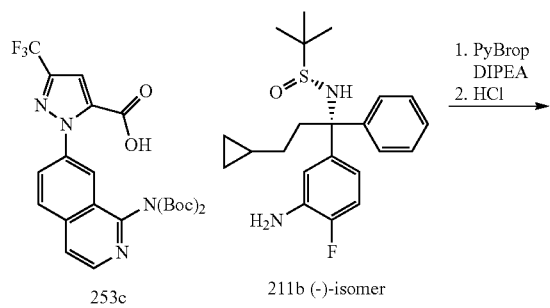

253c     211b (−)-isomer

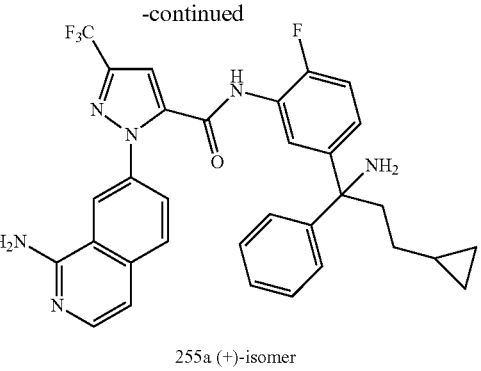

255a (+)-isomer

Preparation of (+)-N-(5-(1-amino-3-cyclopropyl-1-phenylpropyl)-2-fluorophenyl)-1-(1-aminoisoquinolin-7-yl)-3-(trifluoromethyl)-1H-pyrazole-5-carboxamide (255a)

To a solution of 1-(1-(bis(tert-butoxycarbonyl)amino)isoquinolin-7-yl)-3-(trifluoromethyl)-1H-pyrazole-5-carboxylic acid (253c) (60 mg, 0.115 mmol) in DMF (5 mL) was added (R)—N-((−)-1-(3-amino-4-fluorophenyl)-3-cyclopropyl-1-phenylpropyl)-2-methylpropane-2-sulfinamide (211b) (53.5 mg, 0.138 mmol), N-ethyl-N-isopropylpropan-2-amine (30.1 1, 0.172 mmol) and bromo-tris-pyrrolidino phosphoniumhexafluorophosphate(PyBrop, 64.2 mg, 0.138 mmol) at room temperature. The reaction mixture was stirred at room temperature for 12 h and diluted with ethyl acetate (100 mL) washed with water (2×50 mL). brine (50 mL), dried, filtered, and concentrated in vacuum to dryness to furnish crude residue. The residue was dissolved in anhydrous dioxane (5 mL), added HCl (4N in dioxane, 2 mL) and heated at 60° C. for 50 min. The reaction mixture was cooled to room temperature and concentrated in vacuum to dryness. The residue was dissolved in water washed EtOAc (50 mL). The aqueous layer was basified with NaOH (1N) and extracted with EtOAc (2×50 mL). The organic layer were combined, dried, filtered and concentrated in vacuum. The residue obtained was purified by flash column chromatography (silica gel 40 g, eluting with 0-40% CMA-80 in chloroform) to furnish compound 255a as a free base, which was converted in to the HCl salt to furnish (+)-N-(5-(1-amino-3-cyclopropyl-1-phenylpropyl)-2-fluorophenyl)-1-(1-aminoisoquinolin-7-yl)-3-(trifluoromethyl)-1H-pyrazole-5-carboxamide (255a) (22 mg, 0.037 mmol, 32.5% yield) hydrochloride salt as a white solid; $^1$H NMR (300 MHz, DMSO-d$_6$) δ 10.84 (s, 1H), 9.22 (s, 4H), 8.86 (s, 1H), 8.07 (s, 2H), 7.87 (s, 1H), 7.80 (d, J 20=7.0 Hz, 1H), 7.53 (dd, J=7.0, 2.0 Hz, 2H), 7.49-7.22 (m, 8H), 2.44 (d, J=8.3 Hz, 2H), 1.17-1.00 (m, 2H), 0.72-0.53 (m, 1H), 0.38-0.23 (m, 2H), −0.03−−0.09 (m, 2H); $^{19}$F NMR (282 MHz, DMSO) δ −60.70, −120.69; MS (ES$^+$): MS (ES+) 589.4 (M+1); 587.4 (M−1); Optical rotation: [α]$_D$=(+) 8.42 (0.285, methanol); Analysis calculated for: $C_{32}H_{28}F_4N_6O.2HCl.3H_2O$; C, 53.71; H, 5.07; N, 11.74; Found: C, 53.63; H, 4.98; N, 11.65.

Scheme 256

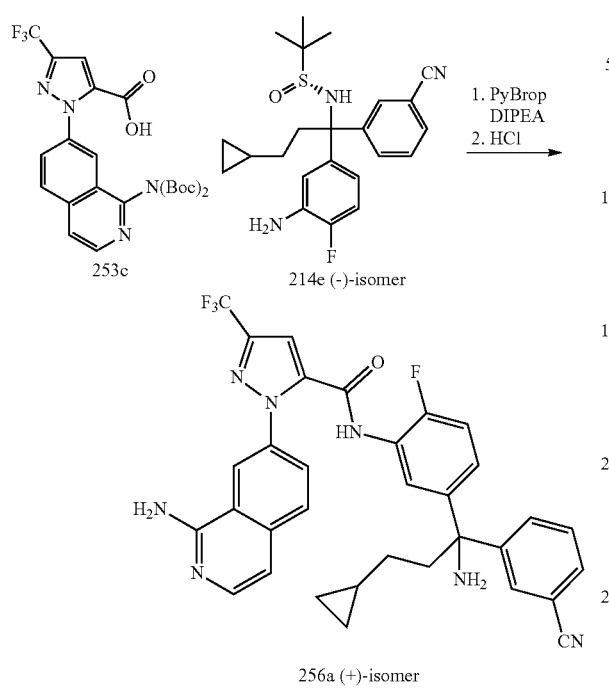

Preparation of (+)-N-(5-(1-amino-1-(3-cyanophenyl)-3-cyclopropylpropyl)-2-fluorophenyl)-1-(1-aminoisoquinolin-7-yl)-3-(trifluoromethyl)-1H-pyrazole-5-carboxamide (256a)

To a solution of 1-(1-(bis(tert-butoxycarbonyl)amino)isoquinolin-7-yl)-3-(trifluoromethyl)-1H-pyrazole-5-carboxylic acid (253c) (40 mg, 0.077 mmol) in DMF (5 mL) was added (R)—N-((−)-1-(3-amino-4-fluorophenyl)-1-(3-cyanophenyl)-3-cyclopropylpropyl)-2-methylpropane-2-sulfinamide (214e) (31.7 mg, 0.077 mmol), N-ethyl-N-isopropylpropan-2-amine (13.37 l, 0.077 mmol) and bromo-tri s-pyrrolidinophosphonium hexafluorophosphate (PyBrop, 35.7 mg, 0.077 mmol) at room temperature. The reaction mixture was stirred at room temperature for 12 h, diluted with ethyl acetate (100 mL), washed with water (2×50 mL), brine (50 mL), dried, filtered, and concentrated in vacuum to dryness to furnish crude residue. The residue was dissolved in anhydrous dioxane (5 mL) added HCl (4N in dioxane, 2 mL) and heated at 60° C. for 50 min. The reaction mixture was cooled to room temperature and concentrated in vacuum to dryness. The residue obtained was purified by flash column chromatography (silica gel 40 g, eluting with 0-40% CMA-80 in chloroform) to furnish compound 256a as a free base, which was converted in to the HCl salt to furnish (+)-N-(5-(1-amino-1-(3-cyanophenyl)-3-cyclopropylpropyl)-2-fluorophenyl)-1-(1-aminoisoquinolin-7-yl)-3-(trifluoromethyl)-1H-pyrazole-5-carboxamide (256a) (7 mg, 0.011 mmol, 14.90% yield) hydrochloride as a white solid; $^1$H NMR (300 MHz, DMSO-$d_6$) δ 13.37 (s, 1H), 10.81 (s, 1H), 9.36 (s, 3H), 9.16 (s, 3H), 8.83 (d, J=1.5 Hz, 1H), 8.07 (d, J=1.2 Hz, 2H), 7.92-7.81 (m, 3H), 7.79 (d, J=6.9 Hz, 1H), 7.66-7.63 (m, 2H), 7.56-7.51 (m, 1H), 7.42 (dd, J=10.0, 8.7 Hz, 1H), 7.31 (dd, J=7.4, 4.0 Hz, 2H), 2.61-2.38 (m, 2H), 1.07 (m, 2H), 0.65 (m, 1H), 0.31 (m, 2H), −0.06 (m, 2H); $^{19}$F NMR (282 MHz, DMSO) δ −60.69, −120.30; MS (ES$^+$): MS (ES+) 614.4 (M+1); 612.4 (M−1); Optical rotation: $[α]_D$= (+) 15.38 (0.13, methanol).

Scheme 257

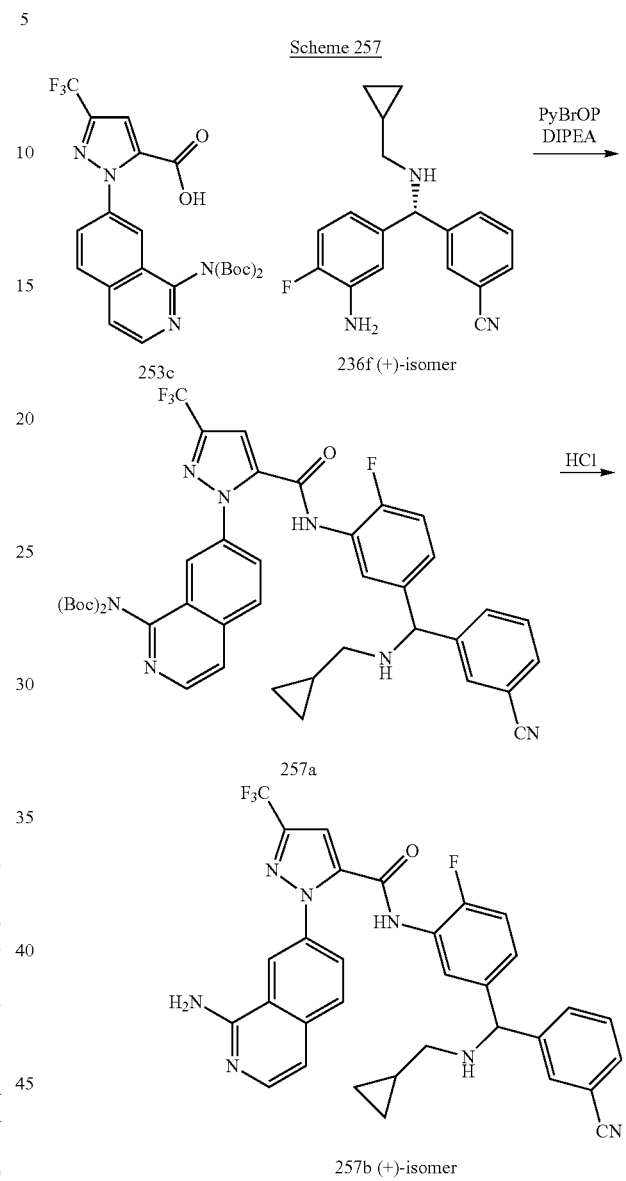

Preparation of (+)-1-(1-aminoisoquinolin-7-yl)-N-(5-(((3-cyanophenyl)(cyclopropylmethylamino)methyl)-2-fluorophenyl)-3-(trifluoromethyl)-1H-pyrazole-5-carboxamide (257b)

Step-1: Preparation of di-tert-butyl (7-(5-(((5-((3-cyanophenyl)((cyclopropylmethyl)amino)methyl)-2-fluorophenyl)carbamoyl)-3-(trifluoromethyl)-1H-pyrazol-1-yl)isoquinolin-1-yl)carbamate (257a)

Compound 257a was prepared from 1-(1-(bis(tert-butoxycarbonyl)amino)isoquinolin-7-yl)-3-(trifluoromethyl)-1H-pyrazole-5-carboxylic acid (253c) (0.839 g, 1.60 mmol) and (+)-3-((3-amino-4-fluorophenyl)(cyclopropylmethylamino)methyl)benzonitrile (236f) (0.569 g, 1.927 mmol) according to the procedure reported in step-3 of scheme-208 for compound 208c gave after workup crude 257a which was used as such in the next step; MS (ES+) 800.4 (M+1), 822.4 (M+Na); MS (ES−) 798.4 (M−1).

Step-2: Preparation of (+)-1-(1-aminoisoquinolin-7-yl)-N-(5-((3-cyanophenyl)(cyclopropyl methylamino)methyl)-2-fluorophenyl)-3-(trifluoromethyl)-1H-pyrazole-5-carboxamide (257b)

To a stirred solution of di-tert-butyl (7-(5-((5-((3-cyanophenyl)((cyclopropylmethyl) amino)methyl)-2-fluorophenyl)carbamoyl)-3-(trifluoromethyl)-1H-pyrazol-1-yl)isoquinolin-1-yl)carbamate (257a)(2.58 g, 3.23 mmol) in dioxane (30 mL) was added 4M HCl (dioxane) (4.84 mL, 19.35 mmol) and heated at reflux for 1 h. The reaction was cooled to room temperature and evaporated to dryness. The residue was dissolved in water (10 mL) washed with MTBE (2×50 mL), the aqueous layer was basified with 1N NaOH and extracted with ethyl acetate (2×50 mL). The ethyl acetate layers were combined dried over anhydrous MgSO$_4$, filtered, and evaporated to dryness. The residue was purified by flash chromatography [first column; silica gel 24 g, eluting with ethyl acetate/methanol (9:1) in hexanes 0-100%, second column; silica gel 12 g, eluting with ethyl CMA80 in chloroform 0-100%, third column; silica gel 12 g, eluting with CMA80 in chloroform from 0-40%] to afford Compound 257b (0.10 g, 0.167 mmol, 5.17% yield) free base as a white solid; $^1$H NMR (300 MHz, DMSO-d$_6$) δ 10.52 (s, 1H, D$_2$O exchangeable), 8.42 (d, J=2.0 Hz, 1H), 7.93-7.87 (m, 2H), 7.79 (d, J=8.7 Hz, 1H), 7.75-7.63 (m, 4H), 7.59 (dd, J=7.5, 2.2 Hz, 1H), 7.49 (t, J=7.7 Hz, 1H), 7.34 (m, 1H), 7.21 (dd, J=10.3, 8.6 Hz, 1H), 6.98 (m, 3H, D$_2$O exchangeable, 2H), 4.91 (s, 1H), 2.69 (bs, 1H), 2.24 (m, 2H), 0.88 (m, 1H), 0.52-0.23 (m, 2H), 0.09--0.06 (m, 2H); $^1$H NMR (300 MHz, DMSO-d$_6$ D$_2$O) δ 8.41 (d, J=2.0 Hz, 1H), 7.92-7.80 (m, 3H), 7.69 (m, 4H), 7.62-7.56 (m, 1H), 7.51 (t, J=7.7 Hz, 1H), 7.35 (ddd, J=8.6, 4.8, 2.2 Hz, 1H), 7.21 (dd, J=10.2, 8.6 Hz, 1H), 7.10-7.00 (m, 1H), 4.92 (s, 1H), 2.24 (m, 2H), 0.89 (m, 1H), 0.49-0.27 (m, 2H), 0.05--0.02 (m, 2H); $^{19}$F NMR (282 MHz, DMSO-d$_6$) δ −60.73, −122.79; MS (ES$^+$): MS (ES+) 600.3 (M+1); MS (ES−) 598.3 (M−1).

To a stirred solution of free base of 257b (0.093 g, 0.155 mmol) in methanol (10 mL) was added HCl (3M in methanol) (0.517 mL, 1.551 mmol), stirred at room temperature for 1 h, evaporated to dryness, triturated with MTBE (50 mL), filtered, rinsed with MTBE, and dried. The residue was dissolved in water, filtered, lyophilized to dryness afford (+)-1-(1-aminoisoquinolin-7-yl)-N-(5-((3-cyanophenyl)(cyclopropylmethylamino)methyl)-2-fluorophenyl)-3-(trifluoromethyl)-1H-pyrazole-5-carboxamide (257b) (0.070 g, 0.117 mmol, 75% yield) hydrochloride salt as a white solid; $^1$H NMR (300 MHz, DMSO-d$_6$) δ 10.84 (s, 1H, D$_2$O exchangeable), 10.24 (s, 2H, D$_2$O exchangeable), 9.09 (s, 2H, D$_2$O exchangeable), 8.83 (s, 1H), 8.22 (s, 1H), 8.07 (s, 2H), 8.01 (d, J=7.9 Hz, 1H), 7.92 (dd, J=7.2, 2.3 Hz, 1H), 7.89-7.84 (m, 2H), 7.80 (d, J=6.9 Hz, 1H), 7.67 (q, J=7.4 Hz, 2H), 7.42 (dd, J=10.2, 8.6 Hz, 1H), 7.30 (d, J=6.9 Hz, 1H), 5.74 (s, 1H), 2.70 (m, 2H), 1.13 (d, J=11.9 Hz, 1H), 0.63-0.47 (m, 2H), 0.29 (h, J=4.1 Hz, 2H); $^1$H NMR (300 MHz, DMSO-d$_6$ D$_2$O) δ 8.81 (d, J=1.3 Hz, 1H), 8.13 (t, J=1.7 Hz, 1H), 8.07 (d, J=1.4 Hz, 2H), 7.98-7.82 (m, 4H), 7.78 (d, J=6.9 Hz, 1H), 7.72-7.57 (m, 2H), 7.50-7.39 (m, 1H), 7.31 (d, J=6.9 Hz, 1H), 5.73 (s, 1H), 2.72 (m, 2H), 1.08 (m, 1H), 0.63-0.48 (m, 2H), 0.28 (m, 2H); $^{19}$F NMR (282 MHz, DMSO-d$_6$) δ −60.88, −119.84; MS (ES+): MS (ES+) 600.3 (M+1); MS (ES−) 598.3 (M−1), 634.2 (M+Cl); Optical rotation: (+) 0.73 [0.275, MeOH]; Analysis: calculated for C$_{32}$H$_{25}$F$_4$N$_7$O.2HCl.2H$_2$O: C, 54.24; H, 4.41; Cl, 10.01; N, 13.84; Found: C, 54.37; H, 4.45; Cl, 9.79; N, 13.87.

Scheme 258

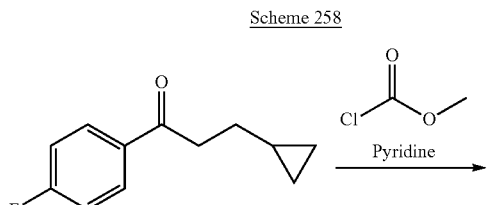

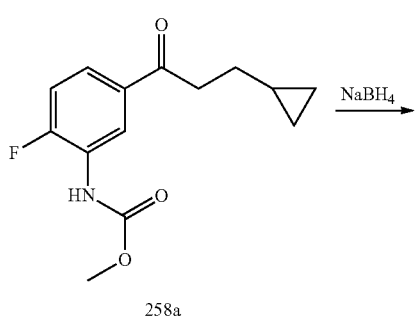

258a

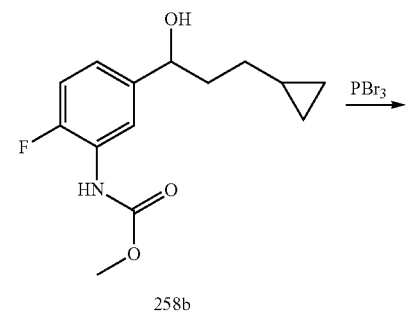

258b

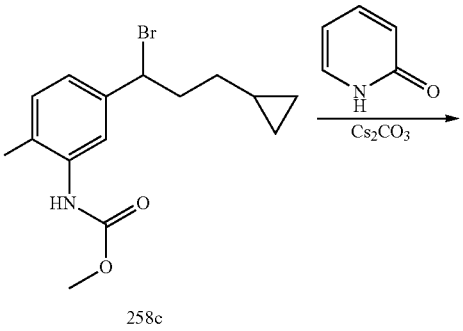

258c

905

-continued

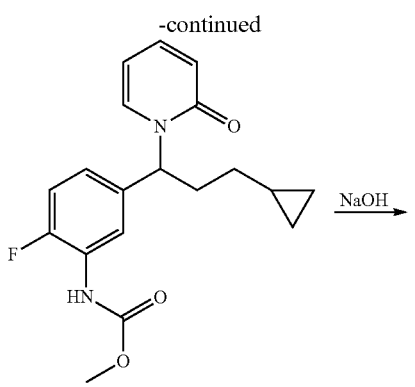

258d

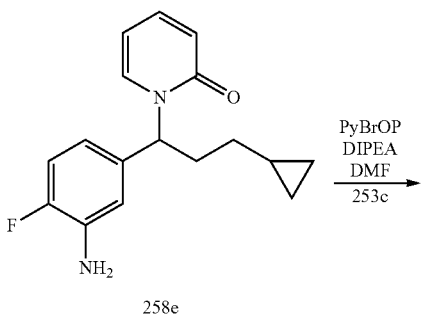

258e

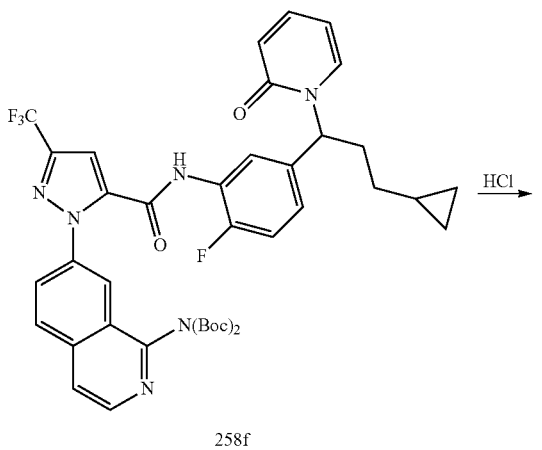

258f

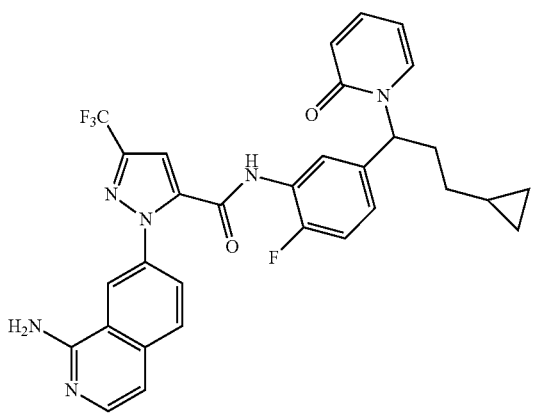

258g

906

Preparation of 1-(1-aminoisoquinolin-7-yl)-N-(5-(3-cyclopropyl-1-(2-oxopyridin-1(2H)-yl)propyl)-2-fluorophenyl)-3-(trifluoromethyl)-1H-pyrazole-5-carboxamide (258g)

Step-1: Preparation of methyl 5-(3-cyclopropylpropanoyl)-2-fluorophenylcarbamate (258a)

To a solution of 1-(3-amino-4-fluorophenyl)-3-cyclopropylpropan-1-one (248e) (0.207 g, 1.000 mmol) in dichloromethane (4 mL) at 0° C. was added pyridine (0.121 mL, 1.5 mmol) and methyl chloroformate (0.077 mL, 1 mmol). The reaction was slowly warmed to room temperature overnight and evaporated to dryness. The residue was treated with water (25 mL) and extracted with ethyl acetate (2×50 mL), combined organics were dried over anhydrous MgSO$_4$, filtered, evaporated to dryness to afford methyl 5-(3-cyclopropylpropanoyl)-2-fluorophenylcarbamate (258a) (0.254 g, 96% yield) as a clear oil; $^1$H NMR (300 MHz, DMSO-d$_6$) δ 9.59 (s, 1H, D$_2$O exchangeable), 8.30 (dd, J=7.9, 2.2 Hz, 1H), 7.85-7.72 (m, 1H), 7.37 (dd, J=10.6, 8.6 Hz, 1H), 3.69 (s, 3H), 3.06 (t, J=7.3 Hz, 2H), 1.51 (q, J=7.2 Hz, 2H), 0.85-0.65 (m, 1H), 0.47-0.33 (m, 2H), 0.12-0.02 (m, 2H); $^{19}$F NMR (282 MHz, DMSO-d$_6$) δ −117.74; MS (ES+): 266.1 (M+1); MS (ES−) 264.2 (M−1).

Step-2: Preparation of methyl 5-(3-cyclopropyl-1-hydroxypropyl)-2-fluorophenylcarbamate (258b)

Compound 258b was prepared from methyl 5-(3-cyclopropylpropanoyl)-2-fluorophenylcarbamate (258a) (2.51 g, 9.46 mmol) according to the procedure reported in step-5 of scheme-248 for preparation of compound 248f gave after purification by flash column chromatography [silica gel 40 g, eluting with ethyl acetate in hexanes from 0-50%] methyl 5-(3-cyclopropyl-1-hydroxypropyl)-2-fluorophenylcarbamate (258b) (2.387 g, 94% yield) as a colorless oil; $^1$H NMR (300 MHz, DMSO-d$_6$) δ 9.32 (s, 1H, D$_2$O exchangeable), 7.70-7.51 (m, 1H), 7.18 (dd, J=10.6, 8.4 Hz, 1H), 7.09 (ddd, J=8.4, 4.9, 2.1 Hz, 1H), 5.21 (d, J=4.4 Hz, 1H, D$_2$O exchangeable), 4.60-4.43 (m, 1H), 3.69 (s, 3H), 1.68 (m, 2H), 1.21 (m, 2H), 0.79-0.57 (m, 1H), 0.39 (m, 2H), 0.11--0.09 (m, 2H); $^{19}$F NMR (282 MHz, DMSO-d$_6$) δ −127.49; MS (ES+): 290.2 (M+Na); MS (ES−) 266.2 (M−1).

Step-3: Preparation of methyl 5-(1-bromo-3-cyclopropylpropyl)-2-fluorophenylcarbamate (258c)

Compound 258c was prepared from methyl 5-(3-cyclopropyl-1-hydroxypropyl)-2-fluorophenylcarbamate (258b) (2.303 g, 8.62 mmol) according to the procedure reported in step-2 of scheme-251 for preparation of compound 251b gave after purification by flash column chromatography [silica gel 40 g, eluting with ethyl acetate in hexanes from 0-100%] methyl 5-(1-bromo-3-cyclopropylpropyl)-2-fluorophenylcarbamate (258c) (1.289 g, 3.90 mmol, 45.3% yield) as a colorless oil; $^1$H NMR (300 MHz, DMSO-d$_6$) δ 9.43 (s, 1H, D$_2$O exchangeable), 7.78 (dd, J=7.7, 2.0 Hz, 1H), 7.36-7.11 (m, 2H), 5.29 (dd, J=8.1, 6.9 Hz, 1H), 3.67 (s, 3H), 2.41-2.06 (m, 2H), 1.39-1.09 (m, 2H), 0.71 (m, 1H), 0.39 (m, 2H), 0.11--0.09 (m, 2H); $^{19}$F NMR (282 MHz, DMSO-d$_6$) δ −124.45; MS (ES−) 328.1 (M−2).

Step-4: Preparation of methyl 5-(3-cyclopropyl-1-(2-oxopyridin-1(2H)-yl)propyl)-2-fluorophenylcarbamate (258d)

To a solution of methyl 5-(1-bromo-3-cyclopropylpropyl)-2-fluorophenylcarbamate (258c) (1.21 g, 3.66 mmol) in DMF (10 mL) was added pyridin-2(1H)-one (0.418 g, 4.40 mmol) cesium carbonate (1.791 g, 5.50 mmol) and stirred at room temperature overnight. The reaction mixture was diluted with water (50 mL), extracted with ethyl acetate (2×75 mL), combined organics were dried over anhydrous MgSO$_4$, filtered and evaporated to dryness. The residue was purified by flash column chromatography [silica gel 24 g, eluting with ethyl acetate in hexanes from 0-50%] to furnish of methyl 5-(3-cyclopropyl-1-(2-oxopyridin-1(2H)-yl)propyl)-2-fluorophenylcarbamate (258d) (0.606 g, 48.0% yield) as a colorless oil; $^1$H NMR (300 MHz, DMSO-d$_6$) δ 9.37 (s, 1H, D$_2$O exchangeable), 7.76-7.58 (m, 2H), 7.36 (m, 1H), 7.28-7.09 (m, 2H), 6.44-6.34 (m, 1H), 6.23 (td, J=6.7, 1.5 Hz, 1H), 6.06 (t, J=8.0 Hz, 1H), 3.65 (s, 3H), 2.20 (m, 2H), 1.26-0.92 (m, 2H), 0.80-0.63 (m, 1H), 0.46-0.30 (m, 2H), −0.01--0.03 (m, 2H); $^{19}$F NMR (282 MHz, DMSO-d$_6$) δ −125.28; MS (ES+) 367.3 (M+Na); MS (ES−) 343.3 (M−1).

Step-5: Preparation of 1-(1-(3-amino-4-fluorophenyl)-3-cyclopropylpropyl)pyridin-2(1H)-one (258e)

To a solution of methyl 5-(3-cyclopropyl-1-(2-oxopyridin-1(2H)-yl)propyl)-2-fluorophenylcarbamate (258d) (0.558 g, 1.620 mmol) in methanol (7 mL) was added 2.5 M NaOH (6.48 mL, 16.20 mmol) and refluxed for 13 h. The reaction mixture was diluted with water and extracted with ethyl acetate (2×50 mL), combined organics were dried over anhydrous MgSO$_4$, filtered, evaporated to dryness. The residue was purified by flash column chromatography [silica gel 12 g, eluting with ethyl acetate in hexanes from 0-25%] to furnish of 1-(1-(3-amino-4-fluorophenyl)-3-cyclopropylpropyl)pyridin-2(1H)-one (258e) (0.409 g, 88% yield) as an yellow oil; $^1$H NMR (300 MHz, DMSO-d$_6$) δ 7.59 (ddd, J=6.9, 2.1, 0.7 Hz, 1H), 7.35 (ddd, J=8.8, 6.5, 2.0 Hz, 1H), 6.95 (dd, J=11.4, 8.3 Hz, 1H), 6.75 (dd, J=8.8, 2.2 Hz, 1H), 6.53 (ddd, J=8.4, 4.3, 2.3 Hz, 1H), 6.44-6.33 (m, 1H), 6.21 (td, J=6.7, 1.5 Hz, 1H), 5.99 (dd, J=9.0, 7.0 Hz, 1H), 5.20 (s, 2H), 2.14 (m, 2H), 1.14-1.07 (m, 1H), 1.05-0.92 (m, 1H), 0.70 (m, 1H), 0.47-0.30 (m, 2H), 0.00--0.10 (m, 2H); MS (ES+): 309.2 (M+Na), MS (ES−) 285.2 (M−1), 321.2 (M+Cl).

Step-6: Preparation of di-tert-butyl 7-(5-(5-(3-cyclopropyl-1-(2-oxopyridin-1(2H)-yl)propyl)-2-fluorophenylcarbamoyl)-3-(trifluoromethyl)-1H-pyrazol-1-yl)isoquinolin-1-ylcarbamate (258f)

Compound 258f was prepared from 1-(1-(bis(tert-butoxycarbonyl)amino)isoquinolin-7-yl)-3-(trifluoromethyl)-1H-pyrazole-5-carboxylic acid (253c) (281 mg, 0.538 mmol) and 1-(1-(3-amino-4-fluorophenyl)-3-cyclopropylpropyl)pyridin-2(1H)-one (258e) (0.154 g, 0.538 mmol) according to the procedure reported in step-3 of scheme-208 for compound 208c gave after workup crude di-tert-butyl 7-(5-(5-(3-cyclopropyl-1-(2-oxopyridin-1(2H)-yl)propyl)-2-fluorophenylcarbamoyl)-3-(trifluoromethyl)-1H-pyrazol-1-yl)isoquinolin-1-ylcarbamate (258f) as a brown wax which was used as such in next step; MS (ES+): 813.5 (M+1).

Step-7: Preparation of 1-(1-aminoisoquinolin-7-yl)-N-(5-(3-cyclopropyl-1-(2-oxopyridin-1(2H)-yl)propyl)-2-fluorophenyl)-3-(trifluoromethyl)-1H-pyrazole-5-carboxamide (258g)

To a stirred solution of di-tert-butyl 7-(5-(5-(3-cyclopropyl-1-(2-oxopyridin-1(2H)-yl)propyl)-2-fluorophenylcarbamoyl)-3-(trifluoromethyl)-1H-pyrazol-1-yl)isoquinolin-1-ylcarbamate (258f) (0.801 g, 1.013 mmol) in methanol (10 mL) was added HCl (3M in methanol) (2.026 mL, 6.08 mmol) and heated at reflux for 1 h. The reaction was cooled to room temperature and evaporated to dryness. The residue was basified with aq. ammonium hydroxide and evaporated to dryness. The residue was purified by flash chromatography [silica gel 12 g, eluting with CMA80 in chloroform from 0-100%]. The sample was dissolved in minimum amount of methanol/1N HCl, and purified by "reverse phase" flash chromatography [C$_{18}$ column, eluting with water (0.1% TFA) in methanol from 0-100%]. The compound isolated was triturated with methanolic 3N HCl, and sonicated and evaporated to dryness. The residue was dissolved in minimum amount of acetonitrile and water, lyophilized to afford 1-(1-aminoisoquinolin-7-yl)-N-(5-(3-cyclopropyl-1-(2-oxopyridin-1(2H)-yl)propyl)-2-fluorophenyl)-3-(trifluoromethyl)-1H-pyrazole-5-carboxamide (258g) (10 mg, 2% yield) hydrochloride salt as a white solid; $^1$H NMR (300 MHz, DMSO-d$_6$) δ 13.38 (s, 1H, D$_2$O exchangeable), 10.71 (s, 1H, D$_2$O exchangeable), 9.20 (s, 3H, D$_2$O exchangeable), 8.84 (s, 1H), 8.09 (s, 2H), 7.85-7.75 (m, 2H), 7.70 (dd, J=7.0, 2.0 Hz, 1H), 7.54 (s, 1H), 7.34 (dd, J=8.9, 4.8 Hz, 3H), 6.39 (d, J=9.0 Hz, 1H), 6.23 (t, J=6.6 Hz, 1H), 6.04 (t, J=8.0 Hz, 1H), 2.20 (m, 2H), 1.05 (m, 2H), 0.76-0.62 (m, 1H), 0.42-0.31 (m, 2H), −0.05 (m, 2H); $^{19}$F NMR (282 MHz, DMSO-d$_6$) δ −60.70, −121.04; MS (ES+): 591.3 (M+1); MS (ES−) 625.3 (M+Cl); Analysis calculated for C$_{31}$H$_{26}$F$_4$N$_6$O$_2$.2HCl.2H$_2$O: C, 53.23; H, 4.61; N, 12.01; Found: C, 53.18; H, 4.56; N, 12.38.

Scheme 259

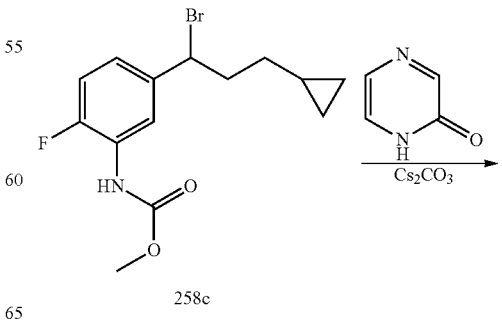

258c

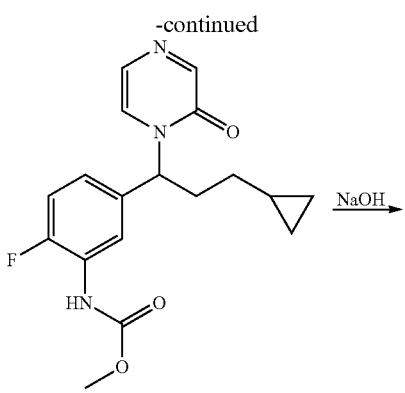

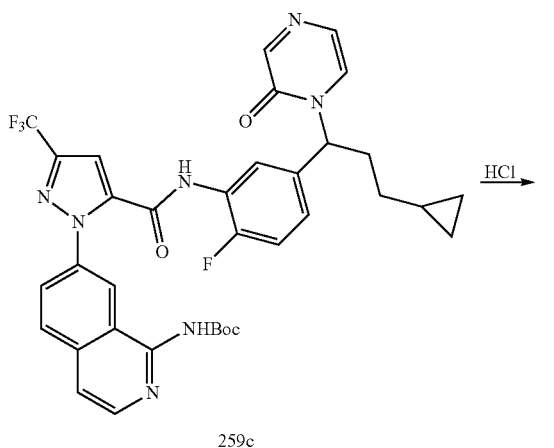

Preparation of 1-(1-aminoisoquinolin-7-yl)-N-(5-(3-cyclopropyl-1-(2-oxopyrazin-1(2H)-yl)propyl)-2-fluorophenyl)-3-(trifluoromethyl)-1H-pyrazole-5-carboxamide (259d)

Step-1: Preparation of methyl 5-(3-cyclopropyl-1-(2-oxopyrazin-1(2H)-yl)propyl)-2-fluorophenylcarbamate (259a)

To a solution of methyl 5-(1-bromo-3-cyclopropylpropyl)-2-fluorophenylcarbamate (258c) (0.925 g, 2.80 mmol) in DMF (10 mL) was added pyrazin-2(1H)-one (0.323 g, 3.36 mmol) cesium carbonate (0.867 g, 2.66 mmol) and stirred at room temperature overnight. The reaction mixture was diluted with water (50 mL), extracted with ethyl acetate (2×75 mL), combined organics were dried over anhydrous MgSO₄, filtered and evaporated to dryness. The residue was purified by flash column chromatography [silica gel 24 g, eluting with ethyl acetate/methanol (9:1) in hexanes from 0-75%] to furnish methyl 5-(3-cyclopropyl-1-(2-oxopyrazin-1(2H)-yl)propyl)-2-fluorophenylcarbamate (259a) (0.304 g, 31% yield) as a colorless wax. MS (ES+): 368.3 (M+Na), MS (ES−) 344.2 (M−1).

Step-2: Preparation of 1-(1-(3-amino-4-fluorophenyl)-3-cyclopropylpropyl)pyrazin-2(1H)-one (259b)

Compound 259b was prepared from methyl 5-(3-cyclopropyl-1-(2-oxopyrazin-1(2H)-yl)propyl)-2-fluorophenylcarbamate (259a) (301 mg, 0.872 mmol) according to the procedure reported in step-5 of scheme-258 for compound 258e to afford after purification by flash column chromatography [silica gel 12 g, eluting with ethyl acetate/methanol (9:1) in hexanes from 0-75%) 1-(1-(3-amino-4-fluorophenyl)-3-cyclopropylpropyl)pyrazin-2(1H)-one (259b) (61 mg, 24% yield) as a yellow solid; $^1$H NMR (300 MHz, DMSO-$d_6$) δ 8.02 (d, J=1.2 Hz, 1H), 7.65 (d, J=4.6 Hz, 1H), 7.33 (d, J=4.5 Hz, 1H), 6.97 (dd, J=11.4, 8.3 Hz, 1H), 6.76 (dd, J=8.8, 2.3 Hz, 1H), 6.57 (dt, J=7.3, 3.4 Hz, 1H), 5.81 (t, J=8.0 Hz, 1H), 5.22 (s, 2H, D₂O exchangeable), 2.18 (m, 2H), 1.08 (m, 2H), 0.69 (m, 1H), 0.43-0.29 (m, 2H), −0.02 (s, 2H); $^{19}$F NMR (282 MHz, DMSO-$d_6$) δ −135.69; MS (ES+): 310.2 (M+Na), MS (ES−) 286.3 (M−1), 322.2 (M+Cl).

Step-3: Preparation of tert-butyl 7-(5-(5-(3-cyclopropyl-1-(2-oxopyrazin-1(2H)-yl)propyl)-2-fluorophenylcarbamoyl)-3-(trifluoromethyl)-1H-pyrazol-1-yl)isoquinolin-1-ylcarbamate (259c)

Compound 259c was prepared from and 1-(1-(tert-butoxycarbonylamino)isoquinolin-7-yl)-3-(trifluoromethyl)-1H-pyrazole-5-carboxylic acid (253f) (0.102 g, 0.242 mmol) and 1-(1-(3-amino-4-fluorophenyl)-3-cyclopropylpropyl)pyrazin-2(1H)-one (259b) (58 mg) according to the procedure reported in step-3 of scheme-208 for compound 208c gave after workup crude tert-butyl 7-(5-(5-(3-cyclopropyl-1-(2-oxopyrazin-1(2H)-yl)propyl)-2-fluorophenylcarbamoyl)-3-(trifluoromethyl)-1H-pyrazol-1-yl)isoquinolin-1-ylcarbamate (259c) (359 mg) as a brown wax which was used as such in next step; MS (ES+) 692.2 (M+1).

Step-4: Preparation of 1-(1-aminoisoquinolin-7-yl)-N-(5-(3-cyclopropyl-1-(2-oxopyrazin-1(2H)-yl)propyl)-2-fluorophenyl)-3-(trifluoromethyl)-1H-pyrazole-5-carboxamide (259d)

To a solution of crude tert-butyl 7-(5-(5-(3-cyclopropyl-1-(2-oxopyrazin-1(2H)-yl)propyl)-2-fluorophenylcarbamoyl)-3-(trifluoromethyl)-1H-pyrazol-1-yl)isoquinolin-1-yl-carbamate (259c) (0.338 g, crude reaction mixture) in methanol (10 mL) was added 3 M methanolic HCl (0.977 mL, 2.93 mmol) and heated at reflux for 1.5 h. The reaction was cooled to room temperature and evaporated to dryness. The residue was basified with aq. ammonium hydroxide and evaporated to dryness. The residue was purified by flash chromatography [silica gel 12 g, eluting with CMA80 in chloroform from 0-100%] to afford compound 259d (12 mg, 4% yield) free base as a colorless solid.

$^1$H NMR (300 MHz, DMSO-$d_6$) δ 10.65 (s, 1H, D$_2$O exchangeable), 8.57-8.38 (m, 1H), 8.07 (d, J=1.1 Hz, 1H), 7.94 (d, J=5.7 Hz, 1H), 7.88-7.69 (m, 4H), 7.66-7.58 (m, 1H), 7.44-7.30 (m, 3H), 7.10-6.94 (m, 3H), 5.92 (dd, J=9.0, 6.9 Hz, 1H), 2.41-2.17 (m, 2H), 1.12 (m, 2H), 0.73 (m, 1H), 0.49-0.31 (m, 2H), 0.04--0.04 (m, 2H); $^{19}$F NMR (282 MHz, DMSO-$d_6$) δ −60.73, −120.86; MS (ES+) 592.3 (M+1), 614.2 (M+Na); MS (ES−) 590.3 (M−1), 626.3 (M+Cl).

Scheme 260

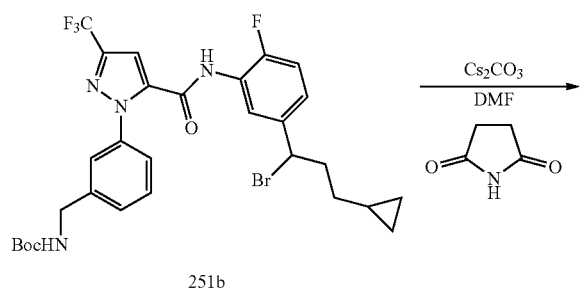

251b

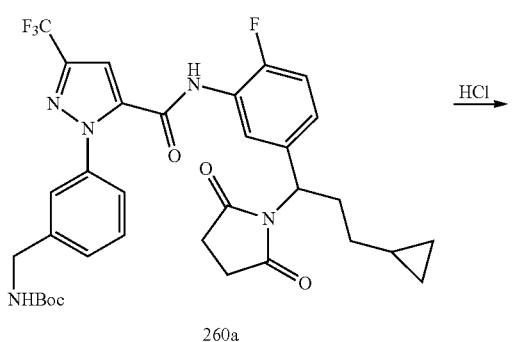

260a

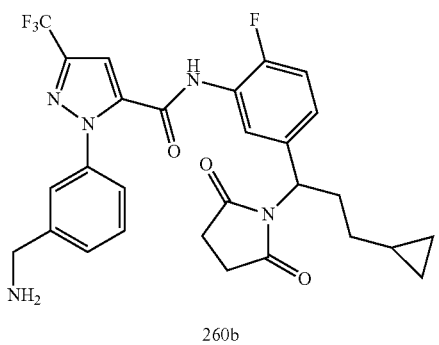

260b

Preparation of 1-(3-(aminomethyl)phenyl)-N-(5-(3-cyclopropyl-1-(2,5-dioxopyrrolidin-1-yl)propyl)-2-fluorophenyl)-3-(trifluoromethyl)-1H-pyrazole-5-carboxamide (260b)

Step-1: Preparation of tert-butyl 3-(5-(5-(3-cyclopropyl-1-(2,5-dioxopyrrolidin-1-yl)propyl)-2-fluorophenylcarbamoyl)-3-(trifluoromethyl)-1H-pyrazol-1-yl)benzylcarbamate (260a)

Compound 260a was prepared from tert-butyl 3-(5-(5-(1-bromo-3-cyclopropylpropyl)-2-fluorophenylcarbamoyl)-3-(trifluoromethyl)-1H-pyrazol-1-yl)benzylcarbamate (251b) (0.7 g, 1.09 mmol) and pyrrolidine-2,5-dione (0.217 g, 2.19 mmol) according to the procedure reported in step-4 of scheme-258 for preparation of compound 258d gave after purification by flash column chromatography (silica gel 40 g, eluting with ethyl acetate in hexanes from 0-50%) to tert-butyl 3-(5-(5-(3-cyclopropyl-1-(2,5-dioxopyrrolidin-1-yl)propyl)-2-fluorophenylcarbamoyl)-3-(trifluoromethyl)-1H-pyrazol-1-yl)benzylcarbamate (260a) (0.19 g, 0.29 mmol, 26.4% yield) as colorless foam; $^1$H NMR (300 MHz, DMSO-$d_6$) δ 10.60 (s, 1H), 7.59 (m, 2H), 7.53-7.14 (m, 7H), 5.07 (dd, J=9.5, 6.4 Hz, 1H), 4.20 (d, J=6.2 Hz, 2H), 2.70-2.57 (m, 4H), 2.47-2.31 (m, 1H), 2.16 (m, 1H), 1.37 (s, 11H), 0.66 (s, 1H), 0.37 (m, 2H), −0.01--0.12 (m, 2H); $^{19}$F NMR (282 MHz, DMSO) δ −60.85, −121.00; MS (ES+) 680.3 (M+Na).

Step-2: Preparation of 1-(3-(aminomethyl)phenyl)-N-(5-(3-cyclopropyl-1-(2,5-dioxopyrrolidin-1-yl)propyl)-2-fluorophenyl)-3-(trifluoromethyl)-1H-pyrazole-5-carboxamide (260b)

To a solution of tert-butyl 3-(5-(5-(3-cyclopropyl-1-(2,5-dioxopyrrolidin-1-yl)propyl)-2-fluorophenylcarbamoyl)-3-(trifluoromethyl)-1H-pyrazol-1-yl)benzylcarbamate (260a) (0.15 g, 0.23 mmol) in methanol (5 mL) was added hydrogen chloride in 3 M in methanol (0.76 mL, 2.28 mmol) and stirred at room temperature for 20 h. The solution was concentrated in vacuum and resultant residue was partitioned between NaHCO$_3$ solution (40 mL) and EtOAc (30 mL). Layers were separated; aqueous layer was extracted with EtOAc (25 mL). The combined organics were washed with brine, dried over MgSO$_4$, filtered and concentrated in vacuum. The residue was purified by flash chromatography (silica gel 12 g, eluting with 0-100% CMA80 in chloroform) to afford 1-(3-(aminomethyl)phenyl)-N-(5-(3-cyclopropyl-1-(2,5-dioxopyrrolidin-1-yl)propyl)-2-fluorophenyl)-3-(trifluoromethyl)-1H-pyrazole-5-carboxamide (260b) (0.105 g, 0.188 mmol, 83% yield) as colorless foam; $^1$H NMR (300 MHz, DMSO-$d_6$) δ 10.59 (s, 1H), 8.32 (s, 1H), 7.71-7.14 (m, 9H), 5.07 (dd, J=9.5, 6.4 Hz, 1H), 3.80 (s, 2H), 2.70-2.57 (m, 4H), 2.43 (m, 1H) 2.16 (m, 1H), 1.10 (m, 2H), 0.64 (m, 1H), 0.37 (m, 2H), −0.00 (m, 2H). $^{19}$F NMR (282 MHz, DMSO) δ −60.75, −122.08; MS (ES+) 558.3 (M+1).

Scheme 261
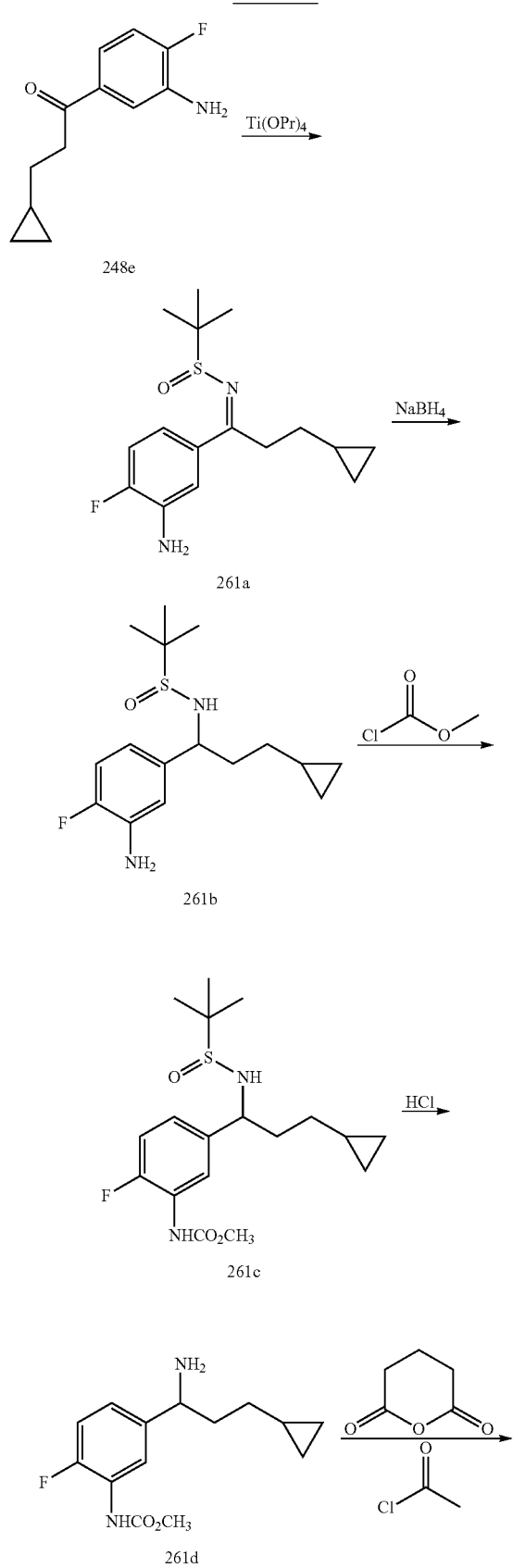
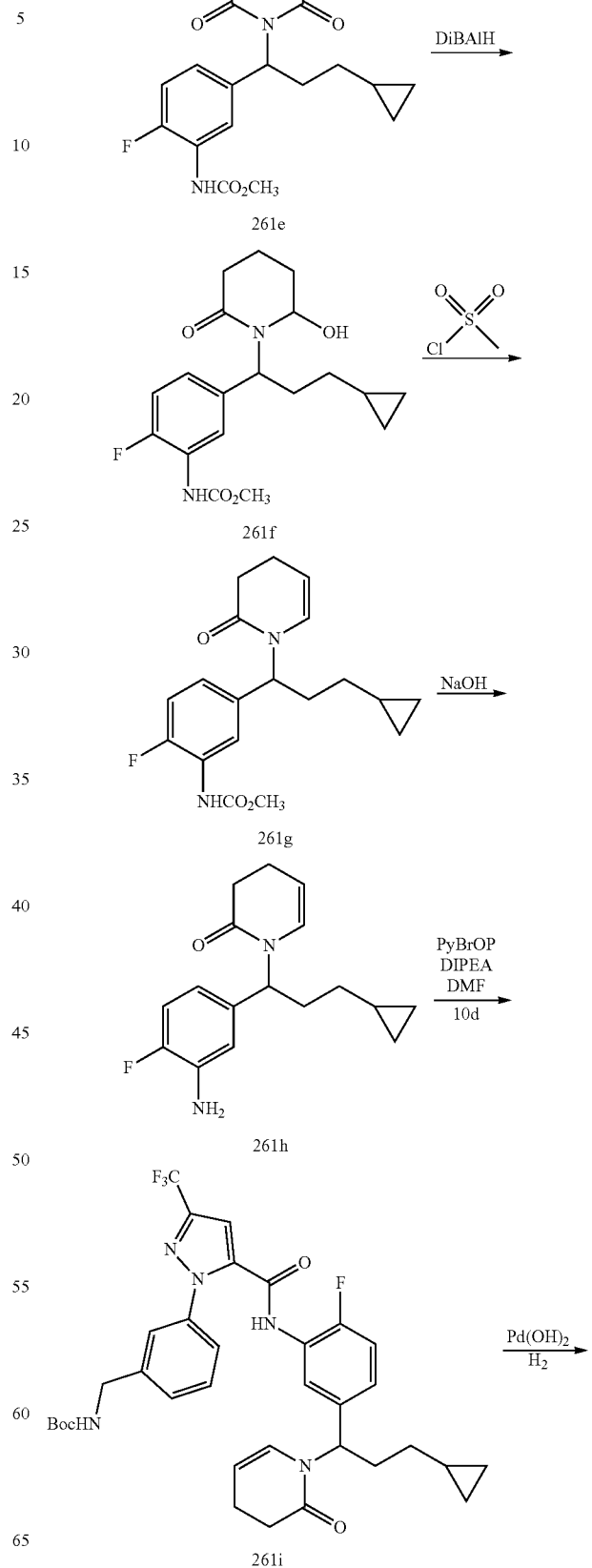

-continued

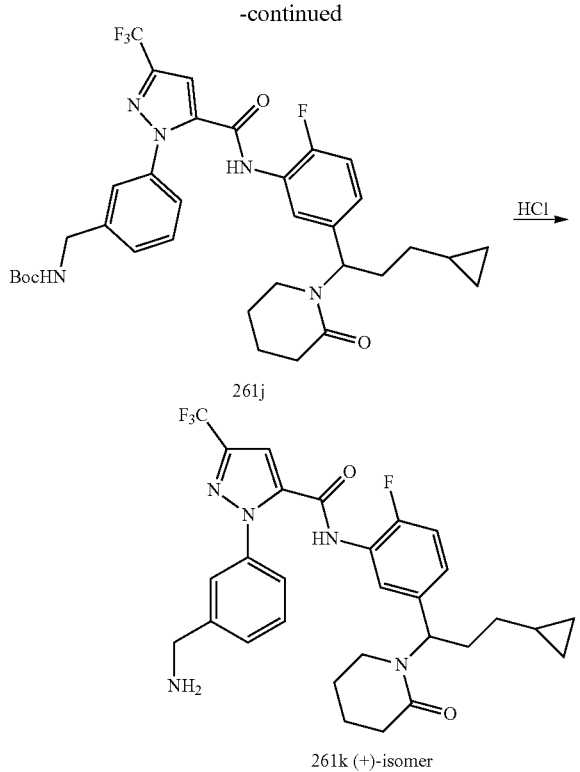

261j 261k (+)-isomer

Preparation of (+)-1-(3-(aminomethyl)phenyl)-N-(5-(3-cyclopropyl-1-(2-oxopiperidin-1-yl)propyl)-2-fluorophenyl)-3-(trifluoromethyl)-1H-pyrazole-5-carboxamide (261k)

Step-1: Preparation of N-(1-(3-amino-4-fluorophenyl)-3-cyclopropylpropylidene)-2-methylpropane-2-sulfinamide (261a)

Compound 261a was prepared from 1-(3-amino-4-fluorophenyl)-3-cyclopropylpropan-1-one (248e) (19.5 g, 94 mmol) and 2-methylpropane-2-sulfinamide (14.83 g, 122 mmol) according to the procedure reported in step-1 of scheme 208 for preparation of compound 208a (reaction time 62 h) to afford after purification by flash column chromatography [silica gel with hexanes/ethyl acetate (1:0 to 4:1, then 2:1, 1:1)] to give N-(1-(3-amino-4-fluorophenyl)-3-cyclopropylpropylidene)-2-methylpropane-2-sulfinamide (261a) (14.26 g, 48.9%) as a yellow gum; $^1$H NMR (300 MHz, DMSO-$d_6$) δ 7.33 (d, J=8.9 Hz, 1H), 7.10-7.03 (m, 2H), 5.39 (s, 2H), 3.32-3.04 (m, 2H), 1.54-1.36 (m, 2H), 1.21 (s, 9H), 0.82-0.66 (m, 1H), 0.53-0.27 (m, 2H), 0.15--0.05 (m, 2H); $^{19}$F NMR (282 MHz, DMSO-$d_6$) δ −129.99; MS (ES+): 333.2 (M+Na).

Step-2: Preparation of N-(1-(3-amino-4-fluorophenyl)-3-cyclopropylpropyl)-2-methylpropane-2-sulfinamide (261b)

Compound 261b was prepared from N-(1-(3-amino-4-fluorophenyl)-3-cyclopropylpropylidene)-2-methylpropane-2-sulfinamide (261a) (4 g, 12.89 mmol) according to the procedure reported in step-5 of scheme 248 for preparation of compound 248f (reaction temp −78° C.) to afford N-(1-(3-amino-4-fluorophenyl)-3-cyclopropylpropyl)-2-methylpropane-2-sulfinamide (261b) (4.15 g) as a light yellow gum which was used as such for next step.

Step-3: Preparation of methyl 5-(3-cyclopropyl-1-(1,1-dimethylethylsulfinamido)propyl)-2-fluorophenylcarbamate (261c)

To a biphasic solution of N-(1-(3-amino-4-fluorophenyl)-3-cyclopropylpropyl)-2-methylpropane-2-sulfinamide (261b) (4.5 g, 14.40 mmol) in ethyl acetate (100 mL) and saturated aqueous NaHCO$_3$ (100 mL) was added methyl chloroformate (1.673 mL, 21.60 mmol) and stirred at room temperature for 16 h. Aqueous layers was separated, extracted with ethyl acetate (2×150 mL) and combined organic layers were washed with brine, dried over MgSO$_4$, filtered, concentrated and purified by flash column chromatography to afford methyl 5-(3-cyclopropyl-1-(1,1-dimethylethylsulfinamido)propyl)-2-fluorophenylcarbamate (261c) (4.86 g, 13.12 mmol, 91% yield) as gummy solid; $^1$H NMR (300 MHz, DMSO-$d_6$) δ 9.30 (s, 1H), 7.69-7.52 (m, 1H), 7.25-6.98 (m, 2H), 5.60 (d, J=8.2 Hz, 1H), 4.12 (m, 1H), 3.66 (s, 3H), 1.97-1.79 (m, 1H), 1.68 (m, 1H), 1.08 (m, 11H), 0.63 (m, 1H), 0.42-0.26 (m, 2H), −0.01--0.12 (m, 2H); $^{19}$F NMR (282 MHz, DMSO-$d_6$) δ −127.03 (d, J=44.3 Hz).

Step-4: Preparation of methyl 5-(1-amino-3-cyclopropylpropyl)-2-fluorophenylcarbamate (261d)

To a stirred solution of methyl 5-(3-cyclopropyl-1-(1,1-dimethylethylsulfinamido)propyl)-2-fluorophenylcarbamate (261c) (4.85 g, 13.09 mmol) in methanol (100 mL) was added hydrochloric acid 4N solution in 1,4-dioxane (16.36 mL, 65.5 mmol) and stirred at room temperature for 30 minutes. The reaction was concentrated in vacuum, residue was dissolved in water (100 mL) basified with saturated sodium bicarbonate solution and extracted with ethyl acetate (3×100 mL). The combined organic layers were washed with water (2×50 mL), brine (50 mL), dried, filtered and concentrated in vacuum to afford methyl 5-(1-amino-3-cyclopropylpropyl)-2-fluorophenylcarbamate (261d) (3.57 g, 13.41 mmol, 102% yield) as a thick syrup which was used as such for next step; $^1$H NMR (300 MHz, DMSO-$d_6$) δ 9.25 (s, 1H), 7.75-7.39 (m, 1H), 7.30-6.85 (m, 2H), 3.65 (s, 3H), 3.37 (m, 1H), 2.04 (s, 2H), 1.59 (m, 2H), 1.27-1.13 (m, 1H), 1.08-0.91 (m, 1H), 0.73-0.51 (m, 1H), 0.41-0.24 (m, 2H), −0.06 (m, 2H); $^{19}$F NMR (282 MHz, DMSO-$d_6$) δ −127.68.

Step-5: Preparation of methyl 5-(3-cyclopropyl-1-(2,6-dioxopiperidin-1-yl)propyl)-2-fluorophenylcarbamate (261e)

To a stirred solution of methyl 5-(1-amino-3-cyclopropylpropyl)-2-fluorophenylcarbamate (261d) (3.2 g, 12.02 mmol) in dichloromethane (70 mL) was added dihydro-2H-pyran-2,6(3H)-dione (1.508 g, 13.22 mmol). The reaction was stirred at room temperature for 30 mins added acetyl chloride (17.09 mL, 240 mmol) and heated at reflux for 2 h. The reaction was concentrated in vacuum and purified by flash column chromatography (silica gel, 40 g, eluting with ethyl acetate in hexanes 0 to 100%) to afford methyl 5-(3-cyclopropyl-1-(2,6-dioxopiperidin-1-yl)propyl)-2-fluorophenylcarbamate (261e) (4.078 g, 11.25 mmol, 94% yield) as a colorless solid; $^1$H NMR (300 MHz, DMSO-$d_6$) δ 9.28 (s, 1H), 7.57 (d, J=7.7 Hz, 1H), 7.25-6.90 (m, 2H), 5.71 (dd, J=9.2, 6.5 Hz, 1H), 3.65 (s, 3H), 2.62 (m, 4H), 2.37-2.12 (m, 2H), 1.88-1.75 (m, 2H), 1.20-0.99 (m, 2H), 0.68 (m, 1H), 0.47-0.32 (m, 2H), 0.05-0.00 (m, 1H), −0.01--0.07 (m, 1H); $^{19}$F NMR (282 MHz, DMSO-d$_6$) δ −127.01.

Step-6: Preparation of methyl 5-(3-cyclopropyl-1-(2-hydroxy-6-oxopiperidin-1-yl)propyl)-2-fluorophenylcarbamate (261f)

To a stirred solution of methyl 5-(3-cyclopropyl-1-(2,6-dioxopiperidin-1-yl)propyl)-2-fluorophenylcarbamate (261e) (3.55 g, 9.80 mmol) in dichloromethane (200 mL) at −78° C. was added diisobutylaluminum hydride (29.4 mL, 29.4 mmol) and stirred at −78° C. for 1 h. Reaction was quenched with methanol (3 mL) and warmed to room temperature. Reaction was diluted with 2 N sodium hydroxide (4 mL) washed with saturated disodium tartarate solution. The layers were separated and aqueous layer was extracted with dichloromethane (2×150 mL). the organic layers were combined washed with brine (100 mL), dried, filtered and concentrated to afford methyl 5-(3-cyclopropyl-1-(2-hydroxy-6-oxopiperidin-1-yl)propyl)-2-fluorophenylcarbamate (261f) (3.204 g, 8.79 mmol, 90% yield) which was used as such for next step; $^1$H NMR (300 MHz, DMSO-d$_6$) δ 9.51-9.07 (m, 1H), 7.68-7.41 (m, 1H), 7.37-6.95 (m, 2H), 5.58 (dd, J=30.4, 6.5 Hz, 1H), 5.45 (m, 0.5H), 4.96 (m, 0.5H), 4.87 (m, 0.5H), 4.62 (m, 0.5H), 3.65 (2s, 3H), 2.35-1.99 (m, 4H), 1.81-1.59 (m, 2H), 1.59-1.36 (m, 2H), 1.27-1.06 (m, 2H), 0.70 (m, 1H), 0.45-0.25 (m, 2H), 0.05--0.18 (m, 2H); $^{19}$F NMR (282 MHz, DMSO-d$_6$) δ −126.93.

Step-7: Preparation of methyl 5-(3-cyclopropyl-1-(2-oxo-3,4-dihydropyridin-1(2H)-yl)propyl)-2-fluorophenylcarbamate (261g)

To a stirred solution of methyl 5-(3-cyclopropyl-1-(2-hydroxy-6-oxopiperidin-1-yl)propyl)-2-fluorophenylcarbamate (261f) (3.2 g, 8.78 mmol) in dichloromethane (100 mL) cooled to 0° C. was added triethylamine (7.34 mL, 52.7 mmol) and methanesulfonyl chloride (1.369 mL, 17.56 mmol). The reaction was allowed to warm to room temperature and stirred for 30 min. The reaction was diluted with dichloromethane (200 mL) and water (50 mL). The aqueous layer was separated and extracted with dichloromethane (2×50 mL). The organic layers were combined washed with water (2×25 mL), brine (25 mL), dried and concentrated. The crude residue was purified by flash column chromatography (silica gel, 40 g eluting with ethyl acetate in hexanes 0 to 50 to 100%) to afford methyl 5-(3-cyclopropyl-1-(2-oxo-3,4-dihydropyridin-1(2H)-yl)propyl)-2-fluorophenylcarbamate (261g) (2.35 g, 6.78 mmol, 77% yield) as a clear syrup; $^1$H NMR (300 MHz, DMSO-d$_6$) δ 9.35 (s, 1H), 7.58 (dd, J=8.0, 2.1 Hz, 1H), 7.18 (dd, J=10.6, 8.5 Hz, 1H), 7.06 (m, 1H), 6.15 (dt, J=7.9, 1.6 Hz, 1H), 5.64 (dd, J=9.9, 6.2 Hz, 1H), 5.17 (dt, J=8.4, 4.4 Hz, 1H), 3.66 (s, 3H), 2.43 (m, 2H), 2.20 (m, 2H), 2.08-1.80 (m, 2H), 1.25-1.00 (m, 2H), 0.71 (m, 1H), 0.45-0.31 (m, 2H), 0.05 (m, 1H), 0.00--0.08 (m, 1H); $^{19}$F NMR (282 MHz, DMSO-d$_6$) δ −126.28.

Step-8: Preparation of 1-(1-(3-amino-4-fluorophenyl)-3-cyclopropylpropyl)-3,4-dihydropyridin-2(1H)-one (261h)

Compound 261h was prepared from methyl 5-(3-cyclopropyl-1-(2-oxo-3,4-dihydropyridin-1(2H)-yl)propyl)-2-fluorophenylcarbamate (261g) (1.2 g, 3.46 mmol) according to the procedure reported in step-5 of scheme 248 for preparation of compound 258e to afford 1-(1-(3-amino-4-fluorophenyl)-3-cyclopropylpropyl)-3,4-dihydropyridin-2(1H)-one (261h) (0.89 g, 3.09 mmol, 89% yield) as a white solid.
$^1$H NMR (300 MHz, DMSO-d$_6$) δ 6.91 (dd, J=11.5, 8.4 Hz, 1H), 6.69 (dd, J=8.8, 2.3 Hz, 1H), 6.44 (m, 1H), 6.09 (dt, J=7.8, 1.6 Hz, 1H), 5.56 (dd, J=10.1, 5.9 Hz, 1H), 5.20-5.06 (m, 3H), 2.48-2.35 (m, 2H), 2.27-2.12 (m, 2H), 1.98-1.77 (m, 2H), 1.16-0.93 (m, 2H), 0.78-0.63 (m, 1H), 0.44-0.33 (m, 2H), 0.10--0.11 (m, 2H); $^{19}$F NMR (282 MHz, DMSO) δ −137.03.

Step-9: Preparation of tert-butyl 3-(5-(5-(3-cyclopropyl-1-(2-oxo-3,4-dihydropyridin-1(2H)-yl)propyl)-2-fluorophenylcarbamoyl)-3-(trifluoromethyl)-1H-pyrazol-1-yl)benzylcarbamate (261i)

Compound 261i was prepared from 1-(3-((tert-butoxycarbonylamino)methyl)phenyl)-3-(trifluoromethyl)-1H-pyrazole-5-carboxylic acid (10d) (0.53 g, 1.38 mmol) and 1-(1-(3-amino-4-fluorophenyl)-3-cyclopropylpropyl)-3,4-dihydropyridin-2(1H)-one (261h) (0.4 g, 1.39 mmol) according to the procedure reported in step-3 of scheme 208 for preparation of compound 208c to afford after purification by flash column chromatography (silica gel 40 g, eluting with ethyl acetate in hexanes from 0-40%) tert-butyl 3-(5-(5-(3-cyclopropyl-1-(2-oxo-3,4-dihydropyridin-1 (2H)-yl)propyl)-2-fluorophenylcarbamoyl)-3-(trifluoromethyl)-1H-pyrazol-1-yl)benzylcarbamate (261i) (0.48 g, 0.73 mmol, 52.8% yield) as colorless foam; $^1$H NMR (300 MHz, DMSO-d$_6$) δ 10.60 (s, 1H), 7.60 (s, 1H), 7.44 (ddd, J=26.7, 13.8, 5.9 Hz, 6H), 7.31-7.15 (m, 2H), 6.17 (d, J=7.9 Hz, 1H), 5.71-5.57 (m, 1H), 5.25-5.08 (m, 1H), 4.19 (d, J=6.2 Hz, 2H), 2.49-2.35 (m, 2H), 2.27-2.12 (m, 2H), 2.05-1.88 (m, 2H), 1.37 (s, 9H), 1.27 (m, 1H), 1.16-1.01 (m, 1H), 0.71 (m, 1H), 0.38 (m, 2H), −0.00 (m, 2H). $^{19}$F NMR (282 MHz, DMSO-d$_6$) δ −122.72, −60.80.

Step-10: Preparation of tert-butyl 3-(5-(5-(3-cyclopropyl-1-(2-oxopiperidin-1-yl)propyl)-2-fluorophenylcarbamoyl)-3-(trifluoromethyl)-1H-pyrazol-1-yl)benzylcarbamate (261j)

Palladium(II)hydroxide (6.43 mg, 0.023 mmol) was added to a solution of tert-butyl 3-(5-(5-(3-cyclopropyl-1-(2-oxo-3,4-dihydropyridin-1(2H)-yl)propyl)-2-fluorophenylcarbamoyl)-3-(trifluoromethyl)-1H-pyrazol-1-yl)benzylcarbamate (261i) (0.15 g, 0.23 mmol) in ethyl acetate (5 mL) and mixture was hydrogenated under H$_2$ atmosphere for 36 h. Mixture was filtered over celite pad, washed with EtOAc (2×10 mL), concentrated in vacuum and purified by flash column chromatography (silica gel 24 g, eluting with ethyl acetate in hexanes from 0-40%) to afford tert-butyl 3-(5-(5-(3-cyclopropyl-1-(2-oxopiperidin-1-yl)propyl)-2-fluorophenylcarbamoyl)-3-(trifluoromethyl)-1H-pyrazol-1-yl)benzylcarbamate (261j) (0.09 g, 0.137 mmol, 59.8% yield) as gummy mass; $^1$H NMR (300 MHz, DMSO-d$_6$) δ 10.60 (s, 1H), 7.60 (s, 1H), 7.42 (m, 6H), 7.23 (dt, J=13.4, 6.7 Hz, 2H), 5.77 (t, J=8.0 Hz, 1H), 4.19 (d, J=6.3 Hz, 2H), 3.16-3.00 (m, 1H), 2.82-2.64 (m, 1H), 2.39-2.18 (m, 2H), 1.99 (m, 3H), 1.74-1.43 (m, 3H), 1.37 (s, 9H), 1.30 (m, 1H), 1.08 (m, 1H), 0.72 (m, 1H), 0.38 (m, 2H), −0.00 (m, 2H); $^{19}$F NMR (282 MHz, DMSO-d$_6$) δ −123.10, −60.81.

Step-11: Preparation of (+)-1-(3-(aminomethyl)phenyl)-N-(5-(3-cyclopropyl-1-(2-oxopiperidin-1-yl)propyl)-2-fluorophenyl)-3-(trifluoromethyl)-1H-pyrazole-5-carboxamide (261k)

To a solution of tert-butyl 3-(5-(5-(3-cyclopropyl-1-(2-oxopiperidin-1-yl)propyl)-2-fluorophenylcarbamoyl)-3-(trifluoromethyl)-1H-pyrazol-1-yl)benzylcarbamate (261j) (0.09 g, 0.137 mmol) in methanol (4 mL) was added HCl (0.46 mL, 1.37 mmol, 3 M in methanol), stirred at room temperature for 20 h and concentrated in vacuum. The residue was partitioned between NaHCO$_3$ solution (40 mL) and EtOAc (30 mL). Layers were separated, aqueous layer was extracted with EtOAc (25 mL) and combined organics were washed with brine, dried over MgSO$_4$, filtered concentrated. The residue was purified by flash column chromatography [silica gel 12 g, eluting with CMA80 and chloroform from 0-30%] to afford (+)-1-(3-(aminomethyl) phenyl)-N-(5-(3-cyclopropyl-1-(2-oxopiperidin-1-yl)propyl)-2-fluorophenyl)-3-(trifluoromethyl)-1H-pyrazole-5-carboxamide (261k) (0.06 g, 0.11 mmol, 79% yield) as colorless foam; $^1$H NMR (300 MHz, DMSO-d$_6$) δ 10.59 (s, 1H), 7.58 (s, 1H), 7.54-7.38 (m, 4H), 7.38-7.10 (m, 3H), 5.76 (t, J=8.0 Hz, 1H), 3.78 (s, 2H), 3.16-3.00 (m, 1H), 2.72 (dd, J=12.2, 6.2 Hz, 1H), 2.29 (q, J=6.8 Hz, 2H), 1.95 (dd, J=15.5, 8.1 Hz, 2H), 1.76-1.43 (m, 4H), 1.34-0.96 (m, 3H), 0.91-0.65 (m, 2H), 0.38 (m, 2H), 0.11-0.00 (m, 2H); $^{19}$F NMR (282 MHz, DMSO-d$_6$) δ −123.14, −60.74; MS(ES+) 558.3 (M+1); MS(ES−) 556.3 (M−1), 592.3 (M+Cl). Optical rotation: [α]$_D$=(+) 49.12 [0.285, MeOH].

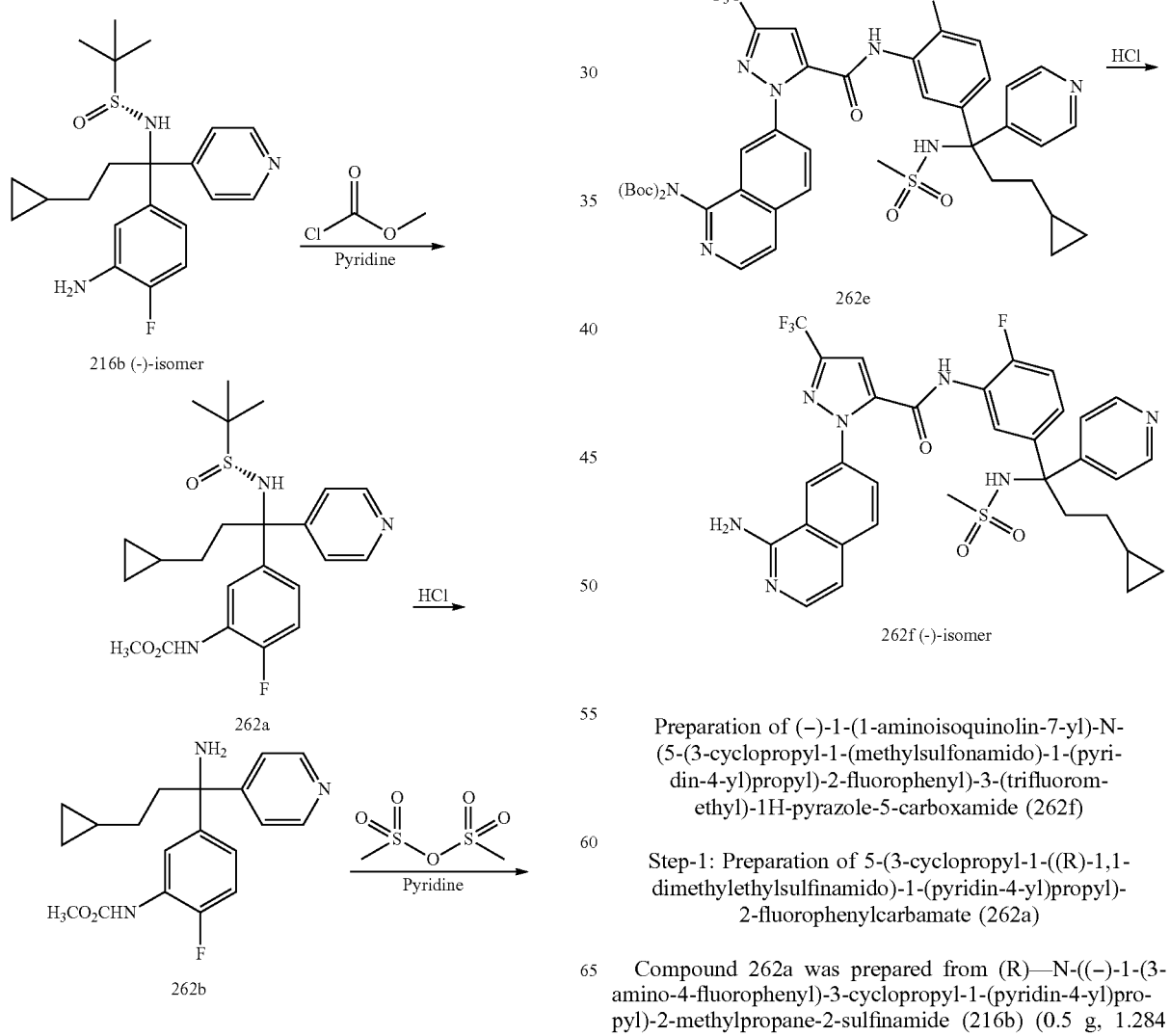

Preparation of (−)-1-(1-aminoisoquinolin-7-yl)-N-(5-(3-cyclopropyl-1-(methylsulfonamido)-1-(pyridin-4-yl)propyl)-2-fluorophenyl)-3-(trifluoromethyl)-1H-pyrazole-5-carboxamide (262f)

Step-1: Preparation of 5-(3-cyclopropyl-1-((R)-1,1-dimethylethylsulfinamido)-1-(pyridin-4-yl)propyl)-2-fluorophenylcarbamate (262a)

Compound 262a was prepared from (R)—N-((−)-1-(3-amino-4-fluorophenyl)-3-cyclopropyl-1-(pyridin-4-yl)propyl)-2-methylpropane-2-sulfinamide (216b) (0.5 g, 1.284 mmol) according to the procedure reported in step-1 of scheme 258 for preparation of compound 258a to afford 5-(3-cyclopropyl-1-((R)-1,1-dimethylethylsulfinamido)-1-(pyridin-4-yl)propyl)-2-fluorophenylcarbamate (262a) (0.573 g, 100% yield) as a yellow solid which was used as such in next step; $^1$H NMR (300 MHz, DMSO-d$_6$) δ 9.35 (s, 1H), 8.53-8.45 (m, 2H), 7.67 (d, J=7.5 Hz, 1H), 7.34-7.28 (m, 2H), 7.21-7.08 (m, 2H), 5.51 (s, 1H), 3.64 (s, 3H), 2.71-2.40 (m, 2H), 1.15 (s, 9H), 1.10-0.85 (m, 2H), 0.73-0.55 (m, 1H), 0.43-0.29 (m, 2H), −0.02--0.11 (m, 2H); $^{19}$F NMR (282 MHz, DMSO-d$_6$) δ −126.83; MS (ES$^+$): MS (ES+) 448.3 (M+1); MS (ES−) 446.3 (M−1), 482.3 (M+Cl).

Step-2: Preparation of methyl 5-(1-amino-3-cyclopropyl-1-(pyridin-4-yl)propyl)-2-fluorophenylcarbamate (262b)

To a stirred solution of 5-(3-cyclopropyl-1-((R)-1,1-dimethylethylsulfinamido)-1-(pyridin-4-yl)propyl)-2-fluorophenylcarbamate (262a) (0.551 g, 1.231 mmol) in methanol (12 mL) was added 3M methanolic HCl (2.462 mL, 7.39 mmol) and heated at reflux. The reaction was cooled to room temperature, concentrated in vacuum, basified with saturated aqueous NaHCO$_3$ solution and extracted with ethyl acetate (2×30 mL). The combined organic layer was dried over anhydrous MgSO$_4$, filtered, evaporated to dryness to afford methyl 5-(1-amino-3-cyclopropyl-1-(pyridin-4-yl)propyl)-2-fluorophenylcarbamate (262b) (0.418 g, 1.217 mmol, 99% yield) as a yellow syrup; $^1$H NMR (300 MHz, DMSO-d$_6$) δ 9.25 (s, 1H), 8.53-8.35 (m, 2H), 7.64 (d, J=7.6 Hz, 1H), 7.42-7.31 (m, 2H), 7.25-7.04 (m, 2H), 3.63 (s, 3H), 2.35 (s, 2H), 2.20 (t, J=8.1 Hz, 2H), 1.12-0.91 (m, 2H), 0.73-0.56 (m, 1H), 0.41-0.29 (m, 2H), −0.03--0.10 (m, 2H); $^{19}$F NMR (282 MHz, DMSO-d$_6$) δ −127.63; MS (ES$^+$): MS (ES+) 344.2 (M+1); MS (ES−) 342.2 (M−1).

Step-3: Preparation of methyl 5-(3-cyclopropyl-1-(methylsulfonamido)-1-(pyridin-4-yl)propyl)-2-fluorophenylcarbamate (262c)

To a stirred solution of methyl 5-(1-amino-3-cyclopropyl-1-(pyridin-4-yl)propyl)-2-fluorophenylcarbamate (262b) (0.401 g, 1.168 mmol) in dichloromethane (20 mL) at 0° C. was added pyridine (0.471 mL, 5.84 mmol), methanesulfonic anhydride (0.407 g, 2.336 mmol). The resulting mixture was allowed to warm to room temperature overnight. Additional pyridine (0.471 mL, 5.84 mmol) and methanesulfonic anhydride (0.407 g, 2.336 mmol) was added and mixture was stirred for another 3 h at room temperature. Reaction mixture was diluted with brine (20 mL), extracted with dichloromethane (2×30 mL), combined organic layers were dried over anhydrous MgSO$_4$, filtered, evaporated to dryness. The residue was purified by flash column chromatography [silica gel 12 g, eluting with CMA80 in chloroform from 0-75%] to afford methyl 5-(3-cyclopropyl-1-(methylsulfonamido)-1-(pyridin-4-yl)propyl)-2-fluorophenylcarbamate (262c) (0.489 g, 1.160 mmol, 99% yield) which was used as such in next step; MS (ES$^+$): MS (ES+) 444.2 (M+Na); MS (ES−) 456.2 (M+Cl).

Step-4: Preparation of (+)-N-(1-(3-amino-4-fluorophenyl)-3-cyclopropyl-1-(pyridin-4-yl)propyl)methanesulfonamide (262d)

Compound 262d was prepared from methyl 5-(3-cyclopropyl-1-(methyl sulfonamido)-1-(pyridin-4-yl)propyl)-2-fluorophenylcarbamate (262c) (0.483 g, 1.146 mmol) according to the procedure reported in step-5 of scheme 258 for preparation of compound 258e to afford (+)-N-(1-(3-amino-4-fluorophenyl)-3-cyclopropyl-1-(pyridin-4-yl)propyl)methanesulfonamide (262d) (0.311 g, 0.856 mmol, 74.7% yield) as a white solid; $^1$H NMR (300 MHz, DMSO-d$_6$) δ 8.61-8.30 (m, 2H), 7.67 (s, 1H), 7.37-7.18 (m, 2H), 6.95 (dd, J=11.2, 8.5 Hz, 1H), 6.82 (dd, J=8.9, 2.4 Hz, 1H), 6.50-6.36 (m, 1H), 5.21 (s, 2H), 2.66-2.54 (m, 1H), 2.35-2.24 (m, 1H), 2.21 (s, 3H), 1.15-0.97 (m, 1H), 0.87-0.67 (m, 1H), 0.64-0.47 (m, 1H), 0.40-0.20 (m, 2H), −0.02--0.20 (m, 2H); MS (ES+): MS (ES−) 362.2 (M−1), 725.3 (2M−1); Optical rotation: [α]$_D$=(+) 21.0 [0.2, MeOH].

Step-5: Preparation of di-tert-butyl 7-(5-(5-(3-cyclopropyl-1-(methyl sulfonamido)-1-(pyridin-4-yl)propyl)-2-fluorophenylcarbamoyl)-3-(trifluoromethyl)-1H-pyrazol-1-yl)isoquinolin-1-ylcarbamate (262e)

Compound 262e was prepared from 1-(1-(bis(tert-butoxycarbonyl)amino)isoquinolin-7-yl)-3-(trifluoromethyl)-1H-pyrazole-5-carboxylic acid (253c)(0.519 g, 0.994 mmol) and (+)-N-(1-(3-amino-4-fluorophenyl)-3-cyclopropyl-1-(pyridin-4-yl)propyl)methanesulfonamide (262d) (0.301 g, 0.828 mmol) according to the procedure reported in step-3 of scheme 208 for preparation of compound 208c to afford di-tert-butyl 7-(5-(5-(3-cyclopropyl-1-(methylsulfonamido)-1-(pyridin-4-yl)propyl)-2-fluorophenylcarbamoyl)-3-(trifluoromethyl)-1H-pyrazol-1-yl)isoquinolin-1-ylcarbamate (262e), the crude reaction mixture was used as such in the next step; MS (ES+): 868.3 (M+1).

Step-6: Preparation of (−)-1-(1-aminoisoquinolin-7-yl)-N-(5-(3-cyclopropyl-1-(methylsulfonamido)-1-(pyridin-4-yl)propyl)-2-fluorophenyl)-3-(trifluoromethyl)-1H-pyrazole-5-carboxamide (262f)

Compound 262f was prepared from di-tert-butyl 7-(5-(5-(3-cyclopropyl-1-(methylsulfonamido)-1-(pyridin-4-yl)propyl)-2-fluorophenylcarbamoyl)-3-(trifluoromethyl)-1H-pyrazol-1-yl)isoquinolin-1-ylcarbamate (262e) (1.439 g, 1.658 mmol) according to the procedure reported in step-7 of scheme 258 for preparation of compound 258f to afford after purification compound 262f (78 mg, 7% yield) yellow solid as a free-base; $^1$H NMR (300 MHz, DMSO-d$_6$) δ 10.61 (s, 1H), 8.69-8.45 (m, 2H), 8.43 (s, 1H), 7.98-7.51 (m, 6H), 7.40-7.14 (m, 3H), 7.10-6.84 (m, 3H), 2.31-2.22 (m, 2H), 2.27 (s, 3H), 1.21-0.93 (m, 2H), 0.90-0.71 (m, 1H), 0.65-0.48 (m, 1H), 0.38-0.20 (m, 2H), −0.05--0.21 (m, 2H); $^{19}$F NMR (282 MHz, DMSO-d$_6$) δ −60.70, −121.52;

To a solution of free base of compound 262f (0.069 g, 0.103 mmol) in methanol (10 mL) was added HCl (3M in methanol) (0.207 mL, 0.620 mmol), evaporated to dryness, dissolved in minimum amount of water and lyophilized to afford (−)-1-(1-aminoisoquinolin-7-yl)-N-(5-(3-cyclopropyl-1-(methylsulfonamido)-1-(pyridin-4-yl)propyl)-2-fluorophenyl)-3-(trifluoromethyl)-1H-pyrazole-5-carboxamide (262f) (34 mg, 49% yield) hydrochloride salt as a white solid; $^1$H NMR (300 MHz, DMSO-d$_6$) δ 13.67 (s, 1H, D$_2$O exchangeable), 10.90 (s, 1H, D$_2$O exchangeable), 9.33 (s, 2H, D$_2$O exchangeable), 8.99-8.85 (m, 1H), 8.78 (d, J=6.0 Hz, 2H), 8.19-8.03 (m, 3H), 7.89 (s, 1H), 7.90-7.67 (m, 3H), 7.67-7.55 (m, 1H), 7.39-7.21 (m, 3H), 2.76-2.41 (m, 2H), 2.39 (s, 3H), 1.11-0.95 (m, 1H), 0.88-0.69 (m, 1H), 0.65-0.50 (m, 1H), 0.38-0.19 (m, 2H), −0.02--0.21 (m, 2H); $^{19}$F NMR (282 MHz, DMSO-d$_6$) δ −60.90, −120.70; $^1$H NMR (300 MHz, DMSO-d$_6$/D$_2$O) δ 8.97 (s, 1H), 8.91-8.83 (m, 2H), 8.30-8.14 (m, 2H), 8.00-7.84 (m, 4H), 7.76 (dd, J=7.2, 2.4 Hz, 1H), 7.54-6.79 (m, 3H), 2.86-2.58 (m, 2H), 2.55 (s, 3H), 1.26-1.04 (m, 2H), 1.05-0.83 (m, 1H), 0.80-0.62 (m, 1H), 0.53-0.32 (m, 2H), 0.11--0.08 (m, 2H); MS (ES+): MS (ES+) 668.2 (M+1), 702.2 (M+Cl); Optical rotation: $[\alpha]_D=$ (−) 2.0 [0.1, MeOH]; Analysis calculated for: $C_{32}H_{29}F_4N_{7}O_3S$·2.25HCl·4.25H$_2$O: C, 46.51; H, 4.85; Cl, 9.65; N, 11.87; Found: C, 46.66; H, 4.56; Cl, 9.27; N, 12.03.

Scheme 263

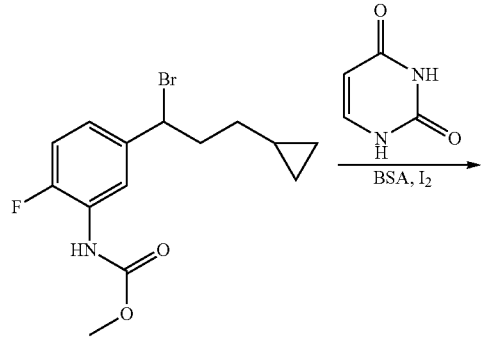

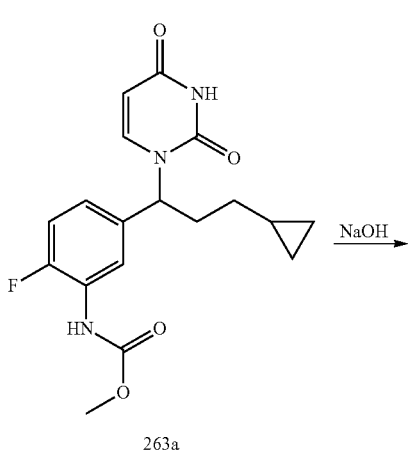

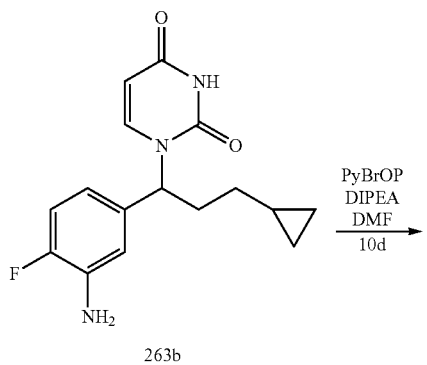

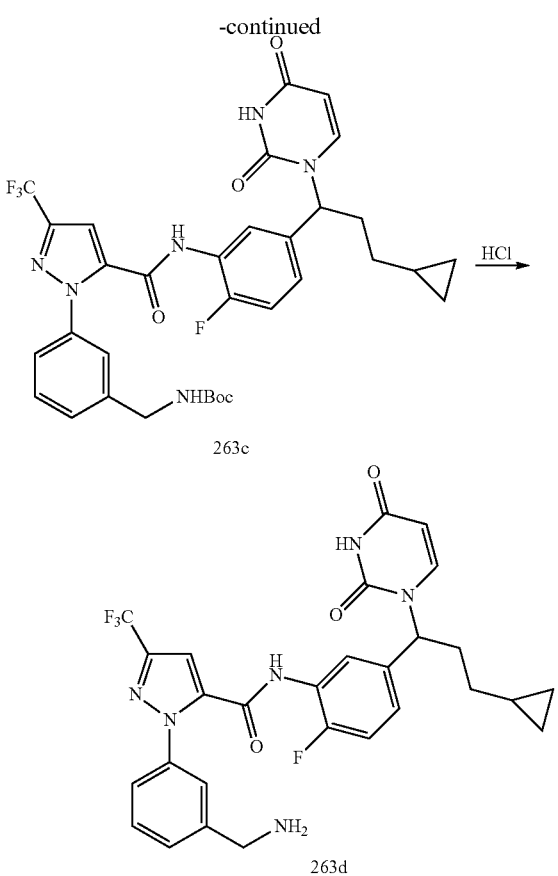

Preparation of 1-(3-(aminomethyl)phenyl)-N-(5-(3-cyclopropyl-1-(2,4-dioxo-3,4-dihydropyrimidin-1(2H)-yl)propyl)-2-fluorophenyl)-3-(trifluoromethyl)-1H-pyrazole-5-carboxamide (263d)

Step-1: Preparation of methyl (5-(3-cyclopropyl-1-(2,4-dioxo-3,4-dihydropyrimidin-1(2H)-yl)propyl)-2-fluorophenyl)carbamate (263a)

To a suspension of uracil (1 g, 8.92 mmol) in acetonitrile (60 mL) was added N,O-bis trimethylsilyl acetamide (BSA, 4.54 g, 22.30 mmol) and stirred for 30 min. To the reaction mixture was added methyl 5-(1-bromo-3-cyclopropylpropyl)-2-fluorophenylcarbamate (528c) (3.54 g, 10.71 mmol), iodine (0.226 g, 0.892 mmol) and heated at reflux until all starting material was consumed. The reaction mixture was cooled to room temperature, concentrated in vacuum, diluted with ethyl acetate (100 mL), and washed with H$_2$O (50 mL). The organic layer was dried, filtered and concentrated in vacuum. The residue obtained was purified by flash column chromatography (silica gel 40 g, eluting with 0-90% EtOAc in hexane) to furnish methyl 5-(3-cyclopropyl-1-(2,4-dioxo-3,4-dihydropyrimidin-1(2H)-yl)propyl)-2-fluorophenylcarbamate (263a) (785 mg, 0.498 mmol, 24.4% yield) as a white solid; $^1$H NMR (300 MHz, DMSO-d$_6$) δ 11.33 (s, 1H), 9.40 (s, 1H), 7.72 (d, J=8.0 Hz, 1H), 7.65 (d, J=6.2 Hz, 1H), 7.29-7.16 (m, 1H), 7.19-7.09 (m, 1H), 5.58 (t, J=7.5 Hz, 2H), 3.66 (s, 3H), 2.24-2.05 (m, 2H), 1.24-1.02 (m, 2H), 0.75-0.64 (m, 1H), 0.46-0.32 (m, 2H), 0.05--0.03 (m, 2H); $^{19}$F NMR (282 MHz, DMSO-d$_6$) δ −125.34; MS (ES+) 362.2 (M+1), 360.2 (M−1).

Step-2: Preparation of 1-(1-(3-amino-4-fluorophenyl)-3-cyclopropylpropyl)pyrimidine-2,4(1H,3H)-dione (263b)

Compound 263b was prepared from methyl 5-(3-cyclopropyl-1-(2,4-dioxo-3,4-dihydropyrimidin-1(2H)-yl)propyl)-2-fluorophenylcarbamate (263a) (765 mg, 2.117 mmol) according to the procedure reported in step-5 of scheme 258 for preparation of compound 258e to afford after purification by flash column chromatography [silica gel 12 g, eluting with 0-60% ethyl acetate in hexanes] 1-(1-(3-amino-4-fluorophenyl)-3-cyclopropylpropyl)pyrimidine-2,4(1H,3H)-dione (263b) (450 mg, 1.484 mmol, 70.1% yield) as a white solid.
$^1$H NMR (300 MHz, DMSO-$d_6$) δ 11.31 (s, 1H), 7.62 (d, J=8.0 Hz, 1H), 6.96 (dd, J=11.2, 8.5 Hz, 1H), 6.71 (d, J=7.3 Hz, 1H), 6.56-6.48 (m, 1H), 5.57 (d, J=6.3 Hz, 1H), 5.49 (t, J=7.7 Hz, 1H), 5.21 (s, 2H), 2.21-1.97 (m, 2H), 1.21-1.00 (m, 2H), 0.76-0.59 (m, 1H), 0.42-0.32 (m, 2H), 0.10--0.12 (m, 2H); $^{19}$F NMR (282 MHz, DMSO-$d_6$) δ -136.17.

Step-3: Preparation of tert-butyl 3-(5-((5-(3-cyclopropyl-1-(2,4-dioxo-3,4-dihydropyrimidin-1 (2H)-yl)propyl)-2-fluorophenyl)carbamoyl)-3-(trifluoromethyl)-1H-pyrazol-1-yl)benzylcarbamate (263c)

Compound 263c was prepared from 1-(1-(3-amino-4-fluorophenyl)-3-cyclopropylpropyl)pyrimidine-2,4(1H,3H)-dione (263b) (410 mg, 1.352 mmol) and 1-(3-((tert-butoxycarbonylamino)methyl)phenyl)-3-(trifluoromethyl)-1H-pyrazole-5-carboxylic acid (10d) (781 mg, 2.027 mmol) according to the procedure reported in step-3 of scheme 208 for preparation of compound 208c to afford after purification by flash column chromatography [silica gel 24 g, eluting with 0-90% EtOAc/MeOH (9:1, v/v) in hexane] tert-butyl 3-(5-(5-(3-cyclopropyl-1-(2,4-dioxo-3,4-dihydropyrimidin-1(2H)-yl)propyl)-2-fluorophenylcarbamoyl)-3-(trifluoromethyl)-1H-pyrazol-1-yl)benzylcarbamate (263c) (325 mg, 0.485 mmol, 35.9% yield) as a white solid; $^1$H NMR (300 MHz, DMSO-$d_6$) δ 11.35 (s, 1H), 10.64 (s, 1H), 7.74 (d, J=8.0 Hz, 1H), 7.64-7.25 (m, 9H), 5.59 (d, J=8.0 Hz, 2H), 4.20 (d, J=6.1 Hz, 2H), 2.30-2.04 (m, 2H), 1.37 (s, 9H), 1.24-1.00 (m, 2H), 0.77-0.61 (m, 1H), 0.43-0.31 (m, 2H), 0.08--0.06 (m, 2H); $^{19}$F NMR (282 MHz, DMSO-$d_6$) δ -60.82, -121.69; MS (ES$^+$), 693.2 (M+Na); (ES-) 669.3 (M-1).

Step-4: Preparation of 1-(3-(aminomethyl)phenyl)-N-(5-(3-cyclopropyl-1-(2,4-dioxo-3,4-dihydropyrimidin-1(2H)-yl)propyl)-2-fluorophenyl)-3-(trifluoromethyl)-1H-pyrazole-5-carboxamide (263d)

To a solution of tert-butyl 3-(5-(5-(3-cyclopropyl-1-(2,4-dioxo-3,4-dihydropyrimidin-1 (2H)-yl)propyl)-2-fluorophenylcarbamoyl)-3-(trifluoromethyl)-1H-pyrazol-1-yl)benzylcarbamate (263c) (300 mg, 0.447 mmol) in MeOH (15 mL) was added HCl (3N in MeOH) (1.193 mL, 3.58 mmol) and heated at reflux for 40 min. The solution was cooled to room temperature concentrated in vacuum and the residue was purified by flash column chromatography (silica gel 12 g, eluting with 0-60% CMA80 in CHCl$_3$) to furnish 1-(3-(aminomethyl)phenyl)-N-(5-(3-cyclopropyl-1-(2,4-dioxo-3,4-dihydropyrimidin-1(2H)-yl)propyl)-2-fluorophenyl)-3-(trifluoromethyl)-1H-pyrazole-5-carboxamide (263d) (140 mg, 0.245 mmol, 54.9% yield) as a white solid; $^1$H NMR (300 MHz, DMSO-$d_6$) δ 7.74 (d, J=8.0 Hz, 1H), 7.63-7.48 (m, 3H), 7.48-7.39 (m, 2H), 7.38-7.25 (m, 3H), 5.60 (m, 2H), 3.78 (s, 2H), 2.26-2.05 (m, 2H), 1.22-0.98 (m, 2H), 0.77-0.62 (m, 1H), 0.45-0.32 (m, 2H), 0.00 (m, 2H); $^{19}$F NMR (282 MHz, DMSO-$d_6$) δ -60.75, -121.72; MS (ES+), 571.3 (M+1), 569.3 (M-1).

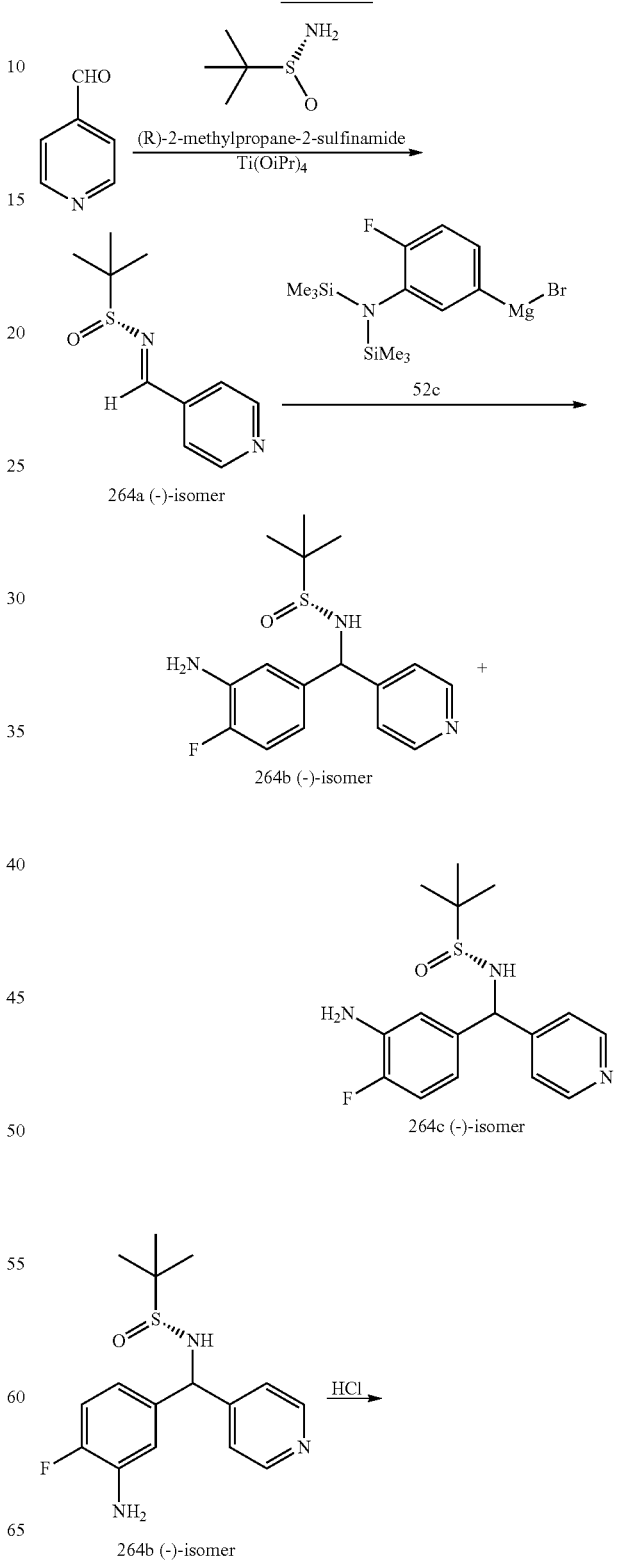

Scheme 264

264a (-)-isomer 264b (-)-isomer 264c (-)-isomer 264b (-)-isomer

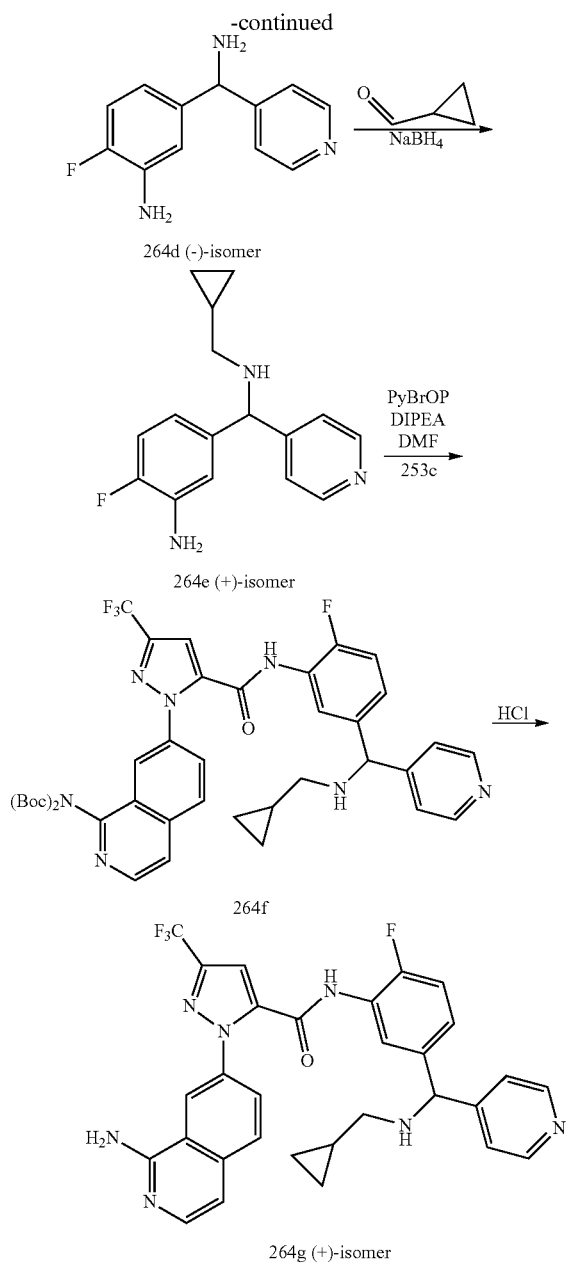

Preparation of (+)-1-(1-aminoisoquinolin-7-yl)-N-(5-(((cyclopropylmethylamino)(pyridin-4-yl)methyl)-2-fluorophenyl)-3-(trifluoromethyl)-1H-pyrazole-5-carboxamide (264g)

Step-1: Preparation of (R)-2-methyl-N-(pyridin-4-ylmethylene)propane-2-sulfinamide (264a)

Compound 264a was prepared from isonicotinaldehyde (11.67 g, 109 mmol) and (R)-2,4,6-triisopropylbenzenesulfinamide (12 g, 99 mmol) according to the procedure reported in step-1 of scheme-222 for the preparation of compound 222a to afford after purification by flash column chromatography (silica gel 120 g, eluting with ethyl acetate in hexanes from 0-70%) (R)-2-methyl-N-(pyridin-4-ylmethylene)propane-2-sulfinamide (264a) (15.60 g, 75% yield) as a crystalline pale yellow solid; $^1$H NMR: $^1$H NMR (300 MHz, DMSO-d$_6$) δ 8.84-8.77 (m, 2H), 8.63 (s, 1H), 7.94-7.81 (m, 2H), 1.21 (s, 9H); MS (ES$^+$): MS (ES+): 211.2 (M+1); Optical rotation: [α]$_D$=(−) 99.25 [0.935, MeOH].

Step-2: Preparation of (R)—N—((S)-(3-amino-4-fluorophenyl)(pyridin-4-yl)methyl)-2-methylpropane-2-sulfinamide (264b) and (R)—N—((R)-(3-amino-4-fluorophenyl)(pyridin-4-yl)methyl)-2-methylpropane-2-sulfinamide (264c)

Compounds 264b and 264c was prepared from (R)-2-methyl-N-(pyridin-4-ylmethylene)propane-2-sulfinamide (264a) (10.73 g, 51 mmol) and freshly prepared 3-(bis(trimethylsilyl)amino)-4-fluorophenyl)magnesium bromide (52c) (107 mL, 81 mmol) according to the procedure reported in step-2 of scheme-222 for the preparation of compound 222b and 222c to afford after purification by flash column chromatography [silica gel 120 g, eluting with CMA80 in chloroform, 0-100%] to afford;

1. (R)—N—((S)-(3-amino-4-fluorophenyl)(pyridin-4-yl)methyl)-2-methylpropane-2-sulfinamide (264b) (6.979 g, 43% yield) as a light red solid; $^1$H NMR (300 MHz, DMSO-d$_6$) δ 8.58-8.42 (m, 2H), 7.43-7.26 (m, 2H), 6.93 (dd, J=11.5, 8.3 Hz, 1H), 6.80-6.66 (m, 1H), 6.64-6.50 (m, 1H), 6.02 (d, J=6.1 Hz, 1H), 5.40 (d, J=6.1 Hz, 1H), 5.15 (s, 2H, D$_2$O exchangeable), 1.14 (s, 9H); $^{19}$F NMR (282 MHz, DMSO-d$_6$) δ −136.78; MS (ES$^+$): MS (ES+) 322.2 (M+1), 344.2 (M+Na); MS (ES−) 320.3 (M−1); Optical rotation: [α]$_D$=(−) 27.41 [0.54, MeOH].
2. (R)—N—((R)-(3-amino-4-fluorophenyl)(pyridin-4-yl)methyl)-2-methylpropane-2-sulfinamide (264c) (5.26 g, 32% yield) as a yellow solid; $^1$H NMR (300 MHz, DMSO-d$_6$) δ 8.59-8.44 (m, 2H), 7.48-7.31 (m, 2H), 6.92 (dd, J=11.4, 8.3 Hz, 1H), 6.69 (dd, J=8.9, 2.2 Hz, 1H), 6.58-6.41 (m, 1H), 6.10 (d, J=6.3 Hz, 1H), 5.36 (d, J=6.2 Hz, 1H), 5.14 (s, 2H, D$_2$O exchangeable), 1.14 (s, 9H); $^{19}$F NMR (282 MHz, DMSO-d$_6$) δ −136.73; MS (ES$^+$): MS (ES+) 322.2 (M+1), 344.2 (M+Na); MS (ES−) 320.3 (M−1), 356.2 (M+Cl); Optical rotation: [α]$_D$=(−) 77.2 [0.5, MeOH].

Step-3: Preparation of (+)-5-(amino(pyridin-4-yl)methyl)-2-fluoroaniline (264d)

Compound 264d was prepared from (R)—N—((S)-3-amino-4-fluorophenyl)(pyridin-4-yl)methyl)-2-methylpropane-2-sulfinamide (264b) (2.26 g, 7.03 mmol) according to the procedure reported in step-3 of scheme-222 for the preparation of compound 222d to afford after purification by flash column chromatography [silica gel 40 g, eluting with methanol in chloroform, 0-100%] (+)-5-(amino(pyridin-4-yl)methyl)-2-fluoroaniline (264d) (0.344 g, 22% yield) as a yellow solid; $^1$H NMR (300 MHz, DMSO-d$_6$) δ 8.55-8.38 (m, 2H), 7.44-7.23 (m, 2H), 6.88 (dd, J=11.5, 8.3 Hz, 1H), 6.74 (dd, J=8.9, 2.2 Hz, 1H), 6.62-6.48 (m, 1H), 5.06 (s, 2H, D$_2$O exchangeable), 4.92 (s, 1H), 2.26 (s, 2H, D$_2$O exchangeable); $^{19}$F NMR (282 MHz, DMSO-d$_6$) δ −137.67; MS (ES$^+$): MS (ES+) 218.2 (M+1); MS (ES−) 216.1 (M−1); Optical rotation: [α]$_D$=(+) 47.55 [0.235, MeOH].

Step-4: Preparation of (+)-5-((cyclopropylmethylamino)(pyridin-4-yl)methyl)-2-fluoroaniline (264e)

Compound 264e was prepared from (+)-5-(amino(pyridin-4-yl)methyl)-2-fluoroaniline (264d) (0.331 g, 1.524 mmol) according to the procedure reported in step-4 of scheme-222 for the preparation of compound 222f to afford after purification by flash column chromatography (silica gel 12 g, eluting with 0-50% CMA80 in chloroform in hexanes) (+)-5-((cyclopropylmethylamino)(pyridin-4-yl)methyl)-2-fluoroaniline (264e) (0.326 g, 1.201 mmol, 79% yield) as a yellow oil; $^1$H NMR (300 MHz, DMSO-$d_6$) δ 8.53-8.41 (m, 2H), 7.48-7.32 (m, 2H), 6.96-6.73 (m, 2H), 6.63-6.45 (m, 1H), 5.10 (s, 2H, $D_2O$ exchangeable), 4.69 (s, 1H), 2.50-2.39 (m, 1H), 2.34-2.17 (m, 2H), 0.98-0.83 (m, 1H), 0.48-0.31 (m, 2H), 0.10--0.01 (m, 2H); $^{19}$F NMR (282 MHz, DMSO-$d_6$) δ -137.28; MS (ES$^+$): MS (ES+) 272.2 (M+1), MS (ES-) 270.2 (M-1); Optical rotation: $[α]_D$=(+) 41.65 [0.485, MeOH].

Step-5: Preparation of bis-di-tert-butyl 7-(5-(5-((cyclopropylmethylamino)(pyridin-4-yl)methyl)-2-fluorophenylcarbamoyl)-3-(trifluoromethyl)-1H-pyrazol-1-yl)isoquinolin-1-ylcarbamate (264f)

Compound 264f was prepared from 1-(1-(bis(tert-butoxycarbonyl)amino)isoquinolin-7-yl)-3-(trifluoromethyl)-1H-pyrazole-5-carboxylic acid (253c) (0.595 g, 1.139 mmol) and (+)-5-((cyclopropylmethylamino)(pyridin-4-yl)methyl)-2-fluoroaniline (264e) (0.309 g, 1.139 mmol) according to the procedure reported in step-3 of scheme 208 for preparation of compound 208c to afford bis-di-tert-butyl 7-(5-(5-((cyclopropylmethylamino)(pyridin-4-yl)methyl)-2-fluorophenylcarbamoyl)-3-(trifluoromethyl)-1H-pyrazol-1-yl)isoquinolin-1-ylcarbamate (264f) as a brown waxy solid which was used as such in next step.

Step-6: (+)-1-(1-aminoisoquinolin-7-yl)-N-(5-((cyclopropylmethylamino)(pyridin-4-yl)methyl)-2-fluorophenyl)-3-(trifluoromethyl)-1H-pyrazole-5-carboxamide (264g)

Compound 264g was prepared from bis-di-tert-butyl 7-(5-(5-((cyclopropylmethylamino)(pyridin-4-yl)methyl)-2-fluorophenylcarbamoyl)-3-(trifluoromethyl)-1H-pyrazol-1-yl)isoquinolin-1-ylcarbamate (264f) (1.4202 g, 1.831 mmol) according to the procedure reported in step-7 of scheme 258 for preparation of compound 258f to afford after purification compound 264g as a free-base. The free base was converted to hydrochloride salt to afford after lypholization (+)-1-(1-aminoisoquinolin-7-yl)-N-(5-((cyclopropylmethylamino)(pyridin-4-yl)methyl)-2-fluorophenyl)-3-(trifluoromethyl)-1H-pyrazole-5-carboxamide (264g) (64 mg, 6% yield) hydrochloride salt as a white solid.

$^1$H NMR (300 MHz, DMSO-$d_6$) δ 13.74 (s, 1H, $D_2O$ exchangeable), 10.96 (s, 1H, $D_2O$ exchangeable), 10.76 (s, 1H, $D_2O$ exchangeable), 9.55-9.18 (m, 2H, $D_2O$ exchangeable), 8.99-8.74 (m, 3H), 8.29-8.13 (m, 2H), 8.10 (s, 1H), 8.00 (d, J=6.6 Hz, 1H), 7.93 (s, 1H), 7.88-7.66 (m, 2H), 7.42 (t, J=9.4 Hz, 1H), 7.39-7.22 (m, 1H), 5.93 (s, 1H), 2.73 (s, 2H), 1.36-1.06 (m, 1H), 0.53 (m, 2H), 0.43-0.10 (m, 2H); $^1$H NMR (300 MHz, DMSO/D20-$d_6$) δ 8.92-8.74 (m, 3H), 8.10 (s, 2H), 7.94 (d, J=5.6 Hz, 2H), 7.94-7.84 (m, 1H), 7.81 (s, 1H), 7.75 (d, J=6.9 Hz, 1H), 7.66-7.55 (m, 1H), 7.44 (t, J=9.4 Hz, 1H), 7.36 (d, J=7.1 Hz, 1H), 5.85 (s, 1H), 2.98-2.68 (m, 2H), 1.19-1.00 (m, 1H), 0.71-0.52 (m, 2H), 0.31 (m, 2H); $^{19}$F NMR (282 MHz, DMSO-$d_6$) δ -60.86, -118.92; MS (ES$^+$): MS (ES+) 576.2 (M+1), 610.2 (M+Cl); HPLC: HPLC (Reverse phase, UV Absorbance 260 nm; Rt=3.010 min (98.17%)]; Optical rotation: $[α]_D$=(+) 23.40 [0.265, MeOH]; Analysis calculated for: $C_{30}H_{25}F_4N_7O \cdot 3HCl \cdot 4H_2O$: C, 47.60; H, 4.79; Cl, 14.05; N, 12.95; Found: C, 47.41; H, 4.80; Cl, 13.88; N, 12.87.

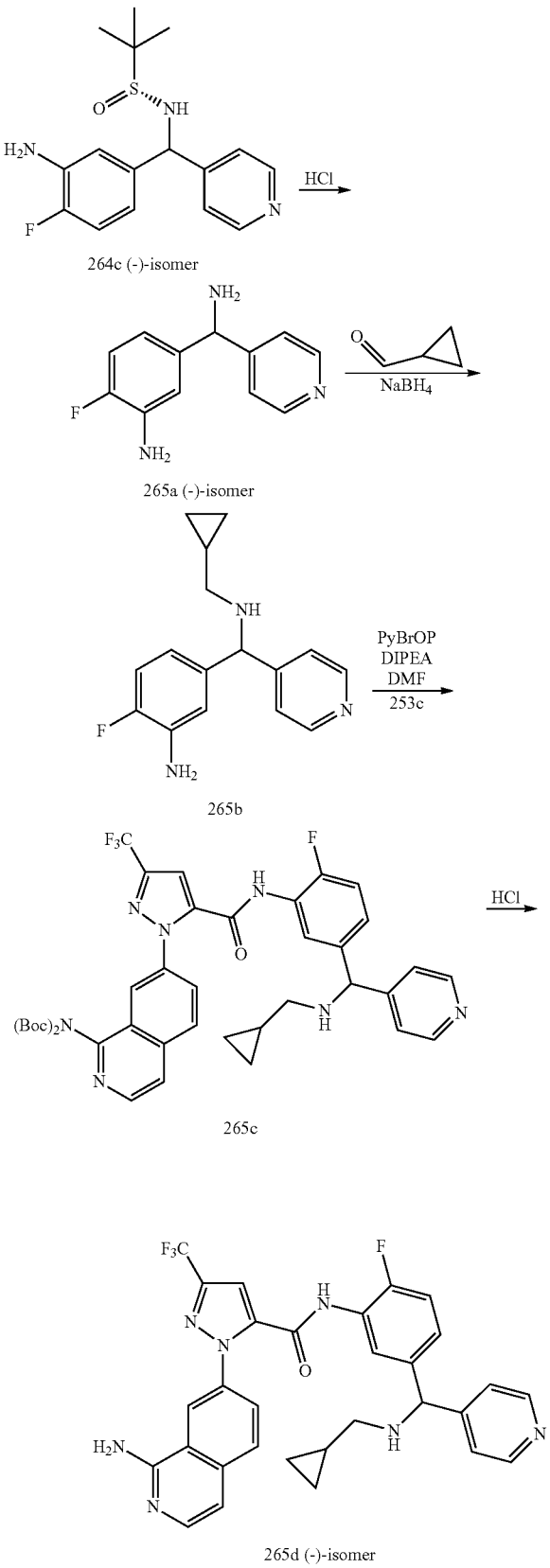

Scheme 265

Preparation of (−)-1-(1-aminoisoquinolin-7-yl)-N-(5-((cyclopropylmethylamino)(pyridin-4-yl)methyl)-2-fluorophenyl)-3-(trifluoromethyl)-1H-pyrazole-5-carboxamide (265d)

Step-1: Preparation of (−)-5-(amino(pyridin-4-yl)methyl)-2-fluoroaniline (265a)

Compound 265a was prepared from (R)—N—((R)-(3-amino-4-fluorophenyl)(pyridin-4-yl)methyl)-2-methylpropane-2-sulfinamide (264c) (2.61 g, 8.12 mmol) according to the procedure reported in step-3 of scheme-222 for the preparation of compound 222d to afford after purification by flash column chromatography [silica gel 40 g, eluting with methanol in chloroform, 0-100%] (−)-5-(amino(pyridin-4-yl)methyl)-2-fluoroaniline (265a) (1.736 g, 98% yield) as a reddish yellow oil which was used as such in the next step; MS (ES$^+$): MS (ES+) 218.2 (M+1); MS (ES−) 216.1 (M−1); Optical rotation: [α]$_D$=(−) 62.35 [0.51, MeOH].

Step-2: Preparation of (−)-5-((cyclopropylmethylamino)(pyridin-4-yl)methyl)-2-fluoroaniline (265b)

Compound 265b was prepared from (−)-5-(amino(pyridin-4-yl)methyl)-2-fluoroaniline (265a) (1.79 g, 8.24 mmol) according to the procedure reported in step-4 of scheme-222 for the preparation of compound 222f to afford after purification by flash column chromatography (silica gel 40 g, eluting with 0-100% CMA80 in chloroform) (−)-5-((cyclopropylmethylamino)(pyridin-4-yl)methyl)-2-fluoroaniline (265b) (0.089 g, 4% yield) as a yellow oil; $^1$H NMR (300 MHz, DMSO-d$_6$) δ 8.68-8.35 (m, 2H), 7.52-7.28 (m, 2H), 6.99-6.74 (m, 2H), 6.64-6.44 (m, 1H), 5.09 (s, 2H), 4.68 (s, 1H), 2.51-2.36 (m, 1H), 2.37-2.18 (m, 2H), 1.00-0.81 (m, 1H), 0.48-0.32 (m, 2H), 0.11-0.00 (m, 2H); $^{19}$F NMR (282 MHz, DMSO-d$_6$) δ −137.26; MS (ES$^+$): MS (ES+) 272.3 (M+1); MS (ES−) 270.3 (M−1).

Step-3: Preparation of bis-di-tert-butyl 7-(5-(5-((cyclopropylmethylamino)(pyridin-4-yl)methyl)-2-fluorophenylcarbamoyl)-3-(trifluoromethyl)-1H-pyrazol-1-yl)isoquinolin-1-ylcarbamate (265c)

Compound 265c was prepared from 1-(1-(bis(tert-butoxycarbonyl)amino)isoquinolin-7-yl)-3-(trifluoromethyl)-1H-pyrazole-5-carboxylic acid (253c) (81 mg, 0.155 mmol) and (−)-5-((cyclopropylmethylamino)(pyridin-4-yl)methyl)-2-fluoroaniline (265b) (50 mg, 0.186 mmol) according to the procedure reported in step-3 of scheme 208 for preparation of compound 208c to afford crude bis-di-tert-butyl 7-(5-(5-((cyclopropylmethylamino)(pyridin-4-yl)methyl)-2-fluorophenylcarbamoyl)-3-(trifluoromethyl)-1H-pyrazol-1-yl)isoquinolin-1-ylcarbamate (265c) which was used as such in next step.

Step-4: Preparation of (−)-1-(1-aminoisoquinolin-7-yl)-N-(5-((cyclopropylmethylamino)(pyridin-4-yl)methyl)-2-fluorophenyl)-3-(trifluoromethyl)-1H-pyrazole-5-carboxamide (265d)

To a solution of crude bis-di-tert-butyl 7-(5-(5-((cyclopropylmethylamino)(pyridin-4-yl)methyl)-2-fluorophenylcarbamoyl)-3-(trifluoromethyl)-1H-pyrazol-1-yl)isoquinolin-1-ylcarbamate (265c) from above step in anhydrous dioxane (5 mL) was added HCl (4N in dioxane, 2 mL) and heated at 60° C. for 50 min. The reaction mixture was cooled to room temperature and concentrated in vacuum to dryness. The residue obtained was purified by flash column chromatography (silica gel 40 g, eluting with 0-40% CMA-80 in chloroform) to furnish compound 265d as a free base, which was converted to the HCl salt to afford (−)-1-(1-aminoisoquinolin-7-yl)-N-(5-((cyclopropylmethylamino)(pyridin-4-yl)methyl)-2-fluorophenyl)-3-(trifluoromethyl)-1H-pyrazole-5-carboxamide (265d) (25 mg, 0.043 mmol, 28.0% yield) hydrochloride as a white solid; $^1$H NMR (300 MHz, DMSO-d$_6$) δ 13.50 (s, 1H), 10.87 (s, 1H), 10.48 (s, 2H), 9.26 (s, 2H), 8.76-8.69 (m, 2H), 8.09 (m, 2H), 8.01-7.84 (m, 5H), 7.80 (d, J=7.0 Hz, 1H), 7.77-7.71 (m, 1H), 7.42 (dd, J=10.3, 8.6 Hz, 1H), 7.33 (d, J=7.0 Hz, 1H), 5.80 (d, J=7.2 Hz, 1H), 2.83-2.62 (m, 2H), 1.26-1.05 (m, 1H), 0.65-0.44 (m, 2H), 0.42-0.21 (m, 2H); MS (ES+) 576.4 (M+1); 574.4 (M−1); Optical rotation: [α]$_D$=(−) 16 [0.25, MeOH]; Analysis calculated for C$_{30}$H$_{25}$F$_4$N$_7$O.3HCl.3.5H$_2$O: C, 48.17; H, 4.72; N, 13.11; Found: C, 48.29; H, 4.70; N, 12.88.

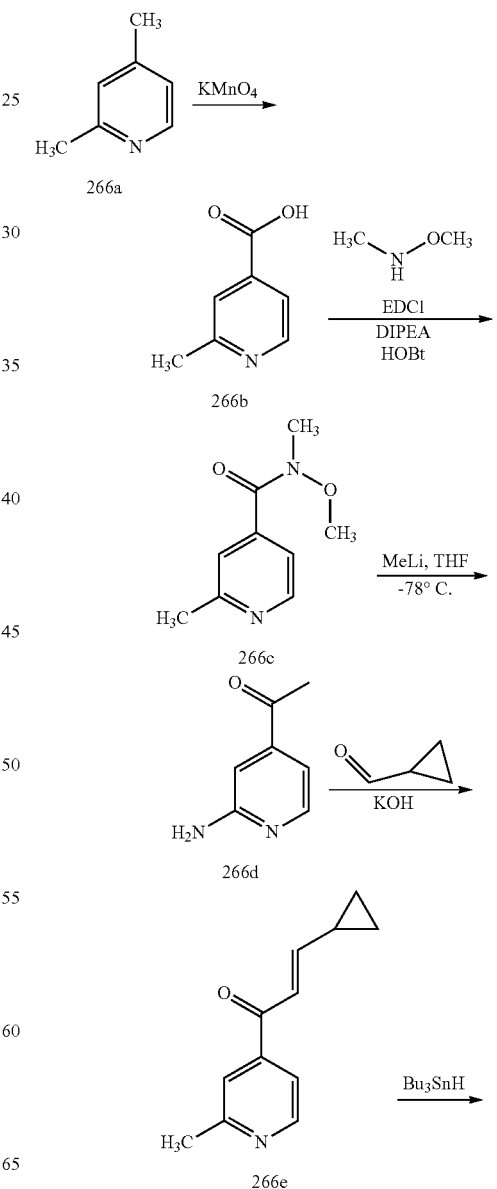

Scheme 266

933
-continued

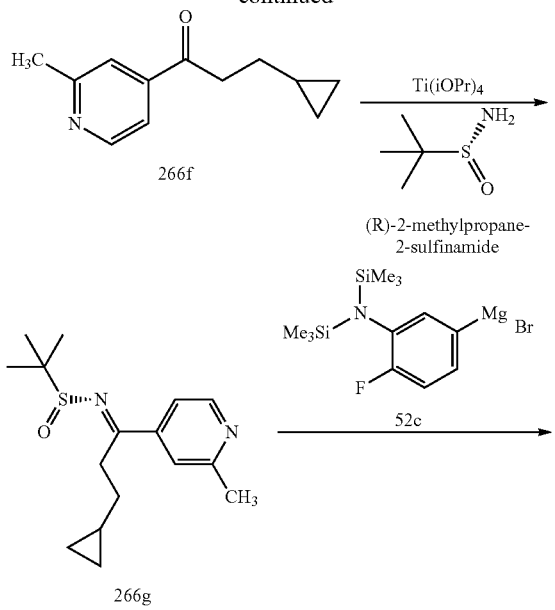

934
-continued

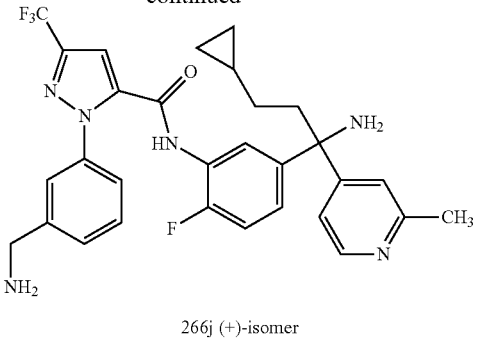

266j (+)-isomer

Preparation of (+)-N-(5-(1-amino-3-cyclopropyl-1-(2-methylpyridin-4-yl)propyl)-2-fluorophenyl)-1-(3-(aminomethyl)phenyl)-3-(trifluoromethyl)-1H-pyrazole-5-carboxamide (266j)

Step-1: Preparation of 2-methyl-isonicotinic Acid (266b)

To a solution of 2,4-dimethyl-pyridine (266a) (100 g, 933.245 mmol) in water (1000 mL) was added potassium permanganate (294.97 g, 1866.489 mmol) portion-wise over a period of 2 h. The resulting reaction mixture was heated at 80° C. for 12 h. The reaction mixture was cooled to room temperature, filtered through celite bed and filtrate was concentrated under reduced pressure to a volume of 250 mL at 50° C. The obtained solution was cooled to 0° C. and pH was adjusted to 3 using 1N HCl (temperature between 0° C. to 5° C.). The solid obtained was collected by filtration washed with chilled water and dried to afford 2-methylisonicotinic acid (266b) (22.3 g, yield: 17.42%); $^1$H NMR (D$_2$O) δ 8.52 (s, 1H), 7.94-7.90 (m, 2H), 2.69 (s, 3H); MS (+) 138.1 (M+1).

Step-2: Preparation of N-methoxy-N,2-dimethylisonicotinamide (266c)

To a stirred solution of 2-methylisonicotinic acid (266b) (17.8 g, 129.798 mmol) in N,N-dimethylformamide (180 mL) was added N,N-diisopropylethylamine (67.105 g, 519.192 mmol) and 1-ethyl-3-(3-dimethylaminopropyl)carbodiimide hydrochloride (EDCI, 40.299 g, 259.596 mmol) and hydroxybenzotriazole (HOBt, 39.753 g, 259.596 mmol) at room temperature. The resulting reaction mixture was stirred for 0.5 h at room temperature followed by the addition of N, O dimethyl hydroxyl amine hydrochloride (13.8 g, 141,479 mmol). The reaction mixture was stirred at room temperature for 12 h, quenched with water (500 mL), extracted with ethyl acetate (5×500 mL). The combined organic layers were dried over sodium sulfate, filtered and concentrated. The residue obtained was purified by column chromatography to afford N-methoxy-N,2-dimethylisonicotinamide (266c) (23 g, 98.4% yield) as a reddish thick solid; $^1$H NMR (CDCl$_3$) δ 8.29-8.27 (d, 1H), 7.08 (s, 1H), 7.02-7.01 (d, 1H), 3.27 (s, 3H), 3.07 (s, 3H), 2.32 (s, 3H); MS (ES+) 181.1 (M+1).

Step-3: Preparation of 1-(2-methylpyridin-4-yl)ethanone (266d)

To a stirred solution of N-methoxy-N,2-dimethylisonicotinamide (266c) (26 g, 144.281 mmol) in THF (520 mL) was

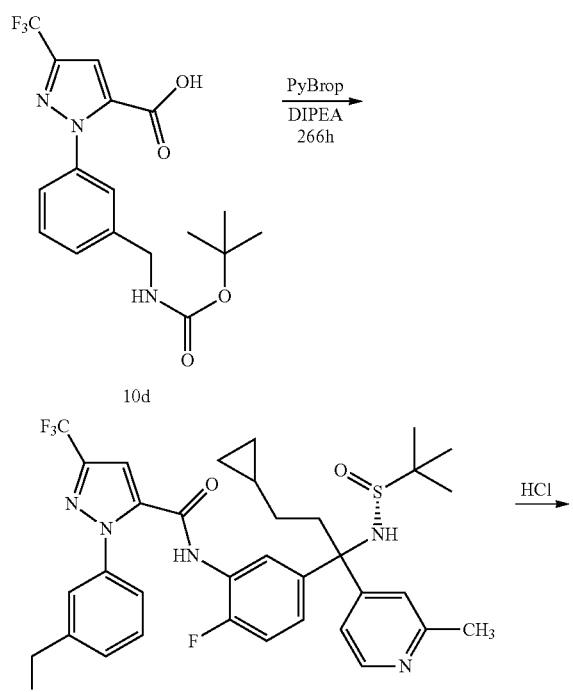

added MeLi (6.342 g, 288.562 mmol, 1 M solution in THF) under nitrogen atmosphere at −78° C. The reaction mixture was warmed to room temperature over a period of 1 h, quenched with saturated NH$_4$Cl solution at 0° C. The resulting reaction mixture was extracted with ethyl acetate and the organic layer was washed with water and brine, dried over sodium sulfate, filtered and concentrated. The residue obtained was purified by column chromatography to afford 1-(2-methylpyridin-4-yl)ethanone (266d) (11 g, 56.4% yield) as a reddish thick liquid; $^1$H NMR (CDCl$_3$) δ 8.61-8.59 (d, 1H), 7.51-7.45 (d, 1H), 7.45-7.44 (m, 1H), 2.56 (s, 3H), 2.53 (s, 3H); MS (ES+) 136.1 (M+1).

Step-4: Preparation of 3-cyclopropyl-1-(2-methylpyridin-4-yl)prop-2-en-1-one (266e)

To a solution of 1-(2-methylpyridin-4-yl)ethanone (266d) (11 g, 81.383 mmol) in methanol (110 mL) at 0° C. was added cyclopropane carboxaldehyde (10.039 g, 143.234 mmol), aqueous potassium hydroxide (1N, 0.911 g, 16.276 mmol) and stirred at room temperature for 12 h. The reaction mixture was cooled to 0° C., added 1N Hydrochloric acid (20.5 mL) and concentrated to remove methanol. The obtained residue was partitioned with ethyl acetate and water (75:75 mL). Aqueous layer was separated and extracted with ethyl acetate (2×75 mL). The combined organic layer were washed with water (100 mL), brine (100 mL), dried over sodium sulfate, filtered and concentrated. The residue obtained was purified by column chromatography to afford 3-cyclopropyl-1-(2-methylpyridin-4-yl)prop-2-en-1-one (266e) (4.5 g, 29.5% yield) as a reddish liquid; MS (ES+) 188.1 (M+1).

Step-5: Preparation of 3-cyclopropyl-1-(2-methylpyridin-4-yl)propan-1-one (266f)

Compound 266f was prepared from 3-cyclopropyl-1-pyridin-4-yl-propenone (266e) (8 g, 42.726 mmol) according to the procedure reported in step-2 of scheme 212 as described for preparation of compound 212c gave after purification by column chromatography 3-cyclopropyl-1-(2-methylpyridin-4-yl)propan-1-one (266f) (5.5 g 68.1% yield) as yellow liquid; $^1$H NMR (CDCl$_3$) δ 8.61-8.59 (d, 1H), 7.53 (s, 1H), 7.47-7.46 (dd, 1H), 3.02-2.97 (m, 2H), 2.58 (s, 3H), 1.60-1.53 (m, 2H), 0.71-0.66 (m, 1H), 0.41-0.37 (m, 2H), 0.05-0.01 (m, 2H); MS (ES+) 190.2 (M+1).

Step-6: Preparation of (R)—N-(3-cyclopropyl-1-(2-methylpyridin-4-yl)propylidene)-2-methylpropane-2-sulfinamide (266g)

Compound 266g was prepared from 3-cyclopropyl-1-(2-methylpyridin-4-yl)propan-1-one (266f) (5.5 g, 29.062 mmol) and R-2-methyl propane-2-sulfinamide (4.209 g, 34.729 mmol) according to the procedure reported in step-1 of scheme 208 as described for preparation of compound 208a gave after purification by column chromatography (R)—N-(3-cyclopropyl-1-(2-methylpyridin-4-yl)propylidene)-2-methylpropane-2-sulfinamide (266g) (7 g, 82.44% yield) as a yellow liquid; $^1$H (CDCl$_3$) δ 8.51-8.49 (d, 1H), 7.51-7.33 (m, 2H), 3.35-3.05 (m, 2H), 2.54 (s, 3H), 1.54-1.49 (m, 2H), 1.24 (s, 9H), 0.75-0.61 (m, 1H), 0.41-0.31 (m, 2H), 0.05-0.01 (m, 2H); MS (ES+) 293.2 (M+1).

Step-7: Preparation of (R)—N-(1-(3-amino-4-fluorophenyl)-3-cyclopropyl-1-(2-methylpyridin-4-yl)propyl)-2-methylpropane-2-sulfinamide (266h)

Compound 266h was prepared from (R)—N-(3-cyclopropyl-1-(2-methylpyridin-4-yl)propylidene)-2-methylpropane-2-sulfinamide (266g) (5.5 g, 29.062 mmol) and R-2-methyl propane-2-sulfinamide (2 g, 6.839 mmol) and freshly prepared (3-(bis(trimethylsilyl)amino)-4-fluorophenyl)magnesium bromide (52c) (19.10 mL, 15.28 mmol) according to the procedure reported in step-2 of scheme 208 as described for preparation of compound 208b gave after purification by column chromatography (R)—N-(1-(3-amino-4-fluorophenyl)-3-cyclopropyl-1-(2-methylpyridin-4-yl)propyl)-2-methylpropane-2-sulfinamide (266h) (0.8 g, 29.0% yield) as a reddish thick liquid; $^1$H NMR (DMSO-d$_6$) δ 8.36-8.34 (d, 1H), 7.24 (s, 1H), 7.12-7.10 (d, 1H), 6.95-6.91 (m, 1H), 6.76-6.72 (m, 1H), 6.59-6.50 (m, 1H), 5.38-5.32 (m, 1H), 5.11 (s, 2H), 2.49 (s, 3H), 2.05-2.01 (m, 2H), 1.55-1.51 (m, 2H), 1.16 (s, 9H), 0.9-0.85 (m, 1H), 0.39-0.37 (m, 2H), 0.03-0.09 (m, 2H); MS (ES+) 404.3 (M+1).

Step-8: Preparation of tert-butyl 3-(5-(5-(3-cyclopropyl-1-((R)-1,1-dimethylethylsulfinamido)-1-(2-methylpyridin-4-yl)propyl)-2-fluorophenylcarbamoyl)-3-(trifluoromethyl)-1H-pyrazol-1-yl)benzylcarbamate (266i)

Compound 266i was prepared from (R)—N-(1-(3-amino-4-fluorophenyl)-3-cyclopropyl-1-(2-methylpyridin-4-yl)propyl)-2-methylpropane-2-sulfinamide (266h) (0.5 g, 1.238 mmol) and 1-(3-((tert-butoxycarbonylamino)methyl)phenyl)-3-(trifluoromethyl)-1H-pyrazole-5-carboxylic acid (10d) (0.573 g, 1.2 mmol) according to the procedure reported in step-3 of scheme 208 as described for preparation of compound 208c gave after purification by column chromatography of tert-butyl 3-(5-(5-(3-cyclopropyl-1-((R)-1,1-dimethylethylsulfinamido)-1-(2-methylpyridin-4-yl)propyl)-2-fluorophenylcarbamoyl)-3-(trifluoromethyl)-1H-pyrazol-1-yl)benzylcarbamate (266i) (0.25 g, 26.2% yield) as a reddish thick liquid; $^1$H NMR (DMSO-d$_6$) δ 10.66 (s, 1H), 8.42-8.40 (d, 1H), 7.65-7.49 (m, 2H), 7.48-7.28 (m, 8H), 7.14 (s, 1H), 5.54 (s, 1H), 4.27-4.25 (d, 2H), 2.58 (s, 3H), 1.47-1.45 (m, 2H), 1.5 (s, 9H), 1.34-1.31 (m, 2H) 1.2 (s, 9H), 0.85-0.71 (m, 1H), 0.45-0.35 (m, 2H), 0.03-0.01 (m, 2H); MS (ES+) 771.4 (M+1).

Step-9: Preparation of (+)-N-(5-(1-amino-3-cyclopropyl-1-(2-methylpyridin-4-yl)propyl)-2-fluorophenyl)-1-(3-(aminomethyl)phenyl)-3-(trifluoromethyl)-1H-pyrazole-5-carboxamide (266j)

To a stirred solution of tert-butyl 3-(5-(5-(3-cyclopropyl-1-((R)-1,1-dimethylethylsulfinamido)-1-(2-methylpyridin-4-yl)propyl)-2-fluorophenylcarbamoyl)-3-(trifluoromethyl)-1H-pyrazol-1-yl)benzylcarbamate (266i) (0.25 g, 0.324 mmol) in ethanol (5 mL) was added HCl (4N in MeOH, 20 mL) at room temperature. The resulting reaction mixture was heated to reflux for 1 hour, cooled to room temperature and concentrated in vacuum. The residue obtained was purified twice by flash chromatography (silica, 12 g, eluting with 0-100% CMA80 in CHCl$_3$) to (+)-N-(5-(1-amino-3-cyclopropyl-1-(2-methylpyridin-4-yl)propyl)-2-fluorophenyl)-1-(3-(aminomethyl)phenyl)-3-(trifluoromethyl)-1H-pyrazole-5-carboxamide (266j) (65 mg, 35.5% yield) free base as a white solid; $^1$H NMR (300 MHz, DMSO-d$_6$) δ 10.53 (s, 1H), 8.29 (d, J=5.3 Hz, 1H), 7.57 (m, 2H), 7.50 (m, 1H), 7.42 (m, 2H), 7.29 (m, 3H), 7.19 (d, J=9.6 Hz, 1H), 7.12 (d, J=6.6 Hz, 1H), 3.77 (s, 2H), 2.40 (s, 3H), 2.31-2.08 (m, 4H), 1.09-0.78 (m, 2H), 0.70-0.52 (m, 1H), 0.40-0.27 (m, 2H), 0.03--0.14 (m, 2H); $^{19}$F NMR (282 MHz, DMSO-d$_6$) δ −60.73, −124.10; MS (ES+) 567.3 (M+1); 565.3 (M−1); Optical Rotation [α]$_D$=(+) 12.38

[0.21, MeOH]. To a solution of free base of compound (266j) (50 mg, 0.088 mmol) in MeOH (3 mL) was added HCl (3N in MeOH) (0.588 mL, 1.765 mmol), stirred for 3 h at room temperature and concentrated in vacuum to dryness. The residue was taken up with water/ACN freeze dried to give (+)-N-(5-(1-amino-3-cyclopropyl-1-(2-methyl-pyridin-4-yl)propyl)-2-fluorophenyl)-1-(3-(aminomethyl)phenyl)-3-(trifluoromethyl)-1H-pyrazole-5-carboxamide (266j) (56 mg, 94% yield) hydrochloride salt as a white solid; $^1$H NMR (300 MHz, DMSO-d$_6$) δ 10.93 (s, 1H), 9.78 (s, 3H), 8.77 (d, J=5.9 Hz, 1H), 8.52 (s, 3H), 7.83-7.77 (m, 1H), 7.74 (m, 2H), 7.71-7.58 (m, 3H), 7.58-7.47 (m, 2H), 7.40 (dd, J=7.0, 1.5 Hz, 2H), 4.11 (d, J=5.8 Hz, 2H), 2.65 (s, 3H), 2.63-2.50 (m, 2H), 1.32-0.94 (m, 2H), 0.67 (m, 1H), 0.48-0.24 (m, 2H), 0.01 (m, 2H); $^{19}$F NMR (282 MHz, DMSO-d$_6$) δ −60.82, −119.73. MS (ES+) 567.3 (M+1), (ES−) 565.4 (M−1).

Scheme 267

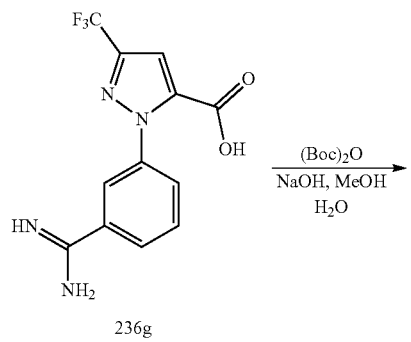

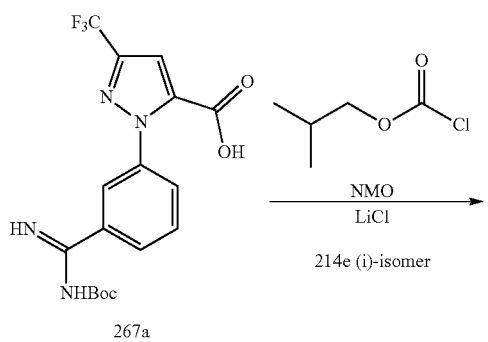

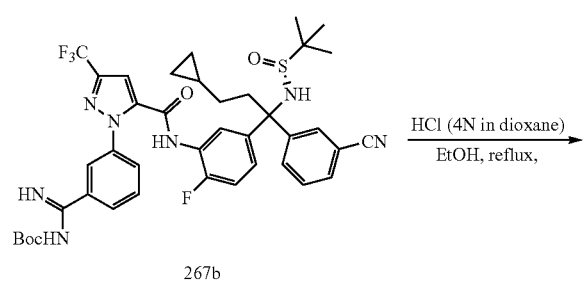

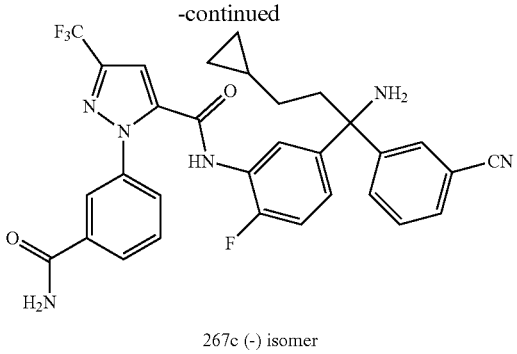

267c (−) isomer

Preparation of (−)-N-(5-(1-amino-1-(3-cyanophenyl)-3-cyclopropylpropyl)-2-fluorophenyl)-1-(3-carbamoylphenyl)-3-(trifluoromethyl)-1H-pyrazole-5-carboxamide (267c)

Step-1: Preparation of 1-(3-(N-(tert-butoxycarbonyl)carbamimidoyl)phenyl)-3-(trifluoromethyl)-1H-pyrazole-5-carboxylic acid (267a)

To a solution of 1-(3-carbamimidoylphenyl)-3-(trifluoromethyl)-1H-pyrazole-5-carboxylic acid (236g) (1.2 g, 4.02 mmol) in MeOH—H$_2$O (50 mL, Ratio: 1:2) was added (Boc)$_{2O}$ (1.121 g, 4.83 mmol) and sodium hydroxide (0.322 g, 8.05 mmol). The resulting mixture was stirred at room temperature for 12 h. Additional (Boc)$_{2O}$ (0.878 g, 4.02 mmol) was added and the resulting mixture was stirred for 8 h, diluted with water (100 mL) and extracted with ethyl acetate (3×100 mL). The organic layers were combined, dried, filtered, and concentrated in vacuum to dryness. The residue obtained was purified by flash column chromatography (silica gel 40 g, eluting with 0-100% CMA-80 in chloroform) to afford 1-(3-(N-(tert-butoxycarbonyl)carbamimidoyl)phenyl)-3-(trifluoromethyl)-1H-pyrazole-5-carboxylic acid (267a) (205 mg, 0.515 mmol, 12.79% yield) as a white solid; $^1$H NMR (300 MHz, DMSO-d$_6$) δ 9.18 (s, 1H), 8.12-7.94 (m, 2H), 7.77-7.65 (m, 1H), 7.57 (t, J=7.8 Hz, 1H), 7.13 (s, 1H), 1.45 (s, 9H); $^{19}$F NMR (282 MHz, DMSO-d$_6$) δ −60.45; MS (ES+): 399.4 (M+1), (ES−) 397.3 (M−1).

Step-2: Preparation of tert-butyl (3-(5-(5-(1-(3-cyanophenyl)-3-cyclopropyl-1-((R)-1,1-dimethylethylsulfinamido)propyl)-2-fluorophenylcarbamoyl)-3-(trifluoromethyl)-1H-pyrazol-1-yl)phenyl)(imino)methylcarbamate (267b)

To a solution of 1-(3-(N-(tert-butoxycarbonyl)carbamimidoyl)phenyl)-3-(trifluoromethyl)-1H-pyrazole-5-carboxylic acid (267a) (150 mg, 0.377 mmol) in THF (20 mL) at 0° C. was added NMO (44.1 mg, 0.377 mmol), isobutylchloroformate (153 mg, 1.125 mmol) and stirred at 0° C. for 1 h. To the reaction mixture was added (R)—N-((−)-1-(3-amino-4-fluorophenyl)-1-(3-cyanophenyl)-3-cyclopropylpropyl)-2-methylpropane-2-sulfinamide (214e) (156 mg, 0.377 mmol), lithium chloride (23.95 mg, 0.565 mmol), stirred at 0° C. for 2 h, quenched with water (10 mL) and extracted with ethyl acetate (3×20 mL). The organic layers were combined, dried, filtered, and concentrated in vacuum to dryness. The residue obtained was purified by flash column chromatography (silica gel 12 g, eluting with 0-100% EtOAc in hexane) to tert-butyl (3-(5-(5-(1-(3-cyanophenyl)-3-cyclopropyl-1-((R)-1,1-dimethylethylsulfinamido)propyl)-2-fluorophenylcarbamoyl)-3-(trifluoromethyl)-1H-pyrazol-1-yl)phenyl)(imino)methylcarbamate (267b) (88 mg, 0.111 mmol, 29.4% yield) as a white solid; $^1$H NMR (300 MHz, Chloroform-d) δ 8.09 (m, 1H), 7.90 (s, 1H), 7.85 (d, J=8.5 Hz, 1H), 7.67-7.61 (m, 1H), 7.55 (d, J=7.9 Hz, 2H), 7.47 (m, 1H), 7.39 (d, J=8.2 Hz, 2H), 7.20 (m, 1H), 7.04 (m, 1H), 6.99-6.92 (m, 1H), 2.58 (m, 2H), 1.49 (s, 9H), 1.19 (s, 9H), 0.97-0.85 (m, 2H), 0.59 (m, 1H), 0.36 (m, 2H), −0.12 (m, 2H); MS (ES+): 794.6 (M+1); IR (KBr) 2232 cm$^{-1}$.

Step-3: Preparation of (−)-N-(5-(1-amino-1-(3-cyanophenyl)-3-cyclopropylpropyl)-2-fluorophenyl)-1-(3-carbamoylphenyl)-3-(trifluoromethyl)-1H-pyrazole-5-carboxamide (267c)

To a solution of to tert-butyl (3-(5-(5-(1-(3-cyanophenyl)-3-cyclopropyl-1-((R)-1,1-dimethylethylsulfinamido)propyl)-2-fluorophenylcarbamoyl)-3-(trifluoromethyl)-1H-pyrazol-1-yl)phenyl)(imino)methylcarbamate (267b) (70 mg, 0.088 mmol) in EtOH (10 mL) was added HCl (4N in dioxane) (0.220 mL, 0.882 mmol) and heated at reflux for 10 min. The solution was concentrated under vacuum to dryness and the residue obtained was purified by flash column chromatography (silica gel, eluting with 0-100% CMA80 in chloroform) to furnish compound 267c (17 mg, 0.029 mmol) free base as a white solid. The free base was converted into HCl salt by using HCl (4N in dioxane, 0.1 mL) and freeze dried to afford (−)-N-(5-(1-amino-1-(3-cyanophenyl)-3-cyclopropylpropyl)-2-fluorophenyl)-1-(3-carbamoylphenyl)-3-(trifluoromethyl)-1H-pyrazole-5-carboxamide (267c), 17 mg, 0.027 mmol, 30.7% yield) as a white solid; $^1$H NMR (300 MHz, DMSO-d$_6$) δ 10.73 (s, 1H), 9.26 (s, 3H), 8.16 (s, 1H), 8.04-7.98 (m, 2H), 7.89 (dt, J=7.3, 1.4 Hz, 1H), 7.83 (s, 1H), 7.71-7.54 (m, 7H), 7.42 (dd, J=10.1, 8.8 Hz, 1H), 7.29-7.19 (m, 1H), 2.50 (dp, J=39.9, 1.8 Hz, 2H), 1.06 (tt, J=12.3, 5.3 Hz, 2H), 0.77-0.59 (m, 1H), 0.48-0.29 (m, 1H), −0.02 (s, 2H); $^{19}$F NMR (282 MHz, MeOH-d$_4$) δ −64.55, −128.38; MS (ES+) 613.5 (M+Na); IR (KBr) 2235 cm$^{-1}$; Analysis calculated for C$_{31}$H$_{26}$F$_4$N$_6$O$_2$·HCl·2.75H$_2$O; C, 55.03; H, 4.84; N, 12.42; Found: C, 55.30; H, 4.81; N, 12.00; Optical rotation: [α]$_D$=(−) 3.2 [0.125, MeOH].

Scheme 268

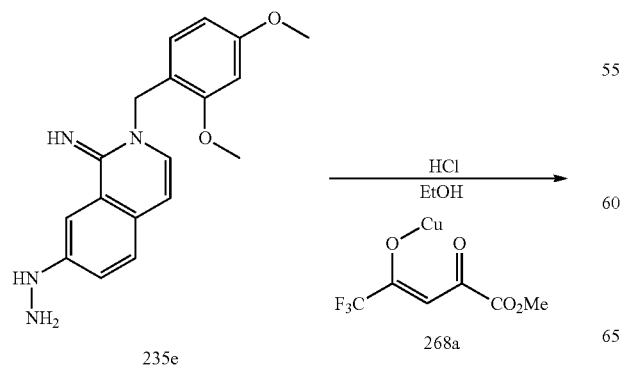

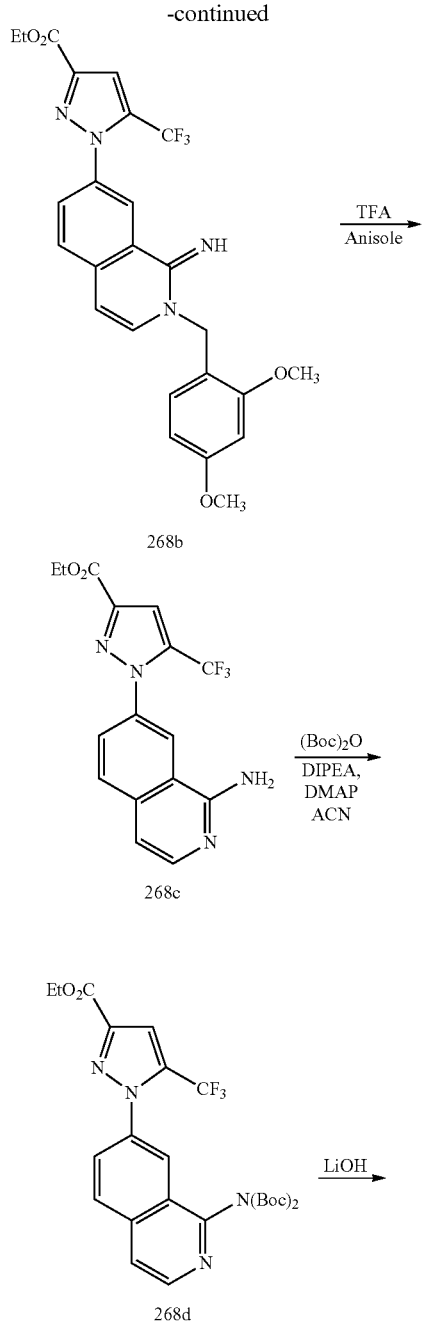

-continued

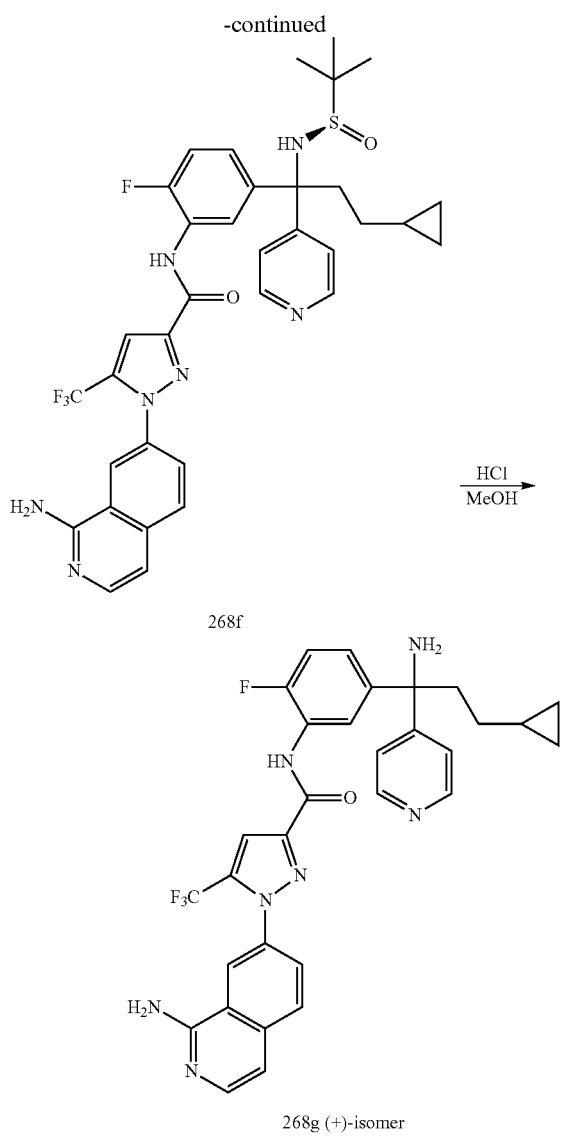

Preparation of (+)-N-(5-(1-amino-3-cyclopropyl-1-(pyridin-4-yl)propyl)-2-fluorophenyl)-1-(1-aminoisoquinolin-7-yl)-5-(trifluoromethyl)-1H-pyrazole-3-carboxamide (268g)

Step-1: Preparation of ethyl 1-(2-(2,4-dimethoxybenzyl)-1-imino-1,2-dihydroisoquinolin-7-yl)-5-(trifluoromethyl)-1H-pyrazole-3-carboxylate (268b)

To a solution of 2-(2,4-dimethoxybenzyl)-7-hydrazinylisoquinolin-1(2H)-imine hydrochloride (235e) (13.434 g, 41.4 mmol) in ethanol (50 mL) was added the copper complex (268a) (prepared according to Russian Chemical Bulletin, 1990, 1273-1277) (10.79 g, 41.4 mmol). The resulting mixture was cooled to 0° C., added conc. HCl (15.10 g, 414 mmol) and stirred at room temperature overnight. Additional HCl (7.02 g, 193 mmol) was added and reaction mixture was heated at reflux overnight, cooled to room temperature and concentrated in vacuum. The residue was purified by flash column chromatography (silica gel, eluting with CMA80 in chloroform 0-70%) to afford ethyl 1-(1-aminoisoquinolin-7-yl)-5-(trifluoromethyl)-1H-pyra- zole-3-carboxylate (268c) (1.90 g, 5.42 mmol, 13.10% yield) and ethyl 1-(2-(2,4-dimethoxybenzyl)-1-imino-1,2-dihydroisoquinolin-7-yl)-5-(trifluoromethyl)-1H-pyrazole-3-carboxylate (268b) (4.1 g, 8.19 mmol, 19.78% yield). $^1$H NMR (300 MHz, DMSO-$d_6$) δ 8.45 (s, 1H), 7.76-7.55 (m, 3H), 7.27 (d, J=7.4 Hz, 1H), 7.06 (d, J=8.4 Hz, 1H), 6.60 (d, J=2.3 Hz, 1H), 6.48 (dd, J=8.4, 2.3 Hz, 1H), 6.21 (d, J=7.4 Hz, 1H), 4.97 (s, 2H), 4.35 (q, J=7.1 Hz, 2H), 3.80 (s, 3H), 3.74 (s, 3H), 1.32 (t, J=7.1 Hz, 3H); $^{19}$F NMR (282 MHz, DMSO) δ −56.85.

Step-2: Preparation of ethyl 1-(1-aminoisoquinolin-7-yl)-5-(trifluoromethyl)-1H-pyrazole-3-carboxylate (268c)

Compound 268c was prepared from ethyl 1-(2-(2,4-dimethoxybenzyl)-1-imino-1,2-dihydroisoquinolin-7-yl)-5-(trifluoromethyl)-1H-pyrazole-3-carboxylate (268b) (4.1 g, 8.19 mmol) according to the procedure reported for the preparation of compound 253a, step-1 scheme-253 gave after purification by column chromatography (silica gel, eluting with CMA80 in chloroform 0-40%) ethyl 1-(1-aminoisoquinolin-7-yl)-5-(trifluoromethyl)-1H-pyrazole-3-carboxylate (268c) (2.4 g, 6.85 mmol, 84% yield) as an off white solid; $^1$H NMR (300 MHz, Chloroform-d) δ 8.49 (s, 1H), 7.86 (q, J=8.6 Hz, 2H), 7.52 (d, J=6.5 Hz, 1H), 7.36 (s, 1H), 7.02 (d, J=6.1 Hz, 1H), 4.38 (q, J=7.0 Hz, 2H), 1.34 (t, J=7.0 Hz, 3H).

Step-3: Preparation of ethyl 1-(1-(bis(tert-butoxycarbonyl)amino)isoquinolin-7-yl)-5-(trifluoromethyl)-1H-pyrazole-3-carboxylate (268d)

To a solution of ethyl 1-(1-aminoisoquinolin-7-yl)-5-(trifluoromethyl)-1H-pyrazole-3-carboxylate (268c) (1.90 g, 5.42 mmol) in acetonitrile (75 mL) was added DIPEA (4.74 mL, 27.1 mmol), Boc anhydride (3.55 g, 16.27 mmol), DMAP (0.066 g, 0.542 mmol) and stirred at room temperature overnight. Additional Boc anhydride (2.368 g, 10.85 mmol) were added, and the reaction mixture was heated at 60° C. for 4 h. The reaction mixture was cooled to room temperature, added Boc anhydride (1.776 g, 8.14 mmol) and heated at 50° C. overnight. The reaction mixture was evaporated to dryness, treated with brine (100 mL) and extracted with ethyl acetate (2×100 mL). The combined organics were dried over MgSO$_4$, filtered, evaporated to dryness and the residue obtained was purified by flash column chromatography (silica gel 40 g, eluting with 0-40% ethyl acetate in hexane) to afford ethyl 1-(1-(bis(tert-butoxycarbonyl)amino)isoquinolin-7-yl)-5-(trifluoromethyl)-1H-pyrazole-3-carboxylate (268d) (647 mg, 1.175 mmol, 21.67% yield) as a white semi-solid. $^1$H NMR (300 MHz, Chloroform-d) δ 8.57 (d, J=5.7 Hz, 1H), 8.16 (s, 1H), 8.05 (d, J=8.8 Hz, 1H), 7.87 (dd, J=8.8, 2.0 Hz, 1H), 7.78 (d, J=5.7 Hz, 1H), 7.42 (s, 1H), 4.48 (q, J=7.1 Hz, 2H), 1.44 (t, J=7.1 Hz, 3H), 1.32 (s, 18H).

Step-4: Preparation of 1-(1-aminoisoquinolin-7-yl)-5-(trifluoromethyl)-1H-pyrazole-3-carboxylic Acid (268e)

To a solution of ethyl 1-(1-(bis(tert-butoxycarbonyl)amino)isoquinolin-7-yl)-5-(trifluoromethyl)-1H-pyrazole-3-carboxylate (268d) (544 mg, 0.988 mmol) in THF/H$_2$O (30 mL, Ratio: 3:1) at room temperature was added lithium hydroxide monohydrate (415 mg, 9.88 mmol) and heated at 67° C. overnight. The reaction mixture was diluted with EtOAc (35 mL), organic layer was separated and the aqueous layer was acidified with conc. HCl to pH 2. The white precipitate obtained was collected by filtration, washed with water (2×5 mL), dried in vacuum to furnish 1-(1-aminoisoquinolin-7-yl)-5-(trifluoromethyl)-1H-pyrazole-3-carboxylic acid (268e) (295 mg, 93%) as a white solid. $^1$H NMR (300 MHz, DMSO-d$_6$) δ 8.52 (s, 1H), 7.98-7.86 (m, 2H), 7.79 (d, J=8.6 Hz, 2H), 7.61 (s, 1H), 7.25 (s, 2H), 7.06 (d, J=5.7 Hz, 1H); $^{19}$F NMR (282 MHz, DMSO) δ −56.71; MS (ES+) 323 (M+1), (ES−) 321 (M−1).

Step-5: Preparation of 1-(1-aminoisoquinolin-7-yl)-N-(5-(3-cyclopropyl-1-((R)-1,1-dimethylethylsulfinamido)-1-(pyridin-4-yl)propyl)-2-fluorophenyl)-5-(trifluoromethyl)-1H-pyrazole-3-carboxamide (2368f)

Compound 268f was prepared from 1-(1-aminoisoquinolin-7-yl)-5-(trifluoromethyl)-1H-pyrazole-3-carboxylic acid (268e) (100 mg, 0.310 mmol) and (R)—N-((−)-1-(3-amino-4-fluorophenyl)-3-cyclopropyl-1-(pyridin-4-yl)propyl)-2-methylpropane-2-sulfinamide (216b) (121 mg, 0.310 mmol) using procedure reported in step-3 of scheme-208 to furnish after purification by column chromatography (silica gel, eluting with 0-40% CMA80 in CHCl$_3$) 1-(1-aminoisoquinolin-7-yl)-N-(5-(3-cyclopropyl-1-((R)-1,1-dimethylethylsulfinamido)-1-(pyridin-4-yl)propyl)-2-fluorophenyl)-5-(trifluoromethyl)-1H-pyrazole-3-carboxamide (268f) (120 mgs) which was used as such without further purification.

Step-6: (+)-N-(5-(1-amino-3-cyclopropyl-1-(pyridin-4-yl)propyl)-2-fluorophenyl)-1-(1-aminoisoquinolin-7-yl)-5-(trifluoromethyl)-1H-pyrazole-3-carboxamide (268g)

To a solution of 1-(1-aminoisoquinolin-7-yl)-N-(5-(3-cyclopropyl-1-((R)-1,1-dimethylethylsulfinamido)-1-(pyridin-4-yl)propyl)-2-fluorophenyl)-5-(trifluoromethyl)-1H-pyrazole-3-carboxamide (268f) (120 mg, 0.173 mmol) in ethanol (10 mL) was added HCl (32 mg, 0.865 mmol) and heated at reflux for 3 h. The reaction mixture was cooled to room temperature, concentrated in vacuum and purified by flash column chromatography (silica gel, eluting with chloroform in CMA80 0-40%) to give (+)-N-(5-(1-amino-3-cyclopropyl-1-(pyridin-4-yl)propyl)-2-fluorophenyl)-1-(1-aminoisoquinolin-7-yl)-5-(trifluoromethyl)-1H-pyrazole-3-carboxamide (268g) (7 mg, 0.012 mmol, 6.86% yield) as a white solid. $^1$H NMR (300 MHz, DMSO-d$_6$) δ 10.20 (s, 1H), 8.54 (d, J=2.3 Hz, 1H), 8.49-8.41 (m, 2H), 7.96-7.89 (m, 2H), 7.86-7.76 (m, 1H), 7.68 (s, 1H), 7.63 (dd, J=7.5, 2.4 Hz, 1H), 7.43-7.38 (m, 2H), 7.32 (m, 1H), 7.19 (dd, J=10.2, 8.6 Hz, 1H), 7.03 (d, J=5.1 Hz, 3H), 2.34 (s, 2H), 2.23 (m, 2H), 1.06 (m, 2H), 0.64 (m, 1H), 0.44-0.31 (m, 2H), −0.01--0.15 (m, 2H); $^{19}$F NMR (282 MHz, DMSO) δ −56.82, −124.34; MS (ES+) 590.3 (M+1); (ES−) 588.3 (M−1); Optical rotation: $[α]_D$=(+) 10.67 [0.225, MeOH].

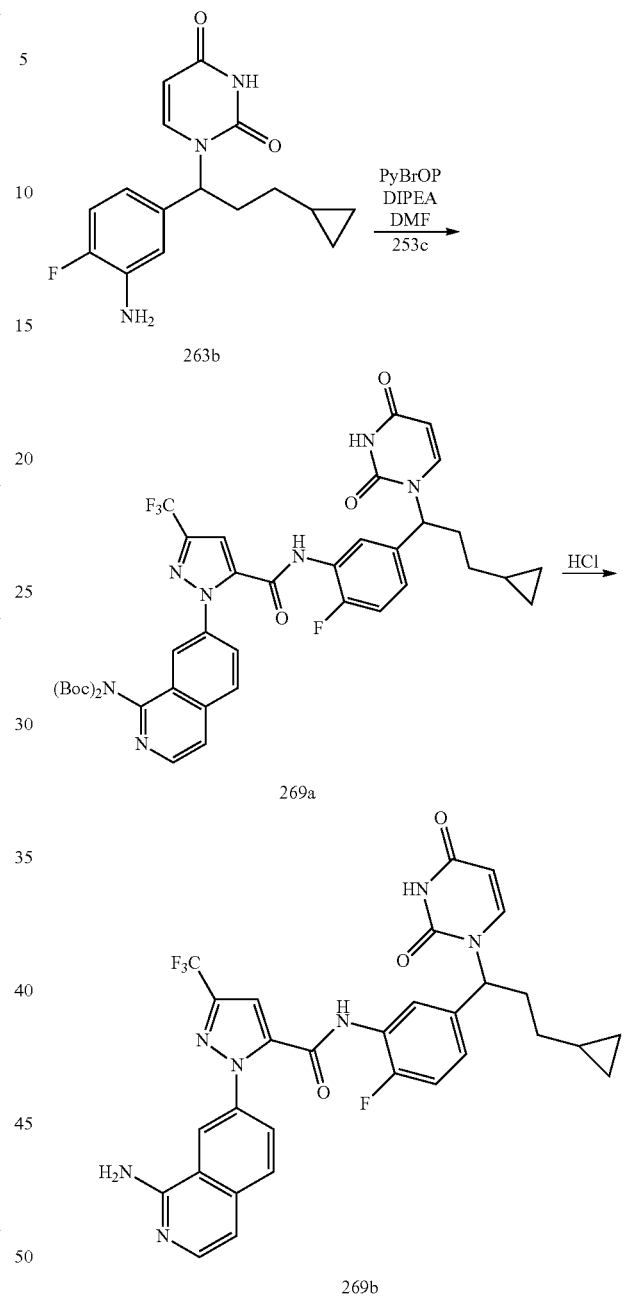

Scheme 269

Preparation of 1-(1-aminoisoquinolin-7-yl)-N-(5-(3-cyclopropyl-1-(2,4-dioxo-3,4-dihydropyrimidin-1(2H)-yl)propyl)-2-fluorophenyl)-3-(trifluoromethyl)-1H-pyrazole-5-carboxamide (269b)

Step-1: Preparation of 1-(1-bis(tert-butoxycarbonyl)amino)isoquinolin-7-yl)-N-(5-(3-cyclopropyl-1-(2,4-dioxo-3,4-dihydropyrimidin-1(2H)-yl)propyl)-2-fluorophenyl)-3-(trifluoromethyl)-1H-pyrazole-5-carboxamide (269a)

Compound 269a was prepared from 1-(1-(3-amino-4-fluorophenyl)-3-cyclopropylpropyl)pyrimidine-2,4(1H, 3H)-dione (263b) (163 mg, 0.537 mmol) and 1-(1-(bis(tert-butoxycarbonyl)amino)isoquinolin-7-yl)-3-(trifluoromethyl)-1H-pyrazole-5-carboxylic acid (253c) (337 mg, 0.645 mmol) according to the procedure reported in step-3 of scheme 208 for preparation of compound 208c to afford after purification by flash column chromatography [silica gel 40 g, eluting with 0-90% EtOAc/MeOH (9:1, v/v) in hexane] 1-(1-bis(tert-butoxycarbonyl)amino)isoquinolin-7-yl)-N-(5-(3-cyclopropyl-1-(2,4-dioxo-3,4-dihydropyrimidin-1(2H)-yl)propyl)-2-fluorophenyl)-3-(trifluoromethyl)-1H-pyrazole-5-carboxamide (269a) (55 mg, 0.068 mmol, 12.7% yield) as a white solid; MS (ES+), 830.4 (M+Na); (ES−) 806.4 (M−1).

Step-2: Preparation of 1-(1-aminoisoquinolin-7-yl)-N-(5-(3-cyclopropyl-1-(2,4-dioxo-3,4-dihydropyrimidin-1(2H)-yl)propyl)-2-fluorophenyl)-3-(trifluoromethyl)-1H-pyrazole-5-carboxamide (269b)

To a solution of 1-(1-bis(tert-butoxycarbonyl)amino)isoquinolin-7-yl)-N-(5-(3-cyclopropyl-1-(2,4-dioxo-3,4-dihydropyrimidin-1(2H)-yl)propyl)-2-fluorophenyl)-3-(trifluoromethyl)-1H-pyrazole-5-carboxamide (269a) (55 mg, 0.068 mmol) in MeOH (15 mL) was added HCl (3N in MeOH) (0.45 mL, 1.36 mmol) and stirred at room temperature overnight. The reaction was concentrated in vacuum and the residue obtained was purified by flash column chromatography (silica gel 24 g, eluting with 0-40% CMA80 in CHCl$_3$) to furnish 1-(1-aminoisoquinolin-7-yl)-N-(5-(3-cyclopropyl-1-(2,4-dioxo-3,4-dihydropyrimidin-1(2H)-yl)propyl)-2-fluorophenyl)-3-(trifluoromethyl)-1H-pyrazole-5-carboxamide (269b) (9.0 mg, 0.015 mmol, 41.4% yield) as a white solid; $^1$H NMR (300 MHz, DMSO-d$_6$) δ 11.36 (s, 1H), 10.60 (s, 1H), 8.42 (s, 1H), 7.88 (d, J=5.7 Hz, 1H), 7.79 (d, J=8.7 Hz, 1H), 7.74-7.63 (m, 3H), 7.52 (d, J=7.2 Hz, 1H), 7.29 (d, J=7.9 Hz, 2H), 6.98 (m, 3H), 5.57 (m, 2H), 2.31-1.98 (m, 2H), 1.32-0.95 (m, 2H), 0.78-0.57 (m, 1H), 0.47-0.29 (m, 2H), 0.13--0.12 (m, 2H); $^{19}$F NMR (282 MHz, DMSO-d$_6$) δ −60.73, −121.27.

Scheme 270

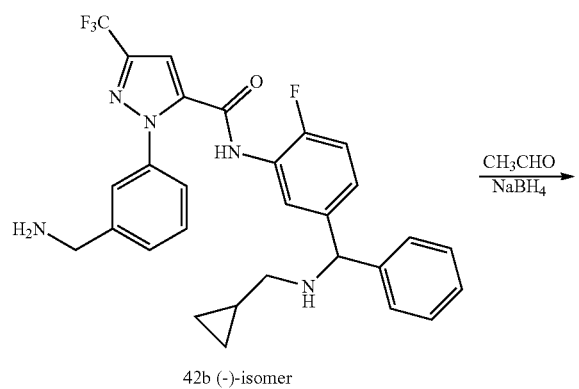

42b (−)-isomer

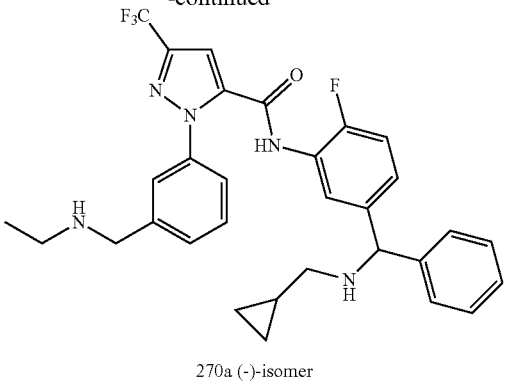

270a (−)-isomer

Preparation of (−)-N-(5-((cyclopropylmethylamino)(phenyl)methyl)-2-fluorophenyl)-1-(3-((ethylamino)methyl)phenyl)-3-(trifluoromethyl)-1H-pyrazole-5-carboxamide (270a)

To a solution of (−)-1-(3-(aminomethyl)phenyl)-N-(5-((cyclopropylmethylamino)(phenyl)methyl)-2-fluorophenyl)-3-(trifluoromethyl)-1H-pyrazole-5-carboxamide (42b) (0.25 g, 0.46 mmol) in MeOH (10 mL) was added acetaldehyde (0.16 mL, 2.8 mmol) and stirred at room temperature for 10 mins. To the reaction mixture was added sodium borohydride (0.035 g, 0.93 mmol) and continued stirring at room temperature for 6 h. The reaction mixture was diluted with water (50 mL) and extracted with ethyl acetate (2×40 ml). The combined organics were washed with brine, dried (MgSO$_4$), filtered and concentrated in vacuum. The residue obtained was purified by flash chromatography [silica gel 24 g, eluting with 0 to 30% CMA80 in chloroform) to afford compound 270a (0.11 g, 0.194 mmol, 41.8% yield) free base as a white solid; $^1$H NMR (300 MHz, DMSO-d$_6$) δ 10.53 (s, 1H), 7.63 (d, J=7.2 Hz, 1H), 7.56 (s, 1H), 7.50-7.24 (m, 9H), 7.22-7.14 (m, 2H), 4.83 (s, 1H), 3.73 (s, 2H), 2.45 (m, 2H), 2.26 (d, J=6.6 Hz, 2H), 0.96 (m, 4H), 0.43-0.30 (m, 2H), 0.04 (m, 2H); 19F NMR (282 MHz, DMSO-d$_6$) δ −60.54, −123.79; MS (ES+) 566.4 (M+1); MS (ES−) 564.4 (M−1), 600.3 (M+Cl); The free base (0.7 g) was converted to HCl salt using 3N HCl (5 eq) to obtain (−)-N-(5-((cyclopropylmethylamino)(phenyl)methyl)-2-fluorophenyl)-1-(3-((ethylamino)methyl)phenyl)-3-(trifluoromethyl)-1H-pyrazole-5-carboxamide (270a) hydrochloride as a white solid; $^1$H NMR (300 MHz, DMSO-d$_6$) δ 10.81 (s, 1H), 10.16 (s, 2H), 9.20 (s, 2H), 7.94 (d, J=7.2 Hz, 1H), 7.80-7.11 (m, 12H), 5.75-5.57 (m, 1H), 4.21 (t, J=5.8 Hz, 2H), 3.05-2.83 (m, 2H), 2.70 (m, 2H), 1.18 (m, 4H), 0.60-0.50 (m, 2H), 0.29 (m, 2H); Optical rotation: [α]$_D$=(−) 3.57 [0.28, MeOH].

Example 271

Plasma Kallikrein Activity Assay.

The effect of compounds of the invention on human plasma kallikrein activity was determined using the chromogenic substrates (DiaPharma Group, Inc., West Chester, Ohio, USA). In these experiments, 2 nM kallikrein (Enzyme Research Laboratories, South Bend, Ind., USA) was incubated with 80 µM S2302 (H-D-Pro-Phe-Arg-p-nitroaniline) in the absence or presence of increasing concentrations of compounds of the invention in a final volume of 200 µL Tris-HCl buffer (200 mM NaCl; 2.5 mM CaCl$_2$; 50 mM Tris-HCl, pH 7.8).

After incubation at 30° C., the activity of kallikrein was measured as a change in absorbance at OD 405 nm using BioTek PowerWave X340 Microplate Reader (Winooski, Vt., USA). Data were analyzed using SigmaPlot software (Systat Software, Inc., San Jose, Calif., USA) (Four Parameter Logistic Curve). Ki values for the inhibitors were determined using the Cheng-Prusoff equation (*Biochem. Pharmacol.* 1973, 22, 3099).

The compounds disclosed in this application have Ki values less than 1 micromolar (µM) for the plasma kallikrein enzyme. See Table 1.

TABLE 1

Measured Ki values for compounds.

| Compound | Ki (nM) | Compound | Ki (nM) | Compound | Ki (nM) |
|---|---|---|---|---|---|
| 161e | >100 | 28f | >100 | 77e | 0.1-50 |
| 162c | >100 | 29e | 0.1-50 | 43f | 0.1-50 |
| 163g | >100 | 30g | >100 | 44c | 0.1-50 |
| 17d | >100 | 31f | >100 | 78d | 0.1-50 |
| 18f | >100 | 32f | >50-100 | 79f | 0.1-50 |
| 19d | >100 | 33e | >100 | 80h | 0.1-50 |
| 20d | >100 | 33f | >100 | 87f | 0.1-50 |
| 18g | >50-100 | 34d | >100 | 88b | 0.1-50 |
| 22b | >100 | 35g | >50-100 | 82f | 0.1-50 |
| 23c | >100 | 34c | 0.1-50 | 83c | 0.1-50 |
| 24c | >100 | 18e | >100 | 46g | 0.1-50 |
| 25b | >50-100 | 81c | >100 | 205f | >100 |
| 25c | >100 | 39e | >100 | 89g | 0.1-50 |
| 26f | >100 | 40b | >100 | 91a | 0.1-50 |
| 18i | >50-100 | 41e | 0.1-50 | 86g | 0.1-50 |
| 18h | >50-100 | 74a | 0.1-50 | 45g | 0.1-50 |
| 21e | >100 | 75a | >50-100 | 47f | 0.1-50 |
| 18j | >100 | 38d | 0.1-50 | 92g | 0.1-50 |
| 18k | 0.1-50 | 76h | >100 | 84h | 0.1-50 |
| 27f | >50-100 | 36d | 0.1-50 | 85c | 0.1-50 |
| 93b | >100 | 109f | 0.1-50 | 128g | 0.1-50 |
| 94b | 0.1-50 | 110f | 0.1-50 | 129f | 0.1-50 |
| 95i | 0.1-50 | 111f | 0.1-50 | 130g | 0.1-50 |
| 96f | 0.1-50 | 112g | 0.1-50 | 131b | 0.1-50 |
| 48f | 0.1-50 | 113f | 0.1-50 | 132f | 0.1-50 |
| 164e | 0.1-50 | 114f | 0.1-50 | 133g | 0.1-50 |
| 97f | >100 | 115e | >50-100 | 134f | 0.1-50 |
| 98b | 0.1-50 | 116e | 0.1-50 | 135c | 0.1-50 |
| 99g | 0.1-50 | 117e | 0.1-50 | 136a | >100 |
| 100e | 0.1-50 | 118f | 0.1-50 | 137a | 0.1-50 |
| 101e | 0.1-50 | 119e | 0.1-50 | 137b | >100 |
| 102b | 0.1-50 | 120e | 0.1-50 | 138f | 0.1-50 |
| 103b | 0.1-50 | 122g | 0.1-50 | 52h | 0.1-50 |
| 104f | 0.1-50 | 121f | 0.1-50 | 139b | 0.1-50 |
| 105g | 0.1-50 | 123g | 0.1-50 | 140e | 0.1-50 |
| 49h | 0.1-50 | 124f | 0.1-50 | 167f | >100 |
| 106a | 0.1-50 | 51f | 0.1-50 | 141e | 0.1-50 |
| 50f | 0.1-50 | 125g | 0.1-50 | 142f | 0.1-50 |
| 107f | 0.1-50 | 126g | 0.1-50 | 143l | 0.1-50 |
| 108e | 0.1-50 | 127f | 0.1-50 | 144d | 0.1-50 |
| 145c | >100 | 57e | 0.1-50 | 181b | >100 |
| 146g | 0.1-50 | 60e | 0.1-50 | 182b | >100 |
| 147e | 0.1-50 | 71a | 0.1-50 | 183b | >100 |
| 148b | 0.1-50 | 71b | 0.1-50 | 184b | >100 |
| 149b | 0.1-50 | 65a | 0.1-50 | 185b | >100 |
| 53f | 0.1-50 | 65b | 0.1-50 | 186b | >100 |
| 150f | 0.1-50 | 192f | 0.1-50 | 187b | >100 |
| 153b | 0.1-50 | 168b | 0.1-50 | 188b | 0.1-50 |
| 151g | 0.1-50 | 169b | >100 | 189b | >100 |
| 152d | 0.1-50 | 170b | >100 | 190b | >100 |
| 154e | 0.1-50 | 171b | >100 | 193f | 0.1-50 |
| 155c | 0.1-50 | 172b | >100 | 191b | >100 |
| 156c | 0.1-50 | 173b | >100 | 195f | 0.1-50 |
| 54e | 0.1-50 | 174b | >100 | 196f | 0.1-50 |
| 55b | 0.1-50 | 175b | >100 | 197f | 0.1-50 |
| 58c | 0.1-50 | 176b | >100 | 198f | 0.1-50 |
| 56c | 0.1-50 | 177b | >100 | 194f | 0.1-50 |
| 68c | 0.1-50 | 178b | >100 | 199f | 0.1-50 |
| 61e | 0.1-50 | 179b | >100 | 200f | 0.1-50 |
| 59c | 0.1-50 | 180b | >100 | 201f | 0.1-50 |

TABLE 1-continued

Measured Ki values for compounds.

| Compound | Ki (nM) | Compound | Ki (nM) | Compound | Ki (nM) |
|---|---|---|---|---|---|
| 202f | 0.1-50 | 166e | 0.1-50 | 42b | 0.1-50 |
| 203f | >100 | 165e | 0.1-50 | 42a | 0.1-50 |
| 157a | >100 | 50g | 0.1-50 | 67a | 0.1-50 |
| 158a | >100 | 50h | 0.1-50 | 67b | 0.1-50 |
| 159a | >100 | 43g | 0.1-50 | 70a | 0.1-50 |
| 160a | >100 | 43h | 0.1-50 | 70b | 0.1-50 |
| 207j | 0.1-50 | 44d | 0.1-50 | 69a | 0.1-50 |
| 247c | 0.1-50 | 44e | 0.1-50 | 69b | 0.1-50 |
| 247e | 0.1-50 | 47g | 0.1-50 | 68d | 0.1-50 |
| 248j | 0.1-50 | 47h | 0.1-50 | 68e | 0.1-50 |
| 249b | 0.1-50 | 46h | 0.1-50 | 63a | 0.1-50 |
| 250c | 0.1-50 | 46i | 0.1-50 | 63b | 0.1-50 |
| 252c | 0.1-50 | 48g | 0.1-50 | 73a | 0.1-50 |
| 251e | >50-100 | 48h | 0.1-50 | 73b | 0.1-50 |
| 260b | 0.1-50 | 51g | 0.1-50 | 72c | 0.1-50 |
| 262f | 0.1-50 | 51h | 0.1-50 | 72d | 0.1-50 |
| 263d | 0.1-50 | 64a | 0.1-50 | 66a | 0.1-50 |
| 15g | >100 | 64b | 0.1-50 | 66b | 0.1-50 |
| 16b | >100 | 49i | 0.1-50 | 37b | 0.1-50 |
| 90f | >100 | 49j | 0.1-50 | 37a | 0.1-50 |
| 206d | 0.1-50 | 231d | 0.1-50 | 244g | 0.1-50 |
| 205d | 0.1-50 | 232a | >100 | 244h | 0.1-50 |
| 205e | 0.1-50 | 246f | 0.1-50 | 244i | 0.1-50 |
| 208d | 0.1-50 | 234d | >100 | 244j | 0.1-50 |
| 209d | 0.1-50 | 235g | 0.1-50 | 244k | 0.1-50 |
| 210d | 0.1-50 | 218c | 0.1-50 | 253e | 0.1-50 |
| 211d | 0.1-50 | 219c | 0.1-50 | 245c | 0.1-50 |
| 212g | 0.1-50 | 239d | >100 | 257b | 0.1-50 |
| 214g | 0.1-50 | 267c | >100 | 254c | 0.1-50 |
| 213d | 0.1-50 | 240b | 0.1-50 | 255a | 0.1-50 |
| 222k | >100 | 236h | 0.1-50 | 265d | 0.1-50 |
| 223f | >100 | 237a | 0.1-50 | 256a | 0.1-50 |
| 220f | 0.1-50 | 238c | 0.1-50 | 268g | >50-100 |
| 224b | >100 | 241a | 0.1-50 | 258g | 0.1-50 |
| 225a | 0.1-50 | 215d | >100 | 248l | 0.1-50 |
| 226a | >100 | 238d | 0.1-50 | 248k | 0.1-50 |
| 227d | 0.1-50 | 221i | 0.1-50 | 264g | 0.1-50 |
| 228a | 0.1-50 | 216d | 0.1-50 | 261k | 0.1-50 |
| 229i | 0.1-50 | 243a | 0.1-50 | 259d | 0.1-50 |
| 230a | >100 | 217d | >50-100 | 266j | 0.1-50 |
|  |  |  |  | 269b | 0.1-50 |
|  |  |  |  | 270a | >50-100 |

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound, or a pharmaceutically acceptable salt thereof, selected from the group consisting of:

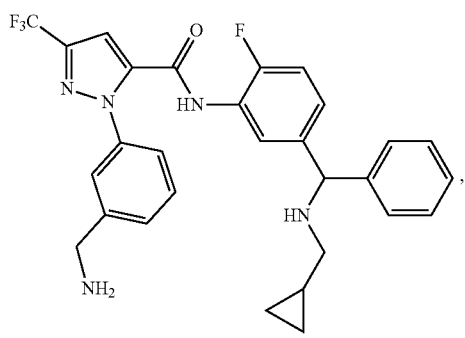
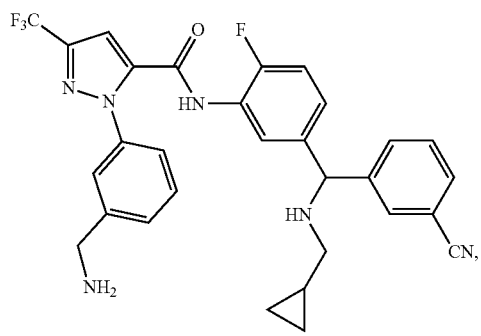
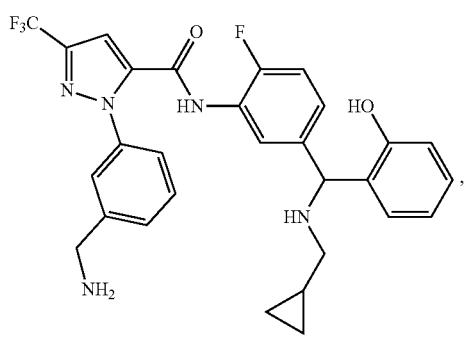
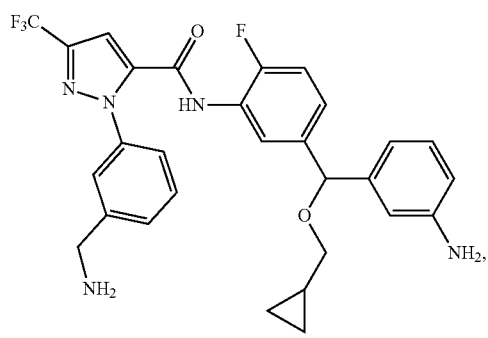
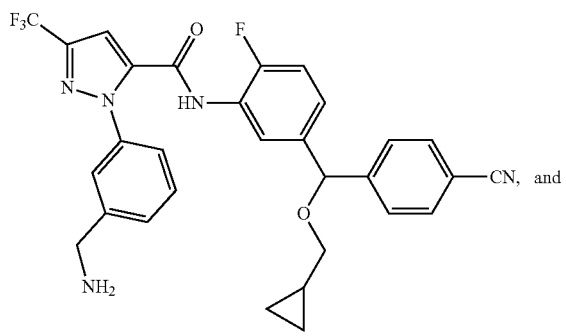
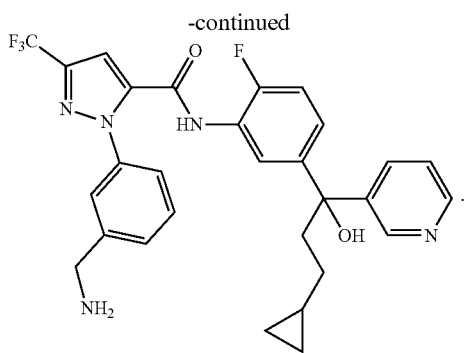
2. The compound of claim 1, wherein the compound is
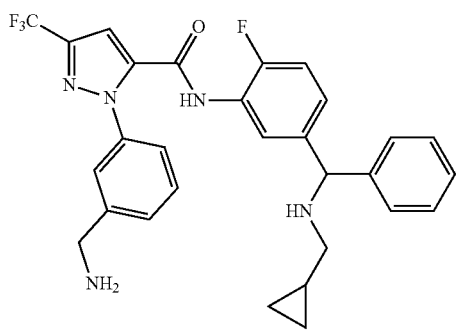
or a pharmaceutically acceptable salt thereof.
3. The compound of claim 1, wherein the compound is
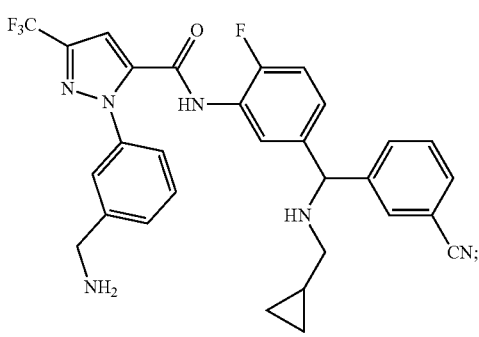 [SMILES: N#Cc1cccc(C(NCC2CC2)c2ccc(F)c(NC(=O)c3cc(C(F)(F)F)nn3-c3cccc(CN)c3)c2)c1]
or a pharmaceutically acceptable salt thereof.
4. The compound of claim 1, wherein the compound is
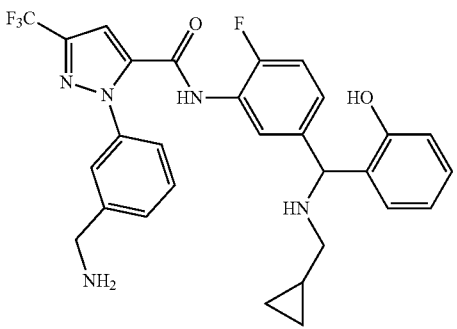
or a pharmaceutically acceptable salt thereof.

5. The compound of claim 1, wherein the compound is

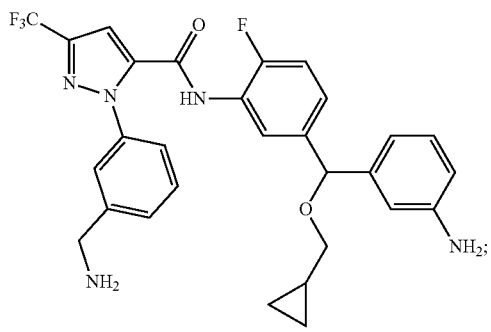 [SMILES: NCc1cccc(-n2nc(C(F)(F)F)cc2C(=O)Nc2cc(C(OCC3CC3)c3cccc(N)c3)ccc2F)c1]

or a pharmaceutically acceptable salt thereof.

6. The compound of claim 1, wherein the compound is

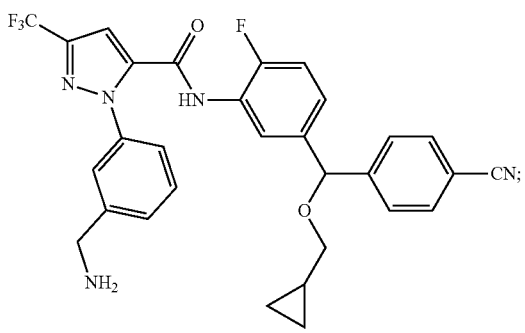 [SMILES: N#Cc1ccc(C(OCC2CC2)c2ccc(F)c(NC(=O)c3cc(C(F)(F)F)nn3-c3cccc(CN)c3)c2)cc1]

or a pharmaceutically acceptable salt thereof.

7. The compound of claim 1, wherein the compound is

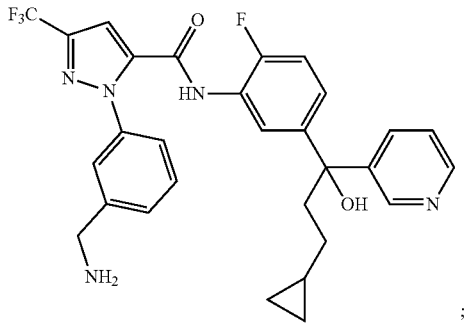 [SMILES: NCc1cccc(-n2nc(C(F)(F)F)cc2C(=O)Nc2cc(C(O)(CCC3CC3)c3cccnc3)ccc2F)c1]

or a pharmaceutically acceptable salt thereof.

8. A compound, or a pharmaceutically acceptable salt thereof, selected from the group consisting of:

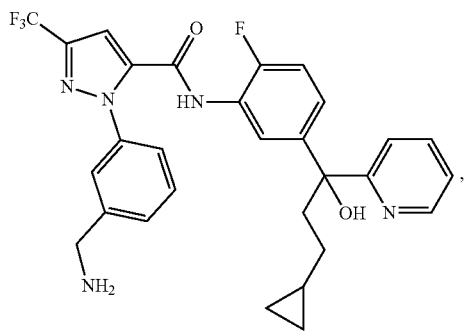

-continued

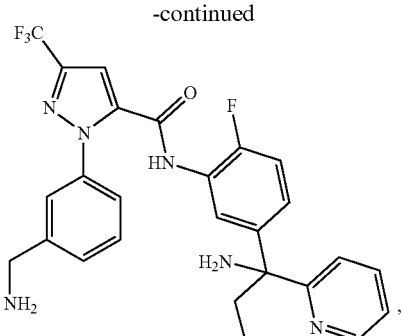

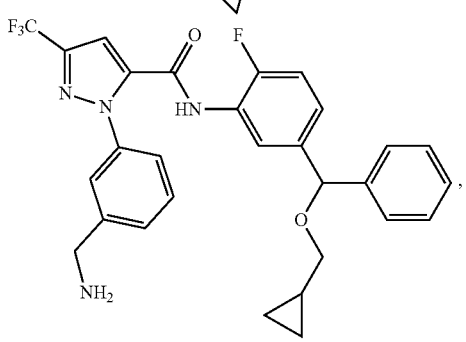

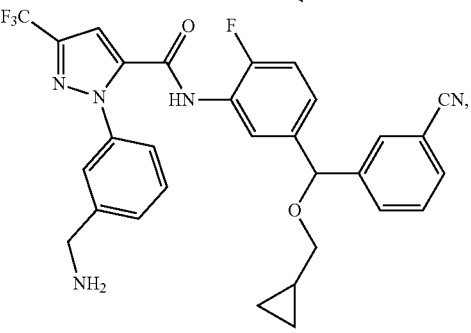

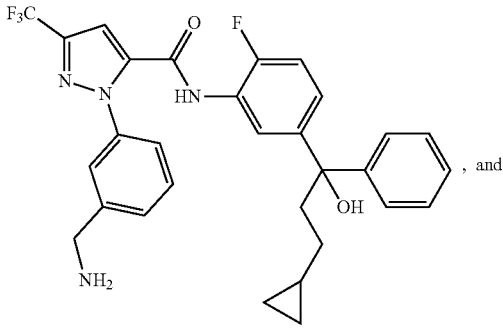

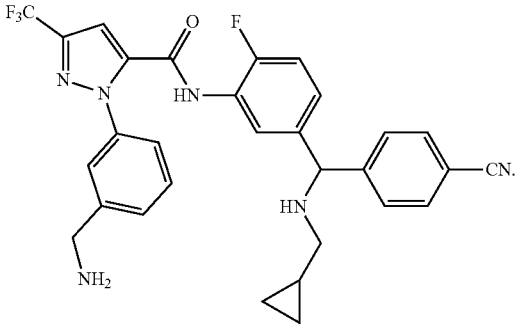 [SMILES: N#Cc1ccc(C(NCC2CC2)c2ccc(F)c(NC(=O)c3cc(C(F)(F)F)nn3-c3cccc(CN)c3)c2)cc1]

9. The compound of claim 8, wherein the compound is

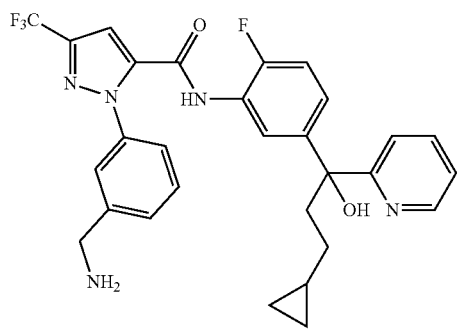

;

or a pharmaceutically acceptable salt thereof.

10. The compound of claim 8, wherein the compound is

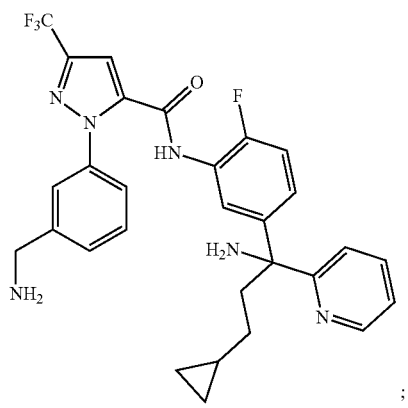 [SMILES: NCc1cccc(-n2nc(C(F)(F)F)cc2C(=O)Nc2cc(C(N)(CCC3CC3)c3ccccn3)ccc2F)c1]

;

or a pharmaceutically acceptable salt thereof.

11. The compound of claim 8, wherein the compound is

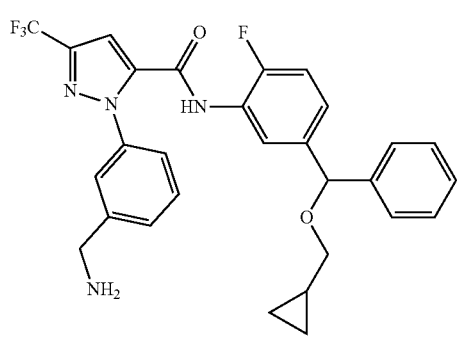

;

or a pharmaceutically acceptable salt thereof.

12. The compound of claim 8, wherein the compound is

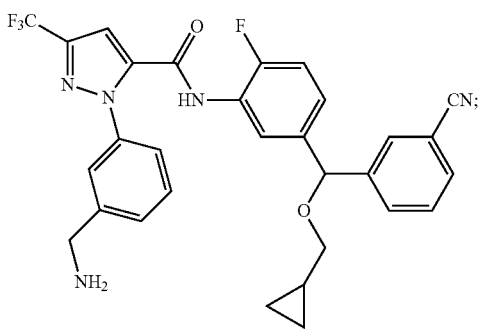 [SMILES: N#Cc1cccc(C(OCC2CC2)c2ccc(F)c(NC(=O)c3cc(C(F)(F)F)nn3-c3cccc(CN)c3)c2)c1]

or a pharmaceutically acceptable salt thereof.

13. The compound of claim 8, wherein the compound is

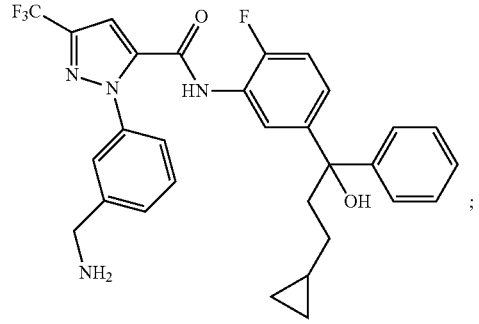 [SMILES: NCc1cccc(-n2nc(C(F)(F)F)cc2C(=O)Nc2cc(C(O)(CCC3CC3)c3ccccc3)ccc2F)c1]

;

or a pharmaceutically acceptable salt thereof.

14. The compound of claim 8, wherein the compound is

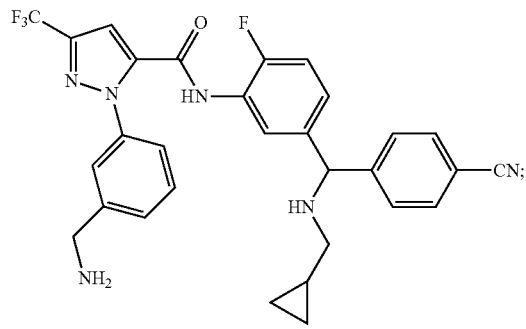 [SMILES: N#Cc1ccc(C(NCC2CC2)c2ccc(F)c(NC(=O)c3cc(C(F)(F)F)nn3-c3cccc(CN)c3)c2)cc1]

or a pharmaceutically acceptable salt thereof.

15. A compound, or a pharmaceutically acceptable salt thereof, selected from the group consisting of:

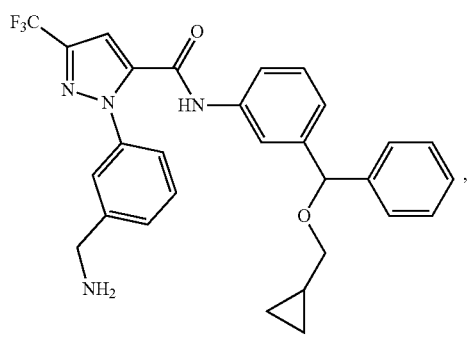
,
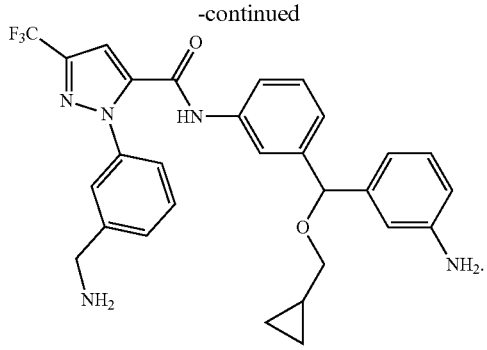
-continued
16. The compound of claim 15, wherein the compound is
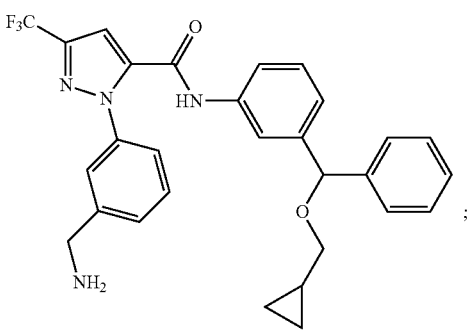 [SMILES: NCc1cccc(-n2nc(C(F)(F)F)cc2C(=O)Nc2cccc(C(OCC3CC3)c3ccccc3)c2)c1]
;
or a pharmaceutically acceptable salt thereof.
17. The compound of claim 15, wherein the compound is
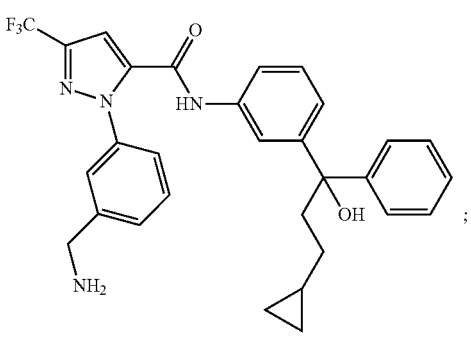 [SMILES: NCc1cccc(-n2nc(C(F)(F)F)cc2C(=O)Nc2cccc(C(O)(CCC3CC3)c3ccccc3)c2)c1]
;
or a pharmaceutically acceptable salt thereof.
18. The compound of claim 15, wherein the compound is
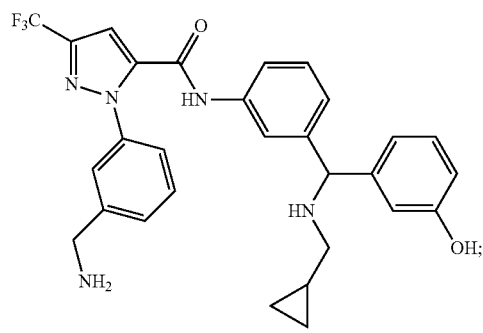 [SMILES: NCc1cccc(-n2nc(C(F)(F)F)cc2C(=O)Nc2cccc(C(NCC3CC3)c3cccc(O)c3)c2)c1]
;
or a pharmaceutically acceptable salt thereof.

19. The compound of claim 15, wherein the compound is

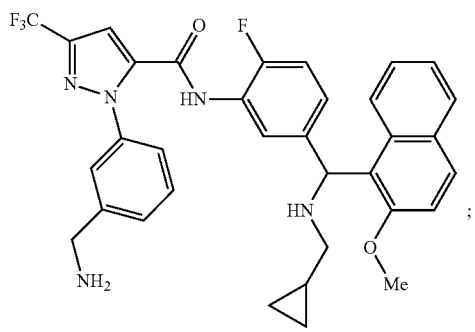 [SMILES: COc1ccc2ccccc2c1C(NCC1CC1)c1ccc(F)c(NC(=O)c2cc(C(F)(F)F)nn2-c2cccc(CN)c2)c1]

or a pharmaceutically acceptable salt thereof.

20. The compound of claim 15, wherein the compound is

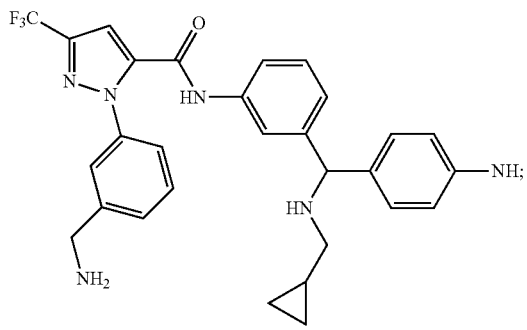

or a pharmaceutically acceptable salt thereof.

21. The compound of claim 15, wherein the compound is

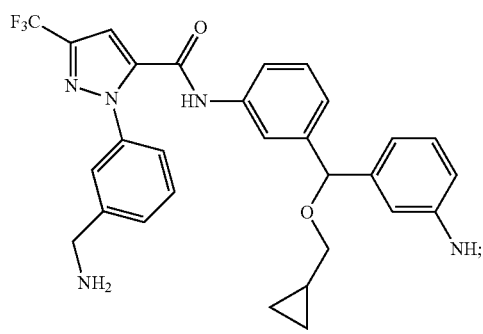

or a pharmaceutically acceptable salt thereof.

22. A compound, or a pharmaceutically acceptable salt thereof, selected from the group consisting of:

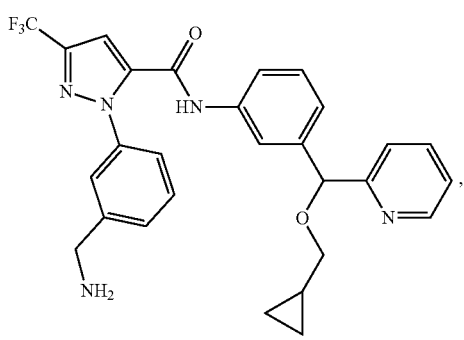

-continued

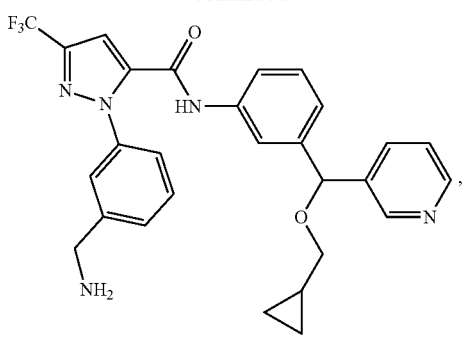

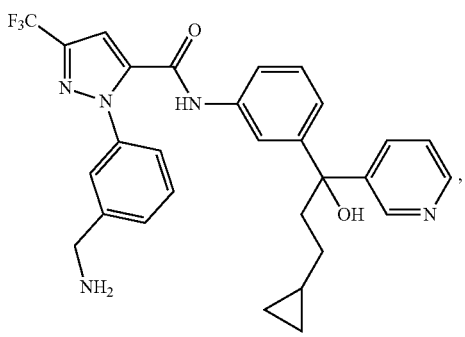

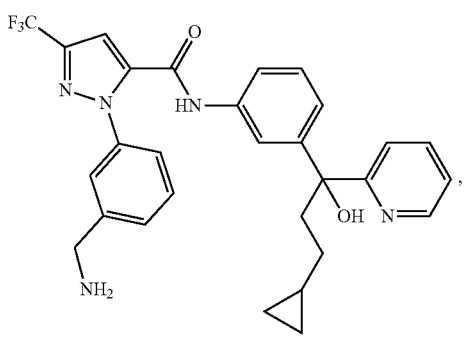

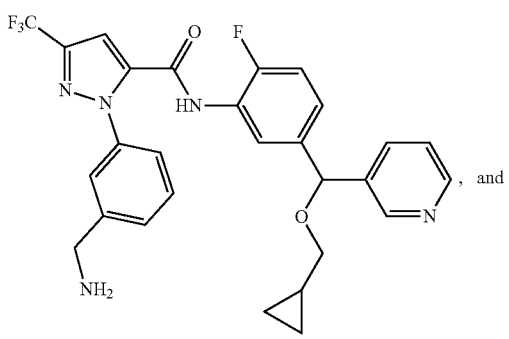

, and

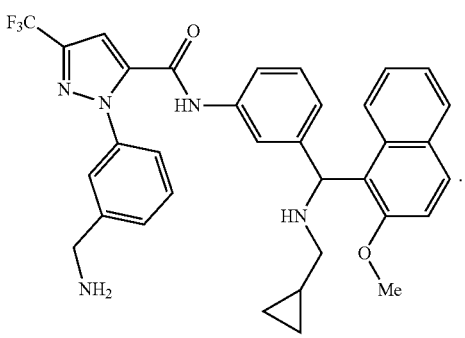 [SMILES: COc1ccc2ccccc2c1C(NCC1CC1)c1cccc(NC(=O)c2cc(C(F)(F)F)nn2-c2cccc(CN)c2)c1]

.

23. The compound of claim 22, wherein the compound is

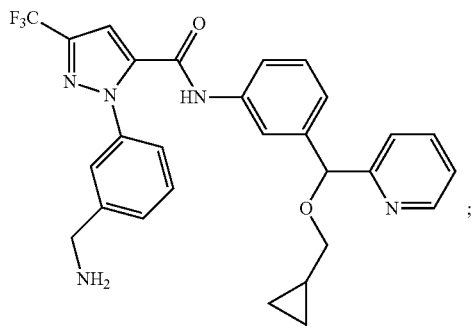 [SMILES: NCc1cccc(-n2nc(C(F)(F)F)cc2C(=O)Nc2cccc(C(OCC3CC3)c3ccccn3)c2)c1]

or a pharmaceutically acceptable salt thereof.

24. The compound of claim 22, wherein the compound is

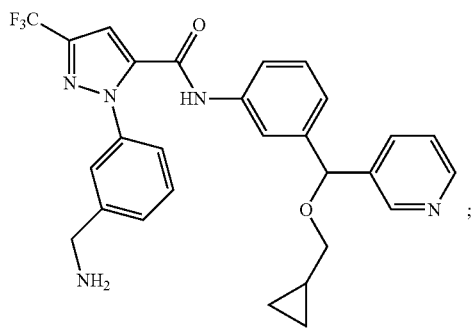 [SMILES: NCc1cccc(-n2nc(C(F)(F)F)cc2C(=O)Nc2cccc(C(OCC3CC3)c3cccnc3)c2)c1]

or a pharmaceutically acceptable salt thereof.

25. The compound of claim 22, wherein the compound is

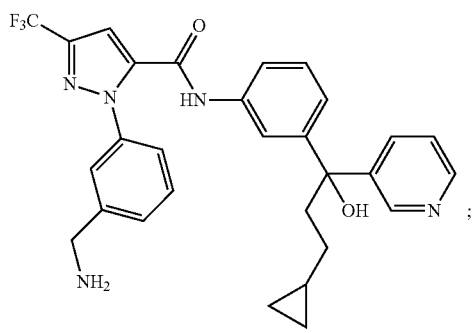 [SMILES: NCc1cccc(-n2nc(C(F)(F)F)cc2C(=O)Nc2cccc(C(O)(CCC3CC3)c3cccnc3)c2)c1]

or a pharmaceutically acceptable salt thereof.

26. The compound of claim 22, wherein the compound is

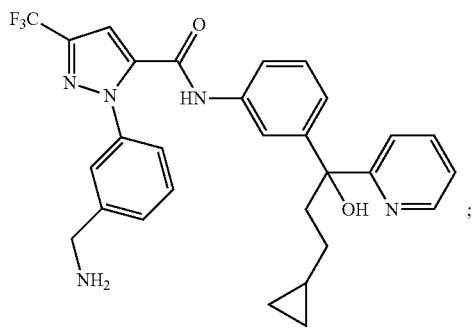 [SMILES: NCc1cccc(-n2nc(C(F)(F)F)cc2C(=O)Nc2cccc(C(O)(CCC3CC3)c3ccccn3)c2)c1]

or a pharmaceutically acceptable salt thereof.

27. The compound of claim 22, wherein the compound is

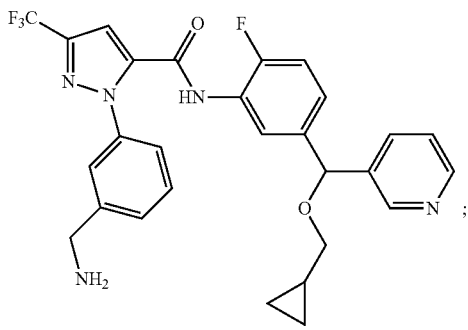 [SMILES: NCc1cccc(-n2nc(C(F)(F)F)cc2C(=O)Nc2cc(C(OCC3CC3)c3cccnc3)ccc2F)c1]

or a pharmaceutically acceptable salt thereof.

28. The compound of claim 22, wherein the compound is

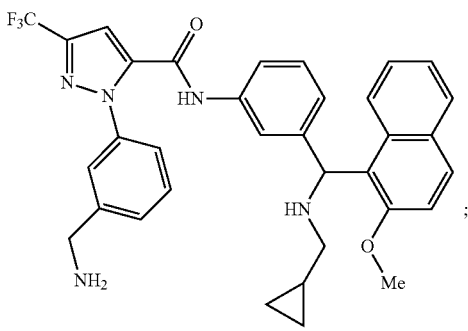 [SMILES: COc1ccc2ccccc2c1C(NCC1CC1)c1cccc(NC(=O)c2cc(C(F)(F)F)nn2-c2cccc(CN)c2)c1]

or a pharmaceutically acceptable salt thereof.

29. The compound of claim 1, wherein the pharmaceutically acceptable salt thereof is a hydrochloride salt.

30. The compound of claim 1, wherein the compound is:
- (+)-1-(3-(aminomethyl)phenyl)-N-(5-(((cyclopropylmethyl)amino)(phenyl)methyl)-2-fluorophenyl)-3-(trifluoromethyl)-1H-pyrazole-5-carboxamide;
- (−)-1-(3-(aminomethyl)phenyl)-N-(5-(((cyclopropylmethyl)amino)(phenyl)methyl)-2-fluorophenyl)-3-(trifluoromethyl)-1H-pyrazole-5-carboxamide;
- (+)-1-(3-(aminomethyl)phenyl)-N-(5-((3-cyanophenyl)(cyclopropylmethylamino)methyl)-2-fluorophenyl)-3-(trifluoromethyl)-1H-pyrazole-5-carboxamide;
- (−)-1-(3-(aminomethyl)phenyl)-N-(5-((3-cyanophenyl)(cyclopropylmethylamino)methyl)-2-fluorophenyl)-3-(trifluoromethyl)-1H-pyrazole-5-carboxamide;
- (+)-1-(3-(aminomethyl)phenyl)-N-(5-((cyclopropylmethylamino)(2-hydroxyphenyl)methyl)-2-fluorophenyl)-3-(trifluoromethyl)-1H-pyrazole-5-carboxamide;
- (−)-1-(3-(aminomethyl)phenyl)-N-(5-((cyclopropylmethylamino)(2-hydroxyphenyl)methyl)-2-fluorophenyl)-3-(trifluoromethyl)-1H-pyrazole-5-carboxamide;
- (+)-1-(3-(aminomethyl)phenyl)-N-(5-((3-aminophenyl)(cyclopropylmethoxy)methyl)-2-fluorophenyl)-3-(trifluoromethyl)-1H-pyrazole-5-carboxamide;
- (−)-1-(3-(aminomethyl)phenyl)-N-(5-((3-aminophenyl)(cyclopropylmethoxy)methyl)-2-fluorophenyl)-3-(trifluoromethyl)-1H-pyrazole-5-carboxamide;
- (+)-1-(3-(aminomethyl)phenyl)-N-(5-((4-cyanophenyl)(cyclopropylmethoxy)methyl)-2-fluorophenyl)-3-(trifluoromethyl)-1H-pyrazole-5-carboxamide;
- (−)-1-(3-(aminomethyl)phenyl)-N-(5-((4-cyanophenyl)(cyclopropylmethoxy)methyl)-2-fluorophenyl)-3-(trifluoromethyl)-1H-pyrazole-5-carboxamide;

(+)-1-(3-(aminomethyl)phenyl)-N-(5-(3-cyclopropyl-1-hydroxy-1-(pyridin-3-yl)propyl)-2-fluorophenyl)-3-(trifluoromethyl)-1H-pyrazole-5-carboxamide;

(−)-1-(3-(aminomethyl)phenyl)-N-(5-(3-cyclopropyl-1-hydroxy-1-(pyridin-3-yl)propyl)-2-fluorophenyl)-3-(trifluoromethyl)-1H-pyrazole-5-carboxamide;

or a pharmaceutically acceptable salt thereof.

31. The compound of claim 30, wherein the pharmaceutically acceptable salt thereof is a hydrochloride salt.

32. The compound of claim 30, wherein the compound is:
(+)-1-(3-(aminomethyl)phenyl)-N-(5-((3-cyanophenyl)(cyclopropylmethylamino)methyl)-2-fluorophenyl)-3-(trifluoromethyl)-1H-pyrazole-5-carboxamide;

(−)-1-(3-(aminomethyl)phenyl)-N-(5-((3-cyanophenyl)(cyclopropylmethylamino)methyl)-2-fluorophenyl)-3-(trifluoromethyl)-1H-pyrazole-5-carboxamide;

or a pharmaceutically acceptable salt thereof.

33. The compound of claim 32, wherein the compound is (+)-1-(3-(aminomethyl)phenyl)-N-(5-((3-cyanophenyl)(cyclopropylmethylamino)methyl)-2-fluorophenyl)-3-(trifluoromethyl)-1H-pyrazole-5-carboxamide; or a pharmaceutically acceptable salt thereof.

34. The compound of claim 32, wherein the compound is (−)-1-(3-(aminomethyl)phenyl)-N-(5-((3-cyanophenyl)(cyclopropylmethylamino)methyl)-2-fluorophenyl)-3-(trifluoromethyl)-1H-pyrazole-5-carboxamide; or a pharmaceutically acceptable salt thereof.

35. The compound of claim 32, wherein the pharmaceutically acceptable salt thereof is a hydrochloride salt.

36. The compound of claim 35, wherein the pharmaceutically acceptable salt thereof is a bis(hydrochloride) salt.

37. The compound of claim 8, wherein the pharmaceutically acceptable salt thereof is a hydrochloride salt.

38. The compound of claim 8, wherein the compound is:
(+)-1-(3-(aminomethyl)phenyl)-N-(5-(3-cyclopropyl-1-hydroxy-1-(pyridin-2-yl)propyl)-2-fluorophenyl)-3-(trifluoromethyl)-1H-pyrazole-5-carboxamide;

(−)-1-(3-(aminomethyl)phenyl)-N-(5-(3-cyclopropyl-1-hydroxy-1-(pyridin-2-yl)propyl)-2-fluorophenyl)-3-(trifluoromethyl)-1H-pyrazole-5-carboxamide;

(+)-N-(5-(1-amino-3-cyclopropyl-1-(pyridin-2-yl)propyl)-2-fluorophenyl)-1-(3-(aminomethyl)phenyl)-3-(trifluoromethyl)-1H-pyrazole-5-carboxamide;

(−)-N-(5-(1-amino-3-cyclopropyl-1-(pyridin-2-yl)propyl)-2-fluorophenyl)-1-(3-(aminomethyl)phenyl)-3-(trifluoromethyl)-1H-pyrazole-5-carboxamide;

(+)-1-(3-(aminomethyl)phenyl)-N-(5-((cyclopropylmethoxy)(phenyl)methyl)-2-fluorophenyl)-3-(trifluoromethyl)-1H-pyrazole-5-carboxamide;

(−)-1-(3-(aminomethyl)phenyl)-N-(5-((cyclopropylmethoxy)(phenyl)methyl)-2-fluorophenyl)-3-(trifluoromethyl)-1H-pyrazole-5-carboxamide;

(+)-1-(3-(aminomethyl)phenyl)-N-(5-((3-cyanophenyl)(cyclopropylmethoxy)methyl)-2-fluorophenyl)-3-(trifluoromethyl)-1H-pyrazole-5-carboxamide;

(−)-1-(3-(aminomethyl)phenyl)-N-(5-((3-cyanophenyl)(cyclopropylmethoxy)methyl)-2-fluorophenyl)-3-(trifluoromethyl)-1H-pyrazole-5-carboxamide;

(+)-1-(3-(aminomethyl)phenyl)-N-(5-(3-cyclopropyl-1-hydroxy-1-phenylpropyl)-2-fluorophenyl)-3-(trifluoromethyl)-1H-pyrazole-5-carboxamide;

(−)-1-(3-(aminomethyl)phenyl)-N-(5-(3-cyclopropyl-1-hydroxy-1-phenylpropyl)-2-fluorophenyl)-3-(trifluoromethyl)-1H-pyrazole-5-carboxamide;

(+)-1-(3-(aminomethyl)phenyl)-N-(5-((4-cyanophenyl)(cyclopropylmethylamino)methyl)-2-fluorophenyl)-3-(trifluoromethyl)-1H-pyrazole-5-carboxamide;

(−)-1-(3-(aminomethyl)phenyl)-N-(5-((4-cyanophenyl)(cyclopropylmethylamino)methyl)-2-fluorophenyl)-3-(trifluoromethyl)-1H-pyrazole-5-carboxamide;

or a pharmaceutically acceptable salt thereof.

39. The compound of claim 38, wherein the pharmaceutically acceptable salt thereof is a hydrochloride salt.

40. The compound of claim 15, wherein the pharmaceutically acceptable salt thereof is a hydrochloride salt.

41. The compound of claim 15, wherein the compound is:
(+)-1-(3-(aminomethyl)phenyl)-N-(3-((cyclopropylmethoxy)(phenyl)methyl)phenyl)-3-(trifluoromethyl)-1H-pyrazole-5-carboxamide;

(−)-1-(3-(aminomethyl)phenyl)-N-(3-((cyclopropylmethoxy)(phenyl)methyl)phenyl)-3-(trifluoromethyl)-1H-pyrazole-5-carboxamide;

(+)-1-(3-(aminomethyl)phenyl)-N-(3-(3-cyclopropyl-1-hydroxy-1-phenylpropyl)phenyl)-3-(trifluoromethyl)-1H-pyrazole-5-carboxamide;

(−)-1-(3-(aminomethyl)phenyl)-N-(3-(3-cyclopropyl-1-hydroxy-1-phenylpropyl)phenyl)-3-(trifluoromethyl)-1H-pyrazole-5-carboxamide;

(+)-1-(3-(aminomethyl)phenyl)-N-(3-((cyclopropylmethylamino)(3-hydroxyphenyl)methyl)phenyl)-3-(trifluoromethyl)-1H-pyrazole-5-carboxamide;

(−)-1-(3-(aminomethyl)phenyl)-N-(3-((cyclopropylmethylamino)(3-hydroxyphenyl)methyl)phenyl)-3-(trifluoromethyl)-1H-pyrazole-5-carboxamide;

(+)-1-(3-(aminomethyl)phenyl)-N-(5-((cyclopropylmethylamino)(2-methoxynaphthalen-1-yl)methyl)-2-fluorophenyl)-3-(trifluoromethyl)-1H-pyrazole-5-carboxamide;

(−)-1-(3-(aminomethyl)phenyl)-N-(5-((cyclopropylmethylamino)(2-methoxynaphthalen-1-yl)methyl)-2-fluorophenyl)-3-(trifluoromethyl)-1H-pyrazole-5-carboxamide;

(+)-1-(3-(aminomethyl)phenyl)-N-(3-((4-aminophenyl)(cyclopropylmethyl-amino)methyl)phenyl)-3-(trifluoromethyl)-1H-pyrazole-5-carboxamide;

(−)-1-(3-(aminomethyl)phenyl)-N-(3-((4-aminophenyl)(cyclopropylmethyl-amino)methyl)phenyl)-3-(trifluoromethyl)-1H-pyrazole-5-carboxamide;

(+)-1-(3-(aminomethyl)phenyl)-N-(3-((3-aminophenyl)(cyclopropyl-methoxy)methyl)phenyl)-3-(trifluoromethyl)-1H-pyrazole-5-carboxamide;

(−)-1-(3-(aminomethyl)phenyl)-N-(3-((3-aminophenyl)(cyclopropyl-methoxy)methyl)phenyl)-3-(trifluoromethyl)-1H-pyrazole-5-carboxamide;

or a pharmaceutically acceptable salt thereof.

42. The compound of claim 41, wherein the pharmaceutically acceptable salt thereof is a hydrochloride salt.

43. The compound of claim 22, wherein the pharmaceutically acceptable salt thereof is a hydrochloride salt.

44. The compound of claim 22, wherein the compound is:
(+)-1-(3-(aminomethyl)phenyl)-N-(3-((cyclopropylmethoxy)(pyridin-2-yl)methyl)-phenyl)-3-(trifluoromethyl)-1H-pyrazole-5-carboxamide;

(−)-1-(3-(aminomethyl)phenyl)-N-(3-((cyclopropylmethoxy)(pyridin-2-yl)methyl)-phenyl)-3-(trifluoromethyl)-1H-pyrazole-5-carboxamide;

(+)-1-(3-(aminomethyl)phenyl)-N-(3-((cyclopropylmethoxy)(pyridin-3-yl)methyl)phenyl)-3-(trifluoromethyl)-1H-pyrazole-5-carboxamide;

(−)-1-(3-(aminomethyl)phenyl)-N-(3-((cyclopropylmethoxy)(pyridin-3-yl)methyl)phenyl)-3-(trifluoromethyl)-1H-pyrazole-5-carboxamide;

(+)-1-(3-(aminomethyl)phenyl)-N-(3-(3-cyclopropyl-1-hydroxy-1-(pyridin-3-yl)propyl)phenyl)-3-(trifluoromethyl)-1H-pyrazole-5-carboxamide;

(−)-1-(3-(aminomethyl)phenyl)-N-(3-(3-cyclopropyl-1-hydroxy-1-(pyridin-3-yl)propyl)phenyl)-3-(trifluoromethyl)-1H-pyrazole-5-carboxamide;

(+)-1-(3-(aminomethyl)phenyl)-N-(3-(3-cyclopropyl-1-hydroxy-1-(pyridin-2-yl)propyl)phenyl)-3-(trifluoromethyl)-1H-pyrazole-5-carboxamide;

(−)-1-(3-(aminomethyl)phenyl)-N-(3-(3-cyclopropyl-1-hydroxy-1-(pyridin-2-yl)propyl)phenyl)-3-(trifluoromethyl)-1H-pyrazole-5-carboxamide;

(+)-1-(3-(aminomethyl)phenyl)-N-(5-((cyclopropylmethoxy)(pyridin-3-yl)methyl)-2-fluorophenyl)-3-(trifluoromethyl)-1H-pyrazole-5-carboxamide;

(−)-1-(3-(aminomethyl)phenyl)-N-(5-((cyclopropylmethoxy)(pyridin-3-yl)methyl)-2-fluorophenyl)-3-(trifluoromethyl)-1H-pyrazole-5-carboxamide;

(+)-1-(3-(Aminomethyl)phenyl)-N-(3-((cyclopropylmethylamino)(2-methoxynaphthalen-1-yl)methyl)phenyl)-3-(trifluoromethyl)-1H-pyrazole-5-carboxamide;

(−)-1-(3-(Aminomethyl)phenyl)-N-(3-((cyclopropylmethylamino)(2-methoxynaphthalen-1-yl)methyl)phenyl)-3-(trifluoromethyl)-1H-pyrazole-5-carboxamide;

or a pharmaceutically acceptable salt thereof.

45. The compound of claim 44, wherein the pharmaceutically acceptable salt thereof is a hydrochloride salt.

* * * * *